(12) United States Patent
Clemens et al.

(10) Patent No.: US 11,866,450 B2
(45) Date of Patent: Jan. 9, 2024

(54) MODULATORS OF CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATORS

(71) Applicant: Vertex Pharmaceuticals Incorporated, Boston, MA (US)

(72) Inventors: Jeremy J. Clemens, San Diego, CA (US); Alexander Russell Abela, Escondido, CA (US); Corey Don Anderson, San Diego, CA (US); Brett B. Busch, San Diego, CA (US); Weichao George Chen, San Diego, CA (US); Thomas Cleveland, San Marcos, CA (US); Timothy Richard Coon, Carlsbad, CA (US); Bryan Frieman, La Jolla, CA (US); Senait G. Ghirmai, San Diego, CA (US); Peter Grootenhuis, Del Mar, CA (US); Anton V. Gulevich, San Diego, CA (US); Sara Sabina Hadida Ruah, La Jolla, CA (US); Clara Kuang-Ju Hsia, San Diego, CA (US); Ping Kang, San Diego, CA (US); Haripada Khatuya, San Diego, CA (US); Jason McCartney, Cardiff by the Sea, CA (US); Mark Thomas Miller, San Diego, CA (US); Prasuna Paraselli, San Diego, CA (US); Fabrice Pierre, La Jolla, CA (US); Sara E. Swift, San Diego, CA (US); Andreas Termin, Encinitas, CA (US); Johnny Uy, San Diego, CA (US); Carl V. Vogel, Carlsbad, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 17/323,267

(22) Filed: May 18, 2021

(65) Prior Publication Data
US 2022/0106331 A1    Apr. 7, 2022

Related U.S. Application Data

(62) Division of application No. 16/276,350, filed on Feb. 14, 2019, now Pat. No. 11,066,417.

(60) Provisional application No. 62/631,453, filed on Feb. 15, 2018.

(51) Int. Cl.
| | | |
|---|---|---|
| C07D 513/22 | (2006.01) | |
| A61K 31/439 | (2006.01) | |
| A61P 11/00 | (2006.01) | |
| A61K 31/47 | (2006.01) | |
| A61K 31/404 | (2006.01) | |
| C07D 515/22 | (2006.01) | |

(52) U.S. Cl.
CPC .......... *C07D 513/22* (2013.01); *A61K 31/404* (2013.01); *A61K 31/439* (2013.01); *A61K 31/47* (2013.01); *A61P 11/00* (2018.01); *C07D 515/22* (2013.01)

(58) Field of Classification Search
CPC .................................................. C07D 513/22
See application file for complete search history.

(56) References Cited

U.S. PATENT DOCUMENTS

| | | | |
|---|---|---|---|
| 2,677,682 A | 5/1954 | Fahrenbach et al. | |
| 9,663,508 B2 | 5/2017 | Bregman et al. | |
| 9,782,408 B2 | 10/2017 | Miller et al. | |
| 9,981,910 B2 | 5/2018 | Altenbach et al. | |
| 10,118,916 B2 | 11/2018 | Altenbach et al. | |
| 10,131,670 B2 | 11/2018 | Strohbach et al. | |
| 10,138,227 B2 | 11/2018 | Altenbach et al. | |
| 10,208,053 B2 | 2/2019 | Strohbach et al. | |
| 10,258,624 B2 | 4/2019 | Miller et al. | |
| 11,066,417 B2 * | 7/2021 | Clemens .............. | A61K 31/404 |
| 2011/0098311 A1 | 4/2011 | Van Goor et al. | |
| 2013/0317000 A1 | 11/2013 | Chowdhury et al. | |

(Continued)

FOREIGN PATENT DOCUMENTS

| | | |
|---|---|---|
| CL | 2017000824 A1 | 1/2018 |
| CL | 2019002734 A1 | 1/2020 |

(Continued)

OTHER PUBLICATIONS

"A Phase 1/2 Study of VX-121 in Healthy Subjects and in Subjects with Cystic Fibrosis," EU Clinical Trials Register, May 3, 2019 (May 3, 2019), XP055903414, Retrieved from the Internet: URL:https://www.clinicaltrialsregister.eu/ctr-search/trial/2018-000126-55/NL [retrieved on Mar. 21, 2022].

(Continued)

*Primary Examiner* — John S Kenyon
(74) *Attorney, Agent, or Firm* — Finnegan, Henderson, Farabow, Garrett & Dunner, LLP

(57) ABSTRACT

Compounds of Formula (I):

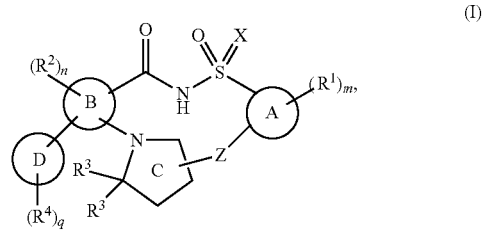

pharmaceutically acceptable salts thereof, deuterated derivatives of any of the foregoing, and metabolites of any of the foregoing are disclosed. Pharmaceutical compositions comprising the same, methods of treating cystic fibrosis using the same, and methods for making the same are also disclosed.

41 Claims, 43 Drawing Sheets

(56) References Cited

U.S. PATENT DOCUMENTS

| | | |
|---|---|---|
| 2013/0317001 A1 | 11/2013 | Andrez et al. |
| 2014/0073667 A1 | 3/2014 | Morgan et al. |
| 2016/0095858 A1* | 4/2016 | Vertex .............. A61K 31/415 546/261 |
| 2018/0099932 A1 | 4/2018 | Altenbach et al. |
| 2018/0141954 A1 | 5/2018 | Strohbach et al. |
| 2018/0162839 A1 | 6/2018 | Abela et al. |
| 2018/0170938 A1 | 6/2018 | Strohbach |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0119253 A1 | 4/2019 | Dhamankar et al. |
| 2019/0153000 A1 | 5/2019 | Munoz et al. |
| 2019/0240197 A1 | 8/2019 | Chu et al. |
| 2019/0248809 A1 | 8/2019 | Clemens et al. |
| 2019/0269683 A1 | 9/2019 | Miller et al. |
| 2022/0041621 A1 | 2/2022 | Clemens et al. |
| 2022/0047564 A1 | 2/2022 | Altshuler et al. |
| 2022/0106331 A1 | 4/2022 | Clemens et al. |
| 2022/0127247 A1 | 4/2022 | Azimioara et al. |

FOREIGN PATENT DOCUMENTS

| | | | |
|---|---|---|---|
| CL | | 2019001553 A1 | 3/2020 |
| CL | | 2020000122 A1 | 7/2020 |
| CL | | 2020000856 A1 | 8/2020 |
| CN | | 102227424 A | 10/2011 |
| CN | | 106432213 A | 2/2017 |
| EC | | SP19028690 A | 4/2019 |
| EC | | SP19048759 A | 7/2019 |
| EC | | SP20003147 A | 2/2020 |
| EC | | SP20053845 A | 9/2020 |
| EP | | 0 846 687 A1 | 6/1998 |
| JP | | 2014-526500 A | 10/2014 |
| JP | | 2021-512117 A | 5/2021 |
| JP | | 6896619 B2 | 6/2021 |
| JP | | 6916285 B2 | 7/2021 |
| JP | | 7061115 B2 | 4/2022 |
| TW | | 201713617 A | 4/2017 |
| WO | WO 2001/090092 A1 | | 11/2001 |
| WO | WO 2005/049018 A1 | | 6/2005 |
| WO | WO 2005/075435 A1 | | 8/2005 |
| WO | WO 2006/002421 A2 | | 1/2006 |
| WO | WO 2007/021982 A2 | | 2/2007 |
| WO | WO 2007/053641 A2 | | 5/2007 |
| WO | WO 2007/075946 A1 | | 7/2007 |
| WO | WO 2007/079139 A2 | | 7/2007 |
| WO | WO 2007/087066 A2 | | 8/2007 |
| WO | WO 2007/117715 A2 | | 10/2007 |
| WO | WO 2007/134279 A2 | | 11/2007 |
| WO | WO 2008/127399 A2 | | 10/2008 |
| WO | WO 2008/154241 A1 | | 12/2008 |
| WO | WO 2009/006315 A1 | | 1/2009 |
| WO | WO 2009/038683 A2 | | 3/2009 |
| WO | WO 2009/073757 A1 | | 6/2009 |
| WO | WO 2009/076142 A2 | | 6/2009 |
| WO | WO 2009/108657 A2 | | 9/2009 |
| WO | WO 2010/019239 A2 | | 2/2010 |
| WO | WO 2010/048526 A2 | | 4/2010 |
| WO | WO 2010/053471 A1 | | 5/2010 |
| WO | WO 2010/054138 A2 | | 5/2010 |
| WO | WO 2010/108162 A1 | | 9/2010 |
| WO | WO 2011/019413 A1 | | 2/2011 |
| WO | WO 2011/072241 A1 | | 6/2011 |
| WO | WO 2011/116397 A1 | | 9/2011 |
| WO | WO 2011/119984 A1 | | 9/2011 |
| WO | WO 2011/127241 A2 | | 10/2011 |
| WO | WO 2011/127290 A2 | | 10/2011 |
| WO | WO 2011/133751 A2 | | 10/2011 |
| WO | WO 2011/133951 A1 | | 10/2011 |
| WO | WO 2012/027247 A2 | | 3/2012 |
| WO | WO 2012/027731 A2 | | 3/2012 |
| WO | WO 2012/170061 A1 | | 12/2012 |
| WO | WO 2013/064984 A1 | | 5/2013 |
| WO | WO 2013/070961 A1 | | 5/2013 |
| WO | WO 2013/112804 A1 | | 8/2013 |
| WO | WO 2013/130669 A1 | | 9/2013 |
| WO | WO 2013/158121 A1 | | 10/2013 |
| WO | WO 2013/160419 A1 | | 10/2013 |
| WO | WO 2013/185112 A1 | | 12/2013 |
| WO | WO 2014/014841 A1 | | 1/2014 |
| WO | WO 2014/071122 A1 | | 5/2014 |
| WO | WO 2015/073231 A1 | | 7/2015 |
| WO | WO 2015/160787 A1 | | 10/2015 |
| WO | WO 2016/057730 A1 | | 2/2016 |
| WO | WO 2016/057572 A1 | | 4/2016 |
| WO | WO 2016/081556 A1 | | 5/2016 |
| WO | WO 2016/160945 A1 | | 10/2016 |
| WO | WO 2017/053455 A1 | | 3/2017 |
| WO | WO 2013/038386 A1 | | 5/2017 |
| WO | WO 2017/172802 A1 | | 10/2017 |
| WO | WO 2017/173274 A1 | | 10/2017 |
| WO | WO 2017/177124 A1 | | 10/2017 |
| WO | WO 2017/187321 A1 | | 11/2017 |
| WO | WO 2017/223188 A1 | | 12/2017 |
| WO | WO 2018/064632 A1 | | 4/2018 |
| WO | WO 2018/080591 A1 | | 5/2018 |
| WO | WO 2018/081377 A1 | | 5/2018 |
| WO | WO 2018/081378 A1 | | 5/2018 |
| WO | WO 2018/081381 A1 | | 5/2018 |
| WO | WO 2018/107100 A1 | | 6/2018 |
| WO | WO 2018/116185 A1 | | 6/2018 |
| WO | WO 2018/127130 A1 | | 7/2018 |
| WO | WO 2018/183367 A1 | | 10/2018 |
| WO | WO 2018/183964 A1 | | 10/2018 |
| WO | WO 2018/201126 A1 | | 11/2018 |
| WO | WO 2018/227049 A1 | | 12/2018 |
| WO | WO 2019/010092 A1 | | 1/2019 |
| WO | WO 2019/014352 A1 | | 1/2019 |
| WO | WO 2019/018353 A1 | | 1/2019 |
| WO | WO 2019/018395 A1 | | 1/2019 |
| WO | WO 2019/028228 A1 | | 2/2019 |
| WO | WO 2019/071078 A1 | | 4/2019 |
| WO | WO 2019/079760 A1 | | 4/2019 |
| WO | WO 2019/113089 A1 | | 6/2019 |
| WO | WO 2019/113476 A1 | | 6/2019 |
| WO | WO 2019/152940 A1 | | 8/2019 |
| WO | WO 2019/161078 A1 | | 8/2019 |
| WO | WO 2019/026075 A1 | | 10/2019 |
| WO | WO 2019/191620 A1 | | 10/2019 |
| WO | WO 2019/200246 A1 | | 10/2019 |
| WO | WO 2020/102346 A1 | | 5/2020 |
| WO | WO 2020/128925 A1 | | 6/2020 |
| WO | WO 2020/191227 A1 | | 9/2020 |
| WO | WO 2020/206080 A1 | | 10/2020 |
| WO | WO 2020/214921 A1 | | 10/2020 |
| WO | WO 2020/242935 A1 | | 12/2020 |
| WO | WO 2021/030552 A1 | | 2/2021 |
| WO | WO 2021/030554 A1 | | 2/2021 |
| WO | WO 2021/030555 A1 | | 2/2021 |
| WO | WO 2021/030556 A1 | | 2/2021 |
| WO | WO 2021/097054 A1 | | 5/2021 |
| WO | WO 2021/097057 A1 | | 5/2021 |
| WO | WO 2022/032068 A1 | | 2/2022 |
| WO | WO 2022/036060 A1 | | 2/2022 |

OTHER PUBLICATIONS

"A Phase 2 Study to Evaluate Efficacy and Safety of VX-561 in Subjects Aged 18 Years and Older With Cystic Fibrosis," ClinicatTials.gov, Apr. 11, 2019 (Apr. 11, 2019), XP055903562, Retrieved from the Internet: URL:https://clinicaltrials.gov/ct2/show/NCT03911713 [retrieved on Mar. 21, 2022].

"A Study to Evaluate the Safety and Efficacy of VX-121 Combination Therapy in Subjects with Cystic Fibrosis," ClinicalTrials.gov, Apr. 30, 2019 (Apr. 30, 2019), XP55903330, Retrieved from the Internet: URL:https://clinicaltrials.gov/ct2/show/NCT03912233 [retrieved on Mar. 21, 2022].

Alberti, C. and Tironi, C. (1964), "Sulfanilammidi Pirazoliche," VI. 1-(Tolil)-sulfanilamidopirazoli derivati dal 3-aminopirazolo, dal 4-aminopirazolo e dal 3-metil-5-aminopirazolo, *Il Farmaco—Ed. Sc.* 29(7), 618-637.

(56) References Cited

OTHER PUBLICATIONS

Alberti, C. and Tironi, C. (1971), "Sulfanilammidi Pirazoliche," *Il Farmaco—Ed. Sc.* 26(1), 66-88.
Bastin, Richard J., et al., "Salt selection and optimization procedures for pharmaceutical new chemical entities," *Org. Pro. Res. Dev.* 2000, 4(5), 427-435.
Borhade, Sanjay R., et al., "Synthesis of Novel Aryl and Heteroaryl Acyl Sulfonimidamides via Pd-Catalyzed Carbonylation Using a Nongaseous Precursor," *Organic Letters*, 2013, vol. 15, No. 5, pp. 1056-1059, XP055374206A, © 2013 American Chemical Society, ISSN: 1523-7060, DOI:10.1021/ol4/00049m, published on web Feb. 13, 2013.
Braker, William, et al. (1947), "Substituted Sulfanilamidopyrimidines," *J. Am. Chem. Society*, 69, 3072-3078.
Chen, Liangzhu, et al. (2014), "Synthesis and Antimicrobial Activity of the Hybrid Molecules between Sulfonamides and Active Antimicrobial Pleuromutilin Derivative," Chemical Biology and Drug Design, 86(2), 239-245.
Cherepakha, Artem Yu., et al. (2018), "Hetaryl Bromides Bearing the SO2F Group—Versatile Substrates for Palladium-Catalyzed C-C Coupling Reactions," *Eur J Org Chem*, 47: 6682-6692.
Chio, Li-Chun, et al. (1996), "Identification of a Class of Sulfonamides Highly Active Against Dihydropteroate Synthase from Toxoplasma Gondii, Pneumocystis Carinii, and Mycobacterium Avium," Antimicrobial Agents and Chemotherapy, American Society for Microbiology, 40(3), 727-733.
Gage, J. C., et al. (1947), "2-P-Aminobenzenesulphonamido-4 : 6-Dimethoxypyrimidine: Experimental Evaluation," British Journal of Pharmacology and Chemotherapy, 2(3), 149-162.
Ghorab, Mostafa M. et al., (2017), "Aromatase inhibitors and apoptotic inducers: Design, synthesis, anticancer activity and molecular modeling studies of novel phenothiazine derivatives carrying sulfonamide moiety as hybrid molecules," *Eur. J. Med. Chem.*, 134, 304-315.
Gomes, Paula, et al. (2003), "Amino acids as selective sulfonamide acylating agents," Tetrahedron, 59(38), 7473-7480.
Hassan, Hammed H. A. and Soliman, R. (2000), "Synthesis and GC-EIMS Analyses of Optically Pure 3-Hydroxy-2-azetidinones Having N-sulfonamide Drugs Side Chain," *Synthetic Communications*, 30(14), 2465-2478.
International Patent Application No. PCT/US2021/053853: International Search Report and Written Opinion, dated Dec. 21, 2021 (12 pages).
International Patent Application No. PCT/US2021/053855: International Search Report and Written Opinion, dated Jan. 3, 2022 (12 pages).
International Patent Application No. PCT/US2021/053856: International Search Report and Written Opinion, dated Dec. 22, 2021 (12 pages).
International Patent Application No. PCT/US2021/053858: International Search Report and Written Opinion, dated Mar. 17, 2022 (14 pages).
International Patent Application No. PCT/US2021/053860: International Search Report and Written Opinion, dated Dec. 23, 2021 (12 pages).
International Patent Application No. PCT/US2021/053861: International Search Report and Written Opinion, dated Dec. 22, 2021 (12 pages).
International Patent Application No. PCT/US2021/053862: International Search Report and Written Opinion, dated Dec. 22, 2021 (12 pages).
International Patent Application No. PCT/US2021/053863: International Search Report and Written Opinion, dated Feb. 4, 2022 (16 pages).
International Patent Application No. PCT/US2021/053864: International Search Report and Written Opinion, dated Mar. 15, 2022 (17 pages).
International Patent Application No. PCT/US2021/053865: International Search Report and Written Opinion, dated Jan. 26, 2022 (16 pages).
International Patent Application No. PCT/US2021/062687: International Search Report and Written Opinion, dated Apr. 4, 2022 (16 pages).
Kim, Taehoon, et al. (2018), "Sulfonamidation of Aryl and Heteroaryl Halides through Photosensitized Nickel Catalysis," *Agewandte Chemie*, 57, 3488-3492.
Newkome, George R., et al. (1979), "Nicotinic Acid Crown Ethers. Synthesis, Reactions, and Complexation of Nicotinonitrile Macrocycles," *J Org Chem*, 44(15): 2639-2697.
Nishida, Haruyuki, et al. (2017), "Exploration of pyrrole derivatives to find an effective potassium competitive acid blocker with moderately long-lasting suppression of gastric acid secretion," *Bioorg Med Chem*, 25(13): 3447-3460.
Prashantha, Gunaga, et al. (2017), "Selective IKur Inhibitors for the Potential Treatment of Atrial Fibrillation: Optimization of the Phenyl Quinazoline Series Leading to Clinical Candidate 5-[5-Phenyl-4-(pyridin-2-ylmethylamino)quinazolin-2-yl]pyridine-3-sulfonamide," *J Med Chem*, 60(9): 3795-3803.
Raiziss, George W., et al. (1942), "N1-Sulfanilylaminoalkylpyrimidines," *J. Am. Chem. Soc.* 64, 2340-2342.
Rewcastle, Gordon W., et al. (1996), "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," *J Med Chem*, 39(9): 1823-1835.
Rose, F. L., et al. (1946), "P-Aminobenzenesulphonamide Derivatives of Pyrimidines as Antibacterial Agents," *J. Am. Chem. Soc.*, 81-85.
Sprague, James M., et al. (1941), "Sulfonamido derivatives of thiazoles," *J. Am. Chem. Soc.* 63, 578-580.
Sprague, James M., et al. (1941), "Sulfonamido derivatives of pyrimidines," *J. Am. Chem. Soc.* 63, 3028-3030.
Sugasawa, Shigehiko, et al. (1949), "Reaction between sulfaguanidine and 1,3-keto aldehydes. I. Synthesis of 2-sulfanilamido-4-methylpyrimidine," 69, 82-85.
Tani, Chiaki, et al. (1950), "Syntheses of sulfanilamide derivatives containing diphenylene oxide," *Journal of the Pharmaceutical Society of Japan*, 70, 126-127.
U.S. Appl. No. 16/992,419, filed Aug. 13, 2021, by Angell et al.
U.S. Appl. No. 16/992,441, filed Aug. 13, 2021, by Shi et al.
U.S. Appl. No. 16/992,448, filed Aug. 13, 2021, by Anderson et al.
U.S. Appl. No. 16/992,675, filed Aug. 13, 2021, by Abela et al.
U.S. Appl. No. 17/546,649, filed Dec. 9, 2021, by Borek et al.
U.S. Appl. No. 17/600,829, filed Oct. 1, 2021, by Abela et al.
Anonymous: "Symdeko in Cystic Fibrosis Patients", CiinicalTriais.gov, Jul. 23, 2018 (Apr. 23, 2018). XP055661778, Retrieved from the Internet: URL:https://clinicaltrials.gov/ct2/show/record/NCT03506061 (retrieved on Jan. 24, 2020).
Donaldson. S.H. et al. (2017) "Tezacaftor/Ivacaftor in Subjects with Cystic Fibrosis and F508del/F508del-CFTR or F508del/G551D-CFTR", *Am. J. Respir. Crit. Care Med.*, 197(2): 214-224.
International Patent Application No. PCT/US2019/018042: international Search Report and Written Opinion, dated Apr. 17, 2019 (10 pages).
International Patent Application No. PCT/US2019/061171: International Search Report and Written Opinion, dated Feb. 2, 2020 (14 pages).
International Patent Application No. PCT/U2020/026331: International Search Report and Written Opinion, dated May 29, 2020 (14 pages).

\* cited by examiner

| Mutation cDNA Name | Mutation Protein Name | Mutation Legacy Name |
|---|---|---|
| c.1A>G | | M1V |
| c.54-5940_273+10250del21kb | pSer18ArgfsX16 | CFTRdele2,3 |
| c.91C>T | p.Arg31Cys | R31C |
| c.115C>T | p.Gin39X | Q39X |
| c.137C>A | p.Ala46Asp | A46O |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88llefsX22 | 394delTT |
| c.273+1G>A | No protein name | 405+lG->A |
| c.274-1G>A | No protein name | 406-lG->A |
| c.274G>A | p.Glu92Lys | E92K |
| c.274G>T | p.Glu92X | E92X |
| c.292C>T | p.Gln98X | Q98X |
| c.313delA | p.llel05SerfsX2 | 444delA |
| c.325_327delTATinsG | p.Tyrl09GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.llel48LeufsX5 | 574delA |
| c.443T>C | p.lle148Thr | I148T |

FIG. 2

| Mutation cDNA Name | Mutation Protein Name | Mutation Legacy Name |
|---|---|---|
| c.489+1G>T | No protein name | 621+1G->T |
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| C.59SOT | p.His199Tyr | H199Y |
| C.613CM | p.Pro205Ser | P205S |
| c.617T>G | p.Leu20GTrp | L206W |
| C.6580T | p.Gln220X | Q220X |
| c.580T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ele | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 10799C>A] | p.[Gln359Lys;Thr360Lys] | Q359K/T360K |
| c.1081delT | p.Trp361GlyfsX8 | 1213delT |

FIG. 2 (continued)

| Mutation cDNA Name | Mutation Protein Name | Mutation Legacy Name |
|---|---|---|
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |
| c.1202G>A or c.1203G>A | p.Trp401X | W401X |
| c.1209+1G>A | No protein name | 1341+1G->A |
| c.1210-12[5] | No protein name | 5T |
| c.1210-12(7) | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |

FIG. 2 (continued)

| Mutation cDNA Name | Mutation Protein Name | Mutation Legacy Name |
|---|---|---|
| c.1645A>C or c.1G47T>G | p.Ser549Arg | S549R |
| c.1646G>A | p.Ser549Asn | S549N |
| c.1650delA | p.Gly551ValfsX8 | 1782delA |
| c.1651G>A | p.Gly551Ser | G551S |
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985dell3insAGAAA | p.Arg658 LysfsX4 | 2105-2117dell3insAGAAA |

FIG. 2  (continued)

| Mutation cDNA Name | Mutation Protein Name | Mutation Legacy Name |
|---|---|---|
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G+ |
| c.205 1_2052delAAinsG | p.Lys684SerfsX38 | 2183delAA->G# |
| c.2052_2053insA | p.Gln685Th rfsX4 | 2184insA |
| c.2052delA | p.Lys684AsnfsX38 | 2184delA |
| c.21250T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Va!739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.25470A | p.Tyr849X | Y849X |
| c.2551C>T | p.ArgSSIX | R851X |
| c.2583delT | p.Phe861LeufsX3 | 2711delT |
| c.2657+2_2657+3insA | No protein name | 2789+2insA |

FIG. 2 (continued)

| Mutation cDNA Name | Mutation Protein Name | Mutation Legacy Name |
|---|---|---|
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG | | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |

FIG. 2 (continued)

| Mutation cDNA Name | Mutation Protein Name | Mutation Legacy Name |
| --- | --- | --- |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.3718-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |

FIG. 2 (continued)

| Mutation cDNA Name | Mutation Protein Name | Mutation Legacy Name |
|---|---|---|
| c.37640A | p.Ser1255X | S1255X |
| c.3773_3774insT | p.Leu1258PhefsX7 | 3905insT |
| c.3808G>A | p.Asp1270Asn | D1270N |
| c.3346G>A | p.Trp1282X | W1282X |
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

FIG. 2 (continued)

MODULATORS OF CYSTIC FIBROSIS TRANSMEMBRANE CONDUCTANCE REGULATOR, PHARMACEUTICAL COMPOSITIONS, METHODS OF TREATMENT, AND PROCESS FOR MAKING THE MODULATORS

This application claims priority to U.S. provisional application 62/631,453, filed Feb. 15, 2018, the disclosure of which is incorporated herein by reference in its entirety.

Disclosed herein is a modulator of Cystic Fibrosis Transmembrane Conductance Regulator (CFTR), pharmaceutical compositions containing the modulator, methods of treatment of cystic fibrosis, and a process for making the modulator.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence, and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$-$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for novel treatments of CFTR mediated diseases.

Disclosed herein are novel compounds, including compounds of Formulae (I), (II-A), (II-B), (III-A), (III-B), (IV-A), (IV-B), (IV-C), (V-A), (V-B), (VI-A), (VI-B), (VI-C), and (VI-D), pharmaceutically acceptable salts thereof, and deuterated derivatives of any of the foregoing. For example, compounds of Formula (I) can be depicted as:

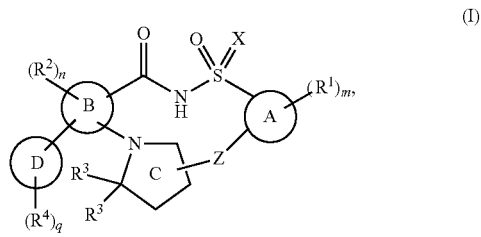

a pharmaceutically acceptable salt thereof, or a deuterated derivative of any of the foregoing,
wherein:
  Ring A is a phenyl, a 5-membered heteroaryl ring, or a 6-membered heteroaryl ring;
  Ring B is a pyridinyl ring;
  Ring D is a phenyl ring, a 5-membered heterocyclyl ring, a 6-membered heterocyclyl ring, a 5-membered heteroaryl ring, or a 6-membered heteroaryl ring;
  X is O, NH, or an $N(C_1$-$C_4$ alkyl);
  each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  m is 0, 1, 2, 3, or 4;
  each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  n is 0, 1, or 2;

each $R^3$ is methyl;

each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups; wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1, 2, 3 or 4; and

Z is a divalent linker of formula $(L)_r$, wherein:

r is 1, 2, 3, 4, 5, or 6;

each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is independently chosen from hydrogen, halogens, $C_1$-$C_2$ haloalkyl groups, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

In some embodiments, Ring D in Formula (I) is pyridin-2(1H)-one, pyrrolidin-2-one, or imidazolidin-2-one.

Also disclosed herein are pharmaceutical compositions comprising at least one of the novel compounds disclosed herein and/or at least one pharmaceutically acceptable salt thereof, which compositions may further include at least one additional active pharmaceutical ingredient and/or at least one carrier. Also disclosed are methods of treating the CFTR-mediated disease cystic fibrosis comprising administering at least one of the novel compounds disclosed herein and/or at least one pharmaceutically acceptable salt thereof, optionally as part of a pharmaceutical composition comprising at least one additional component, to a subject in need thereof.

Also disclosed are methods of treating the CFTR-mediated disease cystic fibrosis comprising administering at least one of the novel compounds disclosed herein and/or at least one pharmaceutically acceptable salt thereof, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II), and N-[2,4-bis(1,1-dimethylethyl)-5-hydroxyphenyl]-1,4-dihydro-4-oxoquinoline-3-carboxamide (Compound III), optionally as part of at least one pharmaceutical composition comprising at least one additional component, to a patient in need thereof.

BRIEF DESCRIPTION OF THE DRAWINGS

FIG. 2 is a representative list of CFTR mutations.

DEFINITIONS

Figure 1:
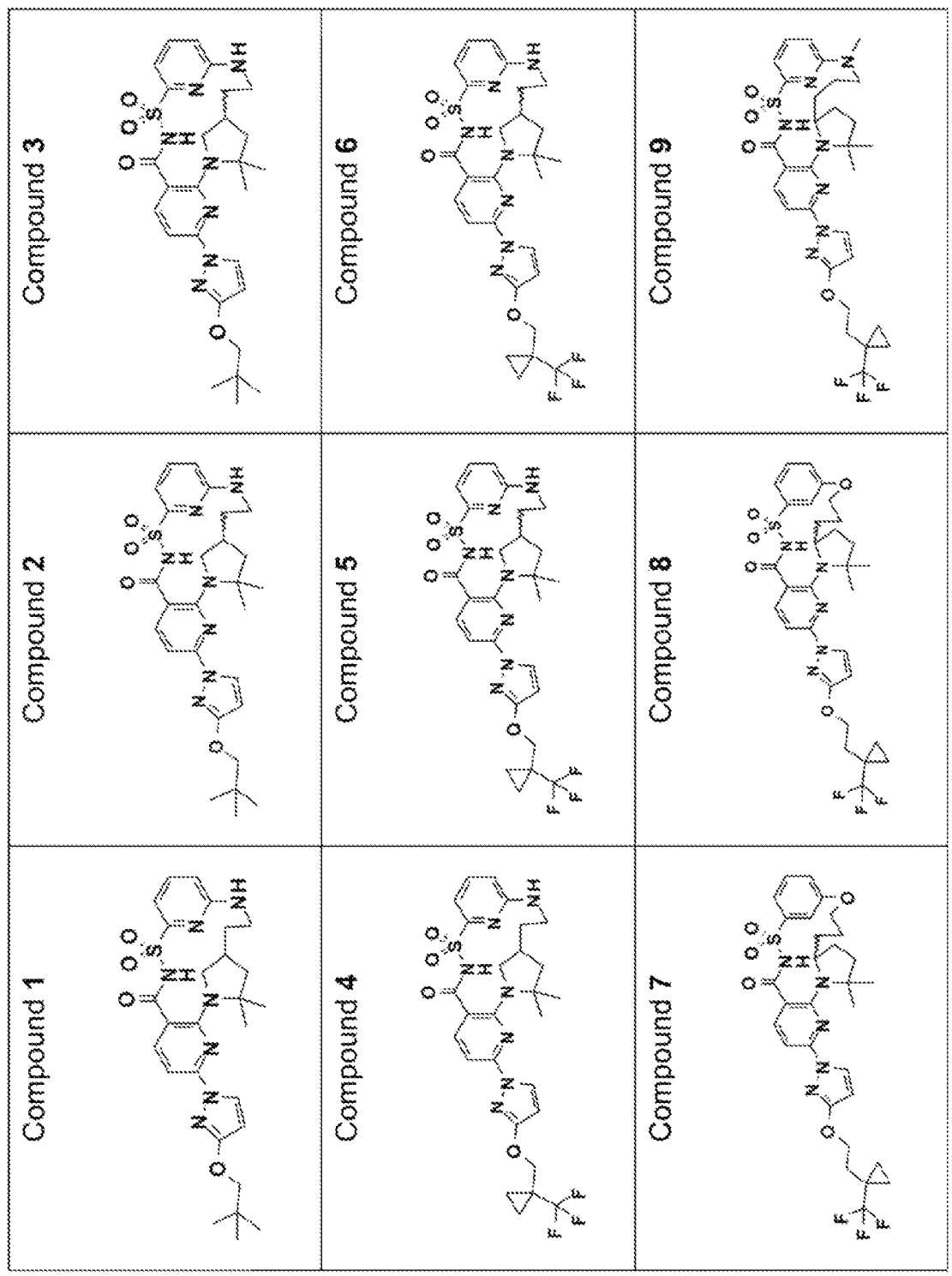
FIG. 1 shows the structures of non-limiting examples of novel compounds disclosed herein.
Figure 1:
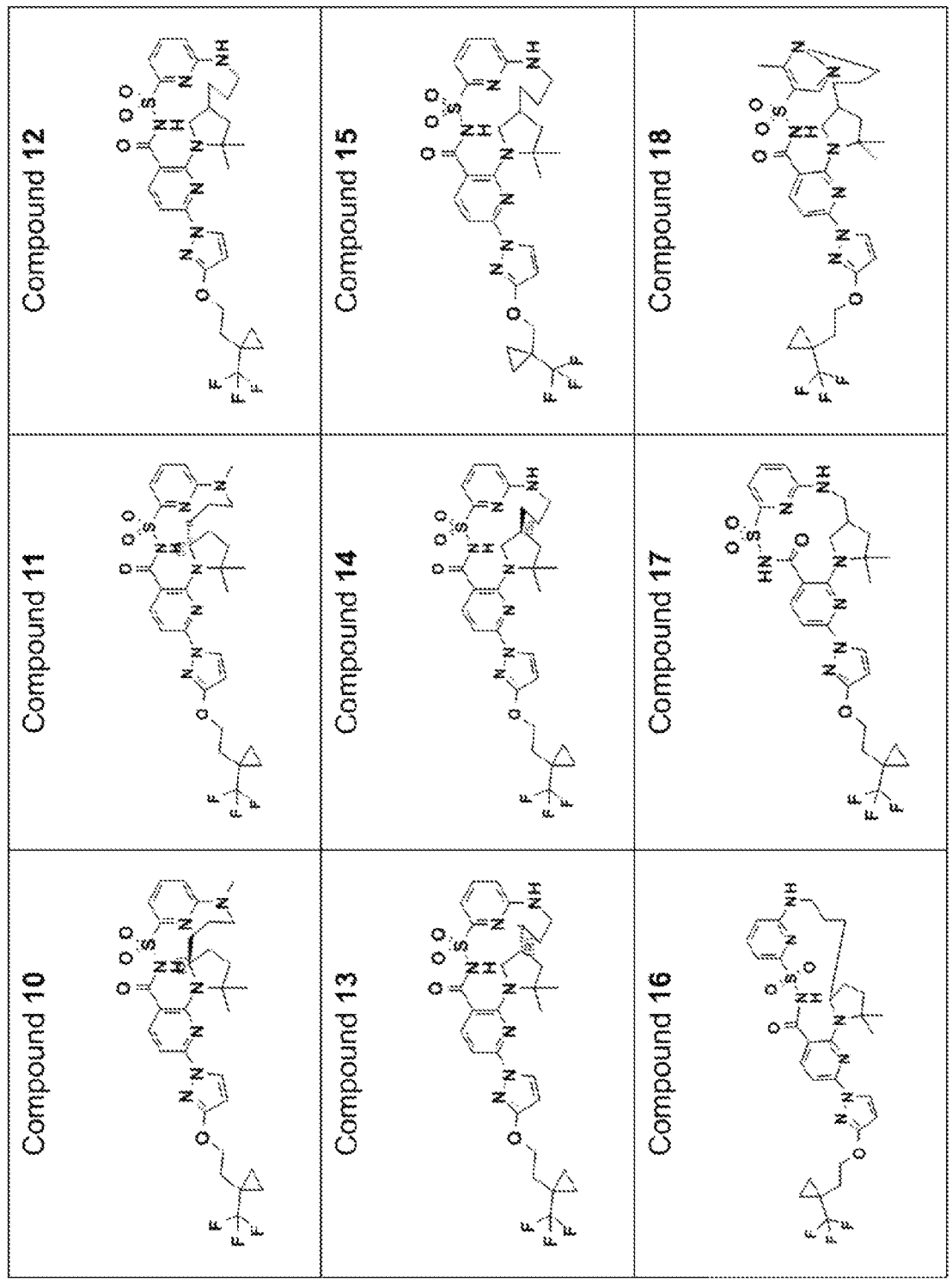
Figure 1:
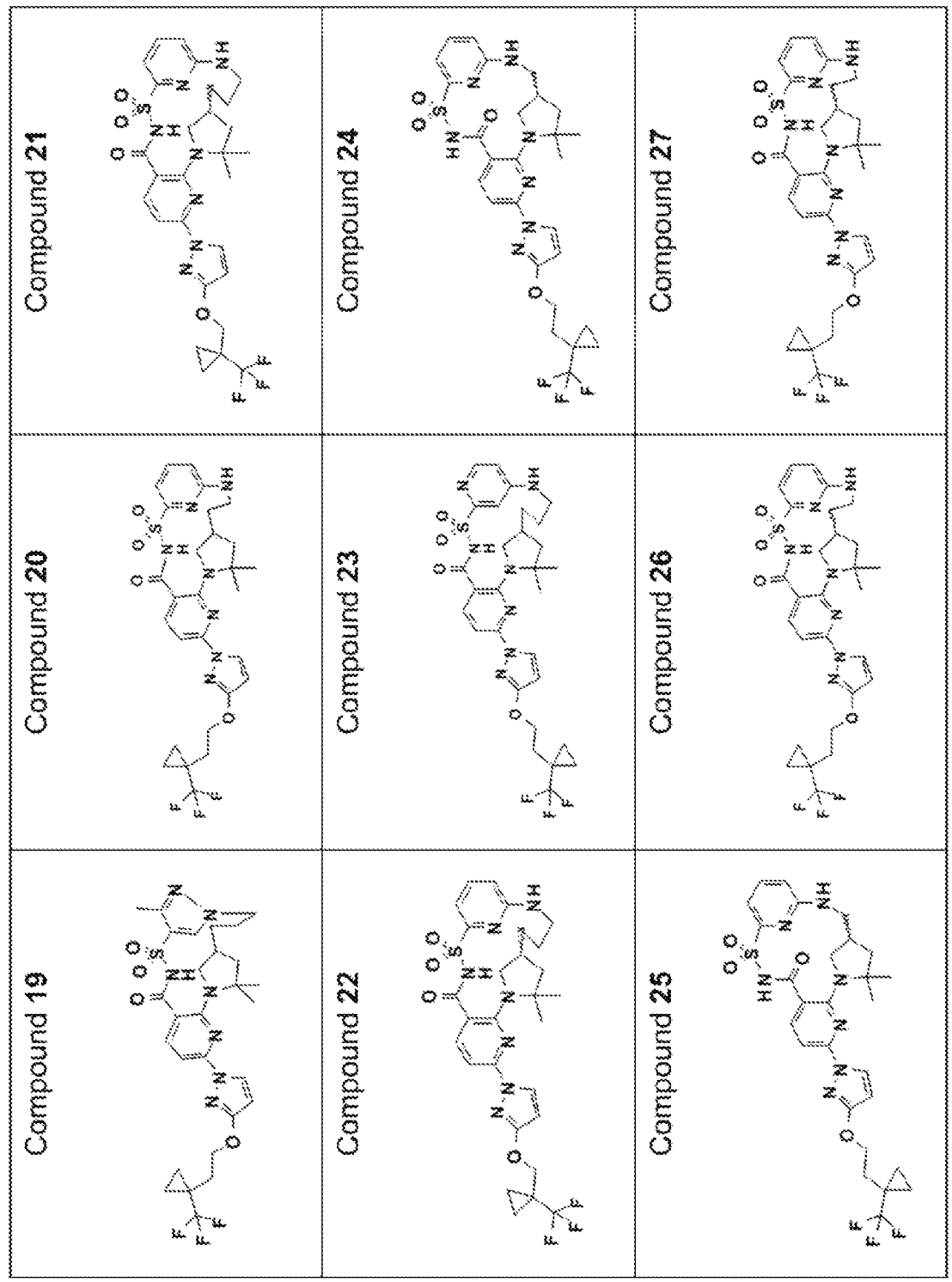
Figure 1:
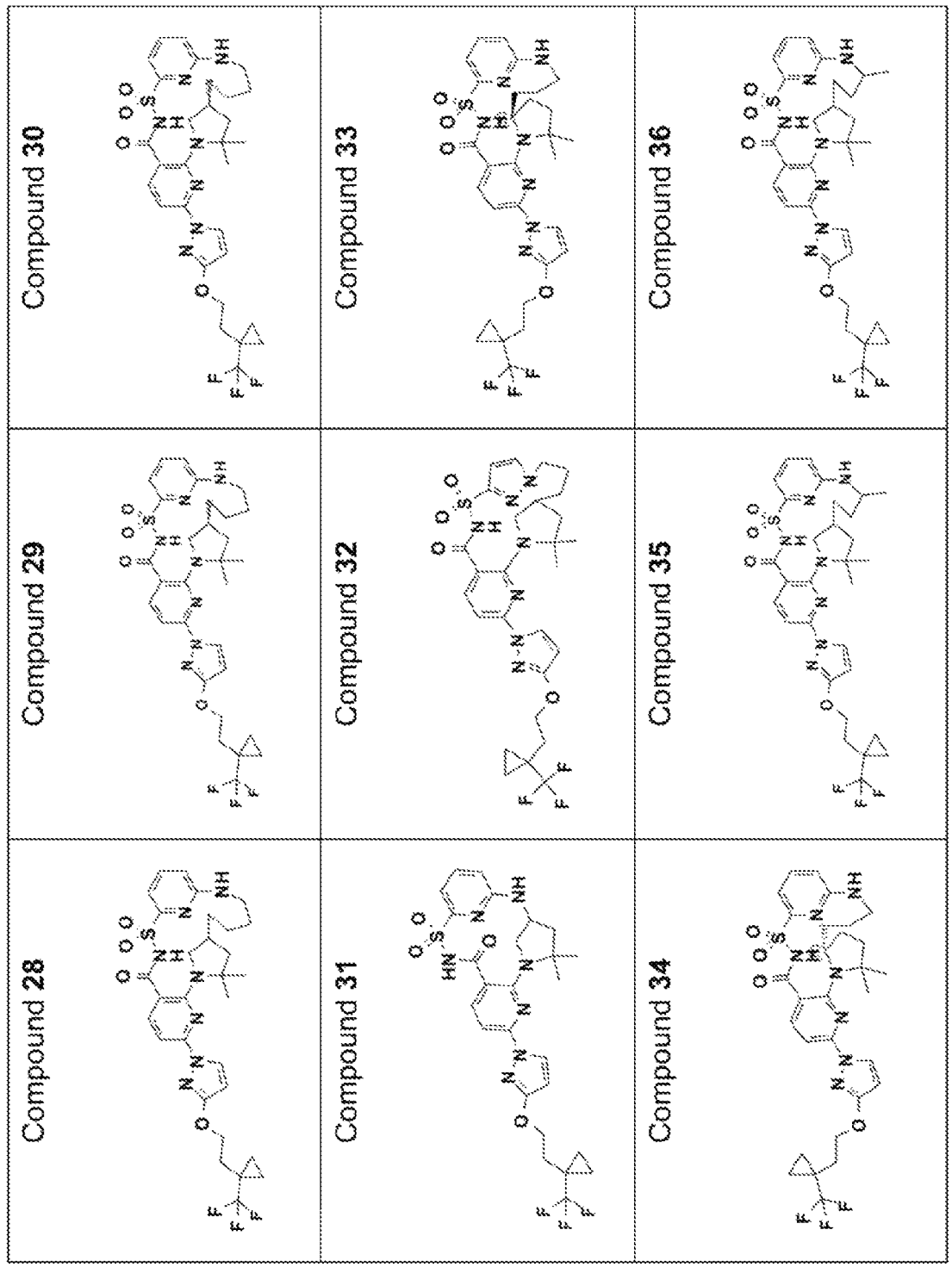
Figure 1:
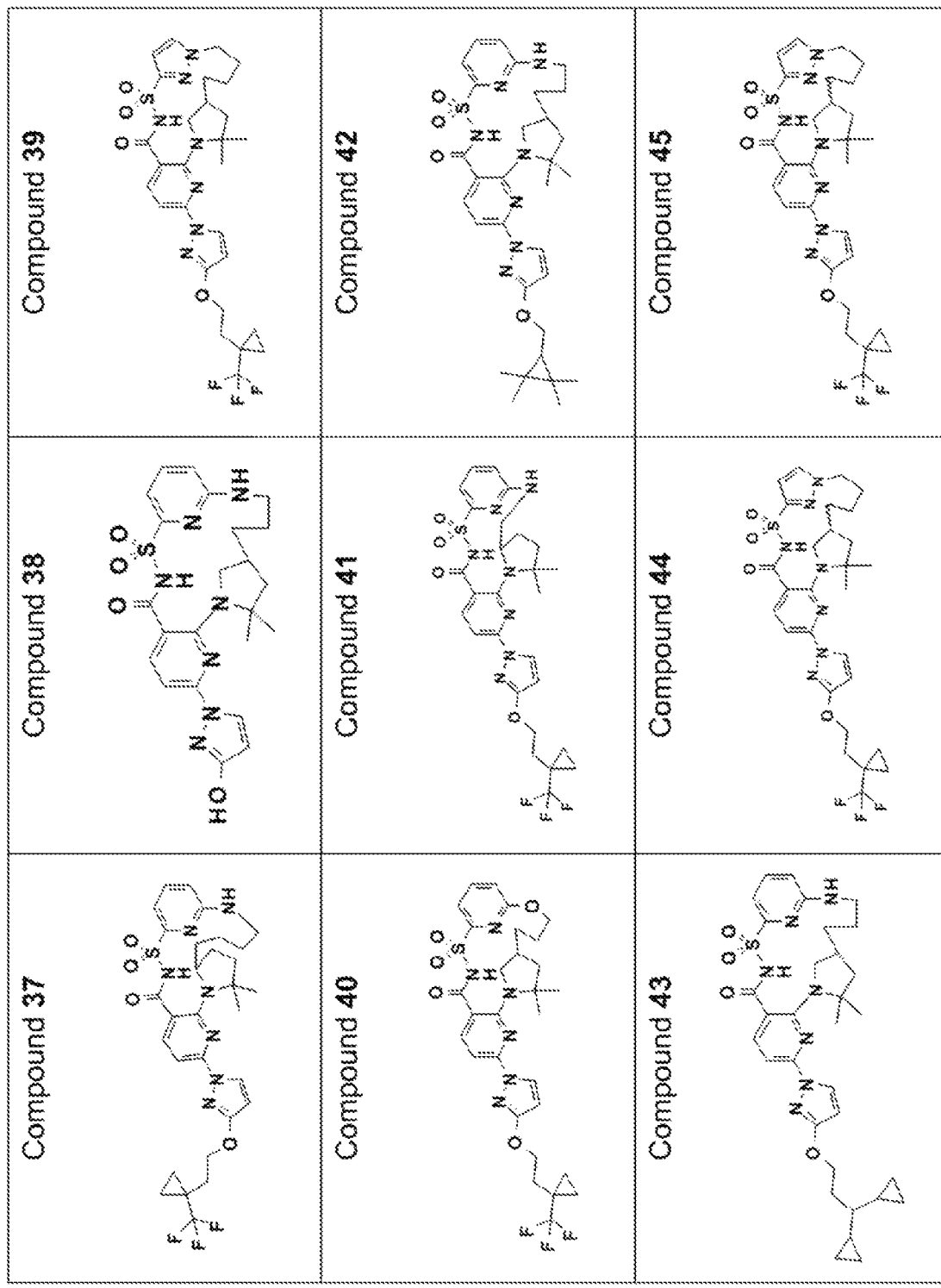
Figure 1:
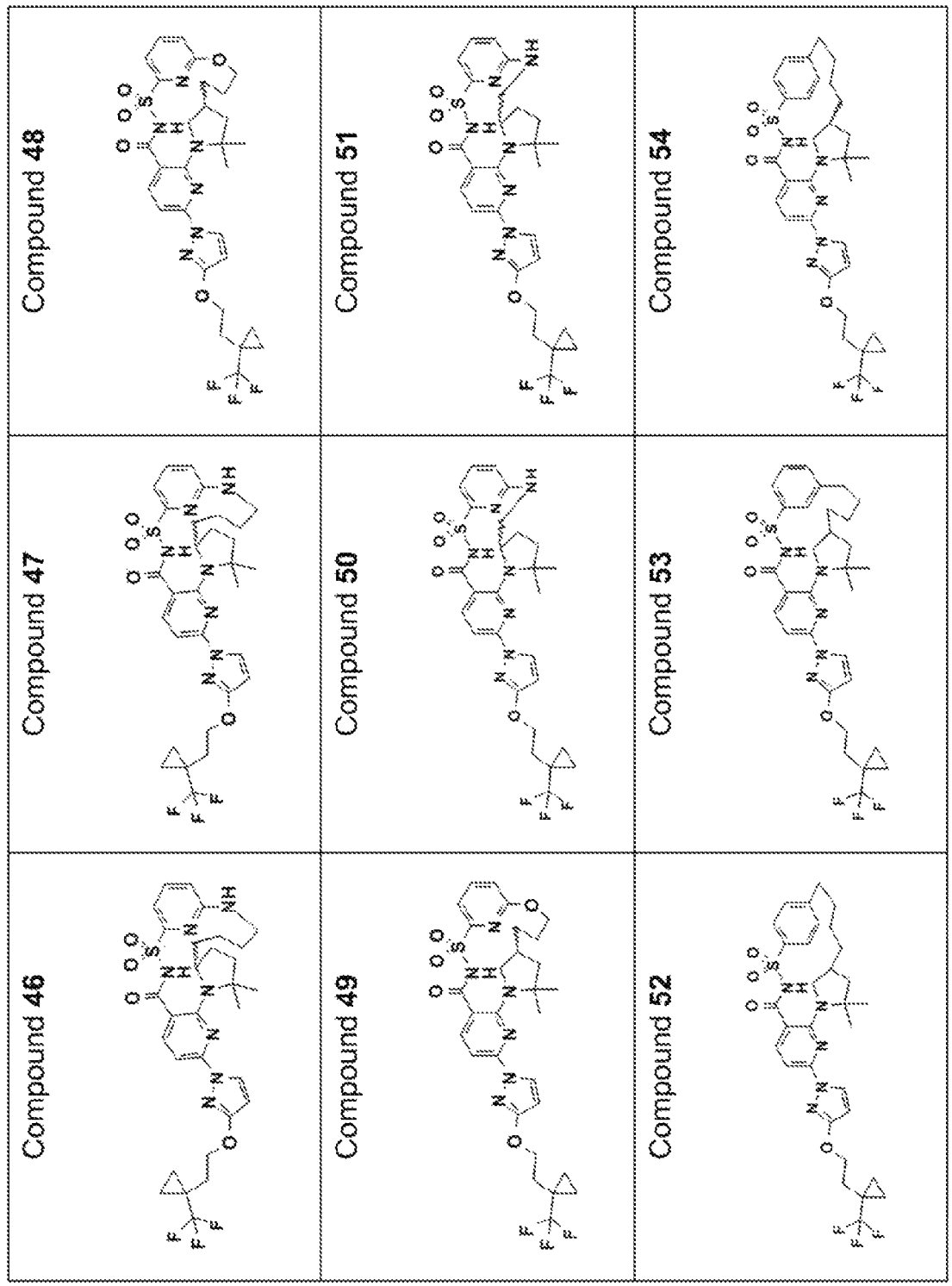
Figure 1:
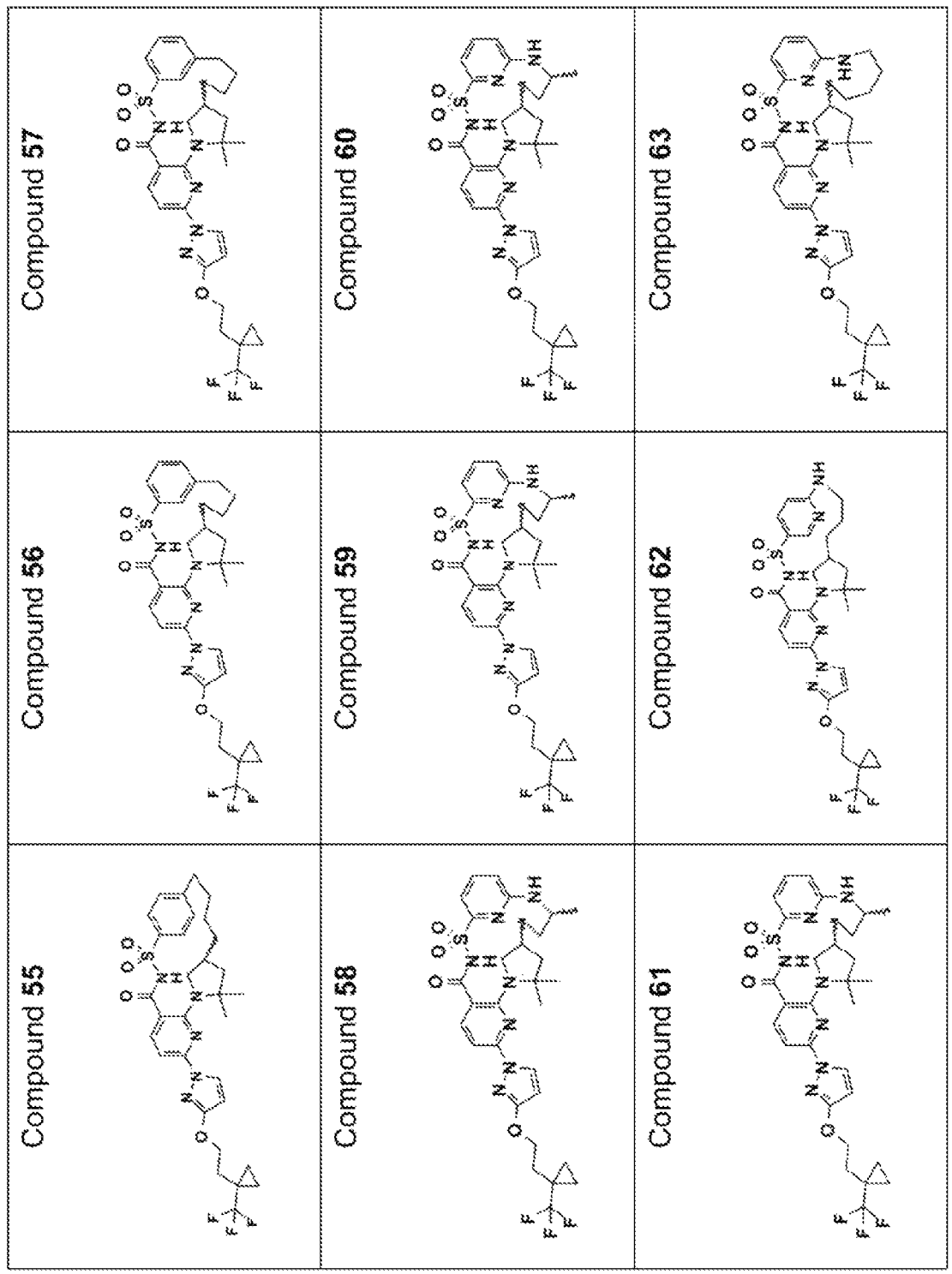
Figure 1:
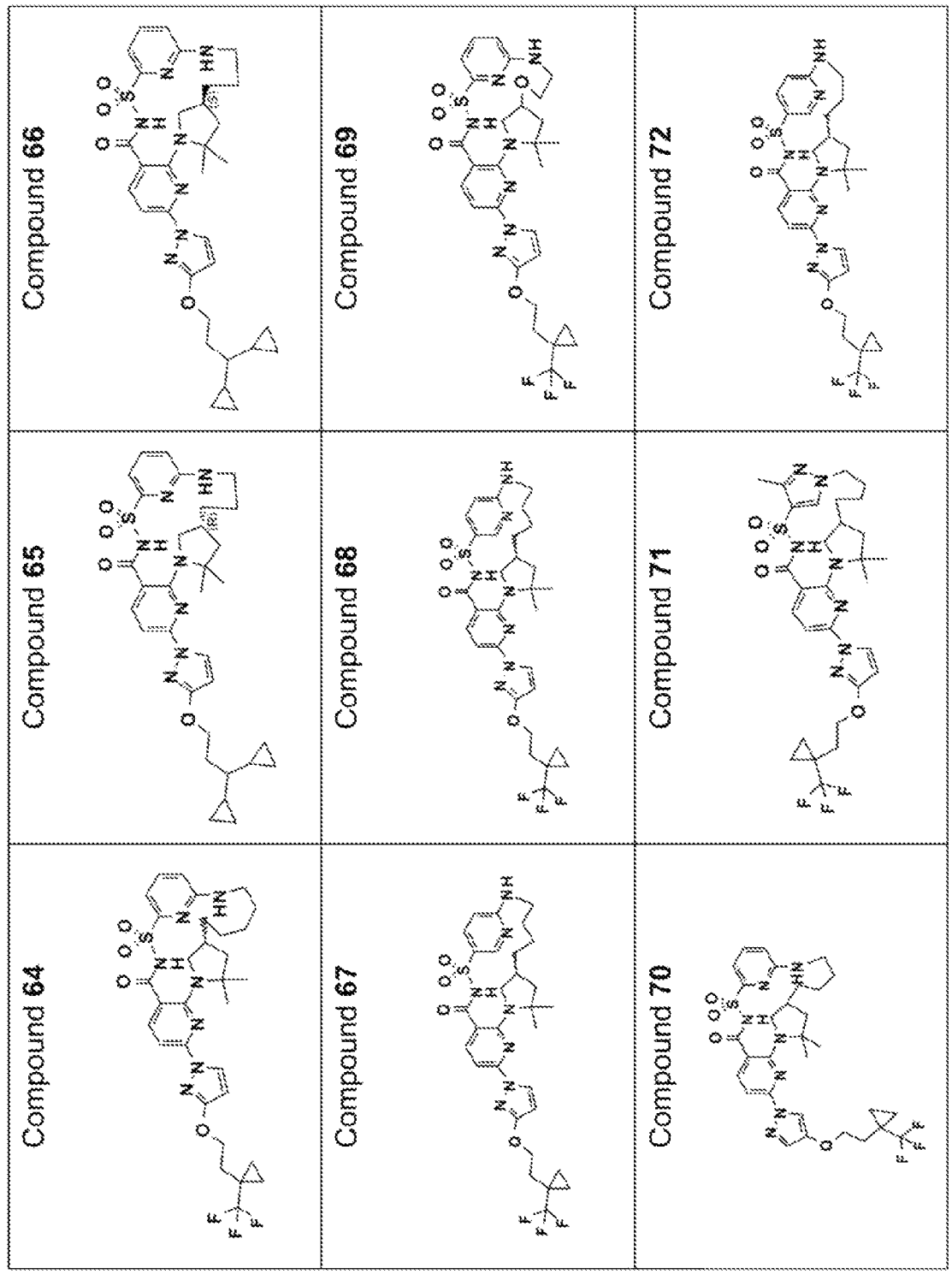
Figure 1:
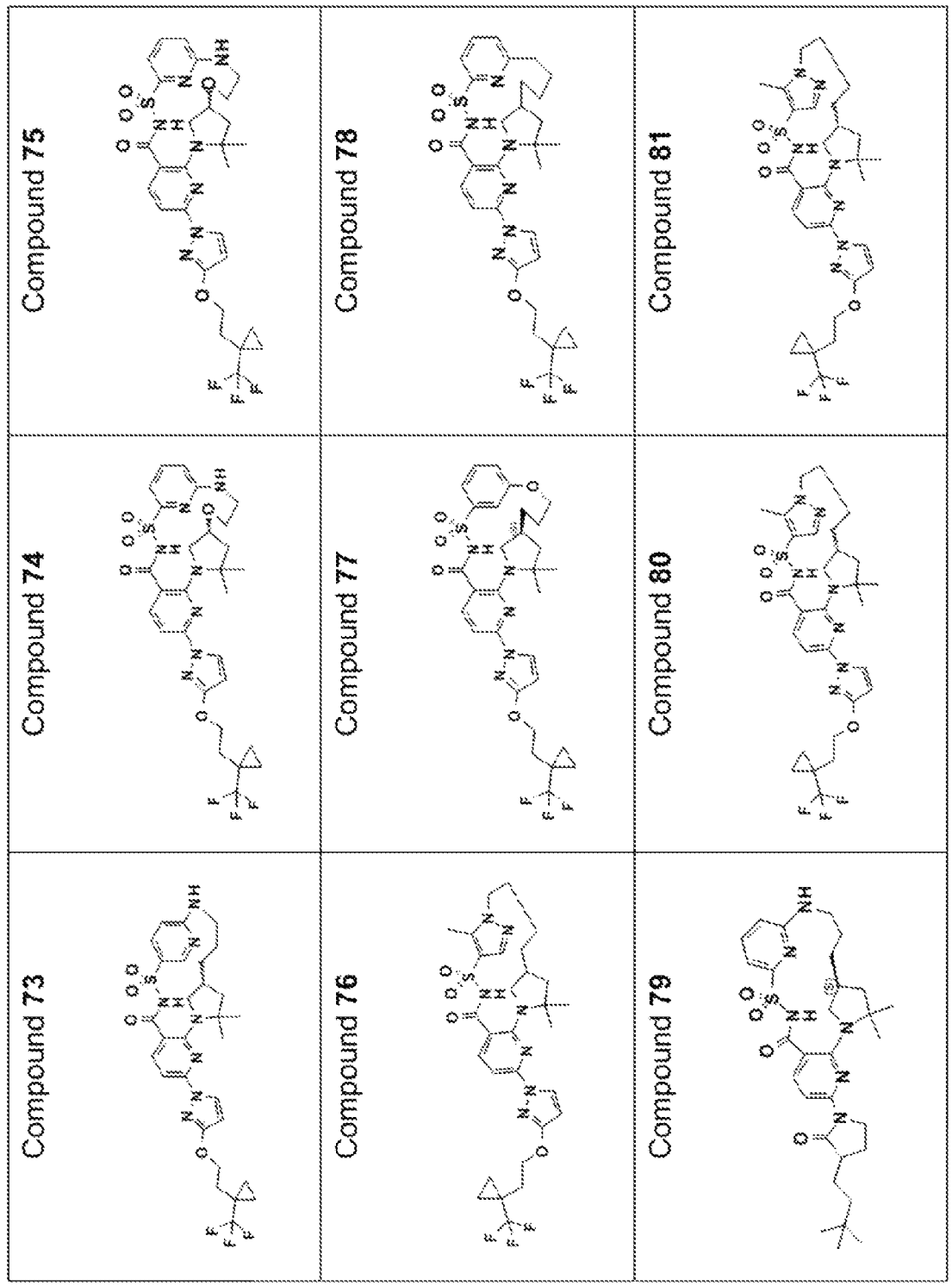
Figure 1:
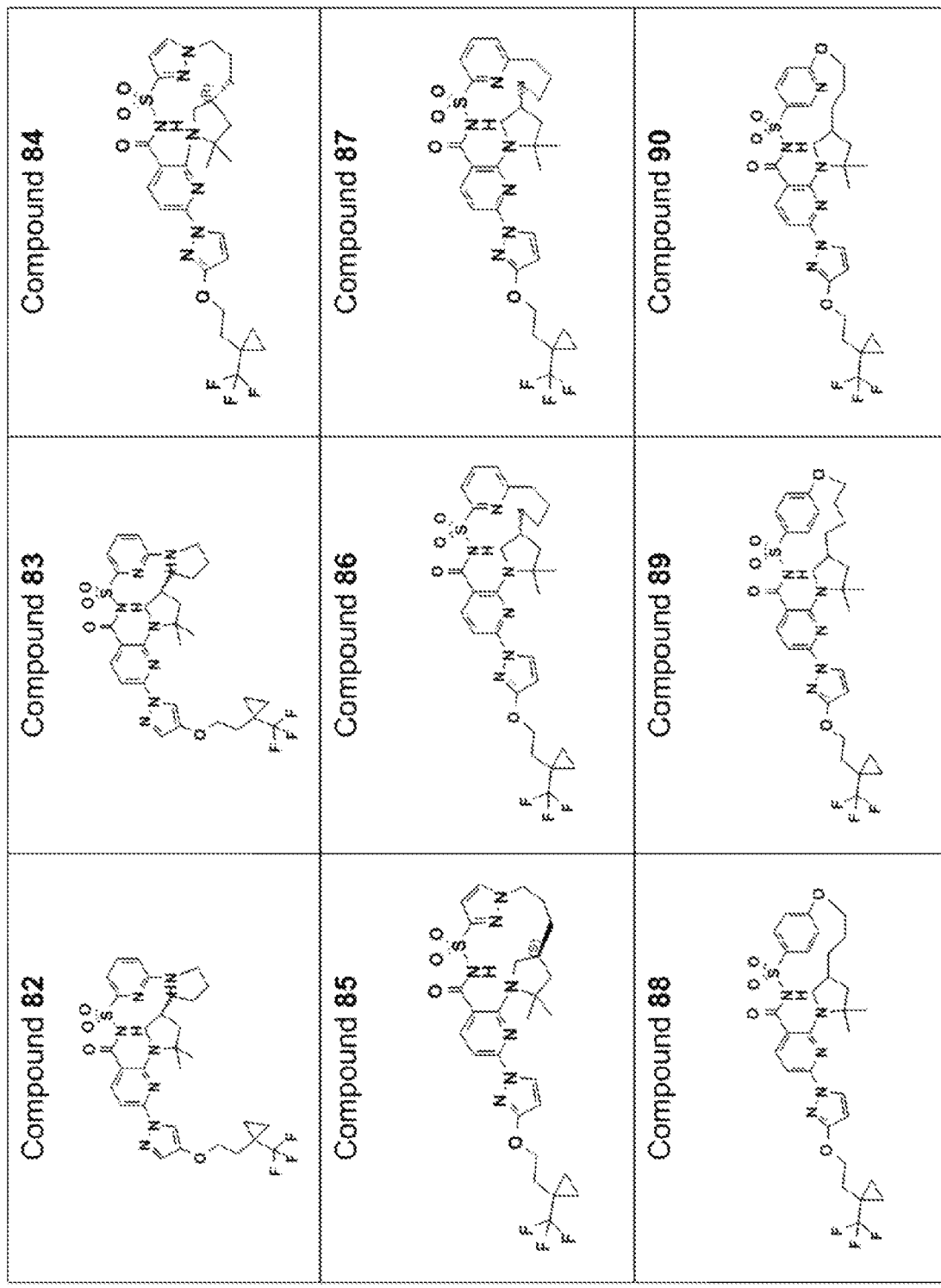
Figure 1:
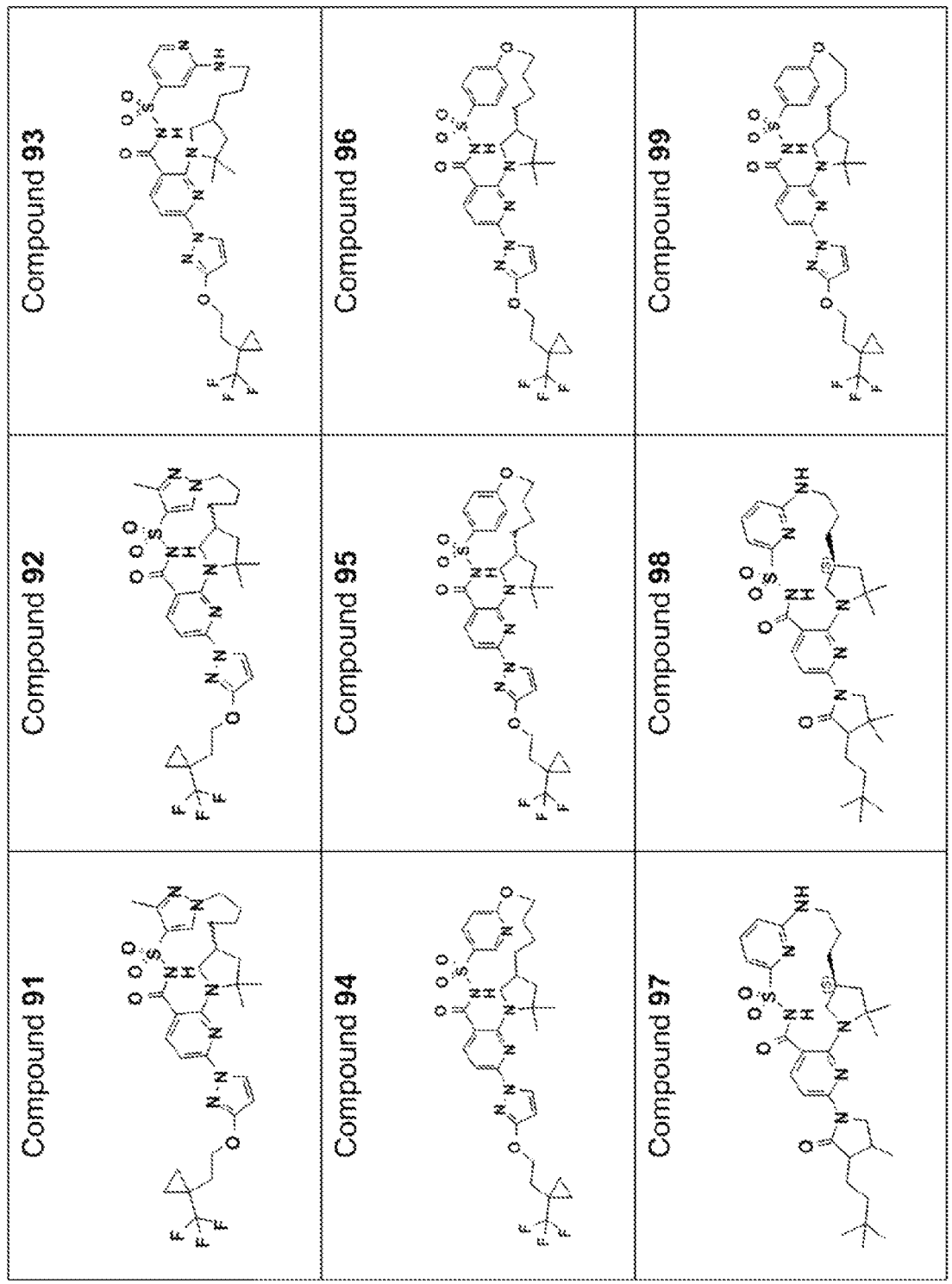
Figure 1:
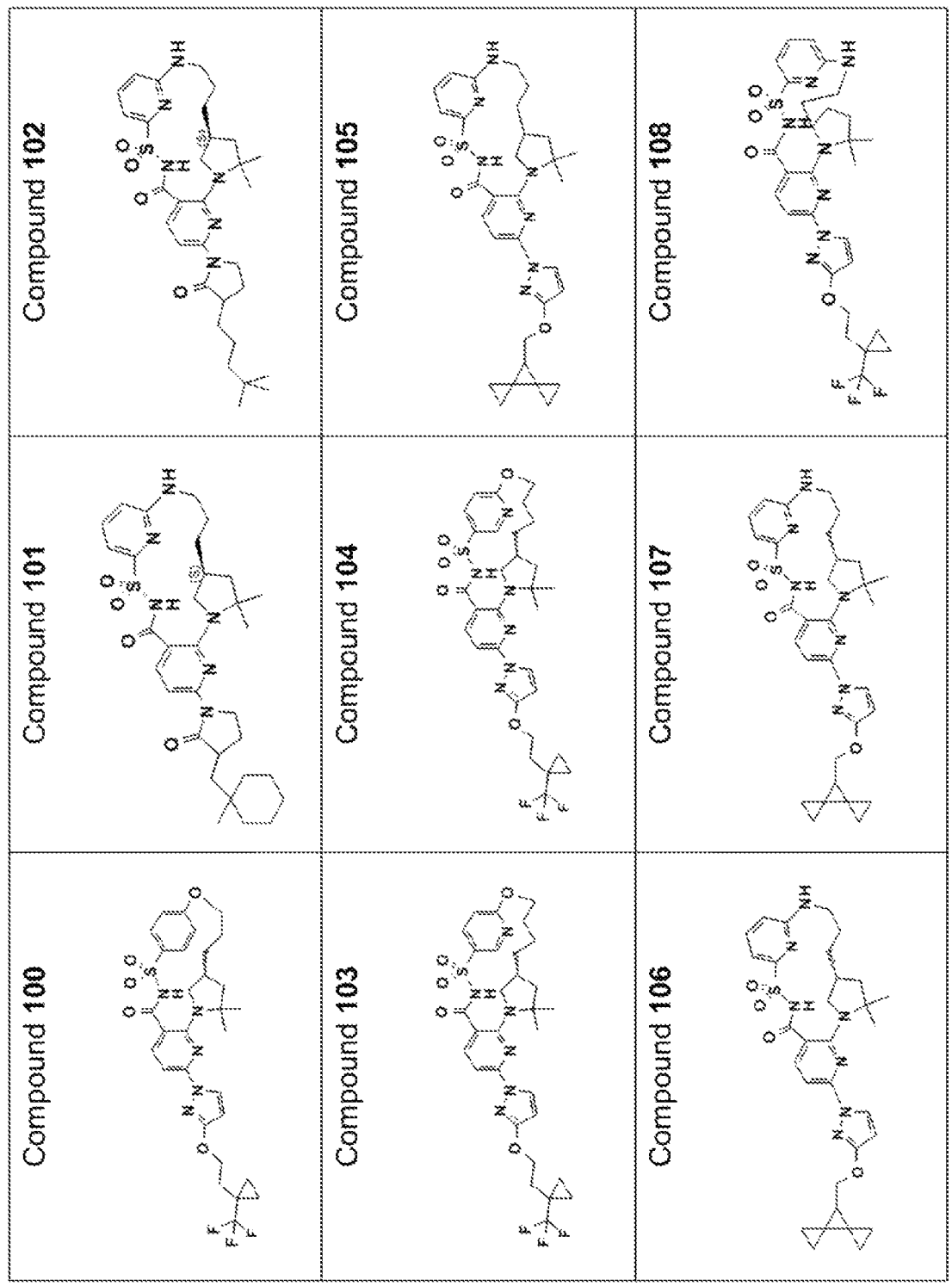
Figure 1:
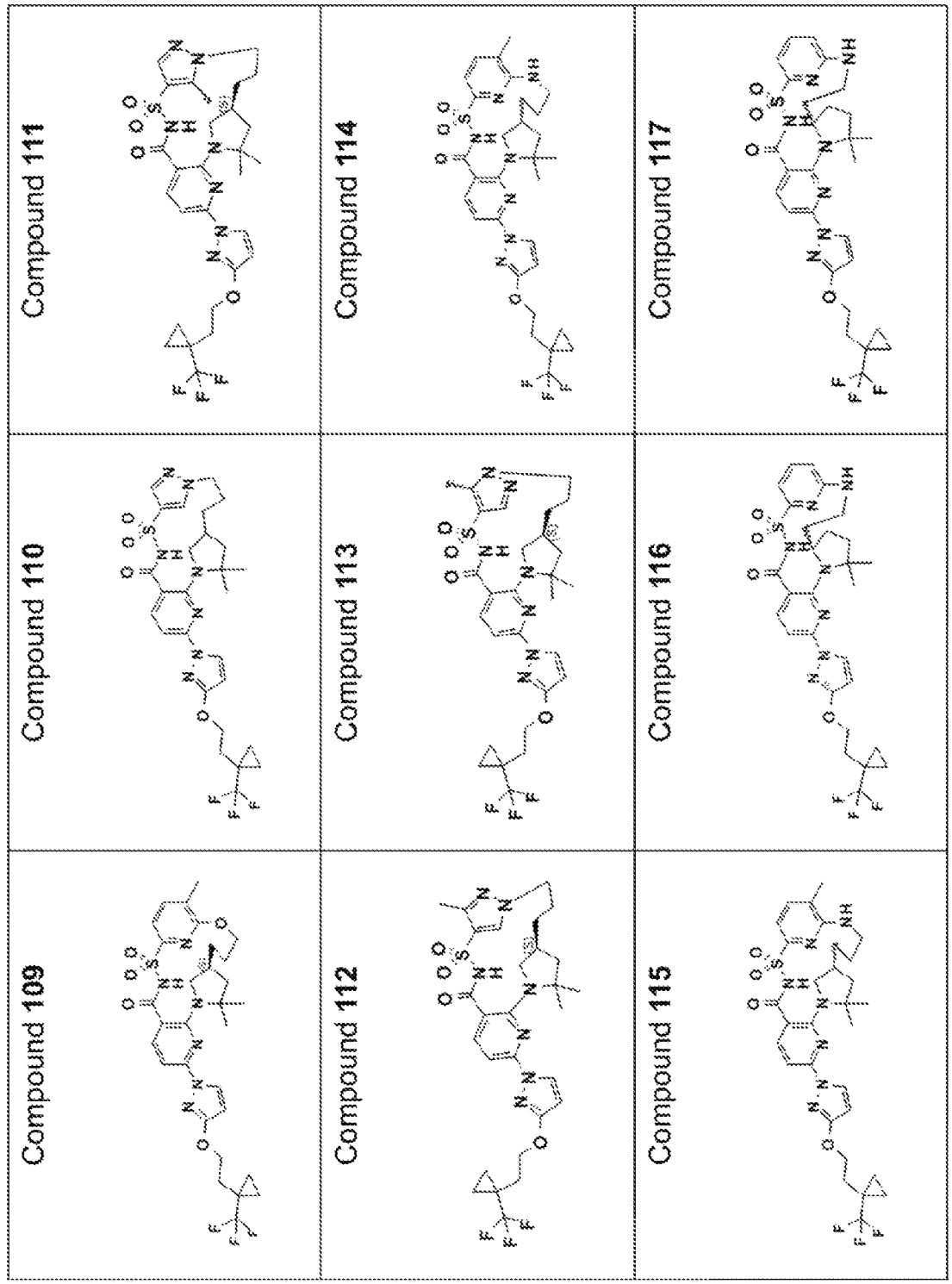
Figure 1:
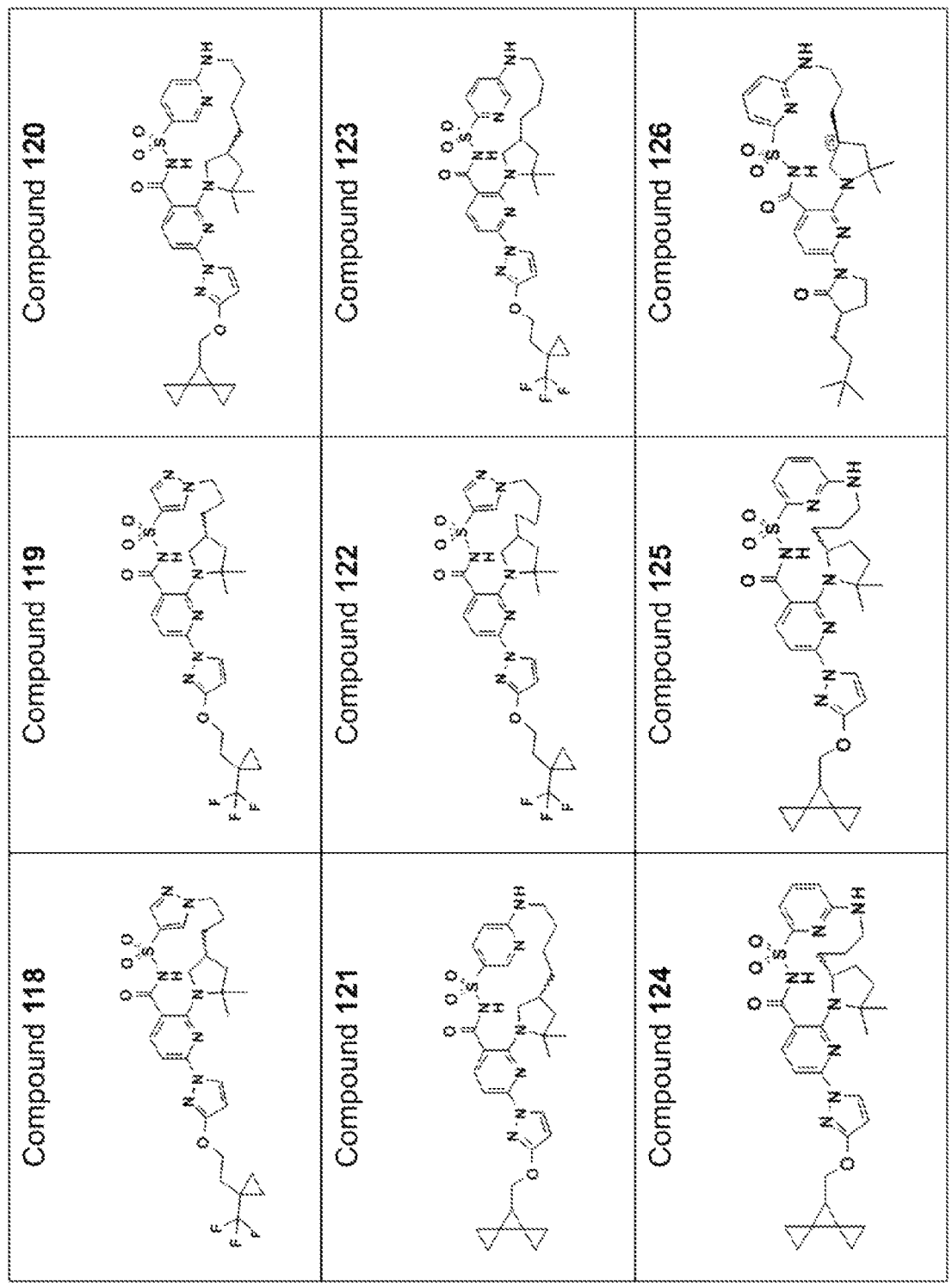
Figure 1:
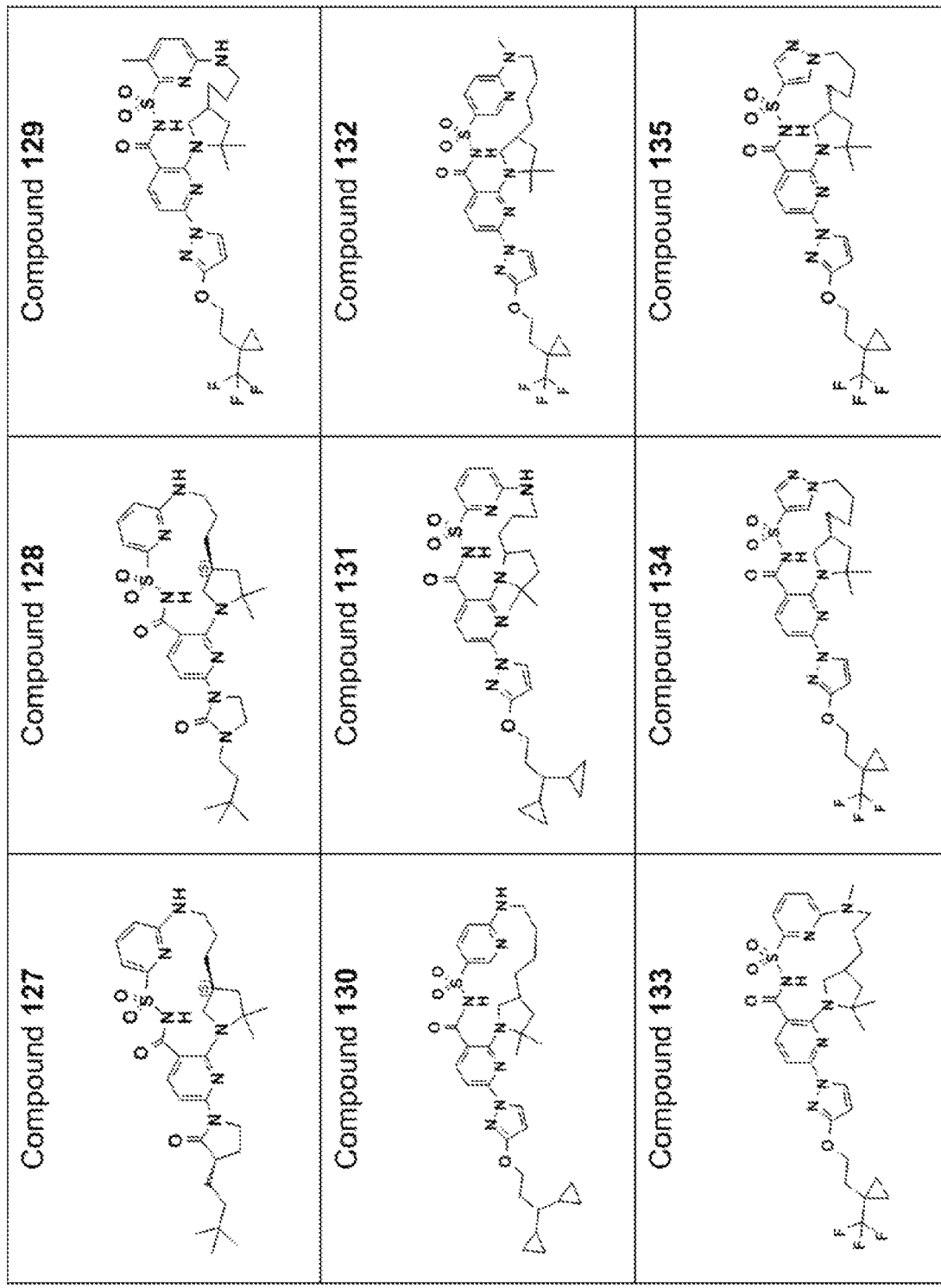
Figure 1:
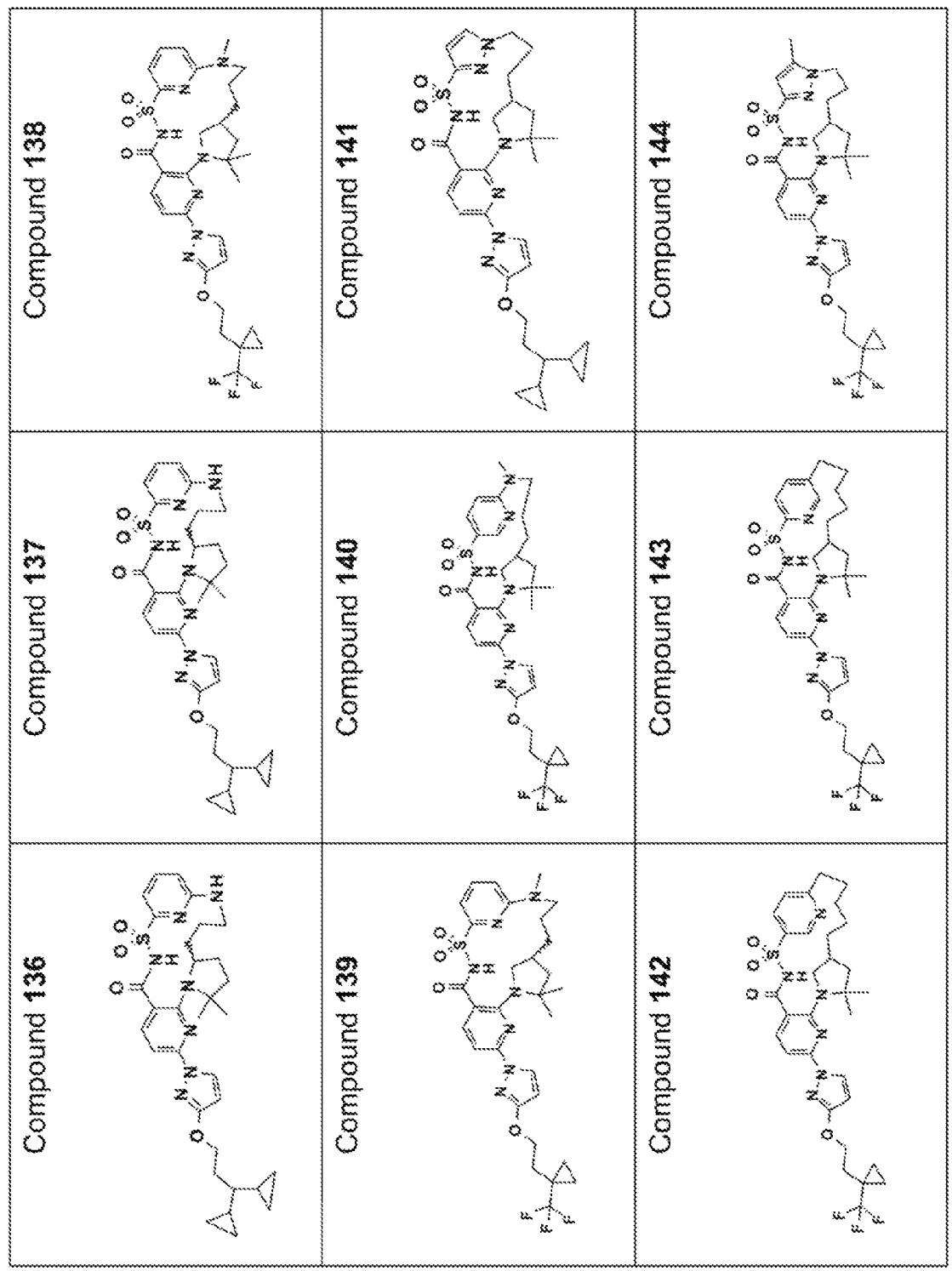
Figure 1:
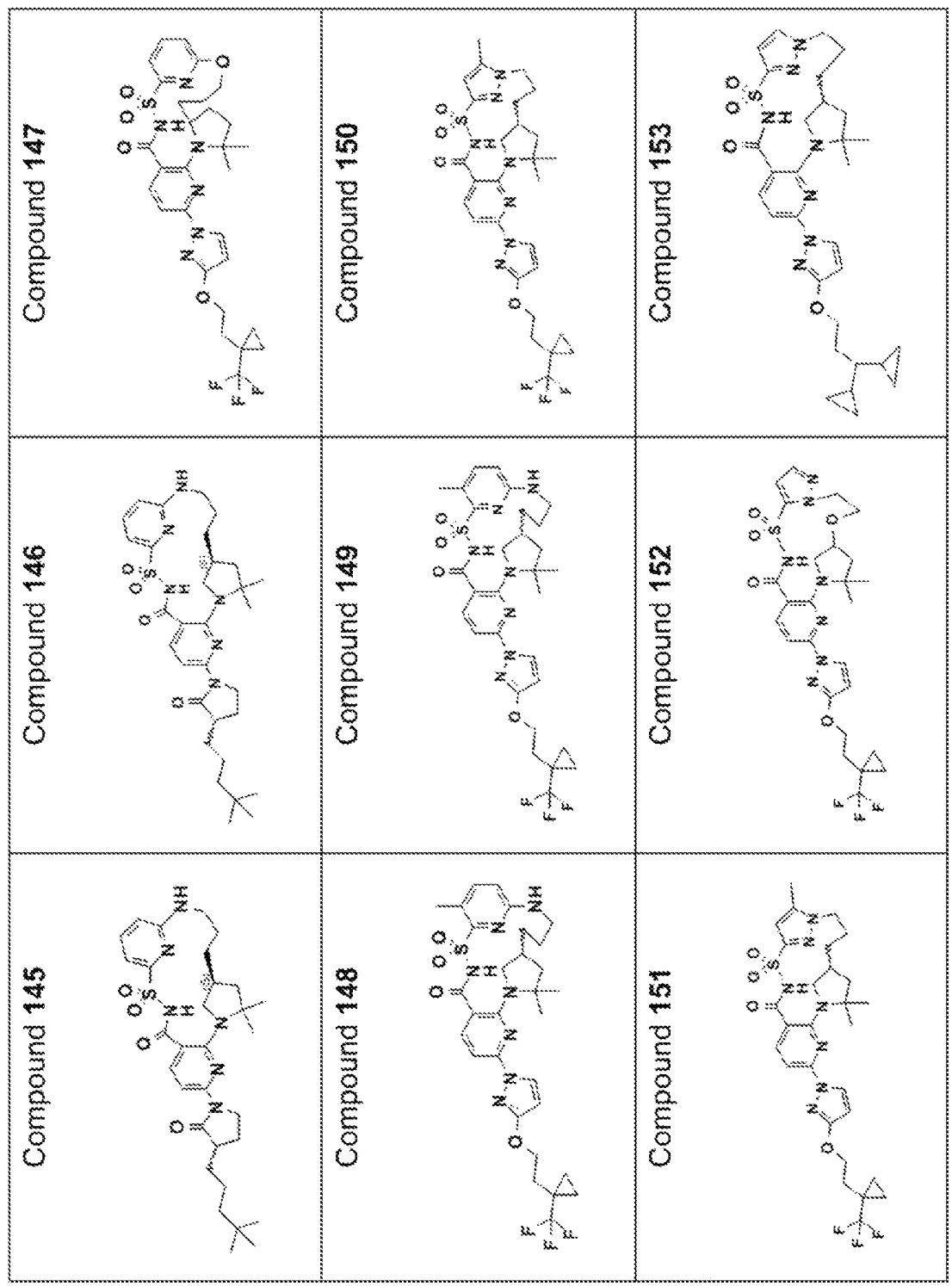
Figure 1:
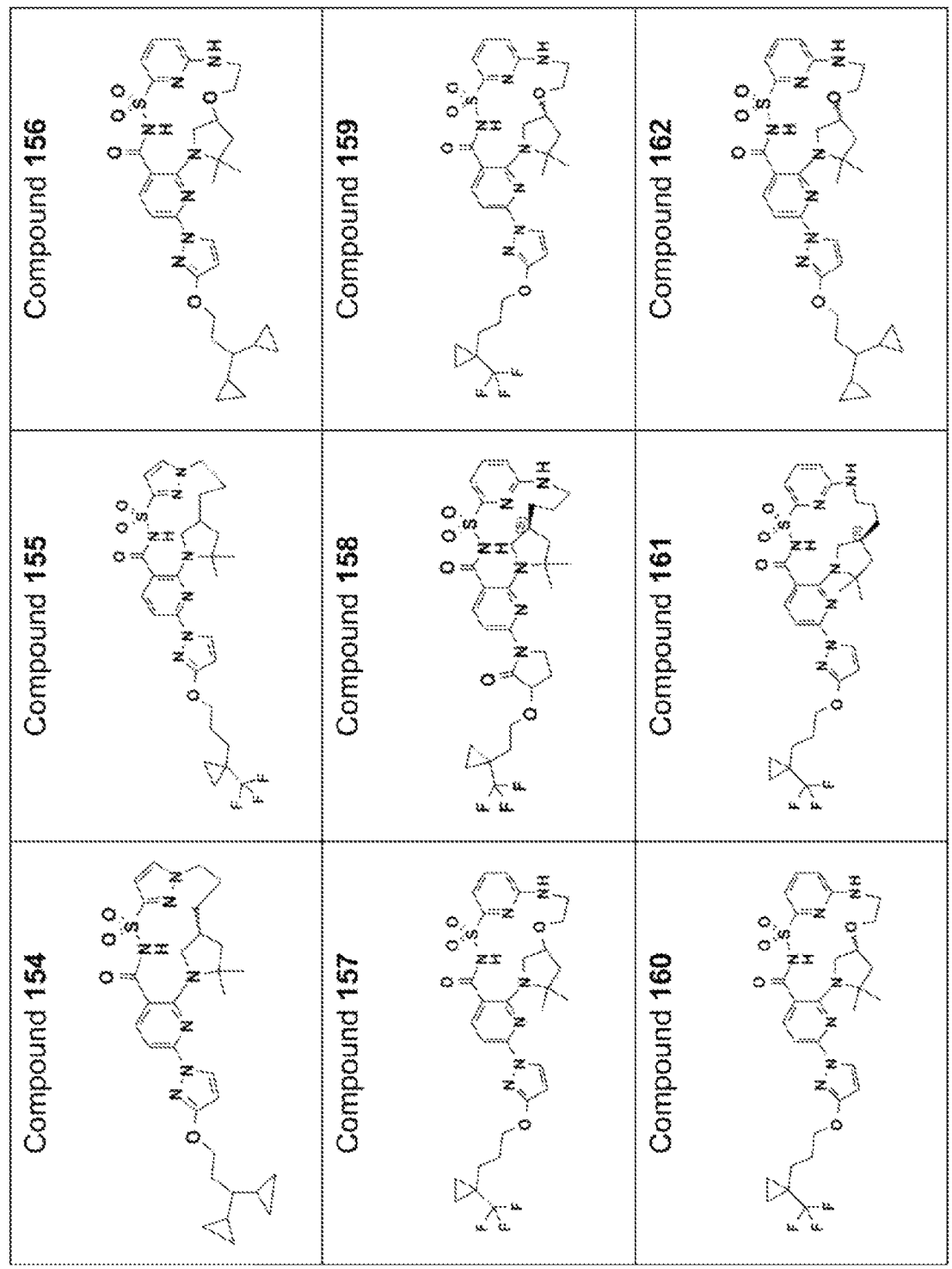
Figure 1:
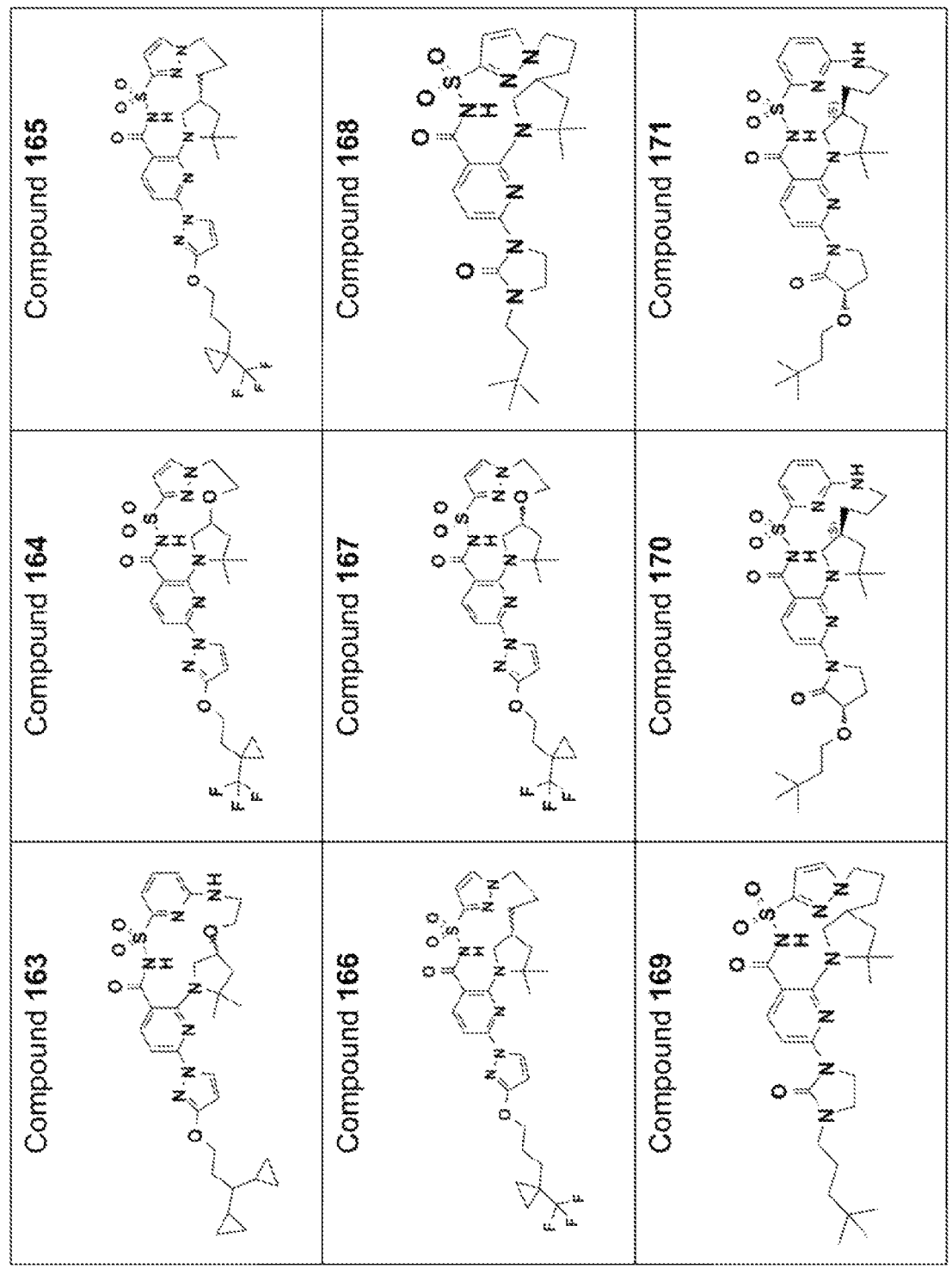
Figure 1:
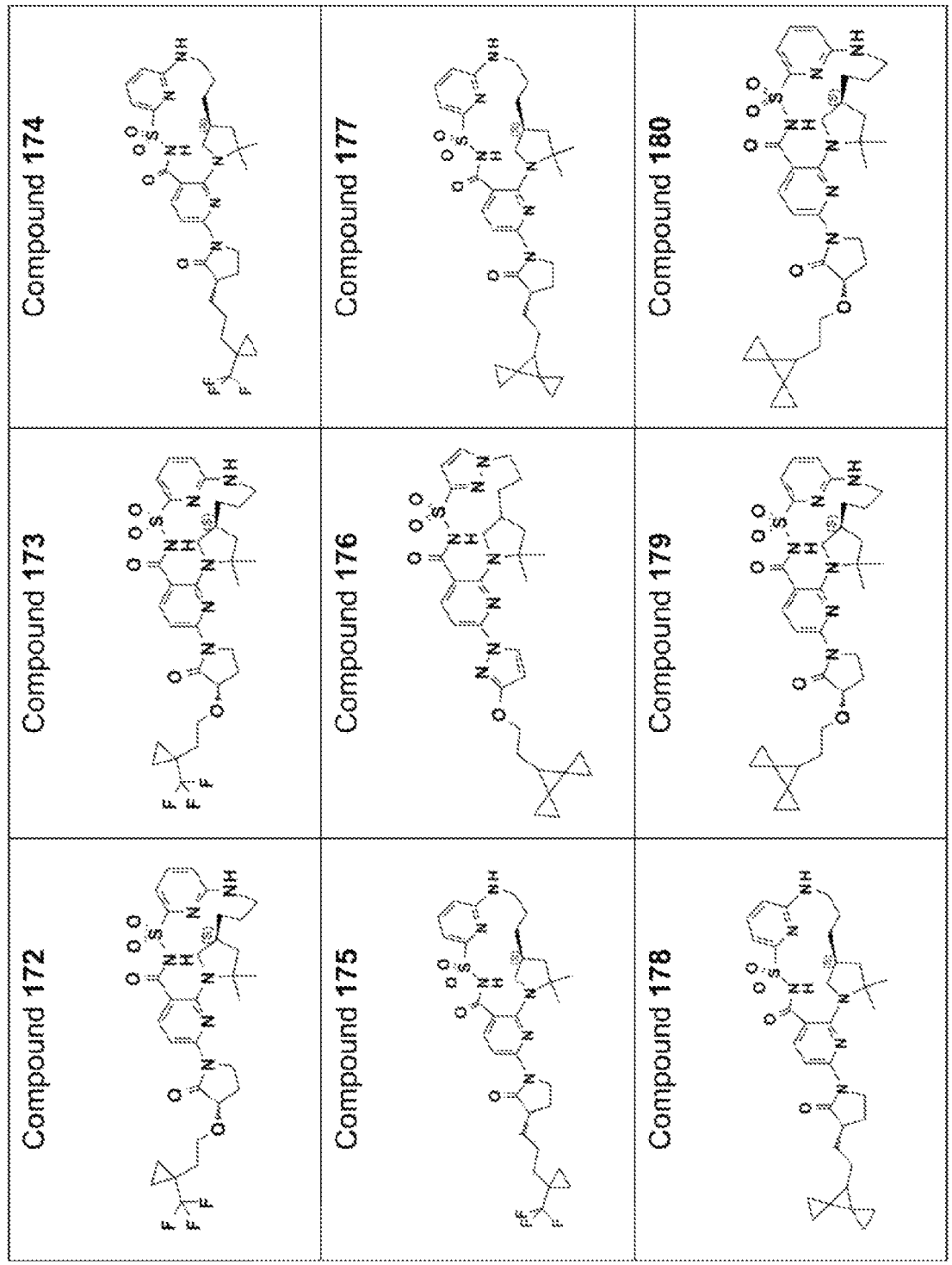
Figure 1:
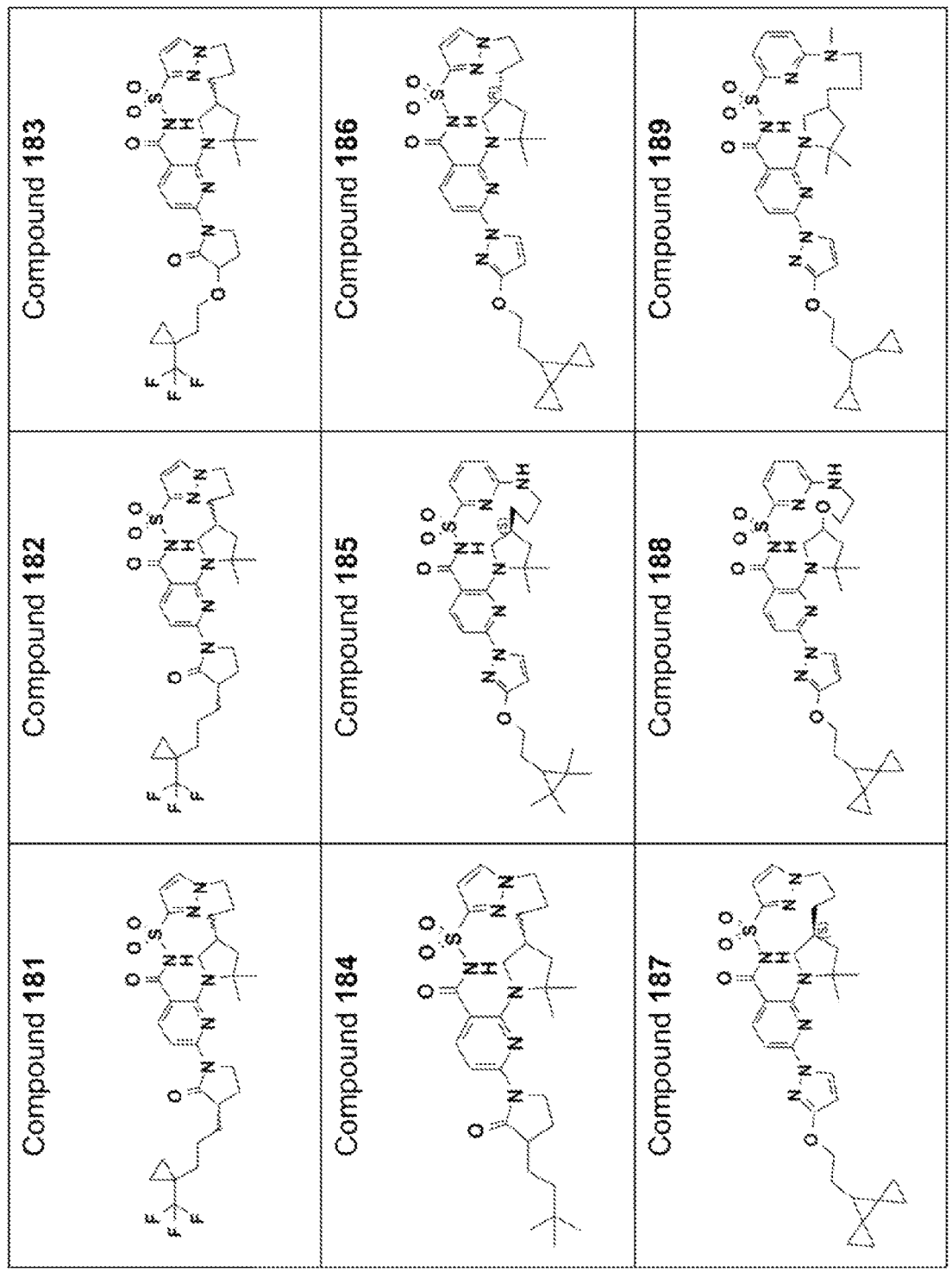
Figure 1:
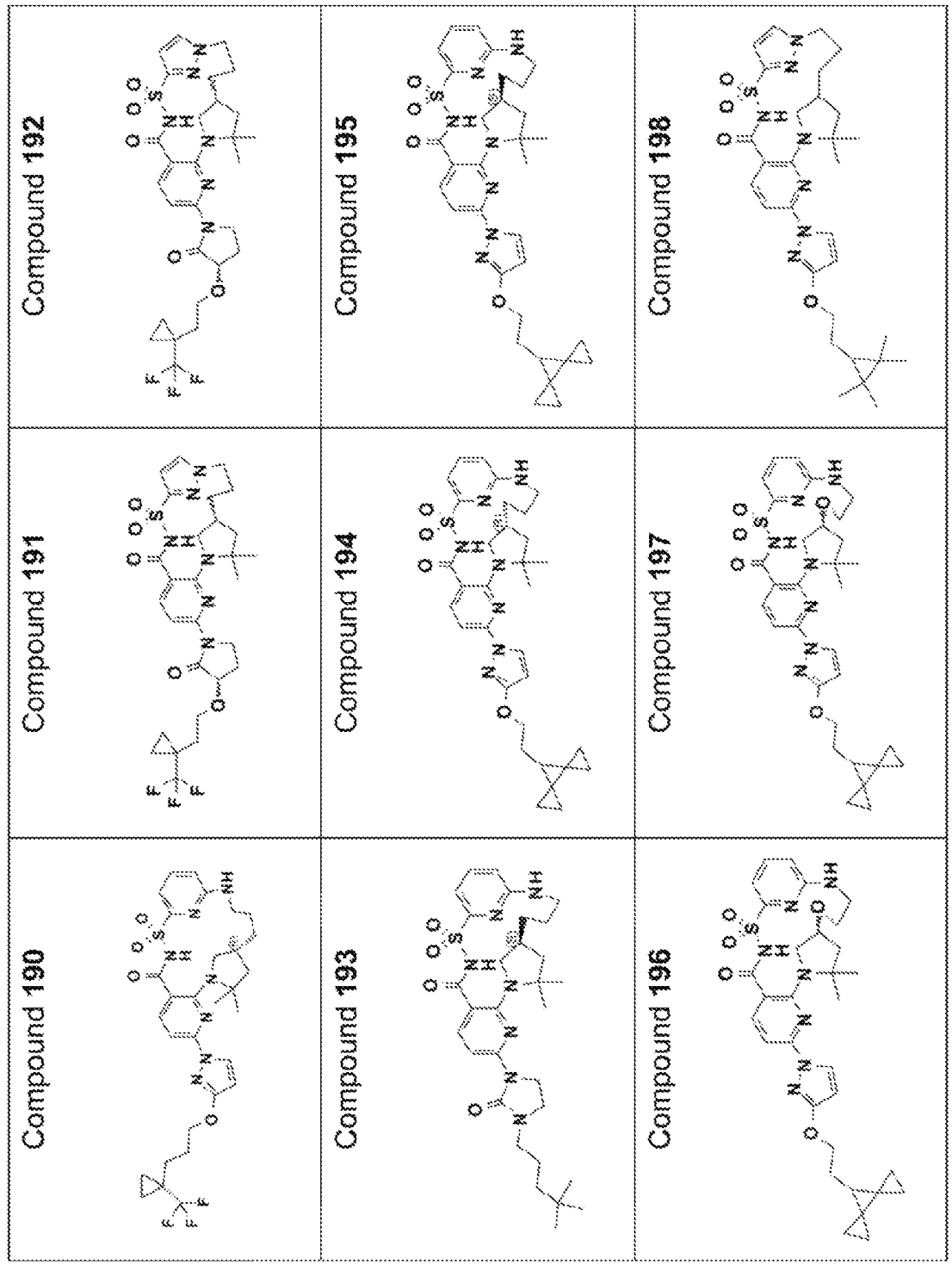
Figure 1:
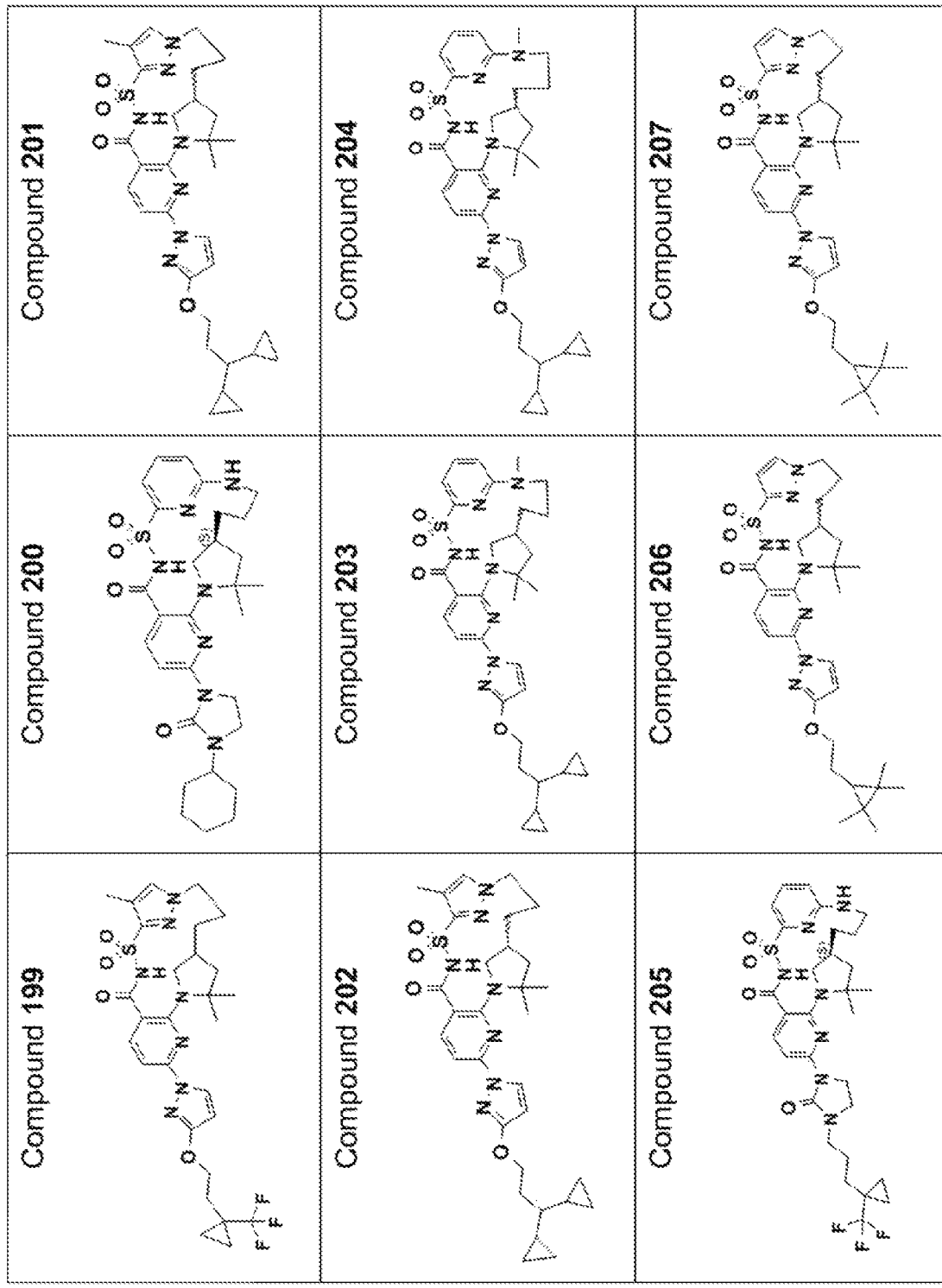
Figure 1:
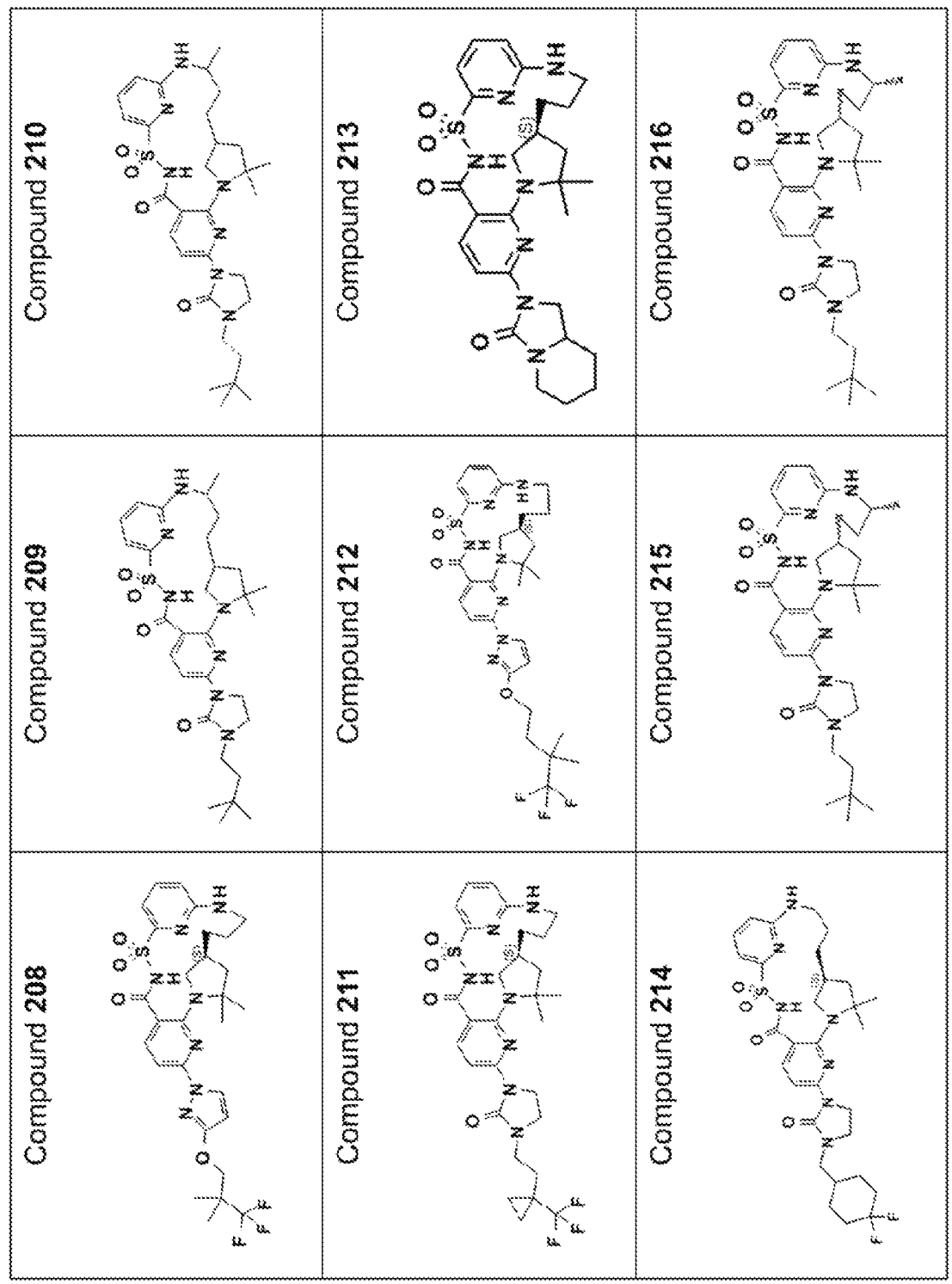
Figure 1:
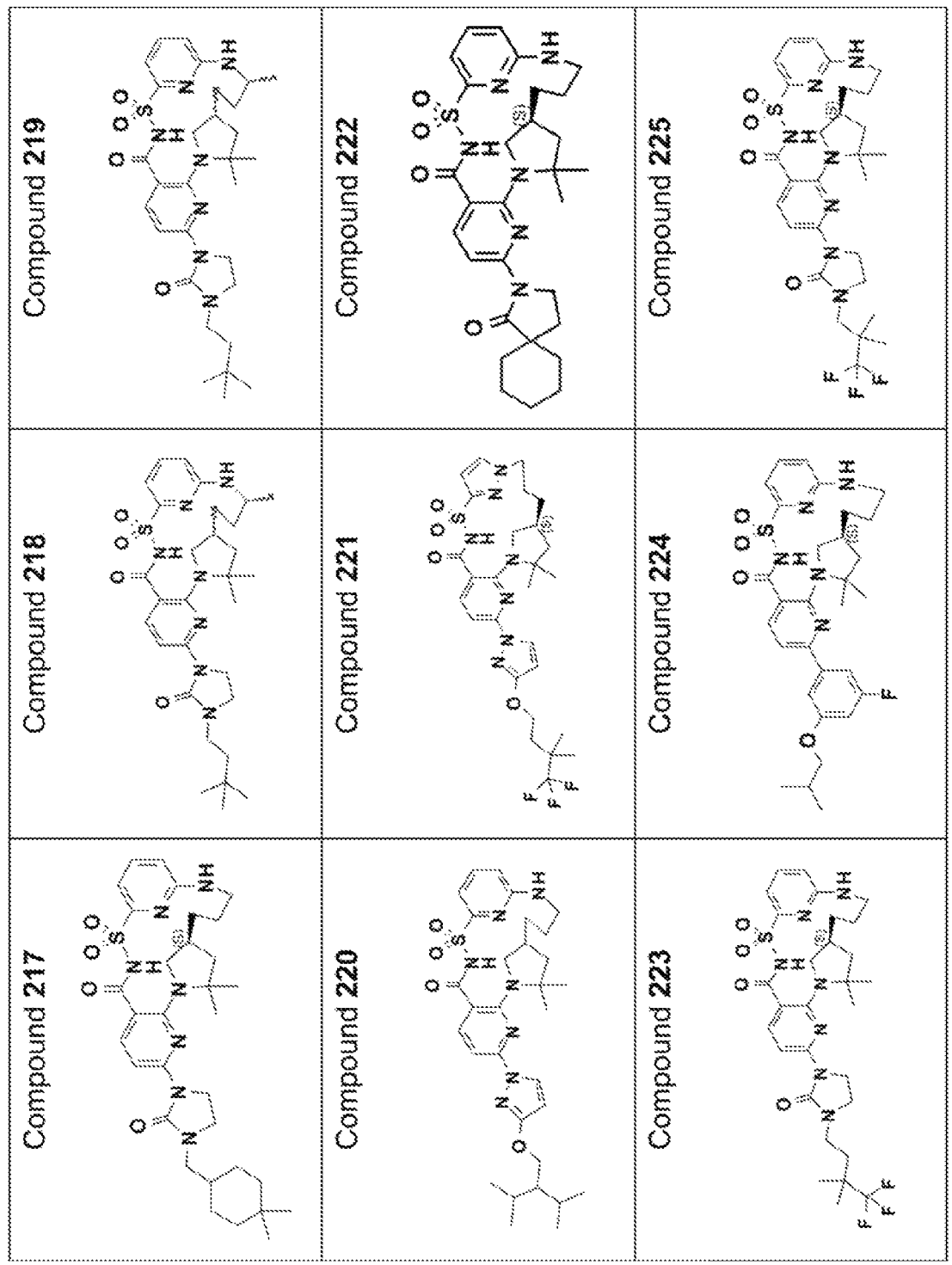
Figure 1:
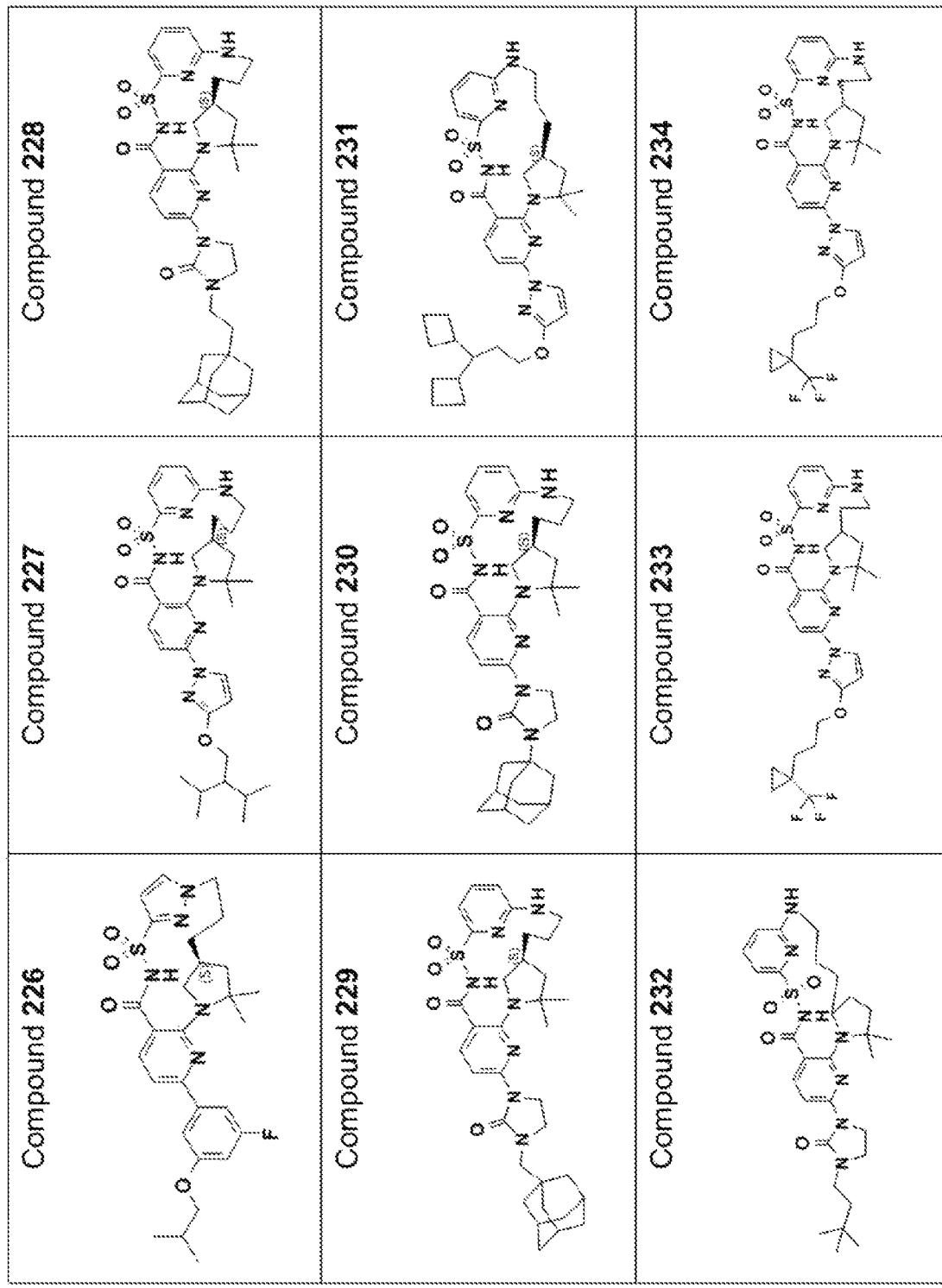
Figure 1:
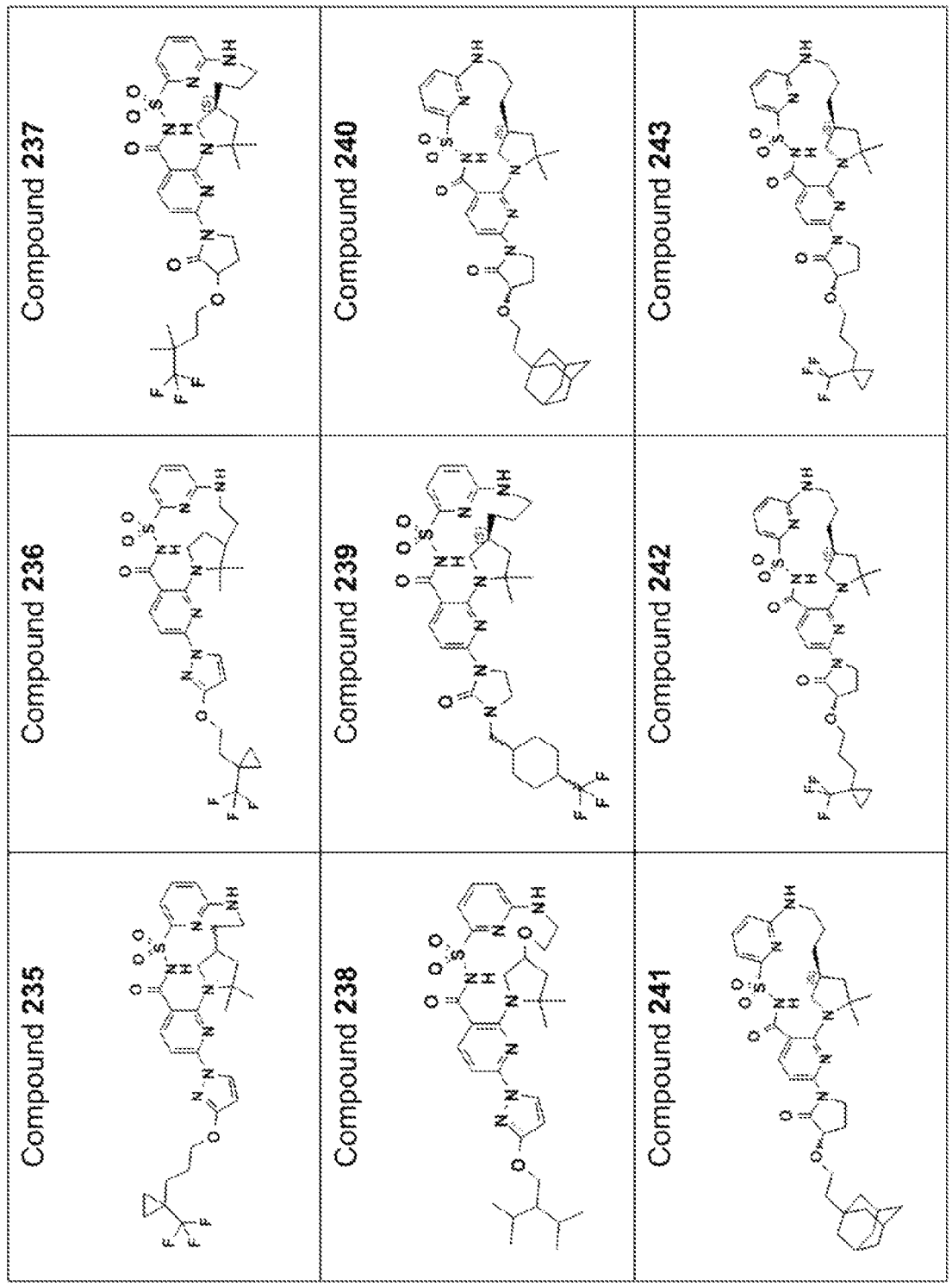
Figure 1:
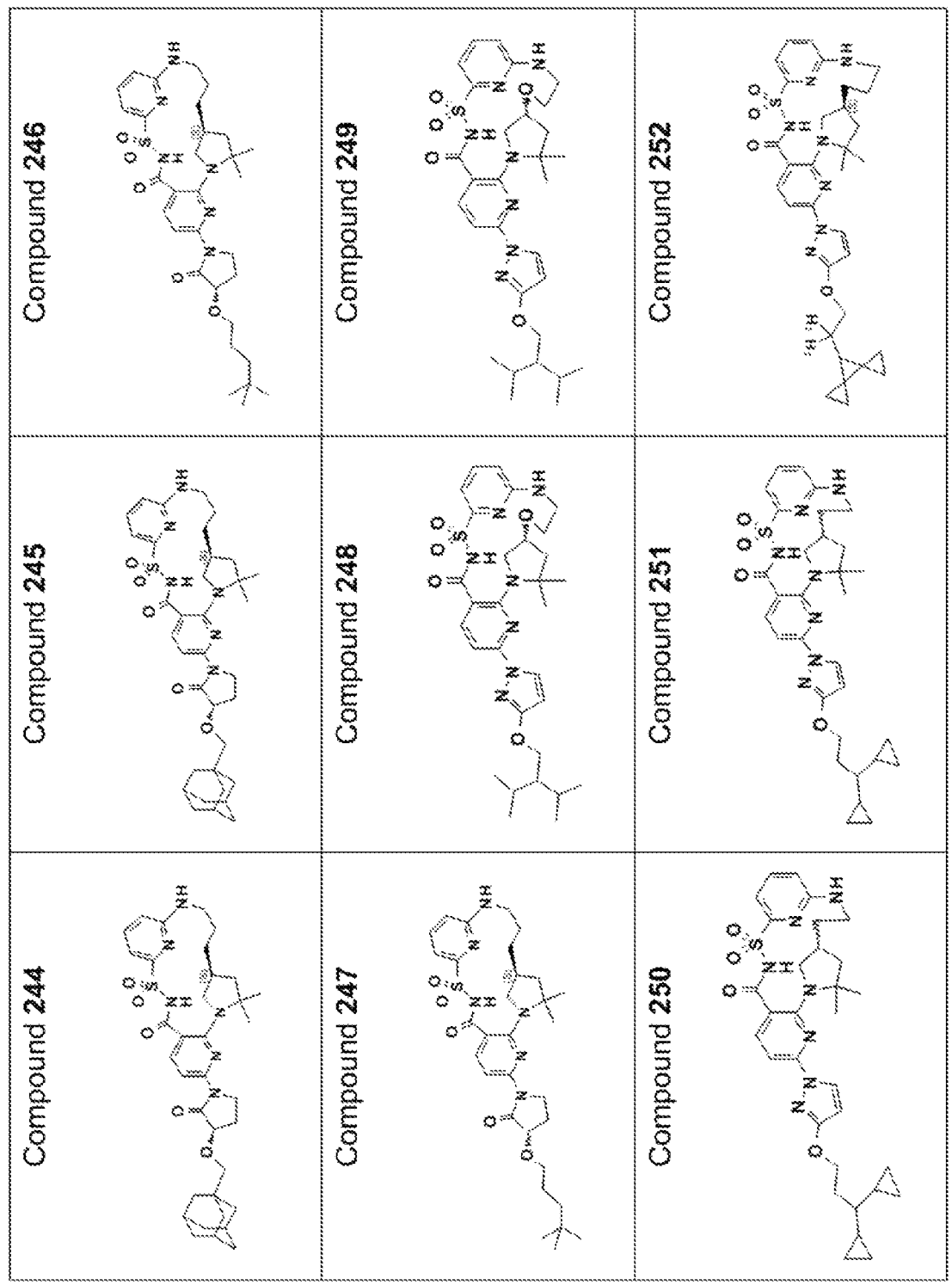
Figure 1:
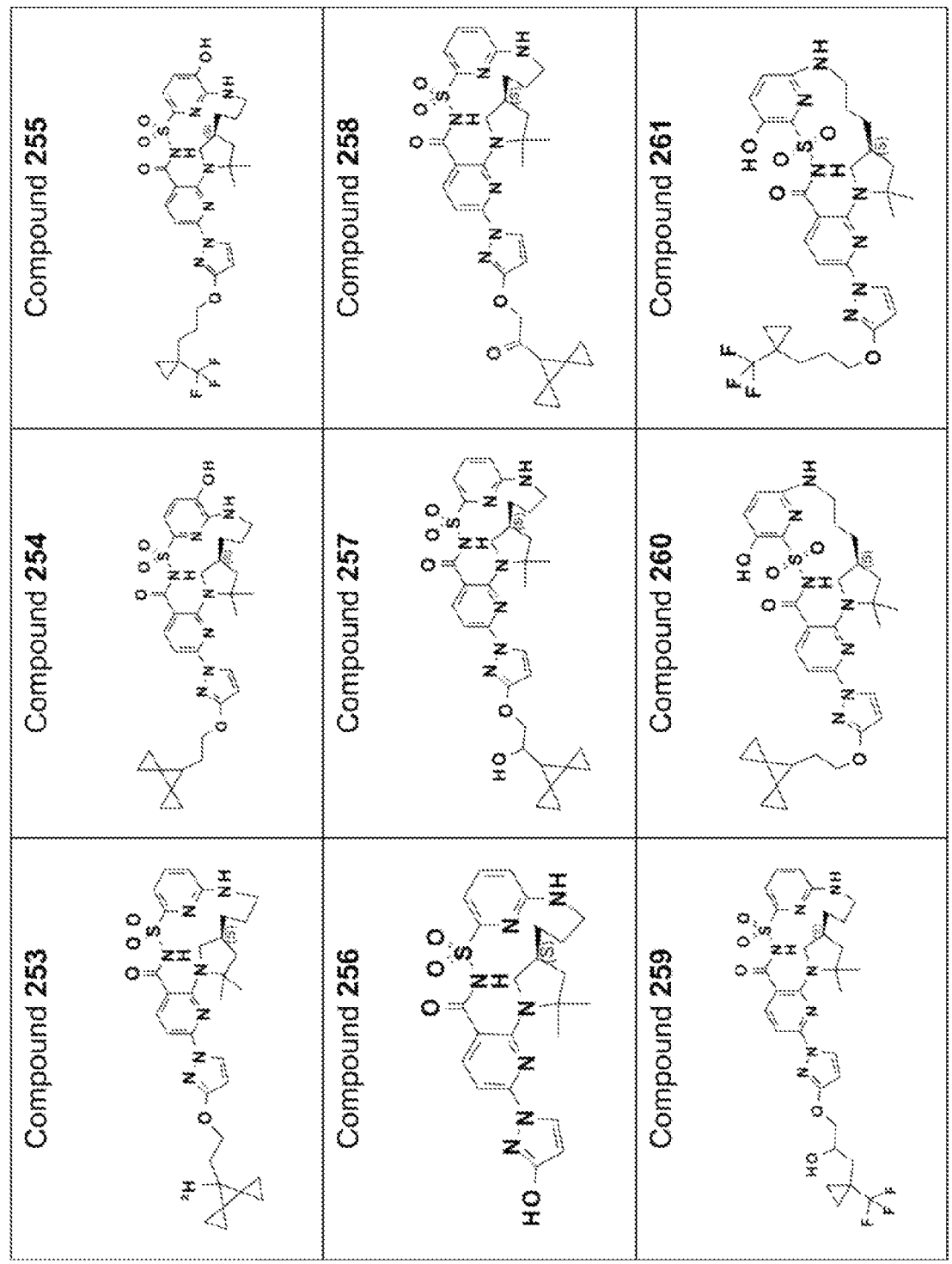
Figure 1:
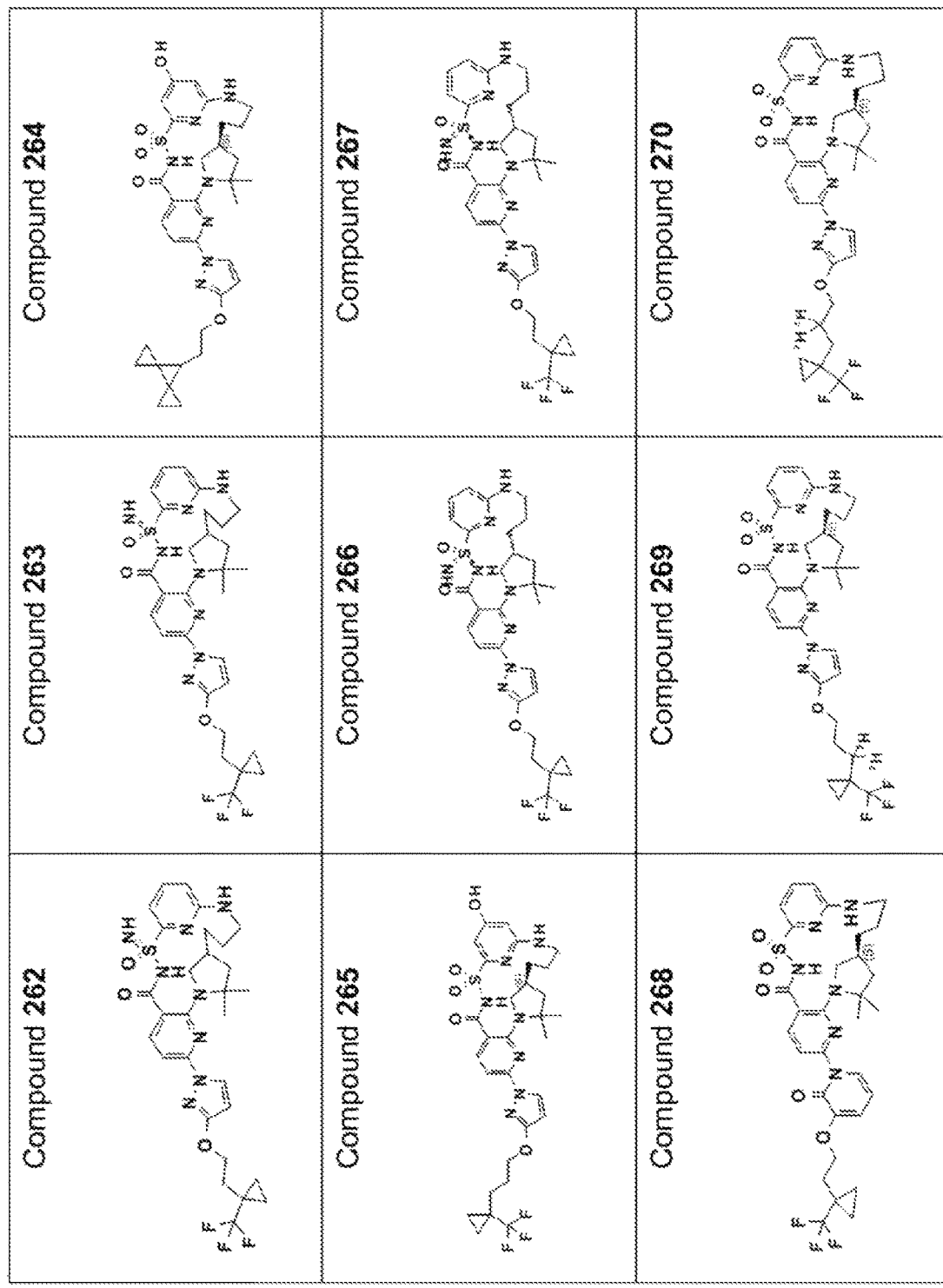
Figure 1:
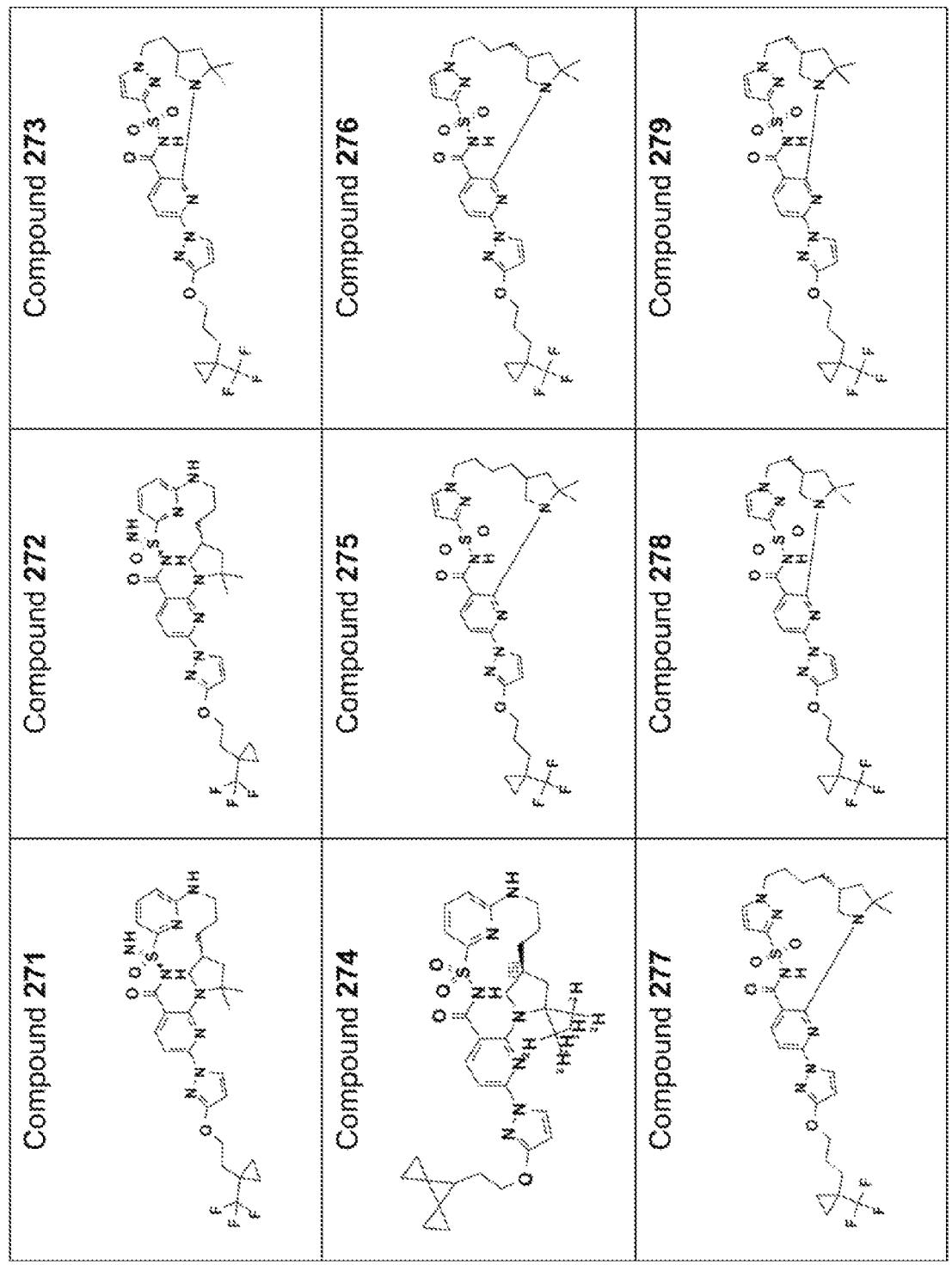
Figure 1:
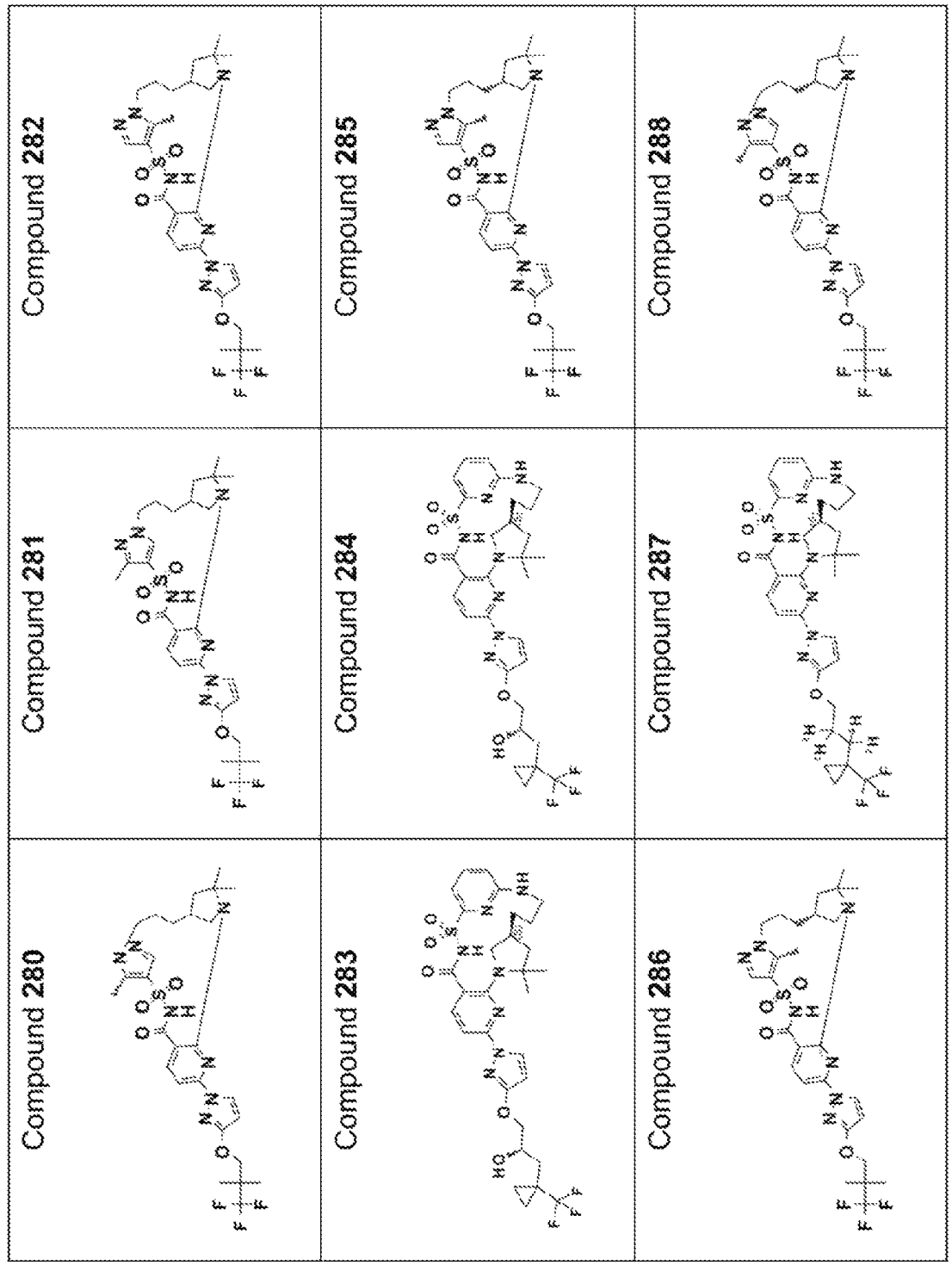
Figure 1:
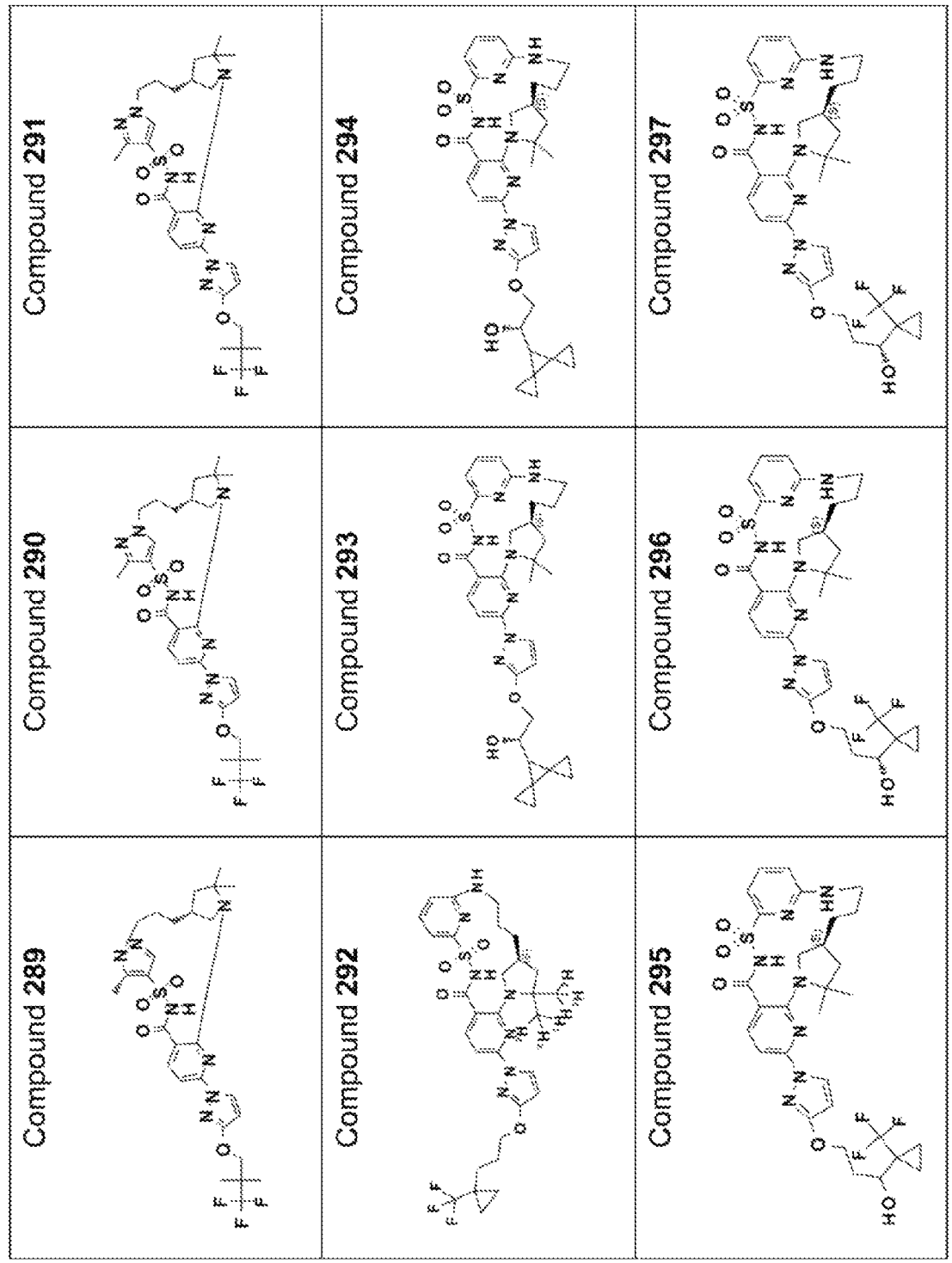
Figure 1:
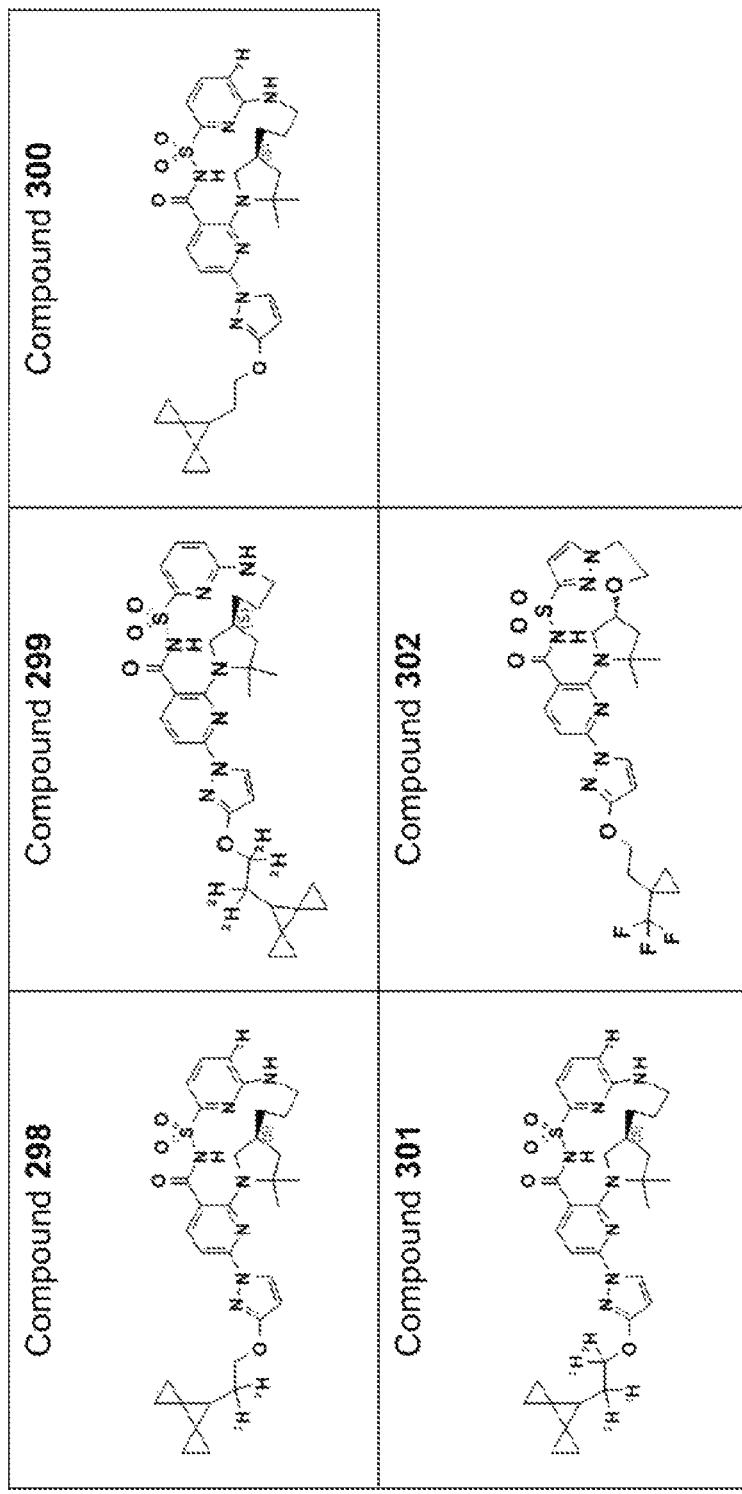
Figure 1:
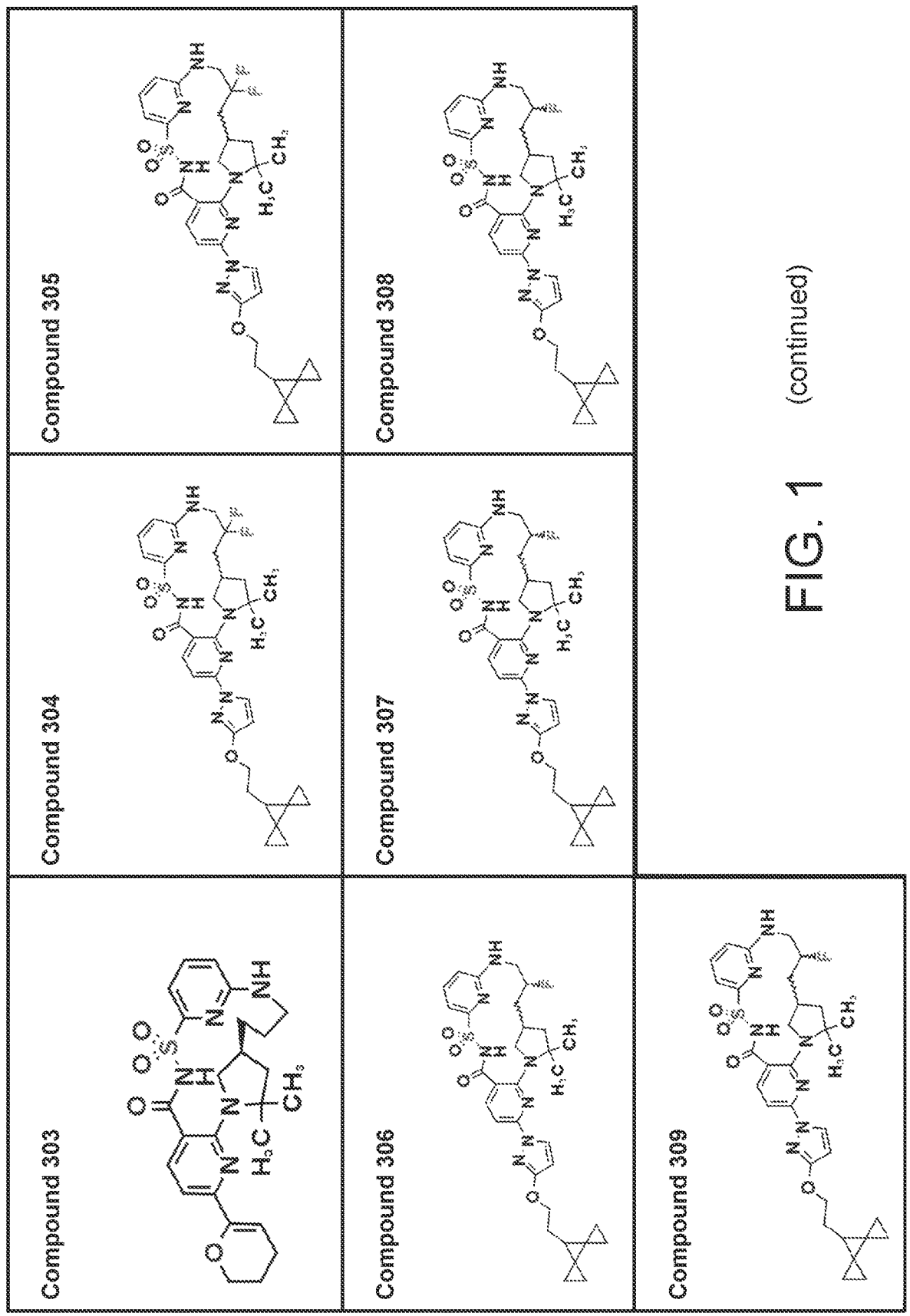

As used herein, the term "alkyl group" refers to a saturated aliphatic hydrocarbon (containing, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted and branched or unbranched.

As used herein, the term "haloalkyl group" refers to an alkyl group substituted with one or more halogen atoms.

As used herein, the term "cycloalkyl group" refers to a cyclic non-aromatic hydrocarbon containing 3 to 12 carbons in a ring (such as, for example 3 to 10 carbons). Cycloalkyl groups encompass monocyclic, bicyclic, tricyclic, polycyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, spiro[2.2]pentane, and dispiro [2.0.2.1]heptane. Cycloalkyl groups may be substituted or unsubstituted.

The term "alkoxy group" as used herein refers to an alkyl or cycloalkyl group covalently bonded to an oxygen atom. Alkoxy groups may be substituted or unsubstituted and branched or unbranched.

As used herein, the term "haloalkoxyl group" refers to an alkoxy group substituted with one or more halogen atoms.

The term "heteroaryl ring" as used herein refers to an aromatic ring comprising at least one ring atom that is a heteroatom, such as O, N, or S.

As used herein, the term "heterocyclyl ring" refers to a non-aromatic hydrocarbon containing 3 to 12 atoms in a ring (such as, for example 3-10 atoms) comprising at least one ring atom that is a heteroatom, such as O, N, or S. "Heterocyclyl" rings encompass monocyclic, bicyclic, tricyclic, polycyclic, bridged, fused, and spiro rings, including mono spiro and dispiro rings.

Examples of protecting groups for nitrogen include, for example, t-butyl carbamate (Boc), benzyl (Bn), paramethoxybenzyl (PMB), tetrahydropyranyl (THP), 9-fluorenylmethyl carbamate (Fmoc), benzyl carbamate (Cbz), methyl carbamate, ethyl carbamate, 2,2,2-trichloroethyl carbamate (Troc), 2-trimethylsilylethyl carbamate (Teoc), allyl carbamate (Aloc or Alloc), formamide, acetamide, benzamide, allylamine, trifluoroacetamide, triphenylmethylamine, benzylideneamine, and p-toluenesulfonamide. A comprehensive list of nitrogen protecting groups can be found in Wuts, P. G. M. "Greene's Protective Groups in Organic Synthesis: Fifth Edition," 2014, John Wiley and Sons.

"Substituted," whether preceded by the term "optionally" or not, indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

As used herein, "deuterated derivative(s)" means the same chemical structure, but with one or more hydrogen atoms replaced by a deuterium atom.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound or molecule such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compounds of Formulae (I), (II-A), (II-B), (III-A), (III-B), (IV-A), (IV-B), (IV-C), (V-A), (V-B), (VI-A), (VI-B), (VI-C), and (VI-D), Compound II, Compound IV, and their pharmaceutically acceptable salts thereof disclosed herein are CFTR correctors.

As used herein, the term "CFTR potentiator" refers to a compound that increases the channel activity of CFTR protein located at the cell surface, resulting in enhanced ion transport. Compound III disclosed herein is a CFTR potentiator.

As used herein, the term "active pharmaceutical ingredient" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describe pharmaceutically acceptable salts in detail in *J. Pharmaceutical Sciences*, 1977, 66, 1-19.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material.

As used herein, the term "substantially amorphous" refers to a solid material having little or no long range order in the position of its molecules. For example, substantially amorphous materials have less than 15% crystallinity (e.g., less than 10% crystallinity or less than 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment, and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately," when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "10 mg of at least one compound chosen from compounds of Formula (I) and pharmaceutically acceptable salts thereof" includes 10 mg of a compound of Formula (I) and a concentration of a pharmaceutically acceptable salt of compounds of Formula (I) equivalent to 10 mg of compounds of Formula (I).

Suitable pharmaceutically acceptable salts are, for example, those disclosed in S. M. Berge, et al. *J. Pharmaceutical Sciences*, 1977, 66, 1-19. For example, Table 1 of that article provides the following pharmaceutically acceptable salts:

TABLE 1

| | | |
|---|---|---|
| Acetate | Hydrobromide | Stearate |
| Benzenesulfonate | Hydrochloride | Subacetate |
| Benzoate | Hydroxynaphthoate | Succinate |
| Bicarbonate | Iodide | Sulfate |
| Bitartrate | Isethionate | Tannate |
| Bromide | Lactate | Tartrate |
| Calcium edetate | Lactobionate | Teociate |
| Camsylate | Malate | Triethiodide |
| Carbonate | Maleate | Benzathine |
| Chloride | Mandelate | Chloroprocaine |
| Citrate | Mesylate | Choline |
| Dihydrochloride | Methylbromide | Diethanolamine |
| Edetate | Methylnitrate | Ethylenediamine |
| Edisylate | Methylsulfate | Meglumine |
| Estolate | Mucate | Procaine |
| Esylate | Napsylate | Aluminum |
| Fumarate | Nitrate | Calcium |
| Gluceptate | Pamoate (Embonate) | Lithium |
| Gluconate | Pantothenate | Magnesium |
| Glutamate | Phosphate/diphosphate | Potassium |
| Glycollylarsanilate | Polygalacturonate | Sodium |
| Hexylresorcinate | Salicylate | Zinc |
| Hydrabamine | | |

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which have the same structures as disclosed herein except that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^3H$)— and/or carbon-14 ($^{14}C$) labelled compounds are particularly useful for various types of assays, such as substrate tissue distribution assays, due to relatively simple preparation and excellent detectability. For example, deuterium ($^2H$)-labelled ones are therapeutically useful with potential therapeutic advantages over the non-$^2H$-labelled compounds. In general, deuterium ($^2H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones. In some specific embodiments, the isotope-labelled compounds and salts are deuterium ($^2$H)-labelled, wherein one or more hydrogen atoms therein have been replaced by deuterium. In chemical structures, deuterium is represented as "$^2$H" or "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. For a further discussion, see S. L. Harbeson and R. D. Tung, *Deuterium In Drug Discovery and Development*, Ann. Rep. Med. Chem. 2011, 46, 403-417; and T. G. Gant "Using deuterium in drug discovery: leaving the label in the drug" J. Med. Chem. 2014, 57, 3595-3611, relevant portions of which are independently incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

One of ordinary skill in the art would understand that deuteration of one or more metabolically labile positions on a compound or active metabolite may lead to improvement of one or more superior DMPK properties while maintaining biological activity as compared to the corresponding hydrogen analogs. The superior DMPK property or properties may have an impact on the exposure, half-life, clearance, metabolism, and/or even food requirements for optimal absorption of the drug product. Deuteration may also change the metabolism at other non-deuterated positions of the deuterated compound.

In some embodiments, the disclosure includes deuterated derivatives of the novel compounds disclosed herein and of their pharmaceutically acceptable salts. Non-limiting examples of deuterated compounds are disclosed in FIG. 1.

Each compound described herein, including compounds of Formulae (I), (II-A), (II-B), (III-A), (III-B), (IV-A), (IV-B), (IV-C), (V-A), (V-B), (VI-A), (VI-B), (VI-C), and (VI-D), Compounds II, III, and IV, pharmaceutically acceptable salts thereof, and deuterated derivatives of any of the foregoing can independently be administered once daily, twice daily, or three times daily. In some embodiments, at least one compound chosen from Compounds of Formulae (I), (II-A), (II-B), (III-A), (III-B), (IV-A), (IV-B), (IV-C), (V-A), (V-B), (VI-A), (VI-B), (VI-C), and (VI-D), pharmaceutically acceptable salts thereof, and deuterated derivatives of any of the foregoing is administered once daily. In some embodiments, at least one compound chosen from Compounds of Formulae (I), (II-A), (II-B), (III-A), (III-B), (IV-A), (IV-B), (IV-C), (V-A), (V-B), (VI-A), (VI-B), (VI-C), and (VI-D), and pharmaceutically acceptable salts thereof, and deuterated derivatives of any of the foregoing are administered twice daily. In some embodiments, at least one compound chosen from Compound II and pharmaceutically acceptable salts thereof is administered once daily. In some embodiments, at least one compound chosen from Compound II and pharmaceutically acceptable salts thereof is administered twice daily. In some embodiments, at least one compound chosen from Compound III and pharmaceutically acceptable salts thereof is administered once daily. In some embodiments, at least one compound chosen from Compound III and pharmaceutically acceptable salts thereof is administered twice daily. In some embodiments, at least one compound chosen from Compound IV and pharmaceutically acceptable salts thereof is administered once daily. In some embodiments, at least one compound chosen from Compound IV and pharmaceutically acceptable salts thereof is administered twice daily. In some embodiments, a deuterated derivative of Compound II, III, and/or IV or a pharmaceutically acceptable salt thereof is employed in any one of these embodiments.

In some embodiments, 10 mg to 1,500 mg of a compound disclosed herein, a pharmaceutically acceptable salt thereof, or a deuterated derivative of such compound or salt are administered daily.

As stated above, disclosed herein are compounds of Formula (I):

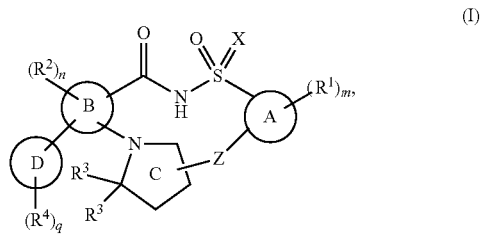

a pharmaceutically acceptable salt thereof, or a deuterated derivative of any of the foregoing,
wherein:
  Ring A is a phenyl, a 5-membered heteroaryl ring, or a 6-membered heteroaryl ring;
  Ring B is a pyridinyl ring;
  Ring D is a phenyl ring, a 5-membered heterocyclyl ring, a 6-membered heterocyclyl ring, a 5-membered heteroaryl ring, or a 6-membered heteroaryl ring;
  X is O, NH, or an N(C1-C4 alkyl);

each R¹ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

m is 0, 1, 2, 3, or 4;

each R² is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each R³ is methyl;

each R⁴ is independently chosen from halogens, an oxo group, a hydroxyl group, a cyano group, and -$(Y)_k$-$R^7$ groups, or optionally two R⁴, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups; wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each R⁵ and R⁶ is independently chosen from hydrogen, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group or oxo;

each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and R⁷ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1, 2, 3 or 4; and

Z is a divalent linker of formula $(L)_r$, wherein:

r is 1, 2, 3, 4, 5, or 6;

each L is independently chosen from $C(R^8)(R^9)$ groups, —O—, and —$NR^b$— groups, wherein a heteroatom in Z is not bonded to another heteroatom in Z, wherein:

each R⁸ and R⁹ is independently chosen from hydrogen, halogens, $C_1$-$C_2$ haloalkyl groups, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

In some embodiments, the compound of Formula I is a compound of Formula (II-A) or (II-B):

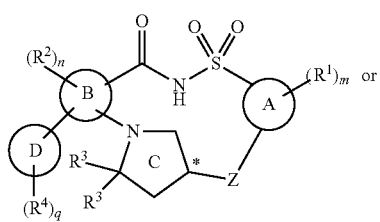

(II-A)

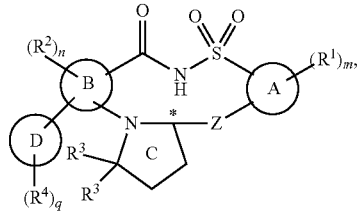

(II-B)

a pharmaceutically acceptable salt thereof, or a deuterated derivative of any of the foregoing, wherein:

the carbon denoted by * has S-stereochemistry or R-stereochemistry;

Ring A is a phenyl, a 5-membered heteroaryl ring, or a 6-membered heteroaryl ring;

Ring B is a pyridinyl ring;

Ring D is a phenyl ring, a 5-membered heterocyclyl ring, a 6-membered heterocyclyl ring, a 5-membered heteroaryl ring, or a 6-membered heteroaryl ring;

each R¹ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

m is 0, 1, 2, 3, or 4;

each R² is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each R³ is methyl;

each R⁴ is independently chosen from halogens, a hydroxyl group, an oxo group, a cyano group, and -$(Y)_k$-$R^7$ groups, or optionally two R⁴, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each R⁵ and R⁶ is independently chosen from hydrogen, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group or oxo;

each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and R⁷ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1, 2, 3, or 4;

Z is a divalent linker of formula $(L)_r$, wherein:
r is 1, 2, 3, 4, 5, or 6;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen, halogens, $C_1$-$C_2$ alkyl groups, $C_1$-$C_2$ haloalkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

In some embodiments, the compound of Formula I is a compound of Formula (III-A) or (III-B):

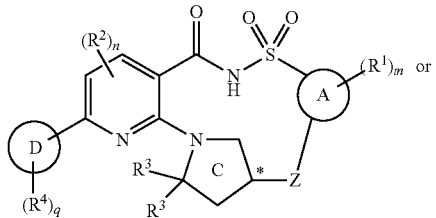

(III-A)

or

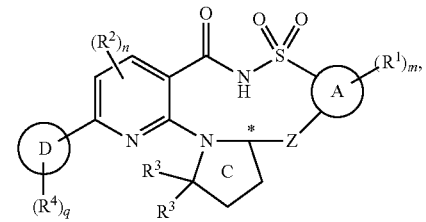

(III-B)

a pharmaceutically acceptable salt thereof, or a deuterated derivative of any of the foregoing,
wherein:
the carbon denoted by * has S-stereochemistry or R-stereochemistry;
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;
q is 1 or 2;
Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

In some embodiments, the compound of Formula I is a compound of Formula IV-A:

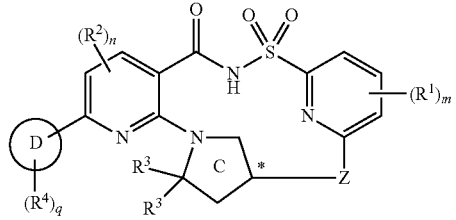

(IV-A)

a pharmaceutically acceptable salt thereof, or a deuterated derivative of any of the foregoing,
wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
X is O, NH, or an $N(C_1$-$C_4$ alkyl);
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and $-(Y)_k-R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —$NR^a$— groups, wherein a heteroatom in $-(Y)_k-R^7$ is not bonded to another heteroatom in $-(Y)_k-R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;

Z is a divalent linker of formula $(L)_r$, wherein:

r is 3, 4, or 5;

each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

In some embodiments, the compound of Formula I is a compound of Formula IV-B:

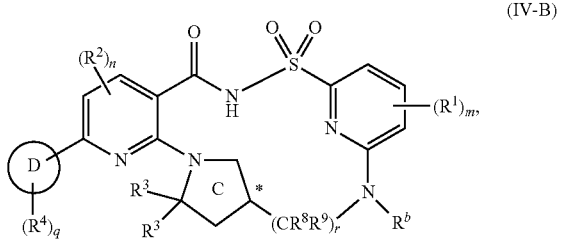

(IV-B)

a pharmaceutically acceptable salt thereof, or a deuterated derivative of any of the foregoing, wherein:

the carbon denoted by * has S-stereochemistry or R-stereochemistry;

Ring D is a phenyl ring, a 5-membered heterocyclyl ring, a 6-membered heterocyclyl ring, a 5-membered heteroaryl ring, or a 6-membered heteroaryl ring;

each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

m is 0, 1, 2, 3, or 4;

each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and $-(Y)_k-R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —$NR^a$— groups, wherein a heteroatom in $-(Y)_k-R^7$ is not bonded to another heteroatom in $-(Y)_k-R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;

r is 3 or 4;

each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

In some embodiments, the compound of Formula I is a compound of Formula IV-C:

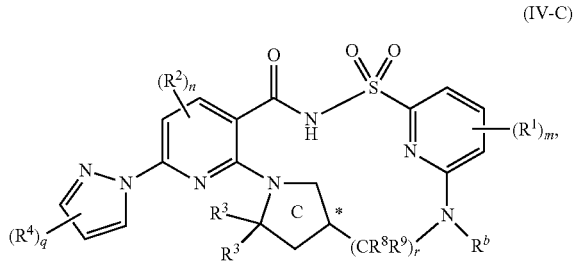

(IV-C)

a pharmaceutically acceptable salt thereof, or a deuterated derivative of any of the foregoing, wherein:
the carbon denoted by * has S-stereochemistry or R-stereochemistry;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;
q is 1 or 2;
r is 3 or 4;
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

In some embodiments, the compound of Formula I is a compound of Formula V-A:

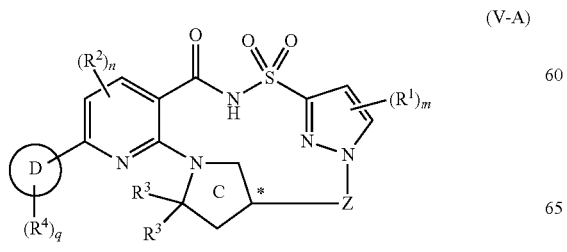

(V-A)

a pharmaceutically acceptable salt thereof, or a deuterated derivative of any of the foregoing,
wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;
q is 1 or 2;
Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

In some embodiments, the compound of Formula I is a compound of Formula V-B:

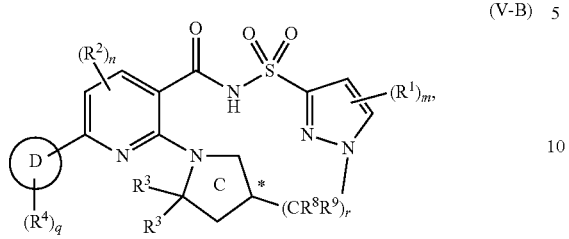

(V-B)

a pharmaceutically acceptable salt thereof, or a deuterated derivative of any of the foregoing,
wherein:
  the carbon denoted by * has S-stereochemistry or R-stereochemistry;
  Ring D is a phenyl ring, a 5-membered heterocyclyl ring, a 6-membered heterocyclyl ring, a 5-membered heteroaryl ring, or a 6-membered heteroaryl ring;
  each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  m is 0, 1, 2, 3, or 4;
  each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  n is 0, 1, or 2;
  each $R^3$ is methyl;
  each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
    k is 0, 1, 2, 3, 4, 5, or 6;
    each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
      each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
        each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
      each $R^a$ is independently chosen from hydrogen and $C_1$-$C_2$ alkyl groups; and
    $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;
  q is 1 or 2;
  r is 3, 4, or 5; and
    each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups.

In some embodiments, the compound of Formula I is a compound of Formula VI-A or VI-B:

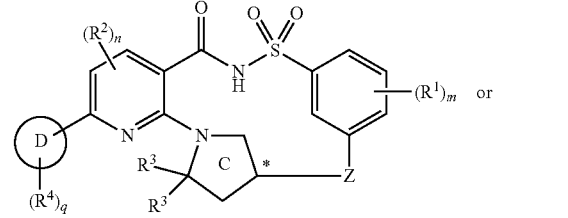

(VI-A)

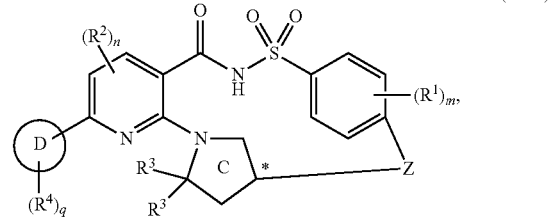

(VI-B)

a pharmaceutically acceptable salt thereof, or a deuterated derivative of any of the foregoing,
wherein:
  the carbon denoted by * has S-stereochemistry or R-stereochemistry;
  Ring D is a phenyl ring, a 5-membered heterocyclyl ring, a 6-membered heterocyclyl ring, a 5-membered heteroaryl ring, or a 6-membered heteroaryl ring;
  each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  m is 0, 1, 2, 3, or 4;
  each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  n is 0, 1, or 2;
  each $R^3$ is methyl;
  each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
    k is 0, 1, 2, 3, 4, 5, or 6;
    each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
      each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
        each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;

Z is a divalent linker of formula $(L)_r$, wherein:
  r is 3, 4, or 5;
  each L is independently chosen from $C(R^8)(R^9)$ groups, —O—, and —$NR^b$— groups, wherein a heteroatom in Z is not bonded to another heteroatom in Z, wherein:
    each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
    each $R^b$ is independently chosen from hydrogen and $C_1$-$C_2$ alkyl groups.

In some embodiments, the compound of Formula I is a compound of Formula VI-C or VI-D:

(VI-C)

(VI-D)

a pharmaceutically acceptable salt thereof, or a deuterated derivative of any of the foregoing,
wherein:
  the carbon denoted by * has S-stereochemistry or R-stereochemistry;
  Ring D is a phenyl ring, a 5-membered heterocyclyl ring, a 6-membered heterocyclyl ring, a 5-membered heteroaryl ring, or a 6-membered heteroaryl ring;
  X is O, NH, or an $N(C_1$-$C_4$ alkyl);
  each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  m is 0, 1, 2, 3, or 4;
  each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
  n is 0, 1, or 2;
  each $R^3$ is methyl;
  each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
    k is 0, 1, 2, 3, 4, 5, or 6;
    each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
      each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
      each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
    each $R^a$ is independently chosen from hydrogen and $C_1$-$C_2$ alkyl groups; and
    $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;
  q is 1 or 2;
  r is 3 or 4; and
  each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups.

Also disclosed herein are compounds having a formula chosen from any one of the formulae depicted in FIG. 1 and pharmaceutically acceptable salts thereof.

In some embodiments, at least one compound chosen from the novel compounds disclosed herein, pharmaceutically acceptable salts thereof, and deuterated derivatives of the foregoing is administered in combination with at least one compound chosen from Compound II, pharmaceutically acceptable salts thereof, and deuterated derivatives of the foregoing. In some embodiments, at least one compound chosen from the novel compounds disclosed herein, pharmaceutically acceptable salts thereof, and deuterated derivatives of the foregoing is administered in combination with at least one compound chosen from Compound III and pharmaceutically acceptable salts thereof. In some embodiments, at least one compound chosen from the novel compounds disclosed herein, pharmaceutically acceptable salts thereof, and deuterated derivatives of the foregoing is administered in combination with at least one compound chosen from Compound IV and pharmaceutically acceptable salts thereof. In some embodiments, at least one compound chosen from the novel compounds disclosed herein, pharmaceutically acceptable salts, and deuterated derivatives of the foregoing thereof is administered in combination with Compounds II or a pharmaceutically acceptable salt or deuterated derivative thereof and at least one compound chosen from Compound III, pharmaceutically acceptable salts thereof, and deuterated derivatives of any of the foregoing. In some embodiments, at least one compound chosen from the novel compounds disclosed herein, pharmaceutically acceptable salts, and deuterated derivatives of any of the foregoing thereof is administered in combination with at least one compound chosen from Compound III, pharmaceutically acceptable salts thereof, and deuterated derivatives of any of the foregoing and at least one compound chosen from Compound IV, pharmaceutically acceptable salts thereof, and deuterated derivatives of any of the foregoing.

In some embodiments, at least one novel compound (and/or at least one pharmaceutically acceptable salt thereof and/or at least one deuterated derivative of such compound or salt) can be administered in combination with at least one additional active pharmaceutical ingredient. In some embodiments, at least one additional active pharmaceutical ingredient is chosen from:

(a) Compound II:

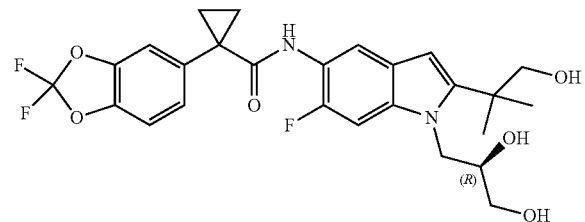

and pharmaceutically acceptable salts thereof.

A chemical name for Compound II is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide;

(b) Compound III:

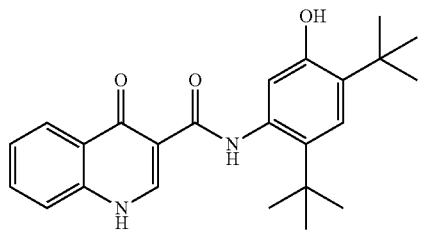

and pharmaceutically acceptable salts thereof.

A chemical name for Compound III is N-(5-hydroxy-2, 4-di-tert-butyl-phenyl)-4-oxo-1H-quinoline-3-carboxamide; and (c) Compund IV:

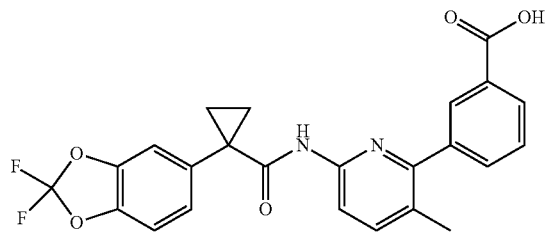

and pharmaceutically acceptable salts thereof.

A chemical name for Compound IV is 3-(6-(1-(2,2-difluorobenzo[d][1,3]dioxol-5-yl)cyclopropane-1-carbox-amido)-3-methylpyridin-2-yl)benzoic acid. In some embodiments, a compound of Formula (I) and/or a pharmaceutically acceptable salt thereof can be administered in combination with Compound II and/or a pharmaceutically acceptable salt thereof. In some embodiments, a compound of Formula (I) and/or a pharmaceutically acceptable salt thereof can be administered in combination with Compound III and/or a pharmaceutically acceptable salt thereof. In some embodiments, a compound of Formula (I) and/or a pharmaceutically acceptable salt thereof can be administered in combination with Compound IV and/or a pharmaceutically acceptable salt thereof. In some embodiments a compound of Formula (I) and/or a pharmaceutically acceptable salt thereof can be administered in combination with Compounds II and/or a pharmaceutically acceptable salt thereof and Compound III and/or a pharmaceutically acceptable salt thereof. In some embodiments a compound of Formula (I) and/or a pharmaceutically acceptable salt thereof can be administered in combination with Compounds II and/or a pharmaceutically acceptable salt thereof and Compound IV and/or a pharmaceutically acceptable salt thereof.

In one aspect, the disclosure features a pharmaceutical composition comprising a compound of Formula (I) and/or a pharmaceutically acceptable salt thereof, and a pharmaceutically acceptable carrier.

In one aspect, the disclosure features a pharmaceutical composition comprising a compound of Formula (I) and/or a pharmaceutically acceptable salt thereof, Compound II and/or a pharmaceutically acceptable salt thereof, and a pharmaceutically acceptable carrier.

In one aspect, the disclosure features a pharmaceutical composition comprising a compound of Formula (I) and/or a pharmaceutically acceptable salt thereof, Compound III and/or a pharmaceutically acceptable salt thereof, and a pharmaceutically acceptable carrier.

In one aspect, the disclosure features a pharmaceutical composition comprising a compound of Formula (I) and/or a pharmaceutically acceptable salt thereof, Compound II and/or a pharmaceutically acceptable salt thereof, Compound III and/or a pharmaceutically acceptable salt thereof, and a pharmaceutically acceptable carrier.

Any of the novel compounds disclosed herein, such as for example, compounds of Formula (I) and their pharmaceutically acceptable salts thereof, and deuterated derivatives of such compounds and salts can be comprised in a single pharmaceutical composition or separate pharmaceutical compositions in combination with other additional active pharmaceutical ingredient(s) (e.g., Compound II, III, or IV, or its pharmaceutically acceptable salt thereof, or a deuterated derivative of such Compound or salt). Such pharmaceutical compositions can be administered once daily or multiple times daily, such as twice daily. In some embodiments, the disclosure features a pharmaceutical composition comprising at least one compound chosen from any of the compounds disclosed herein and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound II and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound II and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from the novel compounds disclosed herein and pharmaceutically acceptable salts thereof, at least one compound chosen from Compound III and pharmaceutically acceptable salts thereof, at least one compound chosen from Compound IV and pharmaceutically acceptable salts thereof, and at least one pharmaceutically acceptable carrier.

In some embodiments, pharmaceutical compositions disclosed herein comprise at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises (i) a compound of Formulae (I), (II-A), (II-B), (III-A), (III-B), (IV-A), (IV-B), (IV-C), (V-A), (V-B), (VI-A), (VI-B), (VI-C), and (VI-D), or a pharmaceutically acceptable salt thereof, or a deuterated derivative of such compound or salt; and (ii) at least two additional active pharmaceutical ingredients, one of which is a CFTR corrector and one of which is a CFTR potentiator.

In some embodiments, at least one additional active pharmaceutical ingredient is selected from mucolytic agents, bronchodialators, antibiotics, anti-infective agents, and anti-inflammatory agents.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure, including a pharmaceutical composition comprising combinations described previously, can be employed in combination therapies; that is, the compositions can be administered concurrently with, prior to, or subsequent to, at least one additional active pharmaceutical ingredient or medical procedures.

Pharmaceutical compositions comprising these combinations are useful for treating cystic fibrosis.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

In some embodiments, the methods of the disclosure employ administering to a patient in need thereof at least one compound chosen from any of the compounds of Formula I and pharmaceutically acceptable salts thereof, and at least one compound chosen from Compound II, Compound III, Compound IV, and pharmaceutically acceptable salts of any of the foregoing.

Any suitable pharmaceutical compositions known in the art can be used for the novel compounds disclosed herein, Compound II, Compound III, Compound IV, and pharmaceutically acceptable salts thereof. Some exemplary pharmaceutical compositions for Compound II and its pharmaceutically acceptable salts can be found in WO 2011/119984 and WO 2014/015841, all of which are incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, all of which are incorporated herein by reference. Exemplary compositions comprising Compound III-d and its pharmaceutically acceptable salts can be found in, e.g., WO 2014/078842 and WO2018/227049, incorporated herein by reference. Some exemplary pharmaceutical compositions for Compound IV and its pharmaceutically acceptable salts can be found in WO 2010/037066, WO 2011/127241, WO 2013/112804, and WO 2014/071122, all of which are incorporated herein by reference.

In some embodiments, a pharmaceutical composition comprising at least one compound chosen from the novel compounds disclosed herein and pharmaceutically acceptable salts thereof is administered with a pharmaceutical composition comprising Compound II and Compound III. Pharmaceutical compositions comprising Compound II and Compound III are disclosed in PCT Publication No. WO 2015/160787, incorporated herein by reference. An exemplary embodiment is shown in the following Table 2:

TABLE 2

Exemplary Tablet Comprising 100 mg Compound II and 150 mg Compound III.

| | Ingredient | Amount per tablet (mg) |
|---|---|---|
| Intra-granular | Compound II SDD (spray dried dispersion) (80 wt % Compound II, 20 wt % HPMC) | 125 |
| | Compound III SDD (80 wt % Compound III, 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadry | 17.7 |
| Total coated Tablet | | 609.6 |

In some embodiments, a pharmaceutical composition comprising at least one compound chosen from the novel compounds disclosed herein and pharmaceutical salts thereof is administered with a pharmaceutical composition comprising Compound III. Pharmaceutical compositions comprising Compound III are disclosed in PCT Publication No. WO 2010/019239, incorporated herein by reference. An exemplary embodiment is shown in the following Table 3:

TABLE 3

Ingredients for Exemplary Tablet of Compound III

| Tablet Formulation | Percent Dose % Wt./Wt. | Dose (mg) | Batch (g) |
|---|---|---|---|
| Compound III SDD (80 wt % Compound III, 19.5 wt % HPMCAS-HG; 0.5 wt % sodium lauryl sulfate) | 34.09% | 187.5 | 23.86 |
| Microcrystalline cellulose | 30.51% | 167.8 | 21.36 |
| Lactose | 30.40% | 167.2 | 21.28 |
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

Additional pharmaceutical compositions comprising Compound III are disclosed in PCT Publication No. WO 2013/130669, incorporated herein by reference. Exemplary mini-tablets (~2 mm diameter, ~2 mm thickness, each mini-tablet weighing about 6.9 mg) was formulated to have approximately 50 mg of Compound III per 26 mini-tablets and approximately 75 mg of Compound III per 39 mini-tablets using the amounts of ingredients recited in Table 4, below.

TABLE 4

Ingredients for mini-tablets for 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Compound III SDD (80 wt % Compound III, 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

In some embodiments, the pharmaceutical compositions are a tablet. In some embodiments, the tablets are suitable for oral administration.

The compounds, pharmaceutically acceptable salts thereof, and deuterated analogs of any of the foregoing, and pharmaceutical compositions, of this disclosure, either in monotherapies or in combo-therapies are useful for treating cystic fibrosis.

In some embodiments, disclosed herein are methods of treating, lessening the severity of, or symptomatically treating cystic fibrosis in a patient comprising administering an effective amount of a compound, pharmaceutically acceptable salt thereof, or a deuterated analog of any of the foregoing; or a pharmaceutical composition, of this disclosure to a patient, such as a human, wherein said patient has cystic fibrosis. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation.

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance. Table C below includes a non-exclusive list of CFTR minimal function mutations, which are detectable by an FDA-cleared genotyping assay. In some embodiments, a mutation is considered a MF mutation if it meets at least 1 of the following 2 criteria:

biological plausibility of no translated protein (genetic sequence predicts the complete absence of CFTR protein), or in vitro testing that supports lack of responsiveness to Compound II, Compound III or the combination of Compound II and Compound III, and evidence of clinical severity on a population basis (as reported in large patient registries).

In some embodiments, the minimal function mutations are those that result in little-to-no functioning CFTR protein and are not responsive in vitro to Compound II, Compound III, or the combination of Compound II and Compound III.

In some embodiments, the minimal function mutations are those that are not responsive in vitro to Compound II, Compound III, or the combination of Compound II and Compound III. In some embodiments, the minimal function mutations are mutations based on in vitro testing met the following criteria in in vitro experiments:
baseline chloride transport that was <10% of wildtype CFTR, and
an increase in chloride transport of <10% over baseline following the addition of Compound II, Compound III, or Compound II/Compound III in the assay.

In some embodiments, patients with at least one minimal function mutation exhibit evidence of clinical severity as defined as:
average sweat chloride>86 mmol/L, and
prevalence of pancreatic insufficiency (PI)>50%.

Patients with an F508del/minimal function genotype are defined as patients that are heterozygous F508del-CFTR with a second CFTR allele containing a minimal function mutation. In some embodiments, patients with an F508del/minimal function genotype are patients that are heterozygous F508del-CFTR with a second CFTR allele containing a mutation that results in a CFTR protein with minimal CFTR function (little-to-no functioning CFTR protein) and that is not responsive in vitro to Compound II, Compound III, or the combination of Compound II and Compound III.

In some embodiments, minimal function mutations can be determined using 3 major sources:
biological plausibility for the mutation to respond (i.e., mutation class)
evidence of clinical severity on a population basis (per CFTR2 patient registry; accessed on 15 Feb. 2016)
average sweat chloride>86 mmol/L, and
prevalence of pancreatic insufficiency (PI)>50%
in vitro testing
mutations resulting in baseline chloride transport<10% of wild-type CFTR were considered minimal function
mutations resulting in chloride transport<10% of wild-type CFTR following the addition of Compound II and/or Compound III were considered nonresponsive.

As used herein, a "residual function mutation" referred to are Class II through V mutations that have some residual chloride transport and result in a less severe clinical phenotype. Residual function mutations are mutations in the CFTR gene that result in reduced protein quantity or function at the cell surface which can produce partial CFTR activity.

Non-limiting examples of CFTR gene mutations known to result in a residual function phenotype include a CFTR residual function mutation selected from 2789+5G→A, 3849+10kbC→T, 3272-26A→G, 711+3A→G, E56K, P67L, R74W, D110E, D1110H, R117C, L206W, R347H, R352Q, A455E, D579G, E831X, S945L, S977F, F1052V, R1070W, F1074L, D1152H, D1270N, E193K, and K1060T. For example, CFTR mutations that cause defective mRNA splicing, such as 2789+507 result in reduced protein synthesis, but deliver some functional CFTR to the surface of the cell to provide residual function. Other CFTR mutations that reduce conductance and/or gating, such as R117H, result in a normal quantity of CFTR channels at the surface of the cell, but the functional level is low, resulting in residual function. In some embodiments, the CFTR residual function mutation is selected from R117H, S1235R, I1027T, R668C, G576A, M470V, L997F, R75Q, R1070Q, R31C, D614G, G1069R, R1162L, E56K, A1067T, E193K, and K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, and A1067T.

Residual CFTR function can be characterized at the cellular (in vitro) level using cell based assays, such as an FRT assay (Van Goor, F. et al. (2009) PNAS Vol. 106, No. 44, 18825-18830; and Van Goor, F. et al. (2011) PNAS Vol. 108, No. 46, 18843-18846), to measure the amount of chloride transport through the mutated CFTR channels. Residual function mutations result in a reduction but not complete elimination of CFTR dependent ion transport. In some embodiments, residual function mutations result in at least about 10% reduction of CFTR activity in an FRT assay. In some embodiments, the residual function mutations result in up to about 90% reduction in CFTR activity in an FRT assay.

Patients with an F508del/residual function genotype are defined as patients that are heterozygous F508del-CFTR with a second CFTR allele that contains a mutation that results in reduced protein quantity or function at the cell surface which can produce partial CFTR activity.

Patients with an F508del/gating mutation genotype are defined as patients that are heterozygous F508del-CFTR with a second CFTR allele that contains a mutation associated with a gating defect and clinically demonstrated to be responsive to Compound III. Examples of such mutations include: G178R, S549N, S549R, G551D, G551S, G1244E, S1251N, S1255P, and G1349D.

In some embodiments, the methods of treating, lessening the severity of, or symptomatically treating cystic fibrosis disclosed herein are each independently produces an increase in chloride transport above the baseline chloride transport of the patient.

In some embodiments, in the methods of treating, lessening the severity of, or symptomatically treating cystic fibrosis disclosed herein, the patient is heterozygous for F508del, and the other CFTR genetic mutation is any CF-causing mutation. In some embodiments, the patient is heterozygous for F508del, and the other CFTR genetic mutation is any CF-causing mutation, and is expected to be and/or is responsive to any of the novel compounds disclosed herein, such as a Compound of Formula (I), Compound II, Compound III and/or Compound IV genotypes based on in vitro and/or clinical data. In some embodiments, the patient is heterozygous for F508del, and the other CFTR genetic mutation is any CF-causing mutation, and is expected to be and/or is responsive to any combinations of (i) the novel compounds disclosed herein, such as a Compound of Formula (I), and (ii) Compound II, and/or Compound III and/or Compound IV genotypes based on in vitro and/or clinical data.

In some embodiments, in the methods of treating, lessening the severity of, or symptomatically treating cystic fibrosis disclosed herein, the patient possesses a CFTR genetic mutation selected from any of the mutations listed in Table A.

TABLE A

CF Mutations

078delT
1078delT
11234V
1154insTC
1161delC
1213delT
1248+1G→A
1249−1G→A
124del23bp
1259insA
1288insTA
1341+1G->A
1342−2A->C
1461ins4
1471delA
1497delGG
1507del
1525−1G→A
1525−2A→G
1548delG
1577delTA
1609del CA
1677delTA
1716G/A
1717−1G→A
1717−8G→A
1782delA
1811+1.6kbA->G
1811+1G->C
1811+1.6kbA→G
1811+1G→C
1812−1G->A
1898+1G->A
1812−1G→A
1824delA
182delT
1119delA
185+1G→T
1898+1G->T
1898+1G→A
1898+1G→C
1898+3A->G
1898+5G->T
1924del7
1949del84
2043delG
2055del9→A
2105−2117del13insAGAAA
2118del14
2143delT
2183AA->G+
2183AA→G
2183AA→G$^a$
2183delAA->G#
2183delAA→G
2184delA
2184insA
2307insA
2347delG
2556insAT
2585delT
2594delGT
2622+1G->A
2622+lG->A
2659delC
2711delT
271delT
2721del11
2732insA
2789+2insA
2789+5G→A
2790−1G->C
2790−lG->C
2869insG
2896insAG
2942insT
2957delT

TABLE A-continued

CF Mutations

296+1G→A
2991del32
3007delG
3028delA
3040G→C
306insA
306insA
1138insG
3120G→A
3121−1G→A
3121−2A→G
3121-977_3499+248del2515
3132delTG
3141del9
3171delC
3195del6
3199del6
3272−26A->G
3500−2A→G
3600+2insT
365−366insT
3659delC
3667ins4
3737delA
3791delC
3821delT
3849+10kbC→T
3849+lOkbC->T
3850−1G→A
3850−3T->G
3850−lG->A
3876delA
3878delG
3905InsT
3905insT
394delTT
4005+1G->A
4005+2T->C
4005+1G→A
4005+lG->A
4010del4
4015delA
4016insT
4021dupT
4040delA
405+1G→A
405+3A→C
405+lG->A
406−1G→A
406−lG->A
4209TGTT->A
4209TGTT→AA
4279insA
4326delTC
4374+1G→T
4374+lG->T
4382delA
4428insGA
442delA
457TAT→G
541delC
574delA
5T
621+1G→T
621+3A->G
663delT
663delT
1548delG
675del4
711+1G->T
711+3A->G
711+1G→T
711+3A→G
711+5G→A
712−1G->T
7T
852del22
935delA TABLE A-continued CF Mutations 991del5
A1006E
A120T
A234D
A349V
A455E
A613T
A46D
A46Db
A559T
A559Tb
A561E
C276X
C524R
C524X
CFTRdel2,3
CFTRdele22-23
D110E
D110H
D1152H
D1270N
D192G
D443Y
D513G
D579G
D614G
D836Y
D924N
D979V
E1104X
E116K
E1371X
E193K
E193X
E403D
E474K
E56K
E585X
E588V
E60K
E822K
E822X
E831X
E92K
E92X
F1016S
F1052V
F1074L
F1099L
F191V
F311del
F311L
F508C
F508del
F575Y
G1061R
G1069R
G1244E
G1249R
G126D
G1349D
G149R
G178R
G194R
G194V
G27R
G27X
G314E
G330X
G458V
G463V
G480C
G542X
G550X
G551D
G551S
G576A
G622D TABLE A-continued CF Mutations G628R
G628R(G->A)
G970D
G673X
G85E
G91R
G970R
G970R
H1054D
H1085P
H1085R
H1375P
H139R
H199R
H199Y
H609R
H939R
I1005R
I1027T
I1234V
I1269N
I1366N
I148T
I175V
I3336K
I502T
I506S
I506T
I507del
I507del
I601F
I618T
I807M
I980K
IVS14b+5G->A
K710X
K710X
K710X
L102R
L1065P
L1077P
L1077Pb
L1254X
L1324P
L1335P
L138ins
L1480P
L15P
L165S
L206W
L218X
L227R
L320V
L346P
L453S
L467P
L467Pb
L558S
L571S
L732X
L927P
L967S
L997F
M1101K
M1101R
M152V
M1T
M1V
M265R
M470V
M952I
M952T
N1303K
P205S
P574H
P5L
P67L
P750L

TABLE A-continued

CF Mutations

P99L
Q1100P
Q1291H
Q1291R
Q1313X
Q1382X
Q1411X
Q1412X
Q220X
Q237E
Q237H
Q452P
Q290X
Q359K/T360K
Q39X
Q414
Q414X
E585X
Q493X
Q525X
Q552X
Q685X
Q890X
Q890X
Q98R
Q98X
R1066C
R1066H
R1066M
R1070Q
R1070W
R1102X
R1158X
R1162L
R1162X
R117C
R117G
R117H
R117L
R117P
R1283M
R1283S
R170H
R258G
R31C
R31L
R334L
R334Q
R334W
R347H
R347L
R347P
R352Q
R352W
R516G
R553Q
R553X
R560K
R560S
R560T
R668C
R709X
R74W
R751L
R75Q
R75X
R764X
R792G
R792X
R851X
R933G
S1118F
S1159F
S1159P
S1196X
S1235R
S1251N
S1255P

TABLE A-continued

CF Mutations

S1255X
S13F
S341P
S434X
S466X
S489X
S492F
S4X
S549N
S549R
S549R(A->C)
S549R(T->G)
S589N
S737F
S912L
S912X
S945L
S977F
T1036N
T1053I
T1246I
T338I
T604I
V1153E
V1240G
V1293G
V201M
V232D
V456A
V456F
V520F
V562I
V754M
W1089X
W1098C
W1098R
W1098X
W1204X
W1282R
W1282X
W361R
W401X
W496X
W57G
W57R
W57X
W846X
Y1014C
Y1032C
Y1092X
Y109N
Y122X
Y161D
Y161S
Y563D
Y563N
Y569C
Y569D
Y569Db
Y849X
Y913C
Y913X

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-

1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→G, 1949del84, 3141del9, 3195del6, 3199del6, 3905InsT, 4209TGTT→A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, I980K, L102R, L1324P, L1335P, L138ins, L1480P, L1SP, L165S, L320V, L346P, L453S, L571S, L967S, M1101R, M152V, M1T, M1V, M265R, M9521, M952T, P574H, PSL, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A→C), S549R (T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, the patient has at least one combination mutation chosen from: G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G.

In some embodiments, the patient has at least one combination mutation chosen from: 1949del84, 3141del9, 3195del6, 3199del6, 3905InsT, 4209TGTT→A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, I980K, L102R, L1324P, L1335P, L138ins, L1480P, L1SP, L165S, L320V, L346P, L453S, L571S, L967S, M1101R, M152V, M1T, M1V, M265R, M9521, M952T, P574H, PSL, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A→C), S549R(T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, in the methods of treating, lessening the severity of, or symptomatically treating cystic fibrosis disclosed herein, the patient possesses a CFTR genetic mutation G551D. In some embodiments, the patient is homozygous for the G551D genetic mutation. In some embodiments, the patient is heterozygous for the G551D genetic mutation. In some embodiments, the patient is heterozygous for the G551D genetic mutation, having the G551D mutation on one allele and any other CF-causing mutation on the other allele. In some embodiments, the patient is heterozygous for the G551D genetic mutation on one allele and the other CF-causing genetic mutation on the other allele is any one of F508del, G542X, N1303K, W1282X, R117H, R553X, 1717-1G→A, 621+1G→T, 2789+5G→A, 3849+10kbC→T, R1162X, G85E, 3120+1G→A, 41507, 1898+1G→A, 3659delC, R347P, R560T, R334W, A455E, 2184delA, or 711+1G→T. In some embodiments, the patient is heterozygous for the G551D genetic mutation, and the other CFTR genetic mutation is F508del. In some embodiments, the patient is heterozygous for the G551D genetic mutation, and the other CFTR genetic mutation is R117H.

In some embodiments, in the methods of treating, lessening the severity of, or symptomatically treating cystic fibrosis disclosed herein, the patient possesses a CFTR genetic mutation F508del. In some embodiments, the patient is homozygous for the F508del genetic mutation. In some embodiments, the patient is heterozygous for the F508del genetic mutation wherein the patient has the F508del genetic mutation on one allele and any CF-causing genetic mutation on the other allele. In some embodiments, the patient is heterozygous for F508del, and the other CFTR genetic mutation is any CF-causing mutation, including, but not limited to G551D, G542X, N1303K, W1282X, R117H, R553X, 1717-1G→A, 621+1G→T, 2789+5G→A, 3849+10kbC→T, R1162X, G85E, 3120+1G→A, 41507, 1898+1G→A, 3659delC, R347P, R560T, R334W, A455E, 2184delA, or 711+1G→T. In some embodiments, the patient is heterozygous for F508del, and the other CFTR genetic mutation is G551D. In some embodiments, the patient is heterozygous for F508del, and the other CFTR genetic mutation is R117H.

In some embodiments, the patient has at least one combination mutation chosen from:
D443Y; G576A; R668C,
F508C; S1251N,
G576A; R668C,
G970R; M470V,
R74W; D1270N,
R74W; V201M, and
R74W; V201M; D1270N.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V and G1069R. In some embodiments, the patient possesses a CFTR genetic mutation selected from G178R, G551S, G970R, G1244E, S1255P, G1349D, S549N, S549R and S1251N. In some embodiments, the patient possesses a CFTR genetic mutation selected from E193K, F1052V and G1069R. In some embodiments, the method produces an increase in chloride transport relative to baseline chloride transport of the patient of the patient.

In some embodiments, in the methods of treating, lessening the severity of, or symptomatically treating cystic fibrosis disclosed herein, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H.

In some embodiments, the patient possesses a CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In some embodiments, the patient possesses a CFTR genetic mutation selected from 1717-1G→A, 1811+1.6kbA→G, 2789+5G→A, 3272-26A→G and 3849+10kbC→T. In some embodiments, the patient possesses a CFTR genetic mutation selected from 2789+5G→A and 3272-26A→G.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and human CFTR mutations selected from F508del, R117H, and G551D.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→G, and a CFTR mutation selected from F508del, R117H, and G551D; and a CFTR mutations selected from F508del, R117H, and G551D.

In some embodiments, the patient possesses a CFTR genetic mutation selected from G178R, G551S, G970R, G1244E, S1255P, G1349D, S549N, S549R, S1251N, E193K, F1052V and G1069R, and a human CFTR mutation selected from F508del, R117H, and G551D. In some embodiments, the patient possesses a CFTR genetic mutation selected from G178R, G551S, G970R, G1244E, S1255P, G1349D, S549N, S549R and S1251N, and a human CFTR mutation selected from F508del, R117H, and G551D.
In some embodiments, the patient possesses a CFTR genetic mutation selected from E193K, F1052V and G1069R, and a human CFTR mutation selected from F508del, R117H, and G551D.

In some embodiments, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H, and a human CFTR mutation selected from F508del, R117H, and G551D.

In some embodiments, the patient possesses a CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D. In some embodiments, the patient possesses a CFTR genetic mutation selected from 1717-1G→A, 1811+1.6kbA→G, 2789+5G→A, 3272-26A→G and 3849+10kbC→T, and a human CFTR mutation selected from F508del, R117H, and G551D. In some embodiments, the patient possesses a CFTR genetic mutation selected from 2789+5G→A and 3272-26A→G, and a human CFTR mutation selected from F508del, R117H.

In some embodiments, the patient is heterozygous having a CF-causing mutation on one allele and a CF-causing mutation on the other allele. In some embodiments, the patient is heterozygous for F508del, and the other CFTR genetic mutation is any CF-causing mutation, including, but not limited to F508del on one CFTR allele and a CFTR mutation on the second CFTR allele that is associated with minimal CFTR function, residual CFTR function, or a defect in CFTR channel gating activity. In some embodiments, the CF-causing mutation is selected from Table A. In some embodiments, the CF-causing mutation is selected from Table B. In some embodiments, the CF-causing mutation is selected from Table C. In some embodiments, the CF-causing mutation is selected from FIG. 2. In some embodiments, the patient is heterozygous having a CF-causing mutation on one CFTR allele selected from the mutations listed in the table from FIG. 2 and a CF-causing mutation on the other CFTR allele is selected from the CFTR mutations listed in Table B:

TABLE B

| CFTR Mutations | | |
| --- | --- | --- |
| Q39X | 1248+1G→A | R560S |
| W57X | 1341+1G→A | A561E |
| E60X | 1717-1G→A | Y569D |
| R75X | 1811+1.6kbA→G | L1065P |
| E92X | 1811+1G→C | R1066C |
| Q98X | 1812-1G→A | R1066M |
| Y122X | 1898+1G→A | L1077P |
| L218X | 2622+1G→A | H1085R |
| Q220X | 3120+1G→A | M1101K |
| C276X | 3120G→A | N1303K |
| Q290X | 3850-1G→A | 3849+10kbC→T |
| G330X | 4005+1G→A | 3272-26A→G |

TABLE B-continued

CFTR Mutations

| | | | | | |
|---|---|---|---|---|---|
| W401X | 4374+1G→T | 711+3A→G | | Q890X | 3791delC | S549R |
| Q414X | 663delT | E56K | | S912X | CFTRdele22-23 | G551D |
| S434X | 2183AA→G | P67L | | W1089X | 457TAT→G | G551S |
| S466X | CFTRdel2,3 | R74W | | Y1092X | 2043delG | G1244E |
| S489X | 3659delC | D110E | | E1104X | 2869insG | S1251N |
| Q493X | 394delTT | D110H | | R1158X | 3600+2insT | S1255P |
| W496X | 2184insA | R117C | | R1162X | 3737delA | G1349D |
| Q525X | 3905insT | L206W | | S1196X | 4040delA | |
| G542X | 2184delA | R347H | | W1204X | 541delC | |
| Q552X | 1078delT | R352Q | | S1255X | A46D | |
| R553X | 1154insTC | A455E | | W1282X | T338I | |
| E585X | 2183delAA→G | D579G | | Q1313X | R347P | |
| G673X | 2143delT | E831X | | 621+1G→T | L927P | |
| R709X | 1677delTA | S945L | | 711+1G→T | G85E | |
| K710X | 3876delA | S977F | | 711+5G→A | S341P | |
| L732X | 2307insA | F1052V | | 712-1G→T | L467P | |
| R764X | 4382delA | R1070W | | 405+1G→A | I507del | |
| R785X | 4016insT | F1074L | | 405+3A→C | V520F | |
| R792X | 2347delG | D1152H | | 406-1G→A | A559T | |
| E822X | 3007delG | D1270N | | 621+1G→T | R560T | |
| W846X | 574delA | G178R | | | | |
| R851X | 2711delT | S549N | | | | |

TABLE C

CFTR Mutations

| Criteria | Mutation | | | | |
|---|---|---|---|---|---|
| Truncation mutations % PI > 50% and/or SwCl⁻ > 86 mmol/L no full-length protein | S4X | C276X | G542X | R792X | E1104X |
| | G27X | Q290X | G550X | E822X | R1158X |
| | Q39X | G330X | Q552X | W846X | R1162X |
| | W57X | W401X | R553X | Y849X | S1196X |
| | E60X | Q414X | E585X | R851X | W1204X |
| | R75X | S434X | G673X | Q890X | L1254X |
| | E92X | S466X | Q685X | S912X | S1255X |
| | Q98X | S489X | R709X | Y913X | W1282X |
| | Y122X | Q493X | K710X | W1089X | Q1313X |
| | E193X | W496X | L732X | Y1092X | E1371X |
| | L218X | C524X | R764X | W1098X | Q1382X |
| | Q220X | Q525X | R785X | R1102X | Q1411X |
| Splice mutations % PI > 50% and/or SwCl⁻ > 86 mmol/L no or little mature mRNA | 185+1G→T | 711+5G→A | 1717-8G→A | 2622+1G→A | 3121-1G→A |
| | 296+1G→A | 712-1G→T | 1717-1G→A | 2790-1G→C | 3500-2A→G |
| | 405+1G→A | 1248+1G→A | 1811+1G→C | 3040G→C | 3600+2insT |
| | 405+3A→C | 1249-1G→A | 1811+1.6kbA→G | (G970R) | 3850-1G→A |
| | 406-1G→A | 1341+1G→A | 1812-1G→A | 3120G→A | 4005+1G→A |
| | 621+1G→T | 1525-2A→G | 1898+1G→A | 3120+1G→A | 4374+1G→T |
| | 711+1G→T | 1525-1G→A | 1898+1G→C | 3121-2A→G | |
| Small (≤3 nucleotide) insertion/deletion (ins/del) frameshift mutations % PI > 50% and/or SwCl⁻ > 86 mmol/L garbled and/or truncated protein | 182delT | 1119delA | 1782delA | 2732insA | 3876delA |
| | 306insA | 1138insG | 1824delA | 2869insG | 3878delG |
| | 365-366insT | 1154insTC | 2043delG | 2896insAG | 3905insT |
| | 394delTT | 1161delC | 2143delT | 2942insT | 4016insT |
| | 442delA | 1213delT | 2183AA→G ᵃ | 2957delT | 4021dupT |
| | 444delA | 1259insA | 2184delA | 3007delG | 4040delA |
| | 457TAT→G | 1288insTA | 2184insA | 3028delA | 4279insA |
| | 541delC | 1471delA | 2307insA | 3171delC | 4326delTC |
| | 574delA | 1497delGG | 2347delG | 3659delC | |
| | 663delT | 1548delG | 2585delT | 3737delA | |
| | 935delA | 1609del CA | 2594delGT | 3791delC | |
| | 1078delT | 1677delTA | 2711delT | 3821delT | |
| Non-small (>3 nucleotide) insertion/deletion (ins/del) frameshift mutations % PI > 50% and/or SwCl⁻ > 86 mmol/L garbled and/or truncated protein | CFTRdele2,3 | 1461ins4 | | | 2991del32 |
| | CFTRdele22,23 | 1924del7 | | | 3667ins4 |
| | 124del23bp | 2055del9→A | | | 4010del4 |
| | 852del22 | 2105-2117del13insAGAAA | | | 4209TGTT→AA |
| | 991del5 | 2721del11 | | | |

TABLE C-continued

CFTR Mutations

| Criteria | Mutation | | | |
|---|---|---|---|---|
| Class II, III, IV mutations not responsive to Compound III alone or in combination with Compound II or Compound IV % PI > 50% and/or SwCl⁻ > 86 mmol/L AND Not responsive in vitro to Compound III alone or in combination with Compound II or Compound IV | A46D[b] G85E R347P L467P[b] I507del | V520F A559T[b] R560T R560S A561E | Y569D[b] L1065P R1066C L1077P[b] M1101K | N1303K |

Note:
% PI: percentage of F508del–CFTR heterozygous patients in the CFTR2 patient registry who are pancreatic insufficient;
SwCl⁻: mean sweat chloride of F508del–CFTR heterozygous patients in the CFTR2 patient registry
[a] Also known as 2183delAA→G.
[b] Unpublished data.

In some embodiments, the patient is: with F508del/MF (F/MF) genotypes (heterozygous for F508del and an MF mutation not expected to respond to CFTR modulators, such as Compound III); with F508del/F508del (F/F) genotype (homozygous for F508del); and/or with F508del/gating (F/G) genotypes (heterozygous for F508del and a gating mutation known to be CFTR modulator-responsive (e.g., Compound III-responsive). In some embodiments, the patient with F508del/MF (F/MF) genotypes has a MF mutation that is not expected to respond to Compound II, Compound III, and both of Compound II and Compound III. In some embodiments, the patient with F508del/MF (F/MF) genotypes has any one of the MF mutations in Table C.

In some embodiments, the patient is heterozygous for F508del, and the other CFTR genetic mutation is any CF-causing mutation, including truncation mutations, splice mutations, small (≤3 nucleotide) insertion or deletion (ins/del) frameshift mutations; non-small (>3 nucleotide) insertion or deletion (ins/del) frameshift mutations; and Class II, III, IV mutations not responsive to Compound III alone or in combination with Compound II or Compound IV.

In some embodiments, the patient is heterozygous for F508del, and the other CFTR genetic mutation is a truncation mutation. In some specific embodiments, the truncation mutation is a truncation mutation listed in Table C.

In some embodiments, the patient is heterozygous for F508del, and the other CFTR genetic mutation is a splice mutation. In some specific embodiments, the splice mutation is a splice mutation listed in Table C.

In some embodiments, the patient is heterozygous for F508del, and the other CFTR genetic mutation is a small (≤3 nucleotide) insertion or deletion (ins/del) frameshift mutation. In some specific embodiments, the small (≤3 nucleotide) insertion or deletion (ins/del) frameshift mutation is a small (≤3 nucleotide) insertion or deletion (ins/del) frameshift mutation listed in Table C.

In some embodiments compounds of Formulae (I), (II-A), (II-B), (III-A), (III-B), (IV-A), (IV-B), (IV-C), (V-A), (V-B), (VI-A), (VI-B), (VI-C), and (VI-D), and pharmaceutically acceptable salts thereof, and their deuterated, the patient is heterozygous for F508del, and the other CFTR genetic mutation is any CF-causing mutation expected to be and/or is responsive to, based on in vitro and/or clinical data, any combination of (i) a novel compound chosen from those disclosed herein (e.g., compounds of Formulae (I), (II-A), (II-B), (III-A), (III-B), (IV-A), (IV-B), (IV-C), (V-A), (V-B), (VI-A), (VI-B), (VI-C), and (VI-D), and pharmaceutically acceptable salts thereof, and their deuterated derivatives), and (ii) Compound II, and/or Compound III, and/or Compound IV.

In some embodiments, the patient is heterozygous for F508del, and the other CFTR genetic mutation is any CF-causing mutation expected to be and/or is responsive, based on in vitro and/or clinical data, to the triple combination of a novel compound chosen from those disclosed herein (e.g., derivatives), and Compound II, and Compound III.

In some embodiments, the patient is heterozygous for F508del, and the other CFTR genetic mutation is a non-small (>3 nucleotide) insertion or deletion (ins/del) frameshift mutation. In some specific embodiments, the non-small (>3 nucleotide) insertion or deletion (ins/del) frameshift mutation is a non-small (>3 nucleotide) insertion or deletion (ins/del) frameshift mutation listed in Table C.

In some embodiments, the patient is heterozygous for F508del, and the other CFTR genetic mutation is a Class II, III, IV mutations not responsive to Compound III alone or in combination with Compound II or Compound IV. In some specific embodiments, the Class II, III, IV mutations not responsive to Compound III alone or in combination with Compound II or Compound IV is a Class II, III, IV mutations not responsive to Compound III alone or in combination with Compound II or Compound IV listed in Table C.

In some embodiments, the patient is heterozygous for F508del, and the other CFTR genetic mutation is any mutation listed in Table C.

In some embodiments, the patient is heterozygous for F508del, and the other CFTR genetic mutation is any mutation, but other than F508del, listed in Table A, B, C, and FIG. 2.

In some embodiments, the patient is heterozygous for F508del, and the other CFTR genetic mutation is any mutation listed in Table A. In some embodiments, the patient is heterozygous for F508del, and the other CFTR genetic mutation is any mutation listed in Table B. In some embodiments, the patient is heterozygous for F508del, and the other CFTR genetic mutation is any mutation listed in Table C. In some embodiments, the patient is heterozygous for F508del, and the other CFTR genetic mutation is any mutation listed in FIG. 2.

In some embodiments, the patient is homozygous for F508del.

In some embodiments, the patient is heterozygous having one CF-causing mutation on one CFTR allele selected from the mutations listed in the table from FIG. 2 and another CF-causing mutation on the other CFTR allele is selected from the CFTR mutations listed in Table C.

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel.

In some embodiments, the patient is heterozygous and has an F508del mutation on one allele and a mutation on the other allele selected from Table 5:

TABLE 5

CFTR Mutations
Mutation

| | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185+1G→T | 711+5G→A | 1717−8G→A | 2622+1G→A | 3121−1G→A |
| 296+1G→A | 712−1G→T | 1717−1G→A | 2790−1G→C | 3500−2A→G |
| 296+1G→T | 1248+1G→A | 1811+1G→C | 3040G→C | 3600+2insT |
| 405+1G→A | 1249−1G→A | 1811+1.6kbA→G | (G970R) | 3850−1G→A |
| 405+3A→C | 1341+1G→A | 1811+1643G→T | 3120G→A | 4005+1G→A |
| 406−1G→A | 1525−2A→G | 1812−1G→A | 3120+1G→A | 4374+1G→T |
| 621+1G→T | 1525−1G→A | 1898+1G→A | 3121−2A→G | |
| 711+1G→T | | 1898+1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |

TABLE 5-continued

CFTR Mutations
Mutation

| | | | | |
|---|---|---|---|---|
| 365–366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |
| CFTRdele1 | CFTRdele16–17b | | 1461ins4 | |
| CFTRdele2 | CFTRdele17a,17b | | 1924del7 | |
| CFTRdele2,3 | CFTRdele17a–18 | | 2055del9→A | |
| CFTRdele2–4 | CFTRdele19 | | 2105–2117del13insAGAAA | |
| CFTRdele3–10,14b–16 | CFTRdele19–21 | | 2372del8 | |
| CFTRdele4–7 | CFTRdele21 | | 2721del11 | |
| CFTRdele4–11 | CFTRdele22–24 | | 2991del32 | |
| CFTR50kbdel | CFTRdele22,23 | | 3667ins4 | |
| CFTRdup6b–10 | 124del23bp | | 4010del4 | |
| CFTRdele11 | 602del14 | | 4209TGTT→AA | |
| CFTRdele13,14a | 852del22 | | | |
| CFTRdele14b–17b | 991del5 | | | |
| A46D | V520F | Y569D | N1303K | |
| G85E | A559T | L1065P | | |
| R347P | R560T | R1066C | | |
| L467P | R560S | L1077P | | |
| I507del | A561E | M1101K | | |

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure includes deuterated derivatives of the novel compounds disclosed herein and of their pharmaceutically acceptable salts. Non-limiting examples of deuterated compounds are disclosed in FIG. 1.

In some embodiments, Compound III-d as used herein includes the deuterated compound disclosed in U.S. Pat. No. 8,865,902 (which is incorporated herein by reference) as:

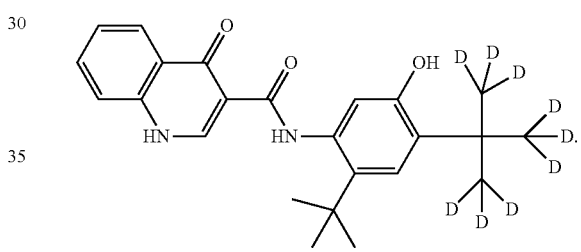

Clinical efficacy of Compound III-d in combination with other CFTR correctors, including combinations with Compound II, have been described in Davies et al., New Engl. J. Med. 379(17):1599-1611 (2018) and Davies et al., New Engl. J. Med. 379(17):1612-1620 (2018).

Exemplary embodiments of the disclosure include: The novel compounds disclosed herein (e.g., compounds of Formulae (I), (II-A), (II-B), (III-A), (III-B), (IV-A), (IV-B), (IV-C), (V-A), (V-B), (VI-A), (VI-B), (VI-C), and (VI-D), pharmaceutically acceptable salts thereof, and deuterated derivatives of any of the foregoing, including the compounds in FIG. 1 and those specifically depicted herein) can be prepared by suitable methods known in the art. For example, they can be prepared in accordance with the exemplary syntheses described below in the Examples. For example, deuterated derivatives of the novel compounds of Formulae (I), (II-A), (II-B), (III-A), (III-B), (IV-A), (IV-B), (IV-C), (V-A), (V-B), (VI-A), (VI-B), (VI-C), and (VI-D) and pharmaceutically acceptable salts thereof can be prepared in a similar manner as those for compounds of Formulae (I), (II-A), (II-B), (III-A), (III-B), (IV-A), (IV-B), (IV-C), (V-A), (V-B), (VI-A), (VI-B), (VI-C), and (VI-D) and pharmaceutically acceptable salts thereof by employing intermediates and/or reagents where one or more hydrogen atoms are replaced with deuterium. For example, see T. G. Gant "Using deuterium in drug discovery: leaving the label in the drug," J. Med. Chem. 2014, 57, 3595-3611, the relevant portions of which are incorporated herein by reference.

In some embodiments, compounds disclosed herein and pharmaceutically acceptable salts thereof, and deuterated derivatives of any of the foregoing are prepared as depicted in Schemes 1-12, wherein the variables therein are each and independently are as those for Formula (I). Suitable condition(s) known in the art can be employed for each step depicted in the schemes. The methods disclosed herein can be used to prepare compounds of Formulae (I), (II-A), (II-B), (III-A), (III-B), (IV-A), (IV-B), (IV-C), (V-A), (V-B), (VI-A), (VI-B), (VI-C), and (VI-D), and any compounds depicted in Table 5 and FIG. 1, salts thereof, or deuterated derivatives of any of the foregoing.

In some embodiments, as shown in Scheme 1, the methods comprise reacting a compound of Formula (A) or a salt thereof with a compound of Formula (B) or a salt thereof to generate a compound of Formula (Y), a salt thereof, or a deuterated derivative of any of the foregoing. The reaction of Formula (A) and Formula (B) can be performed under any suitable coupling reaction between carboxylic acid and sulfonamide, such as with CDI. In some embodiments, the coupling reaction is performed in the presence of a base, such as DBU.

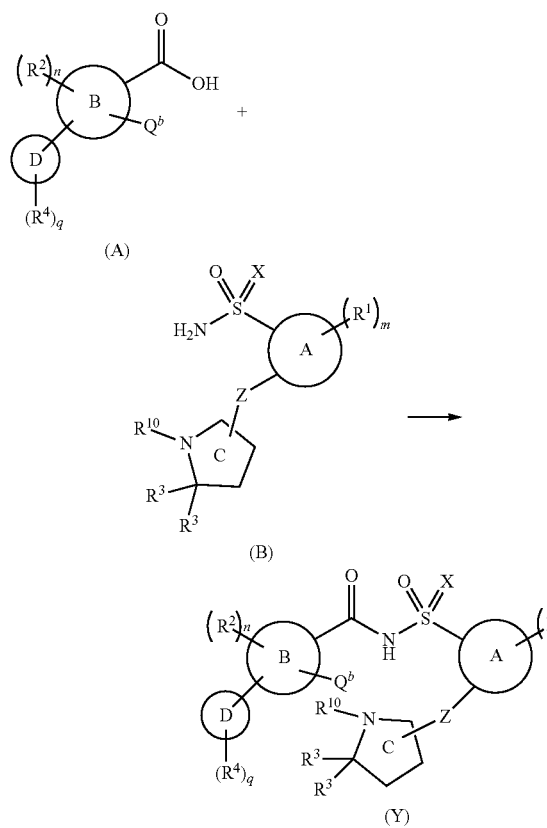

In some embodiments, as shown in Scheme 2, the methods comprise deprotection of a compound of Formula (Y) to generate a compound of Formula (Y-1), a salt thereof, or a deuterated derivative of any of the foregoing. The deprotection of Formula (Y) can be performed under any suitable deprotection conditions, which are readily apparent to a person of skill in the art depending on the protecting group $R^{10}$. In some embodiments, the protecting group $R^{10}$ is Boc, and the deprotection conditions are acidic. In some embodiments, as shown in Scheme 2, the methods comprise reacting a compound of Formula (Y-1) to generate a compound of Formula (I), a salt thereof, or a deuterated derivative of any of the foregoing. The reaction of Formula (Y-1) can be performed under any suitable coupling reaction between an amine and halogen. In some embodiments, this coupling reaction is performed in the presence of a base, such as $K_2CO_3$.

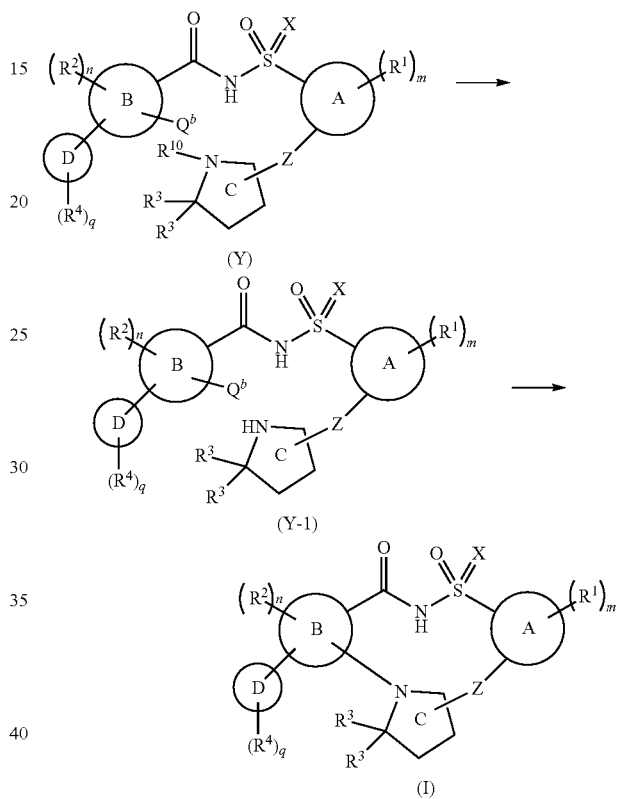

In some embodiments, as shown in Scheme 3, the methods comprise reacting a compound of Formula (A) or a salt thereof with a compound of Formula (B-2) or a salt thereof to generate a compound of Formula (Y-2), a salt thereof, or a deuterated derivative of any of the foregoing. The reaction of Formula (A) and Formula (B-2) can be performed under any suitable coupling reaction between a carboxylic acid and sulfonamide, such as with CDI. In some embodiments, the coupling reaction is performed in the presence of a base, such as DBU.

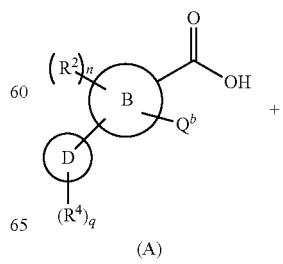

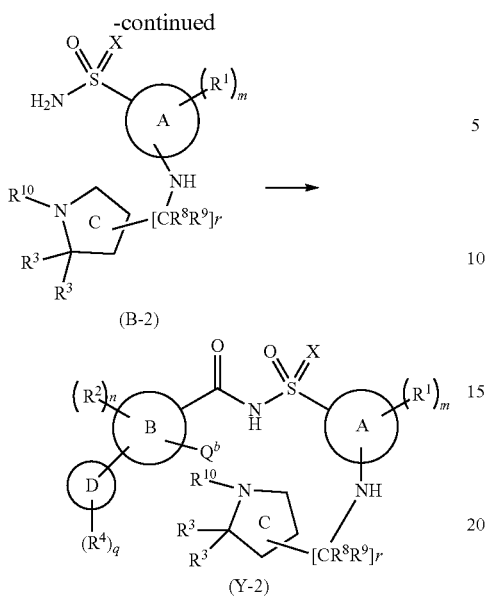

In some embodiments, as shown in Scheme 4, the methods comprise reacting a compound of Formula (D) or a salt thereof with a compound of Formula (E-2) or a salt thereof to generate a compound of Formula (B-2), a salt thereof, or a deuterated derivative of any of the foregoing. The reaction of Formula (D) and Formula (E-2) can be performed under any suitable coupling reaction between an amine and Rd.

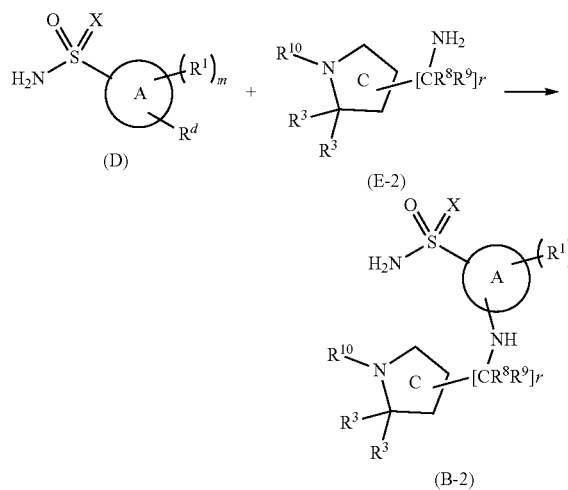

In some embodiments, as shown in Scheme 5, the methods comprise reacting a compound of Formula (A) or a salt thereof with a compound of Formula (B-3) or a salt thereof to generate a compound of Formula (Y-3), a salt thereof, or a deuterated derivative of any of the foregoing. The reaction of Formula (A) and Formula (B-3) can be performed under any suitable coupling reaction between a carboxylic acid and sulfonamide, such as with CDI. In some embodiments, the coupling reaction is performed in the presence of a base, such as DBU.

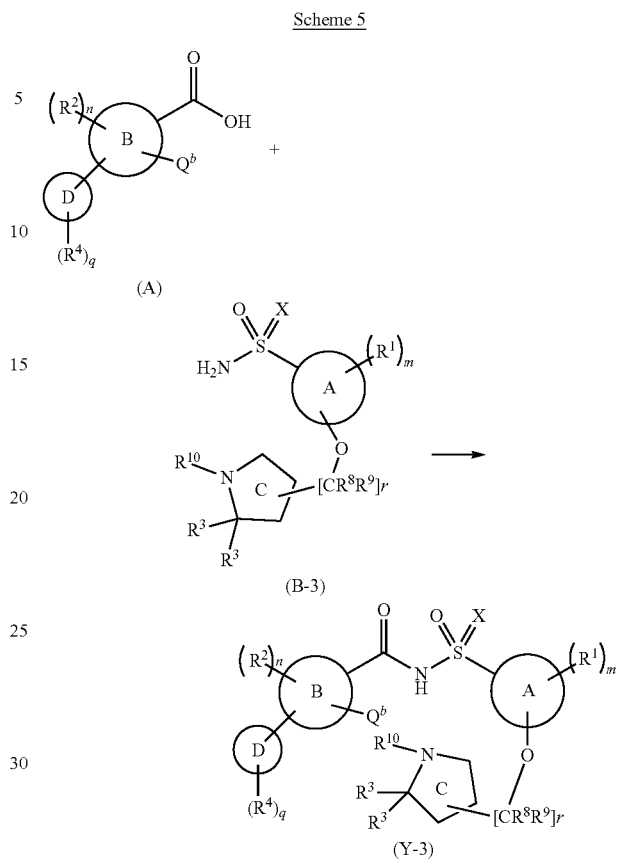

In some embodiments, as shown in Scheme 6, the methods comprise reacting a compound of Formula (D) or a salt thereof with a compound of Formula (E-3) or a salt thereof to generate a compound of Formula (B-3), a salt thereof, or a deuterated derivative of any of the foregoing. The reaction of Formula (A) and Formula (B-3) can be performed under any suitable coupling reaction between an alcohol and $R^d$.

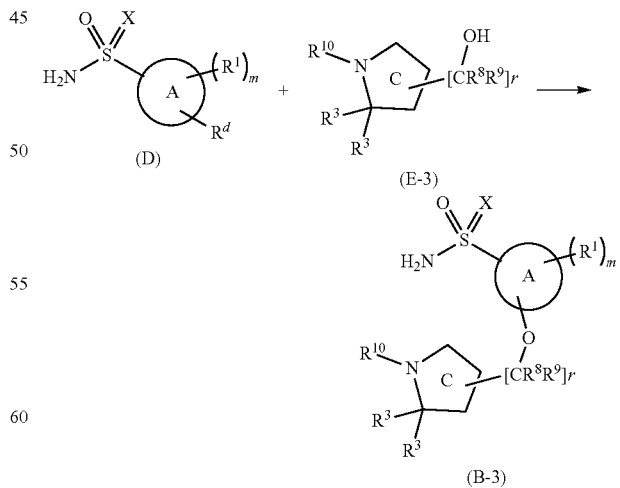

In some embodiments, as shown in Scheme 7, the methods comprise reacting a compound of Formula (Z-1) with a compound of Formula (X) to generate a compound of Formula (I), a salt thereof, or a deuterated derivative of any of the foregoing. The reaction of Formula (Z-1) with a compound of Formula (X) can be performed under any suitable coupling reaction between an nitrogen and halogen.

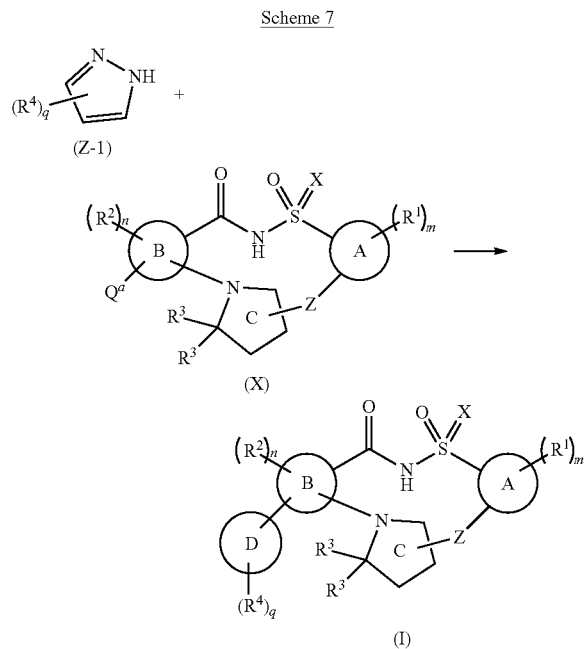

In some embodiments, as shown in Scheme 8, the methods comprise reacting a compound of Formula (Z-1) with a compound of Formula (X-1) to generate a compound of Formula (IV-C), a salt thereof, or a deuterated derivative of any of the foregoing. The reaction of Formula (Z-1) with a compound of Formula (X-1) can be performed under any suitable coupling reaction between a nitrogen and halogen.

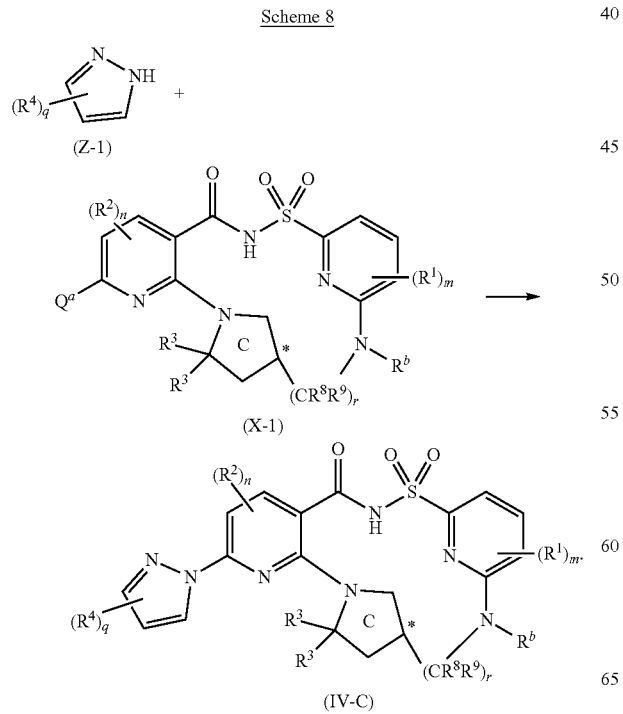

In some embodiments, as shown in Scheme 9, the methods comprise reacting a compound of Formula (F) or a salt thereof with a compound of Formula (G) or a salt thereof to generate a compound of Formula (H), a salt thereof, or a deuterated derivative of any of the foregoing. The reaction of Formula (F) and Formula (G) can be performed under any suitable reaction between an anide and sulfur atom, such as with bromine. In some embodiments, the reaction is performed in the presence of a base, such as pyridine. A compound of Formula (H) or a salt thereof can be oxidized to form a compound of Formula (J) or a salt thereof. In some embodiment, the oxidizing agent is meta-chloroperoxybenzoic acid (m-CPBA).

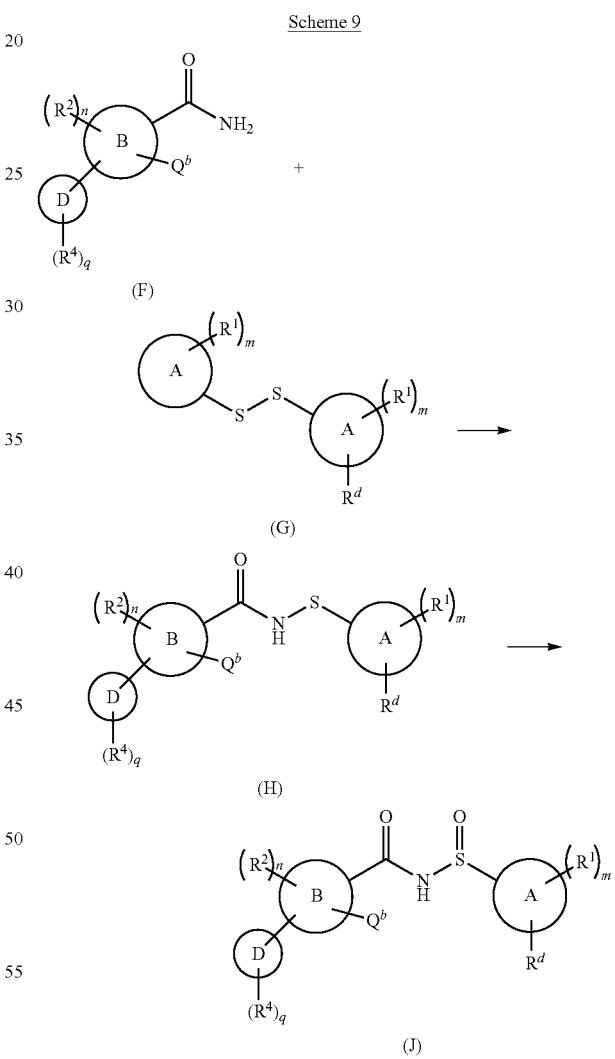

In some embodiments, as shown in Scheme 10, the methods comprise reaction of a compound of Formula (J) with a compound of Formula (L) to generate a compound of Formula (M), a salt thereof, or a deuterated derivative of any of the foregoing. In some embodiments, the reaction is performed in the presence of a base, such as sodium hydride.

Scheme 10

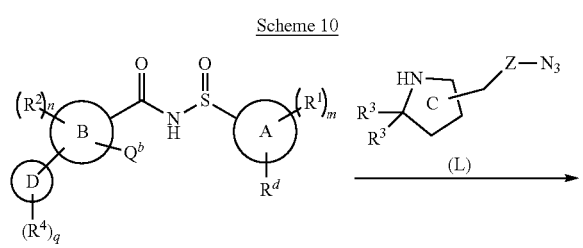

In some embodiments, as shown in Scheme 11, the methods comprise reacting a compound of Formula (M) or a salt thereof with an amine to produce a compound of Formula (N), a salt thereof, or a deuterated derivative of any of the foregoing, wherein X is NH or an $N(C_1\text{-}C_4 \text{ alkyl})$. In some embodiments, the reaction of Formula (M) and the amine can be performed in the presence of N-chlorosuccinimide. The compound of Formula (N) can be converted to a compound of Formula (O), a salt thereof, or a deuterated derivative of any of the foregoing. In some embodiments, the reaction is performed under reducing conditions. In some embodiments, the reaction is performed in the presence of palladium on carbon and hydrogen.

Scheme 11

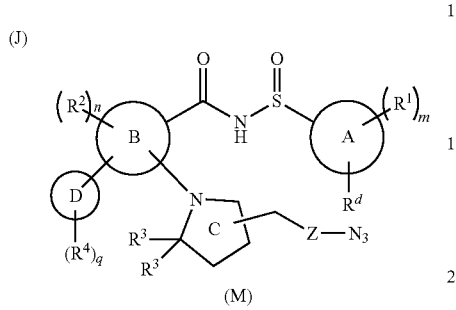

In some embodiments, as shown in Scheme 12, the methods comprise reacting a compound of Formula (O) or a salt thereof to generate a compound of Formula (P), a salt thereof, or a deuterated derivative of any of the foregoing. In some embodiments, the reaction of Formula (O) can be performed in the presence of a base. In some embodiments, the base is triethylamine. In some embodiments, the reaction of Formula (O) can be performed with heating.

Scheme 12

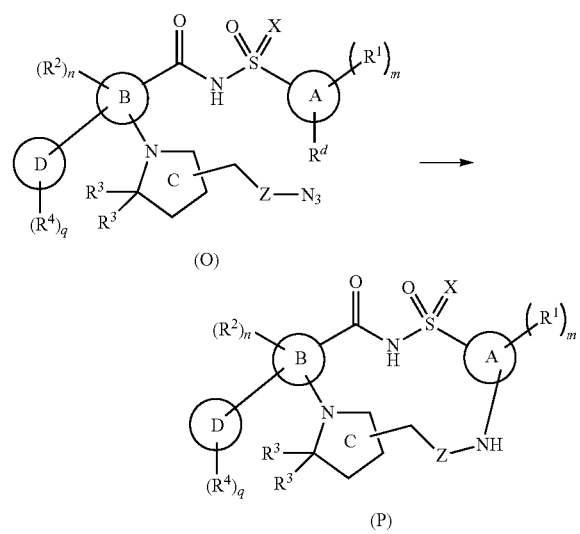

Additional Embodiments Include

1. A compound of Formula I:

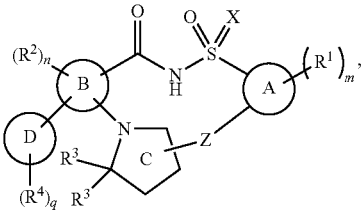

a pharmaceutically acceptable salt thereof, or a deuterated derivative of any of the foregoing,
wherein:
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
X is O, NH, or an N(C1-C4 alkyl);
each $R^1$ is independently chosen from $C_1\text{-}C_2$ alkyl groups, $C_1\text{-}C_2$ alkoxyl groups, $C_1\text{-}C_2$ haloalkyl groups, $C_1\text{-}C_2$ haloalkoxyl groups, halogens, a cyano group, and a hydroxyl group;
m is 0, 1, 2, 3, or 4;
each $R^2$ is independently chosen from $C_1\text{-}C_2$ alkyl groups, $C_1\text{-}C_2$ alkoxyl groups, $C_1\text{-}C_2$ haloalkyl groups, $C_1\text{-}C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups; wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;

q is 1, 2, 3 or 4; and

Z is a divalent linker of formula $(L)_r$, wherein:

r is 1, 2, 3, 4, 5, or 6;

each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is independently chosen from hydrogen, halogens, $C_1$-$C_2$ haloalkyl groups, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

2. The compound of embodiment 1, a pharmaceutically acceptable salt thereof, or a deuterated derivative of any of the foregoing, wherein Ring A is a phenyl ring, a pyridyl ring, or a pyrazolyl ring, wherein Ring A is optionally substituted with $(R^1)_m$.

3. The compound of embodiment 1 or 2, a pharmaceutically acceptable salt thereof, or a deuterated derivative of any of the foregoing, wherein each $R^1$ is independently chosen from deuterium, $C_1$-$C_2$ alkyl groups, and a hydroxyl group, and m is 0 or 1.

4. The compound of any one of embodiments 1 to 3, a pharmaceutically acceptable salt thereof, or a deuterated derivative of any of the foregoing, wherein n is 0.

5. The compound of any one of embodiments 1 to 4, a pharmaceutically acceptable salt thereof, or a deuterated derivative of any of the foregoing, wherein Ring D is a 5-membered heteroaryl ring substituted with $(R^4)_q$.

6. The compound of any one of embodiments 1 to 4, a pharmaceutically acceptable salt thereof, or a deuterated derivative of any of the foregoing, wherein Ring D is a phenyl ring, pyridinyl ring, pyrazolyl ring, imidazolidinone ring, a pyrrolidinone ring, or a pyridinone ring, wherein Ring D is substituted with $(R^4)_q$.

7. The compound of any one of embodiments 1 to 4, a pharmaceutically acceptable salt thereof, or a deuterated derivative of any of the foregoing, wherein Ring D is

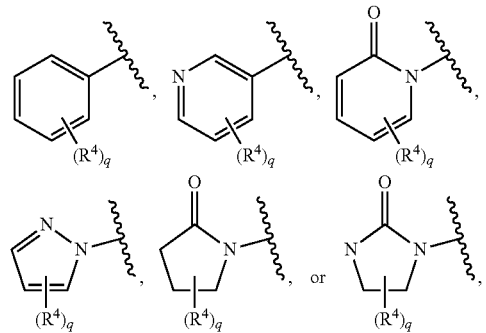

wherein

indicates the point of attachment of Ring D to Ring B.

8. The compound of embodiment 7, a pharmaceutically acceptable salt thereof, or a deuterated derivative of any of the foregoing, wherein Ring D is

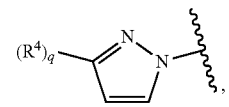

wherein

indicates the point of attachment of Ring D to Ring B.

9. The compound of any one of embodiments 1 to 8, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, and wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

10. The compound of any one of embodiments 1 to 9, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, and wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

11. The compound of any one of embodiments 1 to 8, a pharmaceutically acceptable salt thereof, or a deuterated derivative of any of the foregoing, wherein each $R^4$ is independently chosen from an oxo group or —O-$(Y)_k$-$R^7$ groups, wherein:

k is 0, 1, 2, 3, 4, or 5;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, and wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

12. The compound of any one of embodiments 1 to 8, a pharmaceutically acceptable salt thereof, or a deuterated derivative of any of the foregoing, wherein each $R^4$ is independently chosen from

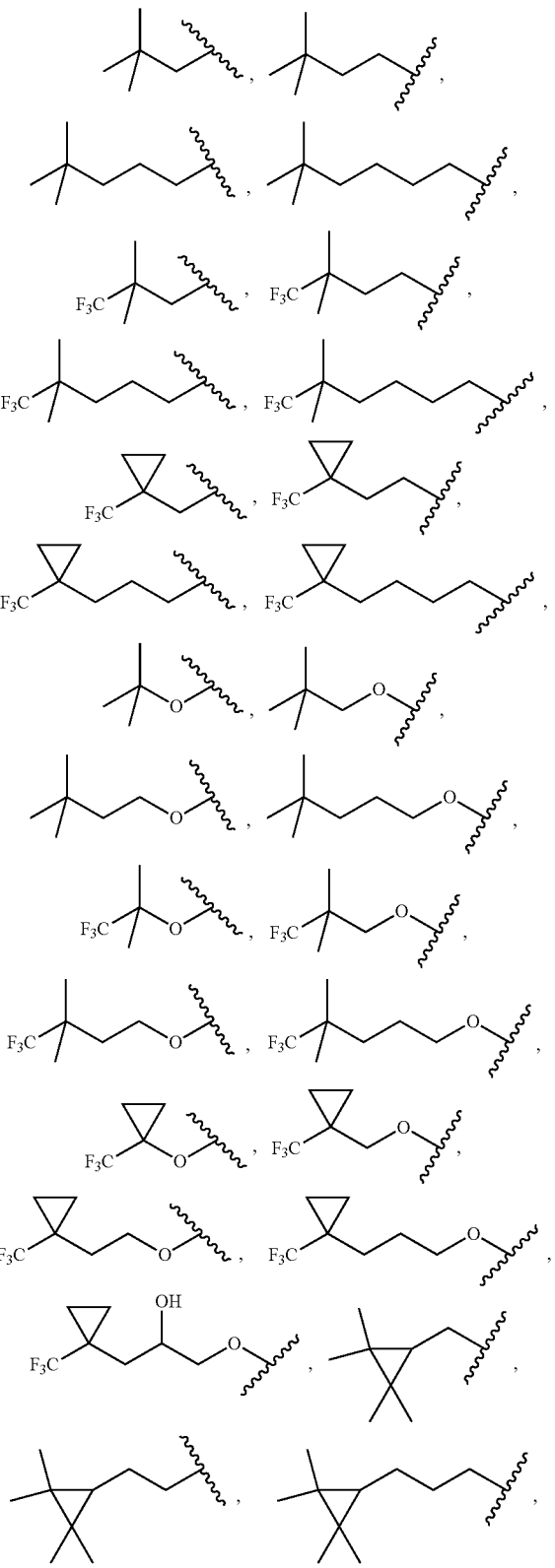

-continued

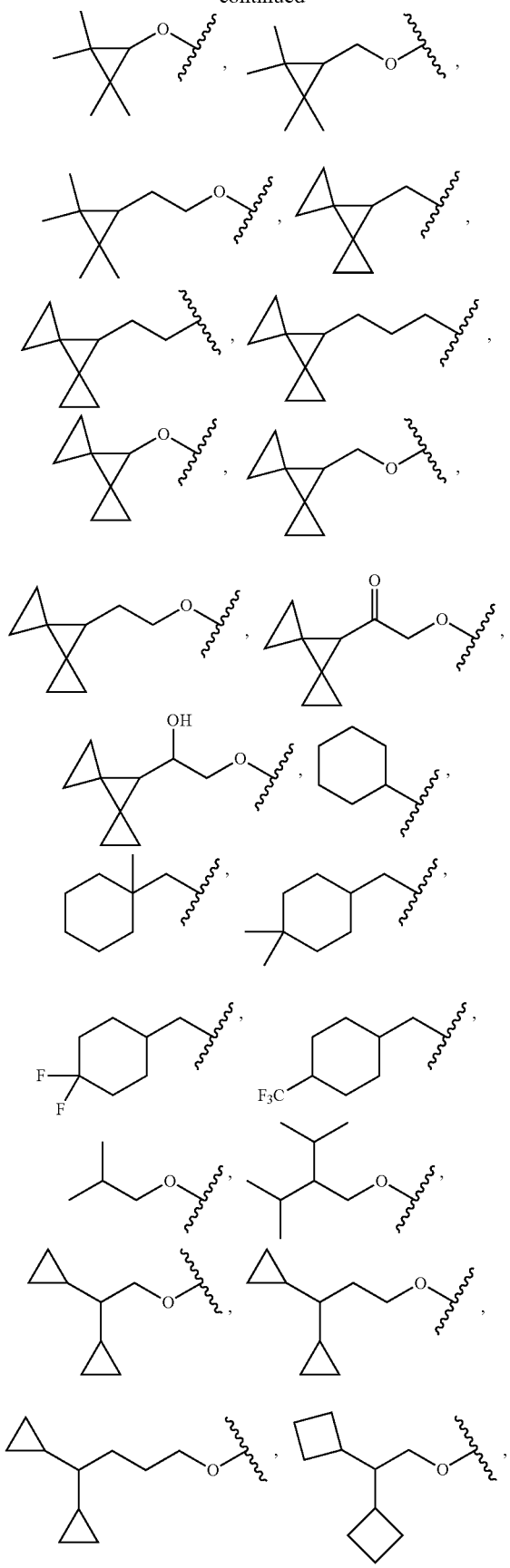

-continued

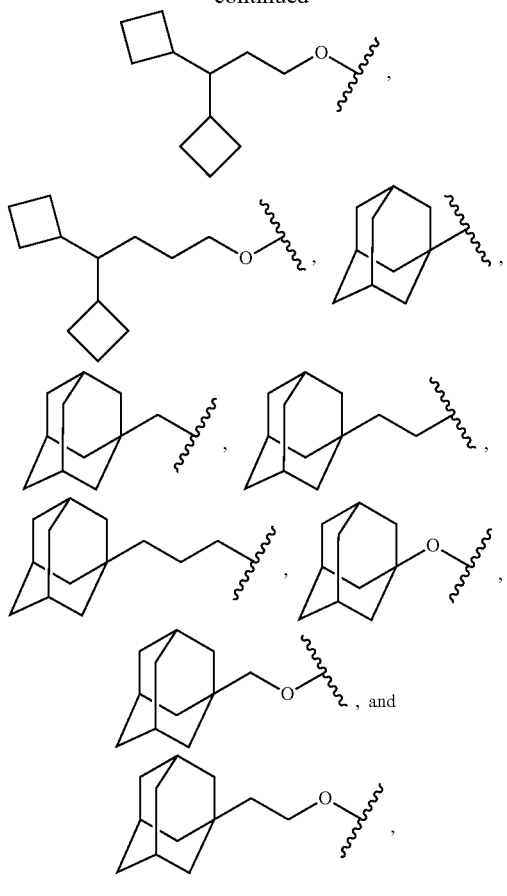

wherein

indicates the point of attachment of $R^4$ to Ring D.

13. The compound of any one of embodiments 1 to 12, a pharmaceutically acceptable salt thereof, or a deuterated derivative of any of the foregoing, wherein k is 3, 4, 5, or 6.

14. The compound of any one of embodiments 1 to 13, a pharmaceutically acceptable salt thereof, or a deuterated derivative of any of the foregoing, wherein q is 1.

15. The compound of any one of embodiments 1 to 14, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, and wherein:
each $R^8$ and $R^9$ is independently chosen from hydrogen and deuterium; and
each $R^b$ is independently chosen from hydrogen and $C_1$-$C_2$ alkyl groups.

16. The compound of any one of embodiments 1 to 14, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R$^8$)(R$^9$) groups and —NR$^b$— groups, wherein a heteroatom in Z is not bonded to another heteroatom in Z, and:
each R$^8$ and R$^9$ is independently chosen from hydrogen and deuterium; and
each R$^b$ is independently chosen from hydrogen and methyl.

17. The compound of any one of embodiments 1 to 14, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R$^8$)(R$^9$) groups and —NR$^b$— groups, wherein a heteroatom in Z is not bonded to another heteroatom in Z, and wherein:
each R$^8$ and R$^9$ is independently chosen from hydrogen and deuterium; and
each R$^b$ is hydrogen.

18. The compound of any one of embodiments 1 to 14, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R$^8$)(R$^9$) groups, —O—, and —NR$^b$— groups, wherein a heteroatom in Z is not bonded to another heteroatom in Z, wherein:
each R$^8$ and R$^9$ is hydrogen; and
each R$^b$ is independently chosen from hydrogen and C$_1$-C$_2$ alkyl groups.

19. The compound of any one of embodiments 1 to 18, a pharmaceutically acceptable salt thereof, or a deuterated derivative of any of the foregoing, wherein each R$^3$ is independently CD$_3$.

20. The compound of embodiment 1, a pharmaceutically acceptable salt thereof, or a deuterated derivative of any of the foregoing, wherein the compound of Formula (I) is a compound of Formula (II-A) or (II-B):

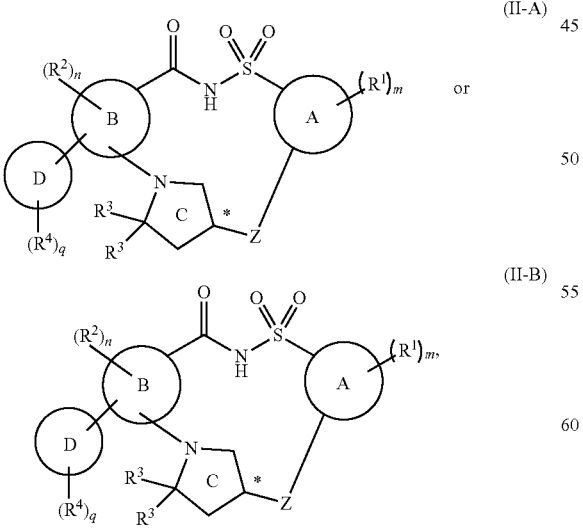

a pharmaceutically acceptable salt thereof, or a deuterated derivative of any of the foregoing, wherein:
the carbon denoted by * has S-stereochemistry or R-stereochemistry;
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
each R$^1$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
m is 0, 1, 2, 3, or 4;
each R$^2$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
n is 0, 1, or 2;
each R$^3$ is methyl;
each R$^4$ is independently chosen from halogens, a hydroxyl group, an oxo group, a cyano group, and -(Y)$_k$-R$^7$ groups, or optionally two R$^4$, together with the atom(s) they are attached to, form a 5-6 membered cycloalkyl or heterocyclyl ring that is optionally and independently substituted with one or more groups chosen from halogens, C$_1$-C$_2$ alkyl groups, haloalkyl groups, a hydroxyl group, C$_1$-C$_2$ alkoxyl groups, and C$_1$-C$_2$ haloalkoxyl groups, wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
each R$^5$ and R$^6$ is independently chosen from hydrogen, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
each R$^a$ is independently chosen from hydrogen and C$_1$-C$_2$ alkyl groups; and
R$^7$ is chosen from hydrogen, halogens, a cyano group, and C$_3$-C$_{10}$ to cycloalkyl groups optionally substituted with one or more groups chosen from C$_1$-C$_2$ alkyl groups, C$_1$-C$_2$ haloalkyl groups, and halogens;
q is 1, 2, 3, or 4;
Z is a divalent linker of formula (L)$_r$, wherein:
r is 1, 2, 3, 4, 5, or 6;
each L is independently chosen from C(R$^8$)(R$^9$) groups, —O—, and —NR$^b$— groups, wherein a heteroatom in Z is not bonded to another heteroatom in Z, wherein:
each R$^8$ and R$^9$ is independently chosen from hydrogen, halogens, C$_1$-C$_2$ alkyl groups, C$_1$-C$_2$ haloalkyl groups, a hydroxyl group, C$_1$-C$_2$ alkoxyl groups, and C$_1$-C$_2$ haloalkoxyl groups; and
each R$^b$ is independently chosen from hydrogen and C$_1$-C$_2$ alkyl groups.

21. The compound of embodiment 20, a pharmaceutically acceptable salt thereof, or a deuterated derivative of any of the foregoing, wherein Ring A is a phenyl ring, a pyridyl ring, or a pyrazolyl ring, wherein Ring A is optionally substituted with $(R^1)_m$.

22. The compound of embodiment 20 or 21, a pharmaceutically acceptable salt thereof, or a deuterated derivative of any of the foregoing, wherein each $R^1$ is independently chosen from deuterium, $C_1$-$C_2$ alkyl groups, and a hydroxyl group, and m is 0 or 1.

23. The compound of any one of embodiments 20 to 22, a pharmaceutically acceptable salt thereof, or a deuterated derivative of any of the foregoing, wherein n is 0.

24. The compound of any one of embodiments 20 to 23, a pharmaceutically acceptable salt thereof, or a deuterated derivative of any of the foregoing, wherein Ring D is a 5-membered heteroaryl ring substituted with $(R^4)_q$.

25. The compound of any one of embodiments 20 to 23, a pharmaceutically acceptable salt thereof, or a deuterated derivative of any of the foregoing, wherein Ring D is a pyrazolyl ring or a pyridinone ring, wherein Ring D is substituted with $R^4$.

26. The compound of any one of embodiments 20 to 23, a pharmaceutically acceptable salt thereof, or a deuterated derivative of any of the foregoing, wherein Ring D is

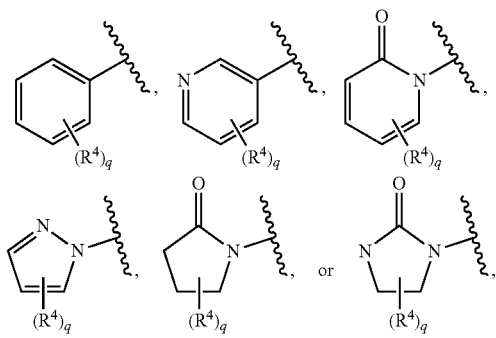

wherein

indicates the point of attachment of Ring D to Ring B.

27. The compound of any one of embodiments 20 to 23, a pharmaceutically acceptable salt thereof, or a deuterated derivative of any of the foregoing, wherein Ring D is

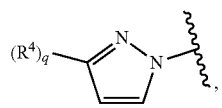

wherein

indicates the point of attachment of Ring D to Ring B.

28. The compound of any one of embodiments 20 to 27, a pharmaceutically acceptable salt thereof, or a deuterated derivative of any of the foregoing, wherein each $R^4$ is independently chosen from an oxo group or $-(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in $-(Y)_k$-$R^7$ is not bonded to another heteroatom in $-(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

29. The compound of any one of embodiments 20 to 28, a pharmaceutically acceptable salt thereof, or a deuterated derivative of any of the foregoing, wherein each $R^4$ is independently chosen from an oxo group or $-(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in $-(Y)_k$-$R^7$ is not bonded to another heteroatom in $-(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

30. The compound of any one of embodiments 20 to 28, a pharmaceutically acceptable salt thereof, or a deuterated derivative of any of the foregoing, wherein each $R^4$ is independently chosen from an oxo group or —O-$(Y)_k$-$R^7$ groups, wherein:

k is 0, 1, 2, 3, 4, or 5;

each Y is independently chosen from $C(R^5)(R^6)$ groups, —O—, and —$NR^a$— groups, wherein a heteroatom in $-(Y)_k$-$R^7$ is not bonded to another heteroatom in $-(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or R5 and R6 on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens.

31. The compound of any one of embodiments 20 to 28, a pharmaceutically acceptable salt thereof, or a deuterated derivative of any of the foregoing, wherein each $R^4$ is independently chosen from

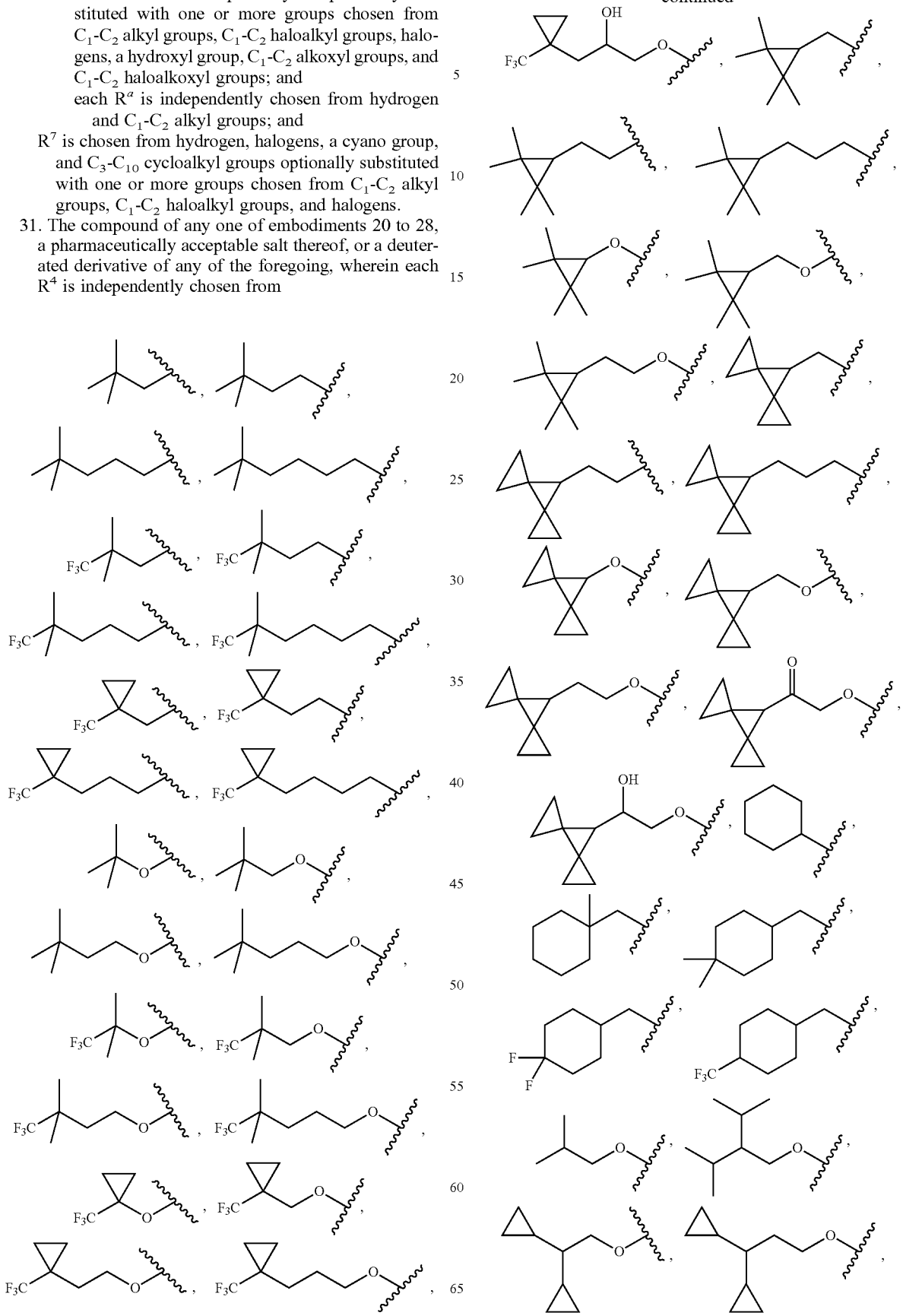

-continued

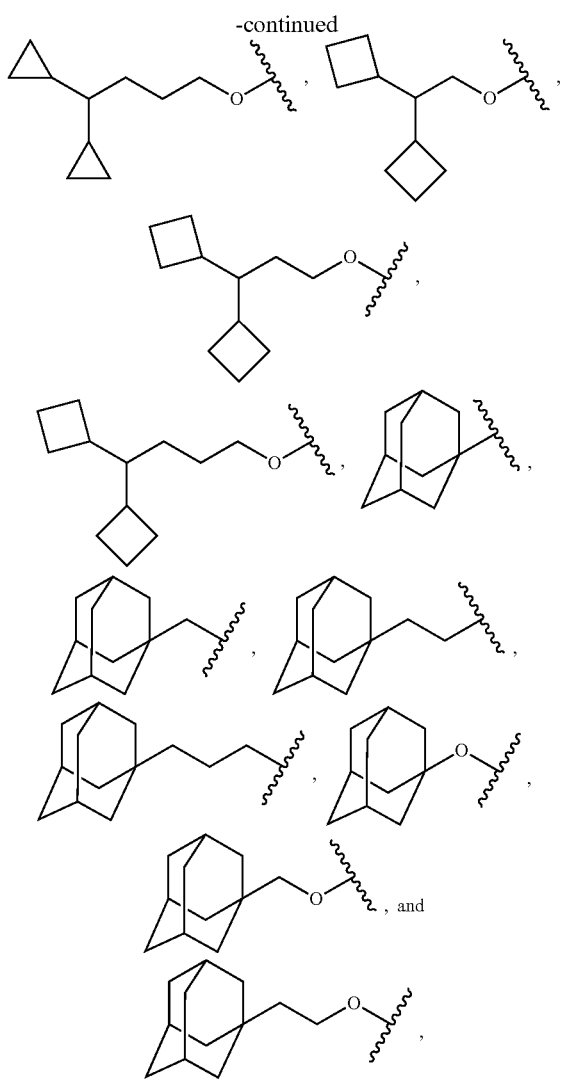

wherein

indicates the point of attachment of $R^4$ to Ring D.

32. The compound of any one of embodiments 20 to 31, a pharmaceutically acceptable salt thereof, or a deuterated derivative of any of the foregoing, wherein k is 3, 4, 5, or 6.

33. The compound of any one of embodiments 20 to 32, a pharmaceutically acceptable salt thereof, or a deuterated derivative of any of the foregoing, wherein q is 1.

34. The compound of any one of embodiments 20 to 33, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen and deuterium; and
each $R^b$ is independently chosen from hydrogen and $C_1$-$C_2$ alkyl groups.

35. The compound of any one of embodiments 20 to 33, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups and —$NR^b$— groups, wherein a heteroatom in Z is not bonded to another heteroatom in Z, wherein:
each $R^8$ and $R^9$ is independently chosen from hydrogen and deuterium; and
each $R^b$ is independently chosen from hydrogen and methyl.

36. The compound of any one of embodiments 20 to 33, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups and —$NR^b$— groups, wherein a heteroatom in Z is not bonded to another heteroatom in Z, wherein:
each $R^8$ and $R^9$ is independently chosen from hydrogen and deuterium; and
each $R^b$ is hydrogen.

37. The compound of any one of embodiments 20 to 33, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is hydrogen; and
each $R^b$ is independently chosen from hydrogen and $C_1$-$C_2$ alkyl groups.

38. The compound of any one of embodiments 20 to 37, a pharmaceutically acceptable salt thereof, or a deuterated derivative of any of the foregoing, wherein each $R^3$ is independently $CD_3$.

39. The compound of embodiment 1, a pharmaceutically acceptable salt thereof, or a deuterated derivative of any of the foregoing, wherein the compound of Formula I is a compound of Formula (III-A) or (III-B):

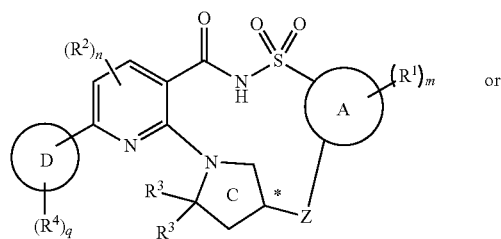

-continued

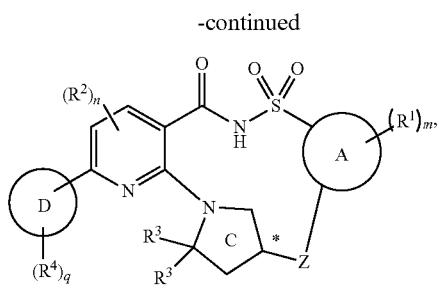

(III-B)

a pharmaceutically acceptable salt thereof, or a deuterated derivative of any of the foregoing,
wherein:
the carbon denoted by * has S-stereochemistry or R-stereochemistry;
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -(Y)$_k$-$R^7$ groups or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from C($R^5$)($R^6$) groups, —O—, and —NR$^a$— groups, wherein a heteroatom in -(Y)$_k$-$R^7$ is not bonded to another heteroatom in -(Y)$_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;
Z is a divalent linker of formula (L)$_r$, wherein:
r is 3, 4, or 5;
each L is independently chosen from C($R^8$)($R^9$) groups, —O—, and —NR$^b$— groups, wherein a heteroatom in Z is not bonded to another heteroatom in Z, wherein:
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

40. The compound of embodiment 39, a pharmaceutically acceptable salt thereof, or a deuterated derivative of any of the foregoing, wherein Ring A is a phenyl ring, a pyridyl ring, or a pyrazolyl ring, wherein Ring A is optionally substituted with ($R^1$)$_m$.

41. The compound of embodiment 39 or 40, a pharmaceutically acceptable salt thereof, or a deuterated derivative of any of the foregoing, wherein each $R^1$ is independently chosen from deuterium, $C_1$-$C_2$ alkyl groups, and a hydroxyl group, and m is 0 or 1.

42. The compound of any one of embodiments 39 to 41, a pharmaceutically acceptable salt thereof, or a deuterated derivative of any of the foregoing, wherein n is 0.

43. The compound of any one of embodiments 39 to 42, a pharmaceutically acceptable salt thereof, or a deuterated derivative of any of the foregoing, wherein Ring D is a 5-membered heteroaryl ring substituted with ($R^4$)$_q$.

44. The compound of any one of embodiments 39 to 42, a pharmaceutically acceptable salt thereof, or a deuterated derivative of any of the foregoing, wherein Ring D is a pyrazolyl ring substituted with ($R^4$)$_q$.

45. The compound of any one of embodiments 39 to 42, a pharmaceutically acceptable salt thereof, or a deuterated derivative of any of the foregoing, wherein Ring D is

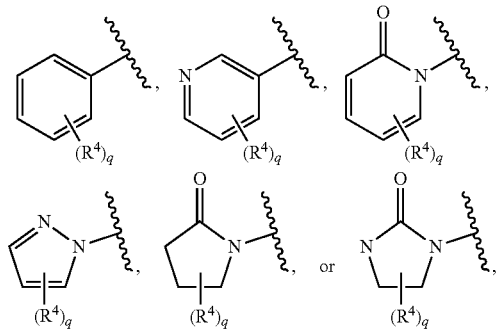

wherein

indicates the point of attachment of Ring D to Ring B.

46. The compound of any one of embodiments 39 to 42, a pharmaceutically acceptable salt thereof, or a deuterated derivative of any of the foregoing, wherein Ring D is

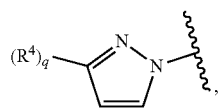

wherein

indicates the point of attachment of Ring D to Ring B.

47. The compound of any one of embodiments 39 to 46, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

48. The compound of any one of embodiments 39 to 47, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

49. The compound of any one of embodiments 39 to 47, a pharmaceutically acceptable salt thereof, or a deuterated derivative of any of the foregoing, wherein each $R^4$ is independently chosen from an oxo group or —O-$(Y)_k$-$R^7$ groups, wherein:

k is 0, 1, 2, 3, 4, or 5;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

50. The compound of any one of embodiments 39 to 47, a pharmaceutically acceptable salt thereof, or a deuterated derivative of any of the foregoing, wherein each $R^4$ is independently chosen from

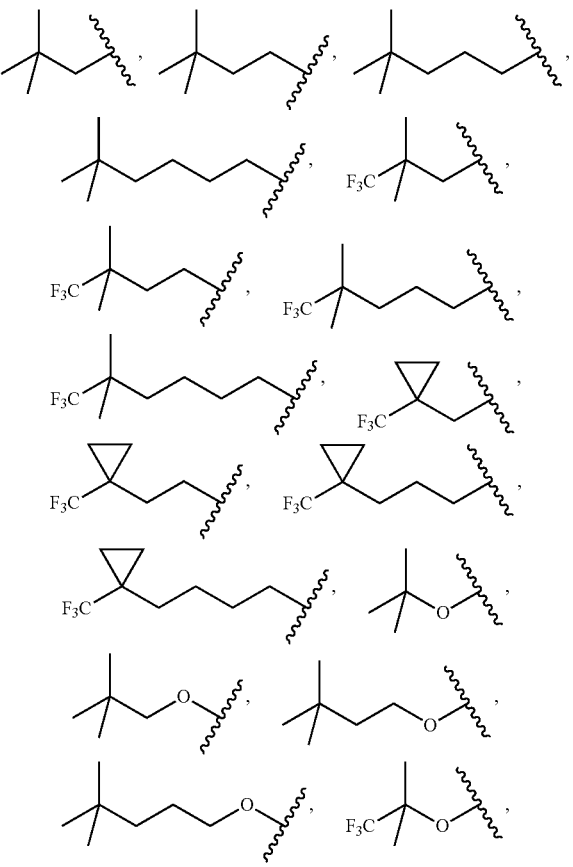

-continued
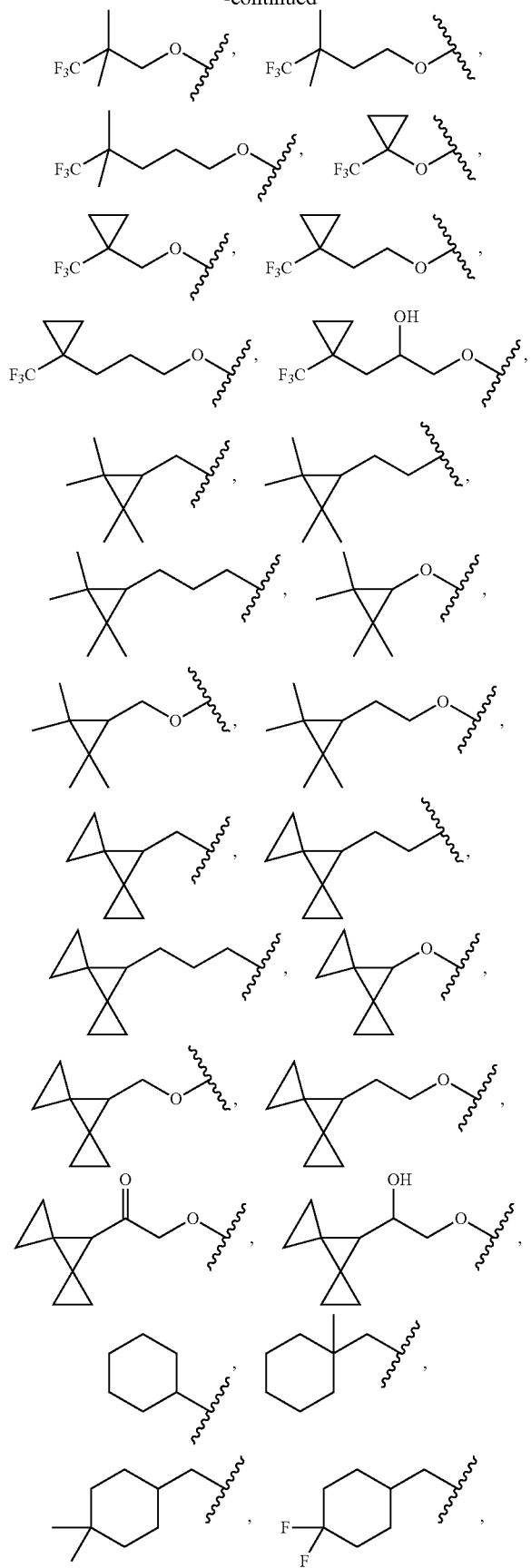
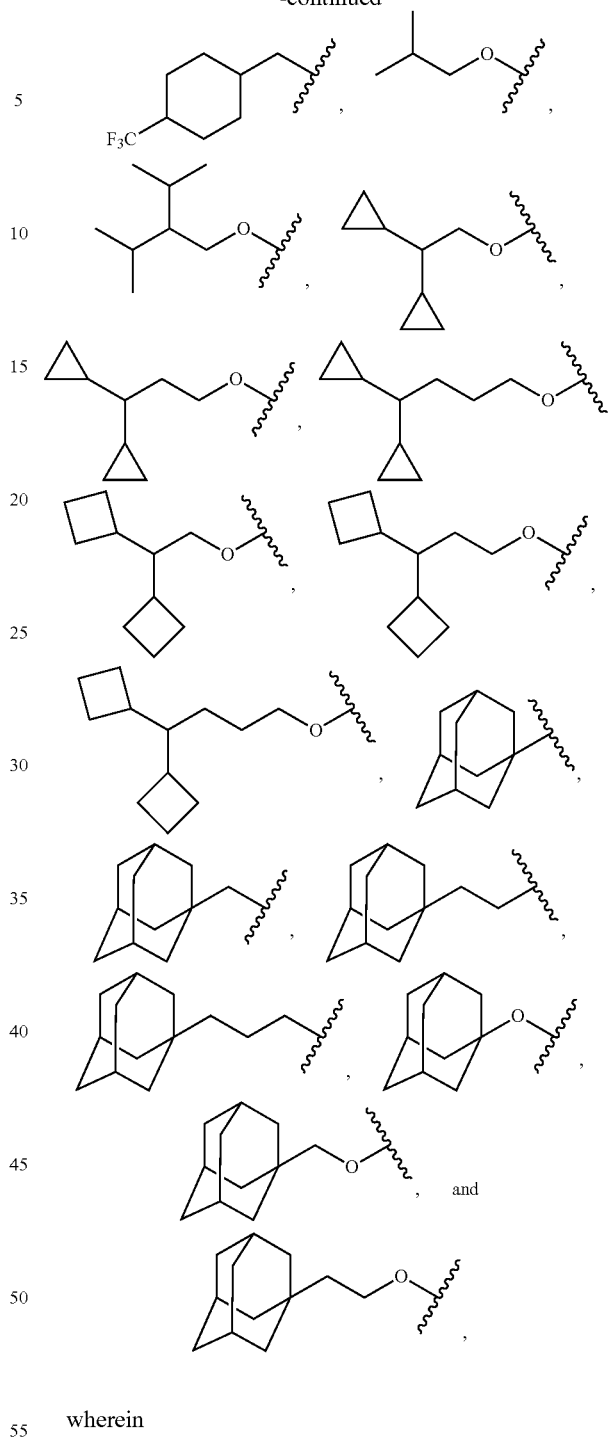
wherein
indicates the point of attachment of $R^4$ to Ring D.
51. The compound of any one of embodiments 39 to 50, a pharmaceutically acceptable salt thereof, or a deuterated derivative of any of the foregoing, wherein k is 3, 4, 5, or 6.

52. The compound of any one of embodiments 39 to 51, a pharmaceutically acceptable salt thereof, or a deuterated derivative of any of the foregoing, wherein q is 1.

53. The compound of any one of embodiments 39 to 52, a pharmaceutically acceptable salt thereof, or a deuterated derivative of any of the foregoing, wherein Z is a divalent linker of formula $(L)_r$, wherein:

r is 3, 4, or 5;

each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is independently chosen from hydrogen and deuterium; and each $R^b$ is independently chosen from hydrogen and $C_1$-$C_2$ alkyl groups.

54. The compound of any one of embodiments 39 to 52, a pharmaceutically acceptable salt thereof, or a deuterated derivative of any of the foregoing, wherein Z is a divalent linker of formula $(L)_r$, wherein:

r is 3, 4, or 5;

each L is independently chosen from $C(R^8)(R^9)$ groups and —$NR^b$— groups, wherein a heteroatom in Z is not bonded to another heteroatom in Z, wherein:

each $R^8$ and $R^9$ is independently chosen from hydrogen and deuterium; and each $R^b$ is independently chosen from hydrogen and methyl.

55. The compound of any one of embodiments 39 to 52, a pharmaceutically acceptable salt thereof, or a deuterated derivative of any of the foregoing, wherein Z is a divalent linker of formula $(L)_r$, wherein:

r is 3, 4, or 5;

each L is independently chosen from $C(R^8)(R^9)$ groups and —$NR^b$— groups, wherein a heteroatom in Z is not bonded to another heteroatom in Z, wherein:

each $R^8$ and $R^9$ is independently chosen from hydrogen and deuterium; and each $R^b$ is hydrogen.

56. The compound of any one of embodiments 39 to 52, a pharmaceutically acceptable salt thereof, or a deuterated derivative of any of the foregoing, wherein Z is a divalent linker of formula $(L)_r$, wherein:

r is 3, 4, or 5;

each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is hydrogen; and each $R^b$ is independently chosen from hydrogen and $C_1$-$C_2$ alkyl groups.

57. The compound of any one of embodiments 39 to 56, a pharmaceutically acceptable salt thereof, or a deuterated derivative of any of the foregoing, wherein each $R^3$ is independently $CD_3$.

58. The compound of embodiment 1, a pharmaceutically acceptable salt thereof, or a deuterated derivative of any of the foregoing, wherein the compound of Formula I is a compound of Formula IV-A:

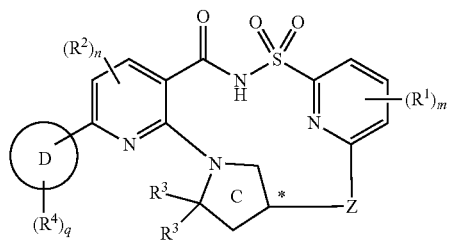

(IV-A)

a pharmaceutically acceptable salt thereof, or a deuterated derivative of any of the foregoing, wherein:

the carbon denoted by * has S-stereochemistry or R-stereochemistry;

Ring D is a phenyl ring, a 5-membered heterocyclyl ring, a 6-membered heterocyclyl ring, a 5-membered heteroaryl ring, or a 6-membered heteroaryl ring;

X is O, NH, or an $N(C_1$-$C_4$ alkyl);

each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

m is 0, 1, 2, 3, or 4;

each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;

q is 1 or 2;

Z is a divalent linker of formula (L)$_r$, wherein:
r is 3, 4, or 5;
each L is independently chosen from C(R$^8$)(R$^9$) groups, —O—, and —NR$^b$— groups, wherein a heteroatom in Z is not bonded to another heteroatom in Z, wherein:
each R$^8$ and R$^9$ is independently chosen from hydrogen, halogens, C$_1$-C$_2$ alkyl groups, a hydroxyl group, C$_1$-C$_2$ alkoxyl groups, and C$_1$-C$_2$ haloalkoxyl groups; and
each R$^b$ is independently chosen from hydrogen and C$_1$-C$_2$ alkyl groups.

59. The compound of embodiment 58, a pharmaceutically acceptable salt thereof, or a deuterated derivative of any of the foregoing, wherein each R$^1$ is independently chosen from deuterium, C$_1$-C$_2$ alkyl groups, and a hydroxyl group, and m is 0 or 1.

60. The compound of embodiment 58 or 59, a pharmaceutically acceptable salt thereof, or a deuterated derivative of any of the foregoing, wherein n is 0.

61. The compound of any one of embodiments 58 to 60, a pharmaceutically acceptable salt thereof, or a deuterated derivative of any of the foregoing, wherein Ring D is a 5-membered heteroaryl ring substituted with (R$^4$)$_q$.

62. The compound of any one of embodiments 58 to 60, a pharmaceutically acceptable salt thereof, or a deuterated derivative of any of the foregoing, wherein Ring D is a pyrazolyl ring substituted with (R$^4$)$_q$.

63. The compound of any one of embodiments 58 to 60, a pharmaceutically acceptable salt thereof, or a deuterated derivative of any of the foregoing, wherein Ring D is

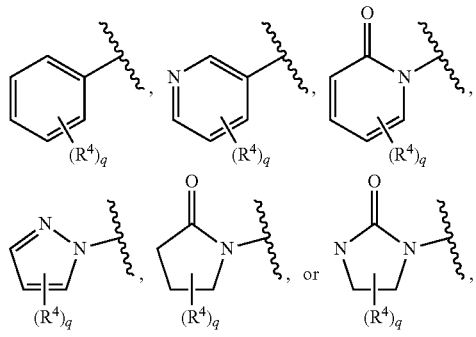

wherein

indicates the point of attachment of Ring D to Ring B.

64. The compound of any one of embodiments 58 to 60, a pharmaceutically acceptable salt thereof, or a deuterated derivative of any of the foregoing, wherein Ring D is

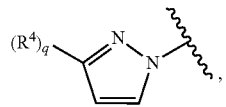

wherein

indicates the point of attachment of Ring D to Ring B.

65. The compound of any one of embodiments 58 to 64, a pharmaceutically acceptable salt thereof, or a deuterated derivative of any of the foregoing, wherein each R$^4$ is independently chosen from an oxo group or -(Y)$_k$-R$^7$ groups, wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
each R$^5$ and R$^6$ is independently chosen from hydrogen, deuterium, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
each R$^a$ is independently chosen from hydrogen and C$_1$-C$_2$ alkyl groups; and
R$^7$ is chosen from hydrogen, halogens, a cyano group, and C$_3$-C$_{10}$ to cycloalkyl groups optionally substituted with one or more groups chosen from C$_1$-C$_2$ alkyl groups, C$_1$-C$_2$ haloalkyl groups, and halogens.

66. The compound of any one of embodiments 58 to 65, a pharmaceutically acceptable salt thereof, or a deuterated derivative of any of the foregoing, wherein each R$^4$ is independently chosen from an oxo group or -(Y)$_k$-R$^7$ groups, wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
each R$^5$ and R$^6$ is independently chosen from hydrogen, deuterium, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group;
each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
each R$^a$ is independently chosen from hydrogen and C$_1$-C$_2$ alkyl groups; and
R$^7$ is chosen from hydrogen, halogens, a cyano group, and C$_3$-C$_{10}$ to cycloalkyl groups optionally substituted with one or more groups chosen from C$_1$-C$_2$ alkyl groups, C$_1$-C$_2$ haloalkyl groups, and halogens.

67. The compound of any one of embodiments 58 to 66, a pharmaceutically acceptable salt thereof, or a deuterated derivative of any of the foregoing, wherein each R$^4$ is independently chosen from an oxo group or —O-(Y)$_k$-R$^7$ groups, wherein:
k is 0, 1, 2, 3, 4, or 5;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

68. The compound of any one of embodiments 58 to 67, a pharmaceutically acceptable salt thereof, or a deuterated derivative of any of the foregoing, wherein each $R^4$ is independently chosen from

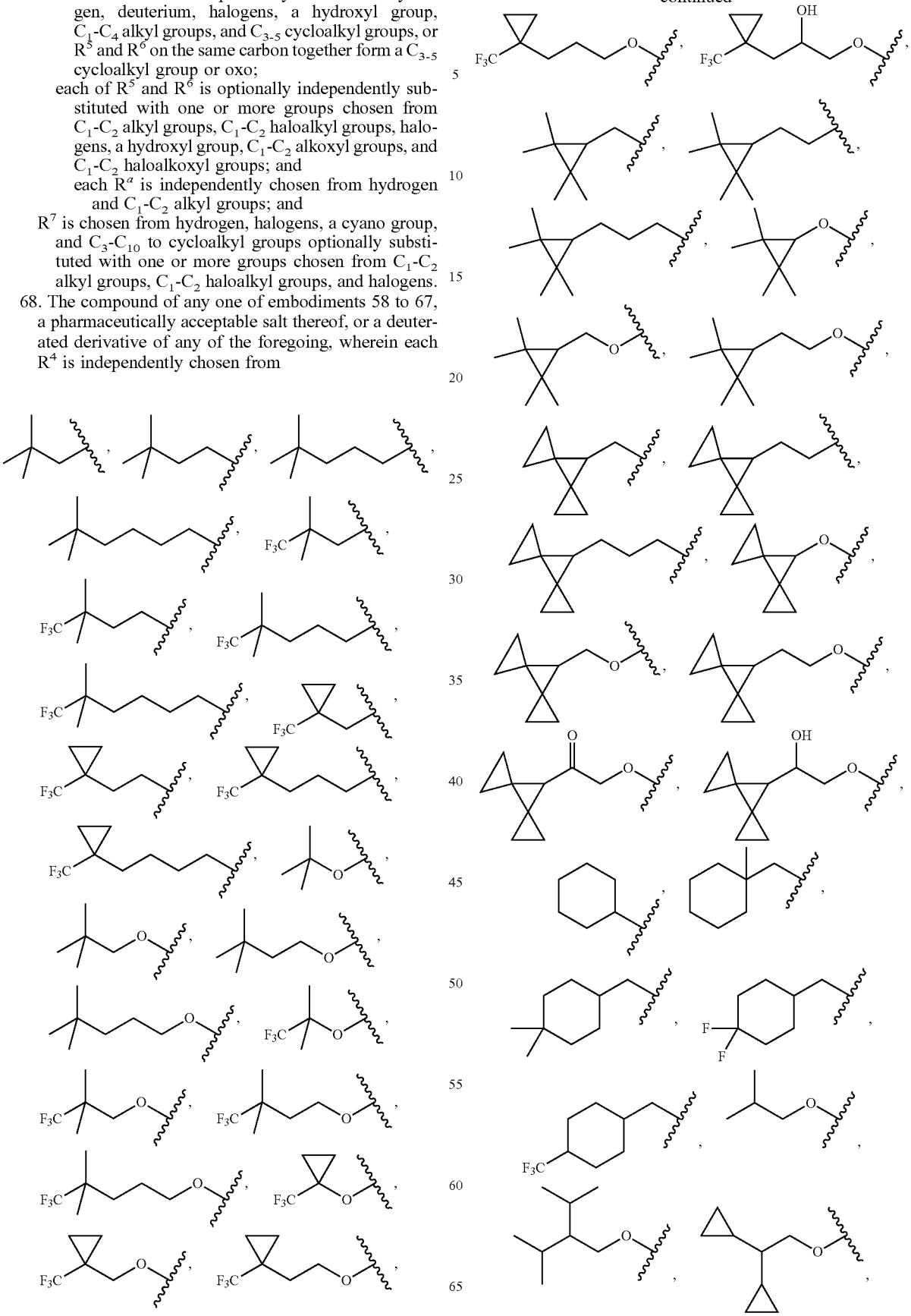

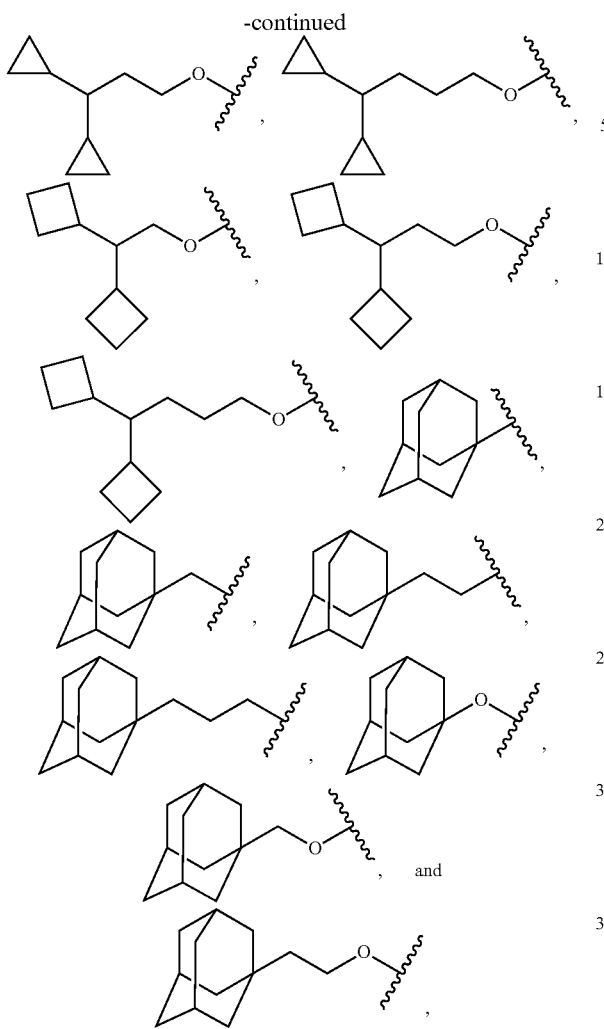

wherein

indicates the point of attachment of $R^4$ to Ring D.

69. The compound of any one of embodiments 58 to 68, a pharmaceutically acceptable salt thereof, or a deuterated derivative of any of the foregoing, wherein k is 3, 4, 5, or 6.

70. The compound of any one of embodiments 58 to 69, a pharmaceutically acceptable salt thereof, or a deuterated derivative of any of the foregoing, wherein q is 1.

71. The compound of any one of embodiments 58 to 70, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen and deuterium; and
each $R^b$ is independently chosen from hydrogen and $C_1$-$C_2$ alkyl groups.

72. The compound of any one of embodiments 58 to 70, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups and —$NR^b$— groups, wherein a heteroatom in Z is not bonded to another heteroatom in Z, wherein:
each $R^8$ and $R^9$ is independently chosen from hydrogen and deuterium; and
each $R^b$ is independently chosen from hydrogen and methyl.

73. The compound of any one of embodiments 58 to 70, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups and —$NR^b$— groups, wherein a heteroatom in Z is not bonded to another heteroatom in Z, wherein:
each $R^8$ and $R^9$ is independently chosen from hydrogen and deuterium; and
each $R^b$ is hydrogen.

74. The compound of any one of embodiments 58 to 70, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is hydrogen; and
each $R^b$ is independently chosen from hydrogen and $C_1$-$C_2$ alkyl groups.

75. The compound of any one of embodiments 58 to 74, a pharmaceutically acceptable salt thereof, or a deuterated derivative of any of the foregoing, wherein each $R^3$ is independently $CD_3$.

76. The compound of embodiment 1, a pharmaceutically acceptable salt thereof, or a deuterated derivative of any of the foregoing, wherein the compound of Formula I is a compound of Formula IV-B:

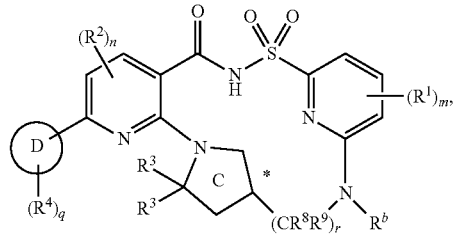

(IV-B)

a pharmaceutically acceptable salt thereof, or a deuterated derivative of any of the foregoing,
wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;

each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

m is 0, 1, 2, 3, or 4;

each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;

q is 1 or 2;

r is 3 or 4;

each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

77. The compound of embodiment 76, a pharmaceutically acceptable salt thereof, or a deuterated derivative of any of the foregoing, wherein each $R^8$ and $R^9$ is independently chosen from hydrogen, deuterium, halogens, $C_1$-$C_2$ alkyl groups, a hydroxyl group, $C_1$-$C_2$ alkoxyl groups, and $C_1$-$C_2$ haloalkoxyl groups.

78. The compound of embodiment 76 or 77, a pharmaceutically acceptable salt thereof, or a deuterated derivative of any of the foregoing, wherein each $R^8$ and $R^9$ is H.

79. The compound of any one of embodiments 76 to 78, a pharmaceutically acceptable salt thereof, or a deuterated derivative of any of the foregoing, wherein each $R^1$ is independently chosen from deuterium, $C_1$-$C_2$ alkyl groups, and a hydroxyl group, and m is 0 or 1.

80. The compound of any one of embodiments 76 to 79, a pharmaceutically acceptable salt thereof, or a deuterated derivative of any of the foregoing, wherein n is 0.

81. The compound of any one of embodiments 76 to 80, a pharmaceutically acceptable salt thereof, or a deuterated derivative of any of the foregoing, wherein Ring D is 5-membered heteroaryl ring substituted with $(R^4)_q$.

82. The compound of any one of embodiments 76 to 80, a pharmaceutically acceptable salt thereof, or a deuterated derivative of any of the foregoing, wherein Ring D is a pyrazolyl ring substituted with $(R^4)_q$.

83. The compound of any one of embodiments 76 to 80, a pharmaceutically acceptable salt thereof, or a deuterated derivative of any of the foregoing, wherein Ring D is

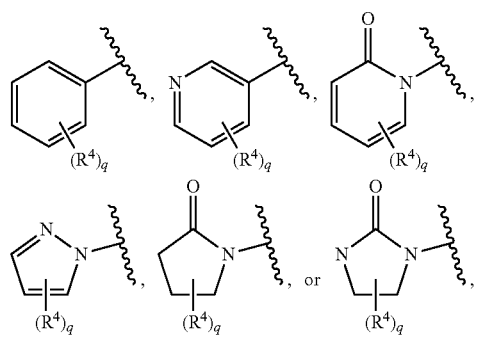

wherein

indicates the point of attachment of Ring D to Ring B.

84. The compound of any one of embodiments 76 to 80, a pharmaceutically acceptable salt thereof, or a deuterated derivative of any of the foregoing, wherein Ring D is

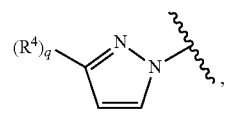

wherein

indicates the point of attachment of Ring D to Ring B.

85. The compound of any one of embodiments 76 to 84, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in -(Y)$_k$-R$^7$ is not bonded to another heteroatom in -(Y)$_k$-R$^7$, wherein:
  each R$^5$ and R$^6$ is independently chosen from hydrogen, deuterium, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
  each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
  each R$^a$ is independently chosen from hydrogen and C$_1$-C$_2$ alkyl groups; and
R$^7$ is chosen from hydrogen, halogens, a cyano group, and C$_3$-C$_{10}$ to cycloalkyl groups optionally substituted with one or more groups chosen from C$_1$-C$_2$ alkyl groups, C$_1$-C$_2$ haloalkyl groups, and halogens.

86. The compound of any one of embodiments 76 to 84, a pharmaceutically acceptable salt thereof, or a deuterated derivative of any of the foregoing, wherein each R$^4$ is independently chosen from an oxo group or -(Y)$_k$-R$^7$ groups, wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
  each R$^5$ and R$^6$ is independently chosen from hydrogen, deuterium, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group;
  each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
  each R$^a$ is independently chosen from hydrogen and C$_1$-C$_2$ alkyl groups; and
R$^7$ is chosen from hydrogen, halogens, a cyano group, and C$_3$-C$_{10}$ to cycloalkyl groups optionally substituted with one or more groups chosen from C$_1$-C$_2$ alkyl groups, C$_1$-C$_2$ haloalkyl groups, and halogens.

87. The compound of any one of embodiments 76 to 84, a pharmaceutically acceptable salt thereof, or a deuterated derivative of any of the foregoing, wherein each R$^4$ is independently chosen from an oxo group or —O-(Y)$_k$-R$^7$ groups, wherein:
k is 0, 1, 2, 3, 4, or 5;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
  each R$^5$ and R$^6$ is independently chosen from hydrogen, deuterium, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
  each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
  each R$^a$ is independently chosen from hydrogen and C$_1$-C$_2$ alkyl groups; and
R$^7$ is chosen from hydrogen, halogens, a cyano group, and C$_3$-C$_{10}$ cycloalkyl groups optionally substituted with one or more groups chosen from C$_1$-C$_2$ alkyl groups, C$_1$-C$_2$ haloalkyl groups, and halogens.

88. The compound of any one of embodiments 76 to 84, a pharmaceutically acceptable salt thereof, or a deuterated derivative of any of the foregoing, wherein each R$^4$ is independently

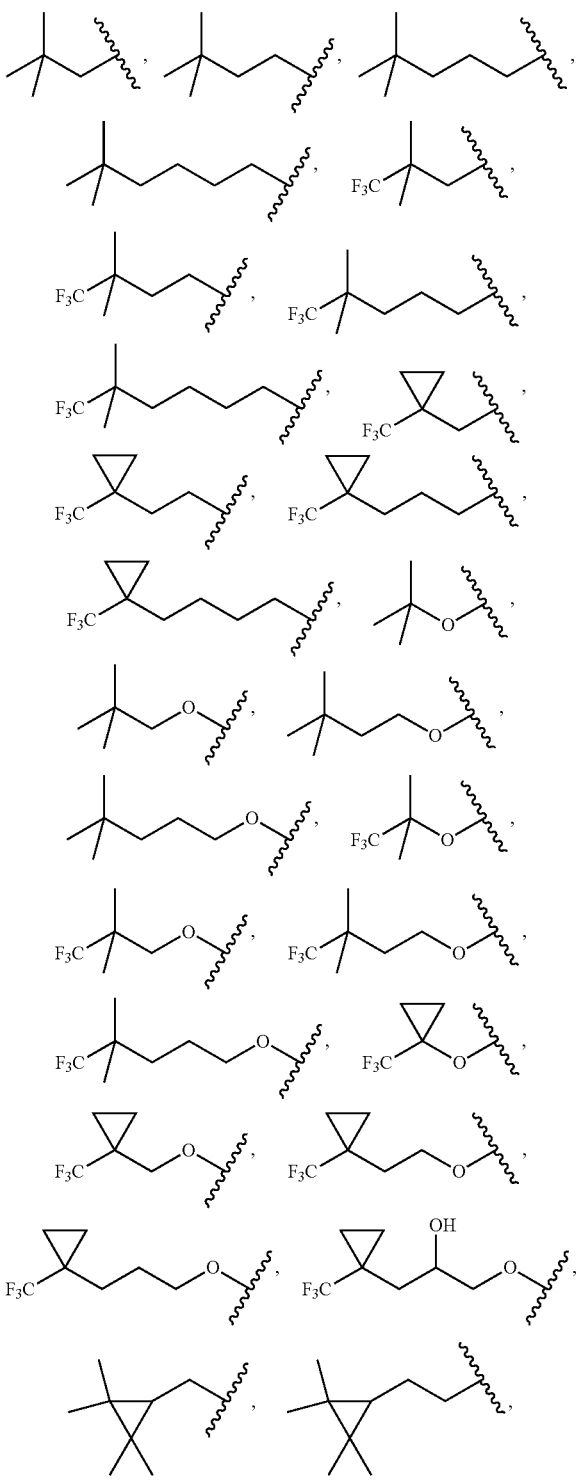

-continued

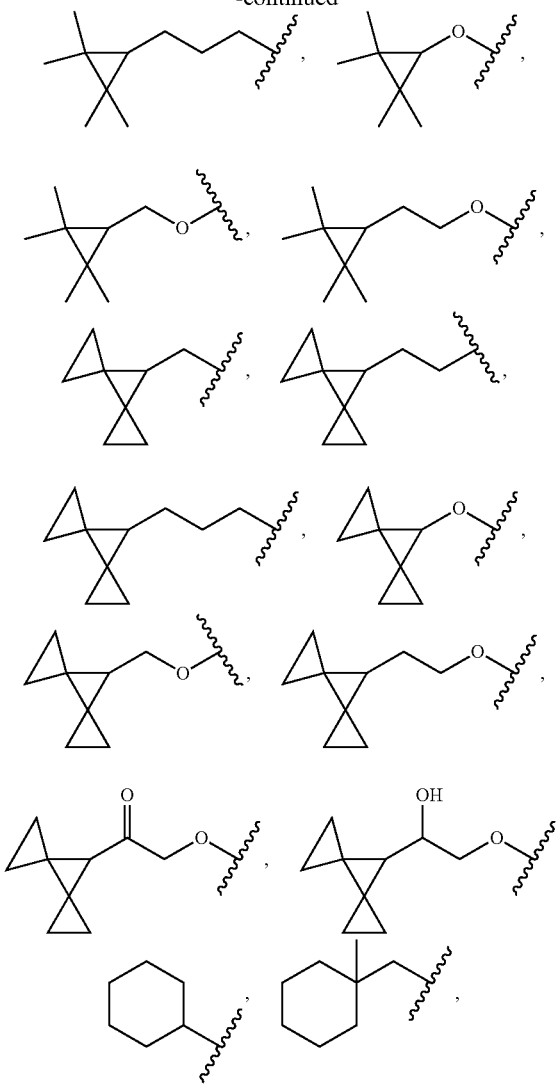

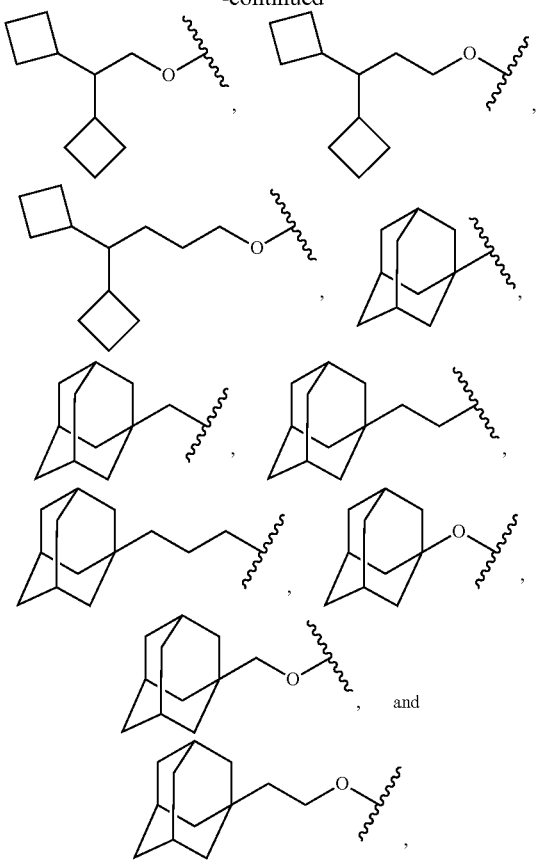

wherein

indicates the point of attachment of $R^4$ to Ring D.

89. The compound of any one of embodiments 76 to 88, a pharmaceutically acceptable salt thereof, or a deuterated derivative of any of the foregoing, wherein k is 3, 4, 5, or 6.

90. The compound of any one of embodiments 76 to 89, a pharmaceutically acceptable salt thereof, or a deuterated derivative of any of the foregoing, wherein q is 1.

91. The compound of any one of embodiments 76 to 90, a pharmaceutically acceptable salt thereof, or a deuterated derivative of any of the foregoing, wherein:
r is 3, 4, or 5;
each $R^8$ and $R^9$ is independently chosen from hydrogen and deuterium; and
each $R^b$ is independently chosen from hydrogen and $C_1$-$C_2$ alkyl groups.

92. The compound of any one of embodiments 76 to 90, a pharmaceutically acceptable salt thereof, or a deuterated derivative of any of the foregoing, wherein:
r is 3, 4, or 5;
each $R^8$ and $R^9$ is independently chosen from hydrogen and deuterium; and
each $R^b$ is independently chosen from hydrogen and methyl.

93. The compound of any one of embodiments 76 to 90, a pharmaceutically acceptable salt thereof, or a deuterated derivative of any of the foregoing, wherein:
r is 3, 4, or 5;
each $R^8$ and $R^9$ is independently chosen from hydrogen and deuterium; and
each $R^b$ is hydrogen.

94. The compound of any one of embodiments 76 to 90, a pharmaceutically acceptable salt thereof, or a deuterated derivative of any of the foregoing, wherein:
r is 3, 4, or 5;
each $R^8$ and $R^9$ is hydrogen; and
each $R^b$ is independently chosen from hydrogen and $C_1$-$C_2$ alkyl groups.

95. The compound of any one of embodiments 76 to 94, a pharmaceutically acceptable salt thereof, or a deuterated derivative of any of the foregoing, wherein each $R^3$ is independently $CD_3$.

96. The compound of embodiment 1, a pharmaceutically acceptable salt thereof, or a deuterated derivative of any of the foregoing, wherein the compound of Formula I is a compound of Formula IV-C:

(IV-C)

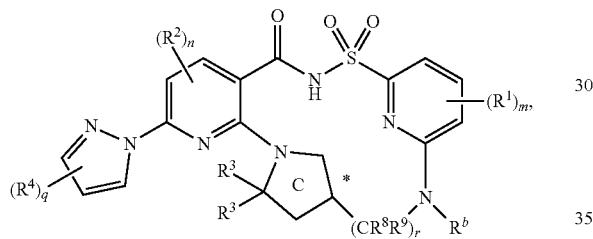

a pharmaceutically acceptable salt thereof, or a deuterated derivative of any of the foregoing,
wherein:
the carbon denoted by * has S-stereochemistry or R-stereochemistry;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -(Y)$_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from C($R^5$)($R^6$) groups, —O—, and —$NR^a$— groups, wherein a heteroatom in -(Y)$_k$-$R^7$ is not bonded to another heteroatom in -(Y)$_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;
q is 1 or 2;
r is 3 or 4;
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

97. The compound of embodiment 96, a pharmaceutically acceptable salt thereof, or a deuterated derivative of any of the foregoing, wherein each $R^8$ and $R^9$ is independently chosen from hydrogen, deuterium, halogens, $C_1$-$C_2$ alkyl groups, a hydroxyl group, $C_1$-$C_2$ alkoxyl groups, and $C_1$-$C_2$ haloalkoxyl groups.

98. The compound of embodiment 96 or 97, a pharmaceutically acceptable salt thereof, or a deuterated derivative of any of the foregoing, wherein each $R^8$ and $R^9$ is H.

99. The compound of any one of embodiments 96 to 98, a pharmaceutically acceptable salt thereof, or a deuterated derivative of any of the foregoing, wherein each $R^1$ is independently chosen from deuterium, $C_1$-$C_2$ alkyl groups, and a hydroxyl group, and m is 0 or 1.

100. The compound of any one of embodiments 96 to 99, a pharmaceutically acceptable salt thereof, or a deuterated derivative of any of the foregoing, wherein n is 0.

101. The compound of any one of embodiments 96 to 100, a pharmaceutically acceptable salt thereof, or a deuterated derivative of any of the foregoing, wherein each $R^4$ is independently chosen from an oxo group or -(Y)$_k$-$R^7$ groups, wherein:
k is 0, 1, 2, 3, 4, 5, or 6;
each Y is independently chosen from C($R^5$)($R^6$) groups, —O—, and —$NR^a$— groups, wherein a heteroatom in -(Y)$_k$-$R^7$ is not bonded to another heteroatom in -(Y)$_k$-$R^7$, wherein:
each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

102. The compound of any one of embodiments 96 to 100, a pharmaceutically acceptable salt thereof, or a deuterated derivative of any of the foregoing, wherein each $R^4$ is independently chosen from an oxo group or -$(Y)_k$-$R^7$ groups, wherein:
  k is 0, 1, 2, 3, 4, 5, or 6;
  each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
    each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group;
    each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
    each $R^a$ is independently chosen from hydrogen and $C_1$-$C_2$ alkyl groups; and
  $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

103. The compound of any one of embodiments 96 to 100, a pharmaceutically acceptable salt thereof, or a deuterated derivative of any of the foregoing, wherein each $R^4$ is independently chosen from an oxo group or —O-$(Y)_k$-$R^7$ groups, wherein:
  k is 0, 1, 2, 3, 4, or 5;
  each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
    each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
    each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
    each $R^a$ is independently chosen from hydrogen and $C_1$-$C_2$ alkyl groups; and
  $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

104. The compound of any one of embodiments 96 to 100, a pharmaceutically acceptable salt thereof, or a deuterated derivative of any of the foregoing, wherein each $R^4$ is independently chosen from

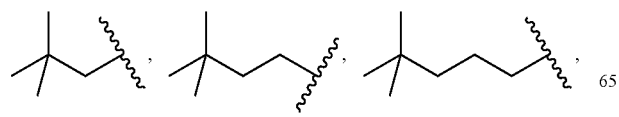

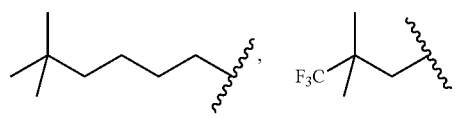

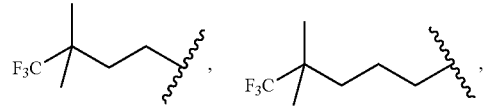

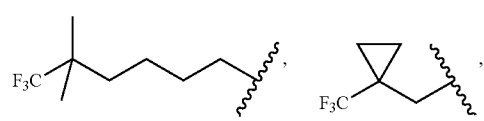

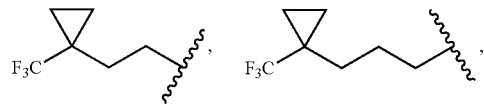

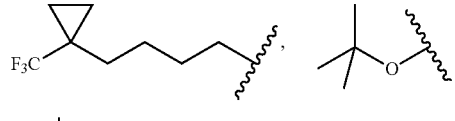

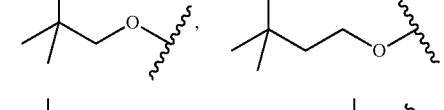

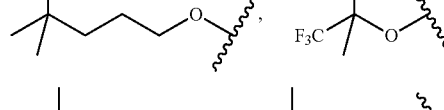

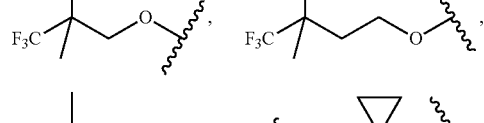

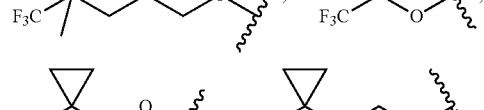

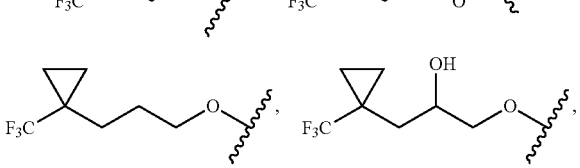

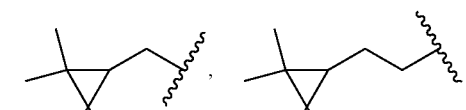

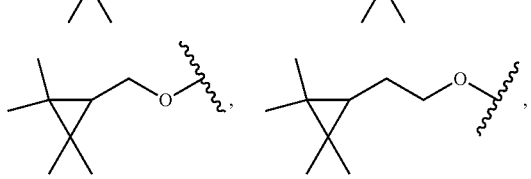

-continued

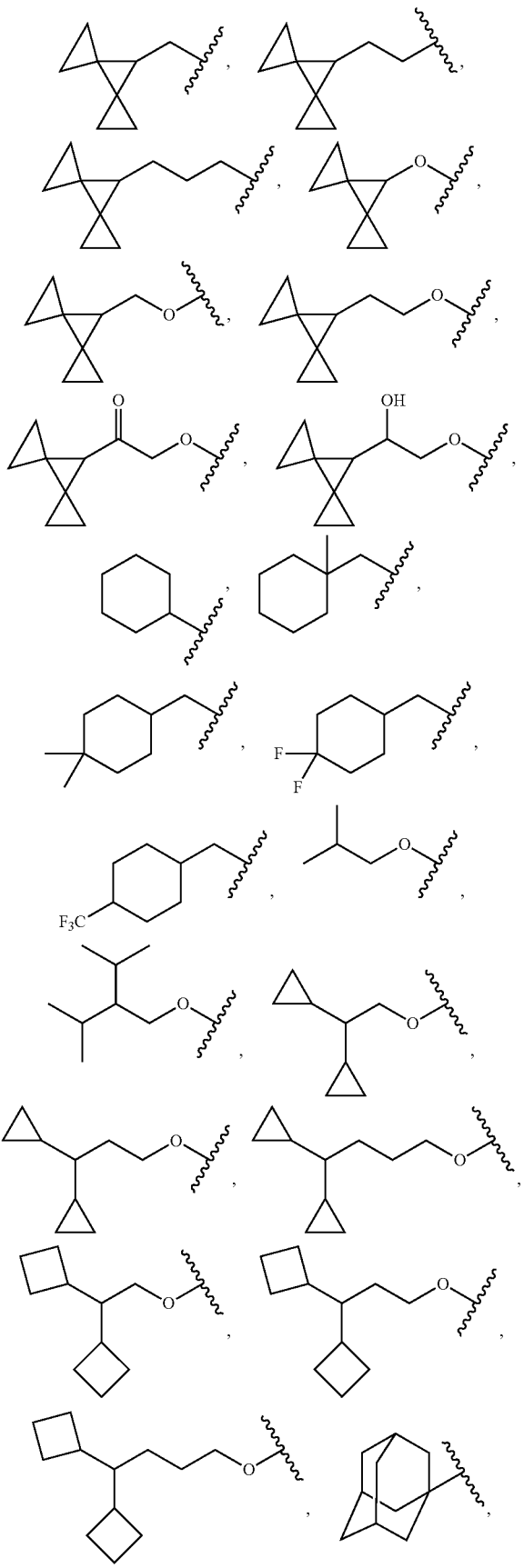

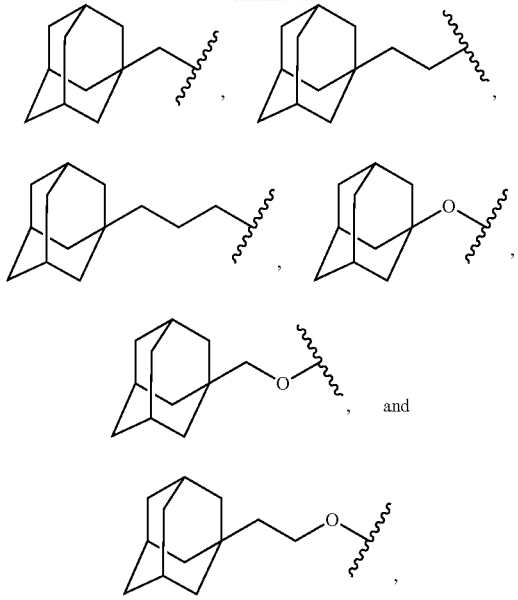

wherein

indicates the point of attachment of $R^4$ to Ring D.

105. The compound of any one of embodiments 96 to 104, a pharmaceutically acceptable salt thereof, or a deuterated derivative of any of the foregoing, wherein k is 3, 4, 5, or 6.

106. The compound of any one of embodiments 96 to 105, a pharmaceutically acceptable salt thereof, or a deuterated derivative of any of the foregoing, wherein q is 1.

107. The compound of any one of embodiments 96 to 106, a pharmaceutically acceptable salt thereof, or a deuterated derivative of any of the foregoing, wherein:
r is 3, 4, or 5;
each $R^8$ and $R^9$ is independently chosen from hydrogen and deuterium; and
each $R^b$ is independently chosen from hydrogen and $C_1$-$C_2$ alkyl groups.

108. The compound of any one of embodiments 96 to 106, a pharmaceutically acceptable salt thereof, or a deuterated derivative of any of the foregoing, wherein:
r is 3, 4, or 5;
each $R^8$ and $R^9$ is independently chosen from hydrogen and deuterium; and
each $R^b$ is independently chosen from hydrogen and methyl.

109. The compound of any one of embodiments 96 to 106, a pharmaceutically acceptable salt thereof, or a deuterated derivative of any of the foregoing, wherein wherein:
r is 3, 4, or 5;
each $R^8$ and $R^9$ is independently chosen from hydrogen and deuterium; and
each $R^b$ is hydrogen.

110. The compound of any one of embodiments 96 to 106, a pharmaceutically acceptable salt thereof, or a deuterated derivative of any of the foregoing, wherein:
r is 3, 4, or 5;
each $R^8$ and $R^9$ is hydrogen; and
each $R^b$ is independently chosen from hydrogen and $C_1$-$C_2$ alkyl groups.

111. The compound of any one of embodiments 96 to 110, a pharmaceutically acceptable salt thereof, or a deuterated derivative of any of the foregoing, wherein each $R^3$ is independently $CD_3$.

112. The compound of embodiment 1, a pharmaceutically acceptable salt thereof, or a deuterated derivative of any of the foregoing, wherein the compound of Formula I is a compound of Formula V-A:

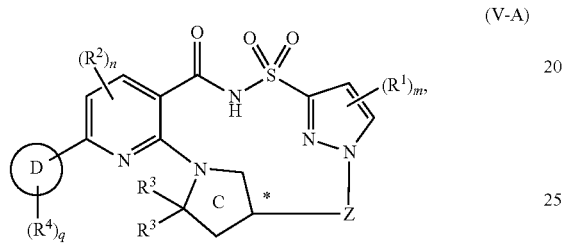

(V-A)

a pharmaceutically acceptable salt thereof, or a deuterated derivative of any of the foregoing,
wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -(Y)$_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from C($R^5$)($R^6$) groups, —O—, and —N$R^a$— groups, wherein a heteroatom in -(Y)$_k$-$R^7$ is not bonded to another heteroatom in -(Y)$_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;
q is 1 or 2;
Z is a divalent linker of formula (L)$_r$, wherein:
r is 3, 4, or 5;
each L is independently chosen from C($R^8$)($R^9$) groups, —O—, and —N$R^b$— groups, wherein a heteroatom in Z is not bonded to another heteroatom in Z, wherein:
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

113. The compound of embodiment 112, a pharmaceutically acceptable salt thereof, or a deuterated derivative of any of the foregoing, wherein each $R^1$ is independently chosen from deuterium, C1-C2 alkyl groups, and a hydroxyl group, and m is 0 or 1.

114. The compound of embodiment 112 or 113, a pharmaceutically acceptable salt thereof, or a deuterated derivative of any of the foregoing, wherein n is 0.

115. The compound of any one of embodiments 112 to 114, a pharmaceutically acceptable salt thereof, or a deuterated derivative of any of the foregoing, wherein Ring D is 5-membered heteroaryl ring substituted with $(R^4)_q$.

116. The compound of any one of embodiments 112 to 114, a pharmaceutically acceptable salt thereof, or a deuterated derivative of any of the foregoing, wherein Ring D is a pyrazolyl ring substituted with $(R^4)_q$.

117. The compound of any one of embodiments 112 to 114, a pharmaceutically acceptable salt thereof, or a deuterated derivative of any of the foregoing, wherein Ring D is

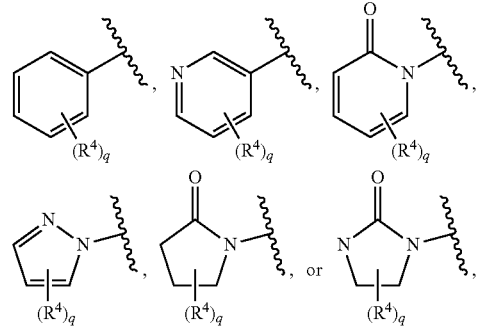

wherein

indicates the point of attachment of Ring D to Ring B.

118. The compound of any one of embodiments 112 to 117, a pharmaceutically acceptable salt thereof, or a deuterated derivative of any of the foregoing, wherein Ring D is

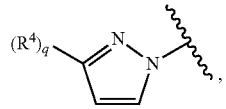

wherein

indicates the point of attachment of Ring D to Ring B.

119. The compound of any one of embodiments 112 to 118, a pharmaceutically acceptable salt thereof, or a deuterated derivative of any of the foregoing, wherein each $R^4$ is independently chosen from an oxo group or -$(Y)_k$-$R^7$ groups, wherein:
k is 0, 1, 2, 3, 4, 5, or 6;
each Y is independently chosen from C($R^5$)($R^6$) groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens.

120. The compound of any one of embodiments 112 to 118, a pharmaceutically acceptable salt thereof, or a deuterated derivative of any of the foregoing, wherein each $R^4$ is independently chosen from an oxo group or -$(Y)_k$-$R^7$ groups, wherein:
k is 0, 1, 2, 3, 4, 5, or 6;
each Y is independently chosen from C($R^5$)($R^6$) groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

121. The compound of any one of embodiments 112 to 118, a pharmaceutically acceptable salt thereof, or a deuterated derivative of any of the foregoing, wherein each $R^4$ is independently chosen from an oxo group or —O-$(Y)_k$-$R^7$ groups, wherein:
k is 0, 1, 2, 3, 4, or 5;
each Y is independently chosen from C($R^5$)($R^6$) groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens.

122. The compound of any one of embodiments 112 to 118, a pharmaceutically acceptable salt thereof, or a deuterated derivative of any of the foregoing, wherein each $R^4$ is independently chosen from

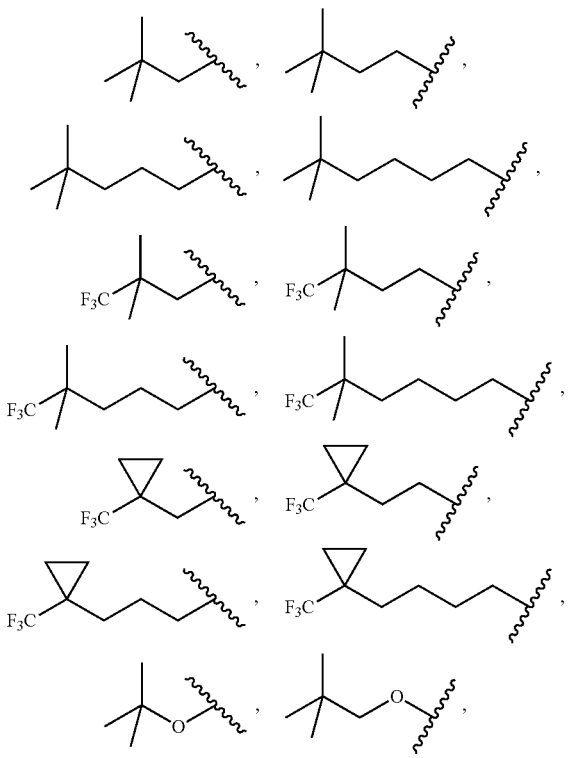

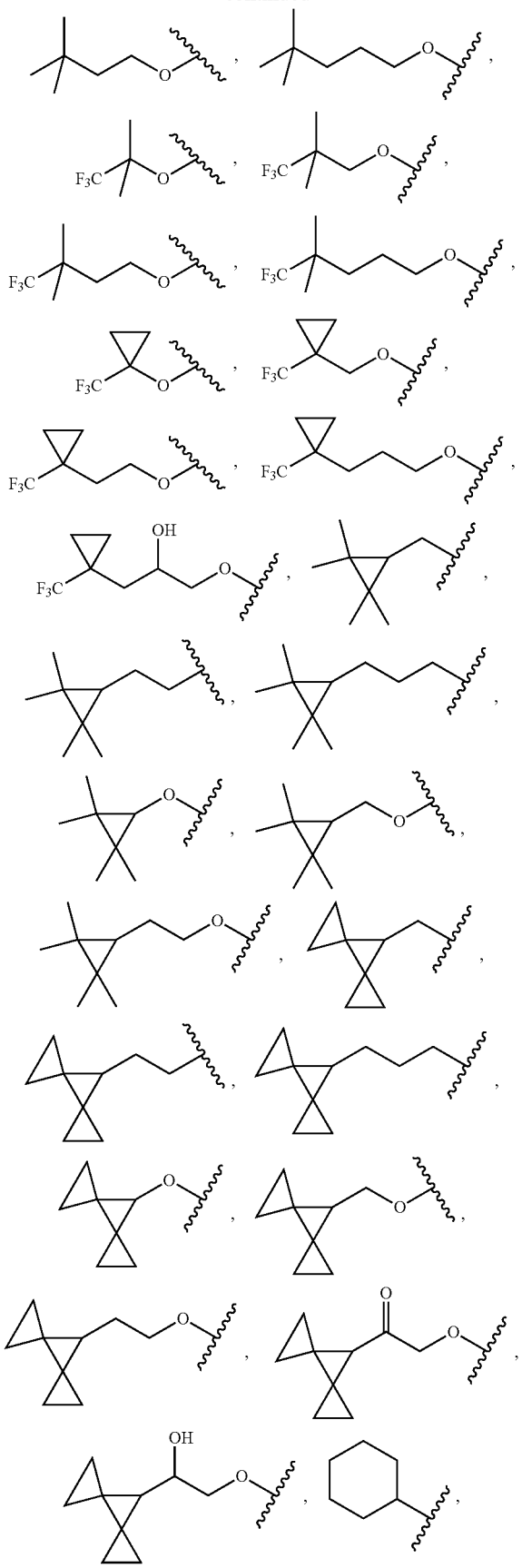
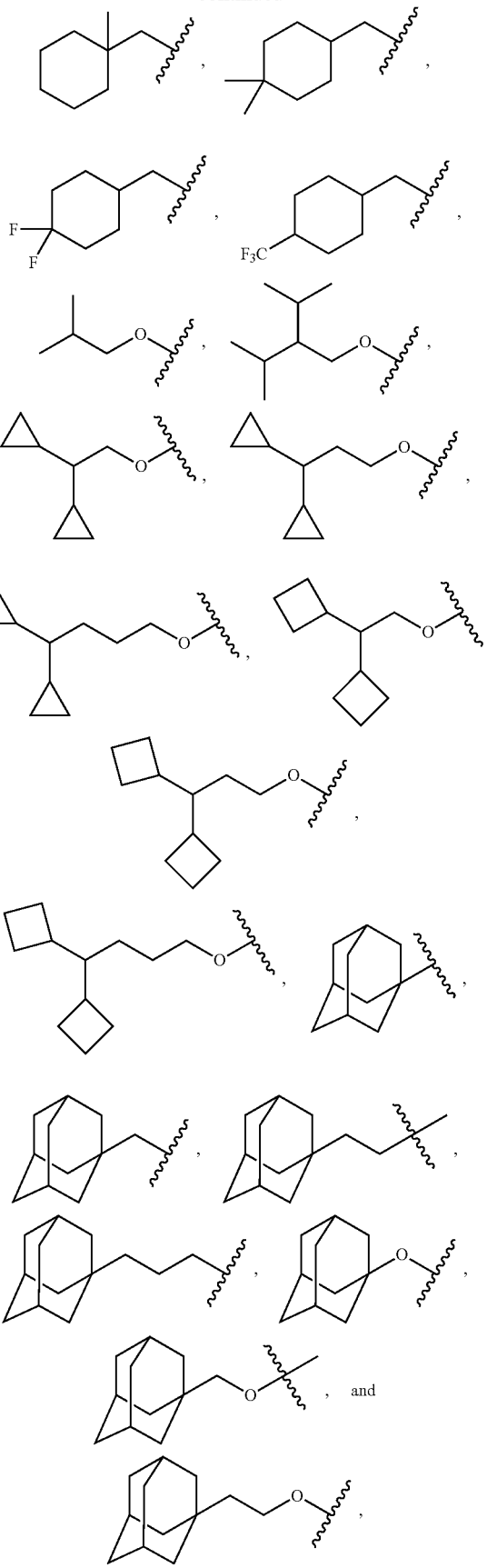

wherein

indicates the point of attachment of R⁴ to Ring D.
123. The compound of any one of embodiments 112 to 122, a pharmaceutically acceptable salt thereof, or a deuterated derivative of any of the foregoing, wherein k is 3, 4, 5, or 6.
124. The compound of any one of embodiments 112 to 123, a pharmaceutically acceptable salt thereof, or a deuterated derivative of any of the foregoing, wherein q is 1.
125. The compound of any one of embodiments 112 to 124, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R⁸)(R⁹) groups, —O—, and —NR$^b$— groups, wherein a heteroatom in Z is not bonded to another heteroatom in Z, wherein:
each R⁸ and R⁹ is independently chosen from hydrogen and deuterium; and
each R$^b$ is independently chosen from hydrogen and $C_1$-$C_2$ alkyl groups.
126. The compound of any one of embodiments 112 to 124, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R⁸)(R⁹) groups and —NR$^b$— groups, wherein a heteroatom in Z is not bonded to another heteroatom in Z, wherein:
each R⁸ and R⁹ is independently chosen from hydrogen and deuterium; and
each R$^b$ is independently chosen from hydrogen and methyl.
127. The compound of any one of embodiments 112 to 124, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R⁸)(R⁹) groups and —NR$^b$— groups, wherein a heteroatom in Z is not bonded to another heteroatom in Z, wherein:
each R⁸ and R⁹ is independently chosen from hydrogen and deuterium; and
each R$^b$ is hydrogen.
128. The compound of any one of embodiments 112 to 124, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R⁸)(R⁹) groups, —O—, and —NR$^b$— groups, wherein a heteroatom in Z is not bonded to another heteroatom in Z, wherein:
each R⁸ and R⁹ is hydrogen; and
each R$^b$ is independently chosen from hydrogen and $C_1$-$C_2$ alkyl groups.
129. The compound of any one of embodiments 112 to 128, a pharmaceutically acceptable salt thereof, or a deuterated derivative of any of the foregoing, wherein each R³ is independently CD₃.
130. The compound of embodiment 1, a pharmaceutically acceptable salt thereof, or a deuterated derivative of any of the foregoing, wherein the compound of Formula I is a compound of Formula V-B:

(V-B)

a pharmaceutically acceptable salt thereof, or a deuterated derivative of any of the foregoing,
wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
each R¹ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each R² is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each R³ is methyl;
each R⁴ is independently chosen from halogens, an oxo group, a hydroxyl group, a cyano group, and -(Y)$_k$-R⁷ groups, or optionally two R⁴, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from C(R⁵)(R⁶) groups, —O—, and —NR$^a$— groups, wherein a heteroatom in -(Y)$_k$-R⁷ is not bonded to another heteroatom in -(Y)$_k$-R⁷, wherein:
each R⁵ and R⁶ is independently chosen from hydrogen, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group or oxo;
each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each R$^a$ is independently chosen from hydrogen and $C_1$-$C_2$ alkyl groups; and
R⁷ is chosen from hydrogen, halogens, a cyano group, and $C_3$-$C_{10}$ to cycloalkyl groups optionally substituted with one or more groups chosen from C$_1$-C$_2$ alkyl groups, C$_1$-C$_2$ haloalkyl groups, and halogens;
q is 1 or 2;
r is 3, 4, or 5; and
each R$^8$ and R$^9$ is independently chosen from hydrogen, halogens, C$_1$-C$_2$ alkyl groups, a hydroxyl group, C$_1$-C$_2$ alkoxyl groups, and C$_1$-C$_2$ haloalkoxyl groups.

131. The compound of embodiment 130, a pharmaceutically acceptable salt thereof, or a deuterated derivative of any of the foregoing, wherein each R$^8$ and R$^9$ is independently chosen from hydrogen, deuterium, halogens, C$_1$-C$_2$ alkyl groups, a hydroxyl group, C$_1$-C$_2$ alkoxyl groups, and C$_1$-C$_2$ haloalkoxyl groups.

132. The compound of embodiment 130 or 131, a pharmaceutically acceptable salt thereof, or a deuterated derivative of any of the foregoing, wherein each R$^8$ and R$^9$ is H.

133. The compound of any one of embodiments 130 to 132, a pharmaceutically acceptable salt thereof, or a deuterated derivative of any of the foregoing, wherein each R$^1$ is independently chosen from deuterium, C$_1$-C$_2$ alkyl groups, and a hydroxyl group, and m is 0 or 1.

134. The compound of any one of embodiments 130 to 133, a pharmaceutically acceptable salt thereof, or a deuterated derivative of any of the foregoing, wherein n is 0.

135. The compound of any one of embodiments 130 to 134, a pharmaceutically acceptable salt thereof, or a deuterated derivative of any of the foregoing, wherein Ring D is a 5-membered heteroaryl ring substituted with (R$^4$)$_q$.

136. The compound of any one of embodiments 130 to 134, a pharmaceutically acceptable salt thereof, or a deuterated derivative of any of the foregoing, wherein Ring D is a pyrazolyl ring substituted with (R$^4$)$_q$.

137. The compound of any one of embodiments 130 to 134, a pharmaceutically acceptable salt thereof, or a deuterated derivative of any of the foregoing, wherein Ring D is

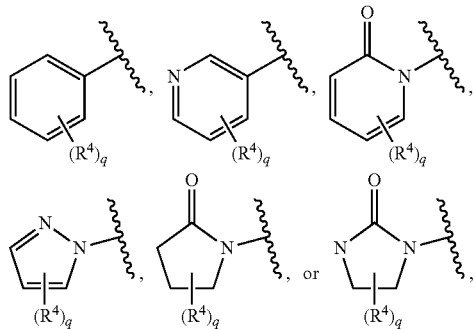

wherein

indicates the point of attachment of Ring D to Ring B.

138. The compound of any one of embodiments 130 to 137, a pharmaceutically acceptable salt thereof, or a deuterated derivative of any of the foregoing, wherein Ring D is

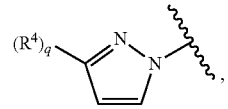

wherein

indicates the point of attachment of Ring D to Ring B.

139. The compound of any one of embodiments 130 to 138, a pharmaceutically acceptable salt thereof, or a deuterated derivative of any of the foregoing, wherein each R$^4$ is independently chosen from an oxo group or -(Y)$_k$-R$^7$ groups, wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
each R$^5$ and R$^6$ is independently chosen from hydrogen, deuterium, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
each R$^a$ is independently chosen from hydrogen and C$_1$-C$_2$ alkyl groups; and
R$^7$ is chosen from hydrogen, halogens, a cyano group, and C$_3$-C$_{10}$ cycloalkyl groups optionally substituted with one or more groups chosen from C$_1$-C$_2$ alkyl groups, C$_1$-C$_2$ haloalkyl groups, and halogens.

140. The compound of any one of embodiments 130 to 138, a pharmaceutically acceptable salt thereof, or a deuterated derivative of any of the foregoing, wherein each R$^4$ is independently chosen from an oxo group or -(Y)$_k$-R$^7$ groups, wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
each R$^5$ and R$^6$ is independently chosen from hydrogen, deuterium, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group;
each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

141. The compound of any one of embodiments 130 to 138, a pharmaceutically acceptable salt thereof, or a deuterated derivative of any of the foregoing, wherein each $R^4$ is independently chosen from an oxo group or —O-(Y)$_k$-$R^7$ groups, wherein:

k is 0, 1, 2, 3, 4, or 5;

each Y is independently chosen from $C(R^5)(R^6)$ groups, —O—, and —$NR^a$— groups, wherein a heteroatom in -(Y)$_k$-$R^7$ is not bonded to another heteroatom in -(Y)$_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens.

142. The compound of any one of embodiments 130 to 138, a pharmaceutically acceptable salt thereof, or a deuterated derivative of any of the foregoing, wherein each $R^4$ is independently chosen from

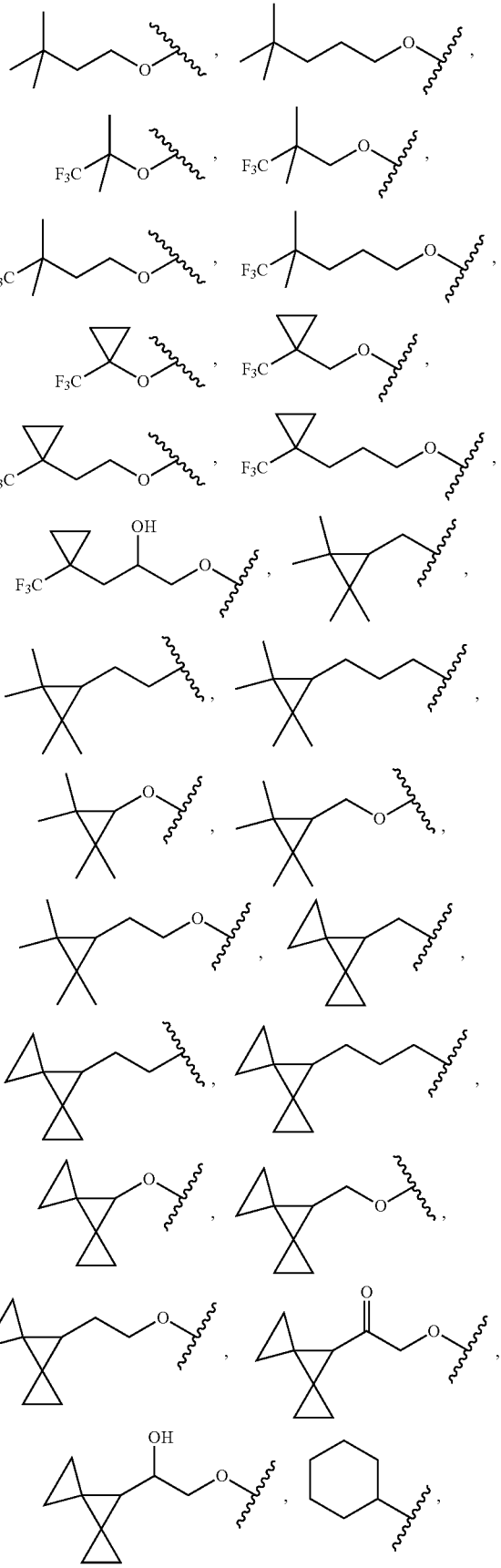

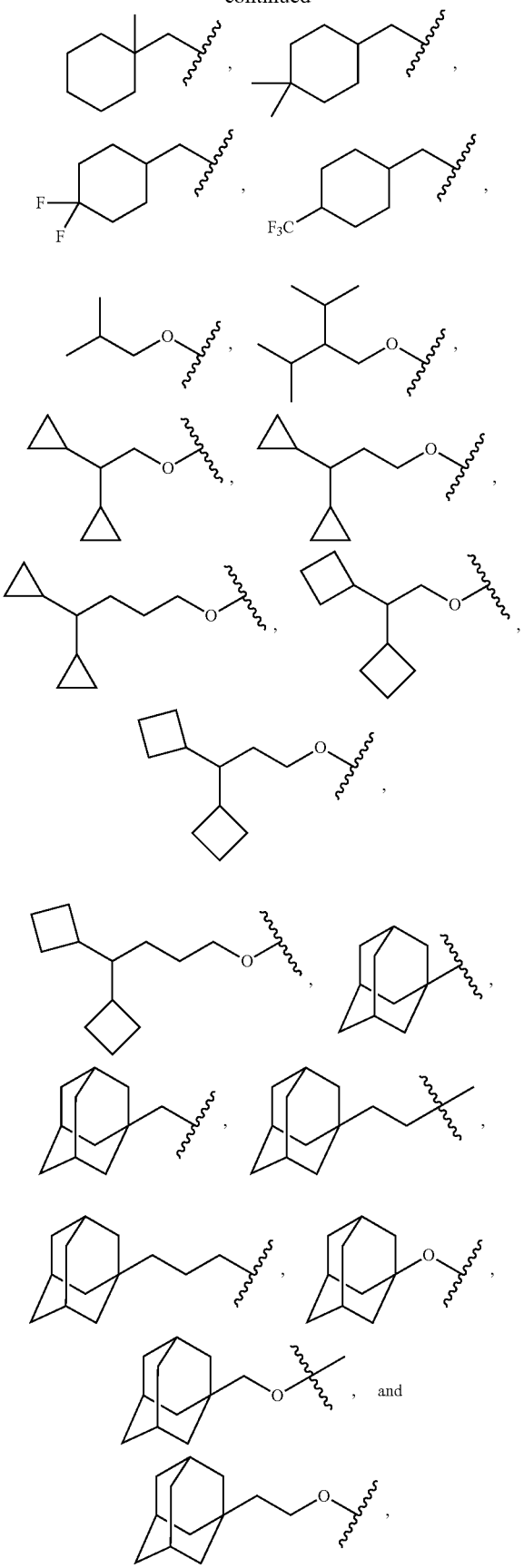

indicates the point of attachment of R⁴ to Ring D.

143. The compound of any one of embodiments 130 to 142, a pharmaceutically acceptable salt thereof, or a deuterated derivative of any of the foregoing, wherein k is 3, 4, 5, or 6.

144. The compound of any one of embodiments 130 to 143, a pharmaceutically acceptable salt thereof, or a deuterated derivative of any of the foregoing, wherein q is 1.

145. The compound of any one of embodiments 130 to 144, a pharmaceutically acceptable salt thereof, or a deuterated derivative of any of the foregoing, wherein:
r is 3, 4, or 5; and
each $R^8$ and $R^9$ is independently chosen from hydrogen and deuterium.

146. The compound of any one of embodiments 130 to 144, a pharmaceutically acceptable salt thereof, or a deuterated derivative of any of the foregoing, wherein:
r is 3, 4, or 5; and
each $R^8$ and $R^9$ is hydrogen.

147. The compound of any one of embodiments 130 to 144, a pharmaceutically acceptable salt thereof, or a deuterated derivative of any of the foregoing, wherein:
r is 3, 4, or 5; and
each $R^8$ and $R^9$ is deuterium.

148. The compound of any one of embodiments 130 to 144, a pharmaceutically acceptable salt thereof, or a deuterated derivative of any of the foregoing, wherein:
r is 3 or 4; and
each $R^8$ and $R^9$ is hydrogen.

149. The compound of any one of embodiments 130 to 148, a pharmaceutically acceptable salt thereof, or a deuterated derivative of any of the foregoing, wherein each $R^3$ is independently $CD_3$.

150. The compound of embodiment 1, a pharmaceutically acceptable salt thereof, or a deuterated derivative of any of the foregoing, wherein the compound of Formula I is a compound of Formula VI-A or VI-B:

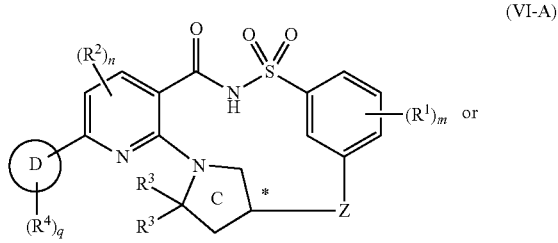

(VI-A)

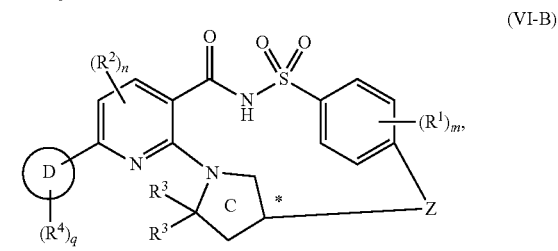

(VI-B)

a pharmaceutically acceptable salt thereof, or a deuterated derivative of any of the foregoing, wherein:

the carbon denoted by * has S-stereochemistry or R-stereochemistry;

Ring D is a phenyl ring, a 5-membered heterocyclyl ring, a 6-membered heterocyclyl ring, a 5-membered heteroaryl ring, or a 6-membered heteroaryl ring;

each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

m is 0, 1, 2, 3, or 4;

each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;

q is 1 or 2;

Z is a divalent linker of formula $(L)_r$, wherein:

r is 3, 4, or 5;

each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

151. The compound of embodiment 150, a pharmaceutically acceptable salt thereof, or a deuterated derivative of any of the foregoing, wherein each $R^1$ is independently chosen from deuterium, $C_1$-$C_2$ alkyl groups, and a hydroxyl group, and m is 0 or 1.

152. The compound of embodiment 150 or 151, a pharmaceutically acceptable salt thereof, or a deuterated derivative of any of the foregoing, wherein n is 0.

153. The compound of any one of embodiments 150 to 152, a pharmaceutically acceptable salt thereof, or a deuterated derivative of any of the foregoing, wherein Ring D is a 5-membered heteroaryl ring substituted with $(R^4)_q$.

154. The compound of any one of embodiments 150 to 152, a pharmaceutically acceptable salt thereof, or a deuterated derivative of any of the foregoing, wherein Ring D is a pyrazolyl ring substituted with $(R^4)_q$.

155. The compound of any one of embodiments 150 to 152, a pharmaceutically acceptable salt thereof, or a deuterated derivative of any of the foregoing, wherein Ring D is

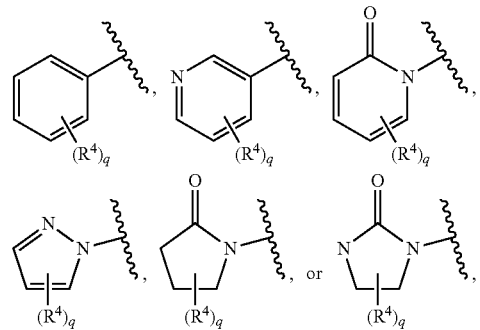

wherein

indicates the point of attachment of Ring D to Ring B.

156. The compound of any one of embodiments 150 to 152, a pharmaceutically acceptable salt thereof, or a deuterated derivative of any of the foregoing, wherein Ring D is

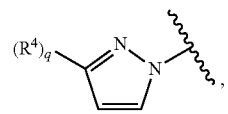

wherein

indicates the point of attachment of Ring D to Ring B.

157. The compound of any one of embodiments 150 to 156, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;
  each Y is independently chosen from C(R⁵)(R⁶) groups, —O—, and —NR$^a$— groups, wherein a heteroatom in -(Y)$_k$-R⁷ is not bonded to another heteroatom in -(Y)$_k$-R⁷, wherein:
  each R⁵ and R⁶ is independently chosen from hydrogen, deuterium, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group or oxo;
  each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
  each R$^a$ is independently chosen from hydrogen and $C_1$-$C_2$ alkyl groups; and
R⁷ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

158. The compound of any one of embodiments 150 to 156, a pharmaceutically acceptable salt thereof, or a deuterated derivative of any of the foregoing, wherein each R⁴ is independently chosen from an oxo group or -(Y)$_k$-R⁷ groups, wherein:
k is 0, 1, 2, 3, 4, 5, or 6;
  each Y is independently chosen from C(R⁵)(R⁶) groups, —O—, and —NR$^a$— groups, wherein a heteroatom in -(Y)$_k$-R⁷ is not bonded to another heteroatom in -(Y)$_k$-R⁷, wherein:
    each R⁵ and R⁶ is independently chosen from hydrogen, deuterium, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group;
    each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
    each R$^a$ is independently chosen from hydrogen and $C_1$-$C_2$ alkyl groups; and
R⁷ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

159. The compound of any one of embodiments 150 to 156, a pharmaceutically acceptable salt thereof, or a deuterated derivative of any of the foregoing, wherein each R⁴ is independently chosen from an oxo group or —O-(Y)$_k$-R⁷ groups, wherein:
k is 0, 1, 2, 3, 4, or 5;
  each Y is independently chosen from C(R⁵)(R⁶) groups, —O—, and —NR$^a$— groups, wherein a heteroatom in -(Y)$_k$-R⁷ is not bonded to another heteroatom in -(Y)$_k$-R⁷, wherein:
    each R⁵ and R⁶ is independently chosen from hydrogen, deuterium, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group or oxo;
    each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each R$^a$ is independently chosen from hydrogen and $C_1$-$C_2$ alkyl groups; and
R⁷ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens.

160. The compound of any one of embodiments 150 to 156, a pharmaceutically acceptable salt thereof, or a deuterated derivative of any of the foregoing, wherein each R⁴ is independently chosen from

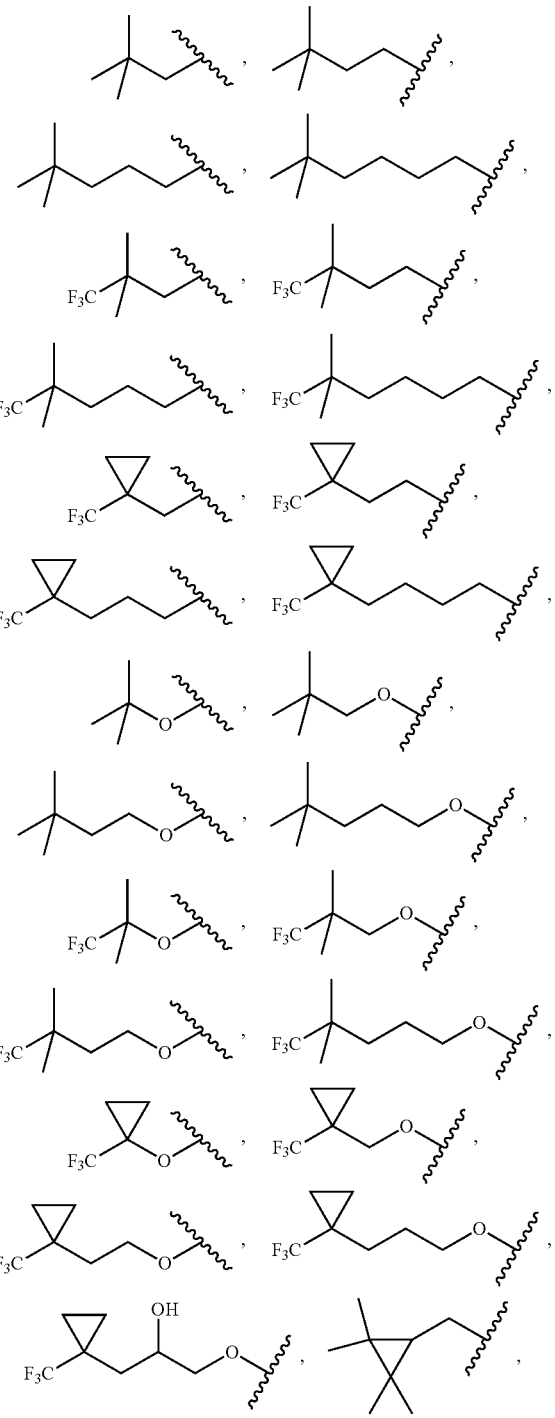

-continued

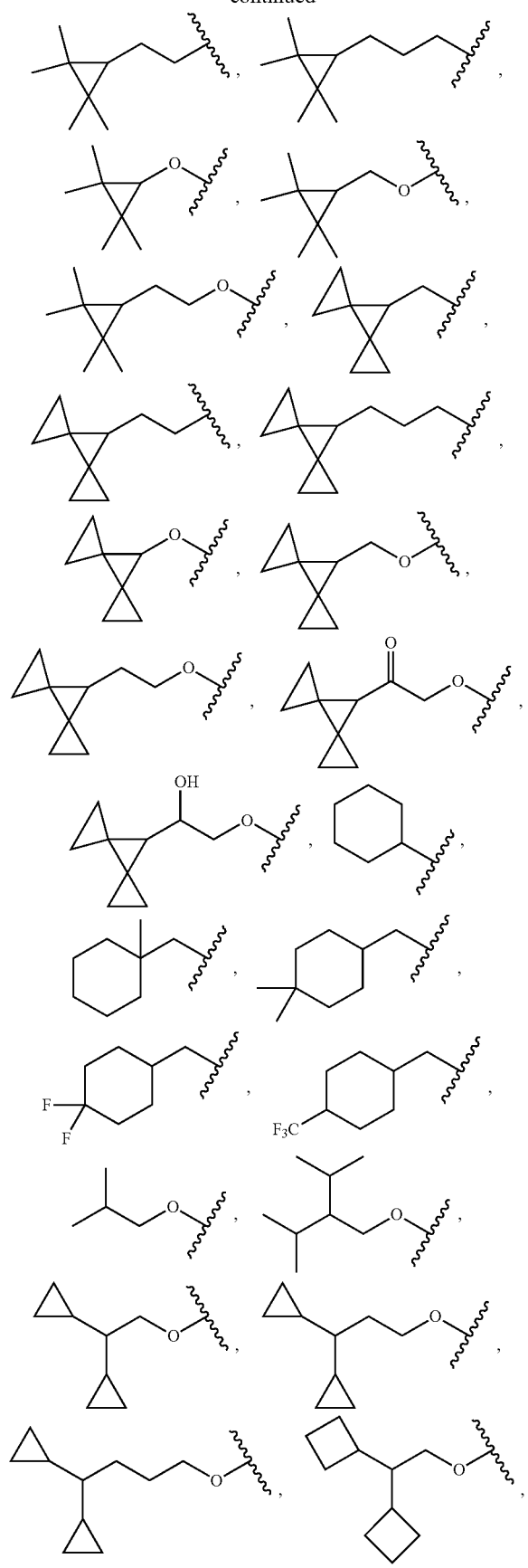

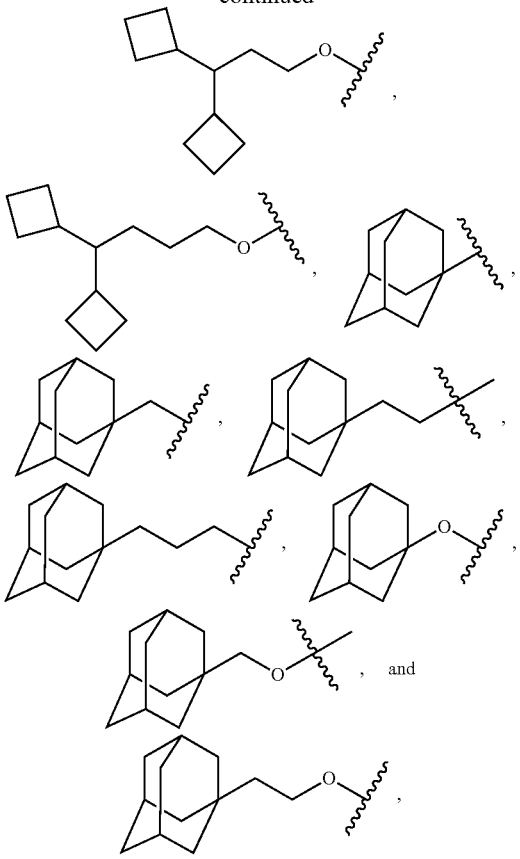

wherein

indicates the point of attachment of R⁴ to Ring D.

161. The compound of any one of embodiments 150 to 160, a pharmaceutically acceptable salt thereof, or a deuterated derivative of any of the foregoing, wherein k is 3, 4, 5, or 6.

162. The compound of any one of embodiments 150 to 161, a pharmaceutically acceptable salt thereof, or a deuterated derivative of any of the foregoing, wherein q is 1.

163. The compound of any one of embodiments 150 to 162, a pharmaceutically acceptable salt thereof, or a deuterated derivative of any of the foregoing, wherein Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
  each $R^8$ and $R^9$ is independently chosen from hydrogen and deuterium; and
  each $R^b$ is independently chosen from hydrogen and $C_1$-$C_2$ alkyl groups.

164. The compound of any one of embodiments 150 to 162, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R$^8$)(R$^9$) groups and —NR$^b$— groups, wherein a heteroatom in Z is not bonded to another heteroatom in Z, wherein:
each R$^8$ and R$^9$ is independently chosen from hydrogen and deuterium; and
each R$^b$ is independently chosen from hydrogen and methyl.

165. The compound of any one of embodiments 150 to 162, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R$^8$)(R$^9$) groups and —NR$^b$— groups, wherein a heteroatom in Z is not bonded to another heteroatom in Z, wherein:
each R$^8$ and R$^9$ is independently chosen from hydrogen and deuterium; and
each R$^b$ is hydrogen.

166. The compound of any one of embodiments 150 to 162, a pharmaceutically acceptable salt thereof, or a deuterated derivative of any of the foregoing, wherein Z is a divalent linker of formula (L)$_r$, wherein:
r is 3, 4, or 5;
each L is independently chosen from C(R$^8$)(R$^9$) groups, —O—, and —NR$^b$— groups, wherein a heteroatom in Z is not bonded to another heteroatom in Z, wherein:
each R$^8$ and R$^9$ is hydrogen; and
each R$^b$ is independently chosen from hydrogen and C$_1$-C$_2$ alkyl groups.

167. The compound of any one of embodiments 150 to 166, a pharmaceutically acceptable salt thereof, or a deuterated derivative of any of the foregoing, wherein each R$^3$ is independently CD$_3$.

168. The compound of embodiment 1, a pharmaceutically acceptable salt thereof, or a deuterated derivative of any of the foregoing, wherein the compound of Formula I is a compound of Formula VI-C or VI-D:

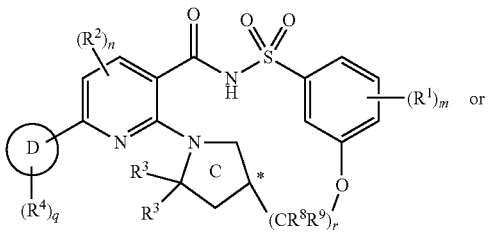

(VI-C)

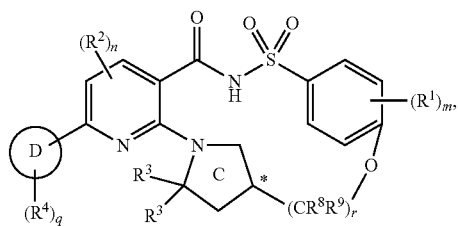

(VI-D)

a pharmaceutically acceptable salt thereof, or a deuterated derivative of any of the foregoing,
wherein:
the carbon denoted by * has S-stereochemistry or R-stereochemistry;

Ring D is a phenyl ring, a 5-membered heterocyclyl ring, a 6-membered heterocyclyl ring, a 5-membered heteroaryl ring, or a 6-membered heteroaryl ring;
X is O, NH, or an N(C$_1$-C$_4$ alkyl);
each R$^1$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
m is 0, 1, 2, 3, or 4;
each R$^2$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
n is 0, 1, or 2;
each R$^3$ is methyl;
each R$^4$ is independently chosen from halogens, an oxo group, a hydroxyl group, a cyano group, and -(Y)$_k$-R$^7$ groups, or optionally two R$^4$, together with the atom(s) they are attached to, form a 5-6 membered cycloalkyl or heterocyclyl ring that is optionally and independently substituted with one or more groups chosen from halogens, C$_1$-C$_2$ alkyl groups, haloalkyl groups, a hydroxyl group, C$_1$-C$_2$ alkoxyl groups, and C$_1$-C$_2$ haloalkoxyl groups, wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
each R$^5$ and R$^6$ is independently chosen from hydrogen, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
each R$^a$ is independently chosen from hydrogen and C$_1$-C$_2$ alkyl groups; and
R$^7$ is chosen from hydrogen, halogens, a cyano group, and C$_3$-C$_{10}$ cycloalkyl groups optionally substituted with one or more groups chosen from C$_1$-C$_2$ alkyl groups, C$_1$-C$_2$ haloalkyl groups, and halogens;
q is 1 or 2;
r is 3 or 4; and
each R$^8$ and R$^9$ is independently chosen from hydrogen, halogens, C$_1$-C$_2$ alkyl groups, a hydroxyl group, C$_1$-C$_2$ alkoxyl groups, and C$_1$-C$_2$ haloalkoxyl groups.

169. The compound of embodiment 168, a pharmaceutically acceptable salt thereof, or a deuterated derivative of any of the foregoing, wherein each R$^8$ and R$^9$ is independently chosen from hydrogen, deuterium, halogens, C$_1$-C$_2$ alkyl groups, a hydroxyl group, C$_1$-C$_2$ alkoxyl groups, and C$_1$-C$_2$ haloalkoxyl groups.

170. The compound of embodiment 169 or 169, a pharmaceutically acceptable salt thereof, or a deuterated derivative of any of the foregoing, wherein each R$^8$ and R$^9$ is H.

171. The compound of any one of embodiments 168 to 170, a pharmaceutically acceptable salt thereof, or a deuterated derivative of any of the foregoing, wherein each $R^1$ is independently chosen from deuterium, $C_1$-$C_2$ alkyl groups, and a hydroxyl group, and m is 0 or 1.

172. The compound of any one of embodiments 168 to 171, a pharmaceutically acceptable salt thereof, or a deuterated derivative of any of the foregoing, wherein n is 0.

173. The compound of any one of embodiments 168 to 172, a pharmaceutically acceptable salt thereof, or a deuterated derivative of any of the foregoing, wherein Ring D a 5-membered heteroaryl ring substituted with $(R^4)_q$.

174. The compound of any one of embodiments 168 to 172, a pharmaceutically acceptable salt thereof, or a deuterated derivative of any of the foregoing, wherein Ring D is a pyrazolyl ring substituted with $(R^4)_q$.

175. The compound of any one of embodiments 168 to 172, a pharmaceutically acceptable salt thereof, or a deuterated derivative of any of the foregoing, wherein Ring D is

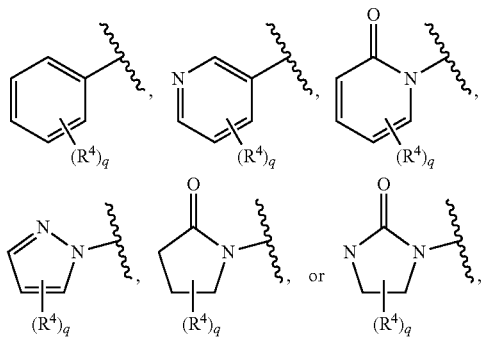

wherein

indicates the point of attachment of Ring D to Ring B.

176. The compound of any one of embodiments 168 to 172, a pharmaceutically acceptable salt thereof, or a deuterated derivative of any of the foregoing, wherein Ring D is

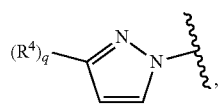

wherein

indicates the point of attachment of Ring D to Ring B.

177. The compound of any one of embodiments 168 to 172, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

178. The compound of any one of embodiments 168 to 176, a pharmaceutically acceptable salt thereof, or a deuterated derivative of any of the foregoing, wherein each $R^4$ is independently chosen from an oxo group or -$(Y)_k$-$R^7$ groups, wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens.

179. The compound of any one of embodiments 168 to 176, a pharmaceutically acceptable salt thereof, or a deuterated derivative of any of the foregoing, wherein each $R^4$ is independently chosen from an oxo group or —O-$(Y)_k$-$R^7$ groups, wherein:

k is 0, 1, 2, 3, 4, or 5;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, deuterium, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of R⁵ and R⁶ is optionally independently substituted with one or more groups chosen from C₁-C₂ alkyl groups, C₁-C₂ haloalkyl groups, halogens, a hydroxyl group, C₁-C₂ alkoxyl groups, and C₁-C₂ haloalkoxyl groups; and each Rᵃ is independently chosen from hydrogen and C₁-C₂ alkyl groups; and R⁷ is chosen from hydrogen, halogens, a cyano group, and C₃-C₁₀ cycloalkyl groups optionally substituted with one or more groups chosen from C₁-C₂ alkyl groups, C₁-C₂ haloalkyl groups, and halogens.

180. The compound of any one of embodiments 168 to 176, a pharmaceutically acceptable salt thereof, or a deuterated derivative of any of the foregoing, wherein each R⁴ is independently chosen from

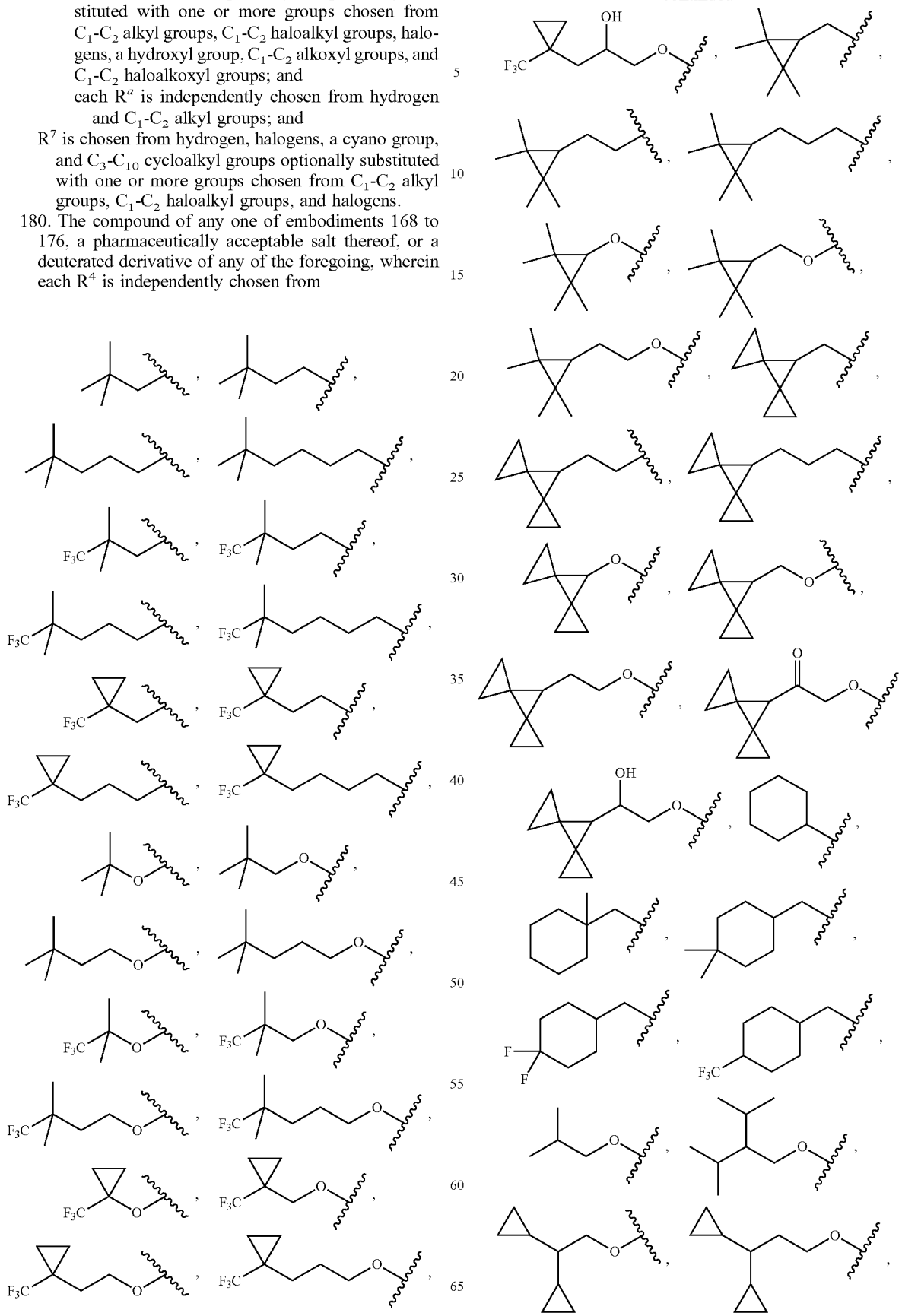

123

-continued

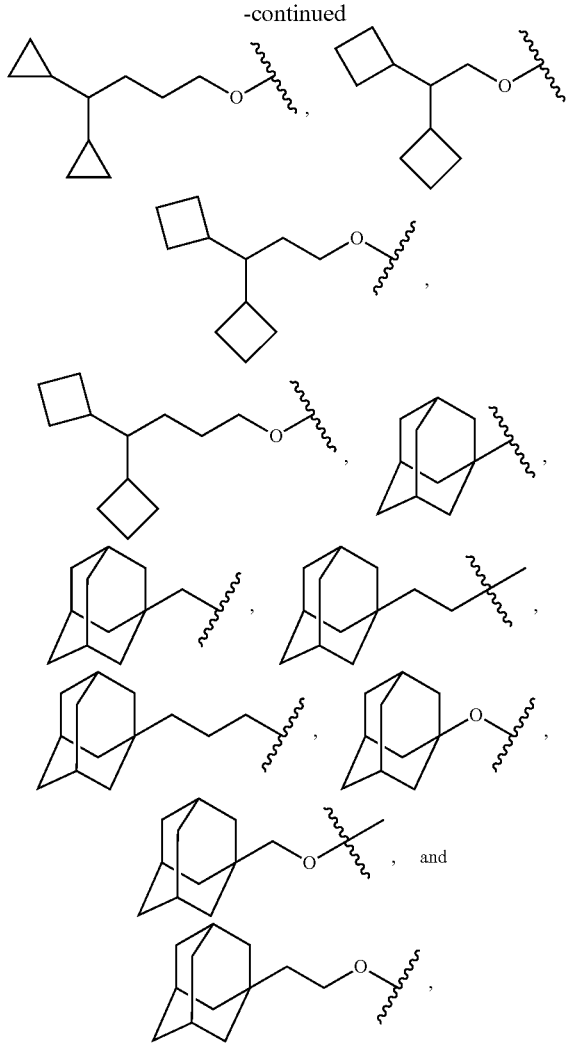

wherein

indicates the point of attachment of $R^4$ to Ring D.

181. The compound of any one of embodiments 168 to 180, a pharmaceutically acceptable salt thereof, or a deuterated derivative of any of the foregoing, wherein k is 3, 4, 5, or 6.

182. The compound of any one of embodiments 168 to 181, a pharmaceutically acceptable salt thereof, or a deuterated derivative of any of the foregoing, wherein q is 1.

183. The compound of any one of embodiments 168 to 182, a pharmaceutically acceptable salt thereof, or a deuterated derivative of any of the foregoing, wherein:
r is 3, 4, or 5; and
each $R^8$ and $R^9$ is independently chosen from hydrogen and deuterium.

184. The compound of any one of embodiments 168 to 182, a pharmaceutically acceptable salt thereof, or a deuterated derivative of any of the foregoing, wherein:

124 r is 3, 4, or 5; and
each $R^8$ and $R^9$ is hydrogen.

185. The compound of any one of embodiments 168 to 182, a pharmaceutically acceptable salt thereof, or a deuterated derivative of any of the foregoing, wherein:
r is 3, 4, or 5; and
each $R^8$ and $R^9$ is deuterium.

186. The compound of any one of embodiments 168 to 182, a pharmaceutically acceptable salt thereof, or a deuterated derivative of any of the foregoing, wherein:
r is 3 or 4; and
each $R^8$ and $R^9$ is hydrogen.

187. The compound of any one of embodiments 168 to 186, wherein each $R^3$ is independently $CD_3$.

188. The compound of any one of embodiments 20-57, a pharmaceutically acceptable salt thereof, or a deuterated derivative of any of the foregoing, wherein the carbon denoted by * of formula (II-A) or (III-A) has S-stereochemistry, and wherein the carbon denoted by * of formula (II-B) or (III-B) has R-stereochemistry.

189. The compound of any one of embodiments 58-187, a pharmaceutically acceptable salt thereof, or a deuterated derivative of any of the foregoing, wherein the carbon denoted by * of any one of formulae (IV-A), (IV-B), (IV-C), (V-A), (V-B), (VI-A), (VI-B), (VI-C), and (VI-D) has S-stereochemistry.

190. The compound of any one of embodiments 58-187, a pharmaceutically acceptable salt thereof, or a deuterated derivative of any of the foregoing, wherein the carbon denoted by * of any one of formulae (IV-A), (IV-B), (IV-C), (V-A), (V-B), (VI-A), (VI-B), (VI-C), and (VI-D) has R-stereochemistry.

191. A compound chosen from compounds Nos. 1-302 depicted in FIG. 1, pharmaceutically acceptable salts thereof, and deuterated derivatives of any of the foregoing.

192. A compound chosen from compounds Nos. 303-309 depicted in FIG. 1, pharmaceutically acceptable salts thereof, and deuterated derivatives of any of the foregoing.

193. A compound selected from:

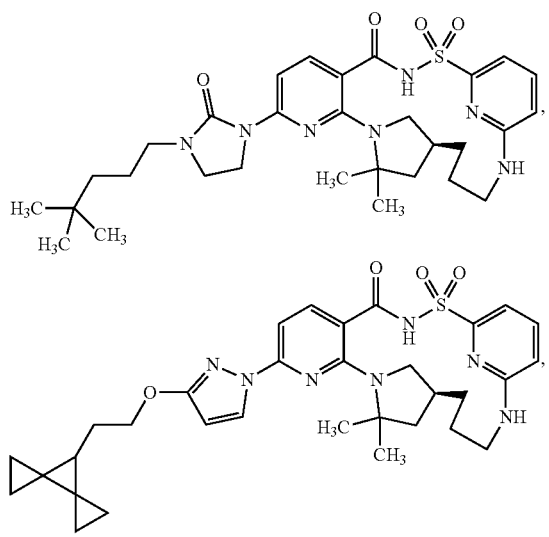

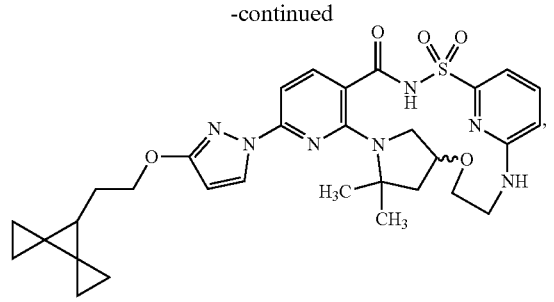

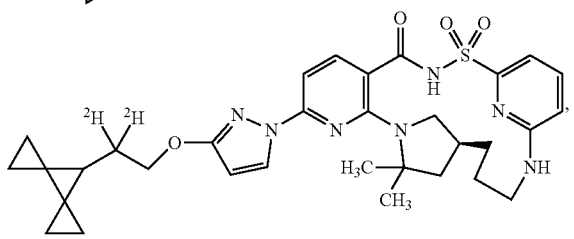

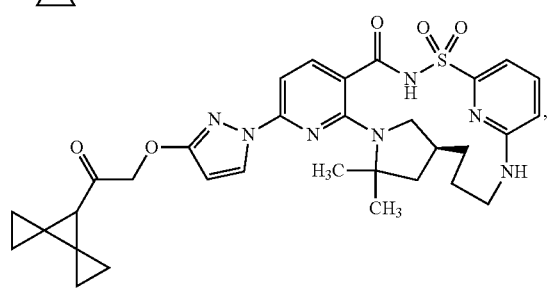

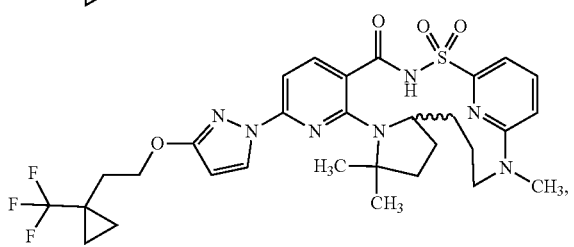

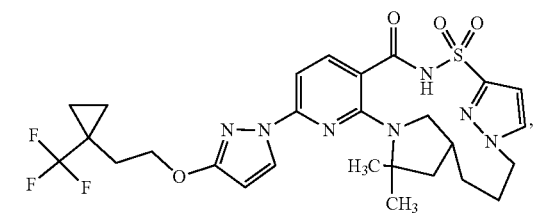

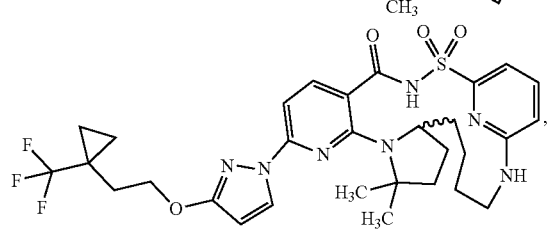

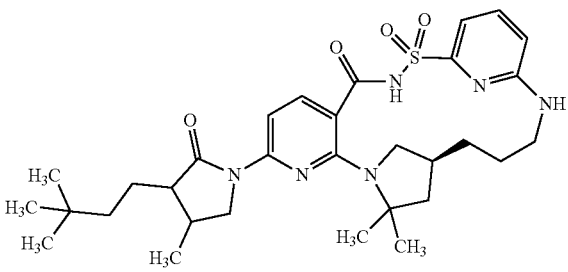

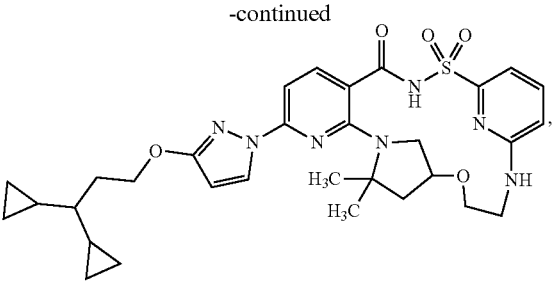

pharmaceutically acceptable salts thereof, and deuterated derivatives of any of the foregoing.

194. A pharmaceutical composition comprising at least one compound chosen from compounds of any one of embodiments 1-191 a pharmaceutically acceptable salt thereof, or a deuterated derivative of any of the foregoing, and optionally one or more of:
(a) Compound II.

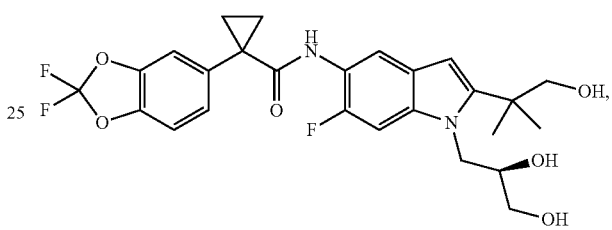

a pharmaceutically acceptable salt thereof, or a deuterated derivative of any of the foregoing;
(b) Compound III:

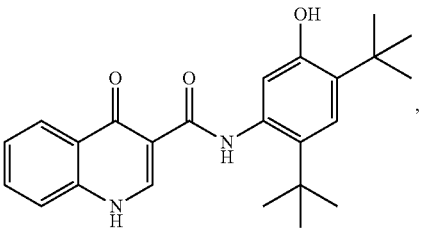

a pharmaceutically acceptable salt thereof, or a deuterated derivative of any of the foregoing; and
(c) a pharmaceutically acceptable carrier.

195. A method of treating cystic fibrosis comprising administering to a patient in need thereof a compound of any one of embodiments 1 to 191 or a pharmaceutical composition according to embodiment 194.

196. Use of at least one compound chosen from compounds of any one of embodiments 1-191 a pharmaceutically acceptable salt thereof, or a deuterated derivative of any of the foregoing, and optionally one or more of:
(a) Compound II:

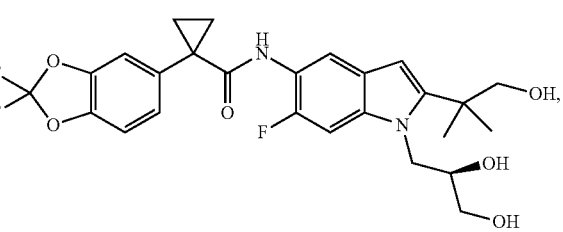

a pharmaceutically acceptable salt thereof, or a deuterated derivative of any of the foregoing:

(b) Compound III:

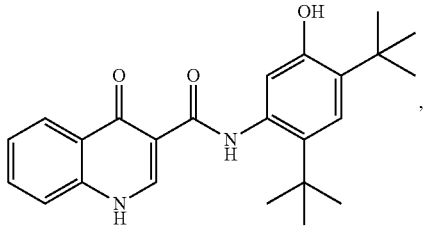

a pharmaceutically acceptable salt thereof, or a deuterated derivative of any of the foregoing;
for treating cystic fibrosis.

197. A compound of Formula (X):

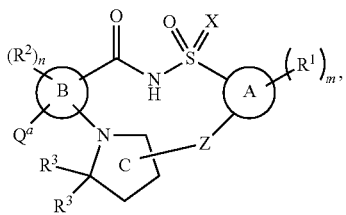

a salt thereof, or a deuterated derivative of any of the foregoing,
wherein:
  $Q^a$ is a halogen;
  Ring A is a phenyl, a 5-membered heteroaryl ring, or a 6-membered heteroaryl ring;
  Ring B is a pyridinyl ring;
  X is O, NH, or an $N(C_1-C_4$ alkyl);
  each $R^1$ is independently chosen from $C_1-C_2$ alkyl groups, $C_1-C_2$ alkoxyl groups, $C_1-C_2$ haloalkyl groups, $C_1-C_2$ haloalkoxyl groups, halogens, a cyano group, and a hydroxyl group;
  m is 0, 1, 2, 3, or 4;
  each $R^2$ is independently chosen from $C_1-C_2$ alkyl groups, $C_1-C_2$ alkoxyl groups, $C_1-C_2$ haloalkyl groups, $C_1-C_2$ haloalkoxyl groups, halogens, a cyano group, and a hydroxyl group;
  n is 0, 1, or 2;
  each $R^3$ is methyl;
  Z is a divalent linker of formula $(L)_r$, wherein:
    r is 1, 2, 3, 4, 5, or 6;
    each L is independently chosen from $C(R^8)(R^9)$ groups, —O—, and —$NR^b$— groups, wherein a heteroatom in Z is not bonded to another heteroatom in Z, wherein:
      each $R^8$ and $R^9$ is independently chosen from hydrogen, halogens, $C_1-C_2$ haloalkyl groups, $C_1-C_2$ alkyl groups, a hydroxyl group, $C_1-C_2$ alkoxyl groups, and $C_1-C_2$ haloalkoxyl groups; and
      each $R^b$ is independently chosen from hydrogen and $C_1-C_2$ alkyl groups.

198. A compound of Formula (Y):

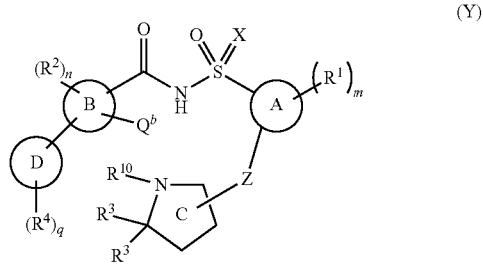

a salt thereof, or a deuterated derivative of any of the foregoing,
wherein:
  $Q^b$ is a halogen;
  $R^{10}$ is hydrogen or a protecting group;
  Ring A is a phenyl, a 5-membered heteroaryl ring, or a 6-membered heteroaryl ring;
  Ring B is a pyridinyl ring;
  Ring D is a phenyl ring, a 5-membered heterocyclyl ring, a 6-membered heterocyclyl ring, a 5-membered heteroaryl ring, or a 6-membered heteroaryl ring;
  X is O, NH, or an $N(C_1-C_4$ alkyl);
  each $R^1$ is independently chosen from $C_1-C_2$ alkyl groups, $C_1-C_2$ alkoxyl groups, $C_1-C_2$ haloalkyl groups, $C_1-C_2$ haloalkoxyl groups, halogens, a cyano group, and a hydroxyl group;
  m is 0, 1, 2, 3, or 4;
  each $R^2$ is independently chosen from $C_1-C_2$ alkyl groups, $C_1-C_2$ alkoxyl groups, $C_1-C_2$ haloalkyl groups, $C_1-C_2$ haloalkoxyl groups, halogens, a cyano group, and a hydroxyl group;
  n is 0, 1, or 2;
  each $R^3$ is methyl;
  each $R^4$ is independently chosen from halogens, an oxo group, a hydroxyl group, a cyano group, and $-(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1-C_2$ alkyl groups, haloalkyl groups, a hydroxyl group, $C_1-C_2$ alkoxyl groups, and $C_1-C_2$ haloalkoxyl groups; wherein:
    k is 0, 1, 2, 3, 4, 5, or 6;
    each Y is independently chosen from $C(R^5)(R^6)$ groups, —O—, and —$NR^a$— groups, wherein a heteroatom in $-(Y)_k$-$R^7$ is not bonded to another heteroatom in $-(Y)_k$-$R^7$, wherein:
      each $R^5$ and $R^6$ is independently chosen from hydrogen, halogens, a hydroxyl group, $C_1-C_4$ alkyl groups, and $C_{3-5}$ cycloalkyl groups, or $R^5$ and $R^6$ on the same carbon together form a $C_{3-5}$ cycloalkyl group or oxo;
      each of $R^5$ and $R^6$ is optionally independently substituted with one or more groups chosen from $C_1-C_2$ alkyl groups, $C_1-C_2$ haloalkyl groups, halogens, a hydroxyl group, $C_1-C_2$ alkoxyl groups, and $C_1-C_2$ haloalkoxyl groups; and
      each $R^a$ is independently chosen from hydrogen and $C_1-C_2$ alkyl groups; and
    $R^7$ is chosen from hydrogen, halogens, a cyano group, and $C_3-C_{10}$ to cycloalkyl groups optionally substituted with one or more groups chosen from C$_1$-C$_2$ alkyl groups, C$_1$-C$_2$ haloalkyl groups, and halogens;
q is 1, 2, 3 or 4; and
Z is a divalent linker of formula (L)$_r$, wherein:
 r is 1, 2, 3, 4, 5, or 6;
 each L is independently chosen from C(R$^8$)(R$^9$) groups, —O—, and —NR$^b$— groups, wherein a heteroatom in Z is not bonded to another heteroatom in Z, wherein:
  each R$^8$ and R$^9$ is independently chosen from hydrogen, halogens, C$_1$-C$_2$ haloalkyl groups, C$_1$-C$_2$ alkyl groups, a hydroxyl group, C$_1$-C$_2$ alkoxyl groups, and C$_1$-C$_2$ haloalkoxyl groups; and
  each R$^b$ is independently chosen from hydrogen and C$_1$-C$_2$ alkyl groups.

199. A method of preparing a compound of Formula (I):

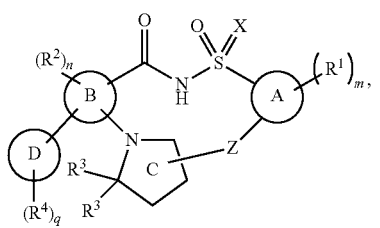

(I)

a pharmaceutically acceptable salt thereof, or a deuterated derivative of any of the foregoing, comprising
coupling the NH group of Ring C and the Q$^b$ group of Ring B of a compound of Formula (Y-I):

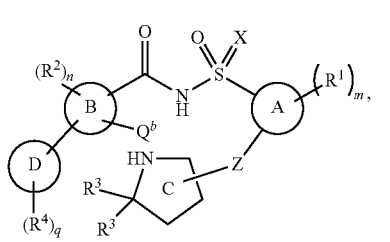

(Y-I)

a salt thereof, or a deuterated derivative of any of the foregoing, wherein:
Q$^b$ is a halogen;
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
X is O, NH, or an N(C$_1$-C$_4$ alkyl);
each R$^1$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
m is 0, 1, 2, 3, or 4;
each R$^2$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
n is 0, 1, or 2;
each R$^3$ is methyl;

each R$^4$ is independently chosen from halogens, an oxo group, a hydroxyl group, a cyano group, and -(Y)$_k$-R$^7$ groups, or optionally two R$^4$, together with the atom(s) they are attached to, form a 5-6 membered cycloalkyl or heterocyclyl ring that is optionally and independently substituted with one or more groups chosen from halogens, C$_1$-C$_2$ alkyl groups, haloalkyl groups, a hydroxyl group, C$_1$-C$_2$ alkoxyl groups, and C$_1$-C$_2$ haloalkoxyl groups; wherein:
k is 0, 1, 2, 3, 4, 5, or 6;
each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
 each R$^5$ and R$^6$ is independently chosen from hydrogen, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
 each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
 each R$^a$ is independently chosen from hydrogen and C$_1$-C$_2$ alkyl groups; and
R$^7$ is chosen from hydrogen, halogens, a cyano group, and C$_3$-C$_{10}$ to cycloalkyl groups optionally substituted with one or more groups chosen from C$_1$-C$_2$ alkyl groups, C$_1$-C$_2$ haloalkyl groups, and halogens;
q is 1, 2, 3 or 4; and
Z is a divalent linker of formula (L)$_r$, wherein:
 r is 1, 2, 3, 4, 5, or 6;
 each L is independently chosen from C(R$^8$)(R$^9$) groups, —O—, and —NR$^b$— groups, wherein a heteroatom in Z is not bonded to another heteroatom in Z, wherein:
  each R$^8$ and R$^9$ is independently chosen from hydrogen, halogens, C$_1$-C$_2$ haloalkyl groups, C$_1$-C$_2$ alkyl groups, a hydroxyl group, C$_1$-C$_2$ alkoxyl groups, and C$_1$-C$_2$ haloalkoxyl groups; and
  each R$^b$ is independently chosen from hydrogen and C$_1$-C$_2$ alkyl groups;
to form a compound of Formula (I), a pharmaceutically acceptable salt thereof, or a deuterated derivative of any of the foregoing.

200. The method of embodiment 198, wherein said coupling is performed in the presence of a base.

201. A method of preparing a compound of Formula (Y)

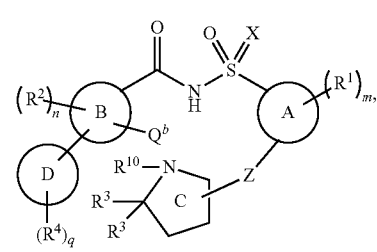

(Y)

a salt thereof, or a deuterated derivative of any of the foregoing, comprising reacting a compound of Formula (A), a salt thereof, or a deuterated derivative of any of the foregoing, with a compound of Formula (B), a salt thereof, or a deuterated derivative of any of the foregoing, to form said compound of Formula (Y), a salt thereof, or a deuterated derivative of any of the foregoing:

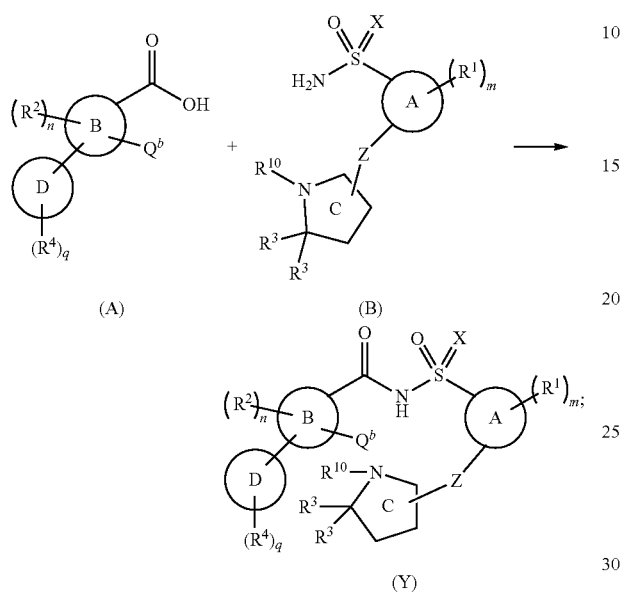

(A)  (B)

(Y)

and optionally deprotecting the N-protecting group of Ring C of Formula (Y), wherein $Q^b$ is a halogen;

$R^{10}$ of Formula (Y) is hydrogen or a N-protecting group;

$R^{10}$ of Formula (B) is a N-protecting group, and

Ring A, Ring B, Ring D, X, $R^1$, m, $R^2$, n, $R^3$, $R^4$, q, Z, $R^{th}$, and the variables therein are as recited in embodiment 1.

202. The method of embodiment 201, wherein said reacting a compound of Formula (A), a salt thereof, or a deuterated derivative of any of the foregoing, with a compound of Formula (B), a salt thereof, or a deuterated derivative of any of the foregoing, is performed in the presence of a base.

203. The method of embodiment 201, wherein said reacting a compound of Formula (A), salt thereof, or a deuterated derivative of any of the foregoing, with a compound of Formula (B), a salt thereof, or a deuterated derivative of any of the foregoing, comprises reacting a compound of Formula (A), salt thereof, or a deuterated derivative of any of the foregoing, with a coupling reagent and subsequently with a compound of Formula (B), salt thereof, or a deuterated derivative of any of the foregoing, in the presence of a base.

204. A method of preparing a compound of Formula (Y-2):

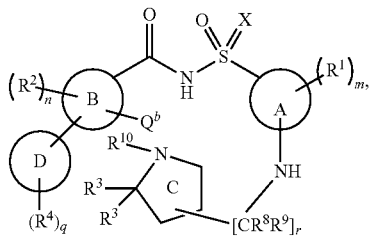

a salt thereof, or a deuterated derivative of any of the foregoing, wherein:

$Q^b$ is a halogen;

Ring A is a phenyl, a 5-membered heteroaryl ring, or a 6-membered heteroaryl ring;

Ring B is a pyridinyl ring;

Ring D is a phenyl ring, a 5-membered heterocyclyl ring, a 6-membered heterocyclyl ring, a 5-membered heteroaryl ring, or a 6-membered heteroaryl ring;

X is O, NH, or an $N(C_1-C_4$ alkyl);

each $R^1$ is independently chosen from $C_1-C_2$ alkyl groups, $C_1-C_2$ alkoxyl groups, $C_1-C_2$ haloalkyl groups, $C_1-C_2$ haloalkoxyl groups, halogens, a cyano group, and a hydroxyl group;

m is 0, 1, 2, 3, or 4;

each $R^2$ is independently chosen from $C_1-C_2$ alkyl groups, $C_1-C_2$ alkoxyl groups, $C_1-C_2$ haloalkyl groups, $C_1-C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and $-(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1-C_2$ alkyl groups, haloalkyl groups, a hydroxyl group, $C_1-C_2$ alkoxyl groups, and $C_1-C_2$ haloalkoxyl groups; wherein:

k is 0, 1, 2, 3, 4, 5, or 6;

each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each $R^5$ and $R^6$ is independently chosen from hydrogen, halogens, a hydroxyl group, $C_1-C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1-C_2$ alkyl groups, $C_1-C_2$ haloalkyl groups, halogens, a hydroxyl group, $C_1-C_2$ alkoxyl groups, and $C_1-C_2$ haloalkoxyl groups; and each $R^a$ is independently chosen from hydrogen and $C_1-C_2$ alkyl groups; and $R^7$ is chosen from hydrogen, halogens, a cyano group, and $C_3-C_{10}$ to cycloalkyl groups optionally substituted with one or more groups chosen from $C_1-C_2$ alkyl groups, $C_1-C_2$ haloalkyl groups, and halogens;

q is 1, 2, 3 or 4;

r is 1, 2, 3, 4 or 5;

each $R^8$ and $R^9$ is independently chosen from hydrogen, halogens, $C_1$-$C_2$ haloalkyl groups, $C_1$-$C_2$ alkyl groups, a hydroxyl group, $C_1$-$C_2$ alkoxyl groups, and $C_1$-$C_2$ haloalkoxyl groups; and $R^{10}$ is hydrogen or a protecting group;

comprising reacting a compound of Formula (A), a salt thereof, or a deuterated derivative of any of the foregoing, with a compound of Formula (B-2), a salt thereof, or a deuterated derivative of any of the foregoing, to form said compound of Formula (Y-2), a salt thereof, or a deuterated derivative of any of the foregoing:

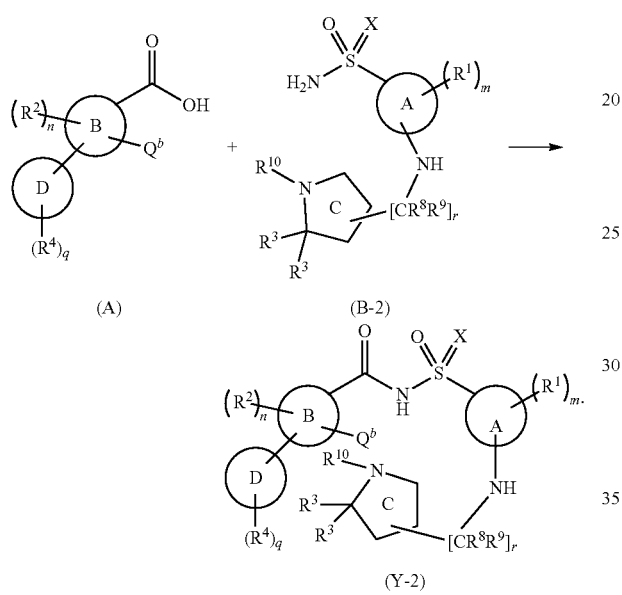

205. The method of embodiment 204, wherein said reacting a compound of Formula (A), a salt thereof, or a deuterated derivative of any of the foregoing, with a compound of Formula (B-2), salt thereof, or a deuterated derivative of any of the foregoing, is performed in the presence of a base.

206. The method of embodiment 205, wherein said reacting a compound of Formula (A), a salt thereof, or a deuterated derivative of any of the foregoing, with a compound of Formula (B-2), a salt thereof, or a deuterated derivative of any of the foregoing, comprises reacting a compound of Formula (A), a salt thereof, or a deuterated derivative of any of the foregoing, with a coupling reagent and subsequently with a compound of Formula (B-2), a salt thereof, or a deuterated derivative of any of the foregoing, in the presence of a base.

207. The method of any one of embodiments 204-206, further comprising reacting a compound of Formula (D), a salt thereof, or a deuterated derivative of any of the foregoing, with a compound of Formula (E-2), a salt thereof, or a deuterated derivative of any of the foregoing, to form said compound of Formula (B-2), a salt thereof, or a deuterated derivative of any of the foregoing:

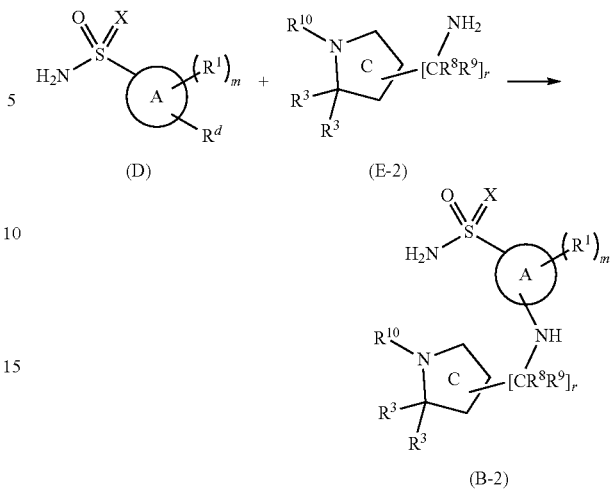

wherein $R^d$ is a halogen.

208. A method of preparing a compound of Formula (Y-3):

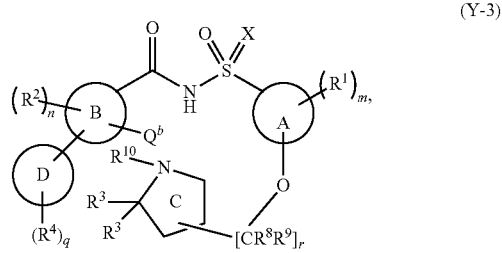

a salt thereof, or a deuterated derivative of any of the foregoing, comprising reacting a compound of Formula (A), a salt thereof, or a deuterated derivative of any of the foregoing, with a compound of Formula (B-3), a salt thereof, or a deuterated derivative of any of the foregoing, to form said compound of Formula (Y-3), a salt thereof, or a deuterated derivative of any of the foregoing:

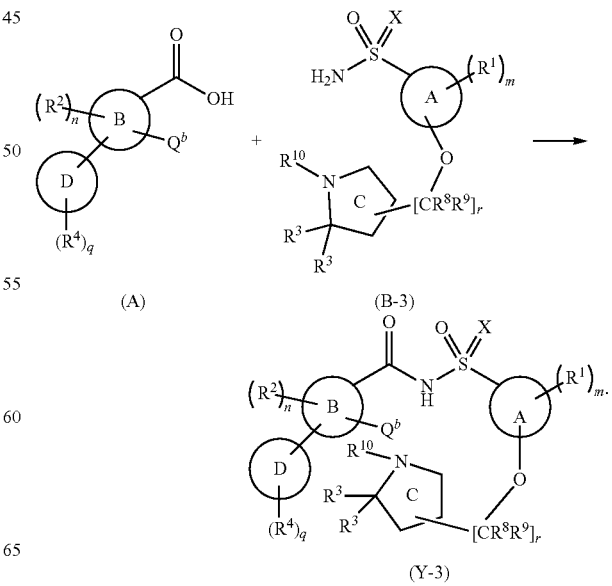

209. The method of embodiment 208 wherein said reacting a compound of Formula (A), a salt thereof, or a deuterated derivative of any of the foregoing, with a compound of Formula (B-3), a salt thereof, or a deuterated derivative of any of the foregoing, is performed in the presence of a base.

210. The method of embodiment 208, wherein said reacting a compound of Formula (A), a salt thereof, or a deuterated derivative of any of the foregoing, with a compound of Formula (B-3), a salt thereof, or a deuterated derivative of any of the foregoing, comprises reacting a compound of Formula (A), a salt thereof, or a deuterated derivative of any of the foregoing, with a coupling reagent and subsequently with a compound of Formula (B-3), a salt thereof, or a deuterated derivative of any of the foregoing, in the presence of a base.

211. The method of any one of embodiments 208-210, further comprising reacting a compound of Formula (D), a salt thereof, or a deuterated derivative of any of the foregoing, with a compound of Formula (E-3), a salt thereof, or a deuterated derivative of any of the foregoing, to form said compound of Formula (B-3), a salt thereof, or a deuterated derivative of any of the foregoing:

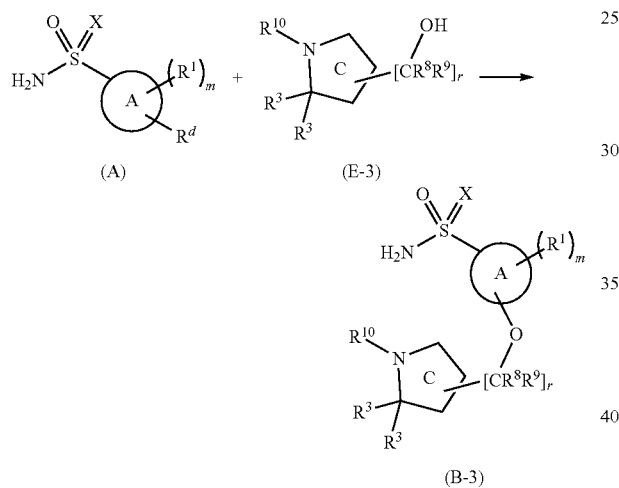

212. A method of preparing a compound of Formula (I)

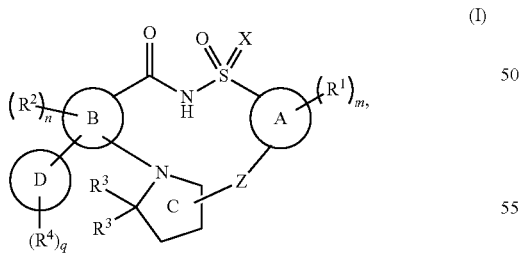

a pharmaceutically acceptable salt thereof, or a deuterated derivative of any of the foregoing, wherein Ring D is

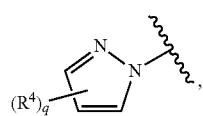

comprising
reacting a compound of Formula (X), a salt thereof, or a deuterated derivative of any of the foregoing, with a compound of Formula (Z-1), a salt thereof, or a deuterated derivative of any of the foregoing:

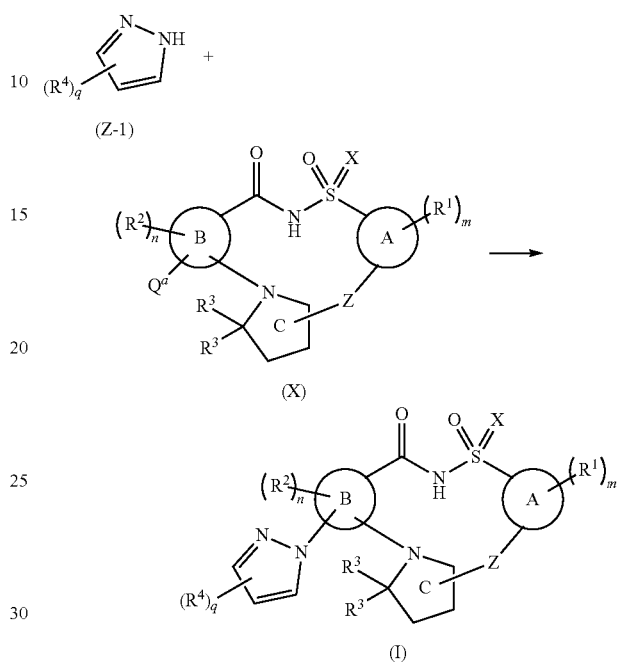

wherein:
$Q^a$ is a halogen;
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
X is O, NH, or an N(C1-C4 alkyl);
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups; wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:

each R⁵ and R⁶ is independently chosen from hydrogen, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group or oxo;

each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and R⁷ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;

q is 1, 2, 3 or 4; and

Z is a divalent linker of formula $(L)_r$, wherein:

r is 1, 2, 3, 4, 5, or 6;

each L is independently chosen from $C(R^8)(R^9)$ groups, —O—, and —NR$^b$— groups, wherein a heteroatom in Z is not bonded to another heteroatom in Z, wherein:

each R⁸ and R⁹ is independently chosen from hydrogen, halogens, $C_1$-$C_2$ haloalkyl groups, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

213. A method of preparing a compound of Formula (IV-C):

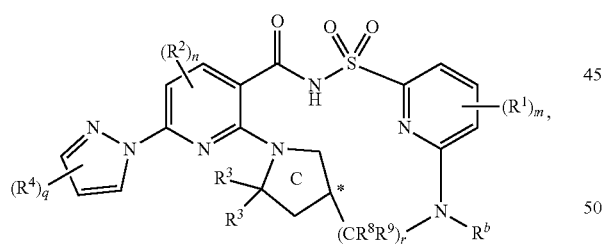

(IV-C)

a pharmaceutically acceptable salt thereof, or a deuterated derivative of any of the foregoing comprising reacting a compound of Formula (X-1), a salt thereof, or a deuterated derivative of any of the foregoing with a compound of Formula (Z-1), a salt thereof, or a deuterated derivative of any of the foregoing

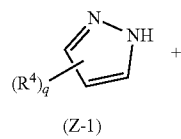

(Z-1)

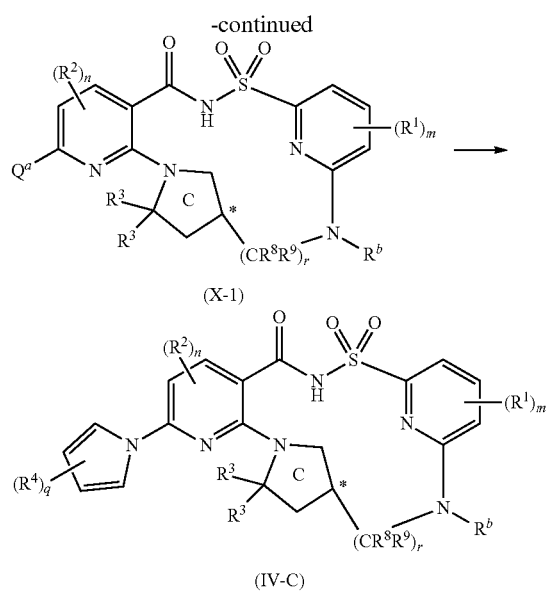

wherein:
$Q^a$ is a halogen;
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
each R¹ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each R² is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each R³ is methyl;
each R⁴ is independently chosen from halogens, an oxo group, a hydroxyl group, a cyano group, and -(Y)$_k$-R⁷ groups, or optionally two R⁴, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —NR$^a$— groups, wherein a heteroatom in -(Y)$_k$-R⁷ is not bonded to another heteroatom in -(Y)$_k$-R⁷, wherein:
each R⁵ and R⁶ is independently chosen from hydrogen, halogens, a hydroxyl group, $C_1$-$C_4$ alkyl groups, and $C_{3-5}$ cycloalkyl groups, or R⁵ and R⁶ on the same carbon together form a $C_{3-5}$ cycloalkyl group or oxo;
each of R⁵ and R⁶ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ to cycloalkyl groups optionally substituted with one or more groups chosen from $C_1$-$C_2$ alkyl groups, $C_1$-$C_2$ haloalkyl groups, and halogens;

q is 1 or 2;

r is 3 or 4;

each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

214. The compound of any one of embodiments 1-190, wherein the compound is in the form of a pharmaceutically acceptable salt.

215. The compound of embodiment 214, wherein the pharmaceutically acceptable salt is a sodium salt, a calcium salt, or a potassium salt.

216. The compound of embodiment 215, wherein the pharmaceutically acceptable salt is a calcium salt.

217. The compound of embodiment 191, wherein the compound is in the form of a pharmaceutically acceptable salt.

218. The compound of embodiment 217, wherein the pharmaceutically acceptable salt is a sodium salt, a calcium salt, or a potassium salt.

219. The compound of embodiment 218, wherein the pharmaceutically acceptable salt is a calcium salt.

220. The compound of embodiment 192, wherein the compound is in the form of a pharmaceutically acceptable salt.

221. The compound of embodiment 220, wherein the pharmaceutically acceptable salt is a sodium salt, a calcium salt, or a potassium salt.

222. The compound of embodiment 221, wherein the pharmaceutically acceptable salt is a calcium salt.

223. The compound of embodiment 193, wherein the compound is in the form of a pharmaceutically acceptable salt.

224. The compound of embodiment 223, wherein the pharmaceutically acceptable salt is a sodium salt, a calcium salt, or a potassium salt.

225. The compound of embodiment 224, wherein the pharmaceutically acceptable salt is a calcium salt.

226. The compound of embodiment 193, wherein the compound is

227. The compound of embodiment 193, wherein the compound is in the form of a calcium salt of:

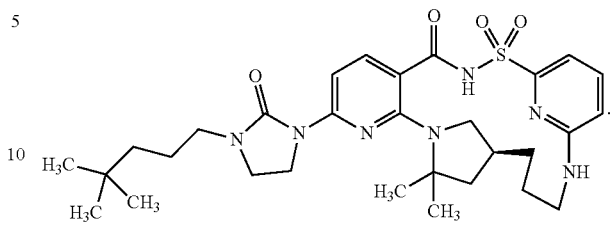

228. The compound of embodiment 193, wherein the compound is

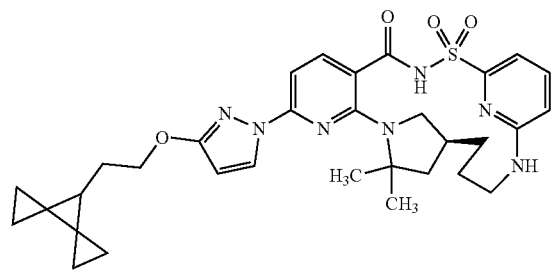

229. The compound of embodiment 193, wherein the compound is in the form of a calcium salt of:

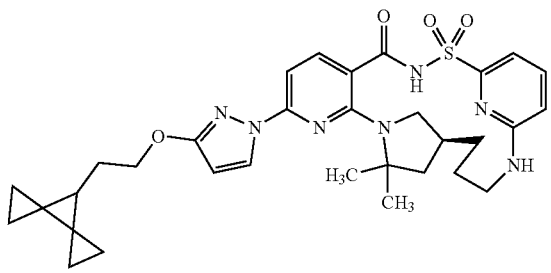

230. The compound of embodiment 193, wherein the compound is

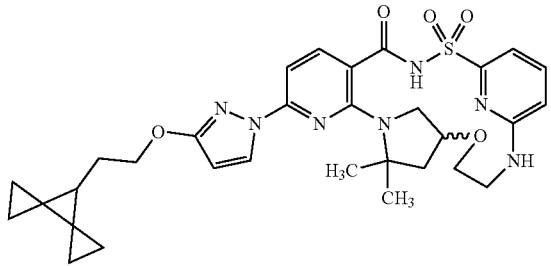

231. The compound of embodiment 193, wherein the compound is in the form of a calcium salt of:

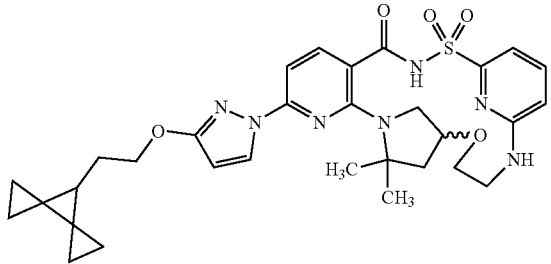

232. The compound of embodiment 193, wherein the compound is

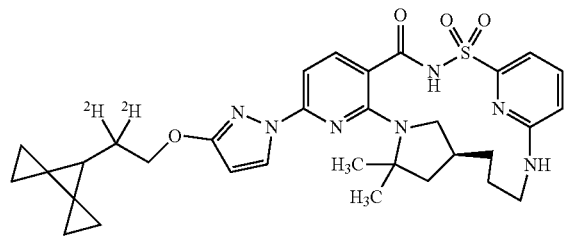

233. The compound of embodiment 193, wherein the compound is in the form of a calcium salt of:

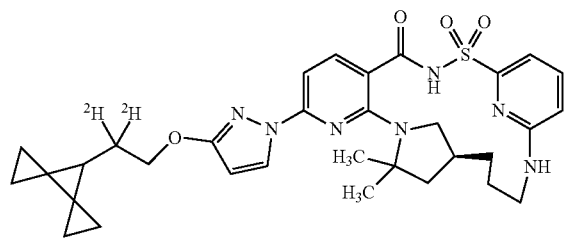

234. The compound of embodiment 193, wherein the compound is

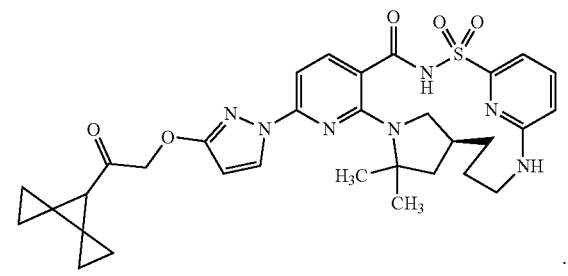 [SMILES: CC1(C)C[C@@H]2CCCNc3cccc(n3)S(=O)(=O)NC(=O)c3ccc(-n4ccc(OCC(=O)C5C6(CC6)C56CC6)n4)nc3N1C2]

235. The compound of embodiment 193, wherein the compound is in the form of a calcium salt of:

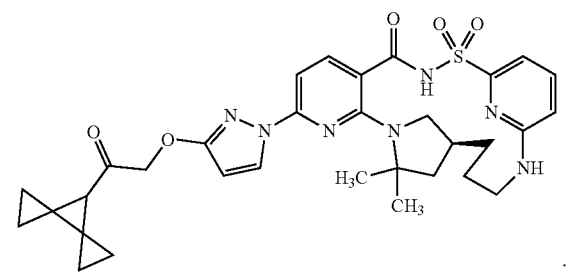 [SMILES: CC1(C)C[C@@H]2CCCNc3cccc(n3)S(=O)(=O)NC(=O)c3ccc(-n4ccc(OCC(=O)C5C6(CC6)C56CC6)n4)nc3N1C2]

236. The compound of embodiment 193, wherein the compound is

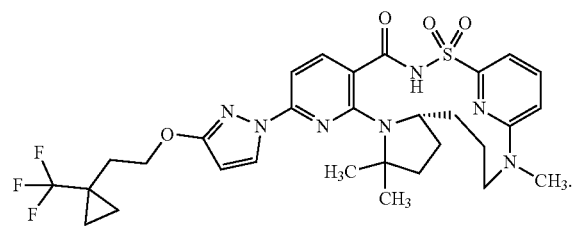 [SMILES: CN1CCC[C@@H]2CCC(C)(C)N2c2nc(-n3ccc(OCCC4(C(F)(F)F)CC4)n3)ccc2C(=O)NS(=O)(=O)c2cccc1n2]

237. The compound of embodiment 193, wherein the compound is in the form of a calcium salt of:

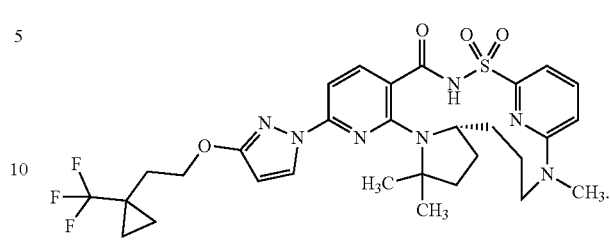

238. The compound of embodiment 193, wherein the compound is

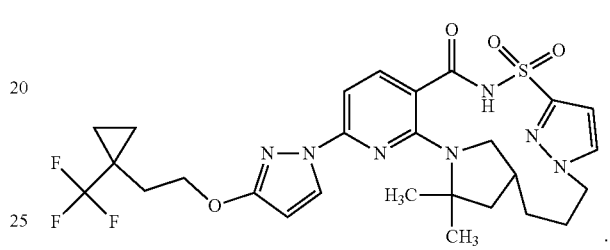

239. The compound of embodiment 193, wherein the compound is in the form of a calcium salt of:

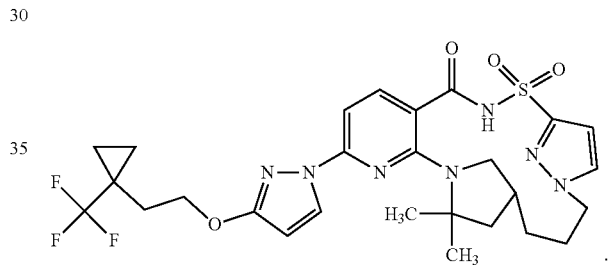

240. The compound of embodiment 193, wherein the compound is

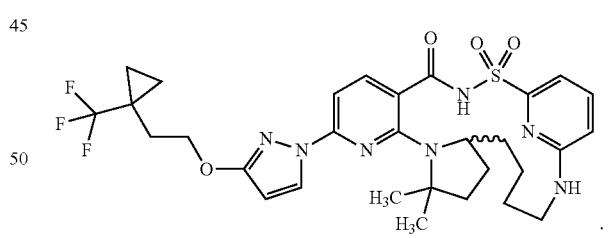

241. The compound of embodiment 193, wherein the compound is in the form of a calcium salt of:

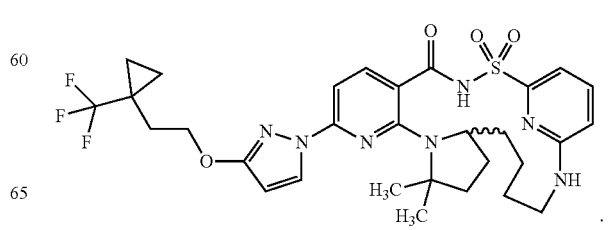

242. The compound of embodiment 193, wherein the compound is

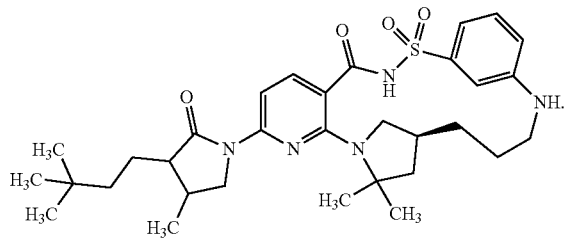 [SMILES: CC1CN(c2ccc3c(n2)N2C[C@@H](CCCNc4cccc(c4)S(=O)(=O)NC3=O)CC2(C)C)C(=O)C1CCC(C)(C)C]

243. The compound of embodiment 193, wherein the compound is in the form of a calcium salt of:

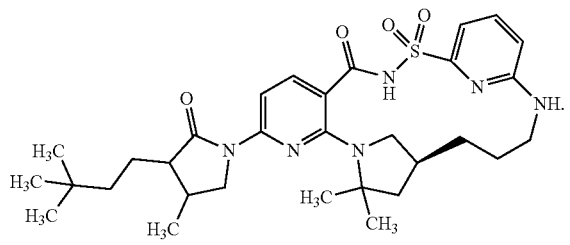 [SMILES: CC1CN(c2ccc3c(n2)N2C[C@@H](CCCNc4cccc(n4)S(=O)(=O)NC3=O)CC2(C)C)C(=O)C1CCC(C)(C)C]

244. The compound of embodiment 193, wherein the compound is

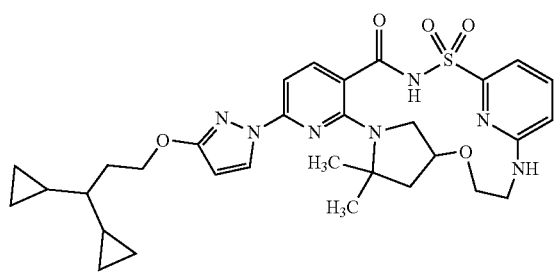

245. The compound of embodiment 193, wherein the compound is in the form of a calcium salt of:

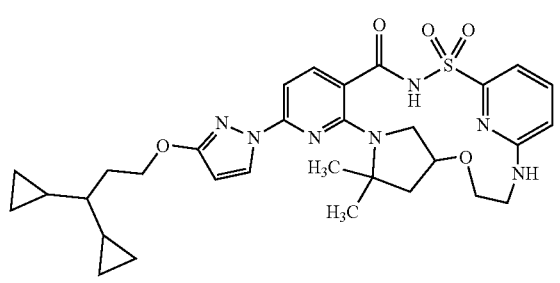

246. The method of treating cystic fibrosis of embodiment 195, wherein the compound is in the form of a pharmaceutically acceptable salt.
247. The method of embodiment 246, wherein the pharmaceutically acceptable salt is a sodium salt, a calcium salt, or a potassium salt.
248. The method of embodiment 247, wherein the pharmaceutically acceptable salt is a calcium salt.

249. A method of treating cystic fibrosis comprising administering to a patient in need thereof a compound of embodiment 192.
250. A method of treating cystic fibrosis comprising administering to a patient in need thereof a compound of any one of embodiments 193 or 226-245.
251. The method of treating cystic fibrosis of embodiment 249 or 250, wherein the compound is in the form of a pharmaceutically acceptable salt.
252. The method of embodiment 251, wherein the pharmaceutically acceptable salt is a sodium salt, a calcium salt, or a potassium salt.
253. The method of embodiment 252, wherein the pharmaceutically acceptable salt is a calcium salt.
254. A method of treating cystic fibrosis comprising administering to a patient in need thereof the compound of any one of embodiments 1-190, wherein the compound is administered in combination with Compound III or a pharmaceutically acceptable salt or deuterated derivative thereof.
255. A method of treating cystic fibrosis comprising administering to a patient in need thereof the compound of embodiment 191, wherein the compound is administered in combination with Compound III or a pharmaceutically acceptable salt or deuterated derivative thereof.
256. A method of treating cystic fibrosis comprising administering to a patient in need thereof the compound of embodiment 192, wherein the compound is administered in combination with Compound III or a pharmaceutically acceptable salt or deuterated derivative thereof.
257. A method of treating cystic fibrosis comprising administering to a patient in need thereof the compound of any one of embodiments 193 or 226-245, wherein the compound is administered in combination with Compound III or a pharmaceutically acceptable salt or deuterated derivative thereof.
258. The method of any one of embodiments 254-257, wherein the deuterated derivative of Compound III is Compound III-d.
259. A method of treating cystic fibrosis comprising administering to a patient in need thereof the compound of any one of embodiments 1-190, wherein the compound is administered in combination with (a) Compound II and (b) Compound III or a deuterated derivative thereof.
260. A method of treating cystic fibrosis comprising administering to a patient in need thereof the compound of embodiment 191, wherein the compound is administered in combination with (a) Compound II and (b) Compound III or a deuterated derivative thereof.
261. A method of treating cystic fibrosis comprising administering to a patient in need thereof the compound of embodiment 192, wherein the compound is administered in combination with (a) Compound II and (b) Compound III or a deuterated derivative thereof.
262. A method of treating cystic fibrosis comprising administering to a patient in need thereof the compound of any one of embodiments 193 or 226-245, wherein the compound is administered in combination with (a) Compound II and (b) Compound III or a deuterated derivative thereof.
263. The method of any one of embodiments 259-262, wherein the deuterated derivative of Compound III is Compound III-d.

264. The method of any one of embodiments 254-262, wherein the compound is in the form of a pharmaceutically acceptable salt.
265. The method of embodiment 264, wherein the pharmaceutically acceptable salt is a sodium salt, a calcium salt, or a potassium salt.
266. The method of embodiment 265, wherein the pharmaceutically acceptable salt is a calcium salt.
267. A pharmaceutical composition comprising the compound of embodiment 191 and a pharmaceutically acceptable carrier.
268. A pharmaceutical composition comprising the compound of embodiment 192 and a pharmaceutically acceptable carrier.
269. A pharmaceutical composition comprising the compound of any one of embodiments 193 or 226-245 and a pharmaceutically acceptable carrier.
270. The pharmaceutical composition of any one of embodiments 267-269, wherein the compound in the form of a pharmaceutically acceptable salt.
271. The pharmaceutical composition of embodiment 270, wherein the pharmaceutically acceptable salt is a sodium salt, a calcium salt, or a potassium salt.
272. The pharmaceutical composition of embodiment 271, wherein the pharmaceutically acceptable salt is a calcium salt.
273. The pharmaceutical composition of any one of embodiments 267-272, further comprising Compound III or pharmaceutically acceptable salt or deuterated derivative thereof.
274. The pharmaceutical composition of embodiment 273, wherein the deuterated derivative of Compound III is Compound III-d.
275. The pharmaceutical composition of any one of embodiments 267-272, further comprising (a) Compound II and (b) Compound III or a deuterated derivative thereof.
276. The pharmaceutical composition of embodiment 275, wherein the deuterated derivative of Compound III is Compound III-d.
277. The compound of any one of embodiments 1-190 for use in the treatment of cystic fibrosis.
278. The compound of embodiment 191 for use in the treatment of cystic fibrosis.
279. The compound embodiment 192 for use in the treatment of cystic fibrosis.
280. The compound of any one of embodiments 193 or 226-245 for use in the treatment of cystic fibrosis.
281. The compound for use of any one of embodiments 277-280, wherein the compound is in the form of a pharmaceutically acceptable salt.
282. The compound for use of embodiment 281, wherein the pharmaceutically acceptable salt is a sodium salt, a calcium salt, or a potassium salt.
283. The compound for use of embodiment 282, wherein the pharmaceutically acceptable salt is a calcium salt.
284. The compound for use of any one of embodiments 277-283, wherein the treatment further comprises administration of Compound III.
285. The compound for use of any one of embodiments 277-283, wherein the treatment further comprises administration of Compound III-d.
286. The compound for use of any one of embodiments 277-283, wherein the treatment further comprises administration of Compound II and Compound III.
287. The compound for use of any one of embodiments 277-283, wherein the treatment further comprises administration of Compound II and Compound III-d.

Other embodiments include:
A. A compound of Formula I:

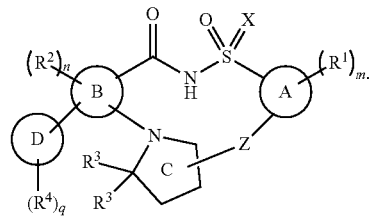

B. A pharmaceutically acceptable salt of a compound of Formula I

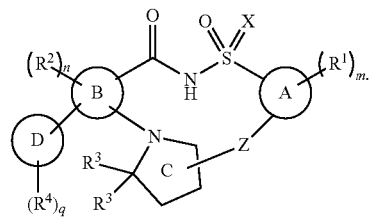

C. A pharmaceutical composition comprising:
(i) a compound of Formula I

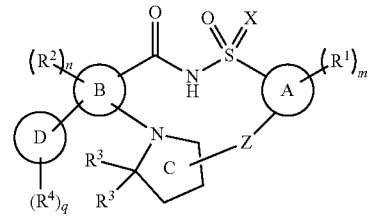

and
(ii) a pharmaceutically acceptable carrier.
D. The pharmaceutical composition of embodiment C further comprising Compound II:

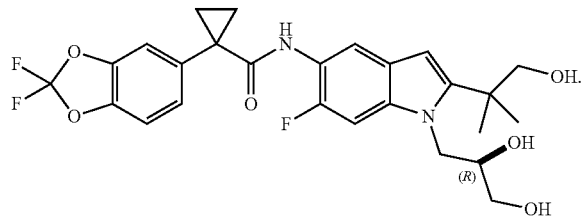

E. The pharmaceutical composition of embodiment C further comprising a pharmaceutically acceptable salt of Compound II:

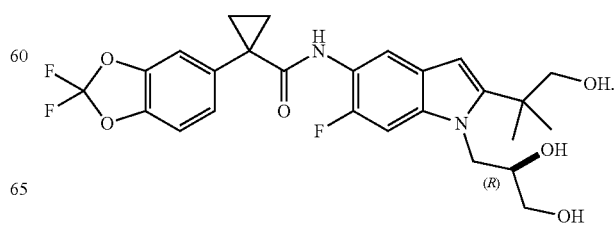

F. The pharmaceutical composition of embodiment C further comprising Compound III:

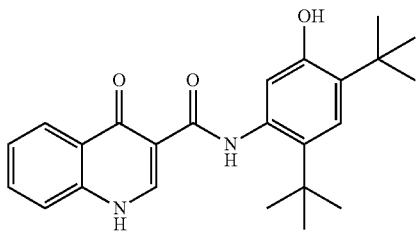

G. The pharmaceutical composition of embodiment C further comprising a pharmaceutically acceptable salt of Compound III:

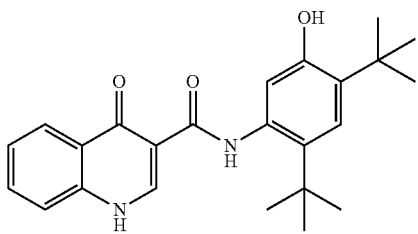

H. The pharmaceutical composition of embodiment D further comprising Compound III:

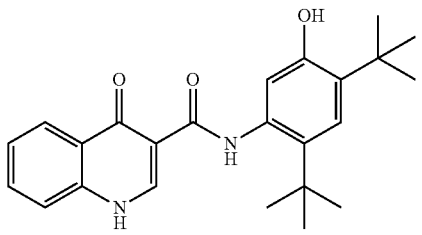

I. The pharmaceutical composition of embodiment D further comprising a pharmaceutically acceptable salt of Compound III:

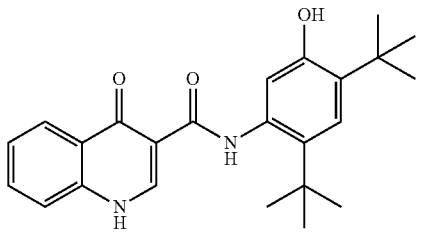

J. The pharmaceutical composition of embodiment E further comprising Compound III:

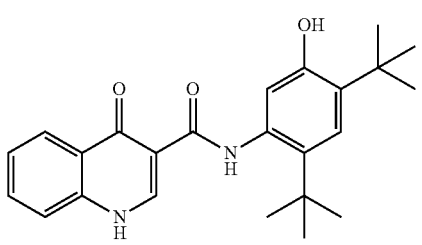

K. The pharmaceutical composition of embodiment E further comprising a pharmaceutically acceptable salt of Compound III:

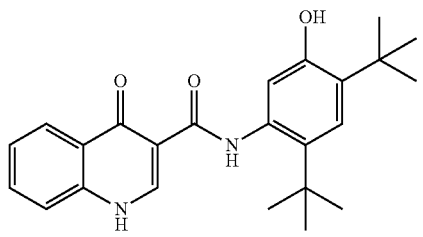

L. A pharmaceutical composition comprising:

(A) a pharmaceutically acceptable salt of a compound of Formula I

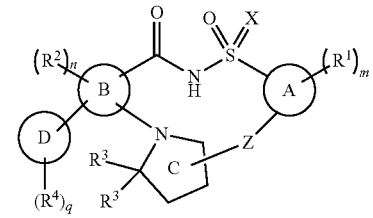

and (B) a pharmaceutically acceptable carrier.

M. The pharmaceutical composition of embodiment L further comprising Compound II:

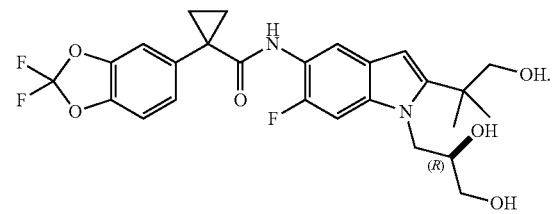

N. The pharmaceutical composition of embodiment L further comprising a pharmaceutically acceptable salt of Compound II:

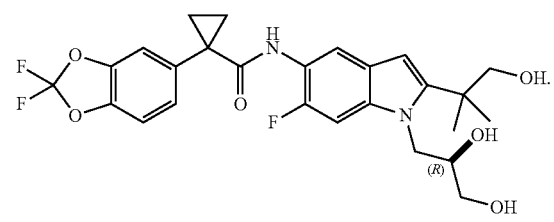

O. The pharmaceutical composition of embodiment L further comprising Compound III:

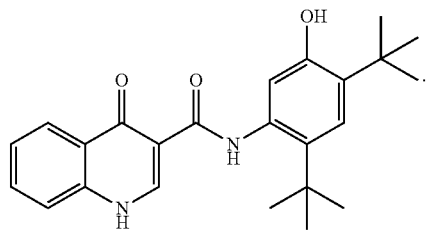

P. The pharmaceutical composition of embodiment L further comprising a pharmaceutically acceptable salt of Compound III:

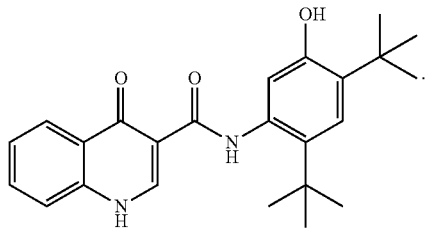

Q. The pharmaceutical composition of embodiment M further comprising Compound III:

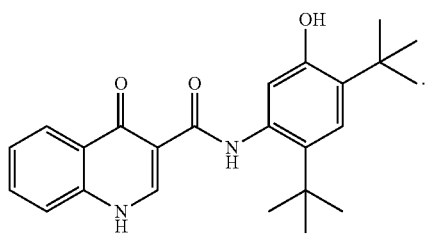

R. The pharmaceutical composition of embodiment M further comprising a pharmaceutically acceptable salt of Compound III:

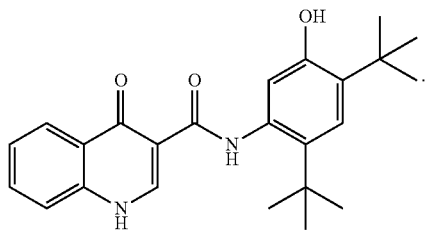

S. The pharmaceutical composition of embodiment M further comprising Compound III:

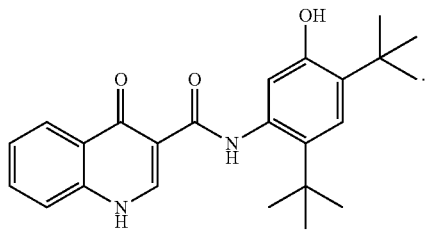

T. The pharmaceutical composition of embodiment M further comprising a pharmaceutically acceptable salt of Compound III:

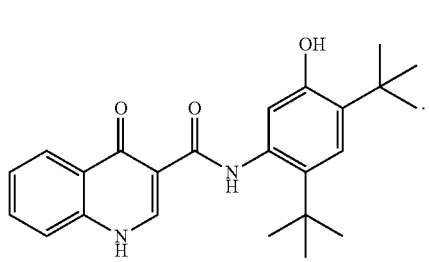

U. A method of treating cystic fibrosis comprising administering to a patient in need thereof a compound of Formula I

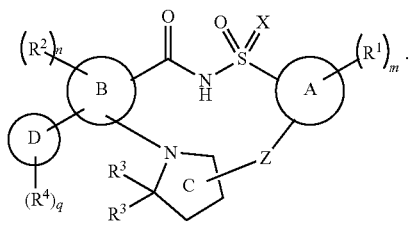

V. A method of treating cystic fibrosis comprising administering to a patient in need thereof a pharmaceutically acceptable salt of a compound of Formula I

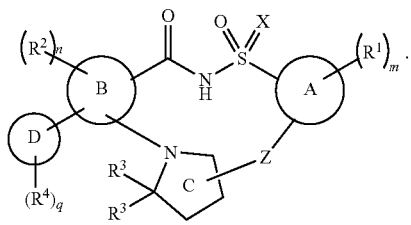

W. A method of treating cystic fibrosis comprising administering to a patient in need thereof a pharmaceutical composition comprising:
(A) a compound of Formula I

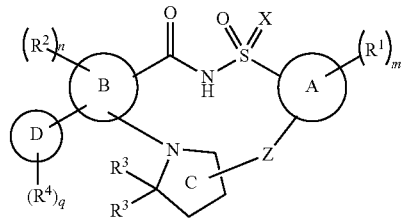

and
(B) a pharmaceutically acceptable carrier.

X. A method of treating cystic fibrosis comprising administering to a patient in need thereof a pharmaceutical composition comprising:
a pharmaceutically acceptable salt of a compound of Formula I

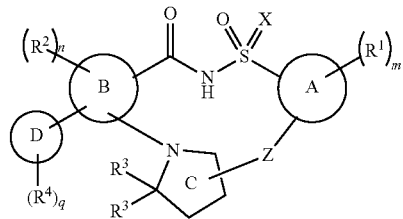

and
a pharmaceutically acceptable carrier.

General Experimental Procedures

The definitions of certain abbreviations for the Examples below are summarized below:

Boc anhydride ((Boc)$_2$O): di-tert-butyl dicarbonate
CDI: carbonyl diimidazole
DABCO: 1,4-diazabicyclo[2.2.2]octane
DBU: 1,8-diazabicyclo(5.4.0)undec-7-ene
DCM: dichloromethane
DIAD: diisopropyl azodicarboxylate
DIEA (DIPEA; N,N-diisopropylethylamine)
DMA: N,N-Dimethylacetamide
DMF: N,N-dimethylformamide
DMSO: dimethyl sulfoxide
Et$_2$O: diethyl ether
EtOH: ethanol
HATU: 1-[Bis(dimethylamino)methylene]-1H-1,2,3-triazolo[4,5-b]pyridinium 3-oxid hexafluorophosphate
IPA: isoproanol
MeOH: methanol
NMP: N-methyl-2-pyrrolidone
MTBE: methyl tert-butyl ether
TBS-Cl: tert-Butyldimethylsilyl chloride
TFA: trifluoroacetic acid
THF: tetrahydrofuran)
p-TsOH: p-Toluenesulfonic Acid
TPPO-DIAD complex: a complex of triphenylphosphine oxide with diisopropyl azodicarboxylate Reagents and starting materials were obtained by commercial sources unless otherwise stated and were used without purification. Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters. Final purity of compounds was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as [M+H]$^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30m× 0.25 mm×0.25 um_df) column, with a 2.0 mL/min flow rate (H$_2$ carrier gas), at an injection temperature of 220° C. and an oven temperature of 120° C., 15 minutes.

SYNTHETIC EXAMPLES

Synthesis of Compound II: (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

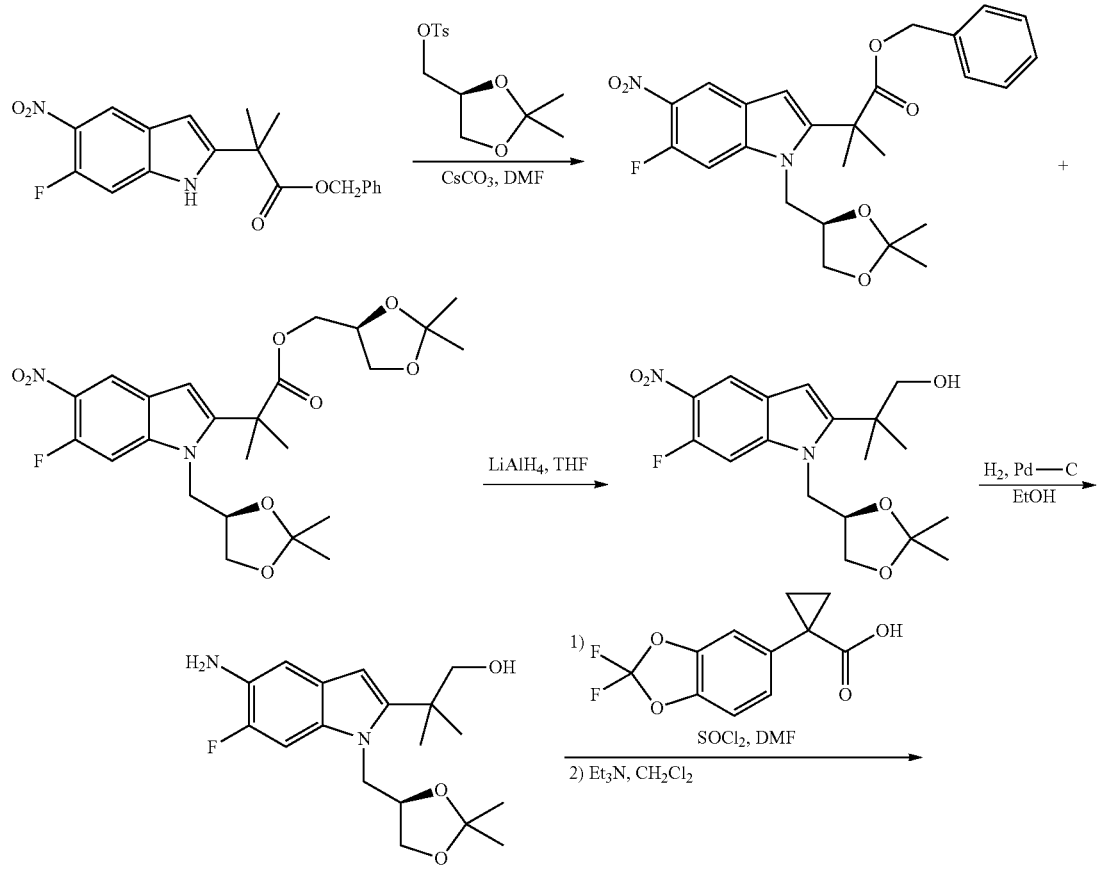

-continued

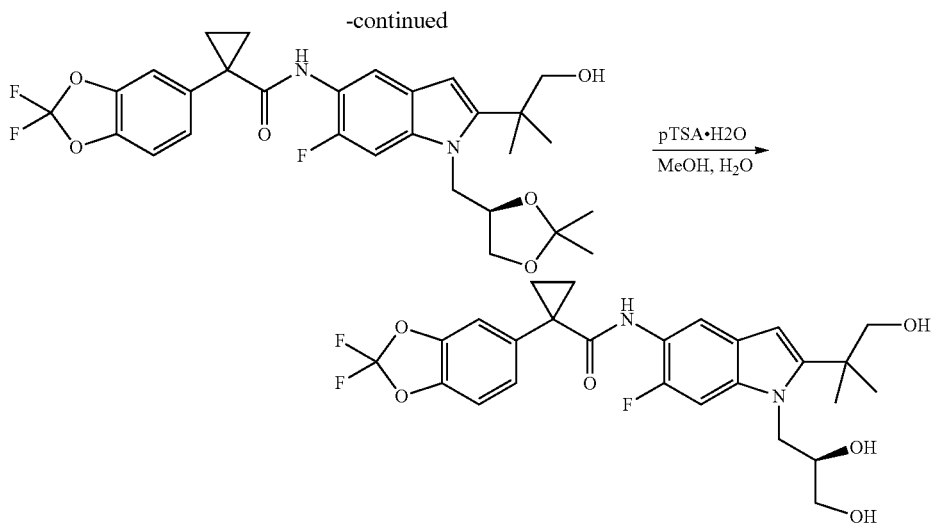

pTSA·H2O
―――――→
MeOH, H₂O

Step 1: (R)-Benzyl 2-(1-((2,2-dimethyl-1,3-dioxolan-4-yl)methyl)-6-fluoro-5-nitro-1H-indol-2-yl)-2-methylpropanoate and ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (N,N-dimethylformamide) (17 mL). The reaction was stirred at 80° C. for 46 hours under a nitrogen atmosphere. The mixture was then partitioned between ethyl acetate and water. The aqueous layer was extracted with ethyl acetate. The combined ethyl acetate layers were washed with brine, dried over MgSO₄, filtered and concentrated. The crude product, a viscous brown oil which contains both of the products shown above, was taken directly to the next step without further purification. (R)-Benzyl 2-(1-((2,2-dimethyl-1,3-dioxolan-4-yl)methyl)-6-fluoro-5-nitro-1H-indol-2-yl)-2-methylpropanoate, ESI-MS m/z calc. 470.2, found 471.5 (M+1)⁺. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m/z calc. 494.5, found 495.7 (M+1)⁺. Retention time 2.01 minutes.

Step 2: (R)-2-(1-((2,2-dimethyl-1,3-dioxolan-4-yl)methyl)-6-fluoro-5-nitro-1H-indol-2-yl)-2-methylpropan-1-ol The crude reaction mixture obtained in step (A) was dissolved in THF (tetrahydrofuran) (42 mL) and cooled in an ice-water bath. LiAlH₄ (16.8 mL of 1 M solution, 16.8 mmol) was added drop-wise. After the addition was complete, the mixture was stirred for an additional 5 minutes. The reaction was quenched by adding water (1 mL), 15% NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain (R)-2-(1-((2,2-dimethyl-1,3-dioxolan-4-yl)methyl)-6-fluoro-5-nitro-1H-indol-2-yl)-2-methylpropan-1-ol as a brown oil (2.68 g, 87% over 2 steps). ESI-MS m/z calc. 366.4, found 367.3 (M+1)⁺. Retention time 1.68 minutes. ¹H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm. (DMSO is dimethylsulfoxide).

Step 3: (R)-2-(5-amino-1-((2,2-dimethyl-1,3-dioxolan-4-yl)methyl)-6-fluoro-1H-indol-2-yl)-2-methylpropan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved in ethanol (70 mL) and the reaction was flushed with N₂. Then Pd-C (250 mg, 5% wt) was added. The reaction was flushed with nitrogen again and then stirred under H₂ (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product (1.82 g, 79%). ESI-MS m/z calc. 336.2, found 337.5 (M+1)⁺. Retention time 0.86 minutes. ¹H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step 4: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO$_3$ solution and brine, dried over MgSO$_4$ and concentrated to yield the product (3 g, 100%). ESI-MS m/z calc. 560.6, found 561.7 (M+1)$^+$. Retention time 2.05 minutes. $^1$H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm.

Step 5: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL). Water (5.2 mL) was added followed by p-TsOH·H$_2$O (p-toluenesulfonic acid hydrate) (204 mg, 1.1 mmol). The reaction was heated at 80° C. for 45 minutes. The solution was concentrated and then partitioned between ethyl acetate and saturated NaHCO$_3$ solution. The ethyl acetate layer was dried over MgSO$_4$ and concentrated. The residue was purified by column chromatography (50-100% ethyl acetate-hexanes) to yield the product. (1.3 g, 47%, ee>98% by SFC). ESI-MS m/z calc. 520.5, found 521.7 (M+1)$^+$. Retention time 1.69 minutes. $^1$H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

Synthesis of Compound III: N-(2,4-di-tert-butyl-5-hydroxyphenyl)-4-oxo-1,4-dihydroquinoline-3-carboxamide Part A: Synthesis of 4-oxo-1,4-dihydroquinoline-3-carboxylic Acid

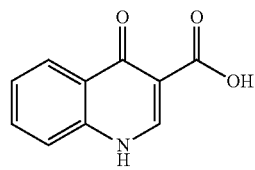 [SMILES: O=C(O)c1c[nH]c2ccccc2c1=O]

Step 1: 2-Phenylaminomethylene-malonic Acid Diethyl Ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. $^1$H NMR (DMSO-d$_6$) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

Step 2: 4-Hydroxyquinoline-3-carboxylic Acid Ethyl Ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous Na$_2$CO$_3$ solution, filtered, washed with water and dried. 4-Hydroxyquinoline-3-carboxylic acid ethyl ester was obtained as a pale brown solid (15.2 g, 70%). The crude product was used in next step without further purification.

Step 3: 4-Oxo-1,4-dihydroquinoline-3-carboxylic Acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). $^1$H NMR (DMSO-d$_6$) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Part B: Synthesis of N-(2,4-di-tert-butyl-5-hydroxyphenyl)-4-oxo-1,4-dihydroquinoline-3-carboxamide

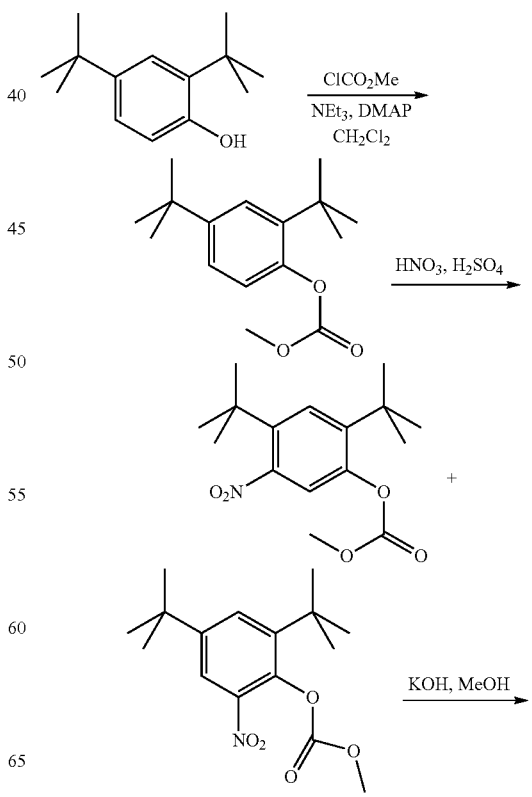

157

-continued

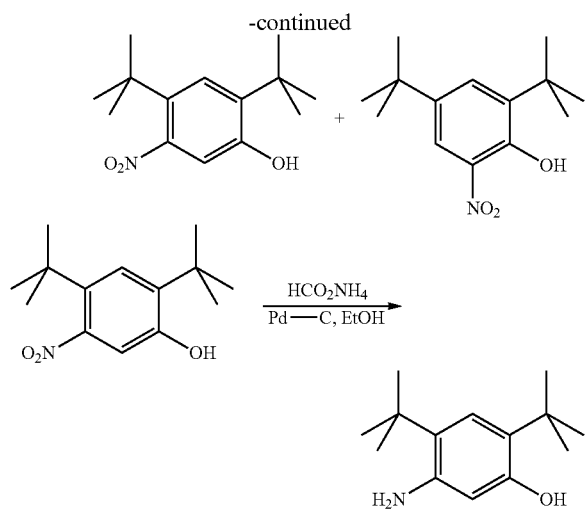

Step 1: Carbonic Acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et$_3$N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate hexanes (4 L) as the eluent. The combined filtrates were concentrated to yield carbonic acid 2,4-di-tert-butyl-phenyl ester methyl ester as a yellow oil (132 g, quant.). $^1$H NMR (400 MHz, DMSO-d$_6$) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Step 2: Carbonic Acid 2,4-di-tert-butyl-5-nitro-phenyl ester methyl ester and Carbonic Acid 2,4-di-tert-butyl-6-nitro-phenyl ester methyl ester To a stirring mixture of carbonic acid 2,4-di-tert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO$_4$), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

Step 3: 2,4-Di-tert-butyl-5-nitro-phenol and 2,4-Di-tert-butyl-6-nitro-phenol

The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO$_4$), concentrated and

158 purified by column chromatography (0-5% ethyl acetate hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: $^1$H NMR (400 MHz, DMSO-d$_6$) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: $^1$H NMR (400 MHz, CDCl$_3$) δ 11.48 (s, 1H), 7.98 (d, J=2.5 Hz, 1H), 7.66 (d, J=2.4 Hz, 1H), 1.47 (s, 9H), 1.34 (s, 9H).

Step 4: 5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). $^1$H NMR (400 MHz, DMSO-d$_6$) δ 8.64 (s, 1H, OH), 6.84 (s, 1H), 6.08 (s, 1H), 4.39 (s, 2H, NH$_2$), 1.27 (m, 18H); HPLC ret. time 2.72 min, 10-99% CH$_3$CN, 5 min run; ESI-MS 222.4 m/z [M+H]$^+$.

Step 5: N-(5-hydroxy-2,4-di-tert-butyl-phenyl)-4-oxo-1H-quinoline-3-carboxamide

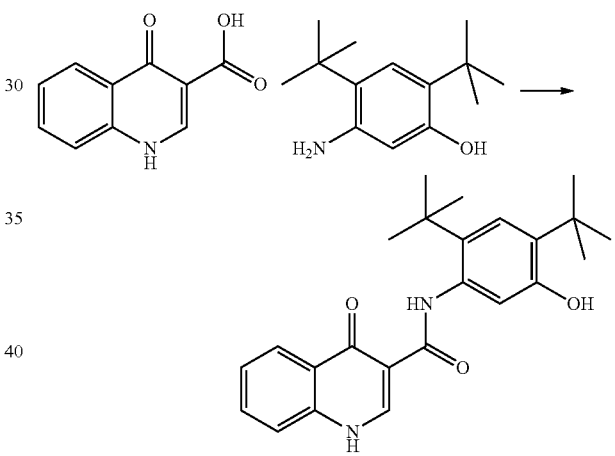

To a suspension of 4-oxo-1,4-dihydroquinolin-3-carboxylic acid (35.5 g, 188 mmol) and HBTU (85.7 g, 226 mmol) in DMF (280 mL) was added Et$_3$N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+ 190, 1.71 min), the solvent was removed in vacuo. EtOH (ethyl alcohol) was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystalate. Et$_2$O (diethyl ether) was added to the solid obtained above until a slurry was formed. The mixture was stirred on a rotovapor (bath temperature 25° C.) for 15 min without placing the system under vacuum. The mixture was filtered and the solid captured. This procedure was performed a total of five times. The solid obtained after the fifth precipitation was placed under vacuum overnight to provide N-(5-hydroxy-2,4-di-tert-butyl-phenyl)-4-oxo-1H-quinoline-3-carboxamide (38 g, 52%). HPLC ret. time 3.45 min, 10-99% CH₃CN, 5 min run; ¹H NMR (400 MHz, DMSO-d₆) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS m/z calc'd 392.21; found 393.3 [M+H]⁺.

Synthesis of Compound IV: 3-(6-(1-(2,2-difluorobenzo[d][1,3]dioxol-5-yl) cyclopropanecarboxamido)-3-methylpyridin-2-yl)benzoic Acid Compound IV may be prepared by coupling an acid chloride moiety with an amine moiety according to Schemes IV-A through IV-D.

Scheme IV-A. Synthesis of the acid chloride moiety.

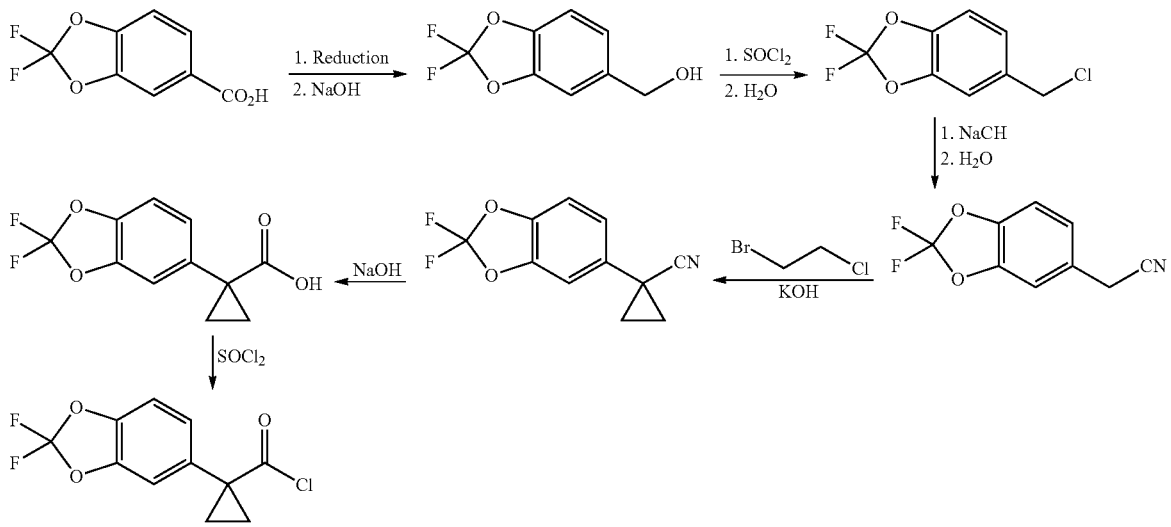

Scheme IV-A depicts the preparation of 1-(2,2-difluorobenzo[d][1,3]dioxol-5-yl)cyclopropanecarbonyl chloride, which is used in Scheme IV-C to make the amide linkage of Compound IV.

The starting material, 2,2-difluorobenzo[d][1,3]dioxole-5-carboxylic acid, is commercially available from Saltigo (an affiliate of the Lanxess Corporation). Reduction of the carboxylc acid moiety in 2,2-difluorobenzo[d][1,3]dioxole-5-carboxylic acid to the primary alcohol, followed by conversion to the corresponding chloride using thionyl chloride (SOCl₂), provides 5-(chloromethyl)-2,2-difluorobenzo[d][1,3]dioxole, which is subsequently converted to 2-(2,2-difluorobenzo[d][1,3]dioxol-5-yl)acetonitrile using sodium cyanide. Treatment of 2-(2,2-difluorobenzo[d][1,3]dioxol-5-yl)acetonitrile with base and 1-bromo-2-chloroethane provides 1-(2,2-difluorobenzo[d][1,3]dioxol-5-yl)cyclopropanecarbonitrile. The nitrile moiety in 1-(2,2-difluorobenzo[d][1,3]dioxol-5-yl)cyclopropanecarbonitrile is converted to a carboxylic acid using base to give 1-(2,2-difluorobenzo[d][1,3]dioxol-5-yl)cyclopropanecarboxylic acid, which is converted to the desired acid chloride using thionyl chloride.

Scheme IV-B. Alternative synthesis of the acid chloride moiety.

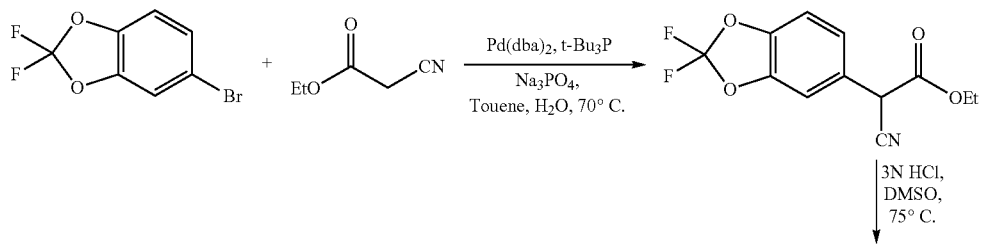

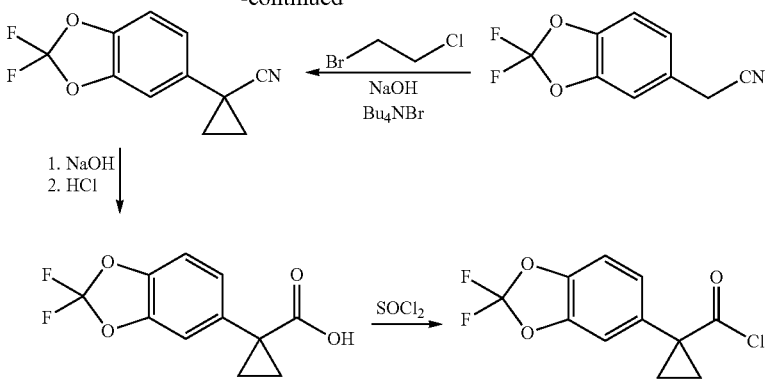

Scheme IV-B depicts an alternative synthesis of the requisite acid chloride. 5-bromomethyl-2,2-difluoro-1,3-benzodioxole is coupled with ethyl cyanoacetate in the presence of a palladium catalyst to form the corresponding alpha cyano ethyl ester. Saponification of the ester moiety to the carboxylic acid gives the cyanoethyl Compound IV. Alkylation of the cyanoethyl compound with 1-bromo-2-chloro ethane in the presence of base gives the cyanocyclopropyl compound. Treatment of the cyanocyclopropyl compound with base gives the carboxylate salt, which is converted to the carboxylic acid by treatment with acid. Conversion of the carboxylic acid to the acid chloride is then accomplished using a chlorinating agent such as thionyl chloride or the like.

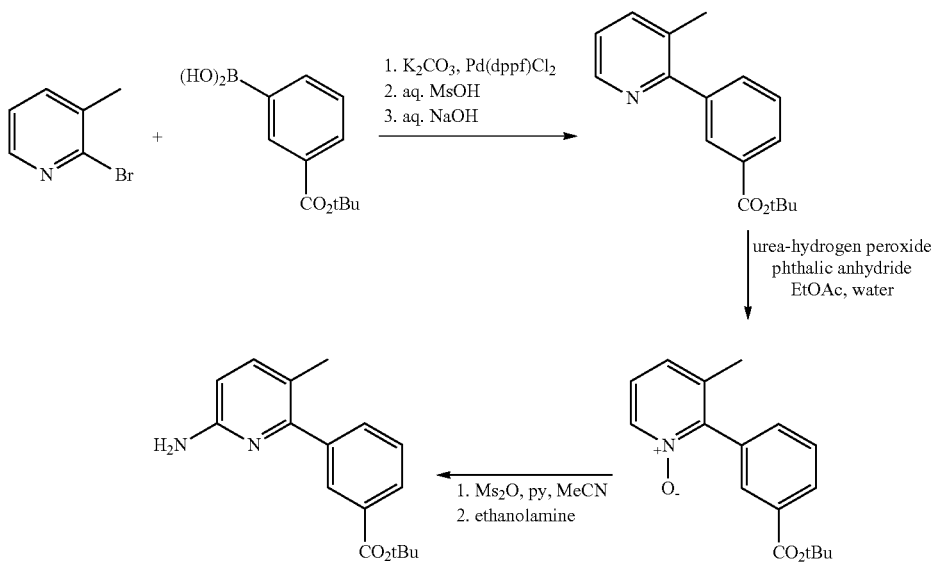

Scheme IV-C. Synthesis of the amine moiety.

Scheme IV-C depicts the preparation of the requisite tert-butyl 3-(6-amino-3-methylpyridin-2-yl)benzoate, which is coupled with 1-(2,2-difluorobenzo[d][1,3]dioxol-5-yl)cyclopropanecarbonyl chloride in Scheme IV-C to give Compound IV. Palladium-catalyzed coupling of 2-bromo-3-methylpyridine with 3-(tert-butoxycarbonyl)phenylboronic acid gives tert-butyl 3-(3-methylpyridin-2-yl)benzoate, which is subsequently converted to the desired compound.

Scheme IV-D.
Formation of an acid salt of 3-(6-(1-(2,2-difluorobenzo[d][1,3]dioxol-5-yl) cyclopropanecarboxamido)-3-methylpyridin-2-yl)benzoic acid.

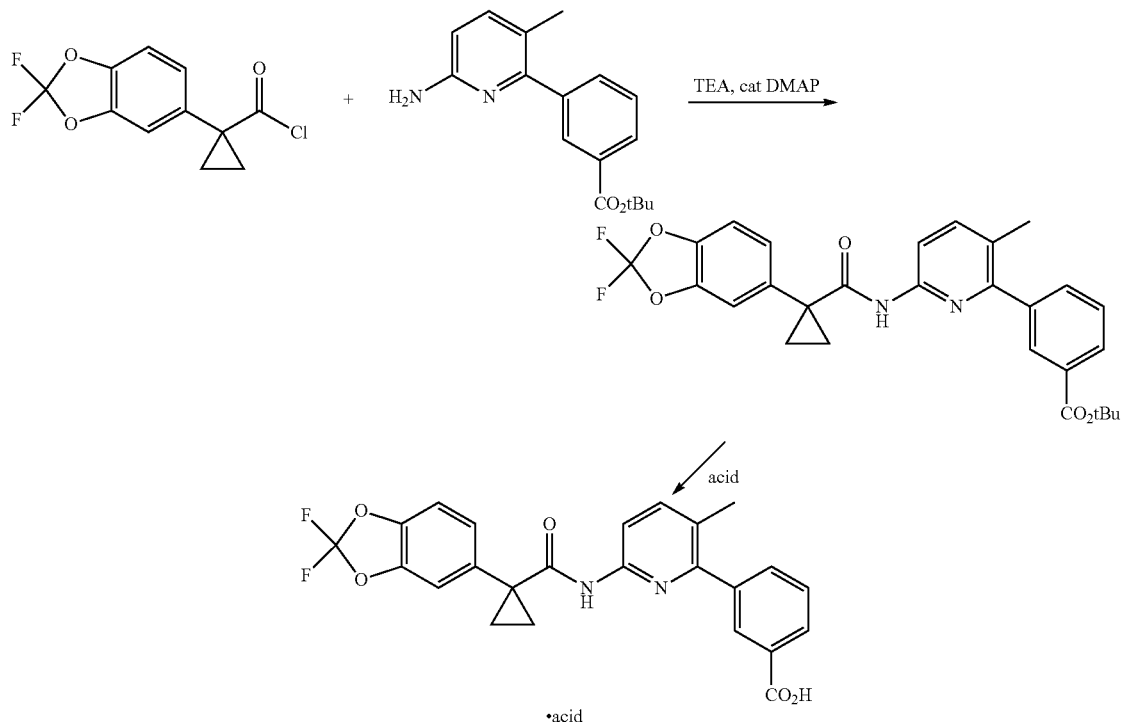

Scheme IV-D depicts the coupling of 1-(2,2-difluorobenzo[d][1,3]dioxol-5-yl)cyclopropanecarbonyl chloride with tert-butyl 3-(6-amino-3-methylpyridin-2-yl)benzoate using triethyl amine and 4-dimethylaminopyridine to initially provide the tert-butyl ester of Compound IV.

Syntheses of Compounds

General UPLC/HPLC Analytical Methods:

Unless indicated, yields of enantiomers separated by chiral SFC are given as a percentage of the theoretical yield for a single enantiomer of the racemate.

LC Method A: Analytical reverse phase UPLC using an Acquity UPLC BEH $C_{18}$ column (30×2.1 mm, 1.7 μm particle) made by Waters (pn: 186002349), and a dual gradient run from 1-99% mobile phase B over 1.2 minutes. Mobile phase A=water (0.05% trifluoroacetic acid). Mobile phase B=acetonitrile (0.035% trifluoroacetic acid). Flow rate=1.5 mL/min, injection volume=1.5 μL, and column temperature=60° C.

LC Method B: Analytical reverse phase UPLC using an Acquity UPLC BEH $C_{18}$ column (50×2.1 mm, 1.7 μm particle) made by Waters (pn: 186002350), and a dual gradient run from 1-99% mobile phase B over 3.0 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method C: Analytical reverse phase HPLC using a Kinetex $C_{18}$ column (50×3.0 mm) and a dual gradient run from 5-100% mobile phase B over 6 min. Mobile phase A=water (0.1% trifluoroacetic acid). Mobile phase B=acetonitrile (0.1% trifluoroacetic acid). Flow rate=1.5 mL/min, injection volume=2 μL, and column temperature=30° C.

LC Method D: Analytical reverse phase UPLC using an Acquity UPLC BEH $C_{18}$ column (50×2.1 mm, 1.7 μm particle) made by Waters (pn: 186002350), and a dual gradient run from 1-99% mobile phase B over 5.0 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method E: Analytical reverse phase UPLC using an Acquity UPLC BEH $C_{18}$ column (50×2.1 mm, 1.7 μm particle) made by Waters (pn: 186002350), and a dual gradient run from 1-99% mobile phase B over 2.5 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method F: Analytical reverse phase UPLC using an Acquity UPLC BEH $C_{18}$ column (50×2.1 mm, 1.7 μm particle) made by Waters (pn: 186002350), and a dual gradient run from 1-99% mobile phase B over 15.0 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method G: Analytical reverse phase UPLC using an Acquity UPLC BEH $C_{18}$ column (50×2.1 mm, 1.7 μm particle) made by Waters (pn: 186002350), and a dual gradient run from 30-99% mobile phase B over 3.0 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method H: Kinetex $C_{18}$ 4.6×50 mm 2.6 μm. Temp: 45° C., Flow: 2.0 mL/min, Run Time: 6 min. Mobile phase:

Initial 95% water (0.1% formic acid) and 5% acetonitrile (0.1% formic acid) linear gradient to 95% acetonitrile (0.1% formic acid) for 4.0 min then hold at 95% acetonitrile (0.1% formic acid) for 2.0 min.

LC Method I: Kinetex $C_{18}$ 4.6×50 mm 2.6 μm. Temp: 45° C., Flow: 2.0 mL/min, Run Time: 3 min. Mobile phase: Initial 95% water (0.1% formic acid) and 5% acetonitrile (0.1% formic acid) linear gradient to 95% acetonitrile (0.1% formic acid) for 2.0 min then hold at 95% acetonitrile (0.1% formic acid) for 1.0 min.

LC Method J: Analytical reverse phase UPLC using an Acquity UPLC BEH $C_{18}$ column (50×2.1 mm, 1.7 μm particle) made by Waters (pn: 186002350), and a dual gradient run from 50-99% mobile phase B over 3.0 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method K: Analytical reverse phase UPLC using an Acquity UPLC BEH $C_{18}$ column (50×2.1 mm, 1.7 μm particle) made by Waters (pn: 186002350), and a dual gradient run from 30-99% mobile phase B over 1.0 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method L: Analytical reverse phase UPLC using an Acquity UPLC BEH $C_{18}$ column (50×2.1 mm, 1.7 μm particle) made by Waters (pn: 186002350), and a dual gradient run from 50-99% mobile phase B over 1.0 minutes. Mobile phase A=water (0.05% trifluoroacetic acid). Mobile phase B=acetonitrile (0.035% trifluoroacetic acid). Flow rate=1.2 mL/min, injection volume=1.5 μL, and column temperature=60° C.

LC Method M: Analytical reverse phase HPLC using a Kinetex $C_{18}$ column (50×3.0 mm) and a dual gradient run from 5-100% mobile phase B over 6 min. Mobile phase A=water (0.1% trifluoroacetic acid). Mobile phase B=acetonitrile (0.1% trifluoroacetic acid). Flow rate=1.5 mL/min, injection volume=10 μL, and column temperature=30° C.

LC Method N: Zorbax $C_{18}$ 4.6×50 mm 3.5 μm. Flow: 2.0 mL/min, 95% water (0.1% trifluoroacetic acid)+5% acetonitrile (0.1% trifluoroacetic acid) to 95% acetonitrile (0.1% trifluoroacetic acid) gradient (2.0 min) then hold at 95% acetonitrile (0.1% trifluoroacetic acid) for 1.0 min.

LC Method O: Zorbax SB-$C_{18}$ 4.6×50 mm 3.5 μm, Temp: 45° C., Flow 2.0 mL/min, Run Time: 4 min. Mobile Phase Conditions: Initial 95% water (0.1% formic acid) and 5% acetonitrile (0.1% formic acid) linear gradient to 95% acetonitrile (0.1% formic acid) for 2.0 min then hold at 95% acetonitrile (0.1% formic acid) for 2.0 min.

LC Method P: Merckmillipore Chromolith SpeedROD $C_{18}$ column (50×4.6 mm) and a dual gradient run from 5-100% mobile phase B over 6 minutes. Mobile phase A=water (0.1% trifluoroacetic acid). Mobile phase B=acetonitrile (0.1% trifluoroacetic acid).

LC Method Q: Merckmillipore Chromolith SpeedROD $C_{18}$ column (50×4.6 mm) and a dual gradient run from 5-100% mobile phase B over 12 minutes. Mobile phase A=water (0.1% trifluoroacetic acid). Mobile phase B=acetonitrile (0.1% trifluoroacetic acid).

LC Method R: Waters Cortex 2.7 μm $C_{18}$ (3.0 mm×50 mm), Temp: 55° C.; Flow: 1.2 mL/min; Mobile phase A: 100% water with 0.1% trifluoroacetic acid. Mobile phase B: 100% acetonitrile with 0.1% trifluoroacetic acid. Gradient: 5% to 100% B over 4 min, with stay at 100% B for 0.5 min, equilibration to 5% B over 1.5 min.

LC Method S: Poroshell 120 EC-$C_{18}$ 3.0×50 mm 2.7 μM, Temp: 45° C., Flow: 2.0 mL/min, Run time: 6 min. Mobile phase conditions: Initial 95% water (0.1% trifluoroacetic acid) and 5% acetonitrile (0.1% trifluoroacetic acid) linear gradient to 95% acetonitrile (0.1% trifluoroacetic acid) for 4.0 min then hold at 95% acetonitrile (0.1% trifluoroacetic acid) for 2.0 min.

LC Method T: Zorbax $C_{18}$ 4.6×50 mm 3.5 μM, Security Guard: AJO-4287 $C_{18}$, 4×3.0 mm. Temp: 45° C., Flow: 2.0 mL/min, Run time: 6 min. Mobile phase: 95% water (0.1% formic acid) and 5% acetonitrile (0.1% formic acid) linear gradient to 95% acetonitrile (0.1% formic acid) for 4.0 min then hold for 2.0 min.

LC Method U: Kinetex EVO $C_{18}$ 4.6×50 mm 2.6 lam, Temp: 45° C., Flow: 2.0 mL/min, Run time: 4 min. Mobile phase: Initial 95% water (0.1% formic acid) and 5% acetonitrile (0.1% formic acid) linear gradient to 95% acetonitrile (0.1% formic acid) for 2.0 min then hold at 95% acetonitrile (0.1% formic acid) for 2.0 min.

Example 1: Preparation of 12,12,19-trimethyl-8-(3-{2-[1-(trifluoromethyl)cyclopropyl]ethoxy}-1H-pyrazol-1-yl)-2$\lambda^6$-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 9)

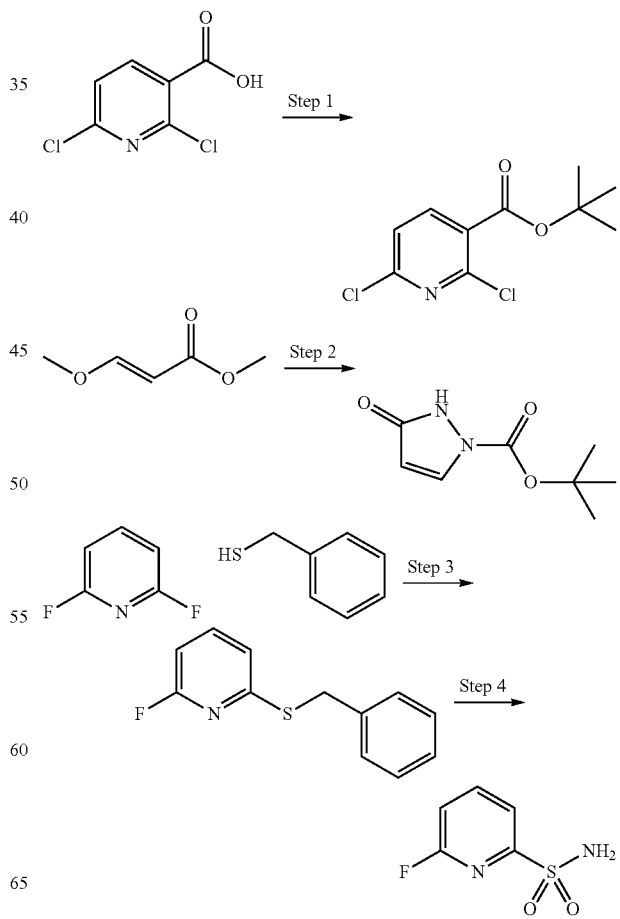

167
-continued
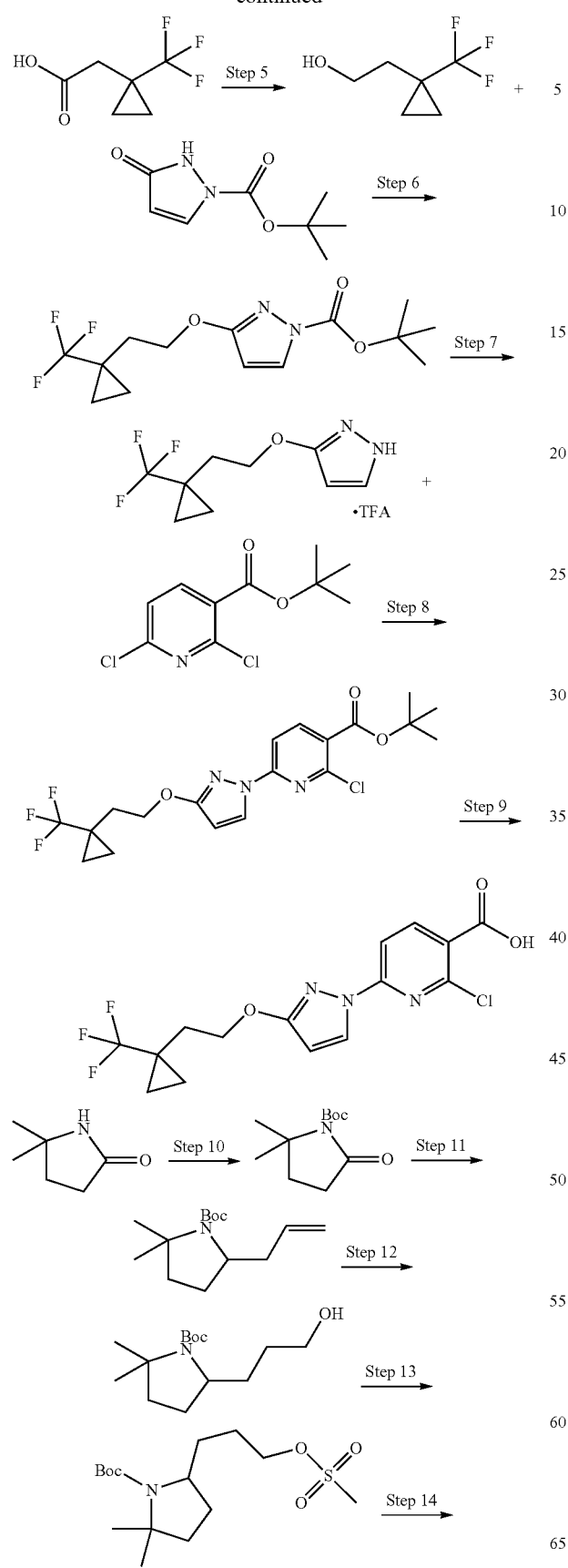
168
-continued
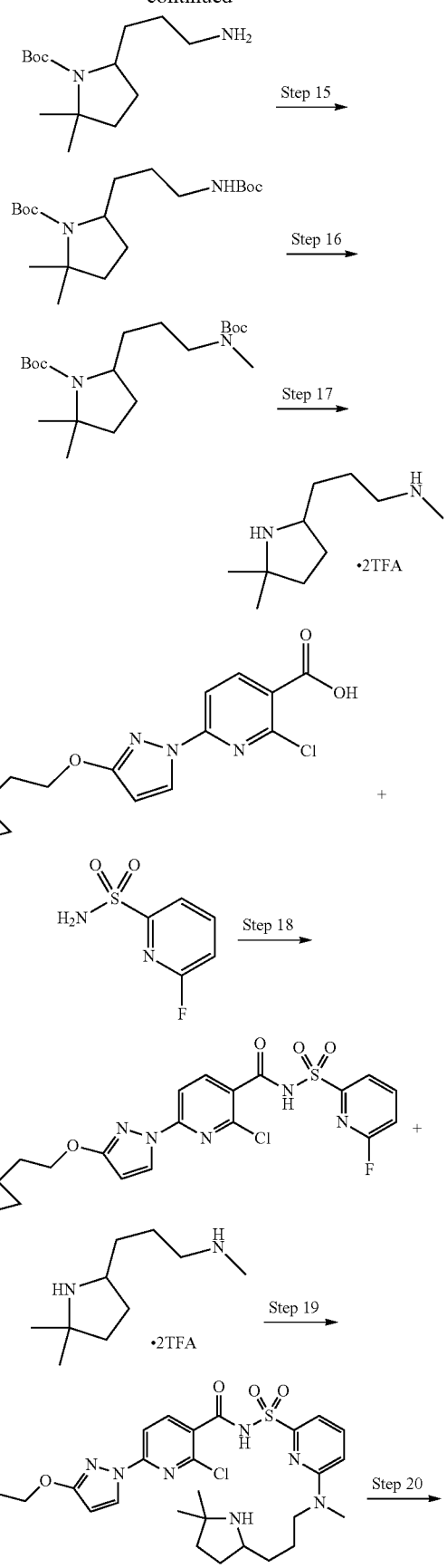

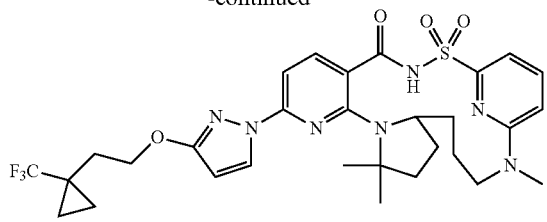

Step 1: tert-Butyl 2,6-dichloropyridine-3-carboxylate

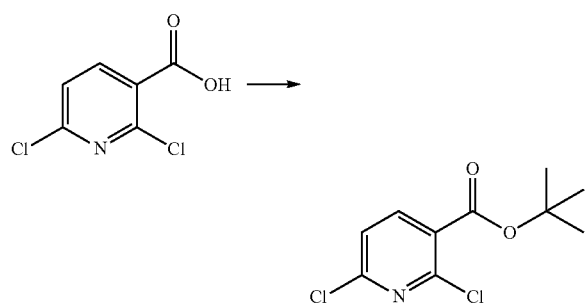

A solution of 2,6-dichloropyridine-3-carboxylic acid (10 g, 52.08 mmol) in tetrahydrofuran (210 mL) was treated successively with di-tert-butyl dicarbonate (17 g, 77.89 mmol) and 4-(dimethylamino)pyridine (3.2 g, 26.19 mmol) and stirred overnight at room temperature. At this point, hydrochloric acid 1N (400 mL) was added, and the mixture was stirred vigorously for about 10 min. The product was extracted with ethyl acetate (2×300 mL), and the combined organic layers were washed with water (300 mL) and brine (150 mL) and dried over sodium sulfate, filtered and concentrated under reduced pressure to give 12.94 g (96% yield) of tert-butyl 2,6-dichloropyridine-3-carboxylate as a colorless oil. $^1$H NMR (300 MHz, CDCl$_3$) δ 1.60 (s, 9H), 7.30 (d, J=7.9 Hz, 1H), 8.05 (d, J=8.2 Hz, 1H). ESI-MS m/z calc. 247.02, found 248.1 (M+1)$^+$; Retention time: 1.79 min (LC Method B).

Step 2: tert-Butyl 3-oxo-2,3-dihydro-1H-pyrazole-1-carboxylate

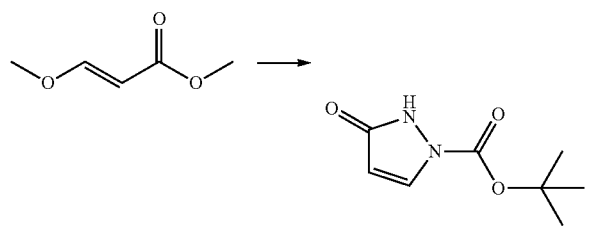

A 50 L reactor was started, and the jacket was set to 20° C., with stirring at 150 rpm, reflux condenser (10° C.) and nitrogen purge. Methanol (2.860 L) and methyl (E)-3-methoxyprop-2-enoate (2.643 kg, 22.76 mol) were added, and the reactor was capped. The reaction was heated to an internal temperature of 40° C. and the system was set to hold jacket temperature at 40° C. Hydrazine hydrate (1300 g of 55% w/w, 22.31 mol) was added portion-wise via addition funnel over 30 min. The reaction was heated to 60° C. for 1 h. The reaction mixture was cooled to 20° C. and triethylamine (2.483 kg, 3.420 L, 24.54 mol) was added portion-wise, maintaining reaction temperature<30° C. A solution of Boc anhydride (4.967 kg, 5.228 L, 22.76 mol) in methanol (2.860 L) was added portion-wise maintaining temperature<45° C. The reaction mixture was stirred at 20° C. for 16 h. The reaction solution was partially concentrated to remove methanol, resulting in a clear, light amber oil. The resulting oil was transferred to the 50 L reactor, stirred and water (7.150 L) and heptane (7.150 L) were added. The additions caused a small amount of the product to precipitate. The aqueous layer was drained into a clean container and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol) which was added dropwise. The jacket was set to 0° C. to absorb the quench exotherm. After the addition was complete (pH=5), the reaction mixture was stirred for 1 h. The solid was collected by filtration and washed with water (7.150 L) then washed a second time with water (3.575 L). The crystalline solid was transferred into a 20 L rotovap bulb and heptane (7.150 L) was added. The mixture was slurried at 45° C. for 30 min and 1-2 volumes of solvent were distilled off. The slurry in the rotovap flask was filtered and the solids were washed with heptane (3.575 L). The solid was further dried in vacuo (50° C., 15 mbar) to give tert-butyl 5-oxo-1H-pyrazole-2-carboxylate (2921 g, 71%) as a coarse, crystalline solid. $^1$H NMR (400 MHz, dimethyl sulfoxide-d6) δ 10.95 (s, 1H), 7.98 (d, J=2.9 Hz, 1H), 5.90 (d, J=2.9 Hz, 1H), 1.54 (s, 9H).

Step 3: 2-Benzylsulfanyl-6-fluoro-pyridine

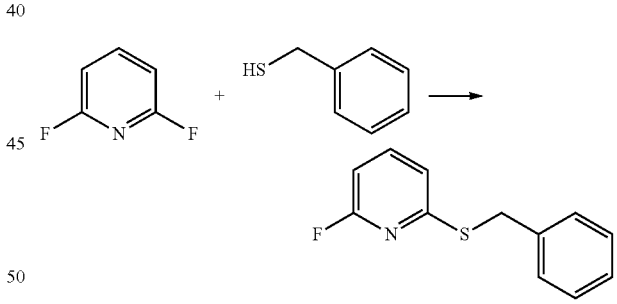

2,6-Difluoropyridine (200 g, 1.738 mol) was dissolved in dimethyl sulfoxide (2 L) in a 5 L three-necked round-bottomed flask equipped with an overhead stirrer, temperature probe and addition funnel. Cesium carbonate (572.4 g, 1.757 mol) was added. Phenylmethanethiol (206 mL, 1.755 mol) was added dropwise via addition funnel. An exotherm was observed during the addition. The temperature rose to approximately 40° C. The reaction was stirred overnight at room temperature. The reaction was poured into water and extracted with dichloromethane. The extract was washed twice with water and filtered over a small plug of silica gel. The plug was eluted with dichloromethane and the filtrate was evaporated in vacuo to afford 2-benzylsulfanyl-6-fluoro-pyridine (366 g, 96%) as a peach-colored oil that solidified under vacuum to huge blocky plates. $^1$H NMR (400 MHz, Chloroform-d) δ 7.58 (q, J=7.9 Hz, 1H), 7.48-7.41 (m, 2H), 7.36-7.25 (m, 4H), 7.06 (dd, J=7.6, 2.1 Hz, 1H), 6.62 (dd, J=7.9, 2.6 Hz, 1H), 4.43 (s, 2H).

Step 4: 6-Fluoropyridine-2-sulfonamide

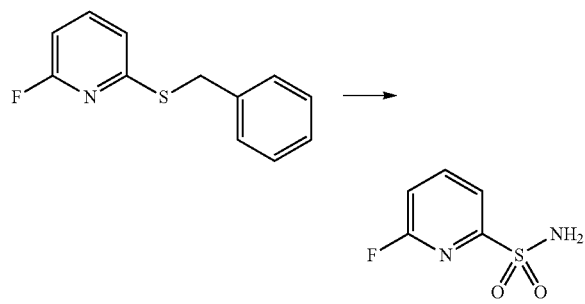

2-Benzylsulfanyl-6-fluoro-pyridine (303.2 g, 1.383 mol) was dissolved in chloroform (2.0 L) in a 12 L three-necked round-bottomed flask equipped with an overhead stirrer and temperature probe. Water (1.5 L) was added and the mixture was cooled in an ice bath to 0° C. and vigorously stirred. Chlorine gas from a lecture bottled was bubbled vigorously into the reaction by way of a Pasteur pipet inserted through a septum on the third neck of the flask. A white precipitate rapidly formed. An exotherm was observed during the addition. The chlorine addition was stopped when the temperature rose to 20° C. The reaction was allowed to cool again before the addition of more chlorine gas. Dosing was continued until the reaction turned a yellowish-green color and stayed that way after stirring for 30 min. At this point, no further exotherms were observed. The reaction was poured into a solution of 40% aqueous sodium bisulfite. The organic layer was separated and the aqueous was extracted with another portion of chloroform. The organic layers were combined, dried over magnesium sulfate, filtered, and evaporated in vacuo to afford a slightly yellow oil. The oil was dissolved in dichloromethane (1.5 L) and added dropwise to ammonium hydroxide (1.5 L of 40% w/v, 17.12 mol) in a 12 L three-necked round-bottomed flask equipped with an overhead stirrer, temperature probe, and addition funnel. The ammonium hydroxide solution was cooled to 0° C. in an ice-bath before the addition. The addition rate was adjusted so the temperature of the reaction stayed below 10° C. The resulting greenish-yellow solution was stirred for an hour and poured into ice. The layers were separated (the organic layer was dark green) and the aqueous layer was extracted with more dichloromethane. The organic layers were discarded. The aqueous layer was cooled in an ice bath and concentrated aqueous hydrochloric acid was added in portions to the aqueous layer until the pH was strongly acidic. The resulting mixture was stirred as each portion was added. The resulting aqueous solution was extracted twice with ethyl acetate. The organic layers were combined, dried over magnesium sulfate, filtered, and evaporated in vacuo to afford a light brown solid. The solid was mixed with dichloromethane (approximately 500 mL) and stirred with a magnetic stirbar until most of the large clumps had broken up. Approximately 1.5 L of pentane was added which precipitated a lot of light brown solid. The resulting mixture was stirred briefly and then filtered. The filter cake was washed with pentane and dried in vacuo to afford 6-fluoro-pyridine-2-sulfonamide (204.1 g, 84%) as a light brown solid. ¹H NMR (300 MHz, dimethyl sulfoxide-d₆) δ 8.52-8.11 (m, 1H), 7.89 (dd, J=7.8, 2.7 Hz, 1H), 7.67 (s, 2H), 7.57-7.44 (m, 1H).

Step 5: 2-[1-(Trifluoromethyl)cyclopropyl]ethanol

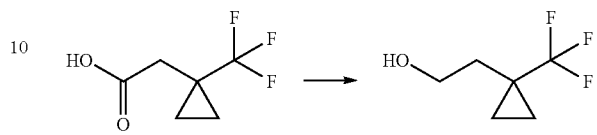

To a solution of lithium aluminum hydride (293 mg, 7.732 mmol) in tetrahydrofuran (10.00 mL) in an ice-bath, 2-[1-(trifluoromethyl)cyclopropyl]acetic acid (1.002 g, 5.948 mmol) in tetrahydrofuran (3.0 mL) was added dropwise over a period of 30 min keeping the reaction temperature below 20° C. The mixture was allowed to gradually warm to ambient temperature and was stirred for 18 h. The mixture was cooled with an ice-bath and sequentially quenched with water (294 mg, 295 μL, 16.36 mmol), sodium hydroxide (297 μL of 6 M, 1.784 mmol), and then water (884.0 μL, 49.07 mmol) to afford a granular solid in the mixture. The solid was filtered off using celite, and the precipitate was washed with ether. The filtrate was further dried with magnesium sulfate and filtered and concentrated in vacuo to afford the product with residual tetrahydrofuran and ether. The mixture was taken directly into the next step without further purification.

Step 6: tert-Butyl 3-[2-[1-(trifluoromethyl)cyclopropyl]ethoxy]pyrazole-1-carboxylate

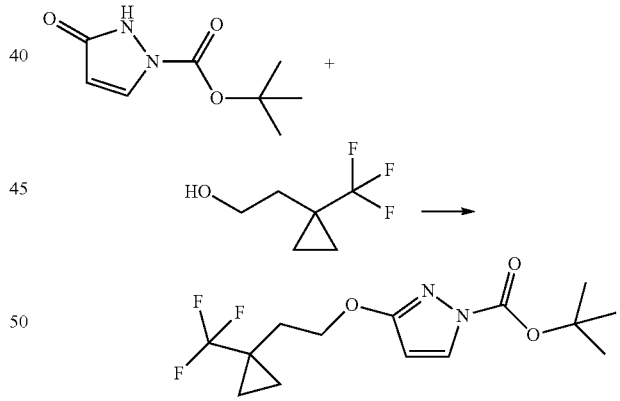

tert-Butyl 5-oxo-1H-pyrazole-2-carboxylate (1.043 g, 5.660 mmol), 2-[1-(trifluoromethyl)cyclopropyl]ethanol (916 mg, 5.943 mmol), and triphenylphosphine (1.637 g, 6.243 mmol) were combined in tetrahydrofuran (10.48 mL) and the reaction was cooled in an ice-bath. Diisopropyl azodicarboxylate (1.288 g, 1.254 mL, 6.368 mmol) was added dropwise to the reaction mixture, and the reaction was allowed to warm to room temperature for 16 h. The mixture was evaporated, and the resulting material was partitioned between ethyl acetate (30 mL) and 1N sodium hydroxide (30 mL). The organic layer was separated, washed with brine (30 mL), dried over sodium sulfate, and concentrated. The crude material was purified by silica gel chromatography eluting with a gradient of ethyl acetate in hexanes (0-30%) to give tert-butyl 3-[2-[1-(trifluoromethyl)cyclopropyl]ethoxy]pyrazole-1-carboxylate (1.03 g, 57%). ESI-MS m/z calc. 320.13, found 321.1 (M+1)+; Retention time: 0.72 min (LC Method A).

Step 7: 3-[2-[1-(Trifluoromethyl)cyclopropyl]ethoxy]-1H-pyrazole

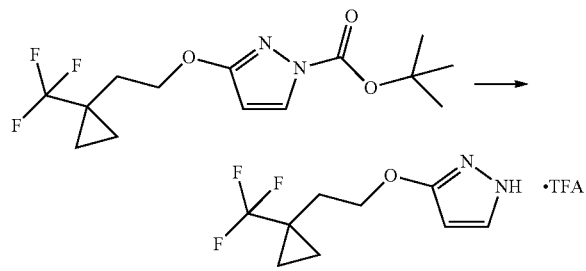

tert-Butyl-3-[2-[1-(trifluoromethyl)cyclopropyl]ethoxy]pyrazole-1-carboxylate (1.03 g, 3.216 mmol) was dissolved in dichloromethane (10.30 mL) with trifluoroacetic acid (2.478 mL, 32.16 mmol), and the reaction was stirred at room temperature for 2 h. The reaction was evaporated, and the resulting oil was partitioned between ethyl acetate (10 mL) and a saturated sodium bicarbonate solution. The organic layer was separated, washed with brine, dried over sodium sulfate, and evaporated to give 3-[2-[1-(trifluoromethyl)cyclopropyl]ethoxy]-1H-pyrazole (612 mg, 86%). $^1$H NMR (400 MHz, dimethyl sulfoxide-$d_6$) δ 11.86 (s, 1H), 7.50 (t, J=2.1 Hz, 1H), 5.63 (t, J=2.3 Hz, 1H), 4.14 (t, J=7.1 Hz, 2H), 2.01 (t, J=7.1 Hz, 2H), 0.96-0.88 (m, 2H), 0.88-0.81 (m, 2H). ESI-MS m/z calc. 220.08, found 221.0 (M+1)$^+$; Retention time: 0.5 min (LC Method A).

Step 8: tert-Butyl 2-chloro-6-[3-[2-[1-(trifluoromethyl)cyclopropyl]ethoxy]pyrazol-1-yl]pyridine-3-carboxylate

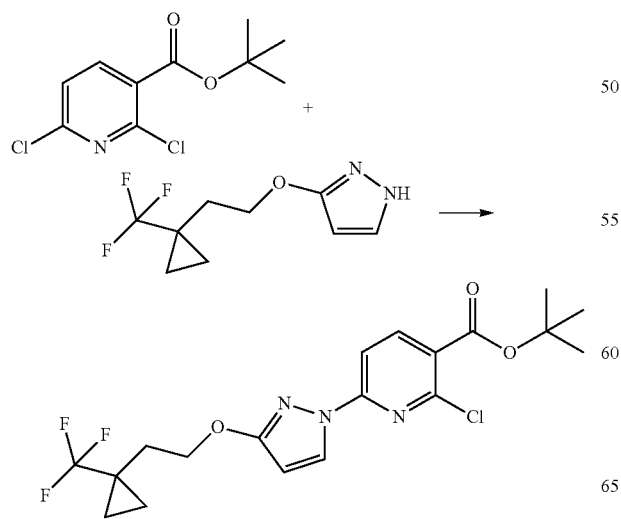

tert-Butyl 2,6-dichloropyridine-3-carboxylate (687 mg, 2.770 mmol), 3-[2-[1-(trifluoromethyl)cyclopropyl]ethoxy]-1H-pyrazole (610 mg, 2.770 mmol), and freshly ground potassium carbonate (459 mg, 3.324 mmol) were combined in anhydrous dimethyl sulfoxide (13.75 mL). 1,4-diazabicyclo[2.2.2]octane (62 mg, 0.5540 mmol) was added, and the mixture was stirred at room temperature under nitrogen for 16 h. The reaction mixture was diluted with water (20 mL) and stirred for 15 min. The resulting solid was collected and washed with water. The solid was dissolved in dichloromethane and dried over magnesium sulfate. The mixture was filtered and concentrated to give tert-butyl 2-chloro-6-[3-[2-[1-(trifluoromethyl)cyclopropyl]ethoxy]pyrazol-1-yl]pyridine-3-carboxylate (1.01 g, 84%). ESI-MS m/z calc. 431.12, found 432.1 (M+1)$^+$; Retention time: 0.88 min (LC Method A).

Step 9: 2-Chloro-6-[3-[2-[1-(trifluoromethyl)cyclopropyl]ethoxy]pyrazol-1-yl]pyridine-3-carboxylic Acid

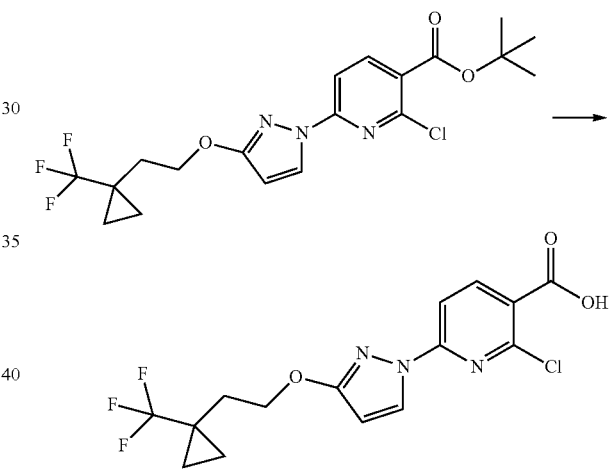

tert-Butyl 2-chloro-6-[3-[2-[1-(trifluoromethyl)cyclopropyl]ethoxy]pyrazol-1-yl]pyridine-3-carboxylate (1.01 g, 2.339 mmol) and trifluoroacetic acid (1.8 mL, 23.39 mmol) were combined in dichloromethane (10 mL) and heated at 40° C. for 3 h. The reaction was concentrated. Hexanes were added, and the mixture was concentrated again to give 2-chloro-6-[3-[2-[1-(trifluoromethyl)cyclopropyl]ethoxy]pyrazol-1-yl]pyridine-3-carboxylic acid (873 mg, 99%) ESI-MS m/z calc. 375.06, found 376.1 (M+1)$^+$; Retention time: 0.69 min (LC Method A).

Step 10: tert-Butyl 2,2-dimethyl-5-oxopyrrolidine-1-carboxylate

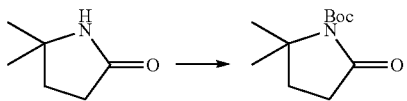

5,5-Dimethylpyrrolidin-2-one (4.77 g, 42.1 mmol), 4-N,N-dimethylamino pyridine (9.19 g, 42.1 mmol) and triethylamine (4.26 g, 42.1 mmol) were dissolved in anhydrous dichloromethane (140 mL) followed by di-tert-butyl dicarbonate (27.6 g, 0.126 mol). The reaction mixture was stirred at room temperature for 48 h. The reaction solution was diluted with dichloromethane (500 mL), washed with 1N hydrogen chloride aqueous solution (100 mL) and brine (2×50 mL). The organic layers were dried over magnesium sulfate, filtered, and concentrated. The residue obtained was subjected to silica gel chromatography using hexanes-ethyl acetate gradient method (0 to 20% ethyl acetate in hexanes) to afford tert-butyl 2,2-dimethyl-5-oxopyrrolidine-1-carboxylate (5.48 g, 58%) as a white solid. $^1$H NMR (250 MHz, CDCl$_3$) δ 2.48 (t, J=8.0 Hz, 2H), 1.85 (t, J=8.0 Hz, 2H), 1.54 (s, 9H), 1.47 (s, 6H). ESI-MS m/z calc. 213.1, found 214.1 (M+1)$^+$. Retention time: 2.36 min (LC Method C).

Step 11: tert-Butyl 5-allyl-2,2-dimethyl-pyrrolidine-1-carboxylate

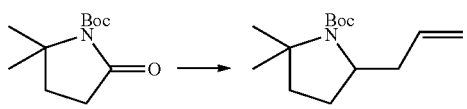 [SMILES: CC(C)(C)OC(=O)N1C(=O)CCC1(C)C ; C=CCC1CCC(C)(C)N1C(=O)OC(C)(C)C]

tert-Butyl 2,2-dimethyl-5-oxopyrrolidine-1-carboxylate (2.72 g, 12.8 mmol) was dissolved in anhydrous ether (36 mL) and anhydrous tetrahydrofuran (36 mL), and then cooled to −78° C. To the above solution was slowly added diisobutylaluminum hydride (14.1 mmol, 14 mL, 1.0M in toluene) and the resulting solution was stirred at −78° C. for 4 h and then warmed to room temperature and further stirred for 3 h. Then, p-toluenesulfonic acid monohydrate (18 mg) in methyl alcohol (40 mL) was added, and the resulting solution was stirred for 19 h. All solvents were removed under reduced pressure. To the residue obtained was added saturated potassium sodium tartrate aqueous solution (100 mL) and stirred for 3 h. The solution was extracted with diethyl ether (3×150 mL). The combined organic layers were washed with brine (2×50 mL), dried over magnesium sulfate, filtered, and concentrated under reduced pressure to afford an intermediate as pale yellow oil (2.65 g). This intermediate and allyltrimethylsilane (2.34 g, 20.5 mmol) were dissolved in anhydrous dichloromethane (60 mL) and cooled to −78° C. Then, boron trifluoride diethyl etherate (1.72 g, 12.1 mmol) was added slowly. After the addition was finished, the reaction solution was stirred at −78° C. for 2 h, and then an additional 2 h at room temperature. 1M Aqueous potassium carbonate solution (25 mL) was added. The organic layer was separated and the aqueous layer was extracted with dichloromethane (3×60 mL). The combined organic layers were washed with brine, dried over magnesium sulfate, filtered and, concentrated under reduced pressure. The residue obtained was subjected to silica gel chromatography using hexanes-ethyl acetate gradient method (0 to 15% ethyl acetate) to afford tert-butyl 5-allyl-2,2-dimethyl-pyrrolidine-1-carboxylate (0.92 g, 30%) as a colorless oil. $^1$H NMR (250 MHz, CDCl$_3$) δ 5.76 (m, 1H), 5.08-5.01 (m, 2H), 3.94-3.82 (m, 1H), 2.43 (m, 1H), 2.13 (m, 1H), 2.00 (m, 2H), 1.70 (m, 2H), 1.57 (s, 9H), 1.41 (s, 3H), 1.28 (s, 3H). ESI-MS m/z calc. 239.2, found 240.1 (M+1)$^+$. Retention time: 3.83 min (LC Method C).

Step 12: tert-Butyl 5-(3-hydroxypropyl)-2,2-dimethylpyrrolidine-1-carboxylate

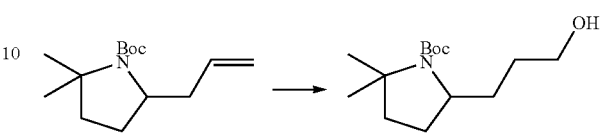

To a solution of tert-butyl 5-allyl-2,2-dimethylpyrrolidine-1-carboxylate (920 mg, 3.85 mmol) in anhydrous tetrahydrofuran (38 mL) at 0° C. was added 9-BBN (15.38 mmol, 30.8 mL, 0.5M in tetrahydrofuran). The resulting solution was stirred at room temperature for 3 h. The reaction solution cooled to 0° C., hydrogen peroxide aqueous solution (38.5 mmol, 4.4 mL, 30% in water) was added followed by sodium hydroxide (19.25 mmol, 3.9 mL, 20% in water). Then, the reaction solution was stirred at room temperature for 1.5 h. Water (50 mL) was added, and the aqueous solution was extracted with diethyl ether (4×80 mL). The combined organic layers were washed with brine, dried over magnesium sulfate, filtered, and concentrated under reduced pressure. The residue obtained was purified by silica gel chromatography using hexanes and ethyl acetate (0 to 35% ethyl acetate in hexanes) to afford tert-butyl 5-(3-hydroxypropyl)-2,2-dimethylpyrrolidine-1-carboxylate (834 mg, 84%) as a colorless oil. $^1$H NMR (250 MHz, dimethyl sulfoxide) δ 4.39 (m, 1H), 3.67 (m, 1H), 3.37 (m, 2H), 1.88-1.49 (m, 6H), 1.40 (s, 6H), 1.38 (s, 3H), 1.31-1.28 (m, 2H), 1.24 (s, 3H). ESI-MS m/z calc. 257.2, found 258.1 (M+1)$^+$. Retention time: 2.79 min (LC Method C).

Step 13: tert-Butyl 2,2-dimethyl-5-(3-methylsulfonyloxypropyl)pyrrolidine-1-carboxylate

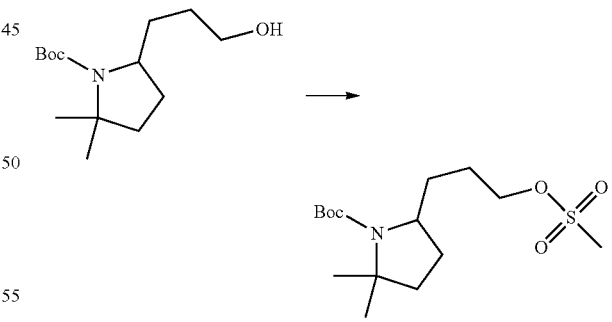

tert-Butyl 5-(3-hydroxypropyl)-2,2-dimethylpyrrolidine-1-carboxylate (3.5 g, 13.6 mmol) and triethylamine (3.8 mL, 27.2 mmol) were dissolved in 40 mL of dichloromethane and chilled in an ice bath. Methanesulfonyl chloride (1.2 mL, 15.0 mmol) was added dropwise over a 10 min period and the resulting mixture was stirred in the ice bath for 20 min. The mixture was quenched with saturated sodium bicarbonate solution (10 mL) and the organic layer was washed with water (10 mL), dried over sodium sulfate, filtered and concentrated under vacuum to obtain tert-butyl 2,2-dimethyl-5-(3-((methylsulfonyl)oxy)propyl)pyrrolidine-1-carboxylate (4.9 g, quantitative yield) as an orange oil. The crude product was used in the next step without further purification. ESI-MS m/z calc. 335.5, found 336.3 (M+1)+; Retention time: 4.24 min (LC Method Q).

Step 14: tert-Butyl 5-(3-aminopropyl)-2,2-dimethyl-pyrrolidine-1-carboxylate

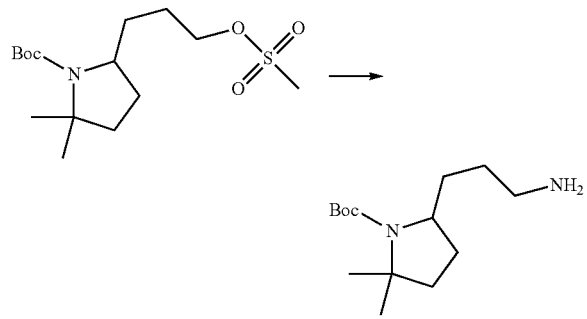

To a solution of 5-(3-methanesulfonyloxy-propyl)-2,2-dimethyl-pyrrolidine-1-carboxylic acid tert-butyl ester (4.9 g, 13.6 mmol) in 1.4-dioxane (70 mL) was added 30% aqueous ammonium hydroxide solution (70 mL) and the resulting mixture was heated in a sealed container at 60° C. for 20 h. The mixture was concentrated under vacuum and extracted with dichloromethane (3×100 mL). The combined organics were concentrated to an oil and purified by silica gel column chromatography using a 0-15% dichloromethane-methanol gradient to obtain tert-butyl 5-(3-aminopropyl)-2,2-dimethyl-pyrrolidine-1-carboxylate (2.14 g, 61% yield over two steps) as a pale oil. $^1$H NMR (500 MHz, dimethyl sulfoxide) δ 3.66 (d, 1H), 2.85 (br s, 2H), 2.58-2.48 (m, 2H), 1.85-1.18 (m, 22H). ESI-MS m/z calc. 256.4, found 257.4 (M+1)+; Retention time: 3.50 min (LC Method Q).

Step 15: tert-Butyl 5-[3-(tert-butoxycarbonylamino)propyl]-2,2-dimethyl-pyrrolidine-1-carboxylate

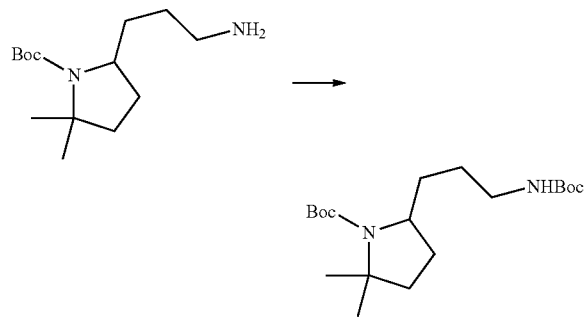

tert-Butyl 5-(3-aminopropyl)-2,2-dimethyl-pyrrolidine-1-carboxylate (640 mg, 2.496 mmol) was dissolved in dichloromethane (6.4 mL) under nitrogen and to it was added triethylamine (1.01 g, 9.981 mmol) followed by di-tert-butyl dicarbonate (1.362 g, 6.241 mmol). The mixture was stirred at room temperature for 1 h. The reaction was diluted with ether and saturated aqueous ammonium chloride and separated. The aqueous layer was washed twice more with ether, the combined organic phases were dried over sodium sulfate, filtered, and concentrated to a light yellow oil which was purified by silica gel chromatography using a shallow gradient from 100% hexanes to 100% Ethyl acetate giving tert-butyl 5-[3-(tert-butoxycarbonylamino)propyl]-2,2-dimethyl-pyrrolidine-1-carboxylate (720 mg, 81%) as a clear oil. ESI-MS m/z calc. 356.26752, found 357.3 (M+1)+; Retention time: 1.73 min (LC Method B).

Step 16: tert-Butyl 5-[3-[tert-butoxycarbonyl(methyl)amino]propyl]-2,2-dimethyl-pyrrolidine-1-carboxylate

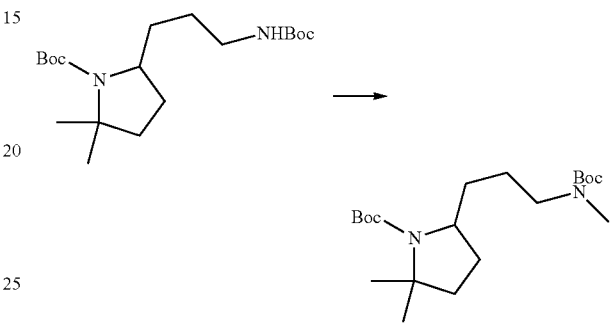

tert-Butyl 5-[3-(tert-butoxycarbonylamino)propyl]-2,2-dimethyl-pyrrolidine-1-carboxylate (720 mg, 2.020 mmol) was dissolved in N,N-dimethylformamide (14.4 mL). Potassium carbonate (837.5 mg, 6.060 mmol) was added followed by methyl iodide (860.2 mg, 6.060 mmol) and the reaction mixture was allowed to stir at room temperature for 16 h. Potassium carbonate (1.396 g, 10.10 mmol) was added followed by methyl iodide (860.2 mg, 6.060 mmol) and the reaction was stirred overnight. Sodium hydride (404 mg, 10.1 mmol) was added and stirred for 6 h. Sodium hydride (121 mg, 5.04 mmol) was added and the reaction was placed in a refrigerator at 4° C. for 3 days. The reaction was warmed to room temperature, methyl iodide (860.2 mg, 6.060 mmol) was added and the reaction was stirred overnight at room temperature. The reaction was diluted with dichloromethane and then washed with water (2×40 mL). The organic layer was washed with brine twice followed by saturated aqueous sodium carbonate to bring the reaction mixture to pH 12. The reaction mixture was then extracted with dichloromethane (3×75 mL). The combined organic fractions were dried over sodium sulfate, filtered, and concentrated to a yellow oil. The residue was purified by silica gel chromatography using a shallow gradient from 100% dichloromethane to 20% methanol/dichloromethane to isolate the product, tert-butyl 5-[3-[tert-butoxycarbonyl(methyl)amino]propyl]-2,2-dimethyl-pyrrolidine-1-carboxylate (695 mg, 93%) as a yellow oil. ESI-MS m/z calc. 370.28317, found 371.5 (M+1)+; Retention time: 0.83 min (LC Method A).

Step 17: 3-(5,5-Dimethylpyrrolidin-2-yl)-N-methyl-propan-1-amine (di-trifluoroacetic Acid Salt)

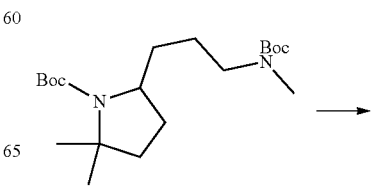

-continued

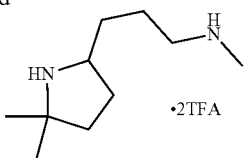

To a stirring solution of tert-butyl 5-[3-[tert-butoxycarbonyl(methyl)amino]propyl]-2,2-dimethyl-pyrrolidine-1-carboxylate (695 mg, 1.876 mmol) in methylene chloride (6.95 mL) at 0° C. was added trifluoroacetic acid (2.891 mL, 37.52 mmol) and the mixture was stirred at room temperature for 5 h. The volatiles were removed under reduced pressure and then evaporated from ether 3 times giving 3-(5,5-dimethylpyrrolidin-2-yl)-N-methyl-propan-1-amine (di-trifluoroacetic acid salt) (747.3 mg, 100%). ESI-MS m/z calc. 170.1783, found 171.3 (M+1)$^+$; Retention time: 0.09 min (LC Method A).

Step 18: 2-Chloro-N-[(6-fluoro-2-pyridyl)sulfonyl]-6-[3-[2-[1-(trifluoromethyl)cyclopropyl]ethoxy]pyrazol-1-yl]pyridine-3-carboxamide

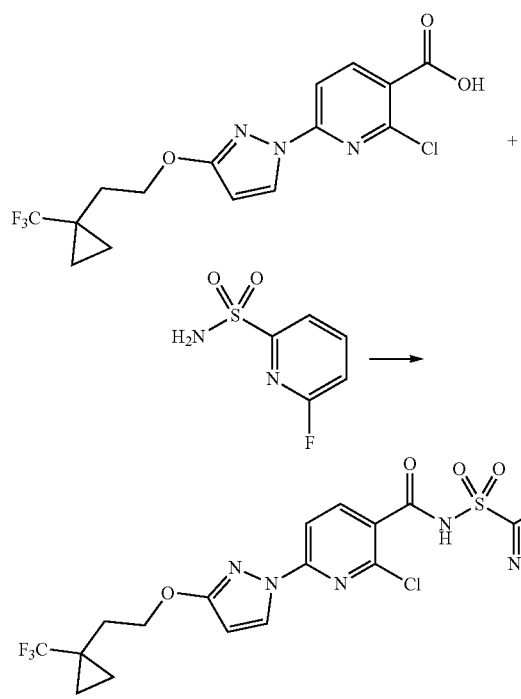

2-Chloro-6-[3-[2-[1-(trifluoromethyl)cyclopropyl]ethoxy]pyrazol-1-yl]pyridine-3-carboxylic acid (1.14 g, 3.03 mmol) and carbonyl diimidazole (590 mg, 3.639 mmol) were combined in tetrahydrofuran (15.3 mL) and stirred for 2 h. At this point, 6-fluoro-2-pyridinesulfonamide (534 mg, 3.03 mmol) was added followed by 1,8-diazabicyclo[5.4.0]undec-7-ene (907 µL, 6.07 mmol) and the reaction was stirred for an additional 30 min at room temperature. The reaction was diluted with ethyl acetate and washed with a 1M citric acid solution, followed by brine. The organics were separated, dried over sodium sulfate, and evaporated to give a white solid. The solid was treated with ether, removed under reduced pressure and then dissolved in minimal hot dichloromethane. The reaction mixture was cooled slowly to room temperature, then in an ice-water bath giving a mass of white solid which was filtered and washed with hexanes. The solid was dried under reduced pressure to afford 2-chloro-N-[(6-fluoro-2-pyridyl)sulfonyl]-6-[3-[2-[1-(trifluoromethyl)cyclopropyl]ethoxy]pyrazol-1-yl]pyridine-3-carboxamide (1.48 g, 89%). ESI-MS m/z calc. 533.05475, found 543.3 (M+1)$^+$; Retention time: 0.72 min (LC Method A).

Step 19: 2-Chloro-N-[[6-[3-(5,5-dimethylpyrrolidin-2-yl)propyl-methyl-amino]-2-pyridyl]sulfonyl]-6-[3-[2-[1-(trifluoromethyl)cyclopropyl]ethoxy]pyrazol-1-yl]pyridine-3-carboxamide

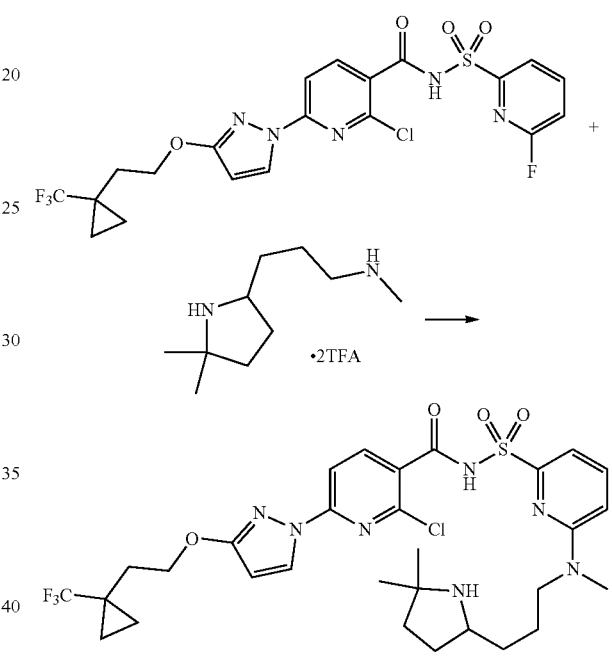

2-chloro-N-[(6-fluoro-2-pyridyl)sulfonyl]-6-[3-[2-[1-(trifluoromethyl)cyclopropyl]ethoxy]pyrazol-1-yl]pyridine-3-carboxamide (1.033 g, 1.876 mmol), 3-(5,5-dimethylpyrrolidin-2-yl)-N-methyl-propan-1-amine (di-trifluoroacetic acid salt) (747.3 mg, 1.876 mmol), potassium carbonate (1.556 g, 11.26 mmol) and dimethyl sulfoxide (5 mL) were added to a vial, capped, and heated to 50° C. for 20 min. The reaction was heated to 65° C. for 90 min. The reaction was cooled back to 50° C. and stirred for 32 h. The reaction was cooled to room temperature and 2-chloro-N-[(6-fluoro-2-pyridyl)sulfonyl]-6-[3-[2-[1-(trifluoromethyl)cyclopropyl]ethoxy]pyrazol-1-yl]pyridine-3-carboxamide (300 mg, 0.5451 mmol) was added and then warmed back to 50° C. and stirred overnight. The reaction was cooled to room temperature and poured into water giving a white precipitate. Concentrated hydrochloric acid was added to bring the pH to 4 and then the white solid was filtered off and washed with water followed by hexanes. The solid was dissolved in dichloromethane, dried (magnesium sulfate), filtered, and concentrated to a white solid. The solid was purified by silica gel chromatography using a shallow gradient from 100% dichloromethane to 20% Methanol/dichloromethane giving 2-chloro-N-[[6-[3-(5,5-dimethylpyrrolidin-2-yl)propyl-methyl-amino]-2-pyridyl]sulfonyl]-6-[3-[2-[1-(trifluoromethyl)cyclopropyl]ethoxy]pyrazol-1-yl]pyridine-3-carboxamide (350 mg, 27%) as a white solid. ESI-MS m/z calc. 683.2268, found 684.5 (M+1)⁺; Retention time: 0.63 min (LC Method A).

Step 20: 12,12,19-Trimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,10.0¹¹,¹⁵]tetracosa-1(23),5,7,9,20(24),21-hexaene-2,2,4-trione (Compound 9)

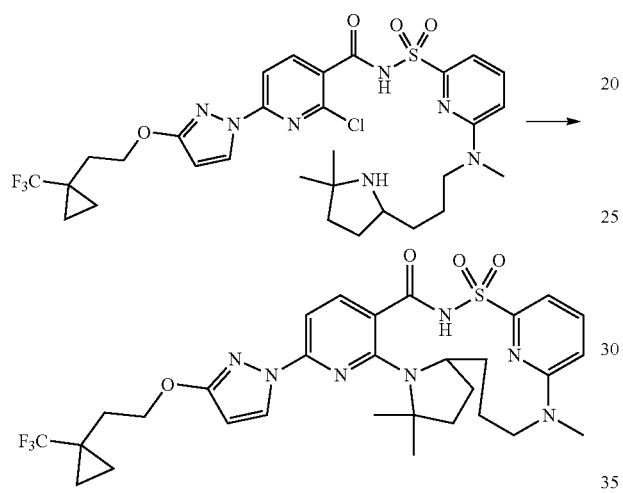

Combined 2-chloro-N-[[6-[3-(5,5-dimethylpyrrolidin-2-yl)propyl-methyl-amino]-2-pyridyl]sulfonyl]-6-[3-[2-[1-(trifluoromethyl)cyclopropyl]ethoxy]pyrazol-1-yl]pyridine-3-carboxamide (350 mg, 0.5116 mmol), potassium carbonate (353.5 mg, 2.558 mmol), cesium fluoride (116.6 mg, 28.34 µL, 0.7674 mmol), 3 Å molecular sieves and dimethyl sulfoxide (7.077 mL) in a vial, purged with nitrogen, capped, heated to 150° C. and stirred for 25 h. Cooled to room temperature then poured into 150 mL of water. Adjusted the pH to 4 by the dropwise addition of concentrated hydrochloric acid giving a tan precipitate which was filtered and washed with water then hexanes. Dissolved the solid in dichloromethane, dried (magnesium sulfate), filtered and concentrated to a tan solid which was purified by silica gel chromatography using a shallow gradient from 100% dichloromethane to 20% methanol/dichloromethane giving 12,12,19-trimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,10.0¹¹,¹⁵]tetracosa-1(23),5,7,9,20(24),21-hexaene-2,2,4-trione (Compound 9) (259.5 mg, 78%). ¹H NMR (400 MHz, dimethyl sulfoxide-d₆) δ 12.62 (s, 1H), 8.22 (d, J=2.8 Hz, 1H), 7.97 (s, 1H), 7.77 (dd, J=8.6, 7.3 Hz, 1H), 7.13 (d, J=7.2 Hz, 1H), 7.04 (s, 1H), 6.82 (d, J=8.7 Hz, 1H), 6.13 (d, J=2.8 Hz, 1H), 4.32 (t, J=7.1 Hz, 2H), 2.96 (s, 3H), 2.08 (t, J=7.0 Hz, 2H), 1.69 (s, 2H), 1.54 (d, J=9.7 Hz, 5H), 1.35 (s, 3H), 1.23 (s, 7H), 0.98-0.95 (m, 2H), 0.89 (td, J=5.8, 4.6, 3.0 Hz, 2H). ESI-MS m/z calc. 647.2502, found 648.2 (M+1)⁺; Retention time: 2.05 min (LC Method B).

Example 2: Preparation of (15S)-12,12,19-trimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,10.0¹¹,¹⁵]tetracosa-1(24),5(10),6,8,20,22-hexaene-2,2,4-trione (Compound 10) and (15R)-12,12,19-trimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,10.0¹¹,¹⁵]tetracosa-1(24),5(10),6,8,20,22-hexaene-2,2,4-trione (Compound 11)

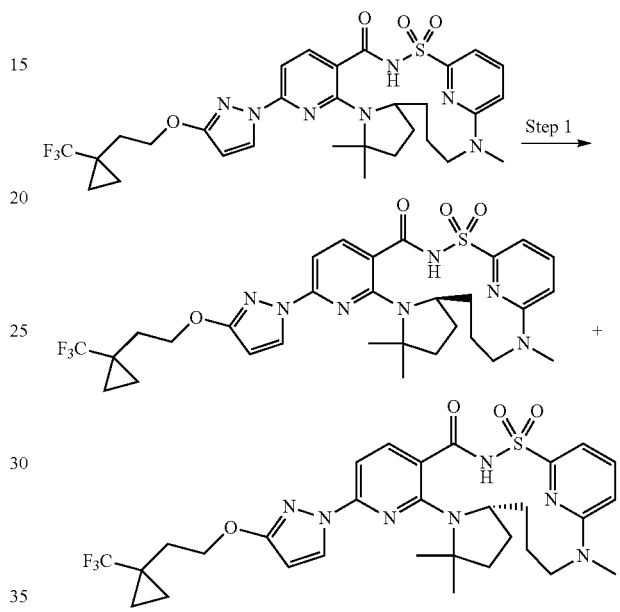

Step 1: (15S)-12,12,19-trimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,10.0¹¹,¹⁵]tetracosa-1(24),5(10),6,8,20,22-hexaene-2,2,4-trione (Compound 10) and (15R)-12,12,19-trimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,10.0¹¹,¹⁵]tetracosa-1(24),5(10),6,8,20,22-hexaene-2,2,4-trione (Compound 11)

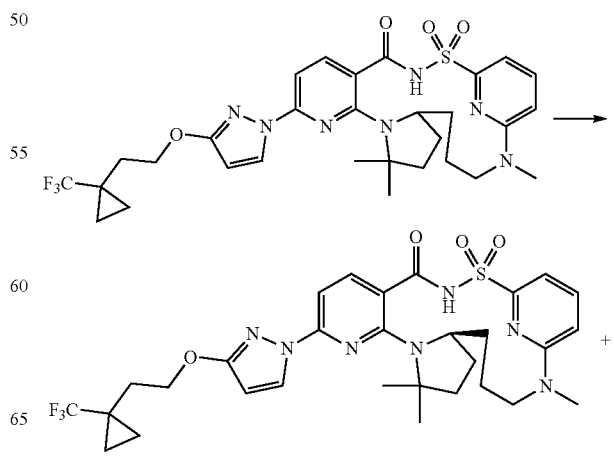

-continued

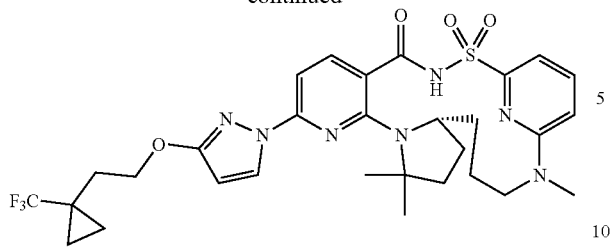

Subjected racemic 12,12,19-trimethyl-8-(3-{2-[1-(trifluoromethyl)cyclopropyl]ethoxy}-1H-pyrazol-1-yl)-2λ$^6$-thia-3,9,11,19,24-pentaazatetracyclo[18.3.1.0$^{5,10}$.0$^{11,15}$]tetracosa-1(23),5,7,9,20(24),21-hexaene-2,2,4-trione (Compound 9) (221.5 mg, 0.3420 mmol) to chiral separation by SFC chromatography using a ChiralPak AS-H (250×21.2 mm column, 5 μm particle size) with 15% Methanol/85% carbon dioxide mobile phase at 10 mL/min over 8.0 min (injection volume=500 μL of 32 mg/mL solution in methanol) giving as the first enantiomer to elute (15S)-12,12,19-trimethyl-8-(3-{2-[1-(trifluoromethyl)cyclopropyl]ethoxy}-1H-pyrazol-1-yl)-2λ$^6$-thia-3,9,11,19,24-pentaazatetracyclo[18.3.1.0$^{5,10}$.0$^{11,15}$]tetracosa-1(24),5(10),6,8,20,22-hexaene-2,2,4-trione (Compound 10) (82.3 mg, 74%) as a white solid; $^1$H NMR (400 MHz, dimethyl sulfoxide-d$_6$) δ 12.64 (s, 1H), 8.22 (d, J=2.8 Hz, 1H), 7.98 (d, J=8.3 Hz, 1H), 7.77 (t, J=7.9 Hz, 1H), 7.12 (d, J=7.2 Hz, 1H), 7.04 (s, 1H), 6.82 (d, J=8.6 Hz, 1H), 6.13 (d, J=2.8 Hz, 1H), 4.32 (t, J=7.0 Hz, 2H), 3.60 (s, 1H), 2.99 (s, 1H), 2.96 (s, 3H), 2.08 (t, J=7.1 Hz, 2H), 1.96-1.84 (m, 1H), 1.69 (s, 3H), 1.52 (s, 6H), 1.35 (s, 3H), 1.02-0.83 (m, 5H), ESI-MS m/z calc. 647.2502, found 648.4 (M+1)$^+$; Retention time: 2.06 min (LC Method B), and as the second enantiomer to elute (15R)-12,12,19-trimethyl-8-(3-{2-[1-(trifluoromethyl)cyclopropyl]ethoxy}-1H-pyrazol-1-yl)-2λ$^6$-thia-3,9,11,19,24-pentaazatetracyclo[18.3.1.0$^{5,10}$.0$^{11,15}$]tetracosa-1(24),5(10),6,8,20,22-hexaene-2,2,4-trione (Compound 11) (81.7 mg, 74%) as a white solid; $^1$H NMR (400 MHz, dimethyl sulfoxide-d$_6$) δ 12.64 (s, 1H), 8.22 (d, J=2.8 Hz, 1H), 7.98 (d, J=8.3 Hz, 1H), 7.77 (t, J=8.0 Hz, 1H), 7.12 (d, J=7.3 Hz, 1H), 7.03 (s, 1H), 6.81 (d, J=8.6 Hz, 1H), 6.12 (d, J=2.7 Hz, 1H), 4.41 (s, 1H), 4.32 (t, J=7.0 Hz, 2H), 3.59 (s, 1H), 3.01 (s, 1H), 2.96 (s, 3H), 2.08 (t, J=7.1 Hz, 2H), 1.92 (d, J=8.7 Hz, 1H), 1.69 (s, 3H), 1.52 (s, 6H), 1.35 (s, 3H), 1.01-0.83 (m, 5H), ESI-MS m/z calc. 647.2502, found 648.4 (M+1)$^+$; Retention time: 2.06 min (LC Method B).

Example 3: Preparation of 12,12-dimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 12)

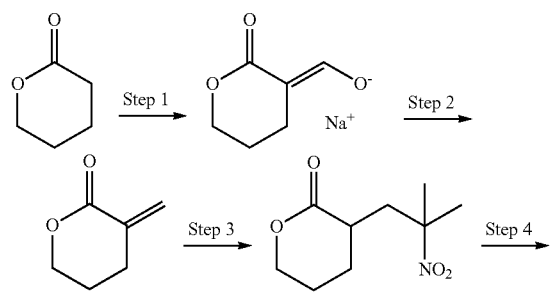

-continued

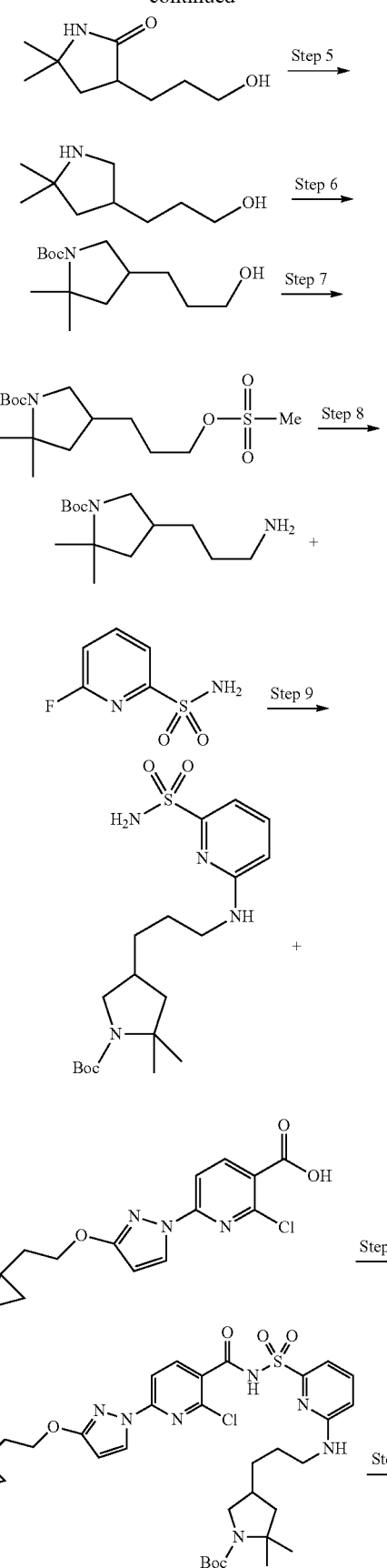

-continued

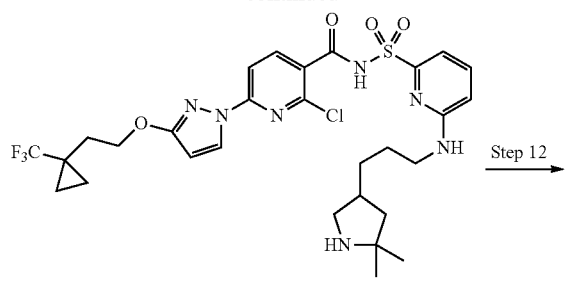

Step 1:
(E)-(2-Oxotetrahydropyran-3-ylidene)methanolate
(Sodium Salt)

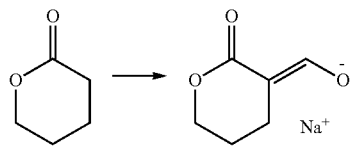 [SMILES: O=C1CCCCO1 ; O=C1OCCC/C1=C\O ; [Na+]]

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with sodium hydride (59.91 g of 60% w/w, 1.498 mol) followed by heptane (1.5 L) which provided a grey suspension. Stirring was commenced and the pot temperature was recorded at 19° C. The vessel was then charged with ethyl alcohol (3.451 g, 74.91 mmol) added via syringe which resulted in gas evolution. The addition funnel was charged with a clear pale yellow solution of tetrahydropyran-2-one (150 g, 1.498 mol) and ethyl formate (111 g, 1.50 mol). The solution was added dropwise over 1 h which resulted in gas evolution and a gradual exotherm to 45° C. The resulting thick white suspension was then heated to 65° C. for 2 h and then allowed to cool to room temperature. The mixture was continued to stir at room temperature overnight (about 10 h). The reaction mixture was vacuum filtered through a glass frit Buchner funnel (medium porosity) under a stream of nitrogen. The filter cake was displacement washed with heptane (2×250 mL) and pulled for a few min. The slightly heptane wet cake was transferred to a glass tray and dried in a vacuum oven at 45° C. for 15 h to provide a white solid (205 g, 1.36 mol, 91% yield) as the desired product, (E)-(2-oxotetrahydropyran-3-ylidene)methanolate (sodium salt).

Step 2: 3-Methylenetetrahydropyran-2-one

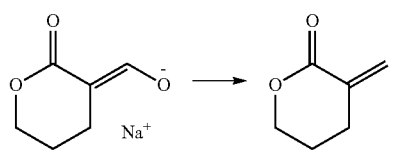

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with (E)-(2-oxotetrahydropyran-3-ylidene)methanolate (sodium salt) (205 g, 1.366 mol) (205 g, 1.366 mol) and tetrahydrofuran (1640 mL) which provided a white suspension. Stirring was commenced and the pot temperature was recorded at 19° C. The vessel was then charged with paraformaldehyde (136.6 g, 4.549 mol) added as a solid in one portion. The resulting suspension was heated to 63° C. and the condition was maintained for 15 h. Upon heating the reaction mixture became slightly gelatinous. The white gelatinous mixture was concentrated under reduced pressure to remove most of the tetrahydrofuran. The remaining residue was partitioned with ethyl acetate (1000 mL), saturated sodium chloride (500 mL) and saturated sodium hydrogen carbonate (500 mL) in a separatory funnel. The organic was removed and the residual aqueous was extracted with ethyl acetate (5×300 mL). The combined organic was dried over sodium sulfate (500 g) and then vacuum filtered through a glass frit Buchner funnel with a 20 mm layer of celite. The filter cake was displacement washed with ethyl acetate (250 mL). The clear filtrate was concentrated under reduced pressure to provide a clear pale yellow oil (135 g) as the desired crude product. The material was purified by silica gel column flash chromatography (liquid load) eluting with a gradient of 100% hexane to 60% ethyl acetate in hexane over 1 h collecting 450 mL fractions. The product was detected by TLC analysis on silica gel eluting with 3:1 hexanes/ethyl acetate and visualized under UV. The product fractions were combined and concentrated under reduced pressure to provide a clear, colorless oil (132 g, 1.18 mol, 72% yield containing 16 wt % residual ethyl acetate by NMR) as the desired product, 3-methylenetetrahydropyran-2-one. $^1$H NMR (400 MHz, dimethyl sulfoxide-$d_6$) δ 6.18 (q, J=1.9 Hz, 1H), 5.60 (q, J=1.9 Hz, 1H), 4.40-4.26 (m, 2H), 2.61 (ddt, J=7.0, 6.3, 2.0 Hz, 2H), 1.90-1.75 (m, 2H).

Step 3:
3-(2-Methyl-2-nitro-propyl)tetrahydropyran-2-one

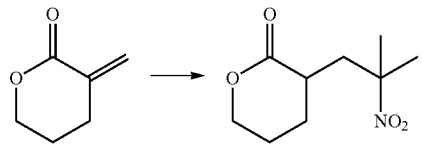

A 5000 mL, 3-neck round bottom flask was fitted with a mechanical stirrer, a cooling bath used as secondary containment, a J-Kem temperature probe, an addition funnel and a nitrogen inlet/outlet. The vessel was charged under a nitrogen atmosphere with 2-nitropropane (104.9 g, 1.177 mol). Stirring was commenced and the pot temperature was recorded at 19° C. The vessel was then charged with 1,8-diazabicyclo[5.4.0]undec-7-ene (22.41 g, 147.2 mmol) added neat in one portion which resulted in a clear light yellow solution. No exotherm was observed. The addition funnel was charged with a solution of 3-methylenetetrahydropyran-2-one (110 g, 981.0 mmol) in acetonitrile (1100 mL) which was added dropwise over 1 h which resulted in a clear light yellow solution and a gradual exotherm to 24° C. The reaction mixture was continued to stir at room temperature for 3.5 h and then concentrated under reduced pressure. The remaining residue was dissolved in dichloromethane (1000 mL) and partitioned with 500 mL of a 3:2 mixture of 1 molar citric acid solution/saturated sodium chloride solution. The resulting organic phase was a clear pale blue solution and the aqueous phase was a slightly cloudy very pale blue solution. The organic was removed and the residual aqueous was extracted with dichloromethane (300 mL). The combined organic was washed with saturated sodium chloride solution (300 mL), dried over sodium sulfate (250 g) and then filtered through a glass frit Buchner funnel. The filtrate was concentrated under reduced pressure to a volume of about 200 mL. The clear pale blue dichloromethane solution was diluted with methyl tert-butyl ether (1500 mL) and the cloudy solution was concentrated under reduced pressure to a volume of about 200 mL which provided a suspension. The mixture was again diluted with methyl tert-butyl ether (1500 mL) and concentrated under reduced pressure to a volume of about 250 mL. The resulting suspension was allowed to stand at room temperature overnight (about 12 h). The solid was collected by vacuum filtration in a glass frit Buchner funnel and the filter cake was displacement washed with cold methyl tert-butyl ether (2×150 mL) and then pulled for 30 min. The material was further dried in a vacuum oven at 45° C. for 5 h to provide (160 g, 0.795 mol, 81% yield) of a white solid as the desired product, 3-(2-methyl-2-nitro-propyl)tetrahydropyran-2-one. $^1$H NMR (400 MHz, dimethyl sulfoxide-d$_6$) δ 4.34 (ddd, J=11.1, 9.3, 4.3 Hz, 1H), 4.20 (dt, J=11.1, 5.1 Hz, 1H), 2.75-2.62 (m, 1H), 2.56 (dd, J=14.9, 5.2 Hz, 1H), 2.01-1.89 (m, 2H), 1.89-1.67 (m, 2H), 1.55 (d, J=6.0 Hz, 6H), 1.44 (dddd, J=12.8, 11.5, 8.1, 6.6 Hz, 1H).

Step 4:
3-(3-Hydroxypropyl)-5,5-dimethyl-pyrrolidin-2-one

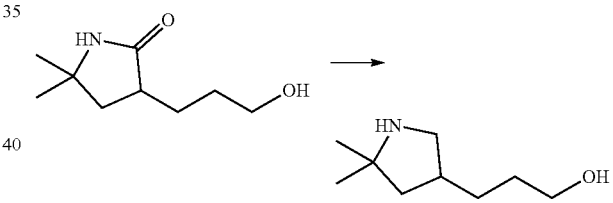

A 1000 mL, 3-neck round bottom flask was fitted with a Teflon stir bar, a heating mantle, a J-Kem temperature probe/controller and rubber septums. The vessel was charged with 3-(2-methyl-2-nitro-propyl)tetrahydropyran-2-one (25 g, 124.2 mmol) and ethyl alcohol (375 mL) which provided a white suspension. Stirring was commenced and the suspension was heated to 40° C. for 10 min which provided a clear colorless solution. The vessel was then fitted with a gas dispersion tube and the solution was degassed with nitrogen for 15 min. The vessel was then charged with Raney Nickel (8.019 g of 50% w/w, 68.31 mmol) and the vessel was then fitted with the septums. The vessel was evacuated and placed under a hydrogen atmosphere. The process was repeated for three cycles. The vessel was then placed under 1 atmosphere hydrogen and the reaction mixture was gradually heated to 60° C. The reaction was continued to stir at 60° C. for 24 h. After cooling to room temperature, the vessel was fitted with a gas dispersion tube and the reaction mixture was degassed with nitrogen for 15 min. The mixture was vacuum filtered through a glass frit Buchner funnel with a 20 mm layer of celite. The filter cake was displacement washed with ethanol (2×100 mL) and pulled until slightly ethyl alcohol wet, then wetted with water and the used Raney nickel catalyst was discarded under water. The clear pale amber filtrate was concentrated under reduced pressure to a clear viscous light amber oil. The oil was diluted with methyl tert-butyl ether (1500 mL) and the cloudy solution was concentrated under reduced pressure to a volume of about 150 mL which provided a suspension. The mixture was again diluted with methyl tert-butyl ether (1500 mL) and concentrated under reduced pressure to a volume of about 150 mL. The resulting suspension was allowed to stand at room temperature overnight (about 12 h). The solid was collected by vacuum filtration in a glass frit Buchner funnel and the filter cake was displacement washed with cold methyl tert-butyl ether (2×50 mL) and then pulled for 30 min. The material was further dried in a vacuum oven at 45° C. for 3 h to provide a white solid (19 g, 0.111 mol, 89% yield) as the product, 3-(3-hydroxypropyl)-5,5-dimethyl-pyrrolidin-2-one. $^1$H NMR (400 MHz, dimethyl sulfoxide-d$_6$) δ 7.63 (s, 1H), 3.38 (t, J=6.5 Hz, 2H), 2.37 (tdd, J=9.8, 8.5, 4.4 Hz, 1H), 2.02 (dd, J=12.3, 8.6 Hz, 1H), 1.72 (tdd, J=9.6, 7.5, 4.4 Hz, 1H), 1.52-1.32 (m, 3H), 1.28-1.03 (m, 7H).

Step 5: 3-(5,5-Dimethylpyrrolidin-3-yl)propan-1-ol

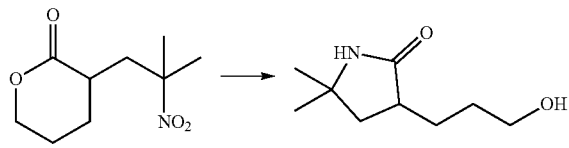

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with lithium aluminum hydride pellets (19.39 g, 510.9 mmol). The vessel was then charged with tetrahydrofuran (500 mL, 20 mL/g). Stirring was commenced and the pot temperature was recorded at 20° C. The mixture was allowed to stir at room temperature for 0.5 h to allow the pellets to dissolve. The pot temperature of the resulting grey suspension was recorded at 24° C. The addition funnel was charged with a solution of 3-(3-hydroxypropyl)-5,5-dimethyl-pyrrolidin-2-one (25 g, 146.0 mmol) in tetrahydrofuran (500 mL) and the clear pale yellow solution was added dropwise over 90 min. Slight heating was required to achieve homogeneity. After the completed addition the pot temperature of the resulting greyish suspension was recorded at 24° C. The mixture was then heated to a pot temperature of 65° C. and the condition was maintained for 72 h. Analysis of the reaction mixture at this point indicated some residual starting material still remaining and no change in product formation. The reaction was subsequently stopped at this point. The heating mantle was removed and the vessel was fitted with a cooling bath. The suspension was cooled to 0° C. with a crushed ice/water cooling bath and then quenched by the very slow dropwise addition of water (19.93 mL), followed by 15 wt % sodium hydroxide solution (19.93 mL) and then finally with water (59.79 mL). The pot temperature of the resulting white suspension was recorded at 5° C. The cooling bath was removed and the vessel was again fitted with a heating mantle. The suspension was warmed to 60° C. and the condition was maintained for 30 min. The warm suspension was vacuum filtered through a glass frit Buchner funnel with a 20 mm layer of celite. The filter cake was then displacement washed with 60° C. tetrahydrofuran (2×250 mL) and then pulled for 30 min. The clear filtrate was concentrated under reduced pressure to provide (23.5 g, 0.149 mol, 99% yield) of a clear light yellow viscous oil as the desired product, 3-(5,5-dimethylpyrrolidin-3-yl)propan-1-ol. $^1$H NMR (400 MHz, dimethyl sulfoxide-$d_6$) δ 3.37 (dt, J=8.3, 6.4 Hz, 3H), 2.95 (dd, J=10.6, 7.6 Hz, 1H), 2.40 (dd, J=10.7, 7.7 Hz, 1H), 2.04 (dt, J=16.1, 8.1 Hz, 1H), 1.69 (dd, J=12.2, 8.2 Hz, 1H), 1.50-1.24 (m, 5H), 1.11-0.94 (m, 7H).

Step 6: tert-Butyl 4-(3-hydroxypropyl)-2,2-dimethyl-pyrrolidine-1-carboxylate

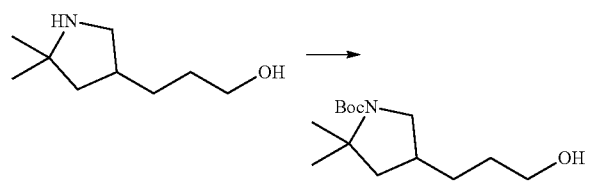

A 1 L, 3-neck round bottom flask was fitted with a mechanical stirrer, a cooling bath, an addition funnel, a J-Kem temperature probe and a nitrogen inlet/outlet. The vessel was charged under a nitrogen atmosphere with 3-(5, 5-dimethylpyrrolidin-3-yl)propan-1-ol (15 g, 95.39 mmol) and dichloromethane (225 mL, 15 mL/g) which provided a clear light yellow solution. Stirring was commenced and the pot temperature was recorded at 19° C. The cooling bath was charged with crushed ice/water and the pot temperature was lowered to 0° C. The addition funnel was charged with triethylamine (12.55 g, 124.0 mmol) which was subsequently added neat dropwise over 5 min. No exotherm was observed. The addition funnel was then charged with di-tert-butyl dicarbonate (22.89 g, 104.9 mmol) dissolved in dichloromethane (225 mL). The clear pale yellow solution was then added dropwise over 30 min which resulted in gentle gas evolution. No exotherm was observed. The cooling bath was removed and the resulting clear light yellow solution was allowed to warm to room temperature and continue to stir at room temperature for 3 h. The reaction mixture was transferred to a separatory funnel and partitioned with water (75 mL). The organic was removed and washed with saturated sodium chloride solution (75 mL), dried over sodium sulfate (150 g) and then filtered through a glass frit Buchner funnel. The filtrate was concentrated under reduced pressure to provide (30 g) of a clear light yellow oil as the desired crude product. The material was purified by silica gel column flash chromatography (liquid load with dichloromethane) eluting with a gradient of 100% dichloromethane to 10% methyl alcohol in dichloromethane over 60 min collecting 50 mL fractions. The desired product fractions were combined and concentrated under reduced pressure to provide tert-butyl 4-(3-hydroxypropyl)-2,2-dimethyl-pyrrolidine-1-carboxylate (22 g, 0.0855 mol, 90% yield) as a clear pale yellow viscous oil. $^1$H NMR (400 MHz, DMSO-$d_6$) δ 4.38 (td, J=5.2, 1.4 Hz, 1H), 3.54 (dt, J=10.3, 6.7 Hz, 1H), 3.38 (td, J=6.6, 3.5 Hz, 2H), 2.76 (q, J=10.3 Hz, 1H), 2.07 (td, J=11.6, 5.7 Hz, 1H), 1.87 (ddd, J=16.7, 12.1, 6.0 Hz, 1H), 1.37 (dd, J=14.2, 10.4 Hz, 17H), 1.24 (s, 3H).

Step 7: tert-Butyl 2,2-dimethyl-4-(3-methylsulfonyl oxypropyl)pyrrolidine-1-carboxylate

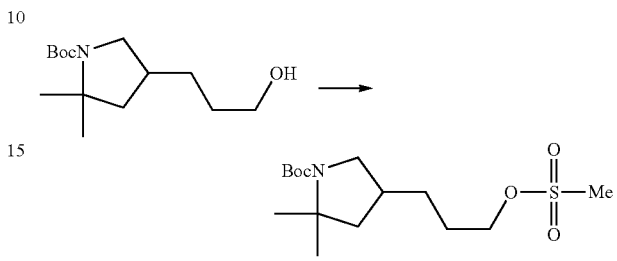

tert-Butyl 4-(3-hydroxypropyl)-2,2-dimethyl-pyrrolidine-1-carboxylate (50.5 g, 196.22 mmol) and triethylamine (39.711 g, 54.698 mL, 392.44 mmol) were dissolved in dichloromethane (500 mL) and the resulting solution was chilled in an ice water bath for 30 min. Mesyl chloride (24.725 g, 16.706 mL, 215.84 mmol) was added dropwise over a 30 min period, then the ice bath was removed and the mixture stirred at room temperature for one hour. The reaction was then quenched with saturated sodium bicarbonate solution (200 mL). The phases were separated and the organic phase was extracted with saturated sodium bicarbonate (200 mL) and water (2×100 mL). The aqueous phases were discarded and the organic phase was dried over sodium sulfate, filtered and concentrated in vacuo to obtain tert-butyl 2,2-dimethyl-4-(3-methylsulfonyl oxypropyl)pyrrolidine-1-carboxylate (64.2 g, 93%) as a pale yellow oil. ESI-MS m/z calc. 335.1766, found 336.4 (M+1)$^+$; Retention time: 5.54 min (LC Method Q).

Step 8: tert-Butyl 4-(3-aminopropyl)-2,2-dimethyl-pyrrolidine-1-carboxylate

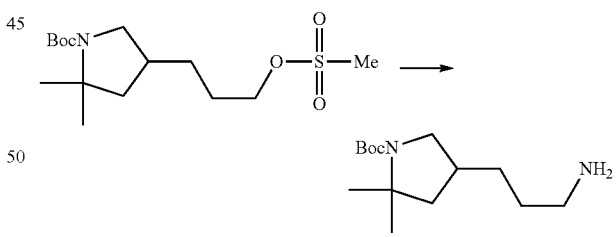

tert-Butyl 2,2-dimethyl-4-(3-methylsulfonyloxypropyl) pyrrolidine-1-carboxylate (64.2 g, 191.38 mmol) was dissolved in dioxane (650 mL) and then ammonium hydroxide (650 mL) was added and the resulting mixture heated to 45° C. for 18 h. After 18 h, the reaction was cooled to room temperature. The solution was diluted with 1M sodium hydroxide (200 mL) and then extracted with diethyl ether (3×650 mL). The aqueous phase was discarded and the combined organic phases were extracted with water (2×200 mL). The aqueous phases were discarded and the organic phase was dried over sodium sulfate, filtered and concentrated in vacuo to afford tert-butyl 4-(3-aminopropyl)-2,2-dimethyl-pyrrolidine-1-carboxylate (48.9 g, 95%) as a pale yellow oil. ESI-MS m/z calc. 256.2151, found 257.3 (M+1)⁺; Retention time: 3.70 min (LC Method Q).

Step 9: tert-Butyl 2,2-dimethyl-4-[3-[(6-sulfamoyl-2-pyridyl)amino]propyl]pyrrolidine-1-carboxylate

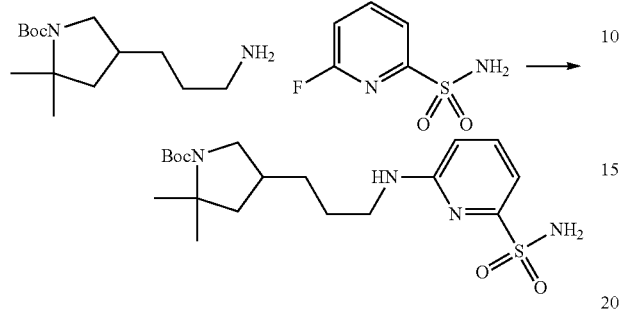

To tert-butyl 4-(3-aminopropyl)-2,2-dimethyl-pyrrolidine-1-carboxylate (8.91 g, 34.8 mmol) and 6-fluoropyridine-2-sulfonamide (6.13 g, 34.8 mmol) in dimethyl sulfoxide (75 mL) was added potassium carbonate (4.91 g, 35.5 mmol) and the mixture stirred at 100° C. for 12 h and then allowed to cool to ambient temperature and stirred for an additional 4 h (16 h total). The reaction mixture was slowly poured into hydrochloric acid (35 mL of 1 M, 35.00 mmol) in water (200 mL) (some foaming) and diluted with ethyl acetate (250 mL). The organic phase was separated and washed with 100 mL of brine. The organic phase was dried over magnesium sulfate, filtered over celite, and concentrated in vacuo to afford a dark yellow oil. The crude product was purified by silica gel chromatography eluting with 0%-100% ethyl acetate in hexanes. Collected both pure (9.0 g) and impure (3 g) fractions. Purified the impure fractions by silica gel chromatography eluting with 0%-100% ethyl acetate in hexanes affording, in total, tert-butyl 2,2-dimethyl-4-[3-[(6-sulfamoyl-2-pyridyl)amino]propyl]pyrrolidine-1-carboxylate (10.0 g, 69%). ¹H NMR (400 MHz, dimethyl sulfoxide-d₆) δ 7.52 (dd, J=8.5, 7.2 Hz, 1H), 7.07 (s, 2H), 6.95 (dd, J=7.2, 0.7 Hz, 2H), 6.61 (d, J=8.5 Hz, 1H), 3.55 (q, J=9.1 Hz, 1H), 3.32-3.24 (m, 2H), 2.79 (q, J=10.0 Hz, 1H), 2.13 (d, J=16.1 Hz, 1H), 1.96-1.82 (m, 1H), 1.51 (dt, J=18.0, 9.3 Hz, 2H), 1.37 (dd, J=12.9, 10.6 Hz, 15H), 1.24 (s, 3H). ESI-MS m/z calc. 412.21442, found 413.1 (M+1)⁺; Retention time: 2.34 min (LC Method D).

Step 10: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate

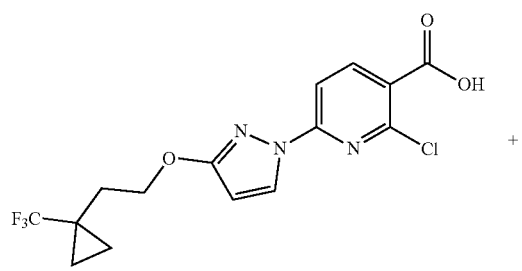

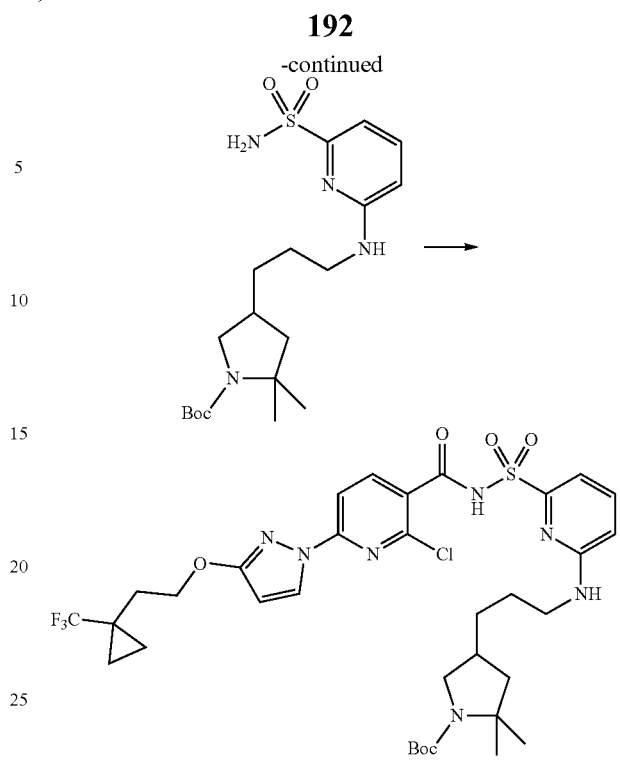

Part A: To 2-chloro-6-[3-[2-[1-(trifluoromethyl)cyclopropyl]ethoxy]pyrazol-1-yl]pyridine-3-carboxylic acid (11.4 g, 30.34 mmol) in tetrahydrofuran (150 mL) was slowly added carbonyl diimidazole (5.9 g, 36 mmol). The mixture was stirred at ambient temperature for 1 hr. Additional carbonyl diimidazole (0.5 g, 3 mmol) was added and the reaction was stirred at ambient temperature for an additional 1 h (2 h total).

Part B: To the activated ester prepared in Part A was added tert-butyl 2,2-dimethyl-4-[3-[(6-sulfamoyl-2-pyridyl)amino]propyl]pyrrolidine-1-carboxylate (10.0 g, 24.24 mmol) in tetrahydrofuran (50 mL) followed by 1,8-diazabicyclo[5.4.0]undec-7-ene (7.5 mL, 50. mmol) and the mixture stirred at ambient temperature for 16 hr. Citric acid (25.1 g, 130.6 mmol) in water (200 mL) was slowly added to the reaction mixture and acidified to pH=3. The mixture became cloudy but no precipitate formed. The mixture was extracted with ethyl acetate (400 mL) and the organic phase washed with brine, dried over magnesium sulfate, filtered over celite, and concentrated in vacuo. The crude product was purified by silica gel chromatography eluting with 0-80% ethyl acetate/hexanes affording the product as a foam, tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate (13.82 g, 74%) ¹H NMR (400 MHz, dimethyl sulfoxide-d₆) δ 12.79 (s, 1H), 8.40 (t, J=2.7 Hz, 1H), 8.11 (d, J=8.4 Hz, 1H), 7.71 (d, J=8.3 Hz, 1H), 7.62 (dd, J=8.5, 7.2 Hz, 1H), 7.21 (d, J=5.8 Hz, 1H), 7.17 (d, J=7.1 Hz, 1H), 6.74 (d, J=8.5 Hz, 1H), 6.19 (t, J=2.3 Hz, 1H), 4.34 (t, J=7.1 Hz, 2H), 3.50 (dt, J=18.3, 9.0 Hz, 1H), 3.23 (d, J=6.7 Hz, 2H), 2.80-2.69 (m, 1H), 2.09 (t, J=7.1 Hz, 2H), 1.79 (td, J=12.4, 6.1 Hz, 1H), 1.52 (dt, J=15.4, 8.0 Hz, 2H), 1.36 (d, J=11.4 Hz, 10H), 1.33-1.25 (m, 5H), 1.17 (s, 2H), 0.99-0.92 (m, 2H), 0.89 (d, J=5.0 Hz, 2H). ESI-MS m/z calc. 769.2636, found 770.1 (M+1)⁺; Retention time: 3.48 min (LC Method D).

Step 11: 2-chloro-{N}-[[6-[3-(5,5-dimethylpyrrolidin-3-yl)propylamino]-2-pyridyl]sulfonyl]-6-[3-[2-[1-(trifluoromethyl)cyclopropyl]ethoxy]pyrazol-1-yl]pyridine-3-carboxamide (Dihydrochloride Salt)

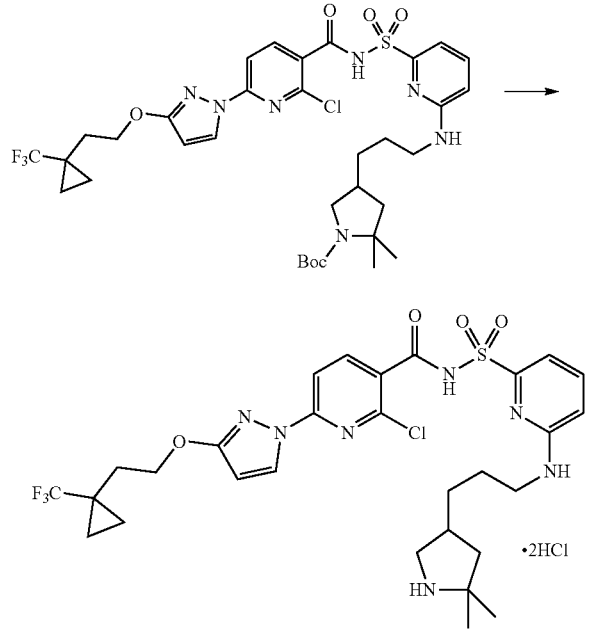

To tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate (13.8 g, 17.92 mmol) in dichloromethane (75 mL) was added hydrochloric acid (15 mL of 4 M, 60.00 mmol) and the mixture stirred at ambient temperature for 16 hr. The solvent was removed in vacuo and the residue diluted with 100 mL of ethyl acetate. The solvent was removed in vacuo and repeated with an additional 100 mL of ethyl acetate affording a foam, 2-chloro-[[6-[3-(5,5-dimethylpyrrolidin-3-yl)propylamino]-2-pyridyl]sulfonyl]-6-[3-[2-[1-(trifluoromethyl)cyclopropyl]ethoxy]pyrazol-1-yl]pyridine-3-carboxamide (dihydrochloride salt) (13.5 g, 101%). ¹H NMR (400 MHz, dimethyl sulfoxide-d₆) δ 12.83 (s, 1H), 9.06 (s, 1H), 8.92 (s, 1H), 8.42 (d, J=2.8 Hz, 1H), 8.11 (d, J=8.4 Hz, 1H), 7.72 (d, J=8.4 Hz, 1H), 7.63 (dd, J=8.5, 7.2 Hz, 1H), 7.29 (s, 1H), 7.18 (dd, J=7.2, 0.7 Hz, 1H), 6.76 (dd, J=8.5, 0.7 Hz, 1H), 6.21 (d, J=2.9 Hz, 1H), 4.95 (s, 2H), 4.35 (t, J=7.0 Hz, 2H), 3.41-3.28 (m, 1H), 3.24 (p, J=6.7 Hz, 2H), 2.80 (tt, J=11.8, 6.7 Hz, 1H), 2.35 (q, J=7.8, 7.3 Hz, 1H), 2.09 (t, J=7.1 Hz, 2H), 1.91 (dd, J=12.8, 7.6 Hz, 1H), 1.58-1.43 (m, 3H), 1.42-1.31 (m, 5H), 1.24 (s, 3H), 1.01-0.93 (m, 2H), 0.90 (dd, J=7.9, 3.2 Hz, 2H). ESI-MS m/z calc. 669.2112, found 670.0 (M+1)⁺; Retention time: 2.26 min (LC Method D).

Step 12: 12,12-Dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 12)

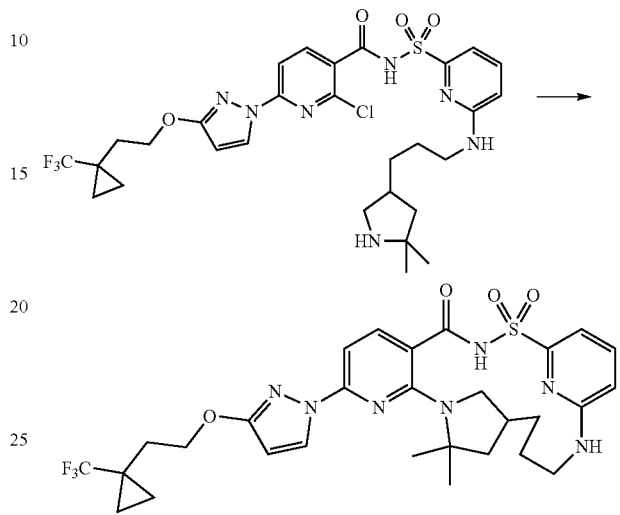

To the 2-chloro-N-[[6-[3-(5,5-dimethylpyrrolidin-3-yl)propylamino]-2-pyridyl]sulfonyl]-6-[3-[2-[1-(trifluoromethyl)cyclopropyl]ethoxy]pyrazol-1-yl]pyridine-3-carboxamide (dihydrochloride salt) (12.9 g, 17.36 mmol) in NMP (120 mL) was added potassium carbonate (9.64 g, 69.8 mmol) followed by cesium fluoride (2.69 g, 17.7 mmol) and the slurry was stirred at 150° C. for 16 hr. The reaction was then allowed to cool to ambient temperature. The mixture was diluted with water (100 mL) and poured into water (400 mL) and the mixture was slowly acidified with hydrochloric acid (27.0 mL of 6 M, 162.0 mmol). The precipitate was collected using a medium frit and washed 3× with 50 mL of water. The solid was air dried for 1 h and then dissolved in ethyl acetate (400 mL). The organic phase was concentrated in vacuo and the crude product purified by silica gel chromatography eluting with 0-100% ethyl acetate/hexanes. 6.3 g of pure product and 6 g of impure fractions were collected. The impure fractions were purified by silica gel chromatography eluting with 0-5% methanol/dichloromethane which provided good separation of product from impurities. The pure product fractions were combined affording 12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 12) (7.4 g, 67%). ¹H NMR (400 MHz, dimethyl sulfoxide-d₆) δ 12.52 (s, 1H), 8.22 (d, J=2.8 Hz, 1H), 7.82 (d, J=8.2 Hz, 1H), 7.58 (dd, J=8.5, 7.2 Hz, 1H), 7.05 (d, J=7.0 Hz, 1H), 7.00 (s, 1H), 6.92 (d, J=8.2 Hz, 1H), 6.71 (d, J=8.2 Hz, 1H), 6.11 (d, J=2.8 Hz, 1H), 4.31 (t, J=7.0 Hz, 2H), 4.02-3.81 (m, 1H), 3.15 (dt, J=10.1, 3.8 Hz, 1H), 2.95 (d, J=13.7 Hz, 1H), 2.78-2.61 (m, 1H), 2.15 (dd, J=5.7, 2.9 Hz, 1H), 2.07 (d, J=6.4 Hz, 2H), 1.92-1.82 (m, 1H), 1.81-1.69 (m, 1H), 1.64-1.53 (m, 6H), 1.51 (s, 3H), 1.36-1.23 (m, 1H), 0.99-0.93 (m, 2H), 0.90 (d, J=10.8 Hz, 2H). ESI-MS m/z calc. 633.2345, found 634.2 (M+1)⁺; Retention time: 2.23 min (LC Method E).

Example 4: Preparation of (14R)-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 13) and (14S)-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 14)

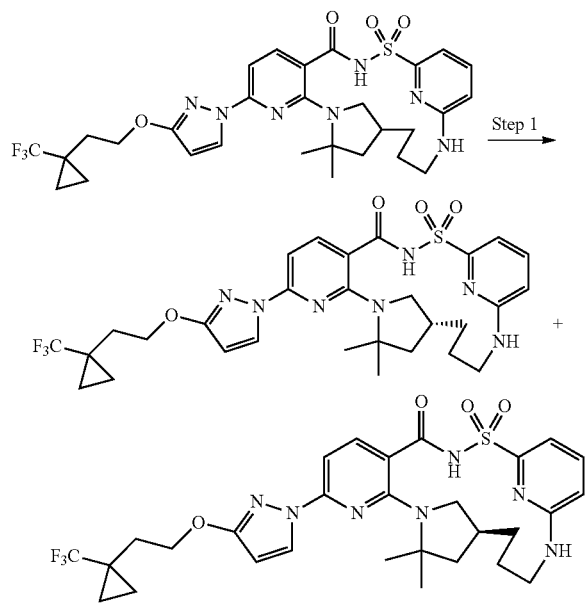

Step 1: (14R)-12,12-Dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 13) and (14S)-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 14)

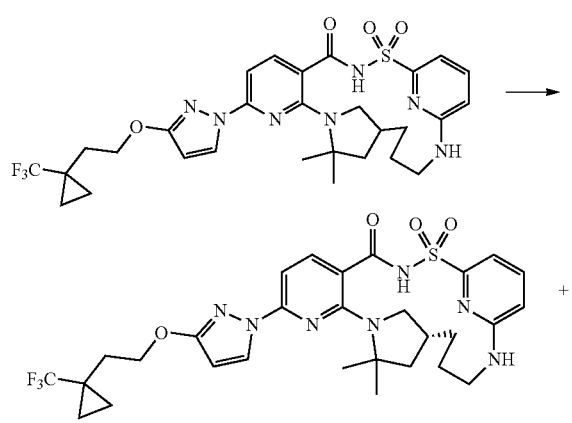

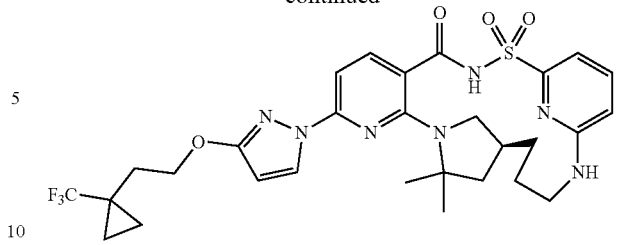

Racemic 12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (7.4 g) was dissolved in 150 mL of acetonitrile and subjected to chiral SFC purification. The sample was separated by chiral SFC chromatography using a ChiralPak AS-H (250×21.2 mm column, 5 μm particle size) with 25% acetonitrile:methanol (90:10))/75% carbon dioxide mobile phase at 70 mL/min giving as the first enantiomer to elute, (14R)-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 13) (2.91 g, 53%); $^1$H NMR (400 MHz, dimethyl sulfoxide-$d_6$) δ 12.51 (s, 1H), 8.21 (d, J=2.7 Hz, 1H), 7.82 (d, J=8.2 Hz, 1H), 7.58 (t, J=7.8 Hz, 1H), 7.05 (d, J=7.0 Hz, 1H), 6.99 (d, J=5.8 Hz, 1H), 6.92 (d, J=8.2 Hz, 1H), 6.71 (d, J=8.5 Hz, 1H), 6.11 (d, J=2.7 Hz, 1H), 4.31 (t, J=7.0 Hz, 2H), 3.93 (s, 1H), 3.16 (s, 1H), 2.95 (d, J=12.7 Hz, 1H), 2.80-2.64 (m, 1H), 2.10 (s, 1H), 2.08 (t, J=7.1 Hz, 2H), 1.86 (dd, J=11.5, 5.4 Hz, 1H), 1.81-1.71 (m, 1H), 1.60 (s, 6H), 1.51 (s, 3H), 1.31 (d, J=12.8 Hz, 1H), 0.95 (d, J=4.3 Hz, 2H), 0.89 (s, 2H); ESI-MS m/z calc. 633.2345, found 634.3 (M+1)⁺; Retention time: 2.19 min; and as the second enantiomer to elute, (14S)-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 14) (3.0 g, 54%) $^1$H NMR (400 MHz, dimethyl sulfoxide-$d_6$) δ 12.52 (s, 1H), 8.22 (d, J=2.8 Hz, 1H), 7.82 (d, J=8.2 Hz, 1H), 7.58 (dd, J=8.5, 7.1 Hz, 1H), 7.05 (d, J=7.2 Hz, 1H), 6.99 (s, 1H), 6.92 (d, J=8.2 Hz, 1H), 6.71 (d, J=8.5 Hz, 1H), 6.11 (d, J=2.8 Hz, 1H), 4.31 (t, J=7.0 Hz, 2H), 3.92 (d, J=12.6 Hz, 1H), 3.15 (s, 1H), 2.95 (d, J=13.2 Hz, 1H), 2.78-2.64 (m, 1H), 2.08 (t, J=7.1 Hz, 3H), 1.86 (dd, J=11.9, 5.3 Hz, 1H), 1.77 (s, 1H), 1.60 (s, 6H), 1.51 (s, 3H), 1.31 (q, J=11.9 Hz, 1H), 1.00-0.92 (m, 2H), 0.90 (d, J=10.4 Hz, 2H). ESI-MS m/z calc. 633.2345, found 634.1 (M+1)⁺; Retention time: 2.2 min (LC Method B).

Example 5: Preparation of 12,12-dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 15)

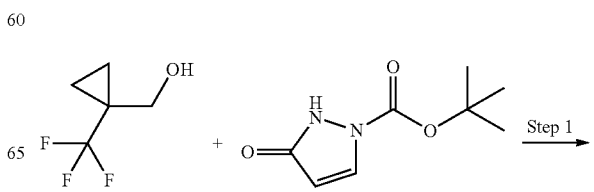

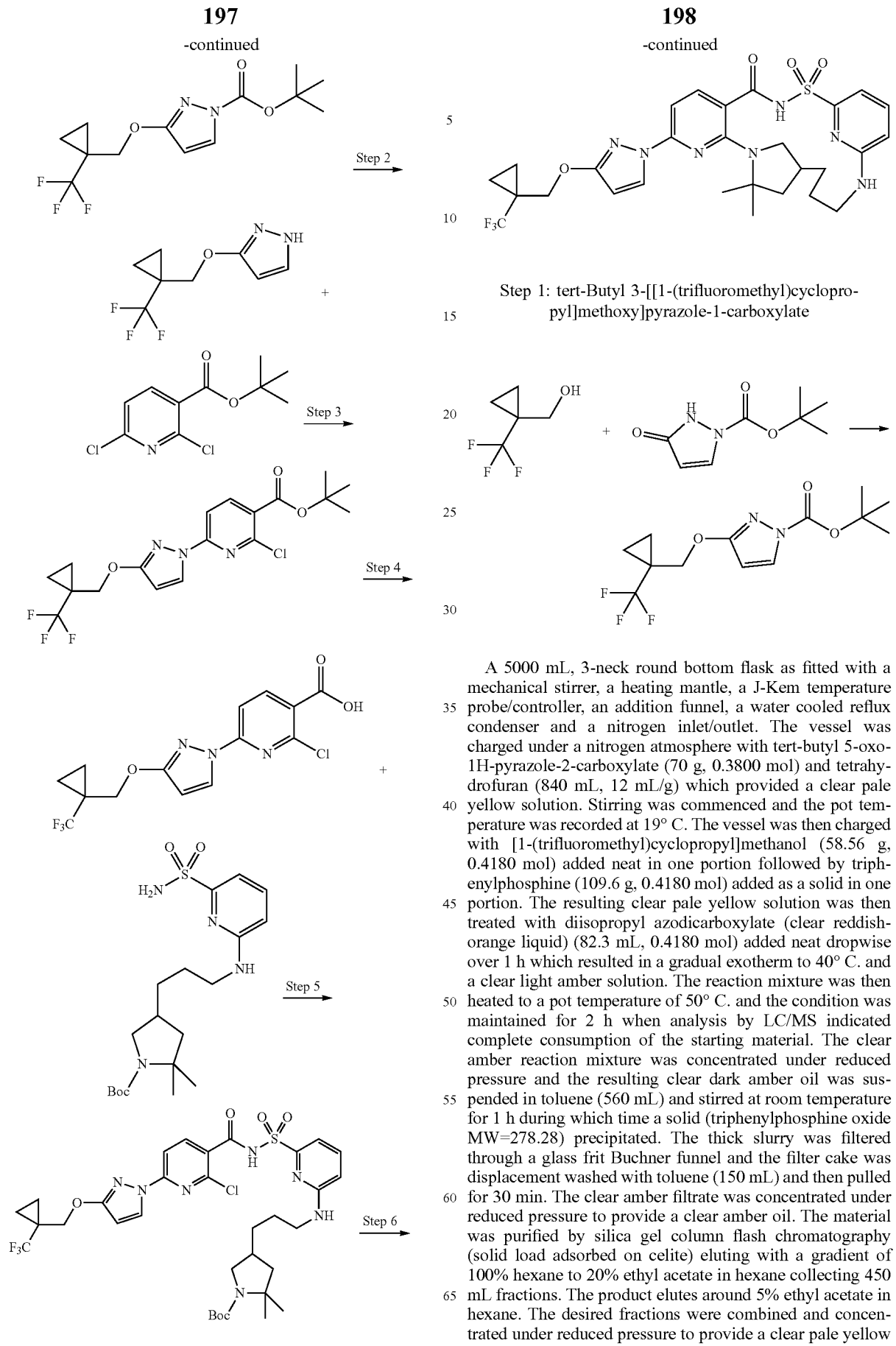

Step 1: tert-Butyl 3-[[1-(trifluoromethyl)cyclopropyl]methoxy]pyrazole-1-carboxylate A 5000 mL, 3-neck round bottom flask as fitted with a mechanical stirrer, a heating mantle, a J-Kem temperature probe/controller, an addition funnel, a water cooled reflux condenser and a nitrogen inlet/outlet. The vessel was charged under a nitrogen atmosphere with tert-butyl 5-oxo-1H-pyrazole-2-carboxylate (70 g, 0.3800 mol) and tetrahydrofuran (840 mL, 12 mL/g) which provided a clear pale yellow solution. Stirring was commenced and the pot temperature was recorded at 19° C. The vessel was then charged with [1-(trifluoromethyl)cyclopropyl]methanol (58.56 g, 0.4180 mol) added neat in one portion followed by triphenylphosphine (109.6 g, 0.4180 mol) added as a solid in one portion. The resulting clear pale yellow solution was then treated with diisopropyl azodicarboxylate (clear reddish-orange liquid) (82.3 mL, 0.4180 mol) added neat dropwise over 1 h which resulted in a gradual exotherm to 40° C. and a clear light amber solution. The reaction mixture was then heated to a pot temperature of 50° C. and the condition was maintained for 2 h when analysis by LC/MS indicated complete consumption of the starting material. The clear amber reaction mixture was concentrated under reduced pressure and the resulting clear dark amber oil was suspended in toluene (560 mL) and stirred at room temperature for 1 h during which time a solid (triphenylphosphine oxide MW=278.28) precipitated. The thick slurry was filtered through a glass frit Buchner funnel and the filter cake was displacement washed with toluene (150 mL) and then pulled for 30 min. The clear amber filtrate was concentrated under reduced pressure to provide a clear amber oil. The material was purified by silica gel column flash chromatography (solid load adsorbed on celite) eluting with a gradient of 100% hexane to 20% ethyl acetate in hexane collecting 450 mL fractions. The product elutes around 5% ethyl acetate in hexane. The desired fractions were combined and concentrated under reduced pressure to provide a clear pale yellow oil as the desired product, tert-butyl 3-[[1-(trifluoromethyl)cyclopropyl]methoxy]pyrazole-1-carboxylate (81 g, 0.264 mol, 70%). $^1$H NMR (400 MHz, dimethyl sulfoxide-d$_6$) δ 8.10 (d, J=2.9 Hz, 1H), 6.14 (d, J=3.0 Hz, 1H), 4.31 (s, 2H), 1.55 (s, 9H), 1.07 (dp, J=4.9, 1.3 Hz, 4H). ESI-MS m/z calc. 306.11914, found 307.0 (M+1)$^+$; Retention time: 1.75 min (LC Method B).

Step 2: 3-[[1-(Trifluoromethyl)cyclopropyl]methoxy]-1H-pyrazole

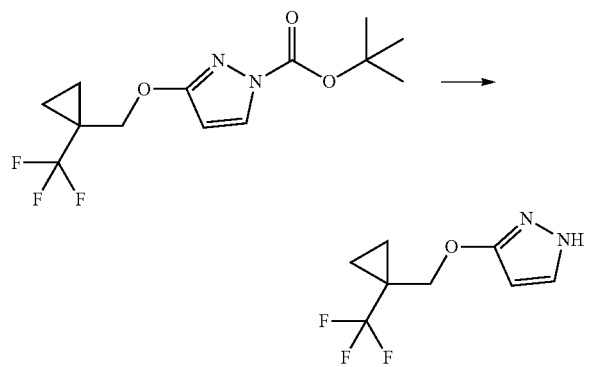

A 5000 mL, 3-neck round bottom flask was fitted with a mechanical stirrer, a heating mantle, a J-Kem temperature probe, a water cooled reflux condenser, an addition funnel and a nitrogen inlet/outlet. The vessel was charged under a nitrogen atmosphere with tert-butyl 3-[[1-(trifluoromethyl)cyclopropyl]methoxy]pyrazole-1-carboxylate (80 g, 0.2612 mol), dichloromethane (320 mL, 4 mL/g) and methyl alcohol (320 mL, 4 mL/g) which provided a clear pale yellow solution. Stirring was commenced and the pot temperature was recorded at 19° C. The addition funnel was charged with 4 M hydrochloric acid in 1,4-dioxane (195.9 mL, 0.7836 mol) which was subsequently added dropwise over 1 h which resulted in a gradual exotherm to 30° C. The resulting clear pale yellow solution was heated to a pot temperature of 45° C. and the condition was maintained for 1 h when analysis by LC/MS indicated reaction completion. The reaction mixture was allowed to cool to room temperature and then concentrated under reduced pressure. The remaining residue was dissolved in tert-butyl methyl ether (640 mL) and then transferred to a separatory funnel and partitioned with 2 M sodium hydroxide solution (391.8 mL, 0.7836 mol). The organic layer was removed and the residual aqueous was extracted with tert-butyl methyl ether (2×200 mL). The combined organic was washed with saturated sodium chloride solution (500 mL), dried over sodium sulfate (300 g) and then filtered through a glass frit Buchner funnel. The clear pale yellow filtrate was concentrated under reduced pressure to provide a clear light yellow oil which solidified upon standing to provide a white solid (49.5 g, 0.240 mol, 92%) as the desired product, 3-[[1-(trifluoromethyl)cyclopropyl]methoxy]-1H-pyrazole. $^1$H NMR (400 MHz, dimethyl sulfoxide-d$_6$) δ 11.90 (s, 1H), 7.51 (d, J=2.4 Hz, 1H), 5.67 (d, J=2.4 Hz, 1H), 4.19 (s, 2H), 1.09-0.97 (m, 4H). ESI-MS m/z calc. 206.0667, found 207.0 (M+1)$^+$; Retention time: 1.08 min (LC Method B).

Step 3: tert-Butyl 2-chloro-6-[3-[[1-(trifluoromethyl)cyclopropyl]methoxy]pyrazol-1-yl]pyridine-3-carboxylate

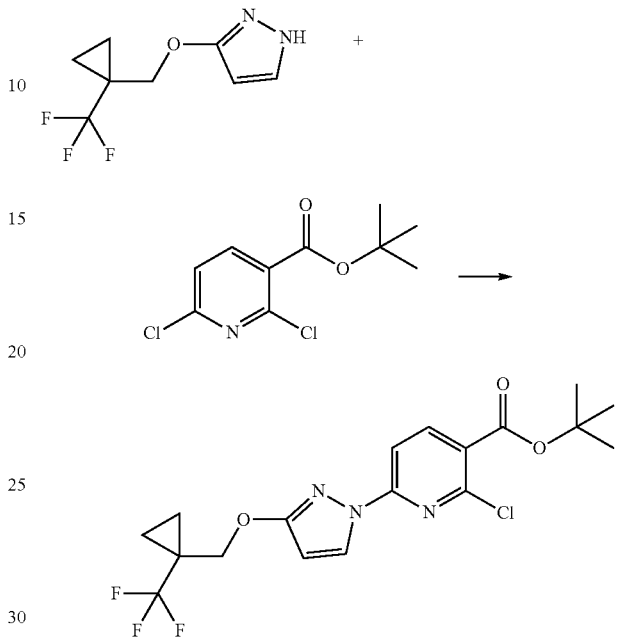

A 5000 mL, 3-neck round bottom flask was fitted with a mechanical stirrer, a cooling bath used as secondary containment, a J-Kem temperature probe, a water cooled reflux condenser, an addition funnel and a nitrogen inlet/outlet. The vessel was charged under a nitrogen atmosphere with 3-[[1-(trifluoromethyl)cyclopropyl]methoxy]-1H-pyrazole (45 g, 0.2183 mol) and N,N-dimethylformamide (540 mL, 12 mL/g) which provided a clear pale yellow solution. Stirring was commenced and the pot temperature was recorded at 17° C. The vessel was then charged with tert-butyl 2,6-dichloropyridine-3-carboxylate (54.16 g, 0.2183 mol) added as a solid in one portion. The resulting clear pale yellow solution was then treated with potassium carbonate (39.22 g, 0.2838 mol) added as a solid in one portion followed by 1,4-diazabicyclo[2.2.2]octane (3.67 g, 0.03274 mol) added as a solid in one portion. The resulting pale yellow suspension was allowed to stir at room temperature for 24 h. The reaction mixture was cooled to 10° C. with a crushed ice/water cooling bath. The addition funnel was charged with water (540 mL) added dropwise over 45 min which resulted in a thick suspension and an exotherm to 15° C. The resulting suspension was continued to stir at 15° C. for 30 min and then filtered through a glass frit Buchner funnel. The filter cake was displacement washed with water (2×500 mL) and then pulled in the Buchner funnel for 2 h. The material was then allowed to air dry overnight to provide (73 g, 0.175 mol, 80%) of a white granular solid, tert-butyl 2-chloro-6-[3-[[1-(trifluoromethyl)cyclopropyl]methoxy]pyrazol-1-yl]pyridine-3-carboxylate. ESI-MS m/z calc. 417.1067, found 418.1 (M+1)$^+$; Retention time: 0.85 min (LC Method A).

Step 4: 2-Chloro-6-[3-[[1-(trifluoromethyl)cyclopropyl]methoxy]pyrazol-1-yl]pyridine-3-carboxylic Acid

Step 5: tert-Butyl 4-[3-[[6-[[2-chloro-6-[3-[[1-(trifluoromethyl)cyclopropyl]methoxy]pyrazol-1-yl]pyridine-3-carbonyl]sulfamoyl]-2-pyridyl]amino]propyl]-2,2-dimethyl-pyrrolidine-1-carboxylate

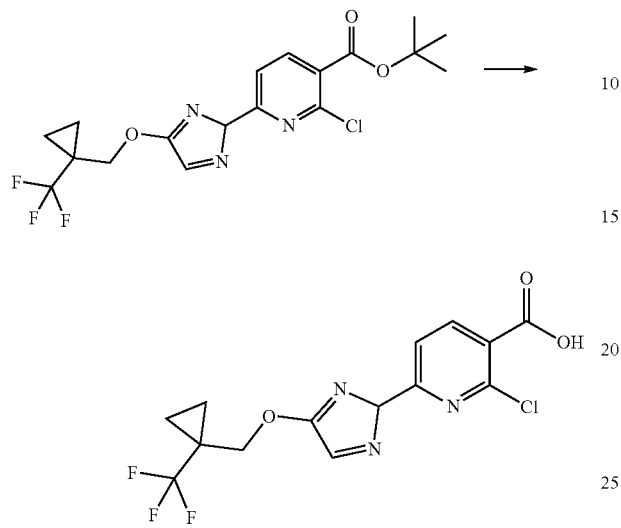

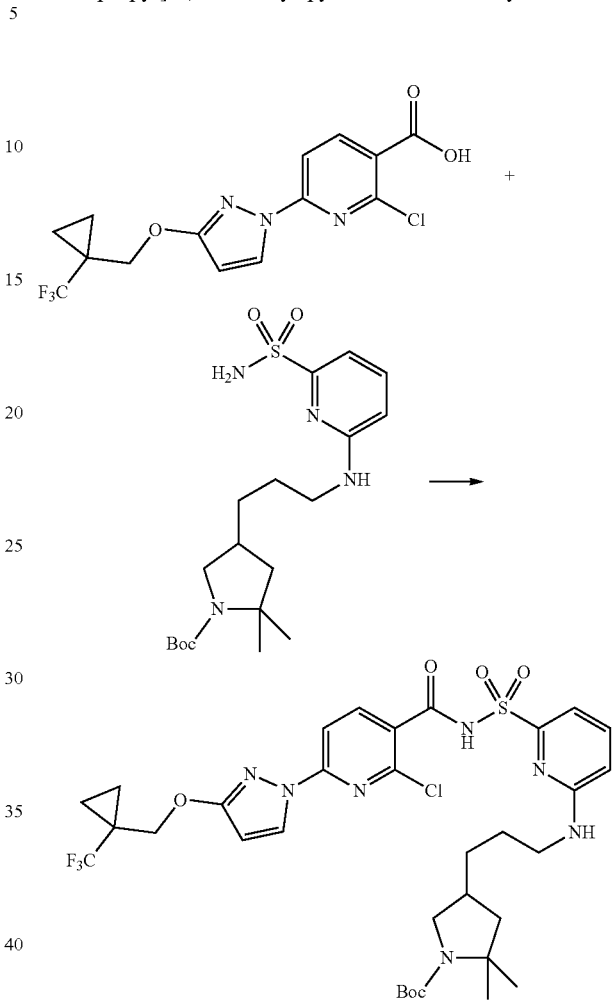

A 1000 mL, 3-neck round bottom flask as fitted with a mechanical stirrer, a heating mantle, a J-Kem temperature probe/controller, an addition funnel, a water cooled reflux condenser and a nitrogen inlet/outlet. The vessel was charged under a nitrogen atmosphere with tert-butyl 2-chloro-6-[3-[[1-(trifluoromethyl)cyclopropyl]methoxy]pyrazol-1-yl]pyridine-3-carboxylate (70 g, 0.1675 mol) and 2-propanol (350 mL) which provided an off-white suspension. Stirring was commenced and the pot temperature was recorded at 19° C. The addition funnel was charged with aqueous 6 M hydrochloric acid (139.6 mL, 0.8375 mol) which was added dropwise over 10 min which resulted in an exotherm to 30° C. The resulting suspension was then heated to reflux (pot temperature~82° C.) Upon heating the suspension turns to a clear pale yellow solution (pot temperature~75° C. at this point). After stirring at reflux for 30 min a solid began to precipitate. The suspension was continued to stir at reflux for an additional 30 min at which point water (210 mL) was added dropwise over 15 min. The heat was then removed and the suspension was continued to stir and allowed to slowly cool to room temperature. The material was collected by vacuum filtration in a glass frit Buchner funnel and the filter cake was displacement washed with 1:1 water/2-propanol (100 mL) followed by water (2×100 mL) and then pulled in the Buchner funnel for 30 min. The material was further dried in a vacuum oven at 45° C. for 24 h to provide 2-chloro-6-[3-[[1-(trifluoromethyl)cyclopropyl]methoxy]pyrazol-1-yl]pyridine-3-carboxylic acid (56 g, 0.155 mol, 92%) as a white solid. $^1$H NMR (400 MHz, dimethyl sulfoxide-$d_6$) δ 13.64 (s, 1H), 8.44 (d, J=2.9 Hz, 1H), 8.41 (d, J=8.4 Hz, 1H), 7.74 (d, J=8.4 Hz, 1H), 6.24 (d, J=2.9 Hz, 1H), 4.41 (s, 2H), 1.16-1.07 (m, 4H). ESI-MS m/z calc. 361.0441, found 362.1 (M+1)$^+$; Retention time: 0.66 min (LC Method A).

2-Chloro-6-[3-[[1-(trifluoromethyl)cyclopropyl]methoxy]pyrazol-1-yl]pyridine-3-carboxylic acid (260 mg, 0.6973 mmol) and carbonyl diimidazole (113.1 mg, 0.6973 mmol) were combined in tetrahydrofuran (3.783 mL) and stirred for 1 h at 45° C. tert-Butyl 2,2-dimethyl-4-[3-[(6-sulfamoyl-2-pyridyl)amino]propyl]pyrrolidine-1-carboxylate (287.7 mg, 0.6973 mmol) was added followed by 1,8-diazabicyclo[5.4.0]undec-7-ene (212.4 mg, 208.6 μL, 1.395 mmol) and the reaction was heated at 45° C. for 4 hrs. The reaction was diluted with ethyl acetate and washed with a 1M citric acid solution, followed by brine. The organics were separated, dried over sodium sulfate, evaporated, then purified by silica gel chromatography (24 gram column) using a gradient from 100% hexanes to 70% ethyl acetate in hexanes to afford as a white solid, tert-butyl 4-[3-[[6-[[2-chloro-6-[3-[[1-(trifluoromethyl)cyclopropyl]methoxy]pyrazol-1-yl]pyridine-3-carbonyl]sulfamoyl]-2-pyridyl]amino]propyl]-2,2-dimethyl-pyrrolidine-1-carboxylate (232 mg, 44%). $^1$H NMR (400 MHz, dimethyl sulfoxide-$d_6$) δ 12.78 (s, 1H), 8.41 (d, J=2.4 Hz, 1H), 8.11 (d, J=8.3 Hz, 1H), 7.72 (d, J=8.3 Hz, 1H), 7.62 (dd, J=8.4, 7.3 Hz, 1H), 7.21 (s, 1H), 7.17 (d, J=7.1 Hz, 1H), 6.74 (d, J=8.5 Hz, 1H), 6.23 (s, 1H), 4.39 (s, 2H), 3.58-3.46 (m, 1H), 3.24 (s, 2H), 2.74 (t, J=10.5 Hz, 1H), 2.02 (s, 1H), 1.79 (td, J=12.2, 6.4 Hz, 1H), 1.50 (ddd, J=21.4, 10.3, 6.2 Hz, 2H), 1.36 (d, J=11.7 Hz, 9H), 1.30 (d, J=13.8 Hz, 6H), 1.17 (s, 3H), 1.11 (s, 2H), 1.09 (s, 2H). ESI-MS m/z calc. 755.248, found 756.5 (M+1)⁺; Retention time: 2.31 min (LC Method E).

Step 6: 12,12-Dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 15)

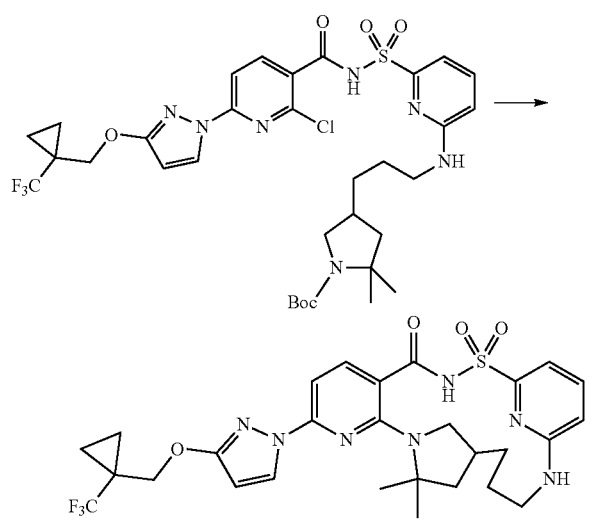

Part A: tert-Butyl 4-[3-[[6-[[2-chloro-6-[3-[[1-(trifluoromethyl)cyclopropyl]methoxy]pyrazol-1-yl]pyridine-3-carbonyl]sulfamoyl]-2-pyridyl]amino]propyl]-2,2-dimethyl-pyrrolidine-1-carboxylate (232 mg, 0.3068 mmol) was dissolved in dichloromethane (5.0 mL) and hydrochloric acid (4M in dioxane) (2.5 mL of 4 M, 10.00 mmol) was added to the mixture and allowed to stir at room temperature for 3 h. The reaction was concentrated to dryness under reduced pressure, redissolved in ethyl acetate, and then aqueous 2M sodium carbonate (5 mL) was added to adjust the solution to pH 10. The organic layer was extracted with ethyl acetate (2×10 mL), washed with brine, dried over sodium sulfate, and evaporated to dryness under reduced pressure.

Part B: To a vial was added the crude amine from Part A, potassium carbonate (235 mg, 1.70 mmol), cesium fluoride (75.3 mg, 0.4957 mmol), 3 Å molecular sieves, and dimethyl sulfoxide (7.0 mL). The vial was purged with nitrogen, capped, heated to 150° C. and stirred for 16 h. The reaction was cooled to room temperature. The reaction was diluted with ethyl acetate and washed with a 1M citric acid solution, followed by brine. The organics were separated, dried over sodium sulfate, evaporated, and then purified by silica gel chromatography (24 gram column) using a gradient from 100% hexanes to 80% ethyl acetate to afford as an off-white solid, 12,12-dimethyl-8-(3-{[1-(trifluoromethyl) cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 15) (101.9 mg, 54%). ¹H NMR (400 MHz, dimethyl sulfoxide-d₆) δ 12.51 (s, 1H), 8.22 (d, J=2.8 Hz, 1H), 7.82 (d, J=8.2 Hz, 1H), 7.66-7.49 (m, 1H), 7.05 (d, J=7.2 Hz, 1H), 6.98 (d, J=5.5 Hz, 1H), 6.92 (d, J=8.2 Hz, 1H), 6.71 (d, J=8.4 Hz, 1H), 6.16 (d, J=2.7 Hz, 1H), 4.36 (q, J=11.9 Hz, 2H), 3.92 (dd, J=24.2, 10.9 Hz, 1H), 3.24-3.07 (m, 1H), 2.95 (d, J=13.0 Hz, 1H), 2.78-2.64 (m, 1H), 2.22-2.08 (m, 1H), 1.86 (dd, J=11.8, 5.0 Hz, 1H), 1.76 (dd, J=15.9, 8.1 Hz, 1H), 1.65-1.54 (m, 6H), 1.51 (s, 3H), 1.31 (dd, J=24.7, 12.0 Hz, 1H), 1.10 (s, 4H). ESI-MS m/z calc. 619.2189, found 620.2 (M+1)⁺; Retention time: 2.1 min (LC Method E).

Example 6: Preparation of 12,12-dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 1) (Compound 21) and 12,12-dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 2) (Compound 22)

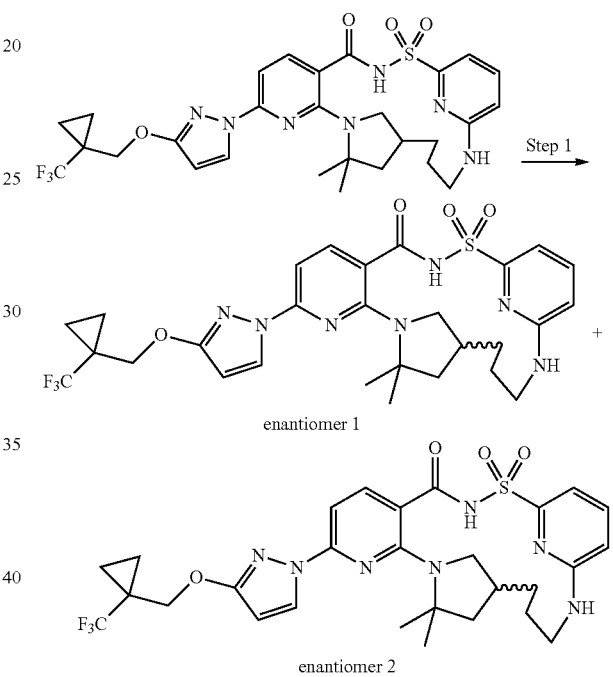

Step 1: 12,12-Dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 1) (Compound 21) and 12,12-dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 2) (Compound 22)

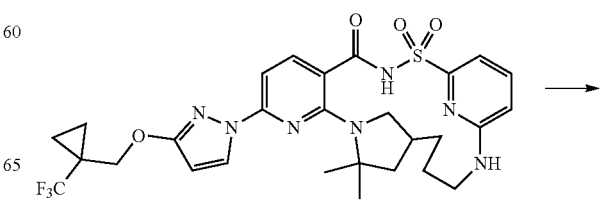

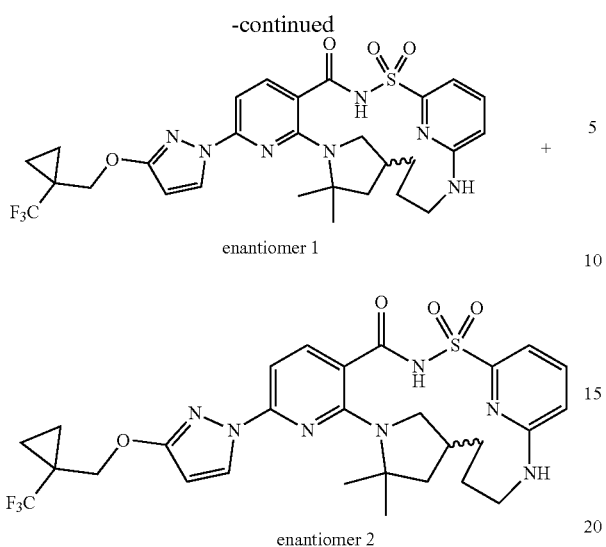

enantiomer 1 enantiomer 2

Racemic 12,12-dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 15) (82.4 mg, 0.133 mmol) was subjected to chiral SFC chromatography using a ChiralPak AS-H (250×21.2 mm column, 5 µm particle size) with 20% acetonitrile (No modifier))/80% carbon dioxide mobile phase at 70 mL/min giving as the first enantiomer to elute, 12,12-dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 1) (Compound 21) (32.38 mg, 78%) as an off-white solid; ¹H NMR (400 MHz, dimethyl sulfoxide-d₆) δ 12.51 (s, 1H), 8.22 (d, J=2.7 Hz, 1H), 7.82 (d, J=8.2 Hz, 1H), 7.72-7.67 (m, 1H), 7.62-7.50 (m, 1H), 7.05 (d, J=7.0 Hz, 1H), 6.92 (d, J=8.2 Hz, 1H), 6.70 (d, J=8.5 Hz, 1H), 6.15 (d, J=2.7 Hz, 1H), 4.36 (q, J=11.9 Hz, 2H), 4.16-4.12 (m, 1H), 3.22-3.10 (m, 1H), 2.95 (d, J=12.9 Hz, 1H), 2.74-2.68 (m, 1H), 2.20-2.03 (m, 1H), 1.86 (dd, J=12.2, 5.0 Hz, 1H), 1.76 (dd, J=10.3, 4.8 Hz, 1H), 1.60 (s, 3H), 1.51 (s, 3H), 1.28 (s, 4H), 1.10 (s, 2H), 0.87 (d, J=5.1 Hz, 2H), ESI-MS m/z calc. 619.2189, found 620.2 (M+1)⁺; Retention time: 2.1 min (LC Method E) and as the second enantiomer to elute, 12,12-dimethyl-8-(3-{[1-(trifluoromethyl)cyclopropyl]methoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 2) (Compound 22) (34.58 mg, 83%) as an off-white solid; ¹H NMR (400 MHz, dimethyl sulfoxide-d₆) δ 12.51 (s, 1H), 8.22 (d, J=2.8 Hz, 1H), 7.82 (d, J=8.3 Hz, 1H), 7.69 (d, J=3.6 Hz, 1H), 7.57 (t, J=7.8 Hz, 1H), 7.05 (d, J=7.2 Hz, 1H), 6.92 (d, J=8.3 Hz, 1H), 6.71 (d, J=8.5 Hz, 1H), 6.16 (d, J=2.8 Hz, 1H), 4.36 (q, J=11.9 Hz, 2H), 4.14 (d, J=2.3 Hz, 1H), 3.16 (s, 1H), 2.95 (d, J=13.4 Hz, 1H), 2.76-2.68 (m, 1H), 2.19-2.07 (m, 1H), 1.86 (dd, J=11.8, 5.1 Hz, 1H), 1.75 (s, 1H), 1.60 (s, 3H), 1.51 (s, 3H), 1.28 (d, J=2.1 Hz, 4H), 1.10 (d, J=2.7 Hz, 2H), 0.88 (s, 2H), ESI-MS m/z calc. 619.2189, found 620.2 (M+1)⁺; Retention time: 2.1 min (LC Method E).

Example 7: Preparation of 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.1¹¹,¹⁴.0⁵,¹⁰]pentacosa-1(23),5,7,9,20(24),21-hexaene-2,2,4-trione (Compound 28)

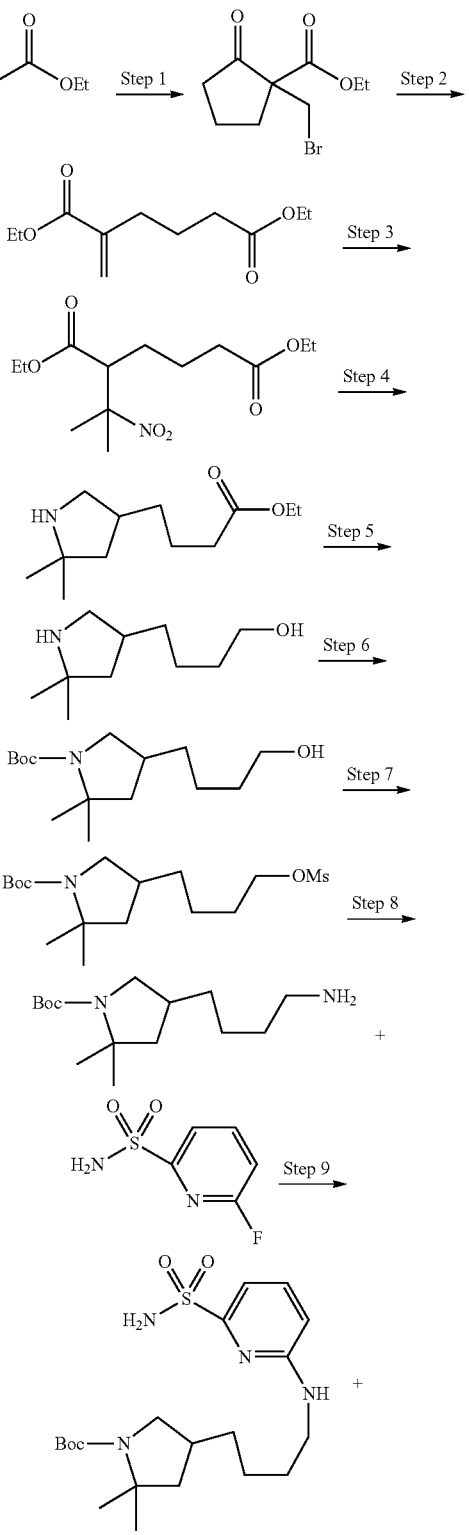

MHz, CDCl$_3$) δ 4.18 (q, J=7.0 Hz, 7.25 Hz, 2H); 3.68 (q, J=22.5 Hz, J=9.5 Hz, 2H); 2.58-2.00 (m, 6H); 1.25 (t, J=7.75 Hz, 3H).

Step 2: Diethyl 2-methylenehexanedioate

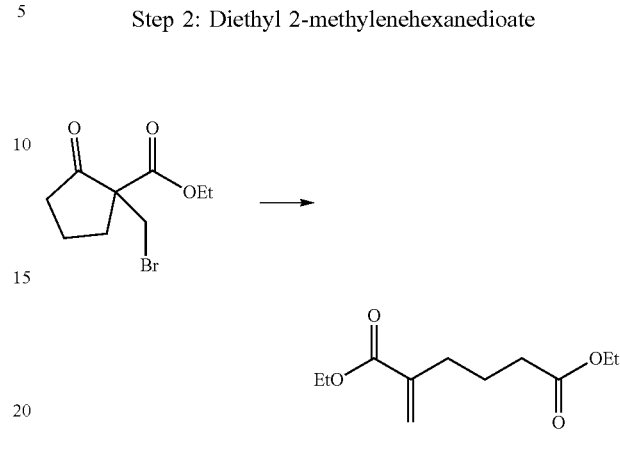

Potassium carbonate (79 g, 572 mmol) was added to a solution of ethyl 1-(bromomethyl)-2-oxocyclopentanecarboxylate (85 g, 341 mmol) in dry ethanol (680 mL) and the mixture was stirred at room temperature for 16 h. The mixture was filtered, evaporated and purified by silica gel column chromatography using 0-5% hexanes-ethyl acetate to provide diethyl 2-methylenehexanedioate (72.7 g, 98%) as a colorless oil. $^1$H NMR (250 MHz, CDCl$_3$) δ 6.16 (s, 1H); 5.54 (s, 1H); 4.24-4.07 (m, 4H); 2.36-2.28 (m, 4H), 1.83-1.77 (m, 2H), 1.32-1.21 (m, 6H).

Step 3: Diethyl 2-(2-methyl-2-nitropropyl)hexanedioate

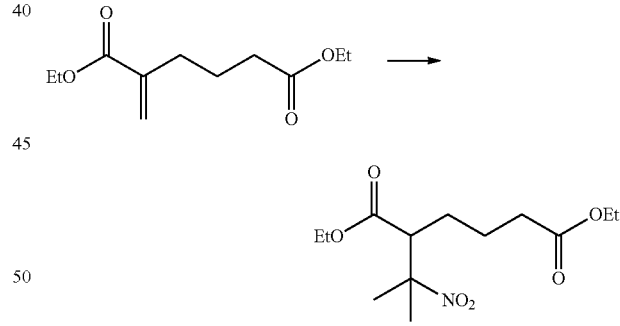

1,8-Diazabicycloundec-7-ene (23 g, 151 mmol) was added to a solution of diethyl 2-methylenehexanedioate (72.7 g, 340 mmol) and 2-nitropropane (36.3 g, 408 mmol) in dry acetonitrile (1000 mL) and the mixture was stirred at room temperature for 16 h. The mixture was evaporated and the residue was dissolved in ethyl acetate (1000 mL) and washed with saturated ammonium chloride (500 mL). The organic phase was concentrated and purified by silica gel column chromatography using 0-10% hexanes-ethyl acetate to provide diethyl 2-(2-methyl-2-nitropropyl)hexanedioate (86 g, 84%) as a colorless oil. $^1$H NMR (250 MHz, CDCl$_3$) δ 4.17-4.07 (m, 4H); 2.41-2.05 (m, 5H), 1.72-1.44 (m, 4H), 1.56 (s, 3H), 1.51 (s, 3H), 1.28-1.21 (m, 6H).

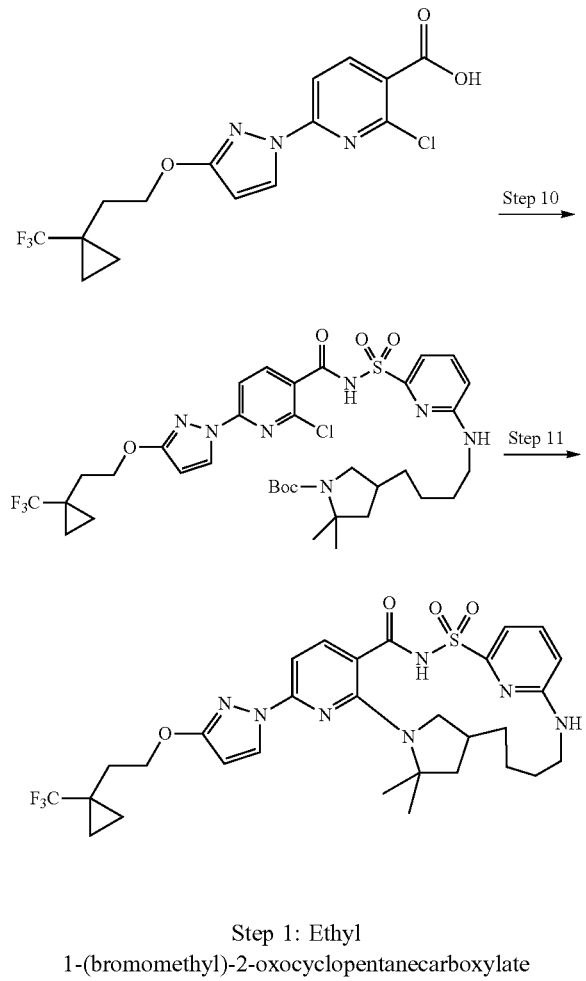

Step 1: Ethyl 1-(bromomethyl)-2-oxocyclopentanecarboxylate

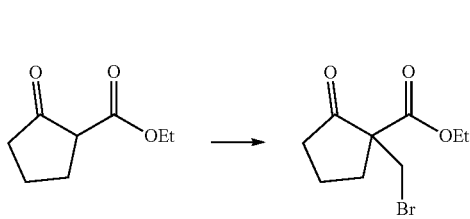 [SMILES: CCOC(=O)C1CCCC1=O ; CCOC(=O)C1(CBr)CCCC1=O]

A solution of ethyl 2-oxocyclopentanecarboxylate (70 g, 449 mmol) in dry tetrahydrofuran (300 mL) was added slowly to a suspension of 67.6% sodium hydride suspension in mineral oil (19.17 g, 540 mmol) in tetrahydrofuran (750 mL) containing hexamethylphosphoramide (97 g, 540 mmol) at room temperature under an argon atmosphere. The reaction mixture was stirred at room temperature for 1 h. Dibromomethane (392 g, 250 mmol) was added and the reaction mixture was refluxed at 80° C. for 16 h. The reaction was allowed to cool to room temperature and diethyl ether (1000 mL) was added and the organic layer was washed with water (5×500 mL), dried over anhydrous sodium sulfate, concentrated and purified by silica gel column chromatography using 0-10% hexanes-ethyl acetate to provide ethyl 1-(bromomethyl)-2-oxocyclopentanecarboxylate (85 g, 76%) of as a colorless oil. $^1$H NMR (250

Step 4: 4-(4,4-Dimethyl-5-oxo-pyrrolidin-2-yl)-butyric acid ethyl ester

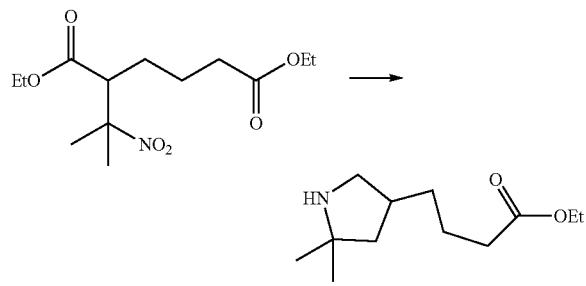

A mixture of diethyl 2-(2-methyl-2-nitropropyl)hexanedioate (43 g, 141.7 mmol) and Raney nickel slurry (12 g) in ethanol (860 mL) was heated at 80° C. for 18 h in a Parr reactor under 2 bar of hydrogen gas. Celite (50 g) was added and the resulting mixture was filtered. The solids were discarded and the filtrate was concentrated to obtain 4-(4,4-dimethyl-5-oxo-pyrrolidin-2-yl)-butyric acid ethyl ester (31.2 g, 97%) as an orange oil. The crude product was used in the next step without further purification. ESI-MS m/z calc. 227.3, found 228.3 (M+1)+. Retention time: 3.23 min (LC Method Q).

Step 5: 4-(4,4-Dimethylpyrrolidin-2-yl)-butan-1-ol

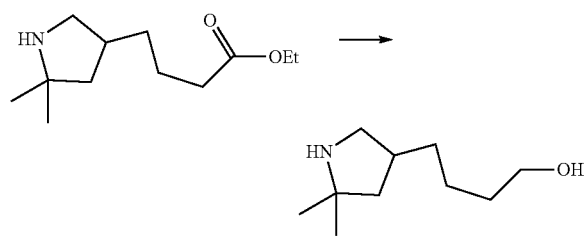

To a solution of 4-(4,4-dimethyl-5-oxo-pyrrolidin-2-yl)-butyric acid ethyl ester (78.8 g, 345.3 mmol) in tetrahydrofuran (1200 mL) was added lithium aluminum hydride (39.3 g, 1036.0 mmol) in portions over a 45 min period and the resulting slurry was heated to reflux under nitrogen for 18 h. The cooled reaction mixture was carefully quenched with a saturated solution of sodium sulfate (100 mL) and the formed solid was filtered. The solids were discarded and the filtrate was concentrated under vacuum to obtain 4-(4,4-dimethylpyrrolidin-2-yl)-butan-1-ol (51.5 g, 87%) as a brown oil. The crude product was used in the next step without further purification. ESI-MS m/z calc. 171.28, found 172.3 (M+1)+. Retention time: 1.05 min (LC Method Q).

Step 6: 2-(4-Hydroxybutyl)-4,4-dimethyl-pyrrolidine-1-carboxylic Acid tert-butyl ester

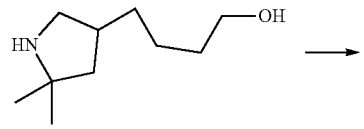

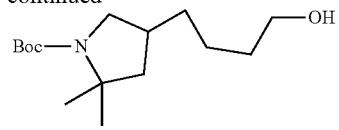

To a solution of 4-(4,4-dimethylpyrrolidin-2-yl)-butan-1-ol (51.5 g, 301 mmol) in dichloromethane (400 mL) was added a solution of sodium bicarbonate (50.6 g, 602 mmol) in water (300 mL) followed by di-tert-butyl dicarbonate (65.6 g, 301 mmol). The resulting biphasic mixture was stirred for 18 h at room temperature. The phases were separated and the aqueous phase was discarded. The organic phase was concentrated and purified by silica gel column chromatography using 0-45% hexanes-ethyl acetate to obtain 2-(4-hydroxybutyl)-4,4-dimethyl-pyrrolidine-1-carboxylic acid tert-butyl ester (57.2 g, 77%) as a clear oil. $^1$H NMR (250 MHz, CDCl$_3$) δ 4.35 (t, 1H), 3.53 (m, 1H), 3.37 (m, 2H), 2.76 (m, 1H), 2.01-1.81 (m, 2H), 1.40-1.24 (m, 23H). ESI-MS m/z calc. 271.4, found 272.4 (M+1)+. Retention time: 4.67 min (LC Method Q).

Step 7: tert-Butyl 2,2-dimethyl-4-(4-methylsulfonyloxybutyl)pyrrolidine-1-carboxylate

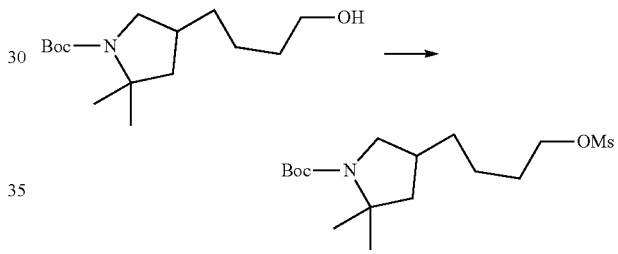

To a solution of tert-butyl 4-(4-hydroxybutyl)-2,2-dimethyl-pyrrolidine-1-carboxylate (2.28 g, 8.401 mmol) in dichloromethane (19 mL) and triethylamine (8.0 mL, 57 mmol) chilled to 0° C. was added methanesulfonyl chloride (2.161 mL, 27.92 mmol) dropwise. The reaction mixture was stirred for 20 h allowing the reaction to warm to room temperature after 1 h (the clear solution turned cloudy orange after 10 min). The reaction mixture was quenched with ice-water and dichloromethane, followed by brine. The aqueous layer was extracted with further dichloromethane (2×20 mL) and the combined organics were dried over sodium sulfate, filtered and concentrated under reduced pressure. The resulting material was dried under vacuum for 1 h to provide tert-butyl 2,2-dimethyl-4-(4-methylsulfonyloxybutyl)pyrrolidine-1-carboxylate (2.9 g, 99%) as a yellow oil. ESI-MS m/z calc. 349.1923, found 350.2 (M+1)+; Retention time: 1.82 min (LC Method E).

Step 8: tert-Butyl 4-(4-aminobutyl)-2,2-dimethylpyrrolidine-1-carboxylate

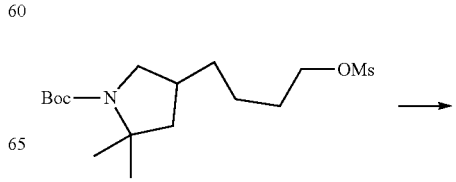

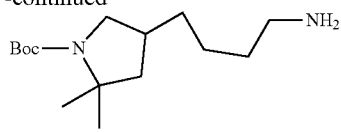

tert-Butyl 2,2-dimethyl-4-(4-methylsulfonyloxybutyl)pyrrolidine-1-carboxylate (2.9 g, 8.298 mmol) was dissolved in a mixture of dioxane (60 mL) and ammonium hydroxide (60 mL of 30% w/v, 510 mmol). The mixture was heated to 50° C. in a sealed vessel for 18 h. The dioxane was concentrated under vacuum and dichloromethane (50 mL) was added. The organic layer was separated, dried over sodium sulfate, filtered and concentrated under vacuum. The crude material was purified by silica gel chromatography (80 gram column) using dichloromethane methanol (containing 5 mL/liter 30% ammonium hydroxide) gradient method (0 to 15% methanol in dichloromethane) to obtain tert-butyl 4-(4-aminobutyl)-2,2-dimethyl-pyrrolidine-1-carboxylate (1.44 g, 64%) as an off-white foam. ¹H NMR (400 MHz, dimethyl sulfoxide-d₆) δ 7.90 (s, 2H), 3.55 (dd, J=18.7, 11.1 Hz, 1H), 3.34 (s, 2H), 3.17 (s, 1H), 2.76 (dd, J=17.0, 9.5 Hz, 2H), 2.06 (s, 1H), 1.95-1.74 (m, 1H), 1.52 (t, J=18.4 Hz, 2H), 1.39 (d, J=9.9 Hz, 9H), 1.35 (s, 1H), 1.34 (s, 2H), 1.31-1.18 (m, 6H). ESI-MS m/z calc. 270.23074, found 271.2 (M+1)⁺; Retention time: 1.21 min (LC Method E).

Step 9: tert-Butyl 2,2-dimethyl-4-[4-[(6-sulfamoyl-2-pyridyl)amino]butyl]pyrrolidine-1-carboxylate

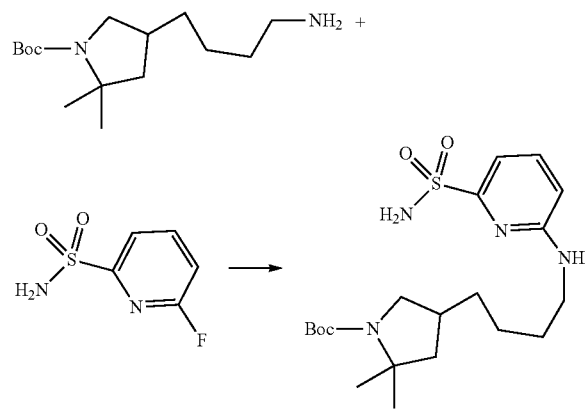

In a 250 mL flask was combined 6-fluoropyridine-2-sulfonamide (894 mg, 5.07 mmol) in dimethyl sulfoxide (20 mL), followed by potassium carbonate (1.1 g, 8.0 mmol) and tert-butyl 4-(4-aminobutyl)-2,2-dimethyl-pyrrolidine-1-carboxylate (1.44 g, 5.33 mmol) under nitrogen and a reflux condenser. The vessel was heated at 60° C. in an oil bath for 18 h. Added potassium carbonate (1.1 g, 8.0 mmol) and increased heat to 80° C. for an additional 4 h. Upon cooling, the reaction mixture was filtered then diluted with ethyl acetate and washed with a 1 M citric acid solution, followed by brine. The organics were separated, dried over sodium sulfate, filtered, evaporated and purified by silica gel chromatography (80 gram column GOLD) using a gradient from 100% hexanes to 75% ethyl acetate in hexanes to afford as a white solid, tert-butyl 2,2-dimethyl-4-[4-[(6-sulfamoyl-2-pyridyl)amino]butyl]pyrrolidine-1-carboxylate (475 mg, 22%). ¹H NMR (400 MHz, dimethyl sulfoxide-d₆) δ 7.51 (dd, J=8.4, 7.3 Hz, 1H), 7.07 (s, 2H), 6.94 (t, J=5.7 Hz, 2H), 6.61 (d, J=8.2 Hz, 1H), 3.54 (dd, J=18.2, 8.5 Hz, 1H), 3.28 (dd, J=12.6, 6.6 Hz, 2H), 2.78 (dd, J=19.7, 10.1 Hz, 1H), 2.07 (s, 1H), 1.94-1.80 (m, 1H), 1.52 (s, 2H), 1.44 (d, J=12.2 Hz, 1H), 1.38 (d, J=10.4 Hz, 9H), 1.35 (d, J=10.9 Hz, 6H), 1.21 (d, J=17.2 Hz, 4H). ESI-MS m/z calc. 426.23007, found 427.2 (M+1)⁺; Retention time: 1.76 min (LC Method E).

Step 10: tert-Butyl 4-[4-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate

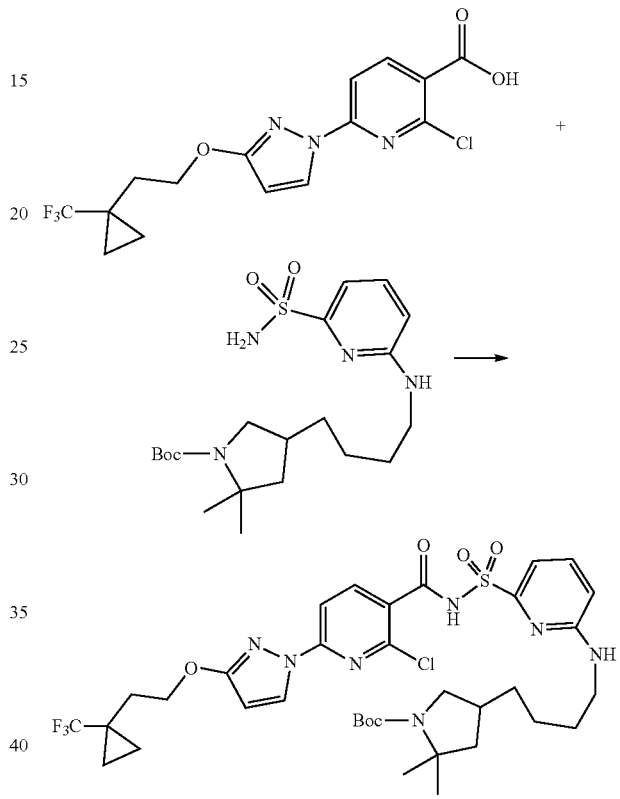

2-Chloro-6-[3-[2-[1-(trifluoromethyl)cyclopropyl]ethoxy]pyrazol-1-yl]pyridine-3-carboxylic acid (425 mg, 1.13 mmol) and carbonyl diimidazole (217 mg, 1.34 mmol) were combined in tetrahydrofuran (7 mL) and stirred for 90 min at 50° C. Then tert-butyl 2,2-dimethyl-4-[4-[(6-sulfamoyl-2-pyridyl)amino]butyl]pyrrolidine-1-carboxylate (475 mg, 1.11 mmol) was added followed by 1,8-diazabicyclo[5.4.0]undec-7-ene (350 µL, 2.34 mmol) and the reaction was heated at 50° C. for 18 h. The reaction was diluted with ethyl acetate and washed with a 1 M citric acid solution, followed by brine. The organics were separated, dried over sodium sulfate, filtered and evaporated then purified by silica gel chromatography (80 gram column) using a gradient from 100% hexanes to 70% ethyl acetate in hexanes to afford tert-butyl 4-[4-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate (613 mg, 83%) as a white solid. ¹H NMR (400 MHz, dimethyl sulfoxide-d₆) δ 12.80 (s, 1H), 8.41 (t, J=3.0 Hz, 1H), 8.11 (d, J=8.4 Hz, 1H), 7.71 (d, J=8.4 Hz, 1H), 7.61 (dd, J=8.4, 7.3 Hz, 1H), 7.22 (s, 1H), 7.16 (d, J=7.0 Hz, 1H), 6.73 (d, J=8.5 Hz, 1H), 6.18 (d, J=2.9 Hz, 1H), 4.34 (t, J=7.0 Hz, 2H), 3.54-3.42 (m, 1H), 3.22 (t, J=6.8 Hz, 2H), 2.72-2.63 (m, 1H), 2.08 (t, J=7.1 Hz, 2H), 2.00-1.88 (m, 1H), 1.71 (td, J=11.2, 5.9 Hz, 1H), 1.53-1.45 (m, 2H), 1.40-1.34 (m, 9H), 1.25 (t, J=11.6 Hz, 6H), 1.20-1.18

(m, 1H), 1.17 (d, J=6.0 Hz, 4H), 0.98-0.92 (m, 2H), 0.88 (s, 2H). ESI-MS m/z calc. 783.27924, found 784.2 (M+1)+; Retention time: 2.4 min (LC Method E).

Step 11: 12,12-Dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (Compound 28)

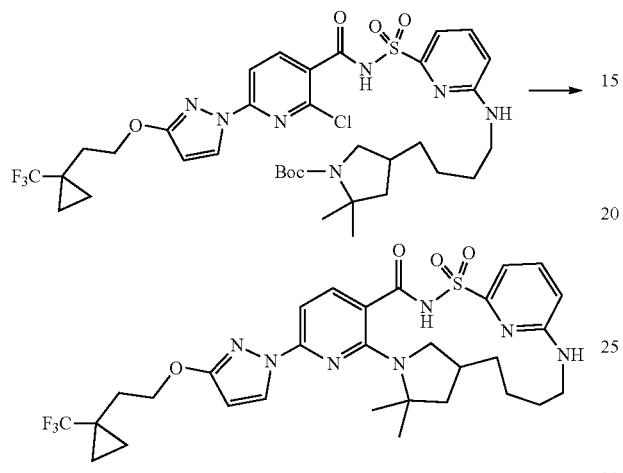

Part A: tert-Butyl 4-[4-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate (538 mg, 0.686 mmol) was dissolved in dichloromethane (12 mL) and to the mixture was added hydrochloric acid (4 M in dioxane) (5 mL of 4 M, 20.0 mmol) and stirred at room temperature for 1 h. Concentrated mixture to dryness under reduced pressure, redissolved in ethyl acetate, then added aqueous 2 M sodium carbonate (5 mL), giving pH~10. Extracted with ethyl acetate (2×10 mL), washed with brine, then dried over sodium sulfate, filtered and evaporated to dryness under reduced pressure.

Part B: Combined material from Part A and potassium carbonate (474 mg, 3.43 mmol), cesium fluoride (156 mg, 1.03 mmol), 3 Å molecular sieves and dimethyl sulfoxide (11 mL) in a vial, purged with nitrogen, capped, heated to 150° C. and stirred for 18 h. Cooled to room temperature. The reaction was diluted with ethyl acetate and washed with a 1 M citric acid solution, followed by brine. The organics were separated, dried over sodium sulfate, filtered and evaporated then purified by silica gel chromatography (40 gram column) using a gradient from 100% hexanes to 80% ethyl acetate in hexanes to afford 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (Compound 28) (270 mg, 60%) as a white solid. ¹H NMR (400 MHz, dimethyl sulfoxide-d₆) δ 12.45 (s, 1H), 8.21 (d, J=2.7 Hz, 1H), 7.86 (d, J=8.3 Hz, 1H), 7.69 (t, J=7.9 Hz, 1H), 7.23 (d, J=7.2 Hz, 1H), 6.93 (d, J=8.3 Hz, 1H), 6.81 (d, J=8.4 Hz, 1H), 6.12 (d, J=2.7 Hz, 1H), 4.32 (t, J=7.0 Hz, 2H), 3.51 (s, 2H), 3.30 (s, 1H), 2.76 (d, J=15.3 Hz, 1H), 2.69-2.58 (m, 1H), 2.14 (d, J=7.4 Hz, 1H), 2.08 (t, J=7.0 Hz, 2H), 1.85 (dd, J=11.6, 5.4 Hz, 1H), 1.56 (s, 2H), 1.55 (t, J=3.3 Hz, 6H), 1.46 (s, 2H), 1.26-1.16 (m, 2H), 0.96 (t, J=5.7 Hz, 2H), 0.89 (s, 2H). ESI-MS m/z calc. 647.2502, found 648.2 (M+1)+; Retention time: 2.26 min (LC Method E).

Example 8: Preparation of 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (Enantiomer 1) (Compound 29) and 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (Enantiomer 2) (Compound 30)

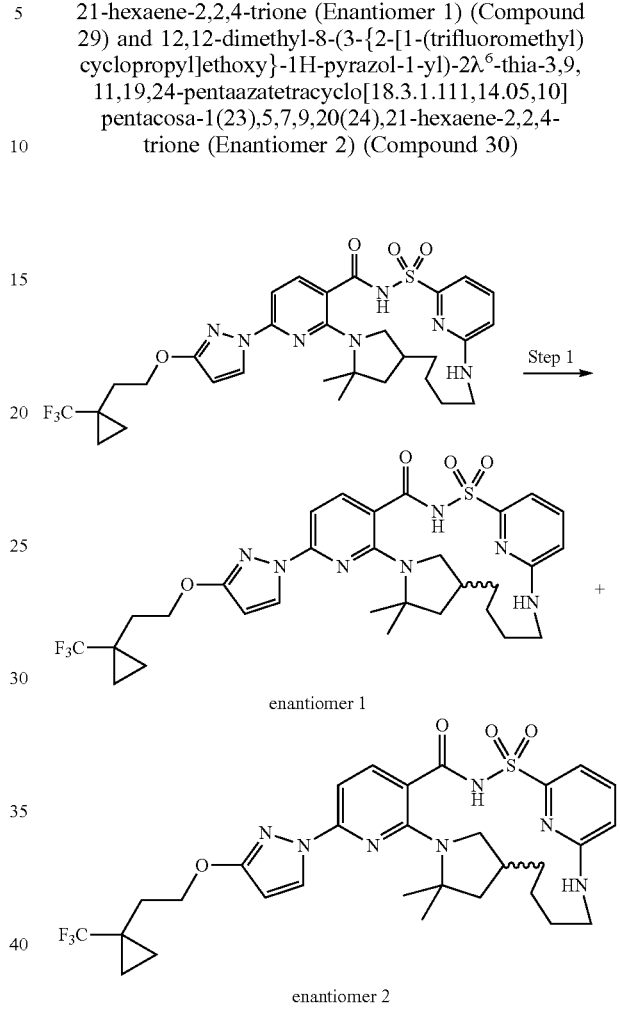

Step 1: 12,12-Dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (Enantiomer 1) (Compound 29) and 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (Enantiomer 2) (Compound 30)

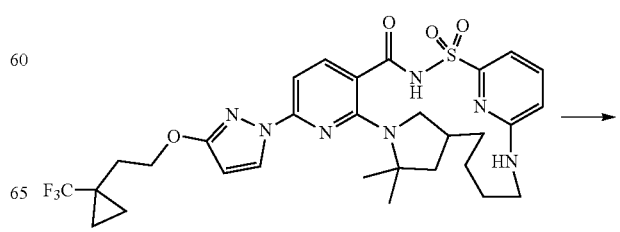

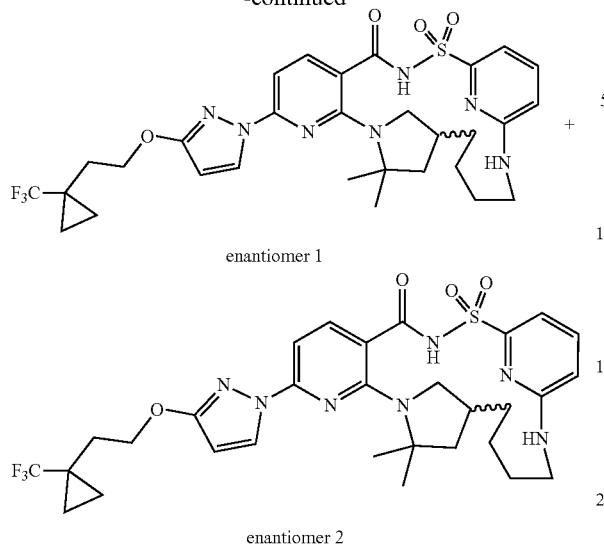

enantiomer 1 enantiomer 2

Racemic 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (Compound 28) (204 mg, 0.3150 mmol) was subjected to chiral SFC chromatography using a ChiralPak AS-H (250×21.2 mm column, 5 μm particle size) with 30% acetonitrile:methanol (90:10))/70% carbon dioxide mobile phase at 0.5 mL/min giving as the first enantiomer to elute, 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (enantiomer 1) (Compound 29) (94.1 mg, 91%) as an off-white solid; ESI-MS m/z calc. 647.2502, found 648.2 (M+1)⁺; Retention time: 2.27 min (LC Method E) and as the second enantiomer to elute, 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.111,14.05,10]pentacosa-1(23),5,7,9,20(24),21-hexaene-2,2,4-trione (enantiomer 2) (Compound 30) (90.0 mg, 87%) as an off-white solid; ¹H NMR (400 MHz, dimethyl sulfoxide-d₆) δ 12.45 (s, 1H), 8.21 (d, J=2.8 Hz, 1H), 7.86 (d, J=8.3 Hz, 1H), 7.69 (t, J=7.9 Hz, 1H), 7.23 (d, J=7.2 Hz, 1H), 6.93 (d, J=8.3 Hz, 1H), 6.81 (d, J=8.1 Hz, 2H), 6.12 (d, J=2.7 Hz, 1H), 4.32 (t, J=7.0 Hz, 2H), 3.29 (dd, J=4.7, 2.4 Hz, 1H), 2.86-2.69 (m, 1H), 2.63 (dd, J=16.0, 11.6 Hz, 1H), 2.13 (s, 1H), 2.08 (t, J=7.1 Hz, 2H), 1.85 (dd, J=11.9, 5.5 Hz, 1H), 1.68-1.56 (m, 2H), 1.55 (d, J=2.9 Hz, 6H), 1.47 (dd, J=22.2, 10.1 Hz, 2H), 1.26-1.16 (m, 2H), 0.96 (dd, J=7.7, 3.7 Hz, 2H), 0.93 (d, J=9.2 Hz, 1H), 0.88 (t, J=5.8 Hz, 2H), ESI-MS m/z calc. 647.2502, found 648.2 (M+1)⁺; Retention time: 2.27 min (LC Method E).

Example 9: Preparation of 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5(10),6,8,19,21-hexaene-2,2,4-trione (Diastereomer Pair 1) (Compound 35), 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5(10),6,8,19,21-hexaene-2,2,4-trione (Diastereomer Pair 2) (Compound 36), 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5(10),6,8,19,21-hexaene-2,2,4-trione (Diastereomer Pair 1, Enantiomer 1) (Compound 58), 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5(10),6,8,19,21-hexaene-2,2,4-trione (Diastereomer Pair 1, Enantiomer 2) (Compound 59), 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5(10),6,8,19,21-hexaene-2,2,4-trione (Diastereomer Pair 2, Enantiomer 1) (Compound 60) and 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5(10),6,8,19,21-hexaene-2,2,4-trione (Diastereomer Pair 2, Enantiomer 2) (Compound 61)

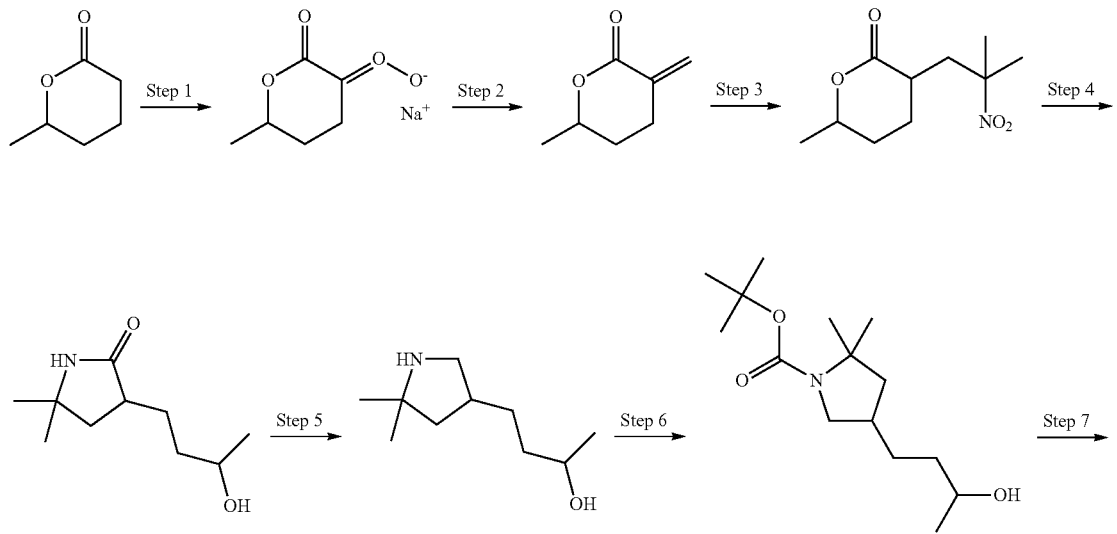

217
218
-continued
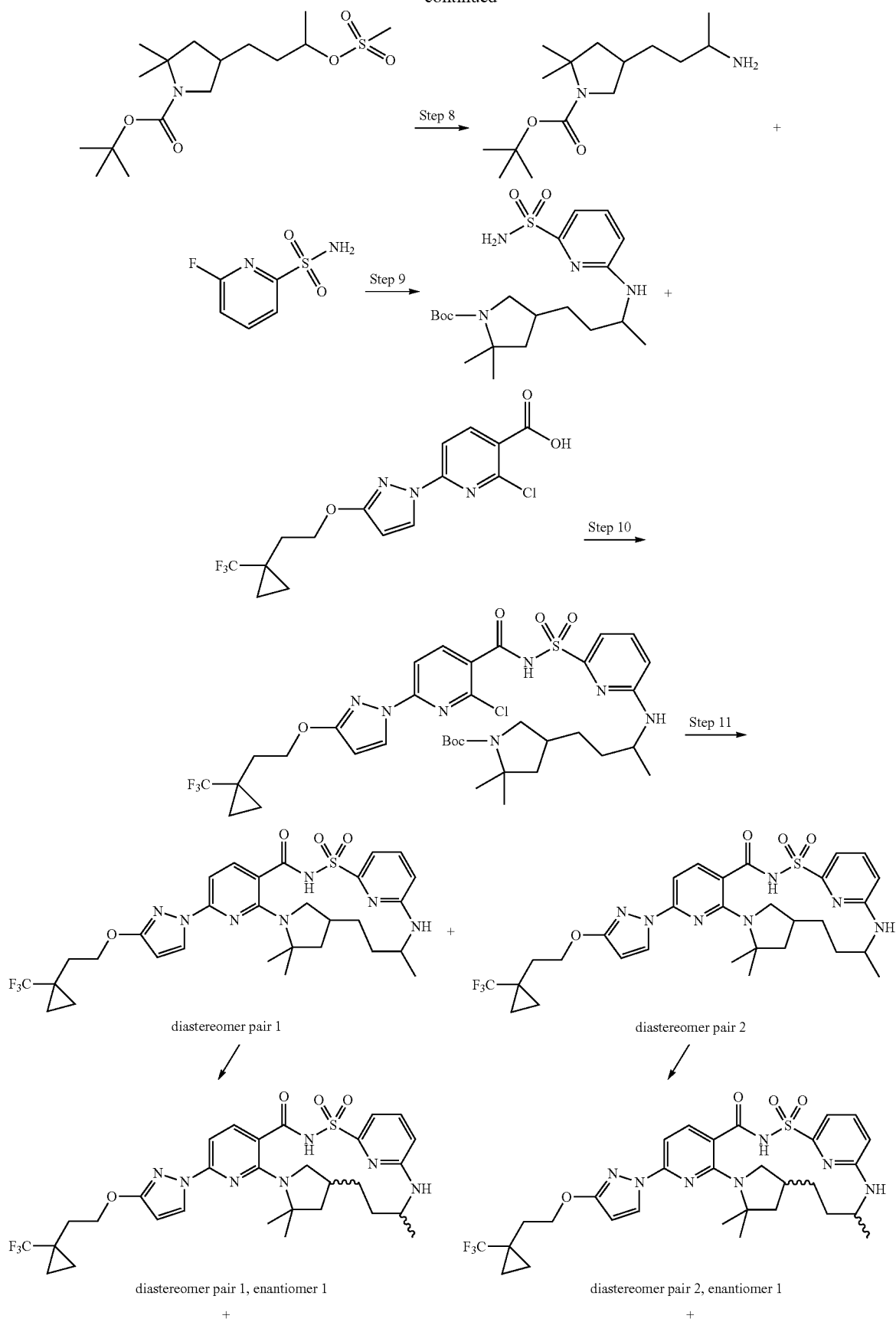
diastereomer pair 1
diastereomer pair 2
diastereomer pair 1, enantiomer 1
+
diastereomer pair 2, enantiomer 1
+

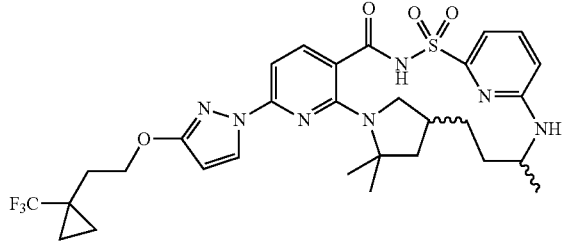

diastereomer pair 1, enantiomer 2

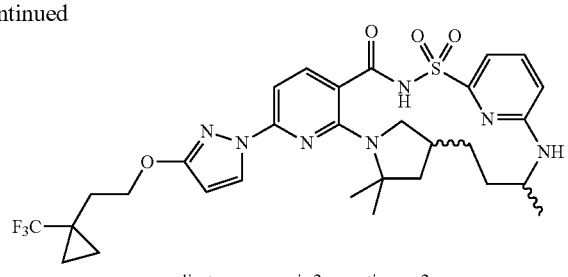

diastereomer pair 2, enantiomer 2

Step 1: (3E)-3-(Hydroxymethylene)-6-methyl-tetrahydropyran-2-one (Sodium Salt)

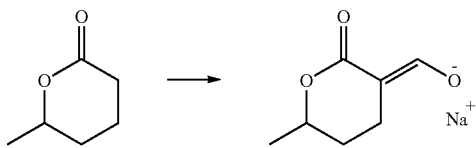

To a suspension of sodium hydride (60% in mineral oil) (2.63 g of 60% w/w, 65.8 mmol) in diethyl ether (56 mL) was added absolute ethanol (300 µL) then a mixture of 6-methyltetrahydropyran-2-one (5.0 g, 43.80 mmol) and ethyl formate (6.0 mL, 74 mmol) was added dropwise at ambient temperature within 30 min. After addition was finished the reaction mixture stirred for 1 h at room temperature. The solid formed in the mixture (sodium salt of product) was collected by filtration, washed with diethyl ether and dried under high vacuum to afford (3E)-3-(hydroxymethylene)-6-methyl-tetrahydropyran-2-one (Sodium salt) (7.1 g, 99%). ESI-MS m/z calc. 142.06299, found 143.2 (M+1)$^+$; Retention time: 0.64 min (LC Method E).

Step 2: 6-Methyl-3-methylene-tetrahydropyran-2-one

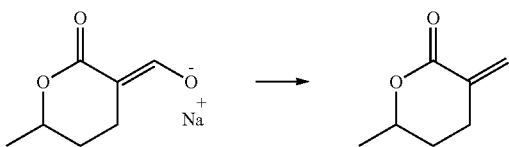

(3E)-3-(Hydroxymethylene)-6-methyl-tetrahydropyran-2-one (Sodium salt) (7.1 g, 43 mmol) was suspended in tetrahydrofuran (100 mL), treated with paraformaldehyde (4.2 g, 140 mmol) under nitrogen and the mixture was heated to 65° C. for 1 h. The mixture was cooled in an ice-water bath, quenched with aqueous saturated potassium carbonate (20 mL) and the organic phase was separated, then the aqueous phase was extracted with diethyl ether (4×10 mL). The organic fractions were combined, washed with brine, dried over anhydrous sodium sulfate, filtered and concentrated under reduced pressure by rotary evaporation with no heating. The residue obtained was purified by silica gel chromatography (120 gram column) using a gradient from 100% hexanes to 40% ethyl acetate in hexanes to afford as a colorless liquid, 6-methyl-3-methylene-tetrahydropyran-2-one (2.96 g, 55%). $^1$H NMR (400 MHz, CDCl$_3$) δ 6.48-6.38 (m, 1H), 5.57 (dt, J=2.7, 1.5 Hz, 1H), 4.49 (dqd, J=10.4, 6.3, 2.6 Hz, 1H), 2.71 (dddt, J=16.2, 5.0, 3.5, 1.3 Hz, 1H), 2.65-2.52 (m, 1H), 2.03-1.93 (m, 1H), 1.67 (dddd, J=13.9, 12.4, 10.5, 5.1 Hz, 1H), 1.40 (d, J=6.3 Hz, 3H). ESI-MS m/z calc. 126.06808, found 127.0 (M+1)$^+$; Retention time: 0.66 min (LC Method E).

Step 3: 6-Methyl-3-(2-methyl-2-nitro-propyl)tetrahydropyran-2-one

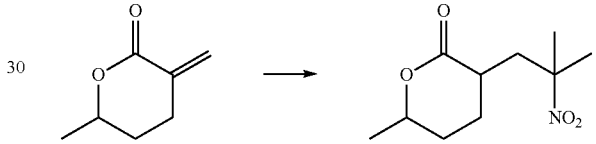

2-Nitropropane (2.6 mL, 29 mmol) was treated with 1,8-diazabicyclo[5.4.0]undec-7-ene (550 µL, 3.68 mmol) and stirred for 5 min under nitrogen then a solution of 6-methyl-3-methylene-tetrahydropyran-2-one (2.96 g, 23.5 mmol) in acetonitrile (32 mL) was added dropwise at room temperature over 45 min. The solution was stirred at room temperature for 4 h. The mixture was evaporated and the residue was then purified by silica gel chromatography (120 gram column) using a gradient from 100% hexanes to 60% ethyl acetate in hexanes to isolate product which was then dried under vacuum to afford as a clear oil which turned into a white solid upon standing, 6-methyl-3-(2-methyl-2-nitropropyl)tetrahydropyran-2-one (4.32 g, 85%). $^1$H NMR (400 MHz, CDCl$_3$) δ 4.57-4.37 (m, 1H), 2.71-2.58 (m, 1H), 2.51-2.32 (m, 1H), 2.24 (dd, J=15.0, 6.9 Hz, 1H), 2.14-2.06 (m, 1H), 2.00-1.87 (m, 1H), 1.68-1.60 (m, 6H), 1.58 (dd, J=4.8, 2.7 Hz, 1H), 1.56-1.47 (m, 1H), 1.36 (dd, J=6.2, 3.2 Hz, 3H). ESI-MS m/z calc. 215.11575, found 216.2 (M+1)$^+$; Retention time: 1.11 min (LC Method E).

Step 4: 3-(3-Hydroxybutyl)-5,5-dimethyl-pyrrolidin-2-one

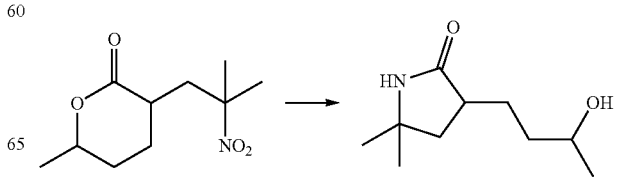

6-methyl-3-(2-methyl-2-nitro-propyl)tetrahydropyran-2-one (4.32 g, 20.07 mmol) was dissolved in ethanol (78 mL) and wet Raney nickel (1.2 g, 20.45 mmol) was added under nitrogen atmosphere. Three vacuum/hydrogen cycles were performed and the resulting mixture was stirred at room temperature under hydrogen (1 atmosphere) for 10 min. Then the suspension was equipped with a reflux condenser and heated to 60° C. and stirred at this temperature under hydrogen for 24 h. Cooled to room temperature and filtered through Celite and washed with ethyl acetate. The filtrates were combined and concentrated under reduced pressure and the residue was purified by silica gel chromatography (120 gram column) using a shallow gradient from 100% dichloromethane to 10% methanol in dichloromethane giving 3-(3-hydroxybutyl)-5,5-dimethyl-pyrrolidin-2-one (2.5 g, 67%) as a white solid. $^1$H NMR (400 MHz, dimethyl sulfoxide-$d_6$) δ 7.63 (s, 1H), 4.36 (d, J=4.7 Hz, 1H), 3.56 (dt, J=11.9, 6.0 Hz, 1H), 2.35 (qd, J=9.3, 4.4 Hz, 1H), 2.01 (dd, J=12.3, 8.6 Hz, 1H), 1.85-1.59 (m, 1H), 1.45-1.35 (m, 1H), 1.31 (ddd, J=10.6, 8.1, 4.1 Hz, 2H), 1.28-1.20 (m, 1H), 1.18 (s, 3H), 1.13 (s, 3H), 1.03 (dd, J=6.2, 1.6 Hz, 3H). ESI-MS m/z calc. 185.14159, found 186.2 (M+1)$^+$; Retention time: 0.74 min (LC Method E).

Step 5: 4-(5,5-Dimethylpyrrolidin-3-yl)butan-2-ol

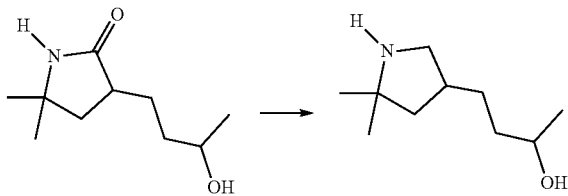

A solution of 3-(3-hydroxybutyl)-5,5-dimethyl-pyrrolidin-2-one (2.5 g, 13.49 mmol) in anhydrous tetrahydrofuran (37 mL) was carefully added (within 20 min) to a suspension of lithium aluminum hydride (686.6 mg, 20.24 mmol) in dry tetrahydrofuran (37 mL) at room temperature under nitrogen atmosphere. After addition was finished the reaction mixture was heated to reflux for 72 h (two extra portions of lithium aluminum hydride (200 mg, 7.00 mmol) were added to the reaction mixture after 24 h and 48 h of refluxing). The mixture was cooled in an ice-water bath; more tetrahydrofuran (25 mL) was added to the mixture followed by slow addition of aqueous saturated sodium potassium tartrate tetrahydrate (Rochelle's salt, 30 mL). The resulting mixture was stirred vigorously for 2 h at room temperature until a clear separation of aqueous and organic phases was achieved; then the organic layer was separated and concentrated under vacuum. The residue was dissolved in dichloromethane (100 mL) and the obtained solution was washed with brine (2×15 mL). The organic phase was dried over sodium sulfate, filtered and concentrated under reduced pressure to afford as a yellow oil, 4-(5,5-dimethylpyrrolidin-3-yl)butan-2-ol (1.6 g, 69%). $^1$H NMR (400 MHz, CDCl$_3$) δ 3.78 (dd, J=11.9, 5.8 Hz, 1H), 3.14 (ddd, J=10.4, 7.6, 2.8 Hz, 1H), 2.59 (dd, J=11.0, 8.1 Hz, 1H), 2.24-2.07 (m, 1H), 1.87-1.78 (m, 1H), 1.73 (s, 2H), 1.54-1.37 (m, 4H), 1.37-1.21 (m, 1H), 1.21-1.13 (m, 9H). ESI-MS m/z calc. 171.16231, found 172.2 (M+1)$^+$; Retention time: 0.53 min (LC Method E).

Step 6: tert-Butyl 4-(3-hydroxybutyl)-2,2-dimethyl-pyrrolidine-1-carboxylate

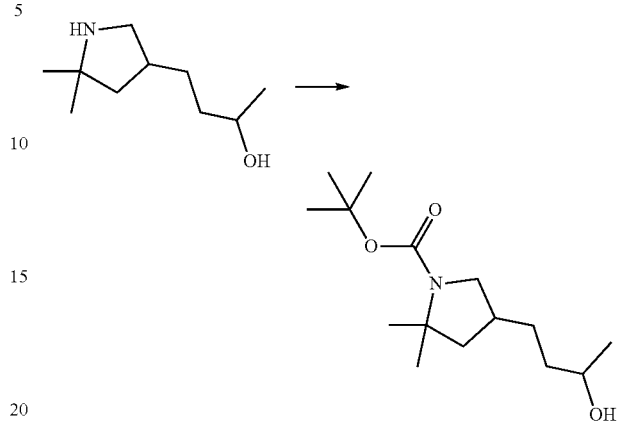

Di-tert-butyl dicarbonate (2.4 mL, 10.45 mmol) and triethylamine (1.7 mL, 12.20 mmol) were added to a solution of 4-(5,5-dimethylpyrrolidin-3-yl)butan-2-ol (1.6 g, 9.341 mmol) dissolved in dichloromethane (40 mL) at 0° C. The reaction mixture was allowed to warm to room temperature and stirred for 30 min. The mixture was washed with water (15 mL), saturated sodium bicarbonate (15 mL) and brine (15 mL) then extracted the organic, dried over sodium sulfate, filtered and concentrated the mixture. The residue was purified by silica gel chromatography (40 gram column) using a gradient from 100% dichloromethane to 10% methanol in dichloromethane to isolate as a clear oil, tert-butyl 4-(3-hydroxybutyl)-2,2-dimethyl-pyrrolidine-1-carboxylate (2.4 g, 95%). $^1$H NMR (400 MHz, CDCl$_3$) δ 3.79 (s, 1H), 3.75-3.56 (m, 1H), 3.00-2.77 (m, 1H), 2.18-2.04 (m, 1H), 1.89 (td, J=12.3, 6.0 Hz, 1H), 1.63 (s, 1H), 1.53 (s, 5H), 1.49-1.43 (m, 12H), 1.38 (s, 1H), 1.34 (dd, J=9.1, 4.5 Hz, 2H), 1.20 (t, J=5.5 Hz, 3H). ESI-MS m/z calc. 271.21475, found 272.2 (M+1)$^+$; Retention time: 1.64 min (LC Method E).

Step 7: tert-Butyl 2,2-dimethyl-4-(3-methylsulfonyloxybutyl)pyrrolidine-1-carboxylate

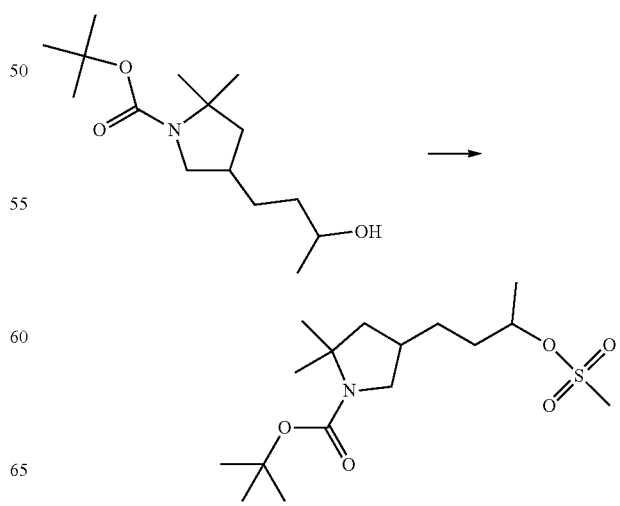

To a solution in dichloromethane (6 mL) chilled to 0° C. of tert-butyl 4-(3-hydroxybutyl)-2,2-dimethyl-pyrrolidine-1-carboxylate (346 mg, 1.275 mmol) and triethylamine (1.2 mL, 8.6 mmol) was added dropwise methanesulfonyl chloride (350 µL, 4.52 mmol). The reaction mixture was stirred for 20 h allowing to warm to room temperature after 1 h (the clear solution turned cloudy orange after 10 min). The reaction mixture was quenched with ice-water and dichloromethane, followed by brine. The aqueous layer was extracted with further dichloromethane (2×20 mL) and the combined organics were dried over sodium sulfate, filtered and concentrated under reduced pressure. The resulting material was dried under vacuum for 1 h to give as a yellow oil, tert-butyl 2,2-dimethyl-4-(3-methylsulfonyloxybutyl)pyrrolidine-1-carboxylate (440 mg, 99%). ESI-MS m/z calc. 349.1923, found 350.1 (M+1)⁺; Retention time: 1.8 min (LC Method E).

Step 8: tert-Butyl 4-(3-aminobutyl)-2,2-dimethyl-pyrrolidine-1-carboxylate

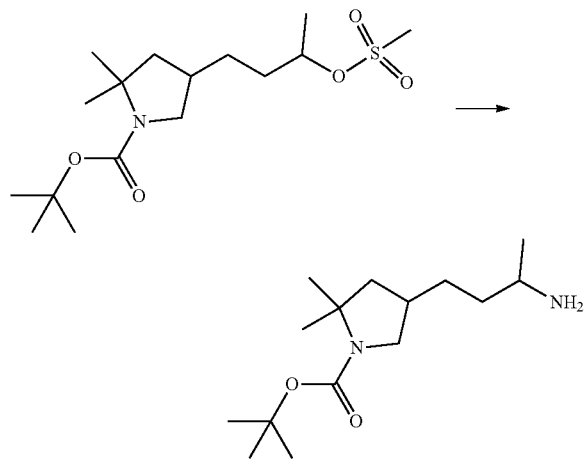

tert-Butyl 2,2-dimethyl-4-(3-methylsulfonyloxybutyl)pyrrolidine-1-carboxylate (440 mg, 1.259 mmol) was dissolved in a mixture of dioxane (10 mL) and ammonium hydroxide (10 mL of 30% w/v, 85.60 mmol). The mixture was heated to 50° C. in a sealed vessel for 72 h. The dioxane was concentrated under vacuum and dichloromethane (50 mL) was added. The organic layer was separated, dried over sodium sulfate, filtered and concentrated under vacuum. The crude material was purified by silica gel chromatography (24 gram column) using dichloromethane methanol (containing 5 mL/liter 30% ammonium hydroxide) gradient method (0 to 15% methanol) to obtain as a light yellow oil, tert-butyl 4-(3-aminobutyl)-2,2-dimethyl-pyrrolidine-1-carboxylate (199 mg, 58%). ¹H NMR (400 MHz, dimethyl sulfoxide) δ 7.86 (s, 2H), 3.62-3.49 (m, 1H), 3.14 (dt, J=17.3, 5.3 Hz, 1H), 2.79 (dd, J=19.2, 10.2 Hz, 1H), 2.08-1.97 (m, 1H), 1.93-1.81 (m, 1H), 1.56 (ddd, J=25.3, 14.2, 6.6 Hz, 1H), 1.49-1.43 (m, 1H), 1.42-1.33 (m, 15H), 1.24 (d, J=5.9 Hz, 4H), 1.16 (d, J=6.5 Hz, 2H).

Step 9: tert-Butyl 2,2-dimethyl-4-[3-[(6-sulfamoyl-2-pyridyl)amino]butyl]pyrrolidine-1-carboxylate

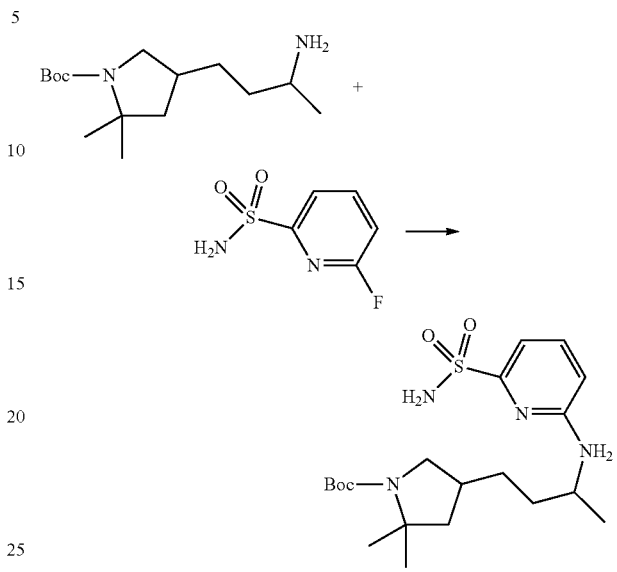

In a sealed 20 mL microwave vial, a solution of 6-fluoropyridine-2-sulfonamide (526 mg, 2.986 mmol), tert-butyl 4-(3-aminobutyl)-2,2-dimethyl-pyrrolidine-1-carboxylate (800 mg, 2.958 mmol) and diisopropylethylamine (2.6 mL, 14.93 mmol) in dimethyl sulfoxide (8 mL) was stirred at 130° C. for 16 h. The solvent was removed in vacuo and the residue was dissolved in dichloromethane and washed with water. Organic extract was dried over sodium sulfate, evaporated and purified by silica gel chromatography using 12 g column (gradient from 0-85% ethyl acetate/hexanes) to afford tert-butyl 2,2-dimethyl-4-[3-[(6-sulfamoyl-2-pyridyl)amino]butyl]pyrrolidine-1-carboxylate (490 mg, 38%). ¹H NMR (400 MHz, dimethyl sulfoxide-d₆) δ 7.49 (dd, J=8.4, 7.3 Hz, 1H), 7.03 (s, 2H), 6.93 (d, J=7.2 Hz, 1H), 6.78 (d, J=8.1 Hz, 1H), 6.59 (d, J=8.4 Hz, 1H), 4.02 (s, 1H), 3.53 (d, J=10.0 Hz, 1H), 2.78 (dd, J=18.9, 10.6 Hz, 1H), 2.02 (d, J=27.8 Hz, 1H), 1.88 (s, 1H), 1.55-1.42 (m, 2H), 1.42-1.29 (m, 16H), 1.23 (s, 3H), 1.11 (d, J=6.4 Hz, 3H). ESI-MS m/z calc. 426.23007, found 427.1 (M+1)⁺; Retention time: 0.66 min (LC Method A).

Step 10: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate

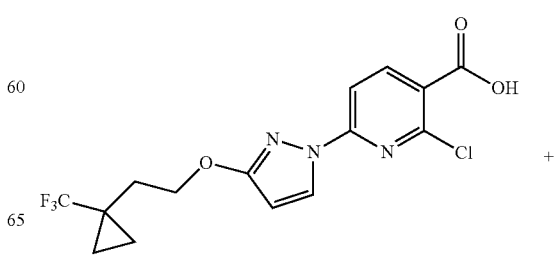

225

-continued

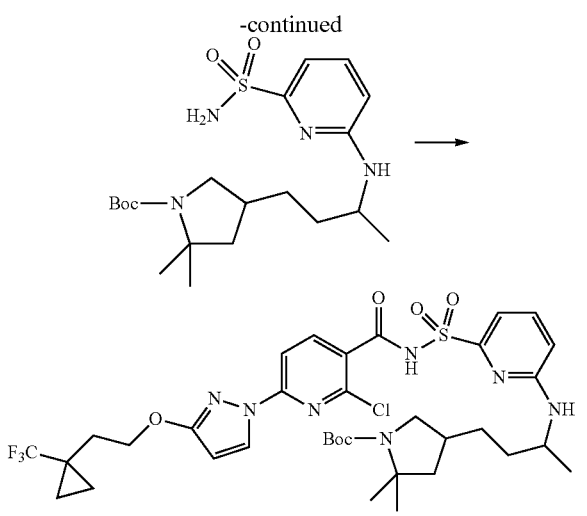

2-Chloro-6-[3-[2-[1-(trifluoromethyl)cyclopropyl]ethoxy]pyrazol-1-yl]pyridine-3-carboxylic acid (160 mg, 0.4258 mmol) and carbonyl diimidazole (69 mg, 0.4255 mmol) were combined in tetrahydrofuran (2.5 mL) and stirred for 120 min at 50° C. Then tert-butyl 2,2-dimethyl-4-[3-[(6-sulfamoyl-2-pyridyl)amino]butyl]pyrrolidine-1-carboxylate (145 mg, 0.3399 mmol) was added followed by 1,8-diazabicyclo[5.4.0]undec-7-ene (110 µL, 0.7356 mmol) and the reaction was heated at 50° C. for 18 h. The reaction was diluted with ethyl acetate and washed with a 1 M citric acid solution, followed by brine. The organics were separated, dried over sodium sulfate, filtered and evaporated and then purified by reverse-phase preparative reverse-phase HPLC utilizing a $C_{18}$ column and method 30-99 A1-B1 (acetonitrile-water+5 mM hydrochloric acid) to afford tert-butyl 4-[3-[[6-[[2-chloro-6-[3-[2-[1-(trifluoromethyl)cyclopropyl]ethoxy]pyrazol-1-yl]pyridine-3-carbonyl]sulfa-

226 moyl]-2-pyridyl]amino]butyl]-2,2-dimethyl-pyrrolidine-1-carboxylate (97 mg, 36%) as a white solid. ESI-MS m/z calc. 783.27924, found 784.2 (M+1)⁺; Retention time: 2.44 min (LC Method E).

Step 11: 12,12,17-Trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.111,14.05,10]tetracosa-1(23),5(10),6,8,19,21-hexaene-2,2,4-trione (Diastereomer Pair 1) (Compound 35), 12,12,17-Trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.111,14.05,10]tetracosa-1(23),5(10),6,8,19,21-hexaene-2,2,4-trione (Diastereomer Pair 2) (Compound 36), 12,12,17-trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.111,14.05,10]tetracosa-1(23),5(10),6,8,19,21-hexaene-2,2,4-trione (Diastereomer Pair 1, Enantiomer 1) (Compound 58), 12,12,17-trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.111,14.05,10]tetracosa-1(23),5(10),6,8,19,21-hexaene-2,2,4-trione (Diastereomer Pair 1, Enantiomer 2) (Compound 59), 12,12,17-trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.111,14.05,10]tetracosa-1(23),5(10),6,8,19,21-hexaene-2,2,4-trione (Diastereomer Pair 2, Enantiomer 1) (Compound 60) and 12,12,17-trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.111,14.05,10]tetracosa-1(23),5(10),6,8,19,21-hexaene-2,2,4-trione (Diastereomer Pair 2, Enantiomer 2) (Compound 61)

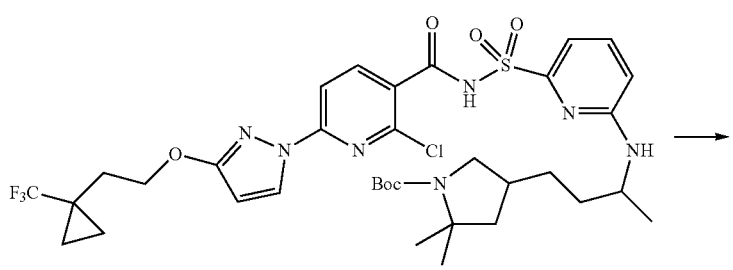

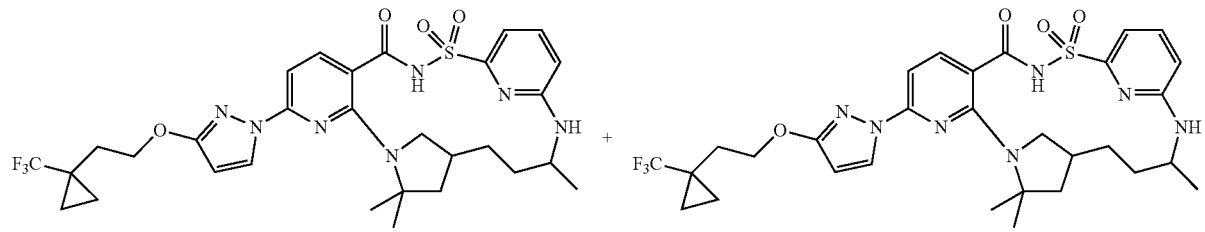

diastereomer pair 1     diastereomer pair 2

-continued

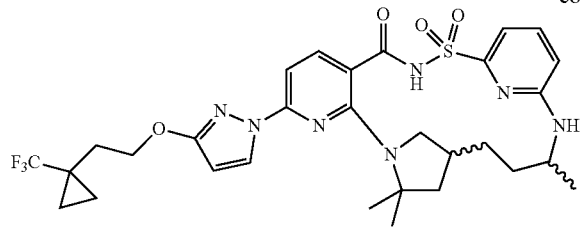

diastereomer pair 1, enantiomer 1

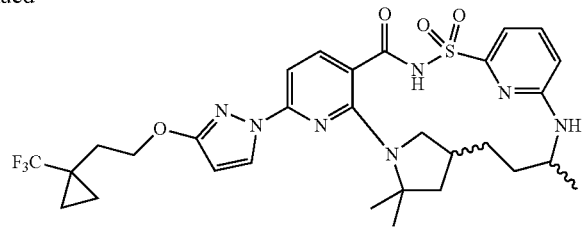

diastereomer pair 2, enantiomer 1

+

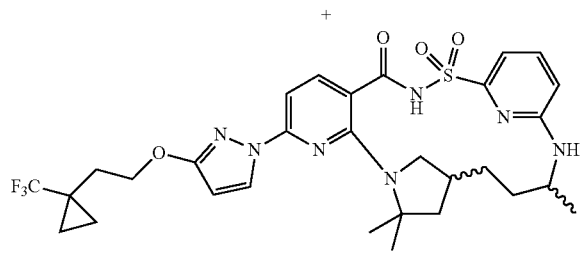

diastereomer pair 1, enantiomer 2

+

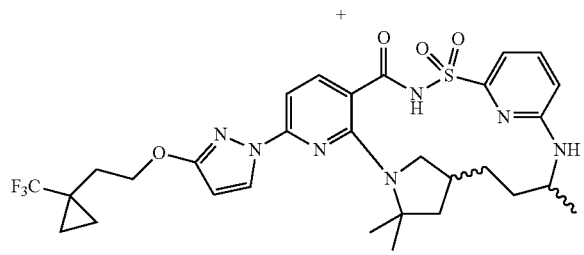

diastereomer pair 2, enantiomer 2

Part A: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate (97 mg, 0.1237 mmol) was dissolved in dichloromethane (2.0 mL) and to the mixture was added hydrochloric acid (4 M in dioxane) (1000 µL of 4 M, 4.000 mmol) and stirred at room temperature for 3 h. Concentrated mixture to dryness under reduced pressure, redissolved in ethyl acetate, then added aqueous 2 M sodium carbonate (5 mL), giving pH~10. Extracted organic layer with ethyl acetate (2×10 mL), washed with brine, then dried over sodium sulfate, filtered and evaporated to dryness under reduced pressure.

Part B: Combined material from Part A and potassium carbonate (90 mg, 0.6512 mmol), cesium fluoride (30 mg, 0.1975 mmol), 3 Å molecular sieves and dimethyl sulfoxide (2.0 mL) in a vial, purged with nitrogen, capped, heated at 150° C. and stirred for 18 h. Cooled to room temperature. The reaction mixture was filtered and then purified by reverse-phase preparative chromatography ($C_{18}$ column, 20% to 99% acetonitrile (no modifier) in water (5 mM hydrochloric acid)) to afford as the first diastereomer pair of enantiomers to elute, 12,12,17-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (diastereomer pair 1) (Compound 35) (9.0 mg, 22%) as an off-white solid; $^1$H NMR (400 MHz, dimethyl sulfoxide-d$_6$) δ 12.62 (s, 1H), 8.21 (d, J=2.8 Hz, 1H), 7.80 (d, J=8.2 Hz, 1H), 7.57 (dd, J=8.5, 7.2 Hz, 1H), 7.05 (d, J=7.2 Hz, 1H), 6.97 (d, J=9.2 Hz, 1H), 6.91 (d, J=8.2 Hz, 1H), 6.68 (d, J=8.5 Hz, 1H), 6.11 (d, J=2.8 Hz, 1H), 4.31 (t, J=7.2 Hz, 2H), 4.17 (s, 1H), 3.10 (d, J=9.4 Hz, 1H), 2.74-2.66 (m, 1H), 2.20-2.10 (m, 1H), 2.08 (t, J=7.1 Hz, 2H), 1.85 (dd, J=11.9, 5.2 Hz, 1H), 1.64 (d, J=7.1 Hz, 1H), 1.62-1.59 (m, 3H), 1.56 (d, J=12.9 Hz, 2H), 1.51 (s, 3H), 1.36-1.24 (m, 2H), 1.04 (d, J=6.3 Hz, 3H), 0.95 (d, J=4.6 Hz, 2H), 0.90 (d, J=11.1 Hz, 2H); ESI-MS m/z calc. 647.2502, found 648.2 (M+1)$^+$; Retention time: 2.25 min (LC Method E); and as the second diastereomer pair of enantiomers to elute, 12,12,17-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (diastereomer pair 2) (Compound 36) (33.6 mg, 82%) as an off-white solid; $^1$H NMR (400 MHz, dimethyl sulfoxide-d$_6$) δ 12.41 (s, 1H), 8.21 (d, J=2.7 Hz, 1H), 7.65 (d, J=7.8 Hz, 1H), 7.58 (dd, J=8.5, 7.3 Hz, 1H), 7.20 (dd, J=12.2, 7.3 Hz, 2H), 6.89 (d, J=8.2 Hz, 1H), 6.70 (d, J=8.2 Hz, 1H), 6.10 (d, J=2.7 Hz, 1H), 4.31 (t, J=7.0 Hz, 2H), 3.65 (d, J=5.0 Hz, 1H), 3.23-2.97 (m, 2H), 2.27 (dd, J=10.1, 5.1 Hz, 1H), 2.07 (t, J=7.1 Hz, 2H), 1.89 (dd, J=11.8, 5.8 Hz, 2H), 1.78-1.67 (m, 1H), 1.62 (s, 3H), 1.58 (d, J=12.0 Hz, 1H), 1.52 (s, 3H), 1.45 (dd, J=14.0, 6.8 Hz, 1H), 1.22 (d, J=6.6 Hz, 3H), 1.15-1.06 (m, 1H), 0.97-0.93 (m, 2H), 0.89 (d, J=11.4 Hz, 2H). ESI-MS m/z calc. 647.2502, found 648.2 (M+1)$^+$; Retention time: 2.29 min (LC Method E).

Part C: 12,12,17-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (diastereomer pair 1) (11.5 mg) was subjected to chiral separation by SFC chromatography using a ChiralPak AS-H (250×10 mm) column (5 µm particle size) with 16% acetonitrile/methanol (90:10)/84% carbon dioxide mobile phase at 10 mL/min over 8.0 min [injection volume=70 µL of 24 mg/mL solution in acetonitrile/methanol (90:10)] giving as the first enantiomer to elute, 12,12,17-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (diastereomer pair 1, enantiomer 1) (Compound 58) (2.6 mg, 45%; >98% ee) as an off-white solid; ESI-MS m/z calc. 647.2502, found 648.2 (M+1)$^+$; Retention time: 2.25 min (LC Method E) and as the second enantiomer to elute, 12,12,17-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (diastereomer pair 1, enantiomer 2) (Compound 59) (3.6 mg, 62%; >98% ee) as an off-white solid; ESI-MS m/z calc. 647.2502, found 648.2 (M+1)$^+$; Retention time: 2.25 min (LC Method E).

Part D: 12,12,17-trimethyl-8-(3-{2-[1-(trifluoromethyl) cyclopropyl]ethoxy}-1H-pyrazol-1-yl)-2λ⁶-thia-3,9,11,18, 23-pentaazatetracyclo[17.3.1.1¹¹,¹⁴.0⁵,¹⁰]tetracosa-1(23), 5(10),6,8,19,21-hexaene-2,2,4-trione (diastereomer pair 2) (55 mg) was subjected to chiral separation by SFC chromatography using a ChiralPak AS-H (250×10 mm) column (5 µm particle size) with 16% acetonitrile/methanol (90:10)/ 84% carbon dioxide mobile phase at 10 mL/min over 8.0 min [injection volume=70 µL of 24 mg/mL solution in acetonitrile/methanol (90:10)] giving as the first enantiomer to elute, 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5 (10),6,8,19,21-hexaene-2,2,4-trione (diastereomer pair 2, enantiomer 1) (Compound 60) (17.9 mg, 64%, >98% ee) as an off-white solid; ESI-MS m/z calc. 647.2502, found 648.2 (M+1)⁺; Retention time: 2.3 min (LC Method E) and as the second enantiomer to elute, 12,12,17-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.05, 10]tetracosa-1 (23),5(10),6,8,19,21-hexaene-2,2,4-trione (diastereomer pair 2, enantiomer 2) (Compound 61) (18.1 mg, 65%, >98% ee) as an off-white solid; ¹H NMR (400 MHz, dimethyl sulfoxide-d₆) δ 12.40 (s, 1H), 8.21 (d, J=2.7 Hz, 1H), 7.59 (dd, J=20.6, 12.9 Hz, 2H), 7.18 (d, J=7.2 Hz, 2H), 6.89 (d, J=8.1 Hz, 1H), 6.70 (d, J=8.3 Hz, 1H), 6.10 (d, J=2.6 Hz, 1H), 4.31 (t, J=7.0 Hz, 2H), 3.63 (s, 1H), 3.12 (d, J=30.7 Hz, 2H), 2.28 (dd, J=21.3, 12.6 Hz, 1H), 2.07 (t, J=7.0 Hz, 2H), 2.03-1.81 (m, 2H), 1.79-1.67 (m, 1H), 1.62 (s, 3H), 1.57 (d, J=12.1 Hz, 1H), 1.52 (s, 3H), 1.49-1.39 (m, 1H), 1.21 (d, J=6.5 Hz, 3H), 1.10 (dd, J=12.8, 4.4 Hz, 1H), 0.99-0.93 (m, 2H), 0.88 (s, 2H), ESI-MS m/z calc. 647.2502, found 648.2 (M+1)⁺; Retention time: 2.3 min (LC Method E).

Example 10: Preparation of 12,12-dimethyl-8-{3-[(2,2,3,3-tetramethylcyclopropyl) methoxy]-1H-pyrazol-1-yl}-2λ⁶-thia-3,9,11,18,23-pentaazatetracyclo[17.3.1.1¹¹,¹⁴.0⁵,¹⁰]tetracosa-1(22),5,7,9,19(23), 20-hexaene-2,2,4-trione (Compound 42)

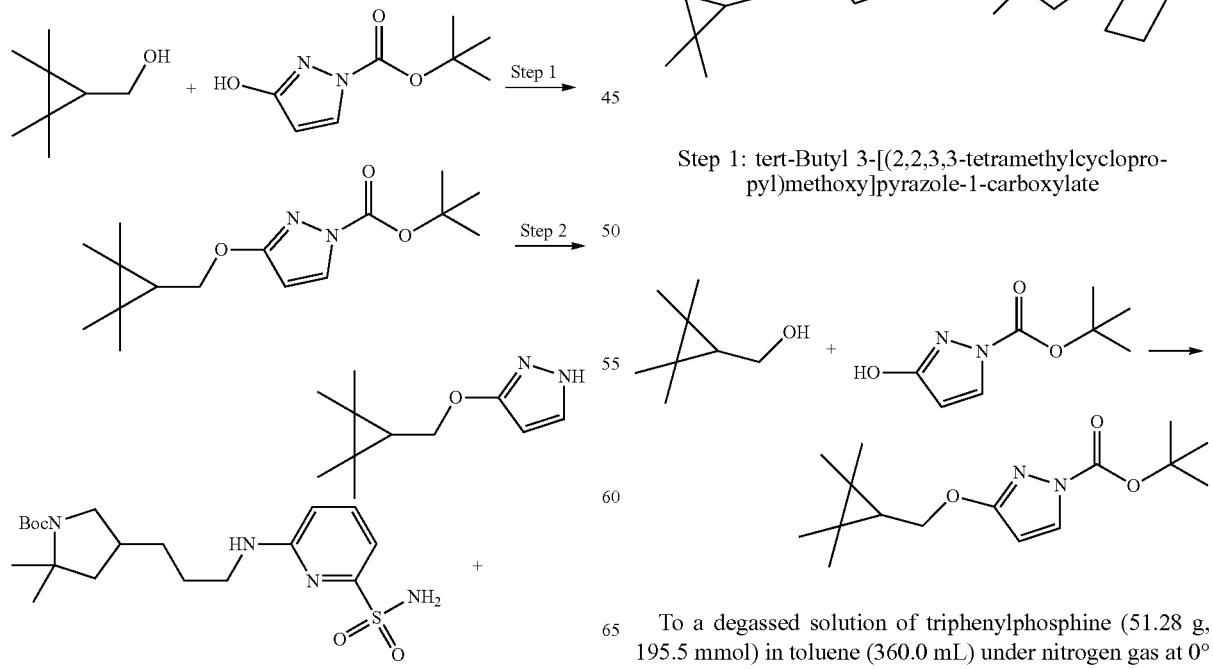

Step 1: tert-Butyl 3-[(2,2,3,3-tetramethylcyclopropyl)methoxy]pyrazole-1-carboxylate To a degassed solution of triphenylphosphine (51.28 g, 195.5 mmol) in toluene (360.0 mL) under nitrogen gas at 0° C. was added DIAD (39.53 g, 37.86 mL, 195.5 mmol)

dropwise. The mixture was stirred at 0° C. for 30 min affording a white slurry. To the mixture was added a solution of (2,2,3,3-tetramethylcyclopropyl)methanol (29.84 g of 70% w/w, 162.9 mmol) and tert-butyl 3-hydroxypyrazole-1-carboxylate (30 g, 162.9 mmol) in toluene (600.0 mL) dropwise at 5° C. over 2 h. The mixture was allowed to warm to ambient temperature and was stirred for 18 h. The mixture was heated to 75° C. for a total of 6 h and then allowed to cool to ambient temperature. The slurry was diluted with heptane (900 mL) and stirred at ambient temperature for 3 h. The slurry was filtered over Celite and the precipitate washed 3× with 100 mL of heptane. The filtrate was concentrated in vacuo affording a thick yellow oil. The crude product was chromatographed on a 750 gram silica gel column loading with dichloromethane and eluting with a 0-20% ethyl acetate/hexanes gradient. Collected fractions containing product were concentrated in vacuo affording an off-white solid, tert-butyl 3-[(2,2,3,3-tetramethylcyclopropyl)methoxy]pyrazole-1-carboxylate (30.1 g, 63%). $^1$H NMR (400 MHz, Chloroform-d) δ 7.82 (d, J=3.0 Hz, 1H), 5.88 (d, J=2.9 Hz, 1H), 4.30 (d, J=7.7 Hz, 2H), 1.61 (s, 9H), 1.12 (s, 6H), 1.04 (s, 6H), 0.70 (t, J=7.8 Hz, 1H). ESI-MS m/z calc. 294.19434, found 295.0 (M+1)$^+$; Retention time: 2.19 min (LC Method B).

Step 2: 3-[(2,2,3,3-Tetramethylcyclopropyl)methoxy]-1H-pyrazole

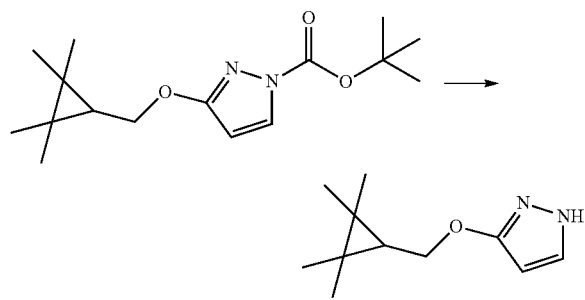

To a solution of tert-butyl 3-[(2,2,3,3-tetramethylcyclopropyl)methoxy]pyrazole-1-carboxylate (127 g, 431.4 mmol) in tetrahydrofuran (317.5 mL) and ethyl alcohol (635.0 mL) was slowly added sodium hydroxide (431.4 mL of 2 M, 862.8 mmol) and the mixture was stirred at room temperature overnight. Most of the solvent was removed under reduced pressure. The aqueous residue was diluted with water (400 mL) and extracted with methyl tert-butyl ether (762.0 mL). The organic phase was washed twice with brine (2×300 mL) and the aqueous phases were back extracted once with methyl tert-butyl ether (250 mL). The combined organic phases were dried, filtered and evaporated to give 3-[(2,2,3,3-tetramethylcyclopropyl)methoxy]-1H-pyrazole (75 g, 89%) as a viscous oil. $^1$H NMR (400 MHz, dimethyl sulfoxide-d$_6$) δ 11.78 (s, 1H), 7.48 (t, J=2.1 Hz, 1H), 5.65 (s, 1H), 4.05 (d, J=7.7 Hz, 2H), 1.08 (s, 6H), 1.00 (s, 6H), 0.67 (t, J=7.7 Hz, 1H). ESI-MS m/z calc. 194.1419, found 195.0 (M+1)$^+$; Retention time: 1.43 min (LC Method B).

Step 3: 2,6-Dichloro-N-[[6-[3-(5,5-dimethylpyrrolidin-3-yl)propylamino]-2-pyridyl]sulfonyl]pyridine-3-carboxamide

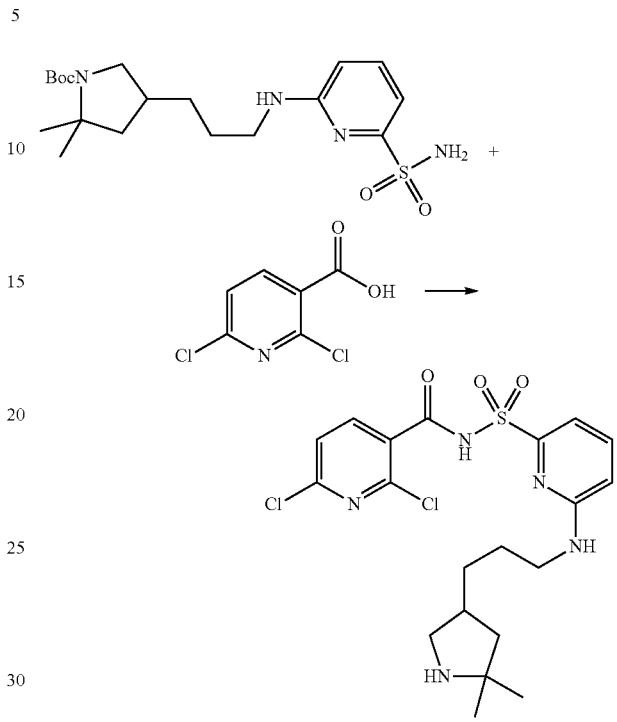

Part A: To a solution of 2,6-dichloropyridine-3-carboxylic acid (200 mg, 1.042 mmol) in tetrahydrofuran (5 mL) was added di(imidazol-1-yl)methanone (169.0 mg, 1.042 mmol) and the reaction mixture was stirred for 90 min at 50° C. tert-Butyl 2,2-dimethyl-4-[3-[(6-sulfamoyl-2-pyridyl)amino]propyl]pyrrolidine-1-carboxylate (343.9 mg, 0.8336 mmol) was added followed by 1,8-diazabicyclo[5.4.0]undec-7-ene (237.9 mg, 233.7 μL, 1.563 mmol) and the reaction was heated at 50° C. for 18 hrs. The reaction was diluted with ethyl acetate and washed with saturated aqueous ammonium chloride solution followed by brine. The organics were separated, dried over sodium sulfate, filtered and evaporated. The resultant brown residue was purified by silica gel column chromatography using a shallow gradient from 100% hexanes to 100% ethyl acetate to afford tert-butyl 4-[3-[[6-[(2,6-dichloropyridine-3-carbonyl)sulfamoyl]-2-pyridyl]amino]propyl]-2,2-dimethyl-pyrrolidine-1-carboxylate (284 mg, 46%) as off white sticky material. ESI-MS m/z calc. 585.15796, found 586.5 (M+1)$^+$; Retention time: 0.79 min (LC Method A).

Part B: The material from Part A was dissolved in dichloromethane (6 mL) and trifluoroacetic acid (1.782 g, 1.204 mL, 15.63 mmol) and stirred at room temperature for 5 hr. The solvent was removed and the residue was dissolved in ethyl acetate and the organics were washed with saturated aqueous sodium bicarbonate solution then brine. The organic layers were dried over anhydrous sodium sulfate, filtered and the solvent was removed. The material was dried under vacuum overnight to afford 2,6-dichloro-N-[[6-[3-(5,5-dimethylpyrrolidin-3-yl)propylamino]-2-pyridyl]sulfonyl]pyridine-3-carboxamide (233 mg, 100%) as an off white sticky material. $^1$H NMR (400 MHz, dimethyl sulfoxide-d$_6$) δ 9.31 (s, 1H), 9.15 (s, 1H), 8.06 (d, J=8.0 Hz, 1H), 7.73 (d, J=8.1 Hz, 1H), 7.62 (dd, J=8.5, 7.2 Hz, 1H), 7.17 (d, J=7.2

Hz, 1H), 6.79 (d, J=8.5 Hz, 1H), 3.34 (dq, J=14.6, 5.7 Hz, 1H), 3.24 (dq, J=6.6, 4.1 Hz, 2H), 2.89-2.75 (m, 1H), 2.45-2.29 (m, 1H), 1.93 (dd, J=12.8, 7.7 Hz, 1H), 1.60-1.45 (m, 3H), 1.43-1.33 (m, 5H), 1.29 (s, 3H). ESI-MS m/z calc. 485.10553, found 486.5 (M+1)$^+$; Retention time: 0.5 min (LC Method A).

Step 4: 8-Chloro-12,12-dimethyl-2$\lambda^6$-thia-3,9,11,18, 23-pentaazatetracyclo[17.3.1.1¹¹,¹⁴.0⁵,¹⁰]tetracosa-1(22),5,7,9,19(23),20-hexaene-2,2,4-trione (Hydrochloride Salt) (Compound C)

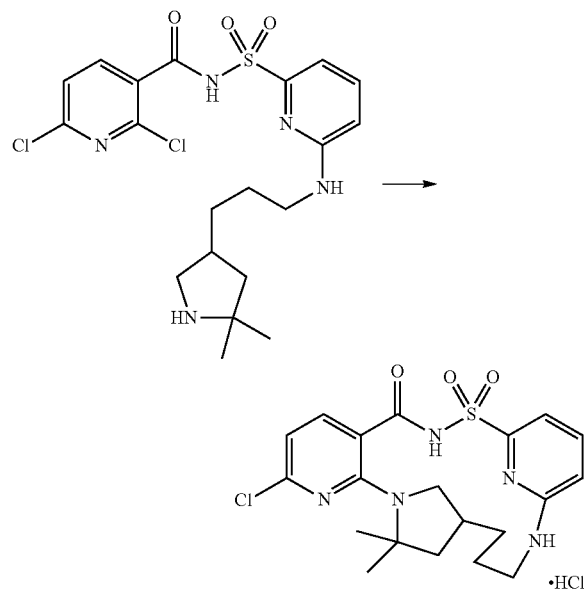

To a solution of 2,6-dichloro-N-[[6-[3-(5,5-dimethylpyrrolidin-3-yl)propylamino]-2-pyridyl]sulfonyl]pyridine-3-carboxamide (200 mg, 0.4112 mmol) in dimethyl sulfoxide (5.0 mL) and 3 Å molecular sieves was stirred at room temperature for 10 min. Cesium fluoride (194 mg, 1.277 mmol) and potassium carbonate (1703 mg, 12.32 mmol) were then added and the reaction mixture was heated at 140° C. overnight. The reaction mixture was filtered through Whatman filter disc (puradisc 25 TF) and the filtrate was purified by a reverse phase HPLC-MS method using a Luna C$_{18}$ (2) column (75×30 mm, 5 µm particle size) sold by Phenomenex (pn: 00C-4252-U0-AX) and a dual gradient run from 30-99% mobile phase B over 15.0 min. Mobile phase A=water (5 mM hydrochloric acid). Mobile phase B=acetonitrile. Flow rate=50 mL/min, injection volume=950 µL and column temperature=25° C. to afford 8-chloro-12,12-dimethyl-2$\lambda^6$-thia-3,9,11,18,23-pentaazatetracyclo[17.3.1.1¹¹,¹⁴.0⁵,¹⁰]tetracosa-1(22),5,7,9,19(23), 20-hexaene-2,2,4-trione (hydrochloride salt) (76 mg, 38%) as white solid. $^1$H NMR (400 MHz, Methanol-d$_4$) δ 7.69 (d, J=7.9 Hz, 1H), 7.54 (dd, J=8.5, 7.3 Hz, 1H), 7.16 (d, J=7.2 Hz, 1H), 6.67 (d, J=8.5 Hz, 1H), 6.56 (d, J=7.9 Hz, 1H), 4.14-3.93 (m, 1H), 3.26-3.15 (m, 1H), 3.09-2.98 (m, 1H), 2.78 (t, J=10.0 Hz, 1H), 2.19 (dd, J=15.6, 5.6 Hz, 1H), 1.92-1.77 (m, 2H), 1.72-1.60 (m, 2H), 1.61 (s, 3H), 1.51 (s, 3H), 1.49-1.34 (m, 2H). ESI-MS m/z calc. 449.12885, found 450.4 (M+1)$^+$; Retention time: 1.92 min (LC Method B).

Step 5: 12,12-Dimethyl-8-{3-[(2,2,3,3-tetramethylcyclopropyl)methoxy]-1H-pyrazol-1-yl}-2$\lambda^6$-thia-3, 9,11,18,23-pentaazatetracyclo[17.3.1.1¹¹,¹⁴.0⁵,¹⁰] tetracosa-1(22),5,7,9,19(23),20-hexaene-2,2,4-trione (Compound 42)

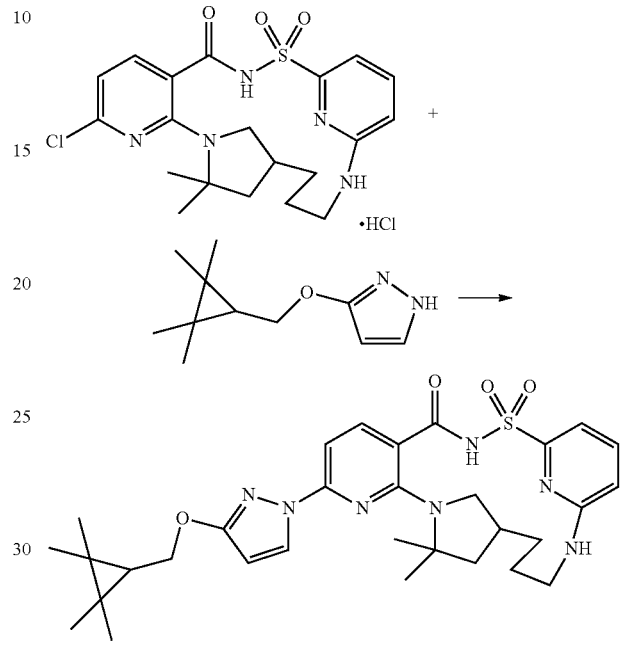

To a solution of 3-[(2,2,3,3-tetramethylcyclopropyl) methoxy]-1H-pyrazole (11.98 mg, 0.06168 mmol) in dimethyl sulfoxide (1 mL) was added scandium triflate (6.073 mg, 0.01234 mmol) and sodium hydride (10.2 mg of 50% w/w, 0.2125 mmol) at 0° C. under a nitrogen atmosphere. The reaction was stirred for 30 min. 8-Chloro-12,12-dimethyl-2$\lambda^6$-thia-3,9,11,18,23-pentaazatetracyclo[17.3.1.1¹¹, 14.05,10]tetracosa-1(22),5,7,9,19(23),20-hexaene-2,2,4-trione (hydrochloride salt) (30 mg, 0.06168 mmol) was then added and the reaction mixture was heated at 120° C. for 16 h. The reaction mixture was cooled to room temperature and quenched with a few drops of water. The resultant mixture was filtered through a Whatman filter disc (puradisc 25 TF) and the filtrate was purified by a reverse phase HPLC-MS method using a dual gradient run from 50-99% mobile phase B over 15.0 min (Mobile phase A=water (no modifier), Mobile phase B=acetonitrile) to afford 12,12-dimethyl-8-{3-[(2,2,3,3-tetramethylcyclopropyl)methoxy]-1H-pyrazol-1-yl}-2$\lambda^6$-thia-3,9,11,18,23-pentaazatetracyclo[17.3.1.111, 14.05,10]tetracosa-1(22),5,7,9,19(23),20-hexaene-2,2,4-trione (Compound 42) (2.6 mg, 7%). $^1$H NMR (400 MHz, Chloroform-d) δ 8.19 (s, 1H), 8.07 (s, 1H), 7.57 (s, 2H), 7.51 (s, 1H), 6.58 (s, 1H), 5.96 (s, 1H), 4.28 (d, J=7.8 Hz, 2H), 3.88 (brs, 1H), 3.41-3.27 (m, 2H), 3.21 (brs, 1H), 3.07 (brs, 1H), 2.61 (brs, 1H), 2.08 (brs, 1H), 1.63 (s, 6H), 1.71-1.53 (m, 3H), 1.26 (brs, 1H), 1.14 (d, J=2.5 Hz, 6H), 1.07 (s, 6H), 0.75 (t, J=7.7 Hz, 1H). ESI-MS m/z calc. 607.29407, found 608.5 (M+1)$^+$; Retention time: 2.86 min (LC Method B).

Example 11: Preparation of 8-[3-(3,3-dicyclopropylpropoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 43)

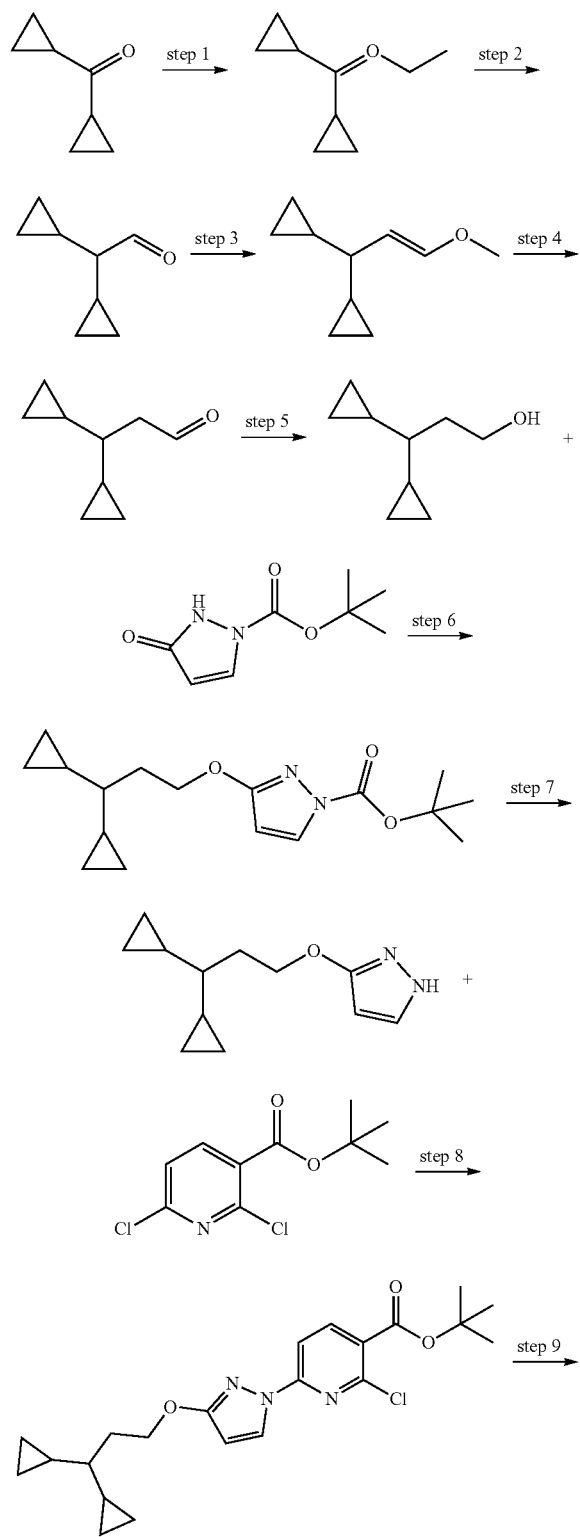

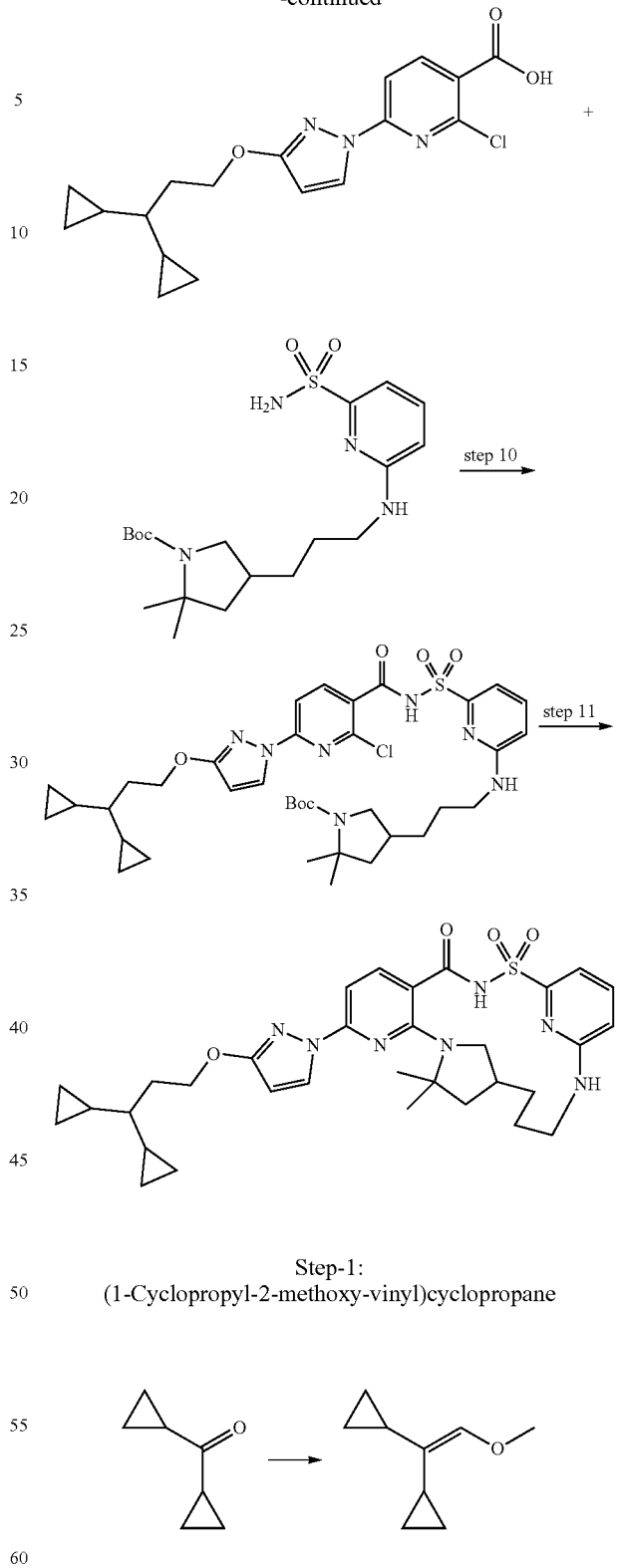

Step-1: (1-Cyclopropyl-2-methoxy-vinyl)cyclopropane

A 5000 mL round bottom flask was fitted with a mechanical stirrer, a cooling bath used as secondary containment, a J-Kem temperature probe, an addition funnel, water cooled reflux condenser and a nitrogen inlet/outlet. The vessel was charged under a nitrogen atmosphere with (methoxymethyl)triphenylphosphonium chloride (97.3 g, 284 mmol) and tetrahydrofuran (375 mL) which provided a white suspension. Stirring was commenced and the pot temperature was recorded at 19° C. The vessel was then charged with potassium tert-butoxide (31.85 g, 0.2838 mol) added as a solid in portions over 10 min which resulted in a reddish orange solution and an exotherm to 21° C. The mixture was continued to stir at room temperature for 30 min. The addition funnel was charged with dicyclopropyl ketone (dicyclopropylmethanone) (25.0 g, 227.0 mmol) which was subsequently added neat, dropwise over 25 min which resulted in a gradual exotherm to 35° C. The resulting reddish orange solution was allowed to gradually cool to room temperature and then continued to stir at room temperature for 4 h. The reaction was then quenched with cold water (375 mL) added dropwise over 25 min. The resulting biphasic mixture was transferred to a separatory funnel and allowed to stand for 5 min. The aqueous was drained and the remaining organic was washed with saturated sodium chloride solution (375 mL). The organic was removed and concentrated under reduced pressure to provide pale yellow oil which still contained some water. The mixture was diluted with ethyl acetate (500 mL) and then transferred to a separatory funnel and partitioned with water (150 mL). The organic was removed, dried over sodium sulfate (150 g) and then filtered through a glass frit Buchner funnel. The filtrate was concentrated under reduced pressure to provide a pale yellow oil with some suspended solids (triphenylphosphine oxide). The mixture was diluted with hexane (500 mL) and then filtered through a glass frit Buchner funnel with a 40 mm layer of silica gel. The filter cake was displacement washed with hexane (2×500 mL). The filtrate was concentrated under reduced pressure to provide (1-cyclopropyl-2-methoxy-vinyl)cyclopropane as a clear pale yellow oil (27 g, 0.1953 mol, 86% yield). ESI-MS m/z calc. 138.10446, found 138.0 (M+1)⁺; Retention time: 1.73 min (LC Method B).

Step-2: 2,2-Dicyclopropylacetaldehyde

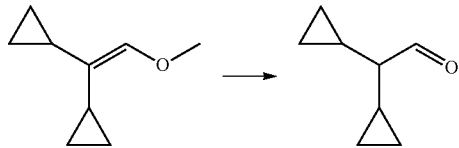

To a solution of (1-cyclopropyl-2-methoxy-vinyl)cyclopropane (128 g, 709.4 mmol) in tetrahydrofuran (700 mL) was added aqueous hydrochloric acid (250 mL of 3 M, 750.0 mmol) and the mixture was stirred at ambient temperature for 16 h then stirred at 55° C. for 4 h and then allowed to cool to ambient temperature over 12 h. The mixture was diluted with 500 mL of brine and the aqueous phase was separated. The aqueous phase was extracted with 500 mL of MTBE and the organic phases were combined. The organic phases were washed with 500 mL of brine, dried over magnesium sulfate, filtered and concentrated in vacuo. The resulting oil was diluted with 250 mL of MTBE and the residual water was removed using a separatory funnel. The organic phase was dried over magnesium sulfate, filtered and concentrated in vacuo affording 2,2-dicyclopropylacetaldehyde (99.2 g, 96%) as a light orange oil. ¹H NMR (400 MHz, Chloroform-d) δ 9.74 (d, J=2.9 Hz, 1H), 1.06 (td, J=8.9, 2.9 Hz, 1H), 0.94-0.81 (m, 2H), 0.64-0.49 (m, 4H), 0.32-0.20 (m, 4H).

Step-3: [(E)-1-Cyclopropyl-3-methoxy-allyl]cyclopropane

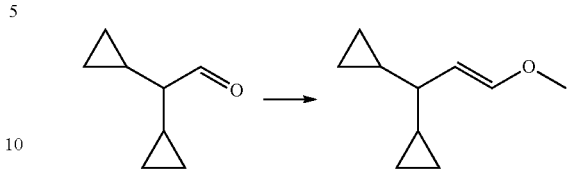

A 5000 mL round bottom flask was fitted with a mechanical stirrer, a heating mantle, a J-Kem temperature probe, an addition funnel, a water cooled reflux condenser and a nitrogen inlet/outlet. The vessel was charged under a nitrogen atmosphere with (methoxymethyl)triphenylphosphonium chloride (116.8 g, 340.7 mmol) and tetrahydrofuran (423 mL) which provided a white suspension. Stirring was commenced and the pot temperature was recorded at 19° C. The vessel was then charged with potassium tert-butoxide (38.22 g, 340.6 mmol) added as a solid in portions over 30 min (12.74 g portion added every 10 min) which resulted in a reddish orange solution and an exotherm to 40° C. The mixture was continued to stir at room temperature for 30 min. The pot temperature was recorded at 36° C. at this point. The addition funnel was then charged with 2,2-dicyclopropylacetaldehyde (47 g of 60% w/w contaminated with triphenylphosphine oxide from previous step, 227.1 mmol) which was subsequently added neat dropwise over 25 min which resulted in a gradual exotherm to 47° C. The resulting reddish orange solution was allowed to gradually cool to room temperature and then continued to stir at room temperature for 15 h. The reaction mixture (pot temp=19° C.) was then quenched with cold water (1000 mL) which resulted in an exotherm to 22° C. The mixture was continued to stir for 10 min. The resulting biphasic mixture was transferred to a separatory funnel and allowed to stand for 5 min. The organic was removed and the residual aqueous was extracted with ethyl acetate (2×300 mL). The combined organic layers were concentrated under reduced pressure to provide a dark amber oil which still contained some water. The mixture was diluted with ethyl acetate (500 mL) and then transferred to a separatory funnel and partitioned with water (150 mL). The organic was removed, washed with saturated sodium chloride solution (200 mL), dried over sodium sulfate (200 g) and then filtered through a glass frit Buchner funnel. The filtrate was concentrated under reduced pressure to provide pale amber oil with some suspended solids (triphenylphosphine oxide). The mixture was diluted with heptane (500 mL) and then allowed to stand at room temperature for 30 min. The suspension was filtered through a glass frit Buchner funnel and the filter cake was displacement washed with heptane (2×100 mL). The filtrate was concentrated under reduced pressure to a volume of about 200 mL. The pale amber solution was cooled to 0° C. in a crushed ice/water cooling bath for 30 min during which time more solids precipitated. The suspension was filtered through a glass frit Buchner funnel and the filter cake was displacement washed with heptane (2×50 mL). The filtrate was concentrated under reduced pressure to provide [(E)-1-cyclopropyl-3-methoxy-allyl]cyclopropane (30 g, 87%). ¹H NMR (400 MHz, Chloroform-d) δ 6.31 (dd, J=12.7, 1.1 Hz, 1H), 4.68 (dd, J=12.7, 7.6 Hz, 1H), 3.51 (s, 3H), 0.77 (qt, J=8.1, 5.0 Hz, 2H), 0.54-0.32 (m, 2H), 0.28-0.12 (m, 5H), 0.08 (ddd, J=9.3, 5.3, 4.1 Hz, 2H).

Step-4: 3,3-Dicyclopropylpropanal

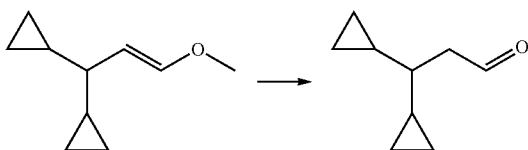

To a solution of [(E)-1-cyclopropyl-3-methoxy-allyl]cyclopropane (141 g, 555.7 mmol) in tetrahydrofuran (500 mL) was added aqueous hydrochloric acid (100 mL of 3 M, 300.0 mmol) and the mixture warmed to 50° C. for 2 h. The mixture was cooled to ambient temperature and the tetrahydrofuran removed in vacuo. The residue was diluted with dichloromethane (700 mL) and the aqueous phase separated (slight emulsion). The organic phase was washed with 500 mL of brine, dried over magnesium sulfate and filtered. To the filtrate was added $MgCl_2$ (50 g, 525.1 mmol) and the mixture was stirred at ambient temperature for 12 h. The slurry was filtered over Celite (blinded the Celite and needed to be scraped off). The filtrate was slightly cloudy and was washed with brine, dried over magnesium sulfate, filtered and concentrated to afford 3,3-dicyclopropylpropanal (76.8 g, 100%), $^1$H NMR (400 MHz, Chloroform-d) δ 9.83 (t, J=2.7 Hz, 1H), 2.71-2.39 (m, 2H), 0.73 (ddt, J=5.5, 4.2, 2.9 Hz, 3H), 0.56-0.47 (m, 2H), 0.42 (dddd, J=9.2, 7.6, 4.0, 2.6 Hz, 2H), 0.28-0.21 (m, 2H), 0.11-0.04 (m, 2H).

Step-5: 3,3-Dicyclopropylpropan-1-ol

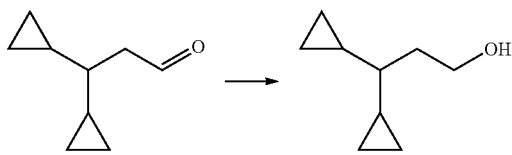 [SMILES: O=CCC(C1CC1)C1CC1 ; OCCC(C1CC1)C1CC1]

To a slurry of lithium aluminum hydride (10.4 g, 266.9 mmol) in tetrahydrofuran (500 mL) was added dropwise a solution of 3,3-dicyclopropylpropanal (76 g, 549.9 mmol) in tetrahydrofuran (150 mL) allowing for a gentle reflux. The mixture was stirred at ambient temperature for 2 h. The reaction was chilled with an ice bath and quenched with the slow addition of water (10.4 mL, 577.3 mmol) followed by aqueous sodium hydroxide (10.4 mL of 4 M, 41.60 mmol), then water (31.2 mL, 1.732 mol). The slurry was filtered over celite, washed with tetrahydrofuran and concentrated in vacuo to afford 3,3-dicyclopropylpropan-1-ol (112 g, 73%), $^1$H NMR (400 MHz, Chloroform-d) δ 3.81 (t, J=6.9 Hz, 2H), 1.76 (q, J=6.9 Hz, 2H), 0.63 (dtt, J=8.8, 8.0, 5.1 Hz, 2H), 0.50-0.34 (m, 4H), 0.27-0.14 (m, 3H), 0.14-0.02 (m, 2H).

Step-6: tert-Butyl 3-(3,3-dicyclopropylpropoxy)pyrazole-1-carboxylate

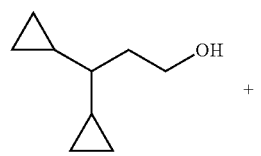
+
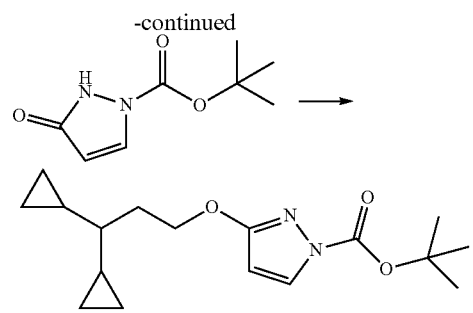

To tert-butyl 3-hydroxypyrazole-1-carboxylate (36.5 g, 198.2 mmol) in tetrahydrofuran (450 mL) under nitrogen was added 3,3-dicyclopropylpropan-1-ol (28.0 g, 199.7 mmol) and triphenylphosphine (57.0 g, 217.3 mmol). To the mixture was added DIAD (43.0 mL, 218.4 mmol) dropwise allowing the mixture to gradually exotherm to 45° C. After the addition, the mixture was stirred at ambient temperature for 1 h. The reaction mixture was diluted with hexanes (450 mL) and removed approximately 50% of the solvent in vacuo affording a slurry. The slurry was filtered using a medium frit and the solid was washed with hexanes (3×50 mL). The filtrate was concentrated in vacuo affording an amber oil. The crude oil was diluted with dichloromethane and chromatographed on a 750 g silica gel column eluting with a gradient from 0%-40% ethyl acetate in hexanes. Collected two main fractions, the second fraction was pure product. The first fraction contained triphenylphosphine and was rechromatographed on a 750 g silica gel column eluting with a gradient from 0%-25% ethyl acetate in hexanes. Combined product from the second column with product obtained from the first column affording as a clear oil, tert-butyl 3-(3,3-dicyclopropylpropoxy)pyrazole-1-carboxylate (39.0 g, 64%). ESI-MS m/z calc. 306.19434, found 307.1 (M+1)$^+$; Retention time: 2.26 min (LC Method B).

Step-7: 3-(3,3-Dicyclopropylpropoxy)-1H-pyrazole (Trifluoroacetate Salt)

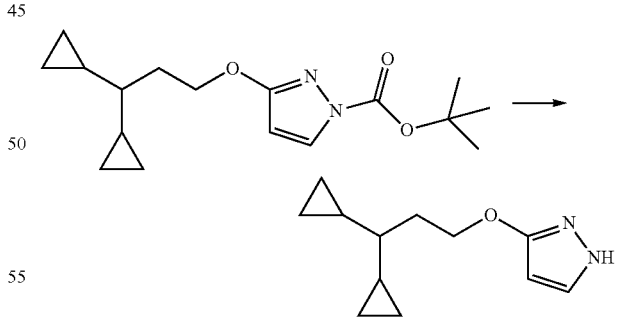

A solution of tert-butyl 3-(3,3-dicyclopropylpropoxy) pyrazole-1-carboxylate (255 mg, 0.8322 mmol) and trifluoroacetic acid (325.0 μL, 4.218 mmol) in dichloromethane (1 mL) was stirred for 2.5 h. The volatiles were removed under vacuum, affording 3-(3,3-dicyclopropylpropoxy)-1H-pyrazole (trifluoroacetate salt) (266 mg, 100%) as a colorless oil which was used directly in the next reaction. ESI-MS m/z calc. 206.1419, found 207.2 (M+1)$^+$; Retention time: 0.59 minutes (LC Method A).

241

Step 8: tert-Butyl 2-chloro-6-[3-(3,3-dicyclopropyl-propoxy) pyrazol-1-yl]pyridine-3-carboxylate

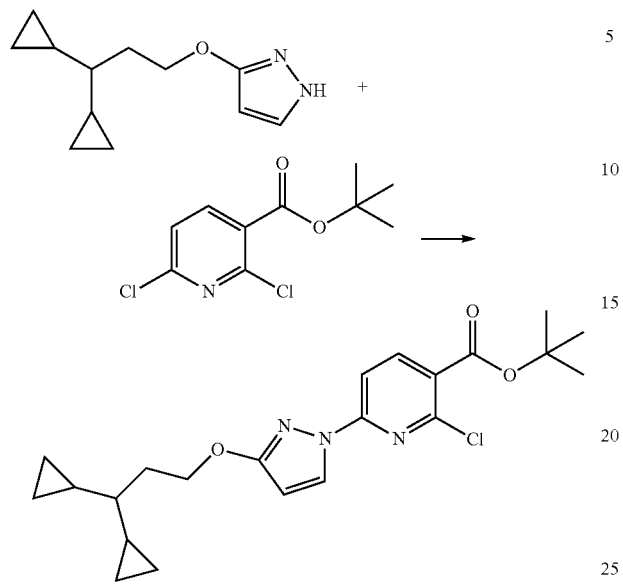

A mixture of tert-butyl 2,6-dichloropyridine-3-carboxylate (220.0 mg, 0.8867 mmol), 3-(3,3-dicyclopropyl-propoxy)-1H-pyrazole (trifluoroacetate salt) (266.0 mg, 0.8305 mmol), potassium carbonate (230 mg, 1.664 mmol) and 1,4-diazabicyclo[2.2.2]octane (20 mg, 0.1783 mmol) in dimethyl sulfoxide (10 mL) was stirred at room temperature for 15 h. The reaction was diluted with water and extracted with ethyl acetate. The combined organic extracts were washed with brine, dried over sodium sulfate, filtered and evaporated. The residue was purified by silica gel column chromatography using a gradient from 100% hexanes to 20% ethyl acetate in hexanes to afford tert-butyl 2-chloro-6-[3-(3,3-dicyclopropylpropoxy)pyrazol-1-yl]pyridine-3-carboxylate (245 mg, 71%) as a colorless oil. ESI-MS m/z calc. 417.18192, found 418.4 (M+1)+; Retention time: 1.28 min (LC Method J).

Step 9: 2-Chloro-6-[3-(3,3-dicyclopropylpropoxy) pyrazol-1-yl]pyridine-3-carboxylic Acid

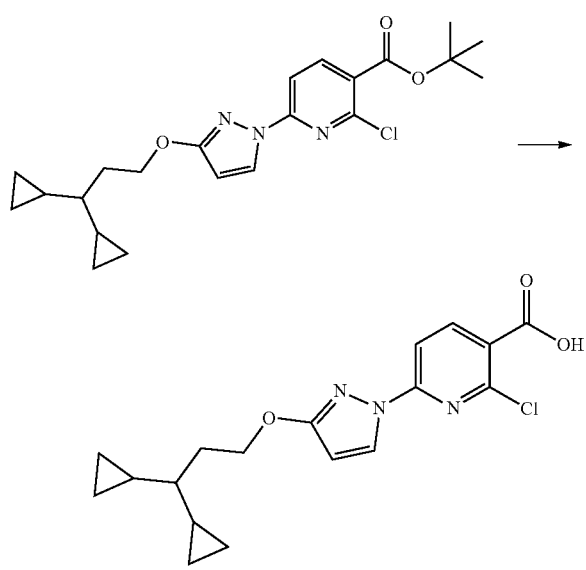

242

A solution of tert-butyl 2-chloro-6-[3-(3,3-dicyclopropy-lpropoxy) pyrazol-1-yl]pyridine-3-carboxylate (245.0 mg, 0.5862 mmol) in trifluoroacetic acid (500.0 μL, 6.490 mmol) and dichloromethane (1.5 mL) was stirred for 4 h at room temperature. The solvent was evaporated, and twice the residue was taken up in tetrahydrofuran and concentrated under vacuum to afford 2-chloro-6-[3-(3,3-dicyclopropyl-propoxy)pyrazol-1-yl]pyridine-3-carboxylic acid (204 mg, 96%) as a white solid which was used directly in the next reaction. $^1$H NMR (400 MHz, Methanol-$d_4$) δ 8.47-8.32 (m, 2H), 7.73 (d, J=8.5 Hz, 1H), 6.03 (d, J=2.9 Hz, 1H), 4.45 (t, J=6.7 Hz, 2H), 1.98 (q, J=7.0 Hz, 2H), 0.75-0.64 (m, 2H), 0.50-0.39 (m, 4H), 0.35-0.26 (m, 1H), 0.26-0.19 (m, 2H), 0.15-0.06 (m, 2H). ESI-MS m/z calc. 361.11932, found 362.3 (M+1)+; Retention time: 0.8 min (LC Method A).

Step-10: tert-Butyl 4-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate

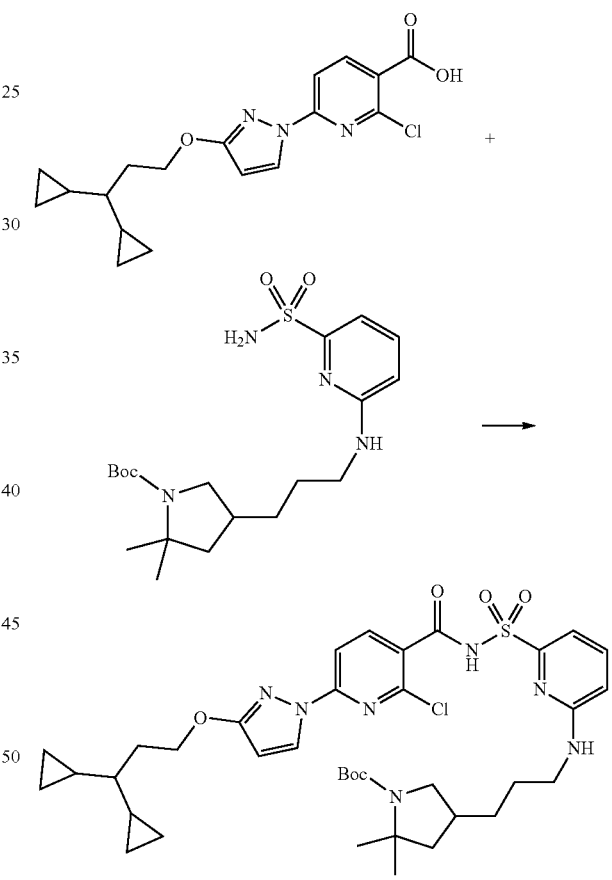

To a solution of 2-chloro-6-[3-(3,3-dicyclopropyl-propoxy)pyrazol-1-yl]pyridine-3-carboxylic acid (505.1 mg, 1.382 mmol) in tetrahydrofuran (5 mL) was added carbonyl diimidazole (224.1 mg, 1.382 mmol) and the mixture was stirred for 120 min at 50° C. Then, tert-butyl 2,2-dimethyl-4-[3-[(6-sulfamoyl-2-pyridyl)amino]propyl] pyrrolidine-1-carboxylate (380 mg, 0.9211 mmol) in tetrahydrofuran (5 mL) was added followed by 1,8-diazabicyclo [5.4.0]undec-7-ene (280.4 mg, 275.4 μL, 1.842 mmol) and the reaction was heated at 50° C. for 16 h. The reaction was diluted with ethyl acetate and washed with a small amount of 1:1 saturated aqueous ammonium chloride/brine. The organics were separated, dried over sodium sulfate, filtered and evaporated. The resultant brown residue was purified by silica gel chromatography using a shallow gradient from 100% dichloromethane to 20% methanol in dichloromethane to afford tert-butyl 4-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate (356 mg, 51%) as a white solid. $^1$H NMR (400 MHz, Chloroform-d) δ 8.31 (d, J=2.9 Hz, 1H), 8.02 (d, J=8.4 Hz, 1H), 7.69 (d, J=8.4 Hz, 1H), 7.58-7.50 (m, 2H), 6.55 (dd, J=7.7, 1.6 Hz, 1H), 5.95 (d, J=2.9 Hz, 1H), 4.92 (s, 1H), 4.42 (t, J=6.9 Hz, 2H), 4.02 (dd, J=10.7, 7.3 Hz, 1H), 3.64-3.54 (m, 1H), 3.17 (t, J=11.7 Hz, 1H), 2.88 (t, J=10.7 Hz, 1H), 2.19 (d, J=9.5 Hz, 1H), 1.97 (q, J=6.8 Hz, 2H), 1.82 (dt, J=15.1, 7.6 Hz, 2H), 1.55 (tdd, J=16.3, 10.8, 5.0 Hz, 1H), 1.40 (s, 11H), 1.30 (s, 3H), 1.25 (s, 3H), 0.76-0.60 (m, 2H), 0.55-0.40 (m, 4H), 0.33 (ddd, J=15.9, 9.0, 6.9 Hz, 1H), 0.20 (dtd, J=9.5, 4.9, 3.6 Hz, 2H), 0.14-0.04 (m, 2H). ESI-MS m/z calc. 755.3232, found 756.5 (M+1)$^+$; Retention time: 0.6 min (LC Method L).

Step-11: 8-[3-(3,3-Dicyclopropylpropoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 43)

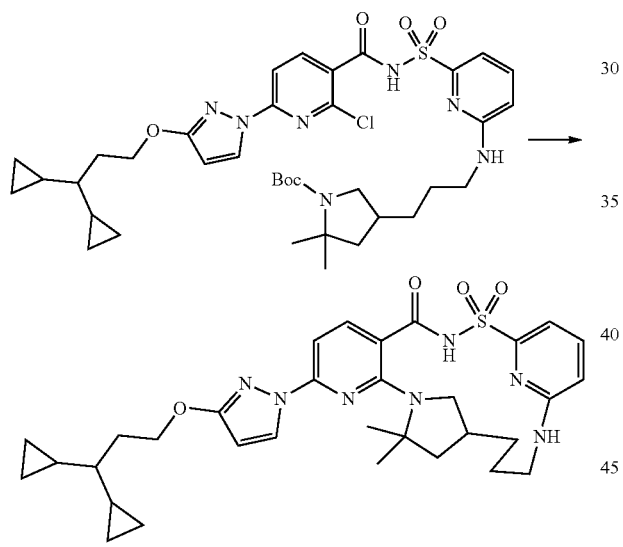

A solution of tert-butyl 4-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate (350 mg, 0.4627 mmol) in dichloromethane (2.917 mL) and trifluoroacetic acid (527.6 mg, 354.1 μL, 4.627 mmol) was stirred at room temperature for 4 h. The solvents were removed in vacuo and the residue was dissolved in ethyl acetate. Washed with 2 mL of saturated aqueous sodium bicarbonate solution and the organic layers were collected and the solvent was removed under vacuum. The material was dissolved in dimethyl sulfoxide (17.50 mL) and 3 Å molecular sieves, cesium fluoride (210.8 mg, 1.388 mmol) and potassium carbonate (191.8 mg, 1.388 mmol) were added and the reaction mixture was heated at 130° C. overnight. The reaction mixture was filtered through Whatman filter disc (puradisc 25 TF) and the filtrate was purified by reverse phase HPLC-MS using a dual gradient run from 20%-80% mobile phase B over 15.0 min (mobile phase A=water (0.05% hydrochloric acid), mobile phase B=acetonitrile) to afford 8-[3-(3,3-dicyclopropylpropoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 43) (158 mg, 55%) as an off-white solid. $^1$H NMR (400 MHz, Chloroform-d) δ 9.99 (s, 1H), 8.19 (d, J=2.8 Hz, 1H), 8.05 (d, J=8.4 Hz, 1H), 7.57 (t, J=7.8 Hz, 1H), 7.50 (d, J=7.2 Hz, 1H), 7.31-7.19 (m, 1H), 6.60 (d, J=8.3 Hz, 1H), 5.91 (d, J=2.8 Hz, 1H), 4.43 (t, J=6.8 Hz, 2H), 3.91 (s, 1H), 3.35 (t, J=8.7 Hz, 1H), 3.18 (d, J=13.9 Hz, 1H), 3.03 (t, J=9.9 Hz, 1H), 2.60 (d, J=18.4 Hz, 1H), 2.07 (dd, J=12.2, 7.8 Hz, 1H), 1.97 (q, J=6.8 Hz, 2H), 1.62 (d, J=6.2 Hz, 11H), 0.73-0.61 (m, 2H), 0.51-0.38 (m, 4H), 0.38-0.29 (m, 1H), 0.24-0.16 (m, 2H), 0.15-0.06 (m, 2H). ESI-MS m/z calc. 619.29407, found 620.4 (M+1)$^+$; Retention time: 1.32 min (LC Method J)

Example 12: Preparation of 12,12-dimethyl-8-(3-{2-[1-(trifluoromethyl)cyclopropyl]ethoxy}-1H-pyrazol-1-yl)-18-oxa-2λ$^6$-thia-3,9,11,23-tetraazatetracyclo[17.3.1.111,14.05,10]tetracosa-1(22),5,7,9,19(23),20-hexaene-2,2,4-trione (Enantiomer 1) (Compound 48) and 12,12-dimethyl-8-(3-{2-[1-(trifluoromethyl)cyclopropyl]ethoxy}-1H-pyrazol-1-yl)-18-oxa-2λ$^6$-thia-3,9,11,23-tetraazatetracyclo[17.3.1.111,14.05,10]tetracosa-1(22),5,7,9,19(23),20-hexaene-2,2,4-trione (Enantiomer 2) (Compound 49)

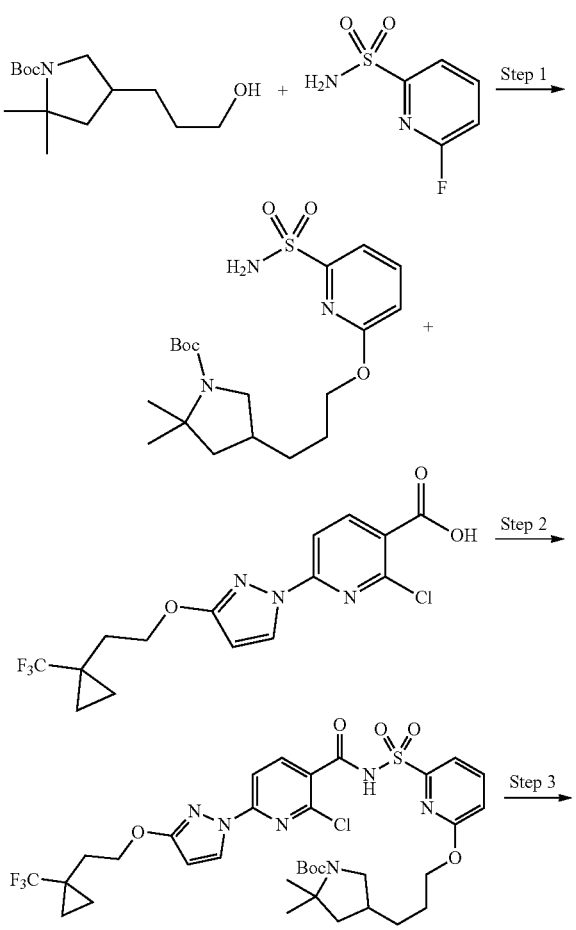

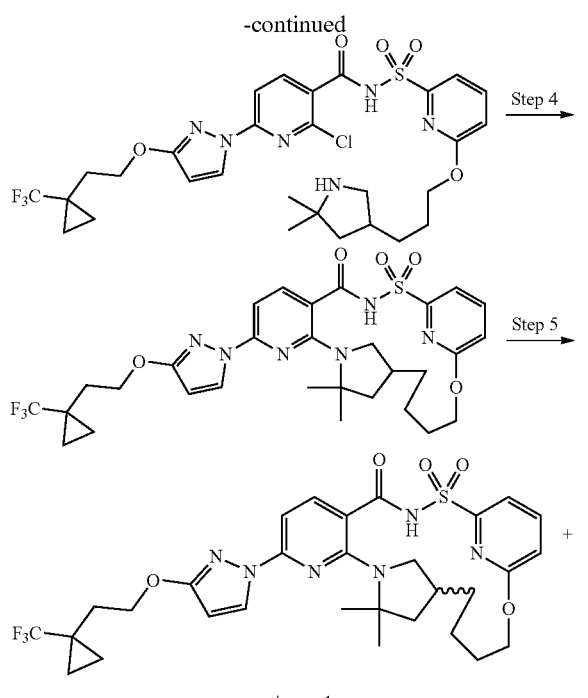

enantiomer 1 enantiomer 2

Step 1: tert-Butyl 2,2-dimethyl-4-[3-[(6-sulfamoyl-2-pyridyl)oxy]propyl]pyrrolidine-1-carboxylate

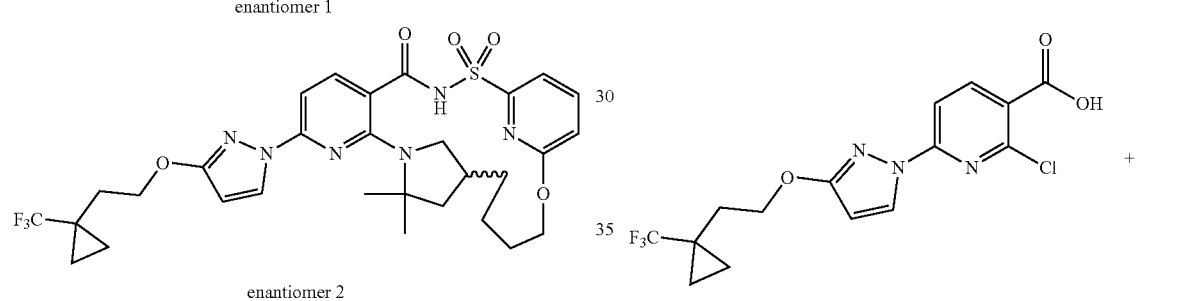

To the tert-butyl 4-(3-hydroxypropyl)-2,2-dimethyl-pyrrolidine-1-carboxylate (257 mg, 0.9986 mmol) stirring under nitrogen atmosphere in N,N-dimethylformamide (2.056 mL) was portionwise added sodium hydride (79.87 mg, 1.997 mmol) (Caution: gas evolution) and the mixture was stirred at room temperature for 20 min. 6-Fluoropyridine-2-sulfonamide (175.9 mg, 0.9986 mmol) was then added and the resulting mixture was stirred at room temperature for 2 h and 20 min then sodium hydride (23.96 mg, 0.9984 mmol) was added (Caution: gas evolution) and the resulting mixture was stirred 20 min then poured into 1N citric acid and extracted with ethyl acetate (2×). Combined organic fractions, dried (sodium sulfate), filtered and concentrated to a clear oil which was purified by silica gel chromatography using a shallow gradient from 100% hexanes to 100% ethyl acetate giving tert-butyl 2,2-dimethyl-4-[3-[(6-sulfamoyl-2-pyridyl)oxy]propyl]pyrrolidine-1-carboxylate (275.2 mg, 67%). ESI-MS m/z calc. 413.19846, found 414.2 (M+1)⁺; Retention time: 0.69 min (LC Method A).

Step 2: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate

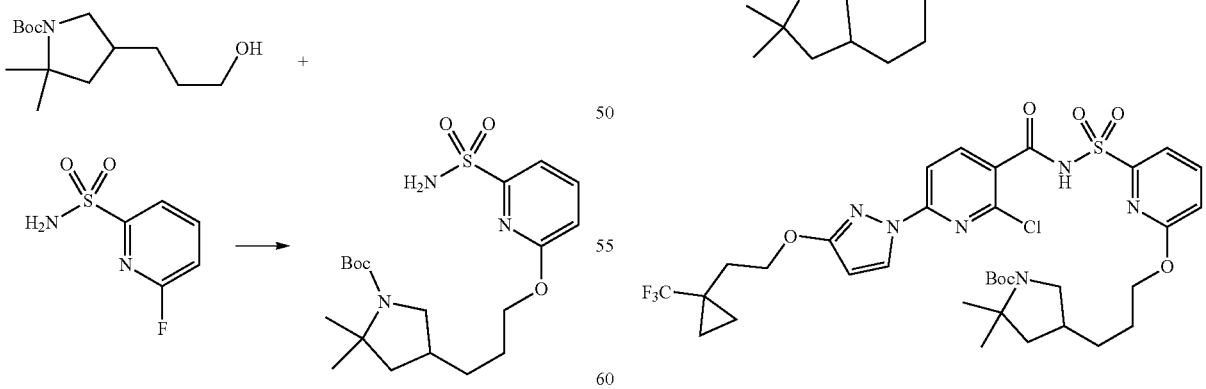

In a 20 mL vial, 2-chloro-6-[3-[2-[1-(trifluoromethyl)cyclopropyl]ethoxy]pyrazol-1-yl]pyridine-3-carboxylic acid (96.86 mg, 0.2578 mmol) and carbonyl diimidazole (45.81 mg, 0.2825 mmol) were combined in tetrahydrofuran (1.53 mL) and stirred for 120 min at 50° C. with a loose cap. Then tert-butyl 2,2-dimethyl-4-[3-[(6-sulfamoyl-2-pyridyl)

oxy]propyl]pyrrolidine-1-carboxylate (193.8 mg, 0.2578 mmol) in tetrahydrofuran (2.04 mL) was added followed by 1,8-diazabicyclo[5.4.0]undec-7-ene (80.81 mg, 79.38 µL, 0.5308 mmol) and the reaction was heated at 50° C. for 16 hrs. The reaction was diluted with ethyl acetate and washed with a 1M citric acid solution, followed by brine. The organics were separated, dried over sodium sulfate, filtered and evaporated then purified by silica gel chromatography using a shallow gradient from 100% dichloromethane to 20% methanol/dichloromethane. Product co-eluted with some impurities. Fractions containing product were combined and re-purified by silica gel chromatography using a shallow gradient from 100% hexanes to 100% ethyl acetate giving tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate (64.7 mg, 33%). ESI-MS m/z calc. 770.2476, found 771.2 (M+1)+; Retention time: 0.94 min (LC Method A).

Step 3: 2-Chloro-N-[[6-[3-(5,5-dimethylpyrrolidin-3-yl)propoxy]-2-pyridyl]sulfonyl]-6-[3-[2-[1-(trifluoromethyl)cyclopropyl]ethoxy]pyrazol-1-yl]pyridine-3-carboxamide

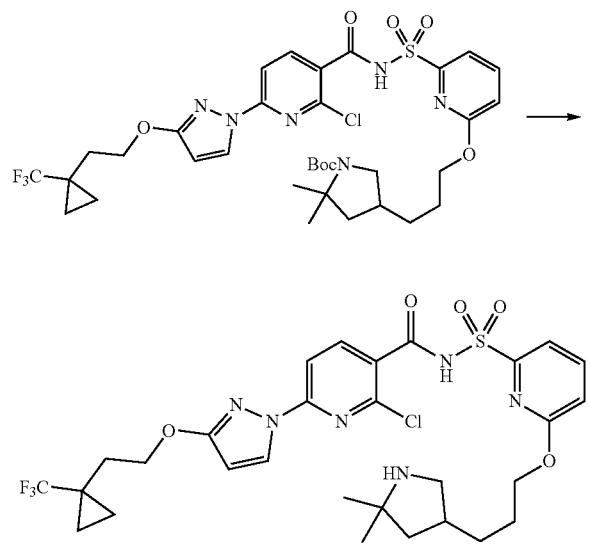

tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate (132.5 mg, 0.1718 mmol) was dissolved in dichloromethane (578.2 µL) and to the mixture was added trifluoroacetic acid (898.7 mg, 607.2 µL, 7.882 mmol) and the mixture was stirred at room temperature for 60 min. Concentrated the mixture to dryness under reduced pressure, took up in saturated aqueous sodium bicarbonate and ethyl acetate and separated the layers. Washed the organic layer with a small amount of brine then dried (sodium sulfate), filtered and concentrated to a white solid, 2-chloro-N-[[6-[3-(5,5-dimethylpyrrolidin-3-yl)propoxy]-2-pyridyl]sulfonyl]-6-[3-[2-[1-(trifluoromethyl)cyclopropyl]ethoxy]pyrazol-1-yl]pyridine-3-carboxamide (110 mg, 95%). ESI-MS m/z calc. 670.1952, found 671.2 (M+1)+; Retention time: 0.64 min (LC Method A).

Step 4: 12,12-Dimethyl-8-(3-{2-[1-(trifluoromethyl)cyclopropyl]ethoxy}-1H-pyrazol-1-yl)-18-oxa-2λ6-thia-3,9,11,23-tetraazatetracyclo[17.3.1.1¹¹,¹⁴.0⁵,¹⁰]tetracosa-1(22),5,7,9,19(23),20-hexaene-2,2,4-trione (Compound 40)

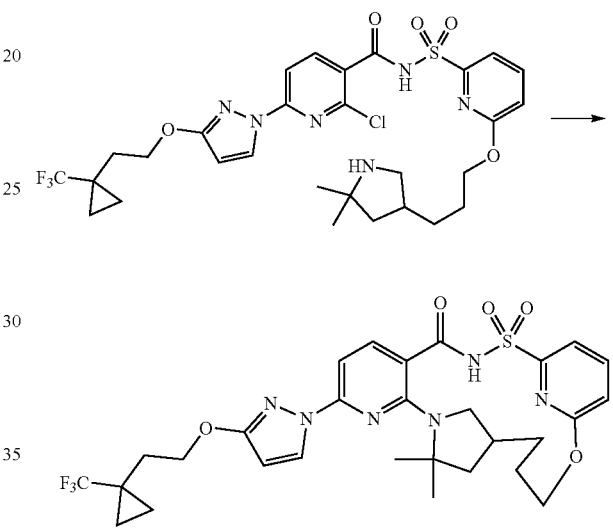

To a solution of 2-chloro-N-[[6-[3-(5,5-dimethylpyrrolidin-3-yl)propoxy]-2-pyridyl]sulfonyl]-6-[3-[2-[1-(trifluoromethyl)cyclopropyl]ethoxy]pyrazol-1-yl]pyridine-3-carboxamide (126.6 mg, 0.1886 mmol) in dimethyl sulfoxide (5.063 mL) was added potassium carbonate (130.3 mg, 0.9430 mmol), cesium fluoride (34.38 mg, 0.2263 mmol) and a small amount of 3 Å molecular sieves. The resulting mixture was capped and heated to 150° C. for 6.5 h then cooled to room temperature and stirred overnight. The mixture was then heated to 165° C. for 90 min then cooled to room temperature, diluted with ethyl acetate and washed with 1:1 saturated aqueous NH4Cl/1M citric acid then brine. The organic phase was dried (sodium sulfate), filtered and concentrated to an orange oil which was purified by silica gel chromatography using a shallow gradient from 100% hexanes to 100% ethyl acetate (product elutes after reaching 100% ethyl acetate) to give 12,12-dimethyl-8-(3-{2-[1-(trifluoromethyl)cyclopropyl]ethoxy}-1H-pyrazol-1-yl)-18-oxa-2λ6-thia-3,9,11,23-tetraazatetracyclo[17.3.1.1¹¹,¹⁴.0⁵,¹⁰]tetracosa-1(22),5,7,9,19(23),20-hexaene-2,2,4-trione (Compound 40) (58.2 mg, 48%) as a white solid. ESI-MS m/z calc. 634.2185, found 635.2 (M+1)+; Retention time: 2.29 min (LC Method B).

Step 5: 12,12-Dimethyl-8-(3-{2-[1-(trifluoromethyl) cyclopropyl]ethoxy}-1H-pyrazol-1-yl)-18-oxa-2λ⁶-thia-3,9,11,23-tetraazatetracyclo[17.3.1.1¹¹,¹⁴.0⁵,¹⁰]tetracosa-1(22),5,7,9,19(23),20-hexaene-2,2,4-trione (Enantiomer 1) (Compound 48) and 12,12-dimethyl-8-(3-{2-[1-(trifluoromethyl)cyclopropyl]ethoxy}-1H-pyrazol-1-yl)-18-oxa-2λ⁶-thia-3,9,11,23-tetraazatetracyclo[17.3.1.1¹¹,¹⁴.0⁵,¹⁰]tetracosa-1(22),5,7,9,19(23),20-hexaene-2,2,4-trione (Enantiomer 2) (Compound 49)

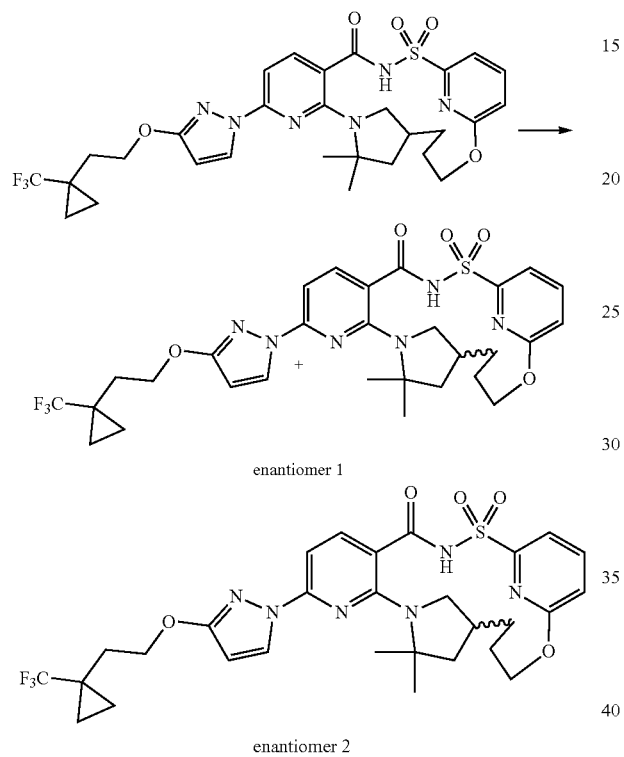

Subjected racemic 12,12-dimethyl-8-(3-{2-[1-(trifluoromethyl)cyclopropyl]ethoxy}-1H-pyrazol-1-yl)-18-oxa-2λ⁶-thia-3,9,11,23-tetraazatetracyclo[17.3.1.1¹¹,¹⁴.0⁵,¹⁰]tetracosa-1(22),5,7,9,19(23),20-hexaene-2,2,4-trione (Compound 40) (45.3 mg, 0.07052 mmol) to chiral separation by SFC chromatography using a ChiralPak AS-H (250× 10 mm column, 5 μm particle size) with 25% acetonitrile/methanol (90:10)/75% carbon dioxide mobile phase at 10 mL/min over 8.0 min (injection volume=70 μL of 24 mg/mL solution in acetonitrile/methanol (90:10)) giving as the first enantiomer to elute. 12,12-dimethyl-8-(3-{2-[1-(trifluoromethyl)cyclopropyl]ethoxy}-1H-pyrazol-1-yl)-18-oxa-2λ⁶-thia-3,9,11,23-tetraazatetracyclo[17.3.1.1¹¹,¹⁴.0⁵,¹⁰]tetracosa-1(22),5,7,9,19(23),20-hexaene-2,2,4-trione (enantiomer 1) (Compound 48) (22.20 mg, 97%) as a white solid; ESI-MS m/z calc. 634.2185, found 635.0 (M+1)⁺; Retention time: 2.30 min (LC Method B) and as the second enantiomer to elute 12,12-dimethyl-8-(3-{2-[1-(trifluoromethyl)cyclopropyl]ethoxy}-1H-pyrazol-1-yl)-18-oxa-2λ⁶-thia-3,9,11,23-tetraazatetracyclo[17.3.1.1¹¹,¹⁴.0⁵,¹⁰]tetracosa-1(22),5,7,9,19(23),20-hexaene-2,2,4-trione (enantiomer 2) (Compound 49) (22.33 mg, 100%) as a white solid; ¹H NMR (400 MHz, dimethyl sulfoxide-d₆) δ 12.81 (s, 1H), 8.21 (d, J=2.8 Hz, 1H), 8.01 (t, J=7.9 Hz, 1H), 7.86 (d, J=8.2 Hz, 1H), 7.63 (d, J=7.4 Hz, 1H), 7.13 (d, J=8.4 Hz, 1H), 6.93 (d, J=8.2 Hz, 1H), 6.12 (d, J=2.8 Hz, 1H), 5.17 (t, J=12.1 Hz, 1H), 4.32 (t, J=7.0 Hz, 2H), 4.11 (d, J=6.5 Hz, 1H), 3.93 (d, J=11.1 Hz, 1H), 3.19-3.15 (m, 4H), 2.18 (s, 1H), 2.08 (t, J=7.0 Hz, 2H), 1.86 (dd, J=11.9, 5.3 Hz, 1H), 1.68 (t, J=13.6 Hz, 2H), 1.60 (s, 3H), 1.51 (s, 3H), 1.00-0.93 (m, 2H), 0.92-0.85 (m, 2H), ESI-MS m/z calc. 634.2185, found 635.1 (M+1)⁺; Retention time: 2.29 min (LC Method B).

Example 13: Preparation of 12,12-dimethyl-8-(3-{2-[1-(trifluoromethyl) cyclopropyl]ethoxy}-1H-pyrazol-1-yl)-2λ⁶-thia-3,9,11-triazatetracyclo[17.3.1.1¹¹,¹⁴.0⁵,¹⁰]tetracosa-1(22),5,7,9,19(23),20-hexaene-2,2,4-trione (Compound 53)

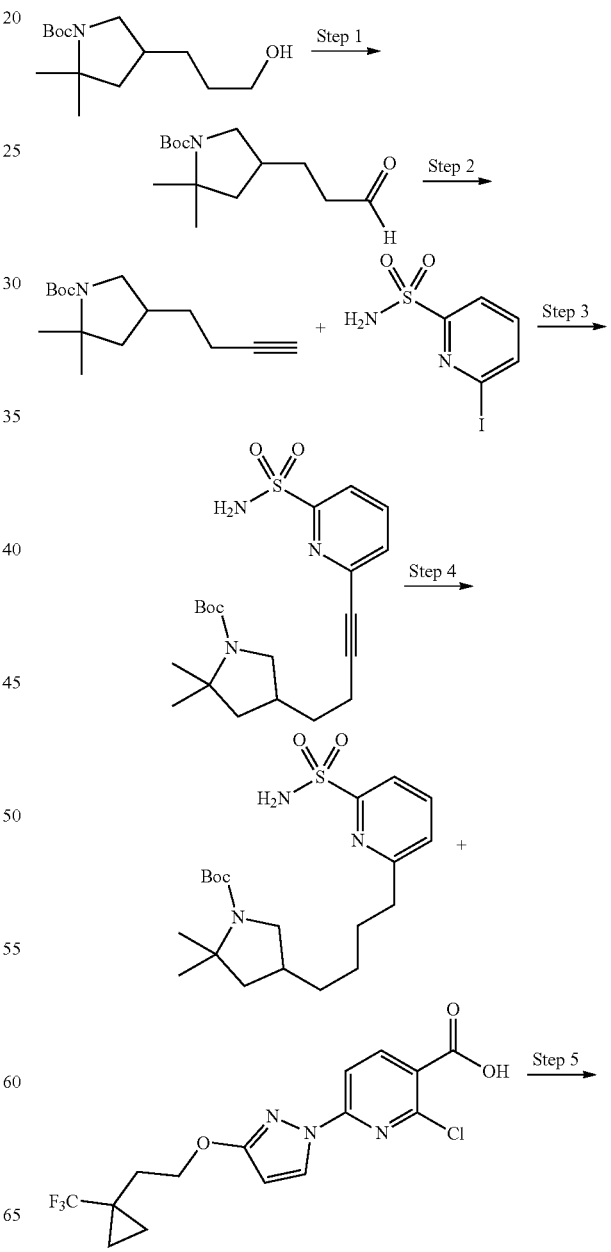

251

-continued

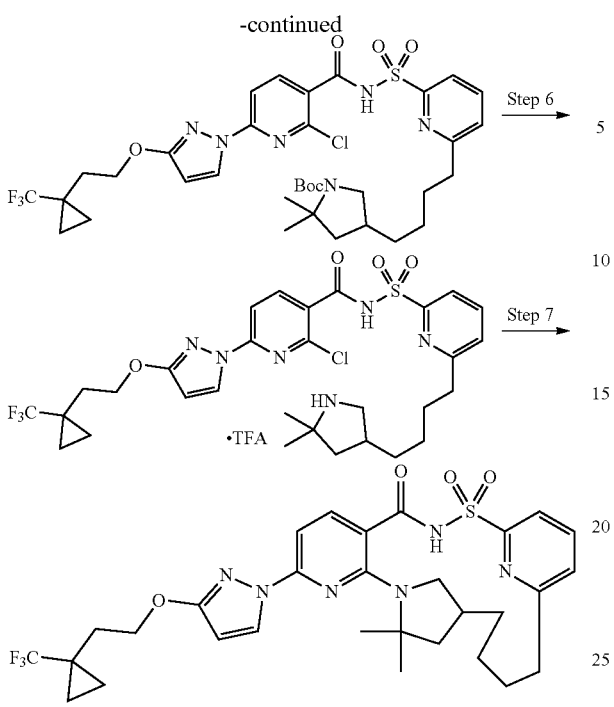

Step 1: tert-Butyl 2,2-dimethyl-4-(3-oxopropyl)pyrrolidine-1-carboxylate

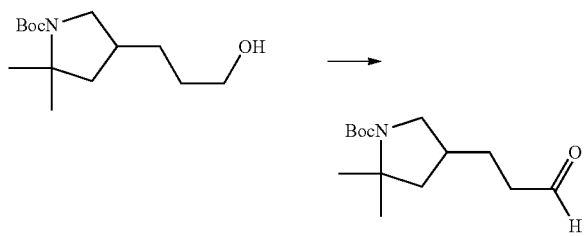

Dess-Martin Periodinane (9.95 g, 23.46 mmol) was added to a stirred solution of tert-butyl 4-(3-hydroxypropyl)-2,2-dimethyl-pyrrolidine-1-carboxylate (5.20 g, 20.20 mmol) in anhydrous CH$_2$Cl$_2$ (40 mL) at 0° C. (ice-water bath) under nitrogen. After 15 min, the reaction was allowed to warm to ambient temperature and stirring continued for another 2 h. The reaction was diluted with ether (200 mL) and saturated aqueous sodium bicarbonate (100 mL) was added slowly (to mitigate carbon dioxide gas evolution). Then 10% sodium thiosulfate (50 mL) was added and stirred at ambient temperature for 30 min. The layers were separated and the aqueous layer was extracted with ether (2×100 mL). The combined organics were washed with brine (100 mL), dried over anhydrous sodium sulfate, filtered and concentrated under reduced pressure to obtain crude material. The crude was purified from medium pressure silica gel chromatography (330 g silica gel column, 5-35% Ethyl acetate in hexanes over 35 min) to furnish desired tert-butyl 2,2-dimethyl-4-(3-oxopropyl)pyrrolidine-1-carboxylate (3.96 g, 77%) as clear viscous material, tert-butyl 2,2-dimethyl-4-(3-oxopropyl)pyrrolidine-1-carboxylate (3.96 g, 77%). $^1$H NMR (400 MHz, Methanol-d$_4$) δ 4.48 (t, J=5.4 Hz, 1H), 3.66 (dd, J=11.2, 6.9 Hz, 1H), 2.87 (q, J=10.7 Hz, 1H), 2.31 (t, J=7.6 Hz, 1H), 2.22-2.07 (m, 1H), 1.95 (ddt, J=17.2, 12.1, 6.1 Hz, 1H), 1.66 (q, J=7.9 Hz, 1H), 1.62-1.55 (m, 1H), 1.54-1.48 (m, 2H), 1.47 (s, 4H), 1.43 (s, 6H), 1.41 (s, 2H), 1.31 (s, 3H). ESI-MS m/z calc. 255.18344, found 256.2 (M+1)$^+$; Retention time: 1.57 min (LC Method B).

252

Step 2: tert-Butyl 4-but-3-ynyl-2,2-dimethyl-pyrrolidine-1-carboxylate

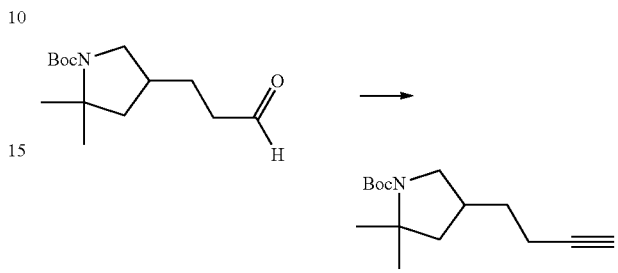

To a solution of tert-butyl 2,2-dimethyl-4-(3-oxopropyl)pyrrolidine-1-carboxylate (1.33 g, 5.208 mmol) in Methanol (31 mL) at 0° C. was added potassium carbonate (1.62 g, 11.72 mmol) followed by dropwise addition of (1-dimethoxyphosphoryl-2-oxo-propylidene)-imino-ammonium (12.5 mL of 10% w/v, 6.473 mmol). On completion of addition, the mixture was warmed to room temperature and stirred 4 h. Removed solvent under reduced pressure and the residue was dissolved in ethyl acetate and washed with saturated aqueous sodium bicarbonate (1×). The aqueous layer was back extracted twice with ethyl acetate and the organic layers were combined, dried (sodium sulfate), filtered and concentrated to a clear oil which was purified by silica gel chromatography using a gradient from 100% hexanes to 50% ethyl acetate in hexanes giving as a clear oil tert-butyl 4-but-3-ynyl-2,2-dimethyl-pyrrolidine-1-carboxylate (1.15 g, 88%). ESI-MS m/z calc. 251.18852, found 252.2 (M+1)$^+$; Retention time: 1.96 min. $^1$H NMR (400 MHz, CDCl$_3$) δ 3.82-3.56 (m, 1H), 2.99-2.80 (m, 1H), 2.35-2.23 (m, 1H), 2.21 (dd, J=9.5, 4.6 Hz, 2H), 1.96 (s, 1H), 1.95-1.86 (m, 1H), 1.63-1.55 (m, 2H), 1.53-1.36 (m, 13H), 1.30 (t, J=10.8 Hz, 3H).

Step 3: tert-Butyl 2,2-dimethyl-4-[4-(3-sulfamoylphenyl)but-3-ynyl]pyrrolidine-1-carboxylate

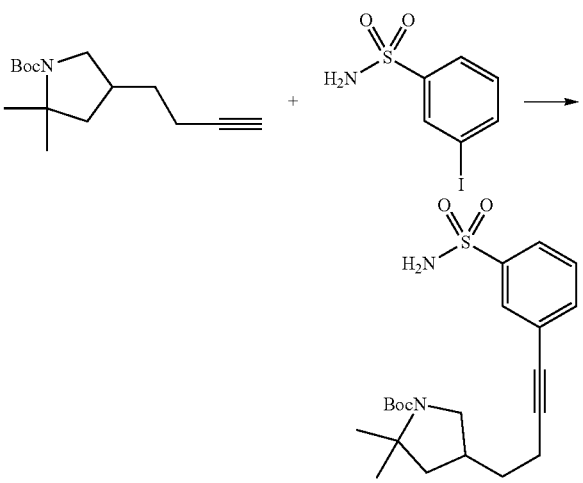

Nitrogen was bubbled through a stirring mixture of 3-iodobenzenesulfonamide (308.0 mg, 1.088 mmol), tert-butyl 4-but-3-ynyl-2,2-dimethyl-pyrrolidine-1-carboxylate (156.3 mg, 0.6218 mmol), Pd(PPh$_3$)$_2$Cl$_2$ (26.19 mg, 0.03731 mmol), iodocopper (11.84 mg, 0.06218 mmol) and N,N-dimethylformamide (1.563 mL) in a vial for 5 min then N-isopropylpropan-2-amine (69.21 mg, 95.86 µL, 0.6840 mmol) was added and the vial was sealed and stirred at 50° C. for 2.5 h then cooled to room temperature and stirred overnight. Cooled to room temperature and poured into water (200 mL) and extracted with dichloromethane (2×100 mL), combined organic layers, washed with water (2×100 mL), dried (magnesium sulfate), filtered and concentrated to an orange oil which was purified by silica gel chromatography using a gradient from 100% hexanes to 100% ethyl acetate giving tert-butyl 2,2-dimethyl-4-[4-(3-sulfamoylphenyl)but-3-ynyl]pyrrolidine-1-carboxylate (307.9 mg, 92%) as a yellow oil. ESI-MS m/z calc. 406.19263, found 407.2 (M+1)$^+$; Retention time: 0.71 min (LC Method A).

Step 4: tert-Butyl 2,2-dimethyl-4-[4-(3-sulfamoylphenyl)butyl]pyrrolidine-1-carboxylate To tert-butyl 2,2-dimethyl-4-[4(3-sulfamoylphenyl)but-3-ynyl]pyrrolidine-1-carboxylate (307.9 mg, 0.5744 mmol) was added platinum oxide (65.20 mg, 0.2871 mmol) followed by EtOH (2.188 mL) and nitrogen was bubbled through the mixture for 1 min followed by hydrogen bubbled through the mixture for 5 min. The mixture was then capped with a hydrogen balloon and stirred for 3 h. Purged with nitrogen, added celite, stirred 1 min then filtered over a pad of celite. Concentrated the filtrate to tert-butyl 2,2-dimethyl-4-[4-(3-sulfamoylphenyl)butyl]pyrrolidine-1-carboxylate (320.4 mg, 82%), an orange oil which was taken directly into the next step. ESI-MS m/z calc. 410.22394, found 411.3 (M+1)$^+$; Retention time: 0.73 min (LC Method A).

Step 5: tert-Butyl 4-[4-[3-[[2-chloro-6-[3-[2-[1-(trifluoromethyl)cyclopropyl]ethoxy]pyrazol-1-yl]pyridine-3-carbonyl]sulfamoyl]phenyl]butyl]-2,2-dimethyl-pyrrolidine-1-carboxylate

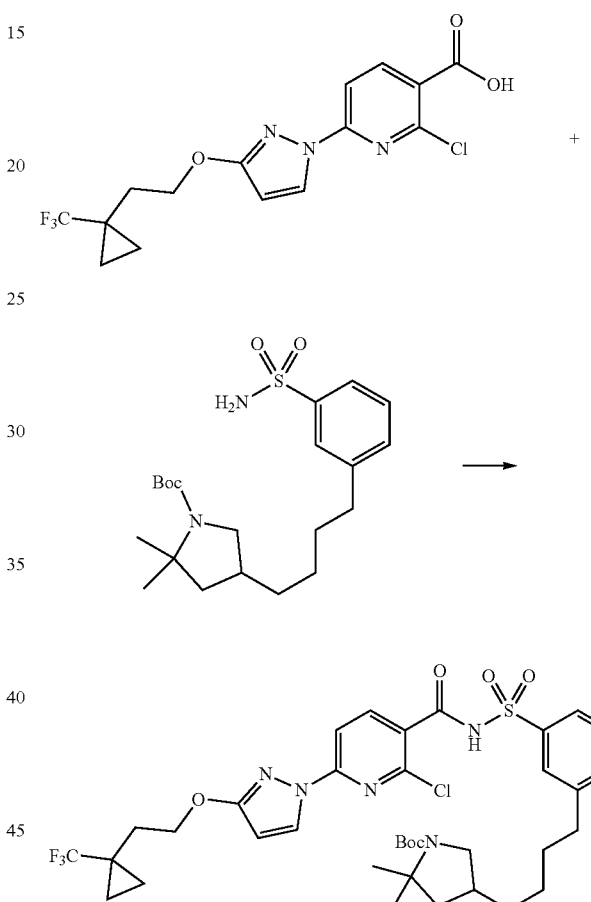

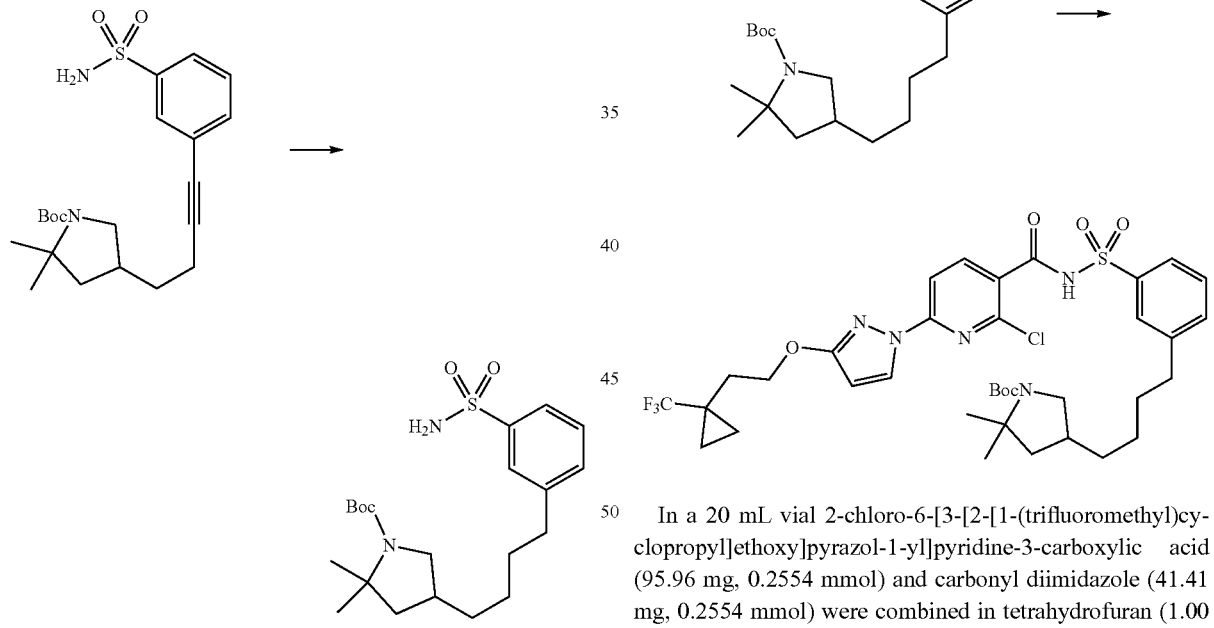

In a 20 mL vial 2-chloro-6-[3-[2-[1-(trifluoromethyl)cyclopropyl]ethoxy]pyrazol-1-yl]pyridine-3-carboxylic acid (95.96 mg, 0.2554 mmol) and carbonyl diimidazole (41.41 mg, 0.2554 mmol) were combined in tetrahydrofuran (1.00 mL) and stirred for 120 min at 50° C. with a loose cap. Then tert-butyl 2,2-dimethyl-4-[4-(3-sulfamoylphenyl)butyl]pyrrolidine-1-carboxylate (69.9 mg, 0.1703 mmol) in tetrahydrofuran (1.338 mL) was added followed by 1,8-diazabicyclo[5.4.0]undec-7-ene (50.93 µL, 0.3406 mmol) and the reaction was heated at 50° C. for 16 hrs. The reaction was diluted with ethyl acetate and washed with a small amount of 1:1 saturated aqueous ammonium chloride/brine. The organics were separated, dried over sodium sulfate, filtered and evaporated then purified by silica gel chromatography using a shallow gradient from 100% dichloromethane to 20% methanol/dichloromethane giving tert-butyl 4-[4-[3-[[2-chloro-6-[3-[2-[1-(trifluoromethyl)cyclopropyl]ethoxy]pyrazol-1-yl]pyridine-3-carbonyl]sulfamoyl]phenyl]butyl]-2,2-dimethyl-pyrrolidine-1-carboxylate (110.5 mg, 84%) as a white solid. ESI-MS m/z calc. 767.27313, found 768.2 (M+1)⁺; Retention time: 0.95 min (LC Method A).

Step 6: 2-Chloro-N-[3-[4-(5,5-dimethyl pyrrolidin-3-yl)butyl]phenyl]sulfonyl-6-[3-[2-[1-(trifluoromethyl)cyclopropyl]ethoxy]pyrazol-1-yl]pyridine-3-carboxamide (Trifluoroacetic Acid Salt)

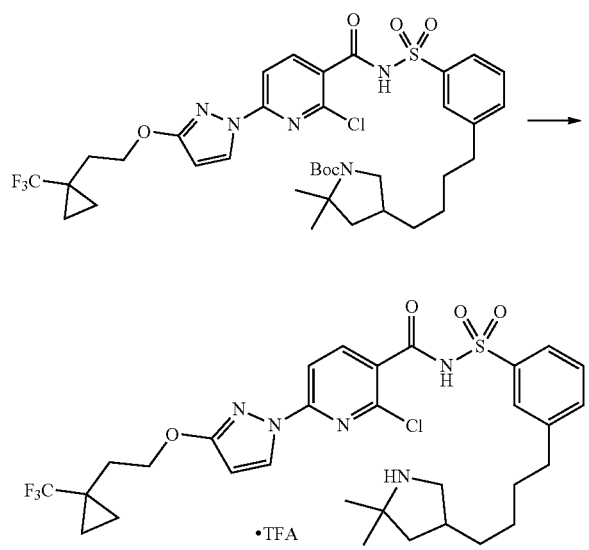 [SMILES: CC(C)(C)OC(=O)N1CC(CCCCc2cccc(S(=O)(=O)NC(=O)c3ccc(-n4ccc(OCCC5(C(F)(F)F)CC5)n4)nc3Cl)c2)CC1(C)C ; CC1(C)CC(CCCCc2cccc(S(=O)(=O)NC(=O)c3ccc(-n4ccc(OCCC5(C(F)(F)F)CC5)n4)nc3Cl)c2)CN1]

tert-Butyl 4-[4-[3-[[2-chloro-6-[3-[2-[1-(trifluoromethyl)cyclopropyl]ethoxy]pyrazol-1-yl]pyridine-3-carbonyl]sulfamoyl]phenyl]butyl]-2,2-dimethyl-pyrrolidine-1-carboxylate (110.5 mg, 0.1438 mmol) was dissolved in dichloromethane (482.2 µL) and to the mixture was added trifluoroacetic acid (508.3 µL, 6.598 mmol) and stirred at room temperature for 40 min. Concentrated mixture to dryness under reduced pressure, took up in sat. aq. sodium bicarbonate and ethyl acetate and separated the layers. Aqueous layer was neutralized with saturated aqueous ammonium chloride and extracted with ethyl acetate. Organic fraction was dried (sodium sulfate), filtered and concentrated to an orange oil which was filtered and purified using a reverse phase HPLC-MS method using a Luna C₁₈ (2) column (75×30 mm, 5 µm particle size) sold by Phenomenex (pn: 00C-4252-U0-AX) and a dual gradient run from 1-99% mobile phase B over 15.0 min (mobile phase A=water (5 mM hydrochloric acid), mobile phase B=acetonitrile, flow rate=50 mL/min, injection volume=950 µL and column temperature=25° C.) to give 2-chloro-N-[3-[4-(5,5-dimethylpyrrolidin-3-yl)butyl]phenyl]sulfonyl-6-[3-[2-[1-(trifluoromethyl)cyclopropyl]ethoxy]pyrazol-1-yl]pyridine-3-carboxamide (trifluoroacetic acid salt) (104.5 mg, 93%). ESI-MS m/z calc. 667.2207, found 668.2 (M+1)⁺; Retention time: 0.67 min (LC Method A).

Step 7: 12,12-Dimethyl-8-(3-{2-[1-(trifluoromethyl)cyclopropyl]ethoxy}-1H-pyrazol-1-yl)-2λ⁶-thia-3,9,11-triazatetracyclo[17.3.1.1¹¹,¹⁴.0⁵,¹⁰]tetracosa-1(22),5,7,9,19(23),20-hexaene-2,2,4-trione (Compound 53)

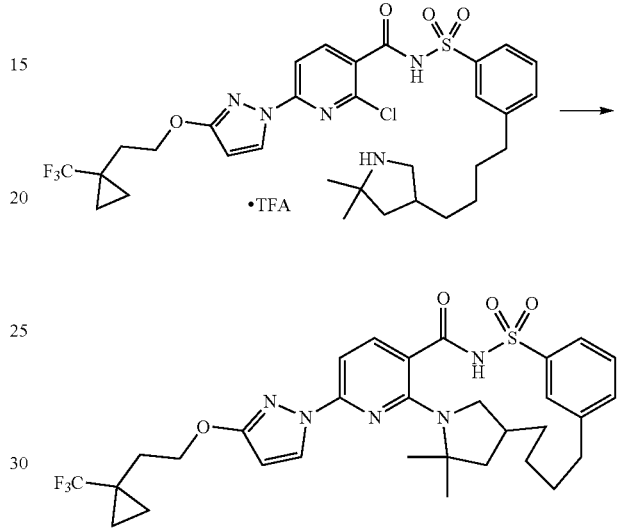

To a solution of 2-chloro-N-[3-[4-(5,5-dimethylpyrrolidin-3-yl)butyl]phenyl]sulfonyl-6-[3-[2-[1-(trifluoromethyl)cyclopropyl]ethoxy]pyrazol-1-yl]pyridine-3-carboxamide trifluoroacetic acid salt (112.5 mg, 0.1438 mmol) in dimethyl sulfoxide (4.499 mL) was added potassium carbonate (119.2 mg, 0.8625 mmol), cesium fluoride (26.22 mg, 0.1726 mmol) and a small amount of 3 Å molecular sieves. The resulting mixture was capped and heated to 165° C. for 6 h. The mixture was then cooled to room temperature, diluted with ethyl acetate and washed with saturated aqueous ammonium chloride and brine. The organic phase was dried (sodium sulfate), filtered and concentrated to an orange oil which was purified by silica gel chromatography using a shallow gradient from 100% hexanes to 100% ethyl acetate to give 12,12-dimethyl-8-(3-{2-[1-(trifluoromethyl)cyclopropyl]ethoxy}-1H-pyrazol-1-yl)-2λ⁶-thia-3,9,11-triazatetracyclo[17.3.1.1¹¹,¹⁴.0⁵,¹⁰]tetracosa-1(22),5,7,9,19(23),20-hexaene-2,2,4-trione (Compound 53) (46.5 mg, 51%) as a yellow solid. ¹H NMR (400 MHz, dimethyl sulfoxide-d₆) δ 12.44 (s, 1H), 8.21 (d, J=2.8 Hz, 1H), 7.84 (s, 1H), 7.81 (s, 1H), 7.78-7.74 (m, 1H), 7.59 (s, 2H), 6.93 (d, J=8.2 Hz, 1H), 6.12 (d, J=2.8 Hz, 1H), 4.31 (t, J=7.0 Hz, 2H), 2.75 (s, 3H), 2.65 (s, 1H), 2.08 (t, J=7.0 Hz, 3H), 1.82 (td, J=13.9, 12.7, 6.0 Hz, 2H), 1.59 (s, 3H), 1.53 (s, 1H), 1.51 (s, 3H), 1.47 (s, 2H), 1.14 (d, J=8.7 Hz, 1H), 1.01-0.93 (m, 3H), 0.90-0.86 (m, 2H), 0.72 (s, 1H). ESI-MS m/z calc. 631.244, found 632.1 (M+1)⁺; Retention time: 2.44 min (LC Method B).

Example 14: Preparation of 12,12-dimethyl-8-(3-{2-[1-(trifluoromethyl) cyclopropyl]ethoxy}-1H-pyrazol-1-yl)-2λ$^6$-thia-3,9,11-triazatetracyclo[17.2.2.1$^{11,14}$.0$^{5,10}$]tetracosa-1(21),5,7,9,19,22-hexaene-2,2,4-trione (Enantiomer 1) (Compound 54) and 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.2.2.1$^{11,14}$.0$^{5,10}$]tetracosa-1(21),5,7,9,19,22-hexaene-2,2,4-trione (Enantiomer 2) (Compound 55)

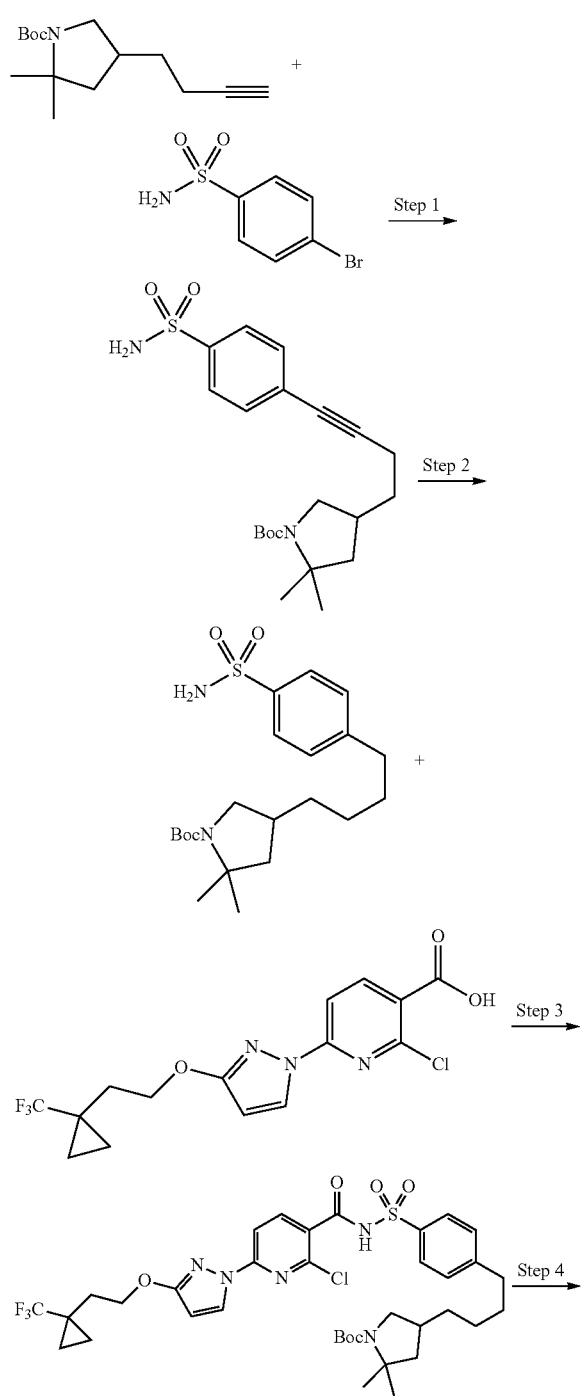

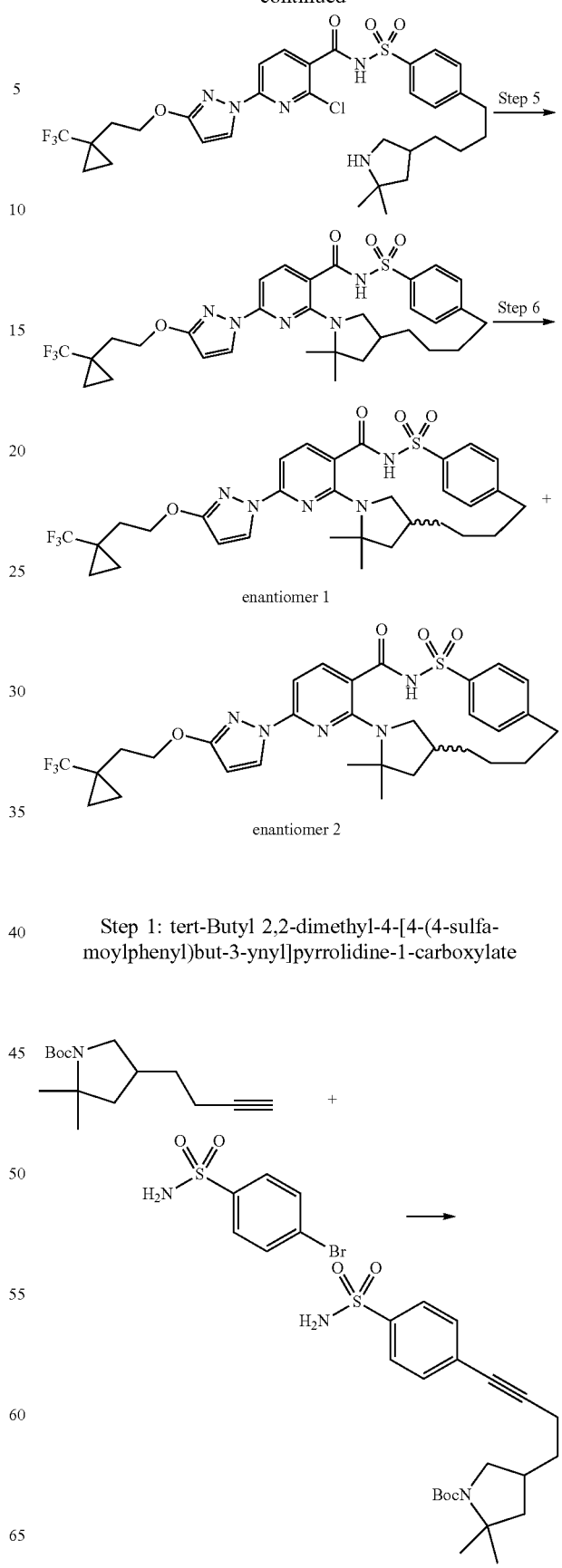

Step 1: tert-Butyl 2,2-dimethyl-4-[4-(4-sulfamoylphenyl)but-3-ynyl]pyrrolidine-1-carboxylate Nitrogen was bubbled through a stirring mixture of 4-bromobenzenesulfonamide (256.9 mg, 1.088 mmol), tert-butyl 4-but-3-ynyl-2,2-dimethyl-pyrrolidine-1-carboxylate (156.3 mg, 0.6218 mmol), Pd(PPh$_3$)$_2$Cl$_2$ (26.19 mg, 0.03731 mmol), iodocopper (11.84 mg, 0.06218 mmol) and N,N-dimethylformamide (1.563 mL) in a vial for 5 min then N-isopropylpropan-2-amine (69.21 mg, 95.86 μL, 0.6840 mmol) was added and the vial was sealed and stirred at 50° C. for 75 min then cooled to room temperature and stirred overnight. Cooled to room temperature and poured into water (200 mL) and extracted with dichloromethane (2×100 mL), combined organic layers, washed with water (2×100 mL), dried (magnesium sulfate), filtered and concentrated to an orange oil which was purified by silica gel chromatography using a gradient from 100% hexanes to 100% ethyl acetate giving tert-butyl 2,2-dimethyl-4-[4-(4-sulfamoylphenyl)but-3-ynyl]pyrrolidine-1-carboxylate (192.5 mg, 76%) as a white solid. ESI-MS m/z calc. 406.19263, found 407.1 (M+1)$^+$; Retention time: 0.71 min (LC Method A).

Step 2: tert-Butyl 2,2-dimethyl-4-[4-(4-sulfamoylphenyl)butyl]pyrrolidine-1-carboxylate

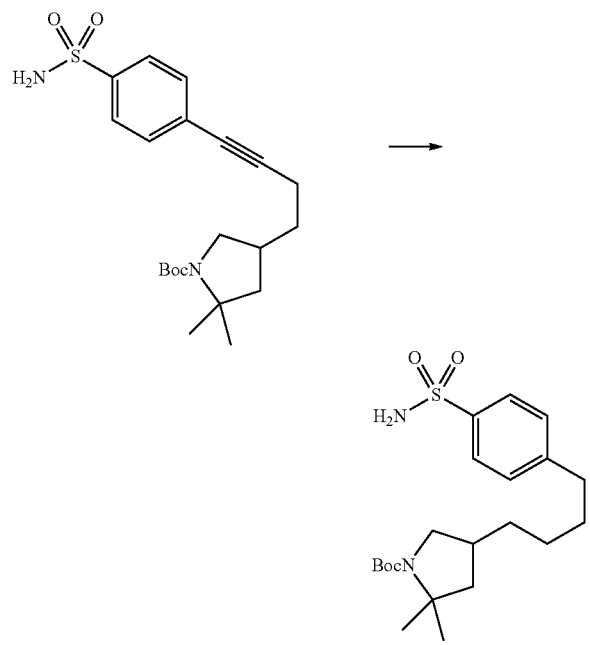

To tert-butyl 2,2-dimethyl-4-[4-(4-sulfamoylphenyl)but-3-ynyl]pyrrolidine-1-carboxylate (192.5 mg, 0.4735 mmol) was added palladium oxide (53.75 mg, 0.2367 mmol) followed by EtOH (1.804 mL) and nitrogen was bubbled through the mixture for 1 min followed by hydrogen bubbled through the mixture for 5 min. The mixture was then capped with a hydrogen balloon and stirred for 3 h. Purged with nitrogen, added celite, stirred 1 min then filtered over a pad of celite. Concentrated the filtrate to tert-butyl 2,2-dimethyl-4-[4-(4-sulfamoylphenyl)butyl]pyrrolidine-1-carboxylate (179.5 mg, 92%), an off-white solid. ESI-MS m/z calc. 410.22394, found 411.2 (M+1)$^+$; Retention time: 0.75 min (LC Method A).

Step 3: tert-Butyl 4-[4-[4-[[2-chloro-6-[3-[2-[1-(trifluoromethyl)cyclopropyl]ethoxy]pyrazol-1-yl]pyridine-3-carbonyl]sulfamoyl]phenyl]butyl]-2,2-dimethyl-pyrrolidine-1-carboxylate

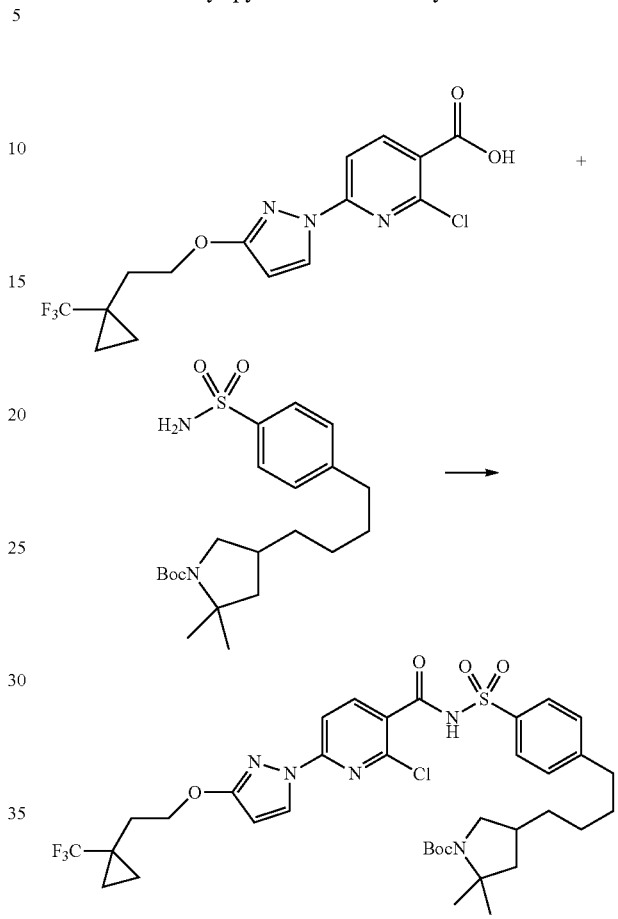

In a 20 mL vial, 2-chloro-6-[3-[2-[1-(trifluoromethyl)cyclopropyl]ethoxy]pyrazol-1-yl]pyridine-3-carboxylic acid (164.3 mg, 0.4372 mmol) and carbonyl diimidazole (77.70 mg, 0.4792 mmol) were combined in tetrahydrofuran (2.576 mL) and stirred for 120 min at 50° C. with a loose cap. Then tert-butyl 2,2-dimethyl-4-[4-(4-sulfamoylphenyl)butyl]pyrrolidine-1-carboxylate (179.5 mg, 0.4372 mmol) in tetrahydrofuran (3.436 mL) was added followed by 1,8-diazabicyclo[5.4.0]undec-7-ene (137.0 mg, 134.6 μL, 0.9002 mmol) and the reaction was heated at 50° C. for 16 hrs. The reaction was diluted with ethyl acetate and washed with saturated aqueous ammonium chloride followed by brine. The organic layer was dried over sodium sulfate, evaporated then purified using a reverse phase HPLC-MS method using a Luna C$_{18}$ (2) column (75×30 mm, 5 μm particle size) sold by Phenomenex (pn: 00C-4252-U0-AX) and a dual gradient run from 30-99% mobile phase B over 15.0 min (mobile phase A=water (5 mM hydrochloric acid), mobile phase B=acetonitrile, flow rate=50 mL/min, injection volume=950 μL and column temperature=25° C.). Fractions of intended product were combined and acetonitrile was removed under reduced pressure. The material was then diluted with ethyl acetate and washed with saturated aqueous sodium bicarbonate (1×) and brine (1×), dried (sodium sulfate), filtered and concentrated to provide tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]phenyl]butyl]-2,2-dimethyl-pyrrolidine-1-carboxylate (132.8 mg, 40%), a clear oil. ESI-MS m/z calc. 767.27313, found 768.2 (M+1)⁺; Retention time: 0.96 min (LC Method A).

Step 4: 2-Chloro-N-[4-[4-(5,5-dimethylpyrrolidin-3-yl)butyl]phenyl]sulfonyl-6-[3-[2-[1-(trifluoromethyl)cyclopropyl]ethoxy]pyrazol-1-yl]pyridine-3-carboxamide

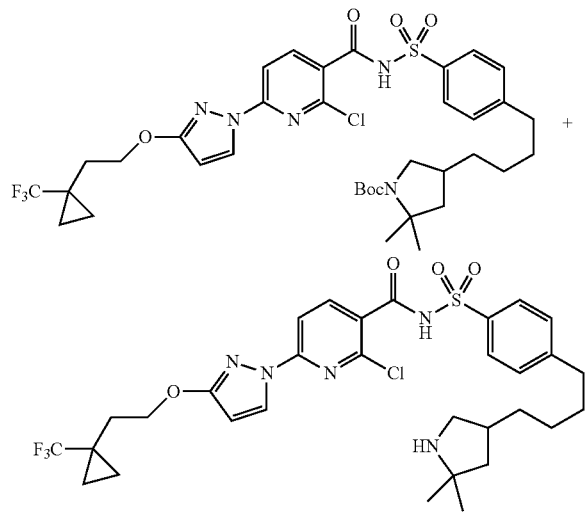

tert-Butyl 4-[4-[4-[[2-chloro-6-[3-[2-[1-(trifluoromethyl)cyclopropyl]ethoxy]pyrazol-1-yl]pyridine-3-carbonyl]sulfamoyl]phenyl]butyl]-2,2-dimethyl-pyrrolidine-1-carboxylate (132.8 mg, 0.1729 mmol) was dissolved in dichloromethane (579.5 µL) and to the mixture was added trifluoroacetic acid (904.5 mg, 611.1 µL, 7.933 mmol) and the mixture was stirred at room temperature for 60 min. Concentrated the mixture to dryness under reduced pressure, took up in saturated aqueous sodium bicarbonate and ethyl acetate and separated the layers. Dried the organic layer (sodium sulfate), filtered and concentrated to a white solid, 2-chloro-N-[4-[4-(5,5-dimethylpyrrolidin-3-yl)butyl]phenyl]sulfonyl-6-[3-[2-[1-(trifluoromethyl) cyclopropyl]ethoxy]pyrazol-1-yl]pyridine-3-carboxamide (99.8 mg, 86%). ESI-MS m/z calc. 667.2207, found 668.3 (M+1)⁺; Retention time: 0.66 min (LC Method A).

Step 5: 12,12-Dimethyl-8-(3-{2-[1-(trifluoromethyl)cyclopropyl]ethoxy}-1H-pyrazol-1-yl)-2λ⁶-thia-3,9,11-triazatetracyclo[17.2.2.1 11,14.0 5,10]tetracosa-1(21),5,7,9,19,22-hexaene-2,2,4-trione (Compound 52)

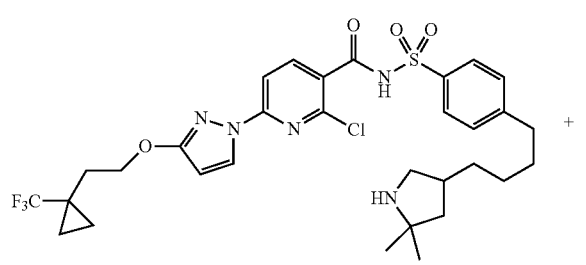

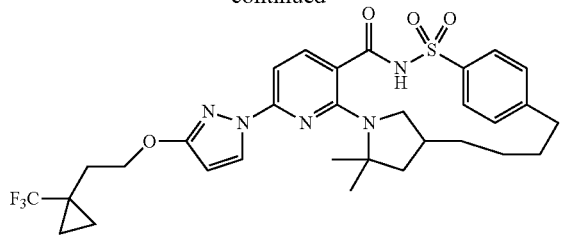

To a solution of 2-chloro-N-[4-[4-(5,5-dimethylpyrrolidin-3-yl)butyl]phenyl]sulfonyl-6-[3-[2-[1-(trifluoromethyl)cyclopropyl]ethoxy]pyrazol-1-yl]pyridine-3-carboxamide (99.8 mg, 0.1494 mmol) in dimethyl sulfoxide (3.991 mL) was added potassium carbonate (103.2 mg, 0.7470 mmol), cesium fluoride (27.24 mg, 0.1793 mmol) and a small amount of 3 Å molecular sieves. The resulting mixture was capped and heated to 155° C. overnight. Cooled to room temperature, diluted with ethyl acetate and washed with saturated aqueous ammonium chloride and brine. The organic phase was dried (sodium sulfate), filtered and concentrated to an orange oil which was purified by silica gel chromatography using a shallow gradient from 100% hexanes to 100% ethyl acetate to give 12,12-dimethyl-8-(3-{2-[1-(trifluoromethyl)cyclopropyl]ethoxy}-1H-pyrazol-1-yl)-2λ⁶-thia-3,9,11-triazatetracyclo[17.2.2.1 11,14.0 5,10]tetracosa-1(21),5,7,9,19,22-hexaene-2,2,4-trione (Compound 51) (25 mg, 26%) as a white solid. ¹H NMR (400 MHz, dimethyl sulfoxide-d₆) δ 12.21 (s, 1H), 8.17 (d, J=2.8 Hz, 1H), 8.07 (d, J=7.8 Hz, 1H), 7.86 (d, J=8.3 Hz, 1H), 7.76 (d, J=8.0 Hz, 1H), 7.46 (d, J=16.6 Hz, 2H), 6.89 (d, J=8.3 Hz, 1H), 6.10 (d, J=2.8 Hz, 1H), 4.31 (t, J=7.0 Hz, 2H), 2.92-2.80 (m, 1H), 2.74 (dt, J=13.9, 6.9 Hz, 1H), 2.19 (s, 1H), 2.07 (t, J=7.1 Hz, 2H), 1.94-1.85 (m, 2H), 1.80 (s, 1H), 1.70 (dd, J=11.7, 5.3 Hz, 1H), 1.60-1.52 (m, 1H), 1.49 (s, 6H), 1.44-1.34 (m, 2H), 1.02 (dt, J=12.8, 6.7 Hz, 1H), 0.98-0.93 (m, 2H), 0.89 (d, J=10.8 Hz, 2H), 0.77 (q, J=11.6 Hz, 1H), 0.36 (s, 1H). ESI-MS m/z calc. 631.244, found 632.1 (M+1)⁺; Retention time: 2.46 min (LC Method B).

Step 6: 12,12-Dimethyl-8-(3-{2-[1-(trifluoromethyl)cyclopropyl]ethoxy}-1H-pyrazol-1-yl)-2λ⁶-thia-3,9,11-triazatetracyclo[17.2.2.1 11,14.0 5,10]tetracosa-1(21),5,7,9,19,22-hexaene-2,2,4-trione (Enantiomer 1) (Compound 54) and 12,12-Dimethyl-8-(3-{2-[1-(trifluoromethyl)cyclopropyl]ethoxy}-1H-pyrazol-1-yl)-2λ⁶-thia-3,9,11-triazatetracyclo[17.2.2.1 11,14.05,10]tetracosa-1(21),5,7,9,19,22-hexaene-2,2,4-trione (Enantiomer 2) (Compound 55)

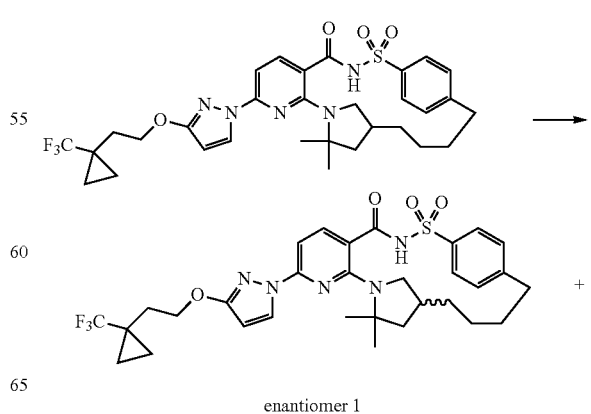

enantiomer 1

263
-continued

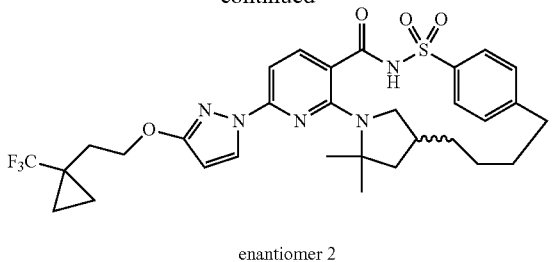

enantiomer 2

Subjected racemic 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.2.2.1$^{11,14}$.0$^{5,10}$]tetracosa-1(21),5,7,9,19,22-hexaene-2,2,4-trione (21.9 mg, 0.03411 mmol) to chiral separation by SFC chromatography using a ChiralPak AS-H (250×10 mm column, 5 μm particle size) with 25% acetonitrile/methanol (90:10)/75% carbon dioxide mobile phase at 10 mL/min over 6.0 min (injection volume=70 μL of 24 mg/mL solution in 85% acetonitrile/methanol (90:10)/15% dimethyl sulfoxide) giving as the first enantiomer to elute, 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.2.2.1$^{11,14}$.0$^{5,10}$]tetracosa-1(21),5,7,9,19,22-hexaene-2,2,4-trione (enantiomer 1) (Compound 54) (10.01 mg, 92%) as a white solid; ESI-MS m/z calc. 631.244, found 632.2 (M+1)$^+$; Retention time: 2.44 min (LC Method B) and as the second enantiomer to elute, 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.2.2.1$^{11,14}$.0$^{5,10}$]tetracosa-1(21),5,7,9,19,22-hexaene-2,2,4-trione (enantiomer 2) (Compound 55) (8.59 mg, 80%) as a white solid; $^1$H NMR (400 MHz, dimethyl sulfoxide-d$_6$) δ 12.20 (s, 1H), 8.17 (d, J=2.8 Hz, 1H), 8.07 (dd, J=8.0, 2.1 Hz, 1H), 7.86 (d, J=8.3 Hz, 1H), 7.76 (dd, J=8.1, 2.0 Hz, 1H), 7.49 (d, J=8.2 Hz, 1H), 7.44 (d, J=8.2 Hz, 1H), 6.90 (d, J=8.3 Hz, 1H), 6.10 (d, J=2.7 Hz, 1H), 4.31 (t, J=7.0 Hz, 2H), 2.87 (dt, J=13.4, 6.4 Hz, 1H), 2.74 (dt, J=14.0, 7.0 Hz, 1H), 2.19 (t, J=10.4 Hz, 1H), 2.07 (t, J=7.1 Hz, 2H), 1.89 (dt, J=13.4, 6.0 Hz, 2H), 1.80 (d, J=8.4 Hz, 1H), 1.70 (dd, J=11.8, 5.4 Hz, 1H), 1.55 (dt, J=14.0, 7.0 Hz, 1H), 1.49 (s, 6H), 1.39 (t, J=12.3 Hz, 2H), 1.02 (dt, J=12.8, 6.5 Hz, 1H), 0.96 (td, J=4.9, 4.4, 3.1 Hz, 2H), 0.91-0.85 (m, 2H), 0.77 (q, J=10.7 Hz, 1H), 0.36 (s, 1H), ESI-MS m/z calc. 631.244, found 632.2 (M+1)$^+$; Retention time: 2.44 min (LC Method B).

Example 15: Preparation of 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.3.1.1$^{11,14}$.0$^{5,10}$]tetracosa-1(22),5,7,9,19(23),20-hexaene-2,2,4-trione (Enantiomer 1) (Compound 56) and 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.3.1.1$^{11,14}$.0$^{5,10}$]tetracosa-1(22),5,7,9,19(23),20-hexaene-2,2,4-trione (Enantiomer 2) (Compound 57)

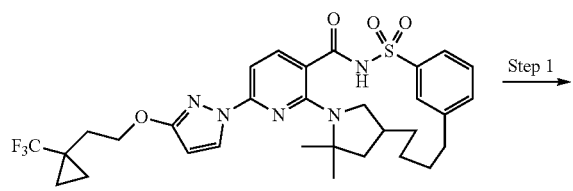

264
-continued

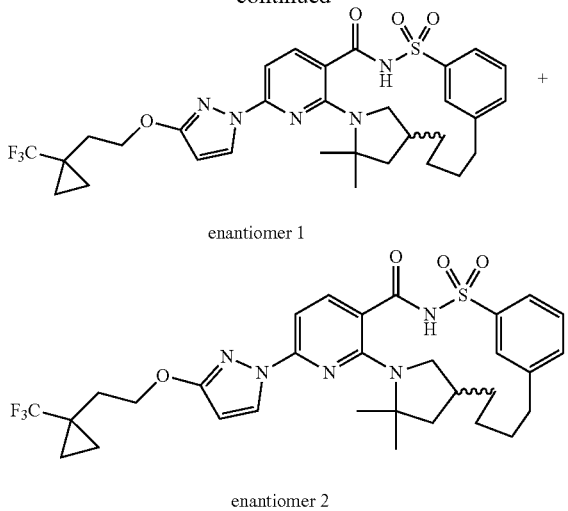

enantiomer 1 enantiomer 2

Step 1: 12,12-Dimethyl-8-(3-{2-[1-(trifluoromethyl)cyclopropyl]ethoxy}-1H-pyrazol-1-yl)-2λ$^6$-thia-3,9,11-triazatetracyclo[17.3.1.1$^{11,14}$.0$^{5,10}$]tetracosa-1(22),5,7,9,19(23),20-hexaene-2,2,4-trione (Enantiomer 1) (Compound 56) and 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.3.1.1$^{11,14}$.0$^{5,10}$]tetracosa-1(22),5,7,9,19(23),20-hexaene-2,2,4-trione (Enantiomer 2) (Compound 57)

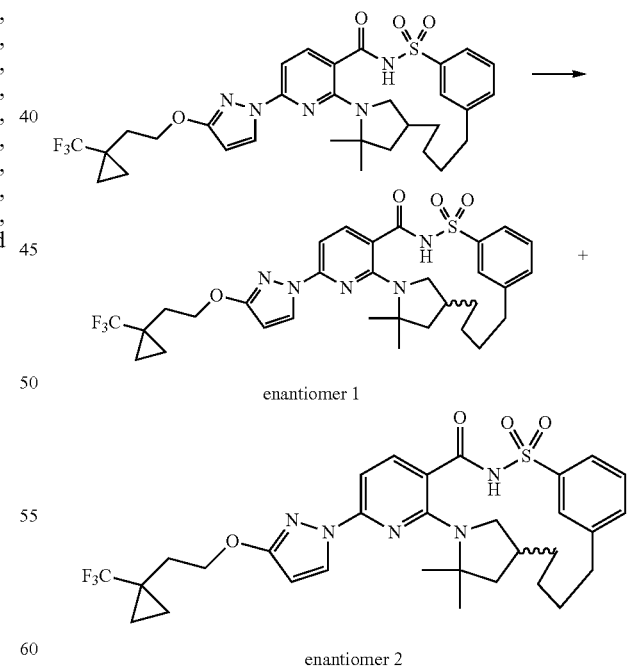

enantiomer 1 enantiomer 2

Subjected racemic 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.3.1.1$^{11,14}$.0$^{5,10}$]tetracosa-1(22),5,7,9,19(23),20-hexaene-2,2,4-trione (41.7 mg, 0.06575 mmol) to chiral separation by SFC chromatography using a ChiralPak AS-H (250×10 mm column, 5 μm particle size) with 25% acetonitrile/methanol (90:10)/75% carbon dioxide mobile phase at 10 mL/min over 8.0 min (injection volume=70 μL of 24 mg/mL solution in 85% acetonitrile/methanol (90:10)/15% dimethyl sulfoxide) giving as the first enantiomer to elute, 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.3.1.1 11,14.0 5,10]tetracosa-1(22),5,7,9,19(23),20-hexaene-2,2,4-trione (enantiomer 1) (Compound 56) (20.2 mg, 97%); ESI-MS m/z calc. 631.244, found 632.2 (M+1)$^+$; Retention time: 2.44 min (LC Method B) and as the second enantiomer to elute, 12,12-dimethyl-8-(3-{2-[1-(trifluoromethyl)cyclopropyl]ethoxy}-1H-pyrazol-1-yl)-2λ$^6$-thia-3,9,11-triazatetracyclo[17.3.1.1 11,14.0 5,10]tetracosa-1(22),5,7,9,19(23),20-hexaene-2,2,4-trione (enantiomer 2) (Compound 57) (15.9 mg, 75%); $^1$H NMR (400 MHz, dimethyl sulfoxide-d$_6$) δ 12.44 (s, 1H), 8.21 (d, J=2.8 Hz, 1H), 7.87-7.75 (m, 3H), 7.63-7.57 (m, 2H), 6.93 (dd, J=8.2, 1.2 Hz, 1H), 6.12 (dd, J=2.8, 0.9 Hz, 1H), 4.31 (t, J=7.0 Hz, 2H), 2.75 (d, J=6.0 Hz, 2H), 2.68-2.62 (m, 1H), 2.11-2.05 (m, 3H), 1.83 (dt, J=12.6, 6.3 Hz, 2H), 1.58 (s, 3H), 1.51 (s, 6H), 1.15 (t, J=8.9 Hz, 1H), 0.97 (d, J=3.4 Hz, 1H), 0.97-0.95 (m, 2H), 0.91 (s, 1H), 0.90 (s, 2H), 0.72 (s, 1H). ESI-MS m/z calc. 631.244, found 632.2 (M+1)$^+$; Retention time: 2.43 min (LC Method B).

Example 16: Preparation of 12,12-dimethyl-8-(3-{2-[1-(trifluoromethyl)cyclopropyl]ethoxy}-1H-pyrazol-1-yl)-2λ$^6$-thia-3,9,11,20,25-pentaazatetracyclo[19.3.1.1 11,14.0 5,10]hexacosa-1(24),5,7,9,21(25),22-hexaene-2,2,4-trione (Enantiomer 1) (Compound 63) and 12,12-dimethyl-8-(3-{2-[1-(trifluoromethyl)cyclopropyl]ethoxy}-1H-pyrazol-1-yl)-2λ$^6$-thia-3,9,11,20,25-pentaazatetracyclo[19.3.1.1 11,14.0 5,10]hexacosa-1(24),5,7,9,21(25),22-hexaene-2,2,4-trione (Enantiomer 2) (Compound 64)

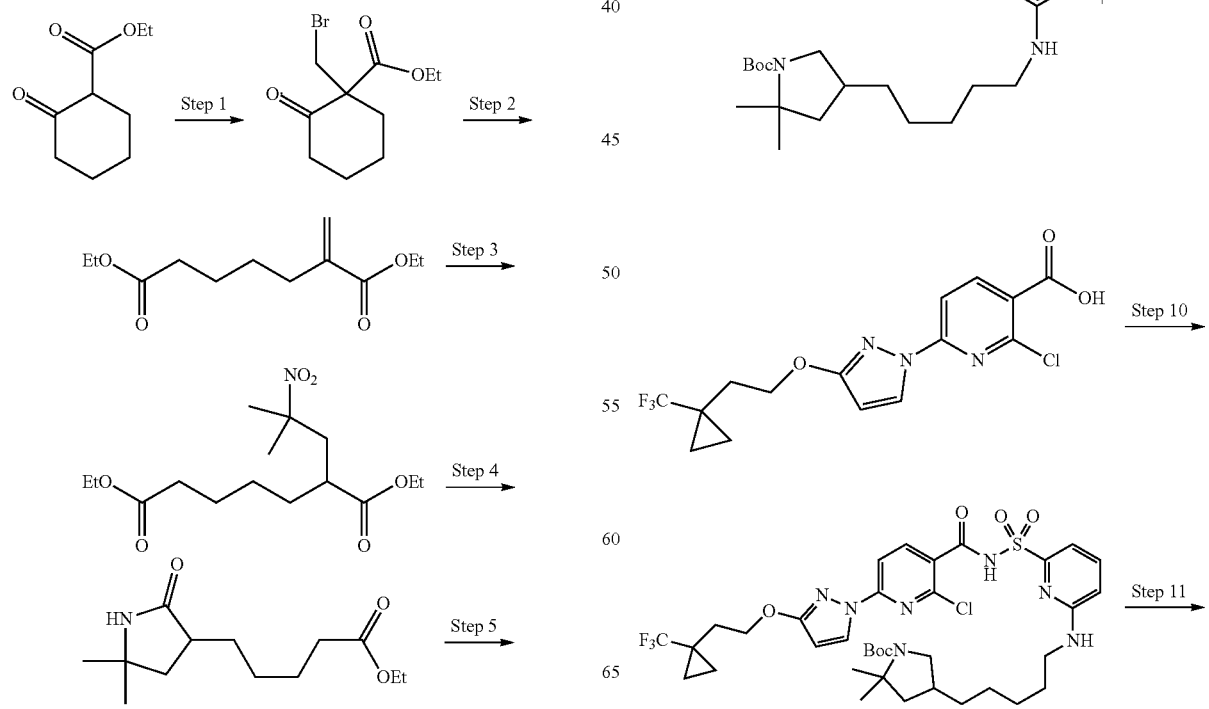

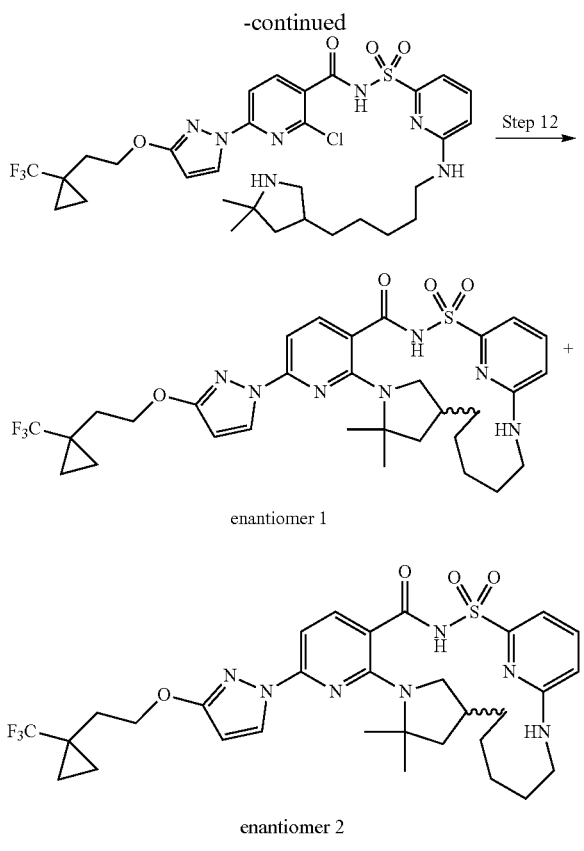

enantiomer 1 enantiomer 2

Step 1: Ethyl 1-(bromomethyl)-2-oxo-cyclohexanecarboxylate

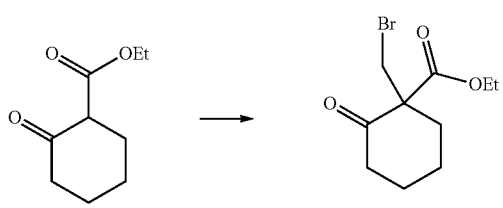 [SMILES: CCOC(=O)C1CCCCC1=O ; CCOC(=O)C1(CBr)CCCCC1=O]

A solution of ethyl 2-cyclohexanonecarboxylate (84.0 g, 493 mmol) in tetrahydrofuran (350 mL) of was added dropwise to a slurry of 60% sodium hydride (25.7 g, 641 mmol) and hexamethylphosphoramide (112 mL, 641 mmol) in tetrahydrofuran (850 mL) over a four h period and the resulting mixture stirred at room temperature for one h. Dibromomethane (173 mL, 2470 mmol) was then added dropwise over a one h period and the mixture was refluxed at 70° C. for 16 h. The reaction mixture was diluted with diethyl ether (6 L) and the organic layer was washed with water (5×850 mL), the aqueous phases were discarded and the organic phase was dried over sodium sulfate and concentrated. The residue was purified by silica gel chromatography using a 0-15% hexanes/ethyl acetate gradient to obtain ethyl 1-(bromomethyl)-2-oxo-cyclohexanecarboxylate (68 g, 52%) as a clear oil. Purity was determined to be approx. 80% by $^1$H NMR. $^1$H NMR (250 MHz, CDCl$_3$) δ 4.35-4.15 (m, 2H), 3.88-3.50 (dd, 2H), 2.75-2.64 (dd, 1H), 2.49-2.41 (m, 2H), 2.30-2.17 (p, 2H), 2.10-1.75 (m, 2H), 1.74-1.53 (m, 2H), 1.32-1.22 (m, 3H). The crude material was used in the next step without further purification.

Step 2: Diethyl 2-methyleneheptanedioate

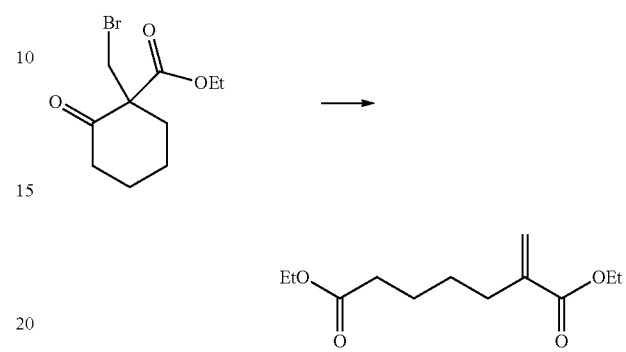

A slurry of ethyl 1-(bromomethyl)-2-oxo-cyclohexanecarboxylate (68 g, 258 mmol) and potassium carbonate (71.4 g, 517 mmol) in ethanol (600 mL) was stirred for 16 h at room temperature. The resulting mixture was filtered, the solids were discarded and the filtrate was concentrated and purified by silica gel chromatography using a 0-15% hexanes/ethyl acetate gradient to obtain diethyl 2-methyleneheptanedioate (45.2 g, 77%) as a clear oil. $^1$H NMR (250 MHz, CDCl$_3$) δ 6.17 (s, 1H), 5.54 (s, 1H), 4.23-4.06 (m, 4H), 2.35-2.15 (t, 4H), 1.73-1.40 (m, 4H), 1.29-1.07 (m, 6H). ESI-MS m/z calc. 228.29, found 229.0 (M+1)$^+$. Retention time: 4.97 min (LC Method Q).

Step 3: Diethyl 2-(2-methyl-2-nitro-propyl)heptanedioate

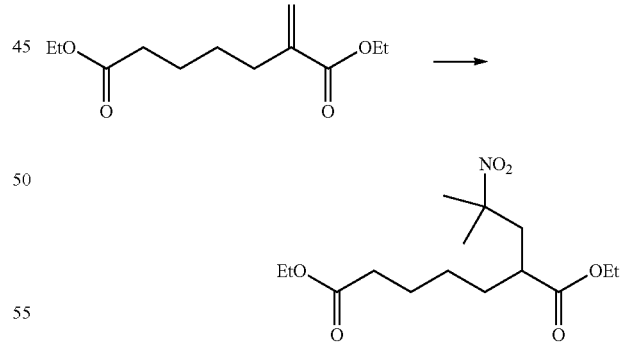

A mixture of diethyl 2-methyleneheptanedioate (48.6 g, 213 mmol), 2-nitropropane (58 mL, 639 mmol) and 1,8-diazabicyclo[5.4.0]undec-7-ene (3.2 mL, 21 mmol) was heated at 85° C. for five h. The mixture was concentrated and purified by silica gel chromatography using a 0-15% hexanes/ethyl acetate gradient to obtain diethyl 2-(2-methyl-2-nitro-propyl)heptanedioate (58 g, 85%) as a clear oil. ESI-MS m/z calc. 317.38, found 318.1 (M+1)$^+$. Retention time: 5.19 min (LC Method Q).

Step 4: Ethyl 5-(5,5-dimethyl-2-oxo-pyrrolidin-3-yl)pentanoate

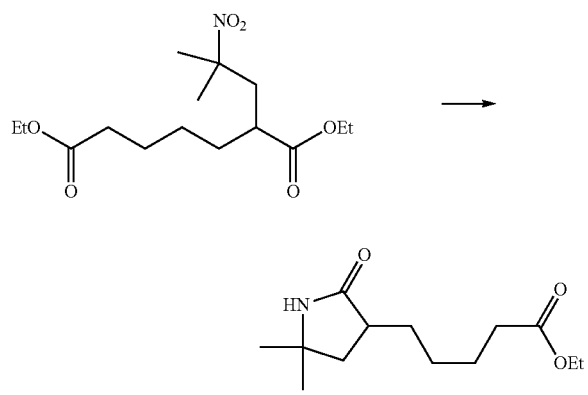

To a solution of diethyl 2-(2-methyl-2-nitro-propyl)heptanedioate (19 g, 59.8 mmol) in ethanol (400 mL) was added Raney Nickel slurry (9 g) and the resulting mixture was heated to 80° C. for 22 h in a Parr reactor under 2 bar of hydrogen. Celite (50 g) was added to the reactor and the mixture was filtered. The solids were discarded and the filtrate was concentrated under vacuum to obtain ethyl 5-(5,5-dimethyl-2-oxo-pyrrolidin-3-yl)pentanoate (13.2 g, 91% yield) as a pale oil. ESI-MS m/z calc. 241.33, found 242.1 (M+1)$^+$. Retention time: 3.79 min (LC Method Q). The crude product was used in the next step without further purification.

Step 5: 5-(5,5-Dimethylpyrrolidin-3-yl)pentan-1-ol

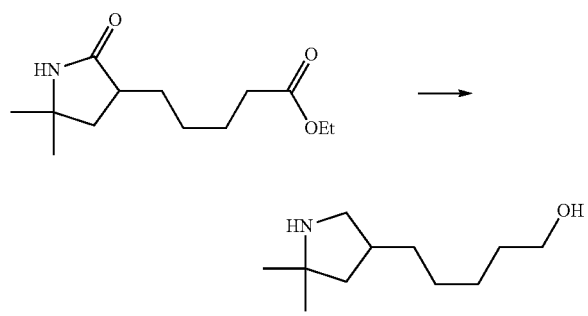

To a solution of ethyl 5-(5,5-dimethyl-2-oxo-pyrrolidin-3-yl)pentanoate (13.2 g, 54.7 mmol) in tetrahydrofuran (200 mL) was added lithium aluminum hydride (6.2 g, 164.1 mmol) in portions, then the resulting slurry was refluxed under nitrogen atmosphere for 17 h. The mixture was carefully quenched with saturated aqueous sodium sulfate solution (50 mL) and filtered. The solids were discarded and the aqueous phase was separated and discarded. The organic phase was concentrated to obtain 5-(5,5-dimethylpyrrolidin-3-yl)-pentan-1-ol (8.8 g) as a pale yellow oil. ESI-MS m/z calc. 185.31, found 186.3 (M+1)$^+$. Retention time: 1.98 min (LC Method Q). The crude product was used in the next step without further purification.

Step 6: tert-Butyl 4-(5-hydroxypentyl)-2,2-dimethyl-pyrrolidine-1-carboxylate

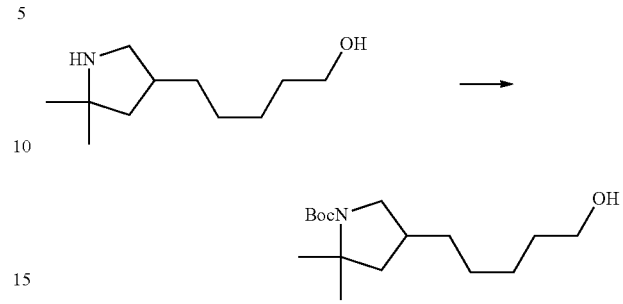

To a solution of 5-(5,5-dimethylpyrrolidin-3-yl)-pentan-1-ol (27.0 g, 145.7 mmol) in dichloromethane (200 mL) was added a solution of sodium bicarbonate (24.5 g, 291.4 mmol) in water (150 mL), followed addition of di-tert-butyl dicarbonate (31.8 g, 145.7 mmol). The resulting heterogeneous mixture was stirred at room temperature for two h. The phases were separated and the aqueous phase was discarded. The organic phase was concentrated under vacuum and purified by silica gel chromatography using a 0-45% hexanes/ethyl acetate gradient to obtain tert-butyl 4-(5-hydroxypentyl)-2,2-dimethyl-pyrrolidine-1-carboxylate (32.0 g, 77%) as a clear oil. $^1$H NMR (250 MHz, CDCl$_3$) δ 4.29 (q, 1H), 3.53 (s, 1H), 3.37 (q, 2H), 2.75 (q, 1H), 2.05 (s, 2H), 1.87 (m, 1H), 1.43-1.17 (m, 23H). ESI-MS m/z calc. 285.43, found 286.4 (M+1)$^+$. Retention time: 5.20 min (LC Method Q).

Step 7: tert-Butyl 2,2-dimethyl-4-(5-methylsulfonyloxypentyl)pyrrolidine-1-carboxylate

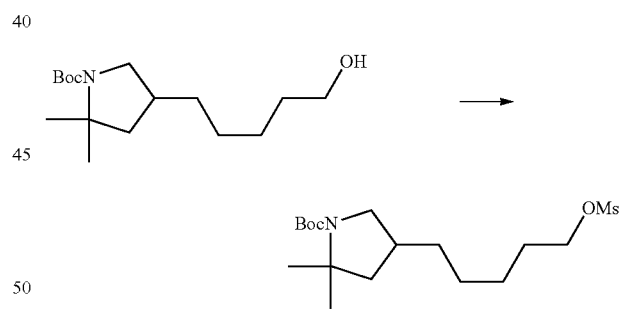

A solution of tert-butyl 4-(5-hydroxypentyl)-2,2-dimethyl-pyrrolidine-1-carboxylate (10.5 g, 36.8 mmol) and triethylamine (10.3 mL, 73.6 mmol) in dichloromethane (100 mL) was chilled in an ice water bath. Then methanesulfonyl chloride (3.2 mL, 40.5 mmol) was added dropwise over a 15 min period and the resulting mixture was stirred for one h in the ice bath. The reaction was quenched with saturated sodium bicarbonate solution (50 mL). The aqueous phase was discarded and the organic phase was concentrated to obtain tert-butyl 2,2-dimethyl-4-(5-methylsulfonyloxypentyl)pyrrolidine-1-carboxylate (13.3 g, 99%) as a yellow oil. ESI-MS m/z calc. 363.16, found 364.3 (M+1)$^+$. Retention time: 5.77 min The crude product was used in the next step without further purification (LC Method Q).

Step 8: tert-Butyl 4-(5-aminopentyl)-2,2-dimethyl-pyrrolidine-1-carboxylate

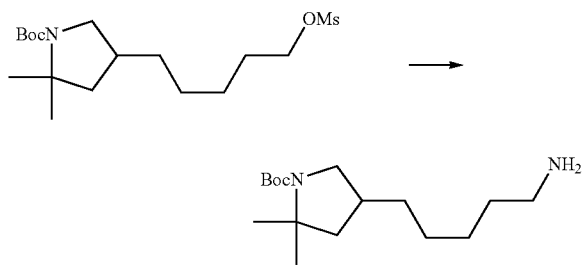

A solution of tert-butyl 2,2-dimethyl-4-(5-methylsulfonyloxypentyl)pyrrolidine-1-carboxylate (13.3 g, 36.6 mmol) in tetrahydrofuran (275 mL) and 28% aqueous ammonium hydroxide (275 mL was stirred at 50° C. for 24 h. Tetrahydrofuran and ammonia were removed under vacuum and the remaining aqueous phase was extracted with dichloromethane (3×100 mL) and the combined organics were concentrated to an oil and purified by silica gel chromatography using a 0-15% dichloromethane/methanol (0.25% ammonium hydroxide) gradient to obtain tert-butyl 4-(5-aminopentyl)-2,2-dimethyl-pyrrolidine-1-carboxylate (5.4 g, 52%) as a pale oil. $^1$H NMR (250 MHz, CDCl$_3$) δ 3.53 (q, 1H), 2.75 (q, 1H), 2.05 (s, 2H), 1.86 (m, 1H), 1.43-1.10 (m, 23H). ESI-MS m/z calc. 284.45, found 285.4 (M+1)$^+$. Retention time: 4.07 min (LC Method Q).

Step 9: tert-Butyl 2,2-dimethyl-4-[5-[(6-sulfamoyl-2-pyridyl)amino]pentyl]pyrrolidine-1-carboxylate

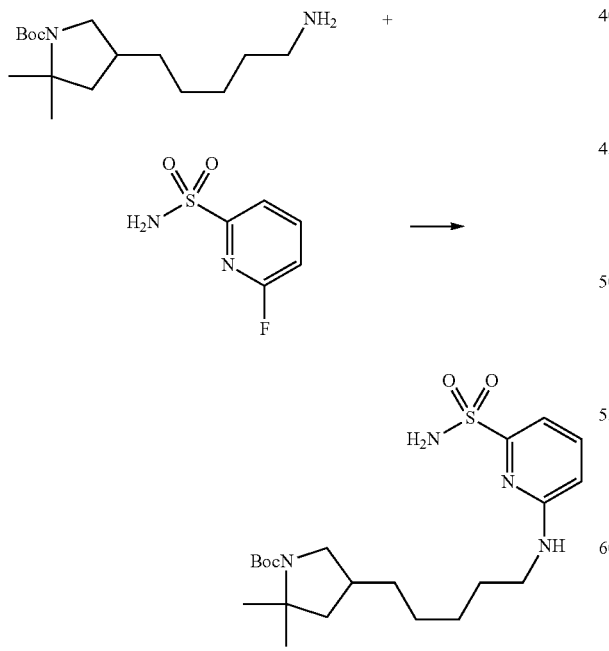

A 100 mL round bottom flask was charged with tert-butyl 4-(5-aminopentyl)-2,2-dimethyl-pyrrolidine-1-carboxylate (1.028 g, 3.614 mmol), 6-fluoropyridine-2-sulfonamide (636 mg, 3.610 mmol) and anhydrous dimethyl sulfoxide (10 mL). Potassium carbonate (519 mg, 3.755 mmol) (freshly ground in a mortar) was added and the mixture stirred at 100° C. for 20 h. After cooling down, the reaction was diluted with ethyl acetate (50 mL) and poured into saturated aqueous ammonium chloride (50 mL). The two phases were separated. The aqueous phase was extracted with ethyl acetate (20 mL) and the combined extracts were washed with brine (40 mL). After drying over sodium sulfate and evaporation, the residue was purified by flash chromatography on silica gel using a gradient of ethyl acetate (0 to 100% over 30 min) in hexanes. The pure fractions were collected and the solvents evaporated to give tert-butyl 2,2-dimethyl-4-[5-[(6-sulfamoyl-2-pyridyl)amino]pentyl]pyrrolidine-1-carboxylate (1.184 g, 74%) as a white solid foam. ESI-MS m/z calc. 440.24573, found 441.3 (M+1)$^+$; Retention time: 1.86 min (LC Method B).

Step 10: tert-Butyl 4-[5-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]pentyl]-2,2-dimethyl-pyrrolidine-1-carboxylate

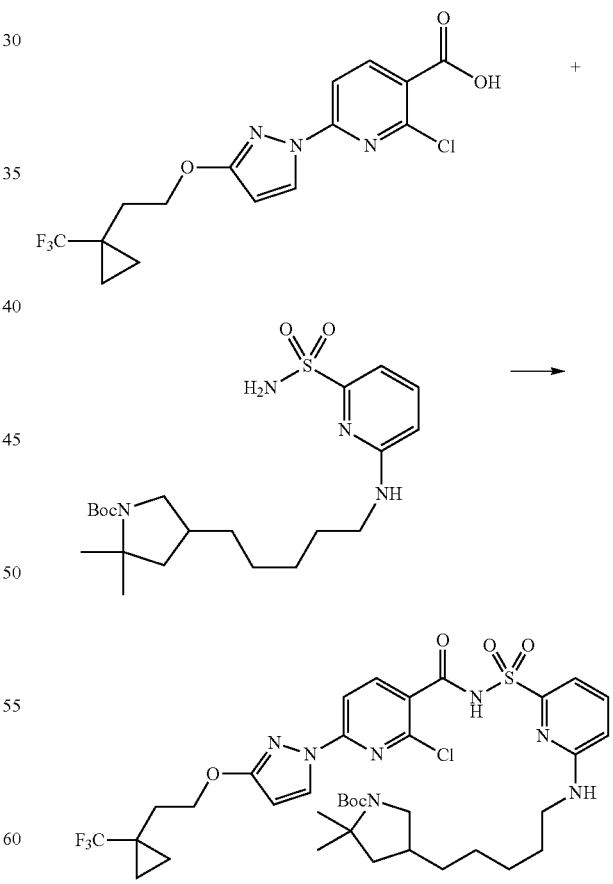

In a 20 mL vial, 2-chloro-6-[3-[2-[1-(trifluoromethyl)cyclopropyl]ethoxy]pyrazol-1-yl]pyridine-3-carboxylic acid (19.8 mg, 0.8511 mmol) and carbonyl diimidazole (138.0 mg, 0.8511 mmol) were combined in tetrahydrofuran (3.588 mL) and stirred for 120 min at 50° C. with a loose cap. Then tert-butyl 2,2-dimethyl-4-[5-[(6-sulfamoyl-2-pyridyl)amino]pentyl]pyrrolidine-1-carboxylate (250 mg, 0.5674 mmol) in tetrahydrofuran (4.785 mL) was added followed by 1,8-diazabicyclo[5.4.0]undec-7-ene (169.7 µL, 1.135 mmol) and the reaction was heated at 50° C. for 16 hrs. The reaction was diluted with ethyl acetate and washed with saturated aqueous ammonium chloride followed by brine. The organics were separated, dried over sodium sulfate, filtered and evaporated then purified by silica gel chromatography using a shallow gradient from 100% hexanes to 100% ethyl acetate giving tert-butyl 4-[5-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]pentyl]-2,2-dimethyl-pyrrolidine-1-carboxylate (416.8 mg, 92%). ESI-MS m/z calc. 797.2949, found 798.3 (M+1)⁺; Retention time: 0.92 min (LC Method A).

Step 11: 2-Chloro-N-[[6-[5-(5,5-dimethylpyrrolidin-3-yl)pentylamino]-2-pyridyl]sulfonyl]-6-[3-[2-[1-(trifluoromethyl)cyclopropyl]ethoxy]pyrazol-1-yl]pyridine-3-carboxamide

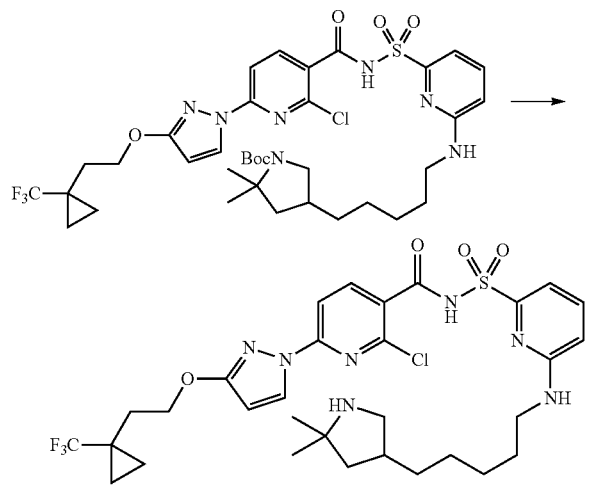

tert-Butyl 4-[5-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]pentyl]-2,2-dimethyl-pyrrolidine-1-carboxylate (416.8 mg, 0.5221 mmol) was dissolved in dichloromethane (1.189 mL) and to the mixture was added trifluoroacetic acid (1.845 mL, 23.95 mmol) and stirred the mixture at room temperature for 60 min. Concentrated mixture to dryness under reduced pressure, took up in saturated aqueous sodium bicarbonate and ethyl acetate and separated the layers. Organic layer was dried (sodium sulfate), filtered and concentrated to a white solid, 2-chloro-N-[[6-[5-(5,5-dimethylpyrrolidin-3-yl)pentylamino]-2-pyridyl]sulfonyl]-6-[3-[2-[1-(trifluoromethyl)cyclopropyl]ethoxy]pyrazol-1-yl]pyridine-3-carboxamide (361 mg, 91%). ESI-MS m/z calc. 697.2425, found 698.2 (M+1)⁺; Retention time: 0.64 min (LC Method A).

Step 12: 12,12-Dimethyl-8-(3-{2-[1-(trifluoromethyl)cyclopropyl]ethoxy}-1H-pyrazol-1-yl)-2λ⁶-thia-3,9,11,20,25-pentaazatetracyclo[19.3.1.1¹¹,¹⁴.0⁵,¹⁰]hexacosa-1(24),5,7,9,21(25),22-hexaene-2,2,4-trione (Enantiomer 1) (Compound 63) and 12,12-dimethyl-8-(3-{2-[1-(trifluoromethyl)cyclopropyl]ethoxy}-1H-pyrazol-1-yl)-2λ⁶-thia-3,9,11,20,25-pentaazatetracyclo[19.3.1.1¹¹,¹⁴.0⁵,¹⁰]hexacosa-1(24),5,7,9,21(25),22-hexaene-2,2,4-trione (Enantiomer 2) (Compound 64)

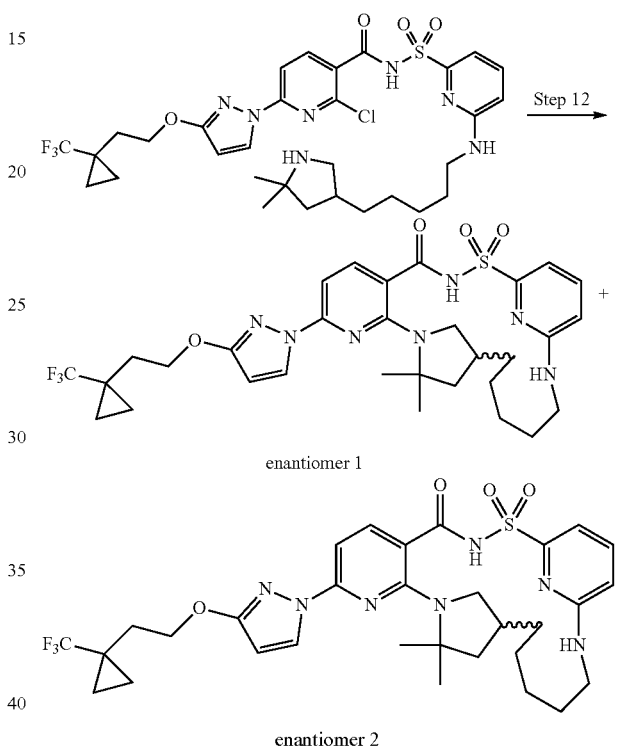

enantiomer 1 enantiomer 2

To a solution of 2-chloro-N-[[6-[5-(5,5-dimethylpyrrolidin-3-yl)pentylamino]-2-pyridyl]sulfonyl]-6-[3-[2-[1-(trifluoromethyl)cyclopropyl]ethoxy]pyrazol-1-yl]pyridine-3-carboxamide (361 mg, 0.4736 mmol) in dimethyl sulfoxide (13.22 mL) was added potassium carbonate (392.6 mg, 2.841 mmol), cesium fluoride (86.33 mg, 0.5683 mmol) and a small amount of 3 Å molecular sieves. The resulting mixture was capped and heated to 165° C. for 16 h. The mixture was then cooled to room temperature, diluted with ethyl acetate and washed with saturated aqueous ammonium chloride and brine. The organic phase was dried (sodium sulfate), filtered and concentrated to 422 mg of a tan amorphous solid which was subjected to chiral separation by SFC chromatography using a LUX 3 (250×21 mm column, 5 µm particle size) with 60% methanol (20 mM NH₃ additive))/40% carbon dioxide mobile phase at 30 mL/min giving as the first enantiomer to elute, 12,12-dimethyl-8-(3-{2-[1-(trifluoromethyl)cyclopropyl]ethoxy}-1H-pyrazol-1-yl)-2λ⁶-thia-3,9,11,20,25-pentaazatetracyclo[19.3.1.1¹¹,¹⁴.0⁵,¹⁰]hexacosa-1(24),5,7,9,21(25),22-hexaene-2,2,4-trione (enantiomer 1) (Compound 63) (74.4 mg, 47%) as a white solid; ¹H NMR (400 MHz, dimethyl sulfoxide-d₆) δ 12.69 (bs, 1H), 8.19 (d, J=2.7 Hz, 1H), 7.78 (d, J=8.2 Hz, 1H), 7.48 (s, 1H), 7.08 (d, J=6.9 Hz, 2H), 6.85 (d, J=8.0 Hz, 1H), 6.58 (s, 1H), 6.07 (d, J=2.6 Hz, 1H), 4.31 (t, J=7.0 Hz, 2H), 3.84 (d, J=14.2 Hz, 1H), 3.06 (s, 1H), 2.89 (s, 1H), 2.79 (s, 1H), 2.08 (t, J=7.1 Hz, 3H), 1.81 (dd, J=11.6, 5.4 Hz, 1H), 1.60 (d, J=9.1 Hz, 1H), 1.55 (d, J=6.2 Hz, 6H), 1.47 (d, J=12.5 Hz, 3H), 1.27 (d, J=26.3 Hz, 3H), 1.01 (s, 1H), 0.98-0.93 (m, 2H), 0.93-0.84 (m, 3H), ESI-MS m/z calc. 661.2658, found 662.2 (M+1)+; Retention time: 2.29 min (LC Method B) and as the second enantiomer to elute, 12,12-dimethyl-8-(3-{2-[1-(trifluoromethyl)cyclopropyl]ethoxy}-1H-pyrazol-1-yl)-2λ$^6$-thia-3,9,11,20,25-pentaazatetracyclo[19.3.1.1$^{11,14}$.0$^{5,10}$]hexacosa-1(24),5,7,9,21(25),22-hexaene-2,2,4-trione (enantiomer 2) (Compound 64) (79.2 mg, 50%) as a white solid; $^1$H NMR (400 MHz, dimethyl sulfoxide-d$_6$) δ 12.50 (s, 1H), 8.21 (d, J=2.8 Hz, 1H), 7.82 (d, J=8.2 Hz, 1H), 7.56 (s, 1H), 7.14 (s, 1H), 6.91 (d, J=7.8 Hz, 2H), 6.70 (s, 1H), 6.11 (s, 1H), 4.31 (t, J=7.0 Hz, 2H), 3.88 (s, 1H), 3.06 (s, 1H), 2.74 (s, 1H), 2.62 (d, J=32.1 Hz, 1H), 2.08 (t, J=7.1 Hz, 2H), 1.83 (dd, J=11.8, 5.3 Hz, 1H), 1.67-1.57 (m, 1H), 1.55 (d, J=10.5 Hz, 6H), 1.48 (t, J=12.1 Hz, 3H), 1.30 (s, 2H), 1.23 (s, 1H), 1.01 (d, J=9.5 Hz, 1H), 0.98-0.95 (m, 2H), 0.95-0.87 (m, 3H), ESI-MS m/z calc. 661.2658, found 662.2 (M+1)+; Retention time: 2.29 min (LC Method B).

Example 17: Preparation of (14S)-8-[3-(3,3-dicyclopropylpropoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 66)

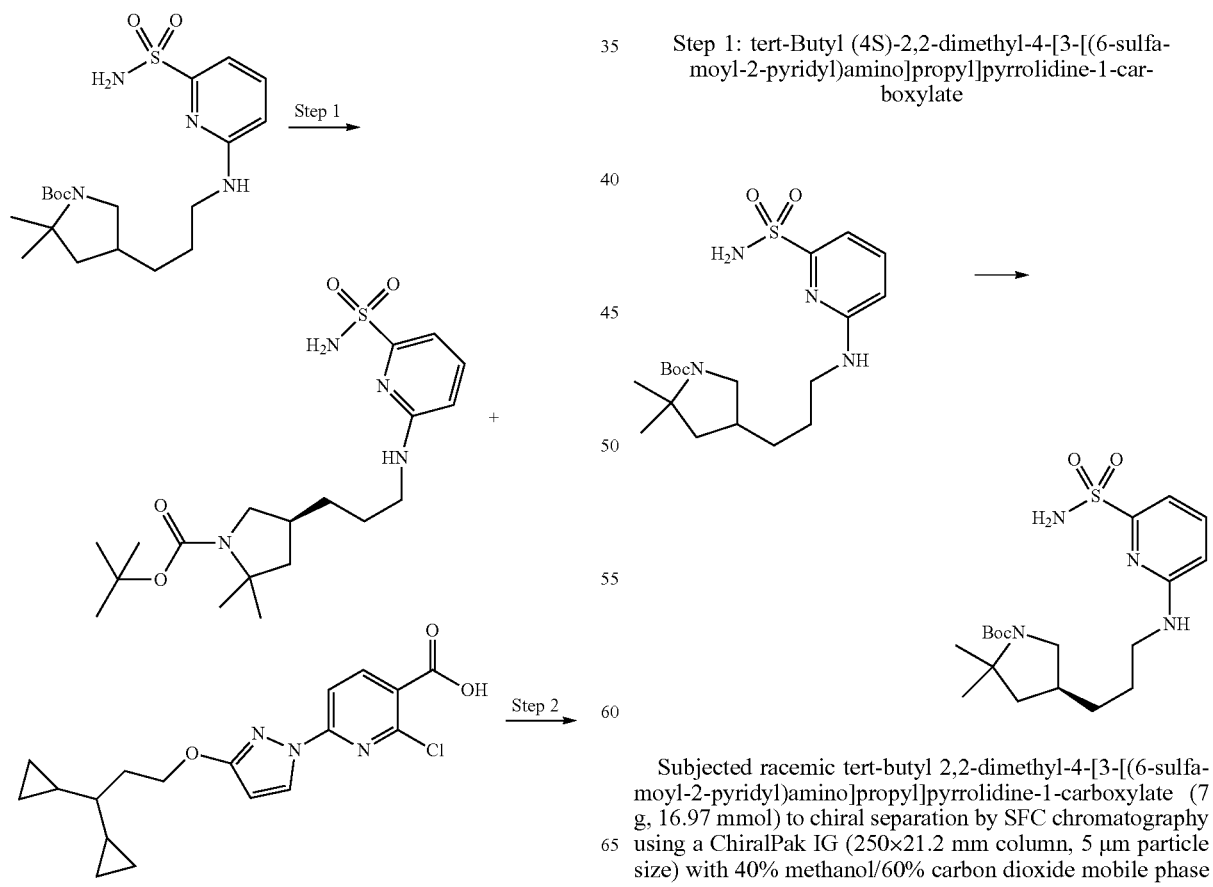

Step 1: tert-Butyl (4S)-2,2-dimethyl-4-[3-[(6-sulfamoyl-2-pyridyl)amino]propyl]pyrrolidine-1-carboxylate Subjected racemic tert-butyl 2,2-dimethyl-4-[3-[(6-sulfamoyl-2-pyridyl)amino]propyl]pyrrolidine-1-carboxylate (7 g, 16.97 mmol) to chiral separation by SFC chromatography using a ChiralPak IG (250×21.2 mm column, 5 µm particle size) with 40% methanol/60% carbon dioxide mobile phase at 70 mL/min over 11.0 min (injection volume=500 µL of 32 mg/mL solution in methanol) giving as the first peak to elute, tert-butyl (4S)-2,2-dimethyl-4-[3-[(6-sulfamoyl-2-pyridyl)amino]propyl]pyrrolidine-1-carboxylate (3.4481 g, 99%). ESI-MS m/z calc. 412.21442, found 413.2 (M+1); Retention time: 0.63 min (LC Method A).

Step 2: tert-Butyl (4S)-4-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate

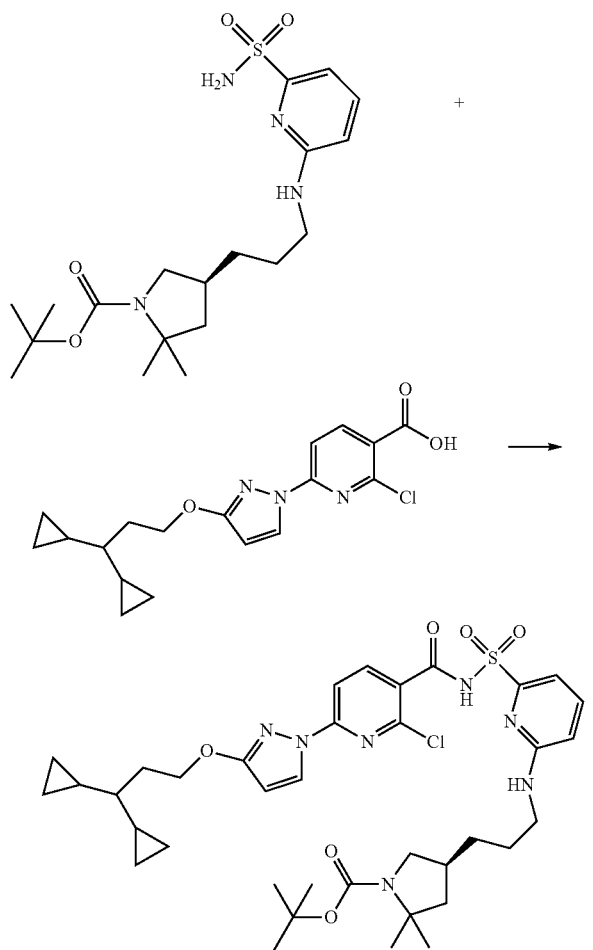

Part A: To 2-chloro-6-[3-(3,3-dicyclopropylpropoxy)pyrazol-1-yl]pyridine-3-carboxylic acid (8.9 g, 24.60 mmol) in tetrahydrofuran (80 mL) was slowly added carbonyl diimidazole (4.4 g, 27.14 mmol). The mixture was stirred at ambient temperature for 1 hr.

Part B: To tert-butyl (4S)-2,2-dimethyl-4-[3-[(6-sulfamoyl-2-pyridyl)amino]propyl]pyrrolidine-1-carboxylate (10.1 g, 24.48 mmol) in tetrahydrofuran (40 mL) was added 2,3,4,6,7,8,9,10-octahydropyrimido[1,2-a]azepine (11.0 mL, 73.56 mmol) followed by the activated ester from Part A and the mixture was stirred at ambient temperature for 16 hr. The reaction was quenched with 50 mL of water and most of the tetrahydrofuran was removed under vacuum. The remaining mixture was diluted with water (250 mL) containing hydrochloric acid (26 mL of 6 M, 156.0 mmol) and acidified to pH=2-3. The clear dark yellow solution was extracted with ethyl acetate (400 mL). The organic phase was washed with 300 mL of brine, dried over magnesium sulfate, filtered and concentrated under vacuum affording a thick yellow oil. The crude reaction mixture was chromatographed on a $C_{18}$ 415 g reverse phase column eluting with 50-100% water/acetonitrile to afford tert-butyl (4S)-4-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate (11.2 g, 60%). ESI-MS m/z calc. 755.3232, found 756.3 (M+1)$^+$; Retention time: 2.53 min (LC Method B).

Step 3: 2-Chloro-6-[3-(3,3-dicyclopropylpropoxy)pyrazol-1-yl]-N-[[6-[3-[(3S)-5,5-dimethylpyrrolidin-3-yl]propylamino]-2-pyridyl]sulfonyl]pyridine-3-carboxamide (Trifluoroacetic Acid Salt)

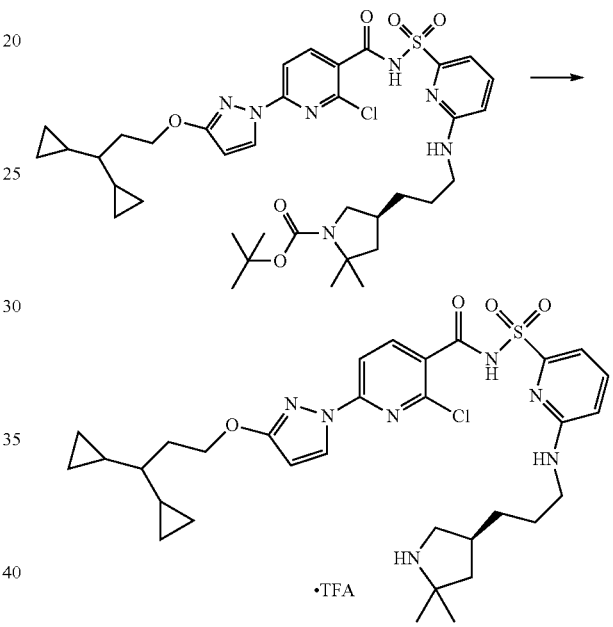

To tert-butyl (4S)-4-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate (16.7 g, 22.08 mmol) in dichloromethane (80 mL) and toluene (40 mL) was added trifluoroacetic acid (10 mL, 129.8 mmol) and the mixture was stirred at ambient temperature for 22 h. The solvent was removed by rotary evaporation at 35° C. affording a thick yellow oil. The oil was diluted with dichloromethane (80 mL) and toluene (120 mL) and the solvent removed by rotary evaporation at 55° C. The process was repeated with dichloromethane and toluene affording 2-chloro-6-[3-(3,3-dicyclopropylpropoxy)pyrazol-1-yl]-N-[[6-[3-[(3S)-5,5-dimethylpyrrolidin-3-yl]propylamino]-2-pyridyl]sulfonyl]pyridine-3-carboxamide (trifluoroacetate salt) (22.6 g, 133%, product contaminated with residual toluene and trifluoroacetic acid) as thick oil. $^1$H NMR (400 MHz, dimethyl sulfoxide-$d_6$) δ 12.73 (s, 1H), 8.60 (s, 2H), 8.39 (d, J=2.9 Hz, 1H), 8.11 (d, J=8.3 Hz, 1H), 7.71 (d, J=8.4 Hz, 1H), 7.63 (dd, J=8.5, 7.2 Hz, 1H), 7.26-7.22 (m, 1H), 6.75 (dd, J=8.5, 0.7 Hz, 1H), 6.20 (d, J=2.9 Hz, 1H), 4.40 (t, J=6.8 Hz, 2H), 3.36 (dq, J=12.0, 5.3 Hz, 1H), 3.24 (hept, J=6.7 Hz, 2H), 2.80 (td, J=11.8, 10.8, 6.1 Hz, 1H), 2.41-2.32 (m, 1H), 2.02-1.85 (m, 3H), 1.61-1.28 (m, 8H), 1.24 (d, J=6.2 Hz, 4H), 0.69 (qt, J=8.3, 5.0 Hz, 2H), 0.49-0.34 (m, 3H), 0.34-0.25 (m, 1H), 0.25-0.14 (m, 2H), 0.11-0.00 (m, 2H). ESI-MS m/z calc. 655.27075, found 656.3 (M+1)+; Retention time: 1.71 min (LC Method B).

Step 4: (14S)-8-[3-(3,3-Dicyclopropylpropoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 66)

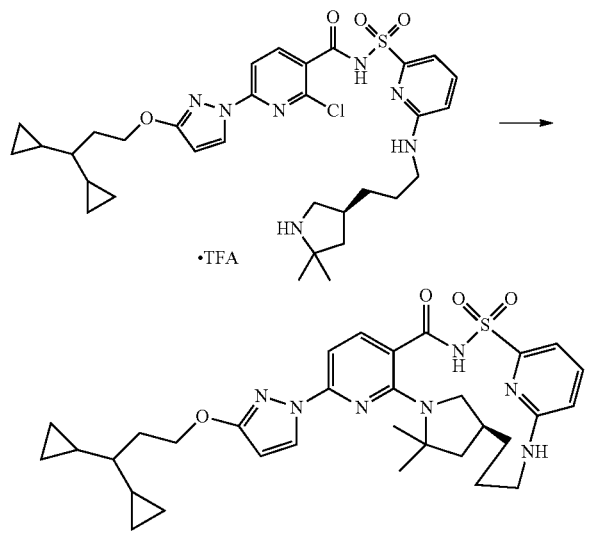

To a solution of 2-chloro-6-[3-(3,3-dicyclopropylpropoxy)pyrazol-1-yl]-N-[[6-[3-[(3S)-5,5-dimethylpyrrolidin-3-yl]propylamino]-2-pyridyl]sulfonyl]pyridine-3-carboxamide (trifluoroacetate salt) (17.5 g, 22.72 mmol) in NMP (300 mL) was added potassium carbonate (15.3 g, 110.7 mmol) followed by cesium fluoride (3.8 g, 25.02 mmol). The mixture was purged with nitrogen for 5 min. The mixture was heated at 150° C. for 20 hr. The reaction mixture was cooled to room temperature, added to water (1200 mL) (used a 5 L flask chilled with an ice-bath) and acidified by careful addition of hydrochloric acid (20 mL of 6 M, 120.0 mmol) and then solid citric acid (45 g, 234.2 mmol). The mixture was stirred in an ice bath for 1 hr. The solid was collected by filtration using a medium frit (slow filtration) and the wet filter cake was dissolved in ethyl acetate (1,000 mL) and washed with 500 mL of brine. The aqueous phase was separated and the organic phase was dried over magnesium sulfate, filtered over Celite and concentrated under vacuum affording a light yellow foam. The crude product was diluted with acetonitrile and split into 3 equal volumes (15 mL) and chromatographed on a $C_{18}$ 415 g reverse phase Column eluting with 50-100% acetonitrile/water to afford (14S)-8-[3-(3,3-dicyclopropylpropoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 66) (8.91 g, 63%). ¹H NMR (400 MHz, dimethyl sulfoxide-$d_6$) δ 12.48 (s, 1H), 8.20 (d, J=3.2 Hz, 1H), 7.81 (d, J=8.0 Hz, 1H), 7.57 (t, J=7.8 Hz, 1H), 7.05 (d, J=7.0 Hz, 1H), 6.97 (s, 2H), 6.71 (d, J=8.4 Hz, 1H), 6.10 (d, J=3.2 Hz, 1H), 4.37 (t, J=6.7 Hz, 2H), 3.91 (s, 1H), 3.15 (s, 1H), 2.95 (d, J=13.3 Hz, 1H), 2.71 (s, 1H), 2.12 (s, 1H), 1.95-1.71 (m, 4H), 1.60 (d, J=3.3 Hz, 6H), 1.51 (s, 3H), 1.39-1.25 (m, 1H), 0.67 (dt, J=8.5, 4.1 Hz, 2H), 0.47-0.33 (m, 4H), 0.30 (t, J=8.0 Hz, 1H), 0.20 (dd, J=9.7, 4.4 Hz, 2H), 0.04 (d, J=8.3 Hz, 2H). ESI-MS m/z calc. 619.29407, found 620.3 (M+1)+; Retention time: 10.3 min (LC Method F).

Example 18: Preparation of 12,12-dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Enantiomer 1) (Compound 72) and 12,12-dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Enantiomer 2) (Compound 73)

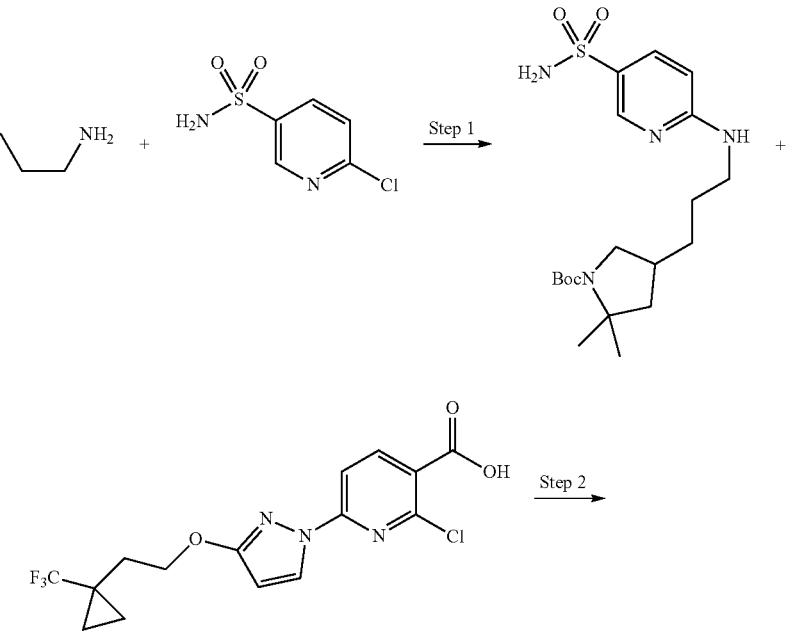

-continued
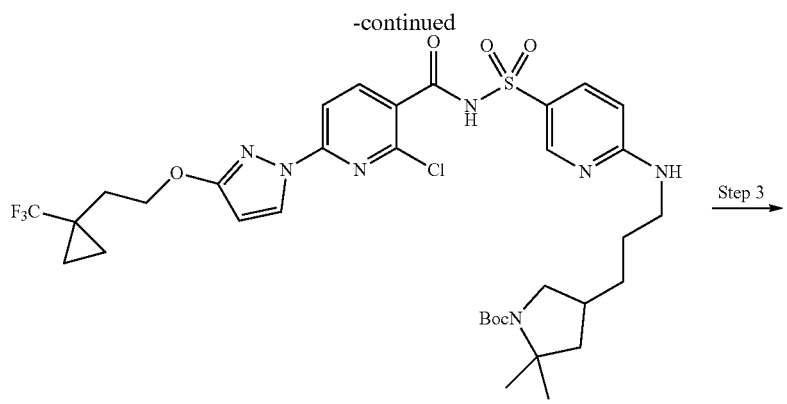
Step 3
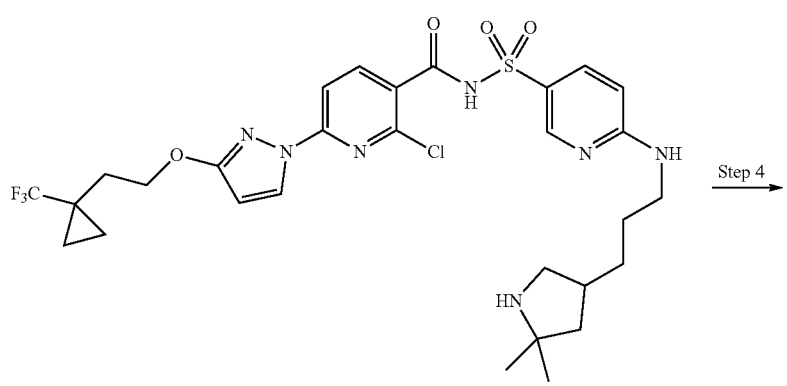
Step 4
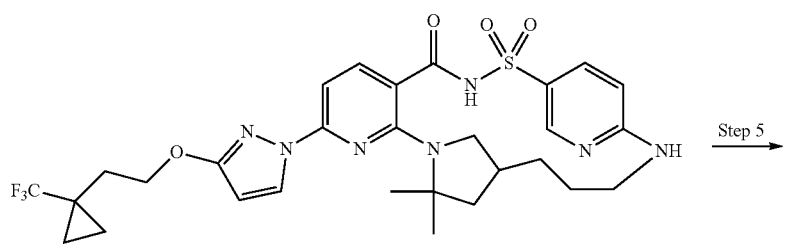
Step 5
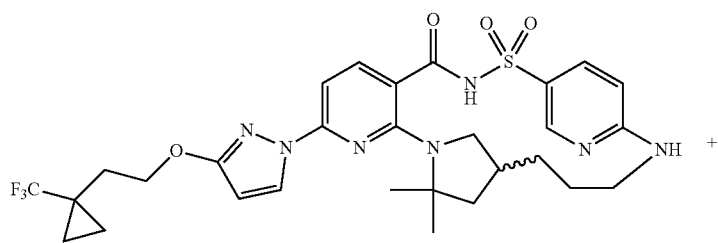
enantiomer 1
+
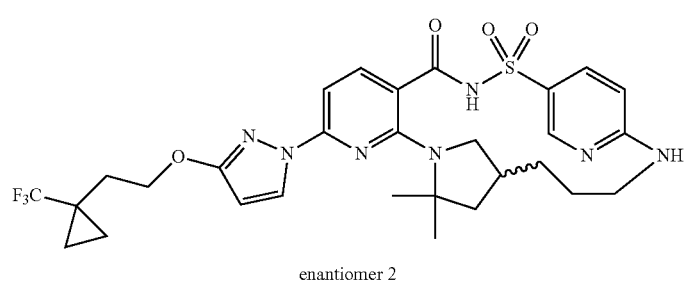 [SMILES: CC1(C)CC2CCCNc3ccc(cn3)S(=O)(=O)NC(=O)c3ccc(-n4ccc(OCCC5(C(F)(F)F)CC5)n4)nc3N1C2]
enantiomer 2

Step 1: tert-Butyl 2,2-dimethyl-4-[3-[(5-sulfamoyl-2-pyridyl)amino]propyl]pyrrolidine-1-carboxylate

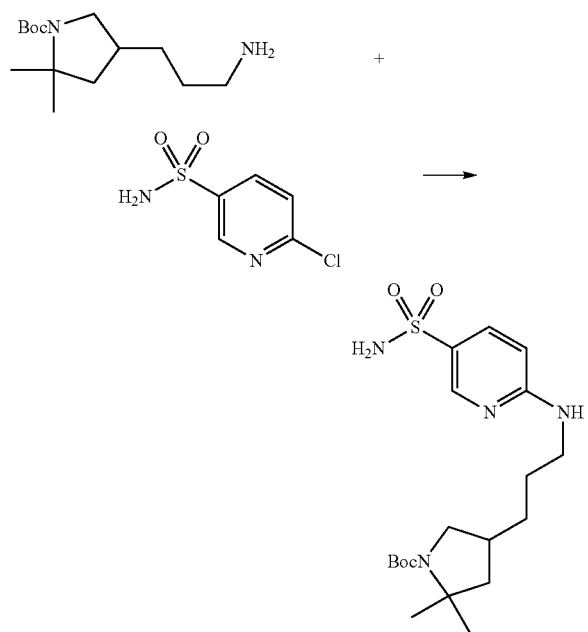

To tert-butyl 4-(3-aminopropyl)-2,2-dimethyl-pyrrolidine-1-carboxylate (400 mg, 1.560 mmol) and 6-chloropyridine-3-sulfonamide (300.5 mg, 1.560 mmol) in dimethyl sulfoxide (3.368 mL) was added potassium carbonate (219.9 mg, 1.591 mmol) and the mixture stirred at 100° C. for 20 h then allowed to cool to room temperature. Diluted with ethyl acetate and poured into saturated aqueous ammonium chloride. Separated the layers then washed the organic layer with saturated aqueous brine, dried (sodium sulfate), filtered and concentrated to a yellow foam which was purified by silica gel chromatography using a shallow gradient from 100% hexanes to 100% ethyl acetate giving tert-butyl 2,2-dimethyl-4-[3-[(5-sulfamoyl-2-pyridyl)amino]propyl]pyrrolidine-1-carboxylate (347 mg, 54%) as a white solid. ESI-MS m/z calc. 412.21442, found 413.2 (M+1)$^+$; Retention time: 0.52 min (LC Method A).

Step 2: tert-Butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate

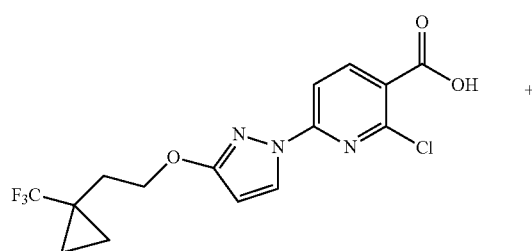

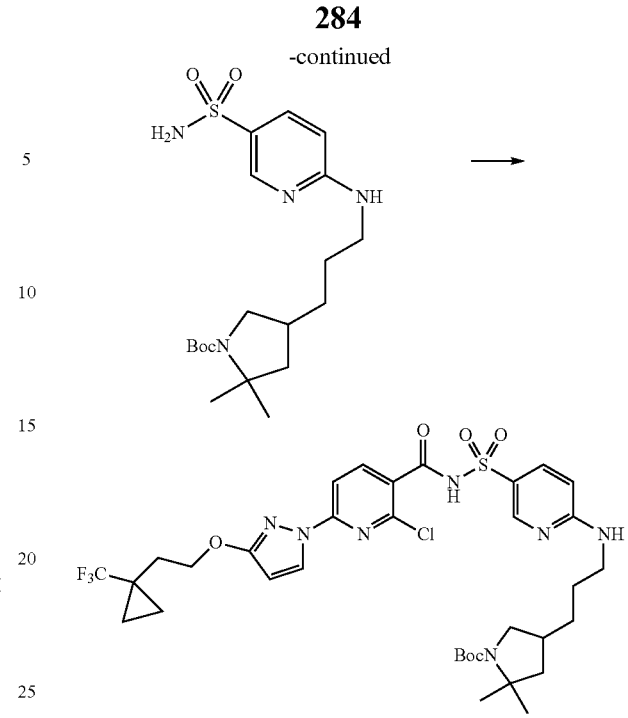

In a 20 mL vial 2-chloro-6-[3-[2-[1-(trifluoromethyl)cyclopropyl]ethoxy]pyrazol-1-yl]pyridine-3-carboxylic acid (474.2 mg, 1.262 mmol) and carbonyl diimidazole (204.6 mg, 1.262 mmol) were combined in tetrahydrofuran (4.979 mL) and stirred for 120 min at 50° C. with a loose cap. Then tert-butyl 2,2-dimethyl-4-[3-[(5-sulfamoyl-2-pyridyl)amino]propyl]pyrrolidine-1-carboxylate (347 mg, 0.8411 mmol) in tetrahydrofuran (6.642 mL) was added followed by 1,8-diazabicyclo[5.4.0]undec-7-ene (251.6 µL, 1.682 mmol) and the reaction was heated at 50° C. for 16 hrs. The reaction was diluted with ethyl acetate and washed with saturated aqueous ammonium chloride followed by brine. The organics were separated, dried over sodium sulfate, filtered and evaporated then purified by silica gel chromatography using a shallow gradient from 100% hexanes to 100% ethyl acetate giving pure product as well as mixed fractions. Mixed fractions were concentrated and repurified using a reverse phase HPLC-MS method using a Luna C$_{18}$ (2) column (75×30 mm, 5 µm particle size) sold by Phenomenex (pn: 00C-4252-U0-AX) and a dual gradient run from 30-99% mobile phase B over 15.0 min (mobile phase A=water (5 mM hydrochloric acid), mobile phase B=acetonitrile, flow rate=50 mL/min, injection volume=950 µL and column temperature=25° C.). Pure fractions from reverse-phase prep purification were combined and acetonitrile was removed by rotary evaporation. The residue was dissolved in ethyl acetate and washed with a small amount of saturated aqueous sodium bicarbonate then dried (sodium sulfate), filtered and concentrated to a white solid which was combined with the pure product from the silica gel column to give tert-butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate (539.2 mg, 83%) as a white solid. ESI-MS m/z calc. 769.2636, found 770.2 (M+1)$^+$; Retention time: 0.84 min (LC Method A).

Step 3: 2-Chloro-N-[[6-[3-(5,5-dimethylpyrrolidin-3-yl)propylamino]-3-pyridyl]sulfonyl]-6-[3-[2-[1-(trifluoromethyl)cyclopropyl]ethoxy]pyrazol-1-yl]pyridine-3-carboxamide

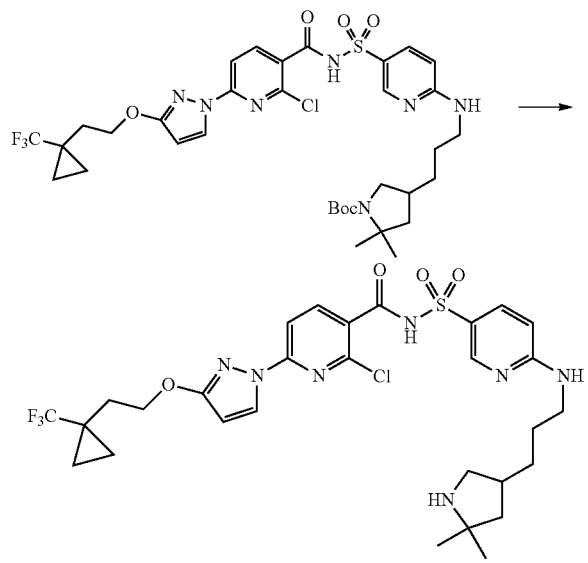

tert-Butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate (539.2 mg, 0.7000 mmol) was dissolved in dichloromethane (2.353 mL) and to the mixture was added trifluoroacetic acid (2.474 mL, 32.11 mmol) and the mixture was stirred at room temperature for 60 min. Concentrated mixture to dryness under reduced pressure, took up in saturated aqueous sodium bicarbonate and ethyl acetate and separated the layers (solubility of product in ethyl acetate under these conditions is poor, addition of some methanol helps, needed to evaporate the organic layer without using solid drying agent). Concentrated the organic layer by rotary evaporation followed by drying under vacuum giving 2-chloro-N-[[6-[3-(5,5-dimethylpyrrolidin-3-yl)propylamino]-3-pyridyl]sulfonyl]-6-[3-[2-[1-(trifluoromethyl)cyclopropyl]ethoxy]pyrazol-1-yl]pyridine-3-carboxamide (423.3 mg, 90%) as an off-white solid. ESI-MS m/z calc. 669.2112, found 670.2 (M+1)+; Retention time: 0.56 min (LC Method A).

Step 4: 12,12-Dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Compound 62)

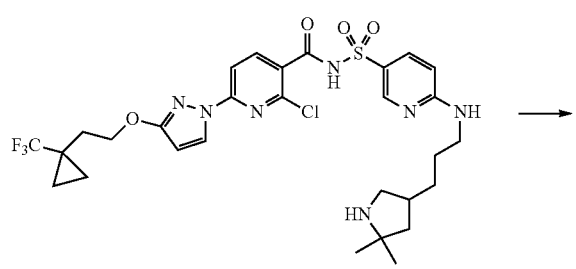

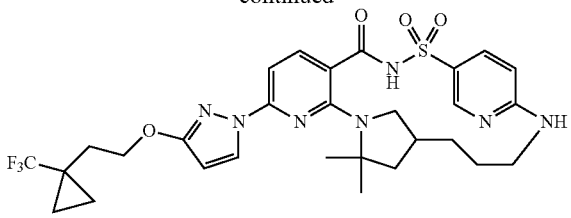

To a solution of 2-chloro-N-[[6-[3-(5,5-dimethylpyrrolidin-3-yl)propylamino]-3-pyridyl]sulfonyl]-6-[3-[2-[1-(trifluoromethyl)cyclopropyl]ethoxy]pyrazol-1-yl]pyridine-3-carboxamide (423.3 mg, 0.6317 mmol) in dimethyl sulfoxide (16.93 mL) was added potassium carbonate (523.8 mg, 3.790 mmol), cesium fluoride (115.1 mg, 0.7577 mmol) and a small amount of 3 Å molecular sieves. The resulting mixture was capped and heated to 165° C. for 16 h. Increased the temperature to 175° C. and stirred 3 h then cooled to room temperature, diluted with ethyl acetate and washed with saturated aqueous ammonium chloride and brine. The organic phase was dried (sodium sulfate), filtered and concentrated to 500 mg of a tan amorphous solid which was filtered and purified using a reverse phase HPLC-MS method using a Luna $C_{18}$ (2) column (75×30 mm, 5 μm particle size) sold by Phenomenex (pn: 00C-4252-U0-AX) and a dual gradient run from 30-99% mobile phase B over 15.0 min (mobile phase A=water (5 mM hydrochloric acid), mobile phase B=acetonitrile, flow rate=50 mL/min, injection volume=950 μL and column temperature=25° C.) giving 12,12-dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Compound 62) (24.2 mg, 6%) as a white solid. ¹H NMR (400 MHz, dimethyl sulfoxide-d₆) δ 12.13 (s, 1H), 8.38 (s, 1H), 8.17 (d, J=2.8 Hz, 1H), 7.91-7.64 (m, 2H), 7.42 (s, 1H), 6.63 (d, J=8.8 Hz, 1H), 6.09 (d, J=2.7 Hz, 1H), 4.30 (t, J=7.1 Hz, 2H), 3.64 (s, 1H), 2.88 (s, 1H), 2.07 (t, J=7.1 Hz, 3H), 2.03-1.92 (m, 2H), 1.80-1.71 (m, 1H), 1.54 (s, 3H), 1.48 (s, 3H), 1.38 (q, J=13.8, 11.4 Hz, 4H), 0.98-0.92 (m, 2H), 0.92-0.85 (m, 3H). ESI-MS m/z calc. 633.2345, found 634.2 (M+1)+; Retention time: 2.03 min (LC Method B).

Step 5: 12,12-Dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Enantiomer 1) (Compound 72) and 12,12-dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Enantiomer 2) (Compound 73)

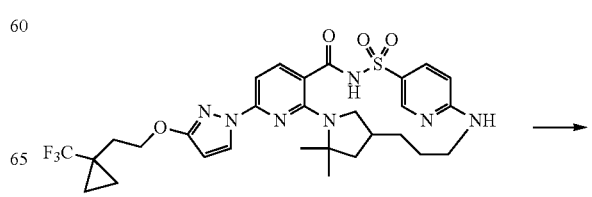

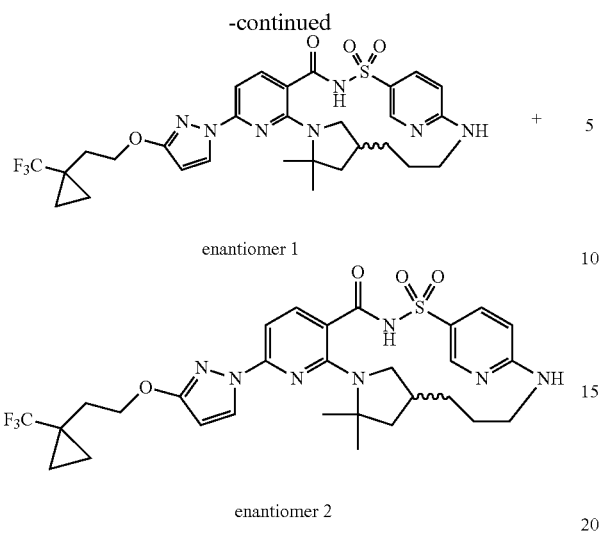

enantiomer 1 enantiomer 2

Subjected racemic 12,12-dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (17 mg, 0.02565 mmol) to chiral separation by SFC chromatography using a ChiralPak AS-H (250×10 mm column, 5 μm particle size) with 18% methanol (20 mM NH₃ additive)/82% carbon dioxide mobile phase at 10 mL/min over 8.0 min (injection volume=70 μL of 24 mg/mL solution in 90% methanol/10% dimethyl sulfoxide giving as the first enantiomer to elute, 12,12-dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (enantiomer 1) (Compound 72) (6.34 mg, 78%) as a white solid; ESI-MS m/z calc. 633.2345, found 634.4 (M+1)⁺; Retention time: 2.08 min (LC Method B) and as the second enantiomer to elute, 12,12-dimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23), 20-hexaene-2,2,4-trione (enantiomer 2) (Compound 73) (5.54 mg, 68%) as a white solid. ¹H NMR (400 MHz, dimethyl sulfoxide-d₆) δ 12.13 (s, 1H), 8.63 (s, 1H), 8.43 (s, 1H), 8.18 (d, J=2.8 Hz, 1H), 7.89 (d, J=8.8 Hz, 1H), 7.85 (d, J=8.4 Hz, 1H), 7.54 (s, 1H), 6.90 (dd, J=8.3, 3.5 Hz, 1H), 6.67 (dd, J=9.0, 3.1 Hz, 1H), 6.11 (d, J=2.8 Hz, 1H), 4.31 (t, J=7.0 Hz, 2H), 3.66 (s, 1H), 2.90 (s, 1H), 2.08 (d, J=7.1 Hz, 2H), 1.92 (s, 3H), 1.77 (d, J=12.5 Hz, 1H), 1.64 (d, J=13.8 Hz, 1H), 1.55 (s, 3H), 1.48 (s, 3H), 1.46-1.34 (m, 3H), 1.34 (s, 1H), 0.97-0.94 (m, 2H), 0.88 (s, 2H). ESI-MS m/z calc. 633.2345, found 634.3 (M+1)⁺; Retention time: 2.08 min (LC Method B).

Example 19: Preparation of (14S)-12,12-dimethyl-8-(3-{2-[1-(trifluoromethyl) cyclopropyl]ethoxy}-1H-pyrazol-1-yl)-18-oxa-2λ⁶-thia-3,9,11-triazatetracyclo[17.3.1.1¹¹,¹⁴.0⁵,¹⁰]tetracosa-1(23),5(10),6,8,19,21-hexaene-2,2,4-trione (Compound 77)

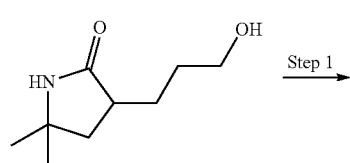

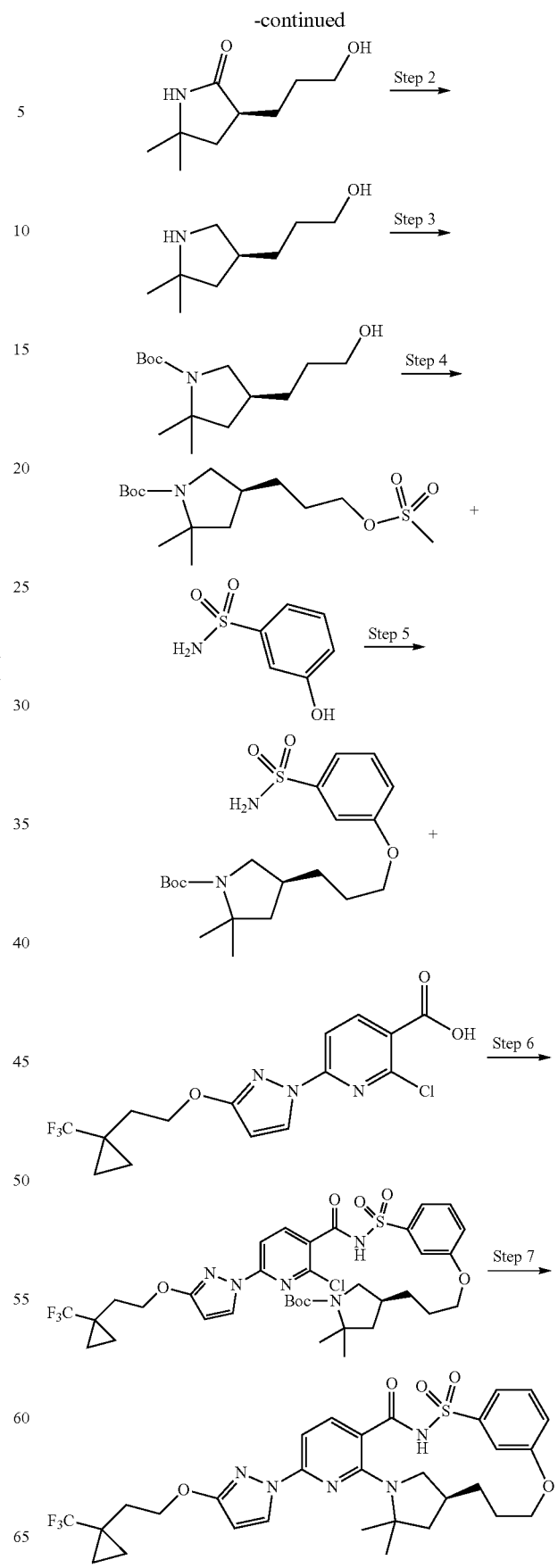

From: (3S)-3-(3-Hydroxypropyl)-5,5-dimethyl-pyrrolidin-2-one

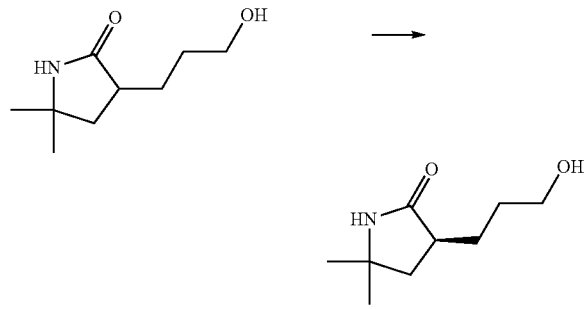

Racemic 3-(3-hydroxypropyl)-5,5-dimethyl-pyrrolidin-2-one (100 g, 566.5 mmol) was separated by chiral SFC chromatography using a ChiralPak AD-H (2×25 cm column) with 30% methanol/carbon dioxide mobile phase at 60 mL/min (injection volume=1 mL of 20 mg/mL solution in methanol giving as the first enantiomer to elute, (3S)-3-(3-hydroxypropyl)-5,5-dimethyl-pyrrolidin-2-one (47 g, 48%) as an off white solid. $^1$H NMR (400 MHz, dimethyl sulfoxide-$d_6$) δ 7.63 (s, 1H), 4.38 (t, J=5.1 Hz, 1H), 3.39 (t, J=5.6 Hz, 2H), 2.37 (ddt, J=13.9, 9.6, 4.4 Hz, 1H), 2.02 (dd, J=12.3, 8.6 Hz, 1H), 1.78-1.64 (m, 1H), 1.42 (td, J=12.8, 12.3, 8.4 Hz, 3H), 1.16 (d, J=17.9 Hz, 7H). ESI-MS m/z calc. 171.12593, found 172.0 (M+1)$^+$; Retention time: 0.61 min (LC Method B).

Step 2: 3-[(3S)-5,5-Dimethylpyrrolidin-3-yl]propan-1-ol

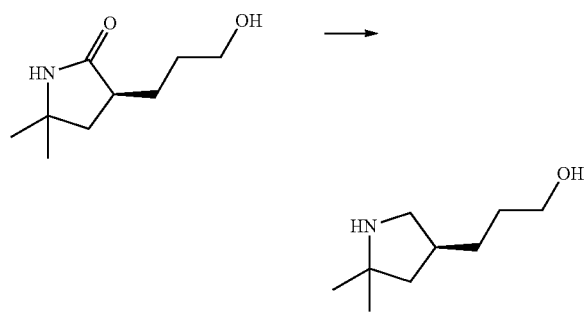

A 5 L, 3-neck round bottom flask was fitted with a mechanical stirrer, a heating mantle, an addition funnel, a J-Kem temperature probe/controller and a nitrogen inlet/outlet. The vessel was charged under a nitrogen atmosphere with lithium aluminum hydride pellets (46.53 g, 1.226 mol) pellets. The vessel was then charged with tetrahydrofuran (500 mL, 20 mL/g). Stirring was commenced and the pot temperature was recorded at 20° C. The mixture was allowed to stir at room temperature for 0.5 h to allow the pellets to dissolve. The pot temperature of the resulting grey suspension was recorded at 24° C. The addition funnel was charged with a solution of (3S)-3-(3-hydroxypropyl)-5,5-dimethyl-pyrrolidin-2-one (60 g, 350.4 mmol) in tetrahydrofuran (600 mL) and the clear pale yellow solution was added dropwise over 90 min. Slight heating was required to get into solution. After the completed addition the pot temperature of the resulting greyish suspension was recorded at 24° C. The mixture was then heated to a pot temperature of 65° C. and the condition was maintained for 72 h. Analysis of the reaction mixture at this point indicated some residual starting material still remaining and no change in product formation. The reaction was subsequently stopped at this point. The heating mantle was removed and the vessel was fitted with a cooling bath. The suspension was cooled to 0° C. with a crushed ice/water cooling bath and then quenched by the very slow dropwise addition of water (46.53 mL), followed by 15 wt % sodium hydroxide solution (46.53 mL) and then finally with water (139.59 mL). The pot temperature of the resulting white suspension was recorded at 5° C. The cooling bath was removed and the vessel was again fitted with a heating mantle. The suspension was warmed to 60° C. and the condition was maintained for 30 min. The warm suspension was vacuum filtered through a glass frit Buchner funnel with a 25 mm layer of celite. The filter cake was then displacement washed with 60° C. tetrahydrofuran (2×350 mL) and then pulled for 30 min. The clear filtrate was concentrated under reduced pressure to provide (55 g, 0.349 mol, 99% yield) of a clear light yellow viscous oil as the desired product, 3-[(3S)-5,5-dimethylpyrrolidin-3-yl]propan-1-ol (55 g, 100%). $^1$H NMR (400 MHz, dimethyl sulfoxide-$d_6$) δ 3.36 (t, J=6.3 Hz, 3H), 2.95 (dd, J=10.6, 7.6 Hz, 1H), 2.40 (dd, J=10.6, 7.7 Hz, 1H), 2.12-1.97 (m, 1H), 1.69 (dd, J=12.1, 8.2 Hz, 1H), 1.47-1.25 (m, 5H), 1.08 (s, 3H), 1.02 (s, 3H).

Step 3: tert-Butyl (4S)-4-(3-hydroxypropyl)-2,2-dimethyl-pyrrolidine-1-carboxylate

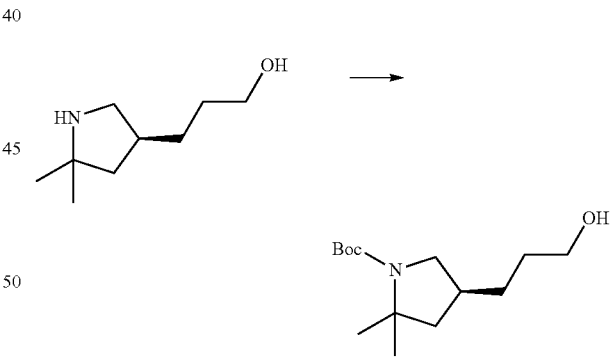

A 1 L, 3-neck round bottom flask was fitted with a mechanical stirrer, a cooling bath, an addition funnel, a J-Kem temperature probe and a nitrogen inlet/outlet. The vessel was charged under a nitrogen atmosphere with 3-[(3S)-5,5-dimethylpyrrolidin-3-yl]propan-1-ol (25 g, 159.0 mmol) and dichloromethane (250 mL) which provided a clear light yellow solution. Stirring was commenced and the pot temperature was recorded at 19° C. The cooling bath was charged with crushed ice/water and the pot temperature was lowered to 0° C. The addition funnel was charged with triethylamine (22.16 mL, 159.0 mmol) which was subsequently added neat dropwise over 5 min. No exotherm was observed. The addition funnel was then charged with di-tert-butyl dicarbonate (31.32 g, 143.5 mmol) dissolved in dichloromethane (150 mL). The clear pale yellow solution was then added dropwise over 30 min which resulted in gentle gas evolution. No exotherm was observed. The cooling bath was removed and the resulting clear light yellow solution was allowed to warm to room temperature and continue to stir at room temperature for 3 h. The reaction mixture was transferred to a separatory funnel and partitioned with water (75 mL). The organic was removed and washed with saturated sodium chloride solution (75 mL), dried over sodium sulfate (150 g) and then filtered through a glass frit Buchner funnel. The filtrate was concentrated under reduced pressure to provide (45 g) of a clear light yellow oil as the desired crude product. The material was purified by silica gel column flash chromatography (liquid load with dichloromethane) eluting with a gradient of 100% dichloromethane to 10% methyl alcohol in dichloromethane over 60 min collecting 50 mL fractions. The desired product fractions were combined and concentrated under reduced pressure to provide tert-butyl (4S)-4-(3-hydroxypropyl)-2,2-dimethyl-pyrrolidine-1-carboxylate (39 g, 95%). $^1$H NMR (400 MHz, dimethyl sulfoxide-d$_6$) δ 4.35 (t, J=5.2 Hz, 1H), 3.54 (dt, J=12.2, 6.3 Hz, 1H), 3.38 (t, J=5.8 Hz, 2H), 2.76 (q, J=10.2 Hz, 1H), 1.47 (s, 3H), 1.44-1.28 (m, 18H), 1.24 (s, 3H). ESI-MS m/z calc. 257.1991, found 258.1 (M+1)$^+$; Retention time: 1.55 min (LC Method B).

Step 4: tert-Butyl (4S)-2,2-dimethyl-4-(3-methyl-sulfonyloxypropyl)pyrrolidine-1-carboxylate

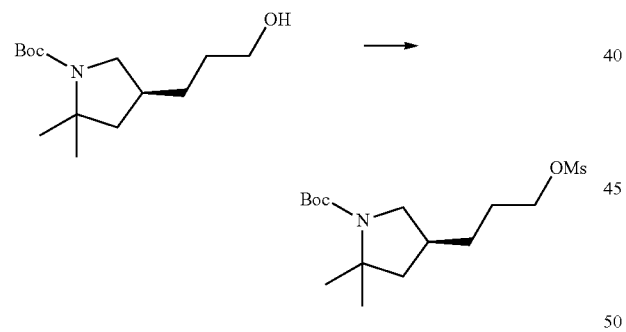

A 500 mL, 3-neck round bottom flask was fitted with a mechanical stirrer, a cooling bath, an addition funnel, a J-Kem temperature probe and a nitrogen inlet/outlet. The vessel was charged under a nitrogen atmosphere with tert-butyl (4S)-4-(3-hydroxypropyl)-2,2-dimethyl-pyrrolidine-1-carboxylate (25 g, 97.14 mmol) and dichloromethane (250 mL) which provided a clear colorless solution. Stirring was commenced and the pot temperature was recorded at 19° C. The cooling bath was charged with crushed ice/water and the pot temperature was lowered to 0° C. The addition funnel was charged with triethylamine (17.60 mL, 126.3 mmol) which was added neat dropwise over 5 min. No exotherm was observed. The addition funnel was then charged with methanesulfonyl chloride (8.277 mL, 106.9 mmol) which was added neat dropwise over 15 min which resulted in a light yellow suspension and an exotherm to 4° C. The mixture was continued to stir at <5° C. for 1 h when analysis by LC/MS indicated complete consumption of the starting material. The reaction mixture was further diluted with dichloromethane (200 mL) and then poured into saturated ammonium chloride solution (250 mL). The biphasic mixture was then transferred to a separatory funnel. The organic was removed, washed with saturated ammonium chloride solution (150 mL), dried over sodium sulfate (150 g) and then filtered through a glass frit Buchner funnel. The filtrate was concentrated under reduced pressure to provide tert-butyl (4S)-2,2-dimethyl-4-(3-methylsulfonyloxypropyl)pyrrolidine-1-carboxylate (29 g, 89%) as a clear amber oil. $^1$H NMR (400 MHz, dimethyl sulfoxide-d$_6$) δ 4.19 (t, J=6.4 Hz, 2H), 3.16 (s, 3H), 2.79 (q, J=10.2 Hz, 1H), 2.11 (s, 1H), 1.90 (td, J=13.5, 6.0 Hz, 1H), 1.66 (ddd, J=15.8, 7.6, 4.0 Hz, 2H), 1.51-1.22 (m, 20H). ESI-MS m/z calc. 335.17664, found 336.1 (M+1)$^+$; Retention time: 1.74 min (LC Method B).

Step 5: tert-Butyl (4S)-2,2-dimethyl-4-[3-(3-sulfamoylphenoxy)propyl]pyrrolidine-1-carboxylate

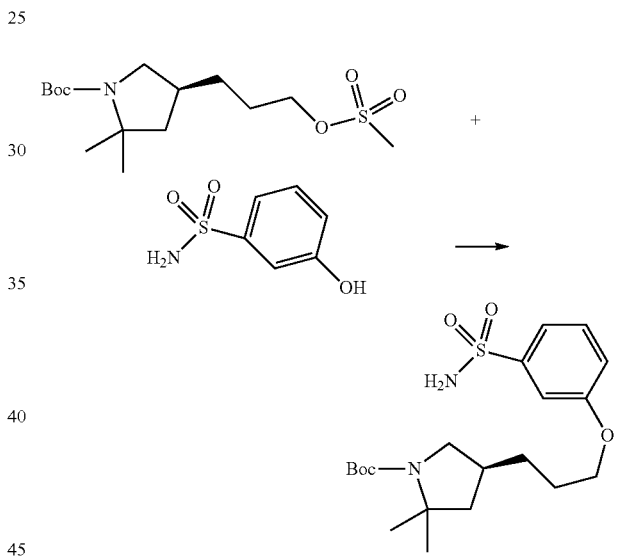

In a 100 mL flask was added 3-hydroxybenzenesulfonamide (750 mg, 4.331 mmol) and N,N-dimethylformamide (15 mL). To the mixture was added potassium carbonate (1.8 g, 13.02 mmol) and tert-butyl (4S)-2,2-dimethyl-4-(3-methylsulfonyloxypropyl)pyrrolidine-1-carboxylate (1.5 g, 4.471 mmol) at room temperature. The resulting mixture was stirred at room temperature for 48 h, then heated to 50° C. for 5 h. The mixture was then poured into 1 N citric acid and extracted with ethyl acetate (2×). Combined organic fractions, dried (sodium sulfate), filtered and concentrated to a yellow oil which was purified via silica gel column chromatography (80 gram column) using a gradient from 100% hexanes to 65% ethyl acetate in hexanes to afford tert-butyl (4S)-2,2-dimethyl-4-[3-(3-sulfamoylphenoxy)propyl]pyrrolidine-1-carboxylate (868 mg, 49%) as a light yellow foam. $^1$H NMR (400 MHz, dimethyl sulfoxide-d$_6$) δ 7.47 (t, J=8.0 Hz, 1H), 7.40-7.36 (m, 1H), 7.34 (d, J=3.7 Hz, 3H), 7.15 (d, J=8.3 Hz, 1H), 4.02 (t, J=6.1 Hz, 2H), 3.58 (dd, J=17.4, 7.1 Hz, 1H), 2.81 (q, J=10.3 Hz, 1H), 2.15 (s, 1H), 1.99-1.85 (m, 1H), 1.74 (dt, J=13.3, 6.4 Hz, 2H), 1.46 (dd, J=14.6, 9.4 Hz, 3H), 1.38 (t, J=10.4 Hz, 12H), 1.25 (s, 3H). ESI-MS m/z calc. 412.2032, found 413.2 (M+1)+; Retention time: 1.86 min (LC Method E).

Step 6: tert-Butyl (4S)-4-[3-[3-[[2-chloro-6-[3-[2-[1-(trifluoromethyl) cyclopropyl]ethoxy]pyrazol-1-yl]pyridine-3-carbonyl]sulfamoyl]phenoxy]propyl]-2,2-dimethyl-pyrrolidine-1-carboxylate

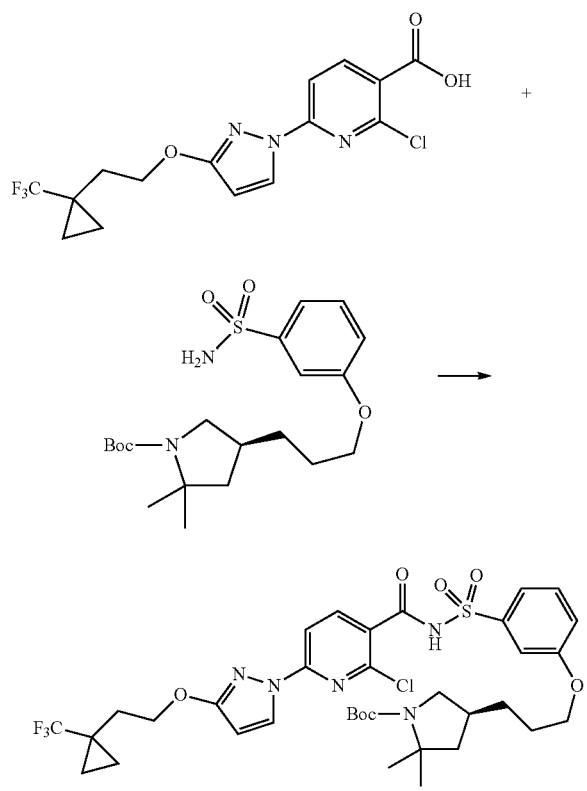

2-Chloro-6-[3-[2-[1-(trifluoromethyl)cyclopropyl] ethoxy]pyrazol-1-yl]pyridine-3-carboxylic acid (342 mg, 0.9102 mmol) and carbonyl diimidazole (148 mg, 0.9127 mmol) were combined in tetrahydrofuran (5.5 mL) and stirred for 1 h at 50° C. Then tert-butyl (4S)-2,2-dimethyl-4-[3-(3-sulfamoylphenoxy)propyl]pyrrolidine-1-carboxylate (250 mg, 0.6060 mmol) was added followed by 1,8-diazabicyclo[5.4.0]undec-7-ene (230 μL, 1.538 mmol) and the reaction was heated at 50° C. for 18 h. The reaction was diluted with ethyl acetate and washed with a 1 M citric acid solution, followed by brine. The organics were separated, dried over sodium sulfate, filtered and evaporated and then purified via silica gel chromatography (40 gram column) using a gradient from 100% hexanes to 75% ethyl acetate in hexanes to afford tert-butyl (4S)-4-[3-[3-[[2-chloro-6-[3-[2-[1-(trifluoromethyl)cyclopropyl]ethoxy]pyrazol-1-yl]pyridine-3-carbonyl]sulfamoyl]phenoxy]propyl]-2,2-dimethyl-pyrrolidine-1-carboxylate (368 mg, 79%) as an off-white solid. ESI-MS m/z calc. 769.2524, found 770.2 (M+1)+; Retention time: 2.12 min (LC Method G).

Step 7: (14S)-12,12-Dimethyl-8-(3-{2-[1-(trifluoromethyl)cyclopropyl]ethoxy}-1H-pyrazol-1-yl)-18-oxa-2λ6-thia-3,9,11-triazatetracyclo[17.3.1.111,14.05,10]tetracosa-1(23),5(10),6,8,19,21-hexaene-2,2,4-trione (Compound 77)

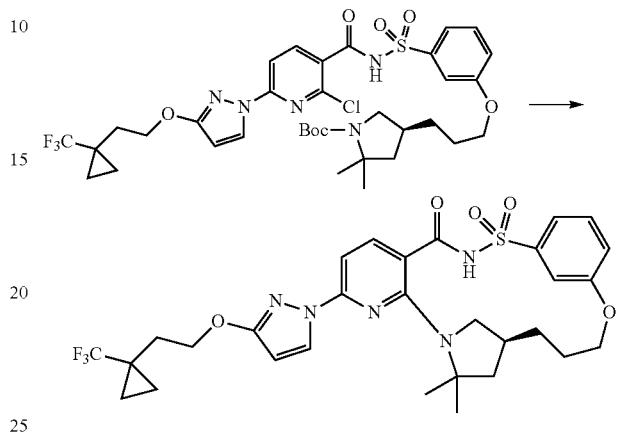

Part A: tert-Butyl (4S)-4-[3-[3-[[2-chloro-6-[3-[2-[1-(trifluoromethyl)cyclopropyl]ethoxy]pyrazol-1-yl]pyridine-3-carbonyl]sulfamoyl]phenoxy]propyl]-2,2-dimethyl-pyrrolidine-1-carboxylate (368 mg, 0.4778 mmol) was dissolved in dichloromethane (7.6 mL) and to the mixture was added hydrochloric acid (4 M in dioxane) (4.0 mL of 4 M, 16.00 mmol) and stirred at room temperature for 30 min. Concentrated mixture to dryness under reduced pressure, redissolved in ethyl acetate, then added aqueous 2 M sodium carbonate (5 mL) to give pH~10. Extracted organic layer with ethyl acetate (2×10 mL), washed with brine, then dried over sodium sulfate, filtered and evaporated to dryness under reduced pressure.

Part B: Combined material from Part A and potassium carbonate (345 mg, 2.496 mmol), cesium fluoride (115 mg, 0.7571 mmol), 3 Å molecular sieves and dimethyl sulfoxide (7.6 mL) in a vial, purged with nitrogen, capped, heated at 150° C. and stirred for 20 h. Cooled to room temperature. The mixture was filtered, then purified by reverse-phase preparative HPLC utilizing a $C_{18}$ column and method 30-99 A1-B1 (acetonitrile-water+5 mM hydrochloric acid) to afford (14S)-12,12-dimethyl-8-(3-{2-[1-(trifluoromethyl) cyclopropyl]ethoxy}-1H-pyrazol-1-yl)-18-oxa-2λ6-thia-3,9,11-triazatetracyclo[17.3.1.111,14.05,10]tetracosa-1(23),5 (10),6,8,19,21-hexaene-2,2,4-trione (Compound 77) (62.1 mg, 20%) as an off-white solid. 1H NMR (400 MHz, dimethyl sulfoxide-d6) δ 12.40 (s, 1H), 8.21 (d, J=2.8 Hz, 1H), 7.85 (d, J=8.3 Hz, 1H), 7.57 (t, J=6.5 Hz, 2H), 7.50 (s, 1H), 7.46-7.32 (m, 1H), 6.94 (d, J=8.2 Hz, 1H), 6.12 (d, J=2.7 Hz, 1H), 4.34 (dt, J=14.1, 5.6 Hz, 3H), 4.21-4.04 (m, 1H), 2.90-2.78 (m, 1H), 2.71 (dd, J=19.5, 9.2 Hz, 1H), 2.26-2.12 (m, 1H), 2.08 (t, J=7.1 Hz, 2H), 1.85 (dd, J=11.8, 5.5 Hz, 1H), 1.75-1.64 (m, 2H), 1.55 (s, 6H), 1.50 (d, J=12.4 Hz, 1H), 1.47-1.36 (m, 1H), 1.28-1.19 (m, 1H), 0.98-0.93 (m, 2H), 0.88 (t, J=5.2 Hz, 2H). ESI-MS m/z calc. 633.22327, found 634.2 (M+1)+; Retention time: 2.3 min (LC Method E).

Example 20: Preparation of (14S)-8-[3-(3,3-dimethylbutyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 79)

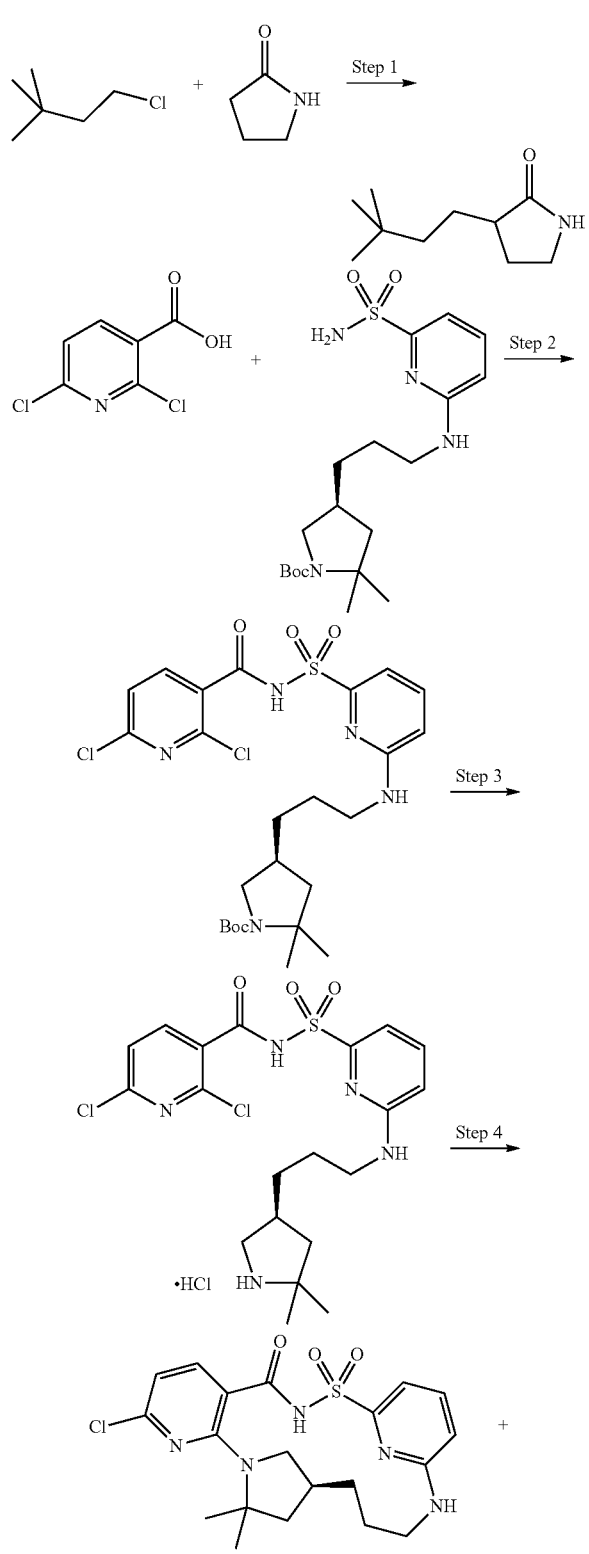

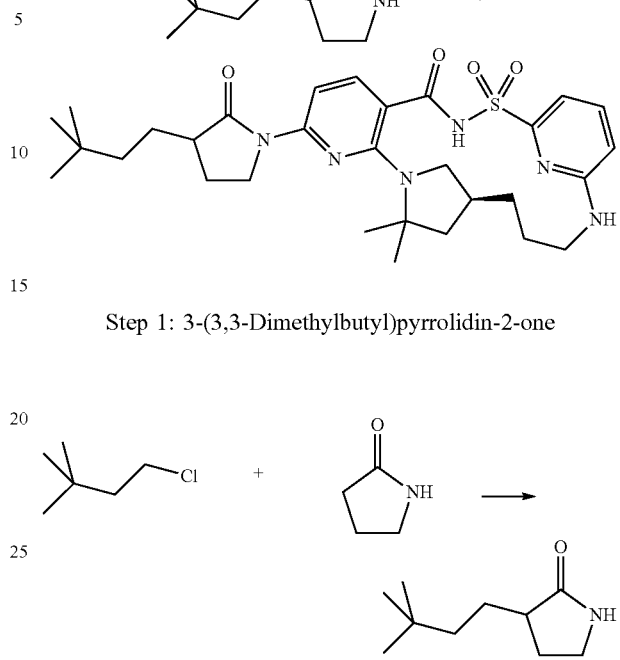

Step 1: 3-(3,3-Dimethylbutyl)pyrrolidin-2-one

To a solution of 2-pyrrolidone (32.0 g, 0.376 mol) in anhydrous tetrahydrofuran (900 mL) was added n-butyllithium (2.3 M in hexane, 343 mL, 0.790 mol) at −78° C. The reaction mixture was stirred at the same temperature for 1 h. A solution of 1-chloro-3,3-dimethylbutane (45.3 g, 0.376 mol) in anhydrous tetrahydrofuran (100 mL) was added to the reaction mixture dropwise at −78° C. The reaction was stirred for 10 min at −78° C. and then slowly raised to room temperature. The reaction was quenched with 20% ammonium chloride aqueous solution (500 mL). Two layers were separated and the aqueous layer was extracted with ethyl acetate (2×250 mL). The combined organic layers were washed with brine (300 mL), dried over anhydrous sodium sulfate, filtered and concentrated under vacuum. The residue was triturated with hexane (50 mL) to yield 3-(3,3-dimethylbutyl)pyrrolidin-2-one (9.091 g, 14%) as a white crystalline solid. ¹H-NMR (250 MHz, CDCl₃) δ 5.70 (s, br, 1H), 3.32 (m, 2H), 2.29 (m, 2H), 1.86 (m, 1H), 1.79 (m, 1H), 1.26 (m, 3H), 0.90 (s, 9H). ESI-MS m/z: calc. 169.1, found 169.9 (M+1)⁺.

Step 2: tert-Butyl (4S)-4-[3-[[6-[(2,6-dichloropyridine-3-carbonyl)sulfamoyl]-2-pyridyl]amino]propyl]-2,2-dimethyl-pyrrolidine-1-carboxylate

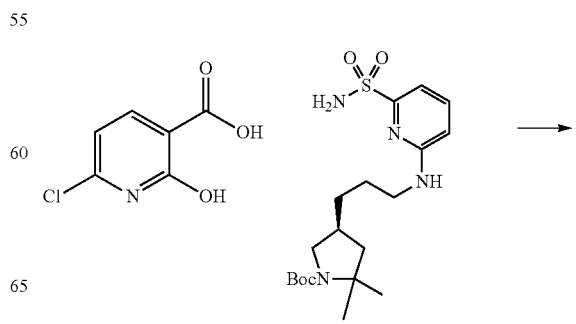

297

-continued

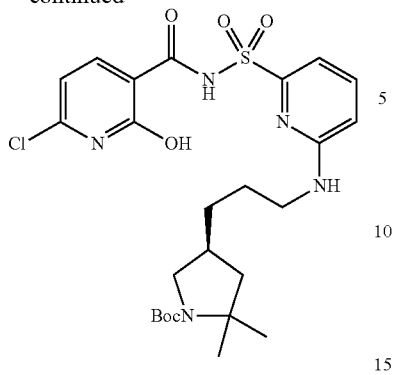

A 250 mL round bottom flask was charged under nitrogen with 2,6-dichloropyridine-3-carboxylic acid (1.14 g, 5.937 mmol) and anhydrous tetrahydrofuran (20 mL). Added carbonyl diimidazole (964 mg, 5.945 mmol) and the mixture was stirred under nitrogen at room temperature for 2 h. In a separate 100 mL flask, a solution of tert-butyl (4S)-2,2-dimethyl-4-[3-[(6-sulfamoyl-2-pyridyl)amino]propyl]pyrrolidine-1-carboxylate (1.529 g, 3.706 mmol) in anhydrous tetrahydrofuran (10 mL) was prepared under a nitrogen atmosphere and it was subsequently added via syringe into the activated ester solution. Added 1,8-diazabicyclo[5.4.0]undec-7-ene (1.2 mL, 8.024 mmol) via a syringe and the reaction mixture was stirred at room temperature under a nitrogen atmosphere for 16 h. The solvents were removed under reduced pressure and the resulting thick oil was treated with ethyl acetate (50 mL) and water (30 mL). Added hydrochloric acid (4 mL of 6 M, 24.00 mmol) and the two phases were separated. The aqueous phase was washed with brine (30 mL) and dried over sodium sulfate. After evaporation of the solvents, the residue was dissolved in dichloromethane and purified by flash chromatography on silica gel (80 g column) using a gradient of ethyl acetate (0 to 100% over 30 min) in hexanes. Evaporation of the solvents provided tert-butyl (4S)-4-[3-[[6-[(2,6-dichloropyridine-3-carbonyl)sulfamoyl]-2-pyridyl]amino]propyl]-2,2-dimethyl-pyrrolidine-1-carboxylate (1.934 g, 89%) as a white foamy solid. $^1$H NMR (400 MHz, dimethyl sulfoxide-d$_6$) δ 12.90 (broad s, 1H), 8.06 (dt, J=8.0, 3.1 Hz, 1H), 7.69 (d, J=8.0 Hz, 1H), 7.61 (dd, J=8.5, 7.2 Hz, 1H), 7.22 (broad s, 1H), 7.16 (d, J=7.2 Hz, 1H), 6.74 (d, J=8.5 Hz, 1H), 3.61-3.41 (m, 1H), 3.31-3.13 (m, 2H), 2.76 (td, J=10.5, 4.8 Hz, 1H), 2.11-1.99 (m, 1H), 1.83 (td, J=14.1, 13.5, 5.9 Hz, 1H), 1.60-1.44 (m, 2H), 1.44-1.26 (m, 15H), 1.21 (s, 3H). ESI-MS m/z calc. 585.15796, found 586.1 (M+1)$^+$; Retention time: 2.02 min (LC Method B). The product was used for the next step without any further purification.

Step 3: 2,6-Dichloro-N-[[6-[3-[(3S)-5,5-dimethylpyrrolidin-3-yl]propylamino]-2-pyridyl]sulfonyl]pyridine-3-carboxamide (Dihydrochloride Salt)

298

-continued

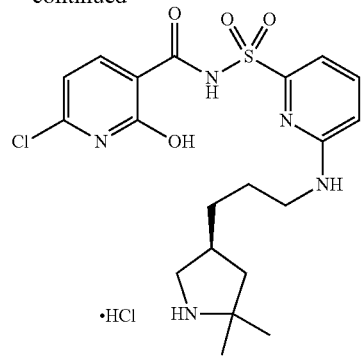

n a 100 mL round bottom flask, tert-butyl (4S)-4-[3-[[6-[(2,6-dichloropyridine-3-carbonyl)sulfamoyl]-2-pyridyl]amino]propyl]-2,2-dimethyl-pyrrolidine-1-carboxylate (1.923 g, 3.279 mmol) was stirred at room temperature in dichloromethane (10 mL) and hydrochloric acid (3 mL of 4 M in dioxane solution, 12.00 mmol). A white gummy precipitate formed rapidly. More dichloromethane (10 mL) was added and the mixture was stirred at room temperature for an additional 2.5 h. An additional 2 mL of hydrochloric acid was added and the mixture was stirred for an additional 2 h. The volatiles were removed by evaporation and the residue was evaporated in the presence of tetrahydrofuran/ethyl acetate/dichloromethane/methanol/hexanes until a foamy solid was obtained. Drying under high vacuum over the weekend provided 2,6-dichloro-N-[[6-[3-[(3S)-5,5-dimethylpyrrolidin-3-yl]propylamino]-2-pyridyl]sulfonyl]pyridine-3-carboxamide (dihydrochloride salt) (1.933 g, 105%) as a foamy off-white solid (approx. 90% pure by LCMS). $^1$H NMR (400 MHz, dimethyl sulfoxide-d$_6$) δ 9.13 (broad s, 1H), 8.98 (broad s, 1H), 8.06 (d, J=8.0 Hz, 1H), 7.72 (d, J=8.0 Hz, 1H), 7.62 (dd, J=8.5, 7.2 Hz, 1H), 7.17 (d, J=7.1 Hz, 1H), 6.77 (dd, J=8.5, 0.8 Hz, 1H), 3.34 (dq, J=11.2, 5.6 Hz, 1H), 3.24 (q, J=6.0 Hz, 2H), 2.80 (td, J=11.8, 11.1, 6.0 Hz, 1H), 2.42-2.29 (m, 1H), 2.14 (tt, J=7.8, 6.9 Hz, 1H), 1.93 (dd, J=12.8, 7.8 Hz, 1H), 1.56-1.32 (m, 7H), 1.28 (s, 3H). ESI-MS m/z calc. 485.10553, found 486.2 (M+1)$^+$; Retention time: 0.89 min (LC Method B).

Step 4: (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound D)

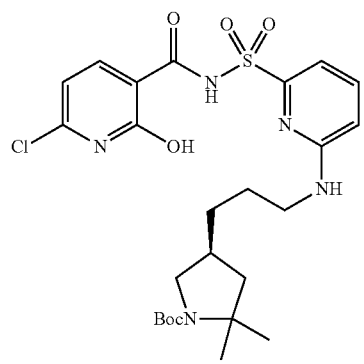

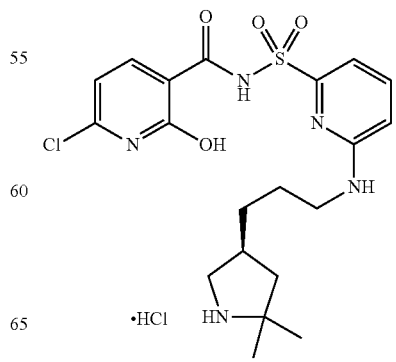

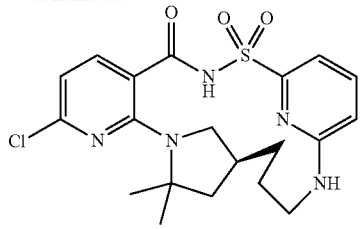

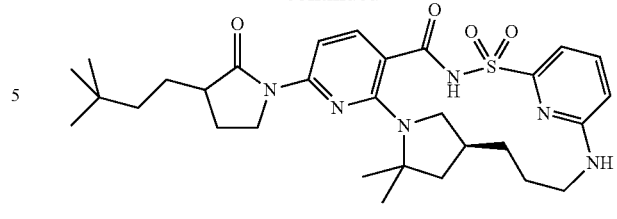

To a 20 mL microwave vial under nitrogen was added 2,6-dichloro-N-[[6-[3-[(3S)-5,5-dimethylpyrrolidin-3-yl]propylamino]-2-pyridyl]sulfonyl]pyridine-3-carboxamide (dihydrochloride salt) (859 mg, 1.536 mmol), anhydrous NMP (13.5 mL), potassium carbonate (1.4 g, 10.13 mmol) (325 mesh), 3 Å molecular sieves and cesium fluoride (285 mg, 1.876 mmol). The vial was sealed under nitrogen and the mixture was vigorously stirred in an oil bath at 150° C. for 22 h. The mixture was poured into cooled water (85 mL) and it was acidified by adding hydrochloric acid (2.1 mL of 6 M, 12.60 mmol) (mild foaming). The resulting suspension was filtered through a ceramic funnel using a paper filter and the solid was briefly air dried. The solid was dissolved in dichloromethane and dried over sodium sulfate. After concentration, the solution was diluted with dichloromethane and purified by chromatography on silica gel using a gradient of ethyl acetate (0 to 100% over 30 min) in hexanes. The product eluted between 55-65% ethyl acetate in hexanes. Evaporation of the solvents and further concentration provided (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (320 mg, 54%). $^1$H NMR (400 MHz, Chloroform-d) δ 9.19 (s, 1H), 7.80 (d, J=7.9 Hz, 1H), 7.56 (t, J=7.8 Hz, 1H), 7.44 (d, J=7.2 Hz, 1H), 6.66 (d, J=7.9 Hz, 1H), 6.59 (d, J=8.3 Hz, 1H), 3.93 (d, J=11.0 Hz, 1H), 3.25 (dd, J=10.1, 7.2 Hz, 1H), 3.17 (d, J=13.6 Hz, 1H), 2.96 (t, J=10.1 Hz, 1H), 2.39 (d, J=9.7 Hz, 1H), 1.96 (dd, J=12.1, 6.8 Hz, 1H), 1.63 (d, J=8.1 Hz, 3H), 1.57 (d, J=15.4 Hz, 7H), 1.47 (d, J=9.5 Hz, 1H). ESI-MS m/z calc. 449.12885, found 450.4 (M+1)$^+$; Retention time: 1.76 min (LC Method E).

Step 5: (14S)-8-[3-(3,3-Dimethylbutyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound 79)

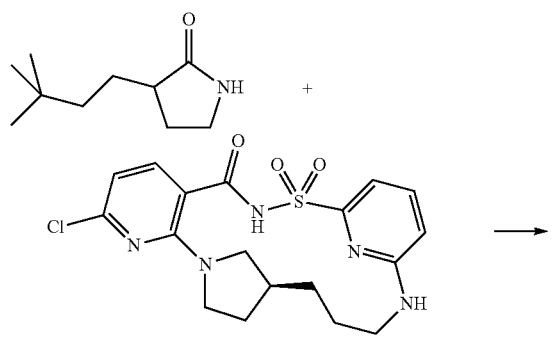

A 4 mL vial was charged with (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (25 mg, 0.05556 mmol), 3-(3,3-dimethylbutyl)pyrrolidin-2-one (12 mg, 0.07090 mmol), Pd$_2$(dba)$_3$ (8 mg, 0.008736 mmol), Xantphos (5 mg, 0.008641 mmol), cesium carbonate (99 mg, 0.3038 mmol) and anhydrous dioxane (400 µL). The mixture was sparged with nitrogen for 1-2 min, capped and stirred at 120° C. for 21 h. The reaction was diluted with dimethyl sulfoxide (900 µL), microfiltered and subjected to reverse phase preparative HPLC (C$_{18}$) using a gradient of acetonitrile in water (1 to 99% over 15 min) and hydrochloric acid as a modifier. The pure fractions were collected and the solvents evaporated to give 4.3 mg of off-white solid. The product was further purified by flash chromatography on silica gel (4 g column) using a gradient of methanol (0 to 5% over 30 min) in dichloromethane. The pure fractions were collected and the solvents evaporated to give (14S)-8-[3-(3,3-dimethylbutyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound 79) (2 mg, 6%) as an off-white solid (diastereomeric mixture). $^1$H NMR (400 MHz, dimethyl sulfoxide-d$_6$) δ 12.41 (s, 1H), 7.68 (d, J=8.4 Hz, 1H), 7.63-7.44 (m, 2H), 7.04 (d, J=7.1 Hz, 1H), 6.97 (broad s, 1H), 6.70 (d, J=8.5 Hz, 1H), 4.16-3.64 (m, 3H), 3.10 (br s, 1H), 2.94 (d, J=13.3 Hz, 1H), 2.74-2.54 (m, 2H), 2.29-2.17 (m, 1H), 2.10 (br s, 1H), 1.87-1.43 (m, 11H), 1.37-1.12 (m, 6H), 0.88 (d, J=3.6 Hz, 9H). ESI-MS m/z calc. 582.2988, found 583.4 (M+1)$^+$; Retention time: 2.25 min (LC Method B).

Example 21: Preparation of 12,12-dimethyl-8-(4-{2-[1-(trifluoromethyl)cyclopropyl]ethoxy}-1H-pyrazol-1-yl)-2λ$^6$-thia-3,9,11,19,24-pentaazatetracyclo[18.3.1.1$^{11,14}$.0$^{5,10}$]pentacosa-1(23),5,7,9,20(24),21-hexaene-2,2,4-trione (Enantiomer 1) (Compound 82) and 12,12-dimethyl-8-(4-{2-[1-(trifluoromethyl) cyclopropyl]ethoxy}-1H-pyrazol-1-yl)-2λ$^6$-thia-3,9,11,19,24-pentaazatetracyclo[18.3.1.1$^{11,14}$.0$^{5,10}$]pentacosa-1(23),5,7,9,20(24),21-hexaene-2,2,4-trione (Enantiomer 2) (Compound 83)

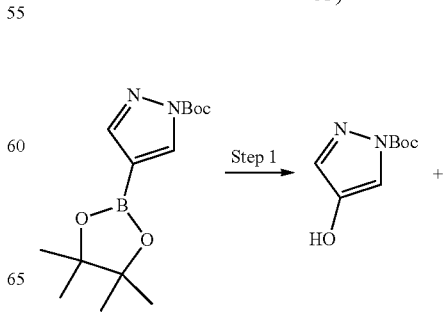

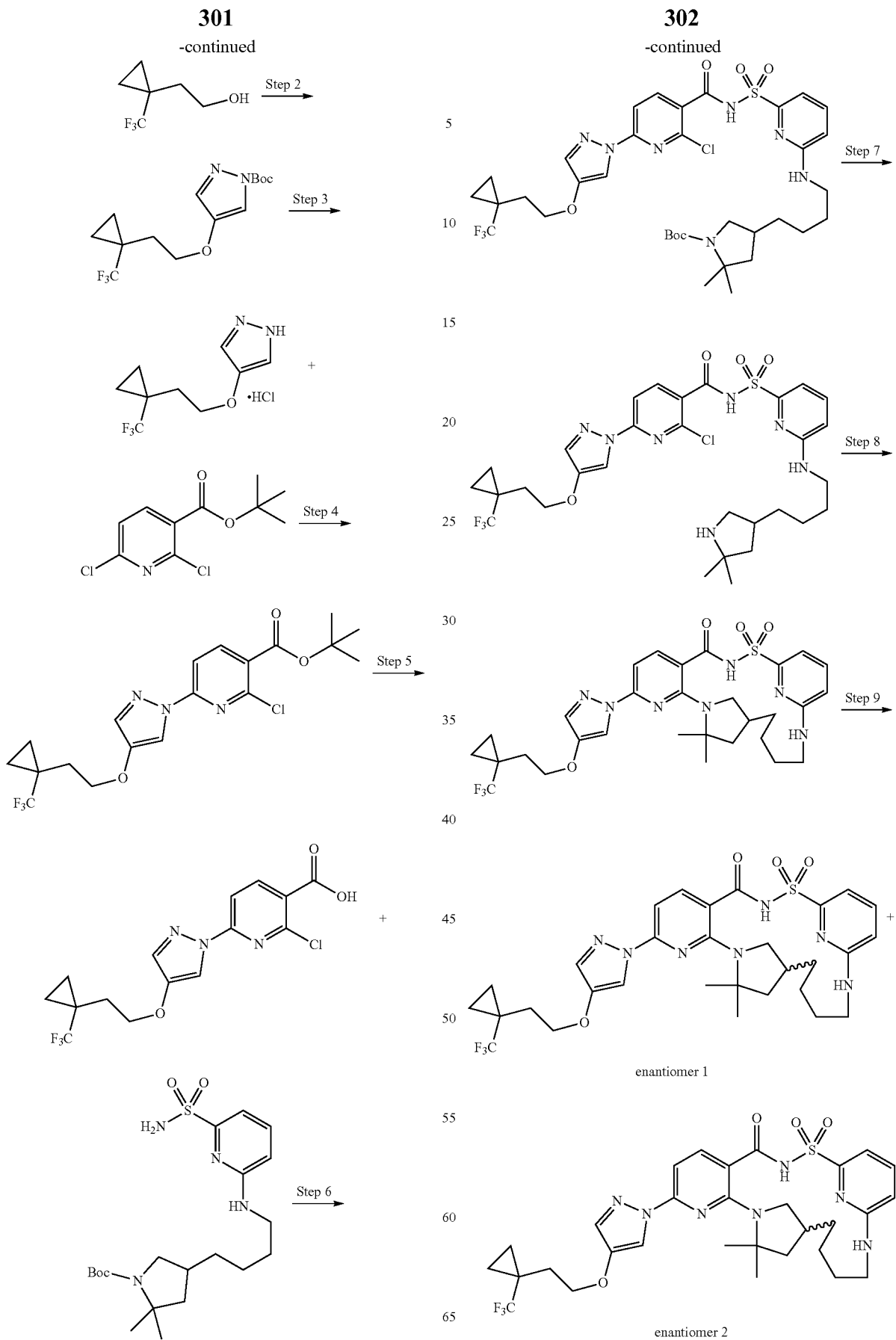

Step 1: tert-Butyl 4-hydroxypyrazole-1-carboxylate

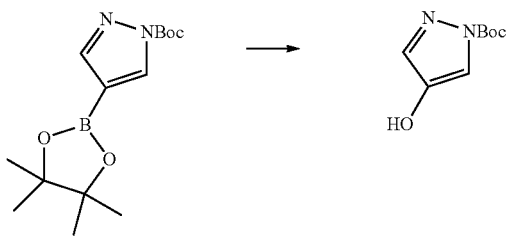 [SMILES: CC(C)(C)OC(=O)n1cc(B2OC(C)(C)C(C)(C)O2)cn1 ; CC(C)(C)OC(=O)n1cc(O)cn1]

Sodium hydroxide (16.32 g, 408.0 mmol) was added to a cold solution (0° C.) of tert-butyl 4-(4,4,5,5-tetramethyl-1,3,2-dioxaborolan-2-yl)pyrazole-1-carboxylate (60 g, 204.0 mmol) in tetrahydrofuran (450 mL) followed by slow addition of hydrogen peroxide (46.26 g, 41.68 mL of 30% w/v, 408.0 mmol). Reaction mixture was stirred at 0° C. for 10 min then at room temperature for 45 min. Reaction was cooled to 0° C. and diluted with dichloromethane (800 mL). 3M hydrochloric acid was added until pH=2 and the organic layer was separated, dried over magnesium sulfate and concentrated under reduced pressure. The residue was triturated in a small amount of dichloromethane and solid was filtrated under vacuum, washed well with more dichloromethane and dried under reduced pressure to afford tert-butyl 4-hydroxypyrazole-1-carboxylate (19.904 g, 53%) as a white solid. $^1$H NMR (300 MHz, dimethyl sulfoxide-$d_6$) δ 1.52 (s, 9H), 7.45 (d, J=0.9 Hz, 1H), 7.51 (d, J=0.9 Hz, 1H), 9.28 (s, 1H). ESI-MS m/z calc. 184.0848, found 129.1 (M-$C_4H_8$+1)$^+$; Retention time: 1.73 min (LC Method H).

Step 2: tert-Butyl 4-[2-[1-(trifluoromethyl)cyclopropyl]ethoxy]pyrazole-1-carboxylate

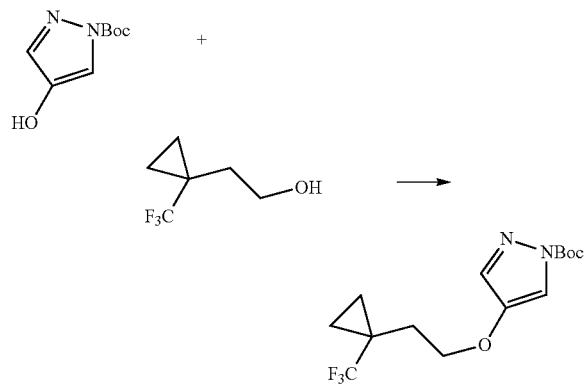

2-[1-(Trifluoromethyl)cyclopropyl]ethanol (28.2 g, 183.0 mmol) was added to a solution of tert-butyl 4-hydroxypyrazole-1-carboxylate (23.7 g, 128.7 mmol) and triphenylphosphine (50.6 g, 192.9 mmol) in tetrahydrofuran (250 mL) at 0° C. Diisopropyl azodicarboxylate (39.03 g, 38.00 mL, 193.0 mmol) was slowly added at 0° C. and the reaction mixture was stirred at 0° C. for 10 min. The reaction was then heated at 70° C. overnight. The reaction was cooled to room temperature and the reaction mixture was diluted with dichloromethane (300 mL) and quenched by addition of 5% aqueous citric acid (150 mL). The organic layer was washed with brine, dried over sodium sulfate, filtered and concentrated under reduced pressure (155 g of yellow oil). The residue was triturated with heptanes and a small amount of ethyl acetate (less than 10%). The solid was filtered and washed with heptane. The filtrate was concentrated under reduced pressure (55 g of yellow oil). The residue was purified by silica gel chromatography using a gradient from 0% to 20% of ethyl acetate in heptanes to afford tert-butyl 4-[2-[1-(trifluoromethyl)cyclopropyl]ethoxy]pyrazole-1-carboxylate (27.31 g, 66%) as a white solid. $^1$H NMR (300 MHz, dimethyl sulfoxide-$d_6$) δ 0.80-0.97 (m, 4H), 1.54 (s, 9H), 2.00 (t, J=6.9 Hz, 2H), 3.99 (t, J=6.8 Hz, 2H), 7.61-7.70 (m, 1H), 7.90 (s, 1H). 19F NMR (282 MHz, dimethyl sulfoxide-$d_6$) δ−68.6 (s, 3F). ESI-MS m/z calc. 320.1348, found 265.1 (M-$C_4H_8$+1)$^+$; Retention time: 2.18 min (LC Method I).

Step 3: 4-[2-[1-(Trifluoromethyl)cyclopropyl]ethoxy]-1H-pyrazole (Hydrochloric Acid Salt)

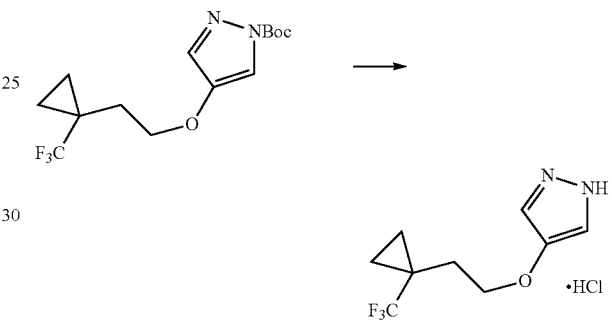

Hydrogen chloride (80 mL of 4 M, 320.0 mmol) was added to a solution of tert-butyl 4-[2-[1-(trifluoromethyl)cyclopropyl]ethoxy]pyrazole-1-carboxylate (10.63 g, 33.19 mmol) in dichloromethane (50 mL) and reaction mixture was stirred at room temperature overnight. Reaction mixture was concentrated under reduced pressure to afford 4-[2-[1-(trifluoromethyl)cyclopropyl]ethoxy]-1H-pyrazole (hydrochloric acid salt) (8.71 g, 100%) as an off-white solid. $^1$H NMR (300 MHz, dimethyl sulfoxide-$d_6$) δ 0.77-0.96 (m, 4H), 1.98 (t, J=6.9 Hz, 2H), 3.91 (t, J=6.9 Hz, 2H), 7.41 (s, 2H). ESI-MS m/z calc. 220.0823, found 221.2 (M+1)$^+$; Retention time: 2.43 min (LC Method H).

Step 4: tert-Butyl 2-chloro-6-[4-[2-[1-(trifluoromethyl)cyclopropyl]ethoxy]pyrazol-1-yl]pyridine-3-carboxylate

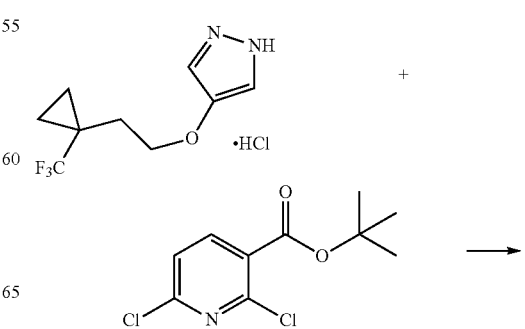

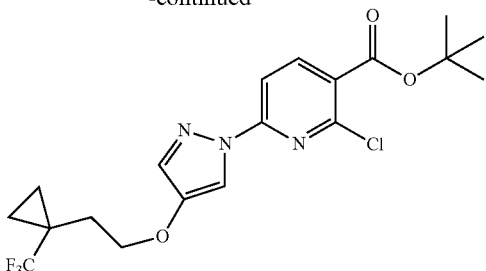

4-[2-[1-(Trifluoromethyl)cyclopropyl]ethoxy]-1H-pyrazole (hydrochloric acid salt) (10 g, 38.963 mmol) was added to N,N-dimethylformamide (80 mL). The reaction was chilled to 0° C. and sodium hydride (1.87 g, 60% w/w, 46.754 mmol) was added portionwise and was allowed to stir for 10 min. A solution of tert-butyl 2,6-dichloropyridine-3-carboxylate (9.67 g, 38.975 mmol) in N,N-dimethylformamide (20 mL) was added and the reaction was heated at 75° C. and allowed to stir overnight. Once cooled to room temperature, the reaction was quenched with brine (100 mL) and extracted with ethyl acetate (3×50 mL). The organic layers were combined, dried over sodium sulfate, filtered and concentrated under reduced pressure. The residue was purified by silica gel chromatography using a gradient from 0% to 10% of ethyl acetate in heptanes to afford tert-butyl 2-chloro-6-[4-[2-[1-(trifluoromethyl)cyclopropyl]ethoxy]pyrazol-1-yl]pyridine-3-carboxylate (7.68 g, 46%) as white solid. $^1$H NMR (300 MHz, CDCl$_3$) δ 0.73 (s, 2H), 0.98-1.10 (m, 2H), 1.62 (s, 9H), 2.03-2.13 (m, 2H), 4.09 (t, J=7.0 Hz, 2H), 7.51 (s, 1H), 7.84 (d, J=8.5 Hz, 1H), 8.12 (s, 1H), 8.21 (d, J=8.5 Hz, 1H). 19F NMR (282 MHz, CDCl$_3$) δ −69.9 (br. s., 3F). ESI-MS m/z calc. 431.1224, found 432.1 (M+1)++; Retention time: 2.56 min (LC Method I).

Step 5: 2-Chloro-6-[4-[2-[1-(trifluoromethyl)cyclopropyl]ethoxy]pyrazol-1-yl]pyridine-3-carboxylic Acid

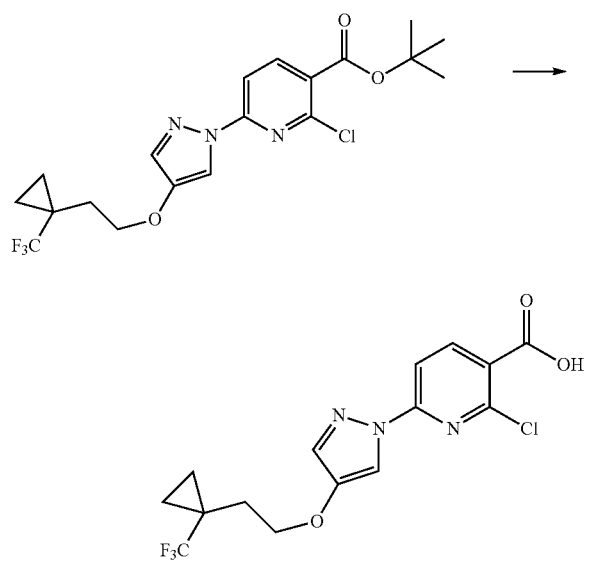

Trifluoroacetic acid (46.620 g, 31.5 mL, 408.86 mmol) was added to a solution of tert-butyl 2-chloro-6-[4-[2-[1-(trifluoromethyl)cyclopropyl]ethoxy]pyrazol-1-yl]pyridine-3-carboxylate (17.59 g, 40.733 mmol) in dichloromethane (150 mL) and the reaction mixture was stirred at room temperature for 4 h. The reaction mixture was concentrated under reduced pressure. The residue was diluted with ethyl acetate (175 mL) and the organic layer was washed with brine (2×100 mL). The organic layer was dried over sodium sulfate, filtered and concentrated under reduced pressure to afford crude 2-chloro-6-[4-[2-[1-(trifluoromethyl)cyclopropyl]ethoxy]pyrazol-1-yl]pyridine-3-carboxylic acid (14.82 g, 77%) as a white solid. $^1$H NMR (300 MHz, dimethyl sulfoxide-d$_6$) δ 0.81-0.97 (m, 4H), 2.04 (t, J=6.9 Hz, 2H), 4.04-4.13 (m, 2H), 7.77 (s, 1H), 7.86 (d, J=8.5 Hz, 1H), 8.25 (s, 1H), 8.37 (d, J=8.5 Hz, 1H). ESI-MS m/z calc. 375.0598, found 376.1 (M+1)+; Retention time: 3.14 min (LC Method H).

Step 6: tert-Butyl 4-[4-[[6-[[2-chloro-6-[4-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate

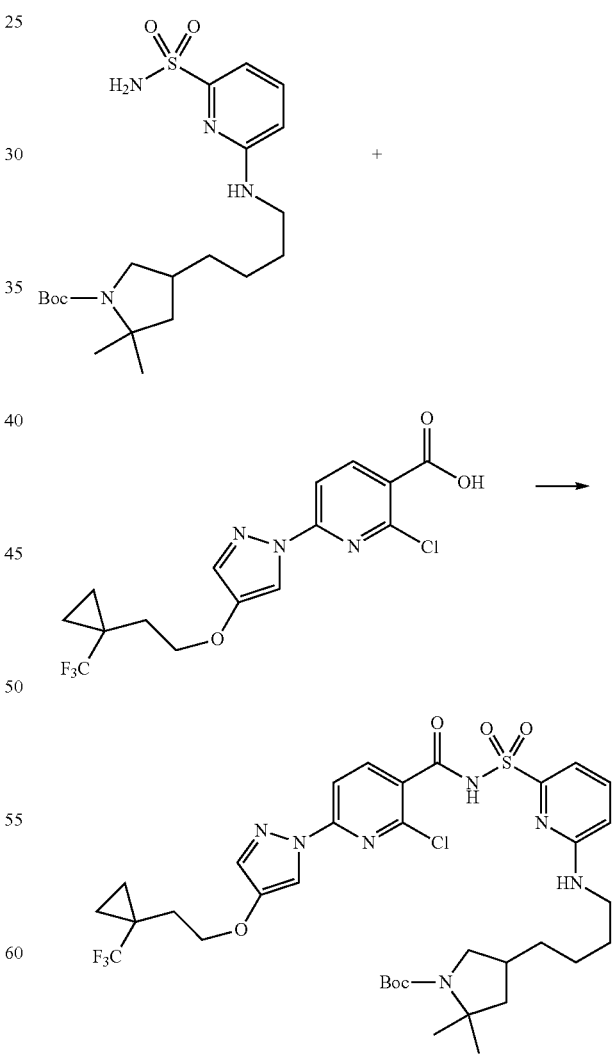

To a round bottom flask was added 2-chloro-6-[4-[2-[1-(trifluoromethyl)cyclopropyl]ethoxy]pyrazol-1-yl]pyridine- 3-carboxylic acid (97 mg, 0.2582 mmol), carbonyl diimidazole (45 mg, 0.2775 mmol) and tetrahydrofuran (3.0 mL). The reaction was heated at 40° C. for 90 min. A solution of tert-butyl 2,2-dimethyl-4-[4-[(6-sulfamoyl-2-pyridyl)amino]butyl]pyrrolidine-1-carboxylate (95 mg, 0.2227 mmol) in tetrahydrofuran (2 mL) was added dropwise followed by 2,3,4,6,7,8,9,10-octahydropyrimido[1,2-a]azepine (120 μL, 0.8024 mmol). The reaction was stirred overnight at room temperature. The reaction was quenched with 1N citric acid and extracted with ethyl acetate. The organic layer was dried over sodium sulfate, filtered and evaporated. The crude reaction mixture was purified via HPLC (20%-99% acetonitrile:water with a 0.1% hydrochloric acid modifier) giving tert-butyl 4-[4-[[6-[[2-chloro-6-[4-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate (82.7 mg, 49%) as a white solid. $^1$H NMR (400 MHz, dimethyl sulfoxide-$d_6$) δ 12.81 (s, 1H), 8.24 (s, 1H), 8.11 (d, J=8.4 Hz, 1H), 7.87 (d, J=8.4 Hz, 1H), 7.77 (d, J=0.9 Hz, 1H), 7.61 (dd, J=8.5, 7.2 Hz, 1H), 7.20 (d, J=4.9 Hz, 1H), 7.16 (d, J=7.2 Hz, 1H), 6.73 (d, J=8.5 Hz, 1H), 4.09 (t, J=6.9 Hz, 2H), 3.54-3.41 (m, 1H), 3.22 (q, J=6.5 Hz, 2H), 2.74-2.63 (m, 1H), 2.05 (t, J=6.9 Hz, 2H), 1.96 (s, 1H), 1.73 (td, J=11.5, 6.0 Hz, 1H), 1.49 (p, J=7.7, 7.3 Hz, 2H), 1.37 (d, J=12.8 Hz, 9H), 1.30-1.12 (m, 11H), 0.98-0.84 (m, 4H). ESI-MS m/z calc. 783.27924, found 784.3 (M+1)$^+$; Retention time: 2.28 min (LC Method B).

Step 7: 2-Chloro-N-[[6-[4-(5,5-dimethylpyrrolidin-3-yl)butylamino]-2-pyridyl]sulfonyl]-6-[4-[2-[1-(trifluoromethyl)cyclopropyl]ethoxy]pyrazol-1-yl]pyridine-3-carboxamide

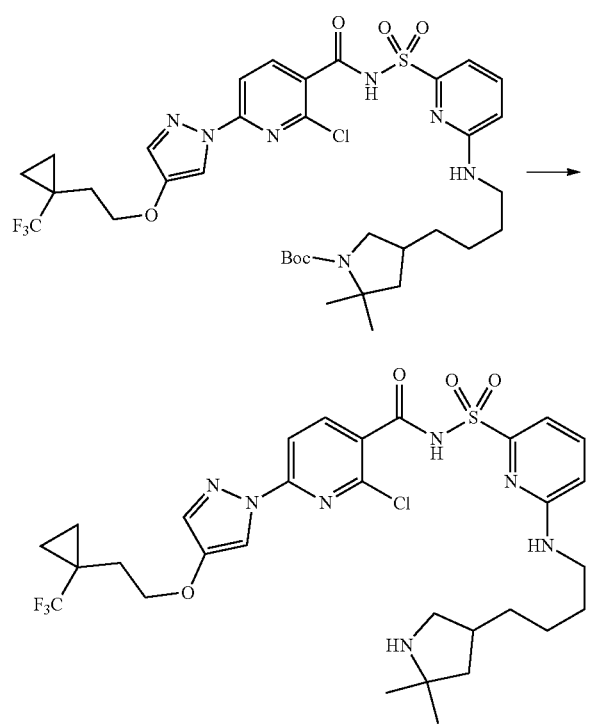

To a round bottom flask containing tert-butyl 4-[4-[[6-[[2-chloro-6-[4-[2-[1-(trifluoromethyl)cyclopropyl]ethoxy] pyrazol-1-yl]pyridine-3-carbonyl]sulfamoyl]-2-pyridyl]amino]butyl]-2,2-dimethyl-pyrrolidine-1-carboxylate (118 mg, 0.1505 mmol) was added dichloromethane (5 mL) and trifluoroacetic acid (650 μL, 8.437 mmol). The reaction was allowed to stir at room temperature for 1 h. The reaction was evaporated to dryness. A solution of saturated sodium bicarbonate was added followed by ethyl acetate. The reaction was extracted 3 times with ethyl acetate, dried over sodium sulfate, filtered and evaporated giving 2-chloro-N-[[6-[4-(5,5-dimethylpyrrolidin-3-yl)butylamino]-2-pyridyl]sulfonyl]-6-[4-[2-[1-(trifluoromethyl)cyclopropyl]ethoxy]pyrazol-1-yl]pyridine-3-carboxamide (102 mg, 99%) which was taken on without further purification. ESI-MS m/z calc. 683.2268, found 684.4 (M+1)$^+$; Retention time: 1.51 min (LC Method B).

Step 8: 12,12-Dimethyl-8-(4-{2-[1-(trifluoromethyl)cyclopropyl]ethoxy}-1H-pyrazol-1-yl)-2λ$^6$-thia-3,9,11,19,24-pentaazatetracyclo[18.3.1.1$^{11,14}$.0$^{5,10}$]pentacosa-1(23),5,7,9,20(24),21-hexaene-2,2,4-trione (Compound 70)

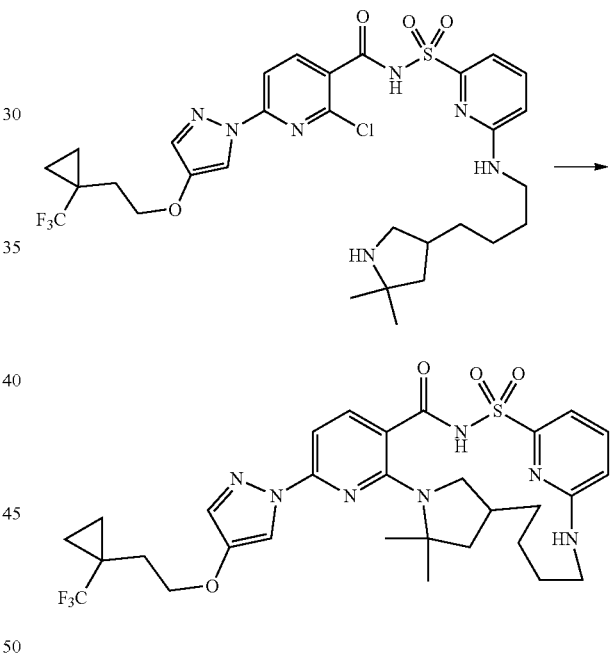

To a microwave vial was added potassium carbonate (92 mg, 0.6657 mmol), cesium fluoride (45 mg, 0.2962 mmol), five 3 Å molecular sieves and a solution of 2-chloro-N-[[6-[4-(5,5-dimethylpyrrolidin-3-yl)butylamino]-2-pyridyl]sulfonyl]-6-[4-[2-[1-(trifluoromethyl)cyclopropyl]ethoxy]pyrazol-1-yl]pyridine-3-carboxamide (90 mg, 0.1315 mmol) in dimethyl sulfoxide (0.8 mL). The reaction was sealed and placed in a preheated 150° C. oil bath overnight. The reaction was cooled to room temperature, filtered and purified via HPLC (10%-99% acetonitrile:water with a 0.1% hydrochloric acid modifier) giving 12,12-dimethyl-8-(4-{2-[1-(trifluoromethyl)cyclopropyl]ethoxy}-1H-pyrazol-1-yl)-2λ$^6$-thia-3,9,11,19,24-pentaazatetracyclo[18.3.1.1$^{11,14}$.0$^{5,10}$]pentacosa-1(23),5,7,9,20(24),21-hexaene-2,2,4-trione (Compound 70) (20.8 mg, 24%) as a white solid. ESI-MS m/z calc. 647.2502, found 648.4 (M+1)$^+$; Retention time: 2.1 min (LC Method B).

Step 9: 12,12-Dimethyl-8-(4-{2-[1-(trifluoromethyl) cyclopropyl]ethoxy}-1H-pyrazol-1-yl)-2λ⁶-thia-3,9,11,19,24-pentaazatetracyclo[18.3.1.1¹¹,¹⁴.0⁵,¹⁰] pentacosa-1(23),5,7,9,20(24),21-hexaene-2,2,4-trione (Enantiomer 1) (Compound 82) and 12,12-dimethyl-8-(4-{2-[1-(trifluoromethyl)cyclopropyl] ethoxy}-1H-pyrazol-1-yl)-2λ⁶-thia-3,9,11,19,24-pentaazatetracyclo[18.3.1.1¹¹,¹⁴.0⁵,¹⁰]pentacosa-1 (23),5,7,9,20(24),21-hexaene-2,2,4-trione (Enantiomer 2) (Compound 83)

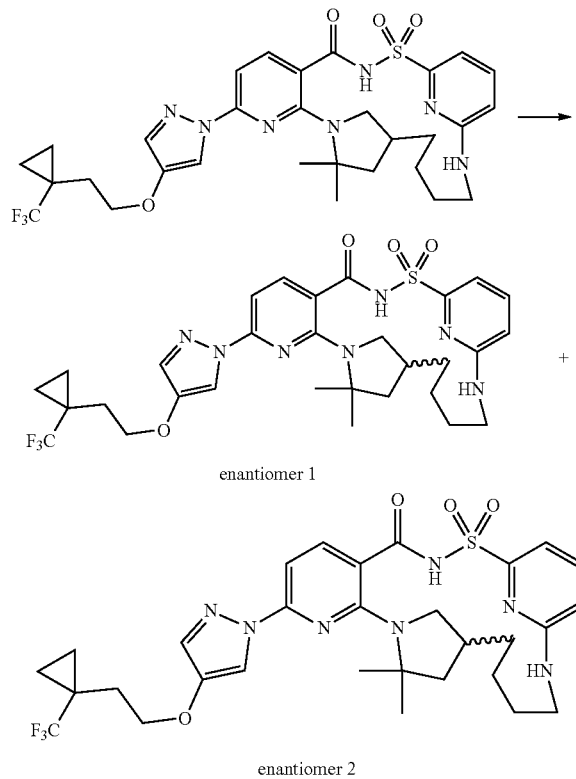

enantiomer 1 enantiomer 2

Racemic 12,12-dimethyl-8-(4-{2-[1-(trifluoromethyl)cyclopropyl]ethoxy}-1H-pyrazol-1-yl)-2λ⁶-thia-3,9,11,19,24-pentaazatetracyclo[18.3.1.1¹¹,¹⁴.0⁵,¹⁰]pentacosa-1(23),5,7,9,20(24),21-hexaene-2,2,4-trione (17 mg, 0.02625 mmol) was subjected to chiral SFC chromatography using a ChiralPak AS-H (250×21.2 mm column, 5 μm particle size) with 20%-25% methanol (NH₃ modifier))/carbon dioxide mobile phase at 50 mL/min giving as the first enantiomer to elute, 12,12-dimethyl-8-(4-{2-[1-(trifluoromethyl)cyclopropyl]ethoxy}-1H-pyrazol-1-yl)-2λ⁶-thia-3,9,11,19,24-pentaazatetracyclo[18.3.1.1¹¹,¹⁴.0⁵,¹⁰]pentacosa-1(23),5,7,9, 20(24),21-hexaene-2,2,4-trione (enantiomer 1) (Compound 82) (7.7 mg, 90%); ESI-MS m/z calc. 647.2502, found 648.2 (M+1)⁺; Retention time: 3.18 min (LC Method D) and as the second enantiomer to elute, 12,12-dimethyl-8-(4-{2-[1-(trifluoromethyl)cyclopropyl]ethoxy}-1H-pyrazol-1-yl)-2λ⁶-thia-3,9,11,19,24-pentaazatetracyclo[18.3.1.1¹¹,¹⁴.0⁵,¹⁰] pentacosa-1(23),5,7,9,20(24),21-hexaene-2,2,4-trione (enantiomer 2) (Compound 83) (7.6 mg, 89%); ¹H NMR (400 MHz, dimethyl sulfoxide-d₆) δ 12.49 (s, 1H), 7.96 (d, J=1.0 Hz, 1H), 7.82 (d, J=8.2 Hz, 1H), 7.62 (d, J=26.0 Hz, 2H), 7.14 (s, 1H), 6.98 (s, 1H), 6.69 (d, J=44.0 Hz, 2H), 4.06 (t, J=7.1 Hz, 2H), 2.86 (s, 1H), 2.04 (t, J=7.0 Hz, 3H), 1.88-1.78 (m, 1H), 1.65-1.47 (m, 7H), 1.21 (d, J=14.6 Hz, 3H), 1.01-0.82 (m, 4H), ESI-MS m/z calc. 647.2502, found 648.2 (M+1)⁺; Retention time: 3.18 min (LC Method D).

Example 22: Preparation of (18R)-20,20-dimethyl-4-(3-{2-[1-(trifluoromethyl) cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 84) and (18S)-20,20-dimethyl-4-(3-{2-[1-(trifluoromethyl) cyclopropyl]ethoxy}-1H-pyrazol-1-yl)-10λ⁶-thia-1, 3,9,14,22-pentaazatetracyclo[16.2.1.1¹¹,¹⁴.0²,⁷] docosa-2,4,6,11(22),12-pentaene-8,10,10-trione (Compound 85)

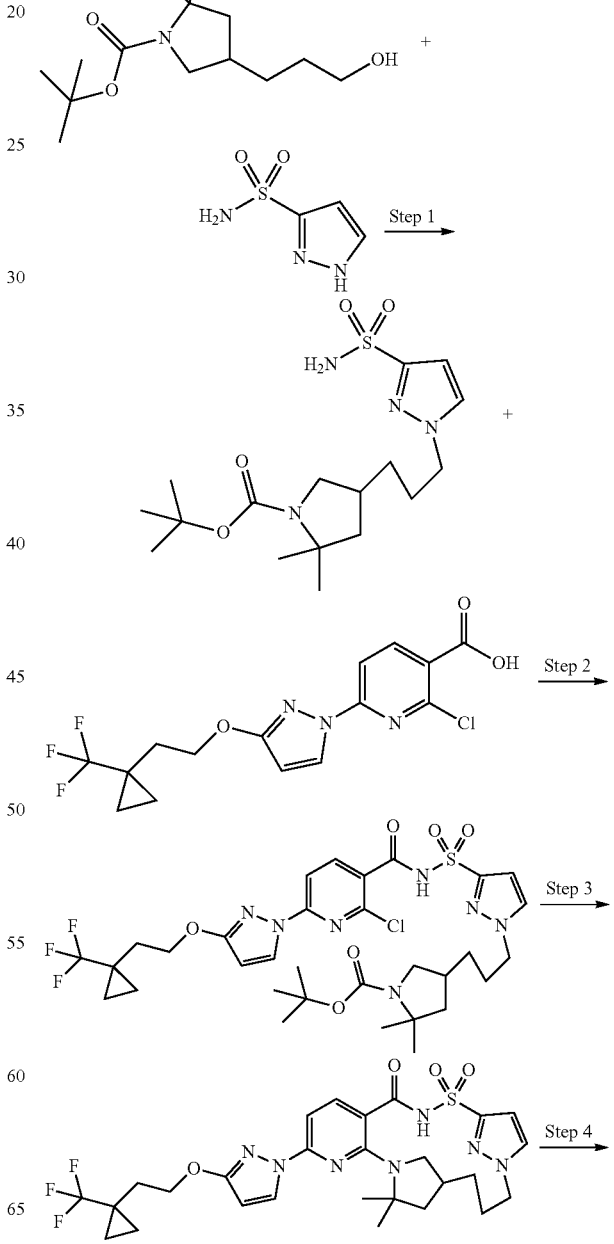

Step 1: tert-Butyl 2,2-dimethyl-4-[3-(3-sulfamoylpyrazol-1-yl)propyl]pyrrolidine-1-carboxylate

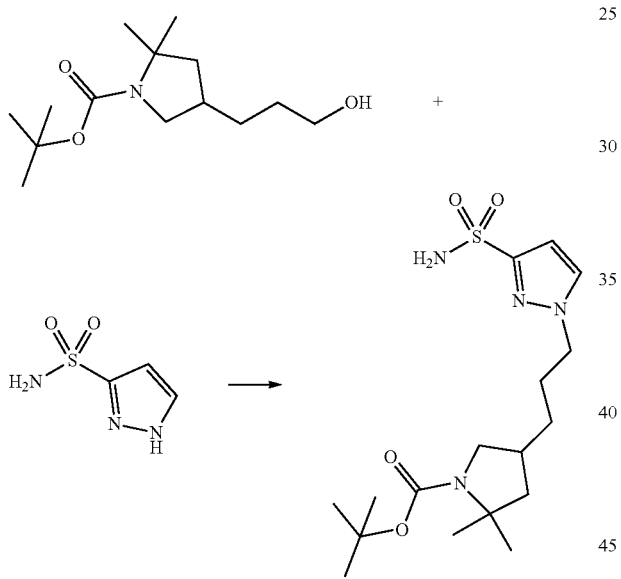

Part A: To a 250 mL round bottom flask tert-butyl 4-(3-hydroxypropyl)-2,2-dimethyl-pyrrolidine-1-carboxylate (10 g, 38.85 mmol) in dry dichloromethane (100 mL) was added triethylamine (8.3 mL, 59.55 mmol). The reaction was cooled to 0° C. over 10 min and methanesulfonyl chloride (3.7 mL, 47.80 mmol) was added dropwise (exothermic, formed white slurry) and the reaction was stirred for 1 h while warming to room temperature. The reaction was then quenched with cold water (150 mL) and extracted with dichloromethane (200 mL) twice. The organic layer was dried over sodium sulfate, filtered and evaporated to provide the mesylate as a yellowish oil.

Part B: The crude mesylate from Part A was dissolved in N,N-dimethylformamide (50 mL) and 1H-pyrazole-3-sulfonamide (5.8 g, 39.41 mmol) was added followed by potassium carbonate (16.3 g, 117.9 mmol) and the reaction mixture was stirred at 70° C. for 20 h. The reaction mixture was cooled to room temperature and poured into crushed ice and extracted with ethyl acetate (3×100 mL), combined organic layers, washed with water (2=×100 mL), dried over sodium sulfate, filtered and concentrated under reduced pressure. The brown residue was purified by silica gel chromatography (330 gram column) using a gradient from 100% hexanes to 100% ethyl acetate to afford tert-butyl 2,2-dimethyl-4-[3-(3-sulfamoylpyrazol-1-yl)propyl]pyrrolidine-1-carboxylate (7.6 g, 51%) as a white solid. ESI-MS m/z calc. 386.19876, found 387.25 (M+1)⁺; Retention time: 0.61 min (LC Method A).

Step 2: tert-Butyl 4-[3-[3-[[2-chloro-6-[3-[2-[1-(trifluoromethyl) cyclopropyl]ethoxy]pyrazol-1-yl]pyridine-3-carbonyl]sulfamoyl]pyrazol-1-yl]propyl]-2,2-dimethyl-pyrrolidine-1-carboxylate

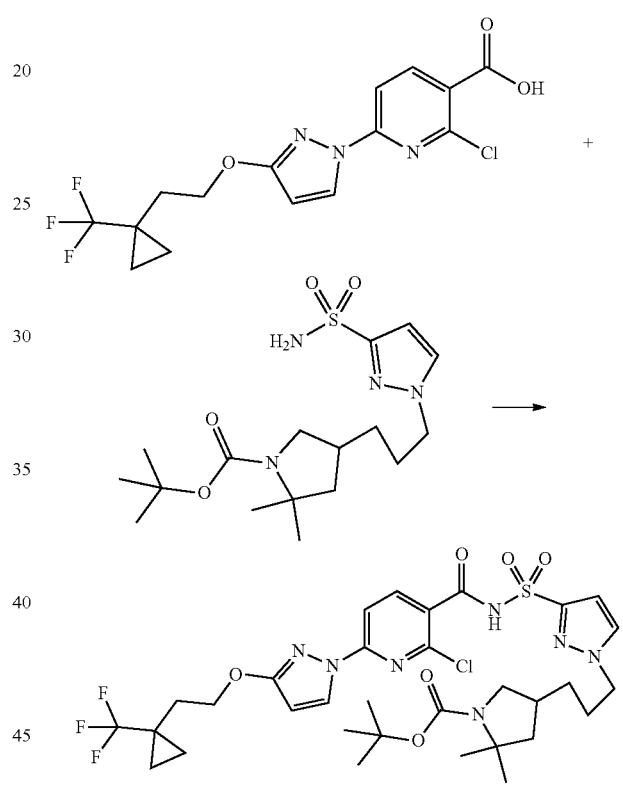

2-chloro-6-[3-[2-[1-(trifluoromethyl)cyclopropyl]ethoxy]pyrazol-1-yl]pyridine-3-carboxylic acid (458 mg, 1.219 mmol) and di(imidazol-1-yl)methanone (208 mg, 1.283 mmol) were combined in tetrahydrofuran (5 mL) and stirred for 120 min at 50° C. Then, tert-butyl 2,2-dimethyl-4-[3-(3-sulfamoylpyrazol-1-yl) propyl]pyrrolidine-1-carboxylate (388 mg, 1.004 mmol) was added followed by 1,8-diazabicyclo[5.4.0]undec-7-ene (300 µL, 2.006 mmol) and the reaction was stirred at room temperature for 20 h. The reaction mixture was diluted with ethyl acetate and washed with saturated ammonium chloride solution, followed by brine. The organics were separated, dried over sodium sulfate, filtered and evaporated and then purified by silica gel chromatography using a gradient from 100% hexanes to 90% ethyl acetate in hexanes to afford tert-butyl 4-[3-[3-[[2-chloro-6-[3-[2-[1-(trifluoromethyl)cyclopropyl]ethoxy] pyrazol-1-yl]pyridine-3-carbonyl]sulfamoyl]pyrazol-1-yl] propyl]-2,2-dimethyl-pyrrolidine-1-carboxylate (247 mg, 33%) as a white solid. ¹H NMR (400 MHz, Chloroform-d)

δ 9.82 (s, 1H), 8.30 (d, J=2.9 Hz, 1H), 8.22 (d, J=8.5 Hz, 1H), 7.73 (d, J=8.5 Hz, 1H), 7.47 (d, J=2.4 Hz, 1H), 7.04 (d, J=2.3 Hz, 1H), 5.96 (d, J=2.9 Hz, 1H), 4.39 (t, J=7.2 Hz, 2H), 4.19 (t, J=7.1 Hz, 2H), 3.75-3.51 (m, 1H), 2.83 (t, J=10.3 Hz, 1H), 2.08 (t, J=7.2 Hz, 2H), 1.87 (ddt, J=19.6, 12.7, 6.9 Hz, 3H), 1.67 (s, 2H), 1.43 (s, 9H), 1.33 (s, 3H), 1.30 (d, J=13.3 Hz, 2H), 1.23 (s, 3H), 1.05-1.00 (m, 2H), 0.76-0.70 (m, 2H). ESI-MS m/z calc. 743.248, found 744.3 (M+1)+; Retention time: 0.86 min (LC Method A).

Step 3: 20,20-Dimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione

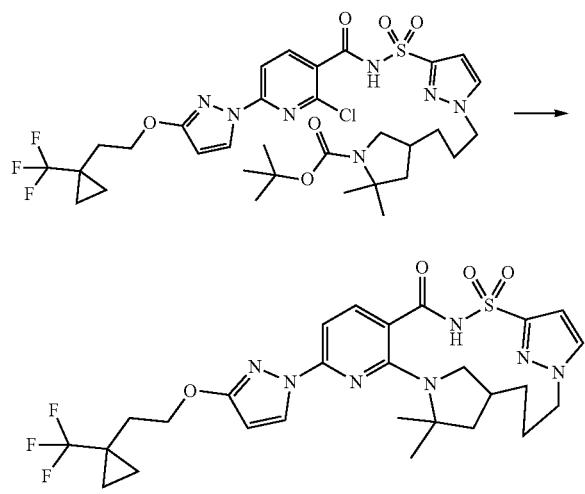

Part A: A solution of tert-butyl 4-[3-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]propyl]-2,2-dimethyl-pyrrolidine-1-carboxylate (247 mg, 0.3319 mmol) in dichloromethane (1 mL) and trifluoroacetic acid (260 µL, 3.398 mmol) was stirred at room temperature for 4 h. The solvents were then evaporated. The residue was dissolved in ethyl acetate, washed with 2 mL of saturated sodium bicarbonate solution and solvent was removed and dried under high vacuum.

Part B: The residue from Part A was dissolved in dimethyl sulfoxide (6 mL) and 3 Å molecular sieves were added and the reaction mixture was stirred for 10 min. Then cesium fluoride (153 mg, 1.007 mmol) and potassium carbonate (142 mg, 1.027 mmol) were added and the reaction mixture was heated at 130° C. overnight. The reaction mixture was filtered through a Whatman filter disc (puradisc 25 TF) and the filtrate was purified by a reverse phase HPLC-MS method using a dual gradient run from 50-90% mobile phase B over 15.0 min (mobile phase A=water (0.05% hydrochloric acid), mobile phase B=acetonitrile) to afford 20,20-dimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2(7),3,5,11(22),12-pentaene-8,10,10-trione (80 mg, 40%) as a white solid. ESI-MS m/z calc. 607.2189, found 608.1 (M+1)+; Retention time: 2.07 min (LC Method B).

Step 4: (18R)-20,20-Dimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Compound 84) and (18S)-20,20-dimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Compound 85)

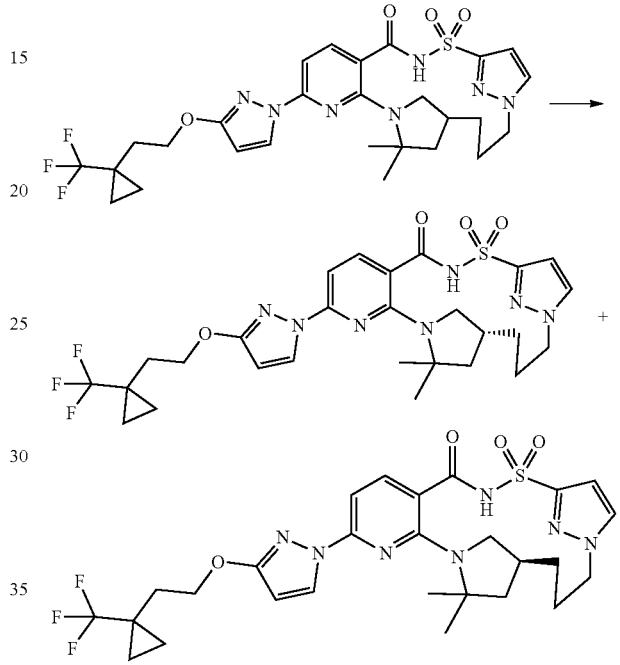

Subjected racemic 20,20-dimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2(7),3,5,11(22),12-pentaene-8,10,10-trione (80 mg) to chiral separation by SFC chromatography using Chiral Pak AS-H (250×10 mm), column, 5 µm particle size) with 27% acetonitrile:methanol, 73% carbon dioxide mobile phase at 10 mL/min over 8.0 min (injection volume=70 µL of 24 mg/mL in acetonitrile:methanol (90:10)) giving as the first enantiomer to elute (18R)-20,20-dimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Compound 84) (27 mg, 27%); 1H NMR (400 MHz, Chloroform-d) δ 8.82 (s, 1H), 8.16 (d, J=2.8 Hz, 1H), 7.66 (d, J=8.2 Hz, 1H), 7.46 (d, J=2.4 Hz, 1H), 7.06 (d, J=2.3 Hz, 1H), 6.96 (d, J=8.2 Hz, 2H), 5.86 (d, J=2.8 Hz, 1H), 4.39 (d, J=7.1 Hz, 2H), 4.31 (dt, J=13.3, 3.3 Hz, 1H), 3.91 (td, J=12.8, 2.7 Hz, 2H), 2.81-2.66 (m, 2H), 2.19-2.07 (m, 3H), 1.97 (t, J=10.1 Hz, 1H), 1.75 (dd, J=11.7, 5.3 Hz, 1H), 1.57 (s, 3H), 1.54 (s, 3H), 1.46 (t, J=12.2 Hz, 1H), 1.08-0.99 (m, 2H), 0.81-0.71 (m, 4H), ESI-MS m/z calc. 607.2189, found 608.1 (M+1)+; Retention time: 2.07 min (LC Method B) and as the second enantiomer to elute (18S)-20,20-dimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Compound 85) (31.5 mg, 31%); 1H NMR (400 MHz, Chloroform-d) δ

8.44 (s, 1H), 8.17 (d, J=2.7 Hz, 1H), 7.68 (d, J=8.2 Hz, 1H), 7.48 (d, J=2.3 Hz, 1H), 7.07 (d, J=2.3 Hz, 1H), 7.00 (d, J=8.3 Hz, 1H), 5.86 (d, J=2.7 Hz, 1H), 4.39 (d, J=7.2 Hz, 2H), 4.33 (d, J=3.5 Hz, 1H), 3.93 (t, J=12.3 Hz, 1H), 2.74 (s, 1H), 2.22-2.12 (m, 2H), 2.09 (t, J=7.2 Hz, 2H), 1.99 (t, J=10.3 Hz, 2H), 1.76 (dd, J=11.9, 5.3 Hz, 1H), 1.59 (s, 3H), 1.55 (s, 3H), 1.47 (t, J=12.2 Hz, 1H), 1.06-1.00 (m, 2H), 0.89-0.68 (m, 4H), ESI-MS m/z calc. 607.2189, found 608.1 (M+1)⁺; Retention time: 2.07 minutes (LC Method B).

Example 23: Preparation of 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (Enantiomer 1) (Compound 95) and 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (Enantiomer 2) (Compound 96)

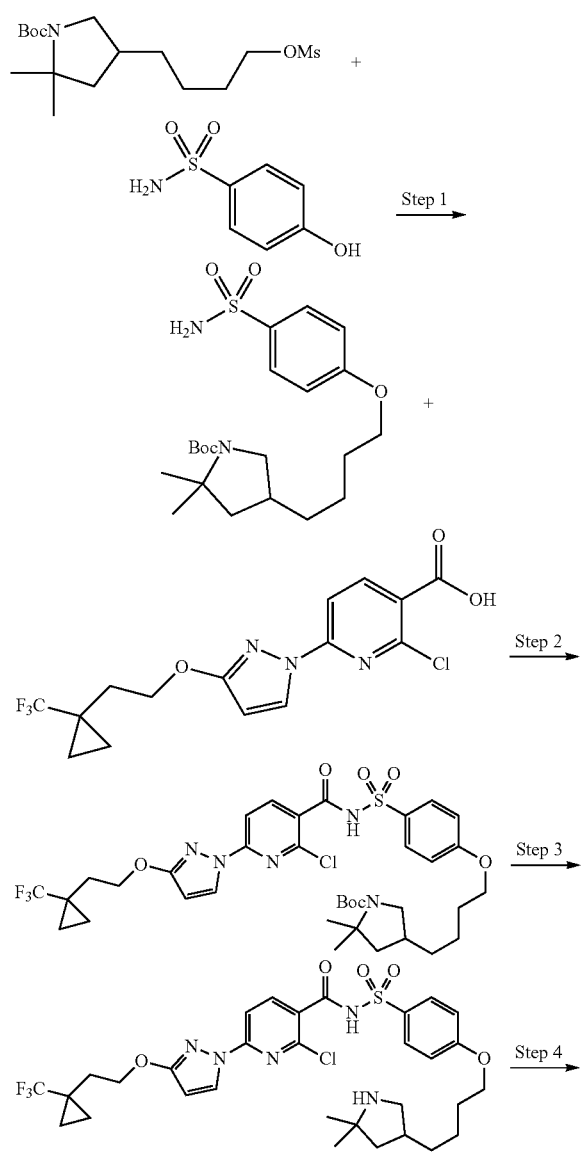

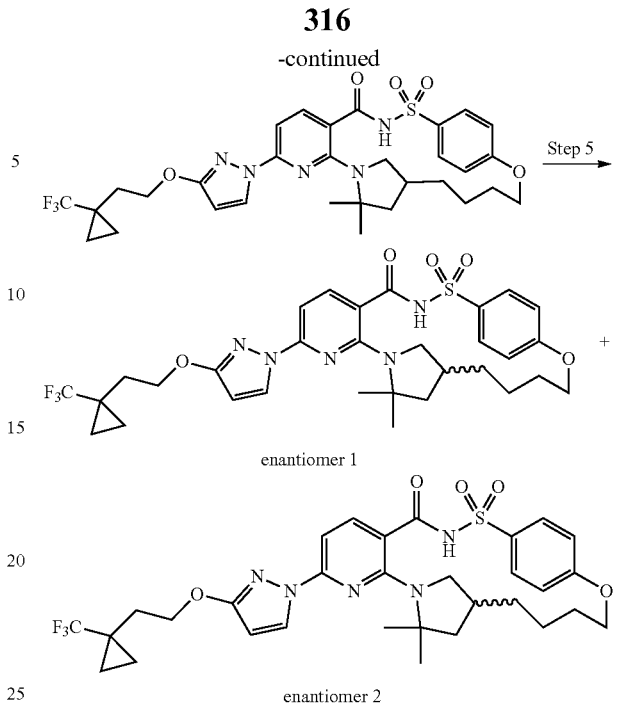

Step 1: tert-Butyl 2,2-dimethyl-4-[4-(4-sulfamoylphenoxy)butyl]pyrrolidine-1-carboxylate

In a 50 mL flask was added 4-hydroxybenzenesulfonamide (319 mg, 1.842 mmol) and N,N-dimethylformamide (12.88 mL). To the mixture was added tert-butyl 2,2-dimethyl-4-(4-methylsulfonyloxybutyl)pyrrolidine-1-carboxylate (643.8 mg, 1.842 mmol) and potassium carbonate (891 mg, 6.447 mmol) at room temperature and stirred at 50° C. overnight. Cooled to room temperature and poured into water (100 mL) and extracted with ethyl acetate (2×100 mL), combined organic layers, washed with water (2×100 mL), dried (sodium sulfate), filtered and concentrated to a brown residue which was purified by silica gel chromatography using a gradient from 100% hexanes to 100% ethyl acetate to afford tert-butyl 2,2-dimethyl-4-[4-(4-sulfamoylphenoxy)butyl]pyrrolidine-1-carboxylate (416.1 mg, 53%) as a light orange oil. ¹H NMR (400 MHz, dimethyl sulfoxide-d₆) δ 7.46 (t, J=8.0 Hz, 1H), 7.39-7.33 (m, 2H), 7.31 (s, 2H), 7.13 (d, J=7.8 Hz, 1H), 4.02 (t, J=6.0 Hz, 2H), 3.85-3.67 (m, 1H), 1.88 (dd, J=11.8, 6.6 Hz, 2H), 1.79-1.61 (m, 4H), 1.51 (dd, J=37.7, 5.8 Hz, 2H), 1.38 (s, 12H), 1.24 (s, 3H). ESI-MS m/z calc. 426.21884, found 427.3 (M+1)⁺; Retention time: 0.75 min (LC Method A).

Step 2: tert-Butyl 4-[4-[4-[[2-chloro-6-[3-[2-[1-(trifluoromethyl)cyclopropyl]ethoxy]pyrazol-1-yl]pyridine-3-carbonyl]sulfamoyl]phenoxy]butyl]-2,2-dimethyl-pyrrolidine-1-carboxylate

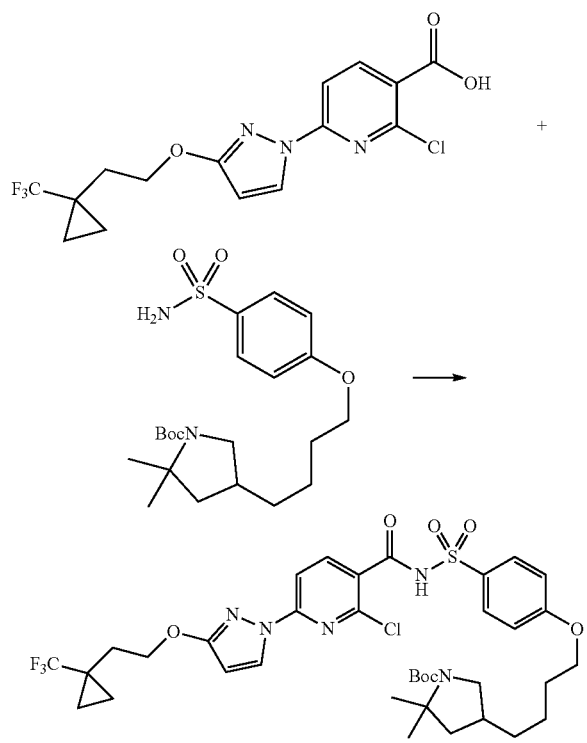

In a 20 mL vial, 2-chloro-6-[3-[2-[1-(trifluoromethyl)cyclopropyl]ethoxy]pyrazol-1-yl]pyridine-3-carboxylic acid (549.7 mg, 1.463 mmol) and carbonyl diimidazole (237.2 mg, 1.463 mmol) were combined in tetrahydrofuran (5.971 mL) and stirred for 120 min at 50° C. with a loose cap. Then tert-butyl 2,2-dimethyl-4-[4-(4-sulfamoylphenoxy)butyl]pyrrolidine-1-carboxylate (416.1 mg, 0.9755 mmol) in tetrahydrofuran (7.964 mL) was added followed by 1,8-diazabicyclo[5.4.0]undec-7-ene (297.0 mg, 291.7 µL, 1.951 mmol) and the reaction was heated at 50° C. for 16 hrs. The reaction was diluted with ethyl acetate and washed with saturated aqueous ammonium chloride followed by brine. The organics were separated, dried over sodium sulfate, filtered and evaporated then purified by silica gel chromatography using a shallow gradient from 100% hexanes to 100% ethyl acetate giving very poor separation. Fractions containing product were combined and concentrated then repurified by silica gel chromatography using a shallow gradient from 100% dichloromethane to 20% methanol/dichloromethane giving tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]phenoxy]butyl]-2,2-dimethyl-pyrrolidine-1-carboxylate (596 mg, 78%) as a light yellow solid. ESI-MS m/z calc. 783.268, found 784.2 (M+1)⁺; Retention time: 2.54 min (LC Method B).

Step 3: 2-chloro-N-[4-[4-(5,5-dimethylpyrrolidin-3-yl)butoxy]phenyl]sulfonyl-6-[3-[2-[1-(trifluoromethyl)cyclopropyl]ethoxy]pyrazol-1-yl]pyridine-3-carboxamide

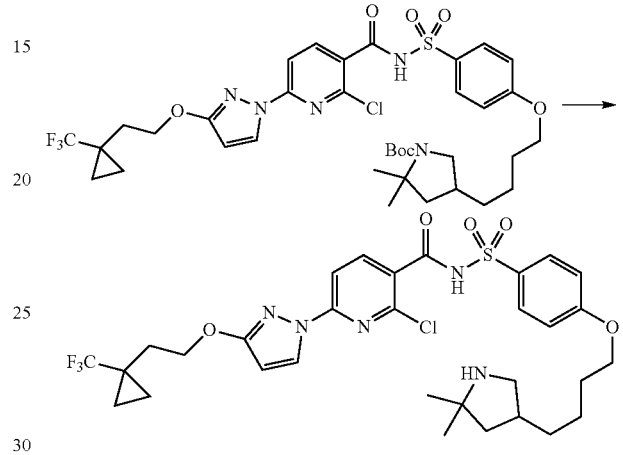

tert-Butyl 4-[4-[4-[[2-chloro-6-[3-[2-[1-(trifluoromethyl)cyclopropyl]ethoxy]pyrazol-1-yl]pyridine-3-carbonyl]sulfamoyl]phenoxy]butyl]-2,2-dimethyl-pyrrolidine-1-carboxylate (596 mg, 0.7599 mmol) was dissolved in dichloromethane (2.600 mL) and to the mixture was added trifluoroacetic acid (3.975 g, 2.686 mL, 34.86 mmol) and stirred at room temperature for 60 min. Concentrated mixture to dryness under reduced pressure, took up in saturated aqueous sodium bicarbonate and ethyl acetate containing a small amount of methanol for solubility and separated the layers. Concentrated the organic layer by rotary evaporation followed by high vacuum pump giving 2-chloro-N-[4-[4-(5,5-dimethylpyrrolidin-3-yl)butoxy]phenyl]sulfonyl-6-[3-[2-[1-(trifluoromethyl)cyclopropyl]ethoxy]pyrazol-1-yl]pyridine-3-carboxamide (403.3 mg, 78%) as an off-white solid. ESI-MS m/z calc. 683.2156, found 684.2 (M+1)⁺; Retention time: 0.66 min (LC Method A).

Step 4: 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (Compound 89)

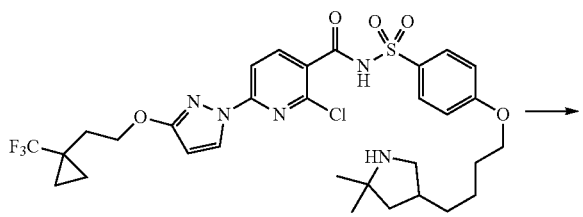

319

-continued

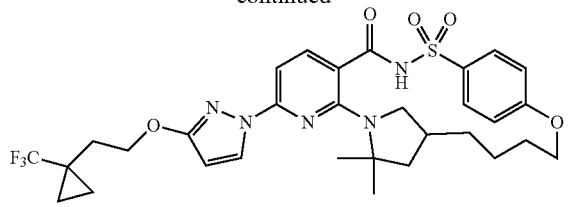

To a solution of 2-chloro-N-[4-[4-(5,5-dimethylpyrrolidin-3-yl)butoxy]phenyl]sulfonyl-6-[3-[2-[1-(trifluoromethyl)cyclopropyl]ethoxy]pyrazol-1-yl]pyridine-3-carboxamide (403.3 mg, 0.5895 mmol) in dimethyl sulfoxide (16.13 mL) was added potassium carbonate (488.7 mg, 3.536 mmol), cesium fluoride (107.5 mg, 0.7077 mmol) and a small amount of 3 Å molecular sieves. The resulting mixture was capped and heated to 165° C. for 18 h. The mixture was then cooled to room temperature, diluted with ethyl acetate and washed with saturated aqueous ammonium chloride and brine. The organic phase was dried (sodium sulfate), filtered and concentrated to a tan amorphous solid which was purified by silica gel chromatography using a shallow gradient from 100% hexanes to 100% ethyl acetate giving 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (Compound 89) (80 mg, 21%). ¹H NMR (400 MHz, dimethyl sulfoxide-d₆) δ 12.22 (s, 1H), 8.19 (d, J=2.8 Hz, 1H), 8.08 (dd, J=8.6, 2.5 Hz, 1H), 7.88 (d, J=8.3 Hz, 1H), 7.77 (dd, J=8.7, 2.5 Hz, 1H), 7.34 (ddd, J=16.6, 8.7, 2.5 Hz, 2H), 6.92 (d, J=8.3 Hz, 1H), 6.11 (d, J=2.7 Hz, 1H), 4.40 (t, J=4.8 Hz, 2H), 4.31 (t, J=7.0 Hz, 2H), 2.40 (s, 1H), 2.07 (t, J=7.1 Hz, 2H), 1.95 (d, J=29.5 Hz, 2H), 1.76 (t, J=6.5 Hz, 2H), 1.59 (s, 1H), 1.52 (d, J=6.7 Hz, 6H), 1.46 (d, J=12.3 Hz, 1H), 1.33 (s, 1H), 1.24 (s, 1H), 1.08-1.00 (m, 1H), 0.96 (q, J=4.7, 4.0 Hz, 2H), 0.88 (s, 2H), 0.67 (s, 1H). ESI-MS m/z calc. 647.23895, found 648.2 (M+1)⁺; Retention time: 2.37 min (LC Method B).

Step 5: 12,12-Dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (Enantiomer 1) (Compound 95) and 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (Enantiomer 2) (Compound 96)

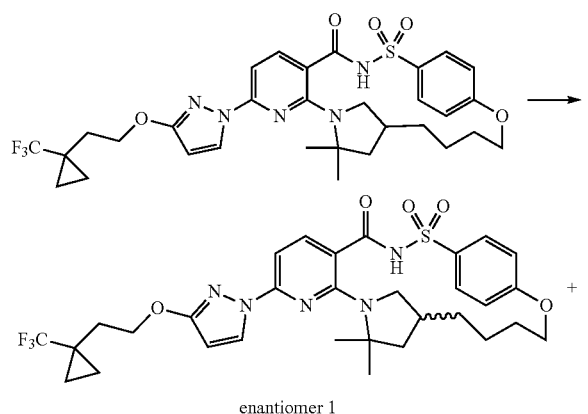

enantiomer 1

320

-continued

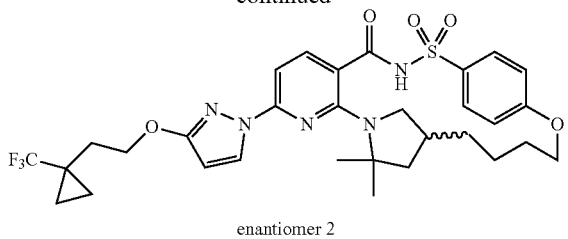

enantiomer 2

Subjected racemic 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (Compound 89) (72.1 mg, 0.1101 mmol) to chiral separation by SFC chromatography using a ChiralCel OD-H (250×10 mm column, 5 μm particle size) with 35% acetonitrile/methanol (90:10)/65% carbon dioxide mobile phase at 10 mL/min over 8.0 min (injection volume=70 μL of 24 mg/mL solution in acetonitrile/methanol (90:10) giving as the first enantiomer to elute, 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (enantiomer 1) (Compound 95) (21.9 mg, 61%); ¹H NMR (400 MHz, dimethyl sulfoxide-d₆) δ 12.23 (s, 1H), 8.19 (d, J=2.8 Hz, 1H), 8.08 (dd, J=8.6, 2.4 Hz, 1H), 7.88 (d, J=8.3 Hz, 1H), 7.76 (dd, J=8.7, 2.4 Hz, 1H), 7.34 (ddd, J=16.3, 8.7, 2.5 Hz, 2H), 6.92 (d, J=8.3 Hz, 1H), 6.11 (d, J=2.7 Hz, 1H), 4.40 (t, J=4.9 Hz, 2H), 4.31 (t, J=7.0 Hz, 2H), 3.17 (d, J=5.2 Hz, 1H), 2.40 (d, J=10.3 Hz, 1H), 2.07 (t, J=7.1 Hz, 2H), 1.92 (d, J=5.4 Hz, 2H), 1.81-1.72 (m, 2H), 1.58 (d, J=15.1 Hz, 1H), 1.53 (s, 3H), 1.51 (s, 3H), 1.33 (t, J=13.3 Hz, 1H), 1.12-0.98 (m, 2H), 0.98-0.94 (m, 2H), 0.88 (tt, J=5.6, 2.4 Hz, 2H), 0.66 (d, J=13.0 Hz, 1H), ESI-MS m/z calc. 647.23895, found 648.2 (M+1)⁺; Retention time: 2.34 min (LC Method B) and as the second enantiomer to elute, 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.2.2.1¹¹,¹⁴.0⁵,¹⁰]pentacosa-1(22),5,7,9,20,23-hexaene-2,2,4-trione (enantiomer 2) (Compound 96) (18.75 mg, 52%); ESI-MS m/z calc. 647.23895, found 648.2 (M+1)⁺; Retention time: 2.33 min (LC Method B).

Example 24: Preparation of (14S)-8-[3-(3,3-dimethylbutyl)-4,4-dimethyl-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (hydrochloric acid salt) (Compound 98)

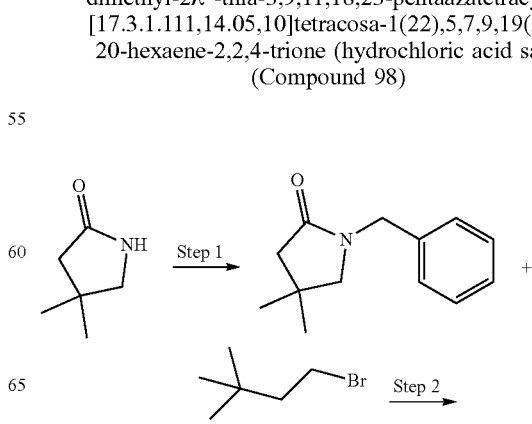

-continued

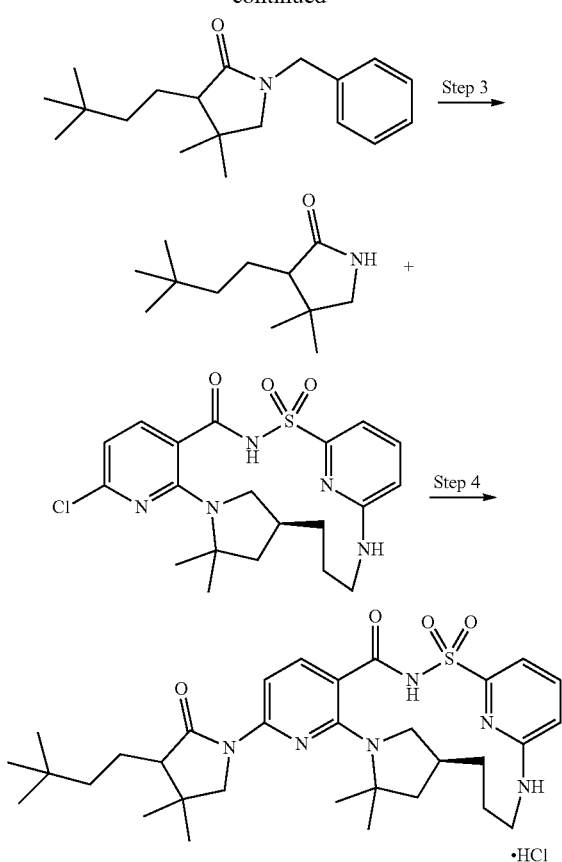

Step 1: 1-Benzyl-4,4-dimethyl-pyrrolidin-2-one

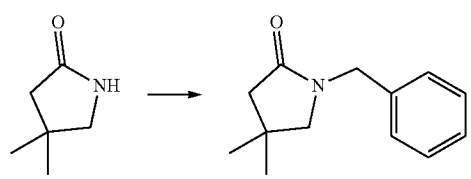

To a 100 mL round bottom flask charged with 4,4-dimethylpyrrolidin-2-one (524 mg, 4.631 mmol) was added tetrahydrofuran (25 mL), followed by 2-methylpropan-2-olate sodium salt) (590 mg, 6.139 mmol) and the mixture was stirred at room temperature for 30 min. Bromomethylbenzene (1000 μL, 8.408 mmol) was added and the reaction mixture was stirred at room temperature for 18 h. The reaction was quenched with water (~15 mL) and the crude mixture was extracted with ethyl acetate (3×30 mL). The combined organic extracts were dried over magnesium sulfate and concentrated in vacuo. The crude reaction mixture was purified via silica gel chromatography (0%-60% ethyl acetate in hexanes gradient) affording 1-benzyl-4,4-dimethyl-pyrrolidin-2-one (834 mg, 89%) as a clear oil. ESI-MS m/z calc. 203.13101, found 204.1 (M+1)$^+$; Retention time: 1.3 min (LC Method B).

Step 2: 1-Benzyl-3-(3,3-dimethylbutyl)-4,4-dimethyl-pyrrolidin-2-one

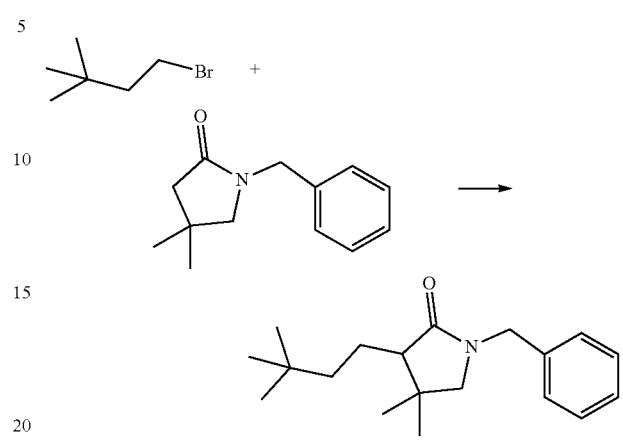

A 100 mL round bottom flask was charged with 1-benzyl-4,4-dimethyl-pyrrolidin-2-one (834 mg, 4.103 mmol) and tetrahydrofuran (20 mL) and the reaction flask was purged with nitrogen for 5 min. The reaction flask was cooled to −78° C. and butyllithium (2.1 mL of 2.5 M, 5.250 mmol) in hexanes was added dropwise and the mixture was stirred at −78° C. for 1 h. 1-bromo-3,3-dimethyl-butane (700 μL, 4.970 mmol) was added dropwise and the reaction mixture was stirred and slowly warmed to room temperature over a period of 18 h. The reaction was quenched with water (10 mL) and brine (10 mL) and extracted with ethyl acetate (3×40 mL). The combined organic extracts were dried over magnesium sulfate and concentrated in vacuo. The crude reaction mixture was purified by silica gel chromatography (0%-40% ethyl acetate in hexanes gradient) affording 1-benzyl-3-(3,3-dimethylbutyl)-4,4-dimethyl-pyrrolidin-2-one (107 mg, 9%) as a clear oil. ESI-MS m/z calc. 287.2249, found 288.1 (M+1)$^+$; Retention time: 2.15 min (LC Method B).

Step 3: 3-(3,3-Dimethylbutyl)-4,4-dimethyl-pyrrolidin-2-one

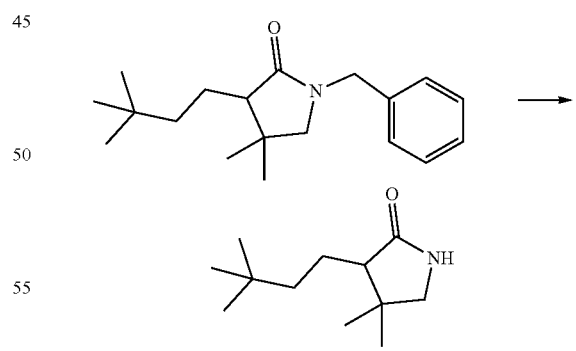

To a nitrogen-purged 50 mL flask charged with 1-benzyl-3-(3,3-dimethylbutyl)-4,4-dimethyl-pyrrolidin-2-one (107 mg, 0.3723 mmol) was added propan-1-amine (3 mL) and ethane-1,2-diamine (200 μL, 2.992 mmol). The solution was cooled to −30° C. and a strip of lithium wire (4 cm, cut into 4 smaller pieces and rinsed with hexanes to remove excess oil) was added. The flask was re-fitted with a septum and the reaction mixture stirred vigorously, with slight warming to −20° C. A blue color eventually formed around the lithium wire, with blue color leeching out into the solution briefly and the reaction was allowed to stir until the solution remained a deep blue color (~20 min). Water (~15 mL) was added and the larger pieces of lithium were removed and the mixture was warmed to room temperature and stirred for 10 min. The crude mixture was extracted with ethyl acetate (3×20 mL), the combined organic extracts washed with water (15 mL), dried over sodium sulfate, filtered and concentrated in vacuo affording crude 3-(3,3-dimethyl-butyl)-4,4-dimethyl-pyrrolidin-2-one (115 mg, 157% (crude product containing impurities)) as a yellow oil, which was used without further purification. ESI-MS m/z calc. 197.17796, found 198.1 (M+1)$^+$; Retention time: 1.58 min (LC Method B).

Step 4: (14S)-8-[3-(3,3-Dimethylbutyl)-4,4-dimethyl-2-oxopyrrolidin-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (Hydrochloric Acid Salt) (Compound 98)

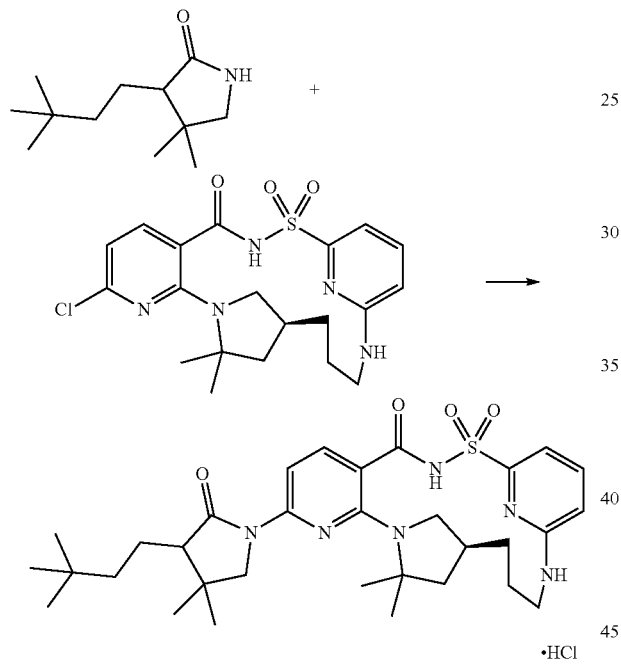

To a 4 mL vial charged with crude 3-(3,3-dimethylbutyl)-4,4-dimethyl-pyrrolidin-2-one (45 mg, 0.2281 mmol) was added (14S)-8-chloro-12,12-dimethyl-2$\lambda^6$-thia-3,9,11,18,23-pentaazatetracyclo[17.3.1.111,14.05,10]tetracosa-1(23),5,7,9,19,21-hexaene-2,2,4-trione (25 mg, 0.05373 mmol), (5-diphenylphosphanyl-9,9-dimethyl-xanthen-4-yl)-diphenyl-phosphane (8 mg, 0.01383 mmol), tris(dibenzylideneacetone)dipalladium(0) (13 mg, 0.01420 mmol), cesium carbonate (25 mg, 0.07673 mmol) and dioxane (1 mL). The headspace was purged with nitrogen, the vial capped and the reaction mixture stirred at 120° C. for 18 h. After cooling to room temperature, the crude mixture was diluted with ethyl acetate (~30 mL) and washed with 1.0M aqueous citric acid (5 mL). The organic layer was dried over magnesium sulfate, filtered and concentrated in vacuo. The crude residue was taken up in a minimal amount of dimethyl sulfoxide (0.4-1 mL) and subjected to HPLC purification (C$_{18}$ reverse-phase, 99:1-1:99 water: acetonitrile, hydrochloric acid modifier). The fractions were then concentrated in vacuo and the residue purified by silica gel chromatography (0%-70%) ethyl acetate in hexanes gradient affording (14S)-8-[3-(3,3-dimethylbutyl)-4,4-dimethyl-2-oxopyrrolidin-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (hydrochloric acid salt) (Compound 98) (4 mg, 11%) as an off-white solid. $^1$H NMR (400 MHz, dimethyl sulfoxide-d$_6$) δ 12.42 (s, 1H), 7.66 (dd, J=8.3, 3.2 Hz, 1H), 7.52 (ddd, J=22.6, 14.8, 8.2 Hz, 2H), 7.03 (d, J=7.2 Hz, 1H), 6.92 (d, J=32.0 Hz, 1H), 6.69 (d, J=8.7 Hz, 1H), 4.46-3.82 (m, 3H), 3.83-3.41 (m, 3H), 3.09 (s, 1H), 2.93 (d, J=13.3 Hz, 1H), 2.80-2.63 (m, 1H), 2.40-2.23 (m, 1H), 2.17-1.98 (m, 1H), 1.90-1.68 (m, 2H), 1.68-1.38 (m, 8H), 1.28 (d, J=40.1 Hz, 5H), 1.18 (d, J=5.6 Hz, 2H), 1.02-0.70 (m, 9H). ESI-MS m/z calc. 610.33014, found 611.2 (M+1)$^+$; Retention time: 2.38 min (LC Method B).

Example 25: Preparation of 12,12-dimethyl-8-(3-{2-[1-(trifluoromethyl)cyclopropyl]ethoxy}-1H-pyrazol-1-yl)-18-oxa-2$\lambda^6$-thia-3,9,11-triazatetracyclo[17.2.2.111,14.05,10]tetracosa-1(21),5,7,9,19,22-hexaene-2,2,4-trione (Enantiomer 1) (Compound 99) and 12,12-dimethyl-8-(3-{2-[1-(trifluoromethyl)cyclopropyl]ethoxy}-1H-pyrazol-1-yl)-18-oxa-2$\lambda^6$-thia-3,9,11-triazatetracyclo[17.2.2.111,14.05,10]tetracosa-1(21),5,7,9,19,22-hexaene-2,2,4-trione (Enantiomer 2) (Compound 100)

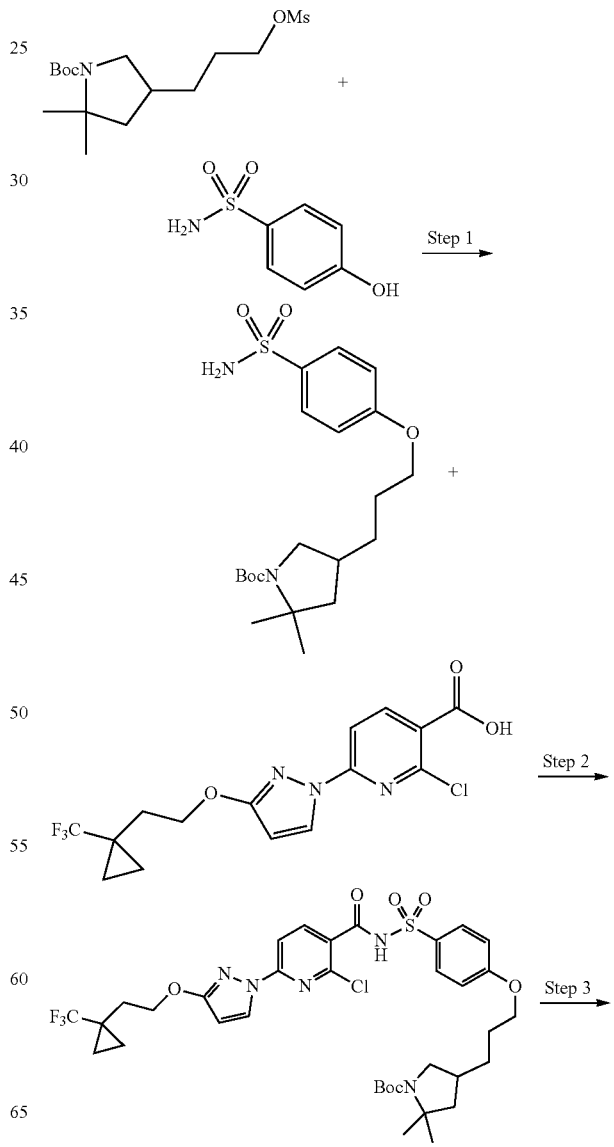

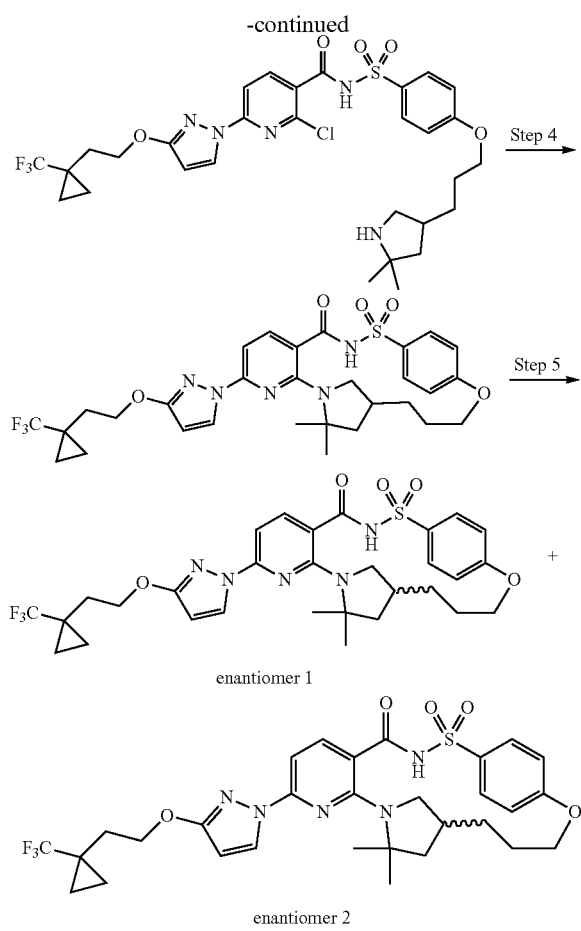

Step 1: tert-Butyl 2,2-dimethyl-4-[3-(4-sulfamoylphenoxy)propyl]pyrrolidine-1-carboxylate

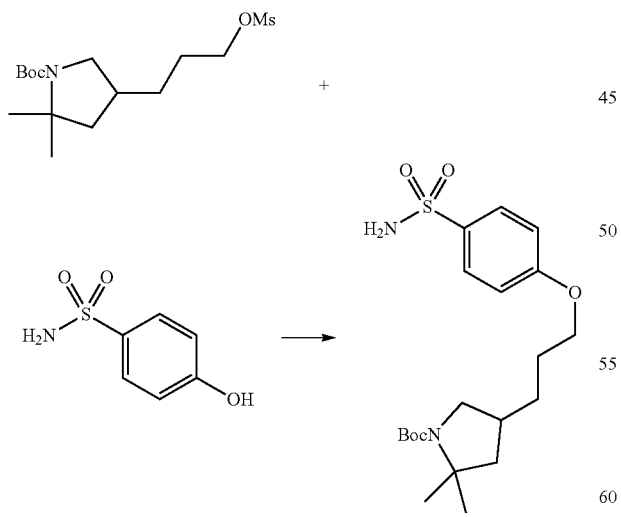

In a 50 mL flask was added 4-hydroxybenzenesulfonamide (471.1 mg, 2.720 mmol) and N,N-dimethylformamide (13.69 mL). To the mixture was added tert-butyl 2,2-dimethyl-4-(3-methylsulfonyloxypropyl)pyrrolidine-1-carboxylate (912.4 mg, 2.720 mmol) and potassium carbonate (1.316 g, 9.520 mmol) at room temperature and stirred at room temperature for 3 h then heated to 50° C. overnight. Cooled to room temperature and poured into water (100 mL) and extracted with ethyl acetate (2×100 mL), combined organic layers, washed with water (2×100 mL), dried (sodium sulfate), filtered and concentrated to a brown residue which was purified by silica gel chromatography using a gradient from 100% hexanes to 100% ethyl acetate to afford tert-butyl 2,2-dimethyl-4-[3-(4-sulfamoylphenoxy)propyl]pyrrolidine-1-carboxylate (578.3 mg, 52%) as a light orange oil. $^1$H NMR (400 MHz, dimethyl sulfoxide-d$_6$) δ 7.46 (t, J=8.0 Hz, 1H), 7.39-7.33 (m, 2H), 7.31 (s, 2H), 7.13 (d, J=7.8 Hz, 1H), 4.02 (t, J=6.0 Hz, 2H), 3.85-3.67 (m, 1H), 1.88 (dd, J=11.8, 6.6 Hz, 2H), 1.79-1.61 (m, 4H), 1.51 (dd, J=37.7, 5.8 Hz, 2H), 1.38 (s, 12H), 1.24 (s, 3H). ESI-MS m/z calc. 412.2032, found 413.3 (M+1)$^+$; Retention time: 0.71 min (LC Method A).

Step 2: tert-Butyl 4-[3-[4-[[2-chloro-6-[3-[2-[1-(trifluoromethyl)cyclopropyl]ethoxy]pyrazol-1-yl]pyridine-3-carbonyl]sulfamoyl]phenoxy]propyl]-2,2-dimethyl-pyrrolidine-1-carboxylate

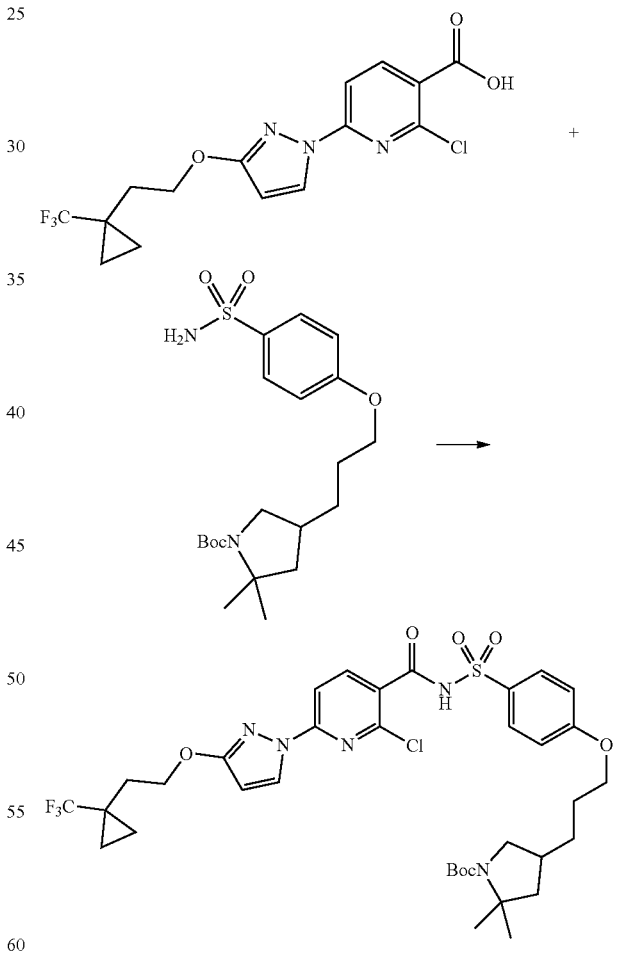

In a 20 mL vial, 2-chloro-6-[3-[2-[1-(trifluoromethyl)cyclopropyl]ethoxy]pyrazol-1-yl]pyridine-3-carboxylic acid (790.2 mg, 2.103 mmol) and carbonyl diimidazole (341.0 mg, 2.103 mmol) were combined in tetrahydrofuran (6 mL) and stirred for 120 min at 50° C. with a loose cap. Then tert-butyl 2,2-dimethyl-4-[3-(4-sulfamoylphenoxy)

propyl]pyrrolidine-1-carboxylate (578.3 mg, 1.402 mmol) in tetrahydrofuran (10 mL) was added followed by 1,8-diazabicyclo[5.4.0]undec-7-ene (426.9 mg, 419.4 µL, 2.804 mmol) and the reaction was heated at 50° C. for 16 hrs. The reaction was diluted with ethyl acetate and washed with saturated aqueous ammonium chloride followed by brine. The organics were separated, dried over sodium sulfate, filtered and evaporated then purified by silica gel chromatography using a shallow gradient from 100% hexanes to 100% ethyl acetate giving very poor separation. Fractions containing product were combined and concentrated then repurified by silica gel chromatography using a shallow gradient from 100% dichloromethane to 20% methanol/dichloromethane giving tert-butyl 4-[3-[4-[[2-chloro-6-[3-[2-[1-(trifluoromethyl)cyclopropyl]ethoxy]pyrazol-1-yl]pyridine-3-carbonyl]sulfamoyl]phenoxy]propyl]-2,2-dimethyl-pyrrolidine-1-carboxylate (953.1 mg, 88%) as a light yellow solid. ESI-MS m/z calc. 769.2524, found 770.1 (M+1)$^+$; Retention time: 2.49 min (LC Method B).

Step 3: 2-Chloro-N-[4-[3-(5,5-dimethylpyrrolidin-3-yl)propoxy]phenyl]sulfonyl-6-[3-[2-[1-(trifluoromethyl)cyclopropyl]ethoxy]pyrazol-1-yl]pyridine-3-carboxamide

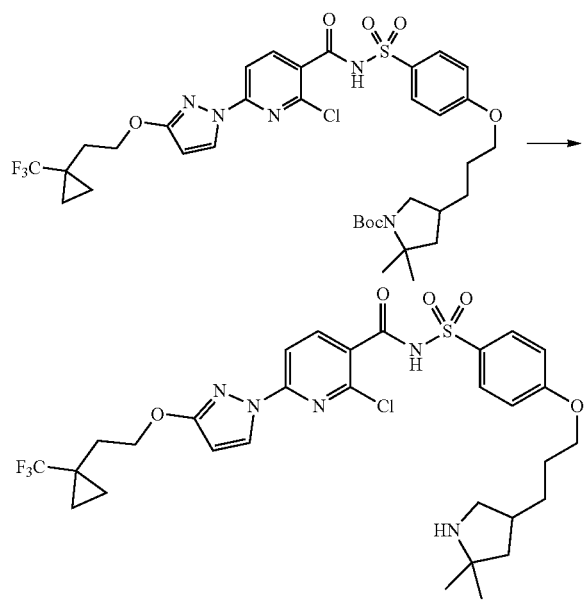

tert-Butyl 4-[3-[4-[[2-chloro-6-[3-[2-[1-(trifluoromethyl)cyclopropyl]ethoxy]pyrazol-1-yl]pyridine-3-carbonyl]sulfamoyl]phenoxy]propyl]-2,2-dimethyl-pyrrolidine-1-carboxylate (953.1 mg, 1.237 mmol) was dissolved in dichloromethane (4.158 mL) and to the mixture was added trifluoroacetic acid (6.471 g, 4.372 mL, 56.75 mmol) and the mixture was stirred at room temperature for 60 min. Concentrated mixture to dryness under reduced pressure, took up in saturated aqueous sodium bicarbonate and ethyl acetate containing a small amount of methanol for solubility and separated the layers. Concentrated the organic layer by rotary evaporation followed by drying on vacuum giving 2-chloro-N-[4-[3-(5,5-dimethylpyrrolidin-3-yl)propoxy]phenyl]sulfonyl-6-[3-[2-[1-(trifluoromethyl)cyclopropyl]ethoxy]pyrazol-1-yl]pyridine-3-carboxamide (738.1 mg, 89%) as an off-white solid. ESI-MS m/z calc. 669.19995, found 670.3 (M+1)$^+$; Retention time: 0.65 min (LC Method A).

Step 4: 12,12-Dimethyl-8-(3-{2-[1-(trifluoromethyl)cyclopropyl]ethoxy}-1H-pyrazol-1-yl)-18-oxa-2$\lambda^6$-thia-3,9,11-triazatetracyclo[17.2.2.1$^{11,14}$.0$^{5,10}$]tetracosa-1(21),5,7,9,19,22-hexaene-2,2,4-trione (Compound 88)

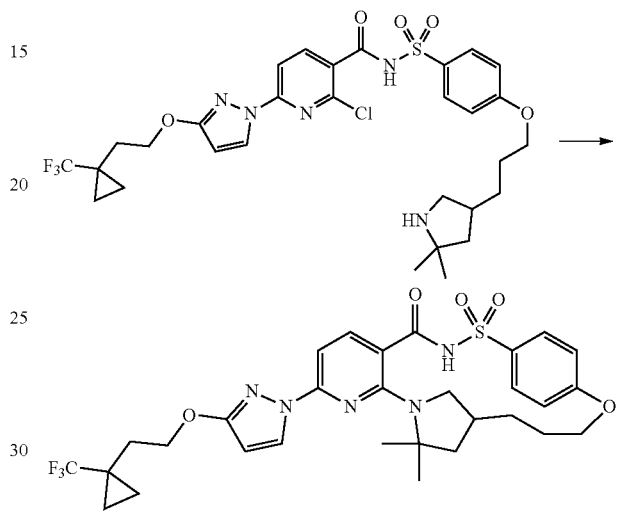

To a solution of 2-chloro-N-[4-[3-(5,5-dimethylpyrrolidin-3-yl)propoxy]phenyl]sulfonyl-6-[3-[2-[1-(trifluoromethyl)cyclopropyl]ethoxy]pyrazol-1-yl]pyridine-3-carboxamide (738.1 mg, 1.101 mmol) in dimethyl sulfoxide (29.52 mL) was added potassium carbonate (912.8 mg, 6.605 mmol), cesium fluoride (200.7 mg, 1.321 mmol) and a small amount of 3 Å molecular sieves. The resulting mixture was capped and heated to 130° C. for 16 h. Continued heating at 150° C. for 16 h. Heated to 170° C. and stirred 3 h then cooled to room temperature, diluted with ethyl acetate and washed with saturated aqueous ammonium chloride and brine. The organic phase was dried (sodium sulfate), filtered and concentrated to a tan amorphous solid which was purified by silica gel chromatography using a shallow gradient from 100% hexanes to 100% ethyl acetate giving 12,12-dimethyl-8-(3-{2-[1-(trifluoromethyl)cyclopropyl]ethoxy}-1H-pyrazol-1-yl)-18-oxa-2$\lambda^6$-thia-3,9,11-triazatetracyclo[17.2.2.1$^{11,14}$.0$^{5,10}$]tetracosa-1(21),5,7,9,19,22-hexaene-2,2,4-trione (30 mg, 4%) as a white solid. $^1$H NMR (400 MHz, dimethyl sulfoxide-d$_6$) δ 12.13 (s, 1H), 8.17 (d, J=2.8 Hz, 1H), 8.06 (d, J=7.8 Hz, 1H), 7.83 (d, J=8.3 Hz, 1H), 7.78 (d, J=8.6 Hz, 1H), 7.30 (dd, J=8.8, 2.4 Hz, 1H), 7.19 (dd, J=8.6, 2.4 Hz, 1H), 6.89 (d, J=8.3 Hz, 1H), 6.10 (d, J=2.7 Hz, 1H), 4.52 (d, J=12.1 Hz, 1H), 4.30 (t, J=7.0 Hz, 2H), 4.27-4.17 (m, 1H), 2.07 (t, J=7.1 Hz, 2H), 1.96 (s, 2H), 1.75 (s, 1H), 1.69 (d, J=12.2 Hz, 1H), 1.53 (s, 5H), 1.46 (s, 3H), 1.44-1.36 (m, 2H), 1.05 (s, 1H), 0.98-0.93 (m, 2H), 0.90-0.84 (m, 2H). ESI-MS m/z calc. 633.22327, found 634.1 (M+1)$^+$; Retention time: 2.28 min (LC Method B).

329

Step 5: 12,12-Dimethyl-8-(3-{2-[1-(trifluoromethyl) cyclopropyl]ethoxy}-1H-pyrazol-1-yl)-18-oxa-2λ⁶-thia-3,9,11-triazatetracyclo[17.2.2.111,14.05,10] tetracosa-1(21),5,7,9,19,22-hexaene-2,2,4-trione (Enantiomer 1) (Compound 99) and 12,12-dimethyl-8-(3-{2-[1-(trifluoromethyl)cyclopropyl] ethoxy}-1H-pyrazol-1-yl)-18-oxa-2λ⁶-thia-3,9,11-triazatetracyclo[17.2.2.111,14.05,10]tetracosa-1(21), 5,7,9,19,22-hexaene-2,2,4-trione (Enantiomer 2) (Compound 100)

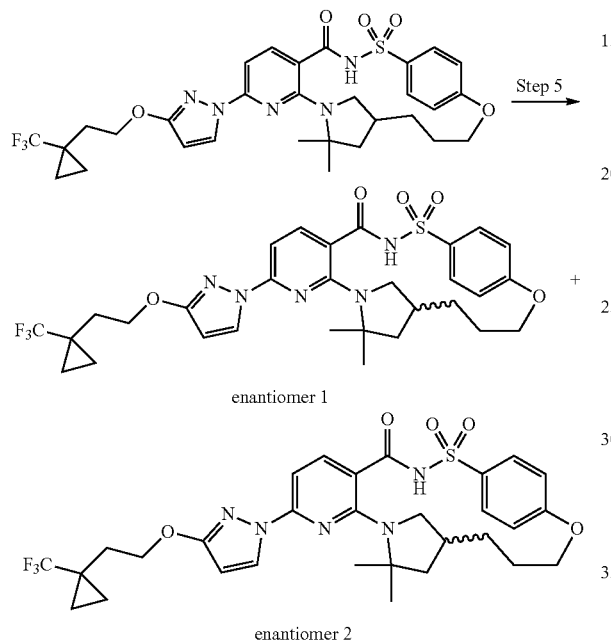

Subjected racemic 12,12-dimethyl-8-(3-{2-[1-(trifluoromethyl)cyclopropyl]ethoxy}-1H-pyrazol-1-yl)-18-oxa-2λ⁶-thia-3,9,11-triazatetracyclo [17.2.2.111,14.05,10]tetracosa-1(21),5,7,9,19,22-hexaene-2,2,4-trione (27.2 mg, 0.04292 mmol) to chiral separation by SFC chromatography using a ChiralCel OD-H (250×10 mm column, 5 μm particle size) with 42% acetonitrile/methanol (90:10)/58% carbon dioxide mobile phase at 10 mL/min over 8.0 min (injection volume=70 μL of 24 mg/mL solution in acetonitrile/methanol (90:10) giving as the first enantiomer to elute, 12,12-dimethyl-8-(3-{2-[1-(trifluoromethyl)cyclopropyl]ethoxy}-1H-pyrazol-1-yl)-18-oxa-2λ⁶-thia-3,9,11-triazatetracyclo [17.2.2.111,14.05,10]tetracosa-1(21),5,7,9,19,22-hexaene-2,2,4-trione (enantiomer 1) (Compound 99) (10.22 mg, 75%) as a white solid; ¹H NMR (400 MHz, dimethyl sulfoxide-d₆) δ 12.13 (s, 1H), 8.17 (d, J=2.8 Hz, 1H), 8.07 (d, J=8.4 Hz, 1H), 7.83 (d, J=8.3 Hz, 1H), 7.79 (d, J=8.8 Hz, 1H), 7.31 (dd, J=8.8, 2.5 Hz, 1H), 7.20 (dd, J=8.6, 2.4 Hz, 1H), 6.90 (d, J=8.3 Hz, 1H), 6.10 (d, J=2.8 Hz, 1H), 4.52 (d, J=11.9 Hz, 1H), 4.30 (t, J=7.1 Hz, 2H), 4.26-4.16 (m, 1H), 2.07 (t, J=7.1 Hz, 2H), 1.96 (s, 2H), 1.77-1.64 (m, 2H), 1.55 (s, 1H), 1.53 (s, 3H), 1.48 (s, 1H), 1.46 (s, 3H), 1.38 (dd, J=22.7, 11.1 Hz, 2H), 1.04 (d, J=8.2 Hz, 1H), 0.99-0.92 (m, 2H), 0.89 (d, J=11.6 Hz, 2H), ESI-MS m/z calc. 633.22327, found 634.1 (M+1)⁺; Retention time: 2.25 min (LC Method B) and as the second enantiomer to elute, 12,12-dimethyl-8-(3-{2-[1-(trifluoromethyl)cyclopropyl]ethoxy}-1H-pyrazol-1-yl)-18-oxa-2λ⁶-thia-3,9,11-triazatetracyclo [17.2.2.111,14.05,10]tetracosa-1(21),5,7,9,19,22-hexaene-2,2,4-trione (enantiomer 2) (Compound 100) (9.72 mg, 71%) as a white solid; ESI-MS m/z calc. 633.22327, found 634.1 (M+1)⁺; Retention time: 2.25 min (LC Method B).

Example 26: Preparation of (14S)-8-[3-(4,4-dimethylpentyl)-2-oxopyrrolidin-1-yl]-12,12-dimethyl-2λ⁶-thia-3,9,11,18,23-pentaazatetracyclo[17.3.1.111, 14.05,10]tetracosa-1(22),5,7,9,19(23),20-hexaene-2, 2,4-trione (Compound 102)

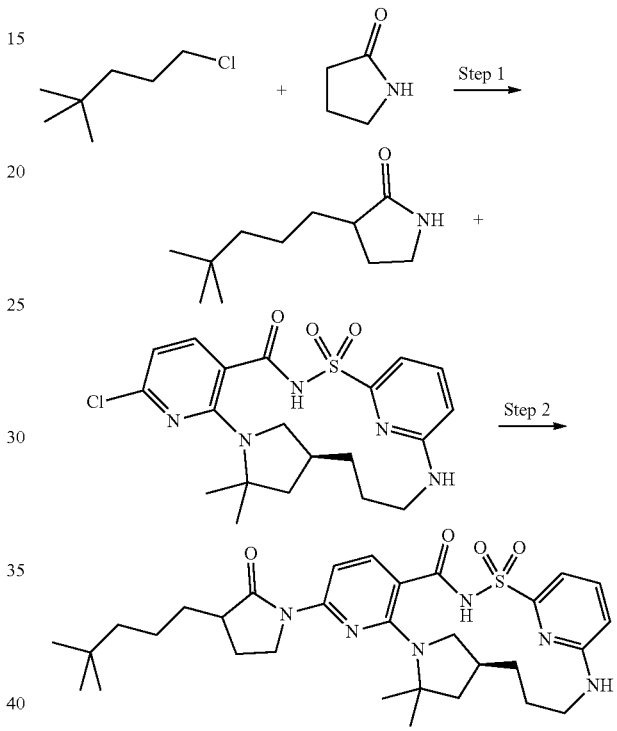

Step 1: 3-(4,4-Dimethylpentyl)pyrrolidin-2-one

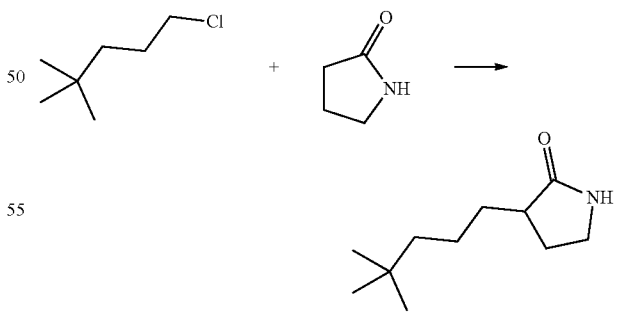

To a solution of pyrrolidin-2-one (4.64 g, 54.52 mmol) in anhydrous tetrahydrofuran (300 mL) at −78° C. was added 2.5 M n-butyllithium solution in hexane (43.6 mL, 0.109 mol) dropwise and the reaction solution was stirred at this temperature for 1 h. A solution of 1-chloro-4,4-dimethylpentane (7.34 g, 54.52 mmol) in anhydrous tetrahydrofuran (20 mL) was added slowly. After the addition was finished, the solution was stirred at −78° C. for 20 min before it was gradually warmed up to ambient temperature. 20% Aqueous ammonium chloride solution (100 mL) was added and the organic layer was separated. The aqueous layer was extracted with ethyl acetate (3×150 mL) and the combined organic layer was washed with brine, dried over sodium sulfate and concentrated. The residue obtained was purified by silica gel column chromatography using a 0-100% ethyl acetate in hexanes gradient to afford 3-(4,4-dimethylpentyl)pyrrolidin-2-one (3.86 g, 39%) as a white solid. $^1$H NMR (250 MHz, CDCl$_3$) δ (ppm): 7.51 (s, 1H), 3.12 (m, 2H), 2.15 (m, 2H), 1.60 (m, 2H), 1.29-1.11 (m, 5H), 0.86 (s, 9H). ESI-MS m/z calc. 183.16, found 184.2 (M+1)$^+$. Retention time: 4.66 min (LC Method Q).

Step 2: (14S)-8-[3-(4,4-Dimethylpentyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 102)

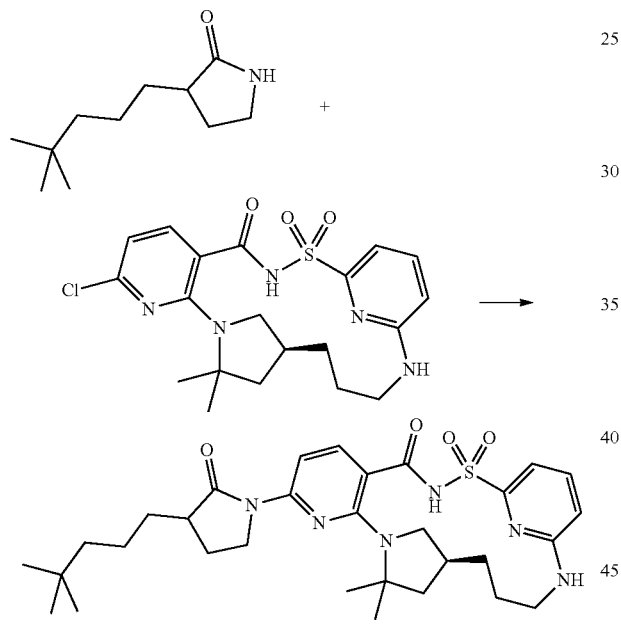

A 4 mL vial was charged with (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (25 mg, 0.05373 mmol), 3-(4,4-dimethylpentyl)pyrrolidin-2-one (29 mg, 0.1582 mmol) (crude material, purity unknown), Pd$_2$(dba)$_3$ (10 mg, 0.01092 mmol), Xantphos (6 mg, 0.01037 mmol), cesium carbonate (87.52 mg, 0.2686 mmol) and anhydrous dioxane (0.4 mL). The mixture was sparged with nitrogen for 1-2 min, capped and stirred at 120° C. for 21 h. The reaction was diluted with dimethyl sulfoxide (700 µL), microfiltered and subjected to reverse phase preparative HPLC (C$_{18}$) using a gradient of acetonitrile in water (1 to 99% over 15 min) and hydrochloric acid as a modifier. The pure fractions were collected, a bit of brine was added and the organic solvents were evaporated. The product was extracted with dichloromethane and the organic phase was dried over sodium sulfate. Evaporation of the solvents gave 8 mg of solid. The product was purified by flash chromatography on silica gel (4 g column) using a gradient of methanol (0 to 5% over 30 min) in dichloromethane. The pure fractions were collected and the solvents evaporated to give (14S)-8-[3-(4,4-dimethylpentyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 102) (5.5 mg, 17%) as a white solid mixture of diastereomers. $^1$H NMR (400 MHz, dimethyl sulfoxide-d$_6$) δ 12.42 (s, 1H), 7.68 (d, J=8.5 Hz, 1H), 7.61-7.48 (m, 2H), 7.04 (d, J=7.1 Hz, 1H), 6.96 (broad s, 1H), 6.70 (d, J=8.5 Hz, 1H), 4.08-3.72 (m, 3H), 3.10 (br d, J=8.8 Hz, 1H), 2.94 (d, J=13.2 Hz, 1H), 2.74-2.60 (m, 2H), 2.33-2.18 (m, 1H), 2.10 (br s, 1H), 1.86-1.66 (m, 4H), 1.65-1.44 (m, 9H), 1.37-1.15 (m, 6H), 0.87 (d, J=1.8 Hz, 9H). ESI-MS m/z calc. 596.31445, found 597.4 (M+1)$^+$; Retention time: 2.29 min (LC Method B).

Example 27: Syntheses of 8-[3-({dispiro[2.0.2.1]heptan-7-yl}methoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Enantiomer 1) (Compound 106) and 8-[3-({dispiro[2.0.2.1]heptan-7-yl}methoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Enantiomer 2) (Compound 107)

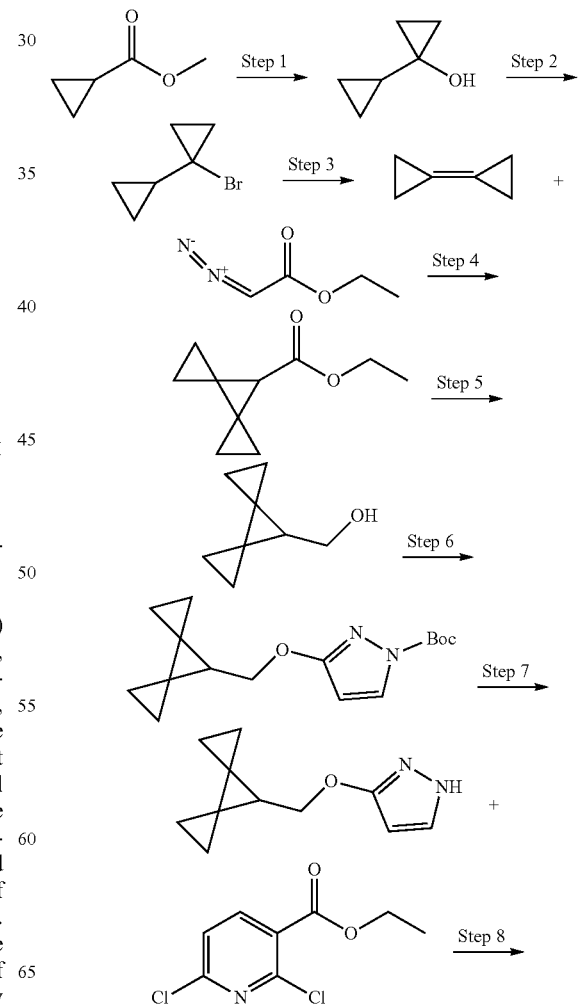

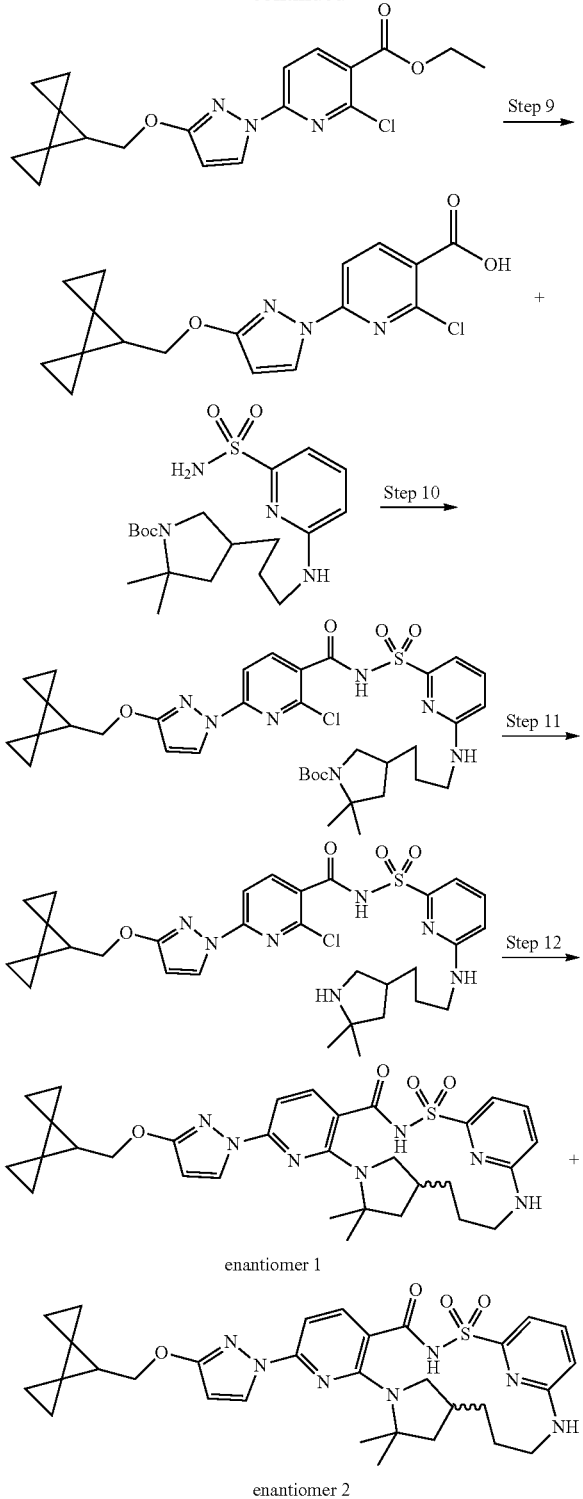

Step 1: 1-Cyclopropylcyclopropanol

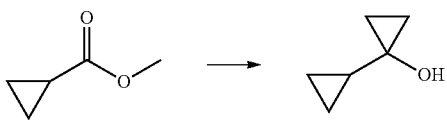

To a solution of methyl cyclopropanecarboxylate (75 g, 749.1 mmol) in ether (450 mL) was added titanium(IV) isopropoxide (55.3 mL, 187.4 mmol). To the mixture was slowly added ethyl magnesium bromide (1.6 L of 1 M, 1.60 mol) over 2 h. The addition is exothermic and controlled with monitoring the addition rate and using a cooling bath. The reaction temperature was kept between 21° C.-26° C. during addition. After addition, the mixture was stirred an additional 2 h at ambient temperature. Next, the mixture was chilled to −5° C. using an acetone/dry ice bath and slowly quenched with sulfuric acid (970 g of 10% w/w, 990 mmol). The reaction mixture was cooled in a dry ice/acetone bath to keep the reaction vessel below 0° C. during the quench. As the quench progressed, a grey/purple solid formed. Following complete addition of aqueous sulfuric acid, the mixture was stirred at 0° C. for 1 h. The precipitate was filtered through Celite using a medium frit and the precipitate washed with diethyl ether (900 mL). The filtrate was transferred to a separatory funnel and the organic phase was washed with brine (1 L), saturated sodium bicarbonate (1 L) and brine (1 L). The organic phase was dried over magnesium sulfate, filtered over Celite and the solvent was evaporated by rotary evaporation at 100 torr and the water bath set at 20° C. The crude product was stored at −23° C. overnight and used without further purification. The product, 1-cyclopropylcyclopropanol (61 g, 83%) was found to contain 50% solvent (tetrahydrofuran and PrOH) and used as such in the next step. $^1$H NMR (400 MHz, Chloroform-d) δ 1.32 (tt, J=8.2, 5.1 Hz, 1H), 0.71-0.61 (m, 2H), 0.51-0.43 (m, 2H), 0.43-0.33 (m, 2H), 0.23-0.14 (m, 2H).

Step 2: 1-Bromo-1-cyclopropyl-cyclopropane

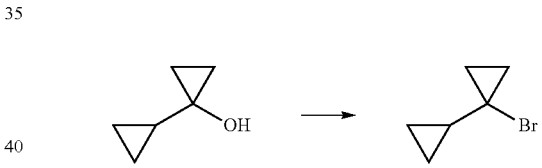

A solution of triphenylphosphine (56.1 g, 213.9 mmol) in dichloromethane (200 mL) was cooled to −10° C. A solution of bromine (11.0 mL, 214 mmol) in dichloromethane (40 mL) was added and the reaction was stirred at −10° C. for an additional 15 min. The reaction was then cooled to −30° C. and pyridine (3.3 mL, 41 mmol) was added. A solution of 1-cyclopropylcyclopropanol (20.0 g, 204 mmol), pyridine (17.3 mL, 214 mmol) and dichloromethane (100 mL) was added dropwise while maintaining the temperature between −15° C. to −20° C. After 30 min, the addition was complete and the reaction was allowed to gradually warm to room temperature. The reaction was then allowed to stir at 40° C. overnight. The reaction was then cooled to room temperature and quenched with water (100 mL). The reaction was then stirred for 10 min and the phases were separated. The organic phase was successively washed with 1 M hydrochloric acid (102 mL) then saturated sodium bicarbonate (50 mL), dried over sodium sulfate, filtered and concentrated (30° C./house vacuum~300 torr) to remove most of the dichloromethane. The crude reaction mixture was flash distilled (40° C./20 torr) to remove further dichloromethane. The solid residue (Ph$_3$PO and product) was re-heated and distilled (50-60° C./20 torr) to afford 21.5 g (65% yield) of 1-bromo-1-cyclopropyl-cyclopropane as a turbid, colorless liquid. $^1$H NMR (400 MHz, Chloroform-d) δ 1.61 (tt, J=8.2, 5.0 Hz, 1H), 1.07-1.02 (m, 2H), 0.78-0.66 (m, 2H), 0.67-0.51 (m, 2H), 0.35-0.21 (m, 2H).

Step 3: Cyclopropylidenecyclopropane

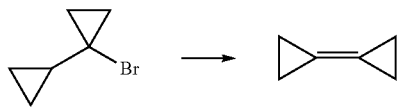

A solution of potassium tert-butoxide (16.7 g, 148.8 mmol) in dimethyl sulfoxide (100 mL) was stirred at room temperature in a 3-neck 250-mL round bottom flask. 1-Bromo-1-cyclopropyl-cyclopropane (20.0 g, 124.2 mmol) was added dropwise and the reaction immediately turned dark and then brown. The reaction was mildly exothermic (maintained temperature between 18° C. to 22° C. using an ice-water bath). After 10 min, the addition was completed. The ice-water bath was removed and the reaction was allowed to stir at room temperature. After 90 min, the reaction mixture was vacuum distilled using a bulb-to-bulb distillation. The distillation took place from 60° C. to 80° C. between 40 and 100 torr. The distillate slowly collected in the receiver to afford 18.2 g (7.3 g of product as a 42 wt % solution in t-BuOH) of a colorless liquid. The distillate was further washed with water (5×10 mL). Dichloromethane (4 g) was added and mixture was dried over magnesium sulfate, filtered (washing with 2 additional portions of 3 g of dichloromethane each) to afford 17.30 g (6.9 g product as a 39.6 wt % solution in dichloromethane; 69% yield) as a colorless liquid. $^1$H NMR (400 MHz, Chloroform-d) δ 1.19 (s, 8H). The 1H NMR confirms the presence of dichloromethane and a small amount of tert-butanol.

Step 4: Ethyl dispiro[2.0.2.1]heptane-7-carboxylate

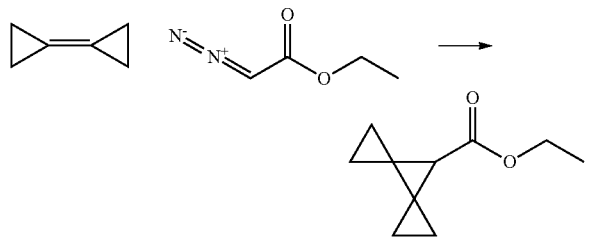

To a solution of cyclopropylidenecyclopropane (49.5 g, 617.8 mmol) in dichloromethane (110 mL) at 0° C. under a nitrogen atmosphere was added rhodium(II) acetate (4.2 g, 9.503 mmol). To the mixture at 0° C. was added ethyl 2-diazoacetate (106.8 mL, 1.016 mol) using a syringe pump set at an addition rate of 0.02 mL/min (1.2 mL/h). The addition was continuous for 89 hr. The crude reaction mixture was filtered through a plug of silica, washing 3× with 150 mL of dichloromethane each. The volatile materials were removed in vacuo affording a crude, dark yellow oil, ethyl dispiro[2.0.2.1]heptane-7-carboxylate (100 g, 97%, contains ~20% dichloromethane, diethyl (E)-but-2-enedioate and diethyl (Z)-but-2-enedioate as contaminants) which was used directly in the next step. $^1$H NMR (400 MHz, Chloroform-d) δ 4.13 (q, J=7.1 Hz, 2H), 2.23 (s, 1H), 1.24 (t, J=7.1 Hz, 3H), 1.08-0.93 (m, 4H), 0.90-0.82 (m, 2H), 0.77 (ddd, J=8.2, 5.0, 3.5 Hz, 2H).

Step 5: Dispiro[2.0.2.1]heptan-7-yl methanol

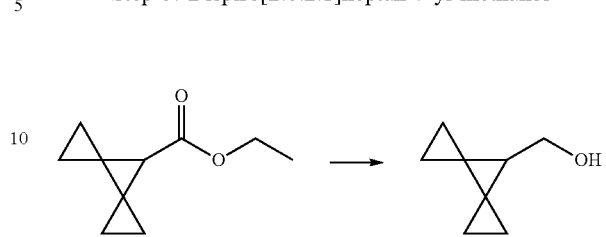

To a slurry of lithium aluminum hydride (7.8 g, 200.2 mmol) in diethyl ether (300 mL) chilled with an ice-water bath was slowly added ethyl dispiro[2.0.2.1]heptane-7-carboxylate (10.77 g, 64.79 mmol). The mixture was allowed to warm to a gentle reflux during the addition and continued to stir at ambient temperature for 1 h. The reaction was chilled with an ice-water bath and slowly quenched with the addition of water (8.0 mL, 440 mmol), followed by sodium hydroxide (8.0 mL of 2 M, 16 mmol) and then water (24.0 mL, 1.33 mol). The light yellow slurry was filtered over Celite and washed 3× with 150 mL of methyl tert-butyl ether. The filtrate was concentrated in vacuo affording 8.87 g of a clear oil, dispiro[2.0.2.1]heptan-7-yl methanol (8.87 g, quantitative yield).

$^1$H NMR (400 MHz, Chloroform-d) δ 3.71 (dd, J=6.7, 5.5 Hz, 2H), 1.76-1.65 (m, 1H), 1.46 (t, J=5.6 Hz, 1H), 0.87 (q, J=1.9 Hz, 4H), 0.72-0.61 (m, 2H), 0.60-0.50 (m, 2H).

Step 6: tert-Butyl 3-(dispiro[2.0.2.1]heptan-7-yl methoxy)-1H-pyrazole-1-carboxylate

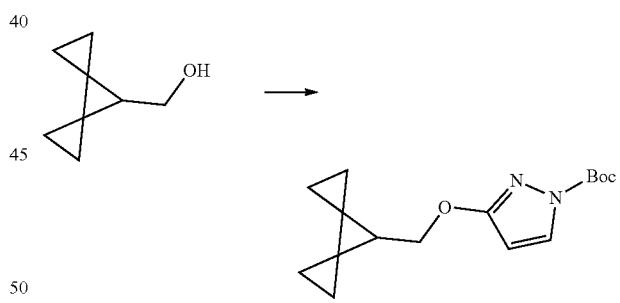

A solution of dispiro[2.0.2.1]heptan-7-yl methanol (1.36 g, 11.0 mmol), tert-butyl 3-hydroxypyrazole-1-carboxylate (2.3 g, 12 mmol) and triphenylphosphine (3.2 g, 12 mmol) in tetrahydrofuran (28 mL) was cooled in an ice bath and diisopropyl azodicarboxylate (2.4 mL, 12 mmol) was slowly added. The cooling bath was removed and the reaction was stirred for 15 h. The reaction was diluted with ethyl acetate, washed with saturated aqueous sodium bicarbonate, dried over sodium sulfate, filtered and evaporated under vacuum. The residue was purified by silica gel chromatography eluting with a gradient of 0-20% ethyl acetate in hexanes to give tert-butyl 3-(dispiro[2.0.2.1]heptan-7-yl methoxy)-1H-pyrazole-1-carboxylate (1.57 g, 49% yield) as a colorless oil. ESI-MS m/z calc. 290.16306, found 291.3 (M+1)$^+$; Retention time: 0.76 min (LC Method A).

Step 7: 3-(Dispiro[2.0.2.1]heptan-7-ylmethoxy)-1H-pyrazole

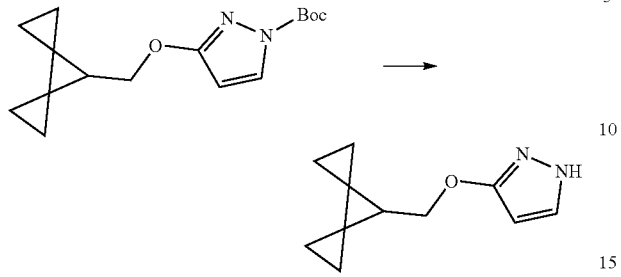

A solution of tert-butyl 3-(dispiro[2.0.2.1]heptan-7-yl methoxy)-1H-pyrazole-1-carboxylate (1.57 g, 5.41 mmol) and trifluoroacetic acid (2.2 mL, 29 mmol) in dichloromethane (20 mL) was stirred for three h. The volatiles were removed under vacuum and the residue was basified with saturated aqueous sodium bicarbonate and extracted with ethyl acetate. The combined extracts were dried over sodium sulfate, filtered and evaporated to give 3-(dispiro[2.0.2.1] heptan-7-ylmethoxy)-1H-pyrazole (0.94 g, 91% yield) as pale yellow oil. ESI-MS m/z calc. 190.11061, found 191.1 (M+1)$^+$; Retention time: 0.52 min (LC Method A).

Step 8: Ethyl 2-chloro-6-(3-(dispiro[2.0.2.1]heptan-7-ylmethoxy)-1H-pyrazol-1-yl)nicotinate

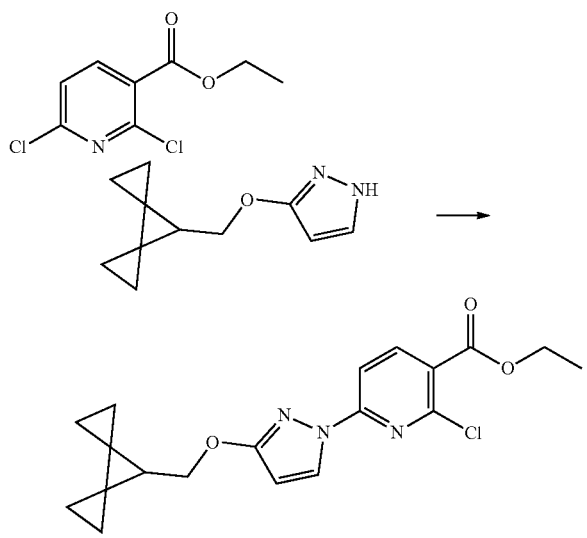

A mixture of 3-(dispiro[2.0.2.1]heptan-7-ylmethoxy)-1H-pyrazole (0.94 g, 4.9 mmol), ethyl 2,6-dichloropyridine-3-carboxylate (1.15 g, 5.23 mmol), potassium carbonate (0.83 g, 6.0 mmol) and 1,4-diazabicyclo[2.2.2]octane (0.12 g, 1.1 mmol) in dimethyl sulfoxide (16 mL) was stirred for 24 h. The reaction was diluted with water and extracted with ethyl acetate. The combined extracts were washed with brine and water, dried over sodium sulfate, filtered and evaporated under vacuum. The residue was purified by silica gel column chromatography eluting with a gradient from 0-20% ethyl acetate in hexanes to give ethyl 2-chloro-6-(3-(dispiro [2.0.2.1]heptan-7-ylmethoxy)-1H-pyrazol-1-yl)nicotinate (1.39 g, 75% yield) as a colorless solid. $^1$H NMR (400 MHz, Chloroform-d) δ 8.36 (d, J=2.8 Hz, 1H), 8.27 (d, J=8.5 Hz, 1H), 7.72 (d, J=8.5 Hz, 1H), 5.96 (d, J=2.9 Hz, 1H), 4.41 (q, J=7.1 Hz, 2H), 4.30 (d, J=7.0 Hz, 2H), 1.94 (t, J=7.0 Hz, 1H), 1.42 (t, J=7.1 Hz, 3H), 1.02-0.89 (m, 4H), 0.75-0.65 (m, 2H), 0.65-0.53 (m, 2H). ESI-MS m/z calc. 373.11932, found 374.2 (M+1)$^+$; Retention time: 0.87 min (LC Method A).

Step 9: 2-Chloro-6-[3-(dispiro[2.0.2.1]heptan-7-ylmethoxy)pyrazol-1-yl]pyridine-3-carboxylic Acid

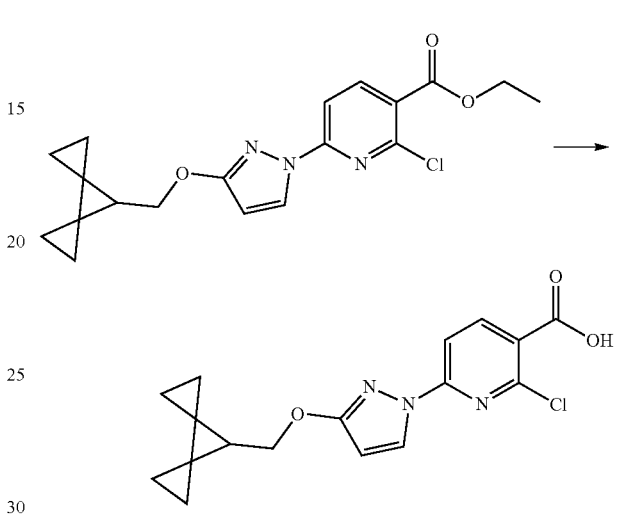

A solution of ethyl 2-chloro-6-(3-(dispiro[2.0.2.1]heptan-7-ylmethoxy)-1H-pyrazol-1-yl)nicotinate (1.39 g, 3.72 mmol) and sodium hydroxide (7.5 mL of 1 M solution, 7.5 mmol) in tetrahydrofuran (6 mL) and ethanol (3 mL) was stirred for 90 min. The volatiles were removed under vacuum and water was added. The reaction was cooled in an ice bath and hydrochloric acid (7.5 mL of 1 M solution, 7.5 mmol) was slowly added. The reaction was diluted with water and extracted with ethyl acetate. The combined extracts were washed with brine, dried over sodium sulfate, filtered and evaporated to give 2-chloro-6-[3-(dispiro [2.0.2.1]heptan-7-ylmethoxy)pyrazol-1-yl]pyridine-3-carboxylic acid (1.16 g, 82% yield) as a colorless solid. $^1$H NMR (400 MHz, dimethyl sulfoxide-d$_6$) δ 8.41 (d, J=2.9 Hz, 1H), 8.38 (d, J=8.4 Hz, 1H), 7.73 (d, J=8.4 Hz, 1H), 6.19 (d, J=2.8 Hz, 1H), 4.27 (d, J=7.0 Hz, 2H), 1.93 (t, J=7.0 Hz, 1H), 0.97-0.79 (m, 4H), 0.76-0.66 (m, 2H), 0.65-0.56 (m, 2H). ESI-MS m/z calc. 345.088, found 346.1 (M+1)$^+$; Retention time: 0.73 min (LC Method A).

Step 10: tert-Butyl 4-[3-[[6-[[2-chloro-6-[3-(dispiro [2.0.2.1]heptan-7-ylmethoxy)pyrazol-1-yl]pyridine-3-carbonyl]sulfamoyl]-2-pyridyl]amino]propyl]-2,2-dimethyl-pyrrolidine-1-carboxylate

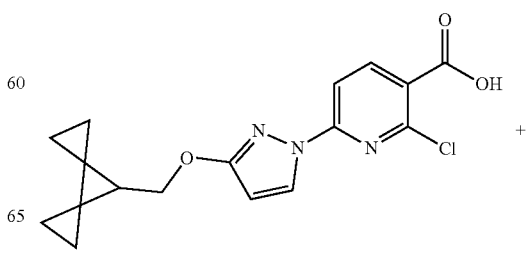

+

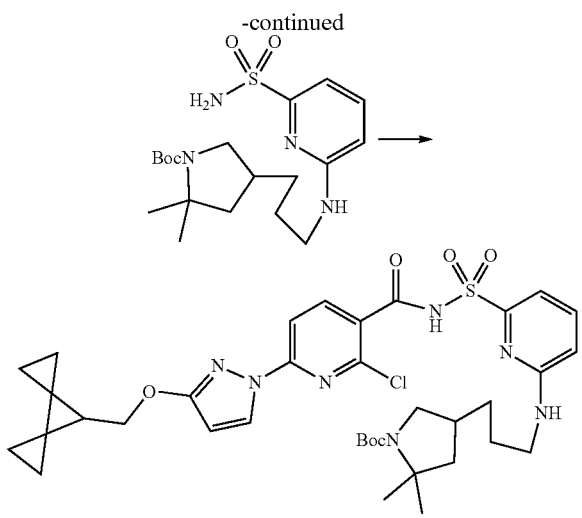

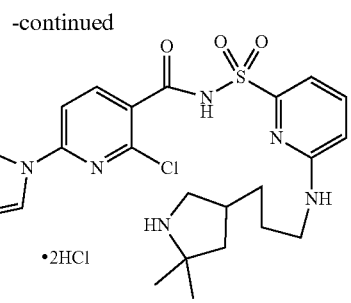

A 100 mL flask was charged under nitrogen with 2-chloro-6-[3-(dispiro[2.0.2.1]heptan-7-ylmethoxy)pyrazol-1-yl]pyridine-3-carboxylic acid (300 mg, 0.8676 mmol) and anhydrous tetrahydrofuran (4 mL). Carbonyl diimidazole (214 mg, 1.320 mmol) was added and the mixture was stirred under nitrogen at room temperature for 2 h. In a separate 20 mL vial maintained under nitrogen atmosphere, a solution of tert-butyl 2,2-dimethyl-4-[3-[(6-sulfamoyl-2-pyridyl)amino]propyl]pyrrolidine-1-carboxylate (358 mg, 0.8678 mmol) in anhydrous tetrahydrofuran (2 mL) was prepared and added via syringe to the activated ester solution. Added 1,8-diazabicyclo[5.4.0]undec-7-ene (0.29 mL, 1.939 mmol) and the mixture was stirred at room temperature for 19 h. The solvent was evaporated and the residue was treated with water (50 mL), ethyl acetate (50 mL) and hydrochloric acid (1 mL of 6 M, 6.000 mmol). The two phases were separated. The aqueous phase was further extracted with ethyl acetate (25 mL). The combined organics were washed with brine (30 mL), dried over sodium sulfate and the solvents were evaporated. The product was dissolved in dichloromethane and purified by flash chromatography on silica gel using a gradient of ethyl acetate (0 to 100% over 30 min) in hexanes. The pure fractions were collected and the solvents were evaporated to give 408 mg of product as a foamy solid. LCMS showed that the material contained 6% of starting carboxylic acid. The product was purified a second time using the same method to give tert-butyl 4-[3-[[6-[[2-chloro-6-[3-(dispiro[2.0.2.1]heptan-7-ylmethoxy)pyrazol-1-yl]pyridine-3-carbonyl]sulfamoyl]-2-pyridyl]amino]propyl]-2,2-dimethyl-pyrrolidine-1-carboxylate (364 mg, 57%) as a colorless resin. ESI-MS m/z calc. 739.2919, found 740.3 (M+1)$^+$: Retention time: 2.45 min (LC Method B).

Step 11: 2-Chloro-N-[[6-[3-(5,5-dimethylpyrrolidin-3-yl)propylamino]-2-pyridyl]sulfonyl]-6-[3-(dispiro[2.0.2.1]heptan-7-ylmethoxy)pyrazol-1-yl]pyridine-3-carboxamide (Dihydrochloride Salt)

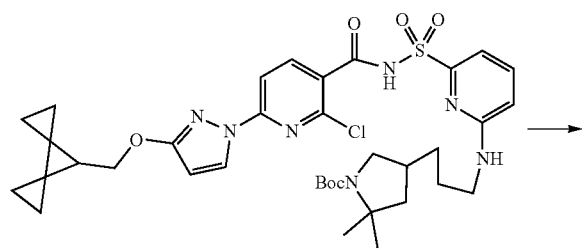

A 100 mL round bottom flask was charged with tert-butyl 4-[3-[[6-[[2-chloro-6-[3-(dispiro[2.0.2.1]heptan-7-ylmethoxy)pyrazol-1-yl]pyridine-3-carbonyl]sulfamoyl]-2-pyridyl]amino]propyl]-2,2-dimethyl-pyrrolidine-1-carboxylate (364 mg, 0.4917 mmol), dichloromethane (5 mL) and hydrochloric acid (0.5 mL of 4 M, 2.000 mmol) (4 M in dioxane). The vial was capped and stirred at room temperature for 5 h. An additional amount of hydrochloric acid (0.5 mL of 4 M, 2.000 mmol) was added and the mixture was stirred for another h. The volatiles were removed by rotary evaporation under vacuum at room temperature. The residue was triturated with dichloromethane/hexanes and the solvents evaporated. The operation was repeated until a white solid was obtained. Drying under vacuum gave 2-chloro-N-[[6-[3-(5,5-dimethylpyrrolidin-3-yl)propylamino]-2-pyridyl]sulfonyl]-6-[3-(dispiro[2.0.2.1]heptan-7-ylmethoxy)pyrazol-1-yl]pyridine-3-carboxamide (dihydrochloride salt) (325 mg, 93%) as a white solid. ESI-MS m/z calc. 639.23944, found 640.3 (M+1)$^+$; Retention time: 1.58 min (LC Method B).

Step 12: 8-[3-({Dispiro[2.0.2.1]heptan-7-yl}methoxy)-1H-pyrazol-1-yl]-12,12-dimethyl-2λ$^6$-thia-3,9,11,18,23-pentaazatetracyclo[17.3.1.111, 14.05,10]tetracosa-1(22),5,7,9,19(23),20-hexaene-2, 2,4-trione (Enantiomer 1) (Compound 106) and 8-[3-({dispiro[2.0.2.1]heptan-7-yl}methoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Enantiomer 2) (Compound 107)

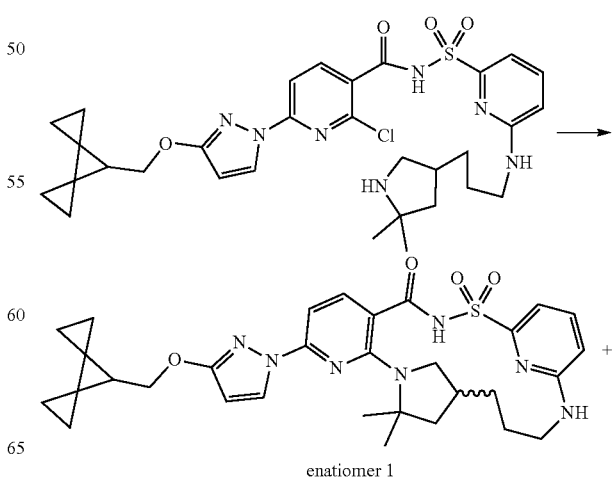

enatiomer 1

341

-continued

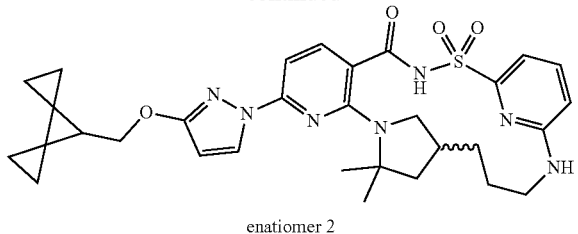

enatiomer 2

A 100 mL round bottom flask equipped with a magnetic stirbar was charged under nitrogen with 2-chloro-N-[[6-[3-(5,5-dimethylpyrrolidin-3-yl)propylamino]-2-pyridyl]sulfonyl]-6-[3-(dispiro[2.0.2.1]heptan-7-ylmethoxy)pyrazol-1-yl]pyridine-3-carboxamide (dihydrochloride salt) (325 mg, 0.4557 mmol), anhydrous NMP (3 mL), potassium carbonate (269 mg, 1.946 mmol) (freshly ground in a mortar) and cesium fluoride (70 mg, 0.4608 mmol). The mixture was vigorously stirred at 140° C. under nitrogen for 15 h. The mixture was diluted with water (20 mL) and it was acidified by slowly adding hydrochloric acid (500 μL of 6 M, 3.000 mmol, final pH=4-5). The resulting solid was filtered and briefly air dried. The solid was dissolved in dichloromethane/ethyl acetate (total volume 75 mL) dried over sodium sulfate, filtered and concentrated to give a solution that was purified by flash chromatography on silica gel using a gradient of methanol (0 to 5% over 30 min) in dichloromethane. Evaporation of the solvents gave racemic 8-[3-({dispiro [2.0.2.1]heptan-7-yl}methoxy)-1H-pyrazol-1-yl]-12,12-dimethyl-2λ$^6$-thia-3,9,11,18,23-pentaazatetracyclo [17.3.1.111,14.05,10]tetracosa-1(22),5,7,9,19(23),20-hexaene-2,2,4-trione (Compound 105) (102 mg, 36%) as a white solid. $^1$H NMR (400 MHz, dimethyl sulfoxide-d$_6$) δ 12.51 (s, 1H), 8.20 (d, J=2.8 Hz, 1H), 7.81 (d, J=8.2 Hz, 1H), 7.58 (dd, J=8.5, 7.2 Hz, 1H), 7.05 (broad d, J=7.2 Hz, 1H), 6.97 (s, 1H), 6.92 (d, J=8.2 Hz, 1H), 6.71 (d, J=8.5 Hz, 1H), 6.11 (d, J=2.7 Hz, 1H), 4.24 (d, J=7.0 Hz, 2H), 4.0-3.85 (m, 1H), 3.15 (br s, 1H), 2.95 (br d, J=13.3 Hz, 1H), 2.75-2.65 (m, 1H), 2.12 (br s, 1H), 1.91 (t, J=7.0 Hz, 1H), 1.89-1.67 (m, 2H), 1.67-1.41 (m, 9H), 1.37-1.26 (m, 1H), 0.97-0.81 (m, 4H), 0.74-0.65 (m, 2H), 0.66-0.53 (m, 2H). ESI-MS m/z calc. 603.26276, found 604.2 (M+1)$^+$; Retention time: 2.26 min (LC Method B). This racemic material (97 mg) was subjected to chiral SFC separation (ChiralPak column AS-H (250×10 mm), 5 μm, 35° C., mobile phase 38% acetonitrile:methanol (90:10 no modifier), 62% carbon dioxide, 10 mL/min, 24 mg/mL in acetonitrile:methanol (90:10 no modifier), injection volume 70 μL, 100 bar). The first enantiomer to elute was collected and the solvents were evaporated and the residue triturated in dichloromethane/hexanes. Evaporation gave 8-[3-({dispiro[2.0.2.1]heptan-7-yl}methoxy)-1H-pyrazol-1-yl]-12,12-dimethyl-2λ$^6$-thia-3, 9,11,18,23-pentaazatetracyclo[17.3.1.111,14.05,10] tetracosa-1(22),5,7,9,19(23),20-hexaene-2,2,4-trione (enantiomer 1) (Compound 106) (46 mg, 32%). $^1$H NMR (400 MHz, dimethyl sulfoxide-d$_6$) δ 12.50 (s, 1H), 8.20 (d, J=2.8 Hz, 1H), 7.81 (d, J=8.2 Hz, 1H), 7.57 (t, J=7.8 Hz, 1H), 7.05 (d, J=7.2 Hz, 1H), 6.98 (broad d, J=7.3 Hz, 1H), 6.91 (d, J=8.2 Hz, 1H), 6.71 (d, J=8.5 Hz, 1H), 6.10 (d, J=2.7 Hz, 1H), 4.23 (d, J=7.0 Hz, 2H), 3.99-3.82 (m, 1H), 3.15 (br s, 1H), 2.95 (br d, J=13.4 Hz, 1H), 2.80-2.62 (m, 1H), 2.12 (br s, 1H), 1.91 (t, J=7.0 Hz, 1H), 1.89-1.68 (m, 2H), 1.68-1.44 (m, 9H), 1.38-1.24 (m, 1H), 0.98-0.81 (m, 4H), 0.75-0.64 (m, 2H), 0.66-0.53 (m, 2H). ESI-MS m/z calc. 603.26276, found 604.3 (M+1)$^+$; Retention time: 2.27 min

342

(LC Method E). The second enantiomer to elute was collected and the solvents were evaporated and the residue triturated in dichloromethane/hexanes. Evaporation gave 8-[3-({dispiro[2.0.2.1]heptan-7-yl}methoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (enantiomer 2) (Compound 107) (43 mg, 31%). $^1$H NMR (400 MHz, dimethyl sulfoxide-d$_6$) δ 12.50 (s, 1H), 8.20 (d, J=2.8 Hz, 1H), 7.81 (d, J=8.2 Hz, 1H), 7.57 (t, J=7.9 Hz, 1H), 7.05 (d, J=7.2 Hz, 1H), 6.98 (broad d, J=8.5 Hz, 1H), 6.91 (d, J=8.2 Hz, 1H), 6.71 (d, J=8.5 Hz, 1H), 6.10 (d, J=2.7 Hz, 1H), 4.23 (d, J=7.0 Hz, 2H), 4.02-3.82 (m, 1H), 3.23-3.06 (m, 1H), 2.95 (br d, J=13.1 Hz, 1H), 2.80-2.62 (m, 1H), 2.12 (br s, 1H), 1.91 (t, J=7.0 Hz, 1H), 1.88-1.68 (m, 2H), 1.68-1.42 (m, 9H), 1.39-1.24 (m, 1H), 0.96-0.81 (m, 4H), 0.74-0.64 (m, 2H), 0.64-0.53 (m, 2H). ESI-MS m/z calc. 603.26276, found 604.3 (M+1)$^+$; Retention time: 2.27 min (LC Method B).

Example 28: Preparation of 12,12,20-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5(10),6,8,19, 21-hexaene-2,2,4-trione (Enantiomer 1) (Compound 114) and 12,12,20-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111, 14.05,10]tetracosa-1(23),5(10),6,8,19,21-hexaene-2, 2,4-trione (Enantiomer 2) (Compound 115)

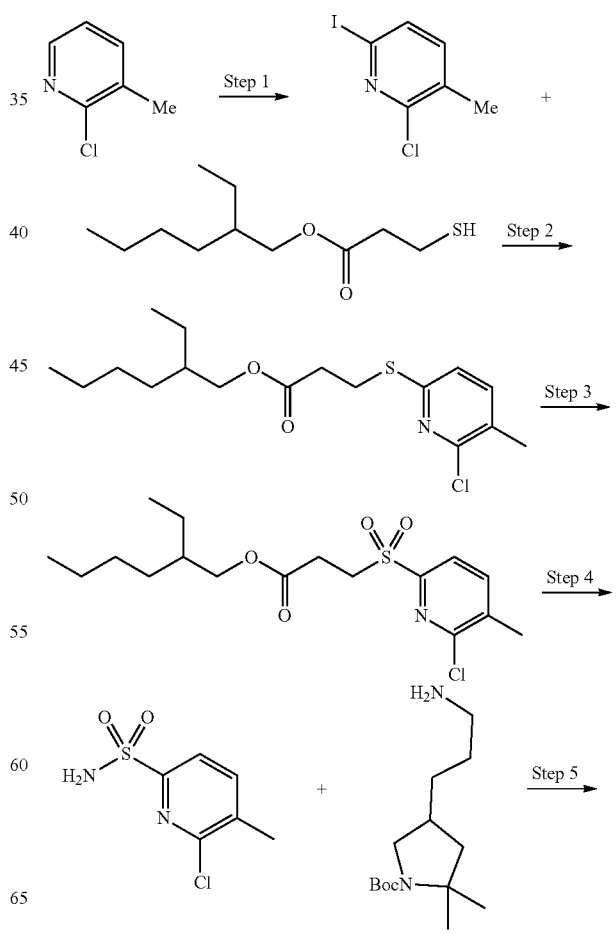

343

-continued

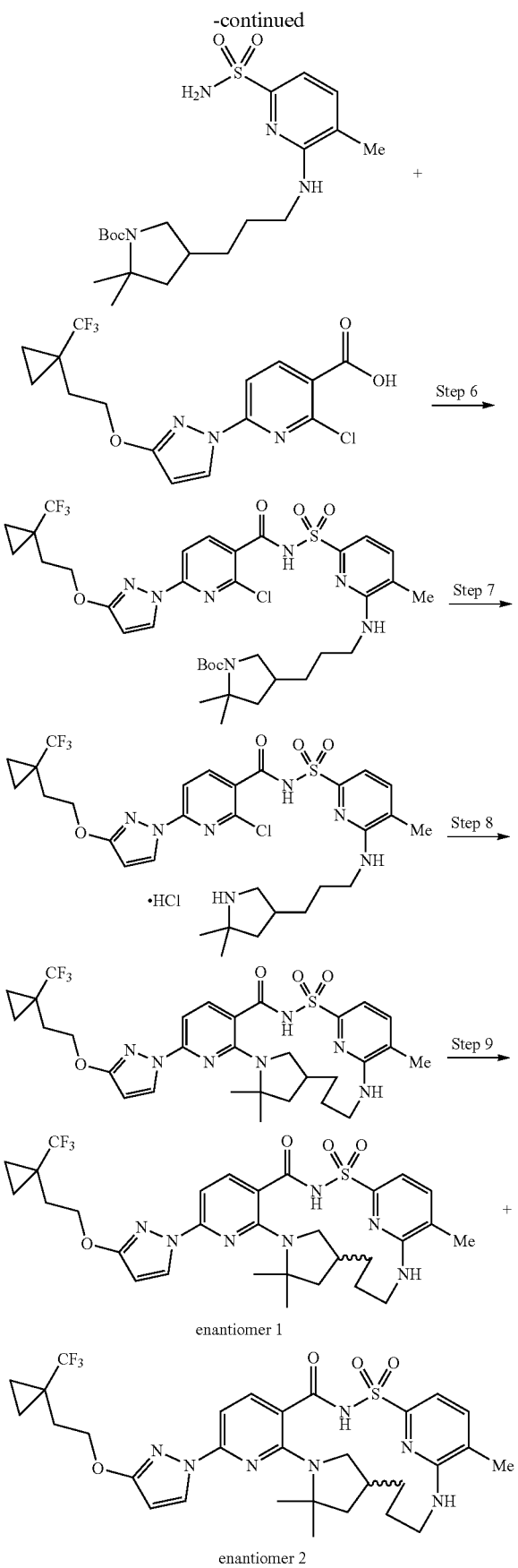

344

Step 1: 2-Chloro-6-iodo-3-methyl-pyridine

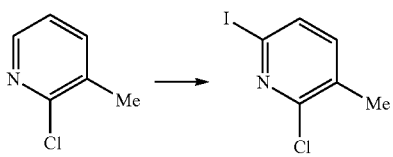 [SMILES: Cc1cccnc1Cl ; Cc1ccc(I)nc1Cl]

A solution of 2-(dimethylamino)ethanol (13.02 g, 14.7 mL, 146.1 mmol) in hexanes (120 mL) was cooled to −5° C. and treated with butyllithium (132 mL of 2.5 M in hexanes, 330.0 mmol) over a period of 45 min. The flask was kept between −5 and 0° C. for 1 h then cooled to −78° C. A solution of 2-chloro-3-methyl-pyridine (7 g, 54.87 mmol) in hexanes (70 mL+10 mL rinse) was added dropwise during 30 min and the mixture was stirred at −78° C. for 2 h. A solution of iodine (56 g, 11.36 mL, 220.6 mmol) in tetrahydrofuran (200 mL) was added dropwise over a period of about 1 h and the reaction mixture was left to gradually warm up to room temperature overnight. The mixture was cooled in an ice bath and quenched slowly with water (250 mL). Transferred to a 1000 mL separatory funnel and the layers were separated. The aqueous layer was extracted with ethyl acetate (2×250 mL) and the organic layers were combined, washed with water containing 10% aqueous sodium thiosulfate (organic layer becomes clear), water (200 mL) and brine (200 mL). The organic layer was dried over sodium sulfate, filtered and concentrated under reduced pressure. The residue was purified by silica gel chromatography on a 220 g column, eluting from 0% to 15% ethyl acetate in heptanes to afford pure and mixed fractions. The mixed fractions were further purified by silica gel chromatography on a 120 g column, eluting from 0% to 15% ethyl acetate in heptanes then triturated in heptanes, dried and combined to the previous pure fractions from the first silica gel column to afford 2-chloro-6-iodo-3-methyl-pyridine (9.7 g, 68%) as a pale yellow solid. $^1$H NMR (300 MHz, CDCl$_3$) ppm 2.32 (s, 3H), 7.18 (d, J=7.6 Hz, 1H), 7.56 (d, J=7.6 Hz, 1H). ESI-MS m/z calc. 252.9155, found 254.0 (M+1)$^+$; Retention time: 2.71 min (LC Method H).

Step 2: 2-Ethylhexyl 3-[(6-chloro-5-methyl-2-pyridyl)sulfanyl]propanoate

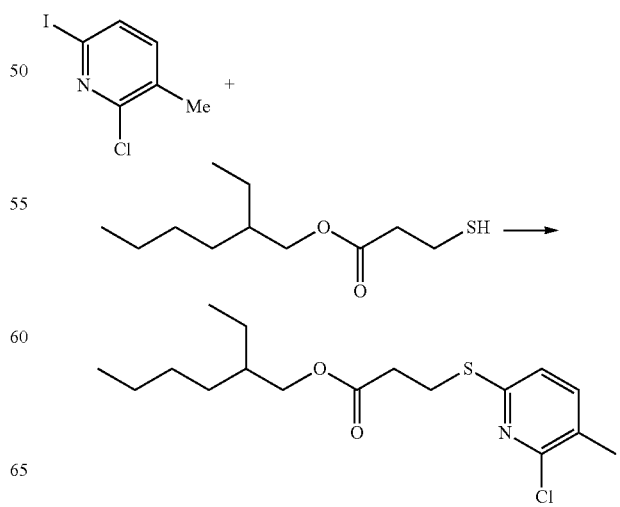

A solution of 2-chloro-6-iodo-3-methyl-pyridine (15.4 g, 60.76 mmol) and diisopropylethylamine (15.73 g, 21.2 mL, 121.7 mmol) in toluene (300 mL) was degassed by bubbling nitrogen for 10 min. Tris(dibenzylideneacetone)dipalladium (0) (1.7 g, 1.856 mmol), Xantphos (2.1 g, 3.629 mmol) and 2-ethylhexyl 3-sulfanylpropanoate (14.6 g, 66.86 mmol) were added and the mixture was heated at 110° C. overnight. The residue was concentrated under reduced pressure and purified by silica-gel column chromatography on a 220 g column, eluting from 0% to 20% ethyl acetate in heptanes to afford 2-ethylhexyl 3-[(6-chloro-5-methyl-2-pyridyl)sulfanyl]propanoate (15.8 g, 76%) as a yellow oil. $^1$H NMR (300 MHz, CDCl$_3$) ppm 0.88 (t, J=7.3 Hz, 6H), 1.20-1.44 (m, 9H), 2.30 (s, 3H), 2.77 (t, J=7.0 Hz, 2H), 3.40 (t, J=6.9 Hz, 2H), 3.97-4.06 (m, 2H), 7.00 (d, J=7.9 Hz, 1H), 7.33 (d, J=7.9 Hz, 1H). ESI-MS m/z calc. 343.912, found 344.2 (M+1)$^+$; Retention time: 2.76 min (LC Method I).

Step 3: 2-Ethylhexyl 3-[(6-chloro-5-methyl-2-pyridyl)sulfonyl]propanoate

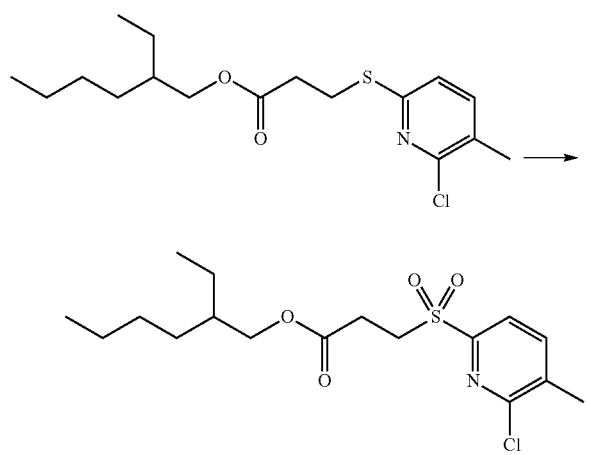

m-Chloroperbenzoic acid (21.6 g, 96.38 mmol) was slowly added to a solution of 2-ethylhexyl 3-[(6-chloro-5-methyl-2-pyridyl)sulfanyl]propanoate (15.8 g, 45.94 mmol) in dichloromethane (135 mL) at room temperature. The mixture was stirred at this temperature for 5 h. Ethyl acetate (500 mL) was added and the resulting mixture was washed with saturated sodium bicarbonate solution (250 mL) then 0.5 M sodium hydroxide solution (2×250 mL). The organic phase was dried over anhydrous sodium sulfate and concentrated under reduced pressure. The residue was purified by silica-gel column chromatography on a 220 g column, eluting from 0% to 40% ethyl acetate in heptanes to afford 2-ethylhexyl 3-[(6-chloro-5-methyl-2-pyridyl)sulfonyl]propanoate (12.36 g, 72%) as a clear oil. $^1$H NMR (300 MHz, CDCl$_3$) ppm 0.82-0.94 (m, 6H), 1.20-1.41 (m, 9H), 2.49 (s, 3H), 2.78-2.89 (m, 2H), 3.66-3.76 (m, 2H), 4.01 (dd, J=6.0, 1.9 Hz, 2H), 7.77-7.84 (m, 1H), 7.89-7.96 (m, 1H). ESI-MS m/z calc. 375.911, found 376.1 (M+1)$^+$; Retention time: 2.43 min (LC Method I).

Step 4: 6-Chloro-5-methyl-pyridine-2-sulfonamide

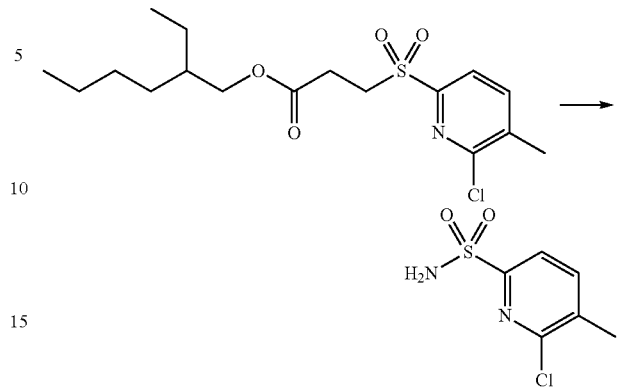

Sodium methoxide (7.1 g, 131.4 mmol) was added to a solution of 2-ethylhexyl 3-[(6-chloro-5-methyl-2-pyridyl)sulfonyl]propanoate (12.36 g, 32.88 mmol) in tetrahydrofuran (100 mL) and methanol (35 mL) at room temperature. The reaction mixture was stirred for 4 h then the mixture was concentrated under reduced pressure to afford a white solid intermediate. To this intermediate was added hydroxylamine-O-sulfonic acid (7.4 g, 65.43 mmol) and sodium acetate (8.1 g, 98.74 mmol) in water (240 mL) at 0° C. The mixture was stirred at room temperature overnight then extracted with ethyl acetate (2×300 mL). The organic phase was dried over sodium sulfate, filtered and concentrated under reduced pressure. The residue was purified by silica-gel column chromatography on a 120 g column, eluting from 20% to 80% of ethyl acetate in heptanes to afford 6-chloro-5-methyl-pyridine-2-sulfonamide (5.9 g, 86%) as a white solid. $^1$H NMR (300 MHz, dimethyl sulfoxide-d$_6$) ppm 2.40 (s, 3H), 7.59 (s, 2H), 7.82 (d, J=7.6 Hz, 1H), 8.04 (d, J=7.6 Hz, 1H). ESI-MS m/z calc. 206.65, found 207.1 (M+1)$^+$; Retention time: 1.44 min (LC Method I).

Step 5: tert-Butyl 2,2-dimethyl-4-[3-[(3-methyl-6-sulfamoyl-2-pyridyl)amino]propyl]pyrrolidine-1-carboxylate

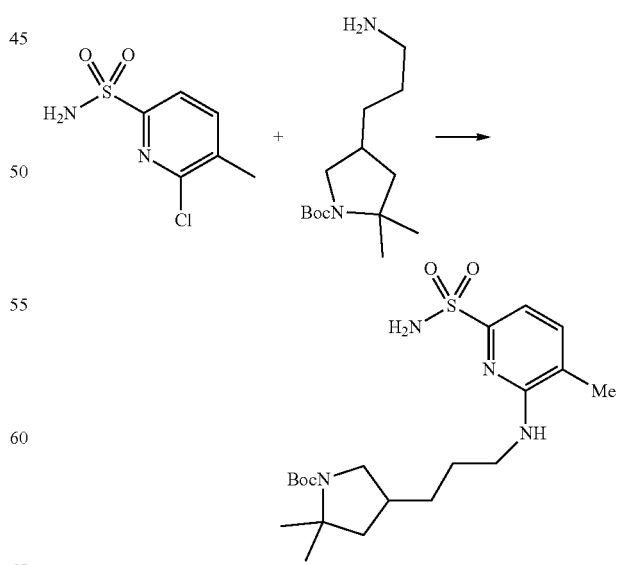

In a 5 mL microwave vial, 6-chloro-5-methyl-pyridine-2-sulfonamide (460 mg, 2.226 mmol), tert-butyl 4-(3-aminopropyl)-2,2-dimethyl-pyrrolidine-1-carboxylate (380 mg, 1.482 mmol) and diisopropylethylamine (1.3 mL, 7.463 mmol) were dissolved in n-BuOH (3 mL). The vial was sealed and stirred at 160° C. overnight. The mixture was filtered and directly purified by preparative reverse phase HPLC ($C_{18}$): 1-99% gradient of acetonitrile in water/hydrochloric acid modifier (15 min) to afford tert-butyl 2,2-dimethyl-4-[3-[(3-methyl-6-sulfamoyl-2-pyridyl)amino]propyl]pyrrolidine-1-carboxylate (130 mg, 21%). ESI-MS m/z calc. 426.23007, found 427.36 (M+1)+; Retention time: 1.36 min (LC Method B).

Step 6: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-3-methyl-2-pyridyl]amino]propyl]-2,2-dimethyl-pyrrolidine-1-carboxylate

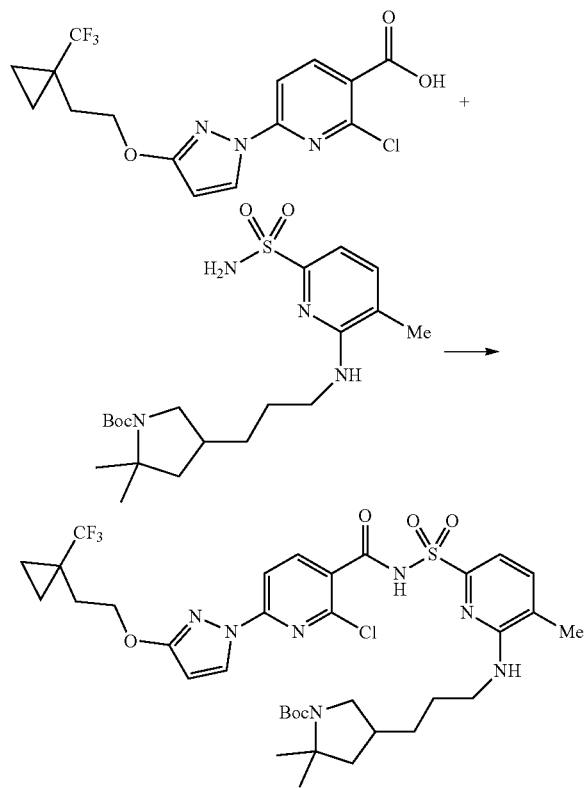

In a 20 mL microwave vial, 2-chloro-6-[3-[2-[1-(trifluoromethyl)cyclopropyl]ethoxy]pyrazol-1-yl]pyridine-3-carboxylic acid (345 mg, 0.9182 mmol) and carbonyl diimidazole (150 mg, 0.9251 mmol) were evacuated/backfilled with nitrogen (3 times). Dry tetrahydrofuran (4 mL) was added and the mixture was stirred for 90 min at 50° C. Next, a solution of tert-butyl 2,2-dimethyl-4-[3-[(3-methyl-6-sulfamoyl-2-pyridyl)amino]propyl]pyrrolidine-1-carboxylate (260 mg, 0.6095 mmol) and 1,8-diazabicyclo[5.4.0]undec-7-ene (228 µL, 1.525 mmol) in tetrahydrofuran (4 mL) was added and the mixture was stirred at 50° C. overnight. The reaction was diluted with ethyl acetate and washed with a 1M aqueous citric acid solution, followed by brine. Organic extract was dried, evaporated and purified by preparative reverse phase HPLC ($C_{18}$): 1-99% gradient of acetonitrile in water/hydrochloric acid modifier (15 min) to afford tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-3-methyl-2-pyridyl]amino]propyl]-2,2-dimethyl-pyrrolidine-1-carboxylate (290 mg, 61%) ESI-MS m/z calc. 783.27924, found 784.31 (M+1)+; Retention time: 2.42 min (LC Method B).

Step 7: 2-Chloro-N-[[6-[3-(5,5-dimethylpyrrolidin-3-yl)propylamino]-5-methyl-2-pyridyl]sulfonyl]-6-[3-[2-[1-(trifluoromethyl)cyclopropyl]ethoxy]pyrazol-1-yl]pyridine-3-carboxamide (Hydrochloride Salt)

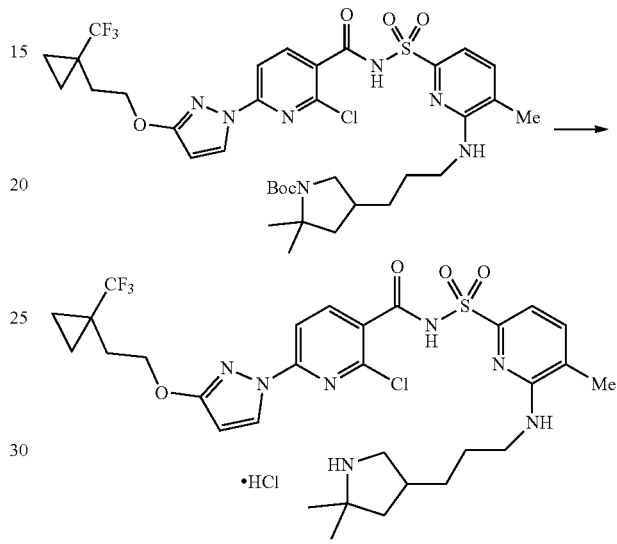

A solution of tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-3-methyl-2-pyridyl]amino]propyl]-2,2-dimethyl-pyrrolidine-1-carboxylate (290 mg, 0.3698 mmol) in dichloromethane (6 mL) was treated with hydrochloric acid (4M in dioxane) (3 mL of 4 M, 12.00 mmol) and stirred at room temperature for 30 min. The mixture was evaporated to dryness under a reduced pressure to afford 2-chloro-N-[[6-[3-(5,5-dimethylpyrrolidin-3-yl)propylamino]-5-methyl-2-pyridyl]sulfonyl]-6-[3-[2-[1-(trifluoromethyl)cyclopropyl]ethoxy]pyrazol-1-yl]pyridine-3-carboxamide (hydrochloride salt) (265 mg, 99%). The product was used in the next step without additional purification.

Step 8: 12,12,20-Trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(23),5(10),6,8,19,21-hexaene-2,2,4-trione

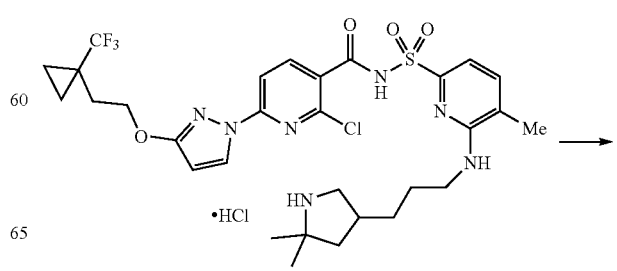

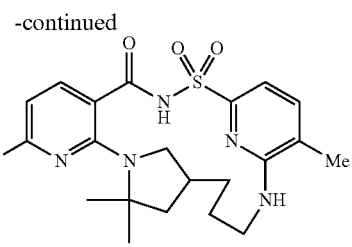

In 5 mL microwave vial, a mixture of 2-chloro-N-[[6-[3-(5,5-dimethylpyrrolidin-3-yl)propylamino]-5-methyl-2-pyridyl]sulfonyl]-6-[3-[2-[1-(trifluoromethyl)cyclopropyl]ethoxy]pyrazol-1-yl]pyridine-3-carboxamide (hydrochloride salt) (265 mg), potassium carbonate (260 mg, 1.881 mmol), cesium fluoride (87 mg, 0.5727 mmol) and 4 Å MS (300 mg) was evacuated/backfilled with nitrogen (3 times). Added dimethyl sulfoxide (6 mL) and the mixture was stirred at 140° C. for 16 h. The reaction mixture was filtered and purified by preparative reverse phase HPLC ($C_{18}$): 1-99% gradient of acetonitrile in water/hydrochloric acid modifier (15 min) to afford 12,12,20-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5(10),6,8,19,21-hexaene-2,2,4-trione (100 mg, 42%). ESI-MS m/z calc. 647.2502, found 648.31 (M+1)$^+$ Step 9: 12,12,20-Trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5(10),6,8,19,21-hexaene-2,2,4-trione (Enantiomer 1) (Compound 114) and 12,12,20-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5(10),6,8,19,21-hexaene-2,2,4-trione (Enantiomer 2) (Compound 115)

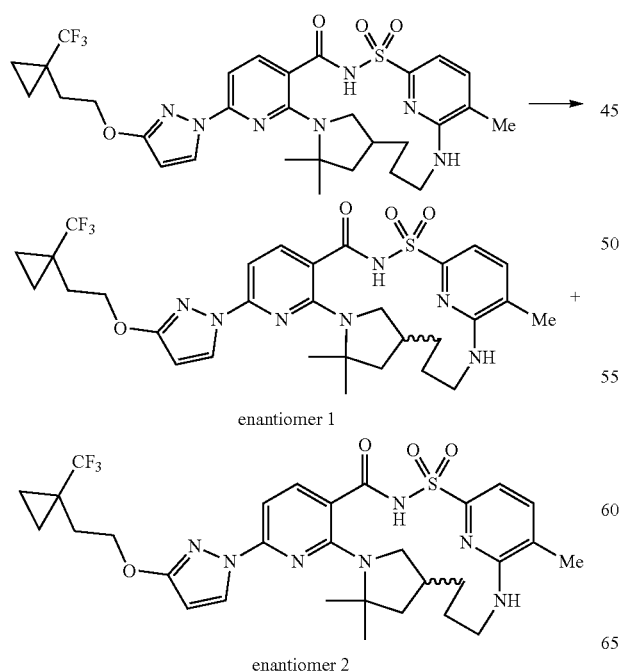

Racemic 12,12,20-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5(10),6,8,19,21-hexaene-2,2,4-trione (100 mg, 0.07052 mmol) was subjected to chiral separation by SFC chromatography using a ChiralPak AS-H (250×10 mm, 5 μm particle size) with 18% methanol (20 mM NH$_3$)/82% carbon dioxide mobile phase at 10 mL/min over 8.0 min (injection volume=70 μL of 24 mg/mL solution in methanol/dimethyl sulfoxide (90:10)) giving as the first enantiomer to elute, 12,12,20-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5(10),6,8,19,21-hexaene-2,2,4-trione (enantiomer 1) (Compound 114) (25.8 mg, 10%); $^1$H NMR (400 MHz, Chloroform-d) δ 8.19 (d, J=2.8 Hz, 1H), 8.08 (d, J=8.4 Hz, 1H), 7.51 (d, J=7.3 Hz, 1H), 7.42 (d, J=7.3 Hz, 1H), 7.24-7.27 (m, 1H), 5.90 (d, J=2.8 Hz, 1H), 4.56 (s, 1H), 4.39 (t, J=7.2 Hz, 2H), 3.93 (s, 1H), 3.44-3.32 (m, 1H), 3.23 (d, J=19.8 Hz, 1H), 3.06 (t, J=9.3 Hz, 1H), 2.72-2.53 (m, 1H), 2.14 (s, 3H), 2.09 (t, J=7.2 Hz, 3H), 1.25 (s, 2H), 1.05-0.99 (m, 2H), 0.81 (dd, J=12.6, 6.6 Hz, 1H), 0.74 (t, J=3.1 Hz, 2H), two methyl groups and one C—H overlapped with residual water; ESI-MS m/z calc. 647.2502, found 648.34 (M+1)$^+$; Retention time: 2.25 min. (LC Method A) and as the second enantiomer to elute, 12,12,20-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5(10),6,8,19,21-hexaene-2,2,4-trione (enantiomer 2) (Compound 115) (24.7 mg, 25%); $^1$H NMR (400 MHz, Chloroform-d) δ 8.19 (d, J=2.8 Hz, 1H), 8.09 (d, J=8.4 Hz, 1H), 7.52 (d, J=7.3 Hz, 1H), 7.43 (d, J=7.4 Hz, 1H), 7.28 (s, 1H), 5.91 (d, J=2.8 Hz, 1H), 4.58 (d, J=8.1 Hz, 1H), 4.39 (t, J=7.2 Hz, 2H), 3.97 (d, J=5.8 Hz, 1H), 3.43-3.31 (m, 1H), 3.28-3.15 (m, 1H), 3.06 (t, J=9.8 Hz, 1H), 2.65 (d, J=3.6 Hz, 1H), 2.14 (s, 3H), 2.09 (t, J=7.2 Hz, 3H), 1.25 (s, 2H), 1.04-1.00 (m, 2H), 0.82 (d, J=8.2 Hz, 2H), 0.74 (t, J=3.2 Hz, 2H). Two Me-groups and one C—H overlap with residual water; ESI-MS m/z calc. 647.2502, found 648.31 (M+1)$^+$; Retention time: 0.85 min (LC Method A).

Example 29: Preparation of 8-[3-({dispiro[2.0.2.1]heptan-7-yl}methoxy)-1H-pyrazol-1-yl]-12,12-dimethyl-2λ$^6$-thia-3,9,11,19,21-pentaazatetracyclo[18.2.2.111,14.05,10]pentacosa-1(23),5,7,9,20(24),21-hexaene-2,2,4-trione (Enantiomer 1) (Compound 120) and 8-[3-({dispiro[2.0.2.1]heptan-7-yl}methoxy)-1H-pyrazol-1-yl]-12,12-dimethyl-2λ$^6$-thia-3,9,11,19,21-pentaazatetracyclo[18.2.2.111,14.05,10]pentacosa-1(23),5,7,9,20(24),21-hexaene-2,2,4-trione (enantiomer 2) (Compound 121)

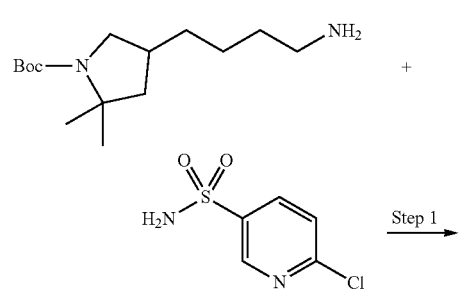

351
-continued

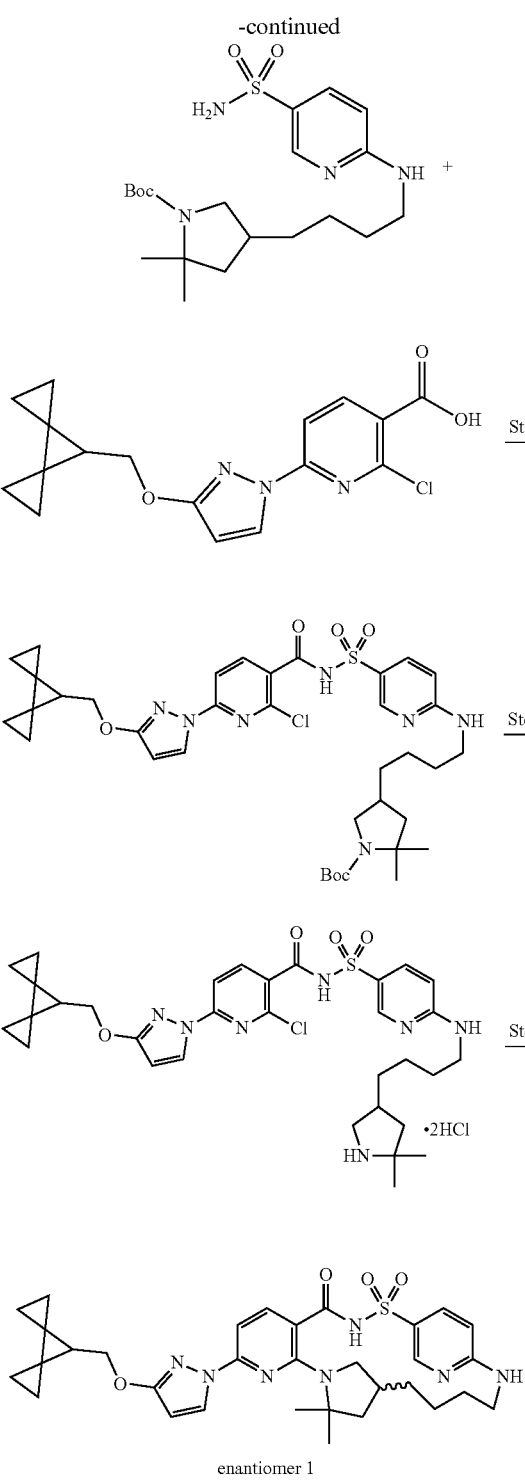

enantiomer 1 enantiomer 2

352

Step 1: tert-Butyl 2,2-dimethyl-4-[4-[(5-sulfamoyl-2-pyridyl)amino]butyl]pyrrolidine-1-carboxylate

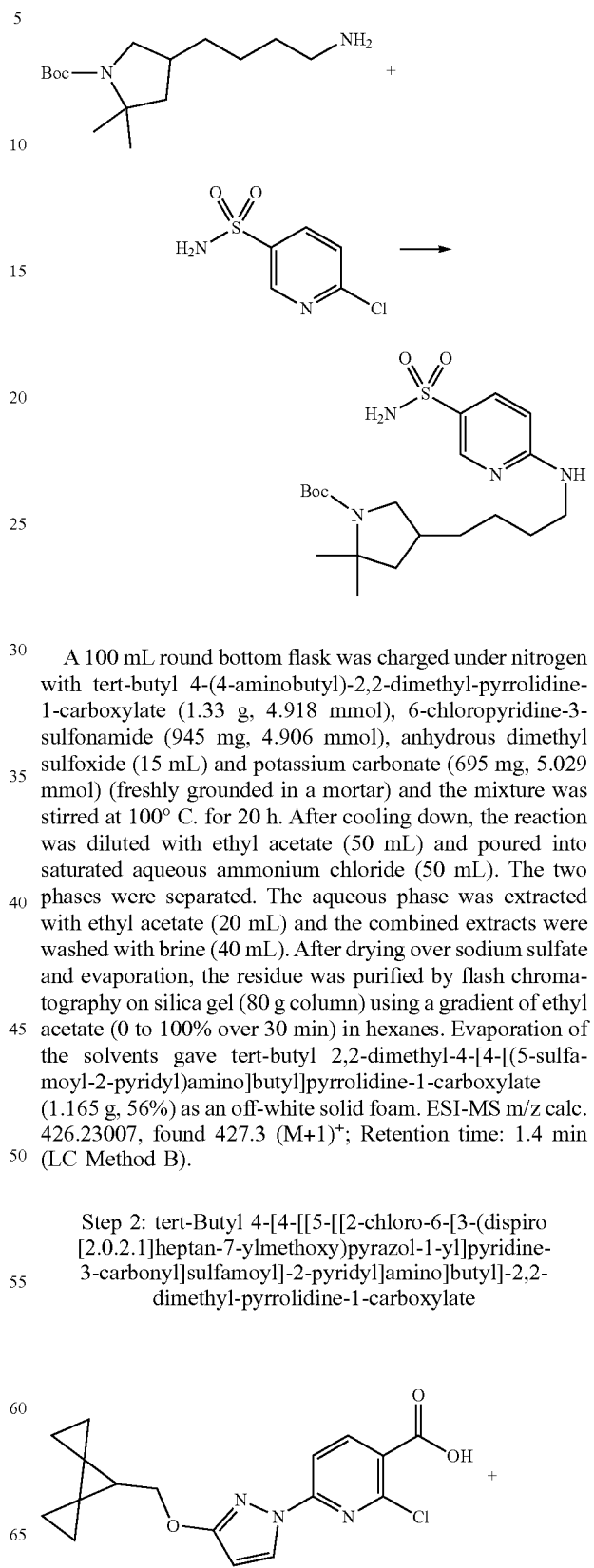

A 100 mL round bottom flask was charged under nitrogen with tert-butyl 4-(4-aminobutyl)-2,2-dimethyl-pyrrolidine-1-carboxylate (1.33 g, 4.918 mmol), 6-chloropyridine-3-sulfonamide (945 mg, 4.906 mmol), anhydrous dimethyl sulfoxide (15 mL) and potassium carbonate (695 mg, 5.029 mmol) (freshly grounded in a mortar) and the mixture was stirred at 100° C. for 20 h. After cooling down, the reaction was diluted with ethyl acetate (50 mL) and poured into saturated aqueous ammonium chloride (50 mL). The two phases were separated. The aqueous phase was extracted with ethyl acetate (20 mL) and the combined extracts were washed with brine (40 mL). After drying over sodium sulfate and evaporation, the residue was purified by flash chromatography on silica gel (80 g column) using a gradient of ethyl acetate (0 to 100% over 30 min) in hexanes. Evaporation of the solvents gave tert-butyl 2,2-dimethyl-4-[4-[(5-sulfamoyl-2-pyridyl)amino]butyl]pyrrolidine-1-carboxylate (1.165 g, 56%) as an off-white solid foam. ESI-MS m/z calc. 426.23007, found 427.3 (M+1)+; Retention time: 1.4 min (LC Method B).

Step 2: tert-Butyl 4-[4-[[5-[[2-chloro-6-[3-(dispiro[2.0.2.1]heptan-7-ylmethoxy)pyrazol-1-yl]pyridine-3-carbonyl]sulfamoyl]-2-pyridyl]amino]butyl]-2,2-dimethyl-pyrrolidine-1-carboxylate

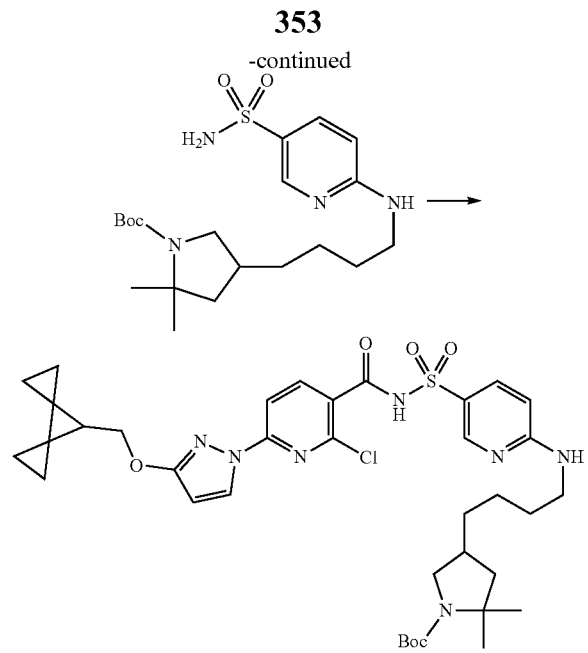

A 100 mL flask was charged under nitrogen with 2-chloro-6-[3-(dispiro[2.0.2.1]heptan-7-ylmethoxy)pyrazol-1-yl]pyridine-3-carboxylic acid (355 mg, 1.027 mmol) and anhydrous tetrahydrofuran (5 mL). Carbonyl diimidazole (183 mg, 1.129 mmol) was added and the mixture was stirred under nitrogen at room temperature for 3.5 h. In a separate 20 mL vial maintained under nitrogen atmosphere, a solution of tert-butyl 2,2-dimethyl-4-[4-[(5-sulfamoyl-2-pyridyl)amino]butyl]pyrrolidine-1-carboxylate (438 mg, 1.027 mmol) in anhydrous tetrahydrofuran (2.5 mL) was prepared and added via syringe to the activated ester solution. Added 1,8-diazabicyclo[5.4.0]undec-7-ene (0.35 mL, 2.340 mmol) and the mixture was stirred at room temperature for 19 h. The solvent was evaporated and the residue was treated with water (50 mL), ethyl acetate (50 mL) and hydrochloric acid (1 mL of 6 M, 6.000 mmol). The two phases were separated. The aqueous phase was further extracted with ethyl acetate (25 mL). The combined organics were washed with brine (30 mL), dried over sodium sulfate and the solvents evaporated. The product was dissolved in dichloromethane and purified by flash chromatography on silica gel (40 g gold column) using a gradient of ethyl acetate (0 to 100% over 30 min) in hexanes. The pure product fractions were collected and the solvents evaporated to give tert-butyl 4-[4-[[5-[[2-chloro-6-[3-(dispiro[2.0.2.1]heptan-7-ylmethoxy)pyrazol-1-yl]pyridine-3-carbonyl]sulfamoyl]-2-pyridyl]amino]butyl]-2,2-dimethyl-pyrrolidine-1-carboxylate (467 mg, 60%) as a white solid. ESI-MS m/z calc. 753.30756, found 754.3 (M+1)⁺; Retention time: 2.34 min (LC Method B).

Step 3: 2-Chloro-N-[[6-[4-(5,5-dimethylpyrrolidin-3-yl)butylamino]-3-pyridyl]sulfonyl]-6-[3-(dispiro[2.0.2.1]heptan-7-ylmethoxy)pyrazol-1-yl]pyridine-3-carboxamide (Dihydrochloride Salt)

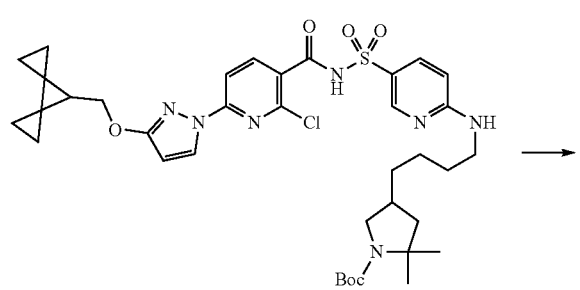

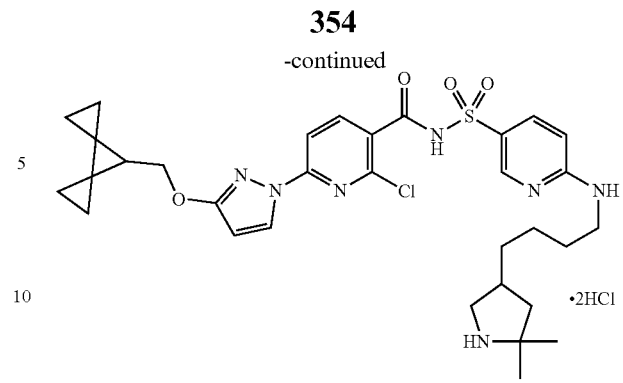

A 100 mL round bottom flask was charged with tert-butyl 4-[4-[[5-[[2-chloro-6-[3-(dispiro[2.0.2.1]heptan-7-ylmethoxy)pyrazol-1-yl]pyridine-3-carbonyl]sulfamoyl]-2-pyridyl]amino]butyl]-2,2-dimethyl-pyrrolidine-1-carboxylate (467 mg, 0.6191 mmol), dichloromethane (6 mL) and hydrochloric acid (0.63 mL of 4 M, 2.520 mmol) (4M in dioxane). The reaction was stirred at room temperature for 3 h. An additional amount of hydrochloric acid (0.5 mL of 4 M, 2.000 mmol) was added and the mixture was stirred for another h. The volatiles were removed by evaporation under vacuum. The residue was triturated with dichloromethane/hexanes and the solvents evaporated. This operation was repeated until a white solid was obtained. Drying under vacuum gave 2-chloro-N-[[6-[4-(5,5-dimethylpyrrolidin-3-yl)butylamino]-3-pyridyl]sulfonyl]-6-[3-(dispiro[2.0.2.1]heptan-7-ylmethoxy)pyrazol-1-yl]pyridine-3-carboxamide (dihydrochloride salt) (420 mg, 93%) as a white solid. The product was used for next step without any further purification. ESI-MS m/z calc. 653.2551, found 654.3 (M+1)⁺; Retention time: 1.58 min (LC Method B).

Step 4: 8-[3-({Dispiro[2.0.2.1]heptan-7-yl}methoxy)-1H-pyrazol-1-yl]-12,12-dimethyl-2λ⁶-thia-3,9,11,19,21-pentaazatetracyclo[18.2.2.111,14.05,10]pentacosa-1(23),5,7,9,20(24),21-hexaene-2,2,4-trione (Enantiomer 1) (Compound 120) and 8-[3-({dispiro[2.0.2.1]heptan-7-yl}methoxy)-1H-pyrazol-1-yl]-12,12-dimethyl-2λ⁶-thia-3,9,11,19,21-pentaazatetracyclo[18.2.2.111,14.05,10]pentacosa-1(23),5,7,9,20(24),21-hexaene-2,2,4-trione (Enantiomer 2) (Compound 121)

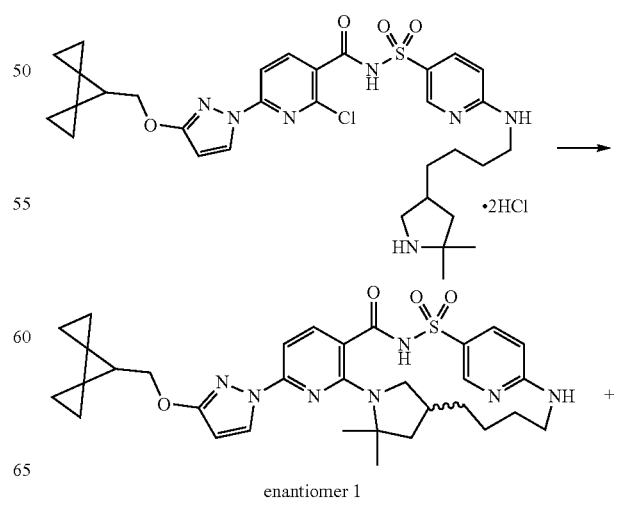

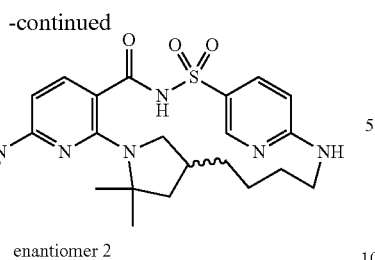

enantiomer 2

A 100 mL round bottom flask equipped with a magnetic stirbar was charged under nitrogen with 2-chloro-N-[[6-[4-(5,5-dimethylpyrrolidin-3-yl)butylamino]-3-pyridyl]sulfonyl]-6-[3-(dispiro[2.0.2.1]heptan-7-ylmethoxy)pyrazol-1-yl]pyridine-3-carboxamide (dihydrochloride salt) (420 mg, 0.5776 mmol), anhydrous NMP (5 mL), potassium carbonate (343 mg, 2.482 mmol) (freshly ground in a mortar) and cesium fluoride (89 mg, 0.5859 mmol). The mixture was vigorously stirred in a dry bath at 145° C. under nitrogen for 13 h then at 165° C. for 8 h. After cooling down to room temperature, the mixture was diluted with water (30 mL) and it was acidified by slowly adding hydrochloric acid (600 μL of 6 M, 3.600 mmol) (final pH=4-5). The resulting solid was filtered and briefly air dried. The solid was dissolved in dichloromethane/ethyl acetate (total volume 50 mL) dried over sodium sulfate, filtered and concentrated to give a solution that was purified by flash chromatography on silica gel (gold 24 g column) using a gradient of methanol (0 to 5% over 30 min) in dichloromethane. Evaporation of the solvents, trituration in dichloromethane/hexanes and evaporation of the solvents again gave the racemic product (79 mg, 22%) as a white solid. This racemic material was subjected to chiral SFC chromatography (ChiralPak AS-H (250×10 mm), 5 μM column; mobile phase 38% acetonitrile/methanol (90:10, no modifier), 62% carbon dioxide, 10 mL/min; concentration 24 mg/mL in acetonitrile/methanol/dimethyl sulfoxide (80:10:10; no modifier); injection volume=70 μL, 100 bar). The first enantiomer to elute was 8-[3-({dispiro[2.0.2.1]heptan-7-yl}methoxy)-1H-pyrazol-1-yl]-12,12-dimethyl-2λ$^6$-thia-3,9,11,19,21-pentaazatetracyclo[18.2.2.1 11,14.0 5,10]pentacosa-1(23),5,7,9,20(24),21-hexaene-2,2,4-trione (enantiomer 1) (Compound 120) (25 mg, 14%), a white solid. $^1$H NMR (400 MHz, dimethyl sulfoxide-d$_6$) δ 12.13 (broad s, 1H, exchangeable by D20), 8.50 (br s, 1H), 8.17 (d, J=2.7 Hz, 1H), 7.88-7.70 (m, 2H), 7.34 (br s, 1H. exch.), 6.90 (d, J=8.3 Hz, 1H), 6.57 (d, J=9.1 Hz, 1H), 6.10 (d, J=2.8 Hz, 1H), 4.23 (d, J=7.0 Hz, 2H), 2.54 (s, 4H), 2.08 (br s, 2H), 1.91 (t, J=7.0 Hz, 1H), 1.73 (d, J=10.4 Hz, 1H), 1.57-1.53 (m, 9H), 1.34-1.15 (m, 1H), 1.05 (br s, 2H), 0.95-0.83 (m, 4H), 0.75-0.64 (m, 2H), 0.59 (d, J=9.0 Hz, 2H). ESI-MS m/z calc. 617.27844, found 618.4 (M+1)$^+$; Retention time: 2.15 min (LC Method B). The second enantiomer to elute was 8-[3-({dispiro[2.0.2.1]heptan-7-yl}methoxy)-1H-pyrazol-1-yl]-12,12-dimethyl-2λ$^6$-thia-3,9,11,19,21-pentaazatetracyclo[18.2.2.1 11,14.0 5,10]pentacosa-1(23),5,7,9,20(24),21-hexaene-2,2,4-trione (enantiomer 2) (Compound 121) (24 mg, 13%), a white solid. $^1$H NMR (400 MHz, dimethyl sulfoxide-d$_6$) δ 12.11 (s, 1H), 8.51 (broad s, 1H), 8.17 (d, J=2.8 Hz, 1H), 7.80 (d, J=8.3 Hz, overlapped with broad s, 2H), 7.33 (br s, 1H), 6.90 (d, J=8.3 Hz, 1H), 6.57 (d, J=8.9 Hz, 1H), 6.10 (d, J=2.7 Hz, 1H), 4.23 (d, J=7.0 Hz, 2H), 2.62-2.49 (m, overlapped with solvent signal, likely 4H), 2.08 (br s, 2H), 1.91 (t, J=7.0 Hz, 1H), 1.72 (br s, 1H), 1.54 (m, 9H), 1.24 (br s, 1H), 1.05 (br s, 2H), 0.92-0.82 (m, 4H), 0.75-0.64 (m, 2H), 0.59 (d, J=9.1 Hz, 2H). ESI-MS m/z calc. 617.27844, found 618.5 (M+1)$^+$; Retention time: 2.15 min (LC Method B).

Example 30: Preparation of 8-[3-({dispiro[2.0.2.1]heptan-7-yl}methoxy)-1H-pyrazol-1-yl]-12,12-dimethyl-2λ$^6$-thia-3,9,11,19,24-pentaazatetracyclo[18.3.1.0 5,10.0 11,15]tetracosa-1(23),5(10),6,8,20(24),21-hexaene-2,2,4-trione (Enantiomer 1) (Compound 124) and 8-[3-({Dispiro[2.0.2.1]heptan-7-yl}methoxy)-1H-pyrazol-1-yl]-12,12-dimethyl-2λ$^6$-thia-3,9,11,19,24-pentaazatetracyclo[18.3.1.0 5,10.0 11,15]tetracosa-1(23),5(10),6,8,20(24),21-hexaene-2,2,4-trione (Enantiomer 2) (Compound 125)

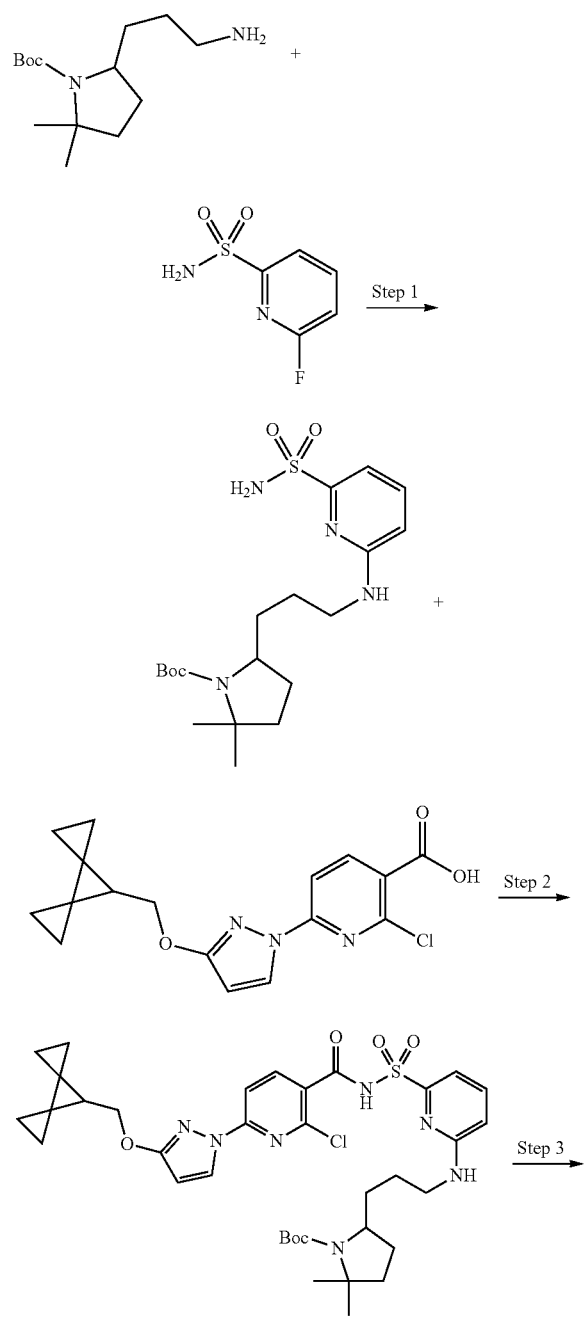

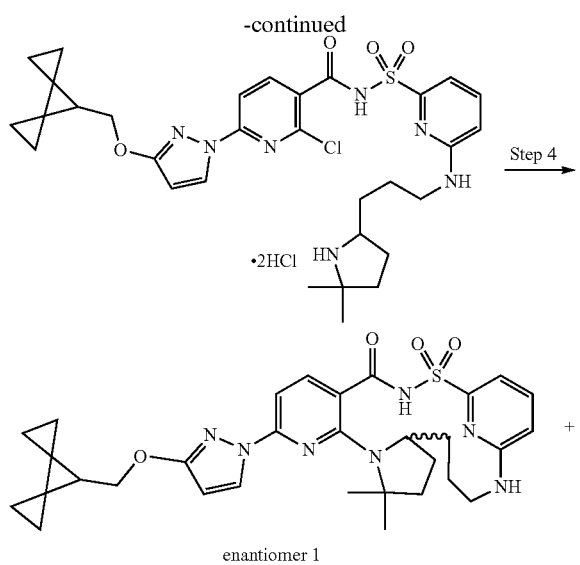

enantiomer 1 enantiomer 2

Step 1: tert-Butyl 2,2-dimethyl-5-[3-[(6-sulfamoyl-2-pyridyl)amino]propyl]pyrrolidine-1-carboxylate

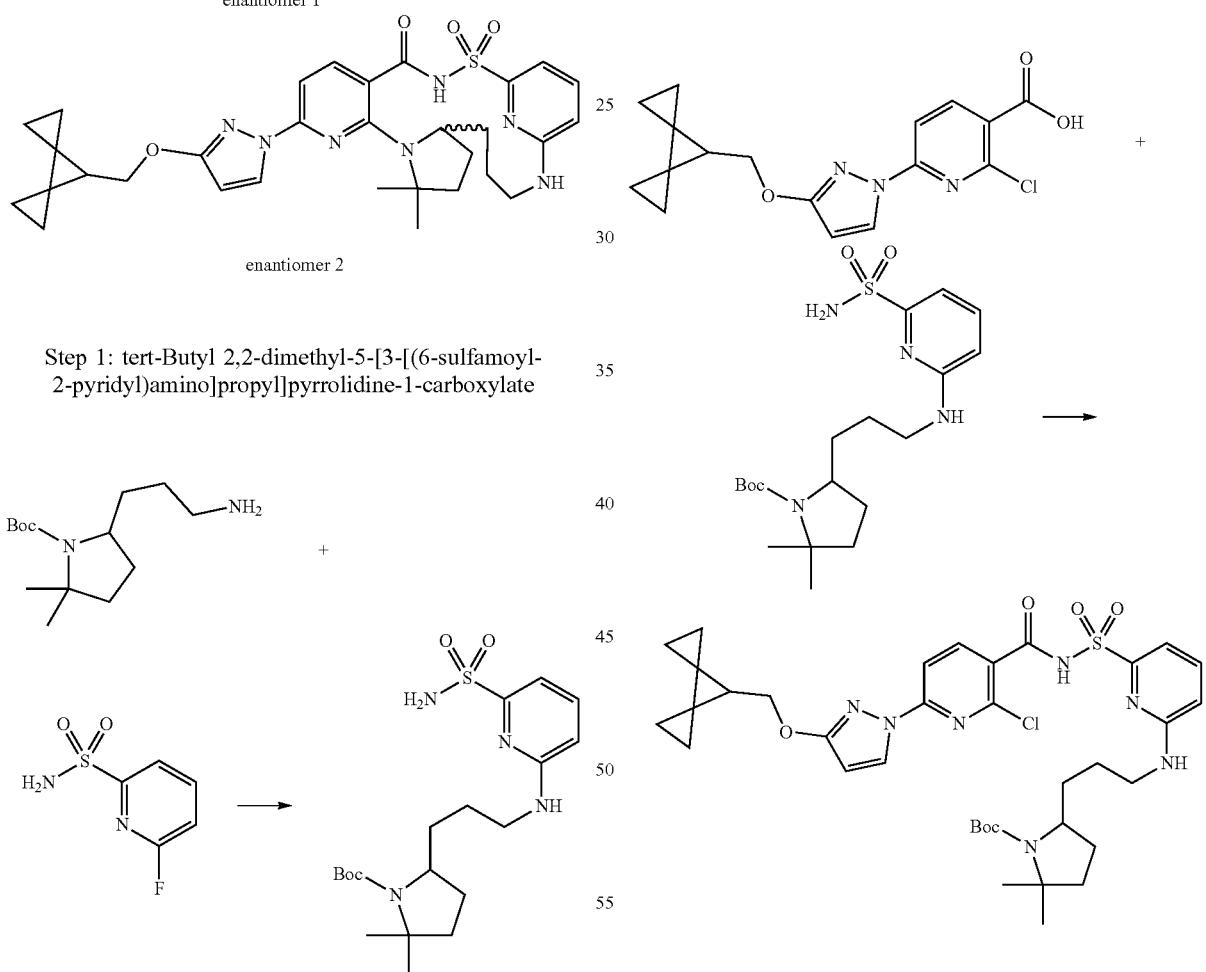

To a solution of tert-butyl 5-(3-aminopropyl)-2,2-dimethyl-pyrrolidine-1-carboxylate (500 mg, 1.950 mmol) in N,N-dimethylformamide (5 mL) was added 6-fluoropyridine-2-sulfonamide (343, 1.950 mmol) followed by potassium carbonate (808 mg, 5.850 mmol). The flask was capped with a septum and heated at 70° C. under a nitrogen balloon in an oil bath for 18 h. The reaction mixture was cooled down to room temperature, then diluted with ethyl acetate and washed with a brine solution. The organics were separated, dried over sodium sulfate, filtered and evaporated and then purified by silica gel chromatography (80 gram column) using a gradient from 100% hexanes to 100% ethyl acetate to afford tert-butyl 2,2-dimethyl-5-[3-[(6-sulfamoyl-2-pyridyl)amino]propyl]pyrrolidine-1-carboxylate (428 mg, 53%) as white foamy solid. $^1$H NMR (400 MHz, Chloroform-d) δ 7.51 (t, J=7.9 Hz, 1H), 7.19 (d, J=7.3 Hz, 1H), 6.55 (d, J=8.5 Hz, 1H), 5.51 (s, 1H), 5.05 (s, 2H), 3.90 (s, 1H), 3.57-3.42 (m, 1H), 3.32 (d, J=9.8 Hz, 2H), 1.91 (s, 2H), 1.77 (d, J=30.5 Hz, 1H), 1.62 (d, J=2.9 Hz, 3H), 1.48 (s, 10H), 1.27 (t, J=3.6 Hz, 3H). ESI-MS m/z calc. 412.21442, found 413.25 (M+1)$^+$; Retention time: 0.65 min (LC Method B).

Step 2: tert-Butyl 5-[3-[[6-[[2-chloro-6-[3-(dispiro[2.0.2.1]heptan-7-ylmethoxy)pyrazol-1-yl]pyridine-3-carbonyl]sulfamoyl]-2-pyridyl]amino]propyl]-2,2-dimethyl-pyrrolidine-1-carboxylate A 100 mL flask was charged under nitrogen with 2-chloro-6-[3-(dispiro[2.0.2.1]heptan-7-ylmethoxy)pyrazol-1-yl]pyridine-3-carboxylic acid (327 mg, 0.9457 mmol) and anhydrous tetrahydrofuran (5 mL). Carbonyl diimidazole (168 mg, 1.036 mmol) was added and the mixture was stirred under nitrogen at room temperature for 2 h (complete activation by LCMS of aliquot in sec-butyl amine). In a separate 20 mL vial maintained under nitrogen atmosphere, a solution of tert-butyl 2,2-dimethyl-5-[3-[(6-sulfamoyl-2-pyridyl)amino]propyl]pyrrolidine-1-carboxylate (390 mg, 0.9453 mmol) in anhydrous tetrahydrofuran (2.5 mL) was prepared and added via syringe to the activated ester solution. Added 1,8-diazabicyclo[5.4.0]undec-7-ene (0.32 mL, 2.140 mmol) and the mixture was stirred at room temperature for 13 h. The solvent was evaporated and the residue was treated with water (50 mL), ethyl acetate (50 mL) and hydrochloric acid (1 mL of 6 M, 6.000 mmol). The two phases were separated. The aqueous phase was further extracted with ethyl acetate (25 mL). The combined organics were washed with brine (30 mL), dried over sodium sulfate and the solvents evaporated. The product was dissolved in dichloromethane and purified by flash chromatography on silica gel (40 g gold column) using a gradient of ethyl acetate (0 to 100% over 30 min) in hexanes. The pure fractions were collected and the solvents evaporated to give tert-butyl 5-[3-[[6-[[2-chloro-6-[3-(dispiro[2.0.2.1]heptan-7-yl-methoxy)pyrazol-1-yl]pyridine-3-carbonyl]sulfamoyl]-2-pyridyl]amino]propyl]-2,2-dimethyl-pyrrolidine-1-carboxylate (435 mg, 62%) as a white solid. ESI-MS m/z calc. 739.2919, found 740.3 (M+1)$^+$; Retention time: 2.47 min (LC Method B).

Step 3: 2-Chloro-N-[[6-[3-(5,5-dimethylpyrrolidin-2-yl)propylamino]-2-pyridyl]sulfonyl]-6-[3-(dispiro[2.0.2.1]heptan-7-ylmethoxy)pyrazol-1-yl]pyridine-3-carboxamide (Dihydrochloride Salt)

A 100 mL round bottom flask was charged with tert-butyl 5-[3-[[6-[[2-chloro-6-[3-(dispiro[2.0.2.1]heptan-7-yl-methoxy)pyrazol-1-yl]pyridine-3-carbonyl]sulfamoyl]-2-pyridyl]amino]propyl]-2,2-dimethyl-pyrrolidine-1-carboxylate (435 mg, 0.5876 mmol), dichloromethane (6 mL) and hydrochloric acid (0.6 mL of 4 M, 2.400 mmol) (4M in dioxane). The reaction was stirred at room temperature for 3 h. An additional amount of hydrochloric acid (500 µL of 4 M, 2.000 mmol) was added and the mixture was stirred for another h. The volatiles were removed by evaporation under vacuum. The residue was triturated with dichloromethane/hexanes and the solvents evaporated. The operation was repeated until a white solid was obtained. Drying under vacuum gave 2-chloro-N-[[6-[3-(5,5-dimethylpyrrolidin-2-yl)propylamino]-2-pyridyl]sulfonyl]-6-[3-(dispiro[2.0.2.1]heptan-7-ylmethoxy)pyrazol-1-yl]pyridine-3-carboxamide (dihydrochloride salt) (439 mg, 105%) as a white solid. The product was used for next step without any further purification. ESI-MS m/z calc. 639.23944, found 640.3 (M+1)$^+$; Retention time: 1.7 min (LC Method B).

Step 4: 8-[3-({Dispiro[2.0.2.1]heptan-7-yl}methoxy)-1H-pyrazol-1-yl]-12,12-dimethyl-2λ$^6$-thia-3,9,11,19,24-pentaazatetracyclo[18.3.1.05,10.011,15]tetracosa-1(23),5(10),6,8,20(24),21-hexaene-2,2,4-trione (Enantiomer 1) (Compound 124) and 8-[3-({Dispiro[2.0.2.1]heptan-7-yl}methoxy)-1H-pyrazol-1-yl]-12,12-dimethyl-2λ$^6$-thia-3,9,11,19,24-pentaazatetracyclo[18.3.1.05,10.011,15]tetracosa-1(23),5(10),6,8,20(24),21-hexaene-2,2,4-trione (Enantiomer 2) (Compound 125)

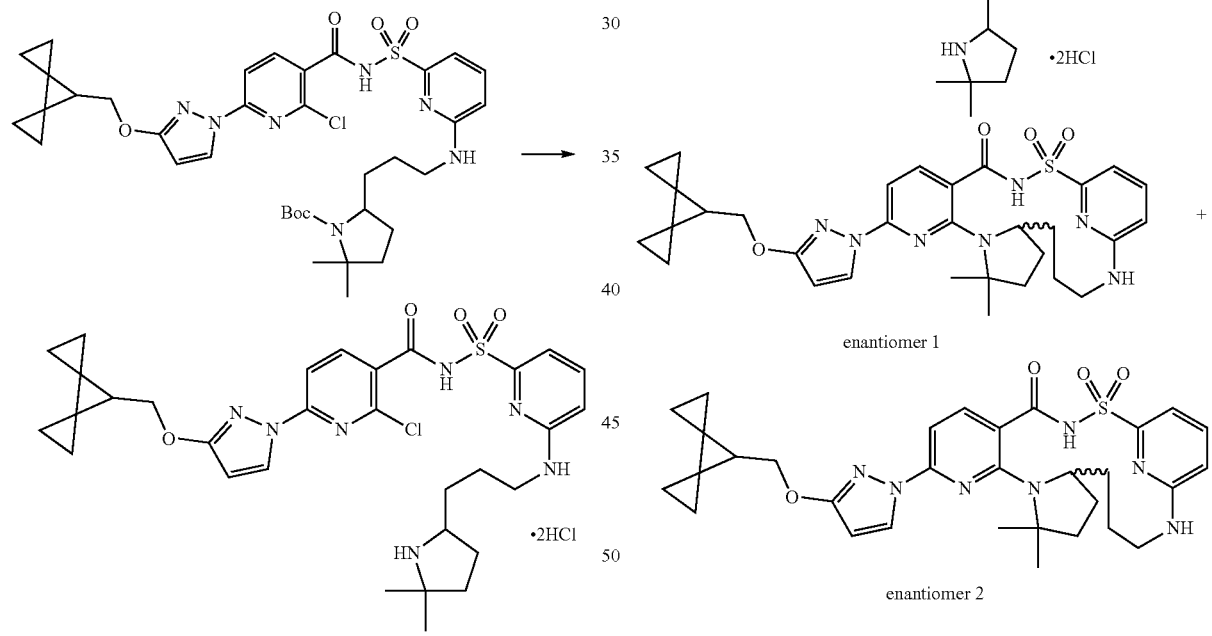

enantiomer 1 enantiomer 2

A 100 mL round bottom flask equipped with a magnetic stirbar was charged under nitrogen with 2-chloro-N-[[6-[3-(5,5-dimethylpyrrolidin-2-yl)propylamino]-2-pyridyl]sulfonyl]-6-[3-(dispiro[2.0.2.1]heptan-7-ylmethoxy)pyrazol-1-yl]pyridine-3-carboxamide (dihydrochloride salt) (439 mg, 0.6156 mmol), anhydrous NMP (5 mL), potassium carbonate (410 mg, 2.967 mmol) (freshly ground in a mortar) and cesium fluoride (94.82 mg, 23.04 µL, 0.6242 mmol). The mixture was vigorously stirred in a dry bath at 145° C. under nitrogen for 46 h then at 155° C. for 14 h. After cooling to room temperature, the mixture was diluted with water (30 mL) and it was acidified by slowly adding hydrochloric acid (500 µL of 6 M, 3.000 mmol) (final pH=4-5). The resulting solid was filtered and briefly air dried. The solid was dissolved in dichloromethane (total volume 50 mL) dried over sodium sulfate, filtered and concentrated then purified by flash chromatography on silica gel (4 g column) using a gradient of methanol (0 to 5% over 30 min) in dichloromethane. Evaporation of the solvents, trituration in dichloromethane/hexanes and evaporation of the solvents again gave the expected racemic product as an off-white solid (154 mg, 41%). The racemic material was subjected to chiral SFC chromatography (ChiralPak IG column (250×21.2 mm), 5 μm, mobile phase 38% acetonitrile:methanol (90:10 no modifier), 62% carbon dioxide, 70 mL/min, 30 mg/mL in acetonitrile:methanol (90:10 no modifier), inj. volume 500 μL, 100 bar). After evaporation of the solvents, the residue was triturated in dichloromethane/hexanes and the solvents were removed. The first enantiomer to elute was 8-[3-({dispiro[2.0.2.1]heptan-7-yl}methoxy)-1H-pyrazol-1-yl]-12,12-dimethyl-2λ$^6$-thia-3,9,11,19,24-pentaazatetracyclo[18.3.1.05,10.011,15]tetracosa-1(23),5(10),6,8,20(24),21-hexaene-2,2,4-trione (enantiomer 1) (Compound 124) (62 mg, 33%) isolated as a white solid. $^1$H NMR (400 MHz, dimethyl sulfoxide-d$_6$) δ 12.70 (broad s, 1H), 8.21 (d, J=2.8 Hz, 1H), 8.00 (broad d, J=8.0 Hz, 1H), 7.58 (dd, J=8.5, 7.2 Hz, 1H), 7.28 (br s, 1H), 7.08 (br s, 1H), 7.03 (d, J=7.2 Hz, 1H), 6.62 (d, J=8.4 Hz, 1H), 6.12 (d, J=2.8 Hz, 1H), 4.24 (d, J=7.0 Hz, 2H), 3.71 (br s, 2H), 3.11 (br s, 1H), 2.00-1.80 (m, 3), 1.73 (br s, 2H), 1.63-1.43 (m, 5H), 1.42-1.31 (m, 4H), 1.09-0.88 (m, 1H), 0.94-0.80 (m, 4H), 0.76-0.64 (m, 2H), 0.66-0.53 (m, 2H). ESI-MS m/z calc. 603.26276, found 604.3 (M+1)$^+$; Retention time: 1.95 min (LC Method B). The second enantiomer to elute was 8-[3-({dispiro[2.0.2.1]heptan-7-yl}methoxy)-1H-pyrazol-1-yl]-12,12-dimethyl-2λ$^6$-thia-3,9,11,19,24-pentaazatetracyclo[18.3.1.05,10.011,15]tetracosa-1(23),5(10),6,8,20(24),21-hexaene-2,2,4-trione (enantiomer 2) (Compound 125) (54 mg, 28%) isolated as a white solid. $^1$H NMR (400 MHz, dimethyl sulfoxide-d$_6$) δ 12.67 (broad s, 1H), 8.21 (d, J=2.8 Hz, 1H), 8.00 (br d, J=7.1 Hz, 1H), 7.58 (t, J=7.8 Hz, 1H), 7.37-7.21 (m, 1H), 7.08 (br s, 1H), 7.03 (d, J=7.1 Hz, 1H), 6.62 (d, J=8.5 Hz, 1H), 6.12 (d, J=2.8 Hz, 1H), 4.24 (d, J=7.1 Hz, 2H), 3.71 (br s, 2H), 3.10 (br s, 1H), 2.02-1.79 (m, 3H), 1.73 (s, 2H), 1.64-1.45 (m, 5H), 1.42-1.28 (m, 4H), 0.99 (br s, 1H), 0.94-0.77 (m, 4H), 0.77-0.65 (m, 2H), 0.64-0.54 (m, 2H). ESI-MS m/z calc. 603.26276, found 604.3 (M+1)$^+$; Retention time: 1.96 min (LC Method B).

Example 31: Preparation of (14S)-8-[3-(3,3-dimethylbutyl)-2-oxopyrrolidin-1-yl]-12,12-dimethyl-2λ$^6$-thia-3,9,11,18,23-pentaazatetracyclo[17.3.1.111,14.05,10]tetracosa-1(23),5,7,9,19,21-hexaene-2,2,4-trione (Diastereomer 1) (Compound 126) and (14S)-8-[3-(3,3-dimethylbutyl)-2-oxopyrrolidin-1-yl]-12,12-dimethyl-2λ$^6$-thia-3,9,11,18,23-pentaazatetracyclo[17.3.1.111,14.05,10]tetracosa-1(23),5,7,9, 19,21-hexaene-2,2,4-trione (Diastereomer 2) (Compound 127)

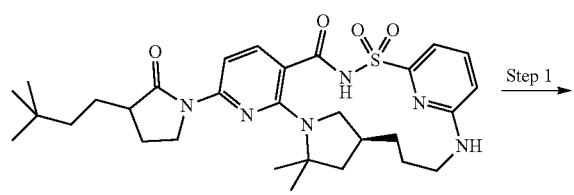

Step 1

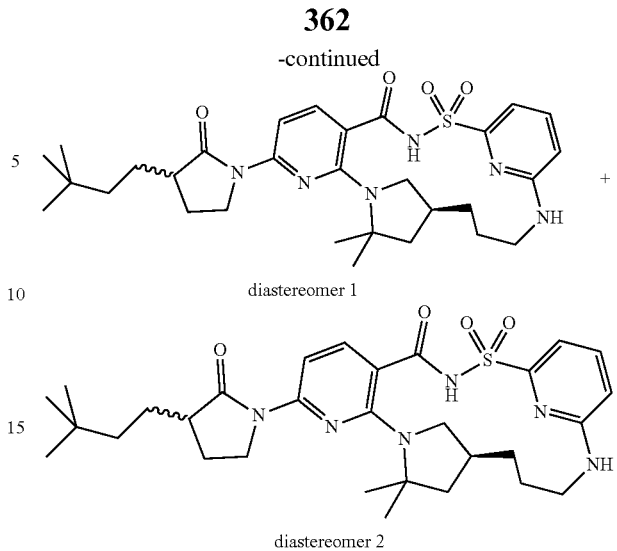

diastereomer 1 diastereomer 2

Step 1: (14S)-8-[3-(3,3-Dimethylbutyl)-2-oxopyrrolidin-1-yl]-12,12-dimethyl-2λ$^6$-thia-3,9,11,18,23-pentaazatetracyclo[17.3.1.111,14.05,10]tetracosa-1(23),5,7,9,19,21-hexaene-2,2,4-trione (Diastereomer 1) (Compound 126) and (14S)-8-[3-(3,3-dimethylbutyl)-2-oxopyrrolidin-1-yl]-12,12-dimethyl-2λ$^6$-thia-3,9,11,18,23-pentaazatetracyclo[17.3.1.111, 14.05,10]tetracosa-1(23),5,7,9,19,21-hexaene-2,2,4-trione (Diastereomer 2) (Compound 127)

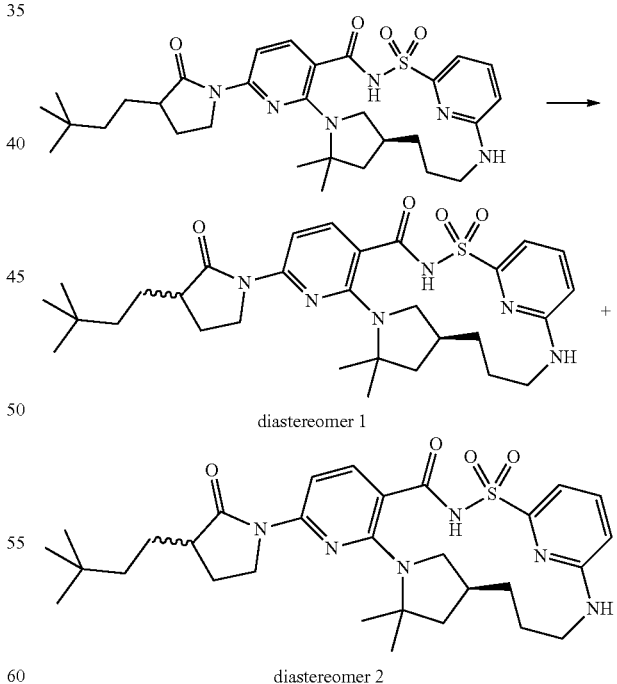

diastereomer 1 diastereomer 2

(14S)-8-[3-(3,3-Dimethylbutyl)-2-oxopyrrolidin-1-yl]-12,12-dimethyl-2λ$^6$-thia-3,9,11,18,23-pentaazatetracyclo[17.3.1.111,14.05,10]tetracosa-1(23),5,7,9,19,21-hexaene-2,2,4-trione was subjected to chiral SFC separation (separation (ChiralCel OJ-H (250×10 mm), 5 μM column;

mobile phase 25% acetonitrile/methanol (90:10, no modifier), 75% carbon dioxide, 10 mL/min; concentration 24 mg/mL in acetonitrile/methanol (90:10); injection volume 70 μL, 100 bar).

For pure collected fractions, the solvents were evaporated and the residue triturated in dichloromethane/hexanes. The first diastereomer to elute was (14S)-8-[3-(3,3-dimethylbutyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (diastereomer 1) (Compound 126) (19 mg, 36%). ¹H NMR (400 MHz, dimethyl sulfoxide-d₆) δ 12.42 (s, 1H), 7.68 (d, J=8.4 Hz, 1H), 7.62-7.46 (m, 2H), 7.03 (d, J=7.0 Hz, 1H), 6.97 (broad s, 1H), 6.70 (d, J=8.6 Hz, 1H), 4.04 (t, J=9.3 Hz, 1H), 3.99-3.83 (m, 1H), 3.74 (q, J=10.3, 9.7 Hz, 1H), 3.10 (br s, 1H), 2.94 (d, J=13.5 Hz, 1H), 2.76-2.63 (m, 1H), 2.24 (dd, J=17.4, 7.7 Hz, 1H), 2.10 (br s, 1H), 1.88-1.64 (m, 4H), 1.65-1.40 (m, 9H), 1.40-1.13 (m, 4H), 0.88 (s, 9H). ESI-MS m/z calc. 582.2988, found 583.4 (M+1)⁺; Retention time: 2.13 min (LC Method B). The second diastereomer to elute was (14S)-8-[3-(3,3-dimethylbutyl)-2-oxopyrrolidin-1-yl]-12,12-dimethyl-2|⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (diastereomer 2) (Compound 127) (17 mg, 32%). ¹H NMR (400 MHz, dimethyl sulfoxide-d₆) δ 12.42 (s, 1H), 7.68 (d, J=8.5 Hz, 1H), 7.61-7.49 (m, 2H), 7.04 (d, J=7.1 Hz, 1H), 6.97 (broad d, J=7.0 Hz, 1H), 6.70 (d, J=8.4 Hz, 1H), 3.96-3.79 (m, 3H), 3.09 (br s, 1H), 2.93 (br d, J=13.3 Hz, 1H), 2.75-2.55 (m, 2H), 2.30-2.18 (m, 1H), 2.09 (br s, 1H), 1.88-1.69 (m, 3H), 1.69-1.41 (m, 10H), 1.34-1.15 (m, 4H), 0.88 (s, 9H). ESI-MS m/z calc. 582.2988, found 583.4 (M+1)⁺; Retention time: 2.14 min (LC Method B).

Example 32: Preparation of 12,12,22-trimethyl-8-(3-{2-[1-(trifluoromethyl) cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 129)

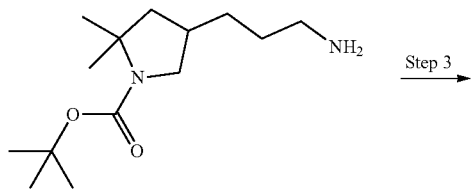

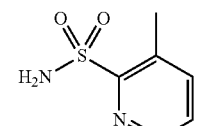

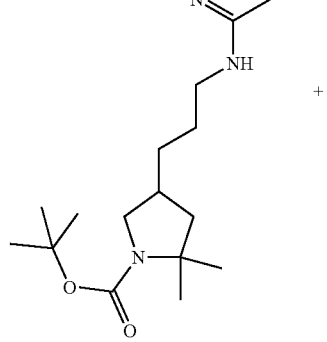

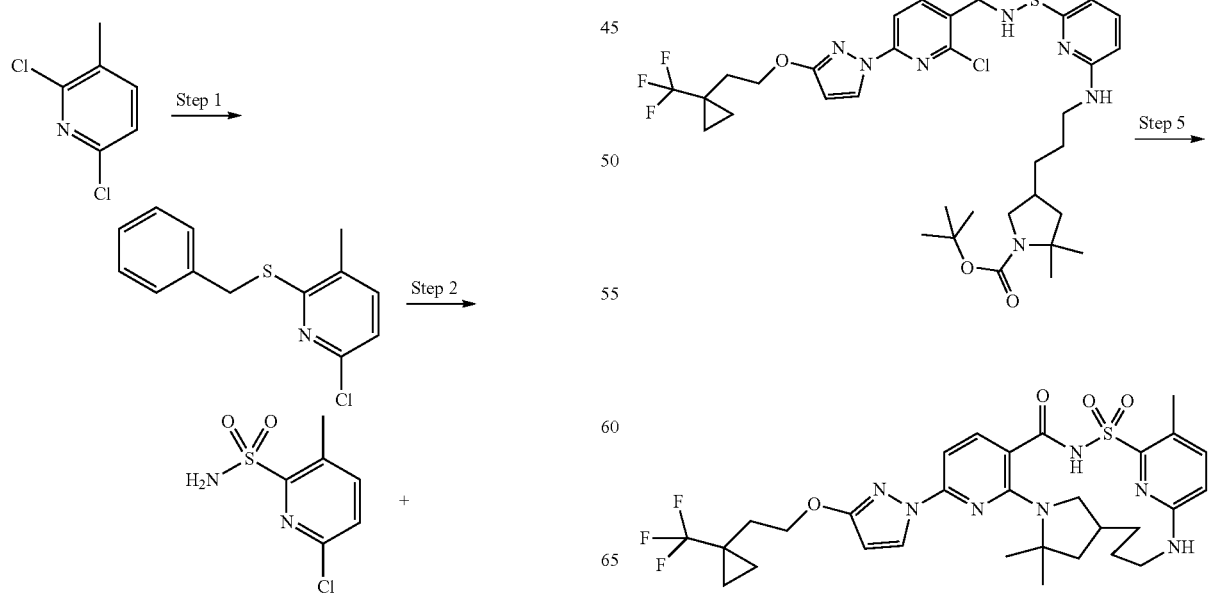

Step 1: 2-Benzylsulfanyl-6-chloro-3-methyl-pyridine

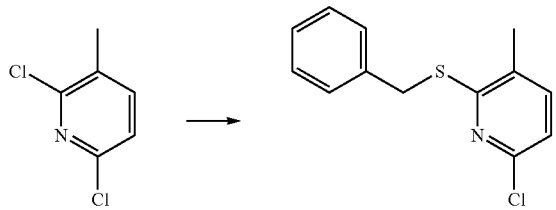

2,6-Dichloro-3-methyl-pyridine (5.05 g, 31.17 mmol) and phenylmethanethiol (3.871 g, 3.659 mL, 31.17 mmol) were dissolved in tetrahydrofuran (50.50 mL) and sodium tert-butoxide (31.17 mL of 2 M, 62.34 mmol) was added. The reaction was stirred for 16 h and partitioned between water and ethyl acetate. The organics were separated, washed with brine, dried over sodium sulfate, filtered and evaporated. The crude material was used without further purification, 2-benzylsulfanyl-6-chloro-3-methyl-pyridine (7.15 g, 92%). ESI-MS m/z calc. 249.0379, found 250.0 (M+1)$^+$; Retention time: 0.81 min (LC Method A).

Step 2: 6-Chloro-3-methyl-pyridine-2-sulfonamide

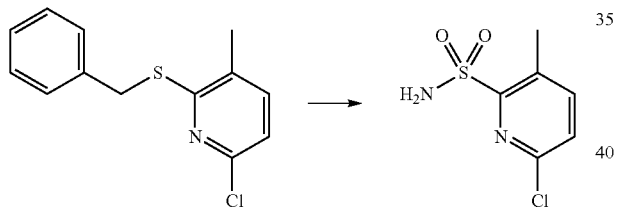

A biphasic mixture of 2-benzylsulfanyl-6-chloro-3-methyl-pyridine (7.15 g, 28.63 mmol) in dichloromethane (42.90 mL), water (14.30 mL), and hydrochloric acid (2.863 mL of 1 M, 2.863 mmol) was cooled in a salt water ice bath. (hydrochloric acid was added to avoid an otherwise delayed exotherm upon the $Cl_2$ addition). $Cl_2$ (8.119 g, 114.5 mmol) was bubbled through the solution (3 times at 2 min intervals) over an h. The reaction was stirred at 0° C. After 1.5 h, the reaction was added dropwise to an ice bath cooled solution of $NH_4OH$ (43.01 mL of 28% w/v, 343.6 mmol). The reaction was warmed to room temperature and stirred for 15 min. The reaction mixture was partitioned between ethyl acetate (60 mL) and water (20 mL). The organics were separated and the aqueous layer was extracted with ethyl acetate (2×60 mL). The organics were combined, washed with brine, dried over sodium sulfate, filtered and evaporated. The resulting solid was triturated with dichloromethane (30 mL) and filtered. The solid was washed with minimal dichloromethane to give an off white solid, 6-chloro-3-methyl-pyridine-2-sulfonamide (2.95 g, 50%).

$^1$H NMR (400 MHz, dimethyl sulfoxide-d$_6$) δ 7.94 (d, J=8.1, 0.9 Hz, 1H), 7.68 (d, J=8.1 Hz, 1H), 7.63 (s, 2H), 2.55 (s, 3H). ESI-MS m/z calc. 205.99167, found 207.1 (M+1)$^+$; Retention time: 0.3 min (LC Method A).

Step 3: tert-Butyl 2,2-dimethyl-4-[3-[(5-methyl-6-sulfamoyl-2-pyridyl)amino]propyl]pyrrolidine-1-carboxylate

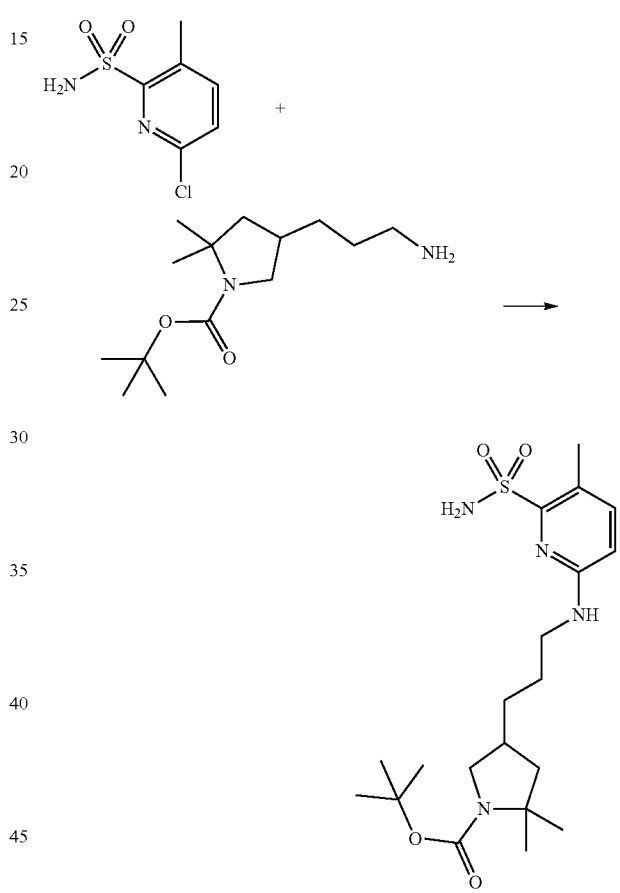

To a nitrogen purged microwave reaction vial was added 6-chloro-3-methyl-pyridine-2-sulfonamide (1.12 g, 5.420 mmol), tert-butyl 4-(3-aminopropyl)-2,2-dimethyl-pyrrolidine-1-carboxylate (1 g, 3.900 mmol)), diisopropylethylamine (2.520 g, 3.396 mL, 19.50 mmol) and n-BuOH (11 mL). The vial was sealed and allowed to stir at 125° C. for 20 h. The solvent was removed in vacuo and the residue was dissolved in dichloromethane and washed with water. Organic extract was dried over sodium sulfate, evaporated and purified by silica gel chromatography (gradient from 0% to 85% ethyl acetate in hexanes) to afford tert-butyl 2,2-dimethyl-4-[3-[(5-methyl-6-sulfamoyl-2-pyridyl)amino] propyl]pyrrolidine-1-carboxylate (360 mg, 22%). ESI-MS m/z calc. 426.23007, found 427.29 (M+1)$^+$; Retention time: 0.67 min (LC Method A).

Step 4: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-5-methyl-2-pyridyl]amino]propyl]-2,2-dimethyl-pyrrolidine-1-carboxylate

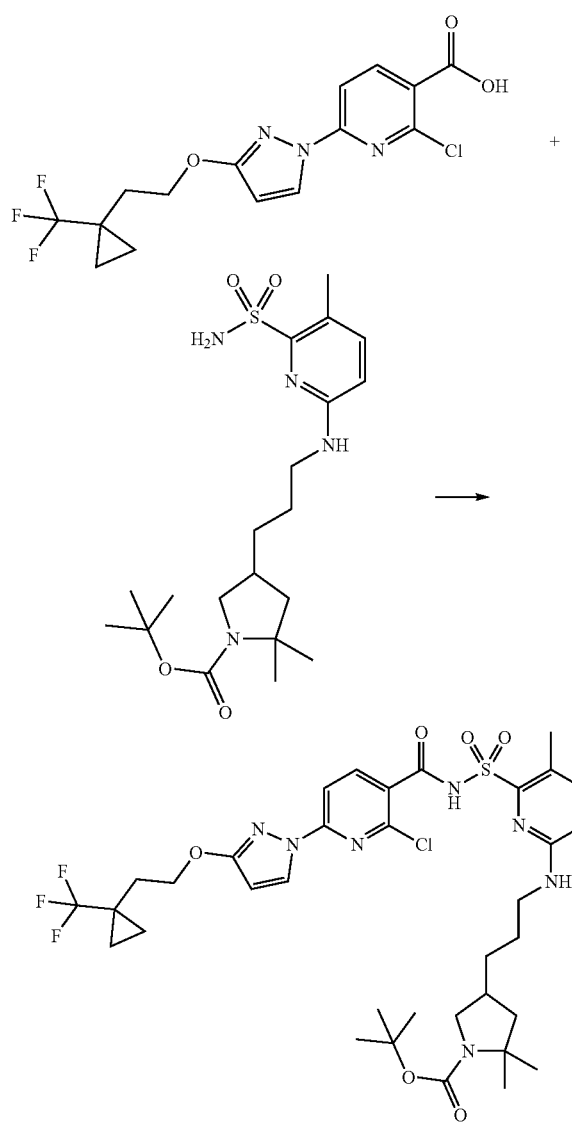

2-Chloro-6-[3-[2-[1-(trifluoromethyl)cyclopropyl]ethoxy]pyrazol-1-yl]pyridine-3-carboxylic acid (317.1 mg, 0.8439 mmol) and carbonyl diimidazole (136.8 mg, 0.8439 mmol) were combined in anhydrous tetrahydrofuran (8.5 mL) and stirred for 90 min at 50° C. Then tert-butyl 2,2-dimethyl-4-[3-[(5-methyl-6-sulfamoyl-2-pyridyl)amino]propyl]pyrrolidine-1-carboxylate (360 mg, 0.8439 mmol) was added followed by 1,8-diazabicyclo[5.4.0]undec-7-ene (128.5 mg, 126.2 µL, 0.8439 mmol) and the reaction was heated at 50° C. for 15 h. The reaction was diluted with ethyl acetate and washed with a 1M citric acid solution, followed by brine. The organics were separated, dried over sodium sulfate, filtered and evaporated and then purified by silica gel using a gradient of 100% hexanes to 75% ethyl acetate in hexanes to afford as an off-white solid, tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-5-methyl-2-pyridyl]amino]propyl]-2,2-dimethyl-pyrrolidine-1-carboxylate (326 mg, 49%). ESI-MS m/z calc. 783.27924, found 784.42 (M+1)$^+$; Retention time: 0.89 min(LC Method A).

Step 5: 12,12,22-Trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 129)

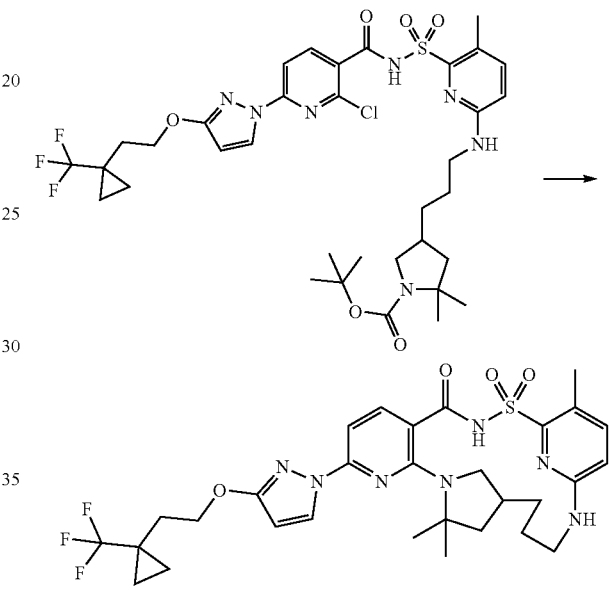

Part A: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-5-methyl-2-pyridyl]amino]propyl]-2,2-dimethyl-pyrrolidine-1-carboxylate (186 mg, 0.2372 mmol) was dissolved in dichloromethane (3 mL) and to the mixture was added hydrochloric acid (4M in dioxane) (2.2 mL of 4 M, 8.800 mmol) and the mixture was stirred at room temperature for 30 min. Concentrated mixture to dryness under reduced pressure and carried on directly to next step.

Part B: Combined material from Part A and potassium carbonate (197 mg, 1.425 mmol), cesium fluoride (60 mg, 0.3950 mmol), 3 Å molecular sieves and dimethyl sulfoxide (3 mL) in a vial, purged with nitrogen, capped, heated to 140° C. and stirred for 16 h. The reaction mixture was allowed to cool to room temperature, was filtered and then purified by reverse-phase preparative HPLC chromatography utilizing a C$_{18}$ column and a 30-99 A1-B1 gradient (acetonitrile-water+5 mM hydrochloric acid 30 min, ×2 injections) to afford as a white solid, 12,12,22-trimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 129) (53 mg, 34%). ESI-MS m/z calc. 647.2502, found 648.31 (M+1)$^+$; Retention time: 2.29 min (LC Method B).

Example 33: Preparation of 8-[3-(3,3-dicyclopropylpropoxy)-1H-pyrazol-1-yl]-12,12-dimethyl-2λ⁶-thia-3,9,11,19,21-pentaazatetracyclo[18.2.2.1¹¹,¹⁴.0⁵,¹⁰]pentacosa-1(22),5,7,9,20,23-hexaene-2,2,4-trione (Compound 130)

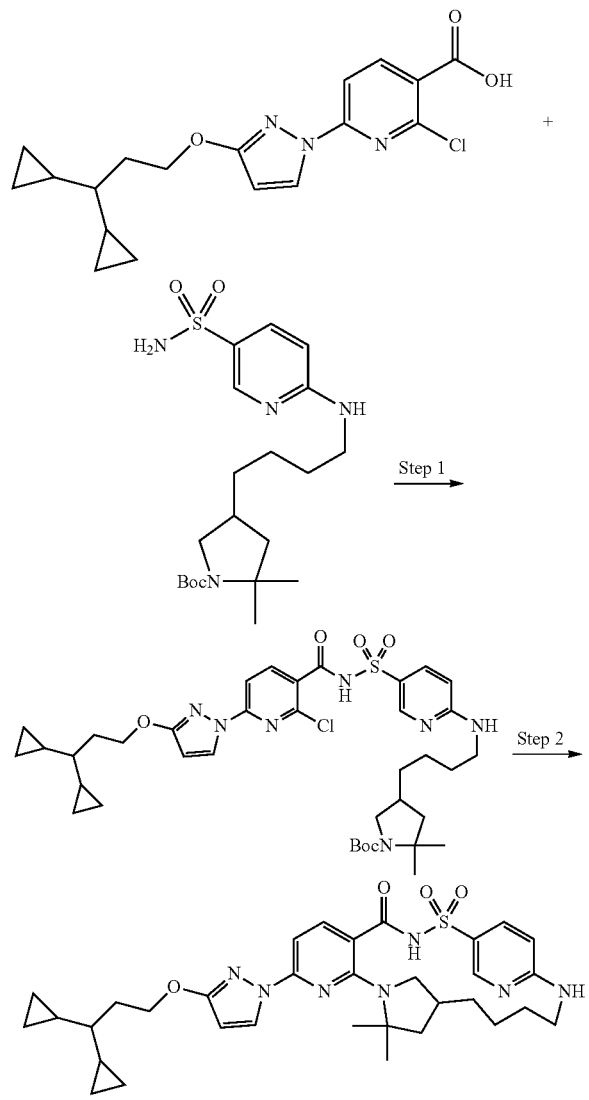

Step 1: tert-Butyl 4-[4-[[5-[[2-chloro-6-[3-(3,3-dicyclopropylpropoxy)pyrazol-1-yl]pyridine-3-carbonyl]sulfamoyl]-2-pyridyl]amino]butyl]-2,2-dimethyl-pyrrolidine-1-carboxylate

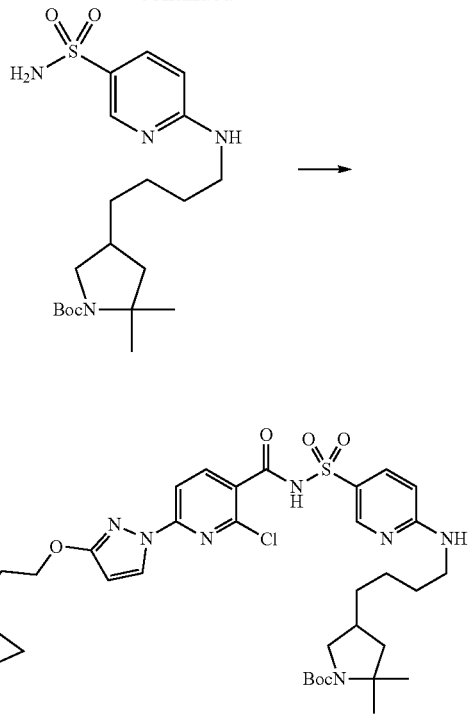

2-Chloro-6-[3-(3,3-dicyclopropylpropoxy)pyrazol-1-yl]pyridine-3-carboxylic acid (356.3 mg, 0.9846 mmol) and carbonyl diimidazole (159.7 mg, 0.9846 mmol) were combined in tetrahydrofuran (5 mL) and stirred at room temperature for 16 h. Then tert-butyl 2,2-dimethyl-4-[4-[(5-sulfamoyl-2-pyridyl)amino]butyl]pyrrolidine-1-carboxylate (350 mg, 0.8205 mmol) and 1,8-diazabicyclo[5.4.0]undec-7-ene (187.4 mg, 184.1 µL, 1.231 mmol) were added and the reaction was stirred at room temperature for 6 h. The reaction was diluted with ethyl acetate and washed with saturated aqueous ammonium chloride solution followed by brine. The organic layers was separated, dried over sodium sulfate, filtered and evaporated then purified by silica gel chromatography using a gradient from 100% dichloromethane to 20% methanol in dichloromethane to afford tert-butyl 4-[4-[[5-[[2-chloro-6-[3-(3,3-dicyclopropylpropoxy)pyrazol-1-yl]pyridine-3-carbonyl]sulfamoyl]-2-pyridyl]amino]butyl]-2,2-dimethyl-pyrrolidine-1-carboxylate (423 mg, 67%) as a white solid. ¹H NMR (400 MHz, Chloroform-d) δ 8.70 (s, 1H), 8.27 (d, J=2.9 Hz, 1H), 8.19 (d, J=8.5 Hz, 1H), 8.08 (d, J=8.9 Hz, 1H), 7.70 (d, J=8.5 Hz, 1H), 6.41 (d, J=8.9 Hz, 1H), 5.95 (d, J=2.9 Hz, 1H), 5.48 (brs, 1H), 4.41 (t, J=6.8 Hz, 2H), 3.64 (dt, J=40.0, 9.2 Hz, 1H), 3.34 (s, 2H), 2.85 (q, J=11.1 Hz, 1H), 2.06 (d, J=14.5 Hz, 1H), 1.96 (q, J=6.8 Hz, 2H), 1.86 (t, J=9.4 Hz, 1H), 1.63 (s, 2H), 1.44 (d, J=6.4 Hz, 10H), 1.36 (d, J=5.8 Hz, 7H), 1.27 (d, J=18.6 Hz, 3H), 0.65 (tq, J=8.3, 5.0, 4.1 Hz, 2H), 0.51-0.36 (m, 4H), 0.35-0.26 (m, 1H), 0.24-0.14 (m, 2H), 0.13-0.04 (m, 2H). ESI-MS m/z calc. 769.3388, found 770.45 (M+1)⁺; Retention time: 0.91 min (LC Method A).

Step 2: 8-[3-(3,3-Dicyclopropylpropoxy)-1H-pyrazol-1-yl]-12,12-dimethyl-2λ⁶-thia-3,9,11,19,21-pentaazatetracyclo[18.2.2.1 11,14.0 5,10]pentacosa-1(22), 5,7,9,20,23-hexaene-2,2,4-trione (Compound 130)

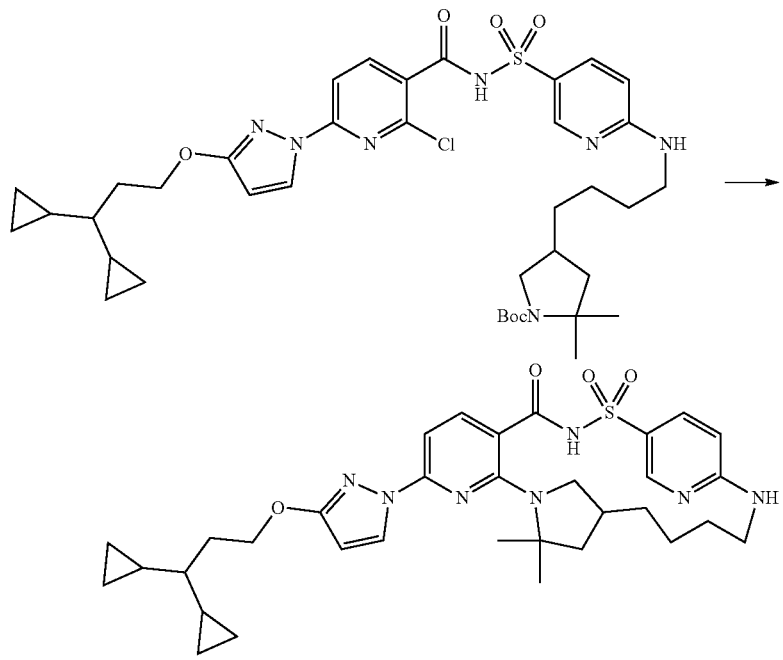

A solution of tert-butyl 4-[4-[[5-[[2-chloro-6-[3-(3,3-dicyclopropylpropoxy)pyrazol-1-yl]pyridine-3-carbonyl]sulfamoyl]-2-pyridyl]amino]butyl]-2,2-dimethyl-pyrrolidine-1-carboxylate (415 mg, 0.5387 mmol) in dichloromethane (2 mL) and trifluoroacetic acid (614.2 mg, 412.2 µL, 5.387 mmol) was stirred at room temperature for 4 h. The solvents were then evaporated. The residue was dissolved in ethyl acetate, washed with 2 mL of saturated sodium bicarbonate solution and the solvent was evaporated giving a residue which was dissolved in dimethyl sulfoxide (5 mL). 3 Å molecular sieves were added and the mixture was stirred for 10 min. Then cesium fluoride (245.5 mg, 1.616 mmol) and potassium carbonate (223.3 mg, 1.616 mmol) were added and the reaction mixture was heated at 160° C. for 24 h. The reaction mixture was filtered through a Whatman filter disc (puradisc 25 TF) and the filtrate was purified by a reverse phase HPLC-MS method using a dual gradient run from 50-90% mobile phase B over 15.0 min (Mobile phase A=water (0.05% hydrochloric acid), Mobile phase B=acetonitrile to afford 8-[3-(3,3-dicyclopropylpropoxy)-1H-pyrazol-1-yl]-12,12-dimethyl-2λ⁶-thia-3,9,11,19,21-pentaazatetracyclo[18.2.2.1 11,14.0 5,10]pentacosa-1(22),5,7,9,20,23-hexaene-2,2,4-trione (Compound 130) (52 mg, 15%) as a white solid. ¹H NMR (400 MHz, Chloroform-d) δ 8.65 (s, 1H), 8.18 (d, J=2.8 Hz, 1H), 7.76 (d, J=8.4 Hz, 1H), 7.01 (d, J=8.3 Hz, 1H), 6.52 (d, J=9.1 Hz, 1H), 5.89 (d, J=2.8 Hz, 1H), 5.24 (s, 1H), 4.41 (t, J=6.8 Hz, 2H), 3.36 (s, 1H), 2.69 (s, 1H), 2.23 (s, 1H), 2.06 (brs, 1H), 1.97 (q, J=6.8 Hz, 2H), 1.78-1.71 (m, 3H), 1.66 (brs, 1H), 1.63 (brs, 1H), 1.60 (s, 3H), 1.58 (s, 3H), 1.20 (brs, 2H), 1.00 (brs, 2H), 0.66 (tq, J=8.7, 5.0, 4.3 Hz, 2H), 0.50-0.38 (m, 4H), 0.32 (dd, J=9.0, 6.9 Hz, 1H), 0.23-0.17 (m, 2H), 0.11 (m, 2H). ESI-MS m/z calc. 633.30975, found 634.22 (M+1)⁺; Retention time: 1.66 min (LC Method B).

Example 34: Preparation of 8-[3-(3,3-dicyclopropylpropoxy)-1H-pyrazol-1-yl]-12,12-dimethyl-2λ⁶-thia-3,9,11,19,24-pentaazatetracyclo[18.3.1.0 5,10.0 11,15]tetracosa-1(23),5(10),6,8,20(24),21-hexaene-2,2,4-trione (Compound 131)

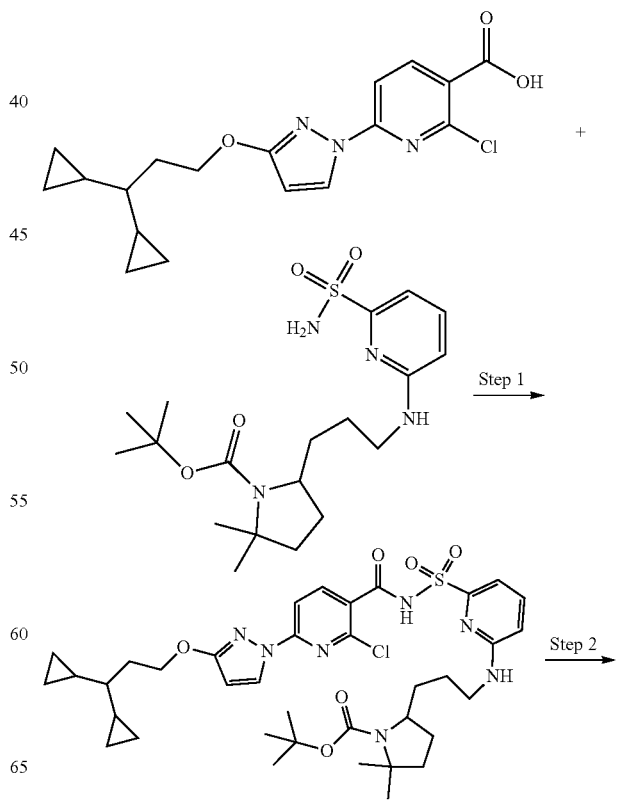

-continued

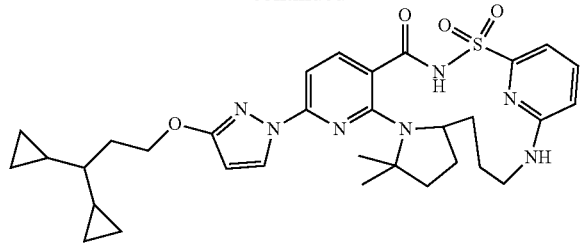

Step 1: tert-Butyl 5-[3-[[6-[[2-chloro-6-[3-(3,3-dicyclopropylpropoxy) pyrazol-1-yl]pyridine-3-carbonyl]sulfamoyl]-2-pyridyl]amino]propyl]-2,2-dimethyl-pyrrolidine-1-carboxylate

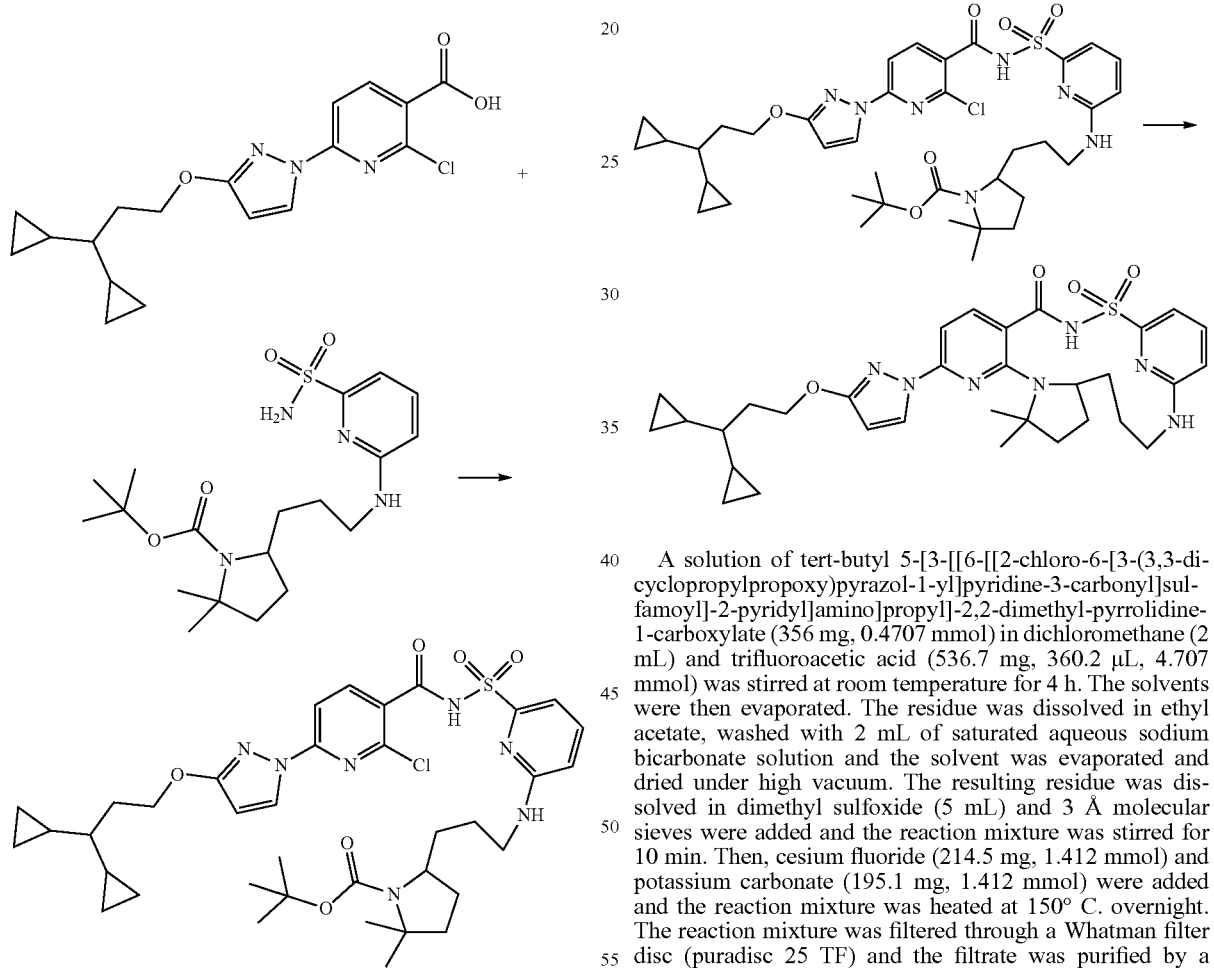

2-Chloro-6-[3-(3,3-dicyclopropylpropoxy)pyrazol-1-yl]pyridine-3-carboxylic acid (300 mg, 0.8291 mmol) and di(imidazol-1-yl)methanone (117.9 mg, 0.7272 mmol) were combined in tetrahydrofuran (2.5 mL) and stirred at room temperature for 16 h. Then, tert-butyl 2,2-dimethyl-5-[3-[(6-sulfamoyl-2-pyridyl)amino]propyl]pyrrolidine-1-carboxylate (250.0 mg, 0.6060 mmol) and 1,8-diazabicyclo[5.4.0]undec-7-ene (138.4 mg, 136.0 µL, 0.9090 mmol) were added and the reaction was stirred at room temperature for 4 h. The reaction was diluted with ethyl acetate and washed with saturated ammonium chloride solution followed by brine. The organics were separated, dried over sodium sulfate, filtered and evaporated. The resultant brown residue was purified by silica gel chromatography using a gradient from 100% dichloromethane to 20% methanol in dichloromethane to afford tert-butyl 5-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate (356 mg, 78%) as a white solid. ESI-MS m/z calc. 755.3232, found 756.5 (M+1)$^+$; Retention time: 0.63 min (LC Method A).

Step 2: 8-[3-(3,3-Dicyclopropylpropoxy)-1H-pyrazol-1-yl]-12,12-dimethyl-2$\lambda^6$-thia-3,9,11,19,24-pentaazatetracyclo[18.3.1.0$^{5,10}$.0$^{11,15}$]tetracosa-1(23),5(10),6,8,20(24),21-hexaene-2,2,4-trione (Compound 131)

A solution of tert-butyl 5-[3-[[6-[[2-chloro-6-[3-(3,3-dicyclopropylpropoxy)pyrazol-1-yl]pyridine-3-carbonyl]sulfamoyl]-2-pyridyl]amino]propyl]-2,2-dimethyl-pyrrolidine-1-carboxylate (356 mg, 0.4707 mmol) in dichloromethane (2 mL) and trifluoroacetic acid (536.7 mg, 360.2 µL, 4.707 mmol) was stirred at room temperature for 4 h. The solvents were then evaporated. The residue was dissolved in ethyl acetate, washed with 2 mL of saturated aqueous sodium bicarbonate solution and the solvent was evaporated and dried under high vacuum. The resulting residue was dissolved in dimethyl sulfoxide (5 mL) and 3 Å molecular sieves were added and the reaction mixture was stirred for 10 min. Then, cesium fluoride (214.5 mg, 1.412 mmol) and potassium carbonate (195.1 mg, 1.412 mmol) were added and the reaction mixture was heated at 150° C. overnight. The reaction mixture was filtered through a Whatman filter disc (puradisc 25 TF) and the filtrate was purified by a reverse phase HPLC-MS method using a dual gradient run from 50-90% mobile phase B over 15.0 min (mobile phase A=water (0.05% hydrochloric acid), mobile phase B=acetonitrile) to afford 8-[3-(3,3-dicyclopropylpropoxy)-1H-pyrazol-1-yl]-12,12-dimethyl-2$\lambda^6$-thia-3,9,11,19,24-pentaazatetracyclo[18.3.1.0$^{5,10}$.0$^{11,15}$]tetracosa-1(23),5(10),6,8,20(24),21-hexaene-2,2,4-trione (Compound 131) (115 mg, 39%) as a white solid. $^1$H NMR (400 MHz, Chloroform-d) δ (s, 1H), 8.47 (d, J=8.6 Hz, 1H), 8.26-8.06 (m, 1H), 7.66 (d, J=15.1 Hz, 1H), 7.51-7.40 (m, 2H), 6.45 (d, J=7.8 Hz, 1H), 5.95 (d, J=2.8 Hz, 1H), 4.82 (s, 1H), 4.43 (t, J=6.8 Hz, 2H), 4.16 (d, J=72.4 Hz, 1H), 3.34 (s, 1H), 3.09 (s, 1H), 2.38 (d, J=8.4 Hz, 2H), 1.97 (q, J=6.8 Hz, 2H), 1.65

(d, J=42.4 Hz, 8H), 1.15 (s, 2H), 0.95 (s, 1H), 0.66 (qt, J=8.3, 5.0 Hz, 2H), 0.53-0.37 (m, 4H), 0.32 (tt, J=9.0, 6.8 Hz, 1H), 0.23-0.16 (m, 2H), 0.09 (dtd, J=9.0, 4.9, 3.4 Hz, 2H). ESI-MS m/z calc. 619.29407, found 620.17 (M+1)+; Retention time: 1.61 min (LC Method B).

Example 35: Preparation of 12,12,19-trimethyl-8-(3-{2-[1-(trifluoromethyl)cyclopropyl]ethoxy}-1H-pyrazol-1-yl)-2λ⁶-thia-3,9,11,19,21-pentaazatetracyclo[18.2.2.1¹¹,¹⁴.0⁵,¹⁰]pentacosa-1(23),5,7,9,20(24),21-hexaene-2,2,4-trione (Compound 132)

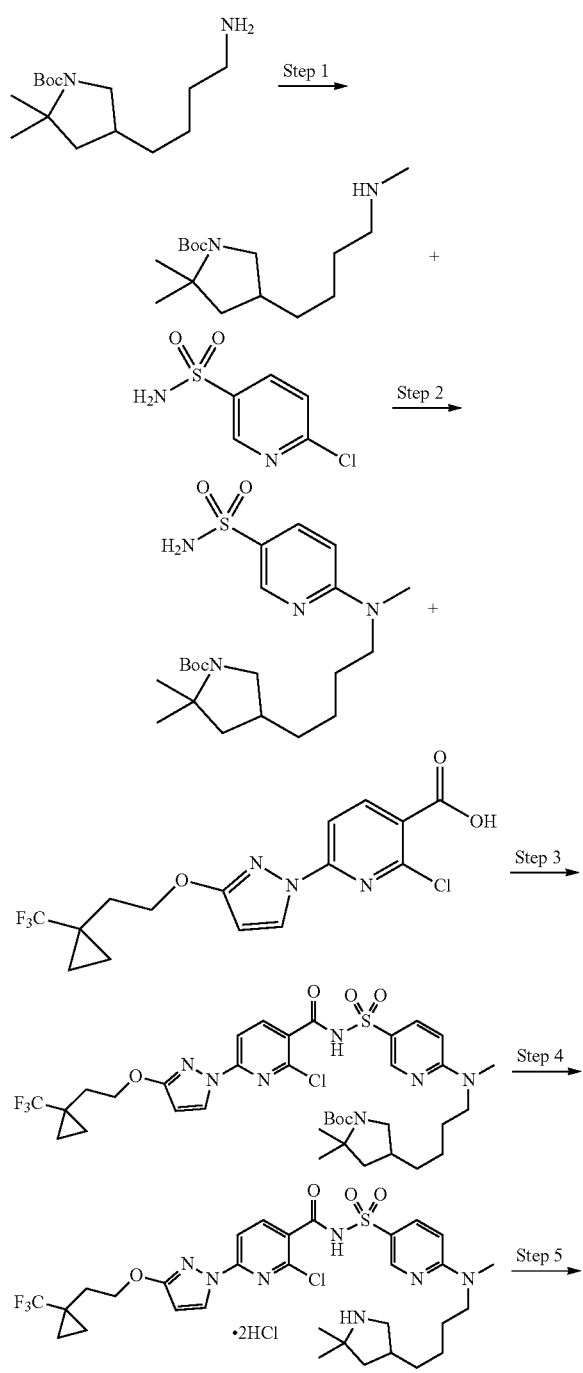

Step 1: tert-Butyl 2,2-dimethyl-4-[4-(methylamino)butyl]pyrrolidine-1-carboxylate

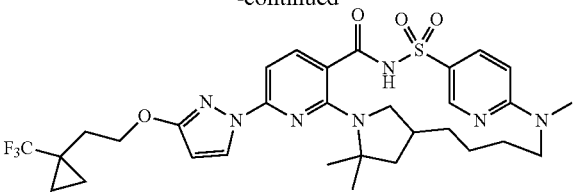

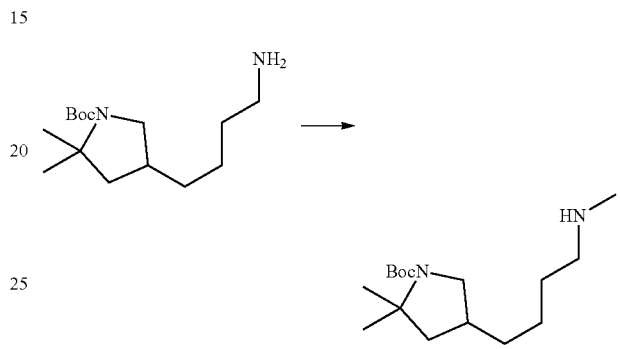

To a 50 mL round bottom flask charged with tert-butyl 4-(4-aminobutyl)-2,2-dimethyl-pyrrolidine-1-carboxylate (850 mg, 3.143 mmol) in dichloromethane (15 mL) was added acetic anhydride (400 μL, 4.239 mmol) followed by triethylamine (1000 μL, 7.175 mmol). The vessel was capped and the reaction mixture stirred at room temperature for 45 min. The reaction was quenched with saturated aqueous sodium carbonate (~10 mL) and extracted with dichloromethane (3×~15 mL). The combined organic extracts were washed with saturated aqueous sodium carbonate (2×~10 mL), dried over sodium sulfate, filtered and concentrated in vacuo affording a clear oil which was charged to a 100 mL round bottom flask and N,N-dimethylformamide (15 mL) was added followed by sodium hydride (200 mg of 60% w/w, 5.000 mmol) and the reaction mixture was stirred for 30 min at room temperature. Iodomethane (800 μL, 12.85 mmol) was added, the vessel capped and the reaction mixture stirred at 50° C. for 48 h. After cooling to room temperature, the reaction was quenched with water (~15 mL). The crude mixture was extracted with dichloromethane (3×25 mL) and the combined organic extracts were dried over sodium sulfate, filtered and concentrated in vacuo. The crude reaction mixture was purified via silica gel column chromatography (0%-30% ethyl acetate in hexanes gradient) giving a yellow oil which was charged to a 100 mL round bottom flask and methanol (30 mL) and potassium hydroxide (1.5 g, 26.74 mmol) were added. The flask was fitted with a reflux condenser and the reaction mixture was stirred at 80° C. for 96 h. After cooling to room temperature, the solvent was removed in vacuo and the residue was dissolved in ethyl acetate (~70 mL) and water (~30 mL). The layers were separated and the aqueous layer extracted with ethyl acetate (3×20 mL). The combined organic extracts were washed with water (2×25 mL), dried over sodium sulfate, filtered and concentrated in vacuo affording crude tert-butyl 2,2-dimethyl-4-[4-(methylamino)butyl]pyrrolidine-1-carboxylate (873 mg, 98%) as an orange/yellow oil, which was used without further purification. ESI-MS m/z calc. 284.24637, found 285.2 (M+1)⁺; Retention time: 1.19 min (LC Method B).

Step 2: tert-Butyl 2,2-dimethyl-4-[4-[methyl-(5-sulfamoyl-2-pyridyl)amino]butyl]pyrrolidine-1-carboxylate

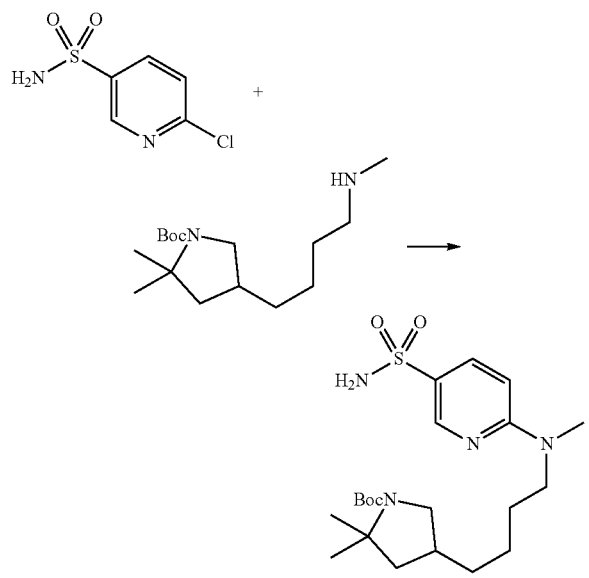

To a 20 mL vial charged with tert-butyl 2,2-dimethyl-4-[4-(methylamino)butyl]pyrrolidine-1-carboxylate (350 mg, 1.230 mmol) was added 6-chloropyridine-3-sulfonamide (249 mg, 1.293 mmol), potassium carbonate (250 mg, 1.809 mmol) and dimethyl sulfoxide (4 mL). The headspace was purged with nitrogen, the vial capped and the reaction mixture was stirred at 120° C. for 18 h. After 18 h, the reaction was cooled to room temperature and diluted with ethyl acetate (~40 mL). The crude mixture was washed with water (10 mL) and brine (5 mL) and the organic layer was dried over sodium sulfate, filtered and concentrated in vacuo. The crude reaction mixture was purified via silica gel column chromatography (0%-100% ethyl acetate in hexanes gradient) to afford tert-butyl 2,2-dimethyl-4-[4-[methyl-(5-sulfamoyl-2-pyridyl)amino]butyl]pyrrolidine-1-carboxylate (143 mg, 26%) as an off-white solid. ESI-MS m/z calc. 440.24573, found 441.2 (M+1)⁺; Retention time: 1.6 min (LC Method B).

Step 3: tert-Butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]butyl]-2,2-dimethyl-pyrrolidine-1-carboxylate

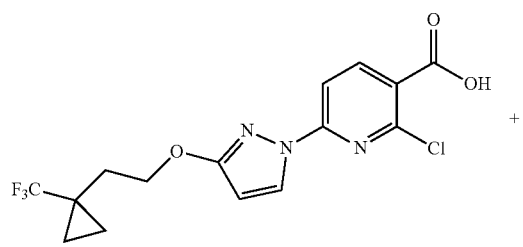

-continued

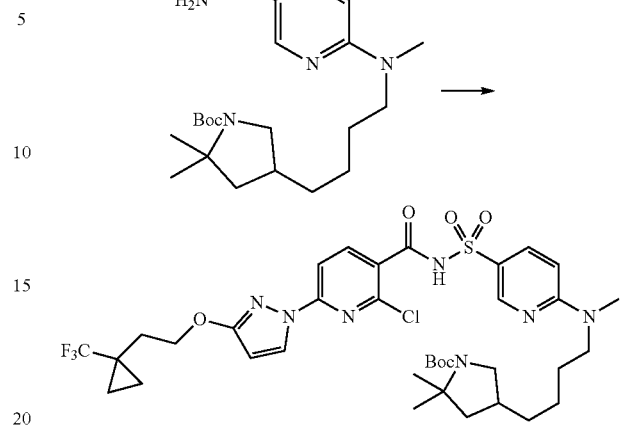

To a 20 mL vial charged with 2-chloro-6-[3-[2-[1-(trifluoromethyl)cyclopropyl]ethoxy]pyrazol-1-yl]pyridine-3-carboxylic acid (136 mg, 0.3620 mmol) was added carbonyl diimidazole (59 mg, 0.3639 mmol) and tetrahydrofuran (2 mL). The vial was capped and the reaction mixture stirred at room temperature for 2 h. At this point, tert-butyl 2,2-dimethyl-4-[4-[methyl-(5-sulfamoyl-2-pyridyl)amino]butyl]pyrrolidine-1-carboxylate (143 mg, 0.3246 mmol) in tetrahydrofuran (2 mL) was added followed by 1,8-diazabicyclo[5.4.0]undec-7-ene (75 µL, 0.5015 mmol). The reaction mixture was stirred at room temperature for 18 h. The reaction was then quenched with water (~4 mL) and 1 M aqueous citric acid (~4 mL) and the crude mixture was extracted with ethyl acetate (3×10 mL). The combined organic extracts were dried over magnesium sulfate, filtered and concentrated in vacuo. The residue was purified via silica gel column chromatography (0%-100% ethyl acetate in hexanes gradient) to afford tert-butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]butyl]-2,2-dimethyl-pyrrolidine-1-carboxylate (167 mg, 64%) as an off-white solid. ESI-MS m/z calc. 797.2949, found 798.4 (M+1)⁺; Retention time: 2.35 min (LC Method B).

Step 4: 2-Chloro-N-[[6-[4-(5,5-dimethylpyrrolidin-3-yl)butyl-methyl-amino]-3-pyridyl]sulfonyl]-6-[3-[2-[1-(trifluoromethyl)cyclopropyl]ethoxy]pyrazol-1-yl]pyridine-3-carboxamide (Dihydrochloride Salt)

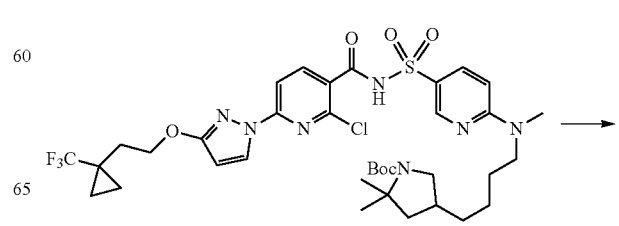

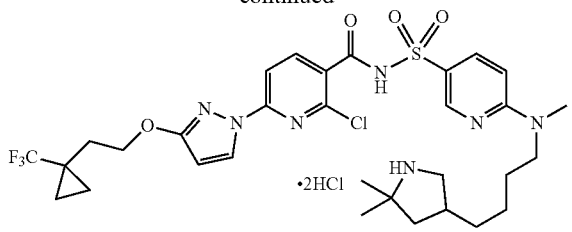

To a 20 mL vial charged with tert-butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]butyl]-2,2-dimethyl-pyrrolidine-1-carboxylate (167 mg, 0.2092 mmol) was added CH$_2$Cl$_2$ (5 mL) and hydrochloric acid (1 mL of 4.0 M, 4.000 mmol) in dioxane. The vial was sealed and the reaction mixture stirred at room temperature for 2 h. The solvent was removed in vacuo affording crude 2-chloro-N-[[6-[4-(5,5-dimethylpyrrolidin-3-yl)butyl-methyl-amino]-3-pyridyl]sulfonyl]-6-[3-[2-[1-(trifluoromethyl)cyclopropyl]ethoxy]pyrazol-1-yl]pyridine-3-carboxamide (dihydrochloride salt) (147 mg, 91%) as a pale yellow solid which was used without further purification. ESI-MS m/z calc. 697.2425, found 698.4 (M+1)$^+$; Retention time: 1.69 min (LC Method B).

Step 5: 12,12,19-Trimethyl-8-(3-{2-[1-(trifluoromethyl)cyclopropyl]ethoxy}-1H-pyrazol-1-yl)-2λ$^6$-thia-3,9,11,19,21-pentaazatetracyclo[18.2.2.1$^{11,14}$.0$^{5,10}$]pentacosa-1(23),5,7,9,20(24),21-hexaene-2,2,4-trione (Compound 132)

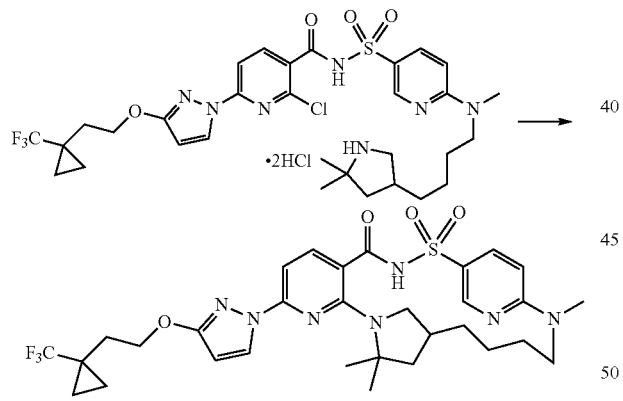

To a 20 mL vial charged with 2-chloro-N-[[6-[4-(5,5-dimethylpyrrolidin-3-yl)butyl-methyl-amino]-3-pyridyl]sulfonyl]-6-[3-[2-[1-(trifluoromethyl)cyclopropyl]ethoxy]pyrazol-1-yl]pyridine-3-carboxamide (dihydrochloride salt) (147 mg, 0.2105 mmol) was added potassium carbonate (152 mg, 1.100 mmol), CsF (96 mg, 0.6320 mmol) and dimethyl sulfoxide (5 mL). The headspace was purged with nitrogen, the vial sealed, and the reaction mixture stirred at 150° C. for 18 h. After cooling to room temperature, the solids were filtered off with ethyl acetate eluent, the crude mixture diluted with ethyl acetate (~35 mL), washed with 1.0 M aqueous citric acid (2×5 mL), brine (5 mL), the organic layer dried over sodium sulfate, filtered and concentrated in vacuo. Column chromatography (silica, gradient from 0% to 5% methanol in dichloromethane) afforded 12,12,19-trimethyl-8-(3-{2-[1-(trifluoromethyl)cyclopropyl]ethoxy}-1H-pyrazol-1-yl)-2λ$^6$-thia-3,9,11,19,21-pentaazatetracyclo[18.2.2.1$^{11,14}$.0$^{5,10}$]pentacosa-1(23),5,7,9,20(24),21-hexaene-2,2,4-trione (dihydrochloride salt) (Compound 132) (64 mg, 39%) as an off-white solid. $^1$H NMR (400 MHz, dimethyl sulfoxide-d$_6$) δ 12.19 (s, 1H), 8.18 (d, J=2.8 Hz, 1H), 7.81 (d, J=8.3 Hz, 1H), 6.90 (d, J=8.3 Hz, 1H), 6.81 (s, 1H), 6.10 (d, J=2.7 Hz, 1H), 4.31 (t, J=7.0 Hz, 2H), 2.98 (d, J=7.8 Hz, 3H), 2.37 (s, 1H), 2.07 (t, J=7.1 Hz, 4H), 1.78-1.68 (m, 1H), 1.52 (s, 8H), 1.39 (d, J=51.3 Hz, 2H), 1.27-1.05 (m, 2H), 1.04-0.75 (m, 6H). ESI-MS m/z calc. 661.2658, found 662.4 (M+1)$^+$; Retention time: 1.84 min (LC Method B).

Example 36: Preparation of 12,12,18-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 133)

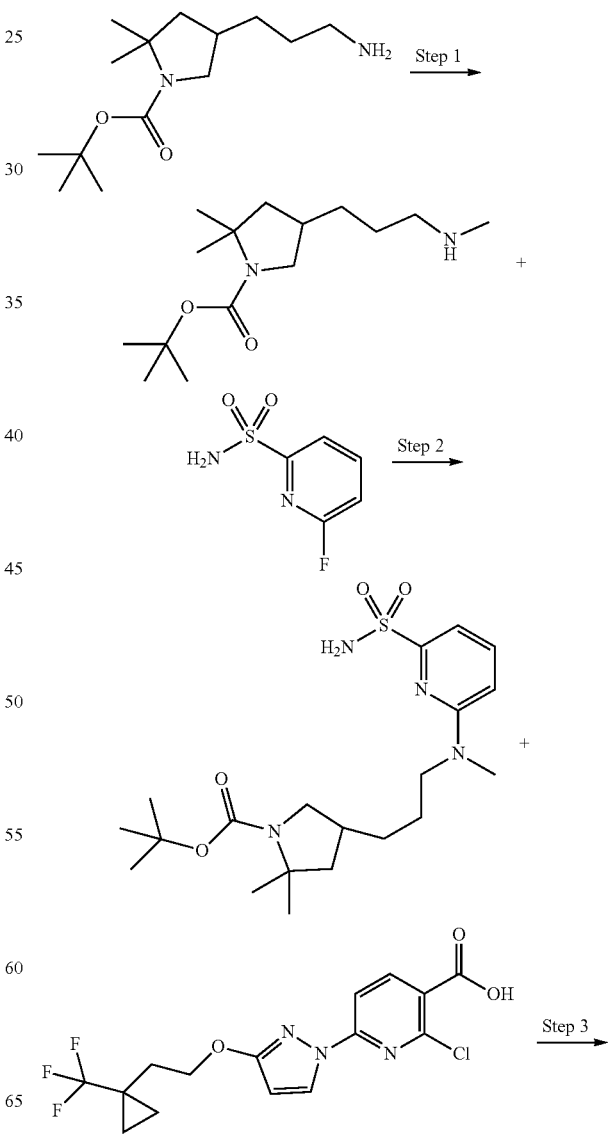

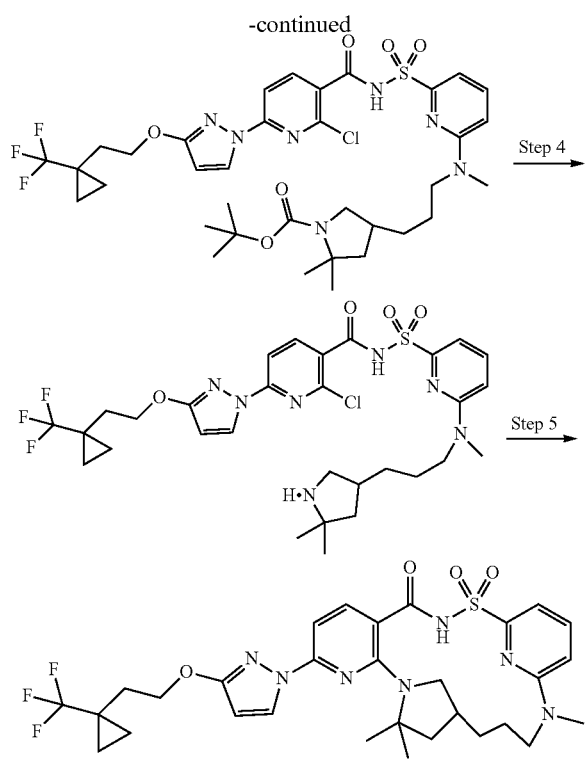

Step 1: tert-Butyl 2,2-dimethyl-4-[3-(methylamino)propyl]pyrrolidine-1-carboxylate

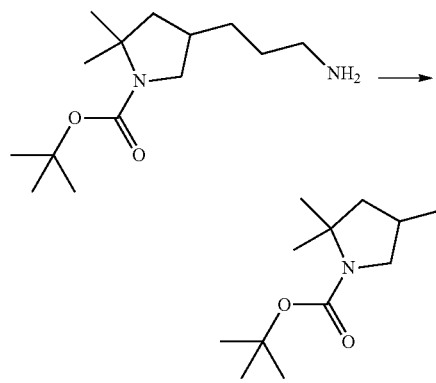

To a 50 ml flask charged with tert-butyl 4-(3-aminopropyl)-2,2-dimethyl-pyrrolidine-1-carboxylate (869 mg, 3.389 mmol) in dichloromethane (15 mL) was added acetic anhydride (527.3 mg, 487.3 μL, 5.165 mmol), followed by Et₃N (884.8 mg, 1.219 mL, 8.744 mmol). The vessel was capped and the reaction mixture stirred at room temperature for 45 min then quenched with saturated aqueous sodium carbonate (10 mL) and extracted with dichloromethane (3×15 mL). The combined organic extracts were washed with saturated aqueous sodium carbonate (2×10 mL), dried over sodium sulfate, filtered and concentrated in vacuo affording the crude acetate which was combined with N,N-dimethylformamide (15 mL), followed by addition of NaH (225 mg of 60% w/w, 5.626 mmol) and the reaction mixture stirred for 30 mi at room temperature. Iodomethane (1000 μL, 16.06 mmol) was added, the vessel capped and the reaction mixture stirred at 50° C. for 48 h. After cooling to room temperature, the reaction was quenched with water (~15 mL) and the crude mixture was extracted with dichloromethane (3×25 mL). The combined organic extracts dried over sodium sulfate, filtered and concentrated in vacuo. Column chromatography (silica gel, 0% to 30% ethyl acetate in hexanes) afforded the methylated intermediate acetate to which was added methanol (30 mL) and KOH (1.5 g, 26.74 mmol). The flask was fitted with a reflux condenser, and the reaction mixture stirred at 80° C. for 96 h. After cooling to room temperature, the solvent was removed in vacuo and the residue was dissolved in ethyl acetate (~70 mL) and water (~30 mL). The layers were separated and the aqueous layer extracted with ethyl acetate (3×20 mL). The combined organic extracts were washed with water (2×25 mL), dried over sodium sulfate, filtered and concentrated in vacuo affording tert-butyl 2,2-dimethyl-4-[3-(methylamino)propyl]pyrrolidine-1-carboxylate (889 mg, 97%) as an orange/yellow oil which was used without further purification. ESI-MS m/z calc. 270.23074, found 271.2 (M+1)⁺; Retention time: 1.1 min (LC Method B).

Step 2: tert-Butyl 2,2-dimethyl-4-[3-[methyl-(6-sulfamoyl-2-pyridyl)amino]propyl]pyrrolidine-1-carboxylate

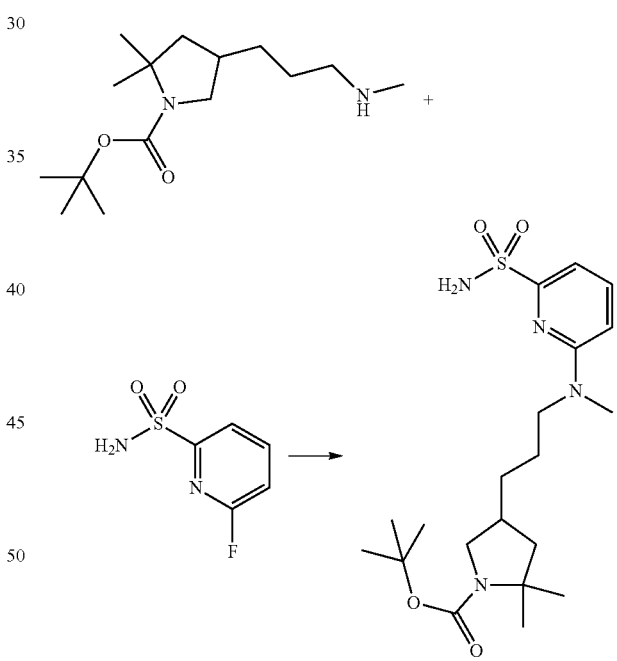

To a solution of tert-butyl 2,2-dimethyl-4-[3-(methylamino)propyl]pyrrolidine-1-carboxylate (154 mg, 0.5695 mmol) in dimethyl sulfoxide (2 mL) was added 6-fluoropyridine-2-sulfonamide (103 mg, 0.5847 mmol) followed by diisopropylethylamine (500 μL, 2.871 mmol). The flask was capped with a septum and heated at 90° C. under nitrogen balloon in an oil bath for 14 h. The reaction mixture was cooled to room temperature then diluted with ethyl acetate and washed with brine solution. The organics were separated, dried over sodium sulfate, filtered and evaporated and then purified by silica gel chromatography (80 gram column) using a gradient system from 100% hexanes to 100% ethyl acetate to afford tert-butyl 2,2-dimethyl-4-[3-[methyl-(6-sulfamoyl-2-pyridyl)amino]propyl]pyrrolidine-1-carboxylate (141 mg, 58%) as white solid. $^1$H NMR (400 MHz, dimethyl sulfoxide-d$_6$) δ 7.65 (dd, J=8.6, 7.2 Hz, 1H), 7.12 (s, 2H), 7.01 (d, J=7.2 Hz, 1H), 6.78 (d, J=8.7 Hz, 1H), 3.53 (q, J=7.8, 7.4 Hz, 3H), 3.17 (d, J=3.6 Hz, 1H), 3.04 (s, 3H), 2.84-2.72 (m, 1H), 2.09 (d, J=9.5 Hz, 1H), 1.88 (td, J=12.8, 5.7 Hz, 1H), 1.53 (dt, J=14.6, 7.4 Hz, 2H), 1.36 (dd, J=15.0, 10.6 Hz, 14H), 1.23 (s, 3H). ESI-MS m/z calc. 426.23007, found 427.3 (M+1)$^+$; Retention time: 0.47 min (LC Method A).

Step 3: tert-Butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]propyl]-2,2-dimethyl-pyrrolidine-1-carboxylate acetate (25 mL) and washed with saturated aqueous ammonium chloride (25 mL) followed by brine (25 mL). The organic layer was separated, dried over sodium sulfate, filtered and evaporated. The crude material was then purified by silica gel chromatography using a shallow gradient from 100% dichloromethane to 20% methanol in dichloromethane. The product (still contaminated with 7% SM) was dissolved in ethyl acetate (50 mL) and washed with saturated aqueous sodium bicarbonate (2×50 mL), dried over sodium sulfate, filtered and concentrated to give tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]propyl]-2,2-dimethyl-pyrrolidine-1-carboxylate (141 mg, 55%, 93% purity) as a light yellow solid. $^1$H NMR (400 MHz, dimethyl sulfoxide-d$_6$) δ 8.40 (q, J=4.2, 3.6 Hz, 1H), 8.16-8.06 (m, 1H), 7.79-7.67 (m, 2H), 7.22 (d, J=7.3 Hz, 1H), 6.92 (d, J=8.7 Hz, 1H), 6.22-6.14 (m, 1H), 4.35 (t, J=7.0 Hz, 2H), 3.49 (dd, J=32.6, 9.1 Hz, 3H), 3.03 (s, 3H), 2.71 (t, J=10.5 Hz, 1H), 2.10 (q, J=7.3 Hz, 3H), 2.00 (s, 2H), 1.85-1.66 (m, 1H), 1.50 (q, J=7.7 Hz, 1H), 1.43-1.31 (m, 9H), 1.27 (t, J=10.5 Hz, 4H), 1.05-0.82 (m, 5H). ESI-MS m/z calc. 783.27924, found 784.42 (M+1)$^+$; Retention time: 2.52 min (LC Method B).

Step 4: 2-Chloro-N-[[6-[3-(5,5-dimethylpyrrolidin-3-yl)propyl-methyl-amino]-2-pyridyl]sulfonyl]-6-[3-[2-[1-(trifluoromethyl)cyclopropyl]ethoxy]pyrazol-1-yl]pyridine-3-carboxamide

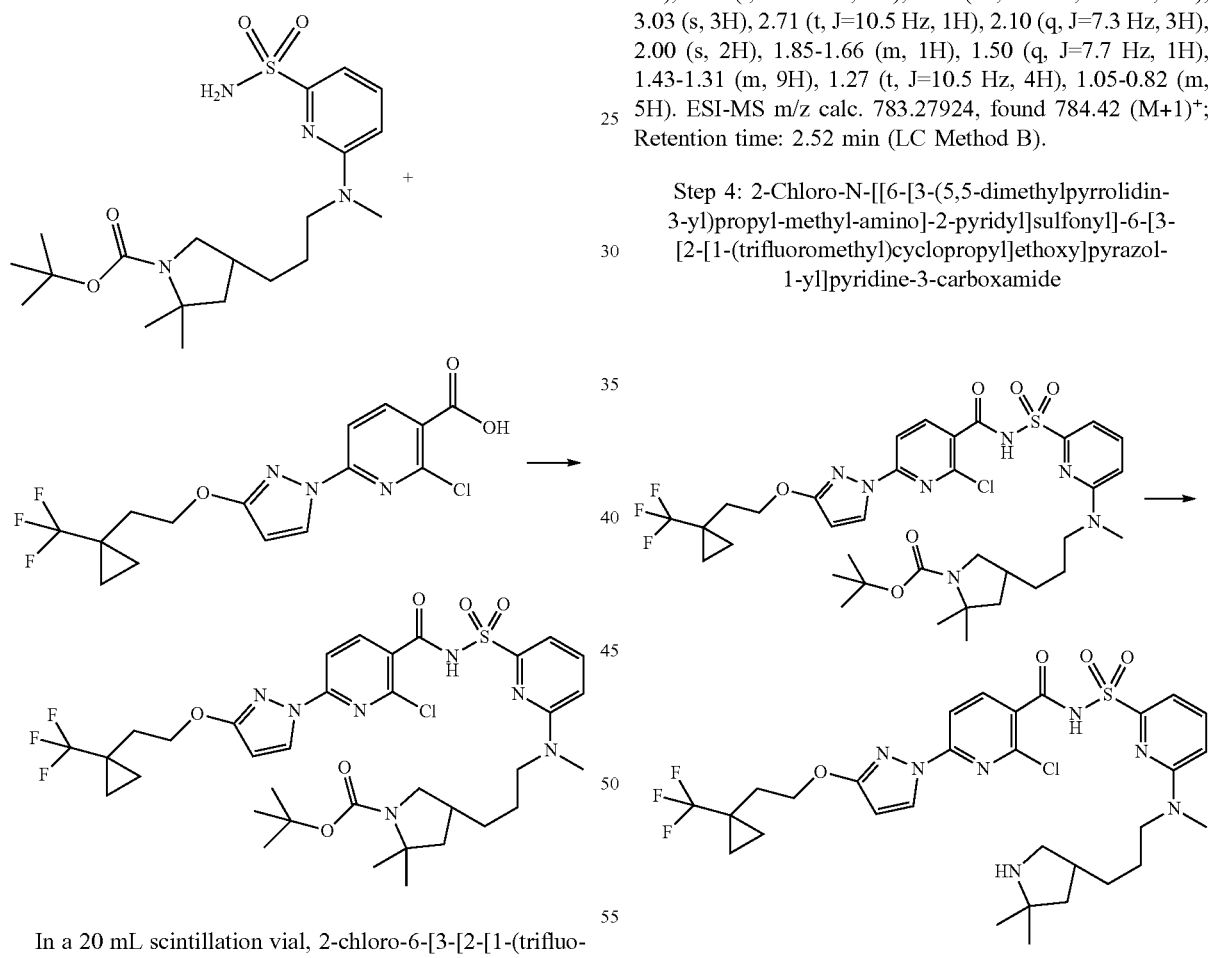

In a 20 mL scintillation vial, 2-chloro-6-[3-[2-[1-(trifluoromethyl) cyclopropyl]ethoxy]pyrazol-1-yl]pyridine-3-carboxylic acid (264 mg, 0.7026 mmol) and carbonyl diimidazole (114 mg, 0.7031 mmol) were combined in tetrahydrofuran (2.2 mL) and stirred for 120 min at 50° C. with a loose cap. Then, tert-butyl 2,2-dimethyl-4-[3-[methyl-(6-sulfamoyl-2-pyridyl)amino]propyl]pyrrolidine-1-carboxylate (130 mg, 0.3048 mmol) in tetrahydrofuran (3 mL) was added followed by 1,8-diazabicyclo[5.4.0]undec-7-ene (92.80 mg, 91.16 µL, 0.6096 mmol). The reaction was heated at 50° C. for 16 h. The reaction was diluted with ethyl To a solution of tert-butyl 4-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]propyl]-2,2-dimethyl-pyrrolidine-1-carboxylate (141 mg, 0.168 mmol, 93% purity) in dichloromethane (2 mL) was added trifluoroacetic acid (1.390 g, 939.2 µL, 12.19 mmol). The reaction was stirred at room temp for 2 h and the mixture was then concentrated to dryness. The crude was treated with saturated sodium bicarbonate and then extracted with dichloromethane. The organic layer was dried over sodium sulfate, filtered and concentrated under reduced pressure to give 2-chloro-N-[[6-[3-(5,5-dimethylpyrrolidin-3-yl)propyl-methyl-amino]-2-pyridyl]sulfonyl]-6-[3-[2-[1-(trifluoromethyl)cyclopropyl]ethoxy]pyrazol-1-yl]pyridine-3-carboxamide (100 mg, 48%). ESI-MS m/z calc. 683.2268, found 684.32 (M+1)+; Retention time: 1.72 min (LC Method B).

Step 5: 12,12,18-Trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 133)

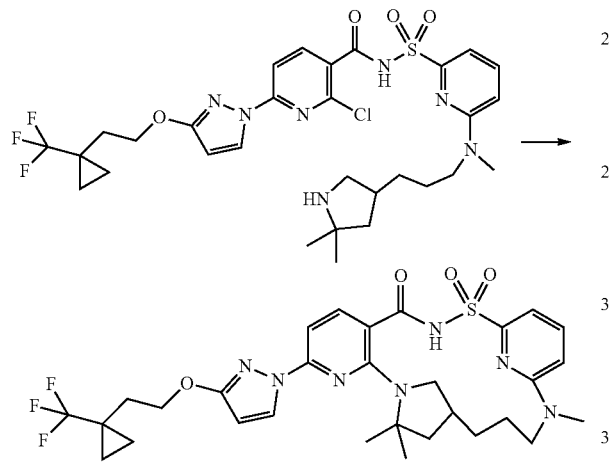

A mixture of 2-chloro-N-[[6-[3-(5,5-dimethylpyrrolidin-3-yl)propyl-methyl-amino]-2-pyridyl]sulfonyl]-6-[3-[2-[1-(trifluoromethyl)cyclopropyl]ethoxy]pyrazol-1-yl]pyridine-3-carboxamide (83 mg, 0.1213 mmol), potassium carbonate (100 mg, 0.7236 mmol), cesium fluoride (22 mg, 0.1448 mmol) and a small amount of 3 Å molecular sieves in dimethyl sulfoxide (4 mL) was capped and heated to 165° C. for 4 h. The mixture was then cooled to room temperature, diluted with ethyl acetate and washed with saturated aqueous ammonium chloride and brine. The organic phase was dried (sodium sulfate), filtered and concentrated to an orange oil which was purified by silica chromatography with a shallow gradient from 100% dichloromethane to 20% methanol in dichloromethane to give 12,12,18-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 133) (32.9 mg, 42%) as a white solid. $^1$H NMR (400 MHz, dimethyl sulfoxide-d$_6$) δ 8.22 (d, J=2.8 Hz, 1H), 7.78 (dd, J=12.5, 8.0 Hz, 2H), 7.19 (d, J=7.3 Hz, 1H), 6.91 (t, J=8.2 Hz, 2H), 6.12 (d, J=2.7 Hz, 1H), 4.52 (s, 1H), 4.32 (t, J=7.0 Hz, 2H), 3.14 (m, 1H), 2.92 (m, 4H), 2.70 (d, J=17.7 Hz, 1H), 2.08 (m, J=7.1 Hz, 3H), 1.94-1.75 (m, 1H), 1.61 (s, 3H), 1.49 (m, J=13.1 Hz, 5H), 1.34 (m, 1H), 1.15-0.77 (m, 5H). ESI-MS m/z calc. 647.2502, found 648.1 (M+1)+; Retention time: 2.29 min (LC Method B).

Example 37: Preparation of 8-[3-(3,3-dicyclopropylpropoxy)-1H-pyrazol-1-yl]-12,12-dimethyl-2λ$^6$-thia-3,9,11,19,24-pentaazatetracyclo[18.3.1.0$^5$,10.0$^{11,15}$]tetracosa-1(23),5(10),6,8,20(24),21-hexaene-2,2,4-trione (enantiomer 1) (Compound 136) and 8-[3-(3,3-Dicyclopropylpropoxy)-1H-pyrazol-1-yl]-12,12-dimethyl-2λ$^6$-thia-3,9,11,19,24-pentaazatetracyclo[18.3.1.0$^5$,10.0$^{11,15}$]tetracosa-1(23),5(10),6,8,20(24),21-hexaene-2,2,4-trione (Enantiomer 2) (Compound 137)

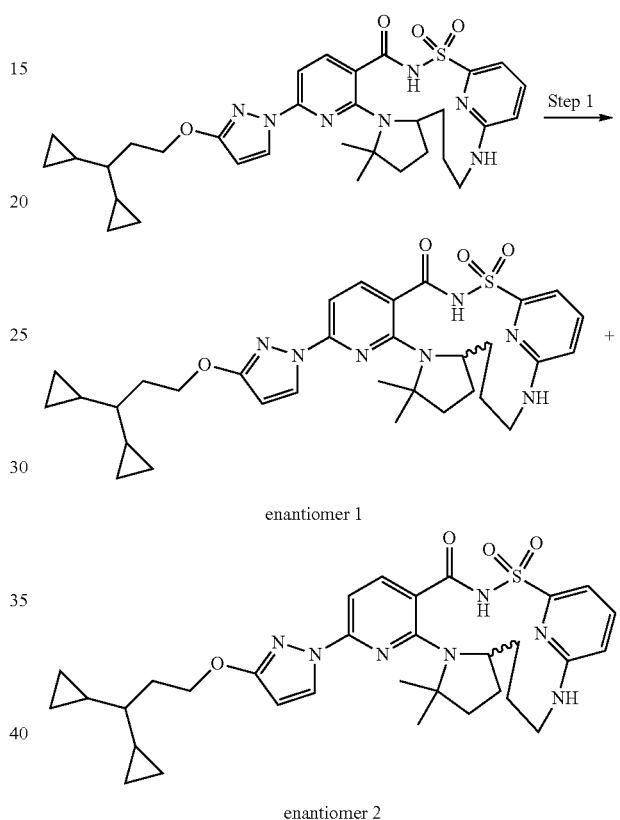

enantiomer 1 enantiomer 2

Step 1: 8-[3-(3,3-Dicyclopropylpropoxy)-1H-pyrazol-1-yl]-12,12-dimethyl-2λ$^6$-thia-3,9,11,19,24-pentaazatetracyclo[18.3.1.0$^5$,10.0$^{11,15}$]tetracosa-1(23),5(10),6,8,20(24),21-hexaene-2,2,4-trione (Enantiomer 1) (Compound 136) and 8-[3-(3,3-Dicyclopropylpropoxy)-1H-pyrazol-1-yl]-12,12-dimethyl-2λ$^6$-thia-3,9,11,19,24-pentaazatetracyclo[18.3.1.0$^5$,10.0$^{11,15}$]tetracosa-1(23),5(10),6,8,20(24),21-hexaene-2,2,4-trione (Enantiomer 2) (Compound 137)

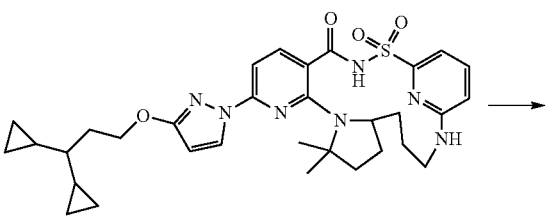

387
-continued

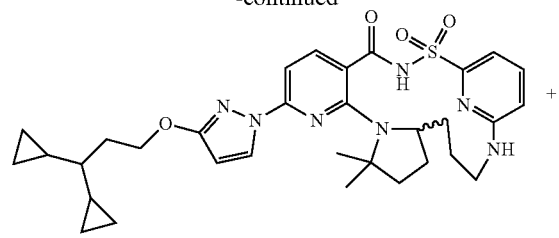

enantiomer 1 lp;2p

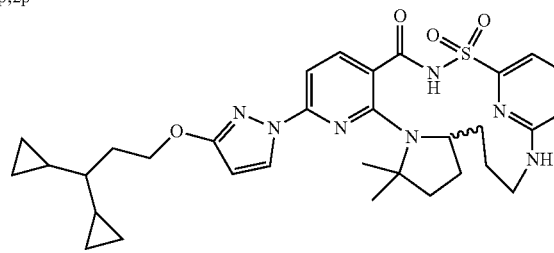

enantiomer 2

Subjected racemic 8-[3-(3,3-dicyclopropylpropoxy)-1H-pyrazol-1-yl]-12,12-dimethyl-2λ$^6$-thia-3,9,11,19,24-pentaazatetracyclo[18.3.1.0$^{5,10}$.0$^{11,15}$]tetracosa-1(23),5(10),6,8,20(24),21-hexaene-2,2,4-trione (115 mg) to chiral separation by SFC chromatography using a Phenomenex LUX-4 (250×21.2 mm) column, 5 µm particle size with 60% methanol, 40% carbon dioxide mobile phase at 70 mL/min over 8.0 min (injection volume=500 µL of ~30 mg/mL in methanol:acetonitrile:dimethyl sulfoxide (40:40:20)) giving as the first enantiomer to elute 8-[3-(3,3-dicyclopropyl-propoxy)-1H-pyrazol-1-yl]-12,12-dimethyl-2λ$^6$-thia-3,9,11,19,24-pentaazatetracyclo[18.3.1.0$^{5,10}$.0$^{11,15}$]tetracosa-1(23),5(10),6,8,20(24),21-hexaene-2,2,4-trione (enantiomer 1) (Compound 136) (34.1 mg, 29%) as a white solid; $^1$H NMR (400 MHz, Chloroform-d) δ 14.55 (s, 1H), 8.47 (d, J=8.6 Hz, 1H), 8.16 (d, J=33.0 Hz, 1H), 7.68 (s, 1H), 7.53-7.39 (m, 2H), 6.45 (d, J=7.9 Hz, 1H), 5.96 (d, J=2.8 Hz, 1H), 4.77 (s, 1H), 4.44 (t, J=6.8 Hz, 2H), 4.16 (d, J=64.7 Hz, 1H), 3.36 (s, 1H), 3.20-2.90 (m, 1H), 2.38 (d, J=8.1 Hz, 2H), 1.97 (q, J=6.8 Hz, 3H), 1.72 (s, 1H), 1.57 (br s, 4H), 1.36-1.02 (m, 3H), 1.01-0.82 (m, 2H), 0.66 (ddt, J=13.4, 8.8, 4.2 Hz, 2H), 0.52-0.38 (m, 4H), 0.37-0.29 (m, 1H), 0.23-0.16 (m, 2H), 0.10 (dt, J=9.4, 4.5 Hz, 2H), ESI-MS m/z calc. 619.29407, found 620.17 (M+1)$^+$; Retention time: 1.82 min (LC Method B) and as the second enantiomer to elute 8-[3-(3,3-dicyclopropylpropoxy)-1H-pyrazol-1-yl]-12,12-dimethyl-2λ$^6$-thia-3,9,11,19,24-pentaazatetracyclo[18.3.1.0$^{5,10}$.0$^{11,15}$]tetracosa-1(23),5(10),6,8,20(24),21-hexaene-2,2,4-trione (enantiomer 2) (Compound 137) (24.5 mg, 17%) as a white solid; $^1$H NMR (400 MHz, Chloroform-d) δ 14.55 (s, 1H), 8.47 (d, J=8.6 Hz, 1H), 8.16 (d, J=32.4 Hz, 1H), 7.68 (s, 1H), 7.52-7.40 (m, 2H), 6.45 (d, J=8.0 Hz, 1H), 5.96 (d, J=2.8 Hz, 1H), 4.77 (s, 1H), 4.44 (t, J=6.8 Hz, 2H), 4.16 (d, J=70.4 Hz, 1H), 3.49 (s, 1H), 3.03 (d, J=51.3 Hz, 1H), 1.97 (q, J=6.8 Hz, 2H), 1.72 (s, 2H), 1.56 (s, 4H), 1.27 (d, J=15.3 Hz, 5H), 1.02-0.85 (m, 2H), 0.66 (ddt, J=13.4, 8.6, 4.2 Hz, 2H), 0.51-0.38 (m, 4H), 0.36-0.27 (m, 1H), 0.25-0.15 (m, 2H), 0.15-0.05 (m, 2H), ESI-MS m/z calc. 619.29407, found 620.17 (M+1)$^+$; Retention time: 1.82 min (LC Method B).

Example 38: Preparation of (14S)-8-[3-(4,4-dimethylpentyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer 1) (Compound 145) and (14S)-8-[3-(4,4-dimethylpentyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer 2) (Compound 146)

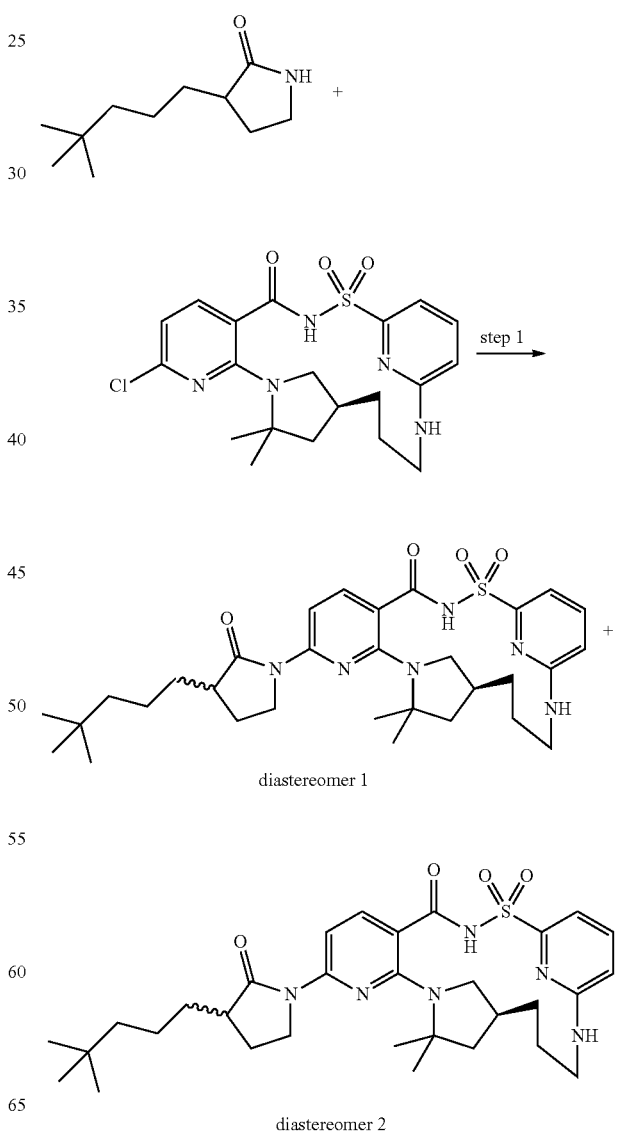

Step 1: (14S)-8-[3-(4,4-Dimethylpentyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 145) and (14S)-8-[3-(4,4-dimethylpentyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 146)

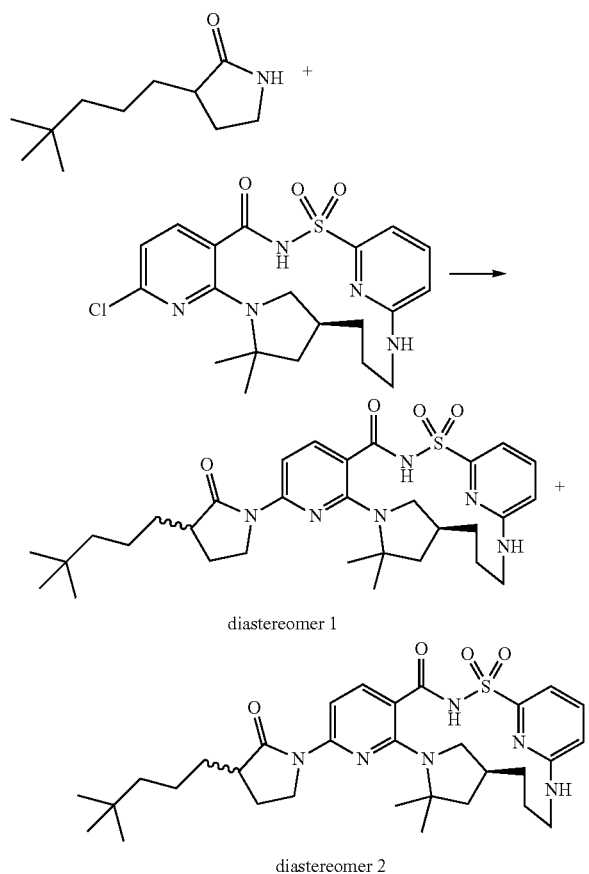

diastereomer 1 diastereomer 2

A 4 mL vial was charged with (14S)-8-chloro-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (148 mg, 0.3181 mmol), 3-(4,4-dimethylpentyl)pyrrolidin-2-one (86 mg, 0.4692 mmol), Pd₂(dba)₃ (92 mg, 0.1005 mmol), Xantphos (58 mg, 0.1002 mmol), cesium carbonate (623 mg, 1.912 mmol) and anhydrous dioxane (3 mL). The mixture was sparged with nitrogen for 2 min, capped and stirred at 120° C. for 21 h. After cooling to room temperature, the solids were filtered off and washed with ethyl acetate and the resulting filtrate concentrated in vacuo. The crude reaction mixture was purified via silica gel column chromatography (0%-5% methanol in dichloromethane gradient) to afford 54 mg of product as a mixture of diastereomers, an off-white solid. The mixture of diastereomers was purified by chiral SFC using a ChiralCel OJ-H (250×10 mm column, 5 μm particle size) with 18% acetonitrile/methanol (90:10; no modifier)/82% carbon dioxide mobile phase at 10 mL/min over 10.0 min (injection volume=70 μL of 24 mg/mL solution in methanol:dimethyl sulfoxide (90:10)) giving as the first diastereomer to elute, (14S)-8-[3-(4,4-dimethylpentyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 1) (Compound 145) (19 mg, 10%); ¹H NMR (400 MHz, dimethyl sulfoxide-d₆) δ 12.38 (s, 1H), 7.67 (d, J=8.4 Hz, 1H), 7.57 (t, J=7.8 Hz, 1H), 7.52 (d, J=8.4 Hz, 1H), 7.04 (d, J=7.2 Hz, 1H), 6.96 (broad d, J=8.0 Hz, 1H), 6.70 (d, J=8.5 Hz, 1H), 4.05 (t, J=9.4 Hz, 1H), 3.91 (broad d, J=10.7 Hz, 1H), 3.75 (q, J=9.3, 8.7 Hz, 1H), 3.11 (br s, 1H), 2.94 (br d, J=13.3 Hz, 1H), 2.82-2.56 (m, 2H), 2.30-2.17 (m, 1H), 2.10 (br s, 1H), 1.87-1.67 (m, 4H), 1.64-1.41 (m, 9H), 1.41-1.27 (m, 4H), 1.25-1.13 (m, 2H), 0.87 (s, 9H). ESI-MS m/z calc. 596.31445, found 597.3 (M+1)⁺; Retention time: 2.32 min (LC Method B), and as the second diastereomer to elute, (14S)-8-[3-(4,4-dimethylpentyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 2) (Compound 146) (15 mg, 8%); ¹H NMR (400 MHz, dimethyl sulfoxide-d₆) δ 12.41 (s, 1H), 7.68 (d, J=8.5 Hz, 1H), 7.61-7.50 (m, 2H), 7.03 (d, J=7.2 Hz, 1H), 6.92 (d, J=27.7 Hz, 1H), 6.69 (d, J=8.5 Hz, 1H), 3.94 (t, J=9.4 Hz, 2H), 3.82 (q, J=9.1 Hz, 1H), 3.09 (s, 1H), 2.93 (d, J=13.3 Hz, 1H), 2.68 (t, J=10.9 Hz, 2H), 2.25 (q, J=8.8 Hz, 1H), 2.08 (d, J=8.3 Hz, 1H), 1.86-1.63 (m, 4H), 1.57 (s, 4H), 1.52 (d, J=4.2 Hz, 1H), 1.46 (s, 3H), 1.41-1.08 (m, 7H), 0.86 (s, 9H); ESI-MS m/z calc. 596.31445, found 597.3 (M+1)⁺; Retention time: 2.33 min (LC Method B).

Example 39: Preparation of 12,12,22-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 1) (Compound 148) and 12,12,22-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 2) (Compound 149)

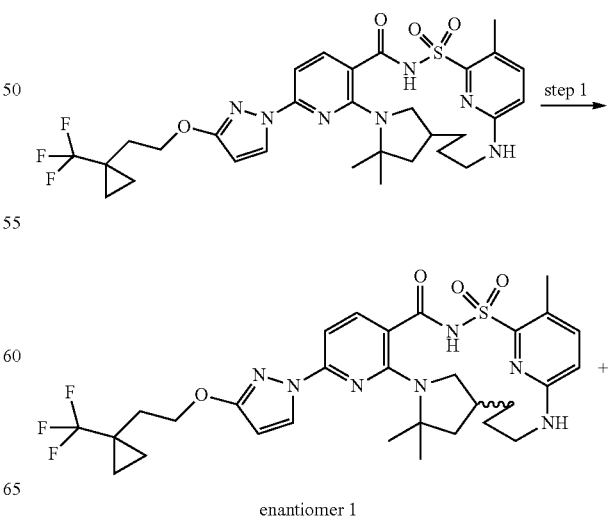

enantiomer 1

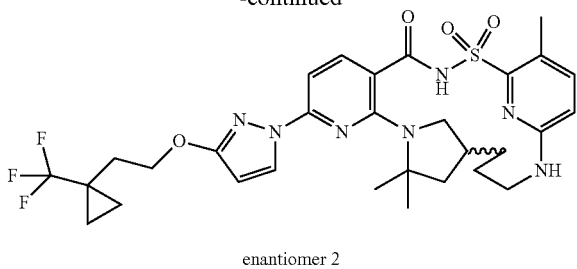

Step 1: 12,12,22-Trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 1) (Compound 148) and 12,12,22-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 2) (Compound 149)

Racemic 12,12,22-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (85 mg, 0.1299 mmol) was subjected to chiral SFC chromatography. The following SFC protocol was employed: ChiralPak AS-3 (150×2.1 mm), 3 μm; 35° C. mobile phase: 30% acetonitrile:methanol (90:10), 70% carbon dioxide. The first enantiomer to elute was 12,12,22-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 1) (Compound 148) (34 mg, 40%). ESI-MS m/z calc. 647.2502, found 648.34 (M+1)⁺; Retention time: 2.24 min (LC Method B). The second enantiomer to elute was 12,12,22-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 2) (Compound 149) (35 mg, 41%). ¹H NMR (400 MHz, dimethyl sulfoxide-d₆) δ 12.46 (s, 1H), 8.23 (d, J=2.8 Hz, 1H), 7.83 (d, J=8.2 Hz, 1H), 7.41 (d, J=8.5 Hz, 1H), 6.93 (d, J=8.2 Hz, 1H), 6.65 (d, J=8.6 Hz, 2H), 6.12 (d, J=2.7 Hz, 1H), 4.32 (t, J=7.0 Hz, 2H), 4.00-3.79 (m, 1H), 3.27-3.14 (m, 1H), 2.93 (d, J=13.2 Hz, 1H), 2.84 (t, J=10.5 Hz, 1H), 2.36 (s, 3H), 2.08 (t, J=7.1 Hz, 2H), 1.87 (dd, J=11.6, 5.2 Hz, 1H), 1.77 (m, 1H), 1.57 (d, J=35.9 Hz, 8H), 1.44-1.29 (m, 1H), 0.96 (d, J=4.4 Hz, 2H), 0.91 (d, J=13.2 Hz, 3H). ESI-MS m/z calc. 647.2502, found 648.34 (M+1)⁺; Retention time: 2.25 min (LC Method B).

Example 40: Preparation of 4-[3-(3,3-dicyclopropylpropoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 1) (Compound 153) and 4-[3-(3,3-dicyclopropylpropoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 2) (Compound 154)

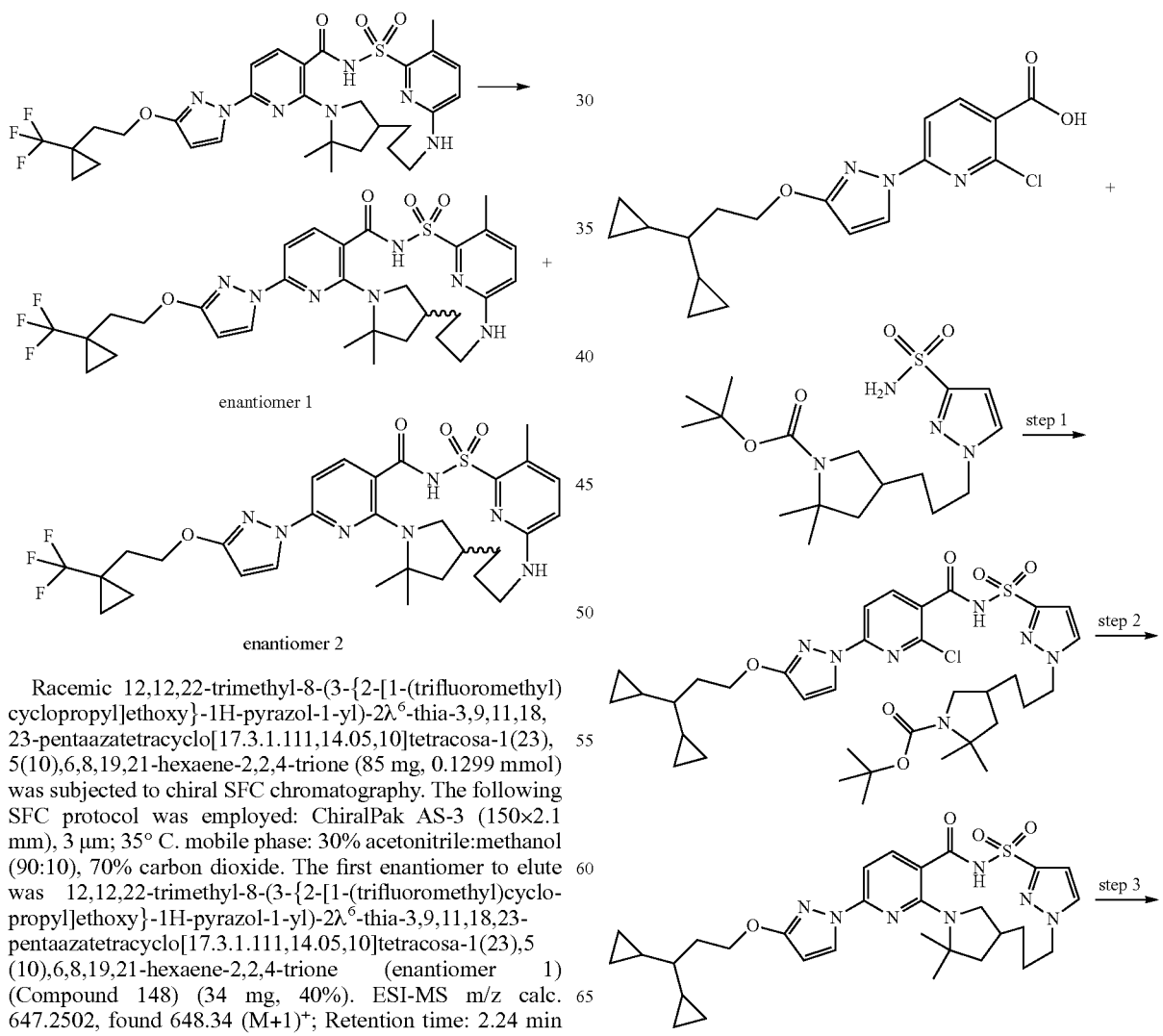

-continued

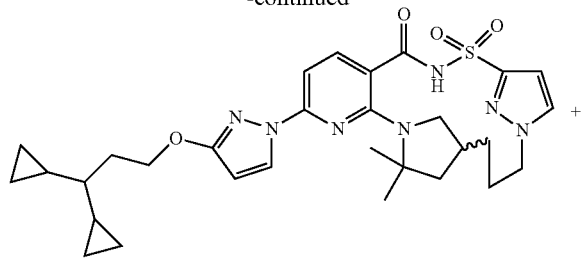

enantiomer 1

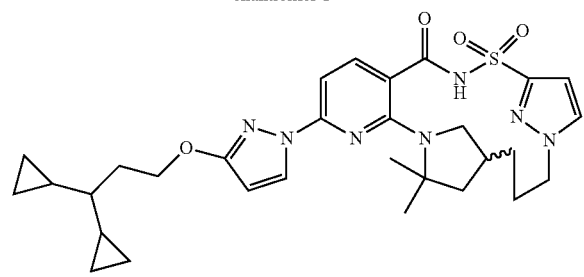

enantiomer 2

Step 1: tert-Butyl 4-[3-[3-[[2-chloro-6-[3-(3,3-dicyclopropylpropoxy) pyrazol-1-yl]pyridine-3-carbonyl]sulfamoyl]pyrazol-1-yl]propyl]-2,2-dimethyl-pyrrolidine-1-carboxylate

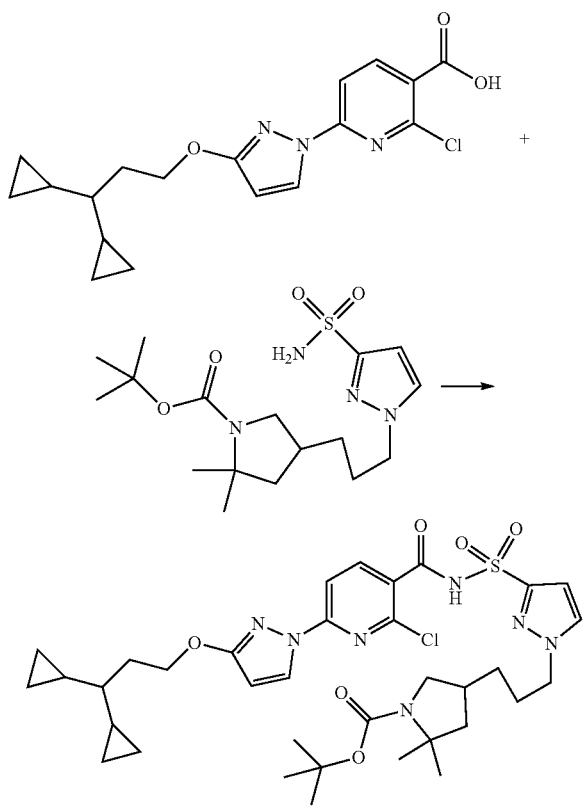

2-Chloro-6-[3-(3,3-dicyclopropylpropoxy)pyrazol-1-yl] pyridine-3-carboxylic acid (521 mg, 1.440 mmol) and carbonyl diimidazole (237 mg, 1.462 mmol) were combined in tetrahydrofuran (5.0 mL) and stirred for 2 h at room temperature. Then, tert-butyl 2,2-dimethyl-4-[3-(3-sulfamoylpyrazol-1-yl)propyl]pyrrolidine-1-carboxylate (460 mg, 1.190 mmol) was added followed by 1,8-diazabicyclo[5.4.0]undec-7-ene (280 μL, 1.872 mmol) and the reaction was stirred at room temperature for 18 h. The reaction was diluted with ethyl acetate and washed with saturated ammonium chloride solution followed by brine. The organics were separated, dried over sodium sulfate, filtered and evaporated. The residue was purified by silica gel chromatography using a gradient from 100% dichloromethane to 20% methanol in dichloromethane to afford tert-butyl 4-[3-[3-[[2-chloro-6-[3-(3,3-dicyclopropylpropoxy)pyrazol-1-yl]pyridine-3-carbonyl]sulfamoyl]pyrazol-1-yl]propyl]-2,2-dimethyl-pyrrolidine-1-carboxylate (270 mg, 31%) as a white solid. $^1$H NMR (400 MHz, Chloroform-d) δ 9.61 (d, J=95.1 Hz, 1H), 8.30 (d, J=2.9 Hz, 1H), 8.24 (t, J=8.9 Hz, 1H), 7.75 (d, J=8.4 Hz, 1H), 7.47 (d, J=2.6 Hz, 1H), 7.05 (d, J=2.3 Hz, 1H), 5.97 (d, J=2.9 Hz, 1H), 4.43 (t, J=6.8 Hz, 2H), 4.20 (t, J=7.1 Hz, 2H), 3.78-3.54 (m, 1H), 2.84 (t, J=10.1 Hz, 1H), 2.07 (s, 1H), 1.97 (q, J=6.8 Hz, 2H), 1.93-1.81 (m, 1H), 1.63 (s, 5H), 1.43 (d, J=4.7 Hz, 9H), 1.37-1.23 (m, 6H), 0.72-0.61 (m, 2H), 0.50-0.38 (m, 4H), 0.33 (tt, J=9.0, 6.8 Hz, 1H), 0.20 (dtd, J=8.2, 4.9, 3.5 Hz, 2H), 0.10 (ddd, J=9.3, 4.8, 3.5 Hz, 2H). ESI-MS m/z calc. 729.30756, found 730.4 (M+1)$^+$; Retention time: 0.92 min (LC Method A).

Step 2: 4-[3-(3,3-Dicyclopropylpropoxy)-1H-pyrazol-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione

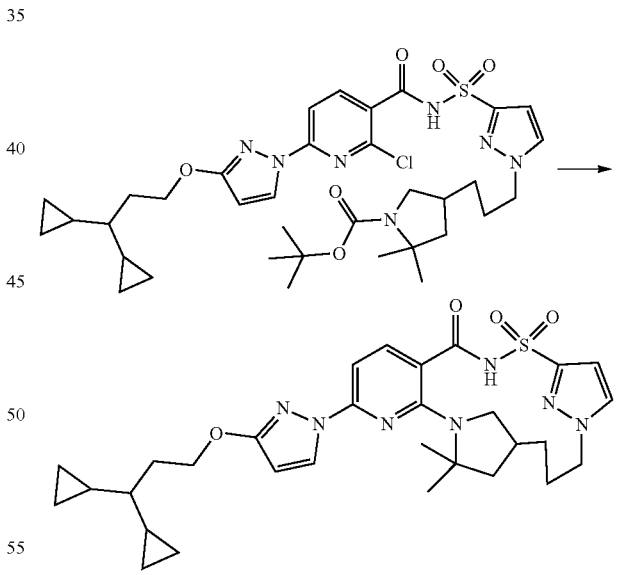

A solution of tert-butyl 4-[3-[3-[[2-chloro-6-[3-(3,3-dicyclopropylpropoxy)pyrazol-1-yl]pyridine-3-carbonyl]sulfamoyl]pyrazol-1-yl]propyl]-2,2-dimethyl-pyrrolidine-1-carboxylate (270 mg, 0.3697 mmol) in dichloromethane (1.862 mL) and trifluoroacetic acid (300 μL, 3.920 mmol) was stirred at room temperature for 4 h. The solvents were then removed in vacuo. The residue was dissolved in ethyl acetate, washed with 2 mL of saturated sodium bicarbonate solution and the solvent was evaporated. The resulting residue was dissolved in dimethyl sulfoxide (5.586 mL) and 3 Å molecular sieves were added and the reaction mixture was stirred for 10 min. Then, cesium fluoride (171 mg, 1.126 mmol) and potassium carbonate (158 mg, 1.143 mmol) were added and the reaction mixture was heated at 150° C. overnight. The reaction mixture was filtered through Whatman filter disc (puradisc 25 TF) and the filtrate was purified by a reverse phase HPLC-MS method using a dual gradient run from 50-99% mobile phase B over 15.0 min (Mobile phase A=water (0.05% hydrochloric acid), Mobile phase B=acetonitrile) to afford racemic 4-[3-(3,3-dicyclopropylpropoxy)-1H-pyrazol-1-yl]-20,20-dimethyl-10λ⁶-thia-1,3,9,14,22 pentaazatetracyclo[16.2.1.1¹¹,¹⁴.0²,⁷]docosa-2,4,6,11(22),12-pentaene-8,10,10-trione (50 mg, 23%) as a white solid. ESI-MS m/z calc. 593.27844, found 594.4 (M+1)⁺; Retention time: 2.36 min (LC Method B).

Step 3: 4-[3-(3,3-dicyclopropylpropoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 1) (Compound 153) and 4-[3-(3,3-dicyclopropylpropoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 2) (Compound 154)

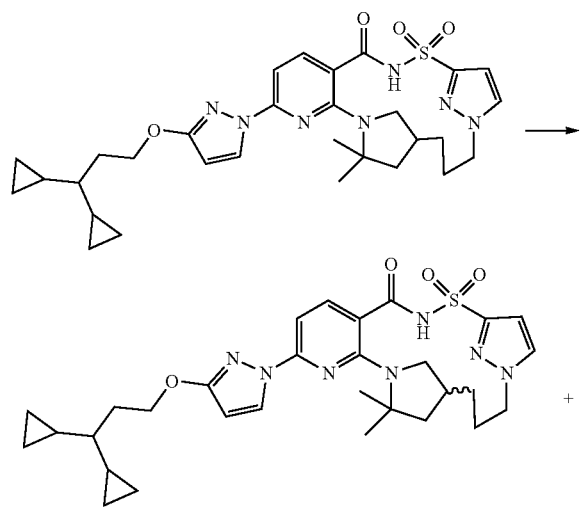

Subjected racemic 4-[3-(3,3-dicyclopropylpropoxy)-1H-pyrazol-1-yl]-20,20-dimethyl-10λ⁶-thia-1,3,9,14,22 pentaazatetracyclo[16.2.1.1¹¹,¹⁴.0²,⁷]docosa-2,4,6,11(22),12-pentaene-8,10,10-trione (50 mg) to chiral separation by SFC chromatography using a ChiralPak AS-H (250×10 mm) column, 5 µm particle size) with 28% acetonitrile/methanol (90:10)/72% carbon dioxide mobile phase at 10 mL/min over 8.0 min (injection volume=70 µL of 24 mg/mL solution in acetonitrile/methanol/dimethyl sulfoxide (82:8:10)) giving as the first enantiomer to elute 4-[3-(3,3-dicyclopropylpropoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (enantiomer 1) (Compound 153) (20 mg, 18%); ¹H NMR (400 MHz, Chloroform-d) δ 8.63 (s, 1H), 8.17 (d, J=2.7 Hz, 1H), 7.67 (d, J=8.3 Hz, 1H), 7.47 (d, J=2.3 Hz, 1H), 7.07 (d, J=2.3 Hz, 1H), 7.02 (d, J=8.2 Hz, 1H), 5.87 (d, J=2.7 Hz, 1H), 4.42 (t, J=6.8 Hz, 2H), 4.33 (dt, J=13.3, 3.4 Hz, 1H), 4.00-3.85 (m, 1H), 2.74 (t, J=8.1 Hz, 1H), 2.12 (ttd, J=14.6, 10.0, 8.8, 4.7 Hz, 2H), 2.01-1.94 (m, 2H), 1.81-1.70 (m, 1H), 1.58 (s, 3H), 1.55 (s, 3H), 1.47 (t, J=12.2 Hz, 1H), 0.87-0.71 (m, OH), 0.71-0.61 (m, 2H), 0.53-0.39 (m, 4H), 0.37-0.30 (m, 1H), 0.24-0.15 (m, 2H), 0.15-0.07 (m, 2H), ESI-MS m/z calc. 593.27844, found 594.4 (M+1)⁺; Retention time: 2.39 min (LC Method B) and as the second enantiomer to elute 4-[3-(3,3-dicyclopropylpropoxy)-1H-pyrazol-1-yl]-20,20-dimethyl-10λ⁶-thia-1,3,9,14,22 pentaazatetracyclo[16.2.1.1¹¹,¹⁴.0²,⁷]docosa-2,4,6,11(22),12-pentaene-8,10,10-trione (enantiomer 2) (Compound 154) (23.6 mg, 47%) as a white solid; ¹H NMR (400 MHz, Chloroform-d) δ 8.16 (d, J=2.7 Hz, 1H), 7.65 (d, J=8.3 Hz, 1H), 7.46 (d, J=2.4 Hz, 1H), 7.06 (d, J=2.3 Hz, 1H), 7.00 (d, J=8.3 Hz, 1H), 5.87 (d, J=2.7 Hz, 1H), 4.42 (t, J=6.8 Hz, 2H), 4.32 (d, J=13.5 Hz, 1H), 4.00-3.83 (m, 1H), 2.73 (t, J=8.1 Hz, 1H), 2.23-2.09 (m, 2H), 1.97 (q, J=6.9 Hz, 3H), 1.74 (dd, J=11.9, 5.2 Hz, 1H), 1.58 (s, 4H), 1.54 (s, 3H), 1.51-1.41 (m, 2H), 0.86-0.72 (m, 1H), 0.71-0.61 (m, 2H), 0.45 (dddd, J=15.6, 8.1, 4.9, 3.7 Hz, 4H), 0.38-0.30 (m, 1H), 0.25-0.18 (m, 2H), 0.12 (ddtd, J=11.4, 5.2, 3.7, 3.1, 1.9 Hz, 2H). ESI-MS m/z calc. 593.27844, found 594.4 (M+1)⁺; Retention time: 2.39 min (LC Method B).

Example 41: Preparation of 12,12-dimethyl-8-(3-{3-[1-(trifluoromethyl) cyclopropyl]propoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Enantiomer 1) (Compound 159) and 12,12-dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Enantiomer 2) (Compound 160)

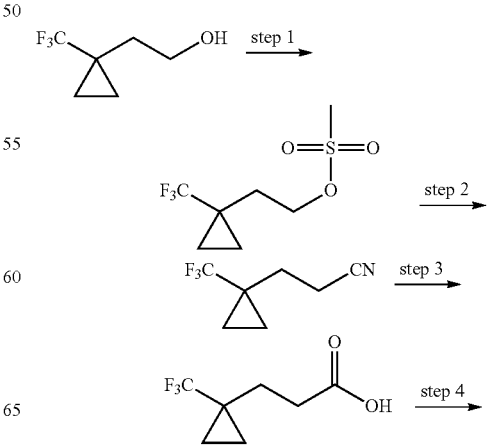

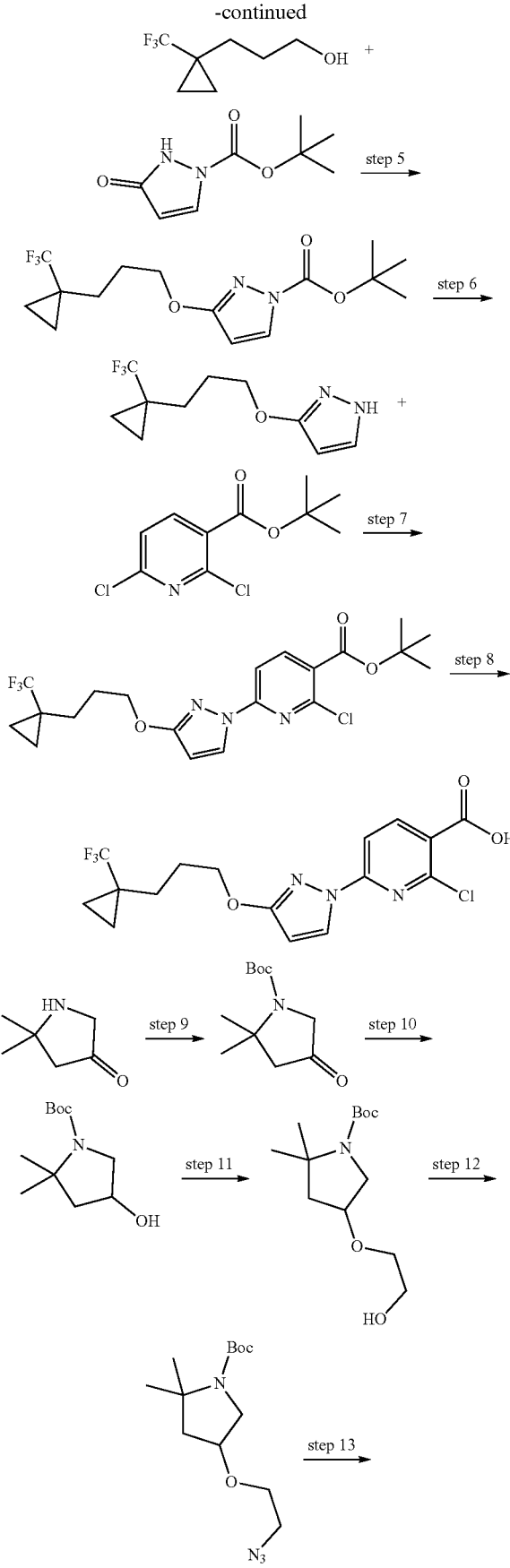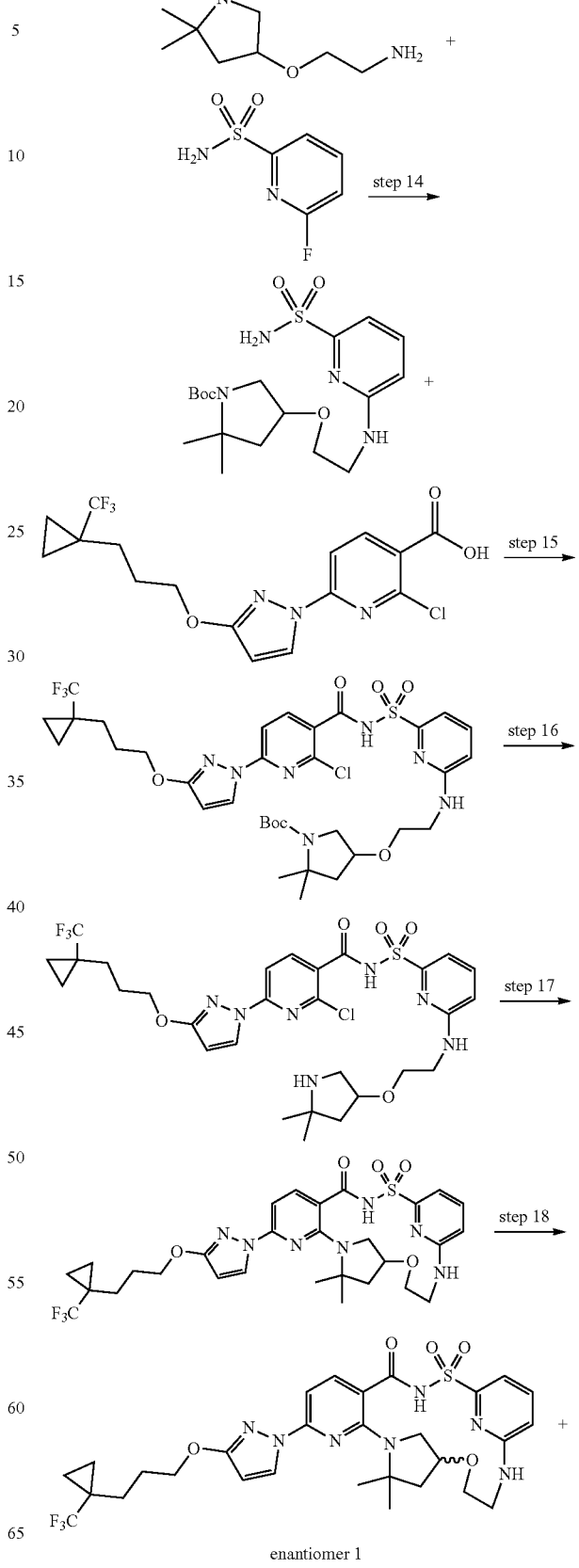

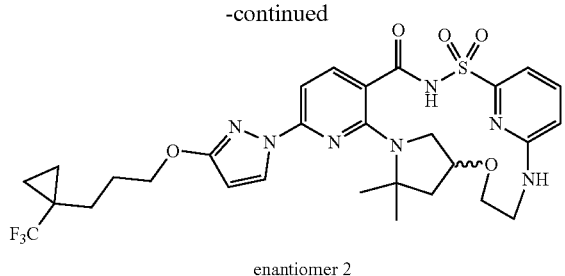

enantiomer 2

Step 1: 2-[1-(Trifluoromethyl)cyclopropyl]ethyl methanesulfonate

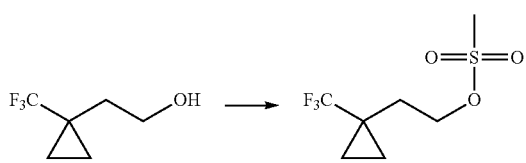

A 1000 mL, 3-neck round bottom flask was fitted with a mechanical stirrer, a cooling bath, a J-Kem temperature probe, an addition funnel and a nitrogen inlet/outlet. The vessel was charged under a nitrogen atmosphere with 2-[1-(trifluoromethyl)cyclopropyl]ethanol (125 g, 811.0 mmol) and 2-methyltetrahydrofuran (625 mL) which provided a clear colorless solution. Stirring was commenced and the pot temperature was recorded at 19° C. The vessel was then charged with triethylamine (124.3 mL, 891.8 mmol) added neat in one portion. The cooling bath was then charged with crushed ice/water and the pot temperature was lowered to 0° C. The addition funnel was charged with a solution of methanesulfonyl chloride (62.77 mL, 811.0 mmol) in 2-methyltetrahydrofuran (125 mL, 2 mL/g) which was subsequently added dropwise over 90 min which resulted in a white suspension and an exotherm to 1° C. The mixture was allowed to slowly warm to room temperature and continue to stir at room temperature for 1 h at which point the mixture was poured into ice cold water (250 mL) and then transferred to a separatory funnel. The organic was removed and washed with 20 wt % potassium bicarbonate solution (250 mL), dried over sodium sulfate (200 g) and then filtered through a glass frit Buchner funnel. The clear filtrate was concentrated under reduced pressure to provide 2-[1-(trifluoromethyl)cyclopropyl]ethyl methanesulfonate (185 g, 98%) as a clear pale yellow oil. $^1$H NMR (400 MHz, Chloroform-d) δ 4.36 (ddt, J=7.1, 6.4, 0.7 Hz, 2H), 3.02 (s, 3H), 2.03 (t, J=7.1 Hz, 2H), 1.11-0.98 (m, 2H), 0.81-0.66 (m, 2H).

Step 2: 3-[1-(Trifluoromethyl)cyclopropyl]propanenitrile

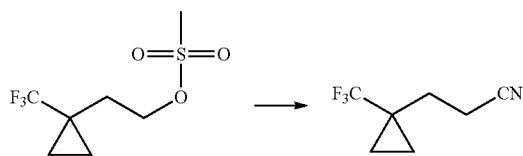

A 1000 mL, 3-neck round bottom flask was fitted with a mechanical stirrer, a heating mantle, a J-Kem temperature probe/controller, a water cooled reflux condenser and a nitrogen inlet/outlet. The vessel was charged under a nitrogen atmosphere with 2-[1-(trifluoromethyl)cyclopropyl]ethyl methanesulfonate (50 g, 215.3 mmol) and dimethyl sulfoxide (250 mL) which provided a clear pale yellow solution. Stirring was commenced and the pot temperature was recorded at 19° C. The vessel was charged with sodium cyanide (13.19 g, 269.1 mmol), added as a solid in one portion. The mixture was heated to a pot temperature of 70° C. and the condition was maintained for 24 h. Upon heating all of the sodium cyanide dissolved and the reaction mixture turned to a light amber suspension. After cooling to room temperature, the reaction mixture was poured into water (500 mL) and then transferred to a separatory funnel and partitioned with methyl tert-butyl ether (500 mL). The organic was removed and the residual aqueous was extracted with methyl tert-butyl ether (3×250 mL). The combined organic layers were washed with water (2×250 mL), dried over sodium sulfate (200 g) and then filtered through a glass frit Buchner funnel. The clear filtrate was concentrated under reduced pressure to provide 3-[1-(trifluoromethyl)cyclopropyl]propanenitrile (30 g, 85%) as a clear amber oil. $^1$H NMR (400 MHz, Chloroform-d) δ 2.55 (t, J=7.6 Hz, 2H), 1.93 (t, J=7.7 Hz, 2H), 1.11-1.04 (m, 2H), 0.78-0.70 (m, 2H).

Step 3: 3-[1-(Trifluoromethyl)cyclopropyl]propanoic Acid

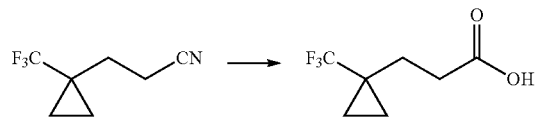 [SMILES: N#CCCC1(C(F)(F)F)CC1 ; O=C(O)CCC1(C(F)(F)F)CC1]

A 1000 mL, 3-neck round bottom flask was fitted with a mechanical stirrer, a heating mantle, a J-Kem temperature probe/controller, a water cooled reflux condenser and a nitrogen inlet/outlet. The vessel was subsequently charged under a nitrogen atmosphere with 3-[1-(trifluoromethyl)cyclopropyl]propanenitrile (25 g, 153.2 mmol) and ethyl alcohol (375 mL) which provided a clear amber solution. Stirring was commenced and the pot temperature was recorded at 19° C. The vessel was then charged with sodium hydroxide (102.1 mL of 6 M, 612.6 mmol), added in one portion. The resulting clear amber solution was heated to a pot temperature of 70° C. and the condition was maintained for 24 h. After cooling to room temperature, the reaction mixture was concentrated to remove the ethyl alcohol. The residual aqueous was diluted with water (150 mL) and then transferred to a separatory funnel and partitioned with methyl tert-butyl ether (50 mL). The aqueous was removed and the pH was adjusted to pH 1 with 6 M hydrochloric acid solution. The resulting aqueous solution was transferred to a separatory funnel and partitioned with methyl tert-butyl ether (250 mL). The organic was removed and the residual aqueous was extracted with methyl tert-butyl ether (2×150 mL). The combined organic was dried over sodium sulfate (150 g) and then filtered through a glass frit Buchner funnel. The clear filtrate was concentrated under reduced pressure to provide 3-[1-(trifluoromethyl)cyclopropyl]propanoic acid (26 g, 93%) as a clear amber oil. $^1$H NMR (400 MHz, Chloroform-d) δ 2.63-2.50 (m, 2H), 1.96-1.84 (m, 2H), 1.03-0.95 (m, 2H), 0.66-0.58 (m, J=1.7 Hz, 2H).

Step 4: 3-[1-(Trifluoromethyl)cyclopropyl]propan-1-ol

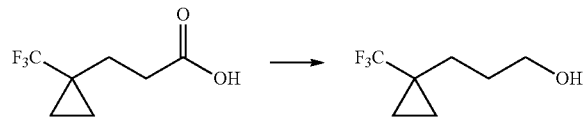 [SMILES: O=C(O)CCC1(C(F)(F)F)CC1 ; OCCCC1(C(F)(F)F)CC1]

A 1000 mL, 3-neck round bottom flask was fitted with a mechanical stirrer, a cooling bath, an addition funnel, a J-Kem temperature probe and a nitrogen inlet/outlet. The vessel was charged under a nitrogen atmosphere with lithium aluminum hydride pellets (6.775 g, 178.5 mmol). The vessel was then charged under a nitrogen atmosphere with tetrahydrofuran (250 mL). Stirring was commenced and the pot temperature was recorded at 20° C. The mixture was allowed to stir at room temperature for 0.5 h to allow the pellets to dissolve. The pot temperature of the resulting grey suspension was recorded at 24° C. The cooling bath was then charged with crushed ice/water and the pot temperature was lowered to 0° C. The addition funnel was charged with a solution of 3-[1-(trifluoromethyl)cyclopropyl]propanoic acid (25 g, 137.3 mmol) in tetrahydrofuran (75 mL, 3 mL/g) and the clear pale yellow solution was added dropwise over 1 h. After the addition was completed, the pot temperature of the resulting greyish-brown suspension was recorded at 5° C. The mixture was allowed to slowly warm to room temperature and continue to stir at room temperature for 24 h. The suspension was cooled to 0° C. with a crushed ice/water cooling bath and then quenched by the very slow dropwise addition of water (6.775 mL), followed by 15 wt % sodium hydroxide solution (6.775 mL) and then finally with water (20.32 mL). The pot temperature of the resulting white suspension was recorded at 5° C. The suspension was continued to stir at 5° C. for 30 min and then filtered through a glass frit Buchner funnel with a 20 mm layer of celite. The filter cake was displacement washed with tetrahydrofuran (2×150 mL) and then dried under vacuum for 15 min. The filtrate was dried over sodium sulfate (250 g) and then filtered through a glass frit Buchner funnel. The filtrate was concentrated under reduced pressure to provide a clear pale amber oil as the desired product, 3-[1-(trifluoromethyl)cyclopropyl]propan-1-ol (21.2 g, 92%). $^1$H NMR (400 MHz, Chloroform-d) δ 3.65 (t, J=6.0 Hz, 2H), 1.78-1.59 (m, 4H), 0.99-0.91 (m, 2H), 0.59 (dp, J=4.7, 1.7 Hz, 2H).

Step 5: tert-Butyl 3-[3-[1-(trifluoromethyl)cyclopropyl]propoxy]pyrazole-1-carboxylate

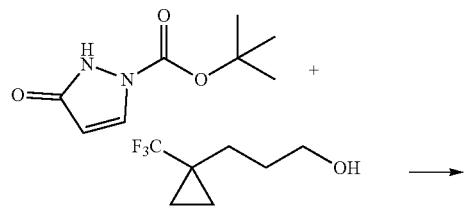

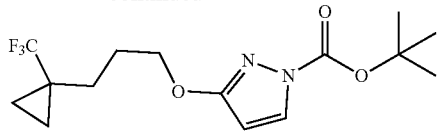

A 5000 mL, 3-neck round bottom flask was fitted with a mechanical stirrer, a heating mantle, a J-Kem temperature probe/controller, an addition funnel, a water cooled reflux condenser and a nitrogen inlet/outlet. The vessel was charged under a nitrogen atmosphere with tert-butyl 5-oxo-1H-pyrazole-2-carboxylate (175 g, 950.1 mmol) and tetrahydrofuran (2100 mL) which provided a clear pale yellow solution. Stirring was commenced and the pot temperature was recorded at 19° C. The vessel was then charged with 3-[1-(trifluoromethyl)cyclopropyl]propan-1-ol (175.7 g, 1.045 mol), added neat in one portion followed by triphenylphosphine (274.1 g, 1.045 mol) added as a solid in one portion. The resulting clear pale yellow solution was then treated with diisopropyl azodicarboxylate (205.7 mL, 1.045 mol) added neat dropwise over 2 h which resulted in a gradual exotherm to 40° C. and a clear light amber solution. The reaction mixture was then heated to a pot temperature of 50° C. and the condition was maintained for 2 h. The clear amber reaction mixture was concentrated under reduced pressure and the resulting clear dark amber oil was suspended in toluene (1400 mL) and stirred at room temperature for 1 h during which time solid triphenylphosphine oxide precipitated. The thick slurry was filtered through a glass frit Buchner funnel and the filter cake was displacement washed with toluene (2×500 mL). The clear amber filtrate was concentrated under reduced pressure to provide a clear pale amber oil (320 g). The material was purified by silica gel column flash chromatography (solid load on celite) eluting with a gradient of 100% hexane to 20% ethyl acetate in hexane. The desired fractions were combined and concentrated under reduced pressure to provide tert-butyl 3-[3-[1-(trifluoromethyl)cyclopropyl]propoxy]pyrazole-1-carboxylate (280 g, 88%) as a clear pale yellow oil. $^1$H NMR (400 MHz, dimethyl sulfoxide-d$_6$) δ 8.07 (d, J=3.0 Hz, 1H), 6.09 (d, J=2.9 Hz, 1H), 4.15 (t, J=6.2 Hz, 2H), 1.91-1.75 (m, 2H), 1.76-1.63 (m, 2H), 1.55 (s, 9H), 0.98-0.84 (m, 2H), 0.74 (dt, J=3.3, 1.9 Hz, 2H).

Step 6: 3-[3-[1-(Trifluoromethyl)cyclopropyl]propoxy]-1H-pyrazole

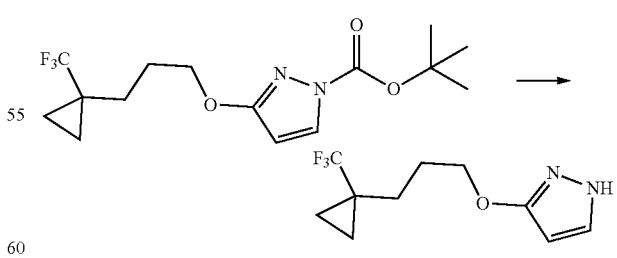

A 5000 mL, 3-neck round bottom flask was fitted with a mechanical stirrer, a heating mantle, a J-Kem temperature probe/controller, a water cooled reflux condenser, an addition funnel and a nitrogen inlet/outlet. The vessel was charged under a nitrogen atmosphere with tert-butyl 3-[3-[1-(trifluoromethyl)cyclopropyl]propoxy]pyrazole-1-carboxylate (280 g, 837.5 mmol), dichloromethane (840 mL) and methyl alcohol (840 mL) which provided a clear pale yellow solution. Stirring was commenced and the pot temperature was recorded at 19° C. The addition funnel was charged with hydrogen chloride in 1,4-dioxane (628 mL of 4 M, 2.512 mol) which was subsequently added dropwise over 2 h which resulted in a gradual exotherm to 30° C. The resulting clear pale yellow solution was heated to a pot temperature of 45° C. and the condition was maintained for 1 h. The reaction mixture was allowed to cool to room temperature and then concentrated under reduced pressure. The remaining residue was dissolved in methyl tert-butyl ether (2.24 L) and then transferred to a separatory funnel and partitioned with ice cold sodium hydroxide (1.256 L of 2 M, 2.512 mol). The organic was removed and the residual aqueous was extracted with tert-butyl methyl ether (2×500 mL). The combined organic was washed with saturated sodium chloride solution (2×500 mL), dried over sodium sulfate (500 g) and then filtered through a glass frit Buchner funnel. The clear pale yellow filtrate was concentrated under reduced pressure to provide 3-[3-[1-(trifluoromethyl)cyclopropyl]propoxy]-1H-pyrazole (190 g, 97%) as a clear light yellow oil. ESI-MS m/z calc. 234.09799, found 235.1 (M+1)$^+$; Retention time: 1.37 min (LC Method B).

Step 7: tert-Butyl 2-chloro-6-[3-[3-[1-(trifluoromethyl)cyclopropyl]propoxy]pyrazol-1-yl]pyridine-3-carboxylate

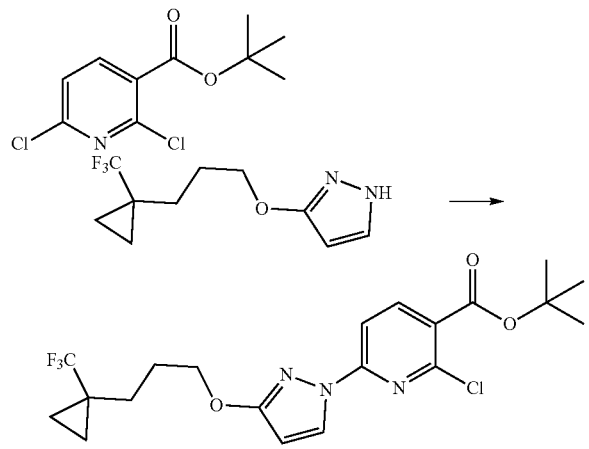

A 5000 mL, 3-neck round bottom flask was fitted with a mechanical stirrer, a cooling bath used as secondary containment, a J-Kem temperature probe, a water cooled reflux condenser, an addition funnel and a nitrogen inlet/outlet. The vessel was charged under a nitrogen atmosphere with 3-[3-[1-(trifluoromethyl)cyclopropyl]propoxy]-1H-pyrazole (188.8 g, 806.1 mmol) and N,N-dimethylformamide (2.40 L) which provided a clear pale yellow solution. Stirring was commenced and the pot temperature was recorded at 17° C. The vessel was then charged with tert-butyl 2,6-dichloro-pyridine-3-carboxylate (200 g, 806.1 mmol) added as a solid in one portion. The resulting clear pale yellow solution was then treated with potassium carbonate (144.8 g, 1.048 mol) added as a solid in one portion followed by 1,4-diazabicyclo [2.2.2]octane (13.56 g, 120.9 mmol), added as a solid in one portion. The resulting pale yellow suspension was allowed to stir at room temperature for 24 h. The reaction mixture was cooled to 10° C. with a crushed ice/water cooling bath. The addition funnel was charged with water (2.40 L) which was added dropwise over 2 h and resulted in a thick suspension and an exotherm to 15° C. The resulting suspension was continued to stir at 15° C. for 30 min and then filtered through a glass frit Buchner funnel. The filter cake was displacement washed with water (3×500 mL) and then dried under vacuum in the Buchner funnel for 2 h. The material was then allowed to air dry overnight to provide tert-butyl 2-chloro-6-[3-[3-[1-(trifluoromethyl)cyclopropyl] propoxy]pyrazol-1-yl]pyridine-3-carboxylate (305 g, 85%) as a white granular solid. The material was used in the next synthetic step without further purification. ESI-MS m/z calc. 445.138, found 446.2 (M+1)$^+$; Retention time: 2.54 min (LC Method B).

Step 8: 2-Chloro-6-[3-[3-[1-(trifluoromethyl)cyclopropyl]propoxy]pyrazol-1-yl]pyridine-3-carboxylic Acid

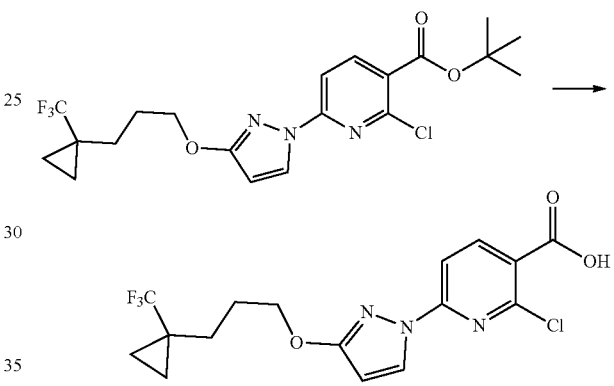

A 1000 mL, 3-neck round bottom flask was fitted with a mechanical stirrer, a heating mantle, a J-Kem temperature probe/controller, an addition funnel, a water cooled reflux condenser and a nitrogen inlet/outlet. The vessel was charged under a nitrogen atmosphere with tert-butyl 2-chloro-6-[3-[3-[1-(trifluoromethyl)cyclopropyl]propoxy] pyrazol-1-yl]pyridine-3-carboxylate (50 g, 112.1 mmol) and 2-propanol (250 mL) which provided an off-white suspension. Stirring was commenced and the pot temperature was recorded at 19° C. The addition funnel was charged with hydrochloric acid (93.42 mL of 6 M, 560.5 mmol) which was added dropwise over 30 min and resulted in an exotherm to 30° C. The resulting suspension was then heated to reflux (pot temperature 82° C.). Upon heating, the suspension turns to a clear pale yellow solution (pot temperature 75° C. at this point). After stirring at reflux for 30 min, a solid began to precipitate. The suspension was continued to stir at reflux for an additional 30 min at which point water (150 mL) was added dropwise over 45 min. The heat was then removed and the suspension was continued to stir and allowed to slowly cool to room temperature. The material was collected by vacuum filtration in a glass frit Buchner funnel and the filter cake was displacement washed with 1:1 water/2-propanol (250 mL) followed by water (2×250 mL) and then dried under vacuum in the Buchner funnel for 30 min. The material was further dried in a vacuum oven at 45° C. for 24 h to provide 2-chloro-6-[3-[3-[1-(trifluoromethyl) cyclopropyl]propoxy]pyrazol-1-yl]pyridine-3-carboxylic acid (41.5 g, 95%) as a white solid. $^1$H NMR (400 MHz, dimethyl sulfoxide-d$_6$) δ 13.59 (s, 1H), 8.50-8.28 (m, 2H), 7.72 (d, J=8.4 Hz, 1H), 6.20 (d, J=3.0 Hz, 1H), 4.23 (t, J=6.2

Hz, 2H), 1.86 (dq, J=10.8, 6.3 Hz, 2H), 1.78-1.66 (m, 2H), 0.98-0.87 (m, 2H), 0.76 (dt, J=4.9, 1.7 Hz, 2H).

Step 9: tert-Butyl 2,2-dimethyl-4-oxo-pyrrolidine-1-carboxylate

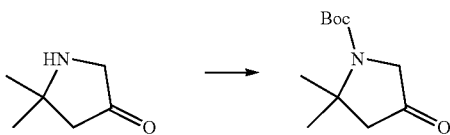

di-tert-Butyl dicarbonate (22.9 g, 24.11 mL, 104.9 mmol) was added to a solution of 5,5-dimethylpyrrolidin-3-one (hydrochloride) (13.08 g, 87.42 mmol), triethylamine (17.71 g, 24.4 mL, 175.0 mmol) and DMAP (1.1 g, 9.004 mmol) in dichloromethane (325 mL) and reaction mixture was stirred at room temperature overnight. The reaction mixture was washed with 1 N hydrochloric acid (300 mL) and the aqueous layer was extracted with dichloromethane (2×250 mL). The organic layers were combined, washed with 5% sodium bicarbonate (250 mL) and brine (150 mL), dried over sodium sulfate, filtered and concentrated under reduced pressure to afford tert-butyl 2,2-dimethyl-4-oxo-pyrrolidine-1-carboxylate (18.5 g, 99%) as a white solid. $^1$H NMR (300 MHz, CDCl$_3$) ppm 1.33-1.66 (m, 15H), 2.51 (s, 2H), 3.85 (br. s., 2H). ESI-MS m/z calc. 213.27, found 158.2 (M-C$_4$H$_8$)$^+$; Retention time: 1.91 min (LC Method I).

Step 10: tert-Butyl 4-hydroxy-2,2-dimethyl-pyrrolidine-1-carboxylate

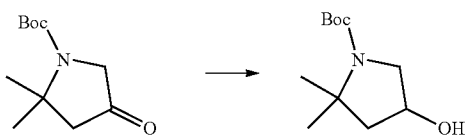

tert-Butyl 2,2-dimethyl-4-oxo-pyrrolidine-1-carboxylate (150 mg, 0.7033 mmol) was dissolved in dry methanol (2.5 mL) and cooled in an ice-bath. NaBH$_4$ (30 mg, 0.7930 mmol) was added carefully and the reaction mixture was stirred at 0° C. for 1.5 h. The reaction mixture was diluted with water (25 mL), and 1M aqueous hydrochloric acid (0.5 mL). The aqueous layer was extracted with ethyl acetate (2×25 mL) and the organic layers were combined, washed with brine (10 mL) dried with sodium sulfate, filtered and concentrated in vacuo giving tert-butyl 4-hydroxy-2,2-dimethyl-pyrrolidine-1-carboxylate (150 mg, 99%) which was used directly in the ensuing step. ESI-MS m/z calc. 215.15215, found 216.2 (M+1)$^+$; Retention time: 0.48 min (LC Method A).

Step 11: tert-Butyl 4-(2-hydroxyethoxy)-2,2-dimethyl-pyrrolidine-1-carboxylate

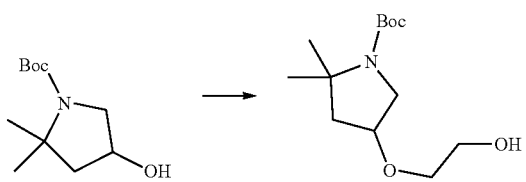 [SMILES: CC(C)(C)OC(=O)N1CC(O)CC1(C)C ; CC(C)(C)OC(=O)N1CC(OCCO)CC1(C)C]

In a 250 mL flask, tert-butyl 4-hydroxy-2,2-dimethyl-pyrrolidine-1-carboxylate (3 g, 13.93 mmol) was dissolved in N,N-dimethylformamide (15 mL) at 0° C. and sodium hydride (1.8 g of 60% w/w in a mineral oil, 45.00 mmol) was carefully added. The mixture was stirred at 0° C. for 15 min and then 2-bromoethoxy-tert-butyl-dimethyl-silane (9 mL, 41.95 mmol) was added dropwise at 0° C. and the mixture was allowed to warm to room temperature. The mixture was stirred for 16 h. The mixture was then cooled to 0° C., quenched with water and extracted with ether. The organic extract was washed with water, dried (sodium sulfate), filtered and concentrated in vacuo. The resulting orange oil was purified by silica gel chromatography eluting with a gradient from 0-30% ethyl acetate in hexanes to afford the tert-butyl(dimethyl)silyl protected intermediate which was dissolved in tetrahydrofuran (20 mL), treated with a tetrahydrofuran solution of TBAF (28 mL of 1 M, 28.00 mmol) and stirred for 2 h at room temperature. The mixture was concentrated and the residue was dissolved in dichloromethane, washed with water, dried over sodium sulfate, filtered and evaporated in vacuo. The obtained crude material was purified by silica gel chromatography eluting with a gradient from 0-20% methanol in dichloromethane to give tert-butyl 4-(2-hydroxyethoxy)-2,2-dimethyl-pyrrolidine-1-carboxylate (1.6 g, 44% yield). $^1$H NMR (400 MHz, Chloroform-d) δ 3.97 (d, J=4.0 Hz, 1H), 3.80-3.34 (m, 6H), 2.05 (t, J=6.1 Hz, 1H), 1.97 (d, J=16.4 Hz, 2H), 1.52-1.30 (m, 15H). ESI-MS m/z calc. 259.17834, found 260.17 (M+1)$^+$; Retention time: 0.55 min (LC Method A).

Step 12: tert-Butyl 4-(2-azidoethoxy)-2,2-dimethyl-pyrrolidine-1-carboxylate

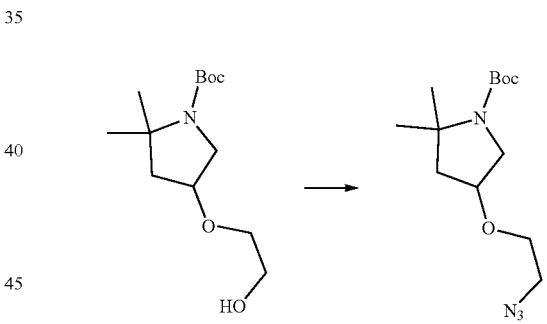

To a solution of tert-butyl 4-(2-hydroxyethoxy)-2,2-dimethyl-pyrrolidine-1-carboxylate (1.6 g, 6.169 mmol) in dichloromethane (20 mL) was added triethylamine (5.2 mL, 37.31 mmol) followed by methanesulfonyl chloride (1.4 mL, 18.09 mmol) at 0° C. The reaction mixture was stirred at room temperature for 20 h. The reaction mixture was quenched with ice-water and dichloromethane and the resulting layers were separated and the organic layer was dried over sodium sulfate, filtered and concentrated in vacuo to afford the crude mesylate which was combined with sodium azide (1.2 g, 18.46 mmol) in N,N-dimethylformamide (10 mL) and the mixture was stirred at 50° C. for 2 h. The reaction was quenched with water and extracted with ether. Organic extract was dried over sodium sulfate, evaporated in vacuo and the residue was purified by silica gel chromatography eluting with a gradient from 0-50% ethyl acetate in hexanes to give tert-butyl 4-(2-azidoethoxy)-2,2-dimethyl-pyrrolidine-1-carboxylate (1.33 g, 76%). $^1$H NMR (400 MHz, Chloroform-d) δ 3.96 (q, J=4.6 Hz, 1H), 3.69-3.31 (m, 6H), 2.06-1.91 (m, 2H), 1.53-1.32 (m, 15H).

Step 13: tert-Butyl 4-(2-aminoethoxy)-2,2-dimethyl-pyrrolidine-1-carboxylate

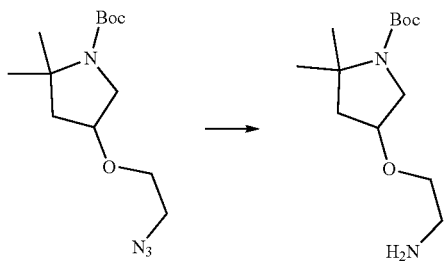 [SMILES: CC(C)(C)OC(=O)N1CC(OCCN=[N+]=[N-])CC1(C)C ; CC(C)(C)OC(=O)N1CC(OCCN)CC1(C)C]

To a solution of tert-butyl 4-(2-azidoethoxy)-2,2-dimethyl-pyrrolidine-1-carboxylate (1.33 g, 4.677 mmol) in methanol (20 mL) was added palladium on carbon (500 mg of 10% w/w, 0.4698 mmol). The mixture was saturated with hydrogen gas and stirred at room temperature while sparging hydrogen through the reaction mixture for 2 h. The mixture was filtered and evaporated in vacuo to afford tert-butyl 4-(2-aminoethoxy)-2,2-dimethyl-pyrrolidine-1-carboxylate (1.188 g, 98%). $^1$H NMR (400 MHz, Chloroform-d) δ 4.00-3.87 (m, 1H), 3.69-3.35 (m, 4H), 2.94-2.71 (m, 2H), 2.07-1.83 (m, 2H), 1.47 (q, J=9.4, 8.4 Hz, 15H).

Step 14: tert-Butyl 2,2-dimethyl-4-[2-[(6-sulfamoyl-2-pyridyl)amino]ethoxy]pyrrolidine-1-carboxylate

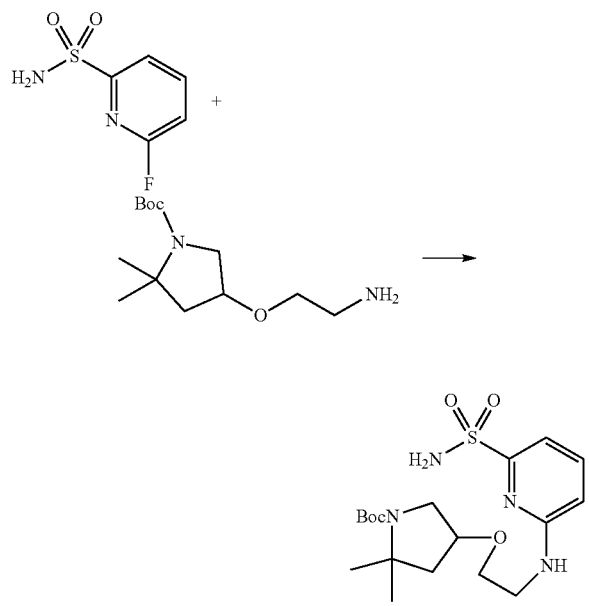

In a sealed 20 mL microwave vial, a solution of tert-butyl 4-(2-aminoethoxy)-2,2-dimethyl-pyrrolidine-1-carboxylate (1.188 mg, 4.598 mmol), 6-fluoropyridine-2-sulfonamide (810 mg, 4.598 mmol) and diisopropylethylamine (4 mL, 22.96 mmol) in n-BuOH (10 mL) was stirred at 150° C. for 16 h. The solvent was removed in vacuo and the residue was dissolved in dichloromethane and washed with water. Organic extract was dried over sodium sulfate, evaporated and purified by silica gel chromatography eluting with a gradient from 0-40% ethyl acetate in hexanes to give tert-butyl 2,2-dimethyl-4-[2-[(6-sulfamoyl-2-pyridyl)amino]ethoxy]pyrrolidine-1-carboxylate (1.500 g, 66%). ESI-MS m/z calc. 414.1937, found 415.3 (M+1)$^+$; Retention time: 0.61 min (LC Method A).

Step 15: tert-Butyl 4-[2-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]ethoxy]-2,2-dimethyl-pyrrolidine-1-carboxylate

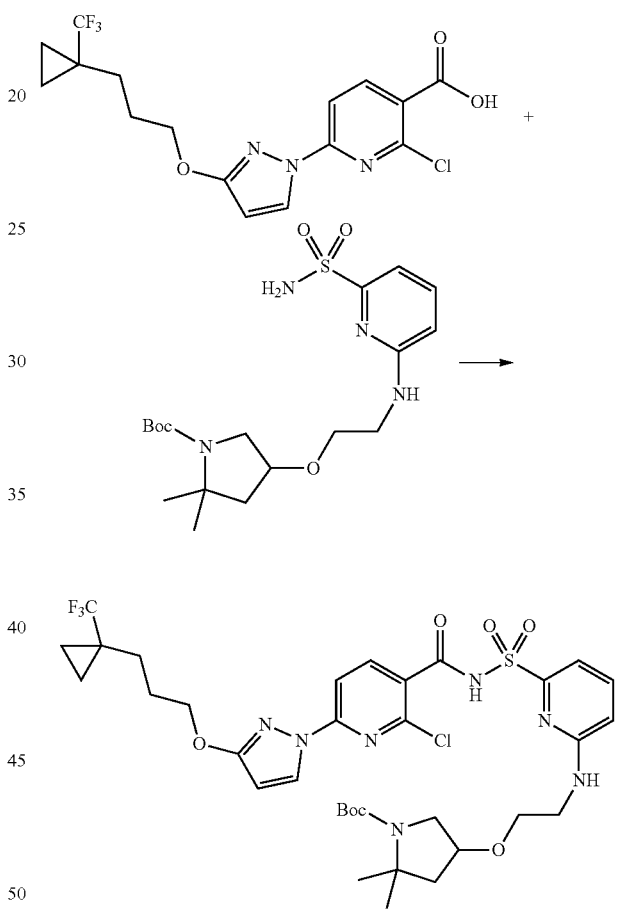

A 50 mL flask charged with carbonyl diimidazole (208 mg, 1.283 mmol) and 2-chloro-6-[3-[3-[1-(trifluoromethyl)cyclopropyl]propoxy]pyrazol-1-yl]pyridine-3-carboxylic acid (500 mg, 1.283 mmol) was evacuated and backfilled with nitrogen (3×). Added tetrahydrofuran (8 mL) and the mixture was stirred at 50° C. for 1 h. Next, a solution of tert-butyl 2,2-dimethyl-4-[2-[(6-sulfamoyl-2-pyridyl)amino]ethoxy]pyrrolidine-1-carboxylate (483 mg, 1.165 mmol) and 1,8-diazabicyclo[5.4.0]undec-7-ene (450 mg, 2.956 mmol) in tetrahydrofuran (6 mL) was added and the mixture was stirred overnight 50° C. The reaction was diluted with ethyl acetate and washed with water. The organic phase was dried over sodium sulfate, evaporated in vacuo and purified by silica gel chromatography eluting with a gradient from 0-50% ethyl acetate in hexanes to afford some pure fractions. Mixed fractions were purified by preparative reverse phase HPLC (C₁₈): 1-99% gradient of acetonitrile in water/hydrochloric acid modifier. Pure fractions from both purifications were combined to give tert-butyl 4-[2-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]ethoxy]-2,2-dimethyl-pyrrolidine-1-carboxylate (483 mg, 53%). ESI-MS m/z calc. 785.25854, found 786.33 (M+1)⁺; Retention time: 0.88 min (LC Method A).

Step 16: 2-Chloro-N-[[6-[2-(5,5-dimethylpyrrolidin-3-yl)oxyethylamino]-2-pyridyl]sulfonyl]-6-[3-[3-[1-(trifluoromethyl)cyclopropyl]propoxy]pyrazol-1-yl]pyridine-3-carboxamide

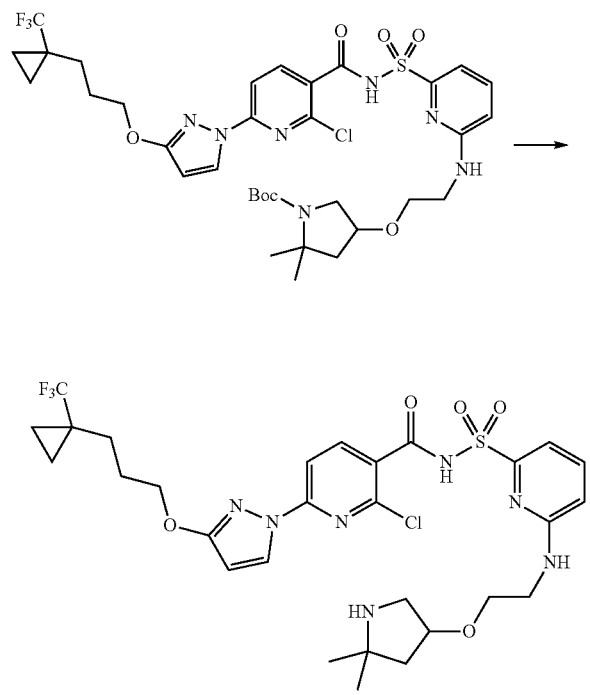 [SMILES: CC(C)(C)OC(=O)N1CC(OCCNc2cccc(S(=O)(=O)NC(=O)c3ccc(-n4ccc(OCCCC5(C(F)(F)F)CC5)n4)nc3Cl)n2)CC1(C)C ; CC1(C)CC(OCCNc2cccc(S(=O)(=O)NC(=O)c3ccc(-n4ccc(OCCCC5(C(F)(F)F)CC5)n4)nc3Cl)n2)CN1]

A solution of tert-butyl 4-[2-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]ethoxy]-2,2-dimethyl-pyrrolidine-1-carboxylate (483 mg, 0.61 mmol) in dioxane (5 mL) was treated with hydrochloric acid in dioxane (6 mL of 6 M, 36.00 mmol) and stirred at room temperature for 2 h. The mixture was evaporated in vacuo and the residue was quenched with aqueous sodium bicarbonate. The formed white precipitate was filtered off and washed with ethyl acetate. The aqueous phase was additionally extracted with ethyl acetate, combined organic extracts were dried over sodium sulfate, filtered and evaporated to additional solid product which was combined with the earlier precipitated solid and dried in vacuo to afford 2-chloro-N-[[6-[2-(5,5-dimethylpyrrolidin-3-yl)oxyethylamino]-2-pyridyl]sulfonyl]-6-[3-[3-[1-(trifluoromethyl)cyclopropyl]propoxy]pyrazol-1-yl]pyridine-3-carboxamide (350 mg, 83%). ESI-MS m/z calc. 685.2061, found 686.3 (M+1)⁺; Retention time: 0.64 min (LC Method A).

Step 17: 12,12-Dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.111,14.05,10]tetracosa-1(23),5,7,9,19,21-hexaene-2,2,4-trione

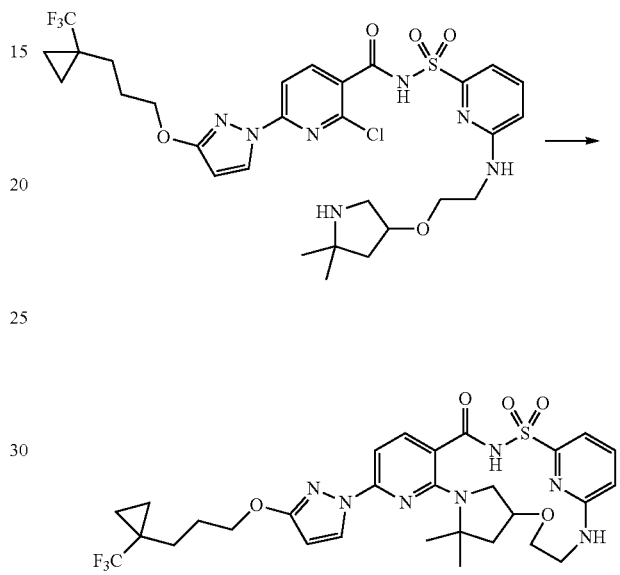

In a 5 mL microwave vial, cesium fluoride (162 mg, 1.066 mmol), potassium carbonate (367 mg, 2.655 mmol) and 4 Å molecular sieves (300 mg) were combined and the vial was evacuated/backfilled with nitrogen. Next, a solution of 2-chloro-N-[[6-[2-(5,5-dimethylpyrrolidin-3-yl)oxyethylamino]-2-pyridyl]sulfonyl]-6-[3-[3-[1-(trifluoromethyl)cyclopropyl]propoxy]pyrazol-1-yl]pyridine-3-carboxamide (360 mg, 0.5247 mmol) in dimethyl sulfoxide (5 mL) was added and the mixture was stirred at 150° C. overnight. The mixture was filtered and purified by preparative reverse phase HPLC (C₁₈): gradient from 1-99% acetonitrile in water/hydrochloric acid modifier (15 min) to afford 12,12-dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.111,14.05,10]tetracosa-1(23),5,7,9,19,21-hexaene-2,2,4-trione (118.2 mg, 34%). ¹H NMR (400 MHz, Chloroform-d) δ 9.51 (s, 1H), 8.16 (d, J=2.7 Hz, 1H), 7.90 (d, J=8.0 Hz, 1H), 7.60 (t, J=7.8 Hz, 1H), 7.52 (d, J=7.2 Hz, 1H), 7.15 (d, J=8.2 Hz, 1H), 6.65 (d, J=7.3 Hz, 1H), 5.90 (d, J=2.7 Hz, 1H), 4.82 (s, 1H), 4.33 (d, J=7.1 Hz, 1H), 4.24 (t, J=6.1 Hz, 2H), 4.06 (s, 1H), 3.82 (t, J=9.5 Hz, 1H), 3.58 (d, J=12.1 Hz, 1H), 3.43-3.28 (m, 2H), 3.15-3.03 (m, 1H), 2.23-2.14 (m, 1H), 1.95 (dq, J=11.0, 6.3 Hz, 3H), 1.75 (dd, J=10.0, 6.2 Hz, 2H), 1.64 (s, 3H), 1.60 (s, 3H), 0.99-0.95 (m, 2H), 0.60 (d, J=4.8 Hz, 2H). ESI-MS m/z calc. 649.22943, found 650.29 (M+1)⁺; Retention time: 2.12 min (LC Method B).

Step 18: 12,12-Dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Enantiomer 1) (Compound 159) and 12,12-Dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Enantiomer 2) (Compound 160)

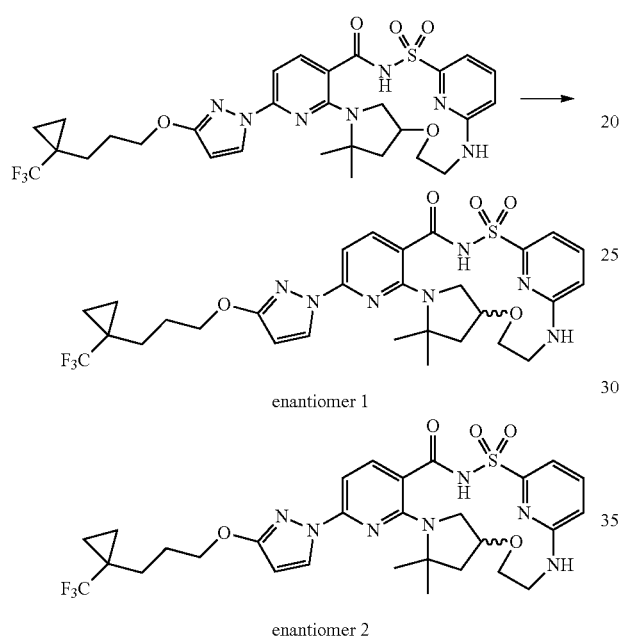

enantiomer 1 enantiomer 2

Racemic 12,12-dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (116 mg, 0.18 mmol) was subjected to chiral separation by SFC chromatography using a ChiralPak AS-H (250×21.2 mm, 5 μm particle size) with 28% acetonitrile/methanol (90:10)/72% carbon dioxide mobile phase at 70 mL/min over 8.0 min (injection volume=500 μL of 32 mg/mL solution in acetonitrile/methanol (90:10)) giving as the first enantiomer to elute, 12,12-dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (enantiomer 1) (Compound 159) (48.3 mg, 28%); ESI-MS m/z calc. 649.22943, found 650.32 (M+1)⁺; Retention time: 2.12 min (LC Method B) and as the second enantiomer to elute 12,12-dimethyl-8-(3-{3-[1-(trifluoromethyl)cyclopropyl]propoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (enantiomer 2) (Compound 160) (56.0 mg, 48%); ¹H NMR (400 MHz, dimethyl sulfoxide-d₆) δ 12.57 (s, 1H), 8.19 (d, J=2.8 Hz, 1H), 7.78 (d, J=8.1 Hz, 1H), 7.58 (t, J=7.7 Hz, 1H), 7.09 (d, J=7.3 Hz, 2H), 6.93 (d, J=8.1 Hz, 1H), 6.70 (d, J=8.3 Hz, 1H), 6.11 (d, J=2.7 Hz, 1H), 4.19 (t, J=6.2 Hz, 2H), 4.17-3.99 (m, 2H), 3.88 (t, J=11.7 Hz, 1H), 3.60 (d, J=12.9 Hz, 1H), 3.27-2.75 (m, 3H), 2.07 (dd, J=11.7, 6.0 Hz, 1H), 1.89-1.70 (m, 5H), 1.57 (d, J=9.3 Hz, 6H), 0.93-0.85 (m, 2H), 0.75 (s, 2H). ESI-MS m/z calc. 649.22943, found 650.43 (M+1)⁺; Retention time: 2.12 min (LC Method B).

Example 42: Preparation of (14S)-12,12-dimethyl-8-(3-{3-[1-(trifluoromethyl) cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 161)

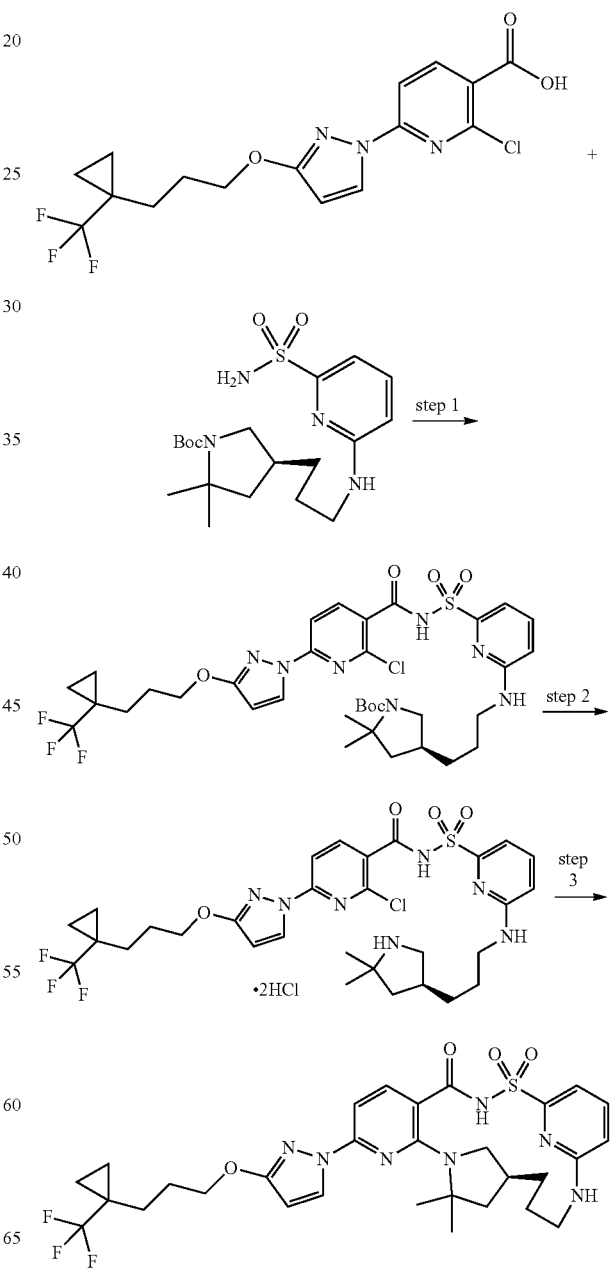

Step 1: tert-Butyl (4S)-4-[3-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate

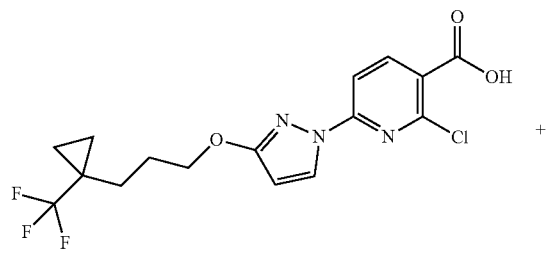

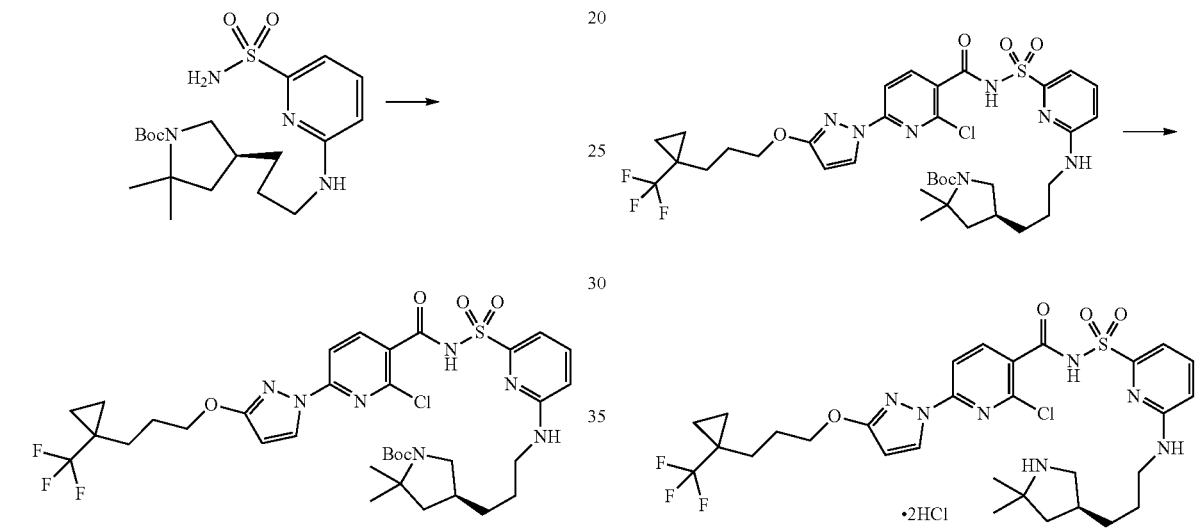

To a solution of 2-chloro-6-[3-[3-[1-(trifluoromethyl)cyclopropyl]propoxy]pyrazol-1-yl]pyridine-3-carboxylic acid (10 g, 25.66 mmol) in tetrahydrofuran (100 mL) was added carbonyl diimidazole (4.7 g, 27.71 mmol) and the mixture stirred at ambient temperature for 90 min. To this mixture was then added tert-butyl (4S)-2,2-dimethyl-4-[3-[(6-sulfamoyl-2-pyridyl)amino]propyl]pyrrolidine-1-carboxylate (12.0 g, 29.09 mmol) in tetrahydrofuran (50 mL) followed by 1,8-diazabicyclo[5.4.0]undec-7-ene (11.5 mL, 76.90 mmol) and the mixture was stirred at ambient temperature for 18 h. The reaction was diluted with water (250 mL) and the mixture slowly acidified with aqueous hydrochloric acid (23 mL of 6 M, 138.0 mmol). The mixture was extracted with ethyl acetate (500 mL) and the organic phase separated. The organic phase was washed with 300 mL of brine, dried over magnesium sulfate, filtered and concentrated in vacuo. The crude product was split into 3 equal portions with acetonitrile and chromatographed on a 415 reverse phase $C_{18}$ column eluting with a gradient from 50%-100% acetonitrile in water affording the product, tert-butyl (4S)-4-[3-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (13.63 g, 68%) as a waxy solid. $^1$H NMR (400 MHz, dimethyl sulfoxide-$d_6$) δ 12.75 (s, 1H), 8.39 (t, J=2.2 Hz, 1H), 8.10 (d, J=8.4 Hz, 1H), 7.70 (d, J=8.3 Hz, 1H), 7.62 (dd, J=8.5, 7.2 Hz, 1H), 7.24-7.14 (m, 2H), 6.74 (d, J=8.5 Hz, 1H), 6.20 (dd, J=8.6, 2.9 Hz, 1H), 4.23 (t, J=6.2 Hz, 2H), 3.51 (dt, J=18.4, 9.2 Hz, 1H), 3.24 (s, 2H), 2.74 (t, J=10.5 Hz, 1H), 2.05-1.96 (m, 1H), 1.91-1.69 (m, 5H), 1.51 (dt, J=15.6, 7.1 Hz, 2H), 1.40-1.27 (m, 15H), 1.18 (s, 3H), 0.97-0.88 (m, 2H), 0.80-0.71 (m, 2H). ESI-MS m/z calc. 783.27924, found 784.3 (M+1)$^+$; Retention time: 2.38 min (LC Method B).

Step 2: 2-Chloro-N-[[6-[3-[(3S)-5,5-dimethylpyrrolidin-3-yl]propylamino]-2-pyridyl]sulfonyl]-6-[3-[3-[1-(trifluoromethyl)cyclopropyl]propoxy]pyrazol-1-yl]pyridine-3-carboxamide (Dihydrochloride Salt)

To a solution of tert-butyl (4S)-4-[3-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (13.5 g, 17.21 mmol) in dichloromethane (100 mL) and toluene (50 mL) was added hydrochloric acid in dioxane (20 mL of 4 M, 80.00 mmol). The mixture was stirred at ambient temperature for 16 h. The solvent was removed in vacuo and the residue further evaporated from 200 mL of toluene giving 2-chloro-N-[[6-[3-[(3S)-5,5-dimethylpyrrolidin-3-yl]propylamino]-2-pyridyl]sulfonyl]-6-[3-[3-[1-(trifluoromethyl)cyclopropyl]propoxy]pyrazol-1-yl]pyridine-3-carboxamide (dihydrochloride salt) (12.7 g, 97%) which was used without further purification. $^1$H NMR (400 MHz, dimethyl sulfoxide-$d_6$) δ 12.80 (s, 1H), 9.31 (s, 1H), 9.14 (s, 1H), 8.41 (d, J=2.9 Hz, 1H), 8.11 (d, J=8.3 Hz, 1H), 7.72 (d, J=8.3 Hz, 1H), 7.63 (dd, J=8.5, 7.2 Hz, 1H), 7.19-7.15 (m, 3H), 6.78 (dd, J=8.6, 0.7 Hz, 1H), 6.21 (d, J=2.9 Hz, 1H), 4.24 (t, J=6.2 Hz, 2H), 3.28 (dh, J=27.2, 6.6, 6.1 Hz, 3H), 2.82 (tq, J=11.8, 7.2, 5.9 Hz, 1H), 2.43-2.32 (m, 1H), 1.95-1.81 (m, 3H), 1.77-1.68 (m, 2H), 1.61-1.31 (m, 8H), 1.25 (s, 3H), 0.96-0.88 (m, 2H), 0.81-0.70 (m, 2H). ESI-MS m/z calc. 683.2268, found 684.3 (M+1)$^+$; Retention time: 2.47 min (LC Method D).

Step 3: (14S)-12,12-Dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 161)

Example 43: Preparation of 8-[3-(3,3-dicyclopropylpropoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Enantiomer 1) (Compound 162) and 8-[3-(3,3-dicyclopropylpropoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Enantiomer 2) (Compound 163)

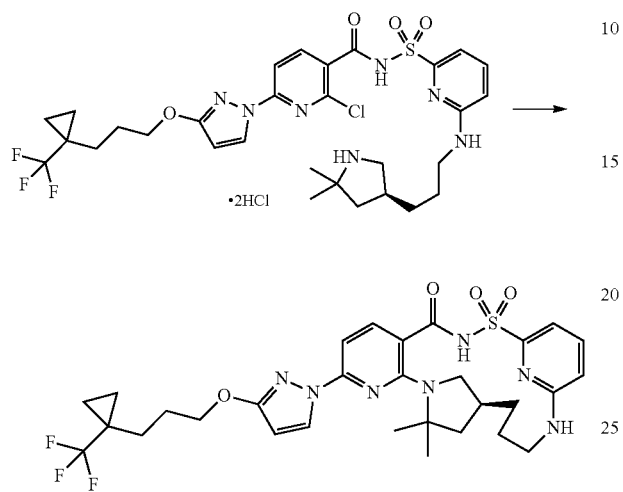

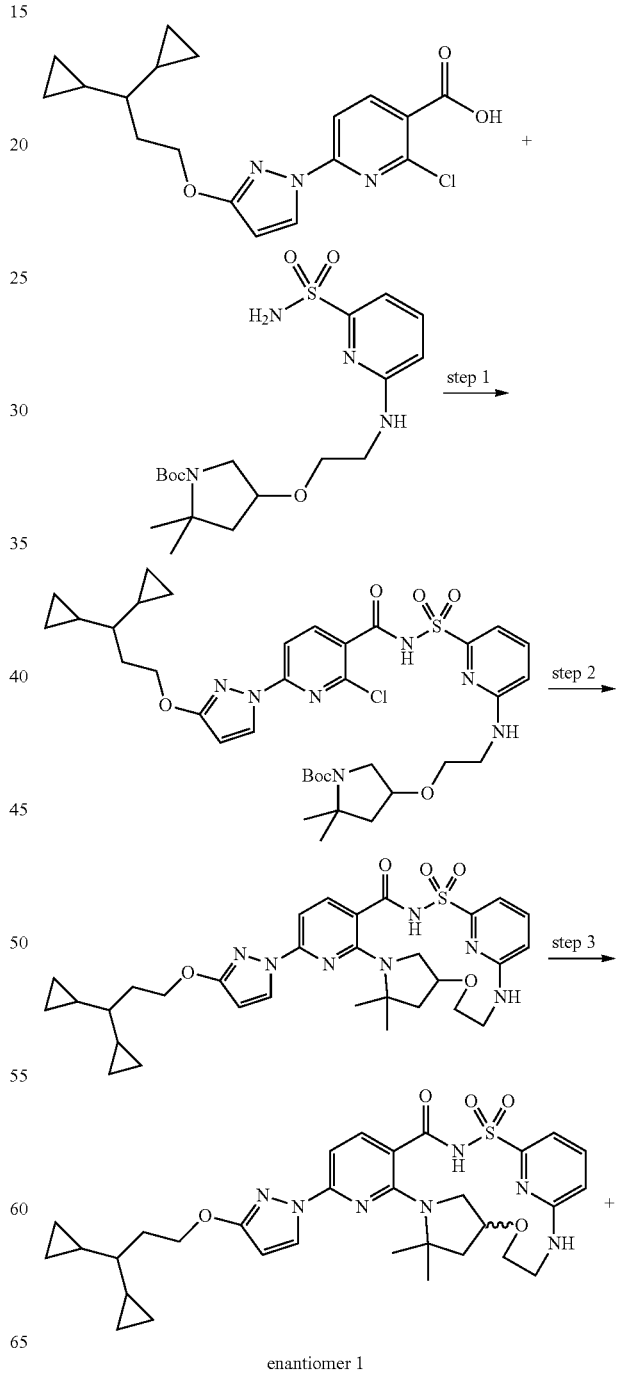

enantiomer 1

To a solution of 2-chloro-N-[[6-[3-[(3S)-5,5-dimethylpyrrolidin-3-yl]propylamino]-2-pyridyl]sulfonyl]-6-[3-[3-[1-(trifluoromethyl)cyclopropyl]propoxy]pyrazol-1-yl]pyridine-3-carboxamide (dihydrochloride salt) (12.7 g, 16.77 mmol) in NMP (200 mL) was added potassium carbonate (11.47 g, 82.99 mmol) followed by cesium fluoride (2.75 g, 18.10 mmol). The mixture was purged with nitrogen for 5 min. The mixture was heated at 150° C. for 22 h. The reaction mixture was then cooled to room temperature and added to chilled water (600 mL). The mixture was carefully acidified with aqueous hydrochloric acid (26 mL of 6 M, 156.0 mmol) affording a cream colored foamy slurry. The slurry was stirred at ambient temperature for 1 h. The solid was collected by filtration using a medium frit Buchner funnel. The wet filter cake was diluted with acetonitrile and chromatographed on a $C_{18}$ reverse phase column eluting with a gradient system of 50%-100% acetonitrile in water giving an off-white foam which was further dried in vacuo at 45° C. for 3 days giving (14S)-12,12-dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 161) (6.0 g, 55%). ¹H NMR (400 MHz, dimethyl sulfoxide-$d_6$) δ 12.48 (s, 1H), 8.21 (d, J=2.7 Hz, 1H), 7.81 (d, J=8.2 Hz, 1H), 7.57 (dd, J=8.5, 7.2 Hz, 1H), 7.05 (d, J=7.1 Hz, 1H), 6.97 (d, J=8.5 Hz, 1H), 6.91 (d, J=8.2 Hz, 1H), 6.71 (d, J=8.5 Hz, 1H), 6.12 (d, J=2.8 Hz, 1H), 4.20 (t, J=6.2 Hz, 2H), 3.92 (d, J=12.5 Hz, 1H), 3.16 (s, 1H), 2.95 (d, J=13.3 Hz, 1H), 2.71 (t, J=11.1 Hz, 1H), 2.12 (s, 1H), 1.84 (q, J=7.8, 6.3 Hz, 3H), 1.80-1.67 (m, 3H), 1.60 (s, 6H), 1.51 (s, 3H), 1.31 (q, J=12.0 Hz, 1H), 0.97-0.87 (m, 2H), 0.76 (q, J=3.0, 1.7 Hz, 2H). ESI-MS m/z calc. 647.2502, found 648.3 (M+1)⁺; Retention time: 9.64 min (LC Method F).

-continued

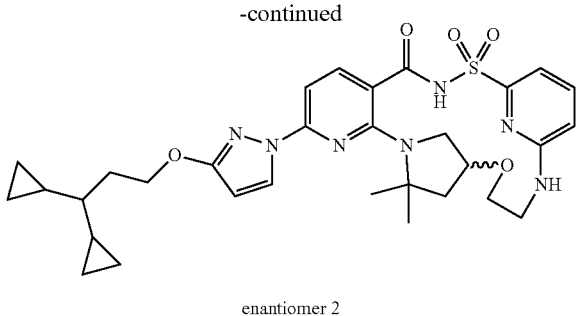

enantiomer 2

Step 1: 2-Chloro-6-[3-(3,3-dicyclopropylpropoxy) pyrazol-1-yl]-N-[[6-[2-(5,5-dimethylpyrrolidin-3-yl) oxyethylamino]-2-pyridyl]sulfonyl]pyridine-3-carboxamide

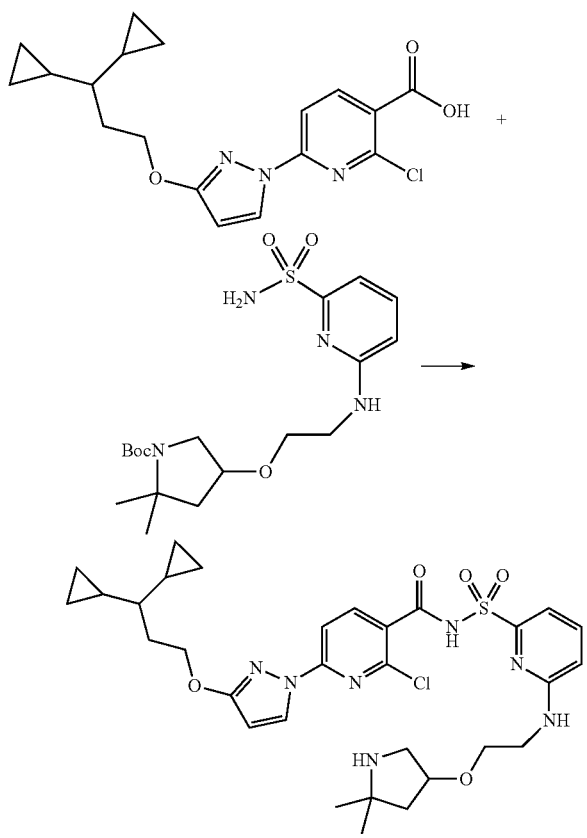

In a 50 mL flask 2-chloro-6-[3-(3,3-dicyclopropylpropoxy)pyrazol-1-yl]pyridine-3-carboxylic acid (400 mg, 1.106 mmol) and carbonyl diimidazole (270 mg, 1.665 mmol) were evacuated and backfilled with nitrogen (3×). Dry tetrahydrofuran (10 mL) was added and the reaction was stirred for 90 min at 50° C. Next, a solution of tert-butyl 2,2-dimethyl-4-[2-[(6-sulfamoyl-2-pyridyl)amino]ethoxy] pyrrolidine-1-carboxylate (158 mg, 0.3812 mmol) and 1,8-diazabicyclo[5.4.0]undec-7-ene (430 mg, 2.825 mmol) in tetrahydrofuran (4 mL) was added. The reaction was heated at 50° C. overnight. The reaction was diluted with ethyl acetate and washed with water. The organic phase was dried over sodium sulfate, evaporated in vacuo and purified by silica gel chromatography, eluting with a gradient from 0-50% ethyl acetate in hexanes to give an intermediate which was dissolved in dichloromethane (5 mL) and was treated with trifluoroacetic acid (1,000 μL, 12.98 mmol) and stirred for 2 h at room temperature. The solvent was removed in vacuo and the residue was quenched with aqueous sodium bicarbonate and ethyl acetate. White solid precipitate is formed. The biphasic mixture was filtered and the solid product was washed with ethyl acetate. Organic extract was separated from aqueous and dried over sodium sulfate, filtered and evaporated in vacuo. Solid material from the filter and evaporation residue were combined and dried in vacuo to afford 2-chloro-6-[3-(3,3-dicyclopropylpropoxy) pyrazol-1-yl]-N-[[6-[2-(5,5-dimethylpyrrolidin-3-yl)oxyethylamino]-2-pyridyl]sulfonyl]pyridine-3-carboxamide (310 mg, 43%). ESI-MS m/z calc. 657.25, found 658.32 (M+1)$^+$; Retention time: 0.68 min (LC Method B).

Step 2: 8-[3-(3,3-Dicyclopropylpropoxy)-1H-pyrazol-1-yl]-12,12-dimethyl-15-oxa-2λ$^6$-thia-3,9,11,18, 23-pentaazatetracyclo[17.3.1.1$^{11,14}$.0$^{5,10}$]tetracosa-1(23),5,7,9,19,21-hexaene-2,2,4-trione (Compound 156)

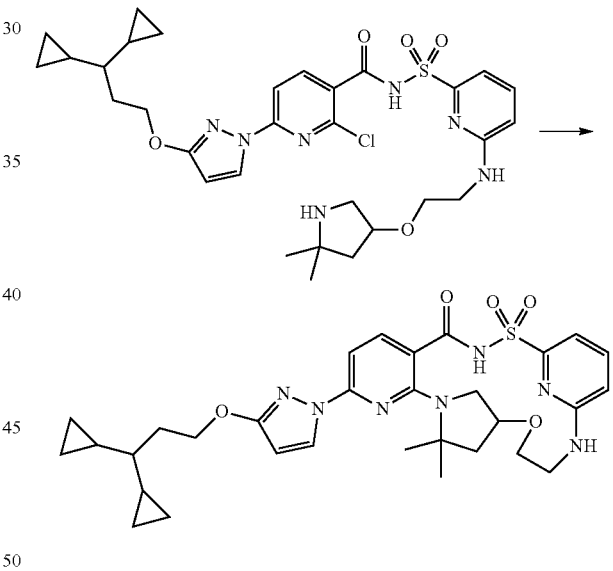

2-Chloro-6-[3-(3,3-dicyclopropylpropoxy)pyrazol-1-yl]-N-[[6-[2-(5,5-dimethylpyrrolidin-3-yl)oxyethylamino]-2-pyridyl]sulfonyl]pyridine-3-carboxamide (320 mg, 0.4862 mmol), potassium carbonate (340 mg, 2.460 mmol), cesium fluoride (150 mg, 0.9875 mmol) and 3 Å molecular sieves (300 mg) were combined and sealed and purged with nitrogen. Added dimethyl sulfoxide (4 mL) and the mixture was stirred at 150° C. overnight. The mixture was filtered and purified by preparative reverse phase HPLC (C$_{18}$): gradient from 1-99% acetonitrile in water/hydrochloric acid modifier to afford 8-[3-(3,3-dicyclopropylpropoxy)-1H-pyrazol-1-yl]-12,12-dimethyl-15-oxa-2λ$^6$-thia-3,9,11,18, 23-pentaazatetracyclo[17.3.1.1$^{11,14}$.0$^{5,10}$]tetracosa-1(23), 5,7,9,19,21-hexaene-2,2,4-trione (Compound 156) (92.5 mg, 30%). ESI-MS m/z calc. 621.2733, found 622.31 (M+1)$^+$; Retention time: 2.26 min (LC Method B).

Step 3: 8-[3-(3,3-Dicyclopropylpropoxy)-1H-pyrazol-1-yl]-12,12-dimethyl-15-oxa-2λ⁶-thia-3,9,11,18,23-pentaazatetracyclo[17.3.1.111,14.05,10]tetracosa-1(23),5,7,9,19,21-hexaene-2,2,4-trione (Enantiomer 1) (Compound 162) and 8-[3-(3,3-dicyclopropylpropoxy)-1H-pyrazol-1-yl]-12,12-dimethyl-15-oxa-2λ⁶-thia-3,9,11,18,23-pentaazatetracyclo[17.3.1.111,14.05,10]tetracosa-1(23),5,7,9,19,21-hexaene-2,2,4-trione (Enantiomer 2) (Compound 163)

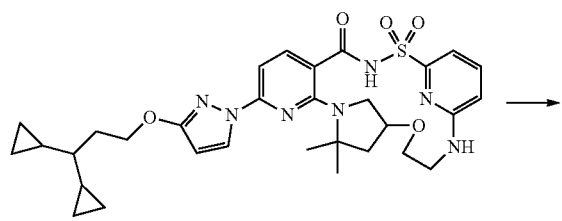

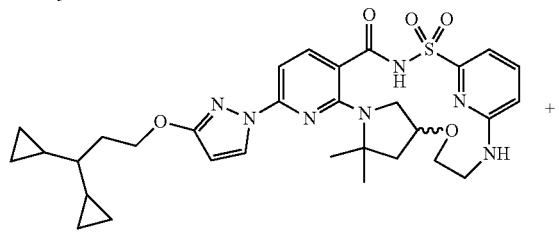

enantiomer 1

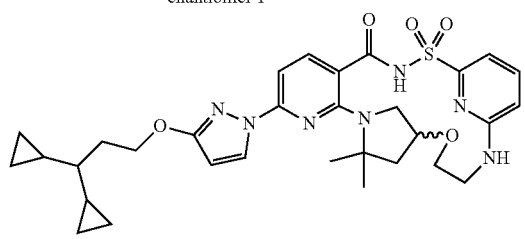

enantiomer 2

Racemic 8-[3-(3,3-dicyclopropylpropoxy)-1H-pyrazol-1-yl]-12,12-dimethyl-15-oxa-2λ⁶-thia-3,9,11,18,23-pentaazatetracyclo[17.3.1.111,14.05,10]tetracosa-1(23),5,7,9,19,21-hexaene-2,2,4-trione (Compound 156) (90 mg, 0.145 mmol) was subjected to chiral separation by SFC chromatography using a ChiralPak AS-H (250×10 mm, 5 µm particle size) with 40% acetonitrile/methanol (90:10)/60% carbon dioxide mobile phase at 10 mL/min over 8.0 min (injection volume=70 µL of 24 mg/mL solution in acetonitrile/methanol (90:10)) giving as the first enantiomer to elute, 8-[3-(3,3-dicyclopropylpropoxy)-1H-pyrazol-1-yl]-12,12-dimethyl-15-oxa-2λ⁶-thia-3,9,11,18,23-pentaazatetracyclo[17.3.1.111,14.05,10]tetracosa-1(23),5,7,9,19,21-hexaene-2,2,4-trione (enantiomer 1) (Compound 162) (28.4 mg, 19%); ESI-MS m/z calc. 621.2733, found 622.38 (M+1)⁺; Retention time: 2.26 min (LC Method B) and as the second enantiomer to elute 8-[3-(3,3-dicyclopropylpropoxy)-1H-pyrazol-1-yl]-12,12-dimethyl-15-oxa-2λ⁶-thia-3,9,11,18,23-pentaazatetracyclo[17.3.1.111,14.05,10]tetracosa-1(23),5,7,9,19,21-hexaene-2,2,4-trione (Compound 163) (enantiomer 2) (35.4 mg, 39%); ¹H NMR (400 MHz, dimethyl sulfoxide-d₆) δ 12.58 (s, 1H), 8.19 (d, J=2.7 Hz, 1H), 7.79 (d, J=8.2 Hz, 1H), 7.62-7.55 (m, 1H), 7.11 (dd, J=16.4, 5.9 Hz, 2H), 6.94 (d, J=8.2 Hz, 1H), 6.70 (d, J=8.5 Hz, 1H), 6.10 (d, J=2.7 Hz, 1H), 4.36 (t, J=6.8 Hz, 2H), 4.19-4.00 (m, 2H), 3.88 (t, J=11.3 Hz, 1H), 3.60 (d, J=13.0 Hz, 1H), 3.22 (s, 1H), 2.86 (d, J=9.5 Hz, 1H), 2.07 (dd, J=11.8, 5.9 Hz, 1H), 1.89 (q, J=6.8 Hz, 2H), 1.78 (t, J=10.9 Hz, 1H), 1.57 (d, J=10.0 Hz, 6H), 0.68 (qt, J=8.4, 5.0 Hz, 2H), 0.39 (q, J=5.9 Hz, 4H), 0.34-0.24 (m, 1H), 0.20 (dt, J=10.4, 5.2 Hz, 2H), 0.03 (dt, J=8.0, 4.0 Hz, 2H), ESI-MS m/z calc. 621.2733, found 622.42 (M+1)⁺; Retention time: 2.25 min (LC Method B).

Example 44: Preparation of 20,20-dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (Enantiomer 1) (Compound 165) and 20,20-dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (Enantiomer 2) (Compound 166)

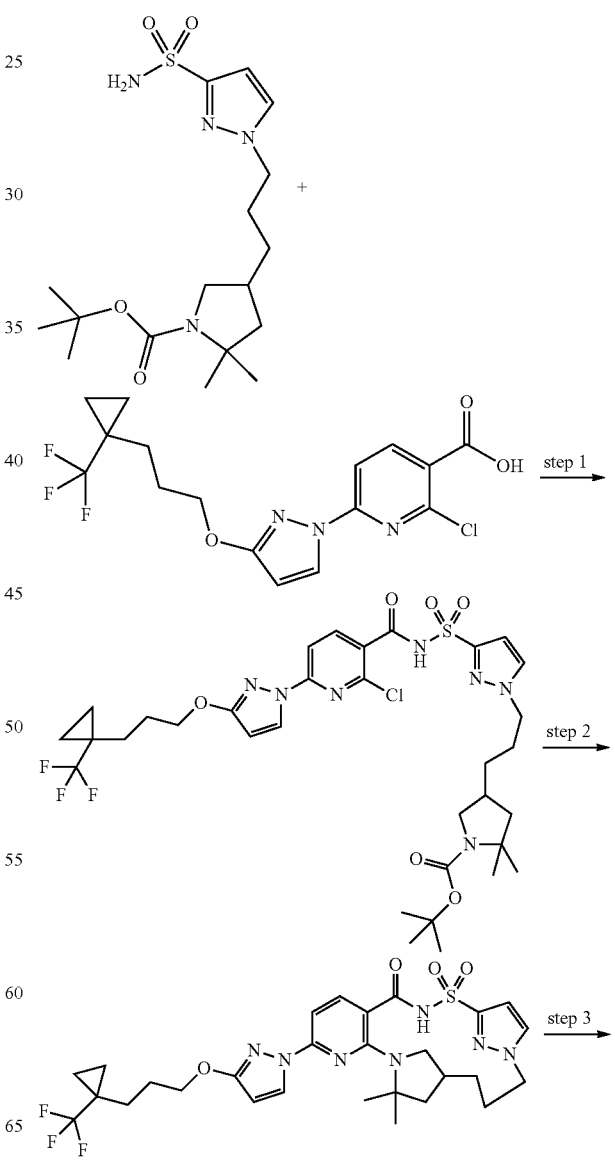

421

-continued

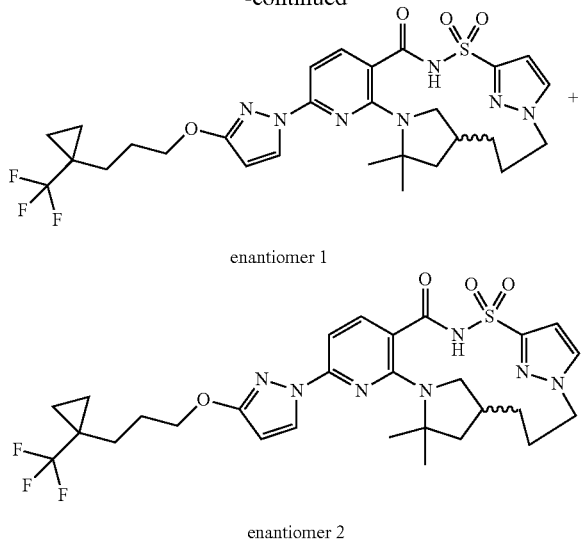

enantiomer 1 enantiomer 2

Step 1: tert-Butyl 4-[3-[3-[[2-chloro-6-[3-[3-[1-(trifluoromethyl)cyclopropyl]propoxy]pyrazol-1-yl]pyridine-3-carbonyl]sulfamoyl]pyrazol-1-yl]propyl]-2,2-dimethyl-pyrrolidine-1-carboxylate

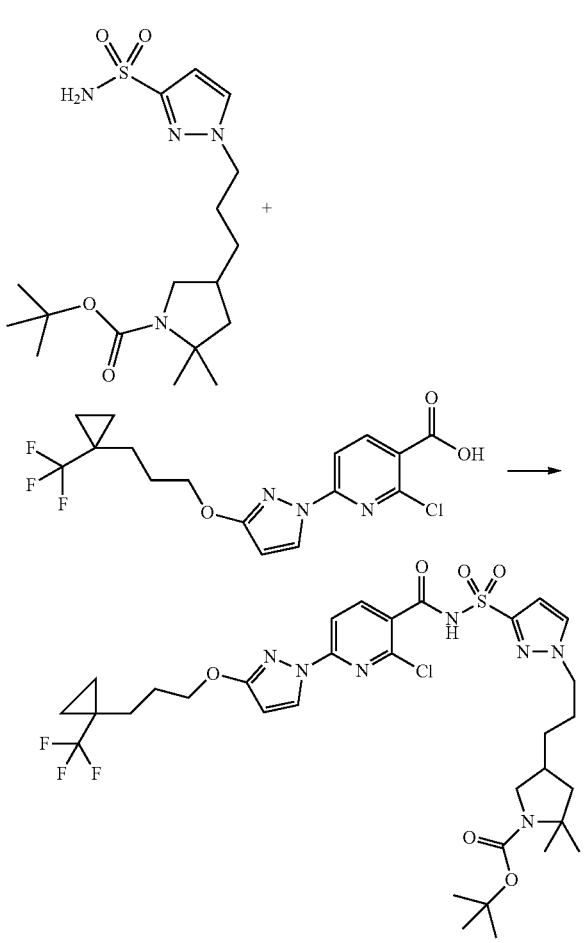

422

2-Chloro-6-[3-[3-[1-(trifluoromethyl)cyclopropyl]propoxy]pyrazol-1-yl]pyridine-3-carboxylic acid (275 mg, 0.7056 mmol) and carbonyl diimidazole (130 mg, 0.8017 mmol) were combined in anhydrous tetrahydrofuran (5 mL) and stirred for 60 min at 50° C. Then a tetrahydrofuran solution (7 mL) of tert-butyl 2,2-dimethyl-4-[3-(3-sulfamoylpyrazol-1-yl)propyl]pyrrolidine-1-carboxylate (206 mg, 0.5330 mmol) and 1,8-diazabicyclo[5.4.0]undec-7-ene (200 µL, 1.337 mmol) was added. The reaction was heated at 50° C. for 4 h. The reaction was diluted with ethyl acetate and washed with a 1M citric acid solution, followed by brine. The organics were separated, dried over sodium sulfate, filtered and evaporated and then purified by silica gel chromatography using a gradient of 100% hexanes to 75% ethyl acetate in hexanes to afford an off-white solid, tert-butyl 4-[3-[3-[[2-chloro-6-[3-[3-[1-(trifluoromethyl)cyclopropyl]propoxy]pyrazol-1-yl]pyridine-3-carbonyl]sulfamoyl]pyrazol-1-yl]propyl]-2,2-dimethyl-pyrrolidine-1-carboxylate (226 mg, 56%). ESI-MS m/z calc. 757.2636, found 758.32 (M+1)⁺; Retention time: 0.88 min (LC Method A).

Step 2: 20,20-Dimethyl-4-(3-{3-[1-(trifluoromethyl)cyclopropyl]propoxy}-1H-pyrazol-1-yl)-10$\lambda^6$-thia-1,3,9,14,22-pentaazatetracyclo[16.2.1.111,14.02,7]docosa-2(7),3,5,11(22),12-pentaene-8,10,10-trione (Compound 155)

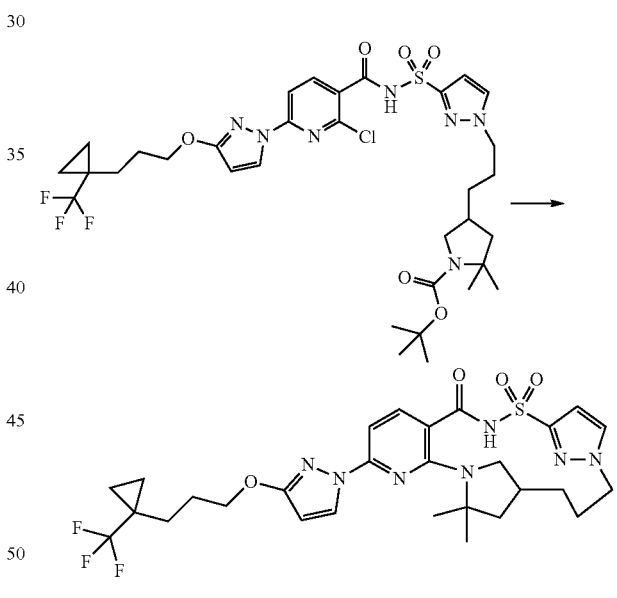

tert-Butyl 4-[3-[3-[[2-chloro-6-[3-[3-[1-(trifluoromethyl)cyclopropyl]propoxy]pyrazol-1-yl]pyridine-3-carbonyl]sulfamoyl]pyrazol-1-yl]propyl]-2,2-dimethyl-pyrrolidine-1-carboxylate (226 mg, 0.2981 mmol) was dissolved in dichloromethane (5 mL) and to the mixture was added hydrochloric acid in dioxane (2 mL of 4 M, 8.000 mmol) and stirred at room temperature for 30 min. Concentrated the mixture to dryness under reduced pressure and combined the residue with potassium carbonate (250 mg, 1.809 mmol), cesium fluoride (73 mg, 0.4806 mmol), 3 Å molecular sieves and dimethyl sulfoxide (6 mL) in a vial, purged with nitrogen, capped, heated to 140° C. and stirred for 16 h. The reaction mixture was allowed to cool to room temperature, filtered and then purified by reverse-phase preparative chromatography (C₁₈ column, 30% to 99% acetonitrile (no modifier) in water (5 mM hydrochloric acid) over 30 min) to afford a white solid characterized as 20,20-dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (Compound 155) (96 mg, 51%). ¹H NMR (400 MHz, dimethyl sulfoxide-d₆) δ 12.69 (s, 1H), 8.18 (d, J=2.8 Hz, 1H), 8.00 (d, J=2.3 Hz, 1H), 7.71 (d, J=8.1 Hz, 1H), 7.04-6.80 (m, 2H), 6.10 (d, J=2.8 Hz, 1H), 4.30-4.05 (m, 4H), 2.07 (s, 3H), 1.99-1.66 (m, 6H), 1.55 (s, 3H), 1.47 (s, 3H), 1.33 (t, J=12.3 Hz, 1H), 0.98-0.87 (m, 2H), 0.75 (s, 2H), 0.64 (s, 1H). ESI-MS m/z calc. 621.2345, found 622.24 (M+1)⁺; Retention time: 2.22 min (LC Method B).

Step 3: 20,20-Dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (Enantiomer 1) (Compound 165) and 20,20-dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (Enantiomer 2) (Compound 166)

Racemic 20,20-dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (Compound 155) (88 mg, 0.1401 mmol) was subjected to chiral SFC chromatography. The following SFC protocol was employed: ChiralPak AS-3 (150×2.1 mm), 3 μm; 35° C., Mobile phase: 28% acetonitrile:methanol (90:10), 72% carbon dioxide with a flow rate of 0.5 mL/min. The first enantiomer to elute was 20,20-dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (enantiomer 1) (Compound 165) (36 mg, 82%). ESI-MS m/z calc. 621.2345, found 622.24 (M+1)⁺; Retention time: 2.21 min (LC Method B). The second enantiomer to elute was 20,20-dimethyl-4-(3-{3-[1-(trifluoromethyl)cyclopropyl]propoxy}-1H-pyrazol-1-yl)-10λ⁶-thia-1,3,9,14,22-pentaazatetracyclo[16.2.1.111,14.02,7]docosa-2(7),3,5,11(22),12-pentaene-8,10,10-trione (enantiomer 2) (Compound 166) (34 mg, 77%). ¹H NMR (400 MHz, dimethyl sulfoxide-d₆) δ 12.69 (s, 1H), 8.18 (d, J=2.8 Hz, 1H), 8.00 (d, J=2.3 Hz, 1H), 7.71 (d, J=8.1 Hz, 1H), 7.04-6.80 (m, 2H), 6.10 (d, J=2.8 Hz, 1H), 4.30-4.05 (m, 4H), 2.74-2.63 (m, 1H), 2.07 (s, 3H), 1.99-1.66 (m, 7H), 1.55 (s, 3H), 1.47 (s, 3H), 1.33 (t, J=12.3 Hz, 1H), 0.98-0.87 (m, 2H), 0.75 (s, 2H), 0.64 (s, 1H). ESI-MS m/z calc. 621.2345, found 622.35 (M+1)⁺; Retention time: 2.21 min (LC Method B).

Example 45: Preparation of (14S)-12,12-dimethyl-8-(2-oxo-3-{3-[1-(trifluoromethyl)cyclopropyl]propyl}pyrrolidin-1-yl)-2λ⁶-thia-3,9,11,18,23-pentaazatetracyclo[17.3.1.111,14.05,10]tetracosa-1(22),5,7,9,19(23),20-hexaene-2,2,4-trione (Diastereomer 1) (Compound 174) and (14S)-12,12-dimethyl-8-(2-oxo-3-{3-[1-(trifluoromethyl)cyclopropyl]propyl}pyrrolidin-1-yl)-2λ⁶-thia-3,9,11,18,23-pentaazatetracyclo[17.3.1.111,14.05,10]tetracosa-1(22),5,7,9,19(23),20-hexaene-2,2,4-trione (Diastereomer 2) (Compound 175)

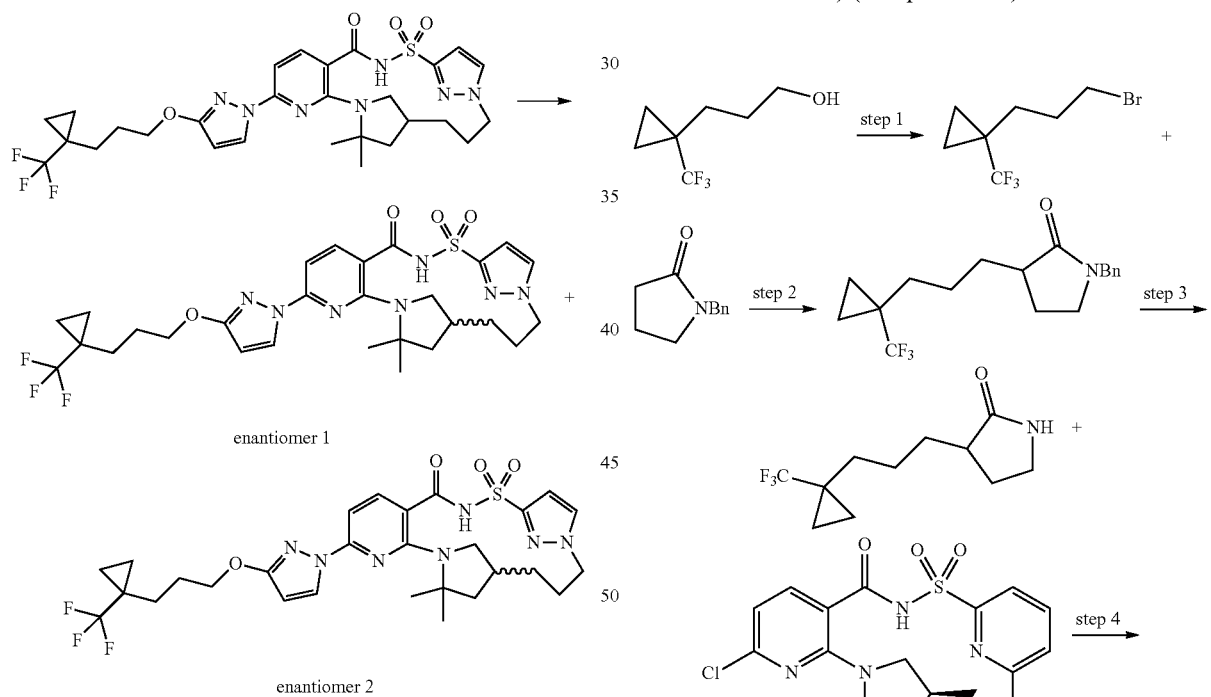

-continued

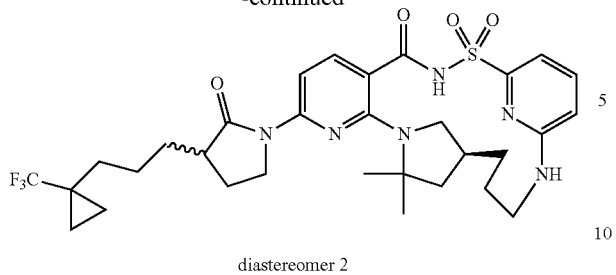

diastereomer 2

Step 1:
1-(3-Bromopropyl)-1-(trifluoromethyl)cyclopropane

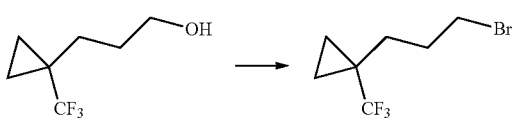

To a stirring solution of triphenylphosphine (655 mg, 2.497 mmol) in anhydrous dichloromethane (10 mL) under nitrogen atmosphere at −15° C. was dropwise added a solution of molecular bromine (130 μL, 2.524 mmol) in dichloromethane (2 mL) over 8 min and on completion of addition (pale yellow solution) the mixture was stirred an additional 15 min at −15° C. The mixture was then cooled to −30° C. and a solution of 3-[1-(trifluoromethyl)cyclopropyl]propan-1-ol (500 mg, 2.379 mmol) and pyridine (202 μL, 2.498 mmol) in dichloromethane (3 mL) was added dropwise over 5 min and on completion of addition the mixture was warmed to −5° C. and stirred for 1 h. The reaction mixture was then poured into pentane (250 mL) resulting in a mass of white precipitate. This suspension was filtered over Celite and the filtrate was reduced under rotary evaporation (250 mbar and 30° C. water bath) to give a white solid. To this solid was added pentane and the mixture briefly sonicated and filtered. Concentration of this filtrate gave a white solid which was again briefly sonicated with pentane and filtered giving crude 1-(3-bromopropyl)-1-(trifluoromethyl)cyclopropane (500 mg, 64%) as a clear oil. ¹H NMR (400 MHz, Chloroform-d) δ, 3.42 (t, J=6.4 Hz, 2H), 2.09-1.95 (m, 2H), 1.71 (d, J=5.8 Hz, 2H), 1.36-1.20 (m, 2H), 1.02-0.93 (m, 2H), 0.61-0.58 (m, 2H). NMR showed purity ~70%. The product was used for the next step without any further purification.

Step 2: 1-Benzyl-3-[3-[1-(trifluoromethyl)cyclopropyl]propyl]pyrrolidin-2-one

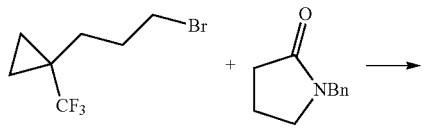

-continued

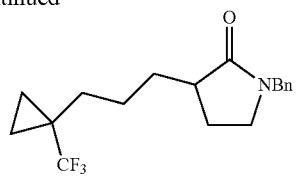

A 100 mL three neck flask was dried with a heat gun under vacuum and filled with nitrogen. The flask was charged with 1-benzylpyrrolidin-2-one (0.21 mL, 1.312 mmol) and anhydrous tetrahydrofuran (2 mL). After cooling to −78° C., a solution of n-butyllithium (0.59 mL of 2.5 M, 1.475 mmol) (2.5 M in hexanes) was added dropwise inducing formation of a pink solution. After stirring at −78° C. for 20 min (the solution turned pale yellow), a solution of 1-(3-bromopropyl)-1-(trifluoromethyl)cyclopropane (500 mg, 1.515 mmol) in tetrahydrofuran (0.5 mL) was added dropwise (color turned darker yellow). The mixture was stirred in the cooling bath that was allowed to slowly warm up to room temperature. After 14 h, the mixture was quenched with the addition of saturated aqueous ammonium chloride (50 mL). The product was extracted with ethyl acetate (2×30 mL). The organic layer was dried over sodium sulfate, filtered and concentrated under reduced pressure. The crude product was purified by silica gel chromatography using a gradient of ethyl acetate (0 to 100% over 30 min) in hexanes giving 1-benzyl-3-[3-[1-(trifluoromethyl)cyclopropyl]propyl]pyrrolidin-2-one (227 mg, 53%) as a colorless oil. ¹H NMR (400 MHz, Chloroform-d) δ 7.37-7.16 (m, 5H), 4.49 (d, J=14.7 Hz, 1H), 4.41 (d, J=14.7 Hz, 1H), 3.22-3.14 (m, 2H), 2.45 (qd, J=8.9, 4.3 Hz, 1H), 2.23-2.10 (m, 1H), 1.94-1.80 (m, 1H), 1.72-1.32 (m, 6H), 0.99-0.88 (m, 2H), 0.61-0.51 (m, 2H). ESI-MS m/z calc. 325.16534, found 326.3 (M+1)⁺; Retention time: 1.9 min (LC Method B).

Step 3: 3-[3-[1-(Trifluoromethyl)cyclopropyl]propyl]pyrrolidin-2-one

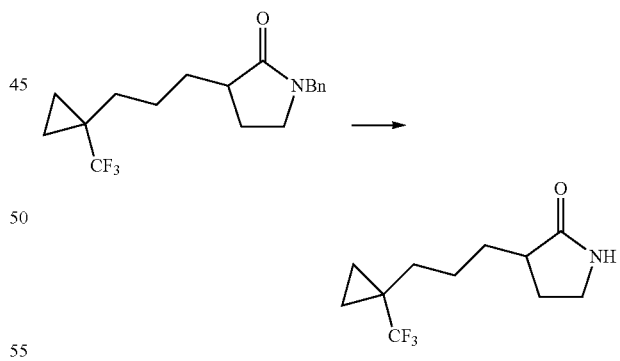

A 100 mL flask was charged under nitrogen with 1-benzyl-3-[3-[1-(trifluoromethyl)cyclopropyl]propyl]pyrrolidin-2-one (227 mg, 0.6977 mmol), propylamine (3 mL) and 1,2-ethandiamine (0.3 mL, 4.488 mmol). The mixture was cooled down to −20° C. (external cooling bath temperature) and lithium (47 mg, 6.771 mmol) (wire, briefly rinsed with hexanes, then freshly cut in small pieces) was added. A blue color developed around the small pieces of lithium and then disappeared quickly in a cyclic manner. After 20 min at −20° C., the blue color became permanent. The reaction was quenched by addition at −10° C. of methanol (400 μL) and water (10 mL). The product was extracted with ethyl acetate (2×25 mL). The combined organic extracts were dried over sodium sulfate and the solvents evaporated to give a crude material that was purified by flash chromatography on silica gel using a gradient of methanol (0%-15% over 30 min) in dichloromethane giving 192 mg of crude material. This material was dissolved in ethyl acetate (30 mL) and the organic phase was washed with 0.1 N hydrochloric acid (2×20 mL) and 1N hydrochloric acid (2×20 mL). The organic phase was then dried over sodium sulfate, filtered and the solvents evaporated to give 3-[3-[1-(trifluoromethyl) cyclopropyl]propyl]pyrrolidin-2-one (108 mg, 66%) as a white solid. $^1$H NMR (400 MHz, Chloroform-d) δ 5.76 (broad s, 1H), 3.41-3.28 (m, 2H), 2.40-2.23 (m, 2H), 1.88-1.73 (m, 2H), 1.67-1.44 (m, 4H), 1.42-1.30 (m, 1H), 0.97-0.90 (m, 2H), 0.61-0.47 (m, 2H).

ESI-MS m/z calc. 235.1184, found 236.2 (M+1)$^+$; Retention time: 1.43 min (LC Method B).

Step 4: (14S)-12,12-Dimethyl-8-(2-oxo-3-{3-[1-(trifluoromethyl)cyclopropyl]propyl}pyrrolidin-1-yl)-2λ$^6$-thia-3,9,11,18,23-pentaazatetracyclo [17.3.1.1$^{11,14}$.0$^{5,10}$]tetracosa-1(22),5,7,9,19(23), 20-hexaene-2,2,4-trione (Diastereomer 1) (Compound 174) and (14S)-12,12-dimethyl-8-(2-oxo-3-{3-[1-(trifluoromethyl)cyclopropyl] propyl}pyrrolidin-1-yl)-2λ$^6$-thia-3,9,11,18,23-pentaazatetracyclo[17.3.1.1$^{11,14}$.0$^{5,10}$]tetracosa-1(22), 5,7,9,19(23),20-hexaene-2,2,4-trione (Diastereomer 2) (Compound 175)

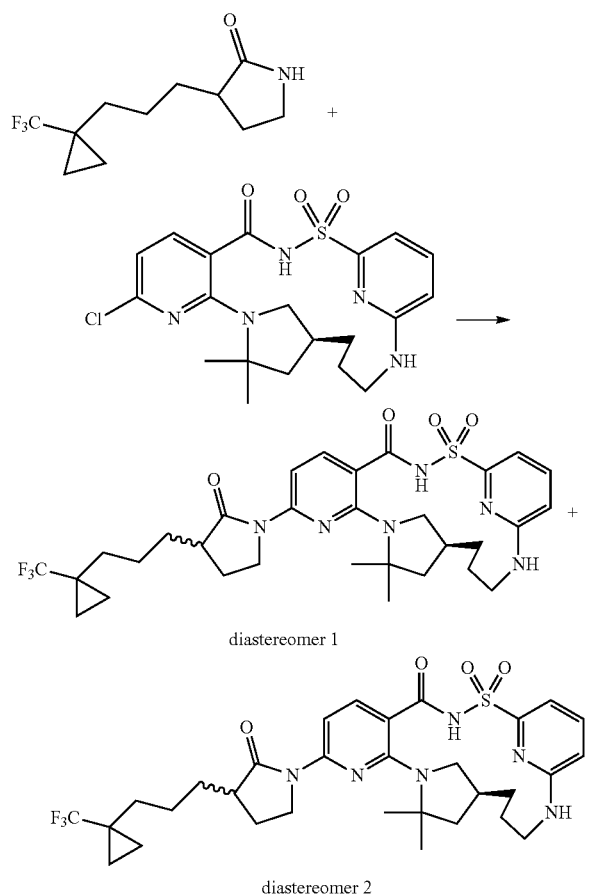

A 4 mL vial was charged with (14S)-8-chloro-12,12-dimethyl-2λ$^6$-thia-3,9,11,18,23-pentaazatetracyclo [17.3.1.1$^{11,14}$.0$^{5,10}$]tetracosa-1(23),5,7,9,19,21-hexaene-2,2,4-trione (100 mg, 0.2222 mmol), 3-[3-[1-(trifluoromethyl)cyclopropyl]propyl]pyrrolidin-2-one (54 mg, 0.2295 mmol), Pd$_2$(dba)$_3$ (33 mg, 0.03604 mmol), Xantphos (21 mg, 0.03629 mmol), cesium carbonate (430 mg, 1.320 mmol) and anhydrous dioxane (1.5 mL). The mixture was sparged with nitrogen for about 5 min (turned into a gel), capped and stirred at 120° C. for 14 h. The organic solvent was evaporated by blowing nitrogen in the vial. The reaction was then diluted with dimethyl sulfoxide (3 mL), microfiltered and subjected to reverse phase preparative HPLC (C$_{18}$) using a gradient of acetonitrile in water (1% to 99% over 15 min) and hydrochloric acid as a modifier (4×950 μL injections, 400 μL). The pure fractions were collected and the organic solvents were evaporated. The resulting aqueous solution was extracted with dichloromethane and the organic phase was dried over sodium sulfate. Filtration followed by evaporation of the filtrate solvent gave 74 mg of solid. The product was then further purified by flash chromatography on silica gel using a gradient of methanol (0% to 5% over 30 min) in dichloromethane to give a mixture of diastereomers that was subjected to chiral SFC separation (ChiralCel OJ-H (250×10 mm), 5 μM column; mobile phase 22% acetonitrile/methanol (90:10, no modifier), 78% carbon dioxide, 10 mL/min; concentration 24 mg/mL in acetonitrile/methanol/dimethyl sulfoxide (85:9:6); injection volume 70 μL, 100 bar). The first diastereomer to elute was (14S)-12,12-dimethyl-8-(2-oxo-3-{3-[1-(trifluoromethyl)cyclopropyl] propyl}pyrrolidin-1-yl)-2λ$^6$-thia-3,9,11,18,23-pentaazatetracyclo[17.3.1.1$^{11,14}$.0$^{5,10}$]tetracosa-1(22),5,7,9,19(23), 20-hexaene-2,2,4-trione (diastereomer 1) (Compound 174) (12.4 mg, 17%). $^1$H NMR (400 MHz, dimethyl sulfoxide-d$_6$) δ 12.39 (s, 1H), 7.67 (d, J=8.4 Hz, 1H), 7.56 (t, J=7.9 Hz, 1H), 7.51 (d, J=8.5 Hz, 1H), 7.04 (d, J=7.1 Hz, 1H), 6.96 (broad d, J=5.3 Hz, 1H), 6.70 (d, J=8.5 Hz, 1H), 4.04 (t, J=9.1 Hz, 1H), 3.91 (br q, J=12.6 Hz, 1H), 3.80-3.67 (m, 1H), 3.11 (bt s, 1H), 2.94 (br d, J=13.3 Hz, 1H), 2.77-2.57 (m, 2H), 2.31-2.19 (m, 1H), 2.10 (br s, 1H), 1.87-1.66 (m, 4H), 1.64-1.22 (m, 15H), 0.92-0.83 (m, 2H), 0.76-0.68 (m, 2H). ESI-MS m/z calc. 648.27057, found 649.5 (M+1)$^+$; Retention time: 2.14 min (LC Method B). The second diastereomer to elute was (14S)-12,12-dimethyl-8-(2-oxo-3-{3-[1-(trifluoromethyl)cyclopropyl]propyl}pyrrolidin-1-yl)-2λ$^6$-thia-3,9,11,18,23-pentaazatetracyclo[17.3.1.1$^{11,14}$, 14.0$^{5,10}$]tetracosa-1(22),5,7,9,19(23),20-hexaene-2,2,4-trione (diastereomer 2) (Compound 175) (12.2 mg, 17%). $^1$H NMR (400 MHz, dimethyl sulfoxide-d$_6$) δ 12.39 (s, 1H), 7.68 (d, J=8.5 Hz, 1H), 7.63-7.48 (m, 2H), 7.04 (d, J=7.1 Hz, 1H), 6.95 (br d, J=5.1 Hz, 1H), 6.70 (d, J=8.5 Hz, 1H), 4.04-3.87 (m, 2H), 3.82 (q, J=9.9, 9.0 Hz, 1H), 3.09 (broad s, 1H), 2.94 (d, J=13.4 Hz, 1H), 2.75-2.61 (m, 2H), 2.24 (q, J=8.7, 7.9 Hz, 1H), 2.17-1.96 (br m, 1H), 1.87-1.64 (m, 4H), 1.64-1.41 (m, 12H), 1.41-1.15 (m, 3H), 0.92-0.84 (m, 2H), 0.71 (s, 2H). ESI-MS m/z calc. 648.27057, found 649.4 (M+1)+; Retention time: 2.12 min (LC Method B).

Example 46: Preparation of 4-[3-(2-{dispiro [2.0.2.1]heptan-7-yl}ethoxy)-1H-pyrazol-1-yl]-20, 20-dimethyl-10λ6-thia-1,3,9,14,22-pentaazatetracyclo[16.2.1.111,14.02,7]docosa-2,4,6,11(22),12-pentaene-8,10,10-trione (Compound 176)

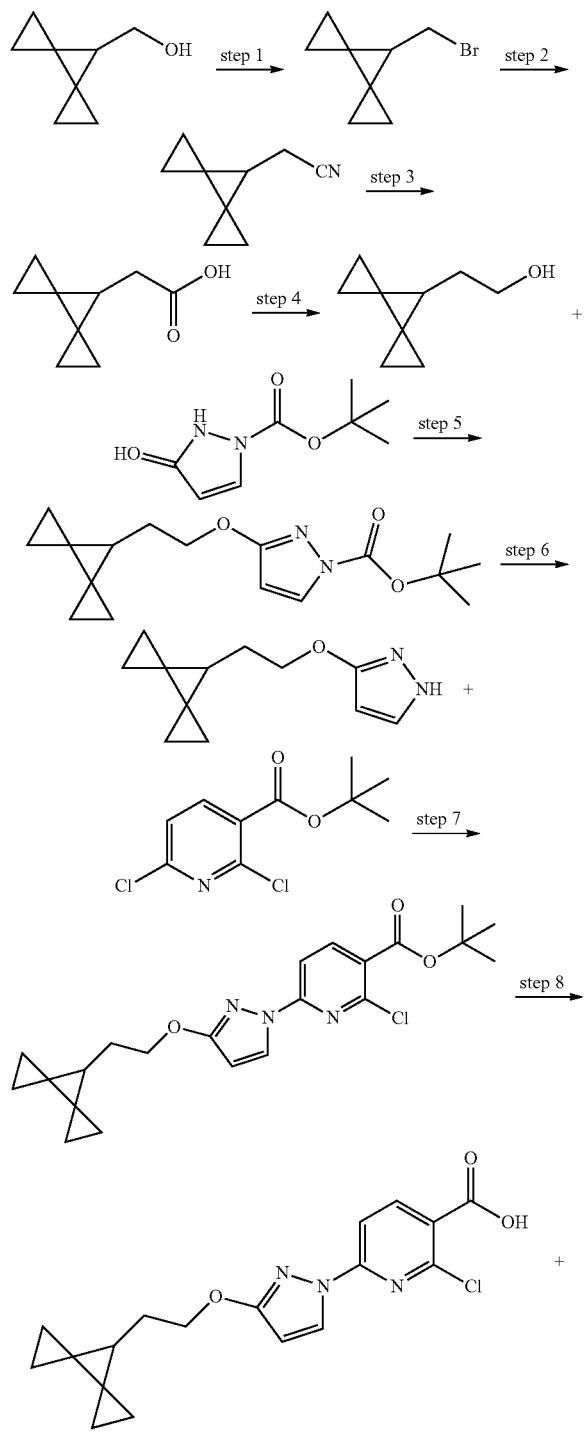

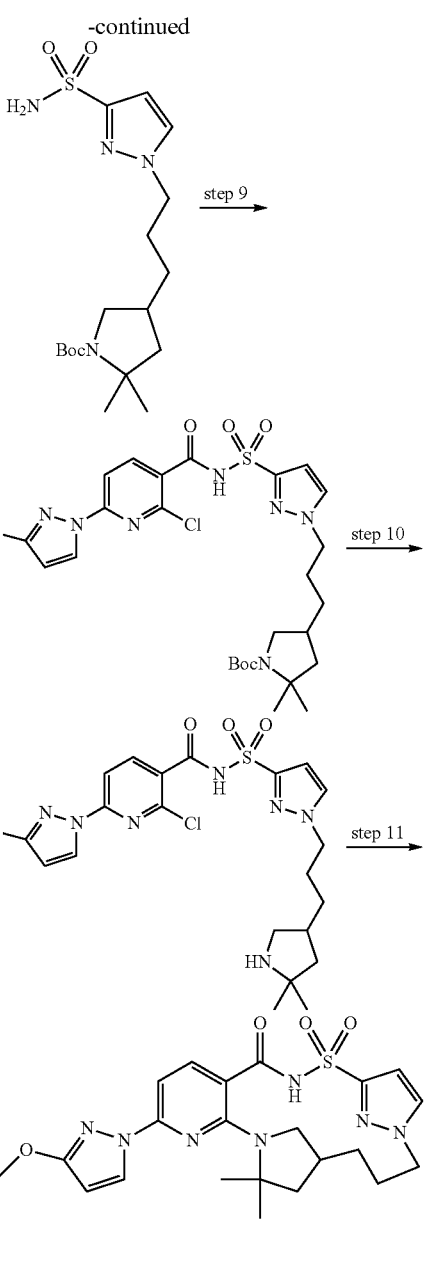

Step 1: 7-(Bromomethyl)dispiro[2.0.2.1]heptane

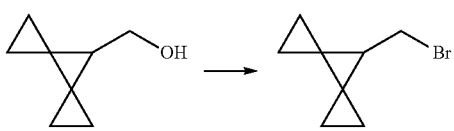 [SMILES: OCC1C2(CC2)C12CC2 ; BrCC1C2(CC2)C12CC2]

A 1000 mL, 3-neck round bottom flask was fitted with a mechanical stirrer, a cooling bath, an addition funnel, a J-Kem temperature probe and a nitrogen inlet/outlet. The vessel was charged under a nitrogen atmosphere with triphenylphosphine (102.7 mL, 443.2 mmol) and dichloromethane (1 L) which provided a clear colorless solution. Stirring was commenced and the cooling bath was charged with acetone. Dry ice was added in portions to the cooling bath until a pot temperature of −15° C. was obtained. The addition funnel was charged with a solution of bromine (22.82 mL, 443.0 mmol) in dichloromethane (220 mL, 10 mL/g) which was subsequently added dropwise over 1 h. Dry ice was added in portions to the cooling bath during the addition to maintain the pot temperature at −15° C. After the addition of bromine was completed, the pale yellow suspension was continued to stir at −15° C. for 15 min at which point the suspension was cooled to −30° C. The addition funnel was charged with a solution of dispiro[2.0.2.1]heptan-7-yl methanol (50 g, 402.6 mmol), pyridine (35.82 mL, 442.9 mmol) and dichloromethane (250 mL, 5 mL/g). The clear pale yellow solution was then added dropwise over 1.5 h maintaining the pot temperature at −30° C. The resulting clear light yellow reaction mixture was allowed to gradually warm to a pot temperature of −5° C. and then continued to stir at −5° C. for 1 h. The reaction mixture then was poured into hexane (2000 mL) which resulted in the formation of a precipitate. The suspension was stirred at room temperature for 30 min and then filtered through a glass frit Buchner funnel with a 20 mm layer of celite. The clear filtrate was concentrated under reduced pressure (water bath temperature at 20° C.) to provide a yellow oil with some precipitate present. The oil was diluted with some hexane, allowed to stand at room temperature for 15 min and then filtered through a glass frit Buchner funnel with a 20 mm layer of celite. The clear filtrate was concentrated under reduced pressure (water bath temperature at 20° C.) to provide 7-(bromomethyl)dispiro[2.0.2.1]heptane (70 g, 93%) as a clear yellow oil. $^1$H NMR (400 MHz, Chloroform-d) δ 3.49 (d, J=7.5 Hz, 2H), 1.90 (t, J=7.5 Hz, 1H), 1.06-0.84 (m, 4H), 0.71 (ddd, J=9.1, 5.1, 4.0 Hz, 2H), 0.54 (dddd, J=8.6, 4.8, 3.8, 1.0 Hz, 2H).

Step 2: 2-Dispiro[2.0.2.1]heptan-7-ylacetonitrile

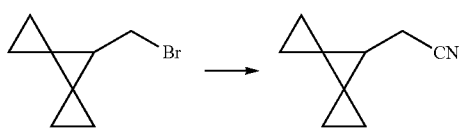 [SMILES: BrCC1C2(CC2)C12CC2 ; N#CCC1C2(CC2)C12CC2]

A 1000 mL, 3-neck round bottom flask was fitted with a mechanical stirrer, a cooling bath used as secondary containment, a J-Kem temperature probe and a nitrogen inlet/outlet. The vessel was charged under a nitrogen atmosphere with 7-(bromomethyl)dispiro[2.0.2.1]heptane (35 g, 187.1 mmol) and dimethyl sulfoxide (245 mL) which provided a clear amber solution. Stirring was commenced and the pot temperature was recorded at 19° C. The vessel was then charged with sodium cyanide (11.46 g, 233.8 mmol) added as a solid in one portion which resulted in a dark solution and a gradual exotherm to 49° C. over 15 min. After a few min the pot temperature began to decrease and the mixture was continued to stir at room temperature overnight (about 15 h). The dark reaction mixture was quenched with ice cold saturated sodium carbonate solution (500 mL) and then transferred to a separatory funnel and partitioned with diethyl ether (500 mL). The organic was removed and the residual aqueous was extracted with diethyl ether (2×250 mL). The combined organics were washed with water (500 mL), dried over sodium sulfate (200 g) and then filtered through a glass frit Buchner funnel. The clear amber filtrate was concentrated under reduced pressure (water bath temperature 20° C.) to provide 2-dispiro[2.0.2.1]heptan-7-ylacetonitrile (21 g, 84%) as a clear dark amber oil. $^1$H NMR (400 MHz, Chloroform-d) δ 2.42 (d, J=6.6 Hz, 2H), 1.69 (t, J=6.6 Hz, 1H), 1.02-0.88 (m, 4H), 0.79-0.70 (m, 2H), 0.66-0.55 (m, 2H).

Step 3: 2-Dispiro[2.0.2.1]heptan-7-ylacetic Acid

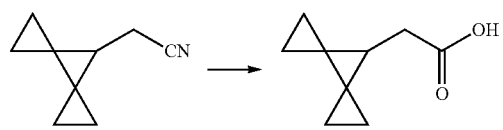 [SMILES: N#CCC1C2(CC2)C12CC2 ; O=C(O)CC1C2(CC2)C12CC2]

To a solution of 2-dispiro[2.0.2.1]heptan-7-ylacetonitrile (2.1 g, 14.19 mmol) in EtOH (32 mL) was added sodium hydroxide (5.12 g, 128.0 mmol) followed by water (13 mL) and the resulting solution was stirred and heated to 70° C. overnight. The mixture was then cooled to room temperature, diluted with water and extracted with diethyl ether. The aqueous phase was adjusted to pH=1 by the addition of 6 N hydrochloric acid (resulting in a cloudy precipitate) and extracted with diethyl ether (3×). The organic phases were dried (magnesium sulfate), filtered and concentrated giving 2-dispiro[2.0.2.1]heptan-7-ylacetic acid (2.19 g, 99% yield, 98% purity) as an orange solid which was used in the next step without further purification. $^1$H NMR (400 MHz, Chloroform-d) δ 2.44 (d, J=6.9 Hz, 2H), 1.67 (t, J=6.9 Hz, 1H), 0.91 (ddd, J=9.0, 5.2, 3.9 Hz, 2H), 0.81 (dddd, J=8.9, 5.2, 3.9, 0.5 Hz, 2H), 0.69 (ddd, J=8.9, 5.2, 3.9 Hz, 2H), 0.56-0.44 (m, 2H).

Step 4: 2-Dispiro[2.0.2.1]heptan-7-ylethanol

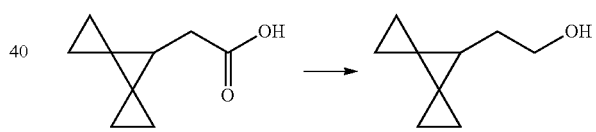

To lithium aluminum hydride (827.4 mg, 902.3 µL, 21.80 mmol) dissolved in tetrahydrofuran (33.71 mL) cooled in an ice/water bath was added 2-dispiro[2.0.2.1]heptan-7-ylacetic acid (2.552 g, 16.77 mmol) in tetrahydrofuran (7.470 mL) dropwise over 15 min keeping the reaction temperature<20° C. The mixture was allowed to stir a total of 18 h, gradually warming to ambient temperature. The mixture was cooled with an ice/water bath and sequentially quenched with slow addition of water (838.4 mg, 838.4 µL, 46.54 mmol), followed by sodium hydroxide (1.006 mL of 5 M, 5.031 mmol), then water (2.493 g, 2.493 mL, 138.4 mmol) affording a white, granular slurry which was filtered over celite. Washed the filtered solid with diethyl ether. The filtrate was concentrated in vacuo at ~300 mbar and 30° C. water bath. Diluted the residue with diethyl ether, dried (magnesium sulfate), filtered and concentrated in vacuo at ~300 mbar and 30° C. water bath followed by ~30 seconds under vacuum to give 2-dispiro[2.0.2.1]heptan-7-ylethanol (2.318 g, 100%) which was used directly in the ensuing step without further purification. $^1$H NMR (400 MHz, Chloroform-d) δ 3.64 (s, 2H), 1.68 (d, J=6.7 Hz, 2H), 1.39 (s, 1H), 1.31 (s, 1H), 0.82 (d, J=14.0 Hz, 4H), 0.65 (s, 2H), 0.50 (d, J=3.6 Hz, 2H).

Step 5: tert-Butyl 3-(2-dispiro[2.0.2.1]heptan-7-ylethoxy)pyrazole-1-carboxylate

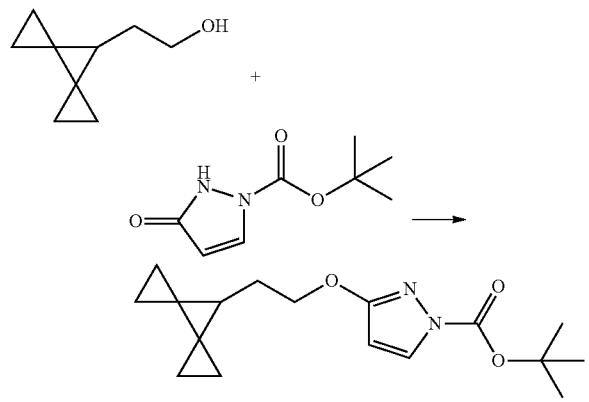

To a solution of tert-butyl 5-oxo-1H-pyrazole-2-carboxylate (2.942 g, 15.97 mmol) and 2-dispiro[2.0.2.1]heptan-7-ylethanol (2.318 g, 16.77 mmol) in tetrahydrofuran (36.78 mL) was added triphenylphosphine (4.399 g, 16.77 mmol). To the mixture was slowly added diisopropyl azodicarboxylate (3.391 g, 3.302 mL, 16.77 mmol) dropwise over 10 min (mild exotherm noted). The reaction mixture was stirred at room temperature for 30 min then at 50° C. for 30 min. The tetrahydrofuran was removed in vacuo. To the crude residue was added toluene (23.54 mL) and the mixture was stirred overnight as a precipitate gradually crystallized. Slurried with Celite then the precipitate was filtered off and washed with toluene (8.705 mL) and again with toluene (8.705 mL). The filtrate was concentrated in vacuo. The crude product was purified by silica gel chromatography using a shallow gradient from 100% hexanes to 100% ethyl acetate giving tert-butyl 3-(2-dispiro[2.0.2.1]heptan-7-ylethoxy)pyrazole-1-carboxylate (3.449 g, 71%). ESI-MS m/z calc. 304.17868, found 305.1 (M+1)$^+$; Retention time: 0.82 min (LC Method A).

Step 6: 3-(2-Dispiro[2.0.2.1]heptan-7-ylethoxy)-1H-pyrazole

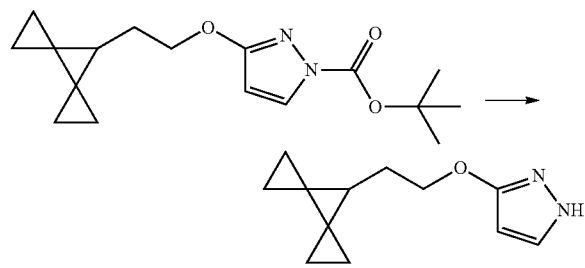

tert-Butyl 3-(2-dispiro[2.0.2.1]heptan-7-ylethoxy)pyrazole-1-carboxylate (5.304 g, 17.43 mmol) was dissolved in dichloromethane (53.04 mL) with trifluoroacetic acid (29.81 g, 20.14 mL, 261.4 mmol) and the reaction was stirred at room temperature for 120 min. The reaction was evaporated and the resulting oil was partitioned between ethyl acetate and a saturated sodium bicarbonate solution and the layers separated. The aqueous portion was extracted two additional times with ethyl acetate, then the organics were combined, washed with brine, dried over sodium sulfate, filtered and evaporated to give an oil, 3-(2-dispiro[2.0.2.1]heptan-7-ylethoxy)-1H-pyrazole (3.56 g, 100%). ESI-MS m/z calc. 204.12627, found 205.1 (M+1)$^+$; Retention time: 0.59 min (LC Method A).

Step 7: tert-Butyl 2-chloro-6-[3-(2-dispiro[2.0.2.1]heptan-7-ylethoxy)pyrazol-1-yl]pyridine-3-carboxylate

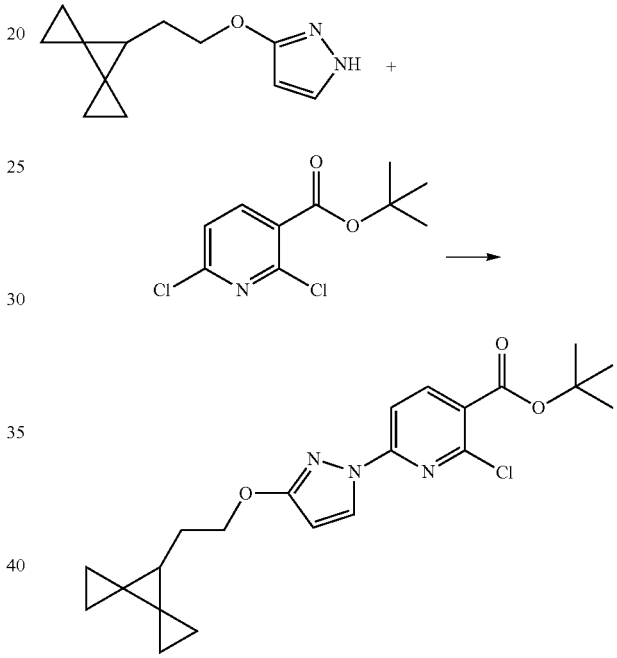

tert-Butyl 2,6-dichloropyridine-3-carboxylate (4.322 g, 17.42 mmol), 3-(2-dispiro[2.0.2.1]heptan-7-ylethoxy)-1H-pyrazole (3.559 g, 17.42 mmol) and potassium carbonate (2.891 g, 20.92 mmol) were combined in anhydrous dimethyl sulfoxide (71.18 mL). 1,4-Diazabicyclo[2.2.2]octane (391.1 mg, 3.487 mmol) was added and the mixture was stirred at room temperature under nitrogen for 16 h. The reaction mixture was diluted with water (136.9 mL) and stirred for 15 min. The resulting white solid was filtered and washed with water. The solid was dissolved in dichloromethane and dried over magnesium sulfate. The mixture was filtered and evaporated to give tert-butyl 2-chloro-6-[3-(2-dispiro[2.0.2.1]heptan-7-ylethoxy)pyrazol-1-yl]pyridine-3-carboxylate (5.69 g, 79%) as a white solid. $^1$H NMR (400 MHz, Chloroform-d) δ 8.35 (d, J=2.9 Hz, 1H), 8.18 (d, J=8.4 Hz, 1H), 7.69 (d, J=8.4 Hz, 1H), 5.94 (d, J=2.9 Hz, 1H), 4.25 (s, 2H), 1.90 (d, J=6.8 Hz, 2H), 1.62 (s, 9H), 1.49 (t, J=6.6 Hz, 1H), 0.85 (d, J=1.5 Hz, 4H), 0.65 (d, J=1.5 Hz, 2H), 0.52 (d, J=1.1 Hz, 2H). ESI-MS m/z calc. 415.16626, found 360.0 (M-tBu)$^+$; Retention time: 2.09 min (LC Method B).

Step 8: 2-Chloro-6-[3-(2-dispiro[2.0.2.1]heptan-7-ylethoxy)pyrazol-1-yl]pyridine-3-carboxylic Acid

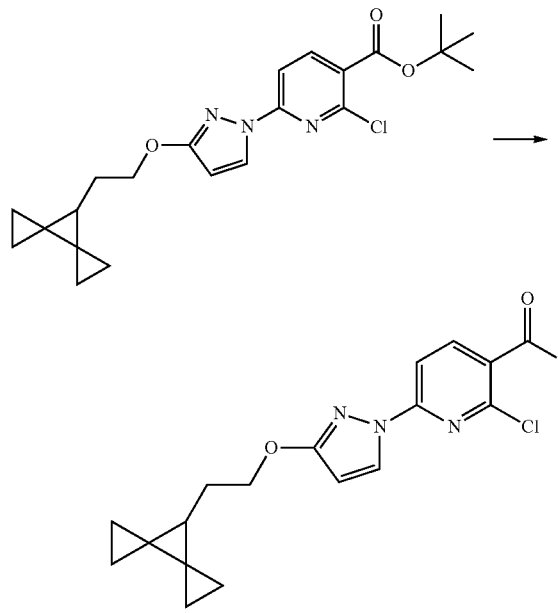

tert-Butyl 2-chloro-6-[3-(2-dispiro[2.0.2.1]heptan-7-ylethoxy)pyrazol-1-yl]pyridine-3-carboxylate (5.85 g, 14.07 mmol) was dissolved in dichloromethane (58.5 mL) with trifluoroacetic acid (16.26 mL, 211.1 mmol) and the reaction was stirred at room temperature for 16 h. The reaction was evaporated and to the resulting solid was added ether and then removed the ether under reduced pressure. This evaporation from ether was repeated twice more resulting in a white solid, 2-chloro-6-[3-(2-dispiro[2.0.2.1]heptan-7-ylethoxy)pyrazol-1-yl]pyridine-3-carboxylic acid (5.06 g, 100%). $^1$H NMR (400 MHz, Chloroform-d) δ 8.41 (d, J=8.5 Hz, 1H), 8.37 (d, J=2.9 Hz, 1H), 7.75 (d, J=8.5 Hz, 1H), 5.97 (d, J=2.9 Hz, 1H), 4.27 (s, 2H), 1.91 (d, J=6.7 Hz, 2H), 1.50 (s, 1H), 0.85 (d, J=1.5 Hz, 4H), 0.71-0.62 (m, 2H), 0.52 (d, J=1.1 Hz, 2H). ESI-MS m/z calc. 359.10367, found 360.2 (M+1)$^+$; Retention time: 2.16 min (LC Method B).

Step 9: tert-Butyl 4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate

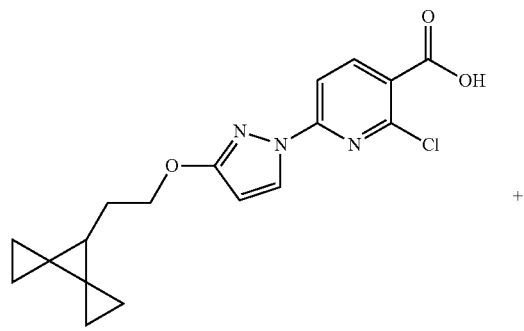

+

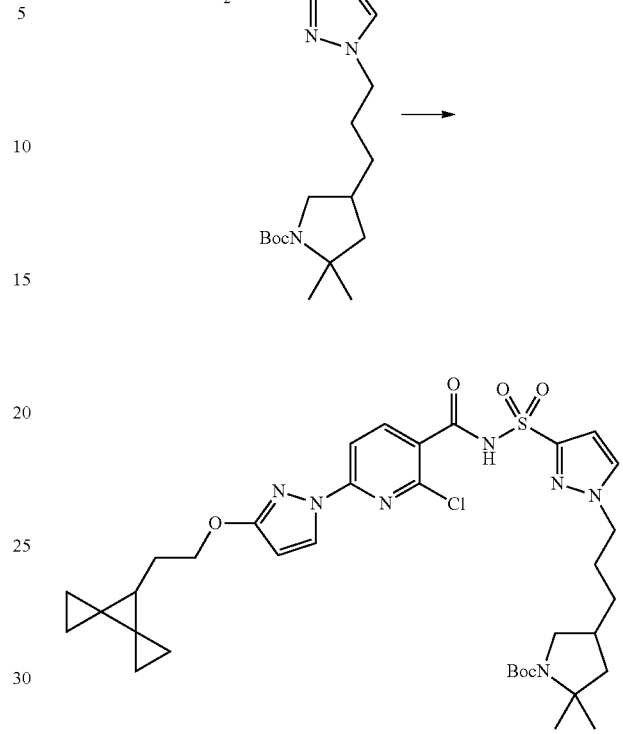

2-Chloro-6-[3-(2-dispiro[2.0.2.1]heptan-7-ylethoxy)pyrazol-1-yl]pyridine-3-carboxylic acid (400 mg, 1.112 mmol) and carbonyl diimidazole (273.5 mg, 1.687 mmol) were combined in tetrahydrofuran (2 mL) and stirred for 90 min at room temperature. Then tert-butyl 2,2-dimethyl-4-[3-(3-sulfamoylpyrazol-1-yl)propyl]pyrrolidine-1-carboxylate (429.5 mg, 1.111 mmol) was added followed by 1,8-diazabicyclo[5.4.0]undec-7-ene (430.8 mg, 2.830 mmol) and the reaction was stirred at room temperature for 1 h then heated to 50° C. and stirred overnight. The reaction was diluted with ethyl acetate and washed with a saturated aqueous sodium bicarbonate solution followed by brine. The organics were separated, dried over sodium sulfate, filtered and evaporated and then purified on silica gel chromatography using a gradient from 100% hexanes to 100% ethyl acetate to afford tert-butyl 4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate (350 mg, 43%) as an off-white solid. $^1$H NMR (400 MHz, dimethyl sulfoxide-d$_6$) δ 8.34 (s, 1H), 8.08 (d, J=8.2 Hz, 1H), 7.77 (s, 1H), 7.62 (d, J=8.3 Hz, 1H), 6.71-6.49 (m, 1H), 6.10 (d, J=2.8 Hz, 1H), 4.23 (s, 2H), 4.13 (s, 2H), 3.52 (s, 1H), 2.73 (d, J=6.0 Hz, 1H), 2.08 (d, J=6.7 Hz, 1H), 1.81 (q, J=6.6 Hz, 5H), 1.47 (t, J=6.5 Hz, 1H), 1.40-1.21 (m, 18H), 0.83 (d, J=2.0 Hz, 4H), 0.66-0.60 (m, 2H), 0.52-0.46 (m, 2H). ESI-MS m/z calc. 727.2919, found 728.1 (M+1)$^+$; Retention time: 0.92 min (LC Method A).

Step 10: 2-Chloro-N-[1-[3-(5,5-dimethylpyrrolidin-3-yl)propyl]pyrazol-3-yl]sulfonyl-6-[3-(2-dispiro[2.0.2.1]heptan-7-ylethoxy)pyrazol-1-yl]pyridine-3-carboxamide

Step 11: 4-[3-(2-{Dispiro[2.0.2.1]heptan-7-yl}ethoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 176)

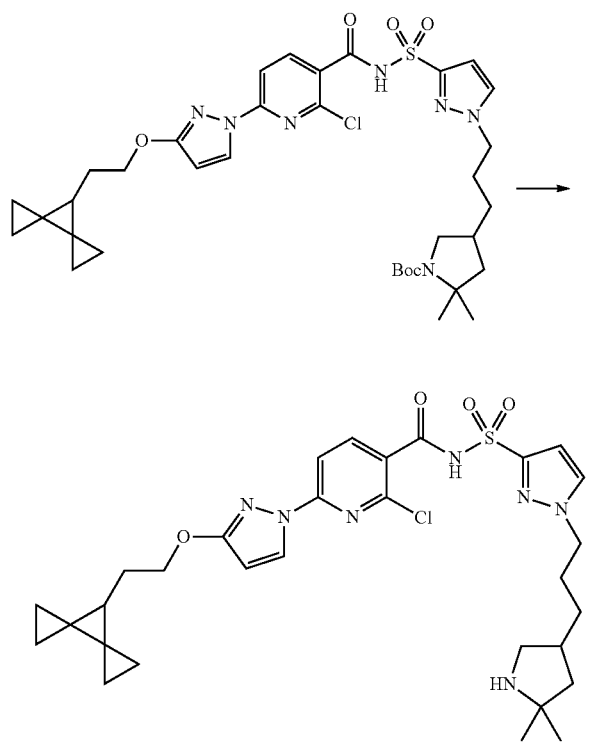

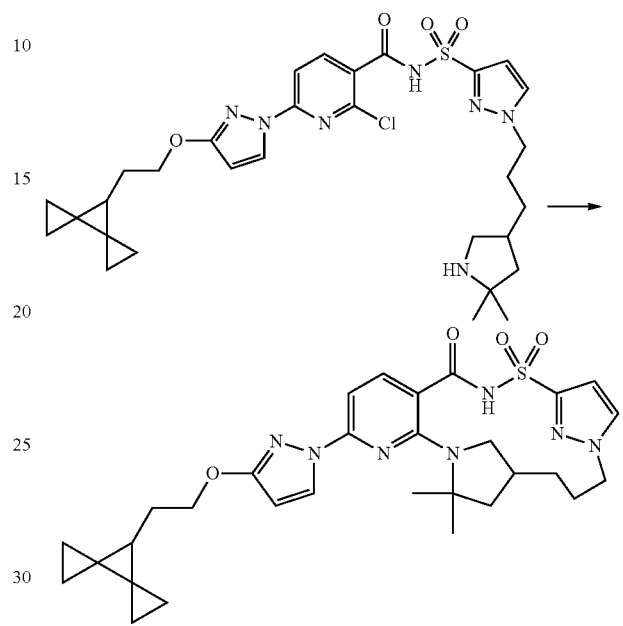

tert-Butyl 4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate (350 mg, 0.4806 mmol) was dissolved in dichloromethane (1.527 mL) and to the mixture was added trifluoroacetic acid (2.192 g, 1.481 mL, 19.22 mmol) and the resulting mixture was stirred at room temperature for 60 min. Concentrated the mixture to dryness under reduced pressure, took up in saturated aqueous sodium bicarbonate and ethyl acetate containing a small amount of methanol for solubility and separated the layers. Concentrated the organic layer by rotary evaporation followed by high vacuum pump giving 2-chloro-N-[1-[3-(5,5-dimethylpyrrolidin-3-yl)propyl]pyrazol-3-yl]sulfonyl-6-[3-(2-dispiro[2.0.2.1]heptan-7-ylethoxy)pyrazol-1-yl]pyridine-3-carboxamide (301.9 mg, 100%) as an off-white solid. ¹H NMR (400 MHz, CDCl₃) δ 8.28 (d, J=2.8 Hz, 1H), 8.21 (d, J=8.3 Hz, 1H), 7.61 (d, J=8.3 Hz, 1H), 7.44 (s, 1H), 6.67 (s, 1H), 5.88 (d, J=2.8 Hz, 1H), 4.22 (t, J=6.8 Hz, 2H), 4.17 (s, 2H), 3.55 (s, 1H), 3.03 (s, 1H), 2.23 (s, 1H), 1.88 (d, J=6.7 Hz, 2H), 1.83 (s, 3H), 1.48 (s, 1H), 1.46-1.35 (m, 5H), 1.35-1.24 (m, 4H), 0.84 (t, J=1.9 Hz, 4H), 0.63 (d, J=1.6 Hz, 2H), 0.51 (d, J=1.1 Hz, 2H).

Combined 2-chloro-N-[1-[3-(5,5-dimethylpyrrolidin-3-yl)propyl]pyrazol-3-yl]sulfonyl-6-[3-(2-dispiro[2.0.2.1]heptan-7-ylethoxy)pyrazol-1-yl]pyridine-3-carboxamide (310 mg, 0.4935 mmol), potassium carbonate (341.1 mg, 2.468 mmol), cesium fluoride (112.8 mg, 0.7426 mmol), 3 Å molecular sieves and dimethyl sulfoxide (9.3 mL) in a vial, purged with nitrogen, capped, heated to 155° C. and stirred for 20 h. Cooled to room temperature then the mixture was filtered, diluted with ethyl acetate and washed with a saturated aqueous sodium bicarbonate solution, followed by brine. The organics were separated, dried over sodium sulfate, evaporated and then purified on silica gel chromatography using a gradient from 100% hexanes to 100% ethyl acetate to afford as a white solid, 4-[3-(2-{dispiro[2.0.2.1]heptan-7-yl}ethoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 176) (117 mg, 40%). ¹H NMR (400 MHz, CDCl₃) δ 8.37 (s, 1H), 8.16 (d, J=2.8 Hz, 1H), 7.68 (d, J=8.3 Hz, 1H), 7.48 (d, J=2.3 Hz, 1H), 7.26 (s, 1H), 7.07 (d, J=2.3 Hz, 1H), 7.02 (d, J=8.3 Hz, 1H), 5.86 (d, J=2.8 Hz, 1H), 4.36 (d, J=13.5 Hz, 1H), 4.24 (s, 2H), 3.95 (d, J=12.4 Hz, 1H), 2.74 (t, J=8.1 Hz, 1H), 2.15 (d, J=4.2 Hz, 2H), 2.08-1.93 (m, 3H), 1.89 (d, J=6.7 Hz, 2H), 1.76 (dd, J=11.9, 5.3 Hz, 1H), 1.59 (s, 3H), 1.55 (s, 5H), 0.85 (q, J=2.0 Hz, 4H), 0.64 (d, J=1.7 Hz, 2H), 0.51 (d, J=1.2 Hz, 2H). ESI-MS m/z calc. 591.26276, found 592.4 (M+1)⁺; Retention time: 2.37 min (LC Method B).

439

Example 47: Preparation of (14S)-8-[3-(2-{dispiro[2.0.2.1]heptan-7-yl}ethyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 177) and (14S)-8-[3-(2-{dispiro[2.0.2.1]heptan-7-yl}ethyl)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 178)

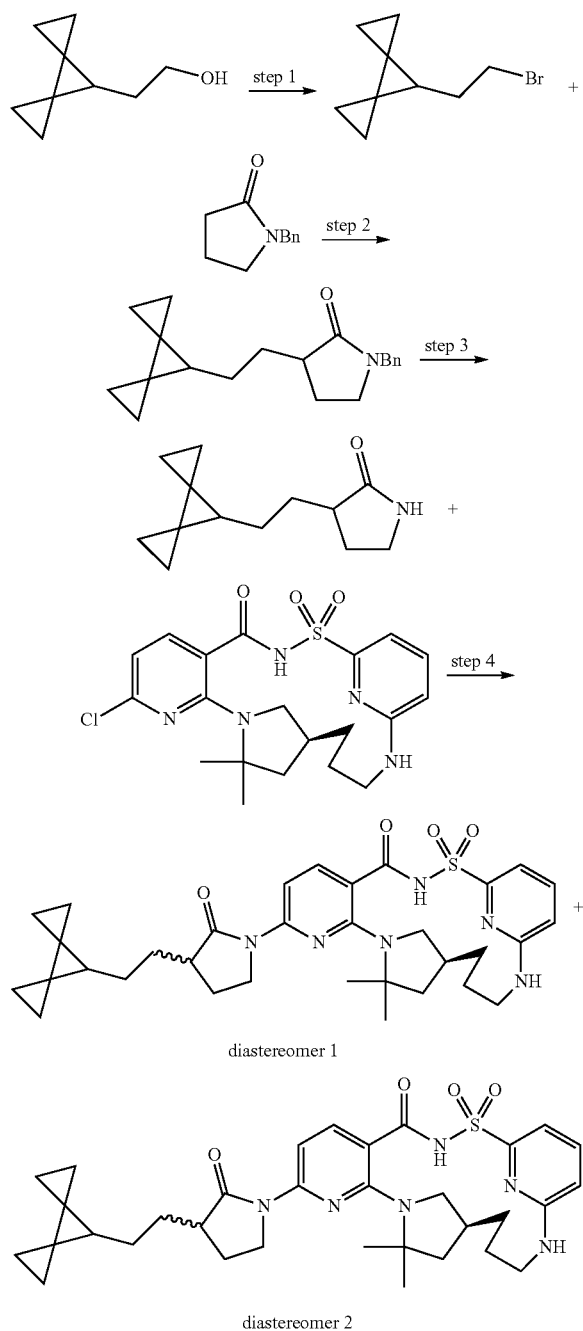

440

Step 1: 7-(2-Bromoethyl)dispiro[2.0.2.1]heptane

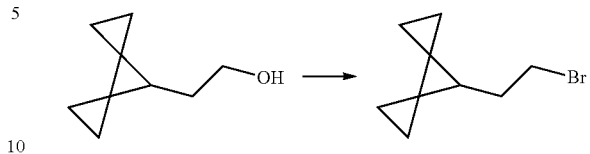

To a stirring solution of triphenylphosphine (1.07 g, 4.080 mmol) in anhydrous dichloromethane (15 mL) under nitrogen atmosphere at −15° was dropwise added a solution of molecular bromine (0.22 mL, 4.271 mmol) in dichloromethane (3 mL) over 10 min and on completion of addition (pale orange solution) the mixture was stirred an additional 15 min at −15° C. The mixture was then cooled to −30° C. and a solution of 2-dispiro[2.0.2.1]heptan-7-ylethanol (537 mg, 3.885 mmol) and pyridine (330 μL, 4.080 mmol) in dichloromethane (4 mL) was added dropwise over 5 min and on completion of addition the mixture was warmed to −5° C. and stirred for 2 h. The reaction mixture was then poured into pentane (350 mL) resulting in a mass of yellow precipitate. This suspension was filtered and the filtrate was reduced under rotary evaporation (250 mbar and 30° C. water bath) to give a white solid. To this solid was added pentane and the mixture briefly sonicated and filtered. Concentration of this filtrate gave 7-(2-bromoethyl)dispiro[2.0.2.1]heptane (634 mg, 81%) as a pale yellow oil which was used for the next step without any further purification. ¹H NMR (400 MHz, Chloroform-d) δ 3.37 (t, J=7.1 Hz, 2H), 2.02-1.96 (m, 2H), 1.46 (t, J=6.4 Hz, 1H), 0.91-0.78 (m, 4H), 0.66 (ddd, J=8.1, 4.8, 3.6 Hz, 2H), 0.50 (dddd, J=9.0, 4.9, 3.7, 0.9 Hz, 2H).

Step 2: 1-Benzyl-3-(2-dispiro[2.0.2.1]heptan-7-ylethyl)pyrrolidin-2-one

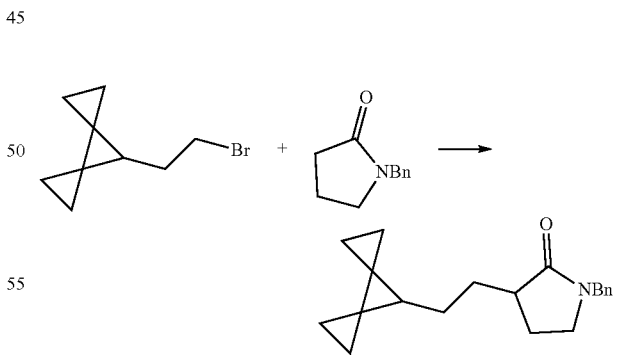

A 100 mL three neck flask was dried with a heat gun under vacuum and filled with nitrogen. The flask was charged with 1-benzylpyrrolidin-2-one (0.46 mL, 2.875 mmol) and anhydrous tetrahydrofuran (5 mL). After cooling to −78° C., a solution of n-butyllithium (1.3 mL of 2.5 M, 3.250 mmol) (2.5 M in hexanes) was added dropwise inducing formation of an orange solution. After stirring at −78° C. for 20 min, a solution of 7-(2-bromoethyl)dispiro[2.0.2.1]heptane (611 mg, 3.038 mmol) in tetrahydrofuran (1 mL) was added dropwise. The mixture was stirred in the cooling bath that was allowed to slowly warm up to room temperature. After 17 h, the mixture was quenched with the addition of saturated aqueous ammonium chloride (50 mL). The product was extracted with ethyl acetate (2×30 mL). The organic layer was dried over sodium sulfate, filtered and concentrated under reduced pressure. The crude product was purified by flash chromatography on silica gel using a gradient of ethyl acetate (0 to 100% over 30 min) in hexanes. Evaporation of the solvents gave 1-benzyl-3-(2-dispiro [2.0.2.1]heptan-7-ylethyl)pyrrolidin-2-one (352 mg, 41%) as a colorless oil. $^1$H NMR (400 MHz, Chloroform-d) δ 7.38-7.17 (m, 5H), 4.45 (q, J=14.7 Hz, 2H), 3.22-3.10 (m, 2H), 2.42 (qd, J=8.8, 4.1 Hz, 1H), 2.21-2.07 (m, 1H), 2.00-1.85 (m, 1H), 1.62 (dq, J=12.7, 8.4 Hz, 1H), 1.51-1.42 (m, 2H), 1.42-1.25 (m, 2H), 0.88-0.71 (m, 4H), 0.68-0.55 (m, 2H), 0.51-0.39 (m, 2H). ESI-MS m/z calc. 295.1936, found 296.3 (M+1)$^+$; Retention time: 2.08 min (LC Method B).

Step 3: 3-(2-Dispiro[2.0.2.1]heptan-7-ylethyl)pyrrolidin-2-one

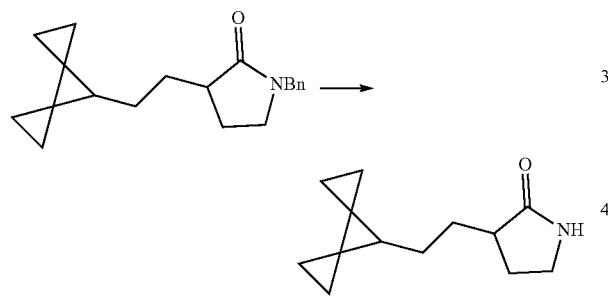

A 100 mL flask was charged under nitrogen with 1-benzyl-3-(2-dispiro[2.0.2.1]heptan-7-ylethyl)pyrrolidin-2-one (350 mg, 1.185 mmol), propylamine (4 mL) and 1,2-ethandiamine (510 µL, 7.629 mmol). The mixture was cooled down to −20° C. (external cooling bath temperature) and lithium (72 mg, 10.37 mmol) (wire, briefly rinsed with hexanes, then freshly cut in small pieces) was added. A blue color developed around the small pieces of lithium and then disappeared quickly. After 2 h at −20° C., the blue color became permanent. The reaction was quenched by addition of methanol (400 µL) at −20° C. and water (40 mL). After warming up to room temperature, the white solid in suspension was filtered, washed with water and briefly air dried (200 mg). The material was purified by flash chromatography on silica gel using a gradient of methanol (0 to 15% over 30 min) in dichloromethane giving 3-(2-dispiro[2.0.2.1] heptan-7-ylethyl)pyrrolidin-2-one (173 mg, 71%) as a white solid. $^1$H NMR (400 MHz, Chloroform-d) δ 5.69 (broad s, 1H), 3.41-3.24 (m, 2H), 2.37-2.20 (m, 2H), 1.88 (dddd, J=13.4, 9.1, 7.4, 3.8 Hz, 1H), 1.83-1.67 (m, 1H), 1.53-1.41 (m, 2H), 1.41-1.29 (m, 2H), 0.86-0.74 (m, 4H), 0.67-0.59 (m, 2H), 0.51-0.39 (m, 2H). ESI-MS m/z calc. 205.14667, found 206.2 (M+1)$^+$; Retention time: 1.61 min (LC Method B).

Step 4: (14S)-8-[3-(2-{Dispiro[2.0.2.1]heptan-7-yl}ethyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer 1) (Compound 177) and (14S)-8-[3-(2-{dispiro[2.0.2.1]heptan-7-yl}ethyl)-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer 2) (Compound 178)

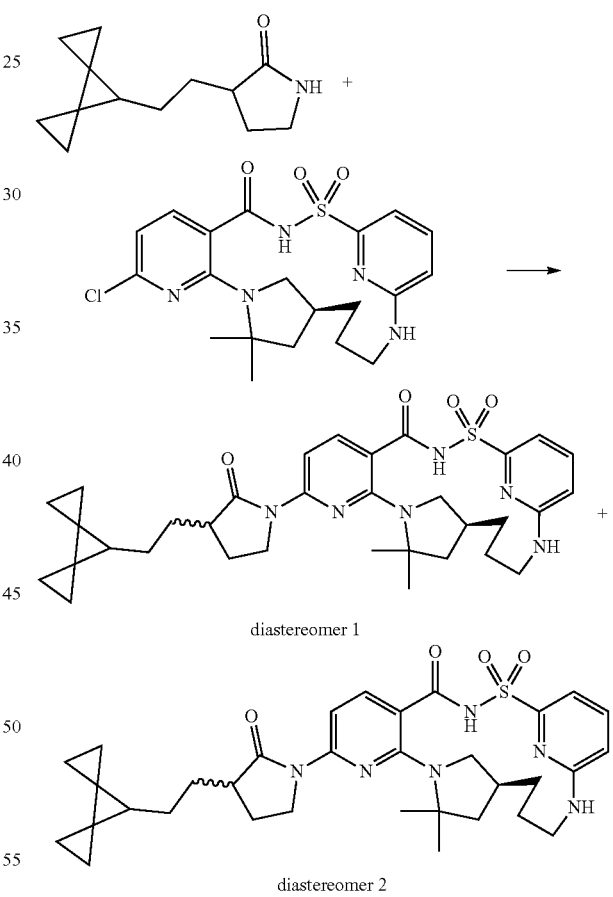

A 4 mL vial was charged with (14S)-8-chloro-12,12-dimethyl-2λ$^6$-thia-3,9,11,18,23-pentaazatetracyclo [17.3.1.1$^{11,14}$.0$^{5,10}$]tetracosa-1(23),5,7,9,19,21-hexaene-2,2,4-trione (100 mg, 0.2222 mmol), 3-(2-dispiro[2.0.2.1] heptan-7-ylethyl)pyrrolidin-2-one (47 mg, 0.2289 mmol), Pd$_2$(dba)$_3$ (32 mg, 0.03495 mmol), Xantphos (19 mg, 0.03284 mmol), cesium carbonate (365 mg, 1.120 mmol) and anhydrous dioxane (1.5 mL). The mixture was sparged with nitrogen for about 5 min, capped and stirred at 120° C. for 16 h. The organic solvent was evaporated by blowing nitrogen in the vial. The reaction was diluted with dimethyl sulfoxide (3 mL), microfiltered and subjected to reverse phase preparative HPLC ($C_{18}$) using a gradient of acetonitrile in water (1 to 99% over 15 min) and hydrochloric acid as a modifier. The pure fractions were collected and the organic solvents were evaporated. The resulting aqueous solution was extracted with dichloromethane and the organic phase was dried over sodium sulfate. Evaporation of the solvents gave a residue which was purified by flash chromatography on silica gel using a gradient of methanol (0 to 5% over 30 min) in dichloromethane. The resulting product was dissolved in dimethyl sulfoxide (2 mL) and further purified by prep HPLC using a 50 to 99% over 15 min gradient of acetonitrile in water (hydrochloric acid as a modifier). The pure fractions were collected and the organic solvents were evaporated. The resulting aqueous solution was extracted with dichloromethane and the organic phase was dried over sodium sulfate. Evaporation of the solvents gave a diastereomeric mixture which was subjected to SFC separation (ChiralCel OJ-H (250×10 mm), 5 μM column; mobile phase 24% acetonitrile/methanol (90:10, no modifier), 76% carbon dioxide, 10 mL/min; concentration 24 mg/mL in acetonitrile/methanol/dimethyl sulfoxide (72:8: 20); injection volume 70 μL, 100 bar). Pure product fractions were combined and the solvents were evaporated and the residue triturated in dichloromethane/hexanes. The first diastereomer to elute was (14S)-8-[3-(2-{dispiro[2.0.24.13]heptan-7-yl}ethyl)-2-oxopyrrolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (diastereomer 1) (Compound 177) (6.3 mg, 9%). $^1$H NMR (400 MHz, dimethyl sulfoxide-d$_6$) δ 12.38 (s, 1H), 7.67 (d, J=8.5 Hz, 1H), 7.62-7.45 (m, 2H), 7.03 (d, J=7.2 Hz, 1H), 6.95 (broad s, 1H), 6.70 (d, J=8.7 Hz, 1H), 4.04 (t, J=8.9 Hz, 1H), 3.91 (br dd, J=25.4, 13.2 Hz, 1H), 3.74 (q, J=9.0, 8.4 Hz, 1H), 3.11 (br s, 1H), 2.94 (br d, J=13.5 Hz, 1H), 2.76-2.63 (m, 1H), 2.64-2.54 (m, 1H), 2.22 (q, J=9.0, 8.2 Hz, 1H), 2.10 (br s, 1H), 1.92-1.63 (m, 4H), 1.64-1.18 (m, 14H), 0.89-0.70 (m, 4H), 0.68-0.57 (m, 2H), 0.53-0.39 (m, 2H). ESI-MS m/z calc. 618.2988, found 619.5 (M+1)$^+$; Retention time: 2.37 min (LC Method B). The second diastereomer to elute was (14S)-8-[3-(2-{dispiro[2.0.2.1]heptan-7-yl}ethyl)-2-oxopyrrolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (diastereomer 2) (Compound 178) (5.2 mg, 7%). $^1$H NMR (400 MHz, dimethyl sulfoxide-d$_6$) δ 12.38 (s, 1H), 7.67 (d, J=8.5 Hz, 1H), 7.62-7.45 (m, 2H), 7.03 (d, J=7.0 Hz, 1H), 6.95 (broad s, 1H), 6.70 (d, J=8.6 Hz, 1H), 3.93 (t, J=9.3 Hz, 2H), 3.82 (q, J=9.9, 8.9 Hz, 1H), 3.10 (br s, 1H), 2.93 (br d, J=13.0 Hz, 1H), 2.76-2.55 (m, 2H), 2.31-2.17 (m, 1H), 2.09 (br s, 1H), 1.86-1.63 (m, 4H), 1.61-1.29 (m, 14H), 0.86-0.73 (m, 4H), 0.67-0.58 (m, 2H), 0.51-0.40 (m, 2H). ESI-MS m/z calc. 618.2988, found 619.5 (M+1)$^+$; Retention time: 2.37 min (LC Method B).

Example 48: Preparation of (14S)-8-[3-(2-{dispiro[2.0.2.1]heptan-7-yl}ethoxy)-2-oxopyrrolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Diastereomer 1) (Compound 179) and (14S)-8-[3-(2-{dispiro[2.0.2.1]heptan-7-yl}ethoxy)-2-oxopyrrolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Diastereomer 2) (Compound 180)

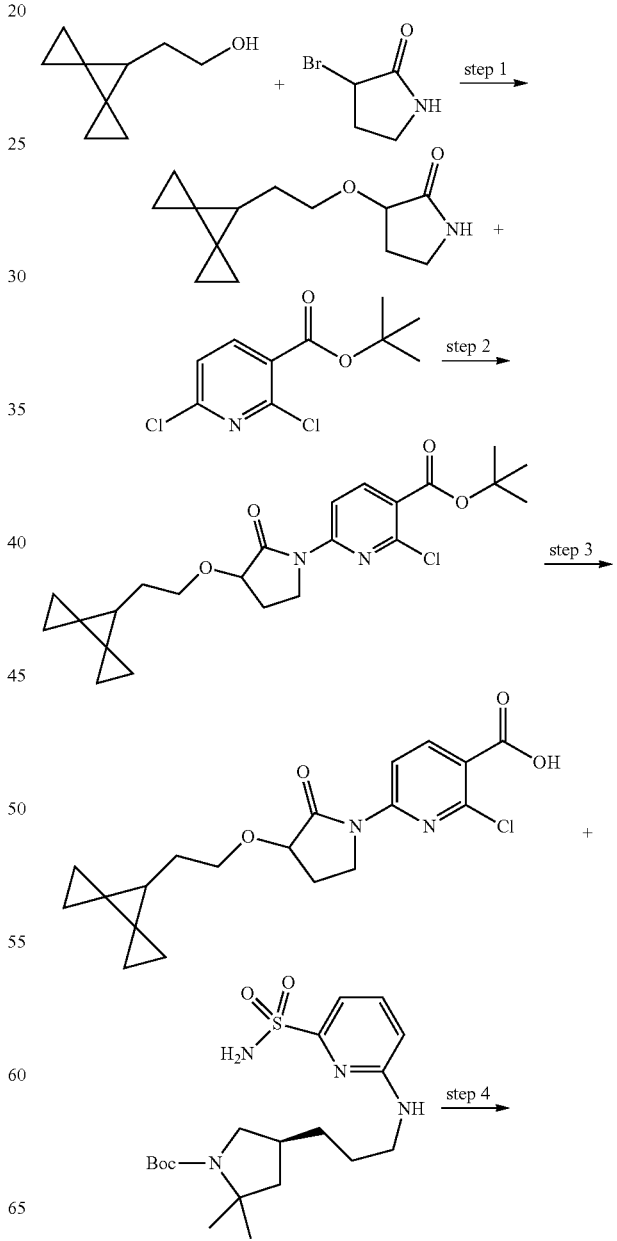

445

-continued

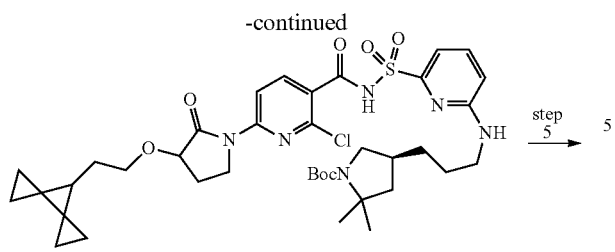

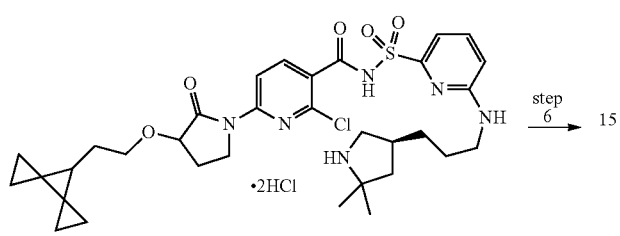

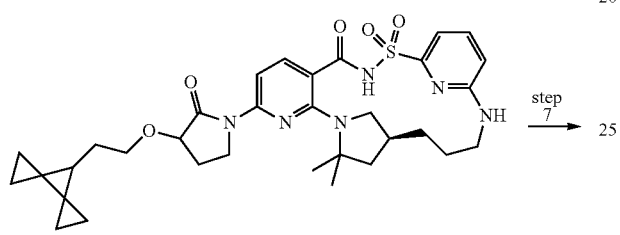


diastereomer 1


diastereomer 2

Step 1: 3-(2-Dispiro[2.0.2.1]heptan-7-ylethoxy)pyrrolidin-2-one

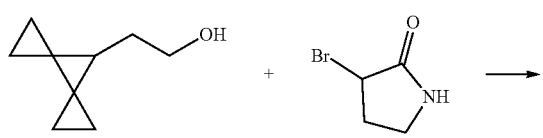

446

-continued

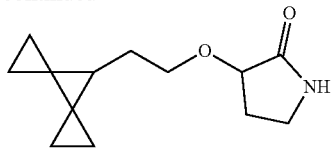

A 100 mL flask was charged under nitrogen with 2-dispiro [2.0.2.1]heptan-7-ylethanol (502 mg of 65% w/w, 2.361 mmol) (contains 35% w/w of residual tetrahydrofuran), 3-bromopyrrolidin-2-one (390 mg, 2.378 mmol) and anhydrous tetrahydrofuran (12 mL). The mixture was cooled down to −50° C. then [bis(trimethylsilyl)amino]potassium (10 mL of 0.5 M in toluene, 5.000 mmol) was added dropwise and the mixture was stirred at −50° C. for 15-20 min, then in an ice-bath at 0° C. for 3 h. The reaction was allowed to slowly warm to room temperature (pinkish reaction mixture). After 14 h, the mixture was cooled down to 0° C. then glacial acetic acid (210 µL, 3.693 mmol) was added to the reaction giving an orange slurry. Brine (75 mL) and ethyl acetate (75 mL) were added and the two phases were separated. The aqueous phase was further extracted with ethyl acetate (2×25 mL). The combined organic extracts were dried over sodium sulfate, filtered and the solvents evaporated. The crude residue was purified by silica gel chromatography (0-15% methanol in dichloromethane gradient over 30 min) to furnish the desired 3-(2-dispiro [2.0.2.1]heptan-7-ylethoxy)pyrrolidin-2-one (399 mg, 76%) as a pale orange resin that slowly solidified. $^1$H NMR (400 MHz, dimethyl sulfoxide-d$_6$) δ 7.74 (broad s, 1H), 3.84 (dd, J=7.7, 7.1 Hz, 1H), 3.71 (dt, J=9.2, 6.7 Hz, 1H), 3.44 (dt, J=9.3, 6.8 Hz, 1H), 3.22-3.01 (m, 2H), 2.27 (dtd, J=12.8, 7.4, 3.7 Hz, 1H), 1.78 (ddt, J=12.8, 8.4, 7.1 Hz, 1H), 1.57 (q, J=6.7 Hz, 2H), 1.35 (t, J=6.6 Hz, 2H), 0.87-0.70 (m, 4H), 0.67-0.55 (m, 2H), 0.54-0.36 (m, 2H). ESI-MS m/z calc. 221.14159, found 222.2 (M+1)$^+$; Retention time: 1.35 min (LC Method B).

Step 2: tert-Butyl 2-chloro-6-[3-(2-dispiro[2.0.2.1] heptan-7-ylethoxy)-2-oxo-pyrrolidin-1-yl]pyridine-3-carboxylate

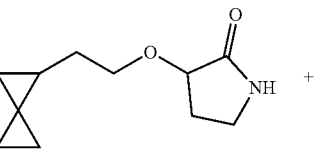

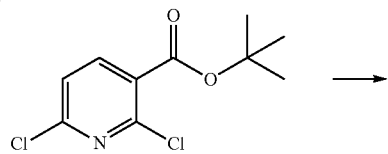

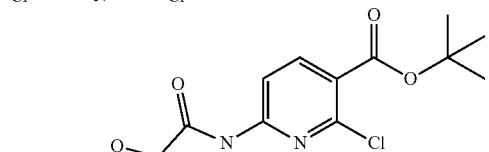

A 100 mL flask was charged under nitrogen with tert-butyl 2,6-dichloropyridine-3-carboxylate (424 mg, 1.709 mmol) and 3-(2-dispiro[2.0.2.1]heptan-7-ylethoxy)pyrrolidin-2-one (376 mg, 1.699 mmol) in anhydrous N,N-dimethylformamide (4 mL). Potassium carbonate (724 mg, 5.239 mmol) (325 mesh) was added followed by 1,4-diazabicyclo[2.2.2]octane (62 mg, 0.5527 mmol). The mixture was stirred at ambient temperature under nitrogen. After 16 h, the reaction was quenched with the addition of water (50 mL) and then extracted with ethyl acetate (3×40 mL). The organic phase was dried over sodium sulfate, filtered and the volatiles were evaporated. The product was purified by flash chromatography on silica gel using a gradient of ethyl acetate (0 to 50% over 30 min) in hexanes. The pure fractions were collected and the solvents evaporated to give tert-butyl 2-chloro-6-[3-(2-dispiro[2.0.2.1]heptan-7-ylethoxy)-2-oxo-pyrrolidin-1-yl]pyridine-3-carboxylate (555 mg, 75%) as a colorless resin. $^1$H NMR (400 MHz, dimethyl sulfoxide-$d_6$) δ 8.33 (d, J=8.6 Hz, 1H), 8.24 (d, J=8.6 Hz, 1H), 4.32 (dd, J=8.8, 7.9 Hz, 1H), 4.07-3.94 (m, 1H), 3.86-3.64 (m, 2H), 3.56 (dt, J=9.2, 6.8 Hz, 1H), 2.49-2.38 (m, 1H), 1.89 (dq, J=12.5, 8.8 Hz, 1H), 1.62 (q, J=6.7 Hz, 2H), 1.55 (s, 9H), 1.39 (t, J=6.6 Hz, 1H), 0.88-0.71 (m, 4H), 0.69-0.57 (m, 2H), 0.46 (d, J=8.8 Hz, 2H). ESI-MS m/z calc. 432.18158, found 433.3 (M+1)$^+$; Retention time: 2.43 min (LC Method B).

Step 3: 2-Chloro-6-[3-(2-dispiro[2.0.2.1]heptan-7-ylethoxy)-2-oxo-pyrrolidin-1-yl]pyridine-3-carboxylic Acid

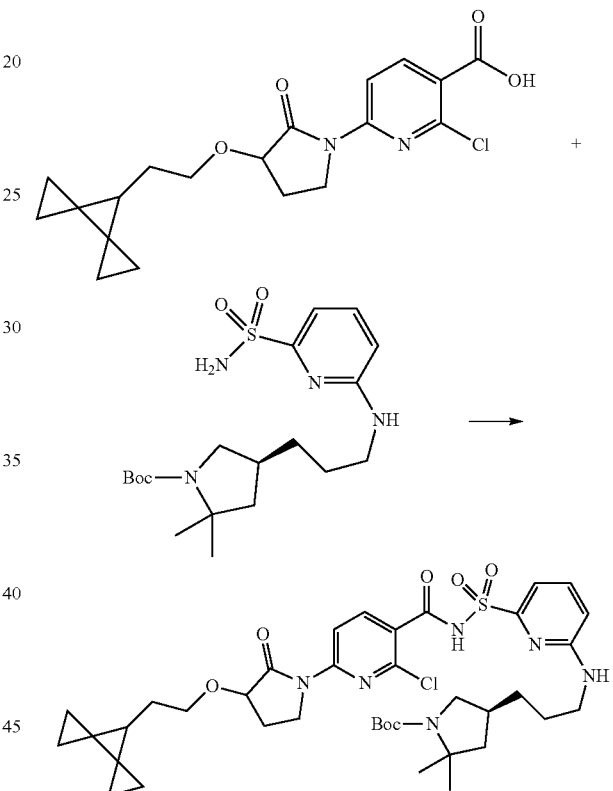

A 100 mL flask was charged with tert-butyl 2-chloro-6-[3-(2-dispiro[2.0.2.1]heptan-7-ylethoxy)-2-oxo-pyrrolidin-1-yl]pyridine-3-carboxylate (533 mg, 1.231 mmol), dichloromethane (5 mL) and trifluoroacetic acid (1.4 mL, 18.17 mmol) (color changed to brown quickly). The mixture was stirred at room temperature for 3 h. The reaction was diluted with dichloromethane and hexanes and the volatiles were evaporated under reduced pressure. The residue was triturated with dichloromethane/hexanes and the volatiles were evaporated (cycle repeated 3 times) to give 2-chloro-6-[3-(2-dispiro[2.0.2.1]heptan-7-ylethoxy)-2-oxo-pyrrolidin-1-yl]pyridine-3-carboxylic acid (479 mg, 103% yield, 93% purity) as a pale grey solid. $^1$H NMR (400 MHz, dimethyl sulfoxide-$d_6$) δ 13.51 (s, 1H), 8.34 (d, J=8.6 Hz, 1H), 8.31 (d, J=8.5 Hz, 1H), 4.32 (t, J=8.3 Hz, 1H), 4.01 (ddd, J=11.2, 8.8, 2.8 Hz, 1H), 3.88-3.63 (m, 2H), 3.56 (dt, J=9.3, 6.7 Hz, 1H), 2.47-2.37 (m, 1H), 1.89 (dq, J=12.2, 8.6 Hz, 1H), 1.62 (q, J=6.7 Hz, 2H), 1.39 (t, J=6.5 Hz, 1H), 0.93-0.69 (m, 4H), 0.69-0.56 (m, 2H), 0.46 (d, J=8.6 Hz, 2H). ESI-MS m/z calc. 376.119, found 377.1 (M+1)$^+$; Retention time: 1.83 min (LC Method B).

Step 4: tert-Butyl (4S)-4-[3-[[6-[[2-chloro-6-[3-(2-dispiro[2.0.2.1]heptan-7-ylethoxy)-2-oxo-pyrrolidin-1-yl]pyridine-3-carbonyl]sulfamoyl]-2-pyridyl]amino]propyl]-2,2-dimethyl-pyrrolidine-1-carboxylate

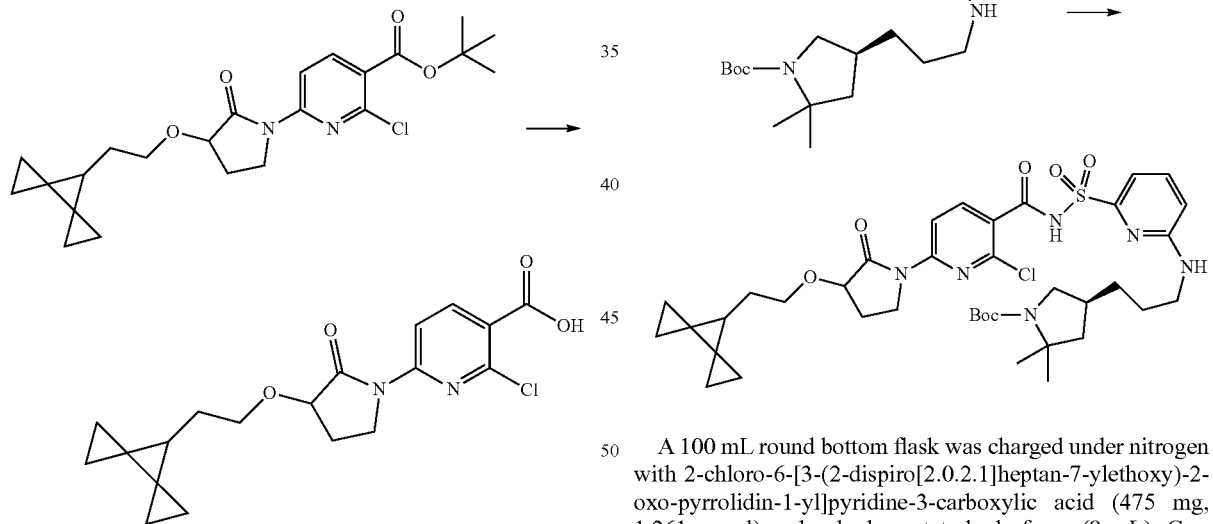

A 100 mL round bottom flask was charged under nitrogen with 2-chloro-6-[3-(2-dispiro[2.0.2.1]heptan-7-ylethoxy)-2-oxo-pyrrolidin-1-yl]pyridine-3-carboxylic acid (475 mg, 1.261 mmol) and anhydrous tetrahydrofuran (8 mL). Carbonyl diimidazole (225 mg, 1.388 mmol) (freshly recrystallized from tetrahydrofuran) was added and the mixture was stirred under nitrogen at room temperature for 2. Another 150 mg of carbonyl diimidazole was added and the mixture was stirred at room temperature for 2 h. In a separate 20 mL flask, a solution of tert-butyl (4S)-2,2-dimethyl-4-[3-[(6-sulfamoyl-2-pyridyl)amino]propyl]pyrrolidine-1-carboxylate (520 mg, 1.260 mmol) in anhydrous tetrahydrofuran (4 mL) was prepared under a nitrogen atmosphere and it was subsequently added via syringe into the activated ester solution. Added 1,8-diazabicyclo[5.4.0]undec-7-ene (0.95 mL, 6.353 mmol) through a syringe and the reaction mixture was stirred at room temperature under nitrogen atmosphere overnight. After 18 h, the solvents were removed under reduced pressure and the resulting thick oil was treated with ethyl acetate (30 mL) and water (30 mL). Aqueous hydrochloric acid (1.4 mL of 6 M, 8.400 mmol) was added slowly (final pH=5) and the two phases were separated. The aqueous phase was extracted again with ethyl acetate (30 mL). The combined organic extracts were washed with brine (30 mL) and dried over sodium sulfate. After filtration and evaporation of the solvents, the residue (1.34 g) was dissolved in dichloromethane and purified by flash chromatography on silica gel using a gradient of ethyl acetate (0 to 100% over 30 min) in hexanes giving still impure product. This material was further purified by flash chromatography on silica gel using a gradient of ethyl acetate (0 to 100% over 30 min) in hexanes to give tert-butyl (4S)-4-[3-[[6-[[2-chloro-6-[3-(2-dispiro[2.0.2.1]heptan-7-ylethoxy)-2-oxo-pyrrolidin-1-yl]pyridine-3-carbonyl]sulfamoyl]-2-pyridyl]amino]propyl]-2,2-dimethyl-pyrrolidine-1-carboxylate (449 mg, 46%) as a white foamy solid. ESI-MS m/z calc. 770.3229, found 771.5 (M+1)$^+$; Retention time: 2.43 min (LC Method B).

Step 5: 2-Chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)-2-oxo-pyrrolidin-1-yl]pyridine-3-carboxamide (Dihydrochloride Salt)

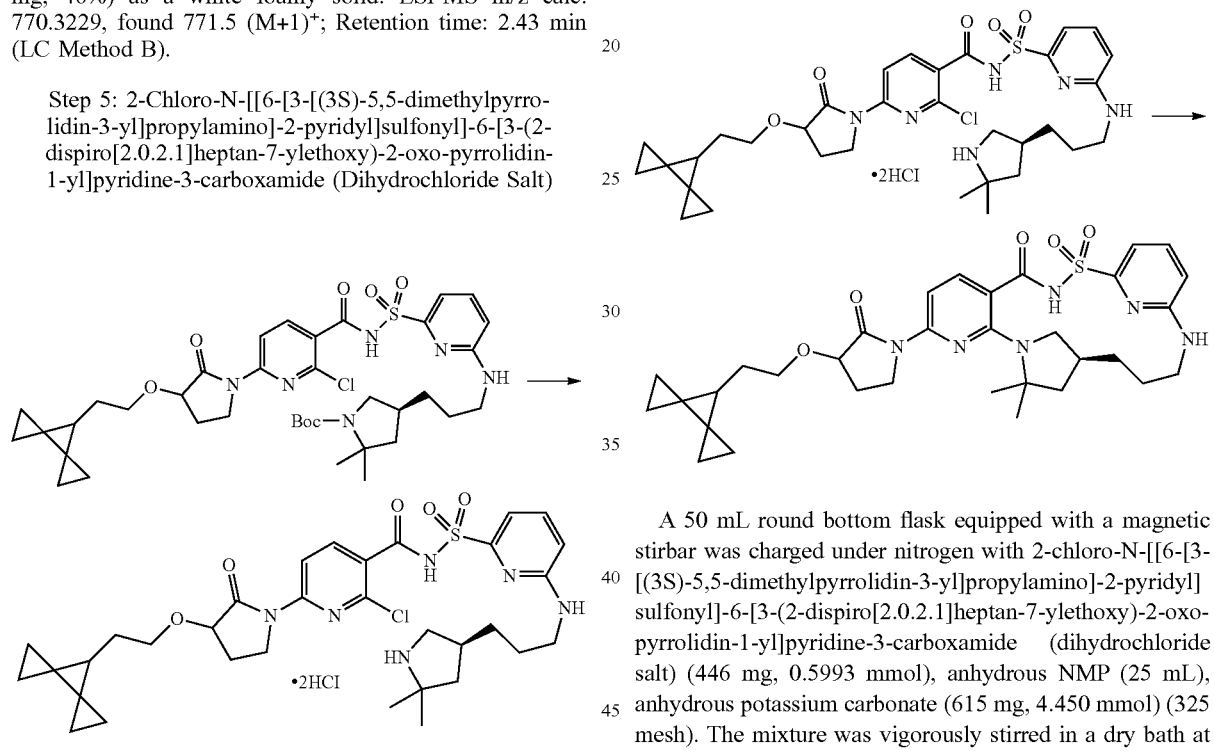

A 100 mL was charged with tert-butyl (4S)-4-[3-[[6-[[2-chloro-6-[3-(2-dispiro[2.0.2.1]heptan-7-ylethoxy)-2-oxo-pyrrolidin-1-yl]pyridine-3-carbonyl]sulfamoyl]-2-pyridyl]amino]propyl]-2,2-dimethyl-pyrrolidine-1-carboxylate (440 mg, 0.5704 mmol), dichloromethane (5 mL) and hydrochloric acid (800 µL of 4 M in dioxane, 3.200 mmol). The reaction was stirred at room temperature for nearly 3 h. The volatiles were removed by evaporation under vacuum. The residue was triturated with dichloromethane/hexanes and the solvents evaporated. The operation was repeated until a white solid was obtained. Drying under vacuum gave 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)-2-oxo-pyrrolidin-1-yl]pyridine-3-carboxamide (dihydrochloride salt) (453 mg, 107%) as a white solid. The product was used in the next step without any further purification. $^1$H NMR (400 MHz, dimethyl sulfoxide-d$_6$) δ 12.75 (broad s, 1H), 9.12 (br s, 1H), 8.99 (br s, 1H), 8.32 (d, J=8.5 Hz, 1H), 8.02 (dd, J=8.5, 0.8 Hz, 1H), 7.61 (dd, J=8.5, 7.2 Hz, 1H), 7.26 (br s, 1H) 7.19-7.11 (m, 1H), 6.75 (dd, J=8.5, 0.7 Hz, 1H), 4.32 (t, J=8.3 Hz, 1H), 3.97 (td, J=8.8, 8.3, 4.7 Hz, 1H), 3.84-3.65 (m, 2H), 3.56 (dt, J=9.2, 6.7 Hz, 1H), 3.35-3.28 (m, 1H) 3.29-3.15 (m, 2H), 2.88-2.73 (m, 1H), 2.49-2.25 (m, 2H), 1.98-1.81 (m, 2H), 1.62 (q, J=6.7 Hz, 2H), 1.56-1.44 (m, 3H), 1.44-1.33 (m, 6H), 1.28-1.26 (m, 3H), 0.82-0.76 (m, 4H), 0.68-0.57 (m, 2H), 0.53-0.39 (m, 2H). ESI-MS m/z calc. 670.27045, found 671.4 (M+1)$^+$; Retention time: 1.65 min (LC Method B).

Step 6: (14S)-8-[3-(2-{dispiro[2.0.2.1]heptan-7-yl}ethoxy)-2-oxopyrrolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione

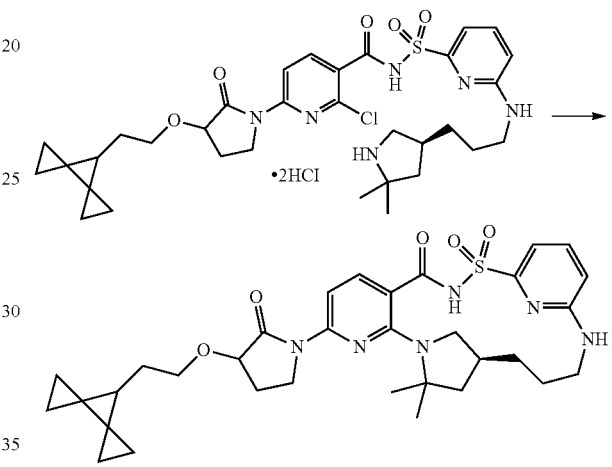

A 50 mL round bottom flask equipped with a magnetic stirbar was charged under nitrogen with 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)-2-oxo-pyrrolidin-1-yl]pyridine-3-carboxamide (dihydrochloride salt) (446 mg, 0.5993 mmol), anhydrous NMP (25 mL), anhydrous potassium carbonate (615 mg, 4.450 mmol) (325 mesh). The mixture was vigorously stirred in a dry bath at 150° C. under nitrogen for 14 h, then at 155° C. for 3 h, then at 160° C. for 3.5 h. After cooling down to room temperature, the mixture was poured into cold water (200 mL) and acidified by adding aqueous hydrochloric acid (1.5 mL of 6 M, 9.000 mmol) (mild foaming). The resulting solid was filtered and briefly air dried. The solid was dissolved in dichloromethane and the resulting cloudy solution was decanted to separate remaining water and dried over sodium sulfate. After concentration, the residue was purified by flash chromatography on silica gel using a gradient of methanol (0 to 5% over 30 min) in dichloromethane. Evaporation of the solvents, followed by trituration in dichloromethane/hexanes and evaporation of the solvents gave (14S)-8-[3-(2-{dispiro[2.0.2.1]heptan-7-yl}ethoxy)-2-oxopyrrolidin-1-yl]-12,12-dimethyl-2λ$^6$-thia-3,9,11,18,23-pentaazatetracyclo[17.3.1.111,14.05,10]tetracosa-1 (22),5,7,9,19(23),20-hexaene-2,2,4-trione (198 mg, 52%) as a white solid. ESI-MS m/z calc. 634.29376, found 635.4 (M+1)$^+$; Retention time: 2.17 min (LC Method B).

Step 7: (14S)-8-[3-(2-{Dispiro[2.0.2.1]heptan-7-yl}ethoxy)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 179) and (14S)-8-[3-(2-{dispiro[2.0.2.1]heptan-7-yl}ethoxy)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 2) (Compound 180)

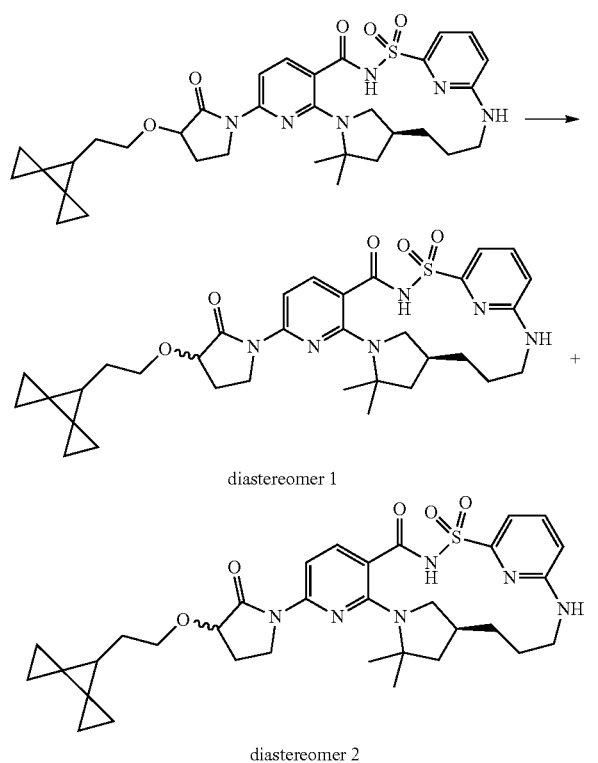

diastereomer 1 diastereomer 2

(14S)-8-[3-(2-{dispiro[2.0.2.1]heptan-7-yl}ethoxy)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (200 mg, 0.3088 mmol) was subjected to chiral separation by SFC chromatography using a ChiralPak OJ-H (250×10 mm) column (5 μm particle size) with 20% acetonitrile/methanol (90:10)/80% carbon dioxide mobile phase at 10 mL/min over 8.0 min [injection volume=70 μL of 24 mg/mL solution in acetonitrile/methanol/dimethyl sulfoxide (85:9:6)] giving as the first diastereomer to elute, (14S)-8-[3-(2-{dispiro[2.0.2.1]heptan-7-yl}ethoxy)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 1) (Compound 179) (86 mg, 43%, >98% ee) as white solid, ¹H NMR (400 MHz, dimethyl sulfoxide-d₆) δ 12.43 (s, 1H), 7.70 (d, J=8.4 Hz, 1H), 7.57 (dd, J=8.5, 7.2 Hz, 1H), 7.51 (d, J=8.4 Hz, 1H), 7.04 (d, J=7.1 Hz, 1H), 6.96 (d, J=9.0 Hz, 1H), 6.70 (d, J=8.5 Hz, 1H), 4.22 (t, J=7.9 Hz, 1H), 4.02 (ddd, J=10.9, 8.6, 3.2 Hz, 1H), 3.91 (q, J=11.4 Hz, 1H), 3.79 (dt, J=9.2, 6.7 Hz, 1H), 3.70 (dt, J=10.5, 7.5 Hz, 1H), 3.55 (dt, J=9.2, 6.7 Hz, 1H), 3.18-3.06 (m, 1H), 2.94 (d, J=13.2 Hz, 1H), 2.76-2.62 (m, 1H), 2.40 (dtd, J=12.3, 7.2, 2.9 Hz, 1H), 2.18-2.01 (m, 1H), 1.97-1.86 (m, 1H), 1.82 (dd, J=12.1, 5.4 Hz, 1H), 1.79-1.68 (m, 1H), 1.62 (q, J=6.7 Hz, 4H) (actually two triplets, 2×2H), 1.57 (s, 3H), 1.55-1.49 (m, 1H), 1.46 (s, 3H), 1.38 (t, J=6.5 Hz, 1H), 1.30-1.23 (m, 1H), 0.84-0.77 (m, 4H), 0.67-0.57 (m, 2H), 0.50-0.41 (m, 2H); ESI-MS m/z calc. 634.29376, found 635.4 (M+1)⁺; Retention time: 2.19 min (LC Method B); and as the second diastereomer to elute, (14S)-8-[3-(2-{dispiro[2.0.2.1]heptan-7-yl}ethoxy)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 2) (Compound 180) (76 mg, 38%, >98% ee) as a white solid; ¹H NMR (400 MHz, dimethyl sulfoxide-d₆) δ 12.41 (s, 1H), 7.70 (d, J=8.5 Hz, 1H), 7.57 (t, J=7.9 Hz, 1H), 7.52 (d, J=8.4 Hz, 1H), 7.04 (d, J=7.2 Hz, 1H), 6.96 (s, 1H), 6.70 (d, J=8.5 Hz, 1H), 4.27 (t, J=8.2 Hz, 1H), 3.91 (t, J=9.9 Hz, 2H), 3.78 (t, J=8.2 Hz, 2H), 3.54 (q, J=8.2 Hz, 1H), 3.14-3.04 (m, 1H), 2.98-2.89 (m, 1H), 2.72-2.63 (m, 1H), 2.16-2.03 (m, 1H), 1.89-1.72 (m, 3H), 1.61 (two triplets, 2×2H), 1.57 (s, 3H), 1.53-1.48 (m, 1H), 1.46 (s, 3H), 1.41-1.35 (m, 1H), 1.35-1.19 (m, 2H), 0.83-0.76 (m, 4H), 0.62 (d, J=8.9 Hz, 2H), 0.46 (d, J=8.8 Hz, 2H); ESI-MS m/z calc. 634.29376, found 635.4 (M+1)⁺; Retention time: 2.18 min (LC Method B).

Example 49: Preparation of (14S)-12,12-dimethyl-8-{3-[2-(2,2,3,3-tetramethylcyclopropyl)ethoxy]-1H-pyrazol-1-yl}-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 185)

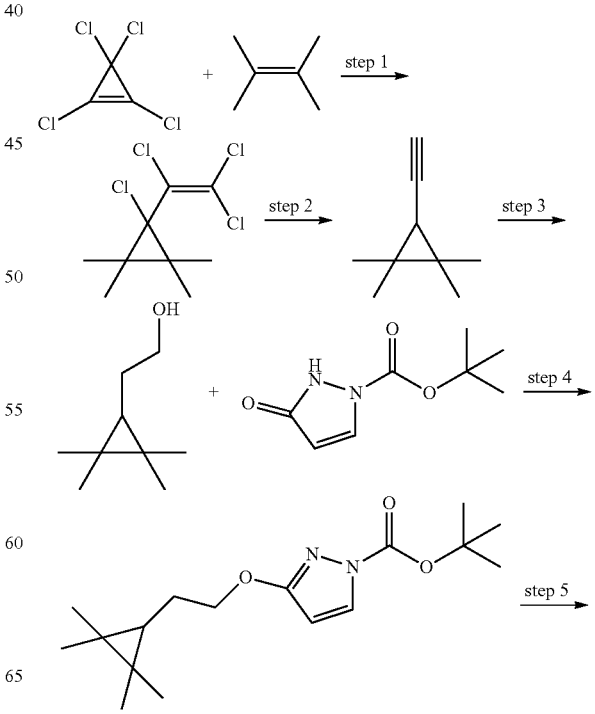

-continued

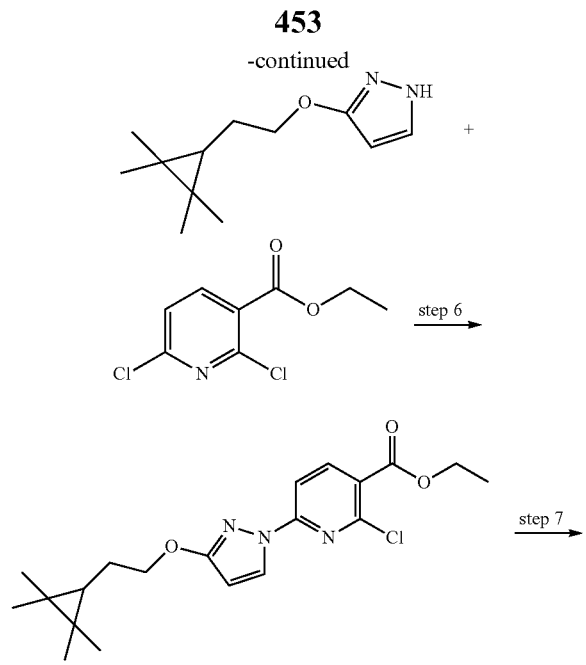

step 6

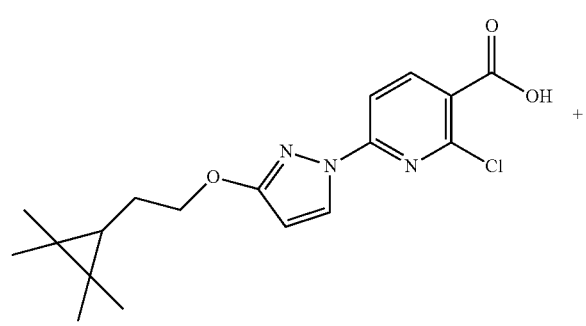

step 7

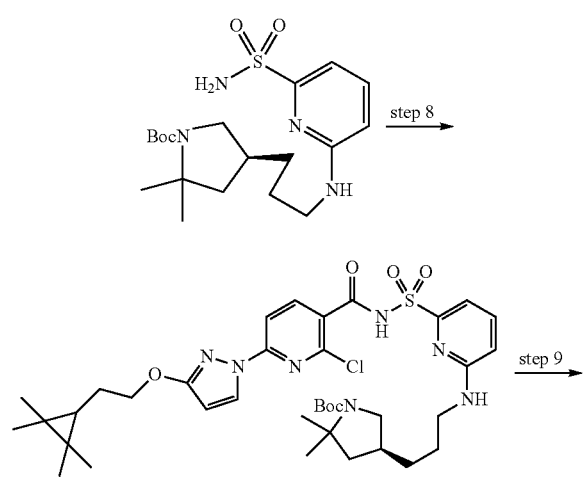

step 8

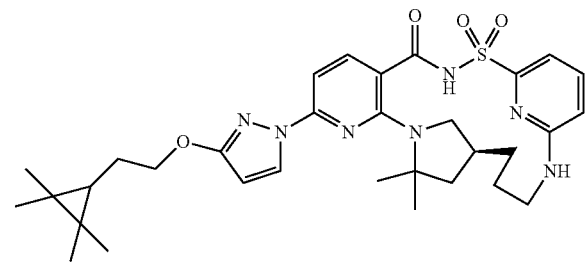

step 9

Step 1: 1-Chloro-2,2,3,3-tetramethyl-1-(1,2,2-trichlorovinyl)cyclopropane

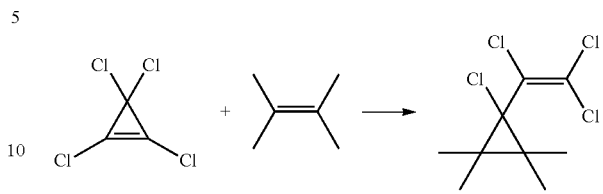

To a microwave vial was added 2,3-dimethylbut-2-ene (20.5 mL, 172.5 mmol) and 1,2,3,3-tetrachlorocyclopropene (29.1 g, 163.6 mmol). The reaction vessel was sealed and heated at 155° C. for 16 h. The reaction was cooled to room temperature and transferred to a flask. The crude reaction was subjected to bulb-to-bulb distillation under vacuum at 195° C. to provide 1-chloro-2,2,3,3-tetramethyl-1-(1,2,2-trichlorovinyl)cyclopropane (37.49 g, 87%) as an orange liquid. $^1$H NMR (400 MHz, Chloroform-d) δ 1.25 (s, 3H), 1.22 (s, 3H), 1.20 (s, 3H), 1.18 (s, 3H).

Step 2: 3-Ethynyl-1,1,2,2-tetramethyl-cyclopropane

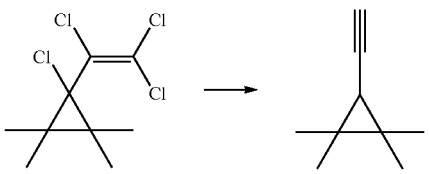

To a 500 mL round bottom flask was added 1-chloro-2,2,3,3-tetramethyl-1-(1,2,2-trichlorovinyl)cyclopropane (17.4 g, 66.41 mmol) and diethyl ether (300 mL). The reaction was chilled to −78° C. and the reaction was stirred for 15 min. A solution of n-butyllithium (118 mL of 2.5 M, 295.0 mmol) was added dropwise over 30 min and allowed the mixture to warm to room temperature over 2 h and additionally stirred at room temperature for 1 h. The reaction was cooled to −10° C. and water (35 mL, 1.943 mol) was added dropwise and allowed the mixture to stir and warm to room temperature over 30 min. The reaction was extracted with ether, dried over sodium sulfate, filtered and evaporated. The crude reaction mixture was purified via distillation at 80° C. under vacuum to provide 3-ethynyl-1,1,2,2-tetramethyl-cyclopropane (6.059 g, 75%). $^1$H NMR (400 MHz, Chloroform-d) δ 1.96 (d, J=2.2 Hz, 1H), 1.11 (d, J=3.8 Hz, 12H), 0.86 (d, J=0.9 Hz, 1H).

Step 3: 2-(2,2,3,3-Tetramethylcyclopropyl)ethanol

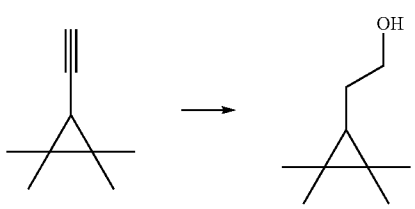

To a dry round bottom flask was added 3-ethynyl-1,1,2,2-tetramethyl-cyclopropane (4.1 g, 33.55 mmol) and tetrahydrofuran (25 mL). The reaction was chilled in a −30° C. bath for 5 min. A solution of borane in tetrahydrofuran (33.6 mL of 1 M, 33.60 mmol) was added dropwise and the reaction was allowed to warm to room temperature over 30 min. The reaction was cooled to −10° C. and sodium hydroxide (28.5 mL of 6 M, 171.0 mmol) was added cautiously followed by hydrogen peroxide (38 mL of 30% w/v, 335.1 mmol). The reaction was allowed to stir for 30 min while warming to room temperature. The reaction was extracted with ether, dried over sodium sulfate, filtered and evaporated to provide the crude aldehyde intermediate. To the crude aldehyde was added methanol (40 mL). The reaction was chilled to 0° C. and sodium borohydride (2.54 g, 67.14 mmol) was added portionwise. The reaction was allowed to stir for 1 h while warming to room temperature. The reaction was quenched with a solution of saturated ammonium chloride and brine and extracted with ether. The organic layer was dried over sodium sulfate, filtered and evaporated to provide 2-(2,2,3,3-tetramethylcyclopropyl) ethanol (1.800 g, 38%) as an oil. $^1$H NMR (400 MHz, Chloroform-d) δ 3.64 (t, J=6.9 Hz, 2H), 1.54 (q, J=7.0 Hz, 2H), 1.06 (s, 6H), 0.93 (s, 6H), 0.13 (t, J=7.1 Hz, 1H). ESI-MS m/z calc. 142.13577, found 143.1 (M+1)$^+$; Retention time: 1.49 min (LC Method B).

Step 4: tert-Butyl 3-[2-(2,2,3,3-tetramethylcyclopropyl)ethoxy]pyrazole-1-carboxylate

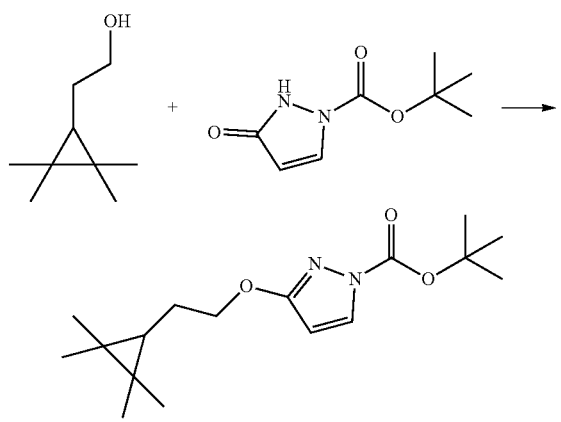

To a solution of tert-butyl 5-oxo-1H-pyrazole-2-carboxylate (884 mg, 4.799 mmol) and 2-(2,2,3,3-tetramethylcyclopropyl)ethanol (650 mg, 4.570 mmol) in tetrahydrofuran (10 mL) was added triphenylphosphine (1.26 g, 4.804 mmol). To the mixture was slowly added diisopropyl azodicarboxylate (970 mg, 4.797 mmol) dropwise over 2 min at room temperature (exotherm noted). The reaction mixture was stirred at room temperature for 30 min. The tetrahydrofuran was removed in vacuo and toluene (30 mL) was added and the mixture was stirred overnight. No precipitate was observed and the mixture was evaporated and purified by silica gel chromatography (0% to 50% ethyl acetate in hexanes gradient) to afford tert-butyl 3-[2-(2,2,3,3-tetramethylcyclopropyl)ethoxy]pyrazole-1-carboxylate (700 mg, 50%). $^1$H NMR (400 MHz, Chloroform-d) δ 7.82 (d, J=2.9 Hz, 1H), 5.86 (d, J=2.9 Hz, 1H), 4.27 (t, J=7.2 Hz, 2H), 1.72 (q, J=7.2 Hz, 2H), 1.61 (s, 10H), 1.05 (s, 6H), 0.95 (s, 6H), 0.22 (t, J=7.2 Hz, 1H). ESI-MS m/z calc. 308.21, found 309.24 (M+1)$^+$; Retention time: 0.89 min (LC Method A).

Step 5: 3-[2-(2,2,3,3-Tetramethylcyclopropyl)ethoxy]-1H-pyrazole

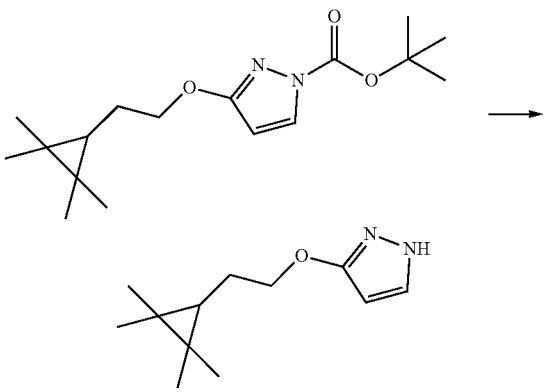

To a solution of tert-butyl 3-[2-(2,2,3,3-tetramethylcyclopropyl)ethoxy]pyrazole-1-carboxylate (700 mg, 2.270 mmol) in methanol (7.0 mL) was added sodium hydroxide (2.35 mL of 2 M, 4.700 mmol) and the mixture was stirred at ambient temperature for 30 min. The majority of the methanol was removed in vacuo and the residue was diluted with water (14 mL) and aqueous hydrochloric acid (4.5 mL of 1 M, 4.500 mmol). The mixture was extracted with ethyl acetate and the organic phase washed with brine, dried over sodium sulfate, filtered and concentrated in vacuo affording a pale yellow oil, 3-[2-(2,2,3,3-tetramethylcyclopropyl)ethoxy]-1H-pyrazole (471 mg, 100%) which was used directly in the next step. ESI-MS m/z calc. 208.15756, found 209.2 (M+1)$^+$; Retention time: 1.77 min (LC Method E).

Step 6: Ethyl 2-chloro-6-[3-[2-(2,2,3,3-tetramethylcyclopropyl)ethoxy]pyrazol-1-yl]pyridine-3-carboxylate

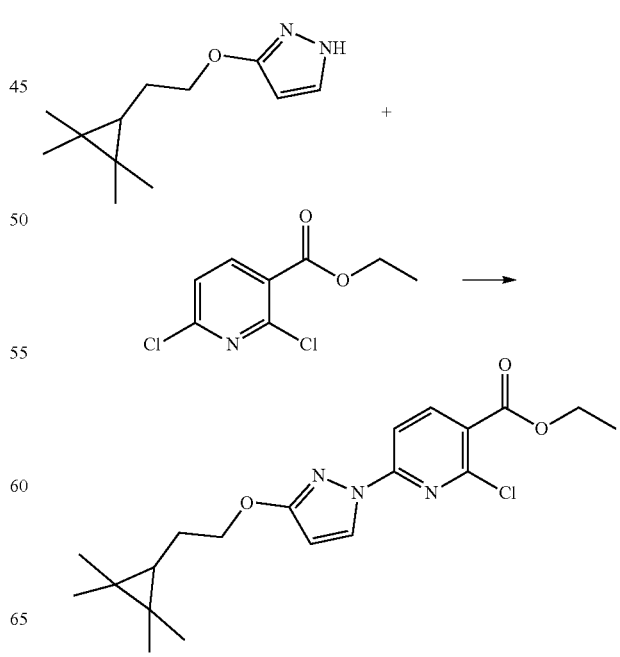

Ethyl 2,6-dichloropyridine-3-carboxylate (494 mg, 2.245 mmol), 3-[2-(2,2,3,3-tetramethylcyclopropyl)ethoxy]-1H-pyrazole (471 mg, 2.261 mmol) and potassium carbonate (373 mg, 2.699 mmol) were combined in anhydrous dimethyl sulfoxide (10 mL). 1,4-Diazabicyclo[2.2.2]octane (50.5 mg, 0.4502 mmol) was added and the mixture was stirred at room temperature under nitrogen for 20 h. The reaction mixture was diluted with water (16 mL) and stirred for 15 min. The resulting white solid was collected by filtration and washed with water. The solid was dissolved in dichloromethane and dried over sodium sulfate. The mixture was filtered and evaporated to provide as an off-white solid, ethyl 2-chloro-6-[3-[2-(2,2,3,3-tetramethylcyclopropyl)ethoxy]pyrazol-1-yl]pyridine-3-carboxylate (800 mg, 91%). $^1$H NMR (400 MHz, Chloroform-d) δ 8.36 (d, J=2.9 Hz, 1H), 8.27 (d, J=8.4 Hz, 1H), 7.72 (d, J=8.5 Hz, 1H), 5.97 (d, J=2.9 Hz, 1H), 4.41 (q, J=7.2 Hz, 2H), 4.25 (t, J=7.2 Hz, 2H), 1.77 (q, J=7.2 Hz, 2H), 1.42 (t, J=7.2 Hz, 3H), 1.08 (s, 6H), 0.97 (s, 6H), 0.25 (t, J=7.2 Hz, 1H). ESI-MS m/z calc. 391.16626, found 392.2 (M+1)$^+$; Retention time: 2.25 min (LC Method E).

Step 7: 2-Chloro-6-[3-[2-(2,2,3,3-tetramethylcyclopropyl)ethoxy]pyrazol-1-yl]pyridine-3-carboxylic Acid

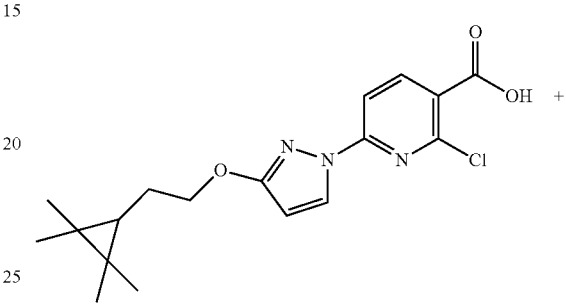

Ethyl 2-chloro-6-[3-[2-(2,2,3,3-tetramethylcyclopropyl)ethoxy]pyrazol-1-yl]pyridine-3-carboxylate (800 mg, 2.041 mmol) in tetrahydrofuran (4.000 mL) and ethanol (1.600 mL) was treated with sodium hydroxide (2.0 mL of 2 M, 4.000 mmol) and the solution was stirred at room temperature for 1 h. The majority of the solvent was removed under reduced pressure and the solution was acidified by slow addition of citric acid (8.0 mL of 10% w/v, 4.164 mmol) under ice cooling. The formed thick suspension (pH=3) was stirred in the ice bath for 1 h, filtered and washed with excess water. The collected solid was fully dissolved in dichloromethane, dried over sodium sulfate, filtered and concentrated to dryness using toluene as an azeotrope and further dried under vacuum for 21 h to give 2-chloro-6-[3-[2-(2,2,3,3-tetramethylcyclopropyl)ethoxy]pyrazol-1-yl]pyridine-3-carboxylic acid (710 mg, 96%) as a white solid. $^1$H NMR (400 MHz, dimethyl sulfoxide-d$_6$) δ 13.56 (s, 1H), 8.52-8.29 (m, 2H), 7.72 (d, J=8.4 Hz, 1H), 6.18 (d, J=2.8 Hz, 1H), 4.23 (t, J=6.8 Hz, 2H), 1.72 (q, J=7.0 Hz, 2H), 1.04 (s, 6H), 0.95 (s, 6H), 0.27 (t, J=7.2 Hz, 1H). ESI-MS m/z calc. 363.13498, found 364.2 (M+1)$^+$; Retention time: 2.35 min (LC Method G).

Step 8: tert-Butyl (4S)-4-[3-[[6-[[2-chloro-6-[3-[2-(2,2,3,3-tetramethylcyclopropyl) ethoxy]pyrazol-1-yl]pyridine-3-carbonyl]sulfamoyl]-2-pyridyl]amino] propyl]-2,2-dimethyl-pyrrolidine-1-carboxylate

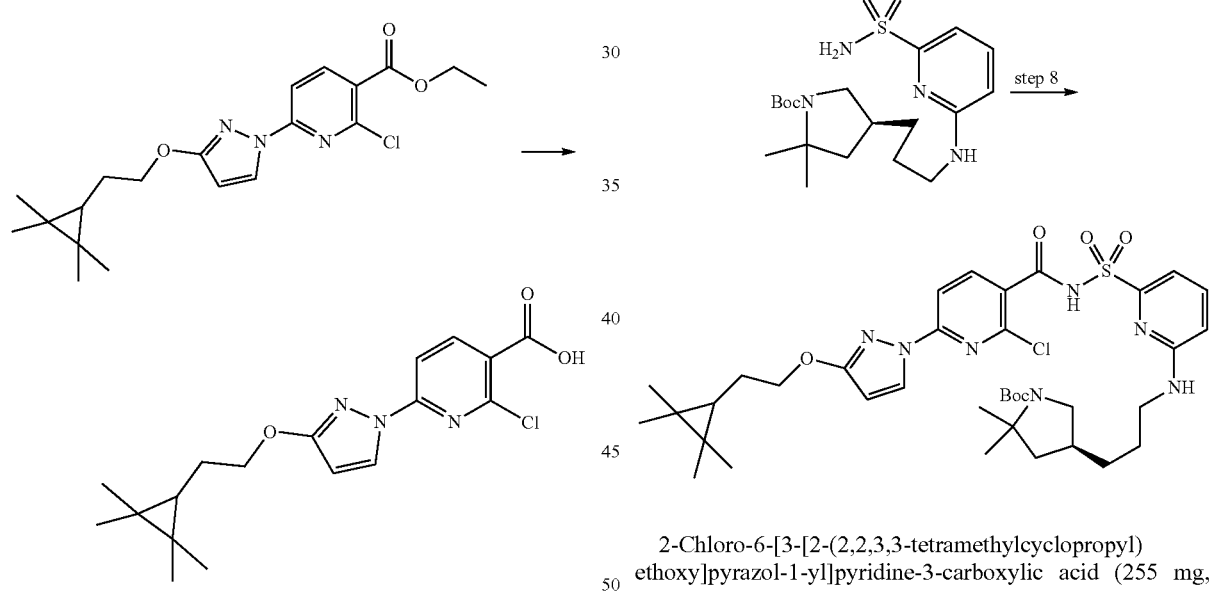

2-Chloro-6-[3-[2-(2,2,3,3-tetramethylcyclopropyl)ethoxy]pyrazol-1-yl]pyridine-3-carboxylic acid (255 mg, 0.7009 mmol) and carbonyl diimidazole (125 mg, 0.7709 mmol) were combined in tetrahydrofuran (5.738 mL) and stirred for 90 min at room temperature. tert-Butyl (4S)-2,2-dimethyl-4-[3-[(6-sulfamoyl-2-pyridyl)amino]propyl]pyrrolidine-1-carboxylate (350 mg, 0.8484 mmol) was added followed by anhydrous 1,8-diazabicyclo[5.4.0]undec-7-ene (275 μL, 1.839 mmol) and the reaction was stirred at room temperature for 20 h. The reaction was diluted with ethyl acetate and washed with a saturated aqueous sodium bicarbonate solution followed by brine. The organics were separated, dried over sodium sulfate, filtered and evaporated under reduced pressure then purified via silica gel chromatography using a gradient from 100% hexanes to 80% ethyl acetate in hexanes to afford tert-butyl (4S)-4-[3-[[2-chloro-6-[3-[2-(2,2,3,3-tetramethylcyclopropyl)ethoxy]pyrazol-1-yl]pyridine-3-carbonyl]sulfamoyl]-2-pyridyl]amino]propyl]-2,2-dimethyl-pyrrolidine-1-carboxylate (261 mg, 49%) as a white solid. ESI-MS m/z calc. 757.3388, found 758.5 (M+1)+; Retention time: 2.43 min (LC Method G).

Step 9: (14S)-12,12-Dimethyl-8-{3-[2-(2,2,3,3-tetramethylcyclopropyl)ethoxy]-1H-pyrazol-1-yl}-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 185)

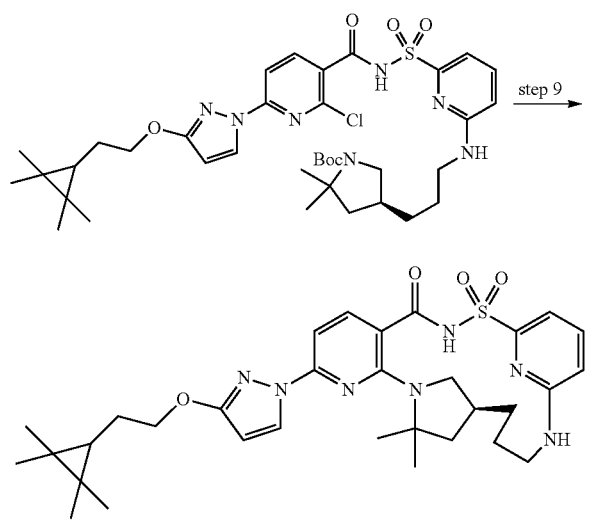

tert-Butyl (4S)-4-[3-[[6-[[2-chloro-6-[3-[2-(2,2,3,3-tetramethylcyclopropyl)ethoxy]pyrazol-1-yl]pyridine-3-carbonyl]sulfamoyl]-2-pyridyl]amino]propyl]-2,2-dimethylpyrrolidine-1-carboxylate (115 mg, 0.1516 mmol), potassium carbonate (125 mg, 0.9045 mmol), 3 Å molecular sieves and dimethyl sulfoxide (4 mL) were combined in a vial, purged with nitrogen, capped, heated to 160° C. and stirred for 72 h. Cooled to room temperature. The mixture was filtered and the filtrate was diluted with ethyl acetate and washed with a sat aqueous sodium bicarbonate solution, followed by brine. The organics were separated, dried over sodium sulfate, and evaporated and then purified by silica gel chromatography using a gradient from 100% hexanes to 70% ethyl acetate in hexanes to afford as an off-white solid (14S)-12,12-dimethyl-8-{3-[2-(2,2,3,3-tetramethylcyclopropyl)ethoxy]-1H-pyrazol-1-yl}-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 185) (18.14 mg, 19%). ¹H NMR (400 MHz, Chloroform-d) δ 9.96 (s, 1H), 8.20 (d, J=2.8 Hz, 1H), 8.07 (d, J=8.3 Hz, 1H), 7.60-7.49 (m, 2H), 7.36-7.23 (m, 2H), 6.56 (d, J=8.0 Hz, 1H), 5.92 (d, J=2.9 Hz, 1H), 4.82-4.58 (m, 1H), 4.25 (t, J=7.2 Hz, 2H), 4.00-3.76 (m, 1H), 3.35 (t, J=8.8 Hz, 1H), 3.17 (d, J=14.3 Hz, 1H), 3.07 (t, J=9.8 Hz, 1H), 2.73-2.50 (m, 1H), 2.09 (dd, J=12.3, 7.9 Hz, 1H), 1.76 (q, J=7.1 Hz, 2H), 1.65-1.59 (m, 6H), 1.53-1.41 (m, 2H), 1.08 (s, 6H), 0.97 (s, 6H), 0.90-0.81 (m, 2H), 0.25 (t, J=7.2 Hz, 1H). ESI-MS m/z calc. 621.30975, found 622.2 (M+1)+; Retention time: 2.22 min (LC Method B).

Example 50: Preparation of (18S)-4-[3-(2-{dispiro[2.0.2.1]heptan-7-yl}ethoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 187)

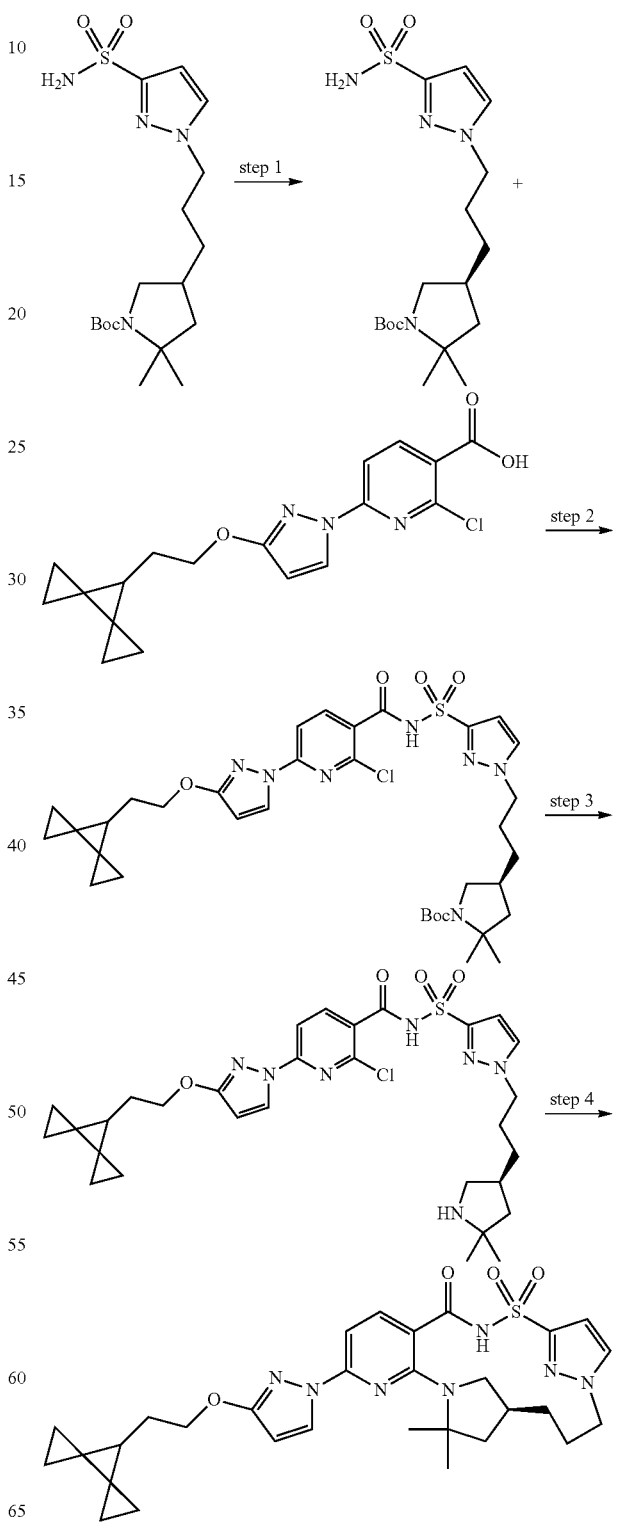

Step 1: tert-Butyl (4S)-2,2-dimethyl-4-[3-(3-sulfamoylpyrazol-1-yl)propyl]pyrrolidine-1-carboxylate

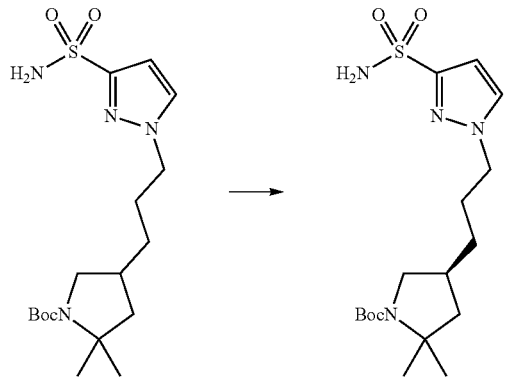 [SMILES: CC(C)(C)OC(=O)N1CC(CCCn2ccc(S(N)(=O)=O)n2)CC1(C)C ; CC(C)(C)OC(=O)N1C[C@@H](CCCn2ccc(S(N)(=O)=O)n2)CC1(C)C]

Subjected racemic tert-butyl 2,2-dimethyl-4-[3-(3-sulfamoylpyrazol-1-yl)propyl]pyrrolidine-1-carboxylate (3.24 g, 8.383 mmol) to chiral separation by SFC chromatography using a ChiralPak IG (250×21.2 mm column, 5 μm particle size) with 28% methanol/72% carbon dioxide mobile phase at 70 mL/min over 14.0 min (injection volume=500 μL of 32 mg/mL solution in methanol giving as the second enantiomer to elute, tert-butyl(4S)-2,2-dimethyl-4-[3-(3-sulfamoylpyrazol-1-yl)propyl]pyrrolidine-1-carboxylate (1.45 g, 90%). $^1$H NMR (400 MHz, CDCl$_3$) δ 7.42 (d, J=2.4 Hz, 1H), 6.72 (d, J=2.5 Hz, 1H), 5.08 (s, 2H), 4.22-4.12 (m, 2H), 3.64 (t, J=9.1 Hz, 1H), 2.80 (t, J=10.8 Hz, 1H), 2.05 (s, 1H), 1.99-1.80 (m, 3H), 1.58 (s, 1H), 1.45 (d, J=2.3 Hz, 9H), 1.40 (d, J=11.4 Hz, 4H), 1.27 (s, 4H). ESI-MS m/z calc. 386.19876, found 387.1 (M+1)$^+$; Retention time: 1.52 min (LC Method B).

Step 2: tert-Butyl (4S)-4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate

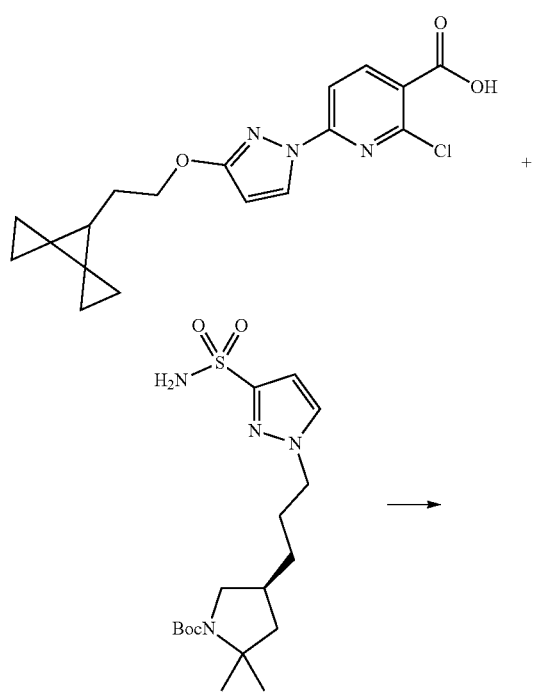

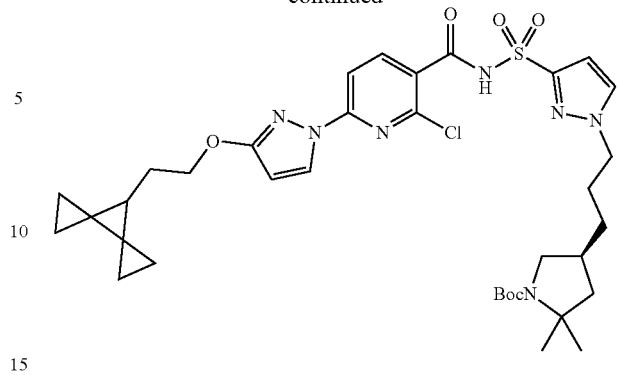

2-Chloro-6-[3-(2-dispiro[2.0.2.1]heptan-7-ylethoxy)pyrazol-1-yl]pyridine-3-carboxylic acid (1.35 g, 3.752 mmol) and carbonyl diimidazole (761.1 mg, 4.694 mmol) (freshly recrystallized from tetrahydrofuran, washed with cold ether and dried on high vacuum) were combined in tetrahydrofuran (17.55 mL) and stirred for 50 min at room temperature. Then tert-butyl (4S)-2,2-dimethyl-4-[3-(3-sulfamoylpyrazol-1-yl)propyl]pyrrolidine-1-carboxylate (1.45 g, 3.752 mmol) in tetrahydrofuran (6.75 mL) was added followed by 1,8-diazabicyclo[5.4.0]undec-7-ene (2.857 g, 18.77 mmol) and the reaction was stirred at room temperature for 16 h. Removed the tetrahydrofuran by rotary evaporation and dissolved in ethyl acetate and washed with saturated aqueous ammonium chloride (1×), then brine (1×), dried (sodium sulfate), filtered and concentrated to a white solid which was chromatographed on a 275 g C$_{18}$ reverse phase column eluting with a gradient from 50-100% acetonitrile/water. Product eluted both in pure fractions and mixed fractions with starting material acid. Pure fractions were combined, concentrated then partitioned between 6N hydrochloric acid and ethyl acetate. Separated the layers, washed the aqueous once more with ethyl acetate then combined the organic phases, dried (sodium sulfate), filtered and concentrated to a white solid. Mixed fractions from the reverse-phase column were combined and concentrated under reduced pressure. The residue was partitioned between 6N hydrochloric acid and ethyl acetate. Separated the layers, washed the aqueous once more with ethyl acetate then combined the organic phases, dried (sodium sulfate), filtered and concentrated to a white solid which was chromatographed on a 275 g C$_{18}$ reverse phase column eluting with a gradient from 50-100% acetonitrile/water. Pure fractions were combined, concentrated and added to the pure material from the first column to give tert-butyl (4S)-4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate (1.96 g, 72%). $^1$H NMR (400 MHz, CDCl$_3$) δ 9.50 (s, 1H), 8.30 (d, J=2.9 Hz, 1H), 8.26 (d, J=8.5 Hz, 1H), 7.75 (d, J=8.5 Hz, 1H), 7.47 (d, J=2.4 Hz, 1H), 7.05 (d, J=2.4 Hz, 1H), 5.96 (d, J=2.9 Hz, 1H), 4.25 (t, J=6.8 Hz, 2H), 4.20 (t, J=7.1 Hz, 2H), 3.66 (s, 1H), 2.83 (t, J=10.6 Hz, 1H), 2.06 (d, J=9.7 Hz, 1H), 1.90

(p, J=7.2 Hz, 5H), 1.48 (t, J=6.7 Hz, 2H), 1.44 (s, 9H), 1.37 (s, 3H), 1.35-1.29 (m, 2H), 1.26 (s, 3H), 0.87-0.82 (m, 4H), 0.69-0.64 (m, 2H), 0.51 (d, J=8.8 Hz, 2H). ESI-MS m/z calc. 727.2919, found 728.1 (M+1)+; Retention time: 0.91 min (LC Method A).

Step 3: 2-Chloro-N-[1-[3-[(3S)-5,5-dimethylpyrrolidin-3-yl]propyl]pyrazol-3-yl]sulfonyl-6-[3-(2-dispiro[2.0.2.1]heptan-7-ylethoxy)pyrazol-1-yl]pyridine-3-carboxamide

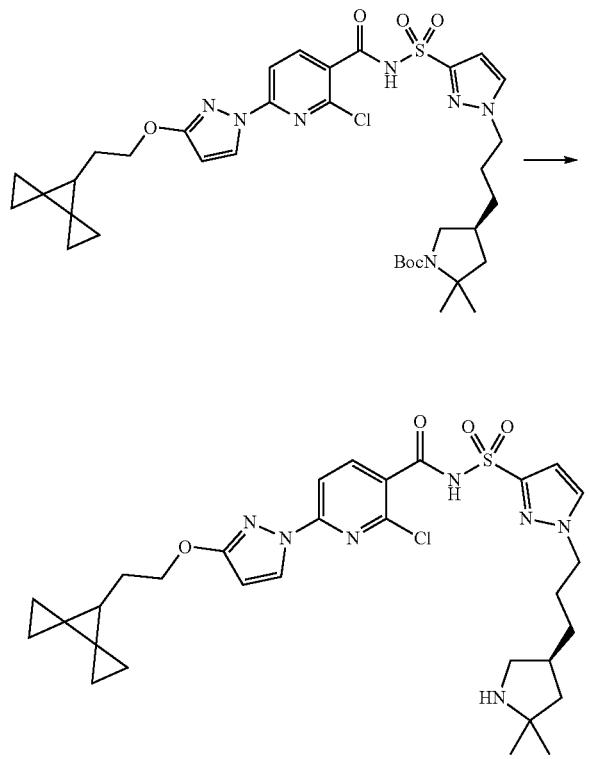

tert-Butyl (4S)-4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate (1.96 g, 2.691 mmol) was dissolved in dichloromethane (8.553 mL) and to the mixture was added trifluoroacetic acid (8.291 mL, 107.6 mmol) and the mixture was stirred at room temperature for 60 min. Concentrated mixture to dryness under reduced pressure, took up in saturated aqueous sodium bicarbonate and ethyl acetate containing some methanol for solubility and separated the layers. Concentrated the organic layer by rotary evaporation followed by high vacuum pump giving 2-chloro-N-[1-[3-[(3S)-5,5-dimethylpyrrolidin-3-yl]propyl]pyrazol-3-yl]sulfonyl-6-[3-(2-dispiro[2.0.2.1]heptan-7-ylethoxy)pyrazol-1-yl]pyridine-3-carboxamide (1.84 g, 109%) as a yellow solid. ESI-MS m/z calc. 627.23944, found 628.1 (M+1)+; Retention time: 0.65 min (LC Method A).

Step 4: (18S)-4-[3-(2-{Dispiro[2.0.2.1]heptan-7-yl}ethoxy)-1H-pyrazol-1-yl]-20,20-dimethyl-10λ6-thia-1,3,9,14,22-pentaazatetracyclo[16.2.1.111,14.02,7]docosa-2,4,6,11(22),12-pentaene-8,10,10-trione (Compound 187)

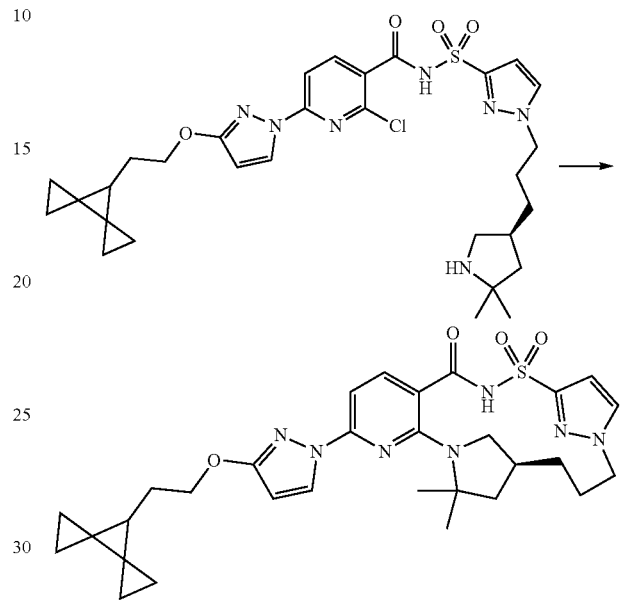

Combined 2-chloro-N-[1-[3-[(3S)-5,5-dimethylpyrrolidin-3-yl]propyl]pyrazol-3-yl]sulfonyl-6-[3-(2-dispiro[2.0.2.1]heptan-7-ylethoxy)pyrazol-1-yl]pyridine-3-carboxamide (1.69 g, 2.690 mmol), potassium carbonate (1.859 g, 13.45 mmol), cesium fluoride (614.9 mg, 4.048 mmol), 3 Å molecular sieves and dimethyl sulfoxide (102.5 mL) in a vial, purged with nitrogen, capped, heated to 155° C. and stirred for 18 h. Cooled to room temperature and the mixture was filtered, diluted with ethyl acetate and washed with a saturated aqueous sodium bicarbonate solution followed by brine. The organics were separated, dried over sodium sulfate, evaporated and then purified on silica gel chromatography using a gradient from 100% hexanes to 100% ethyl acetate to afford as a white solid, (18S)-4-[3-(2-{dispiro[2.0.2.1]heptan-7-yl}ethoxy)-1H-pyrazol-1-yl]-20,20-dimethyl-10λ6-thia-1,3,9,14,22-pentaazatetracyclo[16.2.1.111,14.02,7]docosa-2,4,6,11(22),12-pentaene-8,10,10-trione (Compound 187) (1.14 g, 72%). 1H NMR (400 MHz, dimethyl sulfoxide-d6) δ 12.69 (s, 1H), 8.17 (d, J=2.8 Hz, 1H), 8.00 (d, J=2.3 Hz, 1H), 7.71 (d, J=8.2 Hz, 1H), 6.91-6.84 (m, 2H), 6.06 (d, J=2.7 Hz, 1H), 4.21 (qd, J=7.2, 6.6, 2.7 Hz, 3H), 4.13 (dd, J=13.7, 11.3 Hz, 1H), 2.72-2.62 (m, 1H), 2.09 (d, J=12.0 Hz, 2H), 1.94-1.84 (m, 1H), 1.84-1.75 (m, 5H), 1.55 (s, 3H), 1.47 (s, 3H), 1.47-1.43 (m, 1H), 1.33 (t, J=12.3 Hz, 1H), 0.82 (q, J=2.6 Hz, 4H), 0.68-0.58 (m, 3H), 0.49 (dd, J=7.8, 4.2 Hz, 2H). ESI-MS m/z calc. 591.26276, found 592.1 (M+1)+; Retention time: 2.34 min (LC Method B).

Example 51: Preparation of 8-[3-(3,3-dicyclopropylpropoxy)-1H-pyrazol-1-yl]-12,12,18-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 189)

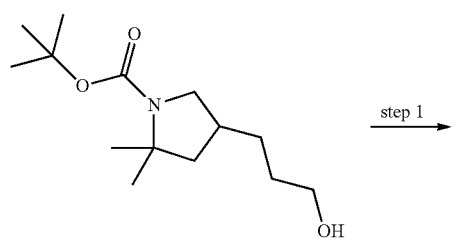

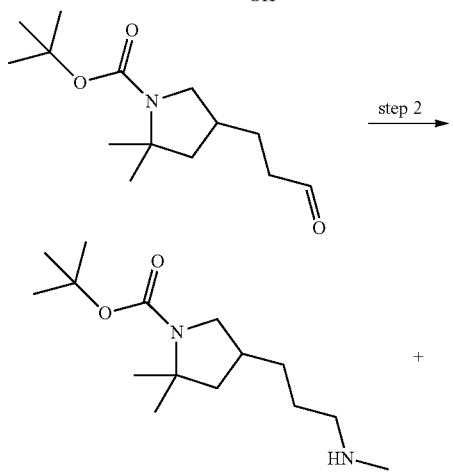

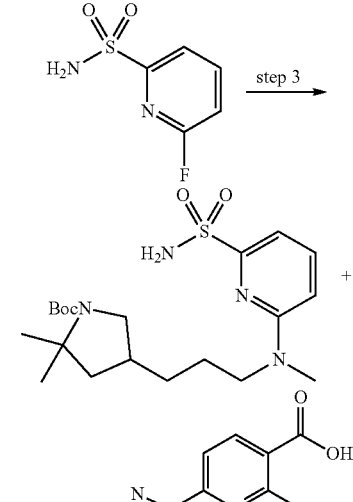

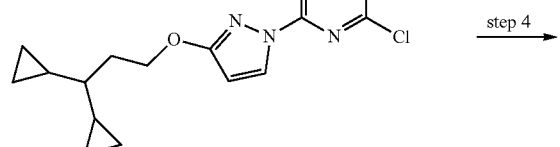

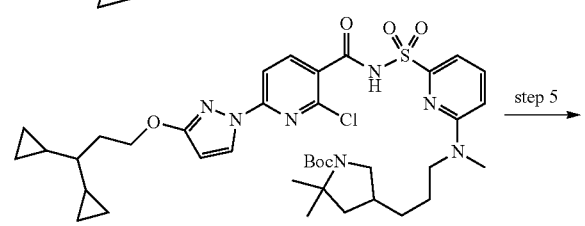

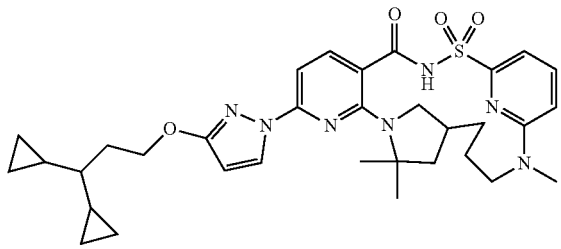

Step 1: tert-Butyl 2,2-dimethyl-4-(3-oxopropyl)pyrrolidine-1-carboxylate

To a solution of tert-butyl 4-(3-hydroxypropyl)-2,2-dimethyl-pyrrolidine-1-carboxylate (1.0 g, 3.885 mmol) in dichloromethane (25 mL) was added slowly Dess-Martin periodinane (2.0 g, 4.715 mmol) at 0° C. under a nitrogen atmosphere. The resultant heterogeneous reaction mixture was slowly warmed to room temperature and stirred for an additional 2 h. The reaction mixture was diluted with diethyl ether and filtered through a pad of celite. The filtrate was concentrated and the residue was purified by a short plug of silica gel using 1:1 mixture of hexanes and ether to afford tert-butyl 2,2-dimethyl-4-(3-oxopropyl)pyrrolidine-1-carboxylate (992 mg, 100%) as a colorless, viscous oil. ESI-MS m/z calc. 255.18344, found 256.2 (M+1)⁺; Retention time: 0.64 min (LC Method A).

Step 2: tert-Butyl 2,2-dimethyl-4-[3-(methylamino)propyl]pyrrolidine-1-carboxylate

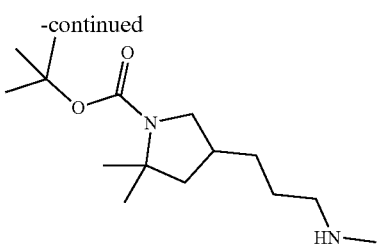

To a solution of tert-butyl 2,2-dimethyl-4-(3-oxopropyl) pyrrolidine-1-carboxylate (500 mg, 1.958 mmol) in dichloromethane (10 mL) was added sodium acetate (241 mg, 2.938 mmol) followed by methylamine (1.2 mL of 2 M, 2.400 mmol). The reaction mixture was stirred at room temperature for 1 h and cooled to 0° C. and sodium cyanoborohydride (372 mg, 5.920 mmol) was added under a nitrogen atmosphere. The heterogeneous reaction mixture was slowly warmed to room temperature and stirred for an additional 16 h. The reaction mixture was quenched with water and slowly extracted with diethyl ether. The combined organic layers were washed with brine, dried over sodium sulfate, filtered and concentrated. The reaction mixture was purified by a reverse phase HPLC-MS method using a dual gradient run from 20-80% mobile phase B over 15.0 min (mobile phase A=water (5 mM hydrochloric acid). mobile phase B=acetonitrile) to afford tert-butyl 2,2-dimethyl-4-[3-(methylamino) propyl]pyrrolidine-1-carboxylate (154 mg, 29%) as viscous oil. $^1$H NMR (400 MHz, Chloroform-d) δ 3.80-3.53 (m, 1H), 3.04-2.81 (m, 3H), 2.69 (q, J=4.8 Hz, 3H), 2.13 (s, 1H), 1.89 (s, 3H), 1.80 (s, 2H), 1.45 (d, J=10.5 Hz, 12H), 1.38 (s, 2H), 1.29 (s, 3H). ESI-MS m/z calc. 270.23074, found 271.3 (M+1)$^+$; Retention time: 0.47 min (LC Method A).

Step 3: tert-Butyl 2,2-dimethyl-4-[3-[methyl-(6-sulfamoyl-2-pyridyl)amino]propyl]pyrrolidine-1-carboxylate

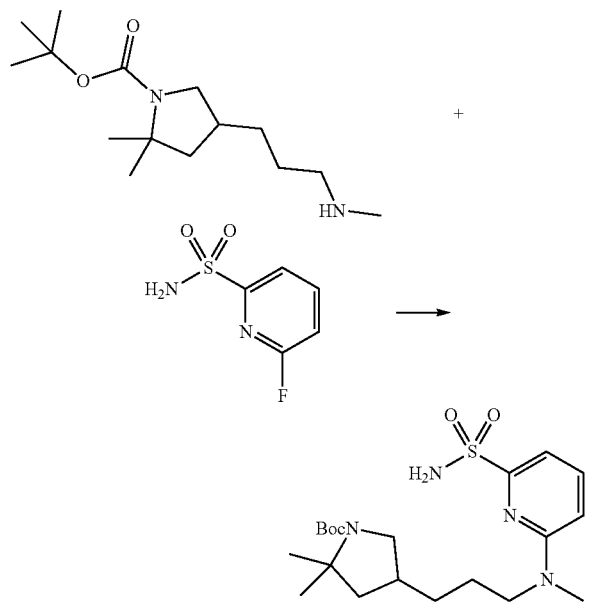

To a solution of tert-butyl 2,2-dimethyl-4-[3-(methylamino) propyl]pyrrolidine-1-carboxylate (154 mg, 0.5695 mmol) in dimethyl sulfoxide (2 mL) was added 6-fluoropyridine-2-sulfonamide (103 mg, 0.5847 mmol) followed by diisopropylethylamine (500 μL, 2.871 mmol). The flask was capped with a septum and heated at 90° C. under nitrogen (balloon) in an oil bath for 14 h. The reaction mixture was cooled to room temperature, then diluted with ethyl acetate and washed with brine solution, dried over sodium sulfate, filtered and evaporated. The resultant residue was purified by silica gel chromatography using a gradient from 100% hexanes to 100% ethyl acetate to afford tert-butyl 2,2-dimethyl-4-[3-[methyl-(6-sulfamoyl-2-pyridyl)amino]propyl]pyrrolidine-1-carboxylate (141 mg, 58%) as a white solid. $^1$H NMR (400 MHz, dimethyl sulfoxide-d$_6$) δ 7.65 (dd, J=8.6, 7.2 Hz, 1H), 7.12 (s, 2H), 7.01 (d, J=7.2 Hz, 1H), 6.78 (d, J=8.7 Hz, 1H), 3.53 (q, J=7.8, 7.4 Hz, 3H), 3.17 (d, J=3.6 Hz, 1H), 3.04 (s, 3H), 2.84-2.72 (m, 1H), 2.09 (d, J=9.5 Hz, 1H), 1.88 (td, J=12.8, 5.7 Hz, 1H), 1.53 (dt, J=14.6, 7.4 Hz, 2H), 1.36 (dd, J=15.0, 10.6 Hz, 14H), 1.23 (s, 3H). ESI-MS m/z calc. 426.23007, found 427.3 (M+1)$^+$; Retention time: 0.47 min (LC Method A).

Step 4: tert-Butyl 4-[3-[[6-[[2-chloro-6-[3-(3,3-dicyclopropylpropoxy)pyrazol-1-yl]pyridine-3-carbonyl]sulfamoyl]-2-pyridyl]-methyl-amino]propyl]-2,2-dimethyl-pyrrolidine-1-carboxylate

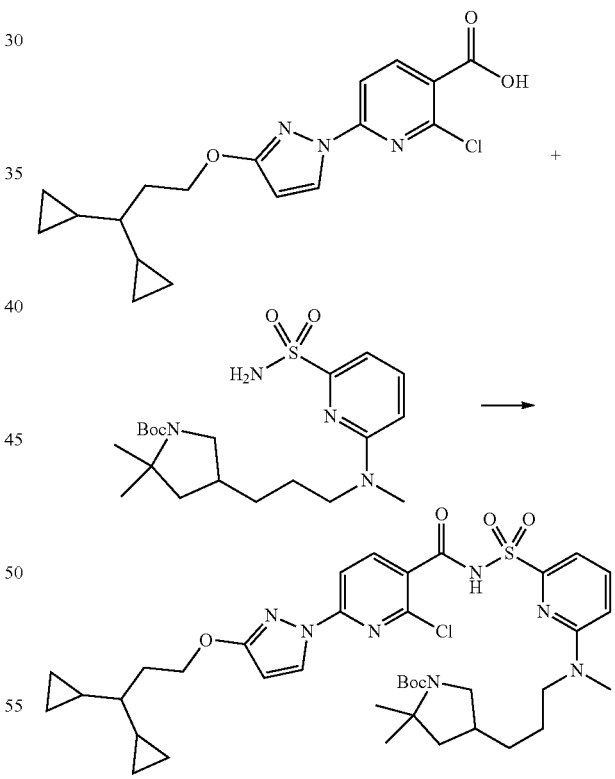

In a 20 mL scintillation vial, 2-chloro-6-[3-(3,3-dicyclopropylpropoxy)pyrazol-1-yl]pyridine-3-carboxylic acid (141 mg, 0.3858 mmol) and carbonyl diimidazole (65 mg, 0.4009 mmol) were combined in tetrahydrofuran (2 mL) and stirred for 2 h at room temperature. Then tert-butyl 2,2-dimethyl-4-[3-[methyl-(6-sulfamoyl-2-pyridyl)amino]propyl]pyrrolidine-1-carboxylate (134 mg, 0.3141 mmol) was added followed by 1,8-diazabicyclo[5.4.0]undec-7-ene (100 μL, 0.6687 mmol) and the reaction was stirred at room temperature for 16 h. The reaction was diluted with ethyl acetate and washed with a small amount of 1:1 saturated aqueous ammonium chloride/brine. The organics were separated, dried over sodium sulfate, filtered and evaporated. The resultant brown residue was purified by silica gel chromatography using a shallow gradient from 100% dichloromethane to 20% methanol in dichloromethane to afford tert-butyl 4-[3-[[6-[[2-chloro-6-[3-(3,3-dicyclopropylpropoxy)pyrazol-1-yl]pyridine-3-carbonyl]sulfamoyl]-2-pyridyl]-methylamino]propyl]-2,2-dimethyl-pyrrolidine-1-carboxylate (158 mg, 65%) as a white solid. $^1$H NMR (400 MHz, Chloroform-d) δ 8.29 (d, J=2.8 Hz, 1H), 7.98 (d, J=8.4 Hz, 1H), 7.77-7.60 (m, 2H), 7.52 (d, J=7.2 Hz, 1H), 6.64 (d, J=8.6 Hz, 1H), 5.98-5.91 (m, 1H), 4.42 (dt, J=8.3, 6.8 Hz, 2H), 4.14-4.04 (m, 1H), 3.91 (d, J=13.9 Hz, 1H), 3.32-3.21 (m, 1H), 3.01 (s, 3H), 2.91 (t, J=10.7 Hz, 1H), 2.18 (d, J=12.8 Hz, 1H), 2.02-1.93 (m, 2H), 1.79 (td, J=16.6, 14.4, 6.6 Hz, 2H), 1.65-1.48 (m, 2H), 1.37 (s, 9H), 1.30 (s, 3H), 1.25 (s, 3H), 1.22-1.14 (m, 2H), 0.67 (tdd, J=13.3, 6.7, 3.6 Hz, 2H), 0.49-0.39 (m, 4H), 0.37-0.30 (m, 1H), 0.23-0.17 (m, 2H), 0.10 (dtd, J=9.4, 5.1, 4.5, 2.3 Hz, 2H). ESI-MS m/z calc. 769.3388, found 770.45 (M+1)$^+$; Retention time: 0.67 min (LC Method A).

Step 5: 8-[3-(3,3-Dicyclopropylpropoxy)-1H-pyrazol-1-yl]-12,12,18-trimethyl-2λ$^6$-thia-3,9,11,18,23-pentaazatetracyclo[17.3.1.111,14.05,10]tetracosa-1 (22),5,7,9,19(23),20-hexaene-2,2,4-trione (Compound 189)

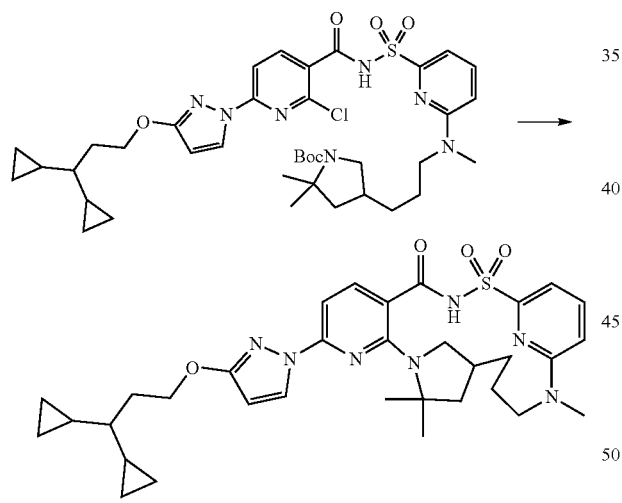

A solution of tert-butyl 4-[3-[[6-[[2-chloro-6-[3-(3,3-dicyclopropylpropoxy)pyrazol-1-yl]pyridine-3-carbonyl]sulfamoyl]-2-pyridyl]-methyl-amino]propyl]-2,2-dimethyl-pyrrolidine-1-carboxylate (153 mg, 0.1986 mmol) in dichloromethane (1.2 mL) and trifluoroacetic acid (150.0 µL, 1.960 mmol) was stirred at room temperature for 4 h. The solvents were then removed under vacuum. The residue was dissolved in ethyl acetate, washed with 2 mL of saturated sodium bicarbonate solution and the solvent was removed and dried under high vacuum. The resulting residue was dissolved in dimethyl sulfoxide (8 mL) and 4 Å molecular sieves were added and the reaction mixture was stirred for 10 min. Then, cesium fluoride (98 mg, 0.6451 mmol) and potassium carbonate (91 mg, 0.6584 mmol) were added and the reaction mixture was heated at 130° C. overnight. The reaction mixture was filtered through a Whatman filter disc (puradisc 25 TF) and the filtrate was purified by a reverse phase HPLC-MS method using a dual gradient run from 20-80% mobile phase B over 15.0 min (mobile phase A=water (0.05% hydrochloric acid), mobile phase B=acetonitrile) to afford 8-[3-(3,3-dicyclopropylpropoxy)-1H-pyrazol-1-yl]-12,12,18-trimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 189) (76 mg, 60%) as an off white solid. $^1$H NMR (400 MHz, Chloroform-d) δ 10.54 (s, 1H), 8.19 (d, J=2.8 Hz, 1H), 8.13 (d, J=8.4 Hz, 1H), 7.67 (dd, J=8.6, 7.3 Hz, 1H), 7.60-7.54 (m, 1H), 7.37 (d, J=8.4 Hz, 1H), 6.69 (dd, J=8.7, 0.8 Hz, 1H), 5.92 (d, J=2.8 Hz, 1H), 4.43 (t, J=6.8 Hz, 2H), 4.37 (s, 1H), 3.37 (dd, J=9.8, 7.2 Hz, 1H), 3.13-3.05 (m, 1H), 3.01 (s, 3H), 2.87 (d, J=26.3 Hz, 1H), 2.24 (dd, J=12.5, 9.1 Hz, 1H), 1.97 (q, J=6.8 Hz, 2H), 1.70 (s, 1H), 1.65 (s, 3H), 1.61 (s, 3H), 1.55 (dd, J=12.5, 8.5 Hz, 1H), 1.50-1.40 (m, 4H), 0.72-0.59 (m, 2H), 0.50-0.39 (m, 4H), 0.34 (ddd, J=15.9, 9.0, 6.9 Hz, 1H), 0.23-0.16 (m, 2H), 0.15-0.07 (m, 2H). ESI-MS m/z calc. 633.30975, found 634.22 (M+1)$^+$; Retention time: 1.55 min (LC Method J).

Example 52: Preparation of (14R)-8-[3-(2-{dispiro [2.0.2.1]heptan-7-yl}ethoxy)-1H-pyrazol-1-yl]-12, 12-dimethyl-2λ$^6$-thia-3,9,11,18,23-pentaazatetracyclo[17.3.1.111,14.05,10]tetracosa-1(22),5,7,9,19(23), 20-hexaene-2,2,4-trione (Compound 194)

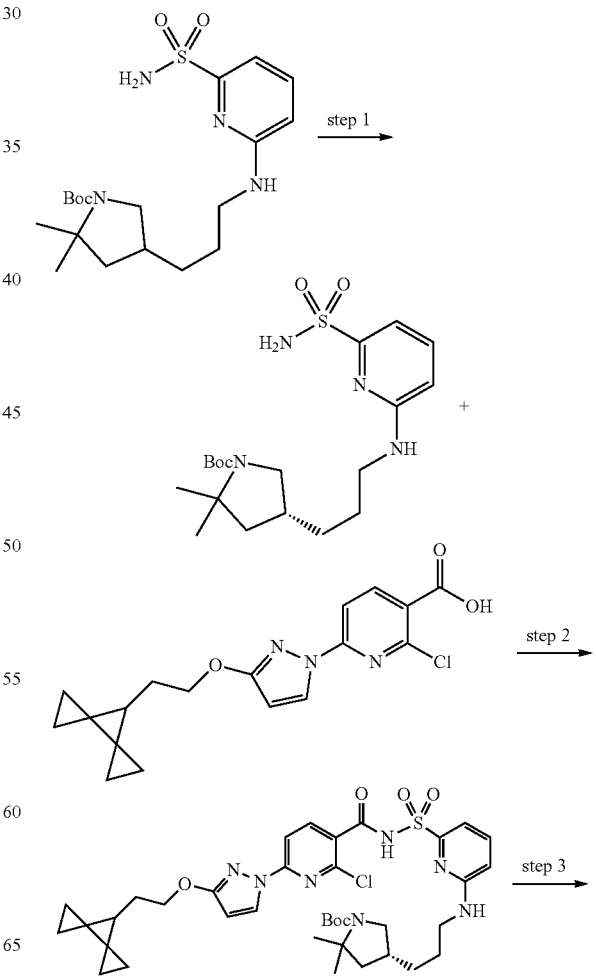

-continued

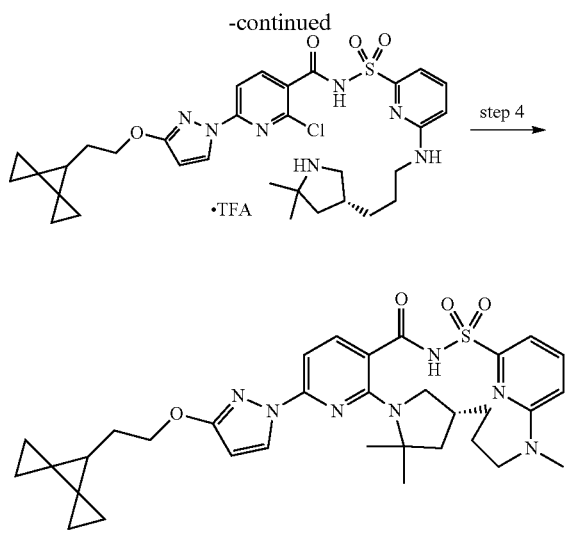

Step 1: tert-Butyl (4R)-2,2-dimethyl-4-[3-[(6-sulfamoyl-2-pyridyl)amino]propyl]pyrrolidine-1-carboxylate

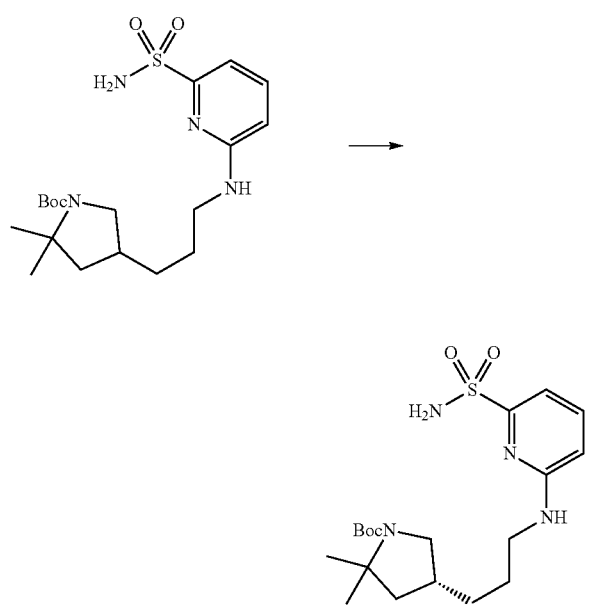

Subjected racemic tert-butyl 2,2-dimethyl-4-[3-[(6-sulfamoyl-2-pyridyl)amino]propyl]pyrrolidine-1-carboxylate (7 g, 16.97 mmol) to chiral separation by SFC chromatography using a ChiralPak IG (250×21.2 mm column, 5 μm particle size) with 40% methanol/60% carbon dioxide mobile phase at 70 mL/min over 11.0 min (injection volume=500 μL of 32 mg/mL solution in methanol giving as the second enantiomer to elute, tert-butyl (4R)-2,2-dimethyl-4-[3-[(6-sulfamoyl-2-pyridyl)amino]propyl]pyrrolidine-1-carboxylate (3.167 g, 90%) ESI-MS m/z calc. 412.21442, found 413.2 (M+1)⁺; Retention time: 0.63 min (LC Method A).

Step 2: tert-Butyl (4R)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate

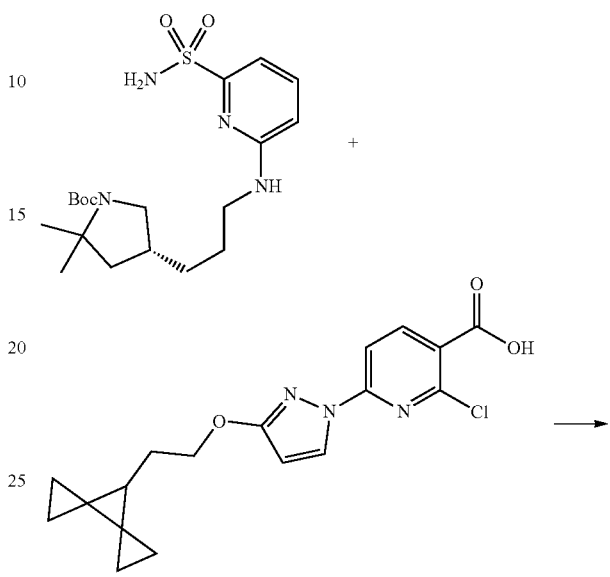

To a solution of 2-chloro-6-[3-(2-dispiro[2.0.2.1]heptan-7-ylethoxy)pyrazol-1-yl]pyridine-3-carboxylic acid (1.95 g, 5.420 mmol) in tetrahydrofuran (20 mL) was added carbonyl diimidazole (1.03 g, 6.073 mmol) and the mixture stirred at ambient temperature for 1 h. To this mixture was added tert-butyl (4R)-2,2-dimethyl-4-[3-[(6-sulfamoyl-2-pyridyl)amino]propyl]pyrrolidine-1-carboxylate (1.95 g, 4.301 mmol) in tetrahydrofuran (9 mL) followed by 1,8-diazabicyclo[5.4.0]undec-7-ene (2.0 mL, 13.37 mmol) and the mixture was stirred at ambient temperature for 16 h. The reaction was diluted with water (50 mL) and the mixture acidified with hydrochloric acid (5 mL of 6 M, 30.00 mmol). The mixture was extracted with ethyl acetate (200 mL) and the organic phase separated. The organic phase was washed with brine and the combined aqueous phases back extracted with 50 mL of ethyl acetate. The combined organic phases were dried over magnesium sulfate, filtered and concentrated in vacuo. The crude product obtained was chromatographed on a 275 g C₁₈ reverse phase column eluting with 50-100% acetonitrile/water. The product fractions were collected and concentrated in vacuo giving tert-butyl (4R)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (2.73 g, 65%). ¹H NMR (400 MHz, dimethyl sulfoxide-d₆) δ 12.76 (s, 1H), 8.38 (t, J=2.3 Hz, 1H), 8.11 (d, J=8.3 Hz, 1H), 7.70 (d, J=8.3 Hz, 1H), 7.62 (dd, J=8.5, 7.2

Hz, 1H), 7.18 (dd, J=12.6, 6.3 Hz, 2H), 6.74 (d, J=8.5 Hz, 1H), 6.16 (dd, J=2.9, 1.4 Hz, 1H), 4.24 (t, J=6.6 Hz, 2H), 3.57-3.44 (m, 1H), 3.24 (t, J=6.0 Hz, 2H), 2.74 (t, J=10.5 Hz, 1H), 2.01 (tt, J=11.9, 6.5 Hz, 1H), 1.82 (q, J=6.6 Hz, 3H), 1.49 (dt, J=13.0, 6.9 Hz, 3H), 1.36 (d, J=11.6 Hz, 10H), 1.33-1.24 (m, 6H), 1.17 (s, 3H), 0.89-0.75 (m, 4H), 0.71-0.60 (m, 2H), 0.54-0.44 (m, 2H). ESI-MS m/z calc. 753.30756, found 754.4 (M+1)⁺; Retention time: 3.69 min (LC Method D).

Step 3: 2-Chloro-N-[[6-[3-[(3R)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (Trifluoroacetate Salt)

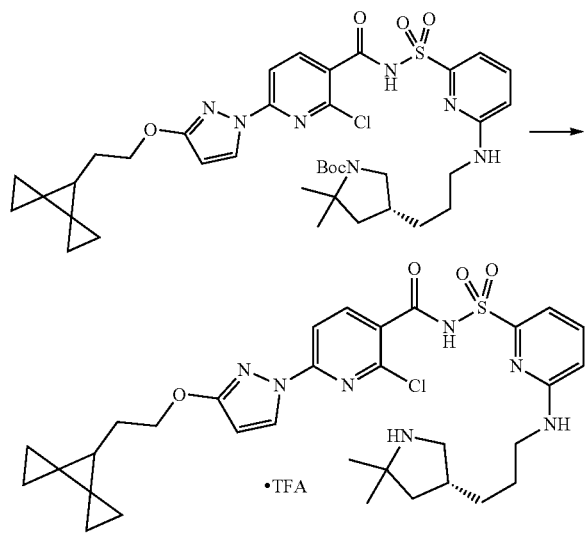

To a solution of tert-butyl (4R)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (2.73 g, 3.619 mmol) in dichloromethane (15 mL) and toluene (5 mL) was added trifluoroacetic acid (3 mL, 38.94 mmol) and the mixture stirred at ambient temperature for 48 h. The solvent was removed in vacuo with the bath temp set at 45° C. affording a thick yellow oil. The oil was diluted with toluene (20 mL) and the solvent removed in vacuo with the bath temp set at 45° C. giving 2-chloro-N-[[6-[3-[(3R)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (2.78 g, 100%) as an oil that was used without further purification. ¹H NMR (400 MHz, dimethyl sulfoxide-d₆) δ 12.78 (s, 1H), 8.61 (s, 2H), 8.39 (d, J=2.9 Hz, 1H), 8.11 (d, J=8.4 Hz, 1H), 7.71 (d, J=8.3 Hz, 1H), 7.63 (dd, J=8.5, 7.2 Hz, 1H), 7.34-7.11 (m, 5H), 6.75 (dd, J=8.6, 0.7 Hz, 1H), 6.18 (d, J=2.9 Hz, 1H), 4.24 (t, J=6.7 Hz, 2H), 3.36 (dt, J=11.6, 6.1 Hz, 1H), 3.25 (q, J=6.6 Hz, 2H), 2.89-2.71 (m, 1H), 2.30 (s, 2H), 1.93 (dd, J=12.9, 7.6 Hz, 1H), 1.89-1.71 (m, 2H), 1.48 (q, J=7.2, 6.3 Hz, 4H), 1.34 (s, 5H), 1.24 (d, J=6.0 Hz, 4H), 0.89-0.75 (m, 4H), 0.70-0.62 (m, 2H), 0.55-0.46 (m, 2H). ESI-MS m/z calc. 653.2551, found 654.3 (M+1)⁺; Retention time: 2.49 min (LC Method D).

Step 4: (14R)-8-[3-(2-{Dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 194)

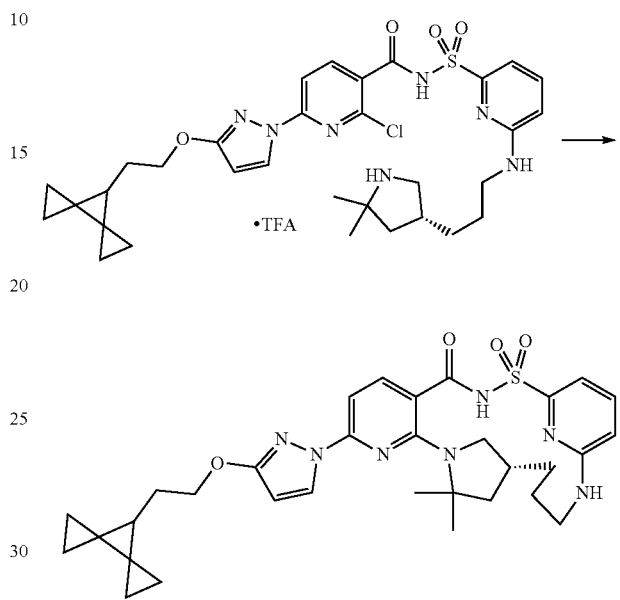

To a solution of 2-chloro-N-[[6-[3-[(3R)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (2.78 g, 3.619 mmol) in NMP (50 mL) was added potassium carbonate (2.5 g, 18.09 mmol). The mixture was purged with nitrogen for 5 min. The mixture was heated at 135° C. for 22 h. The reaction mixture was cooled to room temperature and added to water (150 mL). The mixture was carefully acidified with hydrochloric acid (7 mL of 6 M, 42.00 mmol) affording a foamy slurry. The solid was collected by filtration using a medium frit. The wet filter cake was dissolved in ethyl acetate (200 mL), washed with 100 mL of brine then concentrated in vacuo. The crude product was diluted with acetonitrile and chromatographed on a 250 g reverse phase C18 column eluting with 50-100% water/acetonitrile affording a foam which was dried in a vacuum oven at 45° C. for 48 h giving (14R)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 194) (1.3 g, 57%). ¹H NMR (400 MHz, dimethyl sulfoxide-d₆) δ 12.51 (s, 1H), 8.20 (d, J=2.8 Hz, 1H), 7.82 (d, J=8.3 Hz, 1H), 7.58 (dd, J=8.5, 7.2 Hz, 1H), 7.05 (d, J=7.2 Hz, 1H), 6.99 (d, J=8.9 Hz, 1H), 6.91 (d, J=8.2 Hz, 1H), 6.71 (d, J=8.4 Hz, 1H), 6.09 (d, J=2.7 Hz, 1H), 4.21 (td, J=6.6, 1.4 Hz, 2H), 3.92 (d, J=11.8 Hz, 1H), 3.15 (s, 1H), 2.95 (d, J=13.2 Hz, 1H), 2.78-2.64 (m, 1H), 2.12 (s, 1H), 1.90-1.70 (m, 4H), 1.60 (s, 6H), 1.51 (s, 3H), 1.47 (t, J=6.5 Hz, 1H), 1.31 (q, J=12.0 Hz, 1H), 0.89-0.78 (m, 4H), 0.70-0.61 (m, 2H), 0.55-0.44 (m, 2H). ESI-MS m/z calc. 617.27844, found 618.4 (M+1)+; Retention time: 3.38 min (LC Method D).

Example 53: Preparation of (14S)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Compound 195)

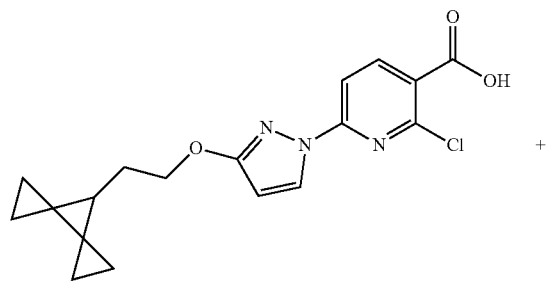

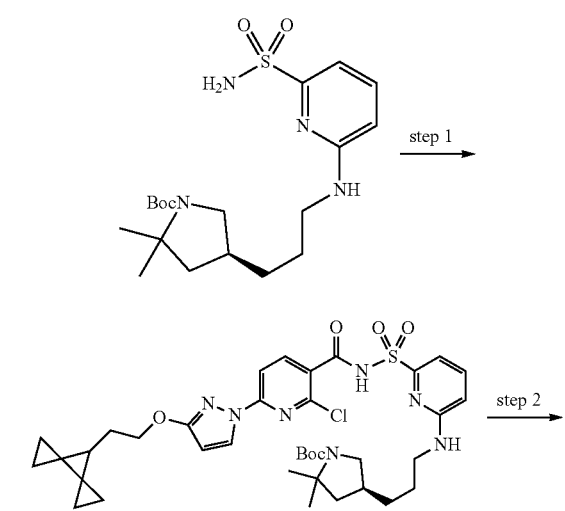

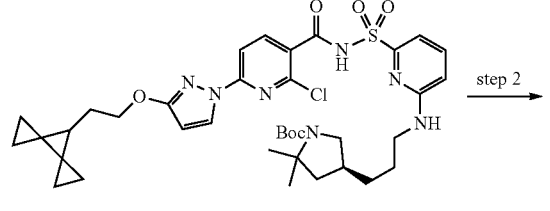

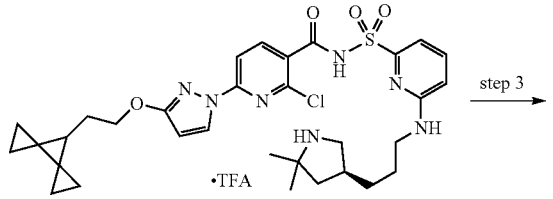

Step 1: tert-Butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate

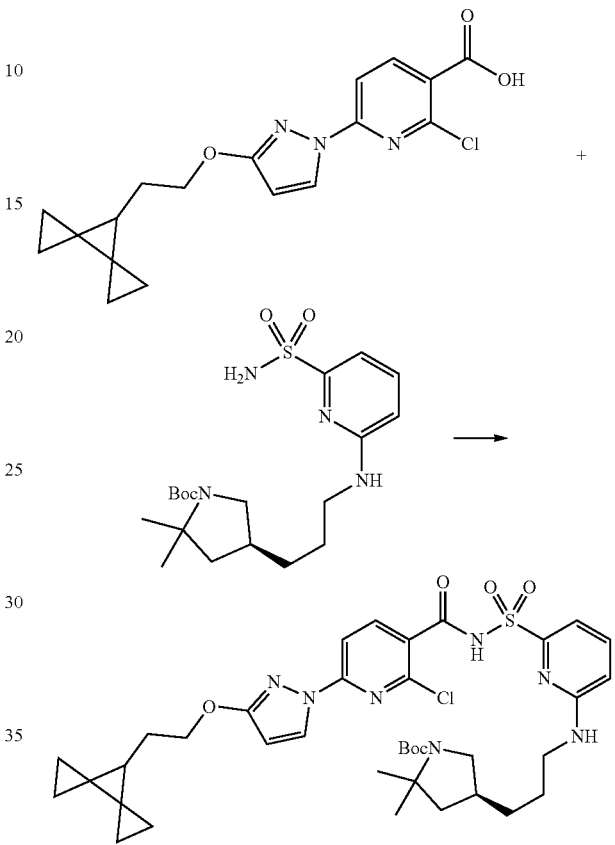

To a solution of 2-chloro-6-[3-(2-dispiro[2.0.2.1]heptan-7-ylethoxy)pyrazol-1-yl]pyridine-3-carboxylic acid (5.2 g, 14.45 mmol) in tetrahydrofuran (100 mL) was added carbonyl diimidazole (2.8 g, 16.51 mmol) and the mixture stirred at ambient temperature for 1 h. To this mixture was added tert-butyl (4S)-2,2-dimethyl-4-[3-[(6-sulfamoyl-2-pyridyl)amino]propyl]pyrrolidine-1-carboxylate (6.0 g, 14.54 mmol) in tetrahydrofuran (15 mL) followed by 1,8-diazabicyclo[5.4.0]undec-7-ene (6.5 mL, 43.47 mmol) and the mixture was stirred at ambient temperature for 16 h. The reaction was diluted with water (150 mL) and the mixture acidified with aqueous hydrochloric acid (15 mL of 6 M, 90.00 mmol). The mixture was extracted with ethyl acetate (300 mL) and the organic phase separated. The organic phase was washed with brine, dried over magnesium sulfate, filtered over Celite and concentrated in vacuo affording a white precipitate. The precipitate was slurried with acetonitrile and the solid collected by filtration using a medium glass frit and washed with acetonitrile. The filtrate was concentrated in vacuo affording a yellow oil. The crude oil was diluted with acetonitrile and some N-methyl-2-pyrrolidone and chromatographed on a 415 g reverse phase C₁₈ column eluting with 50%-100% acetonitrile in water giving tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1- carboxylate (4.5 g, 41%). ESI-MS m/z calc. 753.30756, found 754.4 (M+1)⁺; Retention time: 3.79 min (LC Method D).

Step 2: 2-Chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (Trifluoroacetate Salt)

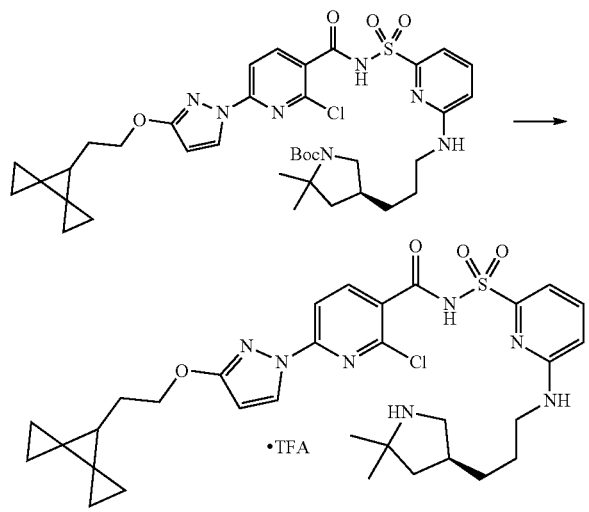

To a solution of tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (5.9 g, 7.821 mmol) in dichloromethane (30 mL) and toluene (15 mL) was added trifluoroacetic acid (6.0 mL, 77.88 mmol) and the mixture stirred at ambient temperature for 18 h. The solvent was removed in vacuo with the bath temp set at 45° C. affording a thick, yellow oil. The oil was diluted with toluene (125 mL) and the solvent removed in vacuo with the bath temp set at 45° C. The oil was diluted with toluene and the solvent removed in vacuo affording a thick, viscous yellow oil, 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (6.0 g, 100%) which was used in the next step without further purification. ESI-MS m/z calc. 653.2551, found 654.3 (M+1)⁺; Retention time: 2.6 min (LC Method B).

Step 3: (14S)-8-[3-(2-{Dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 195)

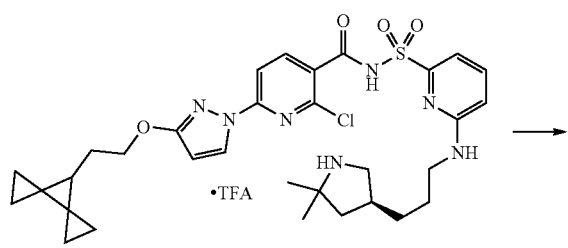

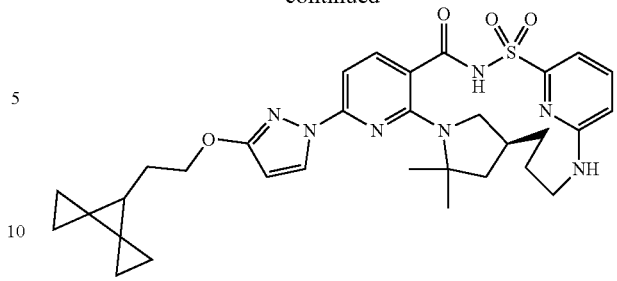

To a solution of 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-ylethoxy)pyrazol-1-yl]pyridine-3-carboxamide (trifluoroacetate salt) (6.0 g, 7.810 mmol) in NMP (140 mL) was added potassium carbonate (5.3 g, 38.35 mmol). The mixture was purged with nitrogen for 5 min. The mixture was then heated at 150° C. for 22 h. The reaction mixture was cooled to room temperature and added to water (300 mL) affording an off-white solid precipitate. The mixture was carefully acidified with aqueous hydrochloric acid (12 mL of 6 M, 72.00 mmol) affording a foamy slurry. The solid was collected by filtration using a medium glass frit. The wet filter cake was dissolved in ethyl acetate (500 mL) and washed with 200 mL of brine. The aqueous phase was slightly cloudy so it was acidified with a small amount of 6N hydrochloric acid and returned to the organic phase. The aqueous phase was separated and the organic phase was dried over magnesium sulfate, filtered and concentrated in vacuo affording a light yellow oil. This crude product was diluted with acetonitrile and chromatographed on a 415 g C₁₈ reverse phase column eluting with 50%-100% acetonitrile in water. The product was isolated as a cream colored foam. The foam was dried in vacuo at 45° C. for 48 h giving (14S)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 195) (3.32 g, 68%). ¹H NMR (400 MHz, dimethyl sulfoxide-d₆) δ 12.48 (s, 1H), 8.20 (d, J=2.8 Hz, 1H), 7.81 (d, J=8.2 Hz, 1H), 7.57 (dd, J=8.5, 7.2 Hz, 1H), 7.05 (d, J=7.1 Hz, 1H), 6.97 (d, J=8.5 Hz, 1H), 6.91 (d, J=8.2 Hz, 1H), 6.71 (d, J=8.5 Hz, 1H), 6.08 (d, J=2.7 Hz, 1H), 4.21 (td, J=6.7, 1.3 Hz, 2H), 3.92 (d, J=12.0 Hz, 1H), 3.16 (s, 1H), 2.95 (d, J=13.3 Hz, 1H), 2.78-2.66 (m, 1H), 2.07 (s, 1H), 1.92-1.72 (m, 4H), 1.60 (s, 6H), 1.51 (s, 3H), 1.47 (t, J=6.5 Hz, 1H), 1.31 (q, J=12.2 Hz, 1H), 0.89-0.77 (m, 4H), 0.69-0.61 (m, 2H), 0.53-0.45 (m, 2H). ESI-MS m/z calc. 617.27844, found 618.4 (M+1)⁺; Retention time: 10.29 min (LC Method F).

Ca²⁺, Na⁺, and K⁺ salts of Compound 195 were made by mixing Compound 195 with Ca(OCH₃)₂, Na(OCH₃), and KOH, respectively: mixing Compound 195 (1 g) and Ca(OCH₃)₂ (83 mg) in methanol (65 mL) at room temperature for 30 minutes and then at 65° C. for 30 minutes; mixing Compound 195 (0.6 g (1 mMol)) in MeOH (40 mL) with 25 wt % Na(OCH₃) in MeOH (250 mL (1 molar equiv)) at 60°

C. for 20 minutes; and mixing Compound 195 (0.6 g) in acetone (11 mL) with 1N KOH (1 molar equivalent) at 50° C. for 1 hour. After filtration of the resulting hot solutions, the filtrates were evaporated to dryness to yield the desired amorphous salts, respectively (PXRD data not shown).

Example 54: Preparation of 8-[3-(2-{dispiro [2.0.2.1]heptan-7-yl}ethoxy)-1H-pyrazol-1-yl]-12, 12-dimethyl-15-oxa-2λ⁶-thia-3,9,11,18,23-pentaazatetracyclo[17.3.1.1¹¹,¹⁴.0⁵,¹⁰]tetracosa-1(23),5(10), 6,8,19,21-hexaene-2,2,4-trione (Enantiomer 1) (Compound 196) and 8-[3-(2-{dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo [17.3.1.1¹¹,¹⁴.0⁵,¹⁰]tetracosa-1(23),5(10),6,8,19, 21-hexaene-2,2,4-trione (Enantiomer 2) (Compound 197)

Step 1: tert-Butyl 4-[2-[[6-[[2-chloro-6-[3-(2-dispiro [2.0.2.1]heptan-7-ylethoxy)pyrazol-1-yl]pyridine-3-carbonyl]sulfamoyl]-2-pyridyl]amino]ethoxy]-2,2-dimethyl-pyrrolidine-1-carboxylate

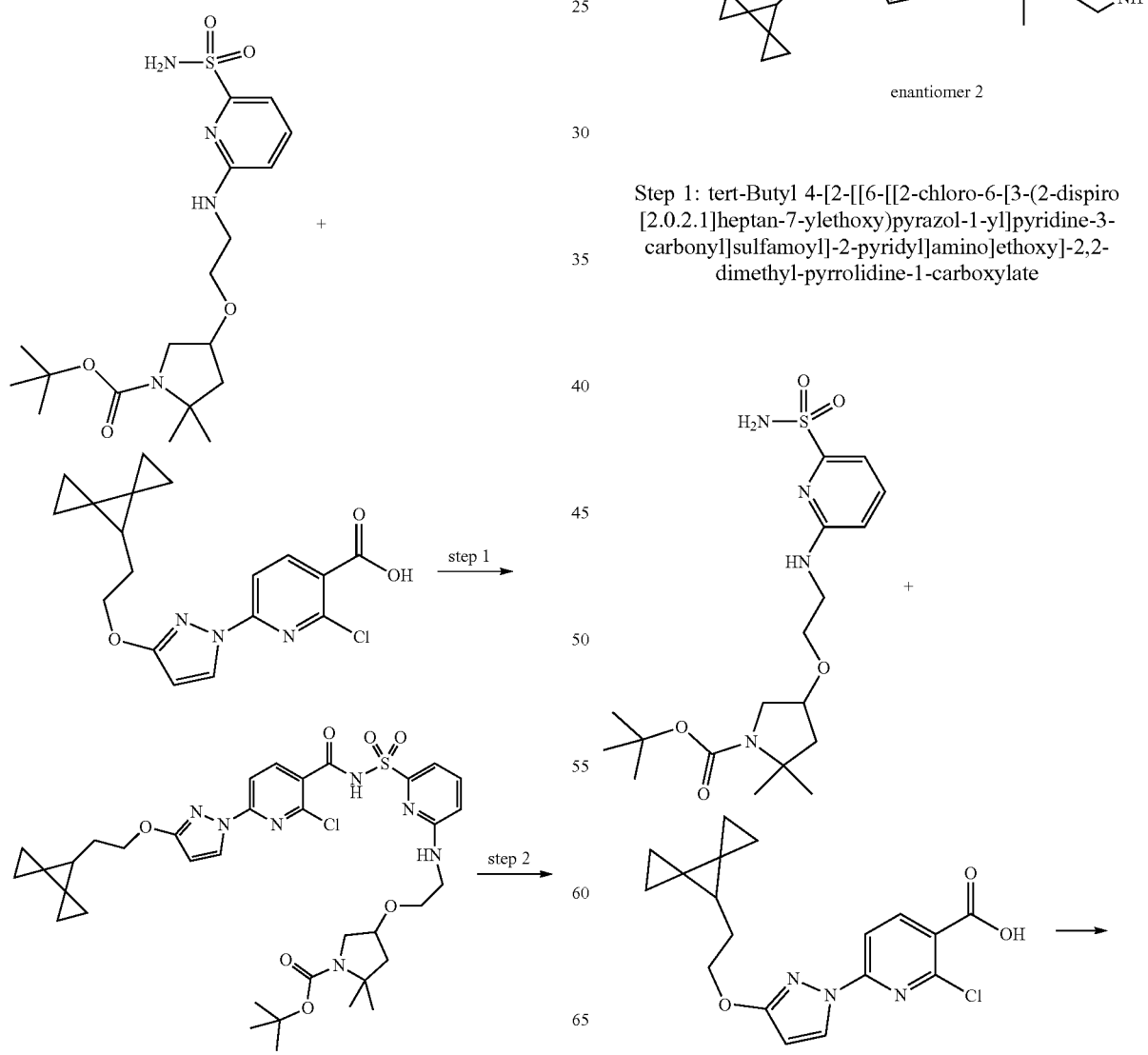

-continued

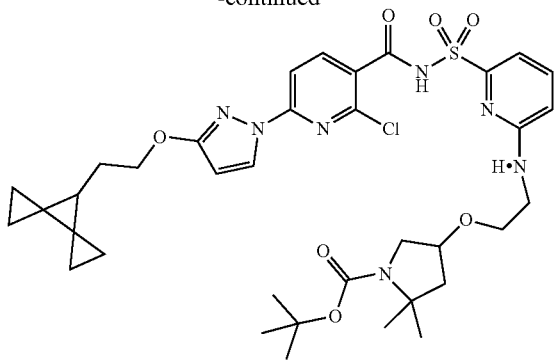

2-Chloro-6-[3-(2-dispiro[2.0.2.1]heptan-7-ylethoxy) pyrazol-1-yl]pyridine-3-carboxylic acid (412 mg, 1.145 mmol) and carbonyl diimidazole (185.7 mg, 1.145 mmol) were combined in anhydrous tetrahydrofuran (10.47 mL) and stirred for 60 min at 50° C. Then a tetrahydrofuran solution (7 mL) of tert-butyl 2,2-dimethyl-4-[2-[(6-sulfamoyl-2-pyridyl)amino]ethoxy]pyrrolidine-1-carboxylate (431.5 mg, 1.041 mmol) and 1,8-diazabicyclo[5.4.0]undec-7-ene (400.7 mg, 393.6 µL, 2.632 mmol) was added. The reaction was heated at 50° C. for 4 h. The reaction was diluted with ethyl acetate and washed with a 1 M aqueous citric acid solution, followed by brine. The organics were separated, dried over sodium sulfate, filtered and evaporated and then purified on silica gel using a gradient of 100% hexanes to 75% ethyl acetate in hexanes to afford as an off-white solid, tert-butyl 4-[2-[[6-[[2-chloro-6-[3-(2-dispiro [2.0.2.1]heptan-7-ylethoxy)pyrazol-1-yl]pyridine-3-carbonyl]sulfamoyl]-2-pyridyl]amino]ethoxy]-2,2-dimethyl-pyrrolidine-1-carboxylate (452 mg, 57%). ESI-MS m/z calc. 755.2868, found 756.41 (M+1)⁺; Retention time: 0.92 min (LC Method A).

Step 2: 8-[3-(2-{Dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 188)

tert-Butyl 4-[2-[[6-[[2-chloro-6-[3-(2-dispiro[2.0.2.1] heptan-7-ylethoxy)pyrazol-1-yl]pyridine-3-carbonyl]sulfamoyl]-2-pyridyl]amino]ethoxy]-2,2-dimethyl-pyrrolidine-1-carboxylate (410 mg, 0.5421 mmol) was dissolved in dichloromethane (6 mL) and to the mixture was added trifluoroacetic acid (800 µL, 10.38 mmol). The reaction solution was stirred at room temperature for 30 min. The reaction solution was concentrated in vacuo to dryness under reduced pressure giving a residue. Combined this residue and potassium carbonate (450 mg, 3.256 mmol), cesium fluoride (105 mg, 0.6912 mmol), 3 Å molecular sieves and dimethyl sulfoxide (5 mL) in a vial, purged with nitrogen, capped, heated to 140° C. and stirred for 20 h. The reaction mixture was allowed to cool to room temperature, filtered and then purified by reverse-phase preparative chromatography (C₁₈ column, 30% to 99% acetonitrile (no modifier) in water (5 mM hydrochloric acid) over 30 min) to afford a white solid, 8-[3-(2-{dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo[17.3.1.1¹¹¹,¹⁴.0⁵,¹⁰]tetracosa-1(23),5(10),6,8,19,21-hexaene-2,2,4-trione (Compound 188) (330 mg, 97%). ¹H NMR (400 MHz, dimethyl sulfoxide-d₆) δ 12.55 (s, 1H), 8.19 (d, J=2.8 Hz, 1H), 7.79 (d, J=8.2 Hz, 1H), 7.59 (t, J=7.9 Hz, 1H), 7.09 (m, 2H), 6.93 (d, J=8.1 Hz, 1H), 6.70 (d, J=8.5 Hz, 1H), 6.08 (d, J=2.8 Hz, 1H), 4.21 (t, J=6.6 Hz, 2H), 4.10 (s, 2H), 3.88 (t, J=11.8 Hz, 1H), 3.60 (d, J=12.4 Hz, 1H), 2.86 (s, 1H), 2.07 (dd, J=11.9, 6.0 Hz, 1H), 1.81 (q, J=6.6 Hz, 3H), 1.57 (d, J=9.2 Hz, 6H), 1.47 (t, J=6.5 Hz, 1H), 1.23 (s, 2H), 0.94-0.75 (m, 4H), 0.64 (dd, J=8.4, 4.5 Hz, 2H), 0.50 (dd, J=7.8, 4.3 Hz, 2H). ESI-MS m/z calc. 619.2577, found 620.33 (M+1)⁺; Retention time: 2.25 min (LC Method B).

Step 3: 8-[3-(2-{Dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 1) (Compound 196) and 8-[3-(2-{dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 2) (Compound 197)

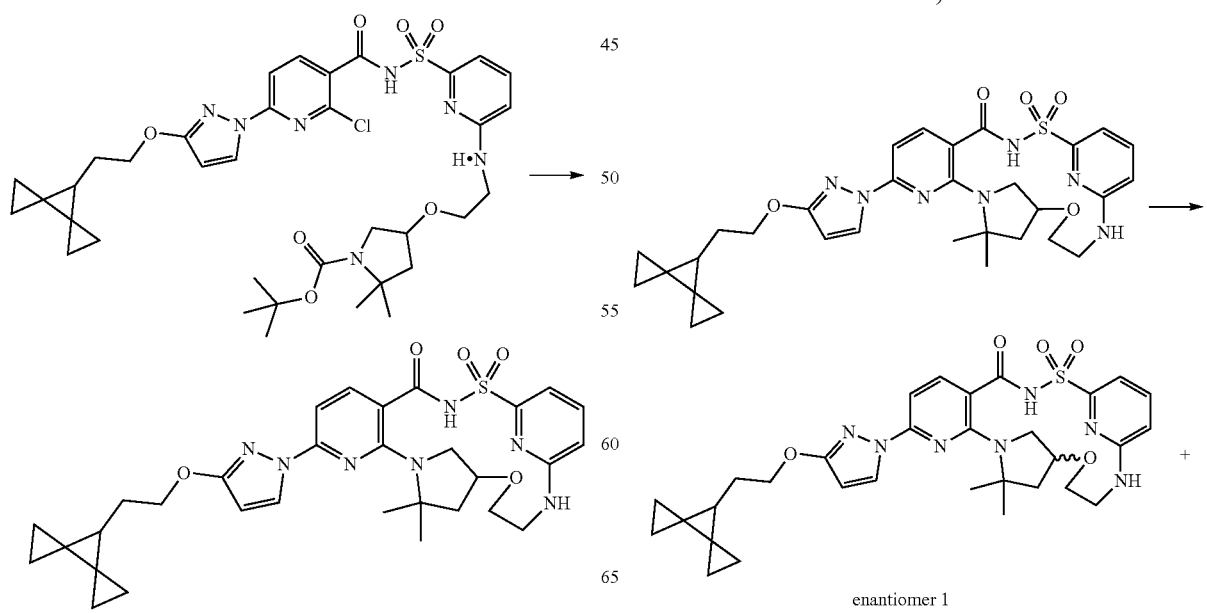

enantiomer 1

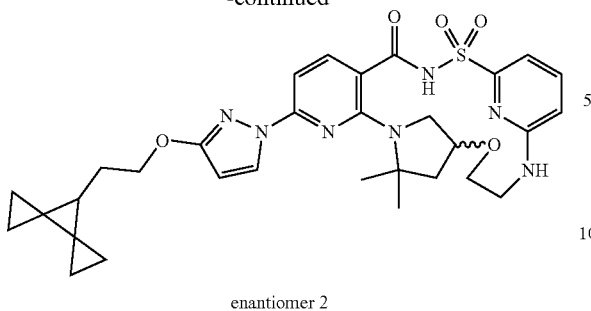

enantiomer 2

The racemic compound 8-[3-(2-{dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 188) (320 mg, 0.5112 mmol) was subjected to chiral SFC chromatography. The following SFC protocol was employed: ChiralPak AS-3 (150×2.1 mm), 3 μm; 35° C. mobile phase: 30% acetonitrile:methanol (90:10), 70% carbon dioxide. The first enantiomer to elute was 8-[3-(2-{dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 1) (Compound 196) (63 mg, 39%). ESI-MS m/z calc. 619.2577, found 620.33 (M+1)⁺; Retention time: 2.18 min (LC Method B). The second enantiomer to elute was 8-[3-(2-{dispiro[2.0.2.1]heptan-7-yl}ethoxy)-1H-pyrazol-1-yl]-12,12-dimethyl-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 2) (Compound 197) (62 mg, 39%). ¹H NMR (400 MHz, dimethyl sulfoxide-d₆) δ 12.56 (s, 1H), 8.19 (d, J=2.8 Hz, 1H), 7.79 (d, J=8.2 Hz, 1H), 7.59 (t, J=7.8 Hz, 1H), 7.09 (d, J=7.2 Hz, 1H), 6.93 (d, J=8.2 Hz, 1H), 6.70 (d, J=8.5 Hz, 1H), 6.08 (d, J=2.8 Hz, 1H), 4.21 (t, J=6.7 Hz, 2H), 3.88 (t, J=11.9 Hz, 1H), 3.60 (d, J=13.0 Hz, 1H), 3.17 (d, J=4.3 Hz, 3H), 2.86 (s, 1H), 2.08 (dd, J=11.8, 5.9 Hz, 1H), 1.81 (q, J=6.5 Hz, 3H), 1.57 (d, J=9.4 Hz, 6H), 1.47 (t, J=6.5 Hz, 1H), 1.42-1.33 (m, 1H), 1.24 (s, 1H), 0.96-0.78 (m, 4H), 0.72-0.57 (m, 2H), 0.57-0.42 (m, 2H). ESI-MS m/z calc. 619.2577, found 620.33 (M+1)⁺; Retention time: 2.18 min (LC Method B).

Example 55: Preparation of 20,20-dimethyl-4-{3-[2-(2,2,3,3-tetramethylcyclopropyl)ethoxy]-1H-pyrazol-1-yl}-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Enantiomer 1) (Compound 206) and 20,20-dimethyl-4-{3-[2-(2,2,3,3-tetramethylcyclopropyl)ethoxy]-1H-pyrazol-1-yl}-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Enantiomer 2) (Compound 207)

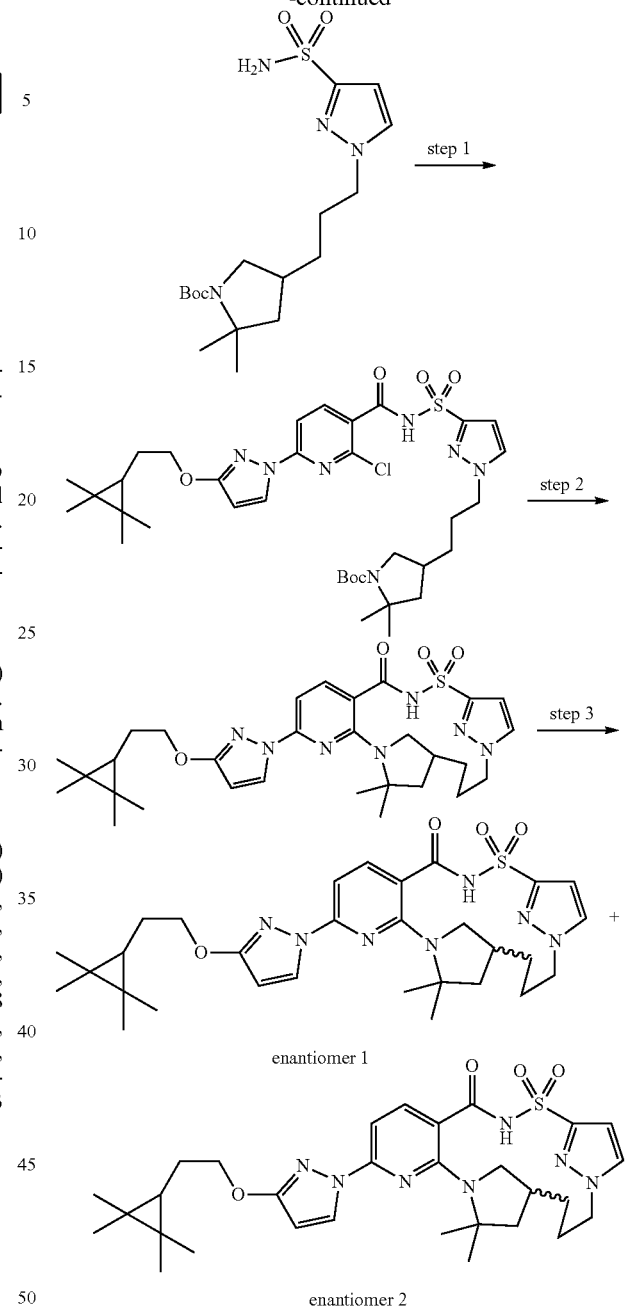

enantiomer 1 enantiomer 2

Step 1: tert-Butyl 4-[3-[3-[[2-chloro-6-[3-[2-(2,2,3,3-tetramethylcyclopropyl)ethoxy]pyrazol-1-yl]pyridine-3-carbonyl]sulfamoyl]pyrazol-1-yl]propyl]-2,2-dimethyl-pyrrolidine-1-carboxylate

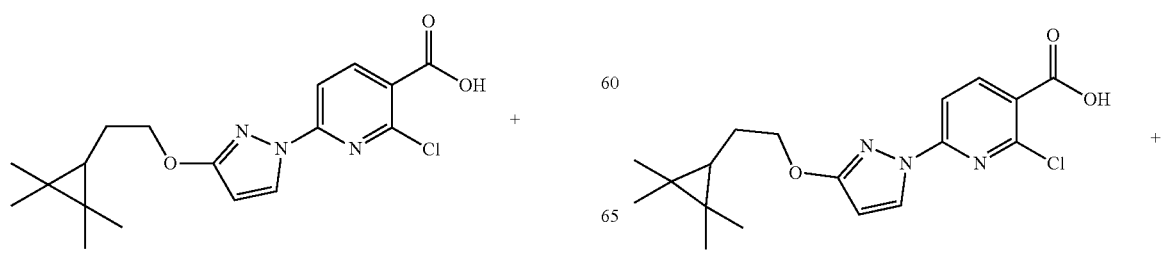

485

-continued

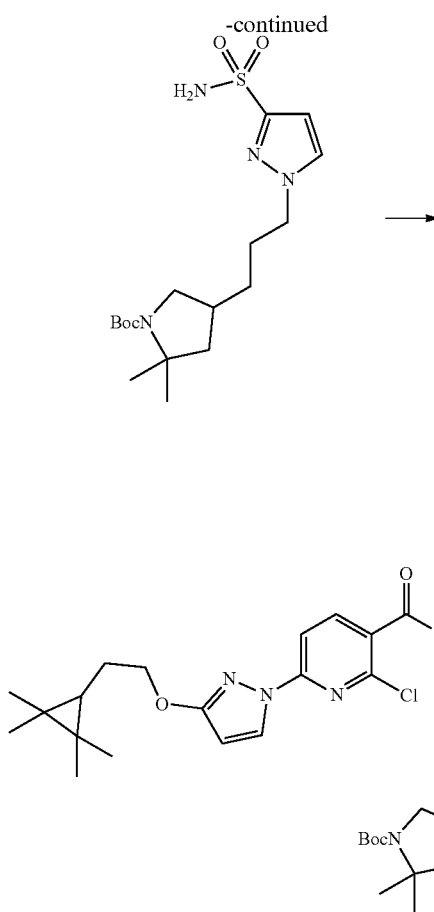

2-Chloro-6-[3-[2-(2,2,3,3-tetramethylcyclopropyl)ethoxy]pyrazol-1-yl]pyridine-3-carboxylic acid (350 mg, 0.9620 mmol) and carbonyl diimidazole (188 mg, 1.159 mmol) were combined in tetrahydrofuran (8.0 mL) and stirred for 90 min at room temperature. Then tert-butyl 2,2-dimethyl-4-[3-(3-sulfamoylpyrazol-1-yl)propyl]pyrrolidine-1-carboxylate (446 mg, 1.154 mmol) was added followed by anhydrous 1,8-diazabicyclo[5.4.0]undec-7-ene (360 μL, 2.407 mmol) and the reaction was stirred at room temperature for 30 min, followed by heating to 40° C. for 20 h. The reaction was diluted with ethyl acetate and washed with a saturated aqueous sodium bicarbonate solution, followed by brine. The organics were separated, dried over sodium sulfate, evaporated and then purified via silica gel chromatography using a gradient from 100% hexanes to 80% ethyl acetate in hexanes followed by a second silica gel column using a gradient from 100% dichloromethane to 15% methanol in dichloromethane to afford tert-butyl 4-[3-[3-[[2-chloro-6-[3-[2-(2,2,3,3-tetramethylcyclopropyl)ethoxy]pyrazol-1-yl]pyridine-3-carbonyl]sulfamoyl]pyrazol-1-yl]propyl]-2,2-dimethyl-pyrrolidine-1-carboxylate (360 mg, 51%) as a white solid. ESI-MS m/z calc. 731.3232, found 732.5 (M+1)⁺; Retention time: 2.14 min (LC Method G).

486

Step 2: 20,20-Dimethyl-4-{3-[2-(2,2,3,3-tetramethylcyclopropyl)ethoxy]-1H-pyrazol-1-yl}-10$\lambda^6$-thia-1,3,9,14,22-pentaazatetracyclo[16.2.1.111,14.02,7]docosa-2(7),3,5,11(22),12-pentaene-8,10,10-trione (Compound 198)

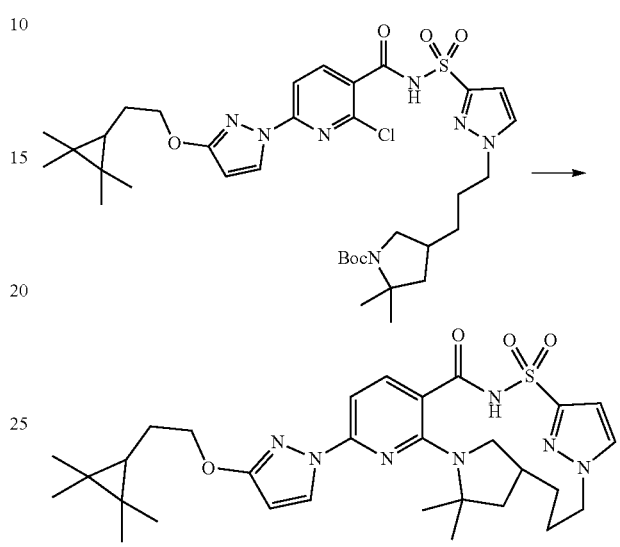

tert-Butyl 4-[3-[3-[[2-chloro-6-[3-[2-(2,2,3,3-tetramethylcyclopropyl)ethoxy]pyrazol-1-yl]pyridine-3-carbonyl]sulfamoyl]pyrazol-1-yl]propyl]-2,2-dimethyl-pyrrolidine-1-carboxylate (360 mg, 0.4916 mmol), potassium carbonate (400 mg, 2.894 mmol), 3 Å molecular sieves and NMP (10 mL) were added to a 20 mL microwave vial, purged with nitrogen, capped, heated to 160° C. and stirred for 96 h. The reaction vessel was cooled to room temperature and was filtered and the filtrate was diluted with ethyl acetate and washed with a saturated aqueous sodium bicarbonate solution, followed by brine. The organics were separated, dried over sodium sulfate, evaporated and then purified by silica gel chromatography using a gradient from 100% hexanes to 90% ethyl acetate in hexanes to afford 20,20-dimethyl-4-[3-[2-(2,2,3,3-tetramethylcyclopropyl)ethoxy]-1H-pyrazol-1-yl]-10$\lambda^6$-thia-1,3,9,14,22-pentaazatetracyclo[16.2.1.111,14.02,7]docosa-2(7),3,5,11(22),12-pentaene-8,10,10-trione (Compound 198) (59.7 mg, 20%) as a white solid. ¹H NMR (400 MHz, Chloroform-d) δ 8.42 (s, 1H), 8.17 (d, J=2.8 Hz, 1H), 7.68 (d, J=8.2 Hz, 1H), 7.48 (d, J=2.3 Hz, 1H), 7.07 (d, J=2.3 Hz, 1H), 7.03 (d, J=8.3 Hz, 1H), 5.88 (d, J=2.7 Hz, 1H), 4.43-4.29 (m, 1H), 4.24 (t, J=7.2 Hz, 2H), 4.00-3.87 (m, 1H), 2.75 (t, J=8.3 Hz, 1H), 2.16-2.12 (m, 1H), 2.03-1.94 (m, 2H), 1.76 (q, J=7.1 Hz, 3H), 1.57 (d, J=15.2 Hz, 6H), 1.47 (t, J=12.3 Hz, 2H), 1.10-1.05 (m, 6H), 0.97 (s, 6H), 0.91-0.75 (m, 2H), 0.25 (t, J=7.2 Hz, 1H). ESI-MS m/z calc. 595.29407, found 596.2 (M+1)⁺; Retention time: 1.94 min (LC Method E).

487

Step 3: 20,20-Dimethyl-4-{3-[2-(2,2,3,3-tetramethylcyclopropyl)ethoxy]-1H-pyrazol-1-yl}-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Enantiomer 1) (Compound 206) and 20,20-dimethyl-4-{3-[2-(2,2,3,3-tetramethylcyclopropyl)ethoxy]-1H-pyrazol-1-yl}-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Enantiomer 2) (Compound 207)

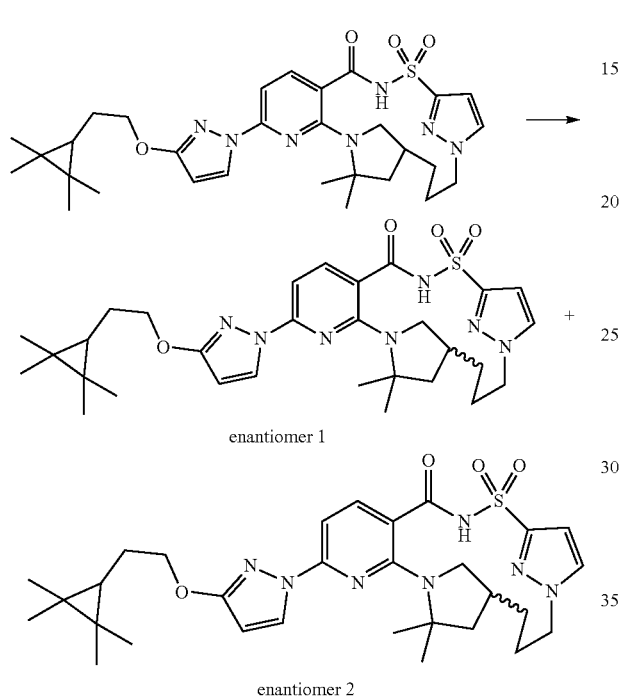

Racemic 20,20-dimethyl-4-[3-[2-(2,2,3,3-tetramethylcyclopropyl)ethoxy]-1H-pyrazol-1-yl]-10λ⁶-thia-1,3,9,14,22-pentaazatetracyclo[16.2.1.1¹¹,14.02,7]docosa-2(7),3,5,11(22),12-pentaene-8,10,10-trione (Compound 198) (45.4 mg, 0.07544 mmol) was separated by chiral SFC chromatography using a ChiralPak AS-H (250×21.2 mm column, 5 μm particle size) with 32% acetonitrile:methanol (90:10; no modifier))/68% carbon dioxide mobile phase at 0.5 mL/min giving as the first enantiomer to elute, 20,20-dimethyl-4-[3-[2-(2,2,3,3-tetramethylcyclopropyl)ethoxy]-1H-pyrazol-1-yl]-10λ⁶-thia-1,3,9,14,22-pentaazatetracyclo[16.2.1.111,14.02,7]docosa-2(7),3,5,11(22),12-pentaene-8,10,10-trione (enantiomer 1) (Compound 206) (18.9 mg, 84%) as a white solid. ESI-MS m/z calc. 595.29407, found 596.2 (M+1)⁺; Retention time: 1.94 min (LC Method E). The second enantiomer to elute was 20,20-dimethyl-4-[3-[2-(2,2,3,3-tetramethylcyclopropyl)ethoxy]-1H-pyrazol-1-yl]-10λ⁶-thia-1,3,9,14,22-pentaazatetracyclo[16.2.1.111,14.02,7]docosa-2(7),3,5,11(22),12-pentaene-8,10,10-trione (enantiomer 2) (Compound 207) (19.2 mg, 85%) as a white solid. ¹H NMR (400 MHz, Chloroform-d) δ 8.38 (s, 1H), 8.17 (d, J=2.8 Hz, 1H), 7.68 (d, J=8.3 Hz, 1H), 7.48 (d, J=2.3 Hz, 1H), 7.12-6.99 (m, 2H), 5.88 (d, J=2.7 Hz, 1H), 4.43-4.30 (m, 1H), 4.24 (t, J=7.2 Hz, 2H), 3.93 (t, J=12.1 Hz, 1H), 2.74 (t, J=8.2 Hz, 1H), 2.17-2.11 (m, 1H), 2.04-1.96 (m, 2H), 1.76 (q, J=7.2 Hz, 3H), 1.59 (s, 6H), 1.47 (t, J=12.1 Hz, 2H), 1.08 (s, 6H), 0.97 (s, 6H), 0.92-0.71 (m, 2H), 0.25 (t, J=7.2

488

Hz, 1H). ESI-MS m/z calc. 595.29407, found 596.2 (M+1)⁺; Retention time: 1.94 min (LC Method E).

Example 56: Preparation of (14S)-12,12-dimethyl-8-[3-(3,3,3-trifluoro-2,2-dimethylpropoxy)-1H-pyrazol-1-yl]-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 208)

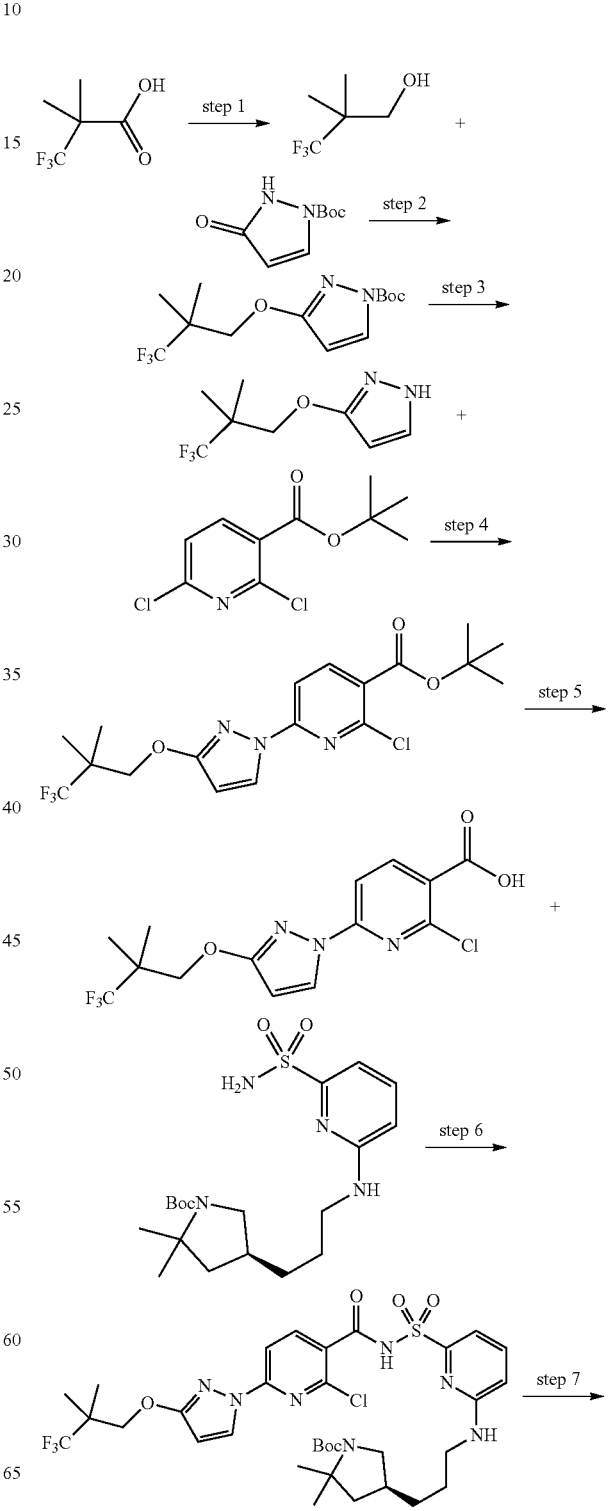

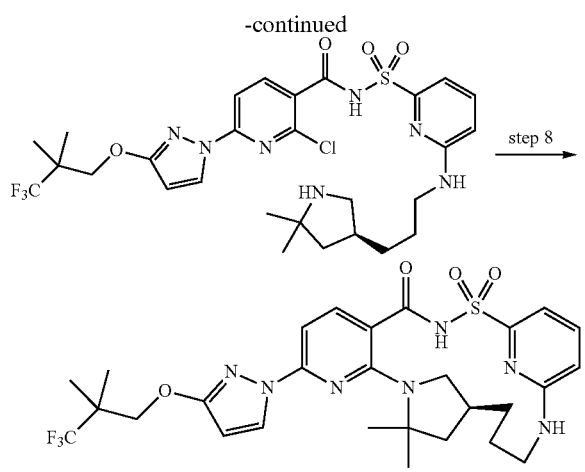

Step 1: 3,3,3-Trifluoro-2,2-dimethyl-propan-1-ol

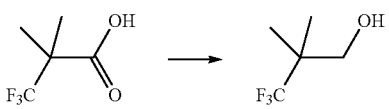

A 1 L, 3-neck round bottom flask was fitted with a mechanical stirrer, a cooling bath, an addition funnel and a J-Kem temperature probe. The vessel was charged with lithium aluminum hydride pellets (6.3 g, 0.1665 mol) under a nitrogen atmosphere. The vessel was then charged with tetrahydrofuran (200 mL) under a nitrogen atmosphere. The mixture was allowed to stir at room temperature for 0.5 h to allow the pellets to dissolve. The cooling bath was then charged with crushed ice in water and the reaction temperature was lowered to 0° C. The addition funnel was charged with a solution of 3,3,3-trifluoro-2,2-dimethyl-propanoic acid (20 g, 0.1281 mol) in tetrahydrofuran (60 mL) and the clear pale yellow solution was added drop wise over 1 h. After the addition was complete the mixture was allowed to slowly warm to room temperature and stirring was continued for 24 h. The suspension was cooled to 0° C. using an ice bath and then quenched by the very slow and drop wise addition of water (6.3 mL), followed by sodium hydroxide solution (15 weight %; 6.3 mL) and then finally with water (18.9 mL). The reaction temperature of the resulting white suspension was recorded at 5° C. The suspension was stirred at 5° C. for 30 min and then filtered through a 20 mm layer of celite. The filter cake was washed with tetrahydrofuran (2×100 mL). The filtrate was dried over sodium sulfate (150 g) and then filtered. The filtrate was concentrated under reduced pressure to provide a clear, colorless oil (15 g) containing a mixture of the product 3,3,3-trifluoro-2,2-dimethyl-propan-1-ol in tetrahydrofuran (73% weight of product (10.95 g) and 27 wt % tetrahydrofuran as determined by $^1$H-NMR). The distillate from the rotary evaporation was distilled at atmospheric pressure using a 30 cm Vigreux column to provide 8.75 g of a residue containing 60% weight of tetrahydrofuran and 40% weight of product (3.5 g). These mixtures of product in tetrahydrofuran were combined giving 3,3,3-trifluoro-2,2-dimethyl-propan-1-ol (14.45 g of 61 wt % in tetrahydrofuran, 79% yield). $^1$H NMR (400 MHz, dimethyl sulfoxide-$d_6$) δ 4.99 (t, J=5.7 Hz, 1H), 3.38 (dd, J=5.8, 0.9 Hz, 2H), 1.04 (d, J=0.9 Hz, 6H).

Step 2: tert-Butyl 3-(3,3,3-trifluoro-2,2-dimethyl-propoxy)pyrazole-1-carboxylate

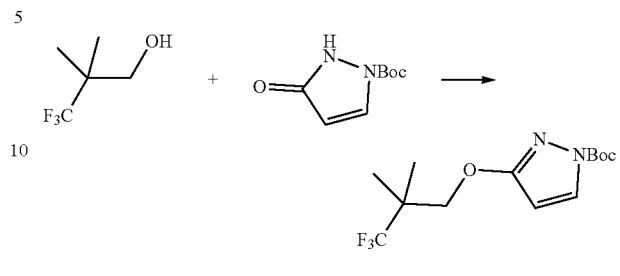

A mixture of 3,3,3-trifluoro-2,2-dimethyl-propan-1-ol (10 g, 70.36 mmol) and tert-butyl 3-hydroxypyrazole-1-carboxylate (12.96 g, 70.36 mmol) in toluene (130 mL) was treated with triphenylphosphine (20.30 g, 77.40 mmol) followed by isopropyl N-isopropoxycarbonyliminocarbamate (14.99 mL, 77.40 mmol) and the mixture was stirred at 110° C. for 16 h. The yellow solution was concentrated under reduced pressure, diluted with heptane (100 mL) and the precipitated triphenylphosphine oxide was removed by filtration and washed with heptane/toluene 4:1 (100 mL). The yellow filtrate was evaporated and the residue purified by silica gel chromatography with a linear gradient of ethyl acetate in hexane (0-40%) to give tert-butyl 3-(3,3,3-trifluoro-2,2-dimethyl-propoxy)pyrazole-1-carboxylate (12.3 g, 57%) as an off white solid. $^1$H NMR (400 MHz, dimethyl sulfoxide-$d_6$) δ 8.10 (d, J=3.0 Hz, 1H), 6.15 (d, J=3.0 Hz, 1H), 4.18 (s, 2H), 1.55 (s, 9H), 1.21 (s, 6H). ESI-MS m/z calc. 308.13477, found 309.0 (M+1)$^+$; Retention time: 1.92 min (LC Method B).

Step 3: 3-(3,3,3-Trifluoro-2,2-dimethyl-propoxy)-1H-pyrazole

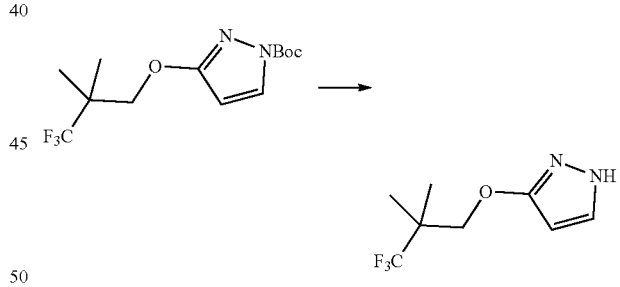

tert-Butyl 3-(3,3,3-trifluoro-2,2-dimethyl-propoxy)pyrazole-1-carboxylate (13.5 g, 43.79 mmol) was treated with 4 M hydrogen chloride in dioxane (54.75 mL, 219.0 mmol) and the mixture was stirred at 45° C. for 1 h. The reaction mixture was evaporated to dryness and the residue was extracted with 1 M aqueous sodium hydroxide (100 mL) and methyl tert-butyl ether (100 mL), washed with brine (50 mL) and extracted with methyl tert-butyl ether (50 mL). The combined organic phases were dried over sodium sulfate, filtered and evaporated to give 3-(3,3,3-trifluoro-2,2-dimethyl-propoxy)-1H-pyrazole (9.0 g, 96%) as an off white waxy solid. $^1$H NMR (400 MHz, dimethyl sulfoxide-$d_6$) δ 11.91 (s, 1H), 7.52 (d, J=2.2 Hz, 1H), 5.69 (t, J=2.3 Hz, 1H), 4.06 (s, 2H), 1.19 (s, 6H). ESI-MS m/z calc. 208.08235, found 209.0 (M+1)$^+$; Retention time: 1.22 min (LC Method B).

Step 4: tert-Butyl 2-chloro-6-[3-(3,3,3-trifluoro-2,2-dimethyl-propoxy)pyrazol-1-yl]pyridine-3-carboxylate

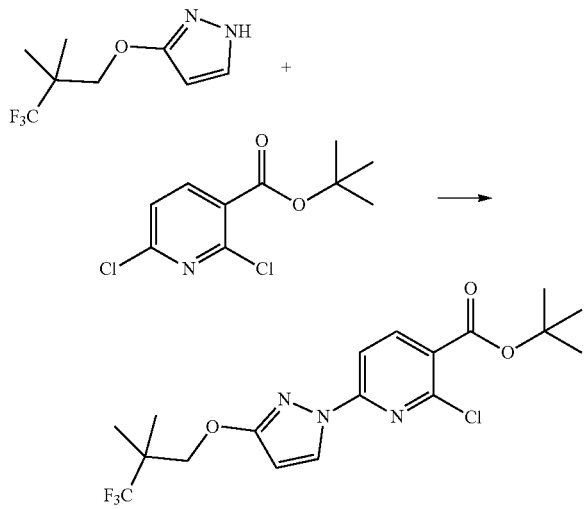

To a solution of tert-butyl 2,6-dichloropyridine-3-carboxylate (10.4 g, 41.9 mmol) and 3-(3,3,3-trifluoro-2,2-dimethyl-propoxy)-1H-pyrazole (9.0 g, 41.93 mmol) in N,N-dimethylformamide (110 mL) was added potassium carbonate (7.53 g, 54.5 mmol) and 1,4-diazabicyclo[2.2.2]octane (706 mg, 6.29 mmol) and the mixture was stirred at room temperature for 16 h. The cream suspension was cooled in a cold water bath and cold water (130 mL) was slowly added. The thick suspension was stirred at room temperature for 1 h, filtered and washed with water to give tert-butyl 2-chloro-6-[3-(3,3,3-trifluoro-2,2-dimethyl-propoxy)pyrazol-1-yl]pyridine-3-carboxylate (17.6 g, 99%) as an off white solid after drying under vacuum. $^1$H NMR (400 MHz, dimethyl sulfoxide-$d_6$) δ 8.44 (d, J=2.9 Hz, 1H), 8.31 (d, J=8.4 Hz, 1H), 7.76 (d, J=8.4 Hz, 1H), 6.26 (d, J=2.9 Hz, 1H), 4.27 (s, 2H), 1.57 (s, 9H), 1.24 (s, 6H). ESI-MS m/z calc. 419.12234, found 420.0 (M+1)$^+$; Retention time: 2.36 min (LC Method B).

Step 5: 2-Chloro-6-[3-(3,3,3-trifluoro-2,2-dimethyl-propoxy)pyrazol-1-yl]pyridine-3-carboxylic Acid

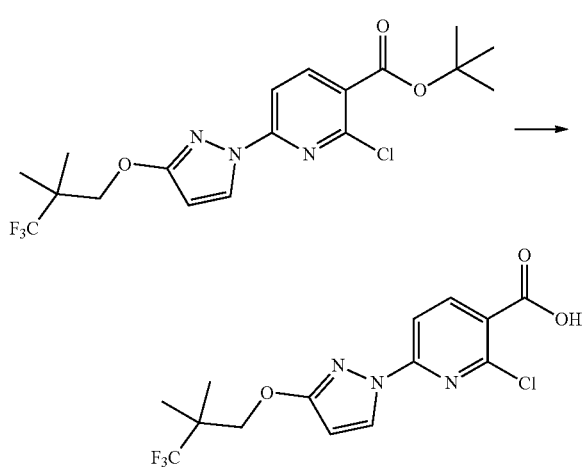

tert-Butyl 2-chloro-6-[3-(3,3,3-trifluoro-2,2-dimethyl-propoxy)pyrazol-1-yl]pyridine-3-carboxylate (17.6 g, 40.25 mmol) was suspended in isopropanol (85 mL) treated with hydrochloric acid (34 mL of 6 M, 201 mmol) and heated to reflux for 3 h (went almost complete into solution at reflux and started to precipitate again). The suspension was diluted with water (51 mL) at reflux and left to cool to room temperature while stirring for 2.5 h. The solid was collected by filtration, washed with isopropanol/water 1:1 (50 mL), additional water and dried in a drying cabinet under vacuum at 45-50° C. with a nitrogen bleed overnight to give 2-chloro-6-[3-(3,3,3-trifluoro-2,2-dimethyl-propoxy)pyrazol-1-yl]pyridine-3-carboxylic acid (13.7 g, 91%) as an off white solid. $^1$H NMR (400 MHz, dimethyl sulfoxide-$d_6$) δ 13.61 (s, 1H), 8.44 (d, J=2.9 Hz, 1H), 8.39 (d, J=8.4 Hz, 1H), 7.77 (d, J=8.4 Hz, 1H), 6.25 (d, J=2.9 Hz, 1H), 4.28 (s, 2H), 1.24 (s, 6H). ESI-MS m/z calc. 363.05975, found 364.0 (M+1)$^+$; Retention time: 1.79 min (LC Method B).

Step 6: tert-Butyl (4S)-4-[3-[[6-[[2-chloro-6-[3-(3,3,3-trifluoro-2,2-dimethyl-propoxy)pyrazol-1-yl]pyridine-3-carbonyl]sulfamoyl]-2-pyridyl]amino]propyl]-2,2-dimethyl-pyrrolidine-1-carboxylate

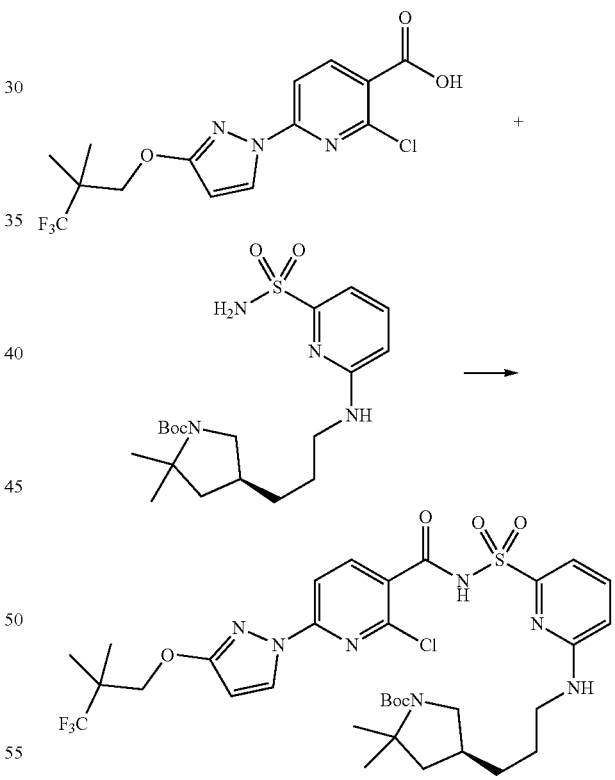

2-Chloro-6-[3-(3,3,3-trifluoro-2,2-dimethyl-propoxy)pyrazol-1-yl]pyridine-3-carboxylic acid (174.5 mg, 0.4702 mmol) and carbonyl diimidazole (95.31 mg, 0.5878 mmol) were combined in tetrahydrofuran (2.223 mL) and stirred for 90 min at room temperature. Then tert-butyl (4S)-2,2-dimethyl-4-[3-[(6-sulfamoyl-2-pyridyl)amino]propyl]pyrrolidine-1-carboxylate (194 mg, 0.4702 mmol) was added as a solution in tetrahydrofuran (855 µL) followed by 1,8-diazabicyclo[5.4.0]undec-7-ene (357.9 mg, 2.351 mmol) and the reaction was stirred at 50° C. for 2.5 h. Continued stirring at room temperature for 4 days. The reaction was then diluted with ethyl acetate and washed with a sat aqueous ammonium chloride solution, followed by brine. The organics were separated, dried over sodium sulfate, evaporated and then purified by silica gel chromatography using a shallow gradient from 100% hexanes to 100% ethyl acetate giving pure product material and fractions mixed with starting material acid. Mixed fractions with starting acid were combined, evaporated and purified using a reverse phase HPLC-MS method using a Luna $C_{18}$ (2) column (75×30 mm, 5 µm particle size) sold by Phenomenex (pn: 00C-4252-U0-AX) and a dual gradient run from 30-99% mobile phase B over 15.0 min (mobile phase A=water (5 mM hydrochloric acid), mobile phase B=acetonitrile, flow rate=50 mL/min, injection volume=950 µL and column temperature=25° C.) and pure product fractions were combined with pure material from the original silica column to give tert-butyl (4S)-4-[3-[[6-[[2-chloro-6-[3-(3,3,3-trifluoro-2,2-dimethyl-propoxy)pyrazol-1-yl]pyridine-3-carbonyl]sulfamoyl]-2-pyridyl]amino]propyl]-2,2-dimethyl-pyrrolidine-1-carboxylate (110.4 mg, 31%) as a white solid. ESI-MS m/z calc. 757.2636, found 758.4 (M+1)+; Retention time: 0.9 min (LC Method A).

Step 7: 2-Chloro-N-[[6-[3-[(3S)-5,5-dimethylpyrrolidin-3-yl]propylamino]-2-pyridyl]sulfonyl]-6-[3-(3,3,3-trifluoro-2,2-dimethyl-propoxy)pyrazol-1-yl]pyridine-3-carboxamide

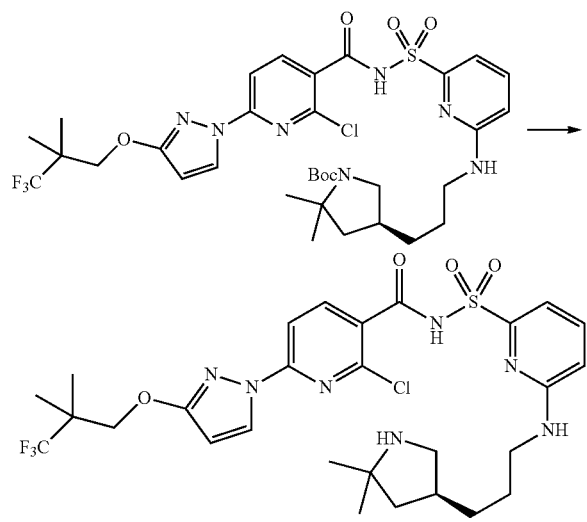

To a round bottom flask containing tert-butyl (4S)-4-[3-[[6-[[2-chloro-6-[3-(3,3,3-trifluoro-2,2-dimethyl-propoxy)pyrazol-1-yl]pyridine-3-carbonyl]sulfamoyl]-2-pyridyl]amino]propyl]-2,2-dimethyl-pyrrolidine-1-carboxylate (110.4 mg, 0.1456 mmol) was added dichloromethane (2 mL) and trifluoroacetic acid (450 µL, 5.841 mmol). After 1 h at room temperature, the reaction was evaporated to dryness. The crude reaction mixture was neutralized with saturated sodium bicarbonate and extracted with ethyl acetate. The product crashed out and a little methanol was used to help in the extraction. The organic layer was separated and evaporated to provide 2-chloro-N-[[6-[3-[(3S)-5,5-dimethylpyrrolidin-3-yl]propylamino]-2-pyridyl]sulfonyl]-6-[3-(3,3,3-trifluoro-2,2-dimethyl-propoxy)pyrazol-1-yl]pyridine-3-carboxamide (95 mg, 99%) as a white solid. ESI-MS m/z calc. 657.2112, found 658.4 (M+1)+; Retention time: 1.62 min (LC Method B).

Step 8: (14S)-12,12-dimethyl-8-[3-(3,3,3-trifluoro-2,2-dimethylpropoxy)-1H-pyrazol-1-yl]-2λ⁶-thia-3,9,11,18,23-pentaazatetracyclo[17.3.1.111,14.05,10]tetracosa-1(22),5,7,9,19(23),20-hexaene-2,2,4-trione (Compound 208)

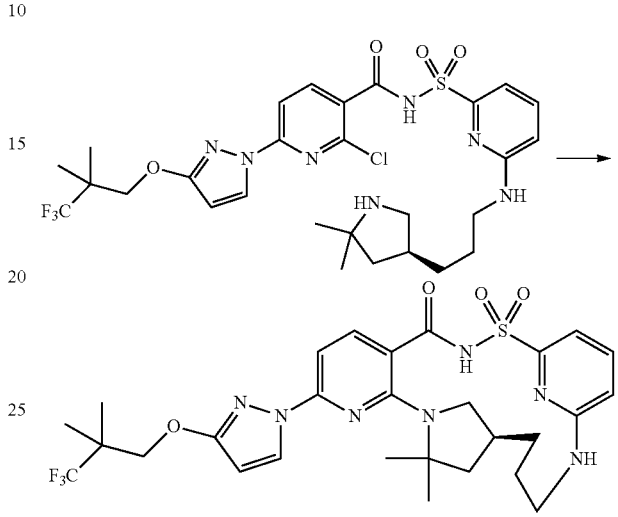

To a vial was added cesium fluoride (33.5 mg, 0.2205 mmol), potassium carbonate (100 mg, 0.7236 mmol), 3 Å molecular sieves and a solution of 2-chloro-N-[[6-[3-[(3S)-5,5-dimethylpyrrolidin-3-yl]propylamino]-2-pyridyl]sulfonyl]-6-[3-(3,3,3-trifluoro-2,2-dimethyl-propoxy)pyrazol-1-yl]pyridine-3-carboxamide (95 mg, 0.1443 mmol) in dimethyl sulfoxide (2.5 mL). The reaction was capped and placed in a preheated 150° C. oil bath overnight. The reaction was cooled to room temperature, filtered and purified via HPLC (30%-99% acetonitrile:water with a 0.1% hydrochloric acid modifier giving (14S)-12,12-dimethyl-8-[3-(3,3,3-trifluoro-2,2-dimethylpropoxy)-1H-pyrazol-1-yl]-2λ⁶-thia-3,9,11,18,23-pentaazatetracyclo[17.3.1.111,14.05,10]tetracosa-1(22),5,7,9,19(23),20-hexaene-2,2,4-trione (Compound 208) (45.5 mg, 51%) as a tan solid. ¹H NMR (400 MHz, dimethyl sulfoxide-d₆) δ 12.49 (s, 1H), 8.23 (d, J=2.8 Hz, 1H), 7.82 (d, J=8.2 Hz, 1H), 7.58 (dd, J=8.5, 7.2 Hz, 1H), 7.05 (d, J=7.1 Hz, 1H), 6.95 (d, J=8.2 Hz, 2H), 6.71 (d, J=8.5 Hz, 1H), 6.18 (d, J=2.7 Hz, 1H), 4.27-4.19 (m, 2H), 3.92 (d, J=12.4 Hz, 1H), 3.16 (s, 1H), 2.95 (d, J=13.5 Hz, 1H), 2.71 (t, J=10.8 Hz, 1H), 2.13 (s, 1H), 1.86 (dd, J=11.8, 5.2 Hz, 1H), 1.77 (s, 1H), 1.65-1.48 (m, 9H), 1.35 (dd, J=25.8, 14.3 Hz, 1H), 1.24 (s, 6H). ESI-MS m/z calc. 621.2345, found 622.3 (M+1)+; Retention time: 2.24 min (LC Method B).

Example 57: Preparation of (14S)-12,12-dimethyl-8-[3-(4,4,4-trifluoro-3,3-dimethylbutoxy)-1H-pyrazol-1-yl]-2λ⁶-thia-3,9,11,18,23-pentaazatetracyclo[17.3.1.111,14.05,10]tetracosa-1(22),5,7,9,19(23),20-hexaene-2,2,4-trione (Compound 212)

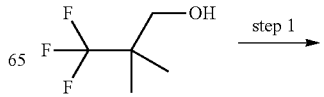

495
-continued

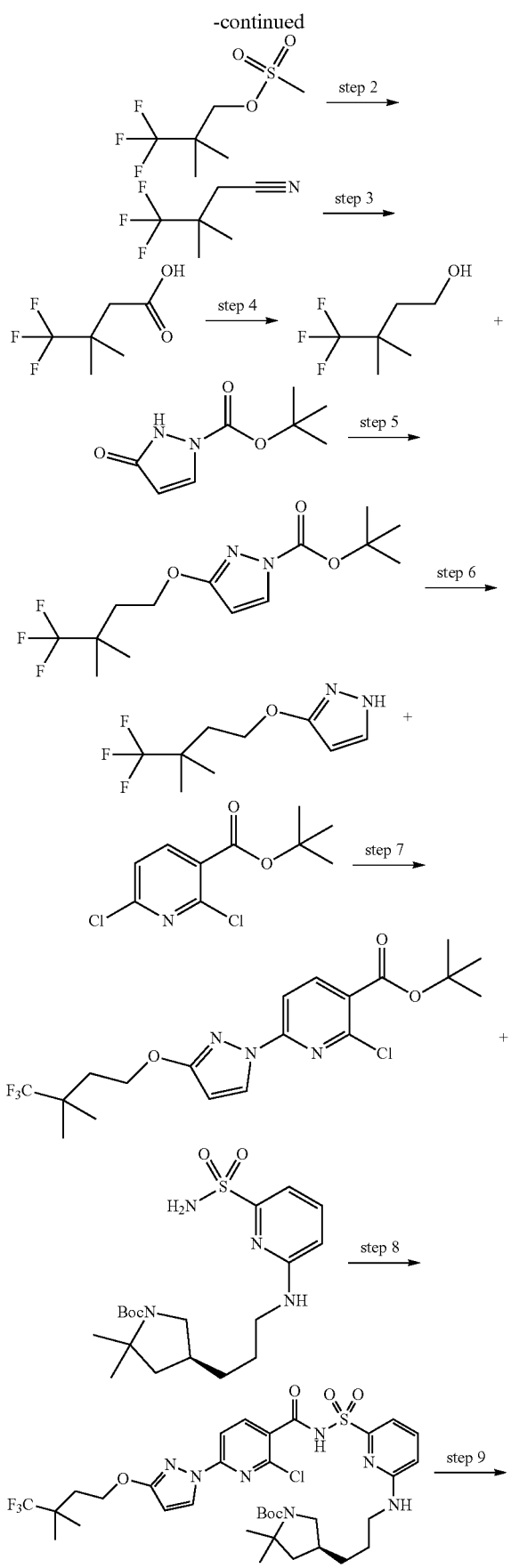

496
-continued

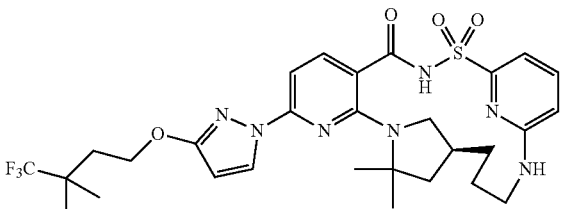

Step 1: (3,3,3-Trifluoro-2,2-dimethyl-propyl) methanesulfonate

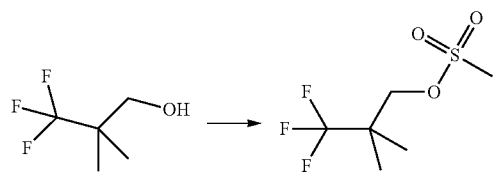

To a solution of 3,3,3-trifluoro-2,2-dimethyl-propan-1-ol (17 g, 104.1 mmol) in dry dichloromethane (150 mL) was added triethylamine (45.0 mL, 322.9 mmol). The reaction was cooled to 0° C. and methanesulfonyl chloride (10 mL, 129.2 mmol) was added slowly dropwise under a nitrogen atmosphere. The resultant heterogeneous mixture was stirred for 1 h while warming to ambient temperature. The reaction was then quenched with cold water (150 mL) and extracted with dichloromethane (200 mL) twice. The organic layer was dried over sodium sulfate, filtered and evaporated (bath temperature 20° C. at 300 mbar) to provide 3,3,3-trifluoro-2,2-dimethyl-propyl methanesulfonate (18.4 g, 80%) as clear yellowish liquid. $^1$H NMR (400 MHz, Chloroform-d) δ 4.13 (d, J=2.4 Hz, 2H), 3.03 (d, J=2.4 Hz, 3H), 1.21 (d, J=2.4 Hz, 6H).

Step 2: 4,4,4-Trifluoro-3,3-dimethyl-butanenitrile

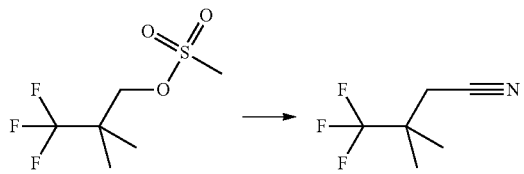

To a solution of (3, 3,3-trifluoro-2,2-dimethyl-propyl) methanesulfonate (30.00 g, 136.2 mmol) in dimethyl sulfoxide (150 mL) was added cyanosodium (20.05 g, 409.1 mmol). The reaction was equipped with a reflux condenser and heated at 120° C. for 3 days. The reaction was then cooled to 0° C. and ice water was added followed by brine. The reaction mixture was then extracted with ether twice, organic layers were combined and dried over sodium sulfate, filtered and evaporated to provide 4,4,4-trifluoro-3,3-dimethyl-butanenitrile (18.43 g, 90%) as an orange liquid. $^1$H NMR (400 MHz, Chloroform-d) δ 2.56 (s, 2H), 1.33 (s, 6H).

Step 3: 4,4,4-Trifluoro-3,3-dimethyl-butanoic Acid

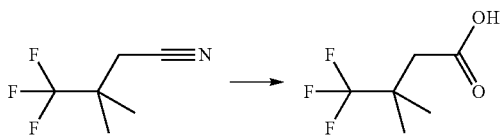

To a solution of 4,4,4-trifluoro-3,3-dimethyl-butanenitrile (12 g, 39.70 mmol) in ethanol (100 mL) was added sodium hydroxide (35 mL of 6 M, 210.0 mmol). The resulting clear amber solution was heated to 70° C. overnight. The reaction mixture was cooled to ambient temperature and water (30 mL) was added to the reaction mixture and it was extracted with ether. The ether layer was washed with 6M sodium hydroxide. The aqueous layers were combined and the aqueous solution was adjusted to pH=1 with concentrated hydrochloric acid cautiously at 0° C. The mixture was then extracted with ether (3×100 mL). The organic extracts were combined and dried over sodium sulfate, filtered and concentrated (bath temperature 20° C. at 300 mbar) to afford 4,4,4-trifluoro-3,3-dimethyl-butanoic acid (3.8 g, 28%). $^1$H NMR (400 MHz, Chloroform-d) δ 2.48 (s, 2H), 1.27-1.26 (s, 6H).

Step 4: 4,4,4-Trifluoro-3,3-dimethyl-butan-1-ol

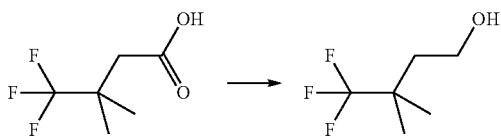

To a slurry of lithium aluminum hydride (438 mg, 11.24 mmol) in ether (30 mL) was added dropwise via an addition funnel a solution of 4,4,4-trifluoro-3,3-dimethyl-butanoic acid (3.8 g, 11.17 mmol) in ether (30 mL) at 0° C. under a nitrogen atmosphere. The resulting slurry was stirred at ambient temperature for 24 h. The reaction mixture was cooled in an ice-bath and sequentially quenched with water (450 µL, 24.98 mmol) (slowly), followed by sodium hydroxide (450 µL of 6 M, 2.700 mmol), then water (1.35 mL, 74.94 mmol) affording a white, granular slurry which was further stirred with anhydrous magnesium sulfate for 30 min then filtered over celite. The precipitate was washed with ether and the filtrate was concentrated (at ~400 mbar and 20° C. water bath) to afford 4,4,4-trifluoro-3,3-dimethyl-butan-1-ol (1.5 g, 86%) as a colorless liquid. $^1$H NMR (400 MHz, Chloroform-d) δ 3.77 (td, J=7.3, 0.8 Hz, 2H), 1.79 (t, J=7.4 Hz, 2H), 1.15 (d, J=0.8 Hz, 6H).

Step 5: tert-Butyl 3-(4,4,4-trifluoro-3,3-dimethyl-butoxy)pyrazole-1-carboxylate

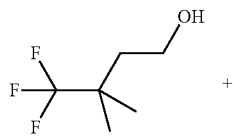

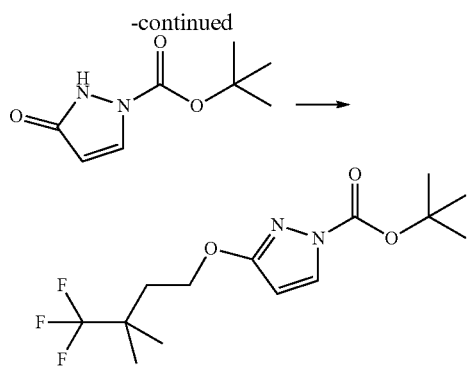

A solution of 4,4,4-trifluoro-3,3-dimethyl-butan-1-ol (1.0 g, 6.404 mmol), tert-butyl 3-hydroxypyrazole-1-carboxylate (1.2 g, 6.515 mmol), triphenylphosphine (1.9 g, 7.244 mmol) in dry tetrahydrofuran (10 mL) was cooled in an ice bath and DIAD (1.5 mL, 7.618 mmol) was slowly added under a nitrogen atmosphere. The reaction was allowed to slowly warm to room temperature and was stirred overnight. The reaction mixture was diluted with ethyl acetate, washed with saturated aqueous sodium bicarbonate then brine and dried over sodium sulfate, filtered and evaporated under vacuum. The residue was purified by silica gel column chromatography using a gradient from 100% hexanes to 50% ethyl acetate in hexanes to afford tert-butyl 3-(4,4,4-trifluoro-3,3-dimethyl-butoxy)pyrazole-1-carboxylate (650 mg, 31%) as colorless oil. $^1$H NMR (400 MHz, Chloroform-d) δ 7.83 (d, J=2.9 Hz, 1H), 5.84 (d, J=3.1 Hz, 1H), 4.38 (t, J=7.2 Hz, 2H), 1.98 (t, J=7.1 Hz, 2H), 1.61 (s, 9H), 1.18 (s, 6H). ESI-MS m/z calc. 322.15042, found 323.18 (M+1)$^+$; Retention time: 0.74 min (LC Method A).

Step 6: 3-(4,4,4-Trifluoro-3,3-dimethyl-butoxy)-1H-pyrazole

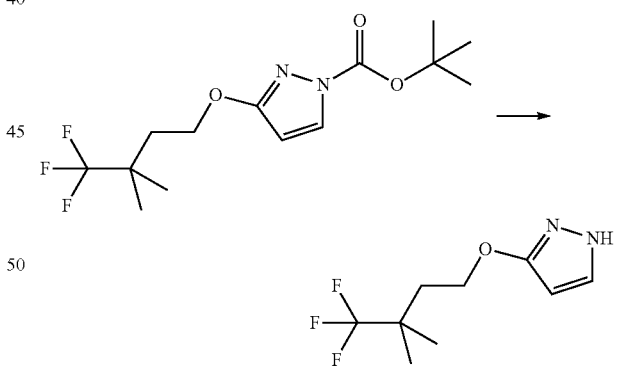

A solution of tert-butyl 3-(4,4,4-trifluoro-3,3-dimethyl-butoxy)pyrazole-1-carboxylate (650 mg, 2.017 mmol) and trifluoroacetic acid (1 mL, 12.98 mmol) in dichloromethane (4 mL) was stirred for 4 h at room temperature. The volatiles were removed under vacuum and the residue was basified with saturated aqueous sodium bicarbonate and extracted with ethyl acetate. The combined extracts were dried over sodium sulfate, filtered and evaporated to afford 3-(4,4,4-trifluoro-3,3-dimethyl-butoxy)-1H-pyrazole (448 mg, 100%) as a colorless oil. ESI-MS m/z calc. 222.09799, found 223.09 (M+1)$^+$; Retention time: 0.53 min (LC Method A).

Step 7: tert-Butyl 2-chloro-6-[3-(4,4,4-trifluoro-3,3-dimethyl-butoxy)pyrazol-1-yl]pyridine-3-carboxylate

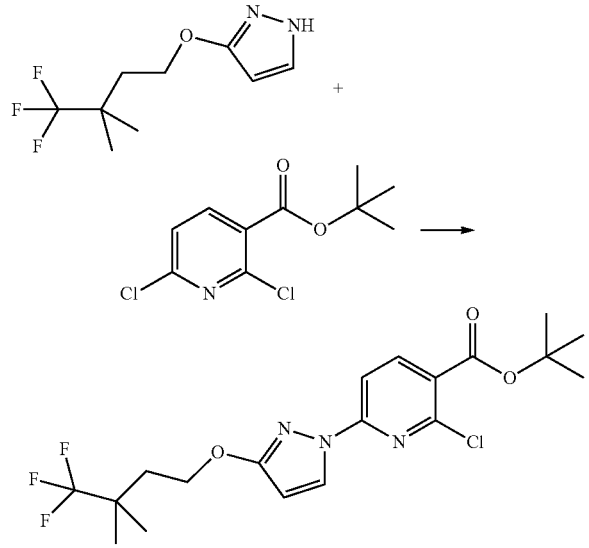

A mixture of 3-(4,4,4-trifluoro-3,3-dimethyl-butoxy)-1H-pyrazole (448 mg, 2.016 mmol), tert-butyl 2,6-dichloropyridine-3-carboxylate (501 mg, 2.019 mmol), potassium carbonate (336 mg, 2.431 mmol) and 1,4-diazabicyclo[2.2.2]octane (46 mg, 0.4101 mmol) in dimethyl sulfoxide (5 mL) was stirred at room temperature for 15 h. The reaction was diluted with water and extracted with ethyl acetate. The combined organic extracts were washed with brine, dried over sodium sulfate, filtered and evaporated. The residue was purified by silica gel column chromatography using a gradient from 100% hexanes to 20% ethyl acetate in hexanes to afford tert-butyl 2-chloro-6-[3-(4,4,4-trifluoro-3,3-dimethyl-butoxy)pyrazol-1-yl]pyridine-3-carboxylate (471 mg, 54%) as a white solid. $^1$H NMR (400 MHz, Chloroform-d) δ 8.36 (d, J=2.8 Hz, 1H), 8.19 (dd, J=8.2, 1.8 Hz, 1H), 7.69 (dd, J=8.2, 1.8 Hz, 1H), 5.94 (d, J=2.8 Hz, 1H), 4.38 (t, J=7.2 Hz, 2H), 2.03 (t, J=7.2 Hz, 2H), 1.62 (d, J=2.1 Hz, 9H), 1.22 (s, 6H). ESI-MS m/z calc. 433.138, found 434.2 (M+1)$^+$; Retention time: 0.91 min (LC Method A).

Step 8: tert-Butyl (4S)-4-[3-[[6-[[2-chloro-6-[3-(4,4,4-trifluoro-3,3-dimethyl-butoxy)pyrazol-1-yl]pyridine-3-carbonyl]sulfamoyl]-2-pyridyl]amino]propyl]-2,2-dimethyl-pyrrolidine-1-carboxylate

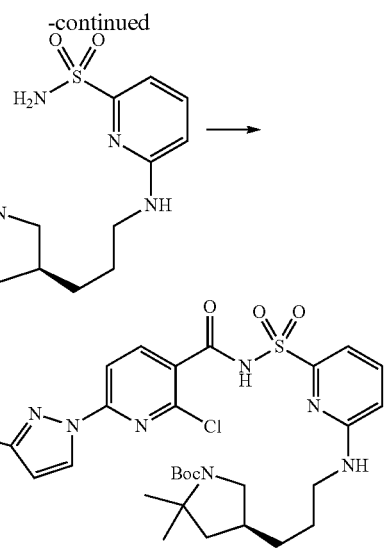

A solution of tert-butyl-2-chloro-6-[3-(4,4,4-trifluoro-3,3-dimethyl-butoxy)pyrazol-1-yl]pyridine-3-carboxylate (150 mg, 0.3457 mmol) in trifluoroacetic acid (150 μL, 1.947 mmol) and dichloromethane (1 mL) was stirred at room temperature for 2 h. The solvent was removed and dried the residue under high vacuum to afford a white solid. To a solution of this solid in tetrahydrofuran (2 mL) was added carbonyl diimidazole (68 mg, 0.4194 mmol) and the reaction mixture was stirred for 4 h at room temperature. Then, tert-butyl (4S)-2,2-dimethyl-4-[3-[(6-sulfamoyl-2-pyridyl)amino]propyl]pyrrolidine-1-carboxylate (146 mg, 0.3539 mmol) in tetrahydrofuran (2 mL) was added followed by 1,8-diazabicyclo[5.4.0]undec-7-ene (110 μL, 0.7356 mmol) and the reaction was stirred for 16 h. The reaction was diluted with ethyl acetate and washed with a mixture of saturated ammonium chloride and brine (1:1). The organics were separated, dried over sodium sulfate, filtered and evaporated. The resulting brown residue was purified by silica gel chromatography using a shallow gradient from 100% dichloromethane to 20% methanol/dichloromethane to afford tert-butyl (4S)-4-[3-[[6-[[2-chloro-6-[3-(4,4,4-trifluoro-3,3-dimethyl-butoxy)pyrazol-1-yl]pyridine-3-carbonyl]sulfamoyl]-2-pyridyl]amino]propyl]-2,2-dimethyl-pyrrolidine-1-carboxylate (82 mg, 31%) as white solid. ESI-MS m/z calc. 771.27924, found 772.36 (M+1)$^+$; Retention time: 0.89 min (LC Method A).

Step 9: (14S)-12,12-Dimethyl-8-[3-(4,4,4-trifluoro-3,3-dimethylbutoxy)-1H-pyrazol-1-yl]-2λ$^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 212)

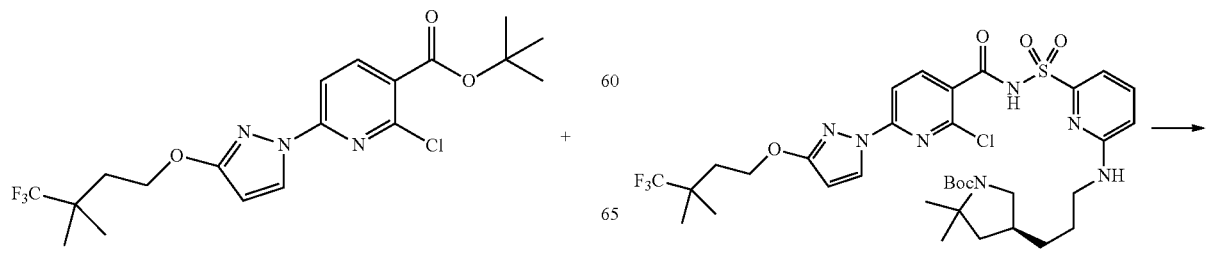

501
-continued

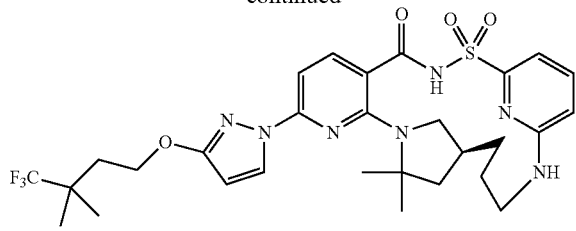

A solution of tert-butyl (4S)-4-[3-[[6-[[2-chloro-6-[3-(4,4,4-trifluoro-3,3-dimethyl-butoxy)pyrazol-1-yl]pyridine-3-carbonyl]sulfamoyl]-2-pyridyl]amino]propyl]-2,2-dimethyl-pyrrolidine-1-carboxylate (82 mg, 0.1062 mmol) in dichloromethane (500 µL) and trifluoroacetic acid (100 µL, 1.307 mmol) was stirred at room temperature for 4 h. The solvents were then removed and the residue was dried under vacuum. This residue was dissolved in dimethyl sulfoxide (5 mL) and oven dried 3 Å molecular sieves were added and the reaction mixture was stirred for 10 min. Then, cesium fluoride (51 mg, 0.3357 mmol) and potassium carbonate (48 mg, 0.3473 mmol) were added and the reaction mixture was heated at 130° C. overnight. The reaction mixture was filtered through a Whatman filter disc (puradisc 25 TF) and the filtrate was purified by a reverse phase HPLC-MS method using a dual gradient run from 50-99% mobile phase B over 15.0 min (mobile phase A=water (0.05% hydrochloric acid). mobile phase B=acetonitrile) to afford (14S)-12,12-dimethyl-8-[3-(4,4,4-trifluoro-3,3-dimethylbutoxy)-1H-pyrazol-1-yl]-2$\lambda^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Compound 212) (34.5 mg, 51%) as white solid. ¹H NMR (400 MHz, Chloroform-d) δ 9.84 (s, 1H), 8.20 (d, J=2.8 Hz, 1H), 8.07 (d, J=8.4 Hz, 1H), 7.54 (dt, J=15.1, 7.2 Hz, 2H), 7.27 (d, J=8.3 Hz, 1H), 6.57 (d, J=8.1 Hz, 1H), 5.91 (d, J=2.8 Hz, 1H), 4.38 (t, J=7.2 Hz, 2H), 3.91 (s, 1H), 3.41-3.31 (m, 1H), 3.17 (d, J=14.5 Hz, 1H), 3.06 (t, J=9.7 Hz, 1H), 2.62 (s, 1H), 2.09 (dd, J=12.3, 7.9 Hz, 1H), 2.03 (t, J=7.2 Hz, 2H), 1.62 (d, J=3.6 Hz, 11H), 1.22 (d, J=0.8 Hz, 6H). ESI-MS m/z calc. 635.2502, found 636.2 (M+1)⁺; Retention time: 1.14 min (LC Method J).

Example 58: Preparation of 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Diastereomer Pair 1) (Compound 209), 8-[3-(3,3-dimethylbutyl)-2-oxoimidazolidin-1-yl]-12,12,1'7-trimethyl-2$\lambda^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Diastereomer Pair 2) (Compound 210), 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Diastereomer Pair 1, Enantiomer 1) (Compound 215), 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Diastereomer Pair 1, Enantiomer 2) (Compound 216), 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1¹¹,14.0⁵,¹⁰]tetracosa-1(22),5,7,9,19(23), 20-hexaene-2,2,4-trione (Diastereomer Pair 2, Enantiomer 1) (Compound 218) and 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1¹¹,14.0⁵,¹⁰]tetracosa-1(22),5,7,9,19(23), 20-hexaene-2,2,4-trione (Diastereomer Pair 2, Enantiomer 2) (Compound 219)

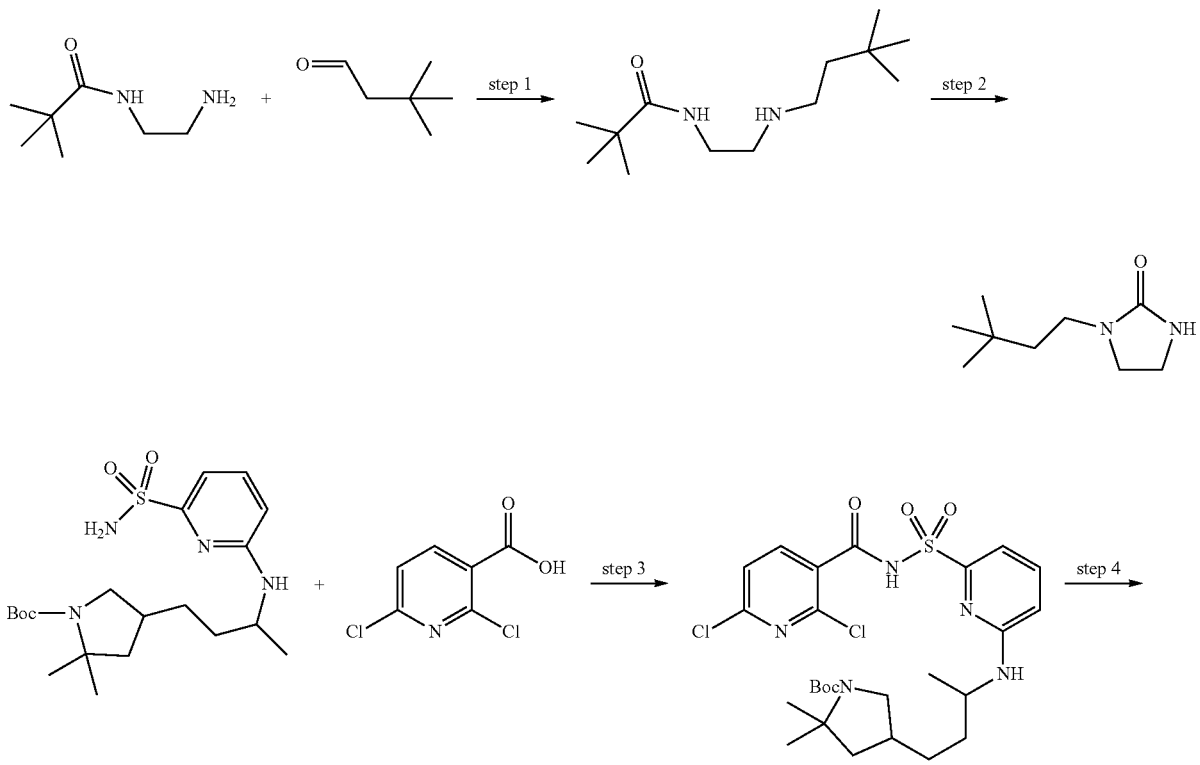

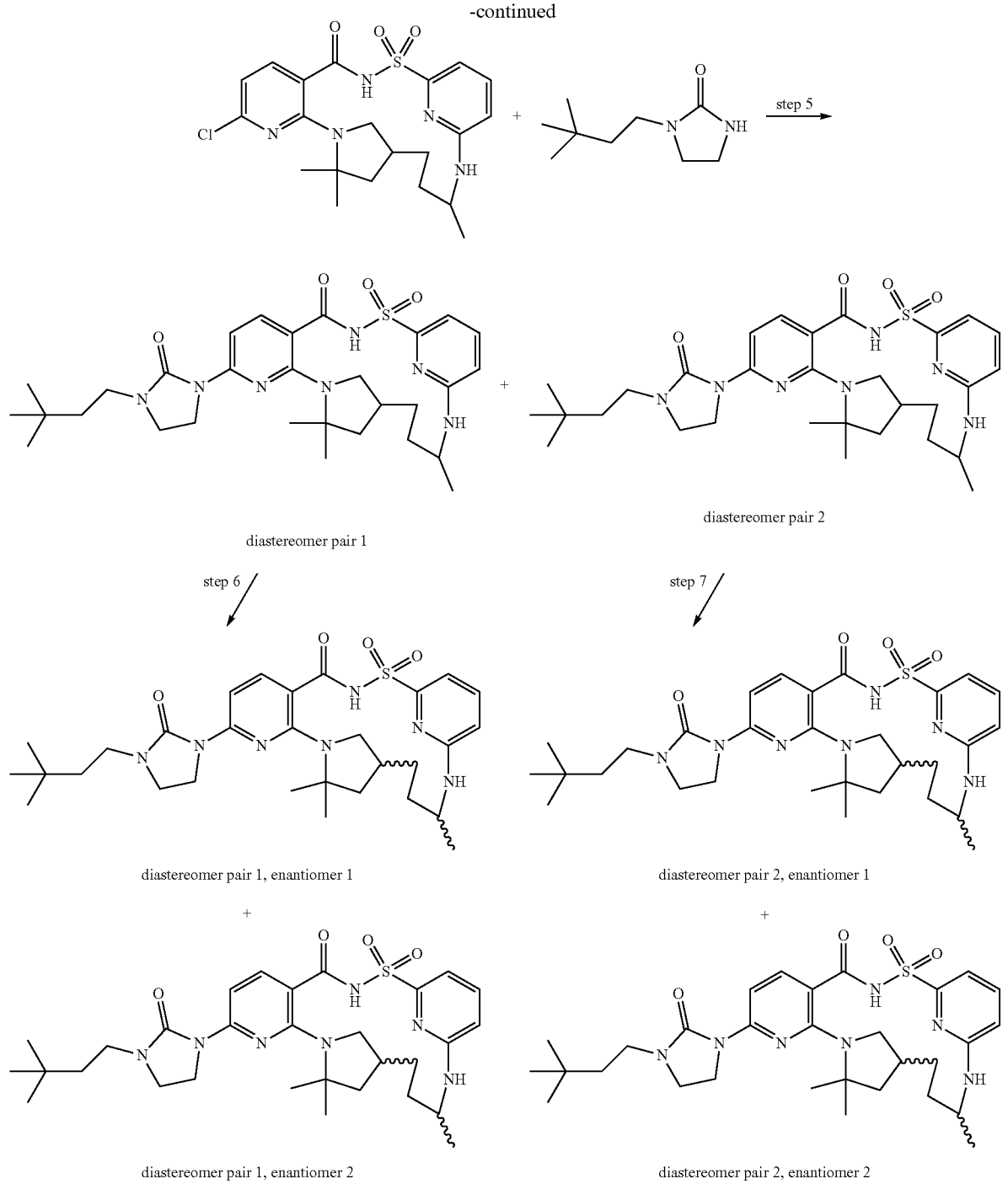
Step 1: tert-Butyl N-[2-(3,3-dimethylbutylamino)ethyl]carbamate
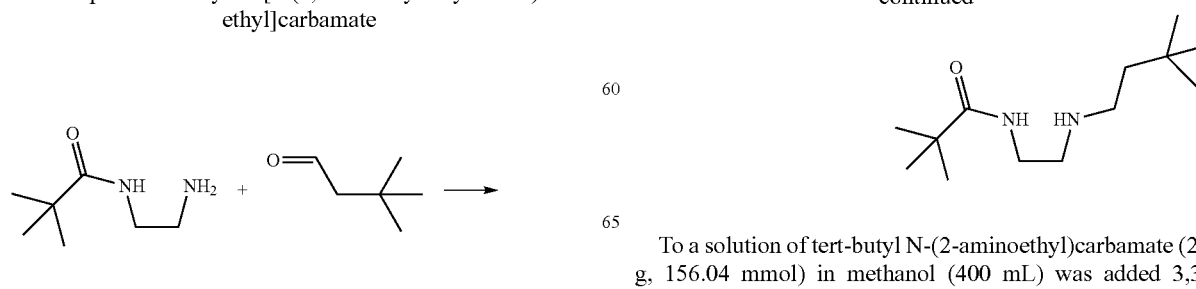
To a solution of tert-butyl N-(2-aminoethyl)carbamate (25 g, 156.04 mmol) in methanol (400 mL) was added 3,3- dimethylbutanal (20 mL, 159.35 mmol). Stirred the mixture at room temperature for 1 h. Cooled to 0° C. and added slowly sodium borohydride (6.2 g, 163.88 mmol). Stirred the resulting mixture at room temperature for 16 h. The reaction was concentrated then the residue was redissolved in ethyl acetate (500 mL). The resulting solution was washed twice with saturated aqueous sodium bicarbonate solution (2×300 mL) and brine (1×500 mL) then dried over sodium sulfate. The solution was filtered and concentrated to give tert-butyl N-[2-(3,3-dimethylbutylamino)ethyl]carbamate (37.5 g, 96%) as an oil. ESI-MS m/z: 244.37, found 245.5 (M+1)$^+$; Retention time: 2.25 min (LC Method P).

Step 2: 1-(3,3-Dimethylbutyl)imidazolidin-2-one

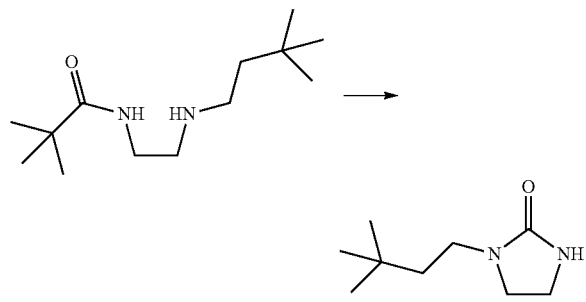

To tert-butyl N-[2-(3,3-dimethylbutylamino)ethyl]carbamate (15.8 g, 64.65 mmol) was added tetrahydrofuran (200 mL) in 1000 mL flask. Solid potassium tert-butoxide (21.77 g, 194.0 mmol) was added and the resulting yellow solution was heated to 60° C. for 3 h. The mixture was cooled to ambient temperature and acidified to pH=1-2 with aqueous hydrochloric acid (1 M) and concentrated under reduced pressure. The aqueous residue was extracted with ethyl acetate (2×200 mL), organic phase washed twice with brine (100 mL), dried over anhydrous sodium sulfate, filtered and concentrated under reduced pressure to give a beige solid which was purified by silica gel flash column chromatography (0% to 10% methanol in ethyl acetate) giving 1-(3,3-dimethylbutyl)imidazolidin-2-one (8.3 g, 72%) as a white solid. $^1$H NMR (300 MHz, dimethyl sulfoxide-d$_6$) ppm 0.89 (s, 9H), 1.26-1.37 (m, 2H), 2.97-3.09 (m, 2H), 3.14-3.22 (m, 2H), 3.24-3.32 (m, 2H), 6.12-6.32 (m, 1H). ESI-MS m/z calc. 170.252, found 171.2 (M+1)$^+$; Retention time: 2.17 min (LC Method H).

Step 3: tert-Butyl 4-[3-[[6-[(2,6-dichloropyridine-3-carbonyl)sulfamoyl]-2-pyridyl]amino]butyl]-2,2-dimethyl-pyrrolidine-1-carboxylate

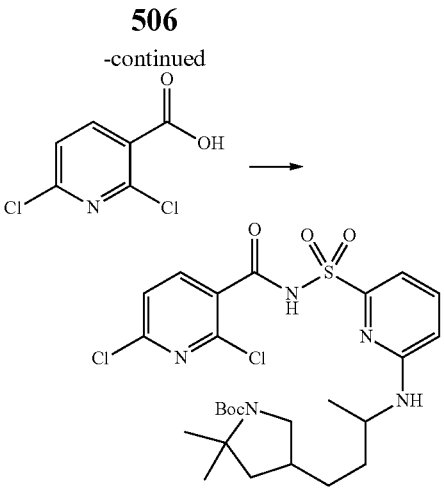

To a nitrogen purged 100 mL round bottom flask was charged under nitrogen with 2,6-dichloropyridine-3-carboxylic acid (220 mg, 1.146 mmol), carbonyl diimidazole (185 mg, 1.141 mmol) and anhydrous tetrahydrofuran (7 mL). The mixture was stirred under nitrogen at room temperature for 1 h. In a separate 100 mL flask, a solution of tert-butyl 2,2-dimethyl-4-[3-[(6-sulfamoyl-2-pyridyl)amino]butyl]pyrrolidine-1-carboxylate (485 mg, 1.137 mmol) in anhydrous tetrahydrofuran (3 mL) was prepared under nitrogen atmosphere and it was subsequently added via syringe into the activated ester solution. Added 1,8-diazabicyclo[5.4.0]undec-7-ene (373 µL, 2.494 mmol) through a syringe and the reaction mixture was stirred at room temperature under a nitrogen atmosphere for 6 h The solvents were removed under reduced pressure and the resulting thick oil was treated with aqueous citric acid. The two phases were separated. The aqueous phase was extracted with ethyl acetate (30 mL). The combined organic extracts were washed with brine (30 mL) and dried over sodium sulfate. After filtration and evaporation of the solvents, the residue was dissolved in dichloromethane and purified by silica gel chromatography using a gradient of ethyl acetate (0% to 100% over 30 min) in hexanes giving tert-butyl 4-[3-[[6-[(2,6-dichloropyridine-3-carbonyl)sulfamoyl]-2-pyridyl]amino]butyl]-2,2-dimethyl-pyrrolidine-1-carboxylate (412 mg, 60%) as a white solid foam mixture of diastereomers. ESI-MS m/z calc. 599.1736, found 600.21 (M+1)$^+$; Retention time: 0.77 min (LC Method A).

Step 4: 8-Chloro-12,12,17-trimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione

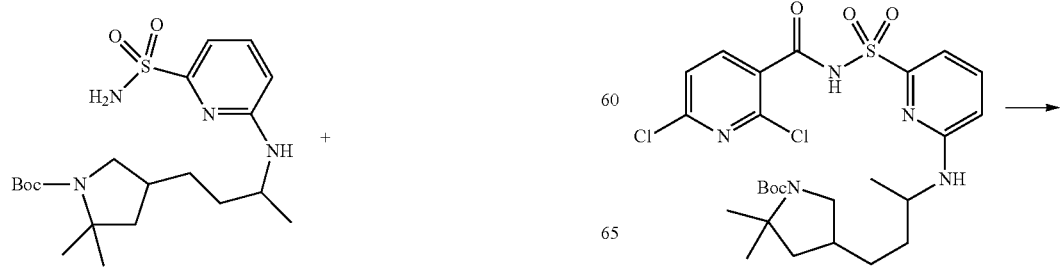

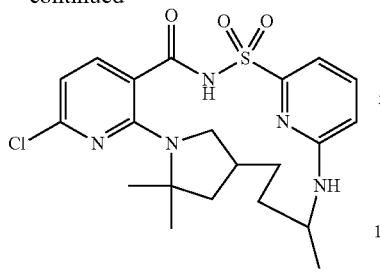

A solution of tert-butyl 4-[3-[[6-[(2,6-dichloropyridine-3-carbonyl)sulfamoyl]-2-pyridyl]amino]butyl]-2,2-dimethyl-pyrrolidine-1-carboxylate (412 mg, 0.6860 mmol) in dichloromethane (4 mL) and trifluoroacetic acid (0.55 mL, 7.187 mmol) was stirred at room temperature for 4 h. The solvents were removed and the residue was dissolved in ethyl acetate (100 mL). This solution was then washed with saturated sodium bicarbonate solution and water. The organic extract was concentrated and dried under vacuum. The resulting residue was dissolved in dimethyl sulfoxide (3 mL) and 3 Å molecular sieves were added and the reaction mixture was stirred for 10 min. Then, cesium fluoride (312.5 mg, 2.057 mmol) and potassium carbonate (288.4 mg, 2.087 mmol) were added and the reaction mixture was heated at 140° C. overnight. The reaction mixture was filtered and water was added to the filtrate. Extracted this solution with ethyl acetate and the organic extract was washed with brine, dried over anhydrous sodium sulfate and concentrated. The resultant brown residue was purified by silica gel column chromatography using a gradient from 100% dichloromethane to 50% dichloromethane/methanol to afford 8-chloro-12,12,17-trimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (98 mg, 31%). ESI-MS m/z calc. 463.1445, found 464.19 (M+1)$^+$; Retention time: 0.74 min (LC Method A).

Step 5: 8-[3-(3,3-Dimethylbutyl)-2-oxoimidazolidin-1-yl]-12,12,17-trimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer Pair 1) (Compound 209) and 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer Pair 2) (Compound 210)

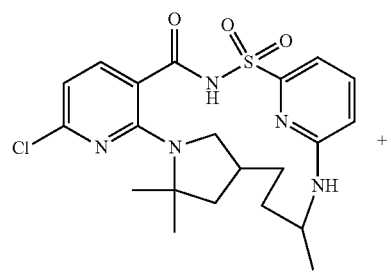

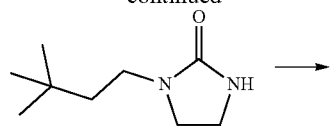

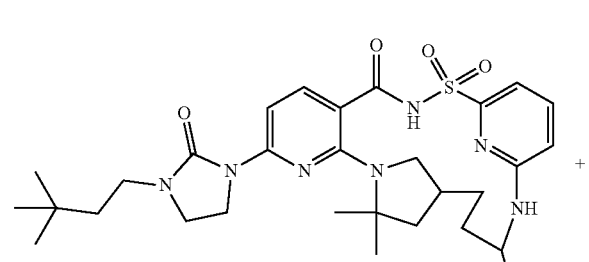

diastereomer pair 1

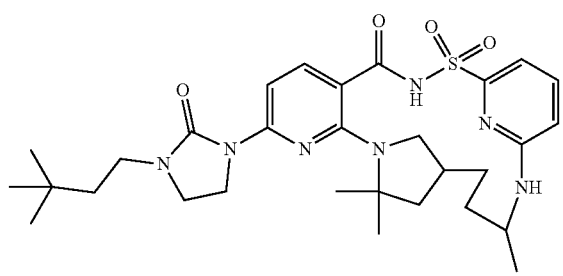

diastereomer pair 2

A 4 mL vial was charged with 8-chloro-12,12,17-trimethyl-2$\lambda^6$-thia-3,9,11,18,23-pentaazatetracyclo[17.3.1.1$^{11}$, 14.0$^{5,10}$]tetracosa-1(22),5,7,9,19(23),20-hexaene-2,2,4-trione (89 mg, 0.1918 mmol), 1-(3,3-dimethylbutyl)imidazolidin-2-one (46 mg, 0.2702 mmol), Pd$_2$(dba)$_3$ (46 mg, 0.05023 mmol), Xantphos (29 mg, 0.05012 mmol), cesium carbonate (314 mg, 0.9637 mmol) and anhydrous dioxane (3 mL). The mixture was sparged with nitrogen for 1-2 min, capped and stirred at 120° C. for 14 h. The solvent was evaporated, the reaction was diluted with dimethyl sulfoxide (900 µL), microfiltered and subjected to reverse phase preparative HPLC (C$_{18}$) using a gradient of acetonitrile in water (1 to 99% over 15 min) and hydrochloric acid as a modifier to afford as the first diastereomer pair to elute, 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (diastereomer pair 1) (Compound 209) (34 mg, 59%); ESI-MS m/z calc. 597.30975, found 598.36 (M+1)$^+$; Retention time: 2.04 min (LC Method B); and as the second diastereomer pair to elute, 8-[3-(3,3-dimethylbutyl)-2-oxoimidazolidin-1-yl]-12,12,17-trimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (diastereomer pair 2) (Compound 210) (63.5 mg, quantitative); ESI-MS m/z calc. 597.30975, found 598.36 (M+1)$^+$; Retention time: 2.07 min (LC Method B).

Step 6: 8-[3-(3,3-dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer Pair 1, Enantiomer 1) (Compound 215) and 8-[3-(3,3-dimethylbutyl)-2-oxoimidazolidin-1-yl]-12,12,1'7-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer Pair 1, Enantiomer 2) (Compound 216)

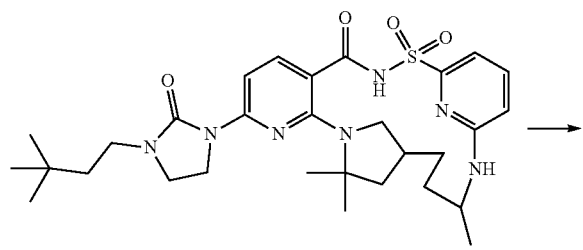

diastereomer pair 1

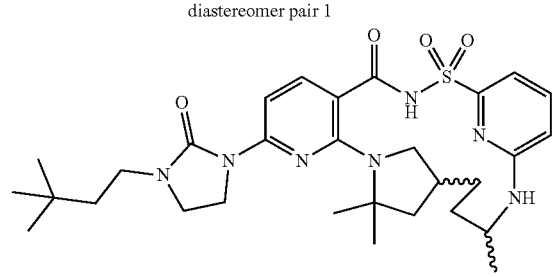

diastereomer pair 1, enantiomer 1

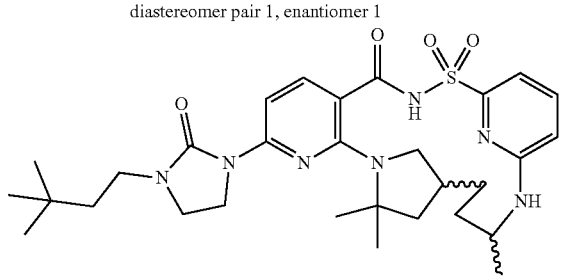

diastereomer pair 1, enantiomer 2

8-[3-(3,3-Dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer pair 1) (Compound 209) (31 mg, 0.05134 mmol) was subjected to chiral SFC chromatography. The following SFC protocol was employed: ChiralPak AS-3 (150×2.1 mm), 3 µm; 35° C. mobile phase: 30% acetonitrile:methanol (90:10), 70% carbon dioxide. The first enantiomer to elute was 8-[3-(3,3-dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer pair 1, enantiomer 1) (Compound 215) (8.1 mg, 52%). ESI-MS m/z calc. 597.30975, found 598.1 (M+1)⁺; Retention time: 2.06 min (LC Method B). The second enantiomer to elute was 8-[3-(3,3-dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer pair 1, enantiomer 2) (Compound 216) (9.1 mg, 58%). ¹H NMR (400 MHz, dimethyl sulfoxide-d₆) δ 12.39 (s, 1H), 7.57 (d, J=8.5 Hz, 1H), 7.38 (s, 1H), 7.10-6.82 (m, 2H), 6.68 (d, J=30.7 Hz, 1H), 4.17 (s, 1H), 4.03-3.79 (m, 2H), 3.46 (p, J=8.5, 7.9 Hz, 2H), 3.21 (dd, J=10.3, 6.1 Hz, 2H), 3.00 (s, 2H), 2.10 (s, 1H), 1.79 (d, J=10.2 Hz, 1H), 1.52 (d, J=50.3 Hz, 9H), 1.40 (t, J=8.1 Hz, 2H), 1.28 (d, J=40.1 Hz, 3H), 1.03 (d, J=6.3 Hz, 3H), 0.92 (s, 9H). ESI-MS m/z calc. 597.30975, found 598.2 (M+1)⁺; Retention time: 2.06 min (LC Method B).

Step 7: 8-[3-(3,3-dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer Pair 2, Enantiomer 1) (Compound 218) and 8-[3-(3,3-dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer Pair 2, Enantiomer 2) (Compound 219)

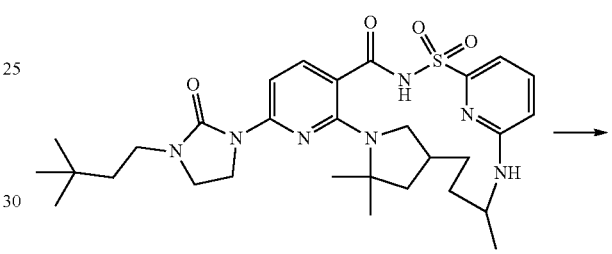

diastereomer pair 2

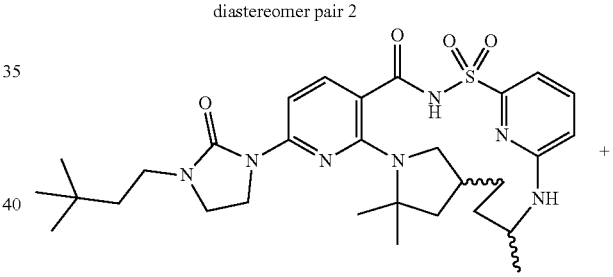

diastereomer pair 2, enantiomer 1

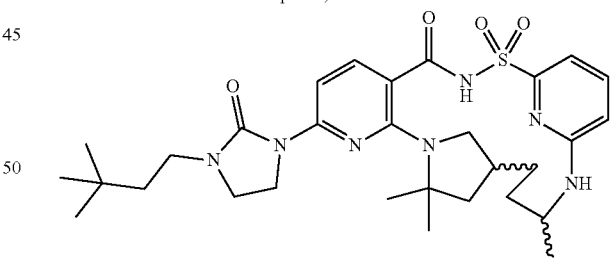

diastereomer pair 2, enantiomer 2

8-[3-(3,3-Dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer pair 2) (Compound 210) (60 mg) was subjected to chiral SFC chromatography. The following SFC protocol was employed: Phenomenex LUX-4 AS-H (250×10 mm), 5 µm; mobile phase: 42% methanol (no modifier), 58% carbon dioxide; 704 injection at 24 mg/mL in methanol at 10 mL/min. The first enantiomer to elute was 8-[3-(3,3-dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer pair 2, enantiomer 1) (Compound 218) (9 mg, 30%). ¹H NMR (400 MHz, dimethyl sulfoxide-d$_6$) δ 12.11 (s, 1H), 7.56 (t, J=7.8 Hz, 1H), 7.51-7.31 (m, 2H), 7.15 (d, J=7.3 Hz, 2H), 6.68 (d, J=8.5 Hz, 1H), 4.03-3.80 (m, 1H), 3.45 (t, J=8.3 Hz, 2H), 3.25-3.16 (m, 2H), 3.08 (s, 2H), 2.25 (d, J=21.1 Hz, 1H), 1.84 (dd, J=11.9, 5.8 Hz, 1H), 1.71 (s, 1H), 1.57 (s, 3H), 1.49 (s, 4H), 1.47-1.33 (m, 3H), 1.29-1.17 (m, 7H), 0.92 (s, 9H). ESI-MS m/z calc. 597.30975, found 598.36 (M+1)⁺; Retention time: 0.82 min (LC Method A). The second enantiomer to elute was 8-[3-(3,3-dimethylbutyl)-2-oxoimidazolidin-1-yl]-12,12,17-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer pair 2, enantiomer 2) (Compound 219) (14 mg, 46%). ESI-MS m/z calc. 597.30975, found 598.33 (M+1)⁺; Retention time: 2.11 min (LC Method B).

Example 59: Preparation of (14S)-8-{3-[(4,4-dimethylcyclohexyl)methyl]-2-oxoimidazolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 217)

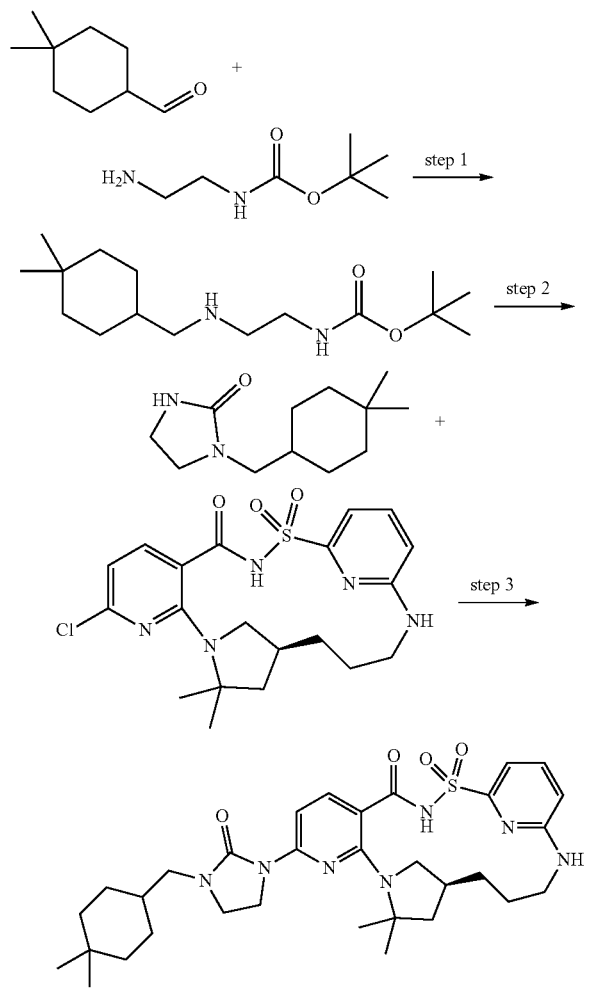

Step 1: tert-Butyl N-[2-[(4,4-dimethylcyclohexyl)methylamino]ethyl]carbamate

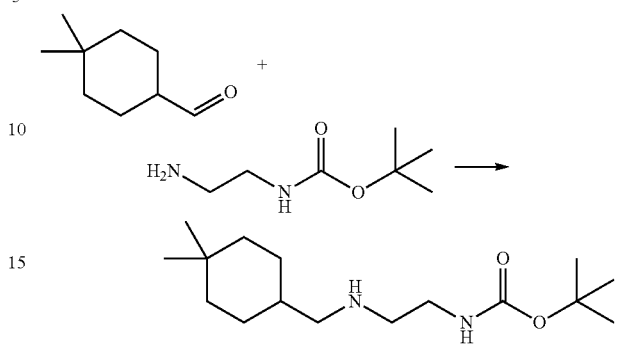

To a stirred solution of 4,4-dimethylcyclohexanecarbaldehyde (250 mg, 1.783 mmol) in anhydrous methanol (10 mL) was added a solution of tert-butyl N-(2-aminoethyl)carbamate (286 mg, 1.785 mmol) and anhydrous methanol (1 mL) under nitrogen. After the yellow solution was stirred at ambient temperature for 1 h, it was cooled to 0° C. (ice-water bath). Then sodium borohydride (142 mg, 3.753 mmol) was slowly added in two batches and the mixture was allowed to warm to ambient temperature and stirring continued for 15 h. The volatiles were removed under reduced pressure. The residue was dissolved in ethyl acetate (30 mL) and washed with saturated aqueous sodium bicarbonate solution (2×15 mL) and brine (15 mL), dried over sodium sulfate, filtered and concentrated under reduced pressure to furnish tert-butylN-[2-[(4,4-dimethylcyclohexyl)methylamino]ethyl]carbamate (481 mg, 95%) as a yellow gum. The crude material was used in the next step without further purification. ESI-MS m/z calc. 284.24637, found 285.3 (M+1)⁺; Retention time: 1.04 min (LC Method B).

Step 2: 1-[(4,4-Dimethylcyclohexyl)methyl]imidazolidin-2-one

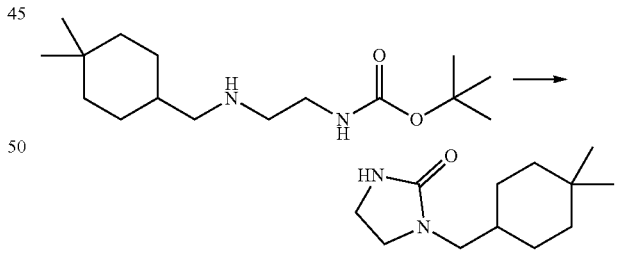

Solid potassium tert-butoxide (300 mg, 2.674 mmol) was added to a solution of tert-butyl N-[2-[(4,4-dimethylcyclohexyl)methylamino]ethyl]carbamate (240 mg, 0.8438 mmol) in anhydrous tetrahydrofuran (12 mL) under nitrogen and the reaction mixture was heated at 70° C. for 13 h. The heterogeneous mixture was allowed to cool to ambient temperature and acidified with hydrochloric acid (3.5 mL of 1.0 M, 3.500 mmol). The volatiles were removed under reduced pressure (not to dryness). The aqueous residue was extracted with ethyl acetate (3×10 mL) and the organic layers were combined, washed with brine (10 mL), dried over anhydrous sodium sulfate, filtered and concentrated under reduced pressure. The residue was purified by silica gel chromatography (gradient from 0-10% methanol in dichloromethane over 30 min) to afford 1-[(4,4-dimethylcyclohexyl)methyl]imidazolidin-2-one (62 mg, 35%) as an off-white solid. $^1$H NMR (400 MHz, Benzene-d$_6$) δ 5.42 (s, 1H), 3.10 (d, J=7.3 Hz, 2H), 2.84-2.77 (m, 2H), 2.77-2.71 (m, 2H), 1.58-1.52 (m, 2H), 1.46-1.42 (m, 2H), 1.38 (dq, J=10.7, 3.5 Hz, 1H), 1.27-1.20 (m, 2H), 1.19-1.12 (m, 2H), 1.00 (s, 3H), 0.92 (s, 3H). ESI-MS m/z calc. 210.17322, found 211.2 (M+1)$^+$; Retention time: 1.17 min (LC Method B).

Step 3: (14S)-8-{3-[(4,4-Dimethylcyclohexyl)methyl]-2-oxoimidazolidin-1-yl}-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 217)

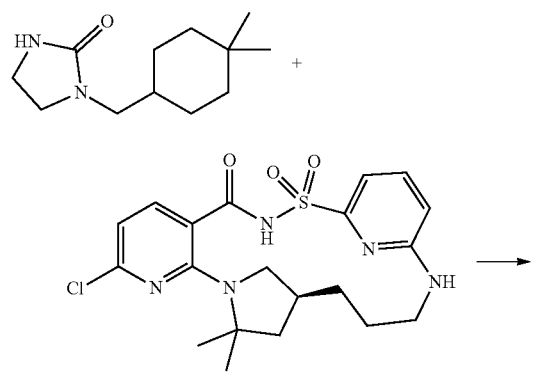

To a 4 mL vial was charged with (14S)-8-chloro-12,12-dimethyl-2λ$^6$-thia-3,9,11,18,23-pentaazatetracyclo[17.3.1.111,14.05,10]tetracosa-1(23),5,7,9,19,21-hexaene-2,2,4-trione (50 mg, 0.1111 mmol), 1-[(4,4-dimethylcyclohexyl)methyl]imidazolidin-2-one (26 mg, 0.1236 mmol), cesium carbonate (130 mg, 0.3990 mmol), 4,5-bis(diphenylphosphino)-9,9-dimethylxanthene (10 mg, 0.01728 mmol) (Xantphos) and anhydrous dioxane (1.5 mL), in that order. Nitrogen was purged through the heterogeneous mixture for 2 min. Then tris(dibenzylideneacetone)dipalladium(0) (10 mg, 0.01092 mmol) was added under nitrogen and nitrogen was purged through the mixture for another 2 min and the vial was capped under nitrogen. The mixture was stirred at 115° C. overnight. The mixture was allowed to cool to ambient temperature and neutralized with glacial acetic acid (60 µL, 1.055 mmol). The volatiles were removed under reduced pressure and the residue was taken up in dimethyl sulfoxide (1.5 mL) and filtered through a Whatman 0.45 µm PTFE syringe filter disc. The sample was purified using preparative reverse-phase HPLC-MS (Luna C$_{18}$ (2) column (75×30 mm, 5 µm particle size) sold by Phenomenex (pn: 00C-4252-U0-AX), dual gradient run from 30-99% acetonitrile in water over 15 min (hydrochloric acid as modifier)). The desired product fractions were combined and concentrated under reduced pressure and the residue was taken up in ethyl acetate (25 mL) and washed with brine (10 mL). The organic layer was dried over anhydrous sodium sulfate, filtered and concentrated under reduced pressure. giving (14S)-8-[3-[(4,4-dimethylcyclohexyl)methyl]-2-oxoimidazolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 217) (7.5 mg, 11%) as light yellowish solid. $^1$H NMR (400 MHz, Methanol-d$_4$) δ 7.70 (d, J=8.6 Hz, 1H), 7.52 (dd, J=8.5, 7.2 Hz, 1H), 7.43 (d, J=8.6 Hz, 1H), 7.15 (dd, J=7.2, 0.8 Hz, 1H), 6.65 (dd, J=8.5, 0.8 Hz, 1H), 4.10-4.07 (m, 1H), 4.07-4.02 (m, 1H), 4.02-3.95 (m, 1H), 3.56-3.52 (m, 1H), 3.51-3.47 (m, 1H), 3.23 (dd, J=10.2, 6.7 Hz, 1H), 3.18-3.09 (m, 2H), 3.07-2.98 (m, 1H), 2.86 (t, J=10.4 Hz, 1H), 2.21-2.07 (m, 1H), 1.83 (dd, J=11.7, 5.4 Hz, 2H), 1.64 (s, 3H), 1.63-1.55 (m, 5H), 1.55 (s, 3H), 1.48-1.35 (m, 3H), 1.31-1.27 (m, 2H), 1.22-1.16 (m, 3H), 0.91 (s, 6H). ESI-MS m/z calc. 623.3254, found 624.4 (M+1)$^+$; Retention time: 2.13 min (LC Method B).

Example 60: Preparation of 12,12-dimethyl-8-{3-[3-methyl-2-(propan-2-yl)butoxy]-1H-pyrazol-1-yl}-2λ$^6$-thia-3,9,11,18,23-pentaazatetracyclo[17.3.1.111,14.05,10]tetracosa-1(23),5(10),6,8,19,21-hexaene-2,2,4-trione (Compound 220)

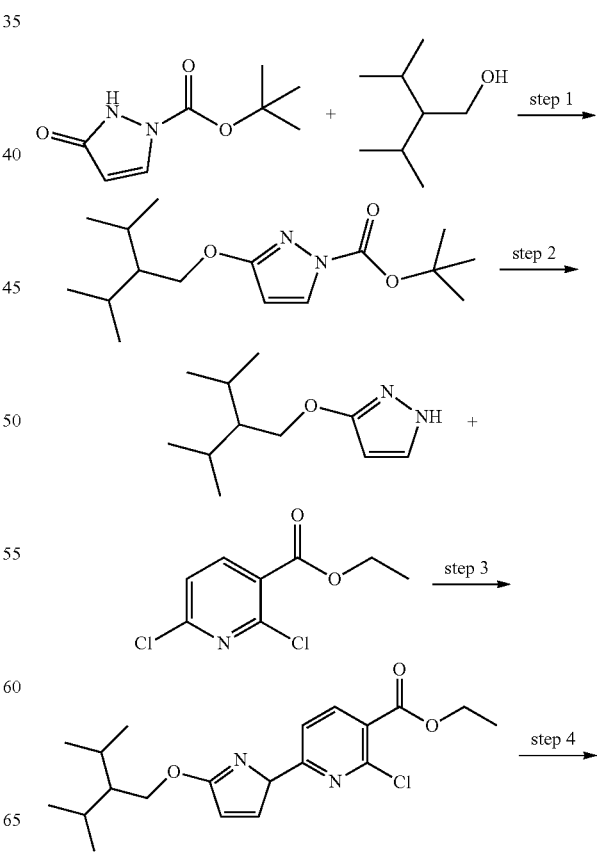

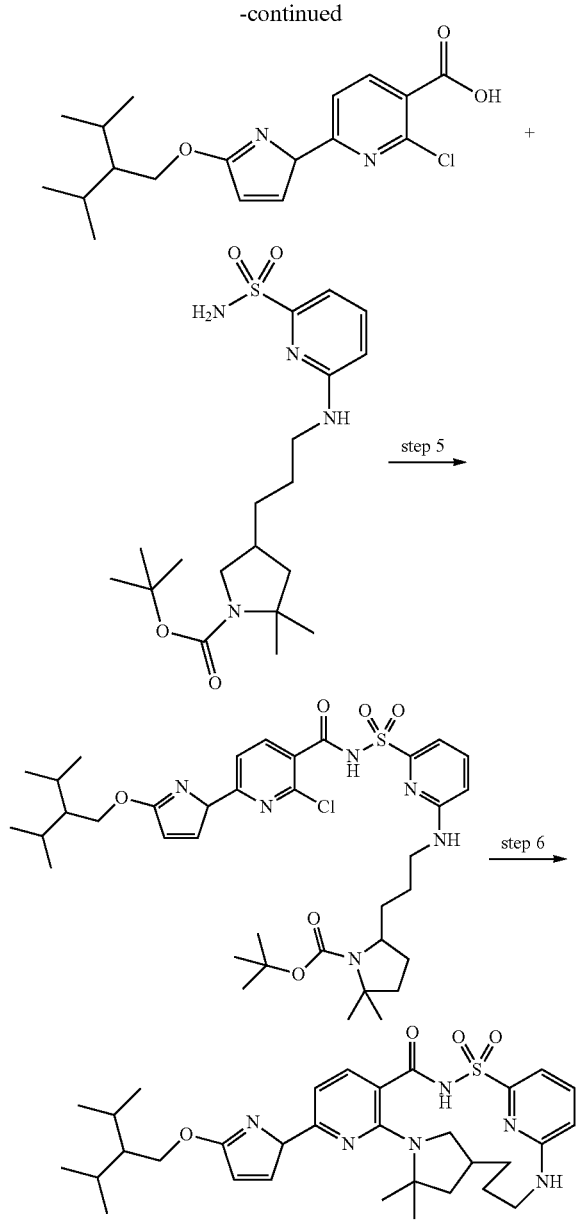

Step 1: tert-Butyl 3-(2-isopropyl-3-methyl-butoxy)pyrazole-1-carboxylate

A solution of 2-isopropyl-3-methyl-butan-1-ol (500 mg, 3.839 mmol), tert-butyl 3-hydroxypyrazole-1-carboxylate (705 mg, 3.828 mmol) and triphenylphosphine (1.16 g, 4.423 mmol) in dry tetrahydrofuran (20 mL) was cooled in an ice bath and DIAD (830 μL, 4.216 mmol) was slowly added under a nitrogen atmosphere. The reaction was allowed to slowly warm to room temperature and was stirred overnight. The reaction mixture was diluted with ethyl acetate, washed with saturated aqueous sodium bicarbonate, brine, dried over sodium sulfate, filtered and evaporated under vacuum. The residue was purified by silica gel chromatography with a 0-50% ethyl acetate in hexanes gradient to afford tert-butyl 3-(2-isopropyl-3-methyl-butoxy)pyrazole-1-carboxylate (980 mg, 86%) as a clear oil. $^1$H NMR (400 MHz, Chloroform-d) δ 7.82 (d, J=3.0 Hz, 1H), 5.84 (d, J=2.9 Hz, 1H), 4.29 (d, J=4.8 Hz, 2H), 1.91 (pd, J=6.9, 5.6 Hz, 2H), 1.61 (s, 9H), 1.44-1.24 (m, 1H), 0.98 (d, J=6.8 Hz, 6H), 0.92 (d, J=6.9 Hz, 6H). ESI-MS m/z calc. 296.21, found 297.21 (M+1)$^+$; Retention time: 0.84 min (LC Method A).

Step 2: 3-(2-Isopropyl-3-methyl-butoxy)-1H-pyrazole

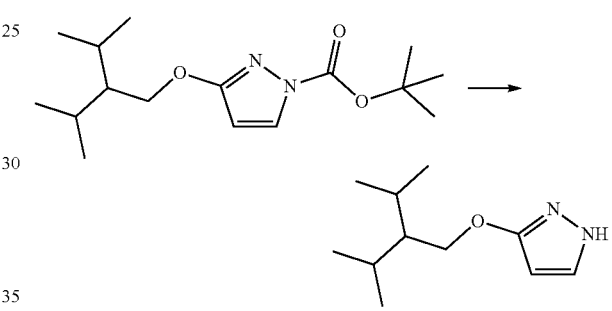

In a 250 mL round bottom flask was placed tert-butyl 3-(2-isopropyl-3-methyl-butoxy)pyrazole-1-carboxylate (980 mg, 3.306 mmol), dichloromethane (10 mL) and methyl alcohol (10 mL). To this clear solution was added hydrogen chloride in 1,4-dioxane (4.1 mL of 4 M, 16.40 mmol) via a syringe. The homogenous solution was stirred at 45° C. for 19 h. Two additional equivalents of 4 M hydrogen chloride in 1,4-dioxane was added and stirred for another hour. The volatiles were removed under reduced pressure. The residue was taken up in ethyl acetate (50 mL) and washed with aqueous 1 N sodium hydroxide. The layers were separated and the aqueous phase was extracted with ethyl acetate (20 mL). The combined organic extracts were washed with brine, dried over sodium sulfate and the solvents evaporated to give 3-(2-isopropyl-3-methyl-butoxy)-1H-pyrazole (490 mg, 76%) as a colorless oil. ESI-MS m/z calc. 196.15756, found 197.1 (M+1)$^+$; Retention time: 0.72 min (LC Method A).

Step 3: Ethyl 2-chloro-6-[3-(2-isopropyl-3-methyl-butoxy)pyrazol-1-yl]pyridine-3-carboxylate

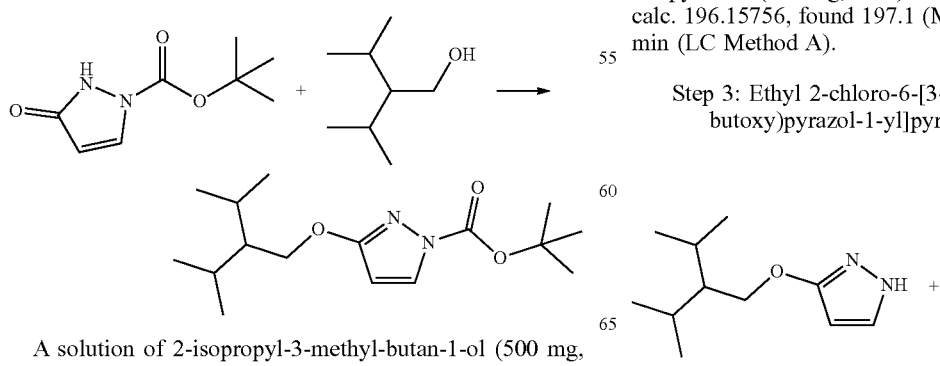

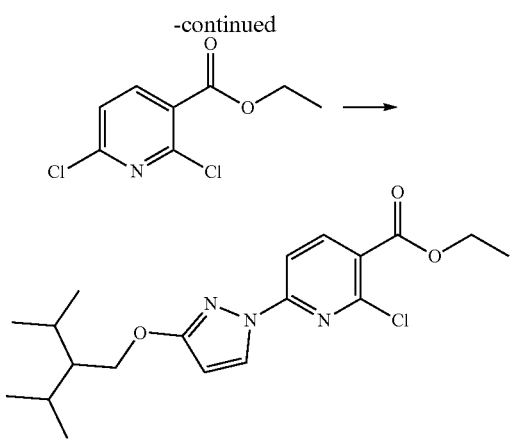

Ethyl 2,6-dichloropyridine-3-carboxylate (547 mg, 2.486 mmol), 3-(2-isopropyl-3-methyl-butoxy)-1H-pyrazole (488 mg, 2.486 mmol) and potassium carbonate (412 mg, 2.981 mmol) were combined in anhydrous dimethyl sulfoxide (6 mL). 1,4-Diazabicyclo[2.2.2]octane (56 mg, 0.4992 mmol) was added and the mixture was stirred at room temperature under nitrogen for 16 h. The reaction mixture was diluted with water (80 mL) and stirred for 15 min. The resulting white solid was collected by filtration and washed with water. The solid was dissolved in dichloromethane and dried over magnesium sulfate. The mixture was filtered and the filtrate evaporated to provide ethyl 2-chloro-6-[3-(2-isopropyl-3-methyl-butoxy)pyrazol-1-yl]pyridine-3-carboxylate (900 mg, 95%). $^1$H NMR (400 MHz, dimethyl sulfoxide-$d_6$) δ 8.42 (d, J=2.9 Hz, 1H), 8.39 (d, J=8.5 Hz, 1H), 7.76 (d, J=8.4 Hz, 1H), 6.20 (d, J=2.9 Hz, 1H), 4.34 (q, J=7.1 Hz, 2H), 4.26 (d, J=4.8 Hz, 2H), 2.02-1.76 (m, 2H), 1.45-1.29 (m, 4H), 0.98 (d, J=6.8 Hz, 6H), 0.92 (d, J=6.8 Hz, 6H). ESI-MS m/z calc. 379.16626, found 380.21 (M+1)$^+$; Retention time: 2.56 min (LC Method B).

Step 4: 2-Chloro-6-[3-(2-isopropyl-3-methyl-butoxy)pyrazol-1-yl]pyridine-3-carboxylic Acid

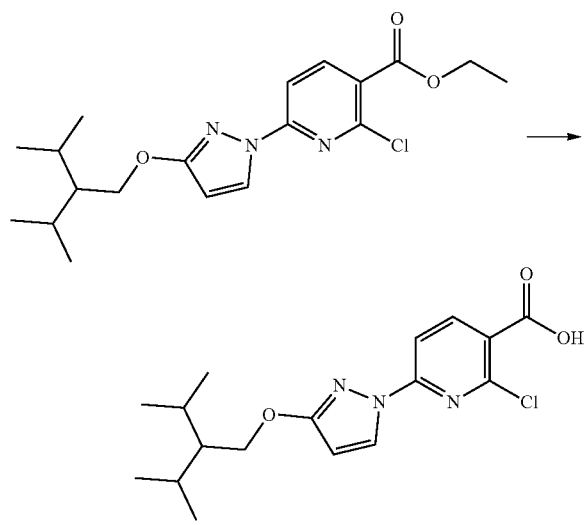

To a round bottom flask was added ethyl 2-chloro-6-[3-(2-isopropyl-3-methyl-butoxy)pyrazol-1-yl]pyridine-3-carboxylate (900 mg, 2.369 mmol), tetrahydrofuran (6 mL) and aqueous sodium hydroxide (1.4 mL of 5 M, 7.000 mmol). The reaction solution was allowed to stir for 4 h at room temperature. The reaction solution was diluted with ethyl acetate (100 mL) and aqueous hydrochloric acid (12 mL of 1 M, 12.00 mmol) was added. The phases were separated and the aqueous was extracted with ethyl acetate (2×30 mL). The combined organic phases were dried over sodium sulfate, filtered and concentrated in vacuo to afford 2-chloro-6-[3-(2-isopropyl-3-methyl-butoxy)pyrazol-1-yl]pyridine-3-carboxylic acid (655 mg, 79%) which was used without further purification. ESI-MS m/z calc. 351.13498, found 352.19 (M+1)$^+$; Retention time: 0.87 min (LC Method A).

Step 5: tert-Butyl 5-[3-[[6-[[2-chloro-6-[3-(2-isopropyl-3-methyl-butoxy)pyrazol-1-yl]pyridine-3-carbonyl]sulfamoyl]-2-pyridyl]amino]propyl]-2,2-dimethyl-pyrrolidine-1-carboxylate

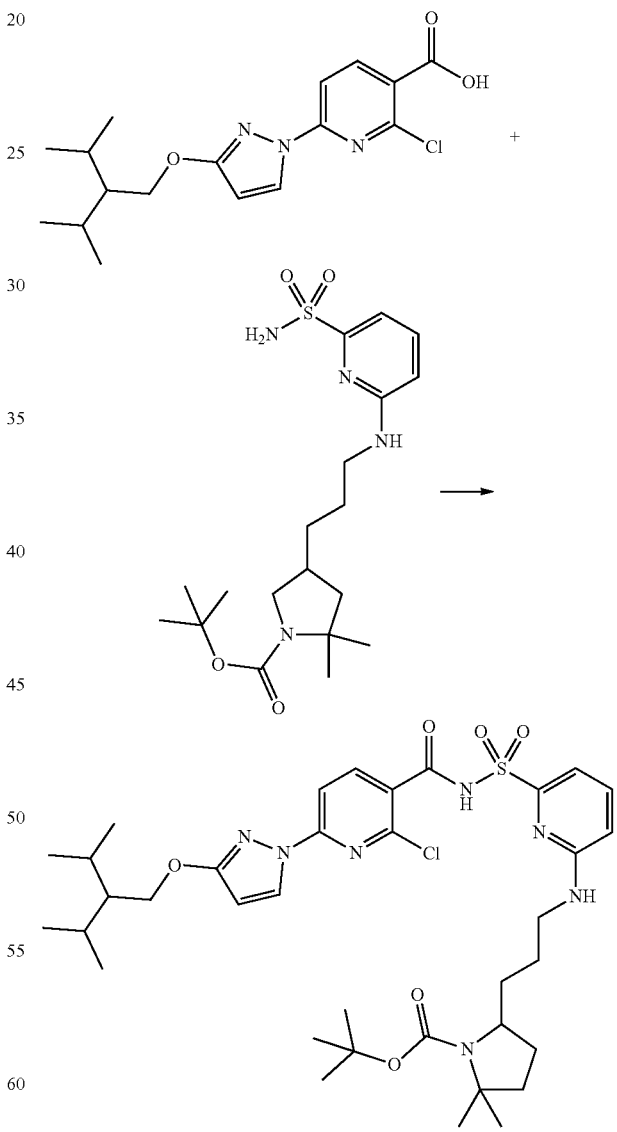

2-Chloro-6-[3-(2-isopropyl-3-methyl-butoxy)pyrazol-1-yl]pyridine-3-carboxylic acid (170 mg, 0.4832 mmol) and carbonyl diimidazole (81 mg, 0.4995 mmol) were combined in anhydrous tetrahydrofuran (4 mL) and stirred for 75 min at 40° C. Then a tetrahydrofuran solution (7 mL) of tert-butyl 2,2-dimethyl-4-[3-[(6-sulfamoyl-2-pyridyl)amino]propyl]pyrrolidine-1-carboxylate (165 mg, 0.400 mmol) and 1,8-diazabicyclo[5.4.0]undec-7-ene (152 µL, 1.016 mmol) was added. The reaction was heated at 50° C. for 4 h. The reaction was diluted with ethyl acetate and washed with a 1 M aqueous citric acid solution, followed by brine. The organic layer was dried over sodium sulfate, filtered and evaporated and then purified on silica gel chromatography using a gradient of 100% hexanes to 75% ethyl acetate in hexanes to afford as an off-white solid, tert-butyl 5-[3-[[6-[[2-chloro-6-[3-(2-isopropyl-3-methyl-butoxy)pyrazol-1-yl]pyridine-3-carbonyl]sulfamoyl]-2-pyridyl]amino]propyl]-2,2-dimethyl-pyrrolidine-1-carboxylate (200 mg, 67%). ESI-MS m/z calc. 745.3388, found 746.3 (M+1)+; Retention time: 0.87 min (LC Method K).

Step 6: 12,12-Dimethyl-8-{3-[3-methyl-2-(propan-2-yl)butoxy]-1H-pyrazol-1-yl}-2λ⁶-thia-3,9,11,18,23-pentaazatetracyclo[17.3.1.111,14.05,10]tetracosa-1(23),5(10),6,8,19,21-hexaene-2,2,4-trione (Compound 220)

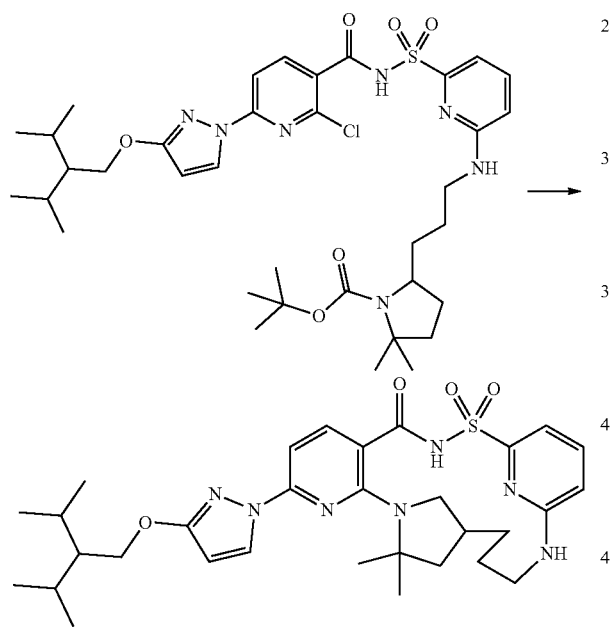

tert-Butyl 5-[3-[[6-[[2-chloro-6-[3-(2-isopropyl-3-methyl-butoxy)pyrazol-1-yl]pyridine-3-carbonyl]sulfamoyl]-2-pyridyl]amino]propyl]-2,2-dimethyl-pyrrolidine-1-carboxylate (200 mg, 0.2680 mmol) was dissolved in dichloromethane (3.5 mL) and to the mixture was added hydrochloric acid (4 mL of 4 M in dioxane, 16.00 mmol). The mixture was stirred at room temperature for 2 h. The reaction mixture was concentrated to dryness under reduced pressure to a residue. Combined this residue and potassium carbonate (223 mg, 1.614 mmol), cesium fluoride (66 mg, 0.4345 mmol), 3 Å molecular sieves and dimethyl sulfoxide (3.2 mL) in a vial, purged with nitrogen, capped, heated to 140° C. and stirred for 16 h. The reaction mixture was allowed to cool to room temperature, filtered and then purified by reverse-phase preparative chromatography ($C_{18}$ column, 30% to 99% acetonitrile (no modifier) in water (5 mM hydrochloric acid) over 30 min) gradient to afford as a white solid, 12,12-dimethyl-8-{3-[3-methyl-2-(propan-2-yl)butoxy]-1H-pyrazol-1-yl}-2λ⁶-thia-3,9,11,18,23-pentaazatetracyclo[17.3.1.111,14.05,10]tetracosa-1(23),5(10),6,8,19,21-hexaene-2,2,4-trione (Compound 220) (65 mg, 39%). ESI-MS m/z calc. 609.30975, found 610.47 (M+1)+; Retention time: 2.52 min (LC Method B).

Example 61: Preparation of (18S)-20,20-dimethyl-4-[3-(4,4,4-trifluoro-3,3-dimethylbutoxy)-1H-pyrazol-1-yl]-10λ⁶-thia-1,3,9,14,22-pentaazatetracyclo[16.2.1.111,14.02,7]docosa-2,4,6,11(22),12-pentaene-8,10,10-trione (Compound 221)

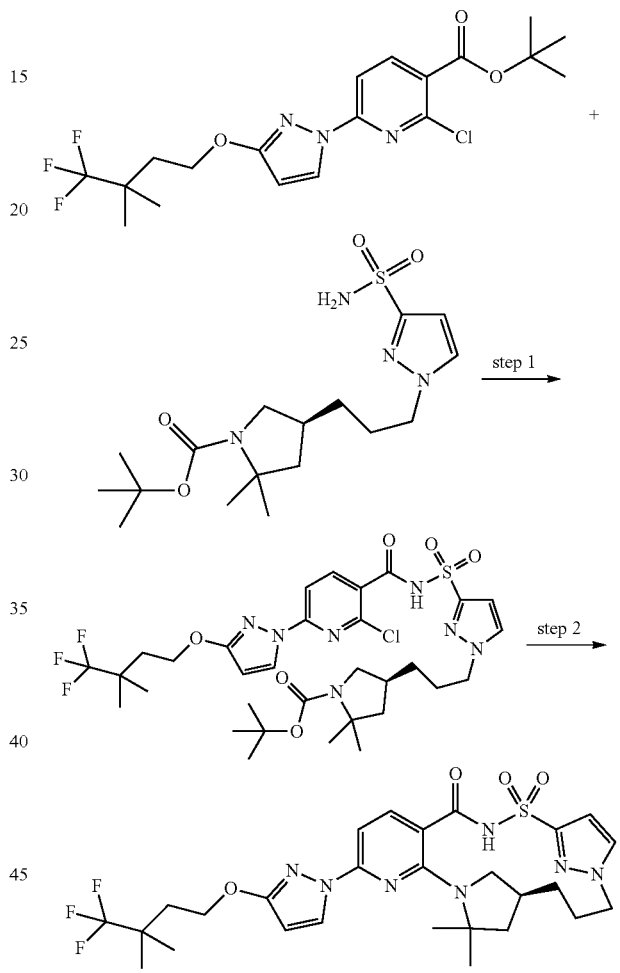

Step 1: tert-Butyl (4S)-4-[3-[3-[[2-chloro-6-[3-(4,4,4-trifluoro-3,3-dimethyl-butoxy)pyrazol-1-yl]pyridine-3-carbonyl]sulfamoyl]pyrazol-1-yl]propyl]-2,2-dimethyl-pyrrolidine-1-carboxylate

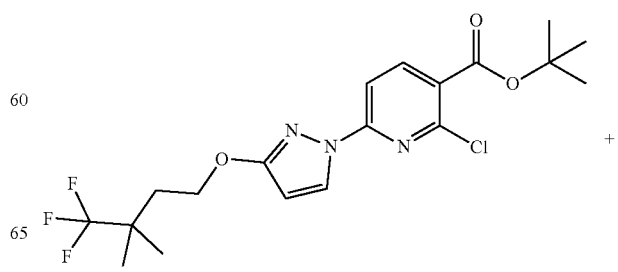

521

-continued

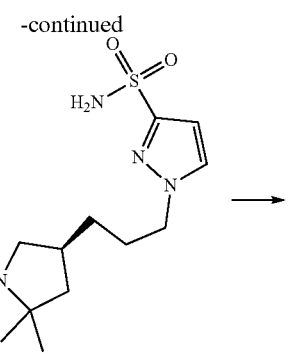

tert-Butyl 2-chloro-6-[3-(4,4,4-trifluoro-3,3-dimethyl-butoxy)pyrazol-1-yl]pyridine-3-carboxylate (150 mg, 0.3457 mmol) in a solution of trifluoroacetic acid (150 µL, 1.947 mmol) in dichloromethane (400 µL) was stirred at room temperature for 2 h. The solvent was removed and the residue dried under vacuum. This material was dissolved in tetrahydrofuran (2 mL) and carbonyl diimidazole (69 mg, 0.4255 mmol) was added and the reaction mixture was stirred for 4 h at room temperature. Then tert-butyl (4S)-2,2-dimethyl-4-[3-(3-sulfamoylpyrazol-1-yl) propyl]pyrrolidine-1-carboxylate (136 mg, 0.3519 mmol) in tetrahydrofuran (2 mL) was added followed by 1,8-diazabicyclo[5.4.0] undec-7-ene (110 µL, 0.7356 mmol) and the reaction was stirred for 16 h. The reaction was diluted with ethyl acetate and washed with a mixture of saturated ammonium chloride/brine (1:1). The organic layer was separated, dried over sodium sulfate, filtered and evaporated. The resultant brown residue was purified by silica gel chromatography using a shallow gradient from 100% dichloromethane to 20% methanol/dichloromethane to afford tert-butyl (4S)-4-[3-[3-[[2-chloro-6-[3-(4,4,4-trifluoro-3,3-dimethyl-butoxy)pyrazol-1-yl]pyridine-3-carbonyl]sulfamoyl]pyrazol-1-yl]propyl]-2,2-dimethyl-pyrrolidine-1-carboxylate (82 mg, 32%) as a white solid. ESI-MS m/z calc. 745.2636, found 746.14 (M+1)$^+$; Retention time: 0.87 min (LC Method A).

522

Step 2: (18S)-20,20-Dimethyl-4-[3-(4,4,4-trifluoro-3,3-dimethylbutoxy)-1H-pyrazol-1-yl]-10$\lambda^6$-thia-1,3,9,14,22-pentaazatetracyclo[16.2.1.1$^{11,14}$.0$^{2,7}$]docosa-2,4,6,11(22),12-pentaene-8,10,10-trione (Compound 221)

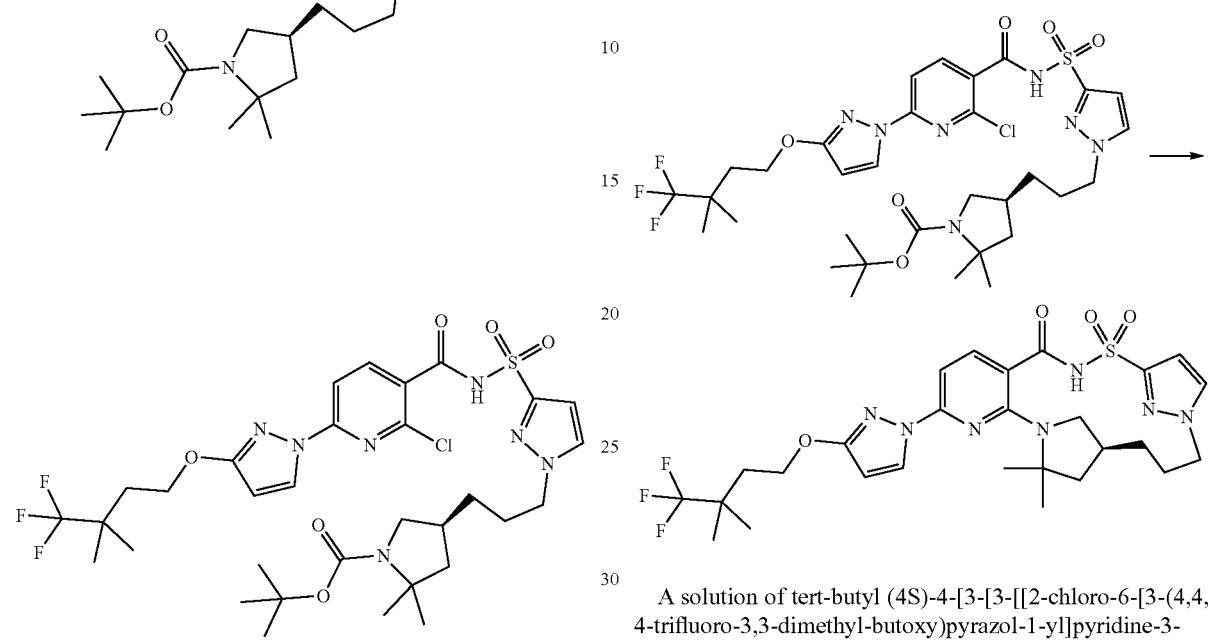

A solution of tert-butyl (4S)-4-[3-[3-[[2-chloro-6-[3-(4,4,4-trifluoro-3,3-dimethyl-butoxy)pyrazol-1-yl]pyridine-3-carbonyl]sulfamoyl]pyrazol-1-yl]propyl]-2,2-dimethyl-pyrrolidine-1-carboxylate (82 mg, 0.1099 mmol) in dichloromethane (400 µL) and trifluoroacetic acid (100 µL, 1.307 mmol) was stirred at room temperature for 2 h. After completion of the reaction, the solvents were evaporated under reduced pressure. The residue was dissolved in ethyl acetate and washed with saturated sodium bicarbonate solution (2 mL) and the organic layer was collected and solvent evaporated. The resulting residue was dissolved in dimethyl sulfoxide (5 mL) and 3 Å molecular sieves were added and the reaction mixture was stirred for 10 min. Then, cesium fluoride (54 mg, 0.3555 mmol) and potassium carbonate (48 mg, 0.3473 mmol) were added and the reaction mixture was heated at 130° C. overnight. The reaction mixture was filtered through Whatman filter disc (puradisc 25 TF) and filtrate was purified by a reverse phase HPLC-MS using a dual gradient run from 50-99% mobile phase B over 15.0 min (mobile phase A=water (0.05% hydrochloric acid), mobile phase B=acetonitrile) to afford (18S)-20,20-dimethyl-4-[3-(4,4,4-trifluoro-3,3-dimethylbutoxy)-1H-pyrazol-1-yl]-10$\lambda^6$-thia-1,3,9,14,22-pentaazatetracyclo[16.2.1.1$^{11,14}$.0$^{2,7}$]docosa-2,4,6,11(22),12-pentaene-8,10,10-trione (Compound 221) (14.3 mg, 21%) as a white solid. $^1$H NMR (400 MHz, Chloroform-d) δ 8.40 (s, 1H), 8.18 (d, J=2.8 Hz, 1H), 7.68 (d, J=8.2 Hz, 1H), 7.48 (d, J=2.3 Hz, 1H), 7.07 (d, J=2.3 Hz, 1H), 7.02 (d, J=8.3 Hz, 1H), 5.87 (d, J=2.7 Hz, 1H), 4.36 (q, J=7.0 Hz, 3H), 3.94 (t, J=12.0 Hz, 1H), 2.74 (t, J=8.2 Hz, 1H), 2.14 (s, 2H), 2.02 (t, J=7.2 Hz, 3H), 1.76 (dd, J=11.8, 5.2 Hz, 1H), 1.59 (s, 5H), 1.55 (s, 3H), 1.47 (t, J=12.1 Hz, 1H), 1.24-1.21 (m, 6H), 0.90-0.73 (m, 1H). ESI-MS m/z calc. 609.2345, found 610.07 (M+1)$^+$; Retention time: 2.17 min (LC Method B).

Example 62: Preparation of (14S)-12,12-dimethyl-8-[2-oxo-3-(4,4,4-trifluoro-3,3-dimethylbutyl)imidazolidin-1-yl]-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 223)

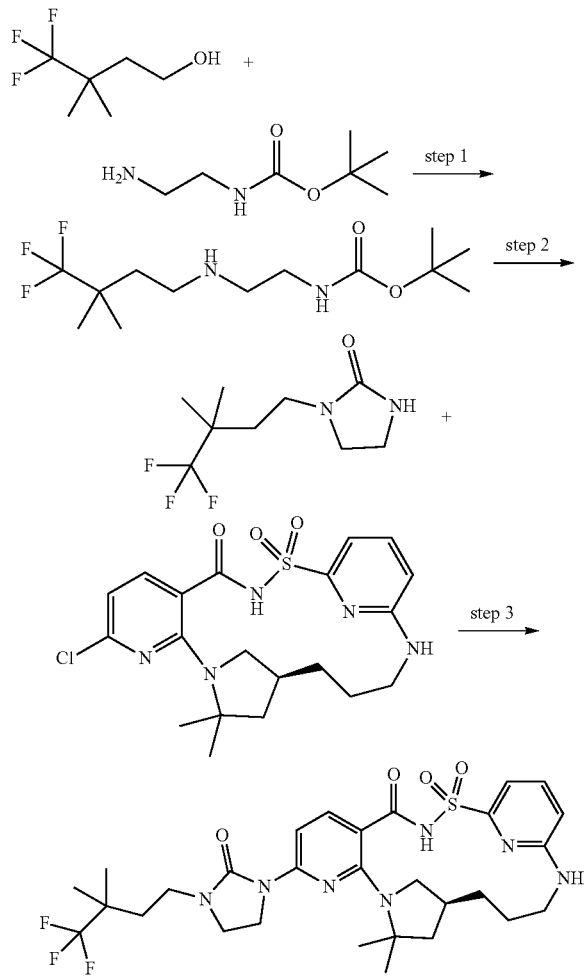

Step 1: tert-Butyl N-[2-[(4,4,4-trifluoro-3,3-dimethyl-butyl)amino]ethyl]carbamate

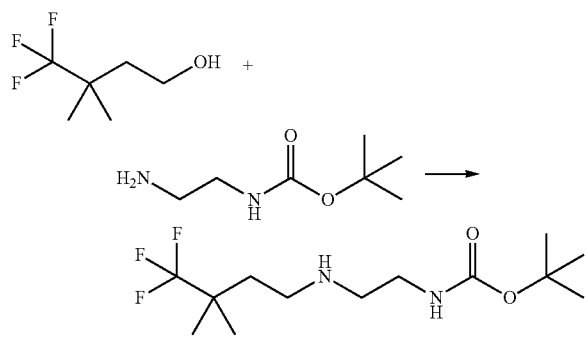

Dess-Martin periodinane (660 mg, 1.556 mmol) was added to a stirred solution of 4,4,4-trifluoro-3,3-dimethyl-butan-1-ol (210 mg, 1.345 mmol) in anhydrous methylene chloride (7 mL) at 0° C. (ice-water bath) under nitrogen. After 15 min, the bath was removed and the reaction was allowed to warm to ambient temperature and stirring continued for another 2 h. The reaction was diluted with ether (60 mL) and saturated aqueous sodium bicarbonate (20 mL) was added slowly (observed carbon dioxide gas evolution). Then sodium thiosulfate (10 mL) was added and stirred at ambient temperature for 30 min. The layers were separated and the aqueous layer was extracted with ether (2×20 mL). The combined organics were washed with brine (20 mL), dried over anhydrous sodium sulfate, filtered and partially concentrated under reduced pressure (to about 2 mL volume) to obtain the intermediate aldehyde as a crude solution. Next, to a stirred solution of tert-butyl N-(2-aminoethyl) carbamate (216 mg, 1.348 mmol) in anhydrous methanol (7 mL) was added the previously obtained ethereal solution of intermediate aldehyde in anhydrous methanol (1 mL) under nitrogen. After the yellow solution was stirred at ambient temperature for 1 h, it was cooled to 0° C. (ice-water bath). Then sodium borohydride (110 mg, 2.908 mmol) was added slowly in two batches and the mixture was allowed to warm to ambient temperature and stirring was continued for 15 h. The volatiles were removed under reduced pressure. The residue was dissolved in ethyl acetate (30 mL) and washed with saturated aqueous sodium bicarbonate solution (2×15 mL) and brine (15 mL), dried over sodium sulfate, filtered and concentrated under reduced pressure to furnish tert-butyl N-[2-[(4,4,4-trifluoro-3,3-dimethyl-butyl)amino]ethyl]carbamate (380 mg, 95%) as clear viscous oil. ESI-MS m/z calc. 298.1868, found 299.2 (M+1)⁺; Retention time: 0.82 min (LC Method B).

Step 2: 1-(4,4,4-Trifluoro-3,3-dimethyl-butyl)imidazolidin-2-one

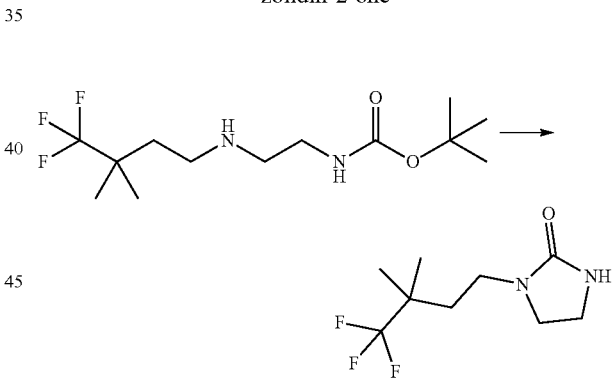

Solid potassium tert-butoxide (440 mg, 3.921 mmol) was added to a stirred solution of tert-butyl N-[2-[(4,4,4-trifluoro-3,3-dimethyl-butyl)amino]ethyl]carbamate (380 mg, 1.274 mmol) in anhydrous tetrahydrofuran (12 mL) under nitrogen and the reaction mixture was heated at 70° C. for 13 h. The heterogeneous mixture was allowed to cool to ambient temperature and was acidified with aqueous hydrochloric acid (5.0 mL of 1.0 M, 5.000 mmol) and the volatiles were removed under reduced pressure. The aqueous residue was extracted with ethyl acetate (3×10 mL) and the combined organics were washed with brine (10 mL), dried over anhydrous sodium sulfate, filtered and concentrated under reduced pressure. The residue was purified by silica gel chromatography (0-10% methanol in dichloromethane gradient over 30 min) to afford 1-(4,4,4-trifluoro-3,3-dimethyl-butyl)imidazolidin-2-one (172 mg, 60%) as an off-white solid. ¹H NMR (400 MHz, Benzene-d₆) δ 5.50 (s, 1H), 3.23-3.12 (m, 2H), 2.71-2.66 (m, 2H), 2.65-2.59 (m, 2H), 1.64-1.53 (m, 2H), 1.01 (s, 6H). $^{19}$F NMR (376 MHz, Methanol-$d_4$) δ −79.87. ESI-MS m/z calc. 224.11365, found 225.1 (M+1)$^+$; Retention time: 1.08 min (LC Method B).

Step 3: (14S)-12,12-Dimethyl-8-[2-oxo-3-(4,4,4-trifluoro-3,3-dimethylbutyl) imidazolidin-1-yl]-2λ$^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 223)

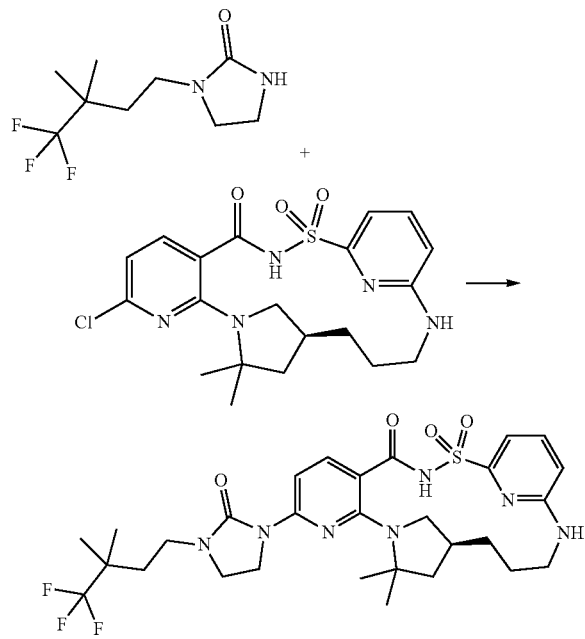

To a 4 mL vial, (14S)-8-chloro-12,12-dimethyl-2λ$^6$-thia-3,9,11,18,23-pentaazatetracyclo[17.3.1.1¹¹,¹⁴.0⁵,¹⁰]tetracosa-1(23),5,7,9,19,21-hexaene-2,2,4-trione (51 mg, 0.1133 mmol), 1-(4,4,4-trifluoro-3,3-dimethyl-butyl)imidazolidin-2-one (31 mg, 0.1383 mmol), cesium carbonate (130 mg, 0.3990 mmol), 4,5-bis(diphenylphosphino)-9,9-dimethyl-xanthene (10 mg, 0.01728 mmol) and anhydrous dioxane (1.5 mL) were added in that order. Nitrogen was bubbled through the heterogeneous mixture for 2 min. Then tris (benzylideneacetone)dipalladium(0) (10 mg, 0.01092 mmol) was added under nitrogen and nitrogen was bubbled for another 2 min and the reaction was capped under nitrogen. The mixture was stirred at 115° C. overnight. The mixture was allowed to cool to ambient temperature and neutralized with glacial acetic acid (50 μL, 0.8792 mmol). The volatiles were removed under reduced pressure and the residue was taken up in dimethyl sulfoxide (1.2 mL), filtered through a Whatman 0.45 μm PTFE syringe filter disc. The sample was purified using preparative reverse-phase HPLC [Luna C$_{18}$ (2) column (75×30 mm, 5 μm particle size) sold by Phenomenex (pn: 00C-4252-U0-AX), (dual gradient run from 30-99% acetonitrile in water over 15 min (hydrochloric acid as modifier)]. The desired product fractions were combined and concentrated under reduced pressure and the residue was taken up in ethyl acetate (25 mL) and washed with brine (10 mL). The organic layer was dried over anhydrous sodium sulfate, filtered and concentrated under reduced pressure to obtain (14S)-12,12-dimethyl-8-[2-oxo-3-(4,4,4-trifluoro-3,3-dimethylbutyl)imidazolidin-1-yl]-2λ$^6$-thia-3,9,11,18,23-pentaazatetracyclo[17.3.1.1¹¹,¹⁴.05,10]tetracosa-1(22),5,7,9,19(23),20-hexaene-2,2,4-trione (Compound 223) (37 mg, 51%) as yellowish solid. $^1$H NMR (400 MHz, Methanol-$d_4$) δ 7.70 (d, J=8.6 Hz, 1H), 7.52 (dd, J=8.5, 7.2 Hz, 1H), 7.44 (d, J=8.6 Hz, 1H), 7.15 (dd, J=7.2, 0.8 Hz, 1H), 6.65 (dd, J=8.5, 0.8 Hz, 1H), 4.10-4.07 (m, 1H), 4.07-4.01 (m, 1H), 4.01-3.95 (m, 1H), 3.58-3.46 (m, 2H), 3.42-3.34 (m, 2H), 3.23 (t, J=8.6 Hz, 1H), 3.08-2.97 (m, 1H), 2.85 (t, J=10.4 Hz, 1H), 2.22-2.07 (m, 1H), 1.89-1.73 (m, 4H), 1.71-1.64 (m, 1H), 1.63 (s, 3H), 1.62-1.55 (m, 2H), 1.54 (s, 3H), 1.47-1.35 (m, 1H), 1.19 (s, 6H). ESI-MS m/z calc. 637.2658, found 638.5 (M+1)$^+$; Retention time: 1.9 min (LC Method B).

Example 63: Preparation of (14S)-8-[3-fluoro-5-(2-methylpropoxy)phenyl]-12,12-dimethyl-2λ$^6$-thia-3,9,11,18,23-pentaazatetracyclo[17.3.1.1¹¹,¹⁴.05,10]tetracosa-1(22),5,7,9,19(23),20-hexaene-2,2,4-trione (Compound 224)

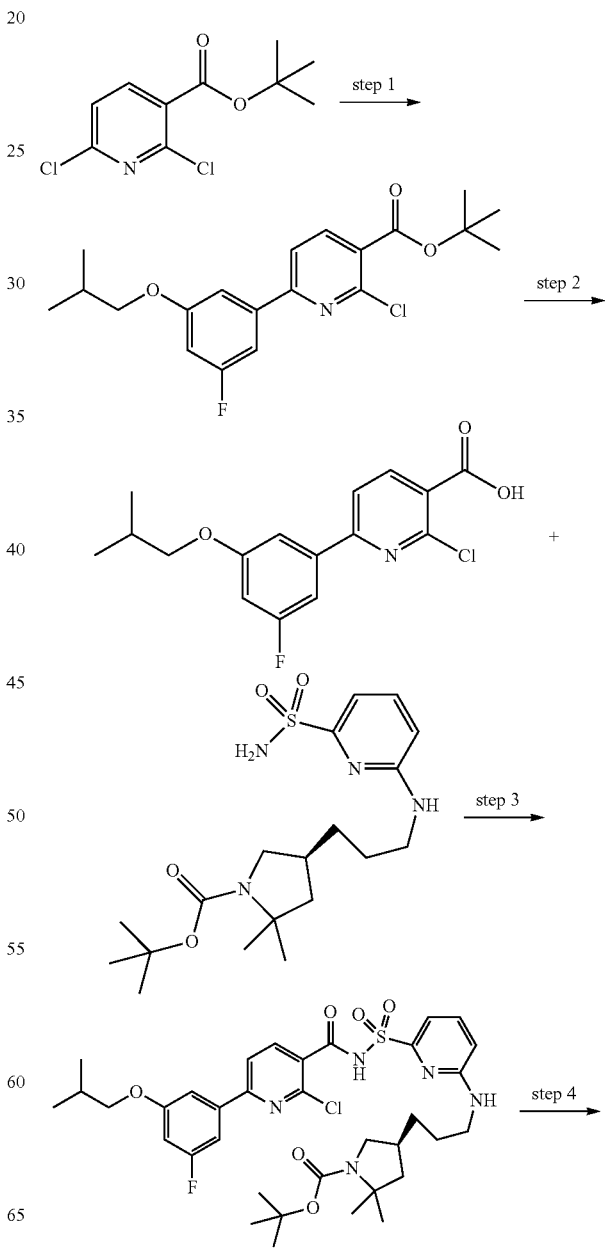

527

-continued

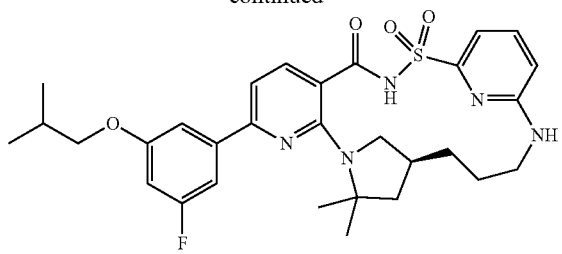

Step 1: tert-Butyl 2-chloro-6-(3-fluoro-5-isobutoxy-phenyl)pyridine-3-carboxylate

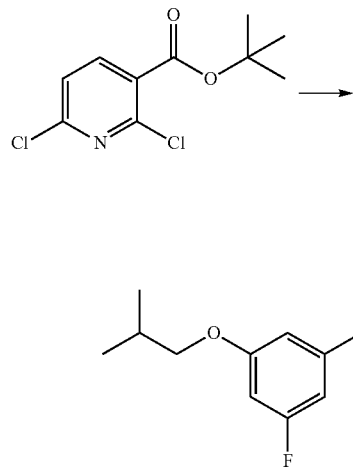

tert-Butyl 2,6-dichloropyridine-3-carboxylate (15.0 g, 60.5 mmol) and (3-fluoro-5-isobutoxy-phenyl)boronic acid (13.46 g, 63.48 mmol) were combined and fully dissolved in ethanol (150 mL) and toluene (150 mL). A suspension of sodium carbonate (19.23 g, 181.4 mmol) in water (30 mL) was added. Tetrakis(triphenylphosphine)palladium(0) (2.096 g, 1.814 mmol) was added under nitrogen. The reaction mixture was allowed to stir at 60° C. for 16 h. Volatiles were removed under reduced pressure. The remaining solids were partitioned between water (100 mL) and ethyl acetate (100 mL). The organic layer was washed with brine (1×100 mL), dried over sodium sulfate, filtered and concentrated under reduced pressure. The material was subjected to silica gel column chromatography (0% to 20% ethyl acetate in hexanes gradient). The material was repurified by silica gel chromatography (isocratic 100% hexane for 10 min, then a 0 to 5% ethyl acetate in hexanes gradient) to yield tert-butyl 2-chloro-6-(3-fluoro-5-isobutoxy-phenyl)pyridine-3-carboxylate (18.87 g, 49.68 mmol, 82%), obtained as a colorless oil. $^1$H NMR (400 MHz, dimethyl sulfoxide-$d_6$) δ 8.24 (d, J=8.0 Hz, 1H), 8.16 (d, J=8.1 Hz, 1H), 7.48 (dd, J=9.4, 2.0 Hz, 2H), 6.99 (dt, J=10.8, 2.2 Hz, 1H), 3.86 (d, J=6.5 Hz, 2H), 2.05 (dt, J=13.3, 6.6 Hz, 1H), 1.57 (d, J=9.3 Hz, 9H), 1.00 (t, J=5.5 Hz, 6H). ESI-MS m/z calc. 379.13504, found 380.2 (M+1)$^+$; Retention time: 2.57 min (LC Method B).

Step 2: 2-Chloro-6-(3-fluoro-5-isobutoxy-phenyl)pyridine-3-carboxylic Acid

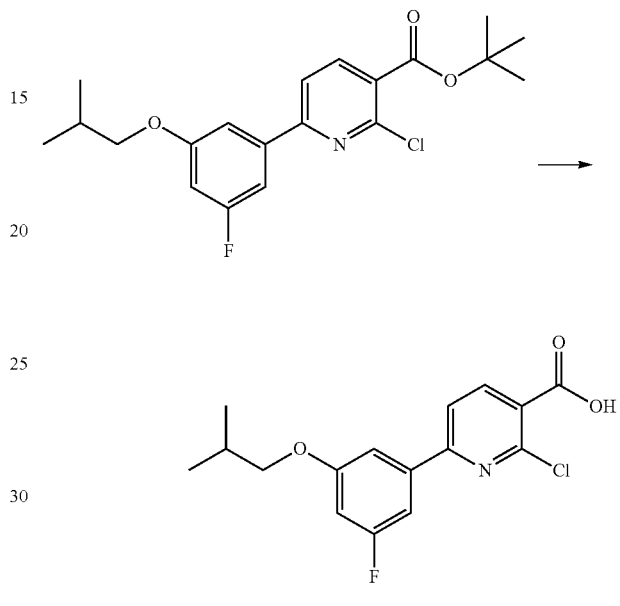

tert-Butyl 2-chloro-6-(3-fluoro-5-isobutoxy-phenyl)pyridine-3-carboxylate (18.57 g, 48.89 mmol) was dissolved in dichloromethane (200 mL). Trifluoroacetic acid (60 mL, 780 mmol) was added and the reaction mixture was allowed to stir at room temperature for 1 h. The reaction mixture was stirred at 40° C. for 2 h. The reaction mixture was concentrated under reduced pressure and taken up in ethyl acetate (100 mL). This solution was washed with a saturated aqueous sodium bicarbonate solution (1×100 mL) and brine (1×100 mL), dried over sodium sulfate, filtered and concentrated under reduced pressure. The crude product was suspended in ethyl acetate (75 mL) and washed with aqueous hydrochloric acid (1 N, 1×75 mL). The organic layer was dried over sodium sulfate, filtered and concentrated under reduced pressure. The resulting solid (17.7 g) was stirred as a slurry in dichloromethane (35 mL) at 40° C. for 30 min. After cooling to room temperature, the slurry was filtered and then rinsed with cold dichloromethane to give 2-chloro-6-(3-fluoro-5-isobutoxy-phenyl)pyridine-3-carboxylic acid (11.35 g, 35.06 mmol, 72%) as a white solid. $^1$H NMR (400 MHz, dimethyl sulfoxide-$d_6$) δ 13.76 (s, 1H), 8.31 (d, J=8.0 Hz, 1H), 8.17 (d, J=8.1 Hz, 1H), 7.54-7.47 (m, 2H), 7.00 (dt, J=10.8, 2.3 Hz, 1H), 3.87 (d, J=6.5 Hz, 2H), 2.05 (dt, J=13.3, 6.6 Hz, 1H), 1.01 (d, J=6.7 Hz, 6H). ESI-MS m/z calc. 323.1, found 324.1 (M+1)$^+$; Retention time: 1.96 min (LC Method B).

Step 3: tert-Butyl (4S)-4-[3-[[6-[[2-chloro-6-(3-fluoro-5-isobutoxy-phenyl) pyridine-3-carbonyl]sulfamoyl]-2-pyridyl]amino]propyl]-2,2-dimethyl-pyrrolidine-1-carboxylate

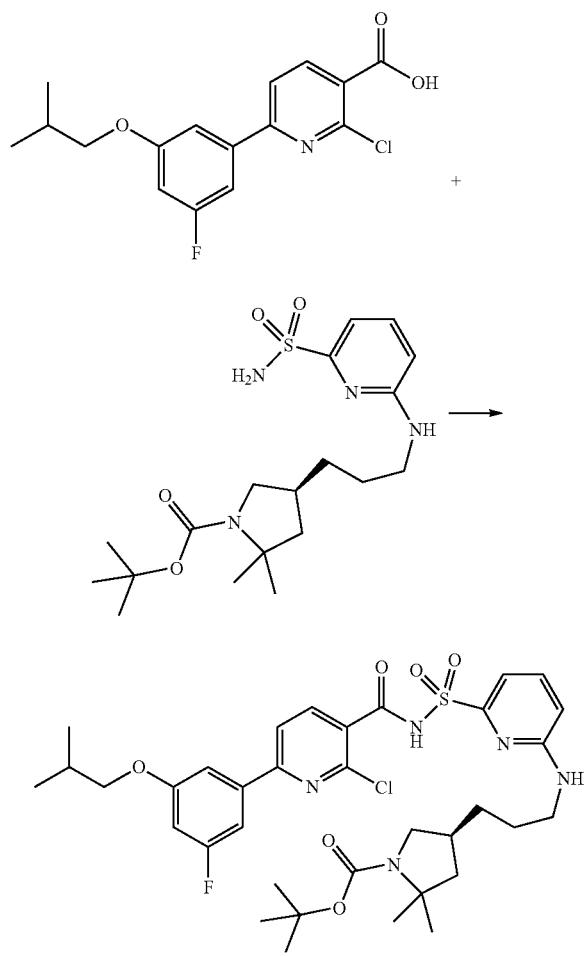 [SMILES: CC(C)COc1cc(F)cc(-c2ccc(C(=O)O)c(Cl)n2)c1 ; CC(C)(C)OC(=O)N1C[C@@H](CCCNc2cccc(S(N)(=O)=O)n2)CC1(C)C ; CC(C)COc1cc(F)cc(-c2ccc(C(=O)NS(=O)(=O)c3cccc(NCCC[C@@H]4CN(C(=O)OC(C)(C)C)C(C)(C)C4)n3)c(Cl)n2)c1]

In a 20 mL scintillation vial, 2-chloro-6-(3-fluoro-5-isobutoxy-phenyl) pyridine-3-carboxylic acid (156 mg, 0.3751 mmol) and carbonyl diimidazole (61 mg, 0.3762 mmol) were combined in tetrahydrofuran (2 mL) and stirred at room temperature for 2 h. Then, tert-butyl (4S)-2,2-dimethyl-4-[3-[(6-sulfamoyl-2-pyridyl) amino]propyl]pyrrolidine-1-carboxylate (100 mg, 0.2424 mmol) in tetrahydrofuran (2 mL) was added followed by 1,8-diazabicyclo [5.4.0]undec-7-ene (110 µL, 0.7356 mmol) and the reaction was stirred for 16 h. The reaction was diluted with ethyl acetate and washed with a small amount of 1:1 saturated aqueous ammonium chloride/brine. The organics were separated, dried over sodium sulfate, filtered and evaporated. The resulting brown residue was purified by silica gel chromatography using a shallow gradient from 100% hexanes to 100% ethyl acetate to afford tert-butyl (4S)-4-[3-[[6-[[2-chloro-6-(3-fluoro-5-isobutoxy-phenyl)pyridine-3-carbonyl]sulfamoyl]-2-pyridyl]amino]propyl]-2,2-dimethyl-pyrrolidine-1-carboxylate (116 mg, 67%). ESI-MS m/z calc. 717.2763, found 718.38 (M+1)$^+$; Retention time: 0.95 min (LC Method A).

Step 4: (14S)-8-[3-Fluoro-5-(2-methylpropoxy)phenyl]-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 224)

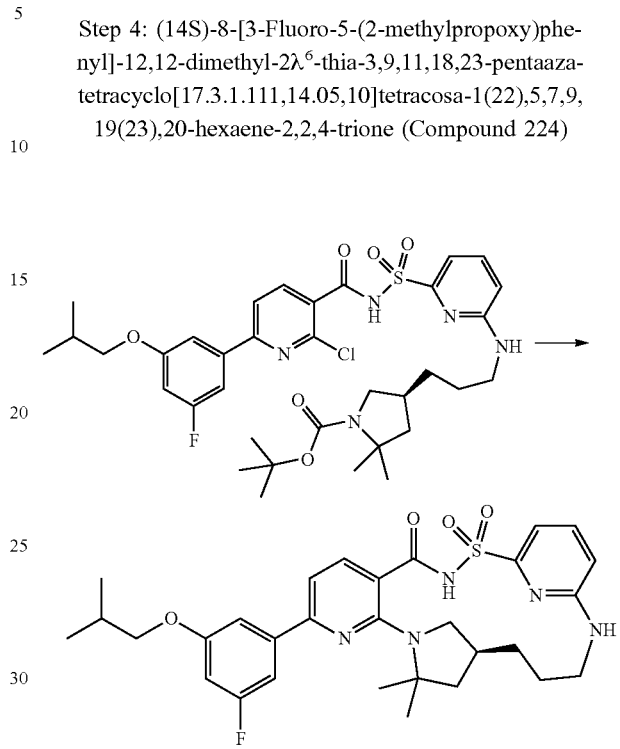

A solution of tert-butyl (4S)-4-[3-[[6-[[2-chloro-6-(3-fluoro-5-isobutoxy-phenyl)pyridine-3-carbonyl]sulfamoyl]-2-pyridyl]amino]propyl]-2,2-dimethyl-pyrrolidine-1-carboxylate (110 mg, 0.1531 mmol) in dichloromethane (1 mL) and trifluoroacetic acid (200 µL, 2.614 mmol) was stirred at room temperature for 4 h. The solvents were then evaporated. The residue was dissolved in ethyl acetate, washed with 2 mL of saturated sodium bicarbonate solution and the solvent was evaporated and dried under vacuum. The resulting residue was dissolved in dimethyl sulfoxide (5 mL) and 3 Å molecular sieves were added and the reaction mixture was stirred for 10 min. Then, cesium fluoride (76 mg, 0.5003 mmol) and potassium carbonate (64 mg, 0.4631 mmol) were added and the reaction mixture was heated at 150° C. for 16 h. The reaction mixture was filtered through a Whatman filter disc (puradisc 25 TF) and the filtrate was purified by a reverse phase HPLC-MS method using a dual gradient run from 20-80% mobile phase B over 15.0 min (mobile phase A=water (0.05% hydrochloric acid), mobile phase B=acetonitrile) to afford (14S)-8-[3-fluoro-5-(2-methylpropoxy)phenyl]-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 224) (12.5 mg, 14%) as an off white solid. $^1$H NMR (400 MHz, Chloroform-d) δ 10.39 (s, 1H), 8.08 (d, J=8.1 Hz, 1H), 7.60-7.46 (m, 2H), 7.36 (t, J=1.9 Hz, 1H), 7.33-7.21 (m, 2H), 6.68 (dt, J=10.4, 2.3 Hz, 1H), 6.57 (dd, J=7.8, 1.4 Hz, 1H), 4.75 (s, 1H), 3.90 (s, 1H), 3.77 (d, J=6.6 Hz, 2H), 3.36 (t, J=8.7 Hz, 1H), 3.17 (d, J=12.6 Hz, 1H), 3.08 (t, J=9.6 Hz, 1H), 2.69 (d, J=10.1 Hz, 1H), 2.12 (dt, J=13.3, 6.7 Hz, 2H), 1.68 (d, J=2.6 Hz, 6H), 1.65-1.54 (m, 5H), 1.04 (d, J=6.7 Hz, 6H). ESI-MS m/z calc. 581.2472, found 582.34 (M+1)$^+$; Retention time: 1.24 min (LC Method J).

Example 64: Preparation of (18S)-4-[3-fluoro-5-(2-methylpropoxy)phenyl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione

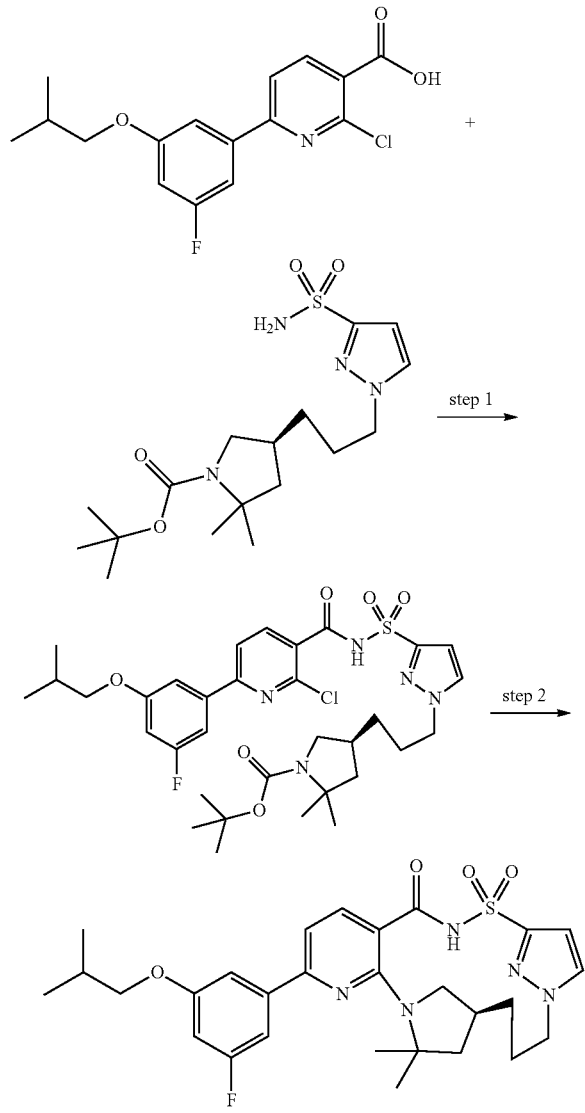

Step 1: tert-Butyl (4S)-4-[3-[3-[[2-chloro-6-(3-fluoro-5-isobutoxy-phenyl) pyridine-3-carbonyl]sulfamoyl]pyrazol-1-yl]propyl]-2,2-dimethyl-pyrrolidine-1-carboxylate

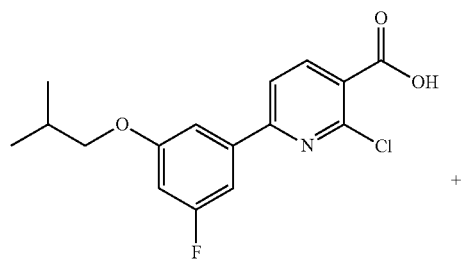

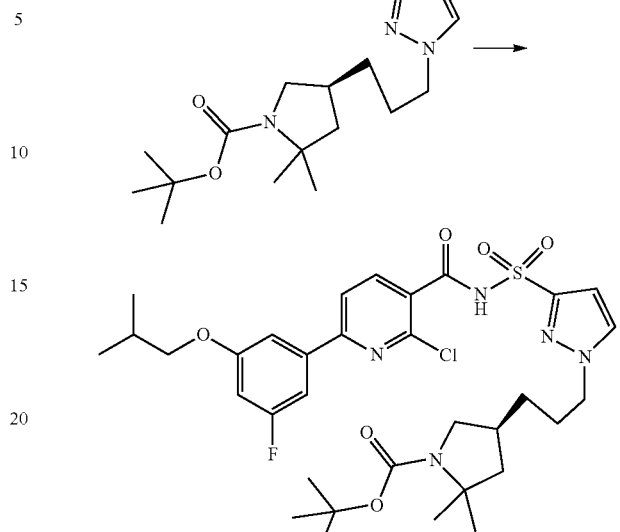

In a 20 mL scintillation vial, 2-chloro-6-(3-fluoro-5-isobutoxy-phenyl) pyridine-3-carboxylic acid (71 mg, 0.1707 mmol) and carbonyl diimidazole (27 mg, 0.1665 mmol) were combined in tetrahydrofuran (2 mL) and stirred for 6 h at room temperature. Then, tert-butyl (4S)-2,2-dimethyl-4-[3-(3-sulfamoylpyrazol-1-yl) propyl]pyrrolidine-1-carboxylate (50 mg, 0.1294 mmol) in tetrahydrofuran (2 mL) was added followed by 1,8-diazabicyclo[5.4.0]undec-7-ene (42 µL, 0.2809 mmol) and the reaction was stirred at room temperature for 16 h. The reaction was diluted with ethyl acetate and washed with a small amount of 1:1 saturated aqueous ammonium chloride/brine. The organics were separated, dried over sodium sulfate, filtered and evaporated. The resultant brown residue was purified by silica gel chromatography using a shallow gradient from 100% dichloromethane to 20% methanol/dichloromethane to afford tert-butyl (4S)-4-[3-[3-[[2-chloro-6-(3-fluoro-5-isobutoxy-phenyl)pyridine-3-carbonyl]sulfamoyl]pyrazol-1-yl]propyl]-2,2-dimethyl-pyrrolidine-1-carb oxy late (52 mg, 58%) as a white solid. ESI-MS m/z calc. 691.2607, found 692.0 (M+1)⁺; Retention time: 0.92 min (LC Method A).

Step 2: (18S)-4-[3-Fluoro-5-(2-methylpropoxy)phenyl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione

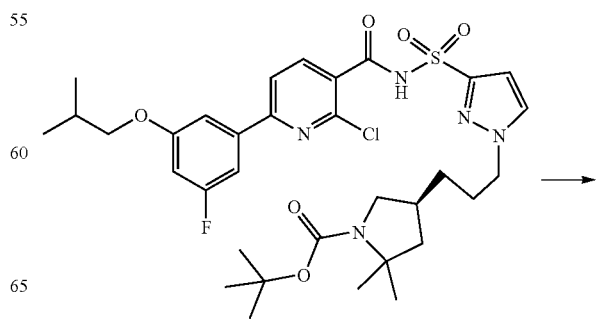

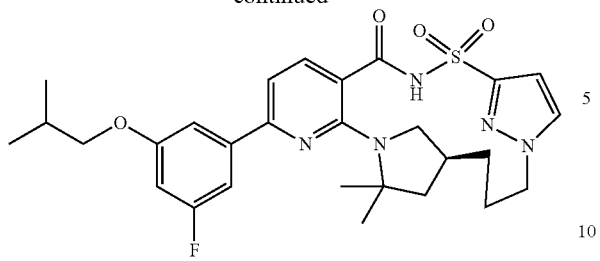

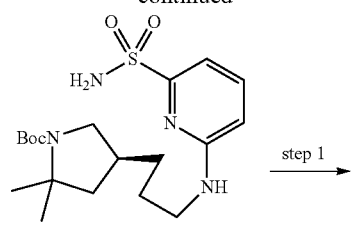

A solution of tert-butyl (4S)-4-[3-[3-[[2-chloro-6-(3-fluoro-5-isobutoxy-phenyl)pyridine-3-carbonyl]sulfamoyl]pyrazol-1-yl]propyl]-2,2-dimethyl-pyrrolidine-1-carboxylate (52 mg, 0.07512 mmol) in dichloromethane (500 µL) and trifluoroacetic acid (100 µL, 1.307 mmol) was stirred at room temperature for 4 h. The solvents were then evaporated. The residue was dissolved in ethyl acetate, washed with 2 mL of saturated sodium bicarbonate solution and the solvent was removed and dried under high vacuum giving a residue that was dissolved in dimethyl sulfoxide (5 mL) and 3 Å molecular sieves were added and the reaction mixture was stirred for 10 min. Then, cesium fluoride (38 mg, 0.2502 mmol) and potassium carbonate (34 mg, 0.2460 mmol) were added and the reaction mixture was heated at 150° C. for 16 h. The reaction mixture was filtered through a Whatman filter disc (puradisc 25 TF) and the filtrate was purified by a reverse phase HPLC-MS method using a dual gradient run from 50-99% mobile phase B over 15.0 min (mobile phase A=water (0.05% hydrochloric acid), mobile phase B=acetonitrile) to afford (18S)-4-[3-fluoro-5-(2-methyl-propoxy)phenyl]-20,20-dimethyl-10$\lambda^6$-thia-1,3,9,14,22-pentaazatetracyclo[16.2.1.1$^{11,14}$.0$^{2,7}$]docosa-2,4,6,11(22),12-pentaene-8,10,10-trione (14.0 mg, 34%) as off white solid. $^1$H NMR (400 MHz, Chloroform-d) δ 7.65 (d, J=7.9 Hz, 1H), 7.47 (d, J=2.3 Hz, 1H), 7.35-7.32 (m, 1H), 7.28-7.23 (m, 1H), 7.08 (s, 1H), 6.95 (d, J=7.9 Hz, 1H), 6.64 (dt, J=10.4, 2.3 Hz, 1H), 4.33 (d, J=13.3 Hz, 1H), 3.92 (dd, J=13.9, 11.2 Hz, 1H), 3.75 (d, J=6.6 Hz, 2H), 2.75 (s, 1H), 2.21-2.07 (m, 3H), 1.98 (dd, J=19.3, 10.6 Hz, 1H), 1.80-1.72 (m, 1H), 1.63 (s, 3H), 1.61 (s, 3H), 1.48 (t, J=12.2 Hz, 1H), 1.38-1.21 (m, 1H), 1.03 (s, 3H), 1.02 (s, 3H), 0.93-0.70 (m, 2H). ESI-MS m/z calc. 555.23157, found 556.14 (M+1)$^+$; Retention time: 1.09 min (LC Method J).

Example 65: Preparation of (14S)-12,12-dimethyl-8-{3-[3-methyl-2-(propan-2-yl)butoxy]-1H-pyrazol-1-yl}-2$\lambda^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 227)

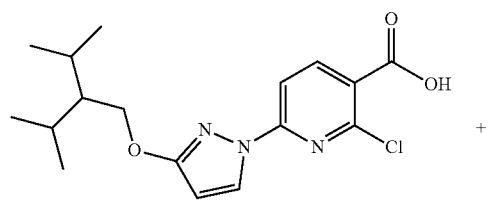

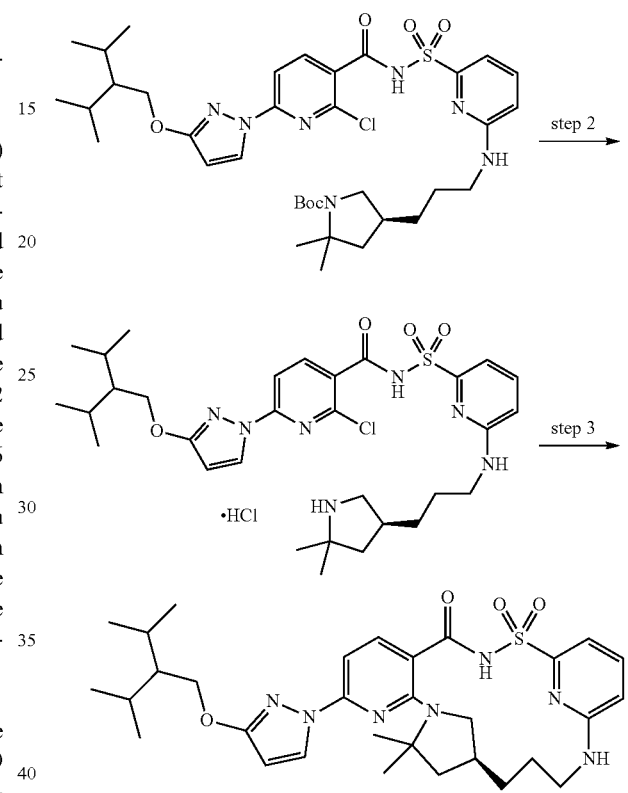

Step 1: tert-Butyl (4S)-4-[3-[[6-[[2-chloro-6-[3-(2-isopropyl-3-methyl-butoxy)pyrazol-1-yl]pyridine-3-carbonyl]sulfamoyl]-2-pyridyl]amino]propyl]-2,2-dimethyl-pyrrolidine-1-carboxylate

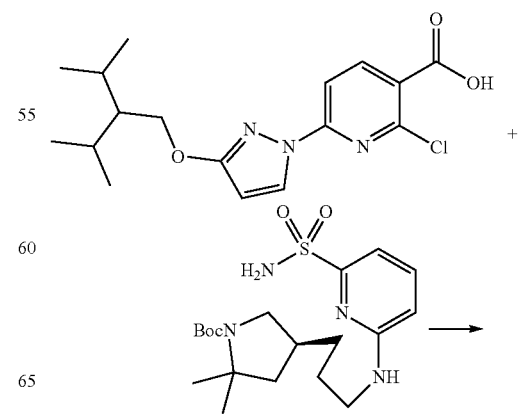

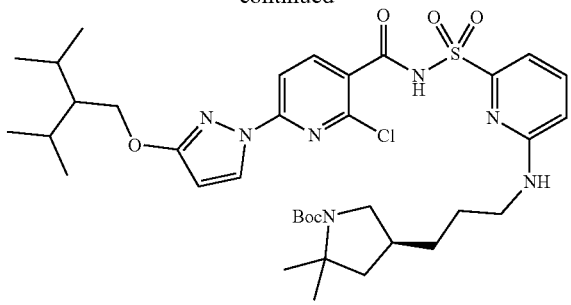

A 50 mL flask charged with carbonyl diimidazole (76 mg, 0.4687 mmol) and 2-chloro-6-[3-(2-isopropyl-3-methyl-butoxy)pyrazol-1-yl]pyridine-3-carboxylic acid (164 mg, 0.4661 mmol) was evacuated/backfilled with nitrogen (3×). Added tetrahydrofuran (5 mL) and the mixture was stirred at 50° C. for 1 h. Next, a solution of tert-butyl (4S)-2,2-dimethyl-4-[3-[(6-sulfamoyl-2-pyridyl)amino]propyl]pyrrolidine-1-carboxylate (160 mg, 0.3878 mmol) and 1,8-diazabicyclo[5.4.0]undec-7-ene (150 mg, 0.9853 mmol) in tetrahydrofuran (5 mL) was added and the mixture was stirred at 50° C. overnight. The reaction was diluted with ethyl acetate and washed with water. The organic phase was dried over sodium sulfate, evaporated in vacuo and purified by preparative reverse phase HPLC ((C$_{18}$): 1-99% acetonitrile in water/hydrochloric acid modifier (15 min)) to afford tert-butyl (4S)-4-[3-[[6-[[2-chloro-6-[3-(2-isopropyl-3-methyl-butoxy)pyrazol-1-yl]pyridine-3-carbonyl]sulfamoyl]-2-pyridyl]amino]propyl]-2,2-dimethyl-pyrrolidine-1-carboxylate (90 mg, 31%). ESI-MS m/z calc. 745.3388, found 746.47 (M+1)$^+$; Retention time: 1.96 min (LC Method B).

Step 2: 2-Chloro-N-[[6-[3-[(3S)-5,5-dimethylpyrrolidin-3-yl]propylamino]-2-pyridyl]sulfonyl]-6-[3-(2-isopropyl-3-methyl-butoxy)pyrazol-1-yl]pyridine-3-carboxamide (Hydrochloride Salt)

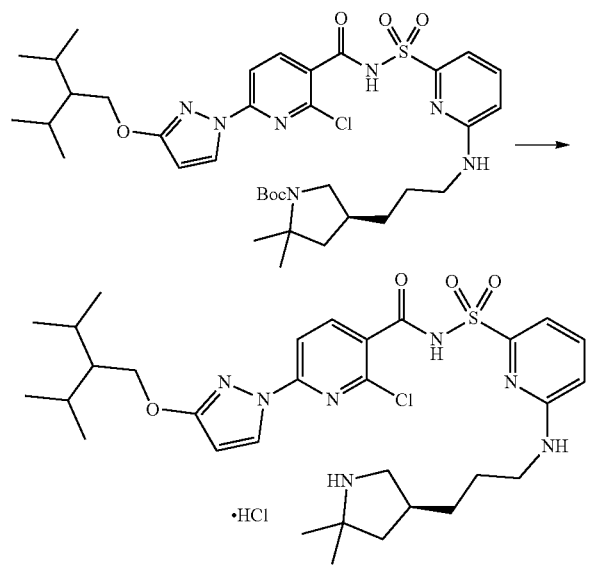

A solution of tert-butyl (4S)-4-[3-[[6-[[2-chloro-6-[3-(2-isopropyl-3-methyl-butoxy)pyrazol-1-yl]pyridine-3-carbonyl]sulfamoyl]-2-pyridyl]amino]propyl]-2,2-dimethyl-pyrrolidine-1-carboxylate (90 mg, 0.12 mmol) in dioxane (5 mL) was treated with a 6 M dioxane solution of hydrochloric acid (1.3 mL, 7.800 mmol) and stirred at room temperature for 3 h. The mixture was evaporated in vacuo to afford 2-chloro-N-[[6-[3-[(3S)-5,5-dimethylpyrrolidin-3-yl]propylamino]-2-pyridyl]sulfonyl]-6-[3-(2-isopropyl-3-methyl-butoxy)pyrazol-1-yl]pyridine-3-carboxamide (hydrochloride salt) (100 mg, 38%). ESI-MS m/z calc. 645.2864, found 646.36 (M+1)$^+$; Retention time: 0.27 min (LC Method A).

Step 3: (14S)-12,12-Dimethyl-8-{3-[3-methyl-2-(propan-2-yl)butoxy]-1H-pyrazol-1-yl}-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 227)

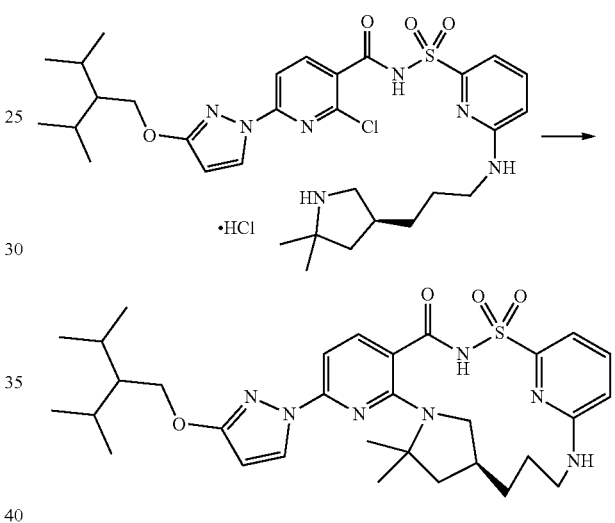

In 5 mL vial, potassium carbonate (102 mg, 0.7380 mmol), cesium fluoride (45 mg, 0.2962 mmol) and 4 Å molecular sieves (300 mg) were sealed and purged with nitrogen. A solution of 2-chloro-N-[[6-[3-[(3S)-5,5-dimethylpyrrolidin-3-yl]propylamino]-2-pyridyl]sulfonyl]-6-[3-(2-isopropyl-3-methyl-butoxy)pyrazol-1-yl]pyridine-3-carboxamide (hydrochloride salt) (100 mg, 0.1465 mmol) in dimethyl sulfoxide (2 mL) was added and the mixture was stirred at 150° C. overnight. The mixture was filtered and purified by preparative reverse phase HPLC ((CB): 50-99% acetonitrile in water/hydrochloric acid modifier (15 min)) to afford (14S)-12,12-dimethyl-8-{3-[3-methyl-2-(propan-2-yl) butoxy]-1H-pyrazol-1-yl}-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 227) (18.0 mg, 20%). $^1$H NMR (400 MHz, Chloroform-d) δ 9.99 (s, 1H), 8.19 (d, J=2.8 Hz, 1H), 8.07 (d, J=8.4 Hz, 1H), 7.60-7.48 (m, 2H), 7.30 (d, J=8.4 Hz, 1H), 6.61-6.52 (m, 1H), 5.91 (d, J=2.8 Hz, 1H), 4.6-4.9 (br. s, 1H), 4.28 (d, J=4.9 Hz, 2H), 3.89 (s, 1H), 3.35 (dd, J=9.9, 7.6 Hz, 1H), 3.17 (dd, J=10.7, 6.7 Hz, 1H), 3.06 (t, J=9.7 Hz, 1H), 2.62 (s, 1H), 2.09 (dd, J=12.3, 8.0 Hz, 1H), 1.99-1.87 (m, 2H), 1.62 (d, J=2.9 Hz, 11H), 1.39 (p, J=5.2 Hz, 1H), 1.01 (d, J=6.9 Hz, 6H), 0.96 (d, J=6.9 Hz, 6H). ESI-MS m/z calc. 609.30975, found 610.39 (M+1)$^+$; Retention time: 1.59 min (LC Method J).

Example 66: Preparation of (14S)-8-{3-[2-(adamantan-1-yl)ethyl]-2-oxoimidazolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 228)

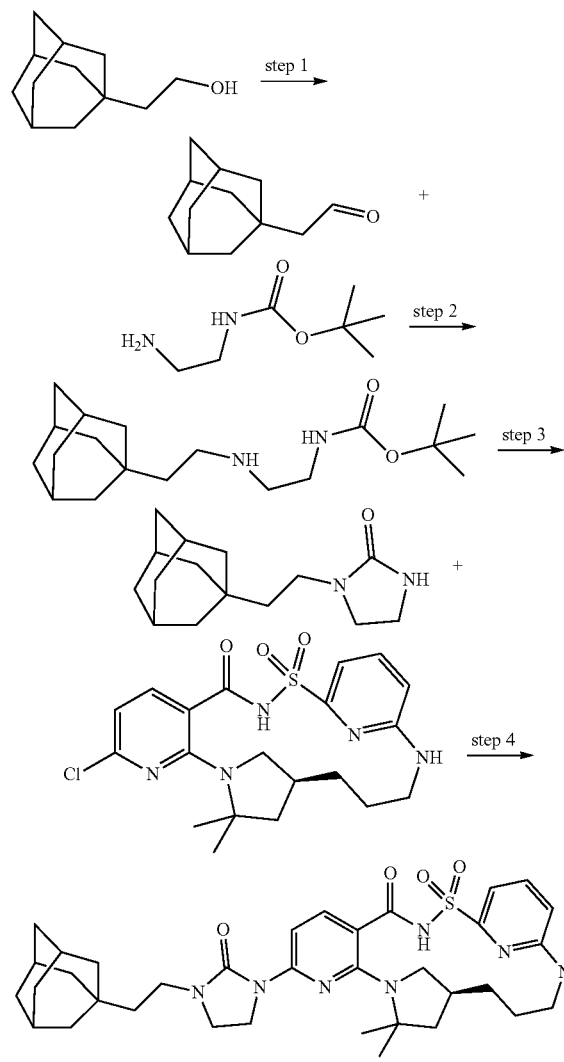

Step 1: 2-(1-Adamantyl)acetaldehyde

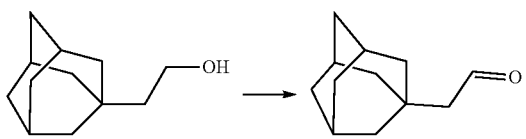 [SMILES: OCCC12CC3CC(CC(C3)C1)C2 ; O=CCC12CC3CC(CC(C3)C1)C2]

Solid Dess-Martin periodinane (825 mg, 1.945 mmol) was added to a stirred solution of 2-(1-adamantyl)ethanol (300 mg, 1.664 mmol) in anhydrous dichloromethane (10 mL) at 0° C. (ice-water bath) under nitrogen. After 15 min, the bath was removed and the reaction was allowed to warm to ambient temperature and stirring continued for another 2 h. The reaction was diluted with ether (60 mL) and saturated aqueous sodium bicarbonate (20 mL) was added slowly (to mitigate carbon dioxide gas evolution). Then sodium thiosulfate (10 mL) was added and stirred at ambient temperature for 30 min. The layers were separated and the aqueous layer was extracted with ether (2×20 mL). The combined organics were washed with brine (20 mL), dried over anhydrous sodium sulfate, filtered and concentrated under reduced pressure to obtain 2-(1-adamantyl)acetaldehyde (149 mg, 50%) as colorless semi solid. It was used in the subsequent step without further drying or purification. ¹H NMR (400 MHz, Benzene-d₆) δ 9.70 (t, J=3.1 Hz, 1H), 1.95-1.93 (m, 1H), 1.89-1.87 (m, 2H), 1.85 (d, J=3.1 Hz, 2H), 1.68 (d, J=3.0 Hz, 3H), 1.59 (dq, J=4.0, 2.0 Hz, 2H), 1.56 (d, J=2.2 Hz, 1H), 1.49 (d, J=2.8 Hz, 6H).

Step 2: tert-Butyl N-[2-[2-(1-adamantyl)ethylamino]ethyl]carbamate

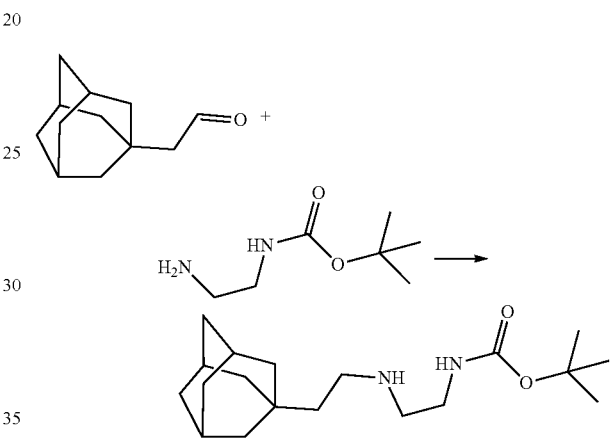

To a stirred solution of 2-(1-adamantyl)acetaldehyde (130.0 mg, 0.7292 mmol) in anhydrous methylene chloride (10 mL) was added a solution of tert-butyl N-(2-aminoethyl)carbamate (117 mg, 0.7303 mmol) in anhydrous methylene chloride (1 mL) followed by addition of glacial acetic acid (50 μL, 0.8792 mmol) at ambient temperature under nitrogen. The cloudy reaction was stirred for 30 min, then sodium triacetoxyborohydride (242 mg, 1.142 mmol) was added in one portion at ambient temperature and stirring continued overnight (13 h). The volatiles were removed under reduced pressure. The residue was taken up in ethyl acetate (30 mL) and washed with saturated aqueous sodium bicarbonate solution (2×15 mL) and brine (15 mL), dried over anhydrous sodium sulfate, filtered and concentrated under reduced pressure to furnish tert-butyl N-[2-[2-(1-adamantyl)ethylamino]ethyl]carbamate (209 mg, 89%) as a yellow gum. The crude material was used in the next step without further purification. ESI-MS m/z calc. 322.26202, found 323.4 (M+1)⁺; Retention time: 1.19 min (LC Method B).

Step 3: 1-[2-(1-Adamantyl)ethyl]imidazolidin-2-one

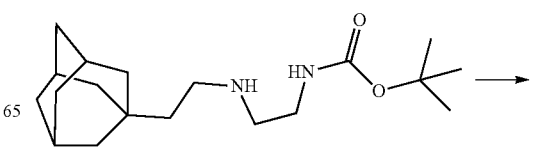

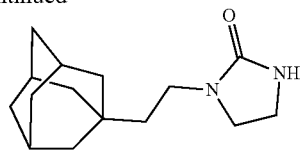

Solid potassium tert-butoxide (212 mg, 1.889 mmol) was added to a stirred solution of tert-butyl N-[2-[2-(1-adamantyl)ethylamino]ethyl]carbamate (200 mg, 0.6202 mmol) in anhydrous tetrahydrofuran (12 mL) under nitrogen and the reaction mixture was heated at 70° C. for 13 h. The heterogeneous mixture was allowed to cool to ambient temperature and was acidified with aqueous hydrochloric acid (3.0 mL of 1.0 M, 3.000 mmol) and the volatiles were removed under reduced pressure. The aqueous residue was extracted with ethyl acetate (3×10 mL) and the combined organics were washed with brine (10 mL), dried over anhydrous sodium sulfate, filtered and concentrated under reduced pressure. The residue was purified by silica gel chromatography (0-10% methanol in dichloromethane gradient over 30 min) to afford 1-[2-(1-adamantyl)ethyl]imidazolidin-2-one (53 mg, 34%) as an off-white solid. $^1$H NMR (400 MHz, Benzene-$d_6$) δ 4.92 (s, 1H), 3.35-3.25 (m, 2H), 2.85-2.76 (m, 2H), 2.74-2.66 (m, 2H), 1.99 (p, J=3.0 Hz, 3H), 1.80-1.73 (m, 3H), 1.69 (dq, J=12.3, 2.3 Hz, 3H), 1.55 (d, J=2.8 Hz, 6H), 1.32-1.21 (m, 2H). ESI-MS m/z calc. 248.18886, found 249.3 (M+1)$^+$; Retention time: 1.67 min (LC Method B).

Step 4: (14S)-8-{3-[2-(Adamantan-1-yl)ethyl]-2-oxoimidazolidin-1-yl}-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 228)

To a 4 mL vial, (14S)-8-chloro-12,12-dimethyl-2λ$^6$-thia-3,9,11,18,23-pentaazatetracyclo[17.3.1.111,14.05,10]tetracosa-1(23),5,7,9,19,21-hexaene-2,2,4-trione (20 mg, 0.04298 mmol), 1-[2-(1-adamantyl)ethyl]imidazolidin-2-one (13 mg, 0.05234 mmol), cesium carbonate (52 mg, 0.1596 mmol), 4,5-bis(diphenylphosphino)-9,9-dimethylxanthene (4 mg, 0.006913 mmol) and anhydrous dioxane (1.0 mL) were added in that order. Nitrogen was bubbled through the heterogeneous mixture for 2 min. Then tris(dibenzylideneacetone)dipalladium(0) (4 mg, 0.004368 mmol) was added under nitrogen and nitrogen was bubbled for another 2 min and the reaction was capped under a nitrogen atmosphere. The mixture was stirred at 115° C. overnight. The mixture was allowed to cool to ambient temperature and neutralized with glacial acetic acid (20 μL, 0.3517 mmol). The volatiles were removed under reduced pressure and the residue was taken up in dimethyl sulfoxide (1.0 mL) and filtered through a Whatman 0.45 μm PTFE syringe filter disc. The sample was purified using preparative reverse-phase HPLC-MS [Luna $C_{18}$ (2) column (75×30 mm, 5 μm particle size) sold by Phenomenex (pn: 00C-4252-U0-AX), (dual gradient run from 30-99% acetonitrile in water over 15 min (hydrochloric acid as modifier)] giving (14S)-8-[3-[2-(adamantan-1-yl)ethyl]-2-oxoimidazolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 228) (13.0 mg, 44%) as yellowish solid. $^1$H NMR (400 MHz, dimethyl sulfoxide-$d_6$) δ 12.29 (s, 1H), 7.59 (d, J=8.6 Hz, 1H), 7.57-7.53 (m, 1H), 7.41 (d, J=8.5 Hz, 1H), 7.03 (d, J=7.2 Hz, 1H), 6.96 (d, J=6.7 Hz, 1H), 6.70 (d, J=8.5 Hz, 1H), 4.00-3.82 (m, 3H), 3.49-3.42 (m, 2H), 3.26-3.16 (m, 2H), 3.13-3.03 (m, 1H), 2.93 (d, J=13.3 Hz, 1H), 2.73-2.64 (m, 1H), 2.18-2.01 (m, 2H), 1.93 (s, 3H), 1.80 (dd, J=12.1, 5.6 Hz, 2H), 1.71-1.59 (m, 7H), 1.58 (s, 3H), 1.55-1.53 (m, 1H), 1.51 (two s, 6H), 1.46 (s, 3H), 1.31-1.22 (m, 3H). ESI-MS m/z calc. 661.341, found 662.5 (M+1)$^+$; Retention time: 1.92 min (LC Method G).

Example 67: Preparation of (14S)-8-[3-(adamantan-1-yl)-2-oxoimidazolidin-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 230)

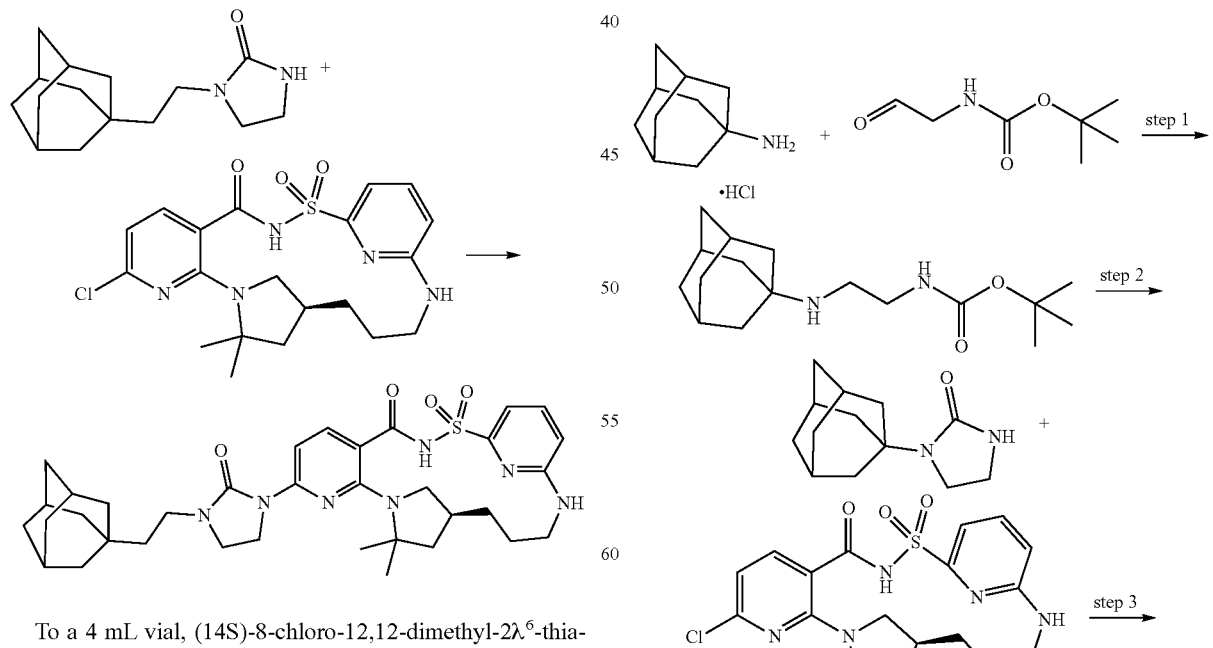

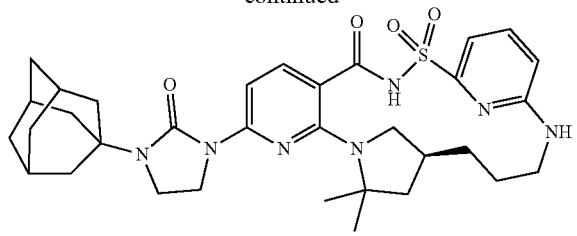

Step 1: tert-Butyl
N-[2-(1-adamantylamino)ethyl]carbamate

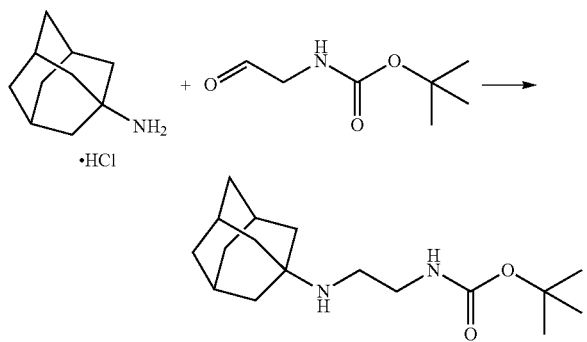

To a stirred solution of tert-butyl N-(2-oxoethyl)carbamate (505 mg, 3.172 mmol) in anhydrous methylene chloride (20 mL) was added solid adamantan-1-amine (hydrochloride salt) (475 mg, 3.141 mmol) followed by addition of triethylamine (500 µL, 3.587 mmol) and glacial acetic acid (200 µL, 3.517 mmol) in that order and the reaction was stirred at ambient temperature under nitrogen. The heterogeneous (white suspension) reaction was stirred for 30 min, then sodium triacetoxyborohydride (1.0 g, 4.718 mmol) was added in one portion at ambient temperature and stirring continued overnight. The volatiles were removed under reduced pressure. The residue was taken up in ethyl acetate (30 mL) and washed with saturated aqueous sodium bicarbonate solution (2×15 mL) and brine (15 mL), dried over anhydrous sodium sulfate, filtered and concentrated under reduced pressure to furnish tert-butyl N-[2-(1-adamantylamino)ethyl]carbamate (731 mg, 79%) as a yellow gum. The crude material was used in the next step without further purification. ESI-MS m/z calc. 294.23074, found 295.4 (M+1)$^+$; Retention time: 0.91 min (LC Method B).

Step 2: 1-(1-Adamantyl)imidazolidin-2-one

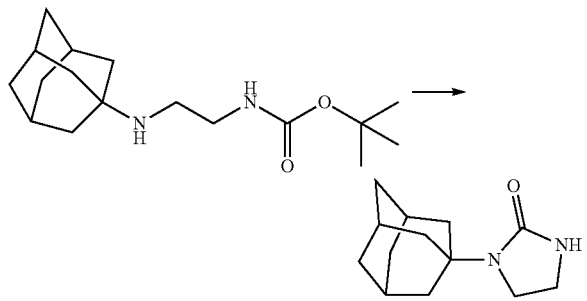

Solid potassium tert-butoxide (465 mg, 4.144 mmol) was added to a stirred solution of tert-butyl N-[2-(1-adamantylamino)ethyl]carbamate (400 mg, 1.359 mmol) in anhydrous tetrahydrofuran (12 mL) under nitrogen and the reaction mixture was heated at 70° C. for 13 h. The heterogeneous mixture was allowed to cool to ambient temperature and acidified with aqueous hydrochloric acid (5.5 mL of 1.0 M, 5.500 mmol) to pH=4-5 and the volatiles were removed under reduced pressure. The aqueous residue was extracted with ethyl acetate (3×10 mL) and the combined organics were washed with brine (10 mL), dried over anhydrous sodium sulfate, filtered and concentrated under reduced pressure. The residue was purified by silica gel chromatography (0-10% methanol in dichloromethane gradient over 30 min) to afford 1-(1-adamantyl)imidazolidin-2-one (69 mg, 23%) as an off-white solid. $^1$H NMR (400 MHz, Benzene-d$_6$) δ 4.91 (s, 1H), 2.90 (dd, J=8.5, 6.7 Hz, 2H), 2.64 (ddd, J=8.5, 6.7, 1.2 Hz, 2H), 2.21 (d, J=2.9 Hz, 6H), 2.06 (dd, J=5.9, 3.0 Hz, 3H), 1.75-1.68 (m, 3H), 1.67-1.60 (m, 3H). ESI-MS m/z calc. 220.15756, found 221.2 (M+1)$^+$; Retention time: 1.36 min (LC Method B).

Step 3: (14S)-8-[3-(Adamantan-1-yl)-2-oxoimidazolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 230)

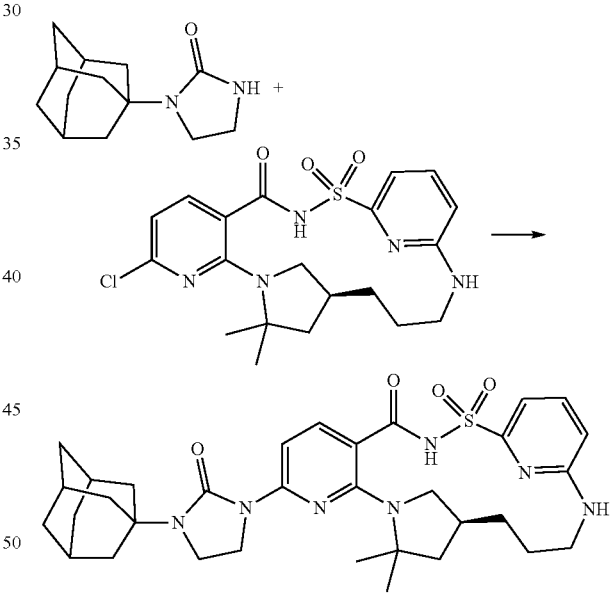

To a 4 mL vial, (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (20 mg, 0.04298 mmol), 1-(1-adamantyl)imidazolidin-2-one (13 mg, 0.05901 mmol), cesium carbonate (52 mg, 0.1596 mmol), 4,5-bis(diphenylphosphino)-9,9-dimethylxanthene (4 mg, 0.006913 mmol) and anhydrous dioxane (1.0 mL) were added, in that order. Nitrogen was bubbled through the heterogeneous mixture for 2 min. Then tris(dibenzylideneacetone)dipalladium(0) (4 mg, 0.004368 mmol) was added under nitrogen and nitrogen was bubbled for another 2 min and capped the vial under a nitrogen atmosphere. The mixture was stirred at 115° C. overnight. The mixture was allowed to cool to ambient temperature and neutralized with glacial acetic acid (20 μL, 0.3517 mmol). The volatiles were removed under reduced pressure and the residue was taken up in dimethyl sulfoxide (1.0 mL), filtered through a Whatman 0.45 μm PTFE syringe filter disc. The sample was purified using preparative reverse-phase HPLC-MS [Luna $C_{18}$ (2) column (75×30 mm, 5 μm particle size) sold by Phenomenex (pn: 00C-4252-U0-AX), (dual gradient run from 30-99% acetonitrile in water over 15 min (hydrochloric acid as modifier))] giving (14S)-8-[3-(adamantan-1-yl)-2-oxoimidazolidin-1-yl]-12,12-dimethyl-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 230) (9 mg, 33%) as a yellowish solid. ¹H NMR (400 MHz, dimethyl sulfoxide-$d_6$) δ 12.28 (s, 1H), 7.61-7.57 (m, 1H), 7.57-7.52 (m, 1H), 7.38 (d, J=8.6 Hz, 1H), 7.03 (d, J=7.1 Hz, 1H), 6.96 (d, J=7.3 Hz, 1H), 6.70 (d, J=8.5 Hz, 1H), 3.96-3.74 (m, 3H), 3.53-3.46 (m, 2H), 3.12-3.03 (m, 1H), 2.93 (d, J=13.4 Hz, 1H), 2.73-2.65 (m, 1H), 2.12-2.02 (m, 8H), 1.83-1.71 (m, 2H), 1.65 (s, 5H), 1.62-1.59 (m, 1H), 1.57 (s, 3H), 1.55-1.48 (m, 3H), 1.46 (s, 3H), 1.36-1.22 (m, 3H). ESI-MS m/z calc. 633.30975, found 634.5 (M+1)⁺; Retention time: 1.66 min (LC Method G).

Example 68: Preparation of (14S)-8-[3-(3,3-dicyclobutylpropoxy)-1H-pyrazol-1-yl]-12,12-dimethyl-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 231)

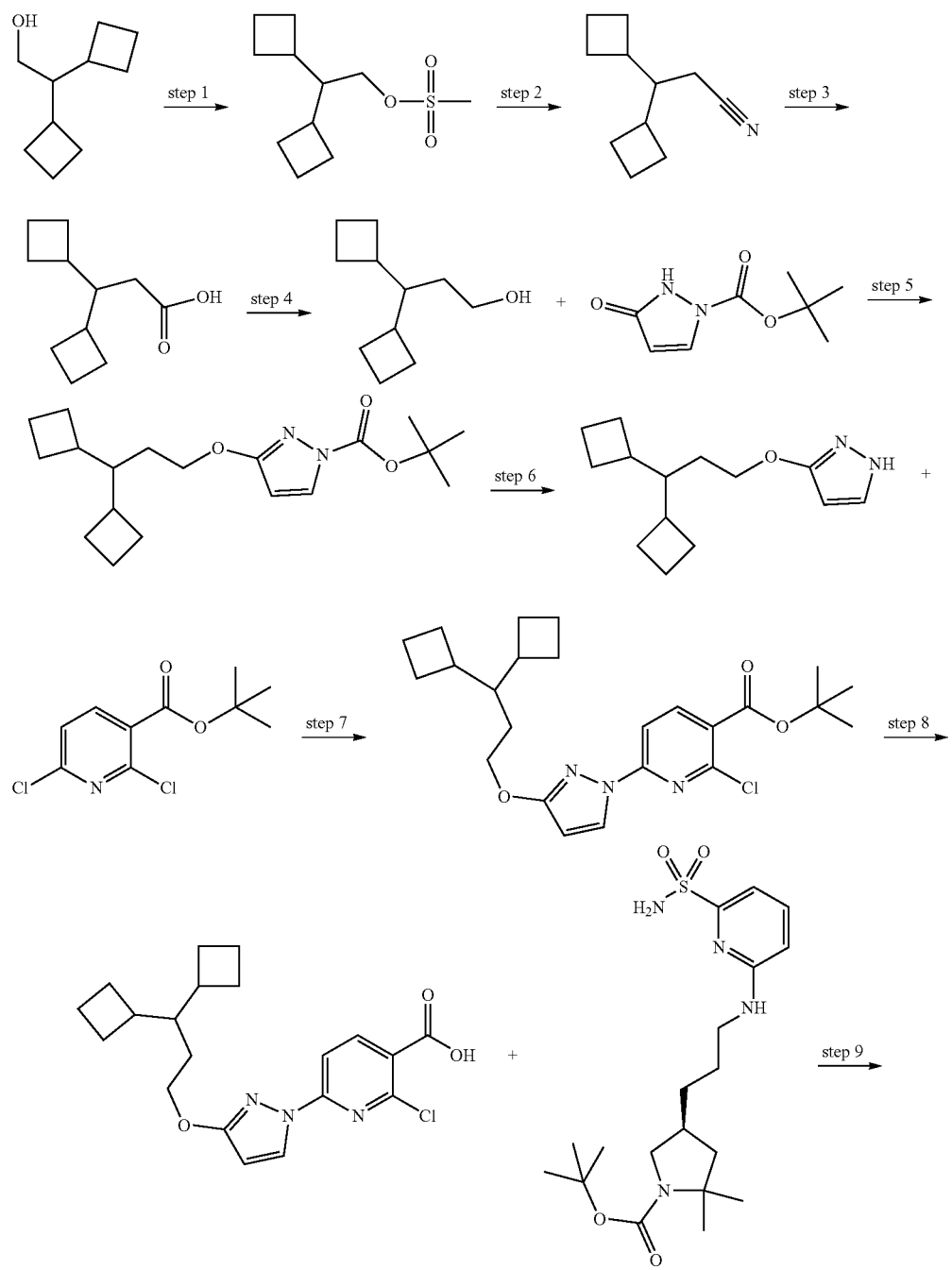

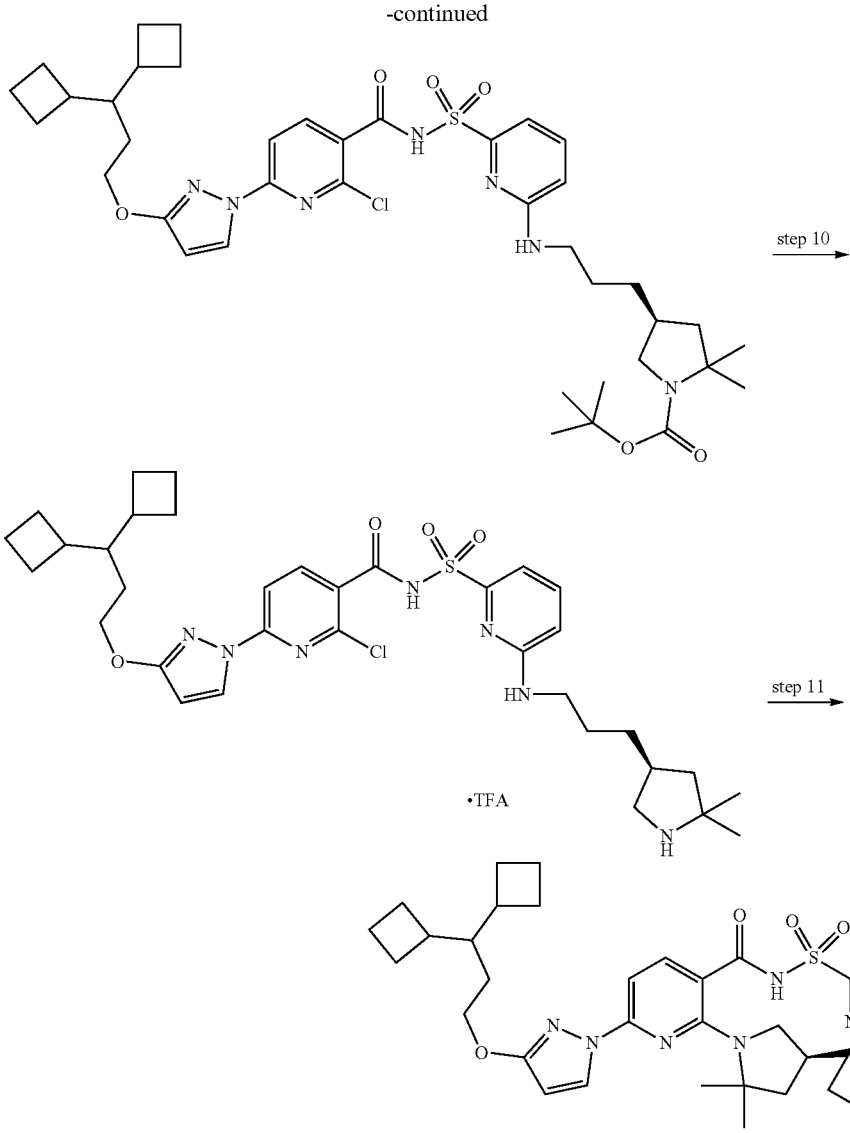

Step 1: 2,2-Di(cyclobutyl)ethyl methanesulfonate

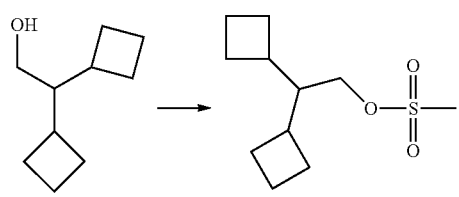

To a 100 mL round bottom flask containing 2,2-di(cyclobutyl)ethanol (1.0 g, 6.483 mmol) in dichloromethane (11.0 mL) was added triethylamine (2.72 mL, 19.51 mmol). The reaction was cooled to 0° C. in an ice bath. Methanesulfonyl chloride (891 mg, 7.778 mmol) was added dropwise (exothermic, formed faint yellowish slurry) and the reaction was stirred for 1 h while warming to room temperature. After 1 h of stirring, the reaction was then quenched with cold water (15 mL) (mixture turned into clear faint yellow solution) and extracted with dichloromethane (20 mL) twice, organic layer was washed with brine. The organic layer was dried over sodium sulfate, filtered and evaporated to provide crude 2,2-di(cyclobutyl)ethyl methanesulfonate (1.5 g, 100%) as a clear colorless to faint yellowish liquid. This product was used for the next reaction without further purification. $^1$H NMR (400 MHz, Chloroform-d) δ 4.03 (d, J=4.6 Hz, 2H), 2.97 (s, 3H), 2.37-2.12 (m, 2H), 2.09-1.47 (m, 13H).

Step 2: 3,3-Di(cyclobutyl)propanenitrile

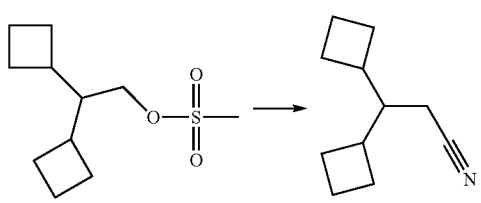

To a solution of 2,2-di(cyclobutyl)ethyl methanesulfonate (1.75 g, 7.532 mmol) in dimethyl sulfoxide (23 mL) was added solid cyanosodium (290 µL, 9.468 mmol) under a nitrogen atmosphere. The mixture was stirred at 70° C. The reaction turned into a light yellow slurry upon heating then into light amber slurry over time. The reaction was allowed to stir for 17 h at 70° C. The reaction mixture was then poured into cold water (25 mL) and extracted with diethyl ether (3×25 mL). The combined organic layers were washed with water (2×25 mL), dried over sodium sulfate, filtered and concentrated to give the crude product, 3,3-di(cyclobutyl)propanenitrile (1.2 g, 98%) as a clear faint amber liquid which was used without further purification. $^1$H NMR (400 MHz, Chloroform-d) δ 3.48 (q, J=7.0 Hz, 1H), 2.38-2.21 (m, 2H), 2.10-1.92 (m, 2H), 1.92-1.64 (m, 8H), 1.63-1.48 (m, 2H), 1.21 (t, J=7.0 Hz, 2H).

Step 3: 3,3-Di(cyclobutyl)propanoic Acid

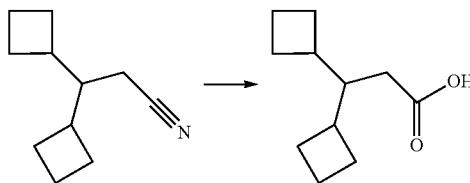

To a solution of 3,3-di(cyclobutyl)propanenitrile (1.2 g, 7.350 mmol) in ethanol (18 mL) was added sodium hydroxide (12.5 mL of 6 M, 75.00 mmol). The resulting clear amber solution was heated to 70° C. for 3 days. Solid sodium hydroxide (3 g, 75.01 mmol) was added and the reaction was stirred for 3 additional days at 100° C. Ethanol was evaporated and the pH of the aqueous layer was adjusted to 1 with 5 M hydrochloric acid. The mixture was then extracted with diethyl ether (3×20 mL). The organic extract was dried over sodium sulfate, filtered and concentrated to give 3,3-di(cyclobutyl)propanoic acid (1 g, 75%) as a light orange thick oil. $^1$H NMR (400 MHz, Chloroform-d) δ 2.16 (dddd, J=13.0, 9.0, 5.4, 2.5 Hz, 2H), 2.10 (d, J=6.3 Hz, 2H), 1.99-1.87 (m, 5H), 1.86-1.60 (m, 8H).

Step 4: 3,3-Di(cyclobutyl)propan-1-ol

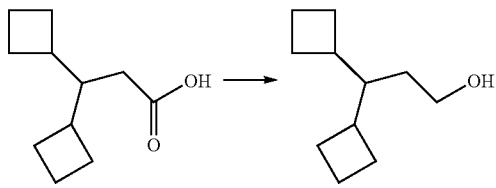 [SMILES: O=C(O)CC(C1CCC1)C1CCC1 ; OCCC(C1CCC1)C1CCC1]

Lithium aluminum hydride (300 mg, 8.844 mmol) (pellets) was suspended in tetrahydrofuran (15 mL) and stirred at room temperature for 30 min at which time the pellets formed a suspension. The mixture was then cooled in an ice/water bath and 3,3-di(cyclobutyl)propanoic acid (988 mg, 5.421 mmol) in tetrahydrofuran (7.2 mL) was added dropwise over 15 min keeping the reaction temperature<20° C. The mixture was allowed to stir a total of 72 h, gradually warming to ambient temperature. The mixture was cooled with an ice-bath and sequentially quenched slowly with water (830 µL, 46.07 mmol), followed by sodium hydroxide (830 µL of 6 M, 4.980 mmol) and then water (2.5 mL, 138.8 mmol). The mixture was stirred until the gray slurry totally converted into a white, granular slurry which was filtered over celite. The solid was washed with ether. The filtrate was concentrated in vacuo at 90 mbar and 30° C. water bath, diluted with diethyl ether, dried (magnesium sulfate), filtered and concentrated in vacuo giving 3,3-di(cyclobutyl)propan-1-ol (868 mg, 95%) as a colorless liquid. $^1$H NMR (400 MHz, Chloroform-d) δ 3.64-3.54 (m, 2H), 2.11 (m, J=13.9, 9.8, 7.4, 6.0, 2.0 Hz, 2H), 2.01-1.84 (m, 4H), 1.83-1.59 (m, 8H), 1.50-1.37 (m, 2H).

Step 5: tert-Butyl 3-[3,3-di(cyclobutyl)propoxy]pyrazole-1-carboxylate

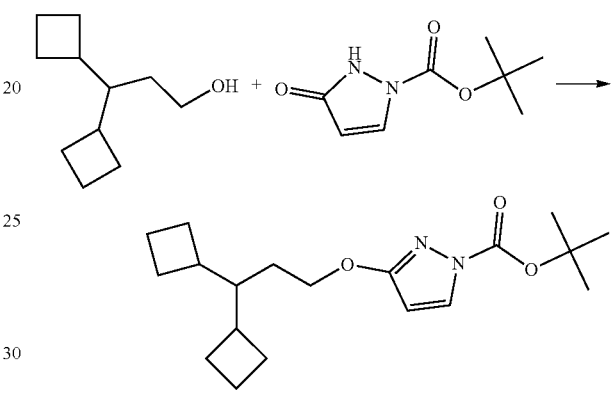

To a solution of tert-butyl 5-oxo-1H-pyrazole-2-carboxylate (530 mg, 2.877 mmol) and 3,3-di(cyclobutyl)propan-1-ol (536 mg, 3.185 mmol) in tetrahydrofuran (8 mL) was added triphenylphosphine (830 mg, 3.164 mmol). To this mixture was slowly added diisopropyl azodicarboxylate (680 µL, 3.454 mmol) dropwise over 10 min. The reaction mixture was stirred at 50° C. for 16 h. The tetrahydrofuran was removed in vacuo. Toluene was added to the crude mixture in order to precipitate the triphenylphosphine oxide. The mixture did not form precipitate. The clear solution was then concentrated to dryness. The thick yellow oil was dissolved in dichloromethane and purified by silica gel chromatography with a gradient of 0% to 20% ethyl acetate in hexanes. Pure fractions were pooled together and concentrated to dryness giving the desired product, tert-butyl 3-[3,3-di(cyclobutyl)propoxy]pyrazole-1-carboxylate (560 mg, 58%) as a white solid. $^1$H NMR (400 MHz, Chloroform-d) δ 7.82 (d, J=2.9 Hz, 1H), 5.85 (d, J=2.9 Hz, 1H), 4.21 (t, J=7.4 Hz, 2H), 2.24-2.11 (m, 2H), 2.02-1.86 (m, 3H), 1.84-1.64 (m, 4H), 1.61 (s, 11H), 1.51-1.29 (m, 1H). ESI-MS m/z calc. 334.22565, found 335.24 (M+1)$^+$; Retention time: 2.47 min (LC Method B).

Step 6: 3-[3,3-Di(cyclobutyl)propoxy]-1H-pyrazole

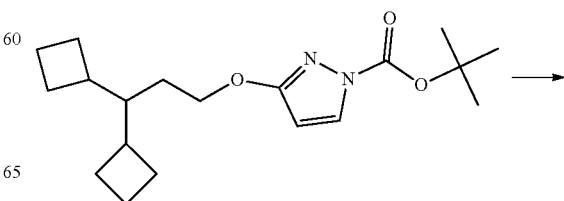

549

-continued

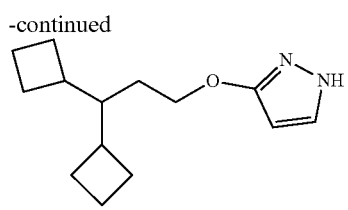

To a solution of tert-butyl 3-[3,3-di(cyclobutyl)propoxy] pyrazole-1-carboxylate (200 mg, 0.5980 mmol) in dichloromethane (2 mL) was added trifluoroacetic acid (700 μL, 9.086 mmol). The mixture was stirred at room temperature for 2 h. The trifluoroacetic acid was removed under reduced pressure and the resulting crude was diluted with ethyl acetate. The organic solution was washed with aqueous sodium bicarbonate. The aqueous was further extracted with ethyl acetate (2×). The combined organic layers were dried over sodium sulfate, filtered and concentrated to dryness to give 3-[3,3-di(cyclobutyl)propoxy]-1H-pyrazole (140 mg, 100%). ESI-MS m/z calc. 234.17322, found 235.15 (M+1)$^+$; Retention time: 1.9 min (LC Method B).

Step 7: tert-Butyl 2-chloro-6-[3-[3,3-di(cyclobutyl) propoxy]pyrazol-1-yl]pyridine-3-carboxylate

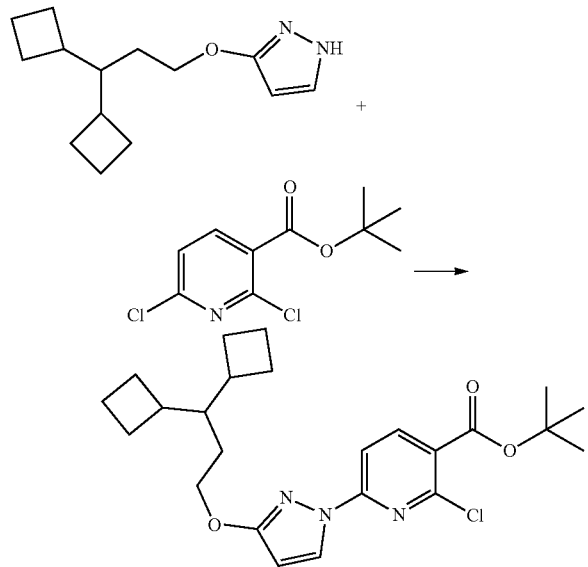

tert-Butyl 2,6-dichloropyridine-3-carboxylate (275 mg, 1.108 mmol), 3-[3,3-di(cyclobutyl)propoxy]-1H-pyrazole (260 mg, 1.110 mmol) and potassium carbonate (185 mg, 1.339 mmol) were combined in anhydrous dimethyl sulfoxide (5.2 mL). 1,4-Diazabicyclo[2.2.2]octane (25 mg, 0.2229 mmol) was added and the mixture was stirred at room temperature under nitrogen for 16 h. The reaction mixture was diluted with water (10 mL) and stirred for 15 min. The resulting white solid was collected and washed with water. The solid was dissolved in dichloromethane and dried over magnesium sulfate. The mixture was filtered and evaporated to give the product as a colorless oil, tert-butyl 2-chloro-6-[3-[3,3-di(cyclobutyl)propoxy]pyrazol-1-yl]pyridine-3-carboxylate (367 mg, 74%). $^1$H NMR (400 MHz, Chloroform-d) δ 8.35 (d, J=2.9 Hz, 1H), 8.18 (d, J=8.4 Hz, 1H), 7.69 (d, J=8.4 Hz, 1H), 5.95 (d, J=2.8 Hz, 1H), 4.20 (t, J=7.5 Hz, 2H), 2.18 (tt, J=9.6, 4.4 Hz, 2H), 2.07-1.86 (m, 4H), 1.87-1.35 (m, 20H). ESI-MS m/z calc. 445.21323, found 446.29 (M+1)$^+$; Retention time: 0.88 min (LC Method L).

Step 8: 2-Chloro-6-[3-[3,3-di(cyclobutyl)propoxy] pyrazol-1-yl]pyridine-3-carboxylic Acid

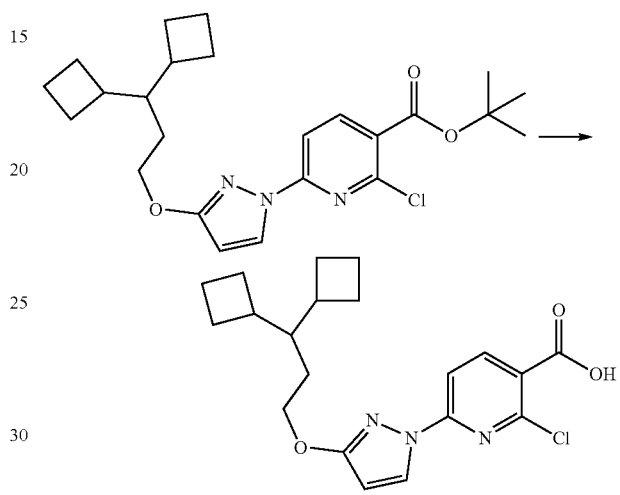

tert-Butyl 2-chloro-6-[3-[3,3-di(cyclobutyl)propoxy] pyrazol-1-yl]pyridine-3-carboxylate (367 mg, 0.8229 mmol) was dissolved in dichloromethane (4 mL) and trifluoroacetic acid (1.5 mL, 19.47 mmol) was added. The reaction was stirred at room temperature for 16 h. The reaction was evaporated and the resulting solid was suspended in ether and the ether was then removed under reduced pressure. This evaporation from ether procedure was repeated twice, resulting in a white solid of 2-chloro-6-[3-[3,3-di(cyclobutyl)propoxy]pyrazol-1-yl]pyridine-3-carboxylic acid (300 mg, 94%). ESI-MS m/z calc. 389.1506, found 390.22 (M+1)$^+$; Retention time: 1.45 min (LC Method J).

Step 9: tert-Butyl (4S)-4-[3-[[6-[[2-chloro-6-[3-[3,3-di(cyclobutyl)propoxy]pyrazol-1-yl]pyridine-3-carbonyl]sulfamoyl]-2-pyridyl]amino]propyl]-2,2-dimethyl-pyrrolidine-1-carboxylate

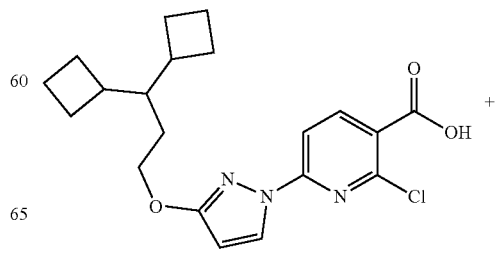

-continued

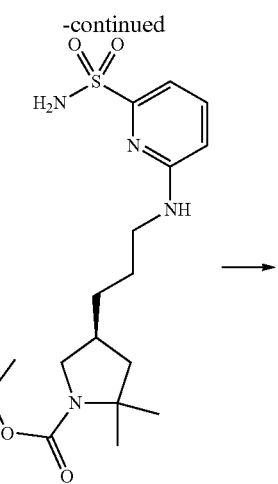

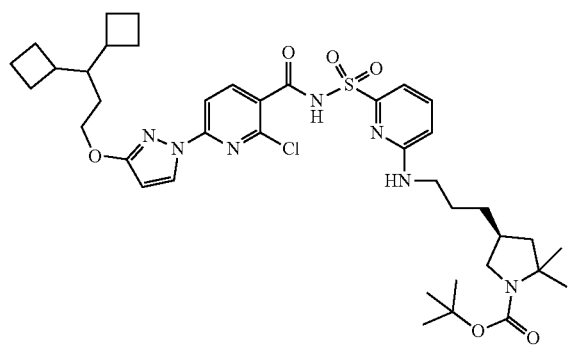

In a 20 mL scintillation vial, 2-chloro-6-[3-[3,3-di(cyclobutyl)propoxy]pyrazol-1-yl]pyridine-3-carboxylic acid (71 mg, 0.1821 mmol) and carbonyl diimidazole (30 mg, 0.1850 mmol) were combined in tetrahydrofuran (550 µL) and stirred for 60 min at 50° C. with a loose cap. Then, tert-butyl (4S)-2,2-dimethyl-4-[3-[(6-sulfamoyl-2-pyridyl)amino]propyl]pyrrolidine-1-carboxylate (50 mg, 0.1212 mmol) in tetrahydrofuran (850 µL) followed by 1,8-diazabicyclo[5.4.0]undec-7-ene (36 µL, 0.2407 mmol) was added and the reaction was heated at 50° C. for 16 h. The reaction mixture was allowed to cool to room temperature then concentrated to an oily residue which was diluted with ethyl acetate, washed with saturated aqueous ammonium chloride followed by brine. The organics were separated, dried over sodium sulfate, filtered and evaporated then purified by silica gel chromatography using a shallow gradient from 100% dichloromethane to 20% methanol in dichloromethane giving tert-butyl (4S)-4-[3-[[6-[[2-chloro-6-[3-[3,3-di(cyclobutyl)propoxy]pyrazol-1-yl]pyridine-3-carbonyl]sulfamoyl]-2-pyridyl]amino]propyl]-2,2-dimethyl-pyrrolidine-1-carboxylate (64.5 mg, 66%) as a light yellow thick oil. ESI-MS m/z calc. 783.3545, found 784.46 (M+1)$^+$; Retention time: 2.21 min (LC Method J).

Step 10: 2-Chloro-6-[3-[3,3-di(cyclobutyl)propoxy]pyrazol-1-yl]-N-[[6-[3-[(3S)-5,5-dimethylpyrrolidin-3-yl]propylamino]-2-pyridyl]sulfonyl]pyridine-3-carboxamide (Trifluoroacetate Salt)

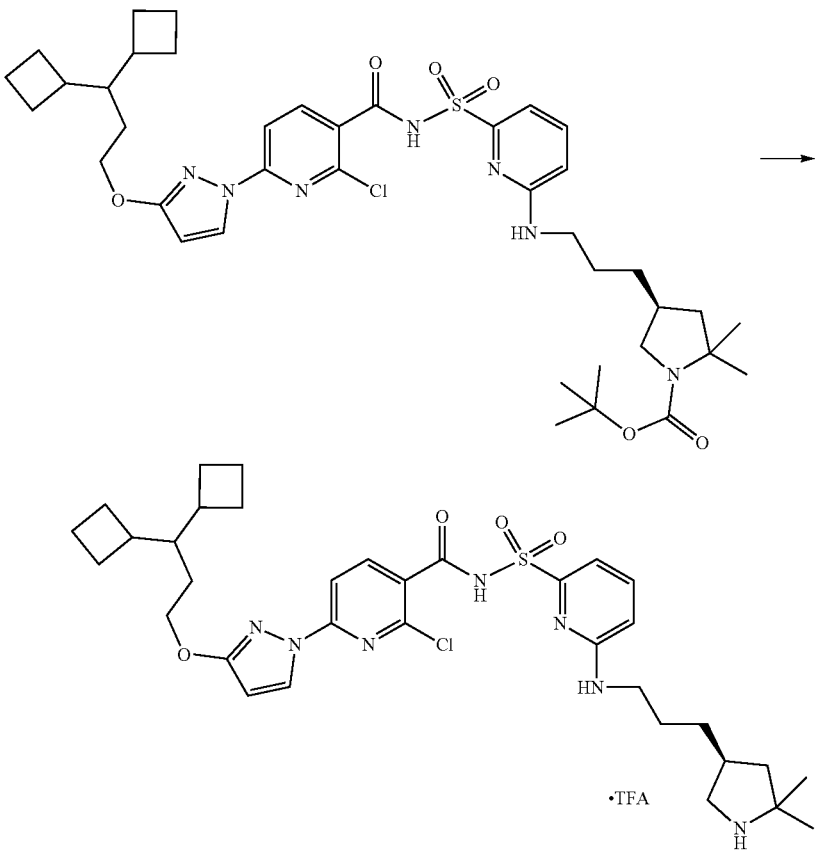

tert-Butyl (4S)-4-[3-[[6-[[2-chloro-6-[3-[3,3-di(cyclobutyl)propoxy]pyrazol-1-yl]pyridine-3-carbonyl]sulfamoyl]-2-pyridyl]amino]propyl]-2,2-dimethyl-pyrrolidine-1-carboxylate (64.5 mg, 0.082 mmol) was dissolved in dichloromethane (1.5 mL). Added trifluoroacetic acid (235 μL, 3.050 mmol) and the resulting reaction mixture was stirred at room temperature for 1 h. The mixture was concentrated under reduced pressure and the resulting crude was dried further under high vacuum to give 2-chloro-6-[3-[3,3-di(cyclobutyl)propoxy]pyrazol-1-yl]-N-[[6-[3-[(3S)-5,5-dimethylpyrrolidin-3-yl]propylamino]-2-pyridyl]sulfonyl]pyridine-3-carboxamide (trifluoroacetate salt) (53 mg, 52%, 97% purity) ESI-MS m/z calc. 683.30206, found 684.39 (M+1)$^+$; Retention time: 0.86 min (LC Method J).

Step 11: (14S)-8-[3-(3,3-Dicyclobutylpropoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 231)

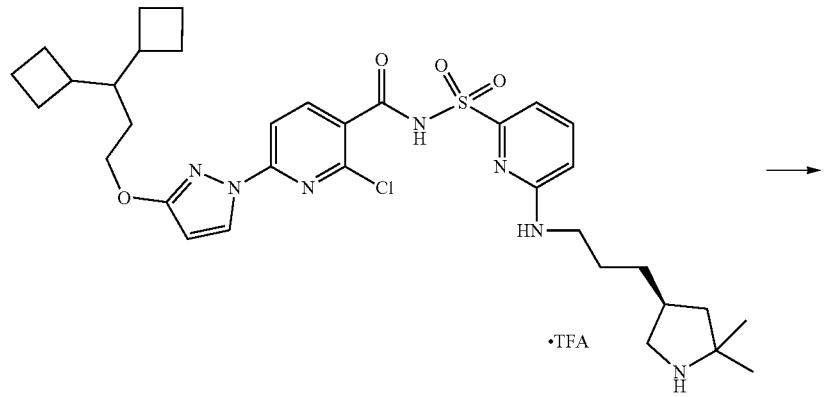

A mixture of 2-chloro-6-[3-[3,3-di(cyclobutyl)propoxy]pyrazol-1-yl]-N-[[6-[3-[(3S)-5,5-dimethylpyrrolidin-3-yl]propylamino]-2-pyridyl]sulfonyl]pyridine-3-carboxamide (trifluoroacetate salt) (52 mg, 0.07599 mmol), potassium carbonate (55 mg, 0.3980 mmol), cesium fluoride (25 mg, 0.1646 mmol), 3 Å molecular sieves and dimethyl sulfoxide (3.6 mL) were placed in a vial, purged with nitrogen, capped, heated to 165° C. and stirred for 16 h. The reaction was cooled to room temperature and the mixture was filtered. The filtrate was purified by reverse phase HPLC-MS using a Luna C$_{18}$ (2) column (75×30 mm, 5 μm particle size) sold by Phenomenex (pn: 00C-4252-U0-AX) and a dual gradient run from 30-99% mobile phase B over 15.0 min (mobile phase A=water (5 mM hydrochloric acid), mobile phase B=acetonitrile, Flow rate=50 mL/min, injection volume=1300 μL and column temperature=25° C.) to afford as a white solid, (14S)-8-[3-(3,3-dicyclobutylpropoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 231) (15.5 mg, 32%). $^1$H NMR (400 MHz, Chloroform-d) δ 9.96 (s, 1H), 8.19 (d, J=2.8 Hz, 1H), 8.07 (d, J=8.4 Hz, 1H), 7.60-7.48 (m, 2H), 7.28 (d, J=8.3 Hz, 1H), 6.56 (dd, J=8.1, 1.1 Hz, 1H), 5.91 (d, J=2.8 Hz, 1H), 4.70 (d, J=7.0 Hz, 1H), 4.20 (t, J=7.4 Hz, 2H), 3.90 (s, 1H), 3.35 (dd, J=10.1, 7.5 Hz, 1H), 3.17 (d, J=14.1 Hz, 1H), 3.06 (t, J=9.8 Hz, 1H), 2.26-2.11 (m, 2H), 2.09 (dd, J=12.3, 7.9 Hz, 1H), 2.03-1.86 (m, 3H), 1.80 (s, 1H), 1.82-1.72 (m, 2H), 1.76-1.62 (m, 3H), 1.62 (d, J=3.3

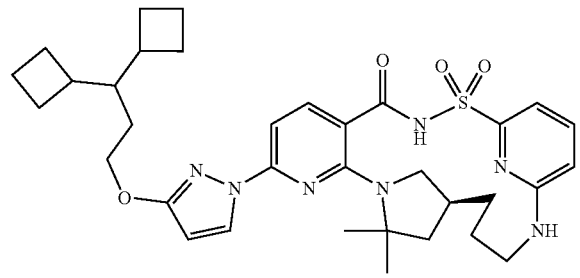

Hz, 7H), 1.46 (ddd, J=14.2, 9.0, 5.2 Hz, 1H), 1.26 (s, 1H), several aliphatic protons obscured by water peak. ESI-MS m/z calc. 647.3254, found 648.38 (M+1)⁺; Retention time: 1.89 min (LC Method J).

Example 69: Preparation of 7,7-dimethyl-11-(3-{3-[1-(trifluoromethyl)cyclopropyl]propoxy}-1H-pyrazol-1-yl)-17λ⁶-thia-2,8,10,16,22-pentaazatetracyclo[16.3.1.1⁵,⁸.0⁹,¹⁴]tricosa-1(22),9,11,13,18,20-hexaene-15,17,17-trione (Enantiomer 1) (Compound 234) and 7,7-dimethyl-11-(3-{3-[1-(trifluoromethyl)cyclopropyl]propoxy}-1H-pyrazol-1-yl)-17λ⁶-thia-2,8,10,16,22-pentaazatetracyclo[16.3.1.1⁵,⁸.0⁹,¹⁴]tricosa-1(22),9,11,13,18,20-hexaene-15,17,17-trione (Enantiomer 2) (Compound 235)

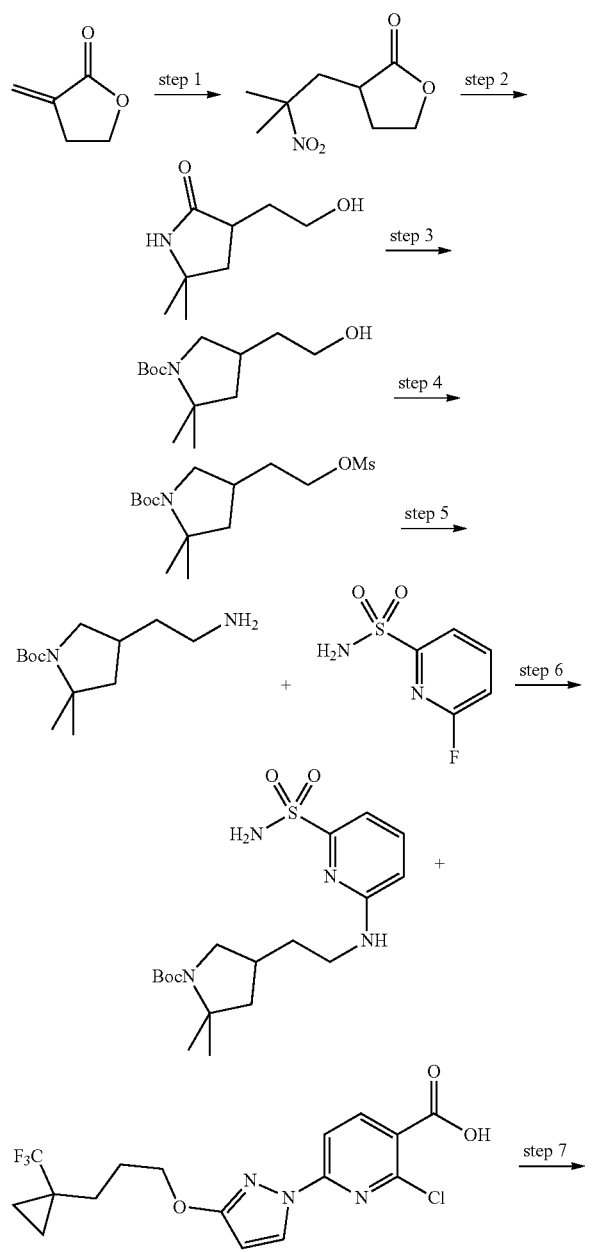

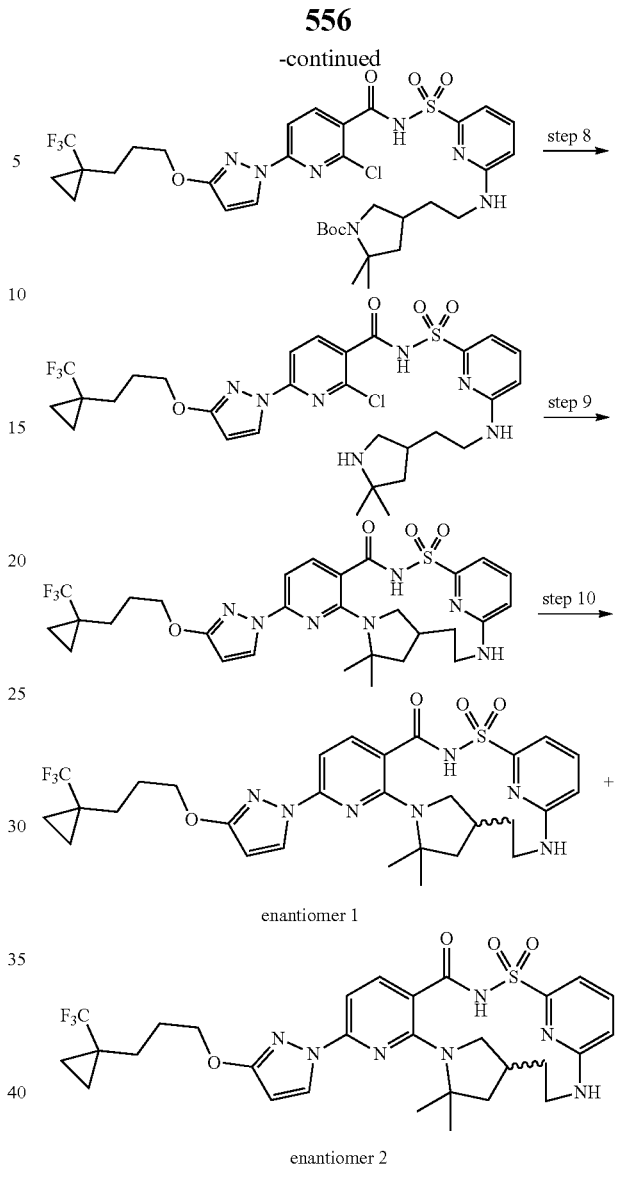

enantiomer 1 enantiomer 2

Step 1:
3-(2-Methyl-2-nitropropyl)-dihydrofuran-2-one

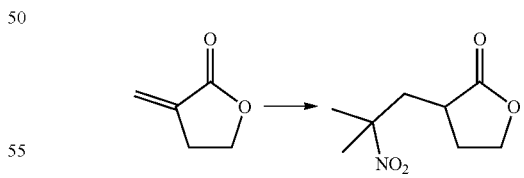

To a mixture of 2-nitropropane (49 mL, 2.2 mol) and 1,8-diazabicyclo[5.4.0]undec-7-ene (4.1 mL, 0.1 mol) under a nitrogen atmosphere, was added 3-methylenedihydrofuran-2(3H)-one (75 g, 776 mmol) dropwise over a period of 45 min. The addition is exothermic: the temperature was kept below 90° C. by controlling the addition rate during the course of the reaction. The mixture was stirred for an additional 4 h at 85° C., cooled to room temperature and diluted with ethyl acetate (500 mL) and 1M hydrochloric acid (60 mL). The organic phase was separated, dried over sodium sulfate, filtered and concentrated under vacuum to obtain a dark-colored oil. Trituration with a small amount of methyl tert-butyl ether produced a copious amount of white precipitate which was collected by filtration to obtain 3-(2-methyl-2-nitropropyl)-dihydrofuran-2-one (75.6 g, 73% yield) as a white solid. The material was used in the next step without further purification. ESI-MS m/z calc. 187.2, found 188.0 (M+1)$^+$. Retention time: 2.34 min (LC Method M).

Step 2:
3-(2-Hydroxyethyl)-5,5-dimethylpyrrolidin-2-one

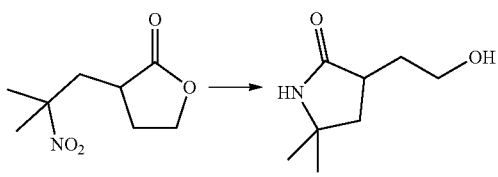

A 1.5 liter Parr reactor was charged with Raney Nickel slurry (10 g), 3-(2-methyl-2-nitropropyl)-dihydrofuran-2-one (75.6 g, 0.86 mol) and ethanol (1.2 L). The reactor was sealed and heated to 60° C. under 2 bars of hydrogen for 16 h and then cooled to room temperature. Approximately 100 g of Celite was added to the reactor. The resulting slurry was filtered through a thin pad of silica gel and rinsed with ethanol (200 mL). The combined filtrates were concentrated under vacuum to obtain 3-(2-hydroxyethyl)-5,5-dimethylpyrrolidin-2-one (64.5 g, quantitative yield) as a white solid The crude material was used in the next step without further purification. ESI-MS m/z calc. 157.2, found 158.1 (M+1)$^+$. Retention time: 1.38 min (LC Method M).

Step 3: (4-(2-hydroxyethyl)-2,2-dimethylpyrrolidine-1-carboxylic Acid tert-butyl ester

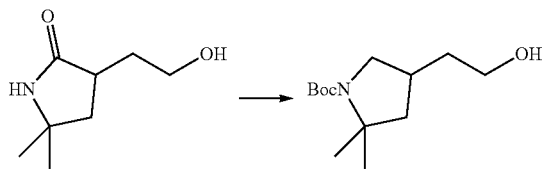 [SMILES: CC1(C)CC(CCO)C(=O)N1 ; CC(C)(C)OC(=O)N1CC(CCO)CC1(C)C]

Lithium aluminum hydride (53.9 g, 1.4 mol) was added to a mixture of 3-(2-hydroxyethyl)-5,5-dimethylpyrrolidin-2-one (55.8 g, 0.36 mol) and tetrahydrofuran (710 mL). The addition was done in small portions over a 45 min period in order to avoid excessive hydrogen evolution. The mixture was refluxed under nitrogen atmosphere for 22 h. The mixture was allowed to cool to room temperature and carefully quenched by the addition of sodium sulfate decahydrate (300 g). The resulting grey slurry was filtered and the solids were washed with tetrahydrofuran (500 mL). To the combined filtrates (1.2 L) was added di-tert-butyl dicarbonate (52.3 g, 225 mmol). The resulting mixture was stirred for 24 h at room temperature. The reaction mixture was concentrated and purified by silica gel chromatography using a 0%-100% gradient of ethyl acetate in hexanes to obtain (4-(2-hydroxyethyl)-2,2-dimethylpyrrolidine-1-carboxylic acid tert-butyl ester as a light-colored oil (40.8 g, 74% yield). ESI-MS m/z calc. 243.3, found 244.1 (M+1)$^+$. Retention Time: 4.01 min (LC Method M).

Step 4: 4-(2-Methanesulfonyloxyethyl)-2,2-dimethylpyrrolidine-1-carboxylic Acid tert-butyl ester


4-(2-Hydroxyethyl)-2,2-dimethylpyrrolidine-1-carboxylic acid tert-butyl ester (32.1 g, 132 mmol) and triethylamine (36.8 mL 264 mmol) were dissolved in dichloromethane (400 mL) and the resulting mixture was chilled in an ice water bath for 15 min. Methanesulfonyl chloride (11.3 mL, 145 mmol) was added dropwise and the reaction was stirred for 30 min. The reaction was quenched by the addition of saturated aqueous sodium bicarbonate (100 mL). The organic layer was separated, washed with water (100 mL), dried over sodium sulfate, filtered and concentered to obtain 4-(2-methanesulfonyloxyethyl)-2,2-dimethylpyrrolidine-1-carboxylic acid tert-butyl ester as an orange oil (41.6 g, 98% yield). The material was used in the next step without further purification. ESI-MS m/z calc. 321.4, found 322.2 (M+1)$^+$. Retention time: 4.88 min (LC Method M).

Step 5: 4-(2-Aminoethyl)-2,2-dimethylpyrrolidine-1-carboxylic Acid Tert-Butyl Ester


A 1.5 liter Parr reactor was charged with of 4-(2-methanesulfonyloxyethyl)-2,2-dimethylpyrrolidine-1-carboxylic acid tert-butyl ester (32.4 g, 101 mmol), dioxane (640 mL) and 30% ammonium hydroxide (640 mL). The reactor was sealed and heated to 50° C. for 18 h. The reaction mixture was concentrated under reduced pressure until most of the dioxane had been removed and then dichloromethane (1 L) was added. The resulting mixture was transferred into a separatory funnel and the phases were separated. The aqueous phase was extracted with dichloromethane (2×250 mL) and discarded. The combined organic phases were dried over sodium sulfate, filtered and concentrated. The crude material was purified by silica gel chromatography using a 0%-15% methanol in dichloromethane gradient containing 5 mL/liter of 30% ammonium hydroxide to obtain 4-(2-aminoethyl)-2,2-dimethylpyrrolidine-1-carboxylic acid tert-butyl ester (20.6 g, 66% yield) as a light-colored oil. $^1$H NMR (500 MHz, CDCl$_3$) δ (ppm): 3.66 (dt, 1H), 2.88 (p, 1H), 2.69 (m, 2H), 2.15 (m, 1H), 1.88 (m, 1H), 1.48-1.14 (m, 20H). ESI-MS m/z calc. 242.3, found 243.0 (M+1)$^+$. Retention time: 3.06 min (LC Method M).

Step 6: tert-Butyl 2,2-dimethyl-4-[2-[(6-sulfamoyl-2-pyridyl)amino]ethyl]pyrrolidine-1-carboxylate

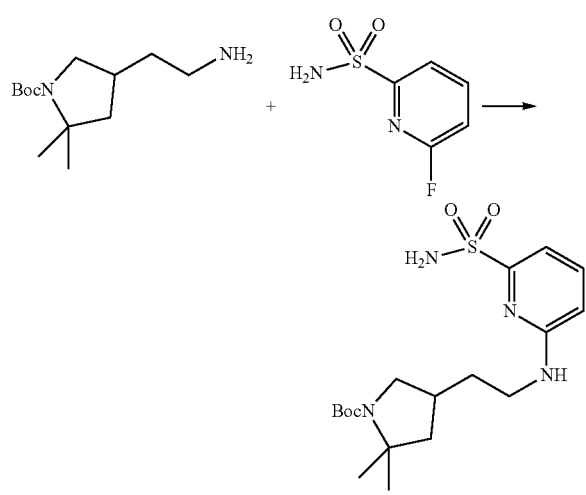

6-Fluoropyridine-2-sulfonamide (2.089 g, 11.86 mmol) and dimethyl sulfoxide (24 mL) were added to a 20 mL microwave vessel. Potassium carbonate (8.60 g, 62.23 mmol) and tert-butyl 4-(2-aminoethyl)-2,2-dimethyl-pyrrolidine-1-carboxylate (3.00 g, 12.38 mmol) were added and the vial was capped and heated to 100° C. on a hot plate for 4 h. The reaction mixture was filtered, then diluted with ethyl acetate and washed with a 1M citric acid solution, followed by brine. The organic layer was separated, dried over sodium sulfate, filtered and evaporated then purified by silica gel chromatography using a gradient from 100% hexanes to 80% ethyl acetate in hexanes to afford as a white solid, tert-butyl 2,2-dimethyl-4-[2-[(6-sulfamoyl-2-pyridyl)amino]ethyl]pyrrolidine-1-carboxylate (1.475 g, 31%). ESI-MS m/z calc. 398.19876, found 399.2 (M+1)$^+$; Retention time: 1.55 min (LC Method B).

Step 7: tert-Butyl 4-[2-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]ethyl]-2,2-dimethyl-pyrrolidine-1-carboxylate

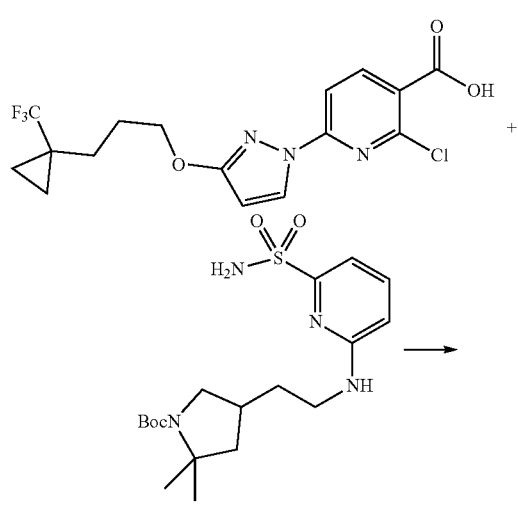

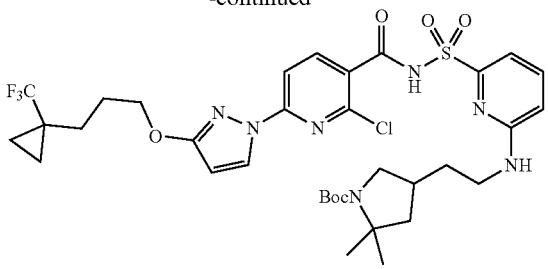

To a round bottom flask was added 2-chloro-6-[3-[3-[1-(trifluoromethyl)cyclopropyl]propoxy]pyrazol-1-yl]pyridine-3-carboxylic acid (361 mg, 0.9262 mmol) and freshly recrystallized carbonyl diimidazole (188 mg, 1.159 mmol). Tetrahydrofuran (5.5 mL) was added and the reaction was heated at 40° C. for 2 h. A solution of tert-butyl 2,2-dimethyl-4-[2-[(6-sulfamoyl-2-pyridyl)amino]ethyl]pyrrolidine-1-carboxylate (370 mg, 0.9284 mmol) in tetrahydrofuran (2 mL) was added followed by 1,8-diazabicyclo[5.4.0]undec-7-ene (450 μL, 3.009 mmol). The reaction turned pale yellow and was allowed to stir overnight at room temperature. The reaction was quenched with saturated sodium bicarbonate and brine and extracted with ethyl acetate. The organic layer was dried over sodium sulfate, filtered and evaporated. The crude residue was then purified via silica gel chromatography using a gradient from 0%-100% ethyl acetate in hexanes giving tert-butyl 4-[2-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]ethyl]-2,2-dimethyl-pyrrolidine-1-carboxylate (400 mg, 56%) as a white foam. ESI-MS m/z calc. 769.2636, found 770.4 (M+1)$^+$; Retention time: 2.01 min (LC Method G).

Step 8: 2-chloro-N-[[6-[2-(5,5-dimethylpyrrolidin-3-yl)ethylamino]-2-pyridyl]sulfonyl]-6-[3-[3-[1-(trifluoromethyl)cyclopropyl]propoxy]pyrazol-1-yl]pyridine-3-carboxamide

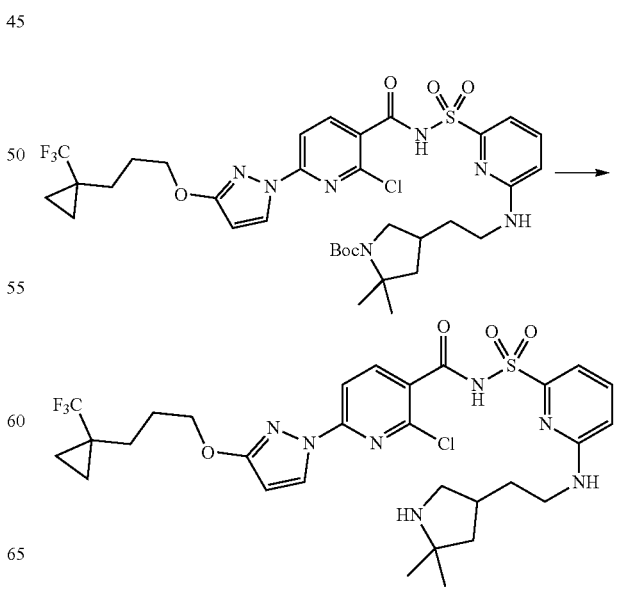

To a round bottom flask containing tert-butyl 4-[2-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]ethyl]-2,2-dimethyl-pyrrolidine-1-carboxylate (400 mg, 0.5193 mmol) was added dichloromethane (10 mL) and trifluoroacetic acid (2.0 mL, 25.96 mmol). The reaction was stirred for 90 min at room temperature. The reaction was then evaporated to dryness. The crude reaction mixture was neutralized with saturated sodium bicarbonate and extracted with ethyl acetate. The product crashed out and a little methanol was used to help in the extraction. The organic layer was separated (not dried over sodium sulfate) and evaporated to provide 2-chloro-N-[[6-[2-(5,5-dimethylpyrrolidin-3-yl)ethylamino]-2-pyridyl]sulfonyl]-6-[3-[3-[1-(trifluoromethyl)cyclopropyl]propoxy]pyrazol-1-yl]pyridine-3-carboxamide (344 mg, 99%) as a white solid. ESI-MS m/z calc. 669.2112, found 670.5 (M+1)$^+$; Retention time: 0.94 min (LC Method G).

Step 9: 7,7-Dimethyl-11-(3-{3-[1-(trifluoromethyl)cyclopropyl]propoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (Compound 233)

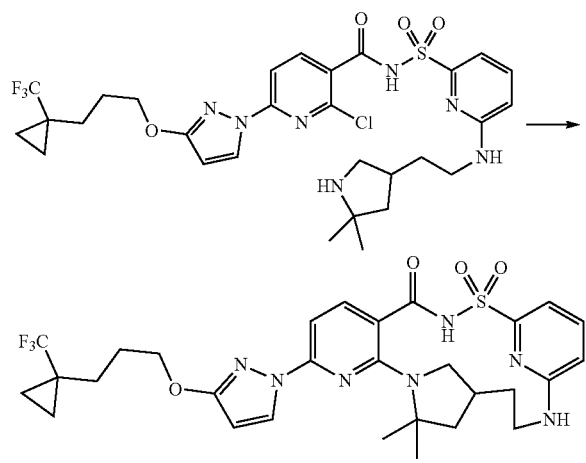

To a microwave vial was added potassium carbonate (355 mg, 2.569 mmol), cesium fluoride (156 mg, 1.027 mmol), several 3 Å molecular sieves and a solution of 2-chloro-N-[[6-[2-(5,5-dimethylpyrrolidin-3-yl)ethylamino]-2-pyridyl]sulfonyl]-6-[3-[3-[1-(trifluoromethyl)cyclopropyl]propoxy]pyrazol-1-yl]pyridine-3-carboxamide (344 mg, 0.5133 mmol) in dimethyl sulfoxide (4 mL). The reaction was capped and placed in a preheated 150° C. oil bath overnight. The reaction was cooled to room temperature, filtered and purified via HPLC 50%-99% acetonitrile in water (0.1% hydrochloric acid modifier) gradient giving 7,7-dimethyl-11-(3-{3-[1-(trifluoromethyl)cyclopropyl]propoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (Compound 233) (138.6 mg, 43%) as a white powder. ESI-MS m/z calc. 633.2345, found 634.3 (M+1)$^+$; Retention time: 2.22 min (LC Method B).

Step 10: 7,7-Dimethyl-11-(3-{3-[1-(trifluoromethyl)cyclopropyl]propoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (Enantiomer 1) (Compound 234) and 7,7-dimethyl-11-(3-{3-[1-(trifluoromethyl)cyclopropyl]propoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (Enantiomer 2) (Compound 235)

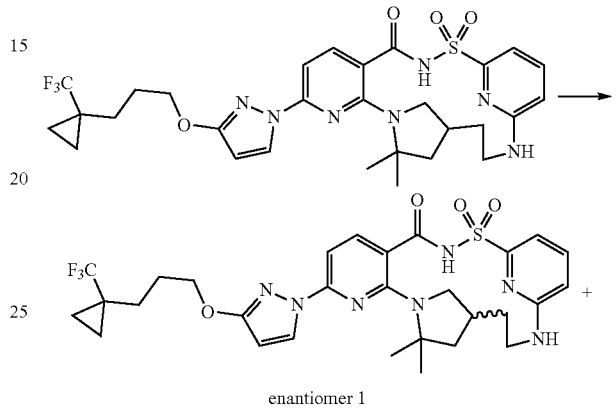

enantiomer 1

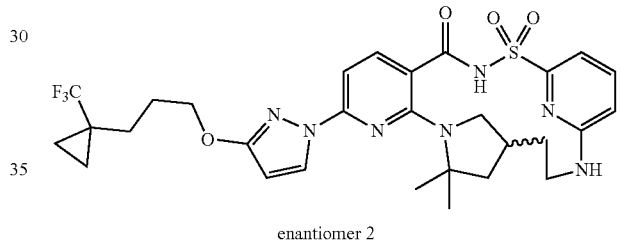

enantiomer 2

Racemic 7,7-dimethyl-11-(3-{3-[1-(trifluoromethyl)cyclopropyl]propoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (Compound 233) (138.6 mg, 0.2187 mmol) was separated by chiral SFC chromatography using a ChiralPak AS-H (250×21.2 mm column, 5 μm particle size) with 28% acetonitrile:methanol (90:10, no modifier))/72% carbon dioxide mobile phase at 70 mL/min giving as the as the first enantiomer to elute, 7,7-dimethyl-11-(3-{3-[1-(trifluoromethyl)cyclopropyl]propoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (enantiomer 1) (Compound 234) (68.1 mg, 98%). ESI-MS m/z calc. 633.2345, found 634.4 (M+1)$^+$; Retention time: 2.22 min (LC Method B). The second enantiomer to elute was 7,7-dimethyl-11-(3-{3-[1-(trifluoromethyl)cyclopropyl]propoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (enantiomer 2) (Compound 235) (59.3 mg, 86%). $^1$H NMR (400 MHz, dimethyl sulfoxide-d$_6$) δ 12.46 (s, 1H), 8.20 (d, J=2.8 Hz, 1H), 7.75 (d, J=33.8 Hz, 2H), 7.18 (s, 1H), 6.90 (d, J=8.2 Hz, 1H), 6.82 (s, 1H), 6.11 (d, J=2.8 Hz, 1H), 4.20 (t, J=6.2 Hz, 2H), 3.72-3.46 (m, 1H), 2.26 (s, 1H), 1.99-1.65 (m, 6H), 1.55 (s, 6H), 1.49-1.15 (m, 2H), 0.95-0.87 (m, 2H), 0.79-0.70 (m, 2H), some protons obscured by solvent. ESI-MS m/z calc. 633.2345, found 634.3 (M+1)$^+$; Retention time: 2.22 min (LC Method B).

Example 70: Preparation of (14S)-12,12-dimethyl-8-[2-oxo-3-(4,4,4-trifluoro-3,3-dimethylbutoxy)pyrrolidin-1-yl]-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 237)

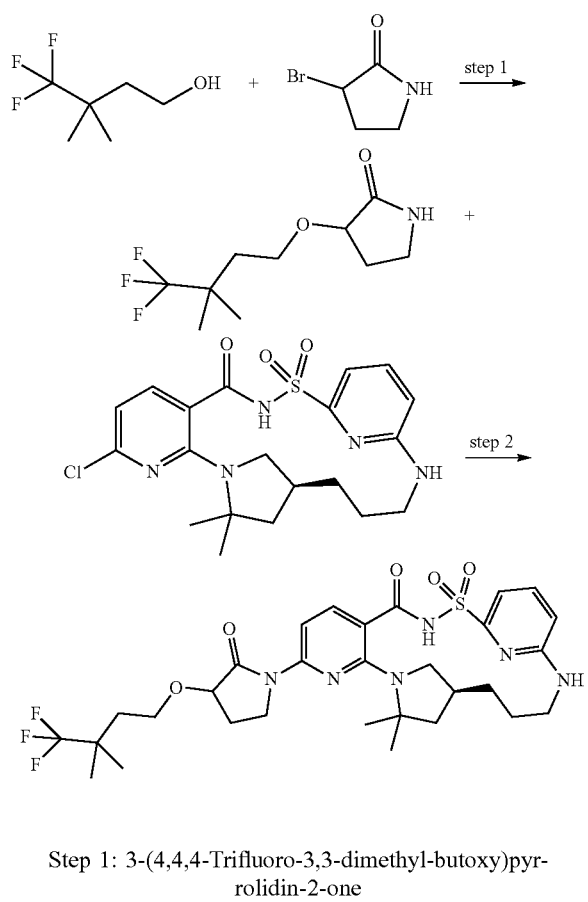

Step 1: 3-(4,4,4-Trifluoro-3,3-dimethyl-butoxy)pyrrolidin-2-one

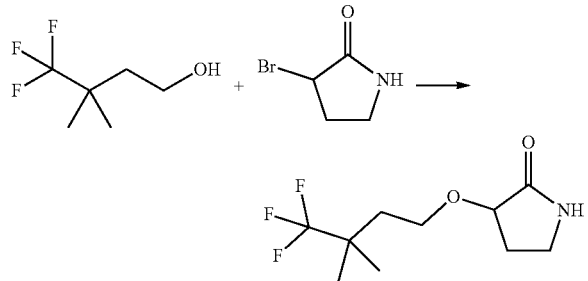

To a stirred solution of 4,4,4-trifluoro-3,3-dimethyl-butan-1-ol (280 mg, 1.793 mmol, contains 29 mol % residual diethyl ether) and 3-bromopyrrolidin-2-one (275 mg, 1.677 mmol) in anhydrous tetrahydrofuran (12 mL) was added [bis(trimethylsilyl)amino]potassium (7.1 mL of 0.5 M in toluene, 3.550 mmol) dropwise at –50° C. to –60° C. over 2 min under nitrogen. After stirring for 15 min at that temperature, the cooling bath was removed and the flask was placed immediately in an ice-water bath at 0° C. The reaction was then allowed to warm to ambient temperature and stirring continued overnight under nitrogen. Glacial acetic acid (200 µL, 3.517 mmol) was added to the reaction and the volatiles were removed under reduced pressure. The residue was purified by silica gel chromatography (0%-10% methanol in dichloromethane gradient over 25 min) to furnish 3-(4,4,4-trifluoro-3,3-dimethyl-butoxy)pyrrolidin-2-one (238 mg, 59%) as an off-white solid. $^1$H NMR (400 MHz, Benzene-$d_6$) δ 5.87 (s, 1H), 4.13 (dt, J=9.6, 7.0 Hz, 1H), 3.42 (dt, J=9.6, 6.8 Hz, 1H), 3.39-3.33 (m, 1H), 2.52-2.41 (m, 1H), 2.25 (dt, J=9.6, 7.0 Hz, 1H), 1.72 (td, J=6.9, 1.5 Hz, 2H), 1.57-1.43 (m, 2H), 0.94 (d, J=3.6 Hz, 6H). $^{19}$F NMR (376 MHz, Benzene-$d_6$) δ –78.62. ESI-MS m/z calc. 239.11331, found 240.2 (M+1)⁺; Retention time: 1.16 min (LC Method B).

Step 2: (14S)-12,12-Dimethyl-8-[2-oxo-3-(4,4,4-trifluoro-3,3-dimethylbutoxy) pyrrolidin-1-yl]-2λ⁶-thia-3,9,11,18,23-pentaazatetracyclo[17.3.1.1¹¹¹,14.0⁵,¹⁰]tetracosa-1(22),5,7,9,19(23),20-hexaene-2,2,4-trione (Compound 237)

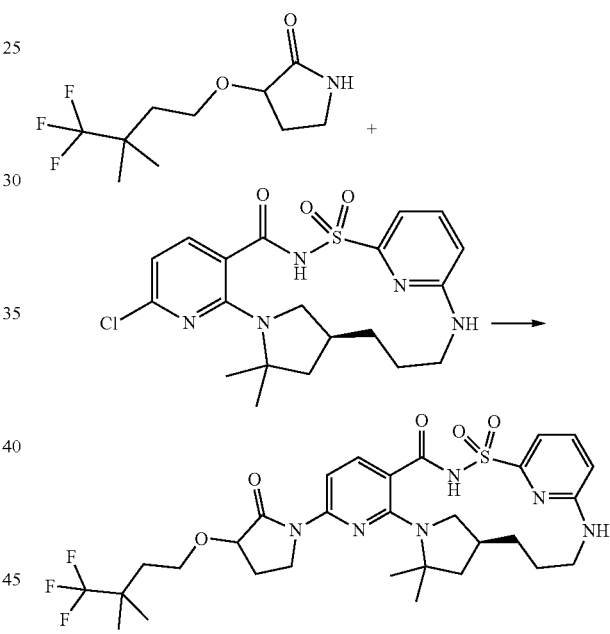

To a 4 mL vial was added, (14S)-8-chloro-12,12-dimethyl-2λ⁶-thia-3,9,11,18,23-pentaazatetracyclo[17.3.1.1¹¹¹,14.05,10]tetracosa-1(23),5,7,9,19,21-hexaene-2,2,4-trione (20 mg, 0.04445 mmol), 3-(4,4,4-trifluoro-3,3-dimethyl-butoxy)pyrrolidin-2-one (13 mg, 0.05434 mmol), cesium carbonate (52 mg, 0.1596 mmol), 4,5-bis(diphenylphosphino)-9,9-dimethylxanthene (4 mg, 0.006913 mmol) and anhydrous dioxane (0.7 mL) in that order. Nitrogen was purged through the heterogeneous mixture for 3 min. Then tris(benzylideneacetone)dipalladium(0) (4 mg, 0.004368 mmol) was added under nitrogen and nitrogen was purged through the mixture for another 2 min and capped under a nitrogen atmosphere. The mixture was stirred at 108° C. overnight. The mixture was allowed to cool to ambient temperature and neutralized with glacial acetic acid (20 µL, 0.3517 mmol). The volatiles were removed under reduced pressure and the residue was taken up in dimethyl sulfoxide (1.5 mL) and filtered through a Whatman 0.45 µm PTFE syringe filter disc. The sample was purified using preparative reverse-phase HPLC-MS [Luna C$_{18}$ (2) column (75×30 mm, 5 lam particle size) sold by Phenomenex (pn: 00C-4252-U0-AX), dual gradient run from 30%-99% acetonitrile in water over 15 min (hydrochloric acid as modifier)] giving (14S)-12,12-dimethyl-8-[2-oxo-3-(4,4,4-trifluoro-3,3-dimethylbutoxy)pyrrolidin-1-yl]-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 237) (8 mg, 27%) as a yellowish solid. $^1$H NMR (400 MHz, dimethyl sulfoxide-d$_6$) δ 12.42 (s, 1H), 7.71 (dd, J=8.4, 1.9 Hz, 1H), 7.57 (dd, J=8.5, 7.2 Hz, 1H), 7.52 (dd, J=8.4, 6.3 Hz, 1H), 7.04 (dt, J=7.3, 0.9 Hz, 1H), 6.96 (d, J=8.8 Hz, 1H), 6.70 (dd, J=8.5, 0.8 Hz, 1H), 4.31 (two t, J=8.3 Hz, 1H), 4.08-3.87 (m, 3H), 3.81-3.64 (m, 2H), 3.17-3.04 (m, 1H), 2.94 (d, J=13.2 Hz, 1H), 2.73-2.63 (m, 1H), 2.47-2.38 (m, 1H), 2.15-2.02 (m, 1H), 1.98-1.86 (m, 1H), 1.82 (dd, J=11.7, 5.1 Hz, 1H), 1.76 (td, J=7.0, 1.8 Hz, 3H), 1.69-1.57 (m, 2H), 1.57 (s, 3H), 1.50 (t, J=12.4 Hz, 1H), 1.46 (s, 3H), 1.29 (dd, J=13.6, 12.8 Hz, 1H), 1.14 (t, J=1.9 Hz, 6H). $^{19}$F NMR (376 MHz, dimethyl sulfoxide-d$_6$) δ−77.59. ESI-MS m/z calc. 652.2655, found 653.4 (M+1)$^+$; Retention time: 2.1 min (LC Method B).

Example 71: Preparation of 12,12-dimethyl-8-{3-[3-methyl-2-(propan-2-yl)butoxy]-1H-pyrazol-1-yl}-15-oxa-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 238)

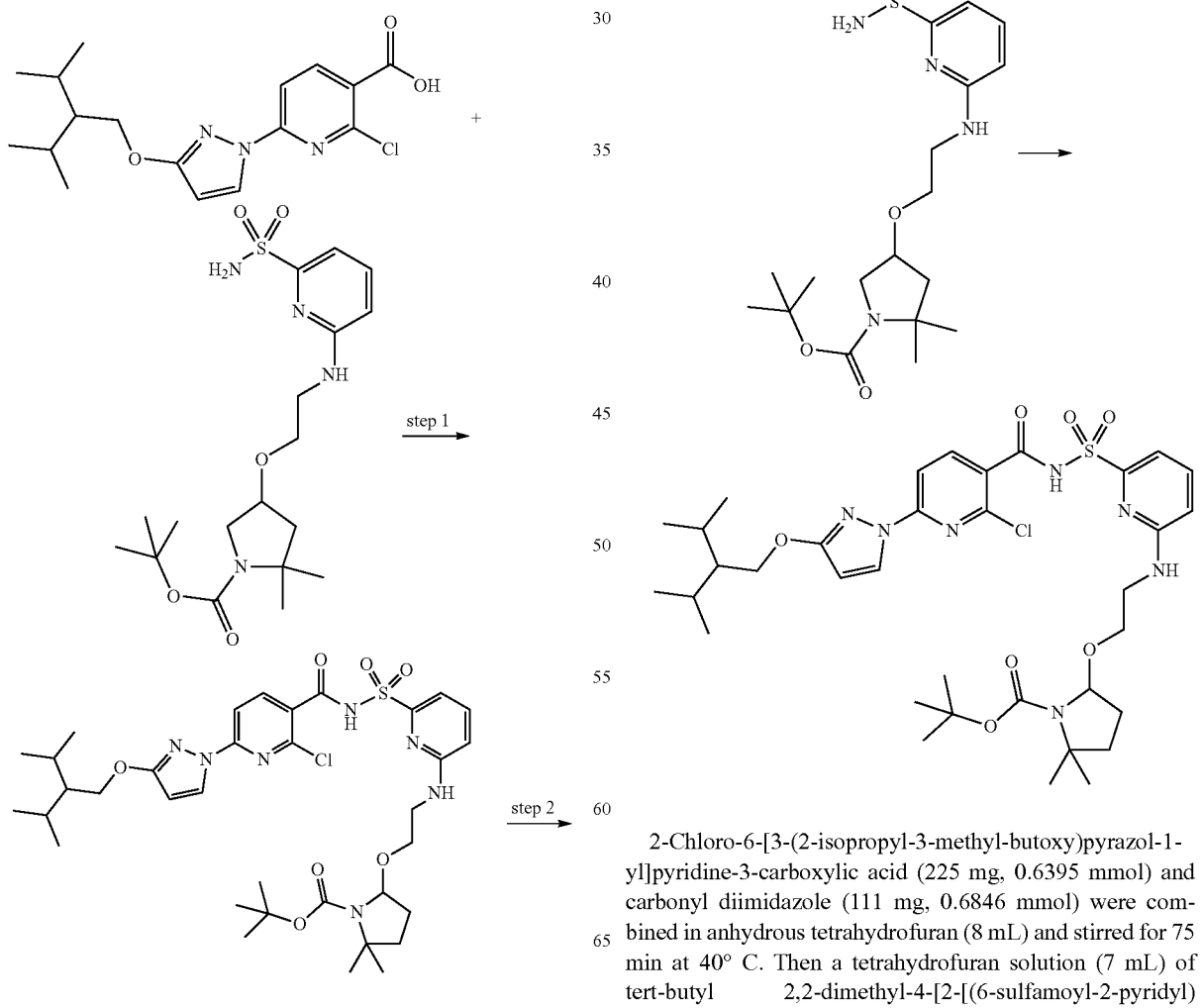

Step 1: tert-Butyl 4-[2-[[6-[[2-chloro-6-[3-(2-isopropyl-3-methyl-butoxy)pyrazol-1-yl]pyridine-3-carbonyl]sulfamoyl]-2-pyridyl]amino]ethoxy]-2,2-dimethyl-pyrrolidine-1-carboxylate 2-Chloro-6-[3-(2-isopropyl-3-methyl-butoxy)pyrazol-1-yl]pyridine-3-carboxylic acid (225 mg, 0.6395 mmol) and carbonyl diimidazole (111 mg, 0.6846 mmol) were combined in anhydrous tetrahydrofuran (8 mL) and stirred for 75 min at 40° C. Then a tetrahydrofuran solution (7 mL) of tert-butyl 2,2-dimethyl-4-[2-[(6-sulfamoyl-2-pyridyl)

amino]ethoxy]pyrrolidine-1-carboxylate (265 mg, 0.6393 mmol) and 1,8-diazabicyclo[5.4.0]undec-7-ene (200 µL, 1.337 mmol) was added. The reaction was heated at 50° C. for 4 h. The reaction was diluted with ethyl acetate and washed with a 1 M citric acid solution, followed by brine. The organics were separated, dried over sodium sulfate, filtered and evaporated and then purified on silica gel chromatography using a gradient of 100% hexanes to 75% ethyl acetate in hexanes to afford as an off-white solid, tert-butyl 4-[2-[[6-[[2-chloro-6-[3-(2-isopropyl-3-methyl-butoxy)pyrazol-1-yl]pyridine-3-carbonyl]sulfamoyl]-2-pyridyl]amino]ethoxy]-2,2-dimethyl-pyrrolidine-1-carboxylate (176 mg, 37%). ESI-MS m/z calc. 747.3181, found 748.41 (M+1)⁺; Retention time: 0.67 min (LC Method A).

Step 2: 12,12-Dimethyl-8-{3-[3-methyl-2-(propan-2-yl)butoxy]-1H-pyrazol-1-yl}-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 238)

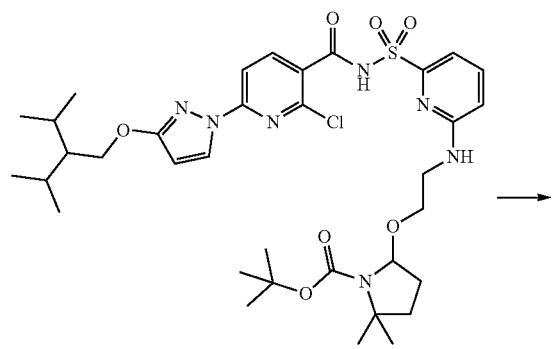

tert-Butyl 4-[2-[[6-[[2-chloro-6-[3-(2-isopropyl-3-methyl-butoxy)pyrazol-1-yl]pyridine-3-carbonyl]sulfamoyl]-2-pyridyl]amino]ethoxy]-2,2-dimethyl-pyrrolidine-1-carboxylate (176 mg, 0.2352 mmol) was dissolved in dichloromethane (3 mL) and to the mixture was added trifluoroacetic acid (550 µL, 7.14 mmol). The reaction solution was stirred at room temperature for 30 min. The reaction mixture was concentrated to dryness under reduced pressure. The resulting residue was combined with potassium carbonate (195 mg, 1.41 mmol), cesium fluoride (53.6 mg, 0.353 mmol), 3 Å molecular sieves and dimethyl sulfoxide (3 mL) in a vial and purged with nitrogen. The vial was capped, heated to 140° C. and stirred for 20 h. The mixture was cooled to room. The reaction mixture was filtered and then purified by reverse-phase preparative chromatography (C₁₈ column, 30% to 99% acetonitrile (no modifier) in water (5 mM hydrochloric acid) over 30 min) to afford as a white solid, 12,12-dimethyl-8-{3-[3-methyl-2-(propan-2-yl)butoxy]-1H-pyrazol-1-yl}-15-oxa-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 238) (64 mg, 44%). ¹H NMR (400 MHz, dimethyl sulfoxide-d₆) δ 12.59 (s, 1H), 8.20 (d, J=2.8 Hz, 1H), 7.79 (d, J=8.2 Hz, 1H), 7.59 (dd, J=8.5, 7.2 Hz, 1H), 7.13 (d, J=9.1 Hz, 1H), 7.10 (d, J=7.2 Hz, 1H), 6.96 (d, J=8.2 Hz, 1H), 6.71 (d, J=8.5 Hz, 1H), 6.11 (d, J=2.8 Hz, 1H), 4.23 (d, J=4.8 Hz, 2H), 4.10 (d, J=8.7 Hz, 2H), 3.88 (t, J=11.9 Hz, 1H), 3.61 (d, J=12.7 Hz, 1H), 3.22 (s, 1H), 2.87 (d, J=9.4 Hz, 1H), 2.08 (dd, J=11.4, 6.0 Hz, 1H), 1.89 (dq, J=13.2, 6.6 Hz, 2H), 1.79 (t, J=10.9 Hz, 1H), 1.58 (d, J=9.7 Hz, 6H), 1.42-1.30 (m, 2H), 0.98 (d, J=6.8 Hz, 6H), 0.92 (d, J=6.8 Hz, 6H). ESI-MS m/z calc. 611.289, found 612.2 (M+1)⁺; Retention time: 2.29 min (LC Method B).

Example 72: Preparation of (14S)-8-{3-[2-(adamantan-1-yl)ethoxy]-2-oxopyrrolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 240) and (14S)-8-{3-[2-(adamantan-1-yl)ethoxy]-2-oxopyrrolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 241)

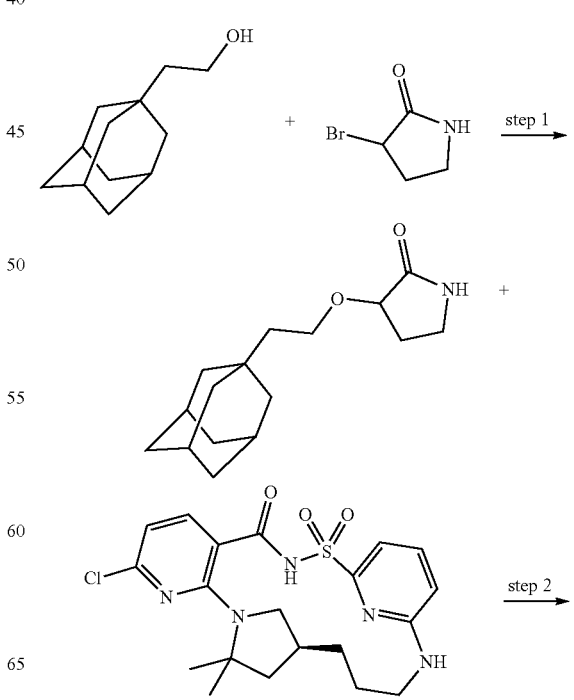

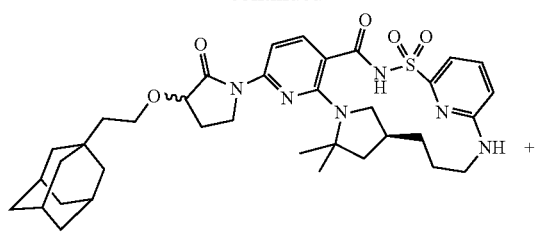

diastereomer 1

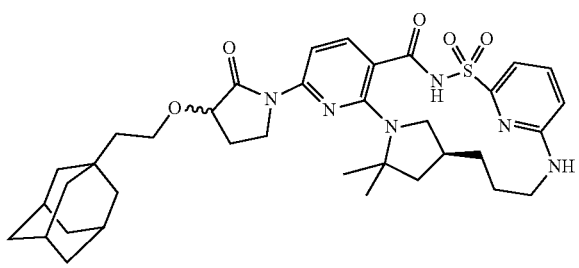

diastereomer 2

Step 1: 3-[2-(1-Adamantyl)ethoxy]pyrrolidin-2-one

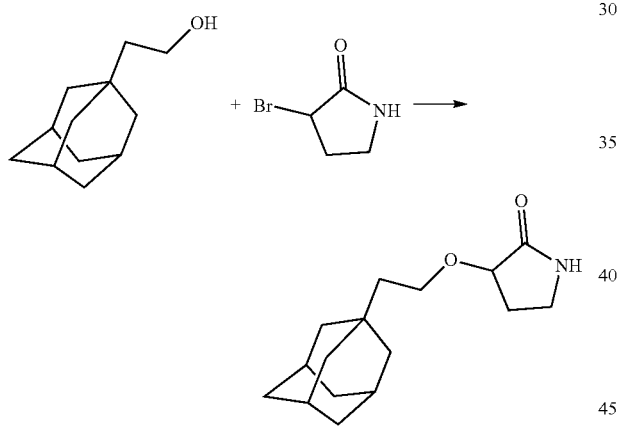

Into a solution of 1-adamantaneethanol (1.099 g, 6.098 mmol) and 3-bromopyrrolidin-2-one (1.00 g, 6.098 mmol) in anhydrous tetrahydrofuran (50 mL) was added potassium bis(trimethylsilyl)amide (1.0 M in tetrahydrofuran, 12.8 mL, 12.8 mmol) at −50° C. dropwise. The reaction was stirred at the same temperature for 20 min, then in an ice bath for 3 h. The reaction was quenched with saturated aqueous ammonium chloride solution (50 mL) and extracted with ethyl acetate (3×50 mL). The combined organic layers were washed with brine (50 mL), dried over anhydrous sodium sulfate, filtered and concentrated. The residue was triturated with hexane and the formed solid was collected by filtration to furnish 3-(2-adamantan-1-yl-ethoxy)-pyrrolidin-2-one (1.192 g, 74%) as an off-white solid. $^1$H NMR (250 MHz, dimethyl sulfoxide-$d_6$) d (ppm): 7.78 (s, br, 1H), 3.81 (m, 2H), 3.51 (q, t=8.8 Hz, 1H), 3.11 (m, 2H), 2.27 (m, 1H), 1.90-1.40 (m, 16H), 1.30 (t, J=7.3 Hz, 2H). ESI-MS m/z: calc. 263.19, found 263.8 (M+1)$^+$. Retention time: 5.24 min (LC Method Q).

Step 2: (14S)-8-{3-[2-(Adamantan-1-yl)ethoxy]-2-oxopyrrolidin-1-yl}-12,12-dimethyl-2λ$^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 240) and (14S)-8-{3-[2-(adamantan-1-yl)ethoxy]-2-oxopyrrolidin-1-yl}-12,12-dimethyl-2λ$^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 241)

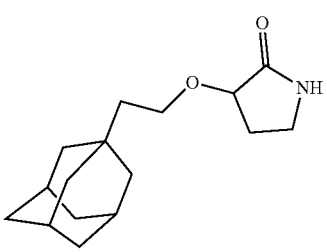

+

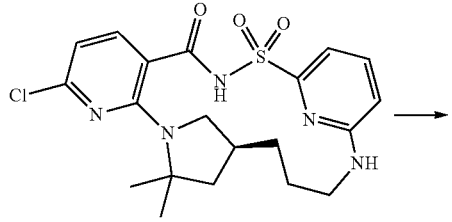

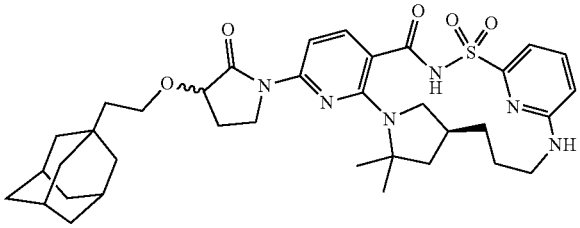

diastereomer 1

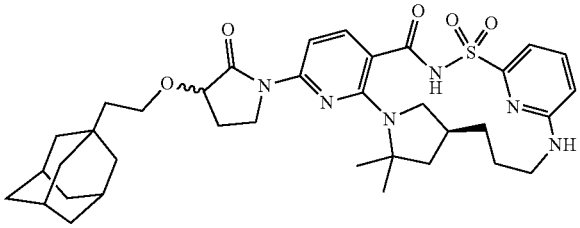

diastereomer 2

A 4 mL vial was charged with (14S)-8-chloro-12,12-dimethyl-2λ$^6$-thia-3,9,11,18,23-pentaazatetracyclo [17.3.1.1¹¹,¹⁴.0⁵,¹⁰]tetracosa-1(23),5,7,9,19,21-hexaene-2,2,4-trione (35 mg, 0.07779 mmol), 3-[2-(1-adamantyl)ethoxy]pyrrolidin-2-one (29 mg, 0.1101 mmol), Pd$_2$(dba)$_3$ (11 mg, 0.01201 mmol), Xantphos (9 mg, 0.01555 mmol), cesium carbonate (129 mg, 0.3959 mmol) and anhydrous dioxane (0.5 mL). The mixture was sparged with nitrogen for about 3 min, capped and stirred at 120° C. for 14 h. The organic solvent was concentrated by blowing nitrogen into the vial. The residue was diluted with dimethyl sulfoxide (900 µL), microfiltered and subjected to reverse phase preparative HPLC (C$_{18}$) using a gradient of acetonitrile in water (30 to 99% over 15 min) and hydrochloric acid as a modifier. The pure fractions were collected and the organic solvents were evaporated. The resulting aqueous solution was extracted with dichloromethane (1×) and ethyl acetate (2×) and the organic phases were combined and dried over sodium sulfate. Filtration then evaporation of the solvents gave a solid that was further purified by flash chromatography on silica gel using a gradient of methanol (0% to 5% over 30 min) in dichloromethane. The pure fractions were combined and the solvents evaporated. The residue was triturated with dichloromethane/hexanes and the solvents evaporated to give a mixture of diastereomers that were separated by chiral SFC (chiralCel OJ-H (250×10 mm), 5 μM column; mobile phase: 24% acetonitrile/methanol (90:10, 20 mM NH₃), 76% carbon dioxide, 10 mL/min; 14 mg/mL in acetonitrile: methanol: dimethyl sulfoxide (81:9:10); injection volume 70 μL, 100 bar).

The first diastereomer to elute was (14S)-8-{3-[2-(adamantan-1-yl)ethoxy]-2-oxopyrrolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 1) (Compound 240) (6.1 mg, 22%, 98% ee). ¹H NMR (400 MHz, dimethyl sulfoxide-d₆) δ 12.45 (broad s, 1H), 7.69 (d, J=8.4 Hz, 1H), 7.60-7.44 (m, 2H), 7.03 (d, J=7.2 Hz, 1H), 6.94 (br s, 1H), 6.68 (br d, J=8.5 Hz, 1H), 4.21 (t, J=8.0 Hz, 1H), 4.02 (t, J=9.5 Hz, 1H), 3.97-3.82 (m, 2H), 3.74-3.65 (m, 1H), 3.64-3.53 (m, 1H), 3.12 (br s, 1H), 2.93 (d, J=13.3 Hz, 1H), 2.77-2.64 (m, 1H), 2.45-2.34 (m, 1H), 2.17-2.03 (m, 1H), 2.00-1.71 (m, 6H), 1.70-1.39 (m, 19H), 1.40-1.13 (m, 5H). ESI-MS m/z calc. 676.3407, found 677.4 (M+1)⁺; Retention time: 2.42 min (LC Method B). The second diastereomer to elute was (14S)-8-{3-[2-(adamantan-1-yl)ethoxy]-2-oxopyrrolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 2) (Compound 241) (5.1 mg, 17%, 93% ee). ¹H NMR (400 MHz, dimethyl sulfoxide-d₆) δ 12.44 (broad s, 1H), 7.70 (d, J=8.4 Hz, 1H), 7.61-7.49 (m, 2H), 7.04 (d, J=7.2 Hz, 1H), 7.00-6.89 (br m, 1H), 6.70 (d, J=8.5 Hz, 1H), 4.26 (t, J=8.2 Hz, 1H), 3.98-3.82 (m, 3H), 3.76 (q, J=8.5 Hz, 1H), 3.58 (q, J=7.7 Hz, 1H), 3.10 (br s, 1H), 2.94 (br d, J=13.3 Hz, 1H), 2.74-2.63 (m, 1H), 2.47-2.34 (m, 1H), 2.10 (br s, 1H), 1.95-1.69 (m, 6H), 1.68-1.39 (m, 19H), 1.37-1.18 (m, 5H). ESI-MS m/z calc. 676.3407, found 677.4 (M+1)⁺; Retention time: 2.41 min (LC Method B).

Example 73: Preparation of (14S)-12,12-dimethyl-8-(2-oxo-3-{3-[1-(trifluoromethyl)cyclopropyl]propoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 242) and (14S)-12,12-dimethyl-8-(2-oxo-3-{3-[1-(trifluoromethyl)cyclopropyl]propoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 243)

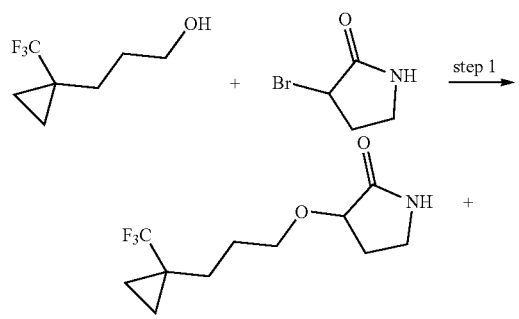

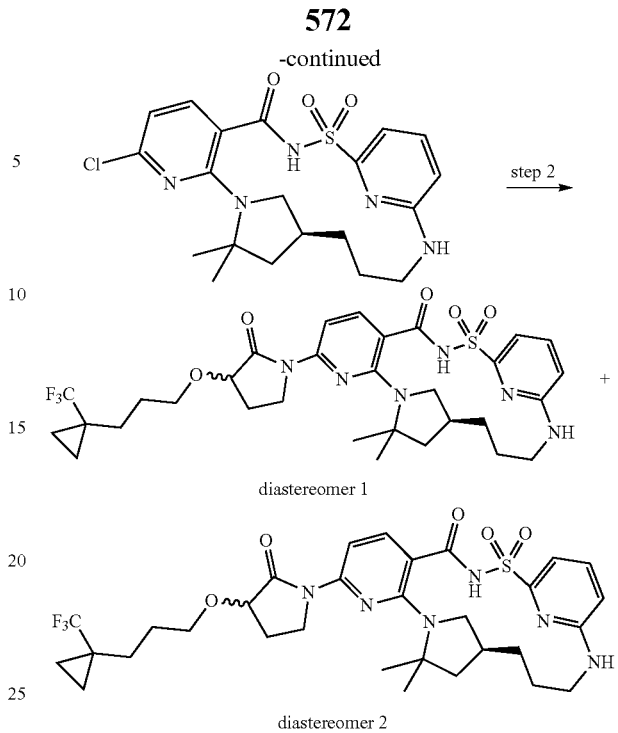

diastereomer 1 diastereomer 2

Step 1: 3-[3-[1-(Trifluoromethyl)cyclopropyl]propoxy]pyrrolidin-2-one

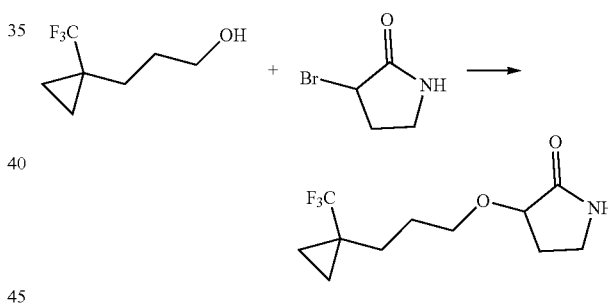

A 100 mL flask was charged under nitrogen with 3-[1-(trifluoromethyl)cyclopropyl]propan-1-ol (450 mg, 2.676 mmol), 3-bromopyrrolidin-2-one (442 mg, 2.695 mmol) and anhydrous tetrahydrofuran (12 mL). The mixture was cooled down to −50° C. [bis(trimethylsilyl)amino]potassium (11.3 mL of 0.5 M in toluene, 5.650 mmol) was added dropwise over 5 min and the yellow mixture was stirred at −50° C. for 15-20 min, then in an ice-bath at 0° C. for at least 3 h. The reaction was stirred in the ice bath that was allowed to slowly warm to room temperature. After 16 h, the mixture was cooled down to 0° C. then glacial acetic acid (250 μL, 4.396 mmol) was added to the reaction giving a pale brown slurry. Brine (75 mL) and ethyl acetate (75 mL) were added and the two phases were separated. The aqueous phase was further extracted with ethyl acetate (2×25 mL). The combined organic extracts were dried over sodium sulfate, filtered and the solvents evaporated. The crude residue was purified by silica gel chromatography (0%-15% methanol in dichloromethane gradient over 30 min) to furnish the desired 3-[3-[1-(trifluoromethyl)cyclopropyl]propoxy]pyrrolidin-2-one (555 mg, 83%) as an off-white solid. ¹H NMR (400

MHz, Chloroform-d) δ 6.65 (broad s, 1H), 3.95 (dd, J=7.7, 7.0 Hz, 1H), 3.84 (dt, J=9.2, 6.2 Hz, 1H), 3.54 (dt, J=9.2, 6.3 Hz, 1H), 3.41 (dddd, J=9.7, 8.5, 3.7, 1.1 Hz, 1H), 3.33-3.23 (m, 1H), 2.40 (dtd, J=13.1, 7.6, 3.7 Hz, 1H), 2.09-1.96 (m, 1H), 1.80-1.69 (m, 2H), 1.69-1.52 (m, 2H), 0.98-0.85 (m, 2H), 0.64-0.47 (m, 2H). ESI-MS m/z calc. 251.11331, found 252.1 (M+1)$^+$; Retention time: 1.32 min (LC Method B).

Step 2: (14S)-12,12-Dimethyl-8-(2-oxo-3-{3-[1-(trifluoromethyl)cyclopropyl]propoxy}pyrrolidin-1-yl)-2λ$^6$-thia-3,9,11,18,23-pentaazatetracyclo [17.3.1.1$^{11,14}$.0$^{5,10}$]tetracosa-1(22),5,7,9,19(23), 20-hexaene-2,2,4-trione (Diastereomer 1) (Compound 242) and (14S)-12,12-dimethyl-8-(2-oxo-3-{3-[1-(trifluoromethyl)cyclopropyl] propoxy}pyrrolidin-1-yl)-2λ$^6$-thia-3,9,11,18,23-pentaazatetracyclo[17.3.1.1$^{11,14}$.0$^{5,10}$]tetracosa-1(22), 5,7,9,19(23),20-hexaene-2,2,4-trione (Diastereomer 2) (Compound 243)

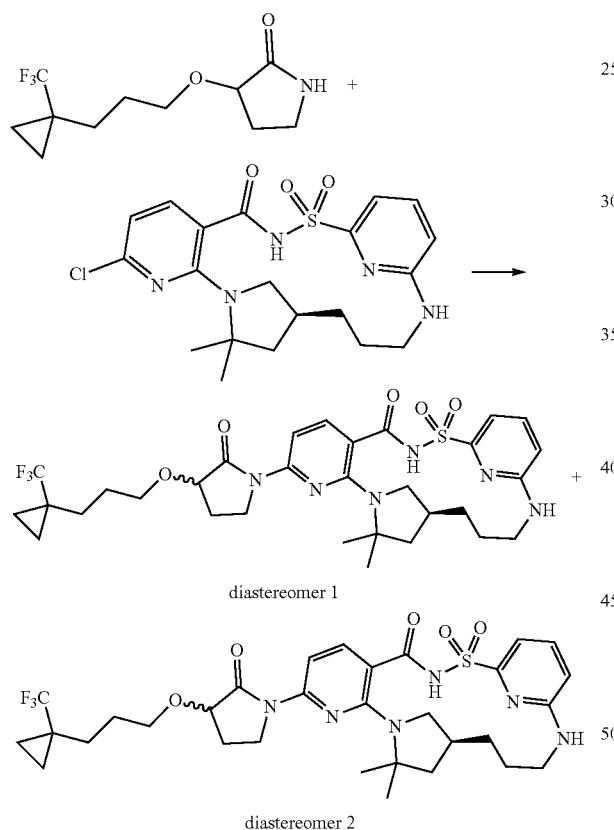

diastereomer 1 diastereomer 2

A 4 mL vial was charged with (14S)-8-chloro-12,12-dimethyl-2λ$^6$-thia-3,9,11,18,23-pentaazatetracyclo [17.3.1.1$^{11,14}$.0$^{5,10}$]tetracosa-1(23),5,7,9,19,21-hexaene-2,2,4-trione (32 mg, 0.07112 mmol), 3-[3-[1-(trifluoromethyl)cyclopropyl]propoxy]pyrrolidin-2-one (25 mg, 0.09950 mmol), Pd$_2$(dba)$_3$ (11 mg, 0.01201 mmol), Xantphos (11 mg, 0.01901 mmol), cesium carbonate (110 mg, 0.3376 mmol) and anhydrous dioxane (0.6 mL). The mixture was sparged with nitrogen for about 3 min, capped and stirred at 120° C. for 16 h. The organic solvent was concentrated by blowing nitrogen in the vial. The reaction was diluted with dimethyl sulfoxide (900 μL), microfiltered and subjected to reverse phase preparative HPLC (C$_{18}$) using a gradient of acetonitrile in water (30% to 99% over 15 min) and hydrochloric acid as a modifier. The pure fractions were collected and the organic solvents were evaporated. The resulting aqueous solution was extracted with ethyl acetate (3×) and the combined organic phases were dried over sodium sulfate. Filtration and evaporation of the solvents gave a solid that was purified by flash chromatography on silica gel using a gradient of methanol (0% to 5% over 30 min) in dichloromethane. The pure fractions were combined and the solvents evaporated. The residue was triturated with dichloromethane/hexanes and the solvents evaporated to give a mixture of diastereomers that were separated by chiral SFC (ChiralCel OJ-H (250×10 mm), 5 μM column; mobile phase: 24% acetonitrile/methanol (90:10; 20 mM NH$_3$), 76% carbon dioxide, 10 mL/min; concentration: 23 mg/mL: in acetonitrile/methanol (90:10; 20 mM NH$_3$); injection volume 70 μL, 100 bar). The first diastereomer to elute was (14S)-12,12-dimethyl-8-(2-oxo-3-{3-[1-(trifluoromethyl)cyclopropyl]propoxy}pyrrolidin-1-yl)-2λ$^6$-thia-3,9,11,18,23-pentaazatetracyclo[17.3.1.1$^{11,14}$, 14.0$^{5,10}$]tetracosa-1(22),5,7,9,19(23),20-hexaene-2,2,4-trione (diastereomer 1) (Compound 242) (6.3 mg, 26%). ESI-MS m/z calc. 664.2655, found 665.4 (M+1)$^+$; Retention time: 2.05 min (LC Method B). The second diastereomer to elute was (14S)-12,12-dimethyl-8-(2-oxo-3-{3-[1-(trifluoromethyl)cyclopropyl]propoxy}pyrrolidin-1-yl)-2λ$^6$-thia-3, 9,11,18,23-pentaazatetracyclo[17.3.1.1$^{11,14}$.0$^{5,10}$]tetracosa-1(22),5,7,9,19(23),20-hexaene-2,2,4-trione (diastereomer 2) (Compound 243) (5.2 mg, 22%). $^1$H NMR (400 MHz, dimethyl sulfoxide-d$_6$) δ 12.45 (broad s, 1H), 7.70 (d, J=8.4 Hz, 1H), 7.61-7.47 (m, 2H), 7.04 (d, J=7.2 Hz, 1H), 6.96 (s, 1H), 6.69 (d, J=8.5 Hz, 1H), 4.30 (t, J=8.4 Hz, 1H), 3.92 (t, J=9.8 Hz, 2H), 3.82-3.70 (m, 2H), 3.60-3.49 (m, 1H), 3.10 (br s, 1H), 2.93 (d, J=13.3 Hz, 1H), 2.74-2.64 (m, 1H), 2.48-2.36 (m, 1H), 2.10 (br s, 1H), 1.93-1.68 (m, 3H), 1.68-1.40 (m, 12H), 1.38-1.20 (m, 2H), 0.93-0.83 (m, 2H), 0.77-0.66 (m, 2H). ESI-MS m/z calc. 664.2655, found 665.4 (M+1)$^+$; Retention time: 2.06 min (LC Method B).

Example 74: Preparation of (14S)-8-{3-[(adamantan-1-yl)methoxy]-2-oxopyrrolidin-1-yl}-12,12-dimethyl-2λ$^6$-thia-3,9,11,18,23-pentaazatetracyclo [17.3.1.1$^{11,14}$.0$^{5,10}$]tetracosa-1(22),5,7,9,19(23), 20-hexaene-2,2,4-trione (Diastereomer 1) (Compound 244) and (14S)-8-{3-[(adamantan-1-yl) methoxy]-2-oxopyrrolidin-1-yl}-12,12-dimethyl-2λ$^6$-thia-3,9,11,18,23-pentaazatetracyclo[17.3.1.1$^{11,14}$, 14.0$^{5,10}$]tetracosa-1(22),5,7,9,19(23),20-hexaene-2, 2,4-trione (Diastereomer 2) (Compound 245)

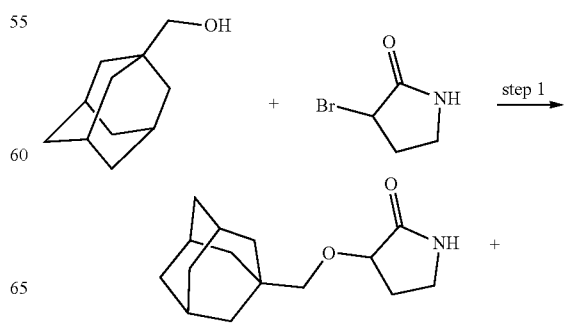

step 1

575
-continued

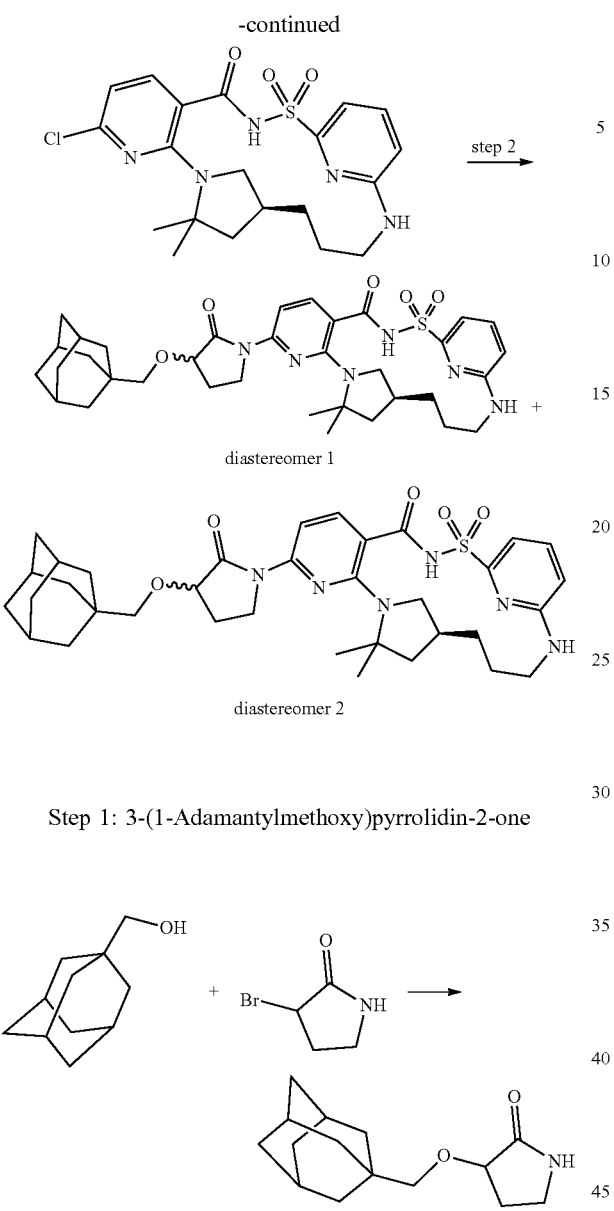

Step 1: 3-(1-Adamantylmethoxy)pyrrolidin-2-one

Into a solution of 1-adamantanemethanol (0.500 g, 3.007 mmol) and 3-bromopyrrolidin-2-one (0.493 g, 3.007 mmol) in anhydrous tetrahydrofuran (20 mL), was added 1 M potassium bis(trimethylsilyl)amide solution in tetrahydrofuran (6.3 mL, 6.30 mmol) at −60° C. The reaction was stirred at this temperature for 20 min, then raised to 0° C. and stirred for another 2 h. The reaction was quenched with saturated aqueous ammonium chloride solution (20 mL) and extracted with ethyl acetate (3×20 mL). The combined organic layers were washed with brine (20 mL), dried over anhydrous sodium sulfate, filtered and concentrated. The residue was triturated with hexane (30 mL) and the formed solid was collected by filtration to furnish 3-(adamantan-1-ylmethoxy)-pyrrolidin-2-one (0.594 g, 79%) as a white solid. $^1$H-NMR (250 MHz, dimethyl sulfoxide-$d_6$) d (ppm): 7.77 (s, br, 1H), 3.82 (t, J=7.3 Hz, 1H), 3.31 (m, 1H), 3.11 (m, 2H), 3.30 (d, J=9 Hz, 1H), 2.26 (m, 1H), 1.92-1.48 (m, 16H). ESI-MS m/z: calc. 249.17, found 250.2 (M+1)$^+$. Retention time: 4.97 min (LC Method Q).

576

Step 2: (14S)-8-{3-[(Adamantan-1-yl)methoxy]-2-oxopyrrolidin-1-yl}-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer 1) (Compound 244) and (14S)-8-{3-[(adamantan-1-yl)methoxy]-2-oxopyrrolidin-1-yl}-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer 2) (Compound 245)

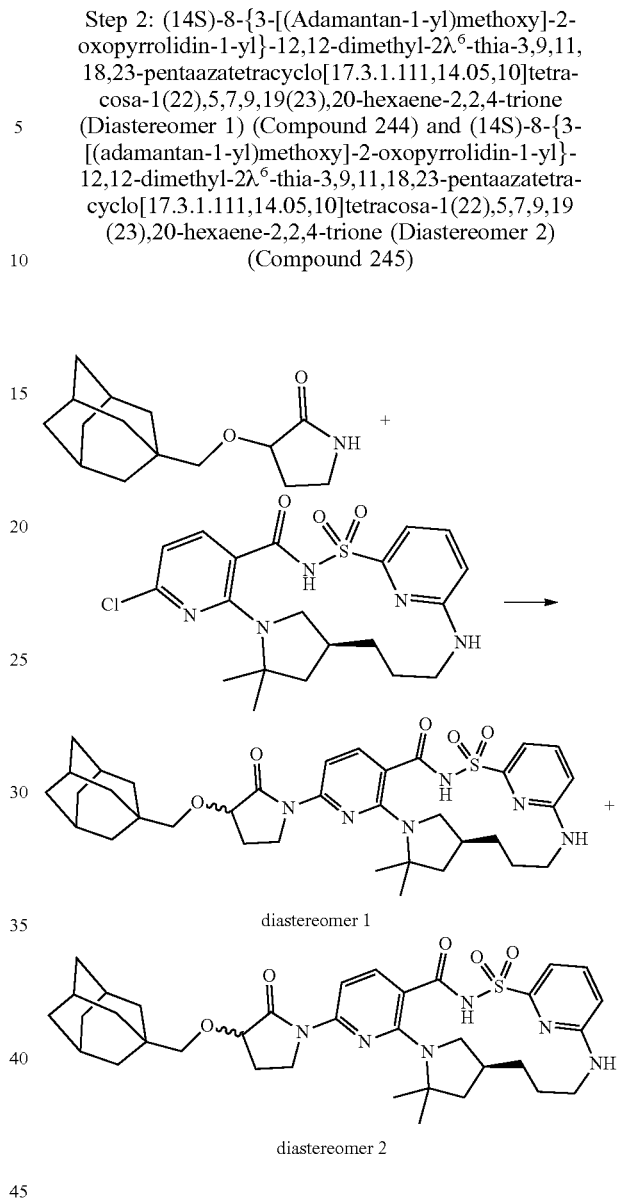

A 4 mL vial was charged with (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (35 mg, 0.07779 mmol), 3-(1-adamantylmethoxy)pyrrolidin-2-one (30 mg, 0.1203 mmol), Pd$_2$(dba)$_3$ (10 mg, 0.01092 mmol), Xantphos (12 mg, 0.02074 mmol), cesium carbonate (130 mg, 0.3990 mmol) and anhydrous dioxane (0.6 mL). The mixture was sparged with nitrogen for about 3 min, capped and stirred at 120° C. for 22 h. The organic solvent was concentrated by blowing nitrogen in the vial. The reaction was diluted with dimethyl sulfoxide (900 µL), microfiltered and subjected to reverse phase preparative HPLC (C$_{18}$) using a gradient of acetonitrile in water (30% to 99% over 15 min) and hydrochloric acid as a modifier (950 µL injection). The pure fractions were collected and the organic solvents were evaporated. The solid was extracted with ethyl acetate (2×) and the organic phase was dried over sodium sulfate. Filtration then evaporation of the solvents gave a solid that was purified by flash chromatography on silica gel using a gradient of methanol (0% to 5% over 30 min) in dichloromethane. The pure fractions were collected and the solvents evaporated.

The residue was triturated with dichloromethane/hexanes and the solvents evaporated to give a mixture of diastereomers which were separated by chiral SFC ((ChiralCel OJ-H (250×10 mm), 5 μM column; mobile phase 31% acetonitrile/methanol (90:10, 20 mM NH₃), 69% carbon dioxide, 10 mL/min; concentration 23 mg/mL in acetonitrile/methanol (90:10; 20 mM NH₃); injection volume 70 μL, 100 bar). The first diastereomer to elute was (14S)-8-{3-[(adamantan-1-yl)methoxy]-2-oxopyrrolidin-1-yl}-12,12-dimethyl-2$\lambda^6$-thia-3,9,11,18,23-pentaazatetracyclo[17.3.1.1¹¹,¹⁴.0⁵,¹⁰] tetracosa-1(22),5,7,9,19(23),20-hexaene-2,2,4-trione (diastereomer 1) (Compound 244) (6.3 mg, 23%). ¹H NMR (400 MHz, dimethyl sulfoxide-d₆) δ 12.46 (broad s, 1H), 7.70 (d, J=8.4 Hz, 1H), 7.56 (t, J=7.9 Hz, 1H), 7.50 (d, J=8.4 Hz, 1H), 7.03 (d, J=7.2 Hz, 1H), 6.95 (br s, 1H), 6.69 (d, J=8.4 Hz, 1H), 4.19 (t, J=8.1 Hz, 1H), 4.02 (t, J=9.3 Hz, 1H), 3.98-3.84 (m, 1H), 3.69 (dt, J=10.4, 7.5 Hz, 1H), 3.41 (d, J=9.0 Hz, 2H), 3.11 (d, J=9.0 Hz, 2H), 2.93 (d, J=13.2 Hz, 1H), 2.76-2.64 (m, 1H), 2.45-2.36 (m, 1H), 2.10 (br s, 1H), 1.98-1.85 (m, 4H), 1.85-1.41 (m, 22H), 1.34-1.26 (m, 1H). ESI-MS m/z calc. 662.325, found 663.5 (M+1)⁺; Retention time: 2.41 min (LC Method B). The second diastereomer to elute was (14S)-8-{3-[(adamantan-1-yl)methoxy]-2-oxopyrrolidin-1-yl}-12,12-dimethyl-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 2) (Compound 245) (5.6 mg, 20%). ¹H NMR (400 MHz, dimethyl sulfoxide-d₆) δ 12.45 (broad s, 1H), 7.70 (d, J=8.4 Hz, 1H), 7.61-7.48 (m, 2H), 7.04 (d, J=7.2 Hz, 1H), 6.95 (br s, 1H), 6.69 (d, J=8.5 Hz, 1H), 4.24 (t, J=8.3 Hz, 1H), 3.92 (t, J=9.5 Hz, 2H), 3.77 (q, J=9.4, 8.8 Hz, 1H), 3.41 (d, J=8.9 Hz, 2H), 3.10 (d, J=9.0 Hz, 2H), 2.93 (d, J=13.3 Hz, 1H), 2.77-2.64 (m, 1H), 2.46-2.38 (m, 1H), 2.10 (br s, 1H), 1.96-1.72 (m, 6H), 1.72-1.42 (m, 20H), 1.38-1.25 (m, 1H). ESI-MS m/z calc. 662.325, found 663.5 (M+1)⁺; Retention time: 2.41 min (LC Method B).

Example 75: Preparation of (14S)-8-{3-[(4,4-dimethylpentyl)oxy]-2-oxopyrrolidin-1-yl}-12,12-dimethyl-2$\lambda^6$-thia-3,9,11,18,23-pentaazatetracyclo [17.3.1.1¹¹,¹⁴.0⁵,¹⁰]tetracosa-1(22),5,7,9,19(23), 20-hexaene-2,2,4-trione (Diastereomer 1) (Compound 246) and (14S)-8-{3-[(4,4-dimethylpentyl)oxy]-2-oxopyrrolidin-1-yl}-12,12-dimethyl-2$\lambda^6$-thia-3,9,11,18,23-pentaazatetracyclo[17.3.1.1¹¹, 14.0⁵,¹⁰]tetracosa-1(22),5,7,9,19(23),20-hexaene-2, 2,4-trione (Diastereomer 2) (Compound 247)

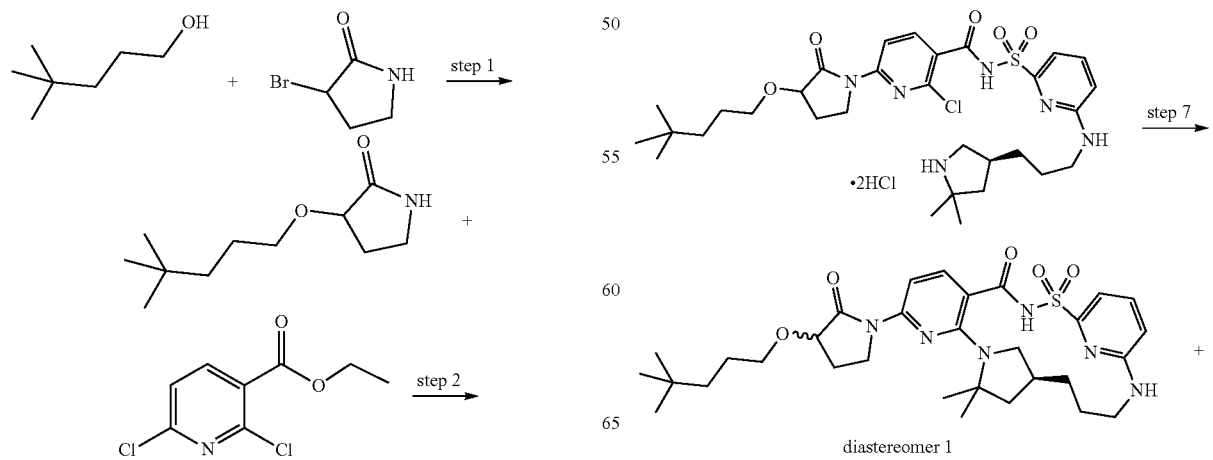

diastereomer 1

-continued

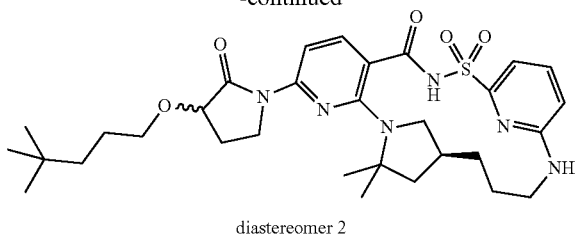

diastereomer 2

Step 1: 3-(4,4-Dimethylpentoxy)pyrrolidin-2-one

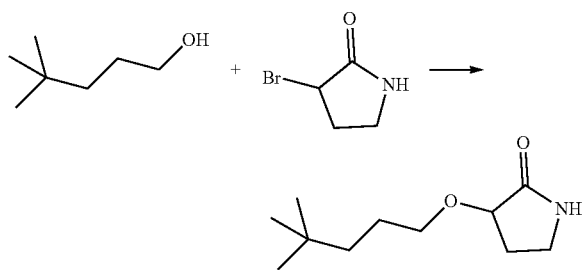

A 100 mL flask was charged under nitrogen with 4,4-dimethylpentan-1-ol (0.97 g, 8.348 mmol), 3-bromopyrrolidin-2-one (1.41 g, 8.598 mmol) and anhydrous tetrahydrofuran (5 mL). The mixture was cooled down in an ice-water bath and a solution of KHMDS (17 mL of 1 M, 17.00 mmol) was added over 10 min (solution turned brown quickly). The mixture was stirred in the cooling bath that was allowed to warm to room temperature overnight. After 24 h, the reaction was cooled down in an ice-water bath and treated with acetic acid (1 mL, 17.58 mmol) and brine (50 mL). The product was extracted with ethyl acetate (2×40 mL). The combined organic extracts were washed over sodium sulfate, filtered and the solvents evaporated to give a crude material (430 mg). The residue was subjected to flash chromatography on silica gel using a gradient of methanol (0% to 15% over 20 min) in dichloromethane giving 3-(4,4-dimethylpentoxy)pyrrolidin-2-one (239 mg, 14%) as a tan solid. $^1$H NMR (400 MHz, Chloroform-d) δ 5.85 (broad s, 1H), 3.97 (dd, J=7.7, 6.9 Hz, 1H), 3.83 (ddd, J=8.9, 7.4, 6.6 Hz, 1H), 3.52 (dt, J=9.0, 7.1 Hz, 1H), 3.43 (dddd, J=9.6, 8.4, 3.8, 1.2 Hz, 1H), 3.29 (dddd, J=9.6, 7.5, 6.7, 0.8 Hz, 1H), 2.42 (dtd, J=13.1, 7.6, 3.9 Hz, 1H), 2.09 (ddt, J=13.0, 8.4, 6.8 Hz, 1H), 1.68-1.49 (m, 2H overlapped with residual solvent), 1.28-1.12 (m, 2H), 0.88 (s, 9H). ESI-MS m/z calc. 199.15723, found 200.2 (M+1)$^+$; Retention time: 1.3 min (LC Method B).

Step 2: Ethyl 2-chloro-6-[3-(4,4-dimethylpentoxy)-2-oxo-pyrrolidin-1-yl]pyridine-3-carboxylate

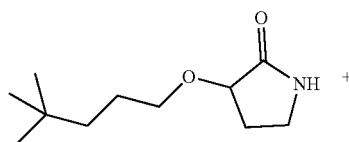

-continued

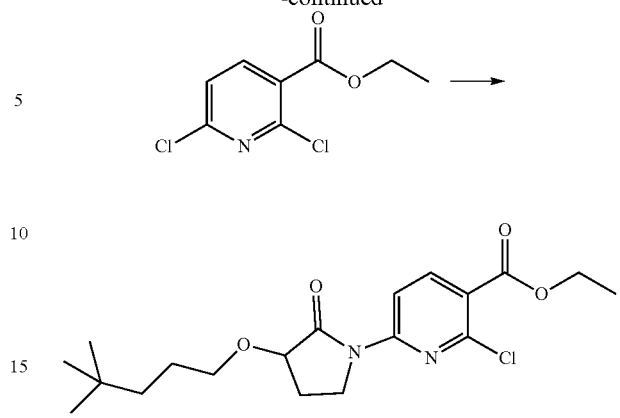

A 100 mL flask was charged under nitrogen with ethyl 2,6-dichloropyridine-3-carboxylate (336 mg, 1.527 mmol) and 3-(4,4-dimethylpentoxy)pyrrolidin-2-one (287 mg, 1.440 mmol) in anhydrous N,N-dimethylformamide (6 mL). Potassium carbonate (271 mg, 1.961 mmol) (325 mesh) was added, followed by 1,4-diazabicyclo[2.2.2]octane (25 mg, 0.2229 mmol). The mixture was stirred at ambient temperature under nitrogen. After 2 days, the reaction was quenched with the addition of water (50 mL) then extracted with ethyl acetate (2×25 mL). The organic phase was dried over sodium sulfate, filtered and the solvents were evaporated. The product was purified by flash chromatography on silica gel using a gradient of ethyl acetate (0% to 50% over 20 min) in hexanes. The pure fractions were collected and the solvents evaporated to give ethyl 2-chloro-6-[3-(4,4-dimethylpentoxy)-2-oxo-pyrrolidin-1-yl]pyridine-3-carboxylate (358 mg, 65%) as a colorless resin that slowly solidified. $^1$H NMR (400 MHz, dimethyl sulfoxide-d$_6$) δ 8.36 (d, J=8.6 Hz, 1H), 8.32 (d, J=8.6 Hz, 1H), 4.38-4.26 (m, 3H), 4.02 (ddd, J=11.1, 8.9, 2.6 Hz, 1H), 3.81-3.67 (m, 2H), 3.54 (dt, J=9.3, 6.6 Hz, 1H), 2.49-2.39 (m, 1H), 1.92 (dq, J=12.4, 8.8 Hz, 1H), 1.58-1.44 (m, 2H), 1.32 (t, J=7.1 Hz, 3H), 1.25-1.16 (m, 2H), 0.87 (s, 9H). ESI-MS m/z calc. 382.16592, found 383.3 (M+1)$^+$; Retention time: 2.26 min (LC Method B).

Step 3: 6-[[3-Carboxy-3-(4,4-dimethylpentoxy)propyl]amino]-2-chloro-pyridine-3-carboxylic Acid

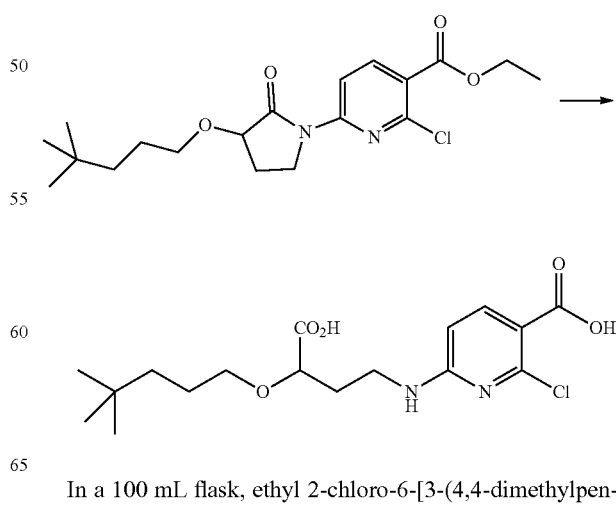

In a 100 mL flask, ethyl 2-chloro-6-[3-(4,4-dimethylpentoxy)-2-oxo-pyrrolidin-1-yl]pyridine-3-carboxylate (335 mg, 0.8749 mmol) in methanol (5 mL) and tetrahydrofuran (5 mL) were stirred until homogenous. To the mixture was added sodium hydroxide (1 mL of 2 M, 2.000 mmol) (2 M aqueous) and the cloudy mixture was stirred at ambient temperature for 9 h. More sodium hydroxide (1 mL of 6 N) was added and the mixture was stirred overnight. The reaction was diluted with water (40 mL). The solution was acidified with the slow addition of 6 N hydrochloric acid until pH=2. The solid was extracted with ethyl acetate (2×50 mL, 1×25 mL) and the combined organic phases were dried over sodium sulfate, filtered and concentrated in vacuo. The residue was triturated with dichloromethane/hexanes and the solvents were evaporated to give 6-[[3-carboxy-3-(4,4-dimethylpentoxy)propyl]amino]-2-chloro-pyridine-3-carboxylic acid (333 mg, quantitative yield) as an off-white solid. $^1$H NMR (400 MHz, dimethyl sulfoxide-$d_6$) δ 12.60 (s, 2H), 7.87 (d, J=8.6 Hz, 1H), 7.61 (t, J=5.6 Hz, 1H), 6.44 (d, J=8.7 Hz, 1H), 3.83 (dd, J=8.9, 3.8 Hz, 1H), 3.50 (dt, J=8.9, 6.6 Hz, 1H), 3.42-3.36 (m, 1H), 3.34 (broad s, partially overlapped with water signal, 1H), 3.25 (dt, J=8.9, 6.7 Hz, 1H), 2.00-1.85 (m, 1H), 1.85-1.73 (m, 1H), 1.52-1.39 (m, 2H), 1.20-1.12 (m, 2H), 0.84 (s, 9H). ESI-MS m/z calc. 372.1452, found 373.2 (M+1)$^+$; Retention time: 1.47 min (LC Method B).

Step 4: 2-Chloro-6-[3-(4,4-dimethylpentoxy)-2-oxo-pyrrolidin-1-yl]pyridine-3-carboxylic Acid

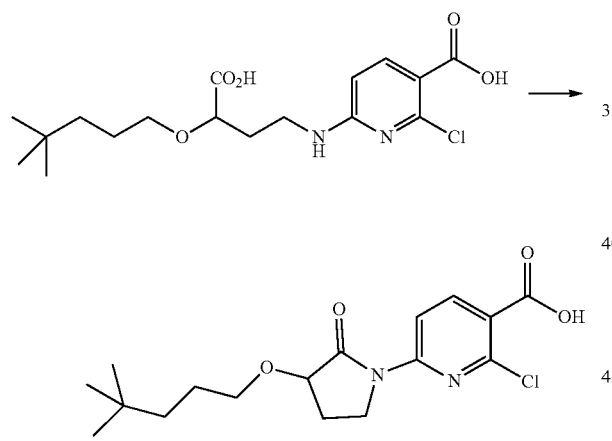

A 100 mL flask was charged under nitrogen with 6-[[3-carboxy-3-(4,4-dimethylpentoxy)propyl]amino]-2-chloro-pyridine-3-carboxylic acid (281 mg, 0.7537 mmol), HATU (292 mg, 0.7680 mmol) and anhydrous tetrahydrofuran (6 mL) (partial suspension). Triethylamine (0.34 mL, 2.439 mmol) was added (turned quickly into a yellow homogenous solution) and the mixture was stirred at room temperature for 2 days. Water (30 mL) was added followed by hydrochloric acid (200 µL of 6 M, 1.200 mmol) (6 N aqueous, final pH=4). The resulting white solid was filtered and washed with water to give pure 2-chloro-6-[3-(4,4-dimethylpentoxy)-2-oxo-pyrrolidin-1-yl]pyridine-3-carboxylic acid (196 mg, 73%) as a white solid. $^1$H NMR (400 MHz, dimethyl sulfoxide-$d_6$) δ 13.51 (s, 1H), 8.34 (d, J=8.6 Hz, 1H), 8.31 (d, J=8.6 Hz, 1H), 4.33 (dd, J=8.9, 7.9 Hz, 1H), 4.01 (ddd, J=11.2, 8.8, 2.6 Hz, 1H), 3.82-3.67 (m, 2H), 3.54 (dt, J=9.2, 6.6 Hz, 1H), 2.48-2.37 (m, 1H), 1.91 (dq, J=12.4, 8.9 Hz, 1H), 1.58-1.44 (m, 2H), 1.27-1.14 (m, 2H), 0.87 (s, 9H). ESI-MS m/z calc. 354.13464, found 355.3 (M+1)$^+$; Retention time: 1.91 min (LC Method B).

Step 5: tert-Butyl (4S)-4-[3-[[6-[[2-chloro-6-[3-(4,4-dimethylpentoxy)-2-oxo-pyrrolidin-1-yl]pyridine-3-carbonyl]sulfamoyl]-2-pyridyl]amino]propyl]-2,2-dimethyl-pyrrolidine-1-carboxylate

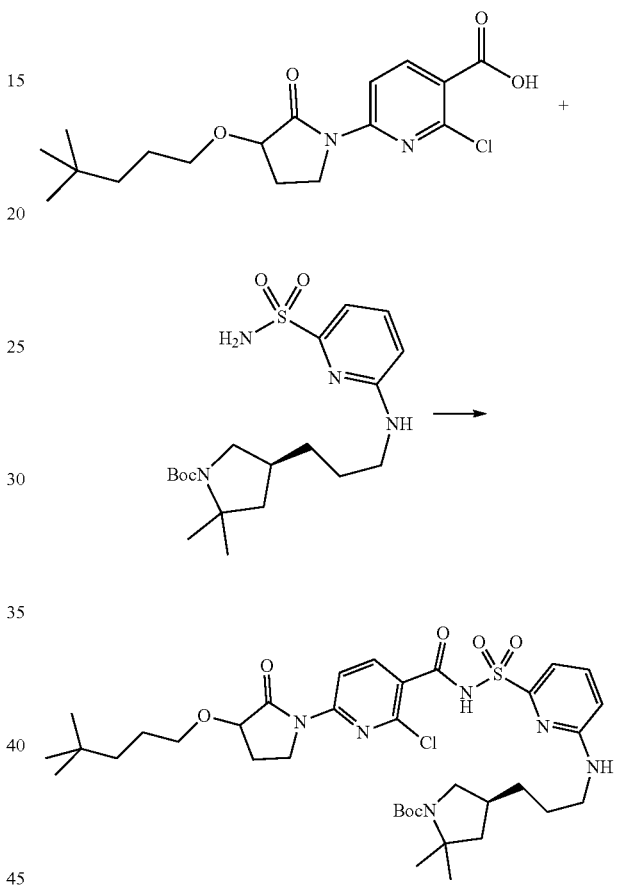

A 100 mL round bottom flask was charged under nitrogen with 2-chloro-6-[3-(4,4-dimethylpentoxy)-2-oxo-pyrrolidin-1-yl]pyridine-3-carboxylic acid (182 mg, 0.5129 mmol) and anhydrous tetrahydrofuran (3 mL). Carbonyl diimidazole (102 mg, 0.6291 mmol) (freshly recrystallized from tetrahydrofuran) was added and the mixture was stirred under nitrogen at room temperature for 3 h. Another 35 mg of carbonyl diimidazole was added and the mixture was stirred at room temperature for 2 h. In a separate 20 mL flask, a solution of tert-butyl (4S)-2,2-dimethyl-4-[3-[(6-sulfamoyl-2-pyridyl)amino]propyl]pyrrolidine-1-carboxylate (211 mg, 0.5115 mmol) in anhydrous tetrahydrofuran (1.5 mL) was prepared under nitrogen atmosphere and it was subsequently added via syringe into the activated ester solution. Added 1,8-diazabicyclo[5.4.0]undec-7-ene (0.38 mL, 2.541 mmol) through a syringe and the reaction mixture was stirred at room temperature under nitrogen atmosphere overnight. After 2 days, the solvents were removed under reduced pressure and the resulting thick oil was treated with ethyl acetate (20 mL) and water (20 mL). Added hydrochloric acid (600 µL of 6 M, 3.600 mmol) slowly (final pH=5) and the two phases were separated. The aqueous phase was extracted with ethyl acetate (30 mL). The combined extracts were washed with brine (30 mL) and dried over sodium sulfate. After evaporation of the solvents, the residue was dissolved in dichloromethane and purified by flash chromatography on silica gel using a gradient of ethyl acetate (0% to 100% over 30 min) in hexanes giving tert-butyl (4S)-4-[3-[[6-[[2-chloro-6-[3-(4,4-dimethylpentoxy)-2-oxo-pyrrolidin-1-yl]pyridine-3-carbonyl]sulfamoyl]-2-pyridyl]amino]propyl]-2,2-dimethyl-pyrrolidine-1-carboxylate (138 mg, 36%, 90% purity) as a colorless resin. ESI-MS m/z calc. 748.3385, found 749.5 (M+1)$^+$; Retention time: 2.42 min (LC Method B).

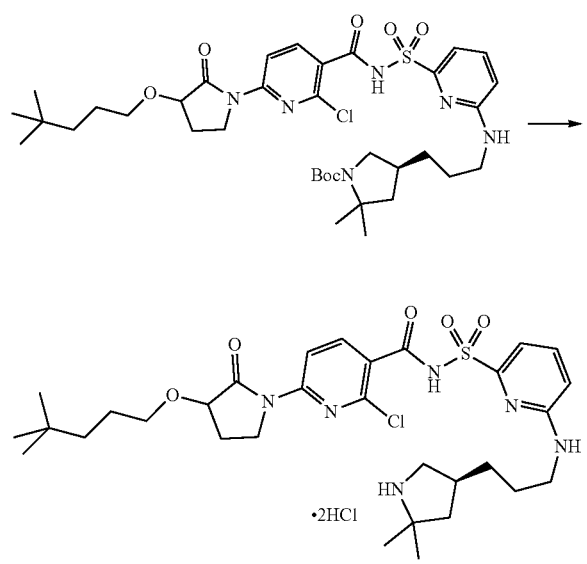

Step 6: 2-Chloro-6-[3-(4,4-dimethylpentoxy)-2-oxo-pyrrolidin-1-yl]-N-[[6-[3-[(3S)-5,5-dimethylpyrrolidin-3-yl]propylamino]-2-pyridyl]sulfonyl]pyridine-3-carboxamide (Dihydrochloride Salt)

A 100 mL flask was charged with tert-butyl (4S)-4-[3-[[6-[[2-chloro-6-[3-(4,4-dimethylpentoxy)-2-oxo-pyrrolidin-1-yl]pyridine-3-carbonyl]sulfamoyl]-2-pyridyl]amino]propyl]-2,2-dimethyl-pyrrolidine-1-carboxylate (138 mg, 0.1842 mmol), dichloromethane (2 mL) and hydrochloric acid (300 µL of 4 M in dioxane, 1.200 mmol). The reaction was stirred at room temperature for 3.5 h (60% conversion). An additional amount of hydrochloric acid (300 µL of 4 M, 1.200 mmol) was added and the reaction was stirred for an additional 2 h. The volatiles were removed by evaporation under vacuum. The residue was triturated with dichloromethane/hexanes and the solvents evaporated. The operation was repeated until a white solid was obtained. Drying under vacuum gave 2-chloro-6-[3-(4,4-dimethylpentoxy)-2-oxo-pyrrolidin-1-yl]-N-[[6-[3-[(3S)-5,5-dimethylpyrrolidin-3-yl]propylamino]-2-pyridyl]sulfonyl]pyridine-3-carboxamide (dihydrochloride salt) (125 mg, 94%) as a white solid. The product was used for next step without any further purification. ESI-MS m/z calc. 648.2861, found 649.4 (M+1)$^+$; Retention time: 1.62 min (LC Method B).

Step 7: (14S)-8-{3-[(4,4-Dimethylpentyl)oxy]-2-oxopyrrolidin-1-yl}-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (diastereomer 1) (Compound 246) and (14S)-8-{3-[(4,4-dimethylpentyl)oxy]-2-oxopyrrolidin-1-yl}-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Diastereomer 2) (Compound 247)

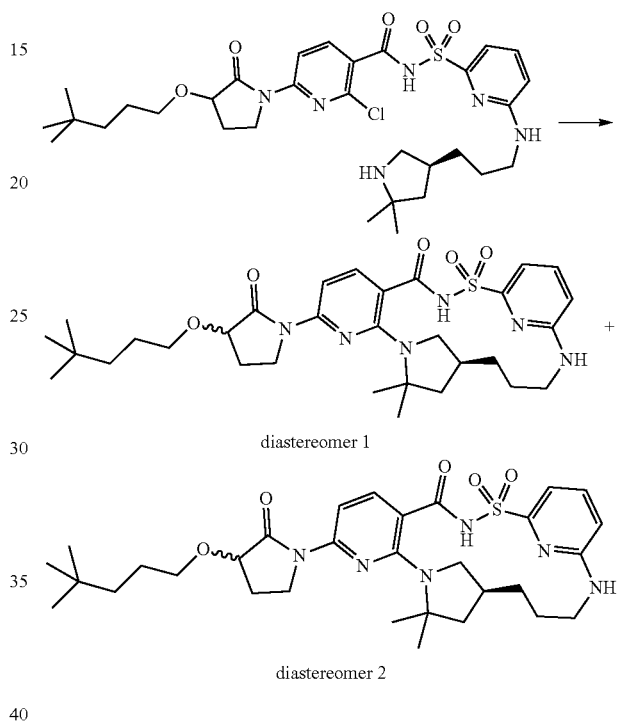

diastereomer 1 diastereomer 2

A 50 mL round bottom flask equipped with a magnetic stirbar was charged under nitrogen with 2-chloro-6-[3-(4,4-dimethylpentoxy)-2-oxo-pyrrolidin-1-yl]-N-[[6-[3-[(3S)-5,5-dimethylpyrrolidin-3-yl]propylamino]-2-pyridyl]sulfonyl]pyridine-3-carboxamide (dihydrochloride salt) (125 mg, 0.1731 mmol), anhydrous NMP (7 mL) and potassium carbonate (465 mg, 3.365 mmol) (325 mesh). The mixture was vigorously stirred in a dry bath at 155° C. under nitrogen for 20 h. After cooling down to room temperature, the mixture was poured into cooled water (50 mL) and it was acidified by adding hydrochloric acid (1 mL of 6 M, 6.000 mmol) (mild foaming). The resulting solid was filtered and briefly air dried. The solid was dissolved in dichloromethane and purified by flash chromatography on silica gel using a gradient of methanol (0% to 5% over 30 min) in dichloromethane giving a mixture of diastereomers that was subjected to chiral SFC separation (ChiralCel OJ-H (250×10 mm), 5 µM column; mobile phase 24% acetonitrile/methanol (90:10, 20 mM NH$_3$), 76% carbon dioxide, 10 mL/min; concentration 23 mg/mL in acetonitrile/methanol (90:10; 20 mM NH$_3$); injection volume 70 µL, 100 bar) giving as the first diastereomer to elute, (14S)-8-[3-[(4,4-dimethylpentyl)oxy]-2-oxopyrrolidin-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (diastereomer 1) (Compound 246) (22 mg, 20%). $^1$H NMR (400 MHz, dimethyl sulfoxide-d$_6$) δ 12.43 (s, 1H), 7.70 (d, J=8.4 Hz, 1H), 7.56 (t, J=7.8 Hz, 1H), 7.51 (d, J=8.3 Hz, 1H), 7.04 (d, J=7.2 Hz, 1H), 6.96 (broad s, 1H), 6.70 (d, J=8.5 Hz, 1H), 4.24 (t, J=8.2 Hz, 1H), 4.03 (t, J=8.7 Hz, 1H), 3.95-3.87 (br m, 1H), 3.81-3.64 (m, 2H), 3.52 (dt, J=9.2, 6.6 Hz, 1H), 3.12 (br s, 1H), 2.94 (d, J=13.5 Hz, 1H), 2.78-2.61 (m, 1H), 2.42 (dq, J=13.0, 7.9, 6.3 Hz, 1H), 2.11 (broad s, 1H), 1.92 (dq, J=12.3, 8.6 Hz, 1H), 1.85-1.68 (m, 2H), 1.64-1.41 (m, 10H), 1.36-1.13 (m, 4H), 0.87 (s, 9H). ESI-MS m/z calc. 612.3094, found 613.4 (M+1)$^+$; Retention time: 2.17 min (LC Method B). The second diastereomer to elute was (14S)-8-{3-[(4,4-dimethylpentyl)oxy]-2-oxopyrrolidin-1-yl}-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (diastereomer 2) (Compound 247) (21 mg, 19%). $^1$H NMR (400 MHz, dimethyl sulfoxide-d$_6$) δ 12.41 (s, 1H), 7.70 (d, J=8.4 Hz, 1H), 7.59-7.51 (m, 2H), 7.04 (d, J=7.2 Hz, 1H), 6.96 (broad s, 1H), 6.70 (d, J=8.5 Hz, 1H), 4.28 (t, J=8.4 Hz, 1H), 3.92 (t, J=9.8 Hz, 2H), 3.83-3.68 (m, 2H), 3.52 (dt, J=9.2, 6.6 Hz, 1H), 3.10 (br s, 1H), 2.94 (br d, J=13.4 Hz, 1H), 2.80-2.59 (m, 1H), 2.48-2.37 (m, 1H), 2.10 (br s, 1H), 1.95-1.68 (m, 3H), 1.64-1.42 (m, 10H), 1.36-1.14 (m, 4H), 0.87 (s, 9H). ESI-MS m/z calc. 612.3094, found 613.4 (M+1)$^+$; Retention time: 2.17 min (LC Method B).

Example 76: Preparation of 12,12-dimethyl-8-{3-[3-methyl-2-(propan-2-yl)butoxy]-1H-pyrazol-1-yl}-15-oxa-2$\lambda^6$-thia-3,9,11,18,23-pentaazatetracyclo[17.3.1.111,14.05,10]tetracosa-1(23),5(10),6,8,19,21-hexaene-2,2,4-trione (Enantiomer 1) (Compound 248) and 12,12-dimethyl-8-{3-[3-methyl-2-(propan-2-yl)butoxy]-1H-pyrazol-1-yl}-15-oxa-2$\lambda^6$-thia-3,9,11,18,23-pentaazatetracyclo[17.3.1.111,14.05,10]tetracosa-1(23),5(10),6,8,19,21-hexaene-2,2,4-trione (Enantiomer 2) (Compound 249)

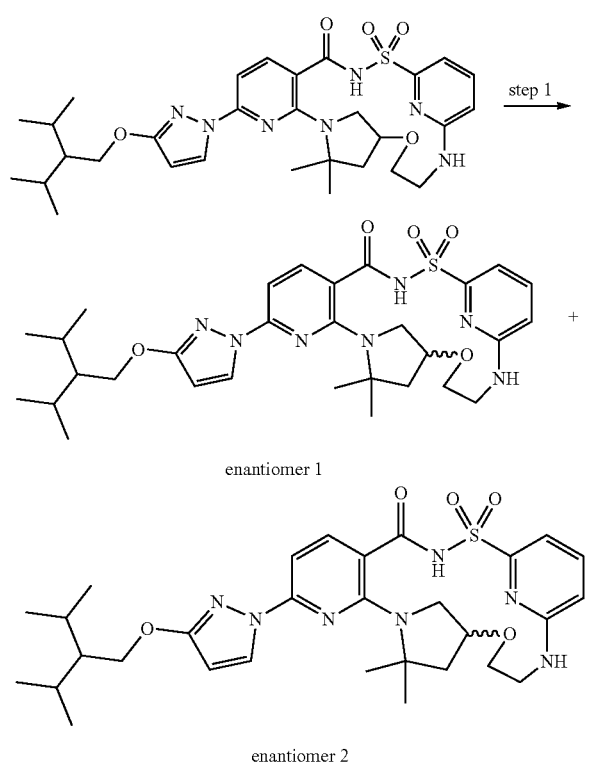

Step 1: 12,12-Dimethyl-8-{3-[3-methyl-2-(propan-2-yl)butoxy]-1H-pyrazol-1-yl}-15-oxa-2$\lambda^6$-thia-3,9,11,18,23-pentaazatetracyclo[17.3.1.111,14.05,10]tetracosa-1(23),5(10),6,8,19,21-hexaene-2,2,4-trione (Enantiomer 1) (Compound 248) and 12,12-dimethyl-8-{3-[3-methyl-2-(propan-2-yl)butoxy]-1H-pyrazol-1-yl}-15-oxa-2$\lambda^6$-thia-3,9,11,18,23-pentaazatetracyclo[17.3.1.111,14.05,10]tetracosa-1(23),5(10),6,8,19,21-hexaene-2,2,4-trione (Enantiomer 2) (Compound 249)

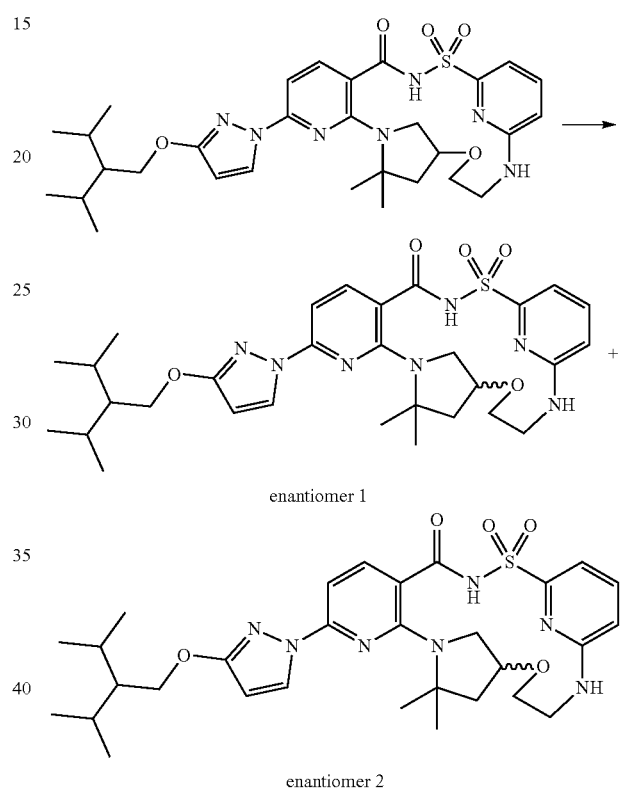

Racemic 12,12-dimethyl-8-{3-[3-methyl-2-(propan-2-yl)butoxy]-1H-pyrazol-1-yl}-15-oxa-2$\lambda^6$-thia-3,9,11,18,23-pentaazatetracyclo[17.3.1.111,14.05,10]tetracosa-1(23),5(10),6,8,19,21-hexaene-2,2,4-trione (60 mg, 0.09612 mmol) was subjected to chiral SFC chromatography. The following SFC protocol was employed: ChiralPak AS-3 (150×2.1 mm), 3 µm; 35° C. Mobile phase: 30% acetonitrile:methanol (90:10), 70% carbon dioxide. The first enantiomer to elute was 12,12-dimethyl-8-{3-[3-methyl-2-(propan-2-yl)butoxy]-1H-pyrazol-1-yl}-15-oxa-2$\lambda^6$-thia-3,9,11,18,23-pentaazatetracyclo[17.3.1.111,14.05,10]tetracosa-1(23),5(10),6,8,19,21-hexaene-2,2,4-trione (enantiomer 1) (Compound 248) (21 mg, 71%). ESI-MS m/z calc. 611.289, found 612.2 (M+1)$^+$; Retention time: 2.30 min (LC Method B). The second enantiomer to elute was 12,12-dimethyl-8-{3-[3-methyl-2-(propan-2-yl)butoxy]-1H-pyrazol-1-yl}-15-oxa-2$\lambda^6$-thia-3,9,11,18,23-pentaazatetracyclo[17.3.1.111,14.05,10]tetracosa-1(23),5(10),6,8,19,21-hexaene-2,2,4-trione (enantiomer 2) (Compound 249) (22 mg, 74%). $^1$H NMR (400 MHz, dimethyl sulfoxide-d$_6$) δ 12.56 (s, 1H), 8.19 (d, J=2.8 Hz, 1H), 7.78 (d, J=8.2 Hz, 1H), 7.59 (dd, J=8.5, 7.2 Hz, 1H), 7.10 (t, J=7.4 Hz, 2H), 6.95 (d, J=8.2 Hz, 1H), 6.70 (d, J=8.5 Hz, 1H), 6.11 (d, J=2.7 Hz, 1H), 4.23 (d, J=4.8 Hz, 2H), 4.11 (t, J=8.3 Hz, 2H), 3.88 (t, J=12.0 Hz, 1H), 3.60 (d, J=12.9 Hz, 1H), 3.23 (s, 1H), 3.07 (s, 1H), 2.87 (d, J=9.4 Hz, 1H), 2.08 (dd, J=11.7, 5.9 Hz, 1H), 1.96-1.85 (m, 2H), 1.79 (t, J=10.9 Hz, 1H), 1.58 (d, J=9.2 Hz, 6H), 1.35 (p, J=5.2 Hz, 1H), 0.98 (d, J=6.8 Hz, 6H), 0.92 (d, J=6.8 Hz, 6H). ESI-MS m/z calc. 611.289, found 612.2 (M+1)+; Retention time: 2.29 min (LC Method B).

Example 77: Preparation of 11-[3-(3,3-dicyclopropylpropoxy)-1H-pyrazol-1-yl]-7,7-dimethyl-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (Enantiomer 1) (Compound 251)

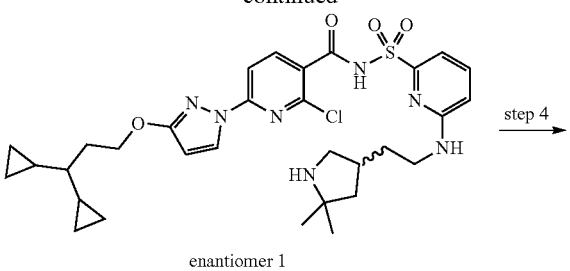

Step 1: tert-Butyl 2,2-dimethyl-4-[2-[(6-sulfamoyl-2-pyridyl)amino]ethyl]pyrrolidine-1-carboxylate

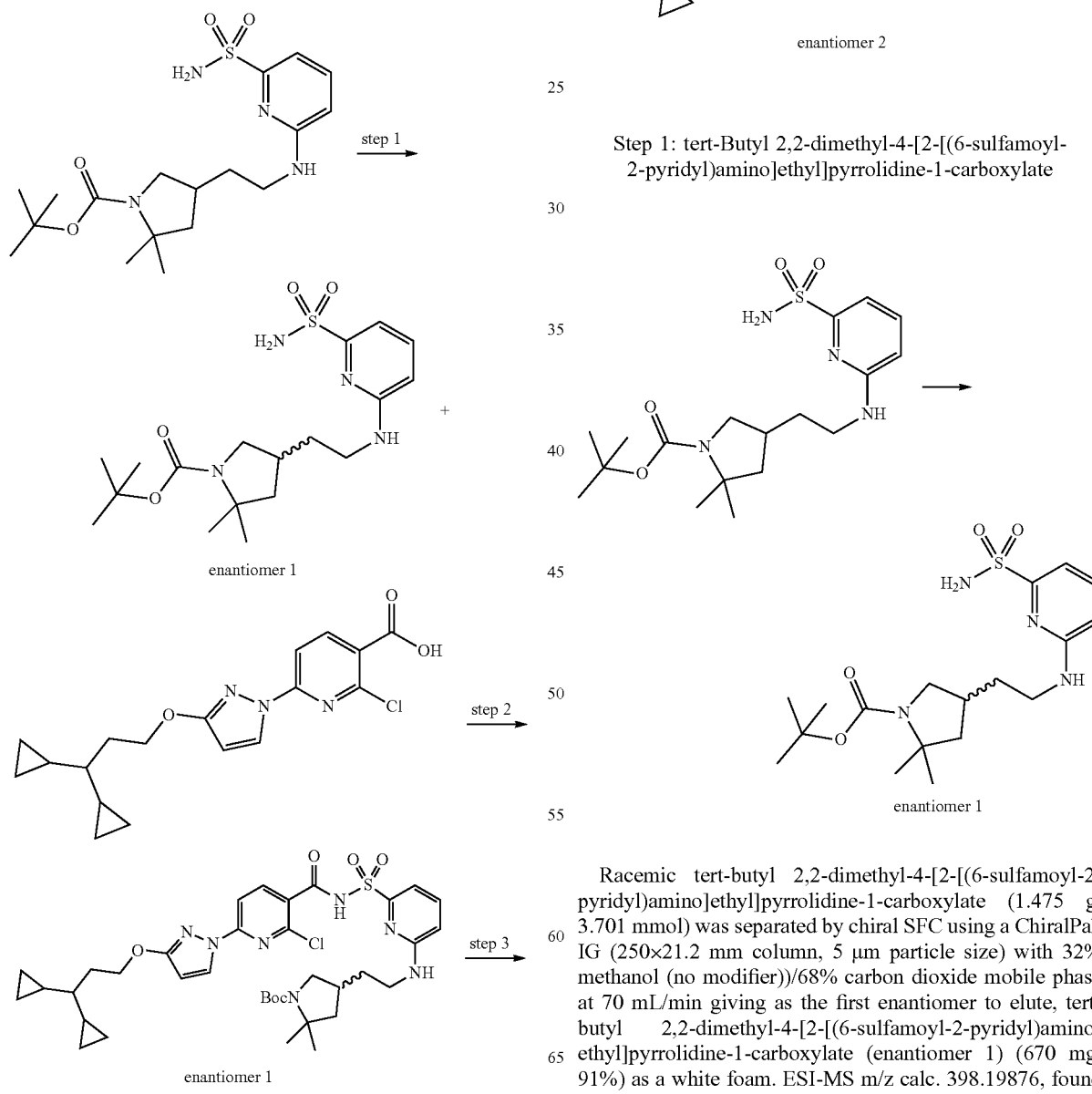

Racemic tert-butyl 2,2-dimethyl-4-[2-[(6-sulfamoyl-2-pyridyl)amino]ethyl]pyrrolidine-1-carboxylate (1.475 g, 3.701 mmol) was separated by chiral SFC using a ChiralPak IG (250×21.2 mm column, 5 μm particle size) with 32% methanol (no modifier))/68% carbon dioxide mobile phase at 70 mL/min giving as the first enantiomer to elute, tert-butyl 2,2-dimethyl-4-[2-[(6-sulfamoyl-2-pyridyl)amino]ethyl]pyrrolidine-1-carboxylate (enantiomer 1) (670 mg, 91%) as a white foam. ESI-MS m/z calc. 398.19876, found 399.3 (M+1)+; Retention time: 1.59 min (LC Method B).

Step 2: tert-Butyl 4-[2-[[6-[[2-chloro-6-[3-(3,3-dicyclopropylpropoxy)pyrazol-1-yl]pyridine-3-carbonyl]sulfamoyl]-2-pyridyl]amino]ethyl]-2,2-dimethyl-pyrrolidine-1-carboxylate (Enantiomer 1)

Step 3: 2-Chloro-6-[3-(3,3-dicyclopropylpropoxy)pyrazol-1-yl]-N-[[6-[2-(5,5-dimethylpyrrolidin-3-yl)ethyl amino]-2-pyridyl]sulfonyl]pyridine-3-carboxamide (Enantiomer 1)

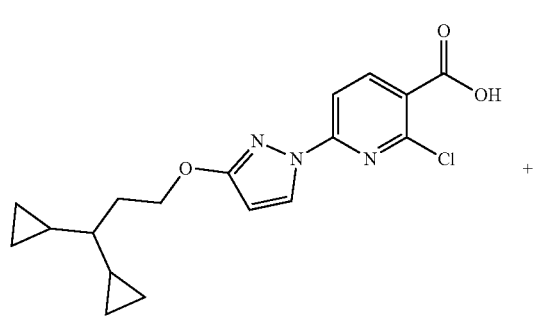

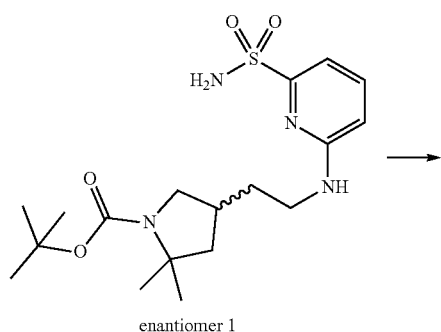

enantiomer 1

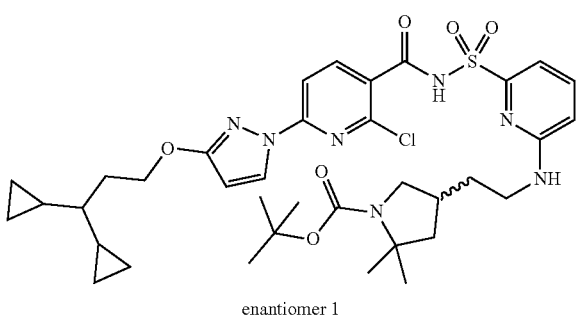

enantiomer 1

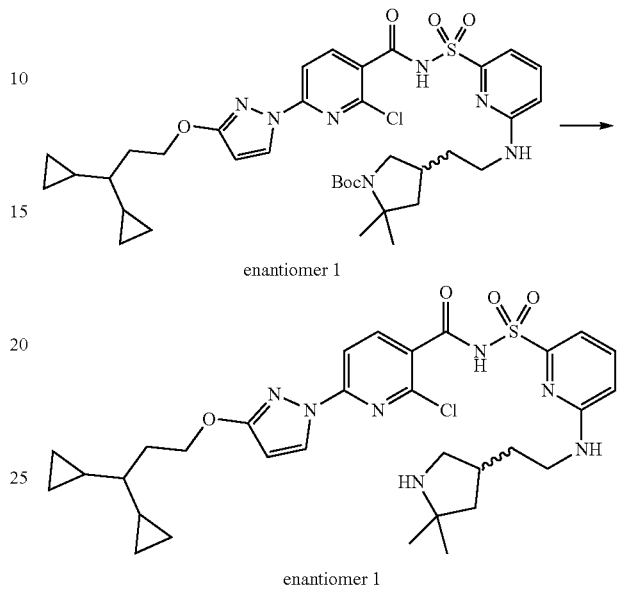

enantiomer 1

To a flask was added 2-chloro-6-[3-(3,3-dicyclopropylpropoxy)pyrazol-1-yl]pyridine-3-carboxylic acid (147.7 mg, 0.4082 mmol), recrystallized carbonyl diimidazole (66.2 mg, 0.4083 mmol) and tetrahydrofuran (4 mL). The reaction was stirred at 40° C. for 90 min. tert-Butyl 2,2-dimethyl-4-[2-[(6-sulfamoyl-2-pyridyl)amino]ethyl]pyrrolidine-1-carboxylate (enantiomer 1) (130 mg, 0.3262 mmol) was then added followed by 1,8-diazabicyclo[5.4.0]undec-7-ene (150 µL, 1.003 mmol). The reaction was stirred for 2 days. The reaction was filtered and purified via HPLC (30%-99% acetonitrile:water gradient with a 0.1% hydrochloric acid modifier) to provide tert-butyl 4-[2-[[6-[[2-chloro-6-[3-(3,3-dicyclopropylpropoxy)pyrazol-1-yl]pyridine-3-carbonyl]sulfamoyl]-2-pyridyl]amino]ethyl]-2,2-dimethyl-pyrrolidine-1-carboxylate (enantiomer 1) (30.4 mg, 13%). ESI-MS m/z calc. 741.30756, found 742.4 (M+1)+; Retention time: 2.2 min (LC Method G).

To a flask containing tert-butyl 4-[2-[[6-[[2-chloro-6-[3-(3,3-dicyclopropylpropoxy)pyrazol-1-yl]pyridine-3-carbonyl]sulfamoyl]-2-pyridyl]amino]ethyl]-2,2-dimethyl-pyrrolidine-1-carboxylate (enantiomer 1) (30.4 mg, 0.04095 mmol) was added dichloromethane (3 mL) and trifluoroacetic acid (125 µL, 1.622 mmol). The reaction was allowed to stir at room temperature for 30 min. The reaction was evaporated to dryness and washed with saturated aqueous sodium bicarbonate solution. The reaction mixture was extracted with ethyl acetate, dried over sodium sulfate, filtered, and evaporated to provide 2-chloro-6-[3-(3,3-dicyclopropylpropoxy)pyrazol-1-yl]-N-[[6-[2-(5,5-dimethylpyrrolidin-3-yl)ethylamino]-2-pyridyl]sulfonyl]pyridine-3-carboxamide (enantiomer 1) (24 mg, 91%). ESI-MS m/z calc. 641.2551, found 642.3 (M+1)+; Retention time: 1.76 min (LC Method B).

Step 4: 11-[3-(3,3-Dicyclopropylpropoxy)-1H-pyrazol-1-yl]-7,7-dimethyl-17λ⁶-thia-2,8,10,16,22-pentaazatetracyclo[16.3.1.1⁵,⁸.0⁹,¹⁴]tricosa-1(22),9,11,13,18,20-hexaene-15,17,17-trione (Enantiomer 1) (Compound 251)

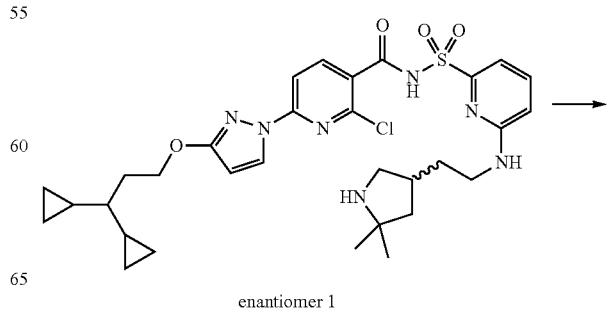

enantiomer 1

591

-continued

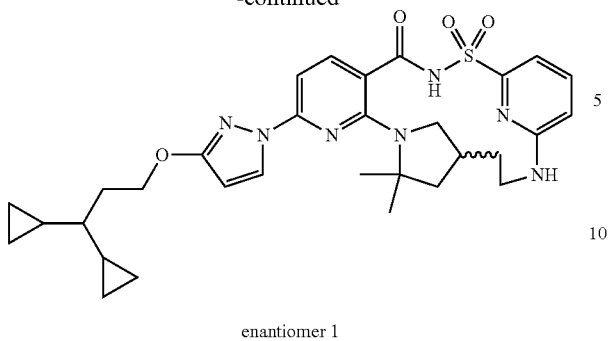

enantiomer 1

To a vial was added potassium carbonate (35 mg, 0.2532 mmol), cesium fluoride (12 mg, 0.07900 mmol), 3 Å molecular sieves and a solution of 2-chloro-6-[3-(3,3-dicyclopropylpropoxy)pyrazol-1-yl]-N-[[6-[2-(5,5-dimethylpyrrolidin-3-yl)ethylamino]-2-pyridyl]sulfonyl]pyridine-3-carboxamide (enantiomer 1) (24 mg, 0.03737 mmol) in dimethyl sulfoxide (1.5 mL). The reaction was placed in a 150° C. oil bath and allowed to stir overnight. The reaction was cooled to room temperature, filtered and purified by HPLC (10%-99% acetonitrile:water gradient with a 0.1% hydrochloric acid modifier) giving 11-[3-(3,3-dicyclopropylpropoxy)-1H-pyrazol-1-yl]-7,7-dimethyl-17$\lambda^6$-thia-2,8,10,16,22-pentaazatetracyclo[16.3.1.1$^{5,8}$.0$^{9,14}$]tricosa-1(22),9,11,13,18,20-hexaene-15,17,17-trione (enantiomer 1) (Compound 251) (9.3 mg, 41%). $^1$H NMR (400 MHz, dimethyl sulfoxide-$d_6$) δ 12.45 (s, 1H), 8.20 (d, J=2.8 Hz, 1H), 7.74 (d, J=33.0 Hz, 2H), 7.17 (s, 1H), 6.90 (d, J=8.2 Hz, 1H), 6.82 (s, 1H), 6.10 (d, J=2.8 Hz, 1H), 4.37 (t, J=6.8 Hz, 2H), 2.25 (s, 3H), 1.90 (q, J=6.8 Hz, 4H), 1.56 (s, 6H), 1.49 (s, 2H), 0.68 (dtd, J=13.4, 8.6, 5.0 Hz, 2H), 0.46-0.34 (m, 5H), 0.30 (ddd, J=15.8, 8.9, 6.7 Hz, 1H), 0.25-0.15 (m, 2H), 0.09-0.02 (m, 2H). Two protons obscured by solvent. ESI-MS m/z calc. 605.27844, found 606.2 (M+1)$^+$; Retention time: 2.3 min (LC Method B).

Example 78: Preparation of (14S)-8-[3-(2-{dispiro[2.0.2.1]heptan-7-yl}-2,2-dideuterio-ethoxy)-1H-pyrazol-1-yl]-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 252)

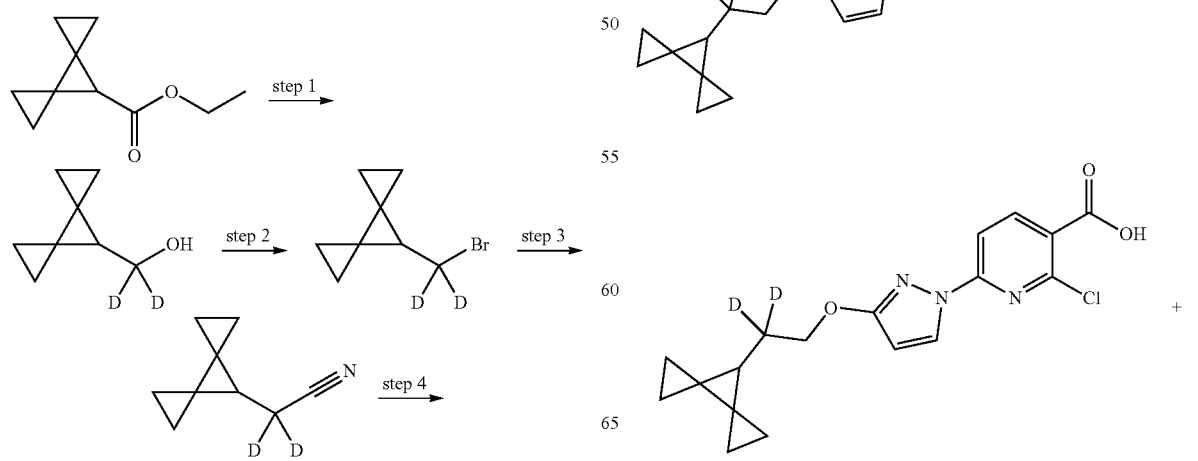

592

-continued

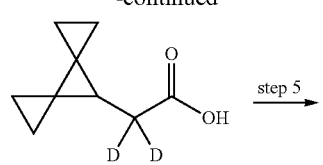

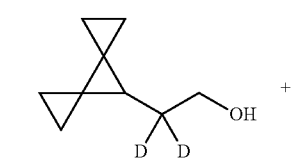

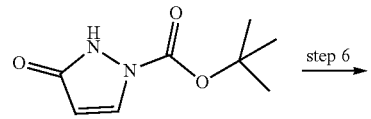

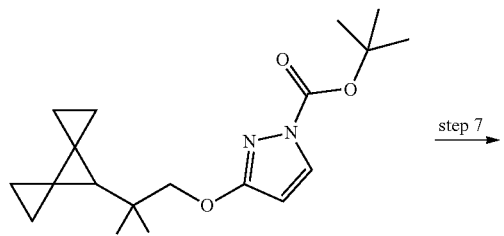

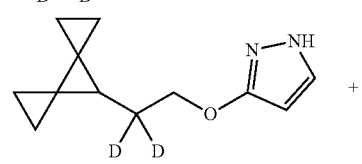

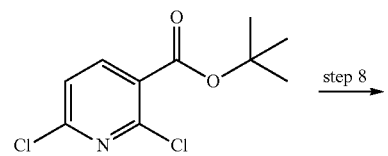

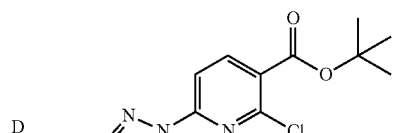

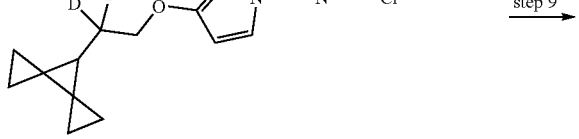

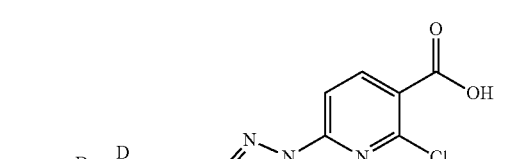

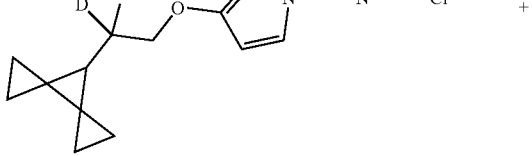

-continued

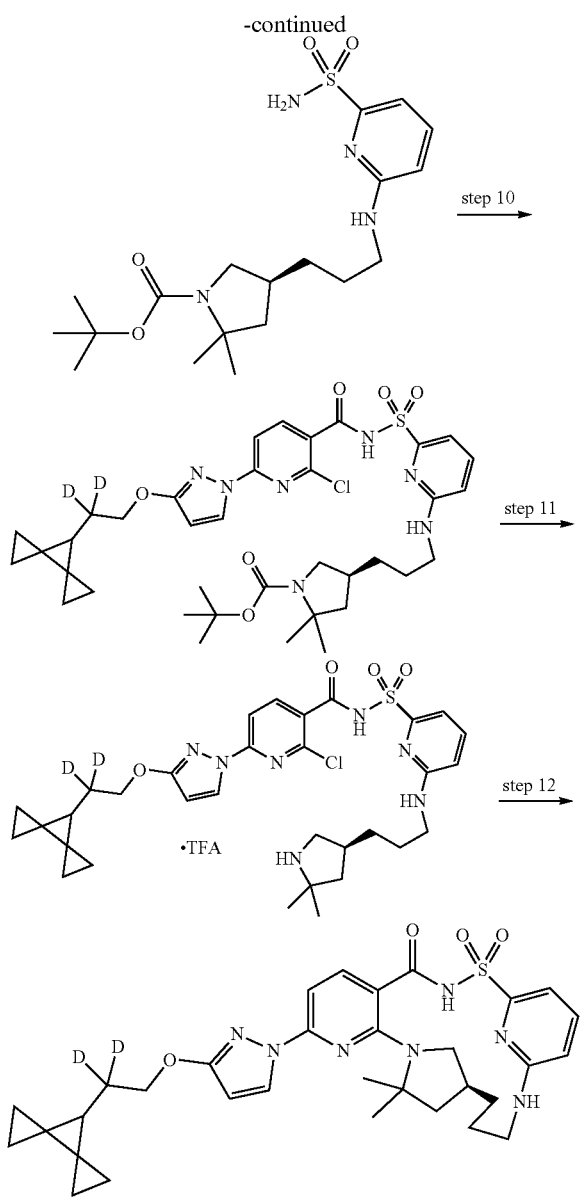

Step 1: Dideuterio(dispiro[2.0.2.1]heptan-7-yl)methanol

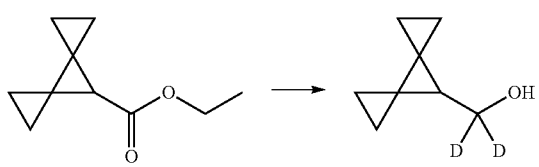

A solution of ethyl dispiro[2.0.2.1]heptane-7-carboxylate (2.8 g, 16.84 mmol) in tetrahydrofuran (35 mL) was cooled in an ice-water bath. Lithium aluminum deuteride (678 mg, 16.14 mmol) was added in small portions within 3 min and the reaction mixture was stirred under a nitrogen atmosphere at ambient temperature for 5 h. The reaction was chilled with an ice-water bath and the reaction mixture was diluted with ether (40 mL) and slowly quenched with the addition of saturated aqueous Rochelle's salt solution (~30 mL) until layers were clearly separated. The lower aqueous layer was extracted with diethyl ether (2×30 mL). The combined organic layers were washed with brine (30 mL), dried over magnesium sulfate, filtered and concentrated to afford dideuterio (dispiro[2.0.2.1]heptan-7-yl)methanol (2.5 g, 98%) as a light yellow oil. $^1$H NMR (400 MHz, Chloroform-d) δ 4.82 (bs, 1H), 1.62 (s, 1H), 0.87 (m, 4H), 0.65-0.48 (m, 4H).

Step 2: 7-[Bromo(dideuterio)methyl]dispiro[2.0.2.1]heptane

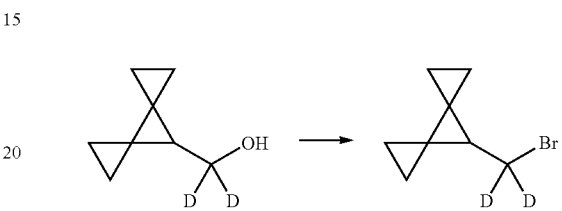

To a solution of triphenylphosphine (5.3 g, 20.1 mmol) in dichloromethane (74 mL) under nitrogen atmosphere at −15° C. was added a solution of bromine (1.1 mL, 21.3 mmol) in dichloromethane (9 mL) over 15 min. The reaction mixture was stirred an additional 15 min at −15° C. and then cooled to −30° C. A solution of dideuterio(dispiro[2.0.2.1]heptan-7-yl)methanol (2.5 g, 16.6 mmol) and pyridine (1.65 mL, 20.5 mmol) in dichloromethane (18 mL) was added dropwise. The mixture was warmed to −5° C. and stirred for 1 h and was poured into pentane (1 L). The formed precipitate was filtered off and the filtrate was concentrated. Pentane (300 mL) was added to the residue and the mixture was sonicated and filtered. The filtrate was concentrated to give a white solid which was again treated with pentane (300 mL) and filtered. The filtrate was concentrated and the residue was purified by silica gel chromatography using a 0%-5% diethyl ether in pentane gradient. Fractions containing product were combined and concentrated at 300 mbar with a 30° C. water bath to afford 7-[bromo(dideuterio)methyl]dispiro[2.0.2.1]heptane (2 g, 58%) as a white solid. $^1$H NMR (250 MHz, Chloroform-d) δ 1.88 (s, 1H), 0.8-1.0 (m, 4H), 0.63-0.72 (m, 2H), 0.48-0.6 (m, 2H).

Step 3: 2,2-Dideuterio-2-dispiro[2.0.2.1]heptan-7-yl-acetonitrile

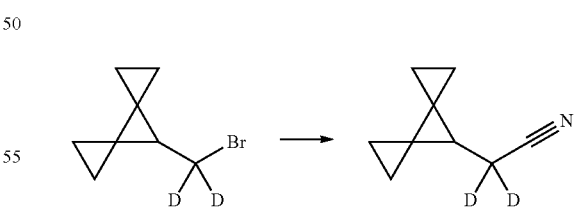

To a solution of 7-[bromo(dideuterio)methyl]dispiro[2.0.2.1]heptane (2.3 g, 22.02 mmol) in dimethyl sulfoxide (30 mL) was added sodium cyanide (753 mg, 27.53 mmol) and the reaction mixture was stirred at room temperature for 2 h. The mixture was diluted with brine (40 mL) and extracted with pentane (2×50 mL). The combined pentane layers were dried over magnesium sulfate, filtered and concentrated to afford 2, 2-dideuterio-2-dispiro[2.0.2.1]heptan-7-yl-acetonitrile (1.8 g, 77%) as colorless oil. $^1$H NMR (250 MHz, Chloroform-d) δ 1.68 (s, 1H), 0.8-1.05 (m, 4H), 0.65-0.8 (m, 2H), 0.54-0.62 (m, 2H).

Step 4: 2,2-Dideuterio-2-dispiro[2.0.2.1]heptan-7-yl-acetic Acid

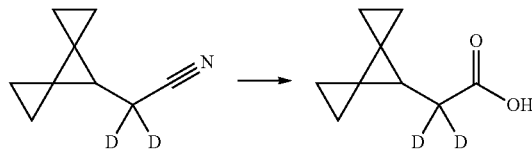 [SMILES: [2H]C([2H])(C#N)C1C2(CC2)C12CC2 ; [2H]C([2H])(C(=O)O)C1C2(CC2)C12CC2]

2,2-Dideuterio-2-dispiro[2.0.2.1]heptan-7-yl-acetonitrile (7.7 g, 56.951 mmol) was dissolved in CH₃CwaterD (105 mL) at room temperature. Sodium deuteroxide (52.2 g, 40% w/w, 509.23 mmol) was added, followed by CH₃CwaterD (105 mL). The mixture was heated at 72° C. in an oil bath under a nitrogen atmosphere (balloon) for 16 h. The mixture was cooled in an ice-water bath for 15 min. D2O (~20 mL) was added. Ether (2×50 mL) was used to extract the aqueous mixture. The aqueous layer was retained and treated with hydrochloric acid (6 N) until pH 2. The mixture was extracted with ether (3×50 mL). The combined ether layers were dried over anhydrous magnesium sulfate, filtered and concentrated to afford 2,2-dideuterio-2-dispiro[2.0.2.1]heptan-7-yl-acetic acid (6 g, 65%) as a pale yellow solid. ¹H NMR (250 MHz, Chloroform-d) δ 1.64 (s, 1H), 1.01-0.73 (m, 4H), 0.67 (ddd, J=8.3, 4.9, 3.5 Hz, 2H), 0.58-0.35 (m, 2H).

Step 5: 2,2-Dideuterio-2-dispiro[2.0.2.1]heptan-7-yl-ethanol

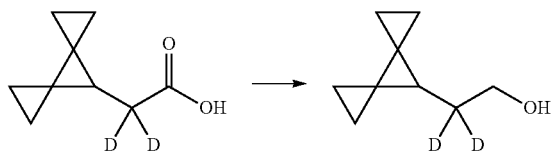 [SMILES: [2H]C([2H])(C(=O)O)C1C2(CC2)C12CC2 ; [2H]C([2H])(CO)C1C2(CC2)C12CC2]

Lithium aluminum hydride (2.84 g, 74.827 mmol) was weighed in a round bottom flask and chilled in an ice water bath under a nitrogen atmosphere (balloon). Added tetrahydrofuran (150 mL) and the mixture was stirred at 0° C. for 10 min. Then, 2,2-dideuterio-2-dispiro[2.0.2.1]heptan-7-yl-acetic acid (8.1 g, 52.528 mmol) in tetrahydrofuran (20 mL, 10 mL rinse) solution was added dropwise over 20 min. The mixture was slowly warmed to room temperature and stirred for 15 h. It was then cooled in an ice-water bath and quenched slowly with Rochelle's salt solution. Ether (200 mL) was added and the layers were separated and the aqueous layer was extracted with more ether (2×150 mL). The combined organics was dried over anhydrous magnesium sulfate, filtered and concentrated to afford 2,2-dideuterio-2-dispiro[2.0.2.1]heptan-7-yl-ethanol (7.5 g, 89%) as a pale yellow oil. ¹H NMR (250 MHz, Chloroform-d) δ 3.62 (s, 2H), 1.69 (s, 1H), 0.73-1.0 (m, 4H), 0.60-0.75 (m, 2H), 0.45-0.59 (m, 2H).

Step 6: tert-Butyl 3-(2,2-dideuterio-2-dispiro[2.0.2.1]heptan-7-yl-ethoxy)pyrazole-1-carboxylate

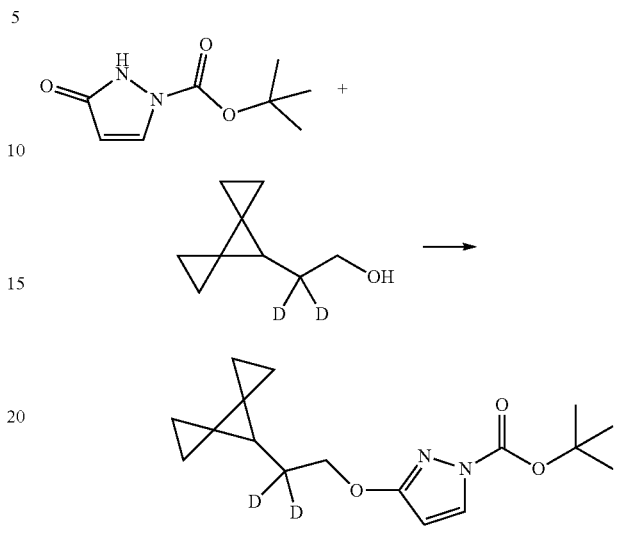

To a solution of tert-butyl 5-oxo-1H-pyrazole-2-carboxylate (10.25 g, 55.65 mmol) and 2,2-dideuterio-2-dispiro[2.0.2.1]heptan-7-yl-ethanol (8.193 g, 58.43 mmol) in tetrahydrofuran (128.1 mL) was added triphenylphosphine (15.33 g, 58.45 mmol). To the mixture was slowly added diisopropyl azodicarboxylate (11.82 g, 58.45 mmol) dropwise over 10 min. The reaction mixture was stirred at room temperature for 2 h. The tetrahydrofuran was removed under reduced pressure and the residue was purified by silica gel chromatography using a shallow gradient from 100% hexanes to 100% ethyl acetate to afford tert-butyl 3-(2,2-dideuterio-2-dispiro[2.0.2.1]heptan-7-yl-ethoxy)pyrazole-1-carboxylate (11.57 g, 68%) as a clear syrup. ESI-MS m/z calc. 306.19125, found 307.2 (M+1)⁺; Retention time: 0.8 min (LC Method A).

Step 7: 3-(2,2-Dideuterio-2-dispiro[2.0.2.1]heptan-7-yl-ethoxy)-1H-pyrazole

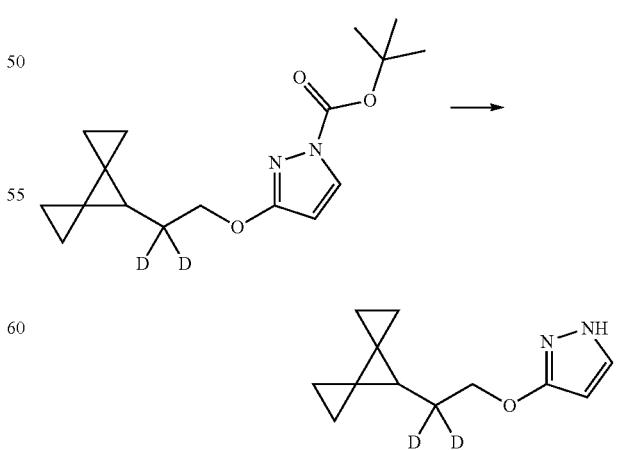

tert-Butyl 3-(2,2-dideuterio-2-dispiro[2.0.2.1]heptan-7-yl-ethoxy)pyrazole-1-carboxylate (11.57 g, 37.76 mmol)

was dissolved in dichloromethane (115.7 mL) with trifluoroacetic acid (43.64 mL, 566.4 mmol) and the reaction was stirred at room temperature for 2 h. The solvent was evaporated and the resulting oil was partitioned between ethyl acetate and saturated sodium bicarbonate solution. The aqueous portion was extracted two additional times with ethyl acetate, then organics were combined, washed with brine, dried over sodium sulfate, filtered and evaporated to afford 3-(2,2-dideuterio-2-dispiro[2.0.2.1]heptan-7-yl-ethoxy)-1H-pyrazole (7.789 g, 100%) as an oil. ESI-MS m/z calc. 206.13881, found 207.1 (M+1)⁺; Retention time: 0.59 min (LC Method A).

Step 8: tert-Butyl 2-chloro-6-[3-(2,2-dideuterio-2-dispiro[2.0.2.1]heptan-7-yl-ethoxy)pyrazol-1-yl]pyridine-3-carboxylate

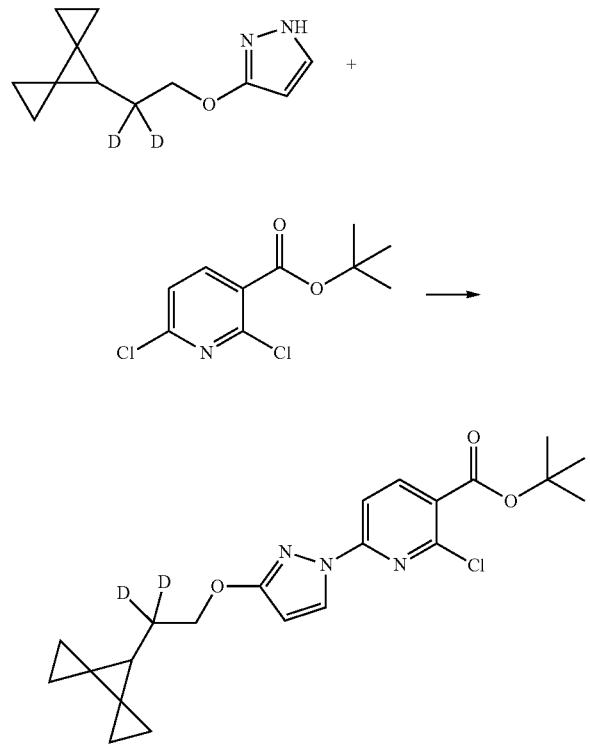

tert-Butyl 2,6-dichloropyridine-3-carboxylate (9.368 g, 37.76 mmol), 3-(2,2-dideuterio-2-dispiro[2.0.2.1]heptan-7-yl-ethoxy)-1H-pyrazole (7.789 g, 37.76 mmol) and potassium carbonate (6.268 g, 45.35 mmol) were combined in anhydrous dimethyl sulfoxide (155.8 mL). 1,4-diazabicyclo[2.2.2]octane (848 mg, 7.560 mmol) was added and the mixture was stirred at room temperature under nitrogen for 16 h. The reaction mixture was diluted with water (300 mL) and stirred for 15 min. Filtered off the solid and washed with water. The solid was dissolved in dichloromethane, dried over magnesium sulfate, filtered and concentrated to afford tert-butyl 2-chloro-6-[3-(2,2-dideuterio-2-dispiro[2.0.2.1]heptan-7-yl-ethoxy)pyrazol-1-yl]pyridine-3-carboxylate (15.54 g, 98%) as a white solid. ESI-MS m/z calc. 417.17883, found 418.1 (M+1)⁺; Retention time: 0.97 min (LC Method A).

Step 9: 2-Chloro-6-[3-(2,2-dideuterio-2-dispiro[2.0.2.1]heptan-7-yl-ethoxy) pyrazol-1-yl]pyridine-3-carboxylic Acid

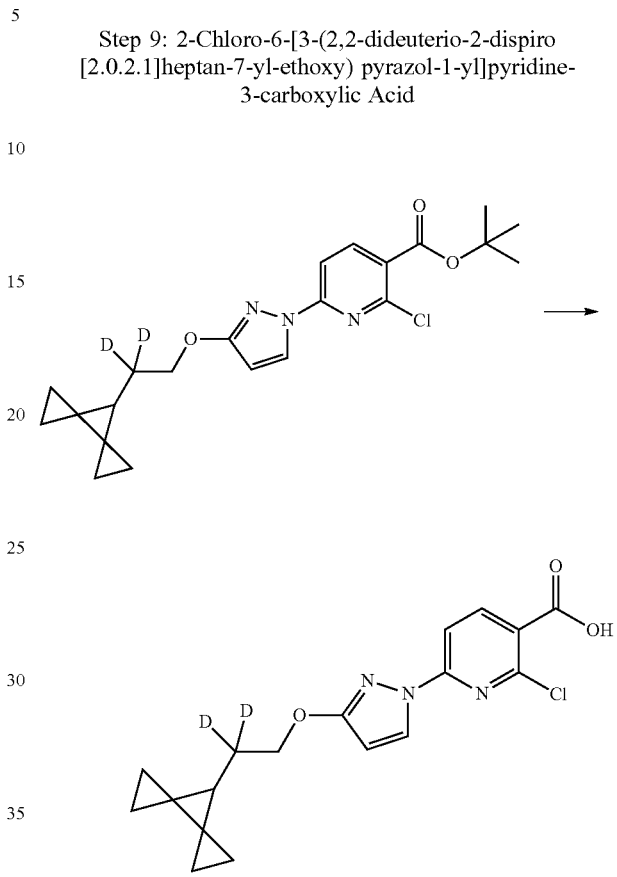

tert-Butyl 2-chloro-6-[3-(2,2-dideuterio-2-dispiro[2.0.2.1]heptan-7-yl-ethoxy)pyrazol-1-yl]pyridine-3-carboxylate (15.54 g, 37.18 mmol) was dissolved in dichloromethane (155.4 mL) with trifluoroacetic acid (42.97 mL, 557.7 mmol) and the reaction was stirred at room temperature for 16 h. The solvent was evaporated and to the resulting solid was added ether and the ether was then removed under reduced pressure. This was repeated twice more resulting in a white solid which was recrystallized from dichloromethane to give pure product as a solid. Product remained in the filtrate which was evaporated giving an off-white solid was dissolved in ethyl acetate and washed with 5N sodium hydroxide (2×), then 1N hydrochloric acid (1×), then dried (sodium sulfate), filtered and concentrated to a white solid which was purified by a reverse phase HPLC-MS method using a Luna C₁₈ (2) column (75×30 mm, 5 μm particle size) sold by Phenomenex (pn: 00C-4252-U0-AX) and a dual gradient run from 20%-80% mobile phase B over 15.0 min (mobile phase A=water (5 mM hydrochloric acid), mobile phase B=acetonitrile, flow rate=50 mL/min, injection volume=950 μL and column temperature=25° C.) giving pure product material which was combined with the originally crystallized material to give 2-chloro-6-[3-(2,2-dideuterio-2-dispiro[2.0.2.1]heptan-7-yl-ethoxy)pyrazol-1-yl]pyridine-3-carboxylic acid (10.43 g, 78%) as white solid. ESI-MS m/z calc. 361.1162, found 362.1 (M+1)⁺; Retention time: 0.78 min (LC Method A).

Step 10: tert-Butyl (4S)-4-[3-[[6-[[2-chloro-6-[3-(2,2-dideuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate

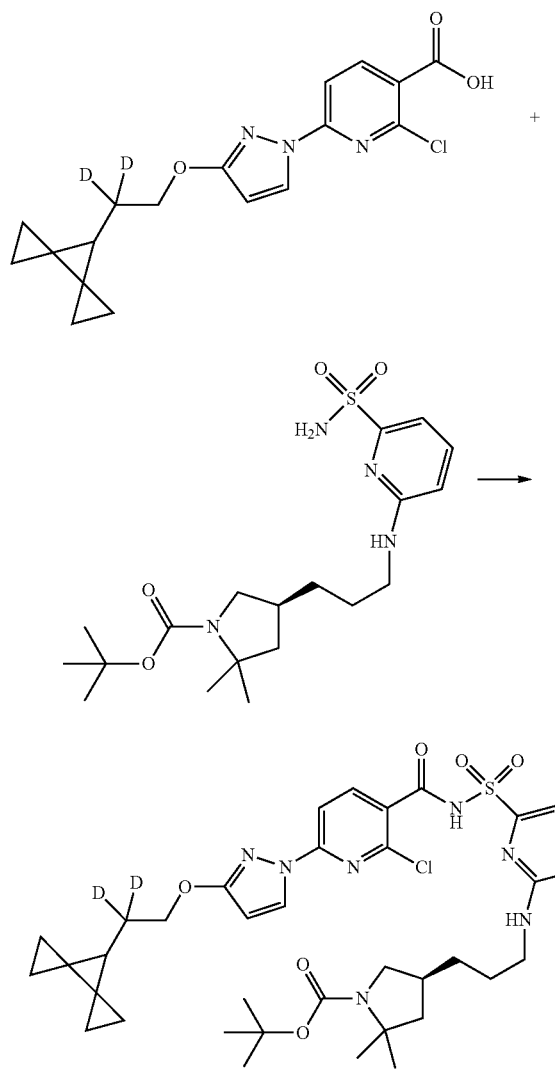

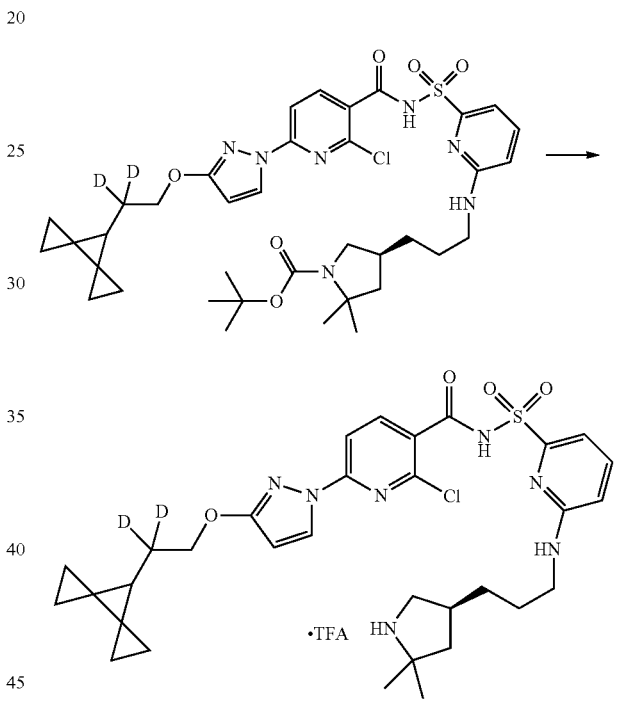

To a solution of 2-chloro-6-[3-(2,2-dideuterio-2-dispiro[2.0.2.1]heptan-7-yl-ethoxy)pyrazol-1-yl]pyridine-3-carboxylic acid (2 g, 5.528 mmol) in tetrahydrofuran (13.66 mL) was added carbonyl diimidazole (1.12 g, 6.907 mmol) (freshly recrystallized from tetrahydrofuran) and the mixture was stirred at room temperature for 3 h. Then tert-butyl (4S)-2,2-dimethyl-4-[3-[(6-sulfamoyl-2-pyridyl)amino]propyl]pyrrolidine-1-carboxylate (2.383 g, 5.776 mmol) was added as a solution in tetrahydrofuran (5 mL) followed by 1,8-diazabicyclo[5.4.0]undec-7-ene (2.594 mL, 17.35 mmol) and the resulting mixture was stirred for 3 h at room temperature. The reaction was diluted with water and ethyl acetate and then hydrochloric acid (6.178 mL of 6 M, 37.07 mmol) was added to the aqueous layer (pH=1). The layers were separated and the organic layer was washed with water (1×) and brine (1×) then dried over sodium sulfate, filtered and concentrated to a white foam which was purified on a 275 g $C_{18}$ reverse phase column eluting with a gradient from 50%-100% acetonitrile/water to afford tert-butyl(4S)-4-[3-[[6-[[2-chloro-6-[3-(2,2-dideuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (3.0854 g, 74%) as a white solid. ESI-MS m/z calc. 755.32007, found 756.1 (M+1)⁺; Retention time: 0.93 min (LC Method A).

Step 11: 2-Chloro-6-[3-(2,2-dideuterio-2-dispiro[2.0.2.1]heptan-7-yl-ethoxy) pyrazol-1-yl]-N-[[6-[3-[(3S)-5,5-dimethylpyrrolidin-3-yl]propylamino]-2-pyridyl]sulfonyl]pyridine-3-carboxamide tert-Butyl (4S)-4-[3-[[6-[[2-chloro-6-[3-(2,2-dideuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (3.0854 g, 4.079 mmol) was dissolved in dichloromethane (13.46 mL) and trifluoroacetic acid (12.57 mL, 163.2 mmol) was added and the mixture was stirred at room temperature for 90 min. The mixture was concentrated to dryness under reduced pressure. Toluene (50 mL) was added and the mixture was evaporated by rotary evaporation (45° C. water bath). Again added toluene (50 mL) and removed by rotary evaporation (45° C. water bath) then dried under vacuum giving 2-chloro-6-[3-(2,2-dideuterio-2-dispiro[2.0.2.1]heptan-7-yl-ethoxy)pyrazol-1-yl]-N-[[6-[3-[(3S)-5,5-dimethylpyrrolidin-3-yl]propylamino]-2-pyridyl]sulfonyl]pyridine-3-carboxamide (trifluoroacetate salt) (3.142 g, 100%) as a white solid. ESI-MS m/z calc. 655.26764, found 656.2 (M+1)⁺; Retention time: 0.65 min (LC Method A).

601

Step 12: (14S)-8-[3-(2-{Dispiro[2.0.2.1]heptan-7-yl}-2,2-dideuterio-ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 252)

602

Example 79: Preparation of (14S)-8-(3-{2-[(7-deuterio)dispiro[2.0.2.1]heptan-7-yl]ethoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 253)

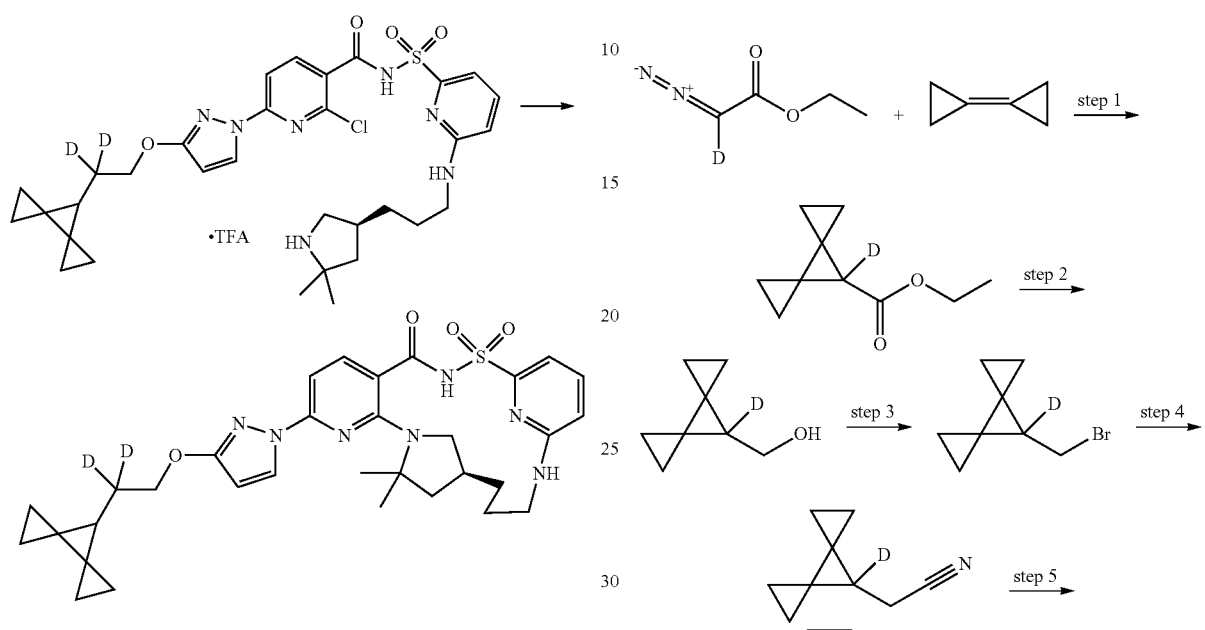

To a solution of 2-chloro-6-[3-(2,2-dideuterio-2-dispiro[2.0.2.1]heptan-7-yl-ethoxy)pyrazol-1-yl]-N-[[3-[(3S)-5,5-dimethylpyrrolidin-3-yl]propylamino]-2-pyridyl]sulfonyl]pyridine-3-carboxamide (trifluoroacetate salt) (3.142 g, 4.079 mmol) in NMP (188.5 mL) was added potassium carbonate (3.946 g, 28.55 mmol). The mixture was purged with nitrogen for 5 min. The mixture was heated at 150° C. for 24 h. The reaction mixture was cooled to room temperature and added to water (~200 mL) affording an off-white solid. The mixture was carefully acidified with hydrochloric acid (6.798 mL of 6 M, 40.79 mmol) affording a foamy slurry. The solid was collected by filtration and the wet filtered cake was dissolved in ethyl acetate and washed with brine (1×) and a small amount of 6N hydrochloric acid to maintain clarity in the layers. The organic layer was dried over magnesium sulfate, filtered and concentrated under vacuum affording a light yellow oil which was chromatographed on a 275 g C₁₈ reverse phase column eluting with 50%-100% acetonitrile/water to afford (14S)-8-[3-(2-{dispiro[2.0.2.1]heptan-7-yl}-2,2-dideuterio-ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 252) (2.16 g, 85%) as a white solid. ¹H NMR (400 MHz, dimethyl sulfoxide-d₆) δ 12.50 (s, 1H), 8.20 (d, J=2.8 Hz, 1H), 7.81 (d, J=8.2 Hz, 1H), 7.58 (dd, J=8.5, 7.2 Hz, 1H), 7.05 (d, J=7.1 Hz, 1H), 6.98 (d, J=8.7 Hz, 1H), 6.91 (d, J=8.2 Hz, 1H), 6.71 (d, J=8.5 Hz, 1H), 6.08 (d, J=2.7 Hz, 1H), 4.20 (d, J=1.4 Hz, 2H), 3.92 (d, J=12.9 Hz, 1H), 3.17 (d, J=5.0 Hz, 1H), 2.95 (d, J=13.1 Hz, 1H), 2.69 (d, J=13.8 Hz, 1H), 2.13 (s, 1H), 1.86 (dd, J=11.6, 5.2 Hz, 1H), 1.77 (s, 1H), 1.59 (d, J=7.7 Hz, 6H), 1.51 (s, 3H), 1.46 (s, 1H), 1.38-1.24 (m, 1H), 0.83 (s, 4H), 0.69-0.60 (m, 2H), 0.55-0.44 (m, 2H). ESI-MS m/z calc. 619.29095, found 620.2 (M+1)⁺; Retention time: 2.37 min (LC Method B).

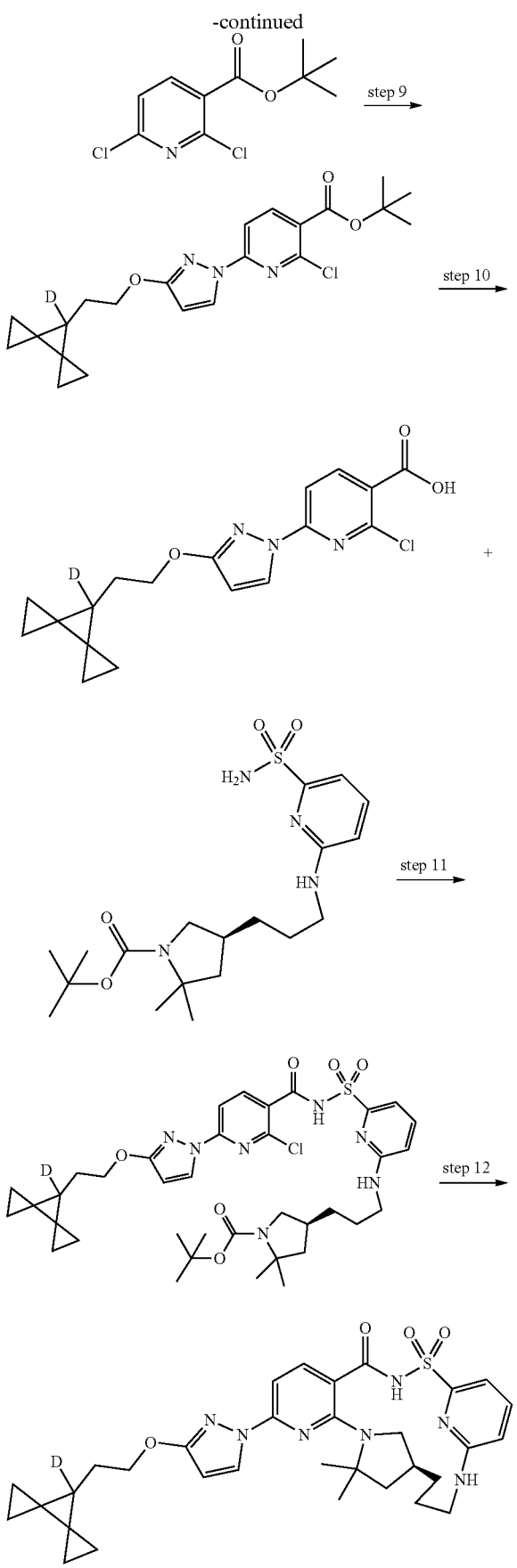

Step 1: Ethyl 7-deuteriodispiro[2.0.2.1]heptane-7-carboxylate

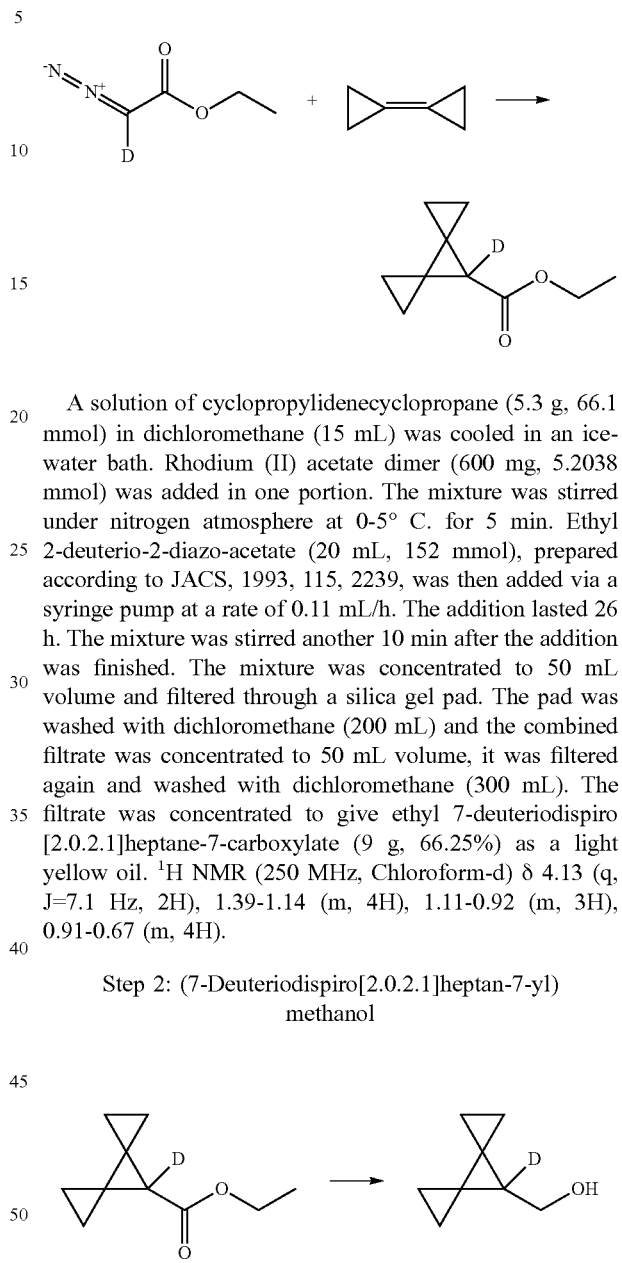

A solution of cyclopropylidenecyclopropane (5.3 g, 66.1 mmol) in dichloromethane (15 mL) was cooled in an ice-water bath. Rhodium (II) acetate dimer (600 mg, 5.2038 mmol) was added in one portion. The mixture was stirred under nitrogen atmosphere at 0-5° C. for 5 min. Ethyl 2-deuterio-2-diazo-acetate (20 mL, 152 mmol), prepared according to JACS, 1993, 115, 2239, was then added via a syringe pump at a rate of 0.11 mL/h. The addition lasted 26 h. The mixture was stirred another 10 min after the addition was finished. The mixture was concentrated to 50 mL volume and filtered through a silica gel pad. The pad was washed with dichloromethane (200 mL) and the combined filtrate was concentrated to 50 mL volume, it was filtered again and washed with dichloromethane (300 mL). The filtrate was concentrated to give ethyl 7-deuteriodispiro [2.0.2.1]heptane-7-carboxylate (9 g, 66.25%) as a light yellow oil. $^1$H NMR (250 MHz, Chloroform-d) δ 4.13 (q, J=7.1 Hz, 2H), 1.39-1.14 (m, 4H), 1.11-0.92 (m, 3H), 0.91-0.67 (m, 4H).

Step 2: (7-Deuteriodispiro[2.0.2.1]heptan-7-yl) methanol

A solution of ethyl 7-deuteriodispiro[2.0.2.1]heptane-7-carboxylate (9 g, 53.82 mmol) in tetrahydrofuran (100 mL) was cooled in an ice-water bath. Lithium aluminum hydride (2.5 g, 65.78 mmol) was added in small portions within 5 min and the mixture was stirred under a nitrogen atmosphere at ambient temperature for 5 h. The reaction was chilled with an ice-water bath for 5 min, diluted with ether (200 mL) and slowly quenched by addition of saturated aqueous Rochelle's salt solution (approx. 30 mL) until the layers were clearly separated. The aqueous layer was extracted with diethyl ether (2×50 mL). The combined ether layers were washed with brine (50 mL), dried over magnesium sulfate and concentrated to afford (7-deuteriodispiro

[2.0.2.1]heptan-7-yl)methanol (4.7 g, 98%) as a light yellow oil. $^1$H NMR (250 MHz, Chloroform-d) δ 3.72 (s, 2H), 1.00-0.75 (m, 4H), 0.74-0.44 (m, 4H).

Step 3: 7-(Bromomethyl)-7-deuterio-dispiro[2.0.2.1] heptane

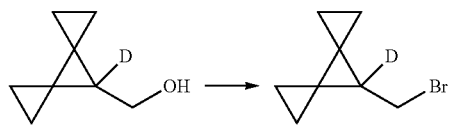 [SMILES: [2H]C1(CO)C2(CC2)C12CC2 ; [2H]C1(CBr)C2(CC2)C12CC2]

A solution of triphenylphosphine (9.38 g, 35.65 mmol) in dichloromethane (130 mL) under a nitrogen atmosphere was cooled to −15° C. using a dry ice acetone bath. A solution of bromine (1.85 mL, 35.65 mmol) in dichloromethane (17 mL) was added over 15 min and the reaction mixture was stirred an additional 15 min at −15° C. The mixture was cooled to −30° C. and a solution of (7-deuteriodispiro [2.0.2.1]heptan-7-yl)methanol (4.5 g, 35.95 mmol) and pyridine (2.9 mL, 36 mmol) in dichloromethane (34 mL) was added dropwise. Then the mixture was warmed to −5° C. and stirred for 1 h. The reaction mixture was poured into pentane (1 L) resulting in a white precipitate formation. The solid was filtered off over Celite and the filtrate was concentrated (250 mbar with approximately 30° C. water bath) to give a white solid. Pentane (300 mL) was added and the mixture was sonicated and filtered. The filtrate was concentrated to give a white solid which was again treated with pentane (300 mL) and filtered. The filtrate was concentrated and the residue was purified by silica gel column chromatography using a 0%-5% diethyl ether in pentane. Fractions containing product were concentrated at 300 mbar with a 30° C. water bath to afford 7-(bromomethyl)-7-deuteriodispiro[2.0.2.1]heptane (6.4 g, 95%) as a clear oil. $^1$H NMR (250 MHz, Chloroform-d) δ 3.49 (s, 2H), 1.42-1.17 (m, 2H), 1.12-0.81 (m, 2H), 0.79-0.64 (m, 2H), 0.62-0.43 (m, 2H).

Step 4: 2-(7-Deuteriodispiro[2.0.2.1]heptan-7-yl) acetonitrile

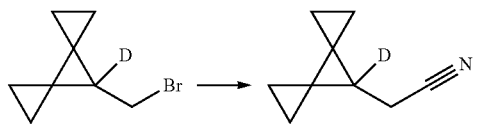 [SMILES: [2H]C1(CBr)C2(CC2)C12CC2 ; [2H]C1(CC#N)C2(CC2)C12CC2]

To a solution of 7-(bromomethyl)-7-deuterio-dispiro [2.0.2.1]heptane (2.3 g, 22.02 mmol) in dimethyl sulfoxide (30 mL) was added sodium cyanide (753 mg, 27.53 mmol) and the reaction mixture was stirred at room temperature for 2 h. The mixture was diluted with brine (40 mL) and extracted with pentane (2×50 mL). The combined pentane layer was dried over magnesium sulfate, filtered and concentrated to afford 2-(7-deuteriodispiro[2.0.2.1]heptan-7-yl) acetonitrile (4 g, 87%) as a clear oil. $^1$H NMR (250 MHz, Chloroform-d) δ 2.42 (s, 2H), 1.04-0.79 (m, 4H), 0.79-0.65 (m, 2H), 0.65-0.44 (m, 2H).

Step 5: 2-(7-Deuteriodispiro[2.0.2.1]heptan-7-yl) acetic Acid

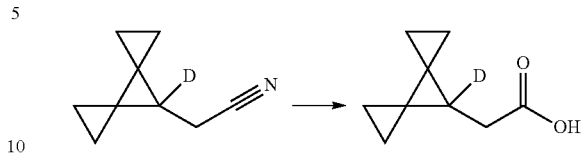

To a solution of 2-(7-deuteriodispiro[2.0.2.1]heptan-7-yl) acetonitrile (4 g, 29.8 mmol) in ethanol (60 mL) was added a solution of sodium hydroxide (12 g, 300 mmol) in water (25 mL) and the resulting solution was stirred at 73° C. for 15 h. The mixture was cooled to room temperature, diluted with water (~40 mL) and extracted with diethyl ether (2×25 mL). The aqueous phase was adjusted to pH=1 by the addition of 6 M hydrochloric acid and then extracted with diethyl ether (2×40 mL). The combined ether layers were dried over magnesium sulfate, filtered and concentrated to give 2-(7-deuteriodispiro[2.0.2.1]heptan-7-yl)acetic acid (2.6 g, 57%) as a slightly yellow solid. $^1$H NMR (250 MHz, Chloroform-d) δ 2.44 (s, 2H), 1.03-0.73 (m, 4H), 0.75-0.61 (m, 2H), 0.59-0.38 (m, 2H).

Step 6: 2-(7-Deuteriodispiro[2.0.2.1]heptan-7-yl) ethanol

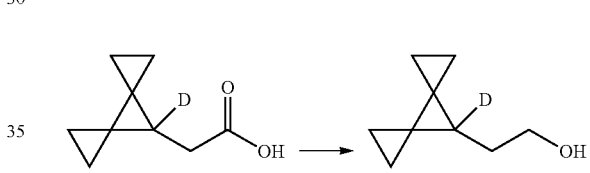

A suspension of lithium aluminum hydride (836 mg, 22 mmol) in tetrahydrofuran (35 mL) was cooled in an ice-water bath. 2-(7-Deuteriodispiro[2.0.2.1]heptan-7-yl)acetic acid (2.59 g, 16.9 mmol) in tetrahydrofuran (15 mL) was added dropwise over 10 min. The mixture was allowed to warm to ambient temperature and stir under a nitrogen atmosphere for 15 h. The reaction mixture was chilled with an ice-water bath for 5 min, then diluted with diethyl ether (60 mL) and slowly quenched with the addition of saturated aqueous Rochelle's salt solution (~40 mL) until layers were clearly separated. The lower aqueous layer was extracted with diethyl ether (2×50 mL). The combined ether layers were washed with brine (40 mL), dried over magnesium sulfate, filtered and concentrated to afford 2-(7-deuteriodispiro[2.0.2.1]heptan-7-yl)ethanol (2.4 g, quantitative yield) as a light yellow oil. $^1$H NMR (250 MHz, Chloroform-d) δ 3.63 (t, J=6.9 Hz, 2H), 1.68 (t, J=6.8 Hz, 2H), 0.94-0.72 (m, 4H), 0.72-0.57 (m, 2H), 0.57-0.38 (m, 2H).

Step 7: tert-Butyl 3-[2-(7-deuteriodispiro[2.0.2.1] heptan-7-yl)ethoxy]pyrazole-1-carboxylate

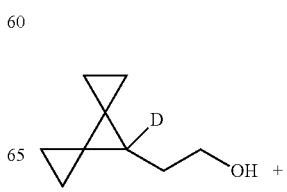

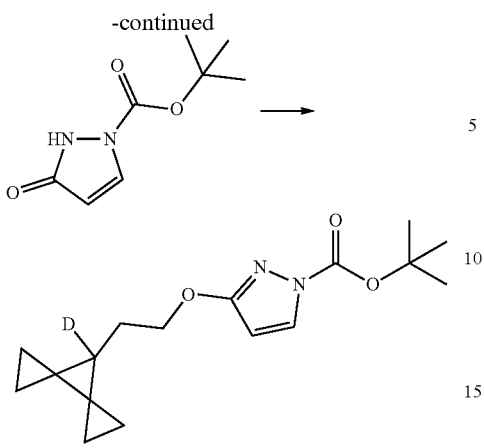

To a solution of tert-butyl 5-oxo-1H-pyrazole-2-carboxylate (1.26 g, 6.84 mmol) and 2-(7-deuteriodispiro[2.0.2.1]heptan-7-yl)ethanol (1 g, 6.48 mmol), triphenylphosphine (1.78 g, 6.8 mmol) in tetrahydrofuran (10 mL) was added diisopropyl azodicarboxylate (1.34 mL, 7.18 mmol) dropwise and the reaction mixture was stirred at 50° C. for 12 h. The mixture was concentrated and the residue was purified by silica gel column chromatography using a gradient from 100% hexanes to 10% ethyl acetate in hexanes to afford tert-butyl 3-[(7-deuteriodispiro[2.0.2.1]heptan-7-yl)methoxy]pyrazole-1-carboxylate (1.75 g, 80%) as a white solid. $^1$H NMR (250 MHz, Chloroform-d) δ 7.82 (d, J=2.9 Hz, 1H), 5.84 (d, J=3.0 Hz, 1H), 4.26 (s, 2H), 1.58 (s, 9H), 1.44 (d, J=6.2 Hz, 2H), 0.93-0.73 (m, 4H), 0.65 (d, J=9.2 Hz, 2H), 0.49 (d, J=8.8 Hz, 2H). ESI-MS m/z calc. 306.2, found 307.3 (M+1)$^+$; Retention time: 4.85 min (LC Method P).

Step 8: 3-[2-(7-Deuteriodispiro[2.0.2.1]heptan-7-yl)ethoxy]-1H-pyrazole

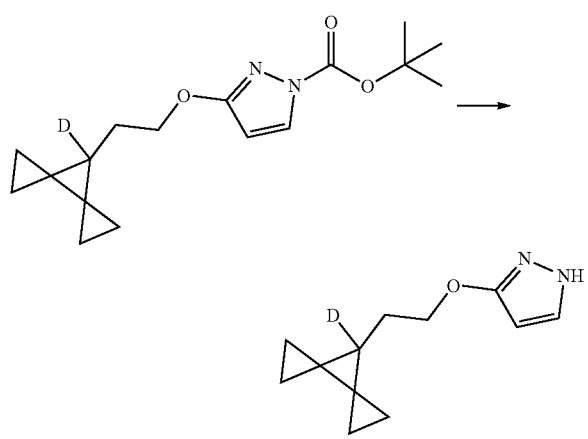

To a solution of tert-butyl 3-[(7-deuteriodispiro[2.0.2.1]heptan-7-yl)methoxy]pyrazole-1-carboxylate (1.75 g, 5.72 mmol) in dichloromethane (20 mL) was added trifluoroacetic acid (10 mL) and the resulting mixture was stirred at room temperature for 2 h. The mixture was concentrated and the residue was partitioned between ethyl acetate (50 mL) and saturated aqueous sodium bicarbonate solution (25 mL). The layers were separated and the aqueous layer was extracted with ethyl acetate (2×25 mL). The combined organic layers were washed with brine, dried over sodium sulfate, filtered and concentrated to give 3-[(7-deuteriodispiro[2.0.2.1]heptan-7-yl)methoxy]-1H-pyrazole (1.2 g, quantitative yield) as a white solid. $^1$H NMR (250 MHz, Chloroform-d) δ 7.35 (d, J=1.3 Hz, 1H), 5.71 (d, J=1.4 Hz, 1H), 4.12 (t, J=7.8 Hz, 2H), 1.87 (t, J=6.7 Hz, 2H), 0.96-0.73 (m, 4H), 0.70-0.58 (m, 2H), 0.56-0.39 (m, 2H). ESI-MS m/z calc. 205.1, found 206.4 (M+1)$^+$; Retention time: 2.95 min (LC Method P).

Step 9: tert-Butyl 2-chloro-6-[3-[2-(7-deuteriodispiro[2.0.2.1]heptan-7-yl)ethoxy]pyrazol-1-yl]pyridine-3-carboxylate

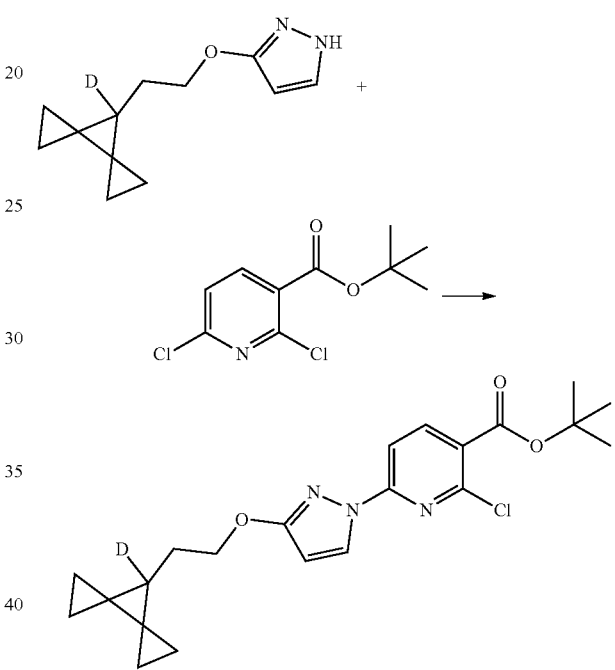

To a mixture of tert-butyl 2,6-dichloropyridine-3-carboxylate (1.44 g, 5.8 mmol) and 3-[(7-deuteriodispiro[2.0.2.1]heptan-7-yl)methoxy]-1H-pyrazole (1.2 g, 3.93 mmol) in anhydrous dimethyl sulfoxide (24 mL) was added potassium carbonate (965 mg, 6.97 mmol) and 1,4-diazabicyclo[2.2.2]octane (130 mg, 1.16 mmol). The resulting mixture was stirred under nitrogen atmosphere at room temperature for 16 h. The mixture then was diluted with water (45 mL) and stirred for 15 min. The resultant white solid was collected by filtration and washed with water (2×20 mL). The solid was dried and purified by silica gel column chromatography using a gradient from 100% hexanes to 60% ethyl acetate in hexanes to afford tert-butyl 2-chloro-6-[3-[(7-deuteriodispiro[2.0.2.1]heptan-7-yl)methoxy]pyrazol-1-yl]pyridine-3-carboxylate (1.8 g, quantitative yield) as a white solid. $^1$H NMR (250 MHz, Chloroform-d) δ 8.34 (dd, J=2.9, 1.1 Hz, 1H), 8.18 (dd, J=8.4, 1.1 Hz, 1H), 7.69 (dd, J=8.4, 1.0 Hz, 1H), 5.93 (dd, J=2.9, 1.1 Hz, 1H), 4.24 (s, 2H), 1.74-1.52 (m, 10H), 1.48 (s, 1H), 0.93-0.77 (m, 4H), 0.71-0.60 (m, 2H), 0.55-0.44 (m, 2H). ESI-MS m/z calc. 416.2, found 417.5 (M+1)$^+$; Retention time: 4.87 min (LC Method P).

Step 10: 2-Chloro-6-[3-[2-(7-deuteriodispiro [2.0.2.1]heptan-7-yl)ethoxy]pyrazol-1-yl]pyridine-3-carboxylic Acid

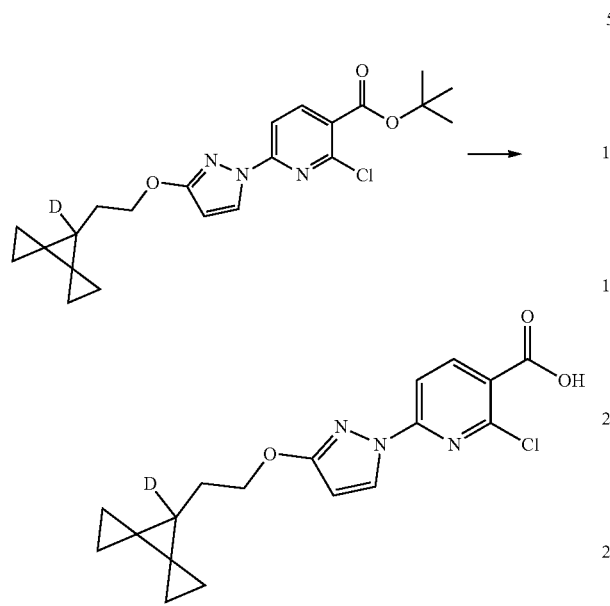

To a solution of tert-butyl 2-chloro-6-[3-[(7-deuteriodispiro[2.0.2.1]heptan-7-yl)methoxy]pyrazol-1-yl]pyridine-3-carboxylate (1.8 g, 4.32 mmol) in dichloromethane (20 mL) was added trifluoroacetic acid (5 mL) and the reaction mixture was stirred at room temperature for 15 h. The mixture was concentrated and the residue was triturated with a mixture of diethyl ether/pentane (20 mL each). The precipitated solid was collected by filtration to afford 2-chloro-6-[3-[(7-deuteriodispiro[2.0.2.1]heptan-7-yl) methoxy]pyrazol-1-yl]pyridine-3-carboxylic acid (1.19 g, 76% yield) as a white solid. $^1$H NMR (250 MHz, dimethyl sulfoxide-$d_6$) δ 8.46-8.34 (m, 2H), 7.72 (dd, J=8.4, 0.8 Hz, 1H), 6.17 (dd, J=2.9, 0.8 Hz, 1H), 4.23 (s, 2H), 1.46 (s, 2H), 0.92-0.74 (m, 4H), 0.64 (dd, J=7.6, 4.3 Hz, 2H), 0.50 (dd, J=7.1, 4.2 Hz, 2H). ESI-MS m/z calc. 361.1, found 361.3 (M+1)$^+$; Retention time: 3.85 min (LC Method P).

Step 11: tert-Butyl (4S)-4-[3-[[6-[[2-chloro-6-[3-[2-(7-deuteriodispiro[2.0.2.1]heptan-7-yl)ethoxy]pyrazol-1-yl]pyridine-3-carbonyl]sulfamoyl]-2-pyridyl] amino]propyl]-2,2-dimethyl-pyrrolidine-1-carboxylate

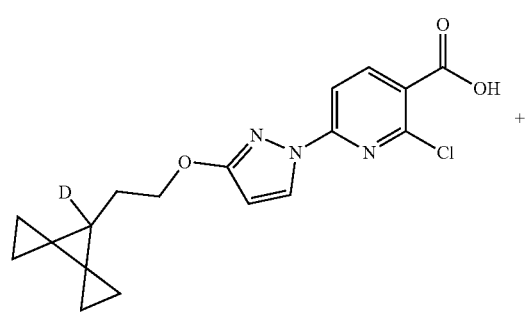

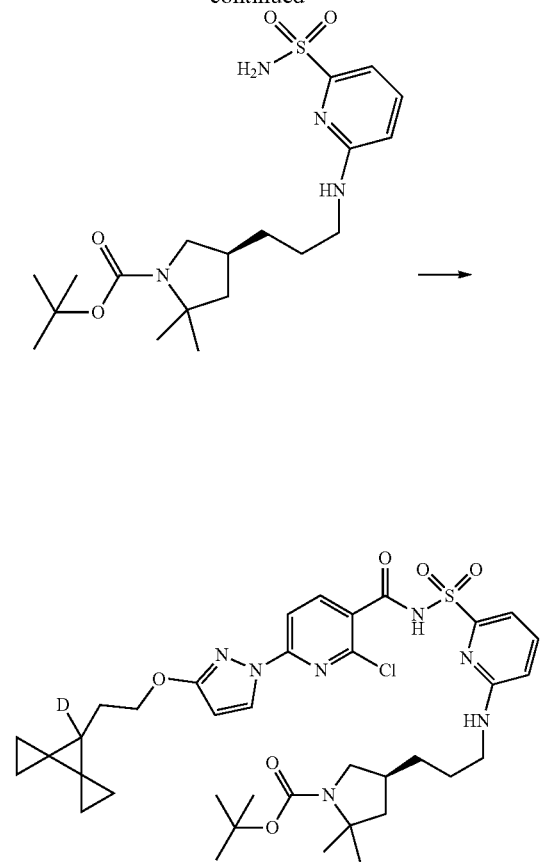

To a solution of 2-chloro-6-[3-[2-(7-deuteriodispiro [2.0.2.1]heptan-7-yl)ethoxy]pyrazol-1-yl]pyridine-3-carboxylic acid (100 mg, 0.2772 mmol) in tetrahydrofuran (2 mL) was added carbonyl diimidazole (54 mg, 0.3330 mmol) and the mixture was stirred under a nitrogen atmosphere (balloon) at room temperature for 2 h. Then, tert-butyl (4S)-2,2-dimethyl-4-[3-[(6-sulfamoyl-2-pyridyl)amino]propyl]pyrrolidine-1-carboxylate (121 mg, 0.2933 mmol) was added followed by 1,8-diazabicyclo[5.4.0]undec-7-ene (130 µL, 0.8693 mmol) and the reaction was stirred for 16 h. The reaction was diluted with ethyl acetate and washed with a 1:1 saturated ammonium chloride/brine solution. The organics were separated, dried over sodium sulfate, filtered and evaporated. The resultant brown residue was purified by silica gel chromatography using a shallow gradient from 100% hexanes to 100% ethyl acetate to afford tert-butyl (4S)-4-[3-[[6-[[2-chloro-6-[3-[2-(7-deuteriodispiro[2.0.2.1] heptan-7-yl)ethoxy]pyrazol-1-yl]pyridine-3-carbonyl]sulfamoyl]-2-pyridyl]amino]propyl]-2,2-dimethyl-pyrrolidine-1-carboxylate (77 mg, 31%) as a white solid. ESI-MS m/z calc. 754.3138, found 755.46 (M+1)$^+$; Retention time: 0.67 min (LC Method G).

Step 12: (14S)-8-(3-{2-[(7-deuterio)dispiro[2.0.2.1]heptan-7-yl]ethoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 253)

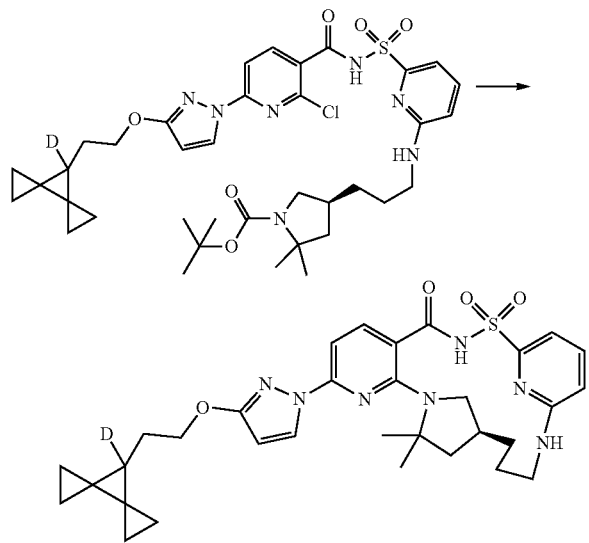

A solution of tert-butyl (4S)-4-[3-[[6-[[2-chloro-6-[3-[2-(7-deuteriodispiro[2.0.2.1]heptan-7-yl)ethoxy]pyrazol-1-yl]pyridine-3-carbonyl]sulfamoyl]-2-pyridyl]amino]propyl]-2,2-dimethyl-pyrrolidine-1-carboxylate (77 mg, 0.1019 mmol) in dichloromethane (400 μL) and trifluoroacetic acid (100 μL, 1.307 mmol) was stirred at room temperature for 4 h. The solvents were removed by evaporation and the resultant residue was dissolved in ethyl acetate. Washed with 2 mL of saturated sodium bicarbonate solution and the organic layer was collected and solvent evaporated. The resultant thick oil was further dried under vacuum. The resulting residue was dissolved in dimethyl sulfoxide (5 mL) and 3 Å molecular sieves were added and the reaction mixture was stirred for 10 min. Then, cesium fluoride (49 mg, 0.3226 mmol) and potassium carbonate (47 mg, 0.3401 mmol) were added and the reaction mixture was heated at 150° C. for 16 h. The reaction mixture was filtered through a Whatman filter disc (puradisc 25 TF) and filtrate was purified by a reverse phase HPLC-MS method using a dual gradient run from 50%-99% mobile phase B over 15.0 min (mobile phase A=water (0.05% hydrochloric acid), mobile phase B=acetonitrile) to afford (14S)-8-(3-{2-[(7-deuterio)dispiro[2.0.2.1]heptan-7-yl]ethoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 253) (26.9 mg, 43%) as white solid. ¹H NMR (400 MHz, Chloroform-d) δ 8.18 (d, J=2.8 Hz, 1H), 8.05 (d, J=8.3 Hz, 1H), 7.58-7.47 (m, 2H), 7.26 (s, 1H), 6.56 (d, J=8.2 Hz, 1H), 5.89 (d, J=2.8 Hz, 1H), 4.71 (s, 1H), 4.24 (t, J=6.8 Hz, 2H), 3.85 (d, J=37.1 Hz, 1H), 3.32 (s, 1H), 3.15 (d, J=13.6 Hz, 1H), 3.02 (d, J=27.8 Hz, 1H), 2.56 (s, 1H), 2.06 (t, J=10.0 Hz, 1H), 1.89 (t, J=6.8 Hz, 2H), 1.74-1.37 (m, 10H), 0.85 (q, J=2.4 Hz, 4H), 0.75-0.58 (m, 2H), 0.55-0.42 (m, 2H). ESI-MS m/z calc. 618.2847, found 619.15 (M+1)⁺; Retention time: 1.96 min (LC Method G).

Example 80: Preparation of (14S)-8-[3-(2-{dispiro[2.0.2.1]heptan-7-yl}ethoxy)-1H-pyrazol-1-yl]-20-hydroxy-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 254)

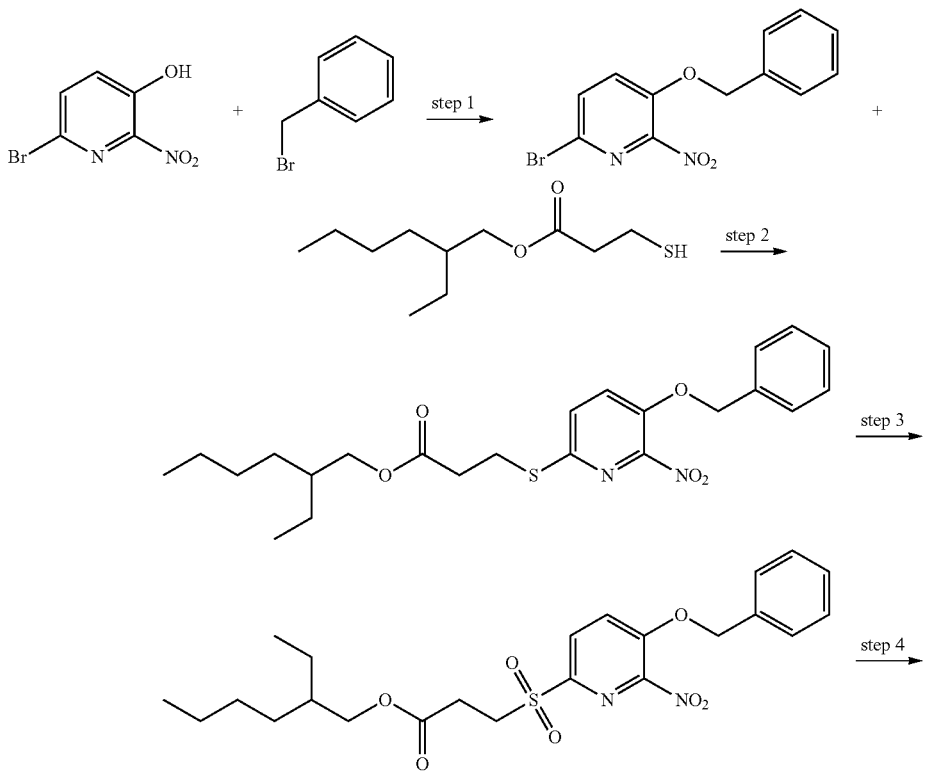

613 614
-continued
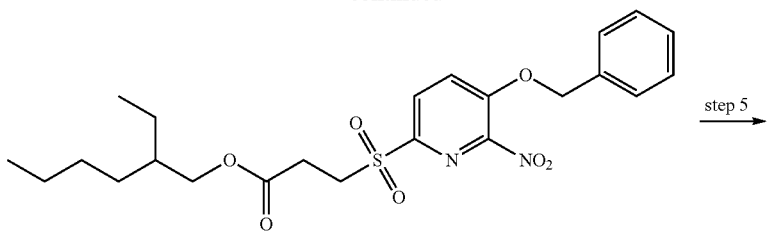
step 5
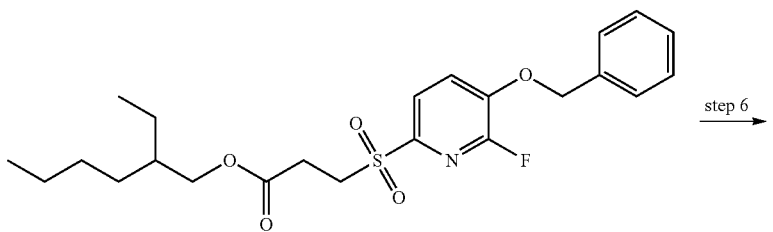
step 6
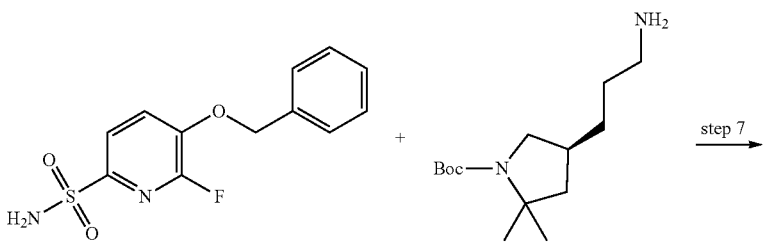
step 7
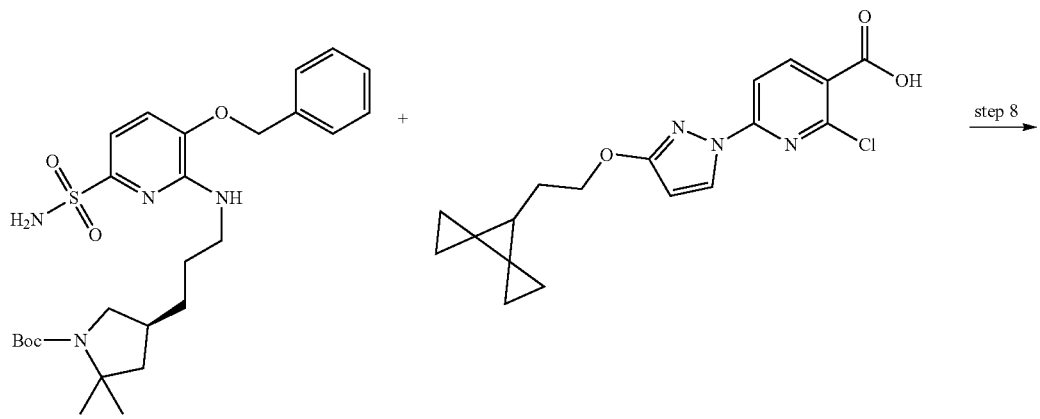
step 8
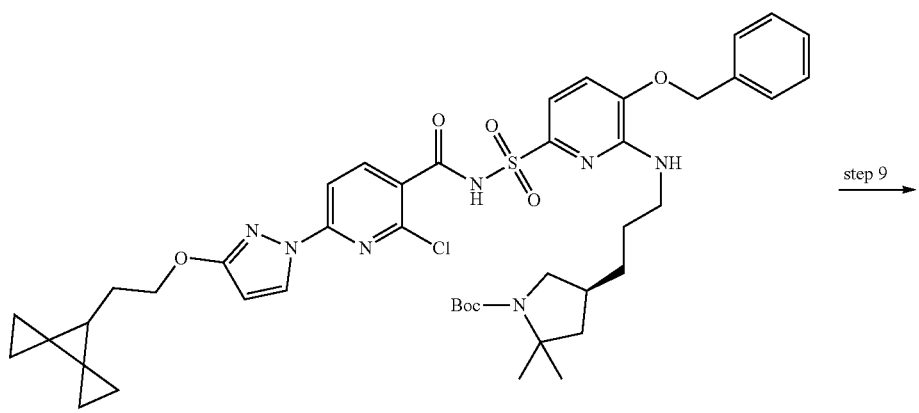
step 9

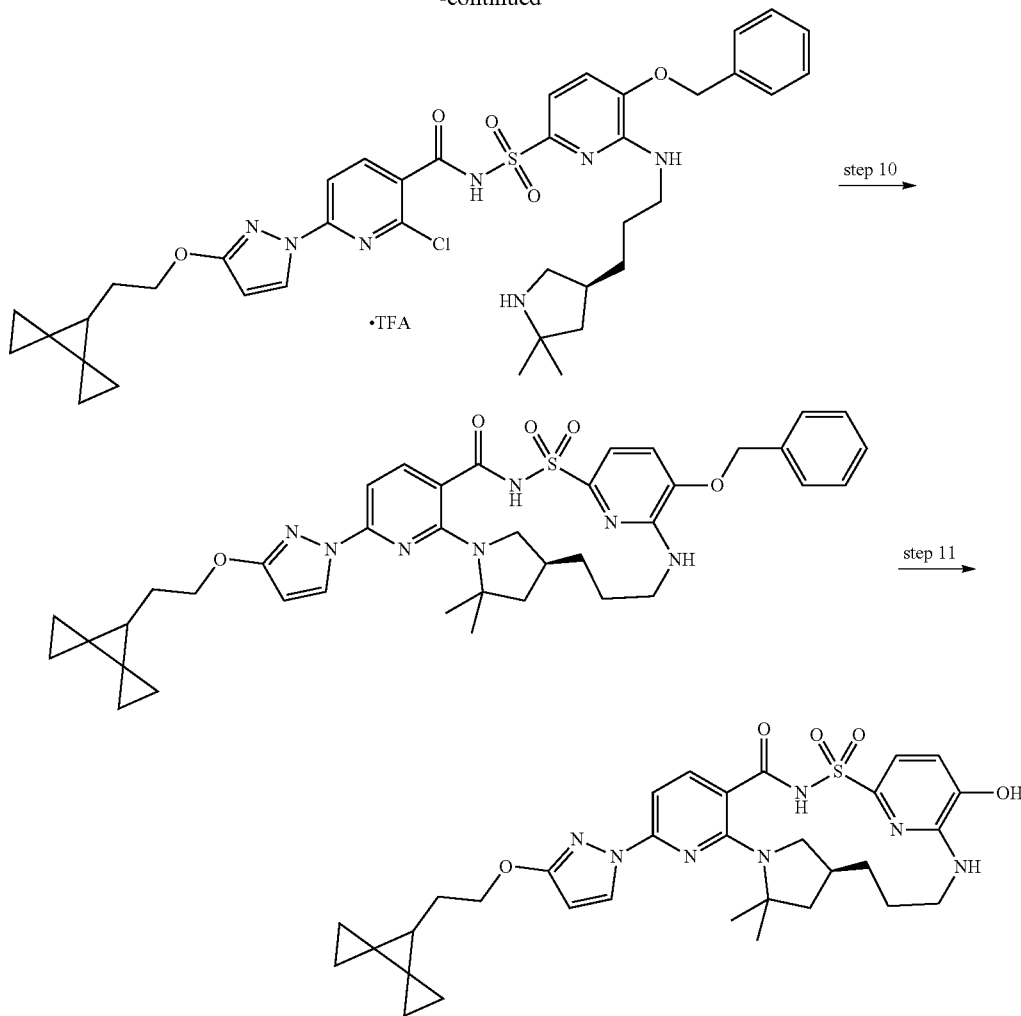

Step 1: 3-Benzyloxy-6-bromo-2-nitro-pyridine

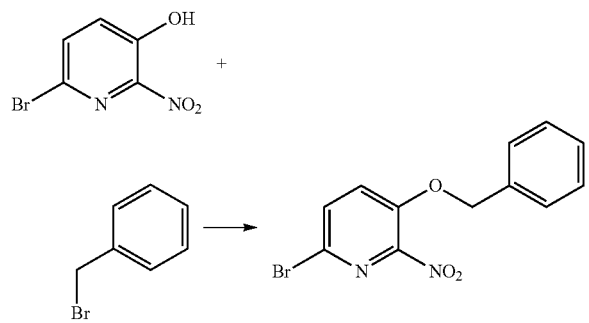

A solution of 6-bromo-2-nitro-pyridin-3-ol (12 g, 54.796 mmol) in dry N,N-dimethylformamide (100 mL) under nitrogen was cooled with an ice-water bath. Sodium hydride (2.49 g, 62.256 mmol, 60% in mineral oil) was added in one portion and the reaction was stirred for 10 min. Then benzyl chloride (7.5900 g, 6.9 mL, 59.961 mmol) was added and the reaction was allowed to warm to room temperature. The reaction was stirred at 60° C. for two days. The reaction was allowed to cool to room temperature, quenched with water (200 mL) and extracted with ethyl acetate (5×100 mL). The combined organic layers were washed with brine (3×70 mL), dried over anhydrous sodium sulfate, filtered and concentrated under reduced pressure. The residue was triturated in a 4:1 heptanes/ethyl acetate mixture (50 mL). The resulting solid was filtered, washed with heptanes and dried under reduced pressure to yield 3-benzyloxy-6-bromo-2-nitro-pyridine (13.643 g, 81%) as a yellow solid. $^1$H NMR (300 MHz, CDCl$_3$) δ 5.23 (s, 2H), 7.33-7.43 (m, 6H), 7.60 (d, J=8.7 Hz, 1H). ESI-MS m/z calc. 307.9797, found 309.0 (M+1)$^+$; Retention time: 2.155 min (LC Method I).

Step 2: 2-Ethylhexyl 3-[(5-benzyloxy-6-nitro-2-pyridyl)sulfanyl]propanoate

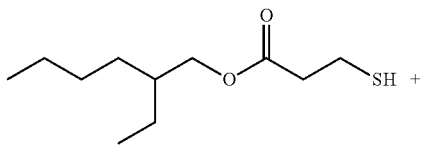

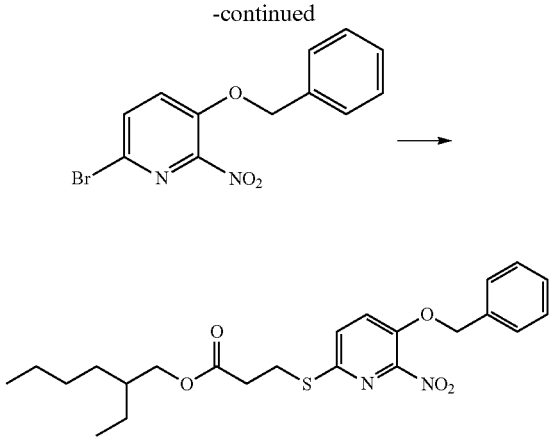

To a degassed solution of 3-benzyloxy-6-bromo-2-nitropyridine (13.143 g, 42.518 mmol) and diisopropylethylamine (11.130 g, 15 mL, 86.117 mmol) in dry toluene (260 mL) was added Xantphos (1.49 g, 2.5751 mmol), tris(dibenzylideneacetone)dipalladium(0) (1.155 g, 1.2613 mmol) and diisopropylethylamine (11.130 g, 15 mL, 86.117 mmol). The reaction was equipped with a reflux condenser and stirred overnight at 110° C. The reaction was cooled to room temperature, filtered and washed with ethyl acetate. The filtrate was concentrated under reduced pressure. The crude product was purified by flash chromatography on silica gel. Companion loaded with heptane (gradient from 100% heptane to 30% ethyl acetate in heptane) to yield 2-ethylhexyl 3-[(5-benzyloxy-6-nitro-2-pyridyl)sulfanyl]propanoate (18.977 g, 95%). ESI-MS m/z calc. 446.1875, found 447.2 (M+1)$^+$; Retention time: 2.262 min (LC Method I).

Step 3: 2-Ethylhexyl 3-[(5-benzyloxy-6-nitro-2-pyridyl)sulfonyl]propanoate

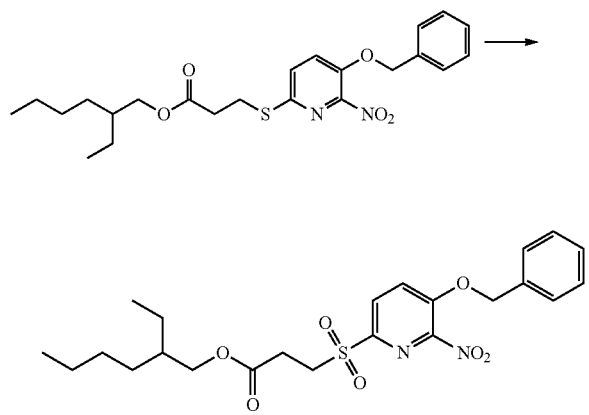

m-Chloroperbenzoic acid (19.795 g, 88.326 mmol) was added portionwise to a solution of 2-ethylhexyl 3-[(5-benzyloxy-6-nitro-2-pyridyl)sulfanyl]propanoate (19.65 g, 44.003 mmol) in dichloromethane (170 mL). The reaction was exothermic and turned turbid. The reaction was stirred overnight at room temperature. Ethyl acetate (200 mL) was added and the reaction was washed successively with aqueous 5% sodium bicarbonate solution (200 mL) and 0.5 M sodium hydroxide aqueous solution (2×200 mL). The organic layer was dried over sodium sulfate, filtered and concentrated under reduced pressure to yield 2-ethylhexyl 3-[(5-benzyloxy-6-nitro-2-pyridyl)sulfonyl]propanoate (20.905 g, 99%) as a yellow oil. $^1$H NMR (300 MHz, CDCl$_3$) δ 0.83-0.94 (m, 6H), 1.22-1.32 (m, 6H), 1.50-1.64 (m, 2H), 2.87 (t, J=7.6 Hz, 2H), 3.70 (t, J=7.6 Hz, 2H), 4.01 (dd, J=6.0, 2.2 Hz, 2H), 5.37 (s, 2H), 7.35-7.48 (m, 5H), 7.69 (d, J=8.5 Hz, 1H), 8.22 (d, J=8.5 Hz, 1H). ESI-MS m/z calc. 478.1774, found 367.1 (M-C$_8$H$_{16}$+1)$^+$; Retention time: 2.419 min (LC Method I).

Step 4: 2-Ethylhexyl 3-[(6-amino-5-benzyloxy-2-pyridyl)sulfonyl]propanoate

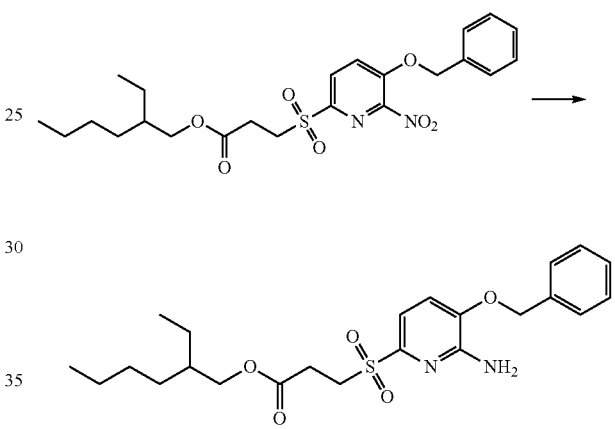

To a solution of 2-ethylhexyl 3-[(5-benzyloxy-6-nitro-2-pyridyl)sulfonyl]propanoate (6.24 g, 13.039 mmol) in ethanol (250 mL) and water (50 mL) was added iron (2.525 g, 45.214 mmol) and ammonium chloride (2.021 g, 37.782 mmol). The reaction was stirred at 100° C. for 1.5 h, cooled to room temperature, filtered over Celite and washed with dichloromethane (200 mL). The filtrate was concentrated under reduced pressure, diluted in dichloromethane (100 mL) and washed with water (2×50 mL). The organic layer was dried over anhydrous sodium sulfate, filtered and concentrated under reduced pressure to yield 2-ethylhexyl 3-[(6-amino-5-benzyloxy-2-pyridyl)sulfonyl]propanoate (6.25 g, quantitative yield) as a yellow oil. ESI-MS m/z calc. 448.2032, found 449.3 (M+1)$^+$; Retention time: 2.565 min (LC Method N).

Step 5: 2-Ethylhexyl 3-[(5-benzyloxy-6-fluoro-2-pyridyl)sulfonyl]propanoate

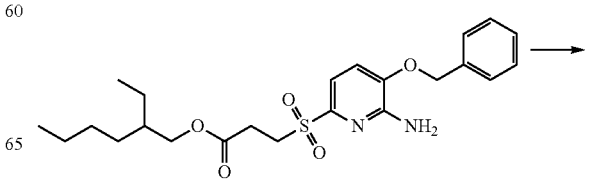

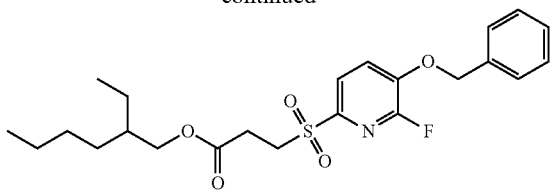

A solution of 2-ethylhexyl 3-[(6-amino-5-benzyloxy-2-pyridyl)sulfonyl]propanoate (6.25 g, 13.933 mmol) in hydrogen fluoride in pyridine (71.500 g, 65 mL, 721.45 mmol) was cooled to −40° C. The resulting red solution was treated with sodium nitrite (1.92 g, 27.828 mmol) and allowed to warm to room temperature. A gas release was observed and the reaction turned orange and turbid. The reaction was stirred overnight at room temperature and slowly poured over ice and water (400 mL). The mixture was neutralized by carefully adding aqueous sodium bicarbonate and was extracted with ethyl acetate (4×150 mL). The combined organic layers were dried over anhydrous sodium sulfate, filtered and concentrated under reduced pressure. The crude product was purified by flash chromatography on silica gel loaded with heptane (gradient from 100% heptane to 40% ethyl acetate in heptane) to yield 2-ethylhexyl 3-[(5-benzyloxy-6-fluoro-2-pyridyl)sulfonyl]propanoate (3.691 g, 59%) as a yellow oil. ESI-MS m/z calc. 451.1829, found 452.2 (M+1)⁺; Retention time: 2.648 min (LC Method O).

Step 6: 5-Benzyloxy-6-fluoro-pyridine-2-sulfonamide

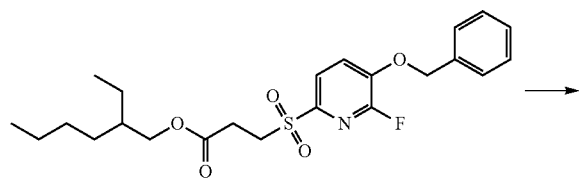

To a solution of 2-ethylhexyl 3-[(5-benzyloxy-6-fluoro-2-pyridyl)sulfonyl]propanoate (3.09 g, 6.8431 mmol) in dimethylsulfoxide (19 mL) was added 1,8-diazabicyclo(5.4.0)undec-7-ene (2.0200 g, 2 mL, 13.269 mmol). The reaction was stirred for 1 h at room temperature and a solution of hydroxylamine-O-sulfonic acid (3.873 g, 34.246 mmol) and sodium acetate (2.246 g, 27.379 mmol) in water (12 mL) was added. The reaction was stirred for 1 h at room temperature, diluted with water (50 mL) and extracted with ethyl acetate (3×20 mL). The combined organic layers were washed with brine (30 mL), dried over anhydrous sodium sulfate, filtered and concentrated under reduced pressure. The crude product was purified by flash chromatography on silica gel loaded with heptane (heptane/ethyl acetate 100:0 to 50:50 gradient) to yield 5-benzyloxy-6-fluoro-pyridine-2-sulfonamide (1.58 g, 80%) as a white solid. ¹H NMR (300 MHz, dimethyl sulfoxide-d₆) δ 5.33 (s, 2H), 7.34-7.52 (m, 7H), 7.79-7.95 (m, 2H). ¹⁹F NMR (282 MHz, dimethyl sulfoxide-d₆) δ −83.6 (d, J=12.2 Hz, 1F). ESI-MS m/z calc. 282.0474, found 283.1 (M+1)⁺; Retention time: 2.33 min (LC Method H).

Step 7: tert-Butyl (4S)-4-[3-[(3-benzyloxy-6-sulfamoyl-2-pyridyl)amino]propyl]-2,2-dimethyl-pyrrolidine-1-carboxylate

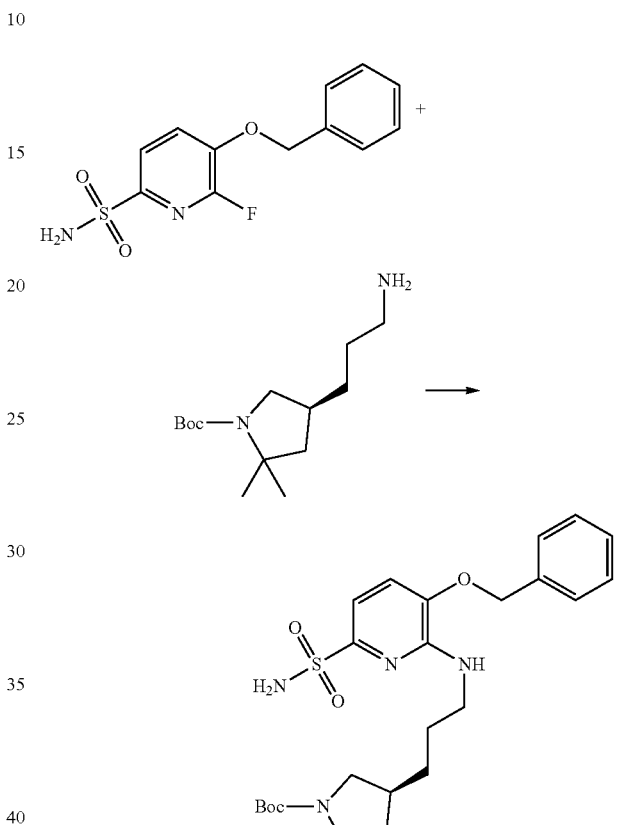

To a stirred solution of tert-butyl (4S)-4-(3-aminopropyl)-2,2-dimethyl-pyrrolidine-1-carboxylate (200 mg, 0.7801 mmol) in anhydrous dimethyl sulfoxide (2.5 mL) was added 5-benzyloxy-6-fluoro-pyridine-2-sulfonamide (221 mg, 0.7829 mmol) and N,N-diisopropylethylamine (200 μL, 1.148 mmol), in that order, under nitrogen. The resulting yellow solution was stirred at 85° C. for 9 h, then at 40° C. for 13 h. The reaction mixture was allowed to cool to ambient temperature, diluted with ethyl acetate (60 mL) and water (50 mL) was added. The solution was then acidified with 10% citric acid (10 mL) and the layers were separated. The organic phase was washed with brine (20 mL), dried over anhydrous sodium sulfate, filtered and concentrated under reduced pressure affording yellow viscous material. The crude reaction mixture was purified via silica gel chromatography (40 g silica gel, eluting with a gradient from 10-60% ethyl acetate in hexanes over 30 min) to furnish the desired tert-butyl (4S)-4-[3-[(3-benzyloxy-6-sulfamoyl-2-pyridyl)amino]propyl]-2,2-dimethyl-pyrrolidine-1-carboxylate (370 mg, 91%) as a white foam. ESI-MS m/z calc. 518.2563, found 519.4 (M+1)⁺; Retention time: 1.75 min (LC Method B).

Step 8: tert-Butyl (4S)-4-[3-[[3-Benzyloxy-6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate

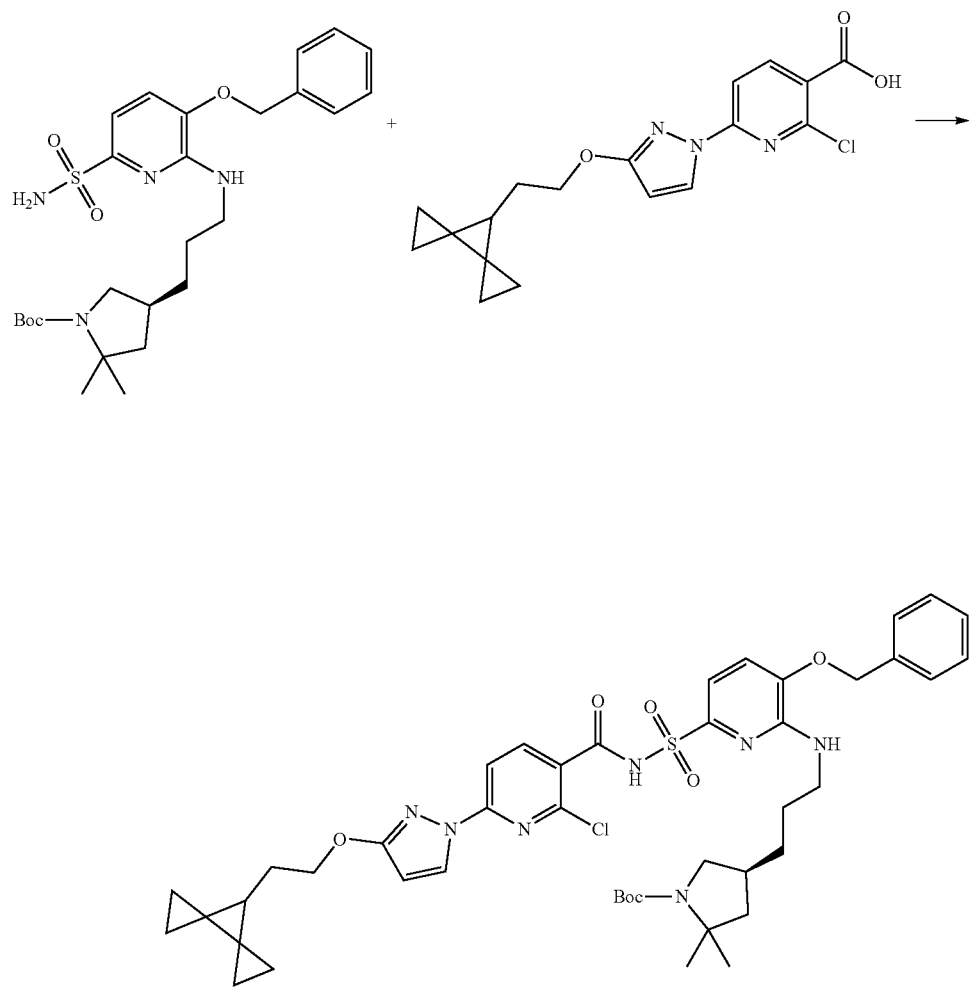

To a stirred solution of 2-chloro-6-[3-(2-dispiro[2.0.2.1]heptan-7-ylethoxy)pyrazol-1-yl]pyridine-3-carboxylic acid (150 mg, 0.4169 mmol) in anhydrous tetrahydrofuran (3 mL) was added carbonyl diimidazole (75 mg, 0.4625 mmol) and stirring continued at ambient temperature under nitrogen for 2 h. To the reaction, a solution of tert-butyl (4S)-4-[3-[(3-benzyloxy-6-sulfamoyl-2-pyridyl)amino]propyl]-2,2-dimethyl-pyrrolidine-1-carboxylate (196 mg, 0.3779 mmol) in anhydrous tetrahydrofuran (1 mL) was added, followed by 1,8-diazabicyclo[5.4.0]undec-7-ene (220 µL, 1.471 mmol) and the mixture was stirred at ambient temperature for 15 h. The volatiles were removed under reduced pressure and the residue was taken up in ethyl acetate (20 mL) and water (10 mL) and the mixture was acidified slowly with hydrochloric acid (1.6 mL of 1.0 M, 1.600 mmol) to about pH=4.0. The layers were separated and the aqueous layer was extracted with ethyl acetate (10 mL). The combined organic phases were washed with brine (15 mL), dried over anhydrous sodium sulfate, filtered and concentrated under reduced pressure. The crude material was purified via silica gel chromatography (24 g silica gel column, 0-70% ethyl acetate in hexanes gradient over 35 min) to furnish tert-butyl (4S)-4-[3-[[3-benzyloxy-6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (171 mg, 37%) as a white solid. ESI-MS m/z calc. 859.34937, found 860.5 (M+1)$^+$; Retention time: 2.49 min (LC Method G).

Step 9: N-[[5-Benzyloxy-6-[3-[(3S)-5,5-dimeth-ylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (Trifluoroacetate Salt)

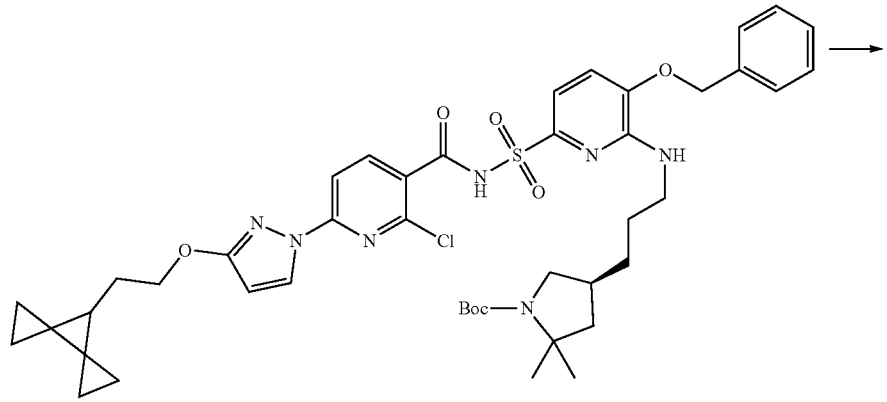

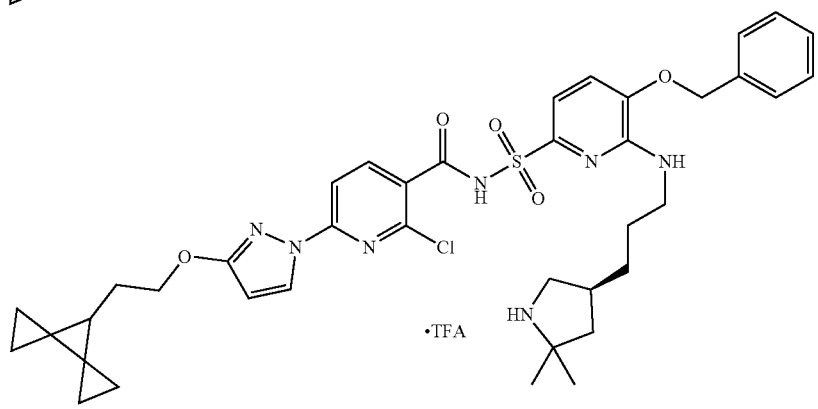

To a stirred solution of tert-butyl (4S)-4-[3-[[3-benzyloxy-6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (75 mg, 0.08716 mmol) in anhydrous methylene chloride (3 mL) was added trifluoroacetic acid (350 μL, 4.543 mmol) at ambient temperature under nitrogen. The orange solution was stirred for 1 h then the volatiles were removed under reduced pressure. To the residue, toluene (20 mL) was added and concentrated under reduced pressure to dryness. The process was repeated once more to remove any residual trifluoroacetic acid and finally dried under vacuum for 2 h to obtain crude N-[[5-benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (66 mg, 87%). The material was taken directly to the next step without further purification. ESI-MS m/z calc. 759.29694, found 760.5 (M+1)$^+$; Retention time: 1.43 min (LC Method B).

Step 10: (14S)-20-(Benzyloxy)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione

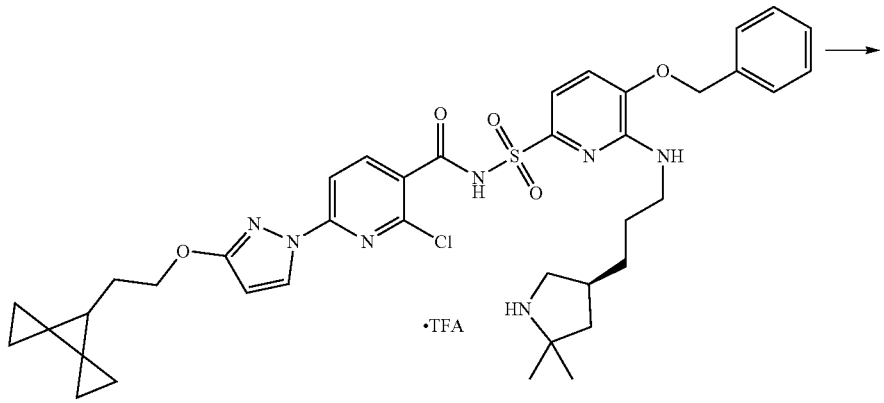

-continued

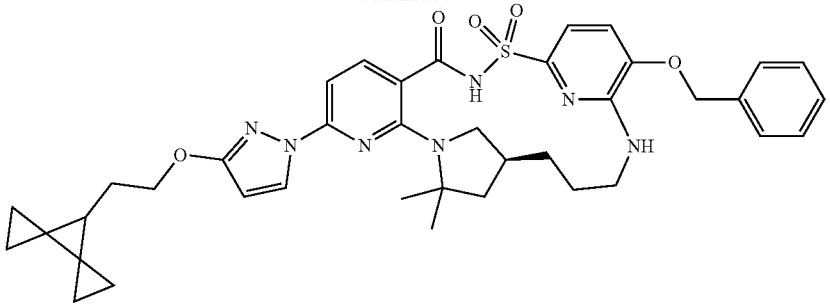

A 20 mL vial was charged with N-[[5-benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (60 mg, 0.06862 mmol), potassium carbonate (60 mg, 0.4341 mmol), cesium fluoride (21 mg, 0.1382 mmol) and anhydrous dimethyl sulfoxide (4 mL), in that order. The vial was purged with a stream of nitrogen for 2 min, capped and stirred at 160° C. for 15 h. The reaction was allowed to cool to ambient temperature and the heterogeneous mixture was diluted with ethyl acetate (30 mL) and water (20 mL) and acidified with hydrochloric acid (1.0 mL of 1.0 M, 1.000 mmol). The layers were separated and the aqueous layer was extracted with additional ethyl acetate (20 mL). The combined organics were washed with brine (20 mL), dried over anhydrous sodium sulfate, filtered and evaporated under reduced pressure. The crude material was purified via silica gel chromatography (0%-10% methanol in dichloromethane over 30 min) affording (14S)-20-(benzyloxy)-8-[3-(2-{dispiro[2.0.2.1]heptan-7-yl}ethoxy)-1H-pyrazol-1-yl]-12,12-dimethyl-2$\lambda^6$-thia-3,9,11,18,23-pentaazatetracyclo[17.3.1.1$^{11,14}$.0$^{5,10}$]tetracosa-1(23),5,7,9,19,21-hexaene-2,2,4-trione (41 mg, 83%) as a white solid. ESI-MS m/z calc. 723.3203, found 724.5 (M+1)$^+$; Retention time: 2.27 min (LC Method G).

Step 11: (14S)-8-[3-(2-{Dispiro[2.0.2.1]heptan-7-yl}ethoxy)-1H-pyrazol-1-yl]-20-hydroxy-12,12-dimethyl-2$\lambda^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound 254)

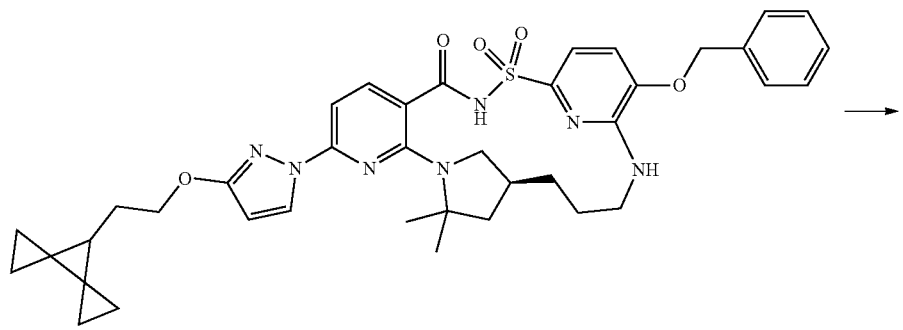

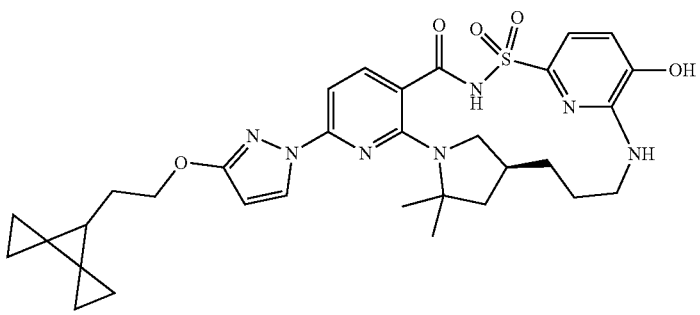

To a stirred solution of (14S)-20-(benzyloxy)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (30 mg, 0.04144 mmol) in anhydrous methanol (6 mL) was added 10% Pd on carbon (wet, Degussa) (16 mg, 0.01503 mmol) under nitrogen. The heterogeneous mixture was stirred under a hydrogen atmosphere (from balloon) for 2.5 h at ambient temperature. The hydrogen balloon was removed and the flask was purged with nitrogen and the black heterogeneous reaction mixture was filtered over a pad of celite. The filtrate was concentrated under reduced pressure and the residue was taken up in dimethyl sulfoxide (1.5 mL) and filtered through a Whatman 0.45 μm PTFE syringe filter disc. The sample was purified using preparative reverse-phase HPLC-MS [Luna C₁₈ (2) column (75×30 mm, 5 μm particle size) sold by Phenomenex (pn: 00C-4252-U0-AX), (dual gradient run from 30%-99% acetonitrile in water over 15 min (no modifier)] giving (14S)-8-[3-(2-{dispiro[2.0.2.1]heptan-7-yl}ethoxy)-1H-pyrazol-1-yl]-20-hydroxy-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 254) (20 mg, 75%) as a pale blue-green solid. ¹H NMR (400 MHz, Methanol-d₄) δ 8.24 (d, J=2.8 Hz, 1H), 7.82 (d, J=8.3 Hz, 1H), 7.19 (d, J=7.8 Hz, 1H), 6.97 (d, J=8.3 Hz, 1H), 6.89 (d, J=7.8 Hz, 1H), 5.94 (d, J=2.7 Hz, 1H), 4.24 (t, J=6.6 Hz, 2H), 4.04 (t, J=13.2 Hz, 1H), 3.37-3.32 (m, 1H), 3.14 (dt, J=13.6, 4.4 Hz, 1H), 2.86 (t, J=10.4 Hz, 1H), 2.30-2.13 (m, 1H), 1.88 (q, J=6.7 Hz, 4H), 1.78-1.66 (m, 2H), 1.66 (s, 3H), 1.63-1.60 (m, 1H), 1.60 (s, 3H), 1.48 (t, J=6.6 Hz, 1H), 1.44-1.33 (m, 1H), 0.92-0.78 (m, 4H), 0.66 (ddd, J=8.7, 4.6, 3.3 Hz, 2H), 0.56-0.47 (m, 2H). ESI-MS m/z calc. 633.2733, found 634.4 (M+1)⁺; Retention time: 1.9 min (LC Method G).

Example 81: Preparation of (14S)-20-hydroxy-12,12-dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 255)

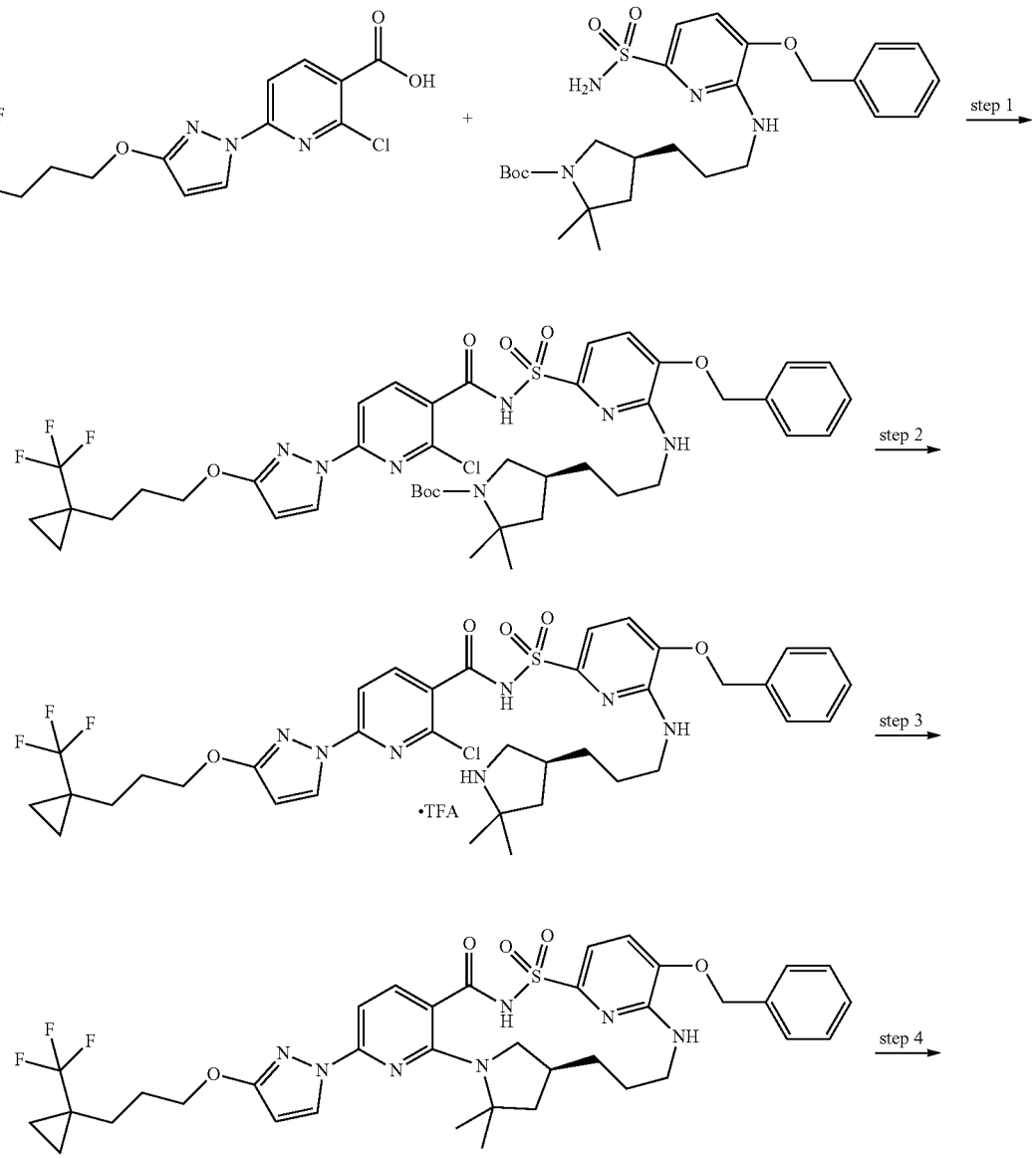

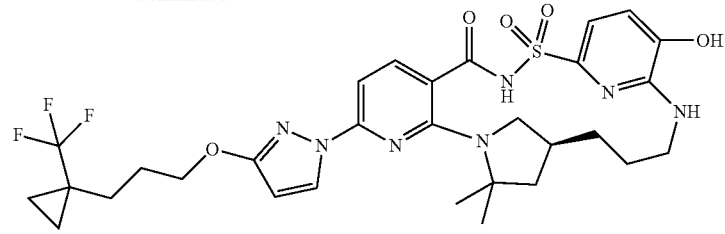

Step 1: tert-butyl (4S)-4-[3-[[3-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethylpyrrolidine-1-carboxylate

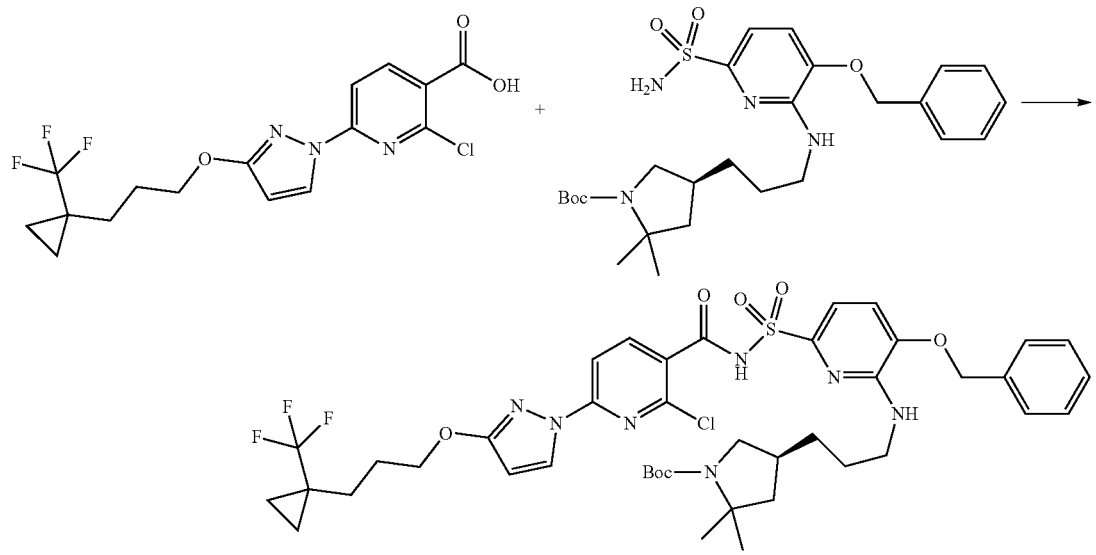

To a stirred solution of 2-chloro-6-[3-[3-[1-(trifluoromethyl)cyclopropyl]propoxy]pyrazol-1-yl]pyridine-3-carboxylic acid (150 mg, 0.3849 mmol) in anhydrous tetrahydrofuran (3 mL) was added carbonyl diimidazole (68 mg, 0.4194 mmol) and stirring continued at ambient temperature under nitrogen for 2 h. To that reaction, a solution of tert-butyl (4S)-4-[3-[(3-benzyloxy-6-sulfamoyl-2-pyridyl)amino]propyl]-2,2-dimethyl-pyrrolidine-1-carboxylate (180 mg, 0.3470 mmol) in anhydrous tetrahydrofuran (1 mL) was added, followed by 1,8-diazabicyclo[5.4.0]undec-7-ene (200 μL, 1.337 mmol) and the mixture was stirred at ambient temperature for 15 h. The volatiles were removed under reduced pressure and the residue was taken up in ethyl acetate (20 mL) and water (10 mL) and the mixture was acidified slowly with hydrochloric acid (1.5 mL of 1.0 M, 1.500 mmol) to about pH=4.0. The layers were separated and the aqueous layer was extracted with ethyl acetate (10 mL). The combined organic phases were washed with brine (15 mL), dried over anhydrous sodium sulfate, filtered and concentrated under reduced pressure. The crude material was purified by silica gel chromatography (0%-70% gradient of ethyl acetate in hexanes over 35 min) to furnish tert-butyl (4S)-4-[3-[[3-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (170 mg, 22%) as a white solid. ESI-MS m/z calc. 889.3211, found 890.5 (M+1)+; Retention time: 2.32 min (LC Method G).

Step 2: N-[[5-Benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (Trifluoroacetate Salt)

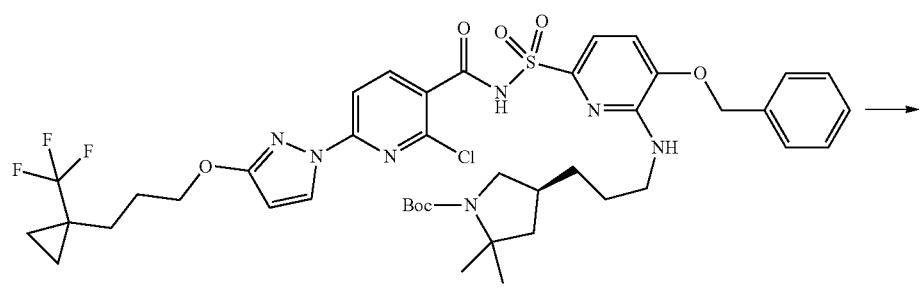

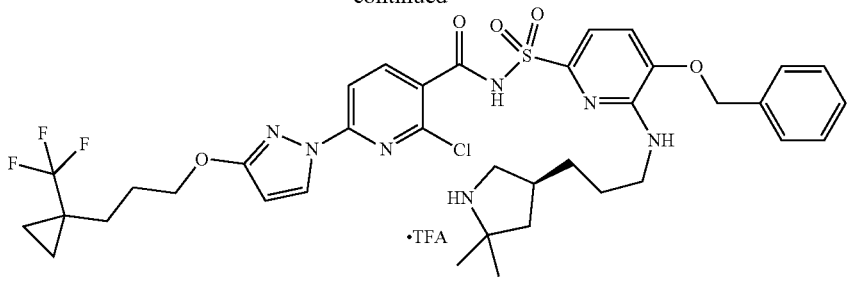

To a stirred solution of tert-butyl (4S)-4-[3-[[3-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (80 mg, 0.08985 mmol) in anhydrous methylene chloride (2.0 mL) was added trifluoroacetic acid (350 µL, 4.543 mmol) at ambient temperature under nitrogen. The orange solution was stirred for 1 h and then the volatiles were removed under reduced pressure. To the residue, toluene (20 mL) was added and then concentrated under reduced pressure to dryness. The process was repeated once more to remove any residual trifluoroacetic acid and finally dried in vacuo for 2 h to obtain crude N-[[5-benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (trifluoroacetate salt) (81 mg, 100%). The material was taken directly to the next step without any purification. ESI-MS m/z calc. 789.2687, found 790.5 (M+1)$^+$; Retention time: 1.9 min (LC Method B).

Step 3: (14S)-20-(Benzyloxy)-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione

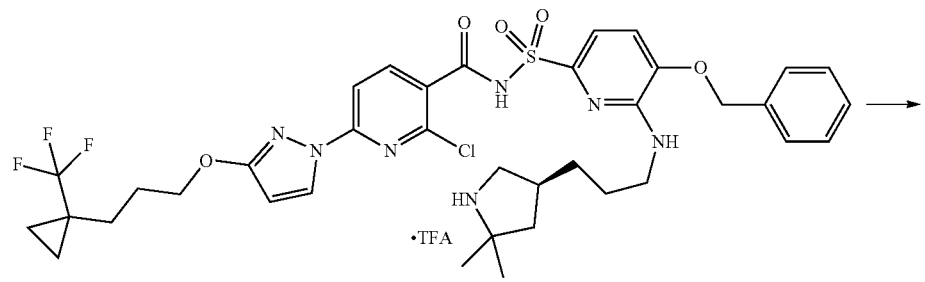

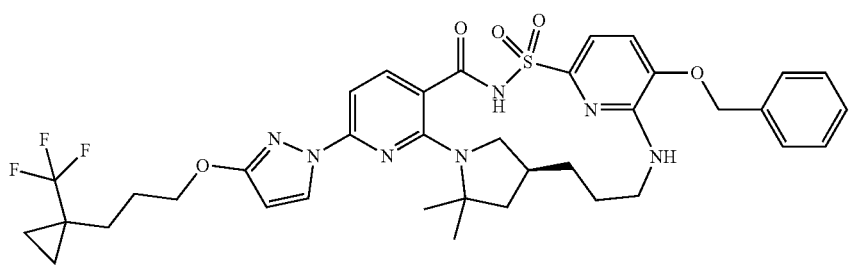

A 20 mL vial was charged with N-[[5-benzyloxy-6-[3-(5,5-dimethylpyrrolidin-3-yl)propylamino]-2-pyridyl]sulfonyl]-2-chloro-6-[3-[3-[1-(trifluoromethyl)cyclopropyl]propoxy]pyrazol-1-yl]pyridine-3-carboxamide (trifluoroacetate salt) (80 mg, 0.08846 mmol), potassium carbonate (75 mg, 0.5427 mmol), cesium fluoride (27 mg, 0.1777 mmol) and anhydrous dimethyl sulfoxide (5 mL), in that order. The vial was purged with a stream of nitrogen for 2 min and was capped and stirred at 160° C. for 15 h. The reaction was allowed to cool to ambient temperature and the heterogeneous mixture was diluted with ethyl acetate (30 mL) and water (20 mL) and acidified with hydrochloric acid (1.5 mL of 1.0 M, 1.500 mmol). The layers were separated and the aqueous layer was extracted with ethyl acetate (20 mL). The combined organics were washed with brine (20 mL), dried over anhydrous sodium sulfate, filtered and evaporated under reduced pressure. The crude residue was purified by silica gel chromatography (0%-10% methanol in dichloromethane gradient over 30 min) affording (14S)-20-(benzyloxy)-12,12-dimethyl-8-(3-{3-[1-(trifluoromethyl)cyclopropyl]propoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (55 mg, 82%) as a white solid. ESI-MS m/z calc. 753.29205, found 754.5 (M+1)⁺; Retention time: 2.11 min (LC Method G).

Step 4: (14S)-20-Hydroxy-12,12-dimethyl-8-(3-{3-[1-(trifluoromethyl)cyclopropyl]propoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 255)

1H-pyrazol-1-yl)-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (42 mg, 0.05572 mmol) in anhydrous methanol (5 mL) was added 10% Pd on carbon (wet, Degussa) (8 mg, 0.007517 mmol) under nitrogen. The heterogeneous mixture was stirred under hydrogen (from balloon) for 2.5 h at ambient temperature. The hydrogen balloon was removed and the flask was purged with nitrogen and the black heterogeneous reaction mixture was filtered over a pad of celite. The filtrate was concentrated under reduced pressure and the residue was taken up in dimethyl sulfoxide (1.5 mL) and filtered through a Whatman 0.45 μm PTFE syringe filter disc. The sample was purified using preparative reverse-phase HPLC-MS [Luna C₁₈ (2) column (75×30 mm, 5 μm particle size) sold by Phenomenex (pn: 00C-4252-U0-AX), (dual gradient run from 30%-99% acetonitrile in water over 15 min (no modifier)] giving (14S)-20-hydroxy-12,12-dimethyl-8-(3-{3-[1-(trifluoromethyl)cyclopropyl]propoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 255) (27 mg, 72%) as a pale blue-green solid. ¹H NMR (400 MHz, Methanol-d₄) δ 8.25 (d, J=2.8 Hz, 1H), 7.82 (d, J=8.1 Hz, 1H), 7.19 (d, J=7.8 Hz, 1H), 6.98 (d, J=8.3 Hz, 1H), 6.89 (d, J=7.8 Hz, 1H), 5.97 (d, J=2.9 Hz, 1H), 4.24 (t, J=6.1 Hz, 2H), 4.03 (t, J=12.8 Hz, 1H), 3.42-3.32 (m, 1H), 3.14 (dt, J=13.9, 4.4 Hz, 1H), 2.85 (s, 1H), 2.32-2.09 (m, 1H), 1.99-1.83 (m, 4H), 1.80-1.74 (m, 2H), 1.74-1.66 (m, 2H), 1.66 (s, 3H), 1.63-1.60 (m, 1H), 1.59 (s, 3H), 1.40 (dd, J=13.3, 10.1 Hz, 1H), 0.98-0.92 (m, 2H), 0.69 (ddd, J=6.0,

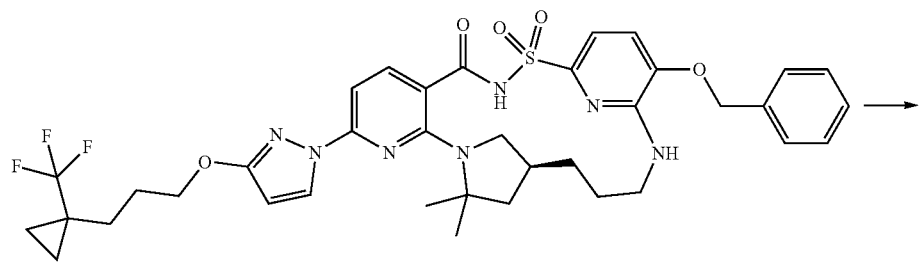

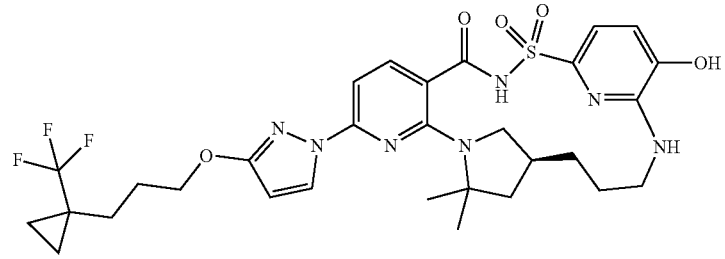

To a stirred solution of (14S)-20-(benzyloxy)-12,12-dimethyl-8-(3-{3-[1-(trifluoromethyl)cyclopropyl]propoxy}-

4.2, 3.0 Hz, 2H). ESI-MS m/z calc. 663.24506, found 664.4 (M+1)⁺; Retention time: 1.7 min (LC Method G).

Example 82: Preparation of (14S)-8-(3-hydroxy-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 256)

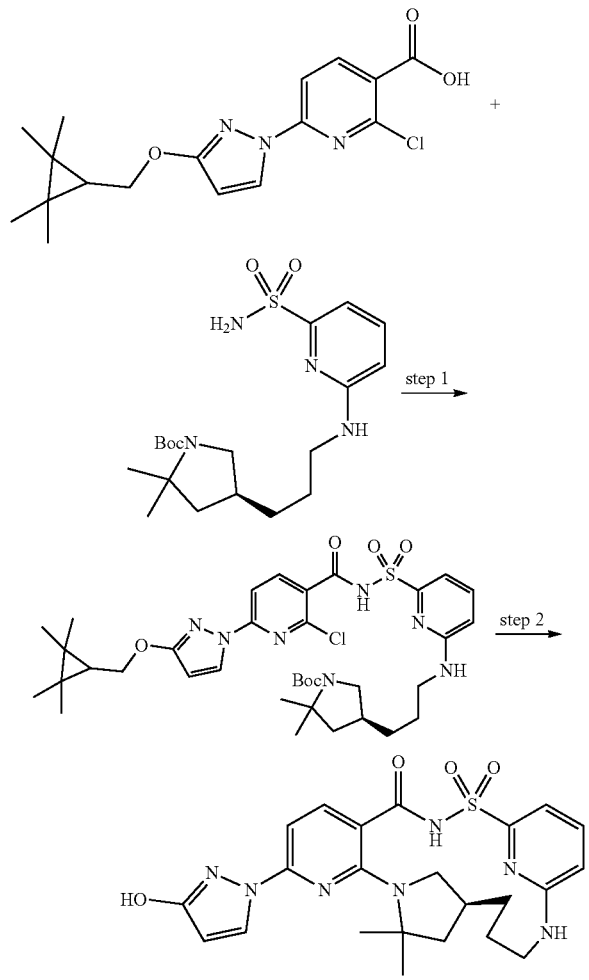

Step 1: tert-Butyl (4S)-4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate

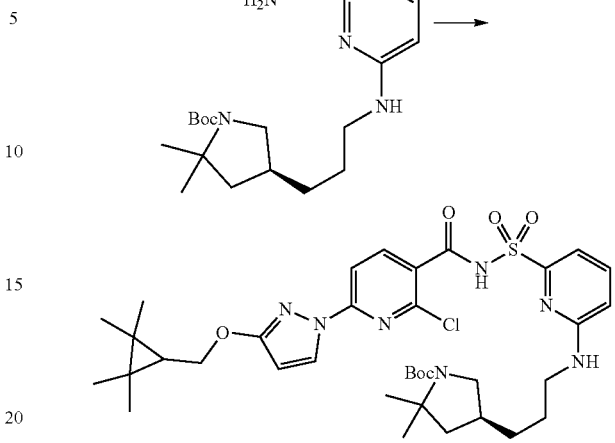

2-Chloro-6-[3-[(2,2,3,3-tetramethylcyclopropyl)methoxy]pyrazol-1-yl]pyridine-3-carboxylic acid (200 mg, 0.5717 mmol) and carbonyl diimidazole (116 mg, 0.7154 mmol) (freshly recrystallized from tetrahydrofuran, washed with cold ether and dried on high vacuum) were combined in tetrahydrofuran (2 mL) and stirred for 2 h at room temperature. Then tert-butyl (4S)-2,2-dimethyl-4-[3-[(6-sulfamoyl-2-pyridyl)amino]propyl]pyrrolidine-1-carboxylate (275 mg, 0.6666 mmol) was added followed by 1,8-diazabicyclo[5.4.0]undec-7-ene (500 μL, 3.343 mmol) and the reaction was stirred at room temperature for 14 h. The reaction mixture was quenched with saturated ammonium chloride and extracted with ethyl acetate. The organic layer was washed with brine, dried (magnesium sulfate), filtered and concentrated. The resultant brown residue was purified by silica gel column chromatography using a shallow gradient from 100% hexanes to 100% ethyl acetate to afford tert-butyl (4S)-4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate (172 mg, 40%) as an off white solid. ESI-MS m/z calc. 743.3232, found 744.45 (M+1)⁺; Retention time: 0.97 min (LC Method A).

Step 2: (14S)-8-(3-Hydroxy-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 256)

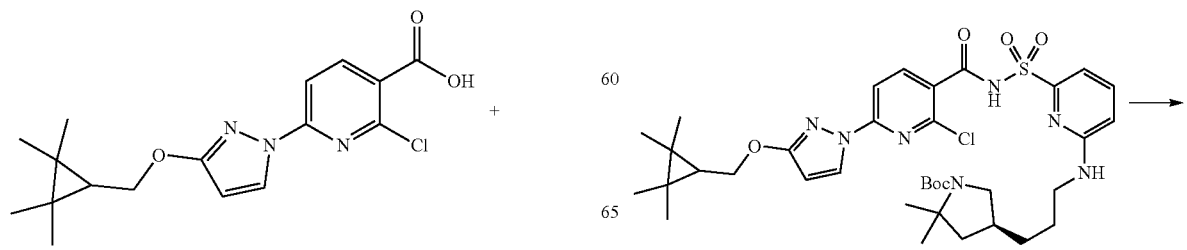

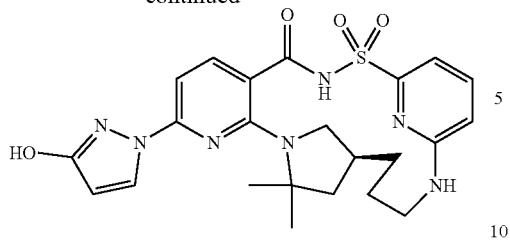

A solution of tert-butyl (4S)-4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate (172 mg, 0.2311 mmol) in dichloromethane (1.5 mL) and trifluoroacetic acid (500 µL, 6.534 mmol) was stirred at room temperature for 4 h. Solvents were removed and the residue was dissolved in ethyl acetate. Washed with 2 mL of saturated aqueous sodium bicarbonate solution and the organic layer was collected and solvent removed in vacuo. The residue was dissolved in dimethyl sulfoxide (10 mL) and 3 Å molecular sieves were added and the reaction mixture was stirred for 10 min. Then cesium fluoride (115 mg, 0.7571 mmol) and potassium carbonate (107 mg, 0.7742 mmol) were added and the reaction mixture was heated at 150° C. for 16 h. The reaction mixture was cooled to room temperature and filtered through Celite and to the filtrate was added saturated ammonium chloride solution. The mixture was extracted with ethyl acetate, the organic layer was washed with brine, dried over anhydrous sodium sulfate, filtered and concentrated. The resultant brown residue was purified by a reverse phase HPLC-MS method using a Luna $C_{18}$ (2) column (75×30 mm, 5 µm particle size) sold by Phenomenex (pn: 00C-4252-U0-AX) and a dual gradient run from 30%-99% mobile phase B over 15.0 min (mobile phase A=water (5 mM hydrochloric acid), mobile phase B=acetonitrile. Flow rate=50 mL/min, injection volume=950 µL and column temperature=25° C.) to afford (14S)-8-(3-hydroxy-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 256) (19.5 mg, 17%) as an off-white solid. ¹H NMR (400 MHz, dimethyl sulfoxide-d₆) δ 12.58 (s, 1H), 10.63 (s, 1H), 8.22 (d, J=2.7 Hz, 1H), 7.87 (d, J=7.8 Hz, 1H), 7.65 (s, 1H), 7.13 (d, J=6.9 Hz, 1H), 6.94 (d, J=8.2 Hz, 1H), 6.79 (s, 1H), 6.00 (d, J=2.7 Hz, 1H), 4.02 (d, J=12.8 Hz, 1H), 3.27 (d, J=5.2 Hz, 1H), 3.04 (d, J=13.3 Hz, 1H), 2.90-2.73 (m, OH), 2.18 (d, J=4.1 Hz, 1H), 1.95 (dd, J=11.7, 5.2 Hz, 1H), 1.86 (s, OH), 1.70 (s, 3H), 1.66 (d, J=13.3 Hz, 5H), 1.61 (s, 3H), 1.49-1.36 (m, 1H). ESI-MS m/z calc. 497.1845, found 498.33 (M+1)⁺; Retention time: 1.47 min (LC Method B).

Example 83: Preparation of (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 257)

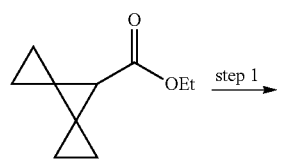

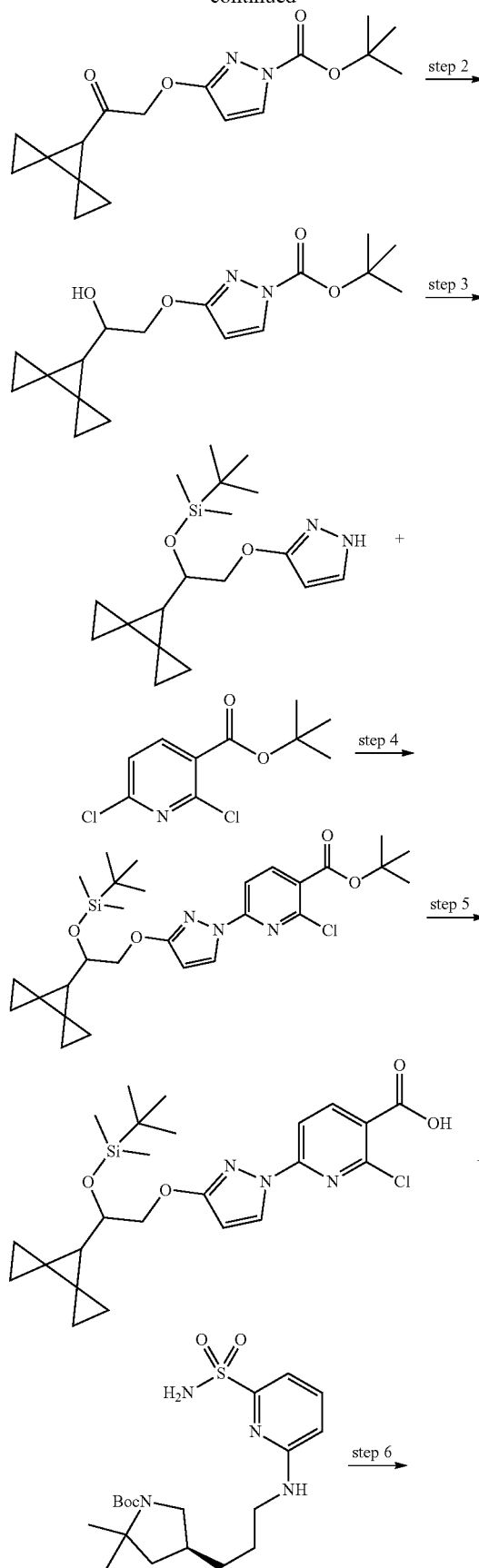

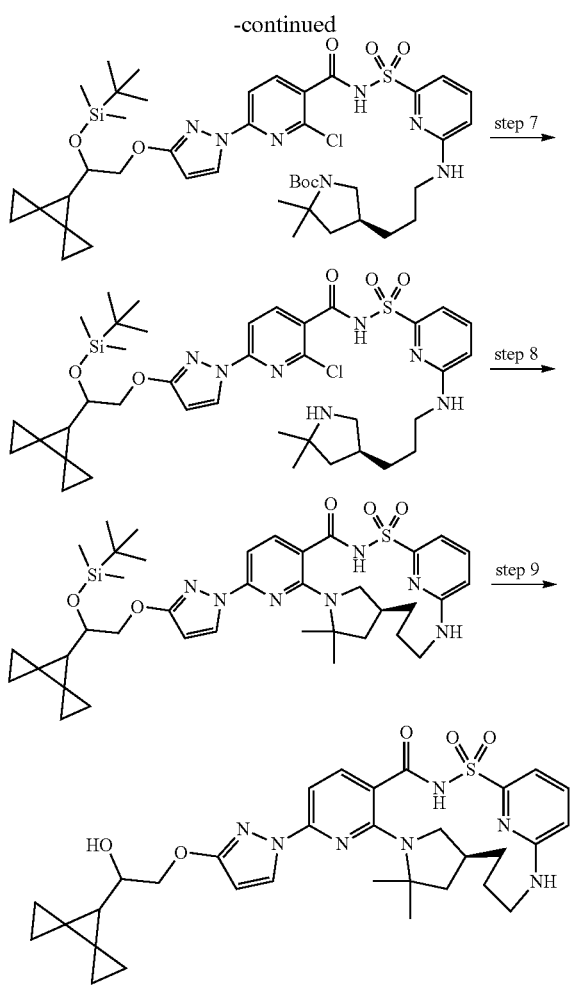

Step 1: tert-Butyl 3-(2-dispiro[2.0.2.1]heptan-7-yl-2-oxo-ethoxy)pyrazole-1-carboxylate

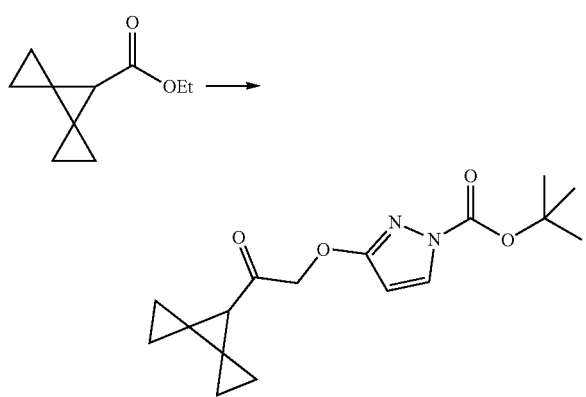

A solution of n-BuLi (16 mL of 2.5 M in hexanes, 40.000 mmol) was added to a tetrahydrofuran (50 mL) solution of diisopropyl amine (4.0432 g, 5.6 mL, 39.957 mmol) which was precooled to −30° C. (flask 1). The mixture was stirred for 20 min in an ice-water bath before cooled down to −78°

C. In a separate flask, ethyl dispiro[2.0.2.1]heptane-7-carboxylate (1.66 g, 9.9869 mmol) was dissolved in 100 mL of tetrahydrofuran. Chloro(iodo)methane (8.8112 g, 3.7 mL, 48.956 mmol) was added and the solution was cooled to −78° C. under a nitrogen balloon (flask 2). The contents of flask 1 were transferred via cannula within 15 min (very quick dropwise) to flask 2. The resulted mixture was further stirred at −78° C. for 1 h. A mixture of acetic acid/tetrahydrofuran (15 mL/15 mL) was added dropwise. Dry ice bath was removed and the mixture was allowed warm up to 0° C. It was then partitioned between water and ethyl acetate. Separated the layers and washed the aqueous layer once more with ethyl acetate. The combined organic layers were washed with brine, dried over anhydrous sodium sulfate, filtered and concentrated. The residue was dissolved in N,N-dimethylformamide (15 mL) at room temperature. tert-Butyl 3-hydroxypyrazole-1-carboxylate (810 mg, 4.3976 mmol) was added, followed by potassium carbonate (1.25 g, 9.0445 mmol) and potassium iodide (62 mg, 0.3735 mmol). The mixture was stirred at 60° C. for 48 h. It was then cooled to room temperature and diluted with ethyl acetate/water (30 mL each). The layers were separated and the aqueous layer was extracted one more time with ethyl acetate (20 mL). The combined organic layers were washed with water (20 mL), brine, dried over anhydrous sodium sulfate and concentrated. The residue was purified by silica gel chromatography using a gradient from 5% to 40% ethyl acetate in hexanes. The desired product (the less polar isomer), tert-butyl 3-(2-dispiro[2.0.2.1]heptan-7-yl-2-oxo-ethoxy)pyrazole-1-carboxylate (620 mg, 47%) was obtained as white solid. $^1$H NMR (250 MHz, Chloroform-d) δ 7.85 (s, 1H), 5.96 (s, 1H), 4.95 (s, 2H), 2.62 (s, 1H), 1.60 (s 9H), 1.34-1.16 (m, 2H), 1.14-0.63 (m, 6H). ESI-MS m/z calc. 318.158, found 319.5 (M+1)$^+$; Retention time: 3.59 min (LC Method P).

Step 2: tert-Butyl 3-(2-dispiro[2.0.2.1]heptan-7-yl-2-hydroxy-ethoxy)pyrazole-1-carboxylate

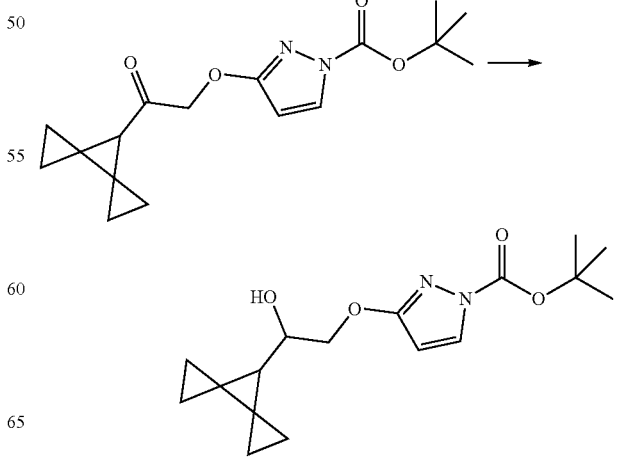

tert-Butyl 3-(2-dispiro[2.0.2.1]heptan-7-yl-2-oxo-ethoxy)pyrazole-1-carboxylate (620 mg, 1.7527 mmol) was dissolved in ethanol (10 mL) and the mixture was cooled in an ice-water bath. Sodium borohydride (66.309 mg, 0.0702 mL, 1.7176 mmol) was added. After 5 min, methanol (0.5 mL) was added. The mixture was stirred at room temperature for 1 h. It was then quenched with saturated aqueous ammonium chloride and partitioned between ethyl acetate and water (20 mL each). The layers were separated and the organic layer was filtered through an anhydrous sodium sulfate pad and concentrated. The crude material was used in the next step without further purification, tert-butyl 3-(2-dispiro[2.0.2.1]heptan-7-yl-2-hydroxy-ethoxy)pyrazole-1-carboxylate (600 mg, 91%). ESI-MS m/z calc. 320.1736, found 321.3 (M+1)$^+$; Retention time: 3.44 min (LC Method P).

Step 3: tert-Butyl-[1-dispiro[2.0.2.1]heptan-7-yl-2-(1H-pyrazol-3-yloxy)ethoxy]-dimethyl-silane

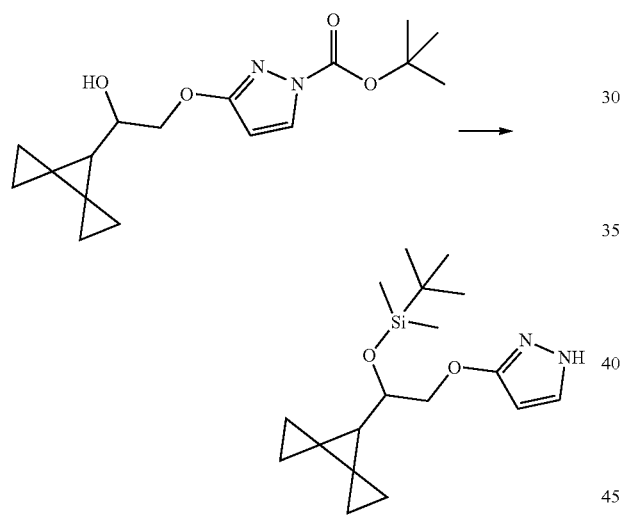

tert-Butyl 3-(2-dispiro[2.0.2.1]heptan-7-yl-2-hydroxy-ethoxy)pyrazole-1-carboxylate (300 mg, 0.8896 mmol) was dissolved in dichloromethane (10 mL) and the mixture was stirred in an ice-water bath under a nitrogen balloon. 2,6-Lutidine (686.96 mg, 0.75 mL, 6.3469 mmol) was added, followed by TBDMSOTf (1.2408 g, 1.1 mL, 4.6001 mmol). The mixture was stirred for 30 min. More 2,6-lutidine (551 mg, 0.6 mL, 5 mmol) was added, followed by TBDMSOTf (1.2408 g, 1.1 mL, 4.6001 mmol). The mixture was stirred for 12 h. It was then diluted with dichloromethane (40 mL) and treated with saturated aqueous sodium bicarbonate (30 mL). The layers were separated and the dichloromethane layer was dried over anhydrous sodium sulfate, filtered and concentrated. The residue was purified by silica gel chromatography using a 0% to 30% ethyl acetate in hexanes gradient to afford tert-butyl-[1-dispiro[2.0.2.1]heptan-7-yl-2-(1H-pyrazol-3-yloxy)ethoxy]-dimethyl-silane (300 mg, 81%) as a colorless oil. ESI-MS m/z calc. 334.2077, found 335.6 (M+1)$^+$; Retention time: 4.55 min (LC Method P).

Step 4: tert-Butyl 6-[3-[2-[tert-butyl(dimethyl)silyl]oxy-2-dispiro[2.0.2.1]heptan-7-yl-ethoxy]pyrazol-1-yl]-2-chloro-pyridine-3-carboxylate

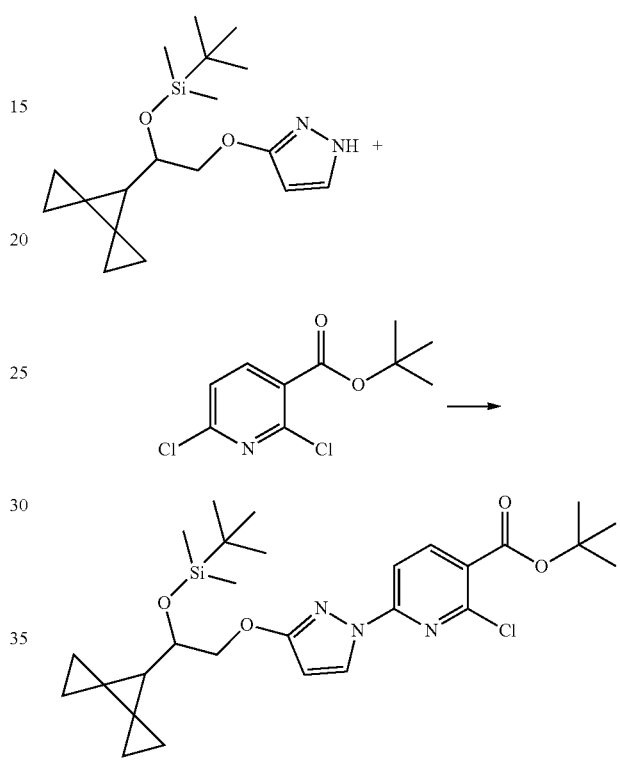

tert-Butyl-[1-dispiro[2.0.2.1]heptan-7-yl-2-(1H-pyrazol-3-yloxy)ethoxy]-dimethyl-silane (300 mg, 0.8071 mmol) was dissolved in dimethyl sulfoxide (8 mL) at room temperature. tert-Butyl 2,6-dichloropyridine-3-carboxylate (210 mg, 0.8464 mmol) was added, followed by potassium carbonate (138 mg, 0.9985 mmol) and 1,4-diazabicyclo[2.2.2]octane (18 mg, 0.1605 mmol). The mixture was stirred at room temperature for 24 h. Ethyl acetate (~25 mL) was added, followed by water (~20 mL). The layers were separated and the aqueous layer was extracted one more time (~20 mL) with ethyl acetate. The combined organics were concentrated and the residue was purified by silica gel chromatography, using a 0%-10% ethyl acetate in hexanes gradient to afford tert-butyl 6-[3-[2-[tert-butyl(dimethyl)silyl]oxy-2-dispiro[2.0.2.1]heptan-7-yl-ethoxy]pyrazol-1-yl]-2-chloro-pyridine-3-carboxylate (490 mg, 100%) as white solid. $^1$H NMR (250 MHz, Chloroform-d) δ 8.35 (dd, J=2.8, 0.9 Hz, 1H), 8.19 (dd, J=8.4, 0.9 Hz, 1H), 7.68 (dd, J=8.4, 0.9 Hz, 1H), 5.93 (dd, J=2.9, 0.9 Hz, 1H), 4.17 (dd, J=5.5, 0.9 Hz, 2H), 4.01-3.80 (m, 1H), 1.78-1.43 (m, 13H), 1.38-1.16 (m, 4H), 1.15-0.45 (m, 22H), 0.20--0.01 (m, 6H).

Step 5: 6-[3-[2-[tert-butyl(dimethyl)silyl]oxy-2-dispiro[2.0.2.1]heptan-7-yl-ethoxy]pyrazol-1-yl]-2-chloro-pyridine-3-carboxylic Acid

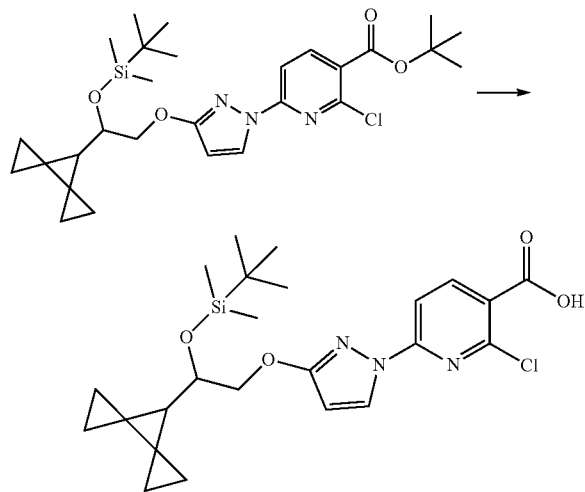

tert-Butyl 6-[3-[2-[tert-butyl(dimethyl)silyl]oxy-2-dispiro[2.0.2.1]heptan-7-yl-ethoxy]pyrazol-1-yl]-2-chloro-pyridine-3-carboxylate (200 mg, 0.3296 mmol) was dissolved in dichloromethane (4 mL) and cooled in an ice-water bath. Triethylamine (200.11 mg, 0.2756 mL, 1.9776 mmol) was added, followed by TBDMSOTf (609.88 mg, 2.3072 mmol). The mixture was stirred at room temperature for 5 h and diluted with dichloromethane (10 mL). Water (~10 mL) was added and the layers were separated. The dichloromethane layer was concentrated and the residue was purified by silica gel chromatography, using a 0%-10% methanol/dichloromethane gradient, to give 6-[3-[2-[tert-butyl(dimethyl)silyl]oxy-2-dispiro[2.0.2.1]heptan-7-yl-ethoxy]pyrazol-1-yl]-2-chloro-pyridine-3-carboxylic acid (50 mg, 22%). $^1$H NMR (250 MHz, Chloroform-d) δ 8.49-8.17 (m, 2H), 7.70 (d, J=8.4 Hz, 1H), 5.94 (d, J=2.9 Hz, 1H), 4.16 (d, J=5.4 Hz, 2H), 3.89 (dt, J=8.6, 5.4 Hz, 1H), 1.65 (t, J=7.6 Hz, 1H), 1.12-0.41 (m, 19H), 0.06 (d, J=2.2 Hz, 6H). ESI-MS m/z calc. 489.1851, found 490.7 (M+1)$^+$; Retention time: 4.53 min (LC Method P).

Step 6: tert-Butyl (4S)-4-[3-[[6-[[6-[3-[2-[tert-butyl(dimethyl)silyl]oxy-2-dispiro[2.0.2.1]heptan-7-yl-ethoxy]pyrazol-1-yl]-2-chloro-pyridine-3-carbonyl]sulfamoyl]-2-pyridyl]amino]propyl]-2,2-dimethyl-pyrrolidine-1-carboxylate

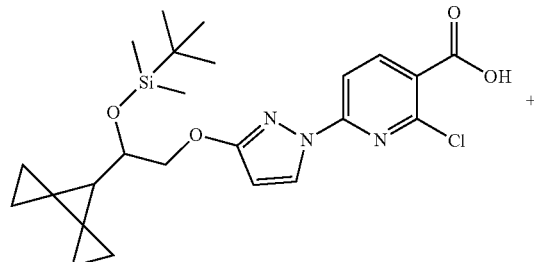

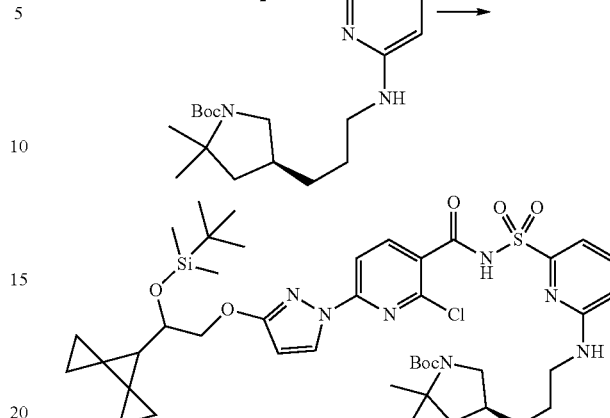

6-[3-[2-[tert-Butyl(dimethyl)silyl]oxy-2-dispiro[2.0.2.1]heptan-7-yl-ethoxy]pyrazol-1-yl]-2-chloro-pyridine-3-carboxylic acid (750 mg, 1.5304 mmol) was dissolved in tetrahydrofuran (5 mL) at room temperature under a nitrogen balloon. Added carbonyl diimidazole (345 mg, 2.0851 mmol) in one portion. The reaction was stirred for 4 h. In a separate flask was weighed tert-butyl (4S)-2,2-dimethyl-4-[3-[(6-sulfamoyl-2-pyridyl)amino]propyl]pyrrolidine-1-carboxylate (695 mg, 1.6847 mmol) and tetrahydrofuran (5 mL) was added, followed by 1,8-diazabicyclo[5.4.0]undec-7-ene (249.90 mg, 0.25 mL, 1.6087 mmol). The mixture of activated acid was then transferred to the 1,8-diazabicyclo[5.4.0]undec-7-ene solution via pipette. The resulted mixture was stirred at room temperature for 14 h. Mixture was then concentrated, taken into ethyl acetate (~30 mL) and washed with brine. Organic fraction was dried (sodium sulfate), filtered and concentrated. Purified by silica gel chromatography using a gradient of 25%-80% ethyl acetate in hexanes giving tert-butyl (4S)-4-[3-[[6-[[6-[3-[2-[tert-butyl(dimethyl)silyl]oxy-2-dispiro[2.0.2.1]heptan-7-yl-ethoxy]pyrazol-1-yl]-2-chloro-pyridine-3-carbonyl]sulfamoyl]-2-pyridyl]amino]propyl]-2,2-dimethyl-pyrrolidine-1-carboxylate (500 mg, 35%) as an oil. ESI-MS m/z calc. 883.3889, found 884.8 (M+1)$^+$; Retention time: 5.39 min (LC Method P).

Step 7: 6-[3-[2-[tert-Butyl(dimethyl)silyl]oxy-2-dispiro[2.0.2.1]heptan-7-yl-ethoxy]pyrazol-1-yl]-2-chloro-N-[[6-[3-[(3S)-5,5-dimethylpyrrolidin-3-yl]propylamino]-2-pyridyl]sulfonyl]pyridine-3-carboxamide

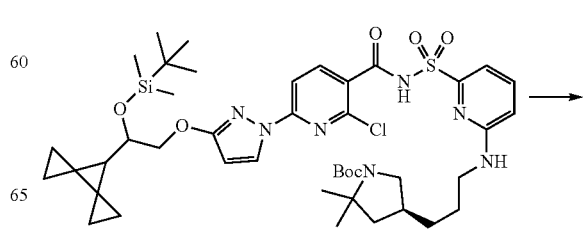

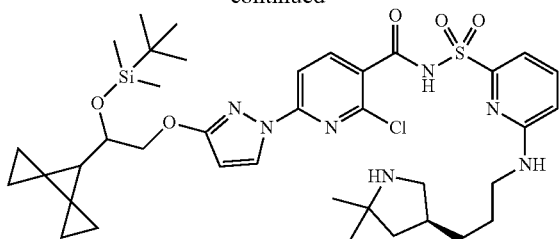

tert-Butyl (4S)-4-[3-[[6-[[6-[3-[2-[tert-butyl(dimethyl)silyl]oxy-2-dispiro[2.0.2.1]heptan-7-yl-ethoxy]pyrazol-1-yl]-2-chloro-pyridine-3-carbonyl]sulfamoyl]-2-pyridyl]amino]propyl]-2,2-dimethyl-pyrrolidine-1-carboxylate (500 mg, 0.5370 mmol) was dissolved in dichloromethane (15 mL) and cooled in an ice-water bath. Triethylamine (232.32 mg, 0.3200 mL, 2.2500 mmol) was added, followed by TBDMSOTf (1.1510 g, 1.0000 mL, 4.2672 mmol) added dropwise. The mixture was then stirred at room temperature for 15 h and subsequently diluted with dichloromethane (20 mL) and quenched with saturated aqueous sodium bicarbonate (20 mL). The organic layer was washed with brine, dried over anhydrous sodium sulfate, filtered and concentrated. The residue was purified by silica gel chromatography, using a 0%-5% methanol in dichloromethane gradient to afford 6-[3-[2-[tert-butyl(dimethyl)silyl]oxy-2-dispiro[2.0.2.1]heptan-7-yl-ethoxy]pyrazol-1-yl]-2-chloro-N-[[6-[3-[(3S)-5,5-dimethylpyrrolidin-3-yl]propylamino]-2-pyridyl]sulfonyl]pyridine-3-carboxamide (310 mg, 70%). ESI-MS m/z calc. 783.3365, found 785.0 (M+1)$^+$; Retention time: 3.29 min (LC Method P).

Step 8: (14S)-8-(3-{2-[(tert-Butyldimethylsilyl)oxy]-2-{dispiro[2.0.2.1]heptan-7-yl}ethoxy}-1H-pyrazol-1-yl)-12,12-dimethyl-2λ$^6$-thia-3,9,11,18,23-pentaazatetracyclo[17.3.1.1$^{11}$,1$^{4.05,10}$]tetracosa-1(23),5,7,9,19,21-hexaene-2,2,4-trione

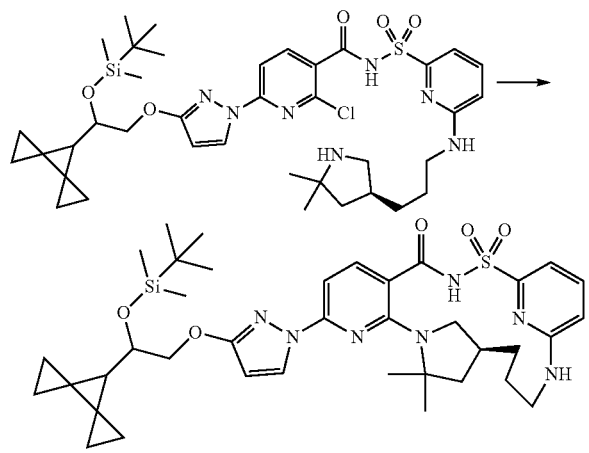

6-[3-[2-[tert-Butyl(dimethyl)silyl]oxy-2-dispiro[2.0.2.1]heptan-7-yl-ethoxy]pyrazol-1-yl]-2-chloro-N-[[6-[3-[(3S)-5,5-dimethylpyrrolidin-3-yl]propylamino]-2-pyridyl]sulfonyl]pyridine-3-carboxamide (310 mg, 0.3952 mmol) was dissolved in dimethyl sulfoxide (40 mL). Potassium carbonate (329 mg, 2.3805 mmol) was added, followed by molecular sieves (0.3952 mmol). The mixture was degassed and protected under nitrogen balloon. It was then heated in a 140° C. oil bath for 12 h. After cooling down to room temperature, the mixture was diluted with brine (20 mL) and extracted with dichloromethane (2×20 mL). The solvent was removed and the residue was purified with a short silica gel pad eluting with ethyl acetate to afford (14S)-8-(3-{2-[(tert-butyldimethylsilyl)oxy]-2-{dispiro[2.0.2.1]heptan-7-yl}ethoxy}-1H-pyrazol-1-yl)-12,12-dimethyl-2λ$^6$-thia-3,9,11,18,23-pentaazatetracyclo[17.3.1.1$^{11}$,1$^{4.05,10}$]tetracosa-1(23),5,7,9,19,21-hexaene-2,2,4-trione (170 mg, 55%) (170 mg, 55%). $^1$H NMR (250 MHz, Chloroform-d) δ 8.20 (d, J=2.8 Hz, 1H), 8.08 (d, J=8.4 Hz, 1H), 7.67-7.42 (m, 2H), 7.33-7.19 (s, 1H), 6.57 (d, J=7.7 Hz, 1H), 5.90 (d, 1H), 4.69 (s, 1H), 4.17 (d, J=5.4 Hz, 2H), 4.02-3.73 (m, 2H), 3.54-2.88 (m, 3H), 2.61 (m, 1H), 2.05 (m, 1H), 1.77-1.40 (m, 8H), 1.26 (s, 6H), 1.11-0.45 (m, 17H), 0.08 (2s, 6H). ESI-MS m/z calc. 747.3598, found 748.8 (M+1)$^+$; Retention time: 4.9 min (LC Method P).

Step 9: (14S)-8-[3-(2-{Dispiro[2.0.2.1]heptan-7-yl}-2-hydroxyethoxy)-1H-pyrazol-1-yl]-12,12-dimethyl-2λ$^6$-thia-3,9,11,18,23-pentaazatetracyclo[17.3.1.1$^{11}$, 1$^{4.05,10}$]tetracosa-1(22),5,7,9,19(23),20-hexaene-2,2,4-trione (Compound 257)

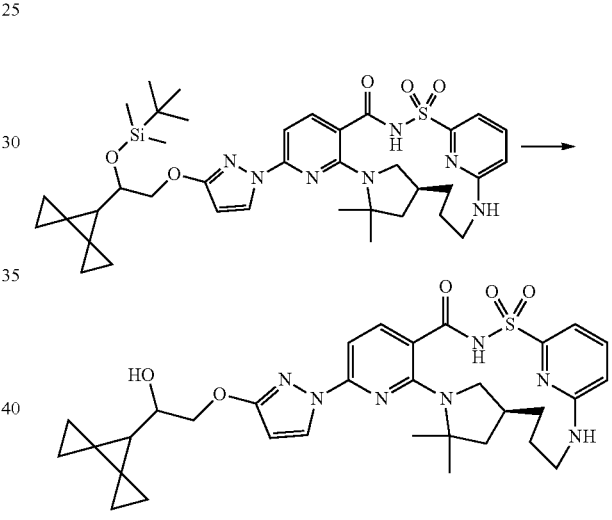

(14S)-8-(3-{2-[(tert-Butyldimethylsilyl)oxy]-2-{dispiro[2.0.2.1]heptan-7-yl}ethoxy}-1H-pyrazol-1-yl)-12,12-dimethyl-2λ$^6$-thia-3,9,11,18,23-pentaazatetracyclo[17.3.1.1$^{11}$,1$^{4.05,10}$]tetracosa-1(23),5,7,9,19,21-hexaene-2,2,4-trione (170 mg, 0.2273 mmol) was dissolved in tetrahydrofuran (5 mL) in a plastic bottle and cooled in an ice water bath. 70% w/w hydrogen fluoride-pyridine (0.5 mL) was added. The mixture was stirred for 10 min at room temperature and recooled in ice water bath. Another portion of 70% w/w hydrogen fluoride-pyridine (~0.5 mL) was added and the mixture was stirred 10 min with ice water bath removed. A third portion of 70% w/w hydrogen fluoride pyridine (~0.5 mL) was added and the mixture was stirred for 10 min. It was then diluted with ethyl acetate (30 mL) and brine (20 mL). The layers were separated and the organics were concentrated under vacuum. Some white precipitate was seen approaching the end of the solvent removal. The residue was treated with a mixture of ethyl acetate and water (30 mL each) and allowed to stand at room temperature for ~2 h. The layers were separated and the organic layer was concentrated and the residue was purified by silica gel chromatography using a 0%-5% methanol in dichloromethane gradient to give (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 257) (63 mg, 44%). $^1$H NMR (250 MHz, CDCl$_3$) δ 8.20 (d, J=2.8 Hz, 1H), 8.03 (d, J=8.2 Hz, 1H), 7.65-7.36 (m, 2H), 7.18 (d, J=8.3 Hz, 1H), 6.55 (d, J=8.0 Hz, 1H), 5.94 (d, J=2.8 Hz, 1H), 4.71 (s, 1H), 4.38-4.03 (m, 3H), 4.03-3.70 (m, 2H), 3.33 (t, J=8.8 Hz, 1H), 3.25-2.89 (m, 2H), 2.56 (s, 2H), 2.05 (s, 2H), 1.62 (m, 6H, overlapping with water peak), 1.38-1.16 (m, 4H), 1.08 (dd, J=8.6, 4.1 Hz, 1H), 1.04-0.76 (m, 5H), 0.67 (d, J=12.8 Hz, 4H). ESI-MS m/z calc. 633.2733, found 634.4 (M+1)$^+$; Retention time: 2.87 min (LC Method R).

Example 84: Preparation of (14S)-8-(3-{2-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Compound 259)

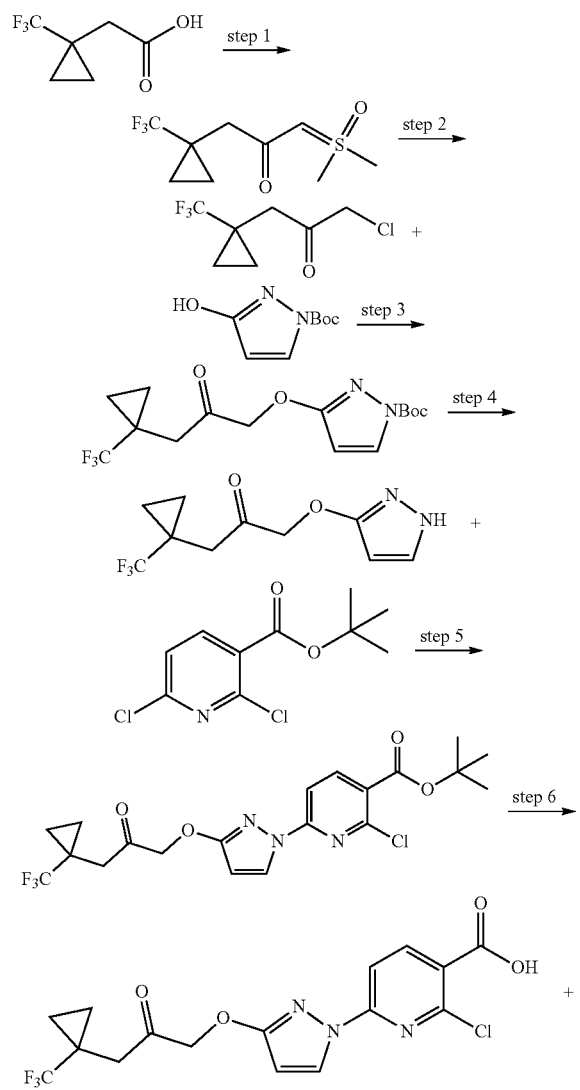

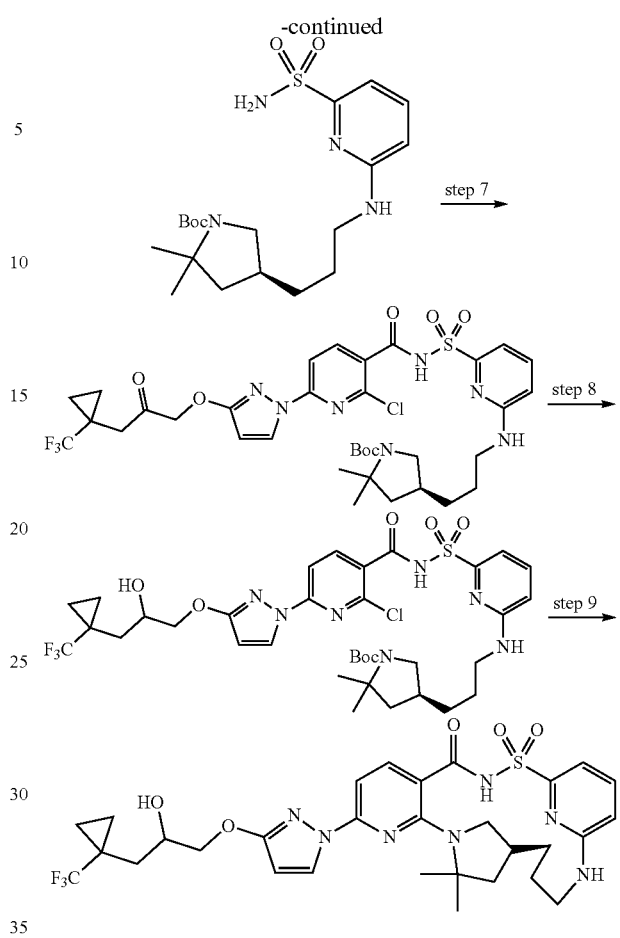

Step 1: Dimethyl({2-oxo-3-[1-(trifluoromethyl)cyclopropyl]propylidene})-λ⁶-sulfanone In a reaction vessel was added 2-[1-(trifluoromethyl)cyclopropyl]acetic acid (3.0 g, 17.85 mmol) and dissolved in dichloromethane (30 mL). The mixture was cooled to 0° C. and added N,N-dimethylformamide (50 μL, 0.6457 mmol) and oxalyl chloride (1.9 mL, 21.78 mmol). The resulting reaction was stirred for 2 h initially at 0° C. allowing to warm to room temperature over that period. The volatiles were then removed by rotary evaporation (vacuum set to 100 mbar and water bath at 20° C.) to give the desired neat acid chloride. The solution of the acid chloride was used directly without further purification. In a separate vessel, added trimethylsulfoxonium iodide (12.2 g, 55.44 mmol) and dissolved in tetrahydrofuran (30 mL). Potassium t-butoxide (6.2 g, 55.25 mmol) was added as a 1 M solution in tetrahydrofuran and the resulting mixture was heated to reflux for 2 h. The mixture was cooled to 0° C. and the acid chloride prepared above was added as a solution in tetrahydrofuran (30 mL), maintaining the temperature below 5° C. Mixture was stirred at 0° C. for 1 h. Added Celite to mixture then filtered over Celite (washing solids with ethyl acetate and concentrating volatiles by rotary evaporation). Washed the resulting mixture into separatory funnel with water and extracted with ethyl acetate (2×100 mL). The combined ethyl acetate layers were washed with brine, dried over sodium sulfate, filtered and concentrated in vacuo to afford dimethyl({2-oxo-3-[1-(trifluoromethyl)cyclopropyl]propylidene})-λ⁶-sulfanone (1.9 g, 44%) as an oil. ¹H NMR (400 MHz, Chloroform-d) δ 3.39 (s, 6H), 2.99 (s, 1H), 2.40 (s, 2H), 1.01 (d, J=2.0 Hz, 2H), 0.94-0.81 (m, 2H). ESI-MS m/z calc. 242.05884, found 243.2 (M+1)⁺; Retention time: 0.72 min (LC Method E).

Step 2: 1-Chloro-3-[1-(trifluoromethyl)cyclopropyl]propan-2-one

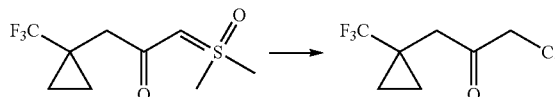

To a 100 mL round bottom flask was added dimethyl({2-oxo-3-[1-(trifluoromethyl)cyclopropyl]propylidene})-λ⁶-sulfanone (1.9 g, 7.843 mmol) under nitrogen dissolved in dry tetrahydrofuran (16.0 mL) and then added hydrochloric acid (4 M in dioxane) (2.5 mL of 4 M, 10.00 mmol). The resulting mixture was heated to 60° C. and stirred for 3 h. The solvent was evaporated in vacuo (130 mbar and water bath at 20° C.) and the resulting residue was partitioned between ethyl acetate and water then added some brine and separated the layers. The organic layer was washed with brine, dried over sodium sulfate, filtered and concentrated in vacuo (100 mbar and water bath at 30° C.) to give 1-chloro-3-[1-(trifluoromethyl)cyclopropyl]propan-2-one (1.57 g, 100%) as an orange oil. ¹H NMR (400 MHz, Chloroform-d) δ 3.70 (s, 2H), 2.04 (s, 2H), 1.17-1.05 (m, 2H), 0.85 (tt, J=3.8, 2.8, 2.2 Hz, 2H).

Step 3: tert-Butyl 3-[2-oxo-3-[1-(trifluoromethyl)cyclopropyl]propoxy]pyrazole-1-carboxylate

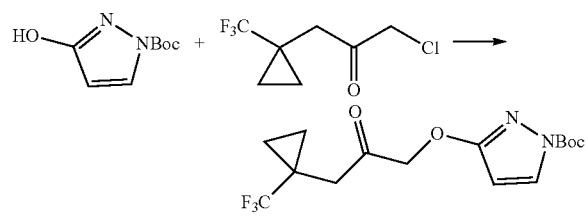

In a 100 mL flask flushed with nitrogen was added tert-butyl 3-hydroxypyrazole-1-carboxylate (1.20 g, 6.515 mmol), potassium carbonate (1.81 g, 13.10 mmol) and sodium iodide (11 mg, 0.07339 mmol) dissolved in N,N-dimethylformamide (15 mL). The mixture was stirred for 5 min and then 1-chloro-3-[1-(trifluoromethyl)cyclopropyl]propan-2-one (1.57 g, 7.827 mmol) was added as a solution in N,N-dimethylformamide (10 mL). The resulting mixture was heated to 65° C. for 16 h. The reaction mixture was poured into a solution of saturated brine. The material was extracted with ethyl acetate (2×150 mL), combined the organic layers, washed with water (2×150 mL), dried over sodium sulfate, filtered and concentrated. The orange residue was purified by silica gel chromatography using a gradient from 100% hexanes to 60% ethyl acetate in hexanes to afford tert-butyl 3-[2-oxo-3-[1-(trifluoromethyl)cyclopropyl]propoxy]pyrazole-1-carboxylate (700 mg, 31%) as a light yellow oil. ¹H NMR (400 MHz, Chloroform-d) δ 7.86 (d, J=2.8 Hz, 1H), 5.96 (d, J=2.8 Hz, 1H), 4.93 (s, 2H), 2.77 (s, 2H), 1.60 (s, 9H), 1.15-1.07 (m, 2H), 0.91-0.86 (m, 2H). ESI-MS m/z calc. 348.1297, found 349.2 (M+1)⁺; Retention time: 1.73 min (LC Method E).

Step 4: 1-(1H-Pyrazol-3-yloxy)-3-[1-(trifluoromethyl)cyclopropyl]propan-2-one

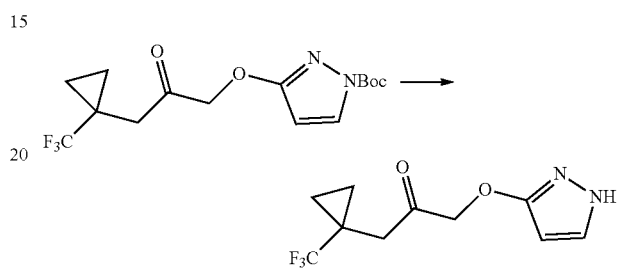

To a solution of tert-butyl 3-[2-oxo-3-[1-(trifluoromethyl)cyclopropyl]propoxy]pyrazole-1-carboxylate (700 mg, 2.010 mmol) in dichloromethane (14 mL) was added trifluoroacetic acid (3.1 mL, 40.24 mmol) and the mixture was stirred for 1 h. The solvent was removed and the resulting oil was evaporated and dried under vacuum to afford a light yellow solid. Dissolved the solid in ethyl acetate and added saturated aqueous sodium bicarbonate and separated the layers. Dried the organic layer over sodium sulfate, filtered and concentrated under reduced pressure to give 1-(1H-pyrazol-3-yloxy)-3-[1-(trifluoromethyl)cyclopropyl]propan-2-one (498 mg, 100%). ESI-MS m/z calc. 248.07726, found 249.2 (M+1)⁺; Retention time: 1.11 min (LC Method E).

Step 5: tert-Butyl 2-chloro-6-[3-[2-oxo-3-[1-(trifluoromethyl)cyclopropyl]propoxy]pyrazol-1-yl]pyridine-3-carboxylate

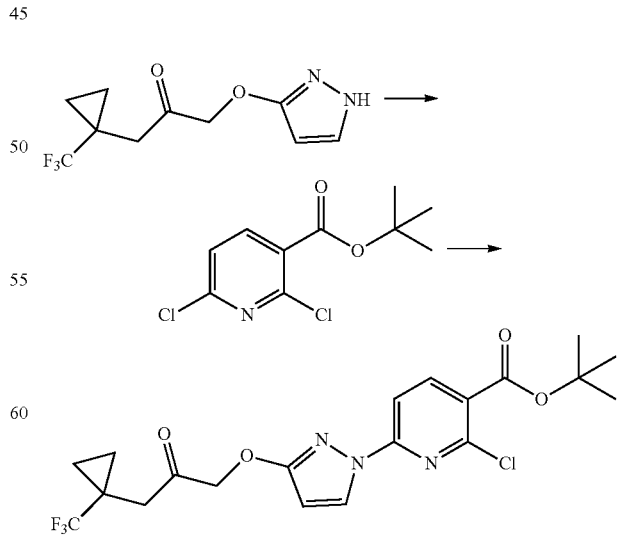

tert-Butyl 2,6-dichloropyridine-3-carboxylate (497 mg, 2.003 mmol), 1-(1H-pyrazol-3-yloxy)-3-[1-(trifluoromethyl)cyclopropyl]propan-2-one (498 mg, 2.006 mmol) and potassium carbonate (625 mg, 4.522 mmol) were combined in anhydrous dimethyl sulfoxide (14 mL).1,4-diazabicyclo[2.2.2]octane (45 mg, 0.4012 mmol) was added and the mixture was stirred at room temperature under nitrogen for 16 h. The reaction mixture was diluted with water (16 mL) and stirred for 15 min. The resulting mixture was diluted with ethyl acetate and washed with water (3×50 mL). The organic layer dried over sodium sulfate, filtered and concentrated under reduced pressure. The orange residue was purified by silica gel chromatography using a gradient from 100% hexanes to 60% ethyl acetate in hexanes to afford a light yellow oil which was then dried under vacuum to give tert-butyl 2-chloro-6-[3-[2-oxo-3-[1-(trifluoromethyl)cyclopropyl]propoxy]pyrazol-1-yl]pyridine-3-carboxylate (500 mg, 54%). $^1$H NMR (400 MHz, Chloroform-d) δ 8.38 (d, J=2.8 Hz, 1H), 8.18 (d, J=8.4 Hz, 1H), 7.59 (d, J=8.4 Hz, 1H), 6.04 (d, J=2.8 Hz, 1H), 4.87 (s, 2H), 2.79 (s, 2H), 1.62 (s, 10H), 1.14-1.09 (m, 2H), 0.85 (dd, J=3.0, 1.7 Hz, 2H). ESI-MS m/z calc. 459.11728, found 460.2 (M+1)$^+$; Retention time: 2.21 min (LC Method E).

Step 6: 2-Chloro-6-[3-[2-oxo-3-[1-(trifluoromethyl)cyclopropyl]propoxy]pyrazol-1-yl]pyridine-3-carboxylic Acid

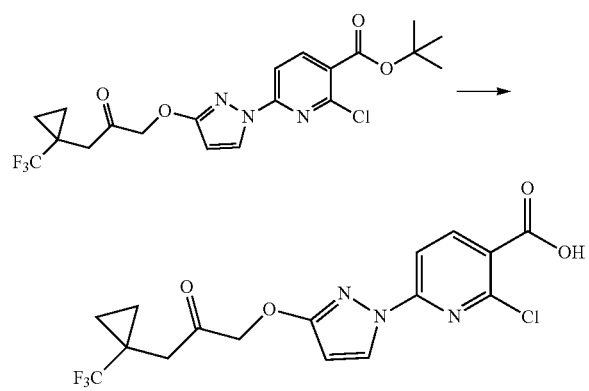

tert-Butyl 2-chloro-6-[3-[2-oxo-3-[1-(trifluoromethyl)cyclopropyl]propoxy]pyrazol-1-yl]pyridine-3-carboxylate (500 mg, 1.087 mmol) was dissolved in dichloromethane (11 mL) and cooled to 0° C. in an ice bath. To the mixture was slowly added hydrochloric acid (1.5 mL of 4 M in dioxane, 6.000 mmol) and the mixture was stirred at 0° C. for 1 h. Added additional hydrochloric acid (5.5 mL of 4 M in dioxane, 22.00 mmol) and stirred for 30 min 0° C. then 2 h at room temperature. Added additional hydrochloric acid (5.435 mL of 4 M in dioxane, 21.74 mmol) and stirred at room temperature over 17 h. The reaction mixture was concentrated under reduced pressure to a white solid which was then slurried in diethyl ether, filtered and slurried again in diethyl ether. The solid was collected by vacuum filtration and dried under vacuum for 20 h to provide 2-chloro-6-[3-[2-oxo-3-[1-(trifluoromethyl)cyclopropyl]propoxy]pyrazol-1-yl]pyridine-3-carboxylic acid (237.5 mg, 54%) as a white solid. ESI-MS m/z calc. 403.05466, found 404.2 (M+1)$^+$; Retention time: 1.59 min (LC Method E).

Step 7: tert-Butyl (4S)-4-[3-[[6-[[2-chloro-6-[3-[2-oxo-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate

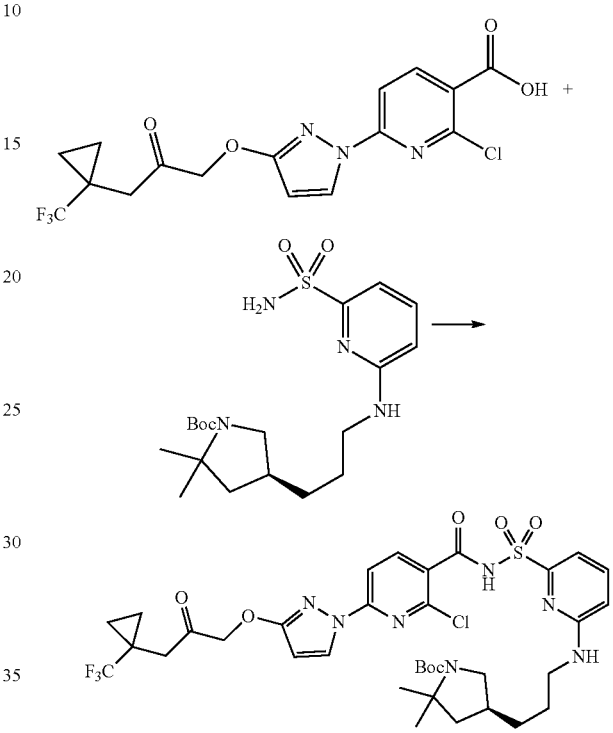

2-Chloro-6-[3-[2-oxo-3-[1-(trifluoromethyl)cyclopropyl]propoxy]pyrazol-1-yl]pyridine-3-carboxylic acid (166 mg, 0.4112 mmol) and carbonyl diimidazole (75 mg, 0.4625 mmol) were combined in tetrahydrofuran (4.0 mL) and stirred for 110 min at room temperature. Then tert-butyl (4S)-2,2-dimethyl-4-[3-[(6-sulfamoyl-2-pyridyl)amino]propyl]pyrrolidine-1-carboxylate (187 mg, 0.4533 mmol) was added followed by anhydrous 1,8-diazabicyclo[5.4.0]undec-7-ene (160 µL, 1.070 mmol) and the reaction was stirred at room temperature for 20 h. The reaction was diluted with ethyl acetate and washed with a saturated aqueous sodium bicarbonate solution, followed by brine. The organic layer was dried over sodium sulfate, filtered, evaporated and then purified by silica gel chromatography using a gradient from 100% hexanes to 100% ethyl acetate followed by a second silica gel column using a gradient from 100% dichloromethane to 15% methanol in dichloromethane to afford tert-butyl (4S)-4-[3-[[6-[[2-chloro-6-[3-[2-oxo-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (173.7 mg, 53%) as a white solid. ESI-MS m/z calc. 797.25854, found 798.2 (M+1)$^+$; Retention time: 2.21 min (LC Method E).

Step 8: tert-Butyl (4S)-4-[3-[[6-[[2-chloro-6-[3-[2-hydroxy-3-[1-(trifluoromethyl)cyclo propyl]propoxy]pyrazol-1-yl]pyridine-3-carbonyl]sulfamoyl]-2-pyridyl]amino]propyl]-2,2-dimethyl-pyrrolidine-1-carboxylate

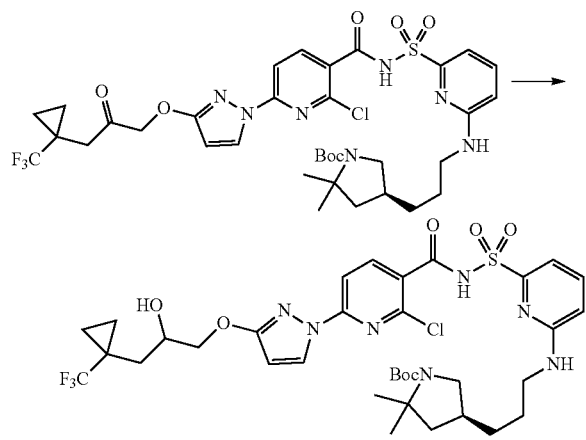

To a stirring solution of tert-butyl (4S)-4-[3-[[6-[[2-chloro-6-[3-[2-oxo-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (80 mg, 0.1002 mmol) in methanol (1.25 mL) under nitrogen was added sodium borohydride (10 mg, 0.2643 mmol) portionwise to control significant effervescence. After complete addition (which took 1 min) the reaction was a solution. The reaction was concentrated by rotary evaporation and then diluted with ethyl acetate and washed with water (2×20 mL), followed by brine (1×). The organic layer was then separated, dried over sodium sulfate, filtered and concentrated. The residue was dried under vacuum to afford tert-butyl (4S)-4-[3-[[6-[[2-chloro-6-[3-[2-hydroxy-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (80 mg, 100%) as a white solid. ESI-MS m/z calc. 799.2742, found 800.3 (M+1)$^+$; Retention time: 2.15 min (LC Method E).

Step 9: (14S)-8-(3-{2-Hydroxy-3-[1-(trifluoromethyl)cyclopropyl]propoxy}-1H-pyrazol-1-yl)-12,12-dimethyl-2λ$^6$-thia-3,9,11,18,23-pentaazatetracyclo[17.3.1.1$^{11,14}$.0$^{5,10}$]tetracosa-1(22),5(10),6,8,19(23),20-hexaene-2,2,4-trione (Compound 259)

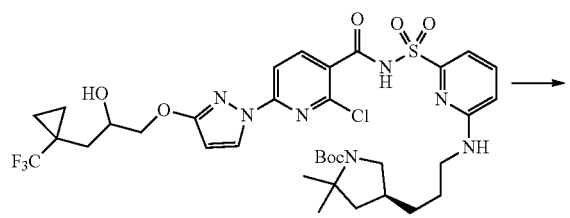

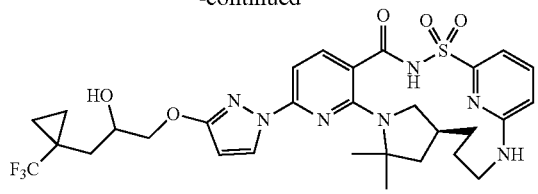

To a flask containing tert-butyl (4S)-4-[3-[[6-[[2-chloro-6-[3-[2-hydroxy-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (80 mg, 0.09996 mmol) was added dichloromethane (2.5 mL) and hydrochloric acid (500 μL of 4 M in dioxane, 2.000 mmol). After 90 min of stirring, the mixture was evaporated to dryness then diluted with ether (5 mL) and reconcentrated by rotary evaporation. The residue was then diluted with ether (5 mL) and reconcentrated by rotary evaporation again. Dried under vacuum overnight to a residue that was combined with potassium carbonate (139 mg, 1.006 mmol), 3 Å molecular sieves and dimethyl sulfoxide (3.5 mL) in a vial, purged with nitrogen, capped, heated to 155° C. and stirred for 4 h. Cooled to room temperature and the mixture was filtered, diluted with ethyl acetate and washed with water (2×20 mL), followed by brine. The organic layer was further washed with water, then dried over sodium sulfate, filtered and concentrated. The residue was purified by silica gel chromatography using a gradient from 100% hexanes to 100% ethyl acetate to afford (14S)-8-(3-{2-hydroxy-3-[1-(trifluoromethyl)cyclopropyl]propoxy}-1H-pyrazol-1-yl)-12,12-dimethyl-2λ$^6$-thia-3,9,11,18,23-pentaazatetracyclo[17.3.1.1$^{11,14}$.0$^{5,10}$]tetracosa-1(22),5(10),6,8,19(23),20-hexaene-2,2,4-trione (Compound 259) (27.91 mg, 42%) as an off-white solid. $^1$H NMR (400 MHz, dimethyl sulfoxide-d$_6$) δ 12.49 (s, 1H), 8.22 (d, J=2.8 Hz, 1H), 7.82 (d, J=8.3 Hz, 1H), 7.58 (dd, J=8.5, 7.2 Hz, 1H), 7.05 (d, J=7.2 Hz, 1H), 6.99 (s, 1H), 6.92 (d, J=8.2 Hz, 1H), 6.71 (d, J=8.5 Hz, 1H), 6.13 (d, J=2.8 Hz, 1H), 5.03 (s, 1H), 4.10 (dd, J=4.9, 2.4 Hz, 2H), 3.97 (d, J=4.7 Hz, 2H), 3.16 (s, 1H), 2.95 (d, J=13.4 Hz, 1H), 2.73-2.65 (m, 1H), 2.47-2.29 (m, 1H), 2.13 (s, 1H), 1.98 (dd, J=13.7, 3.4 Hz, 1H), 1.86 (dd, J=11.6, 3.6 Hz, 1H), 1.77 (s, 1H), 1.70-1.63 (m, 1H), 1.61 (s, 3H), 1.57 (d, J=12.4 Hz, 2H), 1.52 (s, 3H), 1.37-1.27 (m, 1H), 1.01-0.90 (m, 2H), 0.90-0.78 (m, 2H). ESI-MS m/z calc. 663.24506, found 664.4 (M+1)$^+$; Retention time: 1.88 min (LC Method E).

Example 85: Preparation of (14S)-8-[3-(2-{dispiro[2.0.2.1]heptan-7-yl}ethoxy)-1H-pyrazol-1-yl]-22-hydroxy-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 260)
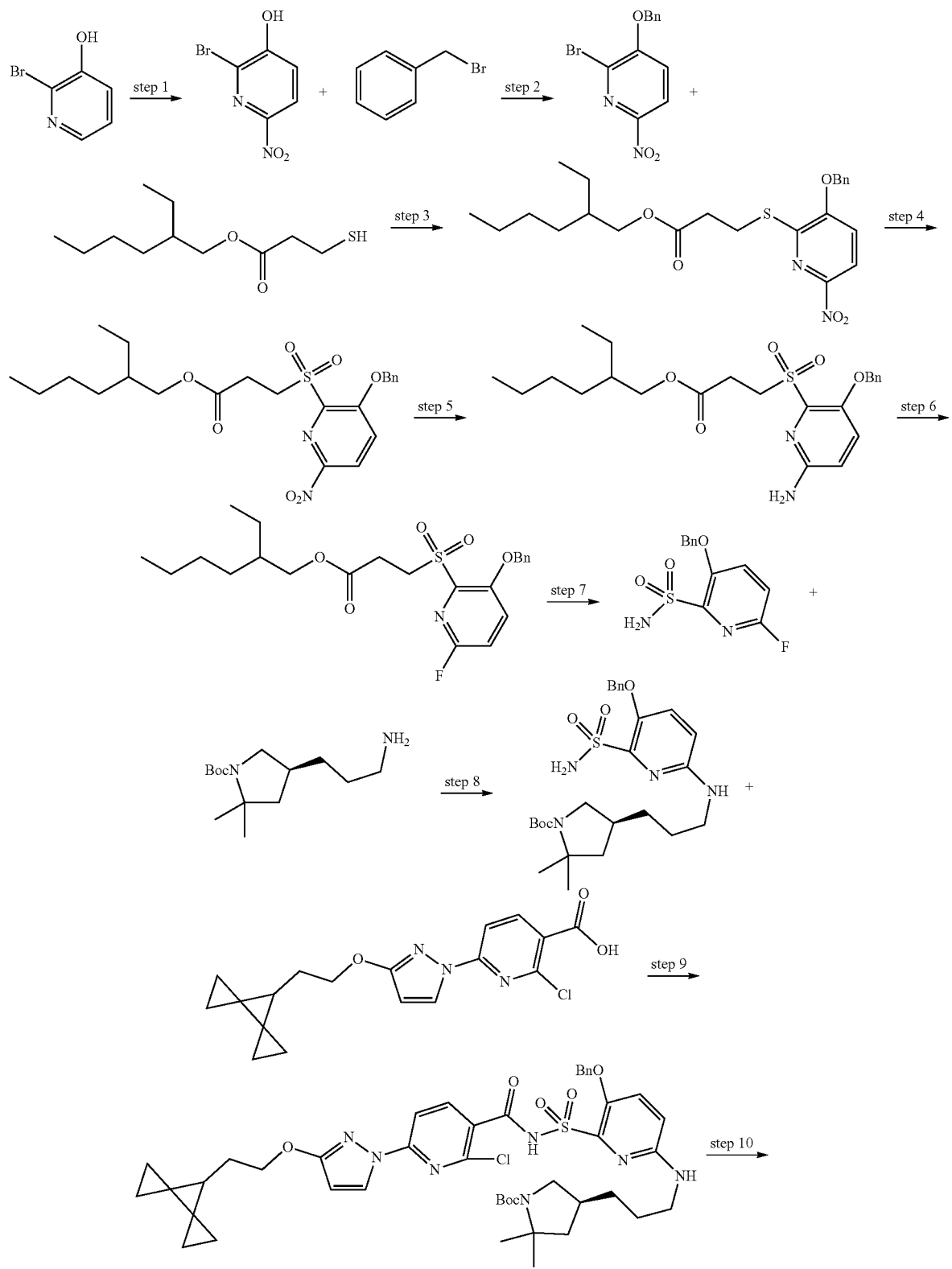

-continued

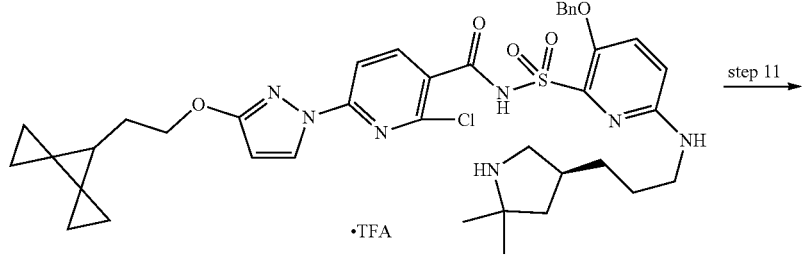

step 11

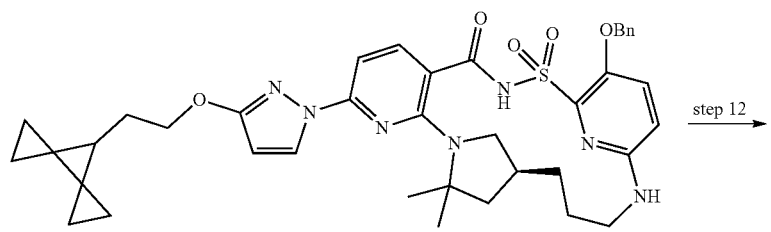

step 12

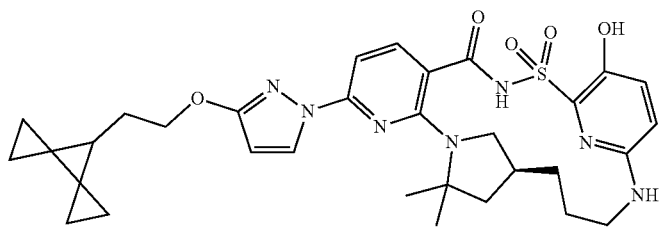

Step 1: 2-Bromo-6-nitro-pyridin-3-ol

Step 2: 3-Benzyloxy-2-bromo-6-nitro-pyridine

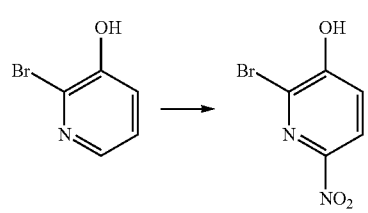 [SMILES: Oc1cccnc1Br ; O=[N+]([O-])c1ccc(O)c(Br)n1]

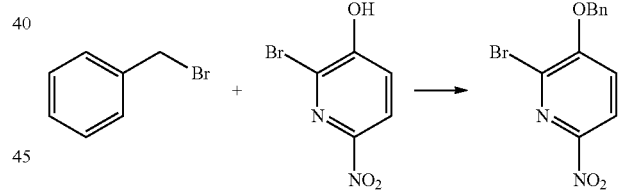

To a solution of 2-bromopyridin-3-ol (46 g, 264.38 mmol) in sulfuric acid (230 mL) was added nitric acid (24.989 g, 17.685 mL, 277.60 mmol) (70%) at 0° C. The reaction mixture was stirred at 0° C. for 30 min then at room temperature for 48 h, then poured on cold water (200 mL) and extracted with ethyl acetate (2×100 mL). The combined organic layers were washed with water (150 mL) and brine (150 mL), dried over sodium sulfate, filtered and the filtrate was concentrated in vacuo. The residue was purified by chromatography (silica gel, 0% to 20% ethyl acetate in heptane) to afford 2-bromo-6-nitro-pyridin-3-ol (9.2 g, 16%) as a yellow solid. $^1$H NMR (300 MHz, CDCl$_3$) δ 8.24 (d, J=8.5 Hz, 1H), 7.54 (d, J=8.5 Hz, 1H), 6.37 (br. s., 1H). ESI-MS m/z calc. 217.9327, found 221.0 (M+1)$^+$; Retention time: 1.492 min (LC Method N).

A solution of 2-bromo-6-nitro-pyridin-3-ol (9 g, 41.097 mmol) in dimethylformamide (60 mL) was added dropwise to a solution of sodium hydride (2 g, 50.005 mmol) at 0° C. in dimethylformamide (30 mL). After 30 min, benzyl bromide (7.4776 g, 5.2 mL, 43.720 mmol) was added, the cold bath was removed and the reaction was stirred at room temperature for 16 h. The crude mixture was diluted with water (75 mL) and extracted with ethyl acetate (3×75 mL). The combined organic layers were washed with water (2×75 mL), brine (100 mL), dried over sodium sulfate, filtered and concentrated under reduced pressure. The solid residue was triturated in a mixture of ethyl acetate/heptane (9/1) (50 mL), then filtered and washed with additional ethyl acetate/heptane (9/1) (50 mL) to afford 3-benzyloxy-2-bromo-6-nitro-pyridine (8.7 g, 68%) as a yellow solid. $^1$H NMR (300 MHz, dimethyl sulfoxide-d$_6$) δ 8.42 (d, J=8.5 Hz, 1H), 7.90 (d, J=8.8 Hz, 1H), 7.30-7.59 (m, 5H), 5.43 (s, 2H). ESI-MS m/z calc. 307.9797, found 311.0 (M+1)$^+$; Retention time: 1.956 min (LC Method S).

Step 3: 2-Ethylhexyl 3-[(3-benzyloxy-6-nitro-2-pyridyl)sulfanyl]propanoate

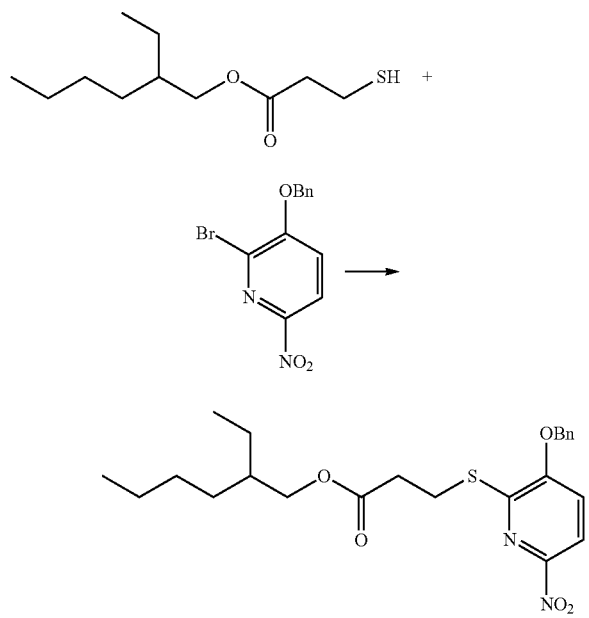

To a solution of 3-benzyloxy-2-bromo-6-nitro-pyridine (14.5 g, 46.908 mmol), Xantphos (1.7 g, 2.9380 mmol), Pd$_2$(dba)$_3$ (1.35 g, 1.4743 mmol) in toluene (300 mL) was added 2-ethylhexyl 3-sulfanylpropanoate (11.5 g, 52.666 mmol) followed by addition of N,N-diisopropylethylamine (12.614 g, 17 mL, 97.599 mmol). The resulting solution was evacuated and back-filled by nitrogen three times and then refluxed at 110° C. overnight. After cooling to room temperature, the reaction was filtered through a pad of Celite and washed with ethyl acetate (75 mL). The combined filtrates were concentrated and the resulting residue was purified by silica gel chromatography (0% to 15% gradient of ethyl acetate in heptanes) to provide 2-ethylhexyl 3-[(3-benzyloxy-6-nitro-2-pyridyl)sulfanyl]propanoate (20 g, 95%). $^1$H NMR (300 MHz, CDCl$_3$) δ 7.94 (d, J=8.5 Hz, 1H), 7.32-7.51 (m, 5H), 7.09-7.17 (m, 1H), 5.25 (s, 2H), 3.97-4.12 (m, 2H), 3.51 (t, J=6.9 Hz, 2H), 2.89 (t, J=6.8 Hz, 2H), 1.51-1.67 (m, 1H), 1.20-1.43 (m, 8H), 0.81-0.96 (m, 6H). ESI-MS m/z calc. 446.1875, found 447.2 (M+1)$^+$; Retention time: 4.181 min (LC Method T).

Step 4: 2-Ethylhexyl 3-[(3-benzyloxy-6-nitro-2-pyridyl)sulfonyl]propanoate

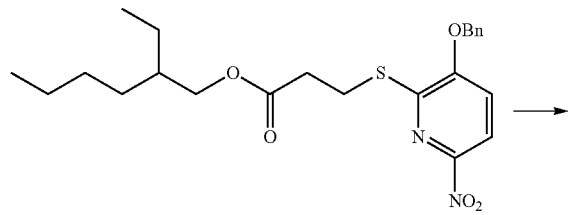

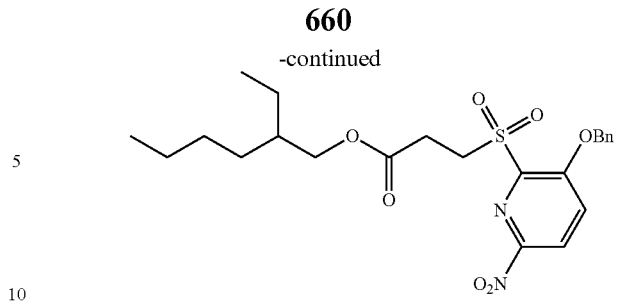

m-Chloroperbenzoic acid (21 g, 77% w/w in tetrahydrofuran, 93.703 mmol) was slowly added to a solution of 2-ethylhexyl 3-[(3-benzyloxy-6-nitro-2-pyridyl)sulfanyl]propanoate (20 g, 44.787 mmol) in dichloromethane (400 mL) at room temperature. The mixture was stirred at this temperature overnight. The solid was filtered off and the mixture was washed with 10% sodium thiosulfate solution (150 mL), 5% sodium bicarbonate solution (2×100 mL), water (100 mL) and brine (100 mL). The organic phase was dried over anhydrous sodium sulfate, filtered and concentrated under reduced pressure to give 2-ethylhexyl 3-[(3-benzyloxy-6-nitro-2-pyridyl)sulfonyl]propanoate (20.5 g, 96%) as a yellow solid. $^1$H NMR (300 MHz, CDCl$_3$) δ 8.39 (d, J=9.1 Hz, 1H), 7.64 (d, J=9.1 Hz, 1H), 7.31-7.52 (m, 5H), 5.45 (s, 2H), 4.03 (dd, J=5.7, 2.5 Hz, 2H), 3.89-4.00 (m, 2H), 3.04 (t, J=7.5 Hz, 2H), 1.50-1.66 (m, 1H), 1.22-1.41 (m, 8H), 0.83-0.95 (m, 6H).

Step 5: 2-Ethylhexyl 3-[(6-amino-3-benzyloxy-2-pyridyl)sulfonyl]propanoate

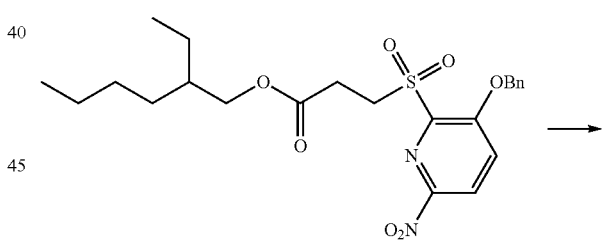


To a solution of 2-ethylhexyl 3-[(3-benzyloxy-6-nitro-2-pyridyl)sulfonyl]propanoate (5 g, 10.448 mmol) in ethanol (280 mL) and water (80 mL) was added iron (2.4 g, 42.976 mmol) and ammonium chloride (1.7 g, 31.781 mmol). The reaction was stirred at 100° C. for 1.5 h. The dark solution was allowed to cool to room temperature, filtered over Celite and washed with dichloromethane (150 mL). The filtrate was concentrated under reduced pressure. The crude product was diluted in water (100 mL) and extracted with dichloromethane (2×75 mL). The combined organic layers were dried over anhydrous sodium sulfate, filtered and concentrated under reduced pressure. The resulting crude was purified by trituration in tert-butyl methyl ether (50 mL), the suspension was filtered and washed with tert-butyl methyl ether (50 mL). The resulting off-white solid was dried under vacuum overnight to provide 2-ethylhexyl 3-[(6-amino-3-benzyloxy-2-pyridyl)sulfonyl]propanoate (4.5 g, 96%). ESI-MS m/z calc. 448.2032, found 449.2 (M+1)+; Retention time: 2.35 min (LC Method I).

Step 6: 2-Ethylhexyl 3-[(3-benzyloxy-6-fluoro-2-pyridyl)sulfonyl]propanoate

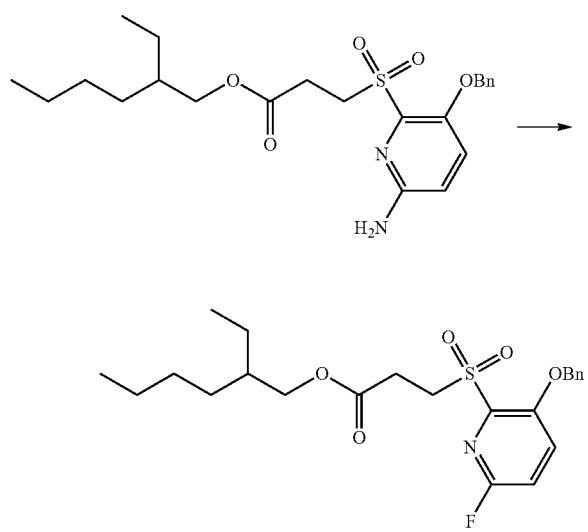

A solution of 2-ethylhexyl 3-[(6-amino-3-benzyloxy-2-pyridyl)sulfonyl]propanoate (4.5 g, 10.032 mmol) in hydrogen fluoride pyridine (55.0 g, 50 mL, 554.96 mmol) was cooled to −52° C. The resulting red solution was treated with sodium nitrite (1.4 g, 20.291 mmol) and was allowed to warm to room temperature. A gas release was observed and the reaction turned to orange and turbid. The reaction was stirred overnight at room temperature and slowly poured over ice and water (50 mL). The mixture was neutralized by carefully adding sodium bicarbonate aqueous and was extracted with ethyl acetate (3×50 mL). The combined organic layers were dried over anhydrous sodium sulfate, filtered and concentrated under reduced pressure to provide crude 2-ethylhexyl 3-[(3-benzyloxy-6-fluoro-2-pyridyl)sulfonyl]propanoate (4 g, 88%). ESI-MS m/z calc. 451.1829, found 452.2 (M+1)+; Retention time: 2.46 min (LC Method I).

Step 7: 3-Benzyloxy-6-fluoro-pyridine-2-sulfonamide

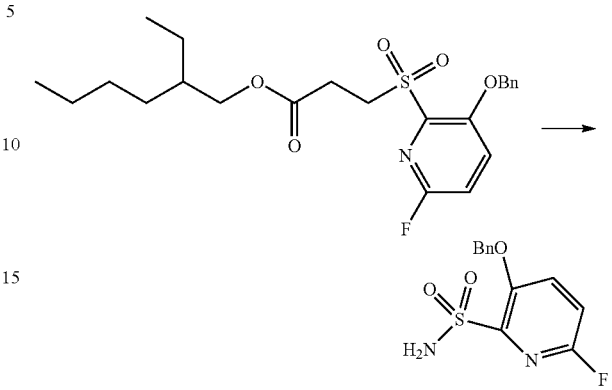

To a solution of 2-ethylhexyl 3-[(3-benzyloxy-6-fluoro-2-pyridyl)sulfonyl]propanoate (8 g, 17.717 mmol) in dimethylsulfoxide (48 mL) was added 1,8-diazabicyclo(5.4.0)undec-7-ene (5.5550 g, 5.5 mL, 36.489 mmol). The reaction was stirred 1 h at room temperature and a solution of hydroxylamine-O-sulfonic acid (10.1 g, 89.307 mmol) and sodium acetate (6 g, 73.141 mmol) in water (32 mL) was added. The reaction was stirred 1 h at room temperature, diluted with water (100 mL) and extracted with ethyl acetate (3×75 mL). The combined organic layers were washed with brine (30 mL), dried over anhydrous sodium sulfate, filtered and concentrated under reduced pressure. The crude product was purified by flash chromatography on silica gel (gradient from 10% to 40% ethyl acetate in heptane) to yield 3-benzyloxy-6-fluoro-pyridine-2-sulfonamide (4.1 g, 82%) as an off white solid. $^1$H NMR (300 MHz, dimethyl sulfoxide-$d_6$) δ 5.38 (s, 2H), 7.25-7.48 (m, 4H), 7.49-7.57 (m, 4H), 7.96 (dd, J=9.0, 6.0 Hz, 1H); $^{19}$F NMR (282 MHz, dimethyl sulfoxide-$d_6$) δ −78.5-78.2 (m, 1F). ESI-MS m/z calc. 282.0474, found 283.1 (M+1)+: Retention time: 2.14 min (LC Method H).

Step 8: tert-Butyl (4S)-4-[3-[(5-benzyloxy-6-sulfamoyl-2-pyridyl)amino]propyl]-2,2-dimethyl-pyrrolidine-1-carboxylate

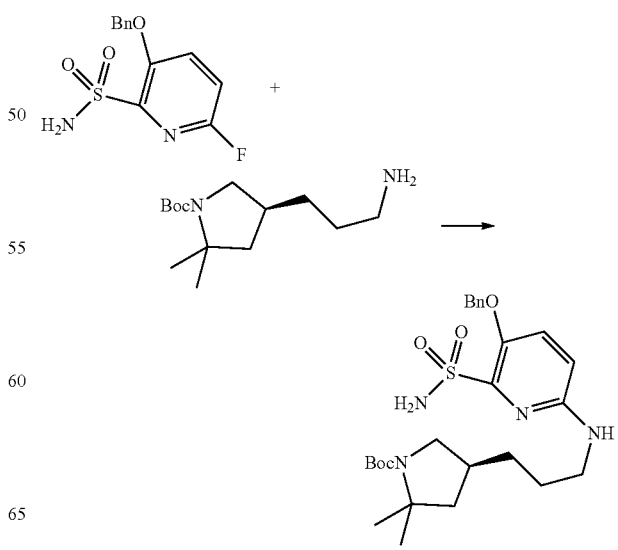

A 20 mL vial was charged under nitrogen with tert-butyl (4S)-4-(3-aminopropyl)-2,2-dimethyl-pyrrolidine-1-carboxylate (291 mg, 1.135 mmol), 3-benzyloxy-6-fluoro-pyridine-2-sulfonamide (321 mg, 1.137 mmol), anhydrous dimethyl sulfoxide (3 mL) and N,N-diisopropylethylamine (0.3 mL, 1.722 mmol). The vial was capped and stirred at 85° C. for 3 h then at 110° C. for 16 h then at 120° C. for 29 h. The mixture was diluted with ethyl acetate (50 mL), water (50 mL) and 10% citric acid (10 mL). The two phases were separated. The organic phase was washed with brine (30 mL) dried over sodium sulfate and the solvents were evaporated. The product was purified by flash chromatography on silica gel using a gradient of ethyl acetate (0% to 60% over 30 min.) in hexanes giving tert-butyl (4S)-4-[3-[(5-benzyloxy-6-sulfamoyl-2-pyridyl)amino]propyl]-2,2-dimethyl-pyrrolidine-1-carboxylate (342 mg, 58% yield, 92% purity) as a foamy solid. $^1$H NMR (400 MHz, dimethyl sulfoxide-$d_6$) δ 7.54-7.47 (m, 2H), 7.44 (d, J=9.0 Hz, 1H), 7.41-7.33 (m, 2H), 7.33-7.22 (m, 1H), 6.94 (s, 2H), 6.60 (d, J=8.9 Hz, 1H), 6.49 (t, J=5.5 Hz, 1H), 5.11 (s, 2H), 3.55 (q, J=8.7 Hz, 1H), 3.27-3.16 (m, 2H), 2.79 (q, J=10.1 Hz, 1H), 2.10 (broad s, 1H), 1.93-1.85 (m, 1H), 1.54-1.43 (m, 2H), 1.43-1.37 (m, 15H), 1.24 (s, 3H). ESI-MS m/z calc. 518.2563, found 519.4 (M+1)$^+$; Retention time: 1.88 min (LC Method B).

Step 9: tert-Butyl (4S)-4-[3-[[5-benzyloxy-6-[[2-chloro-6-[3-(2-dispiro[2.0.2.1]heptan-7-yletoxy) pyrazol-1-yl]pyridine-3-carbonyl]sulfamoyl]-2-pyridyl]amino]propyl]-2,2-dimethyl-pyrrolidine-1-carboxylate

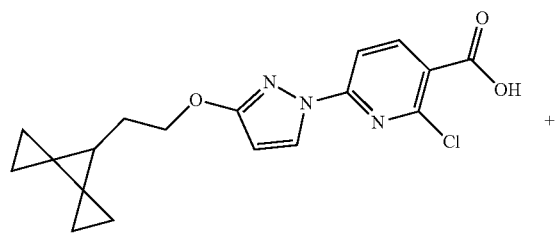

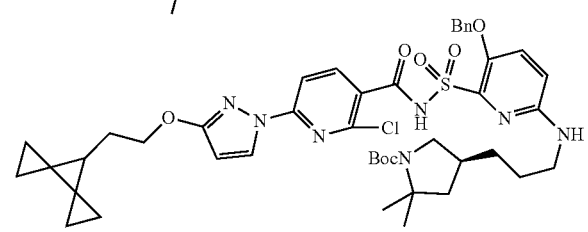

A 20 mL vial was charged under nitrogen with 2-chloro-6-[3-(2-dispiro[2.0.2.1]heptan-7-yletoxy)pyrazol-1-yl] pyridine-3-carboxylic acid (100 mg, 0.2779 mmol) and anhydrous tetrahydrofuran (2 mL). Added carbonyl diimidazole (45 mg, 0.2775 mmol) and the mixture was stirred under nitrogen at room temperature for 4 h. A second amount of carbonyl diimidazole (45 mg, 0.2775 mmol) was added and the mixture was stirred at room temperature for 3 h. In a separate 20 mL flask, a solution of tert-butyl (4S)-4-[3-[(5-benzyloxy-6-sulfamoyl-2-pyridyl)amino]propyl]-2,2-dimethyl-pyrrolidine-1-carboxylate (121 mg, 0.2333 mmol) in anhydrous tetrahydrofuran (1 mL) was prepared under nitrogen atmosphere and it was subsequently added via syringe into the activated ester solution. Added 1,8-diazabicyclo[5.4.0]undec-7-ene (0.18 mL, 1.204 mmol) through a syringe and the reaction mixture was stirred at room temperature under nitrogen atmosphere. After 17 h, the solvents were removed under reduced pressure and the resulting thick oil was treated with ethyl acetate (25 mL) and water (25 mL). Aqueous hydrochloric acid (250 µL of 6 M, 1.500 mmol) was added slowly (final pH=5) and the two phases were separated. The aqueous phase was extracted with ethyl acetate (30 mL). The combined organic extracts were washed with brine (30 mL) and dried over sodium sulfate. After filtration and evaporation of the solvents, the residue was dissolved in dichloromethane and purified by flash chromatography on silica gel using a gradient of ethyl acetate (0% to 100% over 30 min) in hexanes giving tert-butyl (4S)-4-[3-[[5-benzyloxy-6-[[2-chloro-6-[3-(2-dispiro[2.0.2.1]heptan-7-yletoxy)pyrazol-1-yl]pyridine-3-carbonyl]sulfamoyl]-2-pyridyl]amino]propyl]-2,2-dimethyl-pyrrolidine-1-carboxylate (99 mg, 49% yield, 93% purity) as a colorless film. ESI-MS m/z calc. 859.34937, found 860.5 (M+1)$^+$; Retention time: 1.82 min (LC Method B).

Step 10: N-[[3-Benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-yletoxy) pyrazol-1-yl]pyridine-3-carboxamide (Trifluoroacetate Salt)

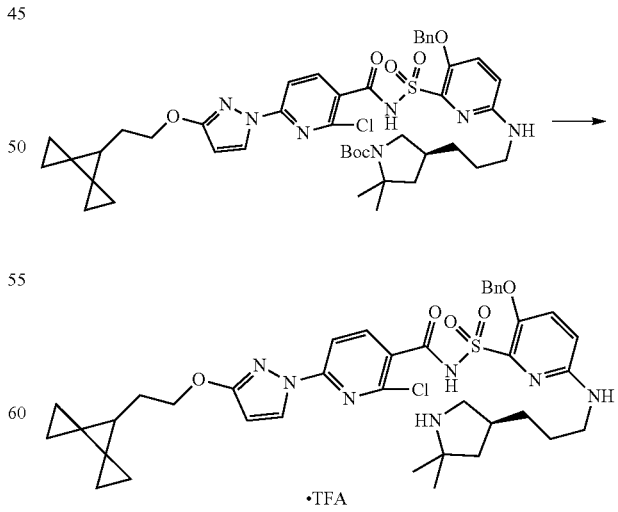

To a solution of tert-butyl (4S)-4-[3-[[5-benzyloxy-6-[[2-chloro-6-[3-(2-dispiro[2.0.2.1]heptan-7-yletoxy)pyrazol- 1-yl]pyridine-3-carbonyl]sulfamoyl]-2-pyridyl]amino]propyl]-2,2-dimethyl-pyrrolidine-1-carboxylate (99 mg, 0.1151 mmol) in dichloromethane (0.5 mL) and toluene (0.2 mL) was added trifluoroacetic acid (100 µL, 1.298 mmol) and the mixture stirred at ambient temperature for 23 h. The solvent was removed in vacuo with the bath temperature set at 40° C. affording a thick yellow oil. The oil was diluted with toluene (5 mL) and the solvent removed in vacuo at 40° C. affording N-[[3-benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (100 mg, 99%) as a yellow resin. ESI-MS m/z calc. 759.29694, found 760.4 (M+1)$^+$; Retention time: 1.9 min (LC Method B).

Step 11: (14S)-22-(Benzyloxy)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione

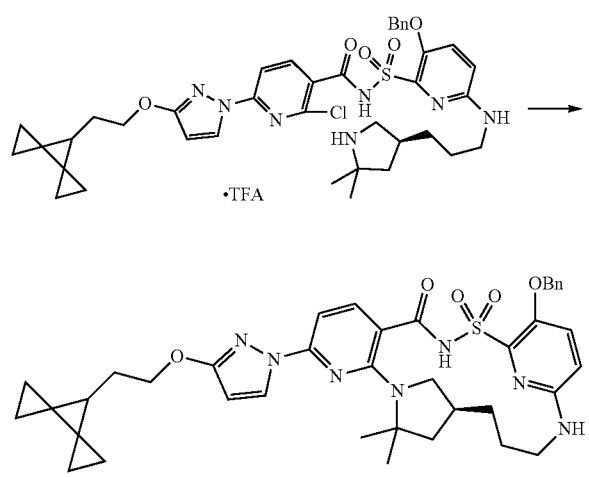

To a solution of N-[[3-benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (100 mg, 0.1144 mmol) in NMP (2 mL) was added potassium carbonate (180 mg, 1.302 mmol). The mixture was purged with nitrogen for 5 min. The mixture was heated at 150° C. for 20 h. The reaction mixture was cooled to room temperature and added to water (8 mL). The mixture was carefully acidified with aqueous hydrochloric acid (500 µL of 6 M, 3.000 mmol) until pH=1 affording a foamy slurry. The solid was collected by filtration on paper. The wet solid was dissolved in ethyl acetate and the solution was dried over sodium sulfate then filtered. The solvents were removed and the residue was purified by flash chromatography on silica gel using a gradient of methanol (0% to 5% over 30 min) in dichloromethane giving (14S)-22-(benzyloxy)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (31 mg, 37%) as an off-white solid. ESI-MS m/z calc. 723.3203, found 724.5 (M+1)$^+$; Retention time: 2.19 min (LC Method B).

Step 12: (14S)-8-[3-(2-{Dispiro[2.0.2.1]heptan-7-yl}ethoxy)-1H-pyrazol-1-yl]-22-hydroxy-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 260)

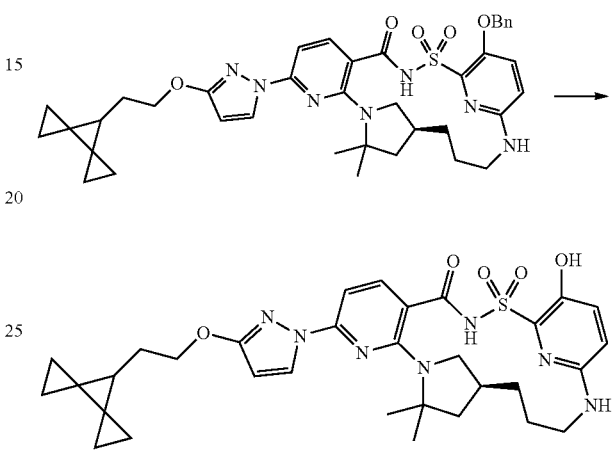

A 100 mL flask was charged with (14S)-22-(benzyloxy)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (31 mg, 0.04282 mmol) and methanol (6 mL). The solution was sparged with nitrogen. 10% Palladium on carbon (wet, Degussa, 21 mg, 0.01973 mmol) was added and the mixture was stirred under an atmosphere of hydrogen (balloon) for 3 h. The solution was sparged with nitrogen, diluted with methanol and filtered through celite. After evaporation of the solvents, the residue was dissolved in dimethyl sulfoxide (1 mL). The solution was microfiltered and purified by reverse phase preparative HPLC (C$_{18}$) using a gradient of acetonitrile in water (30% to 99% over 15 min, 9504 injection, no modifier). The pure fractions were collected and the solvents removed under evaporation. The residue was treated with dichloromethane/hexanes and the solvents were evaporated to give (14S)-8-[3-(2-{dispiro[2.0.2.1]heptan-7-yl}ethoxy)-1H-pyrazol-1-yl]-22-hydroxy-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 260) (10 mg, 36%) as an off-white solid. $^1$H NMR (400 MHz, dimethyl sulfoxide-d$_6$) δ 12.39 (br s, 1H), 9.07 (br s, 1H, exch.), 8.21 (d, J=2.8 Hz, 1H), 7.80 (br d, J=8.0 Hz, 1H), 7.20 (br s, 1H), 6.91 (br d, J=8.2 Hz, 1H), 6.69 (br d, J=8.8 Hz, 1H), 6.28 (br s, 1H, exch.), 6.08 (d, J=2.6 Hz, 1H), 4.21 (t, J=6.7 Hz, 2H), 3.77 (br s, 1H), 3.20 (br s, 1H), 2.96-2.79 (m, 2H), 2.12 (br s, 1H), 1.91-1.50 (m, 13H), 1.47 (t, J=6.5 Hz, 1H), 1.42-1.29 (m, 1H), 0.89-0.78 (m, 4H), 0.68-0.60 (m, 2H), 0.53-0.44 (m, 2H). ESI-MS m/z calc. 633.2733, found 634.3 (M+1)$^+$; Retention time: 2.39 min (LC Method B).

Example 86: Preparation of (14S)-22-hydroxy-12, 12-dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.111,14.05,10]tetracosa-1(22),5,7,9,19(23),20-hexaene-2,2,4-trione
(Compound 261)
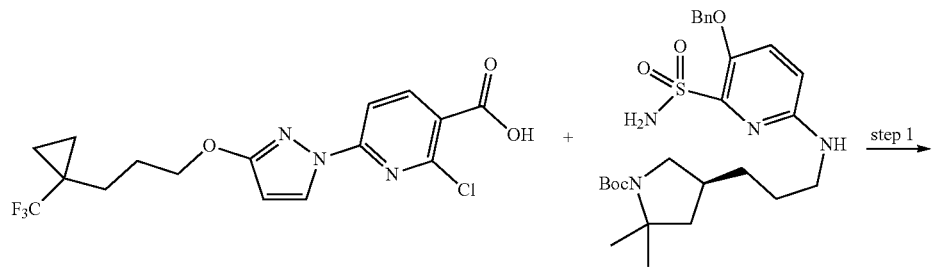
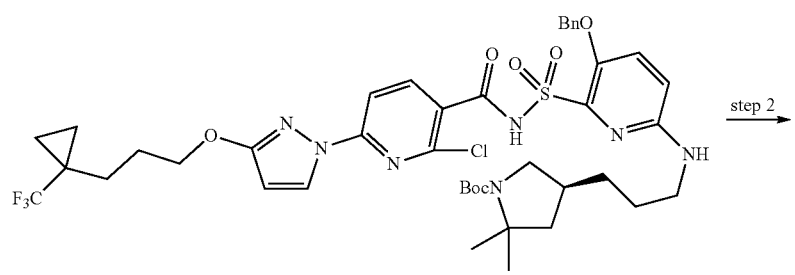
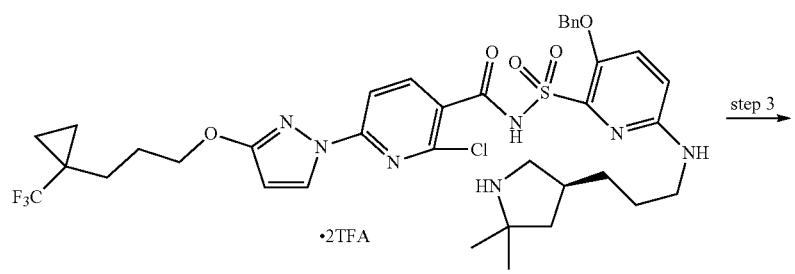
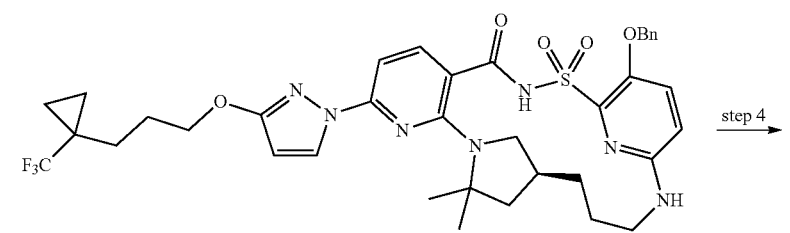
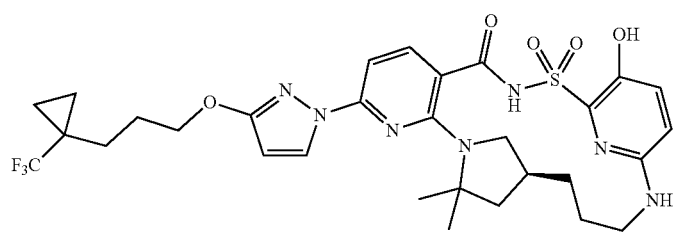

Step 1: tert-Butyl (4S)-4-[3-[[5-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate

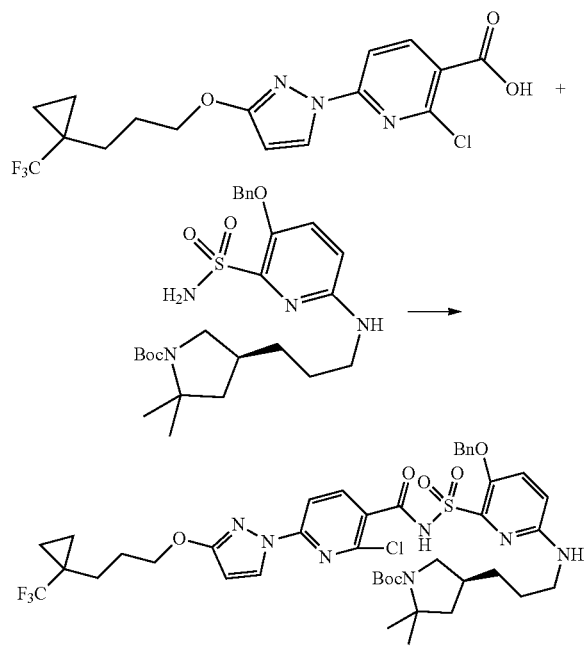

A 20 mL vial was charged under nitrogen with 2-chloro-6-[3-[3-[1-(trifluoromethyl)cyclopropyl]propoxy]pyrazol-1-yl]pyridine-3-carboxylic acid (188 mg, 0.4824 mmol) and anhydrous tetrahydrofuran (3 mL). Added carbonyl diimidazole (75 mg, 0.4625 mmol) and the mixture was stirred under nitrogen at room temperature for 4 h. A second amount of carbonyl diimidazole (75 mg, 0.4625 mmol) was added and the mixture was stirred at room temperature for 2 h. In a separate 20 mL flask, a solution of tert-butyl (4S)-4-[3-[(5-benzyloxy-6-sulfamoyl-2-pyridyl)amino]propyl]-2,2-dimethyl-pyrrolidine-1-carboxylate (204 mg, 0.3933 mmol) in anhydrous tetrahydrofuran (2 mL) was prepared under nitrogen atmosphere and it was subsequently added via syringe into the activated ester solution. Added 1,8-diazabicyclo[5.4.0]undec-7-ene (0.31 mL, 2.073 mmol) through a syringe and the reaction mixture was stirred at room temperature under nitrogen atmosphere for 5 days. The solvents were removed under reduced pressure and the resulting thick oil was treated with ethyl acetate (50 mL) and water (50 mL). Added hydrochloric acid (450 μL of 6 M, 2.700 mmol) slowly (final pH=5) and the two phases were separated. The aqueous phase was extracted with ethyl acetate (30 mL). The combined organic extracts were washed with brine (30 mL) and dried over sodium sulfate. After filtration and evaporation of the solvents, the residue was dissolved in dichloromethane and purified by flash chromatography on silica gel using a gradient of ethyl acetate (0% to 100% over 30 min) in hexanes. The product co-eluted with an impurity which was removed with a second purification by silica gel chromatography under the same conditions as the first column. The fractions containing the expected material were combined and the solvents evaporated to give tert-butyl (4S)-4-[3-[[5-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (109 mg, 31% yield, 86% purity) as an off-white film. ESI-MS m/z calc. 889.3211, found 890.4 (M+1)⁺; Retention time: 2.49 min (LC Method B).

Step 2: N-[[3-Benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (Ditrifluoroacetate Salt)

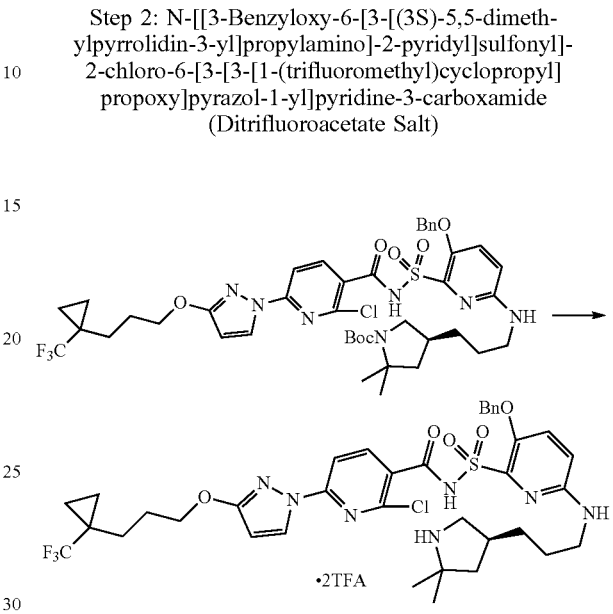

To a solution of tert-butyl (4S)-4-[3-[[5-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (109 mg, 0.1224 mmol) in dichloromethane (0.5 mL) and toluene (0.2 mL) was added trifluoroacetic acid (100 μL, 1.298 mmol) and the mixture stirred at ambient temperature for 23 h. The solvents were removed in vacuo with the bath temperature set at 40° C. The residue was diluted with toluene (5 mL) and the solvent removed in vacuo with the bath temperature set at 40° C. The residue was treated with dichloromethane/hexanes and the solvents evaporated to give N-[[3-benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (ditrifluoroacetate salt) (130 mg, quantitative yield) as an off-white solid. ESI-MS m/z calc. 789.2687, found 790.5 (M+1)⁺; Retention time: 1.85 min (LC Method B).

Step 3: (14S)-22-(Benzyloxy)-12,12-dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione

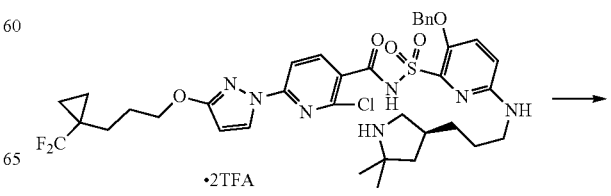

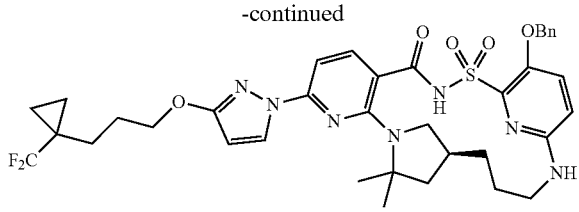

To a solution of N-[[3-benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (ditrifluoroacetate salt) (130 mg, 0.1277 mmol) in NMP (3 mL) was added potassium carbonate (230 mg, 1.664 mmol). The mixture was purged with nitrogen for 5 min. The mixture was heated at 150° C. for 22 h. The reaction mixture was cooled to room temperature and added to water (10 mL). The mixture was carefully acidified with aqueous hydrochloric acid (500 µL of 6 M, 3.000 mmol) until pH=1, affording a foamy slurry. The solid was collected by filtration on paper. The wet solid was dissolved in ethyl acetate and the solution was dried over sodium sulfate and filtered. The solvents were evaporated and the residue was purified by flash chromatography on silica gel using a gradient of methanol (0% to 5% over 30 min) in dichloromethane giving (14S)-22-(benzyloxy)-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (38 mg, 39%) as a white solid. ESI-MS m/z calc. 753.29205, found 754.5 (M+1)$^+$; Retention time: 2.38 min (LC Method B).

Step 4: (14S)-22-Hydroxy-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 261)

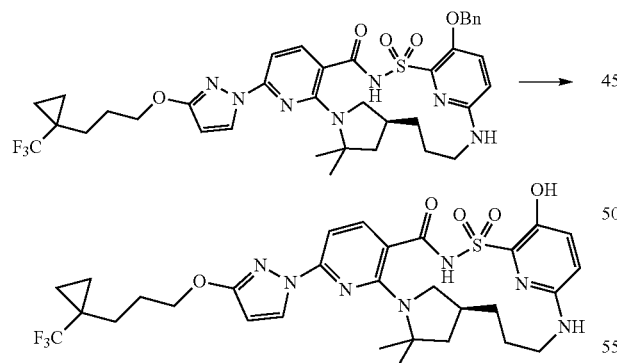

A 100 mL flask was charged with (14S)-22-(benzyloxy)-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (39 mg, 0.05174 mmol) and methanol (8 mL). The solution was sparged with nitrogen. 10% Palladium on carbon (wet, Degussa, 27 mg, 0.02537 mmol) was added and the mixture was stirred under an atmosphere of hydrogen (balloon) for 4 h. The solution was sparged with nitrogen, diluted with methanol and filtered through celite. After evaporation of the solvents, the residue was dissolved in dimethyl sulfoxide (1 mL). The solution was microfiltered and purified by reverse phase preparative HPLC (C$_{18}$) using a gradient of acetonitrile in water (30% to 99% over 15 min, 9504 injection, no modifier). The pure fractions were collected and the solvents removed under evaporation. The residue was treated with dichloromethane/hexanes and the solvents were evaporated to give (14S)-22-hydroxy-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 261) (22 mg, 63%) as an off-white solid. $^1$H NMR (400 MHz, dimethyl sulfoxide-d$_6$) δ 12.38 (broad s, 1H), 9.07 (br s, 1H), 8.21 (d, J=2.7 Hz, 1H), 7.79 (br s, 1H), 7.20 (br s, 1H), 6.90 (br s, 1H), 6.68 (br s, 1H), 6.28 (br s, 1H), 6.10 (br s, 1H), 4.20 (t, J=6.2 Hz, 2H), 3.76 (br s, 1H), 3.21 (br s, 1H), 2.98-2.75 (m, 2H), 2.12 (br s, 1H), 1.93-1.77 (m, 3H), 1.78-1.66 (m, 3H), 1.68-1.46 (m, 8H), 1.37 (br m, 2H), 0.95-0.88 (m, 2H), 0.79-0.68 (m, 2H). ESI-MS m/z calc. 663.24506, found 664.3 (M+1)$^+$; Retention time: 2.24 min (LC Method B).

Example 87: Preparation of 2-imino-12,12-dimethyl-8-(3-{2-[1-(trifluoromethyl)cyclo propyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5,7,9,19,21-hexaene-2,4-dione (Diastereomer Pair 1) (Compound 262) and 2-imino-12,12-dimethyl-8-(3-{2-[1-(trifluoromethyl)cyclo propyl]ethoxy}-1H-pyrazol-1-yl)-2λ$^6$-thia-3,9,11,18,23-pentaazatetracyclo[17.3.1.1$^{11,14}$.0$^{5,10}$]tetracosa-1(23),5,7,9,19,21-hexaene-2,4-dione (Diastereomer Pair 2) (Compound 263)

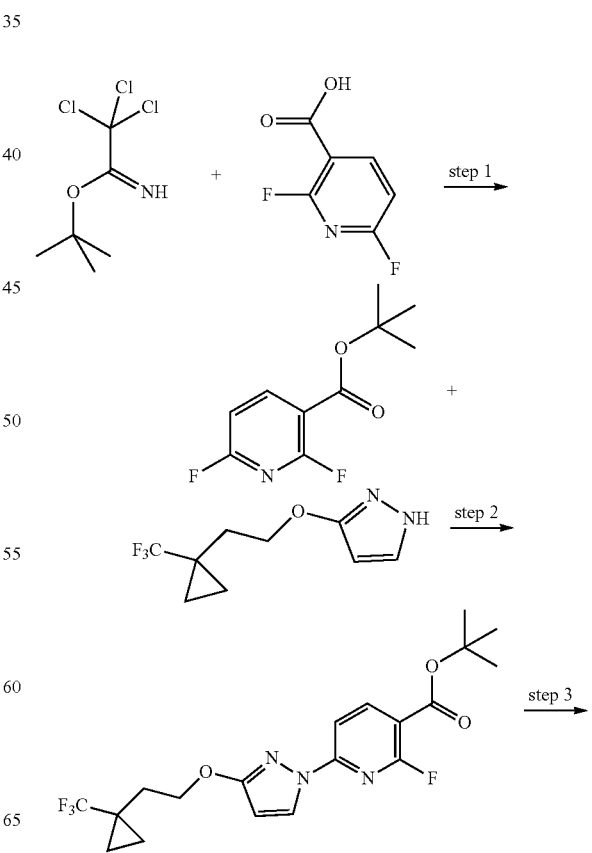

673
-continued
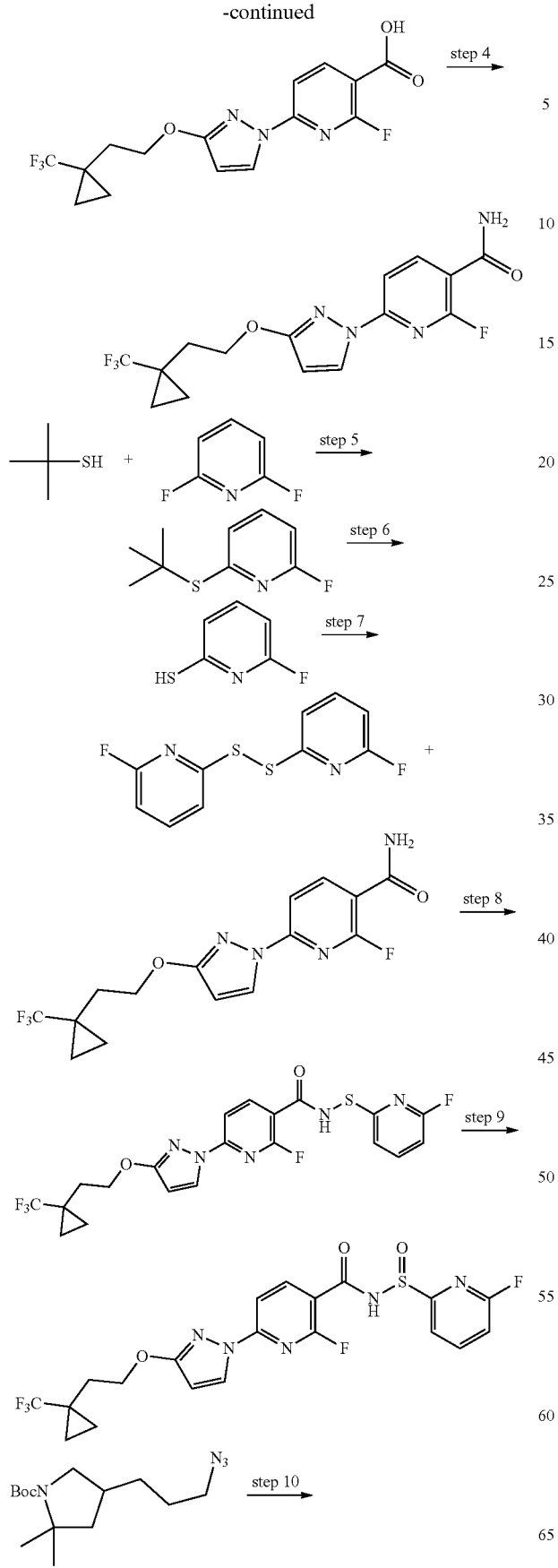
674
-continued
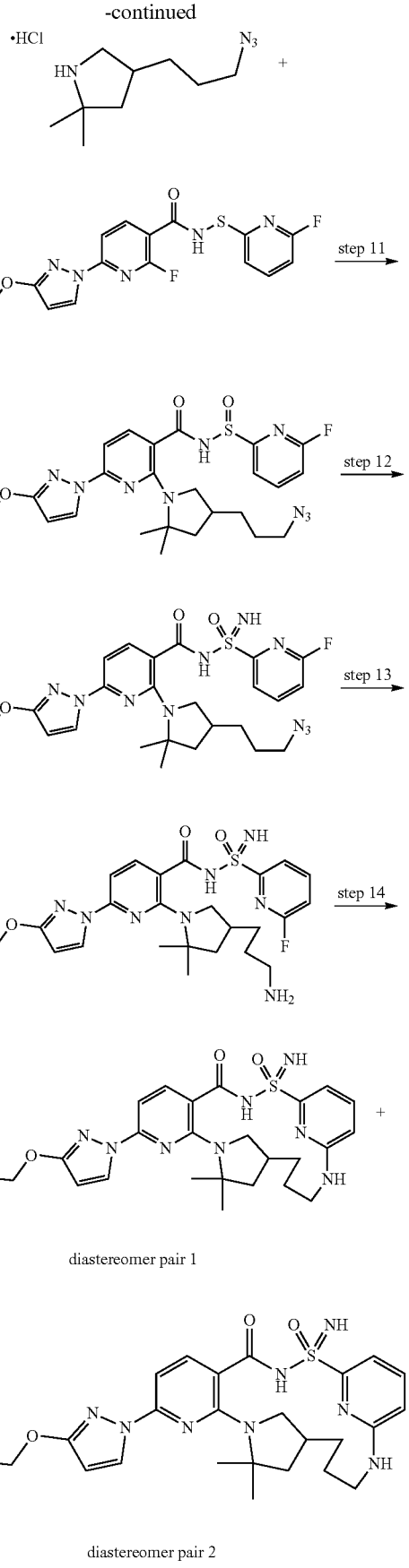
diastereomer pair 1
diastereomer pair 2

Step 1: tert-Butyl 2,6-difluoropyridine-3-carboxylate

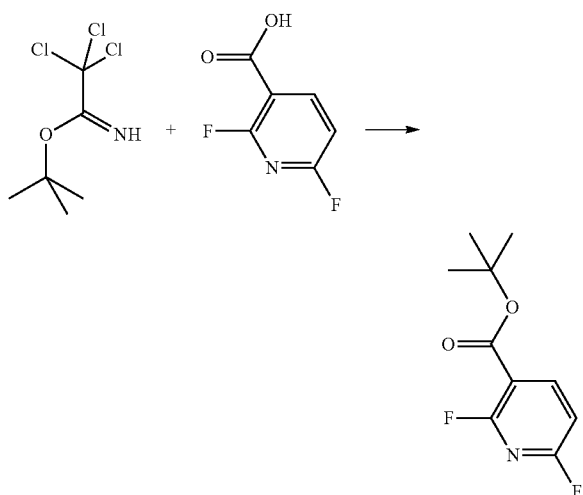

To a solution of 2,6-difluoropyridine-3-carboxylic acid (10 g, 62.858 mmol) and BF$_3$·Et$_2$O (0.4 mL, 3.2 mmol, 0.05 eq.) in dry tetrahydrofuran (60 mL) at 0° C. was slowly added tert-butyl 2,2,2-trichloroethanimidate (10 g, 45.8 mmol) over 10 min. The reaction solution was stirred at room temperature for 2 h under nitrogen atmosphere. More tert-butyl 2,2,2-trichloroethanimidate (20 g, 91.5 mmol) and BF$_3$·Et$_2$O (0.4 mL) were added at room temperature. The reaction was stirred for 1 h. It was then allowed to stand over the weekend before being quenched with saturated aqueous sodium bicarbonate. The mixture was extracted with ethyl acetate (2×60 mL). The combined organic layers were washed with brine, dried over anhydrous sodium sulfate, filtered and concentrated under reduced pressure. The residue was purified by silica gel chromatography using a gradient from 0%-20% ethyl acetate in heptanes to obtain tert-butyl 2,6-difluoropyridine-3-carboxylate (12 g, 89%) as a white solid. ESI-MS m/z calc. 215.0758, found 216.1 (M+1)$^+$; Retention time: 2.13 min (LC Method I).

Step 2: tert-Butyl 2-fluoro-6-[3-[2-[1-(trifluoromethyl)cyclopropyl]ethoxy]pyrazol-1-yl]pyridine-3-carboxylate

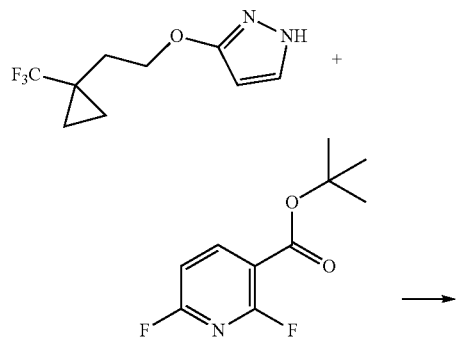

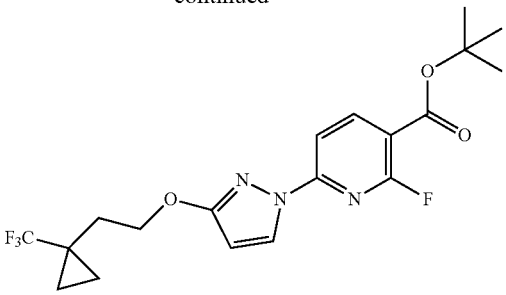

1,4-Diazabicyclo[2.2.2]octane (125 mg, 1.1144 mmol) was added to a solution of tert-butyl 2,6-difluoropyridine-3-carboxylate (1.2 g, 5.5763 mmol) and 3-[2-[1-(trifluoromethyl)cyclopropyl]ethoxy]-1H-pyrazole (1.29 g, 5.8585 mmol). The mixture was stirred for 10 min and potassium carbonate (1.2 g, 8.6827 mmol) was added. The mixture was stirred at 20° C. under nitrogen for 16 h. The reaction mixture was diluted with ethyl acetate (100 mL), washed with water (3×30 mL), brine (30 mL), dried over sodium sulfate, filtered and evaporated. The residue was purified by silica chromatography, eluting with a gradient of ethyl acetate in heptanes (0%-15%) to give tert-butyl 2-fluoro-6-[3-[2-[1-(trifluoromethyl)cyclopropyl]ethoxy]pyrazol-1-yl]pyridine-3-carboxylate (1.46 g, 63% yield) as a white solid. $^1$H NMR (300 MHz, CDCl$_3$) δ 0.71-0.78 (m, 2H), 1.01-1.05 (m, 2H), 1.60 (s, 9H), 2.10 (t, J=7.1 Hz, 2H), 4.41 (t, J=7.1 Hz, 2H), 5.95 (d, J=2.9 Hz, 1H), 7.63 (dd, J=8.2, 1.2 Hz, 1H), 8.29 (d, J=2.8 Hz, 1H), 8.32-8.38 (m, 1H). $^{19}$F NMR (282 MHz, CDCl$_3$) δ −69.9 (s, 3F), − 62.4 (d, J=9.2 Hz, 1F). ESI-MS m/z calc. 415.1519, found 416.2 (M+1)$^+$; Retention time: 2.69 min (LC Method U).

Step 3: 2-Fluoro-6-[3-[2-[1-(trifluoromethyl)cyclopropyl]ethoxy]pyrazol-1-yl]pyridine-3-carboxylic Acid

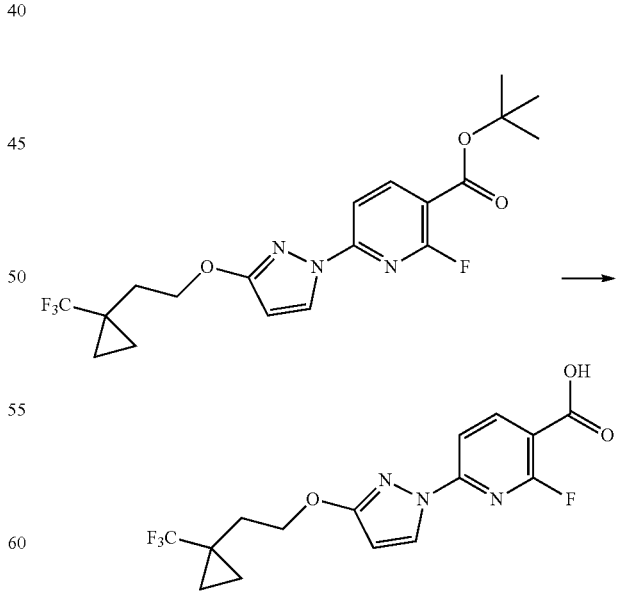

Trifluoroacetic acid (3 mL) was added to a solution of tert-butyl 2-fluoro-6-[3-[2-[1-(trifluoromethyl)cyclopropyl]ethoxy]pyrazol-1-yl]pyridine-3-carboxylate (1.46 g, 3.5148 mmol) in dichloromethane (12 mL). The mixture was stirred at 40° C. for 4 h. The mixture was then concentrated under reduced pressure and dried under vacuum to provide 2-fluoro-6-[3-[2-[1-(trifluoromethyl)cyclopropyl]ethoxy]pyrazol-1-yl]pyridine-3-carboxylic acid (1.26 g, 100%) as a white solid. ¹H NMR (300 MHz, CDCl₃) δ 0.84-0.091 (m, 2H), 0.93-0.99 (m, 2H), 2.09 (t, J=7.0 Hz, 2H), 4.35 (t, J=7.0 Hz, 2H), 6.21 (d, J=2.7 Hz, 1H), 7.67 (d, J=9.3 Hz, 1H), 8.42 (d, J=3.1 Hz, 1H), 8.50 (dd, J=9.3, 8.5 Hz, 1H), 13.48 (br. s., 1H). ¹⁹F NMR (282 MHz, CDCl₃) δ −68.38 (s, 3F), −63.25 (d, J=9.5 Hz, 1F). ESI-MS m/z calc. 359.0893, found 360.1 (M+1)⁺; Retention time: 2.19 min (LC Method I).

Step 4: 2-Fluoro-6-[3-[2-[1-(trifluoromethyl)cyclopropyl]ethoxy]pyrazol-1-yl]pyridine-3-carboxamide

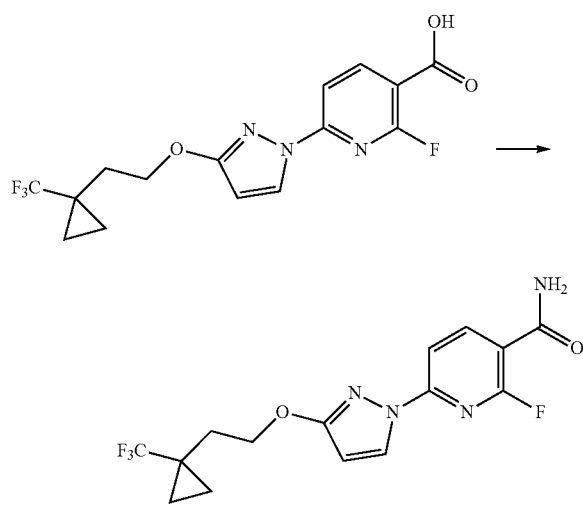

To a suspension of 2-fluoro-6-[3-[2-[1-(trifluoromethyl)cyclopropyl]ethoxy]pyrazol-1-yl]pyridine-3-carboxylic acid (1.26 g, 3.5071 mmol) in dichloromethane (20 mL) was added one drop of N,N-dimethylformamide (0.015 mL) followed by the dropwise addition of oxalyl chloride (625.65 mg, 0.43 mL, 4.9293 mmol). The reaction was stirred at room temperature for 2 h until bubbling had stopped. The solvent was removed under reduced pressure. The resulting white solid was dissolved in anhydrous tetrahydrofuran (10 mL) and added to a mixture of 28% aqueous ammonium hydroxide (10 mL) and tetrahydrofuran (5 mL) that was cooled with an ice-water bath. The reaction was then stirred at room temperature for 1 h and then diluted with ethyl acetate (100 mL), washed with water (20 mL), dried over anhydrous sodium sulfate, filtered and concentrated under reduced pressure to afford 2-fluoro-6-[3-[2-[1-(trifluoromethyl)cyclopropyl]ethoxy]pyrazol-1-yl]pyridine-3-carboxamide (1.3 g, quantitative yield) as a white solid. ¹H NMR (300 MHz, CDCl₃) δ 0.70-0.79 (m, 2H), 0.99-1.08 (m, 2H), 2.10 (t, J=7.2 Hz, 2H), 4.42 (t, J=7.1 Hz, 2H), 5.80 (br.s, 1H), 5.97 (d, J=2.9 Hz, 1H), 6.61-6.71 (m, 1H), 7.74 (dd, J=8.3, 2.0 Hz, 1H), 8.28 (d, J=2.8 Hz, 1H), 8.62 (dd, J=9.8, 8.3 Hz, 1H). ¹⁹F NMR (282 MHz, CDCl₃) δ −69.86 (s, 3F), −65.44 (t, J=8.8 Hz, 1F). ESI-MS m/z calc. 358.1053, found 359.1 (M+1)⁺; Retention time: 2.08 min (LC Method I).

Step 5: 2-tert-Butylsulfanyl-6-fluoro-pyridine

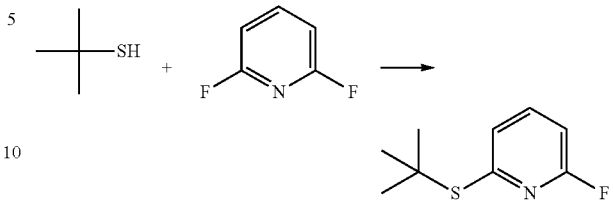

2-Methylpropane-2-thiol (9.0400 g, 11.3 mL, 100.24 mmol) was added to a suspension of sodium hydride (4.8 g, 120 mmol, 60% in oil, washed with 20 mL anhydrous ether) in anhydrous tetrahydrofuran (200 mL) at 0° C. The gray suspension was stirred at room temperature for 30 min then 2,6-difluoropyridine (10 mL, 110.3 mmol) was added. The mixture was stirred at room temperature overnight. The mixture was then cooled with an ice-water bath and then quenched with water. The resulting mixture was diluted with ethyl acetate (60 mL), washed with water (20 mL), brine (20 mL), dried over anhydrous sodium sulfate, filtered and concentrated under reduced pressure to give 2-tert-butylsulfanyl-6-fluoro-pyridine (22 g, 96% yield, 81% purity) as a pale yellow oil which was taken directly to the ensuing step. ¹H NMR (300 MHz, CDCl₃) δ 1.55 (s, 9H), 6.64 (ddd, J=8.1, 2.9, 0.5 Hz, 1H), 7.12 (dd, J=7.6, 2.2, 0.5 Hz, 1H), 7.57 (q, J=8.0 Hz, 1H). ESI-MS m/z calc. 185.0674, found 186.1 (M+1)⁺; Retention time: 2.21 min (LC Method I).

Step 6: 6-Fluoropyridine-2-thiol

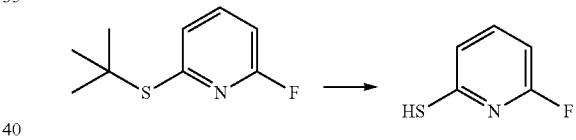

At room temperature (about 20° C.), 100 mL (100 mmol) of a 1 M boron tribromide solution in dichloromethane was added dropwise to a solution of 2-tert-butylsulfanyl-6-fluoro-pyridine (22 g, 81% purity, 96.188 mmol) in 150 mL of dichloromethane. The reaction mixture was stirred at room temperature for 2.5 h. Further boron tribromide (50.00 mL of 1 M in dichloromethane, 50 mmol) was added. After 10 min, the reaction was diluted with 100 mL of dichloromethane, washed with water (2×100 mL), shaken vigorously until two clear phases were obtained, dried over magnesium sulfate, filtered and concentrated under reduced pressure to give crude 6-fluoropyridine-2-thiol (28 g, 100% yield, 45% purity) as a yellow oil. ¹H NMR (300 MHz, CDCl₃) δ 6.65 (dd, J=8.1, 2.5 Hz, 1H), 7.07 (dd, J=7.6, 2.2 Hz, 1H), 7.60 (q, J=7.9 Hz, 1H). ¹⁹F NMR (282 MHz, CDCl₃) δ− 66.78 (s, 1F).

Step 7: 2-Fluoro-6-[(6-fluoro-2-pyridyl)disulfanyl]pyridine

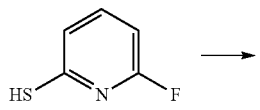

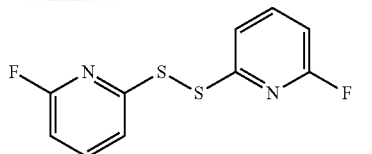

Bromine (17.063 g, 5.5 mL, 106.77 mmol) was slowly added to a solution of 6-fluoropyridine-2-thiol (28 g, 45% purity, 97.557 mmol) in ethyl ether (160 mL) at room temperature until an orange color remained. The addition was stopped and the reaction mixture was diluted with ethyl acetate (100 mL), washed with a 1:1 mixture of saturated sodium bicarbonate and 10% sodium thiosulfate solution, brine, and concentrated under reduced pressure. The residue was purified by silica gel chromatography eluting with a gradient of ethyl acetate in heptanes (0%-20%) to afford 2-fluoro-6-[(6-fluoro-2-pyridyl)disulfanyl]pyridine (10.5 g, 84%) as a brown solid. $^1$H NMR (300 MHz, CDCl$_3$) δ 6.75 (dd, J=8.0, 2.6 Hz, 1H), 7.49 (dd, J=7.7, 2.1 Hz, 1H), 7.72 (q, J=7.7 Hz, 1H). $^{19}$F NMR (282 MHz, CDCl$_3$) δ– 66.37 (d, J=6.8 Hz, 1F). ESI-MS m/z calc. 255.994, found 257.1 (M+1)$^+$; Retention time: 2.12 min (LC Method I).

Step 8: 2-Fluoro-N-[(6-fluoro-2-pyridyl)sulfanyl]-6-[3-[2-[1-(trifluoromethyl)cyclopropyl]ethoxy]pyrazol-1-yl]pyridine-3-carboxamide

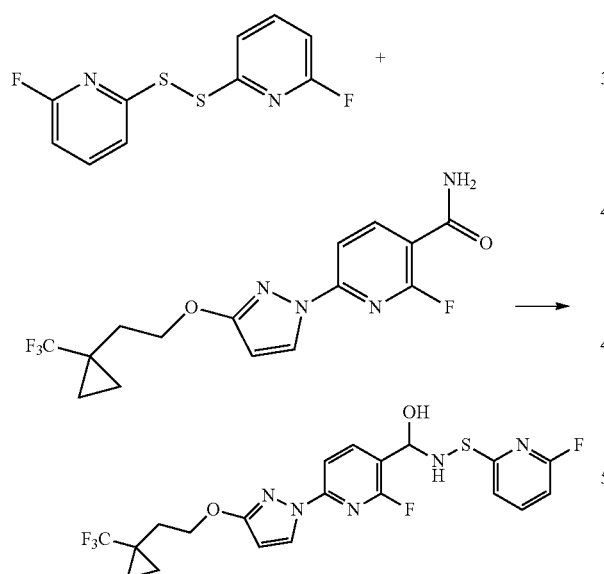

Bromine (310.25 mg, 0.1000 mL, 1.9414 mmol) was slowly added to a solution of 2-fluoro-6-[(6-fluoro-2-pyridyl)disulfanyl]pyridine (520 mg, 2.0289 mmol) in anhydrous acetonitrile (4 mL) at 0° C. After being stirred for 2 min at the same temperature, the red solution was added to a solution of 2-fluoro-6-[3-[2-[1-(trifluoromethyl)cyclopropyl]ethoxy]pyrazol-1-yl]pyridine-3-carboxamide (720 mg, 2.0095 mmol) in anhydrous acetonitrile (4 mL) and pyridine (6 mL) at 0° C. The resulting dark mixture was stirred at room temperature overnight. The mixture was concentrated under reduced pressure. The residue was co-evaporated with toluene and purified by silica gel chromatography, using a gradient from 0%-30% ethyl acetate in heptanes to afford 2-fluoro-N-[(6-fluoro-2-pyridyl)sulfanyl]-6-[3-[2-[1-(trifluoromethyl)cyclopropyl]ethoxy]pyrazol-1-yl]pyridine-3-carboxamide (700 mg, 72%) as a white solid. ESI-MS m/z calc. 485.0945, found 486.1 (M+1)$^+$; Retention time: 2.36 min (LC Method I).

Step 9: 2-Fluoro-N-[(6-fluoro-2-pyridyl)sulfinyl]-6-[3-[2-[1-(trifluoromethyl) cyclopropyl]ethoxy]pyrazol-1-yl]pyridine-3-carboxamide

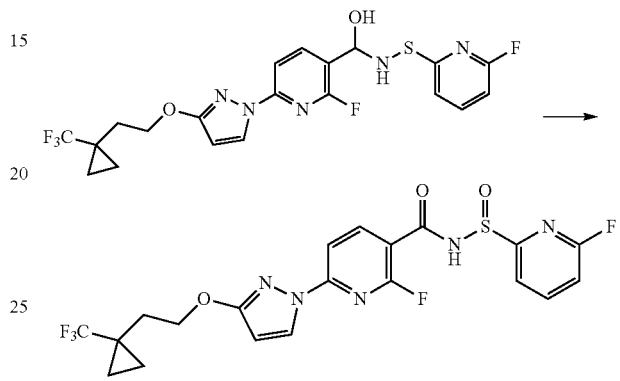

meta-Chloroperoxybenzoic acid (355 mg, 77% purity, 1.58 mmol) was added to a solution of 2-fluoro-N-[(6-fluoro-2-pyridyl)sulfanyl]-6-[3-[2-[1-(trifluoromethyl) cyclopropyl]ethoxy]pyrazol-1-yl]pyridine-3-carboxamide (700 mg, 1.4420 mmol) in dichloromethane (20 mL) at 0° C. and the reaction was stirred at the same temperature for 1 h. The reaction mixture was diluted with dichloromethane (70 mL), washed successively with 10% w/v aqueous sodium thiosulfate, 5% w/v aqueous sodium bicarbonate, dried over anhydrous sodium sulfate, filtered and concentrated under reduced pressure. The residue was purified by silica gel chromatography, eluting with a gradient from 0%-40% ethyl acetate in heptanes to afford racemic 2-fluoro-N-[(6-fluoro-2-pyridyl)sulfinyl]-6-[3-[2-[1-(trifluoromethyl)cyclopropyl] ethoxy]pyrazol-1-yl]pyridine-3-carboxamide (700 mg, 97%) as white solid. ESI-MS m/z calc. 501.0894, found 502.1 (M+1)$^+$; Retention time: 2.25 min (LC Method I).

Step 10: 4-(3-Azidopropyl)-2,2-dimethyl-pyrrolidine (Hydrochloride Salt)

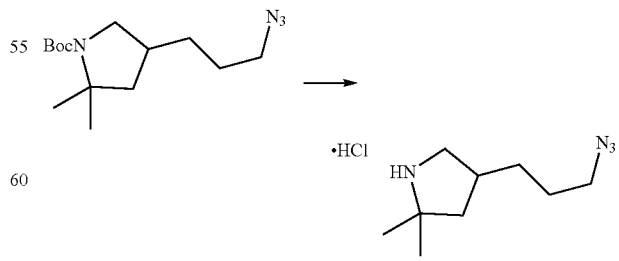

Hydrochloric acid (2 mL of 4 M in 1,4-dioxane, 8.0 mmol) was added to a solution of tert-butyl 4-(3-azidopropyl)-2,2-dimethyl-pyrrolidine-1-carboxylate (1.2 g, 4.2496 mmol) in dichloromethane (10 mL) cooled with an ice-water bath. The mixture was allowed to stir at room temperature overnight. The mixture was concentrated under reduced pressure. The residue was co-evaporated with toluene (40 mL) two times to afford crude 4-(3-azidopropyl)-2,2-dimethyl-pyrrolidine (hydrochloride salt) (930 mg, 100%) as a light yellow oil. $^1$H NMR (300 MHz, CDCl$_3$) δ 1.29 (s, 3H), 1.38-1.54 (m, 8H), 1.99 (dd, J=12.7, 7.7 Hz, 1H), 2.31-2.42 (m, 1H), 2.76-2.89 (m, 1H), 3.32-3.36 (m, 3H), 9.00 (br.s., 1H), 9.11 (br.s., 1H). ESI-MS m/z calc. 182.1531, found 183.2 (M+1)$^+$; Retention time: 0.94 min (LC Method I).

Step 11: 2-[4-(3-Azidopropyl)-2,2-dimethyl-pyrrolidin-1-yl]-N-[(6-fluoro-2-pyridyl)sulfinyl]-6-[3-[2-[1-(trifluoromethyl)cyclopropyl]ethoxy]pyrazol-1-yl]pyridine-3-carboxamide

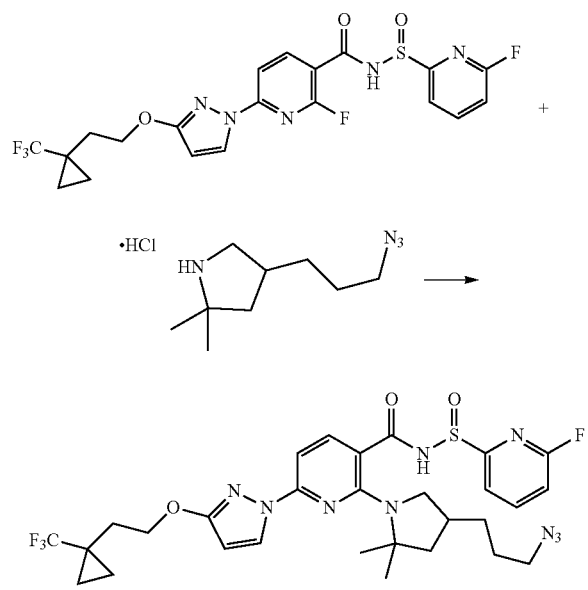

Sodium hydride (193 mg, 60% w/w dispersion in mineral oil, 2.6 mmol) was added to a solution of 4-(3-azidopropyl)-2,2-dimethyl-pyrrolidine (hydrochloride salt) (528 mg, 2.4 mmol) in anhydrous N,N-dimethylformamide (10 mL) cooled with an ice-water bath. The mixture was stirred for 5 min and 2-fluoro-N-[(6-fluoro-2-pyridyl)sulfinyl]-6-[3-[2-[1-(trifluoromethyl)cyclopropyl]ethoxy]pyrazol-1-yl]pyridine-3-carboxamide (930 mg, 1.85 mmol) was added. The mixture was stirred at room temperature for 30 min and then placed in an oil bath (50° C.) and stirred for 4 h. After that, the mixture was allowed to cool down and stand overnight. The mixture was diluted with ethyl acetate (100 mL). The resulting mixture was washed with water (3×30 mL), brine (30 mL), dried over anhydrous sodium sulfate, filtered and concentrated under reduced pressure. The residue was purified by silica gel chromatography using a gradient from 0%-70% ethyl acetate in heptanes to obtain 2-[4-(3-azidopropyl)-2,2-dimethyl-pyrrolidin-1-yl]-N-[(6-fluoro-2-pyridyl)sulfinyl]-6-[3-[2-[1-(trifluoromethyl)cyclopropyl]ethoxy]pyrazol-1-yl]pyridine-3-carboxamide (600 mg, 49%) as a white solid. ESI-MS m/z calc. 663.2363, found 664.3 (M+1)$^+$; Retention time: 2.61 min (LC Method I).

Step 12: 2-[4-(3-Azidopropyl)-2,2-dimethyl-pyrrolidin-1-yl]-N-[(6-fluoro-2-pyridyl)sulfonimidoyl]-6-[3-[2-[1-(trifluoromethyl)cyclopropyl]ethoxy]pyrazol-1-yl]pyridine-3-carboxamide

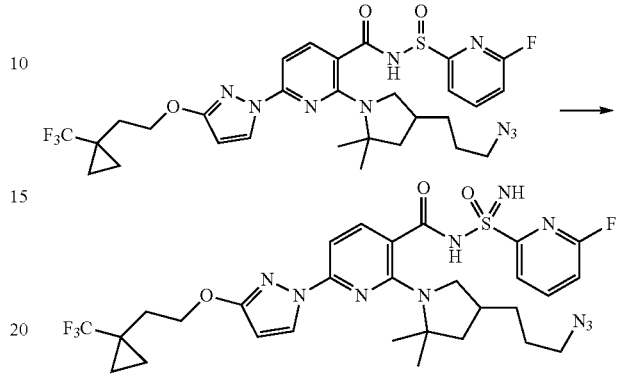

Ammonia (10 mL of a 0.5 M solution in 1,4-dioxane, 5 mmol) was added to a solution of 2-[4-(3-azidopropyl)-2,2-dimethyl-pyrrolidin-1-yl]-N-[(6-fluoro-2-pyridyl)sulfinyl]-6-[3-[2-[1-(trifluoromethyl)cyclopropyl]ethoxy]pyrazol-1-yl]pyridine-3-carboxamide (580 mg, 0.87 mmol) in anhydrous acetonitrile (5 mL) at 0° C. N-Chlorosuccinimide (140 mg, 1.05 mmol) was added in one portion (the mixture turned orange) and the reaction was stirred at 0° C. for 1 h. Additional N-chlorosuccinimide (100 mg, 0.75 mmol) was added and the reaction was stirred at the same temperature for 30 min. The reaction was then quenched with 10% w/v aqueous sodium thiosulfate solution and extracted with ethyl acetate (50 mL). The organic layer was washed with brine (20 mL), dried over anhydrous sodium sulfate, filtered and concentrated under reduced pressure. The residue was purified by silica gel chromatography, eluting with a gradient from 0%-55% ethyl acetate in heptanes to afford 2-[4-(3-azidopropyl)-2,2-dimethyl-pyrrolidin-1-yl]-N-[(6-fluoro-2-pyridyl)sulfonimidoyl]-6-[3-[2-[1-(trifluoromethyl)cyclopropyl]ethoxy]pyrazol-1-yl]pyridine-3-carboxamide (400 mg, 67%) as yellow gummy solid.

Step 13: 2-[4-(3-Aminopropyl)-2,2-dimethyl-pyrrolidin-1-yl]-N-[(6-fluoro-2-pyridyl)sulfonimidoyl]-6-[3-[2-[1-(trifluoromethyl)cyclopropyl]ethoxy]pyrazol-1-yl]pyridine-3-carboxamide

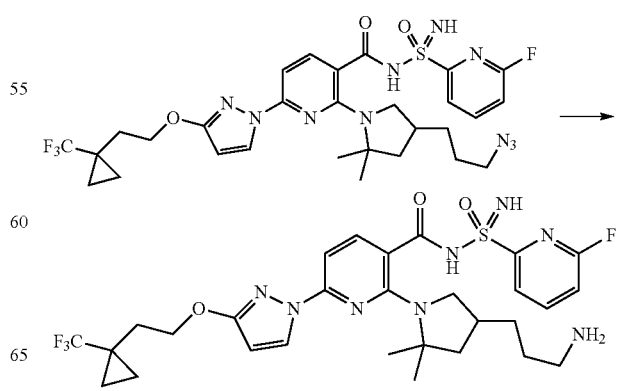

A mixture of 2-[4-(3-azidopropyl)-2,2-dimethyl-pyrrolidin-1-yl]-N-[(6-fluoro-2-pyridyl)sulfonimidoyl]-6-[3-[2-[1-(trifluoromethyl)cyclopropyl]ethoxy]pyrazol-1-yl]pyridine-3-carboxamide (360 mg, 0.5304 mmol), ammonia solution in methanol (7 N, 1 mL) and 10% palladium on carbon (wet, Degussa, 200 mg, 0.094 mmol) in methanol (10 mL) was hydrogenated under 1 atm of H2 (balloon) at room temperature for 3 h. The flask was evacuated and backfilled with nitrogen. The reaction mixture was filtered through a pad of celite. The filtrate was concentrated under reduced pressure to give crude 2-[4-(3-aminopropyl)-2,2-dimethyl-pyrrolidin-1-yl]-N-[(6-fluoro-2-pyridyl)sulfonimidoyl]-6-[3-[2-[1-(trifluoromethyl)cyclopropyl]ethoxy]pyrazol-1-yl]pyridine-3-carboxamide (380 mg, 81% yield, 74% purity) as a yellow solid. The crude product was directly used in the next step without purification. ESI-MS m/z calc. 652.2567, found 653.3 (M+1)+; Retention time: 1.70 min (LC Method I).

Step 14: 2-Imino-12,12-dimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(23),5,7,9,19,21-hexaene-2,4-dione (Diastereomer Pair 1) (Compound 262) and 2-imino-12,12-dimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(23),5,7,9,19,21-hexaene-2,4-dione (Diastereomer Pair 2) (Compound 263)

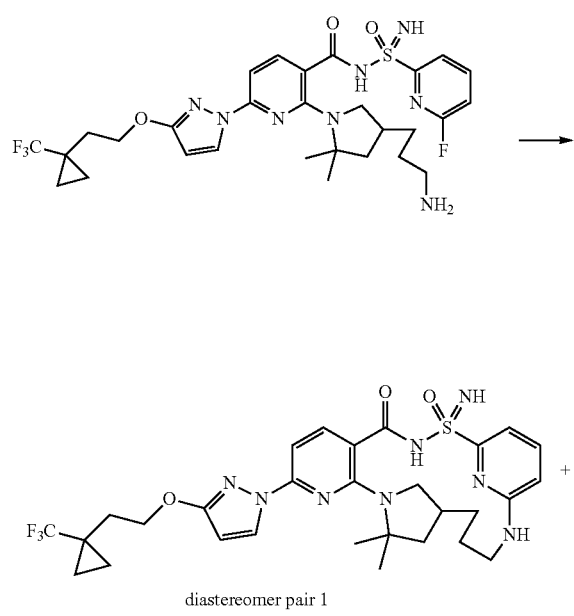

diastereomer pair 1

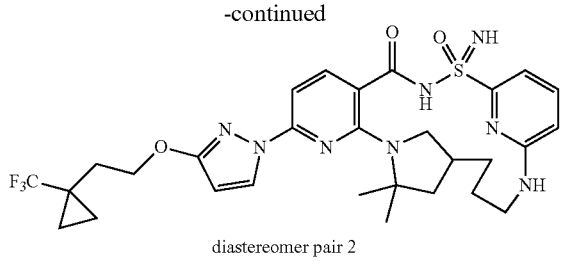

diastereomer pair 2

A mixture of 2-[4-(3-aminopropyl)-2,2-dimethyl-pyrrolidin-1-yl]-N-[(6-fluoro-2-pyridyl)sulfonimidoyl]-6-[3-[2-[1-(trifluoromethyl)cyclopropyl]ethoxy]pyrazol-1-yl]pyridine-3-carboxamide (380 mg, 0.5822 mmol), triethylamine (239.58 mg, 0.33 mL, 2.3676 mmol) and dry dimethyl sulfoxide (25 mL) was stirred in a seal tube at 100° C. for 4 h. The mixture was allowed to cool down to room temperature then diluted with water (100 mL) and extracted with ethyl acetate (3×40 mL). The combined organic layers were washed with water (2×30 mL), brine (30 mL), dried over anhydrous sodium sulfate, filtered and concentrated under reduced pressure. The residue was purified by silica gel chromatography using a gradient from 0%-60% ethyl acetate in heptanes to obtain as the first diastereomeric pair of enantiomers to elute, 2-imino-12,12-dimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(23),5,7,9,19,21-hexaene-2,4-dione (diastereomer pair 1) (Compound 262) (88.76 mg, 23% yield) as a white solid, $^1$H NMR (300 MHz, CDCl$_3$) ppm 0.72-0.80 (m, 2H), 0.96-1.05 (m, 2H), 1.13-1.23 (m, 1H), 1.29-1.44 (m, 1H), 1.59 (s, 3H), 1.67-1.71 (m, 1H), 1.75 (s, 3H), 1.82-1.94 (m, 2H), 2.00-2.31 (m, 4H), 3.09-3.34 (m, 2H), 3.60 (t, J=11.0 Hz, 1H), 3.75-3.94 (m, 1H), 4.39 (t, J=7.0 Hz, 2H), 4.70-4.80 (m, 1H), 5.86 (d, J=2.6 Hz, 1H), 6.47 (d, J=8.5 Hz, 1H), 6.97 (d, J=8.5 Hz, 1H), 7.02 (br. s., 2H), 7.30 (d, J=7.0 Hz, 1H), 7.47 (dd, J=8.2, 7.3 Hz, 1H), 8.17 (d, J=8.2 Hz, 1H), 8.24 (d, J=2.6 Hz, 1H). $^{19}$F NMR (282 MHz, CDCl$_3$) ppm-70.0 (br. s., 3F). ESI-MS m/z calc. 632.2505, found 633.3 (M+1)+; Retention time: 3.98 min (LC Method H) and as the second diastereomeric pair of enantiomers to elute, 2-imino-12,12-dimethyl-8-(3-{2-[1-(trifluoromethyl)cyclopropyl]ethoxy}-1H-pyrazol-1-yl)-2$\lambda^6$-thia-3,9,11,18,23-pentaazatetracyclo[17.3.1.1¹¹,¹⁴.0⁵,¹⁰]tetracosa-1(23),5,7,9,19,21-hexaene-2,4-dione (diastereomer pair 2) (Compound 263) (97.02 mg, 25% yield) as a white solid. $^1$H NMR (300 MHz, CDCl$_3$) δ 0.70-0.78 (m, 2H), 0.97-1.05 (m, 2H), 1.34-1.46 (m, 2H), 1.58-1.63 (m, 7H), 1.64-1.74 (m, 2H), 1.82 (dd, J=11.3, 5.4 Hz, 1H), 2.08-2.12 (m, 3H), 2.96-3.11 (m, 2H), 3.29-3.42 (m, 1H), 4.16-4.25 (m, 1H), 4.32-4.41 (m, 3H), 5.09 (br. s., 2H), 5.84 (d, J=2.6 Hz, 1H), 6.53 (d, J=8.5 Hz, 1H), 6.96 (d, J=8.2 Hz, 1H), 7.35 (d, J=7.0 Hz, 1H), 7.53 (dd, J=8.5, 7.3 Hz, 1H), 8.07 (d, J=8.2 Hz, 1H), 8.20 (d, J=2.6 Hz, 1H). $^{19}$F NMR (282 MHz, CDCl$_3$) δ −70.0 (s, 3F). ESI-MS m/z calc. 632.2505, found 633.3 (M+1)+; Retention time: 3.77 min (LC Method H).

Example 88: Preparation of (14S)-8-[3-(2-{dispiro[2.0.2.1]heptan-7-yl}ethoxy)-1H-pyrazol-1-yl]-21-hydroxy-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 264)
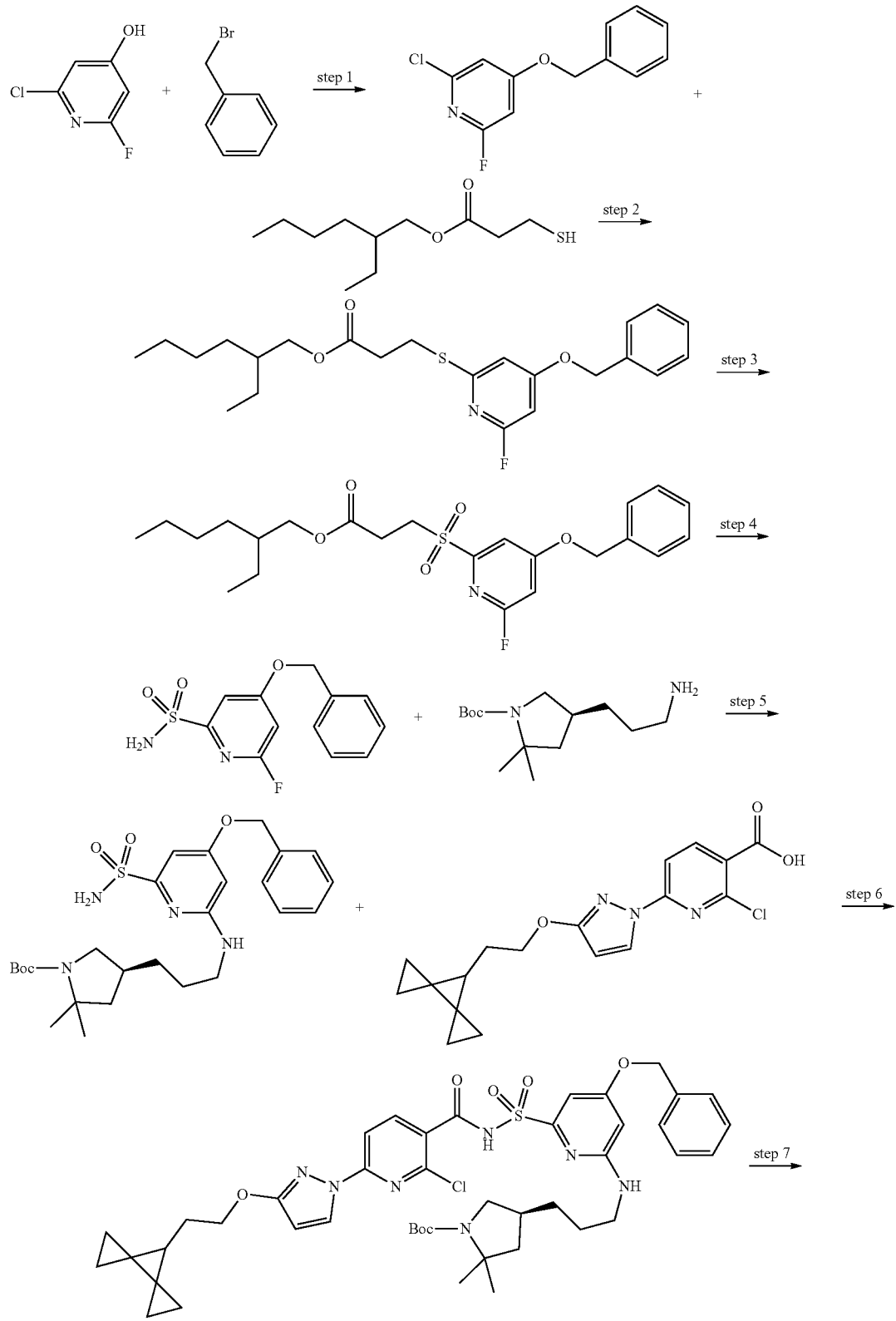

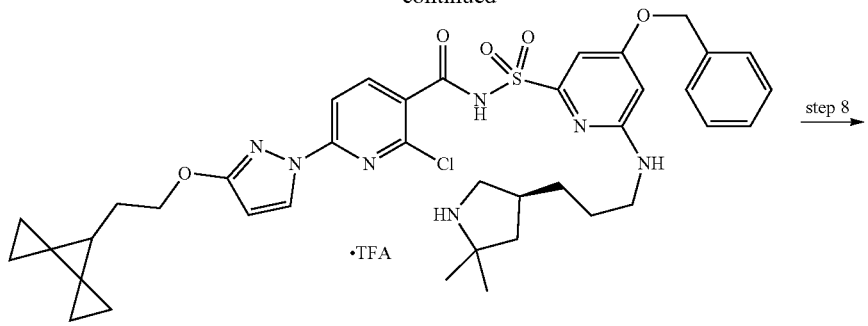

step 8

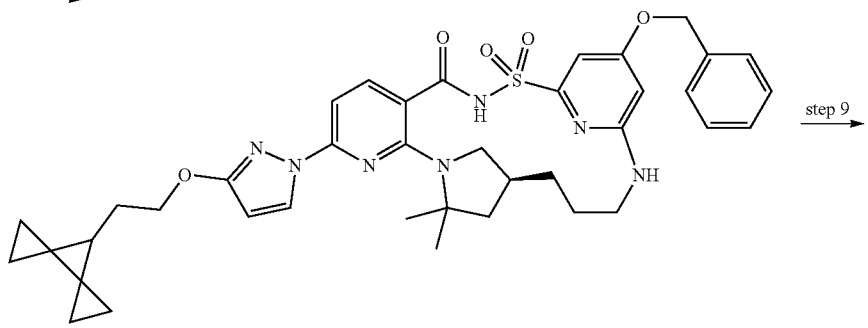

step 9

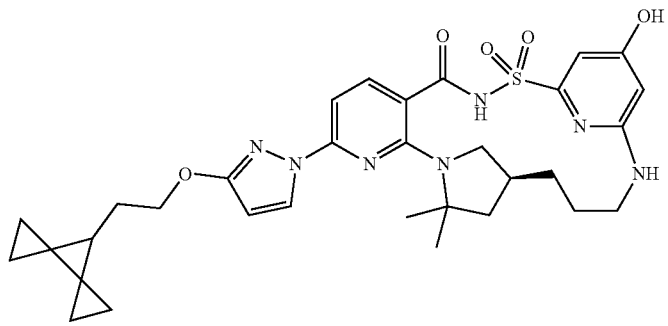

Step 1: 4-Benzyloxy-2-chloro-6-fluoro-pyridine

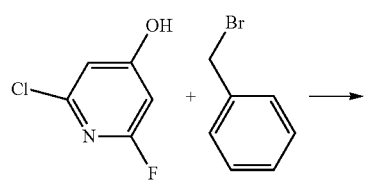

To a solution of 2-chloro-6-fluoro-pyridin-4-ol (4.62 g, 31.315 mmol) in acetonitrile (90 mL) was added cesium carbonate (15.3 g, 46.959 mmol) and benzyl bromide (5.8958 g, 4.1 mL, 34.472 mmol). The reaction was stirred at room temperature overnight. The solution was dissolved in ethyl acetate (350 mL) and water (100 mL). The aqueous phase was removed and the organic phase was washed with water (100 mL) and brine (75 mL). The organic phase was dried over sodium sulfate, filtered and concentrated. The crude was purified by silica gel chromatography eluting with a gradient of 0% to 10% ethyl acetate in heptanes to give 4-benzyloxy-2-chloro-6-fluoro-pyridine (7.01 g, 94%) as a white solid. ESI-MS m/z calc. 237.0357, found 238.1 (M+1)⁺; Retention time: 2.38 min (LC Method N).

Step 2: 2-Ethylhexyl 3-[(4-benzyloxy-6-fluoro-2-pyridyl)sulfanyl]propanoate

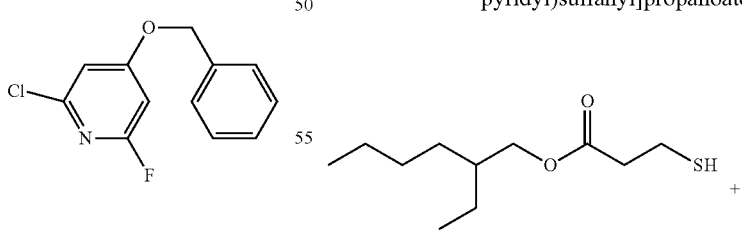

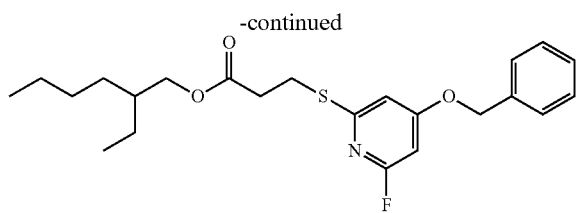

A solution of 4-benzyloxy-2-chloro-6-fluoro-pyridine (6.77 g, 28.486 mmol) and diisopropylethylamine (7.4200 g, 10 mL, 57.411 mmol) in toluene (250 mL) was degassed by bubbling nitrogen for 5 min. Tris(dibenzylideneacetone)dipalladium(0) (783 mg, 0.8551 mmol), Xantphos (990 mg, 1.7110 mmol) and 2-ethylhexyl 3-sulfanylpropanoate (6.5280 g, 6.8 mL, 29.896 mmol) were added and the mixture was heated at 125° C. overnight. The reaction mixture was concentrated under reduced pressure. The residue was purified by silica gel chromatography using a gradient from 0%-10% of ethyl acetate in heptane to afford 2-ethylhexyl 3-[(4-benzyloxy-6-fluoro-2-pyridyl)sulfanyl]propanoate (12.06 g, quantitative yield) as an orange oil. $^1$H NMR (300 MHz, CDCl$_3$) δ 0.80-0.95 (m, 6H), 1.19-1.43 (m, 8H), 1.51-1.63 (m, 1H), 2.77 (t, J=7.0 Hz, 2H), 3.37 (t, J=6.9 Hz, 2H), 4.02 (dd, J=5.9, 1.2 Hz, 2H), 5.07 (s, 2H), 6.18 (d, J=1.8 Hz, 1H), 6.65 (d, J=1.2 Hz, 1H), 7.28-7.49 (m, 5H). $^{19}$F NMR (282 MHz, CDCl$_3$) δ −65.7 (s, 1F). ESI-MS m/z calc. 419.193, found 420.2 (M+1)$^+$; Retention time: 2.8 min (LC Method I).

Step 3: 2-Ethylhexyl 3-[(4-benzyloxy-6-fluoro-2-pyridyl)sulfonyl]propanoate

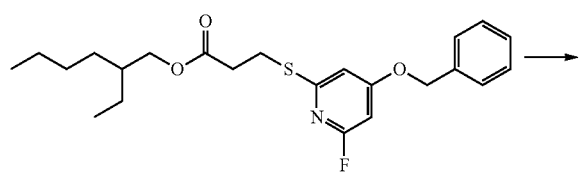

m-Chloroperbenzoic acid (12.9 g, 57.561 mmol) was slowly added at 0° C. to a solution of 2-ethylhexyl 3-[(4-benzyloxy-6-fluoro-2-pyridyl)sulfanyl]propanoate (12.06 g, 28.745 mmol) in dichloromethane (150 mL). The mixture was stirred at this temperature overnight. Ethyl acetate (150 mL) was added and washed with saturated sodium bicarbonate solution (100 mL) and 0.5 M sodium hydroxide solution (2×100 mL). The organic phase was dried over anhydrous sodium sulfate, filtered and concentrated under reduced pressure to afford 2-ethylhexyl 3-[(4-benzyloxy-6-fluoro-2-pyridyl)sulfonyl]propanoate (12.05 g, 93%) as a colorless oil. ESI-MS m/z calc. 451.1829, found 452.2 (M+1)$^+$; Retention time: 2.54 min (LC Method I).

Step 4: 4-Benzyloxy-6-fluoro-pyridine-2-sulfonamide

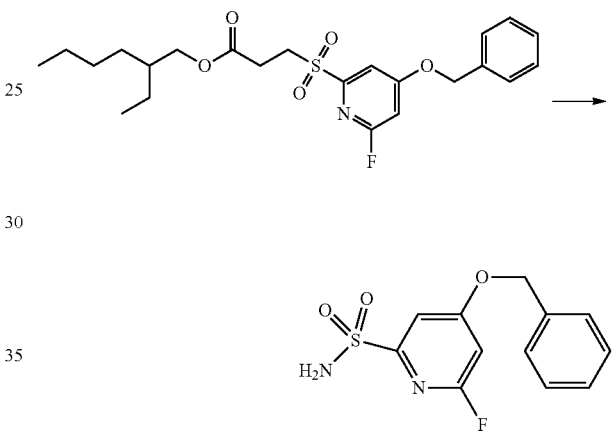

To a solution of 2-ethylhexyl 3-[(4-benzyloxy-6-fluoro-2-pyridyl)sulfonyl]propanoate (10.69 g, 23.674 mmol) in dimethylsulfoxide (60 mL) was added 1,8-diazabicyclo[5.4.0]undec-7-ene (7.0700 g, 7 mL, 46.441 mmol). The reaction was stirred for 1 h at room temperature and a solution of hydroxylamine-O-sulfonic acid (13.3 g, 117.60 mmol) and sodium acetate (7.7 g, 93.864 mmol) in water (40 mL) was added at 10° C. The reaction was stirred for 1 h at room temperature, diluted with water (300 mL) and extracted with ethyl acetate (2×300 mL). The combined organic layers were washed with brine (300 mL), dried over anhydrous sodium sulfate, filtered and concentrated under reduced pressure. The crude material was triturated overnight with a mix of heptane:ethyl acetate 9:1 (100 mL). The product was isolated by filtration. The product was redissolved in ethyl acetate and filtered over a pad of silica gel, eluting with ethyl acetate (500 mL) and concentrated to give 4-benzyloxy-6-fluoro-pyridine-2-sulfonamide (5.56 g, 83%). $^1$H NMR (300 MHz, dimethyl sulfoxide-d$_6$) δ 5.34 (s, 2H), 7.15 (d, J=2.1 Hz, 1H), 7.30-7.54 (m, 6H), 7.62 (s, 2H). $^{19}$F NMR (282 MHz, dimethyl sulfoxide-d$_6$) δ −66.0 (s, 1F). ESI-MS m/z calc. 282.0474, found 283.1 (M+1)$^+$; Retention time: 1.75 min (LC Method I).

Step 5: tert-Butyl (4S)-4-[3-[(4-benzyloxy-6-sulfamoyl-2-pyridyl)amino]propyl]-2,2-dimethyl-pyrrolidine-1-carboxylate

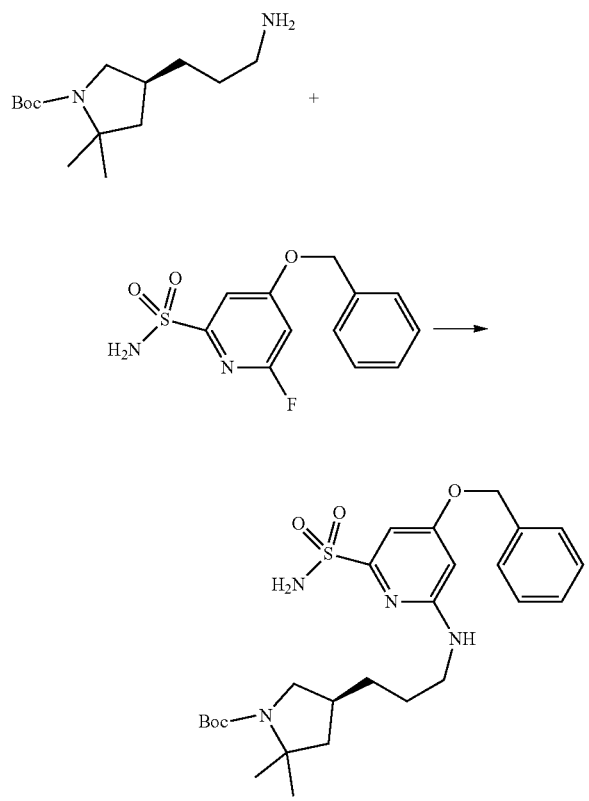

A 20 mL vial was charged under nitrogen with tert-butyl (4S)-4-(3-aminopropyl)-2,2-dimethyl-pyrrolidine-1-carboxylate (312 mg, 1.217 mmol), 4-benzyloxy-6-fluoro-pyridine-2-sulfonamide (344 mg, 1.219 mmol), anhydrous dimethyl sulfoxide (3.5 mL) and diisopropylethylamine (0.32 mL, 1.837 mmol). The vial was capped and stirred at 85° C. for 16 h. The mixture was diluted with ethyl acetate (50 mL), water (50 mL) and 10% citric acid (10 mL). The two phases were separated. The organic phase was washed with brine (30 mL) dried over sodium sulfate, filtered and the solvents were evaporated. The product was purified by chromatography on silica gel using a gradient of ethyl acetate (0% to 70% over 30 min) in hexanes giving tert-butyl (4S)-4-[3-[(4-benzyloxy-6-sulfamoyl-2-pyridyl)amino]propyl]-2,2-dimethyl-pyrrolidine-1-carboxylate (427 mg, 68%) as a white foamy solid. $^1$H NMR (400 MHz, dimethyl sulfoxide-$d_6$) δ 7.47-7.29 (m, 5H), 7.07 (s, 2H), 6.83 (t, J=5.4 Hz, 1H), 6.66 (d, J=2.0 Hz, 1H), 6.15 (d, J=1.8 Hz, 1H), 5.14 (s, 2H), 3.55 (q, J=9.5 Hz, 1H), 3.25 (broad q, J=6.4 Hz, 2H), 2.78 (q, J=9.9 Hz, 1H), 2.10 (br s, 1H), 1.94-1.81 (m, 1H), 1.57-1.43 (m, 2H), 1.45-1.29 (m, 15H), 1.24 (s, 3H). ESI-MS m/z calc. 518.2563, found 519.4 (M+1)$^+$; Retention time: 1.92 min (LC Method B).

Step 6: tert-Butyl (4S)-4-[3-[[4-benzyloxy-6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate

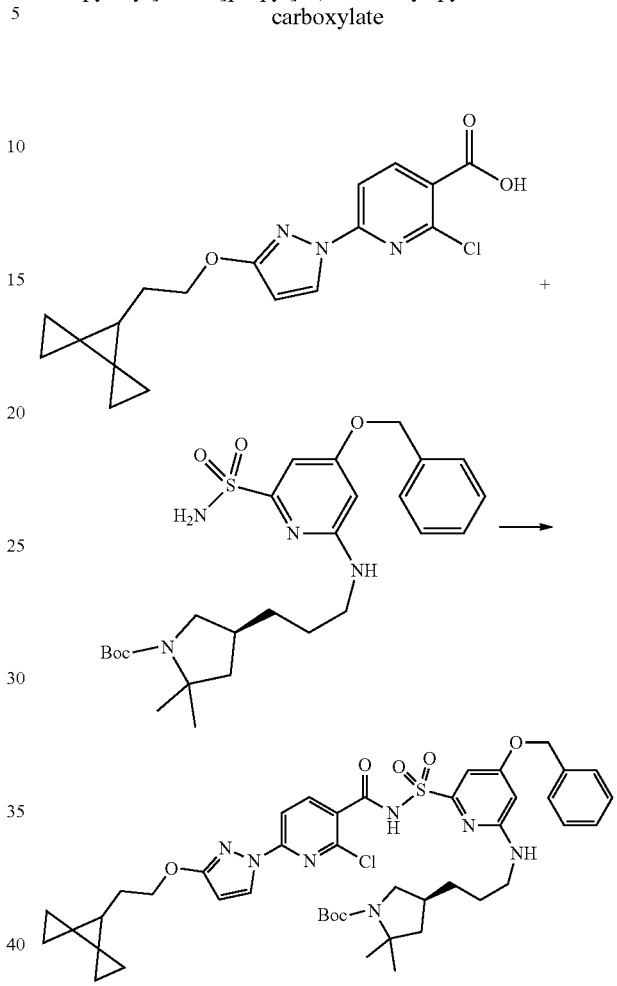

To a stirred solution of 2-chloro-6-[3-(2-dispiro[2.0.2.1] heptan-7-ylethoxy)pyrazol-1-yl]pyridine-3-carboxylic acid (130 mg, 0.3613 mmol) in anhydrous tetrahydrofuran (2 mL) was added carbonyl diimidazole (60 mg, 0.3700 mmol) and the stirring continued at ambient temperature under nitrogen for 2 h. To the reaction, a solution of tert-butyl (4S)-4-[3-[(4-benzyloxy-6-sulfamoyl-2-pyridyl)amino]propyl]-2,2-dimethyl-pyrrolidine-1-carboxylate (160 mg, 0.3085 mmol) in anhydrous tetrahydrofuran (1 mL) was added, followed 1,8-diazabicyclo[5.4.0]undec-7-ene (200 µL, 1.337 mmol) and the mixture was stirred at ambient temperature for 15 h. The volatiles were removed under reduced pressure and the residue was diluted with ethyl acetate (20 mL) and water (20 mL) and the mixture was acidified slowly with 4 M aqueous hydrochloric acid (350 µL of 4 M, 1.400 mmol) to about pH=4.0. The layers were separated and the aqueous layer was extracted with ethyl acetate (15 mL). The combined organic phases were washed with brine (20 mL), dried over anhydrous sodium sulfate, filtered and concentrated under reduced pressure. The crude material was purified via silica gel chromatography (gradient from 0%-70% ethyl acetate in hexanes over 35 min) to furnish tert-butyl (4S)-4-[3-[[4-benzyloxy-6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (72 mg, 27%) as a white solid. ESI-MS m/z calc. 859.34937, found 860.6 (M+1)+; Retention time: 2.41 min (LC Method G).

Step 7: N-[[4-Benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (Trifluoroacetate Salt)

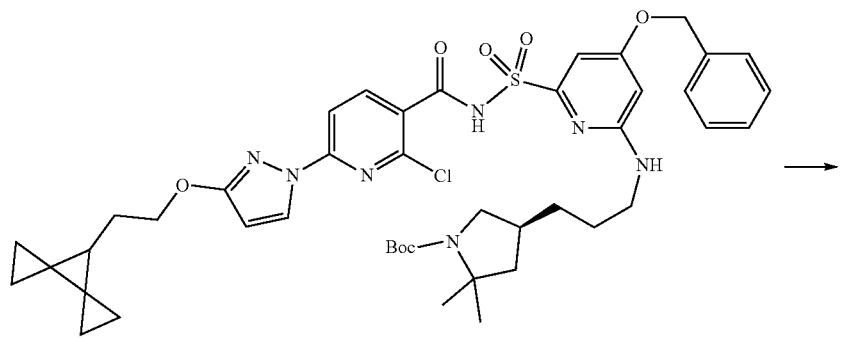

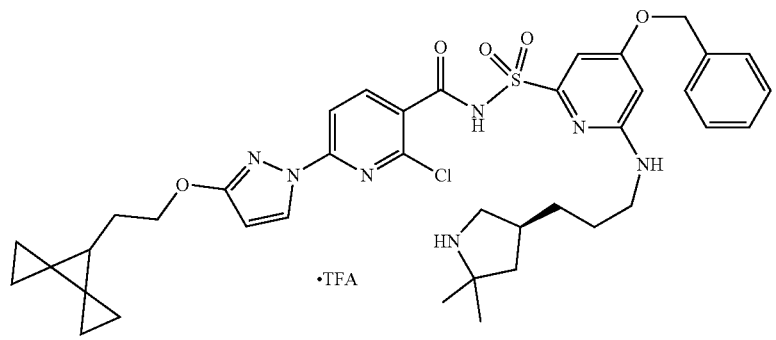

To a stirred solution of tert-butyl (4S)-4-[3-[[4-benzyloxy-6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-dimethyl-pyrrolidine-1-carboxylate (70 mg, 0.08135 mmol) in anhydrous methylene chloride (2 mL) was added trifluoroacetic acid (300 µL, 3.894 mmol) at ambient temperature under nitrogen. The orange solution was stirred for 1 h then the volatiles were removed under reduced pressure. To the residue, toluene (20 mL) was added and concentrated under reduced pressure to dryness. The process was repeated once more to remove any residual trifluoroacetic acid and finally dried in vacuo for 2 h to obtain crude N-[[4-benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (71 mg, 100%). ESI-MS m/z calc. 759.29694, found 760.5 (M+1)+; Retention time: 2.01 min (LC Method B).

Step 8: (14S)-21-(Benzyloxy)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione

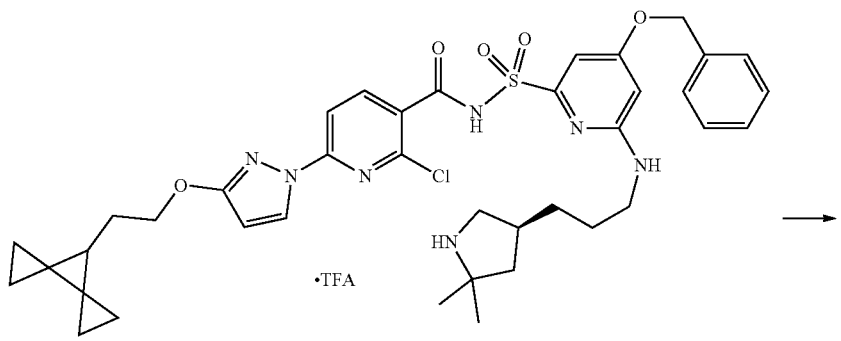

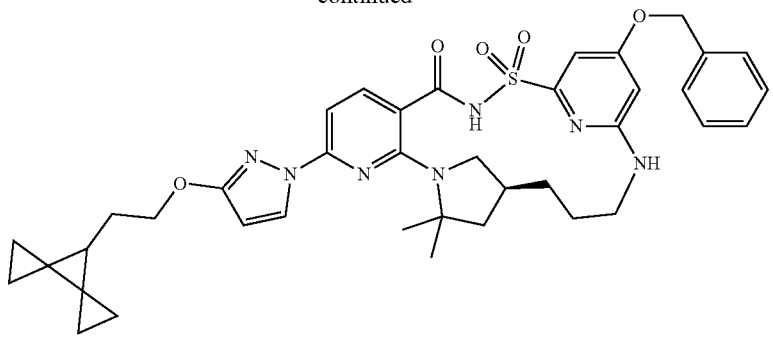

A 20 mL vial was charged with N-[[4-benzyloxy-6-[3-[(3S)-5,5-dimethylpyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (67 mg, 0.07663 mmol), potassium carbonate (65 mg, 0.4703 mmol), cesium fluoride (24 mg, 0.1580 mmol) and anhydrous dimethyl sulfoxide (5 mL), in that order. The vial was purged with a stream of nitrogen for 2 min, capped and stirred at 160° C. for 15 h. The reaction was allowed to cool to ambient temperature and the heterogeneous mixture was diluted with ethyl acetate (30 mL) and water (20 mL) and acidified with hydrochloric acid (1.0 mL of 1.0 M, 1.000 mmol). The layers were separated and the aqueous layer was re-extracted with ethyl acetate (20 mL). The combined organics were washed with brine (20 mL), dried over anhydrous sodium sulfate, filtered and evaporated under reduced pressure. The crude was purified by silica gel chromatography (0%-10% methanol in dichloromethane over 30 min) affording (14S)-21-(benzyloxy)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (34 mg, 61%) as a white solid. ESI-MS m/z calc. 723.3203, found 724.5 (M+1)$^+$; Retention time: 2.22 min (LC Method G).

Step 9: (14S)-8-[3-(2-{Dispiro[2.0.2.1]heptan-7-yl}ethoxy)-1H-pyrazol-1-yl]-21-hydroxy-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound 264)

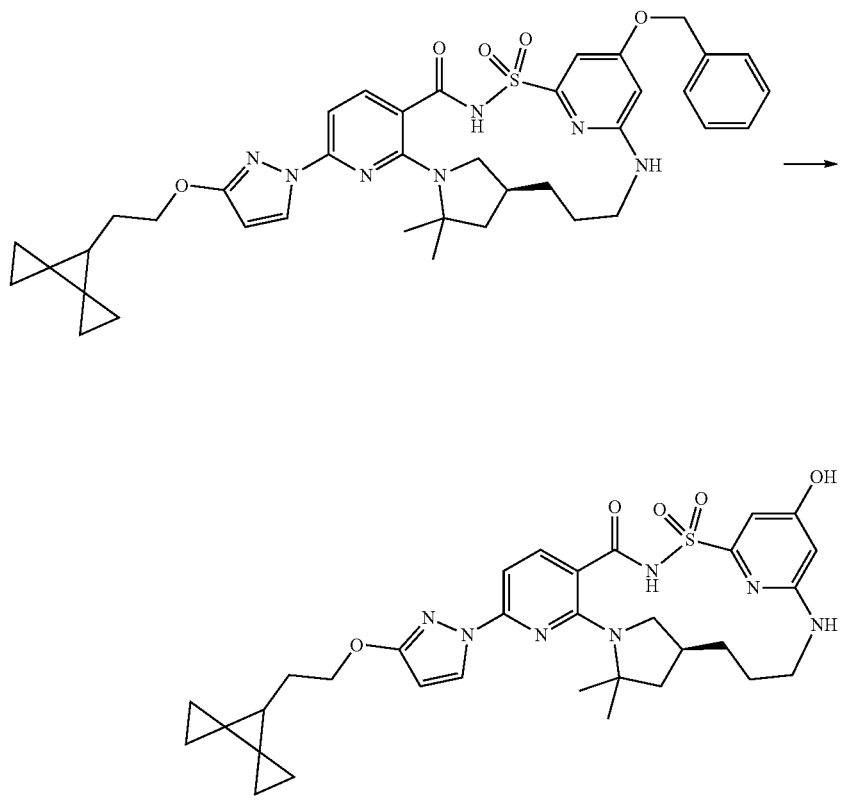

To a stirred solution of (14S)-21-(benzyloxy)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (25 mg, 0.03454 mmol) in anhydrous methanol (5 mL) was added 10% palladium on carbon (wet, Degussa, 12 mg, 0.01128 mmol) under nitrogen. The heterogeneous mixture was stirred under hydrogen (balloon) for 3 h at ambient temperature. The hydrogen balloon was removed and the flask was purged with nitrogen and the black heterogeneous reaction mixture was filtered over a pad of celite. The filtrate was concentrated under reduced pressure and the residue was taken up in dimethyl sulfoxide (1.5 mL) and filtered through a Whatman 0.45 μm PTFE syringe filter disc. The sample was purified using preparative reverse-phase HPLC-MS [Luna C₁₈ (2) column (75×30 mm, 5 μm particle size) sold by Phenomenex (pn: 00C-4252-U0-AX), (dual gradient run from 30%-99% acetonitrile in water over 15 min (no modifier)] to obtain (14S)-8-[3-(2-{dispiro[2.0.2.1]heptan-7-yl}ethoxy)-1H-pyrazol-1-yl]-21-hydroxy-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 264) (8 mg, 36%) as an off-white solid. ¹H NMR (400 MHz, Methanol-d₄) δ 8.24 (d, J=2.8 Hz, 1H), 7.85 (d, J=8.2 Hz, 1H), 6.97 (d, J=8.2 Hz, 1H), 6.75 (d, J=1.9 Hz, 1H), 6.00 (d, J=1.9 Hz, 1H), 5.94 (d, J=2.7 Hz, 1H), 4.24 (t, J=6.6 Hz, 2H), 4.02 (t, J=13.1 Hz, 1H), 3.38-3.32 (m, 2H), 3.08-2.97 (m, 1H), 2.92 (t, J=10.5 Hz, 1H), 2.24-2.09 (m, 1H), 1.88 (q, J=6.6 Hz, 3H), 1.85-1.76 (m, 1H), 1.66 (s, 3H), 1.63 (d, J=5.7 Hz, 2H), 1.60 (s, 3H), 1.49 (d, J=6.5 Hz, 1H), 1.47-1.39 (m, 1H), 0.91-0.79 (m, 4H), 0.66 (ddd, J=8.8, 4.7, 3.4 Hz, 2H), 0.58-0.48 (m, 2H). ESI-MS m/z calc. 633.2733, found 634.5 (M+1)⁺; Retention time: 2.27 min (LC Method B).

Example 89: Preparation of (14S)-21-hydroxy-12,12-dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 265)

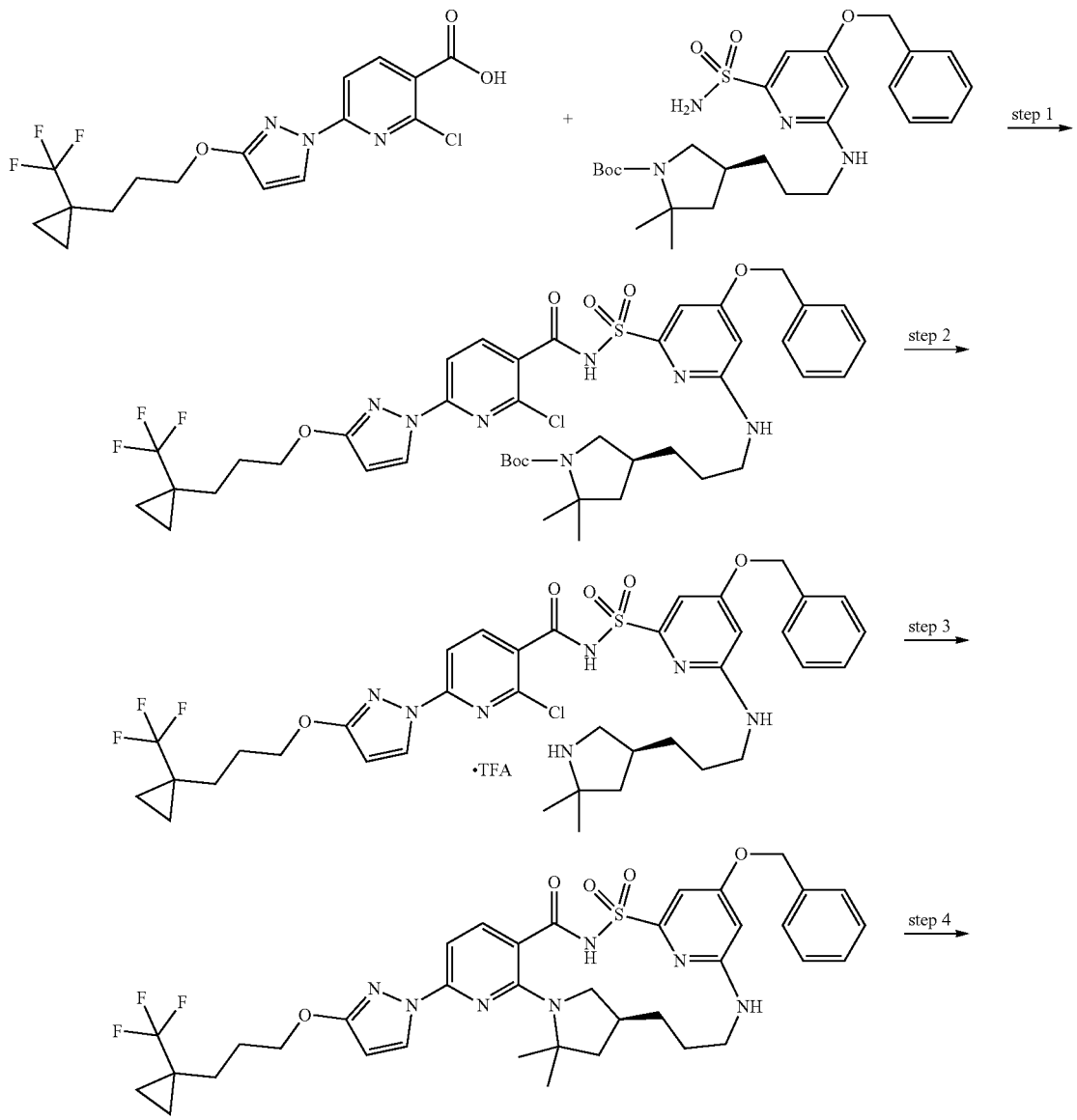

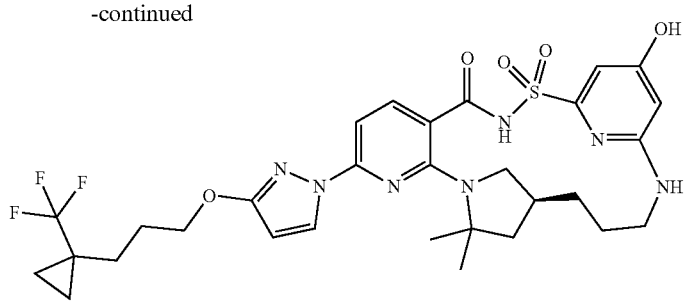

Step 1: tert-Butyl (4S)-4-[3-[[4-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate

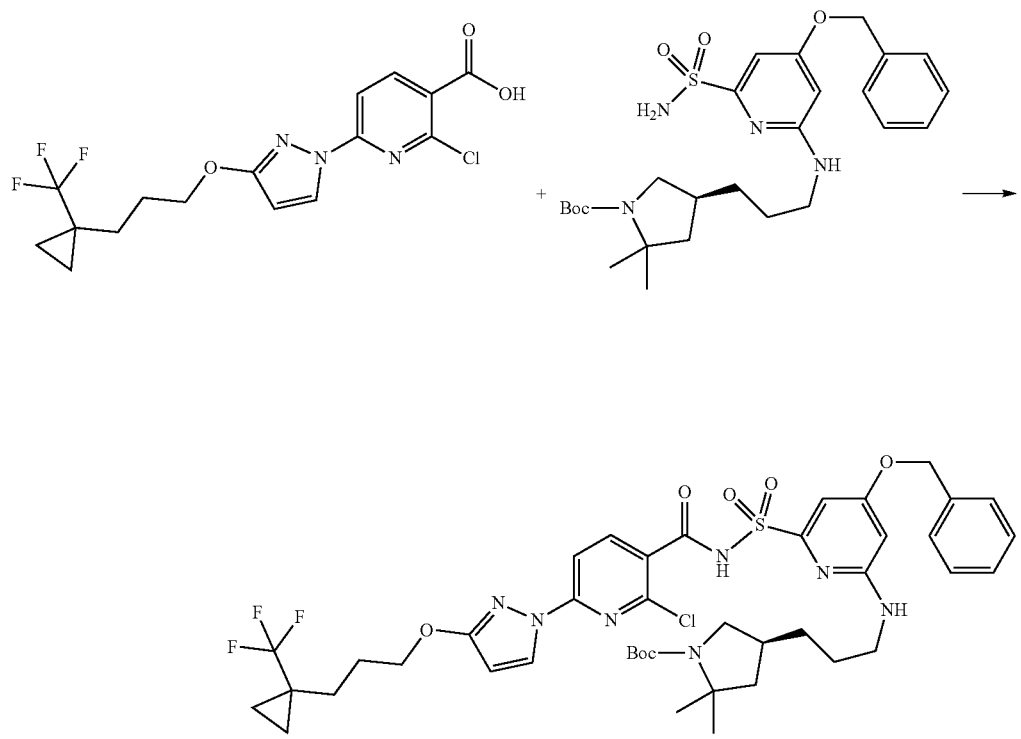

To a stirred solution of 2-chloro-6-[3-[3-[1-(trifluoromethyl)cyclopropyl]propoxy]pyrazol-1-yl]pyridine-3-carboxylic acid (130 mg, 0.3335 mmol) in anhydrous tetrahydrofuran (2 mL) was added carbonyl diimidazole (55 mg, 0.3392 mmol) and stirring continued at ambient temperature under nitrogen for 2 h. To the reaction, a solution of tert-butyl (4S)-4-[3-[(4-benzyloxy-6-sulfamoyl-2-pyridyl)amino]propyl]-2,2-dimethyl-pyrrolidine-1-carboxylate (150 mg, 0.2892 mmol) in anhydrous tetrahydrofuran (1 mL) was added, followed by 1,8-diazabicyclo[5.4.0]undec-7-ene (200 μL, 1.337 mmol) and the mixture was stirred at ambient temperature for 15 h. The volatiles were removed under reduced pressure and the residue was diluted with ethyl acetate (20 mL) and water (20 mL) and the mixture was acidified slowly with 4 M aqueous hydrochloric acid (350 μL of 4 M, 1.400 mmol) to about pH=4.0. The layers were separated and the aqueous layer was extracted with ethyl acetate (15 mL). The combined organic phases were washed with brine (20 mL), dried over anhydrous sodium sulfate, filtered and concentrated under reduced pressure. The crude material was purified via silica gel chromatography (gradient from 0%-70% ethyl acetate in hexanes over 35 min) to furnish tert-butyl (4S)-4-[3-[[4-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (128 mg, 50%) as a white solid. ESI-MS m/z calc. 889.3211, found 890.6 (M+1)$^+$; Retention time: 2.25 min (LC Method G).

Step 2: N-[[4-Benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (Trifluoroacetate Salt)

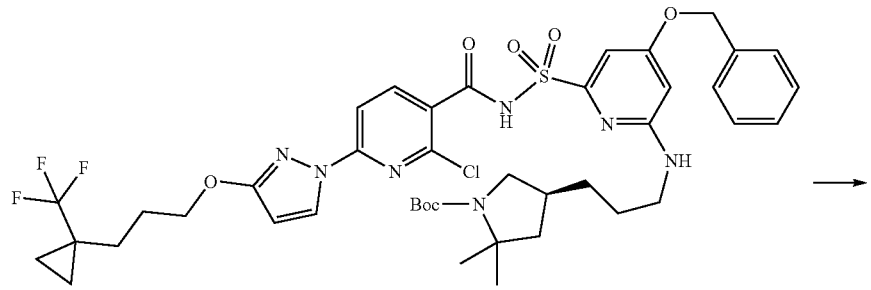

30

To a stirred solution of tert-butyl 4-[3-[[4-benzyloxy-6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (121 mg, 0.1359 mmol) in anhydrous methylene chloride (3 mL) was added trifluoroacetic acid (500 μL, 6.490 mmol) at ambient temperature under nitrogen. The orange solution was stirred for 1 h and then the volatiles were removed under reduced pressure. To the residue, toluene (20 mL) was added and concentrated under reduced pressure to dryness. The process was repeated once more to remove any residual trifluoroacetic acid and finally dried in vacuo for 2 h to obtain crude N-[[4-benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (trifluoroacetate salt) (122 mg, 99%). The material was taken directly to the next step without any purification. ESI-MS m/z calc. 789.2687, found 790.5 (M+1)$^+$; Retention time: 1.9 min (LC Method B).

Step 3: (14S)-21-(Benzyloxy)-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione

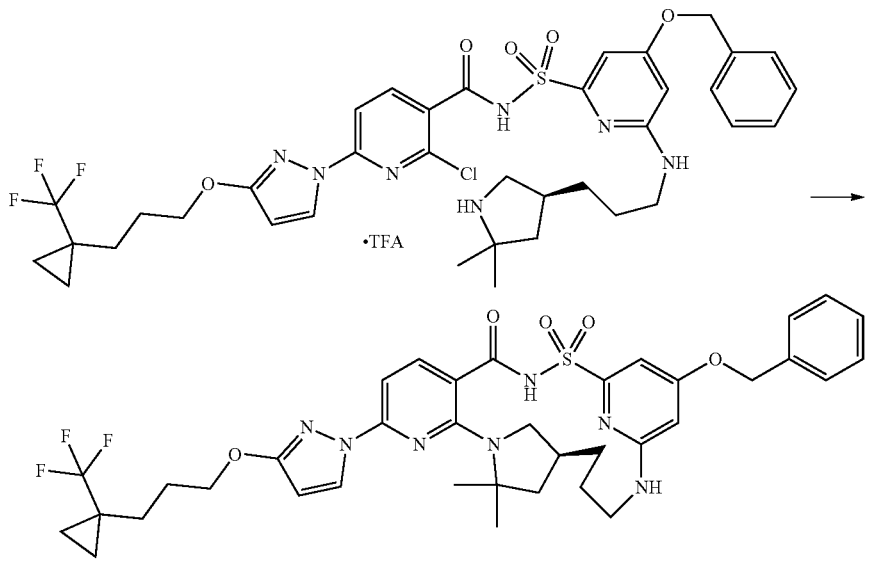

A 20 mL vial was charged with N-[[4-benzyloxy-6-[3-[(3S)-5,5-dimethylpyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (trifluoroacetate salt) (115 mg, 0.1272 mmol), potassium carbonate (110 mg, 0.7959 mmol), cesium fluoride (39 mg, 0.2567 mmol) and anhydrous dimethyl sulfoxide (9 mL), in that order. The vial was purged with a stream of nitrogen for 2 min, capped and stirred at 160° C. for 15 h. The reaction was allowed to cool to ambient temperature and the heterogeneous mixture was diluted with ethyl acetate (40 mL) and water (30 mL) and acidified with hydrochloric acid (1.6 mL of 1.0 M, 1.600 mmol). The layers were separated and the aqueous layer was re-extracted with ethyl acetate (20 mL). The combined organics were washed with brine (20 mL), dried over anhydrous sodium sulfate, filtered and evaporated under reduced pressure. The crude was purified via silica gel chromatography (gradient from 0%-10% methanol in dichloromethane over 30 min) affording (14S)-21-(benzyloxy)-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (54 mg, 56%) as a white solid. ESI-MS m/z calc. 753.29205, found 754.5 (M+1)$^+$; Retention time: 1.51 min (LC Method J).

Step 4: (14S)-21-Hydroxy-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 265)

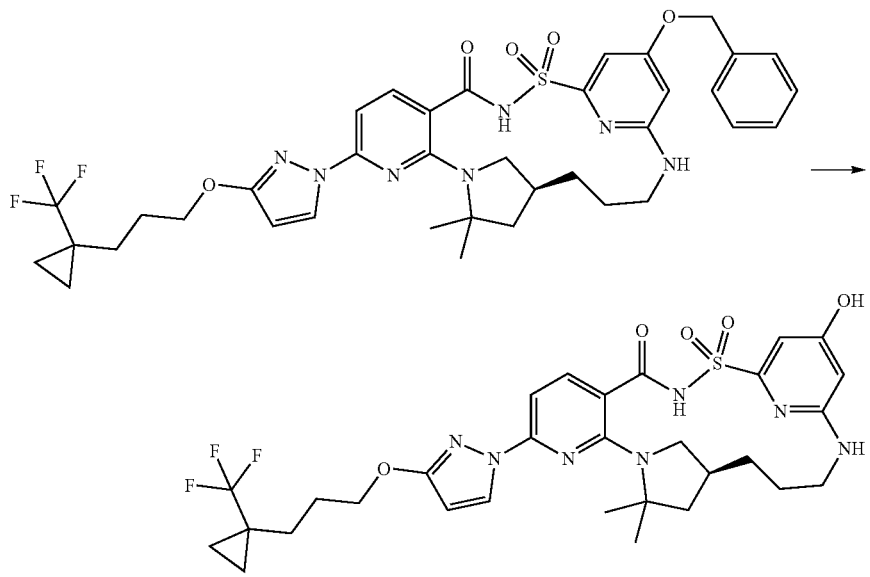

To a stirred solution of (14S)-21-(benzyloxy)-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (40 mg, 0.05306 mmol) in anhydrous methanol (5 mL) was added 10% palladium on carbon (wet, Degussa, 19 mg, 0.01785 mmol) under nitrogen. The heterogeneous mixture was stirred under hydrogen (balloon) for 2.5 h at ambient temperature. The hydrogen balloon was removed and the flask was purged with nitrogen and the black heterogeneous reaction mixture was filtered over a pad of celite. The filtrate was concentrated under reduced pressure and the residue was taken up in dimethyl sulfoxide (1.5 mL) and filtered through a Whatman 0.45 μm PTFE syringe filter disc. The sample was purified using preparative reverse-phase HPLC-MS [Luna C$_{18}$ (2) column (75×30 mm, 5 μm particle size) sold by Phenomenex (pn: 00C-4252-U0-AX), (dual gradient run from 30%-99% acetonitrile in water over 15 min (no modifier)] to obtain (14S)-21-hydroxy-12,12-dimethyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 265) (16 mg, 45%) as a pale blue-green solid. $^1$H NMR (400 MHz, Methanol-d$_4$) δ 8.25 (d, J=2.8 Hz, 1H), 7.85 (d, J=8.2 Hz, 1H), 6.97 (d, J=8.2 Hz, 1H), 6.76 (d, J=1.9 Hz, 1H), 6.00 (d, J=1.9 Hz, 1H), 5.97 (d, J=2.8 Hz, 1H), 4.24 (t, J=6.1 Hz, 2H), 4.01 (t, J=12.8 Hz, 1H), 3.36-3.32 (m, 1H), 3.02 (d, J=13.6 Hz, 1H), 2.94 (t, J=10.5 Hz, 1H), 2.24-2.08 (m, 1H), 1.94 (dq, J=11.0, 6.3 Hz, 2H), 1.90-1.79 (m, 2H), 1.78 (d, J=4.6 Hz, 1H), 1.77-1.74 (m, 1H), 1.66 (s, 3H), 1.63 (d, J=7.0 Hz, 2H), 1.60 (s, 3H), 1.58 (d, J=7.9 Hz, 1H), 1.51-1.36 (m, 1H), 0.98-0.92 (m, 2H), 0.73-0.65 (m, 2H). $^{19}$F NMR (376 MHz, Methanol-$d_4$) δ −70.92. ESI-MS m/z calc. 663.24506, found 665.5 (M+1)$^+$; Retention time: 2.13 min (LC Method B).

Example 90: Preparation of 2-imino-12,12-dimethyl-8-(3-{2-[1-(trifluoromethyl) cyclopropyl]ethoxy}-1H-pyrazol-1-yl)-2=$^6$-thia-3,9,11,18,23-pentaazatetracyclo[17.3.1.111,14.05,10]tetracosa-1(23),5,7,9,19,21-hexaene-2,4-dione (Diastereomer Pair 1, Enantiomer 1) (Compound 266), 2-imino-12,12-dimethyl-8-(3-{2-[1-(trifluoro methyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5,7,9,19,21-hexaene-2,4-dione (Diastereomer Pair 1, Enantiomer 2) (Compound 267), 2-imino-12,12-dimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5,7,9,19,21-hexaene-2,4-dione (Diastereomer Pair 2, Enantiomer 1) (Compound 271) and 2-imino-12,12-dimethyl-8-(3-{2-[1-(trifluoromethyl) cyclopropyl]ethoxy}-1H-pyrazol-1-yl)-2λ$^6$-thia-3,9,11,18,23-pentaazatetracyclo[17.3.1.111,14.05,10] tetracosa-1(23),5,7,9,19,21-hexaene-2,4-dione (Diastereomer Pair 2, Enantiomer 2) (Compound 272)

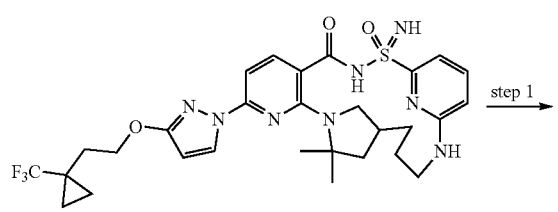

diastereomer pair 1


diastereomer pair 1, enantiomer 1

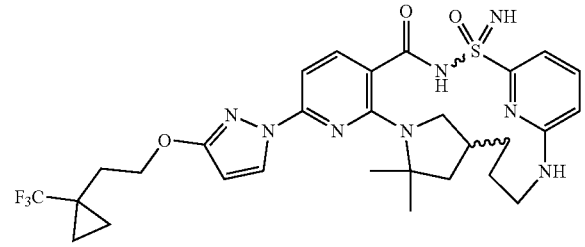

diastereomer pair 1, enantiomer 2


diastereomer pair 2

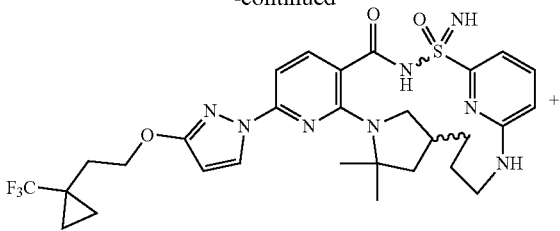

diastereomer pair 2, enantiomer 1

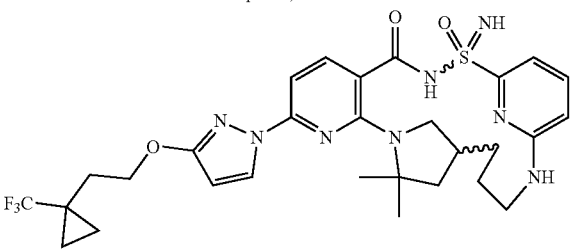

diastereomer pair 2, enantiomer 2

Step 1: 2-Imino-12,12-dimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5,7,9,19,21-hexaene-2,4-dione (Diastereomer Pair 1, Enantiomer 1) (Compound 266) and 2-imino-12,12-dimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.111,14.05,10]tetracosa-1(23),5,7,9,19,21-hexaene-2,4-dione (Diastereomer Pair 1, Enantiomer 2) (Compound 267)

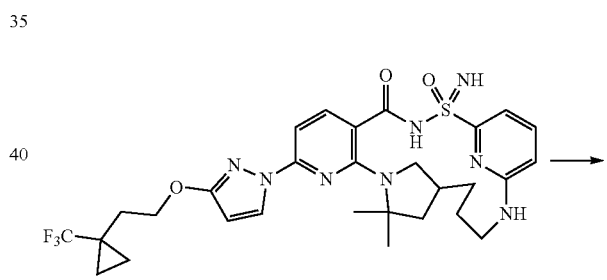

diastereomer pair 1

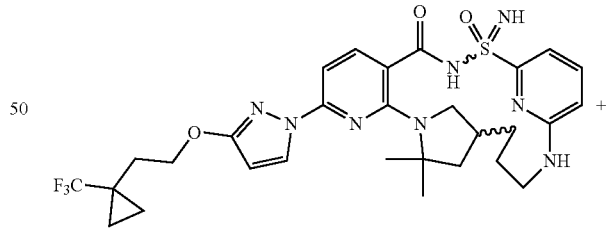

diastereomer pair 1, enantiomer 1

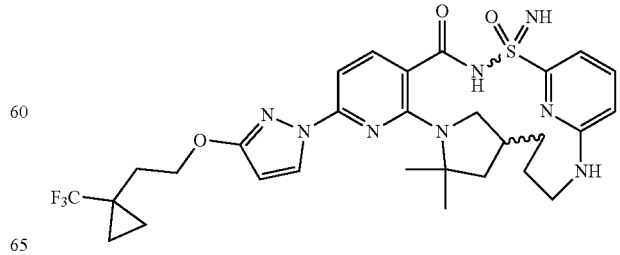

diastereomer pair 1, enantiomer 2

Racemic 2-imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (81 mg, 0.1248 mmol) (diastereomer pair 1) (81 mg) was subjected to chiral SFC (ChiralPak AD-H (250×10 mm), 5 μM column; mobile phase 34% acetonitrile/methanol (50:50, 20 mM NH₃), 66% carbon dioxide, 10 mL/min; concentration 12 mg/mL in acetonitrile/methanol (50:50 20 mM NH₃); injection volume 70 μL, 100 bar) giving as the first enantiomer to elute, 2-imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (diastereomer pair 1, enantiomer 1) (Compound 266) (15.2 mg, 38%), ¹H NMR (400 MHz, dimethyl sulfoxide-d₆) δ 8.14 (d, J=2.7 Hz, 1H), 7.75 (d, J=8.1 Hz, 1H), 7.54-7.43 (m, 1H), 7.03 (t, J=6.8 Hz, 2H), 6.77 (d, J=8.1 Hz, 1H), 6.54 (d, J=8.4 Hz, 1H), 6.00 (d, J=2.6 Hz, 1H), 4.24 (t, J=7.0 Hz, 2H), 3.17 (dd, J=10.8, 7.3 Hz, 1H), 2.12 (s, 1H), 2.05-1.99 (m, 2H), 1.82 (s, 2H), 1.53 (d, J=26.0 Hz, 9H), 1.23 (d, J=51.9 Hz, 4H), 0.85 (d, J=28.0 Hz, 4H); ESI-MS m/z calc. 632.2505, found 633.0 (M+1)⁺; Retention time: 3.16 min (LC Method D); and as the second enantiomer to elute, 2-imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (diastereomer pair 1, enantiomer 2) (Compound 267) (15 mg, 38%). ¹H NMR (400 MHz, dimethyl sulfoxide-d₆) δ 8.21 (s, 1H), 7.82 (d, J=8.1 Hz, 1H), 7.53 (s, 1H), 7.09 (s, 2H), 6.83 (d, J=8.1 Hz, 1H), 6.60 (d, J=8.3 Hz, 1H), 6.07 (s, 1H), 4.30 (s, 2H), 3.48 (s, 1H), 3.24 (s, 1H), 2.20 (s, 1H), 2.07 (d, J=14.1 Hz, 2H), 1.87 (s, 2H), 1.59 (d, J=25.3 Hz, 8H), 1.35 (s, 1H), 1.23 (s, 2H), 0.92 (d, J=27.7 Hz, 4H). ESI-MS m/z calc. 632.2505, found 633.0 (M+1)⁺; Retention time: 3.18 min (LC Method D).

Step 2: 2-Imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (Diastereomer Pair 2, Enantiomer 1) (Compound 271) and 2-imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (Diastereomer Pair 2, Enantiomer 2) (Compound 272)

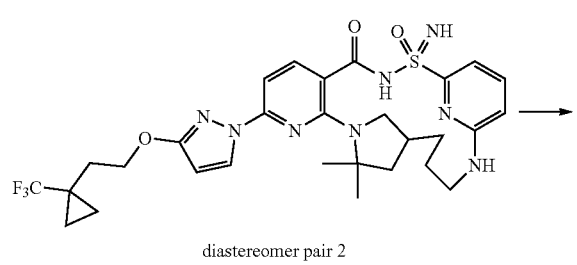

diastereomer pair 2

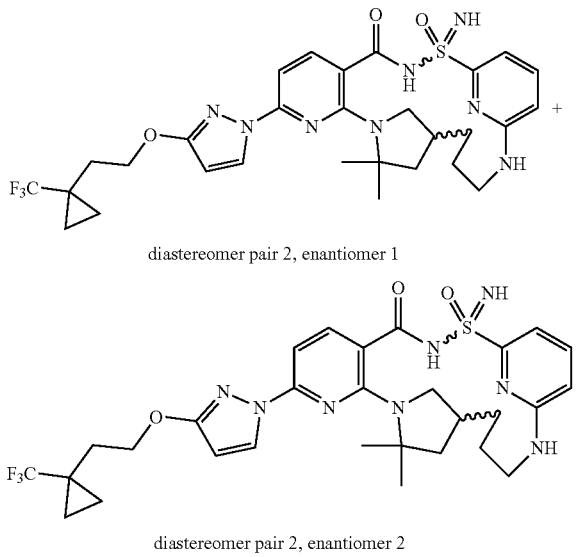

diastereomer pair 2, enantiomer 1 diastereomer pair 2, enantiomer 2

Racemic 2-imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (diastereomer pair 2) (91 mg) was subjected to chiral SFC (Phenomenex LUX-4 (250×21.2 mm), 5 μM column; mobile phase 40% acetonitrile/methanol (90:10, 20 mM NH₃), 60% carbon dioxide, 70 mL/min; concentration 15 mg/mL in acetonitrile/methanol (90:10; 20 mM NH₃); injection volume 700 μL, 100 bar). The first enantiomer to elute was further by reverse phase preparative chromatography using a C₁₈ column and a 15 min. gradient eluent of 50% to 99% acetonitrile in water containing 10 mM ammonium formate to give 2-imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (diastereomer pair 2, enantiomer 1) (Compound 271) (22.4 mg, 50%). ¹H NMR (400 MHz, dimethyl sulfoxide-d₆) δ 8.19 (d, J=2.7 Hz, 1H), 7.93 (d, J=8.1 Hz, 1H), 7.59-7.53 (m, 1H), 7.41 (s, 2H), 7.05 (d, J=7.2 Hz, 1H), 6.86 (t, J=9.5 Hz, 2H), 6.65 (d, J=8.4 Hz, 1H), 4.31 (t, J=7.0 Hz, 2H), 4.08-3.92 (m, 1H), 3.20 (s, 1H), 2.89 (t, J=10.8 Hz, 2H), 2.08 (q, J=7.0, 6.0 Hz, 3H), 1.86-1.72 (m, 2H), 1.55 (d, J=27.1 Hz, 10H), 1.31 (d, J=11.4 Hz, 1H), 0.92 (d, J=28.7 Hz, 5H). ESI-MS m/z calc. 632.2505, found 633.0 (M+1)⁺; Retention time: 3.02 min (LC Method D). The second enantiomer to elute from the SFC separation was 2-imino-12,12-dimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.111,14.05,10]tetracosa-1(23),5,7,9,19,21-hexaene-2,4-dione (diastereomer pair 2, enantiomer 2) (Compound 272) (29.8 mg, 67%). ¹H NMR (400 MHz, dimethyl sulfoxide-d₆) δ 8.19 (d, J=2.6 Hz, 1H), 7.93 (d, J=8.1 Hz, 1H), 7.60-7.52 (m, 1H), 7.41 (s, 2H), 7.05 (d, J=7.2 Hz, 1H), 6.85 (dd, J=12.7, 8.7 Hz, 2H), 6.64 (d, J=8.4 Hz, 1H), 6.06 (d, J=2.6 Hz, 1H), 4.31 (s, 2H), 3.99 (d, J=11.5 Hz, 1H), 3.20 (s, 1H), 2.91 (d, J=10.9 Hz, 2H), 2.08 (t, J=7.0 Hz, 3H), 1.88-1.71 (m, 2H), 1.55 (d, J=27.0 Hz, 9H), 1.31 (d, J=11.2 Hz, 1H), 0.92 (d, J=29.2 Hz, 4H). ESI-MS m/z calc. 632.2505, found 633.0 (M+1)⁺; Retention time: 3.07 min (LC Method D).

Example 91: Preparation of (14S)-12,12-dimethyl-8-(3-{3-[1-(trifluoromethyl)cyclopropyl]-3,3-dideuterio-propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Compound 269)

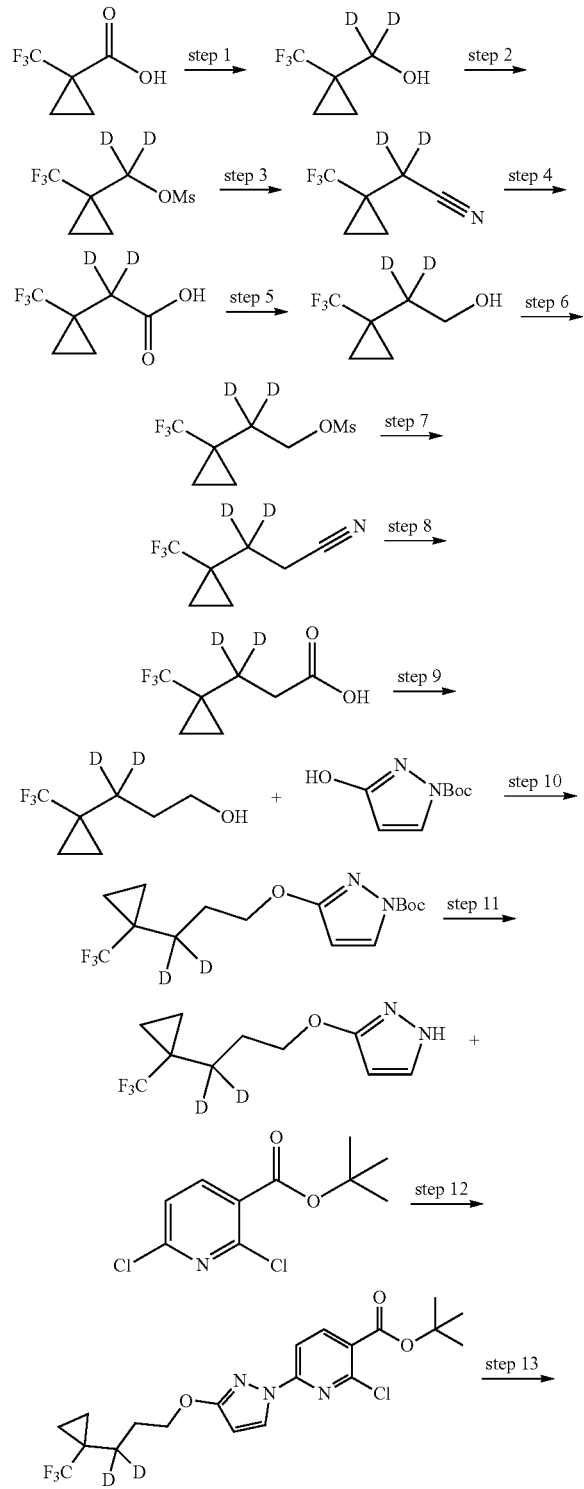

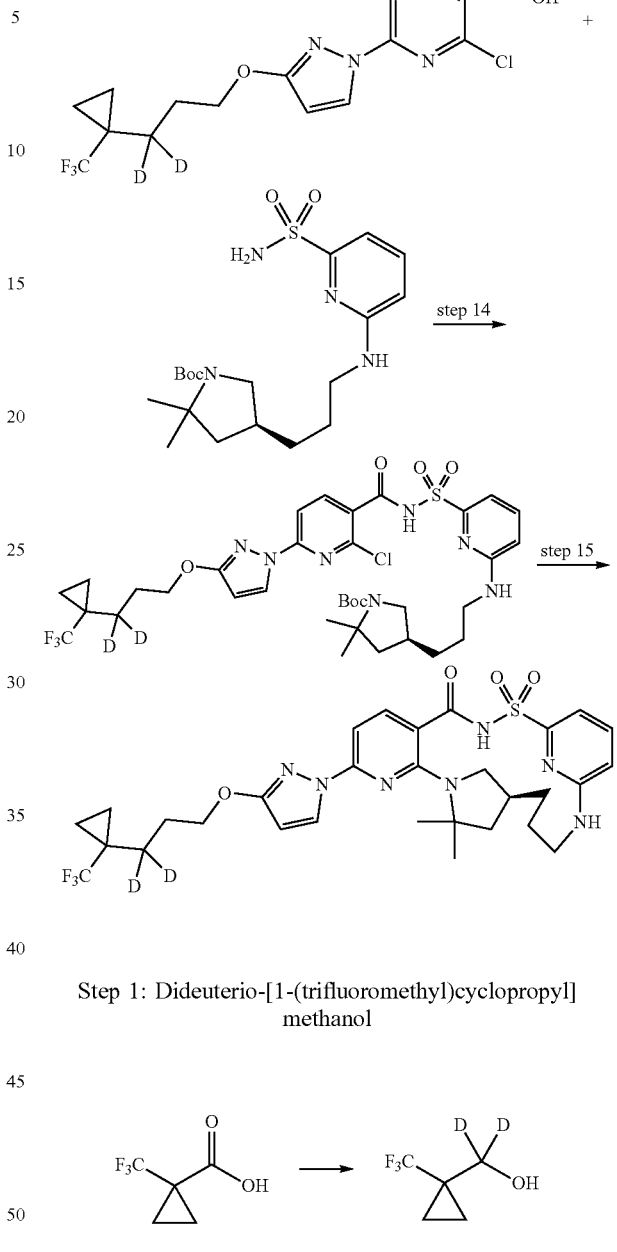

Step 1: Dideuterio-[1-(trifluoromethyl)cyclopropyl]methanol

Into a suspension of lithium aluminum deuteride (2.86 g, 71.563 mmol) in anhydrous tetrahydrofuran (100 mL) was added a solution of 1-(trifluoromethyl)cyclopropanecarboxylic acid (10 g, 64.898 mmol) in anhydrous tetrahydrofuran (50 mL) at 0° C. dropwise. The reaction mixture was stirred at room temperature for 16 h. The reaction was diluted with diethyl ether (100 mL) and quenched with water (2.9 mL), 15% sodium hydroxide (2.9 mL) and water (8.7 mL) sequentially at 0° C. The reaction mixture was stirred at room temperature for 30 min. The white solid was filtered off through a pad of celite. The filtrate was concentrated under vacuum to furnish dideuterio-[1-(trifluoromethyl)cyclopropyl]methanol (10.855 g, 86%) as a clear liquid. ¹H NMR (250 MHz, CDCl₃) δ 1.72 (s, 1H), 1.03 (m, 2H), 0.79 (m, 2H).

Step 2: [Dideuterio-[1-(trifluoromethyl)cyclopropyl]methyl]methanesulfonate

Into a solution of dideuterio-[1-(trifluoromethyl)cyclopropyl]methanol (8.537 g, 54.064 mmol) and triethylamine (10.942 g, 15.072 mL, 108.13 mmol) in dichloromethane (100 mL) was added methanesulfonyl chloride (7.4318 g, 5.0215 mL, 64.877 mmol) dropwise at 0° C. The reaction mixture was stirred at room temperature for 16 h. The reaction mixture was washed with 10% citric acid (50 mL), saturated sodium bicarbonate (50 mL) and brine (50 mL). The organic solution was dried over anhydrous sodium sulfate, filtered and concentrated under reduced pressure. The residue was purified by silica gel chromatography using a gradient of 0% to 70% diethyl ether in hexane to furnish [dideuterio-[1-(trifluoromethyl)cyclopropyl]methyl]methanesulfonate (11.203 g, 88%) as a clear liquid. $^1$H NMR (250 MHz, CDCl$_3$) δ 3.06 (s, 3H), 1.21 (m, 2H), 1.02-0.81 (m, 2H).

Step 3: 2,2-Dideuterio-2-[1-(trifluoromethyl)cyclopropyl]acetonitrile

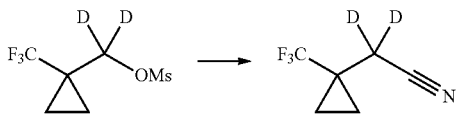 [SMILES: [2H]C([2H])(OS(C)(=O)=O)C1(C(F)(F)F)CC1 ; [2H]C([2H])(C#N)C1(C(F)(F)F)CC1]

Into a solution of [dideuterio-[1-(trifluoromethyl)cyclopropyl]methyl]methanesulfonate (11.203 g, 47.823 mmol) in dimethyl sulfoxide (55 mL) was added sodium cyanide (2.9296 g, 59.779 mmol). The reaction mixture was stirred at 70° C. for 24 h. After cooling to room temperature, water (50 mL) and diethyl ether (50 mL) were added to the reaction mixture. The two layers were separated. The aqueous layer was extracted with diethyl ether (2×70 mL). The combined organic layers were washed with water (2×50 mL) and brine (50 mL), dried over anhydrous magnesium sulfate, filtered and concentrated under vacuum to furnish 2,2-dideuterio-2-[1-(trifluoromethyl)cyclopropyl]acetonitrile (6.828 g, 84%) as a yellow liquid. $^1$H NMR (250 MHz, CDCl$_3$) δ 1.18 (m, 2H), 0.93 (s, 2H).

Step 4: 2,2-Dideuterio-2-[1-(trifluoromethyl)cyclopropyl]acetic Acid

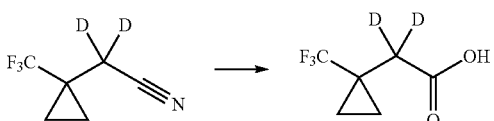

Into a solution of 2,2-dideuterio-2-[1-(trifluoromethyl)cyclopropyl]acetonitrile (6.828 g, 40.211 mmol) in CH$_3$CwaterD (70 mL) was added a solution of sodium deuteroxide (16.487 g, 40% w/w, 160.84 mmol) in deuterium oxide (16 mL). The reaction mixture was stirred at 70° C. for 24 h. After cooling to room temperature, CH$_3$CwaterD was removed under reduced pressure. The solvent was diluted with water (70 mL) and washed with diethyl ether (2×50 mL). The aqueous layer was acidified with 6 N hydrochloric acid to pH=1 and then it was extracted with diethyl ether (3×70 mL). The combined organic layers were washed with brine (50 mL), dried over anhydrous magnesium sulfate, filtered and concentrated under reduced pressure to furnish 2,2-dideuterio-2-[1-(trifluoromethyl)cyclopropyl]acetic acid (6.387 g, 83%) as a yellow liquid. $^1$H NMR (250 MHz, CDCl$_3$) δ 1.18-1.05 (m, 2H), 0.93-0.79 (m, 2H).

Step 5: 2,2-Dideuterio-2-[1-(trifluoromethyl)cyclopropyl]ethanol

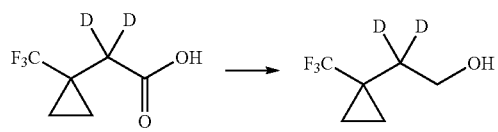 [SMILES: [2H]C([2H])(C(=O)O)C1(C(F)(F)F)CC1 ; [2H]C([2H])(CO)C1(C(F)(F)F)CC1]

Into a suspension of lithium aluminum hydride (952.12 mg, 1.0383 mL, 25.086 mmol) in anhydrous tetrahydrofuran (50 mL) was added a solution of 2,2-dideuterio-2-[1-(trifluoromethyl)cyclopropyl]acetic acid (3.35 g, 19.297 mmol) in anhydrous tetrahydrofuran (50 mL) at 0° C. dropwise. The reaction mixture was stirred at room temperature for 16 h. The reaction mixture was diluted with diethyl ether (50 mL) and cooled down to 0° C. Water (1 mL), 15% aqueous sodium hydroxide (1 mL) and water (3 mL) were added sequentially and the resulting mixture was stirred at room temperature for 15 min. Anhydrous magnesium sulfate was added and the reaction mixture was stirred at room temperature for another 15 min. The solids were filtered off and the filtrate was concentrated under vacuum to furnish 2,2-dideuterio-2-[1-(trifluoromethyl)cyclopropyl]ethanol (3.154 g, 84%) as a clear liquid. $^1$H NMR (250 MHz, CDCl$_3$) δ 3.79 (s, 2H), 1.05-0.78 (m, 2H), 0.78-0.41 (m, 2H).

Step 6: [2,2-Dideuterio-2-[1-(trifluoromethyl)cyclopropyl]ethyl]methanesulfonate

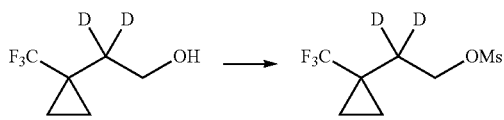 [SMILES: [2H]C([2H])(CO)C1(C(F)(F)F)CC1 ; [2H]C([2H])(COS(C)(=O)=O)C1(C(F)(F)F)CC1]

Into a solution of 2,2-dideuterio-2-[1-(trifluoromethyl)cyclopropyl]ethanol (3.154 g, 16.160 mmol) in dichloromethane (32 mL) was added triethylamine (4.9057 g, 6.7572 mL, 48.480 mmol). The reaction mixture was cooled down to 0° C. and methanesulfonyl chloride (2.2214 g, 1.5009 mL, 19.392 mmol) was added dropwise. The reaction mixture was stirred at room temperature for 2 days. The reaction was diluted with dichloromethane (50 mL) and washed with 10% citric acid aqueous solution (50 mL), saturated sodium bicarbonate (50 mL) and brine (50 mL). The solution was dried over anhydrous magnesium sulfate, filtered and concentrated under vacuum. The residue was purified by silica gel chromatography using a gradient from 0% to 50% diethyl ether in hexane to furnish [2,2-dideuterio-2-[1-(trifluoromethyl)cyclopropyl]ethyl]methanesulfonate (3.28 g, 82%) as a clear liquid. $^1$H NMR (250 MHz, CDCl$_3$) δ 4.36 (s, 2H), 3.20-2.87 (s, 3H), 1.15-0.94 (m, 2H), 0.79-0.59 (m, 2H).

Step 7: 3,3-Dideuterio-3-[1-(trifluoromethyl)cyclopropyl]propanenitrile

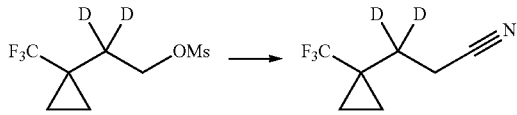 [SMILES: [2H]C([2H])(COS(C)(=O)=O)C1(C(F)(F)F)CC1 ; [2H]C([2H])(CC#N)C1(C(F)(F)F)CC1]

Into a solution of [2,2-dideuterio-2-[1-(trifluoromethyl)cyclopropyl]ethyl]methanesulfonate (3.28 g, 13.303 mmol) in dimethyl sulfoxide (17 mL) was added sodium cyanide (858 mg, 16.6 mmol). The reaction mixture was stirred at 70° C. for 16 h. After cooling to room temperature, the reaction mixture was poured into water (30 mL). The mixture was extracted with diethyl ether (3×50 mL). The combined organic layers were washed with water (2×30 mL) and brine (50 mL), dried over anhydrous magnesium sulfate, filtered and concentrated under reduced pressure to furnish 3,3-dideuterio-3-[1-(trifluoromethyl)cyclopropyl]propanenitrile (2.267 g, 99%) as a clear liquid. $^1$H NMR (250 MHz, CDCl$_3$) δ 2.54 (s, 2H), 1.14-1.00 (m, 2H), 0.80-0.66 (m, 2H).

Step 8: 3,3-Dideuterio-3-[1-(trifluoromethyl)cyclopropyl]propanoic Acid

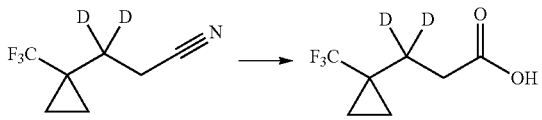 [SMILES: [2H]C([2H])(CC#N)C1(C(F)(F)F)CC1 ; [2H]C([2H])(CC(=O)O)C1(C(F)(F)F)CC1]

Into a solution of 3,3-dideuterio-3-[1-(trifluoromethyl)cyclopropyl]propanenitrile (2.267 g, 13.178 mmol) in ethanol (34 mL) was added a solution of sodium hydroxide (2.1083 g, 52.712 mmol) in water (9 mL). The reaction mixture was stirred at 70° C. for 20 h. After cooling to room temperature, the reaction mixture was concentrated under vacuum then it was diluted with water (30 mL). The aqueous solution was washed with diethyl ether (2×30 mL) and then it was acidified with 6 N hydrochloric acid (aqueous) to pH=1. The aqueous solution was extracted with diethyl ether (3×50 mL). The combined organic layers were washed with brine (30 mL), dried over anhydrous magnesium sulfate, filtered and concentrated under reduced pressure to furnish 3,3-dideuterio-3-[1-(trifluoromethyl)cyclopropyl]propanoic acid (2.652 g, 92%) as a light yellow liquid. $^1$H NMR (250 MHz, CDCl$_3$) δ 2.55 (s, 2H), 1.07-0.82 (m, 2H), 0.61 (m, 2H).

Step 9: 3,3-Dideuterio-3-[1-(trifluoromethyl)cyclopropyl]propan-1-ol

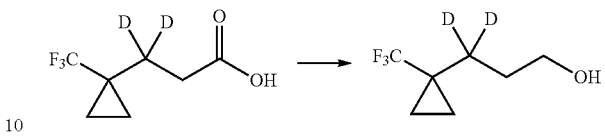

Into a suspension of lithium aluminum hydride (628 mg, 14.940 mmol) in anhydrous tetrahydrofuran (20 mL) was added a solution of 3,3-dideuterio-3-[1-(trifluoromethyl)cyclopropyl]propanoic acid (2.652 g, 12.097 mmol) in anhydrous tetrahydrofuran (20 mL) at 0° C. dropwise. The reaction mixture was stirred at room temperature for 16 h. The reaction was diluted with diethyl ether (20 mL) and cooled to 0° C. Water (0.63 mL), 15% aqueous sodium hydroxide (0.63 mL) and water (1.9 mL) were added to the reaction mixture sequentially. The reaction mixture was stirred at room temperature for 15 min, then magnesium sulfate was added and the reaction was stirred for another 15 min at room temperature. The white precipitate was filtered off. The filtrate was concentrated under reduced pressure to furnish 3,3-dideuterio-3-[1-(trifluoromethyl)cyclopropyl]propan-1-ol (1.78 g, 82%) as a clear liquid. $^1$H NMR (250 MHz, dimethyl sulfoxide-d$_6$) δ 4.45 (t, J=5.1 Hz, 1H), 3.46-3.36 (m, 2H), 1.50 (t, J=6.2 Hz, 2H), 0.86 (m, 2H), 0.69 (m, 2H).

Step 10: tert-Butyl 3-[3,3-dideuterio-3-[1-(trifluoromethyl)cyclopropyl]propoxy]pyrazole-1-carboxylate

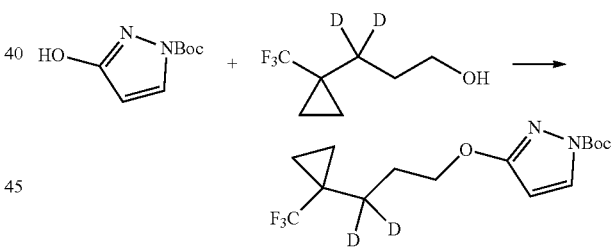

To a solution of tert-butyl 5-oxo-1H-pyrazole-2-carboxylate (910 mg, 4.940 mmol) and 3,3-dideuterio-3-[1-(trifluoromethyl)cyclopropyl]propan-1-ol (880 mg, 5.171 mmol) in tetrahydrofuran (11.25 mL) was added triphenylphosphine (1.36 g, 5.185 mmol). To the mixture was slowly added diisopropyl azodicarboxylate (1.05 g, 5.193 mmol) dropwise over 5 min. The reaction mixture was stirred at room temperature for 30 min. The tetrahydrofuran was removed in vacuo. The crude product was purified by silica gel chromatography using a shallow gradient from 100% hexanes to 20% ethyl acetate in hexanes providing tert-butyl 3-[3,3-dideuterio-3-[1-(trifluoromethyl)cyclopropyl]propoxy]pyrazole-1-carboxylate (1.1 g, 66%) as a colorless oil. $^1$H NMR (400 MHz, Chloroform-d) δ 7.83 (d, J=3.0 Hz, 1H), 5.85 (d, J=3.0 Hz, 1H), 4.27 (t, J=6.2 Hz, 2H), 1.90 (t, J=6.4 Hz, 2H), 1.61 (s, 9H), 1.00-0.91 (m, 2H), 0.64-0.50 (m, J=1.6 Hz, 2H). ESI-MS m/z calc. 336.163, found 337.2 (M+1)$^+$; Retention time: 2.03 min (LC Method E).

Step 11: 3-[3,3-Dideuterio-3-[1-(trifluoromethyl)cyclopropyl]propoxy]-1H-pyrazole

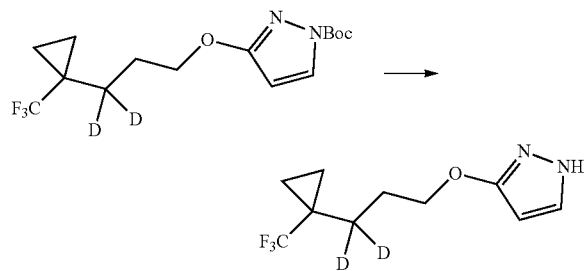

To a flask containing tert-butyl 3-[3,3-dideuterio-3-[1-(trifluoromethyl)cyclopropyl]propoxy]pyrazole-1-carboxylate (1.1 g, 3.270 mmol) was added dichloromethane (22 mL) and trifluoroacetic acid (6.3 mL, 81.77 mmol). After 30 min, the mixture was evaporated to dryness and neutralized with saturated aqueous sodium bicarbonate. The reaction was extracted with ethyl acetate and the organic layer was dried over sodium sulfate, filtered and evaporated to provide 3-[3,3-dideuterio-3-[1-(trifluoromethyl)cyclopropyl]propoxy]-1H-pyrazole (762 mg, 99%) as a colorless oil. ESI-MS m/z calc. 236.11055, found 237.2 (M+1)$^+$; Retention time: 1.43 min (LC Method E).

Step 12: tert-Butyl 2-chloro-6-[3-[3,3-dideuterio-3-[1-(trifluoromethyl)cyclopropyl]propoxy]pyrazol-1-yl]pyridine-3-carboxylate

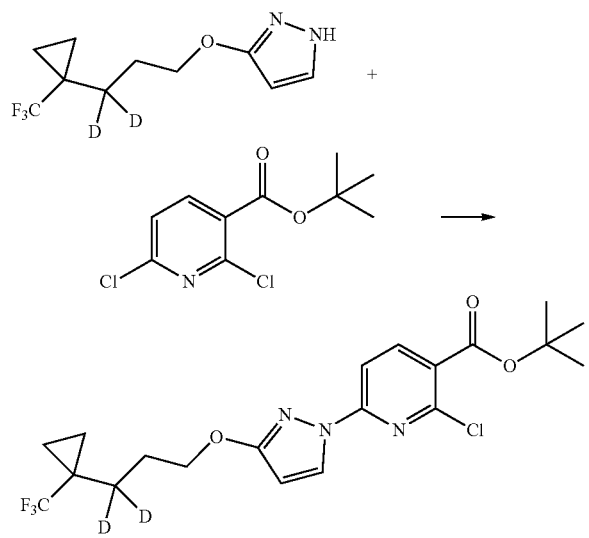

tert-Butyl 2,6-dichloropyridine-3-carboxylate (800 mg, 3.224 mmol), 3-[3,3-dideuterio-3-[1-(trifluoromethyl)cyclopropyl]propoxy]-1H-pyrazole (762 mg, 3.226 mmol) and potassium carbonate (1.1 g, 7.959 mmol) were combined in anhydrous dimethyl sulfoxide (22.0 mL). 1,4-diazabicyclo[2.2.2]octane (72.5 mg, 0.6463 mmol) was added and the mixture was stirred at room temperature under nitrogen for 18 h. The reaction mixture was diluted with water (16 mL) and stirred for 15 min. The resulting solid formed was filtered, collected and dried over high vac. The remaining filtrate was diluted with ethyl acetate, and washed with water (3×20 mL). The organic layers were combined and washed with brine. The organic layer was separated, dried over sodium sulfate, filtered and concentrated under reduced pressure. The residue was purified by silica gel chromatography using a gradient from 100% hexanes to 60% ethyl acetate in hexanes to afford a light yellow oil which was then dried under vacuum to give a pale yellow solid. This purified solid and the solid from the initial filtration were combined to afford tert-butyl 2-chloro-6-[3-[3,3-dideuterio-3-[1-(trifluoromethyl)cyclopropyl]propoxy]pyrazol-1-yl]pyridine-3-carboxylate (1.36 g, 94%). $^1$H NMR (400 MHz, Chloroform-d) δ 8.35 (d, J=2.8 Hz, 1H), 8.18 (d, J=8.4 Hz, 1H), 7.68 (d, J=8.4 Hz, 1H), 5.95 (d, J=2.8 Hz, 1H), 4.26 (t, J=6.2 Hz, 2H), 1.95 (t, J=6.2 Hz, 2H), 1.62 (s, 9H), 1.02-0.94 (m, 2H), 0.66-0.55 (m, J=1.8 Hz, 2H). ESI-MS m/z calc. 447.15054, found 448.2 (M+1)$^+$; Retention time: 2.49 min (LC Method E).

Step 13: 2-Chloro-6-[3-[3,3-dideuterio-3-[1-(trifluoromethyl)cyclopropyl]propoxy]pyrazol-1-yl]pyridine-3-carboxylic Acid

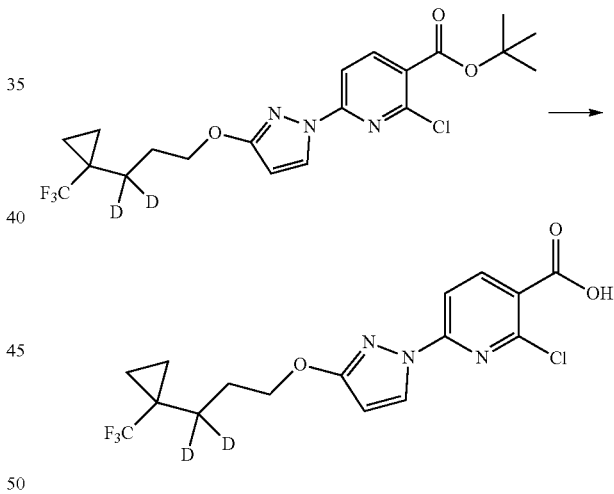

tert-Butyl 2-chloro-6-[3-[3,3-dideuterio-3-[1-(trifluoromethyl)cyclopropyl]propoxy]pyrazol-1-yl]pyridine-3-carboxylate (1.36 g, 3.037 mmol) was dissolved in dichloromethane (30 mL). To the mixture was slowly added trifluoroacetic acid (5.0 mL, 64.90 mmol) and the mixture was kept stirring at room temperature for 2 h. The reaction mixture was concentrated under reduced pressure to a solid which was then slurried in diethyl ether and filtered then the solid was slurried in diethyl ether again and filtered resulting in a solid which was recrystallized from dichloromethane then dried under vacuum for 20 h to give 2-chloro-6-[3-[3,3-dideuterio-3-[1-(trifluoromethyl)cyclopropyl]propoxy]pyrazol-1-yl]pyridine-3-carboxylic acid (1.055 g, 89%) as a white solid. ESI-MS m/z calc. 391.08795, found 392.2 (M+1)$^+$; Retention time: 1.35 min (LC Method E).

Step 14: tert-Butyl (4S)-4-[3-[[6-[[2-chloro-6-[3-[3,3-dideuterio-3-[1-(trifluoromethyl) cyclopropyl] propoxy]pyrazol-1-yl]pyridine-3-carbonyl]sulfamoyl]-2-pyridyl]amino]propyl]-2,2-dimethyl-pyrrolidine-1-carboxylate

Step 15: (14S)-12,12-Dimethyl-8-(3-{3-[1-(trifluoromethyl)cyclopropyl]-3,3-dideuterio-propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Compound 269)

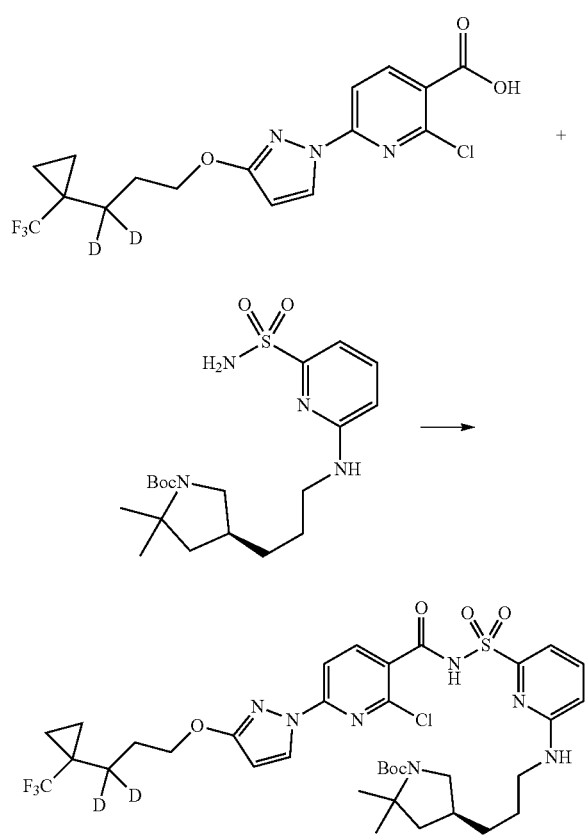

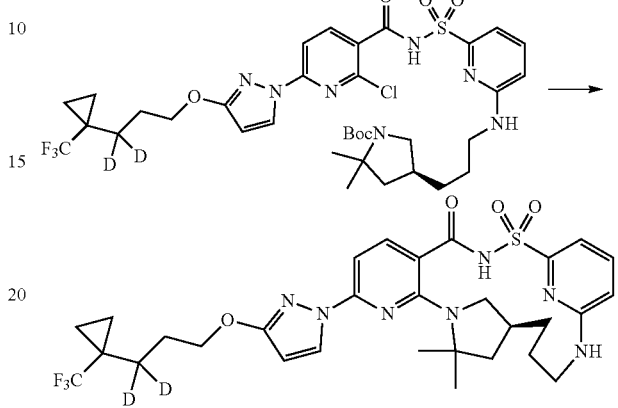

2-Chloro-6-[3-[3,3-dideuterio-3-[1-(trifluoromethyl)cyclopropyl]propoxy]pyrazol-1-yl]pyridine-3-carboxylic acid (250 mg, 0.6381 mmol) and freshly recrystallized carbonyl diimidazole (120 mg, 0.7401 mmol) were combined in tetrahydrofuran (6.0 mL) and stirred for 2 h at room temperature. Then tert-butyl (4S)-2,2-dimethyl-4-[3-[(6-sulfamoyl-2-pyridyl)amino]propyl]pyrrolidine-1-carboxylate (303 mg, 0.7345 mmol) was added followed by anhydrous 1,8-diazabicyclo[5.4.0]undec-7-ene (240 μL, 1.605 mmol) and the reaction was stirred at room temperature for 24 h. The reaction was diluted with ethyl acetate and washed with a saturated aqueous sodium bicarbonate solution followed by brine. The organic layer was separated, dried over sodium sulfate, filtered and evaporated then purified by silica gel chromatography using a gradient from 100% hexanes to 100% ethyl acetate which gave tert-butyl (4S)-4-[3-[[6-[[2-chloro-6-[3-[3,3-dideuterio-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (259 mg, 52%) as a white solid. ESI-MS m/z calc. 785.2918, found 786.2 (M+1)⁺; Retention time: 2.06 min (LC Method E).

tert-Butyl (4S)-4-[3-[[6-[[2-chloro-6-[3-[3,3-dideuterio-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (228 mg, 0.2900 mmol) was dissolved in dichloromethane (7 mL) and to the mixture was added trifluoroacetic acid (900 μL, 11.68 mmol) and stirred at room temperature for 15 min. Concentrated mixture to dryness under reduced pressure, redissolved in ethyl acetate and then added aqueous saturated sodium bicarbonate (10 mL). Separated the layers and further extracted the aqueous layer with ethyl acetate (2×10 mL). Combined organic layers, washed with brine then dried over sodium sulfate, filtered and evaporated to dryness under reduced pressure. Combined the resulting material, potassium carbonate (205 mg, 1.483 mmol), 3 Å molecular sieves and dimethyl sulfoxide (9.5 mL) in a vial, purged with nitrogen, capped, heated to 150° C. and stirred for 16 h. Cooled to room temperature and the mixture was filtered, diluted with ethyl acetate and washed with water (2×20 mL) followed by brine. The organic layer was further washed with water (1×) then dried over sodium sulfate, filtered and evaporated. The residue was purified on silica gel chromatography using a gradient from 100% hexanes to 100% ethyl acetate followed by a second silica gel chromatography column using a gradient from 100% dichloromethane to 10% methanol in dichloromethane to afford (14S)-12,12-dimethyl-8-(3-{3-[1-(trifluoromethyl)cyclopropyl]-3,3-dideuterio-propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Compound 269) (44.8 mg, 24%) as a white solid. ¹H NMR (400 MHz, dimethyl sulfoxide-$d_6$) δ 12.51 (s, 1H), 8.21 (d, J=2.8 Hz, 1H), 7.81 (d, J=8.3 Hz, 1H), 7.57 (t, J=7.9 Hz, 1H), 7.05 (d, J=7.2 Hz, 1H), 6.98 (s, 1H), 6.91 (d, J=8.2 Hz, 1H), 6.71 (d, J=8.6 Hz, 1H), 6.12 (d, J=2.8 Hz, 1H), 4.20 (t, J=6.3 Hz, 2H), 3.92 (d, J=12.0 Hz, 1H), 3.17 (d, J=5.2 Hz, 1H), 2.95 (d, J=13.3 Hz, 1H), 2.69 (d, J=15.6 Hz, 1H), 2.10 (d, J=18.7 Hz, 1H), 1.83 (t, J=6.2 Hz, 3H), 1.79-1.69 (m, 1H), 1.60 (s, 4H), 1.57 (d, J=12.5 Hz, 2H), 1.51 (s, 3H), 1.37-1.22 (m, 2H), 0.93-0.89 (m, 2H), 0.75 (t, J=1.6 Hz, 2H). ESI-MS m/z calc. 649.2627, found 650.2 (M+1)⁺; Retention time: 2.27 min (LC Method E).

Example 92: Preparation of (14S)-12,12-dimethyl-8-(3-{3-[1-(trifluoromethyl)cyclopropyl]-2,2-dideuterio-propoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 270)

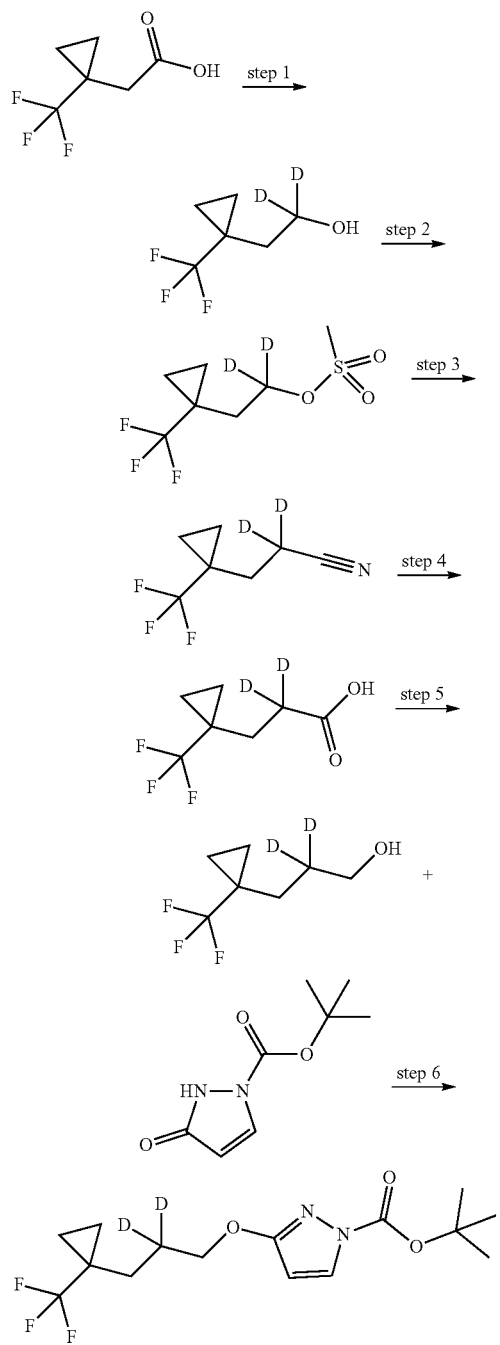

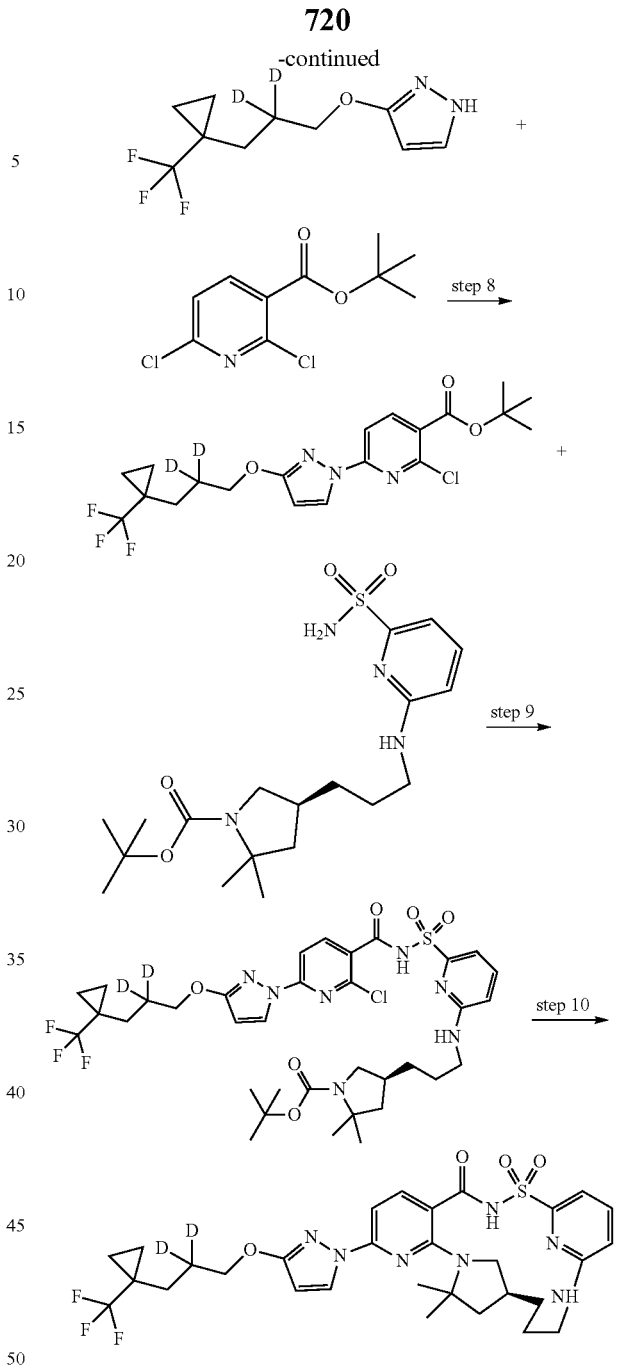

Step 1: 1,1-Dideuterio-2-[1-(trifluoromethyl)cyclopropyl]ethanol

To a suspension of lithium aluminum deuteride (1.0265 g, 25.684 mmol) in anhydrous tetrahydrofuran (50 mL) was added a solution of 2-[1-(trifluoromethyl)cyclopropyl]acetic acid (3.954 g, 19.757 mmol) in anhydrous tetrahydrofuran (50 mL) dropwise at 0° C. The reaction mixture was stirred at room temperature for an additional 16 h. The reaction mixture was diluted with diethyl ether (50 mL) and cooled to 0° C. Water (1 mL), 15% sodium hydroxide (aq.) (1 mL) and water (3 mL) were added to the reaction mixture at 0° C. The reaction was stirred at room temperature for 15 min. Anhydrous magnesium sulfate was added to the reaction mixture. The reaction was stirred for another 15 min. The white precipitate was removed by suction filtration and the solvent was removed under reduced pressure to afford 1,1-dideuterio-2-[1-(trifluoromethyl)cyclopropyl]ethanol (3.629 g, 82%) as a light yellow oil. $^1$H NMR (250 MHz, Chloroform-d) δ 1.83 (s, 2H), 1.43 (s, 1H), 1.04-0.91 (m, 2H), 0.72-0.62 (m, 2H).

Step 2: [1,1-Dideuterio-2-[1-(trifluoromethyl) cyclopropyl]ethyl]methanesulfonate

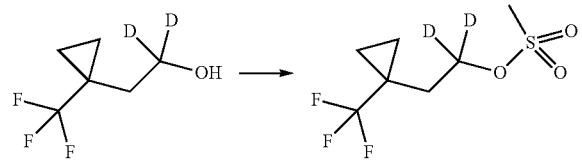 [SMILES: [2H]C([2H])(O)CC1(C(F)(F)F)CC1 ; [2H]C([2H])(CC1(C(F)(F)F)CC1)OS(C)(=O)=O]

To a solution of 1,1-dideuterio-2-[1-(trifluoromethyl)cyclopropyl]ethanol (3.629 g, 16.269 mmol) in dichloromethane (36 mL) was added triethylamine (4.9388 g, 6.8028 mL, 48.807 mmol). The mixture was cooled to 0° C. Methanesulfonyl chloride (2.2364 g, 1.5111 mL, 19.523 mmol) was added to the reaction mixture dropwise. The reaction mixture was stirred at room temperature for 3 h. The reaction mixture was diluted with dichloromethane (100 mL) and washed with 10% citric acid aqueous solution (30 mL), saturated sodium bicarbonate aqueous solution (30 mL) and brine (30 mL). The organic solution was dried over anhydrous sodium sulfate, filtered and concentrated under reduced pressure. The crude product was purified by silica gel chromatography using a gradient from 0% to 70% diethyl ether in hexane to furnish [1,1-dideuterio-2-[1-(trifluoromethyl)cyclopropyl]ethyl]methanesulfonate (3.413 g, 90%) as a clear liquid. $^1$H NMR (250 MHz, Chloroform-d) δ 3.02 (s, 3H), 2.02 (s, 2H), 1.14-0.95 (m, 2H), 0.81-0.63 (m, 2H).

Step 3: 2,2-Dideuterio-3-[1-(trifluoromethyl)cyclopropyl]propanenitrile

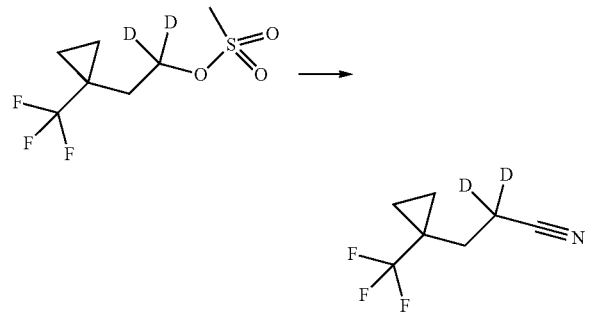

To a solution of [1,1-dideuterio-2-[1-(trifluoromethyl) cyclopropyl]ethyl]methanesulfonate (3.413 g, 14.571 mmol) in dimethyl sulfoxide (17 mL) was added sodium cyanide (892.62 mg, 18.214 mmol). The reaction mixture was stirred at 70° C. for 16 h. After cooled to room temperature, the reaction mixture was diluted with water (30 mL) and extracted with diethyl ether (3×30 mL). The combined organic layers were washed with water (2×30 mL) and brine (30 mL), dried over anhydrous magnesium sulfate, filtered and concentrated under vacuum. The residue was purified by silica gel chromatography using a gradient from 0% to 50% diethyl ether in pentane to furnish 2,2-dideuterio-3-[1-(trifluoromethyl)cyclopropyl]propanenitrile (2.181 g, 81%) as a clear liquid. $^1$H NMR (250 MHz, Chloroform-d) δ 1.92 (s, 2H), 1.14-1.01 (m, 2H), 0.74 (m, 2H).

Step 4: 2,2-Dideuterio-3-[1-(trifluoromethyl)cyclopropyl]propanoic Acid

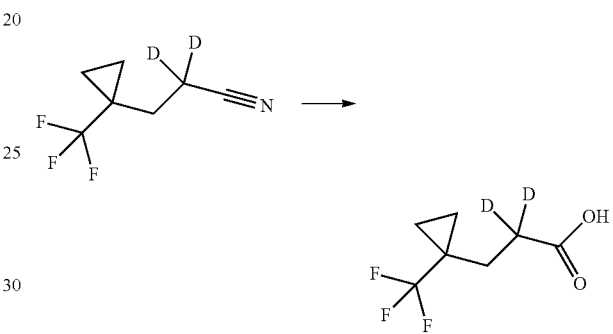

To a solution of 2,2-dideuterio-3-[1-(trifluoromethyl)cyclopropyl]propanenitrile (2.181 g, 11.753 mmol) in CH$_3$CwaterD (30 mL) was added D20 (4 mL) and sodium deuteroxide in D20 (4.8191 g, 40% w/w, 47.012 mmol). The reaction mixture was stirred at 70° C. for 20 h. The CH$_3$CwaterD was removed under reduced pressure. The resulting solution was diluted with D20 (20 mL) and washed with diethyl ether (2×20 mL). The aqueous solution was then acidified with 6 N hydrochloric acid to pH=1 and then it was extracted with diethyl ether (3×20 mL). The combined organic layers were washed with brine (20 mL), dried over anhydrous magnesium sulfate, filtered and concentrated under reduced pressure to furnish 2,2-dideuterio-3-[1-(trifluoromethyl)cyclopropyl]propanoic acid (1.945 g, 89%) as an amber liquid. $^1$H NMR (250 MHz, Chloroform-d) δ 1.89 (s, 2H), 1.10-0.88 (m, 2H), 0.75-0.52 (m, 2H).

Step 5: 2,2-Dideuterio-3-[1-(trifluoromethyl)cyclopropyl]propan-1-ol

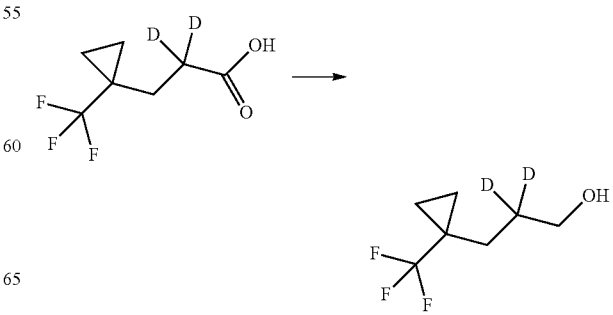

To a suspension of lithium aluminum hydride (521.15 mg, 0.5683 mL, 13.731 mmol) in anhydrous tetrahydrofuran (20 mL) was added a solution of 2,2-dideuterio-3-[1-(trifluoromethyl)cyclopropyl]propanoic acid (1.945 g, 10.562 mmol) in tetrahydrofuran (20 mL) at 0° C. dropwise. The reaction mixture was stirred at room temperature for 16 h. The reaction was diluted with diethyl ether (30 mL) and quenched with water (0.53 mL), 15% sodium hydroxide aqueous solution (0.53 mL) and water (1.59 mL) at 0° C. The reaction mixture was stirred at room temperature for 30 min and then anhydrous magnesium sulfate was added and stirred for an additional 15 min. The solid was filtered off and the filtrate was concentrated under vacuum to furnish 2,2-dideuterio-3-[1-(trifluoromethyl)cyclopropyl]propan-1-ol (1.423 g, 75%) as a clear liquid. $^1$H NMR (250 MHz, dimethyl sulfoxide-d$_6$) δ 4.44 (t, J=5.1 Hz, 1H), 3.38 (s, 2H), 1.57 (s, 2H), 0.87 (t, J=5.8 Hz, 2H), 0.69 (s, 2H).

Step 6: tert-Butyl 3-[2,2-dideuterio-3-[1-(trifluoromethyl)cyclopropyl]propoxy]pyrazole-1-carboxylate

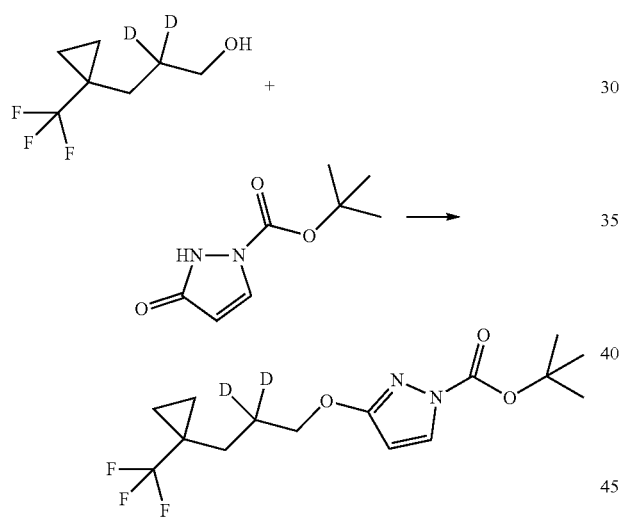

To a solution of tert-butyl 5-oxo-1H-pyrazole-2-carboxylate (775 mg, 4.208 mmol) and 2,2-dideuterio-3-[1-(trifluoromethyl)cyclopropyl]propan-1-ol (750 mg, 4.407 mmol) in tetrahydrofuran (10 mL) was added triphenylphosphine (1.156 g, 4.407 mmol). To the mixture was slowly added diisopropyl azodicarboxylate (870 μL, 4.419 mmol) dropwise over 10 min. The reaction mixture was stirred at room temperature for 30 min then at 50° C. for 30 min. The tetrahydrofuran was removed and the residue was purified by silica gel chromatography using a shallow gradient from 100% hexanes to 20% ethyl acetate in hexanes providing tert-butyl 3-[2,2-dideuterio-3-[1-(trifluoromethyl)cyclopropyl]propoxy]pyrazole-1-carboxylate (0.998 g, 71%) as a colorless oil. $^1$H NMR (400 MHz, Chloroform-d) δ 7.83 (d, J=2.9 Hz, 1H), 5.85 (d, J=2.9 Hz, 1H), 4.26 (s, 2H), 1.70 (s, 2H), 1.61 (s, 9H), 0.99-0.93 (m, 2H), 0.62-0.56 (m, 2H). ESI-MS m/z calc. 336.163, found 337.2 (M+1)$^+$; Retention time: 1.96 min (LC Method B).

Step 7: 3-[2,2-Dideuterio-3-[1-(trifluoromethyl)cyclopropyl]propoxy]-1H-pyrazole

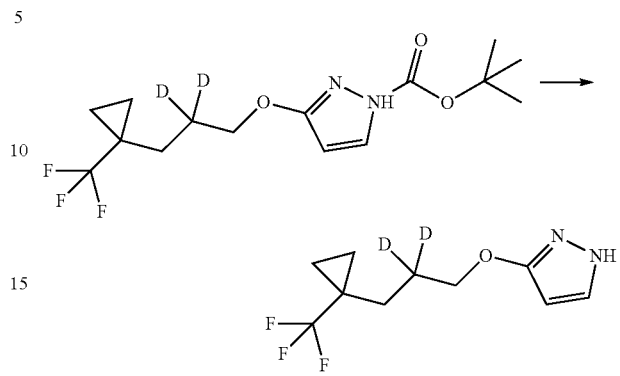

To a round bottom flask containing tert-butyl 3-[2,2-dideuterio-3-[1-(trifluoromethyl)cyclopropyl]propoxy]pyrazole-1-carboxylate (998 mg, 2.967 mmol) was added dichloromethane (20 mL) and trifluoroacetic acid (5.7 mL, 73.98 mmol). After 5 min, the reaction was evaporated to dryness and neutralized with saturated sodium bicarbonate solution. The reaction was extracted with ethyl acetate, the organic layer was dried over sodium sulfate, filtered and evaporated to provide 3-[2,2-dideuterio-3-[1-(trifluoromethyl)cyclopropyl]propoxy]-1H-pyrazole (700 mg, 100%) as a colorless oil. $^1$H NMR (400 MHz, Chloroform-d) δ 7.36 (d, J=2.6 Hz, 1H), 5.73 (d, J=2.5 Hz, 1H), 4.13 (d, J=1.6 Hz, 2H), 1.72 (s, 2H), 0.99-0.93 (m, 2H), 0.63-0.56 (m, 2H). ESI-MS m/z calc. 236.11055, found 237.1 (M+1)$^+$; Retention time: 1.41 min (LC Method B).

Step 8: tert-Butyl 2-chloro-6-[3-[2,2-dideuterio-3-[1-(trifluoromethyl) cyclopropyl]propoxy]pyrazol-1-yl]pyridine-3-carboxylate

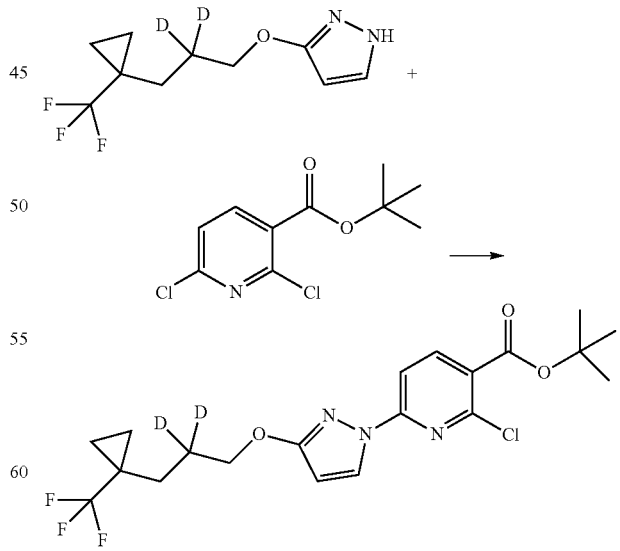

A mixture of 3-[2,2-dideuterio-3-[1-(trifluoromethyl)cyclopropyl]propoxy]-1H-pyrazole (700 mg, 2.963 mmol), tert-butyl 2,6-dichloropyridine-3-carboxylate (742 mg, 2.991 mmol), potassium carbonate (501 mg, 3.625 mmol) and 1,4-diazabicyclo[2.2.2]octane (71 mg, 0.6330 mmol) in dimethyl sulfoxide (5 mL) was stirred at room temperature for 15 h. The reaction was diluted with water and extracted with ethyl acetate. The combined extracts were washed with brine, dried over sodium sulfate, filtered and evaporated. The resultant residue was purified by silica gel column chromatography with a gradient from 100% hexanes to 20% ethyl acetate in hexanes to afford tert-butyl 2-chloro-6-[3-[2,2-dideuterio-3-[1-(trifluoromethyl)cyclopropyl]propoxy]pyrazol-1-yl]pyridine-3-carboxylate (472 mg, 36%) as a white solid. $^1$H NMR (400 MHz, Chloroform-d) δ 8.35 (d, J=2.8 Hz, 1H), 8.18 (d, J=8.4 Hz, 1H), 7.68 (d, J=8.4 Hz, 1H), 5.95 (d, J=2.8 Hz, 1H), 4.25 (s, 2H), 1.74 (s, 2H), 1.61 (s, 9H), 1.02-0.94 (m, 2H), 0.63-0.57 (m, 2H). ESI-MS m/z calc. 447.15054, found 448.23 (M+1)$^+$; Retention time: 0.95 min (LC Method A).

Step 9: tert-Butyl (4S)-4-[3-[[6-[[2-chloro-6-[3-[2,2-dideuterio-3-[1-(trifluoromethyl) cyclopropyl] propoxy]pyrazol-1-yl]pyridine-3-carbonyl]sulfamoyl]-2-pyridyl]amino]propyl]-2,2-dimethyl-pyrrolidine-1-carboxylate

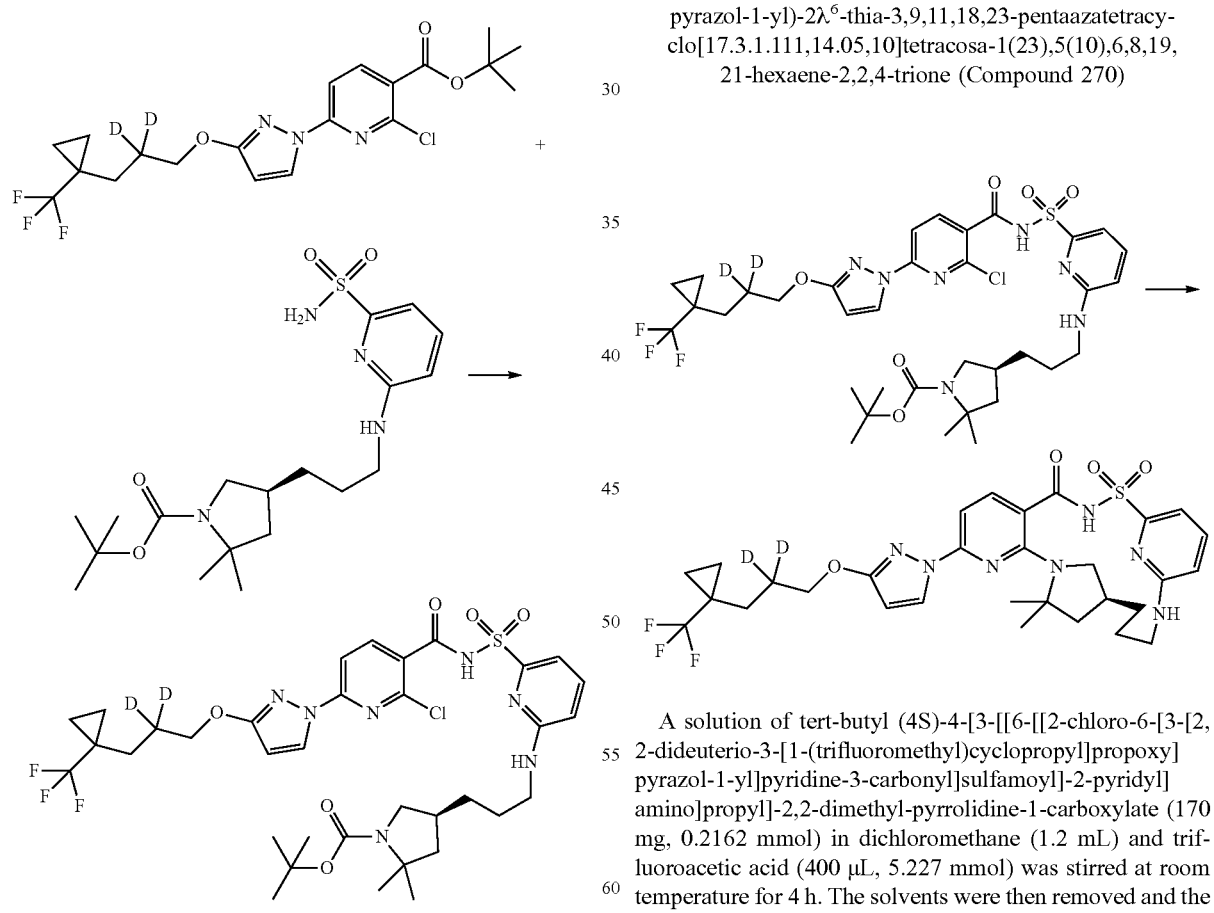

A solution of tert-butyl 2-chloro-6-[3-[2,2-dideuterio-3-[1-(trifluoromethyl)cyclopropyl]propoxy]pyrazol-1-yl]pyridine-3-carboxylate (250 mg, 0.5582 mmol) in dichloromethane (1.5 mL) and trifluoroacetic acid (500 μL, 6.490 mmol) was stirred at room temperature for 4 h. The solvents were then removed and the residue was dried under vacuum. The resultant residue was dissolved in tetrahydrofuran (2 mL) and carbonyl diimidazole (102 mg, 0.6291 mmol) was added and the mixture stirred for 2 h at room temperature. Then, tert-butyl (4S)-2,2-dimethyl-4-[3-[(6-sulfamoyl-2-pyridyl)amino]propyl]pyrrolidine-1-carboxylate (255 mg, 0.6181 mmol) was added followed by 1,8-diazabicyclo[5.4.0]undec-7-ene (130 μL, 0.8693 mmol) and the reaction was stirred for 16 h. The reaction was diluted with ethyl acetate and washed with a small amount of 1:1 saturated aqueous ammonium chloride/brine. The organics were separated, dried over sodium sulfate, filtered and evaporated. The resultant brown residue was purified by silica gel chromatography using a shallow gradient from 100% hexanes to 100% ethyl acetate to afford tert-butyl (4S)-4-[3-[[6-[[2-chloro-6-[3-[2,2-dideuterio-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (172 mg, 39%) as a white solid. ESI-MS m/z calc. 785.2918, found 786.4 (M+1)$^+$; Retention time: 0.93 min (LC Method A).

Step 10: (14S)-12,12-Dimethyl-8-(3-{3-[1-(trifluoromethyl)cyclopropyl]-2,2-dideuterio-propoxy}-1H-pyrazol-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 270)

A solution of tert-butyl (4S)-4-[3-[[6-[[2-chloro-6-[3-[2,2-dideuterio-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (170 mg, 0.2162 mmol) in dichloromethane (1.2 mL) and trifluoroacetic acid (400 μL, 5.227 mmol) was stirred at room temperature for 4 h. The solvents were then removed and the residue was dissolved in ethyl acetate. The mixture was washed with 2 mL of saturated sodium bicarbonate solution and the organic layer was collected and the solvent was removed under vacuum. The resultant residue was dissolved in dimethyl sulfoxide (8 mL) and 3 Å molecular sieves were added and the reaction mixture was stirred for 10 min. Then, cesium fluoride (101 mg, 0.6649 mmol) and potassium carbonate (96 mg, 0.6946 mmol) were added and the reaction mixture was heated at 150° C. for 16 h. The reaction mixture was filtered through Whatman filter disc (puradisc 25 TF) and the filtrate was purified by a reverse phase HPLC-MS method using a dual gradient run from 30%-99% mobile phase B over 15.0 min (mobile phase A=water (0.05% hydrochloric acid), mobile phase B=acetonitrile) to afford (14S)-12,12-dimethyl-8-(3-{3-[1-(trifluoromethyl)cyclopropyl]-2,2-dideuterio-propoxy}-1H-pyrazol-1-yl)-2$\lambda^6$-thia-3,9,11,18,23-pentaazatetracyclo[17.3.1.1 11,14.0 5,10]tetracosa-1(23),5(10),6,8,19,21-hexaene-2,2,4-trione (Compound 270) (62.4 mg, 44%) as an off white solid. $^1$H NMR (400 MHz, Chloroform-d) δ 9.87 (s, 1H), 8.19 (d, J=2.8 Hz, 1H), 8.04 (d, J=8.3 Hz, 1H), 7.56-7.44 (m, 2H), 7.23 (d, J=8.4 Hz, 1H), 6.55 (dd, J=8.2, 1.0 Hz, 1H), 5.91 (d, J=2.8 Hz, 1H), 4.71 (dd, J=8.6, 3.4 Hz, 1H), 4.24 (s, 2H), 3.89 (s, 1H), 3.33 (dd, J=10.1, 7.4 Hz, 1H), 3.15 (dd, J=14.0, 3.6 Hz, 1H), 3.05 (t, J=9.8 Hz, 1H), 2.56 (s, 1H), 2.06 (dd, J=12.2, 7.7 Hz, 1H), 1.74 (s, 2H), 1.61 (t, J=4.0 Hz, 10H), 1.01-0.93 (m, 2H), 0.64-0.57 (m, 2H). ESI-MS m/z calc. 649.2627, found 650.12 (M+1)$^+$; Retention time: 1.75 min (LC Method G).

Example 93: Preparation of (14S)-8-[3-(2-{dispiro[2.0.2.1]heptan-7-yl}ethoxy)-1H-pyrazol-1-yl]-12,12-di(trideuterio)methyl-2$\lambda^6$-thia-3,9,11,18,23-pentaazatetracyclo[17.3.1.1 11,14.0 5,10]tetracosa-1(23),5,7,9,19,21-hexaene-2,2,4-trione (Compound 274)

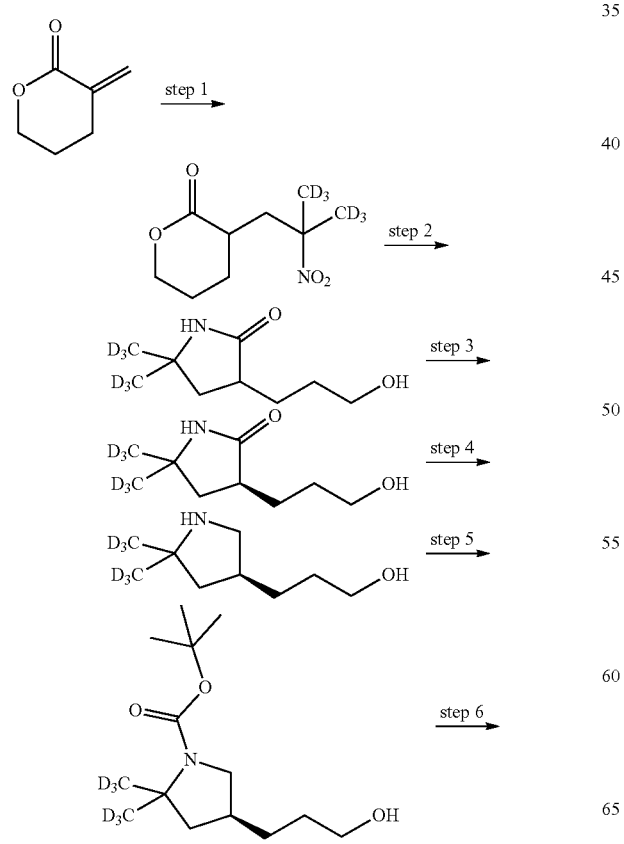

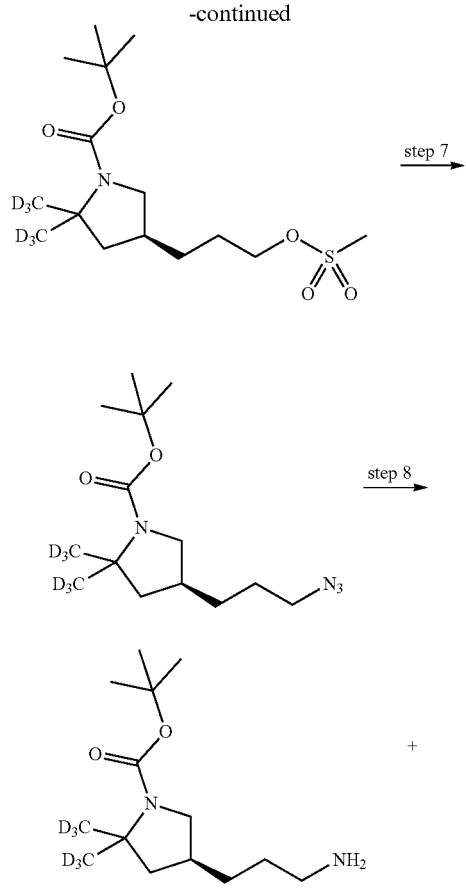

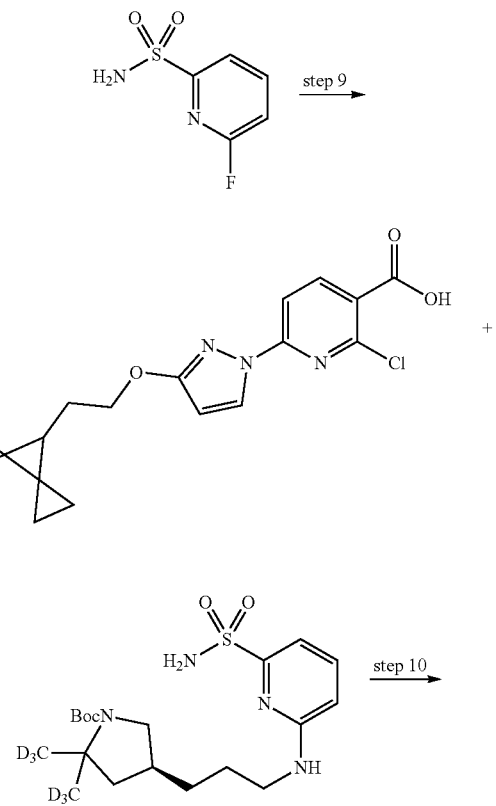

729

-continued

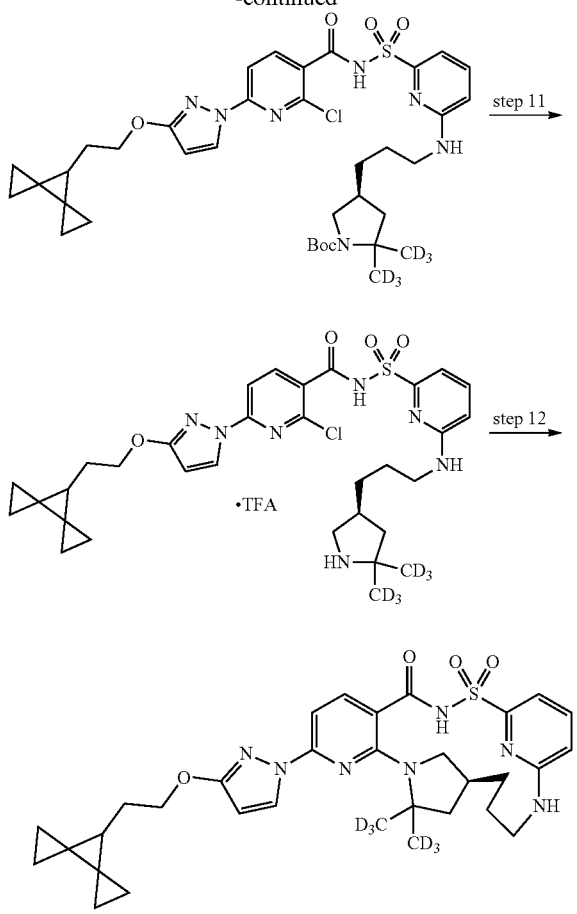

step 11 step 12

·TFA

Step 1: 3-[3,3,3-Trideuterio-2-nitro-2-(trideuteriomethyl)propyl]tetrahydropyran-2-one

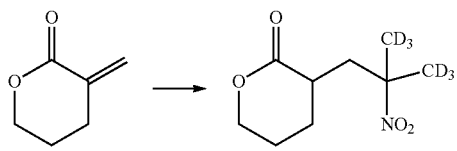

1,8-diazabicyclo[5.4.0]undec-7-ene (7.7 mL, 51.3 mmol) was added to a mixture of 1,1,1,3,3,3-hexadeuterio-2-nitropropane (CDN Isotopes, Quebec, Canada) (23.4 g, 246.2 mmol) and 3-methylene-tetrahydropyran-2-one (23.0 g, 205.2 mmol). The reaction was exothermic: after the initial heat evolution had dissipated the mixture was heated in an 80° C. oil bath for 18 h then cooled to room temperature and diluted with 1M hydrochloric acid (100 mL) and dichloromethane (500 mL). The phases were separated. The aqueous phase was discarded and the organic phase was dried over sodium sulfate, filtered and concentrated in vacuo to obtain 3-[3,3,3-trideuterio-2-nitro-2-(trideuteriomethyl)propyl]tetrahydropyran-2-one (41.8 g, 98%) as a yellow oil. The material was used in the next step without further purification. ESI-MS m/z calc. 207.22, found 208.10 (M+1)$^+$: Retention time: 3.29 min (LC Method Q).

730

Step 2: 3-(3-Hydroxypropyl)-5,5-bis(trideuteriomethyl)pyrrolidin-2-one

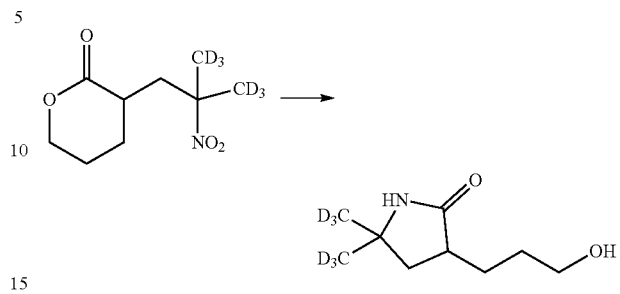

A slurry of Raney Nickel (5 g, 85 mmol) in water (10 mL) was added to a solution of 3-[3,3,3-trideuterio-2-nitro-2-(trideuteriomethyl)propyl]tetrahydropyran-2-one (41.8 g, 201.8 mmol) in ethanol (600 mL). The resulting slurry was hydrogenated under 60 PSI H2 at 80° C. for 22 h, cooled to room temperature, filtered through Celite and then concentrated in vacuo to obtain an orange oil. The orange oil was purified by silica gel chromatography (0%-50% ethyl acetate in hexane gradient) to obtain pure 3-(3-hydroxypropyl)-5,5-bis(trideuteriomethyl)pyrrolidin-2-one (7 g, 20%) as an off-white solid. $^1$H NMR (250 MHz, dimethyl sulfoxide-d$_6$) δ 7.62 (s, 1H), 4.39 (t, 1H), 3.81 (m, 2H), 2.37 (m, 2H), 2.01 (dd, 1H), 1.73 (m, 1H), 1.43 (m, 3H), 1.17 (m, 1H). ESI-MS m/z calc. 177.20, found 178.00 (M+1)$^+$; Retention time: 1.91 min (LC Method Q).

Step 3: (3S)-3-(3-hydroxypropyl)-5,5-bis(trideuteriomethyl)pyrrolidin-2-one

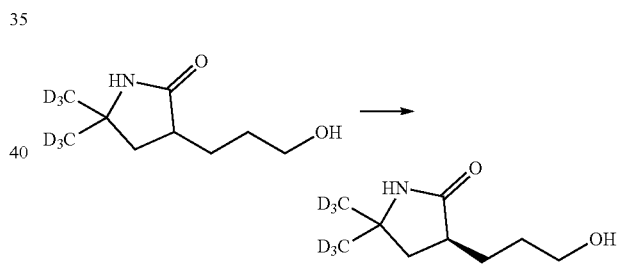

Subjected racemic 3-(3-hydroxypropyl)-5,5-bis(trideuteriomethyl)pyrrolidin-2-one (6.78 g) to chiral separation by SFC chromatography using a ChiralPak IA (250×21.2 mm column, 5 μm particle size) with 10% methanol (no modifier)/90% carbon dioxide mobile phase at 70 mL/min over 7.0 min (injection volume=500 μL of 32 mg/mL solution in methanol) giving as the first enantiomer to elute, (3S)-3-(3-hydroxypropyl)-5,5-bis(trideuteriomethyl)pyrrolidin-2-one (2.4 g, 70.7%) as an off-white solid. ESI-MS m/z calc. 177.20, found 178.00 (M+1)$^+$; Retention time: 1.91 min (LC Method B).

Step 4: 3-[(3S)-5,5-bis(trideuteriomethyl)pyrrolidin-3-yl]propan-1-ol

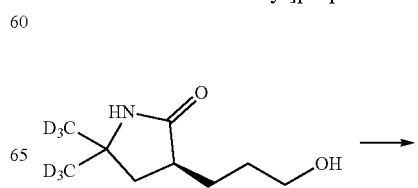

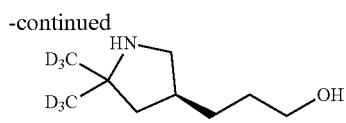

To a suspension of lithium aluminum hydride (1.37 g, 35.16 mmol) (2 pellets) in tetrahydrofuran (22 mL) at room temperature, under a nitrogen atmosphere, was added solid (3S)-3-(3-hydroxypropyl)-5,5-bis(trideuteriomethyl)pyrrolidin-2-one (2.4 g, 13.54 mmol) over 20 min in portions. The internal temperature was maintained below 32° C. during the addition. The reaction was then heated to reflux and stirred under a nitrogen atmosphere. After 19 h, the reaction became thick and was no longer stirring. The reaction was cooled to room temperature. Added tetrahydrofuran (10 mL) and methyl tert-butyl ether (10 mL) to the mixture, followed by the dropwise addition of saturated sodium sulfate (aqueous) until no more bubbles formed. An additional 10 mL of saturated sodium sulfate solution was added to the cloudy solution. The mixture was filtered through Celite and washed with methyl tert-butyl ether. The filtrate was concentrated to provide 3-[(3S)-5,5-bis(trideuteriomethyl)pyrrolidin-3-yl]propan-1-ol (1.85 g, 83%) as a clear oil. $^1$H NMR (400 MHz, dimethyl sulfoxide-$d_6$) δ 4.32 (t, J=5.2 Hz, 1H), 3.36 (q, J=6.2 Hz, 3H), 2.95 (dd, J=10.6, 7.5 Hz, 1H), 2.40 (dd, J=10.6, 7.6 Hz, 1H), 2.03 (hept, J=7.7 Hz, 1H), 1.86 (m, 1H), 1.68 (dd, J=12.1, 8.2 Hz, 1H), 1.47-1.22 (m, 5H), 1.01 (dd, J=12.1, 8.8 Hz, 1H).

Step 5: tert-Butyl (4S)-4-(3-hydroxypropyl)-2,2-bis(trideuteriomethyl)pyrrolidine-1-carboxylate

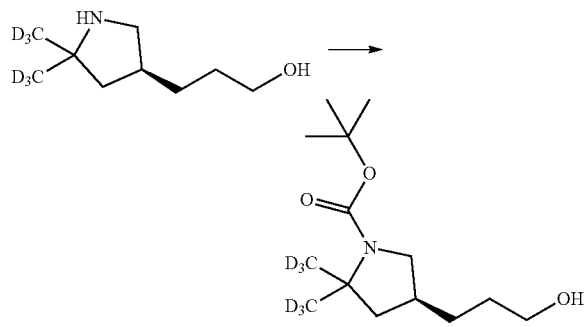

To a solution of 3-[(3S)-5,5-bis(trideuteriomethyl)pyrrolidin-3-yl]propan-1-ol (1.85 g, 11.33 mmol) (1.85 g) in methyl tert-butyl ether (11.5 mL) was added tert-butoxycarbonyl tert-butyl carbonate (2.60 g, 11.91 mmol). The reaction was stirred at room temperature under a nitrogen atmosphere. After 17 h, the reaction was diluted with water and extracted. The aqueous layer was extracted again with methyl tert-butyl ether. The organic layers were combined, dried with sodium sulfate, filtered and concentrated to provide a clear oil (2.94 g). The clear oil was purified by flash chromatography (silica, 30% ethyl acetate in hexanes) to provide tert-butyl (4S)-4-(3-hydroxypropyl)-2,2-bis(trideuteriomethyl)pyrrolidine-1-carboxylate (2.41 g, 81%) as a clear oil. $^1$H NMR (400 MHz, dimethyl sulfoxide-$d_6$) δ 4.36 (t, J=5.2 Hz, 1H), 3.61-3.48 (m, 1H), 3.37 (q, J=6.0 Hz, 2H), 2.76 (q, J=10.1 Hz, 1H), 2.14-1.96 (m, 1H), 1.95-1.77 (m, 1H), 1.48-1.24 (m, 14H).

Step 6: tert-Butyl (4S)-4-(3-methylsulfonyloxypropyl)-2,2-bis(trideuteriomethyl) pyrrolidine-1-carboxylate

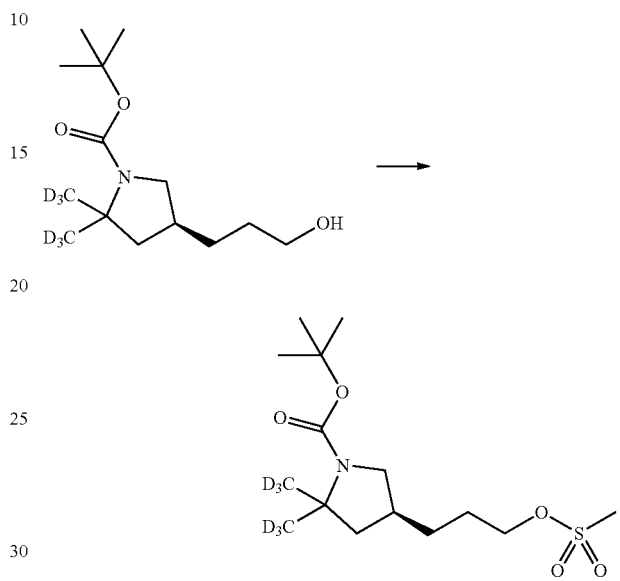

To a solution of tert-butyl (4S)-4-(3-hydroxypropyl)-2,2-bis(trideuterio methyl)pyrrolidine-1-carboxylate (2.41 g, 9.149 mmol) in methyl tert-butyl ether (15 mL) was added triethylamine (1.111 g, 1.530 mL, 10.98 mmol) followed by methanesulfonyl chloride (781 µL, 10.09 mmol) in an ice water bath over 5 min. A white precipitate formed immediately. The reaction mixture was brought to room temperature. The reaction mixture was then diluted with methyl tert-butyl ether, filtered, washed with water, dried over sodium sulfate, filtered and concentrated. After standing overnight, the tert-butyl (4S)-4-(3-methylsulfonyloxypropyl)-2,2-bis(trideuteriomethyl)pyrrolidine-1-carboxylate (2.64 g, 81%) solidified to become a white solid. $^1$H NMR (400 MHz, dimethyl sulfoxide-$d_6$) δ 4.19 (t, J=6.4 Hz, 2H), 3.63-3.50 (m, 1H), 3.16 (s, 3H), 2.79 (q, J=10.3 Hz, 1H), 2.17-2.02 (m, 1H), 1.97-1.80 (m, 1H), 1.73-1.58 (m, 2H), 1.47-1.26 (m, 12H).

Step 7: tert-Butyl (4S)-4-(3-azidopropyl)-2,2-bis(trideuteriomethyl)pyrrolidine-1-carboxylate

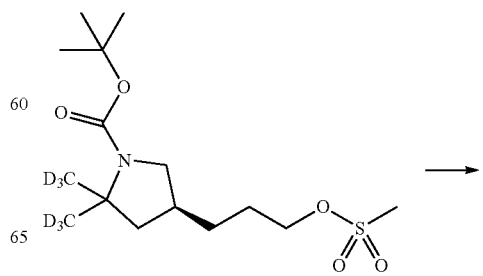

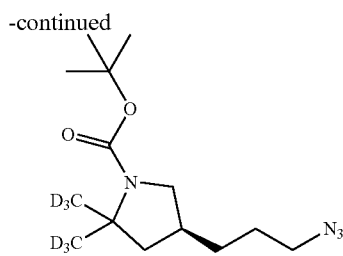

To a solution of tert-butyl (4S)-4-(3-methylsulfonyloxypropyl)-2,2-bis(trideuteriomethyl)pyrrolidine-1-carboxylate (2.64 g, 7.576 mmol) in N,N-dimethylformamide (26 mL) at room temperature was added sodium azide (1.07 g, 16.46 mmol). The reaction was heated to 50° C. and stirred under a nitrogen atmosphere. The reaction was cooled to room temperature and extracted with ethyl acetate (200 mL) and washed with water (50 mL). The organic layer was dried with sodium sulfate, filtered and concentrated. Heptane was added and concentrated to remove any excess N,N-dimethylformamide giving tert-butyl (4S)-4-(3-azidopropyl)-2,2-bis(trideuterio methyl)pyrrolidine-1-carboxylate (1.77 g, 80.2%). $^1$H NMR (400 MHz, dimethyl sulfoxide-d$_6$) δ 3.55 (dt, J=10.7, 7.1 Hz, 1H), 3.32 (t, 2H), 2.85-2.70 (m, 1H), 2.20-2.01 (m, 1H), 1.88 (td, J=14.0, 13.5, 6.1 Hz, 1H), 1.61-1.28 (m, 14H).

Step 8: tert-Butyl (4S)-4-(3-aminopropyl)-2,2-bis(trideuteriomethyl)pyrrolidine-1-carboxylate

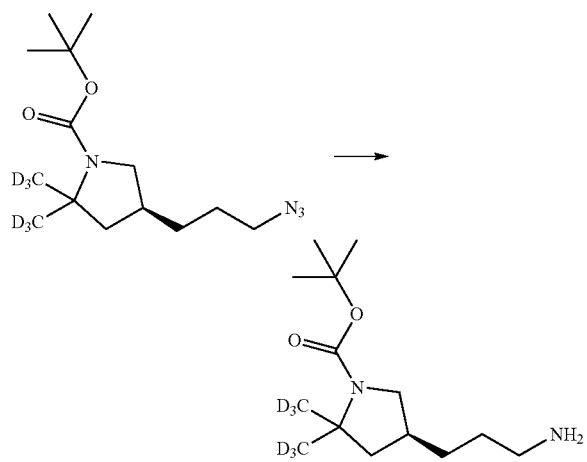

To a solution of tert-butyl (4S)-4-(3-azidopropyl)-2,2-bis(trideuterio methyl)pyrrolidine-1-carboxylate (1.77 g, 6.137 mmol) in ethyl acetate (330.8 mL) was added platinum oxide (50.68 mg, 0.2232 mmol). The reaction mixture was hydrogenated using a Buchiglasuster hydrogenation apparatus. The mixture was purged three times from vacuum with nitrogen, then three times from vacuum with hydrogen (0.4 L). The reaction was stirred under a hydrogen atmosphere at 930 rpm at about 2.18 bars pressure of hydrogen at 25° C. for 18 h. 337 mL of hydrogen gas was consumed. The reaction mixture was filtered through Celite and washed with water (25 mL). The organic layer was washed with brine (25 mL), dried with sodium sulfate, filtered and concentrated to provide tert-butyl (4S)-4-(3-aminopropyl)-2,2-bis(trideuteriomethyl)pyrrolidine-1-carboxylate (1.66 g, quantitative yield) as a dark oil. $^1$H NMR (400 MHz, dimethyl sulfoxide-d$_6$) δ 3.53 (dt, J=12.2, 6.5 Hz, 1H), 2.76 (q, J=10.2 Hz, 1H), 2.18-1.99 (m, 1H), 1.86 (td, J=15.8, 14.2, 6.1 Hz, 1H), 1.55-1.21 (m, 16H).

Step 9: tert-Butyl (4S)-4-[3-[(6-sulfamoyl-2-pyridyl)amino]propyl]-2,2-bis(trideuterio methyl)pyrrolidine-1-carboxylate

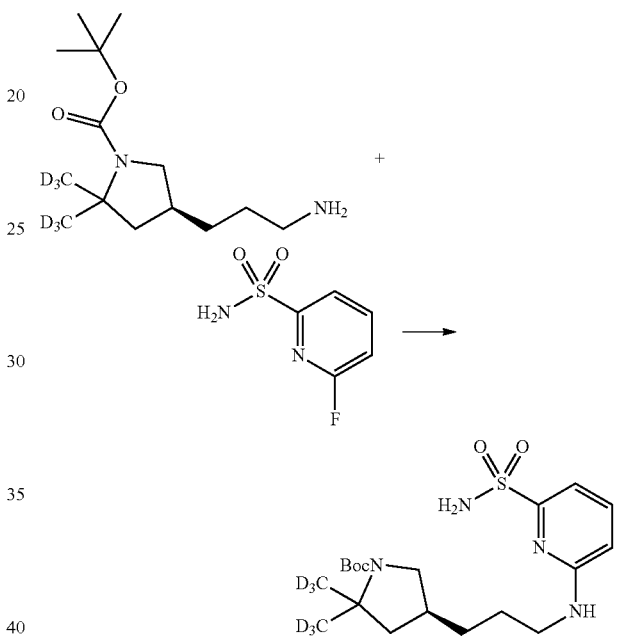

To a solution of tert-butyl (4S)-4-(3-aminopropyl)-2,2-bis(trideuteriomethyl) pyrrolidine-1-carboxylate (1.61 g, 6.135 mmol) in dimethyl sulfoxide (30 mL) was added diisopropylethylamine (1.28 mL, 7.349 mmol) followed by 6-fluoropyridine-2-sulfonamide (1.31 g, 7.436 mmol). The reaction was placed under a nitrogen atmosphere and stirred at 85° C. for 18 h. The reaction mixture was diluted with methyl tert-butyl ether (50 mL) and extracted with water (20 mL). The organic layer was washed with brine, dried over sodium sulfate, filtered and concentrated. The residue was dissolved in dichloromethane and purified by silica gel chromatography (60% ethyl acetate in hexane). To combined fractions containing the product, a second purification was completed by silica gel chromatography (gradient from 0%-5% methanol in dichloromethane) to provide tert-butyl (4S)-4-[3-[(6-sulfamoyl-2-pyridyl)amino]propyl]-2,2-bis(trideuteriomethyl)pyrrolidine-1-carboxylate (1.72 g, 67%) as a white sticky solid. $^1$H NMR (400 MHz, dimethyl sulfoxide-d$_6$) δ 7.51 (t, J=8.5, 7.2 Hz, 1H), 7.06 (s, 2H), 7.01-6.88 (m, 2H), 6.61 (d, J=8.4 Hz, 1H), 3.55 (q, J=9.2 Hz, 1H), 3.30-3.21 (m, 2H), 2.88-2.71 (m, 1H), 2.19-2.00 (m, 1H), 2.01-1.78 (m, 1H), 1.66-1.27 (m, 14H).

Step 10: tert-Butyl (4S)-4-[3-[[6-[[2-chloro-6-[3-(2-dispiro[2.0.2.1]heptan-7-ylethoxy) pyrazol-1-yl]pyridine-3-carbonyl]sulfamoyl]-2-pyridyl]amino]propyl]-2,2-bis(trideuteriomethyl)pyrrolidine-1-carboxylate Step 11: N-[[6-[3-[(3S)-5,5-bis(trideuteriomethyl)pyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide

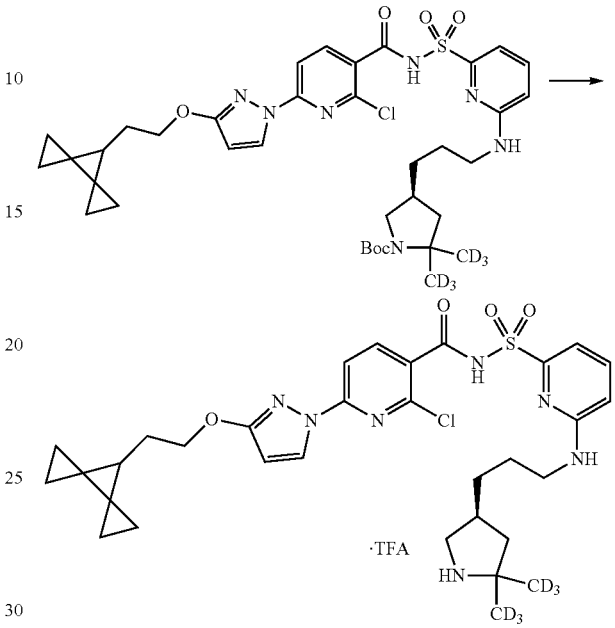

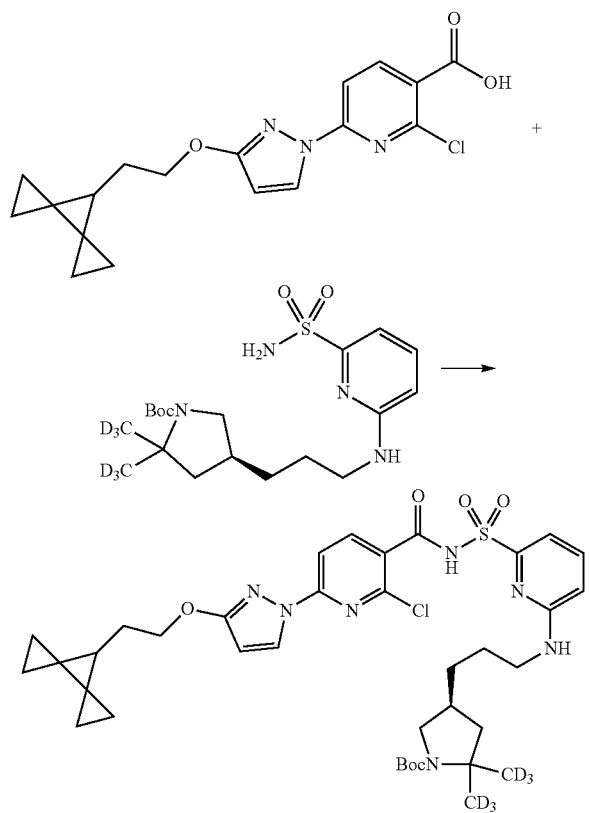

To a solution of 2-chloro-6-[3-(2-dispiro[2.0.2.1]heptan-7-ylethoxy)pyrazol-1-yl]pyridine-3-carboxylic acid (250 mg, 0.6892 mmol) in tetrahydrofuran (2.058 mL) was added carbonyl diimidazole (134 mg, 0.8264 mmol). The reaction stirred at room temperature for 30 min. Added carbonyl diimidazole (11.8 mg, 0.07277 mmol) and allowed to stir for another 30 min. A solution of tert-butyl (4S)-4-[3-[(6-sulfamoyl-2-pyridyl)amino]propyl]-2,2-bis(trideuteriomethyl)pyrrolidine-1-carboxylate (307 mg, 0.7334 mmol) in tetrahydrofuran (420 µL) was added dropwise followed by 1,8-diazabicyclo[5.4.0]undec-7-ene (310 µL, 2.073 mmol). The reaction continued to stir at room temperature under nitrogen gas. After 18 h, water (8.2 mL), ethyl acetate (25 mL) and hydrochloric acid (710 µL of 6 M, 4.260 mmol) were added giving pH=3 in the aqueous layer. The reaction mixture was extracted with ethyl acetate, dried over sodium sulfate, filtered and concentrated. Purification was performed via flash chromatography (50% ethyl acetate in hexane) to provide tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-bis(trideuteriomethyl)pyrrolidine-1-carboxylate (308 mg, 59%). ESI-MS m/z calc. 759.35, found 760.4 (M+1)⁺; Retention time: 2.20 min (LC Method G).

To a solution of tert-butyl (4S)-4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]propyl]-2,2-bis(trideuteriomethyl)pyrrolidine-1-carboxylate (308 mg, 0.3565 mmol) in dichloromethane (1.26 mL) and toluene (624 µL) was added trifluoroacetic acid (411 µL, 5.335 mmol) and the mixture was stirred at ambient temperature for 2.5 h. The reaction mixture was concentrated, diluted with toluene (4.989 mL) and concentrated at 45° C. to give N-[[6-[3-[(3S)-5,5-bis(trideuteriomethyl)pyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (276 mg, 100%). ESI-MS m/z calc. 659.2928, found 660.4 (M+1)⁺; Retention time: 1.11 min (LC Method G).

Step 12: (14S)-8-[3-(2-{Dispiro[2.0.2.1]heptan-7-yl}ethoxy)-1H-pyrazol-1-yl]-12,12-di(trideuterio)methyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 274)

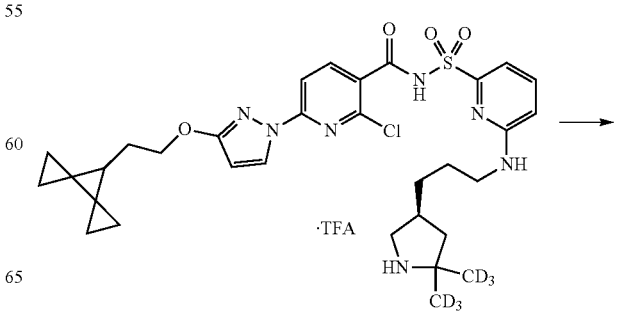

737

-continued

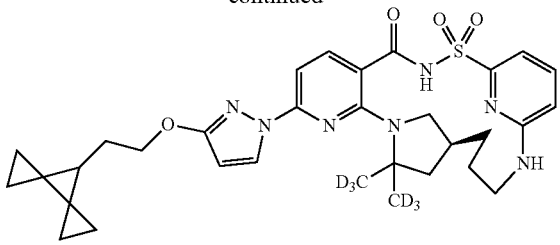

To a solution of N-[[6-[3-[(3S)-5,5-bis(trideuteriomethyl)pyrrolidin-3-yl]propylamino]-2-pyridyl]sulfonyl]-2-chloro-6-[3-(2-dispiro[2.0.2.1]heptan-7-ylethoxy)pyrazol-1-yl]pyridine-3-carboxamide (trifluoroacetate salt) (356 mg, 0.4598 mmol) in NMP (8.6 mL) was added potassium carbonate (322 mg, 2.330 mmol). The mixture was purged with nitrogen 3 times and was heated at 150° C. overnight. The reaction mixture was cooled to room temperature and added to water (18 mL). The mixture was carefully acidified with hydrochloric acid (5 mL of 1 M, 5.000 mmol) affording a foamy slurry. The solid was collected by filtration using a medium frit. The filtrate did not contain product and was discarded. The wet filter cake was dissolved in ethyl acetate (21 mL) and washed with 10 mL of brine. The aqueous phase was separated and the organic phase was dried over magnesium sulfate, filtered and concentrated in vacuo affording a light yellow oil. The crude product was diluted with acetonitrile and chromatographed on a 30 g reverse phase $C_{18}$ column eluting with a gradient from 60%-100% acetonitrile in water giving (14S)-8-[3-(2-{dispiro[2.0.2.1]heptan-7-yl}ethoxy)-1H-pyrazol-1-yl]-12,12-di(trideuterio)methyl-2λ$^6$-thia-3,9,11,18,23-pentaazatetracyclo[17.3.1.111,14.05,10]tetracosa-1(23),5,7,9,19,21-hexaene-2,2,4-trione (Compound 274) (135 mg, 47%) as a cream colored foam. $^1$H NMR (400 MHz, dimethyl sulfoxide-d$_6$) δ 12.50 (s, 1H), 8.20 (d, J=2.8 Hz, 1H), 7.81 (d, J=8.2 Hz, 1H), 7.57 (t, J=7.8 Hz, 1H), 7.19-6.81 (m, 3H), 6.71 (d, J=8.5 Hz, 1H), 6.08 (d, J=2.8 Hz, 1H), 4.21 (t, J=6.7, 1.4 Hz, 2H), 4.08-3.81 (m, 1H), 2.95 (d, J=13.3 Hz, 1H), 2.80-2.57 (m, 1H), 2.18 (d, J=50.0 Hz, 1H), 1.97-1.68 (m, 4H), 1.68-1.42 (m, 4H), 1.42-1.11 (m, 1H), 0.95-0.72 (m, 4H), 0.72-0.56 (m, 2H), 0.56-0.33 (m, 2H). ESI-MS m/z calc. 623.32, found 624.3 (M+1)$^+$; Retention time: 1.98 min (LC Method G).

Example 94: Preparation of 20,20,22-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.111,14.02,7]docosa-2,4,6,11(22),12-pentaene-8,10,10-trione (Racemic Atropisomer 1) (Compound 280), 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.111,14.02,7]docosa-2,4,6,11(22),12-pentaene-8,10,10-trione (Compound 281) and 20,20,22-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.111,14.02,7]docosa-2,4,6,11(22),12-pentaene-8,10,10-trione (Racemic Atropisomer 2) (Compound 282)

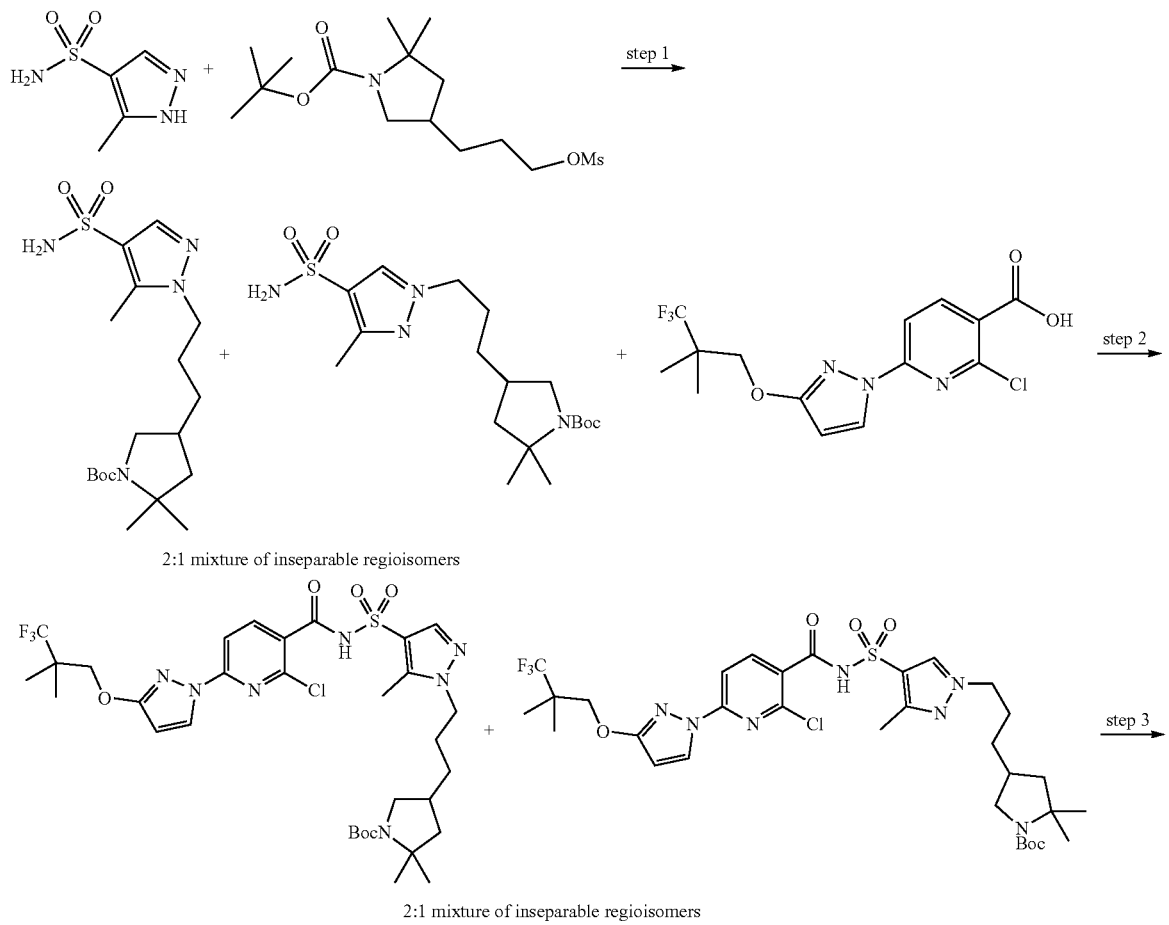

739

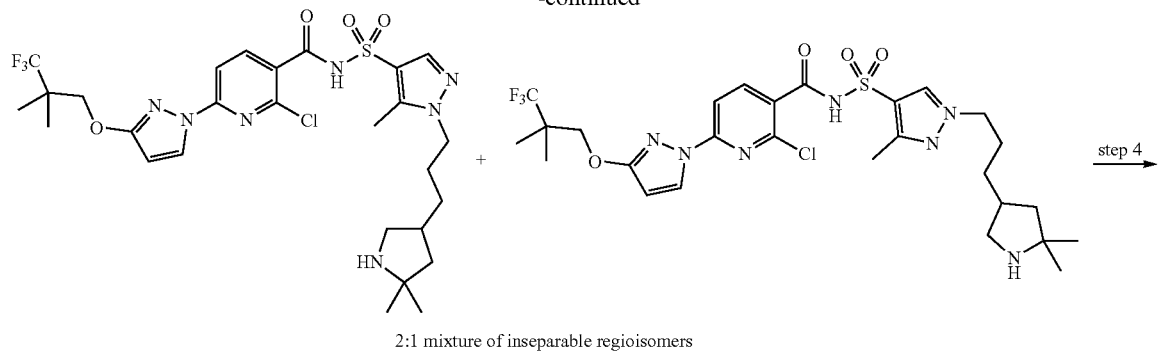

2:1 mixture of inseparable regioisomers

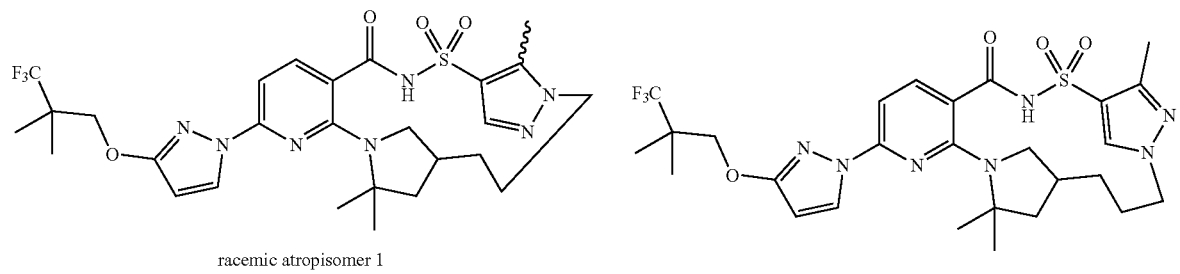

racemic atropisomer 1

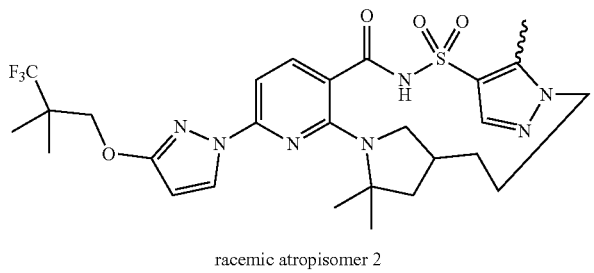

racemic atropisomer 2

Step 1: tert-Butyl 2,2-dimethyl-4-[3-(5-methyl-4-sulfamoyl-pyrazol-1-yl)propyl]pyrrolidine-1-carboxylate and tert-butyl 2,2-dimethyl-4-[3-(3-methyl-4-sulfamoyl-pyrazol-1-yl)propyl]pyrrolidine-1-carboxylate (2:1 Mixture of Inseparable Regioisomers)

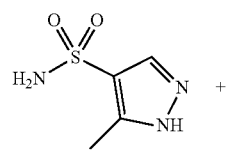

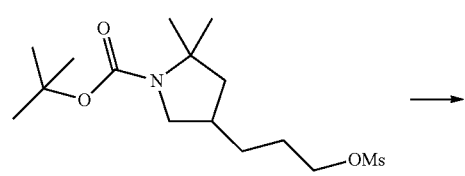

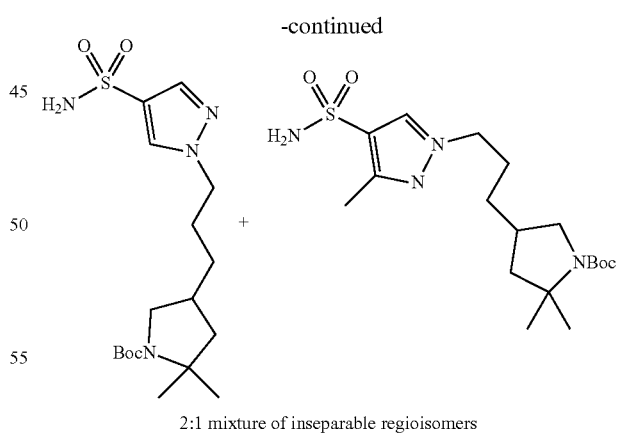

2:1 mixture of inseparable regioisomers

To a round bottom flask containing tert-butyl 2,2-dimethyl-4-(3-methylsulfonyloxypropyl)pyrrolidine-1-carboxylate (1.97 g, 5.873 mmol) was added N,N-dimethylformamide (20 mL), potassium carbonate (2.44 g, 17.65 mmol) and 5-methyl-1H-pyrazole-4-sulfonamide (947 mg, 5.875 mmol). The reaction was heated at 65° C. for 24 h. The reaction was filtered and the flask and filter cake were further washed with ethyl acetate. The filtrate was evaporated and purified via HPLC (20%-80% acetonitrile in water gradient with a 0.1% hydrochloric acid modifier). The purified fractions were evaporated together to provide a white foam. The inseparable regioisomeric products, tert-butyl 2,2-dimethyl-4-[3-(5-methyl-4-sulfamoyl-pyrazol-1-yl)propyl]pyrrolidine-1-carboxylate and tert-butyl 2,2-dimethyl-4-[3-(3-methyl-4-sulfamoyl-pyrazol-1-yl)propyl]pyrrolidine-1-carboxylate (972 mg combined yield, 41%), ESI-MS m/z calc. 400.21442, found 345.2 (M+1)+; Retention time: 1.51 min (LC Method B) were confirmed to be present in the product mixture as a 2:1 ratio by $^1$H NMR analysis.

Step 2: tert-Butyl 4-[3-[4-[[2-chloro-6-[3-(3,3,3-trifluoro-2,2-dimethyl-propoxy)pyrazol-1-yl]pyridine-3-carbonyl]sulfamoyl]-5-methyl-pyrazol-1-yl]propyl]-2,2-dimethyl-pyrrolidine-1-carboxylate and tert-butyl 4-[3-[4-[[2-chloro-6-[3-(3,3,3-trifluoro-2,2-dimethyl-propoxy)pyrazol-1-yl]pyridine-3-carbonyl]sulfamoyl]-3-methyl-pyrazol-1-yl]propyl]-2,2-dimethyl-pyrrolidine-1-carboxylate (2:1 Mixture of Inseparable Regioisomers)

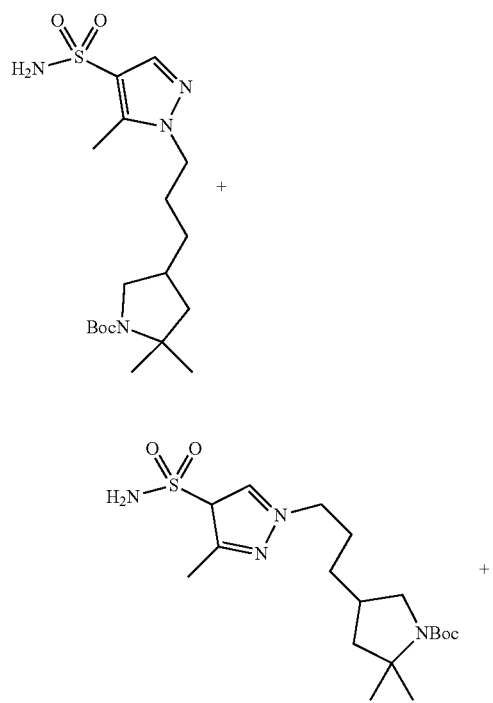

2:1 mixture of inseparable regioisomers

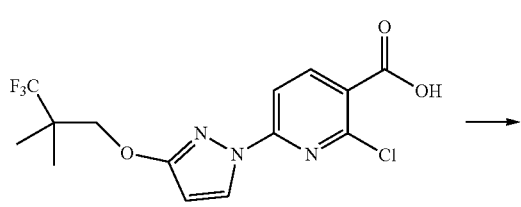

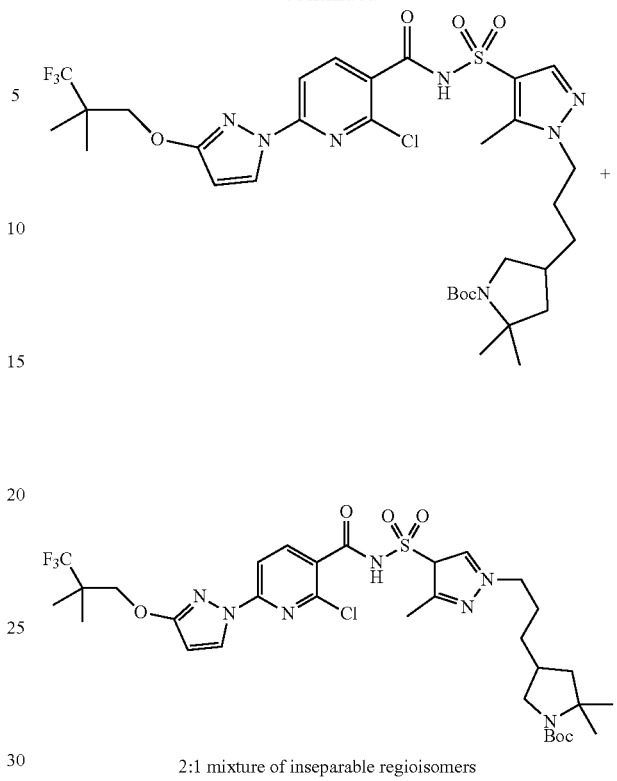

2:1 mixture of inseparable regioisomers

To a round bottom flask was added 2-chloro-6-[3-(3,3,3-trifluoro-2,2-dimethyl-propoxy)pyrazol-1-yl]pyridine-3-carboxylic acid (952 mg, 2.565 mmol), carbonyl diimidazole (469 mg, 2.892 mmol) and tetrahydrofuran (10 mL). The reaction was heated at 35° C. and stirred for 2 h. A 2:1 mixture of tert-butyl 2,2-dimethyl-4-[3-(5-methyl-4-sulfamoyl-pyrazol-1-yl)propyl]pyrrolidine-1-carboxylate and tert-butyl 2,2-dimethyl-4-[3-(3-methyl-4-sulfamoyl-pyrazol-1-yl)propyl]pyrrolidine-1-carboxylate (965 mg, 2.409 mmol) and 1,8-diazabicyclo[5.4.0]undec-7-ene (1.10 mL, 7.356 mmol) were added and the reaction was allowed to stir at room temperature overnight. The reaction was directly purified via silica gel chromatography using a gradient from 20%-100% ethyl acetate in hexanes. The inseparable regioisomeric products, tert-butyl 4-[3-[4-[[2-chloro-6-[3-(3,3,3-trifluoro-2,2-dimethyl-propoxy)pyrazol-1-yl]pyridine-3-carbonyl]sulfamoyl]-5-methyl-pyrazol-1-yl]propyl]-2,2-dimethyl-pyrrolidine-1-carboxylate and tert-butyl 4-[3-[4-[[2-chloro-6-[3-(3,3,3-trifluoro-2,2-dimethyl-propoxy)pyrazol-1-yl]pyridine-3-carbonyl]sulfamoyl]-3-methyl-pyrazol-1-yl]propyl]-2,2-dimethyl-pyrrolidine-1-carboxylate (1.073 g combined yield, 60%) were isolated as a white foam. ESI-MS m/z calc. 745.2636, found 746.4 (M+1)+; Retention time: 1.85 min (LC Method G). The regiochemical ratio of the mixture (2:1) was confirmed by $^1$H NMR.

Step 3: 2-Chloro-N-[1-[3-(5,5-dimethylpyrrolidin-3-yl)propyl]-5-methyl-pyrazol-4-yl]sulfonyl-6-[3-(3,3,3-trifluoro-2,2-dimethyl-propoxy)pyrazol-1-yl]pyridine-3-carboxamide and 2-chloro-N-[1-[3-(5,5-dimethylpyrrolidin-3-yl)propyl]-3-methyl-pyrazol-4-yl]sulfonyl-6-[3-(3,3,3-trifluoro-2,2-dimethyl-propoxy)pyrazol-1-yl]pyridine-3-carboxamide (2:1 Mixture of Inseparable Regioisomers)

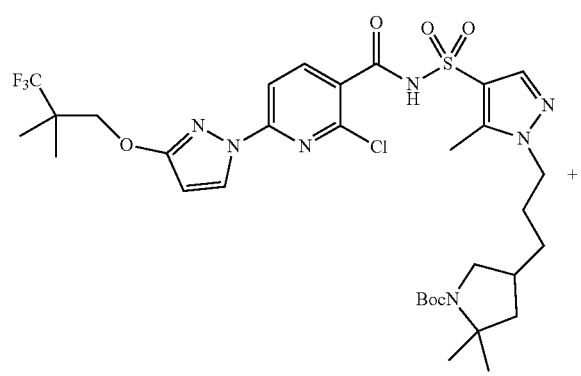

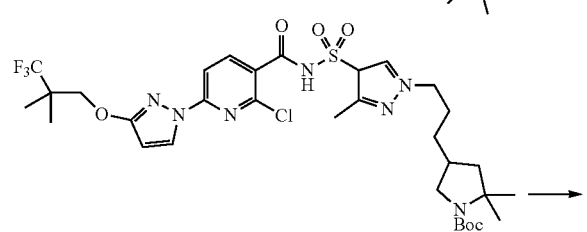

2:1 mixture of inseparable regioisomers

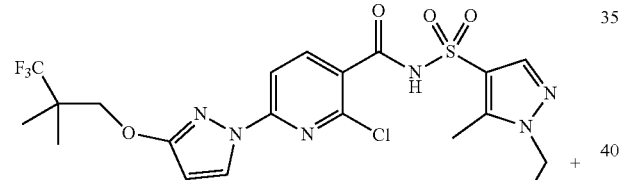

2:1 mixture of inseparable regioisomers

To a round bottom flask containing a 2:1 mixture of tert-butyl 4-[3-[4-[[2-chloro-6-[3-(3,3,3-trifluoro-2,2-dimethyl-propoxy)pyrazol-1-yl]pyridine-3-carbonyl]sulfamoyl]-5-methyl-pyrazol-1-yl]propyl]-2,2-dimethyl-pyrrolidine-1-carboxylate and tert-butyl 4-[3-[4-[[2-chloro-6-[3-(3,3,3-trifluoro-2,2-dimethyl-propoxy)pyrazol-1-yl]pyridine-3-carbonyl]sulfamoyl]-3-methyl-pyrazol-1-yl]propyl]-2,2-dimethyl-pyrrolidine-1-carboxylate (1.068 g, 1.431 mmol) was added dichloromethane (15 mL) and trifluoroacetic acid (4.4 mL, 57.11 mmol). The reaction was allowed to stir for 1 h at room temperature. The reaction was evaporated to dryness. Saturated sodium bicarbonate and brine were added and the reaction was extracted with ethyl acetate. The organic layer was evaporated to provide the product, however, a considerable amount of product after 2 more extractions with ethyl acetate was still in the aqueous layer. Therefore, the aqueous layer was evaporated to dryness and dry acetone was added to the solid and filtered. The acetone solute was evaporated and combined with the organic layers to provide 2-chloro-N-[1-[3-(5,5-dimethylpyrrolidin-3-yl)propyl]-5-methyl-pyrazol-4-yl]sulfonyl-6-[3-(3,3,3-trifluoro-2,2-dimethyl-propoxy)pyrazol-1-yl]pyridine-3-carboxamide and 2-chloro-N-[1-[3-(5,5-dimethylpyrrolidin-3-yl)propyl]-3-methyl-pyrazol-4-yl]sulfonyl-6-[3-(3,3,3-trifluoro-2,2-dimethyl-propoxy)pyrazol-1-yl]pyridine-3-carboxamide (2:1 mixture of inseparable regioisomers) (920 mg, 100%). ESI-MS m/z calc. 645.2112, found 646.3 (M+1)$^+$; Retention time: 1.45 min (LC Method B).

Step 4: 20,20,22-Trimethyl-4-[3-(3,3,3-trifluoro-2,2-dimethylpropoxy)-1H-pyrazol-1-yl]-10$\lambda^6$-thia-1,3,9,13,14-pentaazatetracyclo[16.2.1.111,14.02,7]docosa-2,4,6,11(22),12-pentaene-8,10,10-trione (Racemic Atropisomer 1) (Compound 280), 12,20,20-trimethyl-4-[3-(3,3,3-trifluoro-2,2-dimethylpropoxy)-1H-pyrazol-1-yl]-10$\lambda^6$-thia-1,3,9,13,14-pentaazatetracyclo[16.2.1.111,14.02,7]docosa-2,4,6,11(22),12-pentaene-8,10,10-trione (Compound 281) and 20,20,22-trimethyl-4-[3-(3,3,3-trifluoro-2,2-dimethylpropoxy)-1H-pyrazol-1-yl]-10$\lambda^6$-thia-1,3,9,13,14-pentaazatetracyclo[16.2.1.111,14.02,7]docosa-2,4,6,11(22),12-pentaene-8,10,10-trione (Racemic Atropisomer 2) (Compound 282)

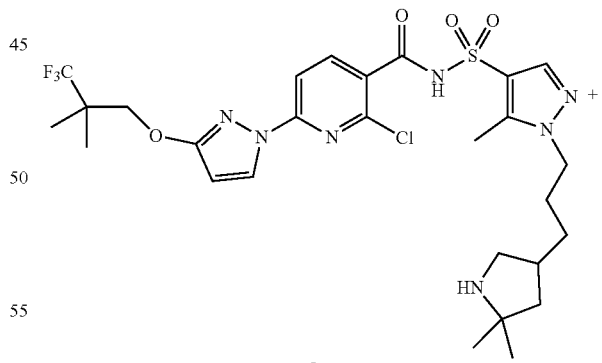

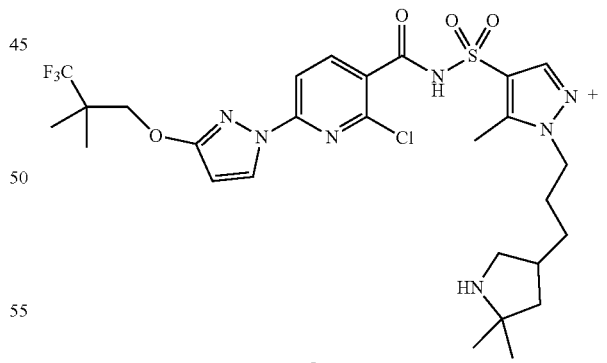

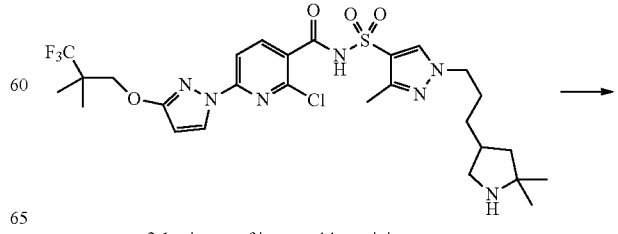

2:1 mixture of inseparable regioisomers

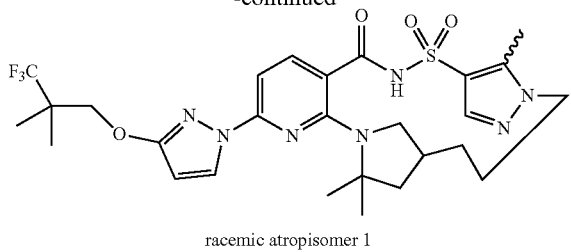

racemic atropisomer 1

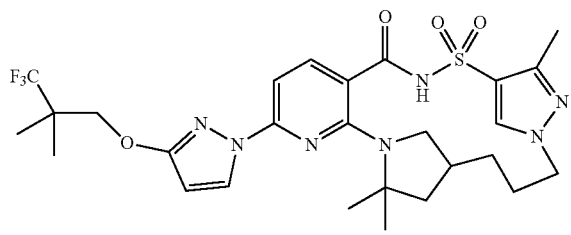

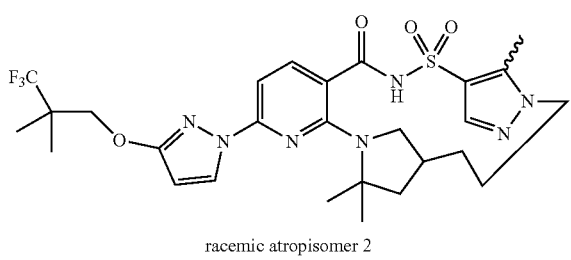

racemic atropisomer 2

To a 250 mL round bottom flask was added cesium fluoride (432 mg, 2.844 mmol), potassium carbonate (984 mg, 7.120 mmol), 3 Å molecular sieves and a solution of a mixture of regioisomers, 2-chloro-N-[1-[3-(5,5-dimethylpyrrolidin-3-yl)propyl]-5-methyl-pyrazol-4-yl]sulfonyl-6-[3-(3,3,3-trifluoro-2,2-dimethyl-propoxy)pyrazol-1-yl]pyridine-3-carboxamide and 2-chloro-N-[1-[3-(5,5-dimethylpyrrolidin-3-yl)propyl]-3-methyl-pyrazol-4-yl]sulfonyl-6-[3-(3,3,3-trifluoro-2,2-dimethyl-propoxy)pyrazol-1-yl]pyridine-3-carboxamide (2:1 mixture of inseparable regioisomers) (920 mg, 1.424 mmol) in dimethyl sulfoxide (55 mL). The reaction was purged with nitrogen and heated at 150° C. overnight. The reaction was cooled to room temperature, filtered, washed with brine and extracted with ethyl acetate. The organic layer was dried over sodium sulfate, filtered and purified via HPLC (10%-70% acetonitrile in water with a 0.1% hydrochloric acid modifier) to provide as the first atropisomer/regioisomer to elute, 20,20,22-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.111,14.02,7]docosa-2,4,6,11(22),12-pentaene-8,10,10-trione (racemic atropisomer 1) (Compound 280) (45 mg, 10%). $^1$H NMR (400 MHz, dimethyl sulfoxide-d$_6$) δ 12.41 (s, 1H), 8.19 (d, J=2.8 Hz, 1H), 7.86 (s, 1H), 7.77 (d, J=8.2 Hz, 1H), 6.93 (d, J=8.2 Hz, 1H), 6.16 (d, J=2.8 Hz, 1H), 4.38 (d, J=14.2 Hz, 1H), 4.23 (s, 2H), 4.01 (t, J=13.7 Hz, 1H), 2.05 (s, 3H), 1.89-1.70 (m, 3H), 1.55 (s, 3H), 1.48 (s, 3H), 1.44-1.28 (m, 2H), 1.23 (s, 6H), 1.08 (d, J=11.1 Hz, 1H). ESI-MS m/z calc. 609.2345, found 610.4 (M+1)$^+$; Retention time: 3.01 min (LC Method D). The second atropisomer/regioisomer to elute was 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.111,14.02,7]docosa-2,4,6,11(22),12-pentaene-8,10,10-trione (Compound 281) (73 mg, 17%). ESI-MS m/z calc. 609.2345, found 610.4 (M+1)$^+$; Retention time: 3.07 min (LC Method D). The third atropisomer/regioisomer to elute was 20,20,22-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.111,14.02,7]docosa-2,4,6,11(22),12-pentaene-8,10,10-trione (racemic atropisomer 2) (Compound 282) (19 mg, 4%). ESI-MS m/z calc. 609.2345, found 610.4 (M+1)$^+$; Retention time: 3.14 min (LC Method D).

Example 95: Preparation of (14S)-8-(3-{2-hydroxy-3-[1-(trifluoromethyl)cyclopropyl]propoxy}-1H-pyrazol-1-yl)-12,12-dimethyl-2λ$^6$-thia-3,9,11,18,23-pentaazatetracyclo[17.3.1.111,14.05,10]tetracosa-1(22),5(10),6,8,19(23),20-hexaene-2,2,4-trione (Diastereomer 1) (Compound 284) and of (14S)-8-(3-{2-hydroxy-3-[1-(trifluoromethyl)cyclopropyl]propoxy}-1H-pyrazol-1-yl)-12,12-dimethyl-2λ$^6$-thia-3,9,11,18,23-pentaazatetracyclo[17.3.1.111,14.05,10]tetracosa-1(22),5(10),6,8,19(23),20-hexaene-2,2,4-trione (Diastereomer 2) (Compound 283)

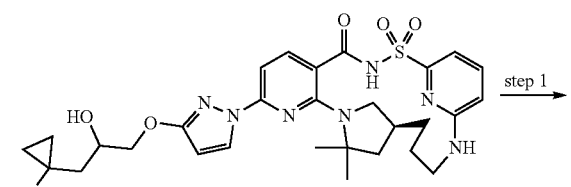

step 1

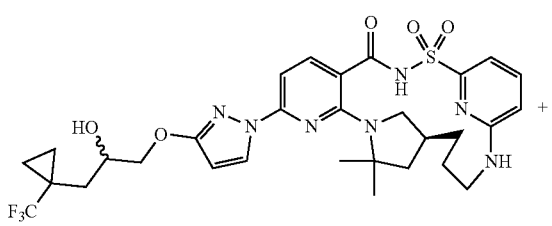

diastereomer 1

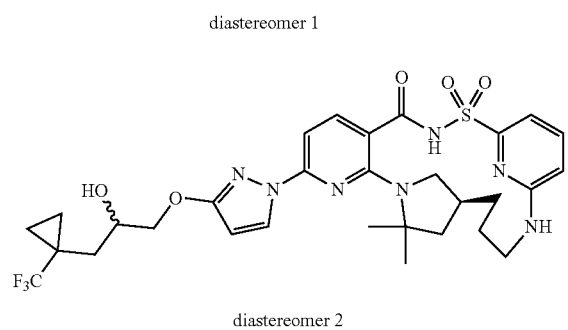

diastereomer 2

Step 1: (14S)-8-(3-{2-Hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Diastereomer 1) (Compound 284) and of (14S)-8-(3-{2-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Diastereomer 2) (Compound 283)

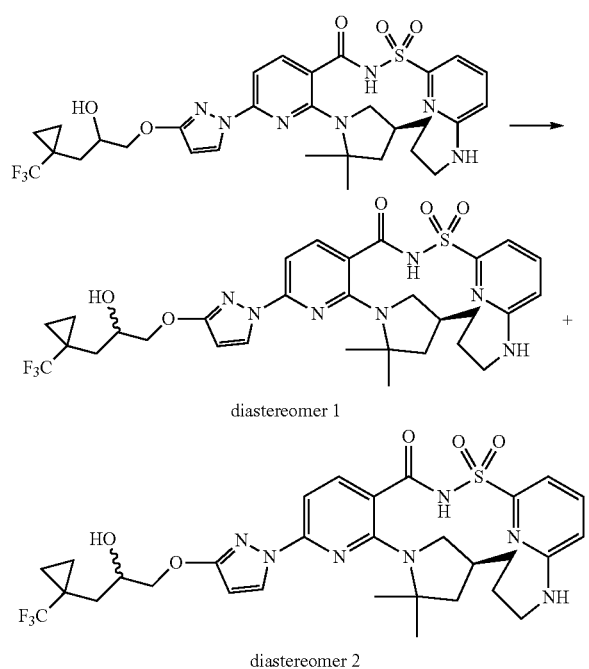

diastereomer 1 diastereomer 2

Subjected (14S)-8-(3-{2-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (3.24 g, 8.383 mmol) to chiral separation by SFC chromatography using a ChiralPak IG column (250×10 mm, 5 μm particle size) with 44% acetonitrile/methanol (90:10)/56% carbon dioxide mobile phase at 10 mL/min over 12.0 min (injection volume=70 μL of 22 mg/mL solution in acetonitrile/methanol (90:10)) giving as the first diastereomer to elute, (14S)-8-(3-{2-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (diastereomer 1) (Compound 284) (6.8 mg, 49%) as a white solid; ¹H NMR (400 MHz, dimethyl sulfoxide-d₆) δ 12.52 (s, 1H), 8.22 (d, J=2.8 Hz, 1H), 7.82 (d, J=8.2 Hz, 1H), 7.57 (t, J=7.9 Hz, 1H), 7.05 (d, J=7.2 Hz, 1H), 6.98 (s, 1H), 6.92 (d, J=8.2 Hz, 1H), 6.71 (d, J=8.5 Hz, 1H), 6.13 (d, J=2.8 Hz, 1H), 5.07 (d, J=5.7 Hz, 1H), 4.10 (d, J=5.2 Hz, 2H), 4.00-3.72 (m, 2H), 3.16 (s, 1H), 2.95 (d, J=13.5 Hz, 1H), 2.71 (s, 1H), 2.35 (d, J=17.2 Hz, 1H), 2.18-2.07 (m, 1H), 1.98 (dd, J=14.9, 4.0 Hz, 1H), 1.86 (dd, J=11.5, 5.2 Hz, 1H), 1.76 (s, 1H), 1.68 (s, 1H), 1.67-1.60 (m, 3H), 1.57 (d, J=12.6 Hz, 2H), 1.52 (s, 3H), 1.33 (t, J=12.0 Hz, 1H), 1.05-0.90 (m, 2H), 0.90-0.70 (m, 2H); ESI-MS m/z calc. 663.24506, found 664.4 (M+1)⁺; Retention time: 1.9 min (LC Method E). and as the second diastereomer to elute, (14S)-8-(3-{2-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (diastereomer 2) (Compound 283) (7.62 mg, 54%) as a white solid; ¹H NMR (400 MHz, dimethyl sulfoxide-d₆) δ 12.52 (s, 1H), 8.22 (d, J=2.8 Hz, 1H), 7.82 (d, J=8.2 Hz, 1H), 7.58 (t, J=7.9 Hz, 1H), 7.06 (d, J=7.2 Hz, 1H), 7.04-6.94 (m, 1H), 6.92 (d, J=8.2 Hz, 1H), 6.71 (d, J=8.5 Hz, 1H), 6.14 (d, J=2.7 Hz, 1H), 4.14-4.06 (m, 2H), 3.96 (dp, J=15.9, 6.0, 5.0 Hz, 2H), 3.16 (s, 1H), 2.95 (d, J=13.3 Hz, 1H), 2.70 (d, J=11.1 Hz, 1H), 2.50-2.36 (m, 1H), 2.13 (s, 1H), 1.98 (dd, J=15.0, 4.0 Hz, 1H), 1.86 (dd, J=11.8, 5.2 Hz, 1H), 1.77 (s, 1H), 1.71-1.65 (m, 1H), 1.63 (s, 1H), 1.61 (s, 3H), 1.57 (d, J=12.3 Hz, 2H), 1.52 (s, 3H), 1.31 (q, J=13.6, 12.7 Hz, 1H), 1.04-0.91 (m, 2H), 0.90-0.77 (m, 2H); ESI-MS m/z calc. 663.24506, found 664.4 (M+1)+; Retention time: 1.9 min (LC Method E).

Example 96: Preparation of (14S)-12,12-dimethyl-8-(3-{3-[1-(trifluoromethyl) cyclopropyl]-2,2,3,3-tetradeuterio-propoxy}-1H-pyrazol-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 287)

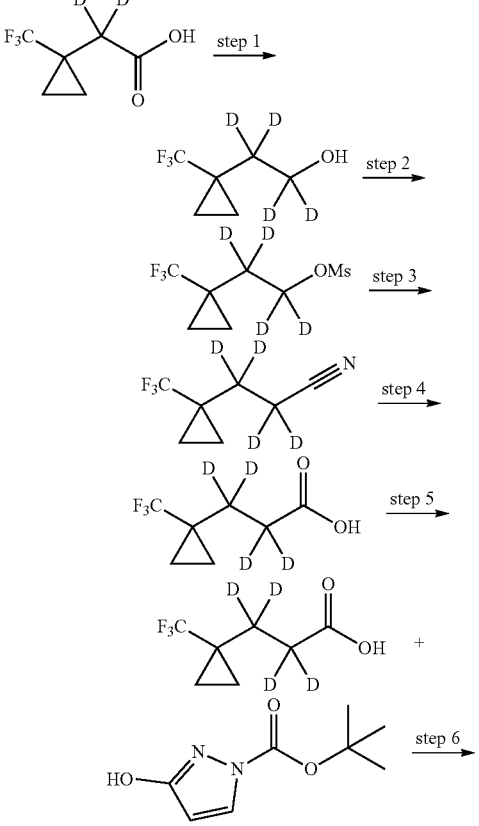

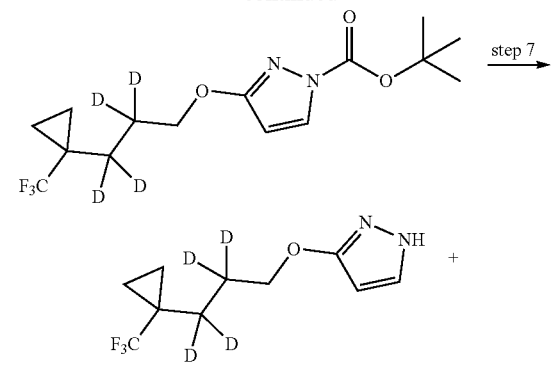

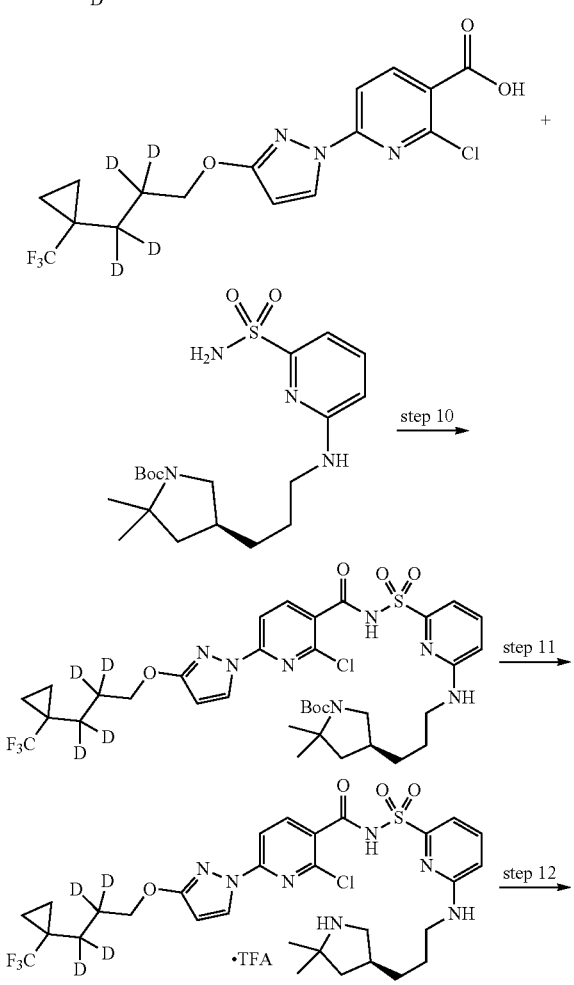

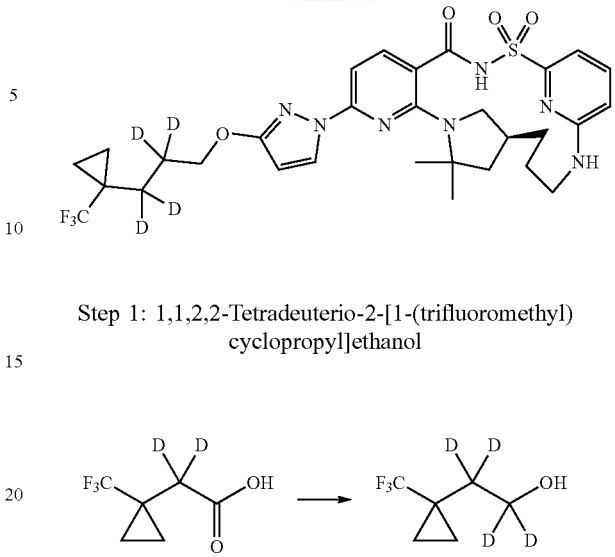

Step 1: 1,1,2,2-Tetradeuterio-2-[1-(trifluoromethyl)cyclopropyl]ethanol

Into a suspension of lithium aluminum deuteride (1.0872 g, 27.204 mmol) in anhydrous tetrahydrofuran (50 mL), was added a solution of 2,2-dideuterio-2-[1-(trifluoromethyl)cyclopropyl]acetic acid (4 g, 20.926 mmol) in anhydrous tetrahydrofuran (50 mL) dropwise at 0° C. The reaction mixture was stirred at room temperature for 16 h. The reaction was diluted with diethyl ether (50 mL) and cooled to 0° C. and then it was quenched sequentially with water (1.1 mL), 15% sodium hydroxide (aqueous, 1.1 mL) and water (3.3 mL). The reaction was stirred at room temperature for 30 min and then it was filtered through a pad of Celite and dried over anhydrous magnesium sulfate. Filtered and the filtrate was concentrated under reduced pressure to furnish 1,1,2,2-tetradeuterio-2-[1-(trifluoromethyl)cyclopropyl]ethanol (3.288 g, 92%) as a clear liquid. $^1$H NMR (250 MHz, CDCl$_3$) δ 1.42 (s, 1H), 1.03-0.89 (m, 2H), 0.67 (m, 2H).

Step 2: [1,1,2,2-Tetradeuterio-2-[1-(trifluoromethyl)cyclopropyl]ethyl]methanesulfonate Into a solution of 1,1,2,2-tetradeuterio-2-[1-(trifluoromethyl)cyclopropyl]ethanol (3.288 g, 19.334 mmol) and triethylamine (5.8692 g, 8.0843 mL, 58.002 mmol) in dichloromethane (35 mL) was added methanesulfonyl chloride (2.6577 g, 1.7957 mL, 23.201 mmol) dropwise at 0° C. The reaction mixture was stirred at room temperature for 1 h and then it was diluted with dichloromethane (50 mL) and 10% citric acid (50 mL). The two layers were separated and the organic layer was washed with saturated sodium bicarbonate (50 mL) and brine (50 mL). The organic solution was dried over anhydrous sodium sulfate and concentrated under vacuum. The residue was purified by silica gel chromatography using a 0% to 70% diethyl ether in hexane gradient to furnish [1,1,2,2-tetradeuterio-2-[1-(trifluoromethyl)cyclopropyl]ethyl]methanesulfonate (3.982 g, 83%) as a clear liquid. $^1$H NMR (250 MHz, CDCl$_3$) δ 3.01 (s, 3H), 1.03 (m, 2H), 0.71 (m, 2H).

Step 3: 2,2,3,3-Tetradeuterio-3-[1-(trifluoromethyl)cyclopropyl]propanenitrile

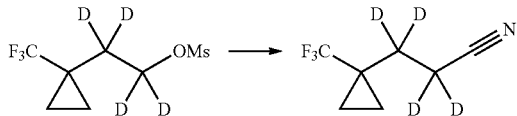 [SMILES: [2H]C([2H])(OS(C)(=O)=O)C([2H])([2H])C1(C(F)(F)F)CC1 ; [2H]C([2H])(C#N)C([2H])([2H])C1(C(F)(F)F)CC1]

Into a solution of [1,1,2,2-tetradeuterio-2-[1-(trifluoromethyl)cyclopropyl]ethyl]methanesulfonate (3.982 g, 16.013 mmol) in dimethyl sulfoxide (20 mL) was added sodium cyanide (980.93 mg, 20.016 mmol). The reaction mixture was stirred at 70° C. for 2 days. After cooling to room temperature, the reaction mixture was poured into water (50 mL). The aqueous solution was extracted with diethyl ether (3×50 mL). The combined organic layers were washed with water (2×50 mL) and brine (50 mL), dried over anhydrous magnesium sulfate, filtered and concentrated under vacuum to furnish 2,2,3,3-tetradeuterio-3-[1-(trifluoromethyl)cyclopropyl]propanenitrile (2.769 g, 96%) as a light yellow oil. $^1$H NMR (250 MHz, CDCl$_3$) δ 1.12-1.00 (m, 2H), 0.78-0.66 (m, 2H).

Step 4: 2,2,3,3-Tetradeuterio-3-[1-(trifluoromethyl)cyclopropyl]propanoic Acid

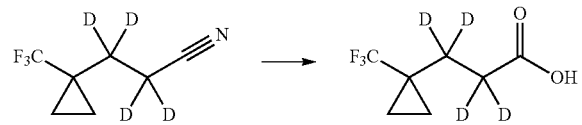 [SMILES: [2H]C([2H])(C#N)C([2H])([2H])C1(C(F)(F)F)CC1 ; [2H]C([2H])(C(=O)O)C([2H])([2H])C1(C(F)(F)F)CC1]

Into a solution of 2,2,3,3-tetradeuterio-3-[1-(trifluoromethyl)cyclopropyl]propanenitrile (2.769 g, 15.405 mmol) in CH$_3$CwaterD (30 mL) was added sodium deuteroxide (6.3166 g, 40% w/w, 61.620 mmol) and deuterium oxide (6 mL). The reaction mixture was stirred at 70° C. for 16 h. The reaction mixture was cooled to room temperature and concentrated under vacuum. The aqueous solution was diluted with water (50 mL) and washed with diethyl ether (2×50 mL). The aqueous phase was then acidified to pH 1 and extracted with diethyl ether (3×50 mL). These combined ether layers were washed with brine (50 mL), dried over anhydrous sodium sulfate, filtered and concentrated under vacuum to furnish 2,2,3,3-tetradeuterio-3-[1-(trifluoromethyl)cyclopropyl]propanoic acid (2.737 g, 91%) as a yellow liquid. $^1$H NMR (250 MHz, CDCl$_3$) δ 1.08-0.83 (m, 2H), 0.72-0.49 (m, 2H).

Step 5: 2,2,3,3-Tetradeuterio-3-[1-(trifluoromethyl)cyclopropyl]propan-1-ol

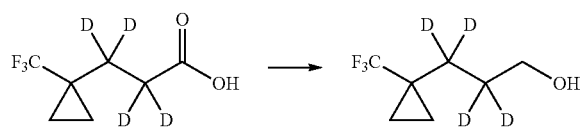 [SMILES: [2H]C([2H])(C(=O)O)C([2H])([2H])C1(C(F)(F)F)CC1 ; [2H]C([2H])(CO)C([2H])([2H])C1(C(F)(F)F)CC1]

Into a suspension of lithium aluminum hydride (689.14 mg, 0.7515 mL, 18.157 mmol) in anhydrous tetrahydrofuran (20 mL) was added a solution of 2,2,3,3-tetradeuterio-3-[1-(trifluoromethyl)cyclopropyl]propanoic acid (2.737 g, 13.967 mmol) in anhydrous tetrahydrofuran (20 mL) dropwise at 0° C. The reaction was stirred at room temperature for 16 h. The reaction mixture was diluted with diethyl ether (20 mL) and cooled to 0° C. Water (0.7 mL), 15% sodium hydroxide (aq.) (0.7 mL) and water (2.1 mL) were added sequentially. The reaction mixture was stirred at room temperature for 30 min and filtered through a pad of celite. The filtrate was dried over anhydrous magnesium sulfate, filtered and concentrated under vacuum to furnish 2,2,3,3-tetradeuterio-3-[1-(trifluoromethyl)cyclopropyl]propan-1-ol (2.04 g, 84%) as a clear liquid. $^1$H NMR (250 MHz, dimethyl sulfoxide-d$_6$) δ 4.44 (t, J=5.1 Hz, 1H), 3.38 (s, 2H), 0.95-0.79 (m, 2H), 0.68 (dd, J=2.2, 1.2 Hz, 2H).

Step 6: tert-Butyl 3-[2,2,3,3-tetradeuterio-3-[1-(trifluoromethyl)cyclopropyl]propoxy]pyrazole-1-carboxylate

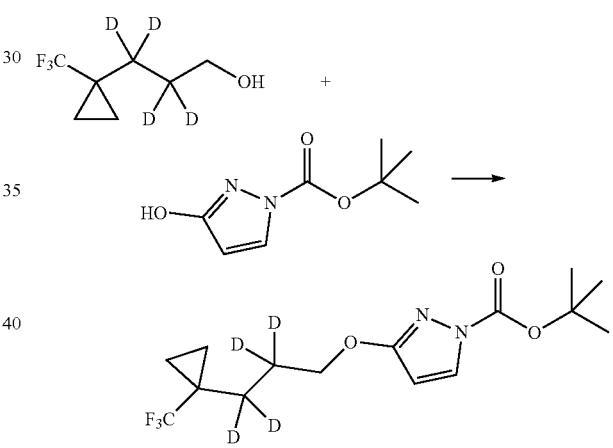

To a solution of tert-butyl 5-oxo-1H-pyrazole-2-carboxylate (2.08 g, 11.29 mmol) and 2,2,3,3-tetradeuterio-3-[1-(trifluoromethyl)cyclopropyl]propan-1-ol (2.04 g, 11.85 mmol) in tetrahydrofuran (26 mL) was added triphenylphosphine (3.108 g, 11.85 mmol). To the mixture was slowly added diisopropyl azodicarboxylate (2.396 g, 11.85 mmol) dropwise over 10 min (exotherm noted). The reaction mixture was stirred at room temperature for 2 h. The tetrahydrofuran was removed in vacuo. To the crude reaction mixture was added toluene (16.64 mL) and the mixture was stirred overnight. The solution was concentrated in vacuo. The crude product was purified by silica gel chromatography using a shallow gradient from 100% hexanes to 100% ethyl acetate giving tert-butyl 3-[2,2,3,3-tetradeuterio-3-[1-(trifluoromethyl)cyclopropyl]propoxy]pyrazole-1-carboxylate (2.43 g, 64%) as a clear syrup. ESI-MS m/z calc. 338.17554, found 339.0 (M+1)$^+$; Retention time: 0.75 min (LC Method A).

Step 7: 3-[2,2,3,3-Tetradeuterio-3-[1-(trifluoromethyl)cyclopropyl]propoxy]-1H-pyrazole

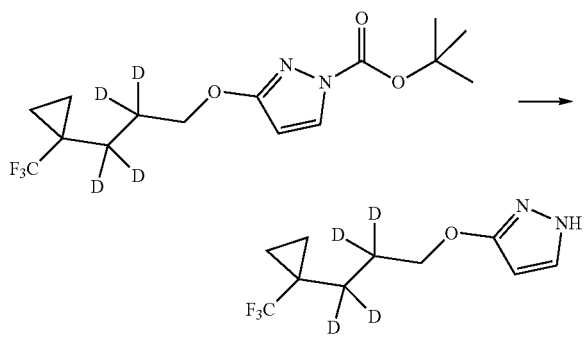

tert-Butyl 3-[2,2,3,3-tetradeuterio-3-[1-(trifluoromethyl)cyclopropyl]propoxy]pyrazole-1-carboxylate (2.43 g, 7.182 mmol) was dissolved in dichloromethane (24.3 mL) with trifluoroacetic acid (8.297 mL, 107.7 mmol) and the reaction was stirred at room temperature for 120 min. The reaction was evaporated and the resulting oil was partitioned between ethyl acetate and a saturated sodium bicarbonate solution. The aqueous portion was extracted two additional times with ethyl acetate then the organics were combined, washed with brine, dried over sodium sulfate, filtered and evaporated to give as an oil, 3-[2,2,3,3-tetradeuterio-3-[1-(trifluoromethyl)cyclopropyl]propoxy]-1H-pyrazole (1.711 g, 100%). ESI-MS m/z calc. 238.12311, found 239.1 (M+1)$^+$; Retention time: 0.54 min (LC Method A).

Step 8: tert-Butyl 2-chloro-6-[3-[2,2,3,3-tetradeuterio-3-[1-(trifluoromethyl)cyclopropyl]propoxy]pyrazol-1-yl]pyridine-3-carboxylate

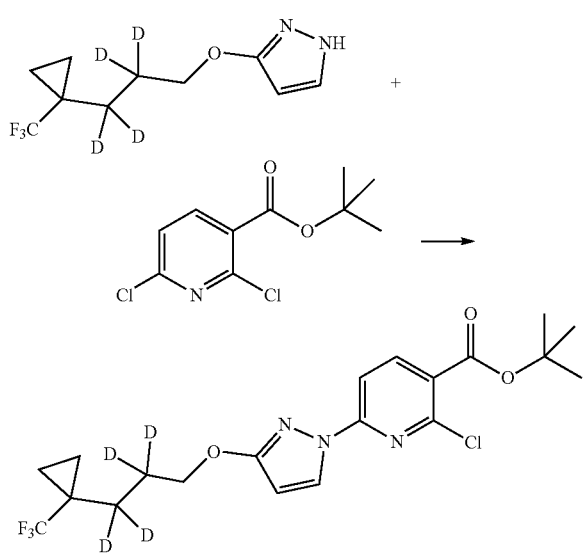

tert-Butyl 2,6-dichloropyridine-3-carboxylate (1.782 g, 7.182 mmol), 3-[2,2,3,3-tetradeuterio-3-[1-(trifluoromethyl)cyclopropyl]propoxy]-1H-pyrazole (1.711 g, 7.182 mmol) and potassium carbonate (1.192 g, 8.625 mmol) were combined in anhydrous dimethyl sulfoxide (34.22 mL). 1,4-diazabicyclo[2.2.2]octane (161.3 mg, 1.438 mmol) was added and the mixture was stirred at room temperature under nitrogen for 16 h. The reaction mixture was diluted with water (65.81 mL) and stirred for 15 min. The resulting white solid was filtered and washed with water. The solid was dissolved in dichloromethane and dried over magnesium sulfate. The mixture was filtered and the filtrate evaporated to give tert-butyl 2-chloro-6-[3-[2,2,3,3-tetradeuterio-3-[1-(trifluoromethyl)cyclopropyl]propoxy]pyrazol-1-yl]pyridine-3-carboxylate (2.58 g, 80%) as a white solid. ESI-MS m/z calc. 449.16312, found 450.0 (M+1)$^+$; Retention time: 0.91 min (LC Method A).

Step 9: 2-Chloro-6-[3-(2,2-dideuterio-2-dispiro[2.0.2.1]heptan-7-yl-ethoxy)pyrazol-1-yl]pyridine-3-carboxylic Acid

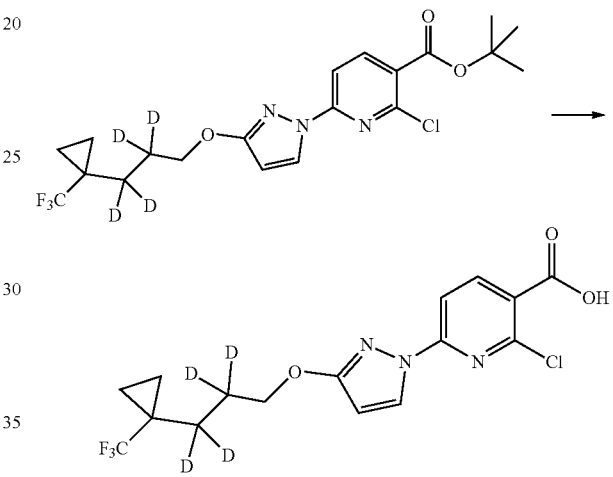

tert-Butyl 2-chloro-6-[3-[2,2,3,3-tetradeuterio-3-[1-(trifluoromethyl)cyclopropyl]propoxy]pyrazol-1-yl]pyridine-3-carboxylate (2.58 g, 5.735 mmol) was dissolved in dichloromethane (25.8 mL) with trifluoroacetic acid (6.627 mL, 86.02 mmol) and the reaction was stirred at room temperature for 16 h. Added trifluoroacetic acid (2.209 mL, 28.67 mmol) and continued stirring for 30 min. The reaction was evaporated and to the resulting solid was added ether and the ether then removed under reduced pressure. This was repeated twice more resulting in a white solid which was recrystallized from dichloromethane to give pure product as a solid (crop 1). Product remained in the filtrate which was evaporated giving an off-white solid which was dissolved in ethyl acetate and washed with 5N sodium hydroxide (2×) then 1N hydrochloric acid (1×) then dried (sodium sulfate), filtered and concentrated to a white solid which was purified by silica gel chromatography using a shallow gradient from 100% dichloromethane to 20% methanol in dichloromethane giving poor separation. Fractions containing product were combined, concentrated, filtered and purified using a reverse phase HPLC-MS method using a Luna C$_{18}$ (2) column (75×30 mm, 5 μm particle size) sold by Phenomenex (pn: 00C-4252-U0-AX) and a dual gradient run from 20%-80% mobile phase B over 15.0 min (mobile phase A=water (5 mM hydrochloric acid), mobile phase B=acetonitrile, flow rate=50 mL/min, injection volume=950 μL and column temperature=25° C.) giving pure product material which was combined with the originally crystallized solid material to give 2-chloro-6-[3-[2,2,3,3-tetradeuterio-3-[1-(trifluoromethyl)cyclopropyl]propoxy]pyrazol-1-yl]pyridine-3-carboxylic acid (1.75 g, 78%) as a white solid. ESI-MS m/z calc. 393.10052, found 394.0 (M+1)$^+$; Retention time: 0.72 min (LC Method A).

Step 10: tert-Butyl (4S)-4-[3-[[6-[[2-chloro-6-[3-[2,2,3,3-tetradeuterio-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate

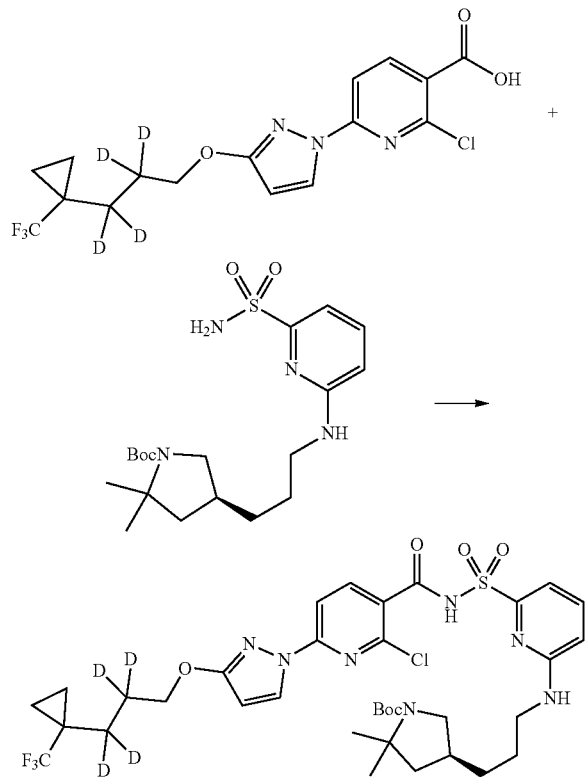

To a solution of 2-chloro-6-[3-[2,2,3,3-tetradeuterio-3-[1-(trifluoromethyl)cyclopropyl]propoxy]pyrazol-1-yl]pyridine-3-carboxylic acid (1 g, 2.539 mmol) in tetrahydrofuran (6.832 mL) was added carbonyl diimidazole (514.7 mg, 3.174 mmol) (recrystallized from tetrahydrofuran) and the mixture was stirred at room temperature for 3 h then tert-butyl (4S)-2,2-dimethyl-4-[3-[(6-sulfamoyl-2-pyridyl)amino]propyl]pyrrolidine-1-carboxylate (1.047 g, 2.538 mmol) was added as a solution in tetrahydrofuran (2.5 mL) followed by 1,8-diazabicyclo[5.4.0]undec-7-ene (1.192 mL, 7.971 mmol) and the resulting mixture was stirred for 6 h at room temperature. The reaction was diluted with water and ethyl acetate then hydrochloric acid (1.418 mL of 12 M, 17.02 mmol) was added, aqueous layer was then pH=1. The layers were separated and the organic layer was washed with water (1×) and brine (1×) then dried over sodium sulfate, filtered and concentrated to a white foam which was purified on a 275 g C$_{18}$ reverse phase column eluting with a gradient from 50%-100% acetonitrile in water giving tert-butyl (4S)-4-[3-[[6-[[2-chloro-6-[3-[2,2,3,3-tetradeuterio-3-[1-(trifluoromethyl)cyclo propyl]propoxy]pyrazol-1-yl]pyridine-3-carbonyl]sulfamoyl]-2-pyridyl]amino]propyl]-2,2-dimethyl-pyrrolidine-1-carboxylate (1.261 g, 63%) as a white solid. ESI-MS m/z calc. 787.3044, found 788.2 (M+1)$^+$; Retention time: 0.89 min (LC Method A).

Step 11: 2-Chloro-N-[[6-[3-[(3S)-5,5-dimethylpyrrolidin-3-yl]propylamino]-2-pyridyl]sulfonyl]-6-[3-[2,2,3,3-tetradeuterio-3-[1-(trifluoromethyl)cyclopropyl]propoxy]pyrazol-1-yl]pyridine-3-carboxamide (Trifluoroacetate Salt)

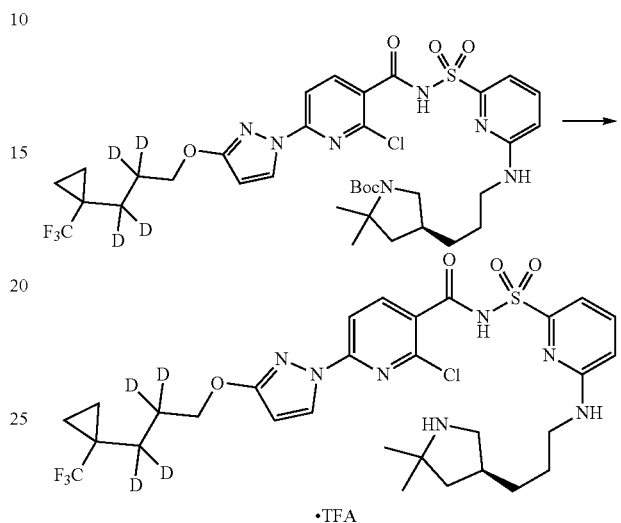

tert-Butyl (4S)-4-[3-[[6-[[2-chloro-6-[3-[2,2,3,3-tetradeuterio-3-[1-(trifluoromethyl)cyclopropyl]propoxy]pyrazol-1-yl]pyridine-3-carbonyl]sulfamoyl]-2-pyridyl]amino]propyl]-2,2-dimethyl-pyrrolidine-1-carboxylate (1.409 g, 1.787 mmol) was dissolved in dichloromethane (6.147 mL) and to the mixture was added trifluoroacetic acid (5.509 mL, 71.51 mmol) and the mixture was stirred at room temperature for 90 min. Concentrated the mixture to dryness under reduced pressure, added 50 mL of toluene and removed by rotary evaporation (45° C. water bath). Again added 50 mL of toluene and removed by rotary evaporation (45° C. water bath) then dried in vacuo giving 2-chloro-N-[[6-[3-[(3S)-5,5-dimethylpyrrolidin-3-yl]propylamino]-2-pyridyl]sulfonyl]-6-[3-[2,2,3,3-tetradeuterio-3-[1-(trifluoromethyl)cyclopropyl]propoxy]pyrazol-1-yl]pyridine-3-carboxamide (trifluoroacetate salt) (1.434 g, 100%) as a white solid. ESI-MS m/z calc. 687.25195, found 688.2 (M+1)$^+$; Retention time: 0.62 min (LC Method A).

Step 12: (14S)-12,12-Dimethyl-8-(3-{3-[1-(trifluoromethyl)cyclopropyl]-2,2,3,3-tetradeuterio-propoxy}-1H-pyrazol-1-yl)-2λ$^6$-thia-3,9,11,18,23-pentaazatetracyclo[17.3.1.111,14.05,10]tetracosa-1(22),5,7,9,19(23),20-hexaene-2,2,4-trione (Compound 287)

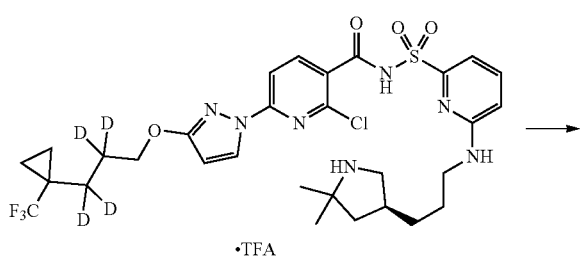

757
-continued

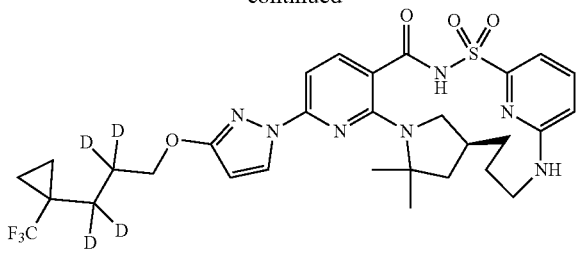

To a solution of 2-chloro-N-[[6-[3-[(3S)-5,5-dimethylpyrrolidin-3-yl]propylamino]-2-pyridyl]sulfonyl]-6-[3-[2,2,3,3-tetradeuterio-3-[1-(trifluoromethyl)cyclopropyl]propoxy]pyrazol-1-yl]pyridine-3-carboxamide (trifluoroacetate salt) (1.434 g, 1.788 mmol) in NMP (86.04 mL) was added potassium carbonate (1.73 g, 12.52 mmol). The mixture was purged with nitrogen for 5 min. The mixture was then heated at 155° C. for 18 h. The reaction mixture was cooled to room temperature and added to water (~200 mL) affording an off-white solid. The mixture was carefully acidified with hydrochloric acid (2.235 mL of 12 M, 26.82 mmol) affording a foamy slurry. The solid was collected by filtration and washed with water. Filtrate was discarded. The wet filter cake was dissolved in ethyl acetate and was dried over magnesium sulfate, filtered and concentrated in vacuo affording a light yellow oil which was chromatographed on a 275 g reverse phase $C_{18}$ column eluting with a gradient from 50%-100% acetonitrile in water giving (14S)-12,12-dimethyl-8-(3-{3-[1-(trifluoromethyl)cyclopropyl]-2,2,3,3-tetradeuterio-propoxy}-1H-pyrazol-1-yl)-2$\lambda^6$-thia-3,9,11,18,23-pentaazatetracyclo[17.3.1.111,14.05,10]tetracosa-1(22),5,7,9,19(23),20-hexaene-2,2,4-trione (Compound 287) (845.2 mg, 73%) as a white solid. $^1$H NMR (400 MHz, dimethyl sulfoxide-$d_6$) δ 12.50 (s, 1H), 8.21 (d, J=2.8 Hz, 1H), 7.81 (d, J=8.2 Hz, 1H), 7.58 (dd, J=8.5, 7.2 Hz, 1H), 7.05 (d, J=7.1 Hz, 1H), 6.99 (s, 1H), 6.91 (d, J=8.2 Hz, 1H), 6.71 (d, J=8.5 Hz, 1H), 6.12 (d, J=2.8 Hz, 1H), 4.19 (s, 2H), 3.92 (d, J=12.2 Hz, 1H), 3.15 (s, 1H), 2.95 (d, J=13.5 Hz, 1H), 2.71 (s, 1H), 2.12 (s, 1H), 1.86 (dd, J=11.9, 5.3 Hz, 1H), 1.77 (s, 1H), 1.60 (s, 4H), 1.57 (d, J=13.9 Hz, 2H), 1.51 (s, 3H), 1.37-1.23 (m, 1H), 0.93-0.86 (m, 2H), 0.75 (s, 2H). ESI-MS m/z calc. 651.27527, found 652.4 (M+1)$^+$; Retention time: 2.25 min (LC Method B).

Example 97: Preparation of 20,20,22-trimethyl-4-[3-(3,3,3-trifluoro-2,2-dimethylpropoxy)-1H-pyrazol-1-yl]-10$\lambda^6$-thia-1,3,9,13,14-pentaazatetracyclo[16.2.1.111,14.02,7]docosa-2,4,6,11(22),12-pentaene-8,10,10-trione (Atropisomer 1, Enantiomer 1) (Compound 288) and 20,20,22-Trimethyl-4-[3-(3,3,3-trifluoro-2,2-dimethylpropoxy)-1H-pyrazol-1-yl]-10$\lambda^6$-thia-1,3,9,13,14-pentaazatetracyclo[16.2.1.111,14.02,7]docosa-2,4,6,11(22),12-pentaene-8,10,10-trione (Atropisomer 1, Enantiomer 2) (Compound 289)

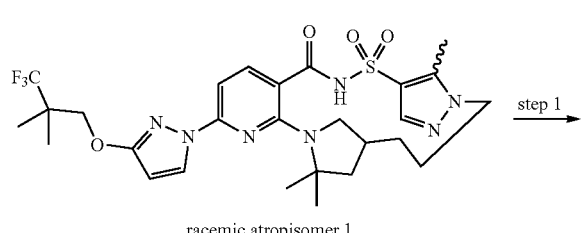

racemic atropisomer 1

758
-continued

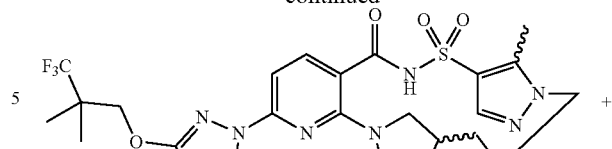

atropisomer 1, enantiomer 1

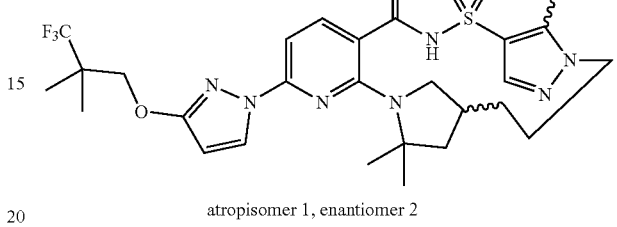

atropisomer 1, enantiomer 2

Step 1: 20,20,22-Trimethyl-4-[3-(3,3,3-trifluoro-2,2-dimethylpropoxy)-1H-pyrazol-1-yl]-10$\lambda^6$-thia-1,3,9,13,14-pentaazatetracyclo[16.2.1.111,14.02,7]docosa-2,4,6,11(22),12-pentaene-8,10,10-trione
(Atropisomer 1, Enantiomer 1) (Compound 288)
and 20,20,22-Trimethyl-4-[3-(3,3,3-trifluoro-2,2-dimethylpropoxy)-1H-pyrazol-1-yl]-10$\lambda^6$-thia-1,3,9,13,14-pentaazatetracyclo[16.2.1.111,14.02,7]docosa-2,4,6,11(22),12-pentaene-8,10,10-trione
(Atropisomer 1, Enantiomer 2) (Compound 289)

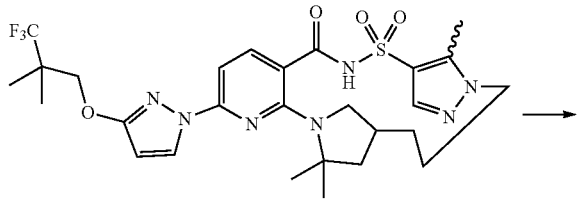

racemic atropisomer 1

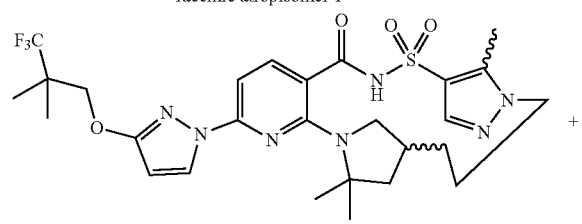

atropisomer 1, enantiomer 1

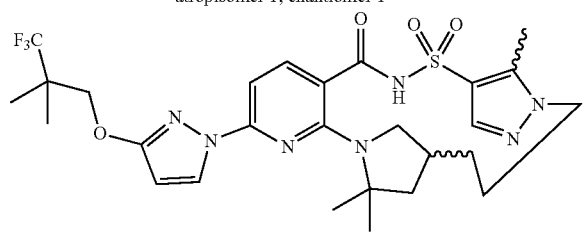

atropisomer 1, enantiomer 2

Racemic 20,20,22-trimethyl-4-[3-(3,3,3-trifluoro-2,2-dimethylpropoxy)-1H-pyrazol-1-yl]-10$\lambda^6$-thia-1,3,9,13,14- pentaazatetracyclo[16.2.1.1¹¹,¹⁴.0²,⁷]docosa-2,4,6,11(22), 12-pentaene-8,10,10-trione (45 mg, 0.07381 mmol) (racemic atropisomer 1) was separated by chiral SFC chromatography using a ChiralPak AS-H (250×21.2 mm column, 5 μm particle size) with 24% acetonitrile:methanol (90:10, 20 mM NH$_3$))/76% carbon dioxide mobile phase at 70 mL/min giving as the first enantiomer to elute, 20,20,22-trimethyl-4-[3-(3,3,3-trifluoro-2,2-dimethylpropoxy)-1H-pyrazol-1-yl]-10λ⁶-thia-1,3,9,13,14-pentaazatetracyclo [16.2.1.1¹¹,¹⁴.0²,⁷]docosa-2,4,6,11(22),12-pentaene-8,10, 10-trione (atropisomer 1, enantiomer 1) (Compound 288) (18.6 mg, 83%). ESI-MS m/z calc. 609.2345, found 610.4 (M+1)⁺; Retention time: 3.0 min (LC Method D). The second enantiomer to elute was 20,20,22-trimethyl-4-[3-(3, 3,3-trifluoro-2,2-dimethylpropoxy)-1H-pyrazol-1-yl]-10λ⁶-thia-1,3,9,13,14-pentaazatetracyclo[16.2.1.1¹¹,¹⁴.0²,⁷]docosa-2,4,6,11(22),12-pentaene-8,10,10-trione (atropisomer 1, enantiomer 2) (Compound 289) (15.5 mg, 69%). ¹H NMR (500 MHz, dimethyl sulfoxide-d$_6$) δ 12.16 (bs, 1H), 8.19 (d, J=2.8 Hz, 1H), 7.82 (s, 1H), 7.81 (d, J=7.9 Hz, 1H), 6.92 (d, J=7.9 Hz, 1H), 6.10 (d, J=2.8 Hz, 1H), 4.35 (m, 1H), 4.22 (bs, 2H), 4.02 (m, 1H), 2.53 (s, 3H), 2.02 (m, 3H), 1.83 (m, 2H), 1.75 (dd, J=12.1 Hz, 5.6 Hz, 1H), 1.54 (s, 3H), 1.47 (s, 3H), 1.36 (q, J=15.6 Hz, 12.4 Hz, 2H), 1.22 (s, 6H), 1.12 (m, 1H). ESI-MS m/z calc. 609.2345, found 610.4 (M+1)⁺; Retention time: 3.0 min (LC Method D).

Example 98: Preparation of (14S)-12,12-di(trideuterio)methyl-8-(3-{3-[1-(trifluoromethyl)cyclopropyl] propoxy}-1H-pyrazol-1-yl)-2λ⁶-thia-3,9,11,18,23-pentaazatetracyclo[17.3.1.1¹¹,¹⁴.0⁵,¹⁰]tetracosa-1 (22),5,7,9,19(23),20-hexaene-2,2,4-trione (Compound 292)

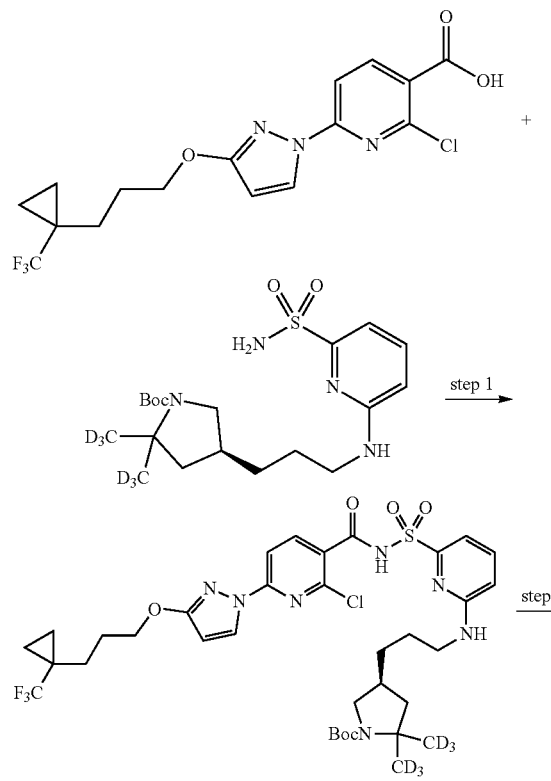

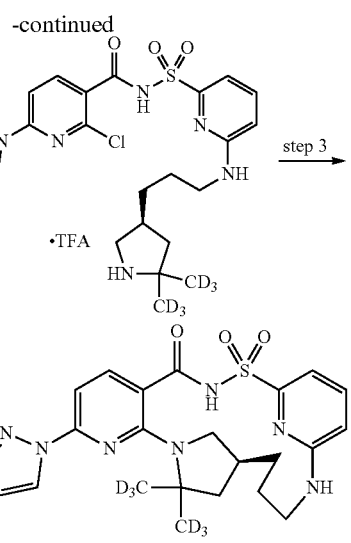

Step 1: tert-Butyl (4S)-4-[3-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino] propyl]-2,2-bis(trideuteriomethyl)pyrrolidine-1-carboxylate

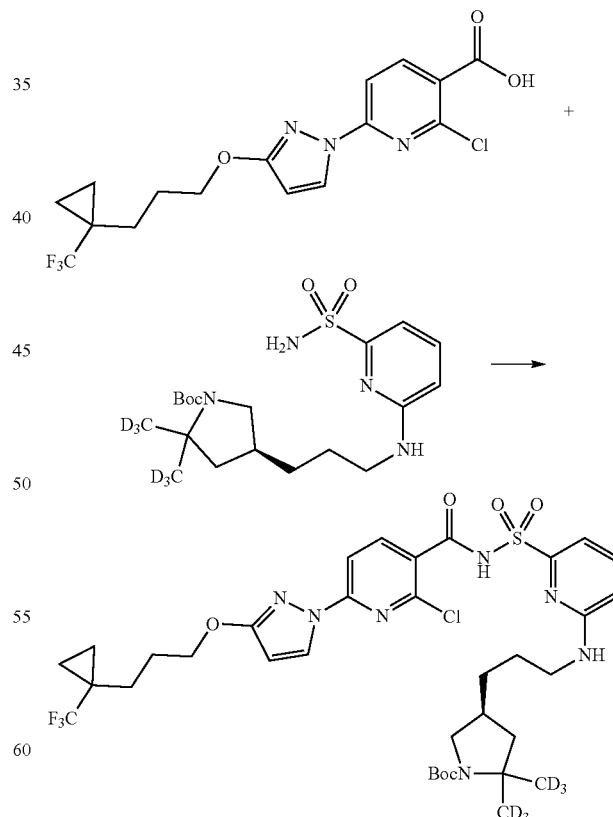

To a solution of 2-chloro-6-[3-[3-[1-(trifluoromethyl)cyclopropyl]propoxy]pyrazol-1-yl]pyridine-3-carboxylic acid (175 mg, 0.4490 mmol) in tetrahydrofuran (1.5 mL) was added carbonyl diimidazole (86 mg, 0.5070 mmol) and the mixture stirred at ambient temperature for 90 min. To this solution was added tert-butyl (4S)-4-[3-[(6-sulfamoyl-2-pyridyl)amino]propyl]-2,2-bis(trideuteriomethyl)pyrrolidine-1-carboxylate (140 mg, 0.3345 mmol) in tetrahydrofuran (1 mL) followed by 1,8-diazabicyclo[5.4.0]undec-7-ene (135 µL, 0.9027 mmol) and the mixture was stirred at ambient temperature for 16 h. The reaction was diluted with water (5 mL) and the mixture slowly acidified with hydrochloric acid (1.7 mL of 1 M, 1.700 mmol). The mixture was extracted with ethyl acetate (10 mL) and the organic phase separated. The organic phase was concentrated in vacuo. The crude product was chromatographed on a 30 gram reverse phase column eluting with 50%-100% acetonitrile in water giving tert-butyl (4S)-4-[3-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-bis(trideuteriomethyl)pyrrolidine-1-carboxylate (200 mg, 76%). ESI-MS m/z calc. 789.31696, found 790.4 (M+1)$^+$; Retention time: 3.47 min (LC Method D).

Step 2: N-[[6-[3-[(3S)-5,5-Bis(trideuteriomethyl) pyrrolidin-3-yl]propylamino]-2-pyridyl]sulfonyl]-2-chloro-6-[3-[3-[1-(trifluoromethyl)cyclopropyl] propoxy]pyrazol-1-yl]pyridine-3-carboxamide (Trifluoroacetate Salt)

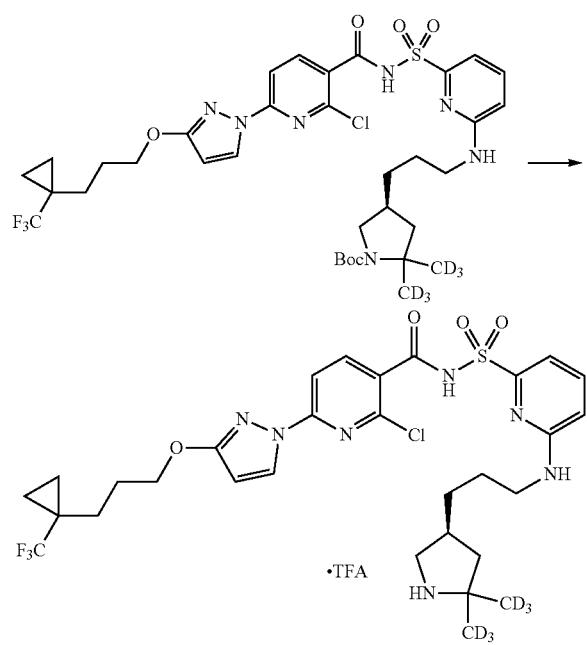

To tert-butyl (4S)-4-[3-[[6-[[2-chloro-6-[3-[3-[1-(trifluoromethyl)cyclopropyl]propoxy]pyrazol-1-yl]pyridine-3-carbonyl]sulfamoyl]-2-pyridyl]amino]propyl]-2,2-bis(trideuteriomethyl)pyrrolidine-1-carboxylate (200 mg, 0.2531 mmol) in dichloromethane (3 mL) and toluene (1 mL) was added trifluoroacetic acid (200 µL, 2.596 mmol). The mixture was stirred at ambient temperature for 18 h. The solvent was removed in vacuo and the residue was treated with 10 mL of toluene and concentrated in vacuo giving N-[[6-[3-[(3S)-5,5-bis(trideuteriomethyl)pyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (trifluoroacetate salt) (204 mg, 100%). ESI-MS m/z calc. 689.2645, found 690.3 (M+1)$^+$; Retention time: 2.23 min (LC Method D).

Step 3: (14S)-12,12-Di(trideuterio)methyl-8-(3-{3-[1-(trifluoromethyl)cyclopropyl]propoxy}-1H-pyrazol-1-yl)-2λ$^6$-thia-3,9,11,18,23-pentaazatetracyclo [17.3.1.1$^{11,14}$.0$^{5,10}$]tetracosa-1(22),5,7,9,19(23), 20-hexaene-2,2,4-trione (Compound 292)

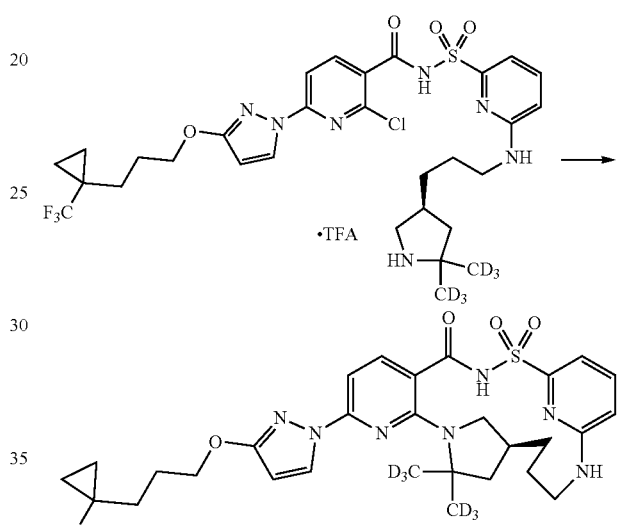

To a solution of N-[[6-[3-[(3S)-5,5-bis(trideuteriomethyl) pyrrolidin-3-yl]propylamino]-2-pyridyl]sulfonyl]-2-chloro-6-[3-[3-[1-(trifluoromethyl)cyclopropyl]propoxy]pyrazol-1-yl]pyridine-3-carboxamide (trifluoroacetate salt) (200 mg, 0.2487 mmol) in NMP (6 mL) was added potassium carbonate (180 mg, 1.302 mmol). The mixture was purged for 5 min with nitrogen and then heated at 135° C. for 22 h. The reaction mixture was cooled to ambient temperature and diluted with water (10 mL). The mixture was carefully acidified with hydrochloric acid (500 µL of 6 M, 3.000 mmol). The slurry was extracted with ethyl acetate (15 mL) and the organic phase washed with brine. The organic phase was concentrated in vacuo. The crude product was chromatographed on a 30 g reverse phase column eluting with gradient from 50%-100% acetonitrile in water affording a foam which was dried in a vacuum oven at 45° C. for 48 h giving (14S)-12,12-di(trideuterio)methyl-8-(3-{3-[1-(trifluoromethyl)cyclopropyl]propoxy}-1H-pyrazol-1-yl)-2λ$^6$-thia-3,9,11,18,23-pentaazatetracyclo[17.3.1.1$^{11,14}$.0$^{5,10}$] tetracosa-1(22),5,7,9,19(23),20-hexaene-2,2,4-trione (Compound 292) (45.2 mg, 27%). $^1$H NMR (400 MHz, dimethyl sulfoxide-d$_6$) δ 12.51 (s, 1H), 8.21 (d, J=2.7 Hz, 1H), 7.81 (d, J=8.3 Hz, 1H), 7.63-7.51 (m, 1H), 7.05 (d, J=7.2 Hz, 1H), 6.99 (s, 1H), 6.91 (d, J=8.2 Hz, 1H), 6.71 (d, J=8.4 Hz, 1H), 6.12 (d, J=2.7 Hz, 1H), 4.20 (t, J=6.2 Hz, 2H), 3.92 (s, 1H), 3.15 (s, 1H), 2.95 (d, J=13.4 Hz, 1H), 2.75-2.65 (m, 1H), 2.10 (d, J=18.4 Hz, 1H), 1.85 (dd, J=11.1, 5.2 Hz, 3H), 1.79-1.67 (m, 3H), 1.54 (t, J=12.5 Hz, 3H), 1.39-1.25 (m, 1H), 0.91 (t, J=3.3 Hz, 2H), 0.75 (s, 2H). ESI-MS m/z calc. 653.28784, found 654.4 (M+1)+; Retention time: 2.21 min (LC Method B).

Example 99: Preparation of (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 294) and (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 293)

Step 1: (14S)-8-[3-(2-{Dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 294) and (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 293)

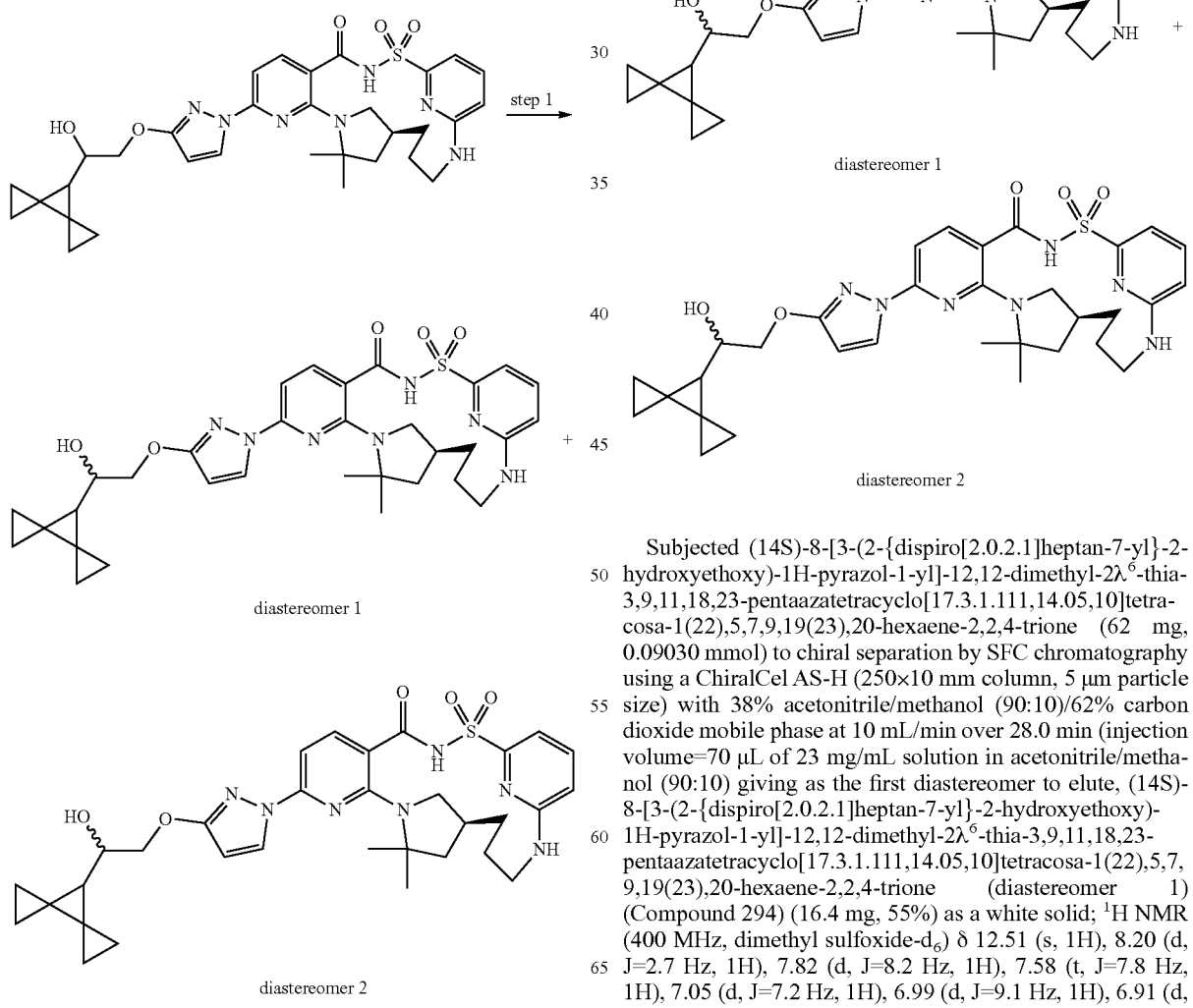

Subjected (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (62 mg, 0.09030 mmol) to chiral separation by SFC chromatography using a ChiralCel AS-H (250×10 mm column, 5 μm particle size) with 38% acetonitrile/methanol (90:10)/62% carbon dioxide mobile phase at 10 mL/min over 28.0 min (injection volume=70 μL of 23 mg/mL solution in acetonitrile/methanol (90:10) giving as the first diastereomer to elute, (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 1) (Compound 294) (16.4 mg, 55%) as a white solid; ¹H NMR (400 MHz, dimethyl sulfoxide-d₆) δ 12.51 (s, 1H), 8.20 (d, J=2.7 Hz, 1H), 7.82 (d, J=8.2 Hz, 1H), 7.58 (t, J=7.8 Hz, 1H), 7.05 (d, J=7.2 Hz, 1H), 6.99 (d, J=9.1 Hz, 1H), 6.91 (d, J=8.2 Hz, 1H), 6.71 (d, J=8.5 Hz, 1H), 6.09 (d, J=2.7 Hz, 1H), 4.87 (dd, J=5.2, 1.3 Hz, 1H), 4.09 (d, J=5.5 Hz, 2H), 3.92 (d, J=12.6 Hz, 1H), 3.57 (dt, J=9.2, 5.3 Hz, 1H), 3.16 (d, J=10.0 Hz, 1H), 2.95 (d, J=13.3 Hz, 1H), 2.69 (d, J=9.6 Hz, 1H), 2.12 (s, 1H), 1.86 (dd, J=11.9, 5.2 Hz, 1H), 1.76 (s, 1H), 1.60 (s, 3H), 1.59-1.53 (m, 3H), 1.52 (s, 3H), 1.31 (q, J=9.4, 7.1 Hz, 1H), 1.08 (ddd, J=8.9, 5.3, 3.6 Hz, 1H), 0.95-0.88 (m, 1H), 0.84 (ddd, J=8.8, 5.2, 3.7 Hz, 1H), 0.73 (ddd, J=8.0, 4.8, 3.3 Hz, 1H), 0.63 (ddd, J=8.7, 5.2, 3.6 Hz, 2H), 0.60-0.54 (m, 2H), 0.52 (dt, J=8.4, 3.8 Hz, 1H); ESI-MS m/z calc. 633.2733, found 634.2 (M+1)⁺; Retention time: 1.95 min (LC Method B) and as the second diastereomer to elute, (14S)-8-[3-(2-{dispiro[2.0.2.1]heptan-7-yl}-2-hydroxyethoxy)-1H-pyrazol-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (diastereomer 2) (Compound 293) (17.3 mg, 60%) as a white solid; ¹H NMR (400 MHz, dimethyl sulfoxide-d₆) δ 12.52 (s, 1H), 8.20 (d, J=2.8 Hz, 1H), 7.82 (d, J=8.2 Hz, 1H), 7.58 (t, J=7.9 Hz, 1H), 7.05 (d, J=7.2 Hz, 1H), 6.99 (d, J=8.9 Hz, 1H), 6.91 (d, J=8.2 Hz, 1H), 6.71 (d, J=8.5 Hz, 1H), 6.09 (d, J=2.7 Hz, 1H), 4.88 (d, J=5.2 Hz, 1H), 4.15-4.05 (m, 2H), 3.92 (d, J=11.8 Hz, 1H), 3.57 (ddd, J=9.2, 4.8, 1.8 Hz, 1H), 3.16 (d, J=9.6 Hz, 1H), 2.95 (d, J=13.2 Hz, 1H), 2.70 (s, 1H), 2.12 (s, 1H), 1.85 (t, J=6.1 Hz, 1H), 1.76 (s, 1H), 1.61 (s, 3H), 1.59-1.53 (m, 3H), 1.51 (d, J=2.2 Hz, 3H), 1.31 (d, J=12.4 Hz, 1H), 1.08 (ddd, J=8.9, 5.3, 3.6 Hz, 1H), 0.92 (dd, J=8.6, 4.2 Hz, 1H), 0.84 (ddt, J=7.4, 5.2, 3.5 Hz, 2H), 0.74-0.70 (m, 1H), 0.63 (ddd, J=8.9, 5.3, 3.8 Hz, 1H), 0.59-0.54 (m, 2H), 0.54-0.48 (m, 1H); ESI-MS m/z calc. 633.2733, found 634.2 (M+1)⁺; Retention time: 1.95 min (LC Method B).

Example 100: Preparation of (14S)-8-(3-{3-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Compound 295)

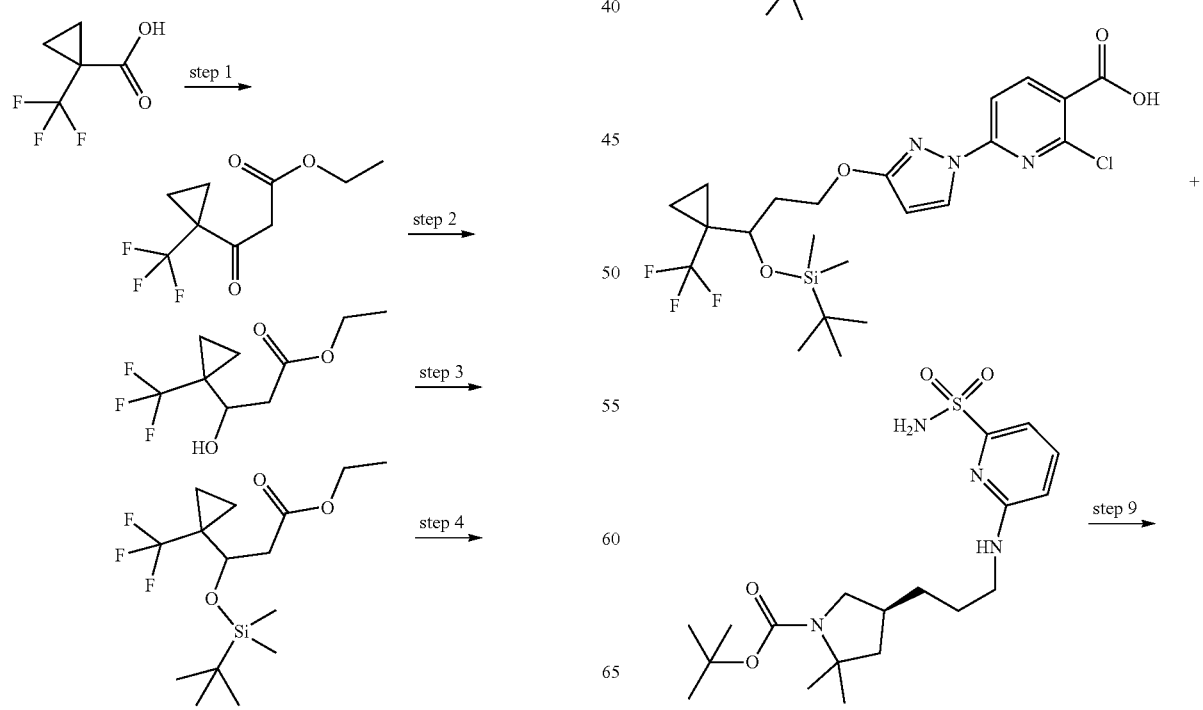

767

-continued

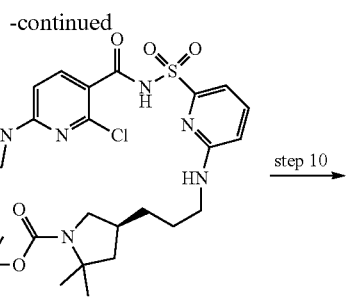

step 10 →

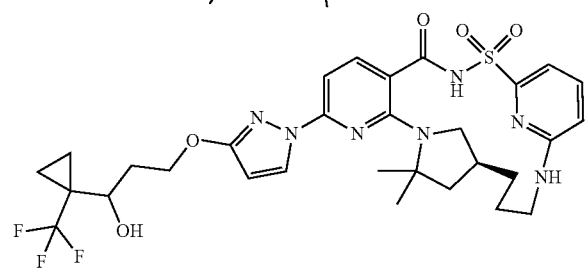

Step 1: Ethyl 3-oxo-3-[1-(trifluoromethyl)cyclopropyl]propanoate

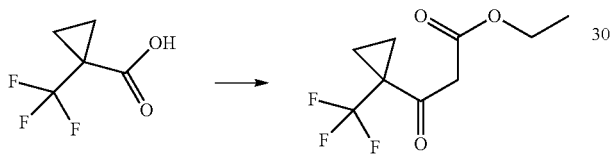

To a suspension of (3-ethoxy-3-oxo-propanoyl)oxypotassium (23.197 g, 136.29 mmol) in acetonitrile (200 mL) was added triethylamine (21.014 g, 28.945 mL, 207.67 mmol) and dichloromagnesium (15.448 g, 162.25 mmol). The mixture was stirred for 2 h at room temperature. A mixture of carbonyl diimidazole (12.628 g, 77.878 mmol) and 1-(trifluoromethyl)cyclopropanecarboxylic acid (10 g, 64.898 mmol) in acetonitrile (40 mL) was added to the mixture and the combined mixture was stirred overnight. The mixture was diluted with ethyl acetate (250 mL) and washed with water (500 mL) and brine (500 mL) before being dried over sodium sulfate then filtered. After concentration of the filtrate in vacuo, the organic residue was purified using silica gel chromatography eluting with 30% hexanes-ethyl acetate to give ethyl 3-oxo-3-[1-(trifluoromethyl)cyclopropyl]propanoate (3.875 g, 25%). $^1$H NMR (250 MHz, CDCl$_3$) δ 4.17 (qd, J=7.1, 0.6 Hz, 2H), 3.73 (s, 2H), 1.41-1.32 (m, 3H), 1.24 (td, J=7.1, 0.6 Hz, 4H).

Step 2: Ethyl 3-hydroxy-3-[1-(trifluoromethyl)cyclopropyl]propanoate

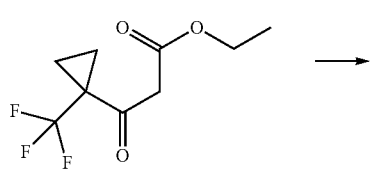

768

-continued

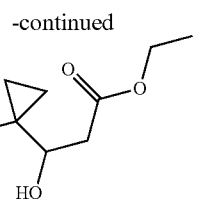

To a solution of ethyl 3-oxo-3-[1-(trifluoromethyl)cyclopropyl]propanoate (3.513 g, 15.671 mmol) in EtOH (35.130 mL) was added NaBH$_4$ (652.16 mg, 0.6901 mL, 17.238 mmol) at −78° C. The mixture was stirred at 0° C. before being quenched with 1M aqueous hydrochloric acid (35 mL). The organic layer was extracted with ethyl acetate (3×100 mL) before being washed with brine (100 mL) and dried over sodium sulfate. Filtered the mixture and the filtrate was concentrated in vacuo to give ethyl 3-hydroxy-3-[1-(trifluoromethyl)cyclopropyl]propanoate (3.31 g, 63%). $^1$H NMR (250 MHz, CDCl$_3$) δ 4.09 (d, J=7.1 Hz, 2H), 3.89 (s, 1H), 2.70 (d, J=3.1 Hz, 2H), 1.26-1.21 (m, 3H), 0.96 (d, J=6.9 Hz, 4H).

Step 3: Ethyl 3-[tert-butyl(dimethyl)silyl]oxy-3-[1-(trifluoromethyl)cyclopropyl]propanoate

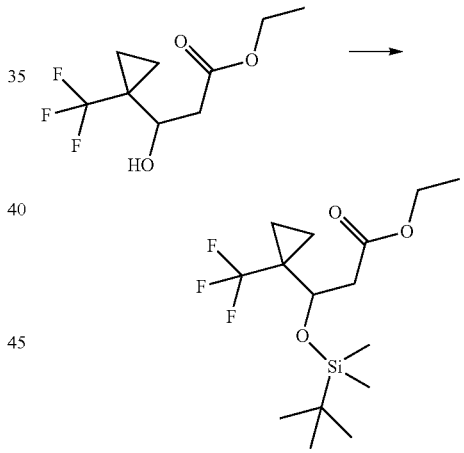

To a solution of ethyl 3-hydroxy-3-[1-(trifluoromethyl)cyclopropyl]propanoate (3.19 g, 14.103 mmol) in dichloromethane (63.800 mL) was added 2,6-lutidine (3.1734 g, 3.4300 mL, 29.616 mmol) and [tert-butyl(dimethyl)silyl] trifluoromethanesulfonate (5.5918 g, 4.8624 mL, 21.154 mmol) at 0° C. The reaction was stirred at room temperature for 3 h. The solution was diluted with diethyl ether (60 mL) and washed with 1 M hydrochloric acid (60 mL), saturated sodium bicarbonate (60 mL) and brine (60 mL). The organic layer was dried over sodium sulfate, filtered and concentrated under vacuum to give ethyl 3-[tert-butyl(dimethyl) silyl]oxy-3-[1-(trifluoromethyl)cyclopropyl]propanoate (3.51 g, 72%) as a clear liquid. $^1$H NMR (250 MHz, CDCl$_3$) δ 4.12 (q, J=7.2 Hz, 2H), 3.95 (ddd, J=8.5, 3.9, 1.1 Hz, 1H), 2.71-2.59 (m, 2H), 1.33-1.19 (m, 3H), 0.89-0.87 (m, 3H), 0.88-0.82 (m, 6H), 0.11-0.05 (m, 4H), 0.04-0.01 (m, 6H).

Step 4: 1-[1-(Trifluoromethyl)cyclopropyl]propane-1,3-diol

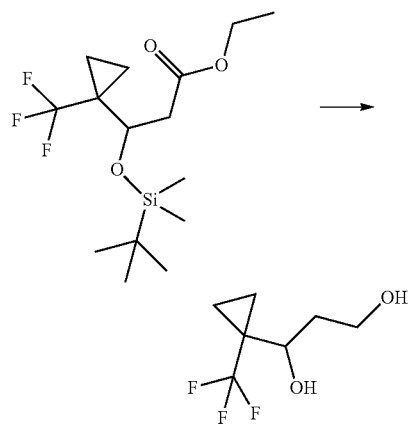

To a solution of ethyl 3-[tert-butyl(dimethyl)silyl]oxy-3-[1-(trifluoromethyl)cyclopropyl]propanoate (3.51 g, 10.310 mmol) in anhydrous tetrahydrofuran (50 mL) was added lithium aluminum hydride (469.57 mg, 0.5121 mL, 12.372 mmol) at 0° C. The reaction was stirred at 0° C. for 1 h. The reaction was diluted with diethyl ether (50 mL) and then it was quenched with water (0.5 mL), 15% sodium hydroxide (0.5 mL) and water (1.5 mL) at 0° C. and it was stirred for 30 min. Magnesium sulfate was added and the solid was removed by filtration. The filtrate was concentrated under vacuum and purified by silica gel chromatography using a gradient from 100% hexanes to 100% ethyl acetate to furnish 1-[1-(trifluoromethyl)cyclopropyl]propane-1,3-diol (1.493 g, 73%) as a clear liquid. $^1$H NMR (250 MHz, Chloroform-d) δ 4.03-3.67 (m, 3H), 2.83 (d, J=4.2 Hz, 1H), 2.16 (s, 1H), 1.96-1.74 (m, 2H), 1.13-0.93 (m, 2H), 0.93-0.69 (m, 2H).

Step 5: tert-Butyl 3-[3-hydroxy-3-[1-(trifluoromethyl) cyclopropyl]propoxy]pyrazole-1-carboxylate

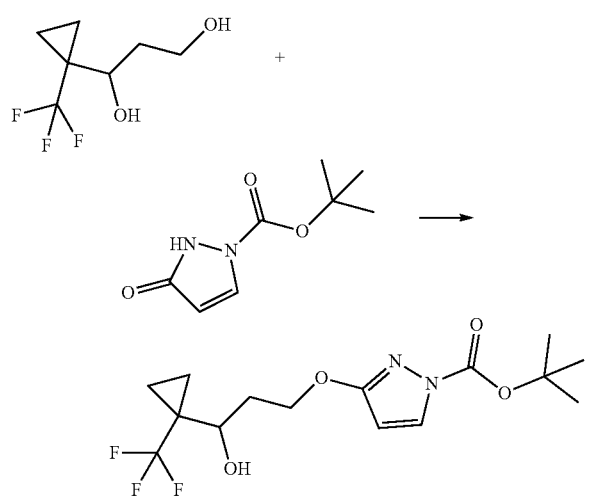

To a solution of 1-[1-(trifluoromethyl)cyclopropyl]propane-1,3-diol (1.493 g, 7.5397 mmol), tert-butyl 3-hydroxypyrazole-1-carboxylate (1.4582 g, 7.9167 mmol) and triphenylphosphine (3.9550 g, 15.079 mmol) in anhydrous tetrahydrofuran (30 mL) was added DIAD (3.0491 g, 15.079 mmol) at 0° C. dropwise. The reaction mixture was stirred at room temperature for 3 h. The reaction was quenched with water (30 mL) and tetrahydrofuran was removed under reduced pressure. The residue was extracted with ethyl acetate (3×30 mL). The combined organic layers were washed with brine (30 mL), dried over anhydrous sodium sulfate, filtered and concentrated under vacuum. The residue was purified by silica gel chromatography using a gradient from 0%-50% ethyl acetate in hexanes to furnish tert-butyl 3-[3-hydroxy-3-[1-(trifluoromethyl)cyclopropyl]propoxy]pyrazole-1-carboxylate (1.04 g, 37%) as a clear liquid. $^1$H NMR (250 MHz, Chloroform-d) δ 7.84 (d, J=2.9 Hz, 1H), 5.85 (d, J=2.9 Hz, 1H), 4.58 (ddd, J=10.9, 9.4, 3.8 Hz, 1H), 4.37 (dt, J=10.6, 4.6 Hz, 1H), 3.79 (d, J=10.6 Hz, 1H), 3.70 (s, 1H), 2.31-2.07 (m, 1H), 1.97-1.75 (m, 1H), 1.60 (s, 9H), 1.06-0.68 (m, 4H). ESI-MS m/z calc. 350.1453, found 351.1 (M+1)$^+$; Retention time: 4.97 min (LC Method Q).

Step 6: tert-Butyl-dimethyl-[3-(1H-pyrazol-3-yloxy)-1-[1-(trifluoromethyl) cyclopropyl]propoxy] silane

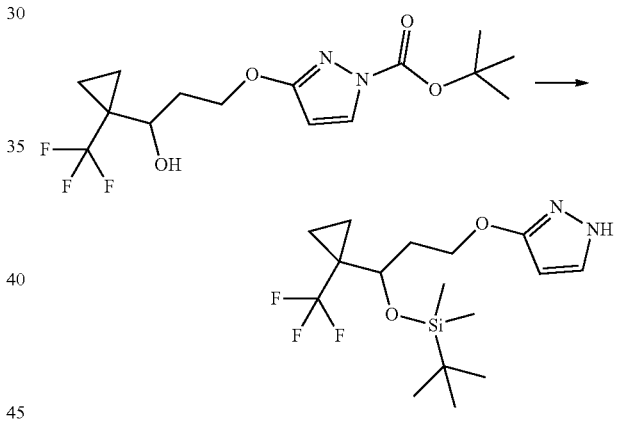

To a solution of tert-butyl 3-[3-hydroxy-3-[1-(trifluoromethyl)cyclopropyl]propoxy]pyrazole-1-carboxylate (1.04 g, 2.9686 mmol) and 2,6-lutidine (1.5905 g, 1.7191 mL, 14.843 mmol) in anhydrous dichloromethane (50 mL) was added [tert-butyl(dimethyl)silyl]trifluoromethanesulfonate (3.1387 g, 2.7269 mL, 11.874 mmol) dropwise at room temperature. The reaction mixture was stirred at room temperature for 2 days then was quenched with 1 N hydrochloric acid (50 mL). Two layers were separated. The aqueous layer was extracted with dichloromethane (2×50 mL). The combined organic layers were washed with aqueous saturated sodium bicarbonate solution (50 mL), dried over anhydrous sodium sulfate, filtered and concentrated under vacuum. The residue was purified by silica gel chromatography using a gradient from 0% to 30% acetone in hexanes to furnish tert-butyl-dimethyl-[3-(1H-pyrazol-3-yloxy)-1-[1-(trifluoromethyl)cyclo propyl]propoxy]silane (895.1 mg, 82%) as a light yellow oil. $^1$H NMR (250 MHz, dimethyl sulfoxide-d$_6$) δ 11.84 (s, 1H), 7.49 (s, 1H), 5.62 (s, 1H), 4.16-3.98 (m, 2H), 3.64-3.55 (m, 1H), 2.12-1.85 (m, 2H), 1.07-0.94 (m, 2H), 0.85 (s, 9H), 0.79-0.62 (m, 2H), 0.06 (s, 3H), −0.02 (s, 3H). ESI-MS m/z calc. 364.1794, found 365.1 (M+1)⁺; Retention time: 6.52 min (LC Method Q).

Step 7: tert-Butyl 6-[3-[3-[cert-butyl (dimethyl) silyl]oxy-3-[1-(trifluoromethyl) cyclopropyl] propoxy]pyrazol-1-yl]-2-chloro-pyridine-3-carboxylate

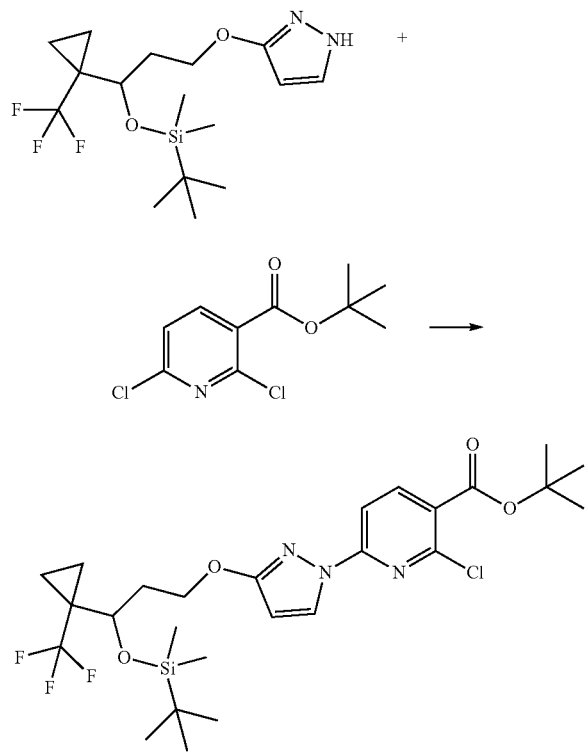

To a solution of tert-butyl 2,6-dichloropyridine-3-carboxylate (378 mg, 1.524 mmol) and tert-butyl-dimethyl-[3-(1H-pyrazol-3-yloxy)-1-[1-(trifluoromethyl) cyclopropyl]propoxy]silane (500 mg, 1.372 mmol) in dimethyl sulfoxide (10 mL) was added potassium carbonate (234 mg, 1.693 mmol) followed by 1,4-diazabicyclo[2.2.2]octane (37 mg, 0.3298 mmol). The heterogeneous mixture was stirred at room temperature under nitrogen for 16 h. The reaction mixture was quenched with ice and stirred for 15 min. The resulting white solid was collected by filtration and washed with water. The solid was dissolved in dichloromethane and dried over magnesium sulfate. The mixture was filtered and the filtrate evaporated and the resultant brown residue was purified by silica gel column chromatography using a shallow gradient 100% hexanes to 100% ethyl acetate to afford tert-butyl 6-[3-[3-[tert-butyl(dimethyl)silyl]oxy-3-[1-(trifluoromethyl)cyclopropyl]propoxy]pyrazol-1-yl]-2-chloro-pyridine-3-carboxylate (640 mg, 81%) as a white solid. ESI-MS m/z calc. 575.2194, found 576.36 (M+1)⁺; Retention time: 0.85 min (LC Method L).

Step 8: 6-[3-[3-[tert-Butyl (dimethyl) silyl]oxy-3-[1-(trifluoromethyl) cyclopropyl]propoxy]pyrazol-1-yl]-2-chloro-pyridine-3-carboxylic Acid

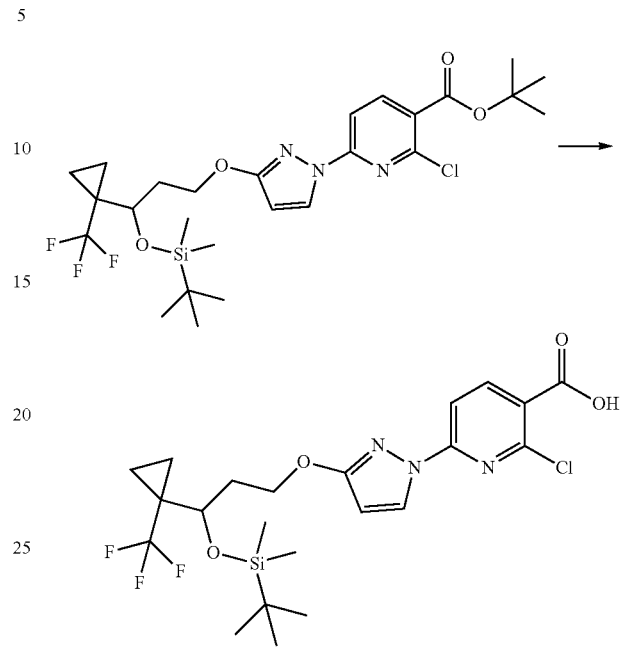

tert-Butyl 6-[3-[3-[tert-butyl(dimethyl)silyl]oxy-3-[1-(trifluoromethyl)cyclopropyl]propoxy]pyrazol-1-yl]-2-chloro-pyridine-3-carboxylate (640 mg, 1.111 mmol) was dissolved in a pre-mixed mixture of dichloromethane (2 mL) with trifluoroacetic acid (500 μL, 6.490 mmol) and the reaction was stirred at room temperature for 60 min. The reaction was evaporated and the resulting oil was partitioned between ethyl acetate and a saturated sodium bicarbonate solution. The aqueous portion was extracted two additional times with ethyl acetate, then the organics were combined, washed with brine, dried over sodium sulfate, filtered and evaporated to afford 6-[3-[3-[tert-butyl(dimethyl)silyl]oxy-3-[1-(trifluoromethyl)cyclopropyl]propoxy]pyrazol-1-yl]-2-chloro-pyridine-3-carboxylic acid (540 mg, 93%). ESI-MS m/z calc. 519.1568, found 520.3 (M+1)⁺; Retention time: 0.6 min (LC Method L).

Step 9: tert-Butyl (4S)-4-[3-[[6-[[6-[3-[3-[tert-butyl (dimethyl)silyl]oxy-3-[1-(trifluoromethyl)cyclopropyl]propoxy]pyrazol-1-yl]-2-chloro-pyridine-3-carbonyl]sulfamoyl]-2-pyridyl]amino]propyl]-2,2-dimethyl-pyrrolidine-1-carboxylate

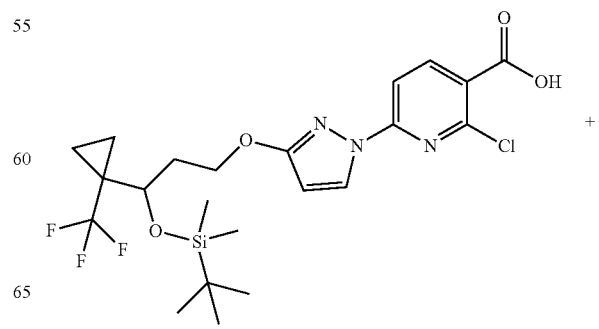

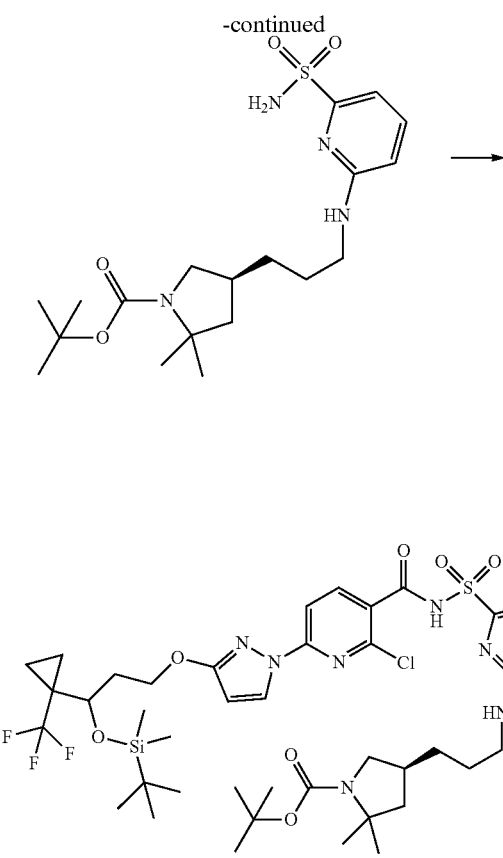

6-[3-[3-[tert-Butyl(dimethyl)silyl]oxy-3-[1-(trifluoromethyl)cyclopropyl]propoxy]pyrazol-1-yl]-2-chloro-pyridine-3-carboxylic acid (540 mg, 1.038 mmol) and carbonyl diimidazole (204 mg, 1.258 mmol) (freshly recrystallized from tetrahydrofuran, washed with cold ether and dried on vacuum) were combined in tetrahydrofuran (5 mL) and stirred for 2 h at room temperature. Then, tert-butyl (4S)-2,2-dimethyl-4-[3-[(6-sulfamoyl-2-pyridyl)amino]propyl]pyrrolidine-1-carboxylate (431 mg, 1.045 mmol) was added followed by 1,8-diazabicyclo[5.4.0]undec-7-ene (800 µL, 5.350 mmol) and the reaction was stirred at room temperature for 14 h. The reaction mixture was quenched with saturated ammonium chloride and extracted with ethyl acetate. Combined organic layers washed with brine, dried over magnesium sulfate, filtered and concentrated to a light brown oil which was purified by silica gel chromatography using a shallow gradient from 100% hexanes to 100% ethyl acetate to afford tert-butyl (4S)-4-[3-[[6-[[6-[3-[3-[tert-butyl(dimethyl)silyl]oxy-3-[1-(trifluoromethyl)cyclopropyl]propoxy]pyrazol-1-yl]-2-chloro-pyridine-3-carbonyl]sulfamoyl]-2-pyridyl]amino]propyl]-2,2-dimethyl-pyrrolidine-1-carboxylate (572 mg, 60%) as a white solid. ESI-MS m/z calc. 913.36066, found 914.5 (M+1)⁺; Retention time: 0.79 min (LC Method L).

Step 10: (14S)-8-(3-{3-Hydroxy-3-[1-(trifluoromethyl)cyclopropyl]propoxy}-1H-pyrazol-1-yl)-12,12-dimethyl-2λ⁶-thia-3,9,11,18,23-pentaazatetra cyclo [17.3.1.111,14.05,10]tetracosa-1(22),5,7,9,19(23),20-hexaene-2,2,4-trione (Compound 295)

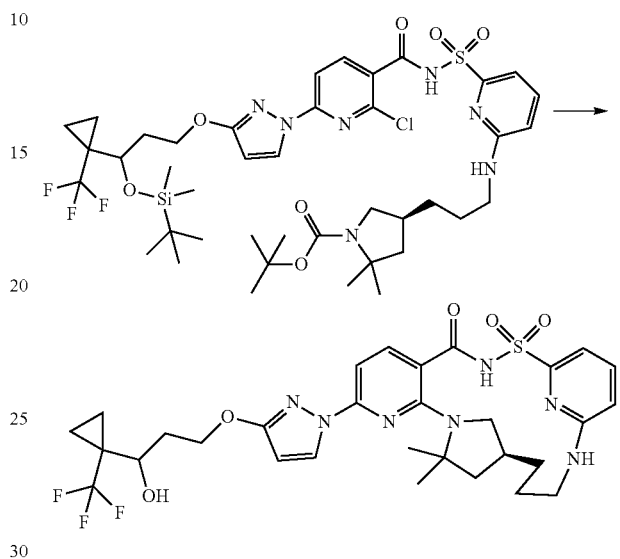

A solution of tert-butyl (4S)-4-[3-[[6-[[6-[3-[3-[tert-butyl(dimethyl)silyl]oxy-3-[1-(trifluoromethyl)cyclopropyl]propoxy]pyrazol-1-yl]-2-chloro-pyridine-3-carbonyl]sulfamoyl]-2-pyridyl]amino]propyl]-2,2-dimethyl-pyrrolidine-1-carboxylate (572 mg, 0.6254 mmol) in dichloromethane (4.8 mL) and trifluoroacetic acid (1.2 mL, 15.68 mmol) was stirred at room temperature for 4 h. The solvents were evaporated and the residue was dissolved in ethyl acetate, washed with 2 mL of saturated sodium bicarbonate solution and the solvent was removed and dried under vacuum. The resulting residue was dissolved in dimethyl sulfoxide (15 mL) and 3 Å molecular sieves were added and the reaction mixture was stirred for 10 min. Then, cesium fluoride (301 mg, 1.982 mmol) and potassium carbonate (284 mg, 2.055 mmol) were added and the reaction mixture was heated at 150° C. for 16 h. The reaction mixture was cooled to room temperature and filtered through Celite and to the filtrate was added saturated ammonium chloride solution. The mixture was extracted with ethyl acetate and the organic layer was washed with brine, dried over anhydrous sodium sulfate, filtered and concentrated. The resultant brown residue was purified by silica gel column chromatography using a shallow gradient from 100% hexanes to 100% ethyl acetate to afford (14S)-8-(3-{3-hydroxy-3-[1-(trifluoromethyl) cyclopropyl]propoxy}-1H-pyrazol-1-yl)-12,12-dimethyl-2λ⁶-thia-3,9,11,18,23-pentaazatetracyclo[17.3.1.111,14.05,10] tetracosa-1(22),5,7,9,19(23),20-hexaene-2,2,4-trione (Compound 295) (192 mg, 46%) as an off white solid. ¹H NMR (400 MHz, Chloroform-d) δ 9.77 (s, 1H), 8.20 (dd, J=2.7, 1.1 Hz, 1H), 8.02 (dd, J=8.4, 0.9 Hz, 1H), 7.54 (d, J=7.5 Hz, 1H), 7.47 (dt, J=7.4, 1.1 Hz, 1H), 7.15 (d, J=8.3 Hz, 1H), 6.54 (d, J=8.2 Hz, 1H), 5.92 (d, J=2.7 Hz, 1H), 4.70 (s, 1H), 4.57 (dddd, J=11.1, 9.1, 4.0, 2.1 Hz, 1H), 4.40 (dt, J=10.5, 5.1 Hz, 1H), 3.90 (s, 1H), 3.80 (dd, J=10.0, 2.5 Hz, 1H), 3.32 (dd, J=10.1, 7.4 Hz, 1H), 3.16 (d, J=13.7 Hz, 1H), 3.08-2.94 (m, 1H), 2.53 (d, J=11.2 Hz, 1H), 2.28-2.16 (m, 1H), 2.11-1.89 (m, 2H), 1.70-1.49 (m, 10H), 1.09-0.93 (m, 2H), 0.92-0.80 (m, 2H). ESI-MS m/z calc. 663.24506, found 664.17 (M+1)+; Retention time: 1.93 min (LC Method B).

Example 101: Preparation of (14S)-8-(3-{3-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 296) and (14S)-8-(3-{3-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹¹,14.0⁵,¹⁰]tetracosa-1(22),5,7,9,19(23),20-hexaene-2,2,4-trione (Diastereomer 2) (Compound 297)

Step 1: (14S)-8-(3-{3-Hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo [17.3.1.1¹¹¹,14.0⁵,¹⁰]tetracosa-1(22),5,7,9,19(23), 20-hexaene-2,2,4-trione (Diastereomer 1) (Compound 296) and (14S)-8-(3-{3-hydroxy-3-[1-(trifluoromethyl)cyclo propyl]propoxy}-1H-pyrazol-1-yl)-12,12-dimethyl-2λ⁶-thia-3,9,11,18,23-pentaazatetracyclo[17.3.1.1¹¹¹,14.0⁵,¹⁰]tetracosa-1(22), 5,7,9,19(23),20-hexaene-2,2,4-trione (Diastereomer 2) (Compound 297)

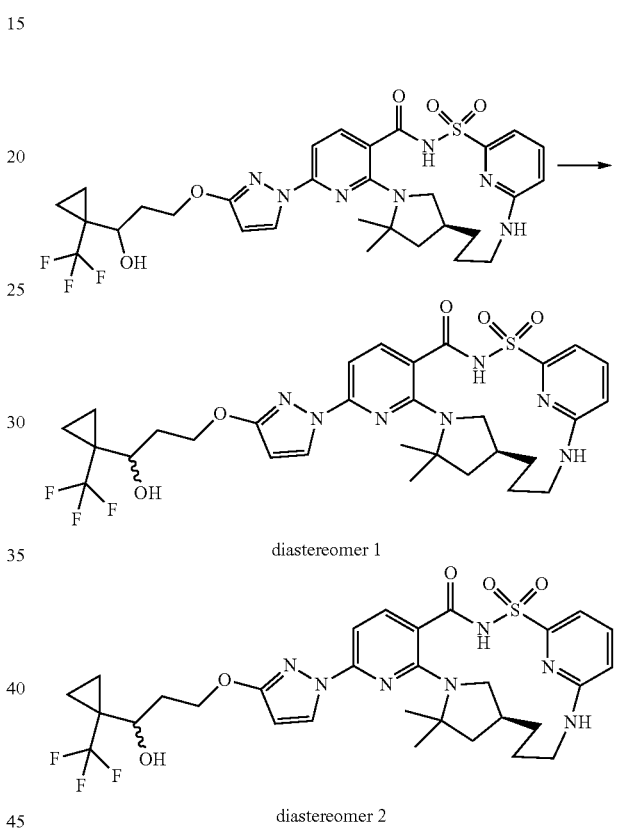

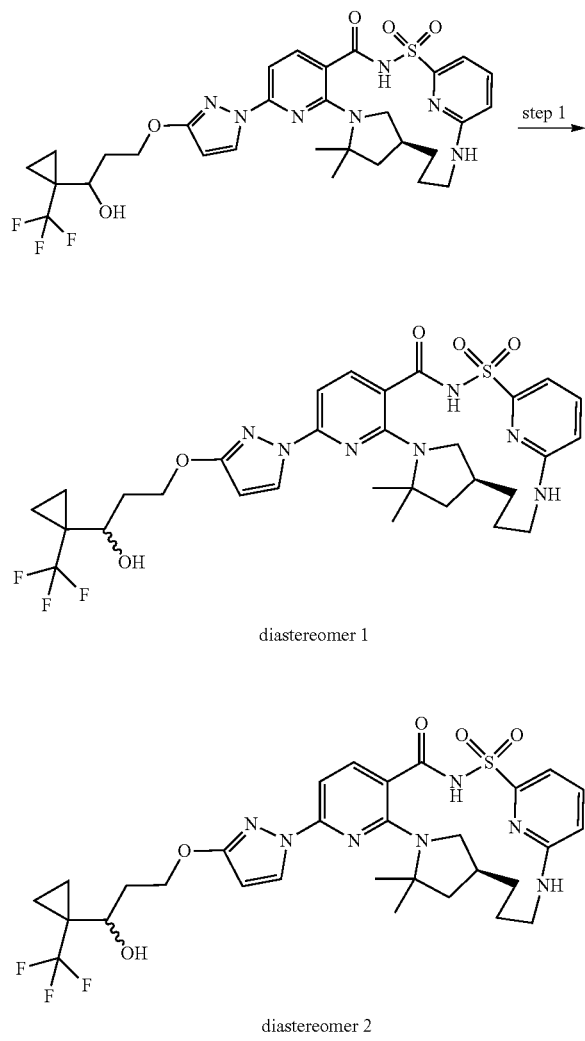 [SMILES: CC1(C)C[C@@H]2CCCNc3cccc(n3)S(=O)(=O)NC(=O)c3ccc(-n4ccc(OCCC(O)C5(C(F)(F)F)CC5)n4)nc3N1C2 ; CC1(C)C[C@@H]2CCCNc3cccc(n3)S(=O)(=O)NC(=O)c3ccc(-n4ccc(OCCC(O)C5(C(F)(F)F)CC5)n4)nc3N1C2 ; CC1(C)C[C@@H]2CCCNc3cccc(n3)S(=O)(=O)NC(=O)c3ccc(-n4ccc(OCCC(O)C5(C(F)(F)F)CC5)n4)nc3N1C2]

Subjected (14S)-8-(3-{3-hydroxy-3-[1-(trifluoromethyl)cyclopropyl]propoxy}-1H-pyrazol-1-yl)-12,12-dimethyl-2λ⁶-thia-3,9,11,18,23-pentaazatetra cyclo[17.3.1.1¹¹¹,14.05,10]tetracosa-1(22),5,7,9,19(23),20-hexaene-2,2,4-trione (187 mg) to chiral separation by SFC chromatography using a Chiral Pak IG (250×21.2 mm) column (5 μm particle size) with 38% methanol, 62% carbon dioxide mobile phase at 70 mL/min over 8.0 min (injection volume=500 μL of ~31 mg/mL in acetonitrile:methanol (90:10)) giving as the first diastereomer to elute (14S)-8-(3-{3-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo [17.3.1.1¹¹¹,14.05,10]tetracosa-1(22),5,7,9,19(23),20-hexaene-2,2,4-trione (diastereomer 1) (Compound 296) (59.2 mg, 32%) as a white solid; ¹H NMR (400 MHz, dimethyl sulfoxide-d₆) δ 12.50 (s, 1H), 8.21 (d, J=2.8 Hz, 1H), 7.82 (d, J=8.2 Hz, 1H), 7.58 (dd, J=8.5, 7.2 Hz, 1H), 7.05 (d, J=7.1 Hz, 1H), 6.98 (d, J=8.5 Hz, 1H), 6.92 (d, J=8.2 Hz, 1H), 6.71 (d, J=8.5 Hz, 1H), 6.13 (d, J=2.7 Hz, 1H), 5.23 (d, J=5.7 Hz, 1H), 4.31 (dd, J=8.2, 5.6 Hz, 2H), 3.92 (d, J=12.8 Hz, 1H), 3.69 (t, J=7.0 Hz, 1H), 3.17 (d, J=4.7 Hz, 1H), 2.95 (d, J=13.2 Hz, 1H), 2.76-2.66 (m, 1H), 2.08 (dd, J=12.4, 7.7 Hz, 2H), 1.82 (dtd, J=16.6, 11.7, 6.2 Hz, 3H), 1.61 (s, 3H), 1.60-1.53 (m, 2H), 1.52 (s, 3H), 1.30 (dt, J=24.6, 12.0 Hz, 1H), 0.93-0.81 (m, 4H); ESI-MS m/z calc. 663.24506, found 664.11 (M+1)+; Retention time: 1.94 min (LC Method B) and as the second diastereomer to elute (14S)-8-(3-{3-hydroxy-3-[1-(trifluoromethyl)cyclopropyl]propoxy}-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 2) (Compound 297) (57.8 mg, 31%) as white solid; ¹H NMR (400 MHz, dimethyl sulfoxide-d₆) δ 12.51 (s, 1H), 8.21 (d, J=2.7 Hz, 1H), 7.81 (d, J=8.2 Hz, 1H), 7.63-7.54 (m, 1H), 7.05 (d, J=7.1 Hz, 1H), 6.98 (s, 1H), 6.92 (d, J=8.2 Hz, 1H), 6.71 (d, J=8.5 Hz, 1H), 6.12 (d, J=2.7 Hz, 1H), 5.24 (d, J=5.7 Hz, 1H), 4.31 (dd, J=7.6, 5.0 Hz, 2H), 3.92 (d, J=13.3 Hz, 1H), 3.69 (t, J=7.4 Hz, 1H), 3.17 (d, J=5.0 Hz, 1H), 2.95 (d, J=13.4 Hz, 1H), 2.69 (d, J=16.0 Hz, 1H), 2.20-2.01 (m, 2H), 1.83 (ddd, J=25.2, 11.4, 6.3 Hz, 3H), 1.61 (s, 3H), 1.57 (d, J=12.7 Hz, 2H), 1.52 (s, 3H), 1.31 (q, J=12.5, 12.1 Hz, 1H), 0.87 (d, J=8.1 Hz, 4H); ESI-MS m/z calc. 663.24506, found 664.11 (M+1)+; Retention time: 1.94 min (LC Method B).

Example 102: Preparation of (14S)-8-[3-(2-{dispiro[2.0.2.1]heptan-7-yl}-1,1,2,2-tetradeuterio-ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Compound 299)

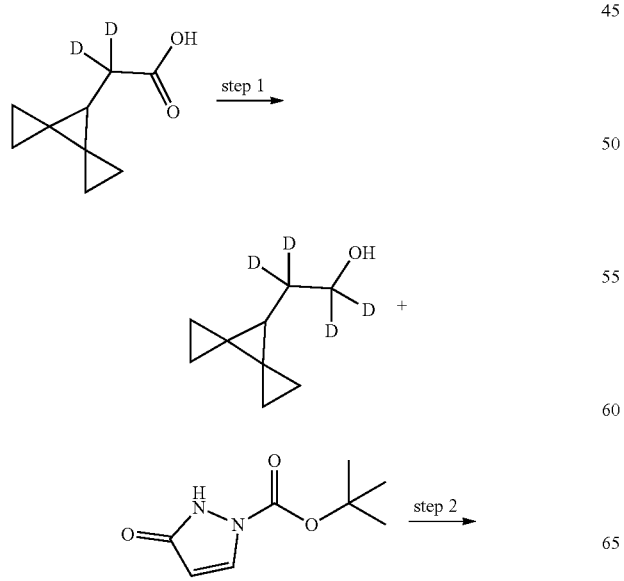

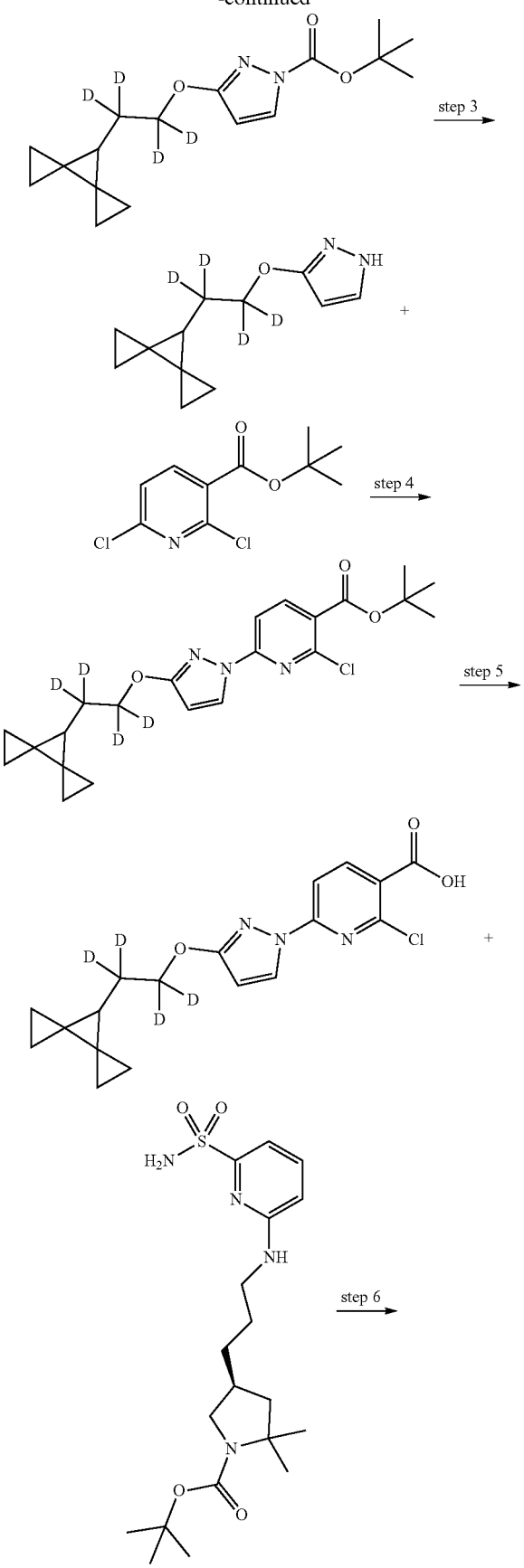

779

-continued

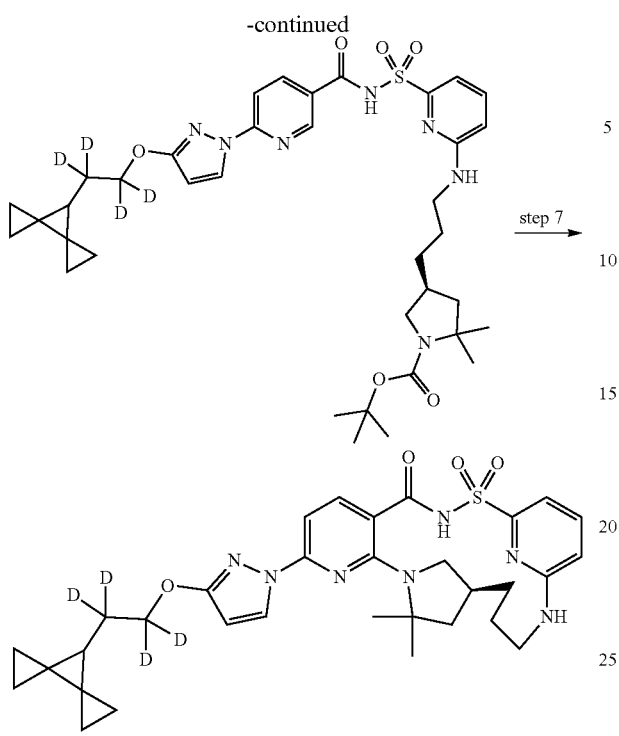

Step 1: 1,1,2,2-Tetradeuterio-2-dispiro[2.0.2.1]heptan-7-ylethanol

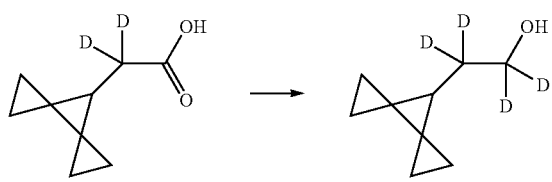 [SMILES: [2H]C([2H])(C(=O)O)C1C2(CC2)C12CC2 ; [2H]C([2H])(O)C([2H])([2H])C1C2(CC2)C12CC2]

Lithium aluminum deuteride (2.8120 g, 68.955 mmol) was weighed in a reaction flask placed in an ice-water bath under nitrogen balloon. Added tetrahydrofuran (160 mL) slowly. The mixture was let to stir in the ice-water bath for 10 min. 2,2-Dideuterio-2-dispiro[2.0.2.1]heptan-7-yl-acetic acid (10.85 g, 63.326 mmol), separately dissolved in tetrahydrofuran (40 mL) was added via syringe in a quick dropwise manner. The mixture was allowed to warm up to room temperature and was stirred for 15 h at room temperature. It was then recooled in an ice-water bath. A solution of Rochelle's salt was added in small portions to quench the unreacted lithium aluminum deuteride. After completion of quenching, more Rochelle's solution (200 mL) was added. The mixture was stirred at room temperature for 10 min and the layers were separated. The aqueous layer was extracted with ether (3×60 mL). The combined organic layers were then washed with brine, dried over anhydrous sodium sulfate, filtered and concentrated at 30° C., 100 mbar to afford 1,1,2,2-tetradeuterio-2-dispiro[2.0.2.1]heptan-7-yl-ethanol (9.72 g, 97%, 90% purity) as a slightly yellow liquid. $^1$H NMR (250 MHz, dimethyl sulfoxide-d$_6$) δ 1.34 (s, 1H), 0.76 (q, J=8.6, 7.1 Hz, 4H), 0.67-0.53 (m, 2H), 0.53-0.33 (m, 2H).

780

Step 2: tert-Butyl 3-(1,1,2,2-tetradeuterio-2-dispiro[2.0.2.1]heptan-7-yl-ethoxy)pyrazole-1-carboxylate

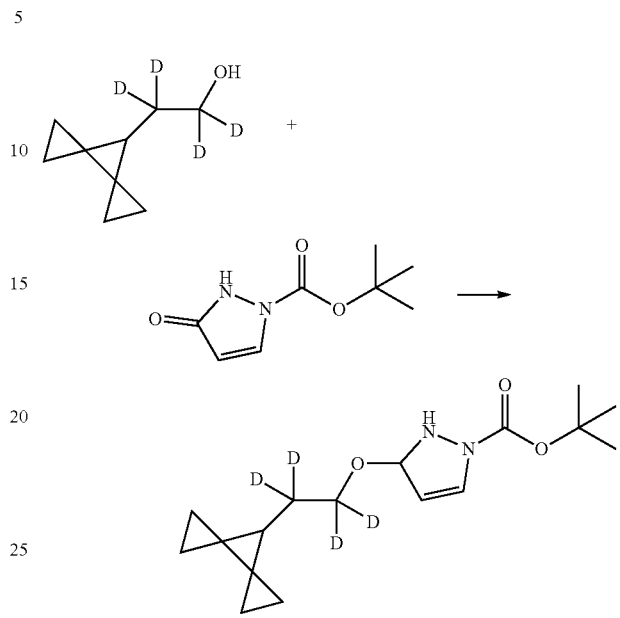

To a solution of tert-butyl 5-oxo-1H-pyrazole-2-carboxylate (6.235 g, 33.85 mmol) and 1,1,2,2-tetradeuterio-2-dispiro[2.0.2.1]heptan-7-yl-ethanol (5.0 g, 35.15 mmol) in tetrahydrofuran (80 mL) was added triphenylphosphine (9.37 g, 35.72 mmol). To the mixture was slowly added diisopropyl azodicarboxylate (7.0 mL, 35.55 mmol) dropwise over 10 min (exotherm noted). The reaction mixture was stirred at room temperature for 2 h. The tetrahydrofuran was removed in vacuo. The crude product was purified by silica gel chromatography using a shallow gradient from 100% hexanes to 20% ethyl acetate in hexanes giving tert-butyl 3-(1,1,2,2-tetradeuterio-2-dispiro[2.0.2.1]heptan-7-yl-ethoxy)pyrazole-1-carboxylate (7.4 g, 71%) as a clear syrup. $^1$H NMR (400 MHz, Chloroform-d) δ 7.82 (d, J=2.9 Hz, 1H), 5.84 (d, J=2.9 Hz, 1H), 1.61 (s, 9H), 1.44 (s, 1H), 0.83 (q, J=1.9 Hz, 4H), 0.68-0.61 (m, 2H), 0.52-0.45 (m, 2H). ESI-MS m/z calc. 308.2038, found 309.2 (M+1)$^+$; Retention time: 2.08 min (LC Method E).

Step 3: 3-(1,1,2,2-Tetradeuterio-2-dispiro[2.0.2.1]heptan-7-yl-ethoxy)-1H-pyrazole

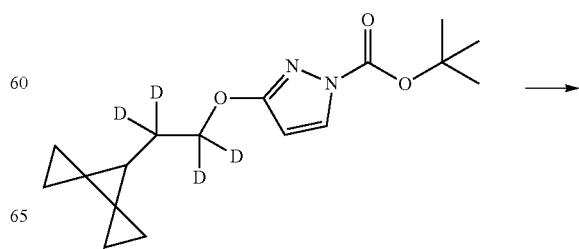

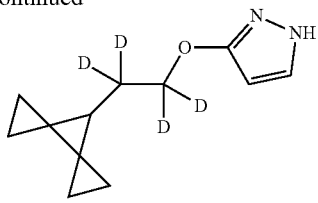

To a flask containing tert-butyl 3-(1,1,2,2-tetradeuterio-2-dispiro[2.0.2.1]heptan-7-yl-ethoxy)pyrazole-1-carboxylate (7.4 g, 23.99 mmol) was added dichloromethane (125 mL) and trifluoroacetic acid (45 mL, 584.1 mmol). After 30 min, the mixture was evaporated to dryness and neutralized with saturated sodium bicarbonate. The reaction was extracted with ethyl acetate and the organic layer was dried over sodium sulfate, filtered, and evaporated to provide a colorless oil, 3-(1,1,2,2-tetradeuterio-2-dispiro[2.0.2.1]heptan-7-yl-ethoxy)-1H-pyrazole (4.95 g, 99%). ESI-MS m/z calc. 208.15137, found 209.2 (M+1)$^+$; Retention time: 1.46 min (LC Method E).

Step 4: tert-Butyl 2-chloro-6-[3-(1,1,2,2-tetradeuterio-2-dispiro[2.0.2.1]heptan-7-yl-ethoxy)pyrazol-1-yl]pyridine-3-carboxylate

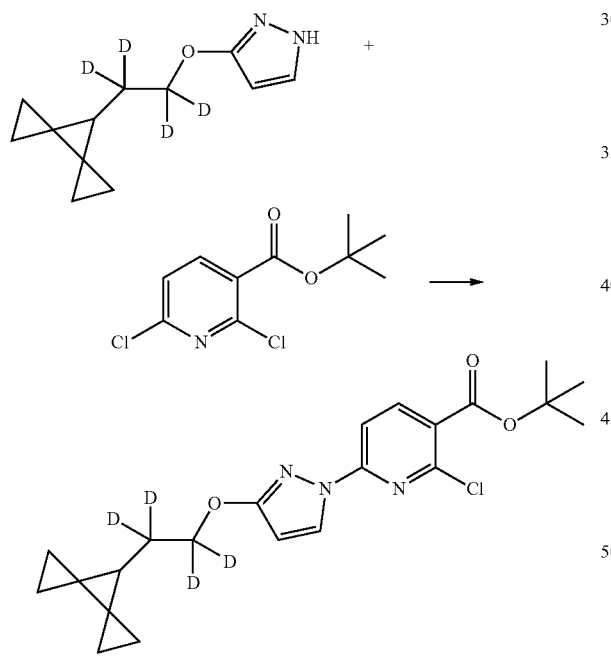

tert-Butyl 2,6-dichloropyridine-3-carboxylate (6.05 g, 24.38 mmol), 3-(1,1,2,2-tetradeuterio-2-dispiro[2.0.2.1]heptan-7-yl-ethoxy)-1H-pyrazole (5.04 g, 24.20 mmol) and potassium carbonate (7.4 g, 53.54 mmol) were combined in anhydrous dimethyl sulfoxide (125 mL). 1,4-Diazabicyclo[2.2.2]octane (545 mg, 4.859 mmol) was added and the mixture was stirred at room temperature under nitrogen for 18 h. The reaction mixture was diluted with water (75 mL) and stirred for 15 min. The resulting solid formed was filtered, collected and dried under vacuum overnight. The remaining filtrate was diluted with ethyl acetate, and washed with water (3×50 mL). The organic layers were combined and washed with brine. The organic layer was separated, dried over sodium sulfate, filtered and concentrated under reduced pressure. The residue was purified by silica gel chromatography using a gradient from 100% hexanes to 60% ethyl acetate in hexanes to afford a light yellow oil which was dried under vacuum to give a pale yellow solid which was combined with the previously filtered solid to give tert-butyl 2-chloro-6-[3-(1,1,2,2-tetradeuterio-2-dispiro[2.0.2.1]heptan-7-yl-ethoxy)pyrazol-1-yl]pyridine-3-carboxylate (9.95 g, 98%). $^1$H NMR (400 MHz, Chloroform-d) δ 8.35 (d, J=2.9 Hz, 1H), 8.19 (d, J=8.5 Hz, 1H), 7.69 (d, J=8.4 Hz, 1H), 5.94 (d, J=2.8 Hz, 1H), 1.62 (s, 9H), 1.48 (s, 1H), 0.88-0.81 (m, 4H), 0.70-0.62 (m, 2H), 0.51 (dt, J=10.7, 1.5 Hz, 2H). ESI-MS m/z calc. 419.19138, found 420.2 (M+1)$^+$; Retention time: 2.58 min (LC Method E).

Step 5: 2-Chloro-6-[3-(1,1,2,2-tetradeuterio-2-dispiro[2.0.2.1]heptan-7-yl-ethoxy)pyrazol-1-yl]pyridine-3-carboxylic Acid

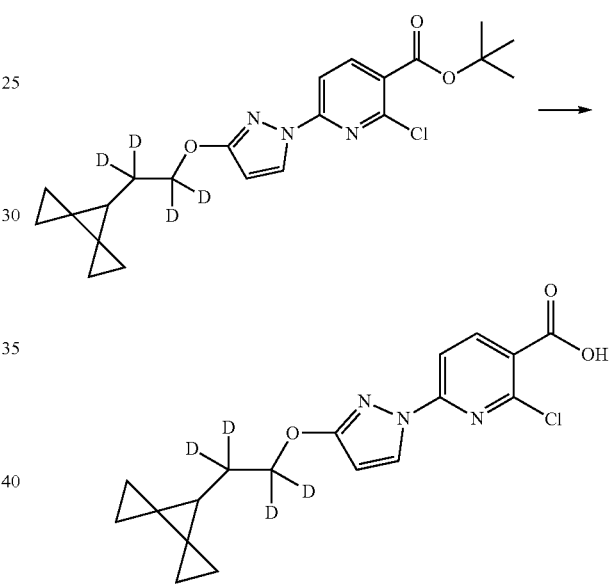

tert-Butyl 2-chloro-6-[3-(1,1,2,2-tetradeuterio-2-dispiro[2.0.2.1]heptan-7-yl-ethoxy)pyrazol-1-yl]pyridine-3-carboxylate (13.15 g, 31.31 mmol) was dissolved in dichloromethane (250 mL). To the mixture was slowly added trifluoroacetic acid (50 mL, 649.0 mmol) and the mixture was kept stirring at room temperature for 5 h. The reaction mixture was concentrated under reduced pressure to a solid, which was then slurried in diethyl ether and filtered (2×) resulting in a solid which was recrystallized from dichloromethane and collected by filtration to give a white solid (crop 1). Product remained in the dichloromethane filtrate which was evaporated giving an off-white solid which was dissolved in ethyl acetate and washed with 5N sodium hydroxide (2×), then 1N hydrochloric acid (1×), then dried (sodium sulfate), filtered and concentrated to a white solid which was chromatographed on a 150 g reverse phase C$_{18}$ column loading with dimethyl sulfoxide and eluting with a gradient from 50%-100% acetonitrile in water giving (after combination with filtered crop 1 solid) 2-chloro-6-[3-(1,1,2,2-tetradeuterio-2-dispiro[2.0.2.1]heptan-7-yl-ethoxy)pyrazol-1-yl]pyridine-3-carboxylic acid (9.05 g, 79%) as a white solid. $^1$H NMR (400 MHz, dimethyl sulfoxide-d$_6$) δ

13.61 (s, 1H), 8.53-8.28 (m, 2H), 7.72 (d, J=8.4 Hz, 1H), 6.17 (d, J=2.9 Hz, 1H), 1.46 (s, 1H), 0.87-0.79 (m, 4H), 0.68-0.61 (m, 2H), 0.53-0.45 (m, 2H). ESI-MS m/z calc. 363.12878, found 364.3 (M+1)+; Retention time: 1.45 min (LC Method G).

Step 6: tert-Butyl (4S)-4-[3-[[6-[[2-chloro-6-[3-(1,1,2,2-tetradeuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate

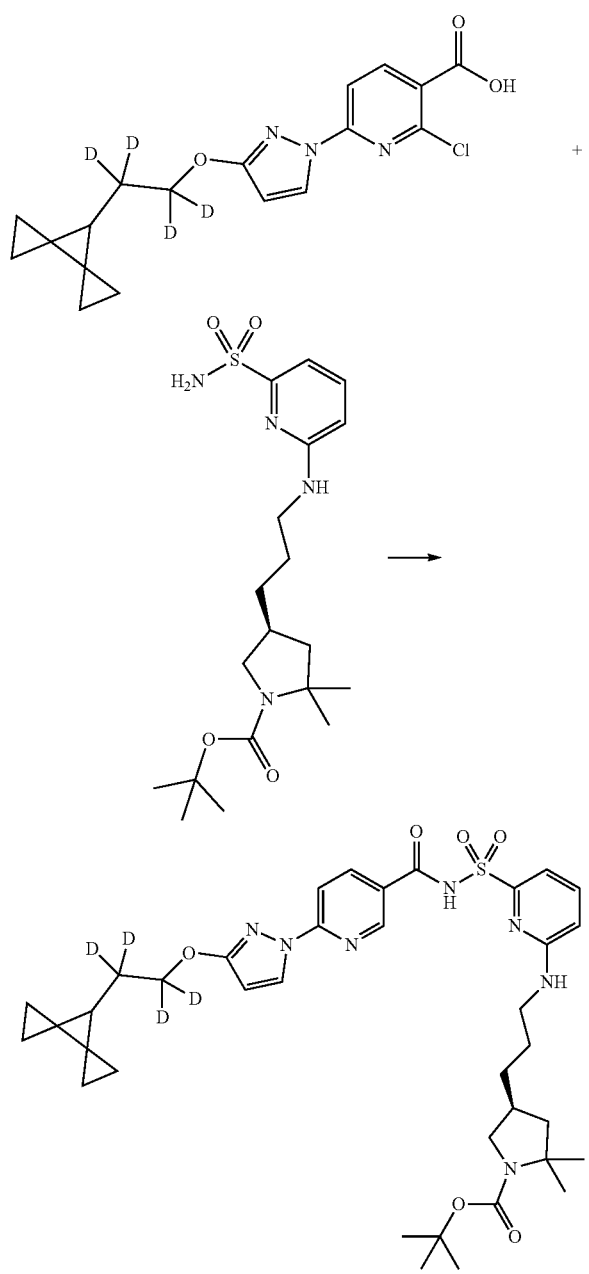

To a solution of 2-chloro-6-[3-(1,1,2,2-tetradeuterio-2-dispiro[2.0.2.1]heptan-7-yl-ethoxy)pyrazol-1-yl]pyridine-3-carboxylic acid (200 mg, 0.5497 mmol) in tetrahydrofuran (1.5 mL) was added carbonyl diimidazole (110 mg, 0.6784 mmol) (recrystallized from tetrahydrofuran) and the mixture was stirred at room temperature for 3 h then tert-butyl (4S)-2,2-dimethyl-4-[3-[(6-sulfamoyl-2-pyridyl)amino]propyl]pyrrolidine-1-carboxylate (240 mg, 0.5818 mmol) was added as a solution in tetrahydrofuran (500 µL) followed by 1,8-diazabicyclo[5.4.0]undec-7-ene (250 µL, 1.672 mmol) and the resulting mixture was stirred for 18 h at room temperature. The reaction was diluted with water and ethyl acetate then hydrochloric acid (600 µL of 6 M, 3.600 mmol) was added (aqueous layer was then pH=1). The layers were separated and the organic layer was washed with water (1×) and brine (1×) then dried over sodium sulfate, filtered and concentrated to a white foam which was purified on a $C_{18}$ reverse phase column eluting with a gradient from 50%-100% acetonitrile in water giving tert-butyl (4S)-4-[3-[[6-[[2-chloro-6-[3-(1,1,2,2-tetradeuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (190 mg, 46%) as an off-white solid. ESI-MS m/z calc. 757.33264, found 758.3 (M+1)+; Retention time: 2.14 min (LC Method G).

Step 7: (14S)-8-[3-(2-{Dispiro[2.0.2.1]heptan-7-yl}-1,1,2,2-tetradeuterio-ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (Compound 299)

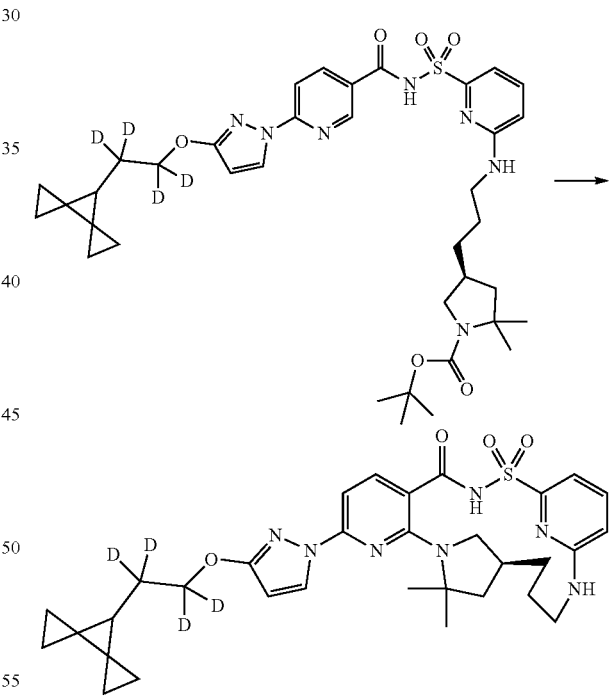

tert-Butyl (4S)-4-[3-[[6-[[2-chloro-6-[3-(1,1,2,2-tetradeuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (160 mg, 0.2110 mmol) was dissolved in dichloromethane (5 mL) and to the mixture was added trifluoroacetic acid (525 µL, 6.814 mmol) and the resulting mixture was stirred at room temperature for 30 min. Concentrated the mixture to dryness under reduced pressure, added 25 mL of toluene and removed by rotary evaporation. Again added 25 mL of toluene and removed by rotary evaporation then dried under vacuum overnight giving a residue which was combined with potassium carbonate (205 mg, 1.483 mmol), 3 Å molecular sieves and NMP (9.5 mL) in a vial, purged with nitrogen, capped, heated to 155° C. and stirred for 5 h. Cooled to room temperature and the mixture was filtered, diluted with ethyl acetate and washed with water (2×20 mL), followed by brine. The organic layer was further washed with water, dried over sodium sulfate, filtered and evaporated. The residue was purified on a $C_{18}$ reverse phase column eluting with a gradient from 50%-100% acetonitrile in water giving material which was then subjected to silica gel column chromatography using a shallow gradient of 100% dichloromethane to 10% methanol in dichloromethane to afford as an off-white solid, (14S)-8-[3-(2-{dispiro [2.0.2.1]heptan-7-yl}-1,1,2,2-tetradeuterio-ethoxy)-1H-pyrazol-1-yl]-12,12-dimethyl-2λ$^6$-thia-3,9,11,18,23-pentaazatetracyclo[17.3.1.111,14.05,10]tetracosa-1(22),5(10),6,8,19(23),20-hexaene-2,2,4-trione (Compound 299) (79.04 mg, 60%). $^1$H NMR (400 MHz, dimethyl sulfoxide-$d_6$) δ 12.51 (s, 1H), 8.20 (d, J=2.8 Hz, 1H), 7.81 (d, J=8.2 Hz, 1H), 7.57 (t, J=7.9 Hz, 1H), 7.05 (d, J=7.1 Hz, 1H), 6.99 (s, 1H), 6.91 (d, J=8.2 Hz, 1H), 6.71 (d, J=8.6 Hz, 1H), 6.08 (d, J=2.8 Hz, 1H), 3.92 (d, J=12.7 Hz, 1H), 3.15 (s, 1H), 2.95 (d, J=13.3 Hz, 1H), 2.78-2.63 (m, 1H), 2.12 (s, 1H), 1.85 (dd, J=11.8, 5.2 Hz, 1H), 1.77 (s, 1H), 1.60 (s, 5H), 1.55 (s, 1H), 1.51 (s, 3H), 1.45 (s, 1H), 1.30 (dt, J=23.8, 11.4 Hz, 1H), 0.87-0.79 (m, 4H), 0.69-0.60 (m, 2H), 0.53-0.46 (m, 2H). ESI-MS m/z calc. 621.3035, found 622.3 (M+1)$^+$; Retention time: 1.87 min (LC Method G).

Example 103: Preparation of (14S)-8-[3-(2-{dispiro [2.0.2.1]heptan-7-yl}-2,2-dideuterio-ethoxy)-1H-pyrazol-1-yl]-12,12-dimethyl(20-deuterio)-2λ$^6$-thia-3,9,11,18,23-pentaazatetracyclo[17.3.1.111,14.05,10]tetracosa-1(23),5,7,9,19,21-hexaene-2,2,4-trione (Compound 298)

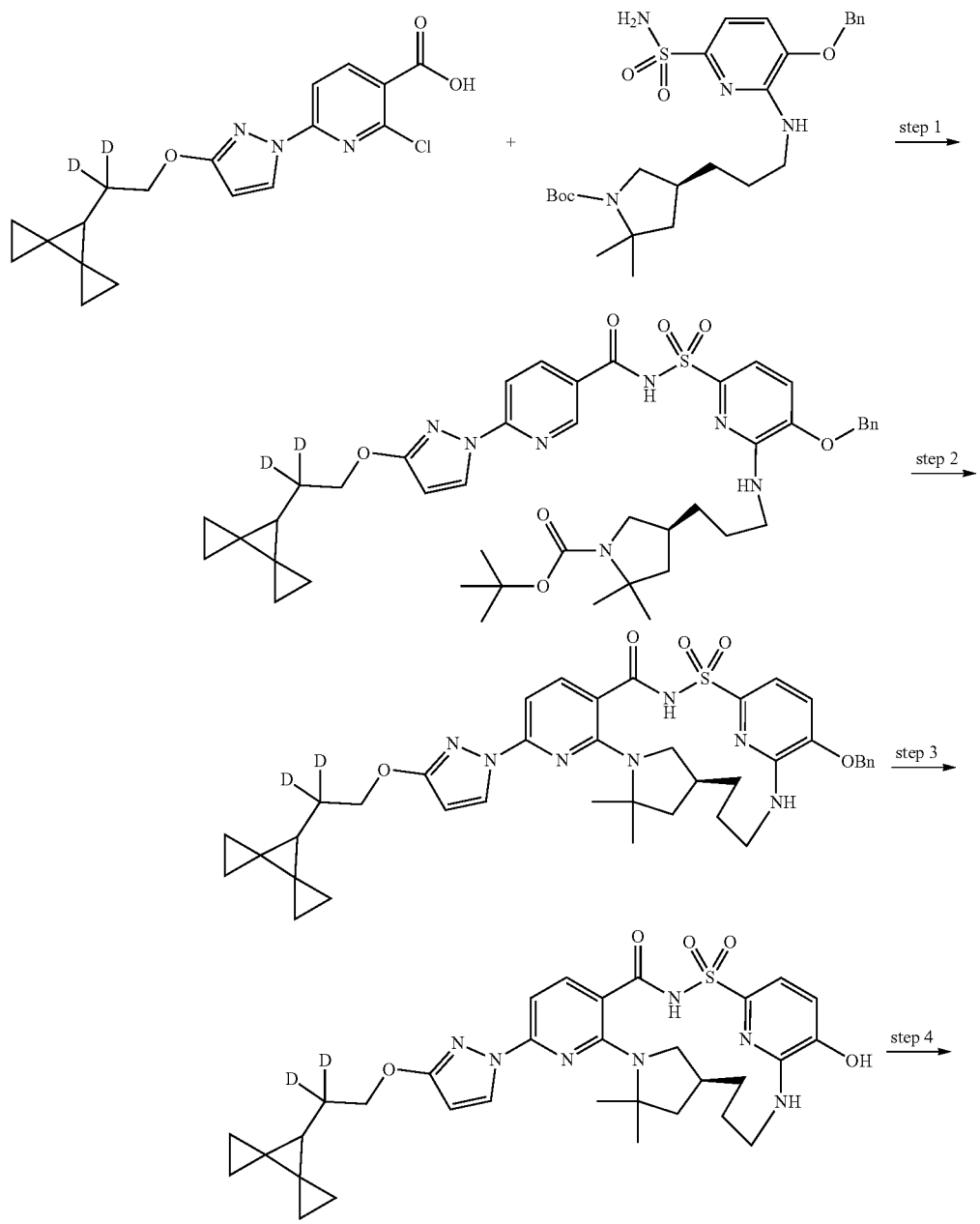

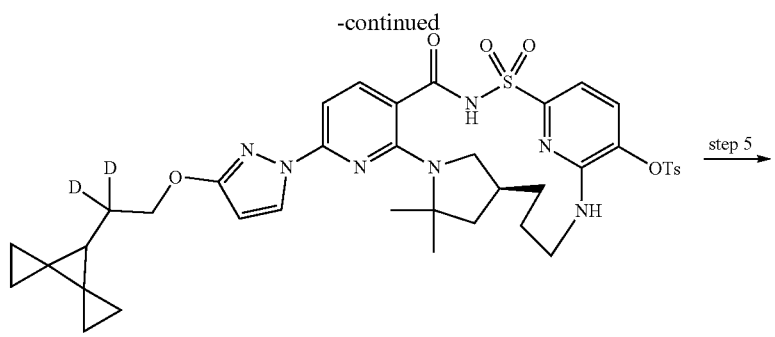

step 5

Step 1: tert-Butyl (4S)-4-[3-[[3-benzyloxy-6-[[2-chloro-6-[3-(2,2-dideuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate

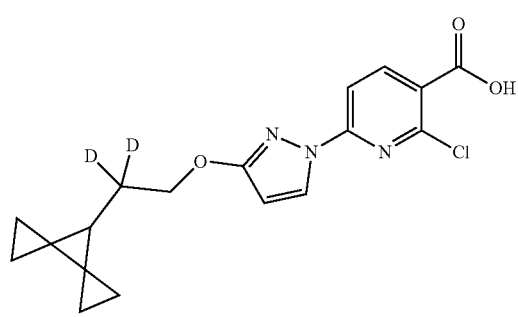

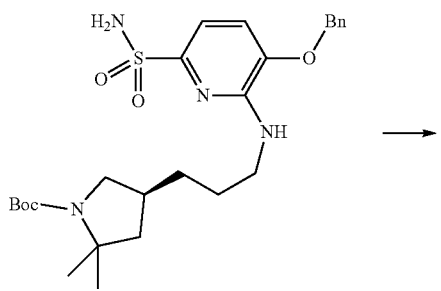

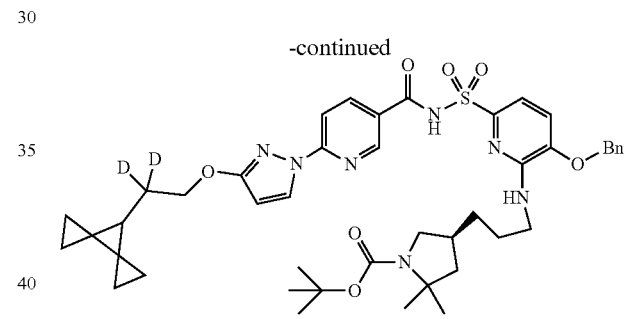

2-Chloro-6-[3-(2,2-dideuterio-2-dispiro[2.0.2.1]heptan-7-yl-ethoxy)pyrazol-1-yl]pyridine-3-carboxylic acid (1.5 g, 4.146 mmol) and carbonyl diimidazole (831 mg, 5.125 mmol) (freshly recrystallized from tetrahydrofuran, washed with cold ether and dried on high vacuum) were combined in tetrahydrofuran (10 mL) and stirred for 2 h at room temperature. Then, tert-butyl (4S)-4-[3-[(3-benzyloxy-6-sulfamoyl-2-pyridyl)amino]propyl]-2,2-dimethyl-pyrrolidine-1-carboxylate (1.5 g, 2.892 mmol) was added followed by 1,8-diazabicyclo[5.4.0]undec-7-ene (3.2 mL, 21.40 mmol) and the reaction was stirred at room temperature for 14 h. The reaction mixture was quenched with saturated ammonium chloride solution and extracted with ethyl acetate. The organic layer was washed with brine, dried over magnesium sulfate, filtered and concentrated. The resultant brown residue was purified by silica gel column chromatography using shallow gradient 100% hexanes to 100% ethyl acetate to afford tert-butyl (4S)-4-[3-[[3-benzyloxy-6-[[2-chloro-6-[3-(2,2-dideuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (2.2 g, 62%) as an off white solid. ESI-MS m/z calc. 861.36194, found 862.3 (M+1)$^+$; Retention time: 0.76 min (LC Method L).

Step 2: (14S)-20-(Benzyloxy)-8-[3-(2-{dispiro[2.0.2.1]heptan-7-yl}(2,2-dideuterio)ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione

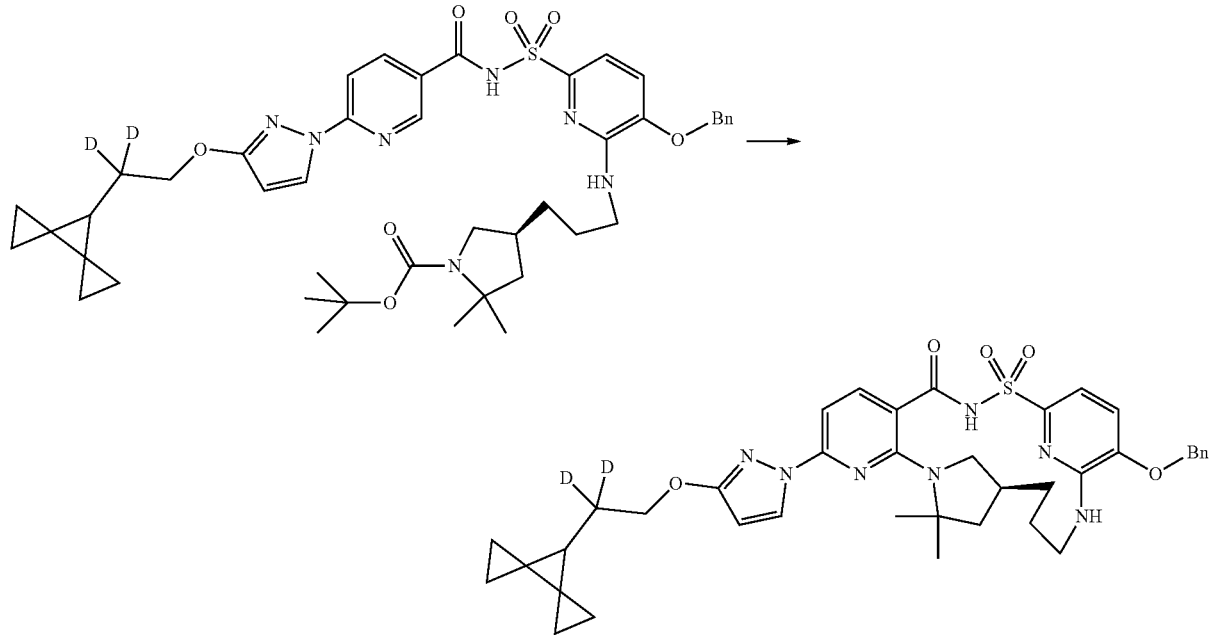

A solution of tert-butyl (4S)-4-[3-[[3-benzyloxy-6-[[2-chloro-6-[3-(2,2-dideuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (2.2 g, 2.551 mmol) in dichloromethane (16 mL) and trifluoroacetic acid (4 mL, 52.27 mmol) was stirred at room temperature for 2 h. The reaction solvents were removed by evaporation. The residue was dissolved in ethyl acetate and washed with saturated aqueous sodium bicarbonate solution (2 mL) and the organic layer was collected and solvent removed. The resulting residue was dissolved in dimethyl sulfoxide (50 mL) and oven dried 4 Å MS were added and the mixture was stirred for 10 min. Then, cesium fluoride (1.2 g, 7.900 mmol) and potassium carbonate (1.1 g, 7.959 mmol) were added and the reaction mixture was heated at 150° C. for 16 h. The reaction mixture was cooled to room temperature and filtered through Celite and washed with ethyl acetate and saturated ammonium chloride solution was added. The mixture was separated and the aqueous layer was extracted with ethyl acetate. Combined the organic layers, washed with brine, dried over anhydrous sodium sulfate, filtered and concentrated. The resultant brown residue was purified by silica gel column chromatography using a shallow gradient 100% hexanes to 100% ethyl acetate to afford (14S)-20-(benzyloxy)-8-[3-(2-{dispiro[2.0.2.1]heptan-7-yl}(2,2-dideuterio)ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (1.26 g, 68%) as an off white solid. ¹H NMR (400 MHz, Chloroform-d) δ 9.99 (s, 1H), 8.19 (d, J=2.7 Hz, 1H), 8.05 (d, J=8.4 Hz, 1H), 7.53 (d, J=8.0 Hz, 1H), 7.47-7.36 (m, 5H), 7.27-7.23 (m, 1H), 6.98 (d, J=8.1 Hz, 1H), 5.89 (d, J=2.7 Hz, 1H), 5.30 (d, J=8.4 Hz, 1H), 5.10 (s, 2H), 4.23 (s, 2H), 3.92 (s, 1H), 3.35 (dd, J=10.1, 7.4 Hz, 1H), 3.19 (d, J=14.1 Hz, 1H), 3.05 (t, J=9.9 Hz, 1H), 2.63 (s, 1H), 2.14-2.05 (m, 1H), 1.62 (t, J=3.2 Hz, 11H), 1.48 (s, 1H), 0.85 (q, J=2.5 Hz, 4H), 0.71-0.60 (m, 2H), 0.55-0.43 (m, 2H). ESI-MS m/z calc. 725.3328, found 726.45 (M+1)⁺; Retention time: 0.7 min (LC Method L).

Step 3: (14S)-8-[3-(2-{Dispiro[2.0.2.1]heptan-7-yl}(2,2-dideuterio)ethoxy)-1H-pyrazol-1-yl]-20-hydroxy-12,12-dimethyl-2λ⁶-thia-3,9,11,18,23-pentaazatetra cyclo[17.3.1.1¹¹,¹⁴.0⁵,¹⁰]tetracosa-1(23),5,7,9,19,21-hexaene-2,2,4-trione

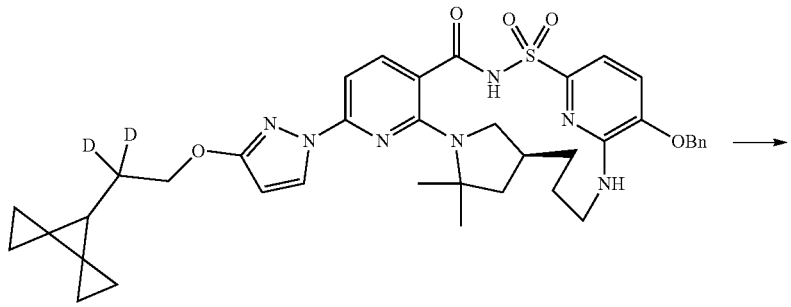

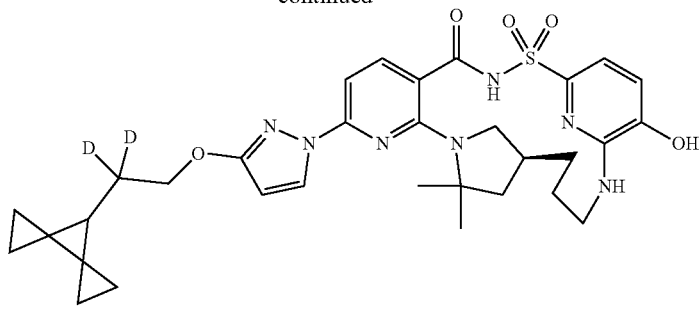

To a stirred solution of (14S)-20-(benzyloxy)-8-[3-(2-{dispiro[2.0.2.1]heptan-7-yl}(2,2-dideuterio)ethoxy)-1H-pyrazol-1-yl]-12,12-dimethyl-2λ$^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (500 mg, 0.6888 mmol) in EtOH (10 mL) was added 10% palladium on carbon (wet, Degussa, 155 mg, 0.1456 mmol) under nitrogen. The heterogeneous mixture was stirred under a hydrogen balloon for 2 h at ambient temperature and the black heterogeneous reaction mixture was filtered over a pad of celite. The filtrate was concentrated under reduced pressure to afford (14S)-8-[3-(2-{dispiro[2.0.2.1]heptan-7-yl}(2,2-dideuterio)ethoxy)-1H-pyrazol-1-yl]-20-hydroxy-12,12-dimethyl-2λ$^6$-thia-3,9,11,18,23-pentaazatetracyclo[17.3.1.1¹¹,¹⁴.0⁵,¹⁰]tetracosa-1(23),5,7,9,19,21-hexaene-2,2,4-trione (156 mg, 36%) as a light brown solid. ¹H NMR (400 MHz, dimethyl sulfoxide-d$_6$) δ 12.31 (s, 1H), 10.84 (s, 1H), 8.20 (d, J=2.8 Hz, 1H), 7.76 (d, J=8.2 Hz, 1H), 7.07 (d, J=7.7 Hz, 1H), 6.91 (dd, J=9.6, 7.9 Hz, 2H), 6.17 (s, 1H), 6.07 (d, J=2.7 Hz, 1H), 4.20 (d, J=1.5 Hz, 2H), 3.92 (s, 1H), 3.18 (s, 1H), 2.99 (d, J=13.1 Hz, 1H), 2.68 (s, 1H), 2.11 (d, J=6.6 Hz, 1H), 1.97-1.81 (m, 2H), 1.66-1.48 (m, 9H), 1.45 (s, 1H), 1.24 (q, J=11.7 Hz, 1H), 0.87-0.79 (m, 4H), 0.69-0.59 (m, 2H), 0.56-0.43 (m, 2H). ESI-MS m/z calc. 635.2859, found 636.39 (M+1)⁺; Retention time: 0.54 min (LC Method L).

Step 4: (14S)-8-[3-(2-{Dispiro[2.0.2.1]heptan-7-yl}(2,2-dideuterio)ethoxy)-1H-pyrazol-1-yl]-12,12-dimethyl-2,2,4-trioxo-2λ$^6$-thia-3,9,11,18,23-pentaazatetra cyclo[17.3.1.1¹¹,¹⁴.0⁵,¹⁰]tetracosa-1(23),5,7,9,19,21-hexaen-20-yl 4-methylbenzene-1-sulfonate

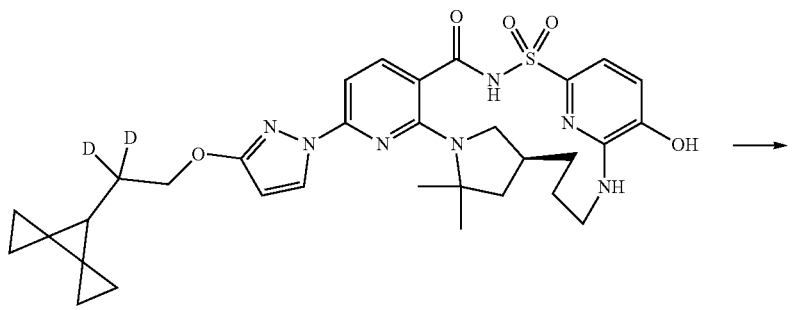

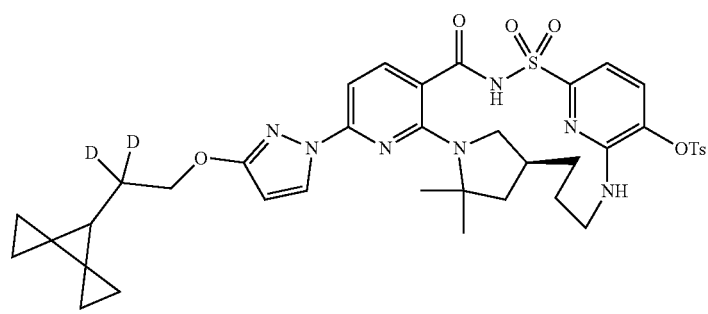

To a stirred solution of (14S)-8-[3-(2-{dispiro[2.0.2.1]heptan-7-yl}(2,2-dideuterio)ethoxy)-1H-pyrazol-1-yl]-20-hydroxy-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (50 mg, 0.07864 mmol) in anhydrous dichloromethane (2 mL) was added 4-methylbenzenesulfonyl chloride (17.8 mg, 0.09337 mmol), triethylamine (30 µL, 0.2152 mmol) and a catalytic amount of N,N-dimethylpyridin-4-amine (2.7 mg, 0.02210 mmol). The reaction mixture was stirred at room temperature overnight. The reaction was quenched with saturated aqueous ammonium chloride solution and extracted with ethyl acetate. Combined organic layers were washed with brine, dried over sodium sulfate, filtered and concentrated. The resultant brown residue was purified by silica gel column chromatography using a shallow gradient 100% hexanes to 100% ethyl acetate to afford (14S)-8-[3-(2-{dispiro[2.0.2.1]heptan-7-yl}(2,2-di deuterio)ethoxy)-1H-pyrazol-1-yl]-12,12-dimethyl-2,2,4-trioxo-2λ$^6$-thia-3,9,11,18,23-pentaazatetracyclo[17.3.1.1$^{11,14}$.0$^{5,10}$]tetracosa-1(23),5,7,9,19,21-hexaen-20-yl 4-methylbenzene-1-sulfonate (36 mg, 58%) as a white solid. $^1$H NMR (400 MHz, dimethyl sulfoxide-d$_6$) δ 12.56 (s, 1H), 8.20 (d, J=2.8 Hz, 1H), 7.92 (d, J=8.4 Hz, 2H), 7.80 (d, J=8.3 Hz, 1H), 7.65 (d, J=8.1 Hz, 1H), 7.47 (d, J=8.2 Hz, 2H), 7.12 (d, J=8.1 Hz, 1H), 6.91 (d, J=8.2 Hz, 1H), 6.76 (s, 1H), 6.08 (d, J=2.7 Hz, 1H), 4.20 (d, J=1.1 Hz, 2H), 3.77 (d, J=13.2 Hz, 1H), 3.34 (m, 1H), 3.03 (s, 1H), 2.79 (d, J=13.2 Hz, 1H), 2.50 (p, J=1.8 Hz, 1H), 2.42 (s, 3H), 2.03 (s, 1H), 1.83 (dd, J=11.8, 5.3 Hz, 2H), 1.58 (s, 3H), 1.51 (s, 3H), 1.48-1.32 (m, 4H), 0.88-0.76 (m, 4H), 0.68-0.59 (m, 2H), 0.54-0.40 (m, 2H). ESI-MS m/z calc. 789.29474, found 690.18 (M+1)$^+$; Retention time: 0.67 min (LC Method L).

Step 5: (14S)-8-[3-(2-{Dispiro[2.0.2.1]heptan-7-yl}-2,2-dideuterio-ethoxy)-1H-pyrazol-1-yl]-12,12-dimethyl(20-deuterio)-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound 298)

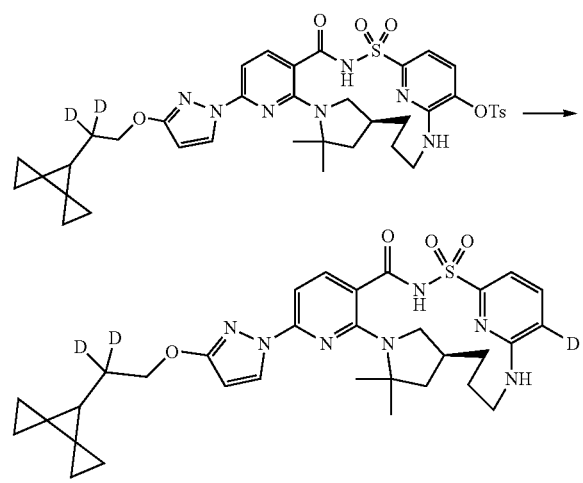

A solution of (14S)-8-[3-(2-{dispiro[2.0.2.1]heptan-7-yl}(2,2-dideuterio)ethoxy)-1H-pyrazol-1-yl]-12,12-dimethyl-2,2,4-trioxo-2λ$^6$-thia-3,9,11,18,23-pentaazatetracyclo[17.3.1.1$^{11,14}$.0$^{5,10}$]tetracosa-1(23),5,7,9,19,21-hexaen-20-yl 4-methylbenzene-1-sulfonate (70 mg, 0.088 mmol) in dry N,N-dimethylformamide (2 mL) was purged with nitrogen for 5 min using a balloon. Then, dichloronickel; triphenylphosphane (15 mg, 0.023 mmol) and tricyclohexylphosphane (18 mg, 0.064 mmol) were added. The resultant green solution was stirred for 5 min under nitrogen atmosphere and tetradeuterioboranuide (sodium salt) (50 mg, 1.195 mmol) was added in one portion. The resultant dark reddish brown mixture was stirred at room temperature for 1 h. Additional dichloronickel; triphenylphosphane (15 mg, 0.023 mmol), tricyclohexylphosphane (18 mg, 0.064 mmol) and tetradeuterioboranuide (sodium salt) (50 mg, 1.195 mmol) were added and the mixture was stirred at room temperature under nitrogen overnight. The reaction mixture was diluted with water, extracted with ethyl acetate, the organic layer dried over magnesium sulfate, filtered and evaporated. The resulting residue was dissolved in dimethyl sulfoxide and filtered through a Whatman filter disc (puradisc 25 TF) and the filtrate was purified by reverse phase HPLC-MS using a dual gradient run from 50%-99% mobile phase B over 15.0 min (mobile phase A=water (5 mM hydrochloric acid), mobile phase B=acetonitrile) to afford (14S)-8-[3-(2-{dispiro[2.0.2.1]heptan-7-yl}-2,2-di deuterio-ethoxy)-1H-pyrazol-1-yl]-12,12-dimethyl(20-deuterio)-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound 298) (22.8 mg, 41%) as a white solid. $^1$H NMR (400 MHz, dimethyl sulfoxide-d$_6$) δ 12.51 (s, 1H), 8.20 (d, J=2.8 Hz, 1H), 7.81 (d, J=8.3 Hz, 1H), 7.57 (d, J=7.3 Hz, 1H), 7.05 (d, J=7.2 Hz, 1H), 7.00 (s, 1H), 6.91 (d, J=8.2 Hz, 1H), 6.08 (d, J=2.7 Hz, 1H), 4.20 (d, J=1.4 Hz, 2H), 3.92 (d, J=12.4 Hz, 1H), 3.16 (s, 1H), 2.95 (d, J=13.2 Hz, 1H), 2.71 (t, J=10.8 Hz, 1H), 2.13 (s, 1H), 1.86 (dd, J=11.8, 5.3 Hz, 1H), 1.77 (s, 1H), 1.60 (s, 5H), 1.51 (s, 3H), 1.46 (s, 1H), 1.31 (q, J=12.6, 12.2 Hz, 1H), 0.90-0.78 (m, 5H), 0.68-0.62 (m, 2H), 0.53-0.46 (m, 2H). ESI-MS m/z calc. 620.29, found 621.24 (M+1)$^+$; Retention time: 1.3 min (LC Method J).

Example 104: Preparation of (14S)-8-[3-(2-{dispiro[2.0.2.1]heptan-7-yl}ethoxy)-1H-pyrazol-1-yl]-12,12-dimethyl(20-deuterio)-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (Compound 300)

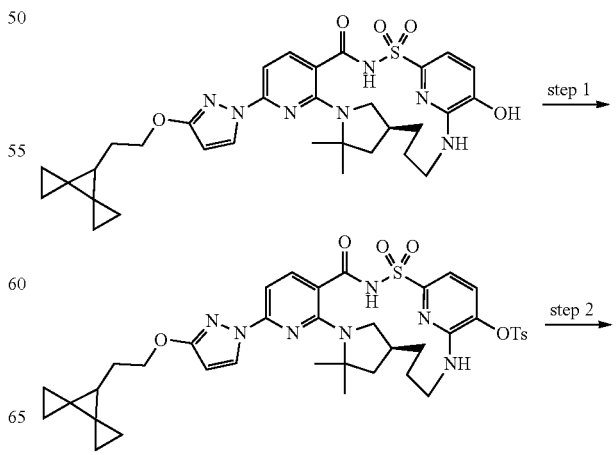

795
-continued

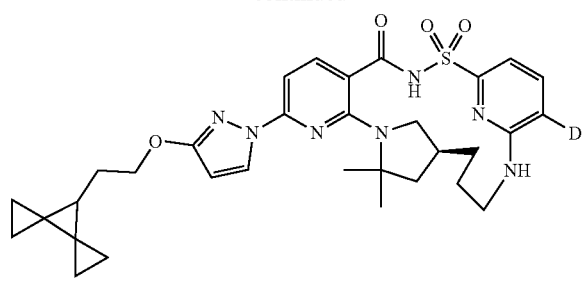 [SMILES: [2H]c1ccc2nc1NCCC[C@@H]1CN(c3nc(-n4ccc(OCC([2H])([2H])C5C6(CC6)C56CC6)n4)ccc3C(=O)NS2(=O)=O)C(C)(C)C1]

Step 1: (14S)-8-[3-(2-{Dispiro[2.0.2.1]heptan-7-yl}ethoxy)-1H-pyrazol-1-yl]-12,12-dimethyl-2,2,4-trioxo-2λ⁶-thia-3,9,11,18,23-pentaazatetracyclo[17.3.1.1¹¹,¹⁴.0⁵,¹⁰]tetracosa-1(23),5,7,9,19,21-hexaen-20-yl 4-methylbenzene-1-sulfonate

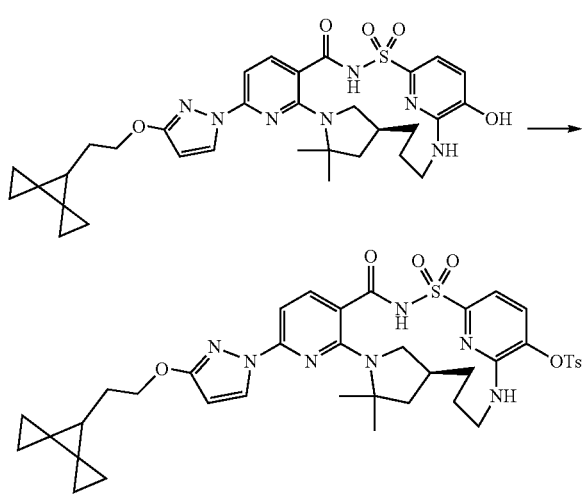

To a stirred solution of (14S)-8-[3-(2-{dispiro[2.0.2.1]heptan-7-yl}ethoxy)-1H-pyrazol-1-yl]-20-hydroxy-12,12-dimethyl-2λ⁶-thia-3,9,11,18,23-pentaazatetracyclo[17.3.1.1¹¹,¹⁴.0⁵,¹⁰]tetracosa-1 (23),5,7,9,19,21-hexaene-2,2,4-trione (150 mg, 0.2367 mmol) in anhydrous dichloromethane (3.000 mL) was added 4-methylbenzenesulfonyl chloride (58 mg, 0.3042 mmol), triethylamine (80 µL, 0.5740 mmol) and catalytic amount of N,N-dimethylpyridin-4-amine (10 mg, 0.08185 mmol). The reaction mixture was stirred at room temperature overnight. The reaction mixture was quenched with saturated aqueous ammonium chloride solution and extracted with ethyl acetate. The organic layer was washed with brine, dried over sodium sulfate and concentrated. The resultant brown residue was purified by silica gel column chromatography using a shallow gradient 100% hexanes to 100% ethyl acetate to afford (14S)-8-[3-(2-{dispiro[2.0.2.1]heptan-7-yl}ethoxy)-1H-pyrazol-1-yl]-12,12-dimethyl-2,2,4-trioxo-2λ⁶-thia-3,9,11,18,23-pentaazatetracyclo[17.3.1.1¹¹,¹⁴.0⁵,¹⁰]tetracosa-1(23),5,7,9,19,21-hexaen-20-yl 4-methylbenzene-1-sulfonate (120 mg, 51%) as a white solid. ESI-MS m/z calc. 787.28217, found 788.42 (M+1)⁺; Retention time: 1.39 min (LC Method J).

796

Step 2: (14S)-8-[3-(2-{Dispiro[2.0.2.1]heptan-7-yl}ethoxy)-1H-pyrazol-1-yl]-12,12-dimethyl(20-deuterio)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 300)

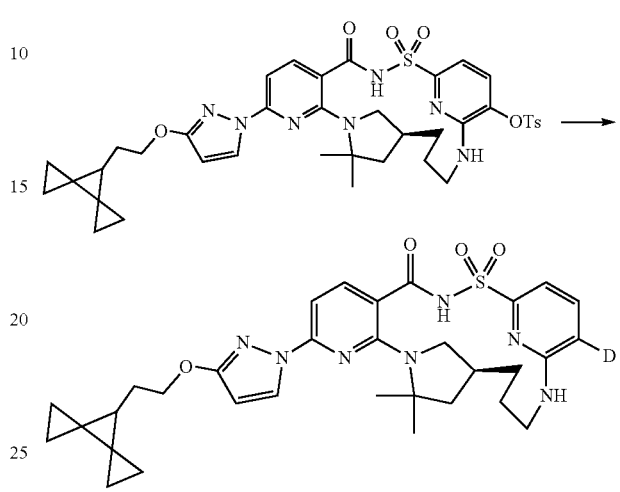

A solution of (14S)-8-[3-(2-{dispiro[2.0.2.1]heptan-7-yl}ethoxy)-1H-pyrazol-1-yl]-12,12-dimethyl-2,2,4-trioxo-2λ⁶-thia-3,9,11,18,23-pentaazatetracyclo[17.3.1.1¹¹,¹⁴.0⁵,¹⁰]tetracosa-1(23),5,7,9,19,21-hexaen-20-yl 4-methylbenzene-1-sulfonate (120 mg, 0.1523 mmol) in dry N,N-dimethylformamide (1 mL) was purged with nitrogen for 5 min using a balloon. Then, dichloronickel; triphenylphosphane (30 mg, 0.04586 mmol) and tricyclohexylphosphane (34 mg, 0.1212 mmol) were added. The resultant green solution was stirred for 5 min under nitrogen atmosphere and tetradeuterioboranuide (sodium salt) (87 mg, 2.079 mmol) was added in one portion. The resultant dark reddish brown mixture was stirred at room temperature for 1 h. Additional dichloronickel; triphenylphosphane (30 mg, 0.04586 mmol), tricyclohexylphosphane (34 mg, 0.1212 mmol) and tetradeuterioboranuide (sodium salt) (87 mg, 2.079 mmol) were added and the mixture was stirred at room temperature under nitrogen overnight. The reaction mixture was diluted with water and extracted with ethyl acetate. The organic layer was dried over magnesium sulfate, filtered and evaporated. The resultant residue was dissolved in dimethyl sulfoxide and filtered through a Whatman filter disc (puradisc 25 TF) and the filtrate was purified by reverse phase HPLC-MS using a dual gradient run from 50%-99% mobile phase B over 15.0 min (mobile phase A=water (5 mM hydrochloric acid), mobile phase B=acetonitrile) to afford (14S)-8-[3-(2-{dispiro[2.0.2.1]heptan-7-yl}ethoxy)-1H-pyrazol-1-yl]-12,12-dimethyl(20-deuterio)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 300) (35 mg, 37%) as a white solid. $^1$H NMR (400 MHz, dimethyl sulfoxide-$d_6$) δ 12.52 (s, 1H), 8.20 (d, J=2.8 Hz, 1H), 7.81 (d, J=8.2 Hz, 1H), 7.56 (d, J=7.1 Hz, 1H), 7.04 (d, J=7.2 Hz, 1H), 6.98 (s, 1H), 6.90 (d, J=8.1 Hz, 1H), 6.08 (d, J=2.7 Hz, 1H), 4.25-4.17 (m, 2H), 3.92 (d, J=12.5 Hz, 1H), 3.17 (s, 1H), 2.94 (d, J=13.2 Hz, 1H), 2.72 (s, 1H), 2.20-2.06 (m, 1H), 1.81 (q, J=6.6 Hz, 4H), 1.60 (s, 3H), 1.56 (d, J=13.5 Hz, 2H), 1.51 (s, 3H), 1.46 (d, J=6.5 Hz, 1H), 1.36-1.26 (m, 1H), 1.23 (s, 1H), 0.87-0.76 (m, 4H), 0.70-0.59 (m, 2H), 0.50 (dd, J=8.0, 4.3 Hz, 2H). ESI-MS m/z calc. 618.2847, found 619.25 (M+1)+; Retention time: 1.28 min (LC Method J).
Example 105: Preparation of (14S)-8-[3-(2-{dispiro[2.0.2.1]heptan-7-yl}-1,1,2,2-tetradeuterio-ethoxy)-1H-pyrazol-1-yl]-12,12-dimethyl(20-deuterio)-2λ6-thia-3,9,11,18,23-pentaazatetracyclo[17.3.1.111,14.05,10]tetracosa-1(23),5,7,9,19,21-hexaene-2,2,4-trione (Compound 301)
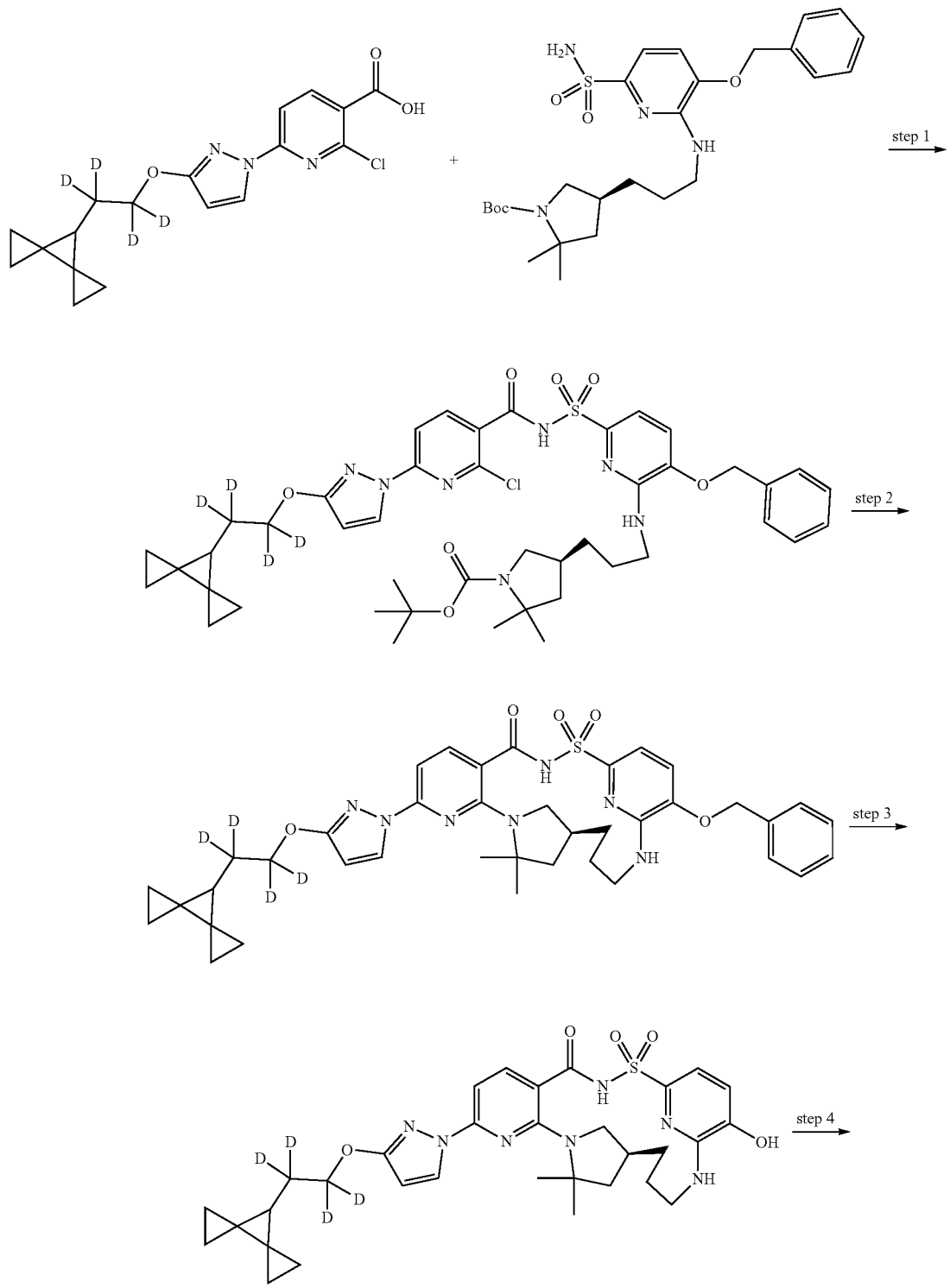

-continued
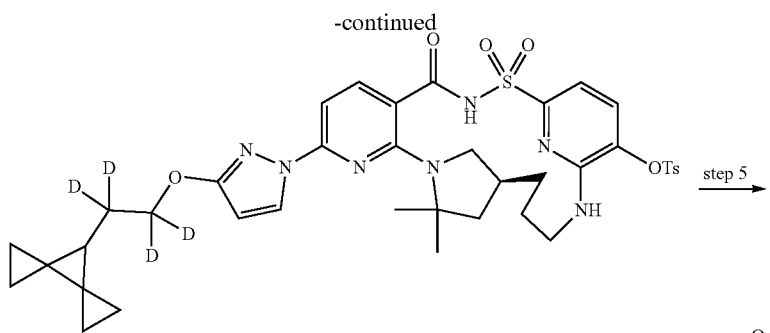
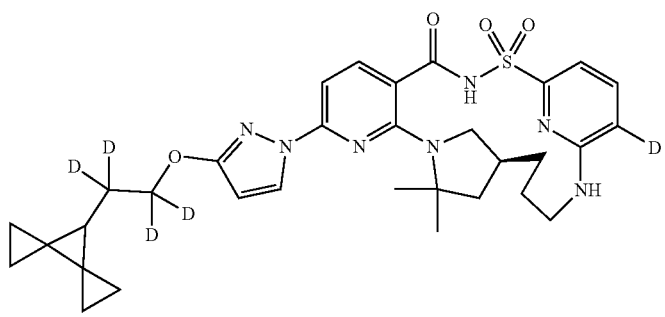 [SMILES: [2H]c1ccc2nc1NCCC[C@@H]1CN(c3nc(-n4ccc(OC([2H])([2H])C([2H])([2H])C5C6(CC6)C56CC6)n4)ccc3C(=O)NS2(=O)=O)C(C)(C)C1]
Step 1: tert-Butyl (4S)-4-[3-[[3-benzyloxy-6-[[2-chloro-6-[3-(1,1,2,2-tetradeuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate
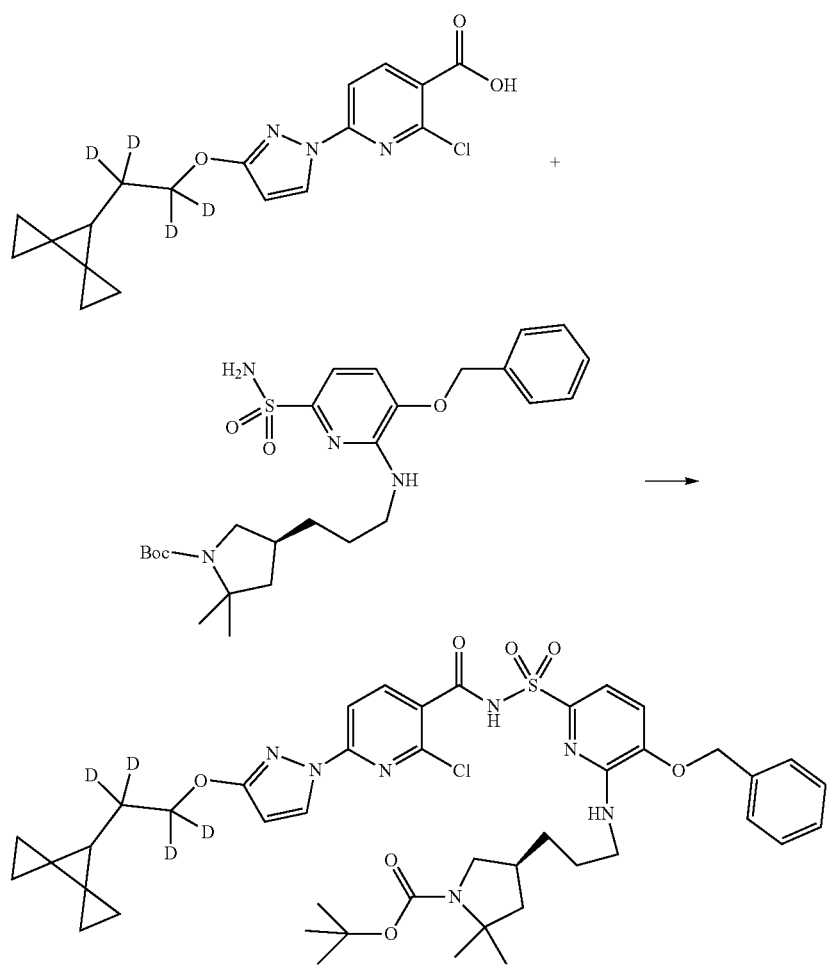

801

To a solution of 2-chloro-6-[3-(1,1,2,2-tetradeuterio-2-dispiro[2.0.2.1]heptan-7-yl-ethoxy)pyrazol-1-yl]pyridine-3-carboxylic acid (500 mg, 1.374 mmol) in dry tetrahydrofuran (5 mL) was added carbonyl diimidazole (207 mg, 1.277 mmol) and the mixture was stirred for 2 h at room temperature. Then tert-butyl (4S)-4-[3-[(3-benzyloxy-6-sulfamoyl-2-pyridyl)amino]propyl]-2,2-dimethyl-pyrrolidine-1-carboxylate (410 mg, 0.7905 mmol) was added followed by 1,8-diazabicyclo[5.4.0]undec-7-ene (600 µL, 4.012 mmol) and the reaction was stirred at room temperature for 14 h. The reaction mixture was quenched with saturated aqueous ammonium chloride solution and extracted with ethyl acetate. The organic layer was washed with brine, dried (magnesium sulfate), filtered and concentrated. The resultant brown residue was purified by silica gel column chromatography using a shallow gradient 100% hexanes to 100% ethyl acetate to afford tert-butyl (4S)-4-[3-[[3-benzyloxy-6-[[2-chloro-6-[3-(1,1,2,2-tetradeuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (436 mg, 37%) as an off white foamy solid. ESI-MS m/z calc. 863.3745, found 864.47 (M+1)+; Retention time: 1.74 min (LC Method L).

Step 2: (14S)-20-(Benzyloxy)-8-[3-(2-{dispiro[2.0.2.1]heptan-7-yl}-1,1,2,2-tetradeuterio-ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione

802

A solution of tert-butyl (4S)-4-[3-[[3-benzyloxy-6-[[2-chloro-6-[3-(1,1,2,2-tetradeuterio-2-dispiro[2.0.2.1]heptan-7-yl-ethoxy)pyrazol-1-yl]pyridine-3-carbonyl]sulfamoyl]-2-pyridyl]amino]propyl]-2,2-dimethyl-pyrrolidine-1-carboxylate (436 mg, 0.5043 mmol) in trifluoroacetic acid (400 µL, 5.192 mmol) and dichloromethane (1.6 mL) was stirred at room temperature for 2 h. The solvents were evaporated and the resulting residue was dissolved in ethyl acetate and washed with saturated aqueous sodium bicarbonate solution (2 mL) and the organic layer was collected and solvent removed. The resulting residue was dissolved in dimethyl sulfoxide (5 mL) and oven dried 4 Å MS were added and the resulting mixture was stirred for 10 min. Then, potassium carbonate (231 mg, 1.671 mmol) was added and the reaction mixture was heated at 140° C. for 16 h. The reaction mixture was filtered through a Whatman filter disc (puradisc 25 TF) and the filtrate was purified by reverse phase HPLC-MS using a dual gradient run from 50%-99% mobile phase B over 15.0 min. (mobile phase A=water (5 mM hydrochloric acid), mobile phase B=acetonitrile) to afford (14S)-20-(benzyloxy)-8-[3-(2-{dispiro[2.0.2.1]heptan-7-yl}-1,1,2,2-tetradeuterio-ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (184 mg, 44%) as an off white solid. ¹H NMR (400 MHz, Chloroform-d) δ 9.96 (s, 1H), 8.19 (d, J=2.8 Hz, 1H), 8.06 (d, J=8.4 Hz, 1H), 7.55 (d, J=8.0 Hz, 1H), 7.46-7.36 (m, 5H), 7.27 (d, J=8.5 Hz, 1H), 7.00 (d, J=8.1 Hz, 1H), 5.90 (d, J=2.8 Hz, 1H), 5.32 (d, J=6.3 Hz, 1H), 5.11 (s, 2H), 3.91 (s, 1H), 3.42-3.31 (m, 1H), 3.19 (d, J=14.1 Hz, 1H), 3.05 (t, J=9.7 Hz, 1H), 2.67 (s, 1H), 2.10 (dd, J=12.2, 8.2 Hz, 1H), 1.62 (s, 3H), 1.61 (s, 3H), 1.58 (br s, 4H), 1.25 (s, 1H), 0.85 (q, J=2.5 Hz, 4H), 0.69-0.61 (m, 2H), 0.54-0.46 (m, 2H). ESI-MS m/z calc. 727.3454, found 728.47 (M+1)+; Retention time: 1.43 min (LC Method J).

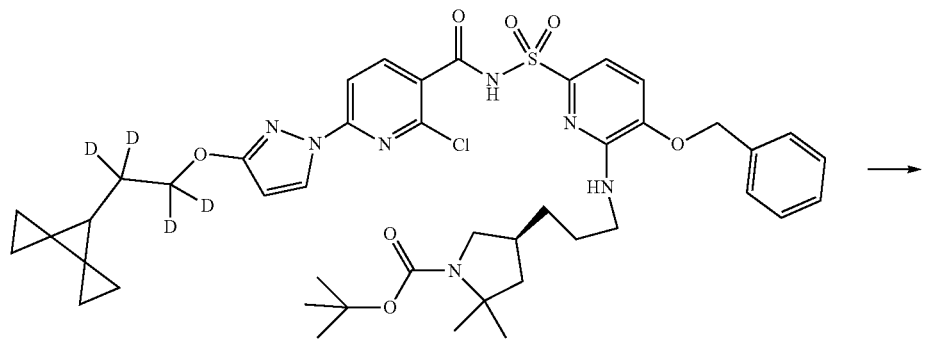

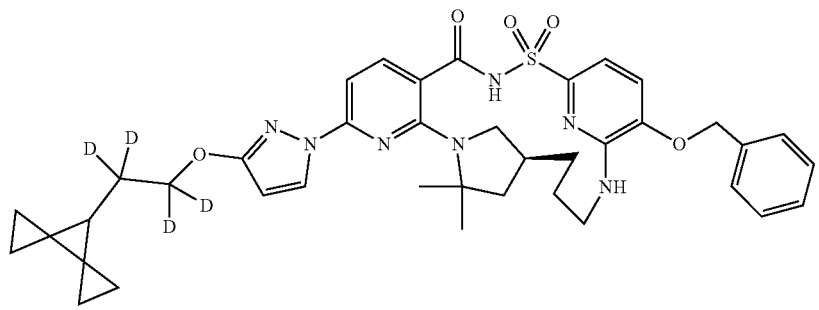

Step 3: (14S)-8-[3-(2-{Dispiro[2.0.2.1]heptan-7-yl}-1,1,2,2-tetradeuterio-ethoxy)-1H-pyrazol-1-yl]-20-hydroxy-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione

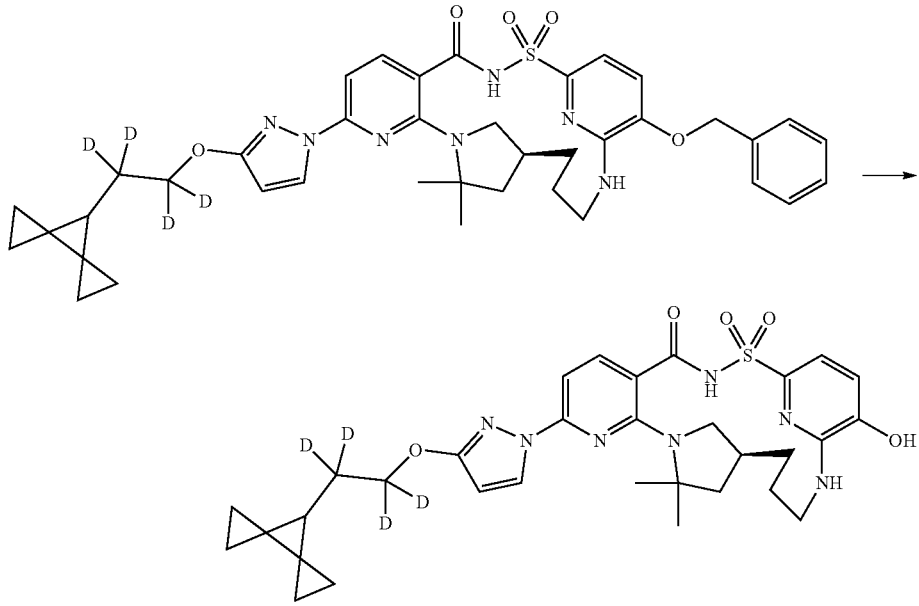

To a stirred solution of (14S)-20-(benzyloxy)-8-[3-(2-{dispiro[2.0.2.1]heptan-7-yl}-1,1,2,2-tetradeuterio-ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (184 mg, 0.2528 mmol) in EtOH (5 mL) was added 10% palladium on carbon (wet, Degussa, 27 mg, 0.02537 mmol) under nitrogen. The heterogeneous mixture was stirred under hydrogen (from balloon) for approximately 2 h at ambient temperature and the black heterogeneous reaction mixture was filtered over a pad of celite. The filtrate was concentrated under reduced pressure to afford (14S)-8-[3-(2-{dispiro[2.0.2.1]heptan-7-yl}-1,1,2,2-tetradeuterio-ethoxy)-1H-pyrazol-1-yl]-20-hydroxy-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (160 mg, 83%) as a light brown solid. ¹H NMR (400 MHz, dimethyl sulfoxide-d₆) δ 12.42 (s, 1H), 11.02 (s, 1H), 8.30 (d, J=2.7 Hz, 1H), 7.86 (d, J=8.2 Hz, 1H), 7.17 (d, J=7.7 Hz, 1H), 7.06 (d, J=7.8 Hz, 1H), 7.00 (d, J=8.2 Hz, 1H), 6.27 (s, 1H), 6.18 (d, J=2.8 Hz, 1H), 4.01 (s, 1H), 3.28 (s, 1H), 3.09 (d, J=12.9 Hz, 1H), 2.86-2.69 (m, 1H), 2.22 (s, 1H), 2.01 (s, 1H), 1.99-1.90 (m, 1H), 1.65 (d, J=34.6 Hz, 9H), 1.55 (s, 1H), 1.40-1.28 (m, 1H), 0.97-0.89 (m, 4H), 0.77-0.70 (m, 2H), 0.62-0.53 (m, 2H). ESI-MS m/z calc. 637.29846, found 638.33 (M+1)⁺; Retention time: 0.91 min (LC Method J).

Step 4: (14S)-8-[3-(2-{dispiro[2.0.2.1]heptan-7-yl}-1,1,2,2-tetradeuterio-ethoxy)-1H-pyrazol-1-yl]-12,12-dimethyl-2,2,4-trioxo-2λ⁶-thia-3,9,11,18,23-pentaazatetracyclo[17.3.1.1¹¹,¹⁴.0⁵,¹⁰]tetracosa-1(23),5,7,9,19,21-hexaen-20-yl 4-methylbenzene-1-sulfonate

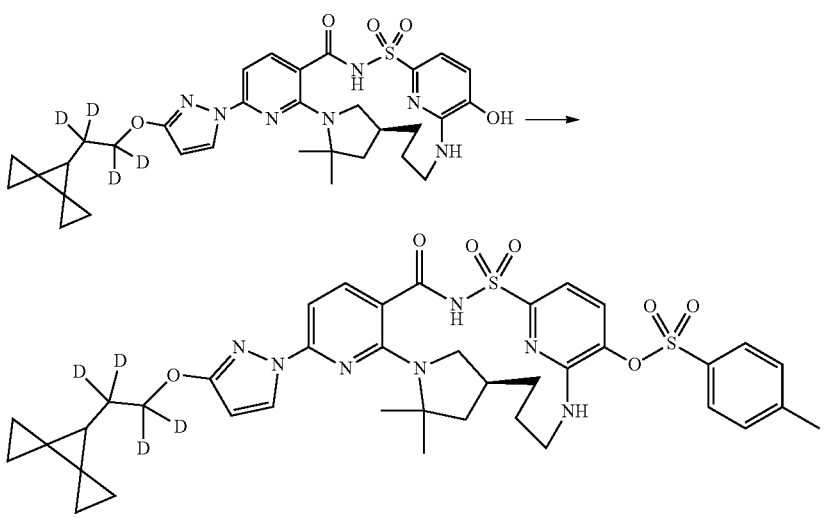

To a stirred solution of (14S)-8-[3-(2-{dispiro[2.0.2.1]heptan-7-yl}-1,1,2,2-tetradeuterio-ethoxy)-1H-pyrazol-1-yl]-20-hydroxy-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (160 mg, 0.2107 mmol) in anhydrous dichloromethane (2 mL) was added 4-methylbenzenesulfonyl chloride (45 mg, 0.2360 mmol), triethylamine (60 μL, 0.4305 mmol) and a catalytic amount of N,N-dimethylpyridin-4-amine (6 mg, 0.04911 mmol). The reaction mixture was stirred at room temperature overnight. The reaction was quenched with saturated aqueous ammonium chloride solution and extracted with ethyl acetate. The organic layer was washed with brine, dried over sodium sulfate and concentrated. The resulting brown residue was purified by silica gel column chromatography using a shallow gradient from 100% hexanes to 100% ethyl acetate to afford (14S)-8-[3-(2-{dispiro[2.0.2.1]heptan-7-yl}-1,1,2,2-tetradeuterio-ethoxy)-1H-pyrazol-1-yl]-12,12-dimethyl-2,2,4-trioxo-2λ⁶-thia-3,9,11,18,23-pentaazatetracyclo[17.3.1.1¹¹,¹⁴.0⁵,¹⁰]tetracosa-1(23),5,7,9,19,21-hexaen-20-yl 4-methylbenzene-1-sulfonate (147 mg, 88%) as a white solid. ¹H NMR (400 MHz, dimethyl sulfoxide-d₆) δ 12.51 (s, 1H), 8.14 (s, 1H), 7.85 (d, J=8.2 Hz, 2H), 7.73 (d, J=8.2 Hz, 1H), 7.59 (d, J=8.0 Hz, 1H), 7.41 (d, J=8.2 Hz, 2H), 7.05 (d, J=8.0 Hz, 1H), 6.84 (d, J=8.2 Hz, 1H), 6.70 (s, 1H), 6.02 (d, J=2.7 Hz, 1H), 3.76-3.64 (m, 1H), 3.24 (d, J=7.0 Hz, 1H), 2.96 (tt, J=11.8, 5.3 Hz, 1H), 2.73 (d, J=13.2 Hz, 1H), 2.35 (s, 3H), 2.02-1.92 (m, 1H), 1.79 (t, J=11.9 Hz, 2H), 1.52 (s, 4H), 1.45 (s, 3H), 1.39 (s, 1H), 1.34 (d, J=12.1 Hz, 2H), 1.19 (d, J=12.7 Hz, 1H), 0.76 (t, J=3.5 Hz, 4H), 0.57 (dd, J=8.1, 4.4 Hz, 2H), 0.43 (d, J=9.2 Hz, 2H). ESI-MS m/z calc. 791.3073, found 792.17 (M+1)⁺; Retention time: 0.65 min (LC Method L).

Step 5: (14S)-8-[3-(2-{dispiro[2.0.2.1]heptan-7-yl}-1,1,2,2-tetradeuterio-ethoxy)-1H-pyrazol-1-yl]-12,12-dimethyl(20-deuterio)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 301)

A solution of (14S)-8-[3-(2-{dispiro[2.0.2.1]heptan-7-yl}-1,1,2,2-tetradeuterio-ethoxy)-1H-pyrazol-1-yl]-12,12-dimethyl-2,2,4-trioxo-2λ⁶-thia-3,9,11,18,23-pentaazatetracyclo[17.3.1.1¹¹,¹⁴.0⁵,¹⁰]tetracosa-1(23),5,7,9,19,21-hexaen-20-yl 4-methylbenzene-1-sulfonate (145 mg, 0.1831 mmol) in dry N,N-dimethylformamide (2 mL) was purged with nitrogen for 5 min using a balloon. Then, dichloronickel; triphenyl-phosphane (42 mg, 0.06420 mmol) and tricyclohexylphosphane (46 mg, 0.1640 mmol) were added. The resulting green solution was stirred for 5 min under nitrogen atmosphere and tetradeuterioboranuide (sodium salt) (108 mg, 2.580 mmol) was added in one portion. The resulting dark reddish brown mixture was stirred at room temperature for 1 h. Additional dichloronickel; triphenylphosphane (42 mg, 0.06420 mmol), tricyclohexylphosphane (46 mg, 0.1640 mmol) and tetradeuterioboranuide (sodium salt) (108 mg, 2.580 mmol) were added and the mixture was stirred at room temperature under nitrogen overnight. The reaction mixture was diluted with water, extracted with ethyl acetate, dried over magnesium sulfate, filtered and evaporated. The resulting residue was dissolved in dimethyl sulfoxide and filtered through a Whatman filter disc (puradisc 25 TF) and the filtrate was purified by reverse phase HPLC-MS using a dual gradient run from 50%-99% mobile phase B over 15.0 min (mobile phase A=water (5 mM hydrochloric acid), mobile phase B=acetonitrile) to afford (14S)-8-[3-(2-{dispiro[2.0.2.1]heptan-7-yl}-1,1,2,2-tetradeuterio-ethoxy)-1H-pyrazol-1-yl]-12,12-dimethyl(20-deuterio)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 301) (26.9 mg, 24%) as a white solid. ¹H NMR (400 MHz, dimethyl sulfoxide-d₆) δ 12.60 (s, 1H), 8.30 (d, J=2.8 Hz, 1H), 7.91 (d, J=8.2 Hz, 1H), 7.70-7.66 (m, 1H), 7.15 (d, J=7.2 Hz, 1H), 7.08 (d, J=8.9 Hz, 1H), 7.01 (d, J=8.2 Hz, 1H), 6.18 (d, J=2.7 Hz, 1H), 4.02 (d, J=12.1 Hz, 1H), 3.26 (d, J=6.9 Hz, 1H), 3.05 (d, J=13.2 Hz, 1H), 2.83-2.76 (m, 1H), 2.20 (d, J=19.9 Hz, 1H), 1.99-1.93 (m, 1H), 1.87 (s, 1H), 1.70 (s, 6H), 1.61 (s, 3H), 1.55 (s, 1H), 1.46-1.37 (m, 1H), 0.97-0.90 (m, 4H), 0.76-0.72 (m, 2H), 0.63-0.57 (m, 2H). ESI-MS m/z calc. 622.3098, found 623.26 (M+1)⁺; Retention time: 1.3 min (LC Method J).

Example 106: Preparation of 11-[3-(2,2-dimethyl-propoxy)-1H-pyrazol-1-yl]-7,7-dimethyl-17λ⁶-thia-2,8,10,16,22-pentaazatetracyclo[16.3.1.1⁵,⁸.0⁹,¹⁴]tricosa-1(21),9(14),10,12,18(22),19-hexaene-15,17,17-trione (Compound 1)

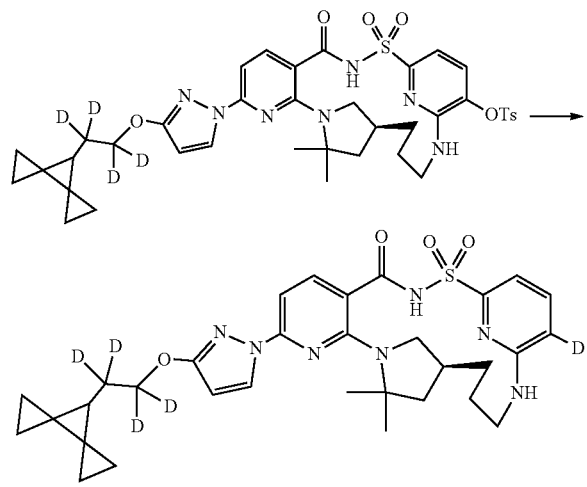

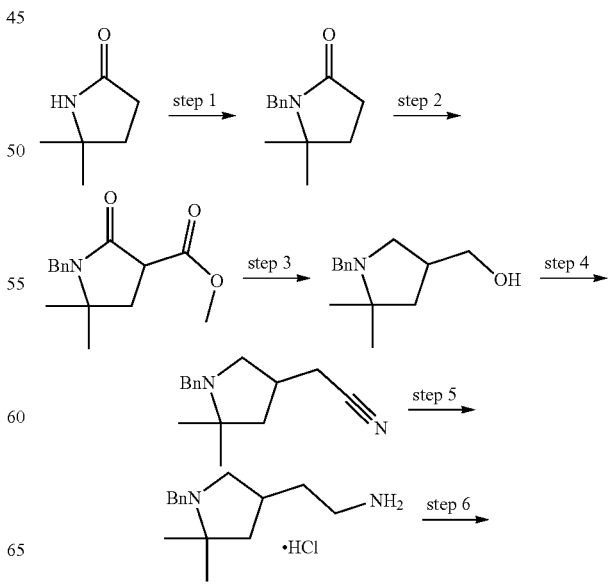

807
-continued

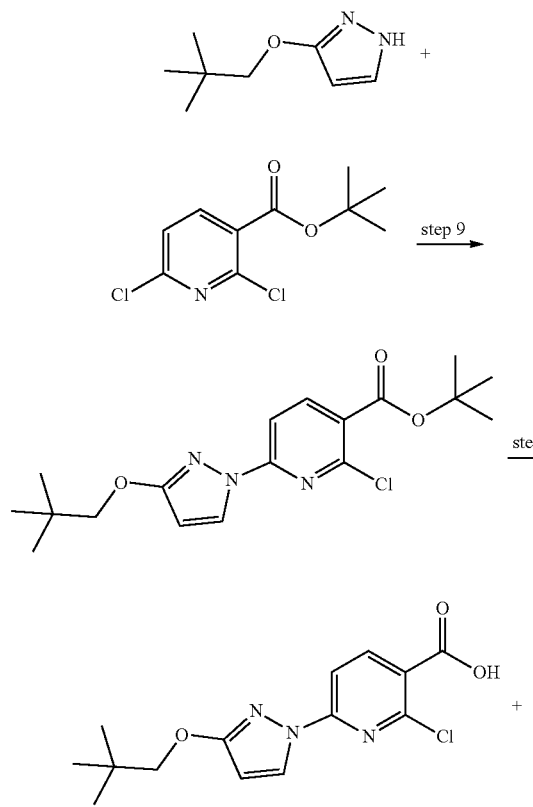

808
-continued

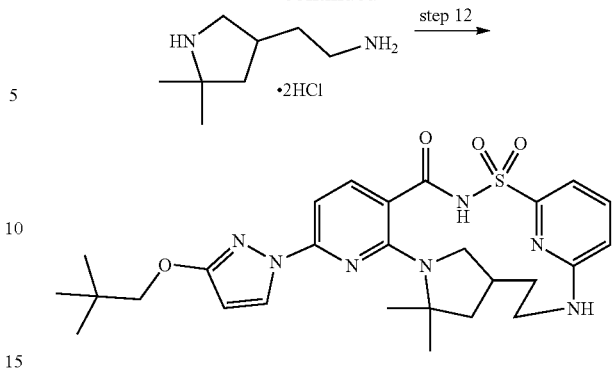

Step 1: 1-Benzyl-5,5-dimethylpyrrolidin-2-one

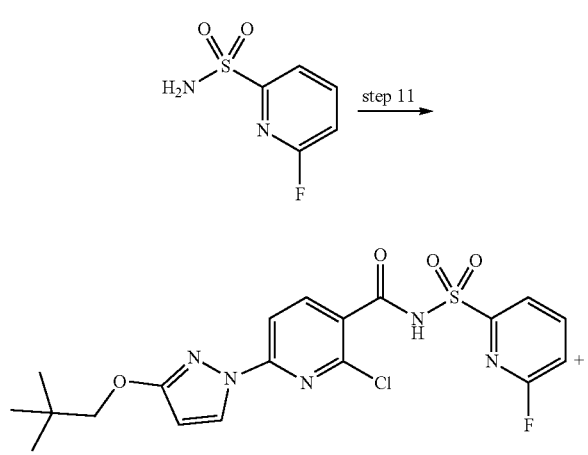

5,5-Dimethylpyrrolidin-2-one (19.6 g, 0.174 mol) was dissolved in N,N-dimethylformamide (100 ml) and cooled to 0° C. followed by the slow addition of NaH (10.4 g, 0.261 mol). The reaction mixture was stirred for 10 min after which time benzyl chloride (22 mL, 0.19 mol) was added. The reaction mixture was allowed to warm to 21° C. over a period of 16 h. The reaction was quenched by the addition of saturated aqueous NH₄Cl, followed by the addition of ethyl acetate. The layers were separated and the aqueous layer was extracted with ethyl acetate (3×20 mL). The combined organic layers were washed with brine, dried over sodium sulfate, filtered and concentrated. The crude product was purified by fast filtration over pad of silica (20% ethyl acetate in heptanes) giving pure 1-benzyl-5,5-dimethylpyrrolidin-2-one (30 g, 85%) as a colorless oil. $^1$H NMR (300 MHz, CDCl₃): δ 7.3 (m, 5H); 4.4 (s, 2H); 2.42 (t, 2H); 1.9 (t, 2H); 1.1 (s, 6H).

Step 2: 1-Benzyl-5,5-dimethyl-2-oxopyrrolidine-3-carboxylate

Diisopropyl amine (27.6 ml, 197 mmol) was dissolved in tetrahydrofuran (200 mL) under atmosphere of nitrogen and cooled to −78° C. n-BuLi (79 mL, 197 mmol, 2.5 M solution in hexanes) was added dropwise and stirring was continued for additional 90 min while allowing to warm to −20° C. The reaction mixture was cooled to −78° C. again and 1-benzyl-5,5-dimethylpyrrolidin-2-one (20 g, 98.4 mmol) was added dissolved in tetrahydrofuran (20 mL) while keeping temperature below −78° C. The stirring was continued for additional 1 h at which point the temperature was corrected to −80° C. and dimethyl carbonate (17.4 mL, 206.6 mmol) was added. The reaction mixture was allowed to warm to −20° C. Water (20 mL) was added slowly followed by the addition of 4 N aqueous hydrochloric acid (20 mL). The layers were separated and the water layer was extracted with ethyl acetate (2×20 mL). The combined organic layers were washed with brine, dried over sodium sulfate, filtered and concentrated. Pure methyl 1-benzyl-5,5-dimethyl-2-oxopyrrolidine-3-carboxylate (7.8 g, 30%) was obtained as a yellow oil after silica gel chromatographic purification (40% ethyl acetate in heptanes). $^1$H NMR (300 MHz, CDCl$_3$): δ 7.3 (m, 5H); 4.4 (dd, 2H); 3.8 (s, 3H); 3.6 (t, 1H); 2.2 (m, 2H); 1.2 (s, 3H); 1.1 (s, 3H).

Step 3: 2-(1-Benzyl-5,5-dimethylpyrrolidin-3-yl)acetonitrile

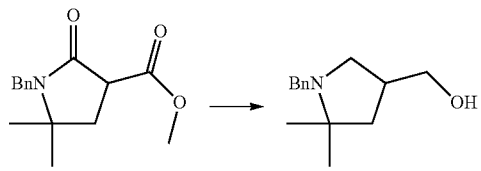 [SMILES: COC(=O)C1CC(C)(C)N(Cc2ccccc2)C1=O ; CC1(C)CC(CO)CN1Cc1ccccc1]

Lithium aluminum hydride (4.2 g, 110.4 mmol) was suspended in tetrahydrofuran (100 mL) and cooled to 0° C. followed by the dropwise addition of methyl 1-benzyl-5,5-dimethyl-2-oxopyrrolidine-3-carboxylate (7.8 g, 29.8 mmol) dissolved in tetrahydrofuran (20 mL). The reaction mixture was allowed to warm to 20° C. over a period of 16 h, quenched with water and extracted with ethyl acetate (3×30 mL). The combined organic layers were dried over sodium sulfate and concentrated. Crude (1-benzyl-5,5-dimethylpyrrolidin-3-yl)methanol (6.6 g, quant.) was used without further purification in the next step. $^1$H NMR (300 MHz, CDCl$_3$): δ 7.3 (m, 5H); 3.8 (d, 1H); 3.5 (m, 2H); 3.2 (d, 1H); 2.8 (bs, 1H); 2.6 (m, 2H); 2.2 (m, 1H); 1.9 (m, 1H); 1.6 (m, 1H); 1.3 (s, 3H); 1.03 (s, 3H).

Step 4: 2-(1-Benzyl-5,5-dimethylpyrrolidin-3-yl)acetonitrile

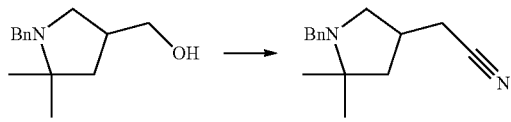 [SMILES: CC1(C)CC(CO)CN1Cc1ccccc1 ; CC1(C)CC(CC#N)CN1Cc1ccccc1]

(1-Benzyl-5,5-dimethylpyrrolidin-3-yl)methanol (5 g, 22.8 mmol) was dissolved in tetrahydrofuran (60 mL) and cooled to −23° C., followed by the addition of Et$_3$N (4.74 mL, 34.2 mmol) and MsCl (2.1 mL, 27.4 mmol). The reaction mixture was stirred at this temperature for 15 min then the cooling bath was removed and the stirring continued for additional 30 min. Water was added, followed by ethyl acetate. The layers were separated and the water layer was washed with ethyl acetate (2×30 mL). The combined organic layers were dried over sodium sulfate and concentrated. The crude material was further dissolved in dimethyl sulfoxide (40 mL) and sodium cyanide (1.7 g, 34.2 mmol) was added. The residue was stirred at 60° C. for 5 h, after which another amount of sodium cyanide (770 mg) was added and the stirring continued for another 5 h. The reaction mixture was cooled down, water was added followed by ethyl acetate. The layers were separated and the water layer was extracted with ethyl acetate (2×20 mL). The combined organic layers were dried over sodium sulfate and concentrated. Pure 2-(1-benzyl-5,5-dimethylpyrrolidin-3-yl)acetonitrile (3 g, 58%) was obtained as a yellow oil after purification by silica gel chromatography (30% ethyl acetate in heptanes). $^1$H NMR (300 MHz, CDCl$_3$): δ 7.3 (m, 5H); 3.7 (d, 1H); 3.4 (d, 1H); 2.78 (t, 1H); 2.4 (m, 2H); 2.0 (m, 1H); 1.6 (m, 2H); 1.2 (s, 3H); 1.05 (s, 3H).

Step 5: 2-(1-Benzyl-5,5-dimethylpyrrolidin-3-yl)ethan-1-amine hydrochloride

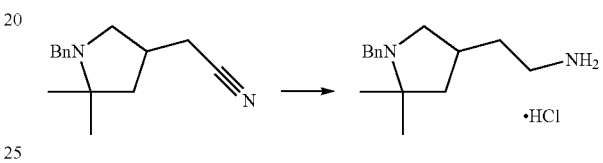

Lithium aluminum hydride (1.25 g, 32.8 mmol) was suspended in tetrahydrofuran (30 mL) and cooled to 0° C. followed by slow addition of 2-(1-benzyl-5,5-dimethylpyrrolidin-3-yl)acetonitrile (3 g, 13.1 mmol) dissolved in tetrahydrofuran (5 mL). The reaction mixture was allowed to warm to 20° C. over a period of 15 h. The reaction was quenched with water (20 mL) and 15% aqueous sodium hydroxide (10 mL). The resulting precipitate was filtered over pad of Celite. The filter cake was washed with ethyl acetate and the layers were separated. The organic layer containing the crude amine was concentrated and the residue was treated with 4 N hydrochloric acid in dioxane then evaporated, giving pure 2-(1-benzyl-5,5-dimethylpyrrolidin-3-yl)ethan-1-amine hydrochloride (3.8 g, 98%) as a yellowish solid. 1H NMR (300 MHz, D$_2$O): d 7.4 (m, 5H); 4.4 (m, 1H); 3.9 (m, 1H); 3.6 (m, 1H); 3.4 and 3.0 (m, 1H); 2.8 (m, 2H); 2.6 (m, 1H); 2.2 (m, 1H); 1.6 (m, 1H); 1.42 (s, 3H); 1.3 (s, 3H).

Step 6: 2-(5,5-Dimethylpyrrolidin-3-yl)ethan-1-amine dihydrochloride

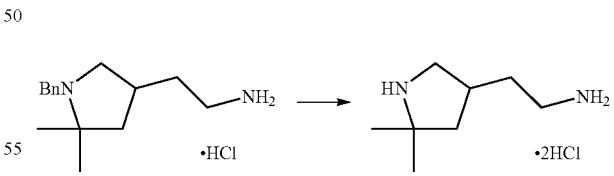

To a solution of 2-(1-benzyl-5,5-dimethylpyrrolidin-3-yl)ethan-1-amine hydrochloride (1 g, 3.720 mmol) in methanol (10 mL) was added palladium hydroxide (653.0 mg, 0.9300 mmol) and hydrochloric acid (155.0 μL of 6 M, 0.9300 mmol). The reaction flask was evacuated and flushed with H2 using balloon with a 3-way adaptor and repeated 3 times. Stirred under H2 atm at room temperature for 48 h. The reaction mixture was filtered through a bed of Celite and washed the bed with methanol. Filtrate was evaporated to afford 2-(5,5-dimethylpyrrolidin-3-yl)ethanamine dihydrochloride (557 mg, 70%). ESI-MS m/z calc. 142.147, found 143.2 (M+1)+; Retention time: 0.09 min (LC Method A).

Step 7: tert-Butyl 3-(2,2-dimethylpropoxy)pyrazole-1-carboxylate

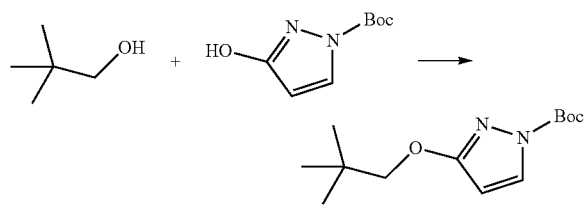

To tert-butyl 3-hydroxypyrazole-1-carboxylate (40 g, 217.2 mmol) in tetrahydrofuran (480.0 mL) under nitrogen was added 2,2-dimethylpropan-1-ol (21.06 g, 238.9 mmol) and triphenylphosphine (62.66 g, 55.35 mL, 238.9 mmol). To the mixture was added DIAD (48.31 g, 47.04 mL, 238.9 mmol) dropwise allowing the mixture to gradually exotherm to 45° C. After the addition, the mixture was heated at 50° C. for 5 h. The mixture was then allowed to cool to ambient temperature. The reaction mixture was diluted with 200 mL of ethyl acetate and the organic phase was washed with 500 mL of 1N sodium hydroxide, 500 mL of brine, dried over magnesium sulfate, filtered over Celite and concentrated in vacuo to a volume of approximately 300 mL. Crystallization of triphenylphosphine oxide began and the light red slurry was allowed to stand overnight. The slurry was filtered using a medium frit and washed 3× with 100 mL of 50% ethyl acetate/hexanes. The filtrate was concentrated in vacuo. The crude pink oil was diluted with dichloromethane and chromatographed on an 750 g silica gel column eluting with 0-25% ethyl acetate/hexanes gradient. Impure fractions collected were rechromatographed on a 330 g silica gel column eluting with 0-25% ethyl acetate/hexanes. Pure fractions from both columns were combined and concentrated giving tert-butyl 3-(2,2-dimethylpropoxy)pyrazole-1-carboxylate (45.8 g, 83%). $^1$H NMR (400 MHz, Chloroform-d) δ 7.83 (d, J=3.2 Hz, 1H), 5.88 (d, J=3.2 Hz, 1H), 3.95 (s, 2H), 1.62 (d, J=2.2 Hz, 9H), 1.01 (d, J=2.7 Hz, 9H). ESI-MS m/z calc. 254.16304, found 199.1 (M+1-13u)+; Retention time: 1.89 min (LC Method B).

Step 8: 3-(2,2-Dimethylpropoxy)-1H-pyrazole

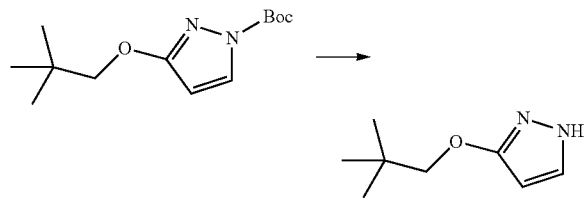

To tert-butyl 3-(2,2-dimethylpropoxy)pyrazole-1-carboxylate (111 g, 436.4 mmol) in dichloromethane (450 mL) and methanol (450 mL) was added hydrochloric acid (330 mL of 4 M in dioxane, 1.320 mol) (gradual exotherm to 35° C.) and the mixture stirred at 45° C. for 1 h. The solvent removed in vacuo and the residue was diluted with MTBE (900 mL) and washed with sodium hydroxide (650 mL of 2 M, 1.300 mol). The aqueous phase was extracted with 500 mL of MTBE and the combined organic phases were washed with 800 mL of brine, dried over magnesium sulfate, filtered and concentrated in vacuo affording as an off-white solid, 3-(2,2-dimethylpropoxy)-1H-pyrazole (65 g, 97%). $^1$H NMR (400 MHz, dimethyl sulfoxide-d$_6$) δ 11.81 (s, 1H), 7.48 (d, J=2.5 Hz, 1H), 5.65 (t, J=1.9 Hz, 1H), 3.70 (s, 2H), 0.96 (s, 9H). ESI-MS m/z calc. 154.11061, found 155.1 (M+1)+; Retention time: 1.48 min (LC Method D).

Step 9: tert-Butyl 2-chloro-6-[3-(2,2-dimethylpropoxy)pyrazol-1-yl]pyridine-3-carboxylate

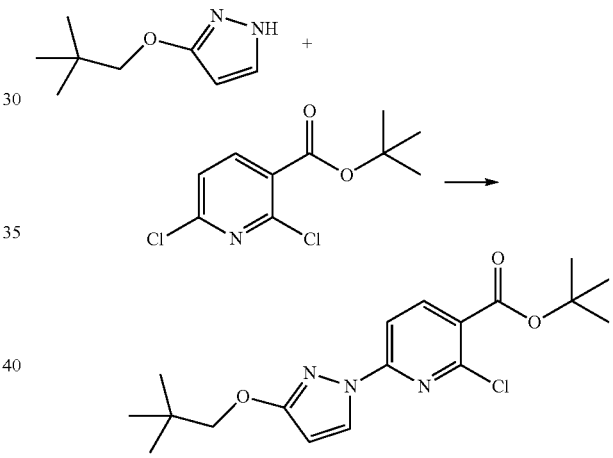

To tert-butyl 2,6-dichloropyridine-3-carboxylate (12.75 g, 51.39 mmol) and 3-(2,2-dimethylpropoxy)-1H-pyrazole (7.925 g, 51.39 mmol) in N,N-dimethylformamide (95.10 mL) was added under nitrogen potassium carbonate (9.232 g, 66.80 mmol) and 1,4-diazabicyclo[2.2.2]octane (864.6 mg, 7.708 mmol) and the reaction was stirred at room temperature for 18 h. The cream fine suspension was diluted with water (95.10 mL) which resulted in precipitation of a gum which started to solidify. The mixture was allowed to sit and the clear solution decanted from the gummy solid. The solid was diluted with 200 mL of water and 25 mL of isopropyl alcohol. The mixture was heated until the solution became homogenous. The mixture was allowed to cool and then placed in an ice bath affording a cream colored semi-solid. The solid was collected using a medium frit and washed 3× with 10 mL of water. The solid was air dried for 18 h providing tert-butyl 2-chloro-6-[3-(2,2-dimethylpropoxy)pyrazol-1-yl]pyridine-3-carboxylate (18 g, 95%). $^1$H NMR (400 MHz, dimethyl sulfoxide-d$_6$) δ 8.41 (d, J=2.9

Hz, 1H), 8.30 (d, J=8.4 Hz, 1H), 7.73 (d, J=8.4 Hz, 1H), 6.22 (d, J=2.9 Hz, 1H), 3.92 (s, 2H), 1.57 (s, 9H), 1.01 (s, 9H). ESI-MS m/z calc. 365.1506, found 366.2 (M+1)⁺; Retention time: 3.53 min (LC Method D).

Step 10: 2-Chloro-6-[3-(2,2-dimethylpropoxy)pyrazol-1-yl]pyridine-3-carboxylic Acid

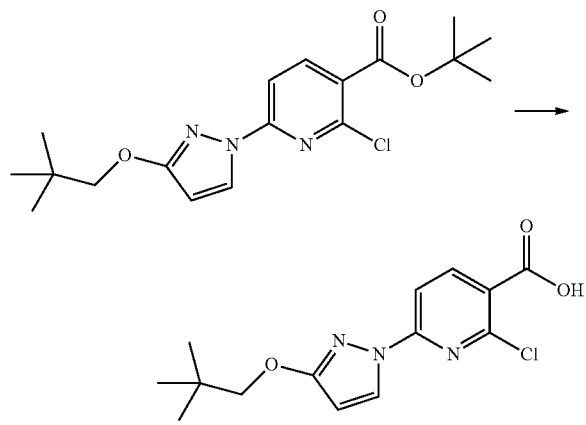

To tert-butyl 2-chloro-6-[3-(2,2-dimethylpropoxy)pyrazol-1-yl]pyridine-3-carboxylate (18 g, 49.20 mmol) in isopropyl alcohol (90.00 mL) was added aqueous hydrochloric acid (41.00 mL of 6 M, 246.0 mmol) and the mixture was heated to reflux for 90 min (oil bath temperature=100° C.). The mixture was allowed to cool to ambient temperature and then was diluted with water (90.00 mL). The slurry was slightly chilled with an ice-water bath and the precipitate collected using a medium frit. The precipitate was washed 3× with 10 mL of water and dried in vacuo at 45° C. for 2 days giving 2-chloro-6-[3-(2,2-dimethylpropoxy)pyrazol-1-yl]pyridine-3-carboxylic acid (12.72 g, 83%). ¹H NMR (400 MHz, dimethyl sulfoxide-d₆) δ 13.62 (s, 1H), 8.42 (d, J=2.9 Hz, 1H), 8.38 (d, J=8.4 Hz, 1H), 7.74 (d, J=8.4 Hz, 1H), 6.22 (d, J=2.9 Hz, 1H), 3.93 (s, 2H), 1.01 (s, 9H). ESI-MS m/z calc. 309.088, found 310.2 (M+1)⁺; Retention time: 2.61 min (LC Method D).

Step 11: 2-Chloro-6-[3-(2,2-dimethylpropoxy)pyrazol-1-yl]-N-[(6-fluoro-2-pyridyl)sulfonyl]pyridine-3-carboxamide

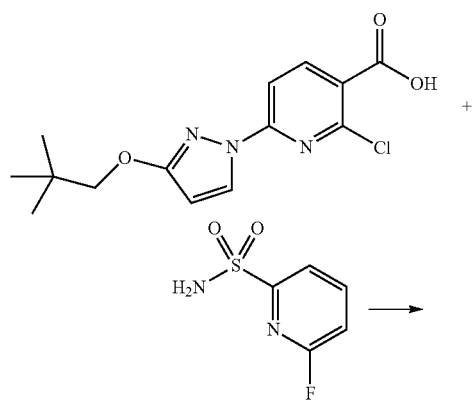

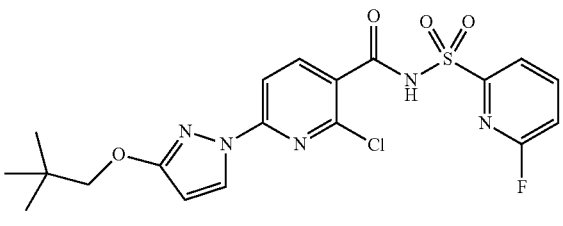

A 40 mL vial was charged under nitrogen with 2-chloro-6-[3-(2,2-dimethylpropoxy)pyrazol-1-yl]pyridine-3-carboxylic acid (1.0 g, 3.228 mmol) and carbonyl diimidazole (785.1 mg, 4.842 mmol). Added N,N-dimethylformamide (9.615 mL) and the mixture was stirred at 45° C. under nitrogen for 1 h. In a separate 40 mL vial, a solution of 6-fluoro-2-pyridinesulfonamide (682.5 mg, 3.874 mmol) was dissolved under nitrogen in anhydrous N,N-dimethylformamide (9.615 mL). Sodium hydride (154.9 mg, 3.874 mmol) (60% oil suspension) was added portionwise and the mixture was stirred under nitrogen until gas evolution stopped. The vial was capped and it was stirred at 45° C. for 45 min. The two mixtures were combined and stirred at room temperature for 2 h. Water and ice was added. Added concentrated hydrochloric acid dropwise until a white precipitate persisted then washed with ethyl acetate (2×), combined organic layers, dried (sodium sulfate), filtered and concentrated to a yellow residue. Dissolved the residue in ethyl acetate and washed with 1:1 saturated aqueous sodium bicarbonate/1N sodium hydroxide (3×), dried over sodium sulfate, filtered and concentrated. The material was further purified by silica gel chromatography using a gradient from 100% hexanes to 100% ethyl acetate to isolate as a pale yellow foam, 2-chloro-6-[3-(2,2-dimethylpropoxy)pyrazol-1-yl]-N-[(6-fluoro-2-pyridyl)sulfonyl]pyridine-3-carboxamide (1.01 g, 67%). ¹H NMR (400 MHz, dimethyl sulfoxide-d₆) δ 8.36 (d, J=2.8 Hz, 1H), 8.21-8.10 (m, 2H), 7.89 (d, J=5.7 Hz, 1H), 7.65 (d, J=8.3 Hz, 1H), 7.30 (d, J=7.1 Hz, 1H), 6.15 (d, J=2.8 Hz, 1H), 3.92 (s, 2H), 1.00 (s, 9H) ESI-MS m/z calc. 467.08304, found 468.2 (M+1)⁺; Retention time: 1.92 min (LC Method E).

Step 12: 11-[3-(2,2-Dimethylpropoxy)-1H-pyrazol-1-yl]-7,7-dimethyl-17λ⁶-thia-2,8,10,16,22-pentaazatetracyclo[16.3.1.1⁵,⁸.0⁹,¹⁴]tricosa-1(21),9(14),10,12,18(22),19-hexaene-15,17,17-trione (Compound 1)

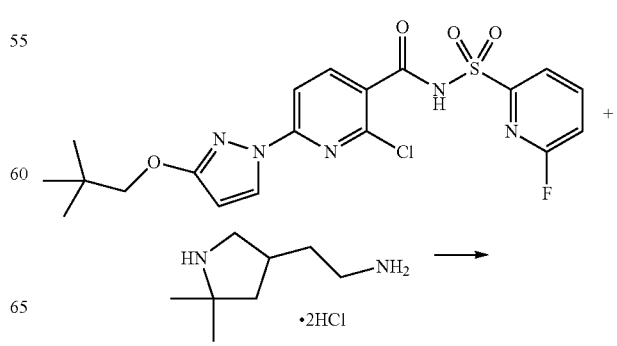

815
-continued

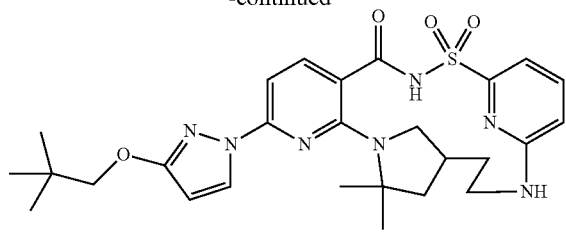

In a 5 mL vial was combined 2-chloro-6-[3-(2,2-dimethylpropoxy)pyrazol-1-yl]-N-[(6-fluoro-2-pyridyl)sulfonyl]pyridine-3-carboxamide (330 mg, 0.6065 mmol) in dimethyl sulfoxide (2.980 mL), potassium carbonate (419.2 mg, 3.033 mmol) and 2-(5,5-dimethylpyrrolidin-3-yl)ethanamine dihydrochloride (108.4 mg, 0.504 mmol). The vial was capped and heated to 120° C. on a hot plate for 20 h. Added additional 2-(5,5-dimethylpyrrolidin-3-yl)ethanamine dihydrochloride (108.4 mg, 0.504 mmol) and heated to 125° C. on a hot plate for 24 h. The reaction mixture was filtered and then purified directly by reverse-phase preparative chromatography utilizing a $C_{18}$ column (10-99 acetonitrile-water+5 mM hydrochloric acid) to afford an off-white solid to which was added excess potassium carbonate (419.2 mg, 3.033 mmol) and dimethyl sulfoxide (2.980 mL) and the mixture was heated for 18 h at 155° C. The reaction mixture was filtered and then purified directly by reverse-phase preparative chromatography utilizing a $C_{18}$ column (10-99 acetonitrile-water+5 mM hydrochloric acid) to afford as the more polar regioisomer, 11-[3-(2,2-dimethylpropoxy)-1H-pyrazol-1-yl]-7,7-dimethyl-17λ$^6$-thia-2,8,10,16,22-pentaazatetracyclo[16.3115,8.09,14]tricosa-1(21),9(14),10,12,18(22),19-hexaene-15,17,17-trione (Compound 1) (34.5 mg, 10%) as a pale yellow solid. $^1$H NMR (400 MHz, dimethyl sulfoxide-d$_6$) δ 12.45 (s, 1H), 8.27-8.16 (m, 1H), 7.74 (d, J=30.7 Hz, 2H), 7.17 (d, J=6.1 Hz, 1H), 6.96-6.88 (m, 1H), 6.88-6.74 (m, 1H), 6.17-6.10 (m, 1H), 3.89 (s, 2H), 3.61 (dd, J=15.1, 8.4 Hz, 1H), 3.35 (s, 1H), 2.48-2.29 (m, 1H), 2.25 (s, 1H), 1.91 (dd, J=10.8, 5.3 Hz, 2H), 1.56 (s, 6H), 1.50 (s, 1H), 1.43-1.28 (m, 1H), 1.19 (dd, J=30.9, 7.8 Hz, 1H), 1.00 (s, 9H). ESI-MS m/z calc. 553.24713, found 554.2 (M+1)$^+$; Retention time: 2.14 min (LC Method E).

Example 107: Preparation of 11-[3-(2,2-dimethylpropoxy)-1H-pyrazol-1-yl]-7,7-dimethyl-17λ$^6$-thia-2,8,10,16,22-pentaazatetracyclo[16.3.1.15,8.09,14]tricosa-1(21),9(14),10,12,18(22),19-hexaene-15,17,17-trione (Enantiomer 1) (Compound 2) and 11-[3-(2,2-dimethylpropoxy)-1H-pyrazol-1-yl]-7,7-dimethyl-17λ$^6$-thia-2,8,10,16,22-pentaazatetracyclo[16.3.1.15,8.09,14]tricosa-1(21),9(14),10,12,18(22),19-hexaene-15,17,17-trione (Enantiomer 2) (Compound 3)

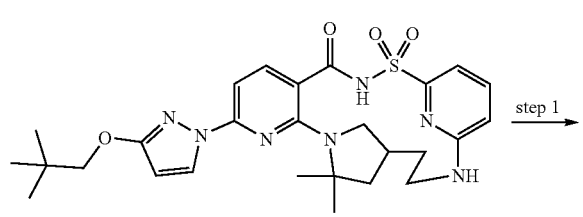

816
-continued

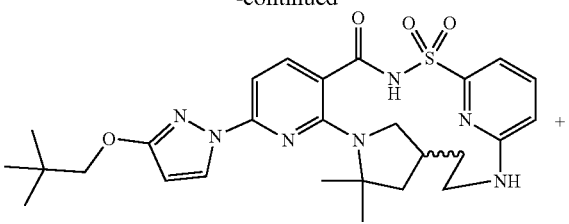
enantiomer 1

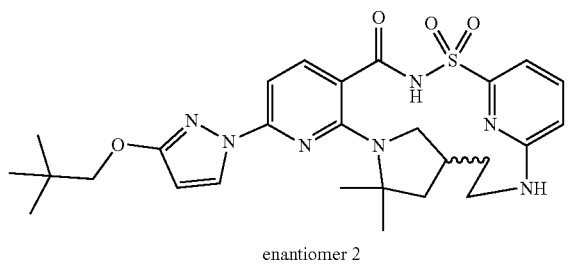
enantiomer 2

Step 1: 11-[3-(2,2-Dimethylpropoxy)-1H-pyrazol-1-yl]-7,7-dimethyl-17λ$^6$-thia-2,8,10,16,22-pentaazatetracyclo[16.3.1.15,8.09,14]tricosa-1(21),9(14),10,12,18(22),19-hexaene-15,17,17-trione (enantiomer 1) (Compound 2) and 11-[3-(2,2-dimethylpropoxy)-1H-pyrazol-1-yl]-7,7-dimethyl-17λ$^6$-thia-2,8,10,16,22-pentaazatetracyclo[16.3.1.15,8.09,14]tricosa-1(21),9(14),10,12,18(22),19-hexaene-15,17,17-trione (Enantiomer 2) (Compound 3)

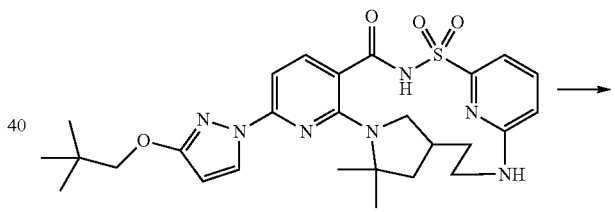

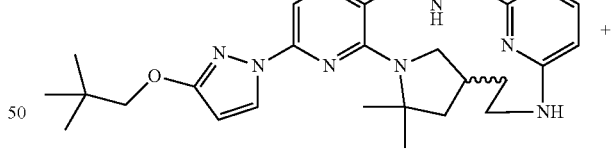
enantiomer 1

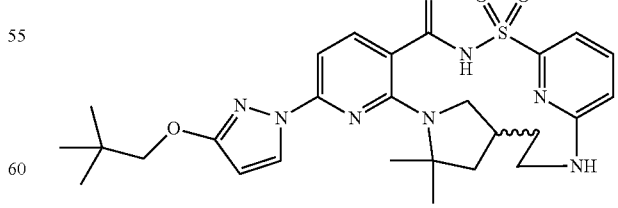
enantiomer 2

Racemic 11-[3-(2,2-dimethylpropoxy)-1H-pyrazol-1-yl]-7,7-dimethyl-17λ$^6$-thia-2,8,10,16,22-pentaazatetracyclo[16.3.1.15,8.09,14]tricosa-1(21),9(14),10,12,18(22),19- hexaene-15,17,17-trione (28.4 mg) was subjected to chiral SFC purification using a ChiralPak AS-H (250×10 mm column, 5 μm particle size) with 28% methanol/72% carbon dioxide mobile phase at 10 mL/min giving as the first enantiomer to elute, 11-[3-(2,2-dimethylpropoxy)-1H-pyrazol-1-yl]-7,7-dimethyl-17λ⁶-thia-2,8,10,16,22-pentaazatetracyclo[16.3.1.15,8.09,14]tricosa-1(21),9(14),10,12,18(22),19-hexaene-15,17,17-trione (enantiomer 1) (Compound 2) (4.4 mg, 32%), ESI-MS m/z calc. 553.24713, found 554.2 (M+1)⁺; Retention time: 2.14 min (LC Method E); and as the second enantiomer to elute, 11-[3-(2,2-dimethylpropoxy)-1H-pyrazol-1-yl]-7,7-dimethyl-17λ⁶-thia-2,8,10,16,22-pentaazatetracyclo[16.3.1.15,8.09,14]tricosa-1(21),9(14),10,12,18(22),19-hexaene-15,17,17-trione (enantiomer 2) (Compound 3) (5.6 mg, 41%), ESI-MS m/z calc. 553.24713, found 554.2 (M+1)⁺; Retention time: 2.15 min (LC Method E).

Example 108: Preparation of 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (Compound 4)

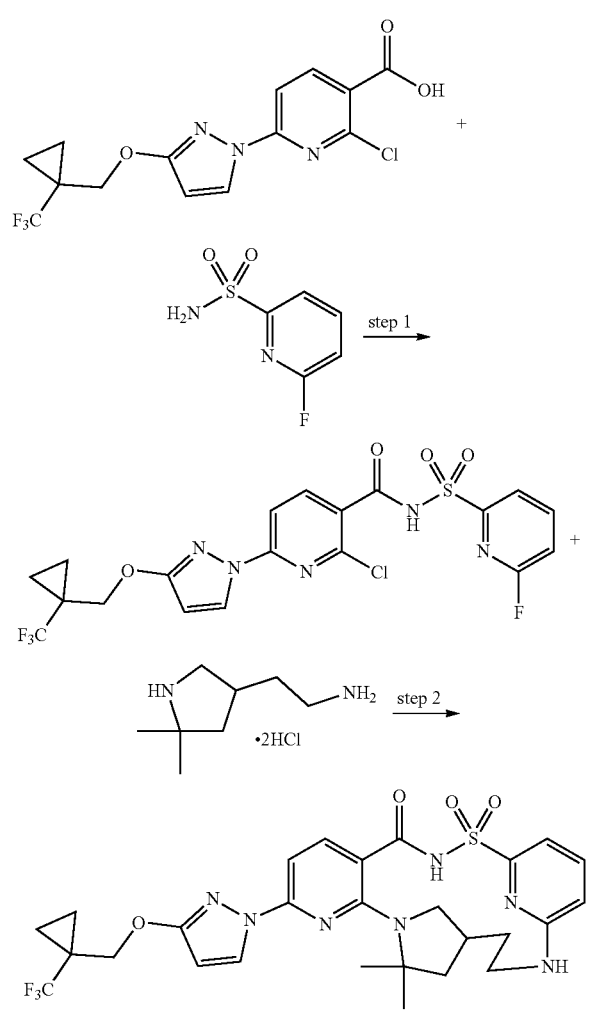

Step 1: 2-Chloro-N-[(6-fluoro-2-pyridyl)sulfonyl]-6-[3-[[1-(trifluoromethyl)cyclopropyl]methoxy]pyrazol-1-yl]pyridine-3-carboxamide

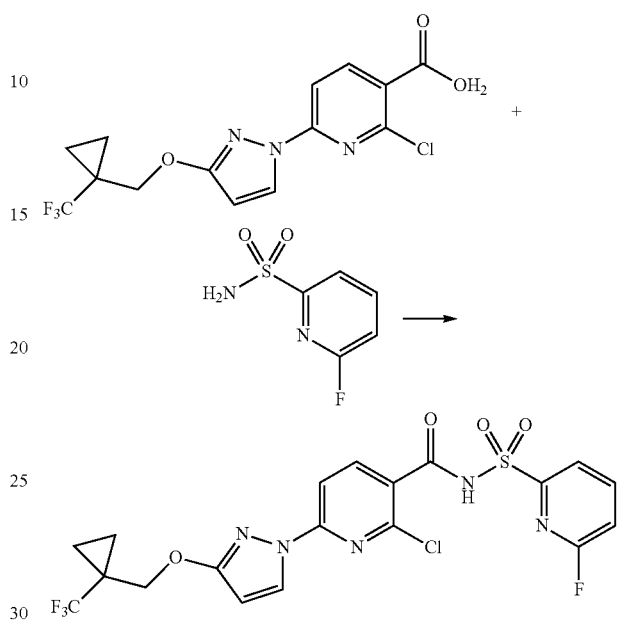

A solution of 2-chloro-6-[3-[[1-(trifluoromethyl)cyclopropyl]methoxy]pyrazol-1-yl]pyridine-3-carboxylic acid (3.5 g, 9.386 mmol) and carbonyl diimidazole (2.283 g, 14.08 mmol) in dimethylformamide (32.64 mL) was stirred at 60° C. for 60 min and a separate solution of 6-fluoro-2-pyridinesulfonamide (1.984 g, 11.26 mmol) and sodium hydride (450.4 mg, 11.26 mmol) in dimethylformamide (32.64 mL) was stirred at 45° C. for 45 min. The two solutions were combined and stirred at 60° C. for 1 h. Cooled to room temperature and poured into water. Added concentrated hydrochloric acid dropwise until a white precipitate persisted then washed with ethyl acetate (2×), combined organic layers, dried (sodium sulfate), filtered and concentrated to a white solid. Dissolved in ethyl acetate and washed with 1:1 saturated aqueous sodium bicarbonate/1N sodium hydroxide (3×), dried (sodium sulfate), filtered and concentrated to an off-white foam. Slurried in ether and removed the ether under reduced pressure. Dissolved the residue in minimal warm dichloromethane, sat for 5 min then cooled to 4° C. overnight. Mass of white solid was filtered and washed with dichloromethane. Filtrate was reduced to a yellow solid, dissolved in minimal warm dichloromethane, and slowly cooled to 4° C. overnight. A formed mass of white solid was filtered and washed with dichloromethane giving 2-chloro-N-[(6-fluoro-2-pyridyl)sulfonyl]-6-[3-[[1-(trifluoromethyl)cyclopropyl]methoxy]pyrazol-1-yl]pyridine-3-carboxamide (3.339 g, 62%). ESI-MS m/z calc. 519.86, found 520.2 (M+1)⁺; Retention time: 1.75 min (LC Method B).

819

Step 2: 7,7-Dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (Compound 4)

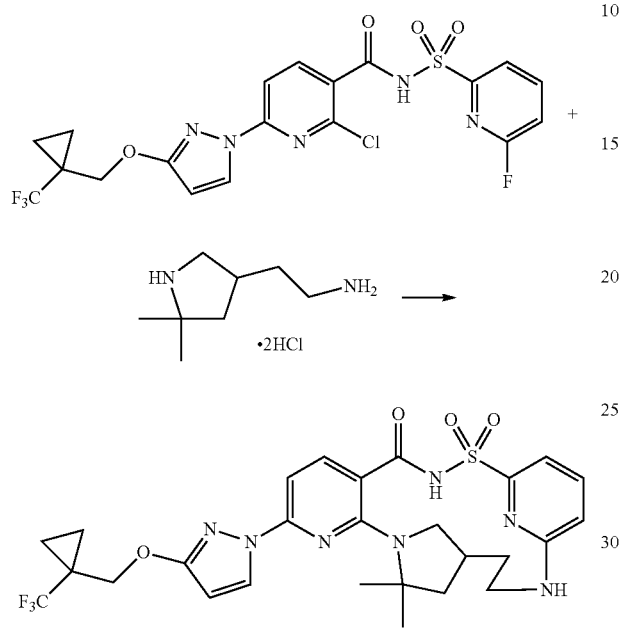

In a 5 mL vial was combined 2-chloro-N-[(6-fluoro-2-pyridyl)sulfonyl]-6-[3-[[1-(trifluoromethyl)cyclopropyl]methoxy]pyrazol-1-yl]pyridine-3-carboxamide (400 mg, 0.7310 mmol) in dimethyl sulfoxide (3.040 mL) followed by potassium carbonate (505.1 mg, 3.655 mmol) and 2-(5,5-dimethylpyrrolidin-3-yl)ethanamine dihydrochloride (137.2 mg, 0.64 mmol). The vial was capped and heated to 75° C. on a hot plate for 92 h then for 20 h at 125° C. The reaction mixture was filtered and then purified directly by reverse-phase preparative chromatography utilizing a $C_{18}$ column (10-99 acetonitrile-water+5 mM hydrochloric acid) to afford product isolated as a tan solid, 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (Compound 4) (35.2 mg, 9%). $^1$H NMR (400 MHz, dimethyl sulfoxide-$d_6$) δ 12.43 (s, 1H), 8.43-8.41 (m, 1H), 8.21 (d, J=2.8 Hz, 1H), 7.74 (d, J=33.4 Hz, 2H), 7.17 (d, J=7.0 Hz, 1H), 6.91 (d, J=8.2 Hz, 1H), 6.82 (s, 1H), 6.15 (d, J=2.7 Hz, 1H), 4.37 (q, J=11.9 Hz, 2H), 3.61 (d, J=9.1 Hz, 1H), 3.41 (d, J=3.9 Hz, 1H), 3.19 (d, J=26.6 Hz, 2H), 2.26 (d, J=5.9 Hz, 1H), 1.91 (d, J=3.5 Hz, 1H), 1.55 (s, 6H), 1.48 (d, J=11.0 Hz, 1H), 1.34 (d, J=12.7 Hz, 1H), 1.18 (d, J=11.8 Hz, 1H), 1.11-1.06 (m, 4H). ESI-MS m/z calc. 605.2032, found 606.2 (M+1)⁺; Retention time: 2.02 min (LC Method E).

820

Example 109: Preparation of 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (Enantiomer 1) (Compound 5) and 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (Enantiomer 2) (Compound 6)

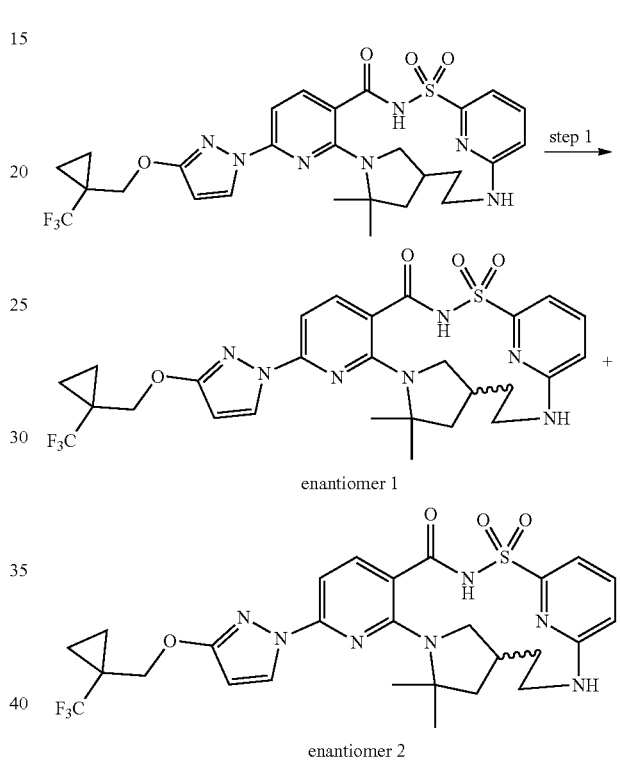

Step 1: 7,7-Dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (Enantiomer 1) (Compound 5) and 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (Enantiomer 2) (Compound 6)

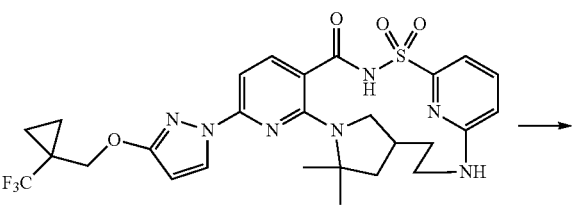

821

-continued

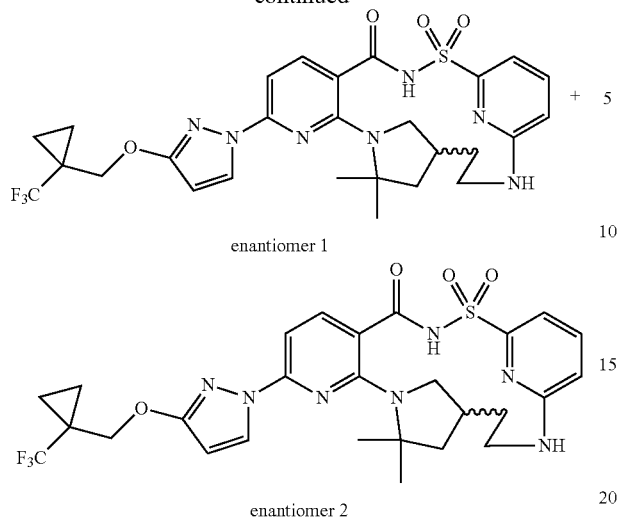

enantiomer 1 enantiomer 2

Racemic 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (31 mg, 0.05119 mmol) was subjected to chiral SFC purification using a ChiralPak AS-H (250×10 mm column, 5 μm particle size) with 20% methanol/80% carbon dioxide mobile phase at 10 mL/min giving as the first enantiomer to elute, 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (enantiomer 1) (Compound 5) (11.5 mg, 74%); ESI-MS m/z calc. 605.2032, found 606.2 (M+1)⁺; Retention time: 2.02 min (LC Method E), and as the second enantiomer to elute, 7,7-dimethyl-11-(3-{[1-(trifluoromethyl)cyclopropyl]methoxy}-1H-pyrazol-1-yl)-17λ⁶-thia-2,8,10,16,22-pentaazatetracyclo[16.3.1.1(5,8).0(9,14)]tricosa-1(21),9(14),10,12,18(22),19-hexaene-15,17,17-trione (enantiomer 2) (Compound 6) (11.4 mg, 72%); ESI-MS m/z calc. 605.2032, found 606.2 (M+1)⁺; Retention time: 2.02 min (LC Method E).

Example 110: Preparation of 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.3.1.0⁵,¹⁰.0¹¹,¹⁵]tetracosa-1(24),5(10),6,8,20,22-hexaene-2,2,4-trione (Enantiomer 1) (Compound 7) and 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.3.1.0⁵,¹⁰.0¹¹,¹⁵]tetracosa-1(24),5(10),6,8,20,22-hexaene-2,2,4-trione (Enantiomer 2) (Compound 8)

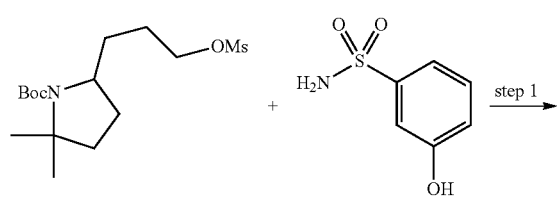

822

-continued

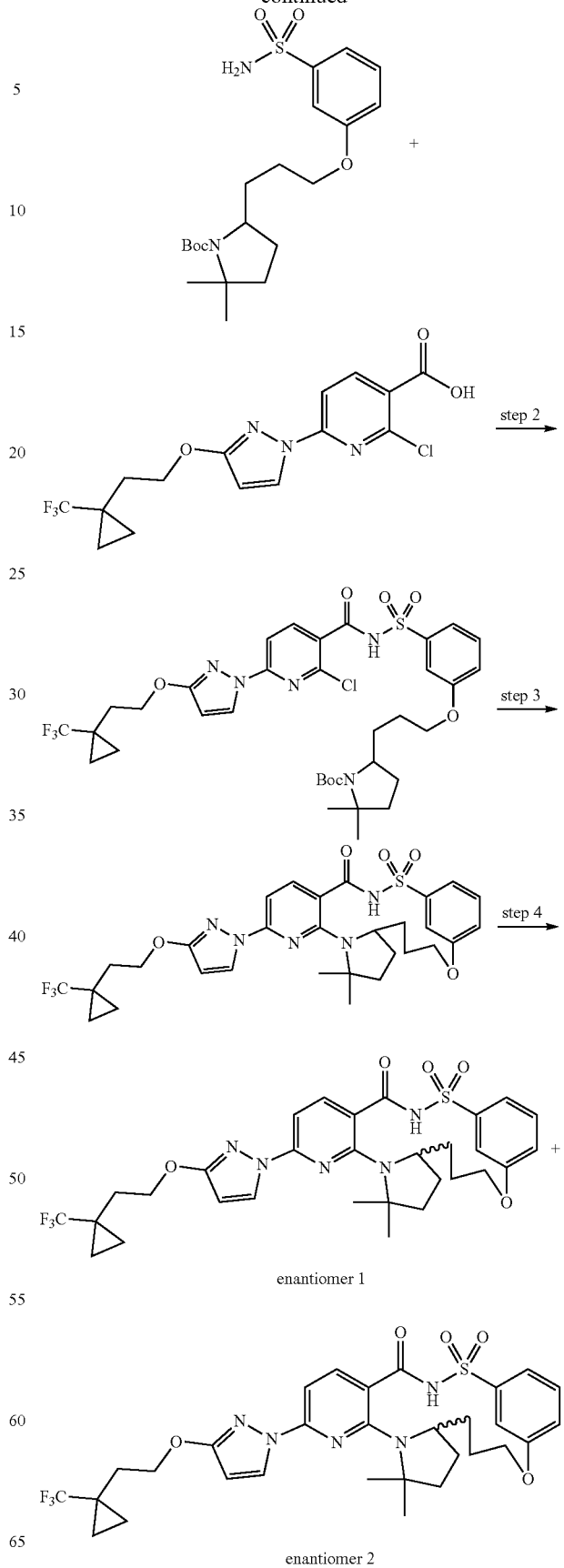

enantiomer 1 enantiomer 2

Step 1: tert-Butyl 2,2-dimethyl-5-[3-(3-sulfamoylphenoxy)propyl]pyrrolidine-1-carboxylate

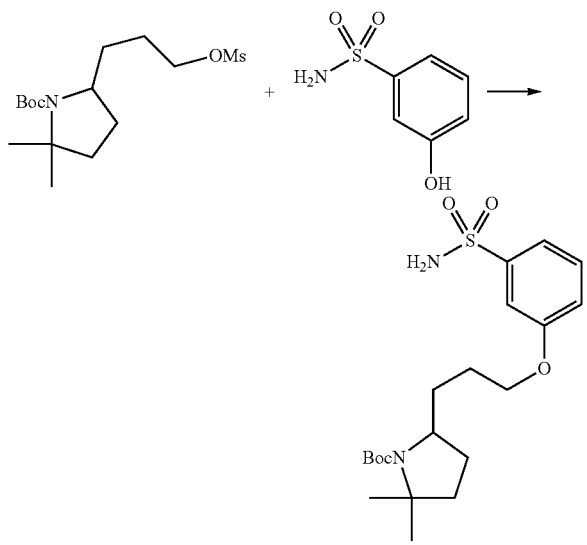

In a 50 mL round bottom flask was added 3-hydroxybenzenesulfonamide (510 mg, 2.945 mmol) and N,N-dimethylformamide (10.20 mL). To the mixture was added potassium carbonate (1.425 g, 10.31 mmol) and tert-butyl 2,2-dimethyl-5-(3-methylsulfonyloxypropyl)pyrrolidine-1-carboxylate (1.017 g, 3.033 mmol) at room temperature and stirred at room temperature for 3 h then heated to 50° C. overnight. Cooled to room temperature and poured into water (100 mL) and extracted with ethyl acetate (2×100 mL), combined organic layers, washed with water (2×100 mL), dried (sodium sulfate), filtered and concentrated. The brown residue was purified by silica gel chromatography using a gradient from 100% hexanes to 100% ethyl acetate to afford as a light orange oil, tert-butyl 2,2-dimethyl-5-[3-(3-sulfamoylphenoxy)propyl]pyrrolidine-1-carboxylate (770 mg, 63%). $^1$H NMR (400 MHz, dimethyl sulfoxide-$d_6$) δ 7.46 (t, J=8.0 Hz, 1H), 7.39-7.33 (m, 2H), 7.31 (s, 2H), 7.13 (d, J=7.8 Hz, 1H), 4.02 (t, J=6.0 Hz, 2H), 3.85-3.67 (m, 1H), 1.88 (dd, J=11.8, 6.6 Hz, 2H), 1.79-1.61 (m, 4H), 1.51 (dd, J=37.7, 5.8 Hz, 2H), 1.38 (s, 12H), 1.24 (s, 3H). ESI-MS m/z calc. 412.2032, found 413.2 (M+1)$^+$; Retention time: 1.81 min (LC Method E).

Step 2: tert-Butyl 5-[3-[3-[[2-chloro-6-[3-[2-[1-(trifluoromethyl)cyclopropyl]ethoxy]pyrazol-1-yl]pyridine-3-carbonyl]sulfamoyl]phenoxy]propyl]-2,2-dimethyl-pyrrolidine-1-carboxylate

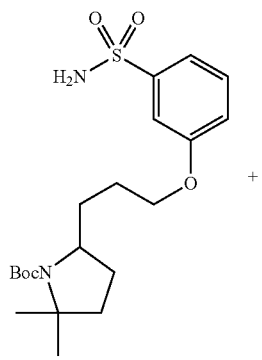

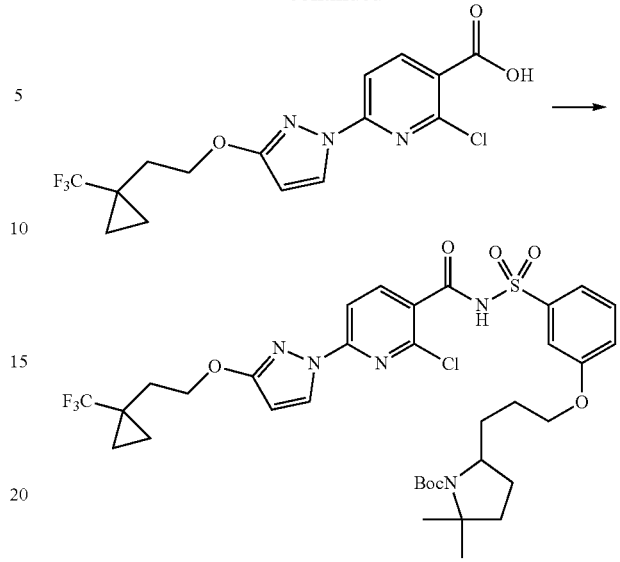

A 100 mL flask was charged under nitrogen with 2-chloro-6-[3-[2-[1-(trifluoromethyl)cyclopropyl]ethoxy]pyrazol-1-yl]pyridine-3-carboxylic acid (650 mg, 1.730 mmol) and carbonyl diimidazole (345 mg, 2.128 mmol). Added N,N-dimethylformamide (5.850 mL) and the mixture was stirred at 40° C. under nitrogen for 1 h. In a separate 100 mL flask, tert-butyl 2,2-dimethyl-5-[3-(3-sulfamoylphenoxy)propyl]pyrrolidine-1-carboxylate (750 mg, 1.818 mmol) was dissolved under nitrogen in anhydrous N,N-dimethylformamide (5.850 mL). NaH (77.0 mg, 1.925 mmol) (60% oil suspension) was added portionwise and the mixture was stirred under nitrogen until gas evolution stopped. The vial was capped and it was stirred at room temperature for 45 min. The two mixtures were combined and stirred at room temperature for 20 h. Heated to 55° C. for additional 4 h. Water and ice were added, followed by concentrated hydrochloric acid dropwise until a white precipitate persisted. The mixture was then washed with ethyl acetate, and combined organic layers were washed with brine then washed with 1:1 saturated aqueous sodium bicarbonate/1N sodium hydroxide (3×), dried over sodium sulfate, vacuum filtered and concentrated. Then the residue was dissolved in 10 mL of dichloromethane and was purified by silica gel chromatography using a shallow gradient from 100% hexanes to 65% ethyl acetate in hexanes to obtain as a white solid, tert-butyl 5-[3-[3-[[2-chloro-6-[3-[2-[1-(trifluoromethyl)cyclopropyl]ethoxy]pyrazol-1-yl]pyridine-3-carbonyl]sulfamoyl]phenoxy]propyl]-2,2-dimethyl-pyrrolidine-1-carboxylate (450 mg, 34%). $^1$H NMR (400 MHz, dimethyl sulfoxide-$d_6$) 1H NMR (400 MHz, dimethyl sulfoxide) δ 8.39 (d, J=2.9 Hz, 1H), 8.11 (d, J=8.3 Hz, 1H), 7.68 (d, J=8.4 Hz, 1H), 7.62-7.51 (m, 2H), 7.46 (d, J=1.9 Hz, 1H), 7.30 (d, J=6.9 Hz, 1H), 6.18 (d, J=2.9 Hz, 1H), 4.48-4.25 (m, 2H), 4.06 (s, 2H), 3.74 (s, 1H), 2.08 (dd, J=9.0, 5.1 Hz, 2H), 1.88 (s, 2H), 1.71 (dd, J=25.9, 15.0 Hz, 4H), 1.55 (d, J=5.7 Hz, 2H), 1.36 (s, 12H), 1.23 (s, 3H), 0.96 (dd, J=7.7, 3.8 Hz, 2H), 0.88 (s, 2H). ESI-MS m/z calc. 769.2524, found 770.5 (M+1)$^+$; Retention time: 2.11 min (LC Method G).

Step 3: 12,12-Dimethyl-8-(3-{2-[1-(trifluoromethyl) cyclopropyl]ethoxy}-1H-pyrazol-1-yl)-19-oxa-2λ⁶-thia-3,9,11-triazatetracyclo[18.3.1.0⁵,¹⁰.0¹¹,¹⁵] tetracosa-1(24),5(10),6,8,20,22-hexaene-2,2,4-trione

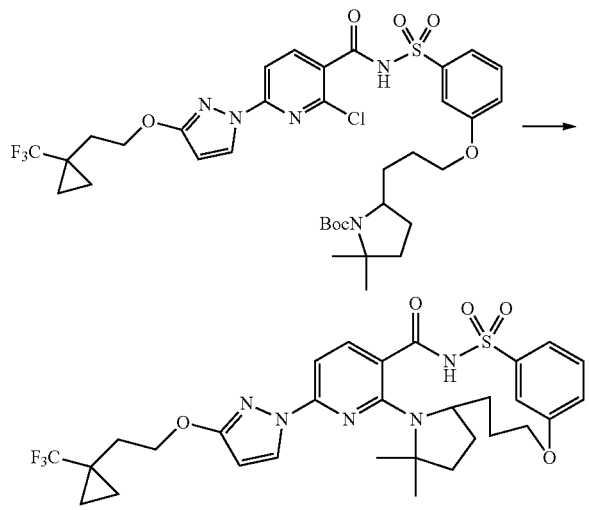

In a 50 mL round bottom flask was combined tert-butyl 5-[3-[3-[[2-chloro-6-[3-[2-[1-(trifluoromethyl)cyclopropyl ethoxy]pyrazol-1-yl]pyridine-3-carbonyl]sulfamoyl]phenoxy]propyl]-2,2-dimethyl-pyrrolidine-1-carboxylate (445 mg, 0.5777 mmol) dissolved in dichloromethane (2.225 mL) followed by addition of hydrochloric acid (4M in dioxane) (1.589 mL of 4 M, 6.355 mmol) and the mixture was stirred for 2 h. Then the material was concentrated under reduced pressure to dryness to afford material which was dissolved in dimethyl sulfoxide (9 mL) followed by addition of excess potassium carbonate (1.0 g, 7.236 mmol). The vial was capped and heated to 150° C. on a hot plate for 20 h. Added cesium fluoride (131.6 mg, 31.98 µL, 0.8666 mmol) and the reaction was heated to 170° C. for an additional 4 h. The reaction mixture was filtered and then purified by reverse-phase preparative chromatography utilizing a C₁₈ column (40-70 acetonitrile-water+5 mM trifluoroacetic acid) giving as an off-white solid, 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.3.1.0⁵,¹⁰.0¹¹,¹⁵]tetracosa-1(24),5(10),6,8,20,22-hexaene-2,2,4-trione (15.3 mg, 4%). ESI-MS m/z calc. 633.22327, found 634.2 (M+1)⁺; Retention time: 1.83 min (LC Method E).

Step 4: 12,12-Dimethyl-8-(3-{2-[1-(trifluoromethyl) cyclopropyl]ethoxy}-1H-pyrazol-1-yl)-19-oxa-2λ⁶-thia-3,9,11-triazatetracyclo[18.3.1.0⁵,¹⁰.0¹¹,¹⁵] tetracosa-1(24),5(10),6,8,20,22-hexaene-2,2,4-trione (Enantiomer 1) (Compound 7) and 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.3.1.0⁵,¹⁰.0¹¹,¹⁵]tetracosa-1(24),5(10),6,8, 20,22-hexaene-2,2,4-trione (Enantiomer 2) (Compound 8)

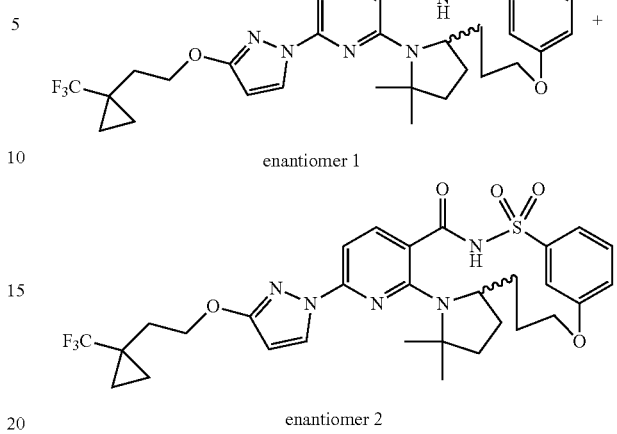

Racemic 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.3.1.0⁵,¹⁰.0¹¹,¹⁵]tetracosa-1(24),5 (10),6,8,20,22-hexaene-2,2,4-trione (15.3 mg, 0.02414 mmol) was subjected to chiral SFC purification using a ChiralPak AS-H (250×10 mm column, 5 µm particle size) with 18% methanol/82% carbon dioxide mobile phase at 10 mL/min giving as the first enantiomer to elute as an off-white solid, 12,12-dimethyl-8-(3-{2-[1-(trifluoromethyl)cyclo propyl]ethoxy}-1H-pyrazol-1-yl)-19-oxa-2λ⁶-thia-3,9,11-triazatetracyclo[18.3.1.0⁵,¹⁰.0¹¹,¹⁵]tetracosa-1(24),5 (10),6,8,20,22-hexaene-2,2,4-trione (enantiomer 1) (Compound 7) (3.4 mg, 44%), ESI-MS m/z calc. 633.22327, found 634.2 (M+1)⁺; Retention time: 1.84 min (LC Method E), and as the second enantiomer to elute as an off-white solid, 12,12-dimethyl-8-(3-{2-[1-(trifluoromethyl)cyclopropyl]ethoxy}-1H-pyrazol-1-yl)-19-oxa-2λ⁶-thia-3,9,11-triazatetracyclo[18.3.1.0⁵,¹⁰.0¹¹,¹⁵]tetracosa-1(24),5(10),6, 8,20,22-hexaene-2,2,4-trione (enantiomer 2) (Compound 8) (3.4 mg, 44%), ESI-MS m/z calc. 633.22327, found 634.2 (M+1)⁺; Retention time: 1.84 min (LC Method E).

Example 111: Preparation of 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,¹⁰.0¹¹,¹⁵]tetracosa-1(23),5,7,9,20(24), 21-hexaene-2,2,4-trione (Compound 16)

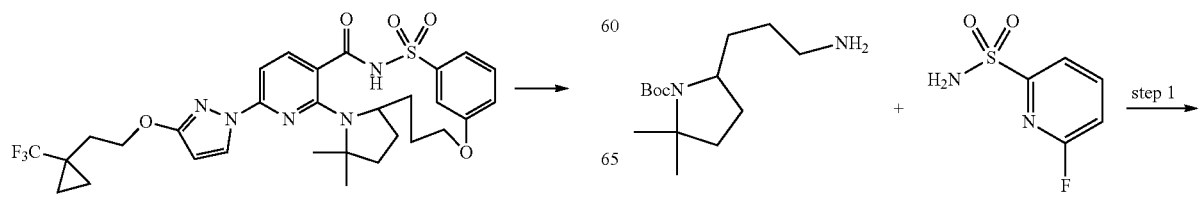

step 1

827

-continued

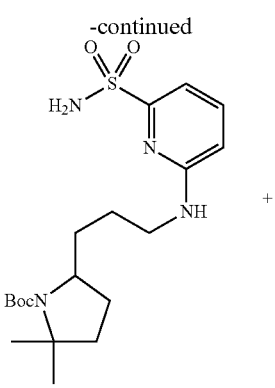

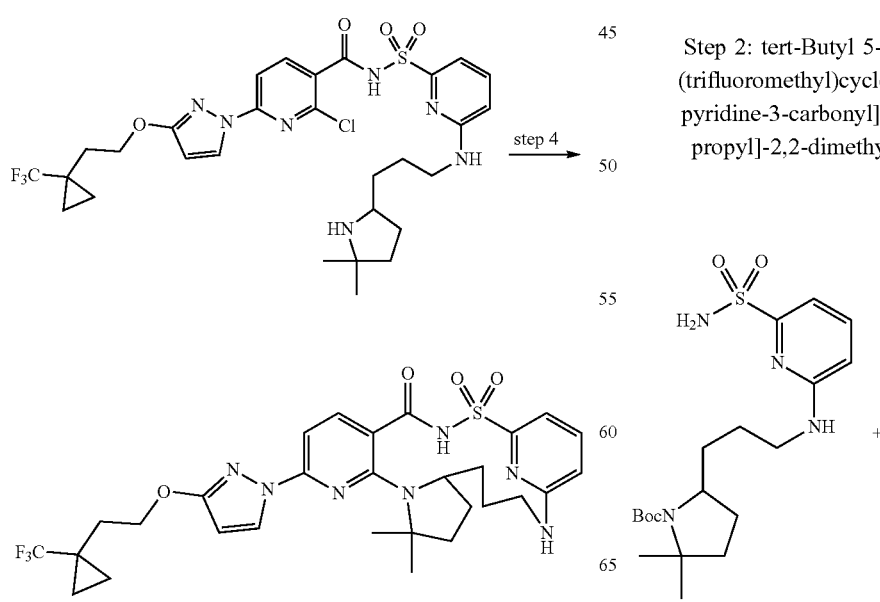

828

Step 1: tert-Butyl 2,2-dimethyl-5-[3-[(6-sulfamoyl-2-pyridyl)amino]propyl]pyrrolidine-1-carboxylate

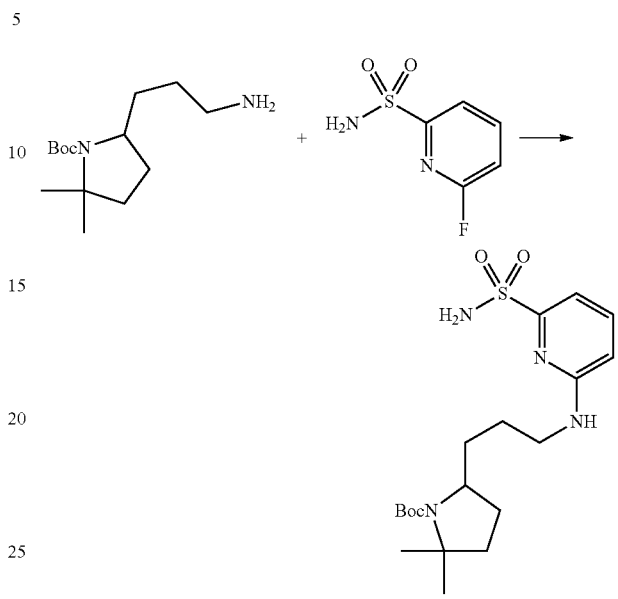

To a vial was added potassium carbonate (495 mg, 3.582 mmol), tert-butyl 5-(3-aminopropyl)-2,2-dimethyl-pyrrolidine-1-carboxylate (304 mg, 1.19 mmol), 6-fluoropyridine-2-sulfonamide (208.9 mg, 1.186 mmol), and dimethyl sulfoxide (3 mL). The reaction was stirred at 80° C. overnight. The reaction was filtered and purified via HPLC (1%-99% acetonitrile/water with a 0.1% hydrochloric acid modifier gradient) giving tert-butyl 2,2-dimethyl-5-[3-[(6-sulfamoyl-2-pyridyl)amino]propyl]pyrrolidine-1-carboxylate (224.7 mg, 46%) as a white foam. ESI-MS m/z calc. 412.21442, found 413.8 (M+1)⁺; Retention time: 0.94 min (LC Method B).

Step 2: tert-Butyl 5-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate

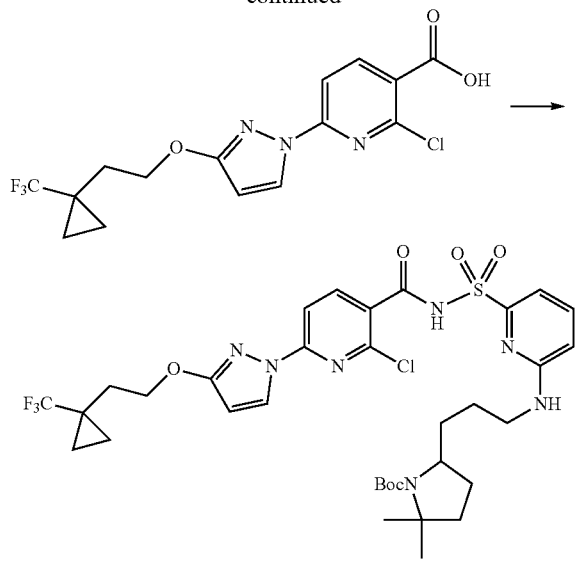

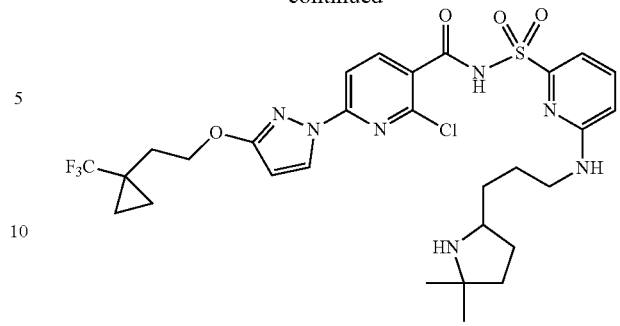

To a round bottom flask was added 2-chloro-6-[3-[2-[1-(trifluoromethyl)cyclopropyl]ethoxy]pyrazol-1-yl]pyridine-3-carboxylic acid (204 mg, 0.5429 mmol), carbonyl diimidazole (93 mg, 0.5735 mmol), and tetrahydrofuran (3 mL). The reaction was purged with nitrogen and placed in a preheated 45° C. oil bath for 90 min. tert-Butyl 2,2-dimethyl-5-[3-[(6-sulfamoyl-2-pyridyl)amino]propyl]pyrrolidine-1-carboxylate (224 mg, 0.5430 mmol) was added followed by 1,8-diazabicyclo[5.4.0]undec-7-ene (250 μL, 1.672 mmol) and the reaction was allowed to stir overnight at room temperature. The reaction was filtered and purified via HPLC (30%-99% acetonitrile/water with a 0.1% hydrochloric acid modifier gradient) giving tert-butyl 5-[3-[[6-[[2-chloro-6-[3-[2-[1-(trifluoromethyl) cyclopropyl]ethoxy] pyrazol-1-yl]pyridine-3-carbonyl]sulfamoyl]-2-pyridyl] amino]propyl]-2,2-dimethyl-pyrrolidine-1-carboxylate (196.5 mg, 47%) as a white solid. ESI-MS m/z calc. 769.2636, found 770.5 (M+1)⁺; Retention time: 1.98 min (LC Method B).

Step 3: 2-Chloro-N-[[6-[3-(5,5-dimethylpyrrolidin-2-yl)propylamino]-2-pyridyl]sulfonyl]-6-[3-[2-[1-(trifluoromethyl)cyclopropyl]ethoxy]pyrazol-1-yl] pyridine-3-carboxamide

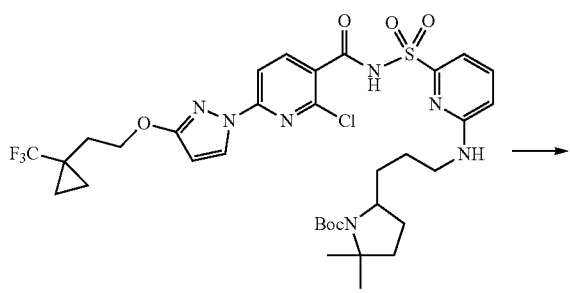

To a round bottom flask was added tert-butyl 5-[3-[[6-[[2-chloro-6-[3-[2-[1-(trifluoromethyl)cyclopropyl]ethoxy] pyrazol-1-yl]pyridine-3-carbonyl]sulfamoyl]-2-pyridyl] amino]propyl]-2,2-dimethyl-pyrrolidine-1-carboxylate (195 mg, 0.2532 mmol) and dichloromethane (5 mL). Added hydrochloric acid (1.3 mL of 4 M in dioxane, 5.200 mmol) dropwise and the reaction was allowed to stir at room temperature for 1 h. The reaction was evaporated to dryness. The reaction was diluted with 3 M potassium carbonate to pH=10 and extracted with ethyl acetate three times. The combined organic layers were dried over sodium sulfate, filtered and evaporated giving 2-chloro-N-[[6-[3-(5,5-dimethylpyrrolidin-2-yl)propylamino]-2-pyridyl]sulfonyl]-6-[3-[2-[1-(trifluoromethyl)cyclopropyl]ethoxy]pyrazol-1-yl] pyridine-3-carboxamide (169 mg, 100%). ESI-MS m/z calc. 669.2112, found 670.5 (M+1)⁺; Retention time: 0.78 min (LC Method B).

Step 4: 12,12-Dimethyl-8-(3-{2-[1-(trifluoromethyl) cyclopropyl]ethoxy}-1H-pyrazol-1-yl)-2λ⁶-thia-3,9, 11,19,24-pentaazatetracyclo[18.3.1.0⁵,¹⁰.0¹¹,¹⁵] tetracosa-1(23),5,7,9,20(24),21-hexaene-2,2,4-trione (Compound 16)

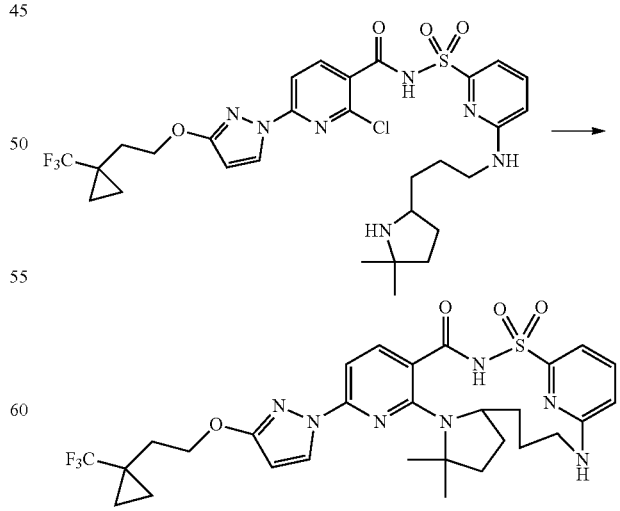

To a vial was added potassium carbonate (175 mg, 1.266 mmol), cesium fluoride (58 mg, 0.3818 mmol), and a solution of 2-chloro-N-[[6-[3-(5,5-dimethylpyrrolidin-2-yl)propylamino]-2-pyridyl]sulfonyl]-6-[3-[2-[1-(trifluoromethyl)cyclopropyl]ethoxy]pyrazol-1-yl]pyridine-3-carboxamide (169 mg, 0.2522 mmol) in dimethyl sulfoxide (3.0 mL). The reaction was heated in a sealed tube overnight at 150° C. The reaction was quenched with brine and extracted with ethyl acetate. The organic layer was dried over sodium sulfate, filtered, and evaporated. The crude reaction mixture was purified via silica gel chromatography (0%-50% ethyl acetate in dichloromethane gradient) giving 12,12-dimethyl-8-(3-{2-[1-(trifluoromethyl)cyclopropyl]ethoxy}-1H-pyrazol-1-yl)-2$\lambda^6$-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 16) (93 mg, 58%) as a white solid. $^1$H NMR (400 MHz, dimethyl sulfoxide-$d_6$) δ 12.75 (s, 1H), 8.23 (d, J=2.7 Hz, 1H), 8.01 (d, J=8.2 Hz, 1H), 7.58 (t, J=7.8 Hz, 1H), 7.29 (s, 1H), 7.03 (d, J=7.2 Hz, 2H), 6.63 (d, J=8.4 Hz, 1H), 6.13 (d, J=2.7 Hz, 1H), 4.32 (t, J=7.1 Hz, 2H), 3.72 (s, 2H), 3.10 (s, 1H), 2.08 (t, J=7.0 Hz, 2H), 1.86 (s, 2H), 1.73 (s, 2H), 1.51 (s, 4H), 1.35 (s, 3H), 1.24 (s, 2H), 1.02-0.93 (m, 3H), 0.90-0.85 (m, 2H). ESI-MS m/z calc. 633.2345, found 634.2 (M+1)$^+$; Retention time: 1.85 min (LC Method B).

Example 112: Preparation of 20,20,22-trimethyl-4-(3-{2-[1-(trifluoromethyl)cyclopropyl]ethoxy}-1H-pyrazol-1-yl)-10$\lambda^6$-thia-1,3,9,13,14-pentaazatetracyclo[16.2.1.1¹¹,¹⁴.0²,⁷]docosa-2,4,6,11(22),12-pentaene-8,10,10-trione (Compound 18) and 12,20,20-trimethyl-4-(3-{2-[1-(trifluoromethyl)cyclopropyl]ethoxy}-1H-pyrazol-1-yl)-10$\lambda^6$-thia-1,3,9,13,14-pentaazatetracyclo[16.2.1.1¹¹,¹⁴.0²,⁷]docosa-2,4,6,11(22),12-pentaene-8,10,10-trione (Compound 19)

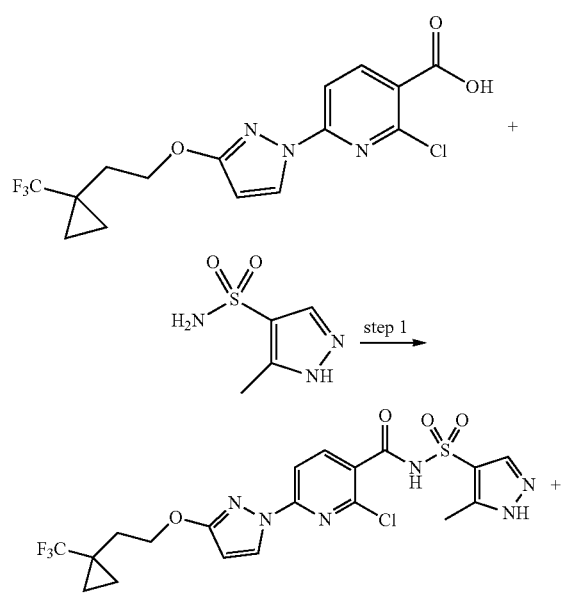

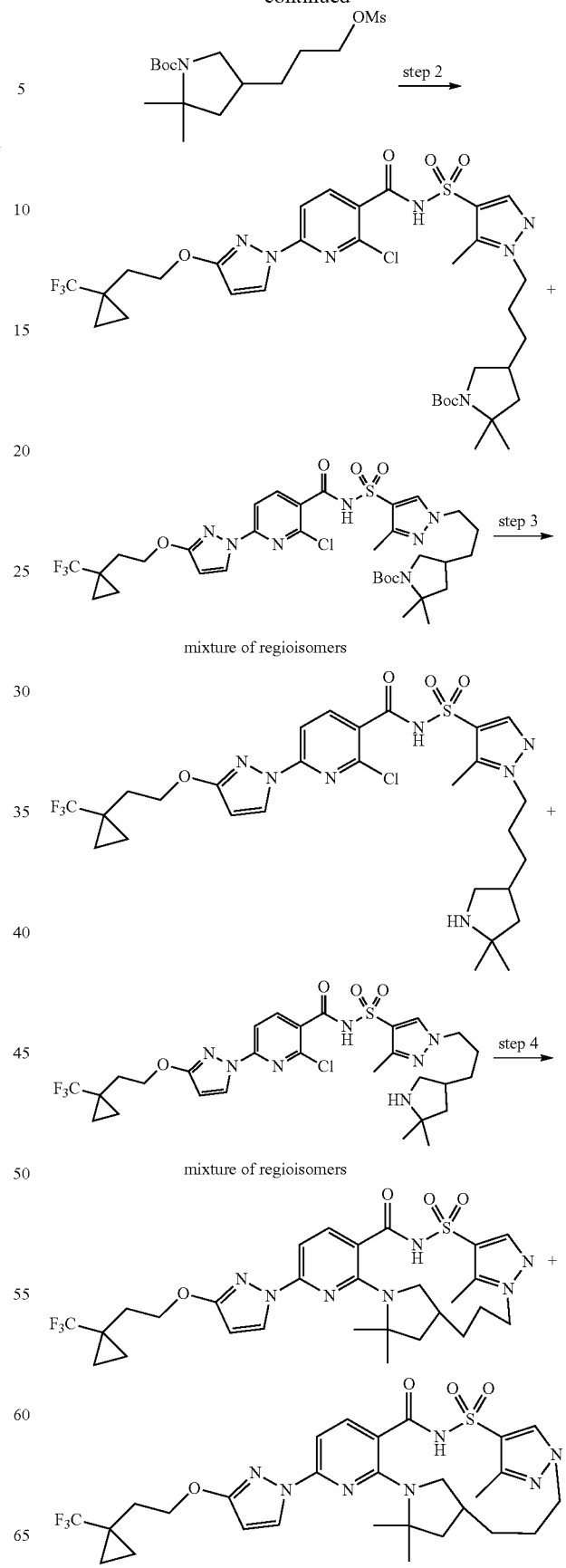

Step 1: 2-Chloro-N-[(5-methyl-1H-pyrazol-4-yl)sulfonyl]-6-[3-[2-[1-(trifluoromethyl)cyclopropyl]ethoxy]pyrazol-1-yl]pyridine-3-carboxamide

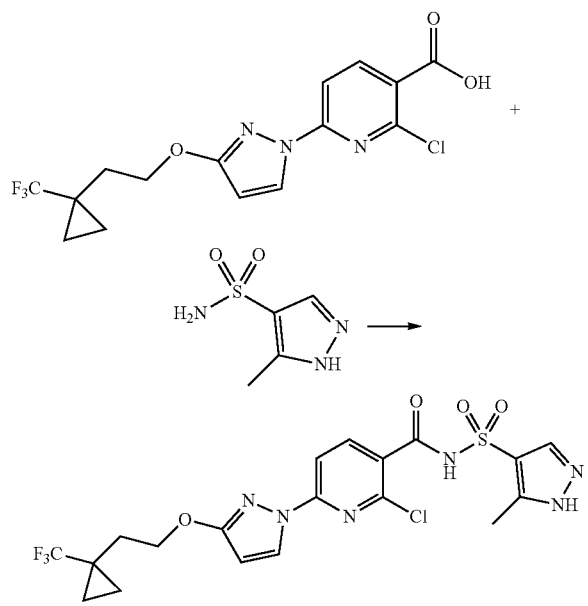

To a vial was added 2-chloro-6-[3-[2-[1-(trifluoromethyl)cyclopropyl]ethoxy]pyrazol-1-yl]pyridine-3-carboxylic acid (100 mg, 0.2661 mmol), carbonyl diimidazole (48 mg, 0.30 mmol), and tetrahydrofuran (1 mL). The reaction was stirred at 45° C. for 1 h. 5-Methyl-1H-pyrazole-4-sulfonamide (43 mg, 0.2668 mmol) and 1,8-diazabicyclo[5.4.0]undec-7-ene (125 µL, 0.836 mmol) were added and the reaction was allowed to stir overnight at 45° C. The crude reaction was filtered and purified via HPLC (10%-99% acetonitrile/water with a 0.1% hydrochloric acid modifier gradient giving 2-chloro-N-[(5-methyl-1H-pyrazol-4-yl)sulfonyl]-6-[3-[2-[1-(trifluoromethyl)cyclopropyl]ethoxy]pyrazol-1-yl]pyridine-3-carboxamide (80.0 mg, 58%). ESI-MS m/z calc. 518.0751, found 519.1 (M+1)+; Retention time: 1.7 min (LC Method B).

Step 2: tert-Butyl 4-[3-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]propyl]-2,2-dimethyl-pyrrolidine-1-carboxylate and tert-butyl 4-[3-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (Mixture of Regioisomers)

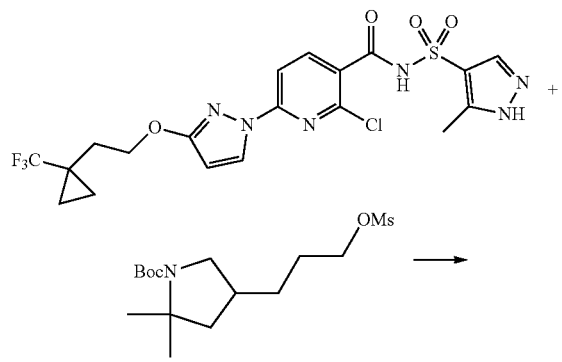

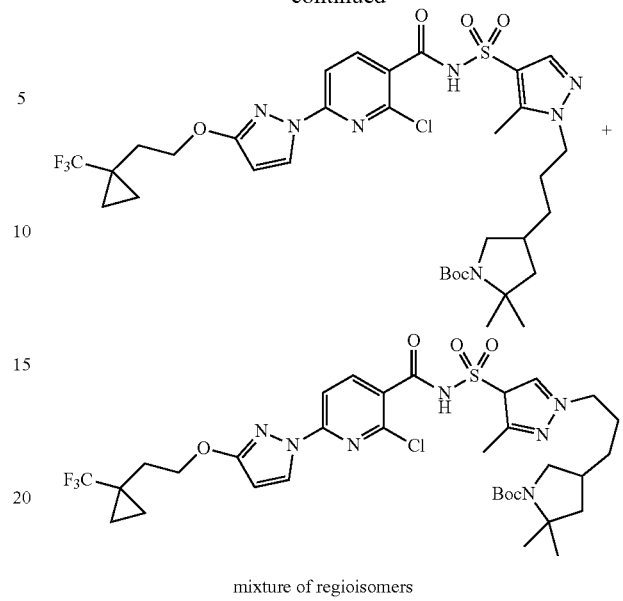

mixture of regioisomers

To a round bottom flask containing 2-chloro-N-[(5-methyl-1H-pyrazol-4-yl)sulfonyl]-6-[3-[2-[1-(trifluoromethyl)cyclopropyl]ethoxy]pyrazol-1-yl]pyridine-3-carboxamide (80 mg, 0.1542 mmol) was added N,N-dimethylformamide (2 mL), potassium carbonate (65 mg, 0.47 mmol), and tert-butyl 2,2-dimethyl-4-(3-methylsulfonyloxypropyl)pyrrolidine-1-carboxylate (68 mg, 0.20 mmol) in N,N-dimethylformamide (2 mL). The reaction was heated at 60° C. and stirred for 4 days. The reaction was filtered and purified via HPLC (30%-99% acetonitrile/water with a 0.1% hydrochloric acid modifier gradient) giving tert-butyl 4-[3-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]propyl]-2,2-dimethyl-pyrrolidine-1-carboxylate and tert-butyl 4-[3-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (mixture of regioisomers) (49.9 mg, 43%) as a white foam. ESI-MS m/z calc. 757.2636, found 758.4 (M+1)+; Retention time: 1.82 min (LC Method G).

Step 3: 2-Chloro-N-[1-[3-(5,5-dimethylpyrrolidin-3-yl)propyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[3-(5,5-dimethylpyrrolidin-3-yl)propyl]-5-methyl-pyrazol-4-yl]sulfonyl-6-[3-[2-[1-(trifluoromethyl)cyclopropyl]ethoxy]pyrazol-1-yl]pyridine-3-carboxamide (Mixture of Regioisomers)

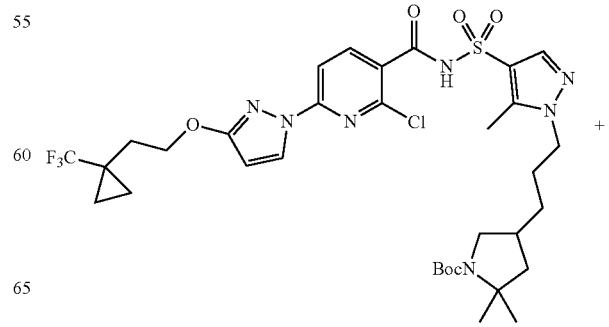

835

-continued

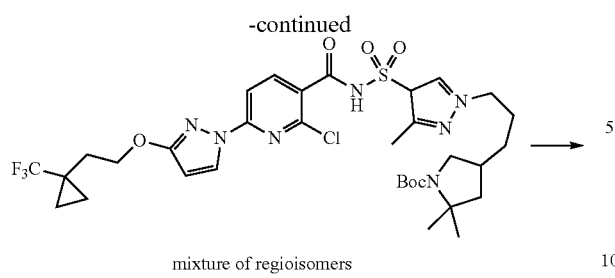

mixture of regioisomers

To a round bottom flask was added tert-butyl 4-[3-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]propyl]-2,2-dimethyl-pyrrolidine-1-carboxylate and tert-butyl 4-[3-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (mixture of regioisomers) (49.9 mg, 0.0658 mmol), dioxane (1 mL) and hydrochloric acid (165 µL of 4 M in dioxane, 0.660 mmol). The reaction was heated at 35° C. overnight. The reaction was quenched with saturated sodium bicarbonate and extracted with ethyl acetate. The organic layer was dried over sodium sulfate, filtered and evaporated to provide 2-chloro-N-[1-[3-(5,5-dimethylpyrrolidin-3-yl)propyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[3-(5,5-dimethylpyrrolidin-3-yl)propyl]-5-methyl-pyrazol-4-yl]sulfonyl-6-[3-[2-[1-(trifluoromethyl)cyclopropyl]ethoxy]pyrazol-1-yl]pyridine-3-carboxamide (mixture of regioisomers) (42 mg, 97%) as a white solid. ESI-MS m/z calc. 657.2112, found 658.4 (M+1)+; Retention time: 0.74 min (LC Method B).

836

Step 4: 20,20,22-Trimethyl-4-(3-{2-[1-(trifluoromethyl)cyclopropyl]ethoxy}-1H-pyrazol-1-yl)-10λ6-thia-1,3,9,13,14-pentaazatetracyclo[16.2.1.111,14.02,7]docosa-2,4,6,11(22),12-pentaene-8,10,10-trione (Compound 18) and 12,20,20-trimethyl-4-(3-{2-[1-(trifluoromethyl)cyclopropyl]ethoxy}-1H-pyrazol-1-yl)-10λ6-thia-1,3,9,13,14-pentaazatetracyclo[16.2.1.111,14.02,7]docosa-2,4,6,11(22),12-pentaene-8,10,10-trione (Compound 19)

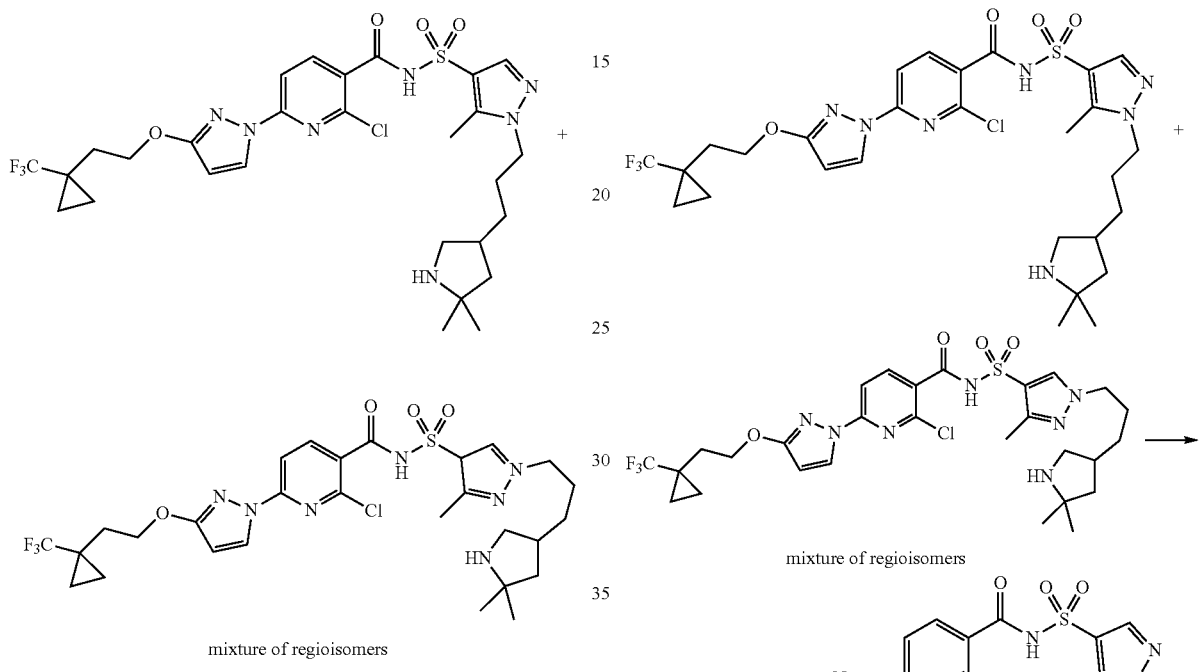

To a round bottom flask containing 2-chloro-N-[1-[3-(5,5-dimethylpyrrolidin-3-yl)propyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[3-(5,5-dimethylpyrrolidin-3-yl)propyl]-5-methyl-pyrazol-4-yl]sulfonyl-6-[3-[2-[1-(trifluoromethyl)cyclopropyl]ethoxy]pyrazol-1-yl]pyridine-3-carboxamide (mixture of regioisomers) (42 mg, 0.06382 mmol) was added potassium carbonate (44 mg, 0.32 mmol), cesium fluoride (50 mg, 0.33 mmol), dimethyl sulfoxide (2 mL), and four 3 Å molecular sieves. The reaction was heated at 150° C. overnight. The reaction was cooled to room temperature, filtered, and purified via HPLC (10%-99% acetonitrile/water with a 0.1% hydrochloric acid modifier gradient) giving as the first isomer to elute, 20,20,22-trimethyl-4-(3-{2-[1-(trifluoromethyl)cyclopropyl]ethoxy}-1H-pyrazol-1-yl)-10λ6-thia-1,3, 9,13,14-pentaazatetracyclo[16.2.1.1¹¹,¹⁴.0²,⁷]docosa-2,4,6,11(22),12-pentaene-8,10,10-trione (Compound 18) (2.8 mg, 7%) as an orange solid; ¹H NMR (400 MHz, dimethyl sulfoxide-$d_6$) δ 12.39 (s, 1H), 8.18 (d, J=2.8 Hz, 1H), 7.86 (s, 1H), 7.77 (d, J=8.3 Hz, 1H), 6.90 (d, J=8.2 Hz, 1H), 6.09 (d, J=2.7 Hz, 1H), 4.43-4.34 (m, 1H), 4.30 (t, J=7.0 Hz, 2H), 4.08-3.96 (m, 1H), 2.06 (q, J=7.4 Hz, 6H), 1.95-1.69 (m, 4H), 1.55 (s, 3H), 1.47 (s, 3H), 1.40-1.08 (m, 4H), 0.96 (td, J=4.9, 4.4, 3.1 Hz, 2H), 0.90-0.85 (m, 2H), ESI-MS m/z calc. 621.2345, found 622.6 (M+1)⁺; Retention time: 1.48 min (LC Method B) and as the second isomer to elute, 12,20,20-trimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,¹⁴.0²,⁷]docosa-2,4,6,11(22),12-pentaene-8,10,10-trione (Compound 19) (3.7 mg, 9%) as an orange solid; ¹H NMR (400 MHz, dimethyl sulfoxide-$d_6$) δ 12.18 (s, 1H), 8.41 (s, 1H), 8.18 (d, J=2.8 Hz, 1H), 7.75 (d, J=8.2 Hz, 1H), 6.89 (d, J=8.2 Hz, 1H), 6.10 (d, J=2.8 Hz, 1H), 4.31 (t, J=7.0 Hz, 2H), 4.22 (dt, J=13.6, 3.8 Hz, 1H), 3.97 (t, J=12.4 Hz, 1H), 2.40 (s, 3H), 2.20 (s, 1H), 2.07 (t, J=7.1 Hz, 4H), 2.02-1.68 (m, 4H), 1.51 (d, J=13.0 Hz, 6H), 1.38 (t, J=12.3 Hz, 1H), 1.03 (s, 1H), 0.96 (td, J=5.0, 4.5, 3.2 Hz, 2H), 0.93-0.84 (m, 2H), ESI-MS m/z calc. 621.2345, found 622.4 (M+1)⁺; Retention time: 1.54 min (LC Method B).

Example 113: Preparation of 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.1⁵,⁸.0⁹,¹⁴]tricosa-1(21),9,11,13,18(22),19-hexaene-15,17,17-trione (Compound 20)

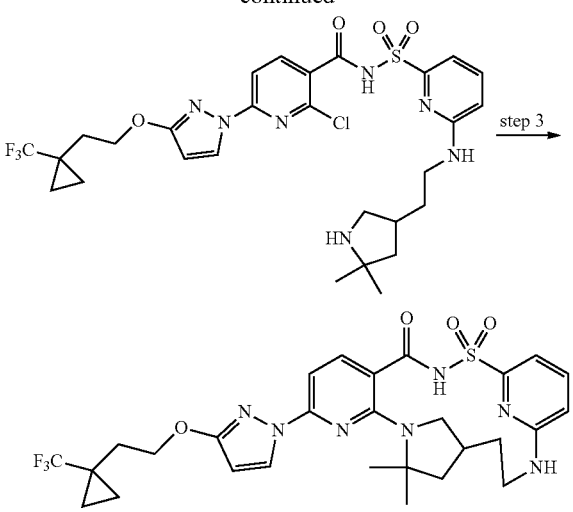

Step 1: tert-Butyl 4-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethyl]-2,2-dimethyl-pyrrolidine-1-carboxylate

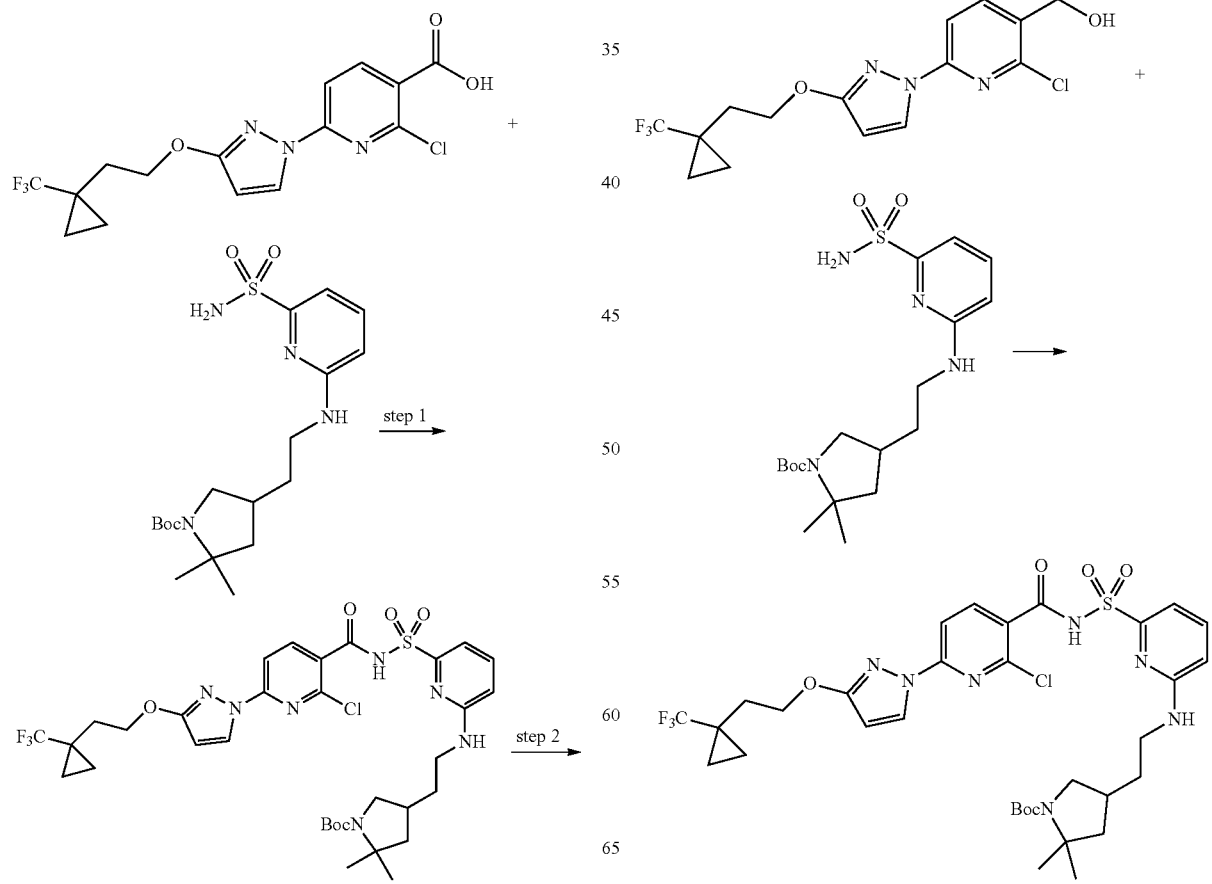

To a vial was added 2-chloro-6-[3-[2-[1-(trifluoromethyl) cyclopropyl]ethoxy]pyrazol-1-yl]pyridine-3-carboxylic acid (615 mg, 1.64 mmol), carbonyl diimidazole (279 mg, 1.72 mmol), and tetrahydrofuran (3 mL). The reaction was stirred at 45° C. for 2 h. tert-Butyl 2,2-dimethyl-4-[2-[(6-sulfamoyl-2-pyridyl)amino]ethyl]pyrrolidine-1-carboxylate (654 mg, 1.641 mmol) was added followed by 1,8-diazabicyclo[5.4.0]undec-7-ene (750 µL, 5.02 mmol) and the reaction was allowed to stir at 45° C. overnight. The reaction was quenched with 1 N citric acid and extracted with ethyl acetate. The organic layer was dried over sodium sulfate, filtered and evaporated. The crude reaction mixture was purified via silica gel chromatography (10%-100% ethyl acetate in hexanes gradient) giving tert-butyl 4-[2-[[6-[[2-chloro-6-[3-[2-[1-(trifluoromethyl)cyclopropyl]ethoxy] pyrazol-1-yl]pyridine-3-carbonyl]sulfamoyl]-2-pyridyl] amino]ethyl]-2,2-dimethyl-pyrrolidine-1-carboxylate (830 mg, 67%) as a white solid. ESI-MS m/z calc. 755.248, found 756.5 (M+1)$^+$; Retention time: 1.8 min (LC Method G).

Step 2: 2-Chloro-N-[[6-[2-(5,5-dimethylpyrrolidin-3-yl)ethylamino]-2-pyridyl]sulfonyl]-6-[3-[2-[1-(trifluoromethyl)cyclopropyl]ethoxy]pyrazol-1-yl] pyridine-3-carboxamide fate, filtered and evaporated to provide 2-chloro-N-[[6-[2-(5,5-dimethylpyrrolidin-3-yl)ethylamino]-2-pyridyl]sulfonyl]-6-[3-[2-[1-(trifluoromethyl)cyclopropyl]ethoxy] pyrazol-1-yl]pyridine-3-carboxamide (715 mg, 99%) as a white solid. $^1$H NMR (400 MHz, dimethyl sulfoxide-d$_6$) δ 8.35 (d, J=2.8 Hz, 1H), 8.11 (d, J=8.3 Hz, 1H), 7.62 (d, J=8.2 Hz, 1H), 7.44 (dd, J=8.3, 7.3 Hz, 1H), 6.98 (dd, J=7.2, 0.8 Hz, 1H), 6.84 (t, J=5.8 Hz, 1H), 6.47 (dd, J=8.3, 0.8 Hz, 1H), 6.12 (d, J=2.8 Hz, 1H), 4.33 (t, J=7.0 Hz, 2H), 3.81-3.69 (m, 1H), 3.17 (dq, J=12.3, 5.8 Hz, 1H), 3.09-2.97 (m, 1H), 2.39 (p, J=8.0 Hz, 1H), 2.08 (t, J=7.1 Hz, 2H), 1.95 (dd, J=12.8, 7.7 Hz, 1H), 1.62 (dp, J=19.9, 6.4 Hz, 2H), 1.35 (dd, J=12.8, 10.2 Hz, 1H), 1.26 (d, J=32.0 Hz, 6H), 1.01-0.84 (m, 4H). ESI-MS m/z calc. 655.19556, found 656.6 (M+1)$^+$; Retention time: 0.78 min (LC Method B).

Step 3: 7,7-Dimethyl-11-(3-{2-[1-(trifluoromethyl) cyclopropyl]ethoxy}-1H-pyrazol-1-yl)-17λ$^6$-thia-2, 8,10,16,22-pentaazatetracyclo[16.3.1.1$^{5,8}$.0$^{9,14}$] tricosa-1(21),9,11,13,18(22),19-hexaene-15,17,17-trione (Compound 20)

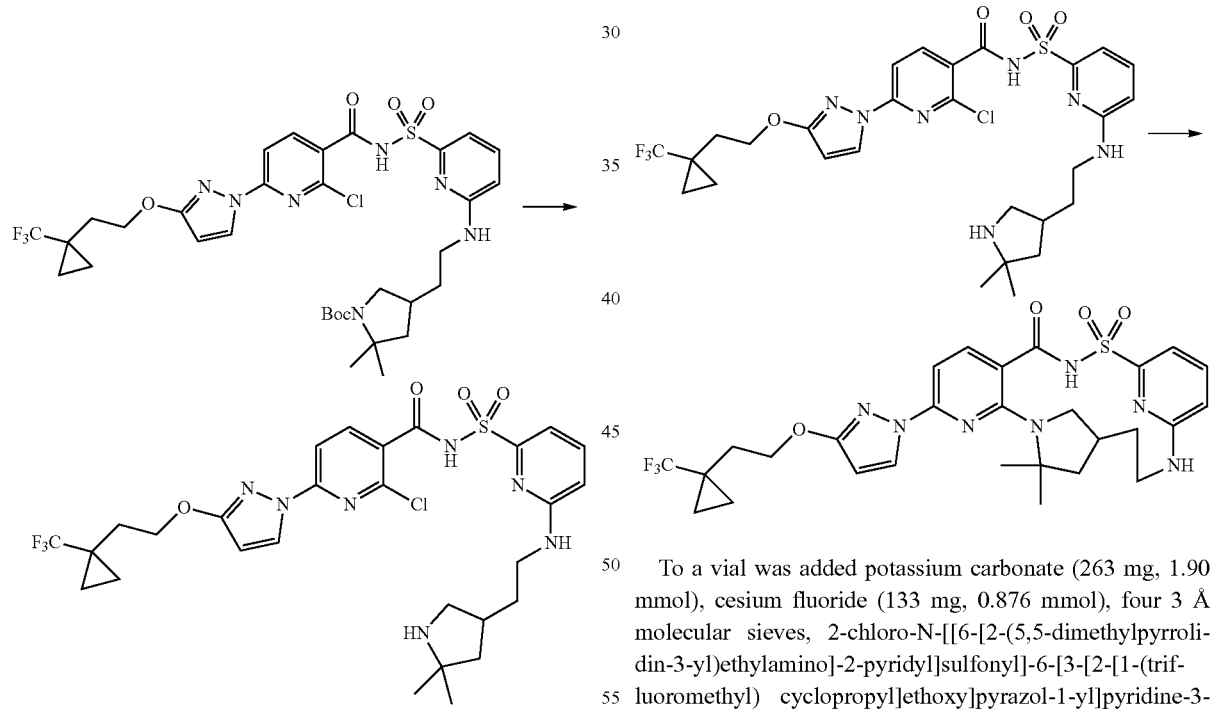

To a vial was added potassium carbonate (263 mg, 1.90 mmol), cesium fluoride (133 mg, 0.876 mmol), four 3 Å molecular sieves, 2-chloro-N-[[6-[2-(5,5-dimethylpyrrolidin-3-yl)ethylamino]-2-pyridyl]sulfonyl]-6-[3-[2-[1-(trifluoromethyl) cyclopropyl]ethoxy]pyrazol-1-yl]pyridine-3-carboxamide (250 mg, 0.381 mmol), and dimethyl sulfoxide (7 mL). The reaction was capped and placed in a preheated 155° C. oil bath overnight. The reaction was diluted with ethyl acetate and quenched with 1N citric acid followed by brine. The reaction was extracted twice with ethyl acetate, dried over sodium sulfate, filtered and evaporated. The crude reaction mixture was purified via silica gel chromatography (0%-100% ethyl acetate in hexanes gradient) to provide 7,7-dimethyl-11-(3-{2-[1-(trifluoromethyl)cyclopropyl] ethoxy}-1H-pyrazol-1-yl)-17λ$^6$-thia-2,8,10,16,22-pentaaza- To a round bottom flask containing tert-butyl 4-[2-[[6-[[2-chloro-6-[3-[2-[1-(trifluoromethyl)cyclopropyl]ethoxy] pyrazol-1-yl]pyridine-3-carbonyl]sulfamoyl]-2-pyridyl] amino]ethyl]-2,2-dimethyl-pyrrolidine-1-carboxylate (830 mg, 1.098 mmol) was added dichloromethane (2 mL) and hydrochloric acid (2.75 mL of 4 M in dioxane, 11.00 mmol). After 40 min, the reaction was quenched with saturated sodium bicarbonate and extracted with ethyl acetate twice. The combined organic layers were dried over sodium sultetracyclo[16.3.1.15,8.09,14]tricosa-1(21),9,11,13,18(22),19-hexaene-15,17,17-trione (Compound 20) (101 mg, 43%). ESI-MS m/z calc. 619.2189, found 620.2 (M+1)+; Retention time: 2.07 min (LC Method B).

Example 114: Preparation of 12,12-dimethyl-8-(3-{2-[1-(trifluoromethyl)cyclopropyl]ethoxy}-1H-pyrazol-1-yl)-2λ6-thia-3,9,11,18,22-pentaazatetracyclo[17.3.1.111,14.05,10]tetracosa-1(23),5(10),6,8,19,21-hexaene-2,2,4-trione (Hydrochloride Salt) (Compound 23)

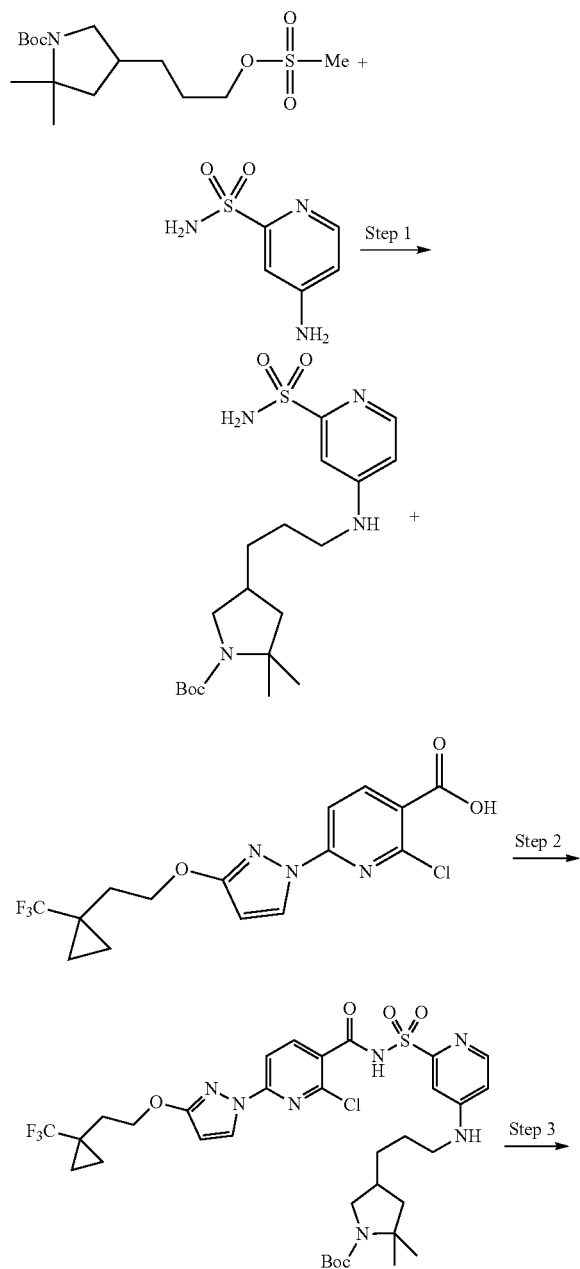

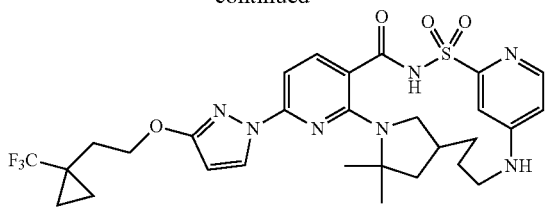

Step 1: tert-Butyl 2,2-dimethyl-4-[3-[(2-sulfamoyl-4-pyridyl)amino]propyl]pyrrolidine-1-carboxylate

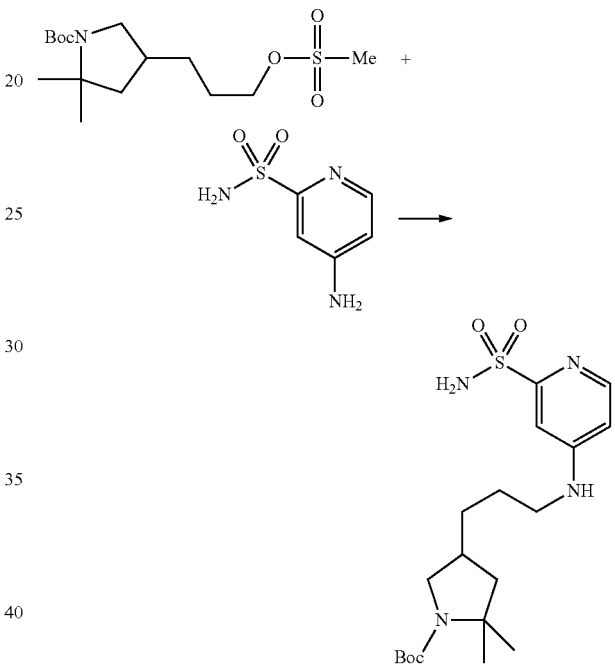

To a solution of tert-butyl 2,2-dimethyl-4-(3-methylsulfonyloxypropyl) pyrrolidine-1-carboxylate (300 mg, 0.894 mmol) in N,N-dimethylformamide (5 mL) was added 4-aminopyridine-2-sulfonamide (310 mg, 1.79 mmol) and cesium carbonate (900 mg, 2.76 mmol). The reaction mixture was stirred at 70° C. for 4 h. The reaction mixture was cooled to room temperature and poured into water (100 mL) and extracted with ethyl acetate (2×100 mL), combined the organic layers, washed with brine, dried (sodium sulfate), filtered and concentrated giving tert-butyl 2,2-dimethyl-4-[3-[(2-sulfamoyl-4-pyridyl)amino]propyl]pyrrolidine-1-carboxylate which was used directly in the next step (369 mg, quant.). $^1$H NMR (400 MHz, dimethyl sulfoxide-$d_6$) δ 8.32 (brs, 2H), 8.12 (dd, J=6.6, 1.6 Hz, 1H), 7.24 (dd, J=6.3, 2.4 Hz, 1H), 6.87 (dt, J=6.7, 2.0 Hz, 1H), 3.50 (q, J=9.0 Hz, 2H), 3.40-3.28 (m, 1H), 2.96 (p, J=7.0, 6.4 Hz, 2H), 2.83-2.68 (m, 1H), 2.07-1.96 (m, 1H), 1.89-1.74 (m, 2H), 1.45-1.26 (m, 14H), 1.23 (s, 3H). ESI-MS m/z calc. 412.21442, found 413.5 (M+1)+; Retention time: 0.52 min (LC Method A).

Step 2: tert-Butyl 4-[3-[[2-[[2-chloro-6-[3-[2-[1-(trifluoromethyl)cyclopropyl]ethoxy]pyrazol-1-yl]pyridine-3-carbonyl]sulfamoyl]-4-pyridyl]amino]propyl]-2,2-dimethyl-pyrrolidine-1-carboxylate

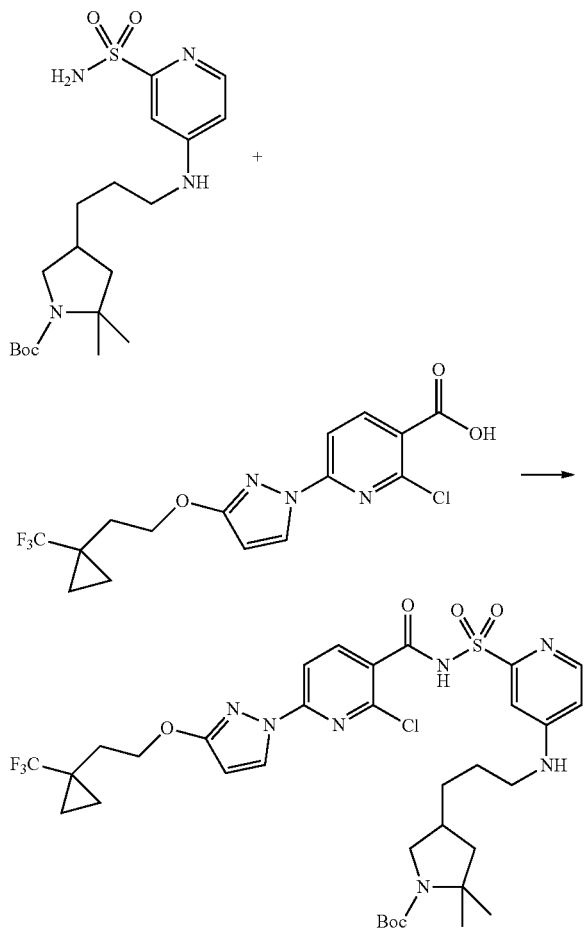

A solution of 2-chloro-6-[3-[2-[1-(trifluoromethyl)cyclopropyl]ethoxy]pyrazol-1-yl]pyridine-3-carboxylic acid (300 mg, 0.798 mmol) and carbonyl diimidazole (130 mg, 0.802 mmol) in tetrahydrofuran (5 mL) was stirred for 45 min. Then, tert-butyl 2,2-dimethyl-4-[3-[(2-sulfamoyl-4-pyridyl)amino]propyl]pyrrolidine-1-carboxylate (330 mg, 0.800 mmol) and 1,8-diazabicyclo[5.4.0]undec-7-ene (150 µL, 1.00 mmol) were added and the reaction mixture was stirred for overnight at room temperature. The reaction mixture was quenched with saturated aqueous ammonium chloride solution and extracted with ethyl acetate. The organic layer was washed with brine, dried over sodium sulfate, filtered and evaporated to give an oily material which was purified by reverse phase HPLC-MS using a Luna $C_{18}$ (2) column (75×30 mm, 5 µm particle size) sold by Phenomenex (pn: 00C-4252-U0-AX), and a dual gradient run from 1%-99% mobile phase B over 15.0 min (mobile phase A=water (5 mM hydrochloric acid), mobile phase B=acetonitrile, Flow rate=50 mL/min, injection volume=950 µL and column temperature=25° C.) to afford the desired product tert-butyl 4-[3-[[2-[[2-chloro-6-[3-[2-[1-(trifluoromethyl)cyclopropyl]ethoxy]pyrazol-1-yl]pyridine-3-carbonyl]sulfamoyl]-4-pyridyl]amino]propyl]-2,2-dimethyl-pyrrolidine-1-carboxylate (23 mg, 4%) as off white sticky material. $^1$H NMR (400 MHz, dimethyl sulfoxide-$d_6$) δ 8.40 (d, J=2.8 Hz, 1H), 8.15 (d, J=5.6 Hz, 1H), 7.96 (d, J=8.3 Hz, 1H), 7.66 (d, J=8.3 Hz, 1H), 7.00 (d, J=2.2 Hz, 1H), 6.80 (s, 2H), 6.69 (dd, J=5.7, 2.2 Hz, 1H), 6.18 (d, J=2.8 Hz, 1H), 4.34 (t, J=7.1 Hz, 2H), 3.81-3.71 (m, 1H), 3.54 (q, J=8.3 Hz, 1H), 2.77 (q, J=10.0 Hz, 1H), 2.18-2.02 (m, 4H), 1.90-1.77 (m, 1H), 1.74-1.65 (m, 1H), 1.43-1.32 (m, 14H), 1.22 (s, 3H), 1.01-0.94 (m, 2H), 0.91-0.87 (m, 2H). ESI-MS m/z calc. 769.2636, found 770.7 (M+1)$^+$; Retention time: 0.87 min (LC Method A).

Step 3: 12,12-Dimethyl-8-(3-{2-[1-(trifluoromethyl)cyclopropyl]ethoxy}-1H-pyrazol-1-yl)-2λ$^6$-thia-3,9,11,18,22-pentaazatetracyclo[17.3.1.1$^{11,14}$.0$^{5,10}$]tetracosa-1(23),5(10),6,8,19,21-hexaene-2,2,4-trione (Hydrochloride Salt) (Compound 23)

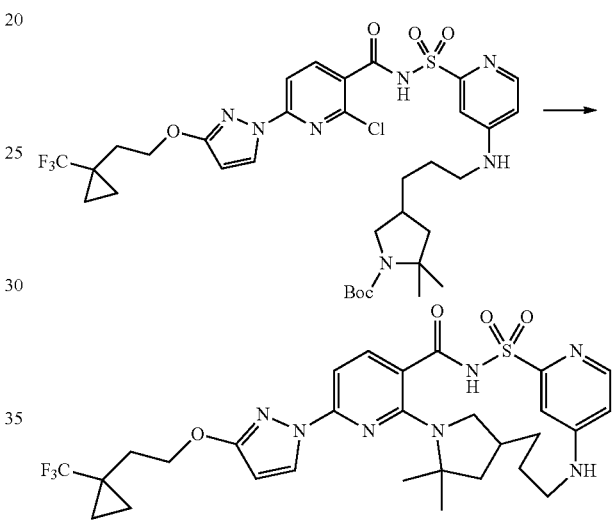

tert-Butyl 4-[3-[[2-[[2-chloro-6-[3-[2-[1-(trifluoromethyl)cyclopropyl]ethoxy]pyrazol-1-yl]pyridine-3-carbonyl]sulfamoyl]-4-pyridyl]amino]propyl]-2,2-dimethyl-pyrrolidine-1-carboxylate (20 mg, 0.026 mmol) was dissolved in dioxane (1.0 mL) and to the mixture was added hydrochloric acid (4M in dioxane) (250 µL of 4 M, 1.0 mmol) and the resulting mixture was stirred at room temperature for 3 h. Concentrated mixture to dryness under reduced pressure, redissolved in ethyl acetate and then added aqueous 2 M sodium carbonate (5 mL), pH~10. Extracted the organic layer with ethyl acetate (2×10 mL), washed with brine, then dried over sodium sulfate, filtered and evaporated to dryness under reduced pressure giving material which was combined with potassium carbonate (20 mg, 0.14 mmol), cesium fluoride (10 mg, 0.066 mmol) and dimethyl sulfoxide (2.0 mL) in a vial. Purged the vial with nitrogen, capped, heated to 150° C. and stirred for 16 h. Cooled to room temperature and the reaction mixture was filtered through Whatman filter disc (puradisc 25 TF) and filtrate was purified by a reverse phase HPLC-MS method using a Luna $C_{18}$ (2) column (75×30 mm, 5 µm particle size) sold by Phenomenex (pn: 00C-4252-U0-AX), and a dual gradient run from 50%-99% mobile phase B over 15.0 min (mobile phase A=water (5 mM hydrochloric acid), mobile phase B=acetonitrile. Flow rate=50 mL/min, injection volume=950 µL and column temperature=25° C.) to afford 12,12-dimethyl-8-(3-{2-[1-(trifluoromethyl)cyclopropyl]ethoxy}-1H-pyrazol-1-yl)-

845

2λ⁶-thia-3,9,11,18,22-pentaazatetracyclo[17.3.1.111,14.05,10]tetracosa-1(23),5(10),6,8,19,21-hexaene-2,2,4-trione (hydrochloride salt) (Compound 23) (1.6 mg, 9%) as white solid. ESI-MS m/z calc. 633.2345, found 634.6 (M+1)⁺; Retention time: 2.15 min (LC Method B).

Example 115: Preparation of 6,6-dimethyl-10-(3-{2-[1-(trifluoromethyl)cyclopropyl]ethoxy}-1H-pyrazol-1-yl)-16λ⁶-thia-2,7,9,15,21-pentaazatetracyclo[15.3.1.14,7.08,13]docosa-1(20),8,10,12,17(21),18-hexaene-14,16,16-trione (Compound 17)

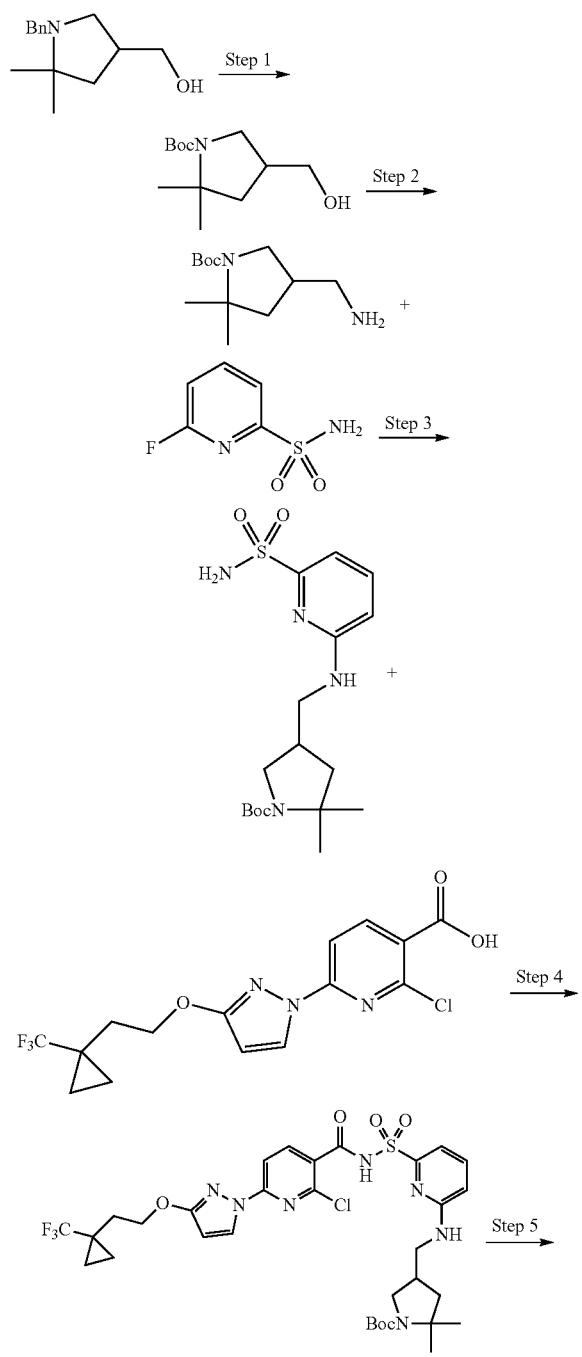

846

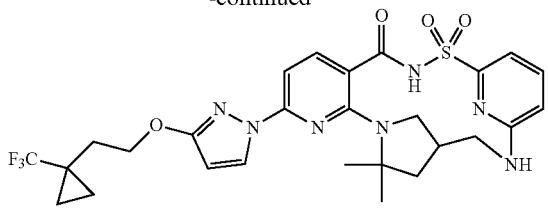

Step 1: tert-Butyl 4-(hydroxymethyl)-2,2-dimethylpyrrolidine-1-carboxylate

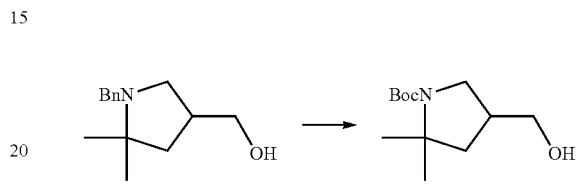

(1-Benzyl-5,5-dimethylpyrrolidin-3-yl)methanol (1 g, 4.56 mmol) was dissolved in EtOH (40 mL), 20% Pd(OH)₂ on carbon (400 mg) was added and the reaction mixture was stirred under hydrogen atmosphere at 20° C. for 24 h. The catalyst was filtered off over Celite. The filter cake was washed with ethyl acetate and the filtrate concentrated. The crude intermediate was dissolved in tetrahydrofuran/water (50 mL/50 mL) and potassium carbonate (3.1 g, 22.8 mmol) was added followed by Boc₂O (1.22 g, 4.56 mmol) at 0° C. The reaction mixture was allowed to warm to 20° C. over 16 h then poured into water and extracted with ethyl acetate (3×20 mL). The combined organic layers were dried over sodium sulfate, filtered and concentrated. Pure tert-butyl 4-(hydroxymethyl)-2,2-dimethylpyrrolidine-1-carboxylate (1.04 g, quant.) was obtained as a colorless oil after silica gel purification (30% ethyl acetate in heptanes eluent). ¹H NMR (300 MHz, CDCl₃): δ 3.6 (m, 4H); 3.1 (m, 1H); 2.4 (m, 1H); 1.9 (m, 1H); 1.4 (m, 15H).

Step 2: tert-Butyl 4-(aminomethyl)-2,2-dimethylpyrrolidine-1-carboxylate

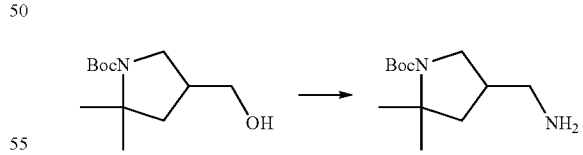

MsCl (0.57 mL, 7.3 mmol) was added slowly to a solution of tert-butyl 4-(hydroxymethyl)-2,2-dimethylpyrrolidine-1-carboxylate (1.4 g, 6.1 mmol) and DIPEA (1.6 mL, 9.15 mmol) in dichloromethane (30 mL) at 0° C. The reaction mixture was stirred for 1 h, water was added, the layers separated and the aqueous layer was extracted with dichloromethane (2×10 mL). The combined organic layers were dried over sodium sulfate, filtered and concentrated. The crude mesylate was dissolved in N,N-dimethylformamide (20 mL), NaN₃ (600 mg, 9.15 mmol) was added and the reaction mixture was stirred in a closed vessel at 100° C. for 16 h. The reaction mixture was poured into water and extracted with ethyl acetate (3×20 mL). The combined organic layers were washed with brine, dried over sodium sulfate, filtered and concentrated. The crude azide was dissolved in tetrahydrofuran/water (18/2 mL), PPh₃ (2.4 g, 9.15 mmol) was added and the reaction mixture was stirred at 50° C. for 3 h. The reaction mixture was cooled down, carefully acidified to pH=3 with 4 N aqueous hydrochloric acid and quickly washed with ethyl acetate (2×20 mL). The aqueous layer was basified to pH=10 and extracted with ethyl acetate (3×10 mL). The combined organic layers were dried over sodium sulfate, filtered and concentrated giving tert-butyl 4-(aminomethyl)-2,2-dimethylpyrrolidine-1-carboxylate was obtained (600 mg, 43%) as a yellow oil after silica gel purification (5% methanol in dichloromethane eluent). ¹H NMR (300 MHz, CDCl₃): δ 3.7 (m, 1H); 3.0 (m, 1H); 2.7 (m, 2H); 2.2 (m, 1H); 1.9 (m, 1H); 1.4 (m, 15H).

Step 3: tert-Butyl 2,2-dimethyl-4-[[(6-sulfamoyl-2-pyridyl)amino]methyl]pyrrolidine-1-carboxylate

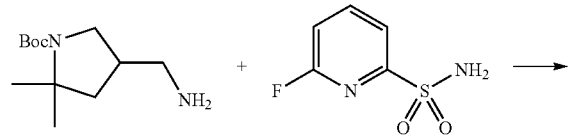

In a 20 mL vial was combined 6-fluoropyridine-2-sulfonamide (340 mg, 1.9 mmol) in dimethyl sulfoxide (4.0 mL) followed by potassium carbonate (1.3 g, 9.4 mmol) and tert-butyl 4-(aminomethyl)-2,2-dimethyl-pyrrolidine-1-carboxylate (460 mg, 2.0 mmol). The vial was capped and heated to 100° C. on a hot plate for 16 h. The reaction mixture was cooled to room temperature then filtered and diluted with ethyl acetate and washed with a 1 M citric acid solution, followed by brine. The organics were separated, dried over sodium sulfate, filtered and evaporated and then purified by silica gel chromatography using a gradient from 100% hexanes to 80% ethyl acetate in hexanes to give tert-butyl 2,2-dimethyl-4-[[(6-sulfamoyl-2-pyridyl)amino]methyl]pyrrolidine-1-carboxylate (222 mg, 30%) as a white solid. ¹H NMR (400 MHz, dimethyl sulfoxide-d₆) δ 7.53 (dd, J=8.4, 7.3 Hz, 1H), 7.10 (s, 2H), 7.06 (d, J=5.5 Hz, 1H), 6.97 (d, J=6.9 Hz, 1H), 6.64 (d, J=8.1 Hz, 1H), 3.65-3.54 (m, 1H), 3.17 (d, J=5.2 Hz, 2H), 2.95 (t, J=10.1 Hz, 1H), 2.47-2.35 (m, 1H), 2.00-1.86 (m, 1H), 1.55 (dt, J=32.7, 12.1 Hz, 1H), 1.42-1.36 (m, 12H), 1.25 (s, 3H). ESI-MS m/z calc. 384.18314, found 385.2 (M+1)⁺; Retention time: 1.46 min (LC Method E).

Step 4: tert-Butyl 4-[[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]methyl]-2,2-dimethyl-pyrrolidine-1-carboxylate

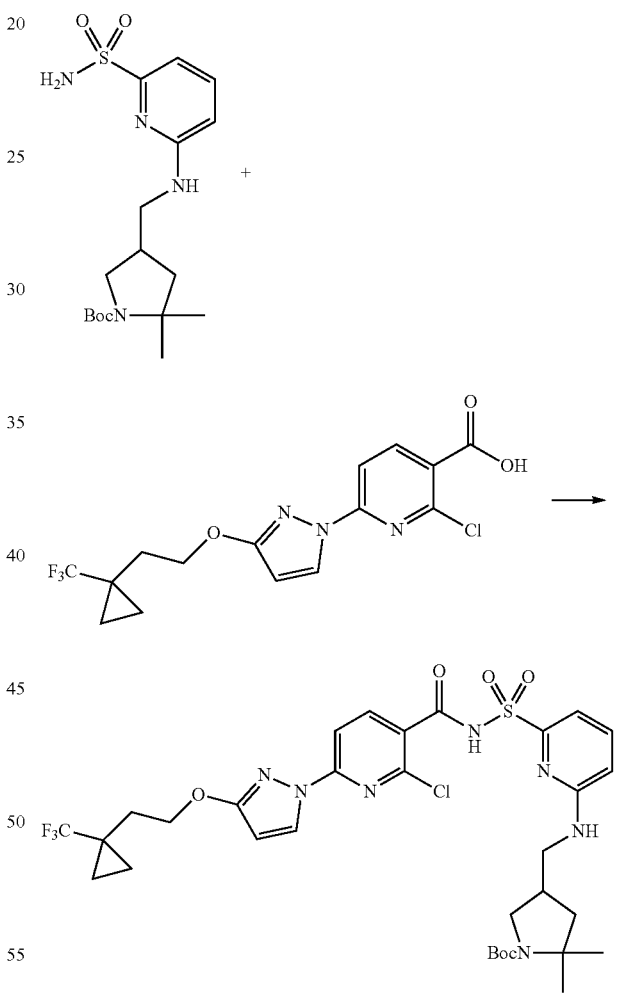

2-Chloro-6-[3-[2-[1-(trifluoromethyl)cyclopropyl]ethoxy]pyrazol-1-yl]pyridine-3-carboxylic acid (202 mg, 0.538 mmol) and carbonyl diimidazole (87.5 mg, 0.540 mmol) were combined in tetrahydrofuran (3.0 mL) and stirred for 2 h at 45° C. Then tert-butyl 2,2-dimethyl-4-[[(6-sulfamoyl-2-pyridyl)amino]methyl]pyrrolidine-1-carboxylate (207 mg, 0.538 mmol) was added followed by 1,8-diazabicyclo[5.4.0]undec-7-ene (175 μL, 1.17 mmol) and the reaction was heated at 50° C. for 16 h. The reaction was diluted with ethyl acetate and washed with a 1 M citric acid solution, followed by brine. The organics were separated, dried over sodium sulfate, filtered and evaporated then purified by silica gel chromatography using a gradient from 100% hexanes to 70% ethyl acetate in hexanes to afford tert-butyl 4-[[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]methyl]-2,2-dimethyl-pyrrolidine-1-carboxylate (234 mg, 59%) as a light yellow solid. $^1$H NMR (400 MHz, dimethyl sulfoxide-$d_6$) δ 12.79 (s, 1H), 8.40 (m, 1H), 8.09 (d, J=8.4 Hz, 1H), 7.70 (t, J=7.0 Hz, 1H), 7.63 (m, 1H), 7.28 (s, 1H), 7.19 (d, J=7.2 Hz, 1H), 6.77 (d, J=8.6 Hz, 1H), 6.19 (dd, J=4.4, 2.9 Hz, 1H), 4.34 (t, J=7.1 Hz, 2H), 3.55 (m, 1H), 3.26 (m, 2H), 2.91 (t, J=10.4 Hz, 1H), 2.41 (m, 1H), 2.09 (t, J=7.1 Hz, 3H), 1.86 (m, 1H), 1.50 (m, 1H), 1.35 (t, J=13.2 Hz, 12H), 1.18 (s, 3H), 0.95 (m, 2H), 0.89 (s, 2H). ESI-MS m/z calc. 741.2323, found 742.2 (M+1)$^+$; Retention time: 2.25 min (LC Method E).

Step 5: 6,6-Dimethyl-10-(3-{2-[1-(trifluoromethyl)cyclopropyl]ethoxy}-1H-pyrazol-1-yl)-16λ$^6$-thia-2,7,9,15,21-pentaazatetracyclo[15.3.1.14,7.08,13]docosa-1(20),8,10,12,17(21),18-hexaene-14,16,16-trione (Compound 17)

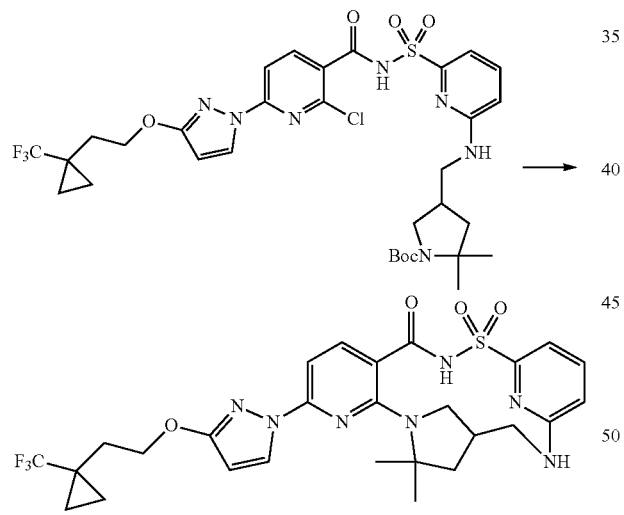

tert-Butyl 4-[[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]methyl]-2,2-dimethyl-pyrrolidine-1-carboxylate (234 mg, 0.315 mmol) was dissolved in dichloromethane (5.0 mL) and to the mixture was added hydrochloric acid (3.0 mL of 4 M in dioxane, 12.0 mmol) and stirred at room temperature for 2 h. Concentrated mixture to dryness under reduced pressure, redissolved in ethyl acetate and then added aqueous 2 M sodium carbonate (2 mL), pH~10. Extracted organic layer with ethyl acetate (2×5 mL), washed with brine, then dried over sodium sulfate, filtered and evaporated to dryness under reduced pressure. Combined this material and potassium carbonate (220 mg, 1.59 mmol), cesium fluoride (72.0 mg, 0.474 mmol), 3 Å molecular sieves and dimethyl sulfoxide (7.0 mL) in a vial, purged with nitrogen, capped, heated to 155° C. and stirred for 16 h. Cooled to room temperature and the reaction was diluted with ethyl acetate and washed with a 1 M citric acid solution, followed by brine. The organics were separated, dried over sodium sulfate, filtered and evaporated then purified by silica gel chromatography using a gradient from 100% hexanes to 80% ethyl acetate in hexanes to afford 6,6-dimethyl-10-(3-{2-[1-(trifluoromethyl)cyclopropyl]ethoxy}-1H-pyrazol-1-yl)-16λ$^6$-thia-2,7,9,15,21-pentaazatetracyclo[15.3.1.14,7.08,13]docosa-1(20),8,10,12,17(21),18-hexaene-14,16,16-trione (Compound 17) (111 mg, 57%) as a white solid. $^1$H NMR (400 MHz, dimethyl sulfoxide-$d_6$) δ 12.52 (s, 1H), 8.19 (d, J=2.7 Hz, 1H), 7.67-7.50 (m, 2H), 7.47 (d, J=8.1 Hz, 1H), 7.16 (d, J=7.2 Hz, 1H), 6.82 (d, J=8.1 Hz, 1H), 6.73 (d, J=8.5 Hz, 1H), 6.09 (d, J=2.7 Hz, 1H), 4.52 (t, J=9.8 Hz, 1H), 4.30 (t, J=7.0 Hz, 2H), 3.54-3.42 (m, 1H), 3.27-3.16 (m, 1H), 3.02 (t, J=8.7 Hz, 1H), 2.32 (dt, J=12.3, 5.7 Hz, 1H), 2.07 (dd, J=8.7, 5.4 Hz, 2H), 1.97 (dd, J=11.4, 5.8 Hz, 1H), 1.68 (s, 3H), 1.64 (d, J=12.2 Hz, 1H), 1.45 (s, 3H), 0.95 (t, J=5.8 Hz, 2H), 0.87 (s, 2H). ESI-MS m/z calc. 605.2032, found 606.4 (M+1)$^+$; Retention time: 2.02 min (LC Method E).

Example 116: Preparation of 6,6-dimethyl-10-(3-{2-[1-(trifluoromethyl)cyclopropyl]ethoxy}-1H-pyrazol-1-yl)-16λ$^6$-thia-2,7,9,15,21-pentaazatetracyclo[15.3.1.14,7.08,13]docosa-1(20),8,10,12,17(21), 18-hexaene-14,16,16-trione (Enantiomer 1) (Compound 24) and 6,6-dimethyl-10-(3-{2-[1-(trifluoromethyl)cyclopropyl]ethoxy}-1H-pyrazol-1-yl)-16λ$^6$-thia-2,7,9,15,21-pentaazatetracyclo[15.3.1.14,7.08,13]docosa-1(20),8,10,12,17(21),18-hexaene-14,16,16-trione (Enantiomer 2) (Compound 25)

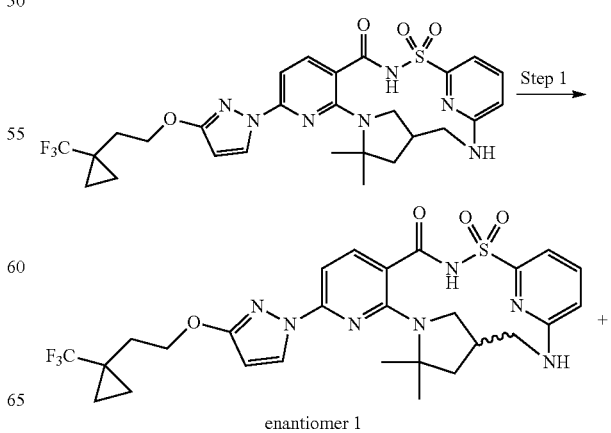

enantiomer 1

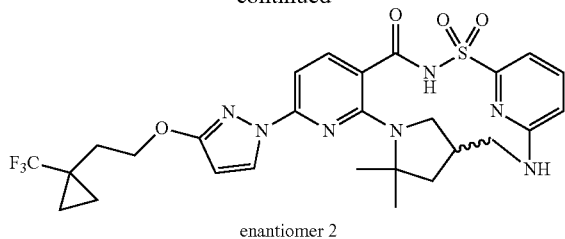

enantiomer 2

Step 1: 6,6-Dimethyl-10-(3-{2-[1-(trifluoromethyl)cyclopropyl]ethoxy}-1H-pyrazol-1-yl)-16λ⁶-thia-2,7,9,15,21-pentaazatetracyclo[15.3.1.1⁴,⁷.0⁸,¹³]docosa-1(20),8,10,12,17(21),18-hexaene-14,16,16-trione (Enantiomer 1) (Compound 24) and 6,6-dimethyl-10-(3-{2-[1-(trifluoromethyl)cyclopropyl]ethoxy}-1H-pyrazol-1-yl)-16λ⁶-thia-2,7,9,15,21-pentaazatetracyclo[15.3.1.1⁴,⁷.0⁸,¹³]docosa-1(20),8,10,12,17(21),18-hexaene-14,16,16-trione (Enantiomer 2) (Compound 25)

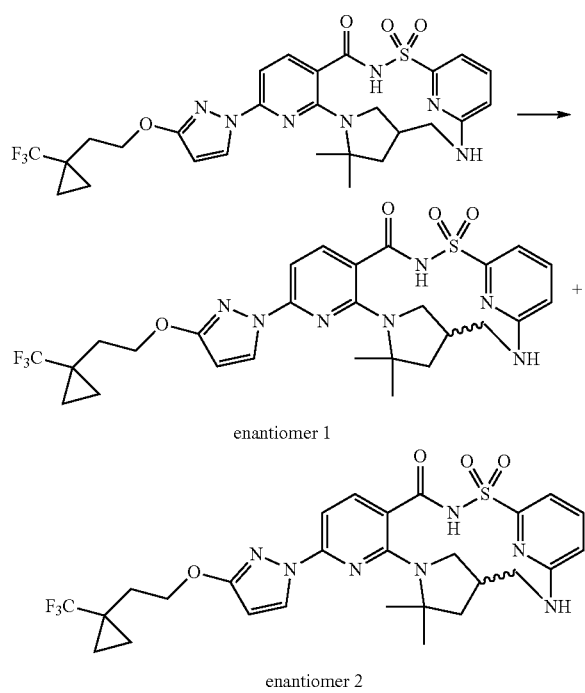

Racemic 6,6-dimethyl-10-(3-{2-[1-(trifluoromethyl)cyclopropyl]ethoxy}-1H-pyrazol-1-yl)-16λ⁶-thia-2,7,9,15,21-pentaazatetracyclo[15.3.1.1⁴,⁷.0⁸,¹³]docosa-1(20),8,10,12,17(21),18-hexaene-14,16,16-trione (131 mg) was subjected to chiral SFC chromatography using a ChiralPak AS-H (250×21.2 mm column, 5 μm particle size) with 15% acetonitrile:methanol (90:10)/85% carbon dioxide mobile phase at 10 mL/min giving as the first enantiomer to elute, 6,6-dimethyl-10-(3-{2-[1-(trifluoromethyl)cyclopropyl]ethoxy}-1H-pyrazol-1-yl)-16λ⁶-thia-2,7,9,15,21-pentaazatetracyclo[15.3.1.1⁴,⁷.0⁸,¹³]docosa-1(20),8,10,12,17(21),18-hexaene-14,16,16-trione (enantiomer 1) (Compound 24) (29.04 mg, 69%) as an off-white solid; ¹H NMR (400 MHz, dimethyl sulfoxide-d₆) δ 12.52 (s, 1H), 8.19 (d, J=2.7 Hz, 1H), 7.61 (dd, J=10.5, 5.2 Hz, 2H), 7.47 (d, J=8.1 Hz, 1H), 7.16 (d, J=7.2 Hz, 1H), 6.82 (d, J=8.1 Hz, 1H), 6.73 (d, J=8.5 Hz, 1H), 6.09 (d, J=2.7 Hz, 1H), 4.51 (t, J=10.0 Hz, 1H), 4.30 (t, J=7.0 Hz, 2H), 3.58-3.38 (m, 1H), 3.22 (d, J=5.6 Hz, 1H), 3.09-2.95 (m, 1H), 2.40-2.20 (m, 1H), 2.07 (t, J=7.0 Hz, 2H), 1.97 (dd, J=12.2, 6.2 Hz, 1H), 1.74-1.60 (m, 4H), 1.45 (s, 3H), 0.95 (t, J=5.7 Hz, 2H), 0.89 (d, J=11.5 Hz, 2H), ESI-MS m/z calc. 605.2032, found 606.2 (M+1)⁺; Retention time: 2.03 min (LC Method E) and as the second enantiomer to elute, 6,6-dimethyl-10-(3-{2-[1-(trifluoromethyl)cyclopropyl]ethoxy}-1H-pyrazol-1-yl)-16λ⁶-thia-2,7,9,15,21-pentaazatetracyclo[15.3.1.1⁴,⁷.0⁸,¹³]docosa-1(20),8,10,12,17(21),18-hexaene-14,16,16-trione (enantiomer 2) (Compound 25) (28.84 mg, 68%) as an off-white solid; ¹H NMR (400 MHz, dimethyl sulfoxide-d₆) δ 12.52 (s, 1H), 8.19 (d, J=2.7 Hz, 1H), 7.61 (dd, J=10.3, 5.4 Hz, 2H), 7.47 (d, J=8.1 Hz, 1H), 7.16 (d, J=7.2 Hz, 1H), 6.82 (d, J=8.1 Hz, 1H), 6.73 (d, J=8.4 Hz, 1H), 6.09 (d, J=2.7 Hz, 1H), 4.51 (t, J=9.9 Hz, 1H), 4.30 (t, J=7.0 Hz, 2H), 3.58-3.41 (m, 1H), 3.22 (dd, J=12.0, 5.7 Hz, 1H), 3.02 (t, J=8.6 Hz, 1H), 2.31 (dd, J=15.2, 6.3 Hz, 1H), 2.07 (t, J=7.0 Hz, 2H), 1.97 (dd, J=12.1, 6.3 Hz, 1H), 1.71-1.59 (m, 4H), 1.45 (s, 3H), 0.95 (t, J=5.7 Hz, 2H), 0.89 (d, J=11.5 Hz, 2H), ESI-MS m/z calc. 605.2032, found 606.2 (M+1)⁺; Retention time: 2.03 min (LC Method E).

Example 117: Preparation of 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.1⁵,⁸.0⁹,¹⁴]tricosa-1(21),9,11,13,18(22),19-hexaene-15,17,17-trione (Enantiomer 1) (Compound 26) and 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.1⁵,⁸.0⁹,¹⁴]tricosa-1(21),9,11,13,18(22),19-hexaene-15,17,17-trione (Enantiomer 2) (Compound 27)

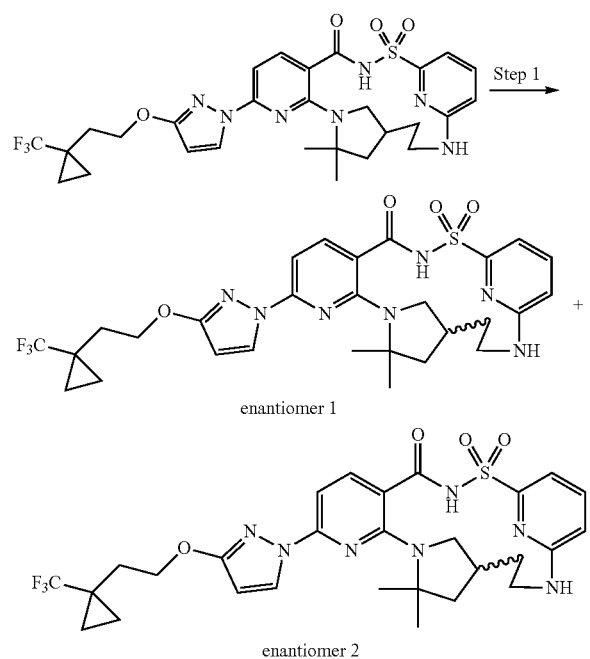

Step 1: 7,7-Dimethyl-11-(3-{2-[1-(trifluoromethyl) cyclopropyl]ethoxy}-1H-pyrazol-1-yl)-17λ⁶-thia-2, 8,10,16,22-pentaazatetracyclo[16.3.1.1⁵,⁸.0⁹,¹⁴] tricosa-1(21),9,11,13,18(22),19-hexaene-15,17,17-trione (Enantiomer 1) (Compound 26) and 7,7-dimethyl-11-(3-{2-[1-(trifluoromethyl)cyclopropyl] ethoxy}-1H-pyrazol-1-yl)-17λ⁶-thia-2,8,10,16,22-pentaazatetracyclo[16.3.1.1⁵,⁸.0⁹,¹⁴]tricosa-1(21),9, 11,13,18(22),19-hexaene-15,17,17-trione (Enantiomer 2) (Compound 27)

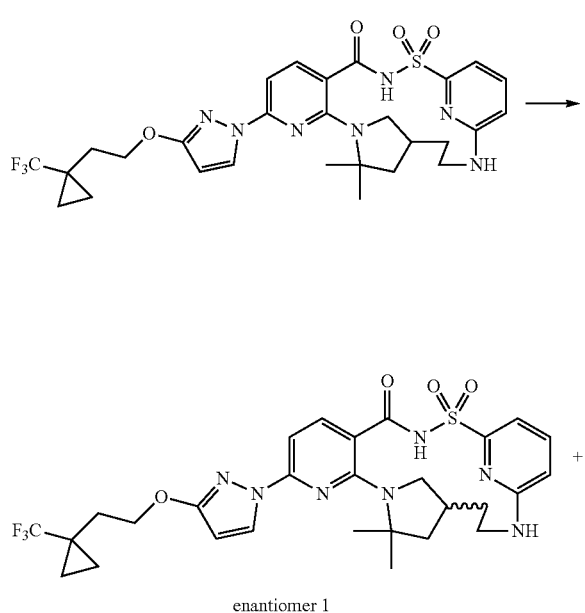

enantiomer 1

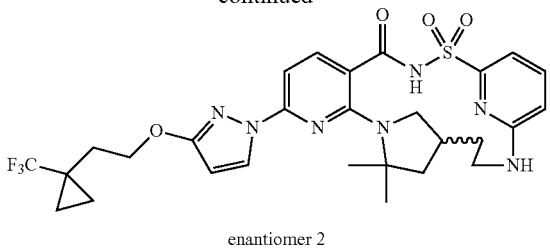

enantiomer 2

Racemic 7,7-dimethyl-11-(3-{2-[1-(trifluoromethyl)cyclopropyl]ethoxy}-1H-pyrazol-1-yl)-17λ⁶-thia-2,8,10,16, 22-pentaazatetracyclo[16.3.1.1⁵,⁸.0⁹,¹⁴]tricosa-1(21),9,11, 13,18(22),19-hexaene-15,17,17-trione (85 mg, 0.1372 mmol) was subjected to chiral SFC chromatography using a ChiralPak AS-H (250×21.2 mm column, 5 μm particle size) with 20% methanol (No modifier))/80% carbon dioxide mobile phase at 10 mL/min giving as the first enantiomer to elute, 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.1⁵,⁸.0⁹,¹⁴]tricosa-1(21),9,11,13,18 (22),19-hexaene-15,17,17-trione (enantiomer 1) (Compound 26) (24.1 mg, 28%); ESI-MS m/z calc. 619.2189, found 620.2 (M+1)⁺; Retention time: 2.07 min (LC Method B) and as the second enantiomer to elute, 7,7-dimethyl-11-(3-{2-[1-(trifluoromethyl)cyclopropyl] ethoxy}-1H-pyrazol-1-yl)-17λ⁶-thia-2,8,10,16,22-pentaazatetracyclo[16.3.1.1⁵,⁸.0⁹,¹⁴]tricosa-1(21),9,11,13,18(22), 19-hexaene-15,17,17-trione (enantiomer 2) (Compound 27) (26 mg, 31%); ESI-MS m/z calc. 619.2189, found 620.2 (M+1)⁺; Retention time: 2.06 min (LC Method B).

Example 118: Preparation of 4-chloro-20,20-dimethyl-10λ⁶-thia-1,3,9,14,22-pentaazatetracyclo [16.2.1.1¹¹,¹⁴.0²,⁷]docosa-2,4,6,11(22),12-pentaene-8,10,10-trione (Compound A) and 4-chloro-21,21-dimethyl-10λ⁶-thia-1,3,9,14,15-pentaazatetracyclo[17.2.1.0²,⁷.0¹¹,¹⁵]docosa-2,4,6, 11,13-pentaene-8,10,10-trione (Compound B)

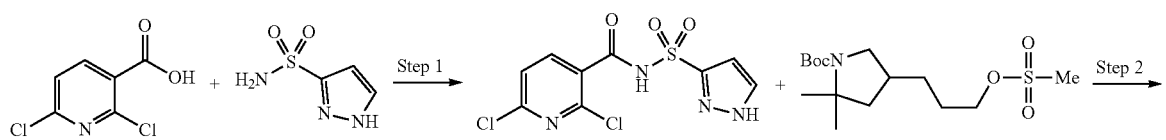

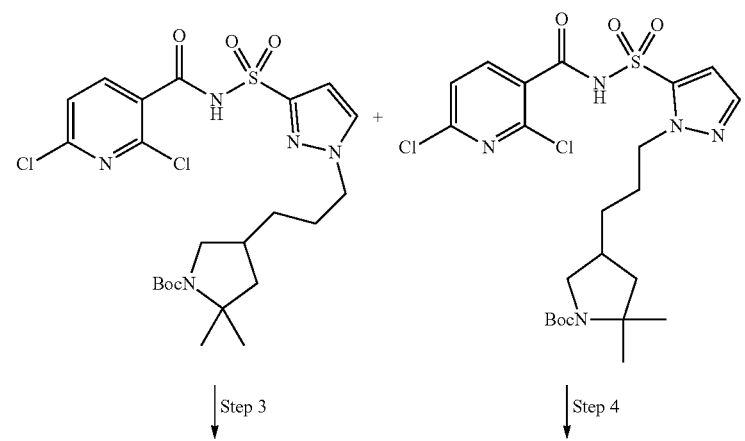

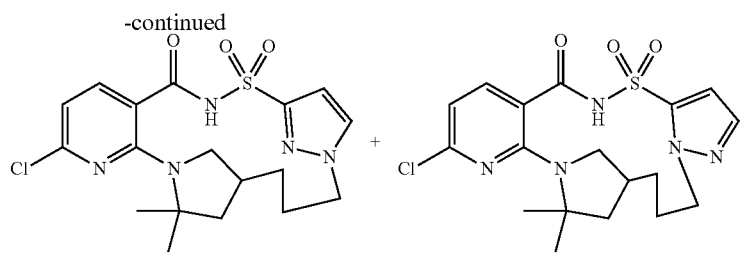

Step 1: 2,6-Dichloro-N-(1H-pyrazol-3-ylsulfonyl) pyridine-3-carboxamide

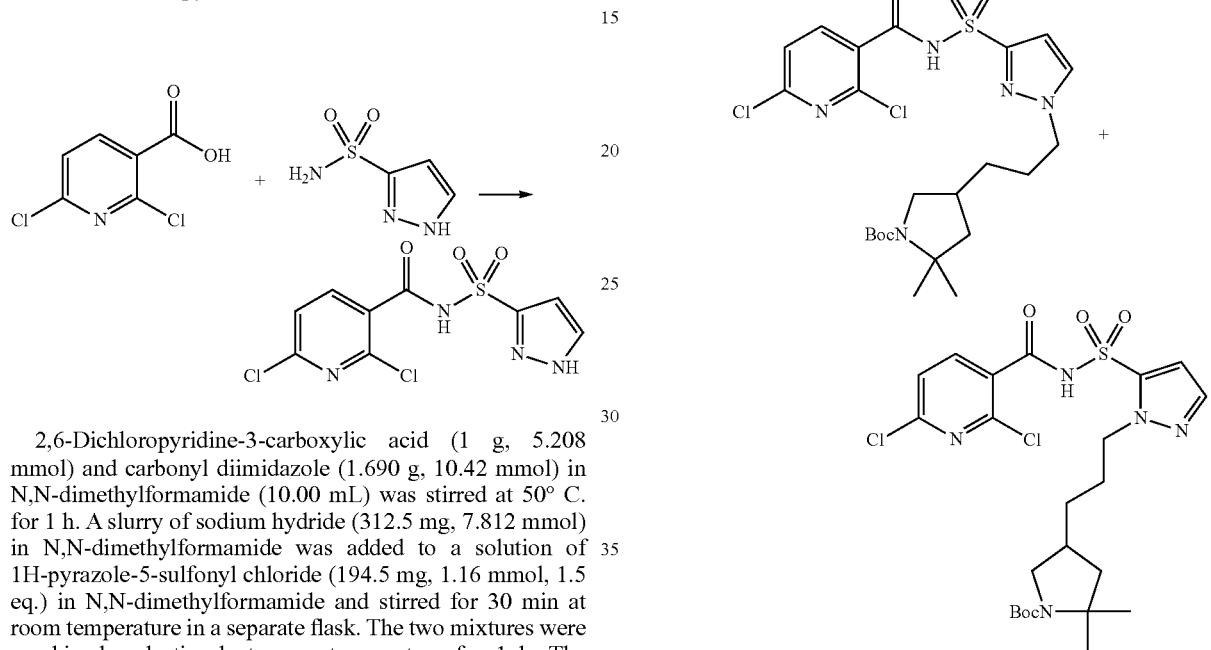

2,6-Dichloropyridine-3-carboxylic acid (1 g, 5.208 mmol) and carbonyl diimidazole (1.690 g, 10.42 mmol) in N,N-dimethylformamide (10.00 mL) was stirred at 50° C. for 1 h. A slurry of sodium hydride (312.5 mg, 7.812 mmol) in N,N-dimethylformamide was added to a solution of 1H-pyrazole-5-sulfonyl chloride (194.5 mg, 1.16 mmol, 1.5 eq.) in N,N-dimethylformamide and stirred for 30 min at room temperature in a separate flask. The two mixtures were combined and stirred at room temperature for 1 h. The reaction mixture was poured over ice and acidified to pH=2 by addition of aqueous 4 M hydrochloric acid. The resulting mixture was extracted with ethyl acetate, the organic layer was dried over sodium sulfate, filtered and volatiles were removed by rotary evaporation. The crude material was purified by silica gel chromatography eluting with 10% methanol in dichloromethane giving 2,6-dichloro-N-(1H-pyrazol-3-ylsulfonyl)pyridine-3-carboxamide (1.341 g, 68%). ESI-MS m/z calc. 319.95377, found 321.0 (M+1)+; Retention time: 0.34 min (LC Method A).

Step 2: tert-Butyl 4-[3-[3-[(2,6-dichloropyridine-3-carbonyl)sulfamoyl]pyrazol-1-yl]propyl]-2,2-dimethyl-pyrrolidine-1-carboxylate

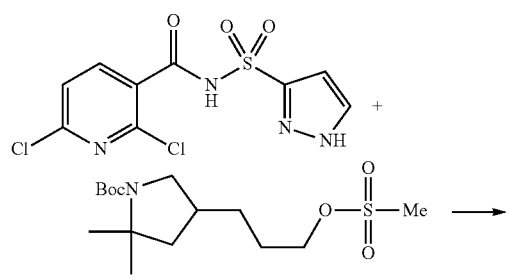

To a solution of tert-butyl 2,2-dimethyl-4-(3-methylsulfonyloxypropyl) pyrrolidine-1-carboxylate (300 mg, 0.894 mmol) in N,N-dimethylformamide (6.00 mL) was added 2,6-dichloro-N-(1H-pyrazol-3-ylsulfonyl)pyridine-3-carboxamide (300 mg, 0.934 mmol) followed by cesium carbonate (875 mg, 2.69 mmol) and the reaction mixture was stirred at 60° C. for 16 h. The reaction mixture was cooled to room temperature and poured into water (100 mL) and extracted with ethyl acetate (2×100 mL). Combined the organic layers, washed with water (2×100 mL), dried (sodium sulfate), filtered and concentrated. The resultant brown residue was purified by silica gel column chromatography using a shallow gradient from 100% hexanes to 100% ethyl acetate to afford as the first regioisomer to elute, tert-butyl 4-[3-[3-[(2,6-dichloropyridine-3-carbonyl)sulfamoyl]pyrazol-1-yl]propyl]-2,2-dimethyl-pyrrolidine-1-carboxylate (327 mg, 65%) as white solid; $^1$H NMR (400 MHz, dimethyl sulfoxide-$d_6$) δ 7.92 (d, J=8.0 Hz, 1H), 7.70 (d, J=2.2 Hz, 1H), 7.51-7.46 (m, 1H), 6.48 (d, J=2.3 Hz, 1H), 4.14-4.05 (m, 2H), 3.53 (dt, J=14.7, 10.3 Hz, 1H), 2.78-2.67 (m, 1H), 2.08 (dq, J=11.7, 5.9, 5.3 Hz, 1H), 1.39 (s, 4H), 1.34 (q, J=11.5, 8.4 Hz, 12H), 1.22 (s, 3H), ESI-MS m/z calc. 559.1423, found 560.5 (M+1)+; Retention time: 0.71 min (LC Method A) and as the second regioisomer to elute, tert-butyl 4-[3-[5-[(2,6-dichloropyridine-3-carbonyl)sulfamoyl]pyrazol-1-yl]propyl]-2,2-dimethyl-pyrrolidine-1-carboxylate (126 mg, 25%) as a viscous colorless oil; $^1$H NMR (400 MHz, dimethyl sulfoxide-$d_6$) δ 8.01 (dd, J=8.0, 5.0 Hz, 1H), 7.95 (s, 1H), 7.50 (dd, J=7.9, 1.5 Hz, 1H), 7.37 (d, J=1.9 Hz, 1H), 6.50 (d, J=1.9 Hz, 1H), 4.34 (t, J=7.3 Hz, 2H), 3.46 (dt, J=14.4, 9.9 Hz, 1H), 2.66 (td, J=10.4, 4.7 Hz, 1H), 1.99 (s, OH), 1.76 (dt, J=17.9, 8.3 Hz, 3H), 1.38 (d, J=12.7 Hz, 9H), 1.30 (d, J=10.5 Hz, 3H), 1.17 (d, J=2.3 Hz, 3H), ESI-MS m/z calc. 559.1423, found 560.5 (M+1)$^+$; Retention time: 0.74 min (LC Method A).

Step 3: 4-Chloro-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Compound A)

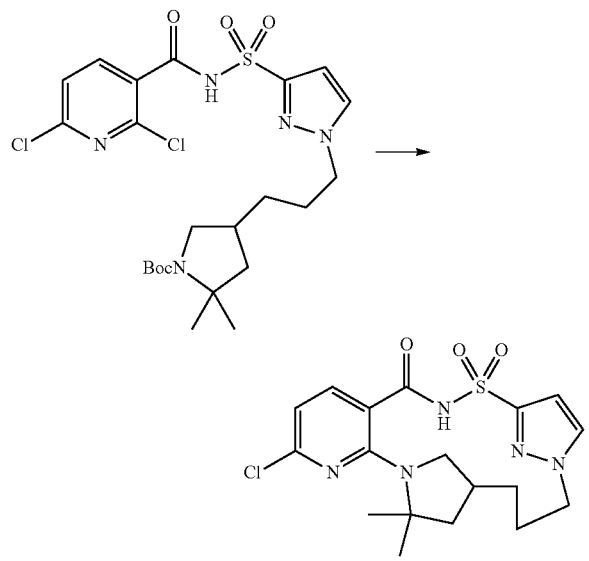

A solution of tert-butyl 4-[3-[5-[(2,6-dichloropyridine-3-carbonyl)sulfamoyl]pyrazol-1-yl]propyl]-2,2-dimethyl-pyrrolidine-1-carboxylate (100 mg, 0.1784 mmol) in dichloromethane (2 mL) and trifluoroacetic acid (150 µL, 1.960 mmol) was stirred at room temperature for 4 h. The solvents were removed by evaporation and 2 M NH$_3$ in methanol (10 mL) was added and the reaction mixture was stirred for 30 min and then concentrated and dried under vacuum. The above residue was dissolved in dimethyl sulfoxide (2 mL) and 3 Å molecular sieves were added and the reaction mixture was stirred for 10 min. Then, cesium fluoride (85 mg, 0.5596 mmol) and potassium carbonate (78 mg, 0.5644 mmol) were added and the reaction mixture was heated at 140° C. for overnight. The reaction mixture was filtered through a Whatman filter disc (puradisc 25 TF) and the filtrate was purified by reverse phase HPLC-MS (Luna C$_{18}$ (2) column (75×30 mm, 5 µm particle size) sold by Phenomenex (pn: 00C-4252-U0-AX), and a dual gradient run from 50%-99% mobile phase B over 15.0 min, mobile phase A=water (5 mM hydrochloric acid), mobile phase B=acetonitrile. Flow rate=50 mL/min, injection volume=950 µL, and column temperature=25° C.) to afford 4-chloro-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (28 mg, 12%) as a white solid. $^1$H NMR (400 MHz, Chloroform-d) δ 8.77 (s, 1H), 7.54-7.44 (m, 2H), 7.07 (d, J=2.3 Hz, 1H), 6.48 (d, J=7.9 Hz, 1H), 4.36-4.24 (m, 1H), 4.06-3.85 (m, 1H), 2.67 (t, J=8.3 Hz, 1H), 2.14 (ddt, J=17.7, 12.1, 6.2 Hz, 2H), 2.07-2.01 (m, 1H), 1.98-1.84 (m, 2H), 1.73 (ddd, J=12.1, 5.5, 1.5 Hz, 1H), 1.55 (s, 3H), 1.50 (s, 3H), 1.44 (t, J=12.3 Hz, 1H), 0.86-0.69 (m, 1H). ESI-MS m/z calc. 423.1132, found 424.4 (M+1)$^+$; Retention time: 1.76 min (LC Method B).

Step 4: 4-Chloro-21,21-dimethyl-10λ$^6$-thia-1,3,9,14,15-pentaazatetracyclo[17.2.1.0$^{2,7}$.0$^{11,15}$]docosa-2,4,6,11,13-pentaene-8,10,10-trione (Compound B)

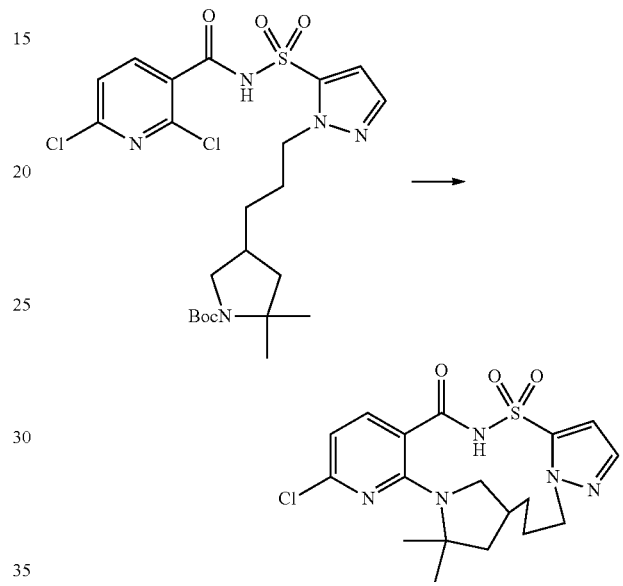

A solution of tert-butyl 4-[3-[3-1(2,6-dichloropyridine-3-carbonyl)sulfamoyl]pyrazol-1-yl]propyl]-2,2-dimethyl-pyrrolidine-1-carboxylate (100 mg, 0.1784 mmol) in dichloromethane (2 mL) and trifluoroacetic acid (150 µL, 1.960 mmol) was stirred at room temperature for 4 h. After completion of the reaction the solvents were removed by evaporation and 2 M NH$_3$ in methanol (10 mL) was added and the reaction mixture was stirred for 30 min and concentrated then dried under vacuum. The residue was dissolved in dimethyl sulfoxide (2 mL) and 3 Å molecular sieves were added and the reaction mixture was stirred for 10 min. Then, cesium fluoride (85 mg, 0.5596 mmol) and potassium carbonate (78 mg, 0.5644 mmol) were added and the reaction mixture was heated at 140° C. for overnight. The reaction mixture was filtered through a Whatman filter disc (puradisc 25 TF) and the filtrate was purified by reverse phase HPLC-MS (Luna C$_{18}$ (2) column (75×30 mm, 5 µm particle size) sold by Phenomenex (pn: 00C-4252-U0-AX), and a dual gradient run from 50%-99% mobile phase B over 15.0 min, mobile phase A=water (5 mM hydrochloric acid), mobile phase B=acetonitrile. Flow rate=50 mL/min, injection volume=950 µL, and column temperature=25° C.) to afford 4-chloro-21,21-dimethyl-10λ$^6$-thia-1,3,9,14,15-pentaazatetracyclo[17.2.1.0$^{2,7}$.0$^{11,15}$]docosa-2,4,6,11,13-pentaene-8,10,10-trione (10.2 mg, 4%) as an off white solid. $^1$H NMR (400 MHz, Chloroform-d) δ 9.16 (s, 1H), 7.76 (d, J=8.0 Hz, 1H), 7.57 (d, J=2.1 Hz, 1H), 7.35 (d, J=2.1 Hz, 1H), 6.82 (d, J=8.0 Hz, 1H), 4.78 (dt, J=13.8, 4.0 Hz, 1H), 4.41-4.29 (m, 1H), 3.20 (t, J=9.7 Hz, 1H), 2.62-2.56 (m, 1H), 2.52 (s, 1H), 2.21-2.06 (m, 1H), 1.91 (s, 1H), 1.81-1.69

(m, 3H), 1.63 (s, 4H), 1.45 (s, 3H). ESI-MS m/z calc. 423.1132, found 424.4 (M+1)⁺; Retention time: 1.9 min (LC Method B).

Example 119: Preparation of 20,20-dimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Compound 32)

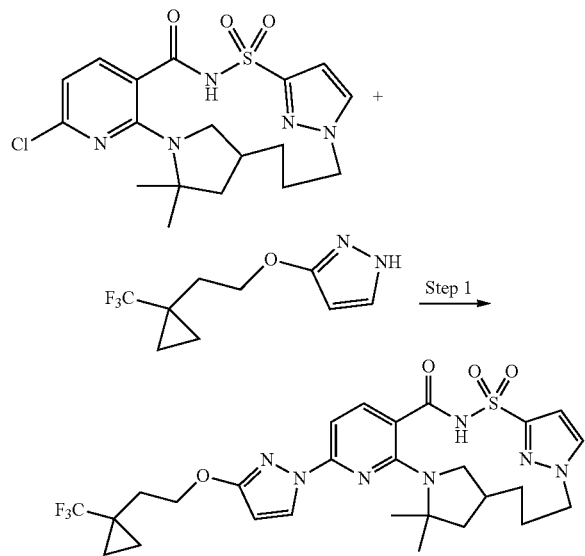

Step 1: 20,20-Dimethyl-4-(3-{2-[1-(trifluoromethyl) cyclopropyl]ethoxy}-1H-pyrazol-1-yl)-10λ⁶-thia-1, 3,9,14,22-pentaazatetracyclo[16.2.1.1¹¹,¹⁴.0²,⁷] docosa-2(7),3,5,11(22),12-pentaene-8,10,10-trione (Compound 32)

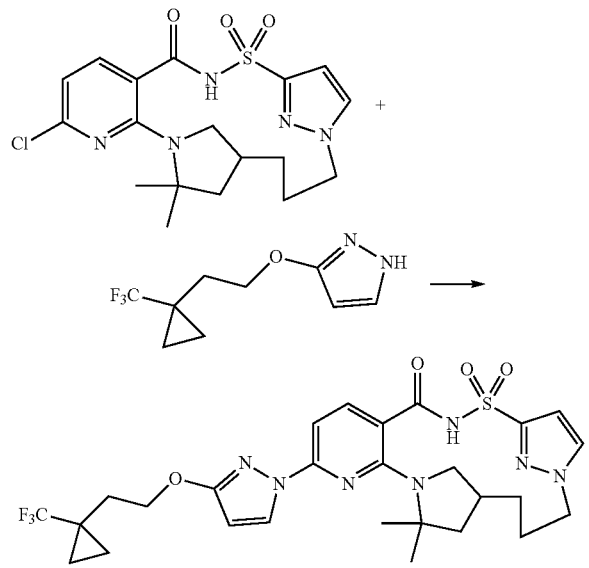

A solution of 4-chloro-20,20-dimethyl-10λ⁶-thia-1,3,9,14,22-pentaazatetracyclo[16.2.1.1¹¹,¹⁴.0²,⁷]docosa-2,4,6, 11(22),12-pentaene-8,10,10-trione (20 mg, 0.04718 mmol), scandium triflate, 3-[2-[1-(trifluoromethyl)cyclopropyl] ethoxy]-1H-pyrazole (31.16 mg, 0.1415 mmol) and NaH (9.435 mg of 60% w/w, 0.2359 mmol) in dimethyl sulfoxide (2.0 mL) was stirred at 140° C. for 16 h. The reaction mixture was quenched with few drops of water and filtered through a Whatman filter disc (puradisc 25 TF) and the filtrate was purified using a reverse phase HPLC-MS method using a Luna C₁₈ (2) column (75×30 mm, 5 μm particle size) sold by Phenomenex (pn: 00C-4252-U0-AX), and a dual gradient run from 1-99% mobile phase B over 15.0 min (mobile phase A=water (5 mM hydrochloric acid), mobile phase B=acetonitrile. Flow rate=50 mL/min, and column temperature=25° C.) to afford 20,20-dimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.02, 7]docosa-2(7),3,5,11(22),12-pentaene-8,10,10-trione (Compound 32) (2.4 mg, 8%) as white solid. ¹H NMR (400 MHz, Chloroform-d) δ 8.49 (s, 1H), 8.17 (d, J=2.7 Hz, 1H), 7.69 (d, J=8.3 Hz, 1H), 7.49 (s, 1H), 7.08 (d, J=2.1 Hz, 1H), 7.01 (d, J=8.2 Hz, 1H), 5.87 (d, J=2.7 Hz, 1H), 4.39 (t, J=7.1 Hz, 2H), 4.35 (s, 1H), 3.94 (t, J=12.9 Hz, 1H), 2.78-2.72 (m, 1H), 2.20-2.13 (m, 2H), 2.10 (d, J=7.0 Hz, 2H), 1.99 (t, J=10.3 Hz, 3H), 1.79-1.74 (m, 1H), 1.59 (s, 3H), 1.55 (s, 3H), 1.47 (t, J=12.0 Hz, 2H), 1.04-1.00 (m, 2H), 0.77-0.73 (m, 2H). ESI-MS m/z calc. 607.2189, found 608.6 (M+1)⁺; Retention time: 2.18 min (LC Method E).

Example 120: Preparation of (15S)-12,12-dimethyl-8-(3-{2-[1-(trifluoromethyl) cyclopropyl]ethoxy}-1H-pyrazol-1-yl)-2λ⁶-thia-3,9,11,19,24-pentaaza tetracyclo[18.3.1.0⁵,¹⁰.0¹¹,¹⁵]tetracosa-1(23),5,7,9,20(24),21-hexaene-2,2,4-trione (Compound 33) and (15R)-12,12-dimethyl-8-(3-{2-[1-(trifluoromethyl) cyclopropyl]ethoxy}-1H-pyrazol-1-yl)-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 34)

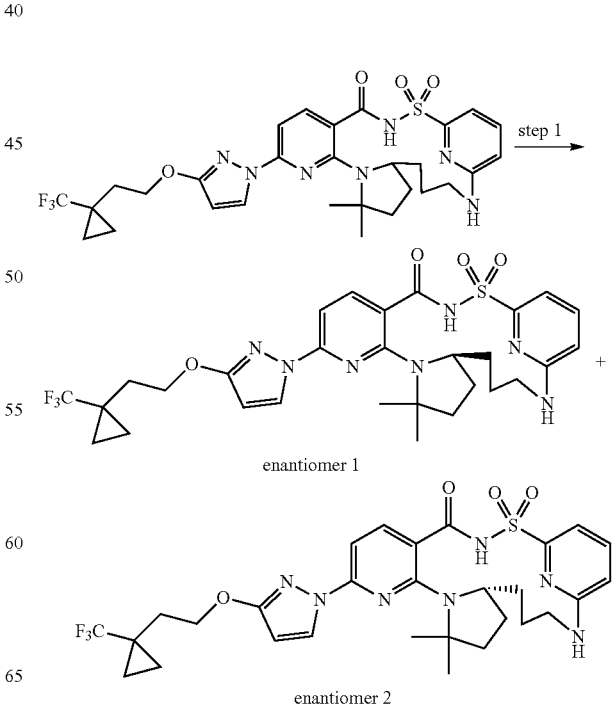

enantiomer 1 enantiomer 2

Step 1: (15S)-12,12-Dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 33) and (15R)-12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 34)

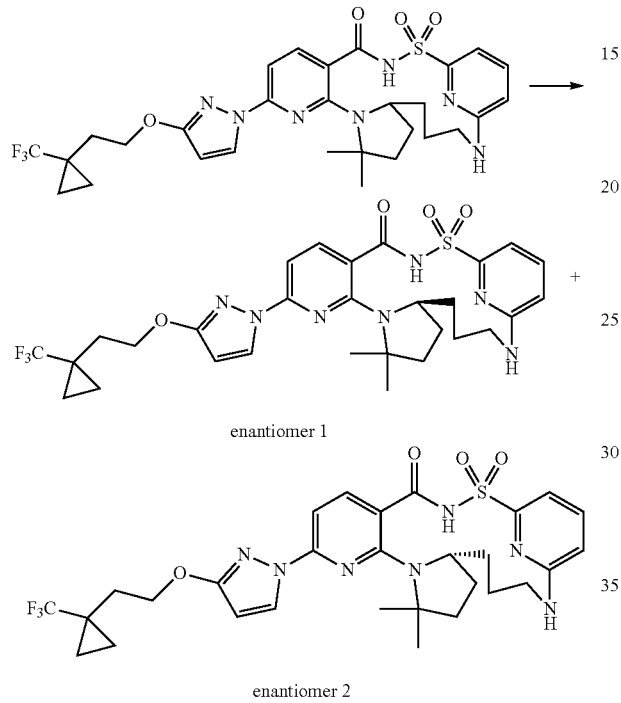

Racemic 12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (90 mg, 0.1420 mmol) was subjected to chiral SFC chromatography using a ChiralPak AS-H (250×10 mm column, 5 μm particle size) with 18% acetonitrile: methanol (90:10; No modifier))/82% carbon dioxide mobile phase at 10 mL/min giving as the first enantiomer to elute, (15S)-12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 33) (28.6 mg, 64%); ¹H NMR (400 MHz, dimethyl sulfoxide-d₆) δ 12.73 (s, 1H), 8.23 (d, J=2.8 Hz, 1H), 8.01 (d, J=8.3 Hz, 1H), 7.58 (t, J=7.8 Hz, 1H), 7.29 (t, J=6.2 Hz, 1H), 7.03 (d, J=7.2 Hz, 2H), 6.63 (d, J=8.4 Hz, 1H), 6.13 (d, J=2.8 Hz, 1H), 4.32 (t, J=6.9 Hz, 2H), 3.72 (s, 2H), 3.10 (s, 2H), 2.11-2.05 (m, 2H), 1.85 (s, 2H), 1.74 (d, J=8.9 Hz, 2H), 1.43 (d, J=65.6 Hz, 9H), 1.01-0.85 (m, 5H), ESI-MS m/z calc. 633.2345, found 634.2 (M+1)⁺; Retention time: 1.85 min (LC Method B) and as the second enantiomer to elute, (15R)-12,12-dimethyl-8-(3-{2-[1-(trifluoromethyl)cyclopropyl]ethoxy}-1H-pyrazol-1-yl)-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 34) (29.1 mg, 65%); ¹H NMR (400 MHz, dimethyl sulfoxide-d₆) δ 12.73 (s, 1H), 8.23 (d, J=2.8 Hz, 1H), 8.01 (d, J=8.2 Hz, 1H), 7.58 (dd, J=8.4, 7.2 Hz, 1H), 7.29 (d, J=6.9 Hz, 1H), 7.03 (d, J=7.2 Hz, 2H), 6.63 (d, J=8.4 Hz, 1H), 6.13 (d, J=2.8 Hz, 1H), 4.38-4.28 (m, 2H), 3.72 (s, 2H), 3.10 (s, 1H), 2.08 (t, J=7.0 Hz, 2H), 1.96-1.68 (m, 4H), 1.51 (s, 5H), 1.35 (s, 4H), 0.99-0.85 (m, 5H), ESI-MS m/z calc. 633.2345, found 634.2 (M+1)⁺; Retention time: 1.85 min (LC Method B).

Example 121: Preparation of 12,12-dimethyl-8-(3-{2-[1-(trifluoromethyl)cyclopropyl]ethoxy}-1H-pyrazol-1-yl)-2λ⁶-thia-3,9,11,20,25-pentaazatetracyclo[19.3.1.0⁵,¹⁰.0¹¹,¹⁵]pentacosa-1(24),5,7,9,21(25),22-hexaene-2,2,4-trione (Compound 37)

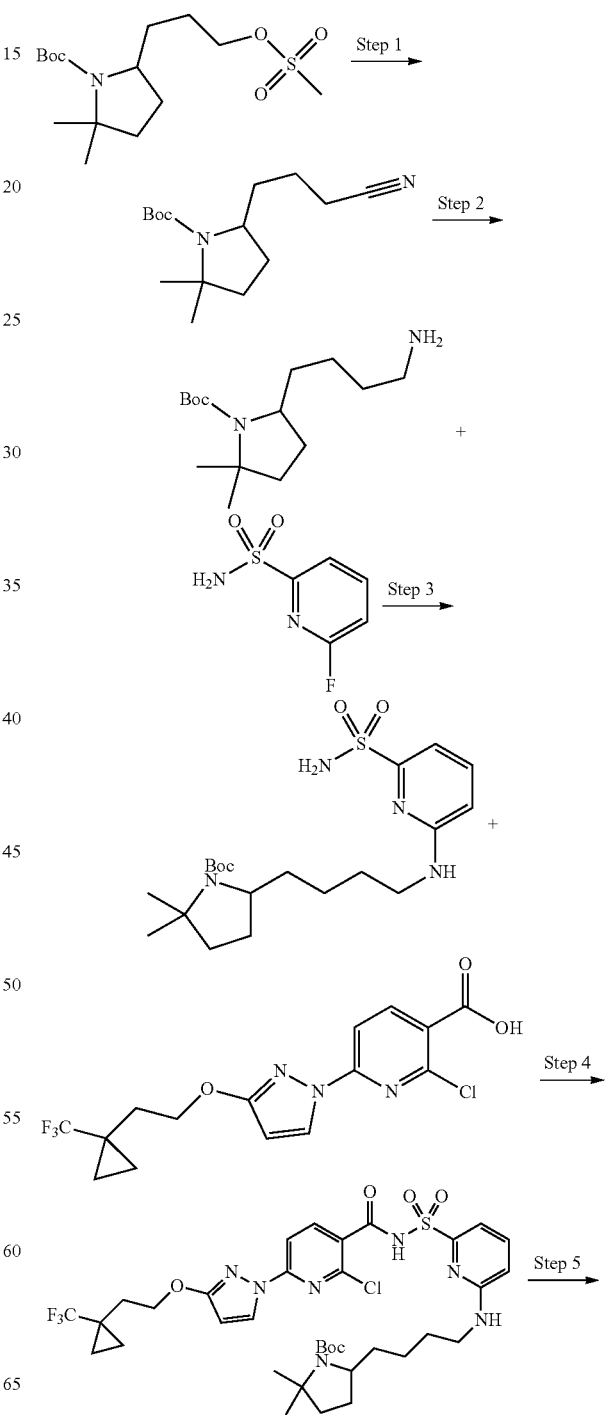

-continued

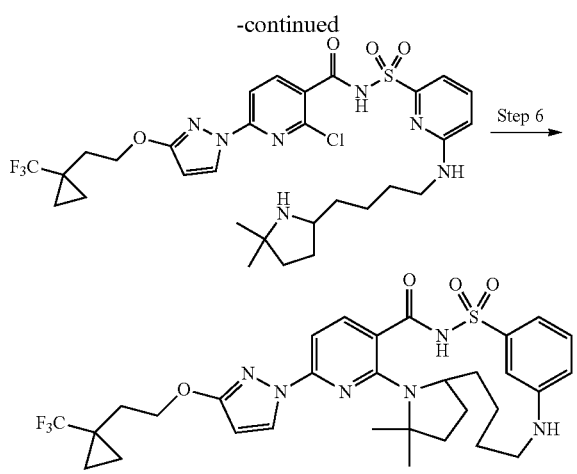

Step 1: tert-Butyl 5-(3-cyanopropyl)-2,2-dimethyl-pyrrolidine-1-carboxylate

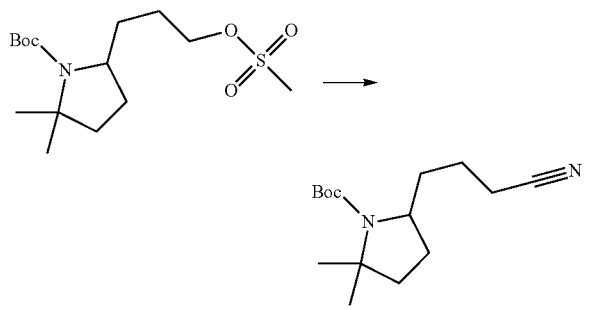

To a round bottom flask was added tert-butyl 2,2-dimethyl-5-(3-methylsulfonyloxypropyl)pyrrolidine-1-carboxylate (650 mg, 1.938 mmol), dimethyl sulfoxide (2 mL) and sodium cyanide (100 mg, 2.041 mmol). The reaction was heated at 80° C. overnight. The reaction was filtered and purified via HPLC (1%-99% acetonitrile in water with a 0.1% hydrochloric acid modifier) giving tert-butyl 5-(3-cyanopropyl)-2,2-dimethyl-pyrrolidine-1-carboxylate (272 mg, 53%). ESI-MS m/z calc. 266.19943, found 211.2 (M+1)$^+$; Retention time: 1.67 min (LC Method B).

Step 2: tert-Butyl 5-(4-aminobutyl)-2,2-dimethyl-pyrrolidine-1-carboxylate

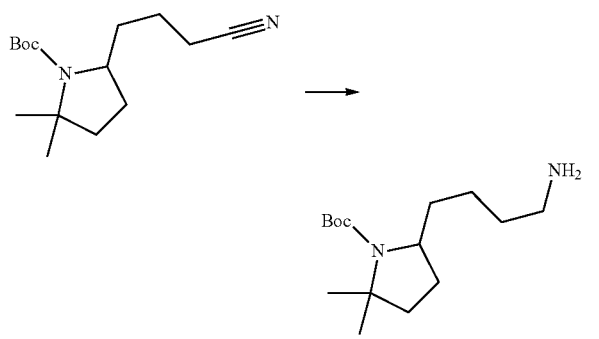

To a round bottom flask was added tert-butyl 5-(3-cyanopropyl)-2,2-dimethyl-pyrrolidine-1-carboxylate (271 mg, 1.017 mmol), methanol (1.50 mL), Raney nickel (100 mg of 50% w/v) and ammonia (2.80 mL of 7 M, 19.60 mmol). The reaction was purged with nitrogen and a balloon of hydrogen (2.050 mg, 1.017 mmol) was attached and stirred the mixture overnight at room temperature. Additional Raney nickel (100 mg of 50% w/v) and ammonia (2.80 mL of 7 M, 19.60 mmol) was added and the reaction was stirred for 4 h. The reaction was filtered and the filter cake was washed with additional methanol and dichloromethane. The filtrate solution was evaporated to dryness to provide tert-butyl 5-(4-aminobutyl)-2,2-dimethyl-pyrrolidine-1-carboxylate (270 mg, 98%) as a clear colorless oil. ESI-MS m/z calc. 270.23074, found 271.3 (M+1)$^+$; Retention time: 1.1 min (LC Method B).

Step 3: tert-Butyl 2,2-dimethyl-5-[4-[(6-sulfamoyl-2-pyridyl)amino]butyl]pyrrolidine-1-carboxylate

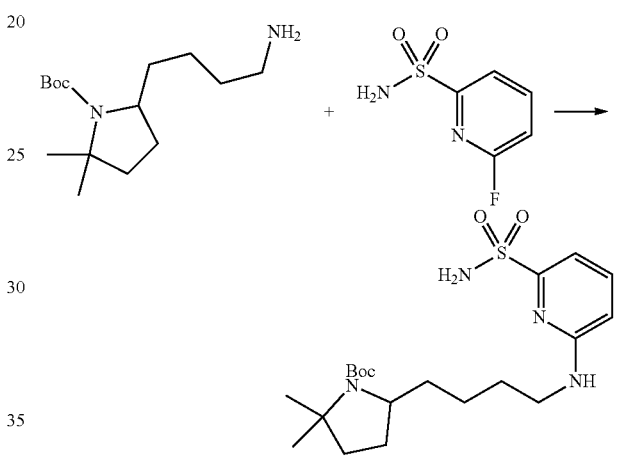

To a vial was added potassium carbonate (415 mg, 3.003 mmol), 6-fluoropyridine-2-sulfonamide (170 mg, 0.9650 mmol) and a solution of tert-butyl 5-(4-aminobutyl)-2,2-dimethyl-pyrrolidine-1-carboxylate (270 mg, 0.9985 mmol) in dimethyl sulfoxide (3 mL). The reaction was placed in a preheated 80° C. oil bath and allowed to stir overnight. The reaction was filtered and purified via HPLC (1%-99% acetonitrile in water with a 0.1% hydrochloric acid modifier) to provide tert-butyl 2,2-dimethyl-5-[4-[(6-sulfamoyl-2-pyridyl)amino]butyl]pyrrolidine-1-carboxylate (155.2 mg, 38%). ESI-MS m/z calc. 426.23007, found 427.3 (M+1)$^+$; Retention time: 1.71 min (LC Method B).

Step 4: tert-Butyl 5-[4-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate

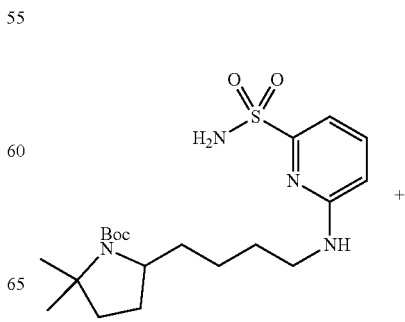

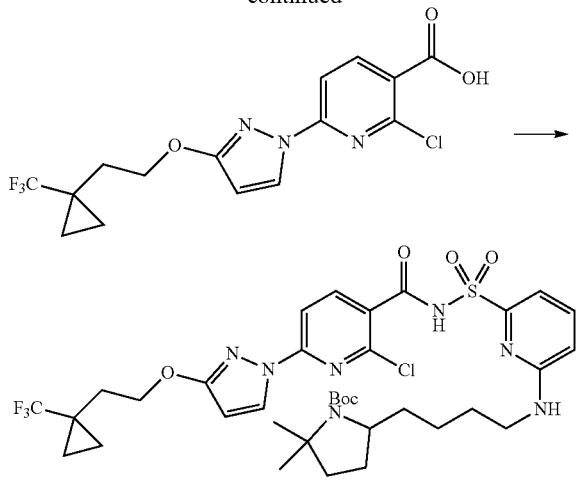

To a round bottom flask was added was added 2-chloro-6-[3-[2-[1-(trifluoromethyl)cyclopropyl]ethoxy]pyrazol-1-yl]pyridine-3-carboxylic acid (166.0 mg, 0.4418 mmol), carbonyl diimidazole (71 mg, 0.4379 mmol) and tetrahydrofuran (2.0 mL). The reaction was heated to 45° C. for 2 h then a solution of tert-butyl 2,2-dimethyl-5-[4-[(6-sulfamoyl-2-pyridyl)amino]butyl]pyrrolidine-1-carboxylate (155.2 mg, 0.3638 mmol) in tetrahydrofuran (2.0 mL) was added followed by 1,8-diazabicyclo[5.4.0]undec-7-ene (165 µL, 1.103 mmol) and the reaction was allowed to stir at room temperature overnight. The reaction was filtered and purified via HPLC (30%-99% acetonitrile in water with a 0.1% hydrochloric acid modifier) giving tert-butyl 5-[4-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate (126 mg, 44%) isolated as a white solid. ESI-MS m/z calc. 783.27924, found 784.5 (M+1)⁺; Retention time: 1.9 min (LC Method G).

Step 5: 2-Chloro-N-[[6-[4-(5,5-dimethylpyrrolidin-2-yl)butylamino]-2-pyridyl]sulfonyl]-6-[3-[2-[1-(trifluoromethyl)cyclopropyl]ethoxy]pyrazol-1-yl]pyridine-3-carboxamide To a round bottom flask was added tert-butyl 5-[4-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate (126 mg, 0.1607 mmol), dichloromethane (2 mL), and hydrochloric acid (400 µL of 4 M in dioxane, 1.600 mmol). The reaction was stirred at room temperature for 1 h. The reaction was quenched with saturated sodium bicarbonate and extracted with ethyl acetate. The organic layer was dried over sodium sulfate, filtered and evaporated to provide 2-chloro-N-[[6-[4-(5,5-dimethylpyrrolidin-2-yl)butylamino]-2-pyridyl]sulfonyl]-6-[3-[2-[1-(trifluoromethyl)cyclopropyl]ethoxy]pyrazol-1-yl]pyridine-3-carboxamide (105 mg, 96%). ESI-MS m/z calc. 683.2268, found 684.5 (M+1)⁺; Retention time: 0.79 min (LC Method B).

Step 6: 12,12-Dimethyl-8-(3-{2-[1-(trifluoromethyl)cyclopropyl]ethoxy}-1H-pyrazol-1-yl)-2λ⁶-thia-3,9,11,20,25-pentaazatetracyclo[19.3.1.0⁵,¹⁰.0¹¹,¹⁵]pentacosa-1(24),5,7,9,21(25),22-hexaene-2,2,4-trione (Compound 37)

To a vial was added potassium carbonate (107 mg, 0.7742 mmol), cesium fluoride (35 mg, 0.2304 mmol) and a solution of 2-chloro-N-[[6-[4-(5,5-dimethylpyrrolidin-2-yl)butylamino]-2-pyridyl]sulfonyl]-6-[3-[2-[1-(trifluoromethyl)cyclopropyl]ethoxy]pyrazol-1-yl]pyridine-3-carboxamide (105 mg, 0.1535 mmol) in dimethyl sulfoxide (1.8 mL). The reaction was heated in a sealed tube overnight at 150° C. The reaction was quenched with brine and extracted with ethyl acetate. The organic layer was dried over sodium sulfate, filtered and evaporated. The crude product was purified via HPLC (30%-99% acetonitrile in water with a 0.1% hydrochloric acid modifier) giving 12,12-dimethyl-8-(3-{2-[1-(trifluoromethyl)cyclopropyl]ethoxy}-1H-pyrazol-1-yl)-2λ⁶-thia-3,9,11,20,25-pentaazatetracyclo[19.3.1.0⁵,¹⁰.0¹¹,¹⁵]pentacosa-1(24),5,7,9,21(25),22-hexaene-2,2,4-trione (Compound 37) (27 mg, 25%). ESI-MS m/z calc. 647.2502, found 648.2 (M+1)⁺; Retention time: 1.97 min (LC Method B).

867

Example 122: Preparation of 8-(3-hydroxy-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Hydrochloride Salt) (Compound 38)

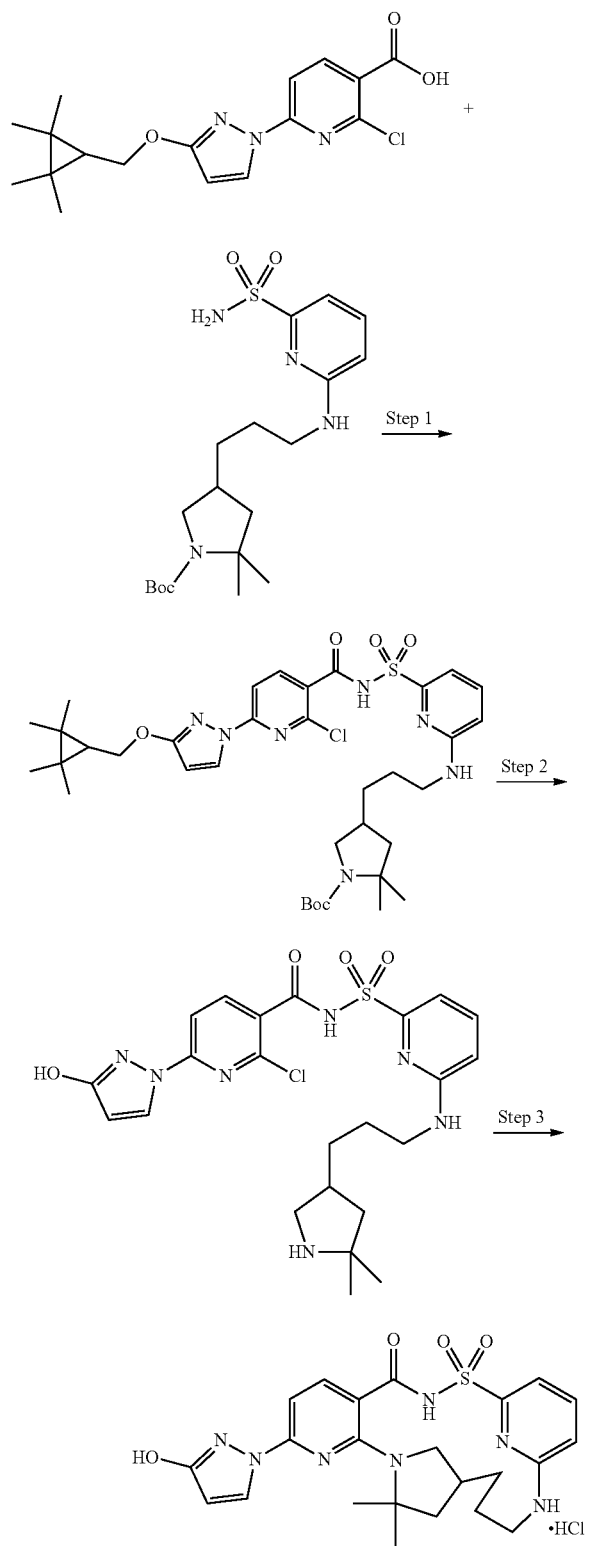

868

Step 1: tert-Butyl 4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate

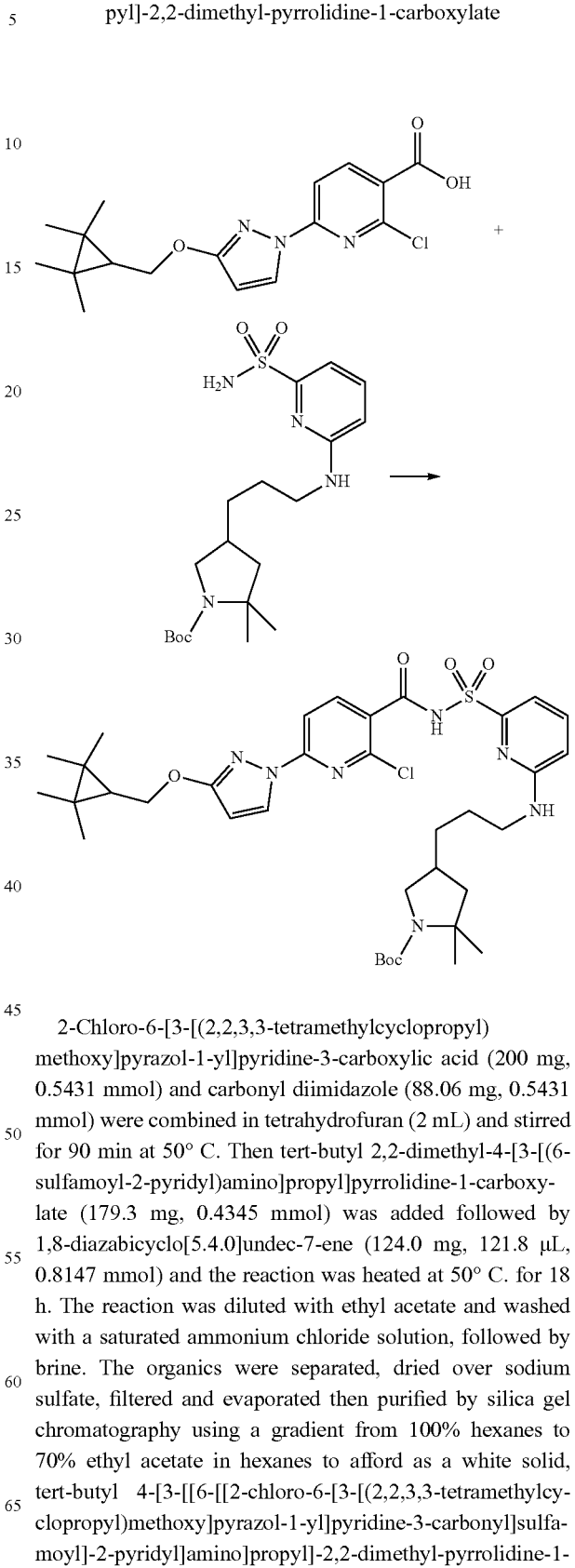

2-Chloro-6-[3-[(2,2,3,3-tetramethylcyclopropyl)methoxy]pyrazol-1-yl]pyridine-3-carboxylic acid (200 mg, 0.5431 mmol) and carbonyl diimidazole (88.06 mg, 0.5431 mmol) were combined in tetrahydrofuran (2 mL) and stirred for 90 min at 50° C. Then tert-butyl 2,2-dimethyl-4-[3-[(6-sulfamoyl-2-pyridyl)amino]propyl]pyrrolidine-1-carboxylate (179.3 mg, 0.4345 mmol) was added followed by 1,8-diazabicyclo[5.4.0]undec-7-ene (124.0 mg, 121.8 µL, 0.8147 mmol) and the reaction was heated at 50° C. for 18 h. The reaction was diluted with ethyl acetate and washed with a saturated ammonium chloride solution, followed by brine. The organics were separated, dried over sodium sulfate, filtered and evaporated then purified by silica gel chromatography using a gradient from 100% hexanes to 70% ethyl acetate in hexanes to afford as a white solid, tert-butyl 4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1- carboxylate (206 mg, 51%). ESI-MS m/z calc. 743.3232, found 744.7 (M+1)⁺; Retention time: 0.95 min (LC Method A).

Step 2: 2-Chloro-N-[[6-[3-(5,5-dimethylpyrrolidin-3-yl)propylamino]-2-pyridyl]sulfonyl]-6-(3-hydroxypyrazol-1-yl)pyridine-3-carboxamide

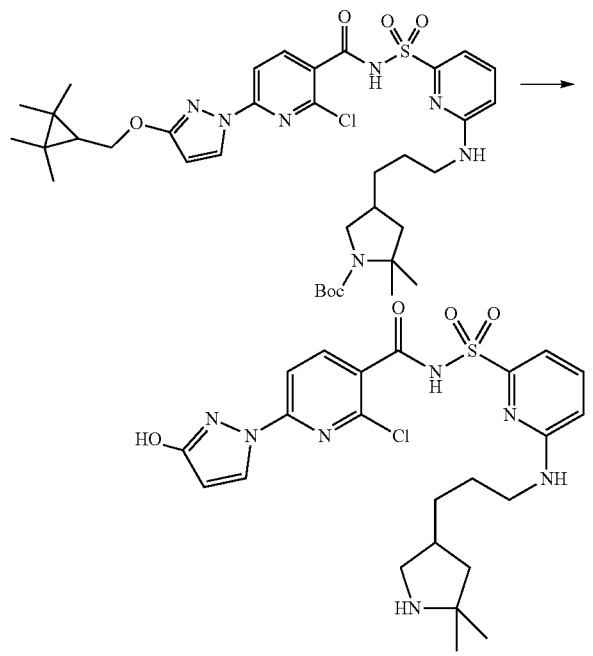

To a solution of tert-butyl 4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate (25 mg, 0.03359 mmol) in dichloromethane (1 mL) was added trifluoroacetic acid (19.16 mg, 12.95 µL, 0.1680 mmol) at 0° C. and the mixture was stirred for 30 min (reaction mixture 1). Separately, to a solution of tert-butyl 4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate (25 mg, 0.03359 mmol) in dioxane (1 mL) was added hydrochloric acid (42.00 µL of 4 M, 0.1680 mmol) at 0° C. and the mixture was stirred for 30 min (reaction mixture 2). Separately, a solution of tert-butyl 4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate (25 mg, 0.03359 mmol) in 2,2,2-trifluoroethanol (1.680 g, 1.224 mL, 16.79 mmol) containing 1% trifluoroacetic acid was stirred for 30 min (reaction mixture 3). Separately, to a solution of tert-butyl 4-[3-[[6-[[2-chloro-6-[3-[(2,2,3,3-tetramethylcyclopropyl)methoxy]pyrazol-1-yl]pyridine-3-carbonyl]sulfamoyl]-2-pyridyl]amino]propyl]-2,2-dimethyl-pyrrolidine-1-carboxylate (25 mg, 0.03359 mmol) in toluene (1 mL) was added silica gel (100 mg) and the mixture was heated at 90° C. for 24 h (reaction mixture 4). Combined all four of the reaction mixtures and purified by a reverse phase HPLC-MS method using a Luna C₁₈ (2) column (75×30 mm, 5 µm particle size) sold by Phenomenex (pn: 00C-4252-U0-AX) and a dual gradient run from 20%- 80% mobile phase B over 15.0 minutes (mobile phase A=water (5 mM hydrochloric acid), mobile phase B=acetonitrile, flow rate=50 mL/min, injection volume=950 µL, and column temperature=25° C.) to afford 2-chloro-N-[[6-[3-(5,5-dimethylpyrrolidin-3-yl)propylamino]-2-pyridyl]sulfonyl]-6-(3-hydroxypyrazol-1-yl)pyridine-3-carboxamide (42 mg, 47%). ¹H NMR (400 MHz, Methanol-d₄) δ 8.31 (d, J=2.9 Hz, 1H), 8.00 (d, J=8.4 Hz, 1H), 7.72-7.63 (m, 2H), 7.30 (dd, J=7.2, 0.8 Hz, 1H), 6.84 (dd, J=8.6, 0.8 Hz, 1H), 5.97 (d, J=2.8 Hz, 1H), 3.50 (dd, J=11.8, 8.4 Hz, 21H), 3.41 (dp, J=20.3, 6.7 Hz, 2H), 2.93 (dd, J=11.8, 9.1 Hz, 1H), 2.54 (dt, J=16.6, 8.3 Hz, 1H), 2.09 (dd, J=13.1, 7.5 Hz, 1H), 1.70-1.59 (m, 2H), 1.59-1.48 (m, 2H), 1.45 (s, 3H), 1.37 (s, 3H). ESI-MS m/z calc. 533.1612, found 534.5 (M+1)⁺; Retention time: 0.45 min (LC Method A).

Step 3: 8-(3-Hydroxy-1H-pyrazol-1-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Hydrochloride Salt) (Compound 38)

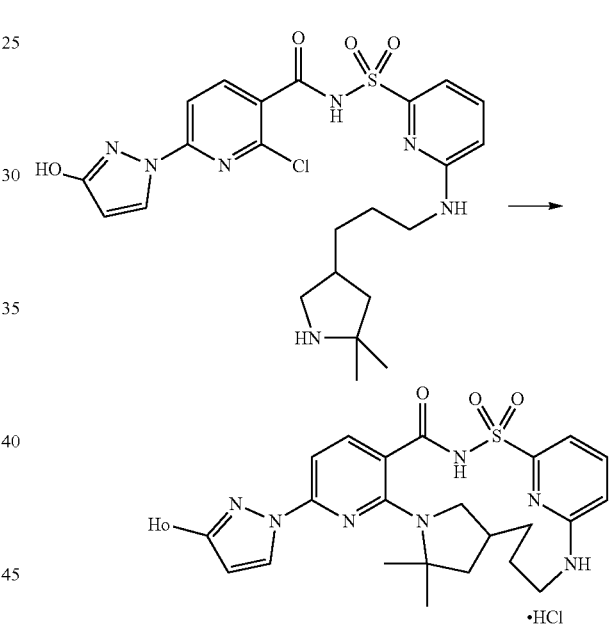

To a solution of 2-chloro-N-[[6-[3-(5,5-dimethylpyrrolidin-3-yl)propylamino]-2-pyridyl]sulfonyl]-6-(3-hydroxypyrazol-1-yl)pyridine-3-carboxamide (42 mg, 0.07865 mmol) in dimethyl sulfoxide (2.0 mL) was added 3 Å molecular sieves and the mixture was stirred at room temperature for 15 min. Then, cesium fluoride (11.95 mg, 0.07865 mmol) and potassium carbonate (10.87 mg, 0.07865 mmol) were added and the reaction mixture was heated at 140° C. for overnight. The reaction mixture was filtered through a Whatman filter disc (puradisc 25 TF) and the filtrate was purified by a reverse phase HPLC-MS method using a Luna C₁₈ (2) column (75×30 mm, 5 µm particle size) sold by Phenomenex (pn: 00C-4252-U0-AX), and a dual gradient run from 30%-80% mobile phase B over 15.0 min (mobile phase A=water (5 mM hydrochloric acid), mobile phase B=acetonitrile, Flow rate=50 mL/min, injection volume=950 µL and column temperature=25° C.) to afford 8-(3-hydroxy-1H-pyrazol-1-yl)-12,12-dimethyl-2λ⁶-thia-3,9,11,18,23-pentaazatetracyclo[17.3.1.1¹¹,¹⁴.0⁵,¹⁰]

tetracosa-1(22),5,7,9,19(23),20-hexaene-2,2,4-trione (hydrochloride salt) (Compound 38) (2.5 mg, 17%) as a white solid. $^1$H NMR (400 MHz, Methanol-$d_4$) δ 8.21 (d, J=2.7 Hz, 1H), 7.84 (d, J=8.2 Hz, 1H), 7.57-7.51 (m, 1H), 7.16 (d, J=7.2 Hz, 1H), 6.92 (d, J=8.3 Hz, 1H), 6.67 (d, J=8.5 Hz, 1H), 5.87 (d, J=2.7 Hz, 1H), 4.10-4.00 (m, 1H), 3.66-3.49 (m, 1H), 3.09-3.00 (m, 1H), 2.90-2.82 (m, 1H), 2.66 (d, J=11.1 Hz, 1H), 2.24-2.12 (m, 1H), 1.92-1.82 (m, 1H), 1.66 (s, 3H), 1.59 (s, 3H), 1.49-1.39 (m, 2H), 0.95-0.83 (m, 2H). ESI-MS m/z calc. 497.1845, found 498.5 (M+1)$^+$; Retention time: 1.48 min (LC Method E).

Example 123: Preparation of 21,21-dimethyl-4-(3-{2-[1-(trifluoromethyl)cyclopropyl]ethoxy}-1H-pyrazol-1-yl)-10λ$^6$-thia-1,3,9,14,23-pentaazatetracyclo[17.2.1.111,14.02,7]tricosa-2,4,6,11(23),12-pentaene-8,10,10-trione (Compound 39)

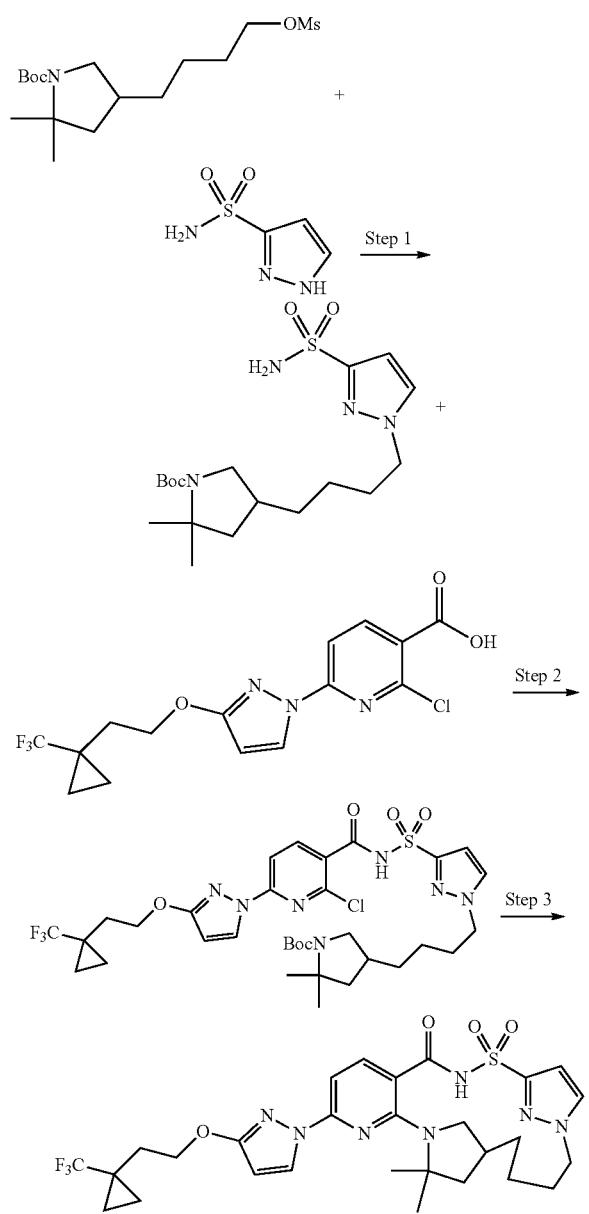

Step 1: tert-Butyl 2,2-dimethyl-4-[4-(3-sulfamoylpyrazol-1-yl)butyl]pyrrolidine-1-carboxylate

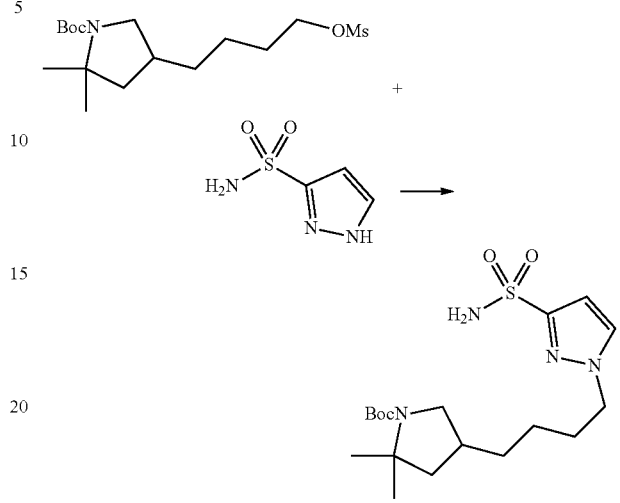

tert-Butyl 2,2-dimethyl-4-(4-methylsulfonyloxybutyl)pyrrolidine-1-carboxylate (848 mg, 2.426 mmol) and 1H-pyrazole-3-sulfonamide (361.5 mg, 2.457 mmol) followed by potassium carbonate (1.2 g, 8.683 mmol) were dissolved in N,N-dimethylformamide (9.0 mL) and stirred at 60° C. in a sealed 20 mL vial for 20 h (UPLC indicates conversion to intended product plus a minor less polar second peak with same mass which is a minor regioisomer side product). Cooled to room temperature, poured into water (100 mL) and extracted with ethyl acetate (2×100 mL), combined organic layers, washed with water (2×100 mL), dried (sodium sulfate), filtered and concentrated. The brown residue was purified by silica gel chromatography using a gradient from 100% hexanes to 100% ethyl acetate to afford as a colorless oil which turned into a white solid under vacuum, tert-butyl 2,2-dimethyl-4-[4-(3-sulfamoylpyrazol-1-yl)butyl]pyrrolidine-1-carboxylate (427 mg, 44%). $^1$H NMR (400 MHz, dimethyl sulfoxide-$d_6$) δ 7.87 (d, J=2.3 Hz, 1H), 7.37 (s, 2H), 6.56 (d, J=2.3 Hz, 1H), 4.15 (t, J=7.1 Hz, 2H), 3.53 (dd, J=11.2, 5.4 Hz, 1H), 2.76 (dd, J=22.3, 10.8 Hz, 1H), 2.05 (s, 1H), 1.94-1.83 (m, 1H), 1.82-1.73 (m, 2H), 1.40-1.35 (m, 12H), 1.33 (s, 3H), 1.30 (d, J=2.5 Hz, 1H), 1.23 (s, 4H). ESI-MS m/z calc. 400.21442, found 401.2 (M+1)$^+$; Retention time: 1.64 min (LC Method E).

Step 2: tert-Butyl 4-[4-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]butyl]-2,2-dimethyl-pyrrolidine-1-carboxylate

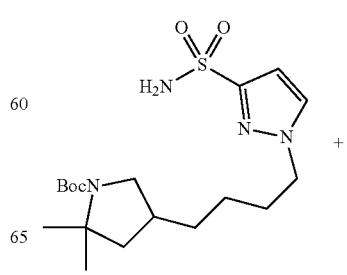

-continued

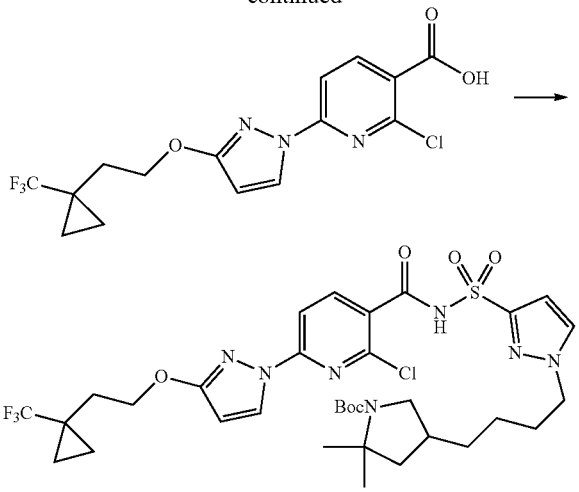

2-Chloro-6-[3-[2-[1-(trifluoromethyl)cyclopropyl]ethoxy]pyrazol-1-yl]pyridine-3-carboxylic acid (500 mg, 1.331 mmol) and carbonyl diimidazole (215 mg, 1.326 mmol) were combined in tetrahydrofuran (8.0 mL) and stirred for 120 min at 50° C. Then tert-butyl 2,2-dimethyl-4-[4-(3-sulfamoylpyrazol-1-yl)butyl]pyrrolidine-1-carboxylate (423 mg, 1.056 mmol) was added followed by 1,8-diazabicyclo[5.4.0]undec-7-ene (350 μL, 2.340 mmol) and the reaction was heated at 50° C. for 20 h. The reaction mixture was diluted with ethyl acetate and washed with a 1M citric acid solution, followed by brine. The organics were separated, dried over sodium sulfate, filtered and evaporated and then purified by silica gel chromatography using a gradient from 100% hexanes to 90% ethyl acetate in hexanes to afford as a white solid, tert-butyl 4-[4-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]butyl]-2,2-dimethyl-pyrrolidine-1-carboxylate (587 mg, 73%). ESI-MS m/z calc. 757.2636, found 758.2 (M+1)+; Retention time: 2.37 min (LC Method E).

Step 3: 21,21-Dimethyl-4-(3-{2-[1-(trifluoromethyl)cyclopropyl]ethoxy}-1H-pyrazol-1-yl)-10λ⁶-thia-1,3,9,14,23-pentaazatetracyclo[17.2.1.1¹¹,¹⁴.0²,⁷]tricosa-2,4,6,11(23),12-pentaene-8,10,10-trione (Compound 39)

tert-Butyl 4-[4-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]butyl]-2,2-dimethyl-pyrrolidine-1-carboxylate (580 mg, 0.7649 mmol) was dissolved in dichloromethane (12 mL) and to the mixture was added hydrochloric acid (6.0 mL of 4M in dioxane, 24.00 mmol) and stirred at room temperature for 1 h. Concentrated the mixture to dryness under reduced pressure, redissolved in ethyl acetate and then added aqueous 2M sodium carbonate (5 mL), giving pH 10. Removed the organic layer and further washed the aqueous layer with ethyl acetate (2×10 mL), combined the organic layers, washed with brine, then dried over sodium sulfate, filtered and evaporated to dryness under reduced pressure. Combined this material and potassium carbonate (550 mg, 3.980 mmol), cesium fluoride (185 mg, 1.218 mmol), 3 Å molecular sieves and dimethyl sulfoxide (12 mL) in a vial, purged with nitrogen, capped, heated to 150° C. and stirred for 18 h. Cooled to room temperature and the reaction was diluted with ethyl acetate and washed with a 1M citric acid solution, followed by brine. The organics were separated, dried over sodium sulfate, filtered and evaporated then purified by silica gel chromatography using a gradient from 100% hexanes to 80% ethyl acetate in hexanes to afford as a white solid, 21,21-dimethyl-4-(3-{2-[1-(trifluoromethyl)cyclopropyl]ethoxy}-1H-pyrazol-1-yl)-10λ⁶-thia-1,3,9,14,23-pentaazatetracyclo[17.2.1.1¹¹,¹⁴.0²,⁷]tricosa-2,4,6,11(23),12-pentaene-8,10,10-trione (Compound 39) (176.9 mg, 37%). ¹H NMR (400 MHz, dimethyl sulfoxide-d₆) δ 12.59 (s, 1H), 8.21 (d, J=2.8 Hz, 1H), 7.99 (d, J=2.1 Hz, 1H), 7.77 (d, J=8.3 Hz, 1H), 6.97-6.81 (m, 2H), 6.12 (d, J=2.7 Hz, 1H), 4.30 (dd, J=15.9, 9.0 Hz, 4H), 2.73 (dt, J=22.6, 11.0 Hz, 2H), 2.31-2.18 (m, 1H), 2.18-2.03 (m, 3H), 2.02-1.92 (m, 1H), 1.89 (dd, J=11.9, 5.5 Hz, 1H), 1.67 (s, 1H), 1.61 (s, 3H), 1.60-1.54 (m, 1H), 1.52 (s, 3H), 1.48 (d, J=12.4 Hz, 1H), 1.16-1.03 (m, 1H), 0.99-0.93 (m, 2H), 0.90 (d, J=10.9 Hz, 2H), 0.77 (s, 1H). ESI-MS m/z calc. 621.2345, found 622.4 (M+1)+; Retention time: 2.2 min (LC Method E).

Example 124: Preparation of 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.0⁴,⁸.0⁹,¹⁴]docosa-1(22),9,11,13,18,20-hexaene-15,17,17-trione (Compound 41)

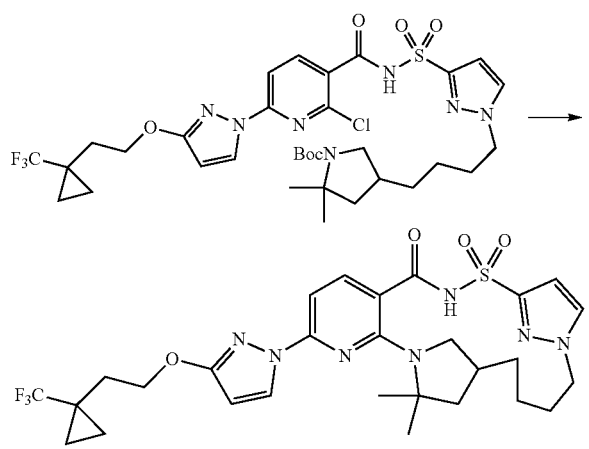

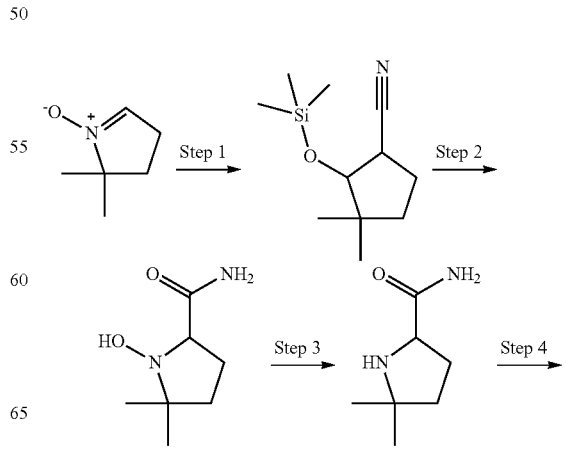

875
-continued

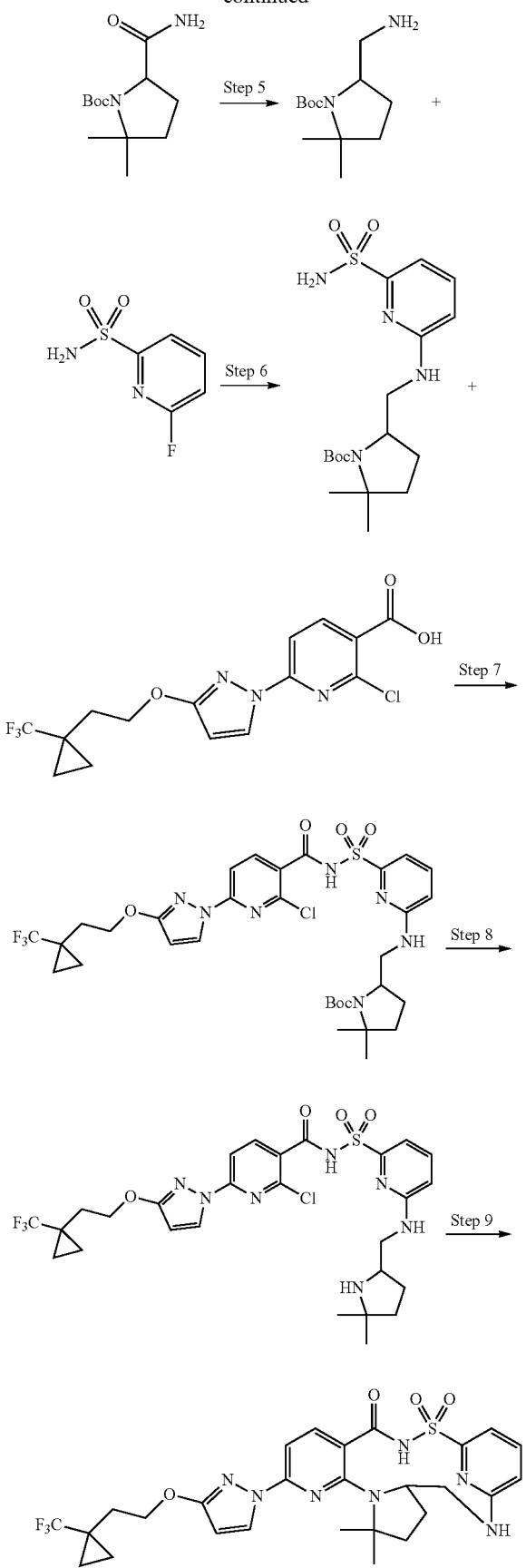

876

Step 1: 5,5-Dimethyl-1-trimethylsilyloxy-pyrrolidine-2-carbonitrile

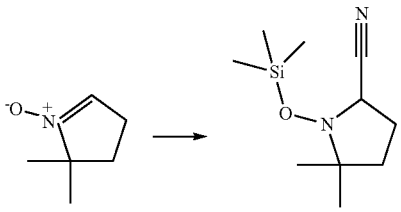

Trimethylsilylformonitrile (30.93 g, 39 mL, 311.8 mmol) was added to 2,2-dimethyl-1-oxido-3,4-dihydropyrrol-1-ium (23.31 g, 206.0 mmol) in dichloromethane (920 mL) and the mixture was left stirring at room temperature overnight. The reaction mixture was concentrated under reduced pressure under safe conditions to provide the desired product 5,5-dimethyl-1-trimethylsilyloxy-pyrrolidine-2-carbonitrile (44.04 g, 101%) as a crude amber oil which was used directly in the next step. ESI-MS m/z calc. 212.13, found 213.2 (M+1)$^+$; Retention time: 2.325 min (LC Method I).

Step 2: 1-Hydroxy-5,5-dimethyl-pyrrolidine-2-carboxamide

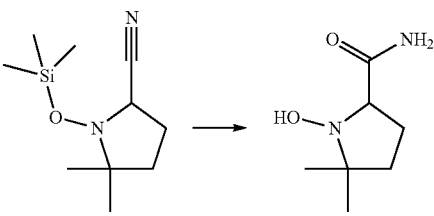

5,5-Dimethyl-1-trimethylsilyloxy-pyrrolidine-2-carbonitrile (13 g, 61.22 mmol) was slowly added to sulfuric acid (160.1 g, 87 mL, 1.632 mol), cooled with an ice bath and left stirring at room temperature for 3 h. The reaction mixture was diluted with ice (400 mL) and the resulting mixture was slowly neutralized with solid sodium hydroxide (125 g, 3.125 mol) divided in 3 portions (the last two portions were dissolved in water (75 mL)) and pH was verified to be weakly basic to neutral. The mixture was extracted with ethyl acetate (3×500 mL). The organic phases were combined, dried over anhydrous sodium sulfate, filtered and then concentrated under reduced pressure then dried under vacuum to provide the desired product, 1-hydroxy-5,5-dimethyl-pyrrolidine-2-carboxamide (8.51 g, 88%) as a pale yellow powder. $^1$H NMR (300 MHz, dimethyl sulfoxide-d$_6$) ppm 0.92 (s, 3H), 1.07 (s, 3H), 1.38-1.59 (m, 3H), 1.91-2.09 (m, 1H), 3.13-3.22 (m, 1H), 6.92 (br. s., 1H), 7.08 (br. s., 1H), 7.62 (s, 1H). ESI-MS m/z calc. 158.198, found 159.2 (M+1)$^+$; Retention time: 1.561 min (LC Method I).

Step 3: 5,5-Dimethylpyrrolidine-2-carboxamide

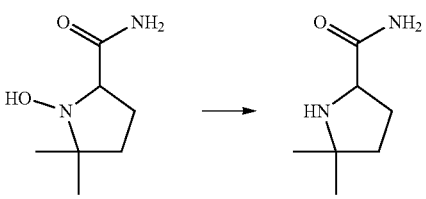

1-Hydroxy-5,5-dimethyl-pyrrolidine-2-carboxamide (8.51 g, 53.79 mmol) dissolved in methanol (200 mL) was stirred overnight with Raney nickel (8.7 g, 148.2 mmol) and hydrogen gas from an inflated balloon having a capacity 8 L of gas. After 5 h, more Raney nickel (8 g, 136.3 mmol) was added and the mixture was stirred overnight. Additional Raney nickel (9.69 g, 165.1 mmol) was put into the mixture and the mixture was further stirred over 3 days. More Raney nickel (9.5 g, 161.9 mmol) was added to the reaction mixture and the mixture was stirred 4 h. The reaction mixture was decanted and nickel solid was washed with methanol (3×250 mL) and to the combined methanol fraction was added some Celite then filtered over Celite and the cake was washed with methanol. The combined filtrate was concentrated under reduced pressure to provide the desired product, 5,5-dimethylpyrrolidine-2-carboxamide (7.29 g, 95%) as a beige solid. $^1$H NMR (300 MHz, CDCl$_3$) ppm 1.16 (s, 3H), 1.19 (s, 3H), 1.45-1.72 (m, 2H), 1.81 (br. s., 1H), 1.92-2.09 (m, 1H), 2.18-2.40 (m, 1H), 3.78 (dd, J=9.4, 6.2 Hz, 1H), 5.70 (br. s., 1H), 7.45 (br. s., 1H). ESI-MS m/z calc. 142.1106, found 143.2 (M+1)$^+$; Retention time: 0.31 min (LC Method I).

Step 4: tert-Butyl 5-carbamoyl-2,2-dimethyl-pyrrolidine-1-carboxylate

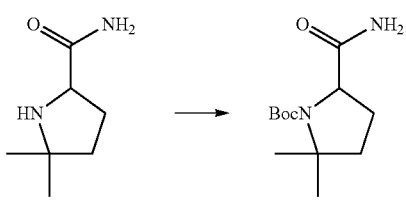

Di-tert-butyl dicarbonate (21 g, 96.22 mmol) was added to 5,5-dimethylpyrrolidine-2-carboxamide (7.25 g, 50.98 mmol) dissolved in dioxane (140 mL) and water (50 mL) was added to the mixture that was then left stirring at room temperature overnight Sodium hydroxide (1.84 g, 46.00 mmol) dissolved in water (100 mL) was added to the mixture and the mixture was left stirring 2 min then ethyl acetate (200 mL) was added and the aqueous phase was discarded. The organic fraction was dried over anhydrous magnesium sulfate, filtered then concentrated under reduced pressure. The resulting oil solidified partially upon standing under vacuum. The solid was triturated in heptane (50 mL), filtered and washed with more heptane (3×100 mL) then dried under vacuum to provide tert-butyl 5-carbamoyl-2,2-dimethyl-pyrrolidine-1-carboxylate (10.95 g, 89%) as a white powder. $^1$H NMR (300 MHz, CDCl$_3$) ppm 1.33 (br. s., 3H), 1.48 (br. s., 12H), 1.70-2.34 (m, 4H), 4.16-4.48 (m, 1H), 5.30-5.58 (m, 1H), 5.71-7.03 (m, 1H). ESI-MS m/z calc. 242.163, found 143.2=(M+1-Boc)$^+$; Retention time: 1.67 min (LC Method I).

Step 5: tert-Butyl 5-(aminomethyl)-2,2-dimethyl-pyrrolidine-1-carboxylate

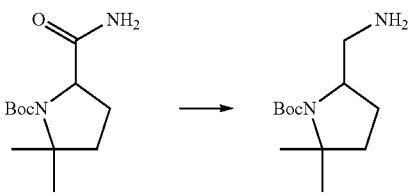 [SMILES: CC(C)(C)OC(=O)N1C(C(N)=O)CCC1(C)C ; CC(C)(C)OC(=O)N1C(CN)CCC1(C)C]

tert-Butyl 5-carbamoyl-2,2-dimethyl-pyrrolidine-1-carboxylate (5.3 g, 21.87 mmol) was added to borane-tetrahydrofuran (102 mL of 1 M in tetrahydrofuran, 102.0 mmol) and after the evolution of hydrogen stopped the reaction mixture was heated to 70° C. overnight. The reaction mixture was quenched slowly with concentrated ammonium chloride (1 mL). This mixture was then transferred into a 1 L round bottom flask containing deionized water (110 mL). With strong stirring, iodine (100 mg, 0.020 mL, 0.394 mmol) was added and left the mixture stirring open to air for 2 h. The reaction mixture was concentrated under reduced pressure and the resulting residue was purified on silica gel using a gradient from 10%-100% methanol in dichloromethane. Additional material was retrieved by applying ammonium hydroxide (2 mL) on top of the column followed by elution with pure methanol (done 3×). This provided tert-butyl 5-(aminomethyl)-2,2-dimethyl-pyrrolidine-1-carboxylate (1.19 g, 24%) as an amber oil. $^1$H NMR (300 MHz, CDCl$_3$) ppm 1.27 (br. s., 3H), 1.33-1.51 (m, 14H), 1.62-1.76 (m, 2H), 1.78-2.03 (m, 2H), 2.53 (dd, J=12.6, 8.2 Hz, 1H), 2.73-3.00 (m, 1H), 3.61-3.99 (m, 1H). ESI-MS m/z calc. 228.331, found 229.3 (M+1)$^+$; Retention time: 1.33 min (LC Method I).

Step 6: tert-Butyl 2,2-dimethyl-5-[[(6-sulfamoyl-2-pyridyl)amino]methyl]pyrrolidine-1-carboxylate

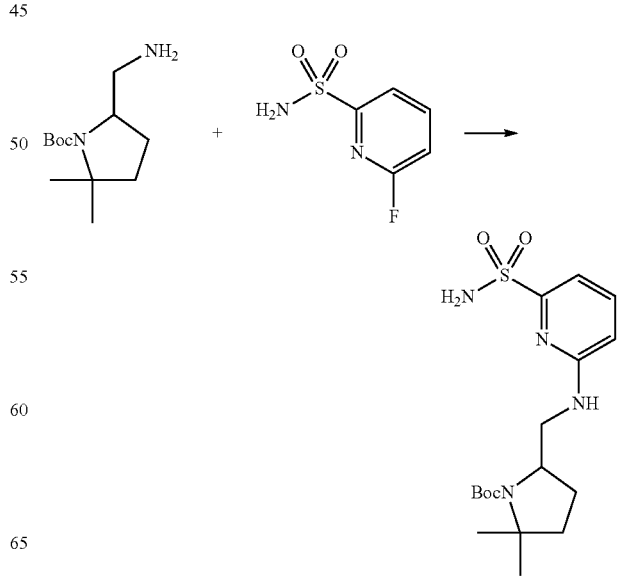

To tert-butyl 5-(aminomethyl)-2,2-dimethyl-pyrrolidine-1-carboxylate (140 mg, 0.6131 mmol) and 6-fluoropyridine-2-sulfonamide (108.0 mg, 0.6131 mmol) in dimethyl sulfoxide (1.179 mL) was added potassium carbonate (86.43 mg, 0.6254 mmol) and the mixture stirred at 100° C. for 20 h then allowed to cool to room temperature. Diluted with ethyl acetate and poured into 1 M citric acid. Separated the layers then washed the organic layer with saturated aqueous brine, dried (sodium sulfate), filtered and concentrated to a yellow foam which was purified by silica gel chromatography using a shallow gradient from 100% hexanes to 100% ethyl acetate giving tert-butyl 2,2-dimethyl-5-[[(6-sulfamoyl-2-pyridyl)amino]methyl]pyrrolidine-1-carboxylate (115.6 mg, 49%) as a white solid. ESI-MS m/z calc. 384.18314, found 385.4 (M+1)$^+$; Retention time: 0.62 min (LC Method A).

Step 7: tert-Butyl 5-[[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]methyl]-2,2-dimethyl-pyrrolidine-1-carboxylate

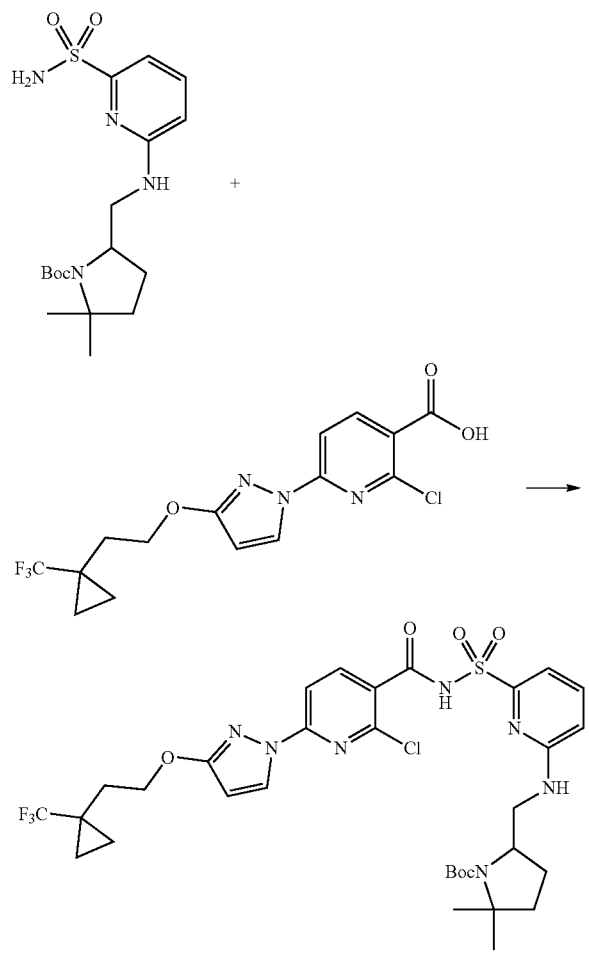

In a 20 mL vial, 2-chloro-6-[3-[2-[1-(trifluoromethyl)cyclopropyl]ethoxy]pyrazol-1-yl]pyridine-3-carboxylic acid (113.0 mg, 0.3007 mmol) and carbonyl diimidazole (53.44 mg, 0.3296 mmol) were combined in tetrahydrofuran (1.659 mL) and stirred for 120 min at 50° C. with a loose cap. Then tert-butyl 2,2-dimethyl-5-[[(6-sulfamoyl-2-pyridyl)amino]methyl]pyrrolidine-1-carboxylate (115.6 mg, 0.3007 mmol) in tetrahydrofuran (2.213 mL) was added followed by 1,8-diazabicyclo[5.4.0]undec-7-ene (94.25 mg, 92.58 µL, 0.6191 mmol) and the reaction was heated at 50° C. for 16 h. The reaction was diluted with ethyl acetate and washed with saturated aqueous ammonium chloride followed by brine. The organics were separated, dried over sodium sulfate, filtered and evaporated then purified using a reverse phase HPLC-MS method using a Luna C$_{18}$ (2) column (75×30 mm, 5 µm particle size) sold by Phenomenex (pn: 00C-4252-U0-AX) and a dual gradient run from 30%-99% mobile phase B over 15.0 min (mobile phase A=water (5 mM hydrochloric acid), mobile phase B=acetonitrile, flow rate=50 mL/min, injection volume=950 µL and column temperature=25° C.) giving tert-butyl 5-[[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]methyl]-2,2-dimethyl-pyrrolidine-1-carboxylate (119.2 mg, 53%). ESI-MS m/z calc. 741.2323, found 742.2 (M+1)$^+$; Retention time: 0.88 min (LC Method A).

Step 8: 2-Chloro-N-[[6-[(5,5-dimethylpyrrolidin-2-yl)methylamino]-2-pyridyl]sulfonyl]-6-[3-[2-[1-(trifluoromethyl)cyclopropyl]ethoxy]pyrazol-1-yl]pyridine-3-carboxamide

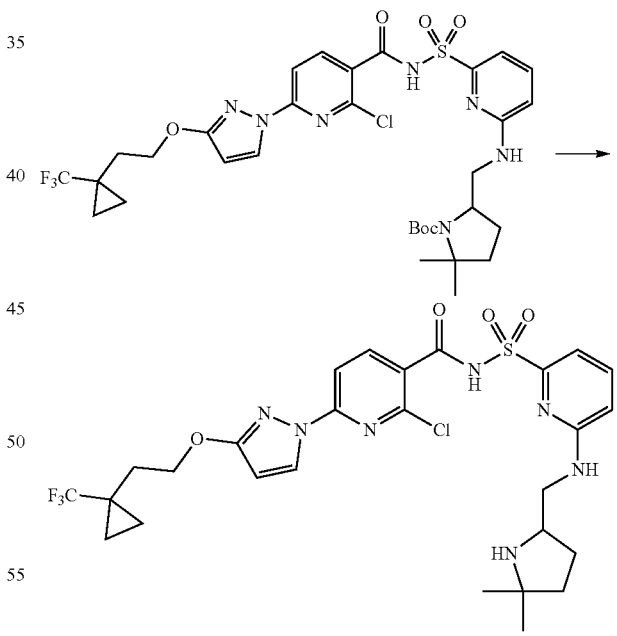

tert-Butyl 5-[[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]methyl]-2,2-dimethyl-pyrrolidine-1-carboxylate (119.2 mg, 0.1606 mmol) was dissolved in dichloromethane (520.2 µL) and to the mixture was added trifluoroacetic acid (840.1 mg, 567.6 µL, 7.368 mmol) and stirred the resulting mixture at room temperature for 60 min. Concentrated the mixture to dryness under reduced pressure, redissolved in dichloromethane and hexanes (1:1) and then material was evaporated to dryness under reduced pressure and placed under vacuum overnight to afford 2-chloro-N-[[6-[(5,5-dimethylpyrrolidin-2-yl)methylamino]-2-pyridyl]sulfonyl]-6-[3-[2-[1-(trifluoromethyl)cyclopropyl]ethoxy]pyrazol-1-yl]pyridine-3-carboxamide (92.9 mg, 90%). ESI-MS m/z calc. 641.1799, found 642.2 (M+1)+; Retention time: 0.63 min (LC Method A).

Step 9: 7,7-Dimethyl-11-(3-{2-[1-(trifluoromethyl)cyclopropyl]ethoxy}-1H-pyrazol-1-yl)-17λ6-thia-2,8,10,16,22-pentaazatetracyclo[16.3.1.04,8.09,14]docosa-1(22),9,11,13,18,20-hexaene-15,17,17-trione (Compound 41)

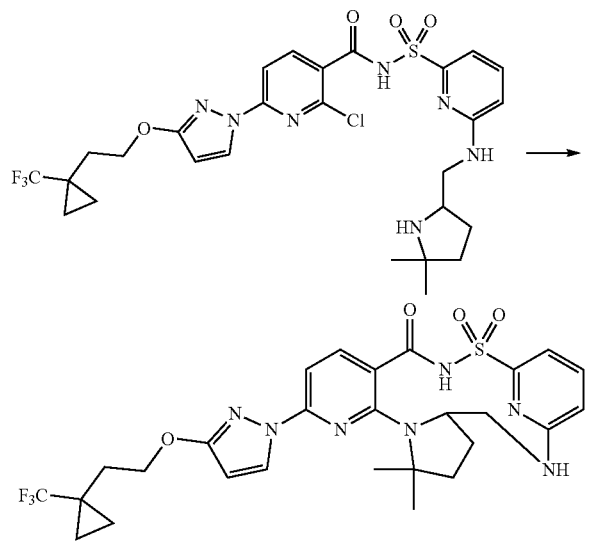

To a solution of 2-chloro-N-[[6-[(5,5-dimethylpyrrolidin-2-yl)methylamino]-2-pyridyl]sulfonyl]-6-[3-[2-[1-(trifluoromethyl)cyclopropyl]ethoxy]pyrazol-1-yl]pyridine-3-carboxamide (92.9 mg, 0.1447 mmol) in dimethyl sulfoxide (3.716 mL) was added potassium carbonate (99.99 mg, 0.7235 mmol), CsF (26.37 mg, 0.1736 mmol) and a small amount of 3 Å molecular sieves. The resulting mixture was capped and heated to 150° C. and stirred overnight. Cooled to room temperature, filtered and purified using a reverse phase HPLC-MS method using a Luna C18 (2) column (75×30 mm, 5 μm particle size) sold by Phenomenex (pn: 00C-4252-U0-AX), and a dual gradient run from 30%-99% mobile phase B over 15.0 min (mobile phase A=water (5 mM hydrochloric acid), mobile phase B=acetonitrile, flow rate=50 mL/min, injection volume=950 μL and column temperature=25° C.). Combined fractions containing product, removed acetonitrile by rotary evaporation, diluted with ethyl acetate and washed with saturated aqueous sodium bicarbonate (1×), dried (sodium sulfate), filtered and concentrated to 7,7-dimethyl-11-(3-{2-[1-(trifluoromethyl)cyclopropyl]ethoxy}-1H-pyrazol-1-yl)-17λ6-thia-2,8,10,16,22-pentaazatetracyclo[16.3.1.04,8.09,14]docosa-1(22),9,11,13,18,20-hexaene-15,17,17-trione (Compound 41) (27.6 mg, 31%) as a white solid. ESI-MS m/z calc. 605.2032, found 606.0 (M+1)+; Retention time: 1.89 min (LC Method B).

Example 125: Preparation of 21,21-dimethyl-4-(3-{2-[1-(trifluoromethyl)cyclopropyl]ethoxy}-1H-pyrazol-1-yl)-10λ6-thia-1,3,9,14,23-pentaazatetracyclo[17.2.1.111,14.02,7]tricosa-2,4,6,11(23),12-pentaene-8,10,10-trione (Enantiomer 1) (Compound 44) and 21,21-dimethyl-4-(3-{2-[1-(trifluoromethyl)cyclopropyl]ethoxy}-1H-pyrazol-1-yl)-10λ6-thia-1,3,9,14,23-pentaazatetracyclo[17.2.1.111,14.02,7]tricosa-2,4,6,11(23),12-pentaene-8,10,10-trione (Enantiomer 2) (Compound 45)

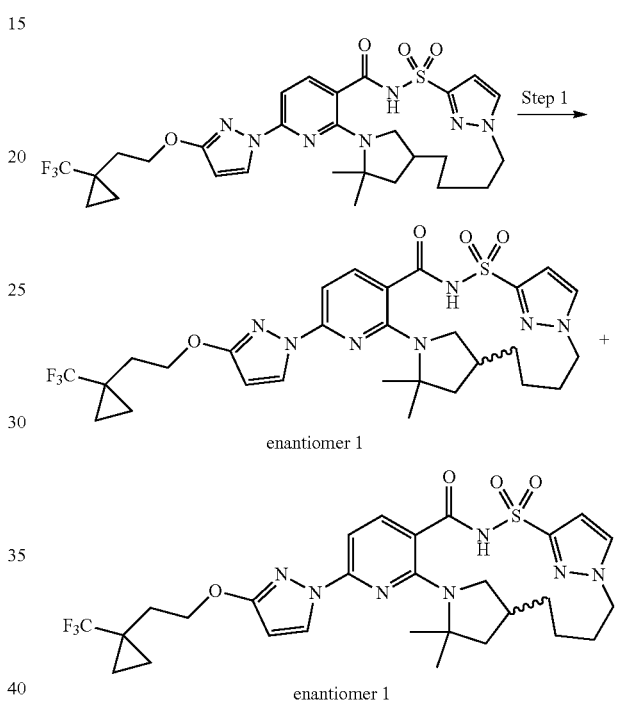

Step 1: 21,21-Dimethyl-4-(3-{2-[1-(trifluoromethyl)cyclopropyl]ethoxy}-1H-pyrazol-1-yl)-10λ6-thia-1,3,9,14,23-pentaazatetracyclo[17.2.1.111,14.02,7]tricosa-2,4,6,11(23),12-pentaene-8,10,10-trione (Enantiomer 1) (Compound 44) and 21,21-dimethyl-4-(3-{2-[1-(trifluoromethyl)cyclopropyl]ethoxy}-1H-pyrazol-1-yl)-10λ6-thia-1,3,9,14,23-pentaazatetracyclo[17.2.1.111,14.02,7]tricosa-2,4,6,11(23),12-pentaene-8,10,10-trione (Enantiomer 2) (Compound 45)

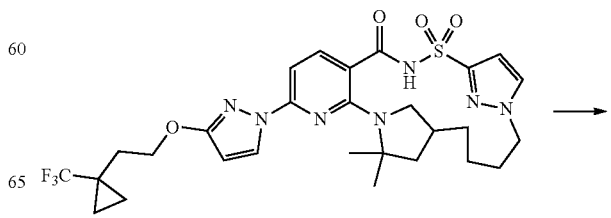

-continued

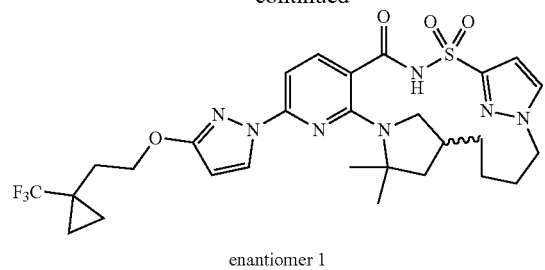

enantiomer 1

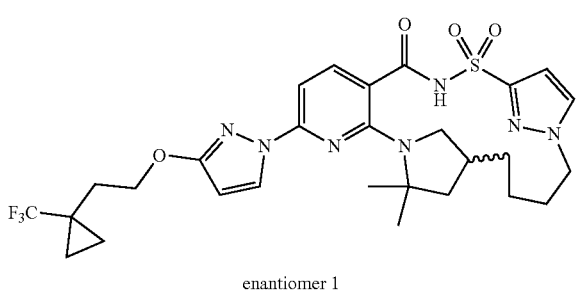

enantiomer 1

Racemic 21,21-dimethyl-4-(3-{2-[1-(trifluoromethyl)cyclopropyl]ethoxy}-1H-pyrazol-1-yl)-10$\lambda^6$-thia-1,3,9,14,23-pentaazatetracyclo[17.2.1.1$^{11,14}$.0$^{2,7}$]tricosa-2,4,6,11(23),12-pentaene-8,10,10-trione (160 mg, 0.2548 mmol) was subjected to chiral SFC chromatography using a ChiralPak AS-H (250×21.2 mm column, 5 μm particle size) with 25% acetonitrile:methanol (90:10)/75% carbon dioxide mobile phase at 70 mL/min giving as the first enantiomer to elute, 21,21-dimethyl-4-(3-{2-[1-(trifluoromethyl)cyclopropyl]ethoxy}-1H-pyrazol-1-yl)-10$\lambda^6$-thia-1,3,9,14,23-pentaazatetracyclo[17.2.1.1$^{11,14}$.0$^{2,7}$]tricosa-2,4,6,11(23),12-pentaene-8,10,10-trione (enantiomer 1) (Compound 44) (65.8 mg, 82%) as a white solid; ESI-MS m/z calc. 621.2345, found 622.4 (M+1)$^+$; Retention time: 2.2 min (LC Method E) and as the second enantiomer to elute, 21,21-dimethyl-4-(3-{2-[1-(trifluoromethyl)cyclopropyl]ethoxy}-1H-pyrazol-1-yl)-10$\lambda^6$-thia-1,3,9,14,23-pentaazatetracyclo[17.2.1.1$^{11,14}$.0$^{2,7}$]tricosa-2,4,6,11(23),12-pentaene-8,10,10-trione (enantiomer 2) (Compound 45) (70.8 mg, 89%) as a white solid; $^1$H NMR (400 MHz, dimethyl sulfoxide-d$_6$) δ 12.59 (s, 1H), 8.21 (d, J=2.8 Hz, 1H), 7.99 (s, 1H), 7.77 (d, J=7.2 Hz, 1H), 7.02-6.80 (m, 2H), 6.12 (d, J=2.7 Hz, 1H), 4.44-4.19 (m, 4H), 2.70 (d, J=21.3 Hz, 2H), 2.20 (s, 1H), 2.08 (t, J=7.1 Hz, 2H), 2.00 (d, J=6.6 Hz, 1H), 1.89 (dd, J=11.9, 5.6 Hz, 1H), 1.67 (d, J=5.7 Hz, 1H), 1.61 (s, 3H), 1.61-1.53 (m, 2H), 1.52 (s, 3H), 1.48 (d, J=12.2 Hz, 1H), 1.18-1.04 (m, 1H), 1.00-0.93 (m, 2H), 0.89 (s, 2H), 0.77 (s, 1H). ESI-MS m/z calc. 621.2345, found 622.4 (M+1)$^+$; Retention time: 2.2 min (LC Method E).

Example 126: Preparation of 12,12-dimethyl-8-(3-{2-[1-(trifluoromethyl)cyclopropyl]ethoxy}-1H-pyrazol-1-yl)-2$\lambda^6$-thia-3,9,11,20,25-pentaazatetracyclo[19.3.1.0$^{5,10}$.0$^{11,15}$]pentacosa-1(24),5,7,9,21(25),22-hexaene-2,2,4-trione (Enantiomer 1) (Compound 46) and 12,12-dimethyl-8-(3-{2-[1-(trifluoromethyl)cyclopropyl]ethoxy}-1H-pyrazol-1-yl)-2$\lambda^6$-thia-3,9,11,20,25-pentaazatetracyclo[19.3.1.0$^{5,10}$.0$^{11,15}$]pentacosa-1(24),5,7,9,21(25),22-hexaene-2,2,4-trione (Enantiomer 2) (Compound 47)

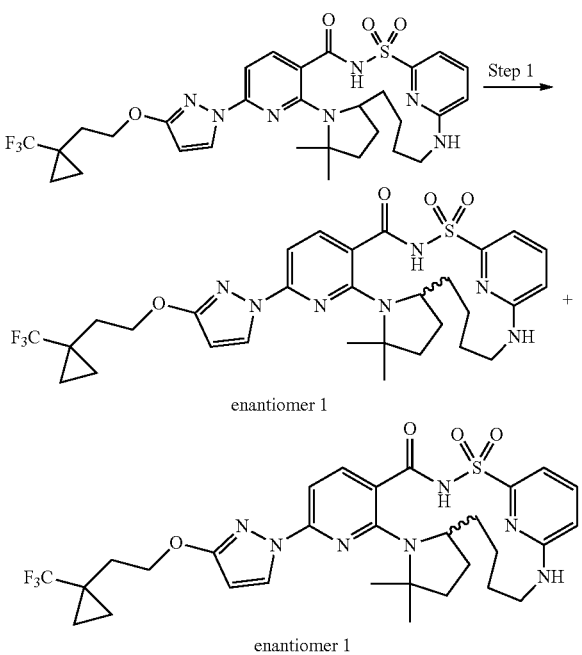

enantiomer 1

Step 1: 12,12-Dimethyl-8-(3-{2-[1-(trifluoromethyl)cyclopropyl]ethoxy}-1H-pyrazol-1-yl)-2$\lambda^6$-thia-3,9,11,20,25-pentaazatetracyclo[19.3.1.0$^{5,10}$.0$^{11,15}$]pentacosa-1(24),5,7,9,21(25),22-hexaene-2,2,4-trione (Enantiomer 1) (Compound 46) and 12,12-dimethyl-8-(3-{2-[1-(trifluoromethyl)cyclopropyl]ethoxy}-1H-pyrazol-1-yl)-2$\lambda^6$-thia-3,9,11,20,25-pentaazatetracyclo[19.3.1.0$^{5,10}$.0$^{11,15}$]pentacosa-1(24),5,7,9,21(25),22-hexaene-2,2,4-trione (Enantiomer 2) (Compound 47)

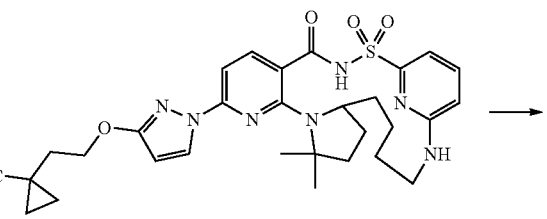

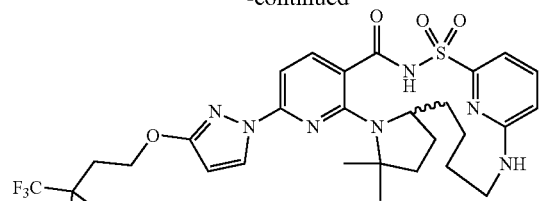

enantiomer 1

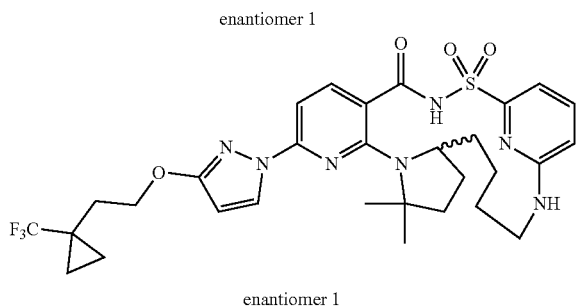

enantiomer 1

12,12-Dimethyl-8-(3-{2-[1-(trifluoromethyl)cyclopropyl]ethoxy}-1H-pyrazol-1-yl)-2$\lambda^6$-thia-3,9,11,20,25-pentaazatetracyclo[19.3.1.05,10.011,15]pentacosa-1(24),5,7,9,21(25),22-hexaene-2,2,4-trione (23 mg, 0.03320 mmol) was subjected to chiral SFC chromatography using a ChiralPak AS-H (250×10 mm column, 5 μm particle size) with 18% acetonitrile:methanol (90:10; No modifier))/82% carbon dioxide mobile phase at 10 mL/min giving as the first enantiomer to elute, 12,12-dimethyl-8-(3-{2-[1-(trifluoromethyl)cyclopropyl]ethoxy}-1H-pyrazol-1-yl)-2$\lambda^6$-thia-3,9,11,20,25-pentaazatetracyclo[19.3.1.05,10.011,15]pentacosa-1(24),5,7,9,21(25),22-hexaene-2,2,4-trione (enantiomer 1) (Compound 46) (6.9 mg, 64%); ESI-MS m/z calc. 647.2502, found 648.3 (M+1)+; Retention time: 1.97 min (LC Method B) and as the second enantiomer to elute, 12,12-dimethyl-8-(3-{2-[1-(trifluoromethyl)cyclopropyl]ethoxy}-1H-pyrazol-1-yl)-2$\lambda^6$-thia-3,9,11,20,25-pentaazatetracyclo[19.3.1.05,10.011,15]pentacosa-1(24),5,7,9,21(25),22-hexaene-2,2,4-trione (enantiomer 2) (Compound 47) (6.8 mg, 63%); ESI-MS m/z calc. 647.2502, found 648.3 (M+1)+; Retention time: 1.97 min (LC Method B).

Example 127: Preparation of 7,7-dimethyl-11-(3-{2-[1-(trifluoromethyl)cyclopropyl]ethoxy}-1H-pyrazol-1-yl)-17$\lambda^6$-thia-2,8,10,16,22-pentaazatetracyclo[16.3.1.04,8.09,14]docosa-1(22),9,11,13,18,20-hexaene-15,17,17-trione (Enantiomer 1) (Compound 50) and 7,7-dimethyl-11-(3-{2-[1-(trifluoromethyl)cyclopropyl]ethoxy}-1H-pyrazol-1-yl)-17$\lambda^6$-thia-2,8,10,16,22-pentaazatetracyclo[16.3.1.04,8.09,14]docosa-1(22),9,11,13,18,20-hexaene-15,17,17-trione (Enantiomer 2) (Compound 51)

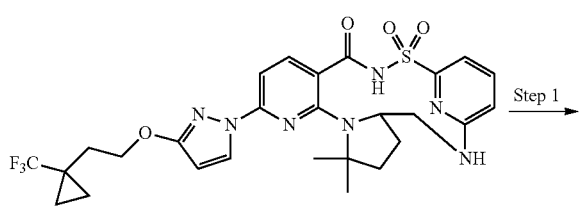

Step 1

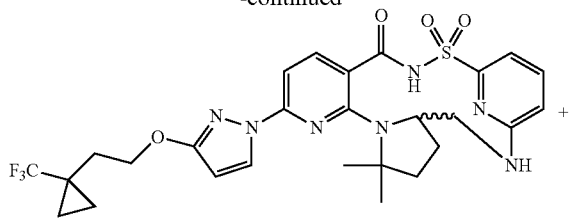

enantiomer 1

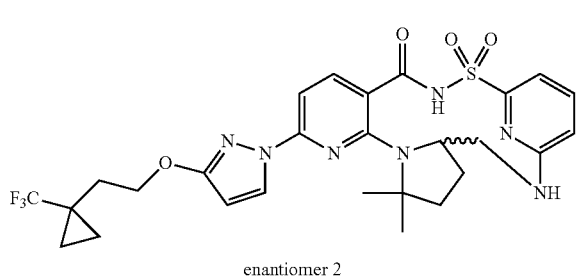

enantiomer 2

Step 1: 7,7-Dimethyl-11-(3-{2-[1-(trifluoromethyl)cyclopropyl]ethoxy}-1H-pyrazol-1-yl)-17$\lambda^6$-thia-2,8,10,16,22-pentaazatetracyclo[16.3.1.04,8.09,14]docosa-1(22),9,11,13,18,20-hexaene-15,17,17-trione (Enantiomer 1) (Compound 50) and 7,7-dimethyl-11-(3-{2-[1-(trifluoromethyl)cyclopropyl]ethoxy}-1H-pyrazol-1-yl)-17$\lambda^6$-thia-2,8,10,16,22-pentaazatetracyclo[16.3.1.04,8.09,14]docosa-1(22),9,11,13,18,20-hexaene-15,17,17-trione (Enantiomer 2) (Compound 51)

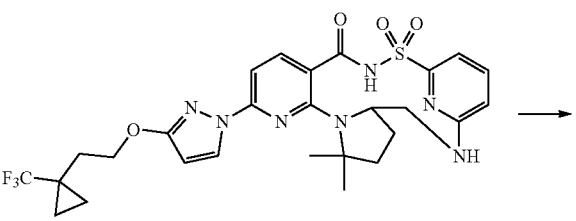

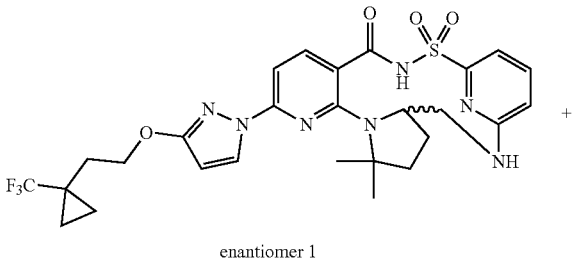

enantiomer 1

887

-continued

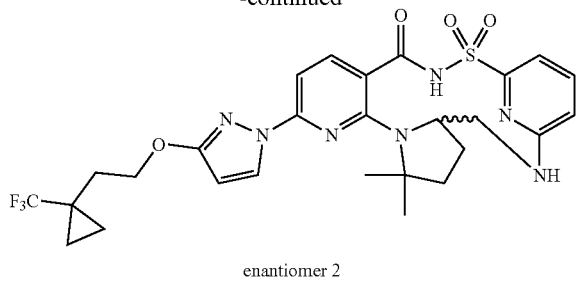

enantiomer 2

Subjected racemic 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.04,8.09,14]docosa-1(22),9,11,13,18,20-hexaene-15,17,17-trione (26 mg, 0.04246 mmol) to chiral separation by SFC chromatography using a ChiralPak AS-H (250×10 mm column, 5 µm particle size) with 32% acetonitrile/methanol (90:10; No modifier)/68% carbon dioxide mobile phase at 10 mL/min (injection volume=70 µL of 24 mg/mL solution in acetonitrile/methanol (90:10)) giving as the first enantiomer to elute 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.04,8.09,14]docosa-1(22),9,11,13,18,20-hexaene-15,17,17-trione (enantiomer 1) (Compound 50) (11.8 mg, 92%) as a white solid; ESI-MS m/z calc. 605.2032, found 606.3 (M+1)⁺; Retention time: 1.93 min (LC Method B) and as the second enantiomer to elute 7,7-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.04,8.09,14]docosa-1(22),9,11,13,18,20-hexaene-15,17,17-trione (enantiomer 2) (Compound 51) (12.8 mg, 100%) as a white solid; ESI-MS m/z calc. 605.2032, found 606.3 (M+1)⁺; Retention time: 1.93 min (LC Method B).

Example 128: Preparation of (14R)-8-[3-(3,3-dicyclopropylpropoxy)-1H-pyrazol-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Compound 65)

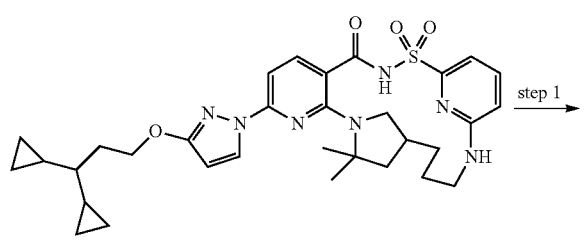

888

-continued

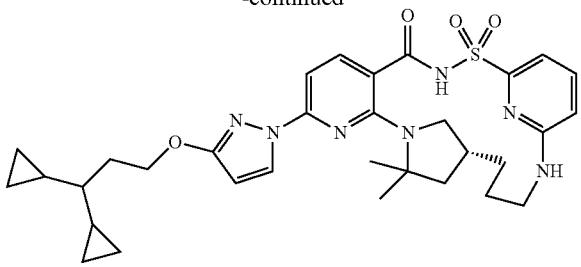

Step 1: (14R)-8-[3-(3,3-Dicyclopropylpropoxy)-1H-pyrazol-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Compound 65)

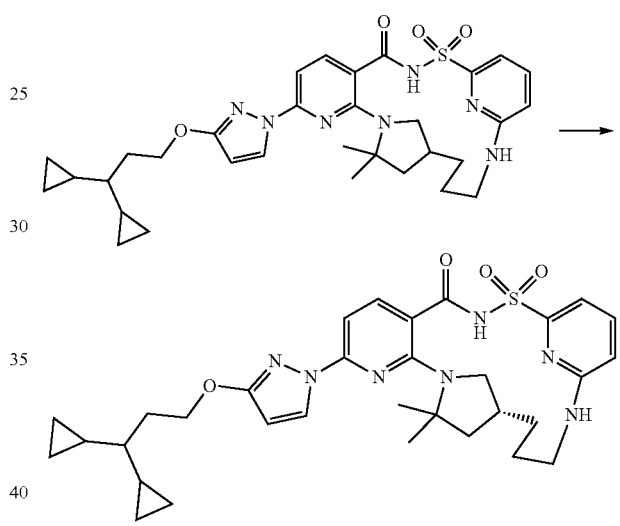

Subjected racemic 8-[3-(3,3-dicyclopropylpropoxy)-1H-pyrazol-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione to chiral separation by SFC chromatography using a ChiralPak AS-H (250×21.2 mm column, 5 µm particle size) with 38% acetonitrile:methanol (90:10))/62% carbon dioxide mobile phase at 70 mL/min giving as the first enantiomer to elute, (14R)-8-[3-(3,3-dicyclopropylpropoxy)-1H-pyrazol-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Compound 65) (51.2 mg, 36%) as a white solid. ¹H NMR (400 MHz, Chloroform-d) δ 10.10 (s, 1H), 8.20 (d, J=2.8 Hz, 1H), 8.06 (d, J=8.2 Hz, 1H), 7.55 (s, 1H), 7.50 (d, J=6.8 Hz, 1H), 7.28 (s, 1H), 6.57 (s, 1H), 5.91 (d, J=2.7 Hz, 1H), 4.69 (s, 1H), 4.43 (t, J=6.8 Hz, 2H), 3.92 (s, 1H), 3.34 (t, J=8.4 Hz, 1H), 3.17 (s, 1H), 3.06 (s, 1H), 2.07 (dd, J=12.1, 7.5 Hz, 1H), 1.97 (q, J=6.8 Hz, 2H), 1.62 (d, J=4.7 Hz, 10H), 0.67 (ddt, J=13.3, 8.5, 4.2 Hz, 2H), 0.44 (tdd, J=8.1, 5.0, 3.7 Hz, 4H), 0.37-0.29 (m, 1H), 0.20 (dq, J=6.5, 4.2, 3.6 Hz, 2H), 0.11 (dp, J=9.7, 4.7 Hz, 2H). ESI-MS m/z calc. 619.29407, found 620.23 (M+1)⁺; Retention time: 1.94 min (LC Method G).

Example 129: Preparation of 12,12-dimethyl-8-(3-{2-[1-(trifluoromethyl)cyclopropyl]ethoxy}-1H-pyrazol-1-yl)-2λ⁶-thia-3,9,11,19,21-pentaazatetracyclo[18.2.2.1¹¹,¹⁴.0⁵,¹⁰]pentacosa-1(23),5,7,9,20(24),21-hexaene-2,2,4-trione (Enantiomer 1) (Compound 67) and 12,12-dimethyl-8-(3-{2-[1-(trifluoromethyl)cyclopropyl]ethoxy}-1H-pyrazol-1-yl)-2λ⁶-thia-3,9,11,19,21-pentaazatetracyclo[18.2.2.1¹¹,¹⁴.0⁵,¹⁰]pentacosa-1(23),5,7,9,20(24),21-hexaene-2,2,4-trione (Enantiomer 2) (Compound 68)
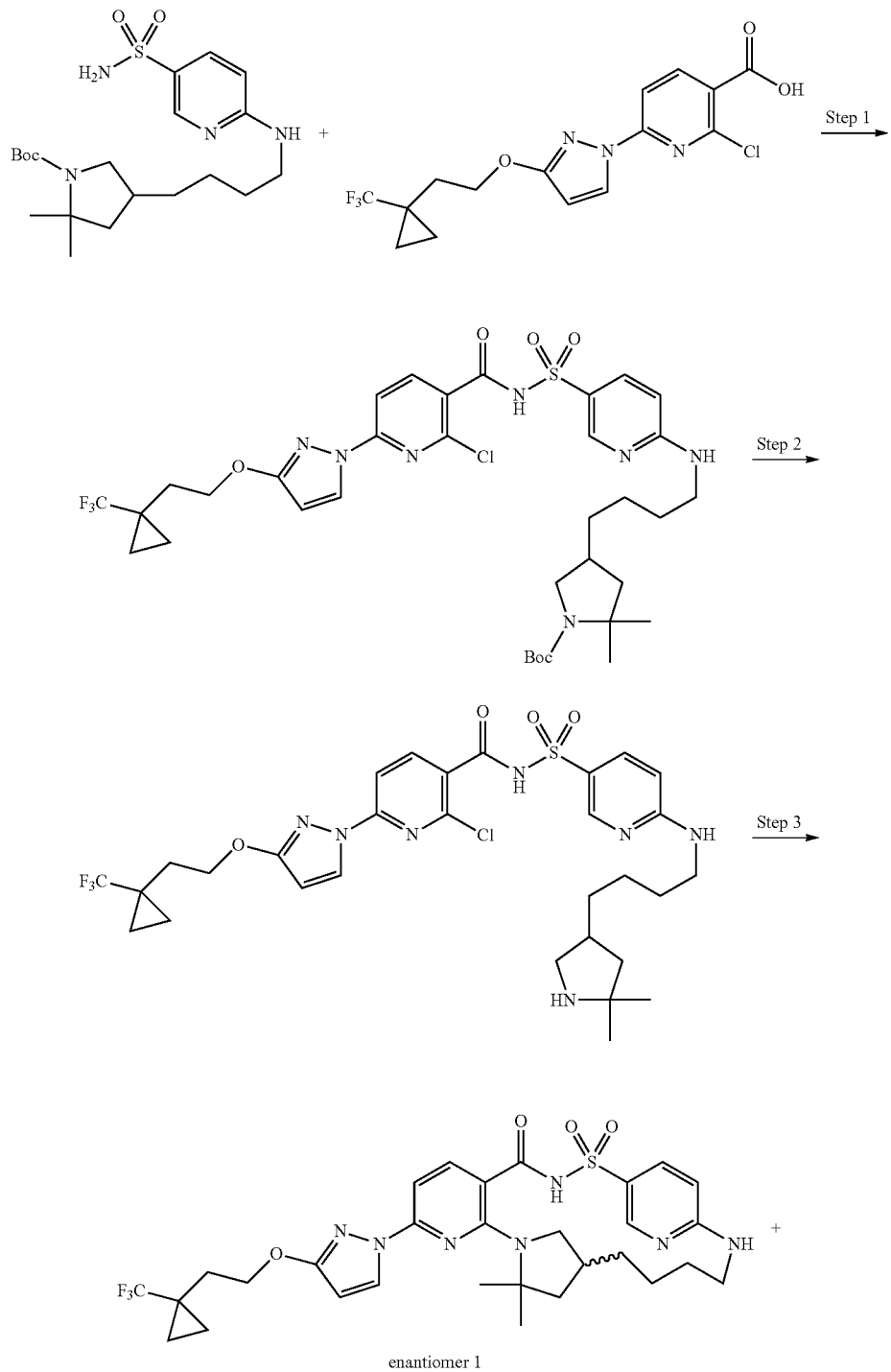

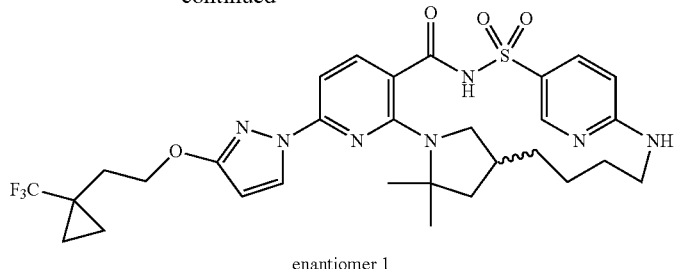

enantiomer 1

Step 1: tert-Butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate

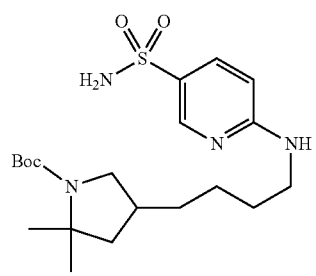

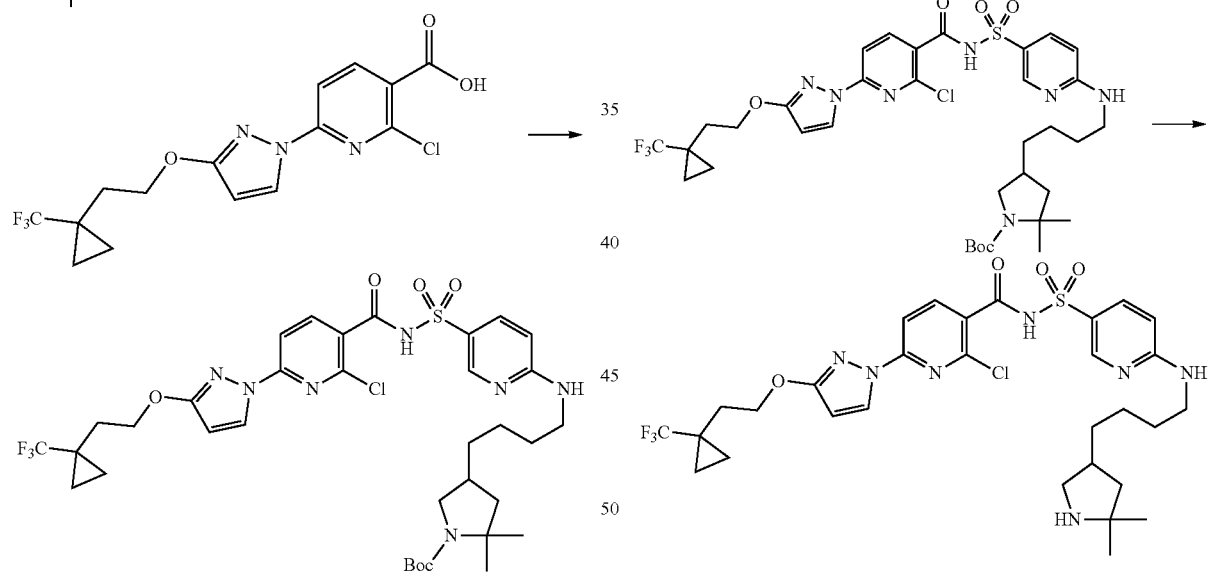

In a 20 mL vial, 2-chloro-6-[3-[2-[1-(trifluoromethyl)cyclopropyl]ethoxy]pyrazol-1-yl]pyridine-3-carboxylic acid (353.0 mg, 0.9396 mmol) and carbonyl diimidazole (152.4 mg, 0.9396 mmol) were combined in tetrahydrofuran (3.834 mL) and stirred for 120 min at 50° C. with a loose cap. Then tert-butyl 2,2-dimethyl-4-[4-[(5-sulfamoyl-2-pyridyl)amino]butyl]pyrrolidine-1-carboxylate (267.2 mg, 0.6264 mmol) in tetrahydrofuran (5.114 mL) was added followed by 1,8-diazabicyclo[5.4.0]undec-7-ene (187.4 μL, 1.253 mmol) and the reaction was heated at 50° C. for 16 h. The reaction was diluted with ethyl acetate and washed with saturated aqueous ammonium chloride followed by brine. The organics were separated, dried over sodium sulfate, filtered and evaporated then purified by silica gel chromatography using a shallow gradient from 100% hexanes to 100% ethyl acetate giving tert-butyl 4-[4-[[5-[[2-chloro-6-[3-[2-[1-(trifluoromethyl)cyclo propyl]ethoxy]pyrazol-1-yl]pyridine-3-carbonyl]sulfamoyl]-2-pyridyl]amino]butyl]-2,2-dimethyl-pyrrolidine-1-carboxylate (422.4 mg, 86%) as a white solid. ESI-MS m/z calc. 783.27924, found 784.2 (M+1)+; Retention time: 0.86 min (LC Method A).

Step 2: 2-Chloro-N-[[6-[4-(5,5-dimethylpyrrolidin-3-yl)butylamino]-3-pyridyl]sulfonyl]-6-[3-[2-[1-(trifluoromethyl)cyclopropyl]ethoxy]pyrazol-1-yl]pyridine-3-carboxamide tert-Butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]amino]butyl]-2,2-dimethyl-pyrrolidine-1-carboxylate (422.4 mg, 0.5386 mmol) was dissolved in dichloromethane (1.843 mL) and to the mixture was added trifluoroacetic acid (1.904 mL, 24.71 mmol) and the mixture was stirred at room temperature for 60 min. Concentrated the mixture to dryness under reduced pressure, took up in saturated aqueous sodium bicarbonate and ethyl acetate and separated the layers. (CAUTION, solubility of product in ethyl acetate under these conditions is poor, addition of some methanol helps, needed to evaporate the organic layer without using solid drying agent). Concentrated the organic layer by rotary evaporation followed by drying under vacuum giving 2-chloro-N-[[6-[4-(5,5-dimethylpyrrolidin-3-yl)butylamino]-3-pyridyl]sulfonyl]-6-[3-[2-[1-(trifluoromethyl)cyclopropyl]ethoxy]pyrazol-1-yl]pyridine-3-carboxamide (323.6 mg, 88%)) as an off-white solid. ESI-MS m/z calc. 683.2268, found 684.2 (M+1)$^+$; Retention time: 0.58 min (LC Method A).

Step 3: 12,12-Dimethyl-8-(3-{2-[1-(trifluoromethyl)cyclopropyl]ethoxy}-1H-pyrazol-1-yl)-2$\lambda^6$-thia-3,9,11,19,21-pentaazatetracyclo[18.2.2.111,14.05,10]pentacosa-1(23),5,7,9,20(24),21-hexaene-2,2,4-trione (Enantiomer 1) (Compound 67) and 12,12-dimethyl-8-(3-{2-[1-(trifluoromethyl)cyclopropyl]ethoxy}-1H-pyrazol-1-yl)-2$\lambda^6$-thia-3,9,11,19,21-pentaazatetracyclo[18.2.2.111,14.05,10]pentacosa-1(23),5,7,9,20(24),21-hexaene-2,2,4-trione (Enantiomer 2) (Compound 68)

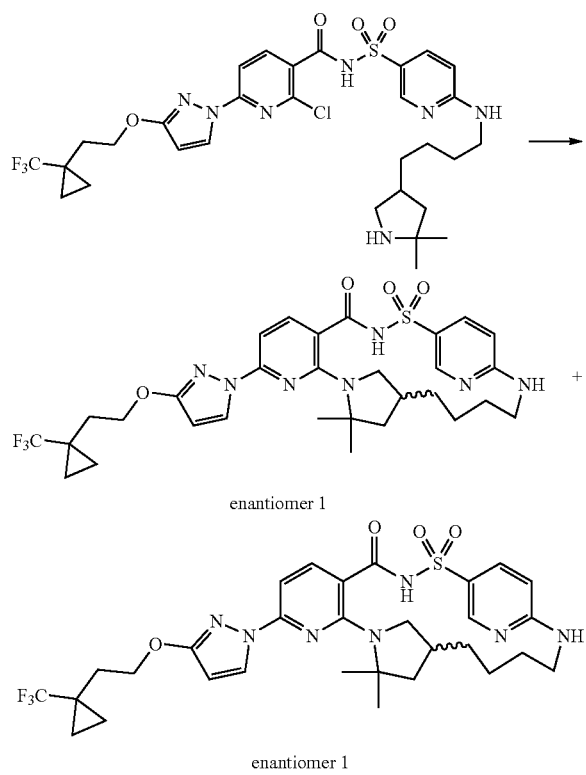

To a solution of 2-chloro-N-[[6-[(5,5-dimethylpyrrolidin-3-yl)butylamino]-3-pyridyl]sulfonyl]-6-[3-[2-[1-(trifluoromethyl)cyclopropyl]ethoxy]pyrazol-1-yl]pyridine-3-carboxamide (323.6 mg, 0.4730 mmol) in dimethyl sulfoxide (12.94 mL) was added potassium carbonate (392.2 mg, 2.838 mmol), CsF (86.22 mg, 0.5676 mmol), and a small amount of 3 Å molecular sieves. The resulting mixture was capped and heated to 165° C. for 16 h. The mixture was then cooled to room temperature, diluted with ethyl acetate and washed with saturated aqueous NH$_4$Cl and brine. The organic phase was dried (sodium sulfate), filtered and concentrated to 422 mg of a tan amorphous solid which was subjected to chiral SFC chromatography using a ChiralPak OD-3 column eluting with isocratic 30% methanol (20 mM NH$_3$ modifier)/70% carbon dioxide mobile phase over a 2 minute run to give a single enantiomer of the expected product (first eluting, peak 1) which still contained some impurities and another single enantiomer of the expected product (second eluting, peak 2) which still contained some impurities, both as white solids.

The first eluting peak 1 from the SFC chiral separation (50.2 mg) was filtered and purified using a reverse phase HPLC-MS method using a Luna C$_{18}$ (2) column (75×30 mm, 5 μm particle size) sold by Phenomenex (pn: 00C-4252-U0-AX) and a dual gradient run from 1%-99% mobile phase B over 15.0 min (mobile phase A=water (5 mM hydrochloric acid), mobile phase B=acetonitrile, flow rate=50 mL/min, injection volume=950 μL and column temperature=25° C.) giving 12,12-dimethyl-8-(3-{2-[1-(trifluoromethyl)cyclopropyl]ethoxy}-1H-pyrazol-1-yl)-2$\lambda^6$-thia-3,9,11,19,21-pentaazatetracyclo[18.2.2.111,14.05,10]pentacosa-1(23),5,7,9,20(24),21-hexaene-2,2,4-trione (enantiomer 1) (Compound 67) (27.7 mg, 18%) as a white solid. $^1$H NMR (400 MHz, dimethyl sulfoxide-d$_6$) δ 12.15 (s, 1H), 8.47 (s, 1H), 8.19 (d, J=2.7 Hz, 1H), 7.81 (d, J=8.3 Hz, 1H), 7.30 (s, 1H), 6.89 (d, J=8.3 Hz, 1H), 6.56 (d, J=8.9 Hz, 1H), 6.10 (d, J=2.7 Hz, 1H), 4.31 (t, J=7.0 Hz, 2H), 2.45 (s, 1H), 2.07 (t, J=7.1 Hz, 3H), 1.99 (s, 1H), 1.72 (s, 1H), 1.54 (s, 10H), 1.25 (d, J=9.7 Hz, 2H), 1.05 (s, 2H), 0.99-0.92 (m, 2H), 0.92-0.84 (m, 2H). ESI-MS m/z calc. 647.2502, found 648.2 (M+1)$^+$; Retention time: 2.12 min (LC Method B).

The second eluting peak 2 from the SFC chiral separation (46.5 mg) was filtered and purified using a reverse phase HPLC-MS method using a Luna C$_{18}$ (2) column (75×30 mm, 5 μm particle size) sold by Phenomenex (pn: 00C-4252-U0-AX) and a dual gradient run from 1%-99% mobile phase B over 15.0 min (mobile phase A=water (5 mM hydrochloric acid), mobile phase B=acetonitrile, flow rate=50 mL/min, injection volume=950 μL and column temperature=25° C.) giving 12,12-dimethyl-8-(3-{2-[1-(trifluoromethyl)cyclopropyl]ethoxy}-1H-pyrazol-1-yl)-2$\lambda^6$-thia-3,9,11,19,21-pentaazatetracyclo[18.2.2.111,14.05,10]pentacosa-1(23),5,7,9,20(24),21-hexaene-2,2,4-trione (enantiomer 2) (Compound 68) (29.4 mg, 19%) as a white solid. $^1$H NMR (400 MHz, dimethyl sulfoxide-d$_6$) δ 12.15 (s, 1H), 8.46 (s, 1H), 8.19 (d, J=2.8 Hz, 1H), 7.80 (d, J=8.5 Hz, 1H), 7.28 (s, 1H), 6.88 (d, J=8.3 Hz, 1H), 6.55 (d, J=8.9 Hz, 1H), 6.10 (d, J=2.7 Hz, 1H), 4.31 (t, J=7.0 Hz, 2H), 2.07 (t, J=7.1 Hz, 3H), 1.99 (s, 1H), 1.72 (d, J=10.9 Hz, 1H), 1.54 (d, J=1.3 Hz, 10H), 1.29-1.14 (m, 2H), 1.04 (s, 2H), 0.97-0.94 (m, 2H), 0.91-0.86 (m, 2H). ESI-MS m/z calc. 647.2502, found 648.2 (M+1)$^+$; Retention time: 2.11 min (LC Method B).

Example 130: Preparation of 12,12-dimethyl-8-(3-{2-[1-(trifluoromethyl)cyclopropyl]ethoxy}-1H-pyrazol-1-yl)-15-oxa-2$\lambda^6$-thia-3,9,11,18,23-pentaazatetracyclo[17.3.1.111,14.05,10]tetracosa-1(22),5(10),6,8,19(23),20-hexaene-2,2,4-trione (Compound 69)

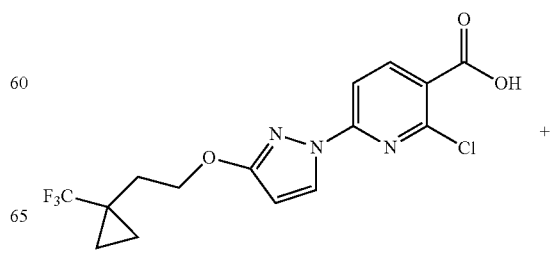

895

-continued

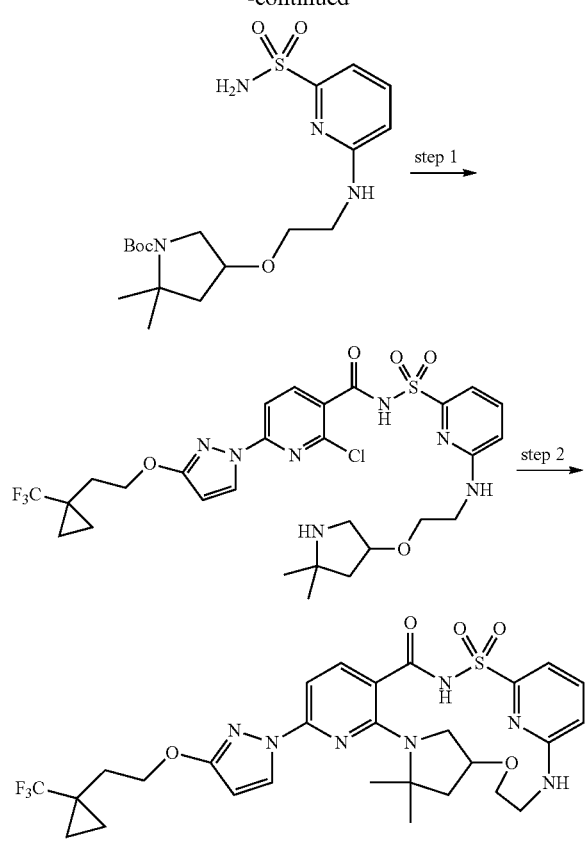

Step 1: tert-Butyl 4-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethoxy]-2,2-dimethyl-pyrrolidine-1-carboxylate

896

-continued

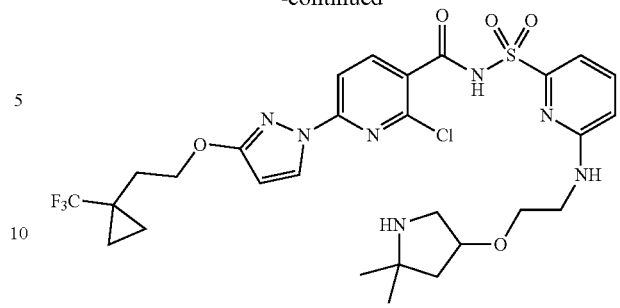

2-Chloro-6-[3-[2-[1-(trifluoromethyl)cyclopropyl]ethoxy]pyrazol-1-yl]pyridine-3-carboxylic acid (154 mg, 0.4099 mmol) and carbonyl diimidazole (66 mg, 0.4070 mmol) were combined in tetrahydrofuran (2.0 mL) and stirred for 90 min at 50° C. Then tert-butyl 2,2-dimethyl-4-[2-[(6-sulfamoyl-2-pyridyl)amino]ethoxy]pyrrolidine-1-carboxylate (94 mg, 0.2268 mmol) was added followed by 1,8-diazabicyclo[5.4.0]undec-7-ene (85.0 μL, 0.5684 mmol) and the reaction was heated at 50° C. for 36 h. The reaction was diluted with ethyl acetate and washed with a 1 M citric acid solution, followed by brine. The organics were separated, dried over sodium sulfate, filtered and evaporated and then purified by reverse-phase preparative chromatography utilizing a $C_{18}$ column (30%-99% acetonitrile in water (5 mM hydrochloric acid) to afford as a white solid, tert-butyl 4-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethoxy]-2,2-dimethyl-pyrrolidine-1-carboxylate (77 mg, 44%). ESI-MS m/z calc. 771.24286, found 772.2 (M+1)$^+$; Retention time: 2.28 min (LC Method E).

Step 2: 12,12-Dimethyl-8-(3-{2-[1-(trifluoromethyl)cyclopropyl]ethoxy}-1H-pyrazol-1-yl)-15-oxa-2λ$^6$-thia-3,9,11,18,23-pentaazatetracyclo[17.3.1.1$^{11,14}$.0$^{5,10}$]tetracosa-1(22),5(10),6,8,19(23),20-hexaene-2,2,4-trione (Compound 69)

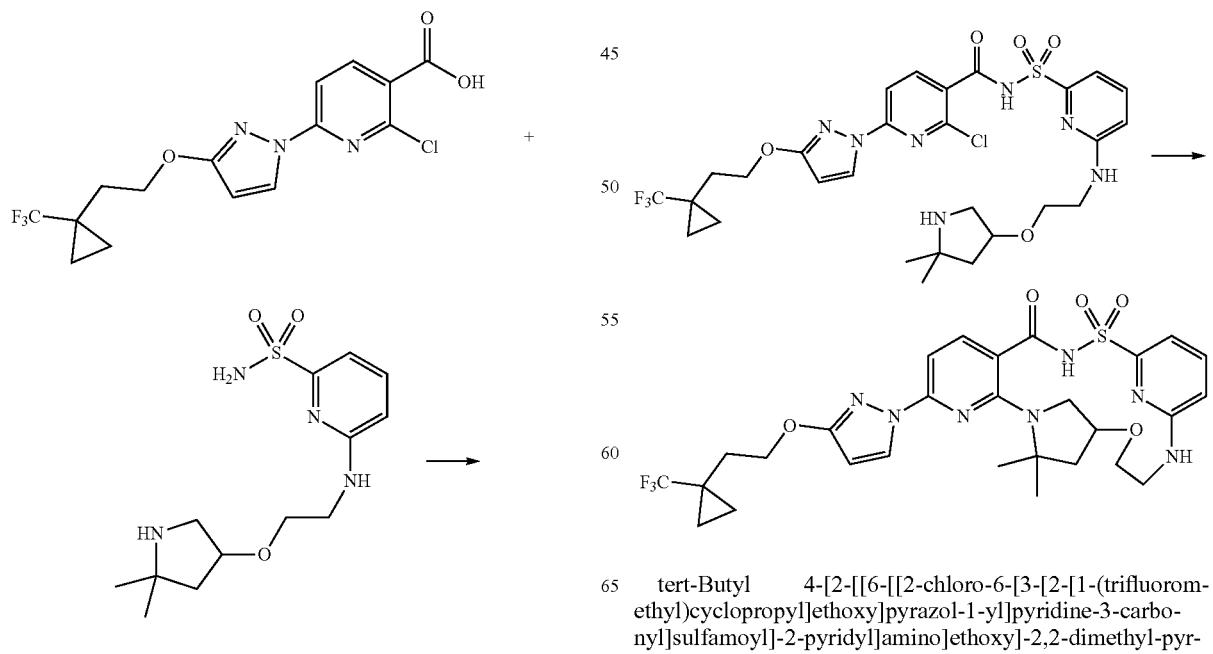

tert-Butyl 4-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethoxy]-2,2-dimethyl-pyrrolidine-1-carboxylate (77 mg, 0.09971 mmol) was dissolved in dichloromethane (1.6 mL) and to the mixture was added hydrochloric acid (800 μL of 4 M in dioxane, 3.200 mmol) and the mixture was stirred at room temperature for 30 min. Concentrated the mixture to dryness under reduced pressure, redissolved in ethyl acetate and then added aqueous 2 M sodium carbonate (5 mL), giving pH~10. Extracted the organic layer with ethyl acetate (2×10 mL), washed with brine, then dried over sodium sulfate, filtered and evaporated to dryness under reduced pressure. Combined the resulting material from and potassium carbonate (72 mg, 0.5210 mmol), cesium fluoride (25.0 mg, 0.1646 mmol), 3 Å molecular sieves and dimethyl sulfoxide (1.6 mL) in a vial, purged with nitrogen, capped, heated to 150° C. and stirred for 20 h. Cooled to room temperature, filtered and then purified by reverse-phase preparative chromatography utilizing a $C_{18}$ column (30%-99% acetonitrile in water (5 mM hydrochloric acid) to afford as a white solid, 12,12-dimethyl-8-(3-{2-[1-(trifluoromethyl)cyclopropyl]ethoxy}-1H-pyrazol-1-yl)-15-oxa-2λ⁶-thia-3,9,11,18,23-pentaazatetracyclo[17.3.1.111,14.05,10]tetracosa-1(22),5(10),6,8,19 (23),20-hexaene-2,2,4-trione (Compound 69) (38.8 mg, 61%). $^1$H NMR (400 MHz, dimethyl sulfoxide-$d_6$) δ 12.59 (s, 1H), 8.20 (d, J=2.8 Hz, 1H), 7.80 (d, J=8.2 Hz, 1H), 7.59 (dd, J=8.5, 7.3 Hz, 1H), 7.13 (d, J=7.7 Hz, 1H), 7.10 (d, J=7.0 Hz, 1H), 6.94 (d, J=8.2 Hz, 1H), 6.71 (d, J=8.2 Hz, 1H), 6.11 (d, J=2.7 Hz, 1H), 4.31 (t, J=7.0 Hz, 2H), 4.11 (td, J=12.8, 5.9 Hz, 2H), 3.88 (t, J=11.6 Hz, 1H), 3.61 (dd, J=8.7, 4.2 Hz, 1H), 3.32-3.20 (m, 1H), 3.06 (dd, J=10.6, 5.0 Hz, 1H), 2.92-2.77 (m, 1H), 2.08 (t, J=7.1 Hz, 3H), 1.79 (t, J=10.9 Hz, 1H), 1.57 (d, J=9.8 Hz, 6H), 1.00-0.93 (m, 2H), 0.88 (s, 2H). ESI-MS m/z calc. 635.21375, found 636.2 (M+1)⁺; Retention time: 2.0 min (LC Method E).

Example 131: Preparation of 21,21,23-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.111,14.02,7]tricosa-2,4,6,11(23),12-pentaene-8,10,10-trione (Compound 76) and 12,21, 21-trimethyl-4-(3-{2-[1-(trifluoromethyl) cyclopropyl]ethoxy}-1H-pyrazol-1-yl)-10λ⁶-thia-1, 3,9,13,14-pentaazatetracyclo[17.2.1.111,14.02,7] tricosa-2,4,6,11(23),12-pentaene-8,10,10-trione (Compound 71)

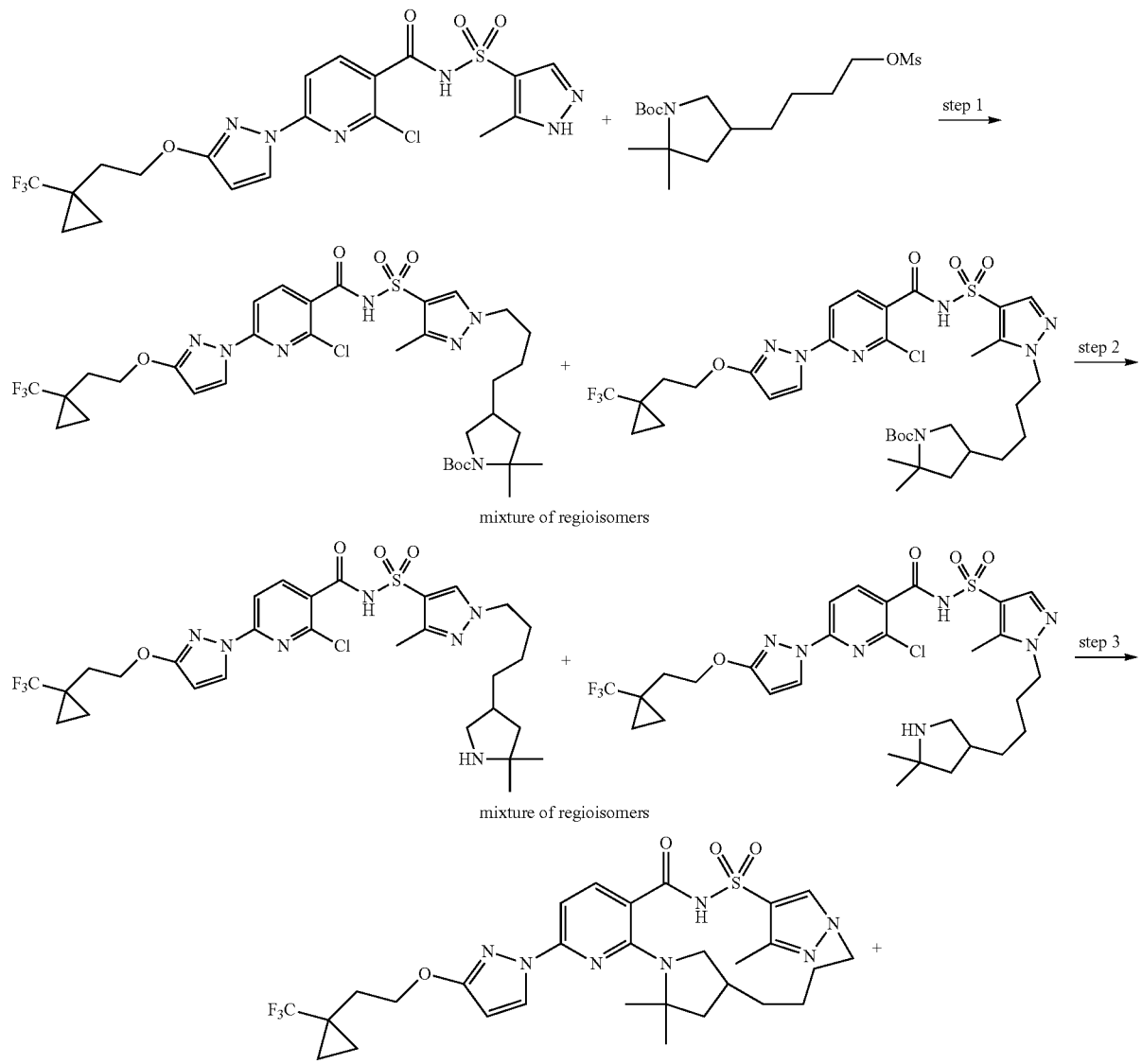

-continued

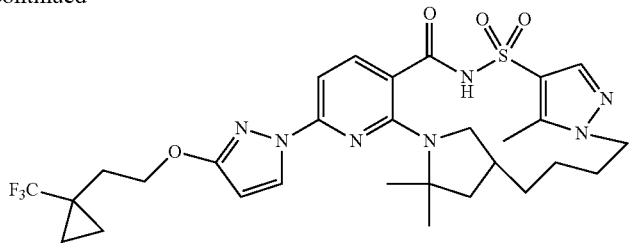

Step 1: tert-Butyl 4-[4-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]butyl]-2,2-dimethyl-pyrrolidine-1-carboxylate and tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]butyl]-2,2-dimethyl-pyrrolidine-1-carboxylate (Mixture of Regioisomers)

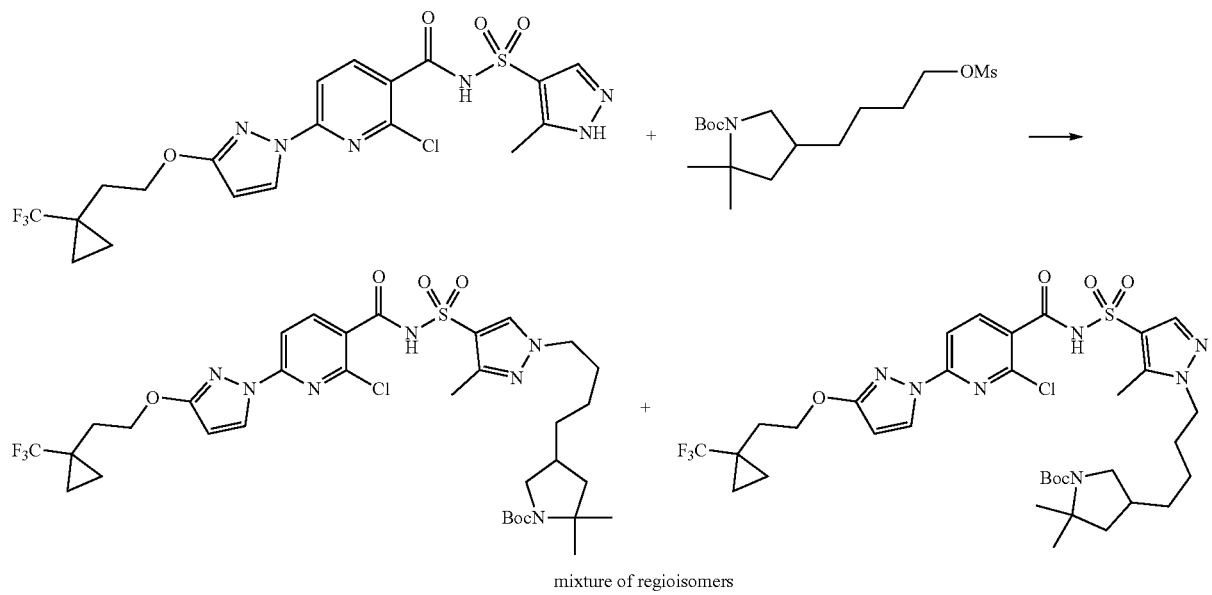

mixture of regioisomers

To a vial was added 2-chloro-N-[(5-methyl-1H-pyrazol-4-yl)sulfonyl]-6-[3-[2-[1-(trifluoromethyl)cyclopropyl]ethoxy]pyrazol-1-yl]pyridine-3-carboxamide (454 mg, 0.8749 mmol), N,N-dimethylformamide (4 mL), and potassium carbonate (424 mg, 3.068 mmol). The reaction was stirred for 5 min and room temperature and then tert-butyl 2,2-dimethyl-4-(4-methylsulfonyloxybutyl)pyrrolidine-1-carboxylate (410 mg, 1.173 mmol) in N,N-dimethylformamide (2 mL) was added dropwise. The reaction was placed in an 80° C. oil bath overnight. The reaction was cooled to room temperature, filtered, and purified via HPLC (10%-99% acetonitrile:water with a 0.1% hydrochloric acid modifier giving tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]butyl]-2,2-dimethyl-pyrrolidine-1-carboxylate and tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]butyl]-2,2-dimethyl-pyrrolidine-1-carboxylate (mixture of regioisomers) (184.3 mg, 27%). ESI-MS m/z calc. 771.27924, found 772.7 (M+1)$^+$; Retention time: 1.85 min (LC Method G).

Step 2: 2-Chloro-N-[1-[4-(5,5-dimethylpyrrolidin-3-yl)butyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[4-(5,5-dimethylpyrrolidin-3-yl)butyl]-5-methyl-pyrazol-4-yl]sulfonyl-6-[3-[2-[1-(trifluoromethyl)cyclopropyl]ethoxy]pyrazol-1-yl]pyridine-3-carboxamide (Mixture of Regioisomers)

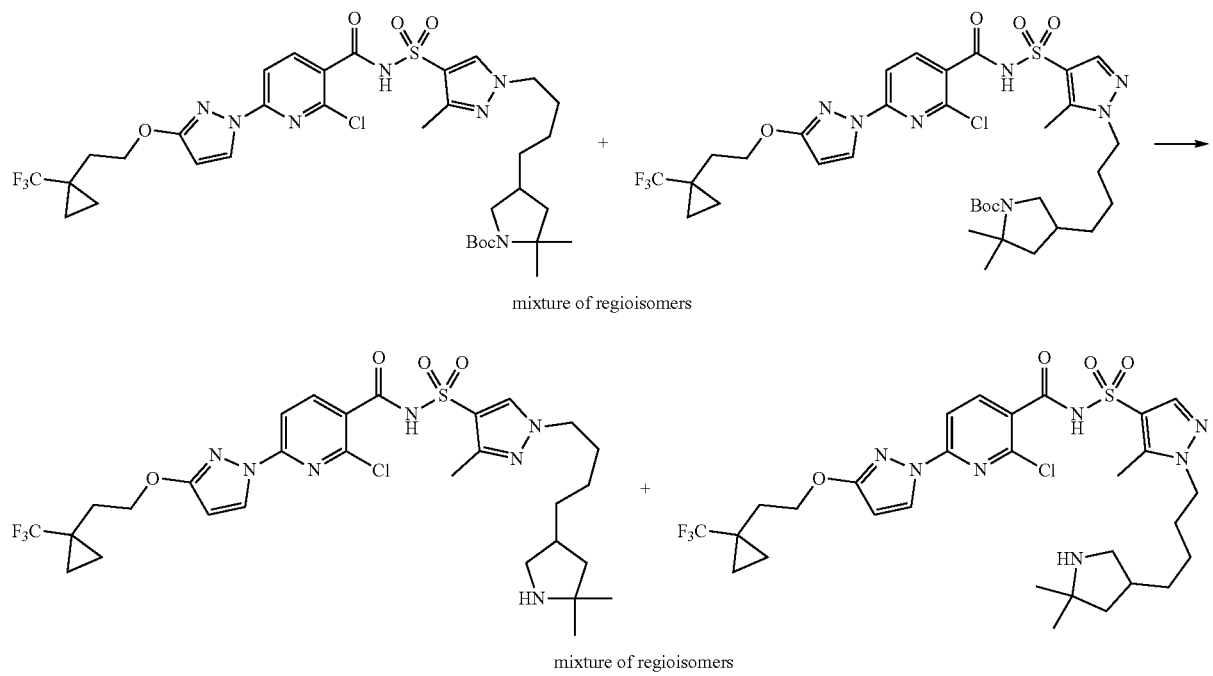

To a flask was added tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]butyl]-2,2-dimethyl-pyrrolidine-1-carboxylate and tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]butyl]-2,2-dimethyl-pyrrolidine-1-carboxylate (mixture of regioisomers) (81 mg, 0.1049 mmol), dichloromethane (3 mL) and trifluoroacetic acid (450 µL, 5.841 mmol). The reaction was stirred at room temperature for 90 min. The reaction was evaporated. The residue was washed with 2 M potassium carbonate and extracted with ethyl acetate. The organic layer was dried over sodium sulfate, filtered and evaporated to provide 2-chloro-N-[1-[4-(5,5-dimethylpyrrolidin-3-yl)butyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[4-(5,5-dimethylpyrrolidin-3-yl)butyl]-5-methyl-pyrazol-4-yl]sulfonyl-6-[3-[2-[1-(trifluoromethyl)cyclopropyl]ethoxy]pyrazol-1-yl]pyridine-3-carboxamide (mixture of regioisomers) (70 mg, 99%). ESI-MS m/z calc. 671.2268, found 672.2 (M+1)$^+$; Retention time: 1.64 min (LC Method B).

Step 3: 21,21,23-Trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Compound 76) and 12,21,21-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Compound 71)

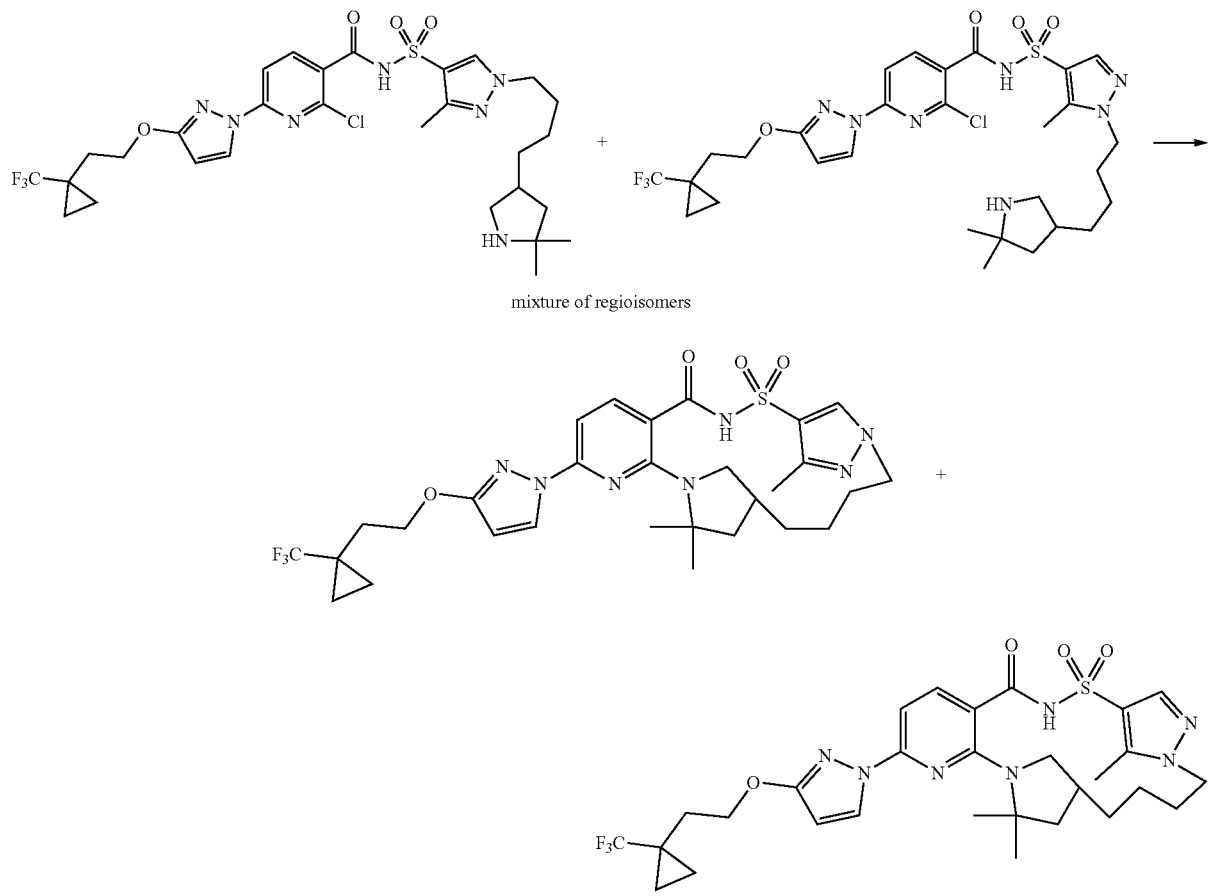

mixture of regioisomers

To 2-chloro-N-[1-[4-(5,5-dimethylpyrrolidin-3-yl)butyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[4-(5,5-dimethylpyrrolidin-3-yl)butyl]-5-methyl-pyrazol-4-yl]sulfonyl-6-[3-[2-[1-(trifluoromethyl)cyclopropyl]ethoxy]pyrazol-1-yl]pyridine-3-carboxamide (mixture of regioisomers) (70 mg, 0.1041 mmol) was added potassium carbonate (72 mg, 0.5210 mmol), cesium fluoride (36 mg, 0.2370 mmol), and dimethyl sulfoxide (800 μL). The reaction was heated at 150° C. overnight. The reaction was cooled to room temperature, filtered and purified via HPLC (20%-80% acetonitrile in water with a 0.1% hydrochloric acid modifier) giving as the first peak to elute, 12,21,21-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Compound 71) (16.6 mg, 50%);

¹H NMR (400 MHz, dimethyl sulfoxide-d₆) δ 12.25 (s, 1H), 8.63 (s, 1H), 8.21 (dd, J=4.5, 2.8 Hz, 1H), 7.85-7.74 (m, 1H), 6.92 (dd, J=8.3, 4.4 Hz, 1H), 6.11 (dd, J=2.7, 1.5 Hz, 1H), 4.31 (q, J=6.4, 5.9 Hz, 3H), 4.10 (dd, J=11.9, 6.8 Hz, 1H), 2.85 (t, J=10.1 Hz, 1H), 2.67 (bs, 1H), 2.39 (s, 3H), 2.15-2.02 (m, 4H), 1.83 (dd, J=11.8, 5.6 Hz, 1H), 1.58 (d, J=6.7 Hz, 4H), 1.51 (d, J=5.9 Hz, 5H), 1.19 (d, J=8.8 Hz, 2H), 1.02-0.93 (m, 2H), 0.93-0.85 (m, 2H), 0.13 (s, 1H), ESI-MS m/z calc. 635.2502, found 636.4 (M+1)⁺; Retention time: 2.14 min (LC Method B) and as the second peak to elute, 21,21,23-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Compound 76) (4.2 mg, 13%); ESI-MS m/z calc. 635.2502, found 636.3 (M+1)⁺; Retention time: 2.08 min (LC Method B)

Example 132: Preparation of 12,12-dimethyl-8-(3-
{2-[1-(trifluoromethyl)cyclopropyl]ethoxy}-1H-
pyrazol-1-yl)-15-oxa-2λ⁶-thia-3,9,11,18,23-pen-
taazatetracyclo[17.3.1.1¹¹,¹⁴.0⁵,¹⁰]tetracosa-1(22),
5(10),6,8,19(23),20-hexaene-2,2,4-trione
(Enantiomer 1) (Compound 74) and 12,12-dim-
ethyl-8-(3-{2-[1-(trifluoromethyl) cyclopropyl]
ethoxy}-1H-pyrazol-1-yl)-15-oxa-2λ⁶-thia-3,9,11,
18,23-pentaazatetracyclo[17.3.1.1¹¹,¹⁴.0⁵,¹⁰]
tetracosa-1(22),5(10),6,8,19(23),20-hexaene-2,2,4-
trione (Enantiomer 2) (Compound 75)

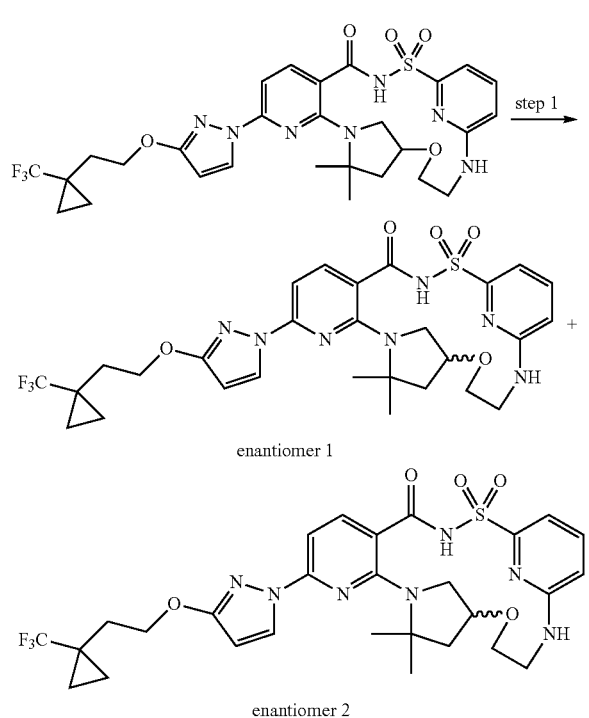

Step 1: 12,12-Dimethyl-8-(3-{2-[1-(trifluoromethyl)
cyclopropyl]ethoxy}-1H-pyrazol-1-yl)-15-oxa-2λ⁶-
thia-3,9,11,18,23-pentaazatetracyclo[17.3.1.1¹¹¹,
14.0⁵,¹⁰]tetracosa-1(22),5(10),6,8,19(23),20-
hexaene-2,2,4-trione (Enantiomer 1) (Compound
74) and 12,12-dimethyl-8-(3-{2-[1-(trifluoromethyl)
cyclopropyl]ethoxy}-1H-pyrazol-1-yl)-15-oxa-2λ⁶-
thia-3,9,11,18,23-pentaazatetracyclo[17.3.1.1¹¹¹,
14.0⁵,¹⁰]tetracosa-1(22),5(10),6,8,19(23),20-
hexaene-2,2,4-trione (Enantiomer 2) (Compound
75)

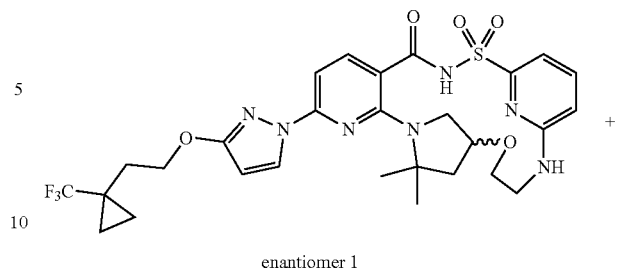

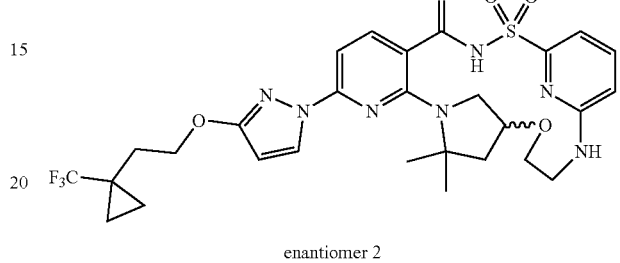

Racemic 12,12-dimethyl-8-(3-{2-[1-(trifluoromethyl)cyclopropyl]ethoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (36 mg, 0.05607 mmol) was subjected to chiral separation by SFC chromatography using a ChiralPak AS-H (250×21.2 mm column, 5 μm particle size) with a gradient from 5% to 60% methanol (20 mM NH₃) in carbon dioxide mobile phase at 50 mL/min giving as the first enantiomer to elute, 12,12-dimethyl-8-(3-{2-[1-(trifluoromethyl)cyclopropyl]ethoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (enantiomer 1) (Compound 74) (9.76 mg, 54%) as an off-white solid; ESI-MS m/z calc. 635.21375, found 636.2 (M+1)⁺; Retention time: 2.0 min (LC Method E) and as the second enantiomer to elute, 12,12-dimethyl-8-(3-{2-[1-(trifluoromethyl)cyclopropyl]ethoxy}-1H-pyrazol-1-yl)-15-oxa-2λ⁶-thia-3,9,11,18,23-pentaazatetracyclo[17.3.1.1¹¹,¹⁴.0⁵,¹⁰]tetracosa-1(22),5(10),6,8,19(23),20-hexaene-2,2,4-trione (enantiomer 2) (Compound 75) (11.29 mg, 63%) as an off-white solid; ESI-MS m/z calc. 635.21375, found 636.2 (M+1)⁺; Retention time: 2.0 min (LC Method E).

Example 133: Preparation of 12,12-dimethyl-8-(3-
{2-[1-(trifluoromethyl)cyclopropyl]ethoxy}-1H-
pyrazol-1-yl)-2λ⁶-thia-3,9,11,23-tetraazatetracyclo
[17.3.1.1¹¹,¹⁴.0⁵,¹⁰]tetracosa-1(23),5,7,9,19,21-
hexaene-2,2,4-trione (Compound 78)

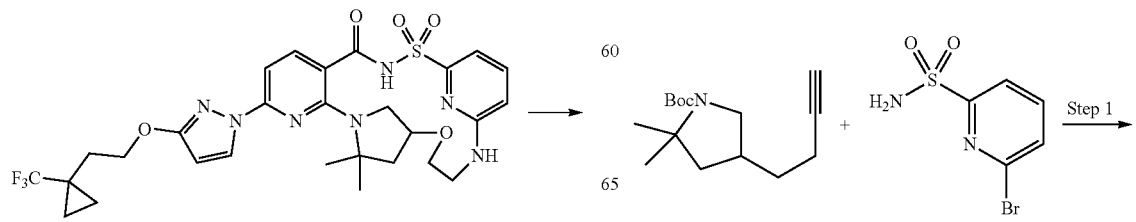

-continued

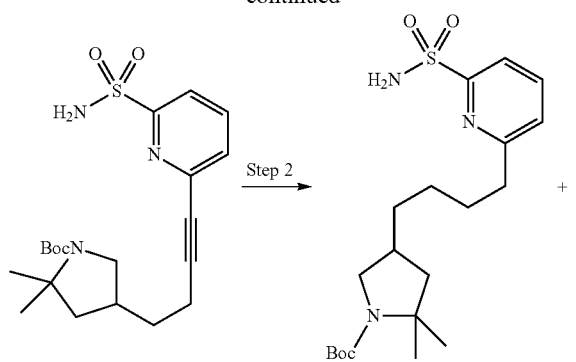

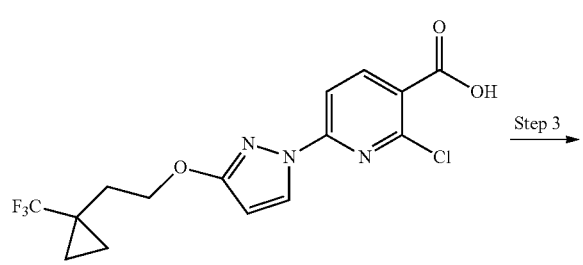

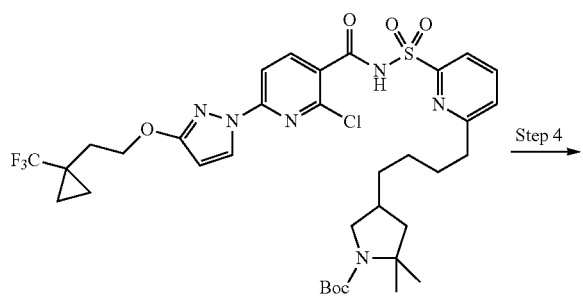

Step 1: tert-Butyl 2,2-dimethyl-4-[4-(6-sulfamoyl-2-pyridyl)but-3-ynyl]pyrrolidine-1-carboxylate

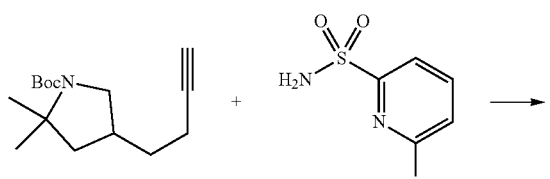

-continued

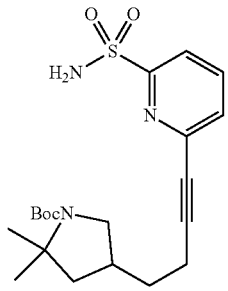

6-Bromopyridine-2-sulfonamide (840 mg, 3.543 mmol), trans-dichlorobis(triphenylphosphine)palladium(II) (125 mg, 0.1781 mmol) and iodocopper (34 mg, 0.1785 mmol) were added in sequence in a round-bottomed flask. To the vessel was then added anhydrous N,N-dimethylformamide (11 mL), sealed with a rubber septum under nitrogen followed by addition of diisopropylamine (1000 µL, 7.135 mmol). Then tert-butyl 4-but-3-ynyl-2,2-dimethyl-pyrrolidine-1-carboxylate (1.15 g, 4.575 mmol) in 3 mL of N,N-dimethylformamide was added and the reaction mixture was heated to 100° C. in an oil bath under nitrogen atmosphere for 2 h. The residue was diluted with ethyl acetate and washed with water (2×50 mL) then brine (50 mL). The organic layers were combined, dried (sodium sulfate), filtered and concentrated to an orange residue which was purified by silica gel chromatography using a gradient from 100% hexanes to 90% ethyl acetate in hexanes to afford as a light yellow foam, tert-butyl 2,2-dimethyl-4-[4-(6-sulfamoyl-2-pyridyl)but-3-ynyl]pyrrolidine-1-carboxylate (1.4 g, 97%). $^1$H NMR (400 MHz, dimethyl sulfoxide-$d_6$) δ 8.04 (t, J=7.8 Hz, 1H), 7.85 (dd, J=7.9, 0.8 Hz, 1H), 7.67 (dd, J=7.7, 3.5 Hz, 1H), 7.53 (s, 2H), 3.63 (dd, J=18.0, 9.0 Hz, 1H), 2.88 (q, J=10.5 Hz, 1H), 2.58-2.52 (m, 1H), 2.24 (s, 1H), 1.94 (dd, J=20.1, 6.4 Hz, 1H), 1.64 (dd, J=14.1, 7.0 Hz, 2H), 1.50 (dd, J=22.0, 9.7 Hz, 1H), 1.39 (dd, J=18.3, 9.6 Hz, 13H), 1.26 (s, 3H). ESI-MS m/z calc. 407.18787, found 408.2 (M+1)$^+$; Retention time: 1.77 min (LC Method E).

Step 2: tert-Butyl 2,2-dimethyl-4-[4-(6-sulfamoyl-2-pyridyl)butyl]pyrrolidine-1-carboxylate

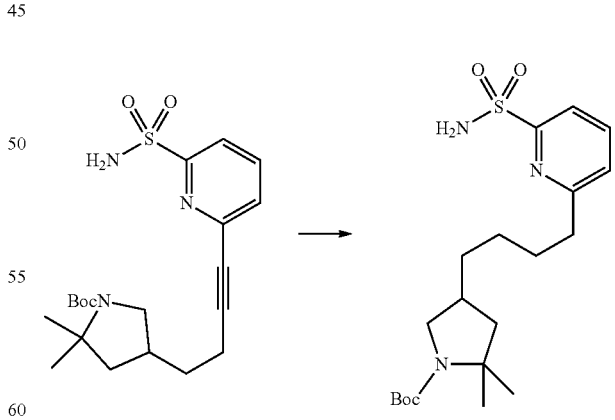

To tert-butyl 2,2-dimethyl-4-[4-(6-sulfamoyl-2-pyridyl)but-3-ynyl]pyrrolidine-1-carboxylate (1.1 g, 2.699 mmol) was added platinum oxide (61.29 mg, 0.2699 mmol) followed by methanol (11.00 mL) and the mixture was purged with nitrogen followed by hydrogen then capped with a hydrogen balloon and stirred for 4 h. Added additional platinum oxide (61.29 mg, 0.2699 mmol) and stirred for 1 h. The reaction mixture was filtered over Celite and washed with excess methanol and then the filtrate was concentrated. The residue was then purified by silica gel chromatography using a gradient from 100% hexanes to 100% ethyl acetate to afford as a yellow foam, tert-butyl 2,2-dimethyl-4-[4-(6-sulfamoyl-2-pyridyl)butyl]pyrrolidine-1-carboxylate (1.10 g, 99%) which was contaminated with a small amount of the olefin intermediate and was used directly in the next step. ESI-MS m/z calc. 411.21918, found 412.2 (M+1)$^+$; Retention time: 1.85 min (LC Method E).

Step 3: tert-Butyl 4-[4-[6-[[2-chloro-6-[3-[2-[1-(trifluoromethyl)cyclopropyl]ethoxy]pyrazol-1-yl]pyridine-3-carbonyl]sulfamoyl]-2-pyridyl]butyl]-2,2-dimethyl-pyrrolidine-1-carboxylate

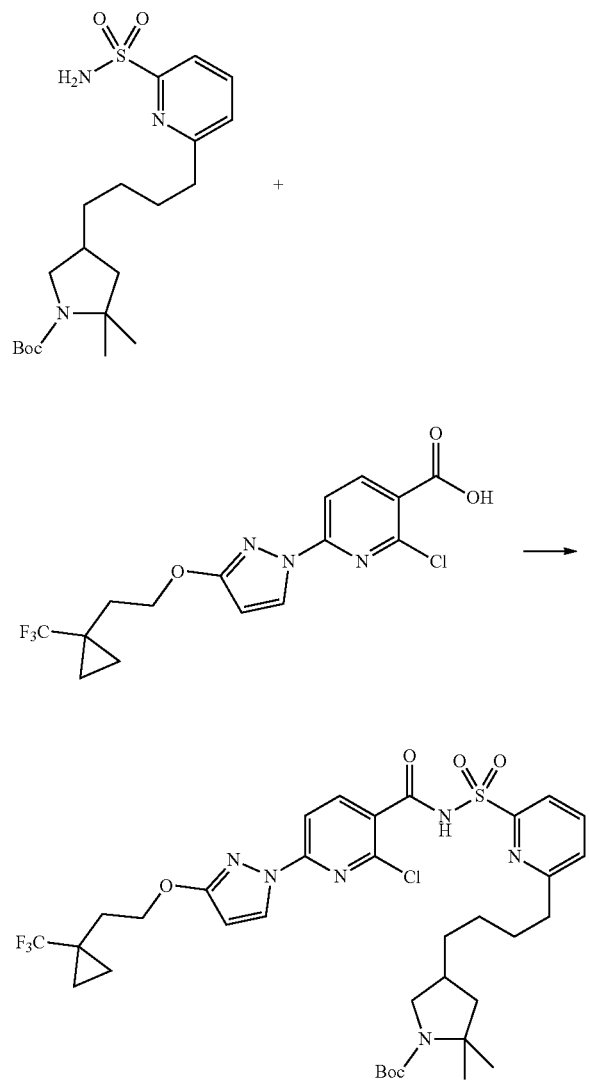

2-chloro-6-[3-[2-[1-(trifluoromethyl)cyclopropyl]ethoxy]pyrazol-1-yl]pyridine-3-carboxylic acid (685 mg, 1.823 mmol) and carbonyl diimidazole (296 mg, 1.825 mmol) were combined in tetrahydrofuran (11 mL) and stirred for 90 min at 50° C. Then tert-butyl 2,2-dimethyl-4-[4-(6-sulfamoyl-2-pyridyl)butyl]pyrrolidine-1-carboxylate (500 mg, 1.215 mmol) was added followed by 1,8-diazabicyclo[5.4.0]undec-7-ene (455 µL, 3.043 mmol) and the reaction was heated at 50° C. for 18 h. The reaction was diluted with ethyl acetate and washed with a 1 M citric acid solution, followed by brine. The organics were separated, dried over sodium sulfate, filtered and evaporated and then purified by silica gel chromatography using a gradient from 100% hexanes to 75% ethyl acetate in hexanes to afford as an off-white solid, tert-butyl 4-[4-[6-[[2-chloro-6-[3-[2-[1-(trifluoromethyl)cyclopropyl]ethoxy]pyrazol-1-yl]pyridine-3-carbonyl]sulfamoyl]-2-pyridyl]butyl]-2,2-dimethyl-pyrrolidine-1-carboxylate (165 mg, 35%). ESI-MS m/z calc. 768.2684, found 769.2 (M+1)$^+$; Retention time: 2.13 min (LC Method G).

Step 4: 12,12-Dimethyl-8-(3-{2-[1-(trifluoromethyl)cyclopropyl]ethoxy}-1H-pyrazol-1-yl)-2λ$^6$-thia-3,9,11,23-tetraazatetracyclo[17.3.1.1$^{11,14}$.0$^{5,10}$]tetracosa-1(23),5,7,9,19,21-hexaene-2,2,4-trione (Compound 78)

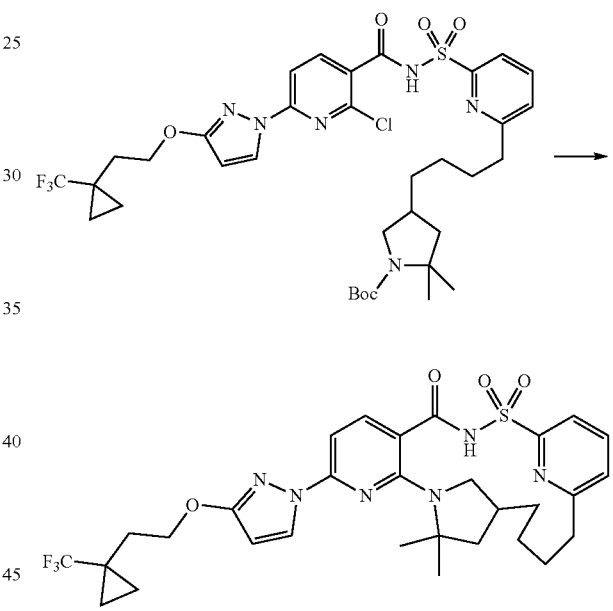

tert-Butyl 4-[4-[6-[[2-chloro-6-[3-[2-[1-(trifluoromethyl)cyclopropyl]ethoxy]pyrazol-1-yl]pyridine-3-carbonyl]sulfamoyl]-2-pyridyl]butyl]-2,2-dimethyl-pyrrolidine-1-carboxylate (125 mg, 0.1625 mmol) was dissolved in dichloromethane (2.5 mL) and to the mixture was added hydrochloric acid (1.5 mL of 4 M in dioxane, 6.000 mmol) and stirred at room temperature for 30 min. Concentrated the mixture to dryness under reduced pressure and combined with potassium carbonate (135 mg, 0.9768 mmol), cesium fluoride (40 mg, 0.2633 mmol), 3 Å molecular sieves and dimethyl sulfoxide (2.5 mL) in a vial, purged with nitrogen, capped, heated to 150° C. and stirred for 20 h. Cooled to room temperature and the mixture was filtered and then purified by reverse-phase preparative chromatography utilizing a C$_{18}$ column (30%-99% acetonitrile in water (5 mM hydrochloric acid) to afford as a white solid, 12,12-dimethyl-8-(3-{2-[1-(trifluoromethyl)cyclopropyl]ethoxy}-1H-pyrazol-1-yl)-2λ$^6$-thia-3,9,11,23-tetraazatetracyclo[17.3.1.1$^{11,14}$.0$^{5,10}$]tetracosa-1(23),5,7,9,19,21-hexaene- 2,2,4-tri one (Compound 78) (37.67 mg, 37%). ESI-MS m/z calc. 632.23926, found 633.2 (M+1)⁺; Retention time: 1.92 min (LC Method G).

Example 134: Preparation of 21,21,23-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.111,14.02,7]tricosa-2,4,6,11(23),12-pentaene-8,10,10-trione (Enantiomer 1) (Compound 80) and 21,21,23-trimethyl-4-(3-{2-[1-(trifluoromethyl)cyclo propyl]ethoxy}-1H-pyrazol-1-yl)-10λ⁶-thia-1,3,9,13,14-pentaazatetracyclo[17.2.1.111, 14.02,7]tricosa-2,4,6,11(23),12-pentaene-8,10,10-trione (Enantiomer 2) (Compound 81)

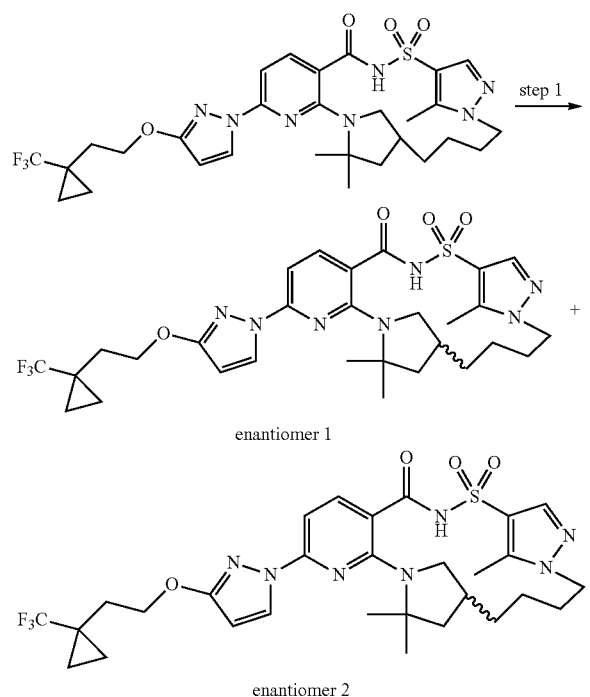

Step 1: 21,21,23-Trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.111, 14.02,7]tricosa-2,4,6,11(23),12-pentaene-8,10,10-trione (Enantiomer 1) (Compound 80) and 21,21,23-trimethyl-4-(3-{2-[1-(trifluoromethyl) cyclopropyl]ethoxy}-1H-pyrazol-1-yl)-10λ⁶-thia-1,3,9,13,14-pentaazatetracyclo[17.2.1.111,14.02,7]tricosa-2,4,6,11(23),12-pentaene-8,10,10-trione (Enantiomer 2) (Compound 81)

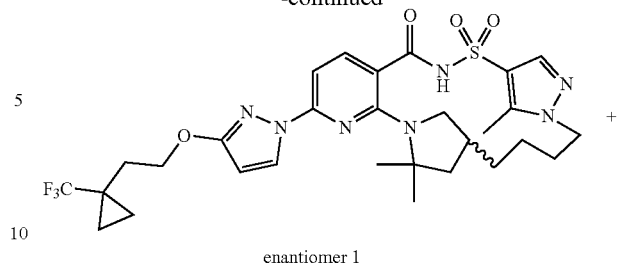

enantiomer 1

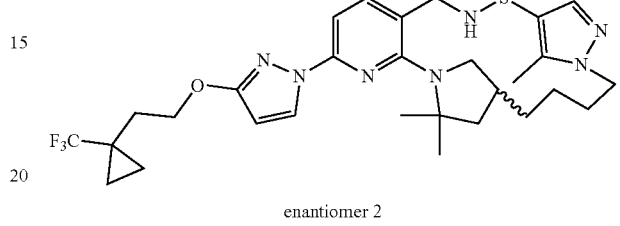

enantiomer 2

Subjected 21,21,23-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.111,14.02,7]tricosa-2,4,6,11(23),12-pentaene-8,10,10-trione (12 mg, 0.01888 mmol) to chiral separation by SFC chromatography using a ChiralPak AS-H (250×21 mm column, 5 μm particle size) with 20%-25% methanol (20 mM NH₃) in carbon dioxide mobile phase at 50 mL/min (injection volume=950 μL of 4 mg/mL solution in 50% methanol in dimethyl sulfoxide) giving as the first enantiomer to elute, 21,21,23-trimethyl-4-(3-{2-[1-(trifluoromethyl) cyclopropyl]ethoxy}-1H-pyrazol-1-yl)-10λ⁶-thia-1,3,9,13,14-pentaazatetracyclo [17.2.1.111,14.02,7]tricosa-2,4,6,11(23),12-pentaene-8,10, 10-trione (enantiomer 1) (Compound 80) (3.3 mg, 55%); ESI-MS m/z calc. 635.2502, found 636.3 (M+1)⁺; Retention time: 2.95 min (LC Method D) and as the second enantiomer to elute, 21,21,23-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.111,14.02,7]tricosa-2,4,6,11(23), 12-pentaene-8,10,10-trione (enantiomer 2) (Compound 81) (3.8 mg, 63%); ESI-MS m/z calc. 635.2502, found 636.3 (M+1)⁺; Retention time: 2.95 min (LC Method D).

Example 135: Preparation of 12,12-dimethyl-8-(3-{2-[1-(trifluoromethyl)cyclopropyl]ethoxy}-1H-pyrazol-1-yl)-2λ⁶-thia-3,9,11,23-tetraazatetracyclo [17.3.1.111,14.05,10]tetracosa-1(23),5,7,9,19,21-hexaene-2,2,4-trione (Enantiomer 1) (Compound 86) and 12,12-dimethyl-8-(3-{2-[1-(trifluoromethyl) cyclopropyl]ethoxy}-1H-pyrazol-1-yl)-2λ⁶-thia-3,9, 11,23-tetraazatetracyclo[17.3.1.111,14.05,10]tetracosa-1(23),5,7,9,19,21-hexaene-2,2,4-trione (Enantiomer 2) (Compound 87)

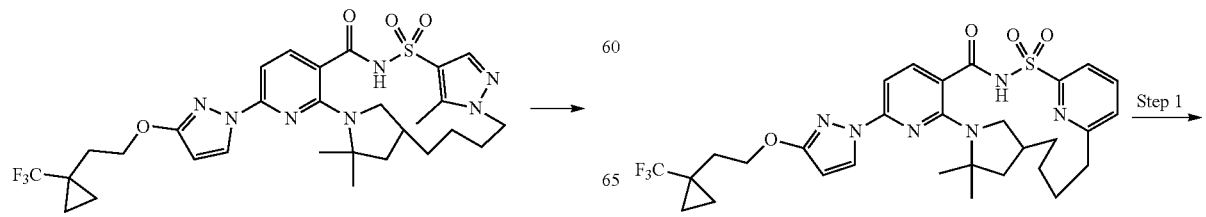

913
-continued

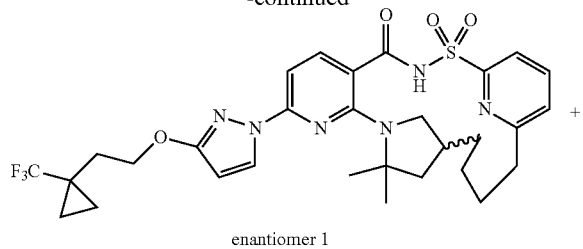

enantiomer 1

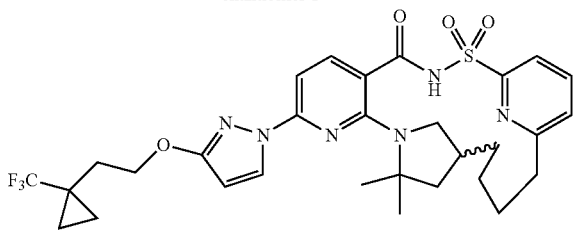

enantiomer 2

Step 1: 12,12-Dimethyl-8-(3-{2-[1-(trifluoromethyl)cyclopropyl]ethoxy}-1H-pyrazol-1-yl)-2λ⁶-thia-3,9,11,23-tetraazatetracyclo[17.3.1.1¹¹,¹⁴.0⁵,¹⁰]tetracosa-1(23),5,7,9,19,21-hexaene-2,2,4-trione (Enantiomer 1) (Compound 86) and 12,12-dimethyl-8-(3-{2-[1-(trifluoromethyl)cyclopropyl]ethoxy}-1H-pyrazol-1-yl)-2λ⁶-thia-3,9,11,23-tetraazatetracyclo[17.3.1.1¹¹,¹⁴.0⁵,¹⁰]tetracosa-1(23),5,7,9,19,21-hexaene-2,2,4-trione (Enantiomer 2) (Compound 87)

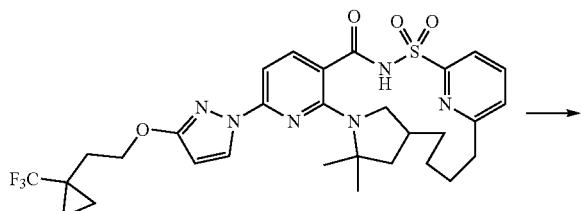

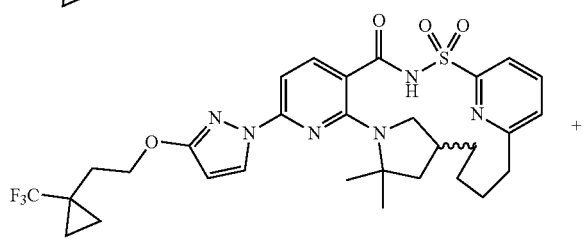

enantiomer 1

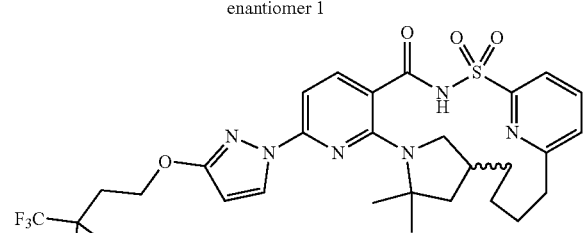

enantiomer 2

Subjected racemic 12,12-dimethyl-8-(3-{2-[1-(trifluoromethyl)cyclopropyl]ethoxy}-1H-pyrazol-1-yl)-2λ⁶-thia- 3,9,11,23-tetraazatetracyclo[17.3.1.1¹¹,¹⁴.0⁵,¹⁰]tetracosa-1(23),5,7,9,19,21-hexaene-2,2,4-trione (34.9 mg, 0.05516 mmol) to chiral separation by SFC chromatography using Chiral Pak AS-H (250×10 mm), column, 5 µm particle size) with 25% acetonitrile:methanol (90:10; no modifier), 75% carbon dioxide mobile phase at 10 mL/min (injection volume=70 µL of 24 mg/mL in acetonitrile:methanol (90:10)) giving as the first enantiomer to elute, 12,12-dimethyl-8-(3-{2-[1-(trifluoromethyl)cyclopropyl]ethoxy}-1H-pyrazol-1-yl)-2λ⁶-thia-3,9,11,23-tetraazatetracyclo[17.3.1.1¹¹,¹⁴.0⁵,¹⁰]tetracosa-1(23),5,7,9,19,21-hexaene-2,2,4-trione (enantiomer 1) (Compound 86) (13.11 mg, 74%) as a white solid; $^1$H NMR (400 MHz, dimethyl sulfoxide-$d_6$) δ 12.74 (s, 1H), 8.21 (d, J=2.7 Hz, 1H), 8.08 (t, J=7.7 Hz, 1H), 8.01 (d, J=7.6 Hz, 1H), 7.78 (d, J=7.6 Hz, 1H), 7.64 (d, J=7.6 Hz, 1H), 6.92 (d, J=8.2 Hz, 1H), 6.12 (d, J=2.7 Hz, 1H), 4.32 (t, J=7.0 Hz, 2H), 2.87 (s, 2H), 2.84-2.77 (m, 1H), 2.67 (t, J=12.6 Hz, 1H), 2.16 (dd, J=11.5, 5.3 Hz, 1H), 2.08 (t, J=7.0 Hz, 2H), 1.98-1.85 (m, 2H), 1.61 (s, 1H), 1.53 (t, J=24.3 Hz, 8H), 1.45 (s, 1H), 1.03 (dd, J=12.9, 7.3 Hz, 1H), 0.96 (t, J=5.7 Hz, 2H), 0.92 (d, J=8.6 Hz, 1H), 0.89 (s, 2H), ESI-MS m/z calc. 632.23926, found 633.2 (M+1)⁺; Retention time: 1.88 min (LC Method G) and as the second enantiomer to elute, 12,12-dimethyl-8-(3-{2-[1-(trifluoromethyl)cyclopropyl]ethoxy}-1H-pyrazol-1-yl)-2λ⁶-thia-3,9,11,23-tetraazatetracyclo[17.3.1.1¹¹,¹⁴.0⁵,¹⁰]tetracosa-1(23),5,7,9,19,21-hexaene-2,2,4-trione (enantiomer 2) (Compound 87) (12.96 mg, 74%) as a white solid; ESI-MS m/z calc. 632.23926, found 633.2 (M+1)⁺; Retention time: 1.92 min (LC Method G).

Example 136: Preparation of 12,12-dimethyl-8-(3-{2-[1-(trifluoromethyl)cyclopropyl]ethoxy}-1H-pyrazol-1-yl)-18-oxa-2λ⁶-thia-3,9,11,20-tetraazatetracyclo[17.2.2.1¹¹,¹⁴.0⁵,¹⁰]tetracosa-1(21),5(10),6,8,19,22-hexaene-2,2,4-trione (Compound 90)

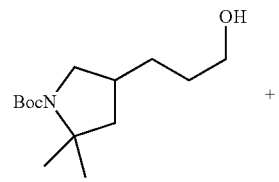

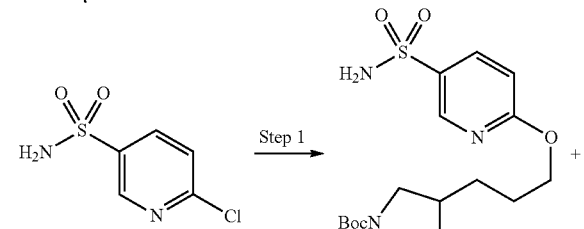

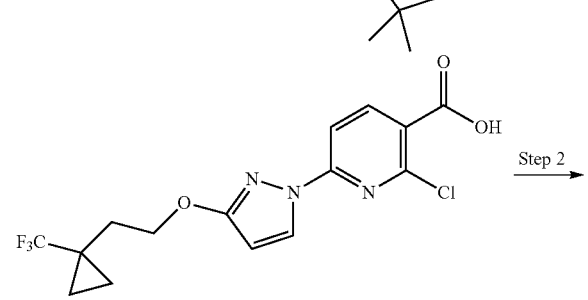

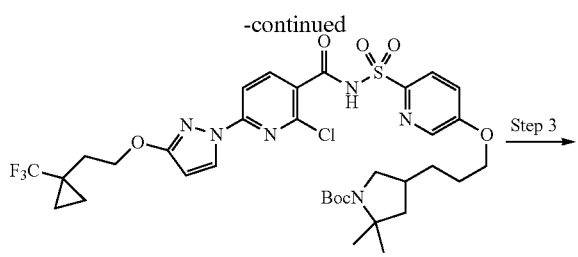

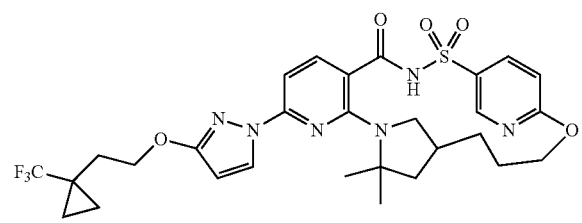

Step 1: tert-butyl 2,2-dimethyl-4-[3-[(5-sulfamoyl-2-pyridyl)oxy]propyl]pyrrolidine-1-carboxylate

To tert-butyl 4-(3-hydroxypropyl)-2,2-dimethyl-pyrrolidine-1-carboxylate (400 mg, 1.554 mmol) stirring under nitrogen atmosphere in N,N-dimethylformamide (4.0 mL) was portionwise added NaH (125 mg, 3.125 mmol) (CAUTION: gas evolution) and the mixture was stirred at room temperature for 20 min. 6-Chloropyridine-3-sulfonamide (296 mg, 1.537 mmol) was then added and the resulting mixture was stirred at room temperature for 140 min then NaH (62 mg, 1.550 mmol) was added (CAUTION: gas evolution) and the resulting mixture was heated to 100° C. after equipping with a reflux condenser for 20 h. Added more 6-chloropyridine-3-sulfonamide (145 mg, 0.750 mmol, NaH (62 mg, 1.55 mmol) and heated to 105° C. for 20 h. The mixture was then poured into 1 N citric acid and extracted with ethyl acetate (2×). Combined organic fractions, dried (sodium sulfate), filtered and concentrated to a yellow oil which was purified by silica gel chromatography using a gradient from 100% hexanes to 65% ethyl acetate in hexanes to afford tert-butyl 2,2-dimethyl-4-[3-[(5-sulfa-moyl-2-pyridyl)oxy]propyl]pyrrolidine-1-carboxylate (50.36 mg, 8%). ESI-MS m/z calc. 413.19846, found 414.2 (M+1)⁺; Retention time: 1.81 min (LC Method E).

Step 2: tert-Butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate

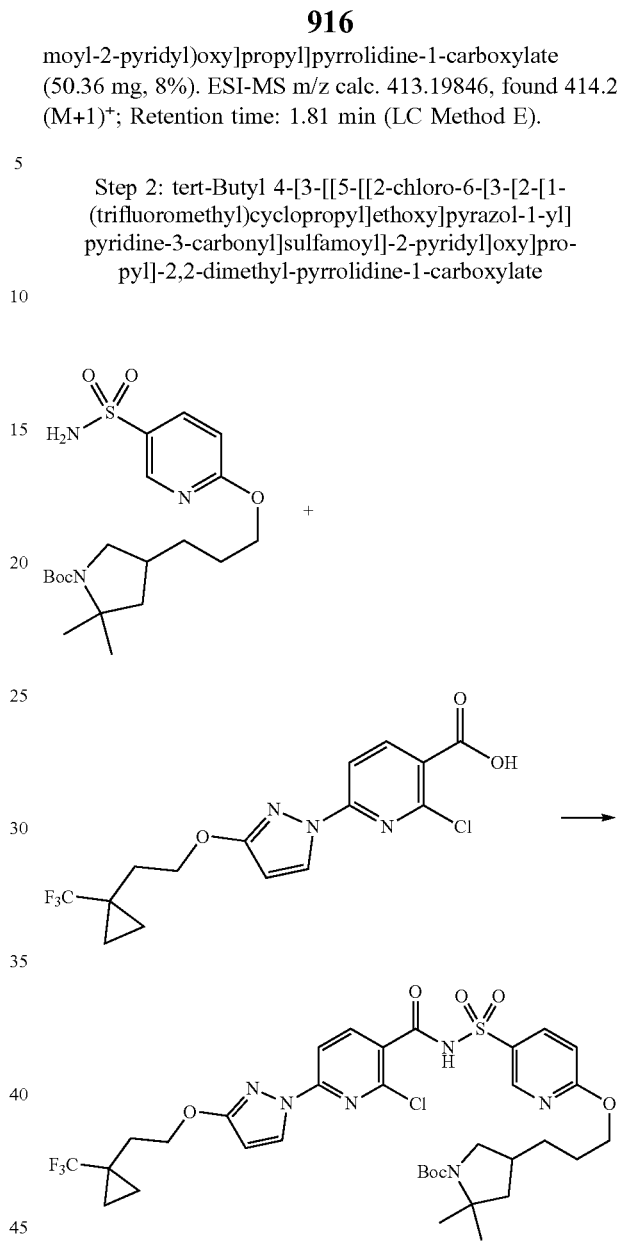

2-Chloro-6-[3-[2-[1-(trifluoromethyl)cyclopropyl]ethoxy]pyrazol-1-yl]pyridine-3-carboxylic acid (69 mg, 0.1836 mmol) and carbonyl diimidazole (30 mg, 0.1850 mmol) were combined in tetrahydrofuran (1.108 mL) and stirred for 90 min at room temperature. Then tert-butyl 2,2-dimethyl-4-[3-[(5-sulfamoyl-2-pyridyl)oxy]propyl]pyrrolidine-1-carboxylate (50.36 mg, 0.1218 mmol) was added followed by 1,8-diazabicyclo[5.4.0]undec-7-ene (50 µL, 0.3343 mmol) and the reaction was heated at 50° C. for 18 h. The reaction was diluted with ethyl acetate and washed with a 1 M citric acid solution, followed by brine. The organics were separated, dried over sodium sulfate, filtered and evaporated then purified by silica gel chromatography using a gradient from 100% hexanes to 75% ethyl acetate in hexanes to afford as an off-white solid, tert-butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate (71 mg, 76%). ESI-MS m/z calc. 770.2476, found 771.2 (M+1)⁺; Retention time: 2.11 min (LC Method E).

Step 3: 12,12-Dimethyl-8-(3-{2-[1-(trifluoromethyl) cyclopropyl]ethoxy}-1H-pyrazol-1-yl)-18-oxa-2λ⁶-thia-3,9,11,20-tetraazatetracyclo[17.2.2.1¹¹,¹⁴.0⁵,¹⁰]tetracosa-1(21),5(10),6,8,19,22-hexaene-2,2,4-trione (Compound 90)

Example 137: Preparation of 12,21,21-trimethyl-4-(3-{2-[1-(trifluoromethyl) cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Enantiomer 1) (Compound 91) and 12,21,21-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,14.02,7]tricosa-2,4,6,11(23),12-pentaene-8,10,10-trione (Enantiomer 2) (Compound 92)

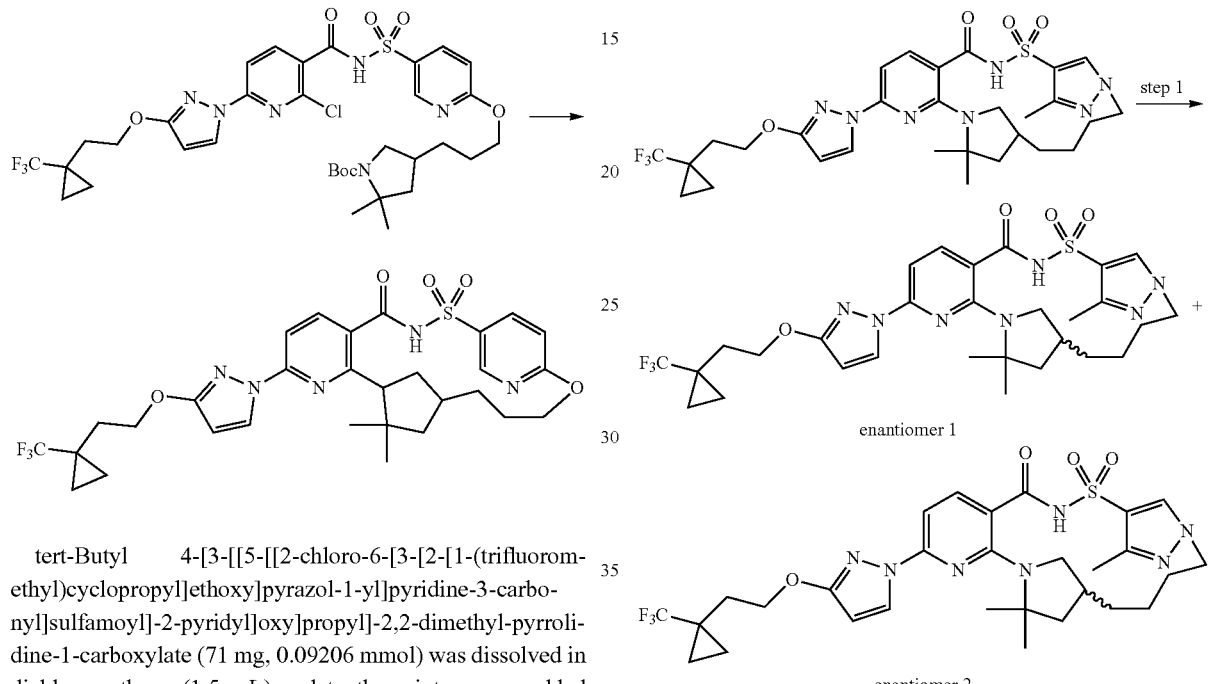

enantiomer 1 enantiomer 2 tert-Butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate (71 mg, 0.09206 mmol) was dissolved in dichloromethane (1.5 mL) and to the mixture was added hydrochloric acid (4M in dioxane) (800 µL of 4 M, 3.200 mmol) and the mixture was stirred at room temperature for 30 min. Concentrated the mixture to dryness under reduced pressure, redissolved in ethyl acetate and then added aqueous 2 M sodium carbonate (5 mL), giving pH 10. Extracted the organic layer with ethyl acetate (2×10 mL), washed with brine then dried over sodium sulfate, filtered and evaporated to dryness under reduced pressure. Combined the resulting material and potassium carbonate (69 mg, 0.4993 mmol), cesium fluoride (23 mg, 0.1514 mmol), 3 Å molecular sieves and dimethyl sulfoxide (1.5 mL) in a vial, purged with nitrogen, capped, heated to 155° C. and stirred for 24 h. Cooled to room temperature, filtered and then purified by reverse-phase preparative chromatography utilizing a C₁₈ column (30%-99% acetonitrile in water (5 mM hydrochloric acid) to afford as an off-white solid, 12,12-dimethyl-8-(3-{2-[1-(trifluoromethyl)cyclopropyl]ethoxy}-1H-pyrazol-1-yl)-18-oxa-2λ⁶-thia-3,9,11,20-tetraazatetracyclo[17.2.2.1¹¹,14.05,10]tetracosa-1 (21),5(10),6,8,19,22-hexaene-2,2,4-trione (Compound 90) (3.95 mg, 7%). ESI-MS m/z calc. 634.2185, found 635.2 (M+1)⁺; Retention time: 2.27 min (LC Method E).

Step 1: 12,21,21-Trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹, 14.02,7]tricosa-2,4,6,11(23),12-pentaene-8,10,10-trione (Enantiomer 1) (Compound 91) and 12,21,21-trimethyl-4-(3-{2-[1-(trifluoromethyl) cyclopropyl]ethoxy}-1H-pyrazol-1-yl)-10λ⁶-thia-1,3,9,13,14-pentaazatetracyclo[17.2.1.1¹¹,14.02,7] tricosa-2,4,6,11(23),12-pentaene-8,10,10-trione (Enantiomer 2) (Compound 92)

Racemic 12,21,21-trimethyl-4-(3-{2-[1-(trifluoromethyl) cyclopropyl]ethoxy}-1H-pyrazol-1-yl)-10λ⁶-thia-1,3,9,13, 14-pentaazatetracyclo[17.2.1.1¹¹,14.02,7]tricosa-2,4,6,11 (23),12-pentaene-8,10,10-trione (35 mg, 0.05506 mmol) was subjected to chiral separation by SFC chromatography using a Chiral Pak AS-H (250×10 mm), column, 5 µm particle size) with 20%-30% methanol (20 mM NH₃) in carbon dioxide mobile phase giving as the first enantiomer to elute, 12,21,21-trimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,14.02,7]tricosa-2,4,6,11(23), 12-pentaene-8,10,10-trione (enantiomer 1) (Compound 91) (12.1 mg, 69%); ESI-MS m/z calc. 635.2502, found 636.3 (M+1)⁺; Retention time: 3.04 min (LC Method G) and as the second enantiomer to elute, 12,21,21-trimethyl-4-(3-{2-[1-(trifluoromethyl)cyclopropyl]ethoxy}-1H-pyrazol-1-yl)-10$\lambda^6$-thia-1,3,9,13,14-pentaazatetracyclo[17.2.1.1¹¹,¹⁴.0²,⁷]tricosa-2,4,6,11(23),12-pentaene-8,10,10-trione (enantiomer 2) (Compound 92) (8.9 mg, 51%); ESI-MS m/z calc. 635.2502, found 636.3 (M+1)⁺; Retention time: 3.03 min (LC Method G).

Example 138: Preparation of 12,12-dimethyl-8-(3-{2-[1-(trifluoromethyl)cyclopropyl]ethoxy}-1H-pyrazol-1-yl)-2$\lambda^6$-thia-3,9,11,18,20-pentaazatetracyclo[17.3.1.1¹¹,¹⁴.0⁵,¹⁰]tetracosa-1(22),5,7,9,19(23),20-hexaene-2,2,4-trione (Compound 93)

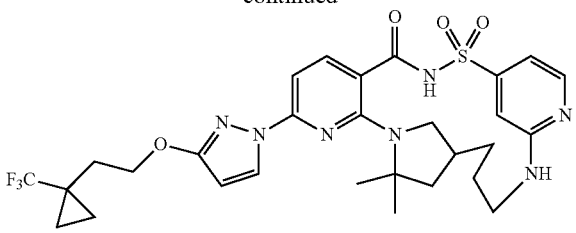

Step 1: tert-Butyl 2,2-dimethyl-4-[3-[(4-sulfamoyl-2-pyridyl)amino]propyl]pyrrolidine-1-carboxylate

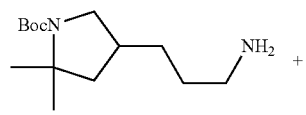

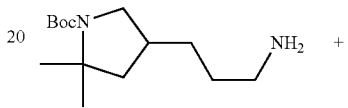

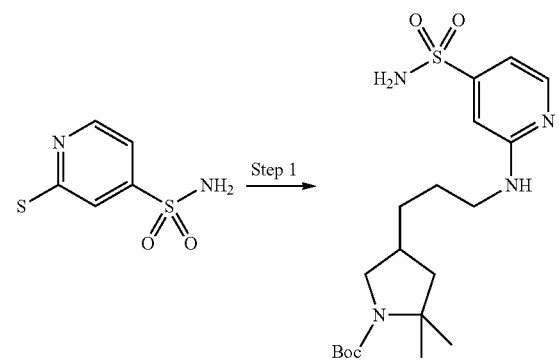

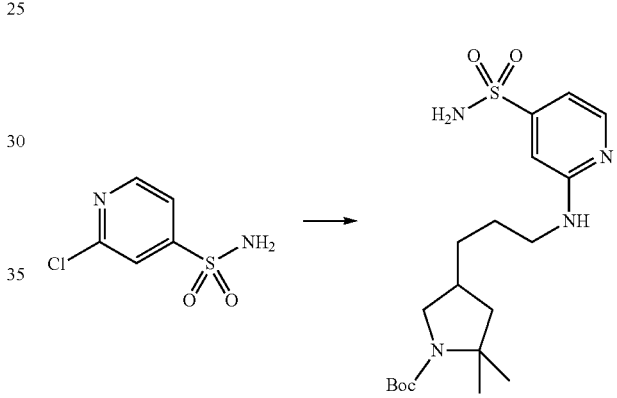

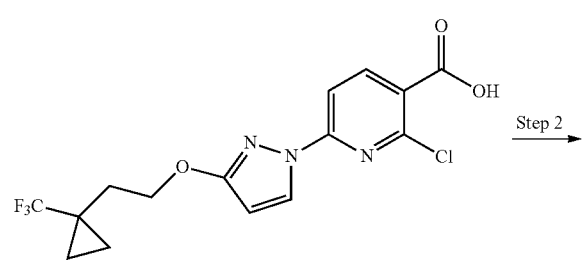

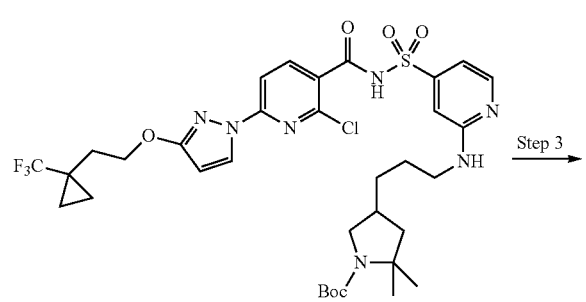

A solution of 2-chloropyridine-4-sulfonamide (300 mg, 1.557 mmol), tert-butyl 4-(3-aminopropyl)-2,2-dimethyl-pyrrolidine-1-carboxylate (399.2 mg, 1.557 mmol), sodium tert-butoxide (224.4 mg, 2.335 mmol) and chloro(2-di-tert-butylphosphino-2',4',6'-tri-i-propyl-1,1'-biphenyl)[2-(2-aminoethyl)phenyl]palladium(II) (202.8 mg, 0.3114 mmol) in dioxane (5.000 mL) was degassed by purging with nitrogen and the mixture was stirred at room temperature for 2 h. The reaction mixture was diluted with ethyl acetate and washed with brine solution. Dried the organic layer over anhydrous sodium sulfate, filtered and concentrated. The resultant brown residue was purified by silica gel column chromatography using a gradient from 100% dichloromethane to 20% methanol in dichloromethane to afford tert-butyl 2,2-dimethyl-4-[3-[(4-sulfamoyl-2-pyridyl)amino]propyl]pyrrolidine-1-carboxylate (175 mg, 27%, 1:1 mixture with tert-butyl 4-[3-[bis(4-sulfamoyl-2-pyridyl)amino]propyl]-2,2-dimethyl-pyrrolidine-1-carboxylate) as a light brown sticky solid which was used directly in the next step. ESI-MS m/z calc. 412.21442, found 413.6 (M+1)⁺; Retention time: 0.5 min (LC Method A).

921

Step 2: tert-Butyl 4-[3-[[4-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate

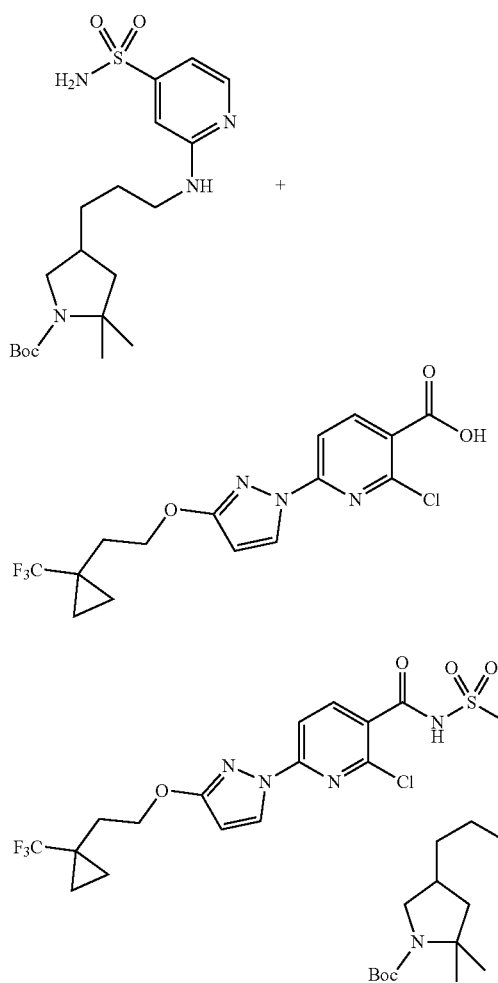

2-Chloro-6-[3-[2-[1-(trifluoromethyl)cyclopropyl]ethoxy]pyrazol-1-yl]pyridine-3-carboxylic acid (154.8 mg, 0.4120 mmol) and carbonyl diimidazole (66.81 mg, 0.4120 mmol) were combined in tetrahydrofuran (2.0 mL) and stirred for 90 min at 50° C. Then, tert-butyl 2,2-dimethyl-4-[3-[(4-sulfamoyl-2-pyridyl)amino]propyl]pyrrolidine-1-carboxylate (85 mg, 0.2060 mmol) was added followed by 1,8-diazabicyclo[5.4.0]undec-7-ene (47.04 mg, 46.21 μL, 0.3090 mmol) and the reaction was heated at 50° C. for 18 h. The reaction was diluted with ethyl acetate and washed with saturated ammonium chloride solution, followed by brine. The organics were separated, dried over sodium sulfate, filtered and evaporated. The resultant brown residue was purified by a reverse phase HPLC-MS method using a dual gradient run from 20%-99% mobile phase B over 15.0 min (mobile phase A=water (5 mM hydrochloric acid), mobile phase B=acetonitrile, flow rate=50 mL/min, injection volume=950 μL, and column temperature=25° C.) to afford tert-butyl 4-[3-[[4-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate (45.6 mg, 29%) as an off white solid.

922

$^1$H NMR (400 MHz, Chloroform-d) δ 8.33-8.28 (m, 1H), 8.28-8.12 (m, 2H), 7.70 (dd, J=8.2, 4.3 Hz, 1H), 7.28 (d, J=6.1 Hz, 1H), 7.21 (d, J=16.4 Hz, 1H), 5.95 (t, J=2.7 Hz, 1H), 4.39 (t, J=7.1 Hz, 2H), 3.77-3.68 (m, 1H), 3.68-3.52 (m, 1H), 3.38 (s, 2H), 2.85 (t, J=11.7 Hz, 1H), 2.23-2.11 (m, 1H), 2.09 (t, J=7.2 Hz, 2H), 1.94-1.79 (m, 1H), 1.75-1.56 (m, 2H), 1.43 (s, 12H), 1.35 (s, 2H), 1.26 (s, 3H), 1.07-0.97 (m, 2H), 0.73 (s, 2H). ESI-MS m/z calc. 769.2636, found 770.4 (M+1)$^+$; Retention time: 0.77 min (LC Method A).

Step 3: 12,12-Dimethyl-8-(3-{2-[1-(trifluoromethyl)cyclopropyl]ethoxy}-1H-pyrazol-1-yl)-2λ$^6$-thia-3,9,11,18,20-pentaazatetracyclo[17.3.1.1${}^{11,14}$.0${}^{5,10}$]tetracosa-1(22),5,7,9,19(23),20-hexaene-2,2,4-trione (Compound 93)

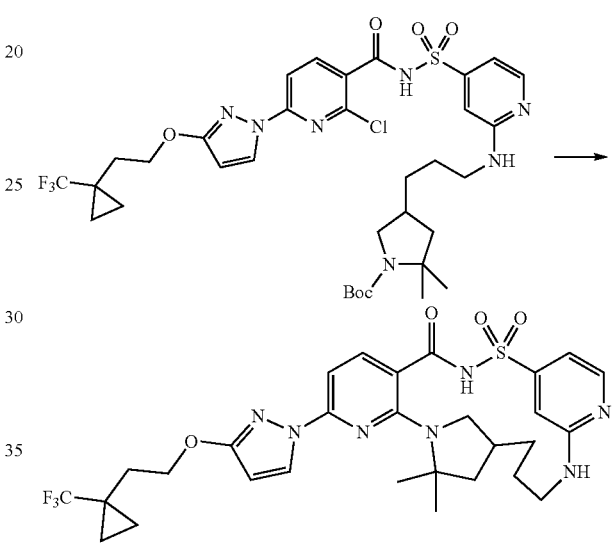

A solution of tert-butyl 4-[3-[[4-[[2-chloro-6-[3-[2-[1-(trifluoromethyl)cyclopropyl]ethoxy]pyrazol-1-yl]pyridine-3-carbonyl]sulfamoyl]-2-pyridyl]amino]propyl]-2,2-dimethyl-pyrrolidine-1-carboxylate (50 mg, 0.06491 mmol) in dichloromethane (416.7 μL) and trifluoroacetic acid (74.01 mg, 49.67 μL, 0.6491 mmol) was stirred at room temperature for 4 h. The solvents were removed and the residue was dissolved in ethyl acetate. Washed with 2 mL of sat sodium bicarbonate solution and the organic layer was collected and solvent removed then dried under vacuum. The resulting residue was dissolved in dimethyl sulfoxide (2.500 mL) and 3 Å molecular sieves were added and the reaction mixture was stirred for 10 min. Then, cesium fluoride (29.58 mg, 0.1947 mmol) and potassium carbonate (26.91 mg, 0.1947 mmol) were added and the reaction mixture was heated at 130° C. for overnight. The reaction mixture was filtered through a Whatman filter disc (puradisc 25 TF) and the filtrate was purified by a reverse phase HPLC-MS method using a dual gradient run from 20%-80% mobile phase B over 15.0 min (mobile phase A=water (0.05% hydrochloric acid), mobile phase B=acetonitrile) to afford 12,12-dimethyl-8-(3-{2-[1-(trifluoromethyl)cyclopropyl]ethoxy}-1H-pyrazol-1-yl)-2λ$^6$-thia-3,9,11,18,20-pentaazatetracyclo[17.3.1.1${}^{11,14}$.0${}^{5,10}$]tetracosa-1(22),5,7,9,19(23),20-hexaene-2,2,4-trione (Compound 93) (12.3 mg, 30%) as light yellow color solid. ¹H NMR (400 MHz, Chloroform-d) δ 8.39-8.22 (m, 1H), 8.16 (s, 1H), 7.94 (s, 2H), 7.61 (s, 1H), 7.20 (s, 1H), 6.98 (s, 1H), 5.91 (s, 1H), 4.37 (s, 2H), 3.47 (d, J=13.7 Hz, 2H), 3.01 (d, J=43.7 Hz, 2H), 2.20 (s, 1H), 2.08 (t, J=7.1 Hz, 3H), 1.86 (s, 2H), 1.71 (s, 2H), 1.65 (s, 3H), 1.61 (s, 3H), 1.30 (d, J=39.7 Hz, 2H), 1.05-0.98 (m, 2H), 0.74 (s, 2H). ESI-MS m/z calc. 633.2345, found 634.4 (M+1)⁺; Retention time: 1.75 min (LC Method B).

Example 139: Preparation of 12,12-dimethyl-8-(3-{2-[1-(trifluoromethyl)cyclopropyl]ethoxy}-1H-pyrazol-1-yl)-19-oxa-2λ⁶-thia-3,9,11,21-tetraazatetracyclo[18.2.2.1¹¹,¹⁴.0⁵,¹⁰]pentacosa-1(23),5,7,9,20(24),21-hexaene-2,2,4-trione (Compound 94)

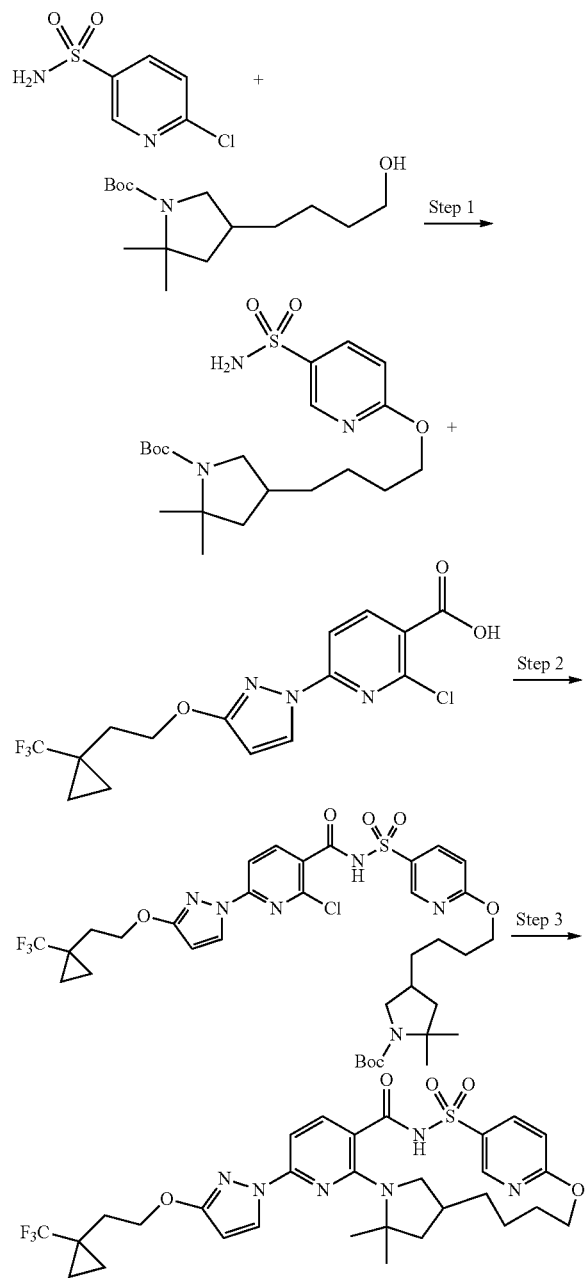

Step 1: tert-Butyl 2,2-dimethyl-4-[4-[(5-sulfamoyl-2-pyridyl)oxy]butyl]pyrrolidine-1-carboxylate

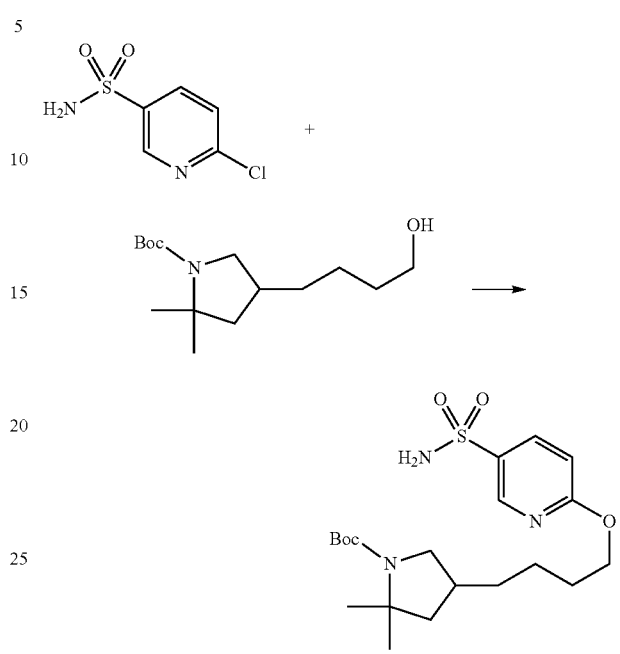

To tert-butyl 4-(4-hydroxybutyl)-2,2-dimethyl-pyrrolidine-1-carboxylate (800 mg, 2.948 mmol) stirring under nitrogen atmosphere in N,N-dimethylformamide (8 mL) was portionwise added NaH (240 mg, 6.001 mmol) (CAUTION: gas evolution) in a 20 mL vial and the mixture was stirred at room temperature for 20 min. 6-chloropyridine-3-sulfonamide (570 mg, 2.959 mmol) was then added and the resulting mixture was stirred at room temperature for 1 h then NaH (120 mg, 3.000 mmol) was added (CAUTION: gas evolution), the vial was capped and the resulting mixture was heated to 100° C. for 20 h. Added additional 6-chloropyridine-3-sulfonamide (145 mg, 0.750 mmol and NaH (62 mg, 1.55 mmol) and heated to 105° C. for 48 h. The mixture was then poured into 1 N citric acid and extracted with ethyl acetate (2×). Combined organic fractions, dried (sodium sulfate), filtered and concentrated to a yellow oil which was purified by silica gel chromatography using a gradient from 100% hexanes to 65% ethyl acetate in hexanes followed by a second purification on silica gel using a gradient from 100% dichloromethane to 15% methanol in dichloromethane to afford as a clear viscous oil, tert-butyl 2,2-dimethyl-4-[4-[(5-sulfamoyl-2-pyridyl)oxy]butyl]pyrrolidine-1-carboxylate (335 mg, 27%). ¹H NMR (400 MHz, dimethyl sulfoxide-d₆) δ 8.54 (d, J=2.1 Hz, 1H), 8.10-7.95 (m, 1H), 7.44 (d, J=6.2 Hz, 2H), 6.98 (d, J=8.8 Hz, 1H), 4.32 (t, J=6.6 Hz, 2H), 3.55 (dd, J=17.1, 6.9 Hz, 1H), 2.78 (q, J=10.5 Hz, 1H), 2.19-2.01 (m, 1H), 1.95-1.80 (m, 1H), 1.76-1.68 (m, 2H), 1.44 (d, J=12.1 Hz, 2H), 1.40-1.36 (m, 12H), 1.32 (d, J=17.3 Hz, 3H), 1.24 (s, 3H). ESI-MS m/z calc. 427.21408, found 428.2 (M+1)⁺; Retention time: 1.87 min (LC Method E).

Step 2: tert-Butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]oxy]butyl]-2,2-dimethyl-pyrrolidine-1-carboxylate

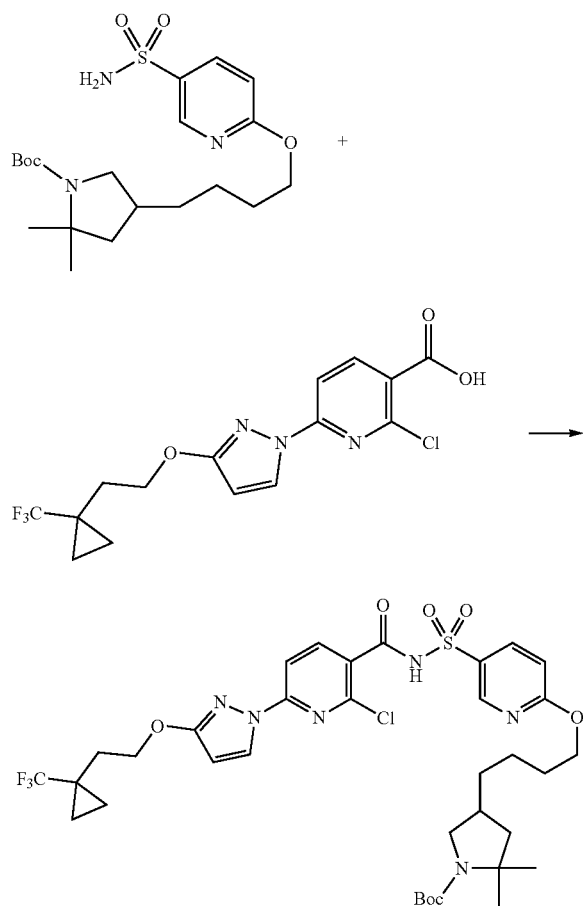

2-Chloro-6-[3-[2-[1-(trifluoromethyl)cyclopropyl]ethoxy]pyrazol-1-yl]pyridine-3-carboxylic acid (437.0 mg, 1.163 mmol) and carbonyl diimidazole (190.0 mg, 1.172 mmol) were combined in tetrahydrofuran (7.260 mL) and stirred for 90 min at 50° C. Then tert-butyl 2,2-dimethyl-4-[4-[(5-sulfamoyl-2-pyridyl)oxy]butyl]pyrrolidine-1-carboxylate (330 mg, 0.7718 mmol) was added followed by 1,8-diazabicyclo[5.4.0]undec-7-ene (322.6 mg, 316.9 μL, 2.119 mmol) and the reaction was heated at 50° C. for 20 h. The reaction was diluted with ethyl acetate and washed with a saturated aqueous sodium bicarbonate solution followed by brine. The organics were separated, dried over sodium sulfate, filtered and evaporated and then purified by silica gel chromatography using a gradient from 100% hexanes to 55% ethyl acetate in hexanes followed by a second purification on silica gel using a gradient from 100% dichloromethane to 15% methanol in dichloromethane to afford as a light yellow solid, tert-butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]oxy]butyl]-2,2-dimethyl-pyrrolidine-1-carboxylate (350 mg, 58%). ESI-MS m/z calc. 784.2633, found 785.2 (M+1)$^+$; Retention time: 2.19 min (LC Method G).

Step 3: 12,12-Dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (Compound 94)

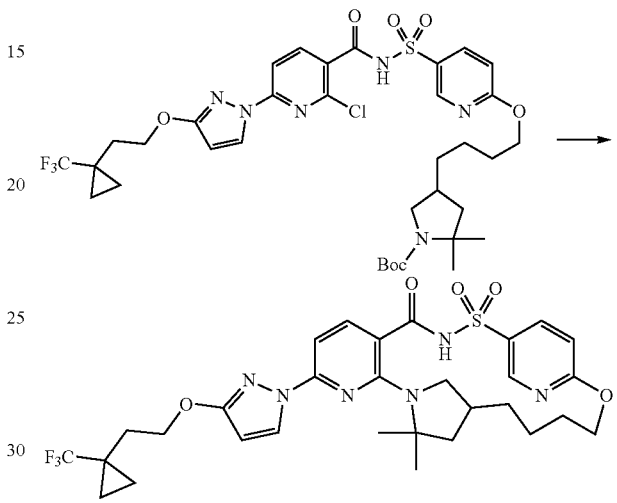

tert-Butyl 4-[4-[[5-[[2-chloro-6-[3-[2-[1-(trifluoromethyl)cyclopropyl]ethoxy]pyrazol-1-yl]pyridine-3-carbonyl]sulfamoyl]-2-pyridyl]oxy]butyl]-2,2-dimethyl-pyrrolidine-1-carboxylate (350 mg, 0.4457 mmol) was dissolved in dichloromethane (7.5 mL) and to the mixture was added hydrochloric acid (4.0 mL of 4 M in dioxane, 16.00 mmol) and stirred at room temperature for 30 min. Concentrated the mixture to dryness under reduced pressure, redissolved in ethyl acetate and then added aqueous 2 M sodium carbonate (5 mL), giving pH 10. Extracted with ethyl acetate (2×10 mL), combined the organic layers, washed with brine then dried over sodium sulfate, filtered and evaporated to dryness under reduced pressure. Combined the resulting material and potassium carbonate (310 mg, 2.243 mmol), cesium fluoride (105 mg, 0.6912 mmol), 3 Å molecular sieves and dimethyl sulfoxide (7.5 mL) in a vial, purged with nitrogen, capped, heated to 150° C. and stirred for 20 h. Cooled to room temperature and the mixture was filtered, diluted with ethyl acetate and washed with a saturated aqueous sodium bicarbonate solution, followed by brine. The organics were separated, dried over sodium sulfate, filtered and evaporated and then purified by silica gel chromatography using a gradient from 100% hexanes to 55% ethyl acetate in hexanes to afford as an off-white solid, 12,12-dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (Compound 94) (76.3 mg, 26%). ESI-MS m/z calc. 648.2342, found 649.2 (M+1)$^+$; Retention time: 2.41 min (LC Method E).

Example 140: Preparation of (14S)-8-[3-(3,3-dimethylbutyl)-4-methyl-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Hydrochloride Salt) (Compound 97)

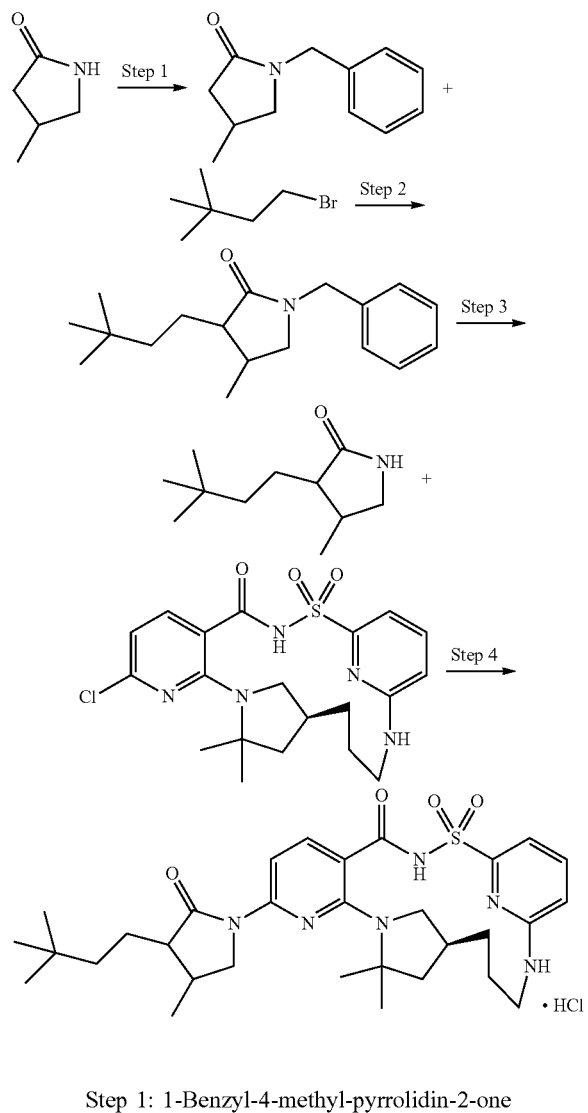

Step 1: 1-Benzyl-4-methyl-pyrrolidin-2-one

A 100 mL flask was charged under nitrogen with 4-methylpyrrolidin-2-one (1.52 g, 15.33 mmol) and anhydrous tetrahydrofuran (30 mL). The mixture was cooled down in an ice bath and NaH (811.9 mg of 60% w/w, 20.30 mmol) was added in small portions. Substantial foaming was noticed and the reaction turned into a difficult to stir slurry. Stirring was eased by adding an additional amount of tetrahydrofuran (10 mL). The mixture was stirred in the cooling bath for 1.5 h. Benzyl bromide (2.2 mL, 18.50 mmol) was added dropwise through a syringe. The mixture was stirred in the cooling bath that was allowed to slowly warm up to room temperature overnight. After 29 h, the reaction was poured on ice/water. The product was extracted with ethyl acetate (2×75 mL) and the organic phase was dried over sodium sulfate, filtered and the solvents were evaporated. The residue was dissolved in dichloromethane and purified by chromatography on silica gel using a gradient of ethyl acetate (0% to 100%) in hexanes giving 1-benzyl-4-methyl-pyrrolidin-2-one (2.52 g, 87%) as a slightly brown oil. $^1$H NMR (400 MHz, Chloroform-d) δ 7.37-7.17 (m, 5H), 4.44 (s, 2H), 3.36 (dd, J=9.6, 7.7 Hz, 1H), 2.82 (dd, J=9.6, 6.0 Hz, 1H), 2.61 (dd, J=16.6, 8.6 Hz, 1H), 2.40 (ddtd, J=8.6, 7.8, 6.9, 6.0 Hz, 1H), 2.08 (dd, J=16.6, 6.9 Hz, 1H), 1.07 (d, J=6.8 Hz, 3H). ESI-MS m/z calc. 189.11537, found 190.1 (M+1)⁺; Retention time: 1.16 min (LC Method B).

Step 2: 1-Benzyl-3-(3,3-dimethylbutyl)-4-methyl-pyrrolidin-2-one

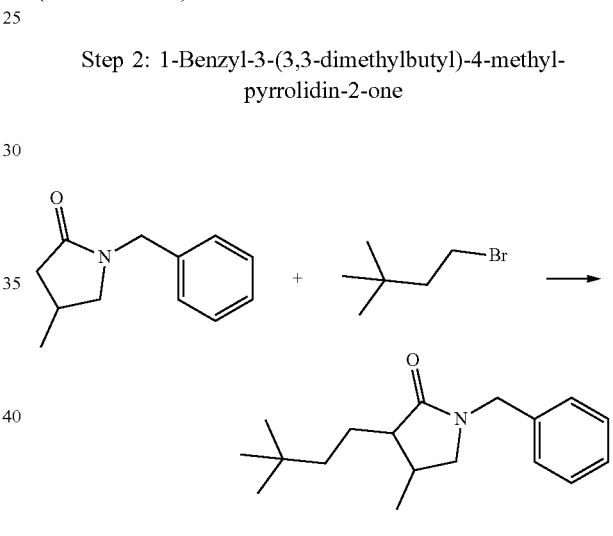

A 100 mL round bottom flask was dried with a heat gun under vacuum and filled with nitrogen. The flask was charged with 1-benzyl-4-methyl-pyrrolidin-2-one (542 mg, 2.864 mmol) and anhydrous tetrahydrofuran (8 mL). After cooling to −78° C., a solution of n-butyllithium (1.3 mL of 2.5 M in hexanes, 3.250 mmol) was added dropwise inducing formation of a red solution. After stirring at −78° C. for 30 min, 1-bromo-3,3-dimethyl-butane (450 μL, 3.195 mmol) was added dropwise. The mixture was stirred in the cooling bath that was then allowed to slowly warm up to room temperature. After 22 h, the mixture was quenched with the addition of saturated aqueous ammonium chloride (50 mL). The product was extracted with ethyl acetate (3×20 mL) and the combined organic extracts were dried over sodium sulfate, filtered and concentrated in vacuo. Column chromatography on silica gel using a gradient from 0% to 40% ethyl acetate in hexanes afforded 1-benzyl-3-(3,3-dimethylbutyl)-4-methyl-pyrrolidin-2-one (342 mg, 44%) as a colorless oil. ESI-MS m/z calc. 273.20926, found 274.2 (M+1)⁺; Retention time: 2.03 min (LC Method B).

929

Step 3: 3-(3,3-Dimethylbutyl)-4-methyl-pyrrolidin-2-one

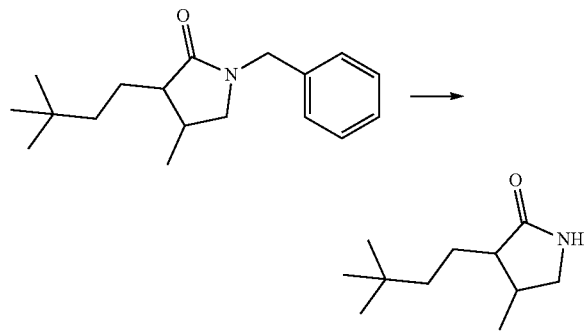

To a nitrogen-purged 50 mL flask charged with 1-benzyl-3-(3,3-dimethylbutyl)-4-methyl-pyrrolidin-2-one (342 mg, 1.251 mmol) was added propan-1-amine (6 mL) and ethane-1,2-diamine (500 µL, 7.479 mmol). The solution was cooled to −30° C. and a strip of lithium wire (6 cm, cut into 6 smaller pieces and rinsed with hexanes to remove excess oil) was added. The flask was re-fitted with a septum, and the reaction mixture stirred vigorously, with slight warming to −20° C. A blue color eventually formed around the lithium wire, with blue color leeching out into the solution briefly and the reaction was allowed to stir until the solution remained a deep blue color (~20 min). water (~15 mL) was added, the larger pieces of lithium removed, and the mixture warmed to room temperature and stirred for 10 min. The crude mixture was extracted with ethyl acetate (3×25 mL). The combined organic extracts were washed with water (15 mL), dried over sodium sulfate, filtered and concentrated in vacuo affording crude 3-(3,3-dimethylbutyl)-4-methyl-pyrrolidin-2-one (388 mg, 169%) as a yellow oil which was used without further purification. ESI-MS m/z calc. 183.16231, found 184.1 (M+1)⁺; Retention time: 1.43 min (LC Method B).

Step 4: (14S)-8-[3-(3,3-Dimethylbutyl)-4-methyl-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Hydrochloride Salt) (Compound 97)

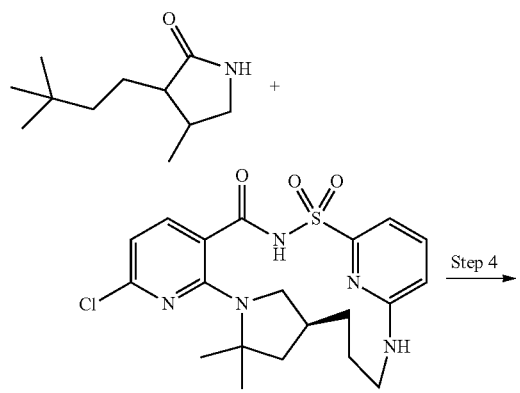

930

-continued

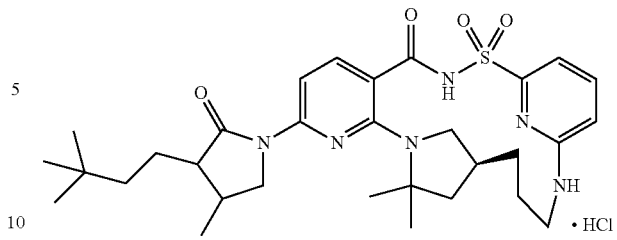

To a vial charged with crude 3-(3,3-dimethylbutyl)-4-methyl-pyrrolidin-2-one (22 mg, 0.1200 mmol) was added (14S)-8-chloro-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (25 mg, 0.05373 mmol), (5-diphenylphosphanyl-9,9-dimethyl-xanthen-4-yl)-diphenyl-phosphane (8 mg, 0.01383 mmol), (1E,4E)-1,5-diphenylpenta-1,4-dien-3-one; palladium (13 mg, 0.01420 mmol), Cs₂CO₃ (23 mg, 0.07059 mmol) and dioxane (1 mL). The headspace was purged with nitrogen, the vial capped, and the reaction mixture stirred at 120° C. for 18 h. After cooling to room temperature, the crude mixture was diluted with ethyl acetate (~30 mL) and washed with 1.0M aqueous citric acid (5 mL). The organic layer was dried over magnesium sulfate, filtered and concentrated in vacuo. The crude residue was taken up in a minimal amount of dimethyl sulfoxide (0.4-1 mL) and subjected to HPLC purification (C₁₈ reverse-phase, 1% to 99% acetonitrile in water with hydrochloric acid modifier). The pure fractions were then concentrated in vacuo and the residue was further purified by silica gel chromatography (0% to 70% ethyl acetate in hexanes) affording (14S)-8-[3-(3,3-dimethylbutyl)-4-methyl-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (hydrochloride salt) (Compound 97) (2 mg, 6%) as an off-white solid. ESI-MS m/z calc. 596.31445, found 597.2 (M+1)⁺; Retention time: 2.32 min (LC Method B).

Example 141: Preparation of (14S)-12,12-dimethyl-8-{3-[(1-methylcyclohexyl)methyl]-2-oxopyrrolidin-1-yl}-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 101)

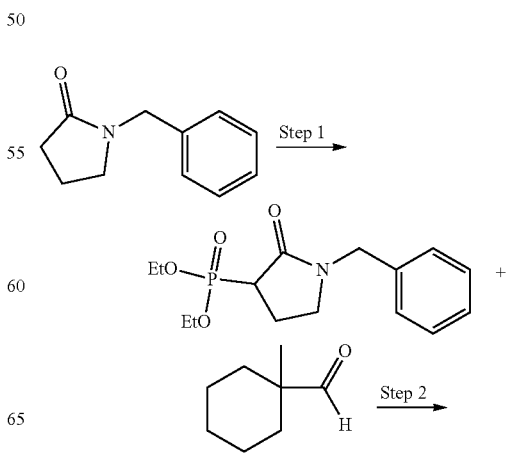

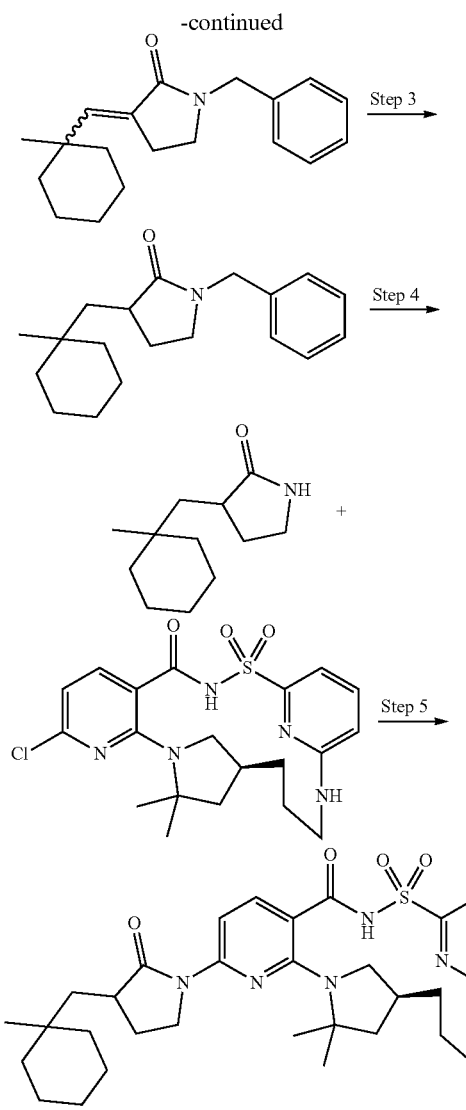

Step 1:
1-Benzyl-3-diethoxyphosphoryl-pyrrolidin-2-one

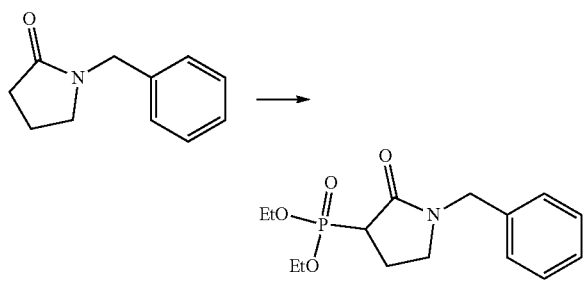

In a 250 mL flask, to a stirred solution of LDA (30 mL of 2.0 M, 60.00 mmol) in dry tetrahydrofuran (140 mL) at −78° C. under nitrogen, a solution of 1-benzylpyrrolidin-2-one (5.000 g, 28.53 mmol) in dry tetrahydrofuran (5 mL) was added dropwise over 5 min. The orange solution was stirred for 1 h and a solution of 1-[chloro(ethoxy)phosphoryl] oxyethane (5.170 g, 29.96 mmol) in dry tetrahydrofuran (5 mL) was added dropwise over 5 min. The reaction was allowed to warm to ambient temperature and stirred for 18 h. The reaction was quenched with cold ice-water (50 mL) and acidified to about pH=2.0 by addition of aqueous 1.0 M hydrochloric acid. The aqueous layer was separated and extracted with ethyl acetate (3×50 mL). The combined organic extracts were dried (sodium sulfate), filtered and concentrated under reduced pressure to produce crude product (8.74 g). Purification by flash silica gel column chromatography (first attempted with 10% to 100% ethyl acetate in hexanes over 40 min but the material did not come out, then switched to 0% to 10% methanol in $CH_2Cl_2$ to elute product) furnished the desired 1-benzyl-3-diethoxyphosphoryl-pyrrolidin-2-one (3.31 g, 37%) as orange viscous oil. $^1$H NMR (400 MHz, dimethyl sulfoxide-$d_6$) δ 7.38-7.31 (m, 2H), 7.31-7.25 (m, 1H), 7.25-7.21 (m, 2H), 4.49 (dd, J=15.1, 1.4 Hz, 1H), 4.30 (d, J=15.1 Hz, 1H), 4.15-3.98 (m, 4H), 3.31-3.14 (m, 3H), 2.34-2.19 (m, 1H), 2.19-2.04 (m, 1H), 1.22 (two sets oft, J=7.2 Hz, 6H). ESI-MS m/z calc. 311.12863, found 312.2 (M+1)$^+$; Retention time: 0.93 min (LC Method B).

Step 2: 1-Benzyl-3-[(1-methyl cyclohexyl)methylene]pyrrolidin-2-one

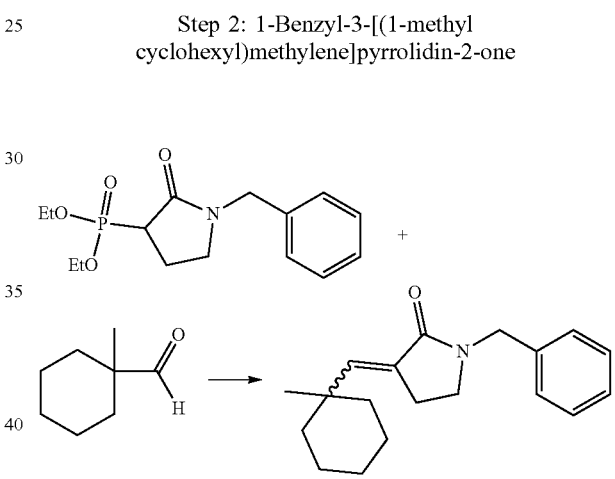

In a 50 mL flask, to a stirred solution of 1-benzyl-3-diethoxyphosphoryl-pyrrolidin-2-one (300 mg, 0.9637 mmol) in dry tetrahydrofuran (10 mL) was added sodium hydride (42.40 mg, 47.11 µL, 1.060 mmol, 60% dispersed in mineral oil) in three portions (to mitigate gas evolution) at 5° C. (ice-water bath) under nitrogen. After stirring for 10 min, a solution of 1-methylcyclohexanecarbaldehyde (182.5 mg, 1.446 mmol) in dry tetrahydrofuran (2 mL) was added dropwise over 3 min. Then stirred at that temperature for 3 h and quenched with saturated $NH_4Cl$ solution (15 mL). The layers were separated and the aqueous layer was extracted with ethyl acetate (3×20 mL). The combined organics were washed successively with water (15 mL) and brine (15 mL), dried over anhydrous sodium sulfate, filtered, and concentrated under reduced pressure to obtain crude olefin product. The crude material was purified through silica gel column chromatography eluting with 5%-60% ethyl acetate in hexanes. The E and Z isomers eluted together. Removal of the volatiles furnished 1-benzyl-3-[(1-methylcyclohexyl) methylene]pyrrolidin-2-one (265 mg, 97%) as yellow viscous oil and mixture of E and Z isomers. ESI-MS m/z calc. 283.1936, found 284.2 (M+1)$^+$; Retention time: 1.98 min (LC Method B).

Step 3: 1-Benzyl-3-[(1-methylcyclohexyl)methyl]pyrrolidin-2-one

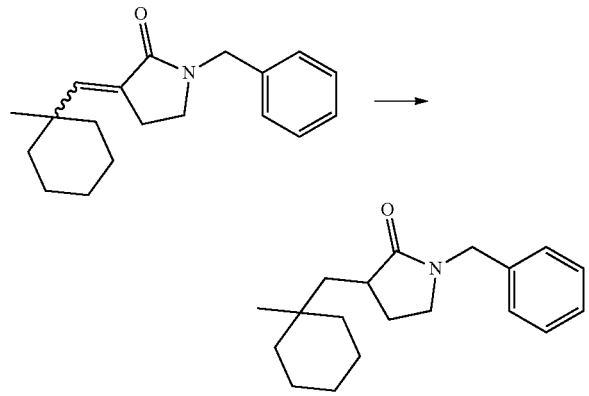

A 50 mL three neck flask under nitrogen was charged with 1-benzyl-3-[(1-methylcyclohexyl)methylene]pyrrolidin-2-one (260 mg, 0.9174 mmol) as a mixture of E and Z isomers and anhydrous methanol (15 mL). The flask was purged with nitrogen then palladium (100 mg, 0.09397 mmol, 10% on activated carbon) was added under nitrogen and stirred under hydrogen (balloon) at 50° C. for 2 days. The reaction was allowed to cool to ambient temperature and the flask was purged with hydrogen then filtered over a pad of celite. The filtrate was concentrated to obtain crude 1-benzyl-3-[(1-methylcyclohexyl)methyl]pyrrolidin-2-one (138 mg, 53%) as brown gum which was used in the subsequent step without further purification.

ESI-MS m/z calc. 285.20926, found 286.3 (M+1)$^+$; Retention time: 1.98 min (LC Method B).

Step 4: 3-[(1-Methylcyclohexyl)methyl]pyrrolidin-2-one

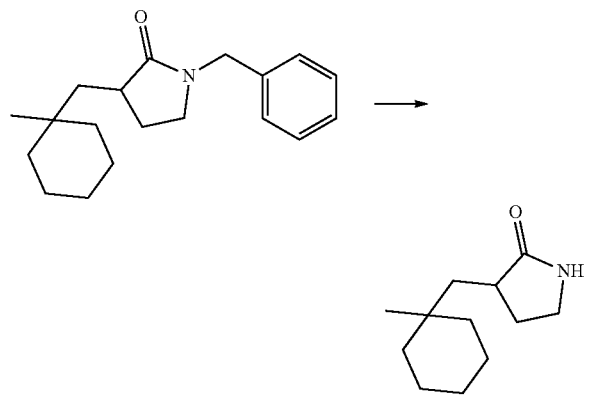

A 50 mL flask was charged under nitrogen with 1-benzyl-3-[(1-methylcyclohexyl)methyl]pyrrolidin-2-one (164 mg, 0.5746 mmol), propan-1-amine (5 mL), and ethane-1,2-diamine (250 µl, 3.740 mmol), in that order, at ambient temperature. The solution was cooled down to −35° C. (dry ice-acetone bath, where 1 or 2 dry ice pallets were added intermittently to keep the temperature steady) and lithium (40 mg, 5.763 mmol, wire, briefly rinsed with hexanes, then freshly cut into small pieces) was added at once. Blue color started to develop around the small pieces of lithium and the deep blue color became permanent after 1 h. The reaction was quenched with saturated ammonium chloride (5 mL) at −35° C. and the reaction was allowed to warm to ambient temperature. The volatiles were removed under reduced pressure and the aqueous residue was extracted with ethyl acetate (3×20 mL). The combined organics were washed with brine (10 mL), dried over anhydrous sodium sulfate and the volatiles were removed under reduced pressure. Upon drying under vacuum, the crude 3-[(1-methylcyclohexyl)methyl]pyrrolidin-2-one (78 mg, 70%) was obtained as white semi-solid and was used without further purification. ESI-MS m/z calc. 195.16231, found 196.1 (M+1)$^+$; Retention time: 1.47 min (LC Method B).

Step 5: (14S)-12,12-dimethyl-8-{3-[(1-methylcyclohexyl)methyl]-2-oxopyrrolidin-1-yl}-2λ$^6$-thia-3,9,11,18,23-pentaazatetracyclo[17.3.1.111,14.05,10]tetracosa-1(22),5,7,9,19(23),20-hexaene-2,2,4-trione (Compound 101)

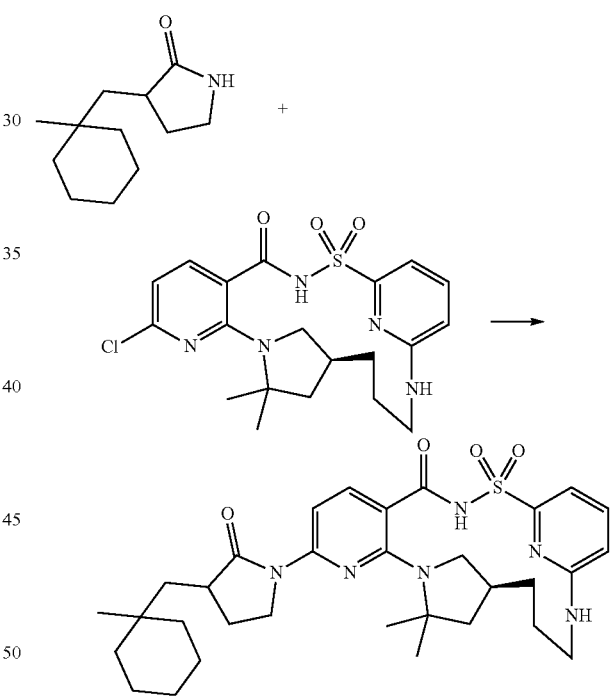

A 4 mL vial was charged with (14S)-8-chloro-12,12-dimethyl-2λ$^6$-thia-3,9,11,18,23-pentaazatetracyclo[17.3.1.111,14.05,10]tetracosa-1(23),5,7,9,19,21-hexaene-2,2,4-trione (25 mg, 0.05373 mmol), 3-[(1-methylcyclohexyl)methyl]pyrrolidin-2-one (10 mg, 0.05120 mmol), Pd$_2$(dba)$_3$ (8 mg, 0.008736 mmol), Xantphos (5 mg, 0.008641 mmol), cesium carbonate (87.52 mg, 0.2686 mmol) and anhydrous dioxane (0.4 mL). The mixture was sparged with nitrogen for 1 to 2 min, capped and stirred at 120° C. for 15 h. The reaction was diluted with dimethyl sulfoxide (1000 µL), microfiltered and subjected to reverse phase preparative HPLC (C$_{18}$) using a gradient of acetonitrile in water (1% to 99% over 15 min) and hydrochloric acid as a modifier. The pure fractions were collected and combined, a bit of brine was added and the organic solvents were evaporated. The product was extracted with dichloromethane and the organic phase was dried over sodium sulfate then filtered. Evaporation of the filtrate gave 10 mg of solid. The product was further purified by silica gel flash chromatography using a gradient of methanol (0% to 5% over 30 min) in dichloromethane giving (14S)-12,12-dimethyl-8-{3-[(1-methylcyclohexyl)methyl]-2-oxopyrrolidin-1-yl}-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 101) (6.4 mg, 19%) as an off-white solid. $^1$H NMR (400 MHz, dimethyl sulfoxide-d$_6$) δ 12.41 (s, 1H), 7.68 (dd, J=8.5, 1.4 Hz, 1H), 7.61-7.47 (m, 2H), 7.04 (d, J=7.1 Hz, 1H), 6.97 (broad d, J=9.0 Hz, 1H), 6.70 (d, J=8.5 Hz, 1H), 4.11-3.65 (m, 3H), 3.10 (br s, 1H), 2.94 (d, J=13.3 Hz, 1H), 2.75-2.57 (m, 2H), 2.43-2.28 (m, 1H), 2.10 (br s, 1H), 2.02-1.93 (m, 1H), 1.89-1.64 (m, 3H), 1.64-1.37 (m, 13H), 1.35-1.10 (m, 8H), 0.89 (d, J=1.7 Hz, 3H). ESI-MS m/z calc. 608.31445, found 609.3 (M+1)$^+$; Retention time: 2.34 min (LC Method B).

Example 142: Preparation of 12,12-dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (Enantiomer 1) (Compound 103) and 12,12-dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (Enantiomer 2) (Compound 104)

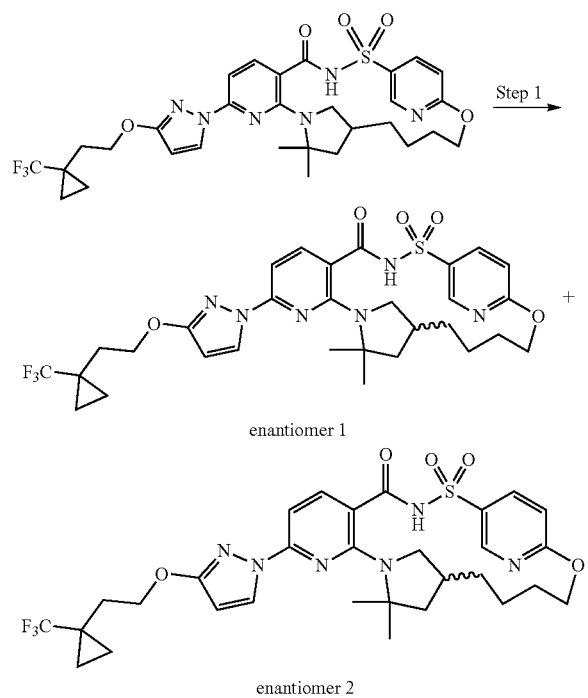

Step 1: 12,12-Dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (Enantiomer 1) (Compound 103) and 12,12-dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (Enantiomer 2) (Compound 104)

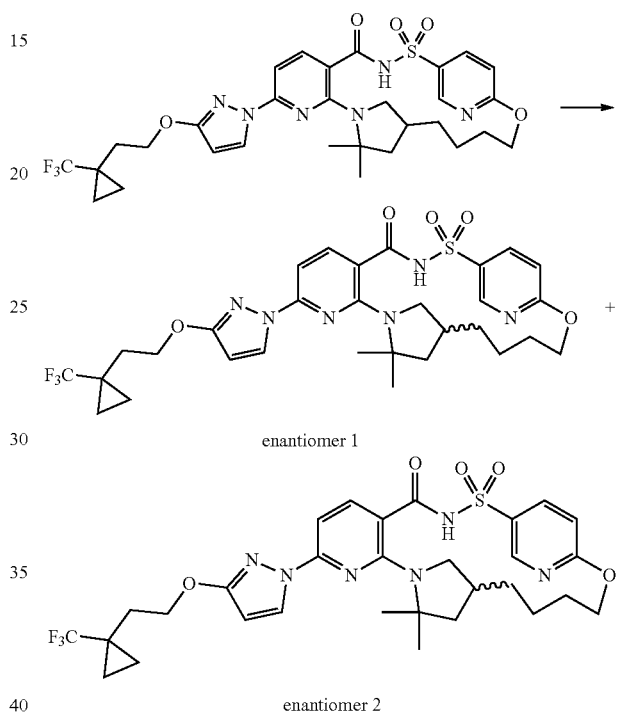

Racemic 12,12-dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (71 mg, 0.1095 mmol) was subjected to chiral separation by SFC chromatography using a ChiralCel OD-H (250×10 mm column, 5 μm particle size) with 42% acetonitrile/methanol (90:10)/58% carbon dioxide mobile phase at 10 mL/min over 8.0 min (injection volume=70 μL of 24 mg/mL solution in acetonitrile/methanol (90:10) giving as the first enantiomer to elute, 12,12-dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (enantiomer 1) (Compound 103) (19.77 mg, 56%) as a white solid; ESI-MS m/z calc. 648.2342, found 649.2 (M+1)$^+$; Retention time: 2.38 min (LC Method E) and as the second enantiomer to elute, 12,12-dimethyl-8-(3-{2-[1-(trifluoromethyl)cyclopropyl]ethoxy}-1H-pyrazol-1-yl)-19-oxa-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (enantiomer 2) (Compound 104) (20.25 mg, 57%) as a white solid. $^1$H NMR (400 MHz, dimethyl sulfoxide-d$_6$) δ 12.46 (s, 1H), 8.77 (s, 1H), 8.19 (d, J=2.8 Hz, 2H), 7.88 (d, J=8.3 Hz, 1H), 7.03 (d, J=8.7 Hz, 1H), 6.92 (d, J=8.3 Hz, 1H), 6.11 (d, J=2.7 Hz, 1H), 4.31 (t, J=7.0 Hz, 2H), 2.41 (dd, J=8.3, 5.3 Hz, 1H), 2.07 (t, J=7.0 Hz, 3H), 2.04-1.98 (m, 1H), 1.73 (d, J=6.4 Hz, 2H), 1.67 (dd, J=7.9, 4.9 Hz, 1H), 1.64-1.55 (m, 1H), 1.51 (d, J=11.5 Hz, 9H), 1.16 (dd, J=9.6, 1.7 Hz, 1H), 1.06-0.97 (m, 1H), 0.95 (d, J=4.3 Hz, 2H), 0.88 (s, 2H), 0.86-0.77 (m, 1H). ESI-MS m/z calc. 648.2342, found 649.2 (M+1)$^+$; Retention time: 2.38 min (LC Method E).

Example 143: Preparation of 8,8-dimethyl-12-(3-{2-[1-(trifluoromethyl)cyclopropyl]ethoxy}-1H-pyrazol-1-yl)-18λ$^6$-thia-2,9,11,17,23-pentaazatetra-cyclo[17.3.1.05,9.010,15]tricosa-1(23),10(15),11,13,19,21-hexaene-16,18,18-trione (Compound 108), 8,8-dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.05,9.010,15]tricosa-1(23),10(15),11,13,19,21-hexaene-16,18,18-trione (Enantiomer 1) (Compound 116) and 8,8-dimethyl-12-(3-{2-[1-(trifluoromethyl)cyclopropyl]ethoxy}-1H-pyrazol-1-yl)-18λ$^6$-thia-2,9,11,17,23-pentaaza-tetracyclo[17.3.1.05,9.010,15]tricosa-1(23),10(15),11,13,19,21-hexaene-16,18,18-trione (Enantiomer 2) (Compound 117)

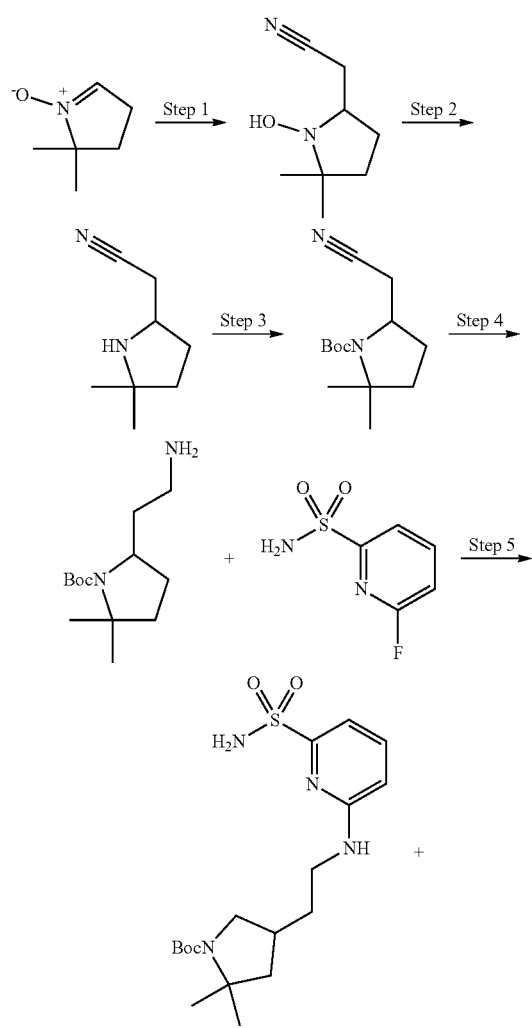

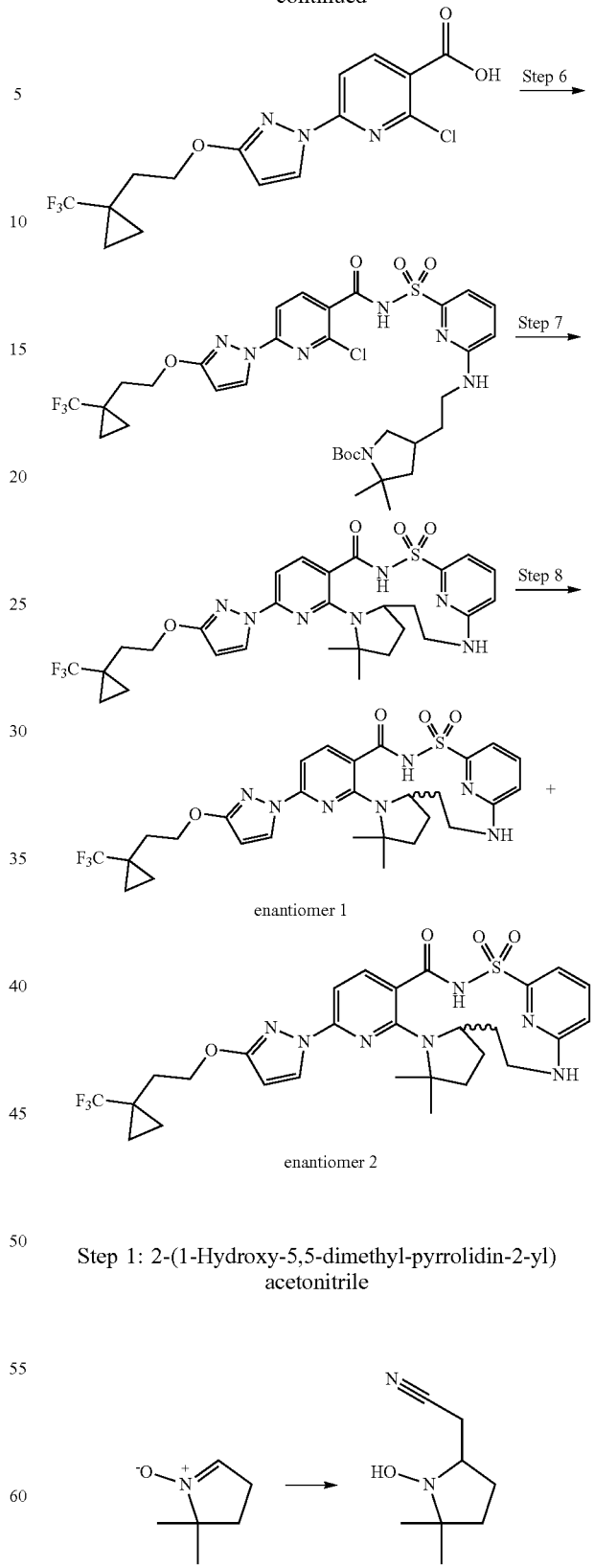

Step 1: 2-(1-Hydroxy-5,5-dimethyl-pyrrolidin-2-yl)acetonitrile n-Butyllithium (127 mL of 2.5 M, 317.5 mmol) was added dropwise to dry tetrahydrofuran (270 mL) cooled at −78° C. The internal temperature was kept below −65° C.

during addition. Then acetonitrile (13.13 g, 16.7 mL, 319.8 mmol) was slowly added, keeping the internal temperature below −70° C. White precipitate of the lithiated acetonitrile was observed after half of acetonitrile was added. After 30 min at −78° C., a solution of 2,2-dimethyl-1-oxido-3,4-dihydropyrrol-1-ium (11.20 g, 99 mmol) in dry tetrahydrofuran (15 mL) was added in such a rate that the internal temperature was not raised above −70° C. The yellow suspension was stirred at −78° C. for 1 h then quenched with saturated ammonium chloride solution (150 mL). After warming up to room temperature, the two layers were separated. The aqueous layer was extracted with ethyl acetate (2×150 mL). The combined organic layers were washed with brine, dried over anhydrous sodium sulfate, filtered and concentrated under reduced pressure to give crude 2-(1-hydroxy-5,5-dimethyl-pyrrolidin-2-yl)acetonitrile (17 g, 80% purity by $^1$H NMR, 89% yield) as a brown oil which was directly used for the next step without further purification. $^1$H NMR (300 MHz, CDCl$_3$) δ 1.04 (s, 3H), 1.18 (s, 3H), 1.48-1.67 (m, 3H), 1.99-2.06 (m, 1H), 2.59 (d, J=5.2 Hz, 2H), 3.17-3.26 (m, 1H), 4.59 (br. s., 1H).

Step 2: 2-(5,5-Dimethylpyrrolidin-2-yl)acetonitrile

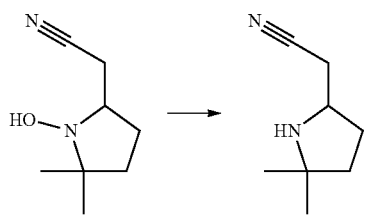

Zinc (4.9 g, 0.6869 mL, 74.935 mmol) was added in several portions to a solution of 2-(1-hydroxy-5,5-dimethyl-pyrrolidin-2-yl)acetonitrile (1.8 g, 8.1707 mmol) in acetic acid (21 mL) in ice-water bath and left the mixture to warm up to room temperature and vigorously stirred and heated to 30° C. for 6 h. The crude mixture was filtered and concentrated under reduced pressure to provide a crude product which was neutralized with 5% sodium bicarbonate (100 mL) and extracted with dichloromethane (2×100 mL). The organics were combined and dried over anhydrous sodium sulfate, filtered and concentrated under reduced pressure to provide a crude product 2-(5,5-dimethylpyrrolidin-2-yl)acetonitrile (0.9 g, 70%) as a pale yellow semi-solid. ESI-MS m/z calc. 138.1157, found 139.2 (M+1)$^+$: Retention time: 0.312 min (LC Method I).

Step 3: tert-Butyl 5-(cyanomethyl)-2,2-dimethyl-pyrrolidine-1-carboxylate

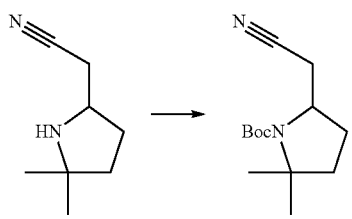

Di-tert-butyl dicarbonate (17.4 g, 18.32 mL, 79.73 mmol) was added to a solution of 2-(5,5-dimethylpyrrolidin-2-yl) acetonitrile (12 g, 51% purity, 44.28 mmol) and triethylamine (8.712 g, 12 mL, 86.10 mmol) in tetrahydrofuran (100 mL). The reaction was stirred at room temperature over a weekend. The reaction mixture was concentrated under reduced pressure to remove tetrahydrofuran. The residue was purified by silica gel chromatography using a gradient from 0%-20% of ethyl acetate in heptanes to afford tert-butyl 5-(cyanomethyl)-2,2-dimethyl-pyrrolidine-1-carboxylate (9.5 g, 63%) as a light yellow oil. ESI-MS m/z calc. 238.326, found 261.2 (M+Na)$^+$; Retention time: 2.12 min (LC Method I).

Step 4: tert-Butyl 5-(2-aminoethyl)-2,2-dimethyl-pyrrolidine-1-carboxylate

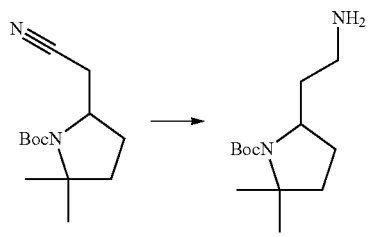 [SMILES: CC(C)(C)OC(=O)N1C(CC#N)CCC1(C)C ; CC(C)(C)OC(=O)N1C(CCN)CCC1(C)C]

A 250 mL round-bottom flask was charged with tert-butyl 5-(cyanomethyl)-2,2-dimethyl-pyrrolidine-1-carboxylate (9.1 g, 38.2 mmol), ammonia (10 mL of 7 M solution in methanol, 70 mmol), methanol (70 mL) and Raney Nickel (slurry in water, roughly 4 g, taken with spatula without weighing accurately). The mixture was vigorously stirred at room temperature under 1 atmosphere of H2 (balloon) for three days. Additional Raney-Nickel (slurry in water, roughly 6 g, taken with spatula without weighing accurately) and ammonia (10 mL of 7 M solution in methanol, 70 mmol) was added. The reaction was stirred overnight. The mixture was filtered through a pad of Celite washing with ethyl acetate. The filtrate was concentrated under reduced pressure to give a yellow oil, which was tert-butyl 5-(2-aminoethyl)-2,2-dimethyl-pyrrolidine-1-carboxylate (8.16 g, 83% yield). $^1$H NMR (300 MHz, CDCl$_3$) ppm 1.16-1.34 (m, 3H), 1.34-1.59 (m, 16H), 1.63-2.00 (m, 4H), 2.60-2.75 (m, 2H), 3.73-3.90 (m, 0.3H), 3.90-4.05 (m, 0.6H). Two rotamers were observed. ESI-MS m/z calc. 242.358, found 243.2 (M+1)$^+$; Retention time: 1.74 min (LC Method H).

Step 5: tert-Butyl 2,2-dimethyl-5-[2-[(6-sulfamoyl-2-pyridyl)amino]ethyl]pyrrolidine-1-carboxylate

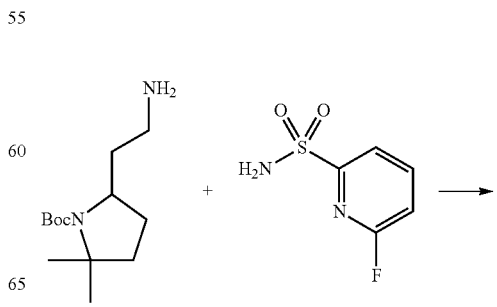

941
-continued

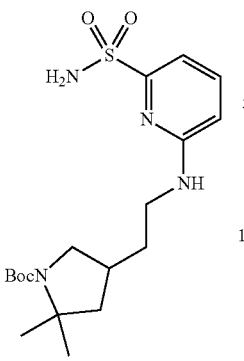

To a solution of tert-butyl 5-(2-aminoethyl)-2,2-dimethyl-pyrrolidine-1-carboxylate (500.0 mg, 2.063 mmol) in N,N-dimethylformamide (5 mL) was added 6-fluoropyridine-2-sulfonamide (302.8 mg, 1.719 mmol) followed by potassium carbonate (712.9 mg, 5.158 mmol). The flask was capped with septa and heated at 90° C. under nitrogen balloon in an oil bath for 14 h. The reaction mixture was cooled to room temperature then diluted with ethyl acetate and washed with brine solution. The organics were separated, dried over sodium sulfate, filtered and evaporated and then purified by silica gel chromatography using a gradient from 100% hexanes to 100% ethyl acetate to afford tert-butyl 2,2-dimethyl-5-[2-[(6-sulfamoyl-2-pyridyl)amino]ethyl]pyrrolidine-1-carboxylate (428 mg, 62%) as a white solid. $^1$H NMR (400 MHz, Chloroform-d) δ 7.48 (t, J=7.9 Hz, 1H), 7.18 (dd, J=7.2, 3.3 Hz, 1H), 6.53 (d, J=8.4 Hz, 1H), 5.68 (d, J=5.8 Hz, 1H), 5.50 (s, 2H), 4.00 (q, J=6.6 Hz, 1H), 3.48 (dq, J=13.0, 6.9 Hz, 1H), 3.20-3.06 (m, 1H), 2.03-1.86 (m, 1H), 1.77 (t, J=5.3 Hz, 1H), 1.59 (dq, J=14.4, 7.1 Hz, 1H), 1.46 (s, 9H), 1.39 (s, 3H), 1.28 (s, 3H). ESI-MS m/z calc. 398.19876, found 399.24 (M+1)$^+$; Retention time: 0.63 min (LC Method A).

Step 6: tert-Butyl 5-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethyl]-2,2-dimethyl-pyrrolidine-1-carboxylate

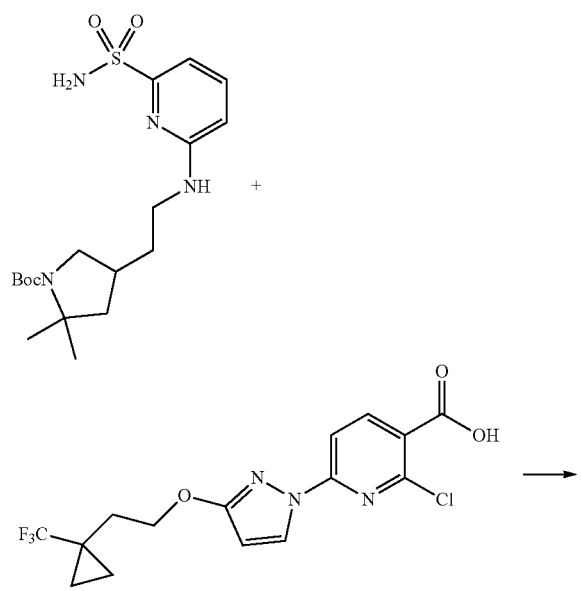

942
-continued

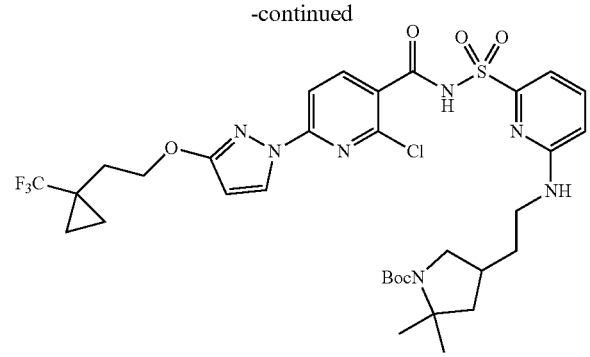

2-Chloro-6-[3-[2-[1-(trifluoromethyl)cyclopropyl]ethoxy]pyrazol-1-yl]pyridine-3-carboxylic acid (237.6 mg, 0.6323 mmol) and carbonyl diimidazole (102.5 mg, 0.6323 mmol) were combined in tetrahydrofuran (3.0 mL) and stirred for 90 min at 50° C. Then tert-butyl 2,2-dimethyl-5-[2-[(6-sulfamoyl-2-pyridyl)amino]ethyl]pyrrolidine-1-carboxylate (210 mg, 0.5269 mmol) was added followed by 1,8-diazabicyclo[5.4.0]undec-7-ene (120.3 mg, 118.2 µL, 0.7904 mmol) and the reaction was stirred at room temperature for 18 h. The reaction was diluted with ethyl acetate and washed with saturated ammonium chloride solution followed by brine. The organics were separated, dried over sodium sulfate, filtered and evaporated then purified by silica gel chromatography using a gradient from 100% dichloromethane to 20% methanol in dichloromethane to afford tert-butyl 5-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethyl]-2,2-dimethyl-pyrrolidine-1-carboxylate (321 mg, 81%) as a white solid. $^1$H NMR (400 MHz, Chloroform-d) δ 8.22 (s, 1H), 8.14 (d, J=8.1 Hz, 1H), 7.54 (d, J=14.9 Hz, 2H), 7.39 (d, J=19.1 Hz, 1H), 6.54 (s, 1H), 6.06 (s, 1H), 5.89 (d, J=2.8 Hz, 1H), 4.36 (t, J=7.2 Hz, 2H), 3.90 (s, 1H), 3.29 (s, 1H), 3.09 (s, 1H), 2.08 (t, J=7.3 Hz, 2H), 1.86 (s, 4H), 1.69 (s, 1H), 1.52 (s, 1H), 1.37 (d, J=37.2 Hz, 12H), 1.22 (s, 3H), 1.06-0.99 (m, 2H), 0.78-0.70 (m, 2H). ESI-MS m/z calc. 755.248, found 756.2 (M+1)$^+$; Retention time: 0.87 min (LC Method A)

Step 7: 8,8-Dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.0$^{5,9}$.0$^{10,15}$]tricosa-1(23),10(15),11,13,19,21-hexaene-16,18,18-trione (Compound 108)

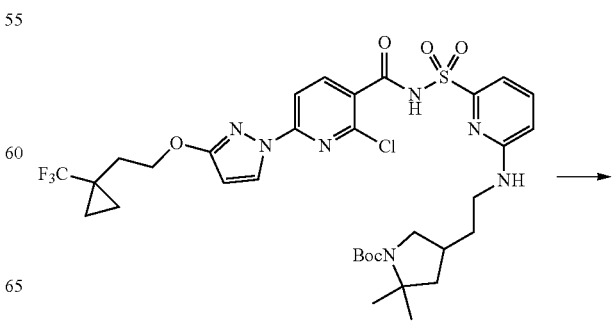

-continued

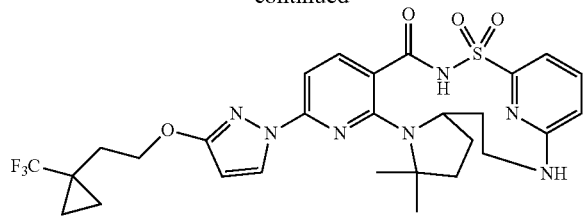

A solution of tert-butyl 5-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethyl]-2,2-dimethyl-pyrrolidine-1-carboxylate (320 mg, 0.4231 mmol) in dichloromethane (2.667 mL) and trifluoroacetic acid (482.4 mg, 323.8 µL, 4.231 mmol) was stirred at room temperature for 4 h. The solvents were removed and the residue was dissolved in ethyl acetate. Washed with 2 mL of saturated sodium bicarbonate solution and the organic layer was collected and solvent removed and the residue dried under vacuum. The above residue was dissolved in dimethyl sulfoxide (5 mL) and 3 Å molecular sieves were added and the reaction mixture was stirred for 10 min. Then, cesium fluoride (192.8 mg, 1.269 mmol) and potassium carbonate (175.4 mg, 1.269 mmol) were added and the reaction mixture was heated at 130° C. for 24 h. The reaction mixture was filtered through Celite and the Celite bed washed with ethyl acetate. The filtrate was again washed with brine solution and the solvent removed. The resultant brown residue was purified by silica gel column chromatography using a shallow gradient from 100% hexanes to 100% ethyl acetate to afford 8,8-dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.0$^{5,9}$.0$^{10,15}$]tricosa-1(23),10(15),11,13,19,21-hexaene-16,18,18-trione (Compound 108) (145 mg, 55%) as a light yellow color solid. $^1$H NMR (400 MHz, Chloroform-d) δ 13.95 (s, 1H), 8.50 (s, 1H), 8.24 (d, J=2.8 Hz, 1H), 7.63 (s, 1H), 7.52 (dd, J=8.3, 7.3 Hz, 1H), 7.28 (d, J=7.3 Hz, 1H), 6.49 (d, J=8.3 Hz, 1H), 5.96 (d, J=2.8 Hz, 1H), 4.85 (s, 1H), 4.42 (t, J=7.1 Hz, 2H), 4.24 (s, 1H), 3.01 (s, 2H), 2.59 (d, J=19.1 Hz, 1H), 2.32 (s, 1H), 2.10 (t, J=7.1 Hz, 2H), 1.91 (s, 2H), 1.60 (s, 3H), 1.13 (s, 3H), 1.06-1.00 (m, 2H), 0.77-0.70 (m, 2H). ESI-MS m/z calc. 619.2189, found 620.06 (M+1)$^+$; Retention time: 1.87 min (LC Method B).

Step 8: 8,8-Dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.0$^{5,9}$.0$^{10,15}$]tricosa-1(23),10(15),11,13,19,21-hexaene-16,18,18-trione (Enantiomer 1) (Compound 116) and 8,8-dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.0$^{5,9}$.0$^{10,15}$]tricosa-1(23),10(15),11,13,19,21-hexaene-16,18,18-trione (Enantiomer 2) (Compound 117)

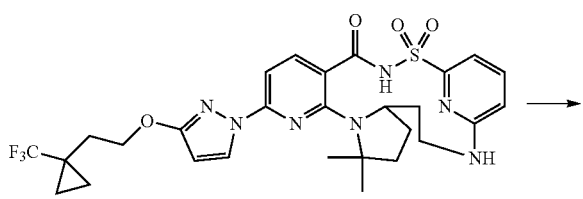

-continued

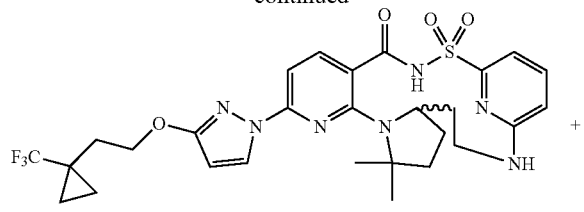

enantiomer 1 enantiomer 2

Racemic 8,8-dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.0$^{5,9}$.0$^{10,15}$]tricosa-1(23),10(15),11,13,19,21-hexaene-16,18,18-trione (Compound 108) (145 mg) was subjected to chiral separation by SFC chromatography using a ChiralPak AS-H (250×21.2 mm column, 5 µm particle size) with 25% acetonitrile/methanol (90:10)/75% carbon dioxide mobile phase at 70 mL/min (injection volume=500 µL of 32 mg/mL solution in acetonitrile/methanol (90:10)) giving as the first enantiomer to elute, 8,8-dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.0$^{5,9}$.0$^{10,15}$]tricosa-1(23),10(15),11,13,19,21-hexaene-16,18,18-trione (enantiomer 1) (Compound 116) (46.5 mg, 34%); $^1$H NMR (400 MHz, Chloroform-d) δ 13.88 (s, 1H), 8.50 (s, 1H), 8.24 (d, J=2.8 Hz, 1H), 7.64 (s, 1H), 7.52 (dd, J=8.4, 7.3 Hz, 1H), 7.28 (s, 1H), 6.50 (d, J=8.3 Hz, 1H), 5.96 (d, J=2.8 Hz, 1H), 4.89 (s, 1H), 4.48-4.38 (m, 2H), 4.24 (s, 1H), 3.01 (s, 2H), 2.59 (d, J=23.4 Hz, 1H), 2.32 (s, 1H), 2.11 (t, J=7.1 Hz, 2H), 1.92 (brs, 2H), 1.61 (d, J=6.7 Hz, 6H), 1.14 (brs, 2H), 1.07-1.00 (m, 2H), 0.79-0.71 (m, 2H), ESI-MS m/z calc. 619.2189, found 620.1 (M+1)$^+$; Retention time: 1.86 min (LC Method B) and as the second enantiomer to elute, 8,8-dimethyl-12-(3-{2-[1-(trifluoromethyl)cyclopropyl]ethoxy}-1H-pyrazol-1-yl)-18λ$^6$-thia-2,9,11,17,23-pentaazatetracyclo[17.3.1.0$^{5,9}$.0$^{10,15}$]tricosa-1(23),10(15),11,13,19,21-hexaene-16,18,18-trione (enantiomer 2) (Compound 117) (66.1 mg, 50%); $^1$H NMR (400 MHz, Chloroform-d) δ 13.87 (s, 1H), 8.50 (s, 1H), 8.25 (s, 1H), 7.63 (s, 1H), 7.54 (s, 1H), 7.28 (s, 1H), 6.52 (s, 1H), 5.96 (s, 1H), 4.81 (s, 1H), 4.42 (s, 2H), 4.25 (s, 1H), 3.04 (s, 2H), 2.58 (s, 1H), 2.33 (s, 1H), 2.11 (t, J=5.0 Hz, 2H), 1.92 (s, 2H), 1.60 (s, 6H), 1.14 (s, 2H), 1.03 (d, J=5.6 Hz, 2H), 0.75 (s, 2H). ESI-MS m/z calc. 619.2189, found 620.1 (M+1)$^+$; Retention time: 1.86 min (LC Method B).

945

Example 144: Preparation of (14S)-12,12,20-trimethyl-8-(3-{2-[1-(trifluoromethyl)cyclopropyl]ethoxy}-1H-pyrazol-1-yl)-18-oxa-2λ⁶-thia-3,9,11,23-tetraazatetracyclo[17.3.1.1¹¹,¹⁴.0⁵,¹⁰]tetracosa-1(23),5(10),6,8,19,21-hexaene-2,2,4-trione (Compound 109)

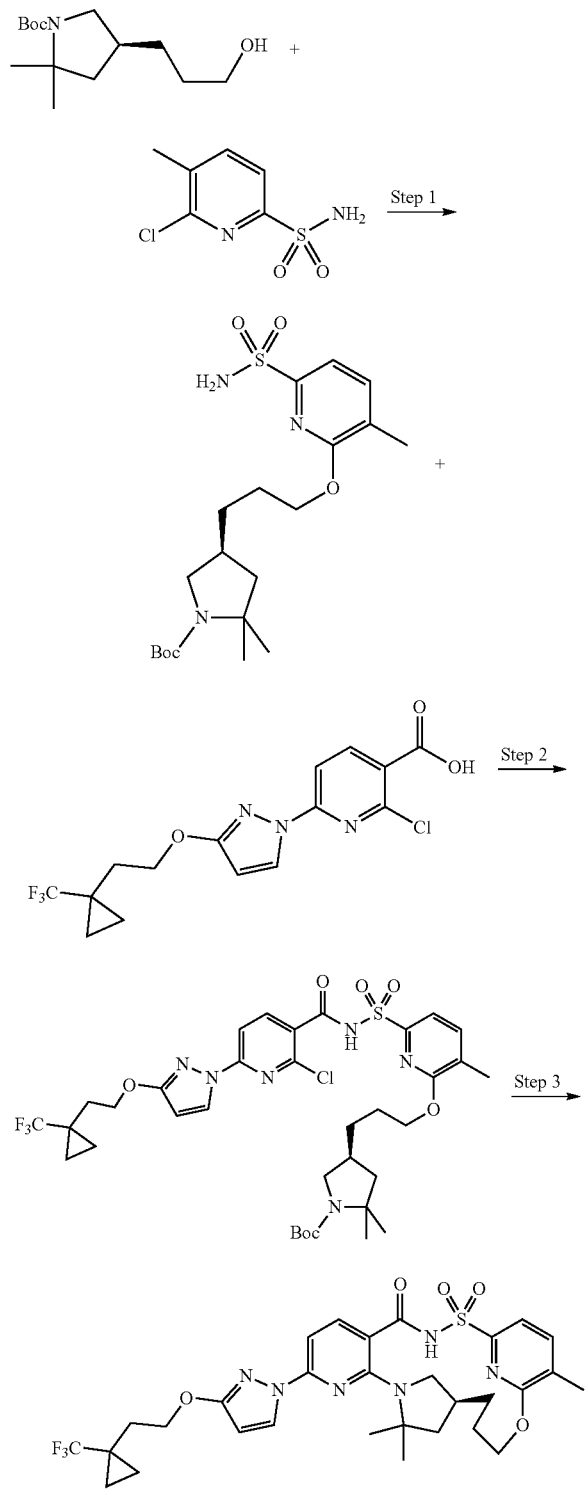

946

Step 1: tert-Butyl (4S)-2,2-dimethyl-4-[3-[(3-methyl-6-sulfamoyl-2-pyridyl)oxy]propyl]pyrrolidine-1-carboxylate

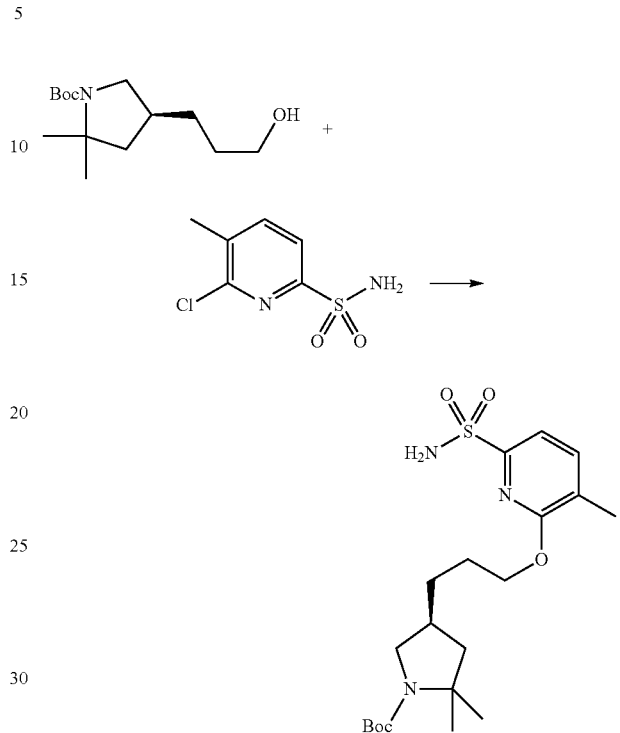

To the tert-butyl (4S)-4-(3-hydroxypropyl)-2,2-dimethyl-pyrrolidine-1-carboxylate (496 mg, 1.927 mmol) stirring under nitrogen atmosphere in N,N-dimethylformamide (6 mL) was portionwise added NaH (154.1 mg, 171.2 µL, 3.854 mmol) and the mixture was stirred at room temperature for 15 min. 6-Chloro-5-methyl-pyridine-2-sulfonamide (398.2 mg, 1.927 mmol) was then added and the resulting mixture was stirred at room temperature for 80 min. To the stirring solution at room temperature was added additional NaH (77.07 mg, 85.63 µL, 1.927 mmol) and the reaction tube was capped. The resulting mixture was stirred at 100° C. for 14 h. The cooled reaction mixture was poured into 1 N citric acid and extracted with ethyl acetate (2×). Combined the organic fractions, dried (sodium sulfate), filtered and concentrated in vacuo to a clear oil which was purified by silica gel chromatography using a mobile phase gradient from 100% hexanes to 100% ethyl acetate giving tert-butyl (4S)-2,2-dimethyl-4-[3-[(3-methyl-6-sulfamoyl-2-pyridyl)oxy]propyl]pyrrolidine-1-carboxylate (336 mg, 41%). ¹H NMR (400 MHz, dimethyl sulfoxide-$d_6$) δ 7.74 (dd, J=7.4, 1.0 Hz, 1H), 7.39 (d, J=7.4 Hz, 1H), 7.29 (s, 2H), 4.36 (s, 2H), 3.58 (q, J=8.4, 7.9 Hz, 1H), 2.81 (q, J=10.1 Hz, 1H), 2.20 (t, J=1.8 Hz, 4H), 1.96 (d, J=26.1 Hz, 1H), 1.75 (dt, J=14.2, 6.9 Hz, 2H), 1.46 (q, J=7.6, 7.1 Hz, 2H), 1.37 (t, J=10.7 Hz, 13H), 1.25 (s, 3H). ESI-MS m/z calc. 427.21408, found 428.21 (M+1)⁺; Retention time: 0.72 min. (LC Method A).

Step 2: tert-Butyl (4S)-4-[3-[[6-[[2-chloro-6-[3-[2-[1-(trifluoromethyl)cyclopropyl]ethoxy]pyrazol-1-yl]pyridine-3-carbonyl]sulfamoyl]-3-methyl-2-pyridyl]oxy]propyl]-2,2-dimethyl-pyrrolidine-1-carboxylate

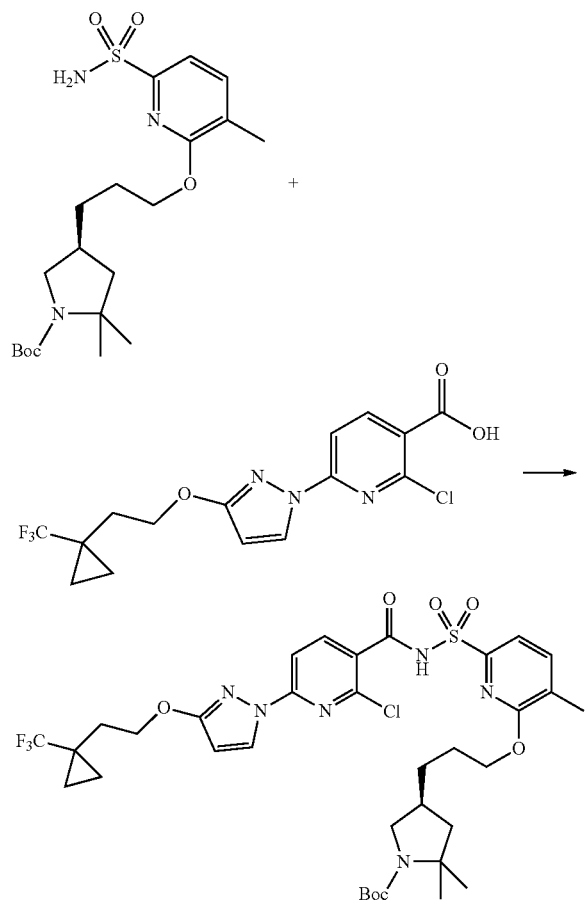

2-Chloro-6-[3-[2-[1-(trifluoromethyl)cyclopropyl]ethoxy]pyrazol-1-yl]pyridine-3-carboxylic acid (175.8 mg, 0.4678 mmol) and carbonyl diimidazole (75.85 mg, 0.4678 mmol) were combined in tetrahydrofuran (4.678 mL) and stirred for 60 min at 50° C. Then tert-butyl (4S)-2,2-dimethyl-4-[3-[(3-methyl-6-sulfamoyl-2-pyridyl)oxy]propyl]pyrrolidine-1-carboxylate (200 mg, 0.4678 mmol) was added followed by 1,8-diazabicyclo[5.4.0]undec-7-ene (71.22 mg, 69.96 µL, 0.4678 mmol) and the reaction was heated at 50° C. for 15 h. The reaction was diluted with ethyl acetate and washed with a 1 M citric acid solution followed by brine. The organics were separated, dried over sodium sulfate, filtered and evaporated and then purified by silica gel chromatography using a gradient from 100% hexanes to 75% ethyl acetate in hexanes to afford as an off-white solid, tert-butyl (4S)-4-[3-[[6-[[2-chloro-6-[3-[2-[1-(trifluoromethyl)cyclopropyl]ethoxy]pyrazol-1-yl]pyridine-3-carbonyl]sulfamoyl]-3-methyl-2-pyridyl]oxy]propyl]-2,2-dimethyl-ethyl-pyrrolidine-1-carboxylate (296 mg, 81%). ESI-MS m/z calc. 784.2633, found 785.1 (M+1)+; Retention time: 0.84 min (LC Method A).

Step 3: (14S)-12,12,20-Trimethyl-8-(3-{2-[1-(trifluoromethyl)cyclopropyl]ethoxy}-1H-pyrazol-1-yl)-18-oxa-2λ⁶-thia-3,9,11,23-tetraazatetracyclo[17.3.1.1¹¹,¹⁴.0⁵,¹⁰]tetracosa-1(23),5(10),6,8,19,21-hexaene-2,2,4-trione (Compound 109)

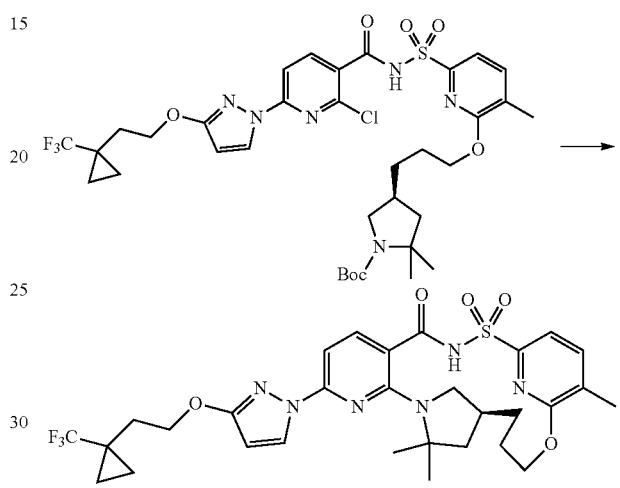

tert-Butyl (4S)-4-[3-[[6-[[2-chloro-6-[3-[2-[1-(trifluoromethyl)cyclopropyl]ethoxy]pyrazol-1-yl]pyridine-3-carbonyl]sulfamoyl]-3-methyl-2-pyridyl]oxy]propyl]-2,2-dimethyl-ethyl-pyrrolidine-1-carboxylate (296 mg, 0.3769 mmol) was dissolved in dichloromethane (5 mL) and to the mixture was added hydrochloric acid (3.5 mL of 4 M in dioxane, 14.00 mmol) and stirred at room temperature for 30 min. The reaction solution was concentrated in vacuo to dryness. Combined the resulting material with potassium carbonate (313 mg, 2.265 mmol), cesium fluoride (93 mg, 0.6122 mmol), 3 Å molecular sieves and dimethyl sulfoxide (6 mL) in a vial, purged with nitrogen, capped, heated to 140° C. and stirred for 16 h. Cooled to room temperature and the reaction mixture was filtered and then purified by reverse-phase preparative chromatography utilizing a $C_{18}$ column (20%-99% acetonitrile-water+5 mM hydrochloric acid) to afford as a white solid, (14S)-12,12,20-trimethyl-8-(3-{2-[1-(trifluoromethyl)cyclopropyl]ethoxy}-1H-pyrazol-1-yl)-18-oxa-2λ⁶-thia-3,9,11,23-tetraazatetracyclo[17.3.1.1¹¹,14.0⁵,¹⁰]tetracosa-1 (23),5(10),6,8,19,21-hexaene-2,2,4-trione (Compound 109) (78 mg, 32%). ¹H NMR (400 MHz, dimethyl sulfoxide-d₆) δ 12.73 (s, 1H), 8.21 (d, J=2.8 Hz, 1H), 7.86 (dd, J=8.3, 7.0 Hz, 2H), 7.58 (d, J=7.4 Hz, 1H), 6.94 (d, J=8.2 Hz, 1H), 6.12 (d, J=2.7 Hz, 1H), 5.18 (t, J=12.2 Hz, 1H), 4.32 (t, J=7.0 Hz, 2H), 3.96 (d, J=11.1 Hz, 1H), 3.14 (t, J=8.4 Hz, 1H), 2.56 (d, J=10.8 Hz, 1H), 2.18 (s, 3H), 2.11-2.01 (m, 3H), 1.85 (dd, J=11.9, 5.3 Hz, 1H), 1.70 (t, J=12.9 Hz, 2H), 1.55 (d, J=39.3 Hz, 8H), 1.22 (q, J=12.6, 12.2 Hz, 1H), 1.03-0.92 (m, 2H), 0.92-0.84 (m, 2H). ESI-MS m/z calc. 648.2342, found 649.41 (M+1)⁺; Retention time: 2.38 min (LC Method B).

Example 145: Preparation of 20,20-dimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.111,14.02,7]docosa-2,4,6,11(22),12-pentaene-8,10,10-trione (Compound 110)

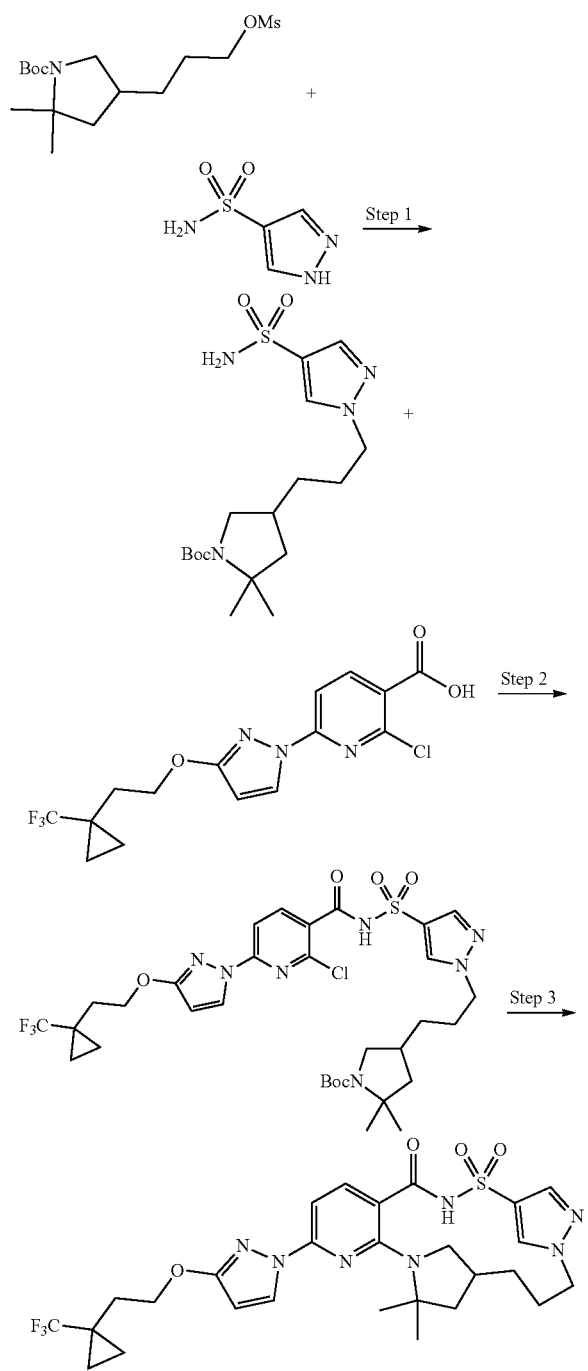

Step 1: tert-Butyl 2,2-dimethyl-4-[3-(4-sulfamoylpyrazol-1-yl)propyl]pyrrolidine-1-carboxylate

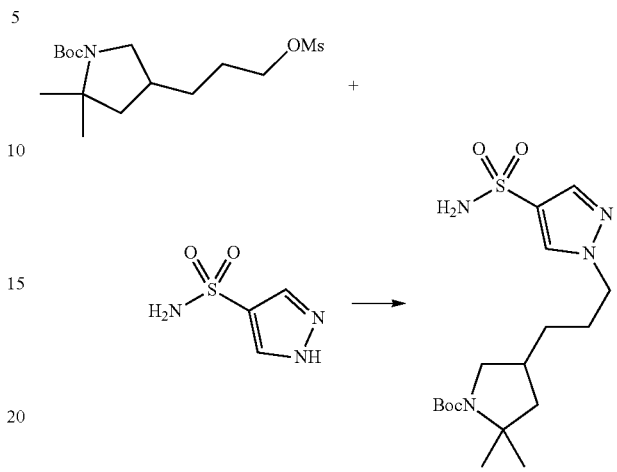

tert-Butyl 2,2-dimethyl-4-(3-methylsulfonyloxypropyl)pyrrolidine-1-carboxylate (490 mg, 1.461 mmol) and 1H-pyrazole-4-sulfonamide (215 mg, 1.461 mmol) followed by potassium carbonate (710 mg, 5.137 mmol) were dissolved in N,N-dimethylformamide (15 mL) and stirred at 50° C. in a 150 mL sealed vessel for 48 h. Cooled to room temperature then poured into water (100 mL) and extracted with ethyl acetate (2×100 mL), combined the organic layers, washed with water (2×100 mL), dried (sodium sulfate), filtered and concentrated. The orange residue was purified by silica gel chromatography using a gradient from 100% hexanes to 100% ethyl acetate to afford as a colorless oil which turned into a white solid upon vacuum drying, tert-butyl 2,2-dimethyl-4-[3-(4-sulfamoylpyrazol-1-yl)propyl]pyrrolidine-1-carboxylate (400 mg, 71%). ¹H NMR (400 MHz, dimethyl sulfoxide-d₆) δ 8.20 (s, 1H), 7.71 (s, 1H), 7.23 (s, 2H), 4.14 (t, J=6.7 Hz, 2H), 3.54 (dd, J=18.0, 10.3 Hz, 1H), 2.74 (q, J=10.2 Hz, 1H), 2.10 (dt, J=10.1, 6.4 Hz, 1H), 1.87 (td, J=13.0, 6.1 Hz, 1H), 1.81-1.69 (m, 2H), 1.38 (d, J=10.5 Hz, 10H), 1.34 (d, J=10.7 Hz, 3H), 1.24 (s, 5H). ESI-MS m/z calc. 386.19876, found 387.2 (M+1)⁺; Retention time: 1.49 min (LC Method E).

Step 2: tert-Butyl 4-[3-[4-[[2-chloro-6-[3-[2-[1-(trifluoromethyl)cyclopropyl]ethoxy]pyrazol-1-yl]pyridine-3-carbonyl]sulfamoyl]pyrazol-1-yl]propyl]-2,2-dimethyl-pyrrolidine-1-carboxylate

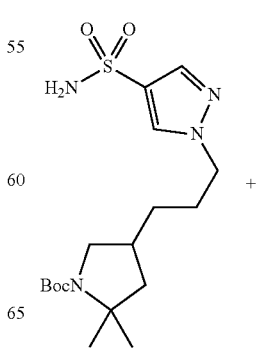

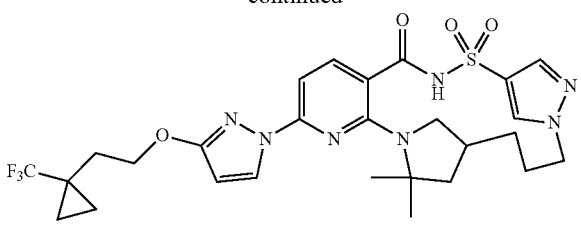

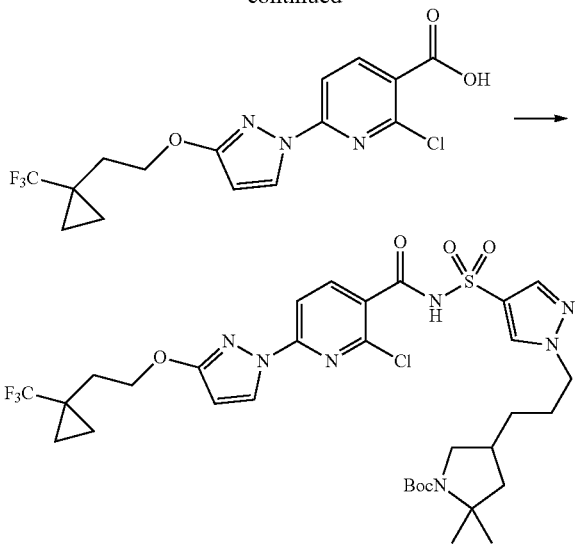

2-Chloro-6-[3-[2-[1-(trifluoromethyl)cyclopropyl]ethoxy]pyrazol-1-yl]pyridine-3-carboxylic acid (335 mg, 0.8916 mmol) and carbonyl diimidazole (143 mg, 0.8819 mmol) were combined in tetrahydrofuran (4.5 mL) and stirred for 60 min at room temperature. Then tert-butyl 2,2-dimethyl-4-[3-(4-sulfamoylpyrazol-1-yl)propyl]pyrrolidine-1-carboxylate (200 mg, 0.5175 mmol) was added followed by 1,8-diazabicyclo[5.4.0]undec-7-ene (225 µL, 1.505 mmol) and the reaction was heated at 50° C. for 18 h. The reaction was diluted with ethyl acetate and washed with a saturated aqueous sodium bicarbonate solution, followed by brine. The organics were separated, dried over sodium sulfate, filtered and evaporated and then purified by silica gel chromatography using a gradient from 100% hexanes to 100% ethyl acetate to afford as an off-white solid, tert-butyl 4-[3-[4-[[2-chloro-6-[3-[2-[1-(trifluoromethyl)cyclopropyl]ethoxy]pyrazol-1-yl]pyridine-3-carbonyl]sulfamoyl]pyrazol-1-yl]propyl]-2,2-dimethyl-pyrrolidine-1-carboxylate (201 mg, 52%). ESI-MS m/z calc. 743.248, found 744.2 (M+1)$^+$; Retention time: 1.84 min (LC Method E).

Step 3: 20,20-Dimethyl-4-(3-{2-[1-(trifluoromethyl)cyclopropyl]ethoxy}-1H-pyrazol-1-yl)-10λ$^6$-thia-1,3,9,13,14-pentaazatetracyclo[16.2.1.111,14.02,7]docosa-2,4,6,11(22),12-pentaene-8,10,10-trione (Compound 110)

tert-Butyl 4-[3-[4-[[2-chloro-6-[3-[2-[1-(trifluoromethyl)cyclopropyl]ethoxy]pyrazol-1-yl]pyridine-3-carbonyl]sulfamoyl]pyrazol-1-yl]propyl]-2,2-dimethyl-pyrrolidine-1-carboxylate (200 mg, 0.2687 mmol) was dissolved in dichloromethane (5.0 mL) and to the mixture was added hydrochloric acid (2.5 mL of 4 M in dioxane, 10.00 mmol) and stirred at room temperature for 30 min. Concentrated the mixture to dryness under reduced pressure, redissolved in ethyl acetate and then added aqueous 2 M sodium carbonate (5 mL), giving pH 10. Extracted the solution with ethyl acetate (2×10 mL), washed with brine, then dried over sodium sulfate, filtered and evaporated to dryness under reduced pressure. Combined the resulting material and potassium carbonate (190 mg, 1.375 mmol), cesium fluoride (65 mg, 0.4279 mmol), 3 Å molecular sieves and dimethyl sulfoxide (6 mL) in a vial, purged with nitrogen, capped, heated to 155° C. and stirred for 20 h. Cooled to room temperature and filtered, diluted with ethyl acetate and washed with a saturated aqueous sodium bicarbonate solution, followed by brine. The organics were separated, dried over sodium sulfate, filtered and evaporated and then purified by silica gel chromatography using a gradient from 100% hexanes to 80% ethyl acetate in hexanes followed by a second column using a gradient from 100% dichloromethane to 10% methanol in dichloromethane to afford as a white solid, 20,20-dimethyl-4-(3-{2-[1-(trifluoromethyl)cyclopropyl]ethoxy}-1H-pyrazol-1-yl)-10λ$^6$-thia-1,3,9,13,14-pentaazatetracyclo[16.2.1.111,14.02,7]docosa-2,4,6,11(22),12-pentaene-8,10,10-trione (Compound 110) (59.6 mg, 36%). $^1$H NMR (400 MHz, dimethyl sulfoxide-d$_6$) δ 12.24 (s, 1H), 8.55 (s, 1H), 8.18 (d, J=2.8 Hz, 1H), 7.88 (s, 1H), 7.74 (d, J=8.2 Hz, 1H), 6.89 (d, J=8.2 Hz, 1H), 6.10 (d, J=2.7 Hz, 1H), 4.31 (t, J=7.0 Hz, 3H), 4.07 (t, J=11.5 Hz, 1H), 2.17 (dd, J=7.3, 5.2 Hz, 1H), 2.07 (t, J=7.1 Hz, 4H), 1.93 (t, J=9.3 Hz, 1H), 1.87-1.69 (m, 2H), 1.60 (d, J=12.4 Hz, 1H), 1.49 (s, 6H), 1.37 (t, J=12.1 Hz, 1H), 1.09-0.99 (m, 1H), 0.98-0.93 (m, 2H), 0.89 (d, J=11.2 Hz, 2H). ESI-MS m/z calc. 607.2189, found 608.2 (M+1)$^+$; Retention time: 2.07 min (LC Method E).

Example 146: Preparation of (18S)-20,20,22-trimethyl-4-(3-{2-[1-(trifluoromethyl) cyclopropyl]ethoxy}-1H-pyrazol-1-yl)-10λ⁶-thia-1,3,9,13,14-pentaazatetra cyclo[16.2.1.1¹¹,¹⁴.0²,⁷]docosa-2,4,6,11(22),12-pentaene-8,10,10-trione (Atropisomer 1) (Compound 111), (18S)-12,20,20-trimethyl-4-(3-{2-[1-(trifluoromethyl)cyclo propyl]ethoxy}-1H-pyrazol-1-yl)-10λ⁶-thia-1,3,9,13,14-pentaazatetra cyclo[16.2.1.1¹¹,¹⁴.0²,⁷]docosa-2,4,6,11(22),12-pentaene-8,10,10-trione (Compound 112) and (18S)-20,20,22-trimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹¹,14.0²,⁷]docosa-2,4,6,11(22),12-pentaene-8,10,10-trione (Atropisomer 2) (Compound 113)

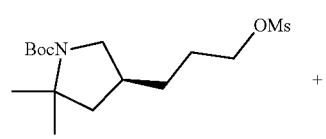

+

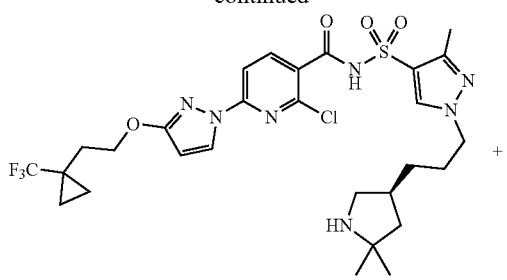

+

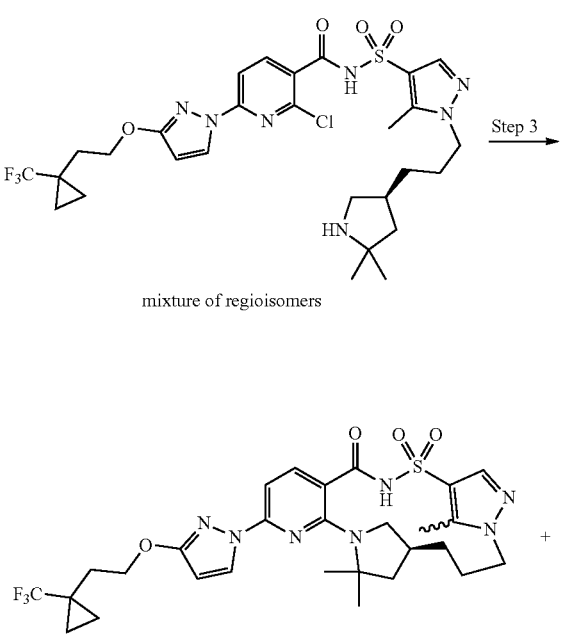

mixture of regioisomers

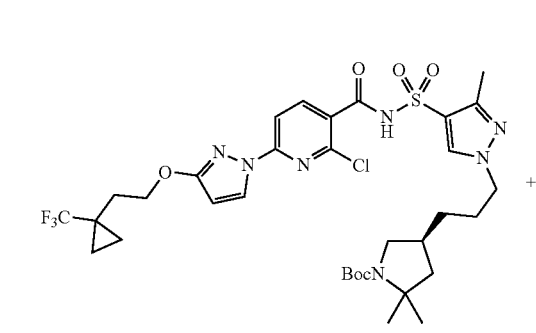

Step 1

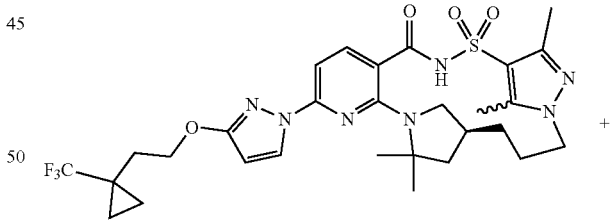

atropisomer 1

+

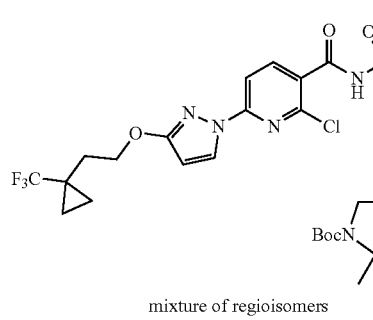

Step 2 mixture of regioisomers

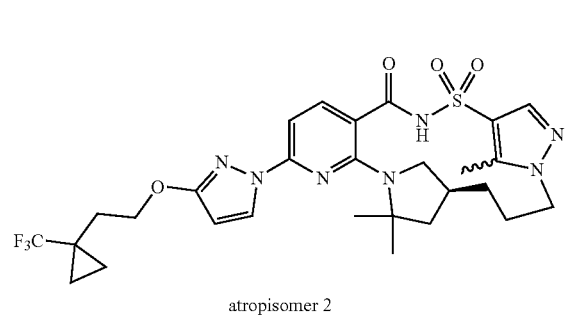

atropisomer 2

Step 1: tert-Butyl (4S)-4-[3-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]propyl]-2,2-dimethyl-pyrrolidine-1-carboxylate and tert-butyl (4S)-4-[3-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (Mixture of Regioisomers)

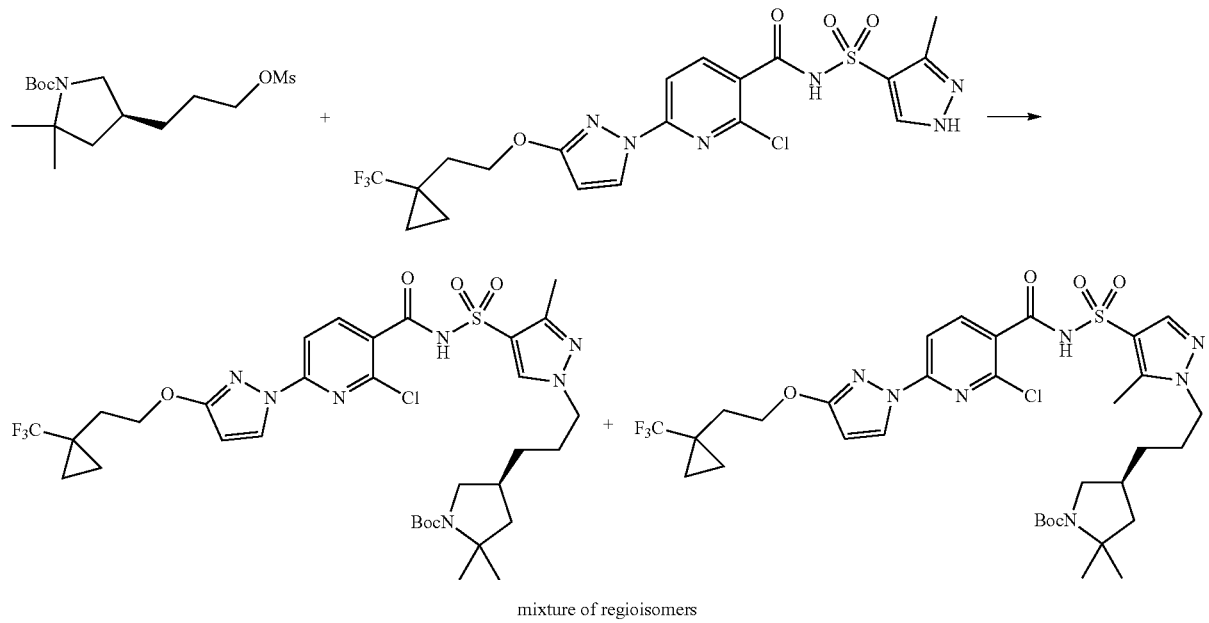

mixture of regioisomers

To a flask containing 2-chloro-N-[(5-methyl-1H-pyrazol-4-yl)sulfonyl]-6-[3-[2-[1-(trifluoromethyl)cyclopropyl]ethoxy]pyrazol-1-yl]pyridine-3-carboxamide (900 mg, 1.734 mmol), potassium carbonate (720 mg, 5.210 mmol), and dimethyl sulfoxide (14 mL) was added a solution of tert-butyl (4S)-2,2-dimethyl-4-(3-methylsulfonyloxypropyl)pyrrolidine-1-carboxylate (699 mg, 2.084 mmol) in dimethyl sulfoxide (2 mL) and the reaction was allowed to stir at 95° C. overnight. The reaction was cooled to room temperature, filtered, and purified via HPLC (30%-99% acetonitrile/water with a 0.1% hydrochloric acid modifier to provide tert-butyl (4S)-4-[3-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]propyl]-2,2-dimethyl-pyrrolidine-1-carboxylate and tert-butyl (4S)-4-[3-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (mixture of regioisomers) (524.1 mg, 40%). ESI-MS m/z calc. 757.2636, found 758.5 (M+1)$^+$; Retention time: 1.93 min (LC Method G).

Step 2: 2-Chloro-N-[1-[3-[(3S)-5,5-dimethylpyrrolidin-3-yl]propyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[3-[(3S)-5,5-dimethylpyrrolidin-3-yl]propyl]-5-methyl-pyrazol-4-yl]sulfonyl-6-[3-[2-[1-(trifluoromethyl)cyclopropyl]ethoxy]pyrazol-1-yl]pyridine-3-carboxamide (Mixture of Regioisomers)

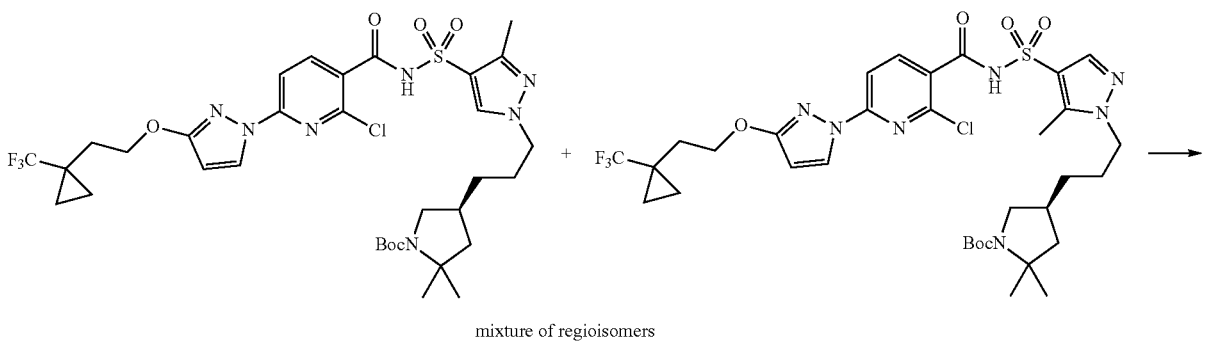

mixture of regioisomers

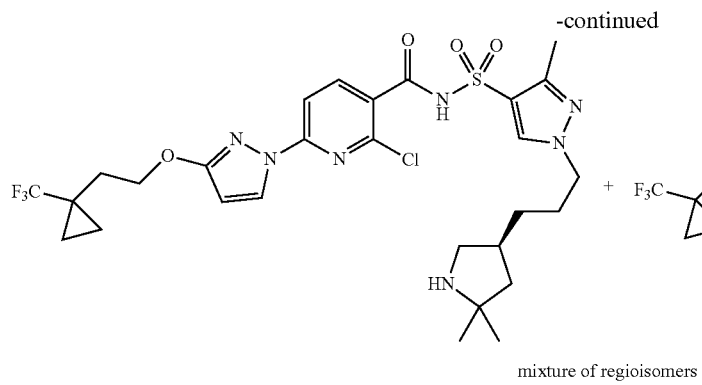

mixture of regioisomers

To a flask provide tert-butyl (4S)-4-[3-[4-[[2-chloro-6-[3-[2-[1-(trifluoromethyl)cyclopropyl]ethoxy]pyrazol-1-yl]pyridine-3-carbonyl]sulfamoyl]-3-methyl-pyrazol-1-yl]propyl]-2,2-dimethyl-pyrrolidine-1-carboxylate and tert-butyl (4S)-4-[3-[4-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (mixture of regioisomers) (524 mg, 0.6911 mmol) was added dichloromethane (10 mL) and Trifluoroacetic acid (2.7 mL, 35.05 mmol). The reaction was stirred for 1 h at room temperature. The reaction was then evaporated to dryness and quenched with saturated sodium bicarbonate. The reaction was extracted with a solution of dichloromethane:methanol (9:1) 3 times, dried over sodium sulfate, and evaporated to provide 2-chloro-N-[1-[3-[(3S)-5,5-dimethylpyrrolidin-3-yl]propyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[3-[(3S)-5,5-dimethylpyrrolidin-3-yl]propyl]-5-methyl-pyrazol-4-yl]sulfonyl-6-[3-[2-[1-(trifluoromethyl)cyclopropyl]ethoxy]pyrazol-1-yl]pyridine-3-carboxamide (mixture of regioisomers) (435 mg, 96%). ESI-MS m/z calc. 657.2112, found 658.3 (M+1)$^+$; Retention time: 1.61 min (LC Method E).

Step 3: (18S)-20,20,22-Trimethyl-4-(3-{2-[1-(trifluoromethyl)cyclopropyl]ethoxy}-1H-pyrazol-1-yl)-10λ$^6$-thia-1,3,9,13,14-pentaazatetracyclo[16.2.1.1$^{11,14}$.0$^{2,7}$]docosa-2,4,6,11(22),12-pentaene-8,10,10-trione (Atropisomer 1) (Compound 111), (18S)-12,20,20-trimethyl-4-(3-{2-[1-(trifluoromethyl)cyclopropyl]ethoxy}-1H-pyrazol-1-yl)-10λ$^6$-thia-1,3,9,13,14-pentaazatetracyclo[16.2.1.1$^{11,14}$.0$^{2,7}$]docosa-2,4,6,11(22),12-pentaene-8,10,10-trione (Compound 112) and (18S)-20,20,22-trimethyl-4-(3-{2-[1-(trifluoromethyl)cyclopropyl]ethoxy}-1H-pyrazol-1-yl)-10λ$^6$-thia-1,3,9,13,14-pentaazatetracyclo[16.2.1.1$^{11,14}$.0$^{2,7}$]docosa-2,4,6,11(22),12-pentaene-8,10,10-trione (Atropisomer 2) (Compound 113)

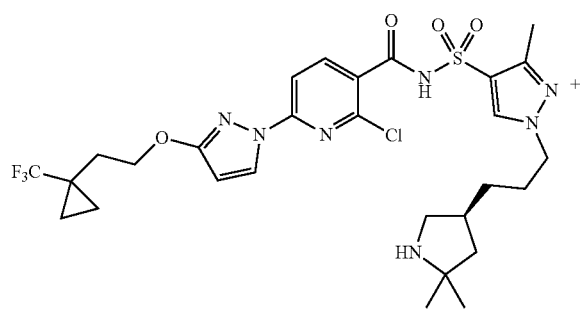

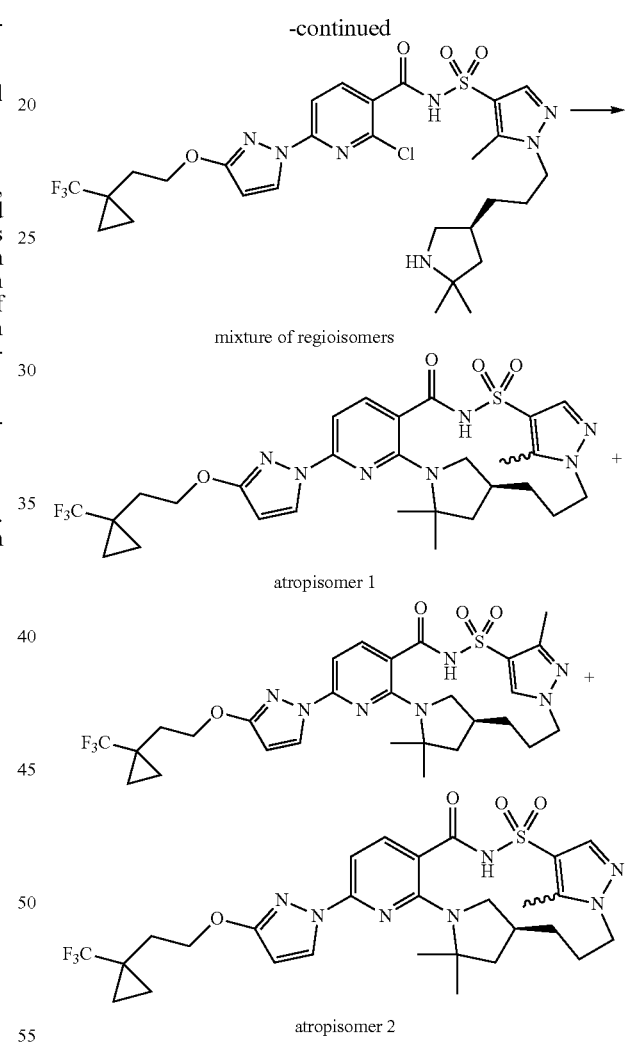

mixture of regioisomers atropisomer 1 atropisomer 2

To a 20 dram vial was added potassium carbonate (458 mg, 3.314 mmol), cesium fluoride (302 mg, 1.988 mmol), and a solution of 2-chloro-N-[1-[3-[(3S)-5,5-dimethylpyrrolidin-3-yl]propyl]-3-methyl-pyrazol-4-yl]sulfonyl-6-[3-[2-[1-(trifluoromethyl)cyclopropyl]ethoxy]pyrazol-1-yl]pyridine-3-carboxamide and 2-chloro-N-[1-[3-[(3S)-5,5-dimethylpyrrolidin-3-yl]propyl]-5-methyl-pyrazol-4-yl]sulfonyl-6-[3-[2-[1-(trifluoromethyl)cyclopropyl]ethoxy]pyrazol-1-yl]pyridine-3-carboxamide (mixture of regioisomers) (435 mg, 0.6610 mmol) in dimethyl sulfoxide (17.50 mL). The reaction was heated at 160° C. overnight.

The reaction was cooled to room temperature, filtered, and purified via HPLC (30%-80% acetonitrile in water with hydrochloric acid modifier) to provide as the first product to elute, (18S)-20,20,22-trimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,¹⁴.0²,⁷]docosa-2,4,6,11(22),12-pentaene-8,10,10-trione (atropisomer 1) (Compound 111) (32.5 mg, 16%). ¹H NMR (400 MHz, dimethyl sulfoxide-d₆) δ 12.39 (s, 1H), 8.18 (d, J=2.8 Hz, 1H), 7.86 (s, 1H), 7.77 (d, J=8.2 Hz, 1H), 6.90 (d, J=8.2 Hz, 1H), 6.10 (d, J=2.7 Hz, 1H), 4.38 (dt, J=14.1, 3.1 Hz, 1H), 4.31 (t, J=7.0 Hz, 2H), 4.01 (td, J=14.0, 2.8 Hz, 1H), 2.06 (q, J=8.0, 7.6 Hz, 5H), 1.90-1.71 (m, 3H), 1.55 (s, 3H), 1.47 (s, 3H), 1.45-1.30 (m, 2H), 1.10 (s, 1H), 0.99-0.93 (m, 2H), 0.93-0.85 (m, 2H). Three protons are obscured by residual solvent. ESI-MS m/z calc. 621.2345, found 622.3 (M+1)⁺; Retention time: 2.96 min (LC Method D). The second product to elute was (18S)-12,20,20-trimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,¹⁴.0²,⁷]docosa-2,4,6,11(22),12-pentaene-8,10,10-trione (Compound 112) (53.9 mg, 26%). ¹H NMR (400 MHz, dimethyl sulfoxide-d₆) δ 12.18 (s, 1H), 8.41 (s, 1H), 8.18 (d, J=2.8 Hz, 1H), 7.75 (d, J=8.2 Hz, 1H), 6.89 (d, J=8.2 Hz, 1H), 6.10 (d, J=2.7 Hz, 1H), 4.31 (t, J=7.0 Hz, 2H), 4.22 (dt, J=13.6, 3.8 Hz, 1H), 4.03-3.92 (m, 1H), 2.40 (s, 3H), 2.22 (d, J=11.8 Hz, 1H), 2.11-1.91 (m, 5H), 1.83 (dt, J=15.7, 7.4 Hz, 1H), 1.75 (dd, J=11.9, 5.0 Hz, 1H), 1.51 (d, J=13.0 Hz, 7H), 1.38 (t, J=12.2 Hz, 1H), 1.03 (s, 1H), 0.99-0.84 (m, 4H). ESI-MS m/z calc. 621.2345, found 622.3 (M+1)⁺; Retention time: 3.01 min (LC Method D). The third product to elute was (18S)-20,20,22-trimethyl-4-(3-{2-[1-(trifluoromethyl)cyclopropyl]ethoxy}-1H-pyrazol-1-yl)-10λ⁶-thia-1,3,9,13,14-pentaazatetra cyclo[16.2.1.1¹¹,¹⁴.0²,⁷]docosa-2,4,6,11(22),12-pentaene-8,10,10-trione (atropisomer 2) (Compound 113) (12.4 mg, 6%). ¹H NMR (400 MHz, dimethyl sulfoxide-d₆) δ 12.10 (s, 1H), 8.18 (d, J=2.8 Hz, 1H), 7.81-7.70 (m, 2H), 6.88 (d, J=8.3 Hz, 1H), 6.10 (d, J=2.8 Hz, 1H), 4.40-4.26 (m, 3H), 4.00 (ddd, J=13.5, 10.2, 2.7 Hz, 1H), 2.68 (s, 3H), 2.43-2.32 (m, 1H), 2.07 (t, J=7.1 Hz, 3H), 1.96-1.57 (m, 5H), 1.57-1.41 (m, 8H), 1.00-0.84 (m, 4H). (2 obscured by residual solvent). ESI-MS m/z calc. 621.2345, found 622.4 (M+1)⁺; Retention time: 3.08 min (LC Method D).

Example 147: Preparation of 20,20-dimethyl-4-(3-{2-[1-(trifluoromethyl)cyclopropyl]ethoxy}-1H-pyrazol-1-yl)-10λ⁶-thia-1,3,9,13,14-pentaazatetra cyclo[16.2.1.1¹¹,¹⁴.0²,⁷]docosa-2,4,6,11(22),12-pentaene-8,10,10-trione (Enantiomer 1) (Compound 118) and 20,20-dimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,14.02⁷]docosa-2,4,6,11(22),12-pentaene-8,10,10-trione (Enantiomer 2) (Compound 119)

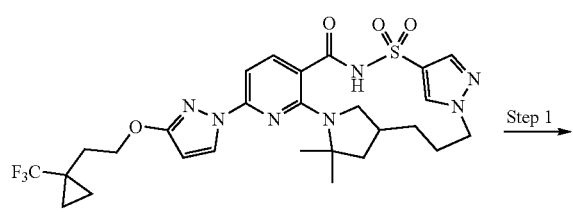

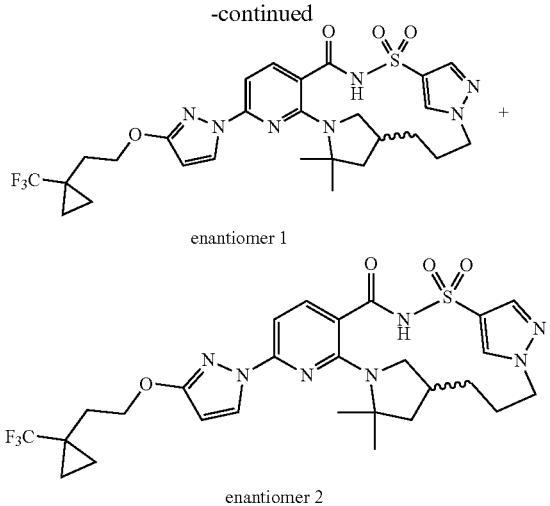

Step 1: 20,20-Dimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,¹⁴.0²,⁷]docosa-2,4,6,11(22),12-pentaene-8,10,10-trione (Enantiomer 1) (Compound 118) and 20,20-dimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,¹⁴.0²,⁷]docosa-2,4,6,11(22),12-pentaene-8,10,10-trione (Enantiomer 2) (Compound 119)

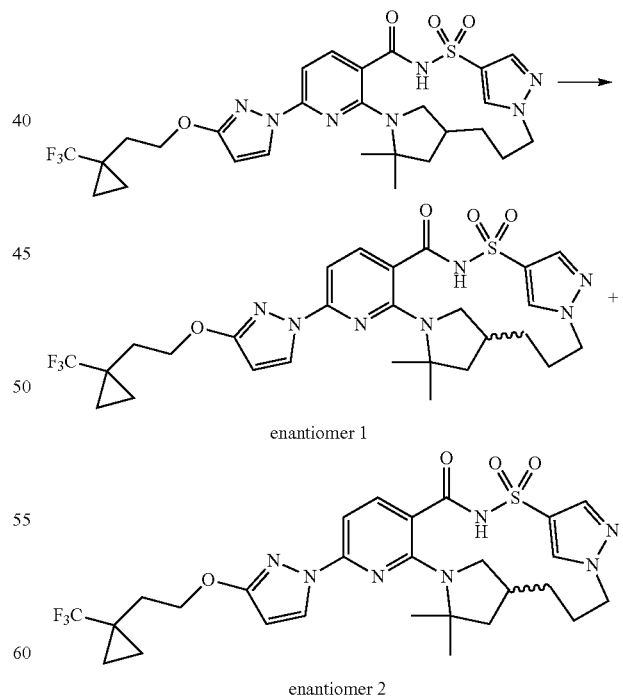

Racemic 20,20-dimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹.14.0²,⁷]docosa-2,4,6,11(22),12-pentaene-8,10,10-trione (57 mg, 0.09287 mmol) was subjected to chiral separation by SFC chromatography using a ChiralPak AS-H (250×10 mm, 5 μm particle size) with 26% acetonitrile:methanol (90:10; no modifier)/74% carbon dioxide mobile phase at 10 mL/min over 8.0 min (injection volume=70 μL of 24 mg/mL solution in methanol/dimethyl sulfoxide (90:10)) giving as the first enantiomer to elute, 20,20-dimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,¹⁴.0²,⁷]docosa-2,4,6,11(22),12-pentaene-8,10,10-trione (enantiomer 1) (Compound 118) (20.76 mg, 74%) as a white solid. ¹H NMR (400 MHz, dimethyl sulfoxide-d₆) δ 12.24 (s, 1H), 8.53 (s, 1H), 8.18 (d, J=2.8 Hz, 1H), 7.87 (s, 1H), 7.73 (d, J=8.2 Hz, 1H), 6.88 (d, J=8.2 Hz, 1H), 6.09 (d, J=2.7 Hz, 1H), 4.30 (t, J=7.1 Hz, 3H), 4.06 (t, J=11.7 Hz, 2H), 2.25-2.10 (m, 1H), 2.05 (dt, J=9.6, 5.0 Hz, 4H), 1.93 (dd, J=16.2, 7.1 Hz, 1H), 1.82 (d, J=12.4 Hz, 1H), 1.76-1.68 (m, 1H), 1.54 (s, 1H), 1.51 (d, J=15.5 Hz, 6H), 1.37 (t, J=12.0 Hz, 1H), 1.08-0.99 (m, 1H), 0.98-0.92 (m, 2H), 0.91-0.84 (m, 2H). ESI-MS m/z calc. 607.2189, found 608.2 (M+1)⁺; Retention time: 2.07 min (LC Method E). The second enantiomer to elute was 20,20-dimethyl-4-(3-{2-[1-(trifluoromethyl)cyclopropyl]ethoxy}-1H-pyrazol-1-yl)-10λ⁶-thia-1,3,9,13,14-pentaazatetracyclo[16.2.1.1¹¹,¹⁴.0²,⁷]docosa-2,4,6,11(22),12-pentaene-8,10,10-trione (enantiomer 2) (Compound 119) (17.84 mg, 63%) as a white solid. ESI-MS m/z calc. 607.2189, found 608.3 (M+1)⁺; Retention time: 2.07 min (LC Method E).

Example 148: Preparation of 21,21-dimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Compound 122)

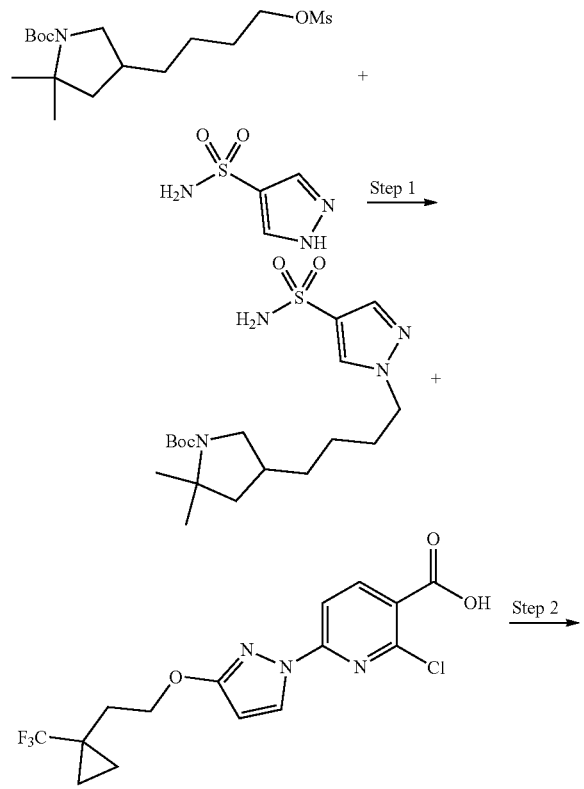

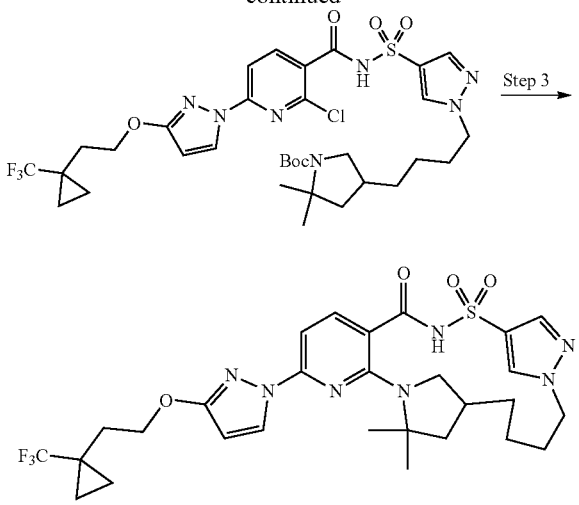

Step 1: tert-Butyl 2,2-dimethyl-4-[4-(4-sulfamoylpyrazol-1-yl)butyl]pyrrolidine-1-carboxylate

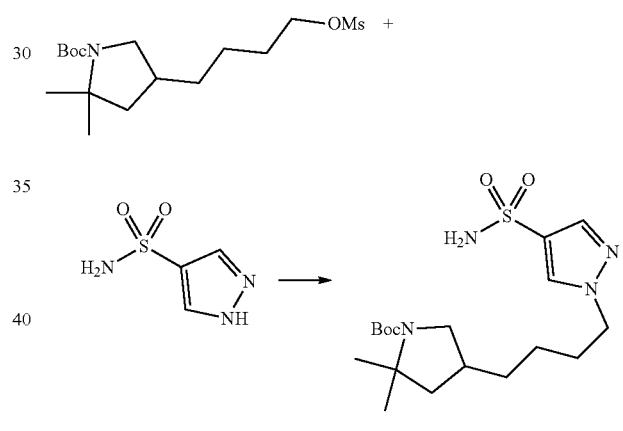

tert-Butyl 2,2-dimethyl-4-(4-methylsulfonyloxybutyl)pyrrolidine-1-carboxylate (600 mg, 1.717 mmol), 1H-pyrazole-4-sulfonamide (256 mg, 1.740 mmol) and potassium carbonate (850 mg, 6.150 mmol) were combined in N,N-dimethylformamide (15 mL) and stirred at 50° C. in a sealed 150 mL vessel for 22 h. Cooled the mixture to room temperature, poured into water (100 mL) and extracted with ethyl acetate (2×100 mL), combined the organic layers, washed with water (2×100 mL), dried (sodium sulfate), filtered and concentrated. The orange residue was purified by silica gel chromatography using a gradient from 100% dichloromethane to 15% methanol in dichloromethane to afford as a colorless oil, tert-butyl 2,2-dimethyl-4-[4-(4-sulfamoylpyrazol-1-yl)butyl]pyrrolidine-1-carboxylate (499 mg, 73%). ¹H NMR (400 MHz, dimethyl sulfoxide-d₆) δ 8.19 (s, 1H), 7.71 (s, 1H), 7.23 (s, 2H), 4.13 (t, J=7.0 Hz, 2H), 3.52 (dd, J=13.9, 8.6 Hz, 1H), 2.06 (d, J=12.0 Hz, 1H), 1.85 (dd, J=16.8, 10.1 Hz, 1H), 1.80-1.71 (m, 2H), 1.42-1.34 (m, 13H), 1.32 (d, J=7.2 Hz, 3H), 1.29 (d, J=5.6 Hz, 1H), 1.23 (s, 4H). ESI-MS m/z calc. 400.21442, found 401.2 (M+1)⁺; Retention time: 1.61 min (LC Method E).

Step 2: tert-Butyl 4-[4-[4-[[2-chloro-6-[3-[2-[1-(trifluoromethyl)cyclopropyl]ethoxy]pyrazol-1-yl]pyridine-3-carbonyl]sulfamoyl]pyrazol-1-yl]butyl]-2,2-dimethyl-pyrrolidine-1-carboxylate Step 3: 21,21-Dimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Compound 122)

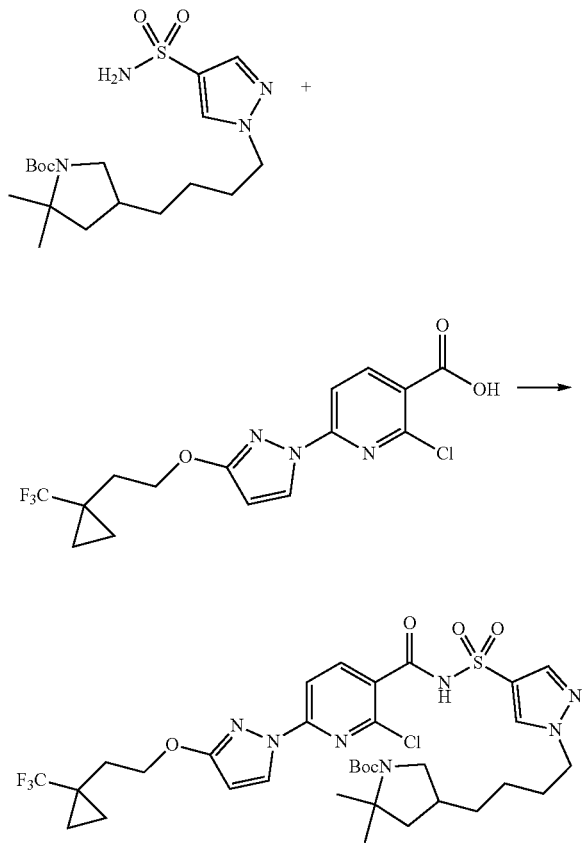

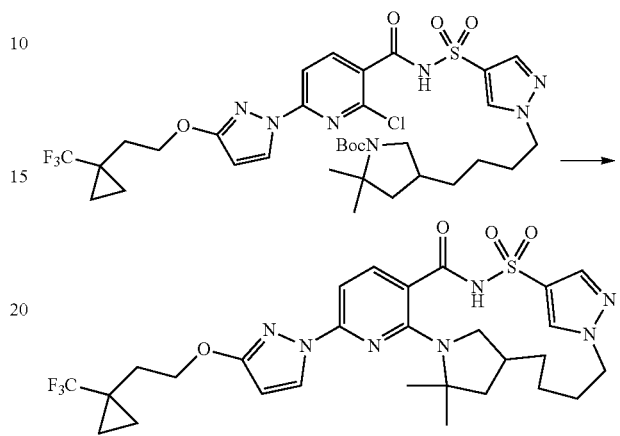

2-Chloro-6-[3-[2-[1-(trifluoromethyl)cyclopropyl]ethoxy]pyrazol-1-yl]pyridine-3-carboxylic acid (410 mg, 1.091 mmol) and carbonyl diimidazole (177 mg, 1.092 mmol) were combined in tetrahydrofuran (6.0 mL) and stirred for 90 min at 50° C. Then tert-butyl 2,2-dimethyl-4-[4-(4-sulfamoylpyrazol-1-yl)butyl]pyrrolidine-1-carboxylate (257 mg, 0.6416 mmol) was added followed by 1,8-diazabicyclo[5.4.0]undec-7-ene (240 µL, 1.605 mmol) and the reaction was heated at 50° C. for 16 h. The reaction was diluted with ethyl acetate and washed with a saturated aqueous sodium bicarbonate solution, followed by brine. The organics were separated, dried over sodium sulfate, filtered and evaporated and then purified by silica gel chromatography using a gradient from 100% dichloromethane to 10% methanol in dichloromethane to afford as an off-white solid, tert-butyl 4-[4-[4-[[2-chloro-6-[3-[2-[1-(trifluoromethyl)cyclopropyl]ethoxy]pyrazol-1-yl]pyridine-3-carbonyl]sulfamoyl]pyrazol-1-yl]butyl]-2,2-dimethyl-pyrrolidine-1-carboxylate (345 mg, 71%). ESI-MS m/z calc. 757.2636, found 758.2 (M+1)⁺; Retention time: 1.93 min (LC Method E).

tert-Butyl 4-[4-[4-[[2-chloro-6-[3-[2-[1-(trifluoromethyl)cyclopropyl]ethoxy]pyrazol-1-yl]pyridine-3-carbonyl]sulfamoyl]pyrazol-1-yl]butyl]-2,2-dimethyl-pyrrolidine-1-carboxylate (315 mg, 0.4154 mmol) was dissolved in dichloromethane (8.5 mL) and to the mixture was added hydrochloric acid (3.25 mL of 4 M in dioxane, 13.00 mmol) and the mixture was stirred at room temperature for 30 min. Concentrated mixture to dryness under reduced pressure, redissolved in ethyl acetate and then added aqueous 2 M sodium carbonate (5 mL), giving pH~10. Extracted the solution with ethyl acetate (2×10 mL), washed with brine then dried over sodium sulfate, filtered and evaporated to dryness under reduced pressure. Combined the resulting material with potassium carbonate (290 mg, 2.098 mmol), cesium fluoride (95 mg, 0.6254 mmol), 3 Å molecular sieves and dimethyl sulfoxide (10.0 mL) in a vial, purged with nitrogen, capped, heated to 155° C. and stirred for 20 h. Cooled to room temperature and filtered, diluted with ethyl acetate and washed with a saturated aqueous sodium bicarbonate solution, followed by brine. The organics were separated, dried over sodium sulfate, filtered and evaporated and then purified by silica gel chromatography using a gradient from 100% dichloromethane to 10% methanol in dichloromethane followed by a second column using a gradient from 100% hexanes to 80% ethyl acetate in hexanes to afford as a white solid, 21,21-dimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (Compound 122) (131 mg, 50%). NMR (400 MHz, dimethyl sulfoxide-d₆) δ 12.34 (s, 1H), 8.83 (s, 1H), 8.21 (d, J=2.7 Hz, 1H), 7.94 (s, 1H), 7.81 (d, J=8.4 Hz, 1H), 6.91 (d, J=8.2 Hz, 1H), 6.12 (d, J=2.6 Hz, 1H), 4.44 (td, J=11.3, 3.3 Hz, 1H), 4.31 (t, J=7.0 Hz, 2H), 4.19 (dd, J=19.3, 5.9 Hz, 1H), 2.97 (t, J=9.5 Hz, 1H), 2.33 (dd, J=12.1, 8.3 Hz, 1H), 2.08 (t, J=6.9 Hz, 4H), 1.85 (dd, J=11.6, 5.2 Hz, 1H), 1.59 (s, 4H), 1.54 (d, J=9.8 Hz, 4H), 1.48 (d, J=9.2 Hz, 1H), 1.27 (dd, J=21.2, 8.7 Hz, 2H), 0.95 (q, J=7.1 Hz, 2H), 0.90 (d, J=10.6 Hz, 2H), 0.02-0.08 (m, 1H). ESI-MS m/z calc. 621.2345, found 622.3 (M+1)⁺; Retention time: 2.16 min (LC Method E).

Example 149: Preparation of 12,12-dimethyl-8-(3-{2-[1-(trifluoromethyl)cyclopropyl]ethoxy}-1H-pyrazol-1-yl)-2λ⁶-thia-3,9,11,19,22-pentaazatetracyclo[18.2.2.1¹¹,¹⁴.0⁵,¹⁰]pentacosa-1(22),5(10),6,8,20,23-hexaene-2,2,4-trione (Compound 123)

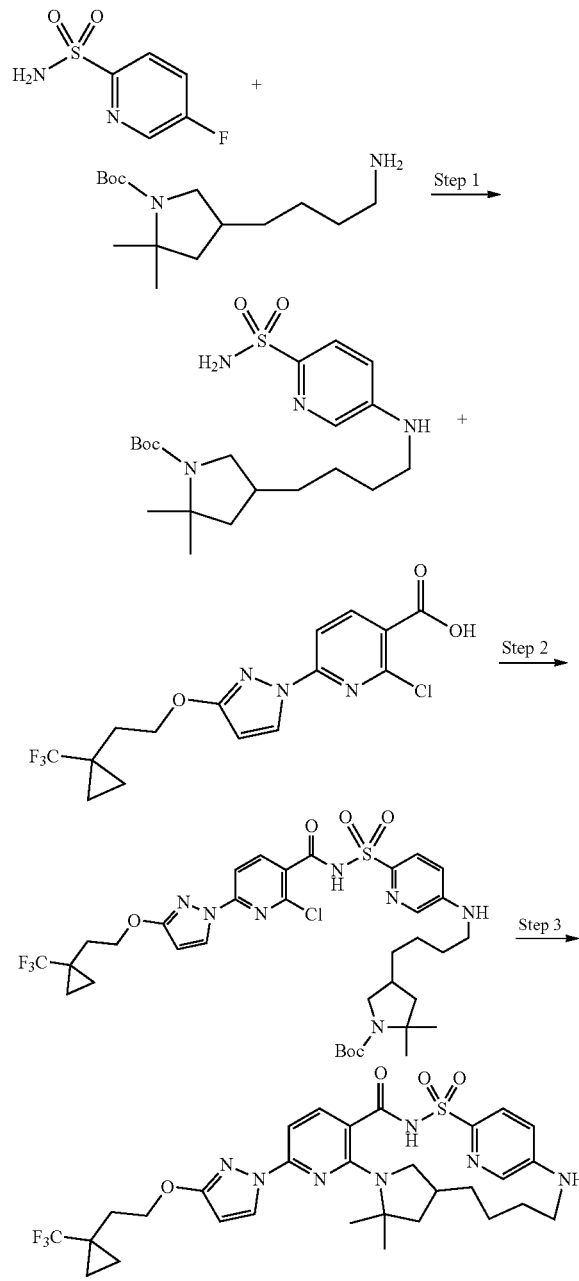

Step 1: tert-Butyl 2,2-dimethyl-4-[4-[(6-sulfamoyl-3-pyridyl)amino]butyl]pyrrolidine-1-carboxylate

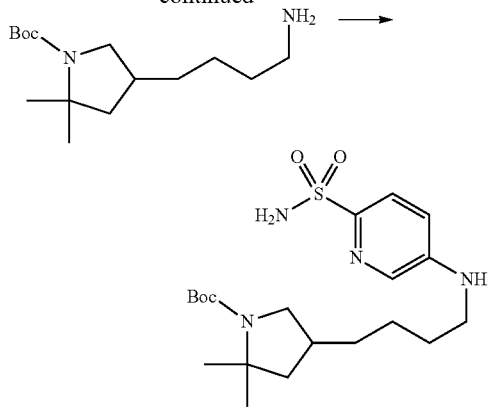

In a sealed 5 mL vial, a solution of tert-butyl 4-(4-aminobutyl)-2,2-dimethyl-pyrrolidine-1-carboxylate (507 mg, 1.875 mmol), 5-fluoropyridine-2-sulfonamide (300 mg, 1.703 mmol), and diisopropyl ethyl amine (1.5 mL, 8.612 mmol) in n-BuOH (3 mL) was stirred at 160° C. for 16 h. The solvent was removed in vacuo and the residue was dissolved in dichloromethane and washed with water. Organic extract was dried over sodium sulfate, filtered, evaporated and purified by silica gel chromatography (0% to 40% ethyl acetate in hexanes) to afford tert-butyl 2,2-dimethyl-4-[4-[(6-sulfamoyl-3-pyridyl)amino]butyl]pyrrolidine-1-carboxylate (210 mg, 29%). ESI-MS m/z calc. 426.23007, found 427.26 (M+1)⁺; Retention time: 1.73 min (LC Method B).

Step 2: tert-Butyl 4-[4-[[6-[[2-chloro-6-[3-[2-[1-(trifluoromethyl)cyclopropyl]ethoxy]pyrazol-1-yl]pyridine-3-carbonyl]sulfamoyl]-3-pyridyl]amino]butyl]-2,2-dimethyl-pyrrolidine-1-carboxylate

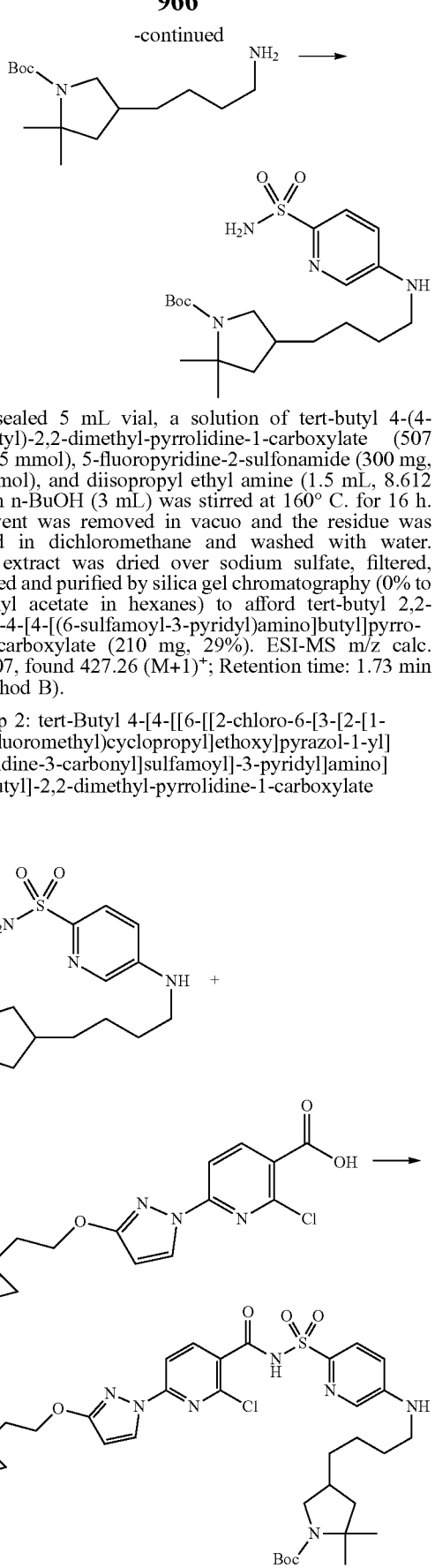

2-Chloro-6-[3-[2-[1-(trifluoromethyl)cyclopropyl]ethoxy]pyrazol-1-yl]pyridine-3-carboxylic acid (278 mg, 0.7399 mmol) and carbonyl diimidazole (120 mg, 0.7401 mmol) were combined in tetrahydrofuran (6 mL) and stirred for 90 min at 50° C. Then a solution of tert-butyl 2,2-dimethyl-4-[4-[(6-sulfamoyl-3-pyridyl)amino]butyl]pyrrolidine-1-carboxylate (210 mg, 0.4923 mmol) and 1,8-diazabicyclo[5.4.0]undec-7-ene (190 mg, 1.248 mmol) in tetrahydrofuran (3 mL) was added. The reaction was heated at 50° C. overnight. The reaction was diluted with ethyl acetate and washed with water. The organic phase was dried over sodium sulfate, filtered and evaporated then purified by preparative reverse phase HPLC ($C_{18}$, 1% to 99% acetonitrile in water with hydrochloric acid modifier to afford tert-butyl 4-[4-[[6-[[2-chloro-6-[3-[2-[1-(trifluoromethyl)cyclopropyl]ethoxy]pyrazol-1-yl]pyridine-3-carbonyl]sulfamoyl]-3-pyridyl]amino]butyl]-2,2-dimethyl-pyrrolidine-1-carboxylate (264.4 mg, 68%). ESI-MS m/z calc. 783.27924, found 784.39 (M+1)$^+$; Retention time: 0.91 min (LC Method A).

Step 3: 12,12-Dimethyl-8-(3-{2-[1-(trifluoromethyl)cyclopropyl]ethoxy}-1H-pyrazol-1-yl)-2λ$^6$-thia-3,9,11,19,22-pentaazatetracyclo[18.2.2.1¹¹,¹⁴.0⁵,¹⁰]pentacosa-1(22),5(10),6,8,20,23-hexaene-2,2,4-trione (Compound 123)

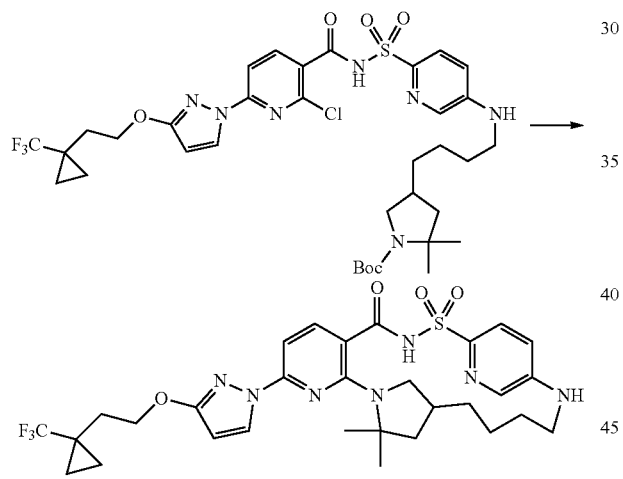

tert-Butyl 4-[4-[[6-[[2-chloro-6-[3-[2-[1-(trifluoromethyl)cyclopropyl]ethoxy]pyrazol-1-yl]pyridine-3-carbonyl]sulfamoyl]-3-pyridyl]amino]butyl]-2,2-dimethyl-pyrrolidine-1-carboxylate (260 mg, 0.3315 mmol) was dissolved in dichloromethane (5 mL) and to the solution was added hydrochloric acid (2.5 mL of 4 M in dioxane, 10.00 mmol) and the resulting mixture was stirred at room temperature for 30 min. The mixture was concentrated to dryness under reduced pressure and the obtained intermediate was combined with potassium carbonate (230 mg, 1.664 mmol), cesium fluoride (80 mg, 0.5266 mmol), 3 Å molecular sieves (300 mg) and dimethyl sulfoxide (3 mL) in a 5 mL vial which was purged with nitrogen and stirred at 150° C. overnight. The mixture was cooled to room temperature, filtered and purified by preparative reverse phase HPLC ($C_{18}$, 1% to 99% acetonitrile in water with hydrochloric acid modifier to afford 12,12-dimethyl-8-(3-{2-[1-(trifluoromethyl)cyclopropyl]ethoxy}-1H-pyrazol-1-yl)-2λ$^6$-thia-3,9,11,19,22-pentaazatetracyclo[18.2.2.1¹¹,¹⁴.0⁵,¹⁰]pentacosa-1(22),5(10),6,8,20,23-hexaene-2,2,4-trione (Compound 123) (8.7 mg, 4%). ESI-MS m/z calc. 647.2502, found 648.34 (M+1)$^+$; Retention time: 2.2 min (LC Method B).

Example 150: Preparation of 21,21-dimethyl-4-(3-{2-[1-(trifluoromethyl)cyclopropyl]ethoxy}-1H-pyrazol-1-yl)-10λ$^6$-thia-1,3,9,13,14-pentaazatetracyclo[17.2.1.1¹¹,¹⁴.0²,⁷]tricosa-2,4,6,11(23),12-pentaene-8,10,10-trione (enantiomer 1) (Compound 134) and 21,21-dimethyl-4-(3-{2-[1-(trifluoromethyl)cyclopropyl]ethoxy}-1H-pyrazol-1-yl)-10λ$^6$-thia-1,3,9,13,14-pentaazatetracyclo[17.2.1.1¹¹,¹⁴.0²,⁷]tricosa-2,4,6,11(23),12-pentaene-8,10,10-trione (Enantiomer 2) (Compound 135)

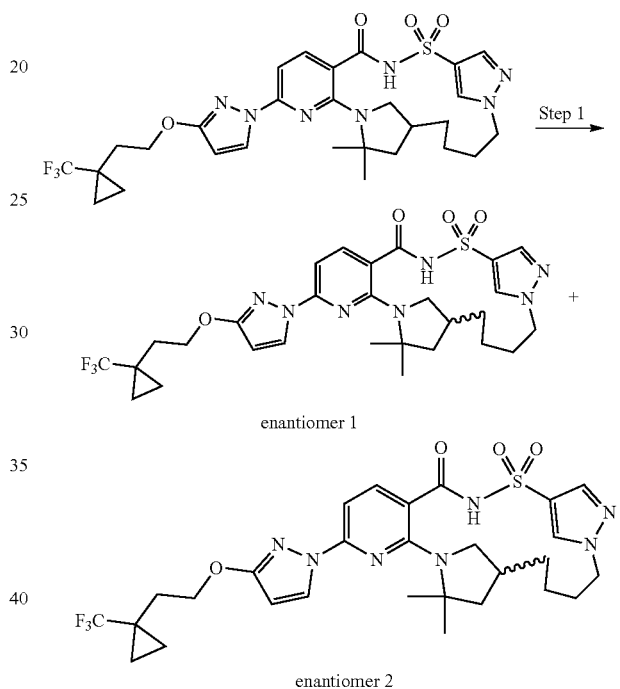

Step 1: 21,21-Dimethyl-4-(3-{2-[1-(trifluoromethyl)cyclopropyl]ethoxy}-1H-pyrazol-1-yl)-10λ$^6$-thia-1,3,9,13,14-pentaazatetracyclo[17.2.1.1¹¹,¹⁴.0²,⁷]tricosa-2,4,6,11(23),12-pentaene-8,10,10-trione (Enantiomer 1) (Compound 134) and 21,21-dimethyl-4-(3-{2-[1-(trifluoromethyl)cyclopropyl]ethoxy}-1H-pyrazol-1-yl)-10λ$^6$-thia-1,3,9,13,14-pentaazatetracyclo[17.2.1.1¹¹,¹⁴.0²,⁷]tricosa-2,4,6,11(23),12-pentaene-8,10,10-trione (Enantiomer 2) (Compound 135)

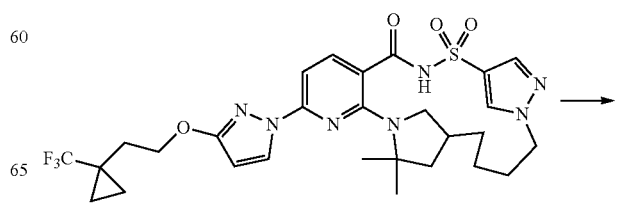

969

-continued

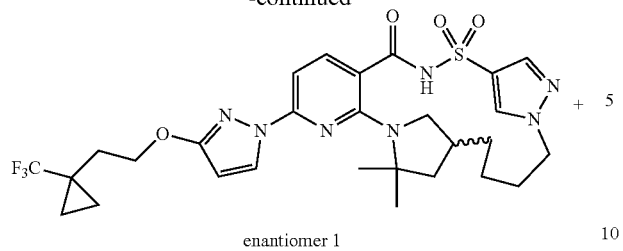
enantiomer 1

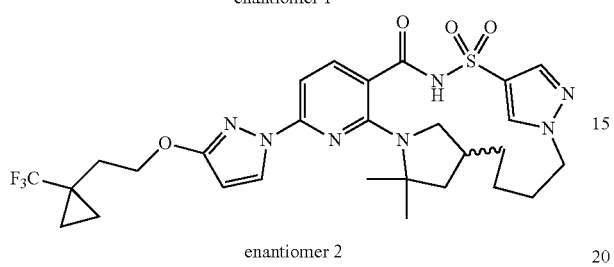
enantiomer 2

Racemic 21,21-dimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (100 mg, 0.1592 mmol) was subjected to chiral SFC chromatography (ChiralPak AS-H (250×10 mm), 5 μM column; mobile phase=34% acetonitrile/methanol (90:10, no modifier), 66% carbon dioxide, 10 mL/min; concentration 24 mg/mL in acetonitrile/methanol/dimethyl sulfoxide (80:10:10; no modifier); injection volume 70 μL, 100 bar). The first enantiomer to elute was 21,21-dimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.0²,⁷]tricosa-2,4,6,11(23),12-pentaene-8,10,10-trione (enantiomer 1) (Compound 134) (24.1 mg, 49%) as a white solid. ESI-MS m/z calc. 621.2345, found 622.3 (M+1)⁺; Retention time: 2.16 min (LC Method E). The second enantiomer to elute was 21,21-dimethyl-4-(3-{2-[1-(trifluoromethyl)cyclopropyl]ethoxy}-1H-pyrazol-1-yl)-10λ⁶-thia-1,3,9,13,14-pentaazatetracyclo[17.2.1.1¹¹,¹⁴.02,7]tricosa-2,4,6,11(23),12-pentaene-8,10,10-trione (enantiomer 2) (Compound 135) (25.4 mg, 51%) as a white solid. ESI-MS m/z calc. 621.2345, found 622.3 (M+1)⁺; Retention time: 2.16 min (LC Method E).

Example 151: Preparation of 12,12,18-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Enantiomer 1) (Compound 138) and 12,12,18-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.05,10]tetracosa-1(23),5(10),6,8,19,21-hexaene-2,2,4-trione (Enantiomer 2) (Compound 139)

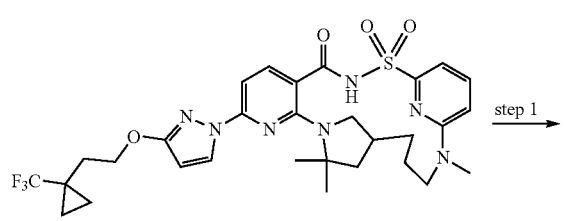 step 1

970

-continued

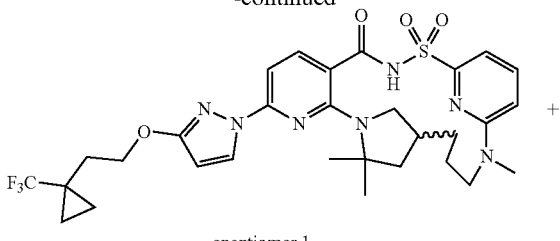
enantiomer 1

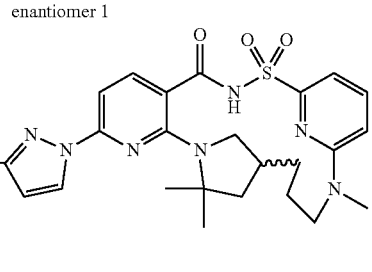
enantiomer 2

Step 1: 12,12,18-Trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.05,10]tetracosa-1(23),5(10),6,8,19,21-hexaene-2,2,4-trione (Enantiomer 1) (Compound 138) and 12,12,18-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.05,10]tetracosa-1(23),5(10),6,8,19,21-hexaene-2,2,4-trione (Enantiomer 2) (Compound 139)

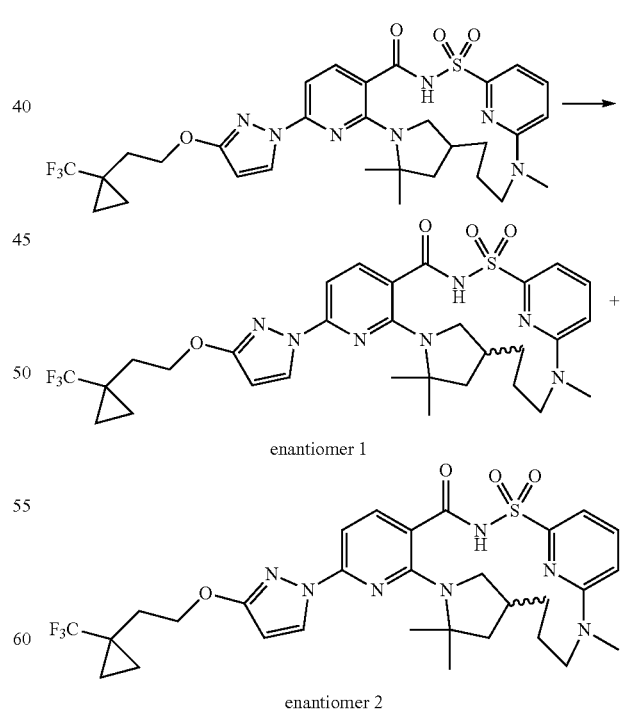

Racemic 12,12,18-trimethyl-8-(3-{2-[1-(trifluoromethyl)cyclopropyl]ethoxy}-1H-pyrazol-1-yl)-2λ⁶-thia-3,9,11,18,23-pentaazatetracyclo[17.3.1.1¹¹,¹⁴.05,10]tetracosa-1(23), 5(10),6,8,19,21-hexaene-2,2,4-trione (29 mg) was subjected to chiral separation by SFC chromatography using a Phenomenex LUX-4 (250×10 mm) column, 5 μm particle size with 22% methanol (0.1% trifluoroacetic acid), 78% carbon dioxide mobile phase at 10 mL/min over 6.0 min (injection volume=70 μL of 24 mg/mL in methanol:dimethyl sulfoxide (85:15)) giving as the first enantiomer to elute, 12,12,18-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 1) (Compound 138) (7.1 mg, 49%); ESI-MS m/z calc. 647.2502, found 648.34 (M+1)⁺; Retention time: 2.38 min (LC Method B) and as the second enantiomer to elute, 12,12,18-trimethyl-8-(3-{2-[1-(trifluoromethyl)cyclopropyl]ethoxy}-1H-pyrazol-1-yl)-2λ$^6$-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (enantiomer 2) (Compound 139) (9.4 mg, 55%); ESI-MS m/z calc. 647.2502, found 648.42 (M+1)⁺; Retention time: 2.38 min (LC Method B).

Example 152: Preparation of 12,12,18-trimethyl-8-(3-{2-[1-(trifluoromethyl)cyclopropyl]ethoxy}-1H-pyrazol-1-yl)-2λ$^6$-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Compound 140)

Step 1: tert-Butyl 2,2-dimethyl-4-[3-[methyl-(5-sulfamoyl-2-pyridyl)amino]propyl]pyrrolidine-1-carboxylate

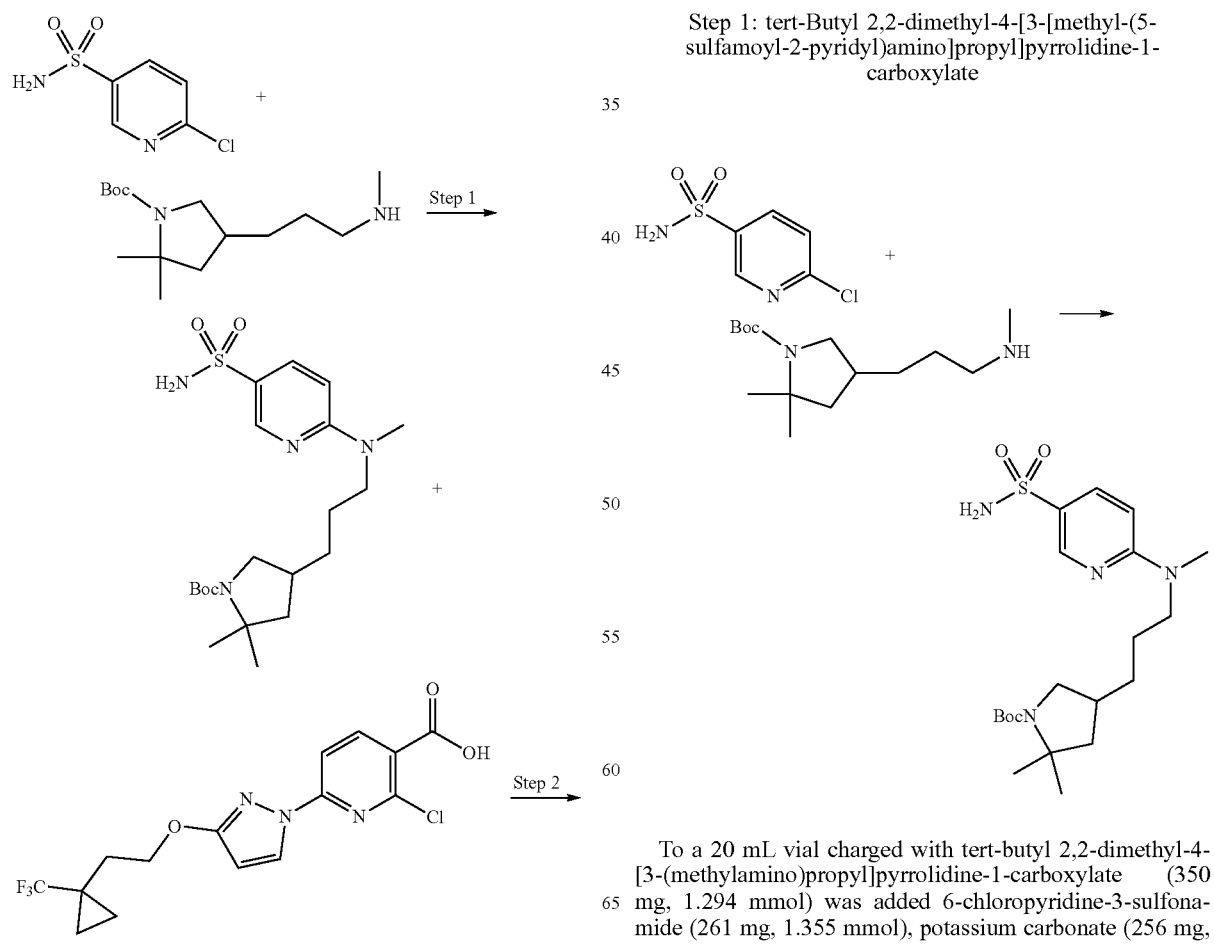

To a 20 mL vial charged with tert-butyl 2,2-dimethyl-4-[3-(methylamino)propyl]pyrrolidine-1-carboxylate (350 mg, 1.294 mmol) was added 6-chloropyridine-3-sulfonamide (261 mg, 1.355 mmol), potassium carbonate (256 mg, 1.852 mmol) and dimethyl sulfoxide (4 mL). The headspace was purged with nitrogen, the vial capped, and the reaction mixture stirred at 120° C. for 18 h. Cooled to room temperature, diluted with ethyl acetate (~40 mL) and the crude mixture washed with water (10 mL), brine (5 mL) and the organic layer dried over sodium sulfate, filtered and concentrated in vacuo. Column chromatography (silica, shallow gradient from 100% hexanes to 100% ethyl acetate) afforded tert-butyl 2,2-dimethyl-4-[3-[methyl-(5-sulfamoyl-2-pyridyl)amino]propyl]pyrrolidine-1-carboxylate (109 mg, 20%) as an off-white solid. ESI-MS m/z calc. 426.23007, found 427.2 (M+1)$^+$; Retention time: 1.49 min (LC Method B).

Step 2: tert-Butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]propyl]-2,2-dimethyl-pyrrolidine-1-carboxylate

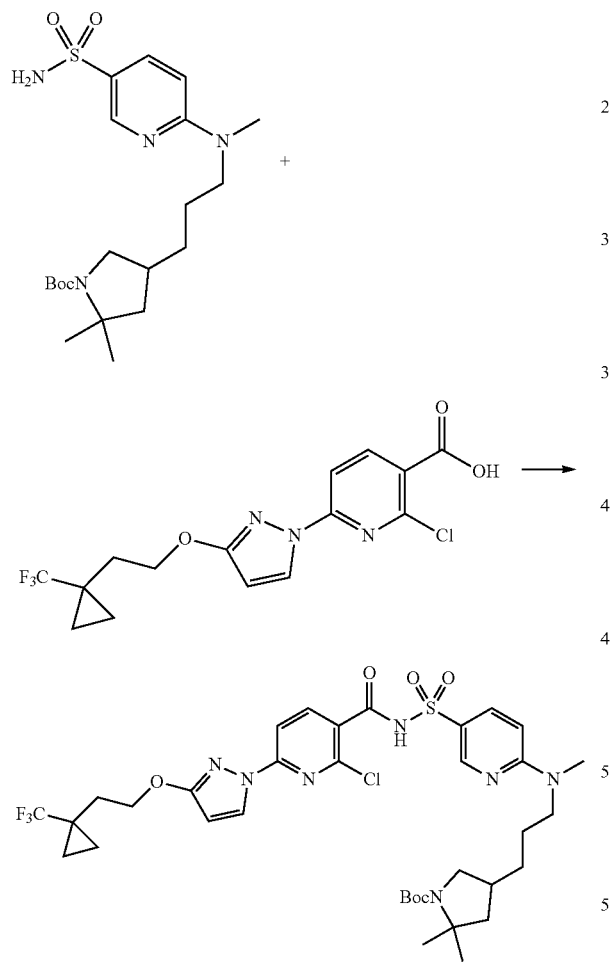

To a 20 mL vial charged with 2-chloro-6-[3-[2-[1-(trifluoromethyl)cyclopropyl]ethoxy]pyrazol-1-yl]pyridine-3-carboxylic acid (106 mg, 0.2821 mmol) was added carbonyl diimidazole (47 mg, 0.2899 mmol) and tetrahydrofuran (2 mL). The vial was capped and the reaction mixture stirred at room temperature for 2 h. At this point, tert-butyl 2,2-dimethyl-4-[3-[methyl-(5-sulfamoyl-2-pyridyl)amino]propyl]pyrrolidine-1-carboxylate (109 mg, 0.2555 mmol) in tetrahydrofuran (2 mL) was added, followed by 1,8-diazabicyclo[5.4.0]undec-7-ene (60 µL, 0.4012 mmol). The reaction mixture was stirred at room temperature for 18 h and quenched with water (~4 mL). Aqueous citric acid (4 mL, 1 M) was added and the crude mixture was extracted with ethyl acetate (3×10 mL). The combined organic extracts were dried over magnesium sulfate, filtered and concentrated in vacuo. Column chromatography (silica, 100% hexanes to 100% ethyl acetate gradient) afforded tert-butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]propyl]-2,2-dimethyl-pyrrolidine-1-carboxylate (87 mg, 43%) as an off-white solid. ESI-MS m/z calc. 783.27924, found 784.4 (M+1)$^+$; Retention time: 2.42 min (LC Method B).

Step 3: 2-Chloro-N-[[6-[3-(5,5-dimethylpyrrolidin-3-yl)propyl-methyl-amino]-3-pyridyl]sulfonyl]-6-[3-[2-[1-(trifluoromethyl)cyclopropyl]ethoxy]pyrazol-1-yl]pyridine-3-carboxamide

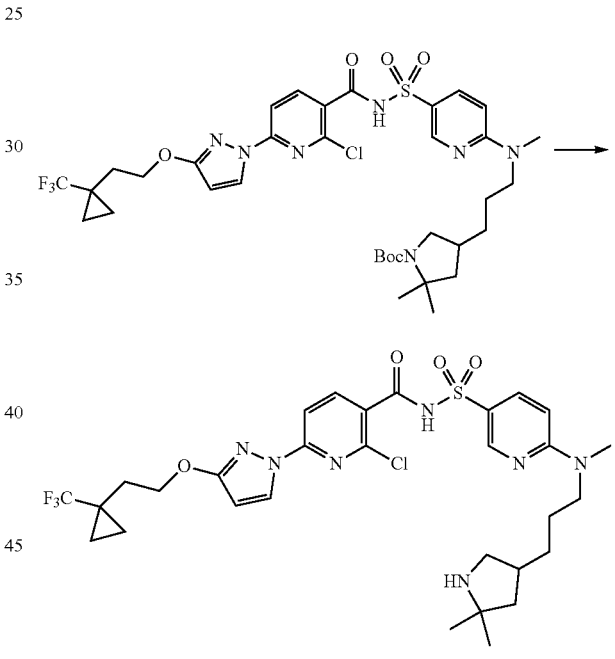

To a vial charged with tert-butyl 4-[3-[[5-[[2-chloro-6-[3-[2-[1-(trifluoromethyl)cyclopropyl]ethoxy]pyrazol-1-yl]pyridine-3-carbonyl]sulfamoyl]-2-pyridyl]-methyl-amino]propyl]-2,2-dimethyl-pyrrolidine-1-carboxylate (87 mg, 0.1109 mmol) was added dichloromethane (5 mL), followed by hydrochloric acid (1 mL of 4 M, 4.000 mmol) in dioxane. The vial was sealed, and the reaction mixture stirred at room temperature for 2 h. The solvent was removed in vacuo affording crude 2-chloro-N-[[6-[3-(5,5-dimethylpyrrolidin-3-yl)propyl-methyl-amino]-3-pyridyl]sulfonyl]-6-[3-[2-[1-(trifluoromethyl)cyclopropyl]ethoxy]pyrazol-1-yl]pyridine-3-carboxamide (75 mg, 99%) as a pale yellow solid, which was used without further purification. ESI-MS m/z calc. 683.2268, found 684.1 (M+1)$^+$; Retention time: 1.61 min (LC Method B).

975

Step 4: 12,12,18-Trimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Compound 140)

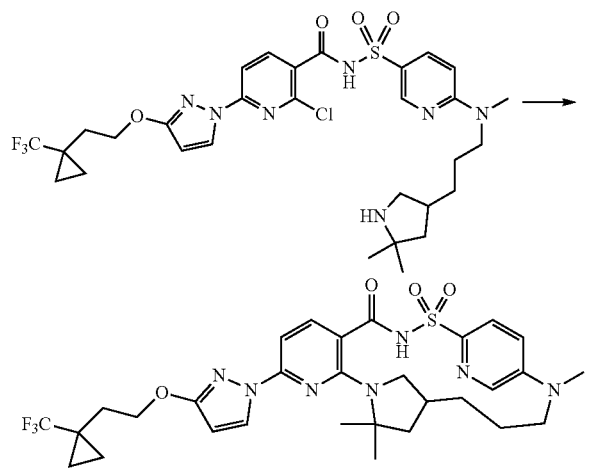

A vial fitted with a stirbar was charged with potassium carbonate (140 mg, 1.013 mmol) and CsF (131 mg, 0.8624 mmol). A solution of 2-chloro-N-[[6-[3-(5,5-dimethylpyrrolidin-3-yl)propyl-methyl-amino]-3-pyridyl]sulfonyl]-6-[3-[2-[1-(trifluoromethyl)cyclopropyl]ethoxy]pyrazol-1-yl]pyridine-3-carboxamide (70 mg, 0.1023 mmol) in dimethyl sulfoxide (10 mL) was added, the vial sealed, and the reaction mixture stirred at 200° C. for 1.5 h in a microwave reactor. After cooling to room temperature, the solids were filtered off with ethyl acetate eluent. The filtrate was diluted with ethyl acetate (~60 mL), washed with 1.0 M aqueous citric acid (10 mL) and brine (5 mL) and the organic layer was dried over sodium sulfate, filtered and concentrated in vacuo. Column chromatography (silica, 0% to 5% methanol in dichloromethane gradient) afforded 12,12,18-trimethyl-8-(3-{2-[1-(trifluoromethyl)cyclopropyl]ethoxy}-1H-pyrazol-1-yl)-2λ⁶-thia-3,9,11,18,20-pentaazatetracyclo[17.2.2.1¹¹,¹⁴.0⁵,¹⁰]tetracosa-1(22),5,7,9,19(23),20-hexaene-2,2,4-trione (Compound 140) (9 mg, 12%) as an off-white solid. ESI-MS m/z calc. 647.2502, found 648.2 (M+1)⁺; Retention time: 2.21 min (LC Method B).

Example 153: Preparation of 4-[3-(3,3-dicyclopropylpropoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 141)

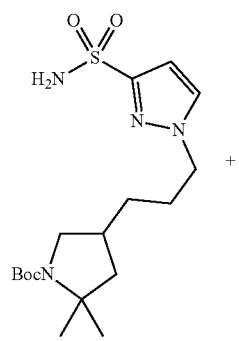

+

976

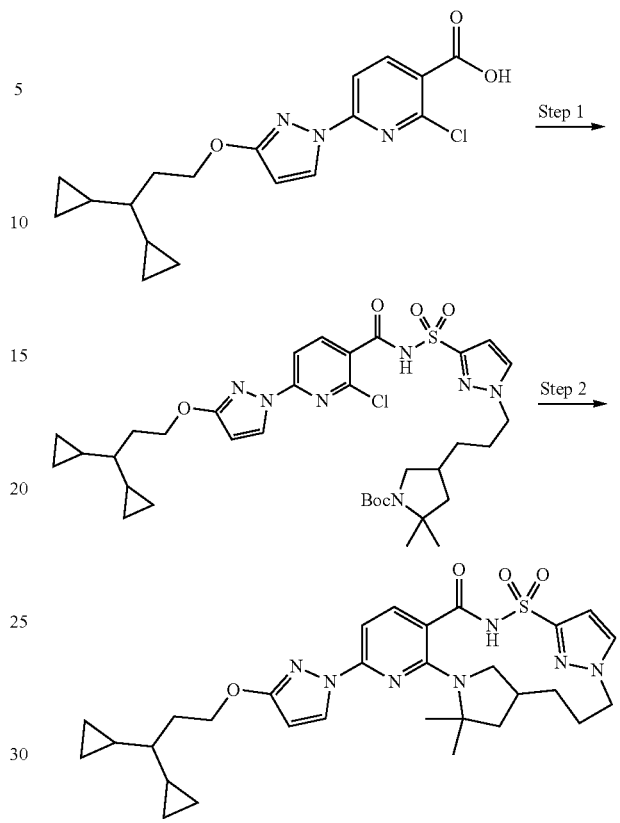

Step 1: tert-Butyl 4-[3-[3-[[2-chloro-6-[3-(3,3-dicyclopropylpropoxy)pyrazol-1-yl]pyridine-3-carbonyl]sulfamoyl]pyrazol-1-yl]propyl]-2,2-dimethyl-pyrrolidine-1-carboxylate

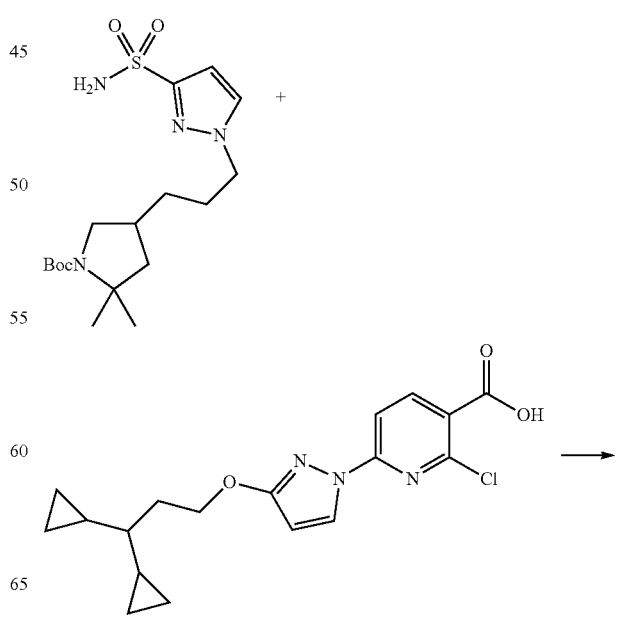

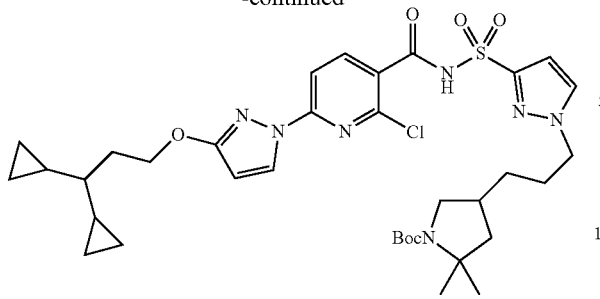
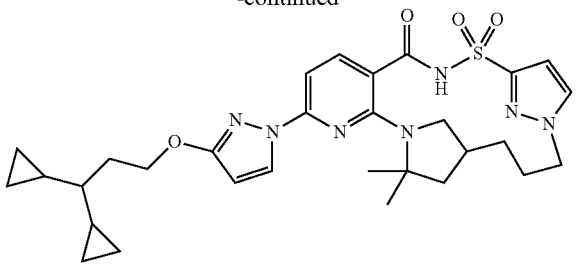

2-Chloro-6-[3-(3,3-dicyclopropylpropoxy)pyrazol-1-yl]pyridine-3-carboxylic acid (107.6 mg, 0.2975 mmol) and carbonyl diimidazole (57.89 mg, 0.3570 mmol) were combined in tetrahydrofuran (2 mL) and stirred for 90 min at 50° C. Then tert-butyl 2,2-dimethyl-4-[3-(3-sulfamoylpyrazol-1-yl)propyl]pyrrolidine-1-carboxylate (115 mg, 0.2975 mmol) was added followed by 1,8-diazabicyclo[5.4.0]undec-7-ene (67.94 mg, 66.74 µL, 0.4463 mmol) and the reaction was stirred at room temperature for 18 h. The reaction was diluted with ethyl acetate and washed with saturated ammonium chloride solution, followed by brine. The organics were separated, dried over sodium sulfate, filtered and evaporated then purified by silica gel chromatography using a gradient from 100% hexanes to 100% ethyl acetate to afford tert-butyl 4-[3-[3-[[2-chloro-6-[3-(3,3-dicyclopropylpropoxy) pyrazol-1-yl]pyridine-3-carbonyl]sulfamoyl]pyrazol-1-yl]propyl]-2,2-dimethyl-pyrrolidine-1-carboxylate (145 mg, 67%) as a white solid. $^1$H NMR (400 MHz, Chloroform-d) δ 9.75 (s, 1H), 8.30 (d, J=2.9 Hz, 1H), 8.27-8.20 (m, 1H), 7.75 (d, J=8.4 Hz, 1H), 7.48 (t, J=3.1 Hz, 1H), 7.05 (d, J=2.5 Hz, 1H), 5.97 (d, J=2.9 Hz, 1H), 4.43 (t, J=6.8 Hz, 2H), 4.20 (t, J=7.0 Hz, 2H), 3.64 (dt, J=42.1, 9.1 Hz, 1H), 2.91-2.75 (m, 1H), 2.07 (s, 1H), 1.97 (q, J=6.8 Hz, 2H), 1.91 (t, J=7.7 Hz, 1H), 1.84 (dd, J=12.1, 5.9 Hz, 1H), 1.69-1.54 (m, 4H), 1.43 (d, J=4.6 Hz, 11H), 1.37-1.22 (m, 6H), 0.67 (qt, J=8.4, 5.1 Hz, 2H), 0.50-0.38 (m, 4H), 0.32 (tt, J=9.0, 6.8 Hz, 1H), 0.20 (dtd, J=9.5, 4.9, 3.6 Hz, 2H), 0.14-0.06 (m, 2H). ESI-MS m/z calc. 729.30756, found 730.37 (M+1)$^+$; Retention time: 0.91 min (LC Method A).

Step 2: 4-[3-(3,3-Dicyclopropylpropoxy)-1H-pyrazol-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Compound 141)

A solution of tert-butyl 4-[3-[3-[[2-chloro-6-[3-(3,3-dicyclopropylpropoxy) pyrazol-1-yl]pyridine-3-carbonyl]sulfamoyl]pyrazol-1-yl]propyl]-2,2-dimethyl-pyrrolidine-1-carboxylate (145 mg, 0.1985 mmol) in dichloromethane (1 mL) and trifluoroacetic acid (150 µL, 1.960 mmol) was stirred at room temperature for 4 h. The solvents were removed and the residue was dissolved in ethyl acetate. Washed with 2 mL of sat sodium bicarbonate solution and the organic layer was collected and the solvent removed followed by drying the residue under vacuum. The above residue was dissolved in dimethyl sulfoxide (3 mL) and 3 Å molecular sieves were added and the reaction mixture was stirred for 10 min. Then, cesium fluoride (94 mg, 0.6188 mmol) and potassium carbonate (86 mg, 0.6223 mmol) were added and the reaction mixture was heated at 150° C. overnight. The reaction mixture was filtered through a Whatman filter disc (puradisc 25 TF) and the filtrate was purified by a reverse phase HPLC-MS method using a dual gradient run from 50%-99% mobile phase B over 15.0 min (mobile phase A=water (0.05% hydrochloric acid), mobile phase B=acetonitrile) to afford 4-[3-(3,3-dicyclopropylpropoxy)-1H-pyrazol-1-yl]-20,20-dimethyl-10λ$^6$-thia-1,3,9,14,22-pentaazatetracyclo [16.2.1.1$^{11,14}$.0$^{2,7}$]docosa-2,4,6,11 (22),12-pentaene-8,10,10-trione (Compound 141) (26 mg, 22%) as a white solid. $^1$H NMR (400 MHz, Chloroform-d) δ 8.62 (s, 1H), 8.17 (d, J=2.8 Hz, 1H), 7.67 (d, J=8.2 Hz, 1H), 7.48 (d, J=2.3 Hz, 1H), 7.07 (d, J=2.3 Hz, 1H), 7.02 (d, J=8.3 Hz, 1H), 5.87 (d, J=2.8 Hz, 1H), 4.41 (t, J=6.8 Hz, 2H), 4.35 (dt, J=13.3, 3.4 Hz, 1H), 4.00-3.87 (m, 1H), 2.75 (t, J=8.2 Hz, 1H), 2.25-1.87 (m, 3H), 1.80-1.71 (m, 1H), 1.62 (s, 4H), 1.59 (s, 3H), 1.55 (s, 3H), 1.47 (t, J=12.3 Hz, 1H), 0.80 (dd, J=12.5, 6.7 Hz, 1H), 0.73-0.60 (m, 2H), 0.52-0.38 (m, 4H), 0.38-0.28 (m, 1H), 0.24-0.15 (m, 2H), 0.11 (dddd, J=8.6, 7.2, 3.9, 2.6 Hz, 2H). ESI-MS m/z calc. 593.27844, found 594.2 (M+1)$^+$; Retention time: 1.82 min (LC Method G).

Example 154: Preparation of 12,12-dimethyl-8-(3-{2-[1-(trifluoromethyl)cyclopropyl]ethoxy}-1H-pyrazol-1-yl)-2λ$^6$-thia-3,9,11,21-tetraazatetracyclo[18.2.2.1$^{11,14}$.0$^{5,10}$]pentacosa-1(23),5,7,9,20(24),21-hexaene-2,2,4-trione (Compound 142)

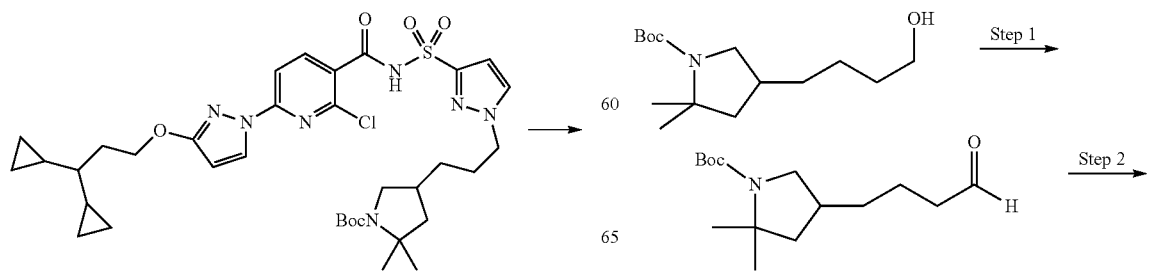

980

Step 1: tert-Butyl 2,2-dimethyl-4-(4-oxobutyl)pyrrolidine-1-carboxylate

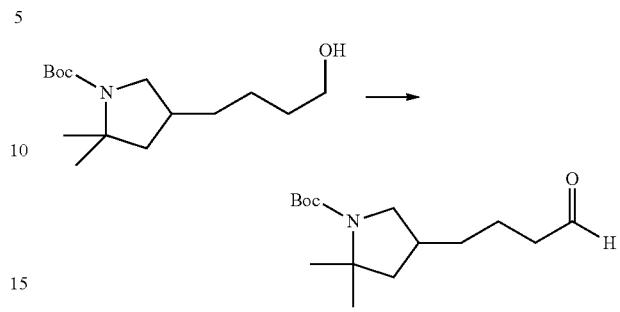

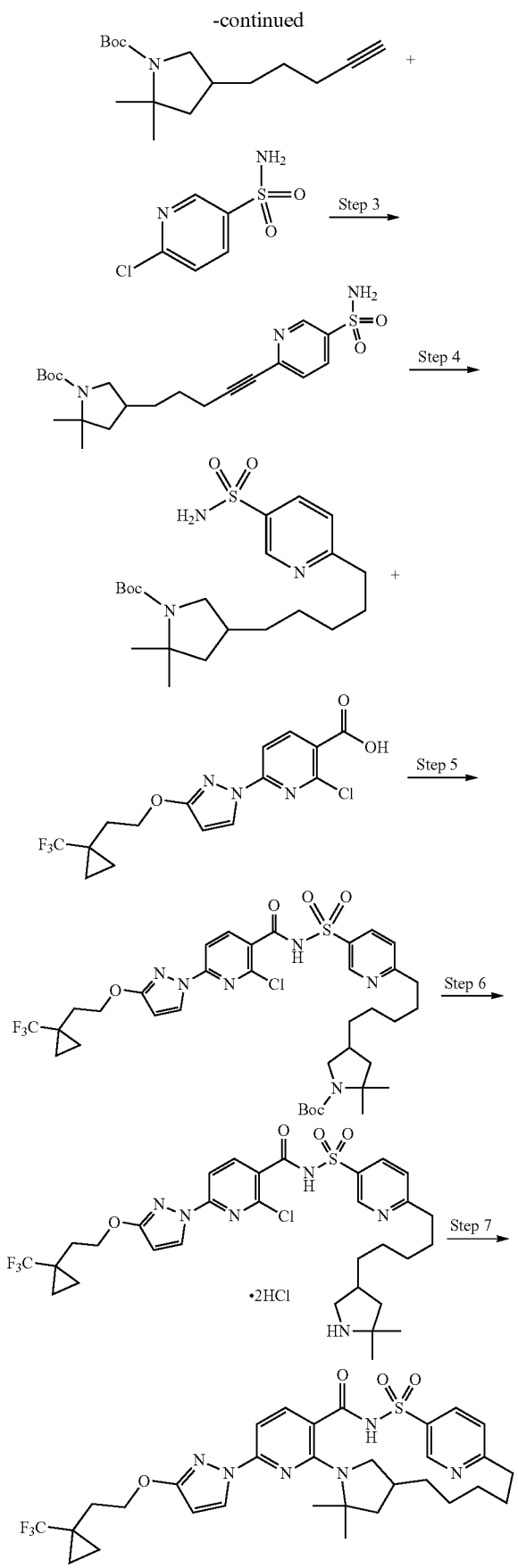

Dess-Martin periodinane (9.59 g, 22.61 mmol) was added to a stirred solution of tert-butyl 4-(4-hydroxybutyl)-2,2-dimethyl-pyrrolidine-1-carboxylate (5.2 g, 19.16 mmol) in anhydrous $CH_2Cl_2$ (35 mL) at 0° C. (ice-water bath) under nitrogen. After 15 min, the reaction was allowed to warm to ambient temperature and stirring was continued for another 3 h. The reaction was diluted with ether (200 mL) and saturated aqueous sodium bicarbonate (100 mL) was added slowly (to mitigate carbon dioxide gas evolution). Then 10% sodium thiosulfate (50 mL) was added and the mixture was stirred at ambient temperature for 30 min. The layers were not clearly separated, thus the mixture was filtered over a fritted filter funnel. The layers were separated from the filtrate and the aqueous layer was extracted with ether (2×100 mL). The combined organics were washed with brine (100 mL), dried over anhydrous sodium sulfate, filtered and concentrated under reduced pressure to obtain crude material. The crude was purified by silica gel chromatography (5%-40% ethyl acetate in hexanes gradient) to furnish desired tert-butyl 2,2-dimethyl-4-(4-oxobutyl)pyrrolidine-1-carboxylate (4.39 g, 85%) as clear viscous material. $^1H$ NMR (400 MHz, Methanol-$d_4$) δ 4.48 (t, J=5.5 Hz, 1H), 3.64 (h, J=4.8 Hz, 1H), 2.86 (td, J=10.6, 5.2 Hz, 1H), 2.30 (t, J=7.3 Hz, 1H), 2.22-2.06 (m, 1H), 1.95 (ddt, J=17.2, 11.6, 5.8 Hz, 1H), 1.67-1.53 (m, 2H), 1.53-1.48 (m, 2H), 1.47 (s, 4H), 1.43 (s, 5H), 1.40 (s, 3H), 1.39-1.34 (m, 2H), 1.31 (s, 3H). ESI-MS m/z calc. 269.1991, found 270.2 $(M+1)^+$; Retention time: 1.7 min (LC Method B).

Step 2: tert-Butyl 2,2-dimethyl-4-pent-4-ynyl-pyrrolidine-1-carboxylate

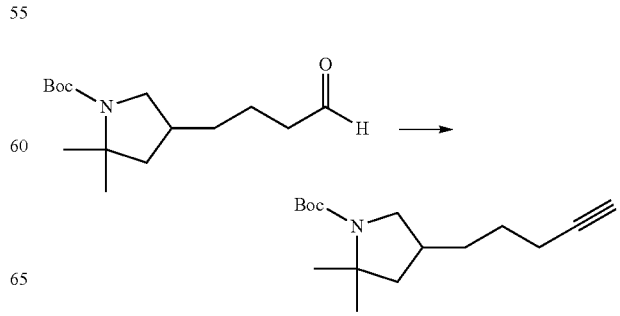

To a stirred solution of tert-butyl 2,2-dimethyl-4-(4-oxobutyl)pyrrolidine-1-carboxylate (3.0 g, 11.14 mmol) in anhydrous methanol (40 mL) at 0° C. (ice-water bath) was added potassium carbonate (3.39 g, 24.53 mmol) followed by dropwise addition of 1-diazo-1-dimethoxyphosphoryl-propan-2-one (2.1 mL, 13.99 mmol). On completion of addition, the mixture was allowed to warm to room temperature and stirred 16 h total (the reaction was completed within 4 h). Removed solvent under reduced pressure and the residue was dissolved in ethyl acetate (50 mL) and washed with brine (20 mL). The aqueous layer was back extracted (2×20 mL) with ethyl acetate and the organic layers were combined, washed with brine (20 mL), dried (over anhydrous sodium sulfate), filtered and concentrated to a clear oil which was purified by silica gel chromatography (0%-20% ethyl acetate in hexanes gradient) giving desired tert-butyl 2,2-dimethyl-4-pent-4-ynyl-pyrrolidine-1-carboxylate (2.29 g, 77%) as a clear oil. $^1$H NMR (400 MHz, Methanol-d$_4$) δ 3.72-3.57 (m, 1H), 2.86 (t, J=10.7 Hz, 1H), 2.27-2.07 (m, 4H), 1.95 (ddd, J=16.7, 12.2, 6.1 Hz, 1H), 1.58-1.48 (m, 4H), 1.47 (s, 5H), 1.43 (s, 5H), 1.41 (s, 2H), 1.31 (s, 3H). ESI-MS m/z calc. 265.2042, found 266.2 (M+1)$^+$; Retention time: 1.77 min (LC Method B).

Step 3: tert-Butyl 2,2-dimethyl-4-[5-(5-sulfamoyl-2-pyridyl)pent-4-ynyl]pyrrolidine-1-carboxylate

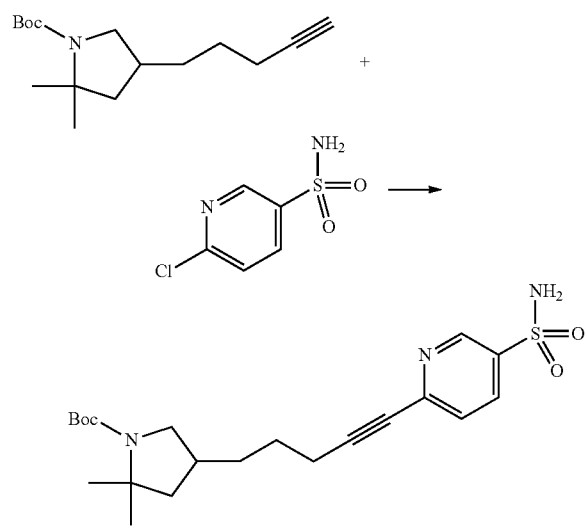

A dry 20 mL vial was charged with tert-butyl 2,2-dimethyl-4-pent-4-ynyl-pyrrolidine-1-carboxylate (700 mg, 2.638 mmol), 6-chloropyridine-3-sulfonamide (900 mg, 4.672 mmol), iodocopper (51 mg, 0.2678 mmol), bis(triphenylphosphine)palladium chloride (112 mg, 0.1596 mmol) and anhydrous N,N-dimethylformamide (6 mL), in that order. Then nitrogen was bubbled through the stirring dark mixture for 3 min and diisopropylamine (700 μL, 4.995 mmol) was added and the vial was capped under nitrogen. The reaction was stirred at 52° C. for 11 h, then cooled to ambient temperature and poured into water (100 mL) and extracted with ethyl acetate (3×50 mL). The combined organics were successively washed with water (2×50 mL) and brine (30 mL), dried (over anhydrous sodium sulfate), filtered and concentrated under reduced pressure to an orange oil which was purified by silica gel chromatography using a gradient from 15%-50% ethyl acetate in hexanes to furnish desired tert-butyl 2,2-dimethyl-4-[5-(5-sulfamoyl-2-pyridyl)pent-4-ynyl]pyrrolidine-1-carboxylate (699 mg, 63%) as a white solid. $^1$H NMR (400 MHz, Methanol-d$_4$) δ 8.91 (dd, J=2.4, 0.9 Hz, 1H), 8.20 (dd, J=8.3, 2.4 Hz, 1H), 7.60 (dd, J=8.2, 0.9 Hz, 1H), 3.71-3.63 (m, 1H), 2.90 (t, J=10.7 Hz, 1H), 2.53 (t, J=6.8 Hz, 2H), 2.28-2.14 (m, 1H), 2.03-1.92 (m, 1H), 1.74-1.62 (m, 2H), 1.62-1.50 (m, 3H), 1.47 (s, 5H), 1.43 (s, 5H), 1.42 (s, 2H), 1.32 (s, 3H). ESI-MS m/z calc. 421.20352, found 422.3 (M+1)$^+$; Retention time: 1.74 min (LC Method B).

Step 4: tert-Butyl 2,2-dimethyl-4-[5-(5-sulfamoyl-2-pyridyl)pentyl]pyrrolidine-1-carboxylate

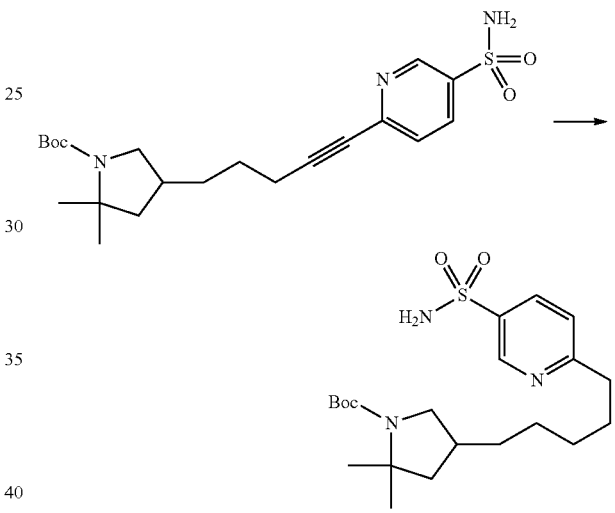

Nitrogen was bubbled through a stirred solution of tert-butyl 2,2-dimethyl-4-[5-(5-sulfamoyl-2-pyridyl)pent-4-ynyl]pyrrolidine-1-carboxylate (698 mg, 1.656 mmol) in ethanol (20 mL). Then platinum oxide (76 mg, 0.3347 mmol) was added under nitrogen and the reaction was stirred under hydrogen (balloon) at ambient temperature. After 2 h, more platinum oxide (110 mg, 0.4844 mmol) was added and the reaction was stirred for another 3 h. Then the reaction was purged with nitrogen, added 5 g Celite and stirred for 20 min. The heterogeneous mixture was filtered over a pad of Celite. The filtrate was concentrated under reduced pressure to obtain crude material that was purified by silica gel chromatography (5%-50% ethyl acetate in hexanes gradient) to furnish tert-butyl 2,2-dimethyl-4-[5-(5-sulfamoyl-2-pyridyl)pentyl]pyrrolidine-1-carboxylate (655 mg, 93%) as a white solid. $^1$H NMR (400 MHz, Methanol-d$_4$) δ 8.90 (dd, J=2.4, 0.8 Hz, 1H), 8.17 (dd, J=8.2, 2.4 Hz, 1H), 7.47 (dd, J=8.2, 0.8 Hz, 1H), 3.66-3.58 (m, 1H), 2.91-2.80 (m, 3H), 2.19-2.05 (m, 1H), 1.98-1.86 (m, 1H), 1.75 (p, J=7.4 Hz, 2H), 1.47 (s, 5H), 1.43 (s, 4H), 1.42 (s, 2H), 1.40 (s, 2H), 1.36 (s, 6H), 1.30 (s, 3H). ESI-MS m/z calc. 425.23483, found 426.3 (M+1)$^+$; Retention time: 1.73 min (LC Method B).

Step 5: tert-Butyl 4-[5-[5-[[2-chloro-6-[3-[2-[1-(trifluoromethyl)cyclopropyl]ethoxy]pyrazol-1-yl]pyridine-3-carbonyl]sulfamoyl]-2-pyridyl]pentyl]-2,2-dimethyl-pyrrolidine-1-carboxylate

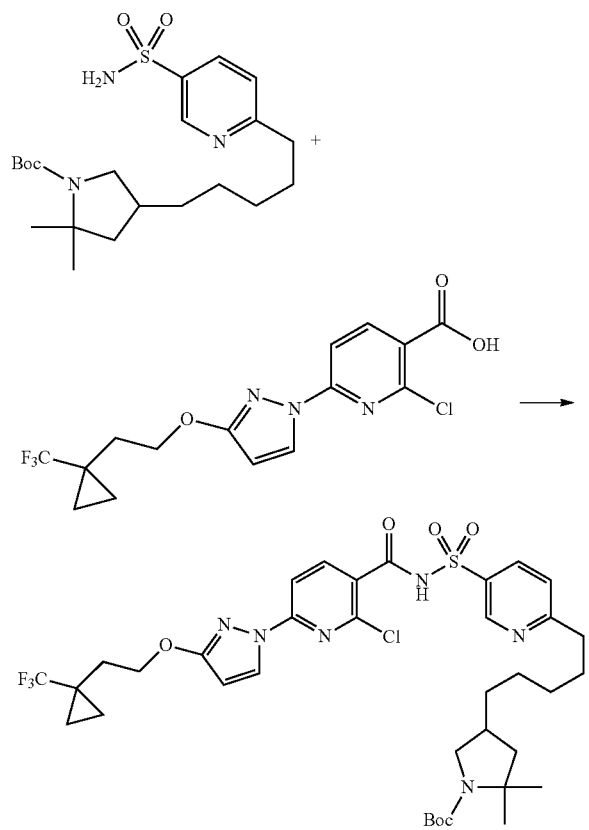

To a solution of 2-chloro-6-[3-[2-[1-(trifluoromethyl)cyclopropyl]ethoxy]yrazol-1-yl]pyridine-3-carboxylic acid (440 mg, 1.171 mmol) in dry tetrahydrofuran (6 mL) was added carbonyl diimidazole (195 mg, 1.203 mmol) at ambient temperature under nitrogen. The mixture was stirred at that temperature for 3 h to form the activated acid. To the solution of the activated acid was added a solution of tert-butyl 2,2-dimethyl-4-[5-(5-sulfamoyl-2-pyridyl)pentyl]pyrrolidine-1-carboxylate (500 mg, 1.175 mmol) in dry tetrahydrofuran (4 mL) followed by 1,8-diazabicyclo[5.4.0]undec-7-ene (400 µL, 2.675 mmol) and the mixture was stirred at ambient temperature for 15 h. The volatiles were removed under reduced pressure and the thick residue was partitioned between water (15 mL) and ethyl acetate (30 mL). The mixture was acidified with aqueous 4 M hydrochloric acid to pH 3-4 and the layers were separated. The organic phase was washed with brine (20 mL) and the combined aqueous layers were re-extracted with ethyl acetate (30 mL). The combined organics were dried over anhydrous sodium sulfate, filtered, and concentrated under reduced pressure to obtain crude material. The crude product was chromatographed (silica gel column, eluting with 0%-80% ethyl acetate in hexanes gradient) to produce tert-butyl 4-[5-[5-[[2-chloro-6-[3-[2-[1-(trifluoromethyl)cyclopropyl]ethoxy]pyrazol-1-yl]pyridine-3-carbonyl]sulfamoyl]-2-pyridyl]pentyl]-2,2-dimethyl-pyrrolidine-1-carboxylate (750 mg, 82%) as a white foam. $^{1}$H NMR (400 MHz, Methanol-$d_4$) δ 9.02 (dd, J=2.3, 0.8 Hz, 1H), 8.69 (s, 1H), 8.32 (d, J=1.0 Hz, 1H), 8.32-8.29 (m, 1H), 7.98 (d, J=8.3 Hz, 1H), 7.65 (d, J=8.2 Hz, 1H), 7.49 (d, J=1.3 Hz, 1H), 7.45 (dd, J=8.2, 0.8 Hz, 1H), 5.97 (d, J=2.8 Hz, 1H), 4.43-4.33 (m, 2H), 3.67-3.56 (m, 1H), 2.86 (t, J=7.7 Hz, 2H), 2.83 (d, J=11.1 Hz, 1H), 2.10 (t, J=7.0 Hz, 2H), 1.92 (td, J=13.9, 13.4, 6.0 Hz, 1H), 1.80-1.69 (m, 2H), 1.46 (s, 5H), 1.42 (s, 4H), 1.41 (s, 2H), 1.39 (s, 3H), 1.36 (s, 6H), 1.29 (s, 3H), 1.03-0.96 (m, 2H), 0.82 (tt, J=5.4, 2.9 Hz, 2H). ESI-MS m/z calc. 782.284, found 783.4 (M+1)$^+$; Retention time: 2.42 min (LC Method B).

Step 6: 2-Chloro-N-[[6-[5-(5,5-dimethylpyrrolidin-3-yl)pentyl]-3-pyridyl]sulfonyl]-6-[3-[2-[1-(trifluoromethyl)cyclopropyl]ethoxy]pyrazol-1-yl]pyridine-3-carboxamide (Dihydrochloride Salt)

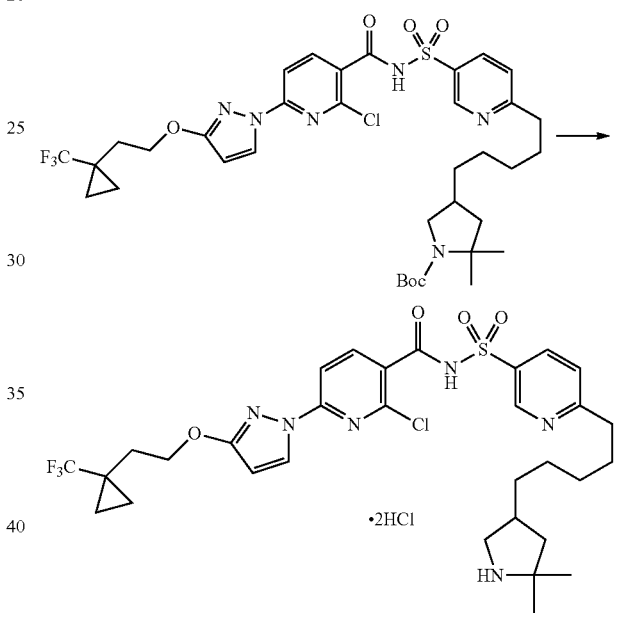

To a solution of tert-butyl 4-[5-[5-[[2-chloro-6-[3-[2-[1-(trifluoromethyl)cyclo propyl]ethoxy]pyrazol-1-yl]pyridine-3-carbonyl]sulfamoyl]-2-pyridyl]pentyl]-2,2-dimethyl-pyrrolidine-1-carboxylate (750 mg, 0.9575 mmol) in anhydrous $CH_2Cl_2$ (15 mL) was added hydrochloric acid (6.0 mL of 4.0 M in dioxane, 24.00 mmol) at 0° C. (ice-water bath) under nitrogen. After 5 min, the bath was removed and the stirring was continued at room temperature for another 20 min. The reaction was concentrated to dryness under reduced pressure. The residue was taken up in ethyl acetate (30 mL) and adjusted the pH to 5 with the addition of saturated aqueous sodium bicarbonate solution. The layers were separated and the aqueous portion was re-extracted with ethyl acetate (2×20 mL). The combined organics were washed with brine, dried over anhydrous sodium sulfate, filtered, and concentrated under reduced pressure to dryness giving 2-chloro-N-[[6-[5-(5,5-dimethylpyrrolidin-3-yl)pentyl]-3-pyridyl]sulfonyl]-6-[3-[2-[1-(trifluoromethyl)cyclopropyl]ethoxy]pyrazol-1-yl]pyridine-3-carboxamide (dihydrochloride salt) (720 mg, 99%) as a white solid. ESI-MS m/z calc. 682.23157, found 683.4 (M+1)$^+$; Retention time: 1.65 min (LC Method B).

Step 7: 12,12-Dimethyl-8-(3-{2-[1-(trifluoromethyl)cyclopropyl]ethoxy}-1H-pyrazol-1-yl)-2λ⁶-thia-3,9,11,21-tetraazatetracyclo[18.2.2.1¹¹,¹⁴.0⁵,¹⁰]pentacosa-1(23),5,7,9,20(24),21-hexaene-2,2,4-trione (Compound 142)

Example 155: Preparation of 12,12-dimethyl-8-(3-{2-[1-(trifluoromethyl)cyclopropyl]ethoxy}-1H-pyrazol-1-yl)-2λ⁶-thia-3,9,11,22-tetraazatetracyclo[18.2.2.1¹¹,¹⁴.0⁵,¹⁰]pentacosa-1(23),5,7,9,20(24),21-hexaene-2,2,4-trione (Compound 143)

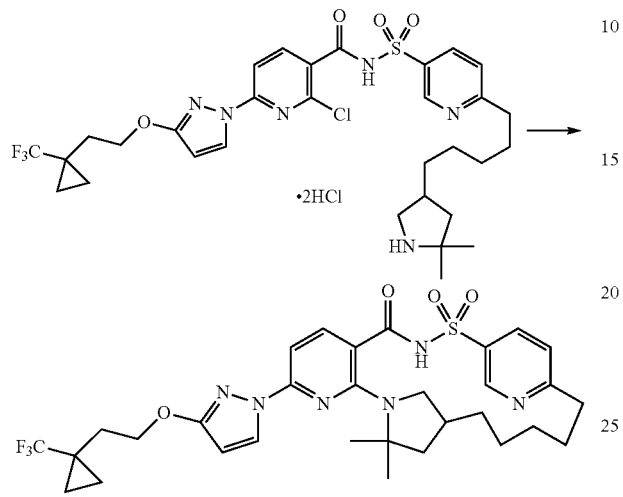

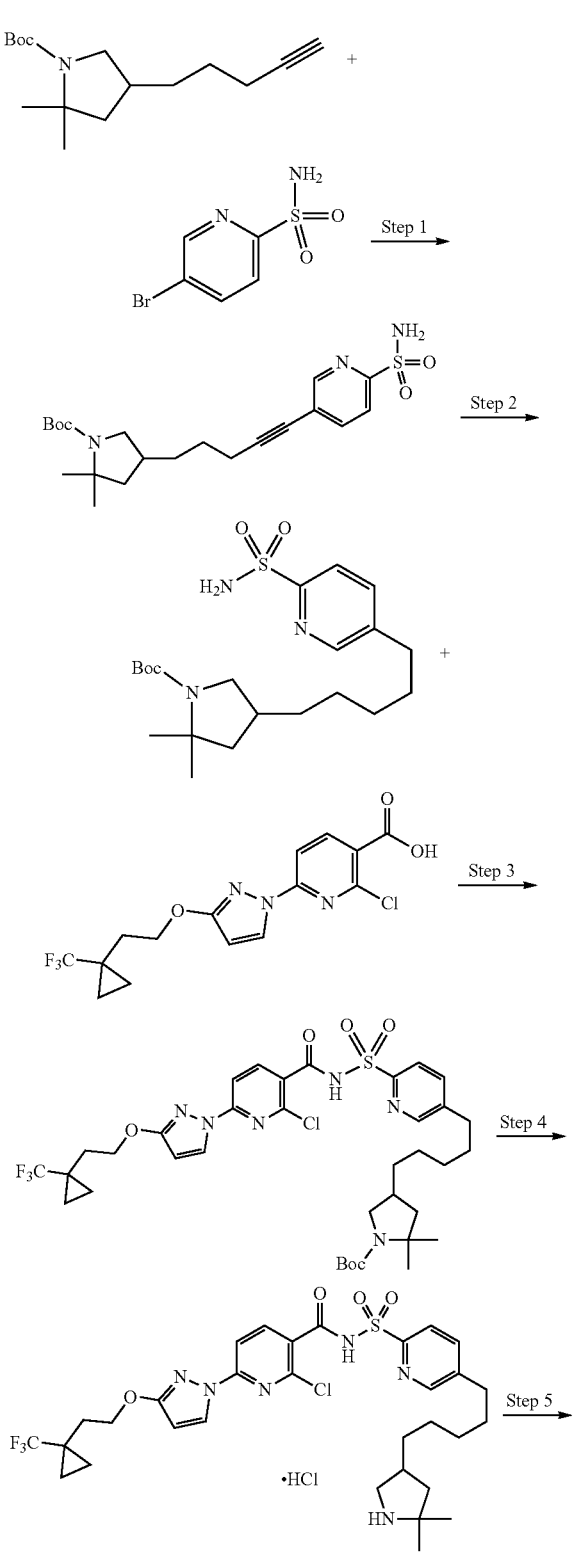

A 20 mL vial was charged with 2-chloro-N-[[6-[5-(5,5-dimethylpyrrolidin-3-yl)pentyl]-3-pyridyl]sulfonyl]-6-[3-[2-[1-(trifluoromethyl)cyclopropyl]ethoxy]pyrazol-1-yl]pyridine-3-carboxamide (dihydrochloride salt) (715 mg, 0.9456 mmol), potassium carbonate (650 mg, 4.703 mmol), cesium fluoride (215 mg, 1.415 mmol) and anhydrous dimethyl sulfoxide (15 mL). The vial was purged with nitrogen for 2 min, capped and stirred at 165° C. for 24 h. The reaction was allowed to cool to ambient temperature and was then diluted with ethyl acetate (50 mL) and ice-water (50 mL). The layers were separated and the organic phase was washed with saturated aqueous sodium bicarbonate solution (20 mL). The aqueous layers were extracted with ethyl acetate (50 mL). The combined organics were washed with brine (30 mL), dried over anhydrous sodium sulfate, filtered, and concentrated under reduced pressure to dryness. The crude was purified by silica gel chromatography (0%-55% ethyl acetate in hexanes gradient) followed by a second silica gel column (0%-10% methanol in dichloromethane) providing 12,12-dimethyl-8-(3-{2-[1-(trifluoromethyl)cyclopropyl]ethoxy}-1H-pyrazol-1-yl)-2λ⁶-thia-3,9,11,21-tetraazatetracyclo[18.2.2.1¹¹,¹⁴.0⁵,¹⁰]pentacosa-1(23),5,7,9,20(24),21-hexaene-2,2,4-trione (Compound 142) (221 mg, 36%) as a white solid. ¹H NMR (400 MHz, dimethyl sulfoxide-$d_6$) δ 12.56 (s, 1H), 9.02 (s, 1H), 8.31 (s, 1H), 8.20 (d, J=2.8 Hz, 1H), 7.93 (d, J=8.2 Hz, 1H), 7.63 (d, J=8.2 Hz, 1H), 6.95 (d, J=8.3 Hz, 1H), 6.12 (d, J=2.7 Hz, 1H), 4.32 (t, J=7.0 Hz, 2H), 3.08-2.93 (m, 1H), 2.91-2.78 (m, 1H), 2.49-2.41 (m, 1H), 2.08 (t, J=7.0 Hz, 2H), 2.02-1.87 (m, 3H), 1.85-1.66 (m, 2H), 1.55 (s, 4H), 1.49 (s, 3H), 1.43 (t, J=11.9 Hz, 1H), 1.33-1.22 (m, 2H), 0.96 (q, J=4.8, 4.2 Hz, 2H), 0.92-0.87 (m, 2H), 0.85 (s, 1H), 0.62 (s, 1H), -0.31 (s, 1H). ESI-MS m/z calc. 646.2549, found 647.5 (M+1)⁺; Retention time: 1.94 min (LC Method B).

987

-continued

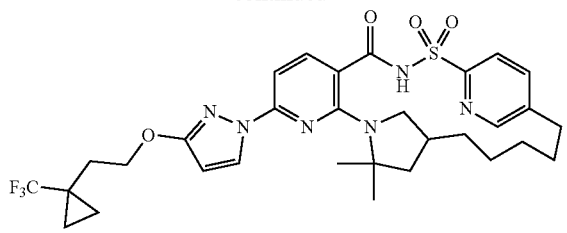

Step 1: tert-Butyl 2,2-dimethyl-4-[5-(6-sulfamoyl-3-pyridyl)pent-4-ynyl]pyrrolidine-1-carboxylate

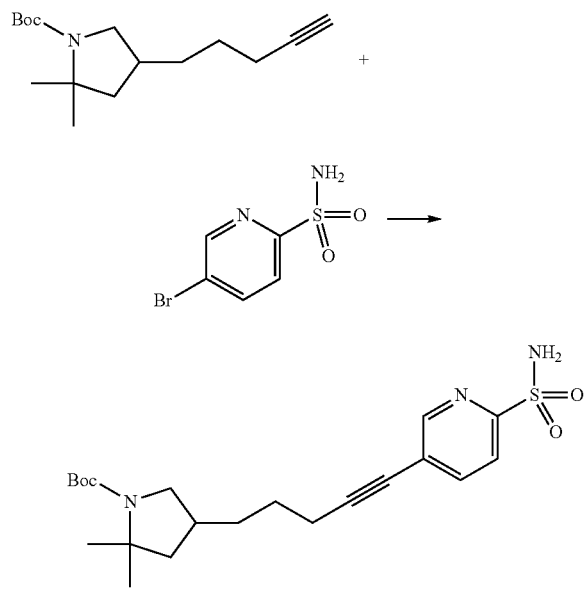

A dry 20 mL vial was charged with tert-butyl 2,2-dimethyl-4-pent-4-ynyl-pyrrolidine-1-carboxylate (600 mg, 2.261 mmol), 5-bromopyridine-2-sulfonamide (640 mg, 2.700 mmol), copper (I) iodide (44 mg, 0.2310 mmol), bis(triphenylphosphine)palladium (II) dichloride (96 mg, 0.1368 mmol) and anhydrous N,N-dimethylformamide (6 mL), in that order. Then, nitrogen was bubbled through the stirring dark mixture for 3 min and diisopropylamine (450 µL, 3.211 mmol) was added and the vial was capped under nitrogen. The reaction was stirred at 52° C. for 12 h then cooled to ambient temperature and poured into water (80 mL) and extracted with ethyl acetate (3×50 mL). The combined organics were successively washed with water (2×50 mL) and brine (30 mL), dried (over anhydrous sodium sulfate), filtered and concentrated under reduced pressure to an orange oil which was purified by silica gel chromatography using a gradient from 15%-50% ethyl acetate in hexanes to furnish desired tert-butyl 2,2-dimethyl-4-[5-(6-sulfamoyl-3-pyridyl)pent-4-ynyl]pyrrolidine-1-carboxylate (889 mg, 93%) as a white solid. ESI-MS m/z calc. 421.20352, found 422.3 (M+1)$^+$; Retention time: 0.72 min (LC Method A).

988

Step 2: tert-Butyl 2,2-dimethyl-4-[5-(6-sulfamoyl-3-pyridyl)pentyl]pyrrolidine-1-carboxylate

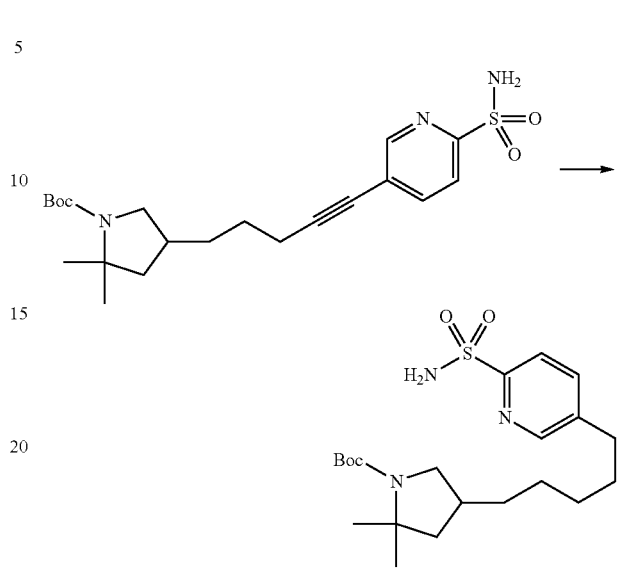

Nitrogen gas was bubbled through a stirred solution of tert-butyl 2,2-dimethyl-4-[5-(6-sulfamoyl-3-pyridyl)pent-4-ynyl]pyrrolidine-1-carboxylate (883 mg, 2.095 mmol) in ethanol (20 mL). Then platinum (IV) oxide (240 mg, 1.057 mmol) was added under nitrogen and the reaction was stirred under hydrogen (balloon) at ambient temperature. After stirring for 2.5 h, the reaction was purged with nitrogen, added 5 g Celite and stirred for 20 min. The heterogeneous mixture was filtered over a pad of Celite. The dark filtrate was concentrated under reduced pressure and the residue was taken up in methylene chloride and again filtered over a pad of silica gel to remove the residual platinum black material. Upon concentrating under reduced pressure, the crude was purified from silica gel chromatography (5%-50% ethyl acetate in hexanes) to furnish desired tert-butyl 2,2-dimethyl-4-[5-(6-sulfamoyl-3-pyridyl)pentyl]pyrrolidine-1-carboxylate (882 mg, 99%) as a white solid. ESI-MS m/z calc. 425.23483, found 426.3 (M+1)$^+$; Retention time: 1.67 min (LC Method B).

Step 3: tert-Butyl 4-[5-[6-[[2-chloro-6-[3-[2-[1-(trifluoromethyl)cyclopropyl]ethoxy]pyrazol-1-yl]pyridine-3-carbonyl]sulfamoyl]-3-pyridyl]pentyl]-2,2-dimethyl-pyrrolidine-1-carboxylate

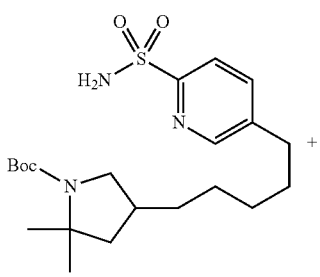

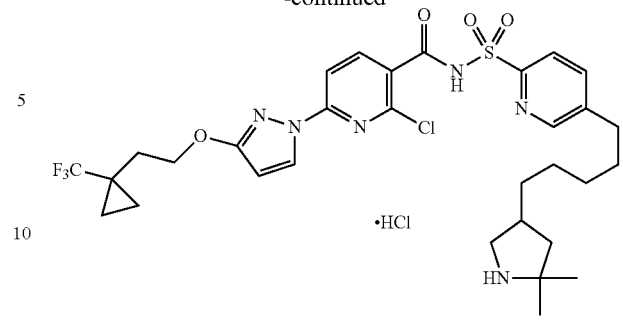

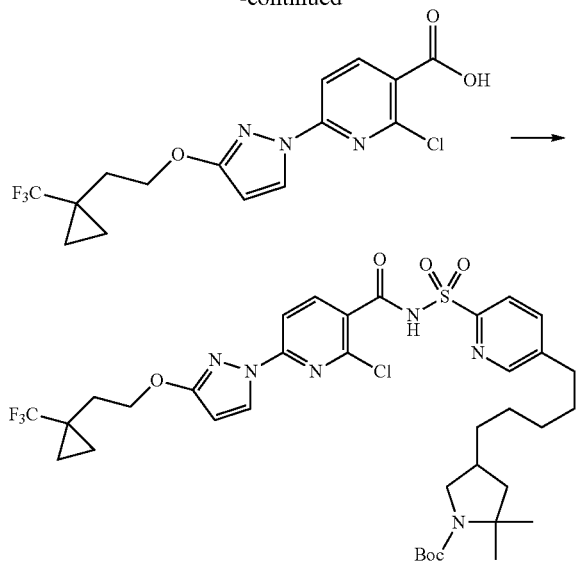

To a solution of 2-chloro-6-[3-[2-[1-(trifluoromethyl)cyclopropyl]ethoxy]pyrazol-1-yl]pyridine-3-carboxylic acid (773 mg, 2.057 mmol) in anhydrous tetrahydrofuran (8 mL) was added carbonyl diimidazole (340 mg, 2.097 mmol) at ambient temperature under nitrogen. The mixture was stirred at 45° C. for 3 h to form the activated acid. To the activated acid solution was added a solution of tert-butyl 2,2-dimethyl-4-[5-(6-sulfamoyl-3-pyridyl)pentyl]pyrrolidine-1-carboxylate (875 mg, 2.056 mmol) in anhydrous tetrahydrofuran (3 mL) followed by 1,8-diazabicyclo[5.4.0]undec-7-ene (650 μL, 4.347 mmol) and the mixture was stirred at ambient temperature for 48 h. The volatiles were removed under reduced pressure and the thick residue was partitioned between water (15 mL) and ethyl acetate (30 mL). The mixture was acidified with aqueous 4 M hydrochloric acid to pH 3-4 and the layers were separated. The organic layer phase was washed with brine (20 mL) and the combined aqueous layers were re-extracted with ethyl acetate (30 mL). The combined organics were dried over anhydrous sodium sulfate, filtered and concentrated under reduced pressure to obtain crude material. The crude product was chromatographed (silica gel column, eluting with 0%-80% ethyl acetate in hexanes gradient) to produce tert-butyl 4-[5-[6-[[2-chloro-6-[3-[2-[1-(trifluoromethyl)cyclopropyl]ethoxy]pyrazol-1-yl]pyridine-3-carbonyl]sulfamoyl]-3-pyridyl]pentyl]-2,2-dimethyl-pyrrolidine-1-carboxylate (854 mg, 53%) as a white foam. ESI-MS m/z calc. 782.284, found 783.5 (M+1)⁺; Retention time: 2.2 min (LC Method B).

Step 4: 2-Chloro-N-[[5-[5-(5,5-dimethylpyrrolidin-3-yl)pentyl]-2-pyridyl]sulfonyl]-6-[3-[2-[1-(trifluoromethyl)cyclopropyl]ethoxy]pyrazol-1-yl]pyridine-3-carboxamide (Hydrochloride Salt)

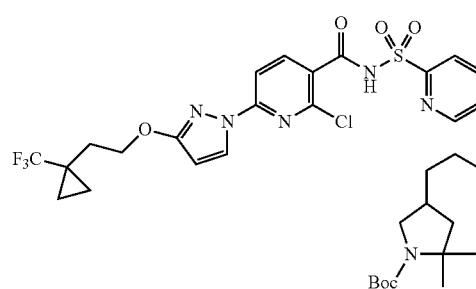

To a stirred solution of tert-butyl 4-[5-[6-[[2-chloro-6-[3-[2-[1-(trifluoromethyl)cyclopropyl]ethoxy]pyrazol-1-yl]pyridine-3-carbonyl]sulfamoyl]-3-pyridyl]pentyl]-2,2-dimethyl-pyrrolidine-1-carboxylate (850 mg, 1.085 mmol) in anhydrous methylene chloride (10 mL) was added hydrochloric acid in dioxane (6.8 mL of 4.0 M, 27.20 mmol), at 0° C. (ice-water bath) under nitrogen. After 10 min, the bath was removed and stirring was continued at room temperature for 30 min. Then, the volatiles were removed under reduced pressure and the residue was taken up in ethyl acetate (30 mL) and washed with saturated aqueous sodium bicarbonate (20 mL). The aqueous layer was re-extracted with ethyl acetate (25 mL). The combined organics were washed with brine, dried over anhydrous sodium sulfate, filtered and concentrated to dryness under reduced pressure to obtain crude 2-chloro-N-[[5-[5-(5,5-dimethylpyrrolidin-3-yl)pentyl]-2-pyridyl]sulfonyl]-6-[3-[2-[1-(trifluoromethyl)cyclopropyl]ethoxy]pyrazol-1-yl]pyridine-3-carboxamide (hydrochloride salt) (781 mg, 100%) as pale yellow foam. ESI-MS m/z calc. 682.23157, found 683.4 (M+1)⁺; Retention time: 1.71 min (LC Method B).

Step 5: 12,12-dimethyl-8-(3-{2-[1-(trifluoromethyl)cyclopropyl]ethoxy}-1H-pyrazol-1-yl)-2λ⁶-thia-3,9,11,22-tetraazatetracyclo[18.2.2.1¹¹,¹⁴.0⁵,¹⁰]pentacosa-1(23),5,7,9,20(24),21-hexaene-2,2,4-trione (Compound 143)

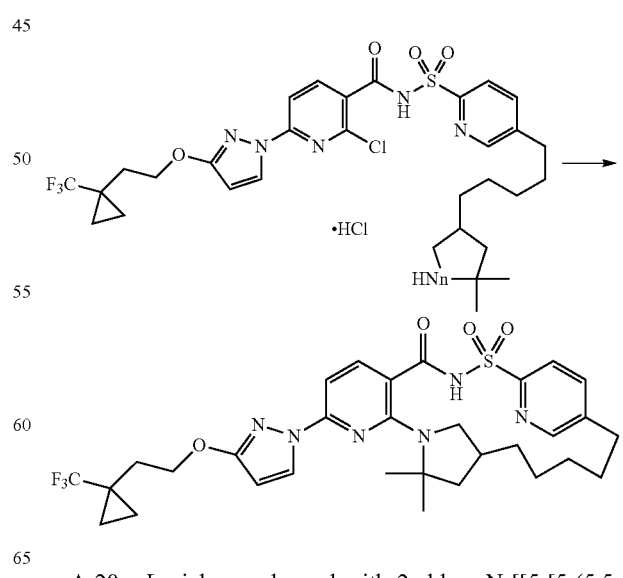

A 20 mL vial was charged with 2-chloro-N-[[5-[5-(5,5-dimethylpyrrolidin-3-yl)pentyl]-2-pyridyl]sulfonyl]-6-[3-

[2-[1-(trifluoromethyl)cyclopropyl]ethoxy]pyrazol-1-yl]pyridine-3-carboxamide (hydrochloride salt) (0.812 g, 1.128 mmol), potassium carbonate (1.11 g, 8.032 mmol), cesium fluoride (0.258 g, 1.698 mmol) and anhydrous dimethyl sulfoxide (25 mL). The vial was purged with a stream of nitrogen for 2 min, capped and stirred at 165° C. for 17 h. The reaction was allowed to cool to ambient temperature and the mixture was diluted with ethyl acetate (30 mL) and washed with a saturated aqueous sodium bicarbonate solution followed by brine. The organics were separated, dried over anhydrous sodium sulfate, filtered and evaporated under reduced pressure. Then silica gel chromatography (0%-55% ethyl acetate in hexanes gradient) followed by another silica gel column (0%-10% methanol in dichloromethane) afforded 12,12-dimethyl-8-(3-{2-[1-(trifluoromethyl)cyclopropyl]ethoxy}-1H-pyrazol-1-yl)-2λ$^6$-thia-3,9,11,22-tetraazatetracyclo[18.2.2.1$^{11,14}$.0$^{5,10}$]pentacosa-1(23),5,7,9,20(24),21-hexaene-2,2,4-trione (Compound 143) (80 mg, 11%) as a white solid. $^1$H NMR (400 MHz, dimethyl sulfoxide-d$_6$) δ 12.59 (s, 1H), 8.69 (s, 1H), 8.19 (d, J=2.8 Hz, 1H), 8.14 (d, J=7.9 Hz, 1H), 7.98 (d, J=8.1 Hz, 1H), 7.91 (d, J=8.3 Hz, 1H), 6.91 (d, J=8.3 Hz, 1H), 6.10 (d, J=2.7 Hz, 1H), 4.32 (t, J=7.0 Hz, 2H), 3.01-2.87 (m, 1H), 2.74-2.62 (m, 1H), 2.47-2.36 (m, 1H), 2.08 (t, J=7.0 Hz, 2H), 2.03-1.82 (m, 3H), 1.80-1.64 (m, 2H), 1.53 (s, 3H), 1.50 (s, 3H), 1.40 (t, J=12.2 Hz, 1H), 1.33-1.27 (m, 1H), 1.23 (s, 2H), 0.98-0.92 (m, 2H), 0.92-0.86 (m, 2H), 0.82 (d, J=12.6 Hz, 1H), 0.73-0.59 (m, 1H), 0.08--0.03 (m, 1H). ESI-MS m/z calc. 646.2549, found 647.5 (M+1)$^+$; Retention time: 1.96 min (LC Method B).

Example 156: Preparation of 13,20,20-trimethyl-4-(3-{2-[1-(trifluoromethyl)cyclopropyl]ethoxy}-1H-pyrazol-1-yl)-10λ$^6$-thia-1,3,9,14,22-pentaaza tetracyclo[16.2.1.1$^{11,14}$.0$^{2,7}$]docosa-2,4,6,11(22),12-pentaene-8,10,10-trione (Compound 144)

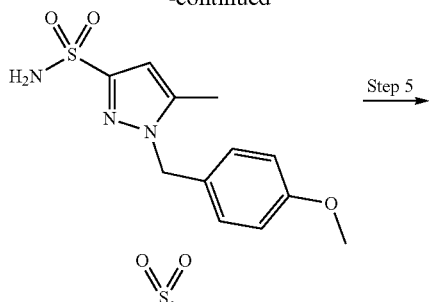

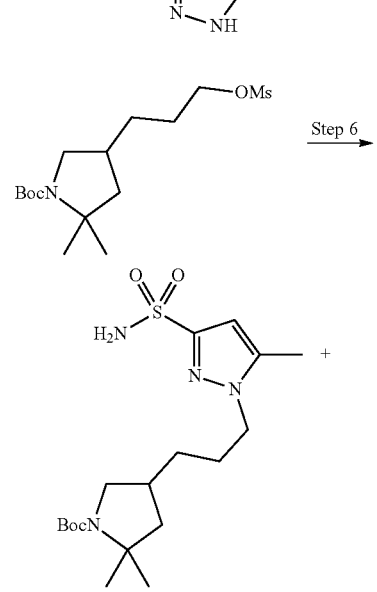

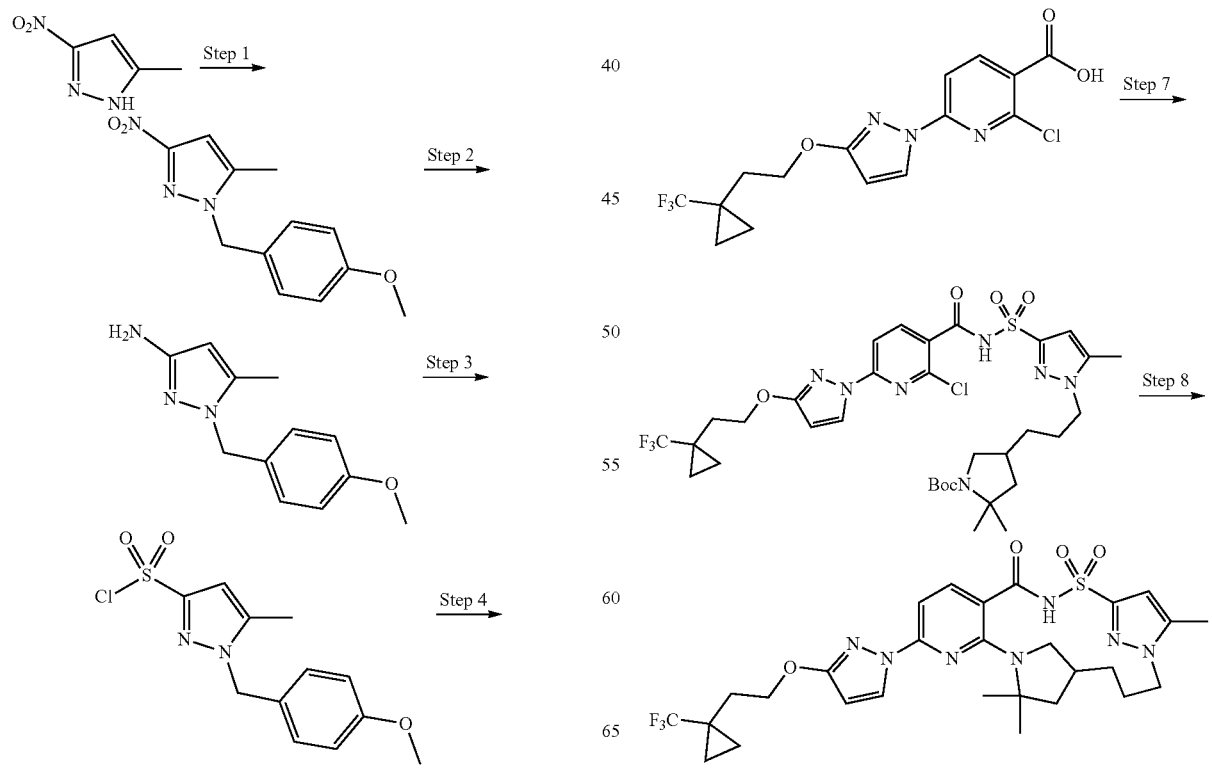

Step 1: 1-[(4-Methoxyphenyl)methyl]-5-methyl-3-nitro-pyrazole

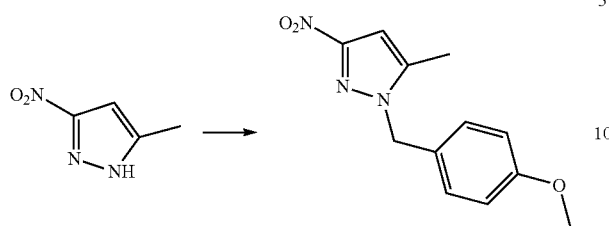

A 100 mL round-bottom flask attached with a reflux condenser was charged with 1-(bromomethyl)-4-methoxybenzene (2.7 g, 13.43 mmol), acetonitrile (20 mL), 5-methyl-3-nitro-1H-pyrazole (1.55 g, 12.20 mmol) and potassium carbonate (2.53 g, 18.31 mmol). The mixture was stirred at 80° C. for 6 h, then at room temperature over 3 days before being concentrated under reduced pressure. The residue was suspended in dichloromethane (80 mL). After stirring for 10 min, the mixture was filtered and the filtrate was mixed with silica gel before being concentrated. The residue was purified by silica gel chromatography using a gradient from 0%-30% ethyl acetate in heptanes to obtain 1-[(4-methoxyphenyl) methyl]-5-methyl-3-nitro-pyrazole (2.4 g, 80%) as a yellow solid. $^1$H NMR (300 MHz, CDCl$_3$) δ 2.25 (s, 3H), 3.79 (s, 3H), 5.28 (s, 2H), 6.67 (s, 1H), 6.87 (d, J=8.7 Hz, 2H), 7.14 (d, J=8.7 Hz, 2H). ESI-MS m/z 270.1 (M+Na)$^+$; Retention time: 1.88 min (LC Method I).

Step 2: 1-[(4-Methoxyphenyl)methyl]-5-methyl-pyrazol-3-amine

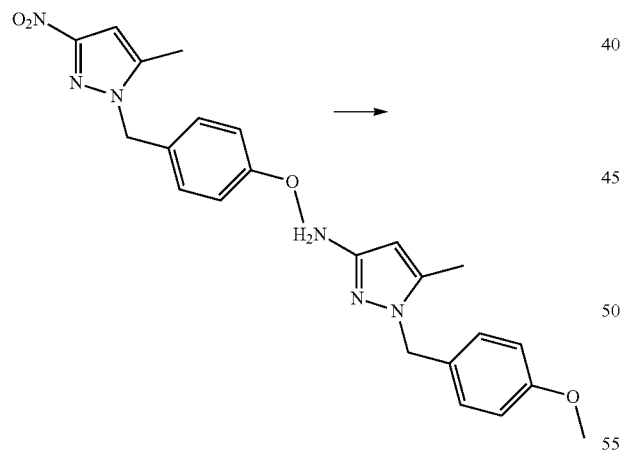

A mixture of 1-[(4-methoxyphenyl)methyl]-5-methyl-3-nitro-pyrazole (2.4 g, 9.707 mmol), NH$_4$Cl (5 g, 3.268 mL, 93.47 mmol), iron (5 g, 89.53 mmol), EtOH (20 mL) and water (4 mL) was stirred at 80° C. overnight. After being cooled to room temperature, the reaction mixture was filtered through a pad of celite, washing with methanol. The filtrate was concentrated and the residue was suspended in water (50 mL) and extracted with ethyl acetate (80 ml). The organic layers were washed with brine, dried over anhydrous sodium sulfate, filtered and concentrated under reduced pressure to afford 1-[(4-methoxyphenyl)methyl]-5-methyl-pyrazol-3-amine as a red oil (2 g, 91% purity by LCMS, 86% yield). $^1$H NMR (300 MHz, CDCl$_3$) δ 2.13 (s, 3H), 3.78 (s, 3H), 5.01 (s, 2H), 5.44 (s, 1H), 6.83 (d, J=8.7 Hz, 2H), 7.04 (d, J=8.7 Hz, 2H). ESI-MS m/z calc. 217.1215, found 218.2 (M+1)$^+$; Retention time: 1.21 min (LC Method I).

Step 3: 1-[(4-Methoxyphenyl)methyl]-5-methyl-pyrazole-3-sulfonyl chloride

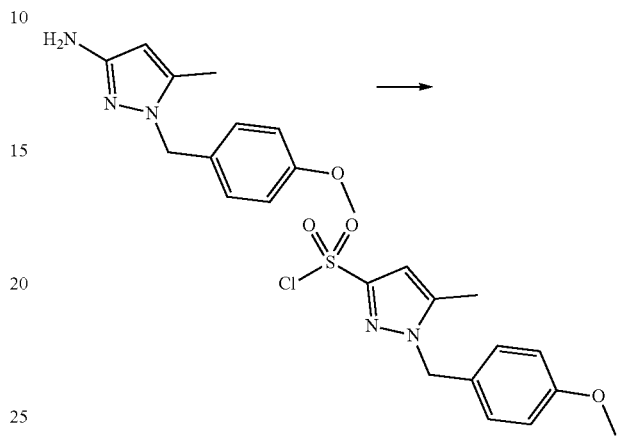

1-[(4-Methoxyphenyl)methyl]-5-methyl-pyrazol-3-amine (20 g, 92 mmol) was dissolved in AcOH (60 mL) and formic acid (20 mL). The mixture was cooled with an ice-methanol bath. Then hydrochloric acid (15.2 mL of 12 M, 182 mmol) was added. After the internal temperature reached around −8° C., a solution of sodium nitrite (6.6 g, 96 mmol) in water (10 mL) was slowly added, keeping internal temperature between −5° C. and −10° C. The mixture was stirred at the same temperature for 5 min, then added this mixture with pipette by portions to a mixture of CuCl (2.74 g, 28 mmol), SO$_2$ (44 g, 343 mmol) and AcOH (60 mL) at room temperature (the SO$_2$ solution in AcOH was made by passing the gas through AcOH at 0° C.). The resulting mixture was allowed to warm up to room temperature for 1 h. The mixture was concentrated under reduced pressure. The residue was mixed with diethyl ether (200 mL) and ice-water (50 mL). There was lots of black oil that was not soluble in either phase. After the mixture was vigorously stirred for 20 min, the two layers were separated. The organic layer was washed with water (2×50 mL), brine (30 mL) and concentrated under reduced pressure and finally co-evaporated with toluene (60 mL) to give 1-[(4-methoxyphenyl)methyl]-5-methyl-pyrazole-3-sulfonyl chloride (9 g, 33%) as a brown oil which was used directly in the next step. ESI-MS m/z calc. 300.0335, found 323.0 (M+Na)$^+$; Retention time: 2.05 min (LC Method I).

Step 4: 1-[(4-Methoxyphenyl)methyl]-5-methyl-pyrazole-3-sulfonamide

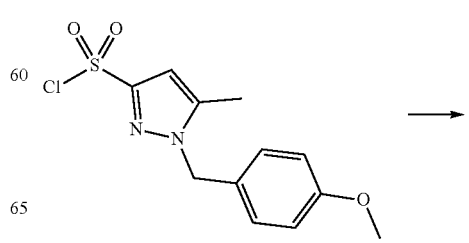

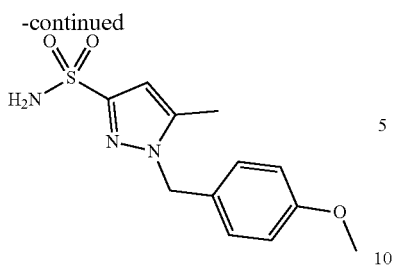

A solution of 1-[(4-methoxyphenyl)methyl]-5-methyl-pyrazole-3-sulfonyl chloride (586 mg, 1.9484 mmol) in dichloromethane (4 mL) was added to a solution of ammonia (15 mL of 0.5 M in 1,4-dioxane, 7.5000 mmol) cooled with ice-water (partially frozen). After 30 min, the cooling bath was removed and the reaction was stirred at room temperature for 2 h before concentrated under reduced pressure. The residue was purified by silica gel chromatography using 0%-70% ethyl acetate in heptanes to obtain 1-[(4-methoxyphenyl)methyl]-5-methyl-pyrazole-3-sulfonamide (200 mg, 36% yield) as a white solid. ESI-MS m/z calc. 281.0834, found 282.1 (M+1)+; Retention time: 1.49 min (LC Method I).

Step 5: 5-Methyl-1H-pyrazole-3-sulfonamide

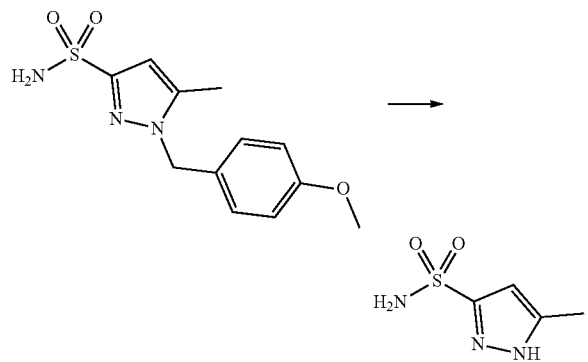

A solution of 1-[(4-methoxyphenyl)methyl]-5-methyl-pyrazole-3-sulfonamide (16.3 g, 57.9 mmol) in trifluoroacetic acid (80 mL) was stirred at 80° C. (oil bath) overnight. The mixture was concentrated and the residue was purified by silica gel chromatography using 0%-100% ethyl acetate in heptanes. The fractions containing the desired product were combined and concentrated. The residue was triturated with dichloromethane (30 mL) to provide 5-methyl-1H-pyrazole-3-sulfonamide as a light yellow solid (6741 mg, 69% yield). ¹H NMR (300 MHz, dimethyl sulfoxide-d₆) ppm 2.25 (s, 3H), 6.32 (s, 1H), 7.28 (s, 2H), 13.11 (br. s., 1H).

Step 6: tert-Butyl 2,2-dimethyl-4-[3-(5-methyl-3-sulfamoyl-pyrazol-1-yl)propyl]pyrrolidine-1-carboxylate

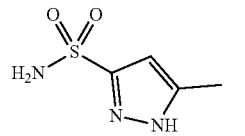

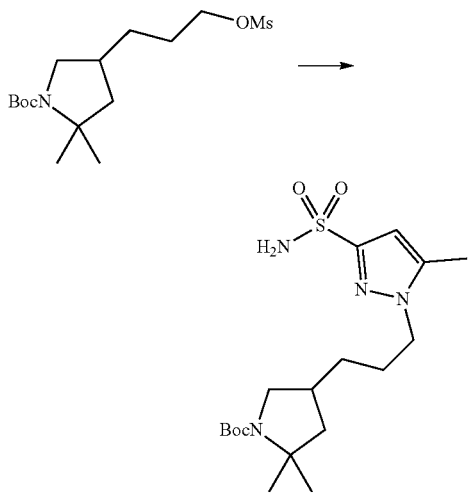

tert-Butyl 2,2-dimethyl-4-(3-methylsulfonyloxypropyl)pyrrolidine-1-carboxylate (1.35 g, 4.024 mmol) and 5-methyl-1H-pyrazole-3-sulfonamide (638 mg, 3.958 mmol) followed by potassium carbonate (1.95 g, 14.11 mmol) were dissolved in N,N-dimethylformamide (41.32 mL) and stirred at 80° C. in a 150 mL sealed vessel for 20 h. Cooled, poured into water (100 mL) and extracted with ethyl acetate (2×100 mL), combined organic layers, washed with water (2×100 mL), dried (sodium sulfate), filtered and concentrated. The orange residue was purified by silica gel chromatography using a gradient from 100% hexanes to 100% ethyl acetate to afford as a colorless oil which turned into a white solid upon drying under vacuum, tert-butyl 2,2-dimethyl-4-[3-(5-methyl-3-sulfamoyl-pyrazol-1-yl)propyl]pyrrolidine-1-carboxylate (419 mg, 52%). ¹H NMR (400 MHz, dimethyl sulfoxide-d₆) δ 7.31 (s, 2H), 6.36 (s, 1H), 4.05 (t, J=6.4 Hz, 2H), 3.54 (dd, J=18.2, 8.1 Hz, 1H), 2.77 (q, J=10.2 Hz, 1H), 2.31 (d, J=15.4 Hz, 3H), 2.12 (d, J=19.6 Hz, 1H), 1.87 (td, J=14.0, 6.4 Hz, 1H), 1.78-1.65 (m, 2H), 1.41-1.28 (m, 15H), 1.24 (s, 3H). ESI-MS m/z calc. 400.21442, found 401.2 (M+1)+; Retention time: 1.54 min (LC Method E).

Step 7: tert-Butyl 4-[3-[3-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate

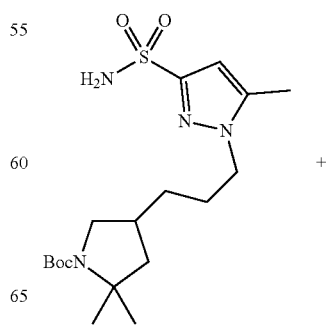

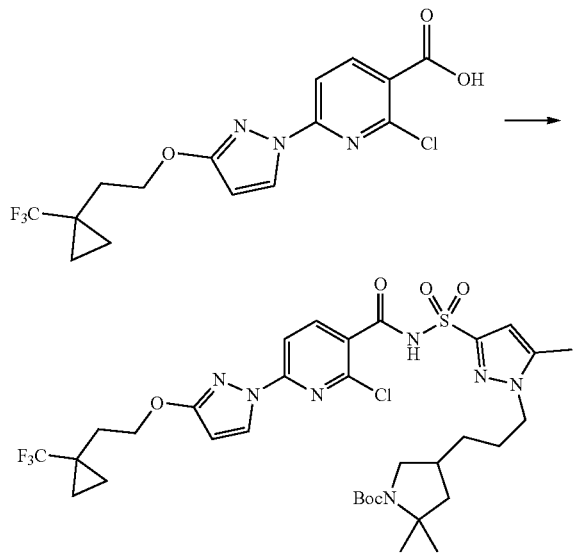

2-Chloro-6-[3-[2-[1-(trifluoromethyl)cyclopropyl]ethoxy]pyrazol-1-yl]pyridine-3-carboxylic acid (485 mg, 1.291 mmol) and carbonyl diimidazole (210 mg, 1.295 mmol) were combined in tetrahydrofuran (8.0 mL) and stirred for 90 min at room temperature. Then tert-butyl 2,2-dimethyl-4-[3-(5-methyl-3-sulfamoyl-pyrazol-1-yl)propyl]pyrrolidine-1-carboxylate (342 mg, 0.8539 mmol) was added followed by 1,8-diazabicyclo[5.4.0]undec-7-ene (325 μL, 2.173 mmol) and the reaction was heated at 50° C. for 16 h. The reaction was diluted with ethyl acetate and washed with a saturated aqueous sodium bicarbonate solution followed by brine. The organics were separated, dried over sodium sulfate, filtered and evaporated and then purified by silica gel chromatography using a gradient from 100% hexanes to 100% ethyl acetate to afford as an off-white solid, tert-butyl 4-[3-[3-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (451 mg, 70%). ESI-MS m/z calc. 757.2636, found 758.2 (M+1)⁺; Retention time: 2.32 min (LC Method E).

Step 8: 13,20,20-Trimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 144)

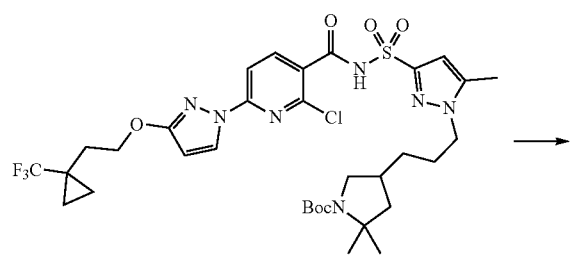

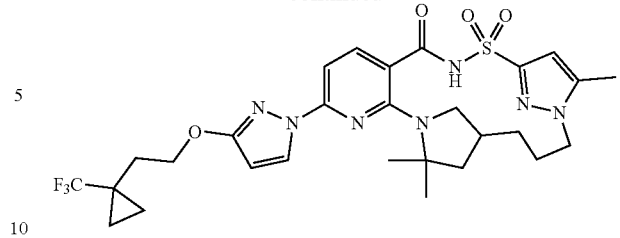

tert-Butyl 4-[3-[3-[[2-chloro-6-[3-[2-[1-(trifluoromethyl)cyclopropyl]ethoxy]pyrazol-1-yl]pyridine-3-carbonyl]sulfamoyl]-5-methyl-pyrazol-1-yl]propyl]-2,2-dimethyl-pyrrolidine-1-carboxylate (451 mg, 0.5948 mmol) was dissolved in dichloromethane (11 mL) and to the mixture was added hydrochloric acid (4.5 mL of 4 M in dioxane, 18.00 mmol) and stirred at room temperature for 45 min. Concentrated mixture to dryness under reduced pressure, redissolved in ethyl acetate and then added aqueous 2 M sodium carbonate (5 mL), giving pH~10. Extracted the solution with ethyl acetate (2×10 mL), washed with brine, then dried over sodium sulfate, filtered and evaporated to dryness under reduced pressure. Combined the resulting material and potassium carbonate (411 mg, 2.974 mmol), cesium fluoride (136 mg, 0.8953 mmol), 3 Å molecular sieves and dimethyl sulfoxide (13.5 mL) in a vial, purged with nitrogen, capped, heated to 155° C. and stirred for 20 h. Cooled to room temperature and filtered, diluted with ethyl acetate and washed with a saturated aqueous sodium bicarbonate solution followed by brine. The organics were separated, dried over sodium sulfate, filtered and evaporated and then purified by silica gel chromatography using a gradient from 100% hexanes to 80% ethyl acetate in hexanes to afford as a white solid, 13,20,20-trimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 144) (141 mg, 38%). ¹H NMR (400 MHz, dimethyl sulfoxide-d₆) δ 12.68 (s, 1H), 8.19 (d, J=2.8 Hz, 1H), 7.70 (d, J=8.2 Hz, 1H), 6.88 (d, J=8.2 Hz, 1H), 6.69 (s, 1H), 6.09 (d, J=2.7 Hz, 1H), 4.30 (t, J=7.0 Hz, 2H), 4.10-3.94 (m, 2H), 2.82-2.71 (m, 1H), 2.34 (d, J=8.9 Hz, 3H), 2.13 (dd, J=8.7, 4.0 Hz, 1H), 2.09-2.02 (m, 3H), 1.96-1.80 (m, 3H), 1.77 (dd, J=11.9, 5.2 Hz, 1H), 1.54 (s, 3H), 1.48 (s, 3H), 1.35 (t, J=12.3 Hz, 1H), 0.99-0.92 (m, 2H), 0.89 (d, J=11.6 Hz, 2H), 0.59-0.39 (m, 1H). ESI-MS m/z calc. 621.2345, found 622.2 (M+1)⁺; Retention time: 2.14 min (LC Method E).

Example 157: Preparation of 12,12-dimethyl-8-(3-{2-[1-(trifluoromethyl)cyclopropyl]ethoxy}-1H-pyrazol-1-yl)-19-oxa-2λ⁶-thia-3,9,11,24-tetraazatetracyclo[18.3.1.0⁵,¹⁰.0¹¹,¹⁵]tetracosa-1(24),5(10),6,8,20,22-hexaene-2,2,4-trione (Compound 147)

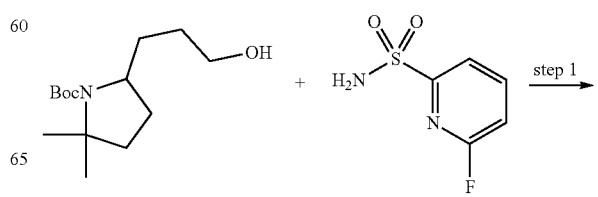

999

-continued

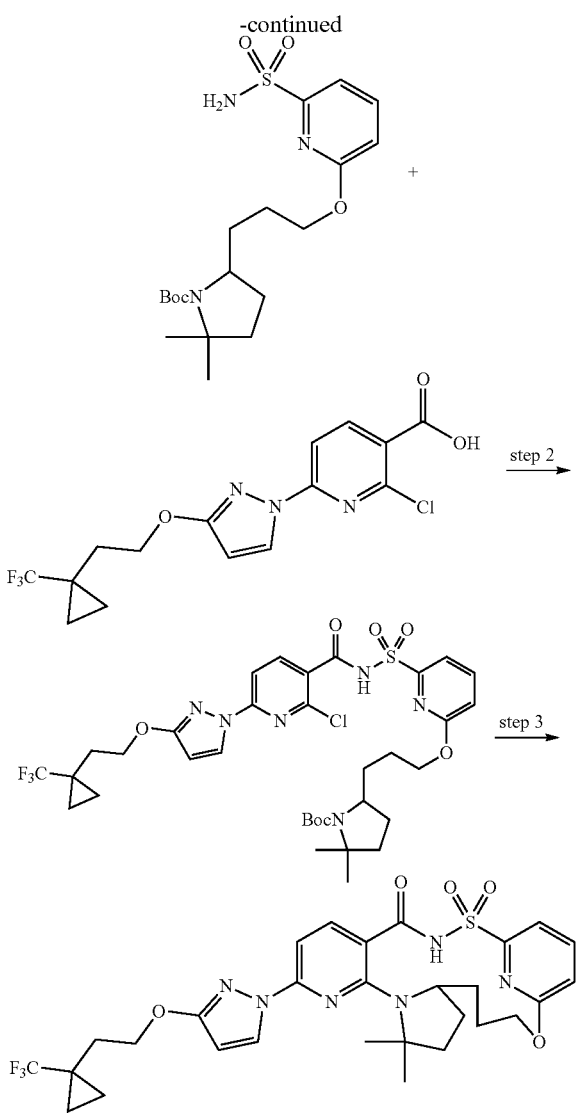

Step 1: tert-Butyl 2,2-dimethyl-5-[3-[(6-sulfamoyl-2-pyridyl)oxy]propyl]pyrrolidine-1-carboxylate

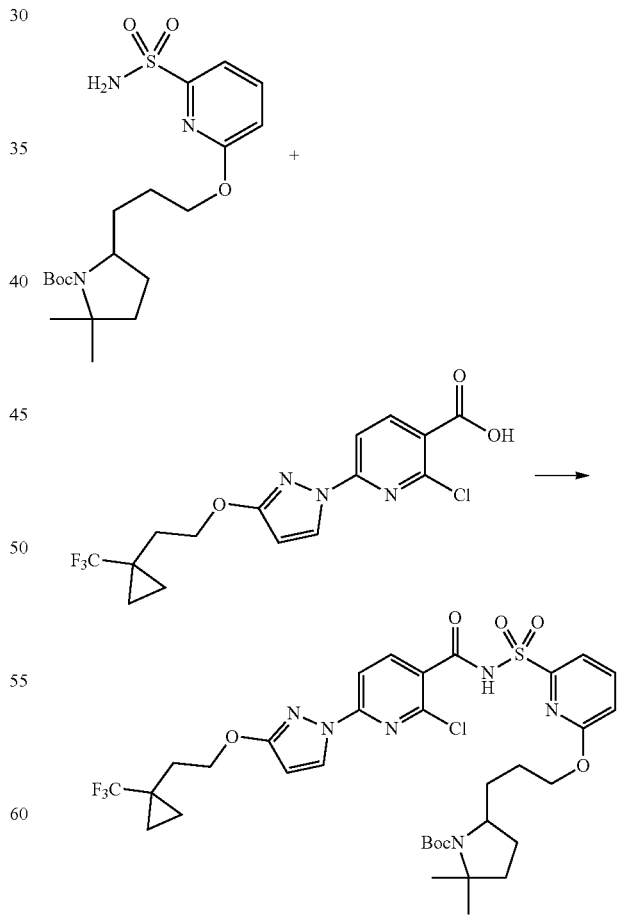

1000

To a 20 mL vial was added tert-butyl 5-(3-hydroxypropyl)-2,2-dimethyl-pyrrolidine-1-carboxylate (631 mg, 2.452 mmol) and anhydrous N,N-dimethylformamide (8 mL). To the solution was added, portionwise, 60% NaH (196 mg, 4.900 mmol) (CAUTION: gas evolution) and the mixture was stirred at room temperature for 15 min. 6-Fluoropyridine-2-sulfonamide (432 mg, 2.452 mmol) was then added and the resulting mixture was stirred at room temperature for 30 min. To the stirring solution at room temperature was added additional NaH (98 mg, 2.450 mmol) and the reaction vial was capped. The resulting mixture was stirred at 100° C. for 14 h. The reaction solution was diluted with ethyl acetate then poured into aqueous 1 N citric acid and extracted with ethyl acetate (2×). The combined organic fractions were dried (sodium sulfate), filtered and concentrated to a clear oil which was purified by silica gel chromatography using a mobile phase gradient of 100% hexanes to 100% ethyl acetate giving tert-butyl 2,2-dimethyl-5-[3-[(6-sulfamoyl-2-pyridyl)oxy]propyl]pyrrolidine-1-carboxylate (350 mg, 35%). ESI-MS m/z calc. 413.19846, found 414.31 (M+1)⁺; Retention time: 0.69 min (LC Method A).

Step 2: tert-Butyl 5-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate 2-Chloro-6-[3-[2-[1-(trifluoromethyl)cyclopropyl]ethoxy]pyrazol-1-yl]pyridine-3-carboxylic acid (387 mg, 1.030 mmol) and carbonyl diimidazole (193 mg, 1.190 mmol) were combined in anhydrous tetrahydrofuran (8 mL) and stirred for 75 min at 50° C. Then a tetrahydrofuran solution (7 mL) of tert-butyl 2,2-dimethyl-5-[3-[(6-sulfamoyl-2-pyridyl)oxy]propyl]pyrrolidine-1-carboxylate (328 mg, 0.7932 mmol) and 1,8-diazabicyclo[5.4.0]undec-7-ene (300 µL, 2.006 mmol) was added. The reaction was heated at 50° C. for 4 h. The reaction was diluted with ethyl acetate and washed with a 1 M citric acid solution, followed by brine. The organics were separated, dried over sodium sulfate, filtered and evaporated and then purified by silica gel chromatography using a gradient of 100% hexanes to 75% ethyl acetate in hexanes to afford as an off-white solid, tert-butyl 5-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate (409 mg, 67%). ESI-MS m/z calc. 770.2476, found 771.37 (M+1)+; Retention time: 0.92 min (LC Method A).

Step 3: 12,12-Dimethyl-8-(3-{2-[1-(trifluoromethyl)cyclopropyl]ethoxy}-1H-pyrazol-1-yl)-19-oxa-2λ6-thia-3,9,11,24-tetraazatetracyclo[18.3.1.05,10.011,15]tetracosa-1(24),5(10),6,8,20,22-hexaene-2,2,4-trione (Compound 147)

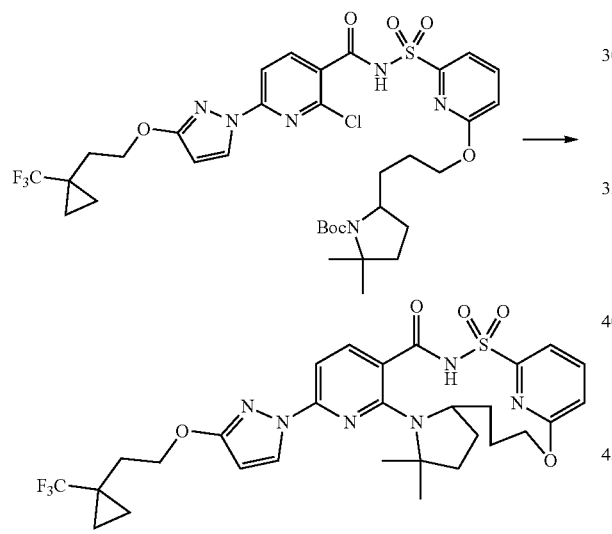

tert-Butyl 5-[3-[[6-[[2-chloro-6-[3-[2-[1-(trifluoromethyl)cyclopropyl]ethoxy]pyrazol-1-yl]pyridine-3-carbonyl]sulfamoyl]-2-pyridyl]oxy]propyl]-2,2-dimethyl-pyrrolidine-1-carboxylate (408 mg, 0.5290 mmol) was dissolved in dichloromethane (7 mL) and to the mixture was added hydrochloric acid (4 mL of 4 M in dioxane, 16.00 mmol) and stirred at room temperature for 30 min. Concentrated the mixture to dryness under reduced pressure and combined the resulting material and potassium carbonate (440 mg, 3.184 mmol), cesium fluoride (130 mg, 0.8558 mmol), 3 Å molecular sieves and dimethyl sulfoxide (8 mL) in a vial, purged with nitrogen, capped, heated to 140° C. and stirred for 16 h. Cooled to room temperature, filtered and then purified by reverse-phase preparative chromatography utilizing a $C_{18}$ column (30%-99% acetonitrile in water+5 mM hydrochloric acid) to afford as a white solid, 12,12-dimethyl-8-(3-{2-[1-(trifluoromethyl) cyclopropyl]ethoxy}-1H-pyrazol-1-yl)-19-oxa-2λ6-thia-3,9,11,24-tetraazatetracyclo [18.3.1.05,10.011,15]tetracosa-1(24),5(10),6,8,20,22-hexaene-2,2,4-trione (Compound 147) (17 mg, 5%). ESI-MS m/z calc. 634.2185, found 635.29 (M+1)+; Retention time: 2.0 min (LC Method B).

Example 158: Preparation of 13,20,20-trimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Enantiomer 1) (Compound 150) and 13,20,20-trimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Enantiomer 2) (Compound 151)

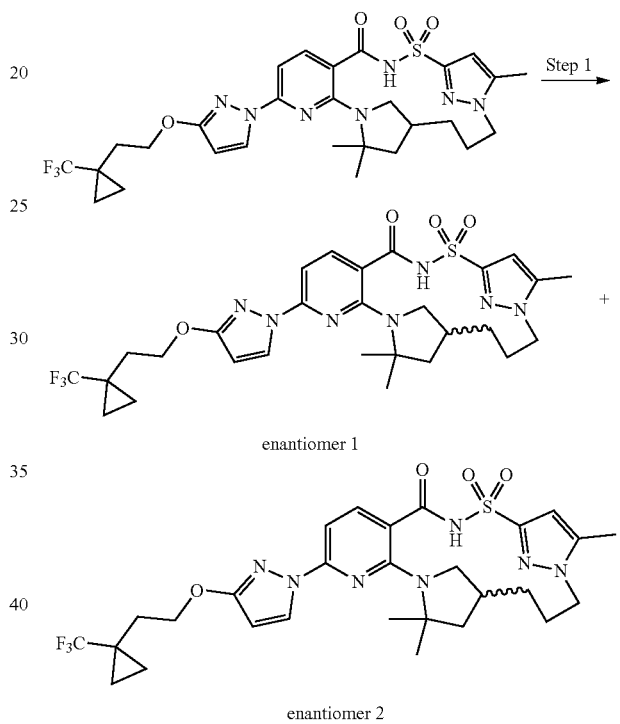

enantiomer 1 enantiomer 2

Step 1: 13,20,20-Trimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Enantiomer 1) (Compound 150) and 13,20,20-trimethyl-4-(3-{2-[1-(trifluoromethyl)cyclopropyl]ethoxy}-1H-pyrazol-1-yl)-10λ6-thia-1,3,9,14,22-pentaazatetracyclo[16.2.1.111,14.02,7]docosa-2,4,6,11(22),12-pentaene-8,10,10-trione (Enantiomer 2) (Compound 151)

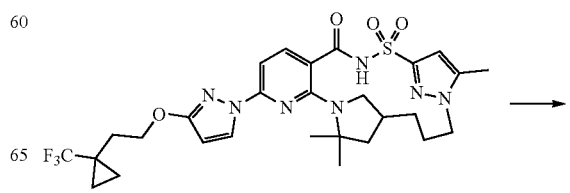

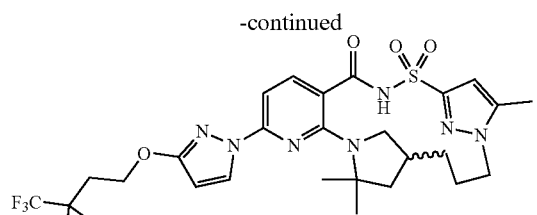

enantiomer 1

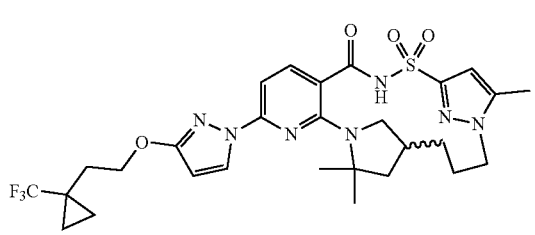

enantiomer 2

Racemic 13,20,20-trimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2,4,6,11(22),12-pentaene-8,10,10-trione (114 mg, 0.1815 mmol) was subjected to chiral SFC chromatography. The following SFC protocol was employed: ChiralPak AS-H (150×21.2 mm), 5 μm; 35° C. mobile phase: 25% acetonitrile:methanol (90:10; no modifier), 75% carbon dioxide at 70 mL/min over 8.0 min (injection volume=70 μL of 32 mg/mL in acetonitrile:methanol (90:10) giving as the first enantiomer to elute, 13,20,20-trimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2,4,6,11(22),12-pentaene-8,10,10-trione (enantiomer 1) (Compound 150) (51.27 mg, 91%) as a white solid. ¹H NMR (400 MHz, dimethyl sulfoxide-d₆) δ 12.66 (s, 1H), 8.19 (d, J=2.8 Hz, 1H), 7.70 (d, J=8.2 Hz, 1H), 6.88 (d, J=8.2 Hz, 1H), 6.69 (s, 1H), 6.09 (d, J=2.7 Hz, 1H), 4.31 (t, J=7.0 Hz, 2H), 4.10-3.93 (m, 2H), 2.85-2.70 (m, 1H), 2.35 (s, 3H), 2.12 (d, J=5.6 Hz, 1H), 2.07 (t, J=7.1 Hz, 3H), 1.97-1.81 (m, 3H), 1.77 (dd, J=11.8, 5.4 Hz, 1H), 1.54 (s, 3H), 1.48 (s, 3H), 1.35 (t, J=12.3 Hz, 1H), 0.99-0.92 (m, 2H), 0.89 (d, J=11.9 Hz, 2H), 0.52 (dd, J=15.5, 8.4 Hz, 1H). ESI-MS m/z calc. 621.2345, found 622.5 (M+1)⁺; Retention time: 2.19 min (LC Method E). The second enantiomer to elute was 13,20,20-trimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2,4,6,11(22),12-pentaene-8,10,10-trione (enantiomer 2) (Compound 151) (31.08 mg, 55%) as a white solid. ESI-MS m/z calc. 621.2345, found 622.5 (M+1)⁺; Retention time: 2.19 min (LC Method E).

Example 159: Preparation of 21,21-dimethyl-4-(3-{2-[1-(trifluoromethyl)cyclopropyl]ethoxy}-1H-pyrazol-1-yl)-18-oxa-10λ⁶-thia-1,3,9,14,15-pentaazatetracyclo[17.2.1.0²,⁷.0¹¹,¹⁵]docosa-2(7),3,5,11,13-pentaene-8,10,10-trione (Compound 152)

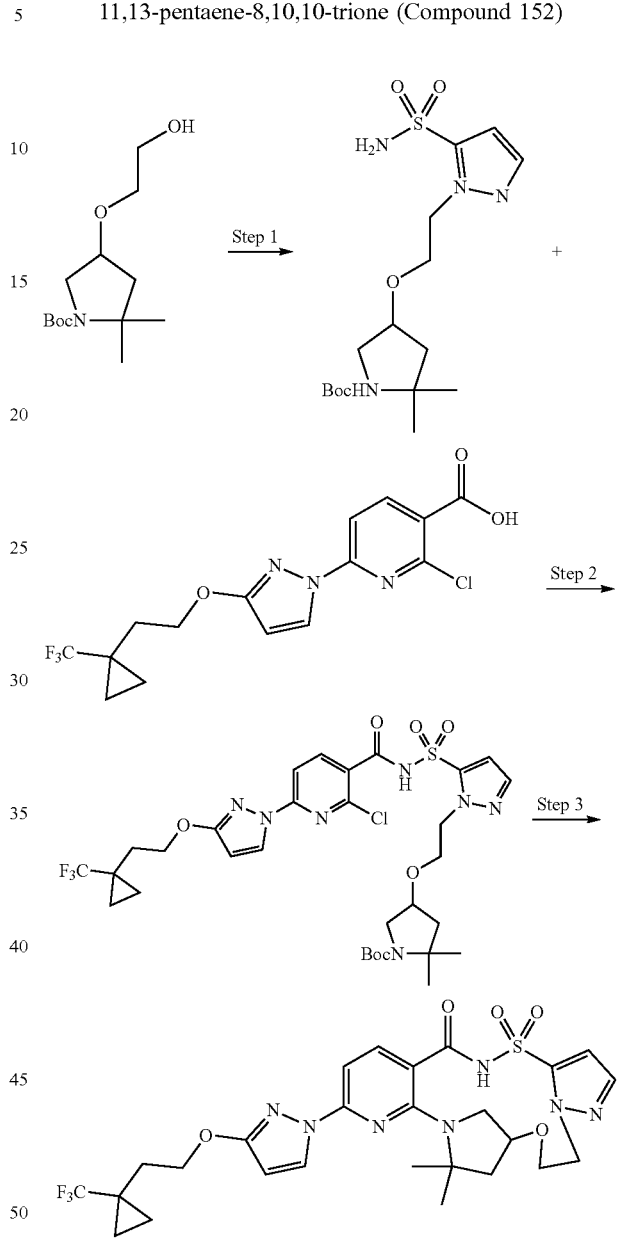

Step 1: tert-Butyl 2,2-dimethyl-4-[2-(3-sulfamoylpyrazol-1-yl)ethoxy]pyrrolidine-1-carboxylate

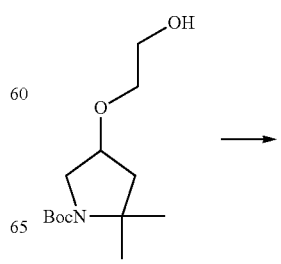

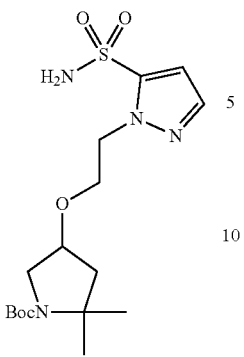

To a nitrogen sparged round bottom flask containing tert-butyl 4-(2-hydroxyethoxy)-2,2-dimethyl-pyrrolidine-1-carboxylate (1.94 g, 7.480 mmol) was added dichloromethane (70 mL). The solution was cooled to 0° C. prior to addition of Et₃N (6 mL, 43.05 mmol) and methanesulfonyl chloride (1.7 mL, 21.96 mmol). The reaction mixture was stirred for 20 h allowing to warm to room temperature after 1 h (the clear solution turned cloudy orange after 10 min). The reaction mixture was quenched by addition of water. Dichloromethane was added followed by brine and the organic layer was separated. The aqueous layer was extracted with further dichloromethane (2×20 mL) and the combined organics were dried over sodium sulfate, filtered and concentrated under reduced pressure. The resulting material was dried under vacuum for 1 h to give a yellow oil which was combined with 1H-pyrazole-3-sulfonamide (1.1 g, 7.475 mmol) in a round bottom flask followed by addition of potassium carbonate (2.23 g, 16.14 mmol) and the mixture was dissolved in N,N-dimethylformamide (13 mL). The reaction mixture was stirred at 50° C. in a 150 mL sealed vessel for 48 h. Cooled the mixture to room temperature, poured into water (100 mL) and extracted with ethyl acetate (2×100 mL), combined organic layers, washed with water (2×100 mL), dried (sodium sulfate), filtered and concentrated. The orange residue was purified by silica gel chromatography using a gradient from 100% hexanes to 100% ethyl acetate to afford as the first eluting, less polar regioisomer, tert-butyl 2,2-dimethyl-4-[2-(5-sulfamoylpyrazol-1-yl)ethoxy]pyrrolidine-1-carboxylate (550 mg, 38%). ESI-MS m/z calc. 388.17804, found 389.1 (M+1)⁺; Retention time: 0.56 min (LC Method A).

Step 2: tert-Butyl 4-[2-3-[[2-chloro-6-[3-[2-[1-(trifluoromethyl)cyclopropyl]ethoxy]pyrazol-1-yl]pyridine-3-carbonyl]sulfamoyl]pyrazol-1-yl]ethoxy]-2,2-dimethyl-pyrrolidine-1-carboxylate

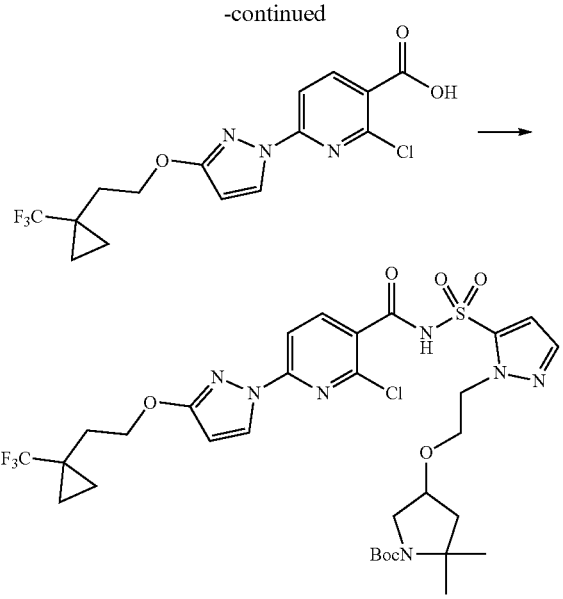

2-Chloro-6-[3-[2-[1-(trifluoromethyl)cyclopropyl] ethoxy]pyrazol-1-yl]pyridine-3-carboxylic acid (183.5 mg, 0.4884 mmol) and carbonyl diimidazole (91.40 mg, 0.5637 mmol) were combined in anhydrous tetrahydrofuran (4 mL) and stirred for 90 min at 50° C. Then a tetrahydrofuran solution (7 mL) of tert-butyl 2,2-dimethyl-4-[2-(3-sulfamoylpyrazol-1-yl)ethoxy]pyrrolidine-1-carboxylate (146 mg, 0.3758 mmol) and 1,8-diazabicyclo[5.4.0]undec-7-ene (142.1 µL, 0.9502 mmol) was added. The reaction was heated at 50° C. for 4 h. The reaction was diluted with ethyl acetate and washed with a 1 M citric acid solution, followed by brine. The organics were separated, dried over sodium sulfate, filtered and evaporated and then purified by silica gel chromatography using a gradient from 100% hexanes to 75% ethyl acetate in hexanes to afford tert-butyl 4-[2-[3-[[2-chloro-6-[3-[2-[1-(trifluoromethyl)cyclopropyl]ethoxy] pyrazol-1-yl]pyridine-3-carbonyl]sulfamoyl]pyrazol-1-yl] ethoxy]-2,2-dimethyl-pyrrolidine-1-carboxylate (162 mg, 58%) as an off-white solid. ESI-MS m/z calc. 745.22723, found 746.22 (M+1)⁺; Retention time: 0.87 min (LC Method A).

Step 3: 21,21-Dimethyl-4-(3-{2-[1-(trifluoromethyl) cyclopropyl]ethoxy}-1H-pyrazol-1-yl)-18-oxa-10λ⁶-thia-1,3,9,14,15-pentaazatetracyclo[17.2.1.0²,⁷.0¹¹,¹⁵]docosa-2(7),3,5,11,13-pentaene-8,10,10-trione (Compound 152)

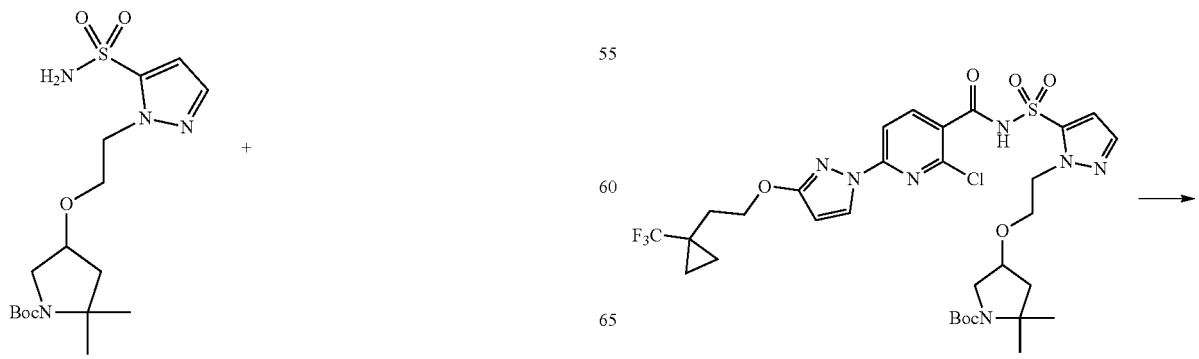

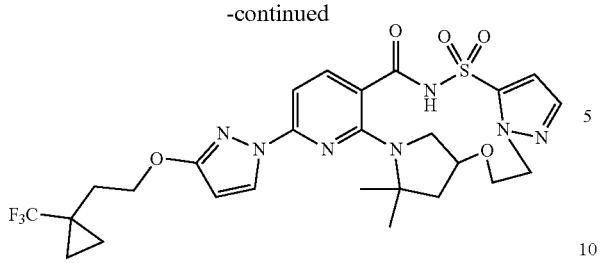

tert-Butyl 4-[2-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]ethoxy]-2,2-dimethyl-pyrrolidine-1-carboxylate (162 mg, 0.2171 mmol) was dissolved in dichloromethane (3 mL) and to the mixture was added hydrochloric acid (1.6 mL of 4 M in dioxane, 6.400 mmol) and stirred at room temperature for 30 min. Concentrated the mixture to dryness under reduced pressure and combined with potassium carbonate (180 mg, 1.302 mmol), cesium fluoride (55 mg, 0.3621 mmol), 3 Å molecular sieves and dimethyl sulfoxide (3.5 mL) in a vial, purged with nitrogen, capped, heated to 140° C. and stirred for 10 h. Cooled to room temperature, filtered and then purified by reverse-phase preparative chromatography utilizing a $C_{18}$ column (30%-99% acetonitrile/water+5 mM hydrochloric acid) to afford as a white solid, 21,21-dimethyl-4-(3-{2-[1-(trifluoromethyl) cyclopropyl]ethoxy}-1H-pyrazol-1-yl)-18-oxa-10$\lambda^6$-thia-1,3,9,14,15-pentaazatetracyclo[17.2.1.02,7.011,15]docosa-2(7),3,5,11,13-pentaene-8,10,10-trione (Compound 152) (45 mg, 34%). $^1$H NMR (400 MHz, dimethyl sulfoxide-$d_6$) δ 13.14 (s, 1H), 8.28 (d, J=2.8 Hz, 1H), 7.96 (d, J=8.3 Hz, 1H), 7.71 (d, J=2.0 Hz, 1H), 7.25 (d, J=8.2 Hz, 1H), 7.05 (d, J=2.0 Hz, 1H), 6.14 (d, J=2.8 Hz, 1H), 4.79-4.63 (m, 1H), 4.61-4.46 (m, 1H), 4.32 (t, J=7.0 Hz, 2H), 4.17-3.98 (m, 2H), 3.89 (ddd, J=11.1, 6.4, 2.7 Hz, 1H), 3.39 (dd, J=11.0, 4.4 Hz, 1H), 3.00 (d, J=10.9 Hz, 1H), 2.06 (dt, J=13.1, 6.6 Hz, 3H), 1.91 (dd, J=13.4, 2.7 Hz, 1H), 1.48 (s, 3H), 1.38 (s, 3H), 1.02-0.92 (m, 2H), 0.92-0.82 (m, 2H). ESI-MS m/z calc. 609.1981, found 610.25 (M+1)$^+$; Retention time: 2.04 min (LC Method B).

Example 160: Preparation of (14S)-12,12-dimethyl-8-(2-oxo-3-{2-[1-(trifluoromethyl) cyclopropyl]ethoxy}pyrrolidin-1-yl)-2$\lambda^6$-thia-3,9,11,18,23-pentaazatetracyclo[17.3.1.111,14.05,10]tetracosa-1(22),5,7,9,19(23),20-hexaene-2,2,4-trione (Compound 158)

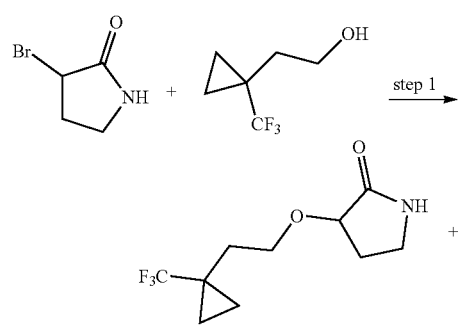

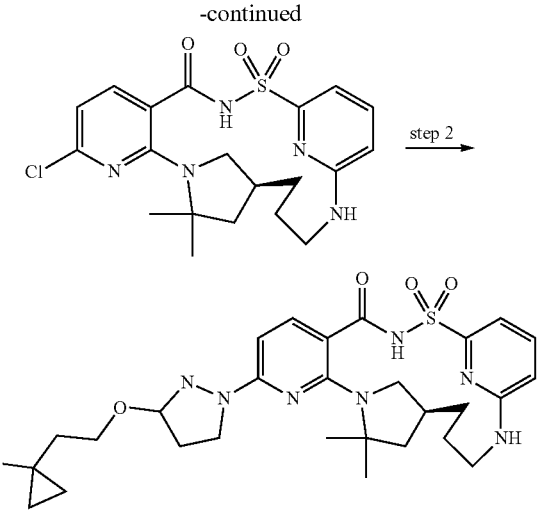

Step 1: 3-[2-[1-(Trifluoromethyl)cyclopropyl]ethoxy]pyrrolidin-2-one

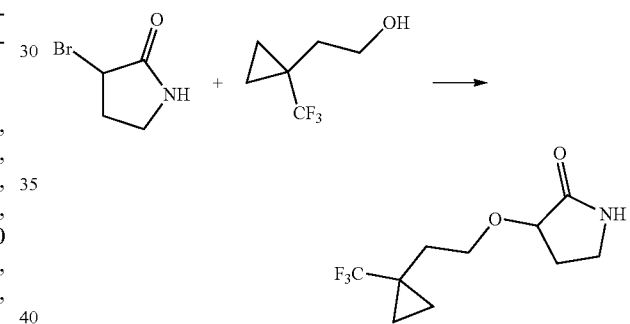

To a stirred solution of 3-bromopyrrolidin-2-one (600 mg, 3.659 mmol) and 2-[1-(trifluoromethyl)cyclopropyl]ethanol (665 mg, 4.315 mmol) in anhydrous tetrahydrofuran (15 mL) was added potassium hexamethyldisilazide (16.0 mL of 0.5 M in toluene, 8.000 mmol) at 0° C. (ice-water bath) over 2 min under nitrogen. The reaction was allowed to warm gradually to ambient temperature overnight (14 h). The reaction was acidified with glacial acetic acid (300 μL, 5.275 mmol) and the volatiles were removed at 20° C. under reduced pressure. The aqueous residue was taken up in ethyl acetate (50 mL) and washed with brine (20 mL). The organic layer was dried (anhydrous sodium sulfate), filtered and concentrated under reduced pressure to obtain brownish crude material. The crude was purified from silica gel chromatography (0%-10% methanol in methylene chloride gradient) to furnish 3-[2-[1-(trifluoromethyl)cyclopropyl]ethoxy]pyrrolidin-2-one (285 mg, 33%) as a white solid. $^1$H NMR (400 MHz, Benzene-$d_6$) δ 6.76 (s, 1H), 4.21 (dt, J=9.4, 6.7 Hz, 1H), 3.73-3.64 (m, 1H), 3.55 (t, J=7.3 Hz, 1H), 2.67 (dddd, J=9.3, 7.6, 4.6, 1.2 Hz, 1H), 2.46 (dt, J=9.6, 7.1 Hz, 1H), 1.95 (dt, J=14.3, 7.1 Hz, 1H), 1.90-1.81 (m, 1H), 1.74-1.58 (m, 2H), 0.86-0.77 (m, 2H), 0.54-0.43 (m, 2H). ESI-MS m/z calc. 237.09766, found 238.1 (M+1)$^+$; Retention time: 0.9 min (LC Method B).

Step 2: (14S)-12,12-Dimethyl-8-(2-oxo-3-{2-[1-(trifluoromethyl)cyclopropyl]ethoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 158)

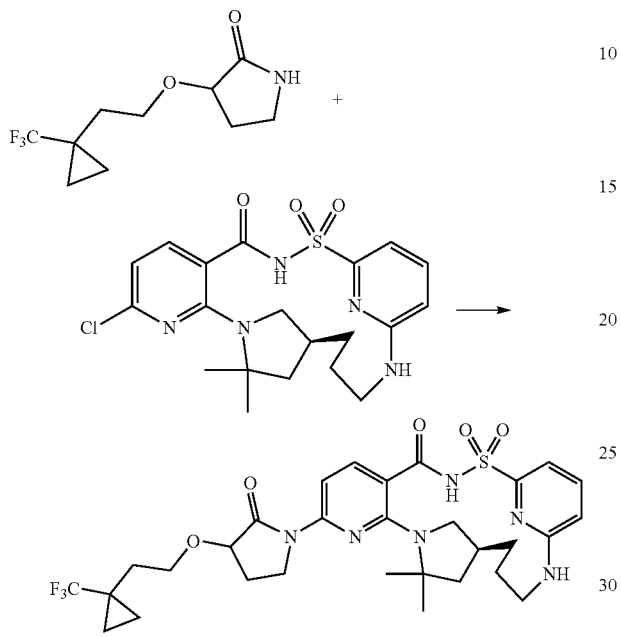

To a 5 mL vial, (14S)-8-chloro-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (100 mg, 0.2222 mmol), 3-[2-[1-(trifluoromethyl)cyclopropyl]ethoxy]pyrrolidin-2-one (63 mg, 0.2656 mmol), cesium carbonate (275 mg, 0.8440 mmol), 4,5-bis(diphenylphosphino)-9,9-dimethylxanthene (20 mg, 0.03457 mmol) (Xantphos) and dry dioxane (2 mL) were added, in that order. Nitrogen was bubbled through the heterogeneous mixture for 3 min. Then Pd₂(dba)₃ (20 mg, 0.02184 mmol) was added under nitrogen and nitrogen was bubbled for another 2 min and capped under nitrogen. The mixture was stirred at 115° C. for 15 h. The mixture was allowed to cool to ambient temperature and neutralized with glacial acetic acid (150 μL, 2.638 mmol). The volatiles were removed under reduced pressure and the residue was taken up in dimethyl sulfoxide (3.0 mL) and filtered through a Whatman 0.45 μm PTFE syringe filter disc. The sample was purified using preparative reverse-phase HPLC-MS (30%-99% acetonitrile in water over 15 min (hydrochloric acid as modifier)). The desired product fractions were combined and concentrated under reduced pressure and the residue was taken up in ethyl acetate (25 mL) and washed successively with saturated aqueous sodium bicarbonate (2×10 mL) and brine (10 mL). The organic layer was dried over anhydrous sodium sulfate, filtered and concentrated under reduced pressure to furnish (14S)-12,12-dimethyl-8-(2-oxo-3-{2-[1-(trifluoromethyl)cyclopropyl]ethoxy}pyrrolidin-1-yl)-2λ⁶-thia-3,9,11,18,23-pentaazatetracyclo[17.3.1.1¹¹,14.0⁵,10]tetracosa-1(22),5,7,9,19(23),20-hexaene-2,2,4-trione (Compound 158) (31 mg, 19%) as an off-white solid. ¹H NMR (400 MHz, Methanol-d₄) δ 7.78 (dd, J=8.4, 2.0 Hz, 1H), 7.59 (dd, J=8.4, 4.4 Hz, 1H), 7.53 (dd, J=8.5, 7.1 Hz, 1H), 7.16 (d, J=7.3 Hz, 1H), 6.65 (d, J=8.5 Hz, 1H), 4.26 (dt, J=12.5, 8.0 Hz, 1H), 4.22-4.00 (m, 2H), 3.97 (dt, J=9.1, 6.8 Hz, 1H), 3.92-3.71 (m, 2H), 3.29-3.21 (m, 1H), 3.03 (d, J=13.9 Hz, 1H), 2.86 (t, J=10.2 Hz, 1H), 2.49 (dqd, J=12.8, 7.7, 3.0 Hz, 1H), 2.24-2.07 (m, 1H), 2.04-1.90 (m, 3H), 1.84 (dd, J=11.5, 5.4 Hz, 2H), 1.71-1.63 (m, 2H), 1.62 (s, 3H), 1.60 (d, J=12.0 Hz, 1H), 1.54 (s, 3H), 1.47-1.36 (m, 1H), 0.96-0.91 (m, 2H), 0.84-0.77 (m, 2H). ESI-MS m/z calc. 650.2498, found 651.4 (M+1)⁺; Retention time: 2.04 min (LC Method B).

Example 161: Preparation of 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,14.0²,⁷]docosa-2(7),3,5,11(22),12-pentaene-8,10,10-trione (Compound 164), 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,14.0²,⁷]docosa-2(7),3,5,11(22),12-pentaene-8,10,10-trione (Enantiomer 1) (Compound 302) and 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,14.0²,⁷]docosa-2(7),3,5,11(22),12-pentaene-8,10,10-trione (Enantiomer 2) (Compound 167)

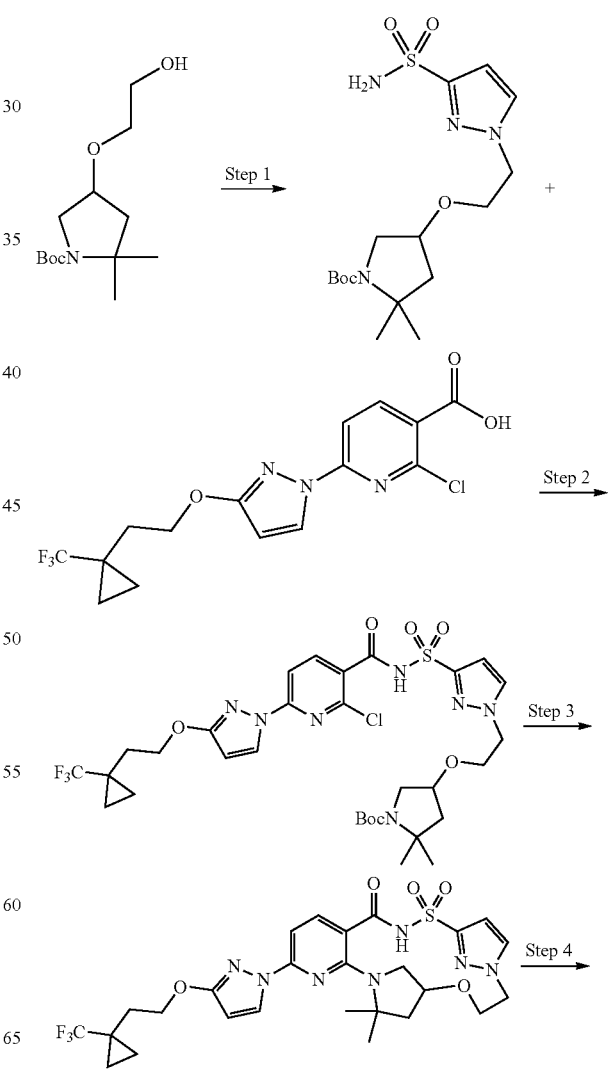

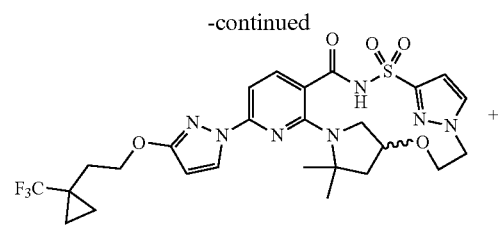

enantiomer 1

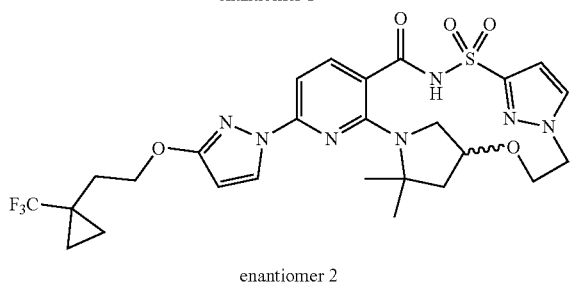

enantiomer 2

Step 1: tert-Butyl 2,2-dimethyl-4-[2-(3-sulfamoylpyrazol-1-yl)ethoxy]pyrrolidine-1-carboxylate

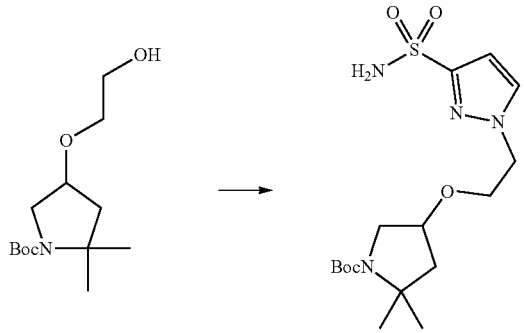 [SMILES: CC(C)(C)OC(=O)N1CC(OCCO)CC1(C)C ; CC(C)(C)OC(=O)N1CC(OCCn2ccc(S(N)(=O)=O)n2)CC1(C)C]

To a nitrogen sparged round bottom flask containing tert-butyl 4-(2-hydroxyethoxy)-2,2-dimethyl-pyrrolidine-1-carboxylate (1.94 g, 7.480 mmol) was added dichloromethane (70 mL). The solution was cooled to 0° C. prior to addition of Et₃N (6 mL, 43.05 mmol) and methanesulfonyl chloride (1.7 mL, 21.96 mmol). The reaction mixture was stirred for 20 h allowing to warm to room temperature after 1 h (the clear solution turned cloudy orange after 10 min). The reaction mixture was quenched by addition of water. Dichloromethane was added followed by brine and the organic layer was separated. The aqueous layer was extracted with further dichloromethane (2×20 mL) and the combined organics were dried over sodium sulfate, filtered and concentrated under reduced pressure. The resulting material was dried under vacuum for 1 h to give a yellow oil which was combined with 1H-pyrazole-3-sulfonamide (1.1 g, 7.475 mmol) in a round bottom flask followed by addition of potassium carbonate (2.23 g, 16.14 mmol) and the mixture was dissolved in N,N-dimethylformamide (13 mL). The reaction mixture was stirred at 50° C. in a 150 mL sealed vessel for 48 h. Cooled the mixture to room temperature, poured into water (100 mL) and extracted with ethyl acetate (2×100 mL), combined organic layers, washed with water (2×100 mL), dried (sodium sulfate), filtered and concentrated. The orange residue was purified by silica gel chromatography using a gradient from 100% hexanes to 100% ethyl acetate to afford as the second eluting, more polar regioisomer, tert-butyl 2,2-dimethyl-4-[2-(3-sulfamoylpyrazol-1-yl)ethoxy]pyrrolidine-1-carboxylate (475 mg, 33%). ESI-MS m/z calc. 388.17804, found 389.1 (M+1)⁺; Retention time: 0.52 min (LC Method A).

Step 2: tert-Butyl 4-[2-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]ethoxy]-2,2-dimethyl-pyrrolidine-1-carboxylate

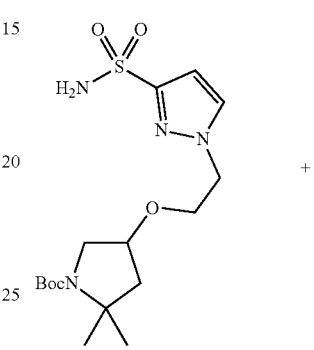

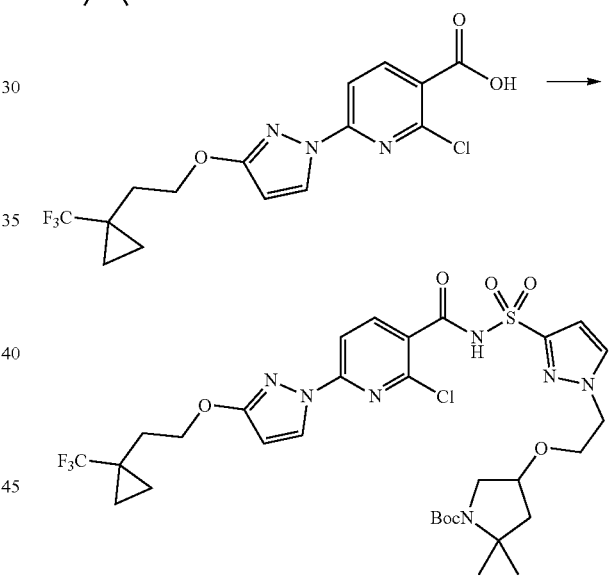

2-Chloro-6-[3-[2-[1-(trifluoromethyl)cyclopropyl] ethoxy]pyrazol-1-yl]pyridine-3-carboxylic acid (691.7 mg, 1.841 mmol) and carbonyl diimidazole (310.0 mg, 1.912 mmol) were combined in anhydrous tetrahydrofuran (15 mL) and stirred for 60 min at 40° C. Then a tetrahydrofuran solution (7 mL) of tert-butyl 2,2-dimethyl-4-[2-(3-sulfamoylpyrazol-1-yl)ethoxy]pyrrolidine-1-carboxylate (550 mg, 1.416 mmol) and 1,8-diazabicyclo[5.4.0]undec-7-ene (538.9 mg, 529.4 µL, 3.540 mmol) was added. The reaction was heated at 40° C. for 14 h. The reaction was diluted with ethyl acetate and washed with a 1 M citric acid solution, followed by brine. The organics were separated, dried over sodium sulfate, filtered and evaporated and then purified by silica gel chromatography using a gradient of 100% hexanes to 75% ethyl acetate in hexanes to afford as an off-white solid, tert-butyl 4-[2-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]ethoxy]-2,2-dimethyl-pyrrolidine-1-carboxylate (493 mg, 47%). ESI-MS m/z calc. 745.22723, found 746.29 (M+1)⁺; Retention time: 0.83 min (LC Method A).

Step 3: 20,20-Dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Compound 164)

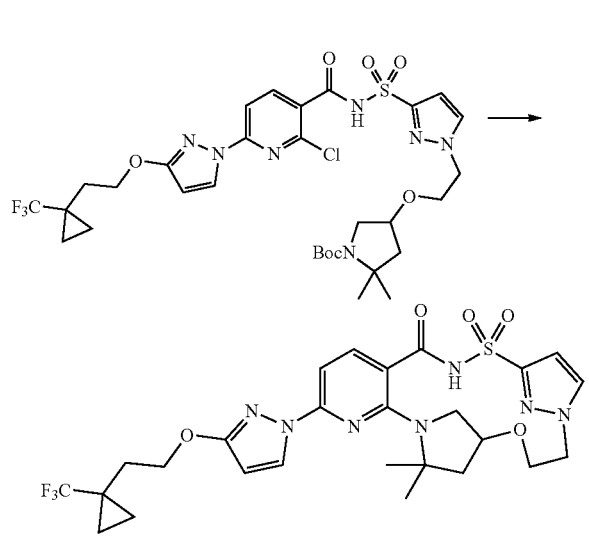

tert-Butyl 4-[2-[3-[[2-chloro-6-[3-[2-[1-(trifluoromethyl)cyclopropyl]ethoxy]pyrazol-1-yl]pyridine-3-carbonyl]sulfamoyl]pyrazol-1-yl]ethoxy]-2,2-dimethyl-pyrrolidine-1-carboxylate (467 mg, 0.6258 mmol) was dissolved in dichloromethane (10 mL) and to the mixture was added hydrochloric acid (4.5 mL of 4 M in dioxane, 18.00 mmol) and the mixture was stirred at room temperature for 30 min. Concentrated the mixture to dryness under reduced pressure and combined with potassium carbonate (520 mg, 3.763 mmol), cesium fluoride (154 mg, 1.014 mmol), 3 Å molecular sieves and dimethyl sulfoxide (10 mL) in a vial, purged with nitrogen, capped, heated to 140° C. and stirred for 16 h. The reaction mixture was allowed to cool to room temperature, filtered and then purified by reverse-phase preparative chromatography utilizing a C₁₈ column (30%-99% acetonitrile-water+5 mM hydrochloric acid) to afford as a white solid, 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Compound 164) (115 mg, 30%). ¹H NMR (400 MHz, dimethyl sulfoxide-d₆) δ 12.74 (s, 1H), 8.17 (d, J=2.8 Hz, 1H), 7.96 (s, 1H), 7.69 (d, J=8.2 Hz, 1H), 6.89 (d, J=8.2 Hz, 2H), 6.08 (d, J=2.8 Hz, 1H), 4.42 (t, J=13.0 Hz, 1H), 4.38-4.07 (m, 5H), 3.88 (t, J=11.4 Hz, 1H), 2.88 (s, 1H), 2.18-2.03 (m, 2H), 2.01 (dd, J=11.5, 6.0 Hz, 1H), 1.78 (t, J=9.1 Hz, 1H), 1.61 (t, J=11.5 Hz, 1H), 1.54 (s, 3H), 1.50 (s, 3H), 1.01-0.92 (m, 2H), 0.92-0.84 (m, 2H). ESI-MS m/z calc. 609.1981, found 610.36 (M+1)⁺; Retention time: 2.03 min (LC Method B).

Step 4: 20,20-Dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Enantiomer 1) (Compound 302) and 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Enantiomer 2) (Compound 167)

enantiomer 1

+ enantiomer 2

The racemic compound, 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Compound 164) (98 mg, 0.1591 mmol) was subjected to chiral preparatory SFC for separation of the enantiomers. The following SFC protocol was employed: ChiralPak AS-3 (150×2.1 mm), 3 μm; 35° C., mobile phase: 30% acetonitrile:methanol (90:10), 70% carbon dioxide. The first enantiomer to elute was 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,¹⁴.0²,⁷]docosa-2(7),3,5,11(22),12-pentaene-8,10,10-trione (enantiomer 1) (Compound 302) (31 mg, 63%); ESI-MS m/z calc. 609.1981, found 610.32 (M+1)⁺; Retention time: 2.01 min (LC Method B). The second enantiomer to elute was 20,20-dimethyl-4-(3-{2-[1-(trifluoromethyl)cyclopropyl]ethoxy}-1H-pyrazol-1-yl)-17-oxa-10λ⁶-thia-1,3,9,14,22-pentaazatetracyclo[16.2.1.1¹¹,¹⁴.0²,⁷]docosa-2(7),3,5,11(22),12-pentaene-8,10,10-trione (enantiomer 2) (Compound 167) (31 mg, 63%); ESI-MS m/z calc. 609.1981, found 610.28 (M+1)⁺; Retention time: 2.0 min (LC Method B).

Example 162: Preparation of 4-chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 1) and 4-chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 2)

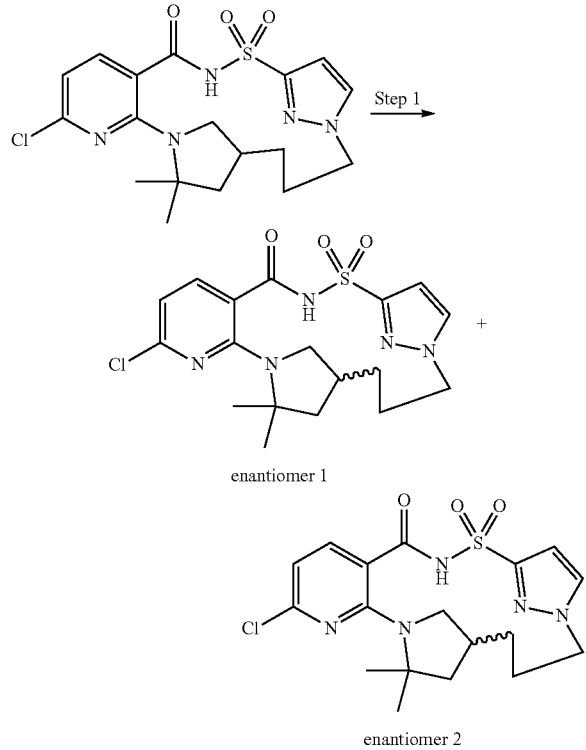

Step 1: 4-Chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 1) (Compound E) and 4-chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Enantiomer 2) (Compound F)

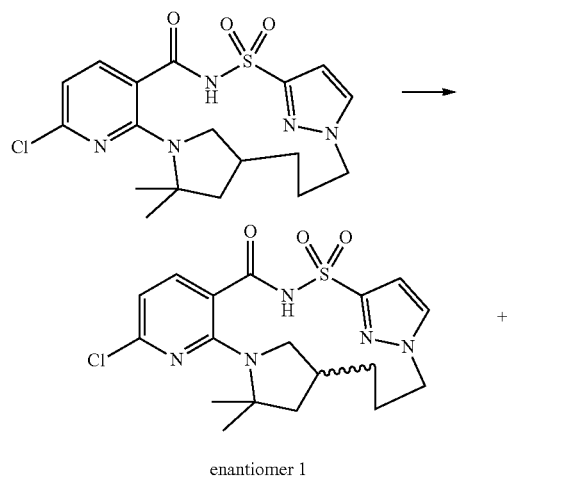

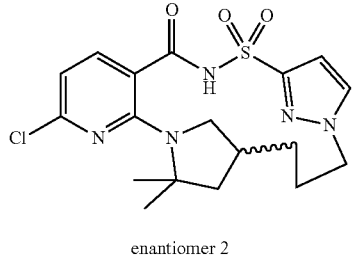

enantiomer 2

Racemic 4-chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (498 mg) was subjected to chiral SFC chromatography. The following SFC protocol was employed: ChiralPak AS-H (250×21.2 mm), 5 μm; 35° C., mobile phase: 18% acetonitrile:methanol (90:10), 82% carbon dioxide with a flow rate of 70 mL/min. The first enantiomer to elute was 4-chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (enantiomer 1) (162 mg, 13%). $^1$H NMR (400 MHz, Chloroform-d) δ 8.73 (s, 1H), 7.57-7.45 (m, 2H), 7.06 (d, J=2.3 Hz, 1H), 6.49 (d, J=7.8 Hz, 1H), 4.28 (dt, J=13.4, 3.3 Hz, 1H), 4.02-3.85 (m, 1H), 2.67 (s, 1H), 2.13 (dt, J=11.4, 5.3 Hz, 2H), 2.08-1.98 (m, 1H), 1.92 (dt, J=15.4, 10.2 Hz, 2H), 1.77-1.70 (m, 1H), 1.54 (s, 3H), 1.49 (s, 3H), 1.44 (t, J=12.3 Hz, 1H), 0.83-0.71 (m, 1H). ESI-MS m/z calc. 423.1132, found 424.04 (M+1)⁺; Retention time: 1.66 min (LC Method B). The second enantiomer to elute was 4-chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (enantiomer 2) (163 mg, 13%). $^1$H NMR (400 MHz, Chloroform-d) δ 8.82 (s, 1H), 7.57-7.45 (m, 2H), 7.06 (d, J=2.3 Hz, 1H), 6.49 (d, J=7.8 Hz, 1H), 4.27 (dt, J=13.3, 3.4 Hz, 1H), 4.01-3.87 (m, 1H), 2.67 (s, 1H), 2.24-2.07 (m, 2H), 2.08-1.98 (m, 1H), 2.00-1.84 (m, 2H), 1.82-1.68 (m, 1H), 1.54 (s, 3H), 1.49 (s, 3H), 1.44 (t, J=12.3 Hz, 1H), 0.77 (dt, J=18.8, 9.0 Hz, 1H). ESI-MS m/z calc. 423.1132, found 424.04 (M+1)⁺; Retention time: 1.67 min (LC Method B).

Example 163: Preparation of 4-[3-(3,3-dimethylbutyl)-2-oxoimidazolidin-1-yl]-20,20-dimethyl-10λ⁶-thia-1,3,9,14,22-pentaazatetracyclo[16.2.1.1¹¹,14.0²,⁷]docosa-2,4,6,11(22),12-pentaene-8,10,10-trione (Compound 168)

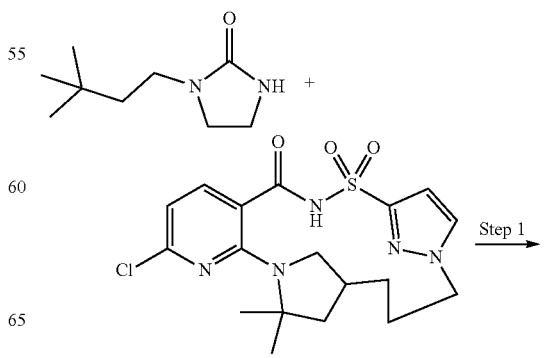

1017

-continued

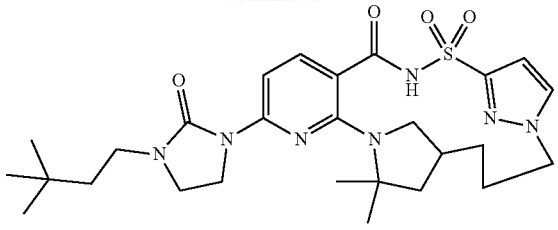

Step 1: 4-[3-(3,3-Dimethylbutyl)-2-oxoimidazolidin-1-yl]-20,20-dimethyl-10λ⁶-thia-1,3,9,14,22-pentaazatetracyclo[16.2.1.111,14.02,7]docosa-2,4,6,11(22),12-pentaene-8,10,10-trione (Compound 168)

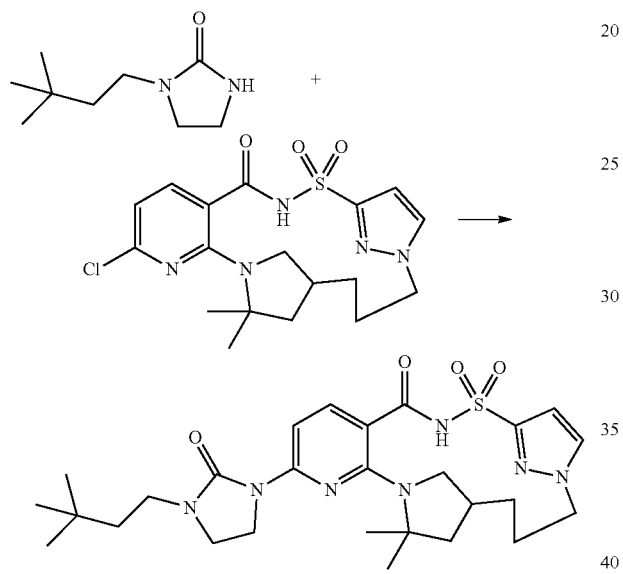

A solution of 4-chloro-20,20-dimethyl-10λ⁶-thia-1,3,9,14,22-pentaazatetracyclo[16.2.1.111,14.02,7]docosa-2,4,6,11(22),12-pentaene-8,10,10-trione (75 mg, 0.1769 mmol), 1-(3,3-dimethylbutyl)imidazolidin-2-one (38 mg, 0.2232 mmol), sodium tert-butoxide (27 mg, 0.2809 mmol) and chloro(2-di-tert-butylphosphino-2',4',6'-tri-i-propyl-1,1'-biphenyl)[2-(2-aminoethyl)phenyl]palladium(II) (31 mg, 0.04760 mmol) in dioxane (2 mL) in a vial was degassed by purging with nitrogen for 2 min. The mixture was then stirred at room temperature for 1 h. Quenched the reaction mixture with 0.5 mL of acetic acid and filtered through a Whatman filter disc (puradisc 25 TF) using small amount of dimethyl sulfoxide and the filtrate was purified by a reverse phase HPLC-MS method using a dual gradient run from 50%-99% mobile phase B over 15.0 min (mobile phase A=water (5 mM hydrochloric acid), mobile phase B=acetonitrile, flow rate=50 mL/min, injection volume=950 μL and column temperature=25° C.) to afford 4-[3-(3,3-dimethylbutyl)-2-oxoimidazolidin-1-yl]-20,20-dimethyl-10λ⁶-thia-1,3,9,14,22-pentaazatetracyclo[16.2.1.111,14.02,7]docosa-2,4,6,11(22),12-pentaene-8,10,10-trione (Compound 168) (24 mg, 24%) as a white solid. ¹H NMR (400 MHz, Chloroform-d) δ 8.38 (s, 1H), 7.55 (s, 2H), 7.46 (d, J=2.3 Hz, 1H), 7.05 (d, J=2.3 Hz, 1H), 4.35 (d, J=11.7 Hz, 1H), 3.96 (dt, J=36.5, 11.0 Hz, 3H), 3.46 (d, J=8.4 Hz, 2H), 3.39-3.27 (m, 2H), 2.71 (s, 1H), 2.12 (s, 2H), 2.02 (s, 2H), 1.92 (s, 1H), 1.72 (d, J=8.8 Hz, 1H), 1.55 (s, 3H), 1.49

1018

(s, 3H), 1.45 (dd, J=10.1, 6.6 Hz, 3H), 0.96 (s, 9H), 0.79 (d, J=9.7 Hz, 1H). ESI-MS m/z calc. 557.27844, found 558.17 (M+1)⁺; Retention time: 1.84 min (LC Method B).

Example 164: Preparation of 4-[3-(4,4-dimethylpentyl)-2-oxoimidazolidin-1-yl]-20,20-dimethyl-10λ⁶-thia-1,3,9,14,22-pentaazatetracyclo[16.2.1.111,14.02,7]docosa-2,4,6,11(22),12-pentaene-8,10,10-trione (Compound 169)

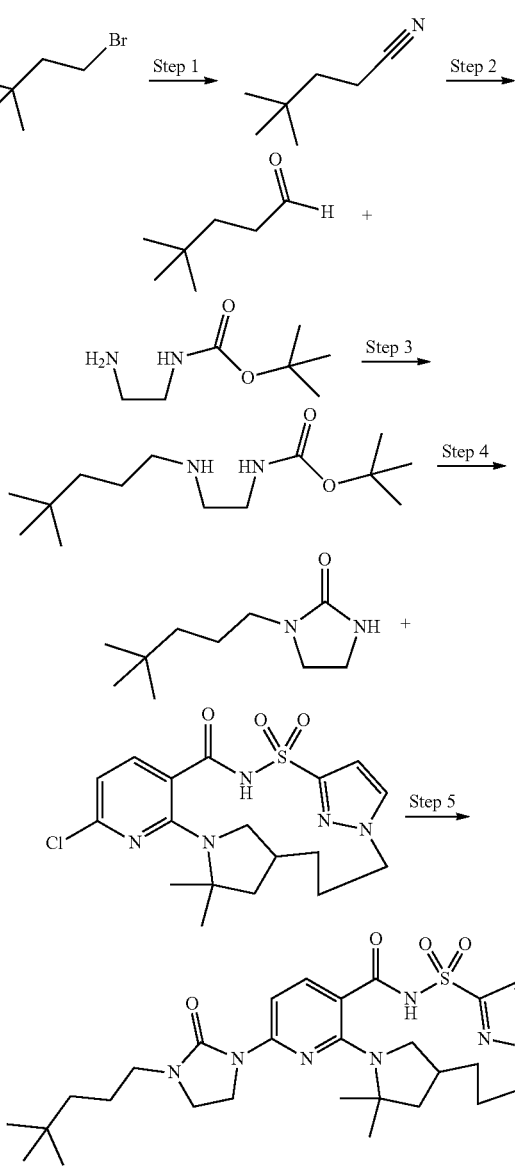

Step 1: 4,4-Dimethylpentanenitrile

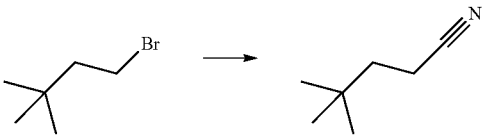

1-Bromo-3,3-dimethyl-butane (25 g, 151.45 mmol) was slowly added to a suspension of sodium cyanide (8.17 g, 166.71 mmol) in dimethyl sulfoxide (80 mL) at 60° C. keeping the internal temperature between 55° C. and 65° C. The reaction mixture was heated at 70° C. for 90 min then cooled to room temperature. The reaction mixture was diluted with water (300 mL) and extracted using diethyl ether (3×150 mL). The organic layers were combined, washed with 5 N hydrochloric acid (75 mL) and water (75 mL), dried over magnesium sulfate, filtered and concentrated under reduced pressure to afford 4,4-dimethylpentanenitrile (17.82 g, 89%) as a clear oil. The crude material was used directly for next step without further purification. $^1$H NMR (300 MHz, CDCl$_3$) ppm 0.93 (s, 9H), 1.56-1.67 (m, 2H), 2.28 (dd, J=8.8, 7.3 Hz, 2H).

Step 2: 4,4-Dimethylpentanal

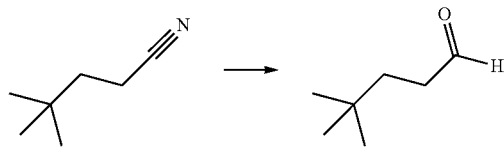

Diisobutylaluminum hydride (226 mL of 1 M in dichloromethane, 226.00 mmol) was added to a solution of 4,4-dimethylpentanenitrile (16.75 g, 150.65 mmol) in dichloromethane (560 mL) at 0° C. The reaction mixture was stirred at 0° C. for 90 min then quenched with 3 M hydrochloric acid. The aqueous layer was separated and extracted with dichloromethane. The combined organic layers were washed with 10% hydrochloric acid, water and brine, dried over magnesium sulfate, filtered and concentrated under reduced pressure to afford 4,4-dimethylpentanal (16.23 g, 94%) as a yellow oil. The crude material was used for next step without any further purification. $^1$H NMR (300 MHz, CDCl$_3$) ppm 0.90 (s, 9H), 1.46-1.61 (m, 2H), 2.40 (td, J=8.1, 1.9 Hz, 2H), 9.78 (t, J=1.9 Hz, 1H).

Step 3: tert-Butyl N-[2-(4,4-dimethylpentylamino)ethyl]carbamate

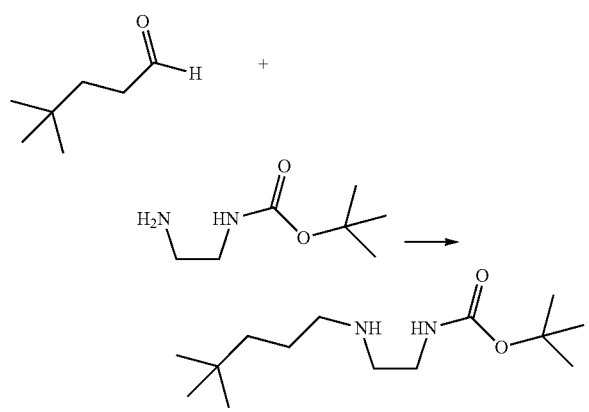

4,4-Dimethylpentanal (15.2 g, 133.12 mmol) was added to a solution of tert-butyl N-(2-aminoethyl)carbamate (20.948 g, 20.7 mL, 130.75 mmol) in methanol (300 mL) and the reaction mixture was stirred at room temperature for 1 h. Once reaction mixture was cooled to 0° C., sodium borohydride (5.2 g, 137.45 mmol) was slowly added and the mixture was stirred at room temperature overnight. The reaction was concentrated under reduced pressure. The residue was dissolved in ethyl acetate (300 mL) and washed with saturated aqueous sodium bicarbonate solution (2×300 mL) and brine (300 mL), dried over sodium sulfate, filtered and concentrated under reduced pressure to afford tert-butyl N-[2-(4,4-dimethylpentylamino)ethyl]carbamate (21.83 g, 65%) as a yellow oil. The crude material was used for next step without any further purification. ESI-MS m/z calc. 258.2307, found 259.3 (M+1)$^+$; Retention time: 1.39 min (LC Method I).

Step 4: 1-(4,4-Dimethylpentyl)imidazolidin-2-one

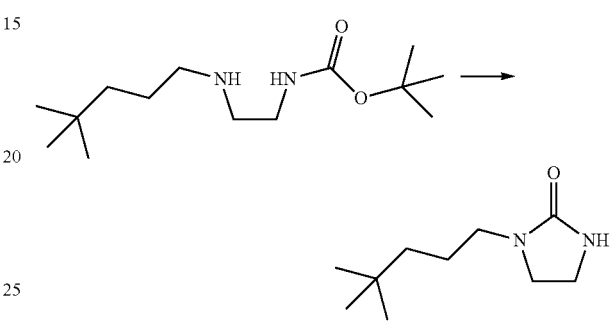

Solid potassium tert-butoxide (28.6 g, 254.87 mmol) was added to a solution of tert-butyl N-[2-(4,4-dimethylpentylamino)ethyl]carbamate (21.83 g, 84.481 mmol) in tetrahydrofuran (260 mL) and the reaction mixture was heated at 60° C. for 3 h. Once cooled to room temperature, the reaction mixture was acidified to pH=1-2 with aqueous hydrochloric acid (1 M) and concentrated under reduced pressure. The aqueous residue was extracted with ethyl acetate (3×250 mL), organic layers were combined, washed with brine (2×200 mL), dried over sodium sulfate, filtered and concentrated under reduced pressure. The residue was purified by silica gel chromatography using a gradient from 0% to 10% of methanol in ethyl acetate to afford 1-(4,4-dimethylpentyl)imidazolidin-2-one (7.36 g, 45%) as an off-white solid. $^1$H NMR (300 MHz, dimethyl sulfoxide-d$_6$) ppm 0.84 (s, 9H), 1.02-1.15 (m, 2H), 1.28-1.43 (m, 2H), 2.96 (t, J=7.2 Hz, 2H), 3.14-3.22 (m, 2H), 3.23-3.31 (m, 2H), 6.20 (br. s., 1H). ESI-MS m/z calc. 184.1576, found 185.3 (M+1)$^+$; Retention time: 2.34 min (LC Method H).

Step 5: 4-[3-(4,4-Dimethylpentyl)-2-oxoimidazolidin-1-yl]-20,20-dimethyl-10$\lambda^6$-thia-1,3,9,14,22-pentaazatetracyclo[16.2.1.111,14.02,7]docosa-2,4,6,11(22),12-pentaene-8,10,10-trione (Compound 169)

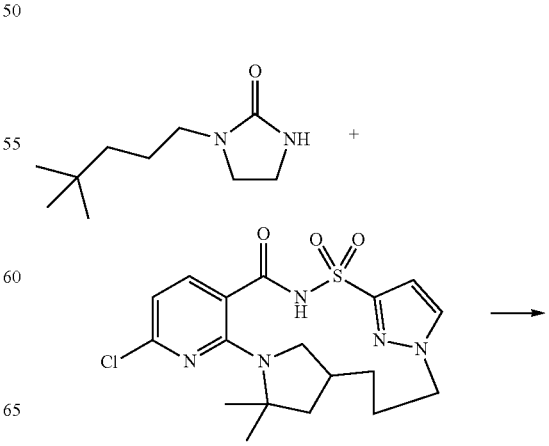

1021

-continued

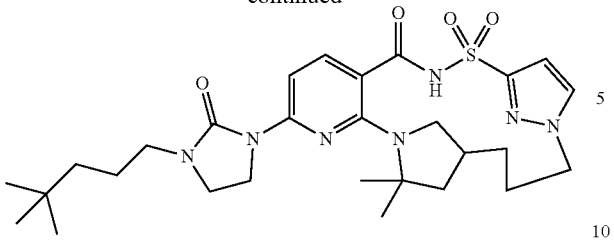

A solution of 4-chloro-20,20-dimethyl-10λ⁶-thia-1,3,9,14,22-pentaazatetracyclo[16.2.1.111,14.02,7]docosa-2,4,6,11(22),12-pentaene-8,10,10-trione (30 mg, 0.07077 mmol), 1-(4,4-dimethylpentyl)imidazolidin-2-one (16 mg, 0.08683 mmol), sodium tert-butoxide (12 mg, 0.1249 mmol) and chloro(2-di-tert-butylphosphino-2',4',6'-tri-i-propyl-1,1'-biphenyl)[2-(2-aminoethyl)phenyl]palladium(II) (14 mg, 0.02150 mmol) in dioxane (2 mL) in a vial was degassed by purging with nitrogen for 2 min. The mixture was stirred at room temperature for about 1 h. Quenched the reaction mixture with 0.5 mL of acetic acid and filtered through a Whatman filter disc (puradisc 25 TF) using small amount of dimethyl sulfoxide and filtrate was purified by a reverse phase HPLC-MS method using a dual gradient run from 50%-99% mobile phase B over 15.0 min (mobile phase A=water (5 mM hydrochloric acid), mobile phase B=acetonitrile, Flow rate=50 mL/min, injection volume=950 μL and column temperature=25° C.) to afford 4-[3-(4,4-dimethylpentyl)-2-oxoimidazolidin-1-yl]-20,20-dimethyl-10λ⁶-thia-1,3,9,14,22-pentaazatetracyclo[16.2.1.111,14.02,7]docosa-2,4,6,11(22),12-pentaene-8,10,10-trione (Compound 169) (6.8 mg, 16%) as an off-white solid. ¹H NMR (400 MHz, Chloroform-d) δ 8.54 (s, 1H), 7.54 (s, 2H), 7.46 (d, J=2.2 Hz, 1H), 7.05 (d, J=2.1 Hz, 1H), 4.35 (d, J=13.2 Hz, 1H), 4.09-3.85 (m, 3H), 3.46 (d, J=8.7 Hz, 2H), 3.27 (t, J=7.3 Hz, 2H), 2.71 (s, 1H), 2.11 (s, 3H), 1.99-1.85 (m, 1H), 1.71 (dd, J=11.7, 5.3 Hz, 1H), 1.60 (s, 3H), 1.55 (s, 3H), 1.49 (s, 3H), 1.48-1.35 (m, 1H), 1.30-1.17 (m, 2H), 0.88 (s, 8H), 0.75 (d, J=19.6 Hz, 2H). ESI-MS m/z calc. 571.29407, found 572.3 (M+1)⁺; Retention time: 2.02 min (LC Method B).

Example 165: Preparation of (14S)-8-[3-(3,3-dimethylbutoxy)-2-oxopyrrolidin-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Diastereomer 1) (Compound 170) and (14S)-8-[3-(3,3-dimethylbutoxy)-2-oxopyrrolidin-1-yl]-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Diastereomer 2) (Compound 171)

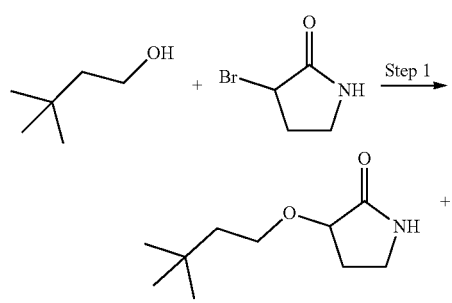

1022

-continued

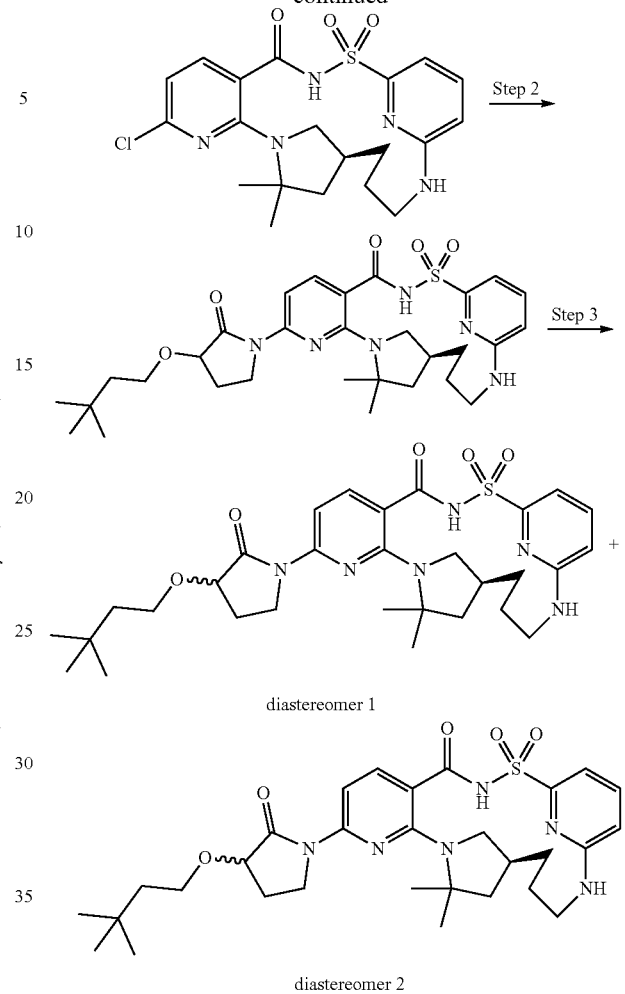

Step 1: 3-(3,3-Dimethylbutoxy)pyrrolidin-2-one

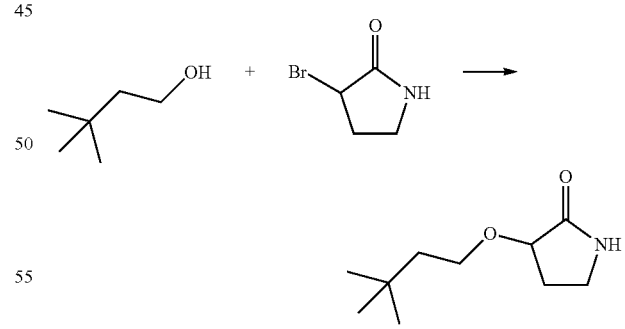

To a stirred solution of 3,3-dimethylbutan-1-ol (540 mg, 5.285 mmol) in anhydrous tetrahydrofuran (20 mL) was added [bis(trimethylsilyl)amino]potassium (10.6 mL of 0.5 M in toluene, 5.300 mmol) at ambient temperature under nitrogen. The milky reaction was stirred for 30 min then a solution of 3-bromopyrrolidin-2-one (830 mg, 4.808 mmol) in anhydrous tetrahydrofuran (3 mL) was added dropwise at 0° C. (ice-water bath). The reaction was allowed to warm gradually to ambient temperature overnight (18 h). The reaction was acidified with 1 M aqueous hydrochloric acid (1.5 mL) and the volatiles were removed under reduced pressure. The residue was taken up in ethyl acetate (30 mL) and washed with brine (15 mL). The organic portion was dried (anhydrous sodium sulfate), filtered and concentrated under reduced pressure to obtain brownish crude material. The crude was purified from silica gel chromatography (0%-10% methanol in dichloromethane gradient) to furnish 3-(3,3-dimethylbutoxy)pyrrolidin-2-one (143 mg, 16%) as a white solid. ESI-MS m/z calc. 185.14159, found 186.2 (M+1)$^+$; Retention time: 0.95 min (LC Method B).

Step 2: (14S)-8-[3-(3,3-Dimethylbutoxy)-2-oxopyr-rolidin-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione

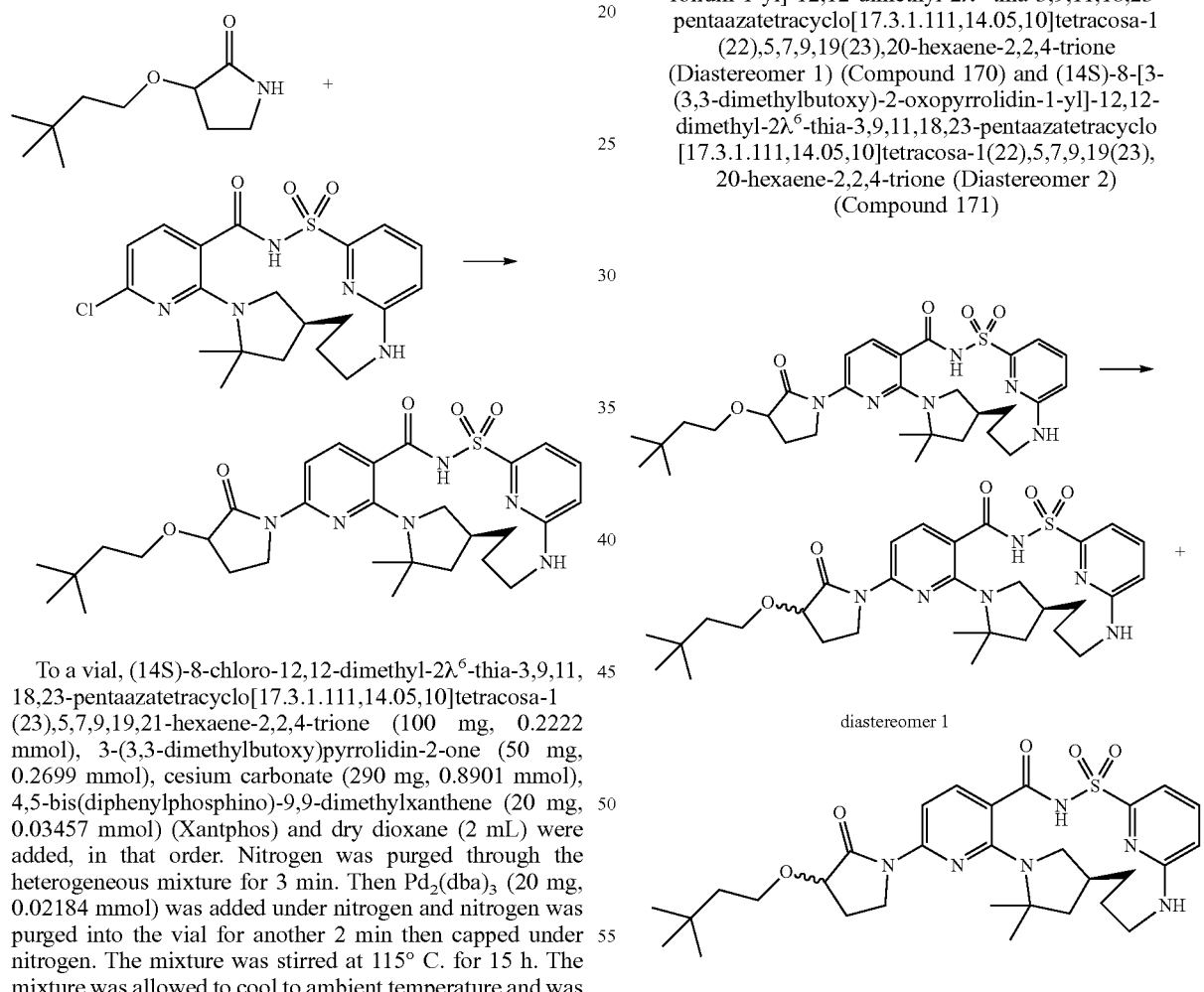

To a vial, (14S)-8-chloro-12,12-dimethyl-2$\lambda^6$-thia-3,9,11,18,23-pentaazatetracyclo[17.3.1.111,14.05,10]tetracosa-1(23),5,7,9,19,21-hexaene-2,2,4-trione (100 mg, 0.2222 mmol), 3-(3,3-dimethylbutoxy)pyrrolidin-2-one (50 mg, 0.2699 mmol), cesium carbonate (290 mg, 0.8901 mmol), 4,5-bis(diphenylphosphino)-9,9-dimethylxanthene (20 mg, 0.03457 mmol) (Xantphos) and dry dioxane (2 mL) were added, in that order. Nitrogen was purged through the heterogeneous mixture for 3 min. Then Pd$_2$(dba)$_3$ (20 mg, 0.02184 mmol) was added under nitrogen and nitrogen was purged into the vial for another 2 min then capped under nitrogen. The mixture was stirred at 115° C. for 15 h. The mixture was allowed to cool to ambient temperature and was neutralized with glacial acetic acid (130 µL, 2.286 mmol). The volatiles were removed under reduced pressure and the residue was taken up in dimethyl sulfoxide (3.0 mL) and filtered through a Whatman 0.45 µm PTFE syringe filter disc. The sample was purified using preparative reverse-phase HPLC-MS (30%-99% acetonitrile in water gradient over 15 min (hydrochloric acid as modifier). The desired product fractions were combined and concentrated under reduced pressure and the residue was taken up in ethyl acetate (25 mL) and washed with brine (10 mL). The organic layer was dried over anhydrous sodium sulfate, filtered and concentrated under reduced pressure to furnish (14S)-8-[3-(3,3-dimethylbutoxy)-2-oxopyrrolidin-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (27 mg, 20%) as an off-white solid mixture of diastereomers. NMR (400 MHz, Methanol-d$_4$) δ 7.78 (dd, J=8.4, 2.1 Hz, 1H), 7.60 (dd, J=8.4, 4.3 Hz, 1H), 7.53 (dd, J=8.5, 7.2 Hz, 1H), 7.16 (dt, J=7.2, 1.0 Hz, 1H), 6.65 (d, J=8.5 Hz, 1H), 4.25 (dt, J=12.8, 8.0 Hz, 1H), 4.20-3.99 (m, 2H), 3.97-3.76 (m, 2H), 3.74-3.65 (m, 1H), 3.03 (d, J=13.8 Hz, 1H), 2.86 (t, J=9.9 Hz, 1H), 2.56-2.44 (m, 1H), 2.17 (s, 1H), 2.04-1.93 (m, 1H), 1.84 (dd, J=11.7, 5.7 Hz, 2H), 1.63 (br, 6H), 1.61-1.55 (m, 4H), 1.54 (s, 2H), 1.44 (t, J=11.6 Hz, 1H), 0.95 (s, 9H). ESI-MS m/z calc. 598.29376, found 651.4 (M+1)$^+$; Retention time: 2.04 min (LC Method B).

Step 3: (14S)-8-[3-(3,3-Dimethylbutoxy)-2-oxopyr-rolidin-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (Diastereomer 1) (Compound 170) and (14S)-8-[3-(3,3-dimethylbutoxy)-2-oxopyrrolidin-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (Diastereomer 2) (Compound 171)

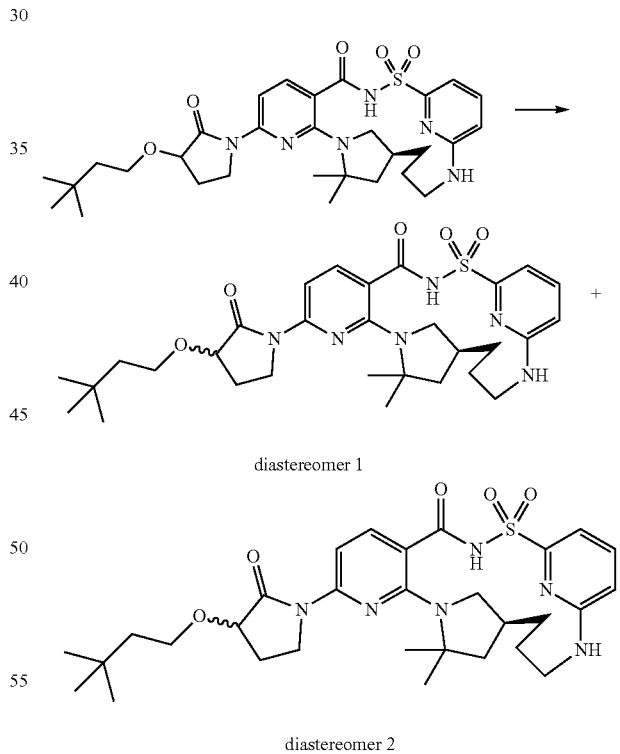

diastereomer 1 diastereomer 2

Racemic diasteromeric (14S)-8-[3-(3,3-dimethylbu-toxy)-2-oxopyrrolidin-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione was subjected to chiral SFC chromatography. The following SFC protocol was employed: ChiralCel OJ-H (250×10 mm), 5 µm; mobile phase: 20% acetonitrile:methanol (90:10; no modifier), 80% carbon dioxide with a flow rate of 10 mL/min to provide as the first diastereomer to elute, (14S)-8-[3-(3,3-dimethylbutoxy)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 1) (Compound 170) (11 mg, 8%); ¹H NMR (400 MHz, dimethyl sulfoxide-d₆) δ 12.43 (s, 1H), 7.70 (d, J=8.3 Hz, 1H), 7.57 (t, J=7.8 Hz, 1H), 7.51 (d, J=8.3 Hz, 1H), 7.04 (d, J=7.2 Hz, 1H), 6.96 (s, 1H), 6.70 (d, J=8.5 Hz, 1H), 4.23 (t, J=8.0 Hz, 1H), 4.07-3.98 (m, 1H), 3.88 (dt, J=8.8, 7.2 Hz, 2H), 3.70 (dt, J=10.5, 7.6 Hz, 1H), 3.60 (dt, J=9.2, 7.2 Hz, 1H), 3.20-3.03 (m, 1H), 2.94 (d, J=13.4 Hz, 1H), 2.77-2.63 (m, 1H), 2.46-2.37 (m, 1H), 2.18-2.04 (m, 1H), 1.91 (dq, J=12.6, 8.4 Hz, 1H), 1.82 (dd, J=11.8, 5.2 Hz, 1H), 1.80-1.68 (m, 1H), 1.64-1.57 (m, 2H), 1.57 (s, 3H), 1.52-1.48 (m, 2H), 1.46 (s, 3H), 1.34-1.26 (m, 1H), 1.24 (s, 1H), 0.91 (d, J=0.9 Hz, 9H), ESI-MS m/z calc. 598.29376, found 599.4 (M+1)⁺; Retention time: 2.21 min (LC Method B) and as the second diastereomer to elute, (14S)-8-[3-(3,3-dimethylbutoxy)-2-oxopyrrolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (diastereomer 2) (Compound 171) (10 mg, 7%); ¹H NMR (400 MHz, dimethyl sulfoxide-d₆) δ 12.41 (s, 1H), 7.70 (d, J=8.4 Hz, 1H), 7.57 (t, J=7.9 Hz, 1H), 7.53 (d, J=8.4 Hz, 1H), 7.04 (d, J=7.2 Hz, 1H), 6.96 (s, 1H), 6.70 (d, J=8.5 Hz, 1H), 4.28 (t, J=8.3 Hz, 1H), 3.97-3.92 (m, 1H), 3.92-3.89 (m, 1H), 3.89-3.84 (m, 1H), 3.77 (dt, J=10.2, 7.5 Hz, 1H), 3.59 (ddd, J=9.3, 7.7, 6.7 Hz, 1H), 3.16-3.03 (m, 1H), 2.94 (d, J=13.3 Hz, 1H), 2.74-2.64 (m, 1H), 2.48-2.39 (m, 1H), 2.20-2.02 (m, 1H), 1.93-1.85 (m, 1H), 1.84-1.79 (m, 1H), 1.79-1.69 (m, 1H), 1.63-1.57 (m, 2H), 1.57 (s, 3H), 1.52-1.47 (m, 2H), 1.46 (s, 3H), 1.29 (d, J=12.4 Hz, 1H), 1.24 (s, 1H), 0.91 (s, 9H). ESI-MS m/z calc. 598.29376, found 599.4 (M+1)⁺; Retention time: 2.18 min (LC Method B).

Example 166: Preparation of (14S)-12,12-dimethyl-8-(2-oxo-3-{2-[1-(trifluoromethyl)cyclopropyl]ethoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 172) and (14S)-12,12-dimethyl-8-(2-oxo-3-{2-[1-(trifluoromethyl)cyclopropyl]ethoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 173)

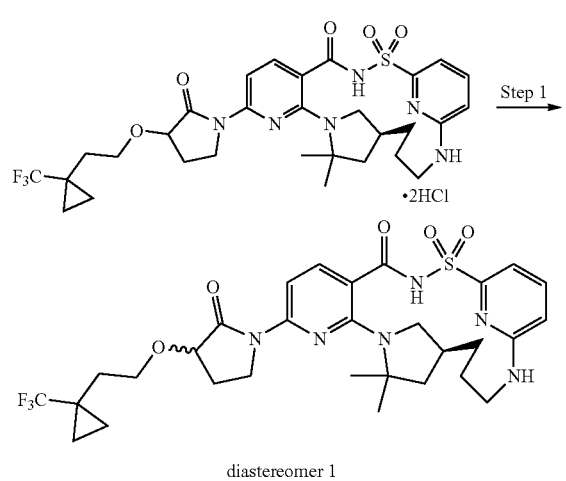

Step 1: (14S)-12,12-Dimethyl-8-(2-oxo-3-{2-[1-(trifluoromethyl)cyclopropyl]ethoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 1) (Compound 172) and (14S)-12,12-dimethyl-8-(2-oxo-3-{2-[1-(trifluoromethyl)cyclopropyl]ethoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Diastereomer 2) (Compound 173)

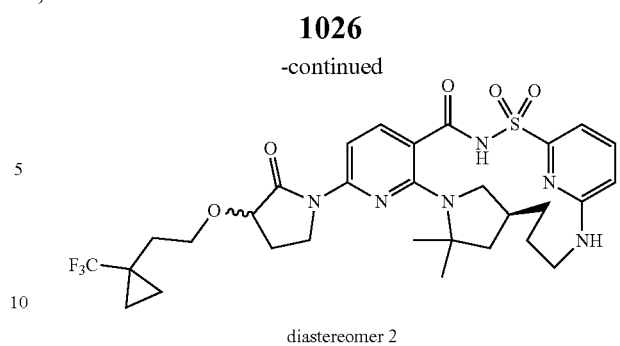

diastereomer 2

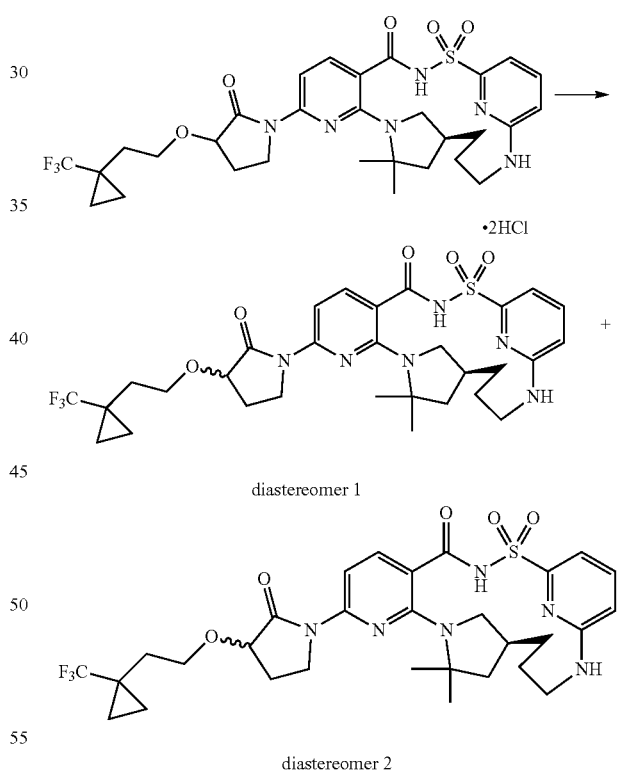

The diastereomeric mixture, (14S)-12,12-dimethyl-8-(2-oxo-3-{2-[1-(trifluoromethyl)cyclopropyl]ethoxy}pyrrolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (dihydrochloride salt) (31 mg) was subjected to chiral SFC purification. The SFC purification method employed used a ChiralCel OJ-H (250×10 mm), 5 μm column; mobile phase: 20% acetonitrile:methanol (90:10; No Modifier), 80% carbon dioxide; Flow: 10 mL/min; Concentration of sample: ~24 mg/mL in acetonitrile:methanol:dimethyl sulfoxide (85:9:6); injection volume: 70 μL; pressure: 100 bar. The first diastereomer to elute was (14S)-12,12-dimethyl-8-(2-oxo-3-{2-[1-(trifluoromethyl)cyclopropyl]ethoxy}pyrrolidin-1-yl)-2λ$^6$-thia-3,9,11,18,23-pentaazatetracyclo[17.3.1.111,14.05,10]tetracosa-1(22),5,7,9,19(23),20-hexaene-2,2,4-trione (diastereomer 1) (Compound 172) (7 mg, 5%). ESI-MS m/z calc. 650.2498, found 651.4 (M+1)$^+$; Retention time: 2.09 min (LC Method B). The second diastereomer to elute was (14S)-12,12-dimethyl-8-(2-oxo-3-{2-[1-(trifluoromethyl)cyclopropyl]ethoxy}pyrrolidin-1-yl)-2λ$^6$-thia-3,9,11,18,23-pentaazatetracyclo[17.3.1.111,14.05,10]tetracosa-1(22),5,7,9,19(23),20-hexaene-2,2,4-trione (diastereomer 2) (Compound 173) (7 mg, 5%). ESI-MS m/z calc. 650.2498, found 651.4 (M+1)$^+$; Retention time: 2.09 min (LC Method B).

Example 167: Preparation of 20,20-dimethyl-4-(2-oxo-3-{3-[1-(trifluoromethyl)cyclo propyl]propyl}pyrrolidin-1-yl)-10λ$^6$-thia-1,3,9,14,22-pentaazatetracyclo[16.2.1.111,14.02,7]docosa-2,4,6,11(22),12-pentaene-8,10,10-trione (Diastereomer 1) (Compound 181) and 20,20-dimethyl-4-(2-oxo-3-{3-[1-(trifluoromethyl)cyclopropyl]propyl}pyrrolidin-1-yl)-10λ$^6$-thia-1,3,9,14,22-pentaazatetracyclo[16.2.1.111,14.02,7]docosa-2,4,6,11(22),12-pentaene-8,10,10-trione (Diastereomer 2) (Compound 182)

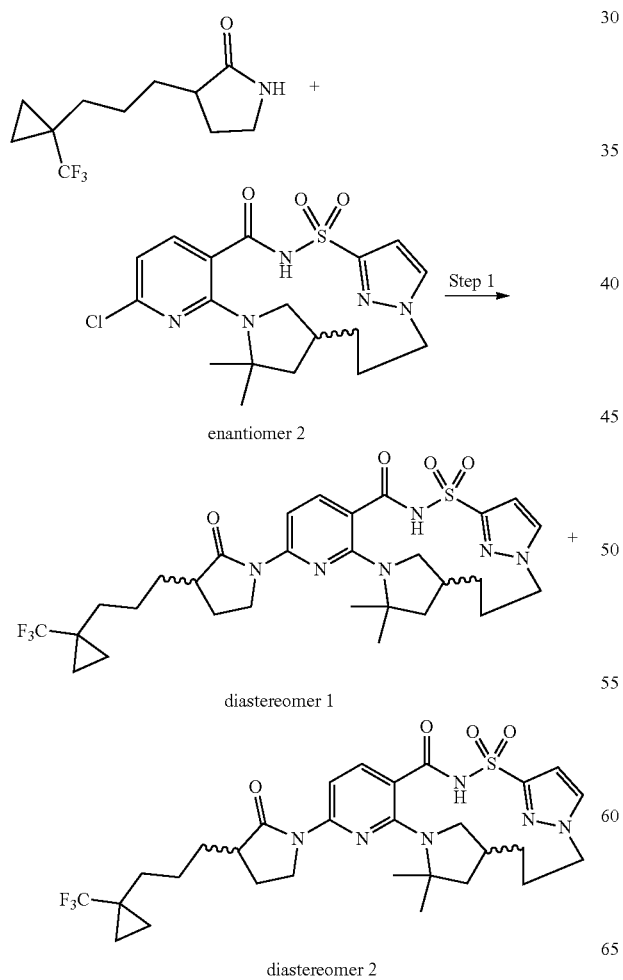

Step 1: 20,20-Dimethyl-4-(2-oxo-3-{3-[1-(trifluoromethyl)cyclopropyl]propyl}pyrrolidin-1-yl)-10λ$^6$-thia-1,3,9,14,22-pentaazatetracyclo[16.2.1.111,14.02,7]docosa-2,4,6,11(22),12-pentaene-8,10,10-trione (Diastereomer 1) (Compound 181) and 20,20-dimethyl-4-(2-oxo-3-{3-[1-(trifluoromethyl)cyclopropyl]propyl}pyrrolidin-1-yl)-10λ$^6$-thia-1,3,9,14,22-pentaazatetracyclo[16.2.1.111,14.02,7]docosa-2,4,6,11(22),12-pentaene-8,10,10-trione (Diastereomer 2) (Compound 182)

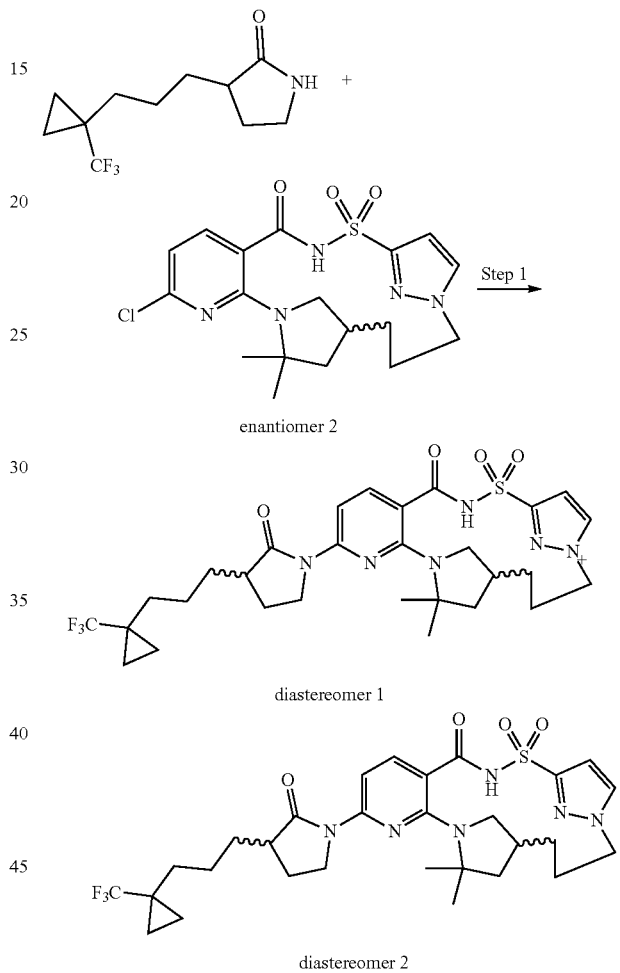

To a vial, 4-chloro-20,20-dimethyl-10λ$^6$-thia-1,3,9,14,22-pentaazatetracyclo[16.2.1.111,14.02,7]docosa-2,4,6,11(22),12-pentaene-8,10,10-trione (enantiomer 2) (40 mg, 0.09436 mmol), 3-[3-[1-(trifluoromethyl)cyclopropyl]propyl]pyrrolidin-2-one (27 mg, 0.1148 mmol), cesium carbonate (110 mg, 0.3376 mmol), 4,5-bis(diphenylphosphino)-9,9-dimethylxanthene (9 mg, 0.01555 mmol) (Xantphos) and dry dioxane (2 mL) were added, in that order. Nitrogen was bubbled through the heterogeneous mixture for 2 min. Then Pd$_2$(dba)$_3$ (9 mg, 0.009960 mmol) was added under nitrogen and nitrogen was bubbled through the reaction for another 2 min and then capped the mixture under nitrogen. The mixture was stirred at 115° C. for 15 h. The mixture was allowed to cool to ambient temperature and neutralized with glacial acetic acid (50 μL, 0.8792 mmol). The volatiles were removed under reduced pressure and the residue was taken up in dimethyl sulfoxide (1.5 mL) and filtered through a Whatman 0.45 μm PTFE syringe filter disc. The sample was purified using preparative reverse-phase HPLC-MS (30%-99% acetonitrile in water over 15 min (hydrochloric acid as modifier). The desired product fractions were combined and concentrated under reduced pressure and the residue was taken up in ethyl acetate (25 mL) and washed successively with saturated aqueous sodium bicarbonate (2×10 mL) and brine (10 mL). The organic layer was dried over anhydrous sodium sulfate, filtered and concentrated under reduced pressure to furnish 20,20-dimethyl-4-(2-oxo-3-{3-[1-(trifluoromethyl)cyclopropyl]propyl}pyrrolidin-1-yl)-10$\lambda^6$-thia-1,3,9,14,22-pentaazatetracyclo[16.2.1.1¹¹,¹⁴.0²,⁷]docosa-2,4,6,11(22),12-pentaene-8,10,10-trione (41 mg, 70%) as off-white solid mixture of diastereomers which was subjected to chiral SFC purification using a ChiralCel OJ-3H (250×10 mm), 5 μm column; mobile phase: 20% acetonitrile:methanol (90:10; No Modifier), 80% carbon dioxide; flow: 10 mL/min; concentration: 24 mg/mL in acetonitrile:methanol:dimethyl sulfoxide (81:9:10); injection volume: 70 μL; pressure: 100 bar; wavelength: 242 nm. The first diastereomer to elute was 20,20-dimethyl-4-(2-oxo-3-{3-[1-(trifluoromethyl)cyclopropyl]propyl}pyrrolidin-1-yl)-10$\lambda^6$-thia-1,3,9,14,22-pentaazatetracyclo[16.2.1.1¹¹,¹⁴.0²,⁷]docosa-2,4,6,11(22),12-pentaene-8,10,10-trione (diastereomer 1) (Compound 181) (11 mg, 18%). ESI-MS m/z calc. 622.2549, found 623.4 (M+1)⁺; Retention time: 2.18 min (LC Method B). The second diastereomer to elute was 20,20-dimethyl-4-(2-oxo-3-{3-[1-(trifluoromethyl)cyclopropyl]propyl}pyrrolidin-1-yl)-10$\lambda^6$-thia-1,3,9,14,22-pentaazatetracyclo[16.2.1.1¹¹,¹⁴.0²,⁷]docosa-2,4,6,11(22),12-pentaene-8,10,10-trione (diastereomer 2) (Compound 182) (10 mg, 17%). ESI-MS m/z calc. 622.2549, found 623.4 (M+1)⁺; Retention time: 2.19 min (LC Method B).

Example 168: Preparation of 20,20-dimethyl-4-(2-oxo-3-{2-[1-(trifluoromethyl)cyclopropyl]ethoxy}pyrrolidin-1-yl)-10$\lambda^6$-thia-1,3,9,14,22-pentaazatetracyclo[16.2.1.1¹¹,¹⁴.0²,⁷]docosa-2,4,6,11(22),12-pentaene-8,10,10-trione (Compound 183), 20,20-dimethyl-4-(2-oxo-3-{2-[1-(trifluoromethyl)cyclopropyl]ethoxy}pyrrolidin-1-yl)-10$\lambda^6$-thia-1,3,9,14,22-pentaazatetracyclo[16.2.1.1¹¹,¹⁴.0²,⁷]docosa-2,4,6,11(22),12-pentaene-8,10,10-trione (Diastereomer 1) (Compound 191) and 20,20-dimethyl-4-(2-oxo-3-{2-[1-(trifluoromethyl)cyclo propyl]ethoxy}pyrrolidin-1-yl)-10$\lambda^6$-thia-1,3,9,14,22-pentaazatetracyclo[16.2.1.1¹¹,¹⁴.0²,⁷]docosa-2,4,6,11(22),12-pentaene-8,10,10-trione (Diastereomer 2) (Compound 192)

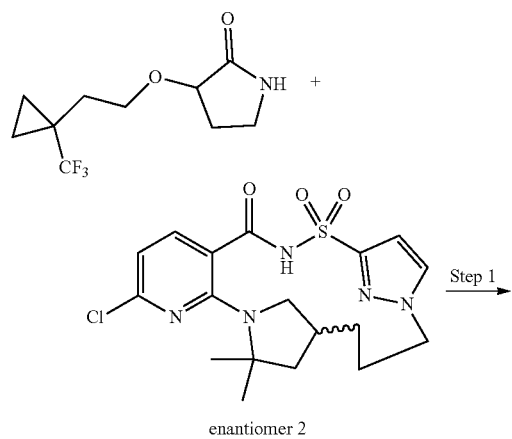

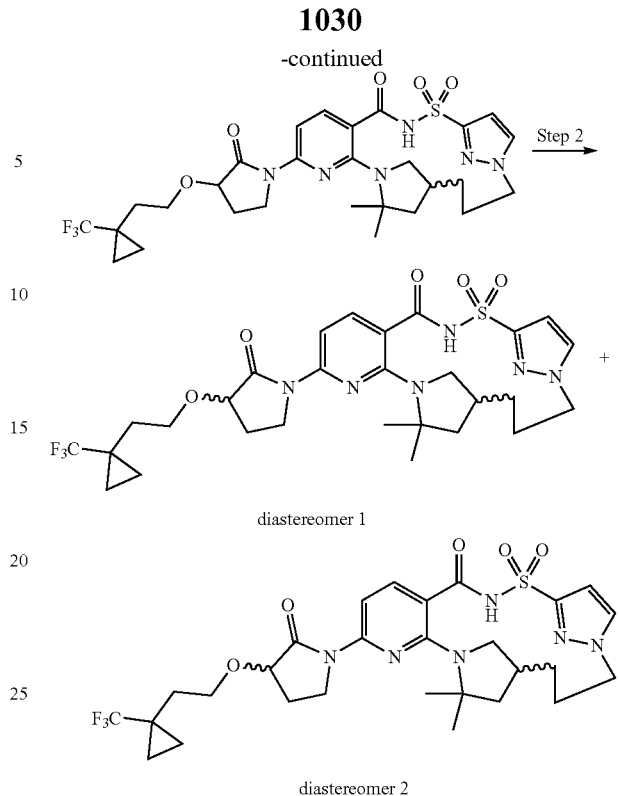

diastereomer 1 diastereomer 2

Step 1: 20,20-Dimethyl-4-(2-oxo-3-{2-[1-(trifluoromethyl)cyclopropyl]ethoxy}pyrrolidin-1-yl)-10$\lambda^6$-thia-1,3,9,14,22-pentaazatetracyclo[16.2.1.1¹¹,14.02,7]docosa-2,4,6,11(22),12-pentaene-8,10,10-trione (Compound 183)

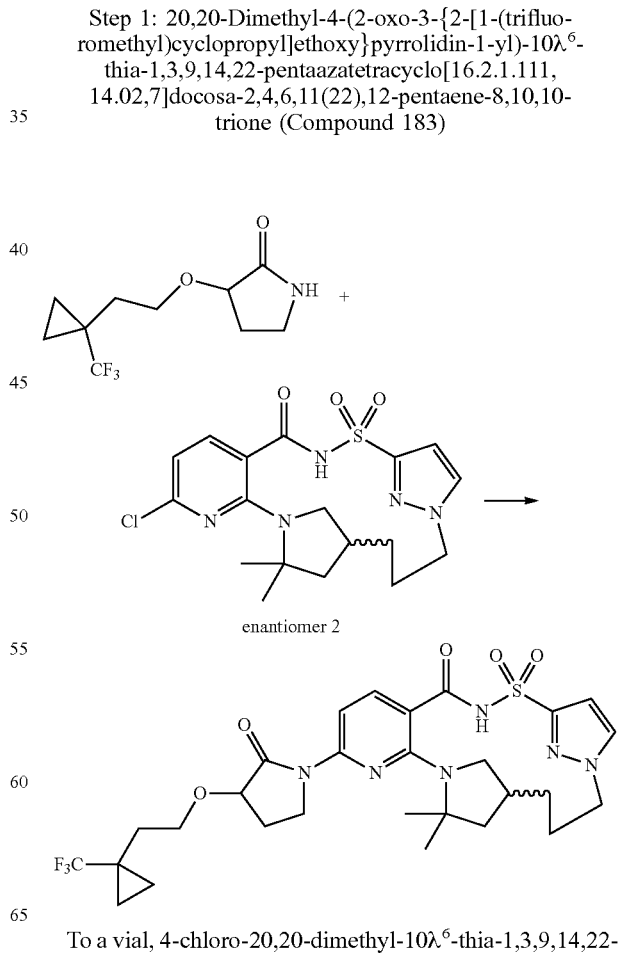

enantiomer 2

To a vial, 4-chloro-20,20-dimethyl-10$\lambda^6$-thia-1,3,9,14,22-pentaazatetracyclo[16.2.1.1¹¹,14.02,7]docosa-2,4,6,11(22), 12-pentaene-8,10,10-trione (enantiomer 2) (40 mg, 0.09436 mmol), 3-[2-[1-(trifluoromethyl)cyclopropyl]ethoxy]pyrrolidin-2-one (23 mg, 0.09696 mmol), cesium carbonate (102 mg, 0.3131 mmol), 4,5-bis(diphenylphosphino)-9,9-dimethylxanthene (8 mg, 0.01383 mmol) (Xantphos) and dry dioxane (1.5 mL) were added, in that order. Nitrogen was bubbled through the heterogeneous mixture for 2 min. Then Pd$_2$(dba)$_3$ (8 mg, 0.008853 mmol) was added under nitrogen and nitrogen was bubbled for another 2 min through the reaction then capped under nitrogen. The mixture was stirred at 115° C. for 15 h. The mixture was allowed to cool to ambient temperature and neutralized with glacial acetic acid (50 µL, 0.8792 mmol). The volatiles were removed under reduced pressure and the residue was taken up in dimethyl sulfoxide (1.5 mL) and filtered through a Whatman 0.45 µm PTFE syringe filter disc. The sample was purified using preparative reverse-phase HPLC-MS (30%-99% acetonitrile in water over 15 min, hydrochloric acid as modifier). The desired product fractions were combined and concentrated under reduced pressure and the residue was taken up in ethyl acetate (25 mL) and washed successively with saturated aqueous sodium bicarbonate (2×10 mL) and brine (10 mL). The organic layer was dried over anhydrous sodium sulfate, filtered and concentrated under reduced pressure to furnish 20,20-dimethyl-4-(2-oxo-3-{2-[1-(trifluoromethyl)cyclopropyl]ethoxy}pyrrolidin-1-yl)-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Compound 183) (41 mg, 74%) as an off-white solid. $^1$H NMR (400 MHz, Methanol-d$_4$) δ 7.79 (d, J=2.3 Hz, 1H), 7.64 (dd, J=8.4, 2.1 Hz, 1H), 7.61-7.54 (m, 1H), 6.91 (dd, J=2.4, 1.1 Hz, 1H), 4.31-4.21 (m, 2H), 4.16 (ddd, J=11.8, 8.8, 3.2 Hz, 1H), 4.12-4.00 (m, 1H), 3.96 (q, J=7.5 Hz, 1H), 3.90-3.72 (m, 2H), 2.83-2.73 (m, 1H), 2.55-2.43 (m, 1H), 2.23-2.08 (m, 2H), 2.02-1.87 (m, 6H), 1.77 (dd, J=11.9, 5.4 Hz, 1H), 1.57 (s, 3H), 1.50 (s, 3H), 1.39 (t, J=12.2 Hz, 1H), 0.96-0.90 (m, 2H), 0.84-0.76 (m, 2H), 0.76-0.68 (m, 1H). ESI-MS m/z calc. 624.2342, found 625.4 (M+1)+; Retention time: 2.05 min (LC Method B).

Step 2: 20,20-Dimethyl-4-(2-oxo-3-{2-[1-(trifluoromethyl)cyclopropyl]ethoxy}pyrrolidin-1-yl)-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Diastereomer 1) (Compound 191) and 20,20-dimethyl-4-(2-oxo-3-{2-[1-(trifluoromethyl)cyclopropyl]ethoxy}pyrrolidin-1-yl)-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Diastereomer 2) (Compound 192)

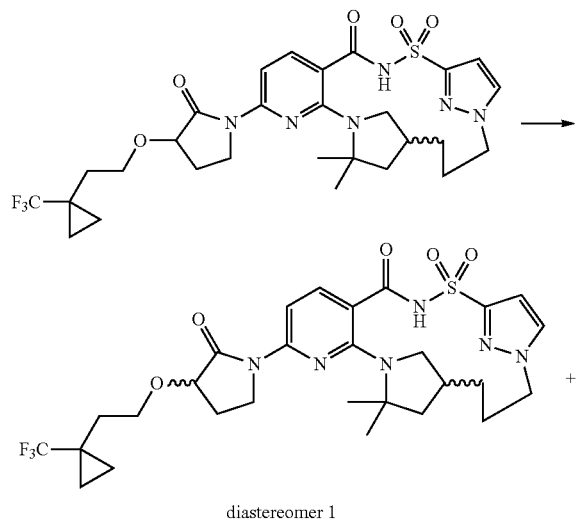

diastereomer 1

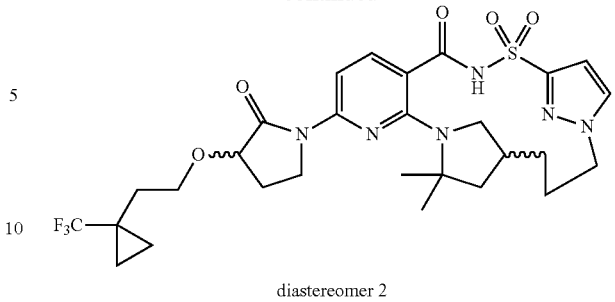

diastereomer 2

20,20-Dimethyl-4-(2-oxo-3-{2-[1-(trifluoromethyl)cyclopropyl]ethoxy}pyrrolidin-1-yl)-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Compound 183) was subjected to chiral SFC using a ChiralPak IG (250×10 mm), 5 µm column; mobile phase: 42% acetonitrile:methanol (90:10; No Modifier), 58% carbon dioxide; flow: 70 mL/min; concentration: 24 mg/mL in acetonitrile:methanol (90:10, no modifier); injection volume: 70 µL; pressure: 100 bar. The first diastereomer to elute was 20,20-dimethyl-4-(2-oxo-3-{2-[1-(trifluoromethyl)cyclopropyl]ethoxy}pyrrolidin-1-yl)-10λ$^6$-thia-1,3,9,14,22-pentaazatetracyclo[16.2.1.1$^{11,14}$.0$^{2,7}$]docosa-2,4,6,11(22),12-pentaene-8,10,10-trione (diastereomer 1) (Compound 191) (13.6 mg, 24%). ESI-MS m/z calc. 624.2342, found 625.4 (M+1)$^+$; Retention time: 1.87 min (LC Method B). The second diastereomer to elute was 20,20-dimethyl-4-(2-oxo-3-{2-[1-(trifluoromethyl)cyclopropyl]ethoxy}pyrrolidin-1-yl)-10λ$^6$-thia-1,3,9,14,22-pentaazatetracyclo[16.2.1.1$^{11,14}$.0$^{2,7}$]docosa-2,4,6,11(22),12-pentaene-8,10,10-trione (diastereomer 2) (Compound 192) (13.5 mg, 24%). ESI-MS m/z calc. 624.2342, found 625.4 (M+1)$^+$; Retention time: 1.88 min (LC Method B).

Example 169: Preparation of 4-[3-(3,3-dimethylbutyl)-2-oxopyrrolidin-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Compound 184)

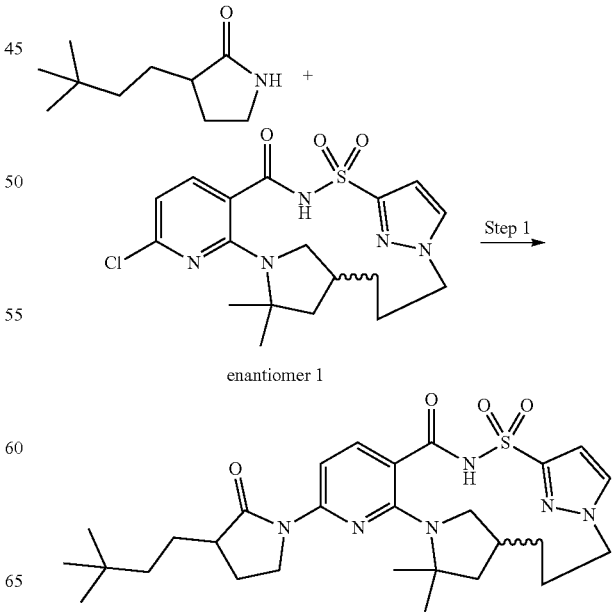

1033

Step 1: 4-[3-(3,3-Dimethylbutyl)-2-oxopyrrolidin-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 184)

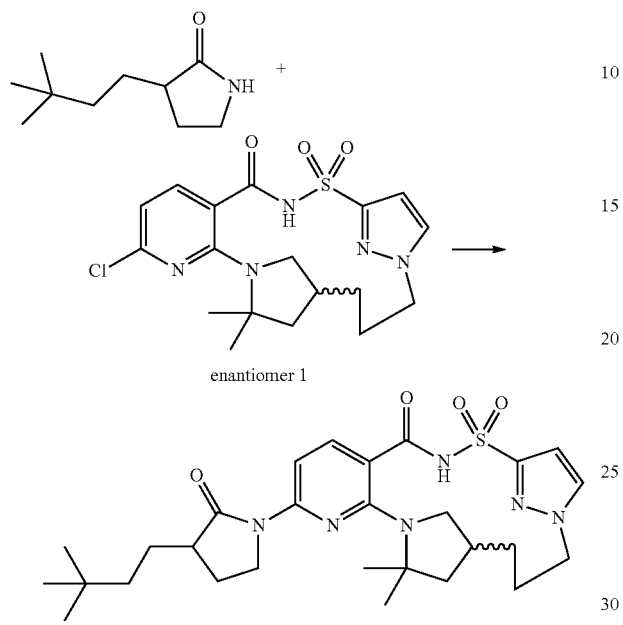

enantiomer 1

To a vial, 4-chloro-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (enantiomer 1) (11 mg, 0.02595 mmol), 3-(3,3-dimethylbutyl)pyrrolidin-2-one (8 mg, 0.04726 mmol), cesium carbonate (32 mg, 0.09821 mmol), 4,5-bis(diphenylphosphino)-9,9-dimethylxanthene (3 mg, 0.005185 mmol) (Xantphos) and dry dioxane (0.8 mL) were added, in that order. Nitrogen was bubbled through the heterogeneous mixture for 2 min. Then Pd₂(dba)₃ (3 mg, 0.003320 mmol) was added under nitrogen and nitrogen was bubbled through the mixture for another 2 min and capped the mixture under nitrogen. The mixture was stirred at 115° C. for 13 h. The mixture was allowed to cool to ambient temperature and was neutralized with glacial acetic acid (20 μL, 0.3517 mmol). The volatiles were removed under reduced pressure and the residue was taken up in dimethyl sulfoxide (1.0 mL) and filtered through a Whatman 0.45 μm PTFE syringe filter disc. The sample was purified using preparative reverse-phase HPLC-MS (30%-99% acetonitrile in water over 15 min (hydrochloric acid as modifier). The desired product fractions were combined and concentrated under reduced pressure to furnish 4-[3-(3,3-dimethylbutyl)-2-oxopyrrolidin-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 184) (7.5 mg, 51%) as a pale yellow solid. ¹H NMR (400 MHz, Methanol-d₄) δ 7.78 (d, J=2.5 Hz, 1H), 7.67-7.60 (m, 1H), 7.56 (dd, J=8.5, 7.0 Hz, 1H), 6.91 (d, J=2.4 Hz, 1H), 4.33-4.22 (m, 1H), 4.20-4.11 (m, 1H), 4.10-3.97 (m, 1H), 3.96-3.78 (m, 1H), 2.83-2.73 (m, 1H), 2.62 (ddd, J=13.7, 9.4, 5.0 Hz, 1H), 2.31 (q, J=9.0 Hz, 1H), 2.21-2.08 (m, 2H), 2.04-1.84 (m, 4H), 1.81-1.69 (m, 2H), 1.57 (s, 3H), 1.51 (s, 3H), 1.39 (t, J=12.4 Hz, 2H), 1.33-1.27 (m, 2H), 0.92 (s, 9H), 0.79-0.66 (m, 1H). ESI-MS m/z calc. 556.2832, found 557.5 (M+1)⁺; Retention time: 2.23 min (LC Method B).

1034

Example 170: Preparation of (18R)-4-[3-(2-{dispiro[2.0.2.1]heptan-7-yl}ethoxy)-1H-pyrazol-1-yl]-20,20-dimethyl-10λ⁶-thia-1,3,9,14,22-pentaazatetracyclo[16.2.1.1¹¹,¹⁴.0²,⁷]docosa-2,4,6,11(22),12-pentaene-8,10,10-trione (Compound 186)

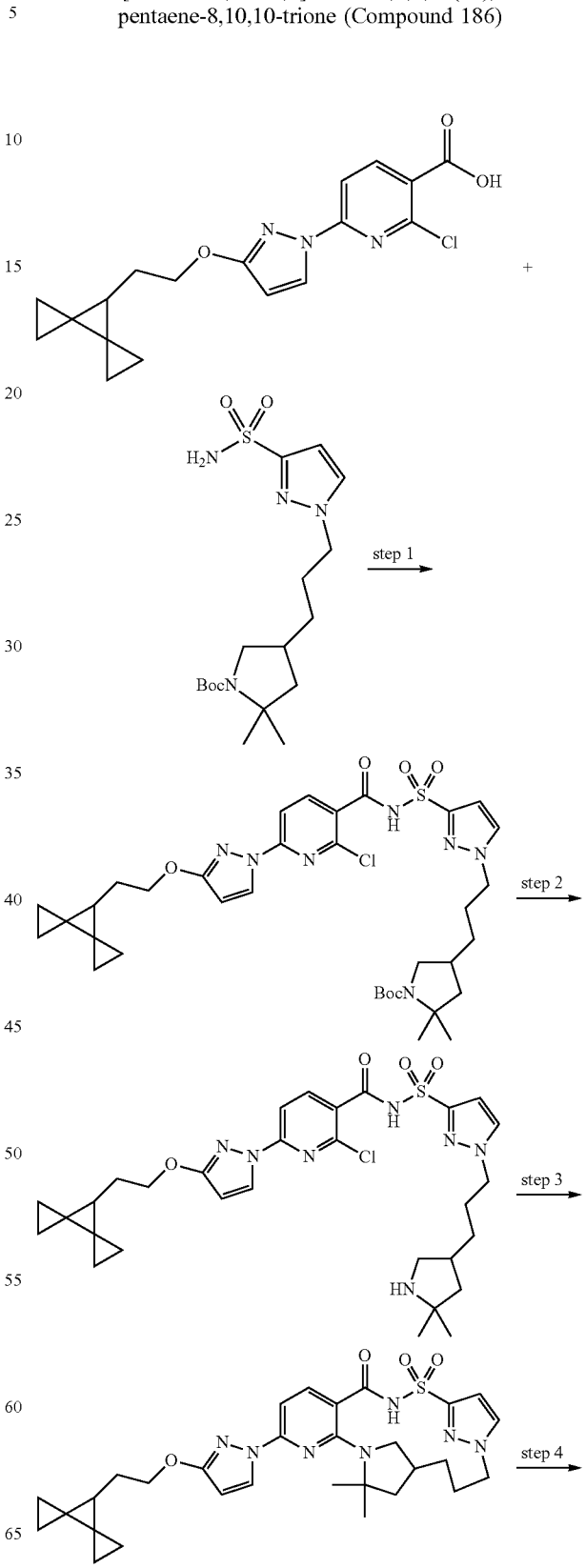

-continued

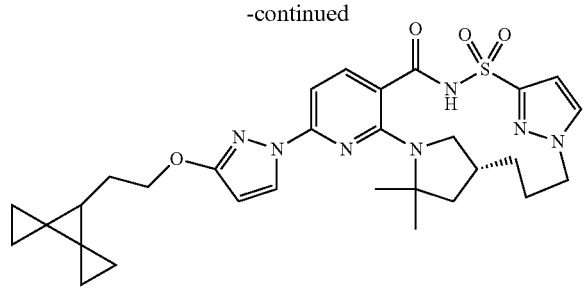

Step 1: tert-Butyl 4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate

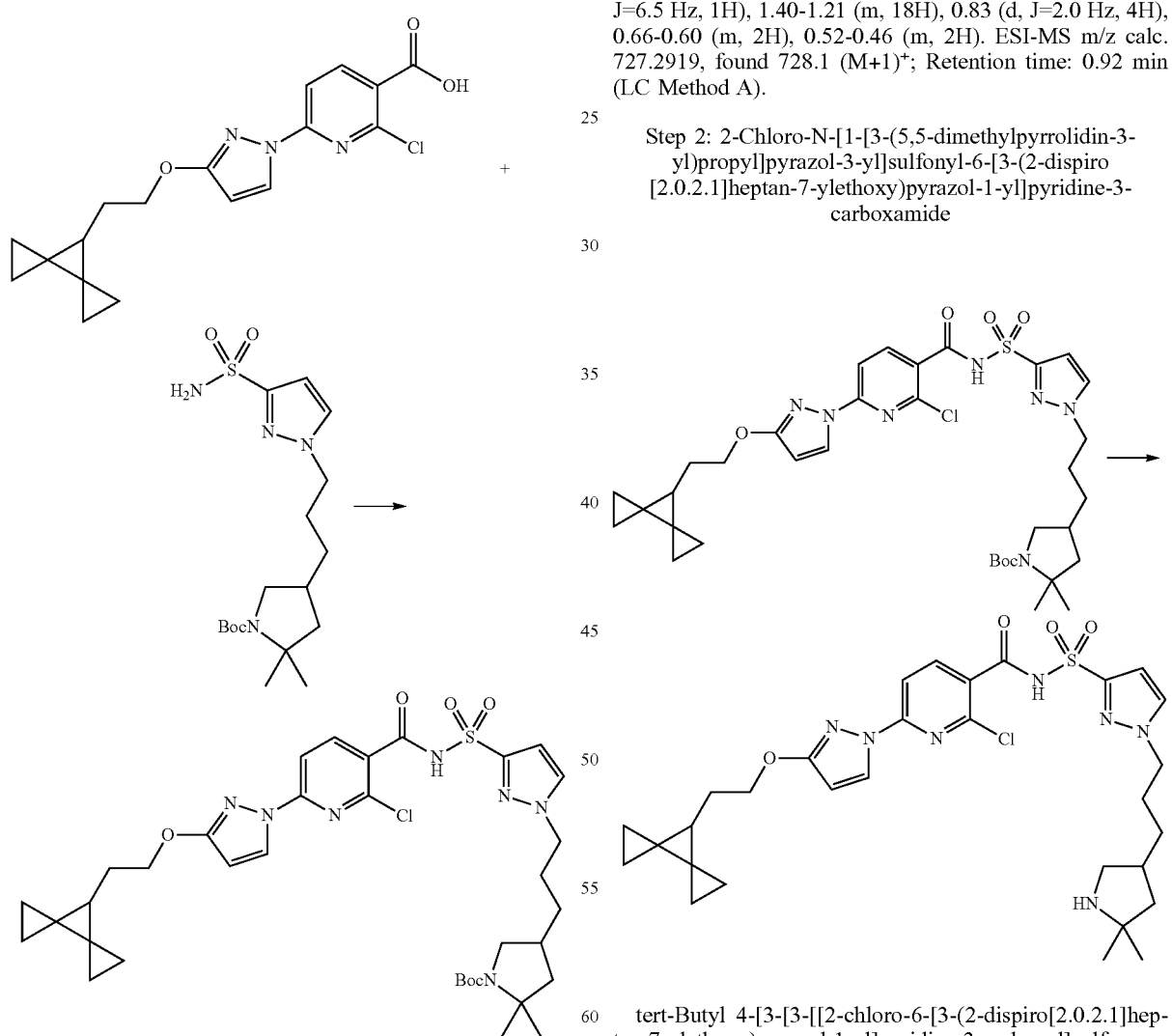

2-Chloro-6-[3-(2-dispiro[2.0.2.1]heptan-7-ylethoxy)pyrazol-1-yl]pyridine-3-carboxylic acid (400 mg, 1.112 mmol) and carbonyl diimidazole (273.5 mg, 1.687 mmol) were combined in tetrahydrofuran (2 mL) and stirred for 90 min at room temperature. Then, tert-butyl 2,2-dimethyl-4-[3-(3-sulfamoylpyrazol-1-yl)propyl]pyrrolidine-1-carboxylate (429.5 mg, 1.111 mmol) was added followed by 1,8-diazabicyclo[5.4.0]undec-7-ene (430.8 mg, 2.830 mmol) and the reaction was stirred at room temperature for 1 h then heated to 50° C. and stirred overnight. The reaction was diluted with ethyl acetate and washed with a saturated aqueous sodium bicarbonate solution, followed by brine. The organics were separated, dried over sodium sulfate, filtered and evaporated and then purified by silica gel chromatography using a gradient from 100% hexanes to 100% ethyl acetate to afford as an off-white solid, tert-butyl 4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate (350 mg, 43%). $^1$H NMR (400 MHz, dimethyl sulfoxide-$d_6$) δ 8.34 (s, 1H), 8.08 (d, J=8.2 Hz, 1H), 7.77 (s, 1H), 7.62 (d, J=8.3 Hz, 1H), 6.71-6.49 (m, 1H), 6.10 (d, J=2.8 Hz, 1H), 4.23 (s, 2H), 4.13 (s, 2H), 3.52 (s, 1H), 2.73 (d, J=6.0 Hz, 1H), 2.08 (d, J=6.7 Hz, 1H), 1.81 (q, J=6.6 Hz, 5H), 1.47 (t, J=6.5 Hz, 1H), 1.40-1.21 (m, 18H), 0.83 (d, J=2.0 Hz, 4H), 0.66-0.60 (m, 2H), 0.52-0.46 (m, 2H). ESI-MS m/z calc. 727.2919, found 728.1 (M+1)$^+$; Retention time: 0.92 min (LC Method A).

Step 2: 2-Chloro-N-[1-[3-(5,5-dimethylpyrrolidin-3-yl)propyl]pyrazol-3-yl]sulfonyl-6-[3-(2-dispiro[2.0.2.1]heptan-7-ylethoxy)pyrazol-1-yl]pyridine-3-carboxamide tert-Butyl 4-[3-[3-[[2-chloro-6-[3-(2-dispiro[2.0.2.1]heptan-7-ylethoxy)pyrazol-1-yl]pyridine-3-carbonyl]sulfamoyl]pyrazol-1-yl]propyl]-2,2-dimethyl-pyrrolidine-1-carboxylate (350 mg, 0.4806 mmol) was dissolved in dichloromethane (1.527 mL) and to the mixture was added trifluoroacetic acid (2.192 g, 1.481 mL, 19.22 mmol) and the resulting mixture was stirred at room temperature for 60 min. The mixture was concentrated to dryness under reduced pressure and taken up in saturated aqueous sodium bicarbonate and ethyl acetate and the layers were separated. (CAUTION, solubility of product in ethyl acetate under these conditions is poor, addition of some methanol helps, needed to evaporate the organic layer without using solid drying agent). Concentrated the organic layer by rotary evaporation followed by drying under vacuum giving 2-chloro-N-[1-[3-(5,5-dimethylpyrrolidin-3-yl)propyl]pyrazol-3-yl]sulfonyl-6-[3-(2-dispiro[2.0.2.1]heptan-7-ylethoxy)pyrazol-1-yl]pyridine-3-carboxamide (301.9 mg, 100%) as an off-white solid which was taken directly to the next step. $^1$H NMR (400 MHz, Chloroform-d) δ 8.28 (d, J=2.8 Hz, 1H), 8.21 (d, J=8.3 Hz, 1H), 7.61 (d, J=8.3 Hz, 1H), 7.44 (s, 1H), 6.67 (s, 1H), 5.88 (d, J=2.8 Hz, 1H), 4.22 (t, J=6.8 Hz, 2H), 4.17 (s, 2H), 3.55 (s, 1H), 3.03 (s, 1H), 2.23 (s, 1H), 1.88 (d, J=6.7 Hz, 2H), 1.83 (s, 3H), 1.48 (s, 1H), 1.46-1.35 (m, 5H), 1.35-1.24 (m, 4H), 0.84 (t, J=1.9 Hz, 4H), 0.63 (d, J=1.6 Hz, 2H), 0.51 (d, J=1.1 Hz, 2H).

Step 3: 4-[3-(2-{Dispiro[2.0.2.1]heptan-7-yl}ethoxy)-1H-pyrazol-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione 100% hexanes to 100% ethyl acetate (product elutes after reaching 100% ethyl acetate) to afford as a white solid, 4-[3-(2-{dispiro[2.0.2.1]heptan-7-yl}ethoxy)-1H-pyrazol-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (117 mg, 40%). $^1$H NMR (400 MHz, Chloroform-d) δ 8.37 (s, 1H), 8.16 (d, J=2.8 Hz, 1H), 7.68 (d, J=8.3 Hz, 1H), 7.48 (d, J=2.3 Hz, 1H), 7.26 (s, 1H), 7.07 (d, J=2.3 Hz, 1H), 7.02 (d, J=8.3 Hz, 1H), 5.86 (d, J=2.8 Hz, 1H), 4.36 (d, J=13.5 Hz, 1H), 4.24 (s, 2H), 3.95 (d, J=12.4 Hz, 1H), 2.74 (t, J=8.1 Hz, 1H), 2.15 (d, J=4.2 Hz, 2H), 2.08-1.93 (m, 3H), 1.89 (d, J=6.7 Hz, 2H), 1.76 (dd, J=11.9, 5.3 Hz, 1H), 1.59 (s, 3H), 1.55 (s, 5H), 0.85 (q, J=2.0 Hz, 4H), 0.64 (d, J=1.7 Hz, 2H), 0.51 (d, J=1.2 Hz, 2H). ESI-MS m/z calc. 591.26276, found 592.4 (M+1)$^+$; Retention time: 2.37 min (LC Method B).

Step 4: (18R)-4-[3-(2-{dispiro[2.0.2.1]heptan-7-yl}ethoxy)-1H-pyrazol-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Compound 186)

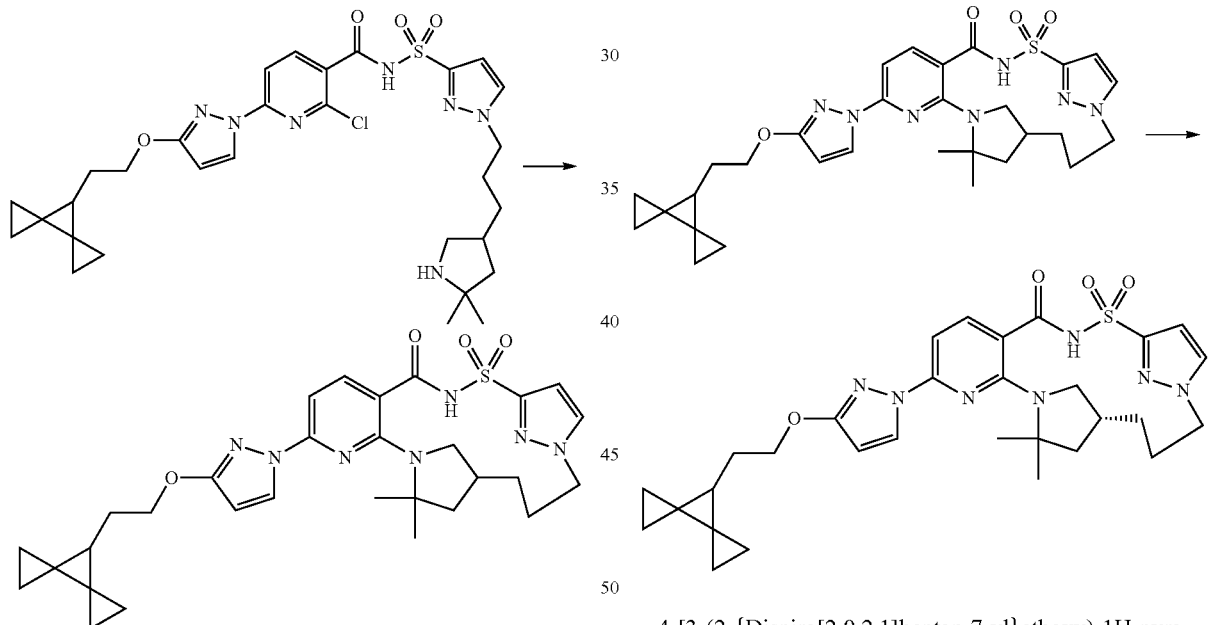

Combined 2-chloro-N-[1-[3-(5,5-dimethylpyrrolidin-3-yl)propyl]pyrazol-3-yl]sulfonyl-6-[3-(2-dispiro[2.0.2.1] heptan-7-ylethoxy)pyrazol-1-yl]pyridine-3-carboxamide (310 mg, 0.4935 mmol), potassium carbonate (341.1 mg, 2.468 mmol), cesium fluoride (112.8 mg, 0.7426 mmol), 3 Å molecular sieves and dimethyl sulfoxide (9.3 mL) in a vial, purged with nitrogen, capped, heated to 155° C. and stirred for 20 h. The mixture was then cooled to room temperature and filtered then diluted with ethyl acetate and washed with a saturated aqueous sodium bicarbonate solution followed by brine. The organics were separated, dried over sodium sulfate, filtered and evaporated and then purified by silica gel chromatography using a gradient from 4-[3-(2-{Dispiro[2.0.2.1]heptan-7-yl}ethoxy)-1H-pyrazol-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (103 mg, 0.1741 mmol) was subjected to chiral separation by SFC chromatography using a ChiralPak AS-H (250×10 mm, 5 μm particle size) with 34% acetonitrile/methanol (90:10)/66% carbon dioxide mobile phase at 10 mL/min over 8.0 min (injection volume=70 μL of 24 mg/mL solution in acetonitrile/methanol (90:10)) giving as the first enantiomer to elute, (18R)-4-[3-(2-{dispiro[2.0.2.1]heptan-7-yl}ethoxy)-1H-pyrazol-1-yl]-20,20-dimethyl-10λ$^6$-thia-1,3,9,14,22-pentaazatetracyclo[16.2.1.1$^{11,14}$.0$^{2,7}$]docosa-2,4,6,11(22),12-pentaene-8,10,10-trione (Compound 186) (40.8 mg, 79%). ESI-MS m/z calc. 591.26276, found 593.1 (M+1)$^+$; Retention time: 2.3 min (LC Method B).

Example 171: Preparation of (14R)-12,12-dimethyl-8-(3-{3-[1-(trifluoromethyl)cyclo propyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 190)

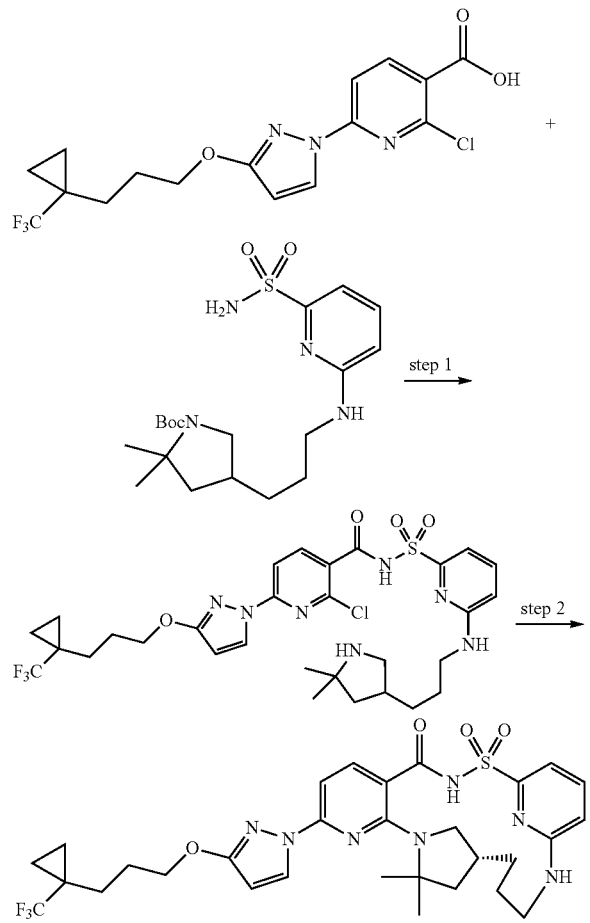

Step 1: 2-Chloro-N-[[6-[3-(5,5-dimethylpyrrolidin-3-yl)propylamino]-2-pyridyl]sulfonyl]-6-[3-[3-[1-(trifluoromethyl)cyclopropyl]propoxy]pyrazol-1-yl]pyridine-3-carboxamide

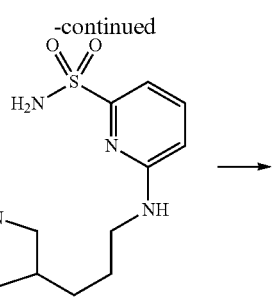

-continued

A 50 mL flask charged with carbonyl diimidazole (216 mg, 1.332 mmol) and 2-chloro-6-[3-[3-[1-(trifluoromethyl)cyclopropyl]propoxy]pyrazol-1-yl]pyridine-3-carboxylic acid (520 mg, 1.334 mmol) was evacuated then backfilled with nitrogen. Added tetrahydrofuran (8 mL) and the mixture was stirred at 50° C. for 1 h. Next, a solution of tert-butyl 2,2-dimethyl-4-[3-[(6-sulfamoyl-2-pyridyl)amino]propyl]pyrrolidine-1-carboxylate (500 mg, 1.212 mmol) and 1,8-diazabicyclo[5.4.0]undec-7-ene (555 mg, 3.646 mmol) in tetrahydrofuran (3 mL) was added and the mixture was stirred overnight at 50° C. The reaction was diluted with ethyl acetate and washed with water. The organic phase was dried over sodium sulfate, evaporated in vacuo and purified by silica gel chromatography (0% to 50% ethyl acetate in hexanes) to afford some pure fractions. Mixed fractions were further purified by preparative reverse phase HPLC (C₁₈): 1%-99% acetonitrile in water with hydrochloric acid modifier. Pure fractions from the silica gel column and preparatory HPLC column were combined to afford the acylsulfonamide intermediate which was dissolved in dioxane (5 mL) and then treated with a dioxane solution of hydrochloric acid (2 mL of 6 M, 12.00 mmol) and then stirred at room temperature for 2 h. The mixture was evaporated in vacuo and the residue was quenched with aqueous sodium bicarbonate. The white precipitate of the product was filtered off and washed with ethyl acetate. The aqueous phase was additionally extracted with ethyl acetate. The organic extract was dried over sodium sulfate, filtered and evaporated to afford, after drying in vacuo, 2-chloro-N-[[6-[3-(5,5-dimethylpyrrolidin-3-yl)propylamino]-2-pyridyl]sulfonyl]-6-[3-[3-[1-(trifluoromethyl)cyclopropyl]propoxy]pyrazol-1-yl]pyridine-3-carboxamide (343 mg, 41%). ESI-MS m/z calc. 683.2268, found 684.32 (M+1)⁺; Retention time: 0.65 min (LC Method A).

Step 2: (14R)-12,12-dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 190)

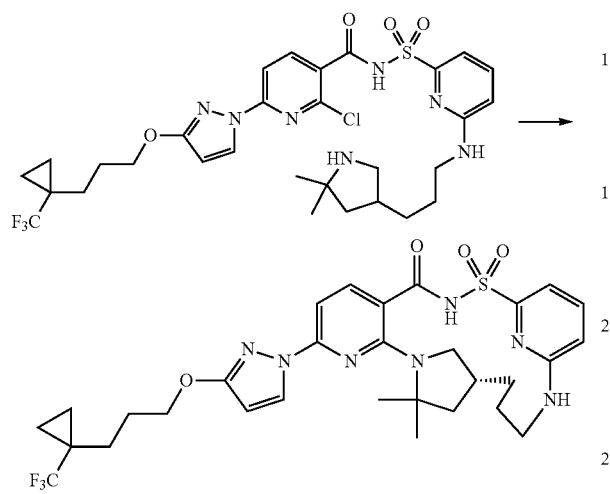

In a 5 mL vial, cesium fluoride (160 mg, 1.053 mmol), potassium carbonate (360 mg, 2.605 mmol) and 4 Å molecular sieves (600 mg) were combined and the vial was evacuated then backfilled with nitrogen. Next, a solution of 2-chloro-N-[[6-[3-(5,5-dimethylpyrrolidin-3-yl)propylamino]-2-pyridyl]sulfonyl]-6-[3-[3-[1-(trifluoromethyl)cyclopropyl]propoxy]pyrazol-1-yl]pyridine-3-carboxamide (350 mg, 0.5116 mmol) in dimethyl sulfoxide (5 mL) was added and the mixture was stirred at 150° C. overnight. The mixture was filtered and purified by preparative reverse phase HPLC (C₁₈): 1%-99% acetonitrile in water/hydrochloric acid modifier to afford the racemic product. The racemate was subjected to chiral separation by SFC chromatography using a ChiralPak AS-H (250×10 mm, 5 μm particle size) with 28% acetonitrile/methanol (90:10)/72% carbon dioxide mobile phase (injection volume=500 μL of 32 mg/mL solution in acetonitrile/methanol (90:10)) giving as the first enantiomer to elute (14R)-12,12-dimethyl-8-(3-{3-[1-(trifluoromethyl)cyclopropyl]propoxy}-1H-pyrazol-1-yl)-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (Compound 190) (82.3 mg, 49%). ESI-MS m/z calc. 647.2502, found 648.1 (M+1)⁺; Retention time: 2.21 min (LC Method B).

Example 172: Preparation of (14S)-8-[3-(4,4-dimethylpentyl)-2-oxoimidazolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 193)

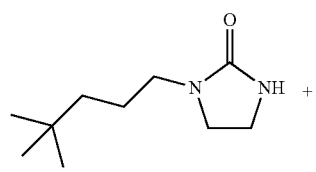

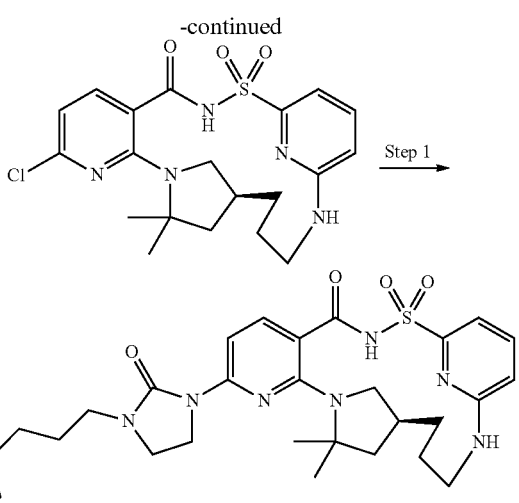

Step 1: (14S)-8-[3-(4,4-dimethylpentyl)-2-oxoimidazolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 193)

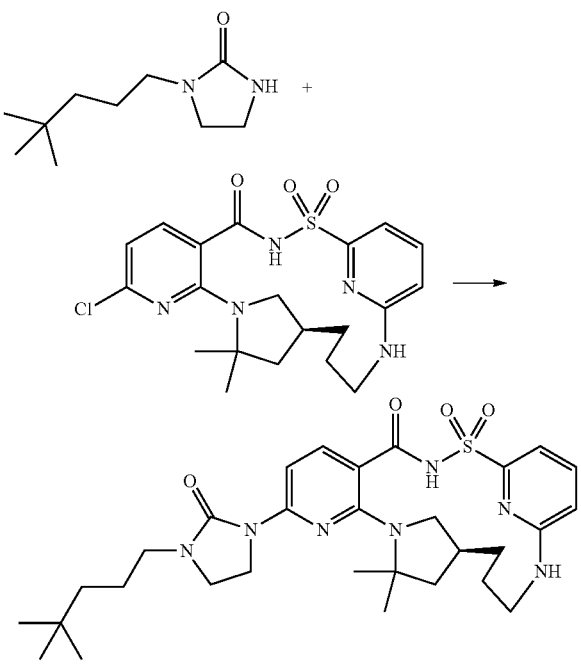

To a vial, (14S)-8-chloro-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (60 mg, 0.1333 mmol), 1-(4,4-dimethylpentyl)imidazolidin-2-one (50 mg, 0.2713 mmol), cesium carbonate (155 mg, 0.4757 mmol), 4,5-bis(diphenylphosphino)-9,9-dimethylxanthene (12 mg, 0.02074 mmol) (Xantphos) and anhydrous dioxane (2.0 mL) were added, in that order. Nitrogen was bubbled through the heterogeneous mixture for 2 min. Then Pd₂(dba)₃ (12 mg, 0.01328 mmol) was added under nitrogen and nitrogen was bubbled into the mixture for another 2 min and then the vial was capped under nitrogen. The mixture was stirred at 115° C. for 13 h. The mixture was allowed to cool to ambient temperature and then neutralized with glacial acetic acid (70 µL, 1.231 mmol). The volatiles were removed under reduced pressure and the residue was taken up in dimethyl sulfoxide (1.5 mL) and filtered through a Whatman 0.45 µm PTFE syringe filter disc. The sample was purified using preparative reverse-phase HPLC-MS [30%-99% acetonitrile in water (hydrochloric acid as modifier)]. The desired product fractions were combined and concentrated under reduced pressure and further dried under high vacuum giving (14S)-8-[3-(4,4-dimethylpentyl)-2-oxoimidazolidin-1-yl]-12,12-dimethyl-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 193) (29 mg, 36%) as pale yellow solid. ¹H NMR (400 MHz, Methanol-d₄) δ 7.70 (d, J=8.6 Hz, 1H), 7.52 (dd, J=8.5, 7.2 Hz, 1H), 7.44 (d, J=8.6 Hz, 1H), 7.15 (d, J=7.2 Hz, 1H), 6.65 (d, J=8.5 Hz, 1H), 4.14-3.94 (m, 3H), 3.52 (ddd, J=9.8, 7.0, 3.2 Hz, 2H), 3.24 (q, J=7.2 Hz, 3H), 3.09-2.97 (m, 1H), 2.86 (t, J=10.4 Hz, 1H), 2.23-2.08 (m, 1H), 1.83 (dd, J=11.3, 5.1 Hz, 2H), 1.65-1.63 (m, 3H), 1.63-1.55 (m, 4H), 1.55 (s, 3H), 1.42 (q, J=11.5 Hz, 1H), 1.29 (s, 1H), 1.26-1.19 (m, 2H), 0.92 (s, 9H). ESI-MS m/z calc. 597.30975, found 598.5 (M+1)⁺; Retention time: 2.08 min (LC Method B).

Example 173: Preparation of 12,20,20-trimethyl-4-(3-{2-[1-(trifluoromethyl)cyclopropyl]ethoxy}-1H-pyrazol-1-yl)-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Compound 199)

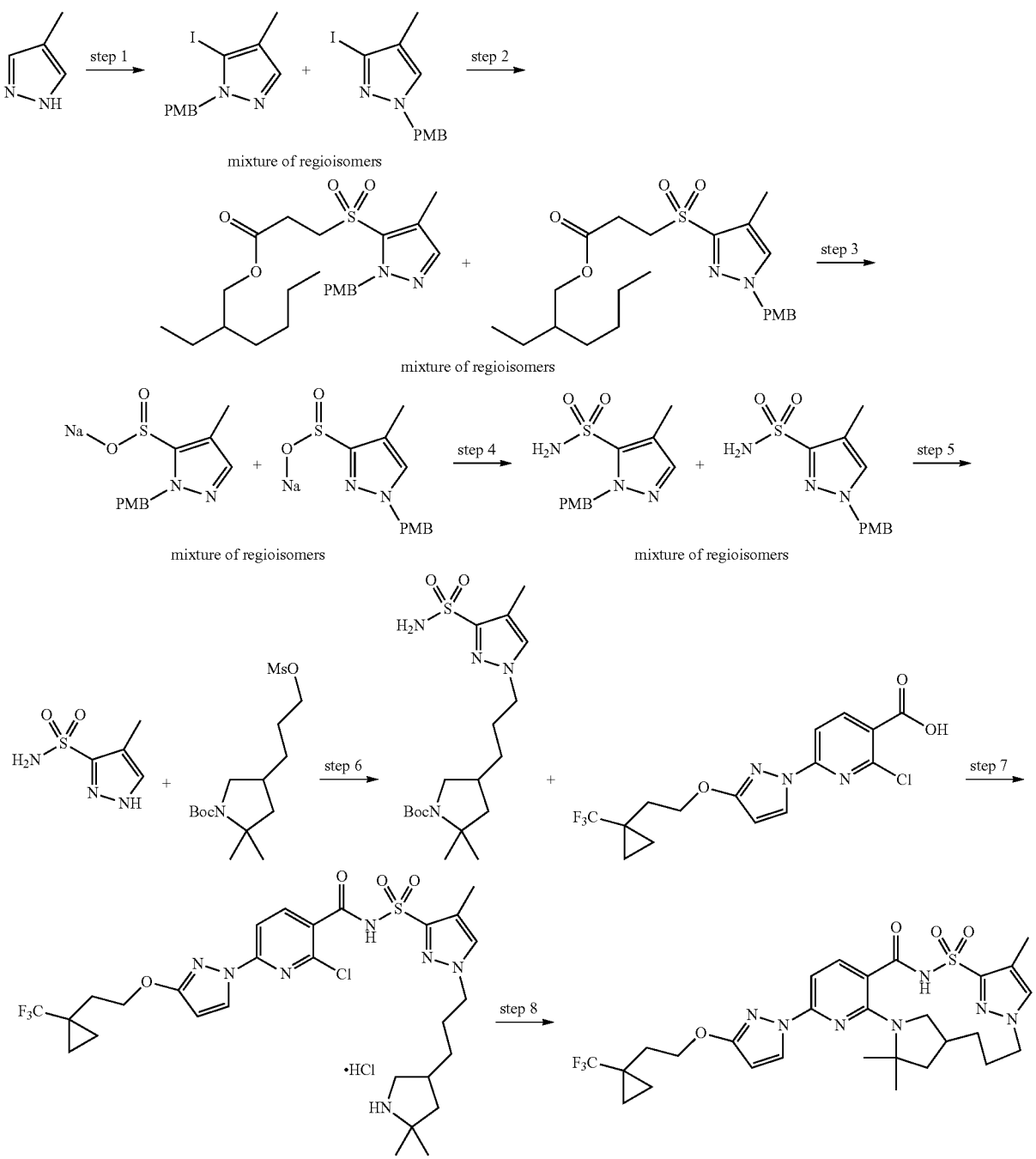

Step 1: 3-Iodo-1-[(4-methoxyphenyl)methyl]-4-methyl-pyrazole and 5-iodo-1-[(4-methoxyphenyl)methyl]-4-methyl-pyrazole (Mixture of Regioisomers)

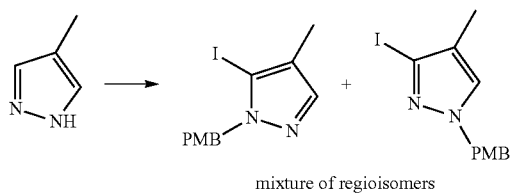

mixture of regioisomers

N-Iodosuccinimide (27.4 g, 121.79 mmol) was added to a solution of 4-methyl-1H-pyrazole (10 g, 121.80 mmol) in dimethylformamide (100 mL) at room temperature. The mixture was stirred overnight then poured in water (700 mL) and extracted with ethyl acetate (4×150 mL). The organic phases were combined and washed with water (3×150 mL) and brine (150 mL), dried with sodium sulfate, filtered and concentrated under reduced pressure to afford crude iodinated intermediate. To a solution of the crude iodinated material (2 g, 9.6154 mmol) and potassium carbonate (2 g, 14.471 mmol) in acetonitrile (15 mL) was added 1-(chloromethyl)-4-methoxy-benzene (1.5015 g, 1.3 mL, 9.5876 mmol). The mixture was stirred at 80° C. overnight before being concentrated under reduced pressure. The residue was suspended in dichloromethane (80 mL). After stirred for 10 min, the mixture was mixed with silica gel before being concentrated. The residue was dry loaded on a silica gel column and eluted using 0%-30% ethyl acetate in heptanes to obtain 3-iodo-1-[(4-methoxyphenyl)methyl]-4-methyl-pyrazole and 5-iodo-1-[(4-methoxyphenyl)methyl]-4-methyl-pyrazole (mixture of regioisomers) (1.36 g, 43%) as a pale yellow solid. ESI-MS m/z calc. 328.0073, found 329.0 (M+1)$^+$; Retention time: 2.02 min (LC Method I).

Step 2: 2-Ethylhexyl 3-[1-[(4-methoxyphenyl)methyl]-4-methyl-pyrazol-3-yl]sulfanylpropanoate and 2-ethylhexyl 3-[2-[(4-methoxyphenyl)methyl]-4-methyl-pyrazol-3-yl]sulfanylpropanoate (Mixture of Regioisomers)

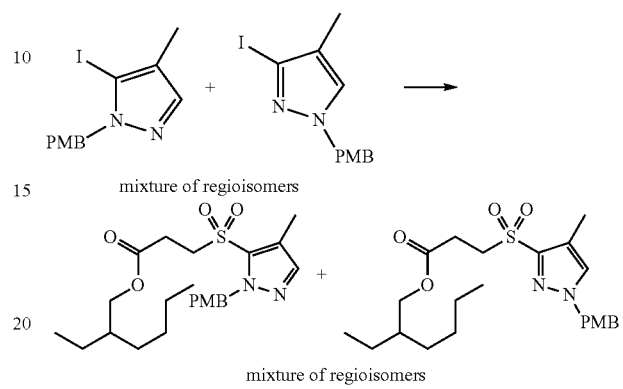

mixture of regioisomers

In a sealed tube, a solution of 3-iodo-1-[(4-methoxyphenyl)methyl]-4-methyl-pyrazole and 5-iodo-1-[(4-methoxyphenyl)methyl]-4-methyl-pyrazole (mixture of regioisomers) (1.34 g, 4.0835 mmol) and diisopropylethylamine (1.0685 g, 1.44 mL, 8.2674 mmol) in toluene (25 mL) was degassed by bubbling nitrogen for 5 min. Tris(dibenzylideneacetone)dipalladium(0) (111 mg, 0.1212 mmol), Xantphos (142 mg, 0.2454 mmol) and 2-ethylhexyl 3-sulfanylpropanoate (986 mg, 4.5156 mmol) were added, the vial was sealed and the mixture was heated at 110° C. overnight. The reaction mixture was concentrated under reduced pressure. The residue was purified by silica gel chromatography using a gradient from 0% to 20% of ethyl acetate in heptanes to afford 2-ethylhexyl 3-[1-[(4-methoxyphenyl)methyl]-4-methyl-pyrazol-3-yl]sulfanylpropanoate and 2-ethylhexyl 3-[2-[(4-methoxyphenyl)methyl]-4-methyl-pyrazol-3-yl]sulfanylpropanoate (mixture of regioisomers) (1.54 g, 90%) as an orange oil. ESI-MS m/z calc. 418.229, found 419.3 (M+1)$^+$; Retention time: 2.58 min (LC Method I).

Step 3: [1-[(4-Methoxyphenyl)methyl]-4-methyl-pyrazol-3-yl]sulfinyloxysodium and [2-[(4-methoxyphenyl)methyl]-4-methyl-pyrazol-3-yl]sulfinyloxysodium (Mixture of Regioisomers)

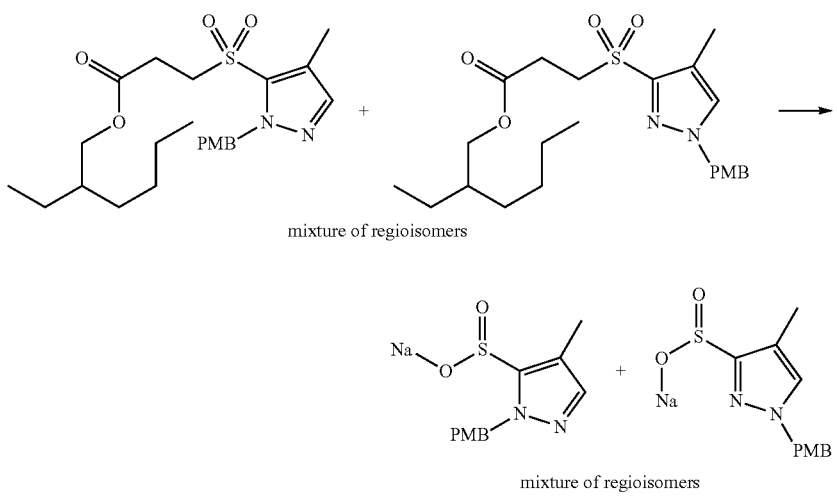

Sodium methoxide (750.17 mg, 13.886 mmol) was added to a solution of 2-ethylhexyl 3-[1-[(4-methoxyphenyl)methyl]-4-methyl-pyrazol-3-yl]sulfonylpropanoate and 2-ethylhexyl 3-[2-[(4-methoxyphenyl)methyl]-4-methyl-pyrazol-3-yl]sulfonylpropanoate (mixture of regioisomers) (1.56 g, 3.4621 mmol) in tetrahydrofuran (4 mL) and methanol (1.4 mL) at room temperature. The reaction mixture was stirred for 2 h then the mixture was concentrated under reduced pressure to afford [1-[(4-methoxyphenyl)methyl]-4-methyl-pyrazol-3-yl]sulfinyloxysodium and [2-[(4-methoxyphenyl)methyl]-4-methyl-pyrazol-3-yl]sulfinyloxysodium (mixture of regioisomers) (1.04 g, 104%) as a beige solid. ESI-MS m/z calc. 288.0545, found 289.1 (M+1)$^+$; Retention time: 1.5 min (LC Method I).

Step 4: 1-[(4-Methoxyphenyl)methyl]-4-methyl-pyrazole-3-sulfonamide and 2-[(4-methoxyphenyl)methyl]-4-methyl-pyrazole-3-sulfonamide (Mixture of Regioisomers)

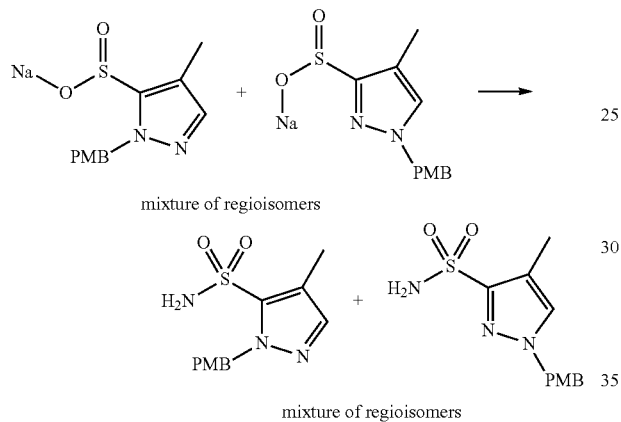

mixture of regioisomers

Hydroxylamine-O-sulfonic acid (9.7 g, 85.770 mmol) was added to a solution of [1-[(4-methoxyphenyl)methyl]-4-methyl-pyrazol-3-yl]sulfinyloxysodium and [2-[(4-methoxyphenyl)methyl]-4-methyl-pyrazol-3-yl]sulfinyloxysodium (mixture of regioisomers) (12.4 g, 43.011 mmol) and sodium acetate (10.5 g, 128.00 mmol) in water (400 mL) at 0° C. The mixture was stirred at room temperature overnight then extracted with ethyl acetate (2×300 mL). The organic phase was dried over sodium sulfate, filtered and concentrated under reduced pressure. The residue was purified by silica-gel column chromatography eluting from 20% to 60% of ethyl acetate in heptanes to afford 1-[(4-methoxyphenyl)methyl]-4-methyl-pyrazole-3-sulfonamide and 2-[(4-methoxyphenyl)methyl]-4-methyl-pyrazole-3-sulfonamide (mixture of regioisomers) (9.72 g, 80%) as an off-white solid. ESI-MS m/z calc. 281.0834, found 282.1 (M+1)$^+$; Retention time: 1.51 min (LC Method I).

Step 5: 4-Methyl-1H-pyrazole-3-sulfonamide

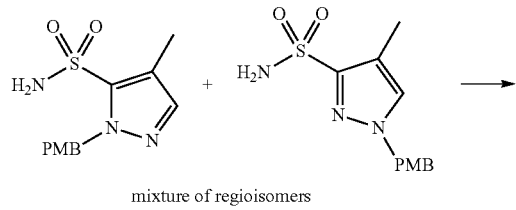

mixture of regioisomers

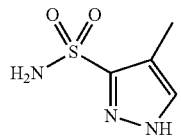

A solution of 1-[(4-methoxyphenyl)methyl]-4-methyl-pyrazole-3-sulfonamide and 2-[(4-methoxyphenyl)methyl]-4-methyl-pyrazole-3-sulfonamide (mixture of regioisomers) (270 mg, 0.9597 mmol) in trifluoroacetic acid (2 mL) was stirred at 80° C. overnight. The mixture was concentrated and the residue was purified by silica gel chromatography using a gradient from 20%-100% ethyl acetate in heptanes then isocratic 10% methanol in ethyl acetate to obtain 4-methyl-1H-pyrazole-3-sulfonamide (120 mg, 78%) as a white solid. $^1$H NMR (300 MHz, dimethyl sulfoxide-d$_6$) ppm 2.12 (s, 3H), 7.29 (s, 2H), 7.64 (s, 1H), 13.11 (br. s., 1H). ESI-MS m/z calc. 161.0259, found 162.1 (M+1)$^+$; Retention time: 0.46 min (LC Method I).

Step 6: tert-Butyl 2,2-dimethyl-4-[3-(4-methyl-3-sulfamoyl-pyrazol-1-yl)propyl]pyrrolidine-1-carboxylate

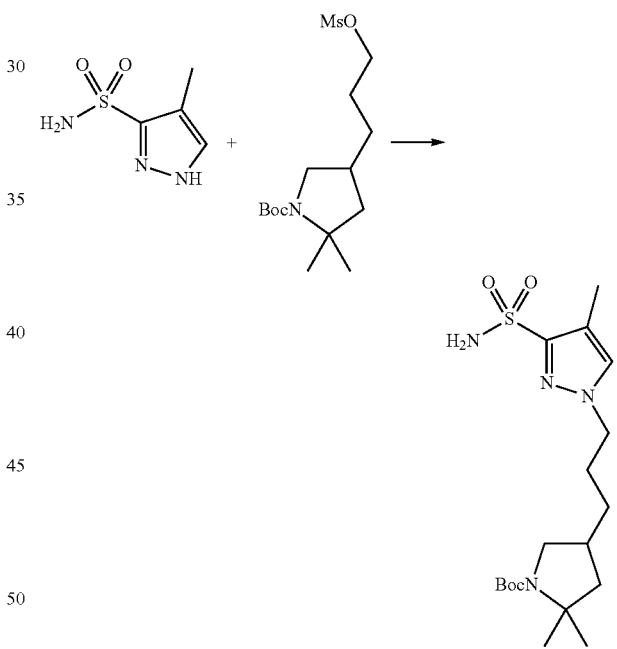

A solution of tert-butyl 2,2-dimethyl-4-(3-methylsulfonyloxypropyl)pyrrolidine-1-carboxylate (750 mg, 2.236 mmol), potassium carbonate (772 mg, 5.586 mmol) and 4-methyl-1H-pyrazole-3-sulfonamide (300 mg, 1.861 mmol) in N,N-dimethylformamide (3 mL) was stirred at 80° C. for 4 h. The mixture was filtered and dissolved in diethyl ether. The mixture was washed with water, dried over sodium sulfate, filtered and evaporated in vacuo. The residue was purified by silica gel chromatography (0% to 30% ethyl acetate in hexanes) giving poor separation. Mixed fractions were combined, evaporated and separated by preparative reverse phase HPLC (C$_{18}$, 1%-99% acetonitrile in water/hydrochloric acid modifier) to afford as the first to elute, major regioisomer, tert-butyl 2,2-dimethyl-4-[3-(4-methyl- 3-sulfamoyl-pyrazol-1-yl)propyl]pyrrolidine-1-carboxylate (200 mg, 27%). $^1$H NMR (400 MHz, Chloroform-d) δ 7.23-7.19 (m, 1H), 5.06 (s, 2H), 4.08 (t, J=7.0 Hz, 2H), 3.65 (dd, J=10.2, 7.6 Hz, 1H), 2.82 (t, J=10.6 Hz, 1H), 2.26 (d, J=0.7 Hz, 3H), 2.11-1.97 (m, 1H), 1.92-1.82 (m, 3H), 1.66-1.58 (m, 1H), 1.46 (s, 9H), 1.39 (s, 3H), 1.37-1.30 (m, 2H), 1.27 (s, 3H). ESI-MS m/z calc. 400.21442, found 401.26 (M+1)$^+$; Retention time: 0.65 min (LC Method A).

Step 7: 2-Chloro-N-[1-[3-(5,5-dimethylpyrrolidin-3-yl)propyl]-4-methyl-pyrazol-3-yl]sulfonyl-6-[3-[2-[1-(trifluoromethyl)cyclopropyl]ethoxy]pyrazol-1-yl]pyridine-3-carboxamide (Hydrochloride Salt)

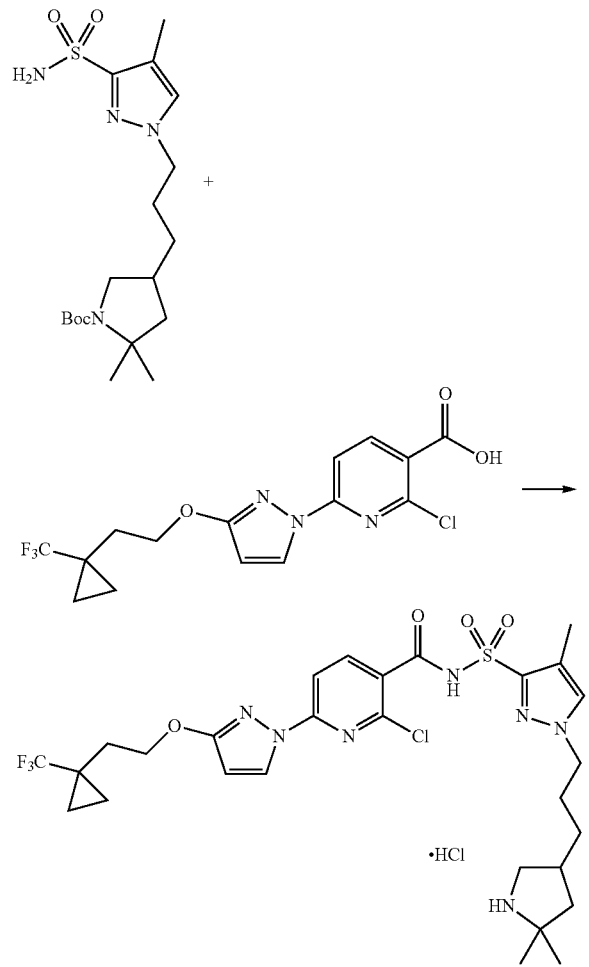

A 50 mL flask charged with carbonyl diimidazole (73 mg, 0.4502 mmol) and 2-chloro-6-[3-[2-[1-(trifluoromethyl)cyclopropyl]ethoxy]pyrazol-1-yl]pyridine-3-carboxylic acid (170 mg, 0.4525 mmol) was evacuated/backfilled with nitrogen. Added tetrahydrofuran (5 mL) and the mixture was stirred at 50° C. for 1 h. Next, a solution of tert-butyl 2,2-dimethyl-4-[3-(4-methyl-3-sulfamoyl-pyrazol-1-yl)propyl]pyrrolidine-1-carboxylate (150 mg, 0.3745 mmol) and 1,8-diazabicyclo[5.4.0]undec-7-ene (143 mg, 0.9393 mmol) in tetrahydrofuran (4 mL) was added and the mixture was stirred overnight at 50° C. The reaction was diluted with ethyl acetate and washed with water. The organic phase was dried over sodium sulfate, evaporated in vacuo and purified by preparative reverse phase HPLC (C$_{18}$, 1%-99% acetonitrile in water/hydrochloric acid modifier) to afford the acylsulfonamide intermediate which was dissolved in dioxane (5 mL) and treated with hydrochloric acid (1.3 mL of 6 M in dioxane, 7.800 mmol) and stirred at room temperature for 3 h. The mixture was evaporated in vacuo to afford 2-chloro-N-[1-[3-(5,5-dimethylpyrrolidin-3-yl)propyl]-4-methyl-pyrazol-3-yl]sulfonyl-6-[3-[2-[1-(trifluoromethyl)cyclopropyl]ethoxy]pyrazol-1-yl]pyridine-3-carboxamide (hydrochloride salt) (57 mg, 22%). ESI-MS m/z calc. 657.2112, found 658.32 (M+1)$^+$; Retention time: 0.6 min (LC Method A).

Step 8: 12,20,20-Trimethyl-4-(3-{2-[1-(trifluoromethyl)cyclopropyl]ethoxy}-1H-pyrazol-1-yl)-10λ$^6$-thia-1,3,9,14,22-pentaazatetracyclo[16.2.1.1$^{11,14}$.0$^{2,7}$]docosa-2(7),3,5,11(22),12-pentaene-8,10,10-trione (Compound 199)

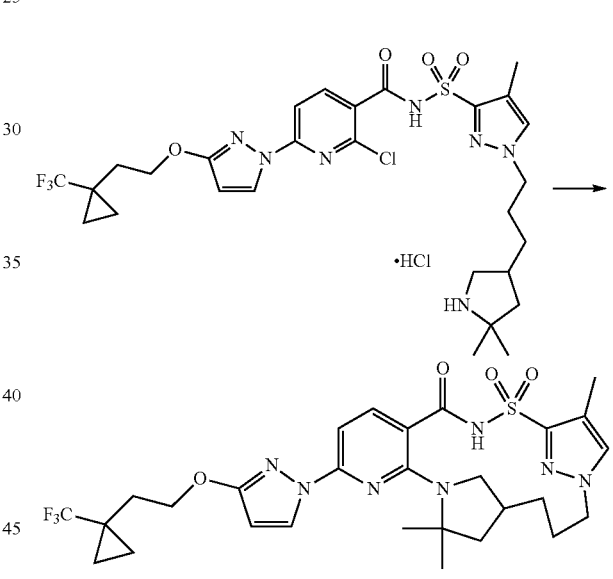

In 5 mL vial, 2-chloro-N-[1-[3-(5,5-dimethylpyrrolidin-3-yl)propyl]-4-methyl-pyrazol-3-yl]sulfonyl-6-[3-[2-[1-(trifluoromethyl)cyclopropyl]ethoxy]pyrazol-1-yl]pyridine-3-carboxamide (hydrochloride salt) (57 mg, 0.08206 mmol), potassium carbonate (58 mg, 0.4197 mmol), cesium fluoride (25 mg, 0.1646 mmol) and 3 Å molecular sieves (300 mg) were sealed and purged with nitrogen. Added dimethyl sulfoxide (3 mL) and the mixture was stirred at 150° C. overnight. The mixture was filtered and purified by preparative reverse phase HPLC (C$_{18}$, 1%-99% acetonitrile in water/hydrochloric acid modifier) to afford 12,20,20-trimethyl-4-(3-{2-[1-(trifluoromethyl)cyclopropyl]ethoxy}-1H-pyrazol-1-yl)-10λ$^6$-thia-1,3,9,14,22-pentaazatetracyclo[16.2.1.1$^{11,14}$.0$^{2,7}$]docosa-2(7),3,5,11(22),12-pentaene-8,10,10-trione (Compound 199) (6.2 mg, 12%). ESI-MS m/z calc. 621.2345, found 622.35 (M+1)$^+$; Retention time: 2.16 min (LC Method B).

Example 174: Preparation of (14S)-8-(3-cyclo-hexyl-2-oxoimidazolidin-1-yl)-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 200)

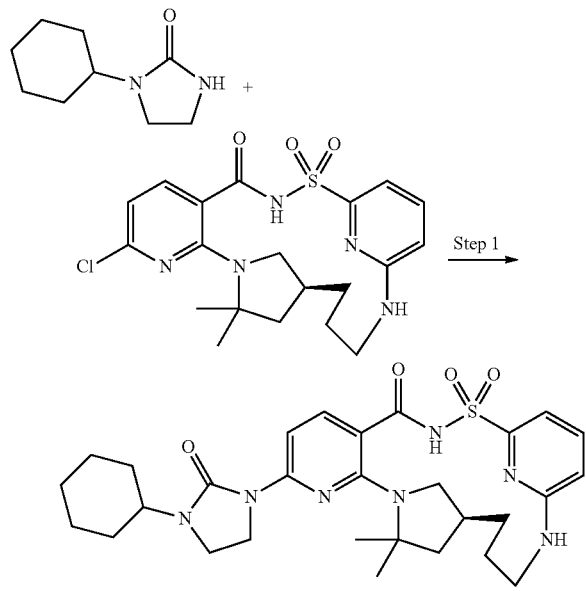

Step 1: (14S)-8-(3-Cyclohexyl-2-oxoimidazolidin-1-yl)-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 200)

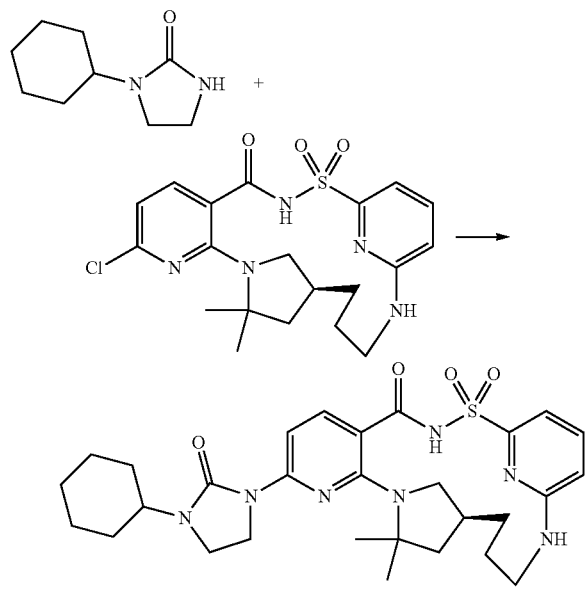

A 5 mL vial was charged with (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (50 mg, 0.1075 mmol), 1-cyclohexylimidazolidin-2-one (26 mg, 0.1545 mmol), Pd$_2$(dba)$_3$ (26 mg, 0.02839 mmol), Xantphos (16 mg, 0.02765 mmol), cesium carbonate (180 mg, 0.5525 mmol) and anhydrous dioxane (800 μL). The mixture was sparged with nitrogen for 1-2 min, capped and stirred at 120° C. for 20 h and then cooled to room temperature. The solvent was evaporated, the reaction was diluted with dimethyl sulfoxide (900 μL), microfiltered and purified by reverse-phase preparative chromatography utilizing a C$_{18}$ column (10%-99% acetonitrile in water+5 mM hydrochloric acid). The product fractions were combined, brine was added and the organic solvents were evaporated. The product was extracted with dichloromethane, the organic phase was dried over sodium sulfate, filtered and evaporation of the solvents gave a solid. The product was further purified by silica gel chromatography using a gradient from 100% dichloromethane to 5% methanol in dichloromethane giving as an off-white solid, (14S)-8-(3-cyclohexyl-2-oxoimidazolidin-1-yl)-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 200) (22.5 mg, 36%). $^1$H NMR (400 MHz, Chloroform-d) δ 10.79 (s, 1H), 8.01 (d, J=8.7 Hz, 1H), 7.90 (d, J=8.8 Hz, 1H), 7.55 (q, J=2.9, 2.1 Hz, 2H), 6.54 (dd, J=5.4, 3.7 Hz, 1H), 4.80 (s, 1H), 3.99 (dd, J=9.1, 7.1 Hz, 2H), 3.83 (s, 2H), 3.45 (t, J=8.1 Hz, 2H), 3.32 (t, J=8.9 Hz, 1H), 3.23-3.10 (m, 1H), 3.04 (t, J=9.4 Hz, 1H), 2.71 (s, 1H), 2.12 (dd, J=12.4, 8.6 Hz, 1H), 1.84-1.76 (m, 4H), 1.69 (d, J=13.2 Hz, 2H), 1.56 (d, J=5.2 Hz, 8H), 1.43-1.36 (m, 4H), 1.15-1.06 (m, 1H), 0.91-0.85 (m, 1H). ESI-MS m/z calc. 581.27844, found 582.2 (M+1)$^+$; Retention time: 1.86 min (LC Method E).

Example 175: Preparation of 4-[3-(3,3-dicyclopropylpropoxy)-1H-pyrazol-1-yl]-12,20,20-trimethyl-10λ$^6$-thia-1,3,9,14,22-pentaazatetracyclo[16.2.1.1$^{11}$,14.0$^{2,7}$]docosa-2(7),3,5,11(22),12-pentaene-8,10,10-trione (Enantiomer 1) (Compound 201) and 4-[3-(3,3-dicyclopropylpropoxy)-1H-pyrazol-1-yl]-12,20,20-trimethyl-10λ$^6$-thia-1,3,9,14,22-pentaazatetracyclo[16.2.1.1$^{11}$,14.0$^{2,7}$]docosa-2(7),3,5,11(22),12-pentaene-8,10,10-trione (Enantiomer 2) (Compound 202)

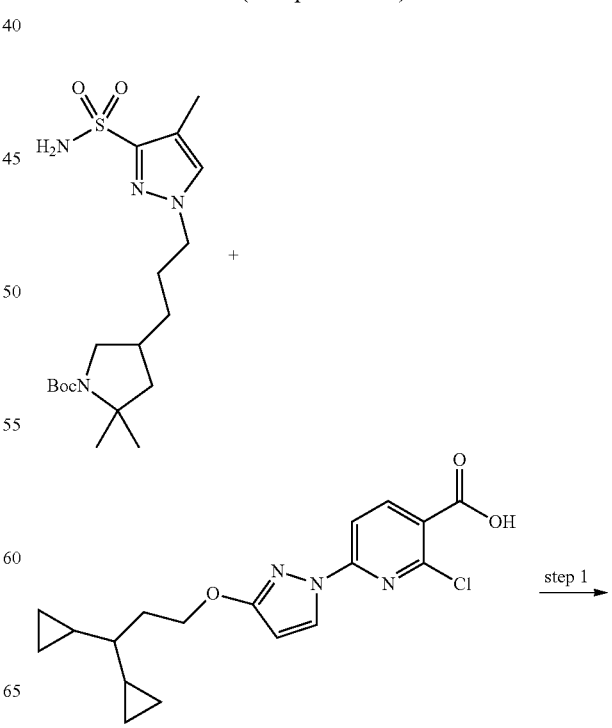

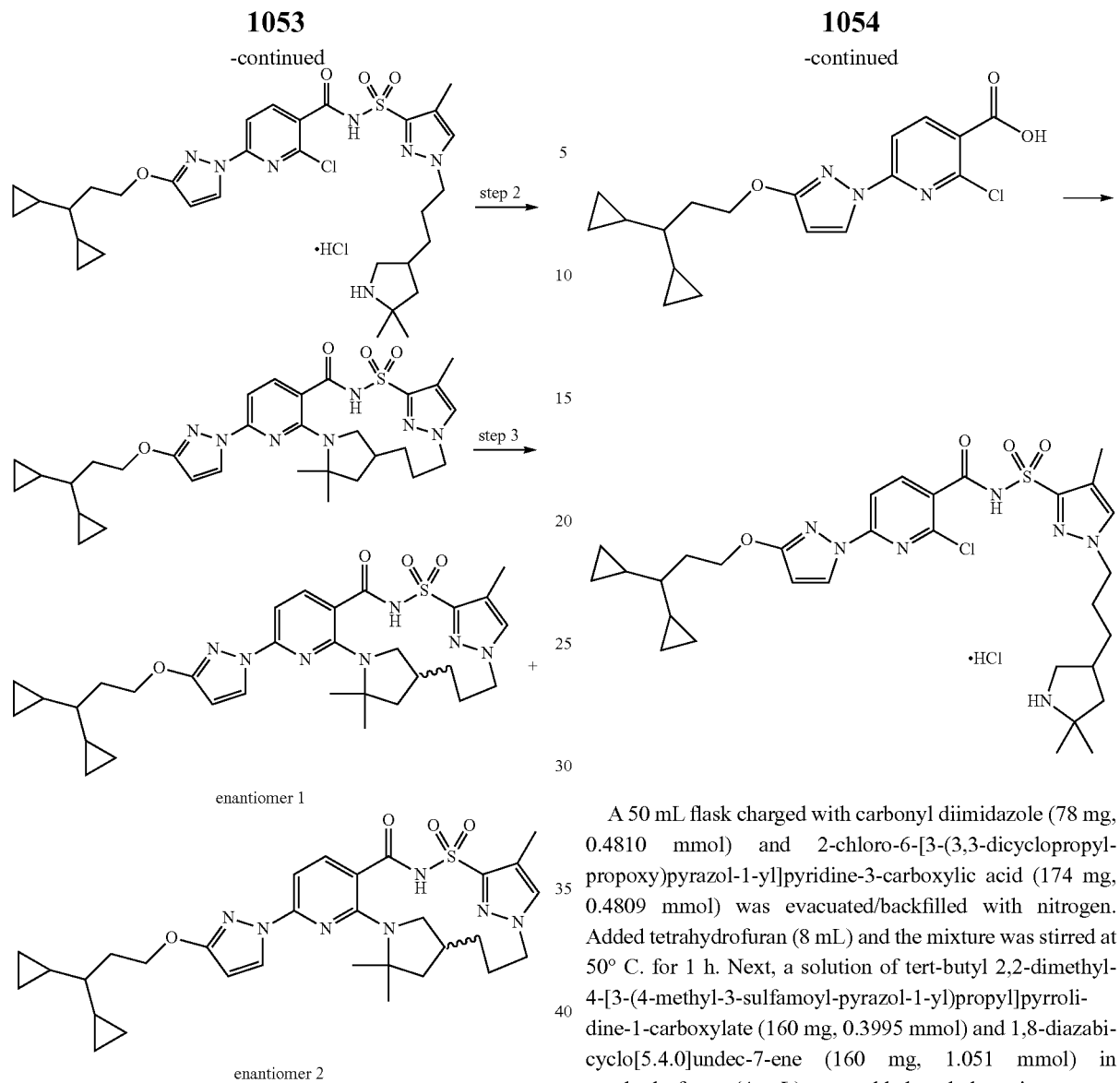

Step 1: 2-Chloro-6-[3-(3,3-dicyclopropylpropoxy) pyrazol-1-yl]-N-[1-[3-(5,5-dimethylpyrrolidin-3-yl) propyl]-4-methyl-pyrazol-3-yl]sulfonyl-pyridine-3-carboxamide (Hydrochloride Salt)

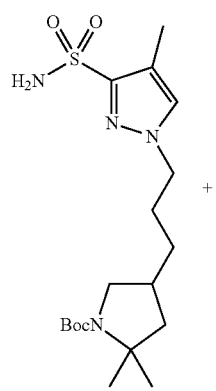

A 50 mL flask charged with carbonyl diimidazole (78 mg, 0.4810 mmol) and 2-chloro-6-[3-(3,3-dicyclopropyl-propoxy)pyrazol-1-yl]pyridine-3-carboxylic acid (174 mg, 0.4809 mmol) was evacuated/backfilled with nitrogen. Added tetrahydrofuran (8 mL) and the mixture was stirred at 50° C. for 1 h. Next, a solution of tert-butyl 2,2-dimethyl-4-[3-(4-methyl-3-sulfamoyl-pyrazol-1-yl)propyl]pyrrolidine-1-carboxylate (160 mg, 0.3995 mmol) and 1,8-diazabi-cyclo[5.4.0]undec-7-ene (160 mg, 1.051 mmol) in tetrahydrofuran (4 mL) was added and the mixture was stirred overnight at 50° C. The reaction was diluted with ethyl acetate and washed with water. The organic phase was dried over sodium sulfate, evaporated in vacuo and purified by silica gel chromatography (0% to 50% ethyl acetate in hexanes) to afford some pure fractions. Mixed fractions were repurified by preparative reverse phase HPLC ($C_{18}$, 1%-99% acetonitrile in water/hydrochloric acid modifier) and the resulting pure material was combined with pure fractions from the initial silica gel column to afford the acylsulfonamide intermediate. A solution of the acylsulfo-namide intermediate in dioxane (5 mL) was treated with hydrochloric acid (1.3 mL of 6 M in dioxane, 7.800 mmol) and stirred at room temperature for 3 h. The mixture was evaporated in vacuo to afford 2-chloro-6-[3-(3,3-dicyclopro-pylpropoxy)pyrazol-1-yl]-N-[1-[3-(5,5-dimethylpyrrolidin-3-yl)propyl]-4-methyl-pyrazol-3-yl]sulfonyl-pyridine-3-carboxamide (hydrochloride salt) (160 mg, 59%). ESI-MS m/z calc. 643.27075, found 644.38 (M+1)$^+$; Retention time: 0.65 min (LC Method A).

1055

Step 2: 4-[3-(3,3-Dicyclopropylpropoxy)-1H-pyrazol-1-yl]-12,20,20-trimethyl-10λ⁶-thia-1,3,9,14,22-pentaazatetracyclo[16.2.1.1¹¹,¹⁴.0²,⁷]docosa-2(7),3,5,11(22),12-pentaene-8,10,10-trione

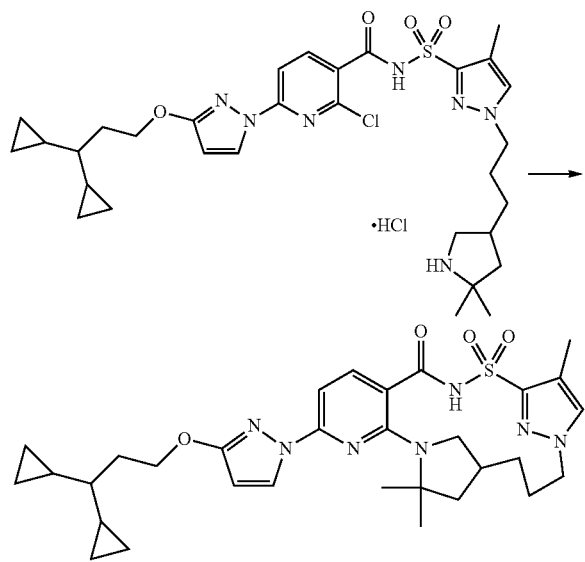

In 5 mL vial, 2-chloro-6-[3-(3,3-dicyclopropylpropoxy)pyrazol-1-yl]-N-[1-[3-(5,5-dimethylpyrrolidin-3-yl)propyl]-4-methyl-pyrazol-3-yl]sulfonyl-pyridine-3-carboxamide (hydrochloride salt) (160 mg, 0.2351 mmol), potassium carbonate (165 mg, 1.194 mmol), cesium fluoride (73 mg, 0.4806 mmol) and 3 Å molecular sieves (300 mg) were sealed and purged with nitrogen. Added dimethyl sulfoxide (4 mL) and the mixture was stirred at 150° C. overnight. The mixture was filtered and purified by preparative reverse phase HPLC (C₁₈, 1%-99% acetonitrile in water/hydrochloric acid modifier) to afford 4-[3-(3,3-dicyclopropylpropoxy)-1H-pyrazol-1-yl]-12,20,20-trimethyl-10λ⁶-thia-1,3,9,14,22-pentaazatetracyclo[16.2.1.1¹¹,¹⁴.0²,⁷]docosa-2(7),3,5,11(22),12-pentaene-8,10,10-trione (53.7 mg, 38%). ESI-MS m/z calc. 607.29407, found 608.41 (M+1)⁺; Retention time: 2.36 min (LC Method B).

Step 3: 4-[3-(3,3-Dicyclopropylpropoxy)-1H-pyrazol-1-yl]-12,20,20-trimethyl-10λ⁶-thia-1,3,9,14,22-pentaazatetracyclo[16.2.1.1¹¹,¹⁴.0²,⁷]docosa-2(7),3,5,11(22),12-pentaene-8,10,10-trione (Enantiomer 1) (Compound 201) and 4-[3-(3,3-dicyclopropylpropoxy)-1H-pyrazol-1-yl]-12,20,20-trimethyl-10λ⁶-thia-1,3,9,14,22-pentaazatetracyclo[16.2.1.1¹¹,14.02,7]docosa-2(7),3,5,11(22),12-pentaene-8,10,10-trione (Enantiomer 2) (Compound 202)

1056

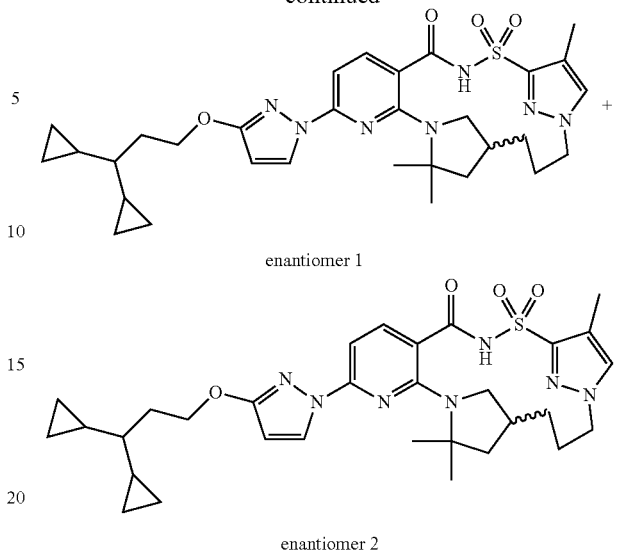

enantiomer 1 enantiomer 2

4-[3-(3,3-Dicyclopropylpropoxy)-1H-pyrazol-1-yl]-12,20,20-trimethyl-10λ⁶-thia-1,3,9,14,22-pentaazatetracyclo[16.2.1.1¹¹,¹⁴.0²,⁷]docosa-2(7),3,5,11(22),12-pentaene-8,10,10-trione (53.7 mg) was subjected to chiral separation by SFC chromatography using a ChiralPak AS-3 (150×2.1 mm, 3 μm particle size) with 32% acetonitrile/methanol (90:10)/68% carbon dioxide mobile phase at 0.5 mL/min over 6.0 min (1.6 mg/mL solution in acetonitrile/methanol (90:10)) giving as the first enantiomer to elute, 4-[3-(3,3-dicyclopropylpropoxy)-1H-pyrazol-1-yl]-12,20,20-trimethyl-10λ⁶-thia-1,3,9,14,22-pentaazatetracyclo[16.2.1.1¹¹,¹⁴.0²,⁷]docosa-2(7),3,5,11(22),12-pentaene-8,10,10-trione (enantiomer 1) (Compound 201) (3.5 mg, 5%). ESI-MS m/z calc. 607.29407, found 608.38 (M+1)⁺; Retention time: 2.36 min (LC Method B). The second enantiomer to elute was 4-[3-(3,3-dicyclopropylpropoxy)-1H-pyrazol-1-yl]-12,20,20-trimethyl-10λ⁶-thia-1,3,9,14,22-pentaazatetracyclo[16.2.1.1¹¹,¹⁴.0²,⁷]docosa-2(7),3,5,11(22),12-pentaene-8,10,10-trione (enantiomer 2) (Compound 202) (5.0 mg, 7%). ESI-MS m/z calc. 607.29407, found 608.3 (M+1)⁺; Retention time: 2.49 min (LC Method B).

Example 176: Preparation of 8-[3-(3,3-dicyclopropylpropoxy)-1H-pyrazol-1-yl]-12,12,18-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Enantiomer 1) (Compound 203) and 8-[3-(3,3-dicyclopropylpropoxy)-1H-pyrazol-1-yl]-12,12,18-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Enantiomer 2) (Compound 204)

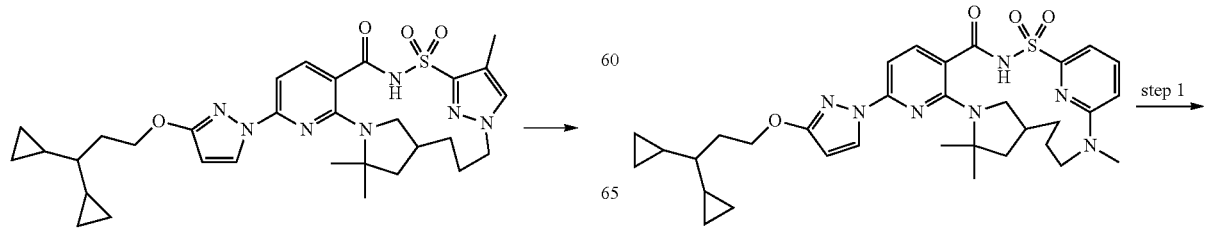

step 1

-continued

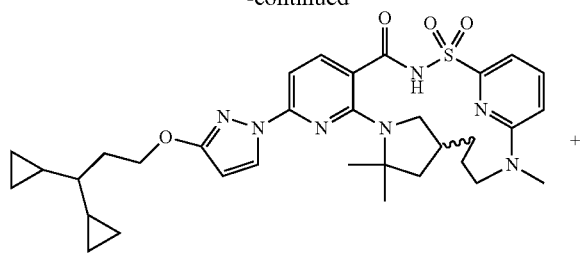

enantiomer 1

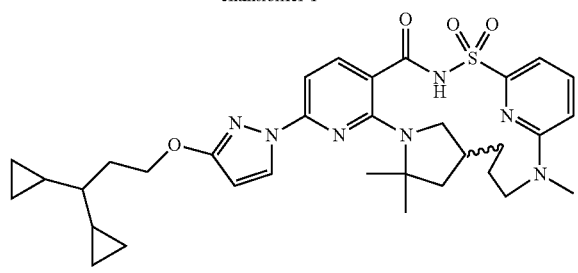

enantiomer 2

Step 1: 8-[3-(3,3-Dicyclopropylpropoxy)-1H-pyrazol-1-yl]-12,12,18-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Enantiomer 1) (Compound 203) and 8-[3-(3,3-dicyclopropylpropoxy)-1H-pyrazol-1-yl]-12,12,18-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Enantiomer 2) (Compound 204)

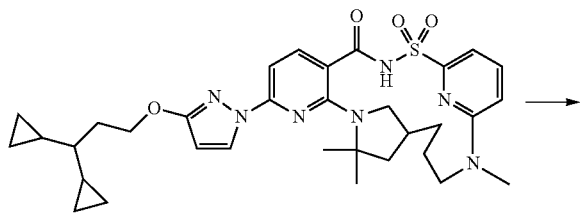

enantiomer 1

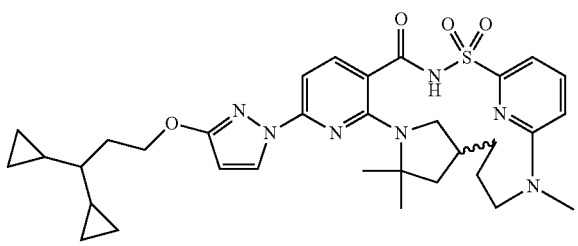

enantiomer 2

Racemic 8-[3-(3,3-dicyclopropylpropoxy)-1H-pyrazol-1-yl]-12,12,18-trimethyl-2λ⁶-thia-3,9,11,18,23-pentaazatetra-cyclo[17.3.1.1¹¹,¹⁴.0⁵,¹⁰]tetracosa-1(22),5,7,9,19(23),20-hexaene-2,2,4-trione (76 mg) was subjected to chiral SFC chromatography. The following SFC protocol was employed: ChiralPak AS-H (250×10 mm), 5 µm; mobile phase: 38% acetonitrile:methanol (90:10), 62% carbon dioxide, 70 µL, injection of a 16 mg/mL solution in acetonitrile:methanol:dimethyl sulfoxide (74:8:18) at 10 mL/min. The first enantiomer to elute was 8-[3-(3,3-dicyclopropylpropoxy)-1H-pyrazol-1-yl]-12,12,18-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (enantiomer 1) (Compound 203) (3.5 mg, 6%) as a white solid. ESI-MS m/z calc. 633.30975, found 634.4 (M+1)⁺; Retention time: 1.54 min (LC Method J). The second enantiomer to elute was 8-[3-(3,3-dicyclopropylpropoxy)-1H-pyrazol-1-yl]-12,12,18-trimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (enantiomer 2) (Compound 204) (3.5 mg, 6%) as a white solid. ESI-MS m/z calc. 633.30975, found 634.4 (M+1)⁺; Retention time: 1.54 min (LC Method J).

Example 177: Preparation of (14S)-12,12-dimethyl-8-(2-oxo-3-{3-[1-(trifluoromethyl)cyclopropyl]propyl}imidazolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 205)

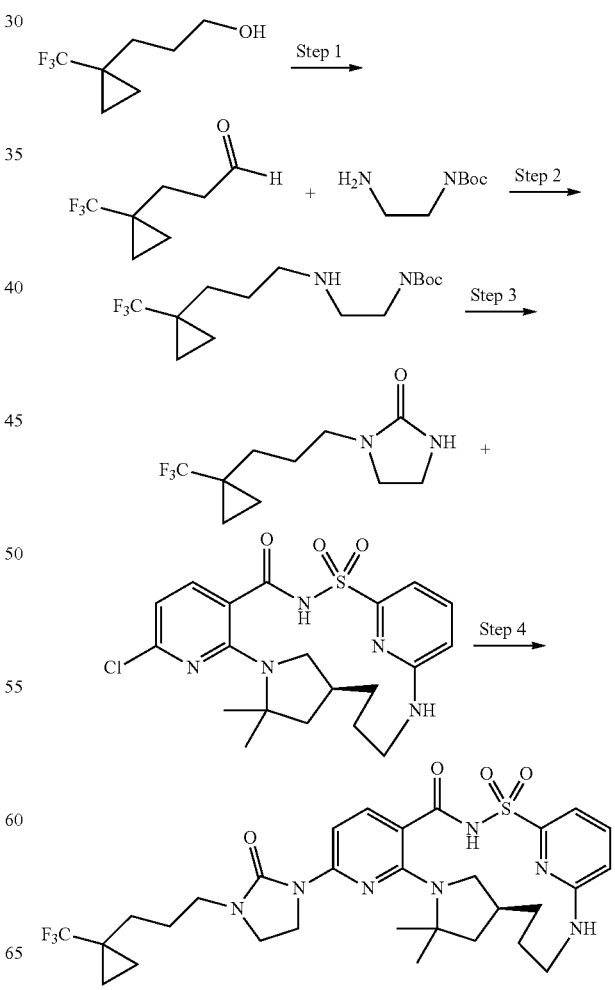

Step 1: 3-[1-(Trifluoromethyl)cyclopropyl]propanal

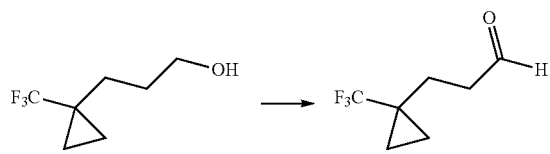 [SMILES: OCCCC1(C(F)(F)F)CC1 ; O=CCCC1(C(F)(F)F)CC1]

Dess-Martin Periodinane (880 mg, 2.075 mmol) was added to a stirred solution of 3-[1-(trifluoromethyl)cyclopropyl]propan-1-ol (350 mg, 1.665 mmol) in anhydrous methylene chloride (10 mL) at 0° C. (ice-water bath) under nitrogen. After 15 min, the bath was removed and the reaction was allowed to warm to ambient temperature and stirring was continued for another 3 h. The reaction was diluted with ether (60 mL) and saturated aqueous sodium bicarbonate (20 mL) was added slowly (to mitigate carbon dioxide gas evolution). Then sodium thiosulfate (10 mL) was added and the mixture was stirred at ambient temperature for 30 min. The layers were separated and the aqueous layer was extracted with ether (2×20 mL). The combined organics were washed with brine (20 mL), dried over anhydrous sodium sulfate, filtered and concentrated under reduced pressure (rotary evaporator, pressure set at 300 mbar in order to not evaporate somewhat volatile product) to afford 3-[1-(trifluoromethyl)cyclopropyl]propanal (250 mg, 90%) as a yellow oil. This material was used in the subsequent reaction without drying to neat material and without further purification. $^1$H NMR (400 MHz, Benzene-d$_6$) δ 9.15 (s, 1H), 1.99-1.90 (m, 2H), 1.52-1.44 (m, 2H), 0.68-0.59 (m, 2H), 0.00 (dd, J=2.5, 1.6 Hz, 2H).

Step 2: tert-Butyl N-[2-[3-[1-(trifluoromethyl)cyclopropyl]propylamino]ethyl]carbamate

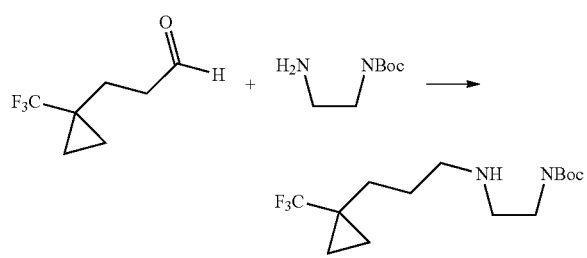

To a stirred solution of tert-butyl N-(2-aminoethyl)carbamate (242 mg, 1.510 mmol) in anhydrous methanol (7 mL) was added a solution of 3-[1-(trifluoromethyl)cyclopropyl]propanal (250 mg, 1.505 mmol) in anhydrous methanol (1 mL) under nitrogen. After the yellow solution was stirred at ambient temperature for 1 h, it was cooled to 0° C. (ice-water bath). Then sodium borohydride (125 mg, 3.304 mmol) was slowly added in two batches and the mixture was allowed to warm to ambient temperature and stirring was continued for 13 h. The volatiles were removed under reduced pressure. The residue was dissolved in ethyl acetate (30 mL) and washed with saturated aqueous sodium bicarbonate solution (2×15 mL) and brine (15 mL), dried over sodium sulfate, filtered and concentrated under reduced pressure to furnish crude tert-butyl N-[2-[3-[1-(trifluoromethyl)cyclopropyl]propylamino]ethyl]carbamate (467 mg, 100%) as a yellow oil contaminated with some bis-adduct. This material was taken directly to the next step. ESI-MS m/z calc. 310.1868, found 311.3 (M+1)$^+$; Retention time: 1.17 min (LC Method B).

Step 3: 1-[3-[1-(Trifluoromethyl)cyclopropyl]propyl]imidazolidin-2-one

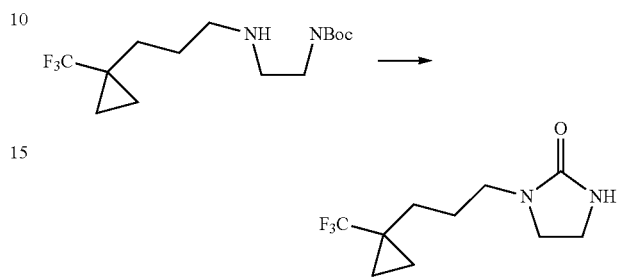

Solid potassium tert-butoxide (275 mg, 2.451 mmol) was added to a solution of crude tert-butyl N-[2-[3-[1-(trifluoromethyl)cyclopropyl]propylamino]ethyl]carbamate (250 mg, 0.8055 mmol, contaminated with some bis-adduct from the previous step) in anhydrous tetrahydrofuran (10 mL) under nitrogen and the reaction mixture was heated at 70° C. for 13 h. The reaction was allowed to cool to ambient temperature and the reaction mixture was acidified to pH=4-5 with aqueous hydrochloric acid (2.5 mL of 1 M, 2.500 mmol). After removing the volatiles under reduced pressure, the aqueous residue was extracted with ethyl acetate (3×25 mL). The combined organics were washed with brine (2×20 mL), dried over anhydrous sodium sulfate, filtered and concentrated under reduced pressure. The residue was purified by silica gel chromatography (0%-10% methanol in methylene chloride gradient) to afford 1-[3-[1-(trifluoromethyl)cyclopropyl]propyl]imidazolidin-2-one (72 mg, 38%) as an off-white solid. $^1$H NMR (400 MHz, Benzene-d$_6$) δ 5.35 (s, 1H), 2.84 (t, J=6.8 Hz, 2H), 2.54-2.41 (m, 4H), 1.33-1.25 (m, 2H), 1.23-1.17 (m, 2H), 0.63-0.54 (m, 2H), 0.05--0.06 (m, 2H). ESI-MS m/z calc. 236.11365, found 237.1 (M+1)$^+$; Retention time: 0.93 min (LC Method B).

Step 4: (14S)-12,12-Dimethyl-8-(2-oxo-3-{3-[1-(trifluoromethyl)cyclopropyl]propyl}imidazolidin-1-yl)-2λ$^6$-thia-3,9,11,18,23-pentaazatetracyclo[17.3.1.1 11,14.0 5,10]tetracosa-1(22),5,7,9,19(23),20-hexaene-2,2,4-trione (Compound 205)

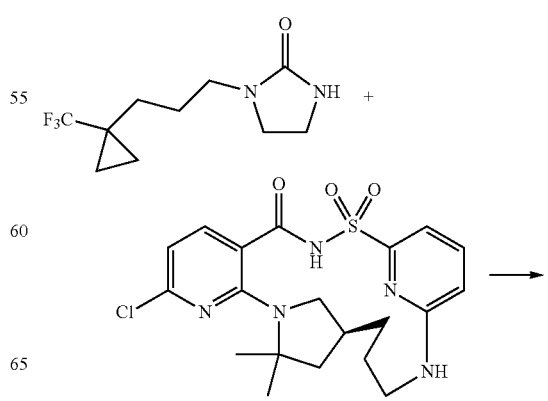

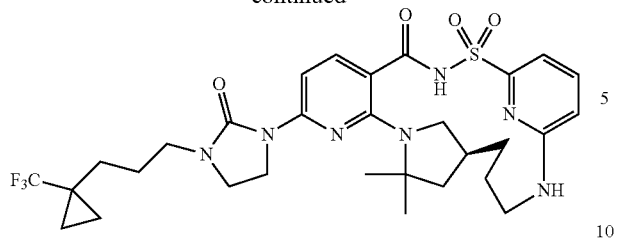

To a 4 mL vial, (14S)-8-chloro-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (50 mg, 0.1111 mmol), 1-[3-[1-(trifluoromethyl)cyclopropyl]propyl]imidazolidin-2-one (32 mg, 0.1355 mmol), cesium carbonate (130 mg, 0.3990 mmol), 4,5-bis(diphenylphosphino)-9,9-dimethylxanthene (10 mg, 0.01728 mmol) (Xantphos) and anhydrous dioxane (1.1 mL) were added, in that order. Nitrogen was bubbled through the heterogeneous mixture for 2 min. Then Pd₂(dba)₃ (10 mg, 0.01107 mmol) was added under nitrogen and nitrogen was bubbled through the reaction for another 2 min and capped the reaction under nitrogen. The mixture was stirred at 115° C. for 14 h. The mixture was allowed to cool to ambient temperature and was neutralized with glacial acetic acid (50 µL, 0.8792 mmol). The volatiles were removed under reduced pressure and the residue was taken up in dimethyl sulfoxide (1.5 mL) and filtered through a Whatman 0.45 µm PTFE syringe filter disc. The sample was purified using preparative reverse-phase HPLC-MS (30%-99% acetonitrile in water (hydrochloric acid as modifier)). The desired product fractions were combined and concentrated under reduced pressure and the residue was taken up in ethyl acetate (25 mL) and washed successively with saturated aqueous sodium bicarbonate (2×10 mL) and brine (10 mL). The organic layer was dried over anhydrous sodium sulfate, filtered and concentrated under reduced pressure to furnish (14S)-12,12-dimethyl-8-(2-oxo-3-{3-[1-(trifluoromethyl)cyclopropyl]propyl}imidazolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 205) (19.0 mg, 26%) as an off-white solid. ¹H NMR (400 MHz, Methanol-d₄) δ 7.70 (d, J=8.5 Hz, 1H), 7.53 (dd, J=8.5, 7.2 Hz, 1H), 7.43 (d, J=8.6 Hz, 1H), 7.15 (dd, J=7.2, 0.8 Hz, 1H), 6.65 (dd, J=8.5, 0.8 Hz, 1H), 4.14-4.07 (m, 1H), 4.07-4.02 (m, 1H), 4.02-3.95 (m, 1H), 3.56-3.45 (m, 2H), 3.29-3.19 (m, 3H), 3.03 (d, J=13.8 Hz, 1H), 2.86 (t, J=10.4 Hz, 1H), 2.21-2.09 (m, 1H), 1.83 (dd, J=11.7, 5.4 Hz, 2H), 1.78-1.69 (m, 2H), 1.69-1.63 (m, 4H, partially obscured by residual water peak), 1.61 (d, J=5.6 Hz, 2H), 1.60-1.57 (m, 1H), 1.55 (s, 3H), 1.42 (q, J=11.5 Hz, 1H), 1.32-1.26 (m, 1H), 0.96-0.90 (m, 2H), 0.72-0.66 (m, 2H). ESI-MS m/z calc. 649.2658, found 650.4 (M+1)⁺; Retention time: 1.92 min (LC Method B).

Example 178: Preparation of (14S)-12,12-dimethyl-8-(2-oxo-3-{2-[1-(trifluoromethyl)cyclopropyl]ethyl}imidazolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 211)

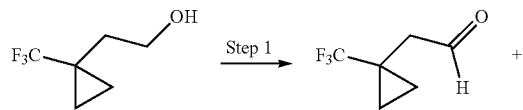

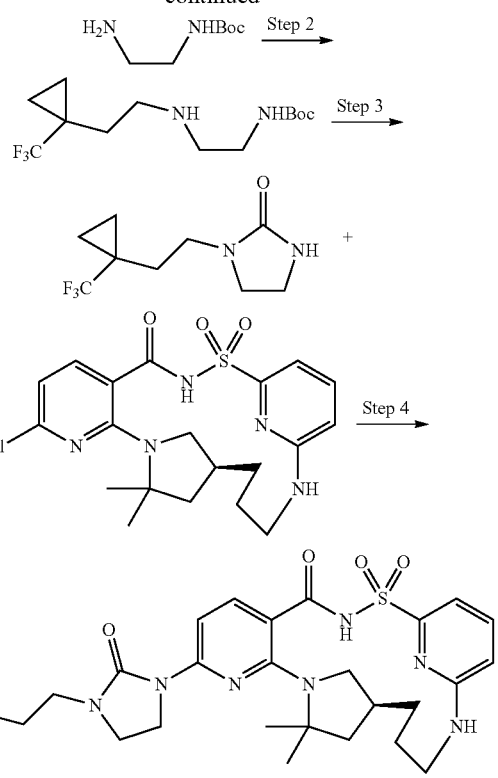

Step 1: 2-[1-(Trifluoromethyl)cyclopropyl]acetaldehyde

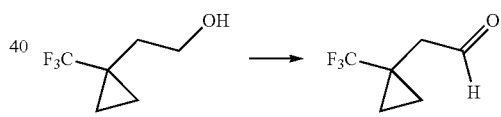

Dess-Martin Periodinane (2.43 g, 5.729 mmol) was added to a stirred solution of 2-[1-(trifluoromethyl)cyclopropyl]ethanol (700 mg, 4.542 mmol) in anhydrous methylene chloride (15 mL) at 0° C. (ice-water bath) under nitrogen. After 15 min, the bath was removed and the reaction was allowed to warm to ambient temperature and stirring was continued for another 3 h. The reaction was diluted with ether (60 mL) and saturated aqueous sodium bicarbonate (20 mL) was added slowly (to mitigate carbon dioxide gas evolution). Then, sodium thiosulfate (10 mL) was added and the mixture was stirred at ambient temperature for 30 min. The layers were separated and the aqueous layer was extracted with ether (2×20 mL). The combined organics were washed with brine (20 mL), dried over anhydrous sodium sulfate, filtered and concentrated under reduced pressure (at 300 mbar to avoid evaporation of the somewhat volatile product) to obtain 2-[1-(trifluoromethyl)cyclopropyl]acetaldehyde (500 mg, 72%) as crude material. Due to volatility, it was not further dried or further purified. ¹H NMR (400 MHz, Benzene-d₆) δ 9.24 (tt, J=2.3, 1.2 Hz, 1H), 1.77 (d, J=2.4 Hz, 2H), 0.66-0.59 (m, 2H), 0.00 (qd, J=4.4, 2.3 Hz, 2H). ¹⁹F NMR (376 MHz, Benzene-d₆) δ− 70.56.

Step 2: tert-Butyl N-[2-[2-[1-(trifluoromethyl)cyclopropyl]ethylamino]ethyl]carbamate

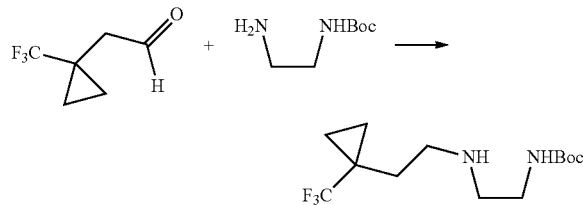

To a stirred solution of tert-butyl N-(2-aminoethyl)carbamate (527 mg, 3.289 mmol) in anhydrous methanol (15 mL) was added a solution of 2-[1-(trifluoromethyl)cyclopropyl]acetaldehyde (500 mg, 3.287 mmol) in anhydrous methanol (1 mL) under nitrogen. After the yellow solution was stirred at ambient temperature for 1 h, it was cooled to 0° C. (ice-water bath). Then sodium borohydride (260 mg, 6.872 mmol) was slowly added in two batches and the mixture was allowed to warm to ambient temperature and stirring continued for 15 h. The volatiles were removed under reduced pressure. The residue was dissolved in ethyl acetate (30 mL) and washed with saturated aqueous sodium bicarbonate solution (2×15 mL) and brine (15 mL), dried over sodium sulfate, filtered and concentrated under reduced pressure to furnish tert-butyl N-[2-[2-[1-(trifluoromethyl)cyclopropyl]ethylamino]ethyl]carbamate (970 mg, 100%) as a yellow oil. The crude material was used in the next step without any further purification. ESI-MS m/z calc. 296.17117, found 297.3 (M+1)+; Retention time: 0.79 min (LC Method B).

Step 3: 1-[2-[1-(Trifluoromethyl)cyclopropyl]ethyl]imidazolidin-2-one

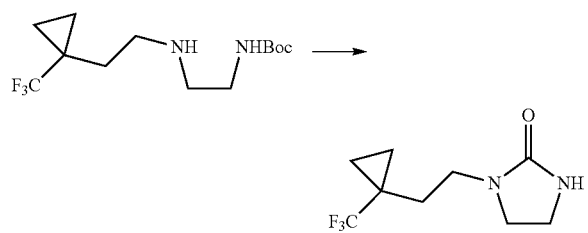

Solid potassium tert-butoxide (460 mg, 4.099 mmol) was added to a solution of tert-butyl N-[2-[2-[1-(trifluoromethyl)cyclopropyl]ethyl amino]ethyl]carbamate (400 mg, 1.350 mmol) in anhydrous tetrahydrofuran (20 mL) and the heterogeneous reaction mixture was heated at 70° C. for 13 h. The reaction mixture was allowed to cool to ambient temperature and acidified with glacial acetic acid (250 µL, 4.396 mmol). The volatiles were removed under reduced pressure and the residue was purified by silica gel chromatography (0%-10% methanol in methylene chloride gradient) to afford 1-[2-[1-(trifluoromethyl)cyclopropyl]ethyl]imidazolidin-2-one (127 mg, 42%) as an off-white solid. $^1$H NMR (400 MHz, Benzene-d$_6$) δ 4.99 (s, 1H), 3.35-3.20 (m, 2H), 2.71-2.56 (m, 4H), 1.70-1.59 (m, 2H), 0.86-0.73 (m, 2H), 0.46-0.33 (m, 2H). ESI-MS m/z calc. 222.09799, found 223.1 (M+1)+; Retention time: 0.78 min (LC Method B).

Step 4: (14S)-12,12-Dimethyl-8-(2-oxo-3-{2-[1-(trifluoromethyl)cyclopropyl]ethyl}imidazolidin-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 211)

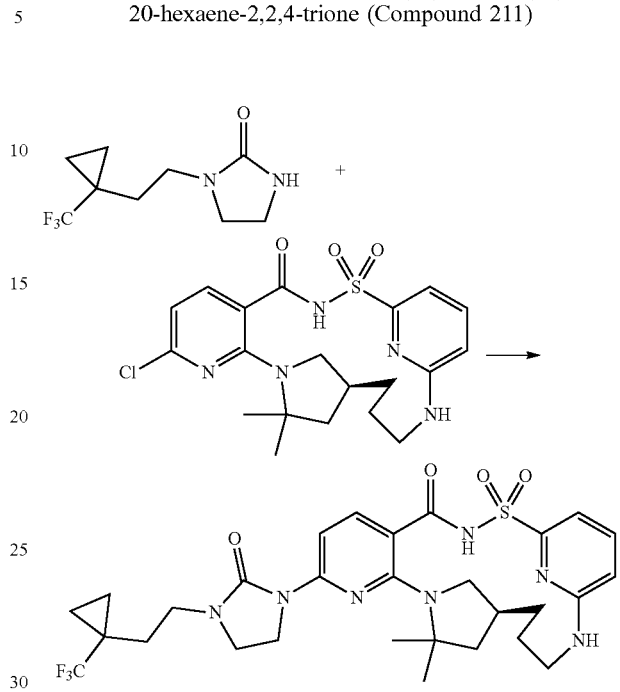

To a 4 mL vial, (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (50 mg, 0.1111 mmol), 1-[2-[1-(trifluoromethyl)cyclopropyl]ethyl]imidazolidin-2-one (30 mg, 0.1350 mmol), cesium carbonate (130 mg, 0.3990 mmol), 4,5-bis(diphenylphosphino)-9,9-dimethylxanthene (10 mg, 0.01728 mmol) (Xantphos) and anhydrous dioxane (1 mL) were added, in that order. Nitrogen was bubbled through the heterogeneous mixture for 2 min. Then Pd$_2$(dba)$_3$ (10 mg, 0.01107 mmol) was added under nitrogen and nitrogen was bubbled through the mixture for another 2 min and then capped under nitrogen. The mixture was stirred at 115° C. for 14 h. The mixture was allowed to cool to ambient temperature and then was neutralized with glacial acetic acid (50 µL, 0.8792 mmol). The volatiles were removed under reduced pressure and the residue was taken up in dimethyl sulfoxide (1.5 mL) and filtered through a Whatman 0.45 µm PTFE syringe filter disc. The sample was purified using preparative reverse-phase HPLC-MS (30%-99% acetonitrile in water (hydrochloric acid as modifier). The desired product fractions were combined and concentrated under reduced pressure and the residue was taken up in ethyl acetate (25 mL) and washed with brine (10 mL). The organic layer was dried over anhydrous sodium sulfate, filtered and concentrated under reduced pressure to obtain yellowish solid. The solid was further purified by silica gel column chromatography (0%-10% methanol in dichloromethane) to furnish (14S)-12,12-dimethyl-8-(2-oxo-3-{2-[1-(trifluoromethyl)cyclopropyl]ethyl}imidazolidin-1-yl)-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 211) (18 mg, 25%) as an off-white solid. $^1$H NMR (400 MHz, Methanol-d$_4$) δ 7.71 (d, J=8.6 Hz, 1H), 7.52 (dd, J=8.5, 7.2 Hz, 1H), 7.42 (d, J=8.6 Hz, 1H), 7.15 (dd, J=7.3, 0.8 Hz, 1H), 6.65 (d, J=8.5 Hz, 1H), 4.17-4.03 (m, 2H), 3.99 (td, J=10.2, 9.7, 6.7 Hz, 1H), 3.53 (ddd, J=9.5, 6.9, 2.5 Hz, 2H), 3.45-3.37 (m, 2H), 3.24 (t, J=8.7 Hz, 1H), 3.03 (d, J=13.7 Hz, 1H), 2.87 (t, J=10.5 Hz, 1H), 2.20-2.09

(m, 1H), 1.89-1.80 (m, 4H), 1.63 (s, 3H), 1.59 (t, J=12.2 Hz, 1H), 1.54 (s, 3H), 1.48-1.38 (m, 1H), 1.29 (s, 2H), 1.02-0.96 (m, 2H), 0.81-0.75 (m, 2H). ESI-MS m/z calc. 635.2502, found 636.4 (M+1)+; Retention time: 1.85 min (LC Method B).

Example 179: Preparation of (14S)-8-{3-[(4,4-difluorocyclohexyl)methyl]-2-oxoimidazolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 214)

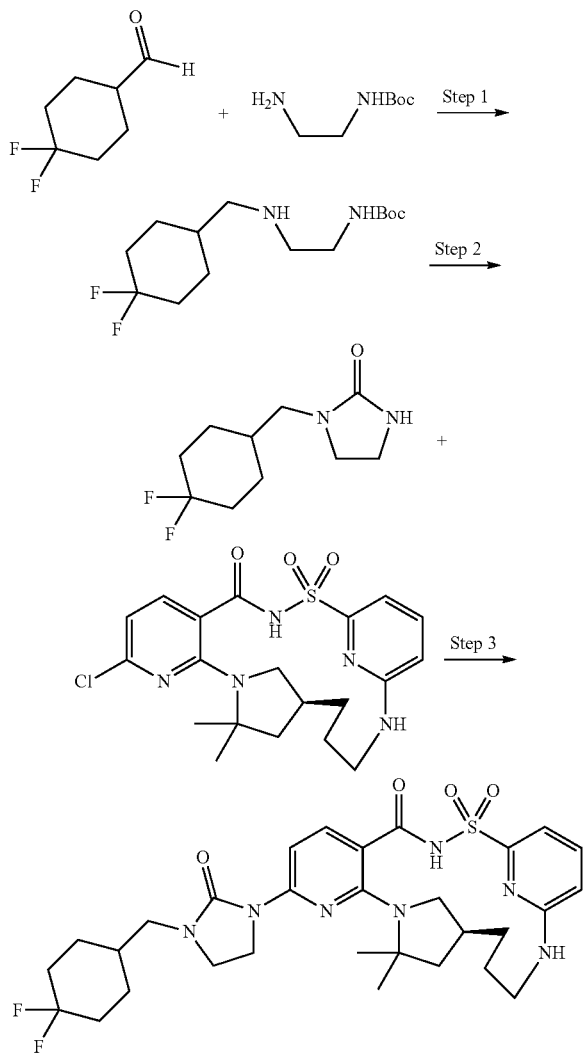

Step 1: tert-Butyl N-[2-[(4,4-difluorocyclohexyl)methylamino]ethyl]carbamate

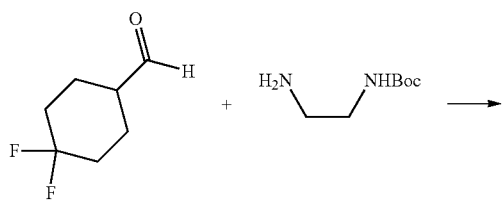

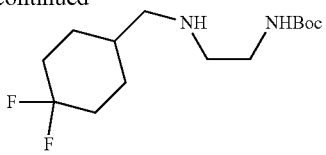

To a stirred solution of tert-butyl N-(2-aminoethyl)carbamate (325 mg, 2.029 mmol) in anhydrous methanol (15 mL) was added a solution of 4,4-difluorocyclohexanecarbaldehyde (300 mg, 2.025 mmol) in anhydrous methanol (1 mL) under nitrogen. After the yellow solution was stirred at ambient temperature for 1 h, it was cooled to 0° C. (ice-water bath). Then sodium borohydride (165 mg, 4.361 mmol) was slowly added in two batches and the mixture was allowed to warm to ambient temperature and stirring continued for 15 h. The volatiles were removed under reduced pressure. The residue was dissolved in ethyl acetate (30 mL) and washed with saturated aqueous sodium bicarbonate solution (2×15 mL) and brine (15 mL), dried over sodium sulfate, filtered and concentrated under reduced pressure to furnish tert-butyl N-[2-[(4,4-difluorocyclohexyl)methylamino]ethyl]carbamate (590 mg, 100%) as a yellow oil. The crude material was used for next step without any further purification. ¹H NMR (400 MHz, Benzene-d₆) δ 4.76 (s, 1H), 3.16 (q, J=5.8 Hz, 2H), 2.35 (t, J=5.9 Hz, 2H), 2.05 (d, J=6.5 Hz, 2H), 2.03-1.97 (m, 1H), 1.59 (s, 9H), 1.54-1.42 (m, 4H), 1.16-1.03 (m, 2H), 1.02-0.84 (m, 1H), 0.48 (s, 2H). ESI-MS m/z calc. 292.19623, found 293.3 (M+1)+; Retention time: 0.73 min (LC Method B).

Step 2: 1-[(4,4-Difluorocyclohexyl)methyl]imidazolidin-2-one

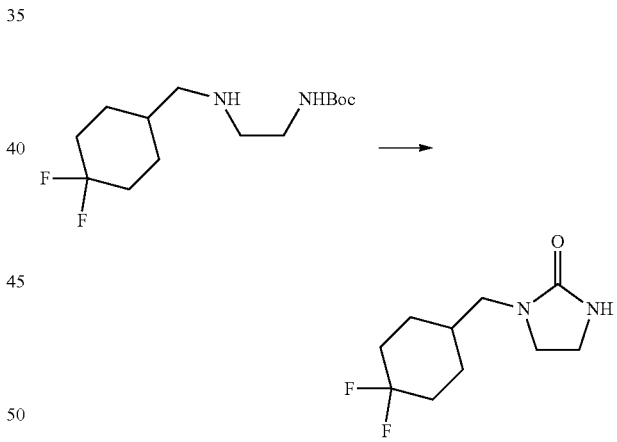

Solid potassium tert-butoxide (866 mg, 7.718 mmol) was added to a stirred solution of tert-butyl N-[2-[(4,4-difluorocyclohexyl)methylamino]ethyl]carbamate (750 mg, 2.565 mmol) in tetrahydrofuran (12 mL) and the heterogeneous reaction mixture was heated at 70° C. for 13 h. Once cooled to room temperature, the reaction mixture was acidified with glacial acetic acid (500 μL, 8.792 mmol) and concentrated under reduced pressure. The residue was partitioned between aqueous sodium bicarbonate (15 mL) and ethyl acetate (25 mL) and the layers were separated. The aqueous portion was extracted further with ethyl acetate (25 mL). The combined organics were washed with brine (20 mL), dried over anhydrous sodium sulfate, filtered and concentrated under reduced pressure to furnish 1-[(4,4-difluorocyclohexyl)methyl]imidazolidin-2-one (379 mg, 68%) as an off-white solid. ¹H NMR (400 MHz, Methanol-d₄) δ 3.51-3.44 (m, 2H), 3.42-3.35 (m, 2H), 3.04 (d, J=7.1 Hz, 2H), 2.09-1.98 (m, 2H), 1.83-1.65 (m, 5H), 1.33-1.20 (m, 2H). ESI-MS m/z calc. 218.12306, found 219.1 (M+1)⁺; Retention time: 0.7 min (LC Method B).

Step 3: (14S)-8-{3-[(4,4-Difluorocyclohexyl)methyl]-2-oxoimidazolidin-1-yl}-12,12-dimethyl-2λ⁶-thia-3,9,11,18,23-pentaazatetracyclo[17.3.1.111,14.0⁵,10]tetracosa-1(22),5,7,9,19(23),20-hexaene-2,2,4-trione (Compound 214)

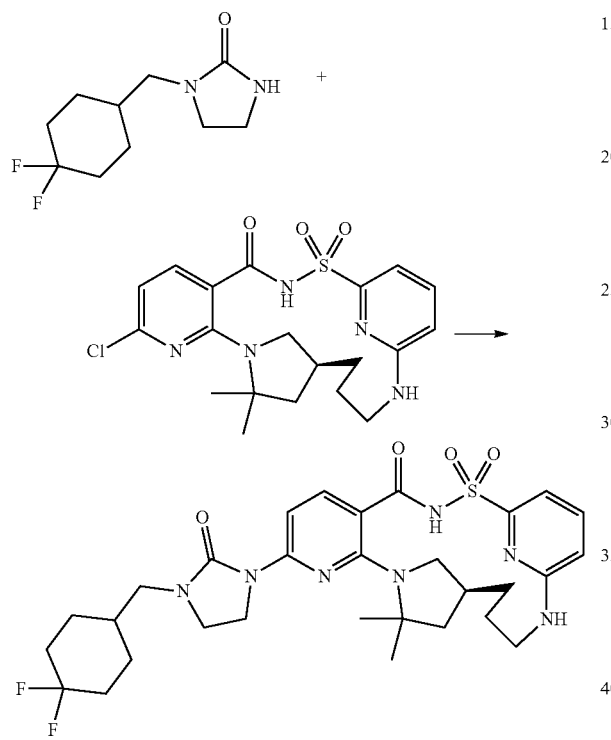

A 4 mL vial was charged with (14S)-8-chloro-12,12-dimethyl-2λ⁶-thia-3,9,11,18,23-pentaazatetracyclo[17.3.1.111,14.0⁵,10]tetracosa-1(23),5,7,9,19,21-hexaene-2,2,4-trione (50 mg, 0.1111 mmol), 1-[(4,4-difluorocyclohexyl)methyl]imidazolidin-2-one (34 mg, 0.1558 mmol), Pd₂(dba)₃ (15 mg, 0.01638 mmol), Xantphos (16 mg, 0.02765 mmol), cesium carbonate (213 mg, 0.6537 mmol) and anhydrous dioxane (0.75 mL). The mixture was sparged with nitrogen for about 5 min, capped and stirred at 120° C. for 22 h. The reaction mixture was concentrated by blowing nitrogen in the vial. The reaction was diluted with dimethyl sulfoxide (1.5 mL), microfiltered and subjected to reverse phase preparative HPLC (C₁₈) using a gradient of acetonitrile in water (1% to 99%) and hydrochloric acid as a modifier. The pure fractions were collected and the organic solvents were evaporated. The solution was extracted with dichloromethane and the organic phase was dried over sodium sulfate then filtered. Evaporation of the filtrate gave a solid that was purified by flash chromatography on silica gel using a gradient of methanol (0% to 5%) in dichloromethane. The pure fractions were collected and the solvents evaporated. The residue was triturated with dichloromethane/hexanes and the solvents evaporated to give (14S)-8-[3-[(4,4-difluorocyclohexyl)methyl]-2-oxoimidazolidin-1-yl]-12,12-dimethyl-2λ⁶-thia-3,9,11,18,23-pentaazatetracyclo[17.3.1.111,14.0⁵,10]tetracosa-1(22),5,7,9,19(23),20-hexaene-2,2,4-trione (Compound 214) (20 mg, 27%) as an off-white solid. ¹H NMR (400 MHz, dimethyl sulfoxide-d₆) δ 12.26 (s, 1H), 7.65-7.51 (m, 2H), 7.40 (d, J=8.6 Hz, 1H), 7.03 (d, J=7.1 Hz, 1H), 6.94 (broad d, J=9.1 Hz, 1H), 6.69 (d, J=8.5 Hz, 1H), 4.03-3.85 (m, 3H), 3.56-3.40 (m, 2H), 3.18-3.03 (m, 3H), 2.94 (d, J=13.3 Hz, 1H), 2.71 (d, J=10.9 Hz, 1H), 2.12-1.96 (m, 3H), 1.86-1.69 (m, 7H), 1.63-1.43 (m, 9H), 1.36-1.27 (m, 1H), 1.23-1.10 (m, 2H). ESI-MS m/z calc. 631.2752, found 632.3 (M+1)⁺; Retention time: 1.79 min (LC Method B).

Example 180: Preparation of (14S)-12,12-dimethyl-8-[2-oxo-3-(3,3,3-trifluoro-2,2-dimethylpropyl)imidazolidin-1-yl]-2λ⁶-thia-3,9,11,18,23-pentaazatetracyclo[17.3.1.111,14.0⁵,10]tetracosa-1(22),5,7,9,19(23),20-hexaene-2,2,4-trione (Compound 225)

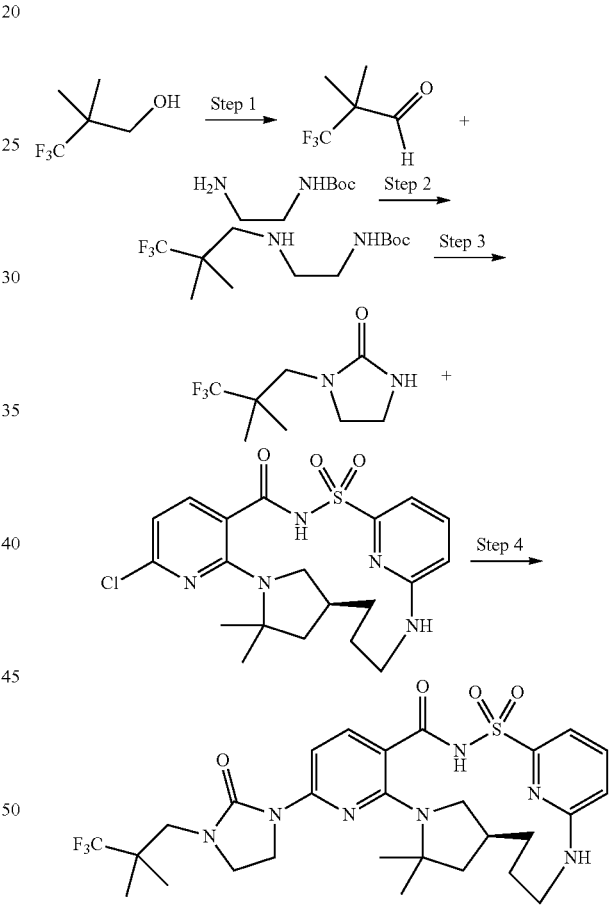

Step 1: 3,3,3-Trifluoro-2,2-dimethyl-propanal

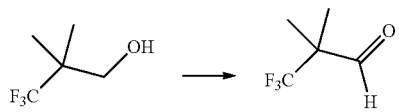

Dess-Martin Periodinane (in dichloromethane) (5.4 g, 12.73 mmol) was added to a stirred solution of 3,3,3- trifluoro-2,2-dimethyl-propan-1-ol (2.0 g of 75% w/w, 10.55 mmol) in anhydrous dichloromethane (30 mL) at 0° C. (ice-water bath) under nitrogen. After 15 min, the bath was removed and the reaction was allowed to warm to ambient temperature and stirring continued for another 2 h. The reaction was diluted with ether (80 mL) and saturated aqueous sodium bicarbonate (30 mL) was added slowly (to mitigate carbon dioxide gas evolution). Then a solution of 10% sodium thiosulfate (10 mL) was added and the mixture was stirred at ambient temperature for 30 min over which time all solids dissolved. The layers were separated and the aqueous layer was extracted with ether (2×30 mL). The combined organics were washed with brine (30 mL), dried over anhydrous sodium sulfate, filtered and partially concentrated under reduced pressure to about 3-5 mL, to obtain 3,3,3-trifluoro-2,2-dimethyl-propanal (1.37 g, 93%) as crude solution in ether which was used directly in the next step. ESI-MS m/z calc. 140.0449, found 141.2 (M+1)$^+$; Retention time: 0.42 min (LC Method E).

Step 2: tert-Butyl N-[2-[(3,3,3-trifluoro-2,2-dimethyl-propyl)amino]ethyl]carbamate

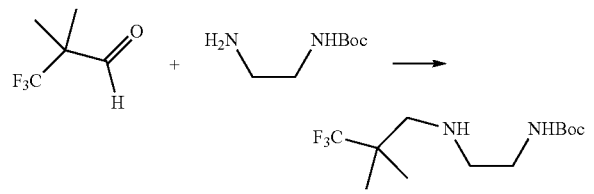

To a stirred solution of tert-butyl N-(2-aminoethyl)carbamate (1.2 g, 7.490 mmol) in anhydrous methanol (45 mL) was added the crude ethereal solution of 3,3,3-trifluoro-2,2-dimethyl-propanal (1.37 g, 9.778 mmol) described in the previous step in anhydrous methanol (8 mL) under nitrogen. After the pale yellow solution was stirred at ambient temperature for 1 h, it was cooled to 0° C. (ice-water bath). Then sodium borohydride (875 mg, 23.13 mmol) was added slowly in two batches and the mixture was allowed to warm to ambient temperature and stirring was continued for 24 h. The volatiles were removed under reduced pressure. The residue was dissolved in ethyl acetate (100 mL) and washed with saturated aqueous sodium bicarbonate solution (2×50 mL) and brine (50 mL), dried over sodium sulfate, filtered and concentrated under reduced pressure to afford tert-butyl N-[2-[(3,3,3-trifluoro-2,2-dimethyl-propyl)amino]ethyl]carbamate (777 mg, 36%) as a clear viscous oil. ESI-MS m/z calc. 284.17117, found 285.2 (M+1)$^+$; Retention time: 0.97 min (LC Method E).

Step 3: 1-(3,3,3-Trifluoro-2,2-dimethyl-propyl)imidazolidin-2-one

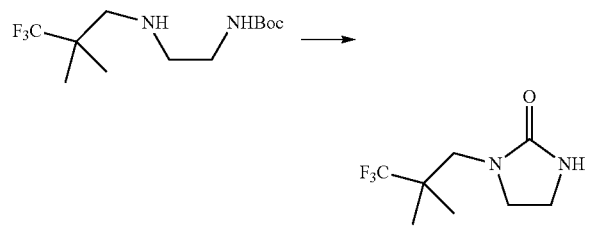

Solid potassium tert-butoxide (860 mg, 7.664 mmol) was added to a solution of tert-butyl N-[2-[(3,3,3-trifluoro-2,2-dimethyl-propyl)amino]ethyl]carbamate (777 mg, 2.733 mmol) in anhydrous tetrahydrofuran (40 mL) and the heterogeneous reaction mixture was heated at 70° C. for 18 h. The reaction mixture was allowed to cool to ambient temperature and acidified to pH 5 with aqueous hydrochloric acid (1 M). The volatiles were removed under reduced pressure and the aqueous residue was extracted with ethyl acetate (3×50 mL). The combined organics were washed with brine (2×40 mL), dried over anhydrous sodium sulfate, filtered and concentrated under reduced pressure. The residue was purified by silica gel chromatography (0%-10% methanol in methylene chloride) to afford 1-(3,3,3-trifluoro-2,2-dimethyl-propyl)imidazolidin-2-one (19.38 mg, 3%) as an off-white solid. $^1$H NMR (400 MHz, Chloroform-d) δ 3.57-3.48 (m, 2H), 3.44-3.39 (m, 2H), 3.25 (d, J=2.5 Hz, 2H), 1.16 (d, J=5.9 Hz, 6H). ESI-MS m/z calc. 210.09799, found 211.1 (M+1)$^+$; Retention time: 0.94 min (LC Method E).

Step 4: (14S)-12,12-dimethyl-8-[2-oxo-3-(3,3,3-trifluoro-2,2-dimethylpropyl) imidazolidin-1-yl]-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound 225)

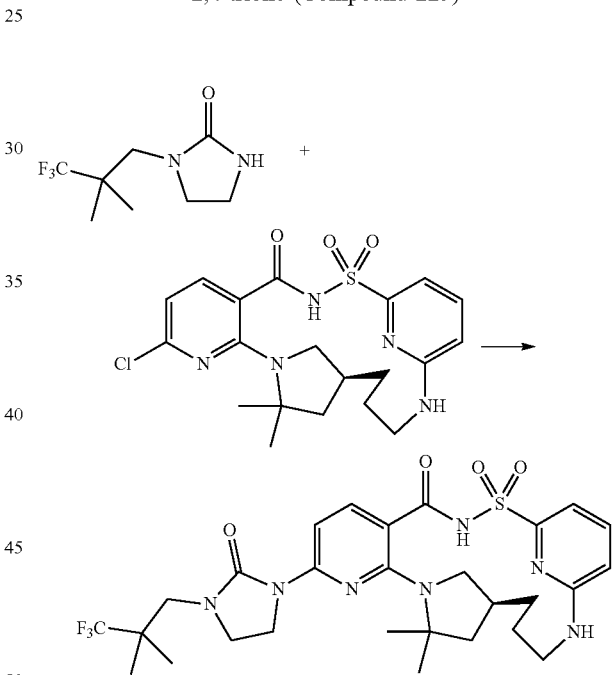

A 5 mL vial was charged with (14S)-8-chloro-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (40 mg, 0.08890 mmol), 1-(3,3,3-trifluoro-2,2-dimethyl-propyl)imidazolidin-2-one (20.56 mg, 0.09781 mmol), Pd$_2$(dba)$_3$ (21.5 mg, 0.02348 mmol), Xantphos (13.5 mg, 0.02333 mmol), cesium carbonate (150 mg, 0.4604 mmol) and anhydrous dioxane (800 μL). The mixture was sparged with nitrogen for 1-2 min, capped and stirred at 120° C. for 20 h and then cooled to room temperature. The solvent was evaporated, the reaction was diluted with dimethyl sulfoxide (900 μL), microfiltered and purified by reverse-phase preparative chromatography utilizing a C$_{18}$ column (10%-99% acetonitrile in water+5 mM hydrochloric acid over a 15 minute run). The product fractions were combined, brine was added and the organic solvents were evaporated. The product was extracted with dichloromethane, the organic phase was dried over sodium sulfate and evaporation of the solvents gave a solid. The solid was purified by silica gel chromatography using a gradient from 100% dichloromethane to 5% methanol in dichloromethane. Pure fractions were collected and the solvents evaporated however impurities remained. The material was diluted with dimethyl sulfoxide (900 μL) and purified by reverse-phase preparative chromatography utilizing a $C_{18}$ column (20%-80% acetonitrile in water+5 mM hydrochloric acid over a 30 minute run) to give as an off-white solid, (14S)-12,12-dimethyl-8-[2-oxo-3-(3,3,3-trifluoro-2,2-dimethylpropyl)imidazolidin-1-yl]-2λ$^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 225) (1.9 mg, 3%). ESI-MS m/z calc. 623.2502, found 624.2 (M+1)$^+$; Retention time: 1.88 min (LC Method E).

Example 181: Preparation of (14S)-8-{3-[(adamantan-1-yl)methyl]-2-oxoimidazolidin-1-yl}-12,12-dimethyl-2λ$^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 229)

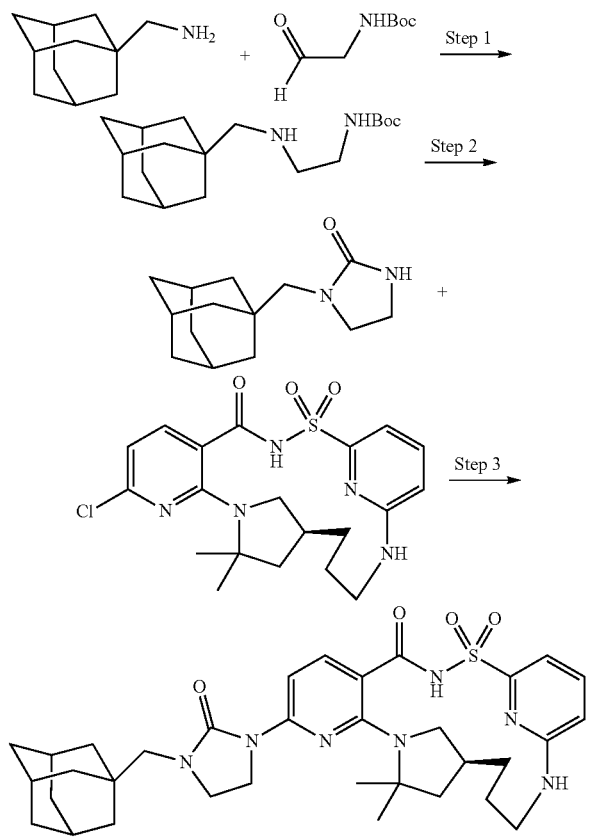

Step 1: tert-Butyl N-[2-(1-adamantylmethylamino)ethyl]carbamate

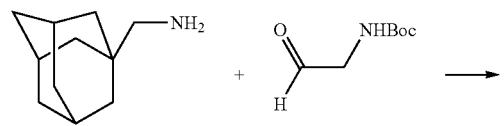

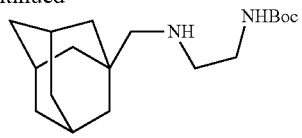

To a stirred solution of tert-butyl N-(2-oxoethyl)carbamate (494 mg, 3.103 mmol) in anhydrous methylene chloride (20 mL) was added a solution of 1-adamantylmethanamine (509 mg, 3.080 mmol) in anhydrous methylene chloride (1 mL) followed by addition of glacial acetic acid (200 μL, 3.517 mmol) at ambient temperature under nitrogen. The clear reaction was stirred for 30 min, then sodium triacetoxyborohydride (1.0 g, 4.718 mmol) was added in one portion at ambient temperature and stirring continued for 13 h. The volatiles were removed under reduced pressure. The residue was taken up in ethyl acetate (30 mL) and washed with saturated aqueous sodium bicarbonate solution (2×15 mL) and brine (15 mL), dried over anhydrous sodium sulfate, filtered and concentrated under reduced pressure to furnish tert-butyl N-[2-(1-adamantylmethylamino)ethyl]carbamate (901 mg, 95%) as a yellow gum. The crude material was used in the next step without further purification. ESI-MS m/z calc. 308.24637, found 309.4 (M+1)$^+$; Retention time: 1.09 min (LC Method B).

Step 2: 1-(1-Adamantylmethyl)imidazolidin-2-one

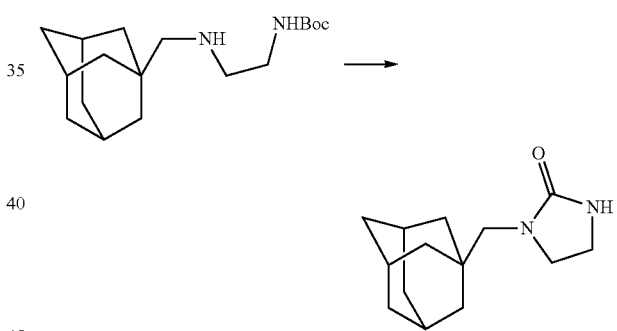

Solid potassium tert-butoxide (520 mg, 4.634 mmol) was added to a stirred solution of tert-butyl N-[2-(1-adamantylmethylamino)ethyl]carbamate (470 mg, 1.524 mmol) in anhydrous tetrahydrofuran (13 mL) under nitrogen and the reaction mixture was heated at 70° C. for 13 h. The heterogeneous mixture was allowed to cool to ambient temperature and was acidified with hydrochloric acid (6.0 mL of 1.0 M, 6.000 mmol) and the volatiles were removed under reduced pressure. The aqueous residue was extracted with ethyl acetate (3×10 mL) and the combined organics were washed with brine (10 mL), dried over anhydrous sodium sulfate, filtered and concentrated under reduced pressure. The residue was purified by silica gel chromatography (0%-10% methanol in $CH_2C_2$) to afford 1-(1-adamantylmethyl)imidazolidin-2-one (49 mg, 14%) as an off-white solid. $^1$H NMR (400 MHz, Benzene-d$_6$) δ 5.31 (s, 1H), 2.90 (dd, J=8.9, 6.6 Hz, 2H), 2.83 (s, 2H), 2.73 (dd, J=8.7, 6.7 Hz, 2H), 2.06-1.98 (m, 3H), 1.80-1.73 (m, 3H), 1.69 (dq, J=12.4, 2.3 Hz, 3H), 1.61 (d, J=2.8 Hz, 6H). ESI-MS m/z calc. 234.17322, found 235.2 (M+1)$^+$; Retention time: 1.51 min (LC Method B).

1073

Step 3: (14S)-8-{3-[(adamantan-1-yl)methyl]-2-oxoimidazolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 229)

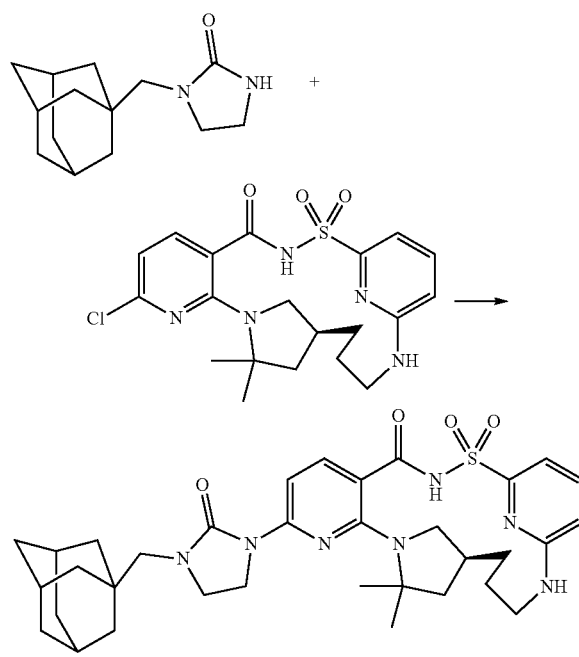

To a 4 mL vial, (14S)-8-chloro-12,12-dimethyl-2λ⁶-thia-3,9,11,18,23-pentaazatetracyclo[17.3.1.1¹¹,¹⁴.0⁵,¹⁰]tetracosa-1 (23),5,7,9,19,21-hexaene-2,2,4-trione (20 mg, 0.04298 mmol), 1-(1-adamantylmethyl)imidazolidin-2-one (13 mg, 0.05548 mmol), cesium carbonate (52 mg, 0.1596 mmol), Xantphos (4 mg, 0.006913 mmol) and anhydrous dioxane (1.0 mL) were added, in that order. Nitrogen was bubbled through the heterogeneous mixture for 2 min. Then Pd₂(dba)₃ (4 mg, 0.004368 mmol) was added under nitrogen and nitrogen was bubbled through the reaction mixture for another 2 min and capped the mixture under nitrogen. The mixture was stirred at 115° C. for 15 h. The mixture was allowed to cool to ambient temperature and was neutralized with glacial acetic acid (20 µL, 0.3517 mmol). The volatiles were removed under reduced pressure and the residue was taken up in dimethyl sulfoxide (1.0 mL) and filtered through a Whatman 0.45 µm PTFE syringe filter disc. The sample was purified using preparative reverse-phase HPLC-MS (30%-99% acetonitrile in water (hydrochloric acid as modifier)) giving (14S)-8-{3-[(adamantan-1-yl)methyl]-2-oxoimidazolidin-1-yl}-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 229) (12 mg, 43%) as a yellowish solid. ESI-MS m/z calc. 647.3254, found 648.5 (M+1)⁺; Retention time: 1.82 min (LC Method G).

1074

Example 182: Preparation of 23,23-dimethyl-11-(3-{2-[1-(trifluoromethyl)cyclo propyl]ethoxy}-1H-pyrazol-1-yl)-17λ⁶-thia-2,8,10,16,22-pentaazatetracyclo[16.3.1.1⁵,⁸.0⁹,¹⁴]tricosa-1(22),9,11,13,18,20-hexaene-15,17,17-trione (Compound 236)

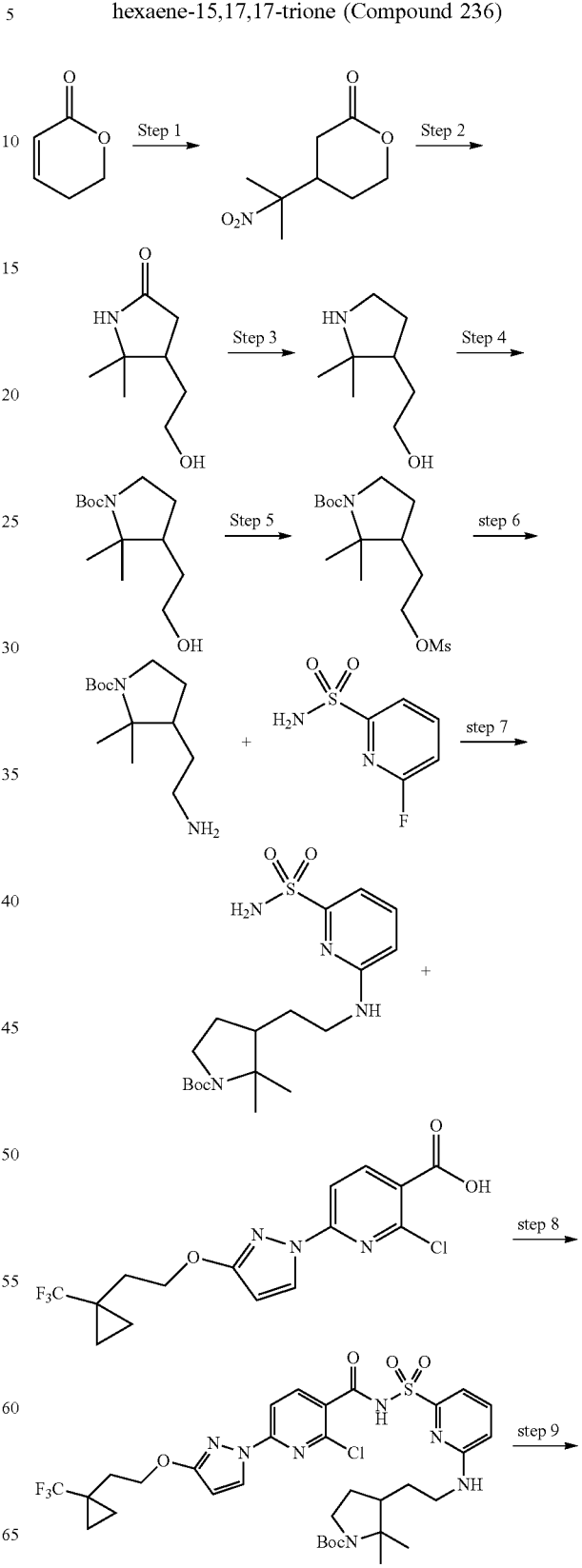

-continued

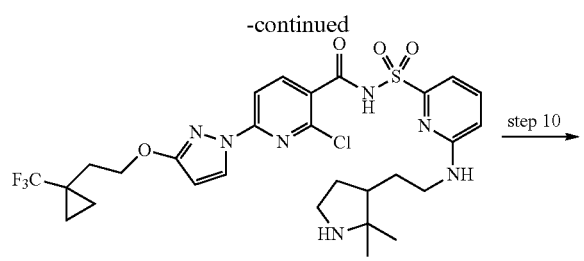

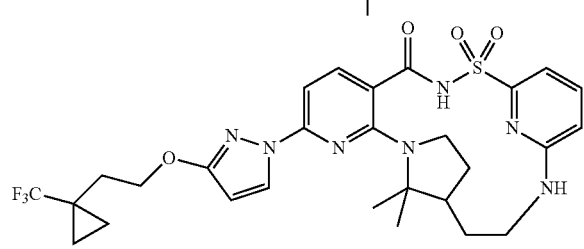

Step 1:
4-(1-Methyl-1-nitroethyl)-tetrahydropyran-2-one

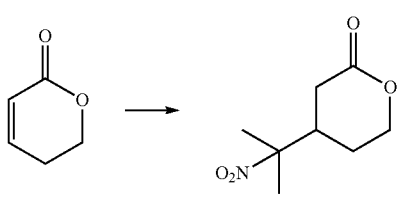

5,6-Dihydropyran-2-one (50 g, 510 mmol) and 1,8-diazabicyclo[5.4.0]undec-7-ene (7.6 mL, 51 mmol) were dissolved in 2-nitropropane (138 mL, 1530 mmol) and the resulting mixture was heated to 100° C. for 2.5 h under nitrogen. The reaction was cooled to room temperature and concentrated in vacuo to remove excess volatiles. The remaining oil was dissolved in ethyl acetate (1 L) and extracted with 1M hydrochloric acid (100 mL) and water (100 mL). The aqueous phases were discarded and the organic phase was dried over sodium sulfate, filtered and concentrated in vacuo to obtain 4-(1-methyl-1-nitroethyl)-tetrahydropyran-2-one (85 g, 79%) as an orange solid. ESI-MS m/z calc. 187.00, found 188.00 (M+1)$^+$; Retention time: 2.62 min (LC Method P).

Step 2:
4-(2-Hydroxyethyl)-5,5-dimethylpyrrolidin-2-one

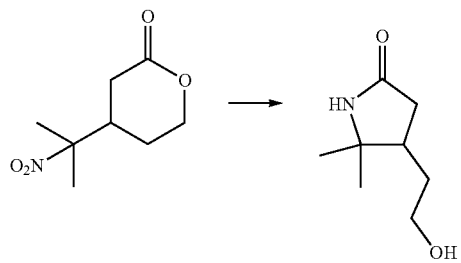

4-(1-Methyl-1-nitroethyl)-tetrahydropyran-2-one (85 g, 454 mmol) was dissolved in ethanol (1.2 L), then Raney Nickel (10 g, 170 mmol) was added and the resulting slurry was hydrogenated at 2 bar H$_2$/80° C. for 25 h. The reaction mixture was filtered, the filter cake was discarded and the filtrate was returned to the reactor and heated to 120° C. for 23 h. The mixture was concentrated to an oil in vacuo to obtain 4-(2-hydroxyethyl)-5,5-dimethylpyrrolidin-2-one (63.5 g, 89%) as a pale yellow solid. ESI-MS m/z calc. 157.00, found 158.20 (M+1)$^+$; Retention time: 1.30 min (LC Method P).

Step 3: 2-(2,2-Dimethylpyrrolidin-3-yl)-ethanol

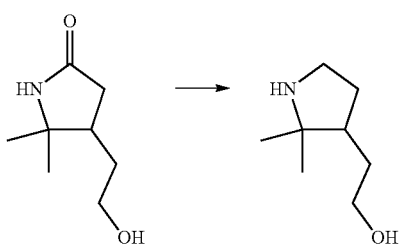

4-(2-Hydroxyethyl)-5,5-dimethylpyrrolidin-2-one (63.5 g, 404 mmol) was dissolved in tetrahydrofuran (2 L). Lithium aluminum hydride (61.3 g, 1616 mmol) was added in small portions and the resulting slurry was refluxed under nitrogen for 45 h, cooled to room temperature and carefully quenched with a saturated solution of sodium sulfate (300 mL). The mixture was diluted with MTBE (1 L) and filtered. The filter cake was discarded and the filtrate was dried over sodium sulfate, filtered and concentrated in vacuo to obtain 2-(2,2-dimethylpyrrolidin-3-yl)-ethanol (50.8 g, 87%) as a pale yellow oil. ESI-MS m/z calc. 143.00, found 144.20 (M+1)$^+$; Retention time: 0.68 min (LC Method P). The crude product was used without further purification.

Step 4: 3-(2-Hydroxyethyl)-2,2-dimethyl-pyrrolidine-1-carboxylic acid tert-butyl ester

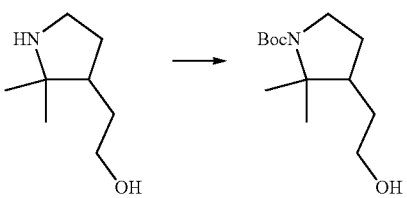

2-(2,2-Dimethylpyrrolidin-3-yl)-ethanol (50.8 g, 355 mmol) was dissolved in a mixture of dichloromethane (350 mL) and water (350 mL). Sodium bicarbonate (59.6 g, 710 mmol) and di-tert butyl dicarbonate (73.6 g, 337 mmol) were added and the resulting mixture was stirred at room temperature for 19 h. Sodium hydroxide (14 g, 350 mmol) and water (50 mL) were then added and the mixture was stirred at room temperature for 18 h then diluted with diethyl ether (1 L). The phases were separated and the aqueous phase was extracted with diethyl ether (2×350 mL). The aqueous phase was discarded and the combined organic phases were dried over sodium sulfate, concentrated in vacuo, then triturated with hexane. The resulting pale yellow solid was collected by vacuum filtration to obtain 3-(2-hydroxyethyl)-2,2-dimethyl-pyrrolidine-1-carboxylic acid tert-butyl ester (60.0 g, 69%) as a pale yellow solid. ESI-MS m/z calc. 243.00, found 244.00 (M+1)+; Retention time: 4.24 min (LC Method P).

Step 5: 3-(2-Methanesulfonyloxyethyl)-2,2-dimethylpyrrolidine-1-carboxylic acid tert-butyl ester

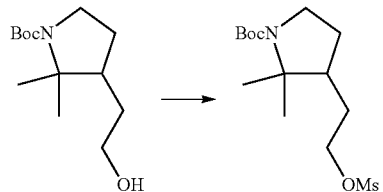 [SMILES: CC(C)(C)OC(=O)N1CCC(CCO)C1(C)C ; CC(C)(C)OC(=O)N1CCC(CCOS(C)(=O)=O)C1(C)C]

3-(2-Hydroxyethyl)-2,2-dimethyl-pyrrolidine-1-carboxylic acid tert-butyl ester (54.5 g, 224 mmol) was dissolved in dichloromethane (545 mL). Triethylamine (62.5 mL, 448 mmol) was added and the resulting solution was chilled in an ice water bath, then methanesulfonyl chloride (19.2 mL, 247 mmol) was added dropwise over the course of 1 h. The ice bath was then removed and the reaction was stirred for 1 h at room temperature and then quenched with saturated aqueous sodium bicarbonate (200 mL). The phases were separated and the organic phase was extracted with water (2×200 mL). The aqueous phases were discarded and the organic phase was dried over sodium sulfate, filtered and concentrated in vacuo to obtain 3-(2-methanesulfonyloxyethyl)-2,2-dimethylpyrrolidine-1-carboxylic acid tert-butyl ester (72.2 g, quant.) as an orange oil. ESI-MS m/z calc. 321.00, found 322.20 (M+1)+; Retention time: 5.24 min (LC Method P).

Step 6: 3-(2-Aminoethyl)-2,2-dimethyl-pyrrolidine-1-carboxylic Acid Tert-Butyl Ester

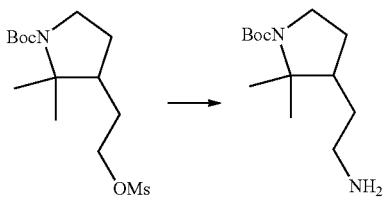 [SMILES: CC(C)(C)OC(=O)N1CCC(CCOS(C)(=O)=O)C1(C)C ; CC(C)(C)OC(=O)N1CCC(CCN)C1(C)C]

3-(2-Methanesulfonyloxyethyl)-2,2-dimethyl-pyrrolidine-1-carboxylic acid tert-butyl ester (10.0 g, 31.1 mmol) was dissolved in 1,4-dioxane (100 mL). 28% Ammonium hydroxide (100 mL) was added and the reaction was heated to 40° C. in a Parr reactor for 26 h. The 1,4-dioxane was removed in vacuo, and the remaining material was extracted with dichloromethane (2×100 mL). The phases were separated and the aqueous phase was discarded and the combined organic phases were dried over sodium sulfate, filtered and concentrated in vacuo. The remaining yellow oil was purified by silica gel chromatography (0%-15% methanol in dichloromethane gradient) to obtain 3-(2-aminoethyl)-2,2-dimethyl-pyrrolidine-1-carboxylic acid tert-butyl ester (5.1 g, 68%) as a pale yellow solid. ESI-MS m/z calc. 242.00, found 243.20 (M+1)+; Retention time: 3.09 min (LC Method P).

Step 7: tert-Butyl 2,2-dimethyl-3-[2-[(6-sulfamoyl-2-pyridyl)amino]ethyl]pyrrolidine-1-carboxylate

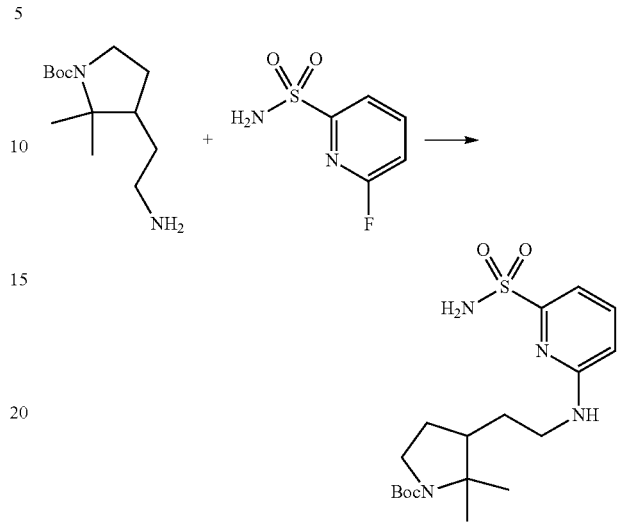

To 3-(2-aminoethyl)-2,2-dimethyl-pyrrolidine-1-carboxylic acid tert-butyl ester (500 mg, 2.063 mmol) and 6-fluoropyridine-2-sulfonamide (363.4 mg, 2.063 mmol) in dimethyl sulfoxide (4.21 mL) was added potassium carbonate (290.8 mg, 2.104 mmol) and the mixture stirred at 100° C. for 20 h then allowed to cool to room temperature Diluted with ethyl acetate and poured into saturated aqueous NH4Cl. Separated the layers then washed the organic layer with saturated aqueous brine, dried (sodium sulfate), filtered and concentrated to a yellow foam which was purified by silica gel chromatography using a shallow gradient from 100% hexanes to 100% ethyl acetate giving tert-butyl 2,2-dimethyl-3-[2-[(6-sulfamoyl-2-pyridyl)amino]ethyl]pyrrolidine-1-carboxylate (497.5 mg, 61%) as a white solid. ESI-MS m/z calc. 398.19876, found 399.1 (M+1)+; Retention time: 0.58 min (LC Method A).

Step 8: tert-Butyl 3-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethyl]-2,2-dimethyl-pyrrolidine-1-carboxylate

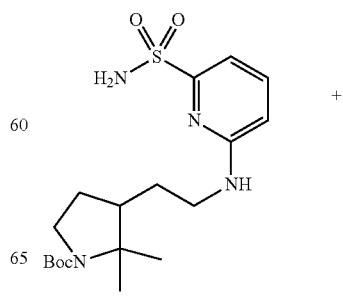

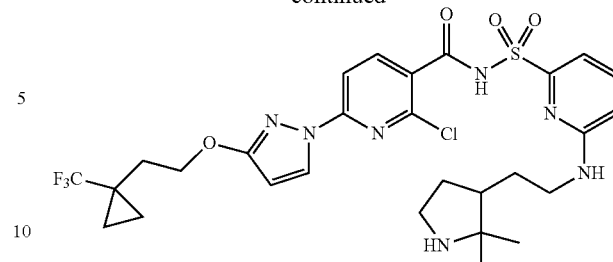

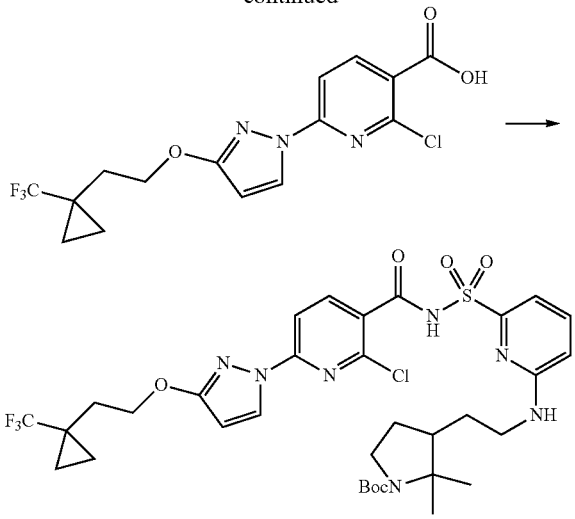

2-Chloro-6-[3-[2-[1-(trifluoromethyl)cyclopropyl]ethoxy]pyrazol-1-yl]pyridine-3-carboxylic acid (499.7 mg, 1.330 mmol) and carbonyl diimidazole (269.8 mg, 1.664 mmol) (recrystallized from tetrahydrofuran) were combined in tetrahydrofuran (6.89 mL) and stirred for 60 min at room temperature Then tert-butyl 2,2-dimethyl-3-[2-[(6-sulfamoyl-2-pyridyl)amino]ethyl]pyrrolidine-1-carboxylate (530 mg, 1.330 mmol) in tetrahydrofuran (2.65 mL) was added followed by 1,8-diazabicyclo[5.4.0]undec-7-ene (1.013 g, 6.654 mmol) and the reaction was stirred at room temperature for 16 h. Removed the tetrahydrofuran by rotary evaporation and dissolved the residue in ethyl acetate and washed with 6 N hydrochloric acid (1×), then brine (1×), dried (sodium sulfate), filtered and concentrated to a white solid which was chromatographed on a 275 g $C_{18}$ reverse phase column eluting with a gradient from 50%-100% acetonitrile in water giving tert-butyl 3-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethyl]-2,2-dimethyl-pyrrolidine-1-carboxylate (497.5 mg, 49%) as a white solid. $^1$H NMR (400 MHz, dimethyl sulfoxide-$d_6$) δ 12.75 (s, 1H), 8.40 (d, J=2.8 Hz, 1H), 8.12 (d, J=8.3 Hz, 1H), 7.70 (d, J=8.3 Hz, 1H), 7.62 (dd, J=8.5, 7.2 Hz, 1H), 7.21 (s, 1H), 7.18 (d, J=7.2 Hz, 1H), 6.74 (d, J=8.4 Hz, 1H), 6.18 (d, J=2.8 Hz, 1H), 4.35 (t, J=7.1 Hz, 2H), 3.25 (s, 2H), 3.02 (d, J=9.1 Hz, 1H), 2.09 (t, J=7.1 Hz, 2H), 1.90-1.57 (m, 4H), 1.41-1.31 (m, 11H), 1.29 (s, 2H), 1.19 (d, J=1.7 Hz, 1H), 0.98 (d, J=5.1 Hz, 2H), 0.96 (t, J=4.2 Hz, 3H), 0.89 (d, J=5.1 Hz, 2H). ESI-MS m/z calc. 755.248, found 756.1 (M+1)$^+$; Retention time: 0.84 min (LC Method A).

Step 9: 2-Chloro-N-[[6-[2-(2,2-dimethylpyrrolidin-3-yl)ethylamino]-2-pyridyl]sulfonyl]-6-[3-[2-[1-(trifluoromethyl)cyclopropyl]ethoxy]pyrazol-1-yl]pyridine-3-carboxamide

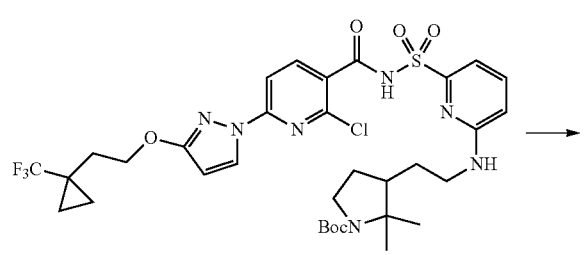

tert-Butyl 3-[2-[[6-[[2-chloro-6-[3-[2-[1-(trifluoromethyl)cyclopropyl]ethoxy]pyrazol-1-yl]pyridine-3-carbonyl]sulfamoyl]-2-pyridyl]amino]ethyl]-2,2-dimethyl-pyrrolidine-1-carboxylate (498.6 mg, 0.6593 mmol) was dissolved in dichloromethane (2.176 mL) and to the mixture was added trifluoroacetic acid (2.032 mL, 26.37 mmol) and the mixture was stirred at room temperature for 60 min. Concentrated the mixture to dryness under reduced pressure, took up in saturated aqueous sodium bicarbonate and ethyl acetate and separated the layers. (solubility of product in ethyl acetate under these conditions is very poor, addition of some methanol helps). Washed the ethyl acetate layer with 6 N hydrochloric acid then dried (sodium sulfate), filtered and concentrated the organic layer by rotary evaporation followed by drying under vacuum giving 2-chloro-N-[[6-[2-(2,2-dimethylpyrrolidin-3-yl)ethylamino]-2-pyridyl]sulfonyl]-6-[3-[2-[1-(trifluoromethyl)cyclopropyl]ethoxy]pyrazol-1-yl]pyridine-3-carboxamide (351.2 mg, 81%) as a white solid. ESI-MS m/z calc. 655.19556, found 656.1 (M+1)$^+$; Retention time: 0.58 min (LC Method A).

Step 10: 23,23-Dimethyl-11-(3-{2-[1-(trifluoromethyl)cyclopropyl]ethoxy}-1H-pyrazol-1-yl)-17λ$^6$-thia-2,8,10,16,22-pentaazatetracyclo[16.3.1.1$^{5,8}$.0$^{9,14}$]tricosa-1(22),9,11,13,18,20-hexaene-15,17,17-trione (Compound 236)

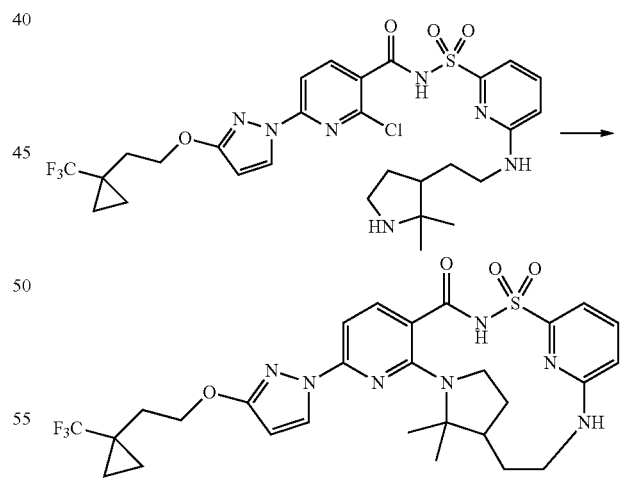

Combined 2-chloro-N-[[6-[2-(2,2-dimethylpyrrolidin-3-yl)ethylamino]-2-pyridyl]sulfonyl]-6-[3-[2-[1-(trifluoromethyl)cyclopropyl]ethoxy]pyrazol-1-yl]pyridine-3-carboxamide (351.2 mg, 0.5353 mmol), potassium carbonate (369.8 mg, 2.676 mmol), 3 Å molecular sieves and dimethyl sulfoxide (21.3 mL) in a vial, purged with nitrogen, capped, heated to 180° C. and stirred for 18 h. Cooled to room temperature and the mixture was filtered, diluted with ethyl acetate and washed with a saturated aqueous sodium bicarbonate solution, followed by brine. The organics were separated, dried over sodium sulfate and evaporated then purified by silica gel chromatography using a gradient from 100% hexanes to 100% ethyl acetate (product elutes after reaching 100% ethyl acetate) to afford as a white solid, 23,23-dimethyl-11-(3-{2-[1-(trifluoromethyl)cyclopropyl]ethoxy}-1H-pyrazol-1-yl)-17λ⁶-thia-2,8,10,16,22-pentaazatetracyclo[16.3.1.15,8.09,14]tricosa-1(22),9,11,13,18,20-hexaene-15,17,17-trione (Compound 236) (5.7 mg, 2%). ESI-MS m/z calc. 619.2189, found 620.1 (M+1)⁺; Retention time: 2.08 min (LC Method B).

Example 183: Preparation of (14S)-12,12-dimethyl-8-(2-oxo-3-{[4-(trifluoromethyl)cyclohexyl]methyl}imidazolidin-1-yl)-2λ⁶-thia-3,9,11,18,23-pentaazatetracyclo[17.3.1.111,14.05,10]tetracosa-1(22),5,7,9,19(23),20-hexaene-2,2,4-trione (Compound 239)

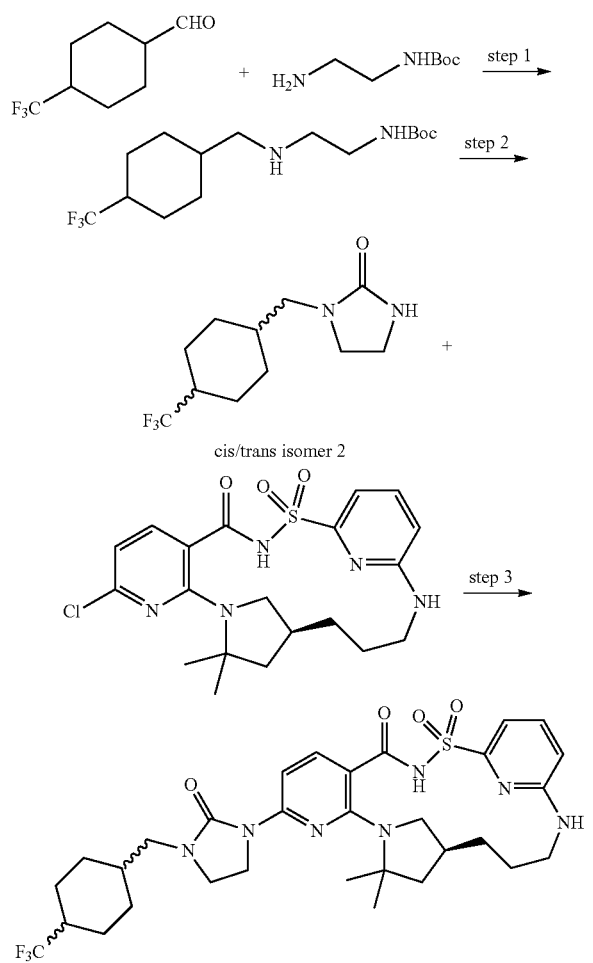

Step 1: tert-Butyl N-[2-[[4-(trifluoromethyl)cyclohexyl]methylamino]ethyl]carbamate

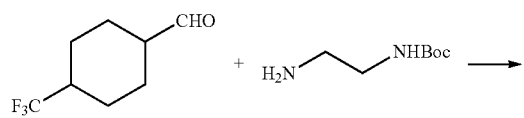

To a stirred solution of 4-(trifluoromethyl)cyclohexanecarbaldehyde (250 mg, 1.388 mmol) in anhydrous methanol (10 mL) was added a solution of tert-butyl N-(2-aminoethyl)carbamate (223 mg, 1.392 mmol) in anhydrous methanol (1 mL) under nitrogen. After the yellow solution was stirred at ambient temperature for 1 h, it was cooled to 0° C. (ice-water bath). Then sodium borohydride (112 mg, 2.960 mmol) was slowly added in two batches and the mixture was allowed to warm to ambient temperature and stirring continued for 15 h. The volatiles were removed under reduced pressure. The residue was dissolved in ethyl acetate (30 mL) and washed with saturated aqueous sodium bicarbonate solution (2×15 mL) and brine (15 mL), dried over sodium sulfate, filtered, and concentrated under reduced pressure to furnish tert-butyl N-[2-[[4-(trifluoromethyl)cyclohexyl]methylamino]ethyl]carbamate (400 mg, 89%) as a yellow gum. The crude material was used for next step without further purification. ESI-MS m/z calc. 324.20245, found 325.3 (M+1)⁺; Retention time: 0.9 min (LC Method B).

Step 2: 1-[[4-(Trifluoromethyl)cyclohexyl]methyl]imidazolidin-2-one (Cis/Trans Isomer 2)

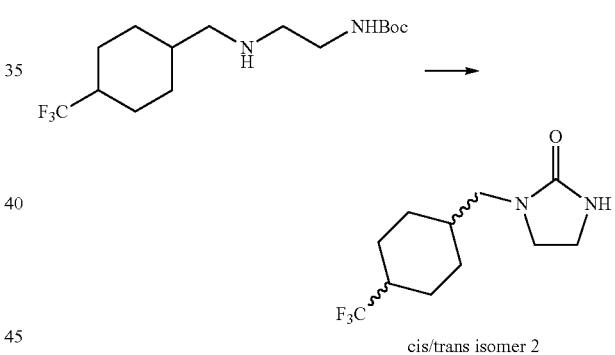

cis/trans isomer 2

Solid potassium tert-butoxide (270 mg, 2.406 mmol) was added to a stirred solution of tert-butyl N-[2-[[4-(trifluoromethyl)cyclohexyl]methylamino]ethyl]carbamate (260 mg, 0.8015 mmol) in anhydrous tetrahydrofuran (10 mL) under nitrogen, and the reaction mixture was heated at 70° C. for 13 h. The heterogeneous mixture was allowed to cool to ambient temperature and then was acidified with aqueous hydrochloric acid (3.0 mL of 1.0 M, 3.000 mmol) and removed the volatiles under reduced pressure. The aqueous residue was extracted with ethyl acetate (3×10 mL). The combined organics were washed with brine (10 mL), dried over anhydrous sodium sulfate, filtered and concentrated under reduced pressure. The residue was purified from preparative reverse-phase HPLC-MS (0%-70% acetonitrile in water (hydrochloric acid as modifier) to give as the second cis/trans isomer to elute, 1-[[4-(trifluoromethyl)cyclohexyl]methyl]imidazolidin-2-one (cis/trans isomer 2) (52 mg, 26%) as an off-white solid. ¹H NMR (400 MHz, Benzene-d₆) δ 4.93 (s, 1H), 2.89 (d, J=7.2 Hz, 2H), 2.77-2.63 (m, 4H), 1.80 (dd, J=13.4, 3.6 Hz, 2H), 1.72-1.57 (m, 1H), 1.52 (dd, J=13.4, 3.5 Hz, 2H), 1.22-1.06 (m, 3H), 0.66 (qd, J=13.3, 3.6 Hz, 2H). ESI-MS m/z calc. 250.1293, found 251.2 (M+1)⁺; Retention time: 1.3 min (LC Method B).

Step 3: (14S)-12,12-dimethyl-8-(2-oxo-3-{[4-(trifluoromethyl)cyclohexyl]methyl}imidazolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 239)

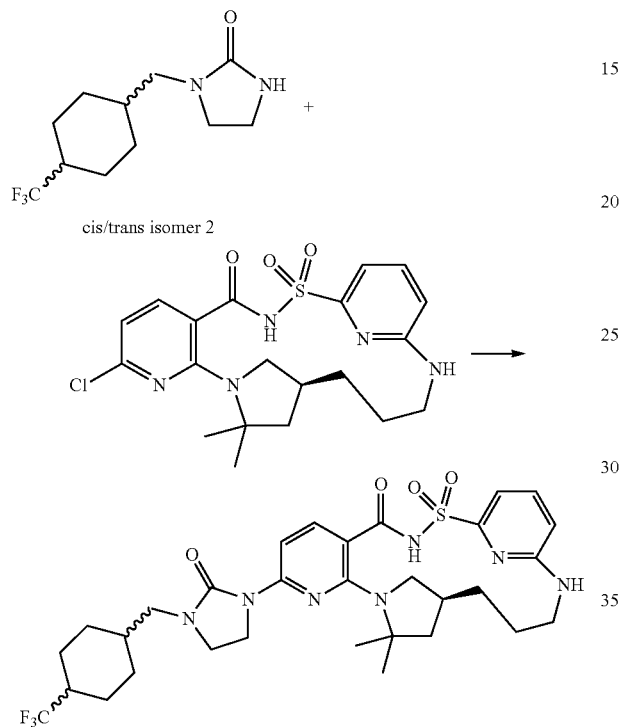

To a vial, (14S)-8-chloro-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (20 mg, 0.04445 mmol), 1-[[4-(trifluoromethyl)cyclohexyl]methyl]imidazolidin-2-one (13 mg, 0.05195 mmol), cesium carbonate (52 mg, 0.1596 mmol), Xantphos (4 mg, 0.006913 mmol) and anhydrous dioxane (0.7 mL) were added, in that order. Nitrogen was purged through the heterogeneous mixture for 3 min. Then Pd₂(dba)₃ (4 mg, 0.004368 mmol) was added under nitrogen and nitrogen was purged through the mixture for another 2 min then capped under nitrogen. The mixture was stirred at 108° C. for 15 h. The mixture was allowed to cool to ambient temperature and neutralized with glacial acetic acid (20 μL, 0.3517 mmol). The volatiles were removed under reduced pressure and the residue was taken up in dimethyl sulfoxide (1.5 mL) and filtered through a Whatman 0.45 μm PTFE syringe filter disc. The sample was purified using preparative reverse-phase HPLC-MS (30%-99% acetonitrile in water (hydrochloric acid as modifier) giving (14S)-12,12-dimethyl-8-(2-oxo-3-{[4-(trifluoromethyl)cyclohexyl]methyl}imidazolidin-1-yl)-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 239) (9 mg, 31%) as yellowish solid. This compound is a single isomer of unknown cis or trans orientation on the cyclohexane ring. ¹H NMR (400 MHz, dimethyl sulfoxide-d₆) δ 12.26 (s, 1H), 7.59 (d, J=8.6 Hz, 1H), 7.58-7.53 (m, 1H), 7.40 (dd, J=8.6, 2.7 Hz, 1H), 7.06-7.01 (m, 1H), 6.94 (d, J=8.7 Hz, 1H), 6.70 (dd, J=8.5, 0.8 Hz, 1H), 4.01-3.83 (m, 3H), 3.51-3.41 (m, 3H), 3.31-3.28 (m, 1H), 3.11-3.04 (m, 2H), 2.94 (d, J=13.4 Hz, 1H), 2.70 (t, J=0.8 Hz, 1H), 2.18 (t, J=8.1 Hz, 1H), 2.13-2.01 (m, 1H), 1.95-1.80 (m, 4H), 1.79-1.74 (m, 2H), 1.58 (s, 3H), 1.57-1.48 (m, 3H), 1.47 (s, 3H), 1.34-1.14 (m, 3H), 1.00 (q, J=12.6 Hz, 2H). ¹⁹F NMR (376 MHz, dimethyl sulfoxide-d₆) δ− 72.24 (d, J=8.9 Hz). ESI-MS m/z calc. 663.28143, found 664.4 (M+1)⁺; Retention time: 2.0 min (LC Method B).

Example 184: Preparation of 11-[3-(3,3-dicyclopropylpropoxy)-1H-pyrazol-1-yl]-7,7-dimethyl-17λ⁶-thia-2,8,10,16,22-pentaazatetracyclo[16.3.1.1⁵,⁸.0⁹,¹⁴]tricosa-1(22),9,11,13,18,20-hexaene-15,17,17-trione (Enantiomer 2) (Compound 250)

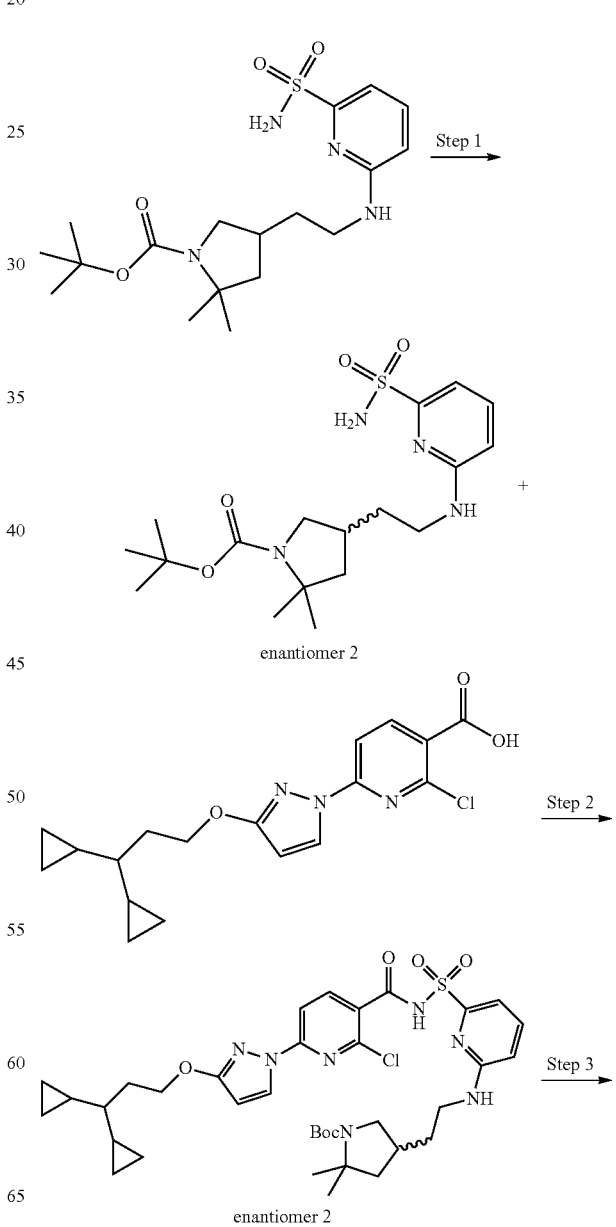

1085

-continued

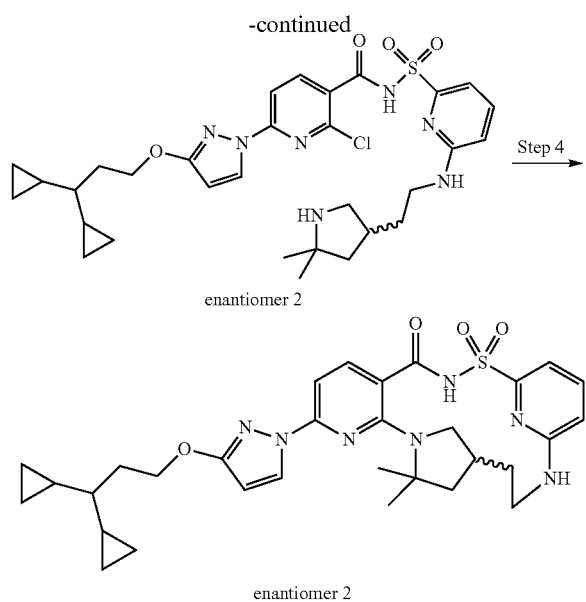

enantiomer 2

Step 1: tert-Butyl 2,2-dimethyl-4-[2-[(6-sulfamoyl-2-pyridyl)amino]ethyl]pyrrolidine-1-carboxylate (enantiomer 2)

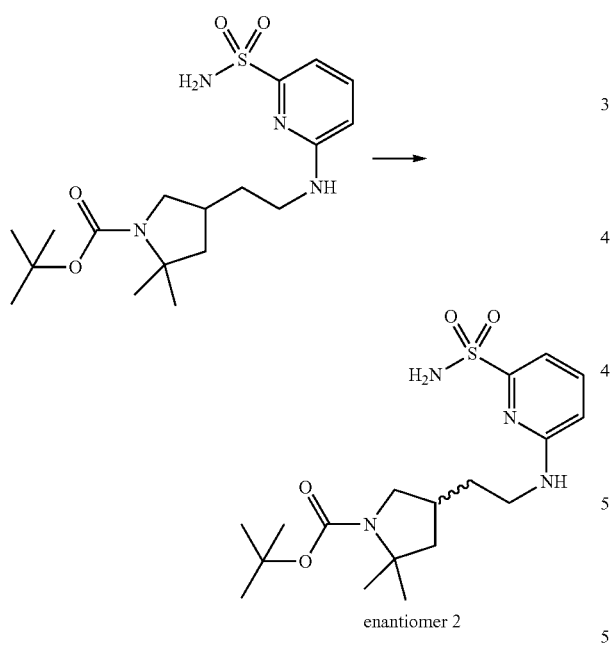

Racemic tert-butyl 2,2-dimethyl-4-[2-[(6-sulfamoyl-2-pyridyl)amino]ethyl]pyrrolidine-1-carboxylate (1.475 g, 3.701 mmol) was separated by chiral SFC using a ChiralPak IG (250×21.2 mm column, 5 μm particle size) with 32% methanol (no modifier))/68% carbon dioxide mobile phase at 70 mL/min giving as the second enantiomer to elute, tert-butyl 2,2-dimethyl-4-[2-[(6-sulfamoyl-2-pyridyl) amino]ethyl]pyrrolidine-1-carboxylate (enantiomer 2) (617 mg, 84%) as a white foam. ESI-MS m/z calc. 398.19876, found 399.3 (M+1)+; Retention time: 1.59 min (LC Method B).

1086

Step 2: tert-Butyl 4-[2-[[6-[[2-chloro-6-[3-(3,3-dicyclopropylpropoxy)pyrazol-1-yl]pyridine-3-carbonyl] sulfamoyl]-2-pyridyl]amino]ethyl]-2,2-dimethyl-pyrrolidine-1-carboxylate (Enantiomer 2)

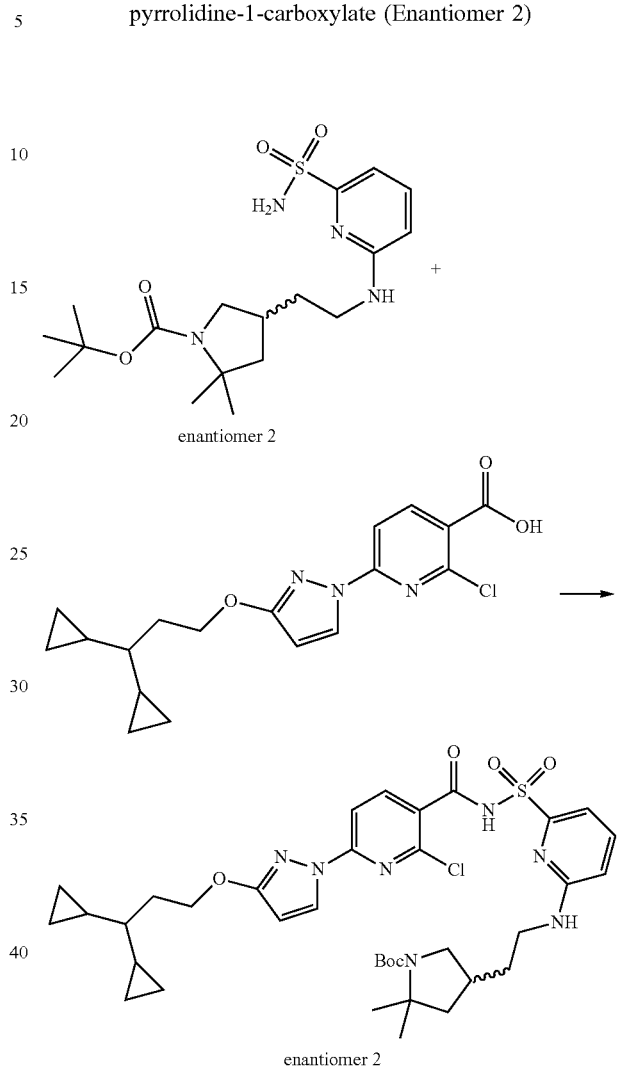

To a flask was added 2-chloro-6-[3-(3,3-dicyclopropylpropoxy)pyrazol-1-yl]pyridine-3-carboxylic acid (147.7 mg, 0.4082 mmol), recrystallized carbonyl diimidazole (66.2 mg, 0.4083 mmol) and tetrahydrofuran (4 mL). The reaction was stirred at 40° C. for 90 min. tert-Butyl 2,2-dimethyl-4-[2-[(6-sulfamoyl-2-pyridyl)amino]ethyl]pyrrolidine-1-carboxylate (enantiomer 2) (130 mg, 0.3262 mmol) was then added followed by 1,8-diazabicyclo[5.4.0]undec-7-ene (150 μL, 1.003 mmol). The reaction was stirred overnight. The reaction was filtered and purified via HPLC (30%-99% acetonitrile in water with a 0.1% hydrochloric acid modifier) to provide tert-butyl 4-[2-[[6-[[2-chloro-6-[3-(3,3-dicyclopropylpropoxy)pyrazol-1-yl]pyridine-3-carbonyl]sulfamoyl]-2-pyridyl]amino]ethyl]-2,2-dimethyl-pyrrolidine-1-carboxylate (enantiomer 2) (64 mg, 26%) as a white foam. ESI-MS m/z calc. 741.30756, found 742.4 (M+1)+; Retention time: 2.19 min (LC Method G).

Step 3: 2-Chloro-6-[3-(3,3-dicyclopropylpropoxy)pyrazol-1-yl]-N-[[6-[2-(5,5-dimethylpyrrolidin-3-yl)ethylamino]-2-pyridyl]sulfonyl]pyridine-3-carboxamide (Enantiomer 2)

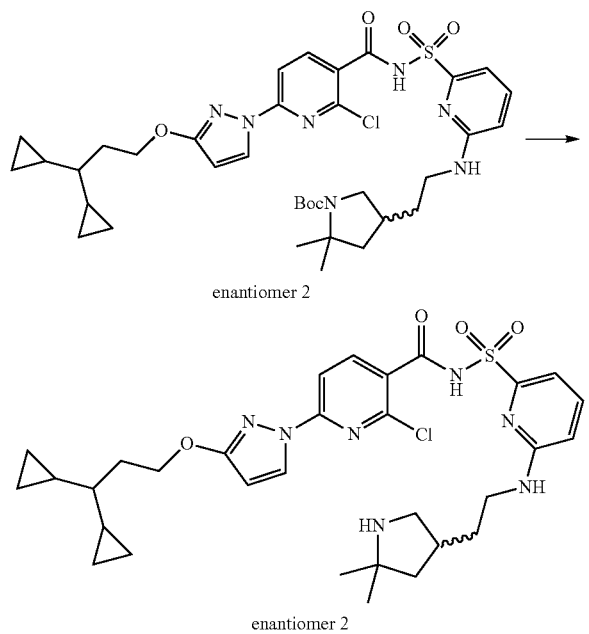

enantiomer 2 enantiomer 2

To a flask was added tert-butyl 4-[2-[[6-[[2-chloro-6-[3-(3,3-dicyclopropylpropoxy)pyrazol-1-yl]pyridine-3-carbonyl]sulfamoyl]-2-pyridyl]amino]ethyl]-2,2-dimethyl-pyrrolidine-1-carboxylate (enantiomer 2) (64 mg, 0.08622 mmol), dichloromethane (5 mL) and trifluoroacetic acid (250 µL, 3.245 mmol). The reaction was stirred for 30 min. The reaction was evaporated to dryness and neutralized with saturated sodium bicarbonate. The reaction was extracted with ethyl acetate dried over sodium sulfate, filtered, and evaporated to provide 2-chloro-6-[3-(3,3-dicyclopropylpropoxy) pyrazol-1-yl]-N-[[6-[2-(5,5-dimethylpyrrolidin-3-yl)ethylamino]-2-pyridyl]sulfonyl]pyridine-3-carboxamide (enantiomer 2) (51 mg, 92%) as a white solid. ESI-MS m/z calc. 641.2551, found 642.3 (M+1)+; Retention time: 1.11 min (LC Method G).

Step 4: 11-[3-(3,3-Dicyclopropylpropoxy)-1H-pyrazol-1-yl]-7,7-dimethyl-17λ6-thia-2,8,10,16,22-pentaazatetracyclo[16.3.1.15,8.09,14]tricosa-1(22),9,11,13,18,20-hexaene-15,17,17-trione (Enantiomer 2) (Compound 250)

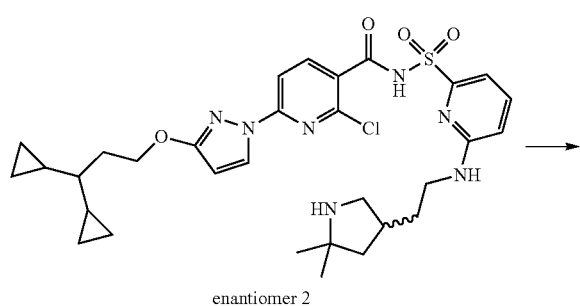

enantiomer 2

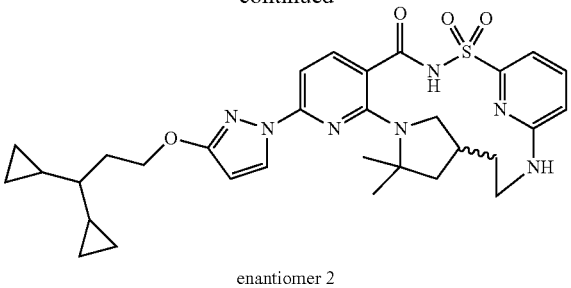

enantiomer 2

To a vial was added potassium carbonate (59 mg, 0.4269 mmol), cesium fluoride (25 mg, 0.1646 mmol), 3 Å molecular sieves and a solution of 2-chloro-6-[3-(3,3-dicyclopropylpropoxy)pyrazol-1-yl]-N-[[6-[2-(5,5-dimethylpyrrolidin-3-yl)ethylamino]-2-pyridyl]sulfonyl]pyridine-3-carboxamide (enantiomer 2) (51 mg, 0.07941 mmol) in dimethyl sulfoxide (3.5 mL). The reaction was placed in a preheated 150° C. oil bath and allowed to stir overnight. The reaction was cooled to room temperature, filtered and purified via HPLC (10%-99% acetonitrile in water with a 0.1% hydrochloric acid modifier) giving 11-[3-(3,3-dicyclopropylpropoxy)-1H-pyrazol-1-yl]-7,7-dimethyl-17λ6-thia-2,8,10,16,22-pentaazatetracyclo[16.3115,8.09,14]tricosa-1(22),9,11,13,18,20-hexaene-15,17,17-trione (enantiomer 2) (Compound 250) (14.1 mg, 29%). ESI-MS m/z calc. 605.27844, found 606.4 (M+1)+; Retention time: 1.9 min (LC Method G).

Example 185: Preparation of (14S)-8-[3-(2-{dispiro[2.0.2.1]heptan-7-yl}-2-oxoethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione (Compound 258)

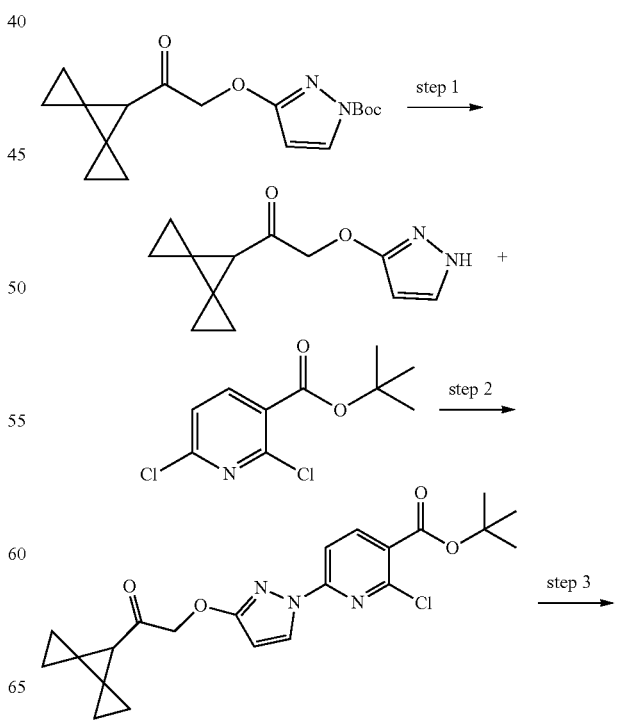

1089
-continued

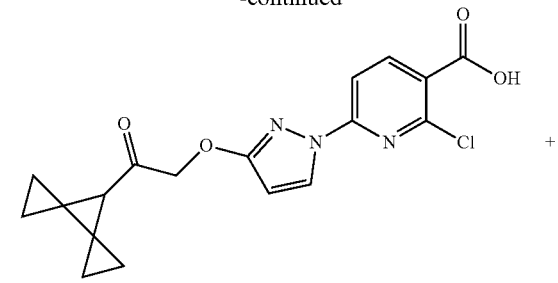

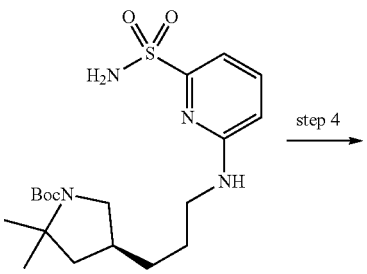

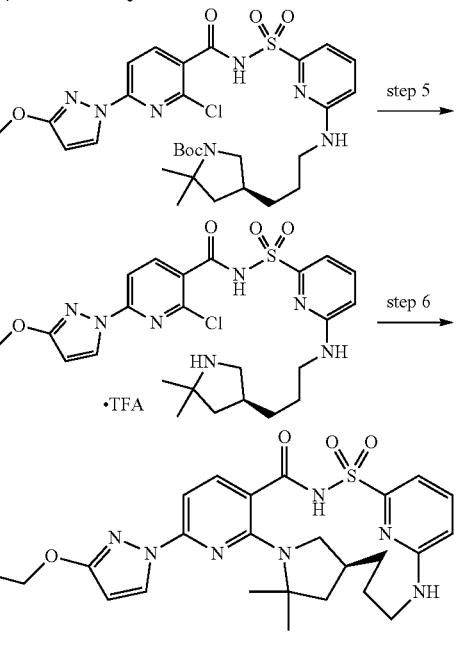

Step 1: 1-Dispiro[2.0.2.1]heptan-7-yl-2-(1H-pyrazol-3-yloxy)ethanone

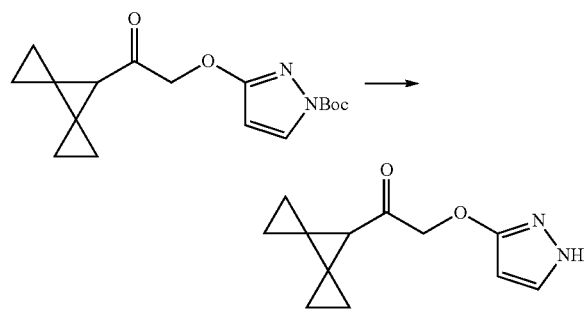

tert-Butyl 3-(2-dispiro[2.0.2.1]heptan-7-yl-2-oxo-ethoxy)pyrazole-1-carboxylate (350 mg, 0.7256 mmol) was dissolved in dichloromethane (2.31 mL) with trifluoroacetic acid (1.241 g, 10.88 mmol) and the reaction was stirred at room temperature for 60 min. The reaction was evaporated and the resulting oil was partitioned between ethyl acetate and a saturated sodium bicarbonate solution. The aqueous portion was extracted two additional times with ethyl acetate, then the organics were combined, washed with brine, dried over sodium sulfate, filtered and evaporated to give an oil, 1-dispiro[2.0.2.1]heptan-7-yl-2-(1H-pyrazol-3-yloxy)ethanone (223.7 mg, 93%). ESI-MS m/z calc. 218.10553, found 219.0 (M+1)⁺; Retention time: 0.43 min (LC Method A).

Step 2: tert-Butyl 2-chloro-6-[3-(2-dispiro[2.0.2.1] heptan-7-yl-2-oxo-ethoxy)pyrazol-1-yl]pyridine-3-carboxylate

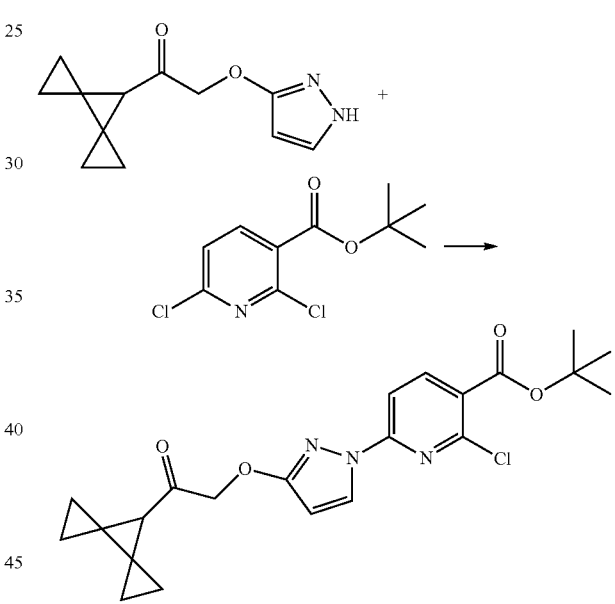

tert-Butyl 2,6-dichloropyridine-3-carboxylate (134.3 mg, 0.5413 mmol), 1-dispiro[2.0.2.1]heptan-7-yl-2-(1H-pyrazol-3-yloxy)ethanone (179.1 mg, 0.5416 mmol) and potassium carbonate (89.88 mg, 0.6503 mmol) were combined in anhydrous dimethyl sulfoxide (2.362 mL). 1,4-diazabicyclo [2.2.2]octane (12.16 mg, 0.1084 mmol) was added and the heterogeneous mixture was stirred at room temperature under nitrogen for 16 h. The reaction mixture was diluted with water (4.542 mL) and stirred for 15 min. The resulting white solid was collected and washed with water. The solid was dissolved in dichloromethane and dried over magnesium sulfate. The mixture was filtered and evaporated to give tert-butyl 2-chloro-6-[3-(2-dispiro[2.0.2.1]heptan-7-yl-2-oxo-ethoxy)pyrazol-1-yl]pyridine-3-carboxylate (148.7 mg, 64%) as a white solid. ESI-MS m/z calc. 429.14554, found 430.0 (M+1)⁺; Retention time: 0.83 min (LC Method A).

Step 3: 2-Chloro-6-[3-(2-dispiro[2.0.2.1]heptan-7-yl-2-oxo-ethoxy)pyrazol-1-yl]pyridine-3-carboxylic Acid

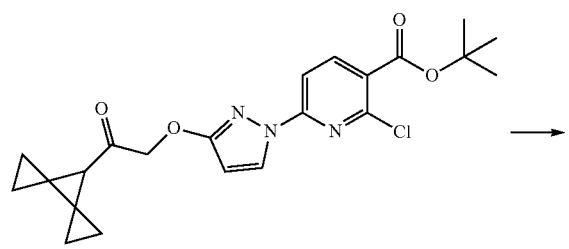

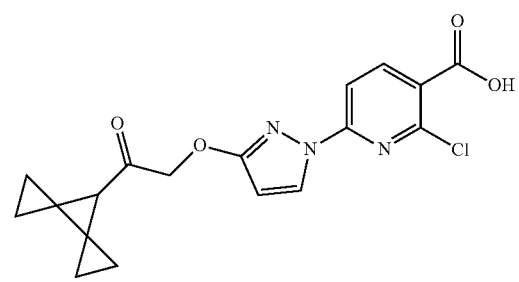

tert-Butyl 2-chloro-6-[3-(2-dispiro[2.0.2.1]heptan-7-yl-2-oxo-ethoxy)pyrazol-1-yl]pyridine-3-carboxylate (145.7 mg, 0.3389 mmol) was dissolved in dichloromethane (1.457 mL) with trifluoroacetic acid (391.7 µL, 5.084 mmol) and the reaction was stirred at room temperature for 2.5 h. Removed volatiles by rotary evaporation (no heating) followed by 30 min of drying under vacuum. Purified the crude material by silica gel chromatography using a shallow gradient from 100% dichloromethane to 20% methanol in dichloromethane which gave 2-chloro-6-[3-(2-dispiro[2.0.2.1]heptan-7-yl-2-oxo-ethoxy)pyrazol-1-yl]pyridine-3-carboxylic acid (89.6 mg, 71%) as a brown solid contaminated with a small amount of the starting material which was taken directly to the next step. ESI-MS m/z calc. 373.08295, found 374.0 (M+1)⁺; Retention time: 0.61 min (LC Method A).

Step 4: tert-Butyl (4S)-4-[3-[[6-[[2-chloro-6-[3-(2-dispiro[2.0.2.1]heptan-7-yl-2-oxo-ethoxy)pyrazol-1-yl]pyridine-3-carbonyl]sulfamoyl]-2-pyridyl]amino]propyl]-2,2-dimethyl-pyrrolidine-1-carboxylate

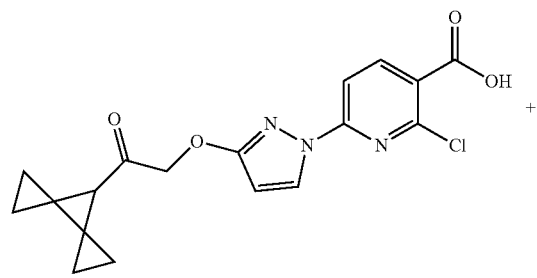

+

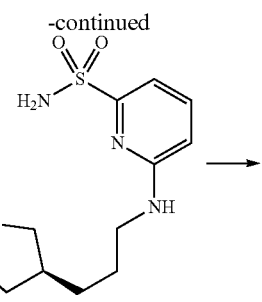

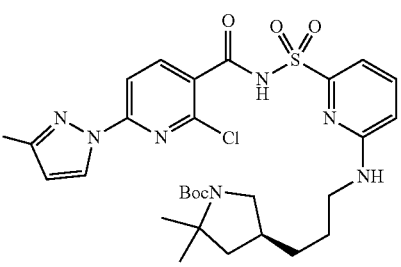

2-Chloro-6-[3-(2-dispiro[2.0.2.1]heptan-7-yl-2-oxo-ethoxy)pyrazol-1-yl]pyridine-3-carboxylic acid (89.6 mg, 0.2397 mmol) and carbonyl diimidazole (48.63 mg, 0.2999 mmol) (freshly recrystallized from tetrahydrofuran) were combined in tetrahydrofuran (1.165 mL) and stirred for 45 min at room temperature. Then, tert-butyl (4S)-2,2-dimethyl-4-[3-[(6-sulfamoyl-2-pyridyl)amino]propyl]pyrrolidine-1-carboxylate (98.89 mg, 0.2397 mmol) in tetrahydrofuran (448 µL) was added followed by 1,8-diazabicyclo[5.4.0]undec-7-ene (179.3 µL, 1.199 mmol) and the reaction was stirred at room temperature for 16 h. Removed the tetrahydrofuran by rotary evaporation then dissolved in ethyl acetate and washed with 1N hydrochloric acid (1×) and brine (1×), dried (magnesium sulfate), filtered and concentrated to a light brown oil which was purified by silica gel chromatography using a shallow gradient from 100% dichloromethane to 20% methanol in dichloromethane giving poor separation of the product from the two starting materials. The material was then filtered and purified using a reverse phase HPLC-MS method (Luna C₁₈ (2) column (75×30 mm, 5 µm particle size) sold by Phenomenex (pn: 00° C.-4252-U0-AX), and a dual gradient run from 1%-99% mobile phase B over 15.0 min (mobile phase A=water (5 mM hydrochloric acid), mobile phase B=acetonitrile, flow rate=50 mL/min, injection volume=950 µL and column temperature=25° C.)) giving tert-butyl (4S)-4-[3-[[6-[[2-chloro-6-[3-(2-dispiro[2.0.2.1]heptan-7-yl-2-oxo-ethoxy)pyrazol-1-yl]pyridine-3-carbonyl]sulfamoyl]-2-pyridyl]amino]propyl]-2,2-dimethyl-pyrrolidine-1-carboxylate (49.5 mg, 27%). ESI-MS m/z calc. 767.2868, found 768.1 (M+1)⁺; Retention time: 0.83 min (LC Method A).

Step 5: 2-Chloro-N-[[6-[3-[(3S)-5,5-dimethylpyrrolidin-3-yl]propylamino]-2-pyridyl]sulfonyl]-6-[3-(2-dispiro[2.0.2.1]heptan-7-yl-2-oxo-ethoxy)pyrazol-1-yl]pyridine-3-carboxamide (Trifluoroacetate Salt)

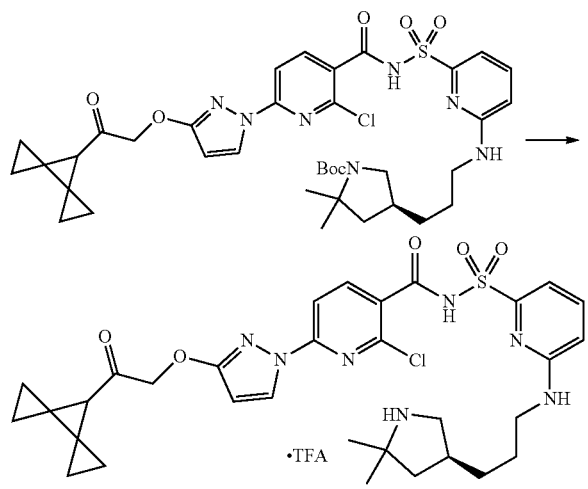

tert-Butyl (4S)-4-[3-[[6-[[2-chloro-6-[3-(2-dispiro[2.0.2.1]heptan-7-yl-2-oxo-ethoxy)pyrazol-1-yl]pyridine-3-carbonyl]sulfamoyl]-2-pyridyl]amino]propyl]-2,2-dimethyl-pyrrolidine-1-carboxylate (49.5 mg, 0.06443 mmol) was dissolved in dichloromethane (1.5 mL) and cooled to 0° C. and to the mixture was dropwise added trifluoroacetic acid (49.64 µL, 0.6443 mmol) and the mixture was stirred at 0° C. for 60 min. Added trifluoroacetic acid (49.64 µL, 0.6443 mmol) dropwise at 0° C. then warmed to room temperature and stirred 30 min, recooled to 0° C., added trifluoroacetic acid (49.64 µL, 0.6443 mmol), warmed to room temperature and stirred 20 min then dropwise added trifluoroacetic acid (49.64 µL, 0.6443 mmol) at room temperature and continued stirring at room temperature for 1 h. Concentrated the mixture to dryness by rotary evaporation with no heating. Co-evaporated with ether (5×), then placed under vacuum for 1 h giving 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-yl-2-oxo-ethoxy)pyrazol-1-yl]pyridine-3-carboxamide (trifluoroacetate salt) (50.4 mg, 100%) as a white solid. ESI-MS m/z calc. 667.2344, found 668.1 (M+1)+; Retention time: 0.55 min (LC Method A).

Step 6: (14S)-8-[3-(2-{Dispiro[2.0.2.1]heptan-7-yl}-2-oxoethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 258)

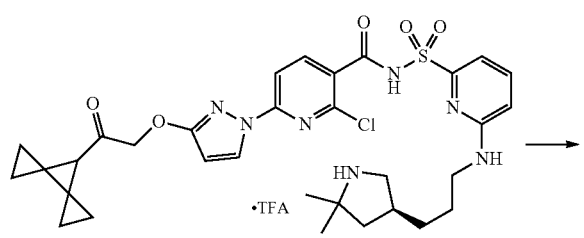

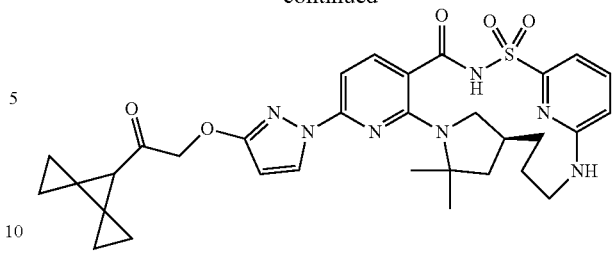

Combined 2-chloro-N-[[6-[3-[(3S)-5,5-dimethylpyrrolidin-3-yl]propylamino]-2-pyridyl]sulfonyl]-6-[3-(2-dispiro[2.0.2.1]heptan-7-yl-2-oxo-ethoxy)pyrazol-1-yl]pyridine-3-carboxamide (trifluoroacetate salt) (50.4 mg, 0.06443 mmol), potassium carbonate (53.43 mg, 0.3866 mmol), 3 Å molecular sieves and dimethyl sulfoxide (3.057 mL) in a vial, purged with nitrogen, capped, heated to 155° C. and stirred for 18 h. Cooled to room temperature and the mixture was filtered, diluted with ethyl acetate and 1N hydrochloric acid and the layers were separated. The aqueous layer was washed once more with ethyl acetate and the organic layers were combined, washed with brine (1×), dried (magnesium sulfate), filtered and concentrated to a brown solid which was purified by silica gel chromatography using a shallow gradient from 100% hexanes to 100% ethyl acetate giving (14S)-8-[3-(2-{dispiro[2.0.2.1]heptan-7-yl}-2-oxoethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (11 mg) which was still contaminated with impurities. For an ensuing reaction, this material was dissolved in methanol (110 µL) at room temperature and NaBH₄ (1.646 mg, 0.04351 mmol) (vigorous bubbling noted) was added and the resulting solution was stirred for 10 min then concentrated by rotary evaporation. Dissolved the residue in dimethyl sulfoxide, filtered and purified using a reverse phase HPLC-MS method using a Luna C₁₈ (2) column (75×30 mm, 5 µm particle size) sold by Phenomenex (pn: 00°C.-4252-U0-AX), and a dual gradient run from 30%-99% mobile phase B over 15.0 min (mobile phase A=water (5 mM hydrochloric acid), mobile phase B=acetonitrile, flow rate=50 mL/min, injection volume=950 µL and column temperature=25° C.)) giving as recovered starting material in the reduction, (14S)-8-[3-(2-{dispiro[2.0.2.1]heptan-7-yl}-2-oxoethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 258) (2.20 mg, 20%) as a white solid. ESI-MS m/z calc. 631.2577, found 632.2 (M+1)+; Retention time: 1.99 min (LC Method B).

Example 186: Preparation of (14S)-12,12-dimethyl-8-(2-oxo-3-{2-[1-(trifluoromethyl) cyclopropyl] ethoxy}-1,2-dihydropyridin-1-yl)-2λ⁶-thia-3,9,11,18,23-pentaaza tetracyclo[17.3.1.1¹¹,¹⁴.0⁵,¹⁰]tetracosa-1(23),5(10),6,8,19,21-hexaene-2,2,4-trione (Compound 268)

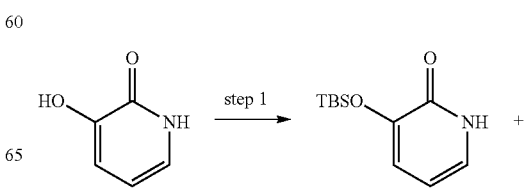

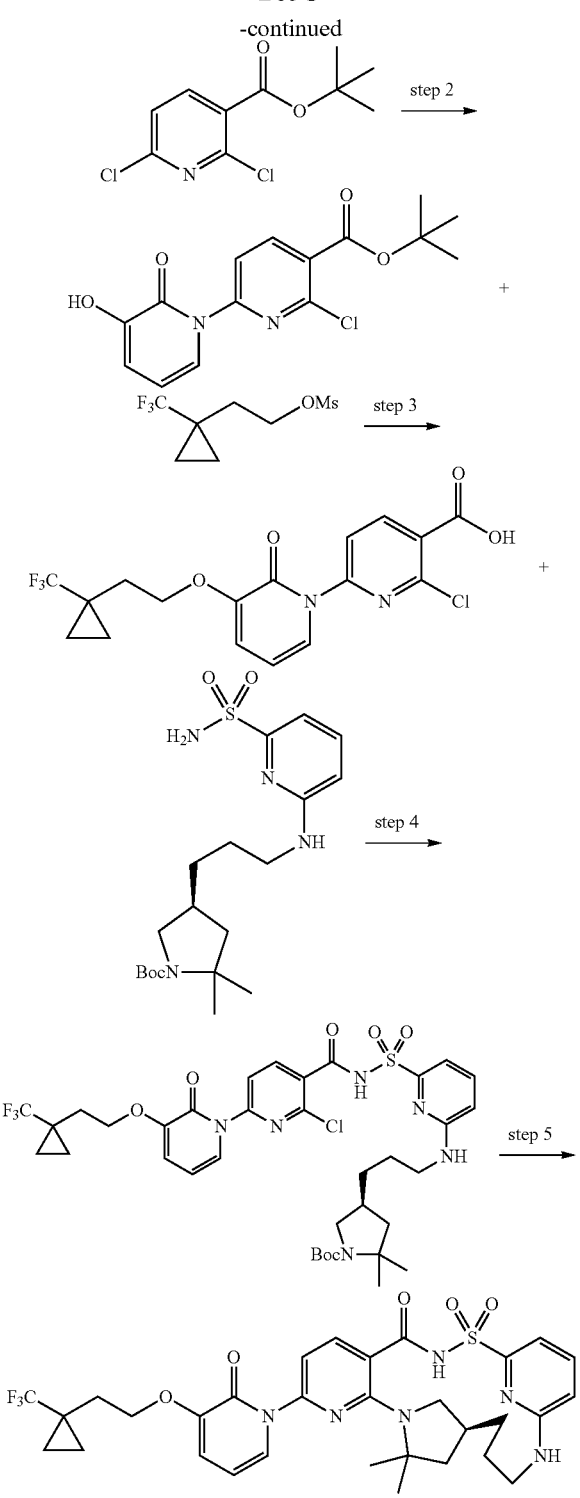

3-Hydroxy-1H-pyridin-2-one (1 g, 9.001 mmol) and imidazole (1.6 g, 23.50 mmol) were suspended in N,N-dimethylformamide (10 mL) under inert atmosphere. A solution of tert-butyl-chloro-dimethyl-silane (1.5 g, 9.952 mmol) in N,N-dimethyl formamide (10 mL) was added dropwise at room temperature over 30 min. The reaction was then allowed to stir overnight. The resulting solution was then poured into water and the mixture extracted with tert-butyl methyl ether (3×50 mL). The combined organic layers were washed with water, brine then dried over sodium sulfate. After filtration, the solvent is removed under reduced pressure to afford 3-[tert-butyl(dimethyl)silyl]oxy-1H-pyridin-2-one (1.8 g, 89%) as a light brown solid which was used directly in the next reaction. $^1$H NMR (400 MHz, Chloroform-d) δ 6.97 (ddd, J=6.4, 1.8, 0.8 Hz, 1H), 6.89 (dd, J=7.2, 1.8 Hz, 1H), 6.14 (dd, J=7.2, 6.5 Hz, 1H), 1.00 (d, J=1.3 Hz, 9H), 0.26 (s, 6H).

Step 2: tert-Butyl 2-chloro-6-(3-hydroxy-2-oxo-1-pyridyl)pyridine-3-carboxylate

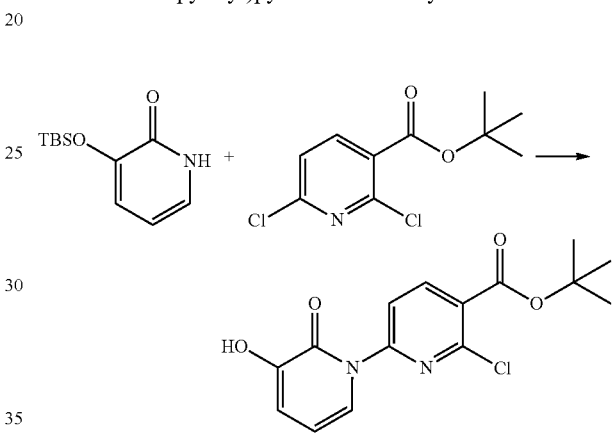

A mixture of tert-butyl 2,6-dichloropyridine-3-carboxylate (1 g, 4.031 mmol), 3-[tert-butyl(dimethyl)silyl]oxy-1H-pyridin-2-one (910 mg, 4.038 mmol), potassium carbonate (1.32 g, 9.551 mmol) and 1,4-diazabicyclo[2.2.2]octane (112 mg, 0.9985 mmol) in dimethyl sulfoxide (10 mL) was stirred at room temperature for 15 h. Poured the reaction mixture on crushed ice and the resultant precipitate was collected by filtration and dried to afford tert-butyl 2-chloro-6-(3-hydroxy-2-oxo-1-pyridyl)pyridine-3-carboxylate (0.82 g, 63%) as a light brown solid. $^1$H NMR (400 MHz, Chloroform-d) δ 12.57 (s, 1H), 8.15 (d, J=8.6 Hz, 1H), 7.36 (dd, J=7.2, 1.8 Hz, 1H), 7.23 (dd, J=6.6, 1.8 Hz, 1H), 6.95 (d, J=8.3 Hz, 1H), 6.29 (t, J=6.9 Hz, 1H), 1.59 (s, 9H). ESI-MS m/z calc. 322.07202, found 323.14 (M+1)$^+$; Retention time: 0.55 min (LC Method G).

Step 3: 2-Chloro-6-[2-oxo-3-[2-[1-(trifluoromethyl)cyclopropyl]ethoxy]-1-pyridyl]pyridine-3-carboxylic Acid Step 1: 3-[tert-Butyl(dimethyl)silyl]oxy-1H-pyridin-2-one

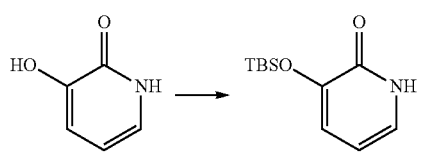 [SMILES: O=c1[nH]cccc1O ; CC(C)(C)[Si](C)(C)Oc1ccc[nH]c1=O]

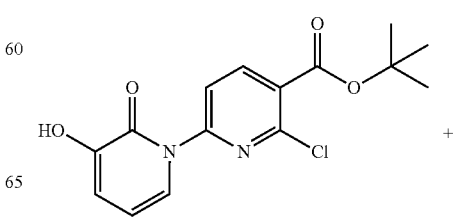

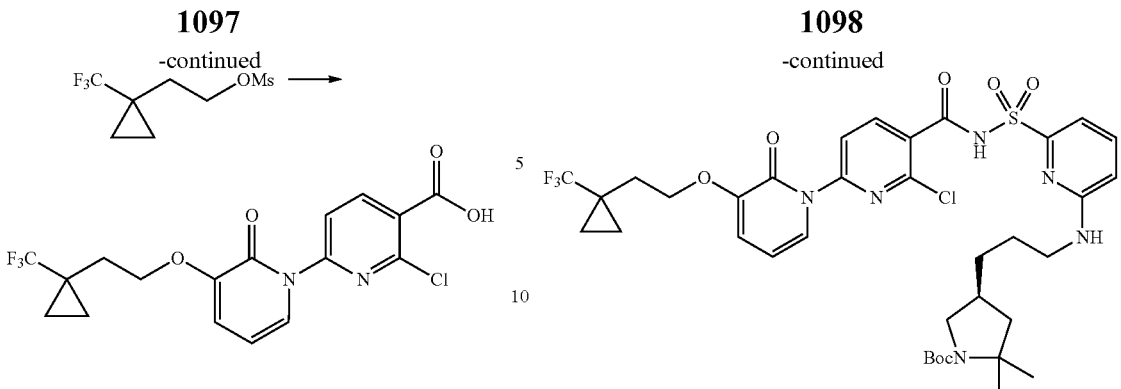

A mixture of 2-[1-(trifluoromethyl)cyclopropyl]ethyl methanesulfonate (362 mg, 1.559 mmol), tert-butyl 2-chloro-6-(3-hydroxy-2-oxo-1-pyridyl)pyridine-3-carboxylate (500 mg, 1.549 mmol), cesium carbonate (1.1 g, 3.376 mmol) in dimethyl sulfoxide (10 mL) was stirred at room temperature for 15 h. The reaction was diluted with water and extracted with ethyl acetate. The combined extracts were washed with brine and water, dried over sodium sulfate, filtered and evaporated. The residue was purified by silica gel column chromatography (0%-80% ethyl acetate in hexanes) and the second regioisomer to elute was isolated and to this material was added trifluoroacetic acid (1.5 mL, 19.47 mmol) and dichloromethane (5 mL) at room temperature with stirring for 2 h followed by evaporation of volatiles to afford 2-chloro-6-[2-oxo-3-[2-[1-(trifluoromethyl)cyclopropyl]ethoxy]-1-pyridyl]pyridine-3-carboxylic acid (120 mg, 19%). $^1$H NMR (400 MHz, Chloroform-d) δ 8.14 (d, J=8.4 Hz, 1H), 7.28 (td, J=7.2, 1.9 Hz, 2H), 6.95 (d, J=8.4 Hz, 1H), 6.22 (t, J=7.1 Hz, 1H), 4.13 (t, J=7.3 Hz, 2H), 2.01 (t, J=7.2 Hz, 2H), 1.58 (s, 9H), 1.01-0.87 (m, 2H), 0.69-0.57 (m, 2H). ESI-MS m/z calc. 402.05942, found 403.13 (M+1)$^+$; Retention time: 0.56 min (LC Method A).

Step 4: tert-Butyl (4S)-4-[3-[[6-[[2-chloro-6-[2-oxo-3-[2-[1-(trifluoromethyl)cyclopropyl]ethoxy]-1-pyridyl]pyridine-3-carbonyl]sulfamoyl]-2-pyridyl]amino]propyl]-2,2-dimethyl-pyrrolidine-1-carboxylate

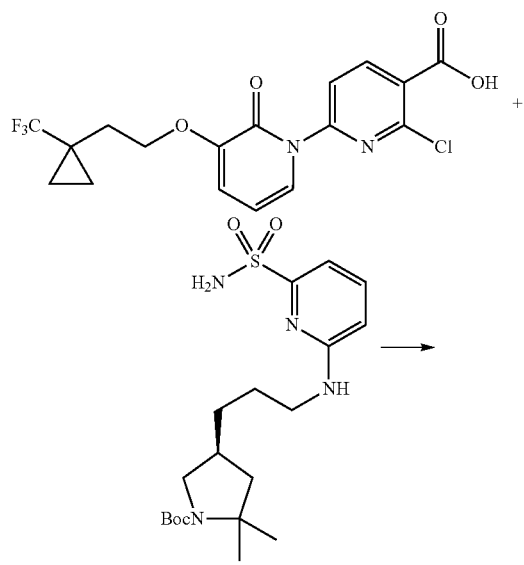

In a 20 mL vial, tert-butyl 2-chloro-6-[2-oxo-3-[2-[1-(trifluoromethyl)cyclopropyl]ethoxy]-1-pyridyl]pyridine-3-carboxylate (100 mg, 0.2483 mmol) and carbonyl diimidazole (47 mg, 0.2899 mmol) were combined in tetrahydrofuran (2 mL) and stirred at room temperature for 2 h. Then, tert-butyl (4S)-2,2-dimethyl-4-[3-[(6-sulfamoyl-2-pyridyl)amino]propyl]pyrrolidine-1-carboxylate (114 mg, 0.2763 mmol) was added followed by 1,8-diazabicyclo[5.4.0]undec-7-ene (50 µL, 0.3343 mmol) and the reaction was stirred for 16 h. The reaction was diluted with ethyl acetate and washed with a small amount of 1:1 saturated aqueous ammonium chloride/brine. The organics were separated, dried over sodium sulfate, filtered and evaporated. The resultant brown residue was purified by silica gel chromatography using a shallow gradient from 100% hexanes to 100% ethyl acetate to afford tert-butyl (4S)-4-[3-[[6-[[2-chloro-6-[2-oxo-3-[2-[1-(trifluoromethyl) cyclopropyl]ethoxy]-1-pyridyl]pyridine-3-carbonyl]sulfamoyl]-2-pyridyl]amino]propyl]-2,2-dimethyl-pyrrolidine-1-carboxylate (48 mg, 24%). ESI-MS m/z calc. 796.2633, found 797.4 (M+1)$^+$; Retention time: 0.81 min (LC Method A).

Step 5: (14S)-12,12-Dimethyl-8-(2-oxo-3-{2-[1-(trifluoromethyl)cyclopropyl]ethoxy}-1,2-dihydropyridin-1-yl)-2λ$^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 268)

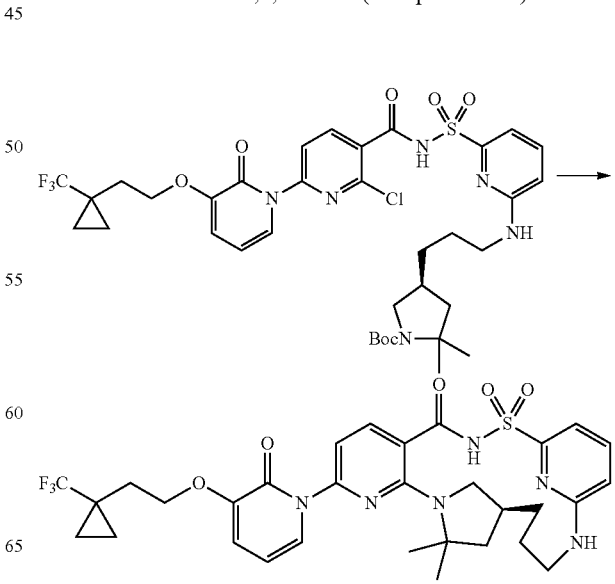

A solution of tert-butyl (4S)-4-[3-[[6-[[2-chloro-6-[2-oxo-3-[2-[1-(trifluoromethyl)cyclopropyl]ethoxy]-1-pyridyl]pyridine-3-carbonyl]sulfamoyl]-2-pyridyl]amino]propyl]-2,2-dimethyl-pyrrolidine-1-carboxylate (48 mg, 0.06020 mmol) in dichloromethane (400 µL) and trifluoroacetic acid (100 µL, 1.307 mmol) was stirred at room temperature for 4 h. The solvents were removed by evaporation and dissolved in ethyl acetate. Washed this solution with 2 mL of saturated sodium bicarbonate solution and the organic layer was collected and solvent removed by evaporation then dried under vacuum. The resulting residue was dissolved in dimethyl sulfoxide (5 mL) and 3 Å molecular sieves were added and the reaction mixture was stirred for 10 min. Then, cesium fluoride (36 mg, 0.2370 mmol) and potassium carbonate (31 mg, 0.2243 mmol) were added and the reaction mixture was heated at 150° C. for 16 h. The reaction mixture was filtered through a Whatman filter disc (puradisc 25 TF) and the filtrate was purified by a reverse phase HPLC-MS method using a dual gradient run from 30%-99% mobile phase B over 15.0 min (mobile phase A=water (0.05% hydrochloric acid), mobile phase B=acetonitrile) to afford (14S)-12,12-dimethyl-8-(2-oxo-3-{2-[1-(trifluoromethyl)cyclopropyl]ethoxy}-1,2-dihydropyridin-1-yl)-2$\lambda^6$-thia-3,9,11,18,23-pentaazatetracyclo[17.3.1.1$^{11,14}$.0$^{5,10}$]tetracosa-1(23),5(10),6,8,19,21-hexaene-2,2,4-trione (Compound 268) (19.5 mg, 49%) as an off white solid. $^1$H NMR (400 MHz, Chloroform-d) δ 7.96 (d, J=8.4 Hz, 1H), 7.59 (s, 1H), 7.46 (d, J=6.7 Hz, 1H), 7.21 (t, J=8.4 Hz, 2H), 6.72 (s, 1H), 6.43 (d, J=8.3 Hz, 1H), 6.21 (t, J=7.0 Hz, 1H), 4.06 (s, 2H), 3.86 (brs, 1H), 3.29-3.13 (m, 2H), 2.89 (brs, 1H), 2.36 (brs, 1H), 1.95 (t, J=7.8 Hz, 2H), 1.85 (brs, 1H), 1.67-1.54 (m, 3H), 1.46 (t, J=11.4 Hz, 2H), 1.18 (s, 3H), 1.14 (s, 3H), 0.99 (s, 2H), 0.67 (s, 2H). ESI-MS m/z calc. 660.2342, found 661.4 (M+1)$^+$; Retention time: 1.83 min (LC Method B).

Example 187: Preparation of 19,19-dimethyl-4-(3-{3-[1-(trifluoromethyl)cyclopropyl]propoxy}-1H-pyrazol-1-yl)-10$\lambda^6$-thia-1,3,9,14,21-pentaazatetracyclo[15.2.1.1$^{11,14}$.0$^{2,7}$]henicosa-2,4,6,11(21),12-pentaene-8,10,10-trione (Compound 273)

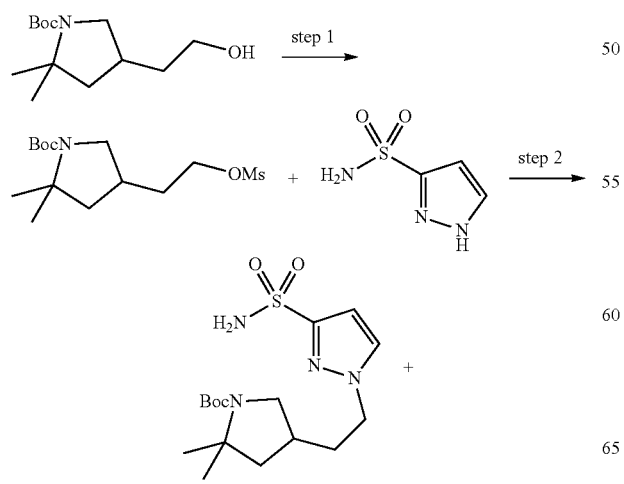

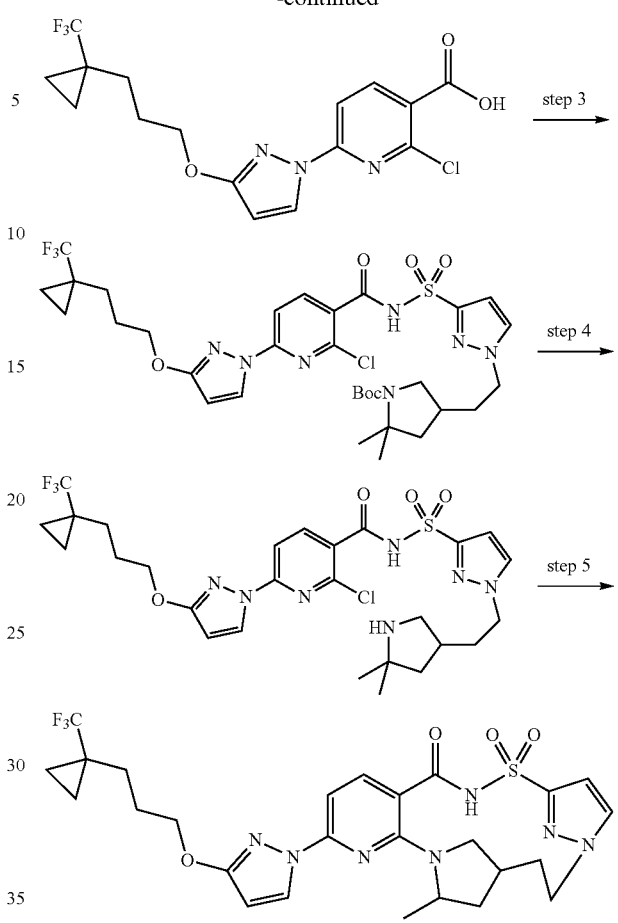

Step 1: tert-Butyl 2,2-dimethyl-4-(2-methylsulfonyloxyethyl)pyrrolidine-1-carboxylate

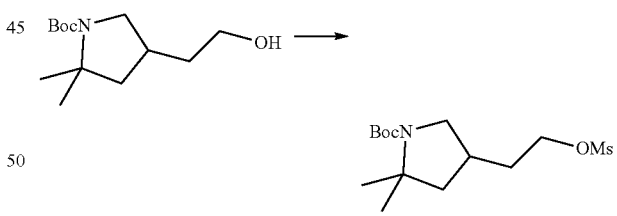

To a flask was added tert-butyl 4-(2-hydroxyethyl)-2,2-dimethyl-pyrrolidine-1-carboxylate (751 mg, 3.086 mmol), dichloromethane (10 mL) and triethylamine (1.75 mL, 12.56 mmol). The reaction flask was chilled to 0° C. and then methanesulfonyl chloride (290 µL, 3.747 mmol) was added dropwise and the reaction was allowed to warm to room temperature and stir for 45 min. The reaction was quenched with ice-water. The reaction was extracted with dichloromethane twice, dried over sodium sulfate, filtered, and evaporated to provide tert-butyl 2,2-dimethyl-4-(2-methylsulfonyloxyethyl)pyrrolidine-1-carboxylate (980 mg, 99%) as a thick yellow oil. ESI-MS m/z calc. 321.16098, found 322.1 (M+1)$^+$; Retention time: 1.22 min (LC Method B).

Step 2: tert-Butyl 2,2-dimethyl-4-[2-(3-sulfamoylpyrazol-1-yl)ethyl]pyrrolidine-1-carboxylate

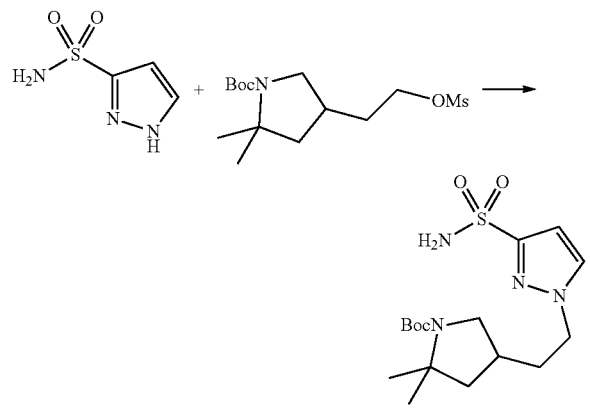

To a 20 mL vial was added potassium carbonate (1.264 g, 9.146 mmol), 1H-pyrazole-3-sulfonamide (449 mg, 3.051 mmol) and a solution of tert-butyl 2,2-dimethyl-4-(2-methylsulfonyloxyethyl)pyrrolidine-1-carboxylate (980 mg, 3.049 mmol) in N,N-dimethylformamide (12 mL). The reaction was capped and placed in a 75° C. oil bath and was allowed to stir for 18 h. The reaction was quenched with brine and extracted with ethyl acetate 3 times. The organic layers were combined, dried over sodium sulfate, filtered, and evaporated. The reaction was purified via column chromatography (0%-30% methanol in dichloromethane gradient) giving tert-butyl 2,2-dimethyl-4-[2-(3-sulfamoylpyrazol-1-yl)ethyl]pyrrolidine-1-carboxylate (259.0 mg, 23%) as a white solid along with a smaller amount of the regioisomeric byproduct. ESI-MS m/z calc. 372.18314, found 373.2 (M+1)+; Retention time: 1.39 min (LC Method B).

Step 3: tert-Butyl 4-[2-[3-[[2-chloro-6-[3-[3-[1-(trifluoromethyl)cyclopropyl]propoxy]pyrazol-1-yl]pyridine-3-carbonyl]sulfamoyl]pyrazol-1-yl]ethyl]-2,2-dimethyl-pyrrolidine-1-carboxylate

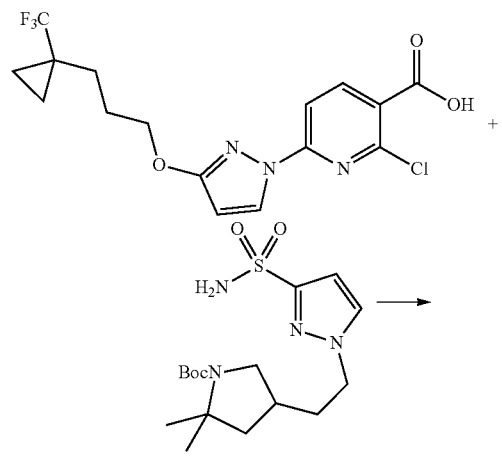

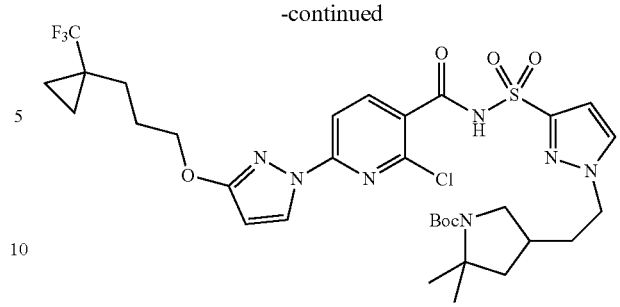

To a flask was added 2-chloro-6-[3-[3-[1-(trifluoromethyl)cyclopropyl]propoxy]pyrazol-1-yl]pyridine-3-carboxylic acid (271 mg, 0.6953 mmol), carbonyl diimidazole (136 mg, 0.8387 mmol) and tetrahydrofuran (3 mL). The reaction was placed in a preheated 35° C. oil bath and allowed to stir for 2 h. The reaction was then removed from the oil bath and solid tert-butyl 2,2-dimethyl-4-[2-(3-sulfamoylpyrazol-1-yl)ethyl]pyrrolidine-1-carboxylate (259 mg, 0.6953 mmol) was added from a flask which was rinsed with tetrahydrofuran (2 mL) into the reaction mixture. Added 1,8-diazabicyclo[5.4.0]undec-7-ene (350 μL, 2.340 mmol) and the reaction was allowed to stir at room temperature overnight. The reaction was quenched with brine and extracted with ethyl acetate. The organic layer was dried over sodium sulfate, filtered, and evaporated to provide a foam. The foam residue was purified by silica gel chromatography (0%-20% methanol in dichloromethane gradient) giving tert-butyl 4-[2-[3-[[2-chloro-6-[3-[3-[1-(trifluoromethyl)cyclopropyl]propoxy]pyrazol-1-yl]pyridine-3-carbonyl]sulfamoyl]pyrazol-1-yl]ethyl]-2,2-dimethyl-pyrrolidine-1-carboxylate (336 mg, 65%) as a white foam. $^1$H NMR (400 MHz, dimethyl sulfoxide-$d_6$) δ 8.35 (d, J=2.8 Hz, 1H), 8.08 (d, J=8.2 Hz, 1H), 7.79 (s, 1H), 7.62 (d, J=8.3 Hz, 1H), 6.59 (s, 1H), 6.13 (d, J=2.8 Hz, 1H), 4.22 (t, J=6.2 Hz, 2H), 4.13 (t, J=7.2 Hz, 2H), 3.54 (dt, J=23.2, 9.6 Hz, 1H), 2.82 (t, J=10.5 Hz, 1H), 2.00 (d, J=8.2 Hz, 1H), 1.91-1.78 (m, 5H), 1.77-1.68 (m, 2H), 1.35 (dd, J=18.7, 10.1 Hz, 13H), 1.18 (d, J=1.7 Hz, 3H), 0.95-0.88 (m, 2H), 0.79-0.72 (m, 2H). ESI-MS m/z calc. 743.248, found 744.4 (M+1)+; Retention time: 1.81 min (LC Method G).

Step 4: 2-Chloro-N-({1-[2-(5,5-dimethylpyrrolidin-3-yl)ethyl]-1H-pyrazol-3-yl}sulfonyl)-6-(3-{3-[1-(trifluoromethyl)cyclopropyl]propoxy}-1H-pyrazol-1-yl)pyridine-3-carboxamide

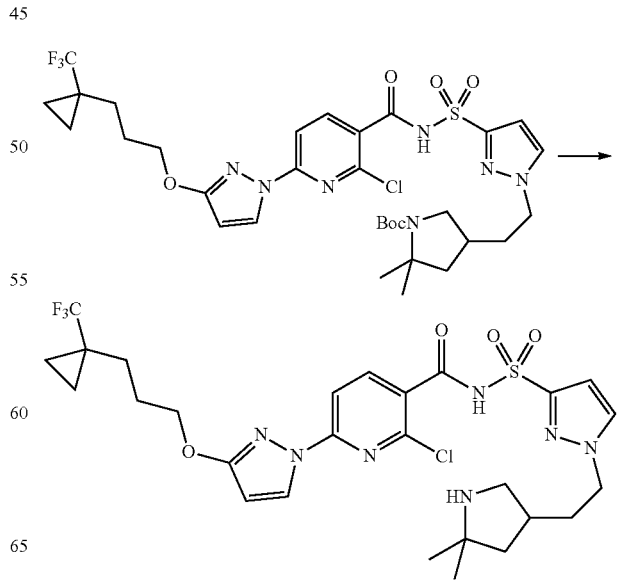

To a flask was added tert-butyl 4-[2-[3-[[2-chloro-6-[3-[3-[1-(trifluoromethyl)cyclopropyl]propoxy]pyrazol-1-yl]pyridine-3-carbonyl]sulfamoyl]pyrazol-1-yl]ethyl]-2,2-dimethyl-pyrrolidine-1-carboxylate (330 mg, 0.4434 mmol) and dichloromethane (6 mL). Trifluoroacetic acid (1.5 mL, 19.47 mmol) was added and the reaction was allowed to stir at room temperature for 1 h. The reaction was evaporated to dryness, neutralized with saturated sodium bicarbonate and extracted with ethyl acetate (poor solubility in ethyl acetate). The organic layer was dried over sodium sulfate and filtered. Most of the desired material was still on the filter cake so the filter cake (primarily sodium sulfate) was dissolved in water and washed with more ethyl acetate. The organic phase was separated and evaporated without drying over sodium sulfate. The product was dried under vacuum to remove residual water prior giving 2-chloro-N-({1-[2-(5,5-dimethylpyrrolidin-3-yl)ethyl]-1H-pyrazol-3-yl}sulfonyl)-6-(3-{3-[1-(trifluoromethyl) cyclopropyl]propoxy}-1H-pyrazol-1-yl)pyridine-3-carboxamide (246 mg, 86%) as a white solid. ESI-MS m/z calc. 643.19556, found 644.3 (M+1)⁺; Retention time: 1.52 min (LC Method B).

Step 5: 19,19-Dimethyl-4-(3-{3-[1-(trifluoromethyl)cyclopropyl]propoxy}-1H-pyrazol-1-yl)-10$\lambda^6$-thia-1,3,9,14,21-pentaazatetracyclo[15.2.1.1¹¹,¹⁴.0²,⁷]henicosa-2,4,6,11(21),12-pentaene-8,10,10-trione (Compound 273)

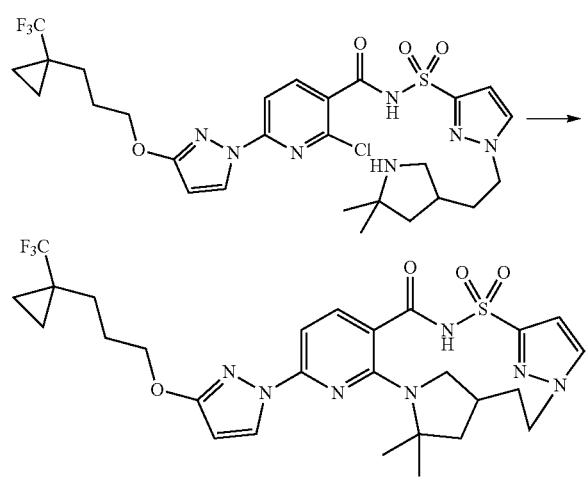

To a 20 mL vial was added 3 Å molecular sieves, potassium carbonate (264 mg, 1.910 mmol), cesium fluoride (116 mg, 0.7636 mmol) and a solution of 2-chloro-N-({1-[2-(5,5-dimethylpyrrolidin-3-yl)ethyl]-1H-pyrazol-3-yl}sulfonyl)-6-(3-{3-[1-(trifluoromethyl)cyclopropyl]propoxy}-1H-pyrazol-1-yl)pyridine-3-carboxamide (246 mg, 0.3819 mmol) in dimethyl sulfoxide (15 mL). The reaction was capped and placed in a preheated 150° C. oil bath and allowed to stir overnight. The reaction was allowed to cool to room temperature, filtered, and purified by reverse phase HPLC (10%-99% acetonitrile in water with a 0.1% hydrochloric acid modifier) giving 19,19-dimethyl-4-(3-{3-(trifluoromethyl)cyclopropyl]propoxy}-1H-pyrazol-1-yl)-10$\lambda^6$-thia-1,3,9,14,21-pentaazatetracyclo[15.2.1.1¹¹,¹⁴.0²,⁷]henicosa-2,4,6,11(21),12-pentaene-8,10,10-trione (Compound 273) (25.5 mg, 11%). ESI-MS m/z calc. 607.2189, found 608.3 (M+1)⁺; Retention time: 2.08 min (LC Method B).

Example 188: Preparation of 21,21-dimethyl-4-(3-{3-[1-(trifluoromethyl)cyclopropyl]propoxy}-1H-pyrazol-1-yl)-10$\lambda^6$-thia-1,3,9,14,23-pentaazatetracyclo[17.2.1.1¹¹,¹⁴.0²,⁷]tricosa-2,4,6,11(23),12-pentaene-8,10,10-trione (Compound 275)

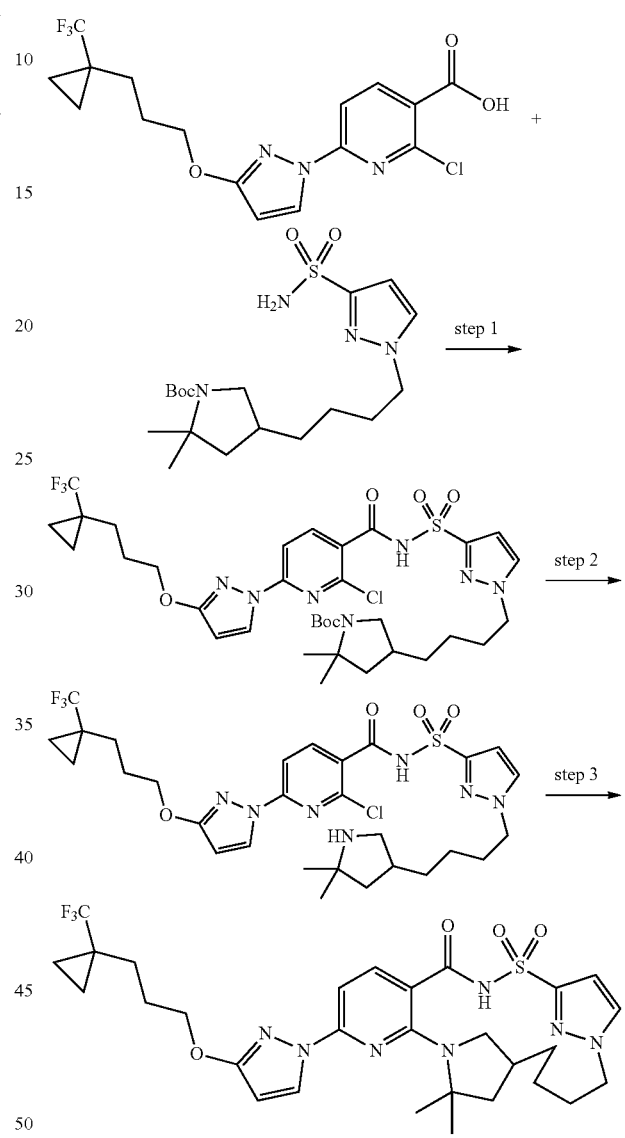

Step 1: tert-Butyl 4-[4-[3-[[2-chloro-6-[3-[3-[1-(trifluoromethyl)cyclopropyl]propoxy]pyrazol-1-yl]pyridine-3-carbonyl]sulfamoyl]pyrazol-1-yl]butyl]-2,2-dimethyl-pyrrolidine-1-carboxylate

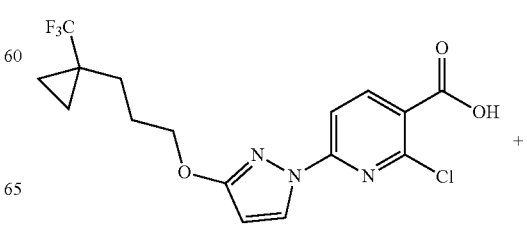

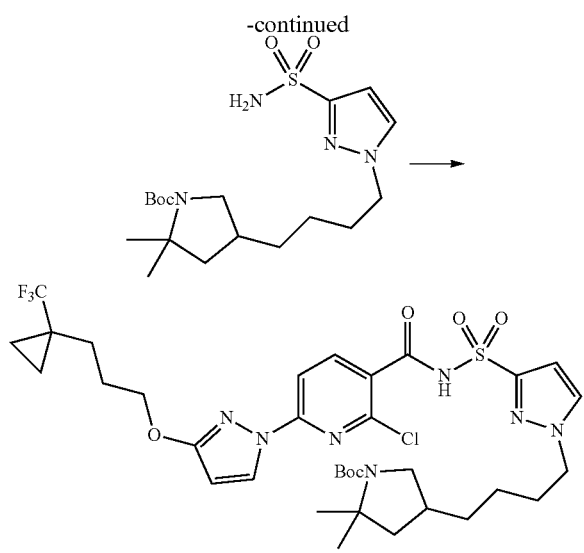

To a flask was added 2-chloro-6-[3-[3-[1-(trifluoromethyl)cyclopropyl]propoxy]pyrazol-1-yl]pyridine-3-carboxylic acid (280 mg, 0.7184 mmol), carbonyl diimidazole (140 mg, 0.8634 mmol) and tetrahydrofuran (3 mL). The reaction was heated at 35° C. for 90 min. The reaction was taken out of the oil bath and a solution of tert-butyl 2,2-dimethyl-4-[4-(3-sulfamoylpyrazol-1-yl)butyl]pyrrolidine-1-carboxylate (288 mg, 0.7190 mmol) in tetrahydrofuran (3 mL) was added followed by 1,8-diazabicyclo[5.4.0]undec-7-ene (350 µL, 2.340 mmol). The reaction was allowed to stir for 18 h and then was quenched with brine and extracted with ethyl acetate. The organic layer was dried over sodium sulfate, filtered, and evaporated to provide a foam. The residual foam was purified by silica gel chromatography (0%-20% methanol in dichloromethane) giving tert-butyl 4-[4-[3-[[2-chloro-6-[3-[3-[1-(trifluoromethyl)cyclopropyl]propoxy]pyrazol-1-yl]pyridine-3-carbonyl]sulfamoyl]pyrazol-1-yl]butyl]-2,2-dimethyl-pyrrolidine-1-carboxylate (159.1 mg, 29%) as a white foam. ¹H NMR (400 MHz, dimethyl sulfoxide-d₆) δ 12.88 (s, 1H), 8.39 (d, J=2.9 Hz, 1H), 8.08 (d, J=8.4 Hz, 1H), 8.00 (d, J=2.4 Hz, 1H), 7.69 (d, J=8.3 Hz, 1H), 6.86 (d, J=2.3 Hz, 1H), 6.19 (d, J=2.9 Hz, 1H), 4.23 (t, J=6.3 Hz, 4H), 3.49 (q, J=10.1 Hz, 1H), 2.73 (q, J=10.0 Hz, 1H), 2.07-1.94 (m, 1H), 1.82 (ddt, J=27.6, 14.2, 7.0 Hz, 5H), 1.74-1.69 (m, 2H), 1.36 (d, J=10.9 Hz, 10H), 1.30 (d, J=11.7 Hz, 5H), 1.18 (s, 4H), 0.95-0.87 (m, 2H), 0.80-0.70 (m, 2H). ESI-MS m/z calc. 771.27924, found 772.4 (M+1)⁺; Retention time: 1.99 min (LC Method G).

Step 2: 2-Chloro-N-({1-[4-(5,5-dimethylpyrrolidin-3-yl)butyl]-1H-pyrazol-3-yl}sulfonyl)-6-(3-{3-[1-(trifluoromethyl)cyclopropyl]propoxy}-1H-pyrazol-1-yl)pyridine-3-carboxamide

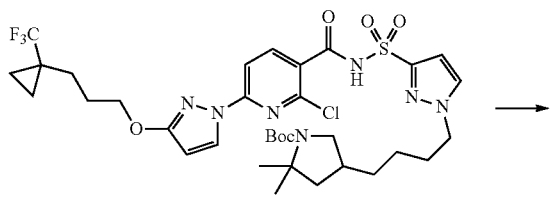

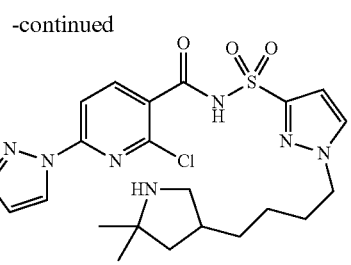

To a flask containing tert-butyl 4-[4-[3-[[2-chloro-6-[3-[3-[1-(trifluoromethyl)cyclopropyl]propoxy]pyrazol-1-yl]pyridine-3-carbonyl]sulfamoyl]pyrazol-1-yl]butyl]-2,2-dimethyl-pyrrolidine-1-carboxylate (156 mg, 0.2020 mmol) was added dichloromethane (6 mL) and trifluoroacetic acid (600 µL, 7.788 mmol). The reaction was allowed to stir at room temperature for 1 h. The reaction was evaporated to dryness and a saturated solution of sodium bicarbonate was added until the reaction mixture was pH=7. Ethyl acetate was added and the mixture was stirred for 3 min. The mixture was separated and the organic layer (not fully dissolved) was evaporated to dryness and dried under vacuum overnight giving 2-chloro-N-({1-[4-(5,5-dimethylpyrrolidin-3-yl)butyl]-1H-pyrazol-3-yl}sulfonyl)-6-(3-{3-[1-(trifluoromethyl)cyclopropyl]propoxy}-1H-pyrazol-1-yl)pyridine-3-carboxamide (133 mg, 98%) as a white solid. ESI-MS m/z calc. 671.2268, found 672.4 (M+1)⁺; Retention time: 1.56 min (LC Method G).

Step 3: 21,21-Dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,¹⁴.0²,⁷]tricosa-2,4,6,11(23),12-pentaene-8,10,10-trione (Compound 275)

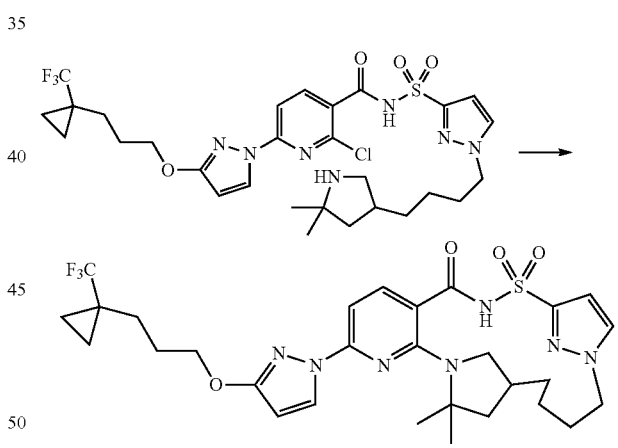

To a vial was added potassium carbonate (137 mg, 0.9913 mmol), cesium fluoride (62 mg, 0.4082 mmol), 3 Å molecular sieves and a solution of 2-chloro-N-({1-[4-(5,5-dimethylpyrrolidin-3-yl)butyl]-1H-pyrazol-3-yl}sulfonyl)-6-(3-{3-[1-(trifluoromethyl)cyclopropyl]propoxy}-1H-pyrazol-1-yl)pyridine-3-carboxamide (133 mg, 0.1979 mmol) in dimethyl sulfoxide (8 mL). The reaction was placed in a preheated 150° C. oil bath and allowed to stir for 18 h. The reaction was filtered and purified by reverse phase HPLC (30%-99% acetonitrile in water with a 0.1% hydrochloric acid modifier) giving 21,21-dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,¹⁴.0²,⁷]tricosa-2,4,6,11(23),12-pentaene-8,10,10-trione (Compound 275) (58.6 mg, 47%) as a white solid. ESI-MS m/z calc. 635.2502, found 636.4 (M+1)⁺; Retention time: 2.22 min (LC Method B).

Example 189: Preparation of 21,21-dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,¹⁴.0²,⁷]tricosa-2,4,6,11(23),12-pentaene-8,10,10-trione (Enantiomer 1) (Compound 276) and 21,21-dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,14.02,7]tricosa-2,4,6,11(23),12-pentaene-8,10,10-trione (Enantiomer 2) (Compound 277)

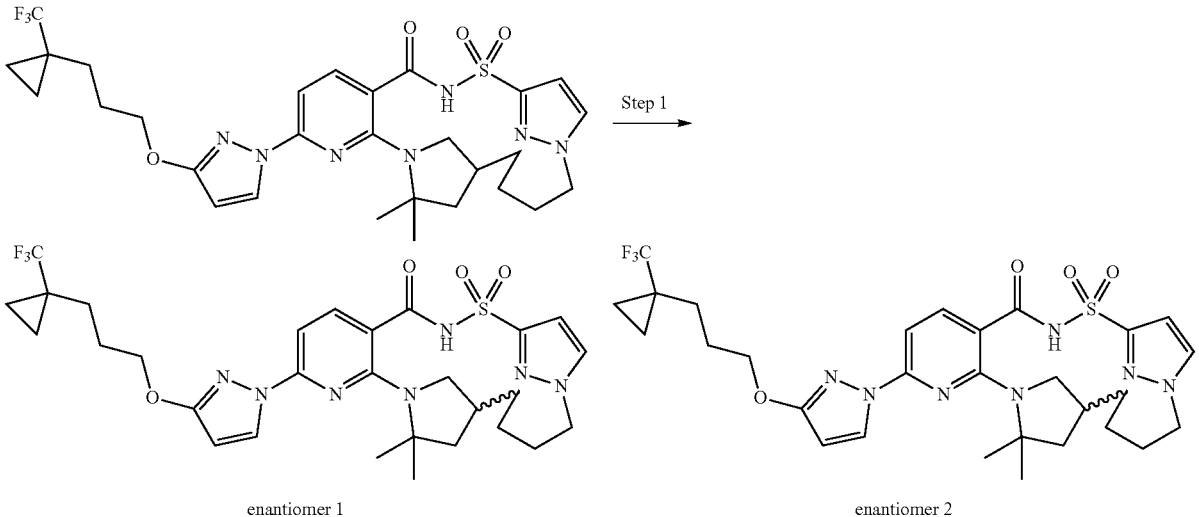

Step 1: 21,21-Dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,14.02,7]tricosa-2,4,6,11(23),12-pentaene-8,10,10-trione (Enantiomer 1) (Compound 276) and 21,21-dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,14.02,7]tricosa-2,4,6,11(23),12-pentaene-8,10,10-trione (Enantiomer 2) (Compound 277)

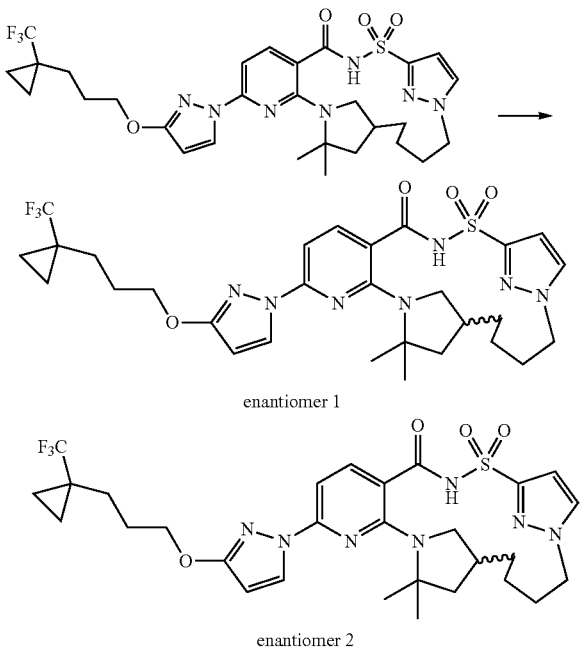

Racemic 21,21-dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,14.02,7]tricosa-2,4,6,11(23),12-pentaene-8,10,10-trione (53 mg, 0.08337 mmol) was separated by chiral SFC using a ChiralPak AS-H (250×21.2 mm column, 5 μm particle size) with 25% acetonitrile:methanol (90:10; 20 mM NH3))/75% carbon dioxide mobile phase at 10 mL/min giving as the first enantiomer to elute, 21,21-dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,14.02,7]tricosa-2,4,6,11(23),12-pentaene-8,10,10-trione (enantiomer 1) (Compound 276) (19.6 mg, 74%); $^1$H NMR (400 MHz, dimethyl sulfoxide-$d_6$) δ 12.57 (s, 1H), 8.20 (d, J=2.8 Hz, 1H), 7.98 (s, 1H), 7.75 (s, 1H), 6.89 (d, J=9.1 Hz, 2H), 6.11 (d, J=2.3 Hz, 1H), 4.27 (s, 2H), 4.20 (t, J=6.2 Hz, 2H), 2.72 (d, J=9.3 Hz, 2H), 2.54 (s, 6H), 1.85 (dd, J=10.3, 5.4 Hz, 3H), 1.75-1.69 (m, 2H), 1.61 (s, 4H), 1.52 (s, 4H), 0.93-0.89 (m, 2H), 0.77-0.73 (m, 2H), ESI-MS m/z calc. 635.2502, found 636.4 (M+1)⁺; Retention time: 2.24 min (LC Method B). The second enantiomer to elute was 21,21-dimethyl-4-(3-{3-[1-(trifluoromethyl)cyclopropyl]propoxy}-1H-pyrazol-1-yl)-10λ⁶-thia-1,3,9,14,23-pentaazatetracyclo[17.2.1.1¹¹,14.02,7]tricosa-2,4,6,11(23),12-pentaene-8,10,10-trione (enantiomer 2) (Compound 277) (16.6 mg, 63%). ESI-MS m/z calc. 635.2502, found 636.4 (M+1)⁺; Retention time: 2.22 min (LC Method B).

Example 190: Preparation of 20,20,22-trimethyl-4-[3-(3,3,3-trifluoro-2,2-dimethylpropoxy)-1H-pyrazol-1-yl]-10λ⁶-thia-1,3,9,13,14-pentaazatetracyclo[16.2.1.1¹¹,¹⁴.0²,⁷]docosa-2,4,6,11(22),12-pentaene-8,10,10-trione (atropisomer 2, Enantiomer 1) (Compound 285) and 20,20,22-trimethyl-4-[3-(3,3,3-trifluoro-2,2-dimethylpropoxy)-1H-pyrazol-1-yl]-10λ⁶-thia-1,3,9,13,14-pentaazatetracyclo[16.2.1.1¹¹,¹⁴.0²,⁷]docosa-2,4,6,11(22),12-pentaene-8,10,10-trione (atropisomer 2, Enantiomer 2) (Compound 286)

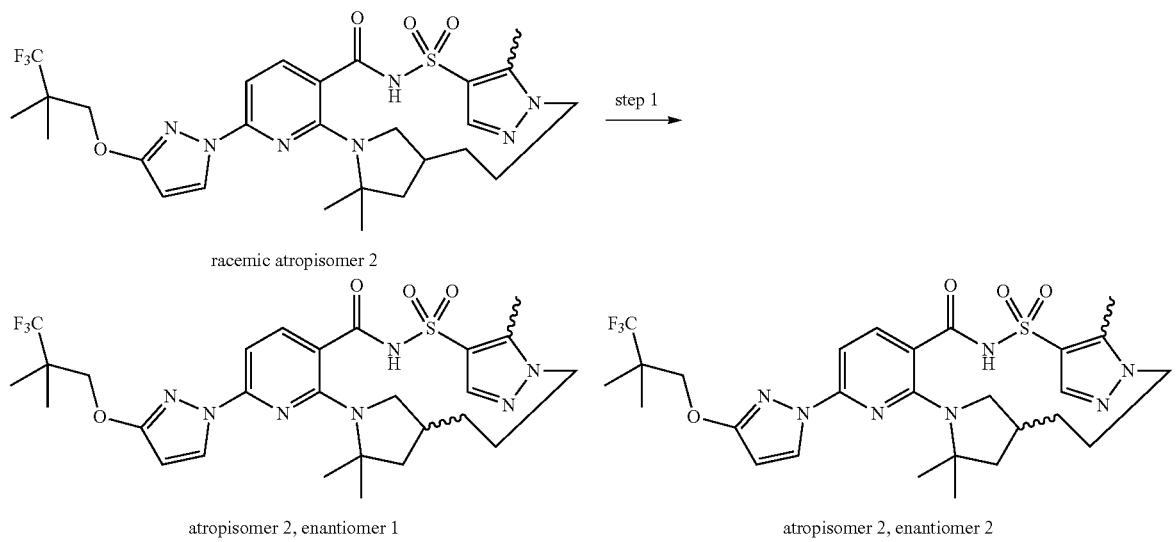

Step 1: 20,20,22-Trimethyl-4-[3-(3,3,3-trifluoro-2,2-dimethylpropoxy)-1H-pyrazol-1-yl]-10λ⁶-thia-1,3,9,13,14-pentaazatetracyclo[16.2.1.1¹¹,¹⁴.0²,⁷]docosa-2,4,6,11(22),12-pentaene-8,10,10-trione (Atropisomer 2, Enantiomer 1) (Compound 285) and 20,20,22-trimethyl-4-[3-(3,3,3-trifluoro-2,2-dimethylpropoxy)-1H-pyrazol-1-yl]-10λ⁶-thia-1,3,9,13,14-pentaazatetracyclo[16.2.1.1¹¹,¹⁴.0²,⁷]docosa-2,4,6,11(22),12-pentaene-8,10,10-trione (Atropisomer 2, Enantiomer 2) (Compound 286)

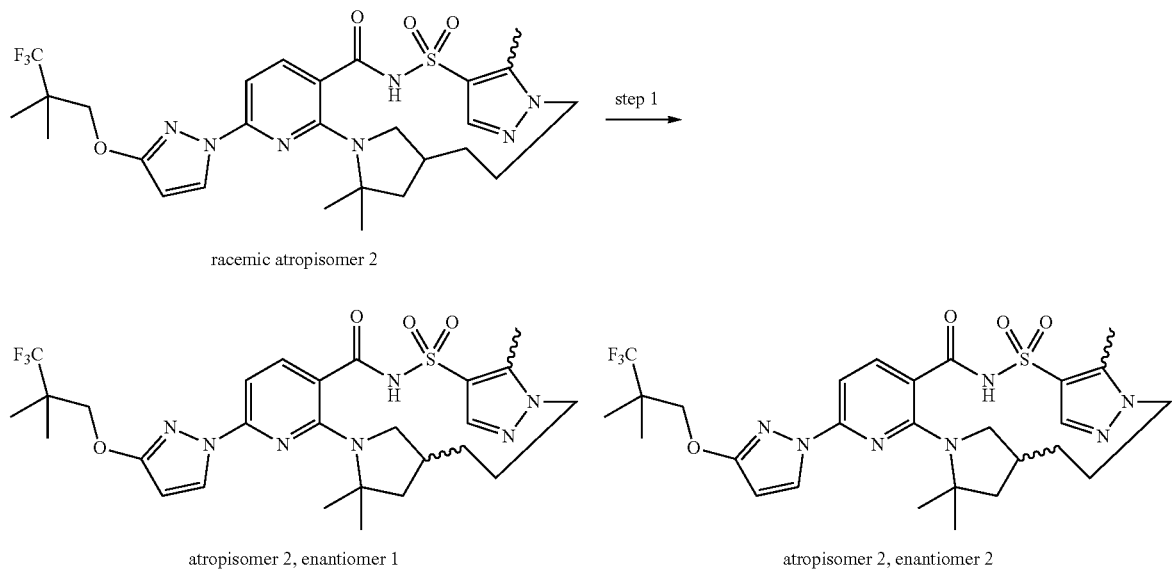

20,20,22-Trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (17 mg, 0.02788 mmol) (racemic atropisomer 2) was separated by chiral SFC using a ChiralPak AS-H (250×10 mm column, 5 μm particle size) with 24% acetonitrile: methanol (90:10; 20 mM NH$_3$))/76% carbon dioxide mobile phase at 10 mL/min giving as the first enantiomer to elute, 20,20,22-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (atropisomer 2, enantiomer 1) (Compound 285) (5.4 mg, 64%) as a yellow solid. $^1$H NMR (400 MHz, dimethyl sulfoxide-d$_6$) δ2.16 (bs, 1H), 8.19 (d, J=2.8 HZ, 1H), 7.81 (d, J=7.9 Hz, 1H), 7.71 (s, 1H), 6.92 (d, J=7.9 HZ, 1H), 6.10 (d, J=2.8 Hz, 1H), 4.35 (m, 1H), 4.22 (bs, 2H), 4.02 (m, 1H), 2.66 (s, 3H), 2.39 (m, 1H), 2.02 (m, 3H), 1.83 (m, 2H), 1.65 (dd, J=12.1 Hz, 5.6 Hz, 1H), 1.50 (q, J=15.6 Hz, 12.4 Hz, 2H), 1.50 (m, 8H), 1.36 (q, J=15.6 Hz, 12.4 Hz, 2H), 1.22 (s, 6H), 1.12 (m, 1H). ESI-MS m/z calc. 609.2345, found 610.4 (M+1)$^+$; Retention time: 3.14 min (LC Method D). The second enantiomer to elute was 20,20,22-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (atropisomer 2, enantiomer 2) (Compound 286) (6.5 mg, 76%), isolated as a yellow foam. ESI-MS m/z calc. 609.2345, found 610.4 (M+1)$^+$; Retention time: 3.14 min (LC Method D).

Example 191: Preparation of 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (Enantiomer 1) (Compound 290) and 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (Enantiomer 2) (Compound 291)

Step 1: 12,20,20-Trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (Enantiomer 1) (Compound 290) and 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (Enantiomer 2) (Compound 291)

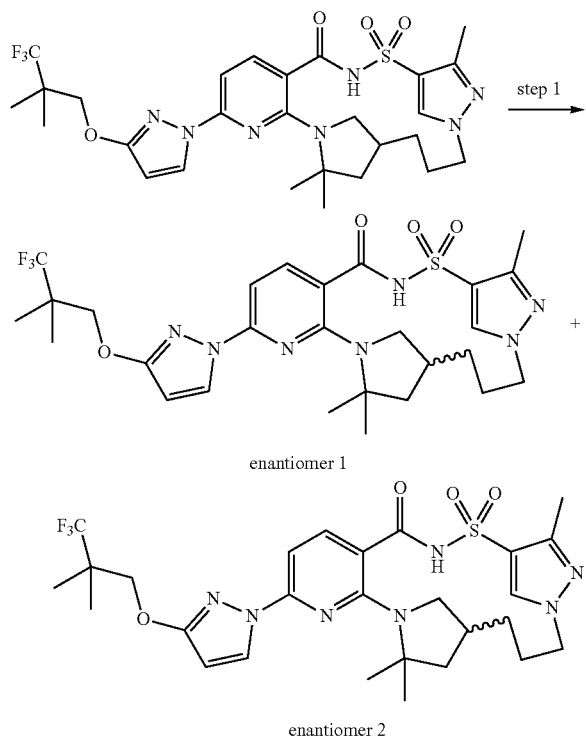

Racemic 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (73 mg, 0.1197 mmol) was subjected to chiral SFC chromatography using a ChiralPak AS-H (250×21.2 mm column, 5 μm particle size) with 20% acetonitrile:methanol (90:10, 20 mM NH$_3$))/80% carbon dioxide mobile phase at 70 mL/min giving as the first enantiomer to elute, 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (enantiomer 1) (Compound 290) (35.1 mg, 92%). ESI-MS m/z calc. 609.2345, found 610.4 (M+1)$^+$; Retention time: 3.07 min (LC Method D). The second enantiomer to elute was 12,20,20-trimethyl-4-[3-(3,3,3-trifluoro-2,2-dimethylpropoxy)-1H-pyrazol-1-yl]-10λ$^6$-thia-1,3,9,13,14-pentaazatetracyclo[16.2.1.1$^{11,14}$.0$^{2,7}$]docosa-2,4,6,11(22),12-pentaene-8,10,10-trione (enantiomer 2) (Compound 291) (28.5 mg, 78%). $^1$H NMR (400 MHz, dimethyl sulfoxide-d$_6$) δ 2.16 (bs, 1H), 8.38 (s, 1H), 8.19 (d, J=2.8 Hz, 1H), 7.81 (d, J=7.9 Hz, 1H), 6.92 (d, J=7.9 Hz, 1H), 6.10 (d, J=2.8 Hz, 1H), 4.35 (m, 1H), 4.22 (bs, 2H), 4.02 (m, 1H), 2.38 (s, 3H), 2.02 (m, 3H), 1.83 (m, 2H), 1.75 (dd, J=12.1 Hz, 5.6 Hz, 1H), 1.54 (s, 3H), 1.47 (s, 3H), 1.36 (q, J=15.6 HZ, 12.4 Hz, 2H), 1.22 (s, 6H), 1.12 (m, 1H). ESI-MS m/z calc. 609.2345, found 610.4 (M+1)$^+$; Retention time: 3.07 min (LC Method D).

Example 192: Preparation of 5,5-dimethyl-9-(3-{2-[1-(trifluoromethyl)cyclopropyl]ethoxy}-1H-pyrazol-1-yl)-15λ⁶-thia-2,6,8,14,20-pentaazatetracyclo[14.3.1.1³,⁶.0⁷,¹²]henicosa-1(20),7,9,11,16,18-hexaene-13,15,15-trione (Compound 31)

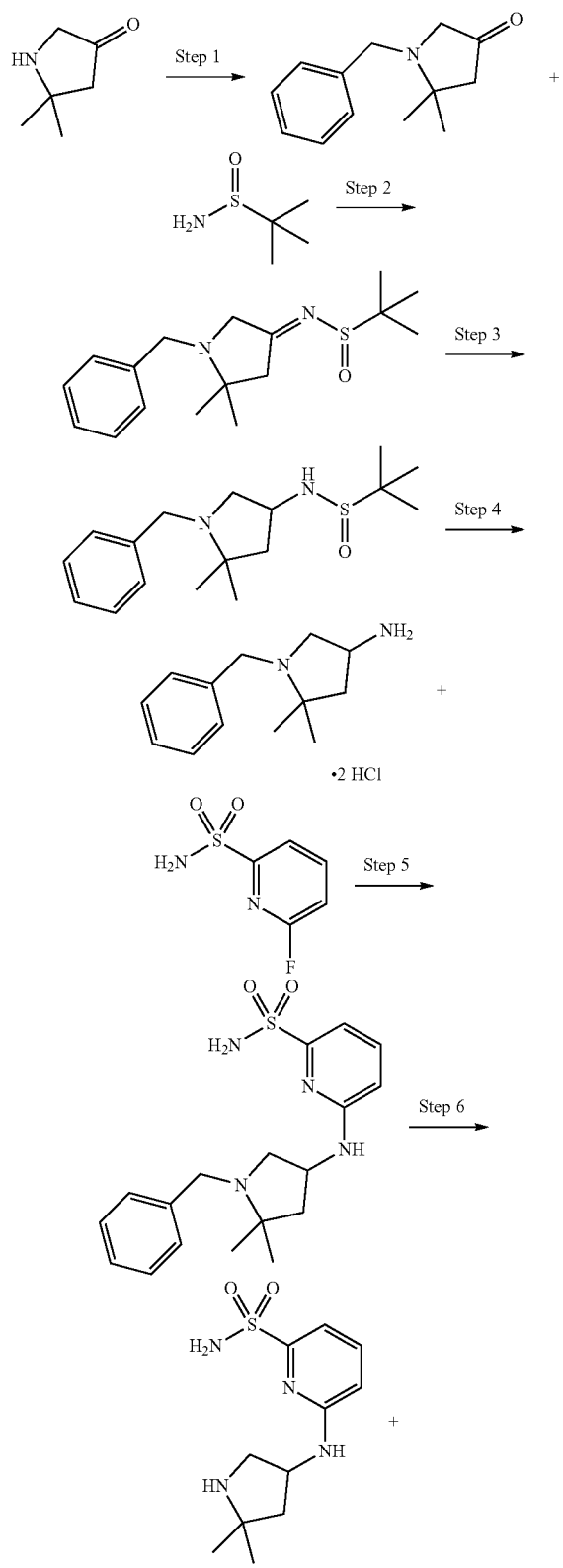

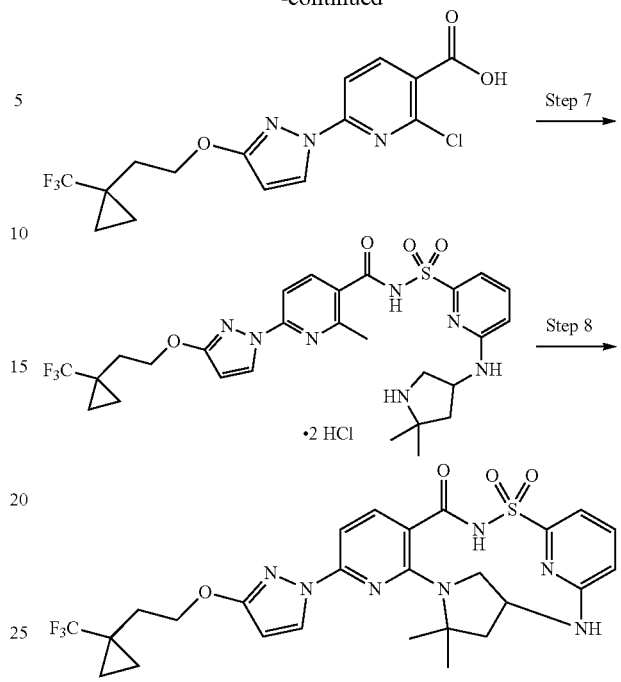

Step 1: 1-Benzyl-5,5-dimethyl-pyrrolidin-3-one

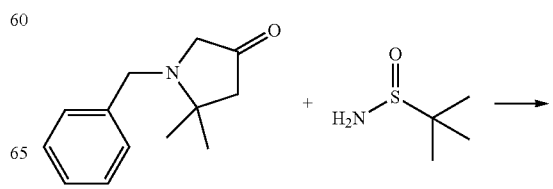

To a stirred solution of 5,5-dimethylpyrrolidin-3-one (1.020 g, 9.014 mmol) in anhydrous acetonitrile (30 mL) was added anhydrous potassium carbonate (5.00 g, 36.18 mmol) under nitrogen at ambient temperature. After stirring for 15 min, benzyl bromide (1.2 mL, 10.09 mmol) was added. After 7 h, the reaction mixture was filtered and the filtrate was concentrated in vacuo to provide the crude product which was extracted from water (20 mL) with ethyl acetate (3×30 mL). The combined organic extracts were washed with water and dried over anhydrous sodium sulfate, filtered over a pad of silica gel and concentrated in vacuo to give the crude product, 1-benzyl-5,5-dimethyl-pyrrolidin-3-one (1.67 g, 91%) as orange viscous material which was used in the subsequent reaction without further purification. ESI-MS m/z calc. 203.13101, found 204.1 (M+1)⁺; Retention time: 0.81 min (LC Method B).

Step 2: (E)-N-(1-benzyl-5,5-dimethylpyrrolidin-3-ylidene)-2-methylpropane-2-sulfinamide

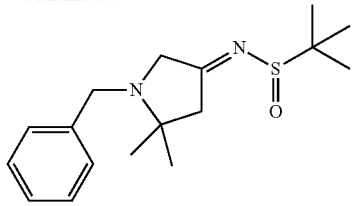

To a stirred solution of 1-benzyl-5,5-dimethyl-pyrrolidin-3-one (1.762 g, 8.668 mmol) and 2-methylpropane-2-sulfinamide (1.157 g, 9.546 mmol) in anhydrous tetrahydrofuran (70 mL) was added titanium(IV) ethoxide (7.3 mL, 34.82 mmol) under nitrogen at ambient temperature. The reaction mixture was allowed to stir at 80° C. for 13 h then was allowed to cool to ambient temperature. The reaction was quenched slowly with saturated aqueous sodium bicarbonate until some precipitation was formed (though the titanium salts are white, due to the product color, the salt looked brownish) (about 40 mL of sodium bicarbonate was used). The inorganic suspension was filtered through a pad of Celite and the filter cake was washed with ethyl acetate (100 mL). After the layers were separated from the filtrate, the aqueous portion was extracted with ethyl acetate (2×50 mL). The combined organic layers were washed with brine, dried over anhydrous sodium sulfate, filtered and concentrated under reduced pressure to furnish (E)-N-(1-benzyl-5,5-dimethylpyrrolidin-3-ylidene)-2-methylpropane-2-sulfinamide (2.602 g, 98%) as brownish solid which was used in the subsequent reaction without further purification. ESI-MS m/z calc. 306.17657, found 307.2 (M+1)+; Retention time: 0.8 min (LC Method B).

Step 3: N-(1-Benzyl-5,5-dimethyl-pyrrolidin-3-yl)-2-methyl-propane-2-sulfinamide

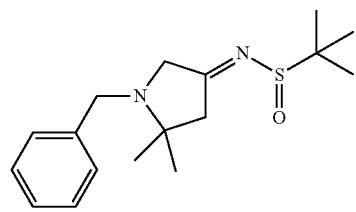

To a stirred solution of (E)-N-(1-benzyl-5,5-dimethylpyrrolidin-3-ylidene)-2-methylpropane-2-sulfinamide (770 mg, 2.51 mmol) in anhydrous methanol (3 mL) and tetrahydrofuran (10 mL) at −10° C. was added sodium borohydride (290 mg, 7.665 mmol) in three portions under nitrogen. The reaction was allowed to warm to 0° C. and stirred at that temperature for 2 h. The reaction was quenched with aqueous NH₄Cl (5 mL), followed by saturated aqueous sodium bicarbonate (20 mL). The volatiles were removed and the remaining aqueous portion was extracted with ethyl acetate (25 mL). The aqueous layer was extracted further with ethyl acetate (2×15 mL). The combined organic layers were dried (magnesium sulfate), filtered, and concentrated to furnish crude N-(1-benzyl-5,5-dimethyl-pyrrolidin-3-yl)-2-methyl-propane-2-sulfinamide (650 mg, 84%) as a brownish solid. ESI-MS m/z calc. 308.19223, found 309.2 (M+1)+; Retention time: 0.63 min (LC Method B).

Step 4: 1-Benzyl-5,5-dimethyl-pyrrolidin-3-amine (Dihydrochloride Salt)

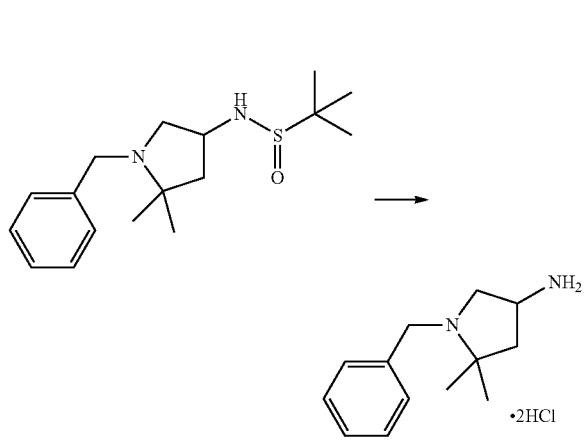

Crude N-(1-benzyl-5,5-dimethyl-pyrrolidin-3-yl)-2-methyl-propane-2-sulfinamide (650 mg, 2.107 mmol) was dissolved in methanol (10 mL) and hydrogen chloride (2.2 mL of 4.0 M in dioxane, 8.800 mmol) was added dropwise at 0° C. and the reaction mixture was stirred at room temperature for 1 h. The volatiles were removed under reduced pressure. Trituration with ether was attempted however the crude made a gummy material, thus the ether was removed under reduced pressure and the resulting material was dried under vacuum to furnish 1-benzyl-5,5-dimethyl-pyrrolidin-3-amine (dihydrochloride salt) (580 mg, 99%) as a brownish gum. It was used in the subsequent reaction without further purification. ESI-MS m/z calc. 204.16264, found 205.1 (M+1)+; Retention time: 0.3 min (LC Method B).

Step 5: 6-[(1-Benzyl-5,5-dimethyl-pyrrolidin-3-yl)amino]pyridine-2-sulfonamide

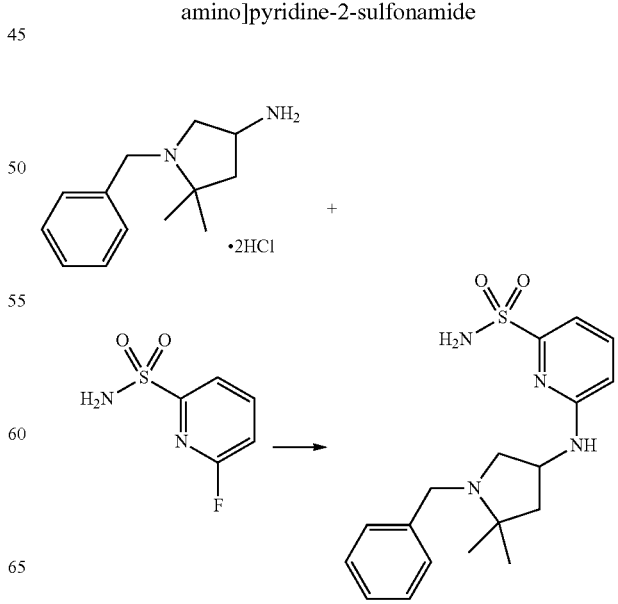

A 20 mL vial was charged with 6-fluoropyridine-2-sulfonamide (0.351 g, 1.992 mmol) and anhydrous dimethyl sulfoxide (5 mL), followed by addition of anhydrous potassium carbonate (1.377 g, 9.963 mmol) and 1-benzyl-5,5-dimethyl-pyrrolidin-3-amine (dihydrochloride salt) (0.580 g, 2.092 mmol), in that order. The vial was capped under nitrogen and stirred to 70° C. in an oil bath for 13 h, then at 90° C. for 8 h, followed by briefly heating at 100° C. for about 30 min. The reaction mixture was filtered over a pad of Celite then diluted with ethyl acetate (30 mL) and neutralized with glacial AcOH to pH 7. Washed with water (15 mL), followed by brine (15 mL). The organics were dried over sodium sulfate, filtered, and evaporated under reduced pressure. The crude material was purified by silica gel chromatography. Initially, using a gradient from 20%-100% ethyl acetate in hexanes did not provide clean product. A second silica gel chromatography purification (0%-15% methanol in dichloromethane) provided the desired compound, 6-[(1-benzyl-5,5-dimethyl-pyrrolidin-3-yl)amino]pyridine-2-sulfonamide (125 mg, 17%) as a light brown solid. ESI-MS m/z calc. 360.162, found 361.2 (M+1)+; Retention time: 0.59 min (LC Method B).

Step 6: 6-[(5,5-Dimethylpyrrolidin-3-yl)amino]pyridine-2-sulfonamide

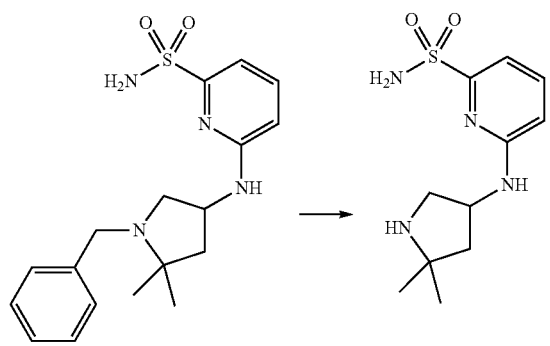 [SMILES: CC1(C)CC(Nc2cccc(S(N)(=O)=O)n2)CN1Cc1ccccc1 ; CC1(C)CC(Nc2cccc(S(N)(=O)=O)n2)CN1]

A stirred solution of 6-[(1-benzyl-5,5-dimethyl-pyrrolidin-3-yl)amino]pyridine-2-sulfonamide (125 mg, 0.3468 mmol) in anhydrous methanol (8 mL) was treated with palladium on carbon (40 mg, 0.03759 mmol) under nitrogen. The reaction was stirred at 52° C. under hydrogen (balloon) for 10 h. The reaction was allowed to cool to ambient temperature and the flask was evacuated, filled with nitrogen then palladium hydroxide (25 mg, 0.03560 mmol) was added. Again, the reaction mixture was stirred at 52° C. under hydrogen (balloon) for 7 h then allowed to cool to ambient temperature. The catalyst was filtered off over a pad of Celite and the filtrate was concentrated under reduced pressure and dried in vacuo to furnish 6-[(5,5-dimethylpyrrolidin-3-yl)amino]pyridine-2-sulfonamide (61 mg, 65%) as a light brown solid which was used in the subsequent reaction without further purification. ESI-MS m/z calc. 270.11505, found 271.1 (M+1)+; Retention time: 0.53 min (LC Method B).

Step 7: 2-Chloro-N-[[6-[(5,5-dimethylpyrrolidin-3-yl)amino]-2-pyridyl]sulfonyl]-6-[3-[2-[1-(trifluoromethyl)cyclopropyl]ethoxy]pyrazol-1-yl]pyridine-3-carboxamide (Dihydrochloride Salt)

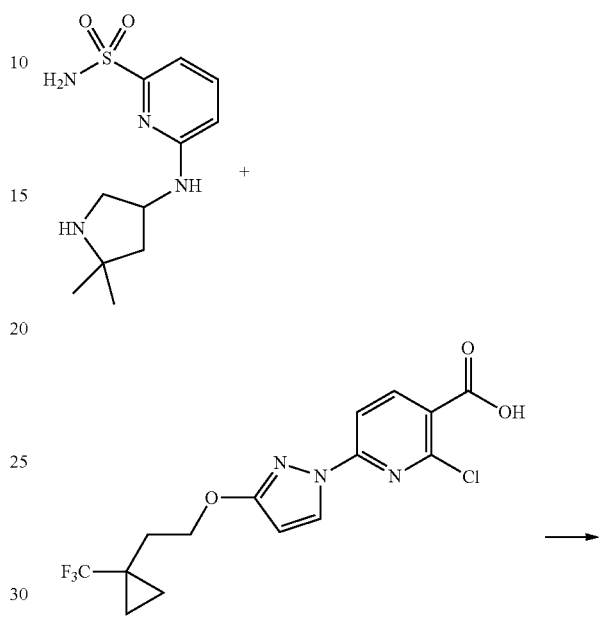

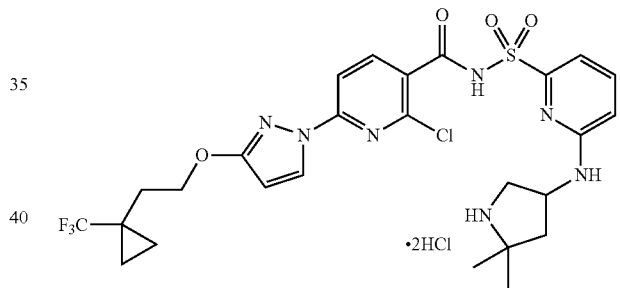

6-[(5,5-Dimethylpyrrolidin-3-yl)amino]pyridine-2-sulfonamide (43 mg, 0.1591 mmol) and carbonyl diimidazole (29 mg, 0.1788 mmol) were combined in dry tetrahydrofuran (3 mL) and stirred under nitrogen at 48° C. for 1 h. Then, a solution of 2-chloro-6-[3-[2-[1-(trifluoromethyl)cyclopropyl]ethoxy]pyrazol-1-yl]pyridine-3-carboxylic acid (60 mg, 0.1597 mmol) in dry tetrahydrofuran (1 mL) was added followed by 1,8-diazabicyclo[5.4.0]undec-7-ene (30 μL, 0.2006 mmol). The reaction was removed from the heat and stirred at ambient temperature for 12 h. The volatiles were removed under reduced pressure and the residue was taken up in dimethyl sulfoxide (1.5 mL), filtered through a Whatman 0.45 μm PTFE syringe filter disc and purified by preparative reverse-phase HPLC (1%-99% acetonitrile in water, hydrochloric acid as modifier) to furnish 2-chloro-N-[[6-[(5,5-dimethylpyrrolidin-3-yl)amino]-2-pyridyl]sulfonyl]-6-[3-[2-[1-(trifluoromethyl) cyclopropyl]ethoxy]pyrazol-1-yl]pyridine-3-carboxamide (dihydrochloride salt) (13 mg, 12%) as an off-white solid. 1H NMR (400 MHz, dimethyl sulfoxide-d6) δ 9.09 (s, 2H), 8.40 (d, J=2.9 Hz, 1H), 8.13 (d, J=8.3 Hz, 1H), 7.77-7.63 (m, 3H), 7.23 (d, J=7.2 Hz, 1H), 6.81 (d, J=8.4 Hz, 1H), 6.18 (d, J=2.9 Hz, 1H), 4.45-4.36 (m, 1H), 4.34 (t, J=7.1 Hz, 2H), 3.72-3.62 (m, 1H), 3.26-3.14 (m, 1H), 2.24 (dd, J=13.4, 8.3 Hz, 1H), 2.08 (t, J=7.1 Hz, 2H), 1.89 (dd, J=14, 4.0 Hz, 1H), 1.48 (s, 3H), 1.28 (s, 3H), 1.00-0.92 (m, 2H), 0.94-0.85 (m, 2H). ESI-MS m/z calc. 627.16425, found 628.2 (M+1)⁺; Retention time: 1.55 min (LC Method B).

Step 8: 5,5-Dimethyl-9-(3-{2-[1-(trifluoromethyl)cyclopropyl]ethoxy}-1H-pyrazol-1-yl)-15λ⁶-thia-2,6,8,14,20-pentaazatetracyclo[14.3.1.1³,⁶.0⁷,¹²]henicosa-1(20),7,9,11,16,18-hexaene-13,15,15-trione (Compound 31)

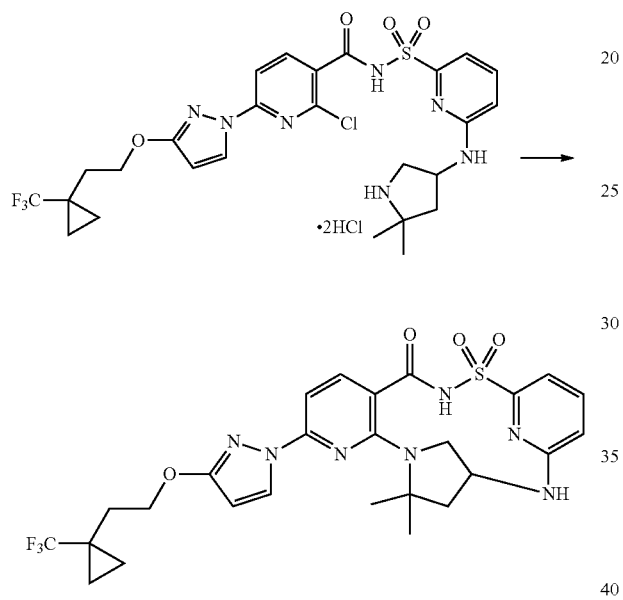

To a solution of 2-chloro-N-[[6-[(5,5-dimethylpyrrolidin-3-yl)amino]-2-pyridyl]sulfonyl]-6-[3-[2-[1-(trifluoromethyl)cyclopropyl]ethoxy]pyrazol-1-yl]pyridine-3-carboxamide (dihydrochloride salt) (11 mg, 0.01569 mmol) in anhydrous dimethyl sulfoxide (1.5 mL) was added cesium fluoride (3 mg, 0.01975 mmol), potassium carbonate (12 mg, 0.08683 mmol) (powdered by mortar & pestle) and a small amount of granular 4 Å molecular sieves (about 500 mg, heated with a heat gun for 5 min under vacuum for dryness). The resulting mixture was capped under nitrogen and heated at 150° C. for 17 h then allowed to cool to ambient temperature letting the solid settle at the bottom. The supernatant was filtered through a Whatman 0.45 μm PTFE syringe filter disc. The filtrate was concentrated and purified using a reverse phase HPLC-MS method using a Luna C₁₈ (2) column and a dual gradient run from 1%-99% acetonitrile in water (no modifier) giving 5,5-dimethyl-9-(3-{2-[1-(trifluoromethyl)cyclopropyl]ethoxy}-1H-pyrazol-1-yl)-15λ⁶-thia-2,6,8,14,20-pentaazatetracyclo[14.3.1.1³,⁶.0⁷,¹²]henicosa-1(20),7,9,11,16,18-hexaene-13,15,15-trione (Compound 31) (3.5 mg, 37%). ESI-MS m/z calc. 591.18756, found 592.3 (M+1)⁺; Retention time: 1.6 min (LC Method B).

Example 193: Preparation of (14S)-12,12-dimethyl-8-{3-oxo-octahydroimidazo[1,5-a]pyridin-2-yl}-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 213)

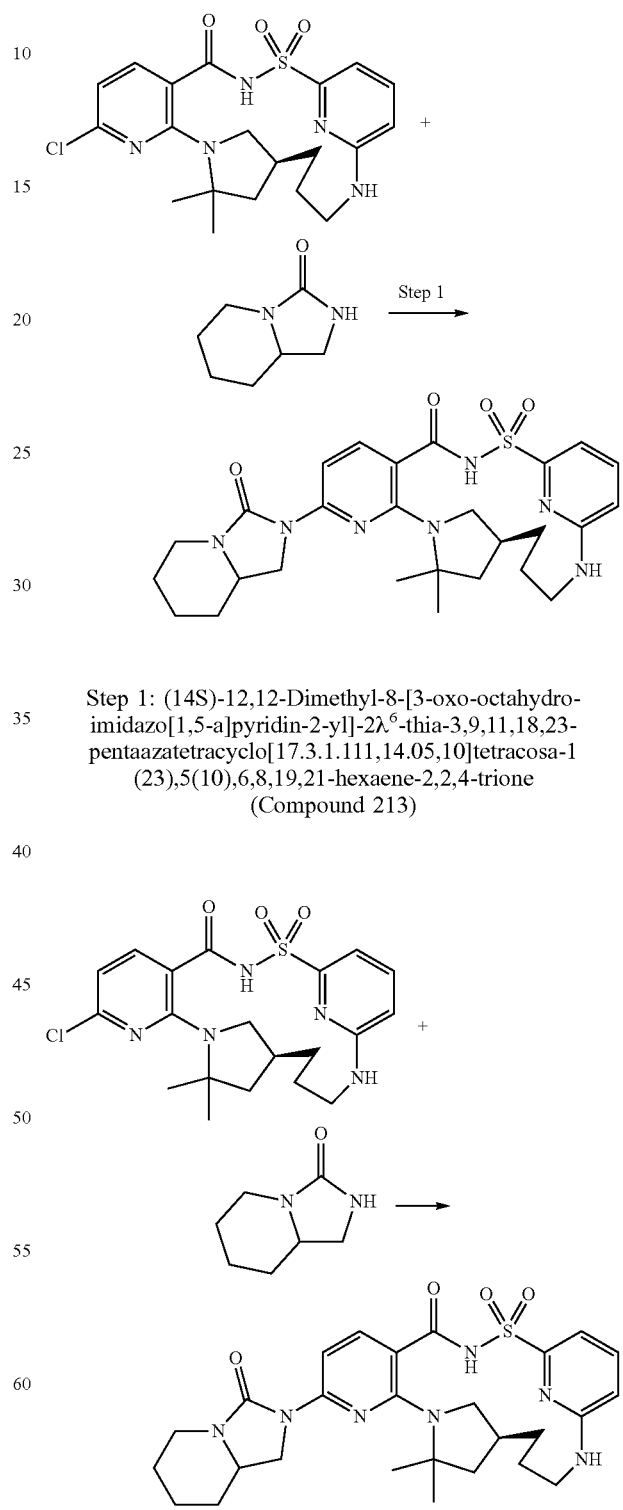

Step 1: (14S)-12,12-Dimethyl-8-[3-oxo-octahydro-imidazo[1,5-a]pyridin-2-yl]-2λ⁶-thia-3,9,11,18,23-pentaazatetracyclo[17.3.1.1¹¹,¹⁴.0⁵,¹⁰]tetracosa-1(23),5(10),6,8,19,21-hexaene-2,2,4-trione (Compound 213)

A 5 mL vial was charged with (14S)-8-chloro-12,12-dimethyl-2λ⁶-thia-3,9,11,18,23-pentaazatetracyclo

[17.3.1.1¹¹,¹⁴.0⁵,¹⁰]tetracosa-1(23),5,7,9,19,21-hexaene-2,2,4-trione (100 mg, 0.2222 mmol), 2,5,6,7,8,8a-hexahydro-1H-imidazo[1,5-a]pyridin-3-one (45 mg, 0.3210 mmol), Pd$_2$(dba)$_3$ (54 mg, 0.05897 mmol), Xantphos (33 mg, 0.05703 mmol), cesium carbonate (375 mg, 1.151 mmol) and anhydrous dioxane (1.6 mL). The mixture was sparged with nitrogen for 1-2 min, capped and stirred at 120° C. for 20 h and then cooled to room temperature. The solvent was evaporated and the reaction was diluted with dimethyl sulfoxide (900 μL), microfiltered and purified by reverse-phase preparative chromatography utilizing a C$_{18}$ column (10%-99% acetonitrile in water+5 mM hydrochloric acid). The product fractions were combined, brine was added and the organic solvents were evaporated. The product was extracted with dichloromethane, the organic phase was dried over sodium sulfate, filtered and evaporation of the solvents gave a solid. The obtained solid was purified by silica gel chromatography using a gradient from 100% dichloromethane to 5% methanol in dichloromethane giving (14S)-12,12-dimethyl-8-[3-oxo-octahydroimidazo[1,5-a]pyridin-2-yl]-2λ$^6$-thia-3,9,11,18,23-pentaazatetra cyclo[17.3.1.1¹¹,14.0⁵,¹⁰]tetracosa-1(23),5(10),6,8,19,21-hexaene-2,2,4-trione (Compound 213) (58.6 mg, 47%). ¹H NMR (400 MHz, Chloroform-d) δ 10.77 (s, 1H), 8.01 (d, J=8.7 Hz, 1H), 7.90 (d, J=8.7 Hz, 1H), 7.61-7.49 (m, 2H), 6.54 (p, J=3.7 Hz, 1H), 4.79 (d, J=7.9 Hz, 1H), 4.21-4.07 (m, 1H), 4.02 (dd, J=12.5, 3.6 Hz, 1H), 3.83 (s, 1H), 3.64-3.48 (m, 2H), 3.32 (t, J=8.9 Hz, 1H), 3.15 (d, J=14.0 Hz, 1H), 3.04 (t, J=9.4 Hz, 1H), 2.83-2.74 (m, 1H), 2.11 (dd, J=12.4, 8.6 Hz, 1H), 2.00-1.85 (m, 2H), 1.71 (d, J=9.8 Hz, 2H), 1.57 (d, J=2.0 Hz, 6H), 1.55 (d, J=1.2 Hz, 3H), 1.51-1.43 (m, 3H), 1.37 (t, J=12.8 Hz, 2H). ESI-MS m/z calc. 553.24713, found 554.2 (M+1)$^+$; Retention time: 1.62 min (LC Method E).

Example 194: Preparation of (14S)-12,12-dimethyl-8-{1-oxo-2-azaspiro[4.5]decan-2-yl}-2λ$^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Compound 222)

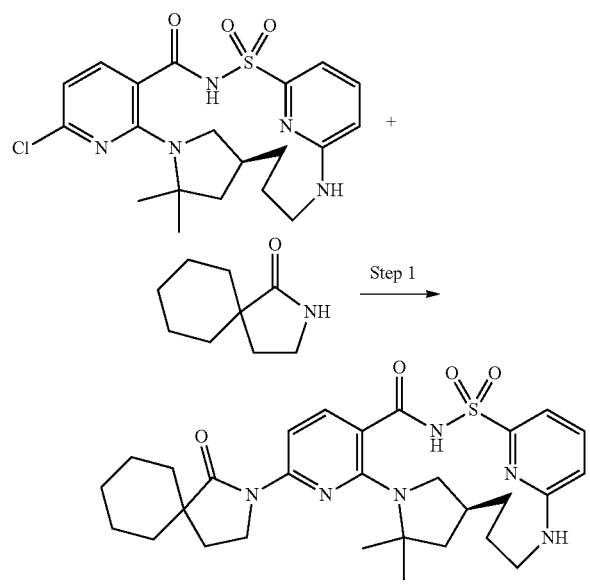

Step 1: (14S)-12,12-Dimethyl-8-{1-oxo-2-azaspiro[4.5]decan-2-yl}-2λ$^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Compound 222)

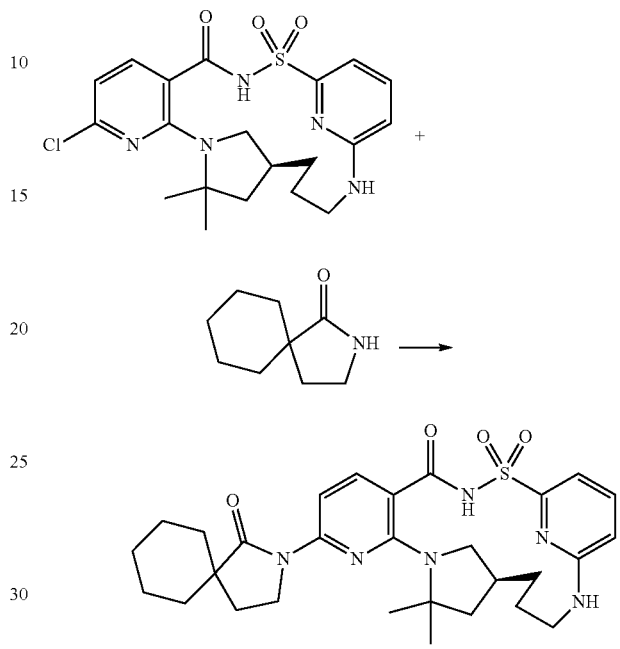

A 5 mL vial was charged with (14S)-8-chloro-12,12-dimethyl-2λ$^6$-thia-3,9,11,18,23-pentaazatetracyclo[17.3.1.1¹¹,14.0⁵,¹⁰]tetracosa-1(23),5,7,9,19,21-hexaene-2,2,4-trione (50 mg, 0.1111 mmol), 2-azaspiro[4.5]decan-1-one (24 mg, 0.1566 mmol), Pd$_2$(dba)$_3$ (26 mg, 0.02839 mmol), Xantphos (16 mg, 0.02765 mmol), cesium carbonate (180 mg, 0.5525 mmol) and anhydrous dioxane (800 μL). The mixture was sparged with nitrogen for 1-2 min, capped and stirred at 120° C. for 20 h and then cooled to room temperature. The solvent was evaporated, the reaction was diluted with dimethyl sulfoxide (900 μL), microfiltered and purified by reverse-phase preparative chromatography utilizing a C$_{18}$ column (10%-99% acetonitrile in water+5 mM hydrochloric acid). The product fractions were combined, brine was added and the organic solvents were evaporated. The product was extracted with dichloromethane, the organic phase was dried over sodium sulfate, filtered and evaporation of the solvents gave a solid. The obtained solid was purified by silica gel chromatography using a gradient from 100% dichloromethane to 5% methanol in dichloromethane. The pure fractions were collected and the solvents evaporated to give as an off-white solid, (14S)-12,12-dimethyl-8-{1-oxo-2-azaspiro[4.5]decan-2-yl}-2λ$^6$-thia-3,9,11,18,23-pentaazatetracyclo[17.3.1.1¹¹,14.0⁵,¹⁰]tetracosa-1(22),5,7,9,19(23),20-hexaene-2,2,4-trione (Compound 222) (13.01 mg, 20%). ¹H NMR (400 MHz, Chloroform-d) δ 10.41 (s, 1H), 8.10-7.95 (m, 2H), 7.62-7.49 (m, 2H), 6.55 (dd, J=6.8, 2.4 Hz, 1H), 4.74 (s, 1H), 3.93 (t, J=7.2 Hz, 2H), 3.90-3.79 (m, 1H), 3.32 (dd, J=10.0, 7.7 Hz, 1H), 3.16 (d, J=14.3 Hz, 1H), 3.07 (s, 1H), 2.68 (dd, J=11.9, 6.4 Hz, 1H), 2.11 (dd, J=12.4, 8.4 Hz, 1H), 2.03 (dd, J=8.0, 6.3 Hz, 2H), 1.78-1.72 (m, 3H), 1.70-1.62 (m, 3H), 1.57 (d, J=5.4 Hz, 8H), 1.38 (q, J=11.0, 9.2 Hz, 4H), 1.24-1.17 (m, 1H), 0.91-0.79 (m, 2H). ESI-MS m/z calc. 566.2675, found 567.2 (M+1)+; Retention time: 2.01 min (LC Method E).

Example 195: Preparation of 8-[3-(3,3-dimethylbutyl)-2-oxoimidazolidin-1-yl]-12,12-dimethyl-2λ6-thia-3,9,11,19,24-pentaazatetracyclo[18.3.1.05,10.011,15]tetracosa-1(23),5,7,9,20(24),21-hexaene-2,2,4-trione (Compound 232)

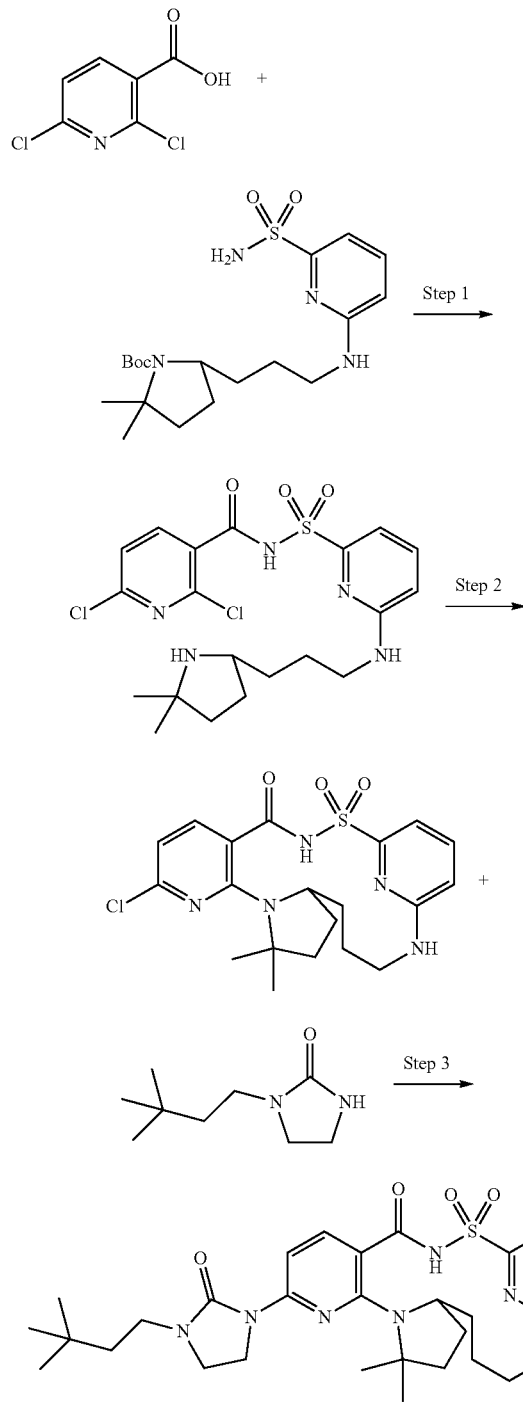

Step 1: 2,6-Dichloro-N-[[6-[3-(5,5-dimethylpyrrolidin-2-yl)propylamino]-2-pyridyl]sulfonyl]pyridine-3-carboxamide (Hydrochloride Salt)

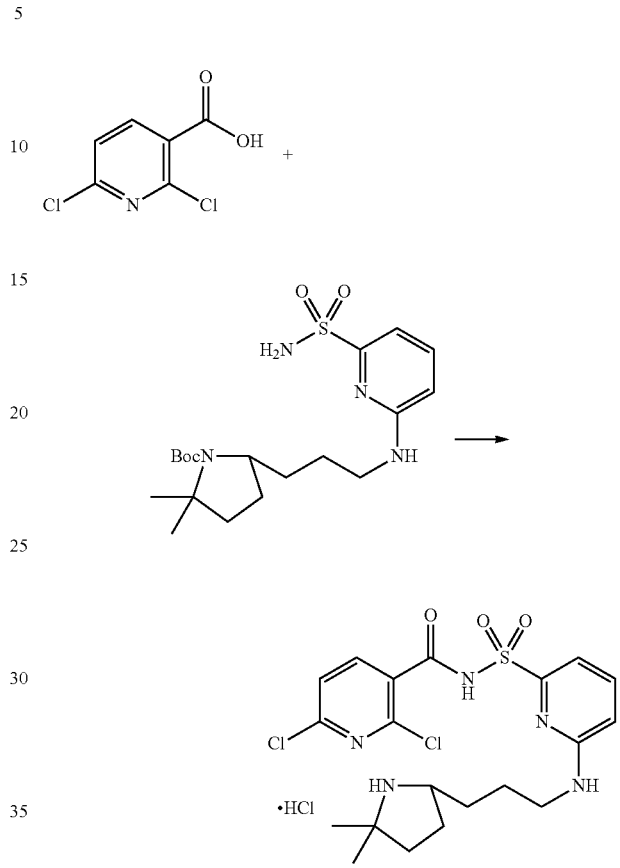

A 50 mL flask charged with 2,6-dichloropyridine-3-carboxylic acid (733 mg, 3.818 mmol) and carbonyl diimidazole (620 mg, 3.824 mmol) was evacuated/backfilled with nitrogen. Added tetrahydrofuran (15 mL) and the mixture was stirred at 50° C. for 1 h. Next, a solution of tert-butyl 2,2-dimethyl-5-[3-[(6-sulfamoyl-2-pyridyl)amino]propyl]pyrrolidine-1-carboxylate (1.5 g, 3.636 mmol) and 1,8-diazabicyclo[5.4.0]undec-7-ene (1385 mg, 9.098 mmol) in tetrahydrofuran (10 mL) was added and the mixture was stirred overnight at 50° C. overnight. The reaction was diluted with ethyl acetate and washed with water. The organic phase was dried over sodium sulfate, filtered and evaporated in vacuo then purified by preparative reverse-phase chromatography using a $C_{18}$ column (5%-95% acetonitrile in water) to afford the acylsulfonamide intermediate. A solution of this intermediate in dioxane (5 mL) was treated with hydrochloric acid (6 mL of 6 M in dioxane, 36.00 mmol) and stirred at room temperature for 3 h. The mixture was evaporated in vacuo to afford 2,6-dichloro-N-[[6-[3-(5,5-dimethylpyrrolidin-2-yl)propylamino]-2-pyridyl]sulfonyl]pyridine-3-carboxamide (hydrochloride salt) (0.9 g, 47%). ESI-MS m/z calc. 485.10553, found 486.15 (M+1)+; Retention time: 0.42 min (LC Method A).

Step 2: 8-Chloro-12,12-dimethyl-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione

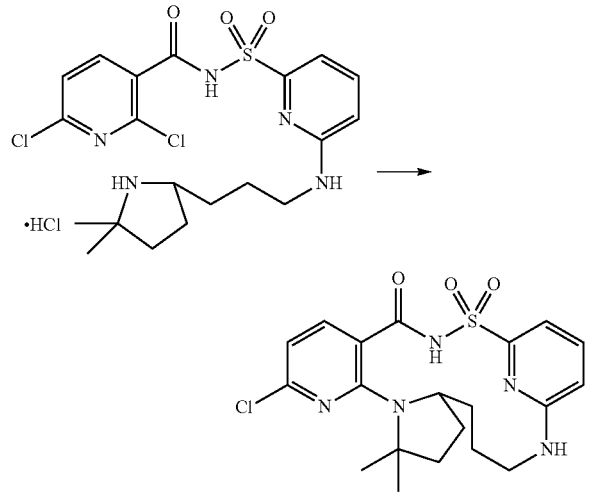

In 5 mL vial, potassium carbonate (133 mg, 0.9623 mmol), cesium fluoride (60 mg, 0.3950 mmol) and 4 Å molecular sieves (300 mg) were sealed and purged with nitrogen. Next, a solution 2,6-dichloro-N-[[6-[3-(5,5-dimethylpyrrolidin-2-yl)propylamino]-2-pyridyl]sulfonyl]pyridine-3-carboxamide (hydrochloride salt) (100 mg, 0.1912 mmol) in dimethyl sulfoxide (3 mL) was added and the mixture was stirred at 150° C. overnight. The mixture was filtered and purified by preparative reverse phase HPLC (C₁₈ column, 1%-99% acetonitrile in water with hydrochloric acid modifier) to afford 8-chloro-12,12-dimethyl-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (20.8 mg, 24%). ESI-MS m/z calc. 449.12885, found 450.18 (M+1)⁺; Retention time: 1.46 min (LC Method B).

Step 3: 8-[3-(3,3-Dimethylbutyl)-2-oxoimidazolidin-1-yl]-12,12-dimethyl-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 232)

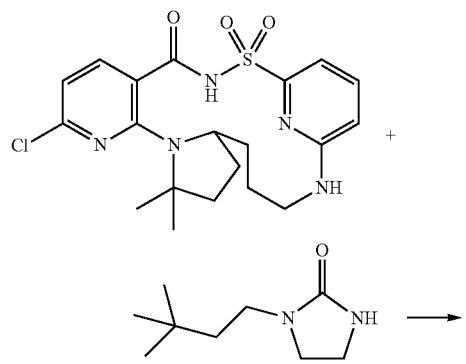

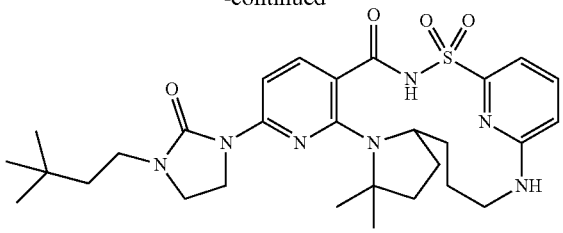

A solution of 8-chloro-12,12-dimethyl-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (200 mg, 0.4445 mmol), 1-(3,3-dimethylbutyl)imidazolidin-2-one (114 mg, 0.6696 mmol), Xantphos (65 mg, 0.1123 mmol), Pd₂(dba)₃ (102 mg, 0.1114 mmol) and cesium carbonate (724 mg, 2.222 mmol) in dioxane (4 mL) were degassed by purging with nitrogen for 2 min. The mixture was stirred at 120° C. overnight. The reaction mixture was filtered and purified by preparative reverse phase HPLC (C₁₈ column, 1%-99% acetonitrile in water with hydrochloric acid modifier) to afford 8-[3-(3,3-dimethylbutyl)-2-oxoimidazolidin-1-yl]-12,12-dimethyl-2λ⁶-thia-3,9,11,19,24-pentaazatetracyclo[18.3.1.0⁵,¹⁰.0¹¹,¹⁵]tetracosa-1(23),5,7,9,20(24),21-hexaene-2,2,4-trione (Compound 232) (9 mg, 3%). ESI-MS m/z calc. 583.29407, found 584.39 (M+1)⁺; Retention time: 1.71 min (LC Method B).

Example 196: Preparation of 19,19-dimethyl-4-(3-{3-[1-(trifluoromethyl)cyclopropyl]propoxy}-1H-pyrazol-1-yl)-10λ⁶-thia-1,3,9,14,21-pentaazatetracyclo[15.2.1.1¹¹,¹⁴.0²,⁷]henicosa-2,4,6,11(21),12-pentaene-8,10,10-trione (Enantiomer 1) (Compound 279) and 19,19-dimethyl-4-(3-{3-[1-(trifluoromethyl)cyclopropyl]propoxy}-1H-pyrazol-1-yl)-10λ⁶-thia-1,3,9,14,21-pentaazatetracyclo[15.2.1.1¹¹,¹⁴.0²,⁷]henicosa-2,4,6,11(21),12-pentaene-8,10,10-trione (Enantiomer 2) (Compound 278)

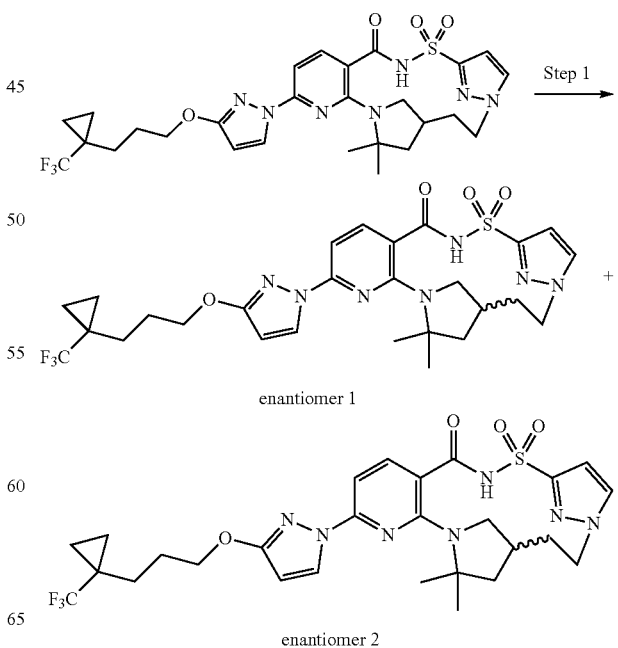

Step 1: 19,19-Dimethyl-4-(3-{3-[1-(trifluoromethyl)
cyclopropyl]propoxy}-1H-pyrazol-1-yl)-10λ⁶-thia-1,
3,9,14,21-pentaazatetracyclo[15.2.1.1¹¹,¹⁴.0²,⁷]
henicosa-2,4,6,11(21),12-pentaene-8,10,10-trione
(enantiomer 1) (Compound 279) and 19,19-dim-
ethyl-4-(3-{3-[1-(trifluoromethyl)cyclopropyl]
propoxy}-1H-pyrazol-1-yl)-10λ⁶-thia-1,3,9,14,21-
pentaazatetracyclo[15.2.1.1¹¹,¹⁴.0²,⁷]henicosa-2,4,
6,11(21),12-pentaene-8,10,10-trione (Enantiomer 2)
(Compound 278)

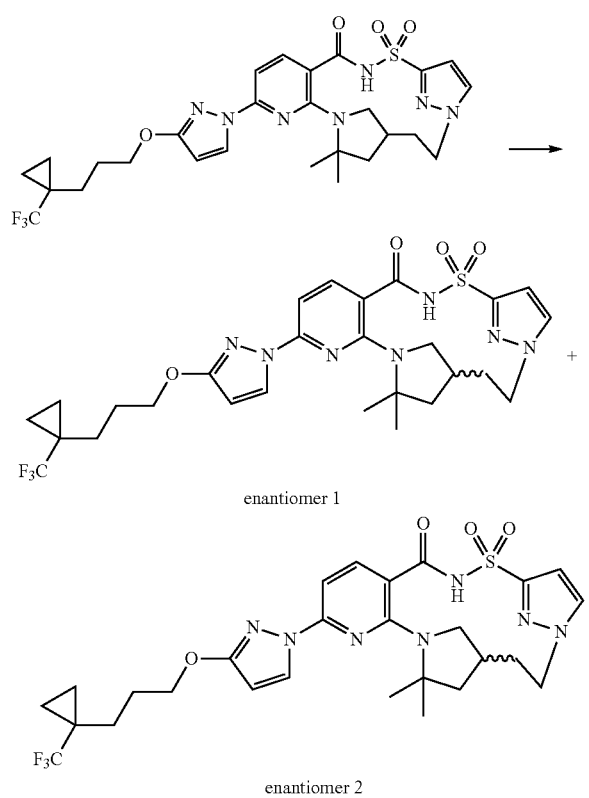

Racemic 19,19-dimethyl-4-(3-{3-[1-(trifluoromethyl)cy-
clopropyl]propoxy}-1H-pyrazol-1-yl)-10λ⁶-thia-1,3,9,14,
21-pentaazatetracyclo[15.2.1.1¹¹,¹⁴.0²,⁷]henicosa-2,4,6,11
(21),12-pentaene-8,10,10-trione (21 mg, 0.03456 mmol)
was subjected to chiral SFC chromatography using a Chi-
ralPak AS-H (250×21.2 mm column, 5 μm particle size)
with 25% acetonitrile:methanol (90:10, 20 mM NH₃))/75%
carbon dioxide mobile phase at 10 mL/min giving as the first
enantiomer to elute, 19,19-dimethyl-4-(3-{3-[1-(trifluorom-
ethyl)cyclopropyl]propoxy}-1H-pyrazol-1-yl)-10λ⁶-thia-1,
3,9,14,21-pentaazatetracyclo[15.2.1.1¹¹,¹⁴.0²,⁷]henicosa-
2,4,6,11(21),12-pentaene-8,10,10-trione (enantiomer 1)
(Compound 279) (7.3 mg, 70%). ¹H NMR (400 MHz,
dimethyl sulfoxide-d₆) δ 12.61 (s, 1H), 8.18 (d, J=2.7 Hz,
1H), 8.01 (s, 1H), 7.65 (d, J=8.2 Hz, 1H), 6.93 (s, 1H), 6.85
(d, J=8.2 Hz, 1H), 6.09 (d, J=2.7 Hz, 1H), 4.59 (d, J=13.9
Hz, 1H), 4.23-4.08 (m, 3H), 3.06 (s, 1H), 2.17 (d, J=14.9 Hz,
1H), 1.94 (dd, J=11.9, 5.7 Hz, 1H), 1.85 (dq, J=10.7, 6.3 Hz,
2H), 1.77-1.65 (m, 3H), 1.56 (s, 3H), 1.49 (s, 4H), 0.95-0.88
(m, 2H), 0.79-0.70 (m, 2H). ESI-MS m/z calc. 607.2189,
found 608.3 (M+1)⁺; Retention time: 2.08 min (LC Method
B). The second enantiomer to elute was 19,19-dimethyl-4-
(3-{3-[1-(trifluoromethyl)cyclopropyl]propoxy}-1H-pyra-
zol-1-yl)-10λ⁶-thia-1,3,9,14,21-pentaazatetracyclo
[15.2.1.1¹¹,¹⁴.0²,⁷]henicosa-2,4,6,11(21),12-pentaene-8,
10,10-trione (enantiomer 2) (Compound 278) (7.8 mg,
70%). ESI-MS m/z calc. 607.2189, found 608.4 (M+1)⁺;
Retention time: 2.08 min (LC Method B).

Example 197: Preparation of (14S)-8-[3-(3,3-dim-
ethylbutyl)-2-oxoimidazolidin-1-yl]-12,12-dimethyl-
2λ⁶-thia-3,9,11,18,23-pentaazatetracyclo[17.3.1.1¹¹,
14.0⁵,¹⁰]tetracosa-1(22),5,7,9,19(23),20-hexaene-2,
2,4-trione (Compound 128)

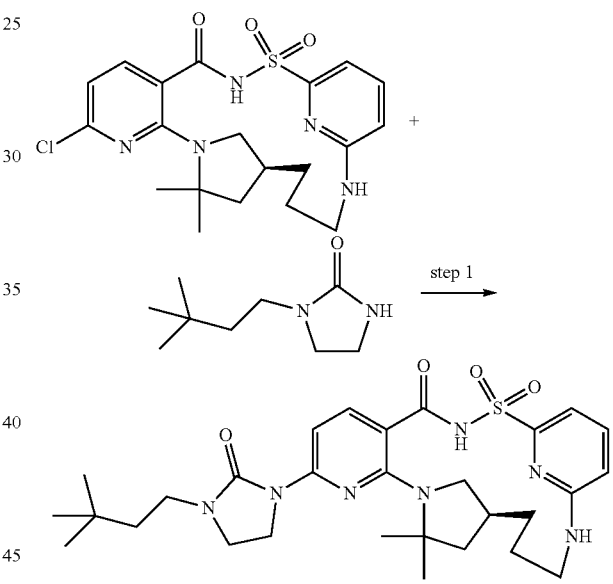

Step 1: (14S)-8-[3-(3,3-Dimethylbutyl)-2-oxoimida-
zolidin-1-yl]-12,12-dimethyl-2λ⁶-thia-3,9,11,18,23-
pentaazatetracyclo[17.3.1.1¹¹,¹⁴.0⁵,¹⁰]tetracosa-1
(22),5,7,9,19(23),20-hexaene-2,2,4-trione
(Compound 128)

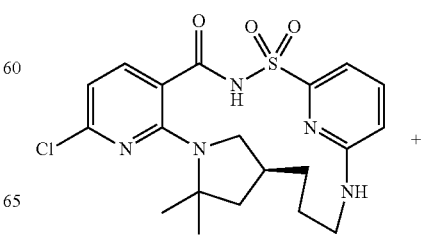

-continued

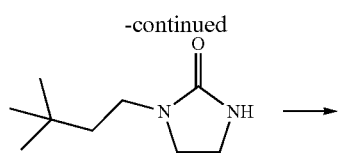

Example 198: Preparation of (14S)-8-(3,4-dihydro-2H-pyran-6-yl)-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 303)

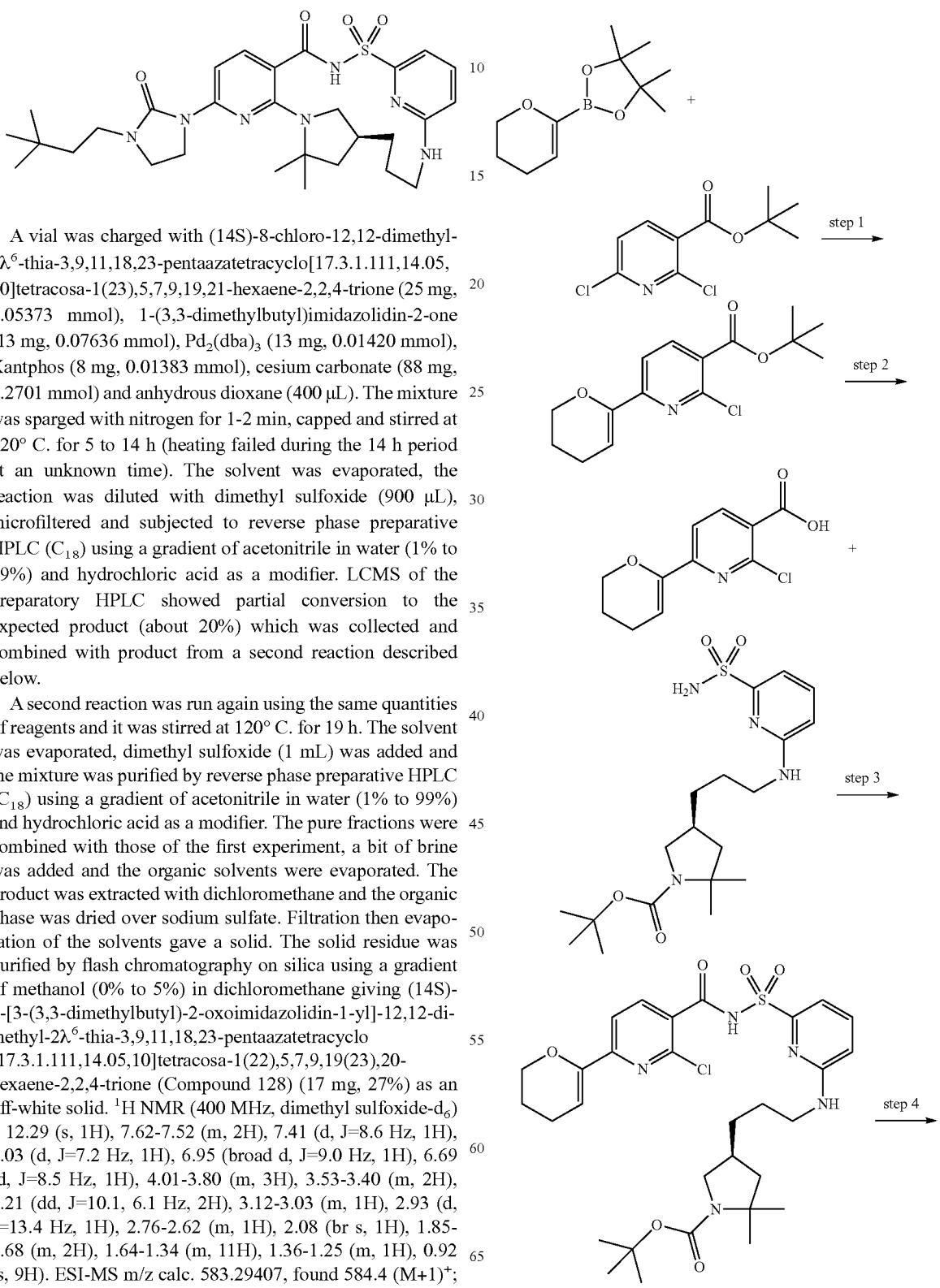

A vial was charged with (14S)-8-chloro-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (25 mg, 0.05373 mmol), 1-(3,3-dimethylbutyl)imidazolidin-2-one (13 mg, 0.07636 mmol), $Pd_2(dba)_3$ (13 mg, 0.01420 mmol), Xantphos (8 mg, 0.01383 mmol), cesium carbonate (88 mg, 0.2701 mmol) and anhydrous dioxane (400 μL). The mixture was sparged with nitrogen for 1-2 min, capped and stirred at 120° C. for 5 to 14 h (heating failed during the 14 h period at an unknown time). The solvent was evaporated, the reaction was diluted with dimethyl sulfoxide (900 μL), microfiltered and subjected to reverse phase preparative HPLC ($C_{18}$) using a gradient of acetonitrile in water (1% to 99%) and hydrochloric acid as a modifier. LCMS of the preparatory HPLC showed partial conversion to the expected product (about 20%) which was collected and combined with product from a second reaction described below.

A second reaction was run again using the same quantities of reagents and it was stirred at 120° C. for 19 h. The solvent was evaporated, dimethyl sulfoxide (1 mL) was added and the mixture was purified by reverse phase preparative HPLC ($C_{18}$) using a gradient of acetonitrile in water (1% to 99%) and hydrochloric acid as a modifier. The pure fractions were combined with those of the first experiment, a bit of brine was added and the organic solvents were evaporated. The product was extracted with dichloromethane and the organic phase was dried over sodium sulfate. Filtration then evaporation of the solvents gave a solid. The solid residue was purified by flash chromatography on silica using a gradient of methanol (0% to 5%) in dichloromethane giving (14S)-8-[3-(3,3-dimethylbutyl)-2-oxoimidazolidin-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound 128) (17 mg, 27%) as an off-white solid. ¹H NMR (400 MHz, dimethyl sulfoxide-$d_6$) δ 12.29 (s, 1H), 7.62-7.52 (m, 2H), 7.41 (d, J=8.6 Hz, 1H), 7.03 (d, J=7.2 Hz, 1H), 6.95 (broad d, J=9.0 Hz, 1H), 6.69 (d, J=8.5 Hz, 1H), 4.01-3.80 (m, 3H), 3.53-3.40 (m, 2H), 3.21 (dd, J=10.1, 6.1 Hz, 2H), 3.12-3.03 (m, 1H), 2.93 (d, J=13.4 Hz, 1H), 2.76-2.62 (m, 1H), 2.08 (br s, 1H), 1.85-1.68 (m, 2H), 1.64-1.34 (m, 11H), 1.36-1.25 (m, 1H), 0.92 (s, 9H). ESI-MS m/z calc. 583.29407, found 584.4 (M+1)⁺; Retention time: 1.88 min (LC Method B).

-continued

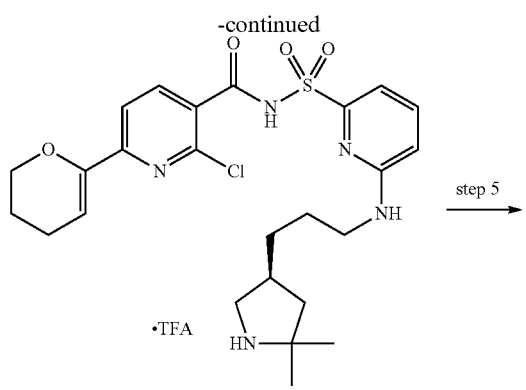

step 5

Step 1: tert-Butyl 2-chloro-6-(3,4-dihydro-2H-pyran-6-yl)pyridine-3-carboxylate

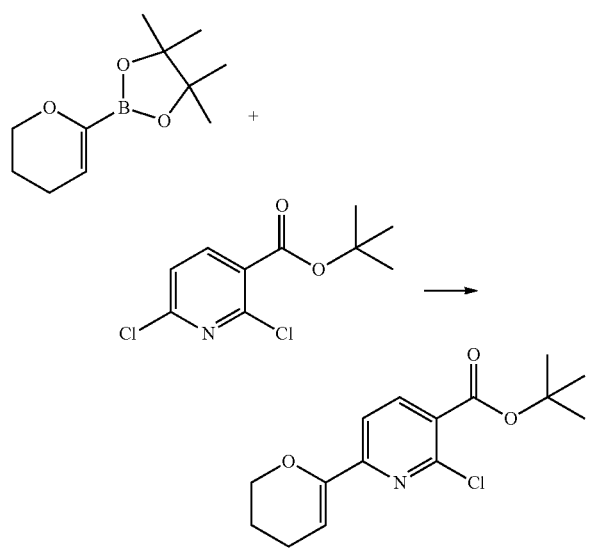

A 50 mL round bottom flask equipped with a magnetic stir bar was charged with tert-butyl 2,6-dichloropyridine-3-carboxylate (10.09 g, 40.668 mmol), 2-(3,4-dihydro-2H-pyran-6-yl)-4,4,5,5-tetramethyl-1,3,2-dioxaborolane (10.55 g, 49.215 mmol) and Pd(PPh$_3$)$_2$Cl$_2$ (1.42 g, 2.0231 mmol) in EtOH (10 mL), toluene (10 mL) and water (2 mL). The mixture was refluxed at 95° C. overnight in an oil bath. The cooled reaction was concentrated then taken up in ethyl acetate and washed with aqueous brine. The organic layer was dried over sodium sulfate, filtered and evaporated to give a crude oil which was purified by silica gel chromatography using a gradient from 100% hexane to 5% ethyl acetate in hexane to provide tert-butyl 2-chloro-6-(3,4-dihydro-2H-pyran-6-yl)pyridine-3-carboxylate (9.2 g, 76%) as a colorless oil. $^1$H NMR (250 MHz, dimethyl sulfoxide-d$_6$) δ 8.17 (d, J=8.0 Hz, 1H), 7.53 (d, J=8.0 Hz, 1H), 6.19-6.04 (m, 1H), 4.27-4.06 (m, 2H), 2.23 (q, J=6.1, 4.4 Hz, 2H), 1.96-1.78 (m, 2H), 1.55 (s, 9H). ESI-MS m/z calc. 295.09753, found 296.0 (M+1)$^+$; Retention time: 6.52 min (LC Method Q).

Step 2: 2-Chloro-6-(3,4-dihydro-2H-pyran-6-yl)pyridine-3-carboxylic Acid

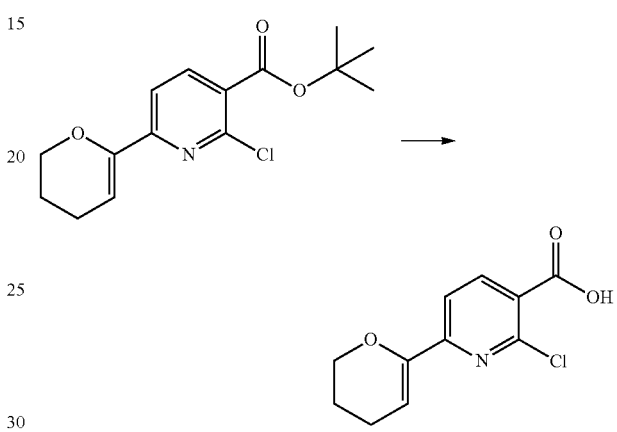

Lithium hydroxide monohydrate (468 mg, 11.153 mmol) was added to a solution of tert-butyl 2-chloro-6-(3,4-dihydro-2H-pyran-6-yl)pyridine-3-carboxylate (320 mg, 1.0711 mmol) in methanol (5 mL), tetrahydrofuran (20 mL) and water (10 mL). The mixture was stirred at 40° C. for 16 hours and cooled down to room temperature. The mixture was acidified with 5% HCl and extracted with EtOAc (2×20 mL). The combined organic layers were washed with brine and dried over Na$_2$SO$_4$, filtered and evaporated to afford 2-chloro-6-(3,4-dihydro-2H-pyran-6-yl)pyridine-3-carboxylic acid (248 mg, 94%) as a white solid. $^1$H NMR (250 MHz, DMSO-d$_6$) δ 8.25 (d, J=8.0 Hz, 1H), 7.55 (d, J=8.0 Hz, 1H), 6.13 (t, J=4.2 Hz, 1H), 4.21-4.12 (m, 2H), 2.24 (q, J=6.3, 5.8 Hz, 2H), 1.86 (p, J=5.9 Hz, 2H). ESI-MS m/z calc. 239.0349, found 240.0 (M+1)$^+$; Retention time: 3.95 min (LC Method Q).

Step 3: tert-Butyl (4S)-4-[3-[[6-[[2-chloro-6-(3,4-dihydro-2H-pyran-6-yl)pyridine-3-carbonyl]sulfamoyl]-2-pyridyl]amino]propyl]-2,2-dimethyl-pyrrolidine-1-carboxylate

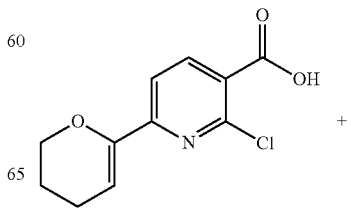

+

1133

-continued

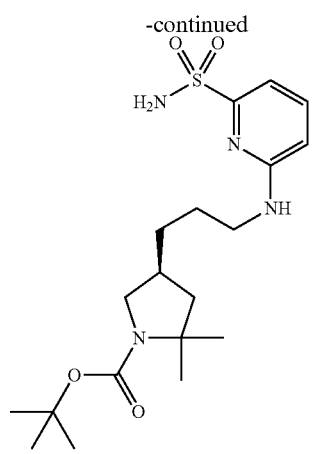

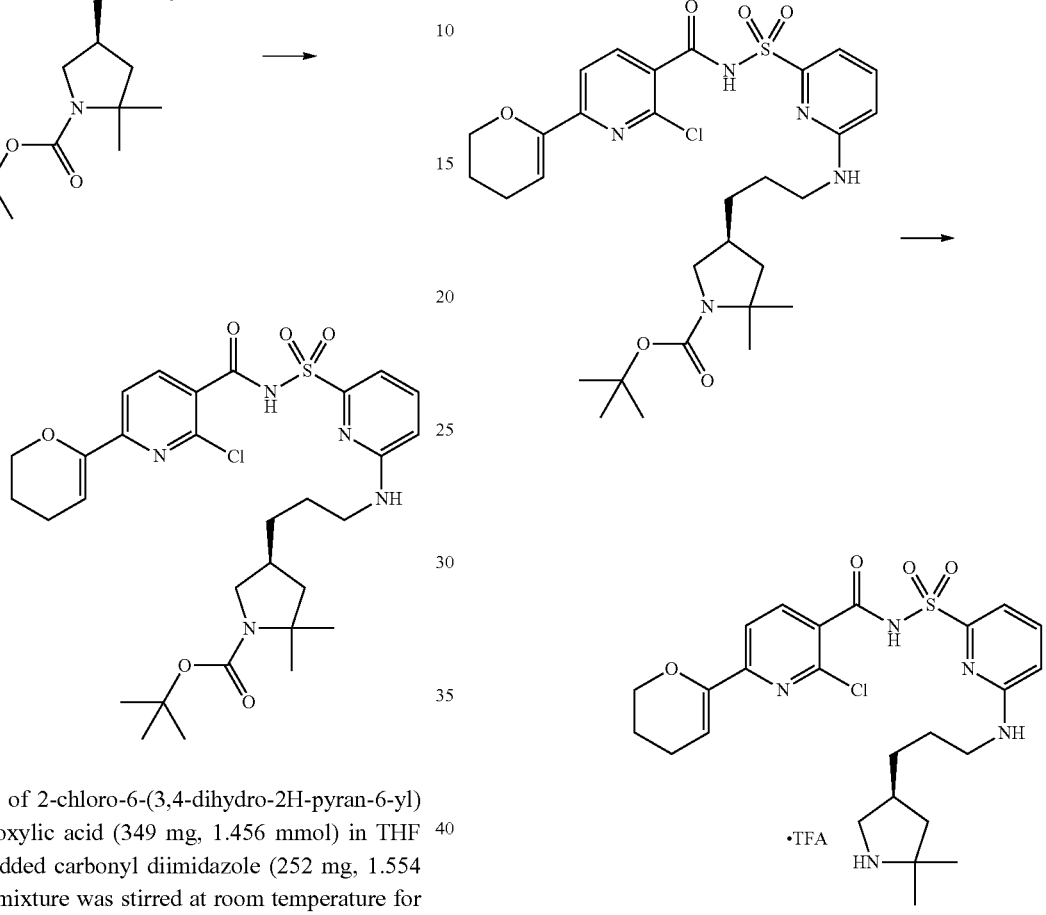

1134

Step 4: 2-Chloro-6-(3,4-dihydro-2H-pyran-6-yl)-N-[[6-[3-[(3S)-5,5-dimethylpyrrolidin-3-yl]propylamino]-2-pyridyl]sulfonyl]pyridine-3-carboxamide (Trifluoroacetate Salt)

To a solution of 2-chloro-6-(3,4-dihydro-2H-pyran-6-yl)pyridine-3-carboxylic acid (349 mg, 1.456 mmol) in THF (8.0 mL) was added carbonyl diimidazole (252 mg, 1.554 mmol) and the mixture was stirred at room temperature for 20 hours. Then, tert-butyl (4S)-2,2-dimethyl-4-[3-[(6-sulfamoyl-2-pyridyl)amino]propyl]pyrrolidine-1-carboxylate (400 mg, 0.9696 mmol) was added followed by DBU (475 μL, 3.176 mmol) and the resulting mixture was stirred for 3 hours at room temperature. The reaction was diluted with ethyl acetate and washed with a saturated aqueous sodium bicarbonate solution. The organic layer was further washed with 10% aqueous citric acid solution followed by brine. The organics were separated, dried over sodium sulfate, filtered, evaporated and then purified by silica gel chromatography using a gradient from 100% hexanes to 100% ethyl acetate. The resulting residue was further purified by preparative reverse phase HPLC ($C_{18}$ column, 30%-99% acetonitrile in water with hydrochloric acid modifier) to afford tert-butyl (4S)-4-[3-[[6-[[2-chloro-6-(3,4-dihydro-2H-pyran-6-yl)pyridine-3-carbonyl]sulfamoyl]-2-pyridyl]amino]propyl]-2,2-dimethyl-pyrrolidine-1-carboxylate (140 mg, 23%) as a white solid. ESI-MS m/z calc. 633.2388, found 634.2 (M+1)$^+$; Retention time: 2.11 min (LC Method B).

tert-Butyl (4S)-4-[3-[[6-[[2-chloro-6-(3,4-dihydro-2H-pyran-6-yl)pyridine-3-carbonyl]sulfamoyl]-2-pyridyl]amino]propyl]-2,2-dimethyl-pyrrolidine-1-carboxylate (140 mg, 0.2208 mmol) was dissolved in dichloromethane (610.8 μL) and to the mixture was added trifluoroacetic acid (681.1 μL, 8.841 mmol) and the mixture was stirred at room temperature for 2 hours. Concentrated the mixture to dryness under reduced pressure, added 1 mL of toluene and removed by rotary evaporation (45° C. water bath). Again added 1 mL of toluene and removed by rotary evaporation (45° C. water bath) then dried under vacuum giving 2-chloro-6-(3,4-dihydro-2H-pyran-6-yl)-N-[[6-[3-[(3S)-5,5-dimethylpyrrolidin-3-yl]propylamino]-2-pyridyl]sulfonyl]pyridine-3-carboxamide (trifluoroacetate salt) (162.3 mg, 100%) as a white solid. ESI-MS m/z calc. 533.18634, found 534.3 (M+1)$^+$; Retention time: 0.52 min (LC Method A).

1135

Step 5: (14S)-8-(3,4-dihydro-2H-pyran-6-yl)-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Compound 303)

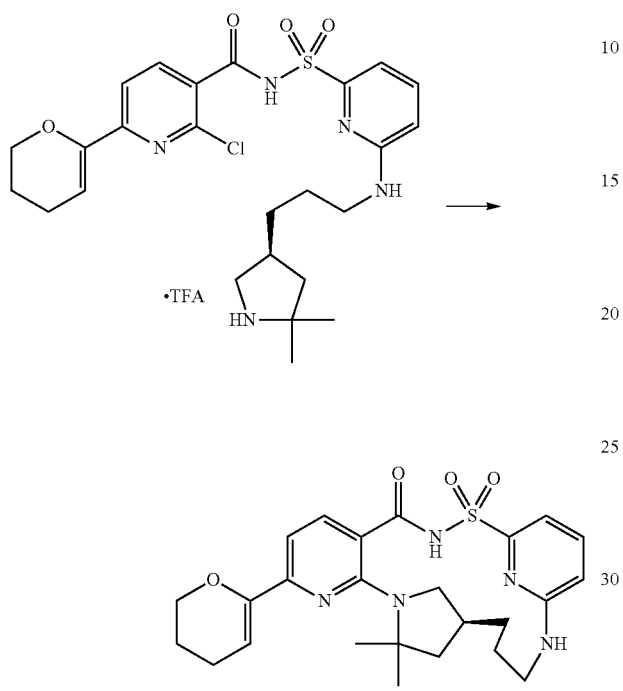

To a solution of 2-chloro-6-(3,4-dihydro-2H-pyran-6-yl)-N-[[6-[3-[(3S)-5,5-dimethylpyrrolidin-3-yl]propylamino]-2-pyridyl]sulfonyl]pyridine-3-carboxamide (trifluoroacetate salt) (162.3 mg, 0.2204 mmol) in NMP (8.591 mL) was added potassium carbonate (213.8 mg, 1.547 mmol). The mixture was purged with nitrogen for 5 min then heated to 180° C. and stirred overnight. Cooled to room temperature, diluted with EtOAc, washed with 1N HCl, dried (sodium sulfate), filtered and concentrated to a brown oil which was filtered and purified by reverse phase HPLC (C$_{18}$ column, 1%-99% acetonitrile in water (5 mM HCl)) giving as a white solid, (14S)-8-(3,4-dihydro-2H-pyran-6-yl)-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (3.31 mg, 3%). $^1$H NMR (400 MHz, dimethyl sulfoxide-d$_6$) δ 12.50 (s, 1H), 7.66 (d, J=7.9 Hz, 1H), 7.57 (t, J=7.9 Hz, 1H), 7.04 (d, J=7.1 Hz, 1H), 6.98 (s, 1H), 6.76 (d, J=8.0 Hz, 1H), 6.70 (d, J=8.5 Hz, 1H), 5.94 (s, 1H), 4.11 (s, 2H), 3.92 (d, J=11.8 Hz, 1H), 3.11 (s, 1H), 2.93 (d, J=13.1 Hz, 1H), 2.66 (s, 1H), 2.20 (d, J=5.3 Hz, 2H), 2.09 (s, 1H), 1.83 (d, J=5.9 Hz, 3H), 1.73 (s, 1H), 1.61 (s, 1H), 1.57 (s, 3H), 1.52 (s, 1H), 1.49 (s, 3H), 1.29 (d, J=12.2 Hz, 1H), 1.24 (s, 1H). ESI-MS m/z calc. 497.2097, found 498.1 (M+1)$^+$; Retention time: 1.98 min (LC Method B).

1136

Example 199: Preparation of 8-[3-(2-{Dispiro[2.0.2.1]heptan-7-yl}ethoxy)-1H-pyrazol-1-yl]-16,16-difluoro-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Enantiomer 1) (Compound 305, SFC Peak 1) and 8-[3-(2-{dispiro[2.0.2.1]heptan-7-yl}ethoxy)-1H-pyrazol-1-yl]-16,16-difluoro-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione (Enantiomer 2) (Compound 304, SFC Peak 2)

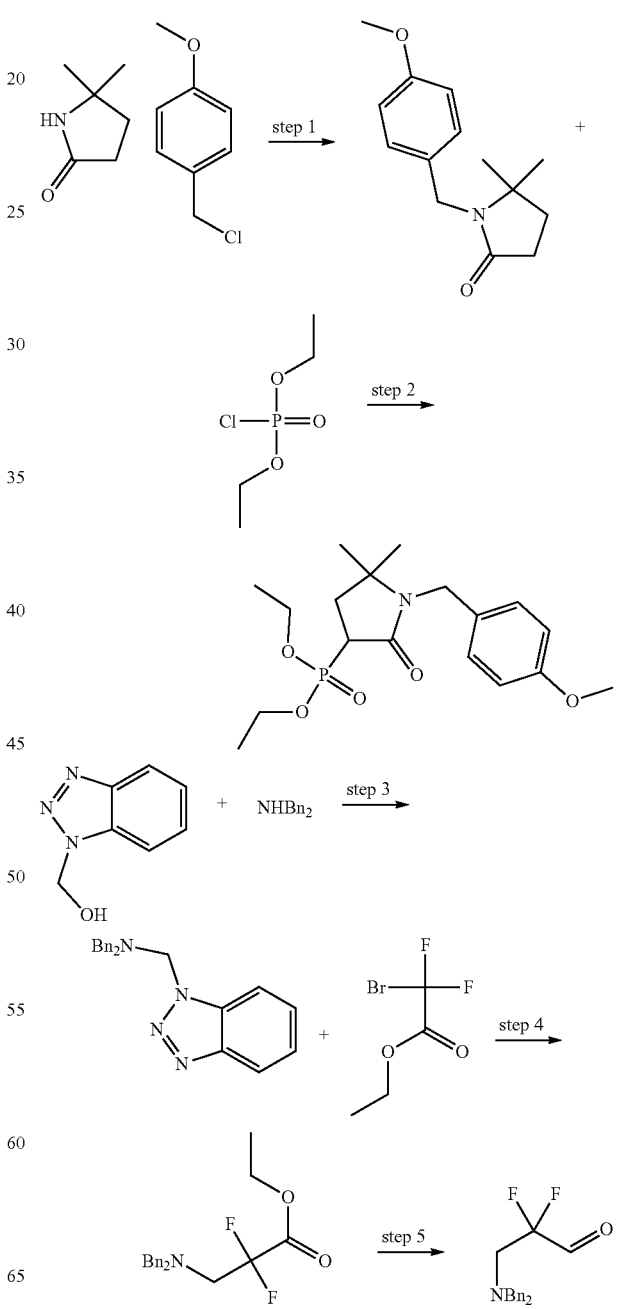

1137
-continued
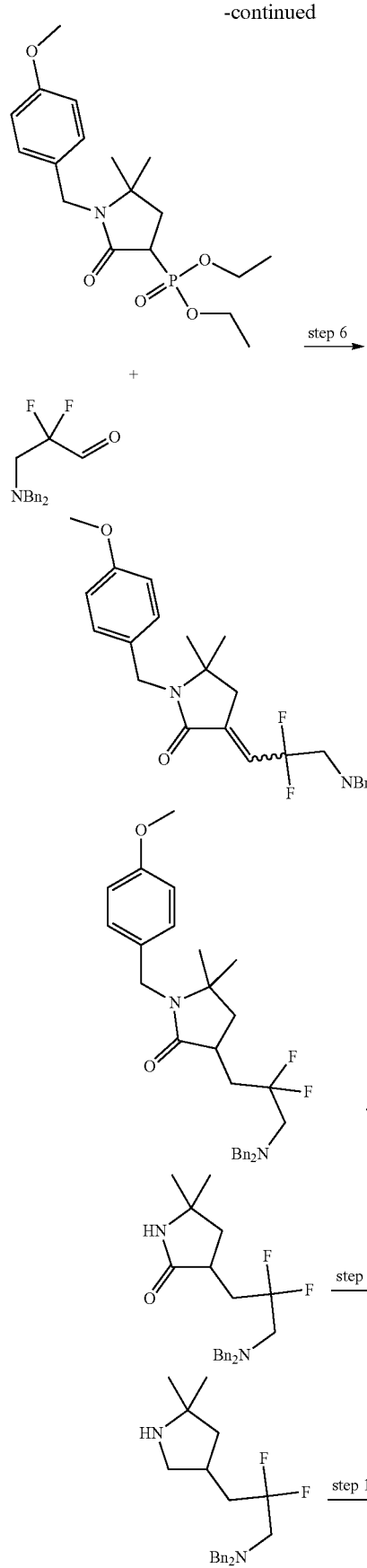
1138
-continued
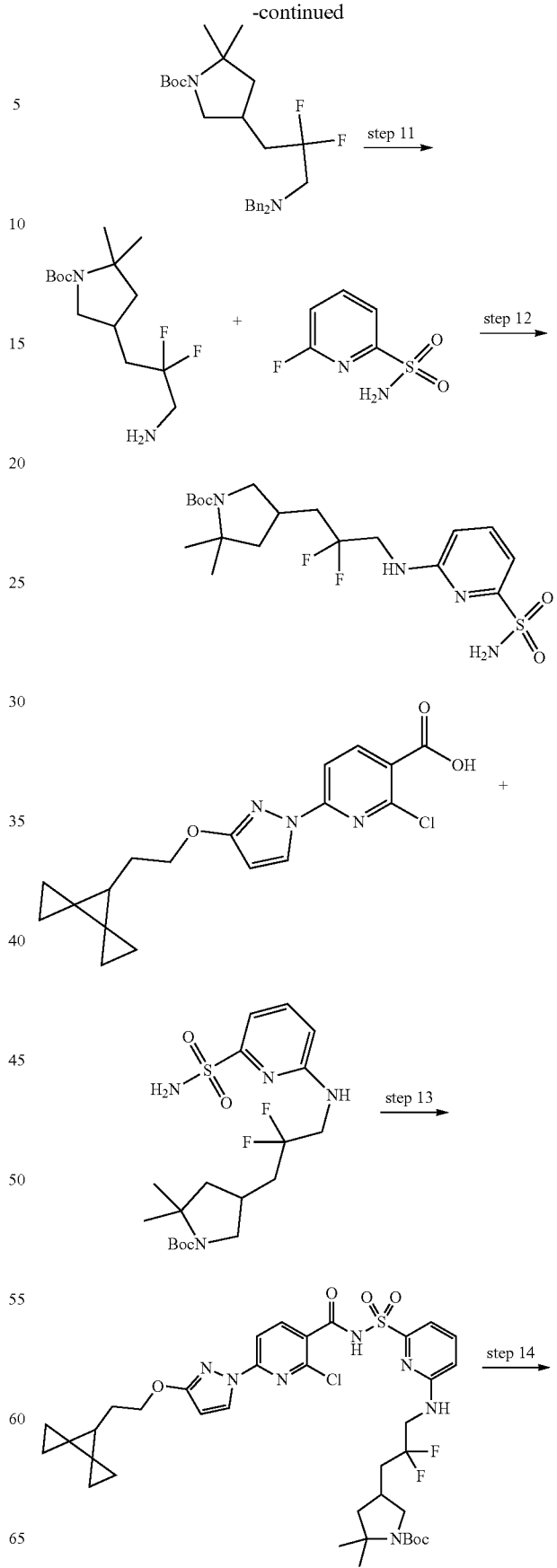

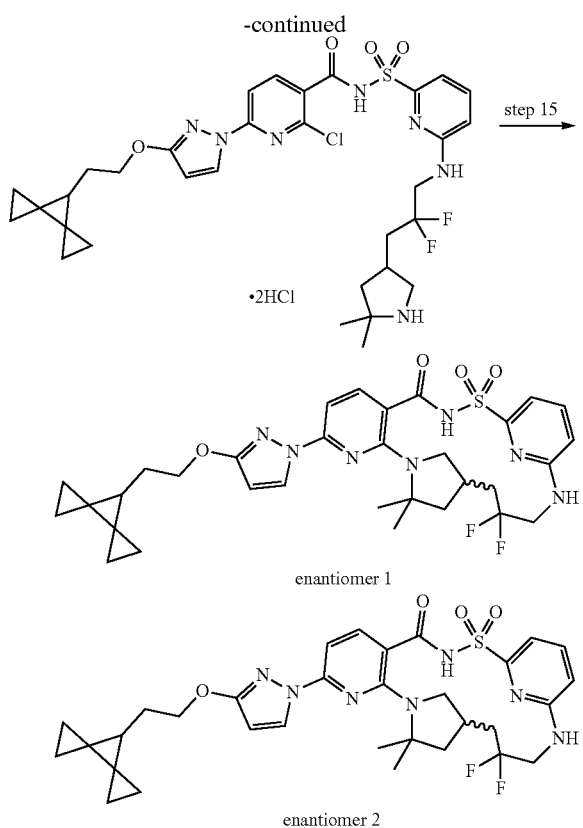

enantiomer 1 enantiomer 2

Step 1: 1-[(4-Methoxyphenyl)methyl]-5,5-dimethyl-pyrrolidin-2-one

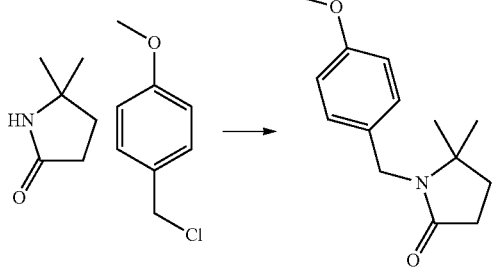

The reaction was run in two batches.

Batch 1: A solution of 5,5-dimethylpyrrolidin-2-one (121 g, 1.0693 mol) in DMF (1.8 L) was chilled to 3° C. in an ice water bath, then 60% NaH in mineral oil (64.150 g, 1.6039 mol) was added in portions over the course of approximately thirty minutes. The mixture was stirred in the ice water bath for an additional thirty minutes, then at room temperature for 1.5 hours. The resulting off-white slurry was again chilled to 3° C. in an ice water bath, then 1-(chloromethyl)-4-methoxy-benzene (251.19 g, 1.6039 mol) was added. The ice water bath was removed after the addition and the mixture was stirred overnight. The reaction mixture was carefully quenched with water (100 mL) and stored in a freezer overnight. The mixture was combined with a second batch of material before workup and purification.

Batch 2: A solution of 5,5-dimethylpyrrolidin-2-one (484 g, 4.2772 mol) in DMF (7.2 L) was chilled to 3° C. in a 20 L jacketed reactor, then 60% NaH in mineral oil (256.61 g, 6.4158 mol) was added in portions over a four hour period. The resulting mixture was stirred at 3° C. for an additional one hour, then at room temperature for two hours. The resulting slurry was again chilled to 3° C., then 1-(chloromethyl)-4-methoxy-benzene (1.0048 kg, 6.4158 mol) was added. The cooling system was deactivated after the addition was completed and the resulting slurry was stirred overnight while being allowed to warm to room temperature. The reaction mixture was carefully quenched with water (500 mL), combined with the Batch 1 reaction mixture, and split into two equal portions. Each portion was processed as follows: It was diluted with saturated ammonium chloride (10 L), then extracted with ethyl acetate (4×2 L). The aqueous phase was discarded, and then the combined organic phases were diluted with hexane (2 L) and extracted with saturated ammonium chloride (2×2 L), then with water (2 L). The aqueous phases were discarded and the organic phase was dried over sodium sulfate. The combined organic phases from both workups were concentrated in vacuo to obtain crude 1-[(4-methoxyphenyl)methyl]-5,5-dimethyl-pyrrolidin-2-one as a brown oil (1.5 kg). One kilogram of the crude product was purified by silica gel chromatography (0-100% ethyl acetate:hexane) to obtain pure 1-[(4-methoxyphenyl)methyl]-5,5-dimethyl-pyrrolidin-2-one (608 g, 58%) as a yellow oil. ESI-MS m/z calc. 233.1416, found 234.3 (M+1)$^+$; Retention time: 3.97 min (LC Method Q).

Step 2: 3-Diethoxyphosphoryl-1-[(4-methoxyphenyl)methyl]-5,5-dimethyl-pyrrolidin-2-one

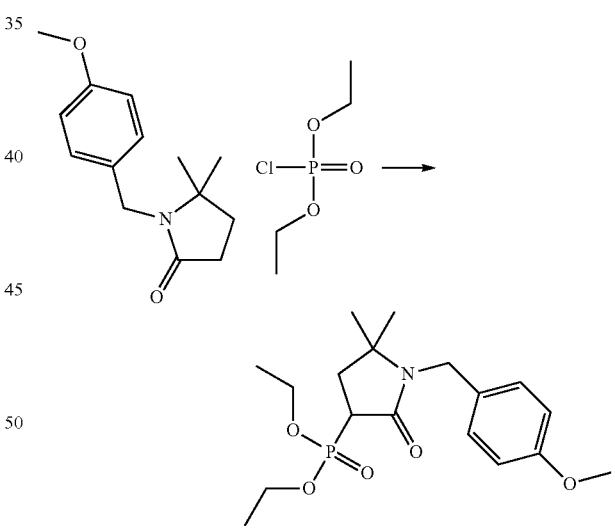

A solution of diisopropylamine (529.14 g, 732.88 mL, 5.2292 mol) in tetrahydrofuran (3.5 L) was chilled to −75° C. in a dry ice-acetone bath, then N-butyllithium (2.092 L of 2.5 M, 5.2292 mol) was added in a slow stream. The temperature was kept below −70° C. during the course of the addition. The resulting yellow solution was stirred for thirty minutes, then a solution of 1-[(4-methoxyphenyl) methyl]-5,5-dimethyl-pyrrolidin-2-one (488 g, 2.0917 mol) in tetrahydrofuran (1.5 L) was added in a slow stream and then stirred for an additional one hour. The temperature was not allowed to exceed −70° C. during the course of the addition. 1-[Chloro (ethoxy)phosphoryl]oxyethane (541.38 g, 451.15 mL, 3.1376 mol) was added dropwise to the reaction mixture, ensuring that the temperature remained below −70° C. during the course of the addition. The resulting mixture was stirred for sixteen hours while being allowed to thaw to room temperature. The reaction was then quenched with 1M hydrochloric acid (3 L) and extracted with ethyl acetate (2×2.4 L). The aqueous phase was discarded and the combined organic phases were extracted with water (3×2.4 L). The aqueous phases were discarded and the organic phase was dried over sodium sulfate and purified by silica gel chromatography (0-100% ethyl acetate/hexane) and then concentrated in vacuo to obtain 3-diethoxyphosphoryl-1-[(4-methoxyphenyl)methyl]-5,5-dimethyl-pyrrolidin-2-one (677 g, 81%). ESI-MS m/z calc. 369.1705, found 370.1 (M+1)$^+$; Retention time: 4.2 min (LC Method Q).

Step 3: N-(Benzotriazol-1-ylmethyl)-N-benzyl-1-phenyl-methanamine

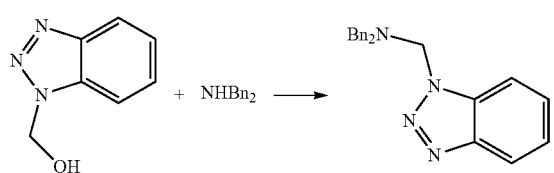

To a solution of benzotriazol-1-ylmethanol (30 g, 201.14 mmol) in EtOH (600 mL) was added N-benzyl-1-phenyl-methanamine (39.680 g, 38.674 mL, 201.14 mmol) at room temperature. The solution was stirred at room temperature for 1 hour before being concentrated in vacuo. The residue was washed with diethyl ether (3×400 mL) to give N-(benzotriazol-1-ylmethyl)-N-benzyl-1-phenyl-methanamine (59.83 g, 91%) as a white solid. $^1$H NMR (250 MHz, CDCl$_3$) δ 7.67-7.23 (m, 14H), 5.47 (s, 2H), 3.79 (s, 4H).

Step 4: Ethyl 3-(dibenzylamino)-2,2-difluoro-propanoate

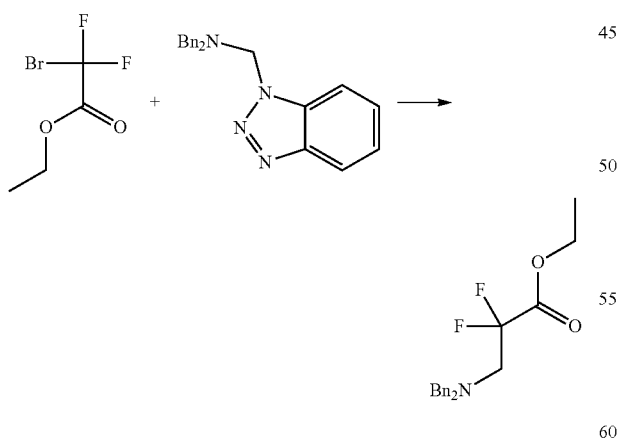

To a suspension of Zn (17.3 g, 2.4253 mL, 264.57 mmol) in THF (175 mL) was added TMS-Cl (28.691 g, 33.4 mL, 264.09 mmol) followed by ethyl 2-bromo-2,2-difluoro-acetate (11.850 g, 7.5 mL, 58.380 mmol) at room temperature. The solution was stirred for 15 min before N-(benzotriazol-1-ylmethyl)-N-benzyl-1-phenyl-methanamine (17.344 g, 52.812 mmol) in THF (100 mL) was added to the reaction dropwise. The combined solution was stirred for 2 hours before being quenched with sodium bicarbonate (350 mL) and extracted with ethyl acetate (3×500 mL). The combined organic layers were washed with water (750 mL) and dried over sodium sulfate before being concentrated in vacuo. The organic residue was purified by silica gel chromatography eluting 0-15% diethyl ether in hexane to give ethyl 3-(dibenzylamino)-2,2-difluoro-propanoate (8.98 g, 49%) as a clear liquid. $^1$H NMR (500 MHz, DMSO-d$_6$) δ 7.37-7.29 (m, 4H), 7.29-7.22 (m, 6H), 4.13 (q, J=7.1 Hz, 2H), 3.61 (s, 4H), 3.15 (t, J=13.5 Hz, 2H), 1.13 (t, J=7.1 Hz, 3H). ESI-MS m/z calc. 333.154, found 334.5 (M+1)$^+$; Retention time: 3.18 min (LC Method P).

Step 5: 3-(Dibenzylamino)-2,2-difluoro-propanal

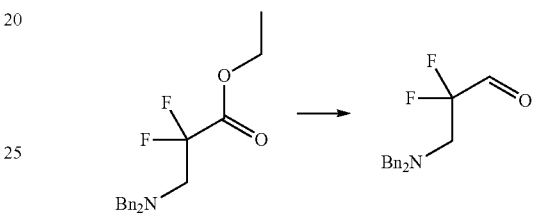

To a solution of ethyl 3-(dibenzylamino)-2,2-difluoro-propanoate (9.01 g, 27.027 mmol) in anhydrous DCM (125 mL) was added diisobutylaluminum hydride (37.8 mL of 1 M, 37.800 mmol) dropwise at −78° C. The reaction was stirred for 40 min before being quenched with citric acid (100 mL) at −78° C. The solution was extracted with diethyl ether (3×200 mL), washed with brine (200 mL) and dried over sodium sulfate before being concentrated in vacuo to give 3-(dibenzylamino)-2,2-difluoro-propanal (9.54 g, 93%). ESI-MS m/z calc. 289.1278, found 290.2 (M+1)$^+$; Retention time: 2.39 minutes (LC Method P).

Step 6: 3-[3-(Dibenzylamino)-2,2-difluoro-propylidene]-1-[(4-methoxyphenyl)methyl]-5,5-dimethyl-pyrrolidin-2-one

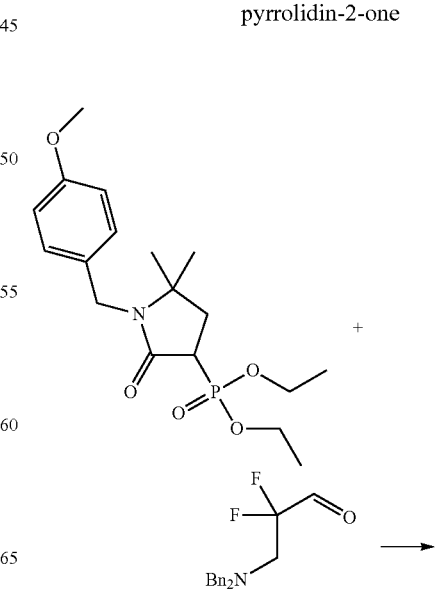

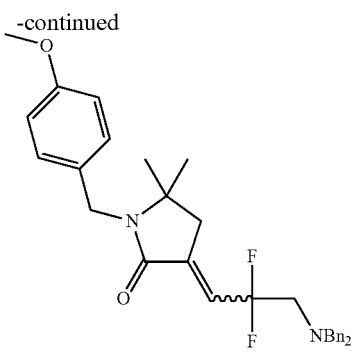

To a solution of 3-diethoxyphosphoryl-1-[(4-methoxyphenyl)methyl]-5,5-dimethyl-pyrrolidin-2-one (11.3 g, 33.105 mmol) in ACN (145 mL) was added DIEA (5.1 g, 6.8733 mL, 39.461 mmol) and LiCl (1.7 g, 40.100 mmol) at 0° C. The solution was stirred at this temperature for 30 min before 3-(dibenzylamino)-2,2-difluoro-propanal (9.544 g, 32.988 mmol) in ACN (50 ml) was added at 0° C. The mixture was warmed up to room temperature as it stirred overnight. The solution was quenched with a saturated ammonium chloride solution (150 mL) and then extracted with diethyl ether (3×200 mL) and washed with brine (300 mL) before being dried over sodium sulfate and concentrated. The residue was purified using silica gel chromatography eluting 0-25% ethyl acetate in hexane to give 3-[3-(dibenzylamino)-2,2-difluoro-propylidene]-1-[(4-methoxyphenyl)methyl]-5,5-dimethyl-pyrrolidin-2-one (E/Z isomer mixture) (8.03 g, 48%). $^1$H NMR (250 MHz, CDCl$_3$) δ 7.36-7.22 (m, 10H), 7.21-7.15 (m, 2H), 6.89-6.72 (m, 2H), 6.67-5.75 (m, 1H), 4.54-4.16 (m, 2H), 3.85-3.60 (m, 7H), 3.60-3.45 (m, 1H), 3.19-2.79 (m, 1H), 2.57-2.33 (m, 2H), 1.22-0.98 (m, 6H). ESI-MS m/z calc. 504.2588, found 505.2 (M+1)$^+$; Retention time: 3.02 min, 3.51 min (LC Method P).

Step 7: 3-[3-(Dibenzylamino)-2,2-difluoro-propyl]-1-[(4-methoxyphenyl)methyl]-5,5-dimethyl-pyrrolidin-2-one

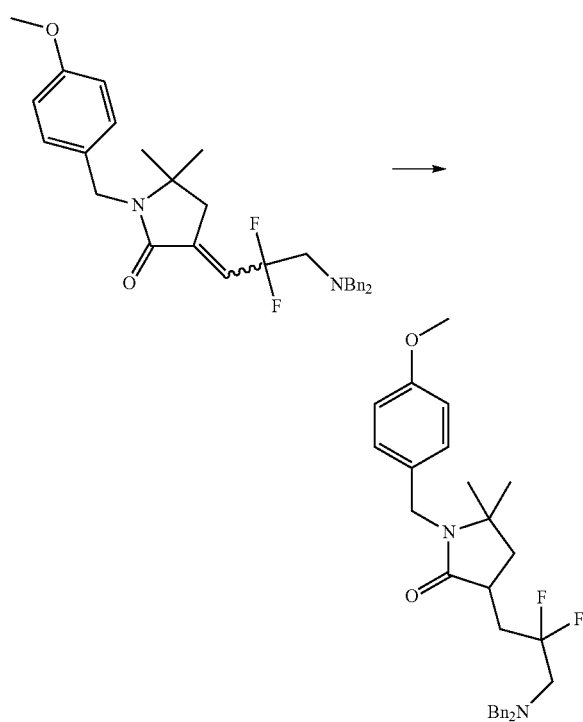

To a solution of 3-[3-(dibenzylamino)-2,2-difluoro-propylidene]-1-[(4-methoxyphenyl)methyl]-5,5-dimethyl-pyrrolidin-2-one (8 g, 15.854 mmol) in ethanol (400 mL) was added Raney-Nickel (8 g, 136.30 mmol). The resulting solution was hydrogenated in Parr-Shaker under 65 PSI for 24 hours, then filtered through Celite and washed with ethanol to provide a crude product. The crude product was purified by flash chromatography (loaded in CH$_2$Cl$_2$) (220 g SiO$_2$, eluting 0 to 20% acetone in hexane) to afford 3-[3-(dibenzylamino)-2,2-difluoro-propyl]-1-[(4-methoxyphenyl)methyl]-5,5-dimethyl-pyrrolidin-2-one (4.97 g, 56%) as a pale yellow liquid. $^1$H NMR (250 MHz, CDCl$_3$) δ 7.43-7.29 (m, 10H), 7.22 (d J=8.6 Hz, 2H), 6.84 (d, J=8.6 Hz, 2H), 4.38 (s, 2H), 3.81 (s, 3H), 3.78-3.50 (m, 6H), 2.97-2.74 (m, 3H), 2.61-2.44 (m, 1H), 2.21-2.01 (m, 1H), 1.16 (s, 3H), 0.93 (s, 3H). ESI-MS m/z calc. 506.2745, found 507.2 (M+1)$^+$; Retention time: 5.75 min (LC Method Q).

Step 8: 3-[3-(Dibenzylamino)-2,2-difluoro-propyl]-5,5-dimethyl-pyrrolidin-2-one

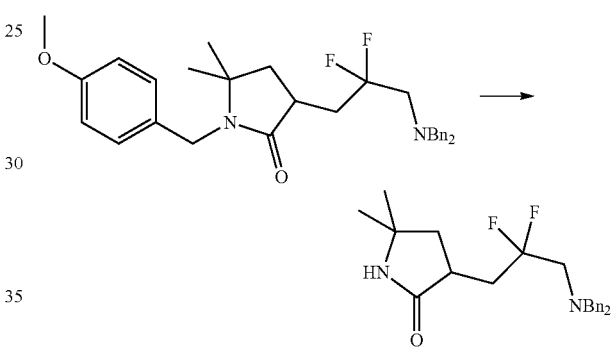

To 3-[3-(dibenzylamino)-2,2-difluoro-propyl]-1-[(4-methoxyphenyl)methyl]-5,5-dimethyl-pyrrolidin-2-one (4.97 g, 8.9271 mmol) in a vessel was added TFA (100 mL), then the vessel was sealed and heated at 100° C. for 11 days. All solvents were removed under reduced pressure. The residue was dissolved in dichloromethane (300 mL), washed with a saturated sodium bicarbonate aqueous solution (3×100 mL), dried over anhydrous sodium sulfate, filtered and concentrated under reduced pressure. The crude product was purified by flash chromatography (loaded in CH$_2$Cl$_2$) (120 g SiO$_2$, eluting 0 to 45% ethyl acetate in hexane) to afford 3-[3-(dibenzylamino)-2,2-difluoro-propyl]-5,5-dimethyl-pyrrolidin-2-one (2.28 g, 66%) as a pale yellow liquid. ESI-MS m/z calc. 386.217, found 387.3 (M+1)$^+$; Retention time: 3.29 min (LC Method Q).

Step 9: N,N-Dibenzyl-3-(5,5-dimethylpyrrolidin-3-yl)-2,2-difluoro-propan-1-amine

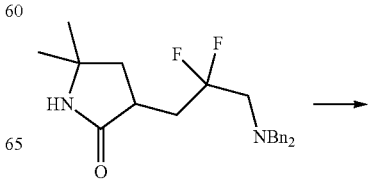

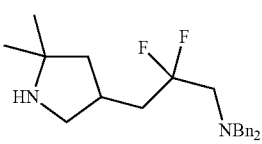

To a stirring solution of 3-[3-(dibenzylamino)-2,2-difluoro-propyl]-5,5-dimethyl-pyrrolidin-2-one (2.23 g, 5.7701 mmol) in anhydrous THF (100 mL) at 0° C. under nitrogen was slowly added a solution of BH$_3$Me$_2$S (40 mL of 2 M, 80.000 mmol) in THF. After the addition was complete, the reaction mixture was heated to 65° C. for 24 hours. The reaction mixture was cooled to 0° C. and slowly quenched with 6 M aqueous HCl (50 mL). Methanol (50 mL) was added and the reaction mixture was heated to 65° C. for 1 hour. After cooling to room temperature, the reaction mixture was basified with saturated aqueous NaHCO$_3$(300 mL) and the volatiles were removed under vacuum. The product was extracted with ethyl acetate (3×150 mL). The combined organic layers were washed with brine (80 mL), dried over anhydrous sodium sulfate and concentrated to afford N,N-dibenzyl-3-(5,5-dimethylpyrrolidin-3-yl)-2,2-difluoro-propan-1-amine (2.46 g, quant.) as a yellow oil. The product was carried to the next step without further purification. ESI-MS m/z calc. 372.2377, found 373.4 (M+1)$^+$; Retention time: 3.87 min (LC Method Q).

Step 10: tert-Butyl 4-[3-(dibenzylamino)-2,2-difluoro-propyl]-2,2-dimethyl-pyrrolidine-1-carboxylate

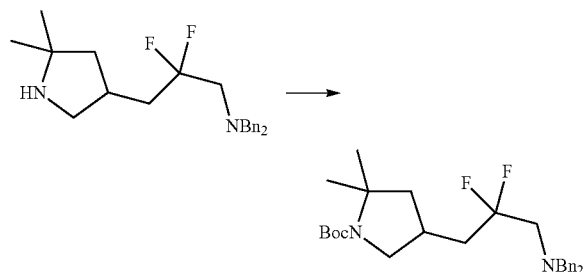

To a stirring solution of N,N-dibenzyl-3-(5,5-dimethylpyrrolidin-3-yl)-2,2-difluoro-propan-1-amine (2.46 g, 5.9437 mmol) in DCM (80 mL) at 0° C. was added triethylamine (1.0164 g, 1.4 mL, 10.044 mmol), followed by Boc$_2$O (1.96 g, 8.9807 mmol). The reaction mixture was stirred at this temperature for 1 hour. The reaction was quenched cold with brine (100 mL) and then warmed up to room temperature. Two layers were separated and the aqueous layer was extracted with DCM (2×50 mL). The combined organic layers were dried over anhydrous sodium sulfate and concentrated. The crude was purified by silica gel chromatography using 0-15% ethyl acetate gradient in hexanes to afford tert-butyl 4-[3-(dibenzylamino)-2,2-difluoro-propyl]-2,2-dimethyl-pyrrolidine-1-carboxylate (2.79 g, 94%) as a colorless oil. ESI-MS m/z calc. 472.2901, found 473.5 (M+1)$^+$; Retention time: 7.45 min (LC Method Q).

Step 11: tert-Butyl 4-(3-amino-2,2-difluoro-propyl)-2,2-dimethyl-pyrrolidine-1-carboxylate

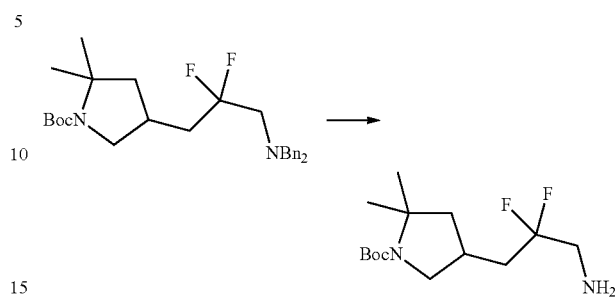

To a stirring solution of tert-butyl 4-[3-(dibenzylamino)-2,2-difluoro-propyl]-2,2-dimethyl-pyrrolidine-1-carboxylate (2.68 g, 5.6706 mmol) in anhydrous methanol (60 mL) at room temperature under nitrogen was added palladium on carbon (2.1 g, 10% w/w, 1.9733 mmol), followed by ammonium formate (3.6 g, 57.092 mmol). The reaction mixture was heated to 65° C. for 6 hours. After cooling to room temperature, the reaction mixture was filtered through a pad of Celite. The filter cake was washed with methanol (2×30 mL), and the combined filtrate was concentrated under vacuum. The crude was purified by silica gel chromatography using 0-10% methanol gradient in dichloromethane to afford tert-butyl 4-(3-amino-2,2-difluoro-propyl)-2,2-dimethyl-pyrrolidine-1-carboxylate (1.34 g, 77%) as a yellow oil. $^1$H NMR (250 MHz, CDCl$_3$) δ 3.87-3.66 (m, 1H), 3.32 (s, 3H), 3.13-2.86 (m, 3H), 2.52-2.32 (m, 1H), 2.08-1.79 (m, 3H), 1.57-1.24 (m, 15H). ESI-MS m/z calc. 292.1962, found 293.5 (M+1)$^+$; Retention time: 3.55 min (LC Method Q).

Step 12: tert-Butyl 4-[2,2-difluoro-3-[(6-sulfamoyl-2-pyridyl)amino]propyl]-2,2-dimethyl-pyrrolidine-1-carboxylate

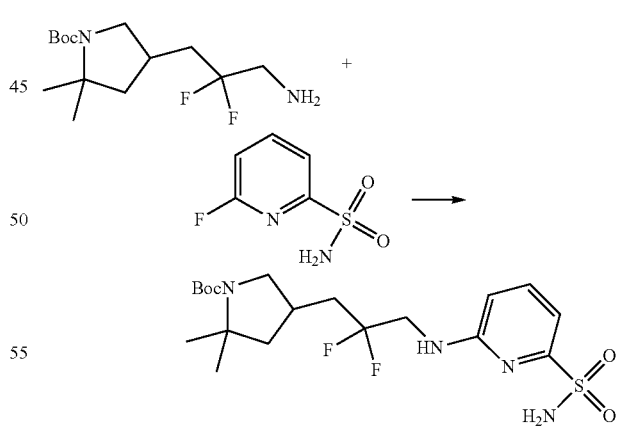

To a stirring solution of tert-butyl 4-(3-amino-2,2-difluoro-propyl)-2,2-dimethyl-pyrrolidine-1-carboxylate (1.24 g, 4.2413 mmol) and 6-fluoropyridine-2-sulfonamide (1.12 g, 6.3934 mmol) in anhydrous DMSO (7 mL) at room temperature under nitrogen was added DIEA (1.7020 g, 2.3 mL, 13.169 mmol). The reaction mixture was heated to 120° C. for 30 hours. After cooling to room temperature, the reaction mixture was diluted with water (50 mL) and brine (150 mL), and the product was extracted with ethyl acetate (3×100 mL). The combined organic layers were washed with brine (50 mL), dried over anhydrous sodium sulfate and concentrated. The crude was purified by reverse phase HPLC using water-acetonitrile gradient method (C$_{18}$ Varian column, 50-90% acetonitrile, 60 mL/min) to afford tert-butyl 4-[2,2-difluoro-3-[(6-sulfamoyl-2-pyridyl)amino]propyl]-2,2-dimethyl-pyrrolidine-1-carboxylate (574 mg, 29%) as white foam. $^1$H NMR (500 MHz, DMSO-d$_6$) δ 7.58 (dd, J=8.4, 7.2 Hz, 1H), 7.37 (t, J=6.4 Hz, 1H), 7.16 (s, 2H), 7.06-7.00 (m, 1H), 6.75 (d, J=8.7 Hz, 1H), 3.96-3.81 (m, 2H), 3.64-3.51 (m, 1H), 2.83 (q, J=10.4 Hz, 1H), 2.42-2.29 (m, 1H), 2.10-1.82 (m, 3H), 1.54-1.42 (m, 1H), 1.41-1.30 (m, 12H), 1.23 (s, 3H). ESI-MS m/z calc. 448.1956, found 449.2 (M+1)$^+$; Retention time: 2.38 min (LC Method P).

Step 13: tert-Butyl 4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]-2,2-difluoro-propyl]-2,2-dimethyl-pyrrolidine-1-carboxylate A 100 mL round bottom flask was charged under nitrogen with 2-chloro-6-[3-(2-dispiro[2.0.2.1]heptan-7-ylethoxy)pyrazol-1-yl]pyridine-3-carboxylic acid (457 mg, 1.270 mmol) and anhydrous THF (8 mL). CDI (355 mg, 2.189 mmol) was added and the mixture was stirred under nitrogen at room temperature for 15 hours. In a separate 20 mL flask, a solution of tert-butyl 4-[2,2-difluoro-3-[(6-sulfamoyl-2-pyridyl)amino]propyl]-2,2-dimethyl-pyrrolidine-1-carboxylate (570 mg, 1.271 mmol) in anhydrous THF (4 mL) was prepared under nitrogen atmosphere and it was subsequently added via syringe into the activated ester solution. DBU (0.78 mL, 5.216 mmol) was added through syringe and the reaction mixture was stirred at room temperature under nitrogen atmosphere for 5 hours. The solvents were removed under reduced pressure and the resulting thick oil was treated with ethyl acetate (35 mL) and water (35 mL). HCl (1.5 mL of 6 M, 9.000 mmol) was added slowly (final pH=5) and the two phases were separated. The aqueous phase was extracted with EtOAc (30 mL). The combined extracts were washed with brine (30 mL) and dried over sodium sulfate. After evaporation of the solvents, the residue was dissolved in DCM and purified by flash chromatography on silica gel (80 g gold column) using a gradient of ethyl acetate (0 to 100% over 30 min) in hexanes. The product eluted at 45-65% EtOAc. The pure fractions were combined and the solvents evaporated to give tert-butyl 4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]-2,2-difluoro-propyl]-2,2-dimethyl-pyrrolidine-1-carboxylate (667 mg, 66%) as a colorless resin. ESI-MS m/z calc. 789.2887, found 790.54 (M+1)$^+$; Retention time: 2.51 min (LC Method B).

Step 14: 2-Chloro-N-[[6-[[3-(5,5-dimethylpyrrolidin-3-yl)-2,2-difluoro-propyl]amino]-2-pyridyl]sulfonyl]-6-[3-(2-dispiro[2.0.2.1]heptan-7-ylethoxy)pyrazol-1-yl]pyridine-3-carboxamide (Dihydrochloride Salt)

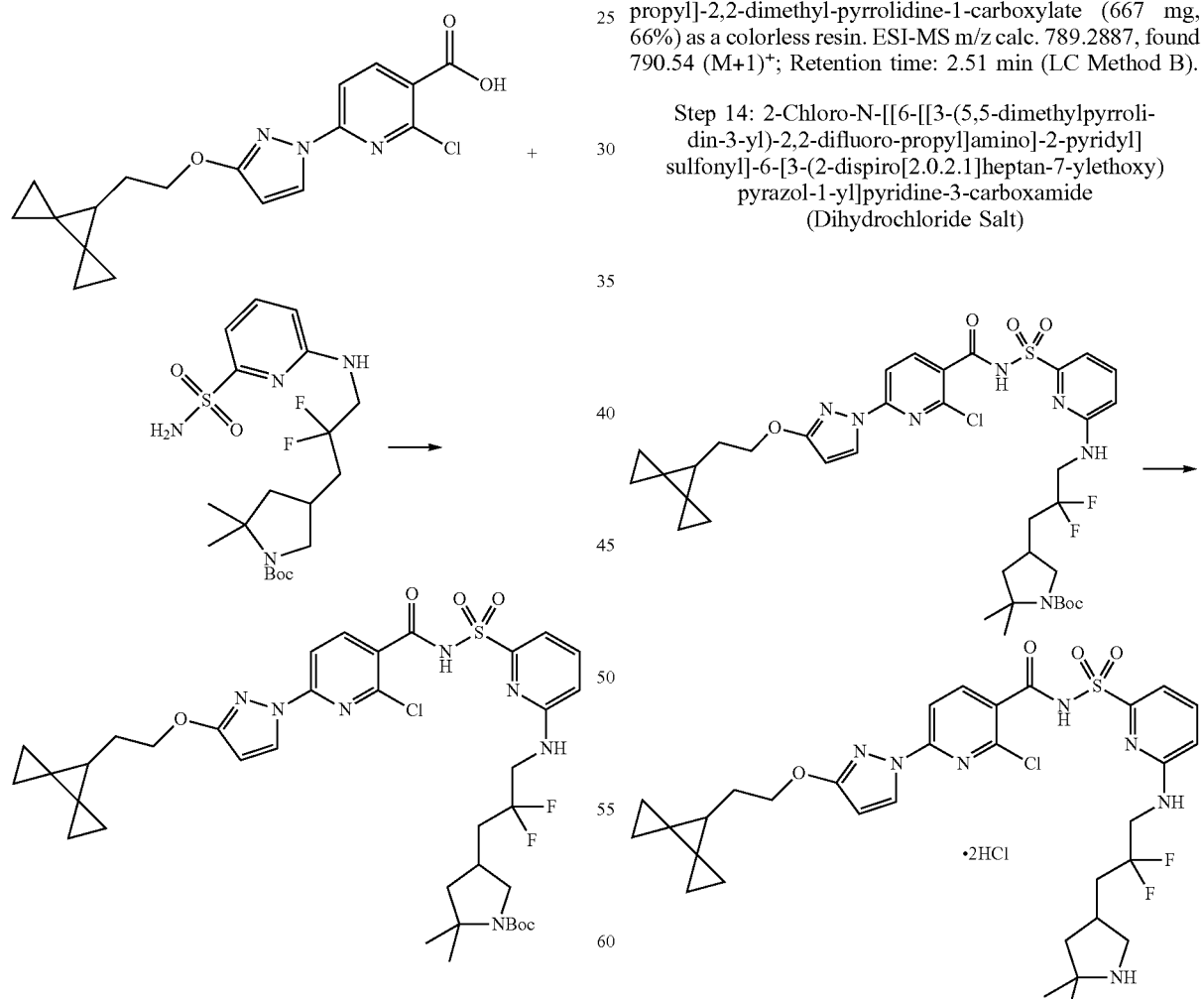

A 100 mL was charged with tert-butyl 4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]-2,2-difluoro-propyl]-2,2-dimethyl-pyrrolidine-1-carboxylate (667 mg, 0.8440 mmol), DCM (8 mL) and HCl (1.25 mL of 4M in dioxane, 5.000 mmol). The reaction was stirred at room temperature for 1.5 hours. The volatiles were removed by evaporation under vacuum. The residue was triturated with DCM/hexanes and the solvents evaporated. The operation was repeated until a nice white solid was obtained. Drying under vacuum gave 2-chloro-N-[[6-[[3-(5,5-dimethylpyrrolidin-3-yl)-2,2-difluoro-propyl]amino]-2-pyridyl]sulfonyl]-6-[3-(2-dispiro[2.0.2.1]heptan-7-ylethoxy)pyrazol-1-yl]pyridine-3-carboxamide (dihydrochloride salt) (570 mg, 89%) as a white solid. ESI-MS m/z calc. 689.23627, found 690.3 (M+1)$^+$; Retention time: 1.77 min (LC Method B).

Step 15: 8-[3-(2-{Dispiro[2.0.2.1]heptan-7-yl}ethoxy)-1H-pyrazol-1-yl]-16,16-difluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Enantiomer 1) (Compound 305, SFC peak 1) and 8-[3-(2-{dispiro[2.0.2.1]heptan-7-yl}ethoxy)-1H-pyrazol-1-yl]-16,16-difluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Enantiomer 2) (Compound 304, SFC Peak 2)

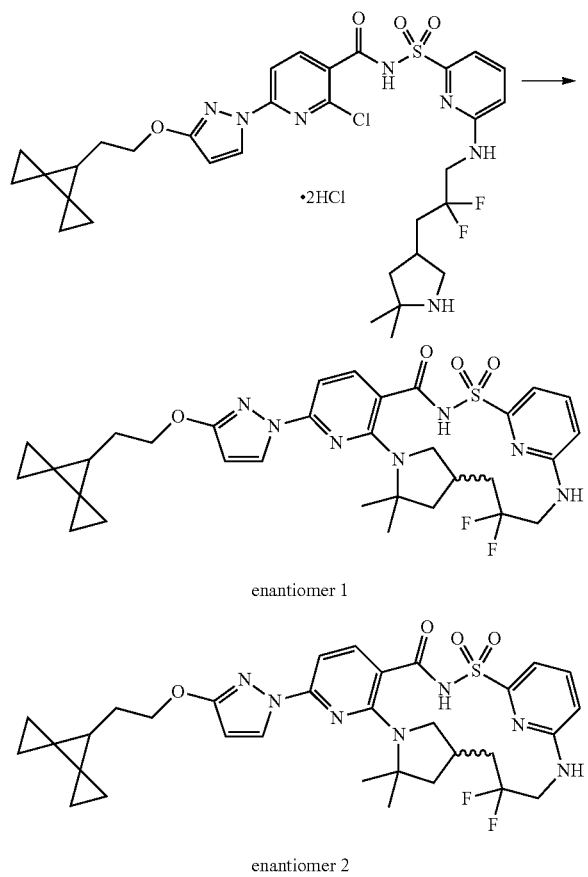

enantiomer 1 enantiomer 2

A 100 mL round bottom flask equipped with a magnetic stirbar was charged under nitrogen with 2-chloro-N-[[6-[[3-(5,5-dimethylpyrrolidin-3-yl)-2,2-difluoro-propyl]amino]-2-pyridyl]sulfonyl]-6-[3-(2-dispiro[2.0.2.1]heptan-7-ylethoxy)pyrazol-1-yl]pyridine-3-carboxamide (dihydrochloride salt) (570 mg, 0.7469 mmol), anhydrous NMP (24 mL) and K$_2$CO$_3$ (766 mg, 5.542 mmol) (325 mesh). The mixture was vigorously stirred in a dry bath at 150° C. under nitrogen for 18 hours. After cooling down to room temperature, the mixture was poured into cooled water (200 mL) and it was acidified by adding HCl (2 mL of 6 M, 12.00 mmol) (mild foaming). The resulting solid was filtered on a Buchner funnel and briefly air dried. The solid was dissolved in DCM and a bit of methanol, and the resulting cloudy solution was evaporated. The product was purified by flash chromatography on silica gel (gold 40 g column) using a gradient of methanol (0 to 5% over 30 min) in dichloromethane. The product eluted around 1% methanol. Evaporation of the solvents, followed by trituration in DCM/hexanes and evaporation of the solvents gave racemic 8-[3-(2-{dispiro[2.0.2.1]heptan-7-yl}ethoxy)-1H-pyrazol-1-yl]-16,16-difluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (404 mg, 83%) as an off-white solid. ESI-MS m/z calc. 653.2596, found 654.33 (M+1)$^+$; Retention time: 2.34 min (LC Method B).

The two enantiomers were separated by chiral SFC using a ChiralPak AS-3 (250×21.2 mm), 5 µM column at 40° C., mobile phase 24% MeOH (no modifier), 76% CO$_2$, flow: 70 mL/min, concentration: 31 mg/mL in MeOH, injection volume: 500 µl, pressure: 156 bar, wavelength: 280 nm. After evaporation of the solvents, each of the enantiomers were purified a second time by flash chromatography on silica gel (24 g column) using a gradient of methanol (0 to 5% over 30 min) in dichloromethane. After evaporation of the solvents, the compounds were triturated in DCM/hexanes. Evaporation of the solvents gave the two enantiomers as white solids.

Compound 305, SFC peak 1. ee>98%. 8-[3-(2-{Dispiro[2.0.2.1]heptan-7-yl}ethoxy)-1H-pyrazol-1-yl]-16,16-difluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (enantiomer 1) (174 mg, 70%). $^1$H NMR (500 MHz, DMSO-d$_6$) δ 12.54 (s, 1H), 8.22 (d, J=2.8 Hz, 1H), 7.87 (d, J=8.2 Hz, 1H), 7.71 (t, J=7.9 Hz, 1H), 7.52 (d, J=10.2 Hz, 1H), 7.22 (d, J=7.2 Hz, 1H), 6.96 (d, J=8.3 Hz, 2H), 6.10 (d, J=2.7 Hz, 1H), 4.48 (dt, J=37.1, 12.7 Hz, 1H), 4.22 (t, J=6.8 Hz, 2H), 3.30 (broad s, 1H), 3.12 (t, J=8.6 Hz, 1H), 2.77 (t, J=10.6 Hz, 1H), 2.39 (br s, 1H), 2.27-2.03 (m, 2H), 1.93 (dd, J=11.7, 5.2 Hz, 1H), 1.82 (q, J=6.6 Hz, 2H), 1.72 (t, J=12.4 Hz, 1H), 1.63 (s, 3H), 1.54 (s, 3H), 1.48 (t, J=6.6 Hz, 1H), 0.90-0.75 (m, 4H), 0.69-0.60 (m, 2H), 0.55-0.39 (m, 2H). ESI-MS m/z calc. 653.2596, found 654.33 (M+1)$^+$; Retention time: 2.34 min (LC Method B).

Compound 304, SFC peak 2. ee>98%. 8-[3-(2-{Dispiro[2.0.2.1]heptan-7-yl}ethoxy)-1H-pyrazol-1-yl]-16,16-difluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (enantiomer 2) (178 mg, 71%). $^1$H NMR (500 MHz, DMSO-d$_6$) δ 12.53 (s, 1H), 8.22 (d, J=2.8 Hz, 1H), 7.87 (d, J=8.2 Hz, 1H), 7.71 (t, J=7.9 Hz, 1H), 7.52 (d, J=10.1 Hz, 1H), 7.21 (d, J=7.2 Hz, 1H), 6.96 (d, J=8.3 Hz, 2H), 6.10 (d, J=2.7 Hz, 1H), 4.48 (dt, J=37.3, 12.4 Hz, 1H), 4.22 (t, J=6.7 Hz, 2H), 3.30 (broad s, 1H), 3.12 (t, J=8.6 Hz, 1H), 2.77 (t, J=10.6 Hz, 1H), 2.39 (br s, 1H), 2.26-2.05 (m, 2H), 1.93 (dd, J=12.0, 5.2 Hz, 1H), 1.82 (q, J=6.6 Hz, 2H), 1.72 (t, J=12.4 Hz, 1H), 1.64 (s, 3H), 1.54 (s, 3H), 1.48 (t, J=6.6 Hz, 1H), 0.90-0.77 (m, 4H), 0.72-0.60 (m, 2H), 0.56-0.45 (m, 2H). ESI-MS m/z calc. 653.2596, found 654.33 (M+1)+; Retention time: 2.34 min (LC Method B).

Example 200: Preparation of 8-[3-(2-{Dispiro [2.0.2.1]heptan-7-yl}ethoxy)-1H-pyrazol-1-yl]-16-fluoro-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Enantiomer 1) (Compound 309, SFC Peak 1), 8-[3-(2-{dispiro [2.0.2.1]heptan-7-yl}ethoxy)-1H-pyrazol-1-yl]-16-fluoro-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Enantiomer 2) (Compound 308, SFC Peak 2), 8-[3-(2-{dispiro [2.0.2.1]heptan-7-yl}ethoxy)-1H-pyrazol-1-yl]-16-fluoro-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Enantiomer 3) (Compound 307, SFC Peak 3) and 8-[3-(2-{dispiro [2.0.2.1]heptan-7-yl}ethoxy)-1H-pyrazol-1-yl]-16-fluoro-12,12-dimethyl-2λ⁶-thia-3,9,11,18,23-pentaazatetracyclo[17.3.1.111,14.05,10]tetracosa-1(22),5,7,9,19(23),20-hexaene-2,2,4-trione (Enantiomer 4) (Compound 306, SFC Peak 4)

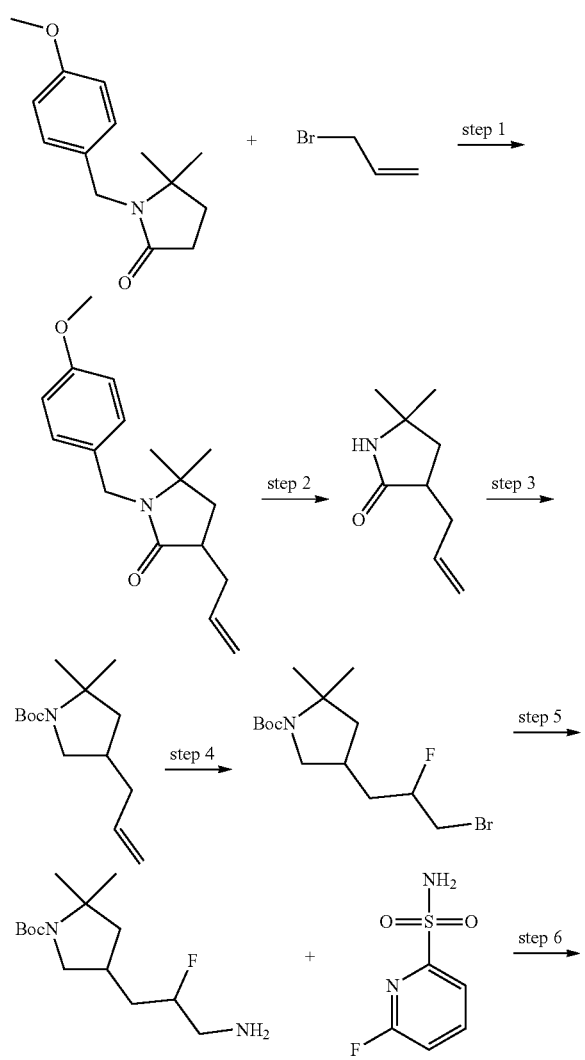

-continued

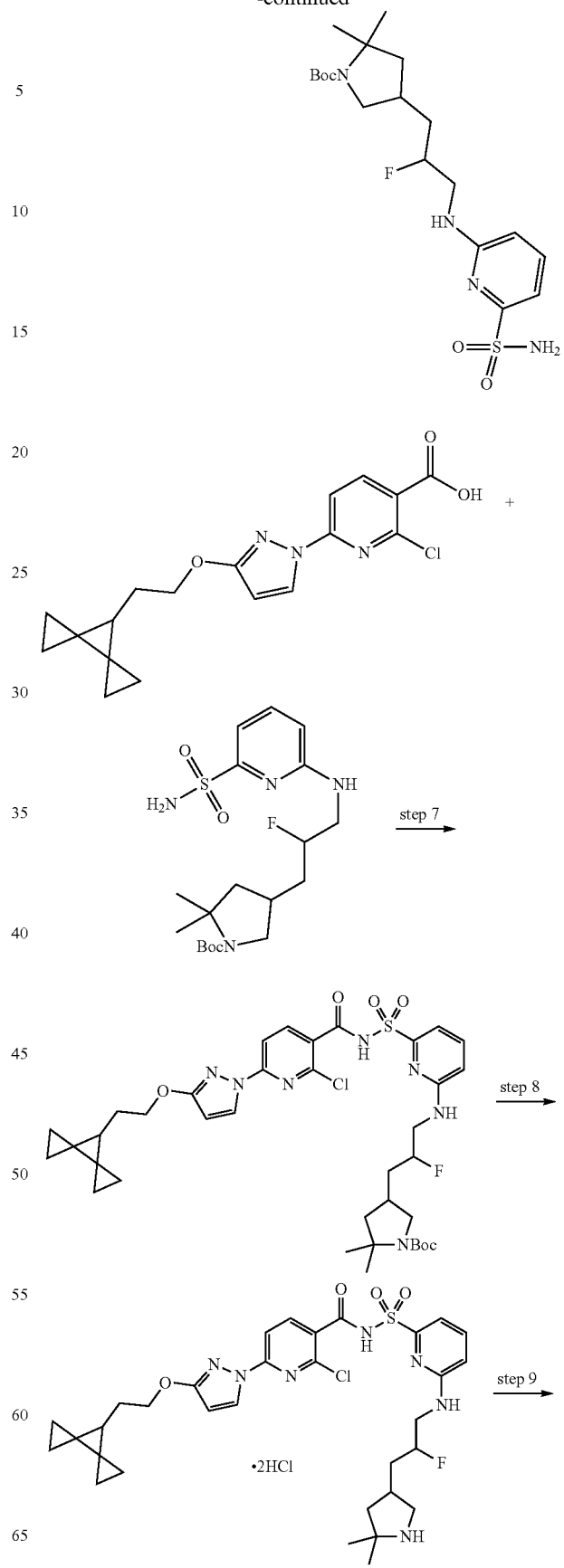

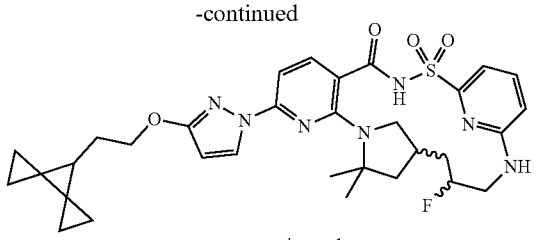

enantiomer 1

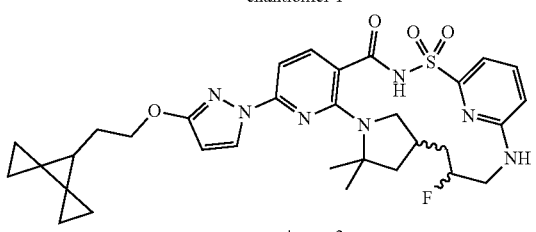

enantiomer 2

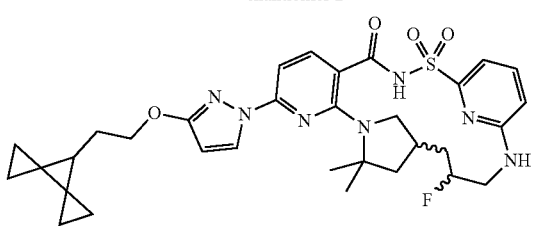

enantiomer 3

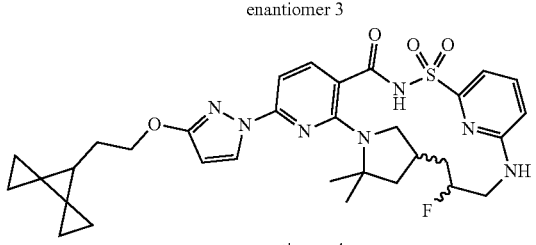

enantiomer 4

Step 1: 3-Allyl-1-[(4-methoxyphenyl)methyl]-5,5-dimethyl-pyrrolidin-2-one

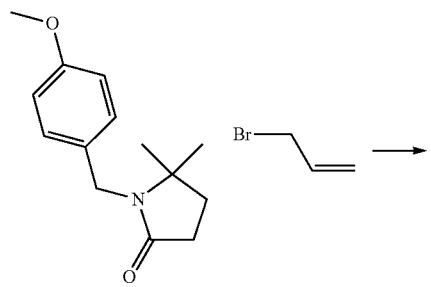

A solution of diisopropylamine (4.3372 g, 6.0 mL, 42.862 mmol) in tetrahydrofuran (100 mL) was chilled to −78° C. and N-butyllithium (17.1 mL of 2.5 M, 42.862 mmol) was added dropwise. The solution was stirred for thirty minutes, then a solution of 1-[(4-methoxyphenyl)methyl]-5,5-dimethyl-pyrrolidin-2-one (10 g, 42.862 mmol) in THF (10 mL) was added in dropwise and then stirred for one hour. 3-Bromoprop-1-ene (5.1853 g, 3.71 mL, 42.862 mmol) was added dropwise to the reaction mixture, stirred for one hour at −78° C. and then allowed to warm up to 0° C. over 30 minutes. The reaction was then quenched with saturated ammonium chloride (100 mL) and extracted with ethyl acetate (3×50 mL). The combined organic phases were dried over sodium sulfate and purified by silica gel chromatography (0-20% ethyl acetate/hexane) to give 3-allyl-1-[(4-methoxyphenyl)methyl]-5,5-dimethyl-pyrrolidin-2-one (8.75 g, 71%). ESI-MS m/z calc. 273.1729, found 274.0 (M+1)⁺; Retention time: 2.97 min (LC Method P).

Step 2: 3-Allyl-5,5-dimethyl-pyrrolidin-2-one

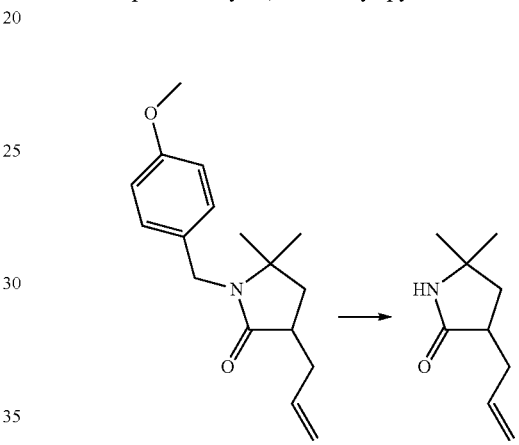

3-Allyl-1-[(4-methoxyphenyl)methyl]-5,5-dimethyl-pyrrolidin-2-one (7.75 g, 28.350 mmol) was dissolved in acetonitrile (140 mL) and water (16 mL), then ceric ammonium nitrate (64.559 g, 113.40 mmol) was added portionwise at room temperature, and the reaction was stirred for 3 hours. Then, it was quenched with brine (300 mL) and extracted with EtOAc (3×150 mL). The organic fractions were combined, dried over sodium sulfate and evaporated, the residue was purified by silica gel column chromatography using 0-100% hexanes-ethyl acetate to give 3-allyl-5,5-dimethyl-pyrrolidin-2-one (3.77 g, 76%). ESI-MS m/z calc. 153.1154, found 154.2 (M+1)⁺; Retention time: 1.61 min (LC Method P).

Step 3: tert-Butyl 4-allyl-2,2-dimethyl-pyrrolidine-1-carboxylate

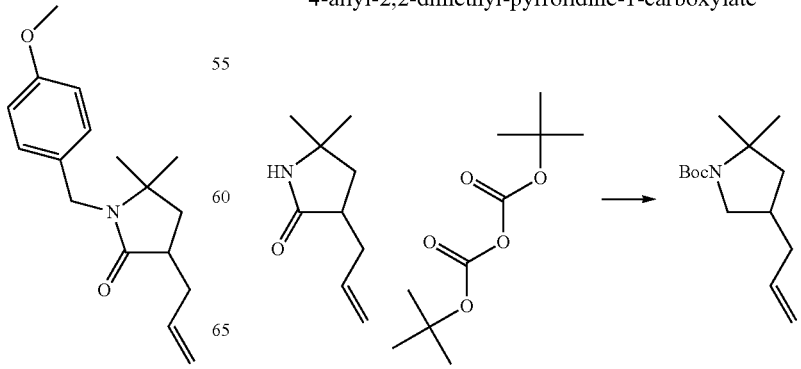

A solution of 3-allyl-5,5-dimethyl-pyrrolidin-2-one (3.77 g, 24.605 mmol) in THF (25 mL) was added dropwise to suspension of LiAlH₄ (2.8016 g, 3.05 mL, 73.815 mmol) in THF (50 mL) at reflux. The mixture was refluxed for 3 hours, cooled to 0° C., and then water (2.8 mL) was added very slowly, followed by 15% w/w sodium hydroxide (2.8 mL) and water (8.4 mL). The mixture was allowed to warm up to room temperature and Boc₂O (6.4440 g, 6.7832 mL, 29.526 mmol) was added. The mixture was stirred for 16 hours, filtered and the filter cake was triturated with THF. The organic fractions were combined and evaporated, the residue was purified by silica gel column chromatography using 0-5% ethyl acetate in hexane to give tert-butyl 4-allyl-2,2-dimethyl-pyrrolidine-1-carboxylate (5.06 g, 77%). ¹H NMR (250 MHz, Chloroform-d) δ 5.93-5.58 (m, 1H), 5.15-4.89 (m, 2H), 3.82-3.48 (m, 1H), 2.90 (q, J=10.9 Hz, 1H), 2.32-1.97 (m, 3H), 1.94-1.75 (m, 1H), 1.50-1.25 (m, 16H). ESI-MS m/z calc. 239.1885, found 240.3 (M+1)⁺; Retention time: 3.53 min (LC Method P).

Step 4: tert-Butyl 4-(3-bromo-2-fluoro-propyl)-2,2-dimethyl-pyrrolidine-1-carboxylate

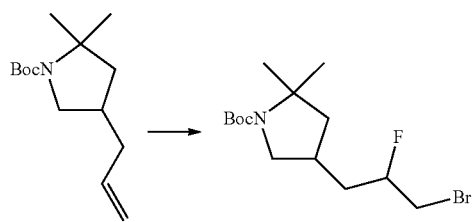 [SMILES: C=CCC1CN(C(=O)OC(C)(C)C)C(C)(C)C1 ; CC(C)(C)OC(=O)N1CC(CC(F)CBr)CC1(C)C]

A solution of tert-butyl 4-allyl-2,2-dimethyl-pyrrolidine-1-carboxylate (500 mg, 1.8801 mmol) and triethylamine trihydrofluoride (710 mg, 1.6296 mmol) in DCM (10 mL) was cooled to 0° C. and NBS (500 mg, 2.8092 mmol) was added. The mixture was allowed to warm up to room temperature and was stirred for 4 hours. The mixture was quenched with saturated sodium bicarbonate (50 mL), the aqueous phase was separated and extracted with DCM (100 mL). The organic fractions were combined, dried over sodium sulfate and evaporated. The residue was purified by silica gel column chromatography using 0-10% ethyl acetate in hexane to give tert-butyl 4-(3-bromo-2-fluoro-propyl)-2,2-dimethyl-pyrrolidine-1-carboxylate (420 mg, 65%) as a colorless oil. ¹H NMR (250 MHz, CDCl₃) δ 4.87-4.42 (m, 1H), 3.86-3.54 (m, 1H), 3.55-3.22 (m, 2H), 3.07-2.75 (m, 1H), 2.56-2.18 (m, 1H), 2.12-1.71 (m, 3H), 1.71-1.57 (m, 1H), 1.51-1.38 (m, 12H), 1.35-1.24 (m, 3H). ESI-MS m/z calc. 337.1053, found 338.5 (M+1)⁺; Retention time: 3.59 min (LC Method P).

Step 5: tert-Butyl 4-(3-amino-2-fluoro-propyl)-2,2-dimethyl-pyrrolidine-1-carboxylate

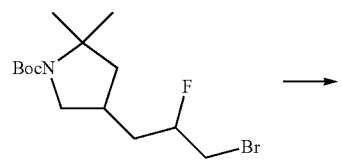

-continued

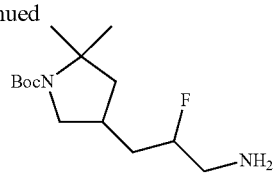

To a solution of tert-butyl 4-(3-bromo-2-fluoro-propyl)-2,2-dimethyl-pyrrolidine-1-carboxylate (2.26 g, 6.5477 mmol) in DMF (28 mL) was added NaN₃ (0.6 g, 9.1832 mmol) and the mixture stirred at 45° C. for 18 hours. The mixture was diluted with water (150 mL) followed by saturated sodium bicarbonate (150 mL) and the mixture was extracted with ethyl acetate (2×200 mL). The organic layer was washed with brine (300 mL), dried over sodium sulfate, filtered and concentrated to give the intermediate azide as a brown oil. To a solution of this azide intermediate oil in ethyl acetate (30 mL) was added platinum oxide monohydrate (0.5 g, 2.2018 mmol). The mixture was hydrogenated in a Parr shaker at 40 psi for 1 hour. The reaction mixture was filtered through a Celite pad. The filtrate was concentrated to afford tert-butyl 4-(3-amino-2-fluoro-propyl)-2,2-dimethyl-pyrrolidine-1-carboxylate (1.59 g, 87%) as a dark oil. ESI-MS m/z calc. 274.2057, found 275.6 (M+1)⁺; Retention time: 3.51 min (LC Method Q).

Step 6: tert-Butyl 4-[2-fluoro-3-[(6-sulfamoyl-2-pyridyl)amino]propyl]-2,2-dimethyl-pyrrolidine-1-carboxylate

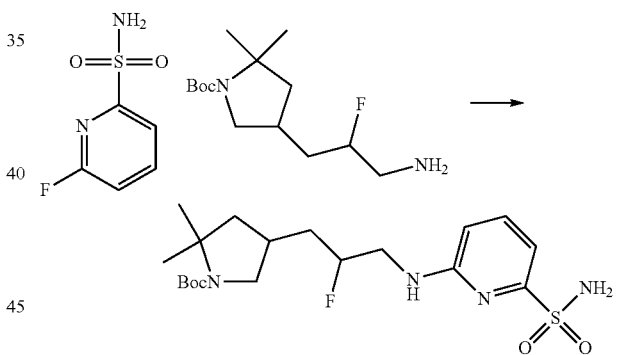

To a mixture of tert-butyl 4-(3-amino-2-fluoro-propyl)-2,2-dimethyl-pyrrolidine-1-carboxylate (1.59 g, 5.6791 mmol) and 6-fluoropyridine-2-sulfonamide (1.3 g, 7.0103 mmol) in DMSO (10 mL) was added DIEA (2.2260 g, 3 mL, 17.223 mmol). The mixture was stirred at 110° C. for 16 hours. The mixture was cooled to room temperature and the mixture was treated with water/brine (100/100 mL) and ethyl acetate (150 mL). The organic layer was dried over sodium sulfate, filtered through a celite pad and concentrated. The residue (2.1 g, was combined with 0.56 g of product from a previous reaction) was dissolved in DMSO (10 mL) and loaded on a prep.-HPLC column (Varian C₁₈ 10 µm 5×30 cm; flow rate: 60 mL/min.; mobile phase A: water; mobile phase B: acetonitrile; method:40-90% B over 45 min.). The pure fractions were combined and concentrated to remove acetonitrile. The resulting aqueous phase was extracted with ethyl acetate (2×100 mL). The organic layer was washed by brine (200 mL), dried over sodium sulfate and concentrated to afford tert-butyl 4-[2-fluoro-3-[(6-sulfamoyl-2-pyridyl)amino]propyl]-2,2-dimethyl-pyrrolidine-1-carboxylate (1.5 g, 58%) as a white solid. ¹H NMR (250 MHz, DMSO-d₆) δ 7.56 (t, J=7.8 Hz, 1H), 7.27 (t, J=5.8 Hz, 1H), 7.12 (s, 2H), 7.00 (d, J=7.1 Hz, 1H), 6.71 (d, J=8.4 Hz, 1H), 4.95-4.46 (m, 1H), 3.77-3.40 (m, 3H), 2.95-2.73 (m, 1H), 2.40-2.15 (m, 1H), 2.02-1.85 (m, 1H), 1.83-1.57 (m, 3H), 1.54-1.29 (m, 12H), 1.25 (s, 3H). ESI-MS m/z calc. 430.205, found 431.5 (M+1)⁺; Retention time: 2.35 min (LC Method R).

Step 7: tert-Butyl 4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]-2-fluoro-propyl]-2,2-dimethyl-pyrrolidine-1-carboxylate A 100 mL round bottom flask was charged under nitrogen with 2-chloro-6-[3-(2-dispiro[2.0.2.1]heptan-7-ylethoxy)pyrazol-1-yl]pyridine-3-carboxylic acid (573 mg, 1.593 mmol) and anhydrous THF (10 mL). CDI (315 mg, 1.943 mmol) was added and the mixture was stirred under nitrogen at room temperature for 2 hours. Another 150 mg of CDI was added and the mixture was stirred at room temperature for 15 hours to reach complete conversion. In a separate 20 mL flask, a solution of tert-butyl 4-[2-fluoro-3-[(6-sulfamoyl-2-pyridyl)amino]propyl]-2,2-dimethyl-pyrrolidine-1-carboxylate (693 mg, 1.610 mmol) in anhydrous THF (5 mL) was prepared under nitrogen atmosphere and it was subsequently added via syringe into the activated ester solution. DBU (0.96 mL, 6.419 mmol) was added through syringe and the reaction mixture was stirred at room temperature under nitrogen atmosphere for 5 hours. The solvents were removed under reduced pressure and the resulting thick oil was treated with ethyl acetate (40 mL) and water (40 mL). HCl (1.8 mL of 6 M, 10.80 mmol) was added slowly (final pH=5) and the two phases were separated. The aqueous phase was extracted with EtOAc (30 mL). The combined organic extracts were washed with brine (30 mL) and dried over sodium sulfate. After evaporation of the solvents, the residue (1.34 g) was dissolved in DCM and purified by flash chromatography on silica gel (80 g gold column) using a gradient of ethyl acetate (0 to 100% over 30 min) in hexanes. The product eluted at 45-65% EtOAc. The pure fractions were combined and the solvents evaporated to give tert-butyl 4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]-2-fluoro-propyl]-2,2-dimethyl-pyrrolidine-1-carboxylate (804 mg, 65%) as a white foamy solid. ESI-MS m/z calc. 771.2981, found 772.39 (M+1)⁺; Retention time: 2 diastereomers visible, 1:1, Rt=2.51 and Rt=2.52 min (LC Method B). The product was used for the next step without any further purification.

Step 8: 2-Chloro-N-[[6-[[3-(5,5-dimethylpyrrolidin-3-yl)-2-fluoro-propyl]amino]-2-pyridyl]sulfonyl]-6-[3-(2-dispiro[2.0.2.1]heptan-7-ylethoxy)pyrazol-1-yl]pyridine-3-carboxamide (Dihydrochloride Salt)

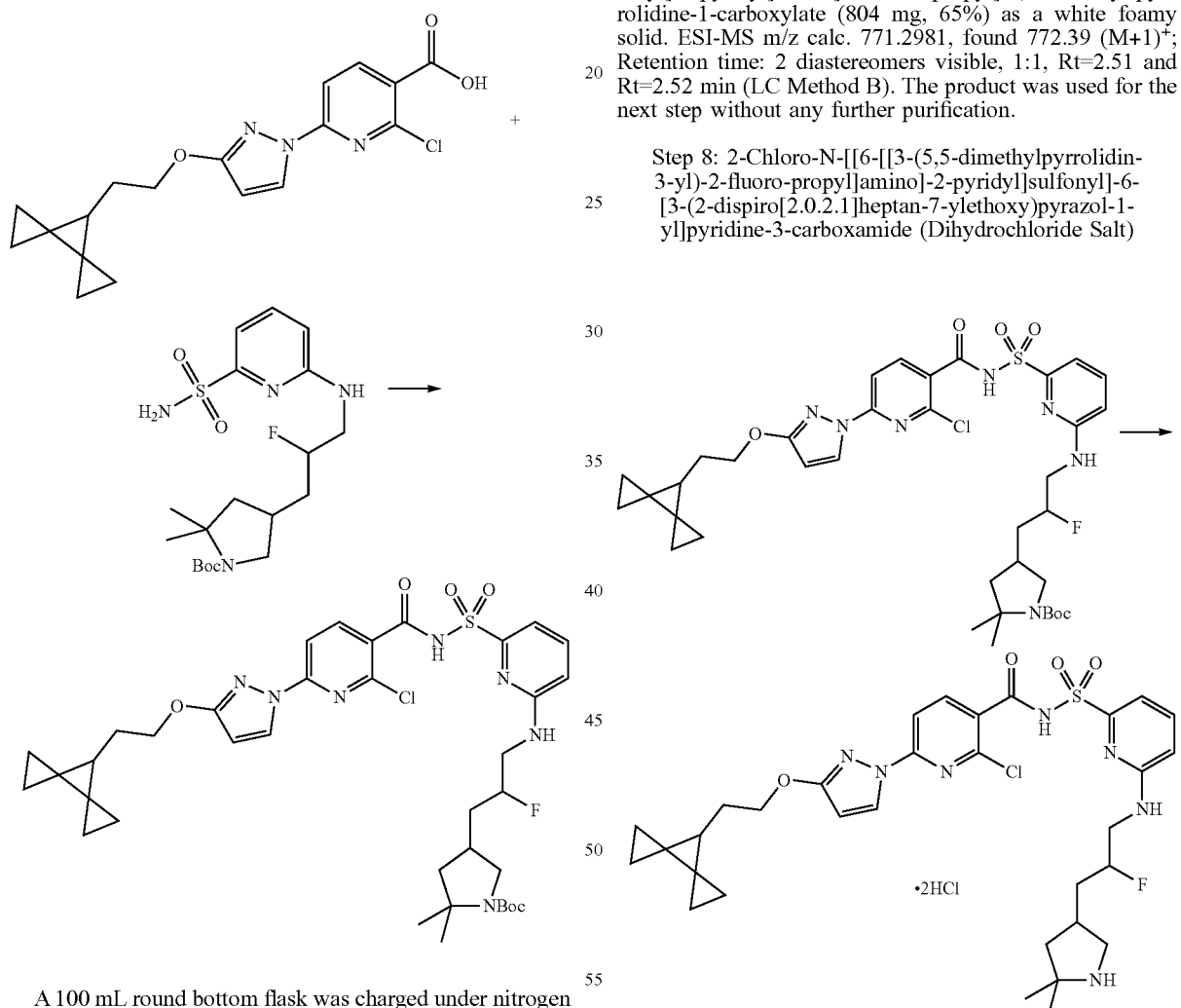

A 100 mL flask was charged with tert-butyl 4-[3-[[6-[[2-chloro-6-[3-(2-dispiro[2.0.2.1]heptan-7-ylethoxy)pyrazol-1-yl]pyridine-3-carbonyl]sulfamoyl]-2-pyridyl]amino]-2-fluoro-propyl]-2,2-dimethyl-pyrrolidine-1-carboxylate (782 mg, 1.013 mmol), DCM (9 mL) and HCl (1.5 mL of 4M in dioxane, 6.000 mmol). The reaction was stirred at room temperature for nearly 5 hours. The volatiles were removed by evaporation under vacuum. The residue was triturated with DCM/hexanes and the solvents evaporated. The operation was repeated until a nice white solid was obtained.

Drying under vacuum gave 2-chloro-N-[[6-[[3-(5,5-dimethylpyrrolidin-3-yl)-2-fluoro-propyl]amino]-2-pyridyl]sulfonyl]-6-[3-(2-dispiro[2.0.2.1]heptan-7-ylethoxy)pyrazol-1-yl]pyridine-3-carboxamide (dihydrochloride salt) (731 mg, 97%) as a white solid. The product was used for next step without any further purification. ESI-MS m/z calc. 671.24567, found 672.44 (M+1)$^+$; Retention time: 1.75 min (LC Method B).

Step 9: 8-[3-(2-{Dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Enantiomer 1) (Compound 309, SFC peak 1), 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Enantiomer 2) (Compound 308, SFC Peak 2), 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (enantiomer 3) (Compound 307, SFC Peak 3) and 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Enantiomer 4) (Compound 306, SFC Peak 4)

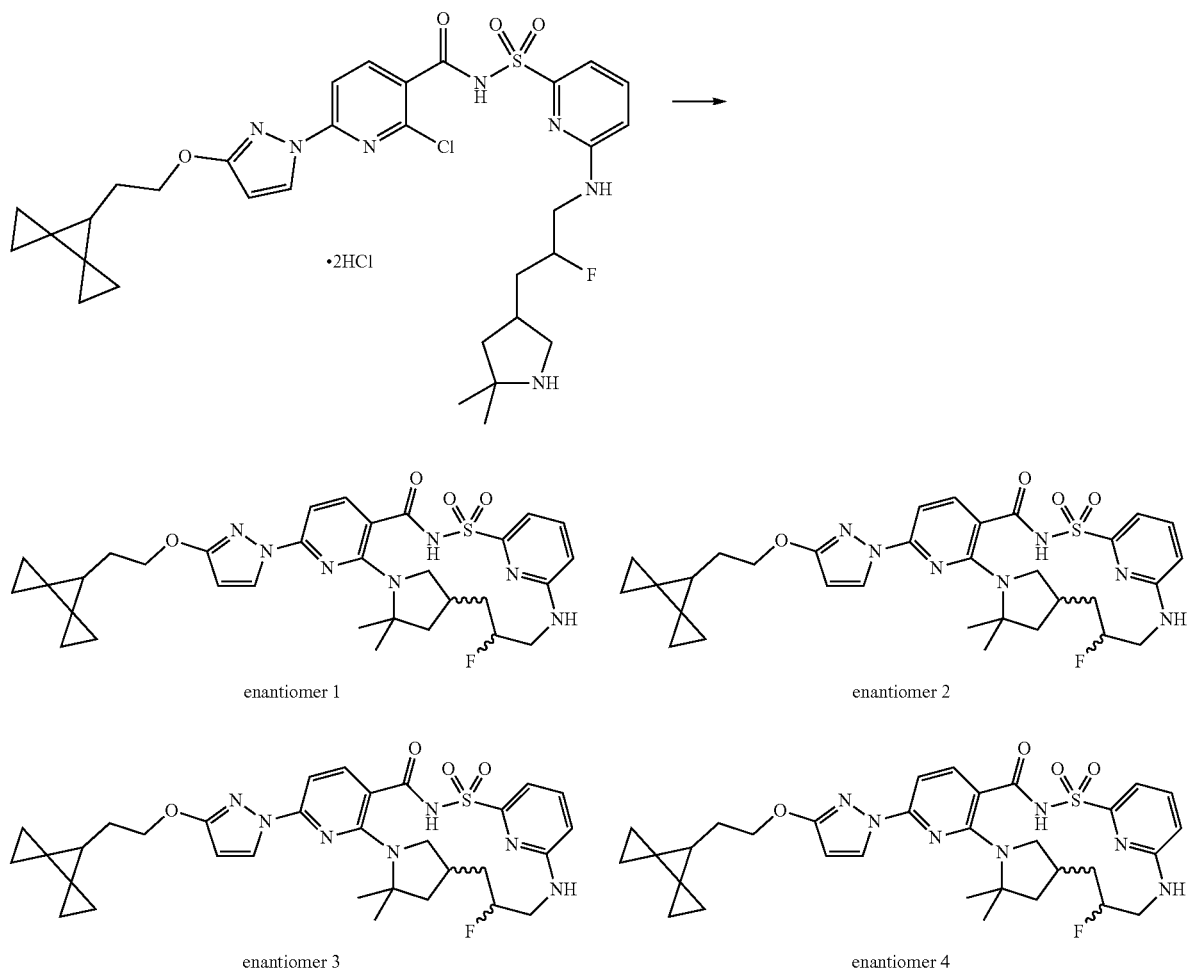

A 100 mL round bottom flask equipped with a magnetic stirbar was charged under nitrogen with 2-chloro-N-[[6-[[3-(5,5-dimethylpyrrolidin-3-yl)-2-fluoro-propyl]amino]-2-pyridyl]sulfonyl]-6-[3-(2-dispiro[2.0.2.1]heptan-7-ylethoxy)pyrazol-1-yl]pyridine-3-carboxamide (dihydrochloride salt) (723 mg, 0.9703 mmol), anhydrous NMP (30 mL) and $K_2CO_3$ (996 mg, 7.207 mmol) (325 mesh). The mixture was vigorously stirred in a dry bath at 150° C. under nitrogen for 18 hours. After cooling down to room temperature, the mixture was poured into cooled water (300 mL) and it was acidified by adding HCl (2.5 mL of 6 M, 15.00 mmol) (mild foaming). The resulting solid was filtered on a Buchner funnel and briefly air dried. The solid was dissolved in DCM and a bit of methanol, and the resulting cloudy solution was dried over sodium sulfate. After concentration (910 mg of crude solid), the solution was purified by flash chromatography on silica gel (gold 80 g column) using a gradient of methanol (0 to 5% over 30 min) in dichloromethane. The product eluted around 2-3% methanol. Evaporation of the solvents, followed by trituration in DCM/hexanes and evaporation of the solvents gave 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (467 mg, 76%) (mixture of 4 isomers) as an off-white solid. $^1$H NMR (500 MHz, DMSO-$d_6$) several diastereomers observed δ 12.57 and 12.50 (two s, total 1H), 8.25-8.19 (m, 1H), 7.83 (d, J=8.2 Hz, 1H), 7.65 (q, J=8.0 Hz, 1H), 7.37-7.11 (m, 2H), 6.98-6.74 (m, 2H), 6.10 (dd, J=4.6, 2.7 Hz, 1H), 4.87 (d, J=43.7 Hz, 1H), 4.32-4.04 (m, 3H), 3.29-2.97 (m, 2H), 2.92-2.60 (m, 1H), 2.47-2.23 (m, 1H), 2.18-1.76 (m, 5H), 1.75-1.44 (m, 8H), 0.87-0.77 (m, 4H), 0.70-0.56 (m, 2H), 0.56-0.43 (m, 2H). ESI-MS m/z calc. 635.269, found 636.37 (M+1)$^+$; Retention time: two peak visible, Rt=2.32 and Rt=2.34 min (LC Method B).

The four stereoisomers were separated by chiral SFC in two stages. The sample was first purified using a normal phase SFC-MS method using a LUX-4 column (250×21.2 mm, 5 μm particle size) sold by Phenomenex (pn: 00G-4491-PO-AX). Mobile phase 41% MeOH (no modifier), 59% $CO_2$, 70 mL/min, 31 mg/mL in MeOH, injection volume=500 μL, column temperature=40° C., pressure 178 Bar, wavelength 280 nM. This separated peak 1 and peak 2 from peaks 3 and 4 which eluted together. After evaporation of the solvents, Peak 3 and 4 (216 mg of solid) were separated using a chiralPak AS-3 column (250×21.2 mm), 5 μM, mobile phase 28% MeOH (no modifier), 72% $CO_2$, 70 mL/min, 31 mg/mL in MeOH, 500 μL injection volume, pressure 156 bar, wavelength 280 mm. After evaporation of the solvent, each compound was purified by flash chromatography on silica gel (12 g column) using a gradient of methanol (0 to 5% over 15 min) in dichloromethane. For each separated isomer, the solvents were evaporated and the residue was triturated in DCM/hexanes. Evaporation of the solvents gave the products as off-white solids. Based on LC retention times, peak ½ and peak ¾ form enantiomeric pairs. This was confirmed by mixing QC solution from peak 2 with peak 3, which resulted in two separate peaks. $^1$H NMR overlay of the 4 isomers confirms the observation: peak 1 and 2 have the same $^1$H NMR spectrum, while peak 3 $^1$H NMR spectrum is identical to peak 4.

Compound 309, SFC peak 1. ee>98%. 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (enantiomer 1) (98 mg, 61%). $^1$H NMR (500 MHz, DMSO-$d_6$) δ 12.50 (broad s, 1H), 8.22 (s, 1H), 7.82 (br s, 1H), 7.66 (t, J=7.9 Hz, 1H), 7.24 (br s, 1H), 7.19-7.13 (br m, 1H), 6.95 (d, J=8.2 Hz, 1H), 6.78 (br s, 1H), 6.10 (d, J=2.9 Hz, 1H), 4.83 (br d, 1H), 4.22 (br s, 2H), 4.12 (br s, 1H), 3.26-3.02 (br m, 2H), 2.82 (br s, 1H), 2.44 (br s, 1H), 2.08 (br s, 1H), 1.98-1.44 (m, 12H), 0.89-0.75 (m, 4H), 0.72-0.60 (m, 2H), 0.55-0.43 (m, 2H). ESI-MS m/z calc. 635.269, found 636.37 (M+1)$^+$; Retention time: 2.33 min (LC Method B).

Compound 308, SFC peak 2. ee>98%. 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (enantiomer 2) (98 mg, 61%). $^1$H NMR (500 MHz, DMSO-$d_6$) δ 12.50 (s, 1H), 8.23 (d, J=2.8 Hz, 1H), 7.84 (d, J=7.4 Hz, 1H), 7.66 (t, J=7.9 Hz, 1H), 7.24 (broad s, 1H), 7.17 (d, J=7.2 Hz, 1H), 6.96 (d, J=8.2 Hz, 1H), 6.78 (br s, 1H), 6.10 (d, J=2.7 Hz, 1H), 4.83 (br d, J=44.5 Hz, 1H), 4.23 (tt, J=6.8, 2.7 Hz, 2H), 4.13 (br s, 1H), 3.15 (br s, 2H), 2.82 (br s, 1H), 2.44 (br s, 1H), 2.08 (br s, 1H), 1.97-1.42 (m, 12H), 0.90-0.76 (m, 4H), 0.73-0.57 (m, 2H), 0.56-0.41 (m, 2H). ESI-MS m/z calc. 635.269, found 636.33 (M+1)$^+$; Retention time: 2.33 min (LC Method B).

Compound 307, SFC peak 3. ee>98%. 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (enantiomer 3) (90 mg, 56%). $^1$H NMR (500 MHz, DMSO-$d_6$) δ 12.57 (s, 1H), 8.21 (d, J=2.8 Hz, 1H), 7.83 (d, J=8.2 Hz, 1H), 7.64 (t, J=7.9 Hz, 1H), 7.33 (broad d, J=9.8 Hz, 1H), 7.14 (d, J=7.2 Hz, 1H), 6.94 (t, J=9.2 Hz, 2H), 6.09 (d, J=2.8 Hz, 1H), 4.88 (d, J=42.8 Hz, 1H), 4.30-4.09 (m, 3H), 3.36 (m, 1H overlapped with water), 3.01 (t, J=8.9 Hz, 1H), 2.64 (t, J=10.7 Hz, 1H), 2.31 (broad s, 1H), 1.94-1.75 (m, 5H), 1.69-1.57 (m, 4H), 1.52 (s, 3H), 1.48 (t, J=6.5 Hz, 1H), 0.90-0.78 (m, 4H), 0.68-0.59 (m, 2H), 0.55-0.41 (m, 2H). ESI-MS m/z calc. 635.269, found 636.37 (M+1)$^+$; Retention time: 2.3 min (LC Method B).

Compound 306, SFC peak 4. ee>98%. 8-[3-(2-{dispiro[2.0.2.1]heptan-7-yl}ethoxy)-1H-pyrazol-1-yl]-16-fluoro-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione (enantiomer 4) (74 mg, 46%). $^1$H NMR (500 MHz, DMSO-$d_6$) δ 12.57 (s, 1H), 8.21 (d, J=2.8 Hz, 1H), 7.83 (d, J=8.2 Hz, 1H), 7.64 (t, J=7.9 Hz, 1H), 7.33 (broad d, J=9.7 Hz, 1H), 7.13 (d, J=7.2 Hz, 1H), 6.94 (dd, J=10.6, 8.4 Hz, 2H), 6.10 (d, J=2.7 Hz, 1H), 4.88 (d, J=43.5 Hz, 1H), 4.28-4.08 (m, 3H), 3.35-3.24 (m, 1H overlapped with water), 3.04-2.92 (m, 1H), 2.63 (t, J=10.9 Hz, 1H), 2.31 (br s, 1H), 1.97-1.75 (m, 5H), 1.67-1.59 (m, 4H), 1.52 (s, 3H), 1.48 (t, J=6.6 Hz, 1H), 0.91-0.76 (m, 4H), 0.67-0.60 (m, 2H), 0.54-0.41 (m, 2H). ESI-MS m/z calc. 635.269, found 636.33 (M+1)$^+$; Retention time: 2.3 min (LC Method B).

Bioactivity Assays

Solutions

Base medium (ADF+++) consisted of Advanced DMEM/Ham's F12, 2 mM Glutamax, 10 mM HEPES, 1 μ/ml penicillin/streptomycin.

Intestinal enteroid maintenance medium (IEMM) consisted of ADF+++, 1× B27 supplement, 1× N2 supplement, 1.25 mM N-acetyl cysteine, 10 mM Nicotinamide, 50 ng/mL hEGF, 10 nM Gastrin, 1 μg/mL hR-spondin-1, 100 ng/mL hNoggin, TGF-b type 1 inhibitor A-83-01, 100 μg/mL Primocin, 10 μM P38 MAPK inhibitor SB202190.

Bath 1 Buffer consisted of 1 mM $MgCl_2$, 160 mM NaCl, 4.5 mM KCl, 10 mM HEPES, 10 mM Glucose, 2 mM $CaCl_2$).

Chloride Free Buffer consisted of 1 mM Magnesium Gluconate, 2 mM Calcium Gluconate, 4.5 mM Potassium Gluconate, 160 mM Sodium Gluconate, 10 mM HEPES, 10 mM Glucose.

Bath1 Dye Solution consisted of Bath 1 Buffer, 0.04% Pluronic F127, 20 µM Methyl Oxonol, 30 µM CaCCinh-A01, 30 µM Chicago Sky Blue.

Chloride Free Dye Solution consisted of Chloride Free Buffer, 0.04% Pluronic F127, 20 µM Methyl Oxonol, 30 µM CaCCinh-A01, 30 µM Chicago Sky Blue.

Chloride Free Dye Stimulation Solution consisted of Chloride Free Dye Solution, 10 µM forskolin, 100 µM IBMX, and 300 nM Compound III.

Cell Culture

Human intestinal epithelial enteroid cells were obtained from the Hubrecht Institute for Developmental Biology and Stem Cell Research, Utrecht, The Netherlands and expanded in T-Flasks as previously described (Dekkers J F, Wiegerinck C L, de Jonge H R, Bronsveld I, Janssens H M, de Winter-de Groot K M, Brandsma A M, de Jong N W M, Bijvelds M J C, Scholte B J, Nieuwenhuis E E S, van den Brink S, Clevers H, van der Ent C K, Middendorp S and M Beekman J M. A functional CFTR assay using primary cystic fibrosis intestinal organoids. Nat Med. 2013 July; 19(7):939-45).

Enteroid Cell Harvesting and Seeding

Cells were recovered in cell recovery solution, collected by centrifugation at 650 rpm for 5 min at 4° C., resuspended in TryPLE and incubated for 5 min at 37° C. Cells were then collected by centrifugation at 650 rpm for 5 min at 4° C. and resuspended in IEMM containing 10 µM ROCK inhibitor (RI) (trans-4-[(1R)-1-aminoethyl]-N-4-pyridinylcyclohexanecarboxamide). The cell suspension was passed through a 40 µm cell strainer and resuspended at 1×106 cells/mL in IEMM containing 10 µM RI. Cells were seeded at 5000 cells/well into multi-well plates and incubated for overnight at 37° C., 95% humidity and 5% $CO_2$ prior to assay.

Membrane Potential Dye Assay

Enteroid cells were incubated with test compound in IEMM for 18-24 hours at 37° C., 95% humidity and 5% $CO_2$. Following compound incubations, a membrane potential dye assay was employed using a FLIPR Tetra to directly measure the potency and efficacy of the test compound on CFTR-mediated chloride transport following acute addition of 10 µM forskolin and 300 nM Compound III. Briefly, cells were washed 5 times in Bath 1 Buffer. Bath 1 Dye Solution was added and the cells were incubated for 25 min at room temperature. Following dye incubation, cells were washed 3 times in Chloride Free Dye Solution. Chloride transport was initiated by addition of Chloride Free Dye Stimulation Solution and the fluorescence signal was read for 15 min. The CFTR-mediated chloride transport for each condition was determined from the AUC of the fluorescence response to acute forskolin and 300 nM Compound III stimulation. Chloride transport was then expressed as a percentage of the chloride transport following treatment with 3 µM Compound A, 3 µM Compound II and 300 nM acute Compound III triple combination control (% Activity). Compound A is:

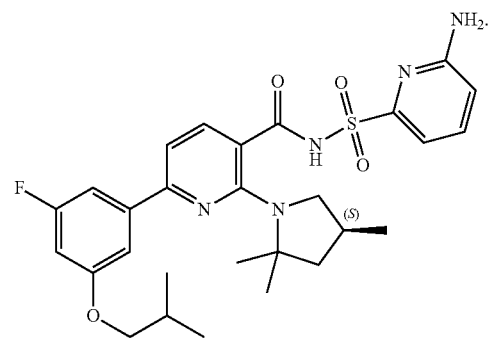

Table 5 reflects the results of bioactivity assays for exemplary compounds of the invention (Max Activity: +++ is >60%; ++ is 30-60%; + is <30%. EC50: +++ is <1 µM; ++ is 1-3 µM; + is >3 µM; and ND is "not determined.")

TABLE 5

| Compound No. | Molecule | Max. Activity | EC50 |
|---|---|---|---|
| 1 | 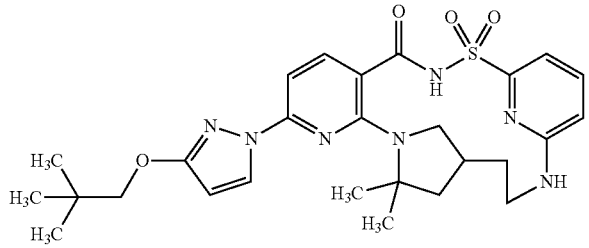 [SMILES: CC(C)(C)COc1ccn(-c2ccc3c(n2)N2CC(CCNc4cccc(n4)S(=O)(=O)NC3=O)CC2(C)C)n1] | +++ | +++ |
| 2 | 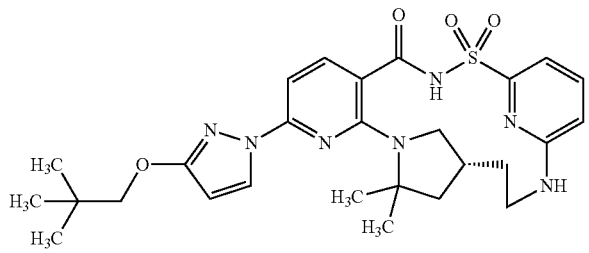 [SMILES: CC(C)(C)COc1ccn(-c2ccc3c(n2)N2C[C@H](CCNc4cccc(n4)S(=O)(=O)NC3=O)CC2(C)C)n1] | +++ | ++ |

TABLE 5-continued

| Compound No. | Molecule | Max. Activity | EC50 |
|---|---|---|---|
| 3 | | +++ | +++ |
| 4 | | +++ | +++ |
| 5 | | +++ | +++ |
| 6 | | +++ | +++ |
| 7 | | ++ | +++ |

TABLE 5-continued

| Compound No. | Molecule | Max. Activity | EC50 |
|---|---|---|---|
| 8 | | + | + |
| 9 | | ++ | +++ |
| 10 | | + | + |
| 11 | | +++ | +++ |
| 12 | | +++ | +++ |

TABLE 5-continued

| Compound No. | Molecule | Max. Activity | EC50 |
|---|---|---|---|
| 13 | | + | ++ |
| 14 | | +++ | +++ |
| 15 | | +++ | +++ |
| 16 | | ++ | +++ |
| 17 | | ++ | ++ |

TABLE 5-continued

| Compound No. | Molecule | Max. Activity | EC50 |
|---|---|---|---|
| 18 | | ++ | +++ |
| 19 | | ++ | ++ |
| 20 | | +++ | +++ |
| 21 | | ++ | + |
| 22 | | +++ | +++ |

TABLE 5-continued

| Compound No. | Molecule | Max. Activity | EC50 |
|---|---|---|---|
| 23 | | + | + |
| 24 | | + | + |
| 25 | | ++ | +++ |
| 26 | | +++ | +++ |
| 27 | | +++ | +++ |

TABLE 5-continued
| Compound No. | Molecule | Max. Activity | EC50 |
|---|---|---|---|
| 28 | 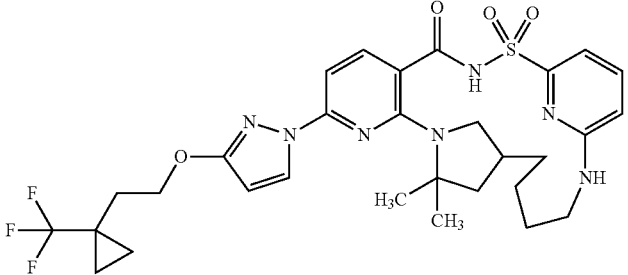 | ++ | +++ |
| 29 | 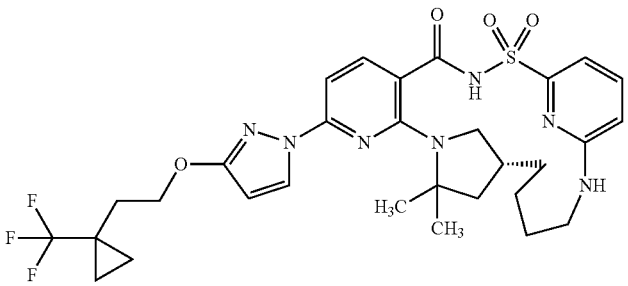 [SMILES: CC1(C)C[C@H]2CCCCNc3cccc(n3)S(=O)(=O)NC(=O)c3ccc(-n4ccc(OCCC5(C(F)(F)F)CC5)n4)nc3N1C2] | ++ | +++ |
| 30 | 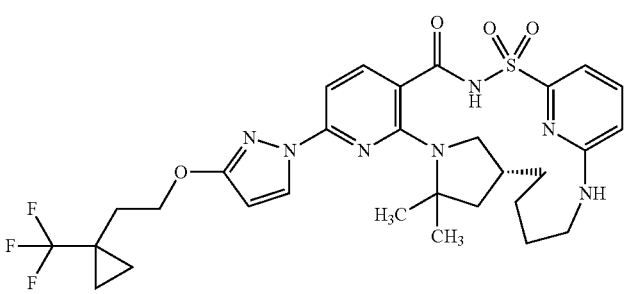 [SMILES: CC1(C)C[C@H]2CCCCNc3cccc(n3)S(=O)(=O)NC(=O)c3ccc(-n4ccc(OCCC5(C(F)(F)F)CC5)n4)nc3N1C2] | +++ | +++ |
| 31 | 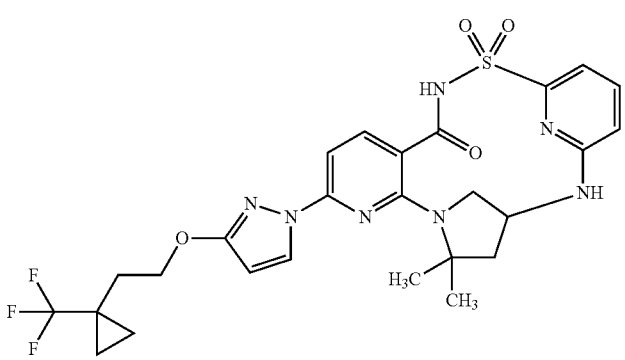 [SMILES: CC1(C)CC2CN1c1nc(-n3ccc(OCCC4(C(F)(F)F)CC4)n3)ccc1C(=O)NS(=O)(=O)c1cccc(n1)N2] | + | + |
| 32 | 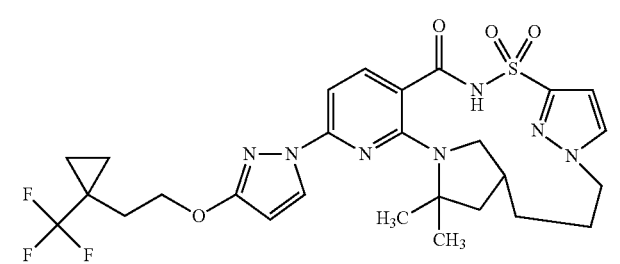 [SMILES: CC1(C)CC2CCCn3ccc(n3)S(=O)(=O)NC(=O)c3ccc(-n4ccc(OCCC5(C(F)(F)F)CC5)n4)nc3N1C2] | +++ | +++ |

TABLE 5-continued

| Compound No. | Molecule | Max. Activity | EC50 |
| --- | --- | --- | --- |
| 33 | | + | + |
| 34 | | +++ | +++ |
| 35 | | +++ | +++ |
| 36 | | +++ | +++ |
| 37 | | + | +++ |
| 38 | | ++ | + |

TABLE 5-continued

| Compound No. | Molecule | Max. Activity | EC50 |
|---|---|---|---|
| 39 | | +++ | ++ |
| 40 | | ++ | +++ |
| 41 | | + | + |
| 42 | | +++ | +++ |
| 43 | | +++ | +++ |

TABLE 5-continued

| Compound No. | Molecule | Max. Activity | EC50 |
|---|---|---|---|
| 44 | | ++ | + |
| 45 | | +++ | +++ |
| 46 | | + | + |
| 47 | | +++ | +++ |
| 48 | | + | + |

TABLE 5-continued
| Compound No. | Molecule | Max. Activity | EC50 |
|---|---|---|---|
| 49 | 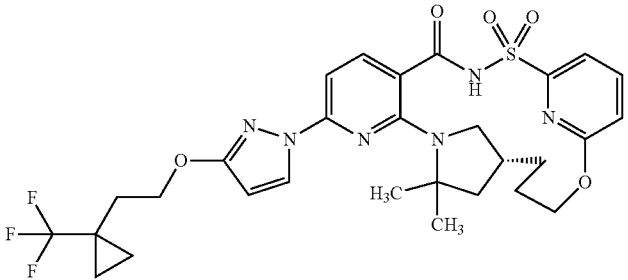 [SMILES: CC1(C)C[C@H]2CCCOc3cccc(n3)S(=O)(=O)NC(=O)c3ccc(-n4ccc(OCCC5(C(F)(F)F)CC5)n4)nc3N1C2] | +++ | +++ |
| 50 | 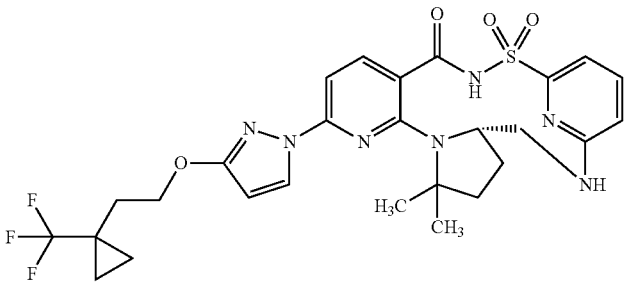 [SMILES: CC1(C)CC[C@H]2CNc3cccc(n3)S(=O)(=O)NC(=O)c3ccc(-n4ccc(OCCC5(C(F)(F)F)CC5)n4)nc3N21] | + | + |
| 51 | 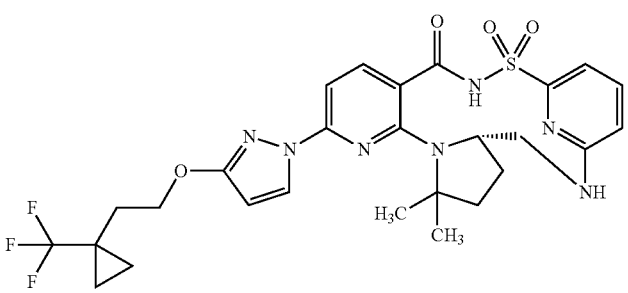 [SMILES: CC1(C)CC[C@H]2CNc3cccc(n3)S(=O)(=O)NC(=O)c3ccc(-n4ccc(OCCC5(C(F)(F)F)CC5)n4)nc3N21] | + | + |
| 52 | 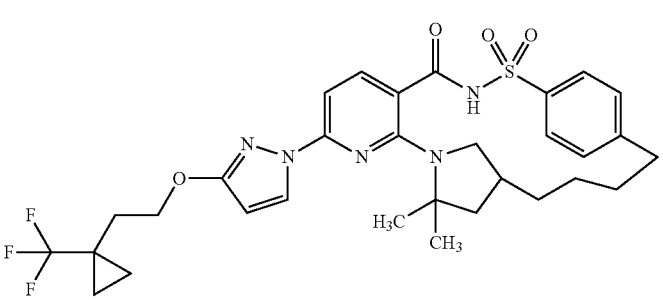 [SMILES: CC1(C)CC2CCCCc3ccc(cc3)S(=O)(=O)NC(=O)c3ccc(-n4ccc(OCCC5(C(F)(F)F)CC5)n4)nc3N1C2] | ++ | +++ |
| 53 | 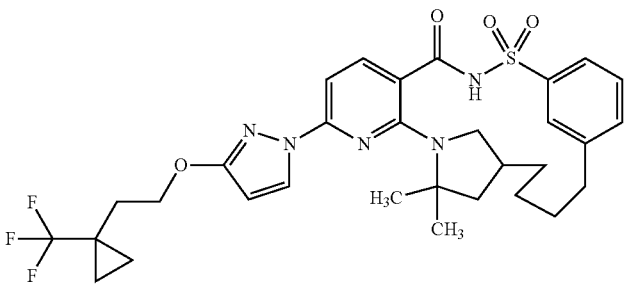 [SMILES: CC1(C)CC2CCCCc3cccc(c3)S(=O)(=O)NC(=O)c3ccc(-n4ccc(OCCC5(C(F)(F)F)CC5)n4)nc3N1C2] | +++ | +++ |

TABLE 5-continued
| Compound No. | Molecule | Max. Activity | EC50 |
|---|---|---|---|
| 54 | 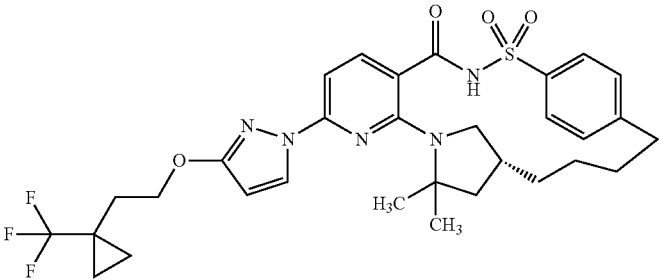 [SMILES: CC1(C)C[C@H]2CCCCc3ccc(cc3)S(=O)(=O)NC(=O)c3ccc(-n4ccc(OCCC5(C(F)(F)F)CC5)n4)nc3N1C2] | ++ | ++ |
| 55 | 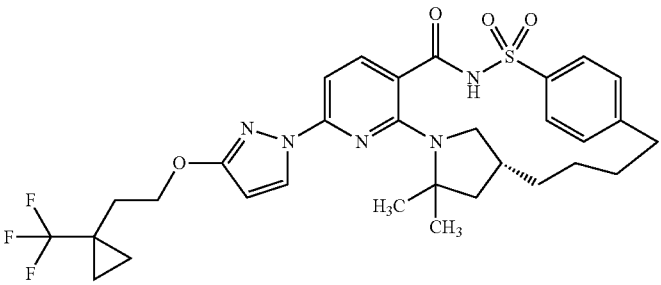 [SMILES: CC1(C)C[C@H]2CCCCc3ccc(cc3)S(=O)(=O)NC(=O)c3ccc(-n4ccc(OCCC5(C(F)(F)F)CC5)n4)nc3N1C2] | +++ | +++ |
| 56 | 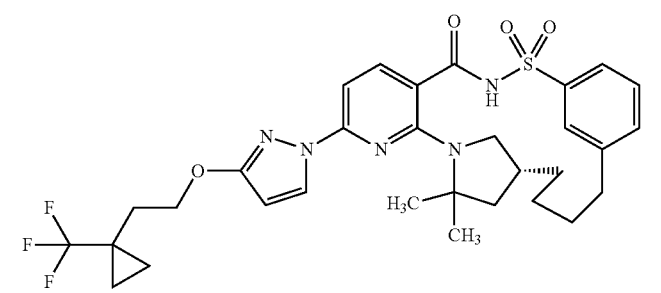 [SMILES: CC1(C)C[C@H]2CCCCc3cccc(c3)S(=O)(=O)NC(=O)c3ccc(-n4ccc(OCCC5(C(F)(F)F)CC5)n4)nc3N1C2] | + | +++ |
| 57 | 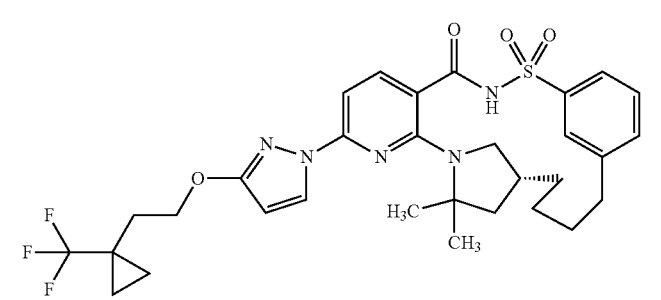 [SMILES: CC1(C)C[C@H]2CCCCc3cccc(c3)S(=O)(=O)NC(=O)c3ccc(-n4ccc(OCCC5(C(F)(F)F)CC5)n4)nc3N1C2] | ++ | +++ |
| 58 | 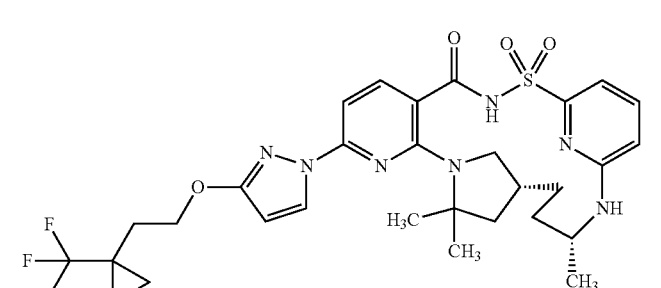 | + | +++ |

TABLE 5-continued

| Compound No. | Molecule | Max. Activity | EC50 |
|---|---|---|---|
| 59 | | +++ | +++ |
| 60 | | +++ | +++ |
| 61 | | +++ | +++ |
| 62 | | +++ | +++ |
| 63 | | +++ | +++ |

TABLE 5-continued

| Compound No. | Molecule | Max. Activity | EC50 |
|---|---|---|---|
| 64 | | ++ | +++ |
| 65 | | ++ | +++ |
| 66 | | +++ | +++ |
| 67 | | +++ | +++ |
| 68 | | ++ | +++ |

TABLE 5-continued

| Compound No. | Molecule | Max. Activity | EC50 |
|---|---|---|---|
| 69 | | +++ | +++ |
| 70 | | ++ | +++ |
| 71 | | + | + |
| 72 | | + | + |
| 73 | | +++ | +++ |

TABLE 5-continued
| Compound No. | Molecule | Max. Activity | EC50 |
|---|---|---|---|
| 74 | 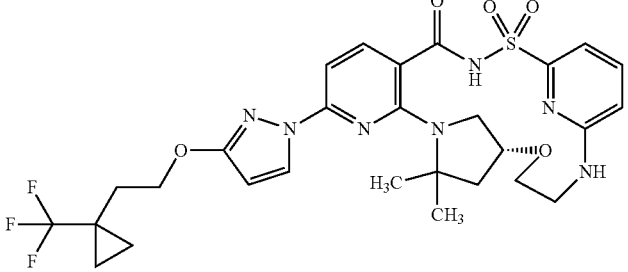 | + | ++ |
| 75 | 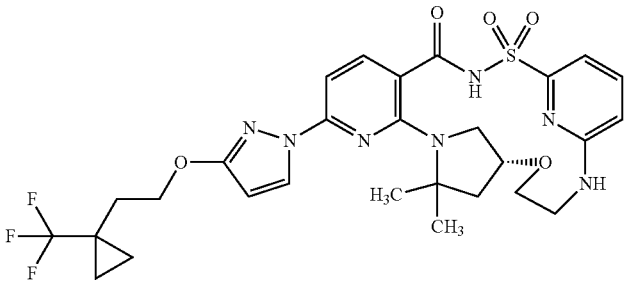 [SMILES: CC1(C)C[C@@H]2CN1c1nc(-n3ccc(OCCC4(C(F)(F)F)CC4)n3)ccc1C(=O)NS(=O)(=O)c1cccc(n1)NCCO2] | +++ | +++ |
| 76 | 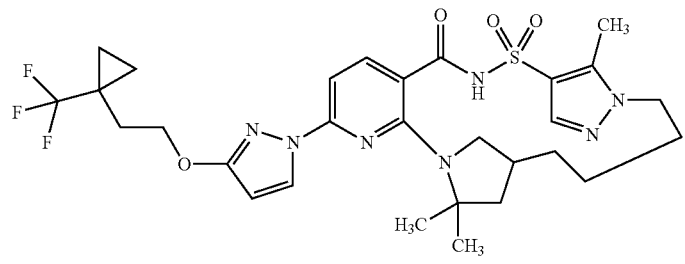 [SMILES: Cc1c2cnn1CCCCC1CN(c3nc(-n4ccc(OCCC5(C(F)(F)F)CC5)n4)ccc3C(=O)NS2(=O)=O)C(C)(C)C1] | ND | ND |
| 77 | 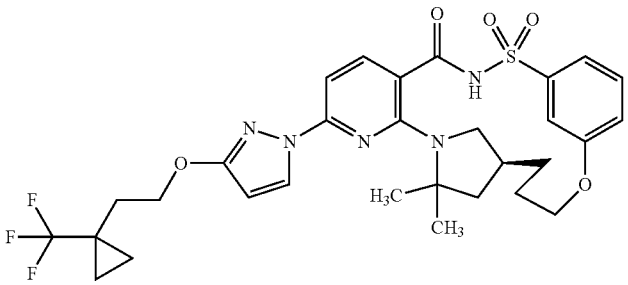 [SMILES: CC1(C)C[C@@H]2CCCOc3cccc(c3)S(=O)(=O)NC(=O)c3ccc(-n4ccc(OCCC5(C(F)(F)F)CC5)n4)nc3N1C2] | +++ | +++ |
| 78 | 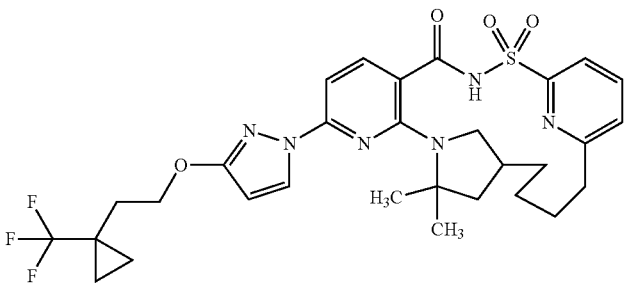 [SMILES: CC1(C)CC2CCCCc3cccc(n3)S(=O)(=O)NC(=O)c3ccc(-n4ccc(OCCC5(C(F)(F)F)CC5)n4)nc3N1C2] | +++ | +++ |

TABLE 5-continued

| Compound No. | Molecule | Max. Activity | EC50 |
|---|---|---|---|
| 79 | | ++ | +++ |
| 80 | | + | + |
| 81 | | ++ | +++ |
| 82 | | + | + |

TABLE 5-continued

| Compound No. | Molecule | Max. Activity | EC50 |
|---|---|---|---|
| 83 | | ++ | +++ |
| 84 | | + | + |
| 85 | | +++ | +++ |
| 86 | | + | + |
| 87 | | +++ | +++ |

TABLE 5-continued
| Compound No. | Molecule | Max. Activity | EC50 |
|---|---|---|---|
| 88 | 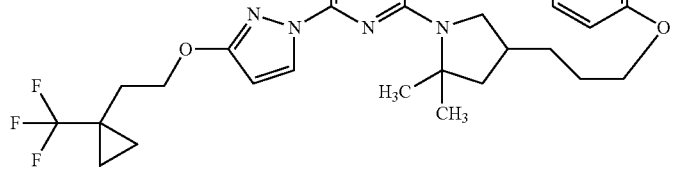 | ++ | +++ |
| 89 | 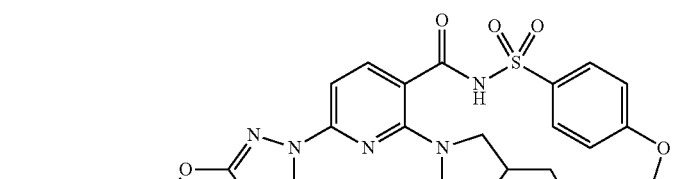 | ++ | +++ |
| 90 |  | ++ | +++ |
| 91 | 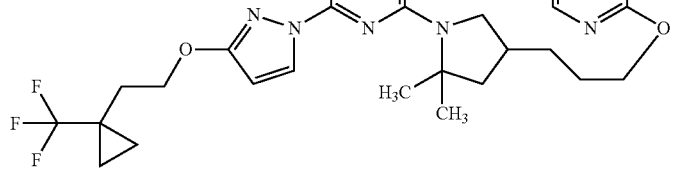 | + | + |
| 92 | 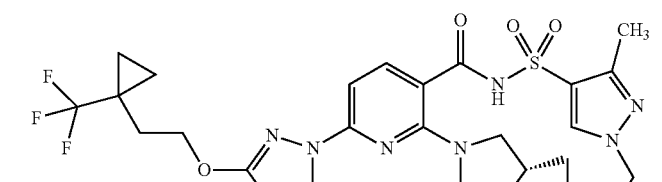 | ++ | +++ |

TABLE 5-continued
| Compound No. | Molecule | Max. Activity | EC50 |
|---|---|---|---|
| 93 | 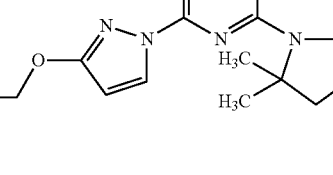 | +++ | +++ |
| 94 | 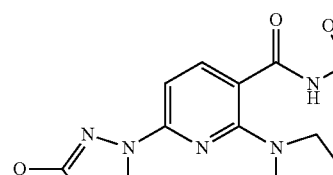 | + | + |
| 95 |  | ++ | +++ |
| 96 | 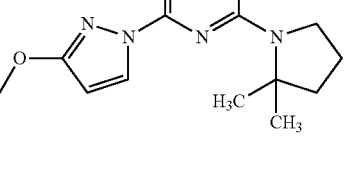 | + | + |
| 97 | 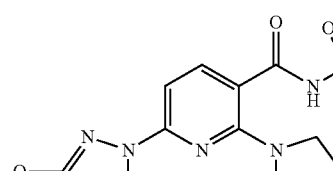 | +++ | +++ |

TABLE 5-continued

| Compound No. | Molecule | Max. Activity | EC50 |
|---|---|---|---|
| 98 | | ++ | +++ |
| 99 | | +++ | +++ |
| 100 | | + | + |
| 101 | | ++ | +++ |
| 102 | | +++ | +++ |

TABLE 5-continued
| Compound No. | Molecule | Max. Activity | EC50 |
|---|---|---|---|
| 103 | 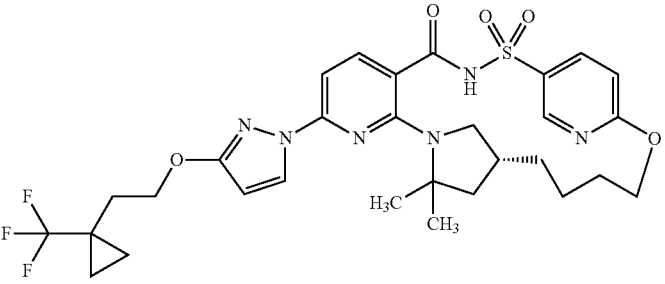 [SMILES: CC1(C)C[C@H]2CCCCOc3ccc(cn3)S(=O)(=O)NC(=O)c3ccc(-n4ccc(OCCC5(C(F)(F)F)CC5)n4)nc3N1C2] | ++ | +++ |
| 104 | 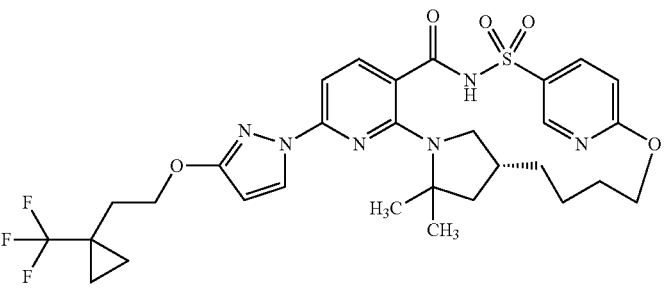 [SMILES: CC1(C)C[C@H]2CCCCOc3ccc(cn3)S(=O)(=O)NC(=O)c3ccc(-n4ccc(OCCC5(C(F)(F)F)CC5)n4)nc3N1C2] | + | + |
| 105 | 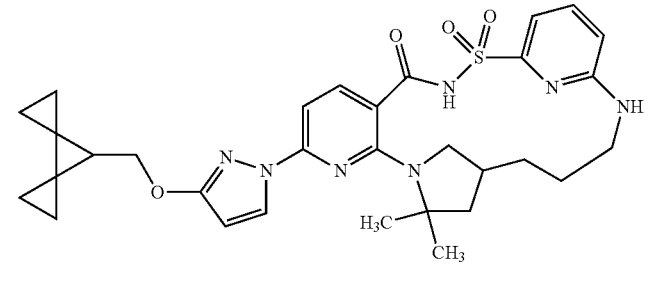 [SMILES: CC1(C)CC2CCCNc3cccc(n3)S(=O)(=O)NC(=O)c3ccc(-n4ccc(OCC5C6(CC6)C56CC6)n4)nc3N1C2] | +++ | +++ |
| 106 | 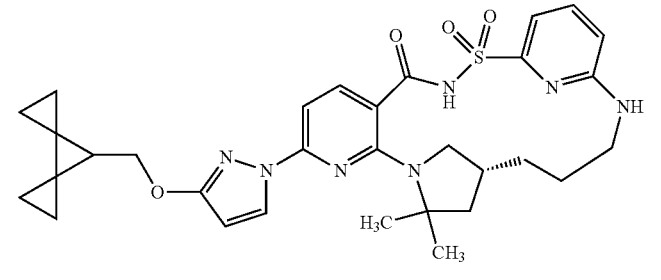 [SMILES: CC1(C)C[C@H]2CCCNc3cccc(n3)S(=O)(=O)NC(=O)c3ccc(-n4ccc(OCC5C6(CC6)C56CC6)n4)nc3N1C2] | +++ | +++ |
| 107 | 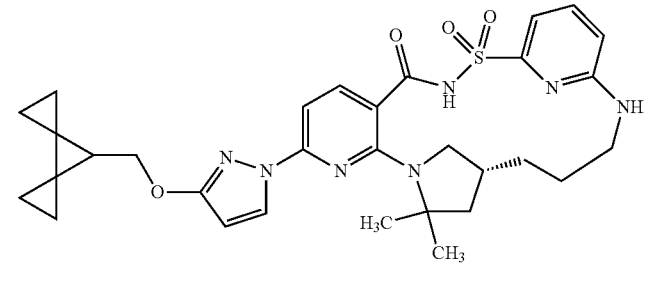 [SMILES: CC1(C)C[C@H]2CCCNc3cccc(n3)S(=O)(=O)NC(=O)c3ccc(-n4ccc(OCC5C6(CC6)C56CC6)n4)nc3N1C2] | +++ | +++ |

TABLE 5-continued
| Compound No. | Molecule | Max. Activity | EC50 |
|---|---|---|---|
| 108 | 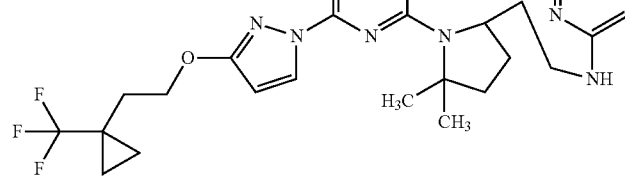 | ++ | +++ |
| 109 | 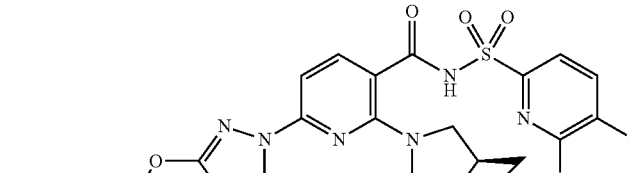 | ++ | +++ |
| 110 |  | ++ | +++ |
| 111 | 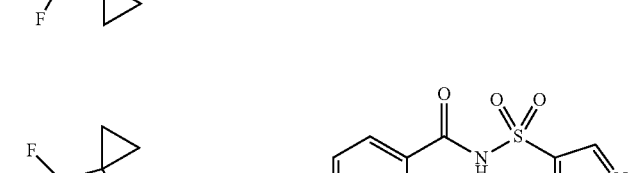 | +++ | +++ |
| 112 | 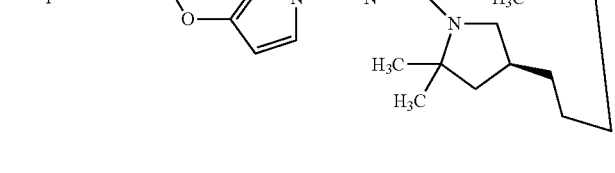 | ++ | +++ |

TABLE 5-continued

| Compound No. | Molecule | Max. Activity | EC50 |
|---|---|---|---|
| 113 | | ++ | ++ |
| 114 | | + | + |
| 115 | | +++ | +++ |
| 116 | | ++ | +++ |
| 117 | | ++ | +++ |

TABLE 5-continued

| Compound No. | Molecule | Max. Activity | EC50 |
|---|---|---|---|
| 118 | | + | ++ |
| 119 | | +++ | +++ |
| 120 | | ++ | +++ |
| 121 | | +++ | +++ |
| 122 | | ++ | +++ |

| Compound No. | Molecule | Max. Activity | EC50 |
|---|---|---|---|
| 123 | 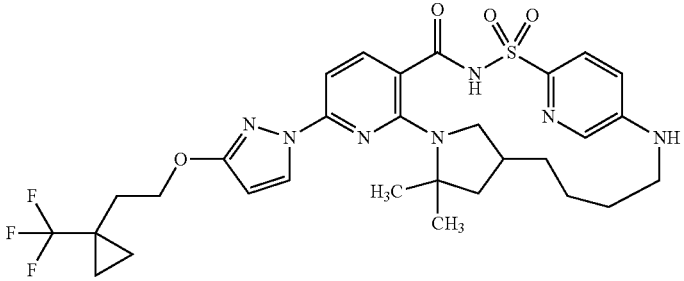 [SMILES: CC1(C)CC2CCCCNc3ccc(nc3)S(=O)(=O)NC(=O)c3ccc(-n4ccc(OCCC5(C(F)(F)F)CC5)n4)nc3N1C2] | +++ | +++ |
| 124 | 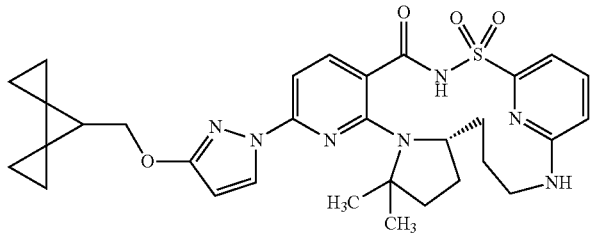 [SMILES: CC1(C)CC[C@H]2CCCNc3cccc(n3)S(=O)(=O)NC(=O)c3ccc(-n4ccc(OCC5C6(CC6)C56CC6)n4)nc3N21] | +++ | +++ |
| 125 | 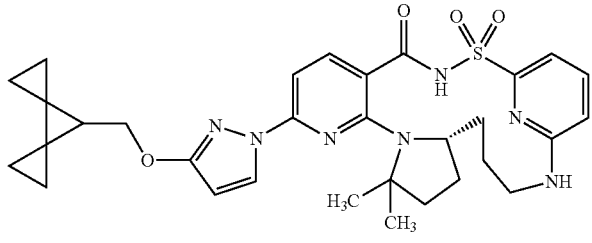 [SMILES: CC1(C)CC[C@H]2CCCNc3cccc(n3)S(=O)(=O)NC(=O)c3ccc(-n4ccc(OCC5C6(CC6)C56CC6)n4)nc3N21] | + | +++ |
| 126 | 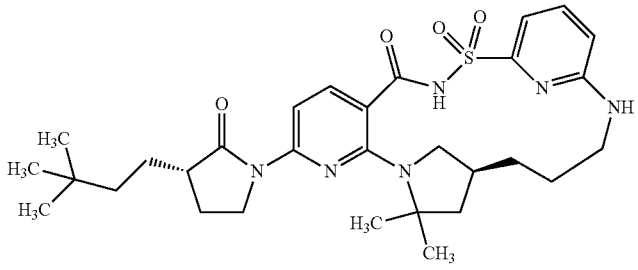 [SMILES: CC(C)(C)CC[C@H]1CCN(c2ccc3c(n2)N2C[C@@H](CCCNc4cccc(n4)S(=O)(=O)NC3=O)CC2(C)C)C1=O] | ++ | +++ |
| 127 | 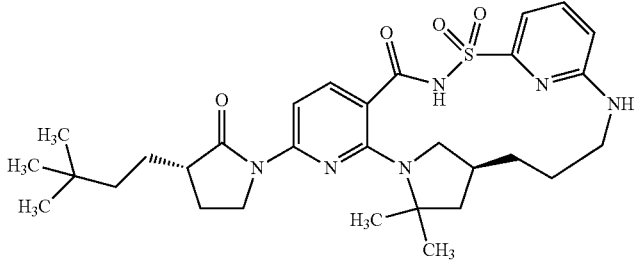 | +++ | +++ |

TABLE 5-continued
| Compound No. | Molecule | Max. Activity | EC50 |
|---|---|---|---|
| 128 | 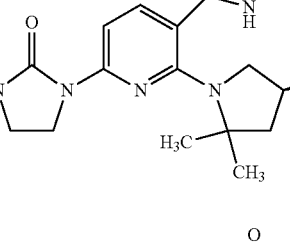 | +++ | +++ |
| 129 | 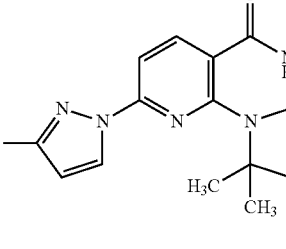 | +++ | +++ |
| 130 | 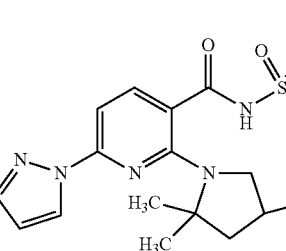 | +++ | +++ |
| 131 | 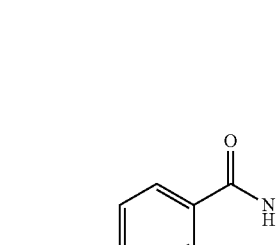 | ++ | +++ |
| 132 | 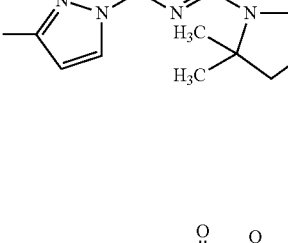 | ++ | +++ |

TABLE 5-continued

| Compound No. | Molecule | Max. Activity | EC50 |
|---|---|---|---|
| 133 | | +++ | +++ |
| 134 | | + | +++ |
| 135 | | +++ | +++ |
| 136 | | +++ | +++ |
| 137 | | + | + |

TABLE 5-continued

| Compound No. | Molecule | Max. Activity | EC50 |
|---|---|---|---|
| 138 | | + | + |
| 139 | | +++ | +++ |
| 140 | | ++ | +++ |
| 141 | | +++ | +++ |
| 142 | | + | +++ |

TABLE 5-continued
| Compound No. | Molecule | Max. Activity | EC50 |
|---|---|---|---|
| 143 | 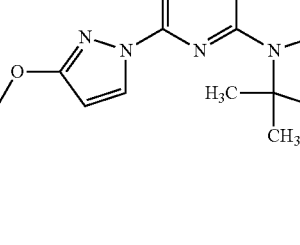 | + | ++ |
| 144 | 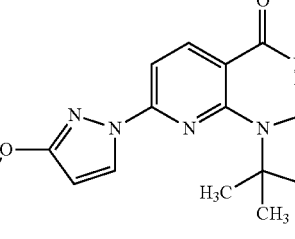 | ++ | +++ |
| 145 | 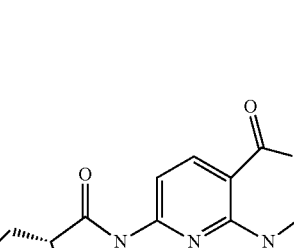 | +++ | +++ |
| 146 | 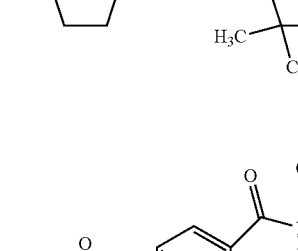 | +++ | +++ |
| 147 | 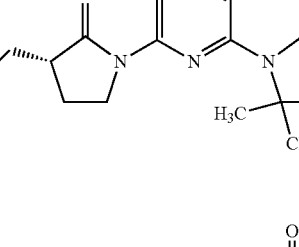 | ++ | +++ |

TABLE 5-continued

| Compound No. | Molecule | Max. Activity | EC50 |
|---|---|---|---|
| 148 | | + | + |
| 149 | | +++ | +++ |
| 150 | | + | ++ |
| 151 | | +++ | +++ |
| 152 | | + | + |

TABLE 5-continued

| Compound No. | Molecule | Max. Activity | EC50 |
|---|---|---|---|
| 153 | | + | + |
| 154 | | +++ | +++ |
| 155 | | +++ | +++ |
| 156 | | +++ | +++ |
| 157 | | +++ | +++ |

TABLE 5-continued

| Compound No. | Molecule | Max. Activity | EC50 |
|---|---|---|---|
| 158 | | +++ | +++ |
| 159 | | + | + |
| 160 | | +++ | +++ |
| 161 | | +++ | +++ |
| 162 | | ++ | ++ |
| 163 | | ++ | +++ |

TABLE 5-continued

| Compound No. | Molecule | Max. Activity | EC50 |
|---|---|---|---|
| 164 | | ++ | ++ |
| 165 | | + | + |
| 166 | | +++ | +++ |
| 167 | | ++ | +++ |
| 168 | | + | + |
| 169 | | ++ | +++ |

TABLE 5-continued

| Compound No. | Molecule | Max. Activity | EC50 |
|---|---|---|---|
| 170 | | ++ | +++ |
| 171 | | +++ | +++ |
| 172 | | ++ | +++ |
| 173 | | +++ | +++ |
| 174 | | +++ | +++ |
| 175 | | +++ | +++ |

US 11,866,450 B2

1233                                                                                             1234

TABLE 5-continued

| Compound No. | Molecule | Max. Activity | EC50 |
|---|---|---|---|
| 176 | | +++ | +++ |
| 177 | | ++ | +++ |
| 178 | | +++ | +++ |
| 179 | | ++ | +++ |
| 180 | | +++ | +++ |

TABLE 5-continued

| Compound No. | Molecule | Max. Activity | EC50 |
|---|---|---|---|
| 181 | | ++ | ++ |
| 182 | | ++ | +++ |
| 183 | | ++ | +++ |
| 184 | | + | ++ |
| 185 | | +++ | +++ |

TABLE 5-continued
| Compound No. | Molecule | Max. Activity | EC50 |
|---|---|---|---|
| 186 | 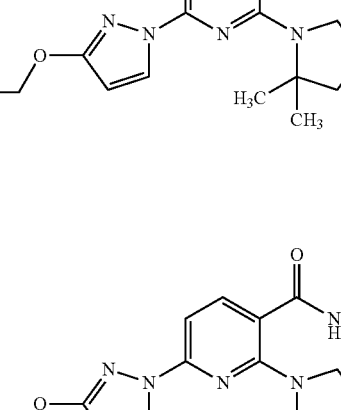 | + | +++ |
| 187 | 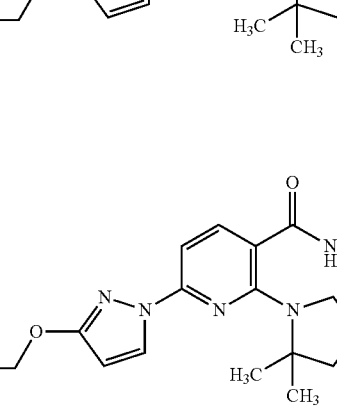 | +++ | +++ |
| 188 | 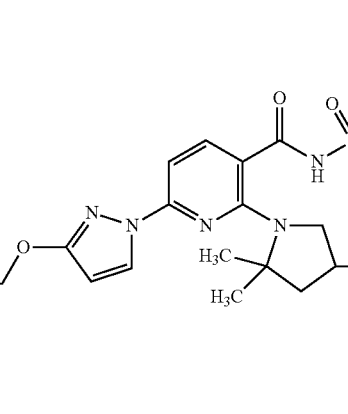 | +++ | +++ |
| 189 | | +++ | +++ |
| 190 | 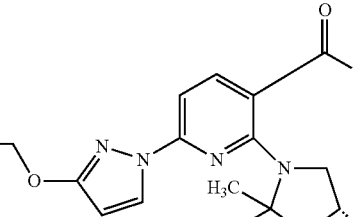 | ++ | +++ |

TABLE 5-continued
| Compound No. | Molecule | Max. Activity | EC50 |
|---|---|---|---|
| 191 | 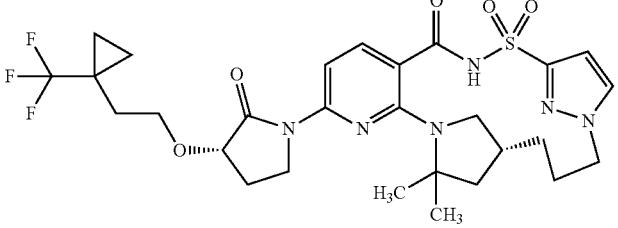 | ++ | +++ |
| 192 | 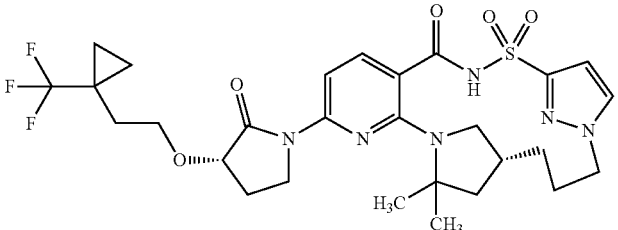 | +++ | +++ |
| 193 | 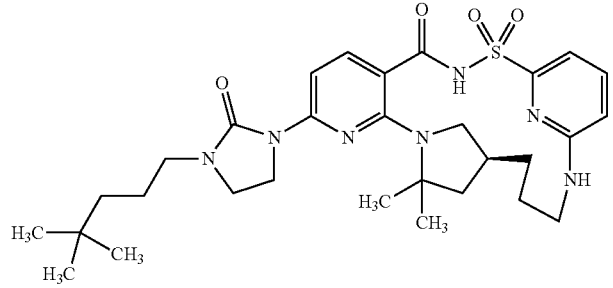 [SMILES: CC(C)(C)CCCN1CCN(c2ccc3c(n2)N2C[C@@H](CCCNc4cccc(n4)S(=O)(=O)NC3=O)CC2(C)C)C1=O] | +++ | +++ |
| 194 | 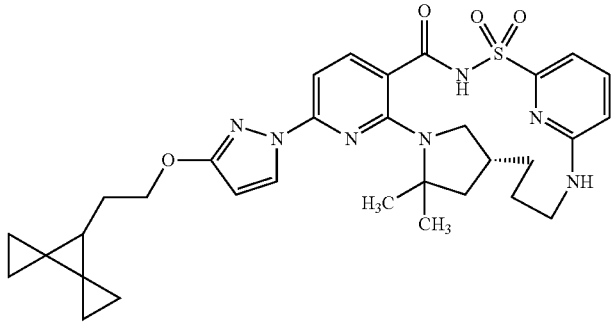 [SMILES: CC1(C)C[C@H]2CCCNc3cccc(n3)S(=O)(=O)NC(=O)c3ccc(-n4ccc(OCCC5C6(CC6)C56CC6)n4)nc3N1C2] | ++ | +++ |
| 195 | 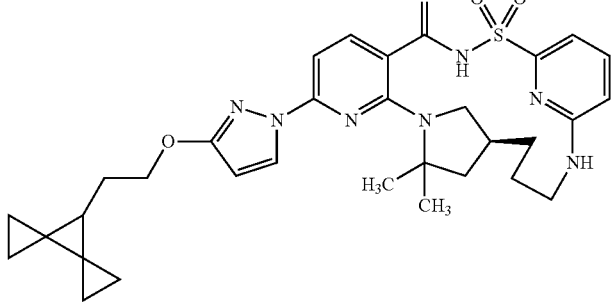 | +++ | +++ |

TABLE 5-continued

| Compound No. | Molecule | Max. Activity | EC50 |
|---|---|---|---|
| 196 | | ++ | ++ |
| 197 | | +++ | +++ |
| 198 | | ND | ND |
| 199 | | ++ | +++ |
| 200 | | + | +++ |

TABLE 5-continued
| Compound No. | Molecule | Max. Activity | EC50 |
|---|---|---|---|
| 201 | 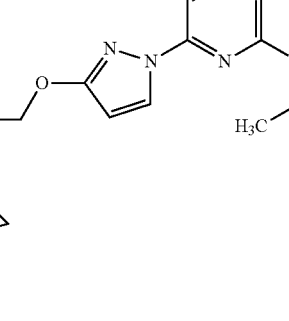 | + | + |
| 202 | 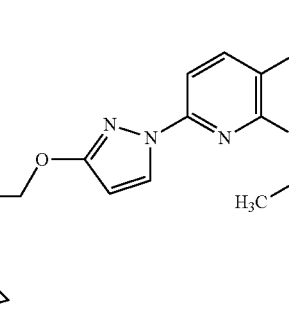 | ++ | +++ |
| 203 | 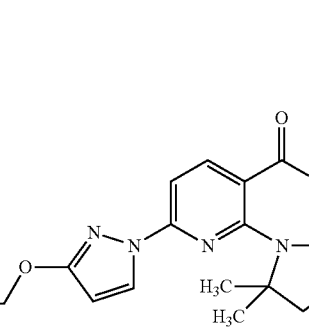 | +++ | +++ |
| 204 | 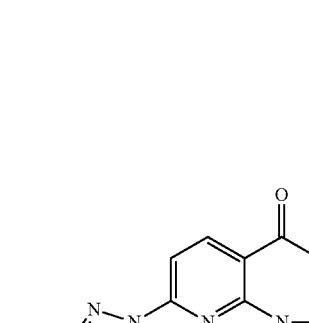 | + | + |

TABLE 5-continued
| Compound No. | Molecule | Max. Activity | EC50 |
|---|---|---|---|
| 205 | 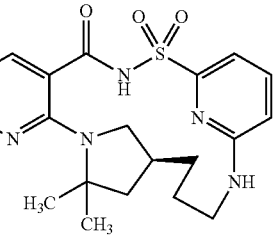 | +++ | +++ |
| 206 | 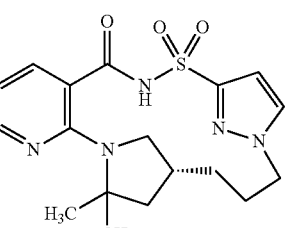 | + | +++ |
| 207 | 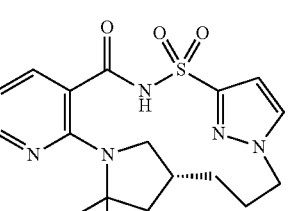 | +++ | +++ |
| 208 | 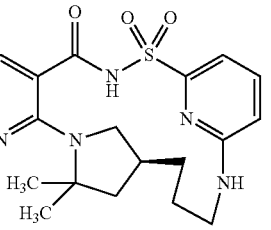 | +++ | +++ |
| 209 | 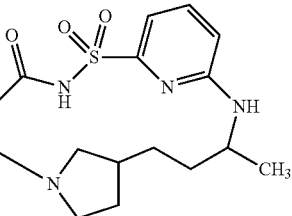 | ++ | +++ |

TABLE 5-continued

| Compound No. | Molecule | Max. Activity | EC50 |
|---|---|---|---|
| 210 | | ++ | +++ |
| 211 | | ++ | +++ |
| 212 | | +++ | +++ |
| 213 | | + | + |
| 214 | | ++ | +++ |

TABLE 5-continued

| Compound No. | Molecule | Max. Activity | EC50 |
|---|---|---|---|
| 215 | | + | + |
| 216 | | +++ | +++ |
| 217 | | ++ | +++ |
| 218 | | + | + |
| 219 | | ++ | +++ |

TABLE 5-continued

| Compound No. | Molecule | Max. Activity | EC50 |
|---|---|---|---|
| 220 | | +++ | +++ |
| 221 | | +++ | +++ |
| 222 | | ++ | +++ |
| 223 | | +++ | +++ |
| 224 | | +++ | +++ |

TABLE 5-continued
| Compound No. | Molecule | Max. Activity | EC50 |
|---|---|---|---|
| 225 | 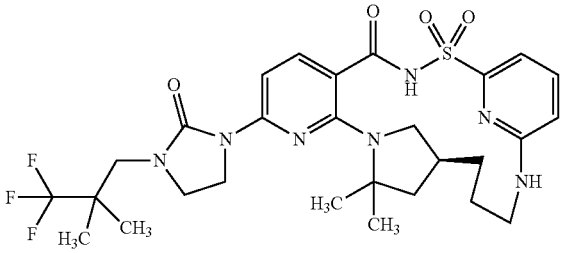 [SMILES: CC1(C)C[C@@H]2CCCNc3cccc(n3)S(=O)(=O)NC(=O)c3ccc(N4CCN(CC(C)(C)C(F)(F)F)C4=O)nc3N1C2] | ++ | +++ |
| 226 | 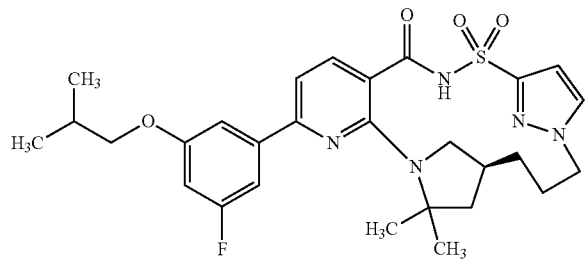 [SMILES: CC(C)COc1cc(F)cc(-c2ccc3c(n2)N2C[C@@H](CCCn4ccc(n4)S(=O)(=O)NC3=O)CC2(C)C)c1] | ++ | +++ |
| 227 | 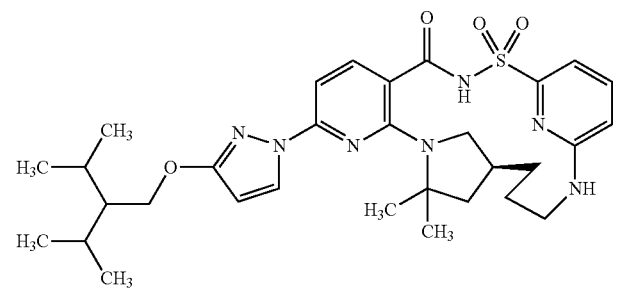 [SMILES: CC(C)C(COc1ccn(-c2ccc3c(n2)N2C[C@@H](CCCNc4cccc(n4)S(=O)(=O)NC3=O)CC2(C)C)n1)C(C)C] | +++ | +++ |
| 228 | 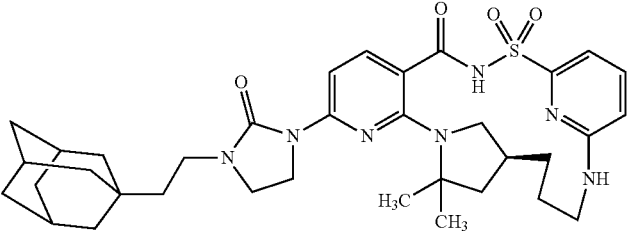 [SMILES: CC1(C)C[C@@H]2CCCNc3cccc(n3)S(=O)(=O)NC(=O)c3ccc(N4CCN(CCC56CC7CC(CC(C7)C5)C6)C4=O)nc3N1C2] | ++ | +++ |
| 229 | 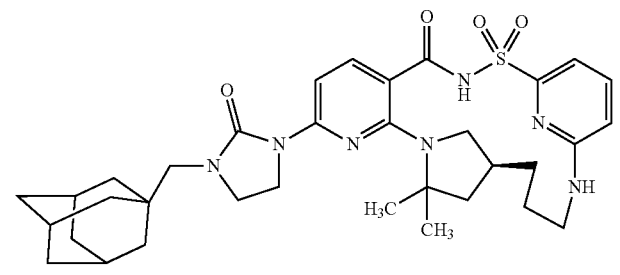 [SMILES: CC1(C)C[C@@H]2CCCNc3cccc(n3)S(=O)(=O)NC(=O)c3ccc(N4CCN(CC56CC7CC(CC(C7)C5)C6)C4=O)nc3N1C2] | ++ | +++ |
| 230 | 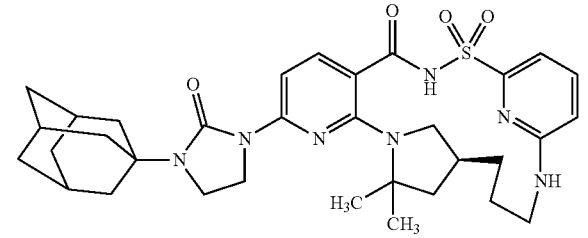 [SMILES: CC1(C)C[C@@H]2CCCNc3cccc(n3)S(=O)(=O)NC(=O)c3ccc(N4CCN(C56CC7CC(CC(C7)C5)C6)C4=O)nc3N1C2] | + | +++ |

TABLE 5-continued

| Compound No. | Molecule | Max. Activity | EC50 |
|---|---|---|---|
| 231 | | +++ | +++ |
| 232 | | + | + |
| 233 | | ND | ND |
| 234 | | ++ | +++ |
| 235 | | +++ | +++ |
| 236 | | + | + |

TABLE 5-continued

| Compound No. | Molecule | Max. Activity | EC50 |
|---|---|---|---|
| 237 | | +++ | +++ |
| 238 | | +++ | +++ |
| 239 | | + | +++ |
| 240 | | ++ | +++ |
| 241 | | ++ | +++ |

TABLE 5-continued

| Compound No. | Molecule | Max. Activity | EC50 |
|---|---|---|---|
| 242 | | ++ | +++ |
| 243 | | +++ | +++ |
| 244 | | ++ | +++ |
| 245 | | +++ | +++ |
| 246 | | ++ | +++ |

TABLE 5-continued

| Compound No. | Molecule | Max. Activity | EC50 |
|---|---|---|---|
| 247 | | +++ | +++ |
| 248 | | ++ | +++ |
| 249 | | +++ | +++ |
| 250 | | ++ | +++ |
| 251 | | ++ | +++ |

TABLE 5-continued

| Compound No. | Molecule | Max. Activity | EC50 |
|---|---|---|---|
| 252 | | +++ | +++ |
| 253 | | +++ | +++ |
| 254 | | ++ | +++ |
| 255 | | ++ | +++ |
| 256 | | ++ | + |

TABLE 5-continued

| Compound No. | Molecule | Max. Activity | EC50 |
|---|---|---|---|
| 257 | | +++ | +++ |
| 258 | | +++ | +++ |
| 259 | | +++ | +++ |
| 260 | | +++ | +++ |
| 261 | | ++ | +++ |

TABLE 5-continued
| Compound No. | Molecule | Max. Activity | EC50 |
|---|---|---|---|
| 262 | 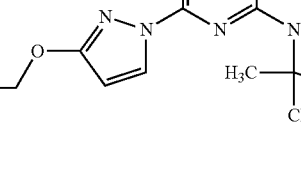 | +++ | +++ |
| 263 | 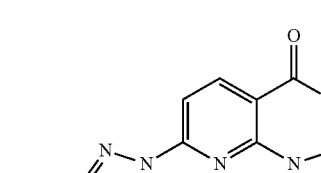 | ++ | +++ |
| 264 |  | +++ | +++ |
| 265 | 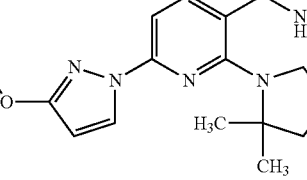 | +++ | +++ |
| 266 | 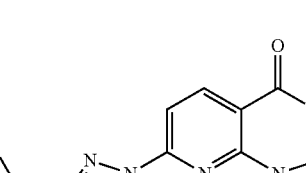 | ++ | +++ |

TABLE 5-continued

| Compound No. | Molecule | Max. Activity | EC50 |
|---|---|---|---|
| 267 | | +++ | +++ |
| 268 | | ++ | + |
| 269 | | +++ | +++ |
| 270 | | +++ | +++ |
| 271 | | +++ | +++ |

TABLE 5-continued

| Compound No. | Molecule | Max. Activity | EC50 |
|---|---|---|---|
| 272 | | + | + |
| 273 | | + | +++ |
| 274 | | +++ | +++ |
| 275 | | ++ | ++ |

TABLE 5-continued

| Compound No. | Molecule | Max. Activity | EC50 |
|---|---|---|---|
| 276 | | ++ | +++ |
| 277 | | + | + |
| 278 | | + | + |
| 279 | | ++ | +++ |

TABLE 5-continued
| Compound No. | Molecule | Max. Activity | EC50 |
|---|---|---|---|
| 280 | 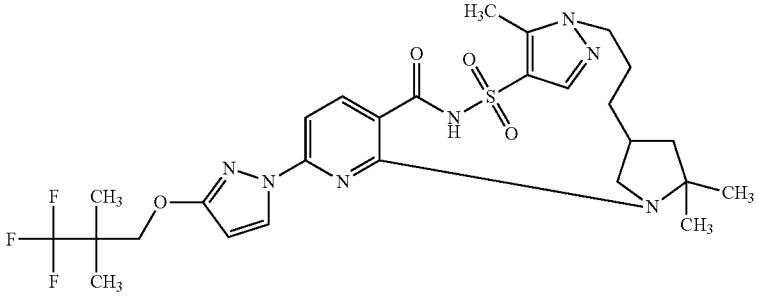 [SMILES: Cc1c2cnn1CCCC1CN(c3nc(-n4ccc(OCC(C)(C)C(F)(F)F)n4)ccc3C(=O)NS2(=O)=O)C(C)(C)C1] | ++ | +++ |
| 281 | 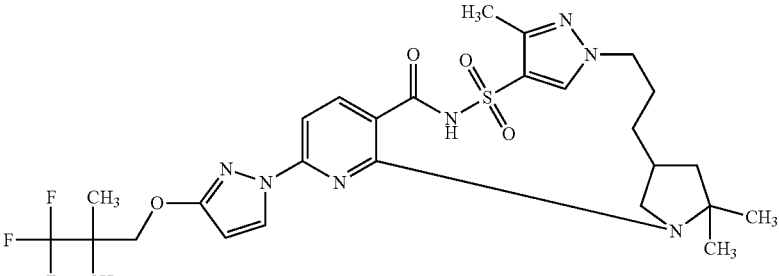 | + | ++ |
| 282 | 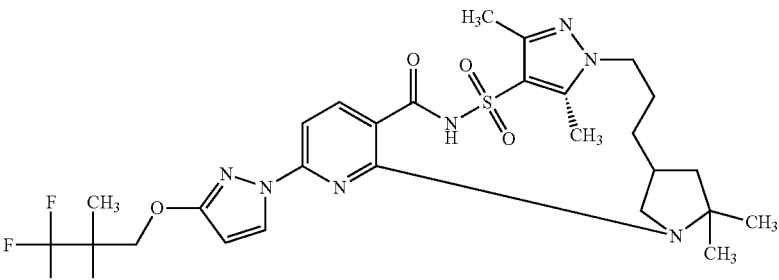 | + | + |
| 283 | 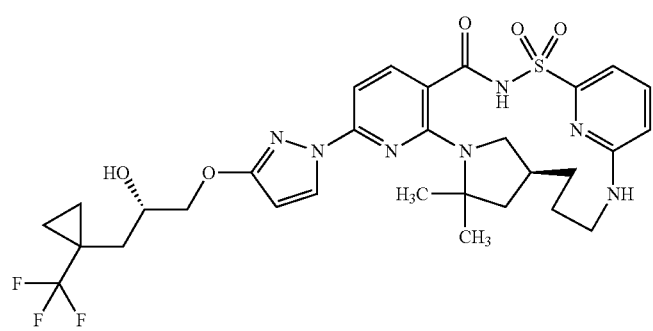 [SMILES: CC1(C)C[C@@H]2CCCNc3cccc(n3)S(=O)(=O)NC(=O)c3ccc(-n4ccc(OC[C@@H](O)CC5(C(F)(F)F)CC5)n4)nc3N1C2] | +++ | +++ |
| 284 | 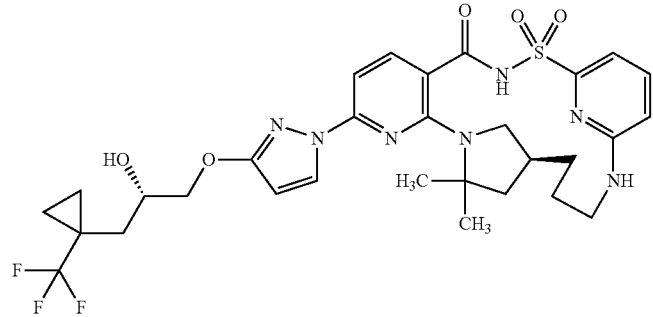 [SMILES: CC1(C)C[C@@H]2CCCNc3cccc(n3)S(=O)(=O)NC(=O)c3ccc(-n4ccc(OC[C@@H](O)CC5(C(F)(F)F)CC5)n4)nc3N1C2] | +++ | +++ |

TABLE 5-continued

| Compound No. | Molecule | Max. Activity | EC50 |
|---|---|---|---|
| 285 | | + | +++ |
| 286 | | + | +++ |
| 287 | | ++ | +++ |
| 288 | | + | ++ |
| 289 | | ++ | +++ |

TABLE 5-continued

| Compound No. | Molecule | Max. Activity | EC50 |
|---|---|---|---|
| 290 | | + | + |
| 291 | | ++ | +++ |
| 292 | | +++ | +++ |
| 293 | | +++ | +++ |
| 294 | | +++ | ++ |

TABLE 5-continued

| Compound No. | Molecule | Max. Activity | EC50 |
|---|---|---|---|
| 295 | | ++ | +++ |
| 296 | | +++ | +++ |
| 297 | | +++ | +++ |
| 298 | | +++ | +++ |

TABLE 5-continued

| Compound No. | Molecule | Max. Activity | EC50 |
|---|---|---|---|
| 299 | | ND | ND |
| 300 | | +++ | +++ |
| 301 | | +++ | +++ |
| 302 | | + | + |
| 303 | | +++ | +++ |

TABLE 5-continued

| Compound No. | Molecule | Max. Activity | EC50 |
|---|---|---|---|
| 304 | | +++ | +++ |
| 305 | | + | + |
| 306 | | +++ | +++ |
| 307 | | + | + |

TABLE 5-continued

| Compound No. | Molecule | Max. Activity | EC50 |
|---|---|---|---|
| 308 | | + | +++ |
| 309 | | +++ | +++ |

OTHER EMBODIMENTS

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A method of treating cystic fibrosis comprising administering to a patient in need thereof a compound of Formula I:

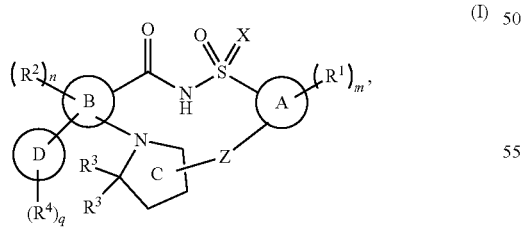

(I)

a pharmaceutically acceptable salt thereof, or a deuterated derivative of any of the foregoing, wherein:
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
X is O, NH, or an N(C1-C4 alkyl);
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups; wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1, 2, 3 or 4; and

Z is a divalent linker of formula $(L)_r$, wherein:
r is 1, 2, 3, 4, 5, or 6;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen, halogens, $C_1$-$C_2$ haloalkyl groups, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

2. The method of claim 1, wherein the compound of Formula (I) is a compound of Formula II-A or II-B:

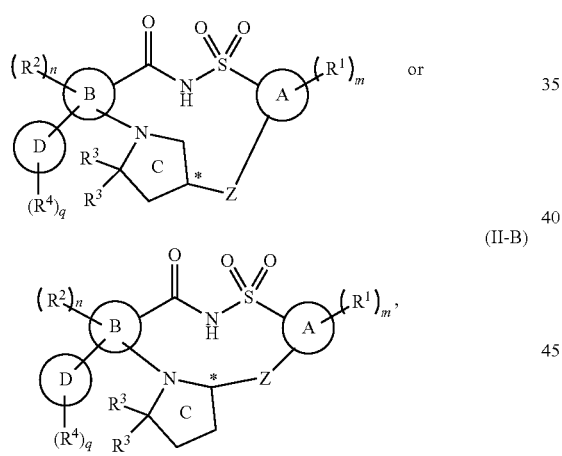

a pharmaceutically acceptable salt thereof, or a deuterated derivative of any of the foregoing, wherein:
the carbon denoted by * has S-stereochemistry or R-stereochemistry;
Ring A is a phenyl, a 5-membered heteroaryl ring, or a 6-membered heteroaryl ring;
Ring B is a pyridinyl ring;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;
each $R^3$ is methyl;
each $R^4$ is independently chosen from halogens, a hydroxyl group, an oxo group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;
q is 1, 2, 3, or 4;
Z is a divalent linker of formula $(L)_r$, wherein:
r is 1, 2, 3, 4, 5, or 6;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen, halogens, $C_1$-$C_2$ alkyl groups, $C_1$-$C_2$ haloalkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

3. The method of claim 1, wherein the compound of Formula I is a compound of Formula III-A or III-B:

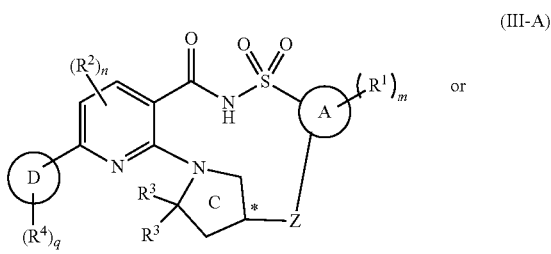

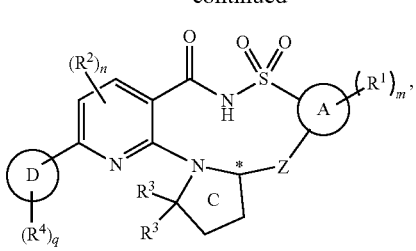

(III-B)

a pharmaceutically acceptable salt thereof, or a deuterated derivative of any of the foregoing, wherein:
the carbon denoted by * has S-stereochemistry or R-stereochemistry;
Ring A is a phenyl, a 5-membered heteroaryl ring, or a 6-membered heteroaryl ring;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;
q is 1 or 2;
Z is a divalent linker of formula (L) r, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

4. The method of claim 1, wherein the compound of Formula I is a compound of Formula IV-A:

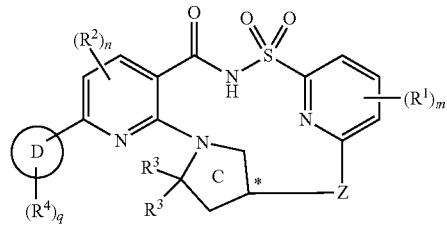

(IV-A)

a pharmaceutically acceptable salt thereof, or a deuterated derivative of any of the foregoing, wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and R⁷ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;

Z is a divalent linker of formula $(L)_r$, wherein:
r is 3, 4, or 5;
each L is independently chosen from $C(R^8)(R^9)$ groups, —O—, and —$NR^b$— groups, wherein a heteroatom in Z is not bonded to another heteroatom in Z, wherein:
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

5. The method of claim 1, wherein the compound of Formula I is a compound of Formula IV-B:

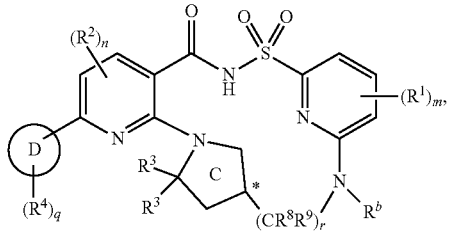

(IV-B)

a pharmaceutically acceptable salt thereof, or a deuterated derivative of any of the foregoing, wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and $-(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in $-(Y)_k$-$R^7$ is not bonded to another heteroatom in $-(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and
each $R^a$ is independently chosen from hydrogen and $C_1$-$C_2$ alkyl groups; and
$R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;
r is 3 or 4;
each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and
each $R^b$ is independently chosen from hydrogen and $C_1$-$C_2$ alkyl groups.

6. The method of claim 1, wherein the compound of Formula I is a compound of Formula IV-C:

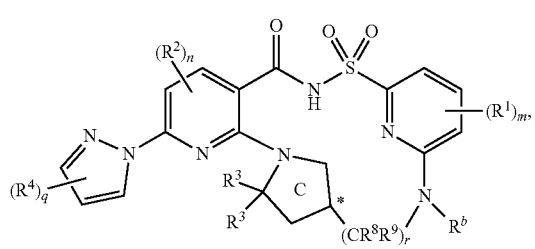

(IV-C)

a pharmaceutically acceptable salt thereof, or a deuterated derivative of any of the foregoing, wherein:
the carbon denoted by * has S-stereochemistry or R-stereochemistry;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and $-(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in -(Y)$_k$-R$^7$ is not bonded to another heteroatom in -(Y)$_k$-R$^7$, wherein:
  each R$^5$ and R$^6$ is independently chosen from hydrogen, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
  each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
  each R$^a$ is independently chosen from hydrogen and C$_1$-C$_2$ alkyl groups; and
  R$^7$ is chosen from hydrogen, halogens, a cyano group, and C$_3$-C$_{10}$ cycloalkyl groups optionally substituted with one or more groups chosen from C$_1$-C$_2$ alkyl groups, C$_1$-C$_2$ haloalkyl groups, and halogens;
q is 1 or 2;
r is 3 or 4;
  each R$^8$ and R$^9$ is independently chosen from hydrogen, halogens, C$_1$-C$_2$ alkyl groups, a hydroxyl group, C$_1$-C$_2$ alkoxyl groups, and C$_1$-C$_2$ haloalkoxyl groups; and
  each R$^b$ is independently chosen from hydrogen and C$_1$-C$_2$ alkyl groups.

7. The method of claim 1, wherein the compound of Formula I is a compound of Formula V-A:

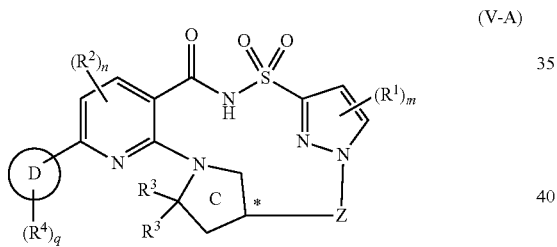

(V-A)

a pharmaceutically acceptable salt thereof, or a deuterated derivative of any of the foregoing, wherein:
  the carbon denoted by * has S-stereochemistry or R-stereochemistry;
  Ring D is a phenyl ring, a 5-membered heterocyclyl ring, a 6-membered heterocyclyl ring, a 5-membered heteroaryl ring, or a 6-membered heteroaryl ring;
  each R$^1$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
  m is 0, 1, 2, 3, or 4;
  each R$^2$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
  n is 0, 1, or 2;
  each R$^3$ is methyl;
  each R$^4$ is independently chosen from halogens, an oxo group, a hydroxyl group, a cyano group, and -(Y)$_k$-R$^7$ groups, or optionally two R$^4$, together with the atom(s) they are attached to, form a 5-6 membered cycloalkyl or heterocyclyl ring that is optionally and independently substituted with one or more groups chosen from halogens, C$_1$-C$_2$ alkyl groups, haloalkyl groups, a hydroxyl group, C$_1$-C$_2$ alkoxyl groups, and C$_1$-C$_2$ haloalkoxyl groups, wherein:
k is 0, 1, 2, 3, 4, 5, or 6;
  each Y is independently chosen from C(R$^5$)(R$^6$) groups, —O—, and —NR$^a$— groups, wherein a heteroatom in -(Y)$_k$-R$^7$ is not bonded to another heteroatom in -(Y)$_k$-R$^7$, wherein:
    each R$^5$ and R$^6$ is independently chosen from hydrogen, halogens, a hydroxyl group, C$_1$-C$_4$ alkyl groups, and C$_{3-5}$ cycloalkyl groups, or R$^5$ and R$^6$ on the same carbon together form a C$_{3-5}$ cycloalkyl group or oxo;
    each of R$^5$ and R$^6$ is optionally independently substituted with one or more groups chosen from C$_1$-C$_2$ alkyl groups, C$_1$-C$_2$ haloalkyl groups, halogens, a hydroxyl group, C$_1$-C$_2$ alkoxyl groups, and C$_1$-C$_2$ haloalkoxyl groups; and
    each R$^a$ is independently chosen from hydrogen and C$_1$-C$_2$ alkyl groups; and
  R$^7$ is chosen from hydrogen, halogens, a cyano group, and C$_3$-C$_{10}$ cycloalkyl groups optionally substituted with one or more groups chosen from C$_1$-C$_2$ alkyl groups, C$_1$-C$_2$ haloalkyl groups, and halogens;
q is 1 or 2;
Z is a divalent linker of formula (L)$_r$, wherein:
  r is 3, 4, or 5;
  each L is independently chosen from C(R$^8$)(R$^9$) groups, —O—, and —NR$^b$— groups, wherein a heteroatom in Z is not bonded to another heteroatom in Z, wherein:
    each R$^8$ and R$^9$ is independently chosen from hydrogen, halogens, C$_1$-C$_2$ alkyl groups, a hydroxyl group, C$_1$-C$_2$ alkoxyl groups, and C$_1$-C$_2$ haloalkoxyl groups; and
    each R$^b$ is independently chosen from hydrogen and C$_1$-C$_2$ alkyl groups.

8. The method of claim 1, wherein the compound of Formula I is a compound of Formula V-B:

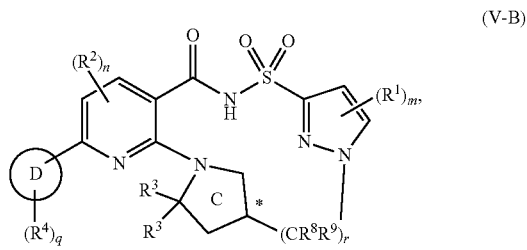

(V-B)

a pharmaceutically acceptable salt thereof, or a deuterated derivative of any of the foregoing, wherein:
  the carbon denoted by * has S-stereochemistry or R-stereochemistry;
  Ring D is a phenyl ring, a 5-membered heterocyclyl ring, a 6-membered heterocyclyl ring, a 5-membered heteroaryl ring, or a 6-membered heteroaryl ring;
  each R$^1$ is independently chosen from C$_1$-C$_2$ alkyl groups, C$_1$-C$_2$ alkoxyl groups, C$_1$-C$_2$ haloalkyl groups, C$_1$-C$_2$ haloalkoxyl groups, halogens, a cyano group, and a hydroxyl group;
  m is 0, 1, 2, 3, or 4;

each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and -(Y)$_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —NR$^a$— groups, wherein a heteroatom in -(Y)$_k$-$R^7$ is not bonded to another heteroatom in -(Y)$_k$-$R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;

r is 3, 4, or 5; and each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups.

9. The method of claim 1, wherein the compound of Formula I is a compound of Formula VI-A or VI-B:

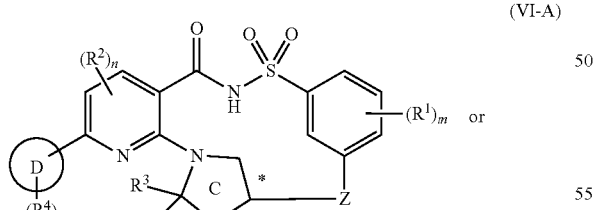

(VI-A)

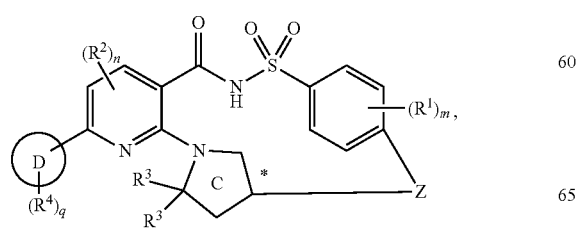

(VI-B)

a pharmaceutically acceptable salt thereof, or a deuterated derivative of any of the foregoing, wherein:

the carbon denoted by * has S-stereochemistry or R-stereochemistry;

Ring D is a phenyl ring, a 5-membered heterocyclyl ring, a 6-membered heterocyclyl ring, a 5-membered heteroaryl ring, or a 6-membered heteroaryl ring;

each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

m is 0, 1, 2, 3, or 4;

each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;

n is 0, 1, or 2;

each $R^3$ is methyl;

each $R^4$ is independently chosen from halogens, an oxo group, a hydroxyl group, a cyano group, and -(Y)$_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:

k is 0, 1, 2, 3, 4, 5, or 6;

each Y is independently chosen from $C(R^5)(R^6)$ groups, —O—, and —NR$^a$— groups, wherein a heteroatom in -(Y)$_k$-$R^7$ is not bonded to another heteroatom in -(Y)$_k$-$R^7$, wherein:

each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;

each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;

Z is a divalent linker of formula (L) r, wherein:

r is 3, 4, or 5;

each L is independently chosen from $C(R^8)(R^9)$ groups, —O—, and —NR$^b$— groups, wherein a heteroatom in Z is not bonded to another heteroatom in Z, wherein:

each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups; and each $R^b$ is independently chosen from hydrogen and $C_1$-$C_2$ alkyl groups.

10. The method of claim 1, wherein the compound of Formula I is a compound of Formula VI-C or VI-D:

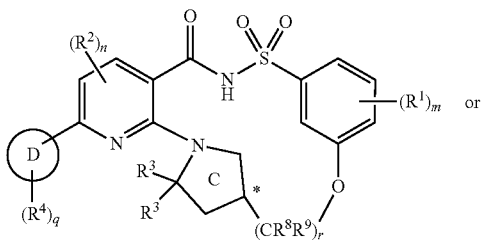
(VI-C)

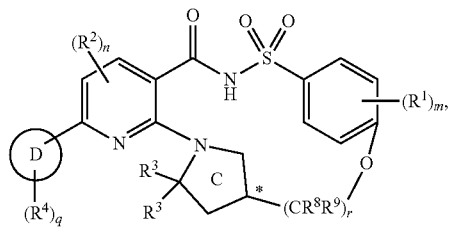
(VI-D)

a pharmaceutically acceptable salt thereof, or a deuterated derivative of any of the foregoing, wherein:
the carbon denoted by * has S-stereochemistry or R-stereochemistry;
Ring D is a phenyl ring, a 5-membered heterocyclyl ring, a 6-membered heterocyclyl ring, a 5-membered heteroaryl ring, or a 6-membered heteroaryl ring;
each $R^1$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
m is 0, 1, 2, 3, or 4;
each $R^2$ is independently chosen from $C_1$-$C_2$ alkyl groups, $C_1$-$C_2$ alkoxyl groups, $C_1$-$C_2$ haloalkyl groups, $C_1$-$C_2$ haloalkoxyl groups, halogens, a cyano group, and a hydroxyl group;
n is 0, 1, or 2;
each $R^3$ is methyl;
each $R^4$ is independently chosen from halogens, an oxo group, a hydroxyl group, a cyano group, and -$(Y)_k$-$R^7$ groups, or optionally two $R^4$, together with the atom(s) they are attached to, form a 5-6 membered cycloalkyl or heterocyclyl ring that is optionally and independently substituted with one or more groups chosen from halogens, $C_1$-$C_2$ alkyl groups, haloalkyl groups, a hydroxyl group, $C_1$-$C_2$ alkoxyl groups, and $C_1$-$C_2$ haloalkoxyl groups, wherein:
k is 0, 1, 2, 3, 4, 5, or 6;
each Y is independently chosen from $C(R^5)(R^6)$ groups, —O—, and —$NR^a$— groups, wherein a heteroatom in -$(Y)_k$-$R^7$ is not bonded to another heteroatom in -$(Y)_k$-$R^7$, wherein:
each $R^5$ and $R^6$ is independently chosen from hydrogen, halogens, a hydroxyl group, $C_1$-$C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1$-$C_2$ alkyl groups, $C_1$-$C_2$ haloalkyl groups, halogens, a hydroxyl group, $C_1$-$C_2$ alkoxyl groups, and $C_1$-$C_2$ haloalkoxyl groups; and each $R^a$ is independently chosen from hydrogen and $C_1$-$C_2$ alkyl groups; and $R^7$ is chosen from hydrogen, halogens, a cyano group, and $C_3$-$C_{10}$ cycloalkyl groups optionally substituted with one or more groups chosen from $C_1$-$C_2$ alkyl groups, $C_1$-$C_2$ haloalkyl groups, and halogens;

q is 1 or 2;

r is 3 or 4; and each $R^8$ and $R^9$ is independently chosen from hydrogen, halogens, $C_1$-$C_2$ alkyl groups, a hydroxyl group, $C_1$-$C_2$ alkoxyl groups, and $C_1$-$C_2$ haloalkoxyl groups.

11. The method of claim 1, wherein Ring A is a phenyl ring, a pyridyl ring, or a pyrazolyl ring, wherein Ring A is optionally substituted with $(R^1)_m$.

12. The method of claim 1, wherein each $R^1$ is independently chosen from deuterium, $C_1$-$C_2$ alkyl groups, and a hydroxyl group, and m is 0 or 1.

13. The method of claim 1, wherein n is 0.

14. The method of claim 1, wherein Ring D is a 5-membered heteroaryl ring substituted with $(R^4)_q$.

15. The method of claim 1, wherein Ring D is a phenyl ring, pyridinyl ring, pyrazolyl ring, imidazolidinone ring, pyrrolidinone ring, or a pyridinone ring, wherein Ring D is substituted with $(R^4)_q$.

16. The method of claim 1, wherein Ring D is a pyrazolyl ring, or a pyridinone ring, wherein Ring D is substituted with $(R^4)_q$.

17. The method of claim 1, a pharmaceutically acceptable salt thereof, or a deuterated derivative of any of the foregoing, wherein Ring D is a pyrazolyl ring, wherein Ring D is substituted with $(R^4)_q$.

18. The method of claim 1, wherein Ring D is

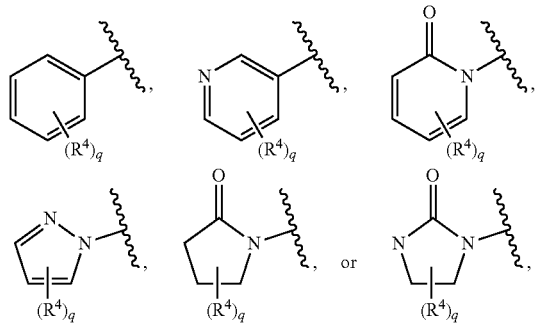

wherein

indicates the point of attachment of Ring D to Ring B.

19. The method of claim 1, wherein Ring D is

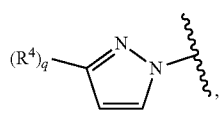

wherein

indicates the point of attachment of Ring D to Ring B.

20. The method of claim 19, wherein each $R^4$ is independently chosen from an oxo group or $-(Y)_k-R^7$ groups, wherein:
k is 0, 1, 2, 3, 4, 5, or 6;
each Y is independently chosen from $C(R^5)(R^6)$ groups, —O—, and —$NR^a$— groups, wherein a heteroatom in $-(Y)_k-R^7$ is not bonded to another heteroatom in $-(Y)_k-R^7$, and wherein:
each $R^5$ and $R^6$ is independently chosen from hydrogen, deuterium, halogens, a hydroxyl group, $C_1-C_4$ alkyl groups, and $C_{3-5}$ cycloalkyl groups, or $R^5$ and $R^6$ on the same carbon together form a $C_{3-5}$ cycloalkyl group;
each of $R^5$ and $R^6$ is optionally independently substituted with one or more groups chosen from $C_1-C_2$ alkyl groups, $C_1-C_2$ haloalkyl groups, halogens, a hydroxyl group, $C_1-C_2$ alkoxyl groups, and $C_1-C_2$ haloalkoxyl groups; and
each $R^a$ is independently chosen from hydrogen and $C_1-C_2$ alkyl groups; and
$R^7$ is chosen from hydrogen, halogens, a cyano group, and $C_3-C_{10}$ cycloalkyl groups optionally substituted with one or more groups chosen from $C_1-C_2$ alkyl groups, $C_1-C_2$ haloalkyl groups, and halogens.

21. The method of claim 19, wherein each $R^4$ is independently chosen from an oxo group or —O-$(Y)_k-R^7$ groups, wherein:
k is 0, 1, 2, 3, 4, or 5;
each Y is independently chosen from $C(R^5)(R^6)$ groups, —O—, and —$NR^a$— groups, wherein a heteroatom in $-(Y)_k-R^7$ is not bonded to another heteroatom in $-(Y)_k-R^7$, and wherein:
each $R^5$ and $R^6$ is independently chosen from hydrogen, deuterium, halogens, a hydroxyl group, $C_1-C_4$ alkyl groups, and $C_{3-5}$ cycloalkyl groups, or $R^5$ and $R^6$ on the same carbon together form a $C_{3-5}$ cycloalkyl group or oxo;
each of $R^5$ and $R^6$ is optionally independently substituted with one or more groups chosen from $C_1-C_2$ alkyl groups, $C_1-C_2$ haloalkyl groups, halogens, a hydroxyl group, $C_1-C_2$ alkoxyl groups, and $C_1-C_2$ haloalkoxyl groups; and
each $R^a$ is independently chosen from hydrogen and $C_1-C_2$ alkyl groups; and
$R^7$ is chosen from hydrogen, halogens, a cyano group, and $C_3-C_{10}$ cycloalkyl groups optionally substituted with one or more groups chosen from $C_1-C_2$ alkyl groups, $C_1-C_2$ haloalkyl groups, and halogens.

22. The method of claim 19, wherein each $R^4$ is independently chosen from

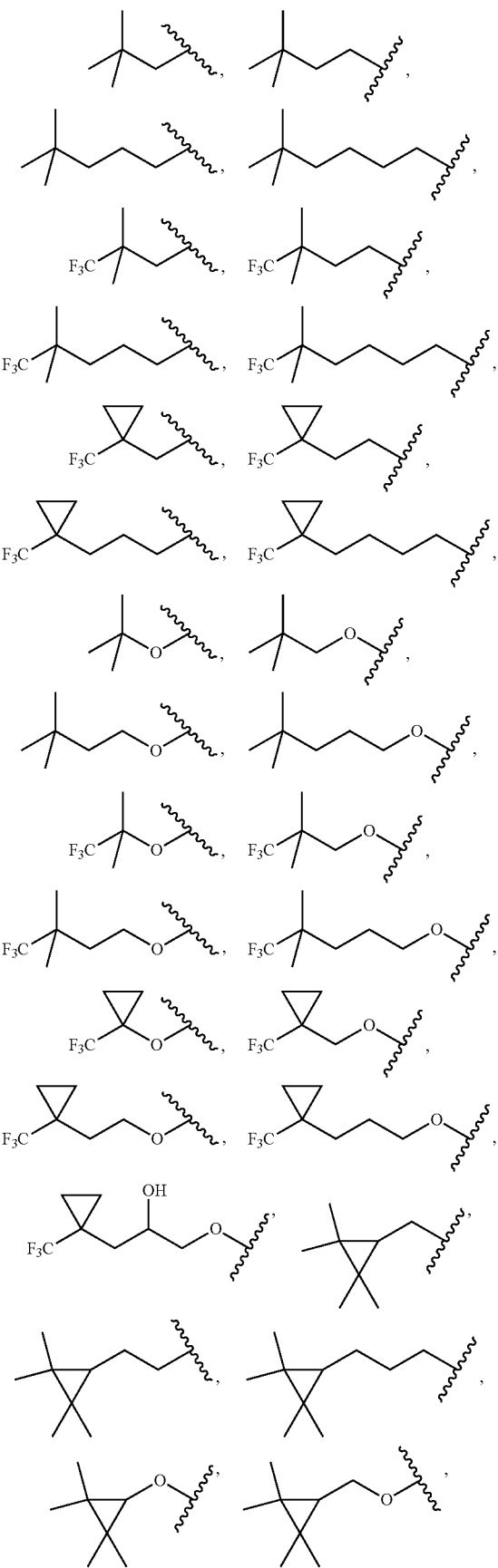

1303
-continued

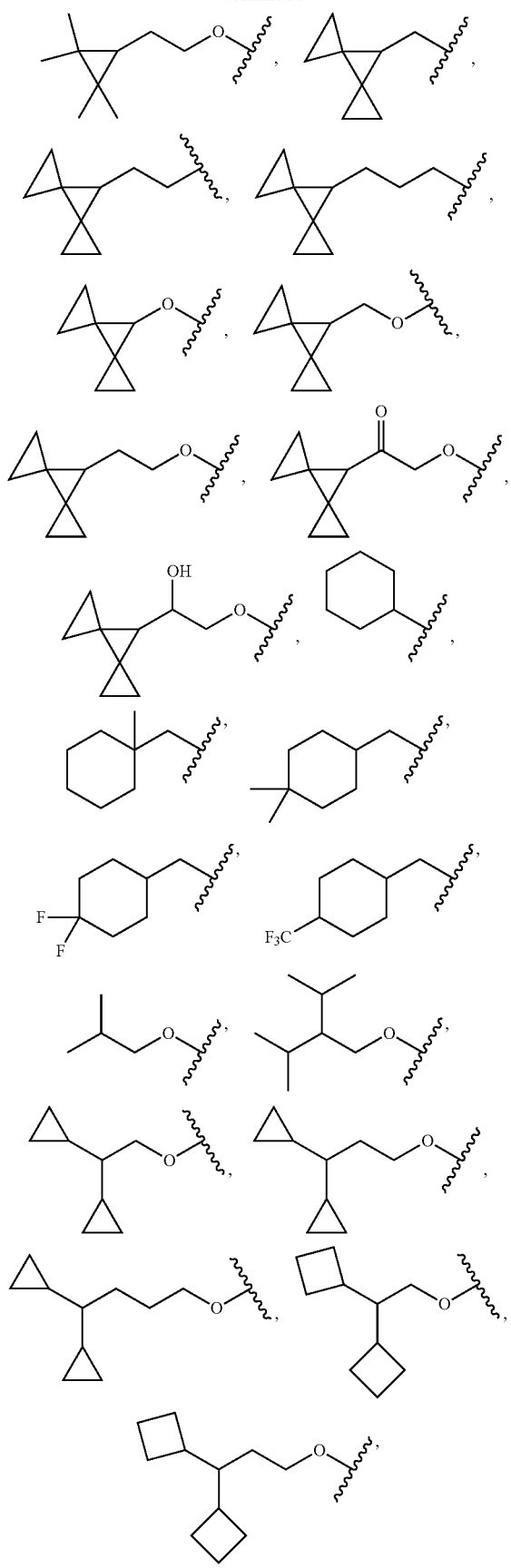

1304
-continued

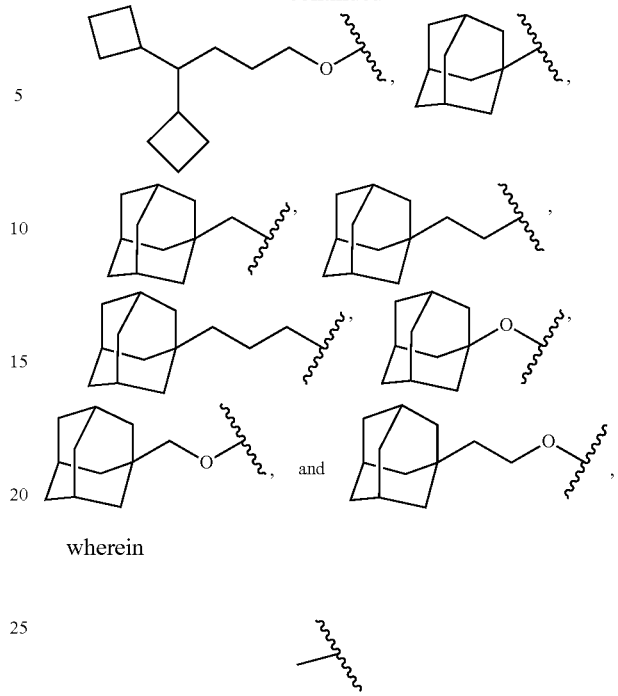

wherein

indicates the point of attachment of R⁴ to Ring D.

23. The method of claim 1, wherein k is 3, 4, 5, or 6.
24. The method of claim 1, wherein q is 1.
25. The method of claim 1, wherein Z is a divalent linker of formula $(L)_r$, wherein:
  r is 3, 4, or 5;
  each L is independently chosen from $C(R^8)(R^9)$ groups, —O—, and —$NR^b$— groups, wherein a heteroatom in Z is not bonded to another heteroatom in Z, and wherein:
    each $R^8$ and $R^9$ is independently chosen from hydrogen and deuterium; and
    each $R^b$ is independently chosen from hydrogen and $C_1$-$C_2$ alkyl groups.
26. The method of claim 1, wherein Z is a divalent linker of formula $(L)_r$, wherein:
  r is 3, 4, or 5;
  each L is independently chosen from $C(R^8)(R^9)$ groups and —$NR^b$— groups, wherein a heteroatom in Z is not bonded to another heteroatom in Z, and:
    each $R^8$ and $R^9$ is independently chosen from hydrogen and deuterium; and
    each $R^b$ is independently chosen from hydrogen and methyl.
27. The method of claim 1, wherein Z is a divalent linker of formula $(L)_r$, wherein:
  r is 3, 4, or 5;
  each L is independently chosen from $C(R^8)(R^9)$ groups and —$NR^b$— groups, wherein a heteroatom in Z is not bonded to another heteroatom in Z, and wherein:
    each $R^8$ and $R^9$ is independently chosen from hydrogen and deuterium; and
    each $R^b$ is hydrogen.
28. The method of claim 1, wherein Z is a divalent linker of formula $(L)_r$, wherein:
  r is 3, 4, or 5;
  each L is independently chosen from $C(R^8)(R^9)$ groups, —O—, and —$NR^b$— groups, wherein a heteroatom in Z is not bonded to another heteroatom in Z, wherein:

each $R^8$ and $R^9$ is hydrogen; and
each $R^b$ is independently chosen from hydrogen and $C_1$-$C_2$ alkyl groups.

29. The method of claim 1, wherein each $R^3$ is independently $CD_3$.

30. The method of claim 5, wherein:
r is 3 or 4;
each $R^8$ and $R^9$ is independently chosen from hydrogen and deuterium; and
each $R^b$ is independently chosen from hydrogen and $C_1$-$C_2$ alkyl groups.

31. The method of claim 5, wherein:
each $R^8$ and $R^9$ is independently chosen from hydrogen and deuterium; and
each $R^b$ is hydrogen.

32. The method of claim 6, wherein each $R^8$ and $R^9$ is independently chosen from hydrogen and deuterium.

33. The method of claim 6, each $R^8$ and $R^9$ is hydrogen.

34. The method of claim 1, wherein the compound is selected from:

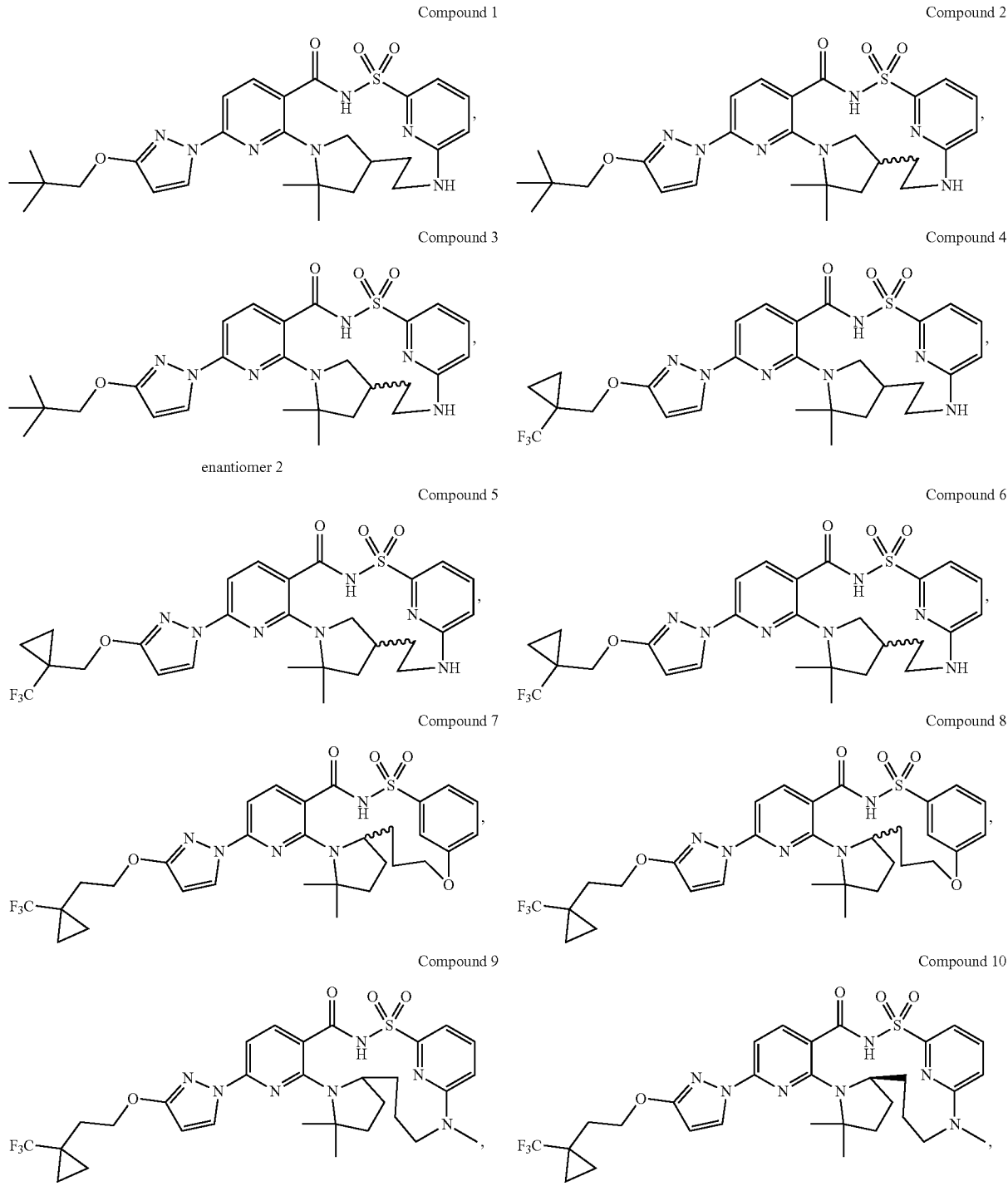

Compound 11
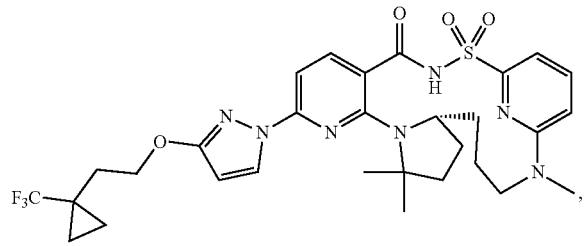
Compound 12
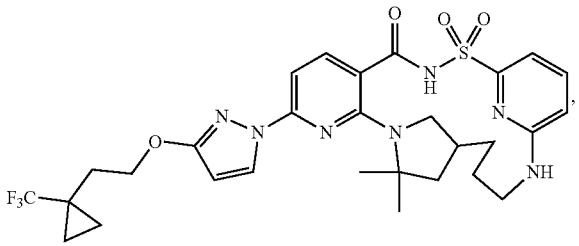
Compound 13
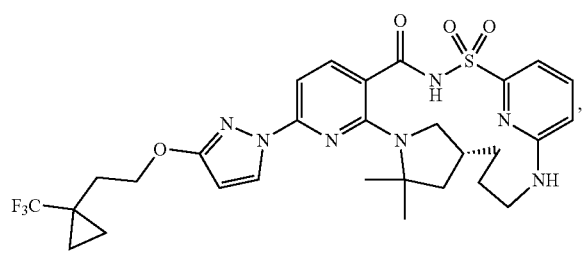
Compound 14
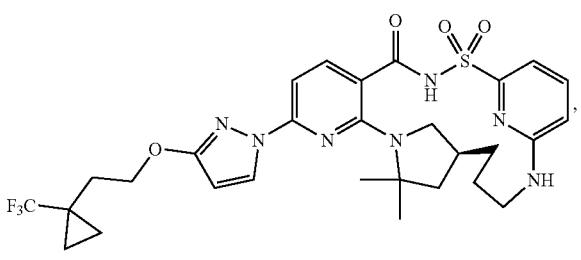
Compound 15
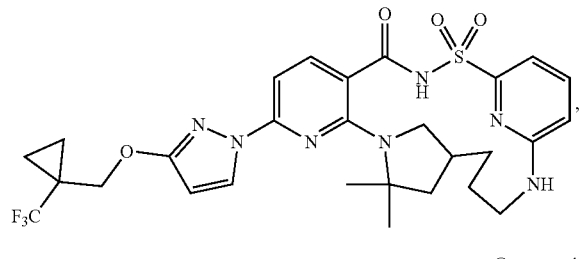
Compound 16
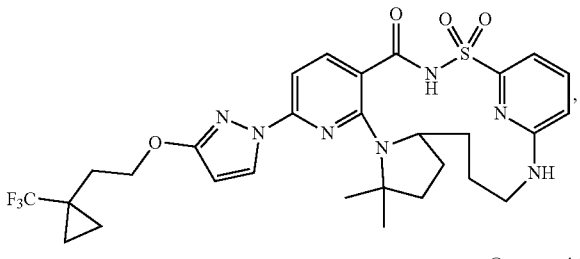
Compound 17
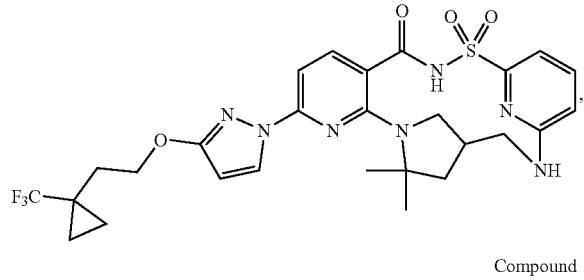
Compound 18
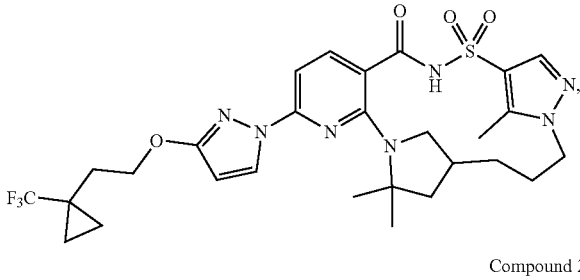
Compound 19
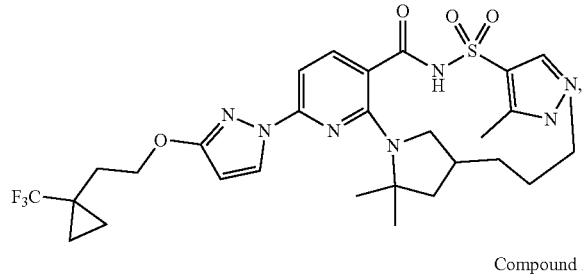
Compound 20
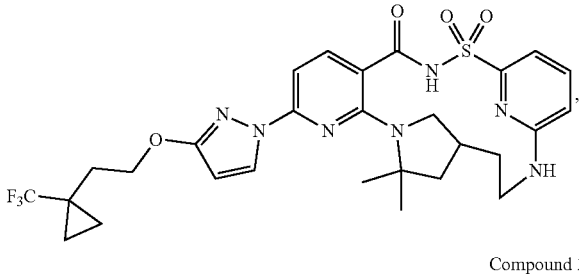
Compound 21
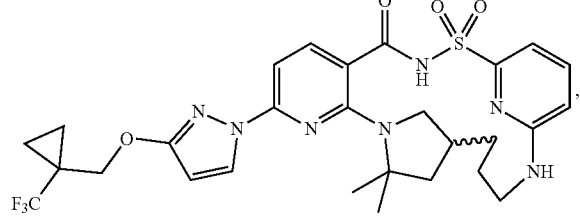
Compound 22

-continued
Compound 23
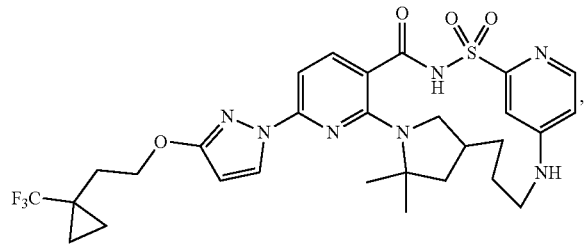
Compound 24
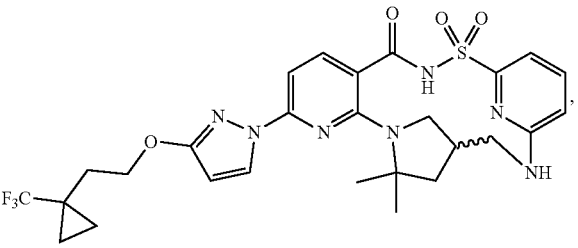
Compound 25
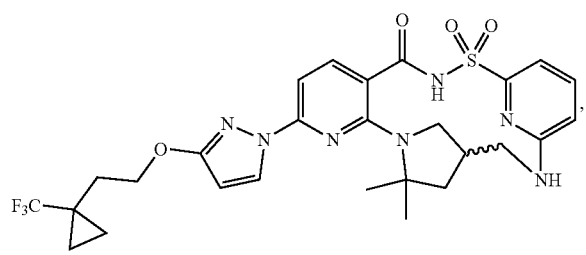
Compound 26
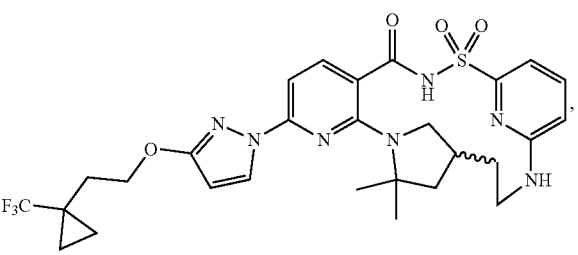
Compound 27
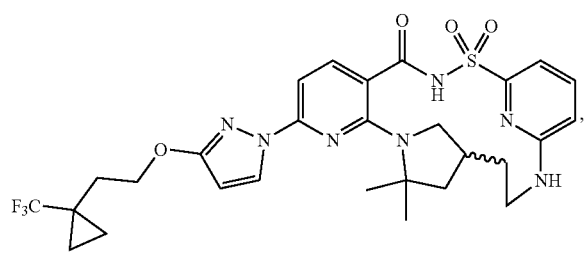
Compound 28
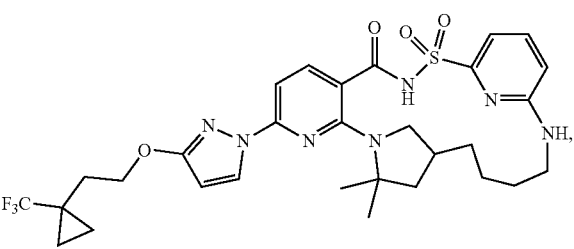
Compound 29
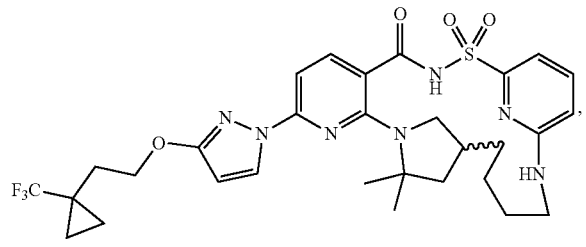
Compound 30
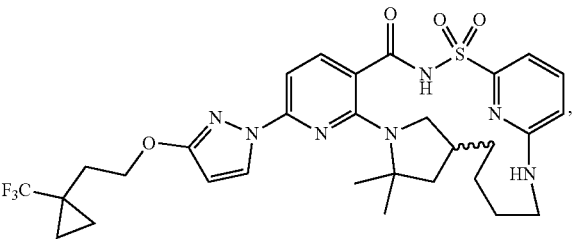
Compound 31
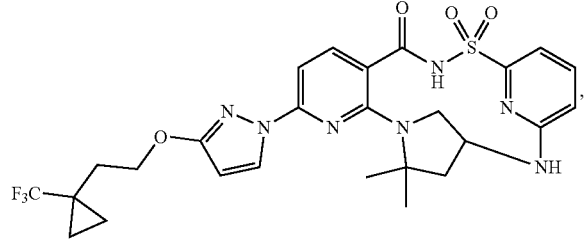
Compound 32
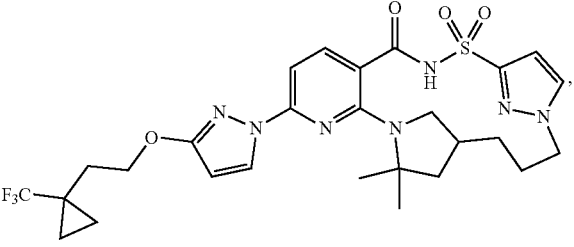
Compound 33
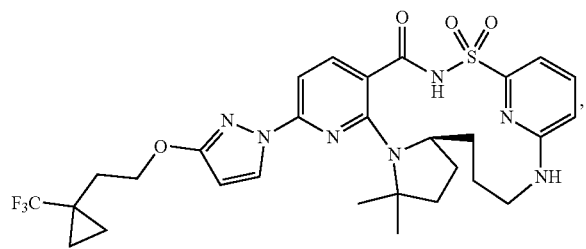
Compound 34
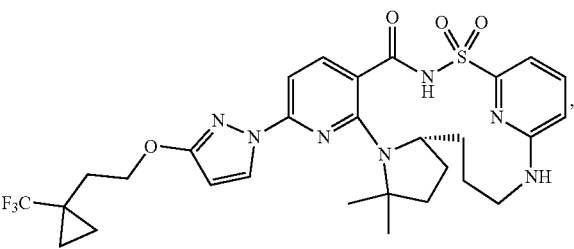

-continued
Compound 35
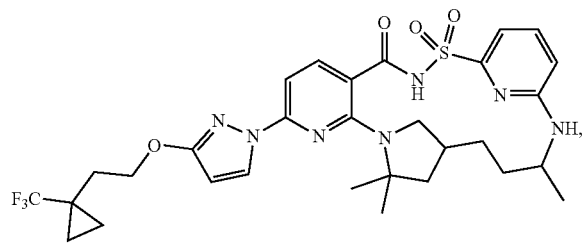
Compound 36
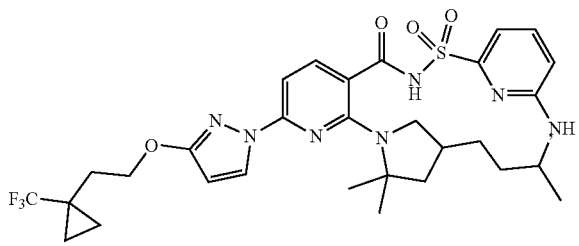
Compound 37
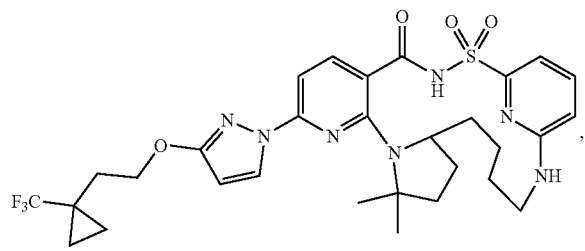
Compound 38
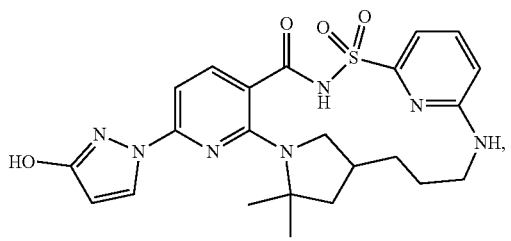
Compound 39
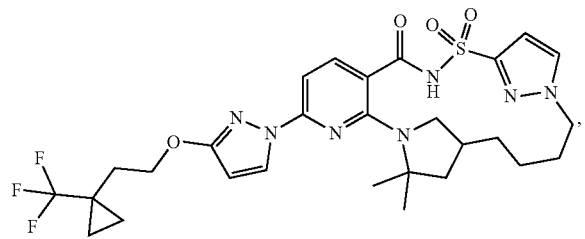
Compound 40
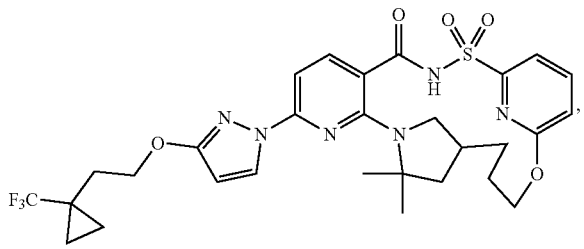
Compound 41
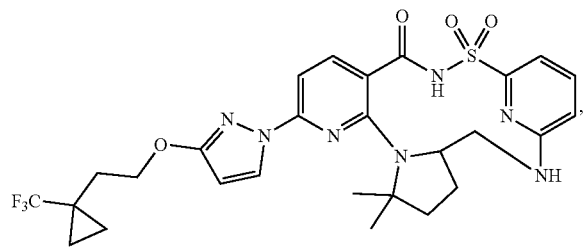
Compound 42
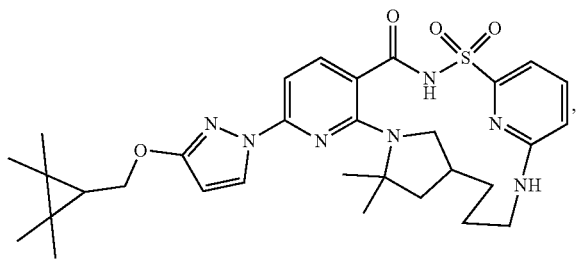
Compound 43
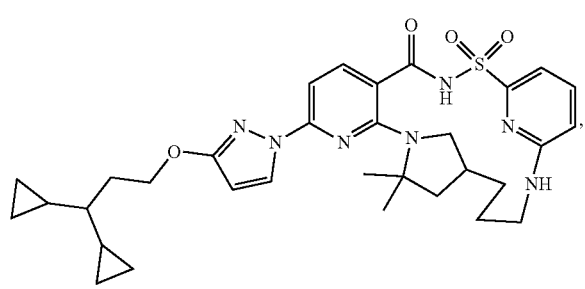
Compound 44
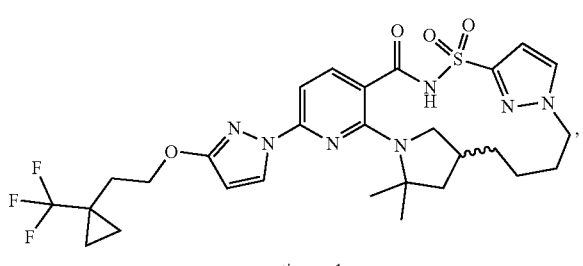
enantiomer 1

-continued
Compound 45
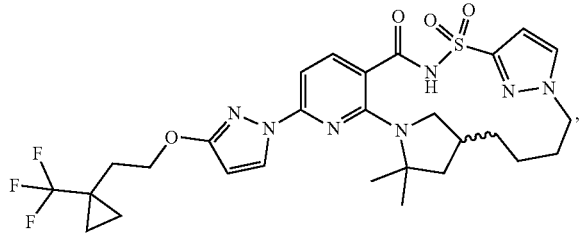
Compound 46
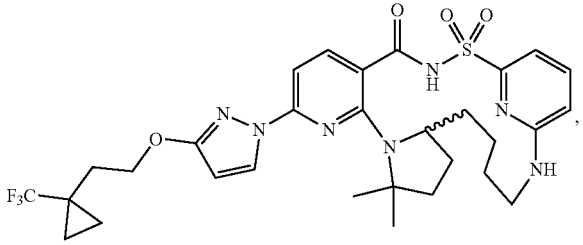
Compound 47
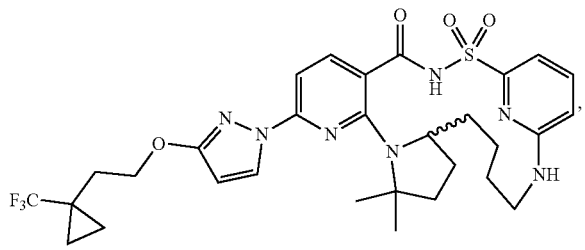
Compound 48
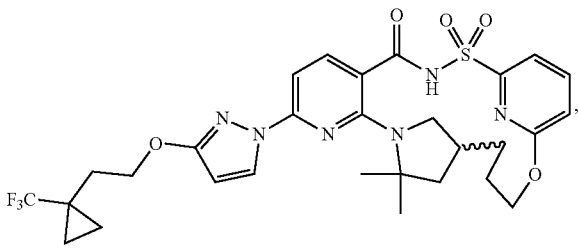
Compound 49
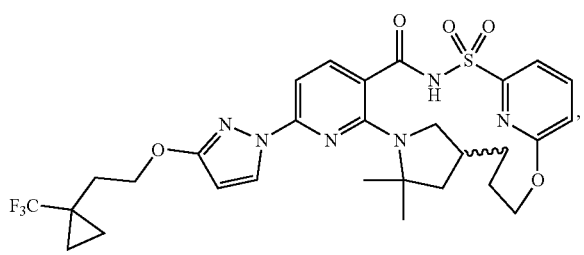
Compound 50
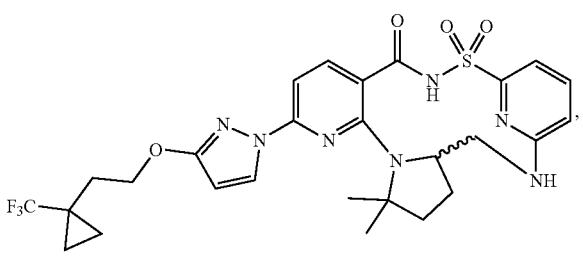
Compound 51
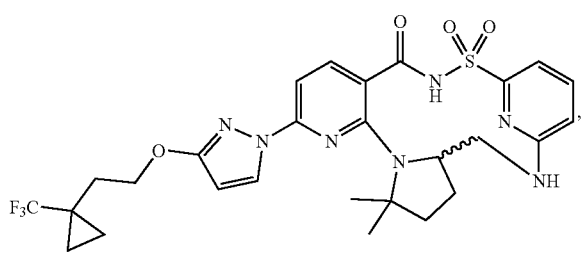
Compound 52
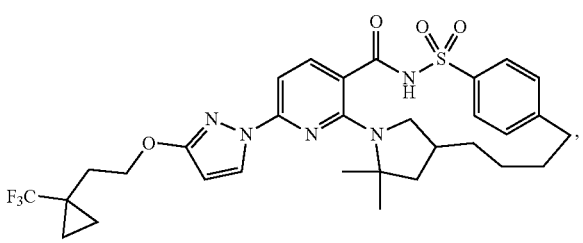
Compound 53
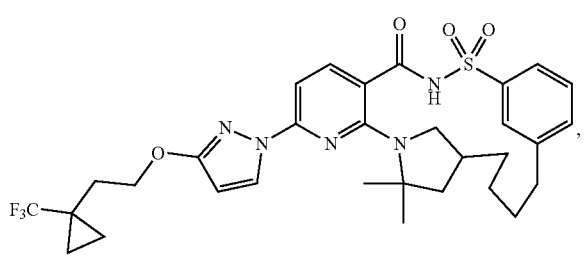
Compound 54
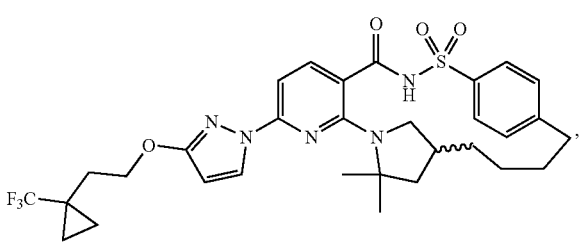
Compound 55
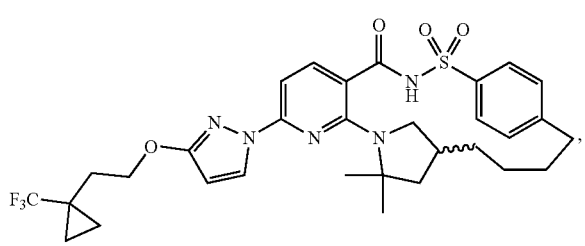
Compound 56
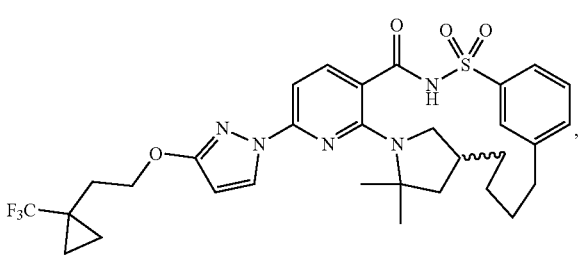

-continued
Compound 57
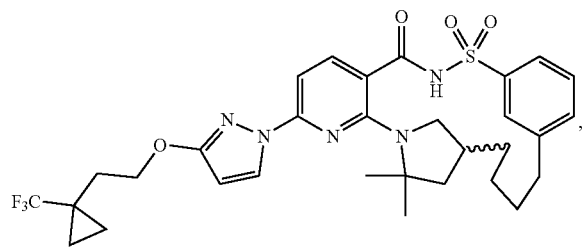
Compound 58
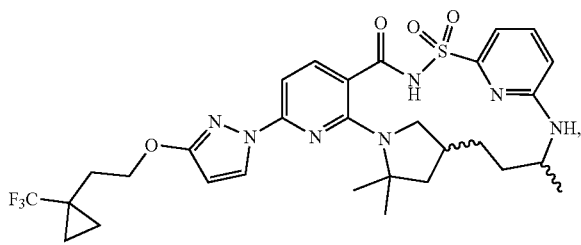
Compound 59
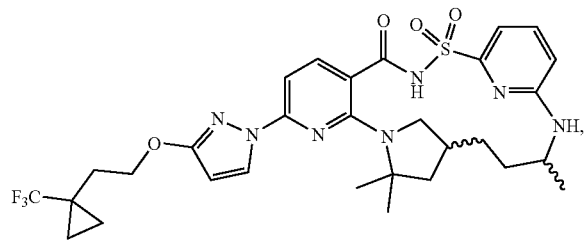
Compound 60
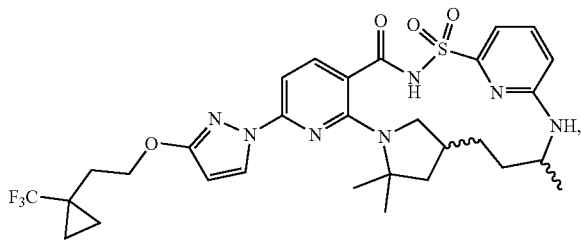
Compound 61
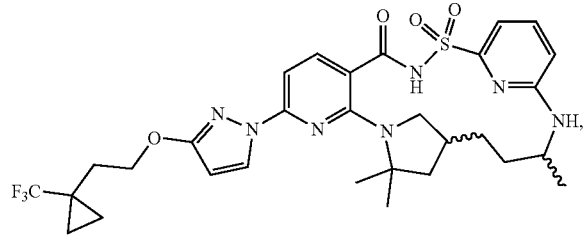
Compound 62
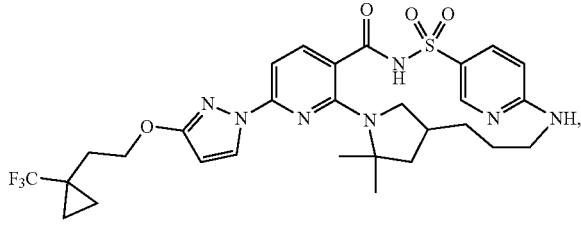
Compound 63
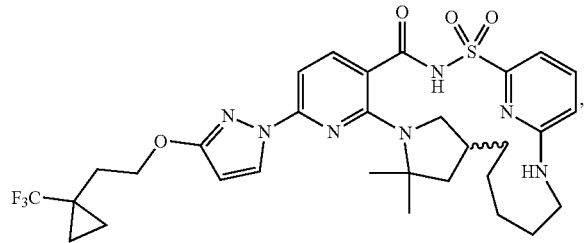
Compound 64
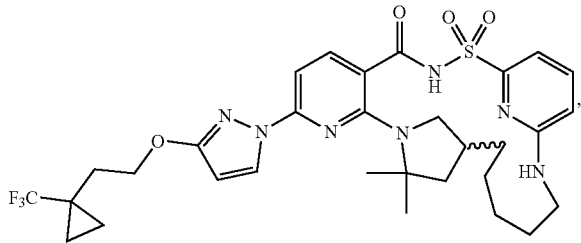
Compound 65
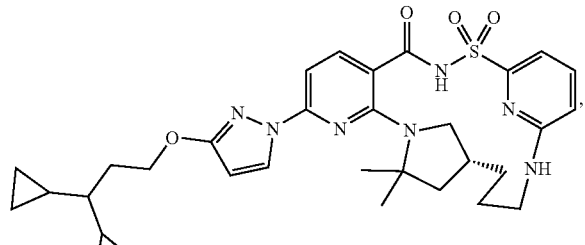
Compound 66
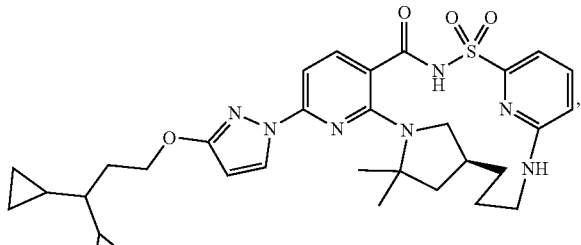
Compound 67
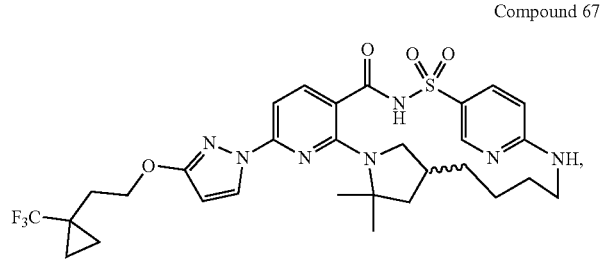
Compound 68
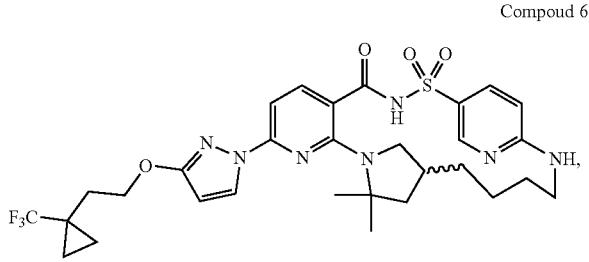

-continued
Compoud 69
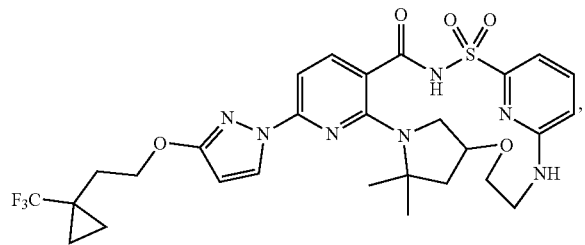
Compound 70
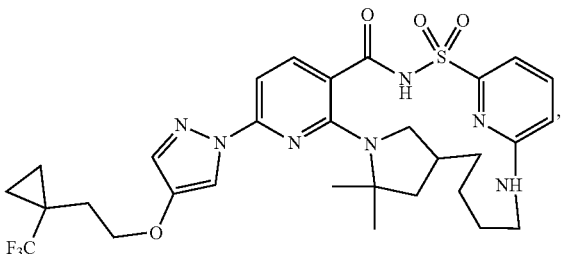
Compound 71
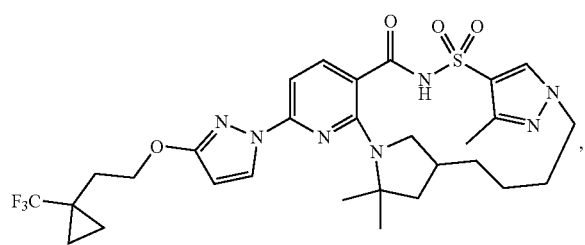
Compound 72
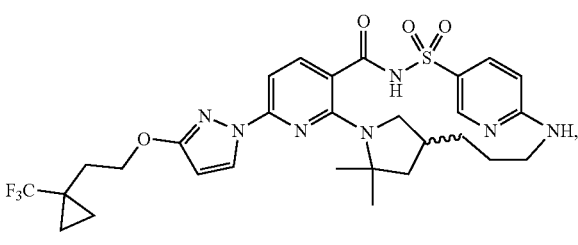
Compound 73
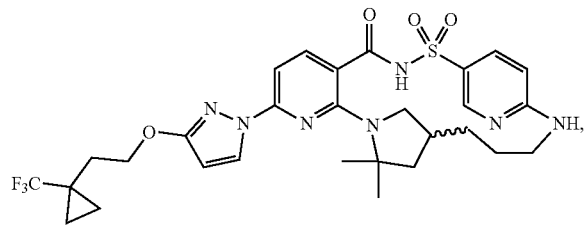
Compound 74
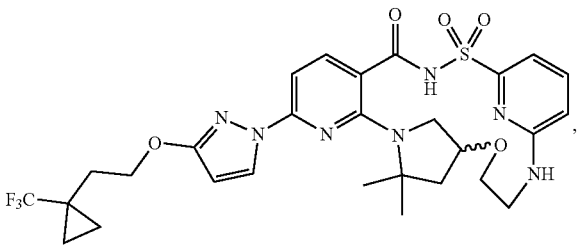
Compound 75
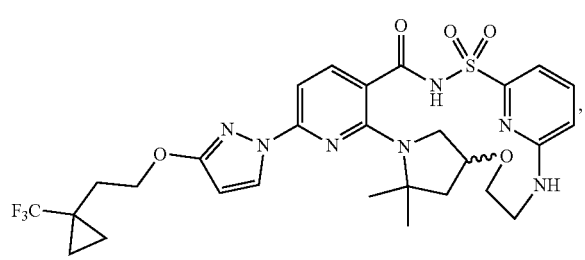
Compound 76
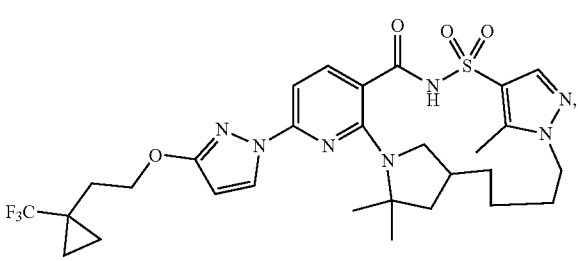
Compound 77
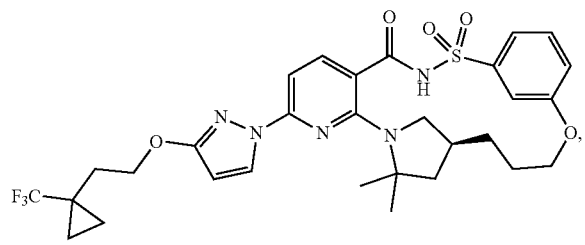
Compound 78
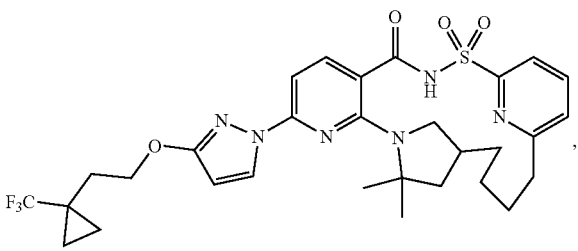
Compound 79
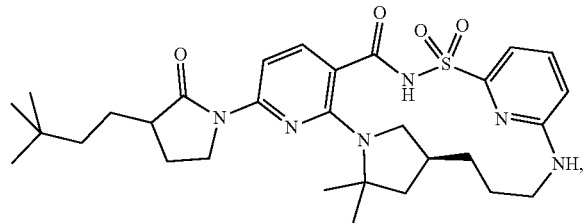
Compound 80
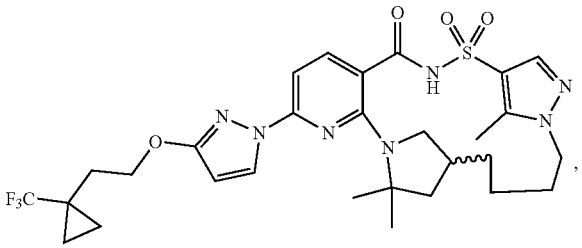

-continued
Compound 81
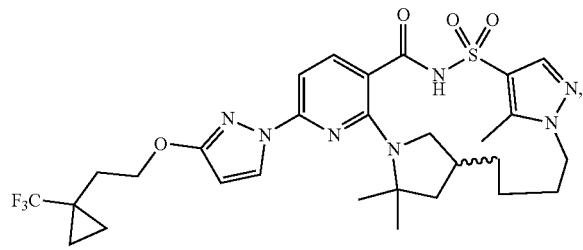
Compound 82
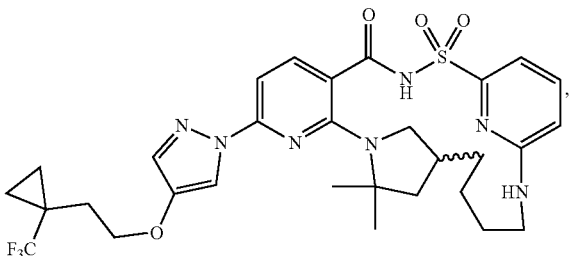
Compound 83
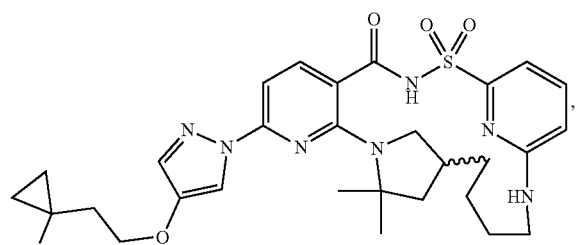
Compound 84
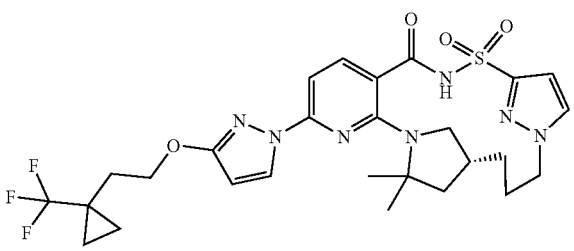
Compound 85
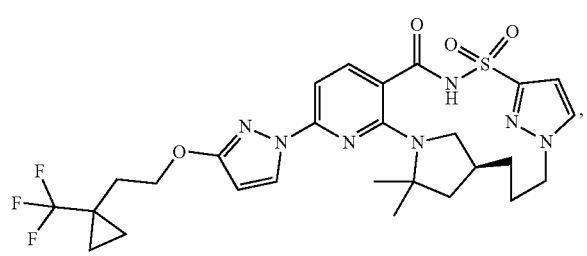
Compound 86
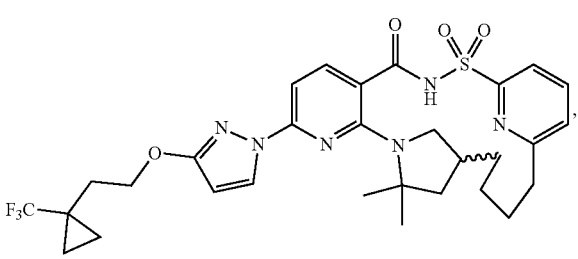
Compound 87
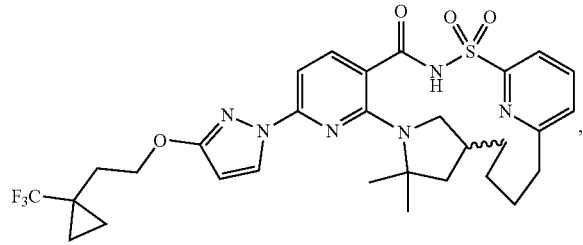
Compound 88
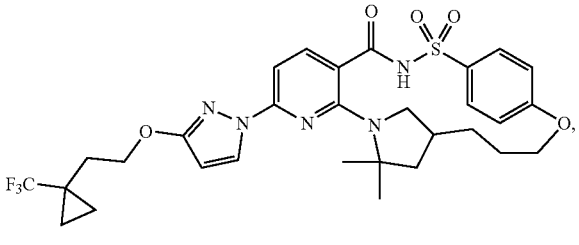
Compound 89
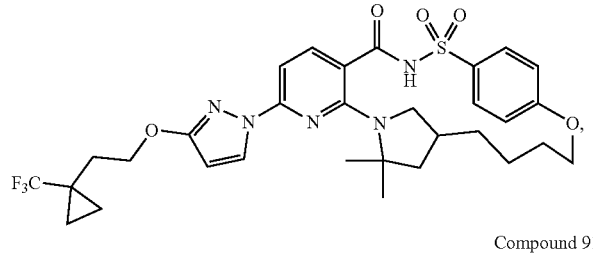
Compound 90
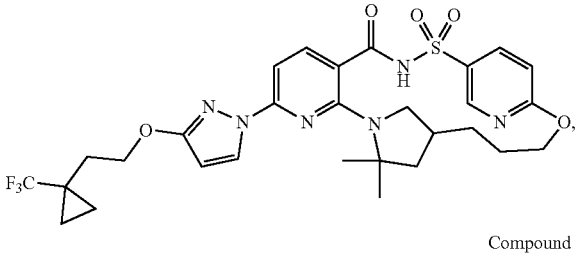
Compound 91
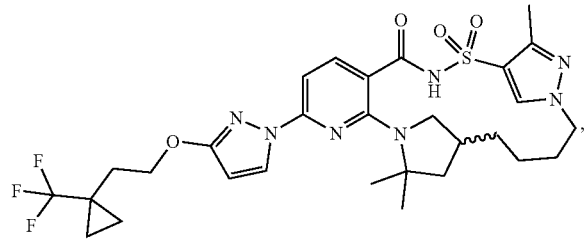
Compound 92
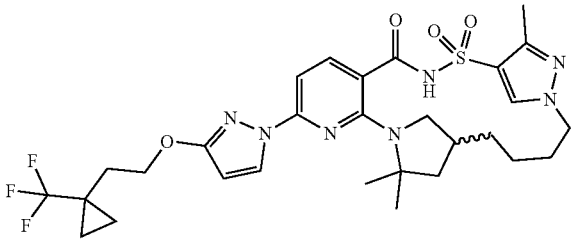

-continued
Compound 93
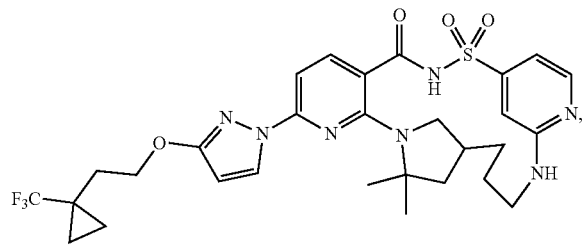
Compound 94
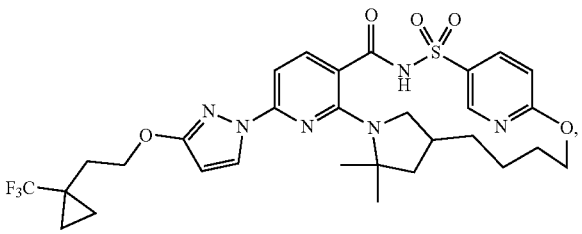
Compound 95
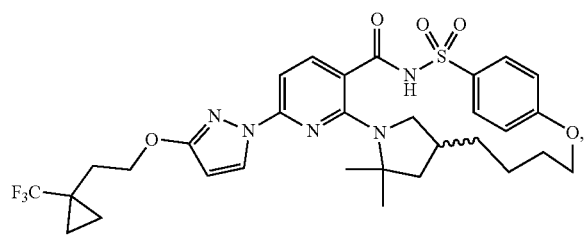
Compound 96
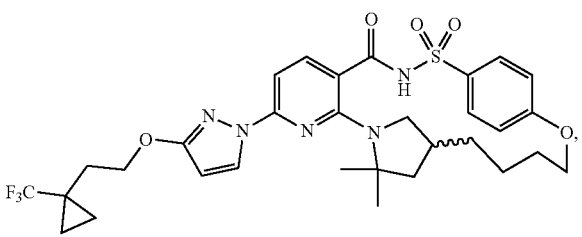
Compound 97
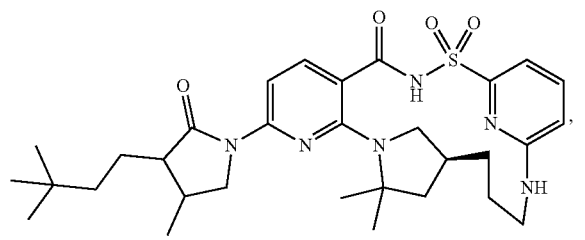
Compound 98
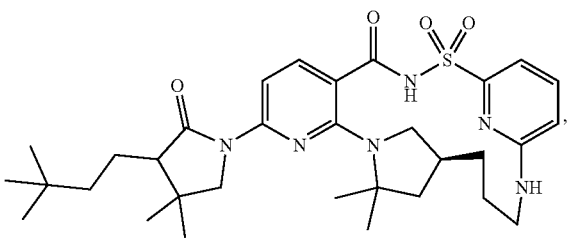
Compound 99
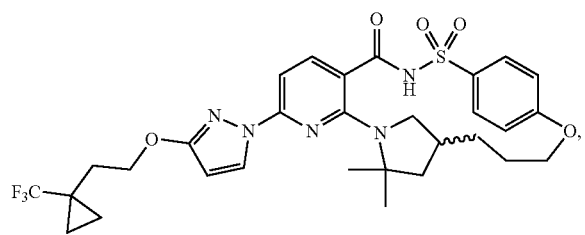
Compound 100
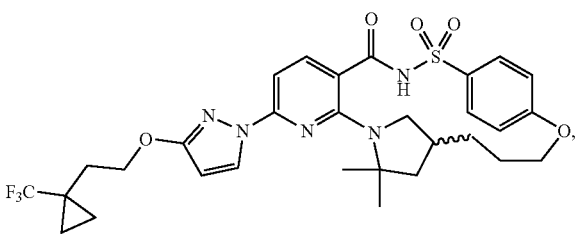
Compound 101
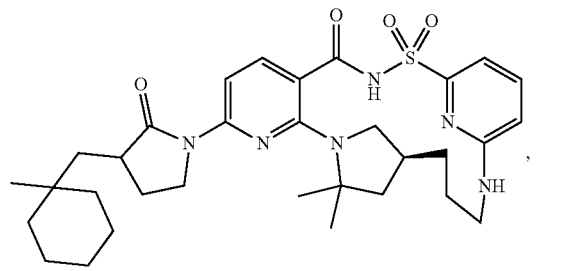
Compound 102
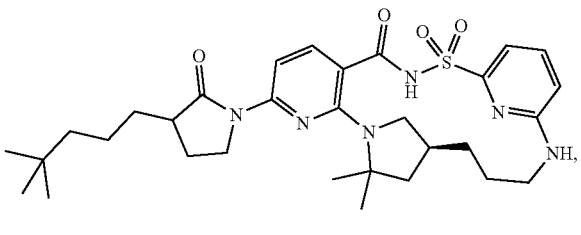
Compound 103
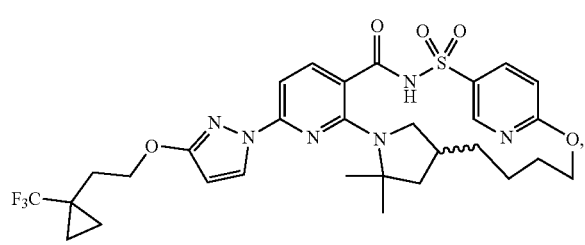
Compound 104
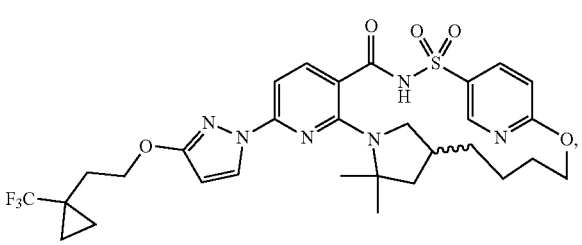

-continued
Compound 105
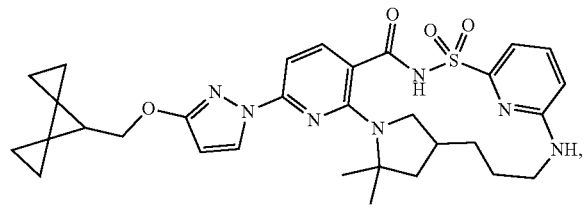
Compound 106
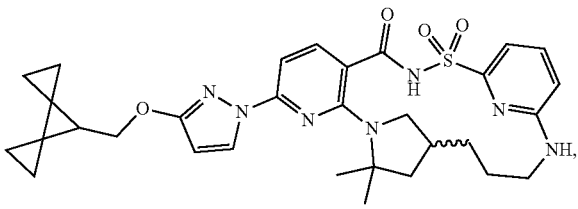
Compound 107
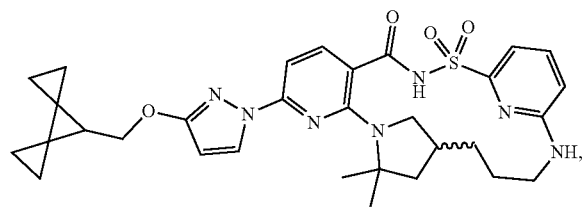
Compound 108
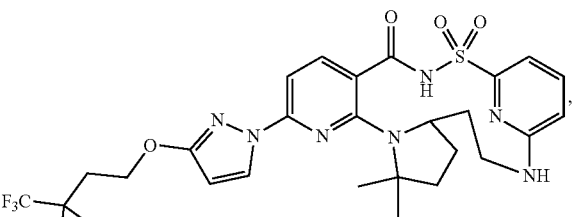
Compound 109
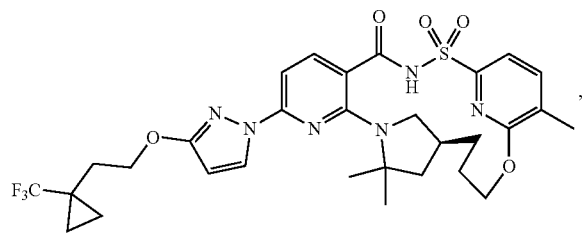
Compound 110
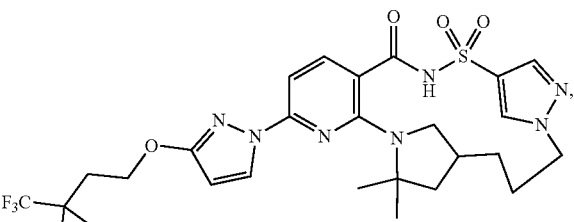
Compound 111
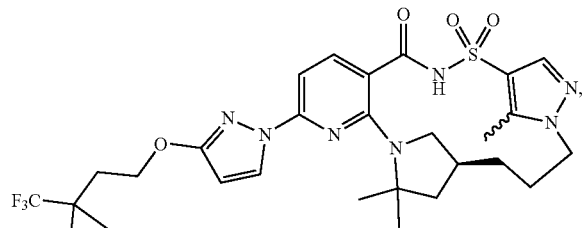
Compound 112
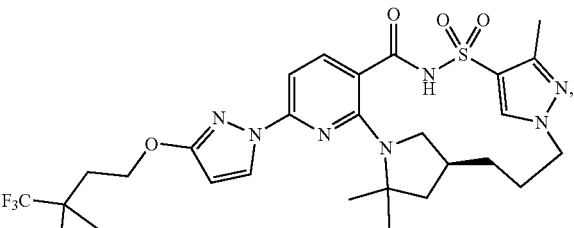
Compound 113
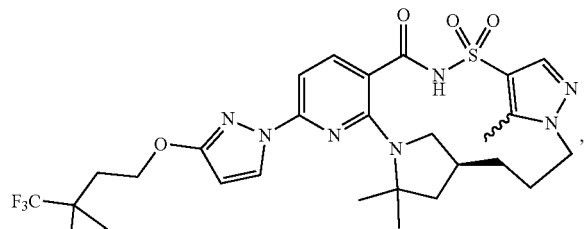
Compoound 114
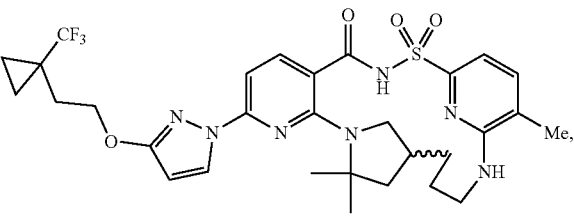
Compound 115
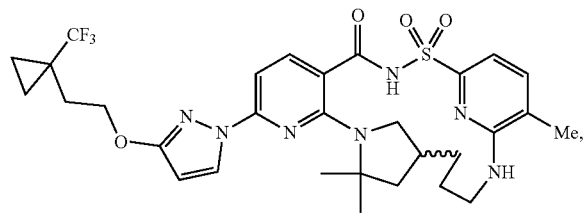
Compound 116
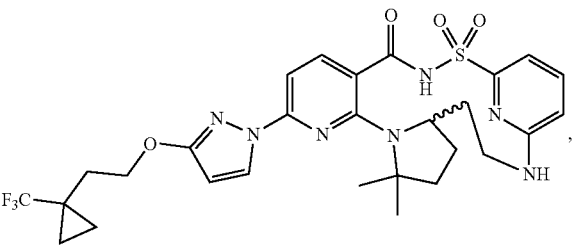

Compound 117
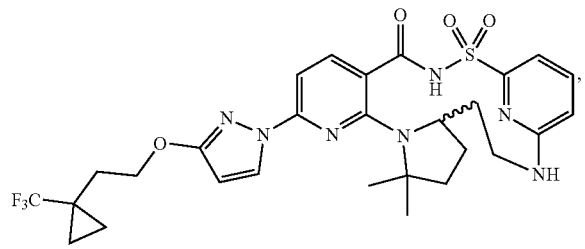
Compound 118
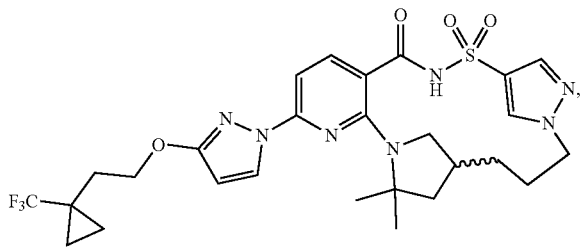
Compound 119
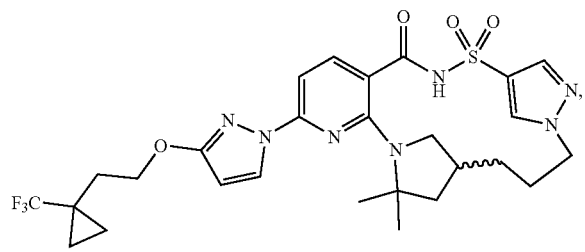
Compound 120
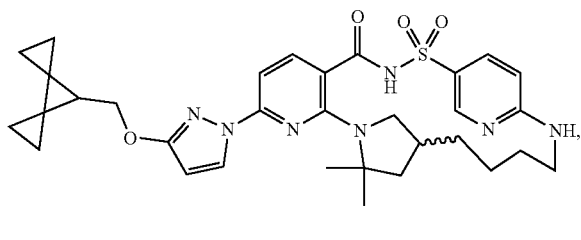
Compound 121
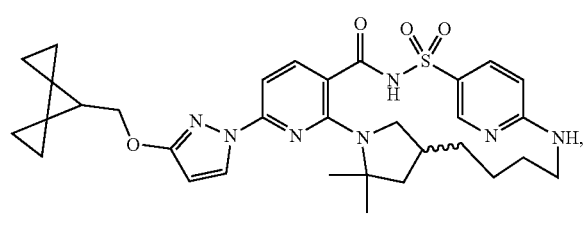
Compound 122
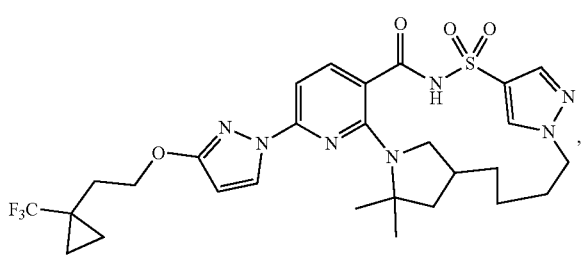
Compound 123
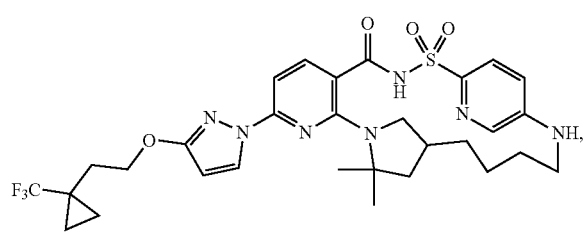
Compound 124
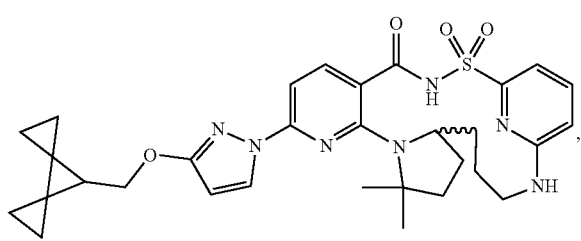
Compound 125
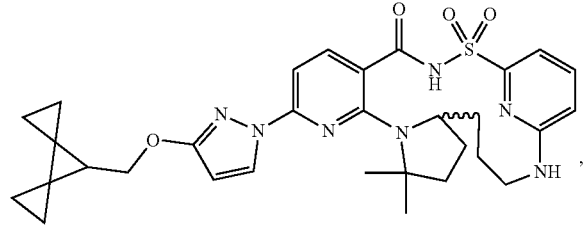
Compound 126
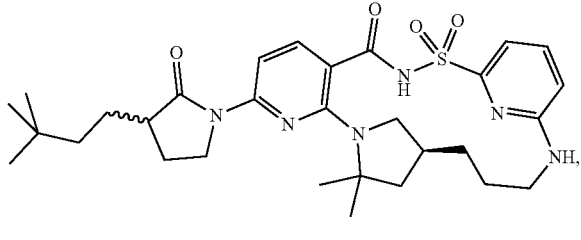
Compound 127
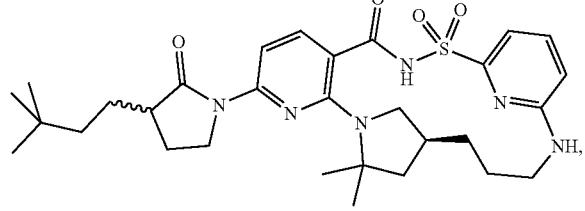
Compound 128
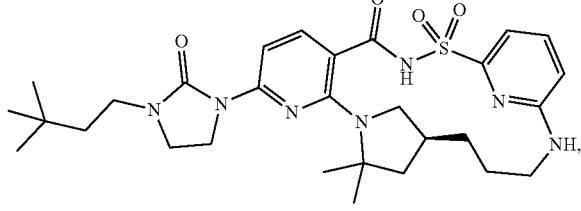

-continued
Compound 129
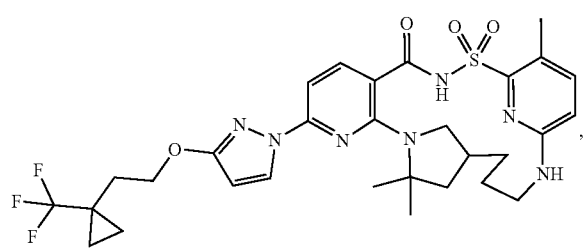
Compound 130
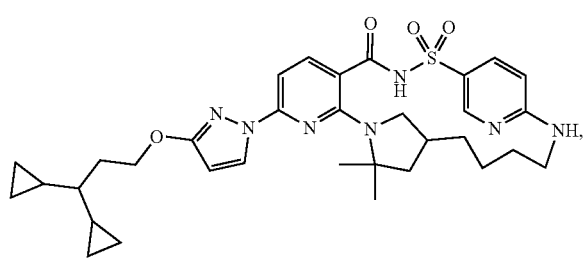
Compound 131
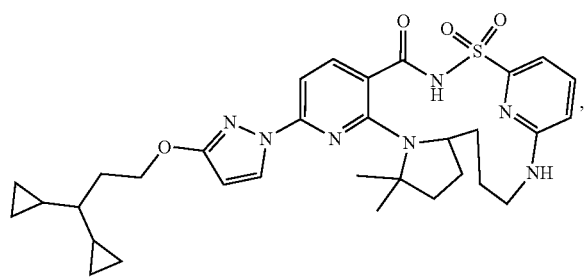
Compound 132
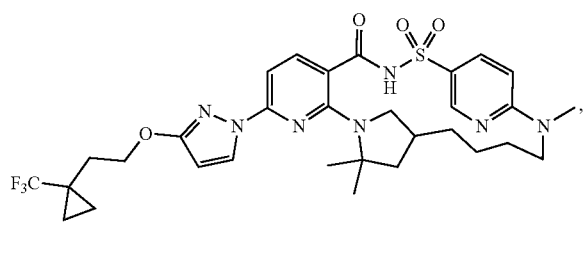
Compound 133
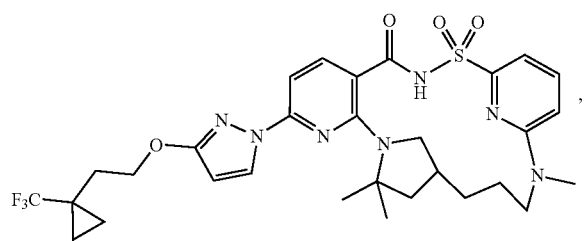
Compound 134
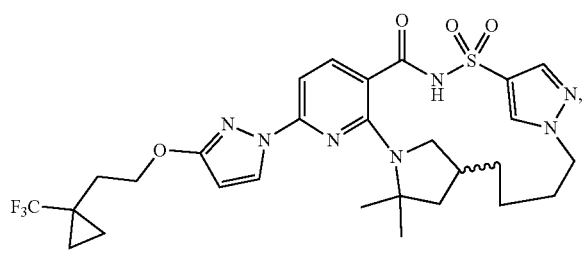
Compound 135
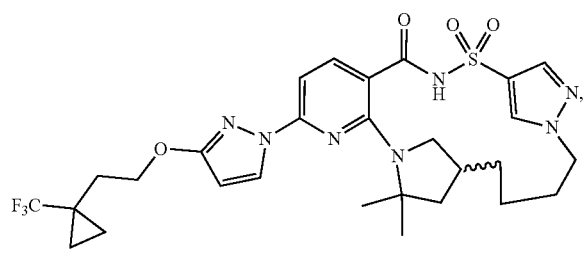
Compound 136
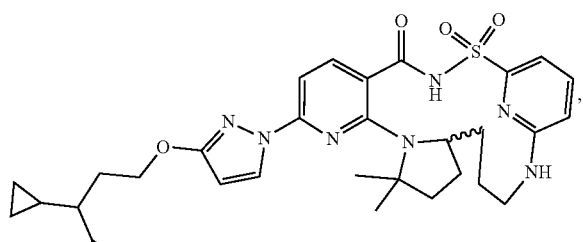
Compound 137
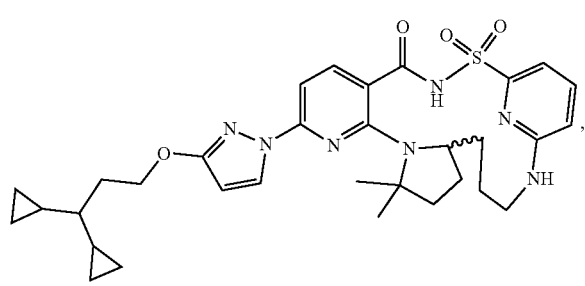
Compound 138
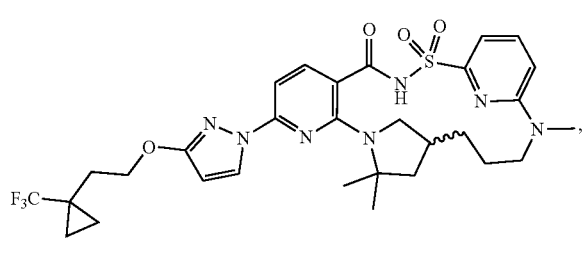

-continued
Compound 139
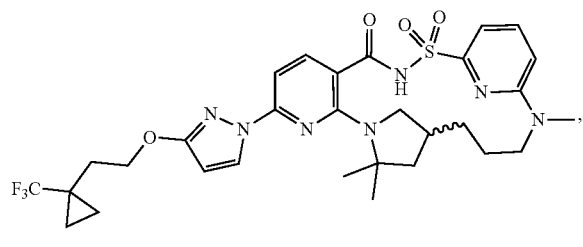
Compound 140
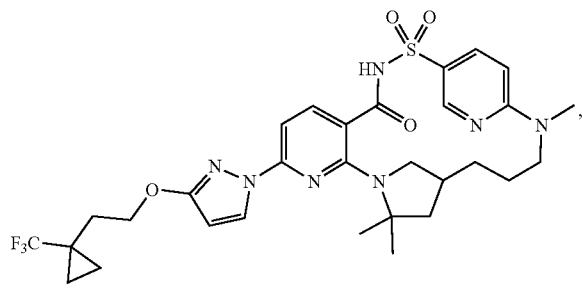
Compound 141
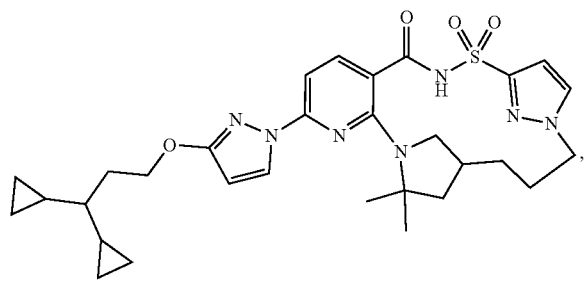
Compound 142
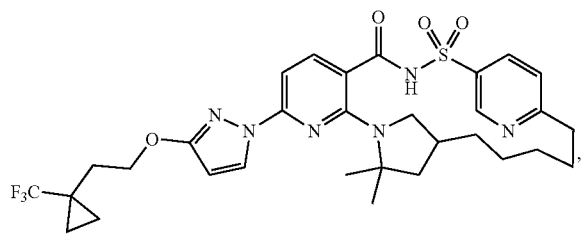
Compound 143
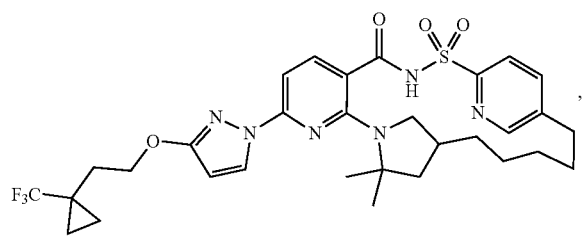
Compound 144
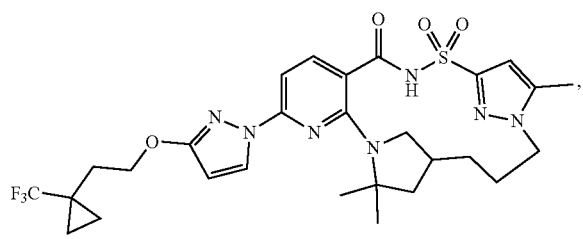
Compound 145
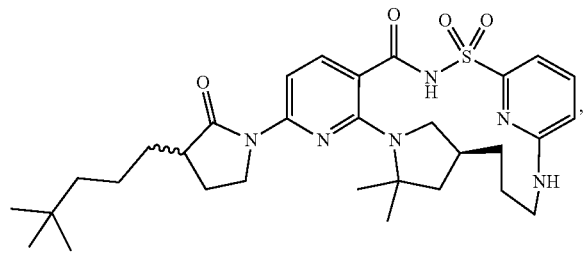
Compound 146
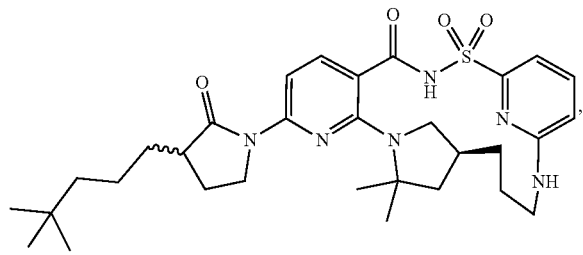
Compound 147
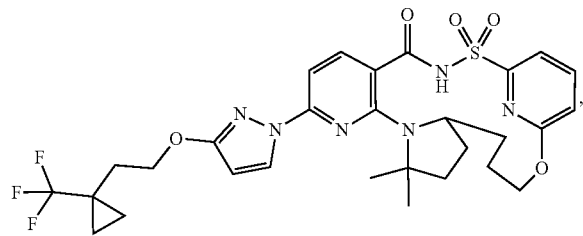
Compound 148
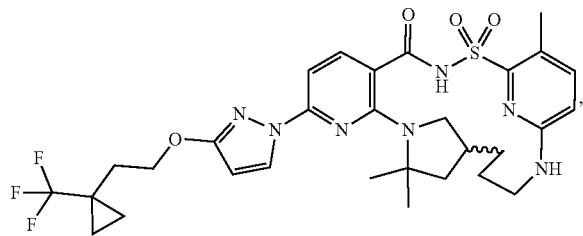

Compound 149
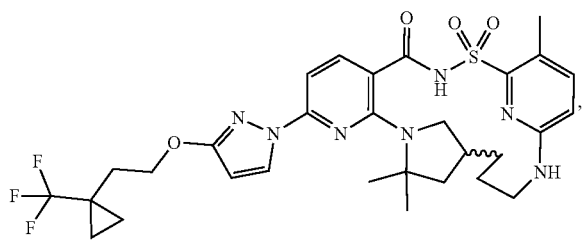
Compound 150
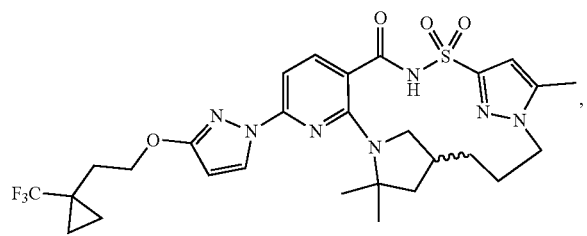
Compound 151
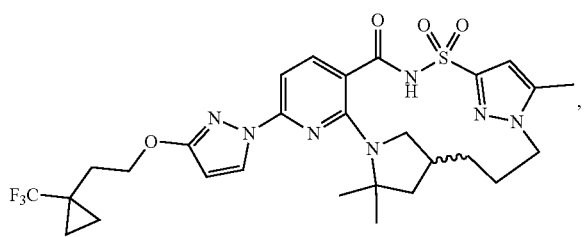
Compound 152
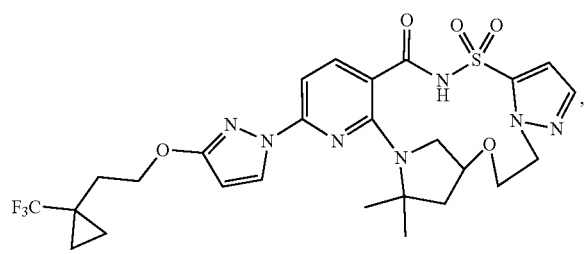
Compound 153
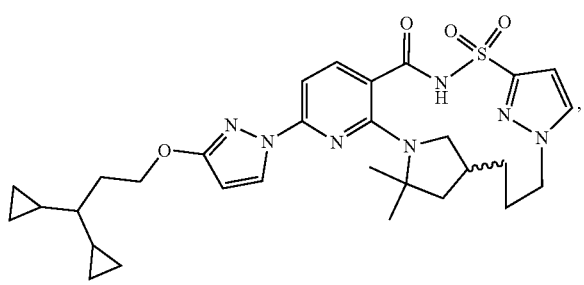
Compound 154
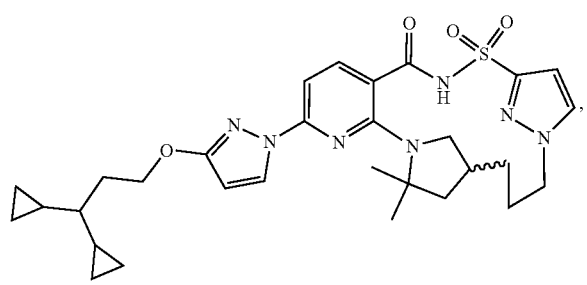
Compound 155
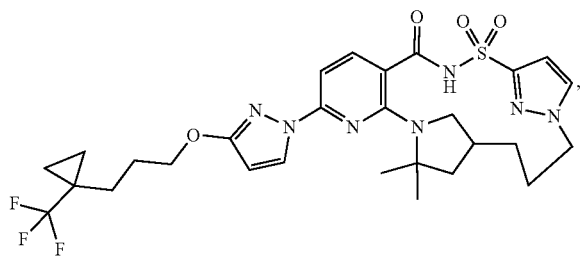
Compound 156
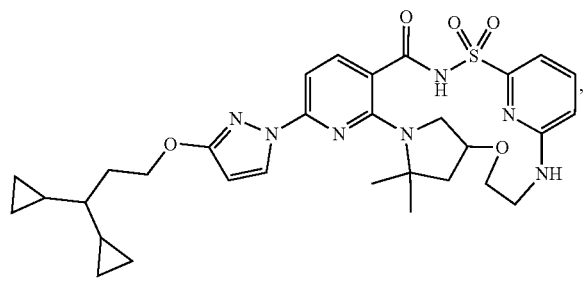
Compound 157
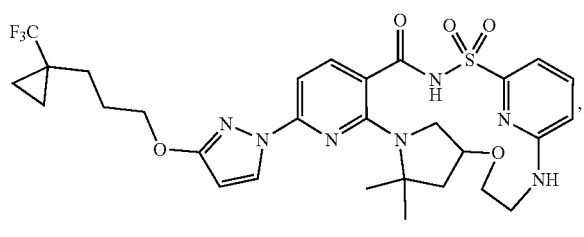
Compound 158
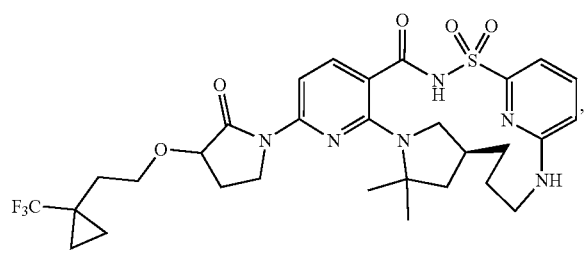

-continued
Compound 159
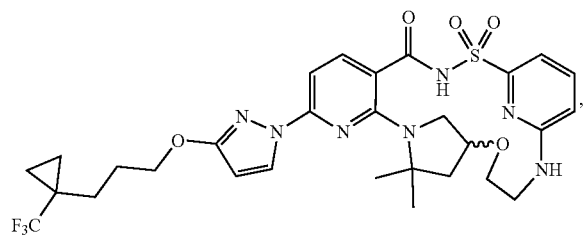
Compound 160
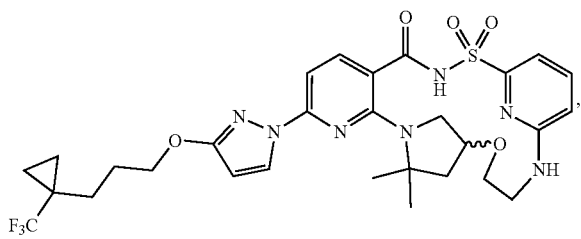
Compound 161
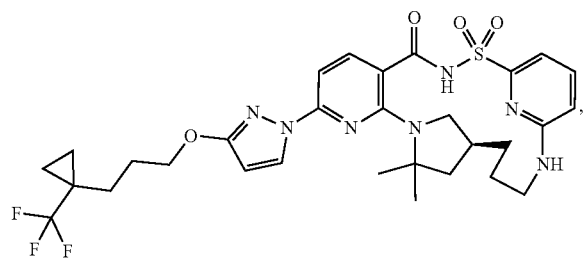
Compound 162
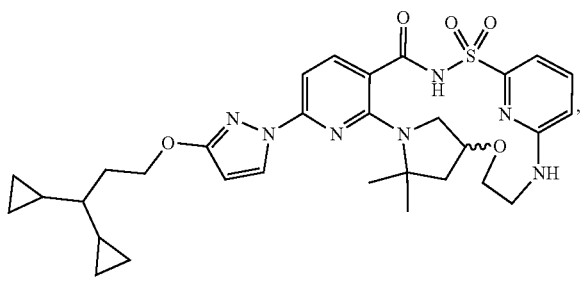
Compound 163
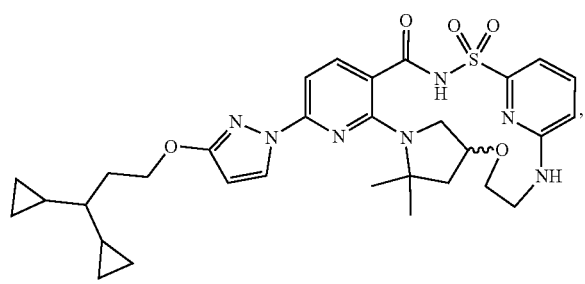
Compound 164
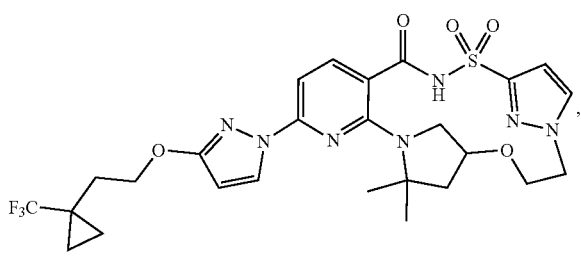
Compound 165
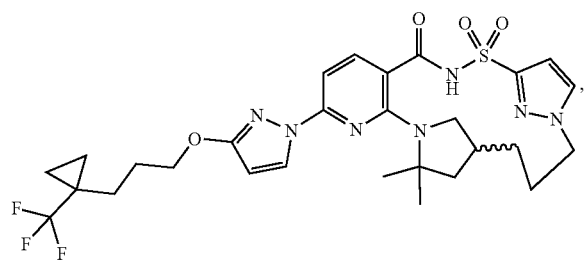
Compound 166
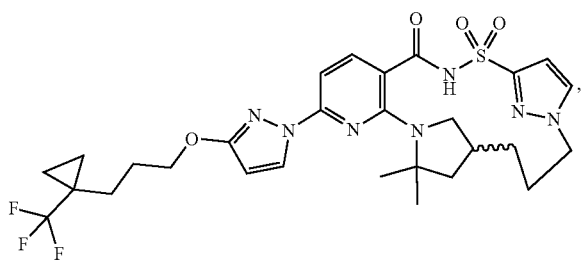
Compound 167
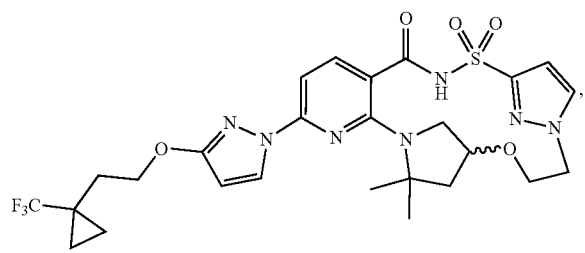
Compound 168
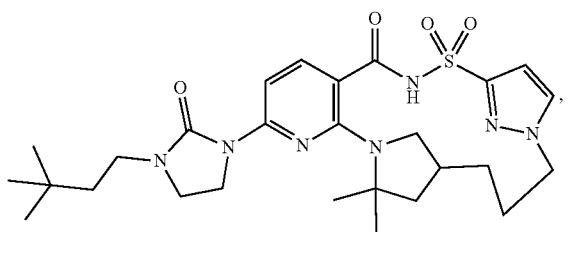

-continued
Compound 169
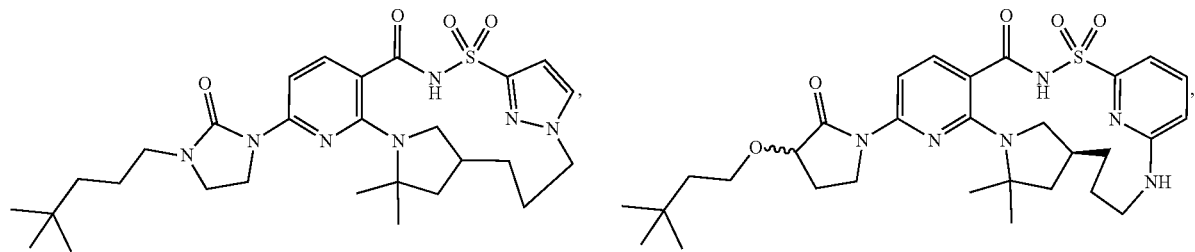
Compound 170
Compound 171
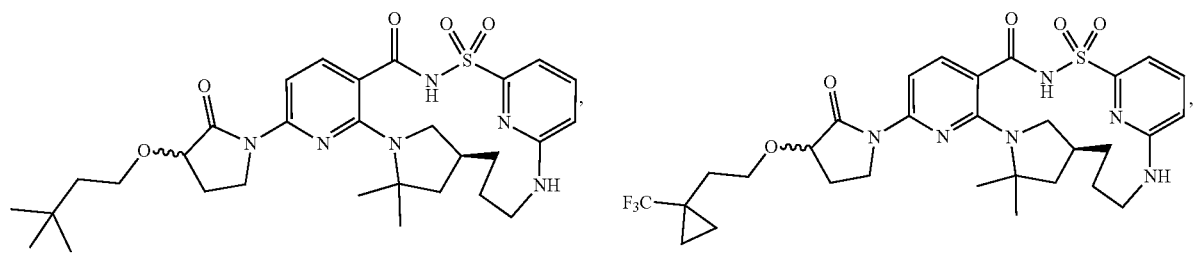
Compound 172
Compound 173
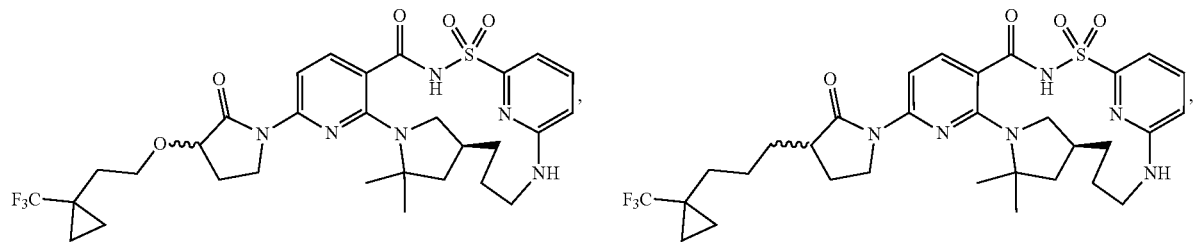
Compound 174
Compound 175
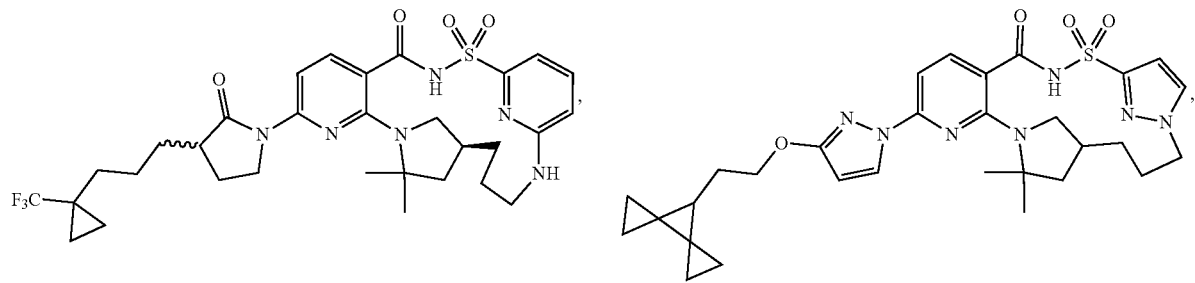
Compound 176
Compound 177
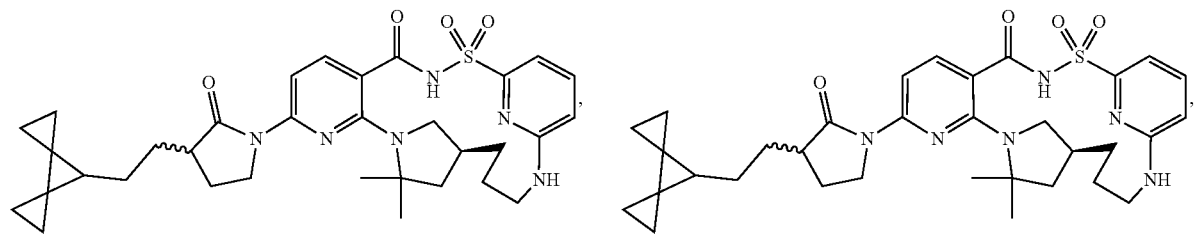
Compound 178

-continued
Compound 179
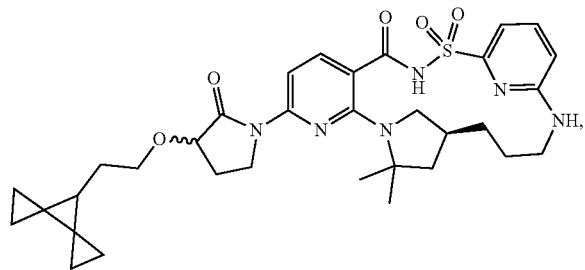
Compound 180
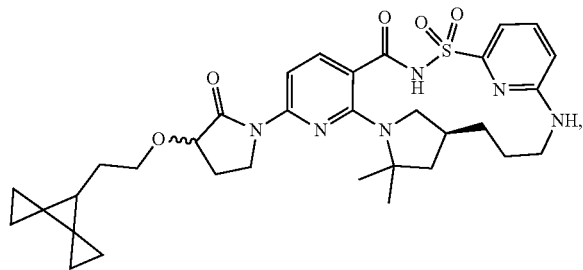
Compound 181
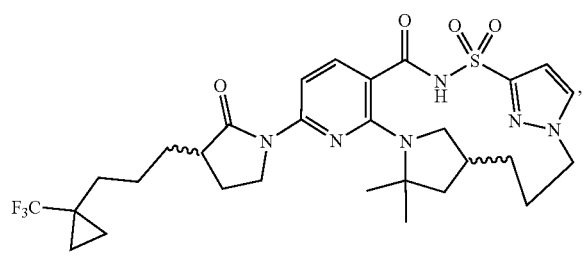
Compound 182
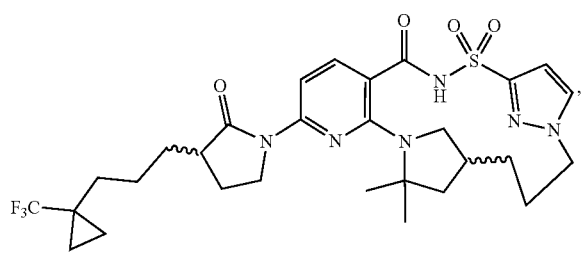
Compound 183
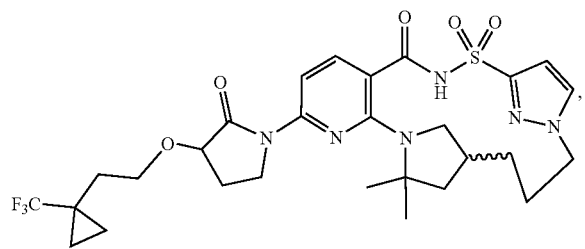
Compound 184
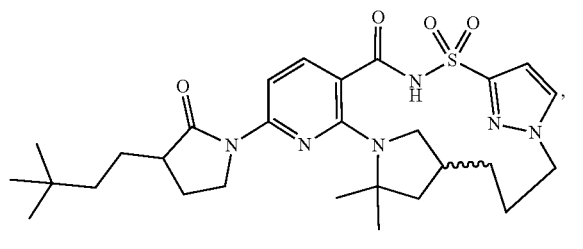
Compound 185
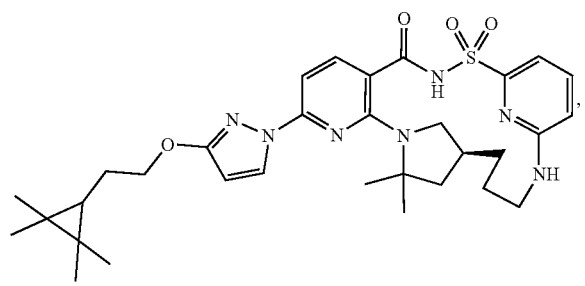
Compound 186
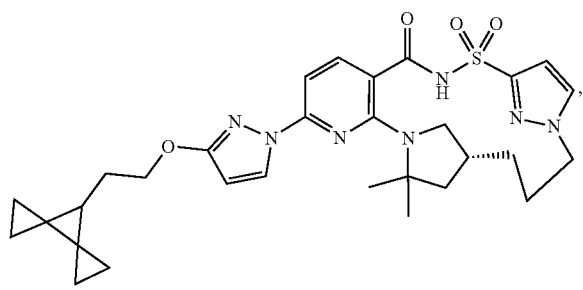
Compound 187
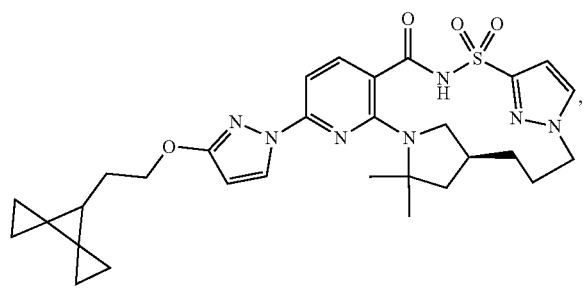
Compound 188
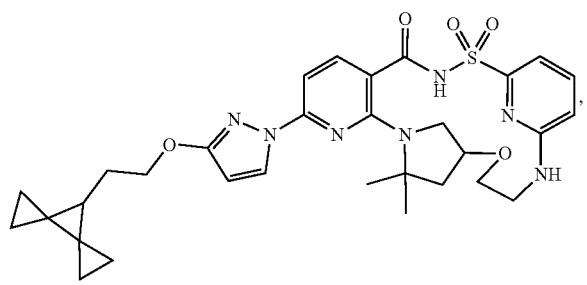

-continued
Compound 189
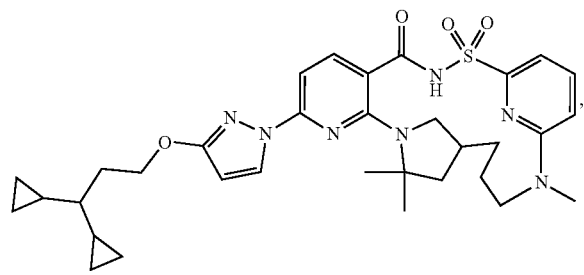
Compound 190
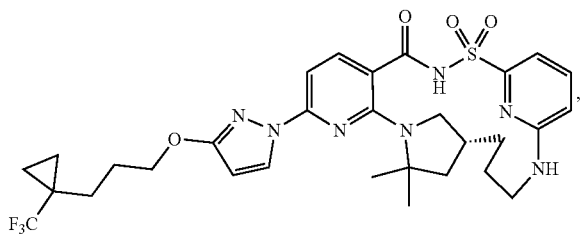
Compound 191
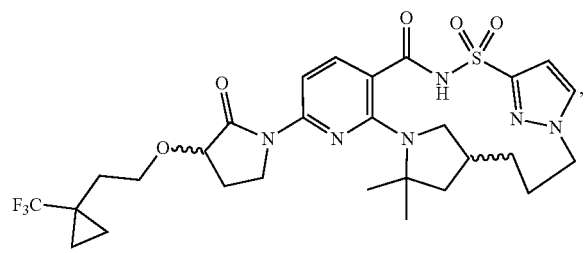
Compound 192
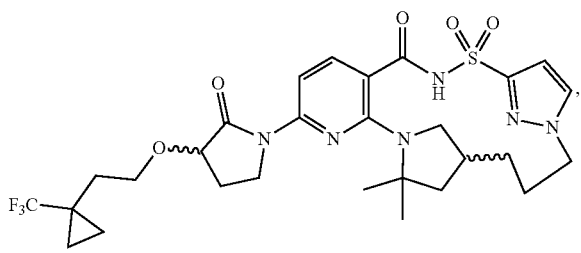
Compound 193
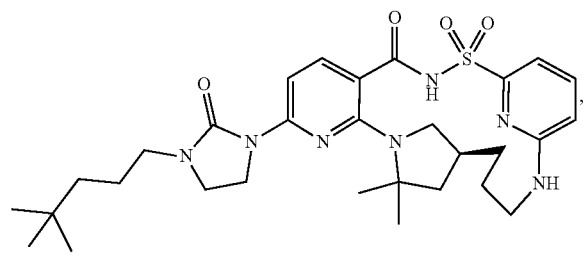
Compound 194
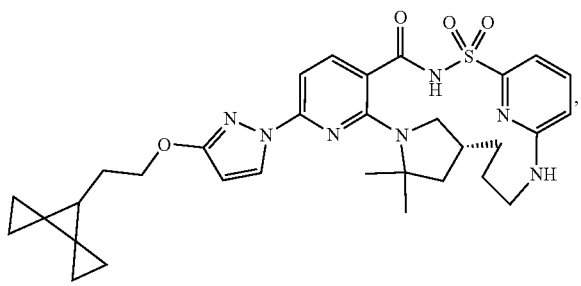
Compound 195
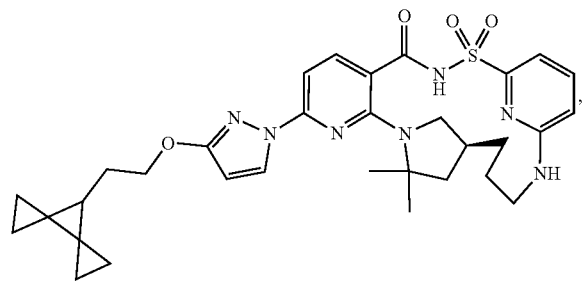
Compound 196
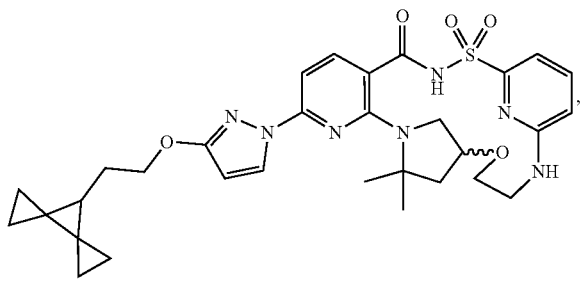
Compound 197
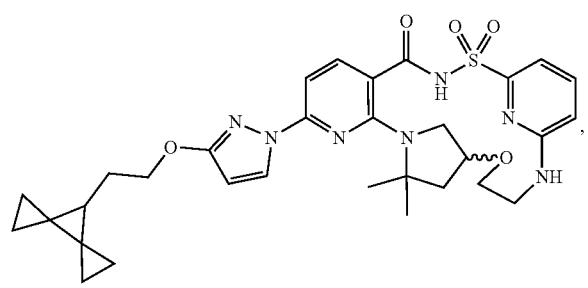
Compound 198
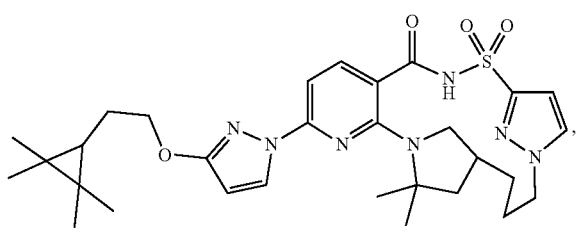

-continued
Compound 199
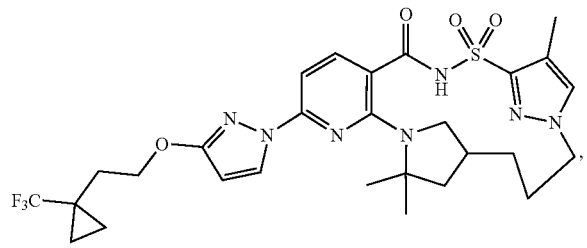
Compound 200
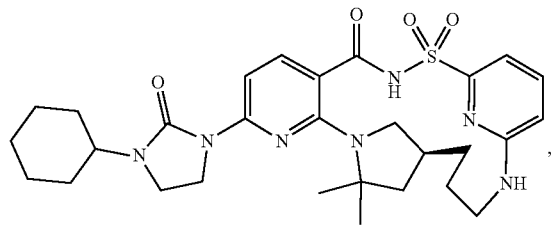
Compound 201
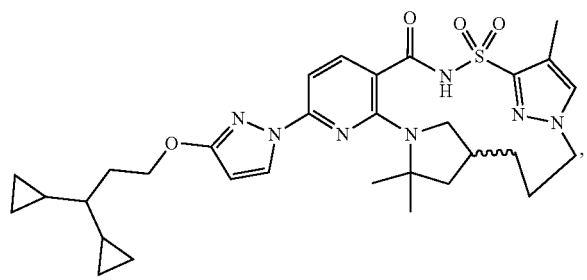
Compound 202
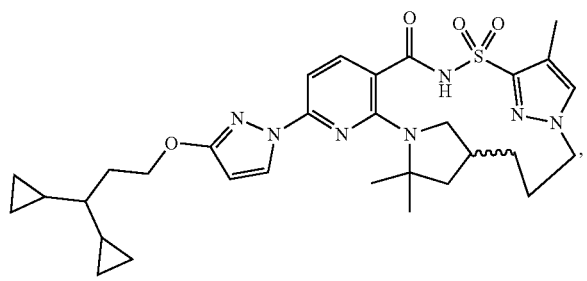
Compound 203
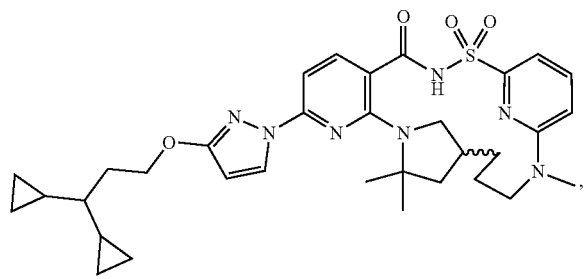
Compound 204
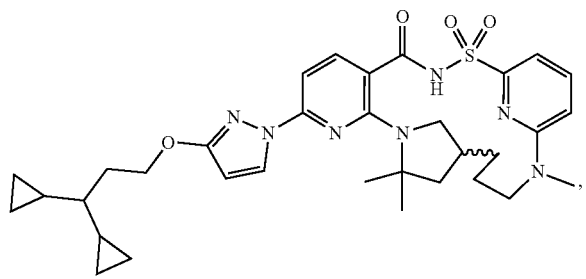
Compound 205
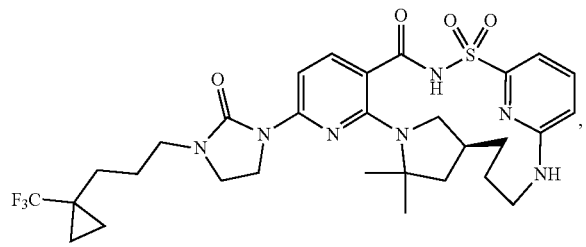
Compound 206
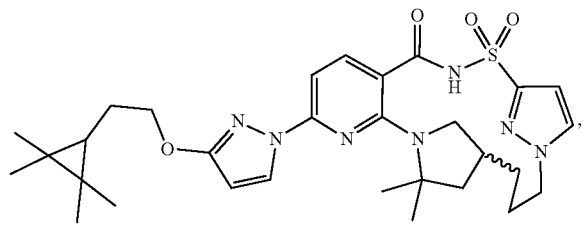
Compound 207
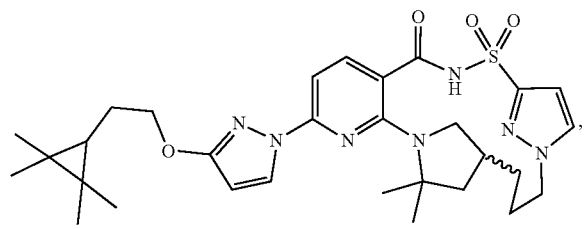
Compound 208
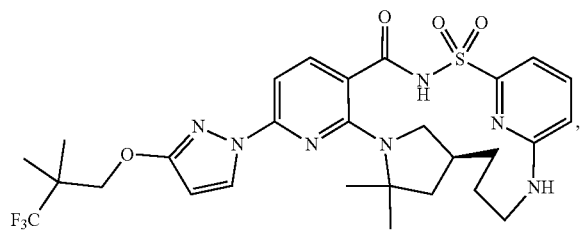

-continued
Compound 209
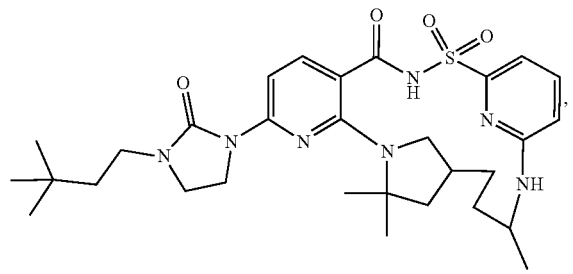
Compound 210
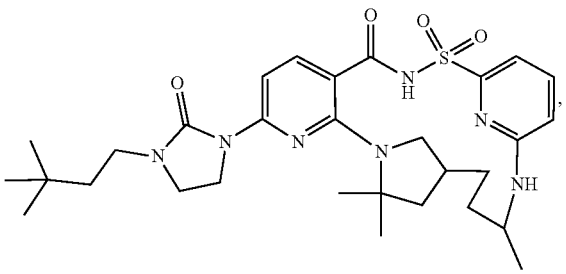
Compound 211
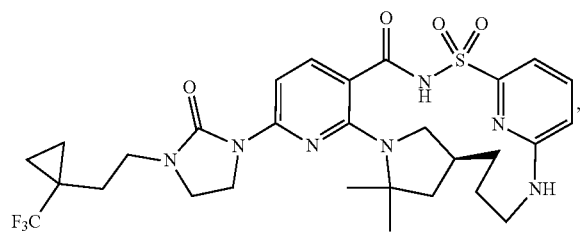
Compound 212
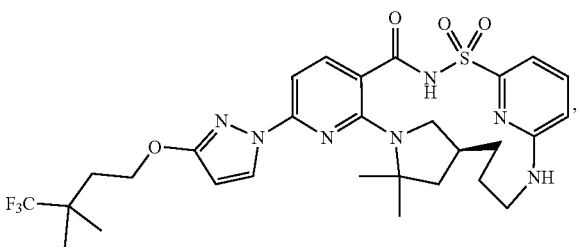
Compound 213
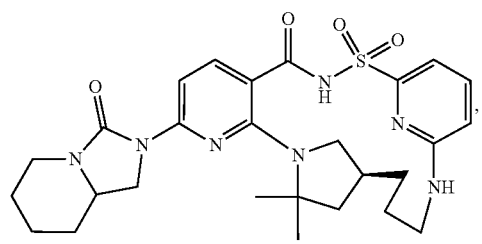
Compound 214
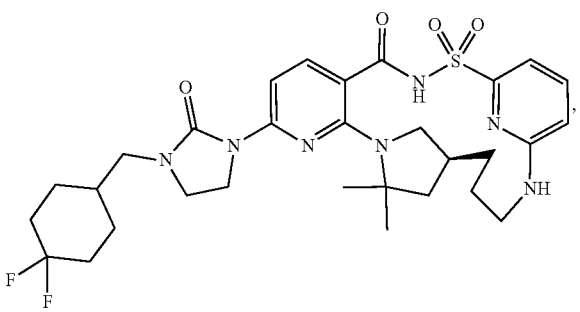
Compound 215
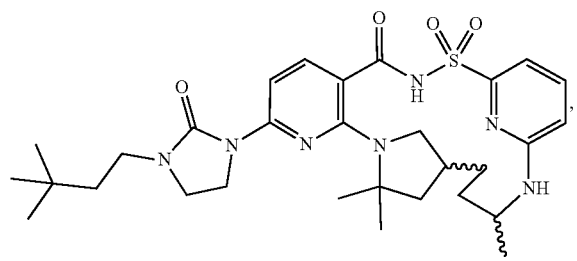
Compound 216
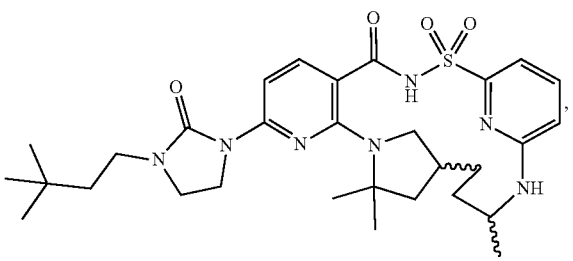
Compound 217
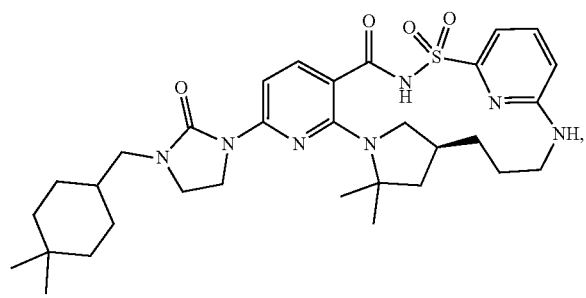
Compound 218
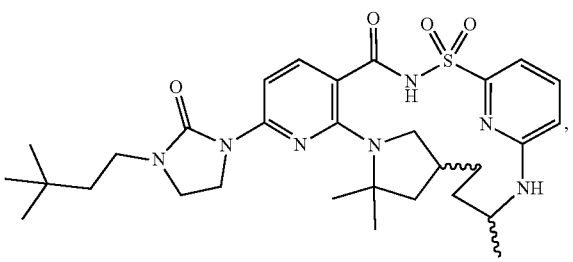

-continued
Compound 219
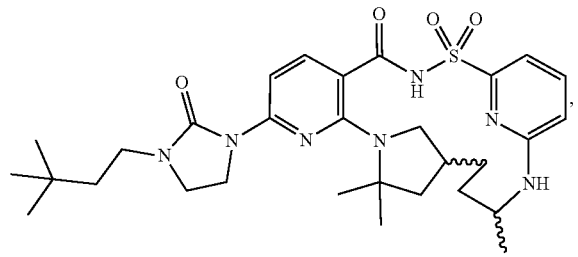
Compound 220
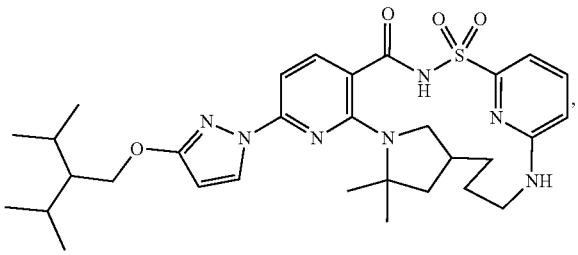
Compound 221
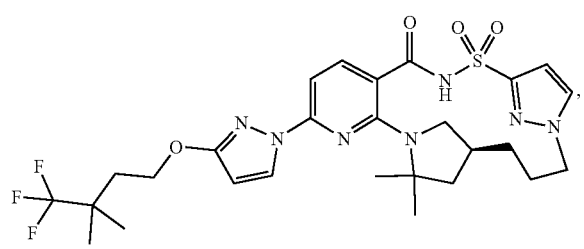
Compound 222
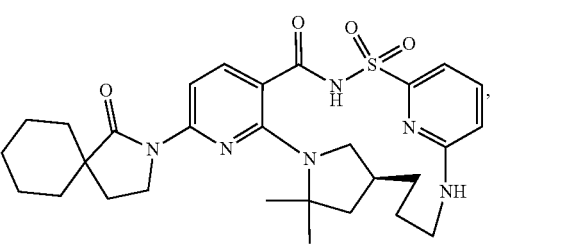
Compound 223
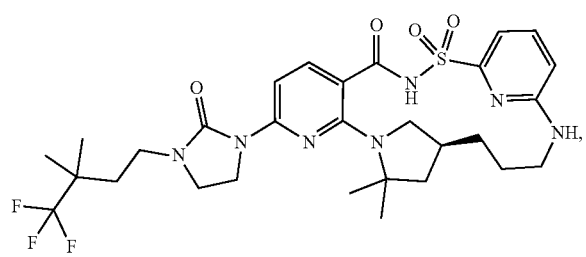
Compound 224
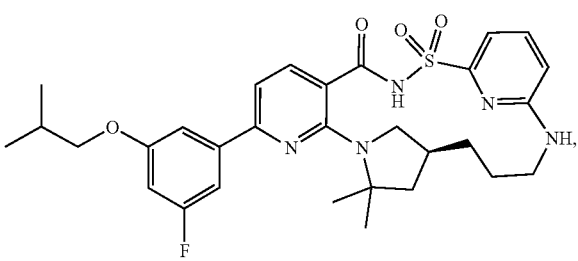
Compound 225
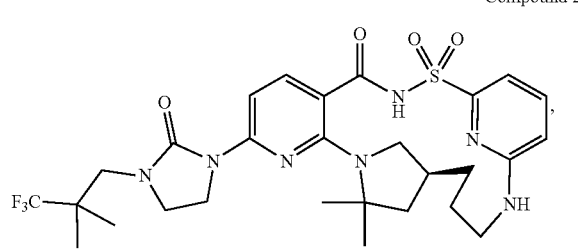
Compound 226
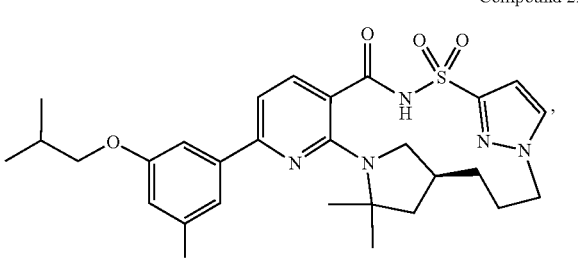
Compound 227
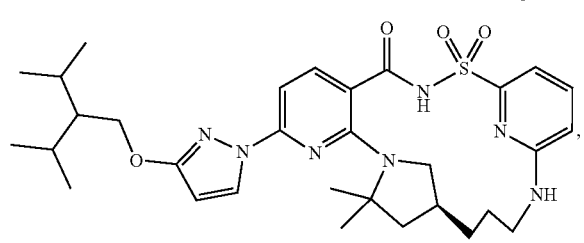
Compound 228
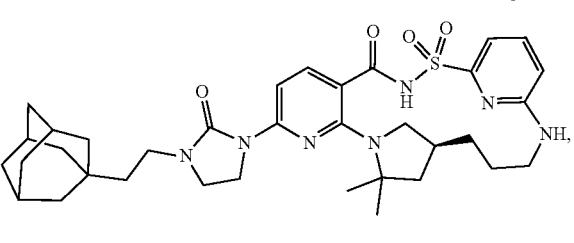
Compound 229
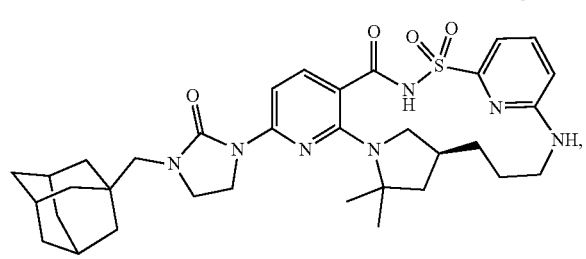
Compound 230
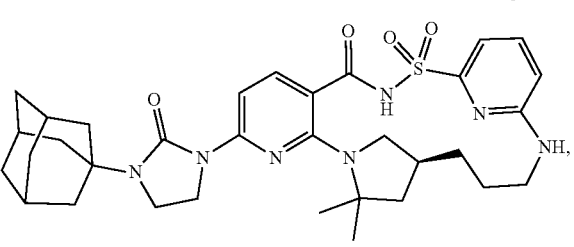

-continued
Compound 231
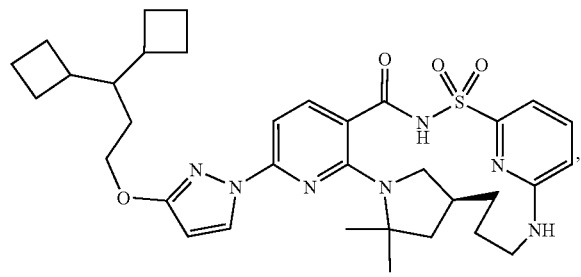
Compound 232
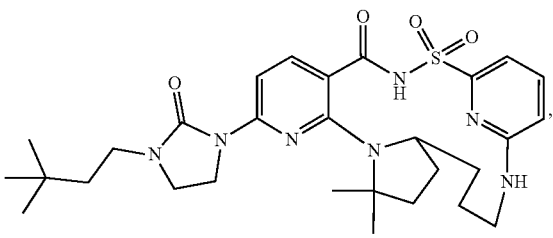
Compound 233
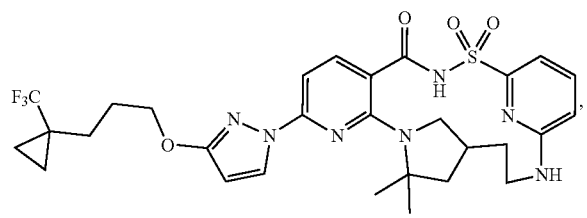
Compound 234
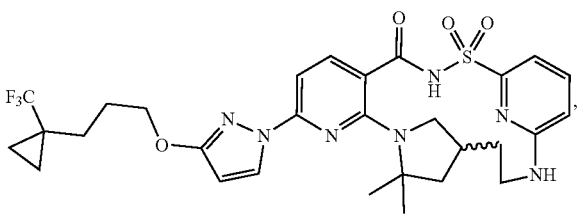
enantiomer 1
Compound 235
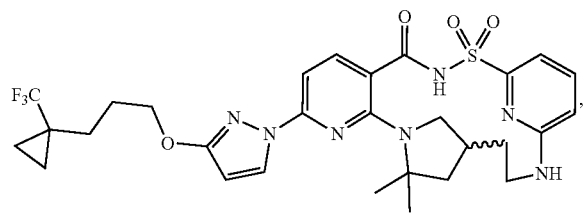
enantiomer 2
Compound 236
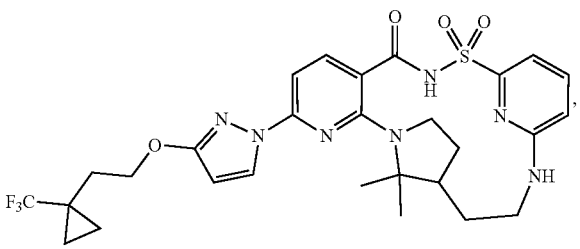
Compound 237
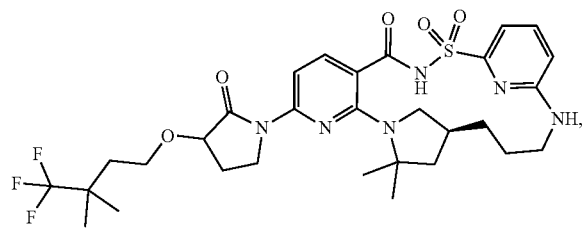
Compound 238
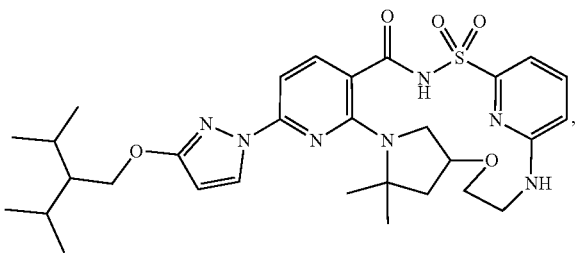
Compound 239
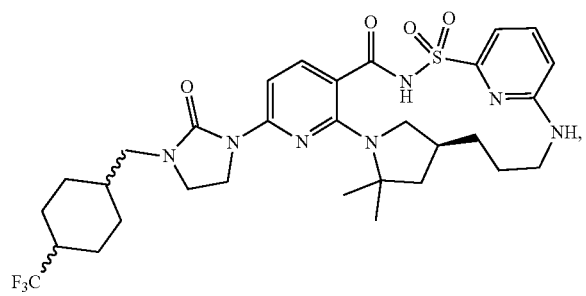
Compound 240
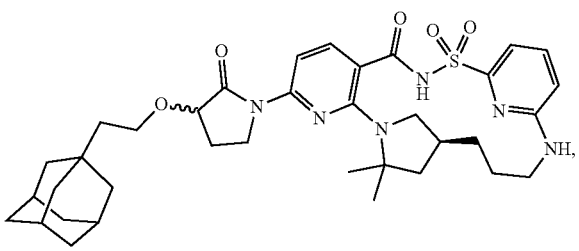

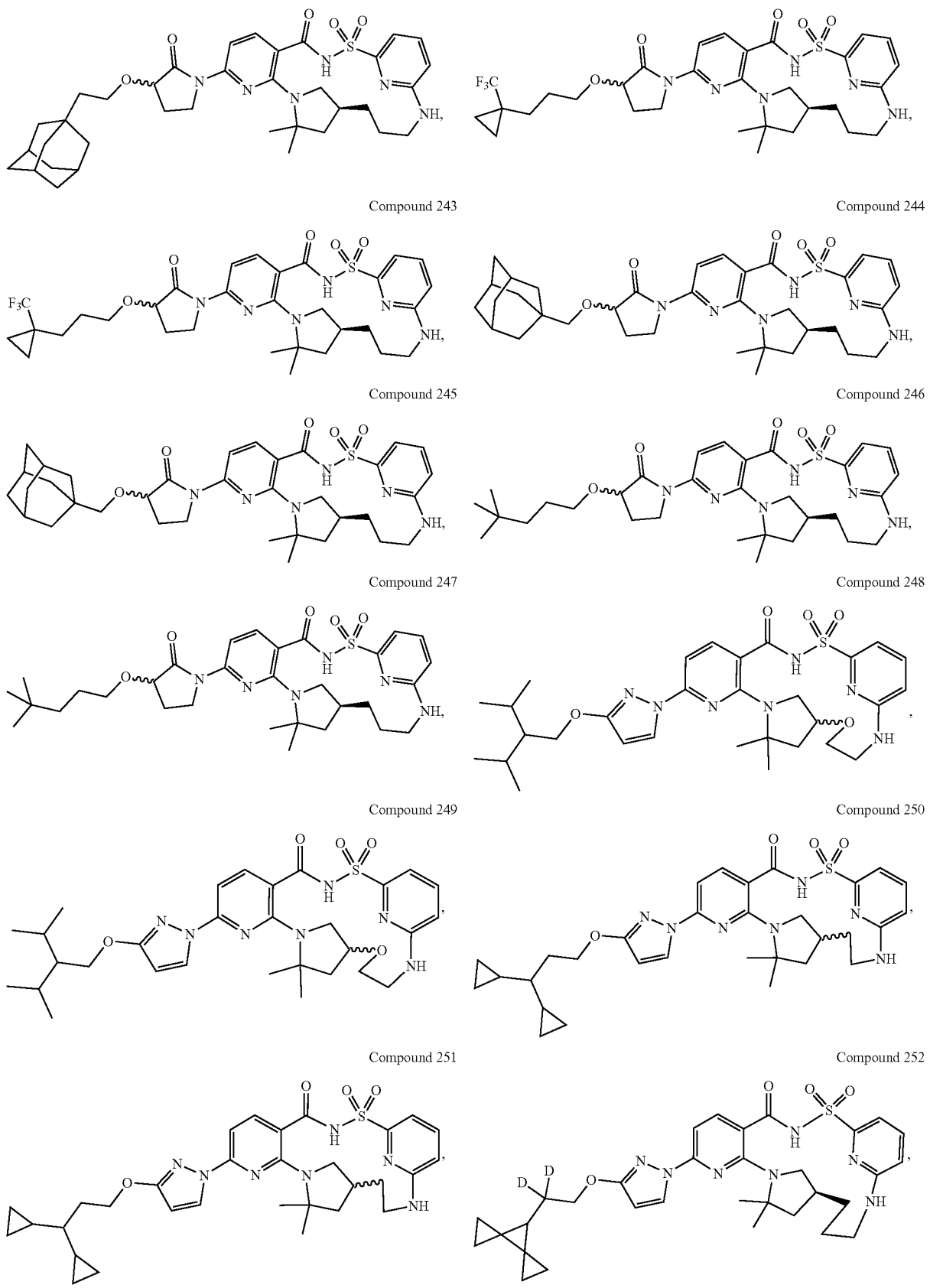

-continued
Compound 253
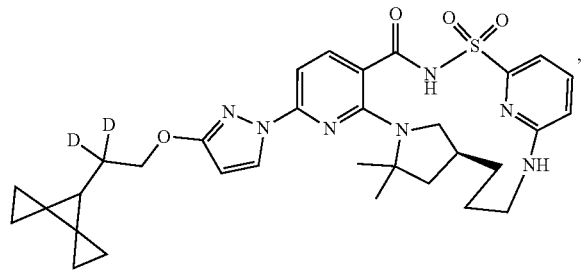
Compound 254
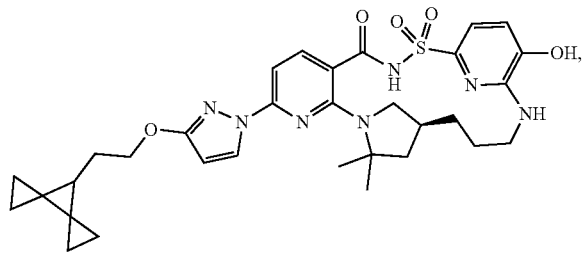
Compound 255
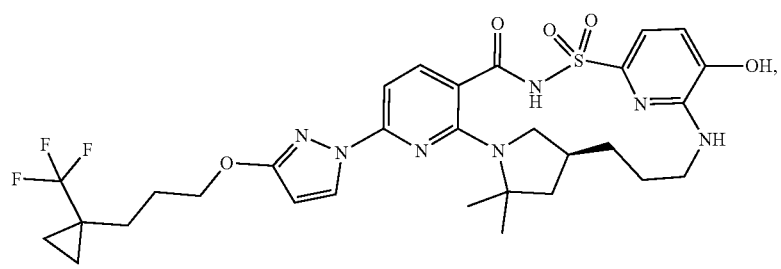
Compound 256
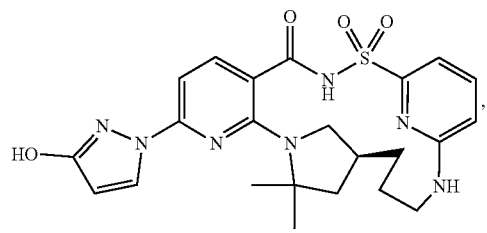
Compound 257
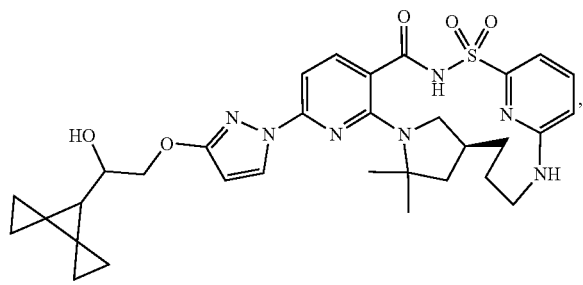
Compound 258
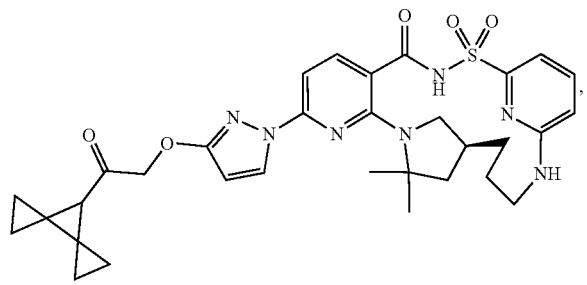
Compound 259
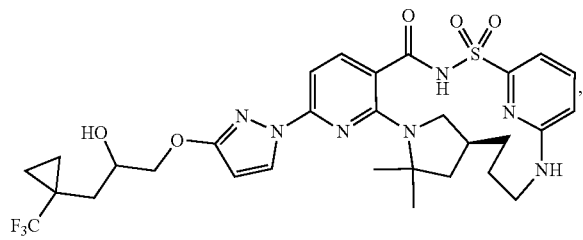
Compound 260
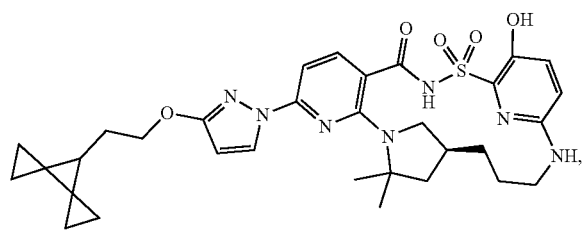
Compound 261
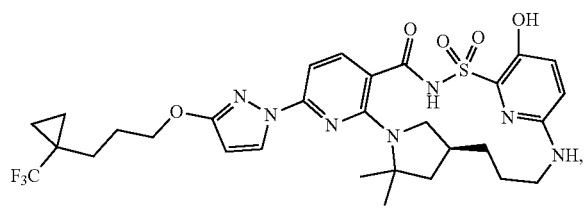

-continued
Compound 262
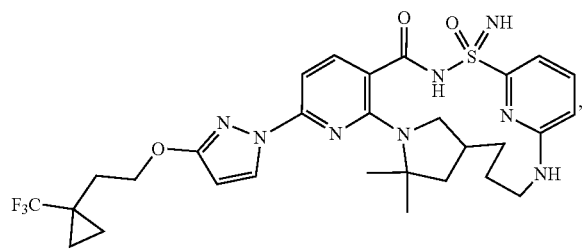
Compound 263
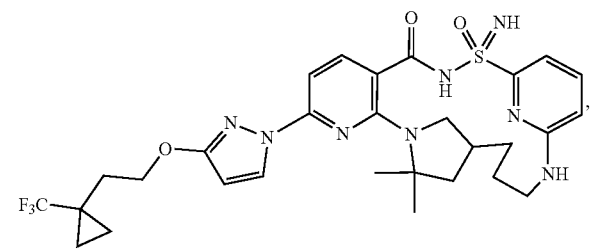
Compound 264
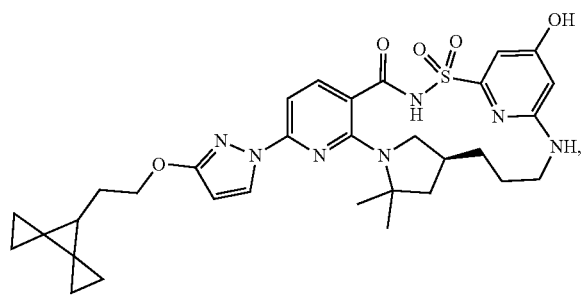
Compound 265
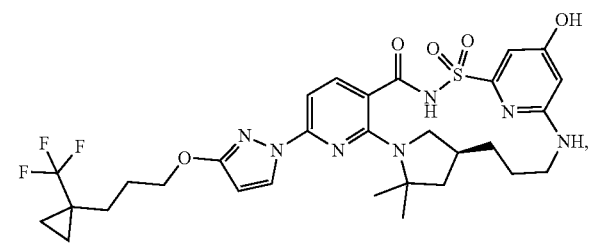
Compound 266
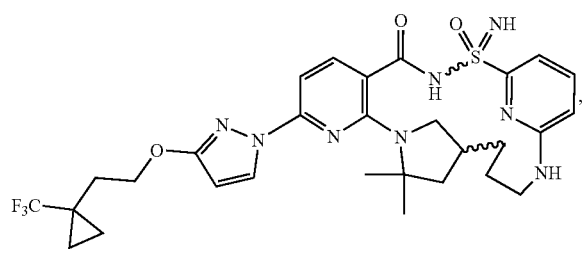
Compound 267
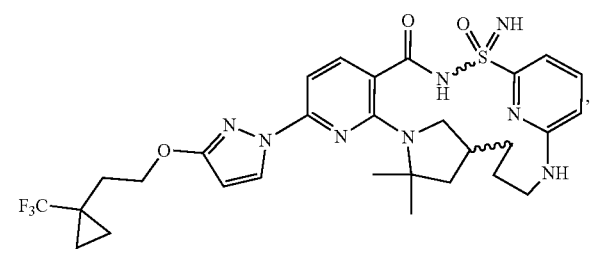
Compound 268
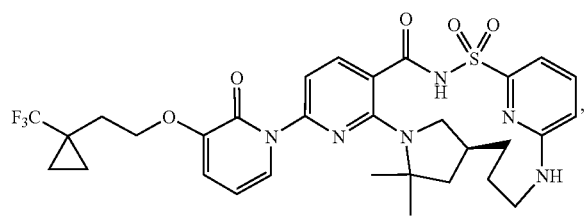
Compound 269
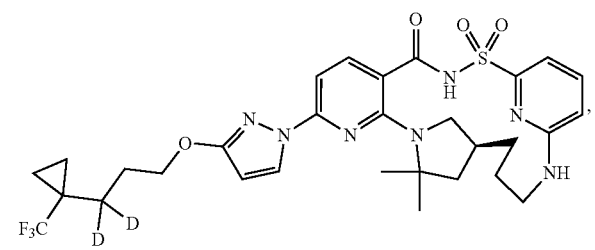
Compound 270
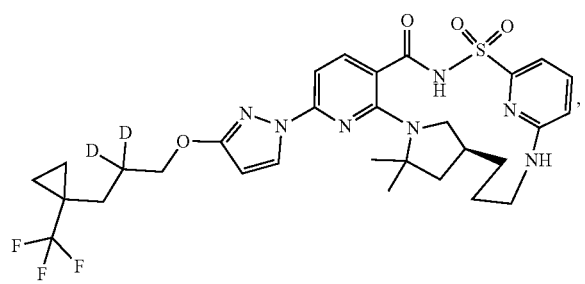
Compound 271
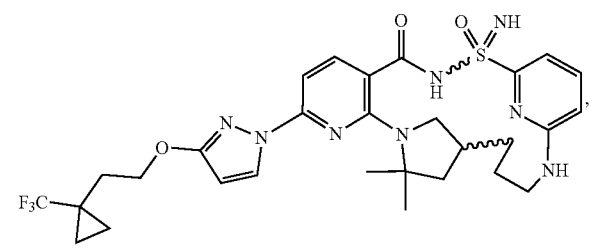

-continued
Compound 272
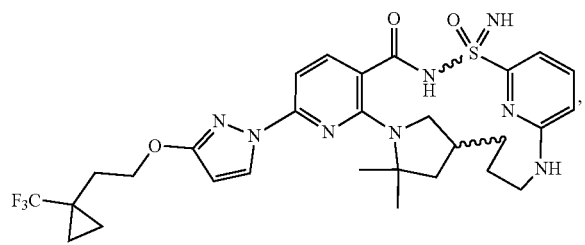
Compound 273
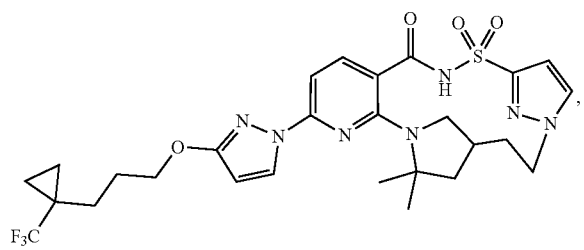
Compound 274
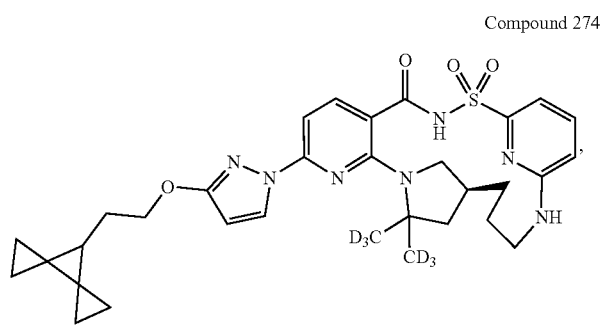
Compound 275
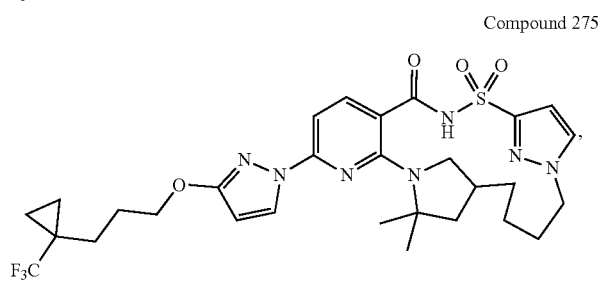
Compound 276
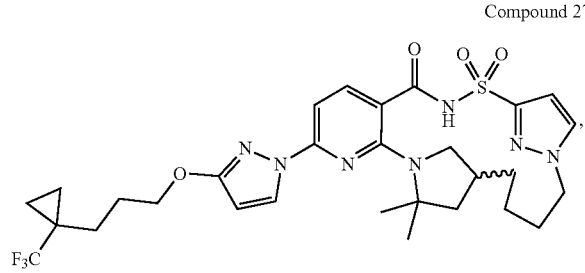
Compound 277
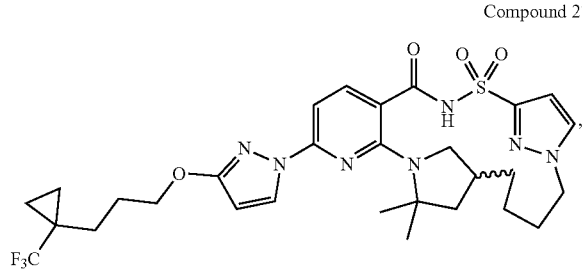
Compound 278
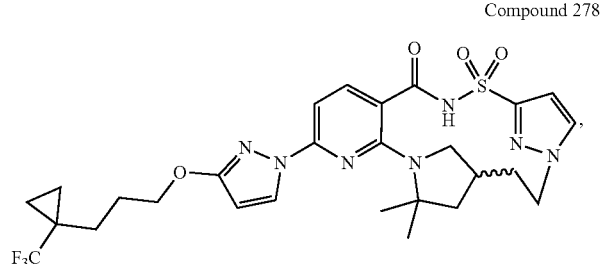
Compound 279
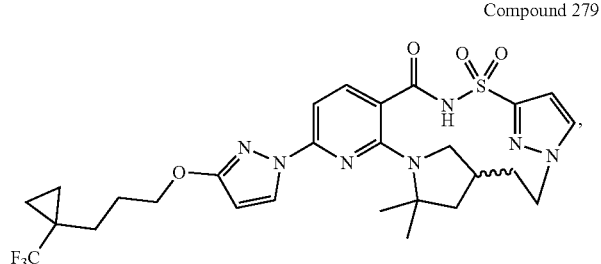
Compound 280
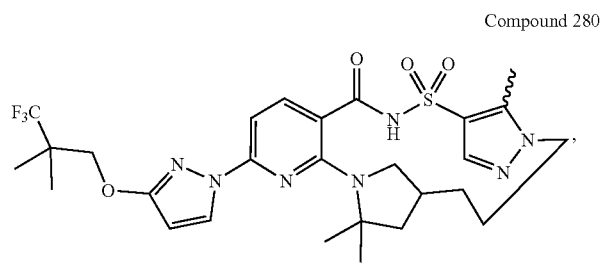
Compound 281
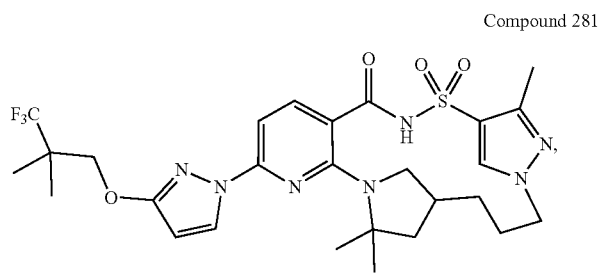
Compound 282
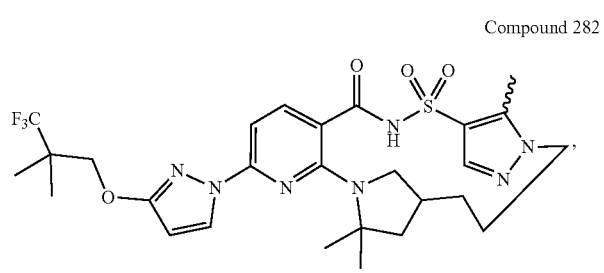
Compound 283
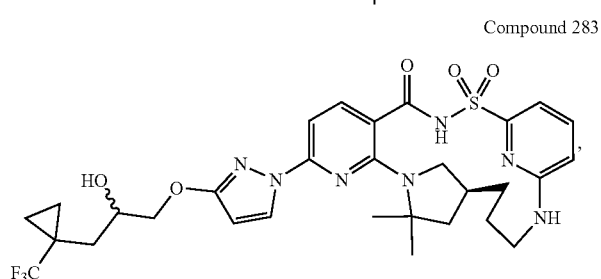

-continued
Compound 284
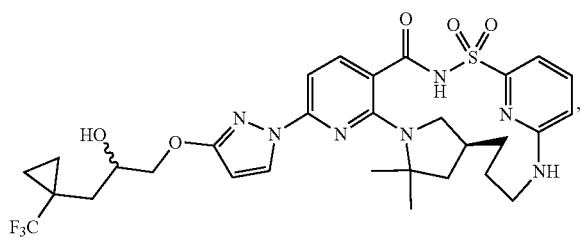
Compound 285
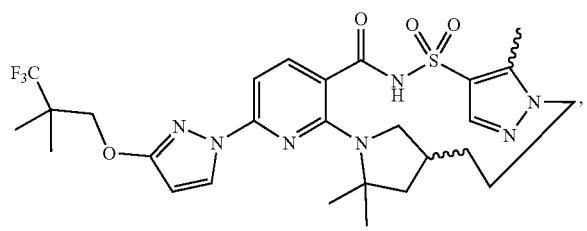
Compound 286
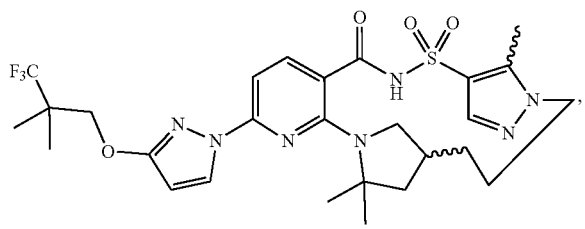
Compound 287
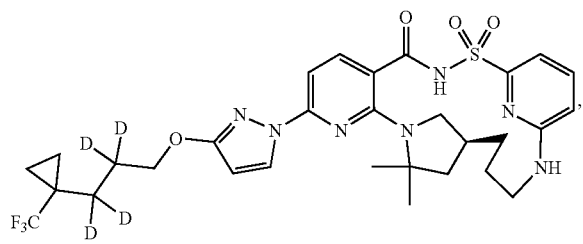
Compound 288
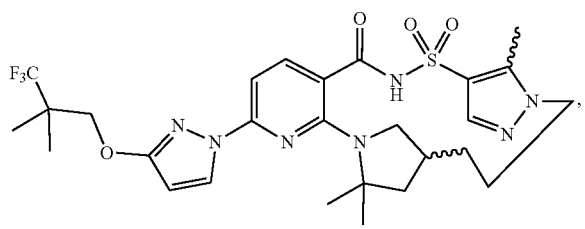
Compound 289
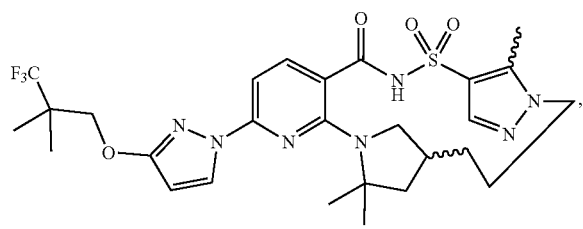
Compound 290
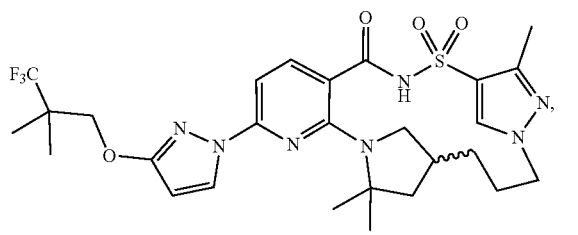
Compound 291
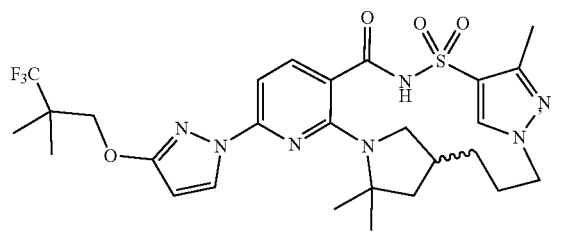
Compound 292
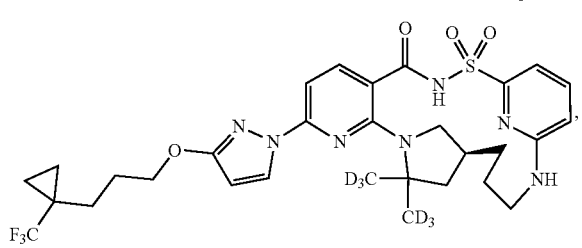
Compound 293
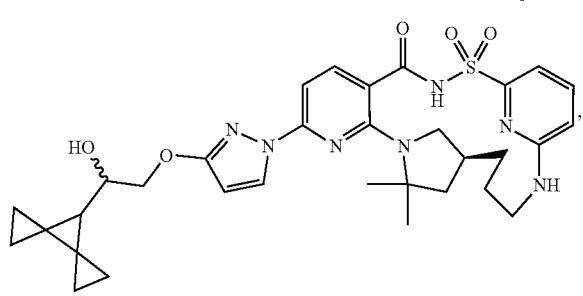
Compound 294
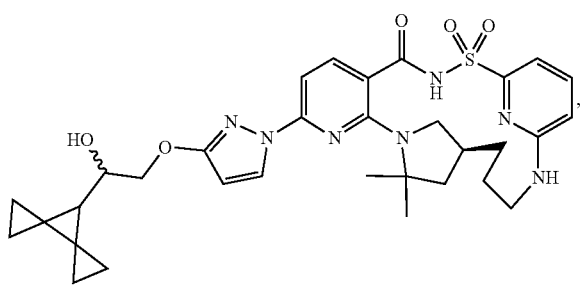
Compound 295
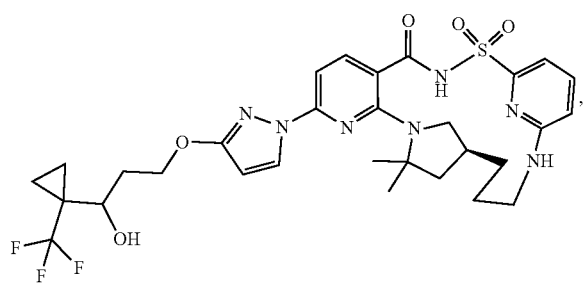

-continued
Compound 296
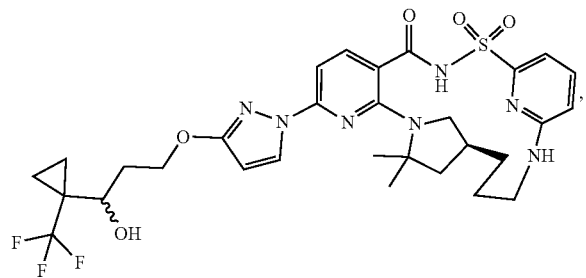
Compound 297
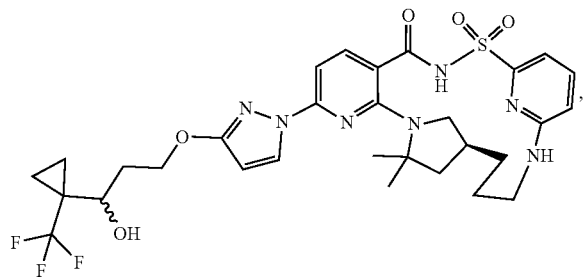
Compound 298
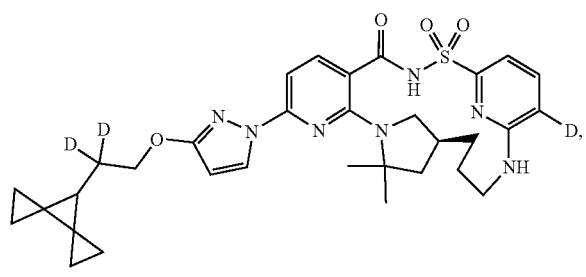
Compound 299
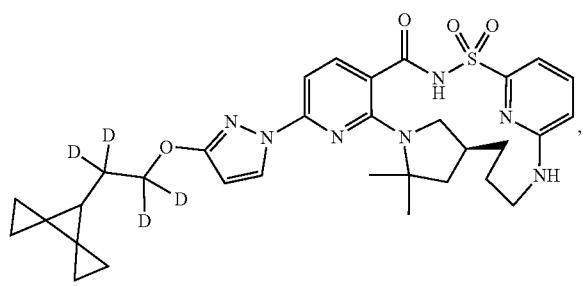
Compound 300
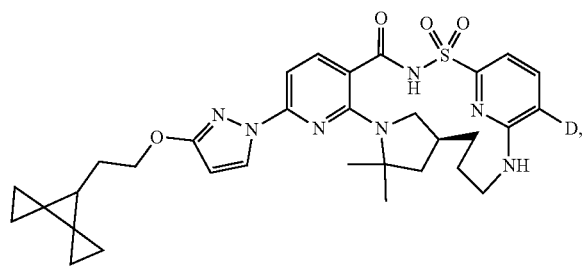
Compound 301
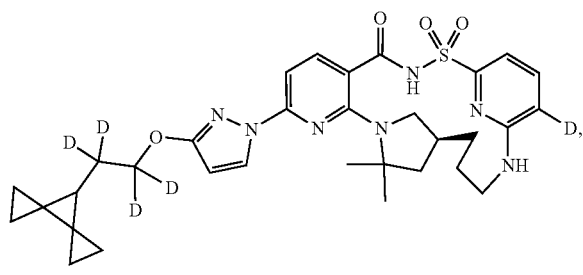
Compound 302
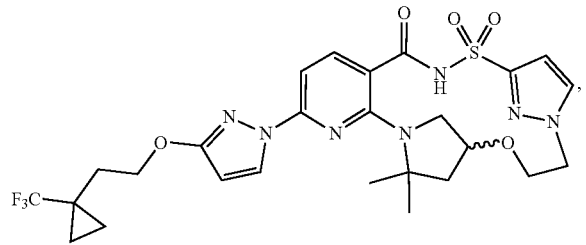
Compound 303
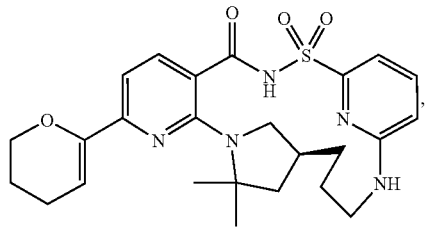
Compound 304
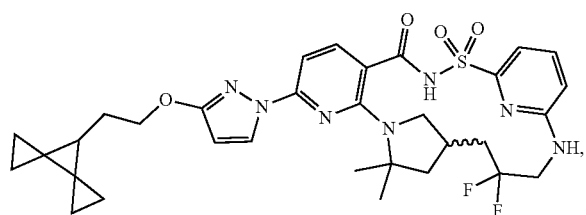
Compound 305
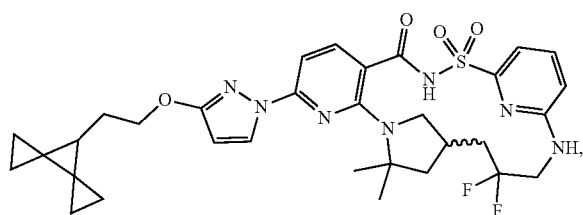

Compound 306

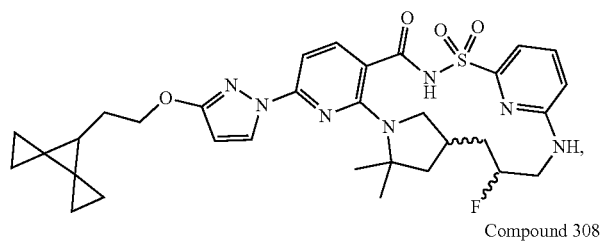

Compound 307

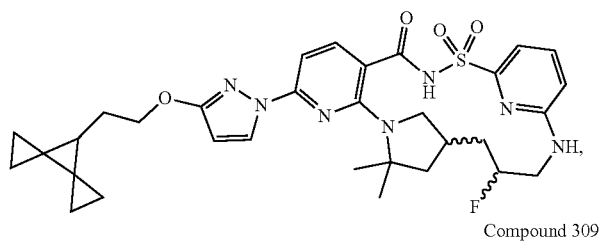

Compound 308

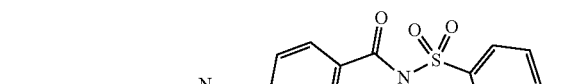

Compound 309

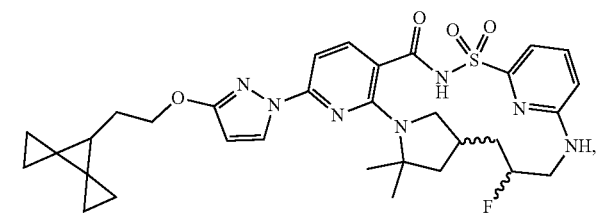

a deuterated derivative thereof, or a pharmaceutically acceptable salt of any of the compounds, or a pharmaceutically acceptable salt of any deuterated derivatives of those compounds.

35. The method of claim 1, wherein the compound is in the form of a pharmaceutically acceptable salt.

36. The method of claim 1, wherein the compound is administered in combination with one or more of:

(a) Compound II:

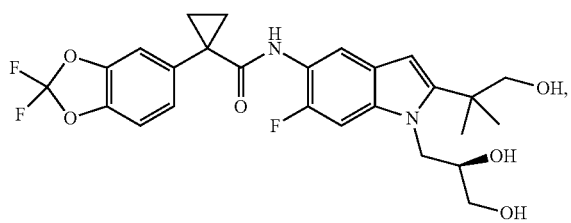

(II)

a pharmaceutically acceptable salt thereof, or a deuterated derivative of any of the foregoing; and (b) Compound III or Compound III-d:

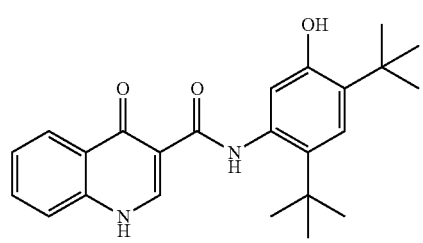

(III)

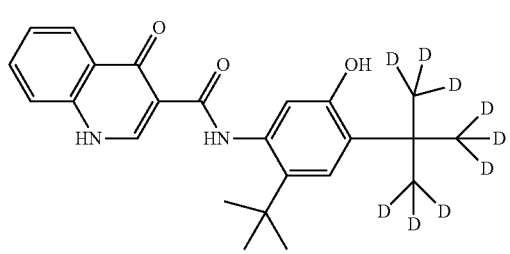

(III-d)

a pharmaceutically acceptable salt thereof, or a deuterated derivative of any of the foregoing.

37. A method of treating cystic fibrosis comprising administering to a patient in need thereof a compound of the formula:

(Compound 195)

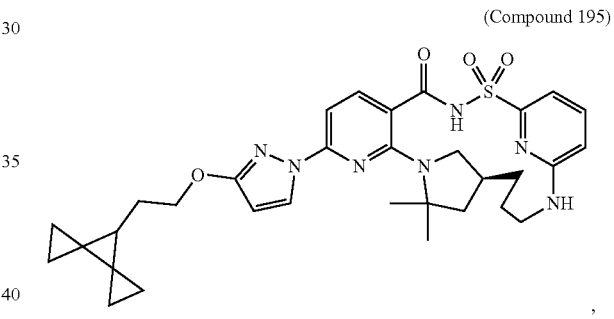

a pharmaceutically acceptable salt thereof, or a deuterated derivative of any of the foregoing.

38. The method of claim 37, wherein the compound is in the form of a pharmaceutically acceptable salt.

39. The method of claim 38, wherein the pharmaceutically acceptable salt is a calcium salt.

40. The method of claim 37, wherein the compound is administered in combination with one or more of:

(a) Compound II:

(II)

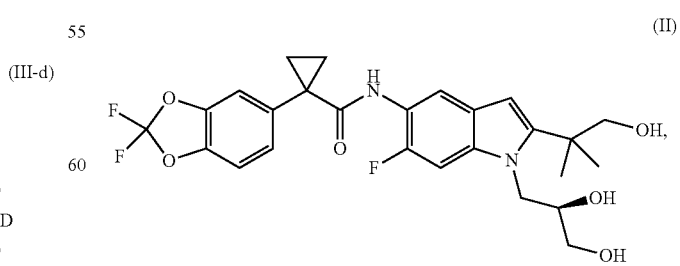

a pharmaceutically acceptable salt thereof, or a deuterated derivative of any of the foregoing; and (b) Compound III or Compound III-d:
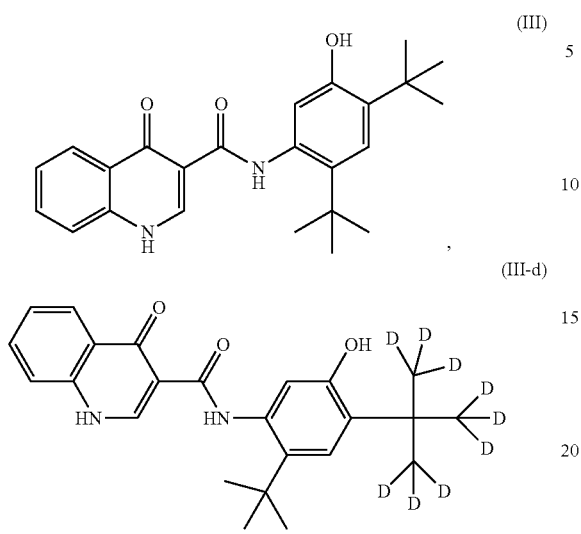
a pharmaceutically acceptable salt thereof, or a deuterated derivative of any of the foregoing.
41. The method of claim 40, wherein the compound is administered in combination with Compound II and Compound III-d.
* * * * *

UNITED STATES PATENT AND TRADEMARK OFFICE
CERTIFICATE OF CORRECTION

PATENT NO. : 11,866,450 B2
APPLICATION NO. : 17/323267
DATED : January 9, 2024
INVENTOR(S) : Jeremy J. Clemens et al.

Page 1 of 1

It is certified that error appears in the above-identified patent and that said Letters Patent is hereby corrected as shown below:

In the Claims

Claim 3, Column 1291, Line 62, "Z is a divalent linker of formula (L) r" should read --Z is a divalent linker of formula $(L)_r$--.

Claim 8, Column 1296, Line 61, "a6-membered heterocyclyl ring," should read --a 6-membered heterocyclyl ring,--.

Claim 34, Column 1351, Compound 253, " 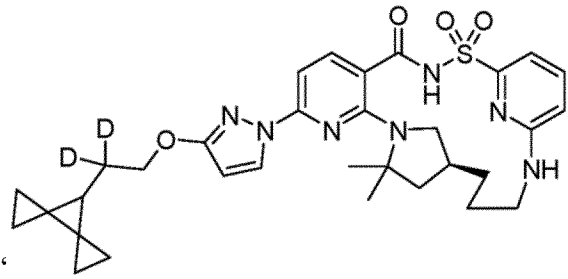 " should read -- 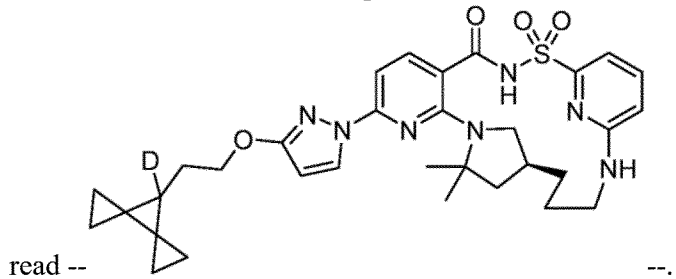 --.

Signed and Sealed this
Seventh Day of May, 2024

Katherine Kelly Vidal
*Director of the United States Patent and Trademark Office*